US012215105B2

(12) United States Patent
Kaila et al.

(10) Patent No.: US 12,215,105 B2
(45) Date of Patent: *Feb. 4, 2025

(54) HPK1 ANTAGONISTS AND USES THEREOF

(71) Applicant: Nimbus Saturn, Inc., Boston, MA (US)

(72) Inventors: Neelu Kaila, Lexington, MA (US); Ian Linney, Saffron Walden (GB); Stuart Ward, Saffron Walden (GB); Grant Wishart, Saffron Walden (GB); Ben Whittaker, Saffron Walden (GB); Alexandre Cote, West New York, NJ (US); Jeremy Robert Greenwood, Brooklyn, NY (US); Abba Leffler, Bronx, NY (US); Steven K. Albanese, Brooklyn, NY (US); Daniel L. Severance, San Diego, CA (US); Robert Griffiths, Saffron Walden (GB)

(73) Assignee: Nimbus Saturn, Inc., Boston, MA (US)

( * ) Notice: Subject to any disclaimer, the term of this patent is extended or adjusted under 35 U.S.C. 154(b) by 121 days.

This patent is subject to a terminal disclaimer.

(21) Appl. No.: 17/018,591

(22) Filed: Sep. 11, 2020

(65) Prior Publication Data
US 2021/0078996 A1 Mar. 18, 2021

Related U.S. Application Data

(60) Provisional application No. 63/032,070, filed on May 29, 2020, provisional application No. 62/900,152, filed on Sep. 13, 2019.

(51) Int. Cl.
C07D 471/04 (2006.01)
C07D 401/14 (2006.01)
C07D 487/04 (2006.01)
C07D 495/04 (2006.01)
C07D 498/04 (2006.01)
C07D 519/00 (2006.01)

(52) U.S. Cl.
CPC ......... C07D 471/04 (2013.01); C07D 401/14 (2013.01); C07D 487/04 (2013.01); C07D 495/04 (2013.01); C07D 498/04 (2013.01); C07D 519/00 (2013.01); C07B 2200/07 (2013.01)

(58) Field of Classification Search
CPC .. C07D 471/04; C07D 401/14; C07D 487/04; C07D 495/04; C07D 498/04; C07D 519/00; C07B 2200/07; A61K 31/4545; A61K 31/496; A61K 31/519; A61K 31/5377; A61K 31/55
USPC ...................................................... 514/394
See application file for complete search history.

(56) References Cited

U.S. PATENT DOCUMENTS

| 2,475,569 | A | 7/1949 | Mowat |
| 4,650,750 | A | 3/1987 | Giese |
| 4,709,016 | A | 11/1987 | Giese |
| 5,360,819 | A | 11/1994 | Giese |
| 5,516,931 | A | 5/1996 | Giese et al. |
| 5,602,273 | A | 2/1997 | Giese et al. |
| 5,604,104 | A | 2/1997 | Giese et al. |
| 5,610,020 | A | 3/1997 | Giese et al. |
| 5,650,270 | A | 7/1997 | Giese et al. |
| 7,390,799 | B2 | 6/2008 | Bruncko et al. |
| 8,138,347 | B2 | 3/2012 | Knight et al. |
| 8,906,682 | B2 | 12/2014 | June et al. |
| 11,021,481 | B2 | 6/2021 | Kaila et al. |
| 11,028,085 | B2 | 6/2021 | Kaila et al. |
| 11,034,694 | B2 | 6/2021 | Kaila et al. |
| 11,078,201 | B2 | 8/2021 | Kaila et al. |
| 2005/0026976 | A1 | 2/2005 | Curtin et al. |
| 2006/0287370 | A1 | 12/2006 | Curtin et al. |
| 2011/0245247 | A1 | 10/2011 | Braje et al. |
| 2016/0311772 | A1* | 10/2016 | Choi .............. C07D 209/48 |
| 2017/0226129 | A1 | 8/2017 | Yu et al. |
| 2018/0179221 | A1 | 6/2018 | Sampson et al. |
| 2018/0282328 | A1 | 10/2018 | Chan et al. |
| 2019/0256500 | A1 | 8/2019 | Vechorkin et al. |
| 2019/0256520 | A1 | 8/2019 | Sokolsky et al. |
| 2020/0038378 | A1 | 2/2020 | Crew et al. |

FOREIGN PATENT DOCUMENTS

| CA | 2988721 A1 | 6/2018 |
| CN | 109721620 A | 5/2019 |
| EP | 2108642 A1 | 10/2009 |
| WO | WO-2001042246 A2 | 6/2001 |
| WO | WO-2002088112 A1 | 11/2002 |
| WO | WO-2003063794 A2 | 8/2003 |
| WO | WO-2004019973 A1 | 3/2004 |
| WO | WO-2004089925 A1 | 10/2004 |
| WO | WO-2004106328 A1 | 12/2004 |
| WO | WO-2005007623 A2 | 1/2005 |

(Continued)

OTHER PUBLICATIONS

PCT International Search Report from PCT/US2020/050524 dated Oct. 31, 2020.
Adams et al., "Big opportunities for small molecules in immuno-oncology," Nature Reviews Drug Discovery. 2015; 14: 603-622.
Berge et al., "Pharmaceutical salts," J. Pharmaceutical Sciences 1977; 66(1):1-19.
Di Bartolo et al. "A novel pathway down-modulating T cell activation involves HPK-1-dependent recruitment of 14-3-3 proteins on SLP-76," J Exp Med. 2007; 204(3): 681-691.
Hu et al., "Human HPK1, a novel human hematopoietic progenitor kinase that activates the JNK/SAPK kinase cascade," Genes & Dev. 1996; 10(18): 2251-64.

(Continued)

Primary Examiner — Ana Z Muresan
(74) Attorney, Agent, or Firm — Dechert LLP; Andrea L. C. Reid; Todd K. Macklin

(57) ABSTRACT

The present invention provides compounds, compositions thereof, and methods of using the same for the inhibition of HPK1, and the treatment of HPK1-mediated disorders.

18 Claims, No Drawings

(56) References Cited

FOREIGN PATENT DOCUMENTS

| | | | |
|---|---|---|---|
| WO | WO-2005113554 | A2 | 12/2005 |
| WO | 2006021457 | A2 | 3/2006 |
| WO | WO-2006029879 | A2 | 3/2006 |
| WO | WO-2006078846 | A1 | 7/2006 |
| WO | WO-2006105021 | A2 | 10/2006 |
| WO | WO-2006122806 | A2 | 11/2006 |
| WO | WO-2007005874 | A3 | 1/2007 |
| WO | WO-2007016176 | A2 | 2/2007 |
| WO | WO-2007044729 | A2 | 4/2007 |
| WO | WO-2007053452 | A1 | 5/2007 |
| WO | WO-2007070514 | A1 | 6/2007 |
| WO | WO-2007084786 | A1 | 7/2007 |
| WO | WO-2007129161 | A2 | 11/2007 |
| WO | WO-2008039218 | A2 | 4/2008 |
| WO | WO-2008109943 | A1 | 9/2008 |
| WO | WO-2008118802 | A1 | 10/2008 |
| WO | WO-2008132601 | A1 | 11/2008 |
| WO | WO-2009009116 | A2 | 1/2009 |
| WO | WO-2009044273 | A3 | 4/2009 |
| WO | WO-2009073620 | A2 | 6/2009 |
| WO | WO-2009074812 | A1 | 6/2009 |
| WO | WO-2009114512 | A1 | 9/2009 |
| WO | WO-2010019570 | A2 | 2/2010 |
| WO | WO-2010077634 | A1 | 7/2010 |
| WO | 2010141406 | A2 | 12/2010 |
| WO | WO-2011028683 | A1 | 3/2011 |
| WO | WO-2011056652 | A1 | 5/2011 |
| WO | WO-2011070024 | A1 | 6/2011 |
| WO | WO-2011090760 | A1 | 7/2011 |
| WO | WO-2011107553 | A1 | 9/2011 |
| WO | WO-2011109400 | A2 | 9/2011 |
| WO | WO-2011131407 | A1 | 10/2011 |
| WO | WO-2011140249 | A2 | 11/2011 |
| WO | WO-2012032433 | A1 | 3/2012 |
| WO | WO-2012142237 | A1 | 10/2012 |
| WO | WO-2013079174 | A1 | 6/2013 |
| WO | WO-2013086397 | A1 | 6/2013 |
| WO | WO-2013087699 | A1 | 6/2013 |
| WO | WO-2013119716 | A1 | 8/2013 |
| WO | WO-2013132044 | A1 | 9/2013 |
| WO | WO-2013169264 | A1 | 11/2013 |
| WO | WO-2014008218 | A1 | 1/2014 |
| WO | WO-2014036357 | A1 | 3/2014 |
| WO | WO-2014074660 | A1 | 5/2014 |
| WO | WO-2014074661 | A1 | 5/2014 |
| WO | WO-2015089143 | A1 | 6/2015 |
| WO | WO-2015131080 | A1 | 9/2015 |
| WO | WO-2016106106 | A2 | 6/2016 |
| WO | 2016205942 | A1 | 12/2016 |
| WO | WO2017147328 | * | 8/2017 |
| WO | 2018049152 | A1 | 3/2018 |
| WO | 2018068017 | A1 | 4/2018 |
| WO | 2018102366 | A1 | 6/2018 |
| WO | 2019090198 | A1 | 5/2019 |
| WO | WO-2020089026 | A2 | 5/2020 |
| WO | 2021262684 | A1 | 12/2021 |

OTHER PUBLICATIONS

Ikegami et al., "The expression of prostaglandin E receptors $EP_2$ and $EP_4$ and their different regulation by lipopolysaccharide in C3H/HeN peritoneal macrophages," J Immunol. 2001; 166(7): 4689-96.

Kiefer et al., "HPK1, a hematopoietic protein kinase activating the SAPK/JNK pathway," EMBO J. 1996; 15(24): 7013-25.

Lasserre et al., "Release of serine/threonine-phosphorylated adaptors from signaling microclusters down-regulates T cell activation," J Cell Biol. 2011; 195(5): 839-853.

Liou et al., "HPK1 is activated by lymphocyte antigen receptors and negatively regulates AP-1," Immunity. 2000; 12(4): 399-408.

Okazaki et al., "A rheostat for immune responses: the unique properties of PD-1 and their advantages for clinical application," Nat. Immunol. 2013; 14(12): 1212-1218.

Ramirez et al "Defining causative factors contributing in the activation of hedgehog signaling in diffuse large B-cell lymphoma" Leuk. Res. (2012); 36(10): 1267-1273.

Ross et al., "Bispecific T cell engager (BITE®) antibody constructs can mediate bystander tumor cell killing," PLoS ONE. 2017; 12(8): e0183390.

Rostovtsev et al., "A stepwise Huisgen cycloaddition process: copper(I)-catalyzed regioselective "ligation" of azides and terminal alkynes," Angew. Chem. Int. Ed., 2002, vol. 41, pp. 2596-2599.

Shui et al., "Hematopoietic progenitor kinase 1 negatively regulates T cell receptor signaling and T cell-mediated immune responses," Nat Immunol. 2007; 8(1): 84-91.

Sun et al., "Carbohydrate and protein immobilization onto solid surfaces by sequential Diels-Alder and azide-alkyne cycloadditions," Bioconjugate Chem., 2006, vol. 17, No. 1, pp. 52-57.

Toogood, "Small molecule immuno-oncology therapeutic agents," Bioorganic & Medicinal Chemistry Letters. 2018; 28(3): 319-329.

Wang et al., "Activation of the hematopoietic progenitor kinase-1 (HPK1)-dependent, stress-activated c-Jun N-terminal kinase (JNK) pathway by transforming growth factor beta (TGF-beta)-activated kinase (TAK1), a kinase mediator of TGF beta signal transduction," J Biol Chem. 1997; 272(36): 22771-5.

Wang et al., "Down-regulation of B cell receptor signaling by hematopoietic progenitor kinase 1 (HPK1)-mediated phosphorylation and ubiquitination of activated B cell linker protein (BLNK)," J Biol Chem. 2012; 287(14): 11037-48.

Zhou et al., "Hematopoietic progenitor kinase 1 is a component of transforming growth factor beta-induced c-Jun N-terminal kinase signaling cascade," J Biol Chem. 1999; 274(19): 13133-8.

Zou et al., "PD-L1 (B7-H1) and PD-1 pathway blockade for cancer therapy: Mechanisms, response biomarkers, and combinations," Sci. Transl. Med. 2016; 8(328): 1-14.

* cited by examiner

HPK1 ANTAGONISTS AND USES THEREOF

CROSS-REFERENCE TO RELATED APPLICATIONS

This application claims the benefit under 35 U.S.C. § 119(e) of U.S. Provisional Application No. 62/900,152, filed Sep. 13, 2019 and U.S. Provisional Application No. 63/032,070, filed May 29, 2020, the contents of each of which is incorporated herein in its entirety by reference.

TECHNICAL FIELD OF THE INVENTION

The present invention relates to compounds and methods useful for antagonizing hematopoietic progenitor kinase 1 (HPK1). The invention also provides pharmaceutically acceptable compositions comprising compounds of the present invention and methods of using said compositions in the treatment of various disorders.

BACKGROUND OF THE INVENTION

The hematopoietic progenitor kinase 1 (HPK1), otherwise known as mitogen activated protein kinase kinase kinase kinase 1 (MAP4K1), is a hematopoietic cell-restricted member of the Ste20 serine/threonine kinase super family. The MAP4Ks family includes MAP4K1/HPK1, MAP4K2/GCK, MAP4K3/GLK, MAP4K4/HGK, MAP4K5/KHS, and MAP4K6/MINK. HPK1 is a tissue-specific upstream activator of the MEKK/JNK/SAPK signaling pathway.

HPK1 is of particular interest because it is predominantly expressed in hematopoietic cells such as T cells, B cells, macrophages, dendritic cells, neutrophils, and mast cells (Hu, M. C., et al., Genes Dev, 1996. 10(18): p. 2251-64; Kiefer, F., et al., EMBO J, 1996. 15(24): p. 7013-25). HPK1 kinase activity has been shown to be induced upon activation of T cell receptors (TCR) (Liou, J., et al., Immunity, 2000. 12(4): p. 399-408), B cell receptors (BCR) (Liou, J., et al., Immunity, 2000. 12(4): p. 399-408), transforming growth factor receptor (TGF-PR) (Wang, W., et al., J Biol Chem, 1997. 272(36): p. 22771-5; Zhou, G., et al., J Biol Chem, 1999. 274(19): p. 13133-8), or Gs-coupled PGE2 receptors (EP2 and EP4) (Ikegami, R., et al., J Immunol, 2001. 166(7): p. 4689-96). As such, HPK1 regulates diverse functions of various immune cells. HPK1 is also an example of a negative regulator of dendritic cell activation, and T and B cell responses that can be targeted to enhance anti-tumor immunity. HPK1 is expressed predominantly by hematopoietic cells, including early progenitors. In T cells, it is believed that HPK1 negatively regulates T cell activation by reducing the persistence of signaling microclusters by phosphorylating SLP76 at Ser376 (Di Bartolo et al. (2007) JEM 204:681-691) and Gads at Thr254, which leads to the recruitment of 14-3-3 proteins that bind to the phosphorylated SLP76 and Gads, releasing the SLP76-Gads-14-3-3 complex from LAT-containing microclusters (Lasserre et al. (2011) J Cell Biol 195(5):839-853). HPK1 can also become activated in response to prostaglandin E2, which is often secreted by tumors, contributing to the escape of tumor cells from the immune system.

HPK1 is important in regulating the functions of various immune cells and it has been implicated in autoimmune diseases and anti-tumor immunity (Shui, J. W., et al., Nat Immunol, 2007. 8(1): p. 84-91; Wang, X., et al., J Biol Chem, 2012. 287(14): p. 11037-48).

SUMMARY OF THE INVENTION

It has now been found that compounds of this invention, and pharmaceutically acceptable compositions thereof, are effective as antagonists of HPK1. In certain embodiments, the invention provides for compounds of the formulae presented herein.

Compounds of the present invention, and pharmaceutically acceptable compositions thereof, are useful for treating a variety of diseases, disorders or conditions, associated with regulation of signaling pathways implicating HPK1 kinases. Such diseases, disorders, or conditions include those described herein.

Compounds provided by this invention are also useful for the study of HPK1 enzymes in biological and pathological phenomena; the study of intracellular signal transduction pathways occurring in bodily tissues; and the comparative evaluation of new HPK1 inhibitors or other regulators of kinases, signaling pathways, and cytokine levels in vitro or in vivo.

DETAILED DESCRIPTION OF CERTAIN EMBODIMENTS

1. General Description of Certain Embodiments of the Invention

In certain aspects, the present invention provides a compound of formula I:

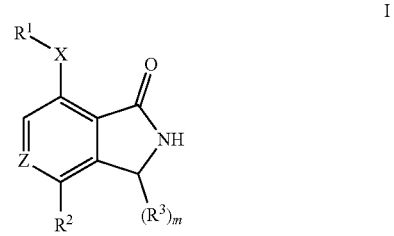

or a pharmaceutically acceptable salt thereof, wherein each of X, Z, $R^1$, $R^2$, $R^3$, and m, is as defined below and described in embodiments herein, both singly and in combination.

In some embodiments, the present invention provides a pharmaceutical composition comprising a compound of formula I and a pharmaceutically acceptable carrier, adjuvant, or diluent.

In some embodiments, the present invention provides a method of treating a HPK1-mediated disease, disorder, or condition comprising administering to a patient in need thereof, a compound of formula I, or a pharmaceutically acceptable salt thereof.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic C3-C6 hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

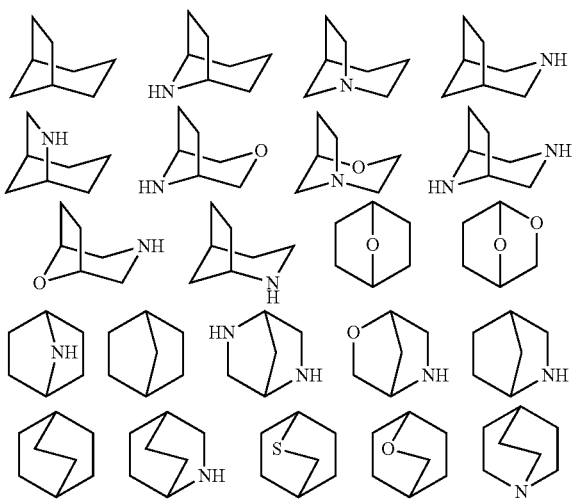

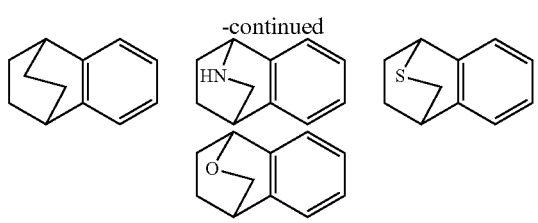

-continued

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., $-(CH_2)_n-$, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14 π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where unless otherwise specified, the radical or point of attachment is on the heteroaromatic ring or on one of the rings to which the heteroaromatic ring is fused. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, and tetrahydroisoquinolinyl. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or $^+$NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, 2-oxa-6-azaspiro[3.3]heptane, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH(OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R°)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —N(R°)C(NR°)N(R°)$_2$, —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)O SiR°$_3$; —(CH$_2$)$_{0-4}$OC(O)R°; —OC(O)(CH$_2$)$_{0-4}$SR°; —SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR°$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; —SiR°$_3$; —(C$_{1-4}$ straight or branched alkylene)O—N(R°)$_2$; or —(C$_{1-4}$ straight or branched)alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^\bullet$, (haloR$^\bullet$), —(CH$_2$)$_{0-2}$OH, —(CH$_2$)$_{0-2}$OR$^\bullet$, —(CH$_2$)$_{0-2}$CH(OR$^\bullet$)$_2$; —O(haloR$^\bullet$), —CN, —N$_3$, —(CH$_2$)$_{0-2}$C(O)R$_\bullet$, —(CH$_2$)$_{0-2}$C(O)OH, —(CH$_2$)$_{0-2}$C(O)OR$^\bullet$, —(CH$_2$)$_{0-2}$SR$^\bullet$, —(CH$_2$)$_{0-2}$SH, —(CH$_2$)$_{0-2}$NH$_2$, —(CH$_2$)$_{0-2}$NHR$^\bullet$, —(CH$_2$)$_{0-2}$NR$^\bullet$$_2$, —NO$_2$, —SiR$^\bullet$$_3$, —OSiR$^\bullet$$_3$, —C(O)SR$^\bullet$, —(C$_{1-4}$ straight or branched alkylene)C(O)OR$^\bullet$, or —SSR$^\bullet$ wherein each R● is unsubstituted or where preceded by "halo" is substituted only with one or more halogens, and is independently selected from $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, $C_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R†, NR†$_2$, —C(O)R†$_2$, —C(O)OR†, —C(O)C(O)R†, —C(O)CH$_2$C(O)R†, —S(O)$_2$R†, —S(O)$_2$NR†$_2$, —C(S)NR†$_2$, —C(NH)NR†$_2$, or —N(R†)S(O)$_2$R†; wherein each R† is independently hydrogen, $C_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R†, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R† are independently halogen, —R●, -(haloR●), —OH, —OR●, —O(haloR●), —CN, —C(O)OH, —C(O)OR●, —NH$_2$, —NHR●, —NR●$_2$, or —NO$_2$, wherein each R● is unsubstituted or where preceded by "halo" is substituted only with one or more halogens, and is independently $C_{1-4}$ aliphatic, —$CH_2Ph$, —$O(CH_2)_{0-1}Ph$, or a 5-6-membered saturated, partially unsaturated, or aryl ring having 0-4 heteroatoms independently selected from nitrogen, oxygen, or sulfur.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}\ alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}$C- or $^{14}$C-enriched carbon are within the scope of this invention. Such compounds are useful, for example, as analytical tools, as probes in biological assays, or as therapeutic agents in accordance with the present invention. In certain embodiments, a warhead moiety, $R^1$, of a provided compound comprises one or more deuterium atoms. In certain embodiments, Ring B of a provided compound may be substituted with one or more deuterium atoms.

The structures as drawn represent relative configurations, unless labeled as absolute configurations. The invention contemplates individual enantiomers and racemic mixtures.

As used herein, a "HPK1 antagonist" or a "HPK1 inhibitor" is a molecule that reduces, inhibits, or otherwise diminishes one or more of the biological activities of HPK1 (e.g., serine/threonine kinase activity, recruitment to the TCR complex upon TCR activation, interaction with a protein binding partner, such as SLP76). Antagonism using the HPK1 antagonist does not necessarily indicate a total elimination of the HPK1 activity. Instead, the activity could decrease by a statistically significant amount including, for example, a decrease of at least about 5%, 10%, 15%, 20%, 25%, 30%, 35%, 40%, 45%, 50%, 55%, 60%, 65%, 70%, 75%, 80%, 85%, 95% or 100% of the activity of HPK1 compared to an appropriate control. In some embodiments, the HPK1 antagonist reduces, inhibits, or otherwise diminishes the serine/threonine kinase activity of HPK1. In some of these embodiments, the HPK1 antagonist reduces, inhibits, or otherwise diminishes the HPK1-mediated phosphorylation of SLP76 and/or Gads. The presently disclosed compounds bind directly to HPK1 and inhibit its kinase activity.

By "specific antagonist" is intended an agent that reduces, inhibits, or otherwise diminishes the activity of a defined target greater than that of an unrelated target. For example, a HPK1 specific antagonist reduces at least one biological activity of HPK1 by an amount that is statistically greater than the inhibitory effect of the antagonist on any other protein (e.g., other serine/threonine kinases). In some embodiments, the $IC_{50}$ of the antagonist for the target is about 90%, 80%, 70%, 60%, 50%, 40%, 30%, 20%, 10%, 5%, 1%, 0.1%, 0.01%, 0.001% or less of the $IC_{50}$ of the antagonist for a non-target. The presently disclosed compounds may or may not be a specific HPK1 antagonist. A specific HPK1 antagonist reduces the biological activity of HPK1 by an amount that is statistically greater than the inhibitory effect of the antagonist on any other protein (e.g., other serine/threonine kinases). In certain embodiments, the HPK1 antagonist specifically inhibits the serine/threonine kinase activity of HPK1. In some of these embodiments, the $IC_{50}$ of the HPK1 antagonist for HPK1 is about 90%, 80%, 70%, 60%, 50%, 40%, 30%, 20%, 10%, 0.1%, 0.01%, 0.001%, or less of the $IC_{50}$ of the HPK1 antagonist for another serine/threonine kinase or other type of kinase (e.g., tyrosine kinase).

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}P$, $^{33}P$, $^{35}S$, or $^{14}C$), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in a HPK1 protein kinase activity between a sample comprising a compound of the present invention, or composition thereof, and a HPK1 protein kinase, and an equivalent sample comprising an HPK1 protein kinase, in the absence of said compound, or composition thereof.

3. Description of Exemplary Embodiments

As described above, in certain embodiments, the present invention provides a compound of formula I:

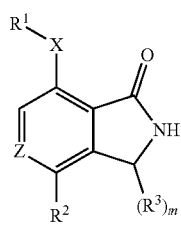

I or a pharmaceutically acceptable salt thereof, wherein:
Z is CR or N;
X is a covalent bond, —O—, —S—, —NR—, —S(O)$_2$—, —S(O)$_2$NR—, —S(O)—, —S(O)NR—, —C(O)—, —C(O)O—, —C(O)NR—, —C(O)N(R)O—, —OC(O)—, —OC(O)NR—, —N(R)C(O)O—, —N(R)C(O)—, —N(R)S(O)$_2$—; or X is a C$_{1-4}$ bivalent saturated or unsaturated, straight or branched hydrocarbon chain wherein one or two methylene units of the chain are optionally and independently replaced by —C(R)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—;
R$^1$ is selected from C$_{1-6}$ aliphatic; phenyl; a 3-7 membered saturated or partially unsaturated monocyclic carbocyclic ring; a 5-6 membered monocyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; and an 8-10 membered saturated or partially unsaturated bicyclic heterocyclic ring having 1-4 heteroatoms independently selected from nitrogen, oxygen, and sulfur; each of which is substituted with q instances of R$^C$;
R$^2$ is a 6-11 membered saturated, partially unsaturated, or unsaturated fused, bridged, or spiro bicyclic ring having 0-3 heteroatoms independently selected from nitrogen, oxygen, and sulfur; each of which is substituted with q instances of R$^C$;
each instance of R$^3$ is independently hydrogen or an optionally substituted C$_{1-6}$ aliphatic group;
each instance of R$^C$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N═S(O)R$_2$, —S(NR)(O)R, —N(R)S(O)R, —N(R)CN, —P(O)(R)NR$_2$, —P(O)(R)OR or —P(O)R$_2$; or each instance of R$^C$ is independently an optionally substituted group selected from C$_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; or a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-11 membered saturated or partially unsaturated spirocyclic ring having 0-3 heteroatoms independently selected from nitrogen, oxygen, and sulfur; or a 6-11 membered saturated or partially unsaturated bicyclic heterocyclic ring having 1-3 heteroatoms independently selected from nitrogen, oxygen, and sulfur; each of which is substituted with r instances of R and s instances of R$^D$;
each instance of R$^D$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N═S(O)R$_2$, —S(NR)(O)R, —N(R)S(O)R, —N(R)CN, —P(O)(R)NR$_2$, —P(O)(R)OR or —P(O)R$_2$;
each R is independently hydrogen, —CN, halogen, or an optionally substituted group selected from C$_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; a 6-11 membered saturated or partially unsaturated bicyclic carbocyclic ring having 1-2 heteroatoms independently selected from nitrogen, oxygen, and sulfur; or:
two R groups on the same nitrogen are taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur; an 8-10 membered bicyclic heteroaryl ring having 1-4 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur;
m is 0, 1, or 2;
each q is independently 0, 1, 2, 3, or 4;
each r is independently 0, 1, 2, 3, or 4; and
each s is independently 0, 1, 2, 3, or 4.
As defined generally above, Z is CR or N.
In some embodiments. Z is CR. In some embodiments, Z is N.

In some embodiments, Z is CH. In some embodiments, Z is CCl. In some embodiments, Z is CF. In some embodiments, Z is CCH$_3$.

In some embodiments, Z is selected from those depicted in Table 1, below.

As defined generally above, X is a covalent bond, —O—, —S—, —NR—, —S(O)$_2$—, —S(O)$_2$NR—, —S(O)—, —S(O)NR—, —C(O)—, —C(O)O—, —C(O)NR—, —C(O)N(R)O—, —OC(O)—, —OC(O)NR—, —N(R)C(O)O—, —N(R)C(O)—, —N(R)S(O)$_2$—; or X is a C$_{1-4}$ bivalent saturated or unsaturated, straight or branched hydrocarbon chain wherein one or two methylene units of the chain are optionally and independently replaced by —C(R)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—.

In certain embodiments, X is —O—, —S—, —NR—, —S(O)$_2$—, —S(O)$_2$NR—, —S(O)—, —S(O)NR—, —C(O)—, —C(O)O—, —C(O)NR—, —C(O)N(R)O—, —OC(O)—, —OC(O)NR—, —N(R)C(O)O—, —N(R)C(O)—, —N(R)C(O)NR—, —N(R)C(NR)NR—, —N(R)NR—, —N(R)S(O)$_2$NR—, or —N(R)S(O)$_2$—.

In some embodiments, X is a C$_{1-4}$ bivalent saturated or unsaturated, straight or branched hydrocarbon chain wherein one or two methylene units of the chain are optionally and independently replaced by —C(R)$_2$—, —N(R)—, —N(R)C(O)—, —C(O)N(R)—, —N(R)S(O)$_2$—, —S(O)$_2$N(R)—, —O—, —C(O)—, —OC(O)—, —C(O)O—, —S—, —S(O)— or —S(O)$_2$—.

In certain embodiments, X is —NR—, —C(O)—, —C(O)O—, —C(O)NR—, —C(O)N(R)O—, —OC(O)—, —OC(O)NR—, —N(R)C(O)O—, —N(R)C(O)—, —N(R)C(O)NR—, —N(R)C(NR)NR—, or —N(R)NR—.

In certain embodiments, X is —NR—. In certain embodiments, X is —NH—.

In some embodiments, X is selected from those depicted in Table 1, below.

As defined generally above, R$^1$ is selected from C$_{1-6}$ aliphatic; phenyl; a 3-7 membered saturated or partially unsaturated monocyclic carbocyclic ring; a 5-6 membered monocyclic heteroaryl ring having 1-4 heteroatoms independently selected from nitrogen, oxygen, and sulfur; a 3-7 membered saturated or partially unsaturated monocyclic heterocyclic ring having 1-2 heteroatoms independently selected from nitrogen, oxygen, and sulfur; and an 8-10 membered saturated or partially unsaturated bicyclic heterocyclic ring having 1-4 heteroatoms independently selected from nitrogen, oxygen, and sulfur; each of which is substituted with q instances of R$^C$.

In some embodiments, R$^1$ is C$_{1-6}$ aliphatic which is substituted with q instances of R$^C$; phenyl which is substituted with q instances of R$^C$; a 3-7 membered saturated or partially unsaturated monocyclic carbocyclic ring, which is substituted with q instances of R$^C$; a 5-6 membered monocyclic heteroaryl ring having 1-4 heteroatoms independently selected from nitrogen, oxygen, and sulfur, which is substituted with q instances of R$^C$; a 3-7 membered saturated or partially unsaturated monocyclic heterocyclic ring having 1-2 heteroatoms independently selected from nitrogen, oxygen, and sulfur, which is substituted with q instances of R$^C$; or an 8-10 membered saturated or partially unsaturated bicyclic heterocyclic ring having 1-4 heteroatoms independently selected from nitrogen, oxygen, and sulfur; which is substituted with q instances of R$^C$.

In some embodiments, R$^1$ is phenyl or a 5-6 membered monocyclic heteroaryl ring having 1-4 heteroatoms independently selected from nitrogen, oxygen, and sulfur, each of which is substituted with q instances of R$^C$.

In certain embodiments, R$^1$ is phenyl, indanyl, tetrahydronaphthyl, acridinyl, azocinyl, benzimidazolyl, benzofuranyl, benzothiofuranyl, benzothiophenyl, benzoxazolyl, benzthiazolyl, benztriazolyl, benztetrazolyl, benzisoxazolyl, benzisothiazolyl, benzimidazolinyl, carbazolyl, NH-carbazolyl, carbolinyl, chromanyl, chromenyl, cinnolinyl, decahydroquinolinyl, 2H,6H-1,5,2-dithiazinyl, dihydrofuro [2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isoindolinyl, isoindolenyl, isobenzofuranyl, isochromanyl, isoindazolyl, isoindolinyl, isoindolyl, isoquinolinyl, isothiazolyl, isoxazolyl, morpholinyl, naphthyridinyl, octahydroisoquinolinyl, oxadiazolyl, 1,2,3-oxadiazolyl, 1,2,4-oxadiazolyl; -1,2,5oxadiazolyl, 1,3,4-oxadiazolyl, oxazolidinyl, oxazolyl, oxazolidinyl, oxetanyl, pyrimidinyl, phenanthridinyl, phenanthrolinyl, phenazinyl, phenothiazinyl, phenoxathiinyl, phenoxazinyl, phthalazinyl, piperazinyl, piperidinyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydropyranyl, tetrahydroisoquinolinyl, tetrahydroquinolinyl, 6H-1,2,5-thiadiazinyl, 1,2,3-thiadiazolyl, 1,2,4-thiadiazolyl, 1,2,5-thiadiazolyl, 1,3,4thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, oxetanyl, azetidinyl, or xanthenyl; each of which is substituted by q instances of R$^C$.

In certain embodiments, R$^1$ is phenyl, furanyl, furazanyl, imidazolidinyl, imidazolinyl, imidazolyl, isothiazolyl, isoxazolyl, morpholinyl, oxadiazolyl, 1,2,3-oxadiazolyl, 1,2,4-oxadiazolyl;- 1,2,5 oxadiazolyl, 1,3,4-oxadiazolyl, oxazolidinyl, oxazolyl, oxazolidinyl, oxetanyl, pyrimidinyl, piperazinyl, piperidinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, 2H-pyrrolyl, pyrrolyl, tetrahydrofuranyl, tetrahydropyranyl, thiazolyl, thienyl, triazinyl, 1,2,3-triazolyl, 1,2,4-triazolyl, 1,2,5-triazolyl, 1,3,4-triazolyl, oxetanyl, azetidinyl, or xanthenyl; each of which is substituted by q instances of R$^C$.

In certain embodiments, R$^1$ is furanyl, furazanyl, imidazolidinyl, imidazolinyl, imidazolyl, isothiazolyl, isoxazolyl, oxadiazolyl, 1,2,3-oxadiazolyl, 1,2,4-oxadiazolyl;-1,2,5-oxadiazolyl, 1,3,4-oxadiazolyl, oxazolidinyl, oxazolyl, oxazolidinyl, oxetanyl, pyrimidinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, 2H-pyrrolyl, pyrrolyl, thiazolyl, thienyl, triazinyl, 1,2,3-triazolyl, 1,2,4-triazolyl, or 1,2,5-triazolyl, 1,3,4-triazolyl; each of which is substituted by q instances of R$^C$.

In certain embodiments, R$^1$ is phenyl, pyrazolyl, pyridinyl, pyrazinyl, or pyrimidinyl; each of which is substituted by q instances of R$^C$.

In certain embodiments, R$^1$ is pyrazolyl or pyridinyl; each of which is substituted by q instances of R$^C$.

In certain embodiments, R$^1$ is pyrazolyl or pyridinyl; each of which is substituted by q instances of R$^C$; wherein each R$^C$ is independently halogen, —CN, —OR, —S(O)$_2$R, —C(O)NR$_2$, or each instance of R$^C$ is independently an optionally substituted group selected from C$_{1-6}$ aliphatic; a 5-10 membered saturated or partially unsaturated bridged bicyclic ring having 0-3 heteroatoms independently selected from nitrogen, oxygen, and sulfur; a 6-12 membered saturated or partially unsaturated spirocyclic ring having 0-3 heteroatoms independently selected from nitrogen, oxygen, and sulfur; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; or two $R^C$ groups together with the atoms to which each is attached, forms a bridged, fused, or spiro 5-6 membered aryl ring, a 3-7 membered saturated or partially unsaturated monocyclic carbocyclic ring, a 3-7 membered saturated or partially unsaturated monocyclic heterocyclic ring having 1-2 heteroatoms independently selected from nitrogen, oxygen, phosphorous, silicon and sulfur; wherein each instance of $R^C$ is independently optionally substituted by R and $R^D$.

In certain embodiments, $R^1$ is

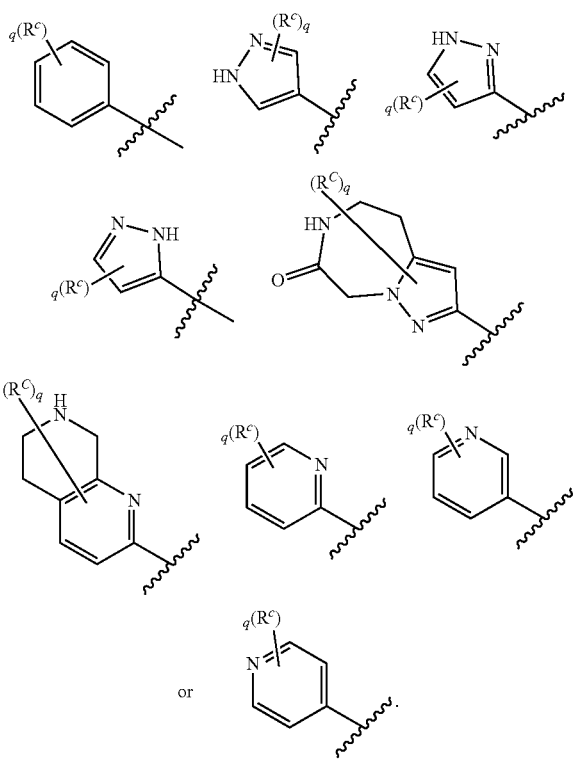

or

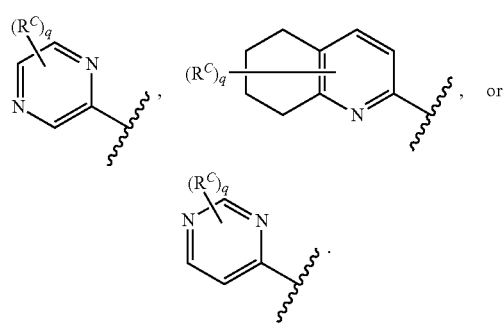

In certain embodiments, $R^1$ is

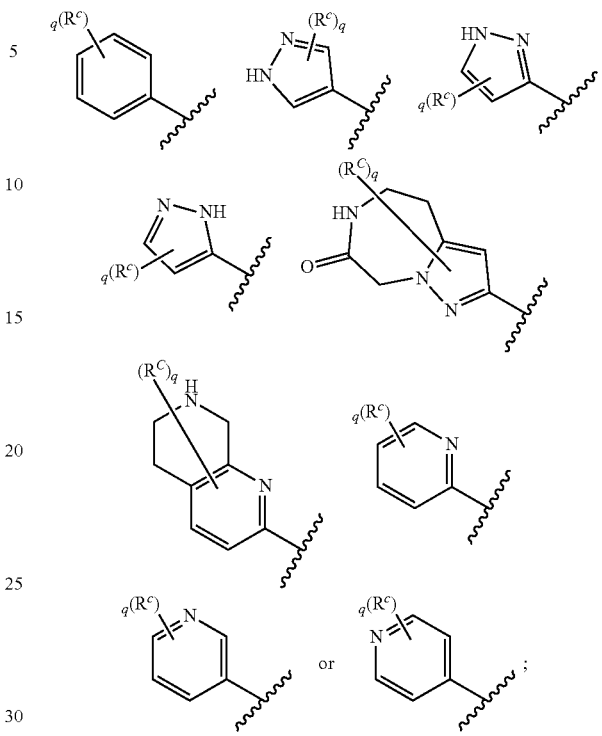

wherein each instance of $R^C$ is independently a 3-7 membered saturated or partially unsaturated monocyclic heterocyclic ring having 1-2 heteroatoms independently selected from nitrogen, oxygen, phosphorous, silicon and sulfur; or a 5-8 membered saturated or partially unsaturated bridged bicyclic ring having 0-3 heteroatoms independently selected from nitrogen, oxygen, and sulfur; each of which is substituted with r instances of R and s instances of $R^D$.

In certain embodiments, $R^1$ is

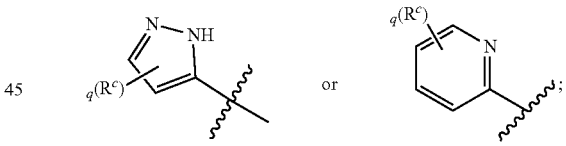

wherein each instance of $R^C$ is independently -Me, -Et, —CN, —F, —OMe, —S(O)$_2$Me,

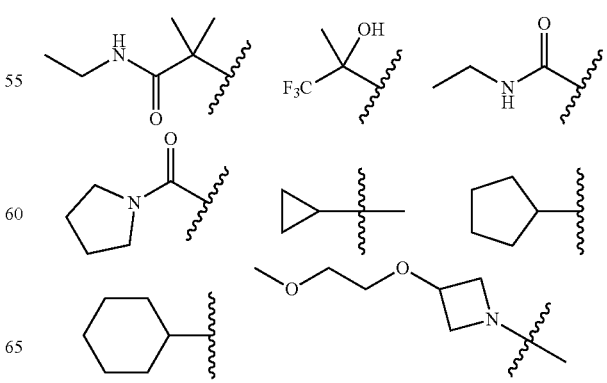

-continued
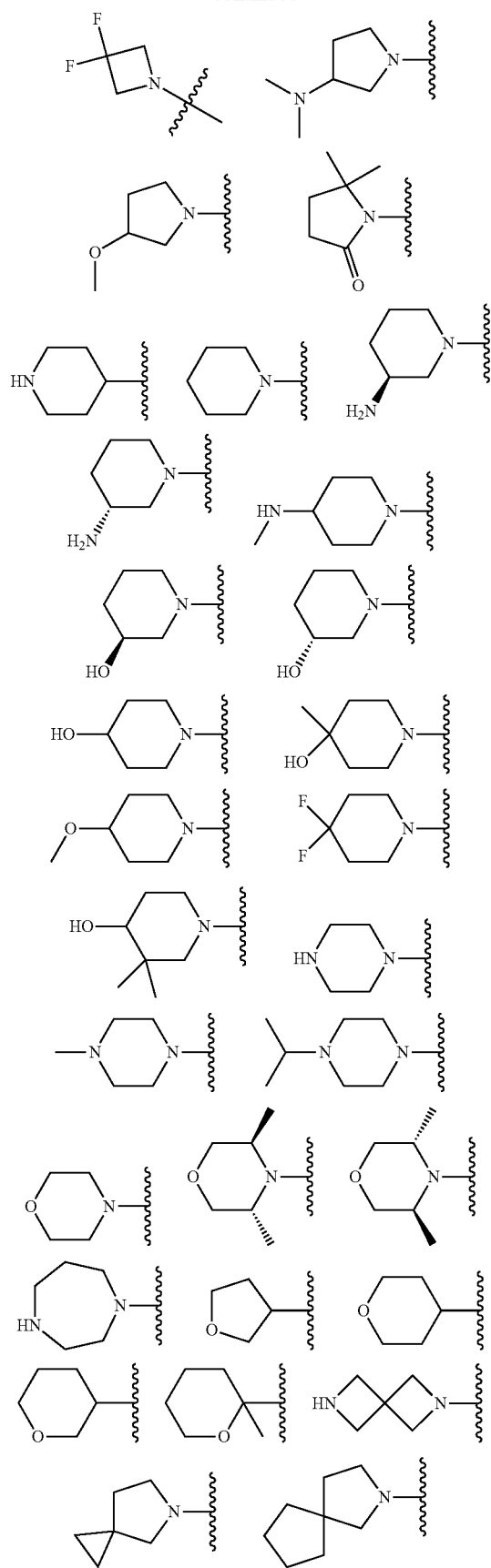
-continued
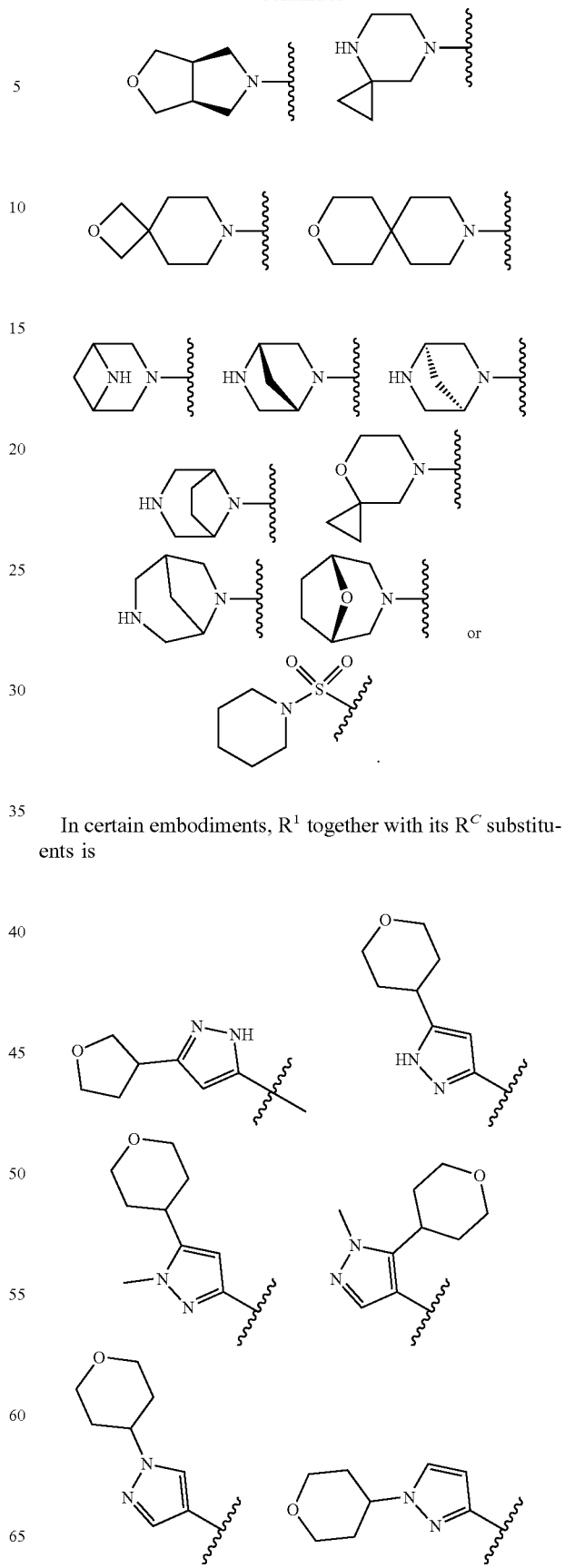
In certain embodiments, R[1] together with its R[C] substituents is

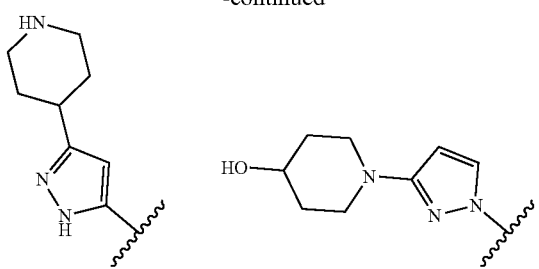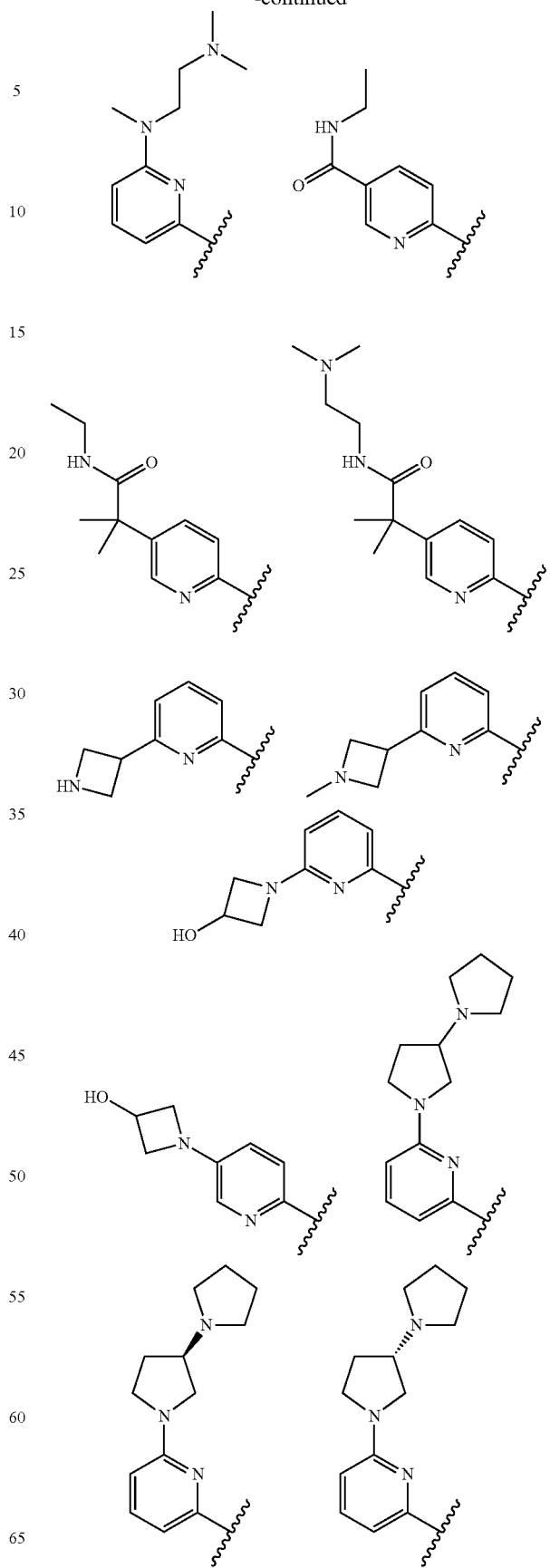

-continued
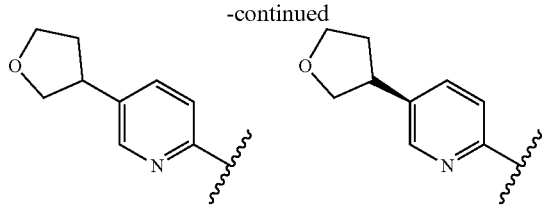
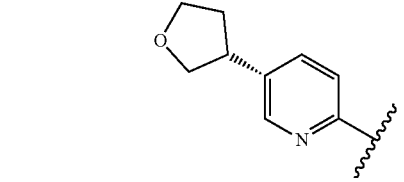
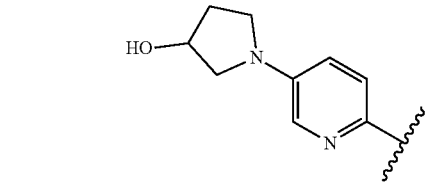
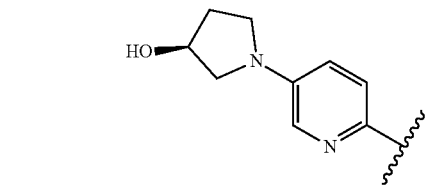
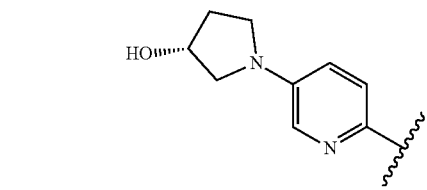
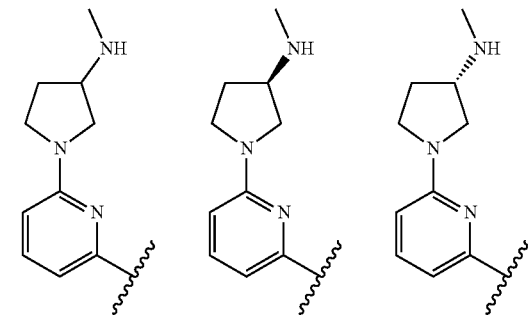
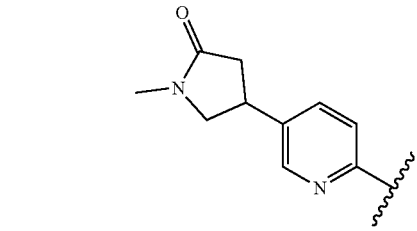
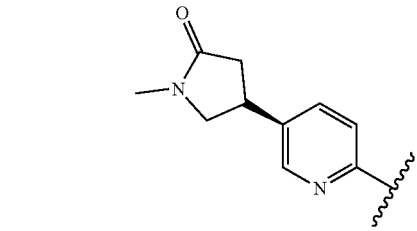
-continued
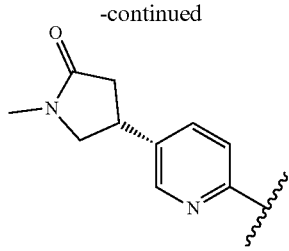
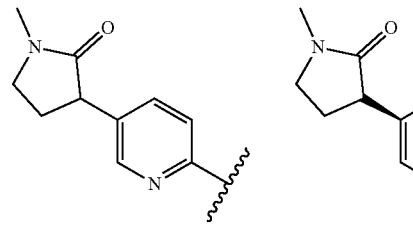
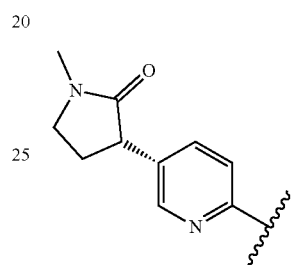
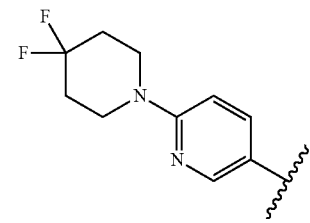
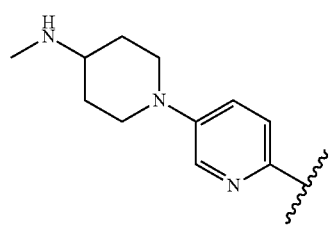
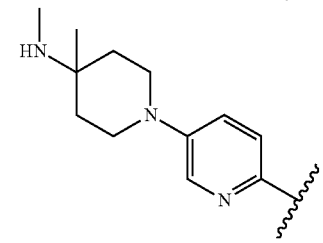
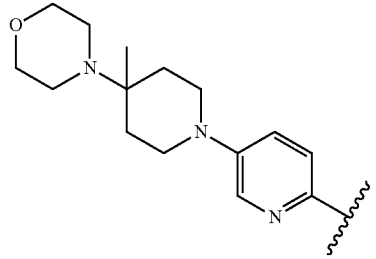
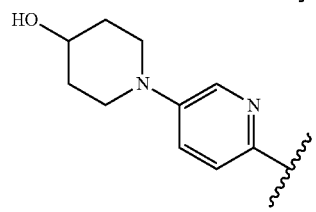

-continued
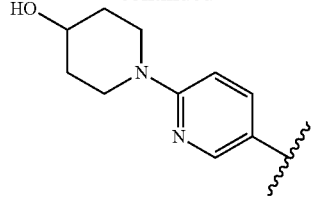
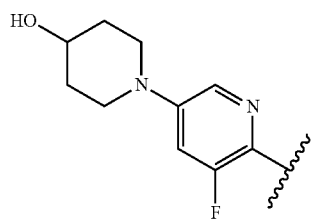
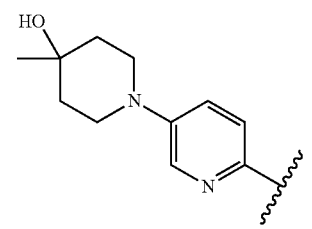
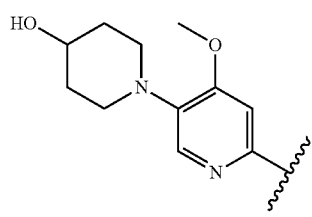
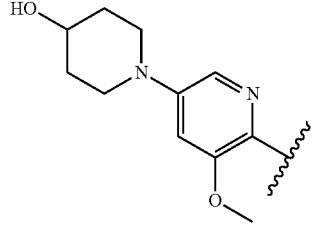
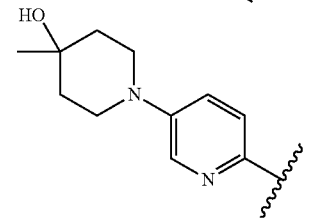
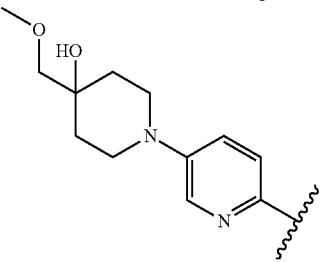
-continued
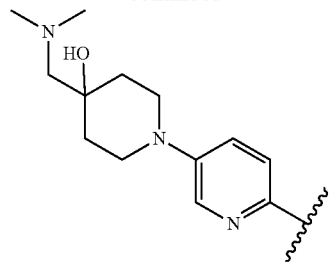
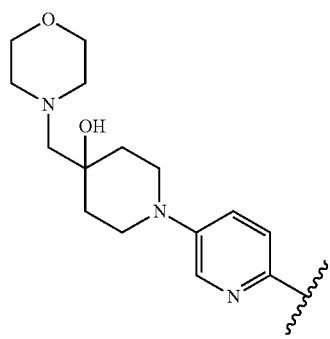
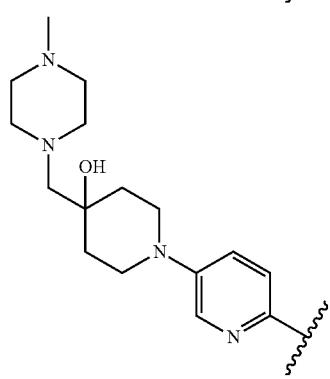
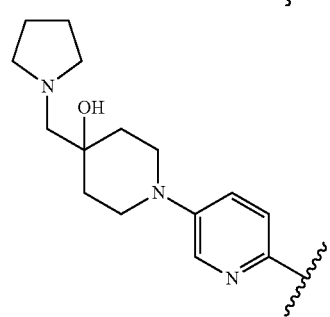
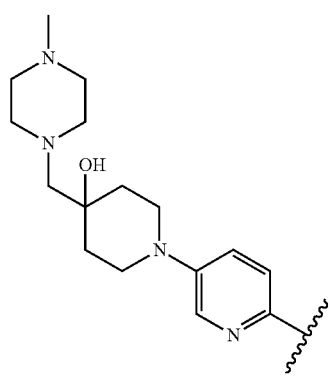

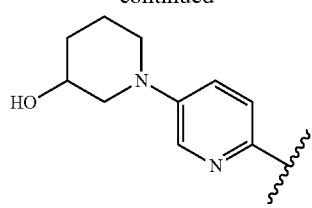
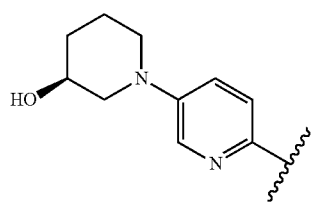
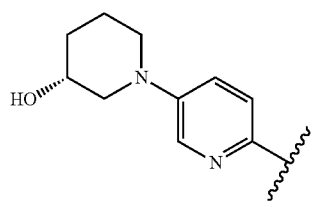
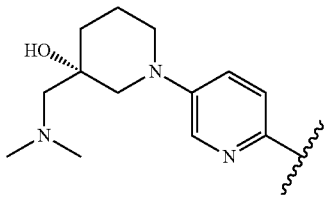
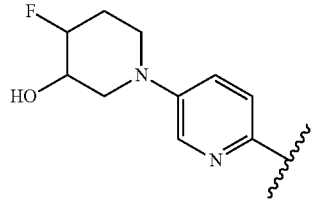
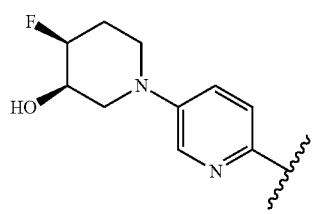
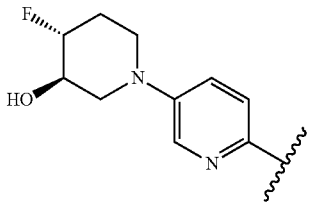
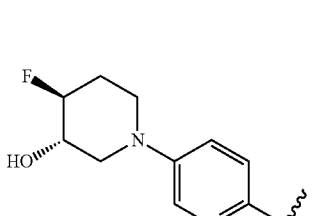
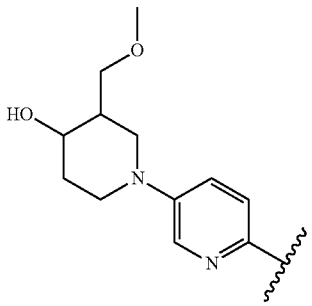
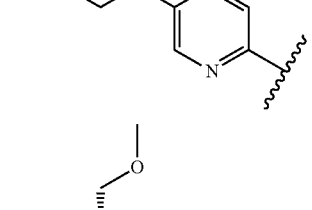
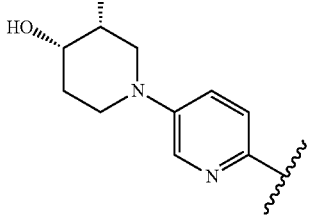

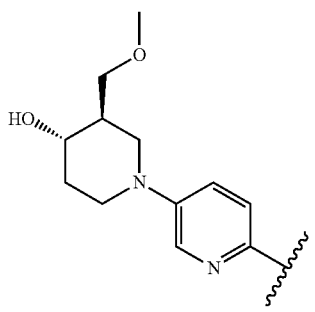
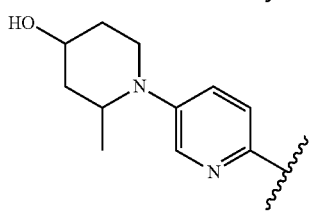
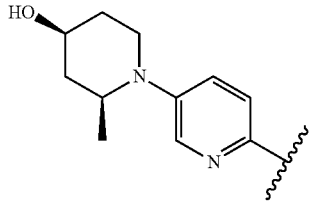
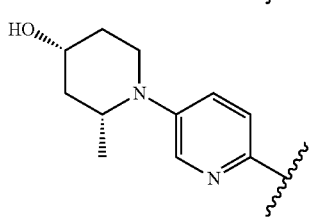
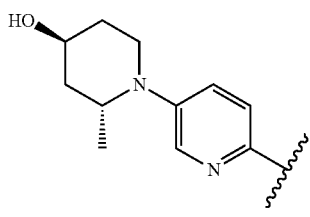
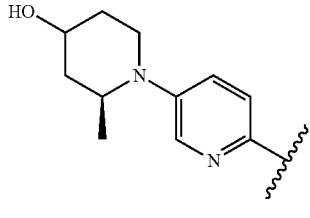
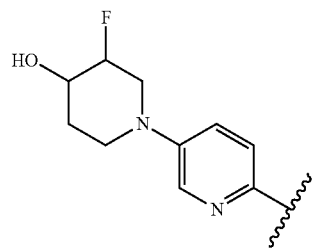
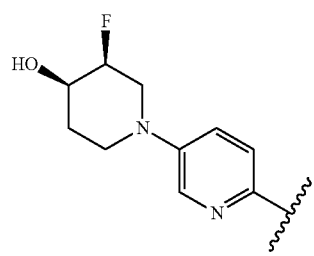
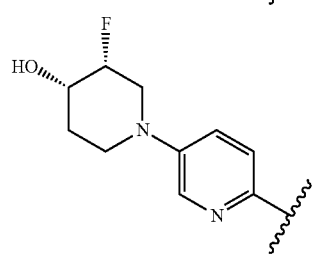
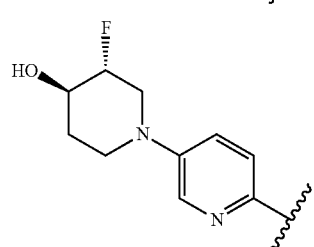
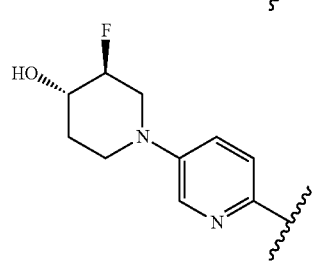
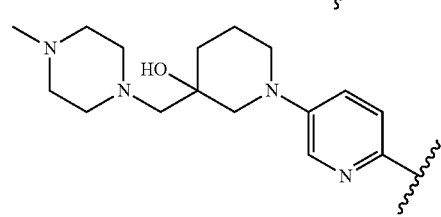
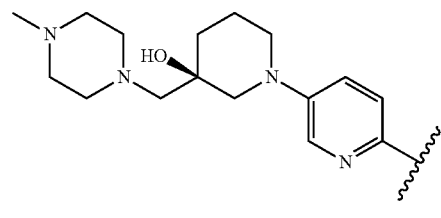

-continued
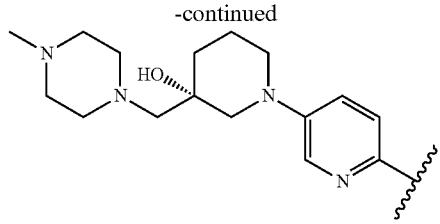 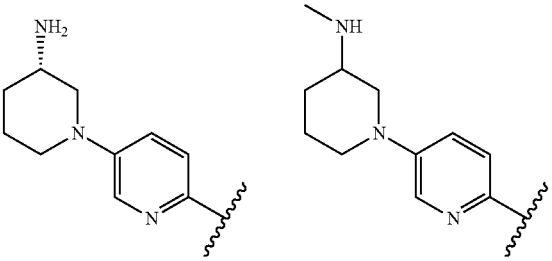
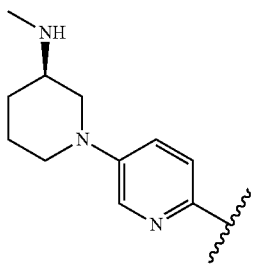
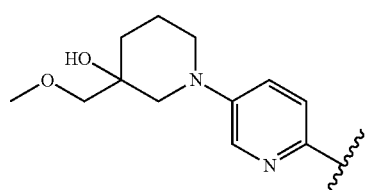 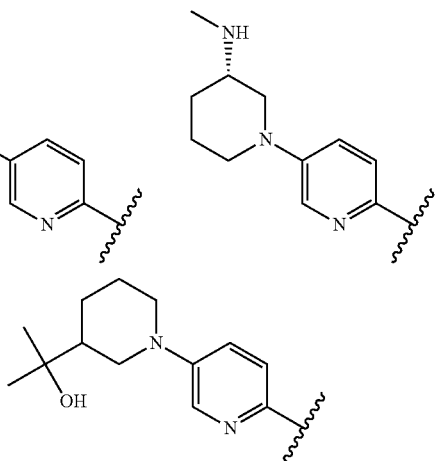
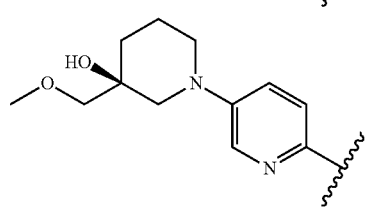
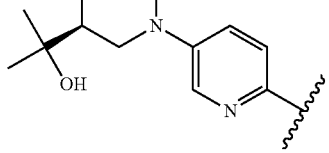
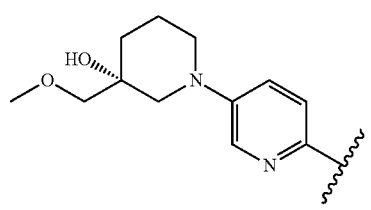
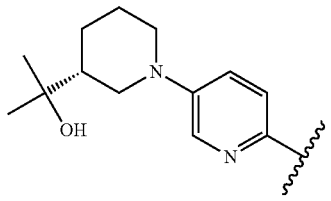
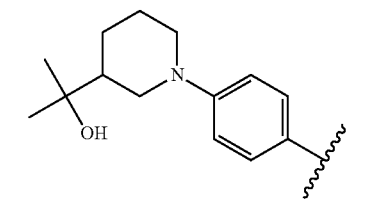
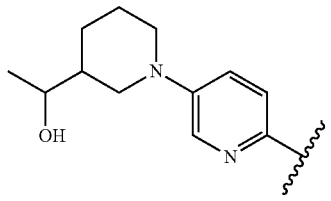
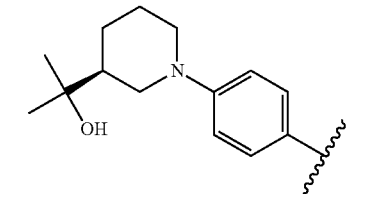
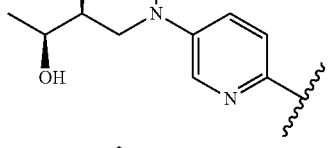
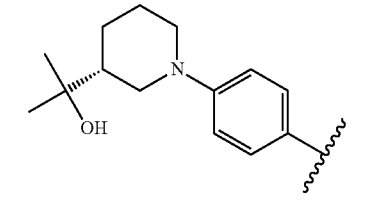
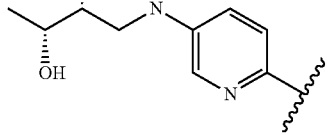
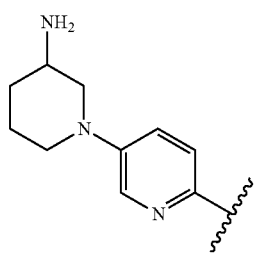 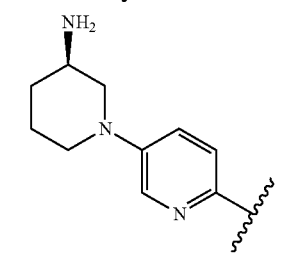

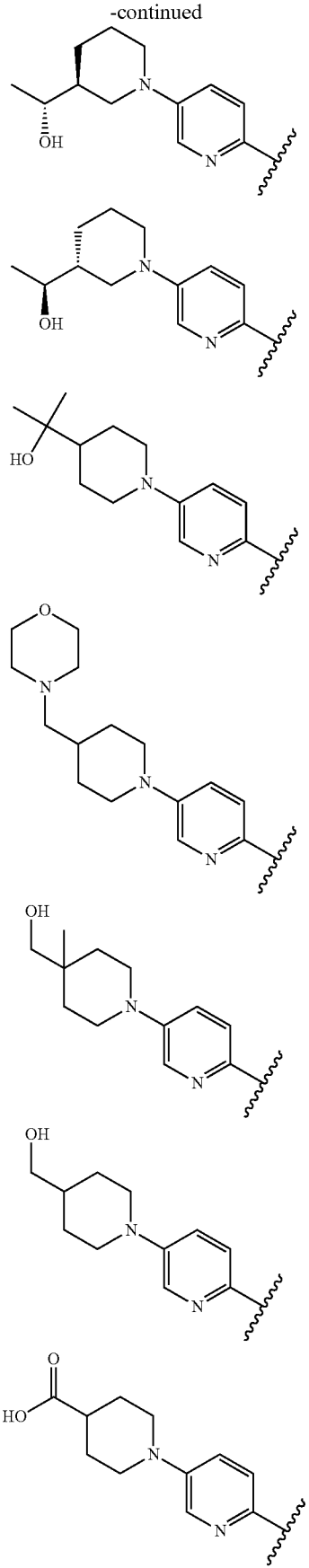
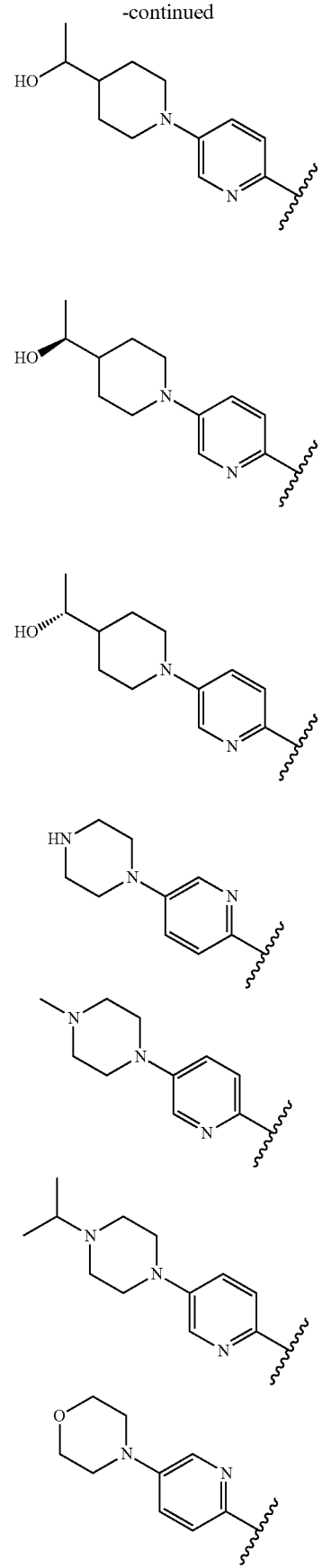

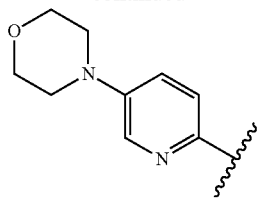
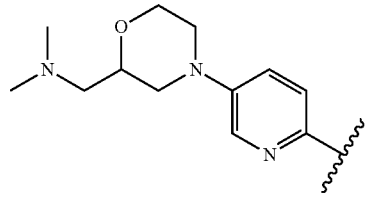
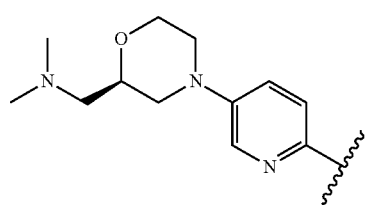
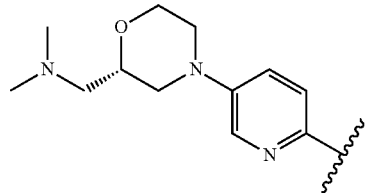
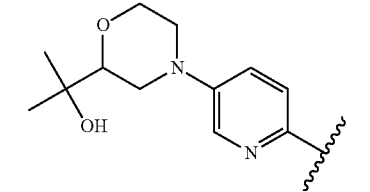
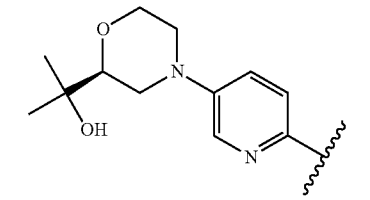
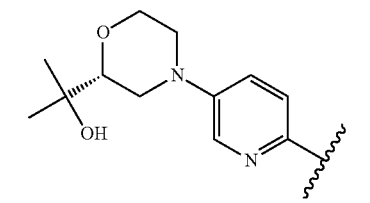
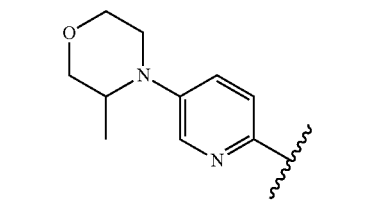
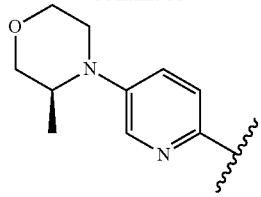
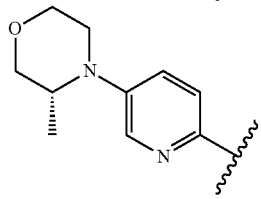
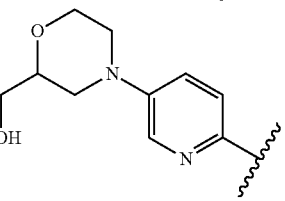
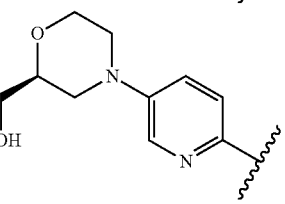
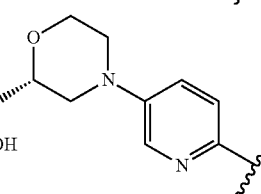
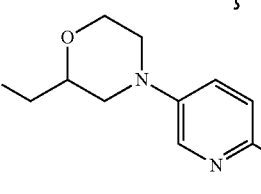
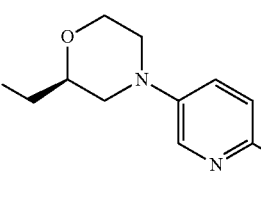
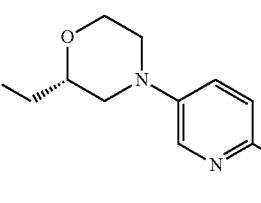
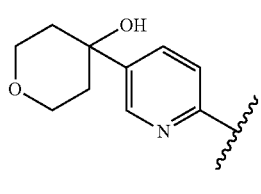

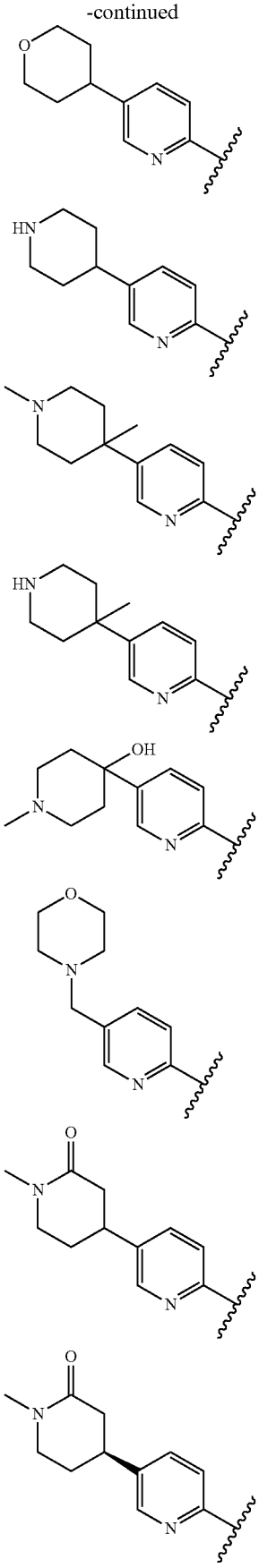
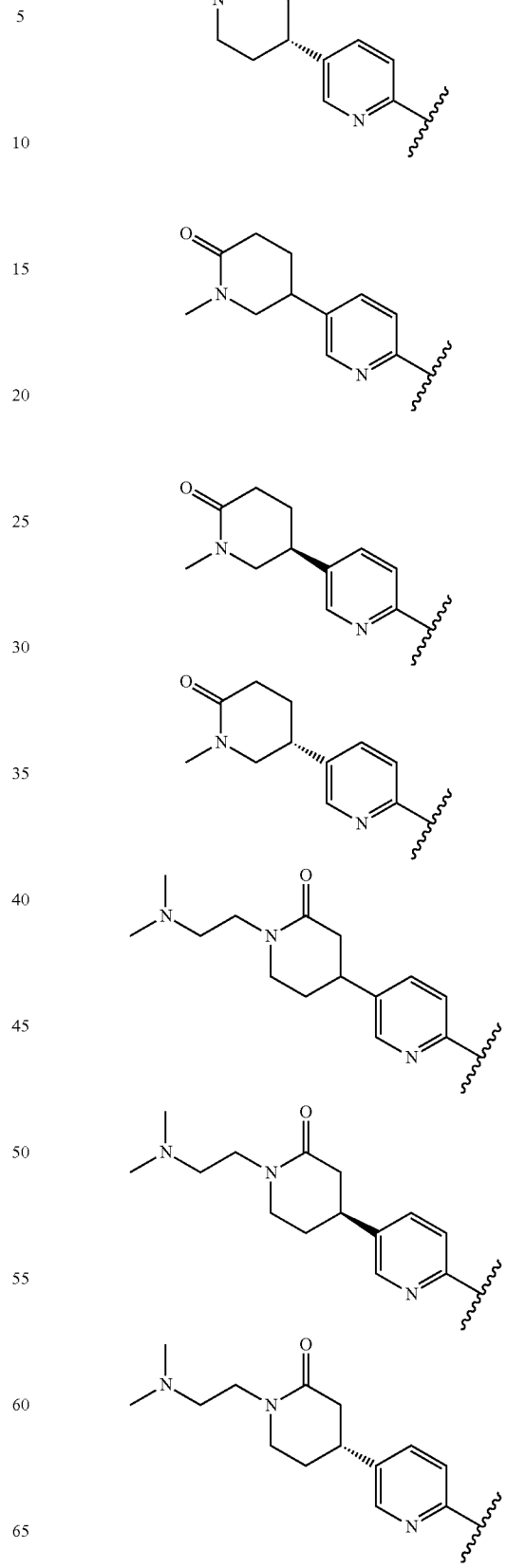

-continued
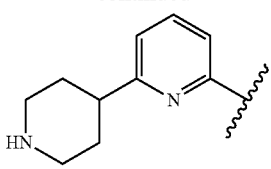
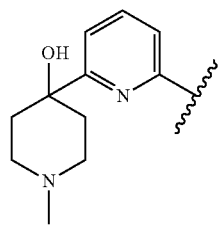
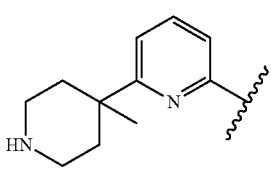
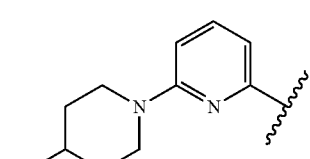
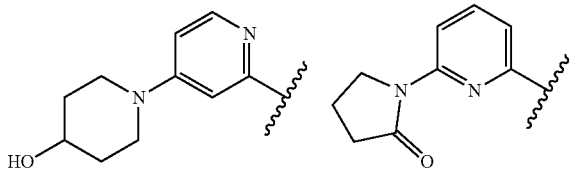
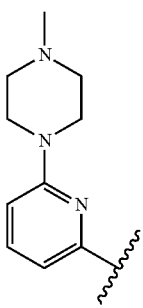 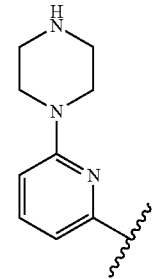 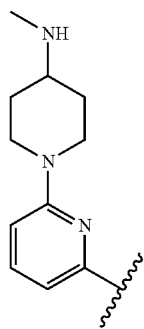
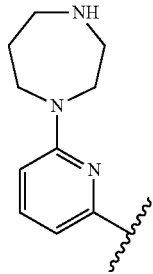 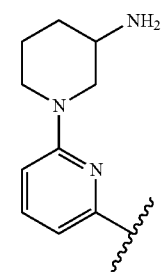 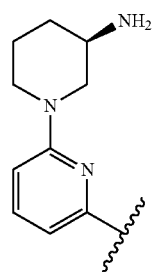
-continued
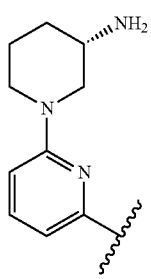 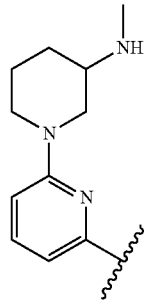 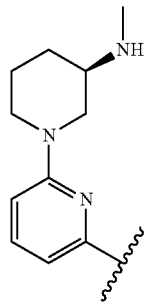
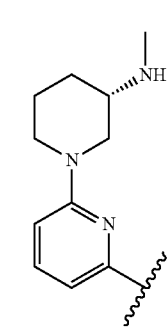
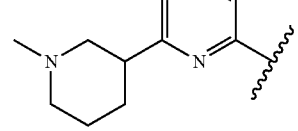
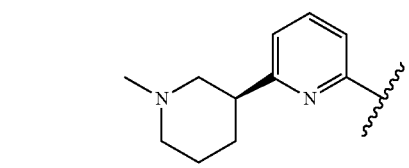
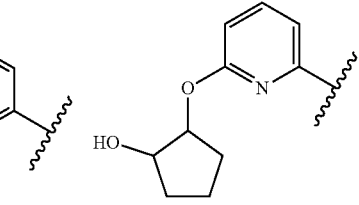
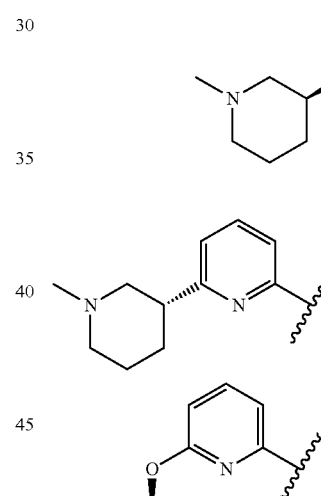
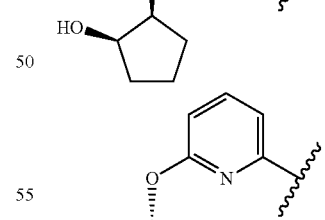
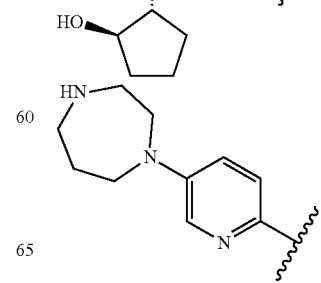
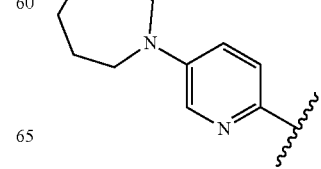

39
-continued
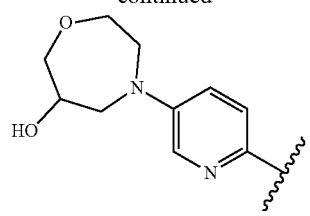
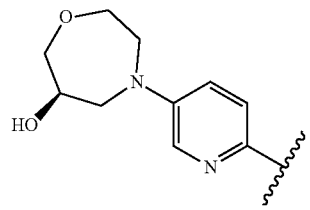
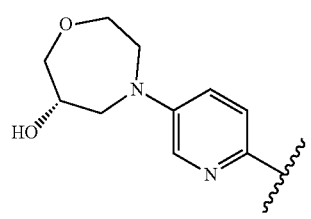
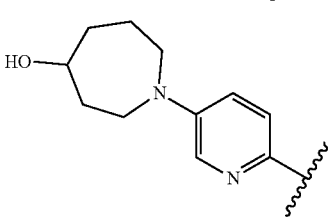
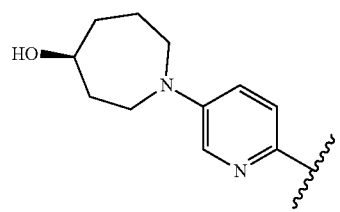
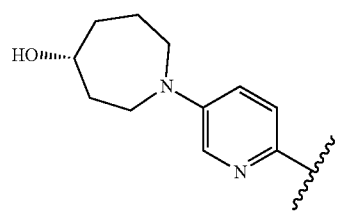
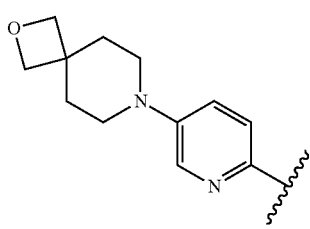
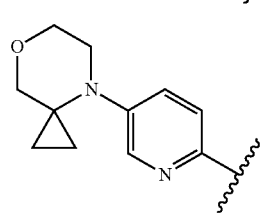
40
-continued
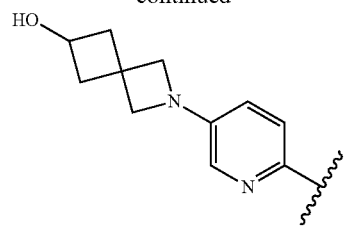
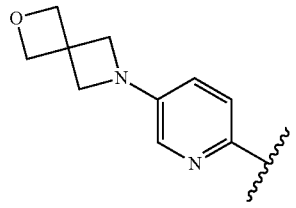
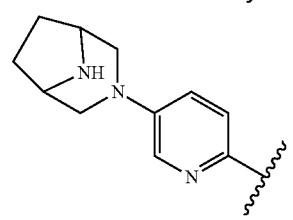
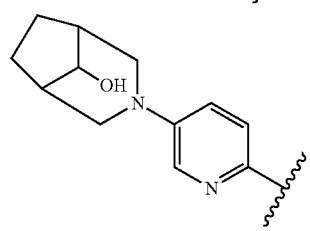
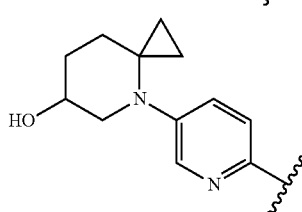
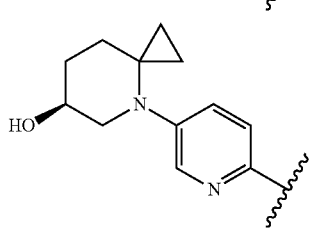
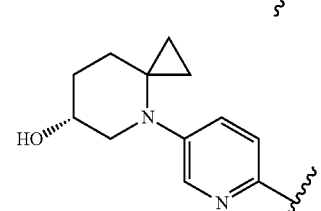
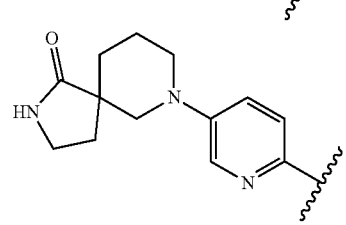

-continued

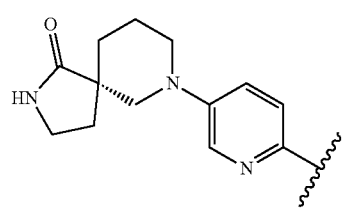
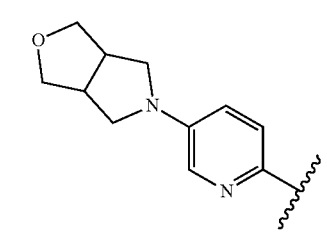
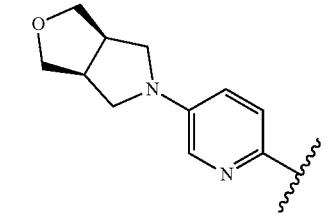
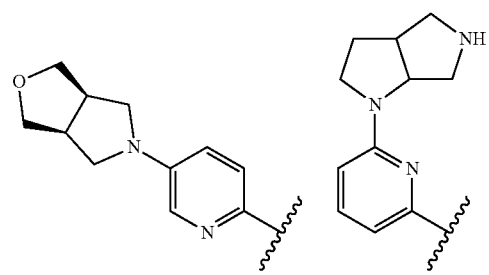
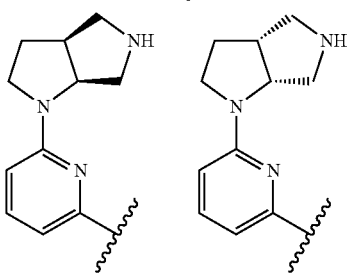
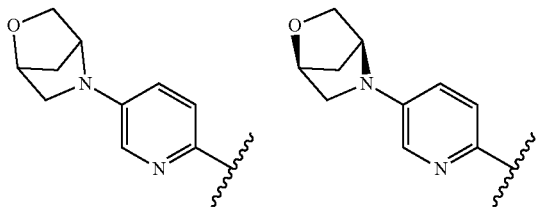
-continued
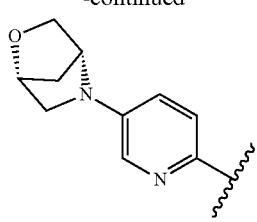
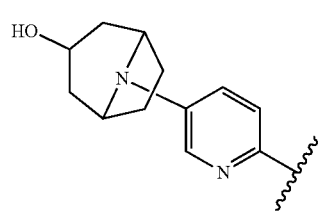
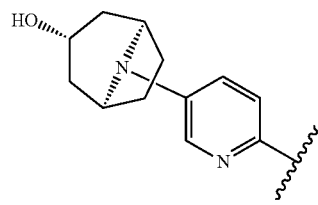
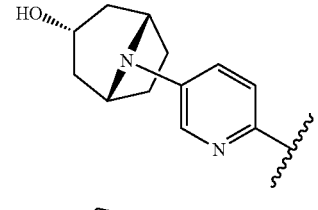

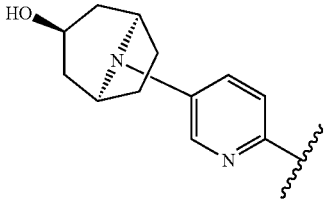
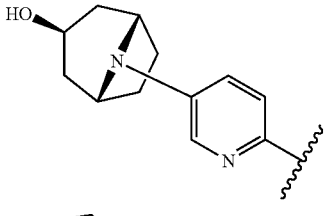
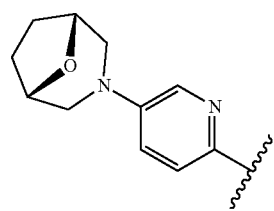

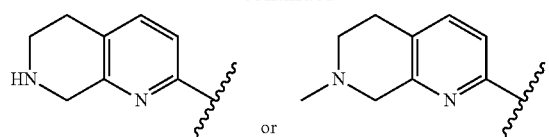
In certain embodiments, R¹ together with its R^C substituents is
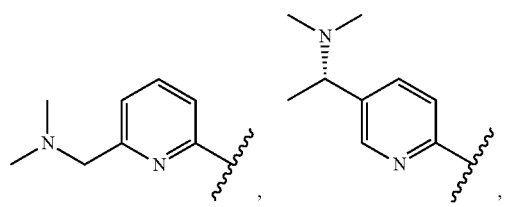
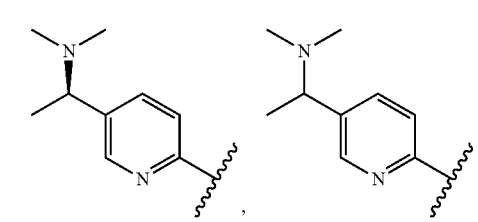
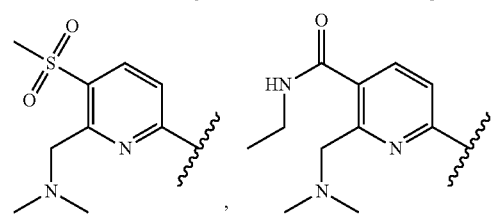
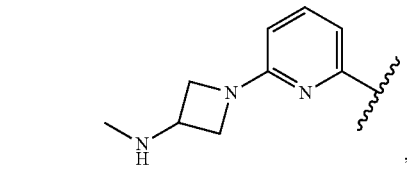
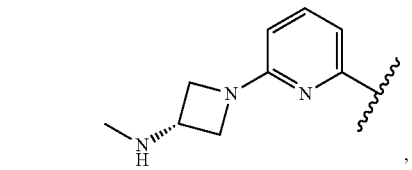
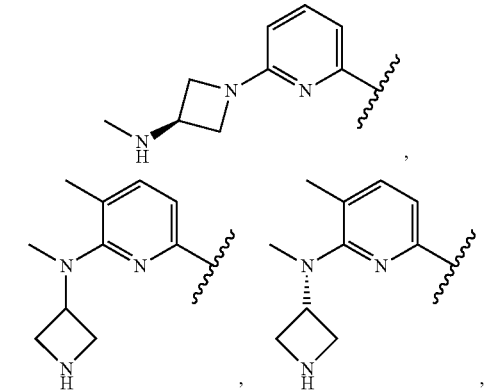
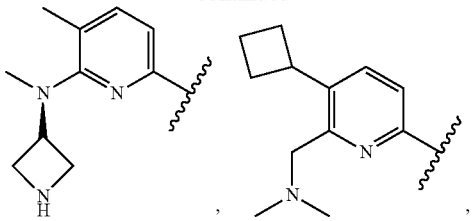
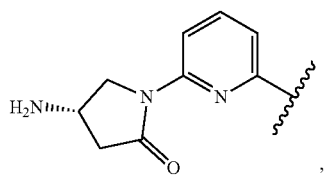
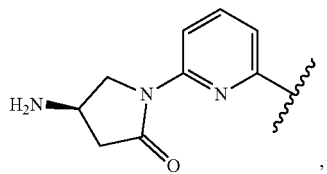
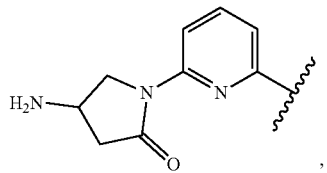
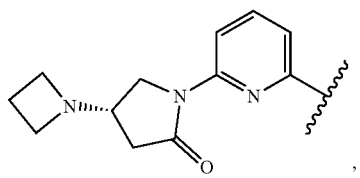
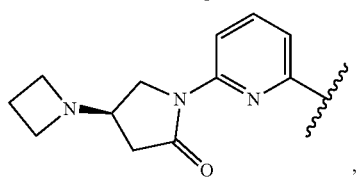
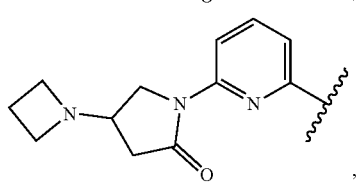
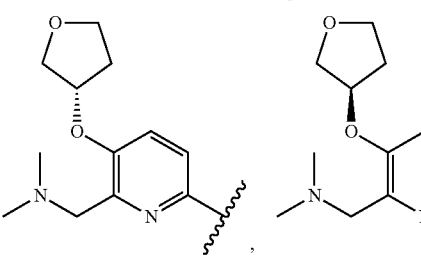

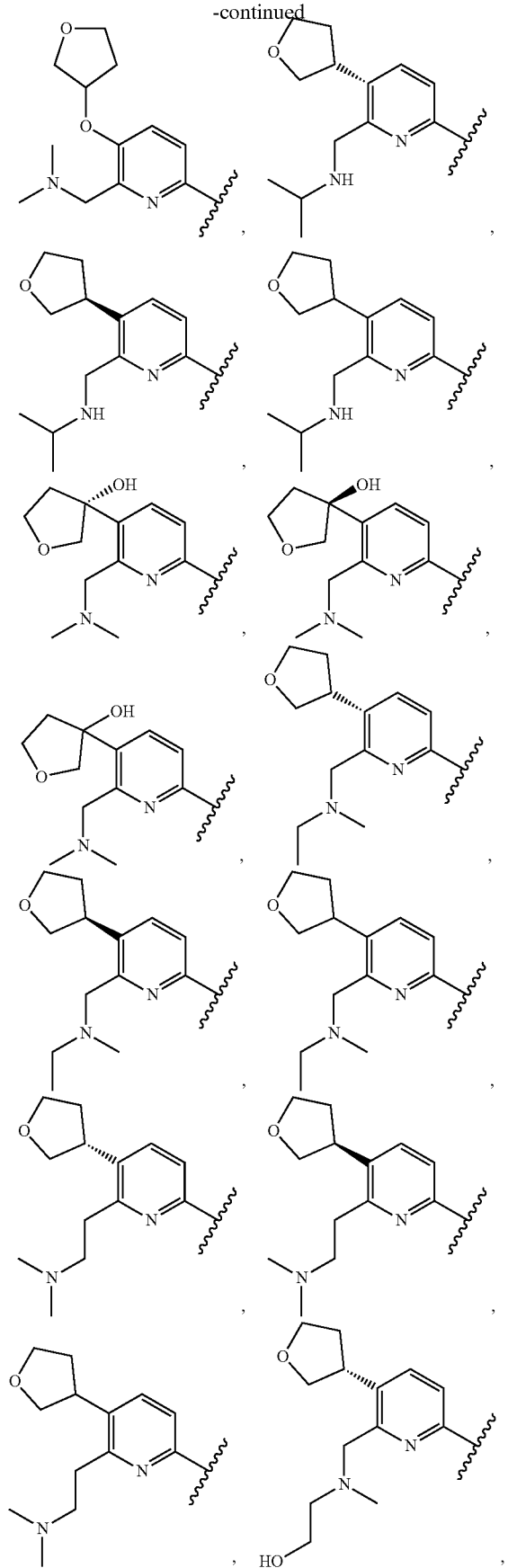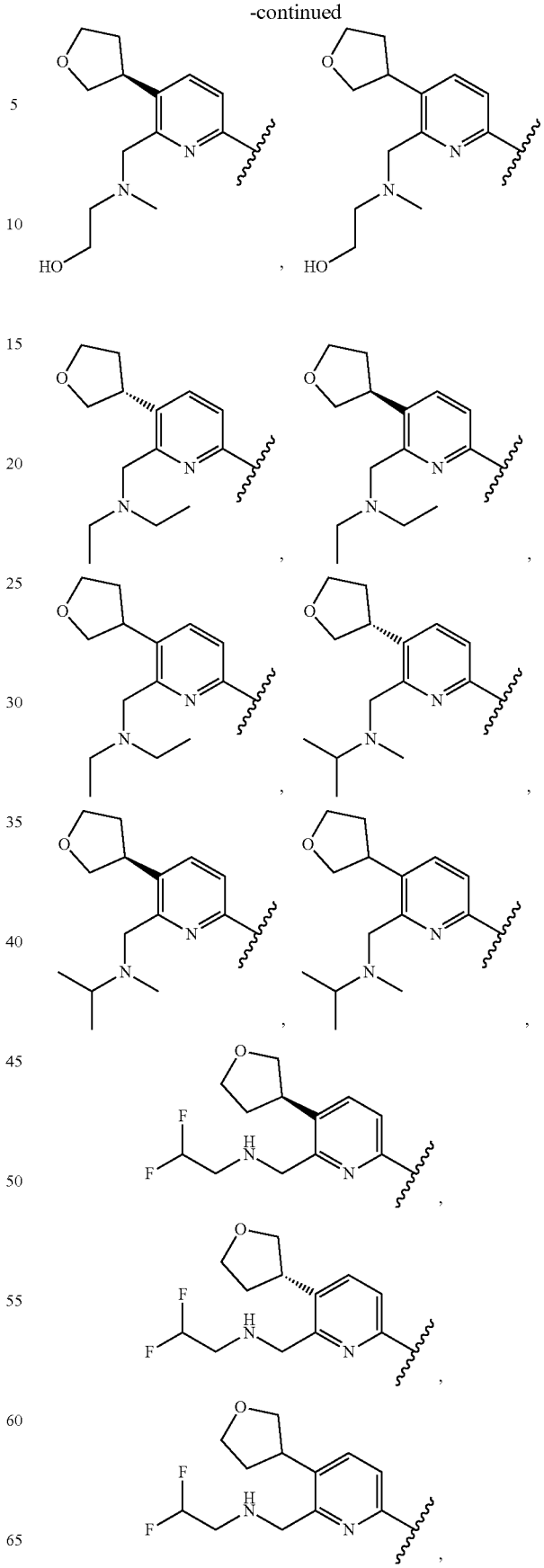

-continued
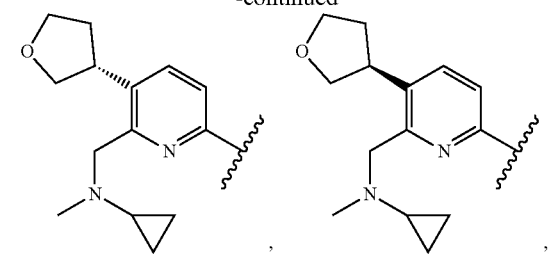
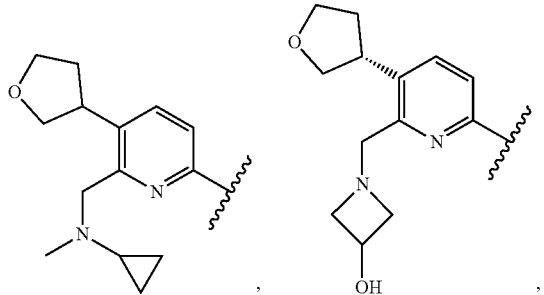
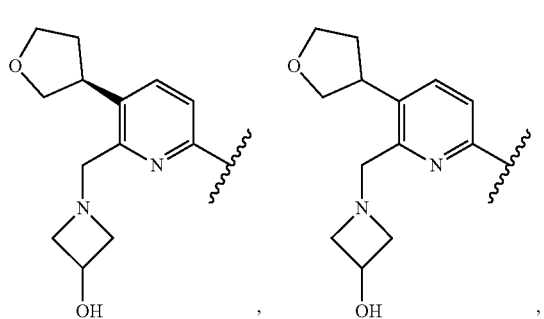
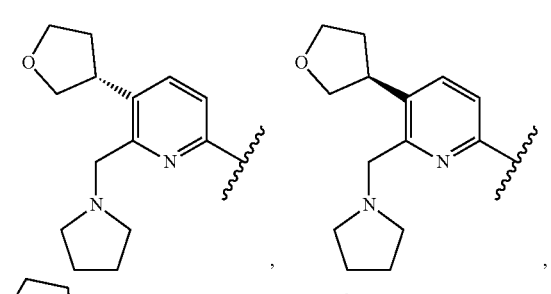
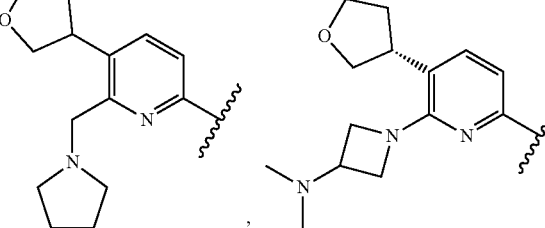
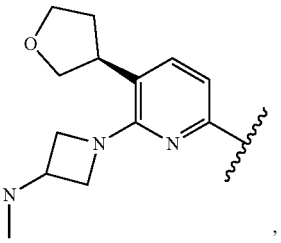
-continued
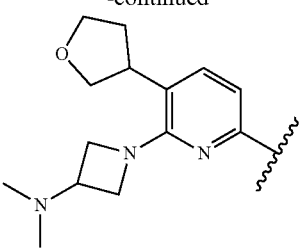
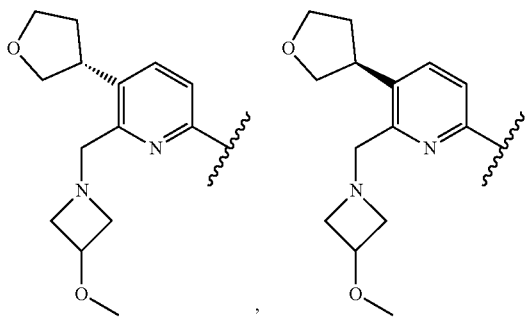
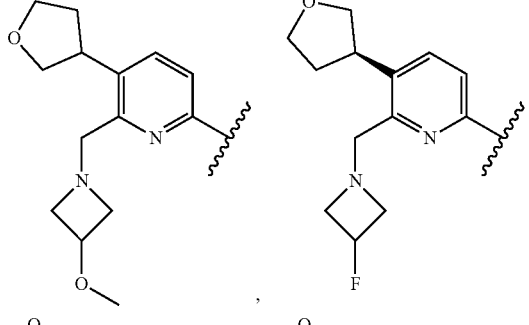
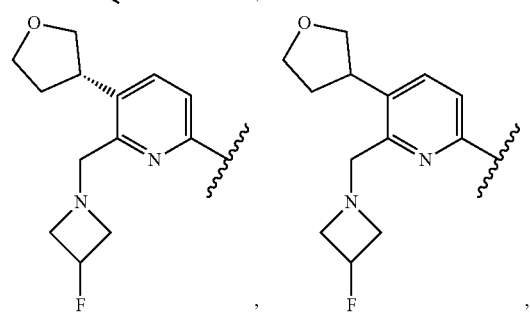
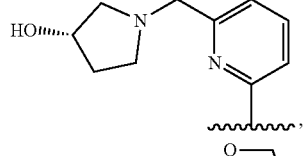
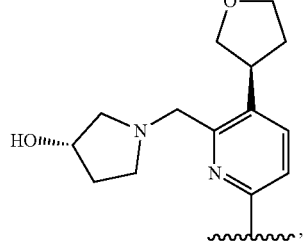

-continued
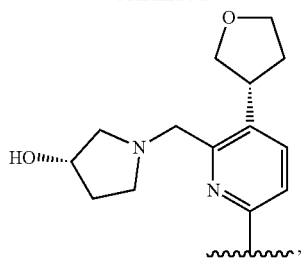
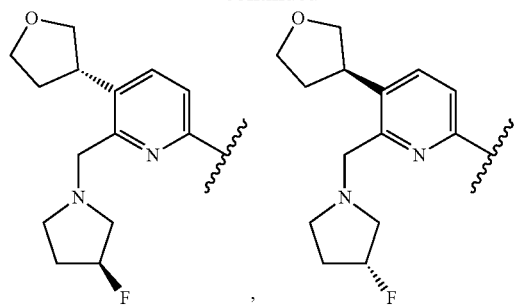
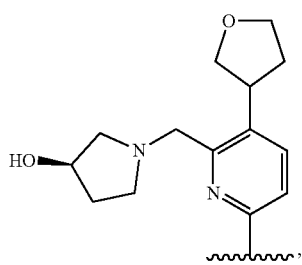
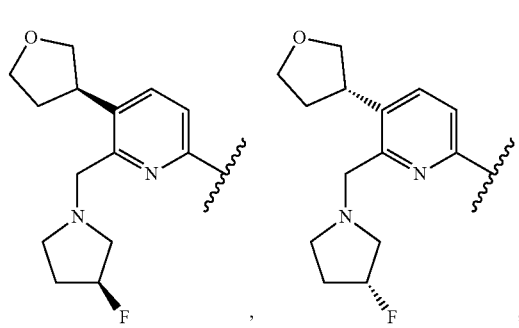
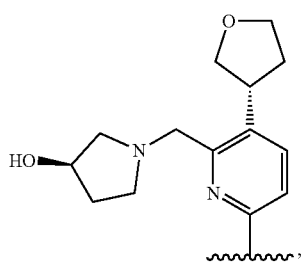
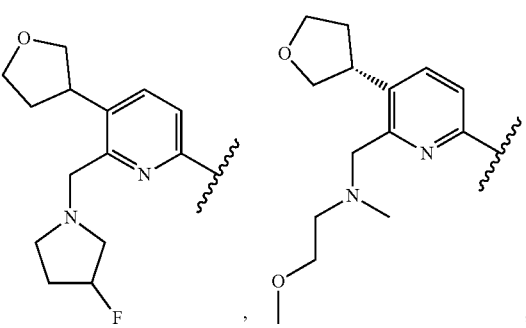
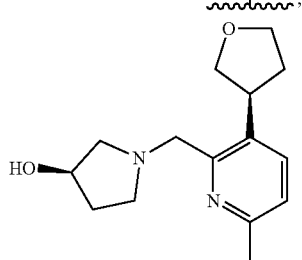
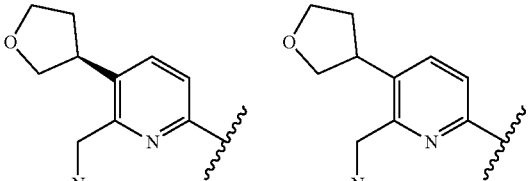
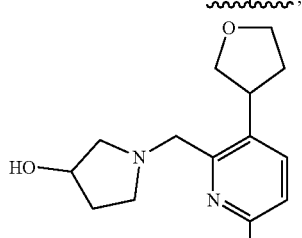
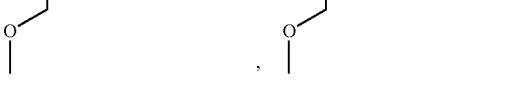
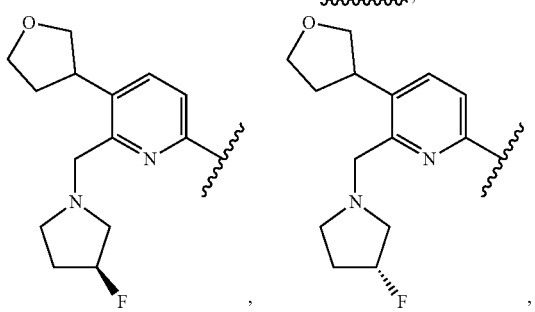
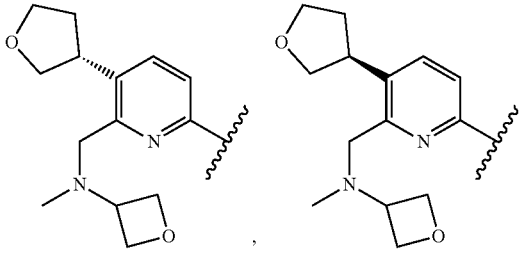

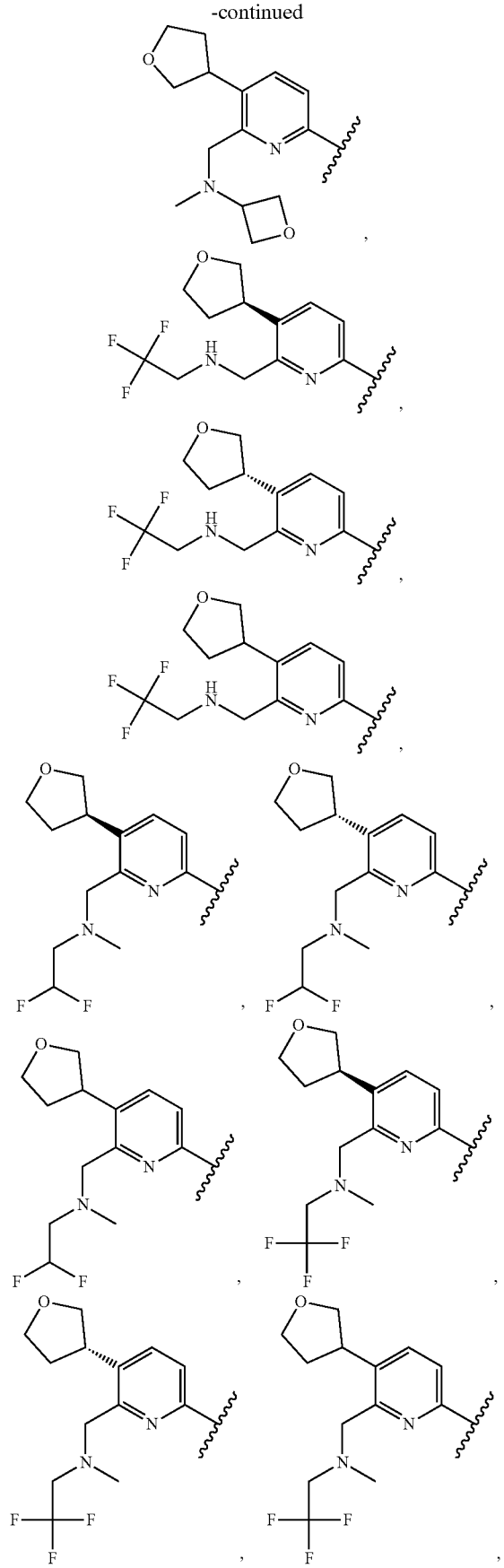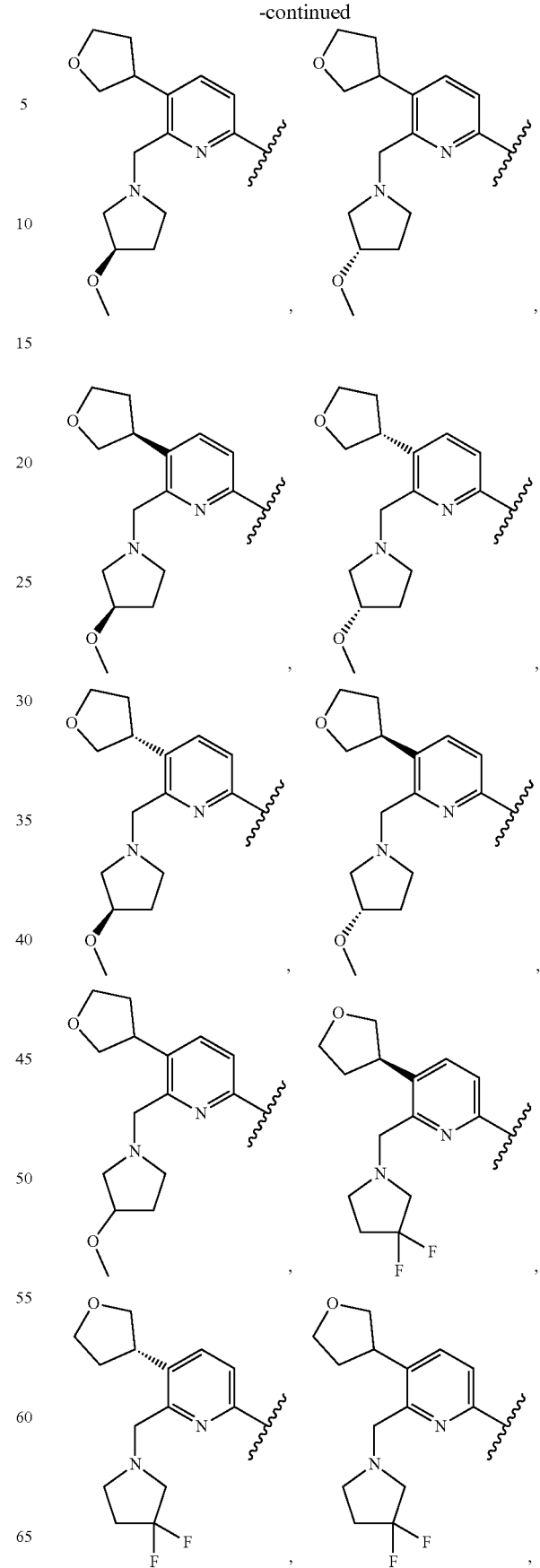

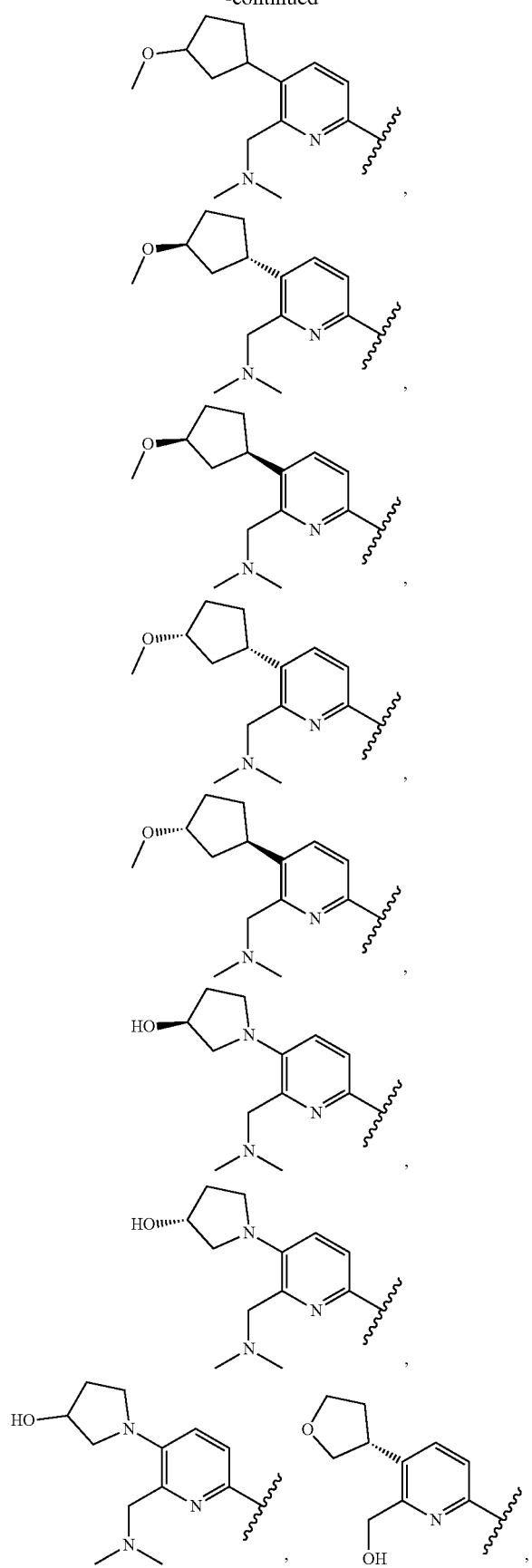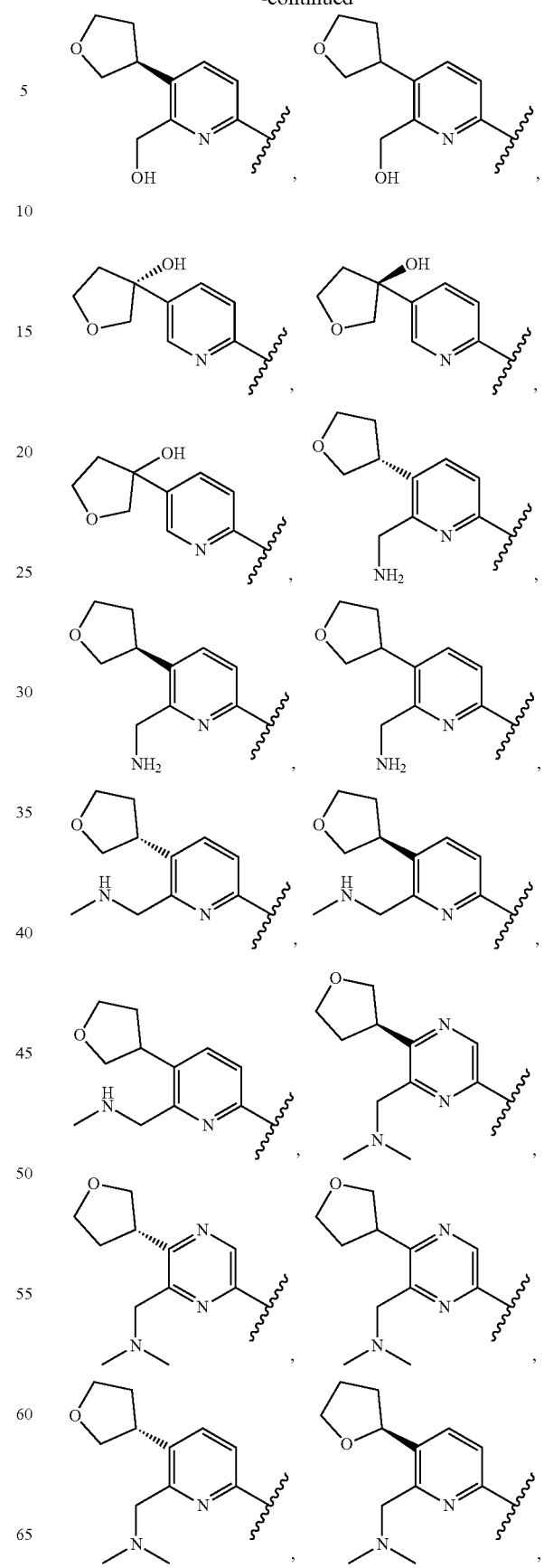

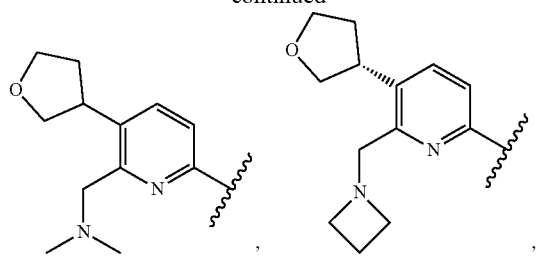
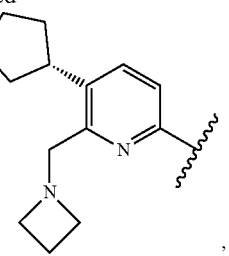
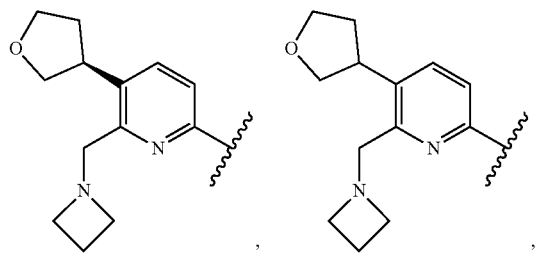
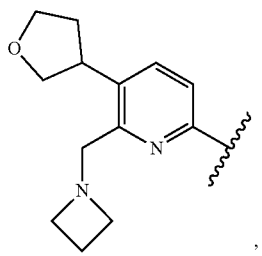
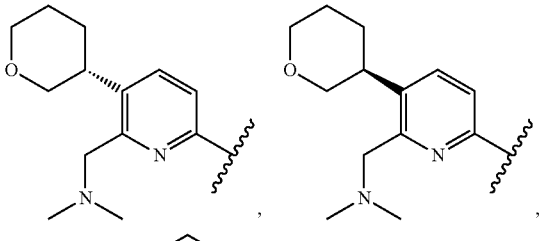
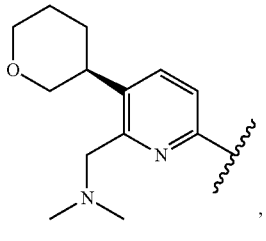
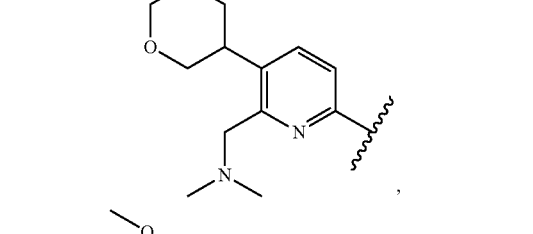
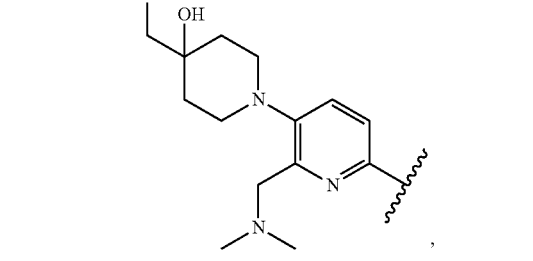
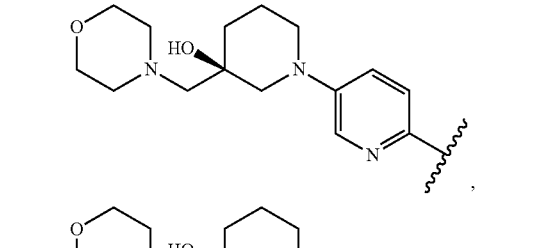
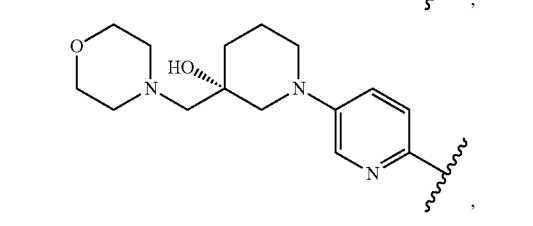
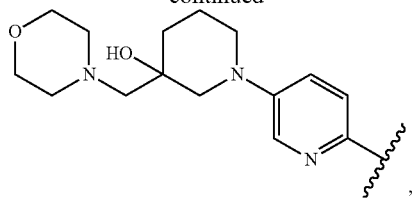
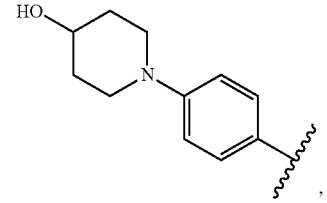
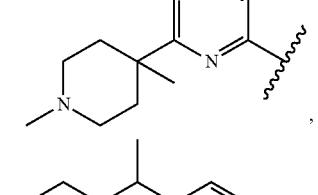
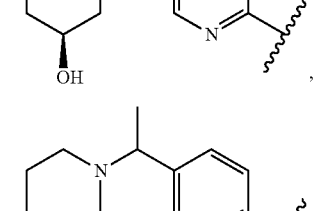
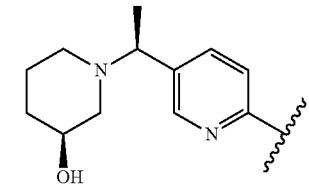
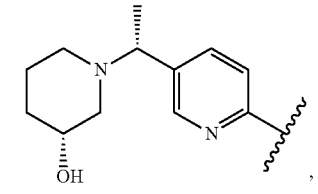
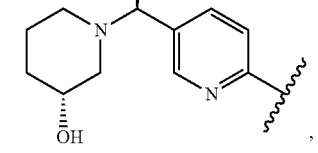

57
-continued
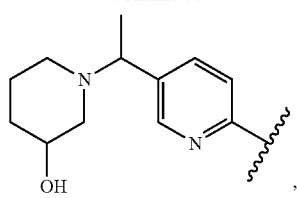
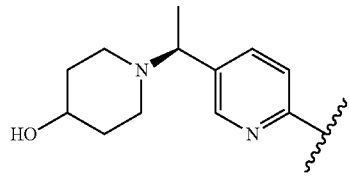
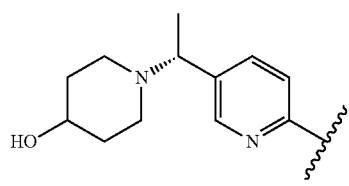
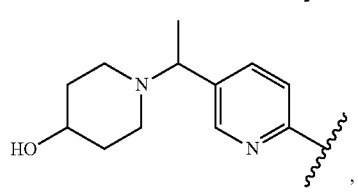
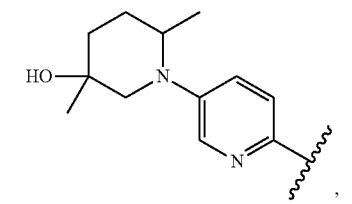
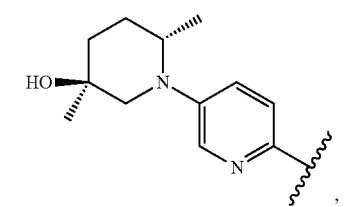
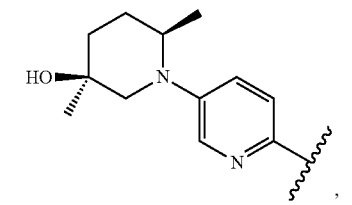
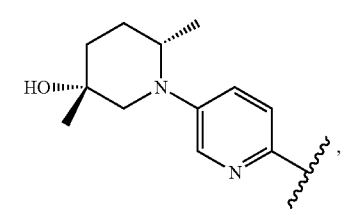
58
-continued
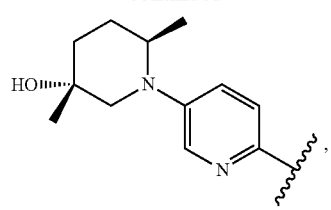
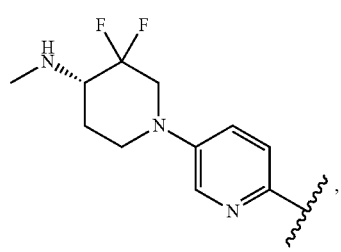
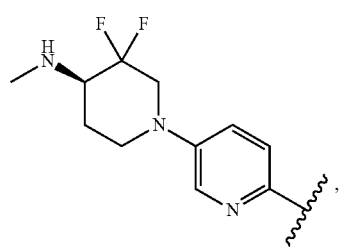
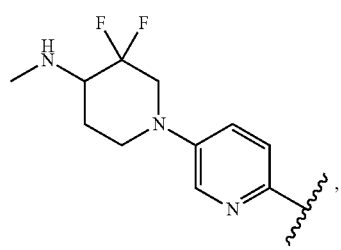
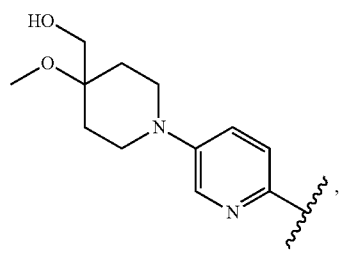
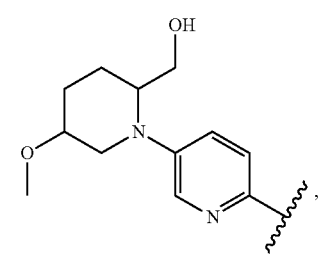
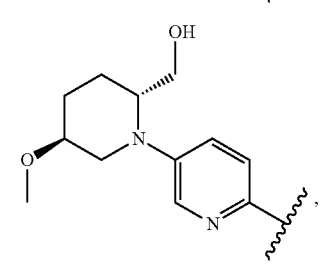

-continued
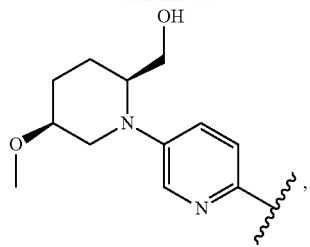,
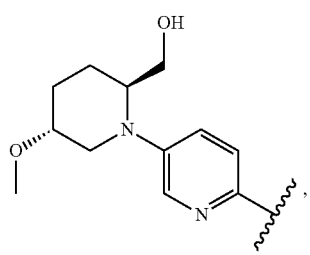,
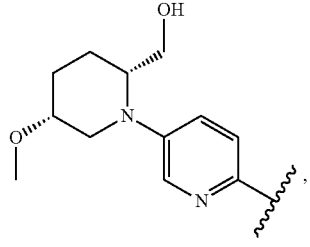,
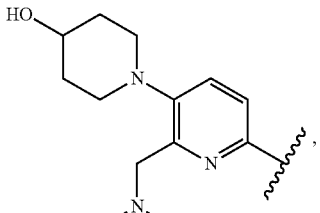,
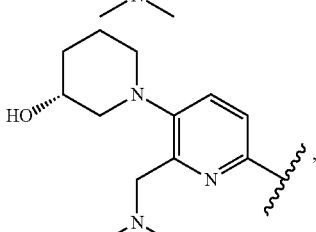,
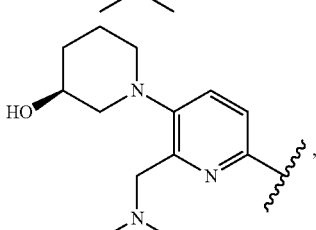,
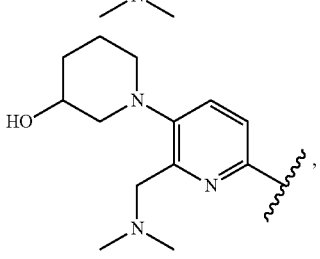,
-continued
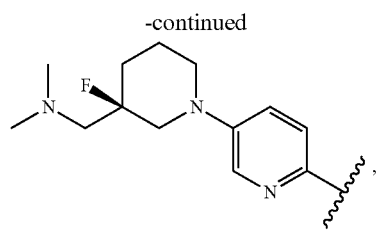,
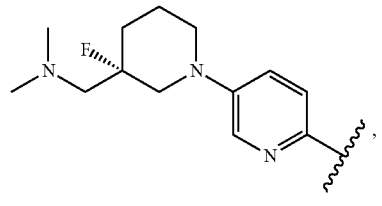,
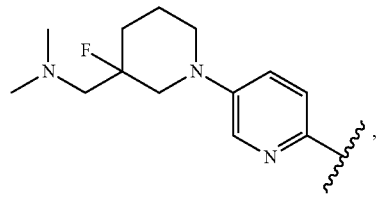,
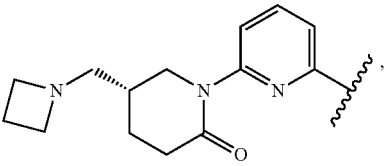,
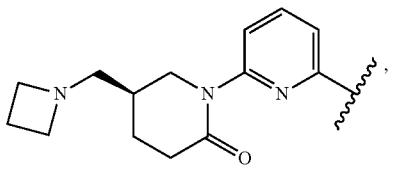,
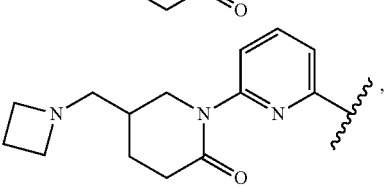,
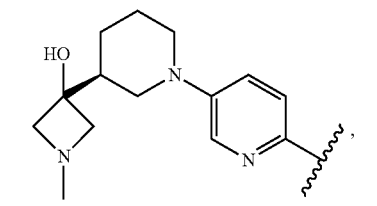,
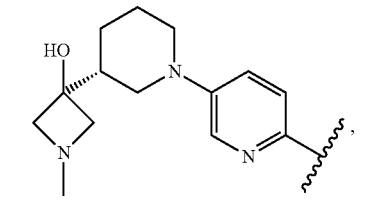,
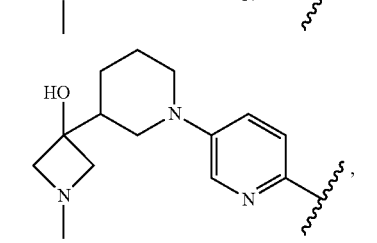,

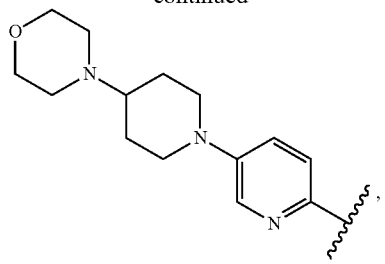
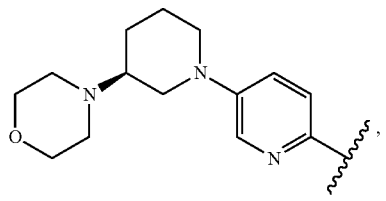
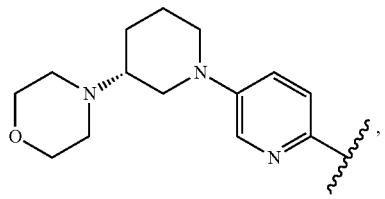

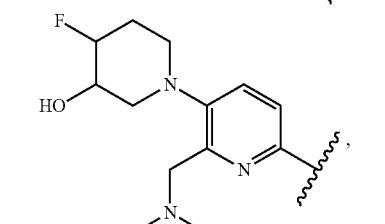
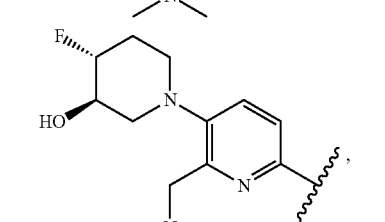
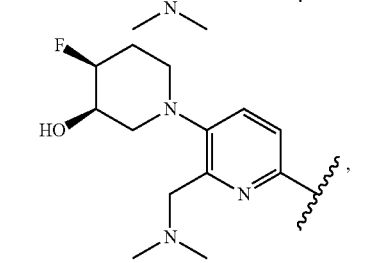
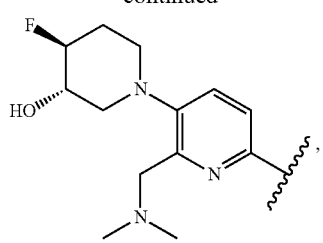
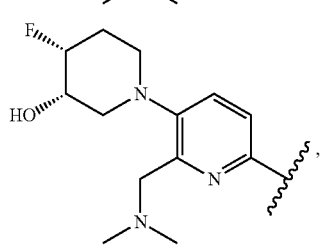
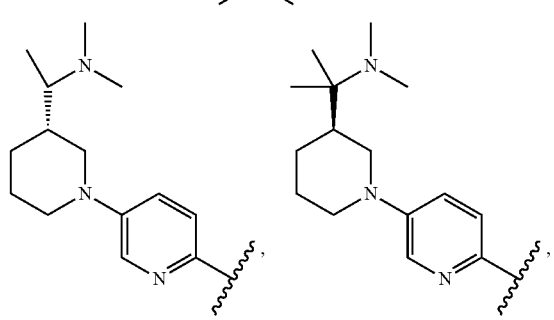
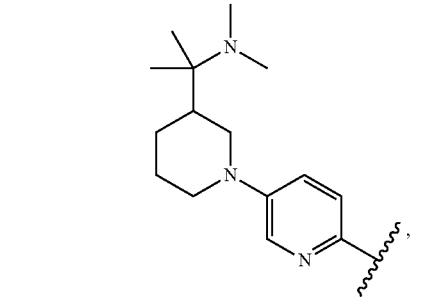
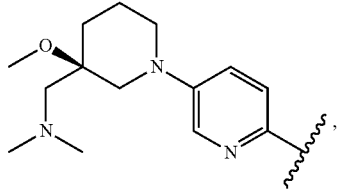
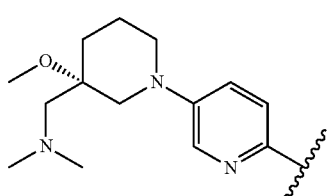
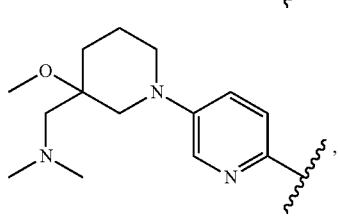

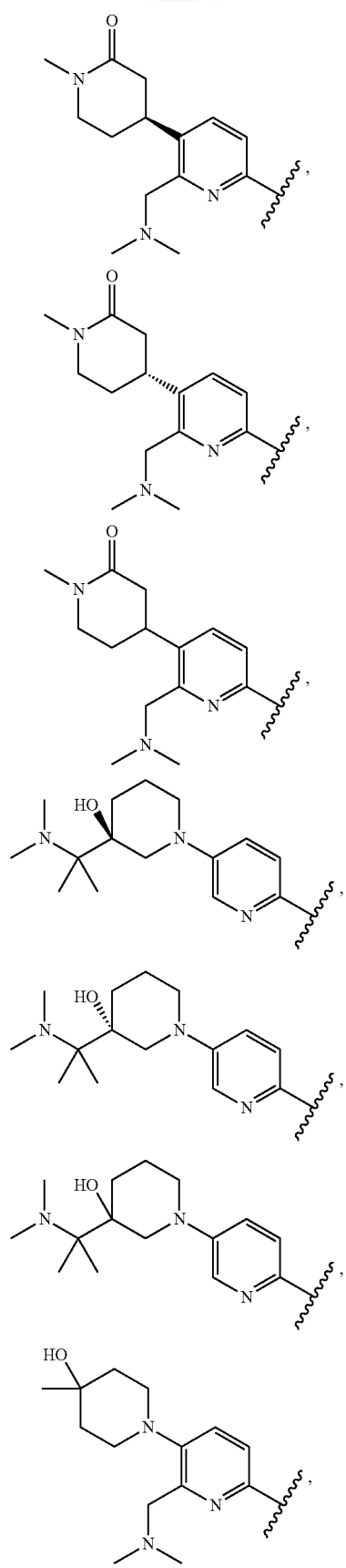
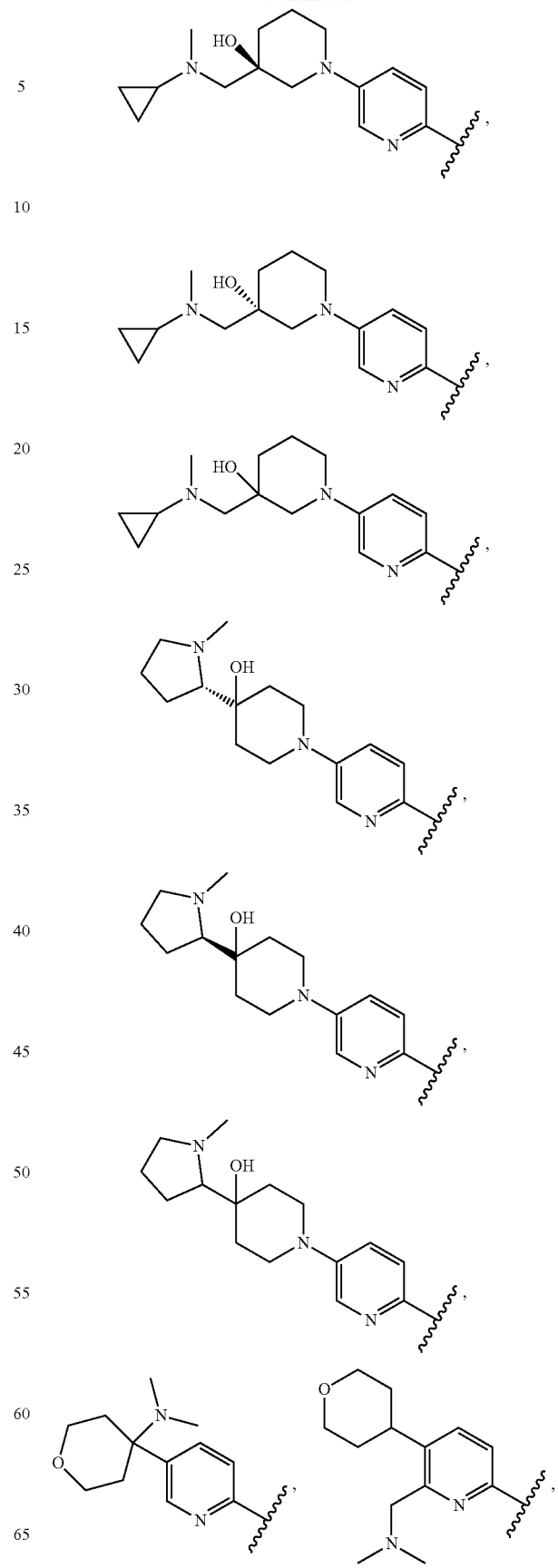

-continued
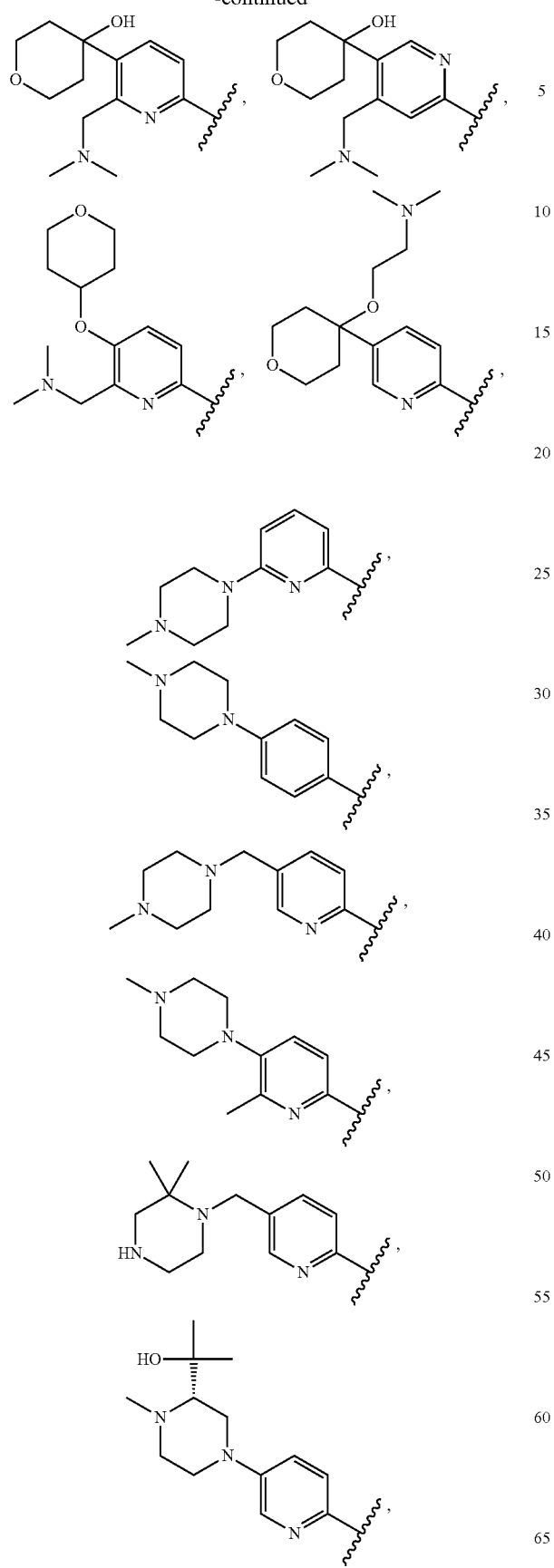
-continued
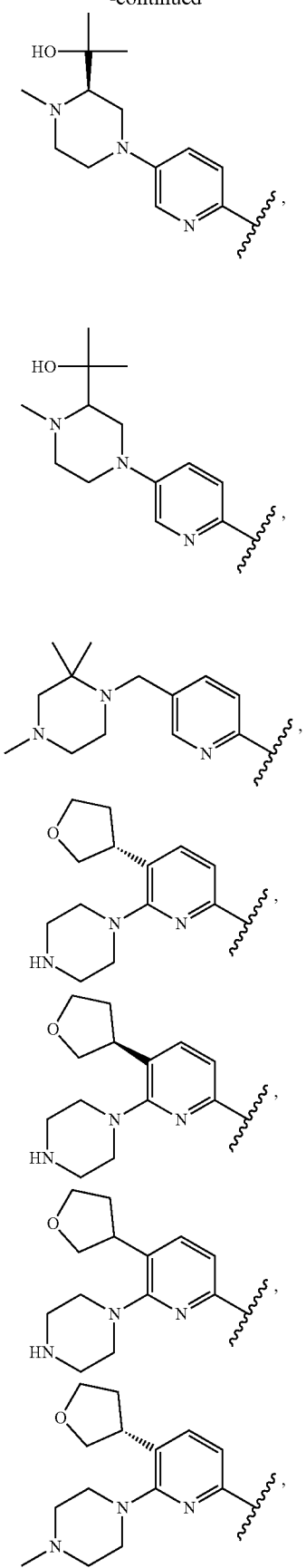

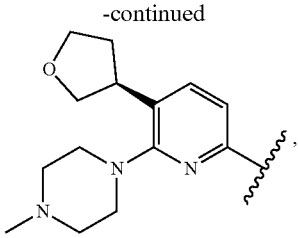
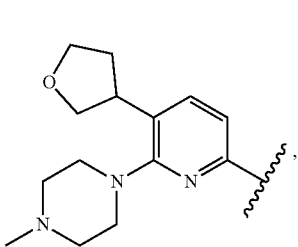
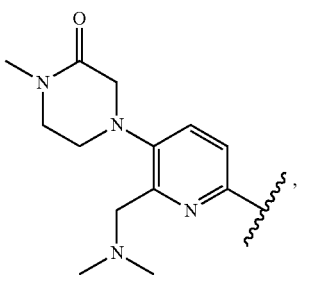
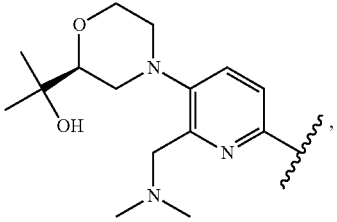
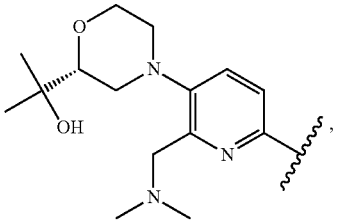
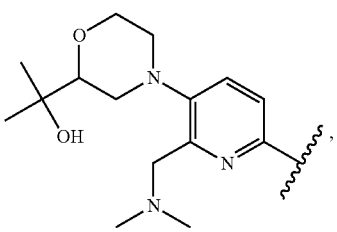
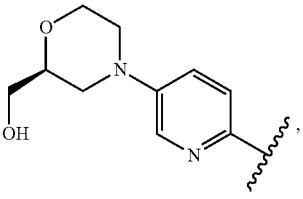
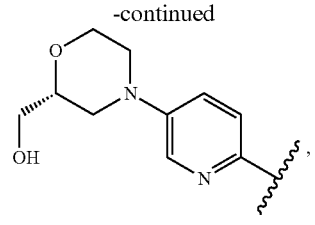
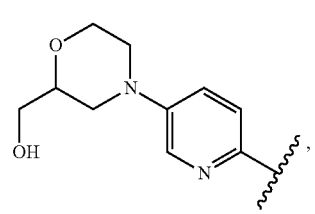
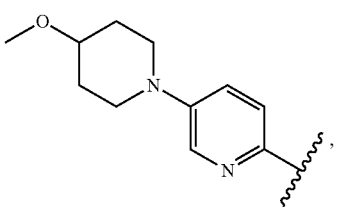
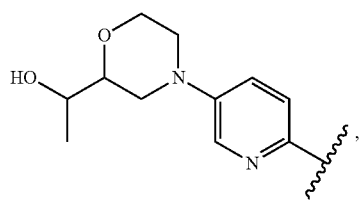
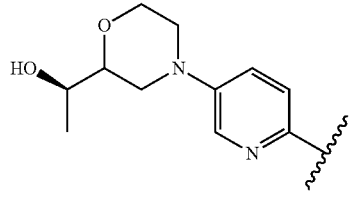
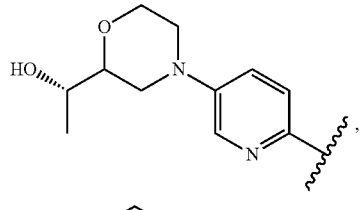
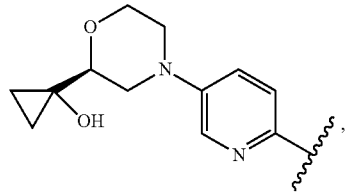
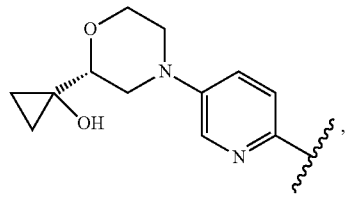

-continued
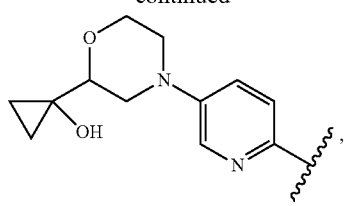,
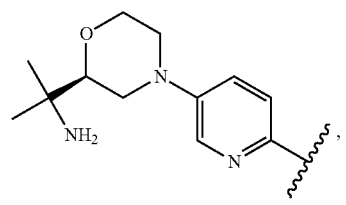,
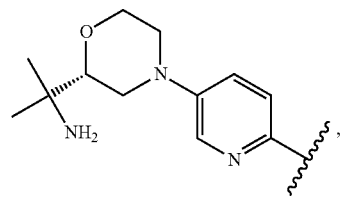,
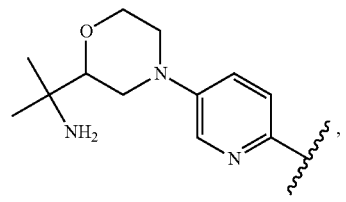,
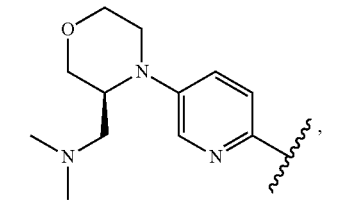,
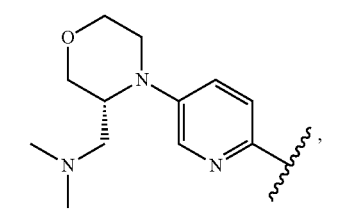,
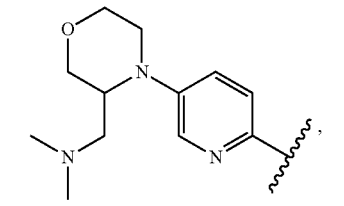,
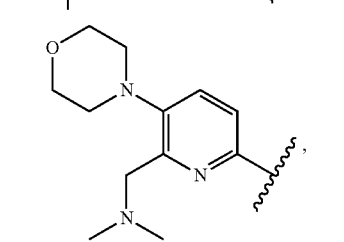,
-continued
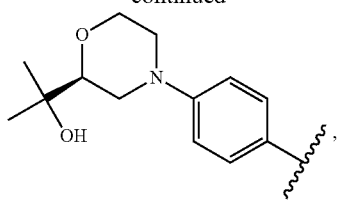,
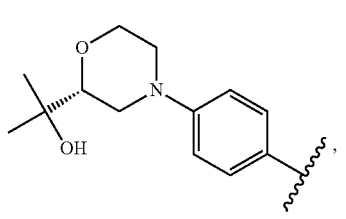,
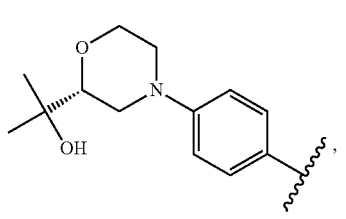,
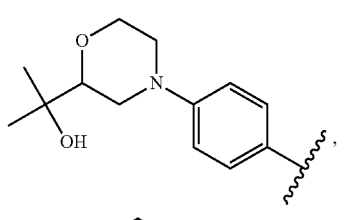,
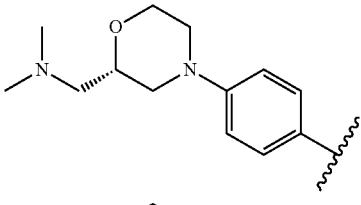,
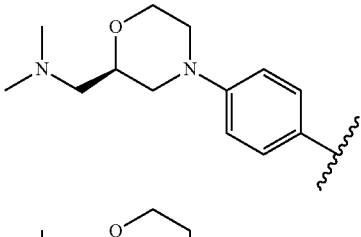,
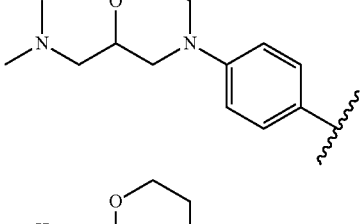,
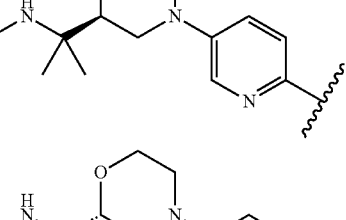,
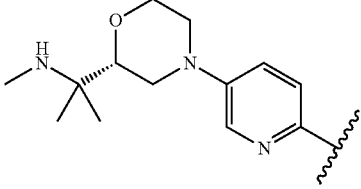,

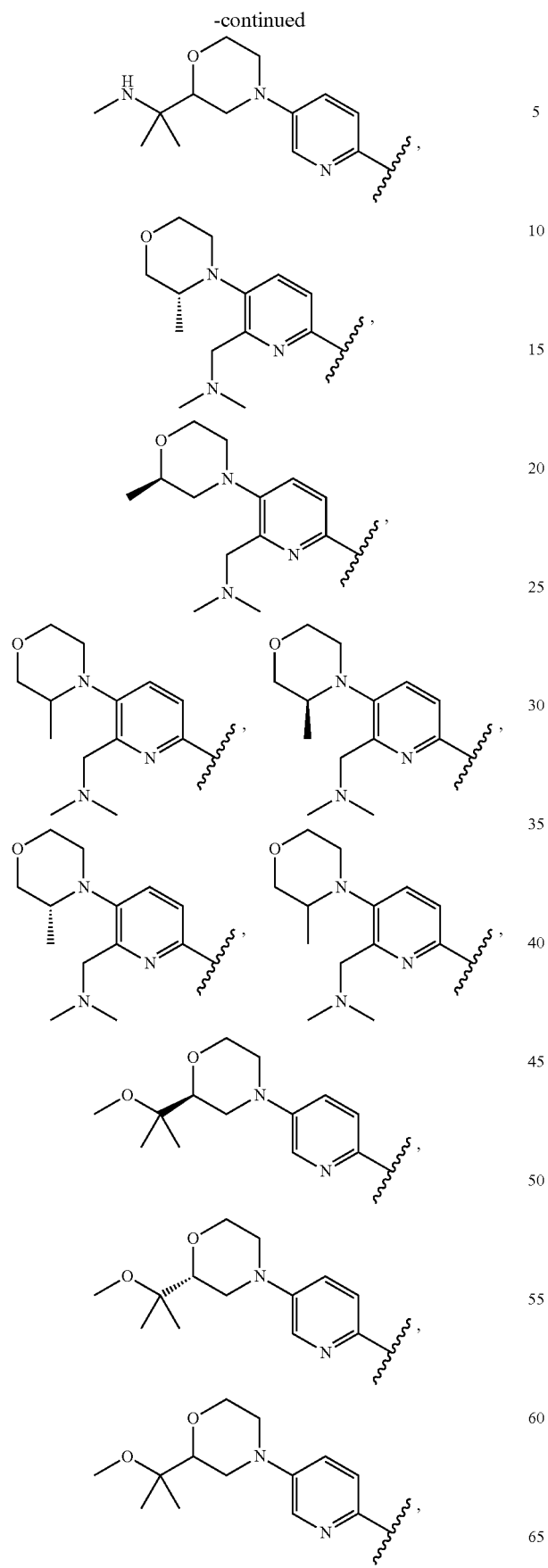
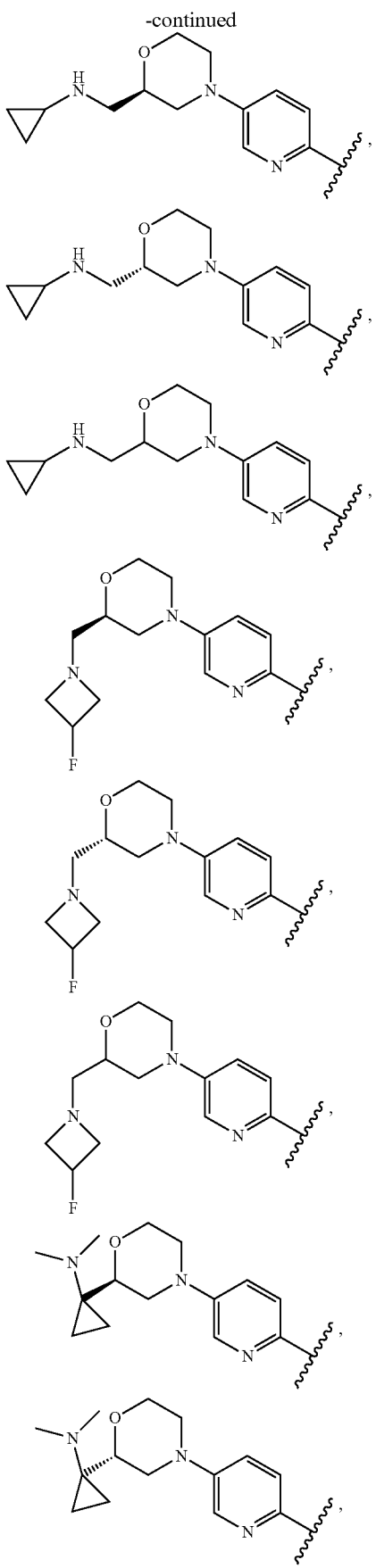

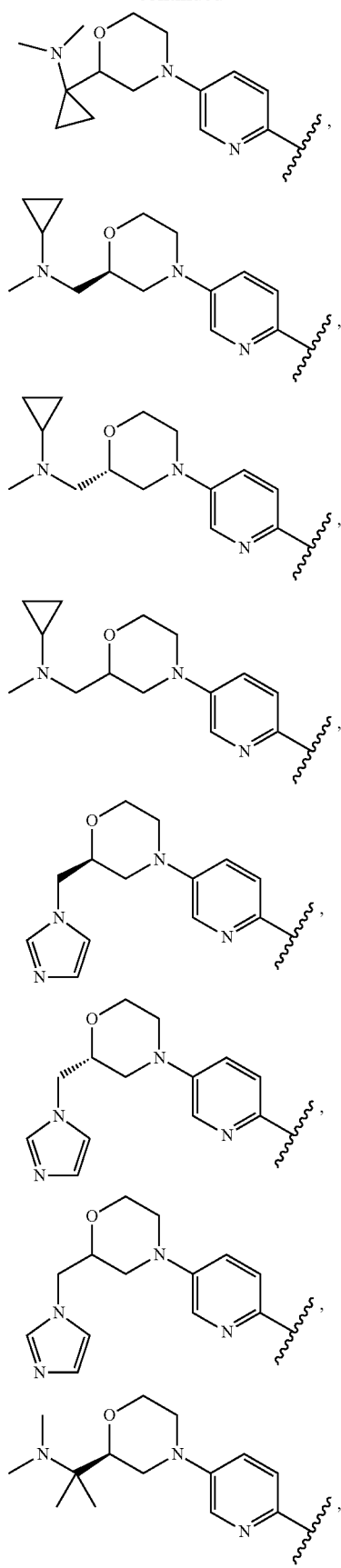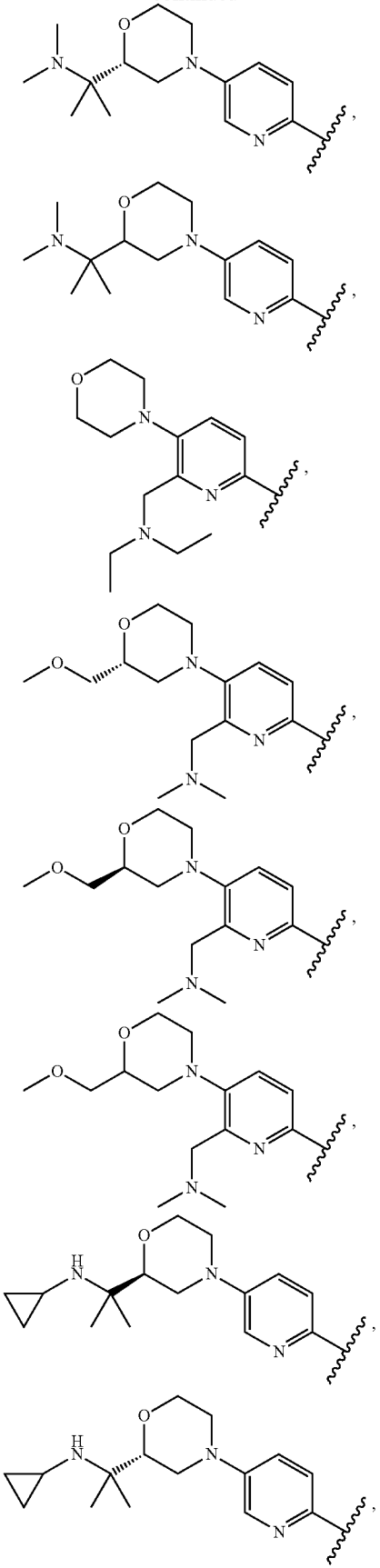

-continued

-continued
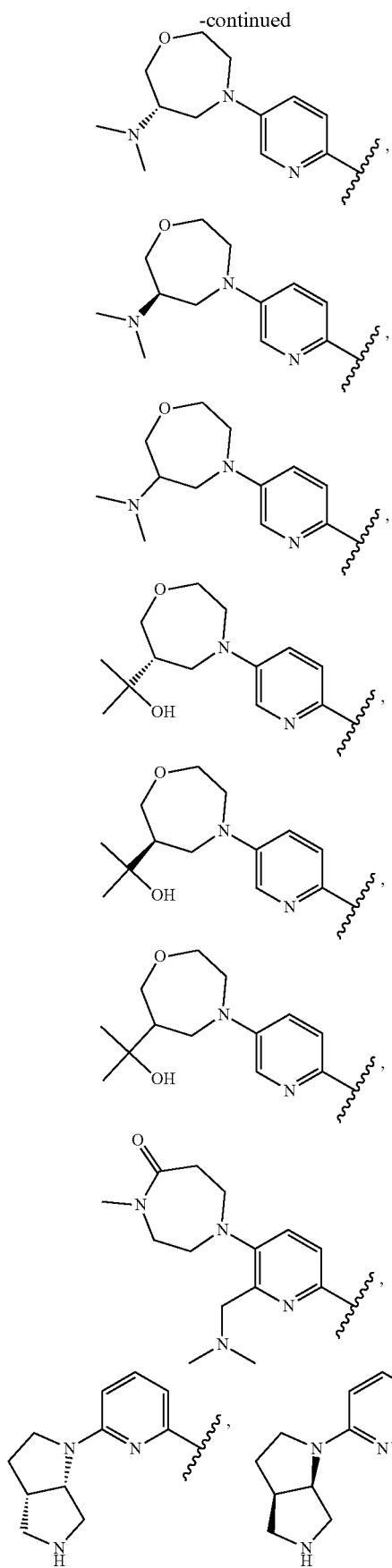
-continued
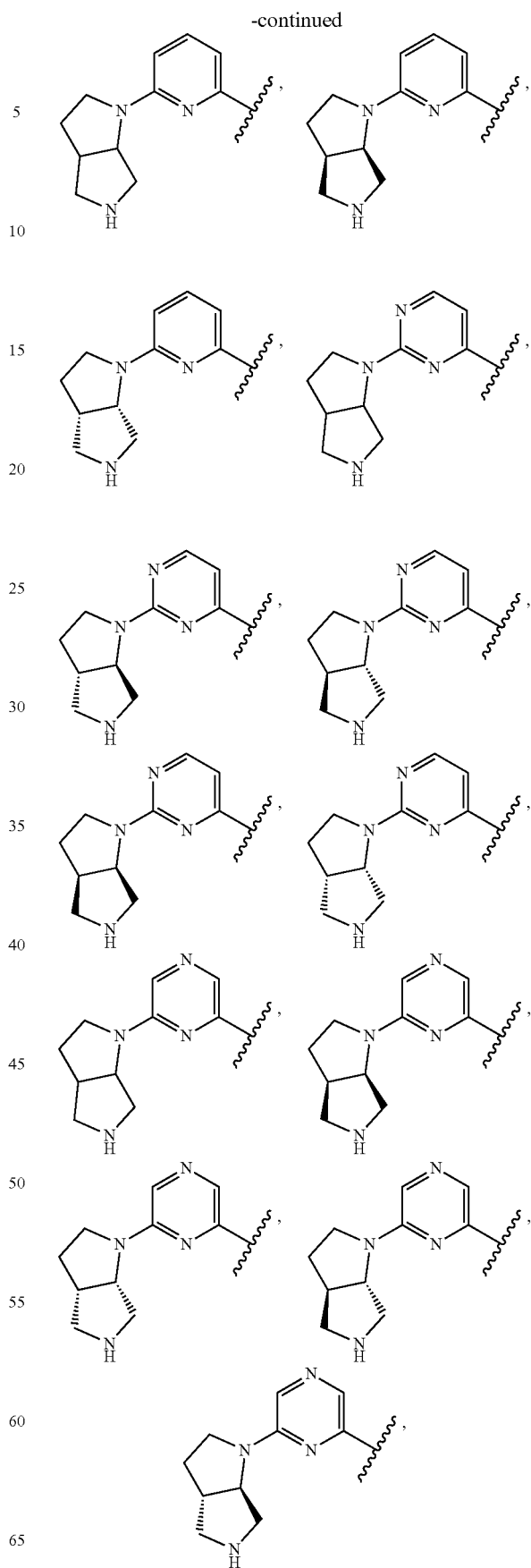

-continued
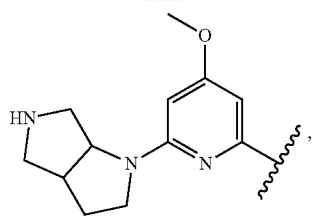,
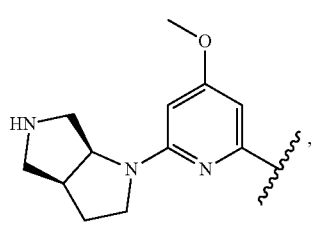,
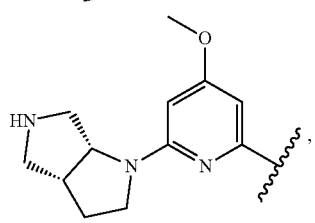,
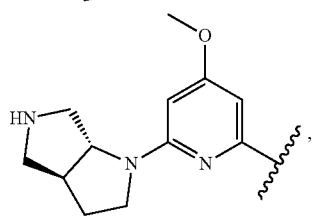,
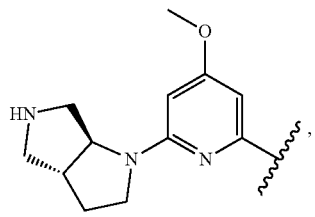,
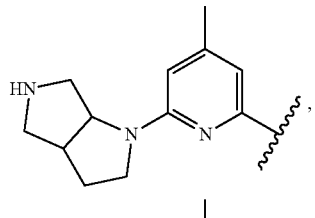,
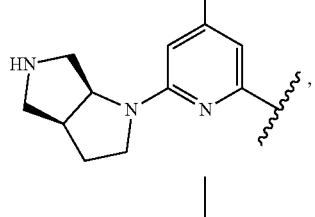,
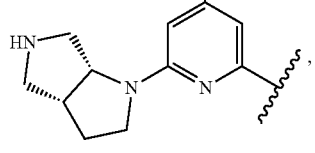,
-continued
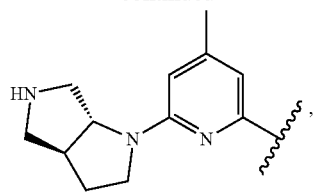,
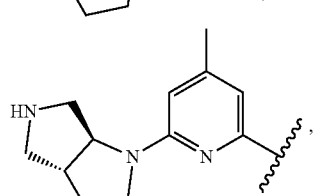,
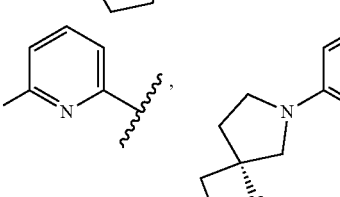,
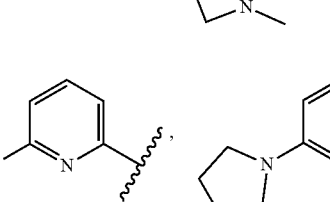,
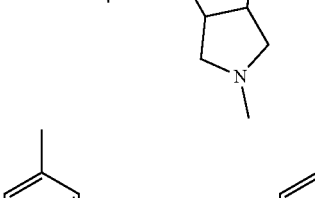,
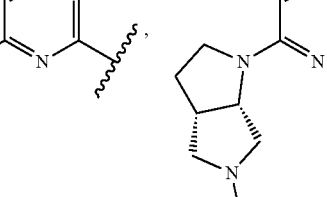,
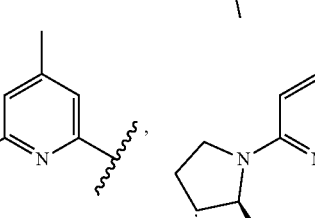,
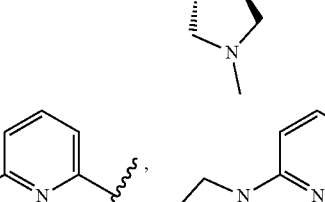,
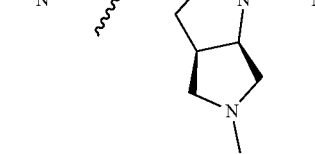,

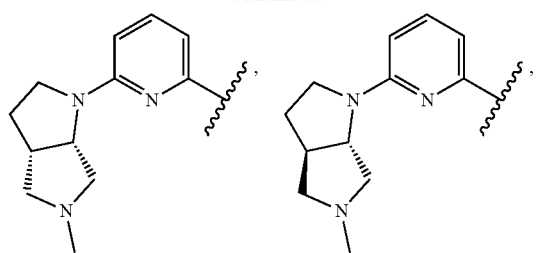
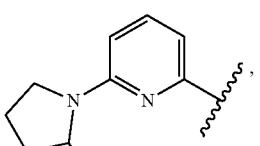
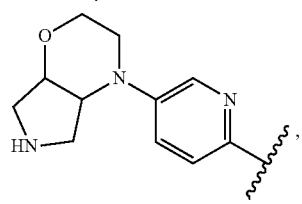

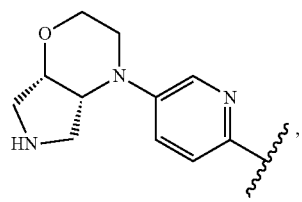

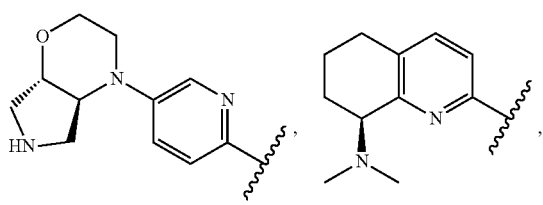
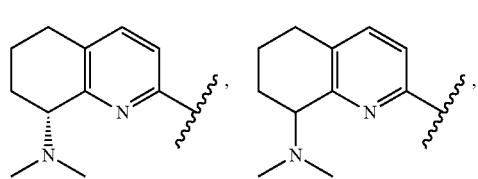
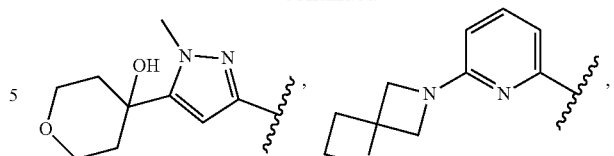
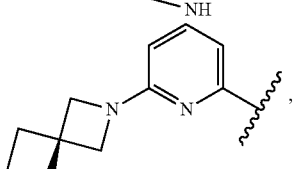
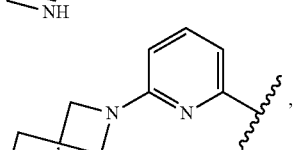
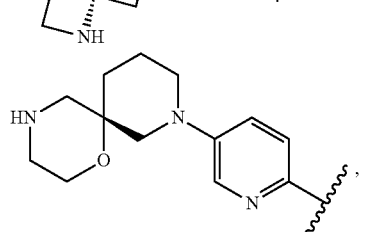
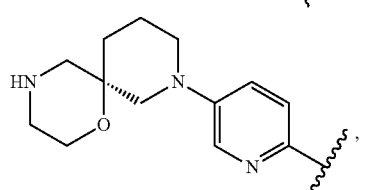
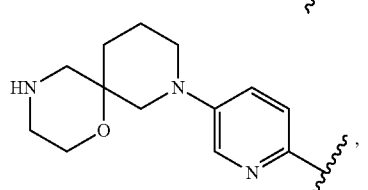
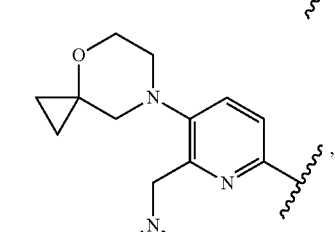
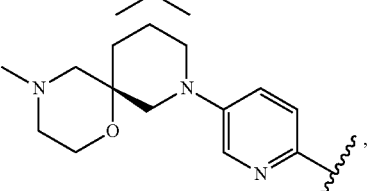
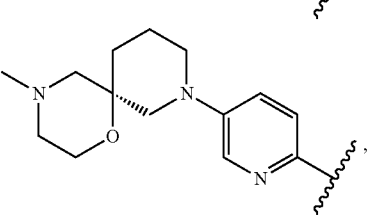

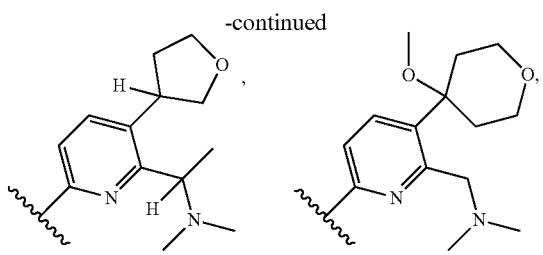
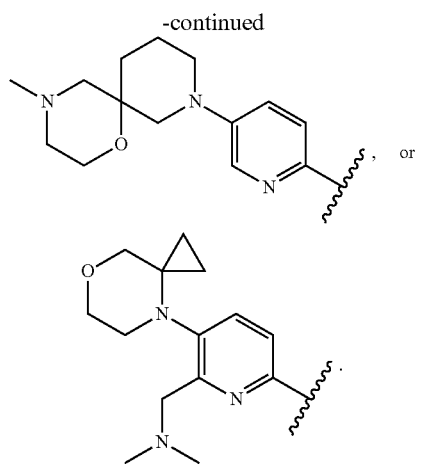
In certain embodiments, $R^1$ together with its $R^C$ substituents is
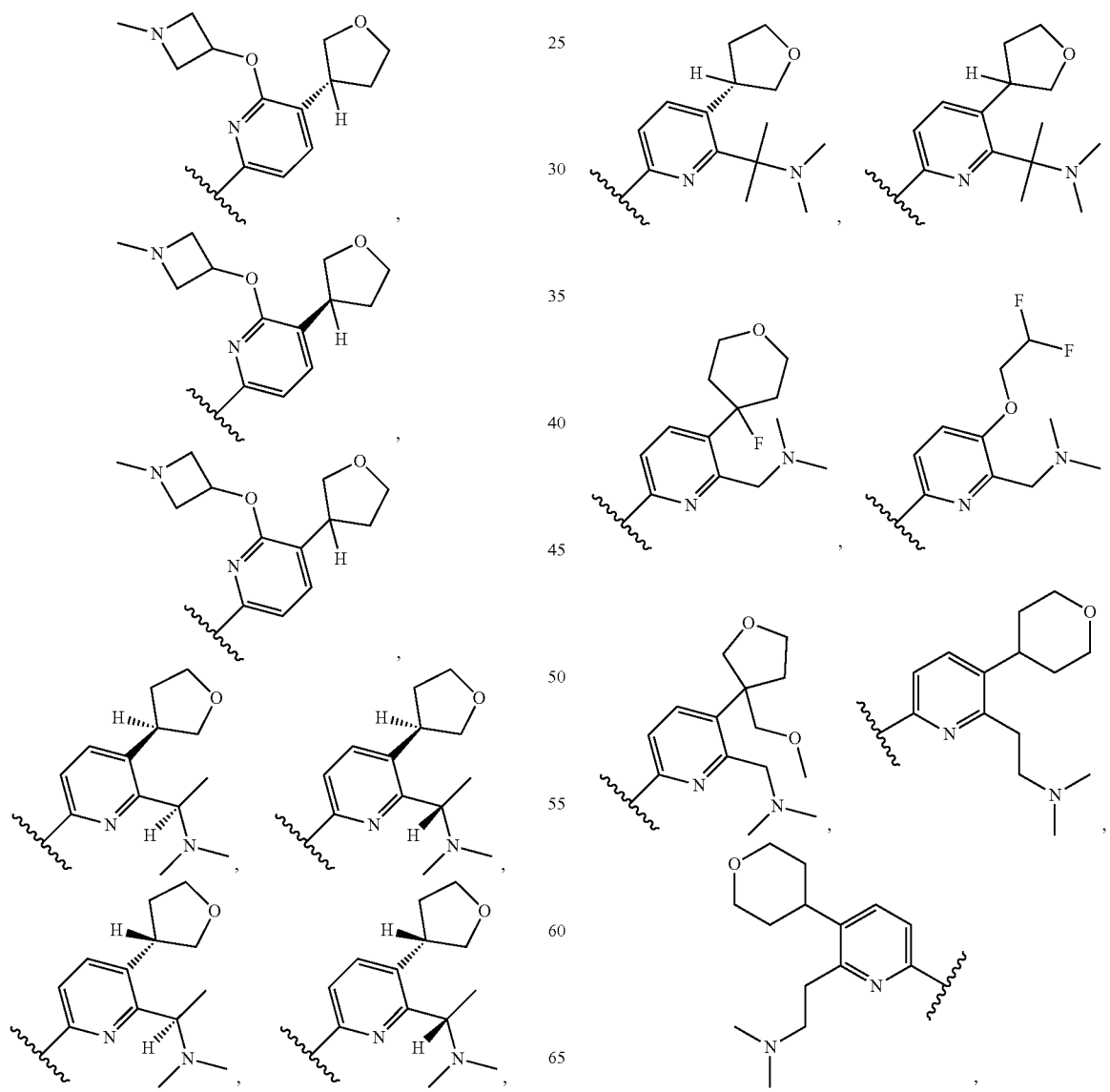

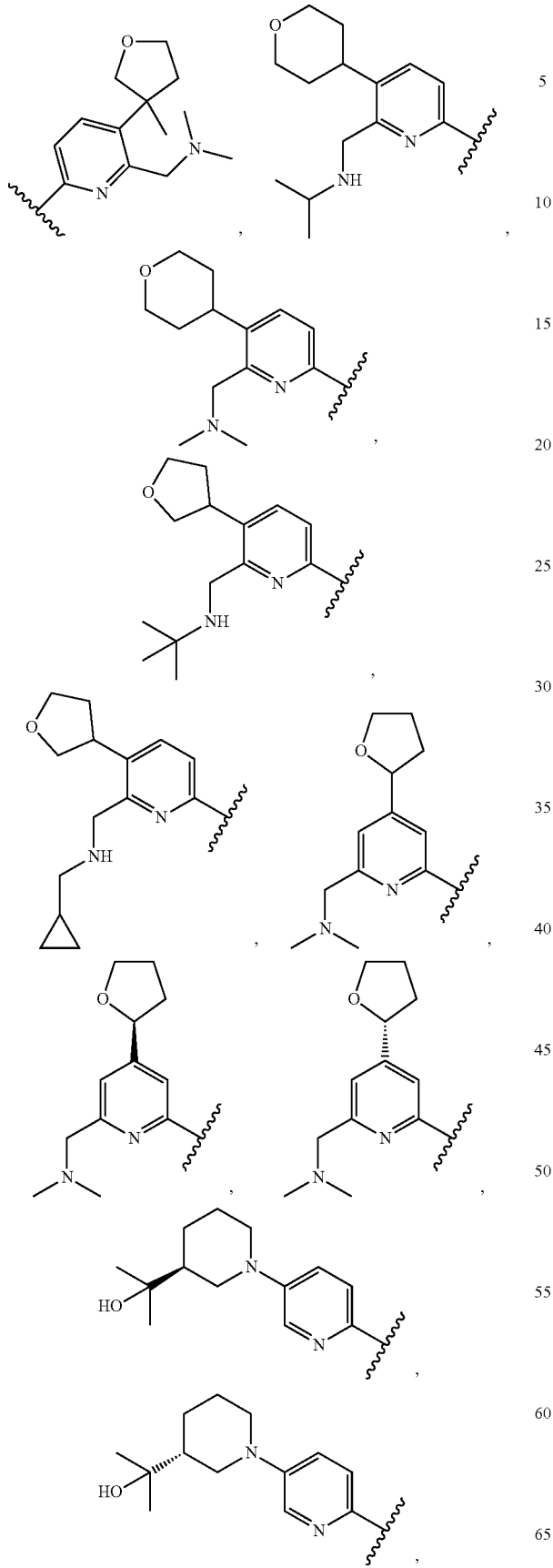
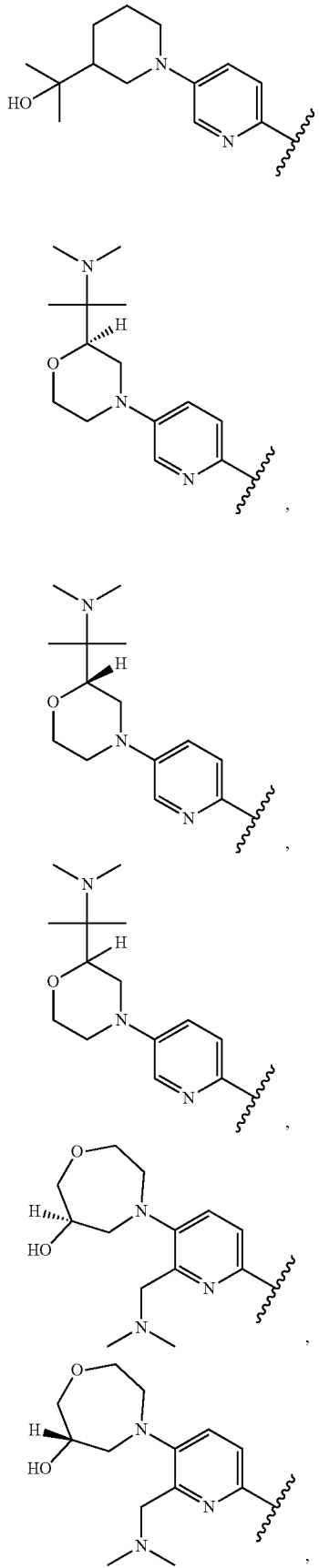

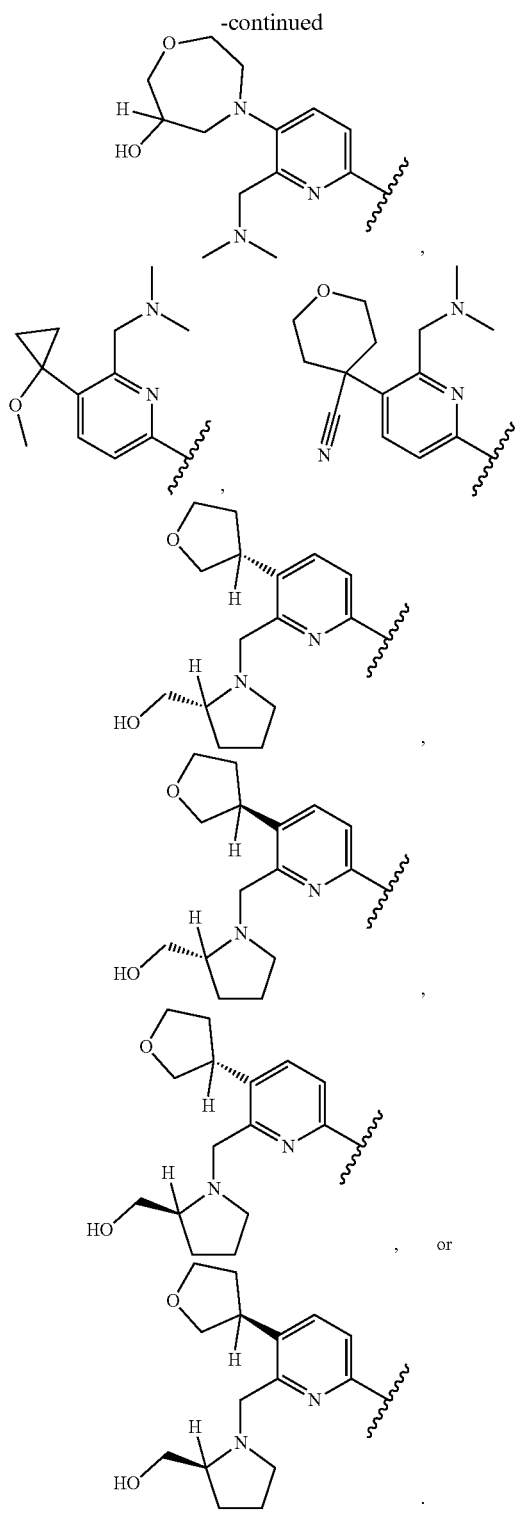

In some embodiments, $R^1$ is selected from those depicted in Table 1, below.

As defined generally above, $R^2$ is a 6-11 membered saturated, partially unsaturated, or unsaturated fused, bridged, or spiro bicyclic ring having 0-3 heteroatoms independently selected from nitrogen, oxygen, and sulfur; each of which is substituted with q instances of $R^C$.

In some embodiments, $R^2$ is a 6-11 membered saturated, partially unsaturated, or unsaturated fused, bridged, or spiro bicyclic ring having 0-3 heteroatoms independently selected from nitrogen, oxygen, and sulfur; substituted with q instances of $R^C$.

In certain embodiments, $R^2$ is a 7-10-membered fused bicyclic ring having 1-3 nitrogen atoms; each of which is substituted by each of which is substituted by q instances of $R^C$.

In certain embodiments, $R^2$ is a 9-membered fused bicyclic ring having 1-3 nitrogen atoms; each of which is substituted by each of which is substituted by q instances of $R^C$; wherein each $R^C$ is independently halogen, —CN, —OR, —C(O)NR$_2$, —NR$_2$; or each instance of $R^C$ is independently an optionally substituted group selected from $C_{1-6}$ aliphatic; phenyl; a 3-7 membered saturated or partially unsaturated monocyclic heterocyclic ring having 1-2 heteroatoms independently selected from nitrogen, oxygen, phosphorous, silicon and sulfur; and a 6-11 membered saturated or partially unsaturated fused, bridged, or spiro bicyclic heterocyclic ring having 1-3 heteroatoms independently selected from nitrogen, oxygen, and sulfur; wherein each instance of $R^C$ is independently optionally substituted by r instances of R and s instances of $R^D$.

In certain embodiments, $R^2$ is

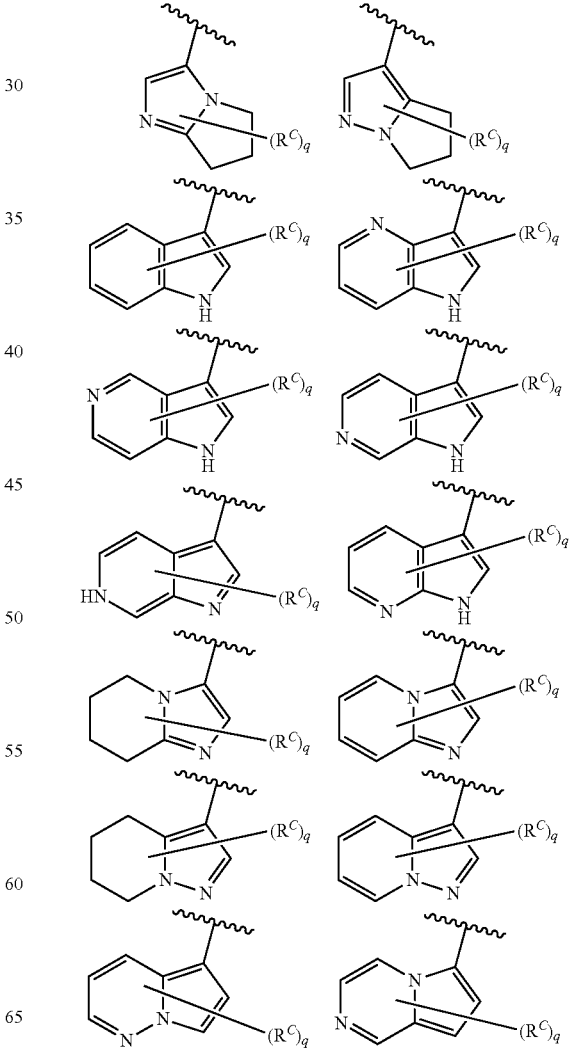

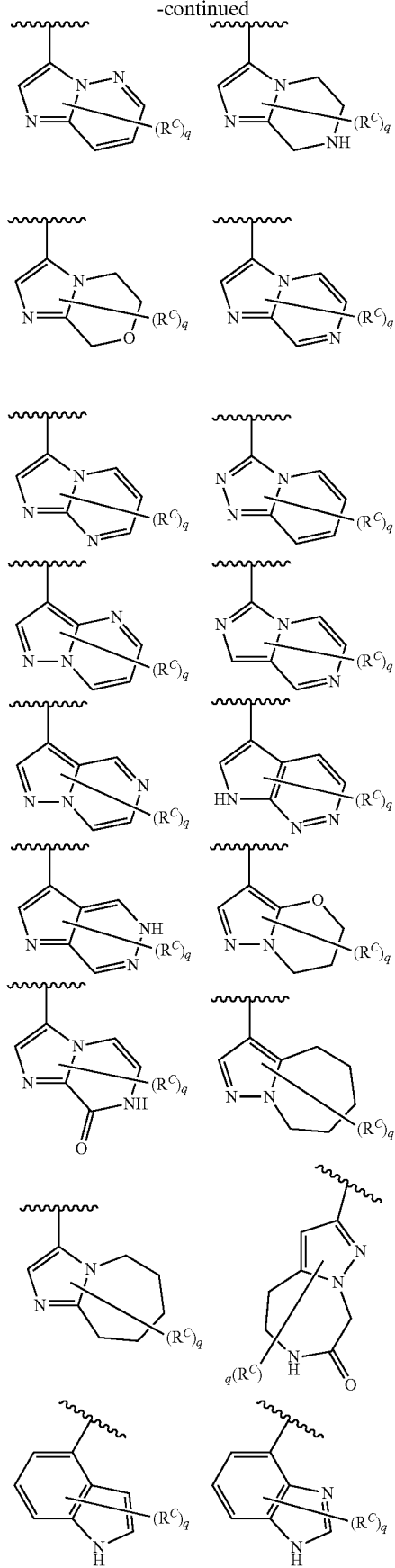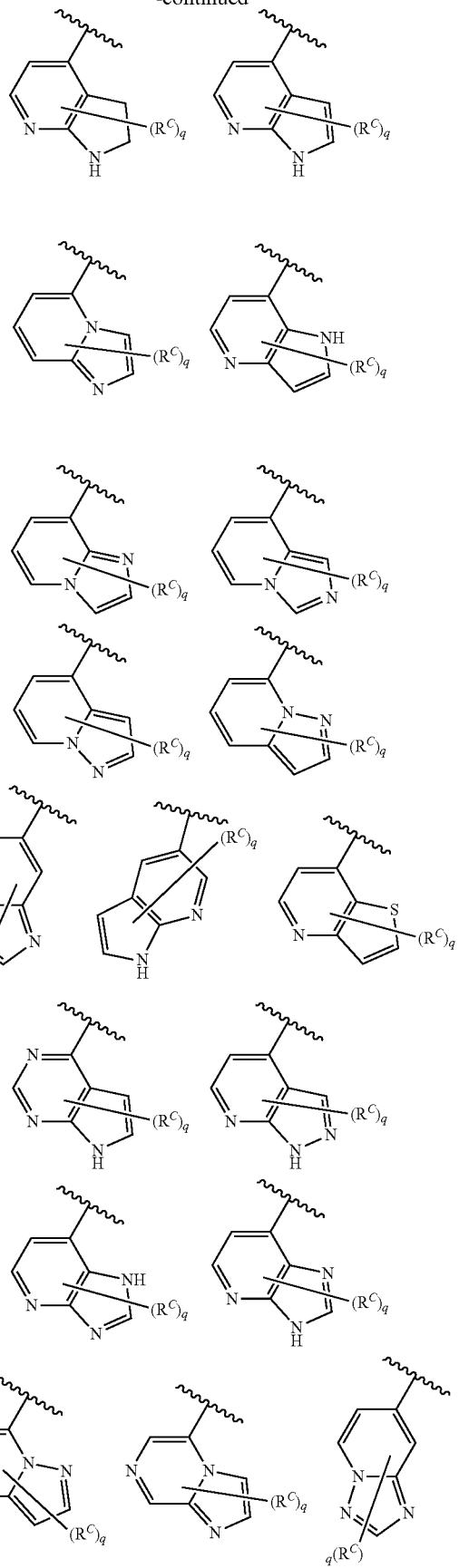

-continued
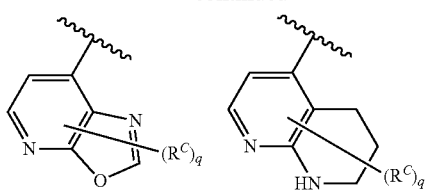
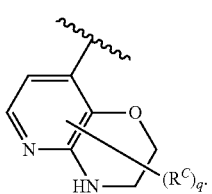
In certain embodiments, R² is
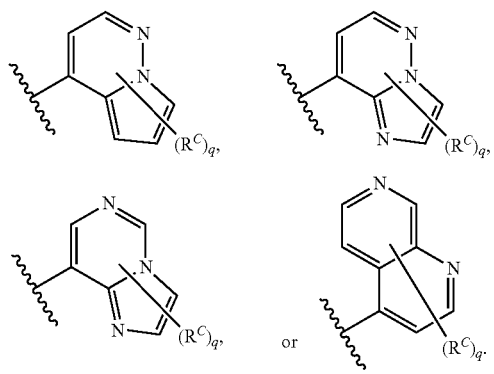
In certain embodiments, R² is
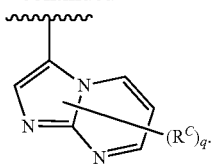 or
In certain embodiments, R² together with its $R^C$ substituents is
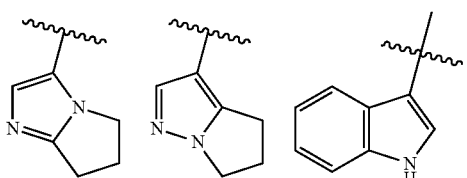
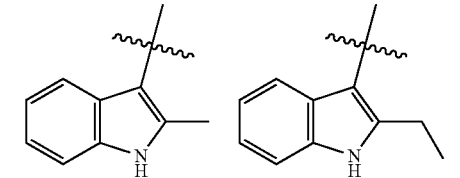
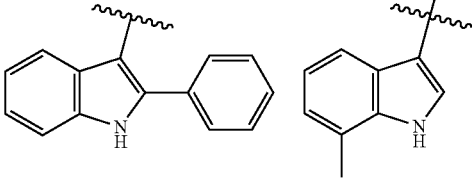
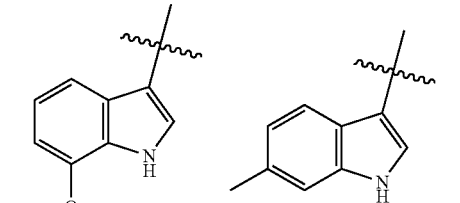
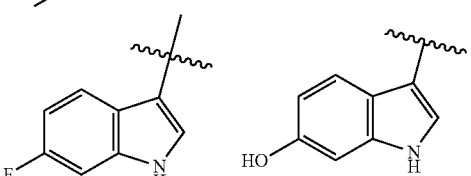
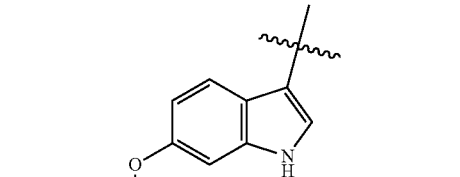
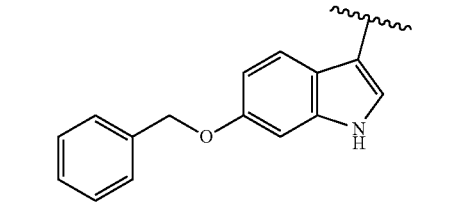

-continued
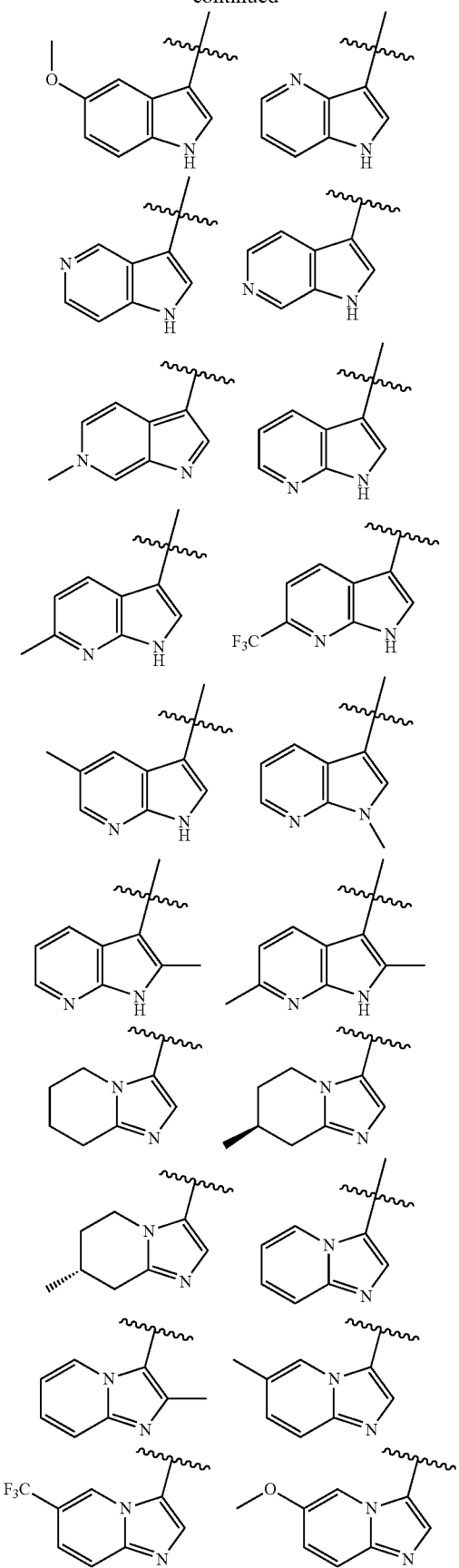
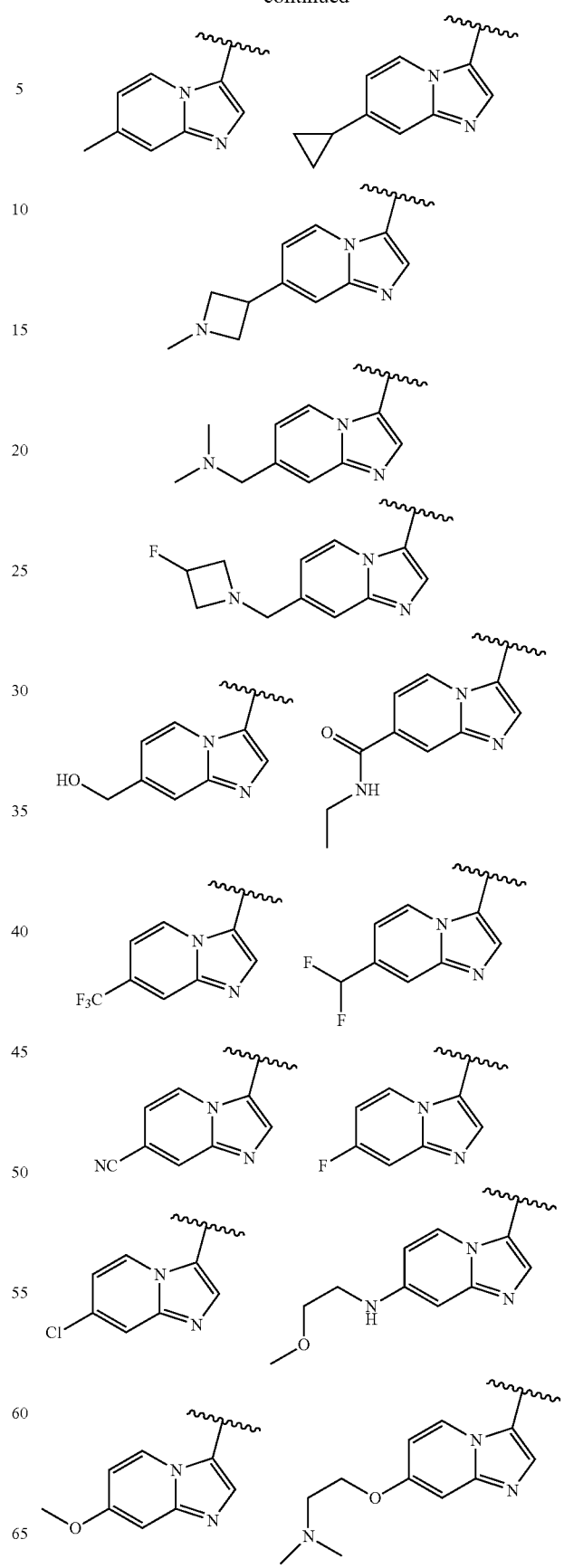

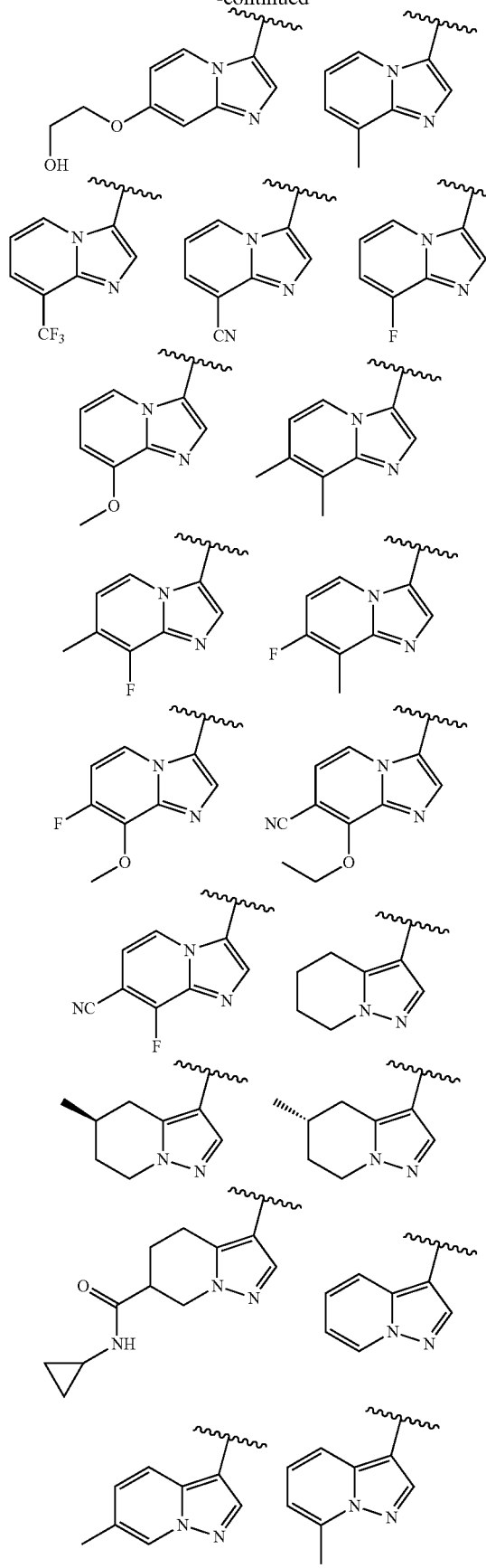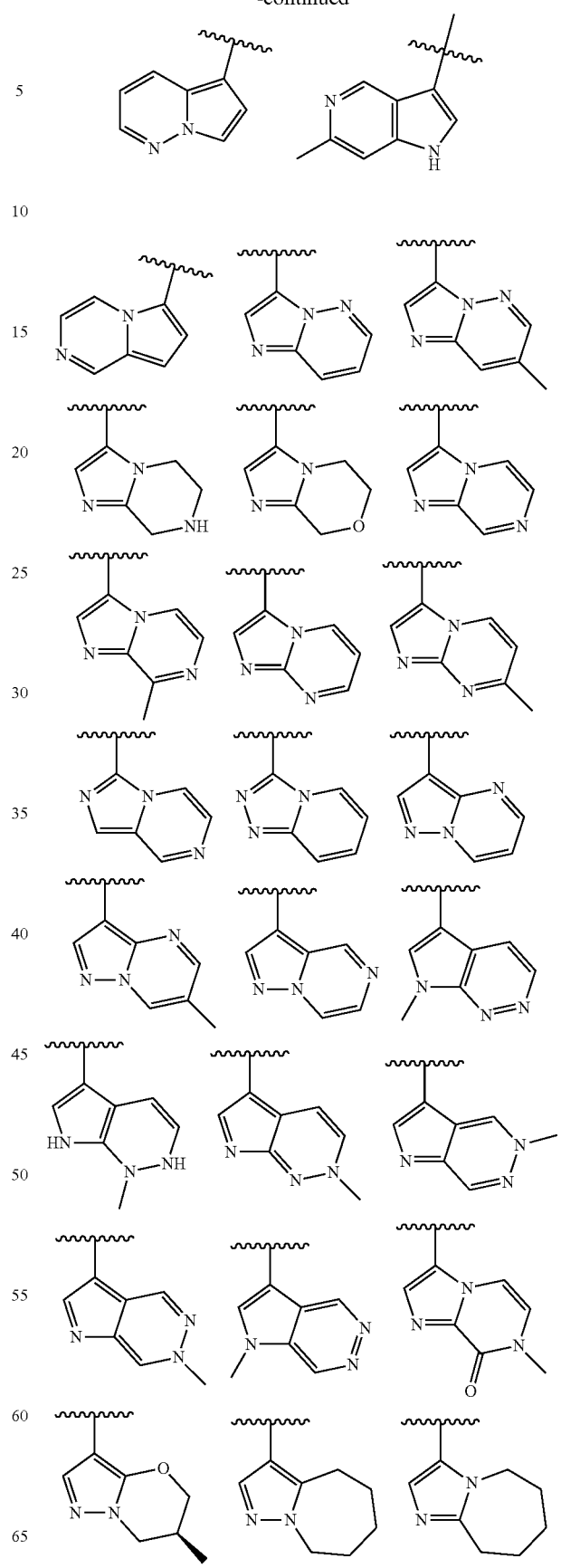

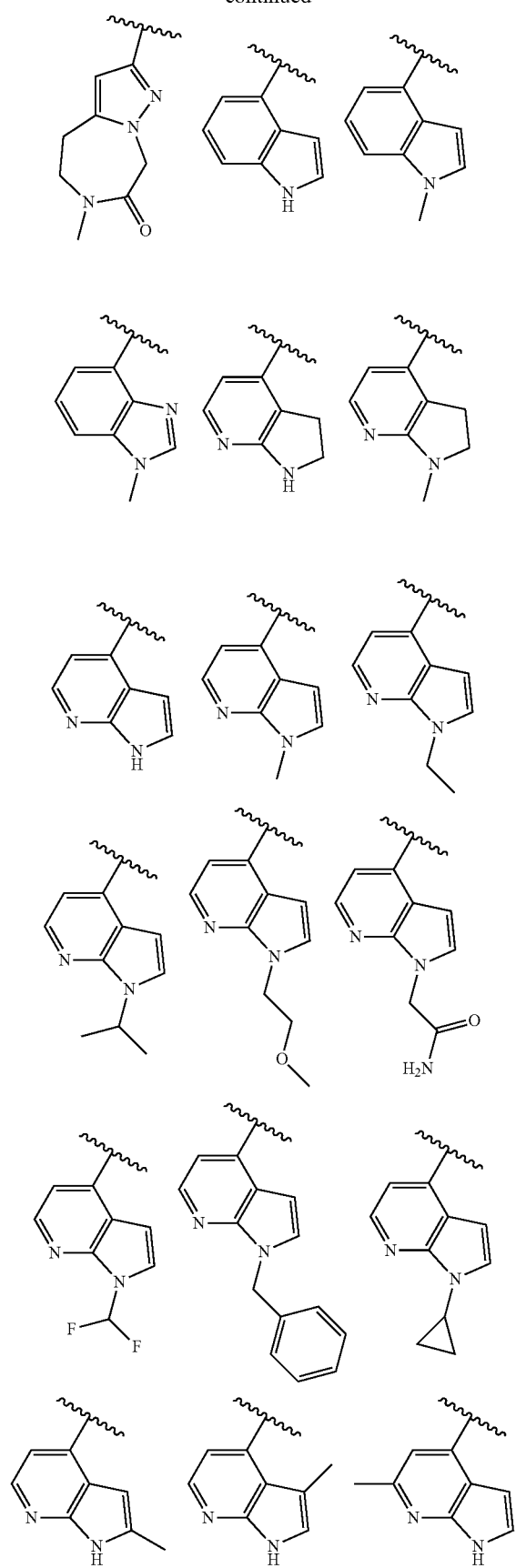
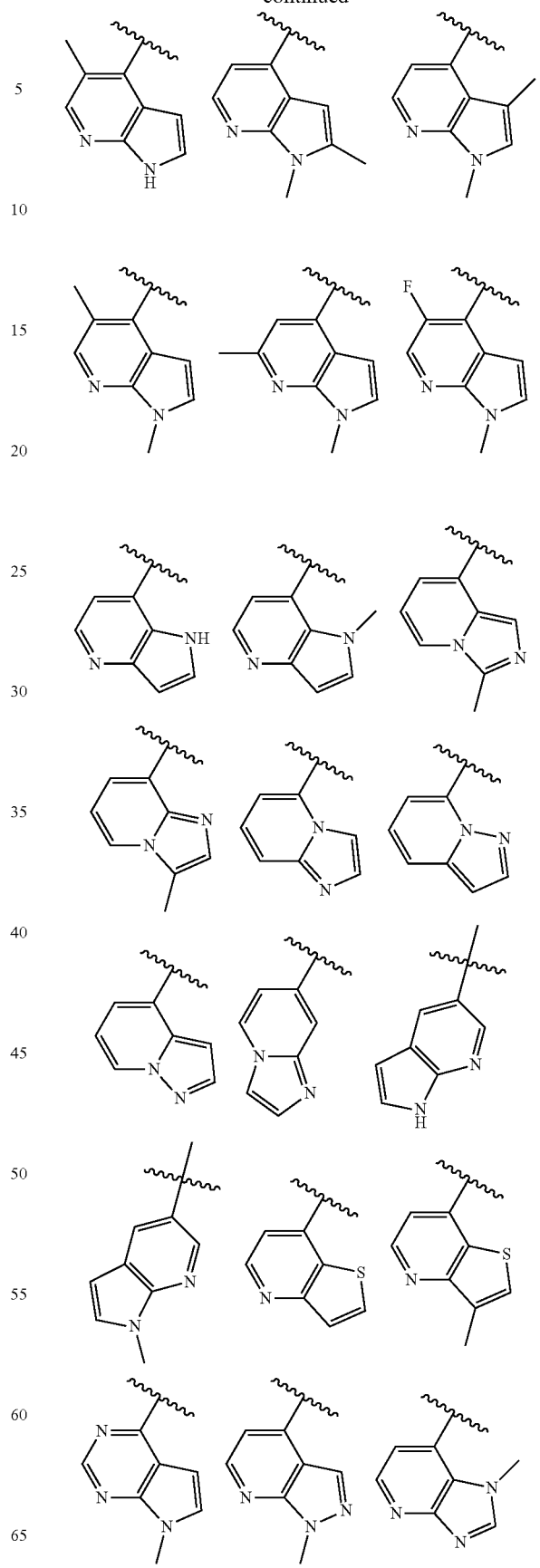

-continued

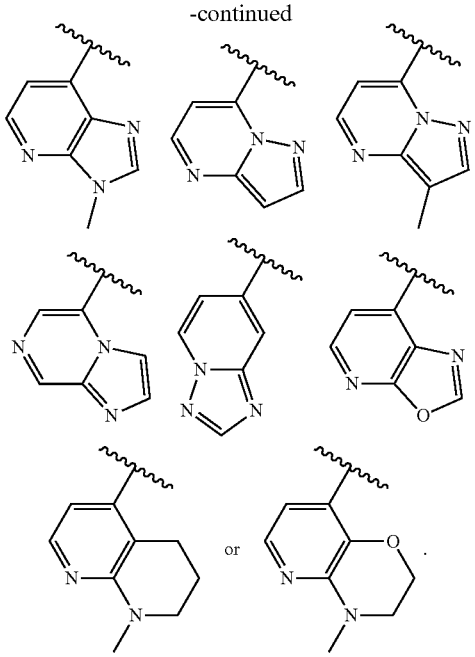

In certain embodiments, R² together with its R^C substituents is

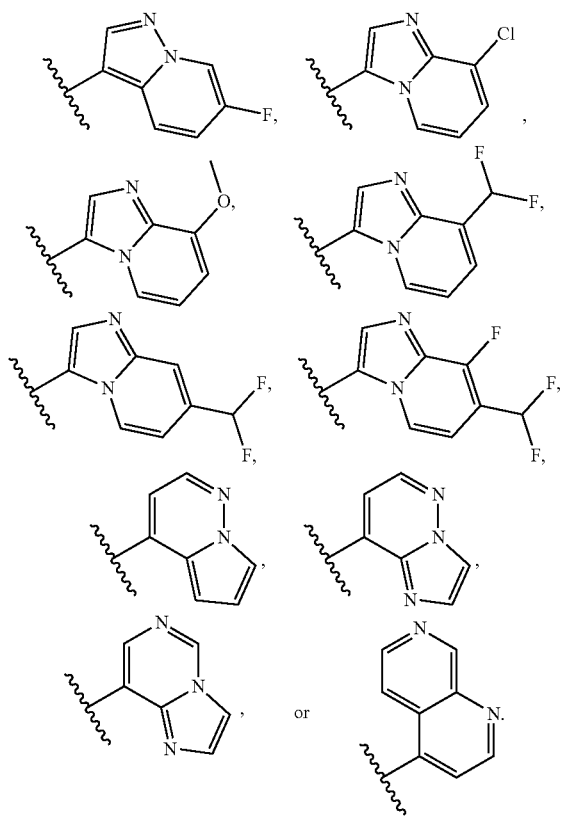

In some embodiments, R² is selected from those depicted in Table 1, below.

As defined generally above, each instance of R³ is independently hydrogen or an optionally substituted C_{1-6} aliphatic group.

In some embodiments, R³ is hydrogen. In some embodiments, R³ is an optionally substituted C_{1-6} aliphatic group.

In some embodiments, R³ is methyl. In some embodiments, R³ is

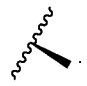

In some embodiments, R³ is

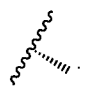

In some embodiments, R³ is selected from those depicted in Table 1, below.

As defined generally above, each instance of R^C is independently oxo, halogen, —CN, —NO₂, —OR, —SR, —NR₂, —S(O)₂R, —S(O)₂NR₂, —S(O)R, —S(O)NR₂, —C(O)R, —C(O)OR, —C(O)NR₂, —C(O)N(R)OR, —OC (O)R, —OC(O)NR₂, —N(R)C(O)OR, —N(R)C(O)R, —N(R)C(O)NR₂, —N(R)C(NR)NR₂, —N(R)NR₂, —N(R) S(O)₂NR₂, —N(R)S(O)₂R, —N═S(O)R₂, —S(NR)(O)R, —N(R)S(O)R, —N(R)CN, —P(O)(R)NR₂, —P(O)(R)OR or —P(O)R₂; or each instance of R^C is independently an optionally substituted group selected from C_{1-6} aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; or a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; or a 6-11 membered saturated or partially unsaturated bicyclic heterocyclic ring having 1-2 heteroatoms independently selected from nitrogen, oxygen, and sulfur; each of which is substituted with r instances of R and s instances of R^D.

In some embodiments, each instance of R^C is independently oxo, halogen, —CN, —NO₂, —OR, —SR, —NR₂, —S(O)₂R, —S(O)₂NR₂, —S(O)R, —S(O)NR₂, —C(O)R, —C(O)OR, —C(O)NR₂, —C(O)N(R)OR, —OC(O)R, —OC(O)NR₂, —N(R)C(O)OR, —N(R)C(O)R, —N(R)C (O)NR₂, —N(R)C(NR)NR₂, —N(R)NR₂, —N(R)S(O)₂ NR₂, —N(R)S(O)₂R, —N═S(O)R₂, —S(NR)(O)R, —N(R)S(O)R, —N(R)CN, —P(O)(R)NR₂, —P(O)(R)OR or —P(O)R₂; or each instance of R^C is independently an optionally substituted group selected from C_{1-6} aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; or a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; or a 6-11 membered saturated or partially unsaturated bicyclic heterocyclic ring having 1-2 heteroatoms independently selected from nitrogen, oxygen, and sulfur.

In some embodiments, each instance of $R^C$ is oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$.

In some embodiments, each instance of $R^C$ is an optionally substituted group selected from C$_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, phosphorous, silicon and sulfur; or a 5-6 membered monocyclic heteroaryl ring having 1-4 heteroatoms independently selected from nitrogen, oxygen, and sulfur; an 8-10 membered bicyclic heteroaryl ring having 1-5 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; or a 6-11 membered saturated or partially unsaturated bicyclic heterocyclic ring having 1-2 heteroatoms independently selected from nitrogen, oxygen, and sulfur.

In some embodiments, $R^C$ is a 6-11 membered saturated or partially unsaturated spirocyclic ring having 0-3 heteroatoms independently selected from nitrogen, oxygen, and sulfur which is substituted with r instances of R and s instances of $R^D$.

In some embodiments, $R^C$ is a 6-11 membered saturated or partially unsaturated bicyclic heterocyclic ring having 1-3 heteroatoms independently selected from nitrogen, oxygen, and sulfur which is substituted with r instances of R and s instances of $R^D$.

In some embodiments, $R^C$ is methyl, oxo, fluoro or methoxy.

In some embodiments, $R^C$ is

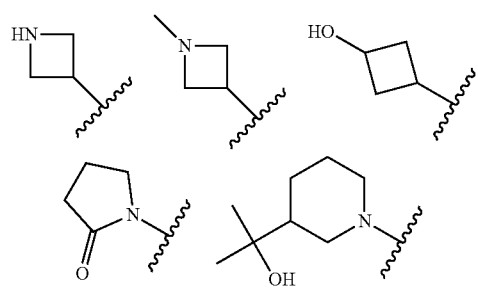

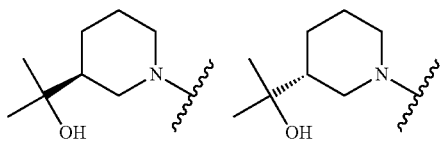

-continued

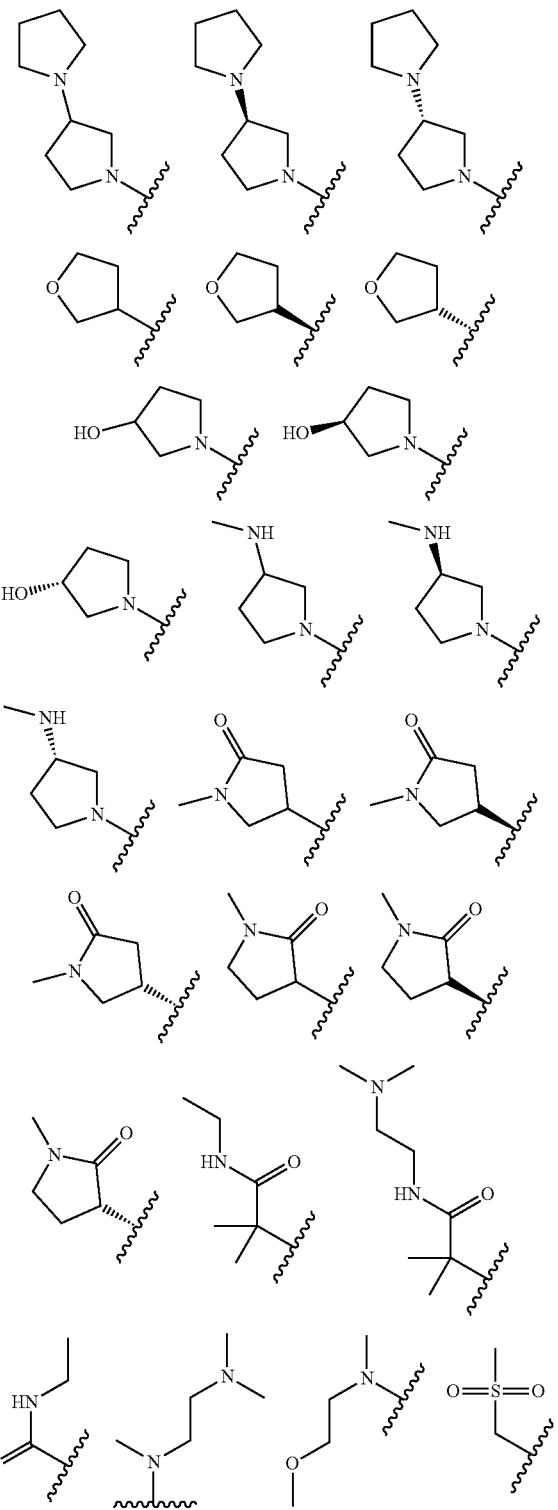

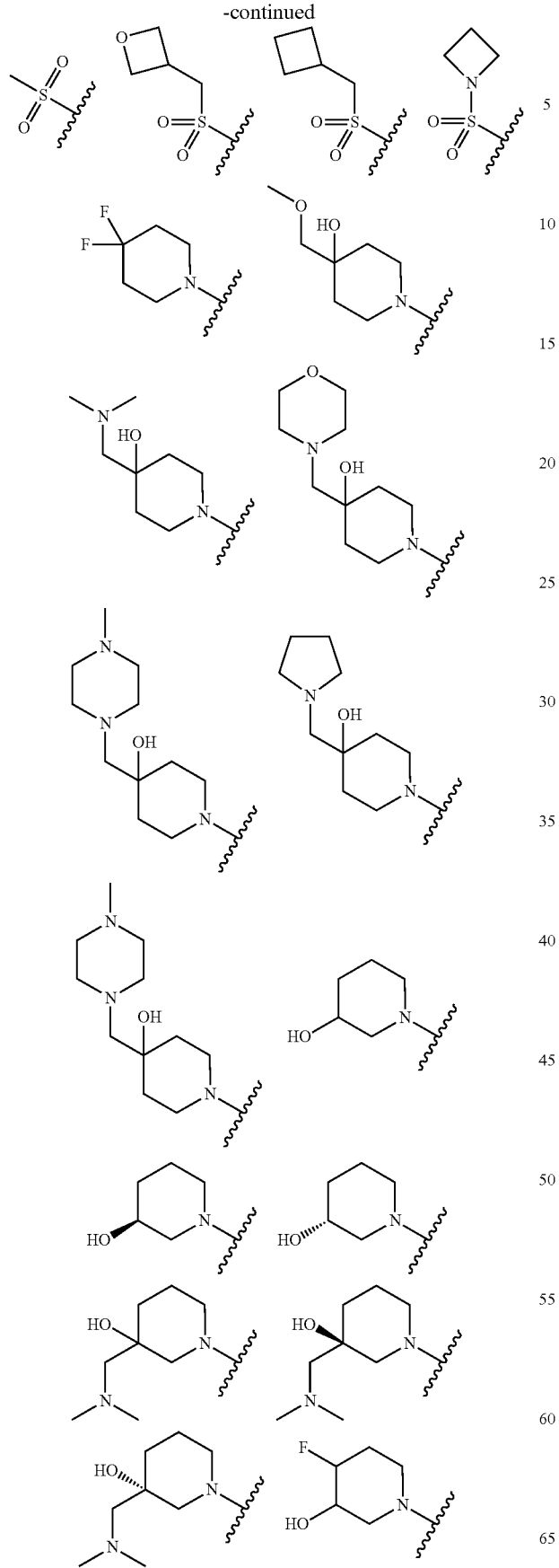
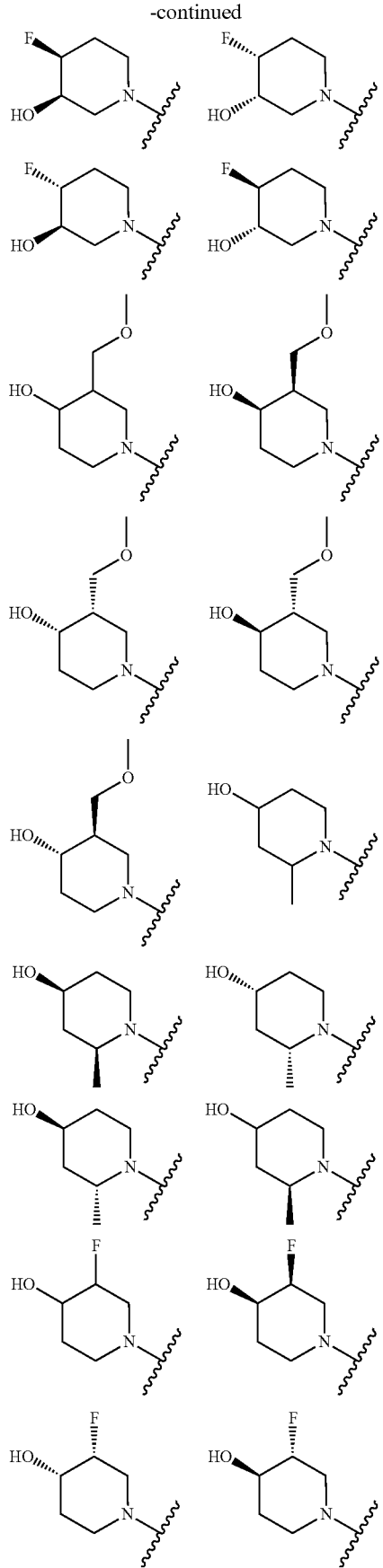

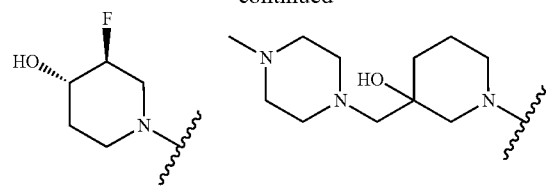
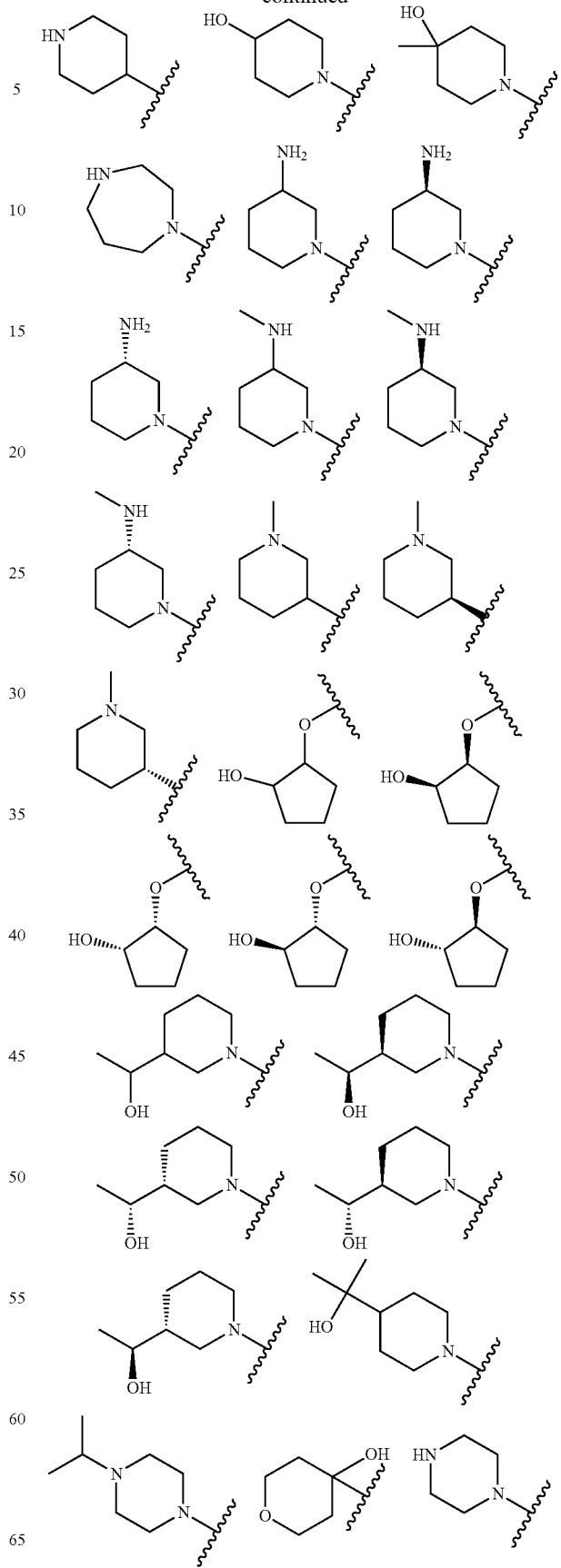

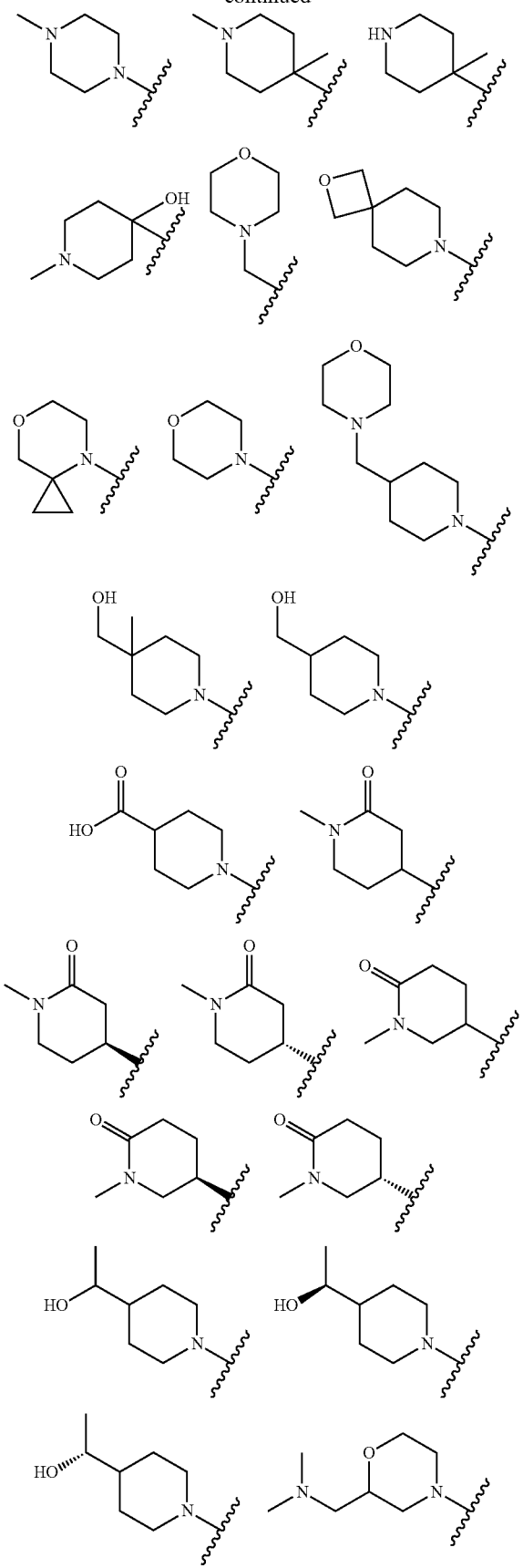
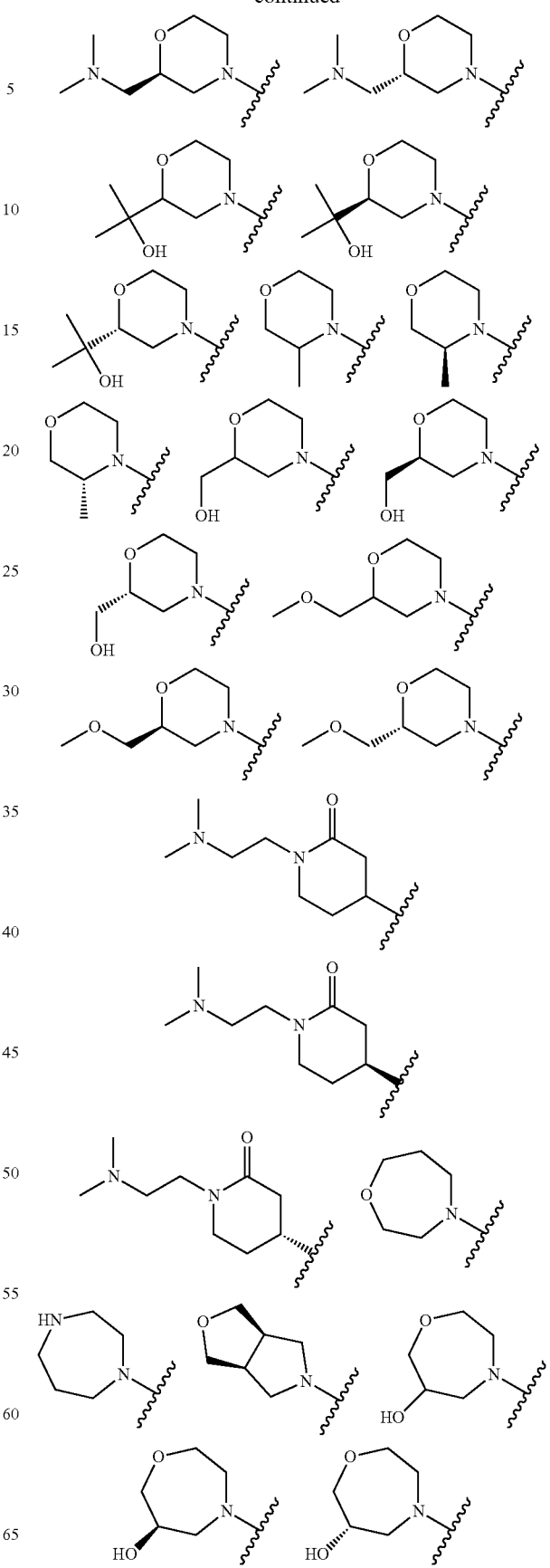

-continued
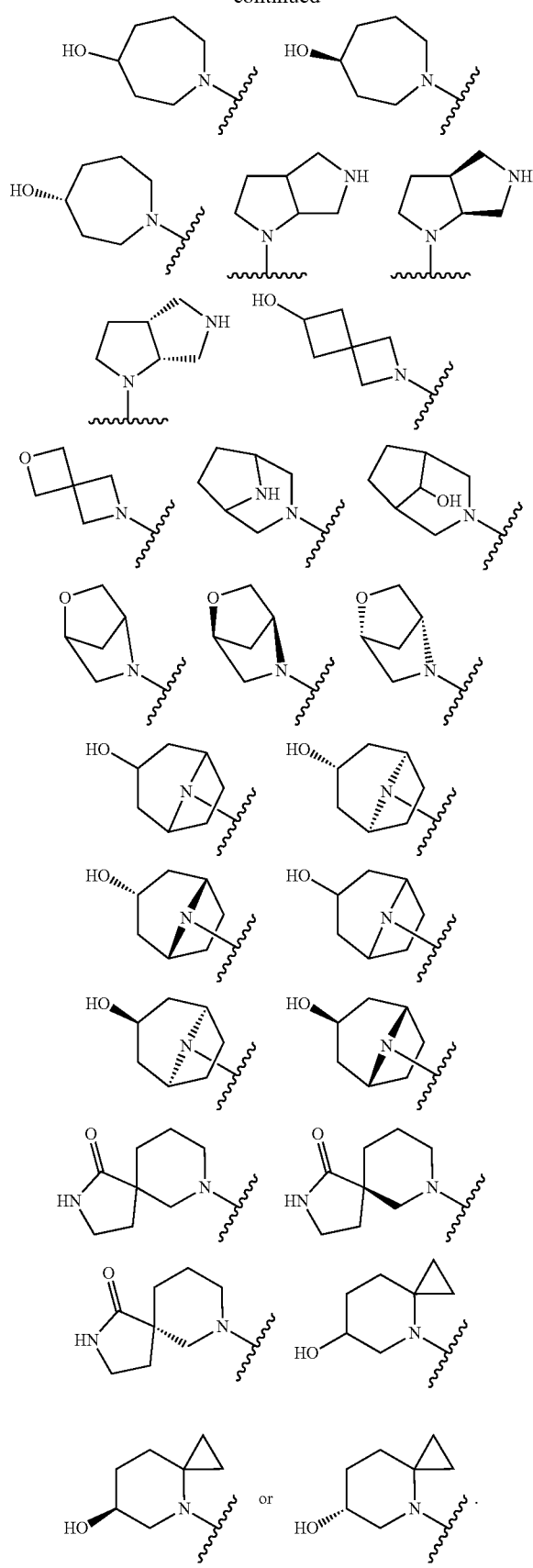
In some embodiments, $R^C$ is —CHF$_2$ or chloro.
In some embodiments, $R^C$ is
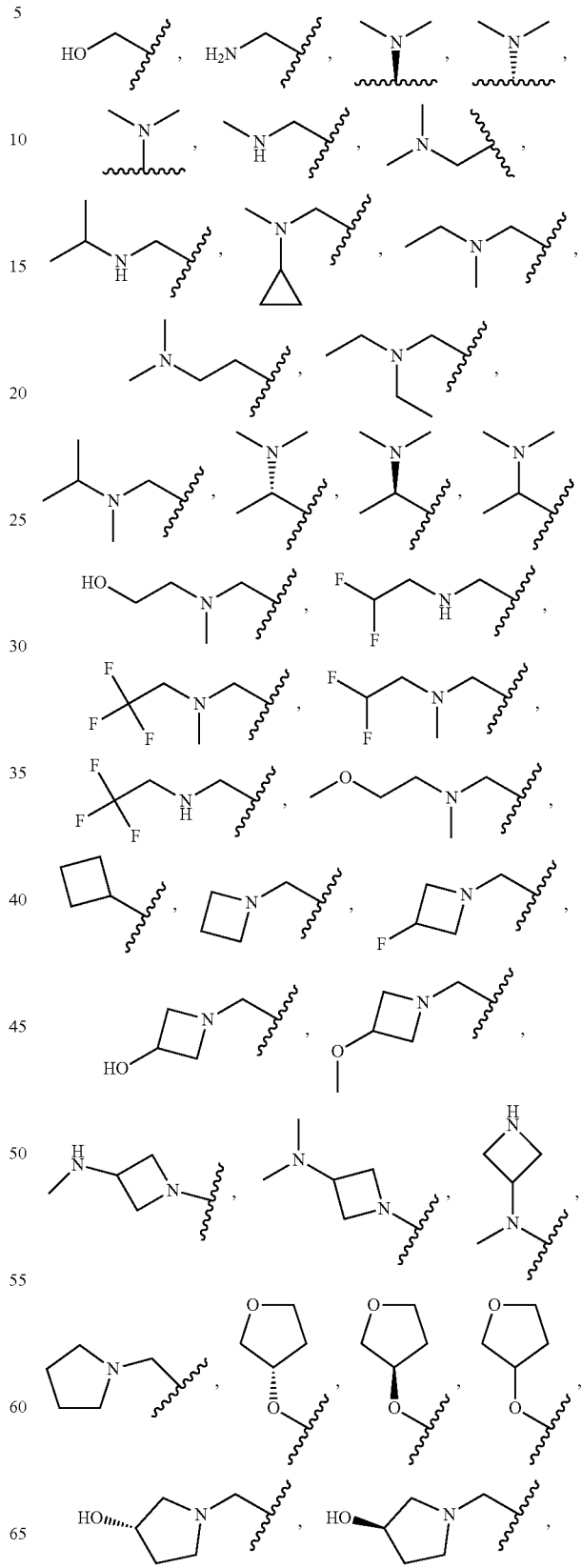

111
-continued
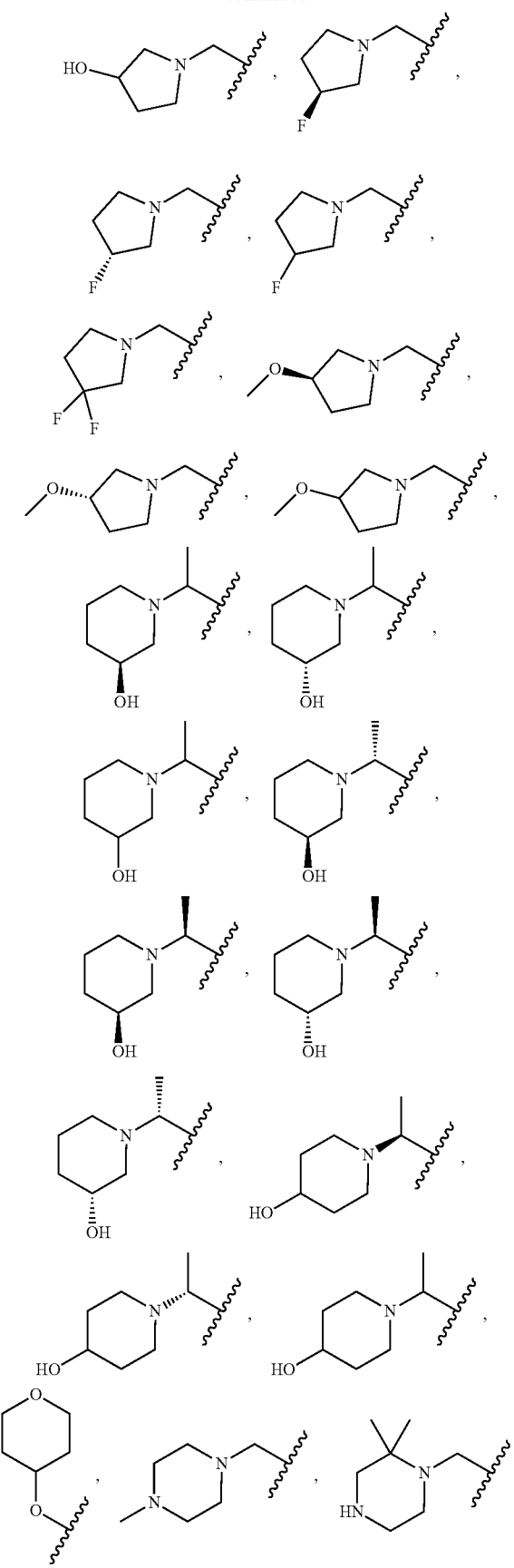
112
-continued
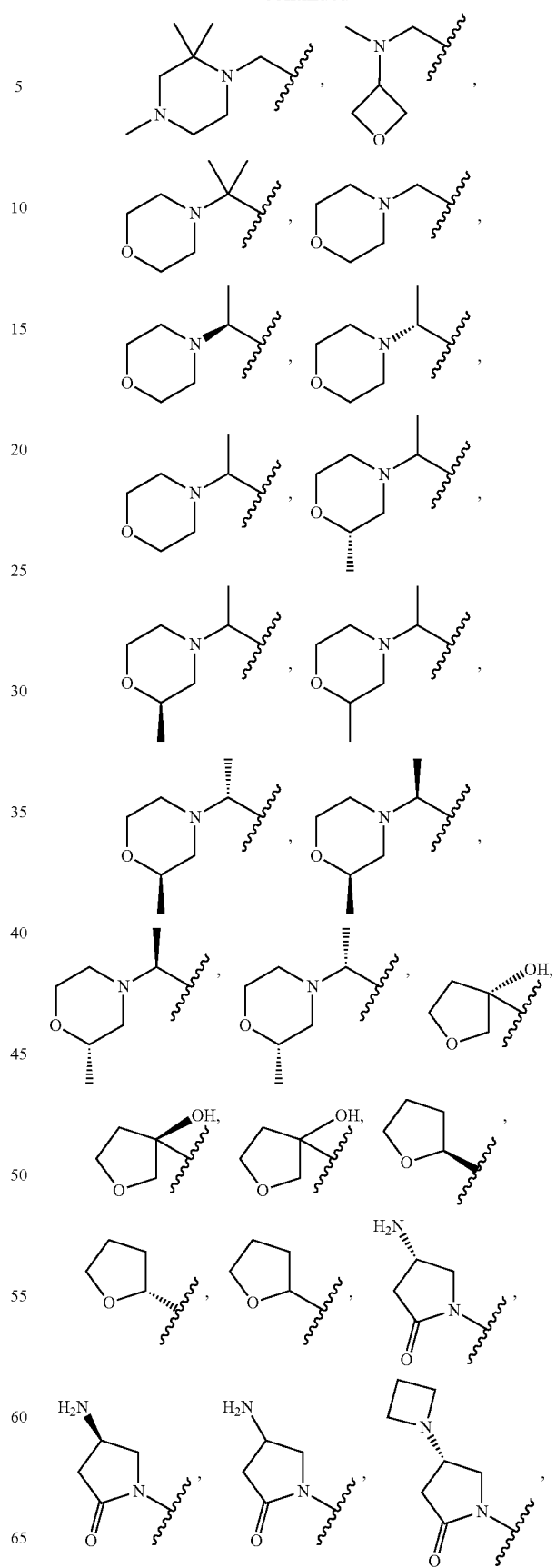

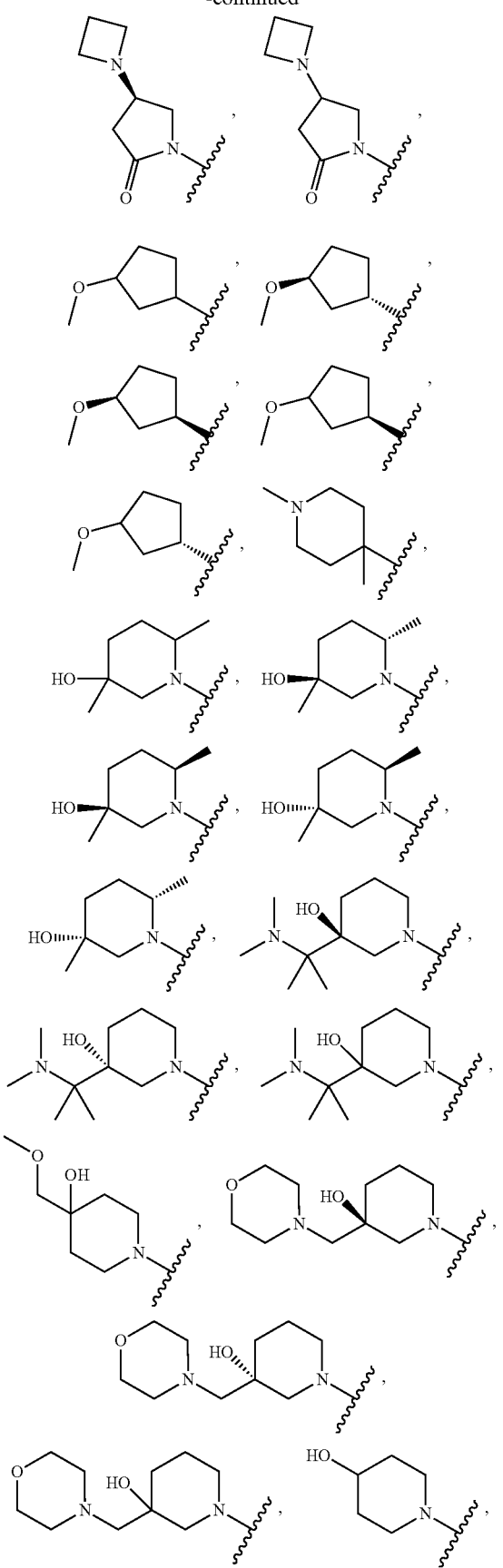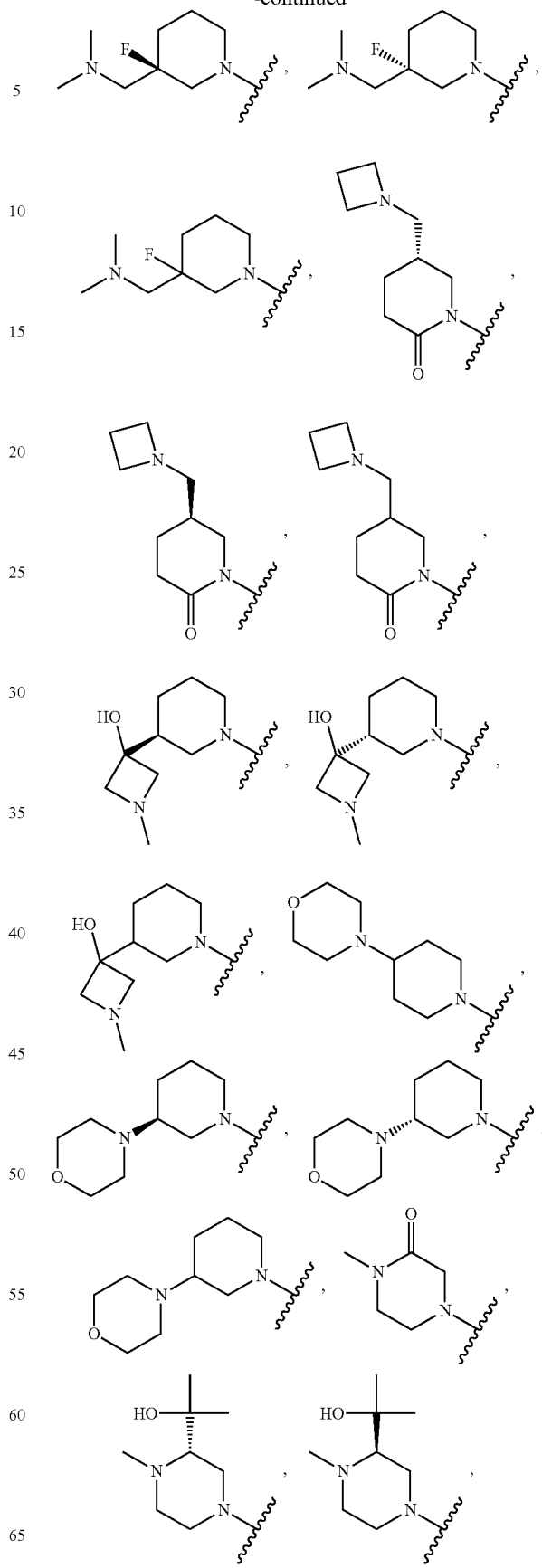

115
-continued
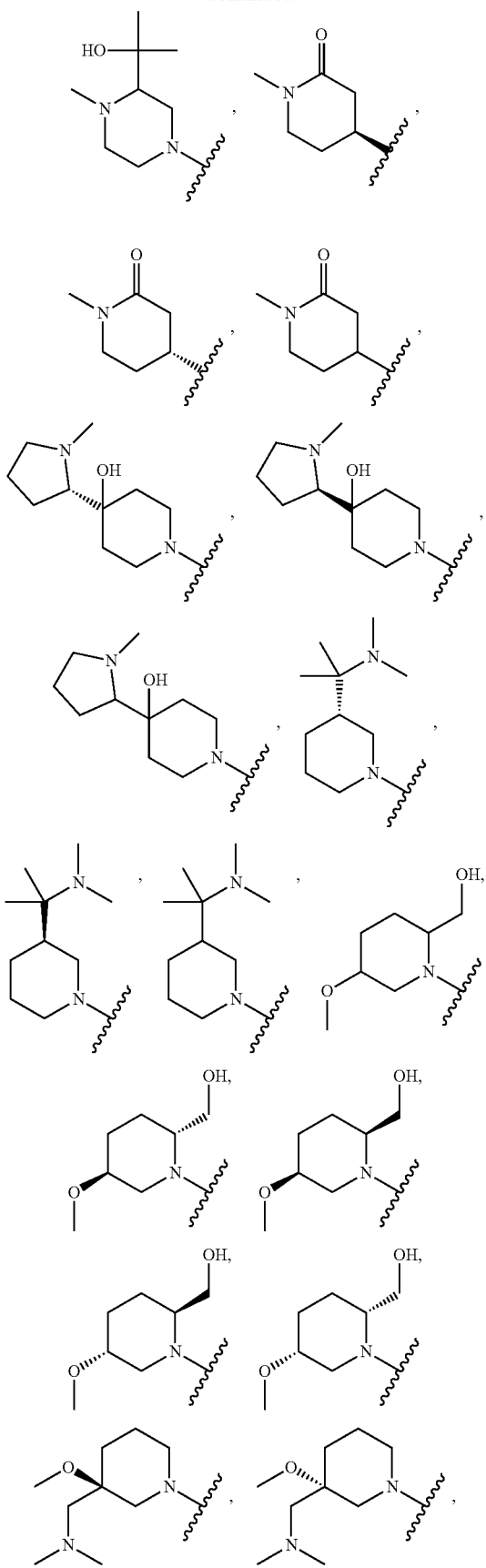
116
-continued
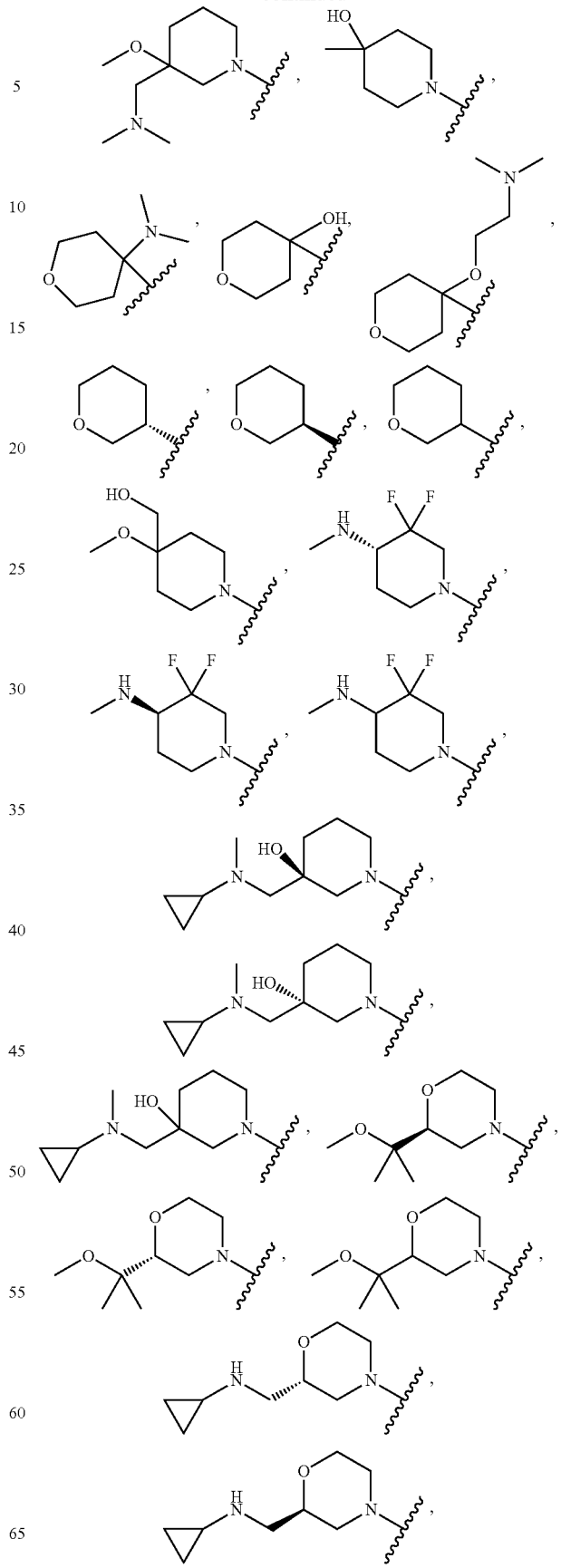

117
-continued
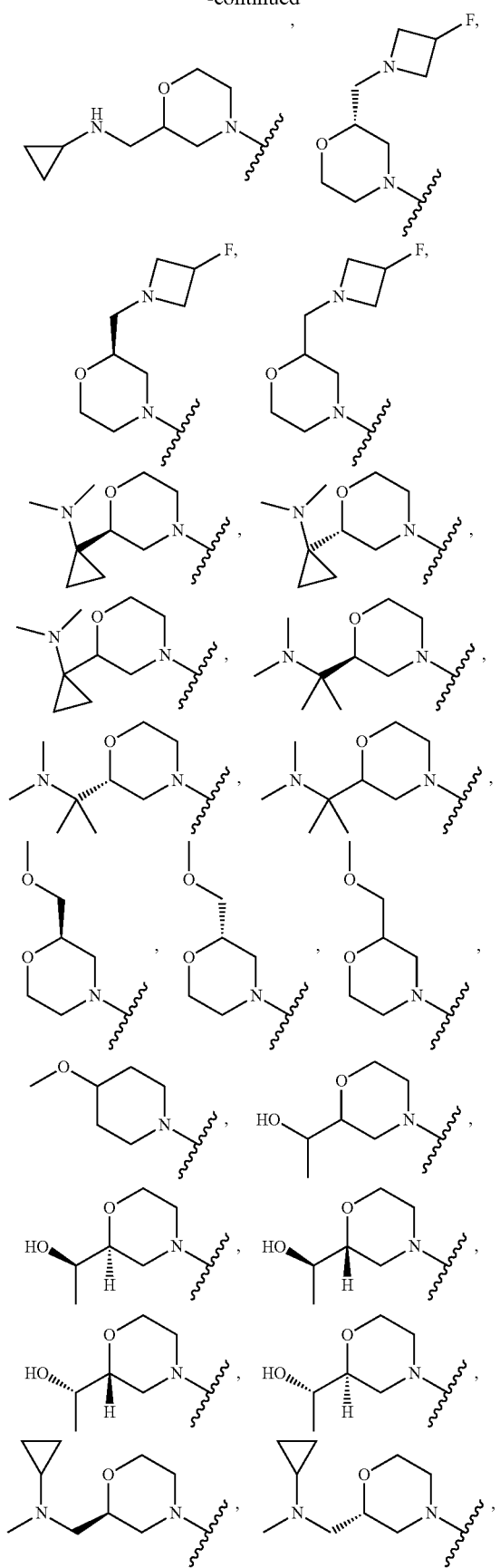
118
-continued
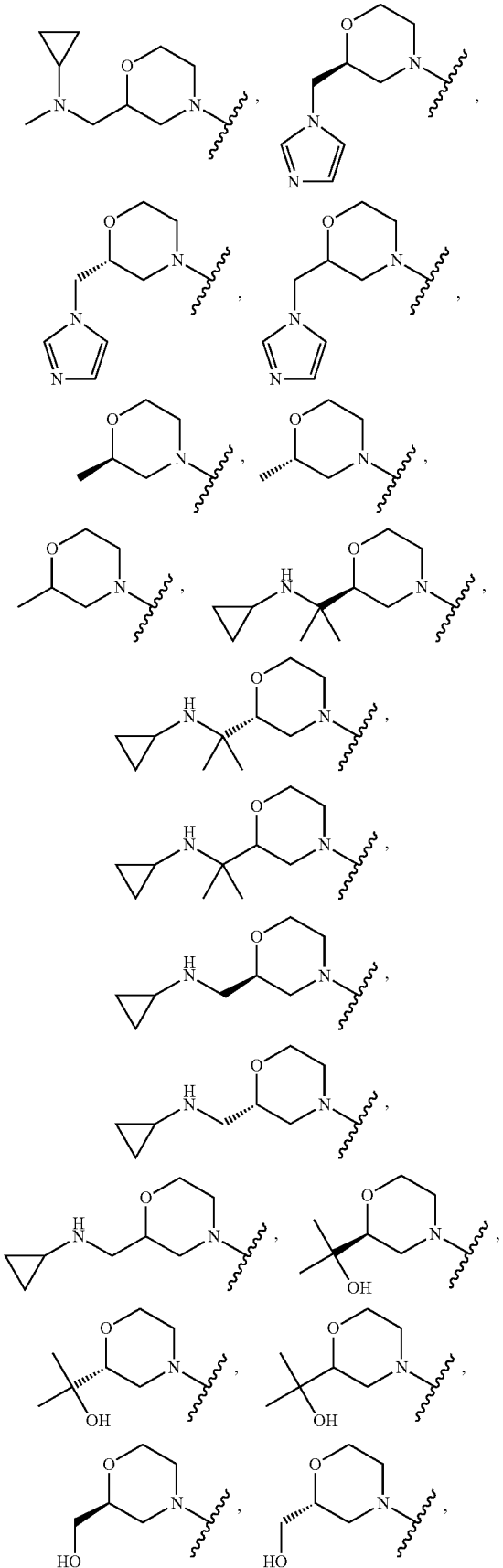

119
-continued
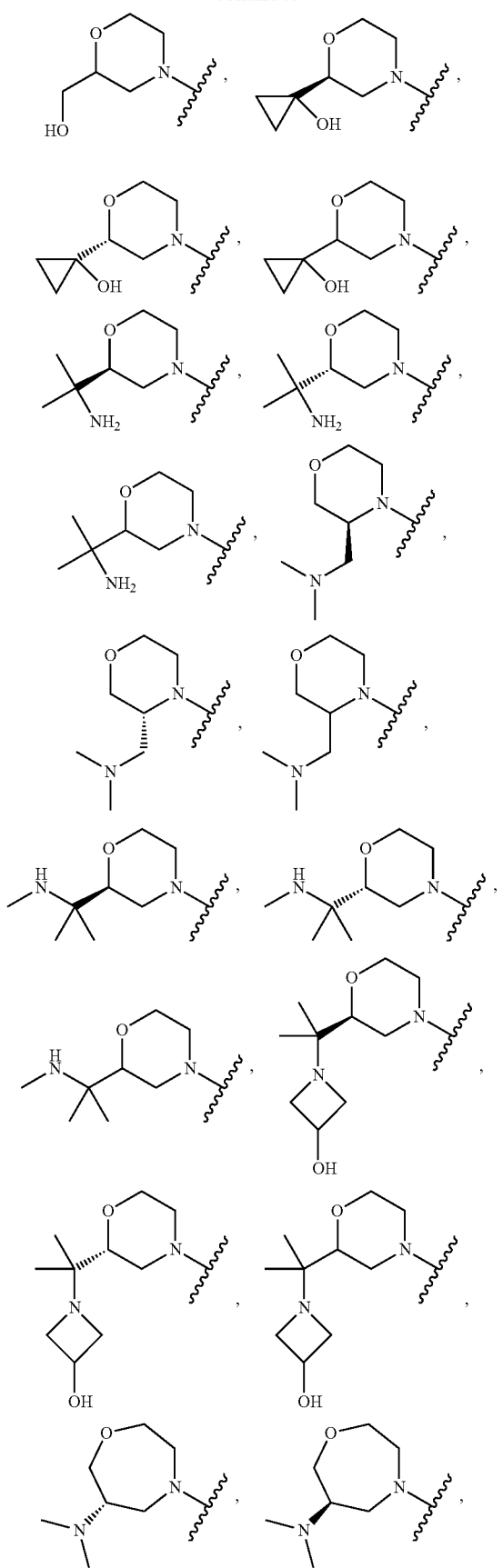
120
-continued
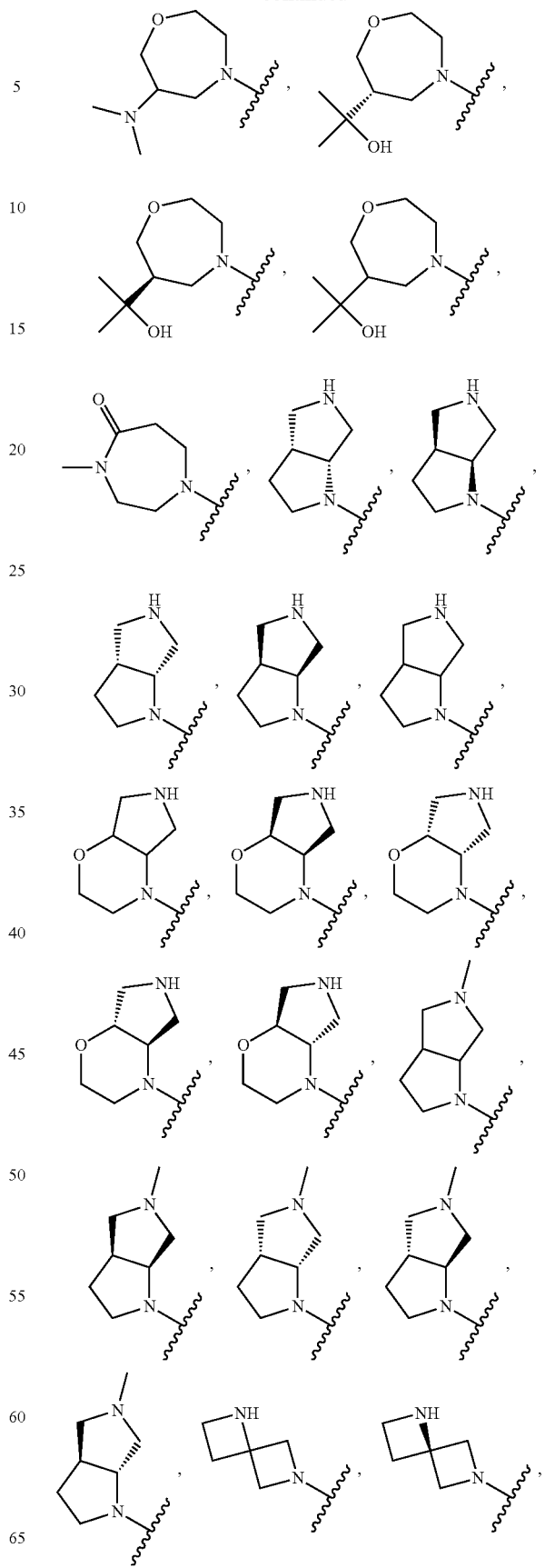

121

-continued

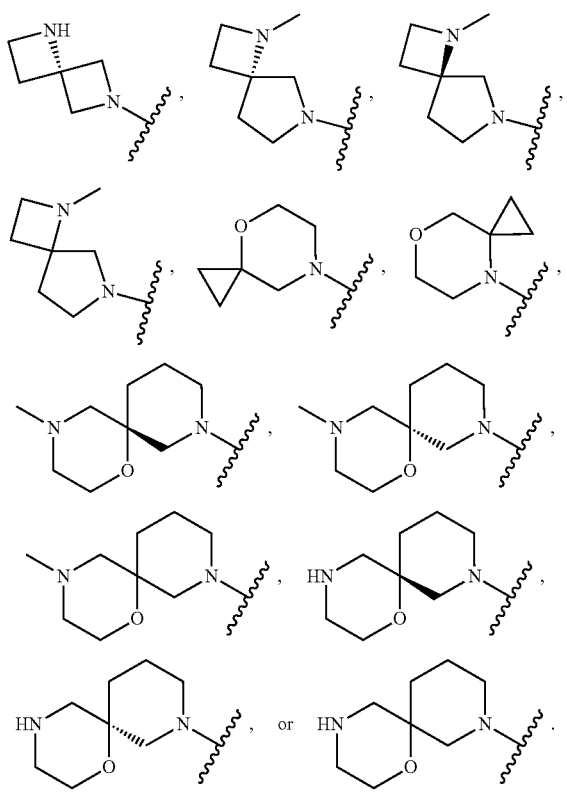

In some embodiments, $R^C$ is

122

-continued

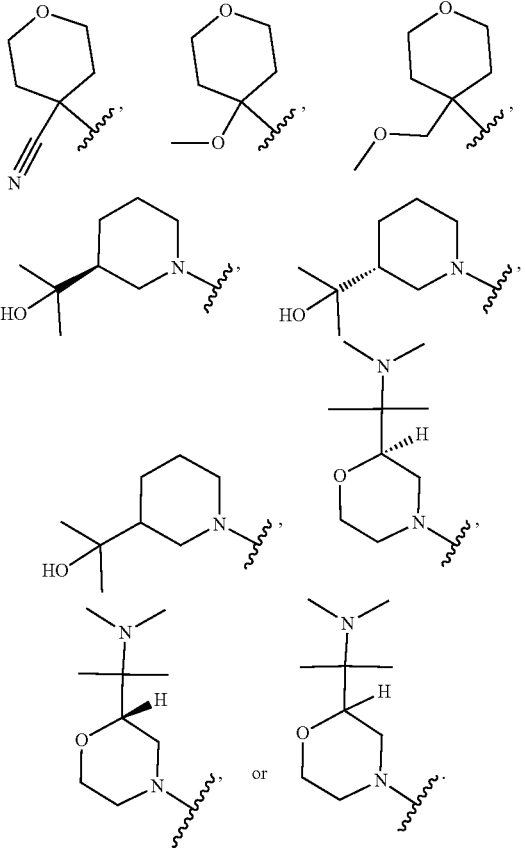

In some embodiments, each instance of $R^C$ is selected from those depicted in Table 1, below.

As defined generally above, each instance of $R^1$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$.

In some embodiments, $R^D$ is oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$.

In some embodiments, $R^D$ is hydroxy, fluoro, or methoxy.
In some embodiments, $R^D$ is

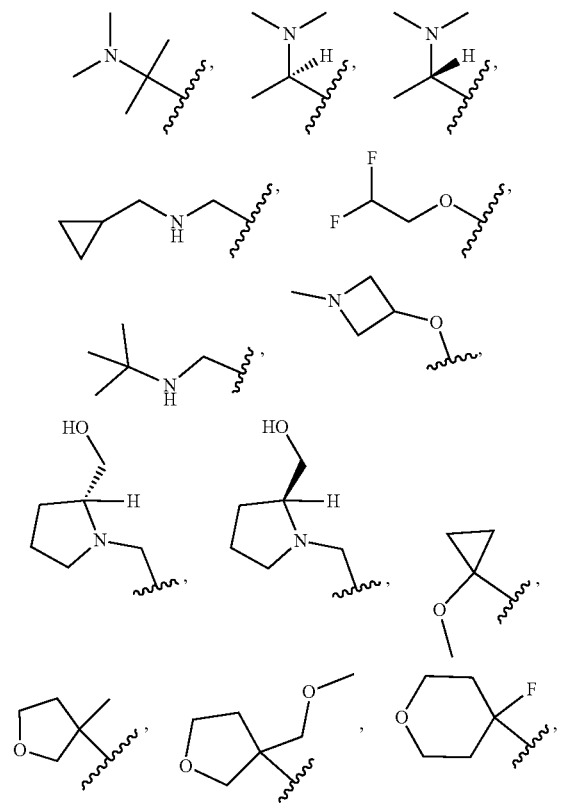

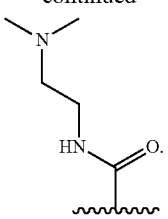

In some embodiments, $R^D$ is oxo.
In some embodiments, $R^D$ is

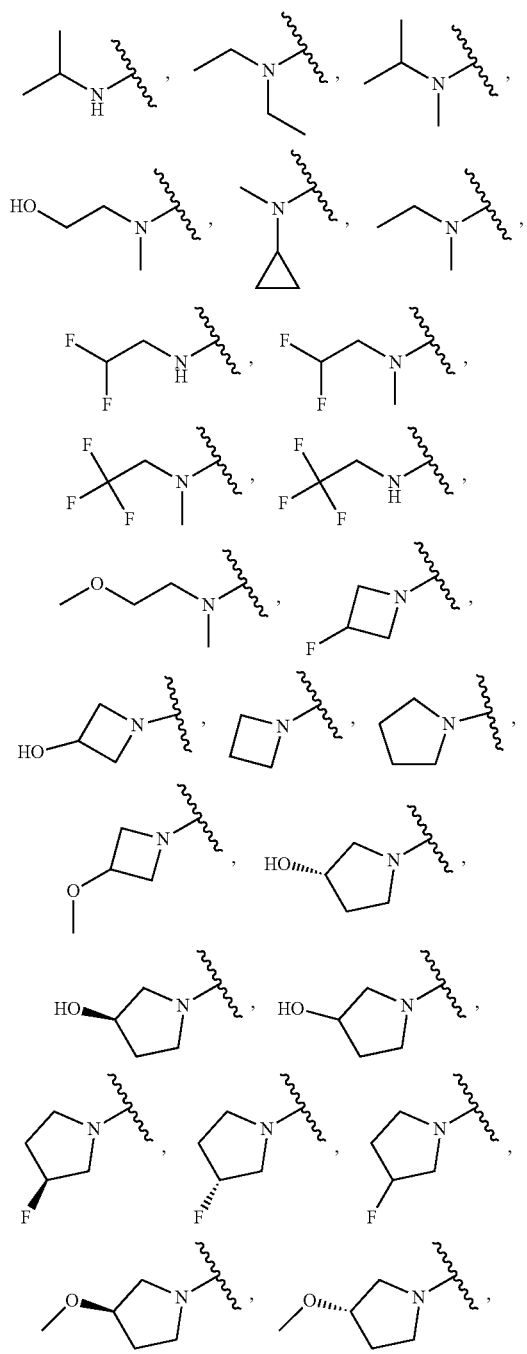

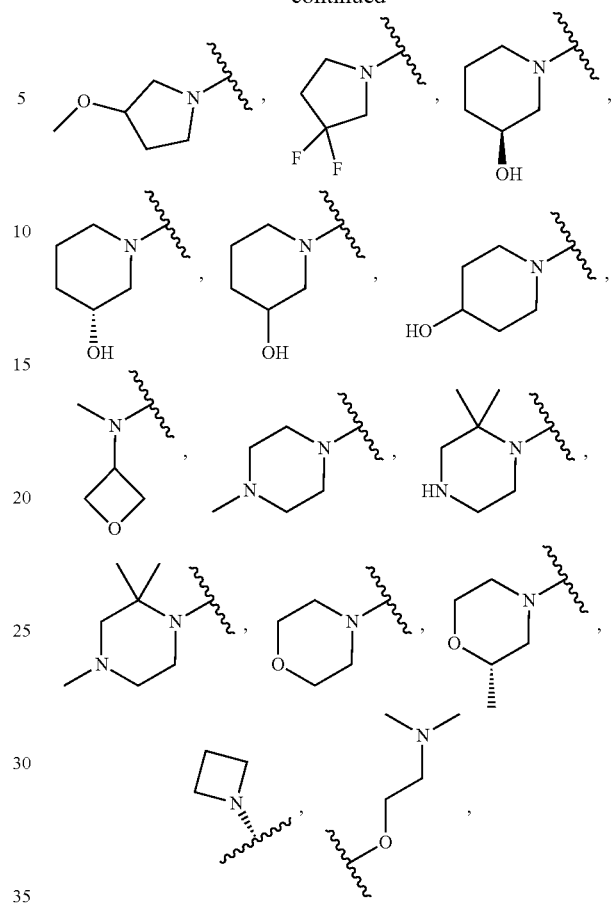

In some embodiments, $R^D$ is selected from those depicted in Table 1, below.

As defined generally above, each R is independently hydrogen, or an optionally substituted group selected from $C_{1-6}$ aliphatic; phenyl; naphthalenyl; a 3-7 membered saturated or partially unsaturated monocyclic carbocyclic ring; a 3-7 membered saturated or partially unsaturated monocyclic heterocyclic ring having 1-2 heteroatoms independently selected from nitrogen, oxygen, and sulfur; a 5-6 membered monocyclic heteroaryl ring having 1-4 heteroatoms independently selected from nitrogen, oxygen, and sulfur; an 8-10 membered bicyclic heteroaryl ring having 1-4 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur; a 5-8 membered saturated or partially unsaturated bridged bicyclic ring having 0-3 heteroatoms independently selected from nitrogen, oxygen, and sulfur; a 6-10 membered saturated or partially unsaturated spirocyclic ring having 0-3 heteroatoms independently selected from nitrogen, oxygen, and sulfur; a 6-11 membered saturated or partially unsaturated bicyclic carbocyclic ring having 1-2 heteroatoms independently selected from nitrogen, oxygen, and sulfur; or:
two R groups on the same nitrogen are taken together with the nitrogen to form an optionally substituted 4-7 membered monocyclic saturated, partially unsaturated, or heteroaryl ring having, in addition to the nitrogen, 0-3 heteroatoms independently selected from nitrogen, oxygen, and sulfur; an 8-10 membered bicyclic heteroaryl ring having 1-4 heteroatoms independently selected from nitrogen, oxygen, and sulfur; a 7-12 membered saturated or partially unsaturated bicyclic heterocyclic ring having 1-4 heteroatoms independently selected from nitrogen, oxygen, and sulfur.
In some embodiments, R is methyl. In some embodiments, R is
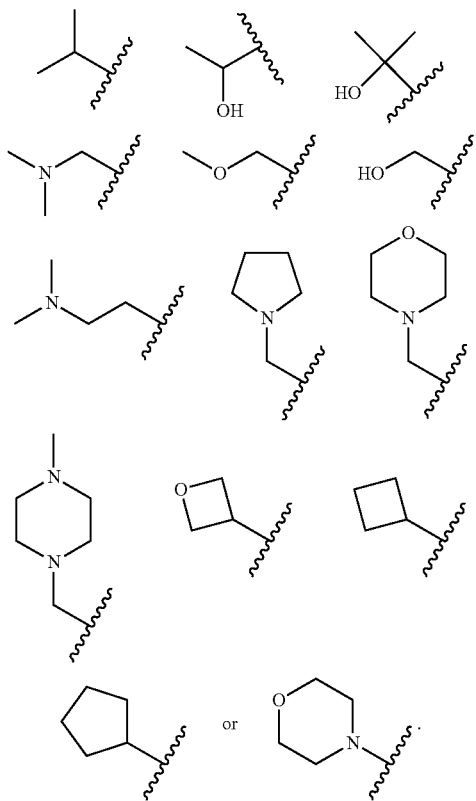
In some embodiments, R is ethyl.
In some embodiments, R is
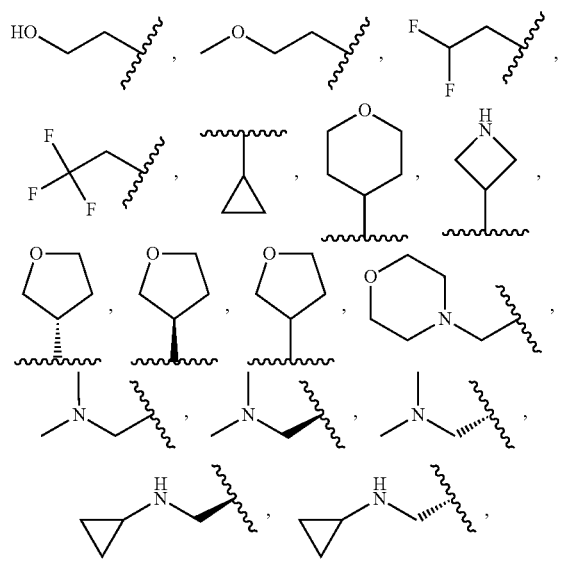
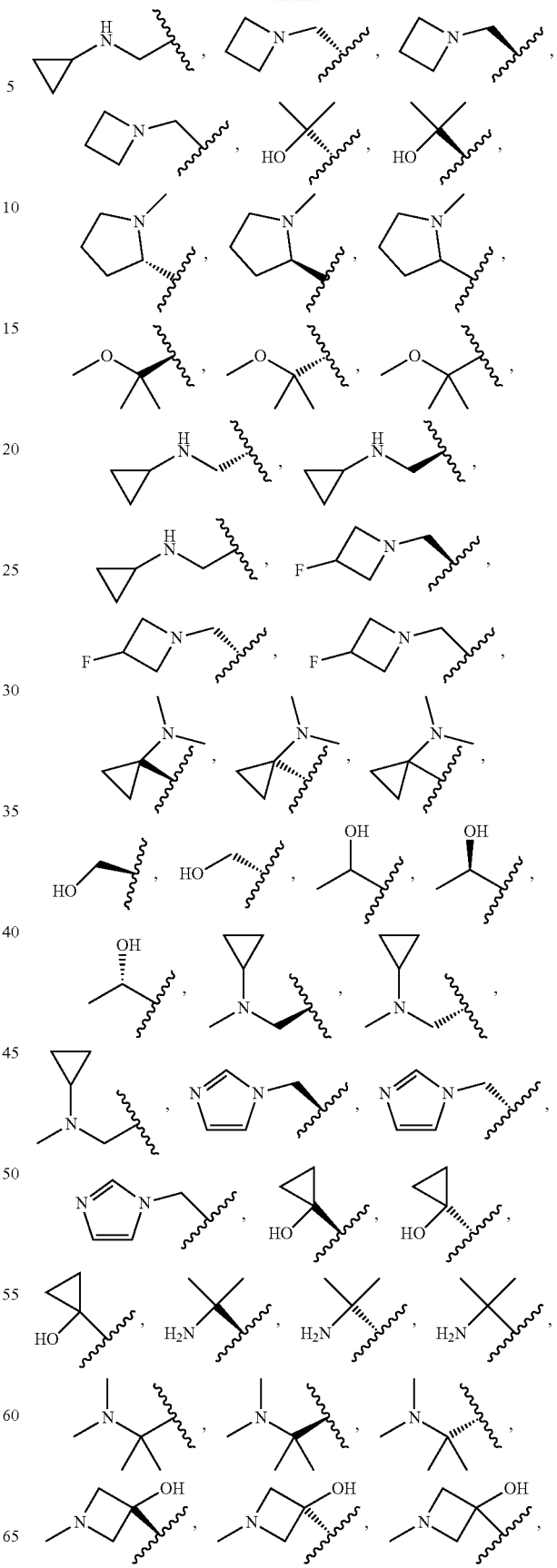

-continued

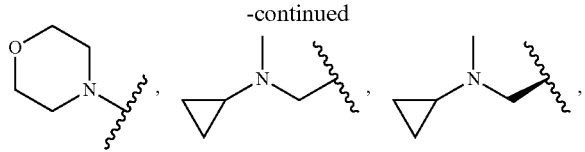

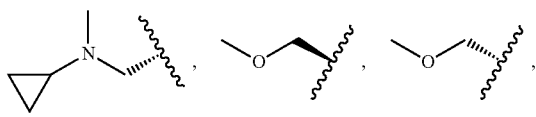

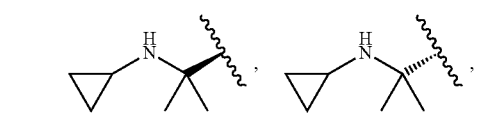

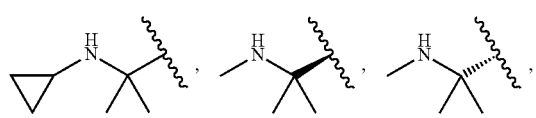

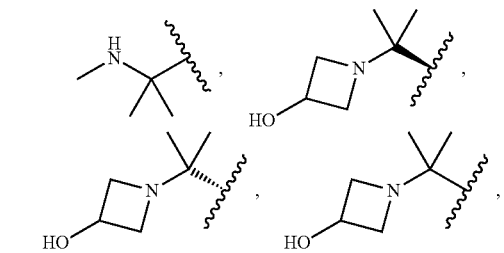

In some embodiments, R is selected from those depicted in Table 1, below.

As defined generally above, each hydrogen bound to carbon can be optionally and independently replaced by deuterium.

In some embodiments, a hydrogen bound to carbon is replaced by deuterium.

As defined generally above, m is 0, 1, or 2.

In some embodiments, m is 0. In some embodiments, m is 1. In some embodiments, m is 2.

In some embodiments, m is selected from those depicted in Table 1, below.

As defined generally above, q is 0, 1, 2, 3, or 4. In some embodiments, q is 0. In some embodiments, q is 1, 2, 3, or 4. In some embodiments, q is 1. In some embodiments, q is 2. In some embodiments, q is 3. In some embodiments, q is 4.

In some embodiments, q is 1, 2, or 3. In some embodiments, q is 1 or 2.

In some embodiments, q is selected from those depicted in Table 1, below.

As defined generally above, r is 0, 1, 2, 3, or 4. In some embodiments, r is 0. In some embodiments, r is 1, 2, 3, or 4. In some embodiments, r is 1. In some embodiments, r is 2. In some embodiments, r is 3. In some embodiments, r is 4.

In some embodiments, r is 1 or 2. In some embodiments, r is 2 or 3. In some embodiments, r is 2, 3, or 4.

In some embodiments, r is selected from those depicted in Table 1, below.

As defined generally above, s is 0, 1, 2, 3, or 4. In some embodiments, s is 0. In some embodiments, s is 1, 2, 3, or 4. In some embodiments, s is 1. In some embodiments, s is 2. In some embodiments, s is 3. In some embodiments, s is 4.

In some embodiments, s is 1 or 2. In some embodiments, s is 2 or 3. In some embodiments, s is 2, 3, or 4.

In some embodiments, s is selected from those depicted in Table 1, below.

In some embodiments, the present invention provides a compound of formula II:

II or a pharmaceutically acceptable salt thereof, wherein each of $R^1$ and $R^2$, is as defined above and described in embodiments herein, both singly and in combination.

In some embodiments, the present invention provides a compound of formula III:

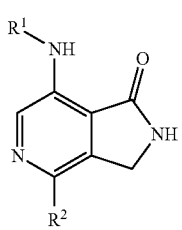

III or a pharmaceutically acceptable salt thereof, wherein each of $R^1$ and $R^2$, is as defined above and described in embodiments herein, both singly and in combination.

In some embodiments, the present invention provides a compound of formula IV:

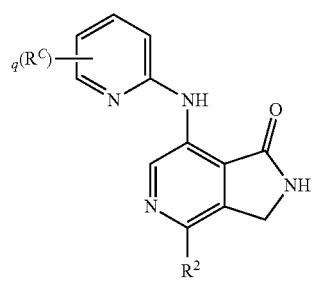

IV or a pharmaceutically acceptable salt thereof, wherein each of $R^2$ and $R^C$ is as defined above and described in embodiments herein, both singly and in combination.

In some embodiments, the present invention provides a compound of formula V:

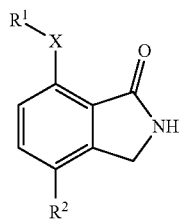

V or a pharmaceutically acceptable salt thereof, wherein each of $R^1$, $R^2$ and X, is as defined above and described in embodiments herein, both singly and in combination.

In some embodiments, the present invention provides a compound of formula VI:

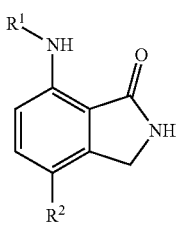

VI or a pharmaceutically acceptable salt thereof, wherein each of $R^1$ and $R^2$, is as defined above and described in embodiments herein, both singly and in combination.

In some embodiments, the present invention provides a compound of formula VII:

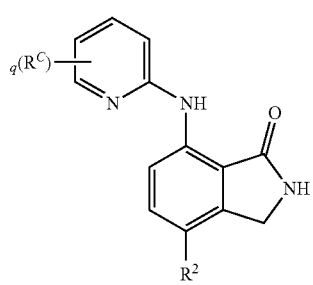

VII or a pharmaceutically acceptable salt thereof, wherein each of $R^2$ and $R^C$ is as defined above and described in embodiments herein, both singly and in combination.

In some embodiments, the present invention provides a compound of formula XI-a, or XI-b:

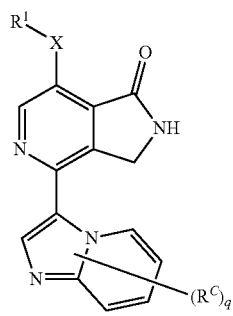

XI-a

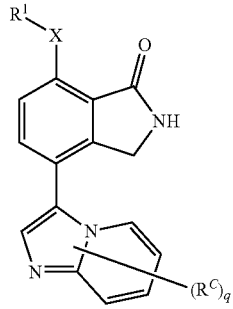

XI-b or a pharmaceutically acceptable salt thereof, wherein each of $R^1$, $R^C$, X, and q, is as defined above and described in embodiments herein, both singly and in combination.

In some embodiments, the present invention provides a compound of formula XII-a or XII-b:

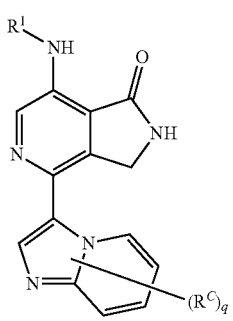

XII-a

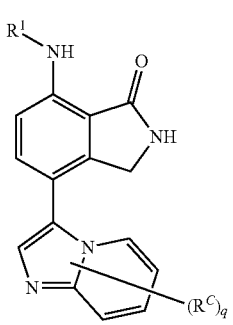

XII-b or a pharmaceutically acceptable salt thereof, wherein each of $R^1$, $R^C$ and q, is as defined above and described in embodiments herein, both singly and in combination.

In some embodiments, the present invention provides a compound of formula XIII-a or XIII-b:

XIII-a

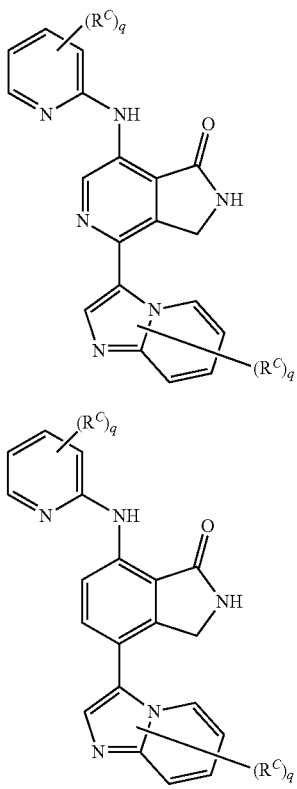

XIII-b

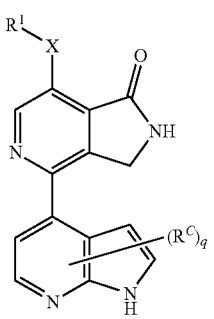

or a pharmaceutically acceptable salt thereof, wherein each of $R^C$ and q is as defined above and described in embodiments herein, both singly and in combination.

In some embodiments, the present invention provides a compound of formula XIV-a or XIV-b:

XIV-a

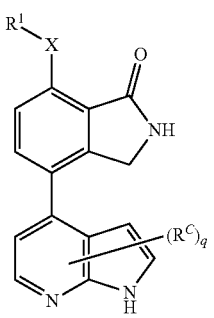

XIV-b or a pharmaceutically acceptable salt thereof, wherein each of $R^1$, $R^C$, X, and q, is as defined above and described in embodiments herein, both singly and in combination.

In some embodiments, the present invention provides a compound of formula XV-a or XV-b:

XV-a

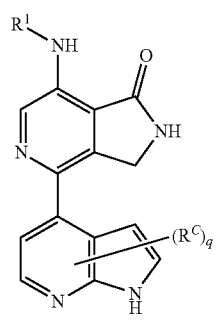

XV-b

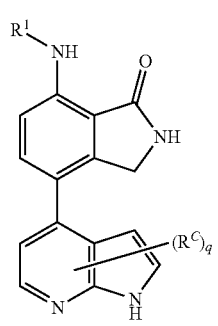

or a pharmaceutically acceptable salt thereof, wherein each of $R^1$, $R^C$ and q is as defined above and described in embodiments herein, both singly and in combination.

In some embodiments, the present invention provides a compound of formula XVI-a or XVI-b:

XVI-a

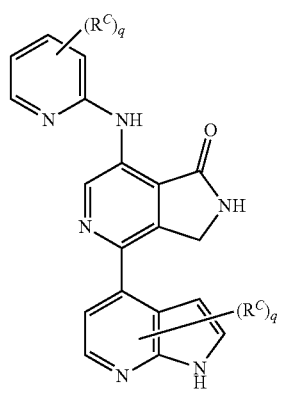

XVI-b

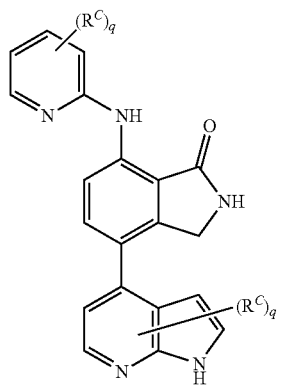

or a pharmaceutically acceptable salt thereof, wherein each of $R^C$ and q is as defined above and described in embodiments herein, both singly and in combination.

In some embodiments, the present invention provides a compound of formula XVII-a or XVII-b:

XVII-a

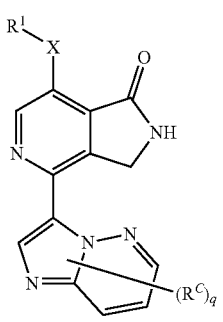

XVII-b

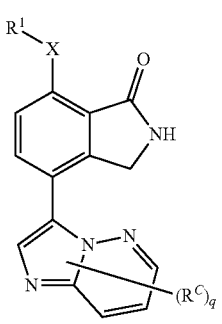

or a pharmaceutically acceptable salt thereof, wherein each of $R^1$, $R^C$, X, and q, is as defined above and described in embodiments herein, both singly and in combination.

In some embodiments, the present invention provides a compound of formula XVIII-a or XVIII-b:

XVIII-a

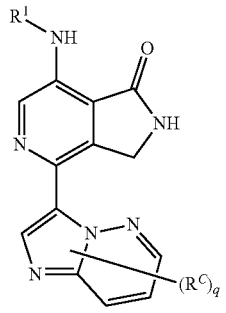

XVIII-b

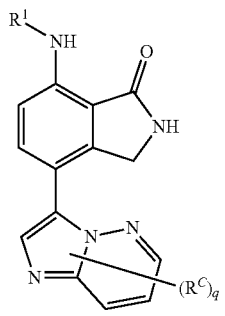

or a pharmaceutically acceptable salt thereof, wherein each of $R^1$, $R^C$ and q is as defined above and described in embodiments herein, both singly and in combination.

In some embodiments, the present invention provides a compound of formula XIX-a or XIX-b:

XIX-a

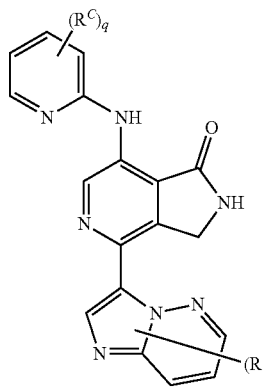

XIX-b

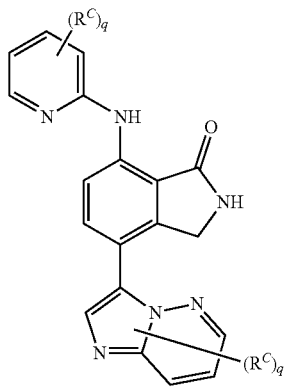

or a pharmaceutically acceptable salt thereof, wherein each of $R^C$ and q is as defined above and described in embodiments herein, both singly and in combination.

In some embodiments, the present invention provides a compound of formula XX-a or XX-b:

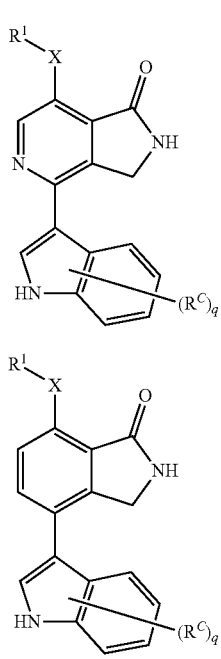

XX-a

XX-b or a pharmaceutically acceptable salt thereof, wherein each of $R^1$, $R^C$, X, and q, is as defined above and described in embodiments herein, both singly and in combination.

In some embodiments, the present invention provides a compound of formula XXI-a or XXI-b:

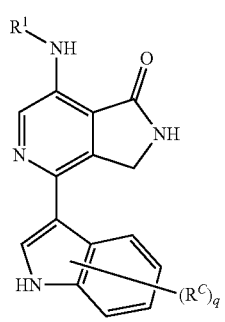

XXI-a

XXI-b or a pharmaceutically acceptable salt thereof, wherein each of $R^1$, $R^C$, X, and q, is as defined above and described in embodiments herein, both singly and in combination.

In some embodiments, the present invention provides a compound of formula XXII-a or XXII-b:

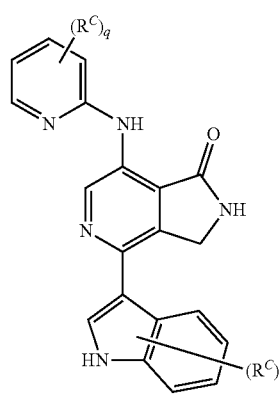

XXII-a

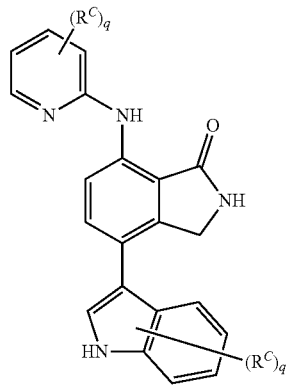

XXII-b or a pharmaceutically acceptable salt thereof, wherein each of $R^1$, $R^C$, X, and q, is as defined above and described in embodiments herein, both singly and in combination.

In some embodiments, the present invention provides a compound of formula XXIII-a or XXIII-b:

XXIII-a

-continued

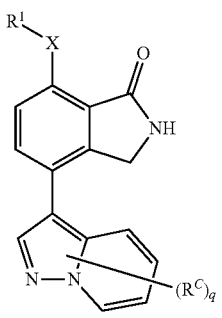

XXIII-b or a pharmaceutically acceptable salt thereof, wherein each of R¹, $R^C$, X, and q, is as defined above and described in embodiments herein, both singly and in combination.

In some embodiments, the present invention provides a compound of formula XXIV-a or XXIV-b:

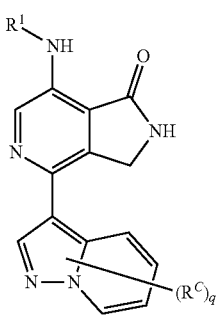

XXIV-a

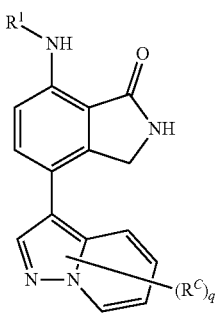

XXIV-b or a pharmaceutically acceptable salt thereof, wherein each of R¹, $R^C$, X, and q, is as defined above and described in embodiments herein, both singly and in combination.

In some embodiments, the present invention provides a compound of formula XXV-a or XXV-b:

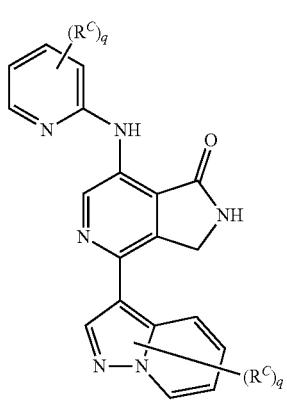

XXV-a

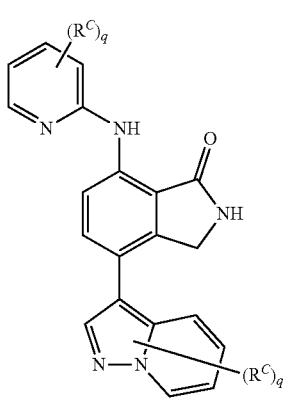

XXV-b or a pharmaceutically acceptable salt thereof, wherein each of R¹, $R^C$, X, and q, is as defined above and described in embodiments herein, both singly and in combination.

In some embodiments, the present invention provides a compound of formula XXVI-a or XXVI-b:

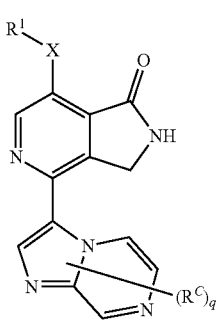

XXVI-a

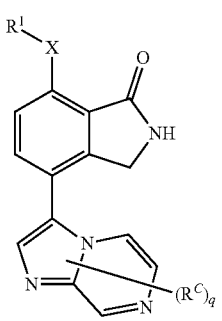

XXVI-b or a pharmaceutically acceptable salt thereof, wherein each of $R^1$, $R^C$, X, and q, is as defined above and described in embodiments herein, both singly and in combination.

In some embodiments, the present invention provides a compound of formula XXVII-a or XXVII-b:

XXVII-a

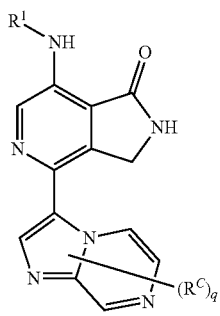

XXVII-b

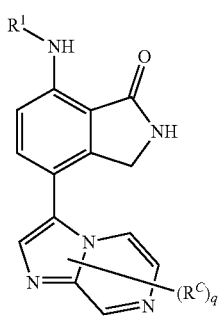

or a pharmaceutically acceptable salt thereof, wherein each of $R^1$, $R^C$, X, and q, is as defined above and described in embodiments herein, both singly and in combination.

In some embodiments, the present invention provides a compound of formula XXVIII-a or XXVIII-b:

XXVIII-a

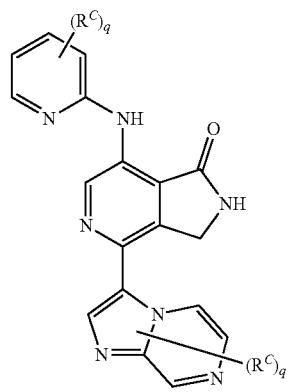

XXVIII-b

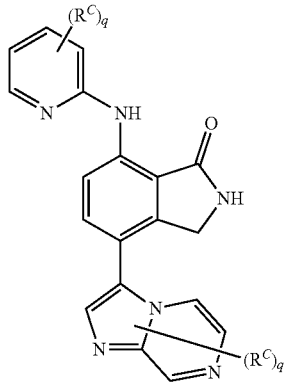

or a pharmaceutically acceptable salt thereof, wherein each of $R^1$, $R^C$, X, and q, is as defined above and described in embodiments herein, both singly and in combination.

In some embodiments, the present invention provides a compound of formula XXIX-a or XXIX-b:

XXIX-a

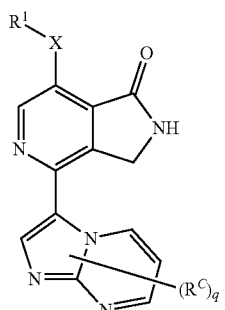

XXIX-b

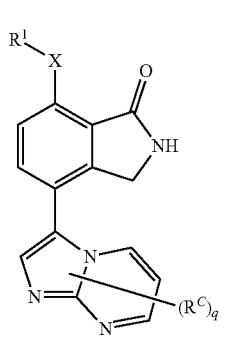

or a pharmaceutically acceptable salt thereof, wherein each of $R^1$, $R^C$, X, and q, is as defined above and described in embodiments herein, both singly and in combination.

In some embodiments, the present invention provides a compound of formula XXX-a or XXX-b:

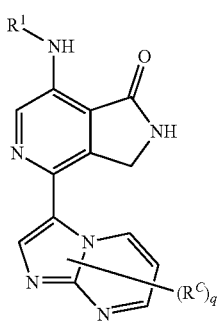

XXX-a

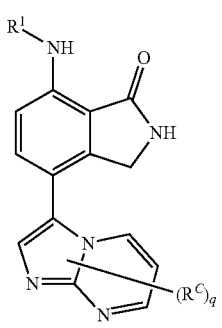

XXX-b


XXXI-a


XXXI-b or a pharmaceutically acceptable salt thereof, wherein each of R', $R^C$, X, and q, is as defined above and described in embodiments herein, both singly and in combination.

In some embodiments, the present invention provides a compound of formula XXXI-a or XXXI-b:

or a pharmaceutically acceptable salt thereof, wherein each of $R^1$, $R^C$, X, and q, is as defined above and described in embodiments herein, both singly and in combination.

Exemplary compounds of the invention are set forth in Table 1, below.

TABLE 1

| Selected Compounds | |
|---|---|
| # | Structure |
| I-1 | |

TABLE 1-continued
Selected Compounds
| # | Structure |
|---|---|
| I-2 | 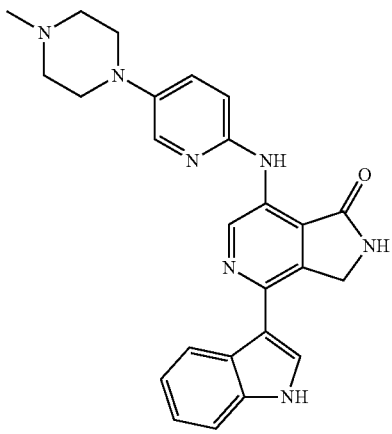 [SMILES: CN1CCN(c2ccc(Nc3cnc(-c4c[nH]c5ccccc45)c4c3C(=O)NC4)nc2)CC1] |
| I-3 | 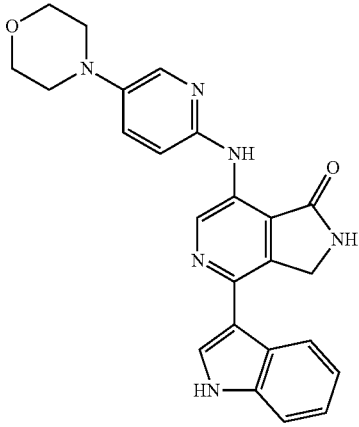 [SMILES: O=C1NCc2c(-c3c[nH]c4ccccc34)ncc(Nc3ccc(N4CCOCC4)cn3)c21] |
| I-4 | 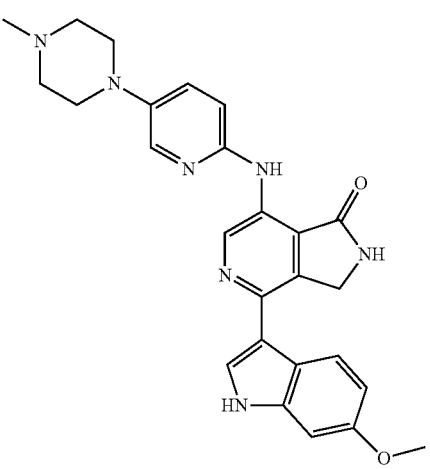 |

TABLE 1-continued
| Selected Compounds | |
|---|---|
| # | Structure |
| I-5 | 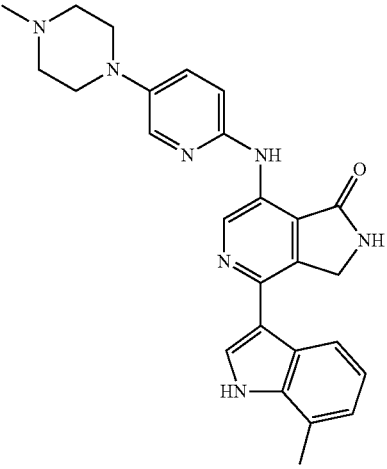 [SMILES: Cc1cccc2c(-c3ncc(Nc4ccc(N5CCN(C)CC5)cn4)c4c3CNC4=O)c[nH]c12] |
| I-6 | 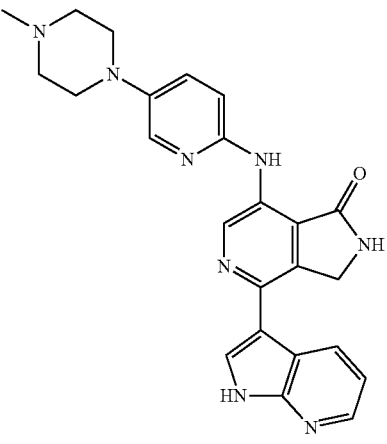 [SMILES: CN1CCN(c2ccc(Nc3cnc(-c4c[nH]c5ncccc45)c4c3C(=O)NC4)nc2)CC1] |
| I-7 | 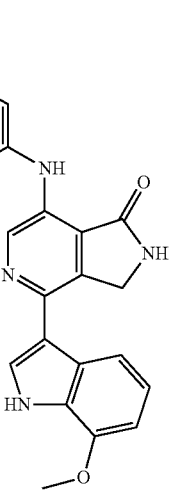 |

TABLE 1-continued
| | Selected Compounds |
|---|---|
| # | Structure |
| I-8 | 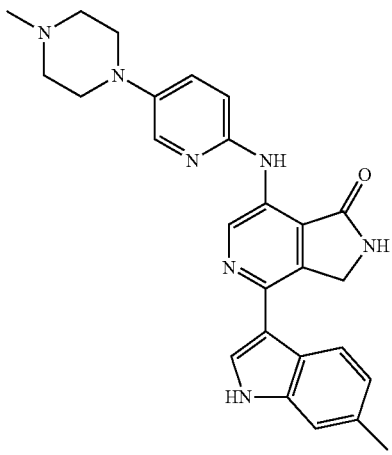 |
| I-9 | 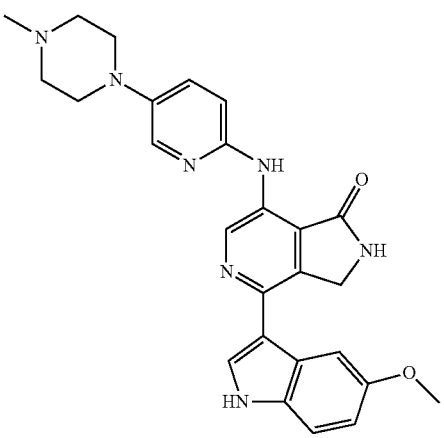 |
| I-10 | 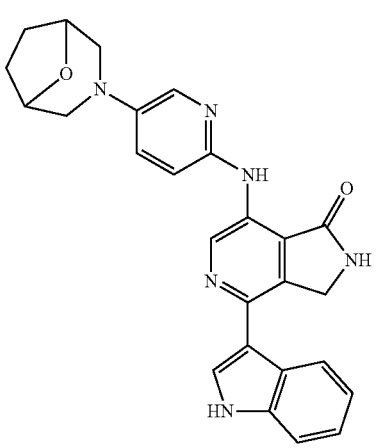 [SMILES: O=C1NCc2c(-c3c[nH]c4ccccc34)ncc(Nc3ccc(N4CC5CCC(C4)O5)cn3)c21] |

TABLE 1-continued

Selected Compounds

| # | Structure |
|---|---|
| I-11 | 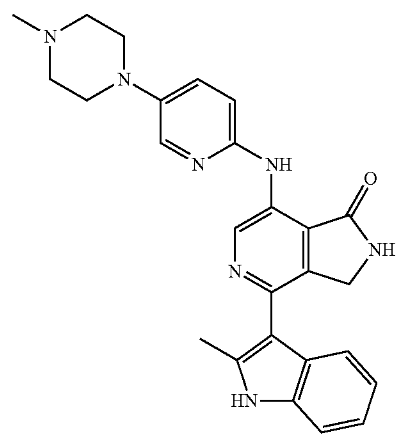 [SMILES: Cc1[nH]c2ccccc2c1-c1ncc(Nc2ccc(N3CCN(C)CC3)cn2)c2c1CNC2=O] |
| I-12 | 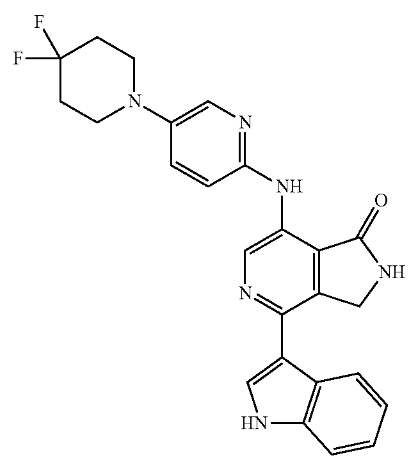 [SMILES: O=C1NCc2c(-c3c[nH]c4ccccc34)ncc(Nc3ccc(N4CCC(F)(F)CC4)cn3)c21] |
| I-13 | 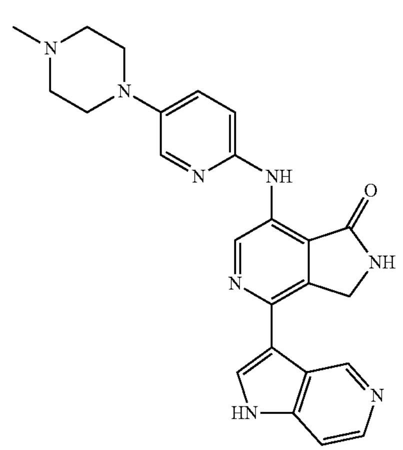 [SMILES: CN1CCN(c2ccc(Nc3cnc(-c4c[nH]c5ccncc45)c4c3C(=O)NC4)nc2)CC1] |

151
TABLE 1-continued
Selected Compounds
| # | Structure |
|---|---|
| I-14 | 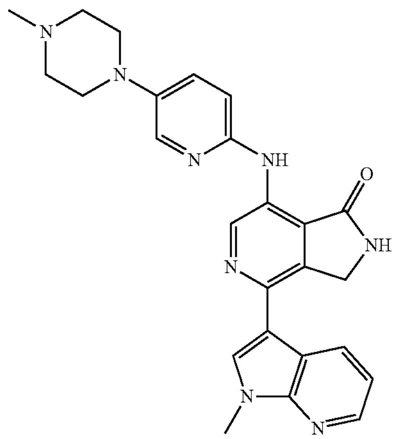 [SMILES: CN1CCN(c2ccc(Nc3cnc(-c4cn(C)c5ncccc45)c4c3C(=O)NC4)nc2)CC1] |
| I-15 | 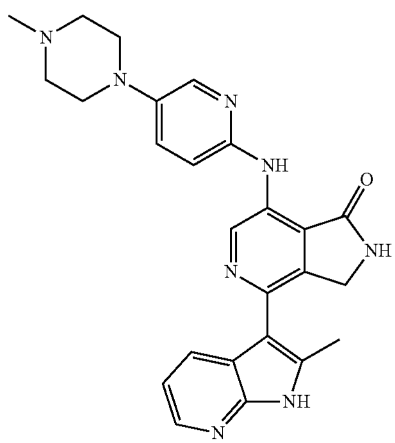 [SMILES: Cc1[nH]c2ncccc2c1-c1ncc(Nc2ccc(N3CCN(C)CC3)cn2)c2c1CNC2=O] |
| I-16 | 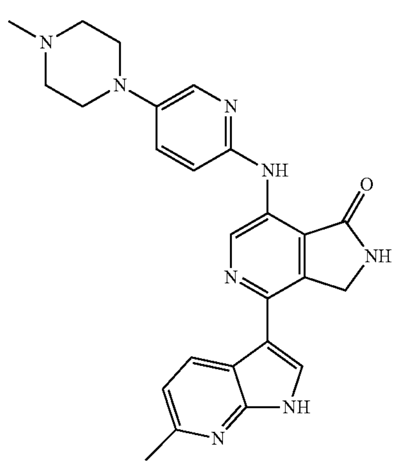 [SMILES: Cc1ccc2c(-c3ncc(Nc4ccc(N5CCN(C)CC5)cn4)c4c3CNC4=O)c[nH]c2n1] |

TABLE 1-continued
Selected Compounds
| # | Structure |
|---|---|
| I-17 | 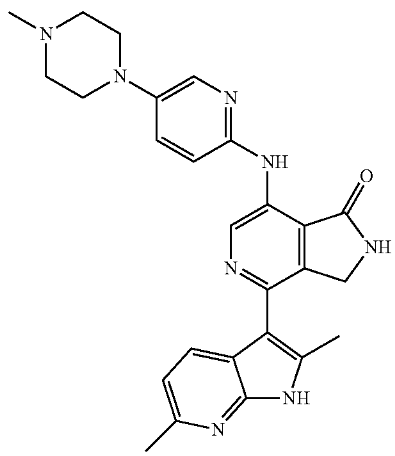 [SMILES: Cc1ccc2c(-c3ncc(Nc4ccc(N5CCN(C)CC5)cn4)c4c3CNC4=O)c(C)[nH]c2n1] |
| I-18 | 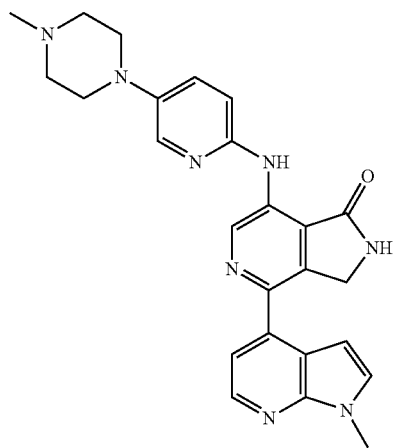 [SMILES: CN1CCN(c2ccc(Nc3cnc(-c4ccnc5c4ccn5C)c4c3C(=O)NC4)nc2)CC1] |
| I-19 | 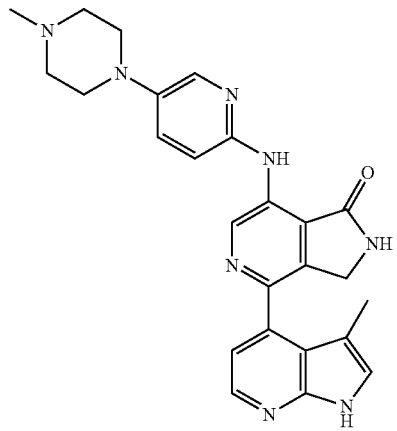 [SMILES: Cc1c[nH]c2nccc(-c3ncc(Nc4ccc(N5CCN(C)CC5)cn4)c4c3CNC4=O)c12] |

TABLE 1-continued
| Selected Compounds | |
|---|---|
| # | Structure |
| I-20 | 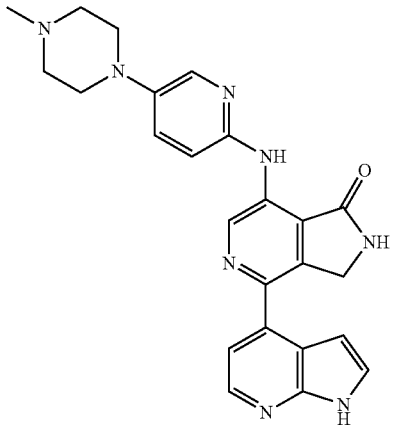 [SMILES: CN1CCN(c2ccc(Nc3cnc(-c4ccnc5[nH]ccc45)c4c3C(=O)NC4)nc2)CC1] |
| I-21 | 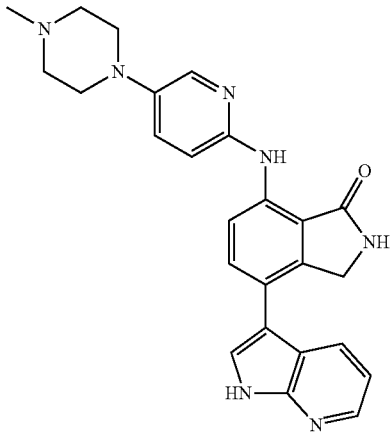 [SMILES: CN1CCN(c2ccc(Nc3ccc(-c4c[nH]c5ncccc45)c4c3C(=O)NC4)nc2)CC1] |
| I-22 | 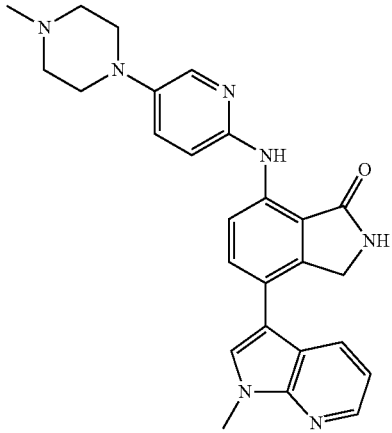 [SMILES: CN1CCN(c2ccc(Nc3ccc(-c4cn(C)c5ncccc45)c4c3C(=O)NC4)nc2)CC1] |

TABLE 1-continued
| Selected Compounds | |
|---|---|
| # | Structure |
| I-23 | 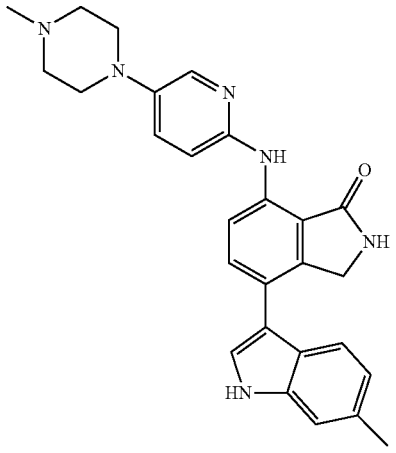 |
| I-24 | 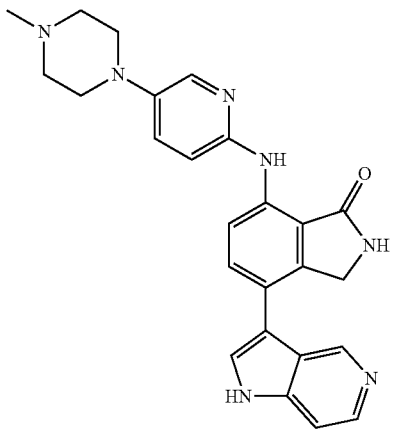 [SMILES: CN1CCN(c2ccc(Nc3ccc(-c4c[nH]c5ccncc45)c4c3C(=O)NC4)nc2)CC1] |
| I-25 | 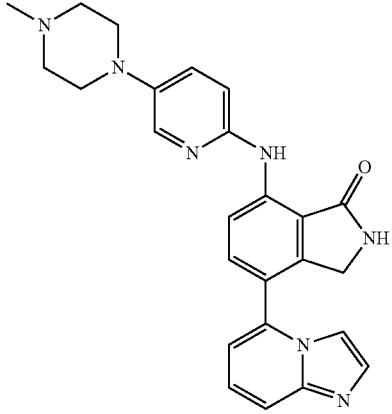 [SMILES: CN1CCN(c2ccc(Nc3ccc(-c4cccc5nccn45)c4c3C(=O)NC4)nc2)CC1] |

TABLE 1-continued
Selected Compounds
| # | Structure |
|---|---|
| I-26 | 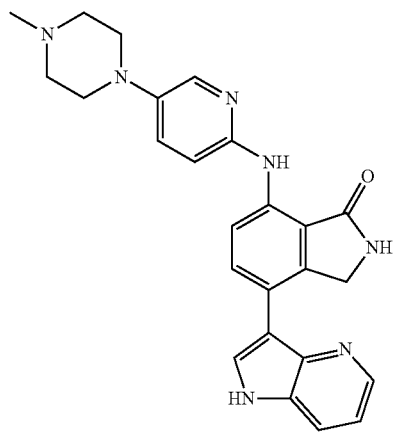 [SMILES: CN1CCN(c2ccc(Nc3ccc(-c4c[nH]c5cccnc45)c4c3C(=O)NC4)nc2)CC1] |
| I-27 | 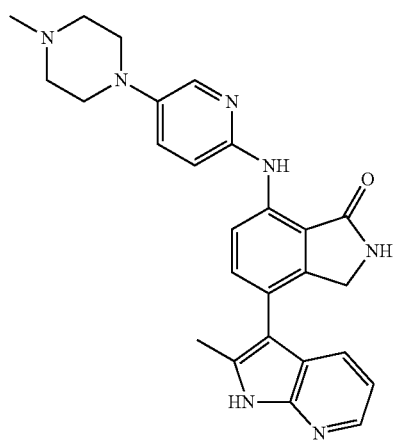 [SMILES: Cc1[nH]c2ncccc2c1-c1ccc(Nc2ccc(N3CCN(C)CC3)cn2)c2c1CNC2=O] |
| I-28 | 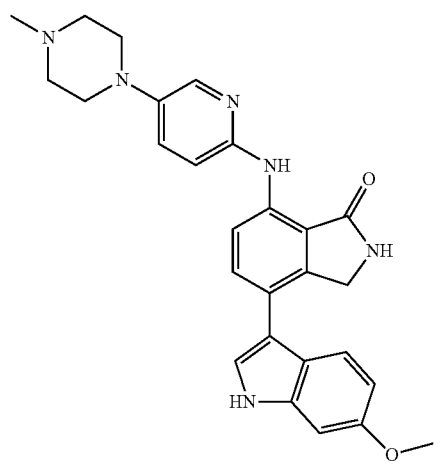 |

TABLE 1-continued
Selected Compounds
| # | Structure |
|---|---|
| I-29 | 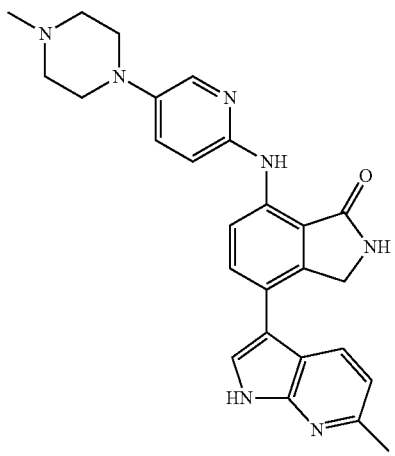 |
| I-30 | 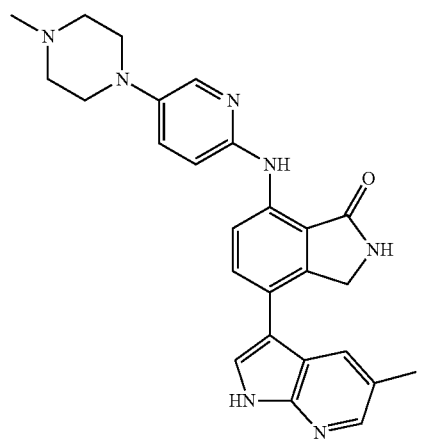 |
| I-31 | 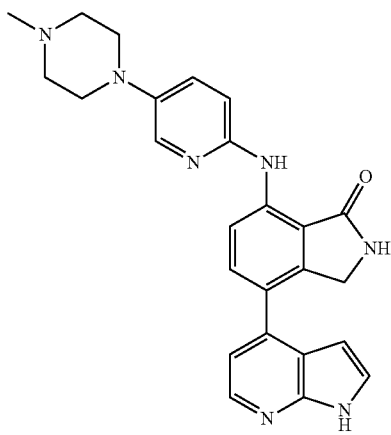 [SMILES: CN1CCN(c2ccc(Nc3ccc(-c4ccnc5[nH]ccc45)c4c3C(=O)NC4)nc2)CC1] |

TABLE 1-continued

Selected Compounds

| # | Structure |
|---|---|
| I-32 | 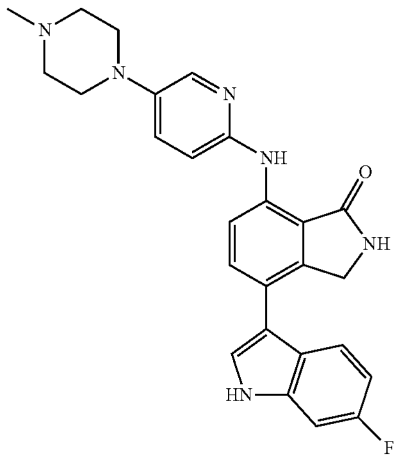 [SMILES: CN1CCN(c2ccc(Nc3ccc(-c4c[nH]c5cc(F)ccc45)c4c3C(=O)NC4)nc2)CC1] |
| I-33 | 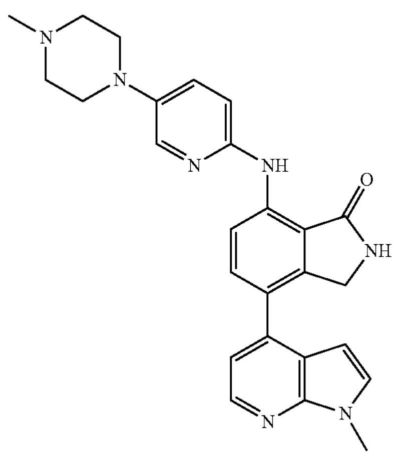 [SMILES: CN1CCN(c2ccc(Nc3ccc(-c4ccnc5c4ccn5C)c4c3C(=O)NC4)nc2)CC1] |
| I-34 | 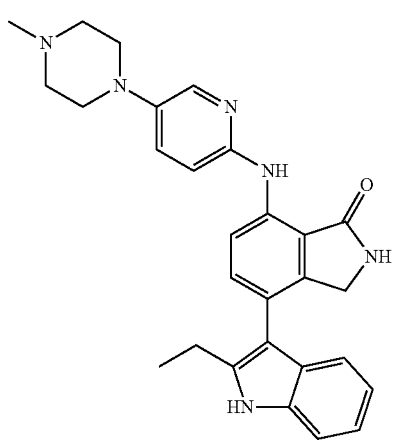 [SMILES: CCc1[nH]c2ccccc2c1-c1ccc(Nc2ccc(N3CCN(C)CC3)cn2)c2c1CNC2=O] |

TABLE 1-continued
| Selected Compounds | |
|---|---|
| # | Structure |
I-35
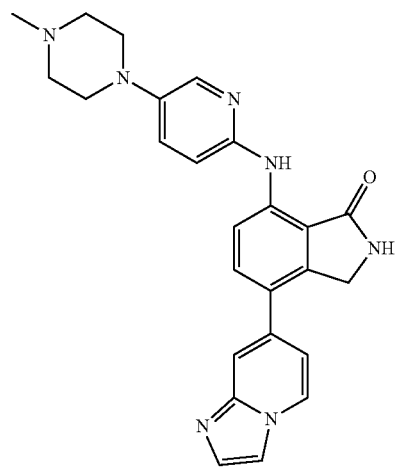 [SMILES: CN1CCN(c2ccc(Nc3ccc(-c4ccn5ccnc5c4)c4c3C(=O)NC4)nc2)CC1]
I-36
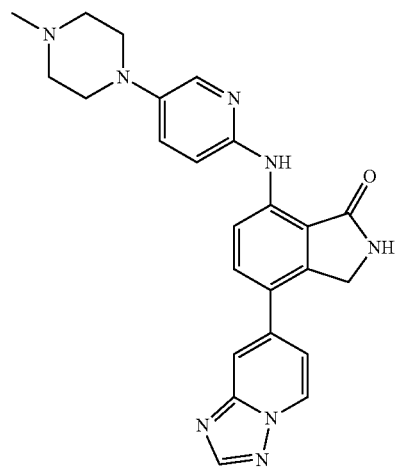 [SMILES: CN1CCN(c2ccc(Nc3ccc(-c4ccn5ncnc5c4)c4c3C(=O)NC4)nc2)CC1]
I-37
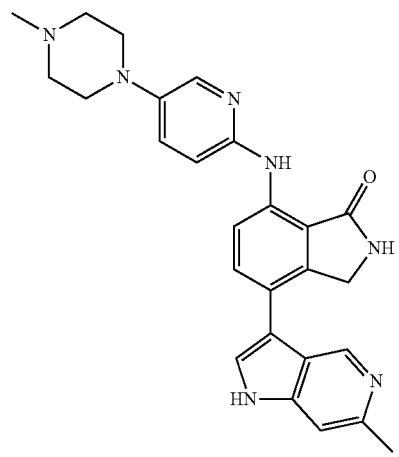

TABLE 1-continued
Selected Compounds
| # | Structure |
|---|---|
| I-38 | 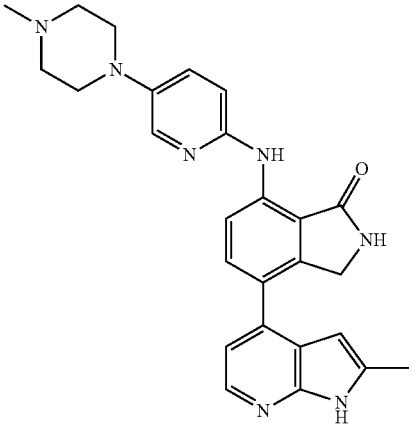 |
| I-39 | 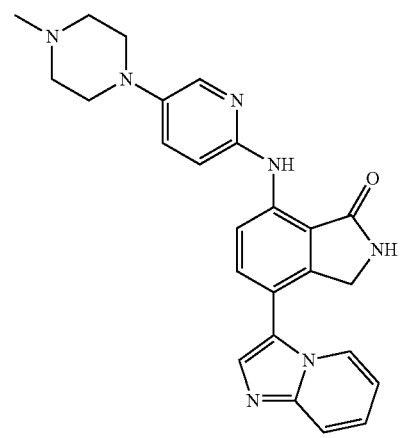 [SMILES: CN1CCN(c2ccc(Nc3ccc(-c4cnc5ccccn45)c4c3C(=O)NC4)nc2)CC1] |
| I-40 | 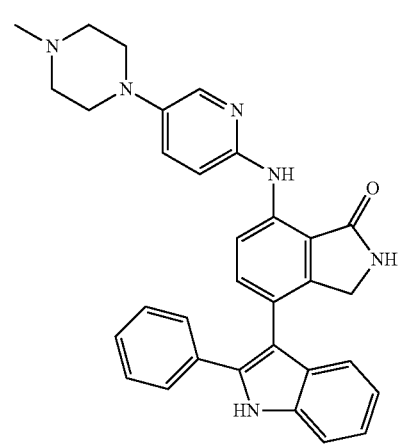 [SMILES: CN1CCN(c2ccc(Nc3ccc(-c4c(-c5ccccc5)[nH]c5ccccc45)c4c3C(=O)NC4)nc2)CC1] |

TABLE 1-continued
Selected Compounds
| # | Structure |
|---|---|
| I-41 | 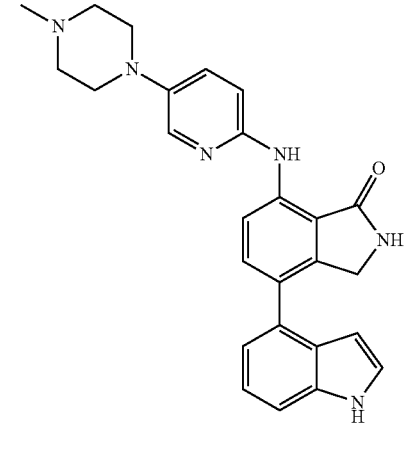 [SMILES: CN1CCN(c2ccc(Nc3ccc(-c4cccc5[nH]ccc45)c4c3C(=O)NC4)nc2)CC1] |
| I-42 | 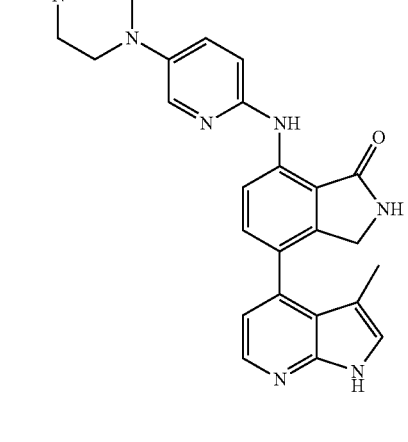 |
| I-43 | 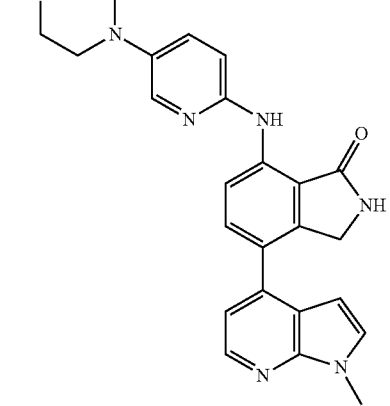 |

TABLE 1-continued
Selected Compounds
| # | Structure |
|---|---|
| I-44 | 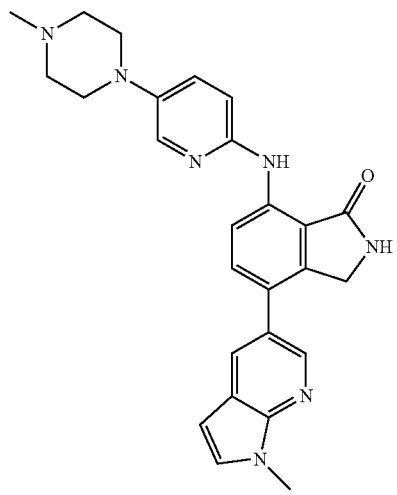 [SMILES: CN1CCN(c2ccc(Nc3ccc(-c4cnc5c(ccn5C)c4)c4c3C(=O)NC4)nc2)CC1] |
| I-45 | 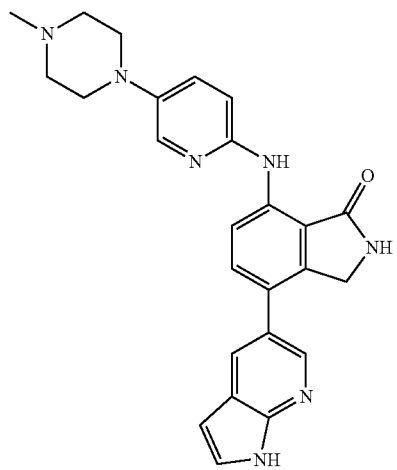 [SMILES: CN1CCN(c2ccc(Nc3ccc(-c4cnc5[nH]ccc5c4)c4c3C(=O)NC4)nc2)CC1] |
| I-46 | 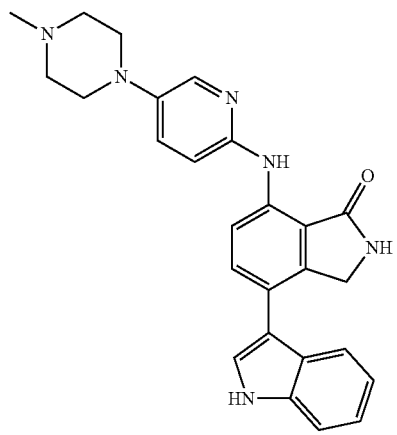 [SMILES: CN1CCN(c2ccc(Nc3ccc(-c4c[nH]c5ccccc45)c4c3C(=O)NC4)nc2)CC1] |

TABLE 1-continued
| | Selected Compounds |
|---|---|
| # | Structure |
| I-47 | 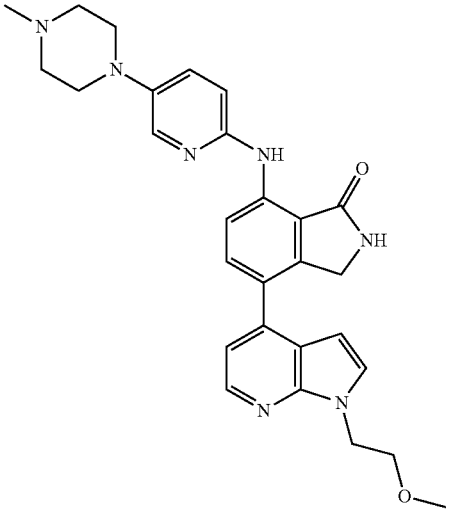 |
| I-48 | 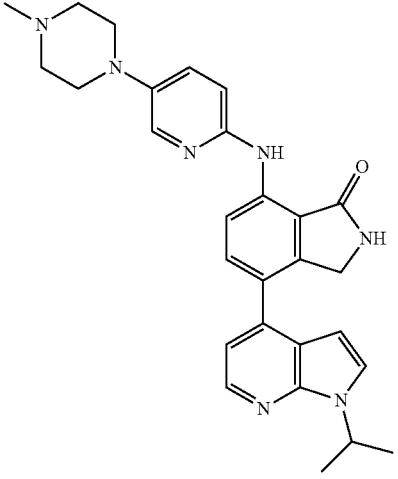 [SMILES: CC(C)n1ccc2c(-c3ccc(Nc4ccc(N5CCN(C)CC5)cn4)c4c3CNC4=O)ccnc21] |
| I-49 | 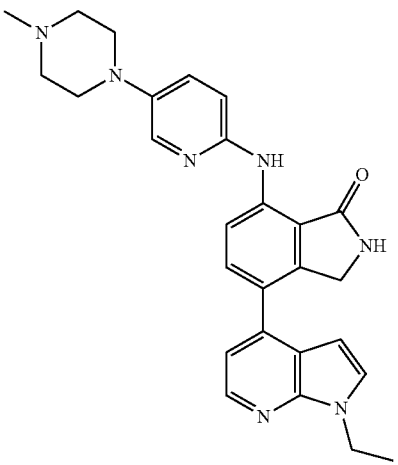 [SMILES: CCn1ccc2c(-c3ccc(Nc4ccc(N5CCN(C)CC5)cn4)c4c3CNC4=O)ccnc21] |

TABLE 1-continued
Selected Compounds
| # | Structure |
|---|---|
| I-50 | 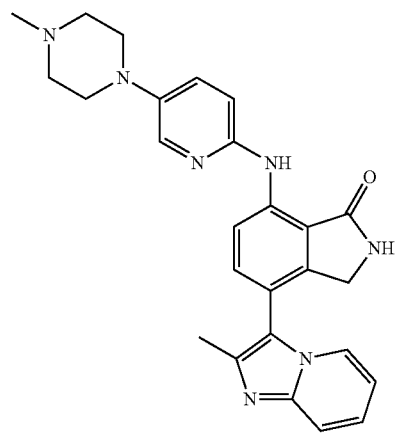 [SMILES: Cc1nc2ccccn2c1-c1ccc(Nc2ccc(N3CCN(C)CC3)cn2)c2c1CNC2=O] |
| I-51 | 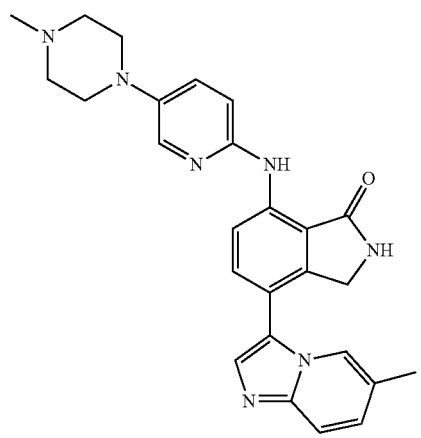 |
| I-52 | 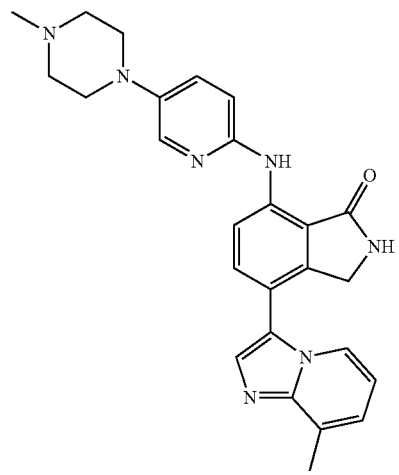 [SMILES: Cc1cccn2c(-c3ccc(Nc4ccc(N5CCN(C)CC5)cn4)c4c3CNC4=O)cnc12] |

TABLE 1-continued
Selected Compounds
| # | Structure |
|---|---|
| I-53 | 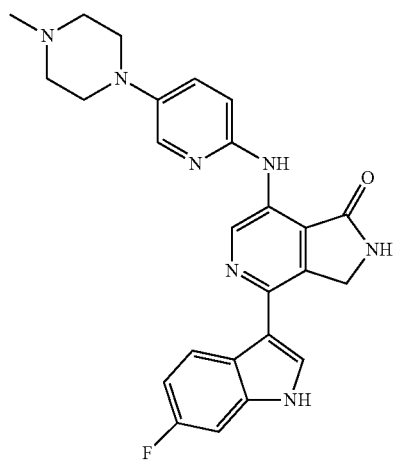 [SMILES: CN1CCN(c2ccc(Nc3cnc(-c4c[nH]c5cc(F)ccc45)c4c3C(=O)NC4)nc2)CC1] |
| I-54 | 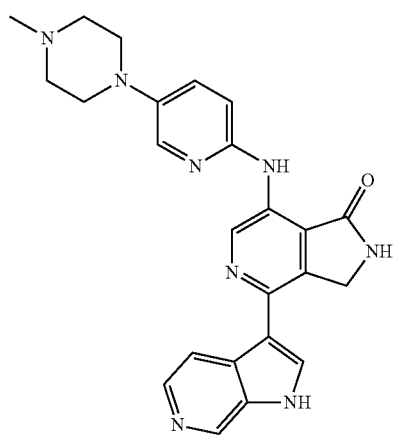 [SMILES: CN1CCN(c2ccc(Nc3cnc(-c4c[nH]c5cnccc45)c4c3C(=O)NC4)nc2)CC1] |
| I-55 | 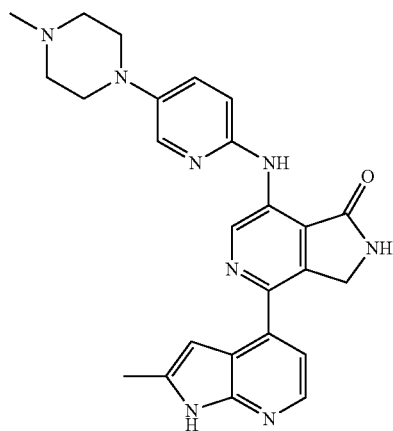 [SMILES: Cc1cc2c(-c3ncc(Nc4ccc(N5CCN(C)CC5)cn4)c4c3CNC4=O)ccnc2[nH]1] |

TABLE 1-continued
| | Selected Compounds |
|---|---|
| # | Structure |
I-56
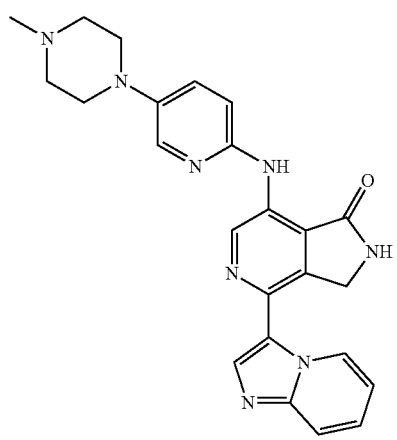 [SMILES: CN1CCN(c2ccc(Nc3cnc(-c4cnc5ccccn45)c4c3C(=O)NC4)nc2)CC1]
I-57
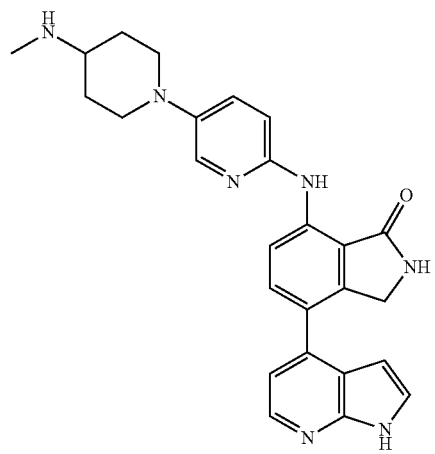 [SMILES: CNC1CCN(c2ccc(Nc3ccc(-c4ccnc5[nH]ccc45)c4c3C(=O)NC4)nc2)CC1]
I-58
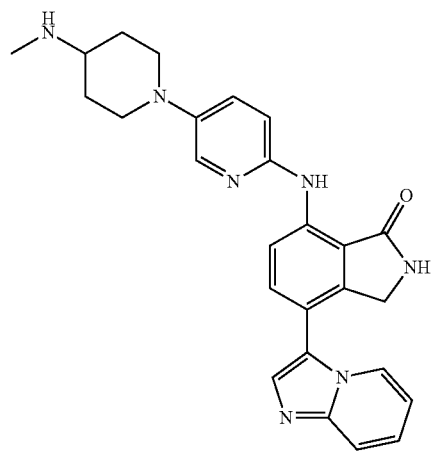 [SMILES: CNC1CCN(c2ccc(Nc3ccc(-c4cnc5ccccn45)c4c3C(=O)NC4)nc2)CC1]

TABLE 1-continued
Selected Compounds
| # | Structure |
|---|---|
| I-59 | 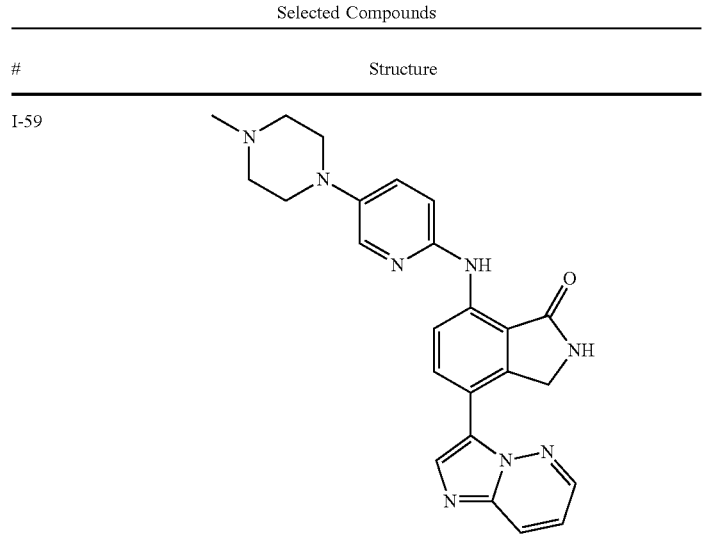 |
| I-60 | 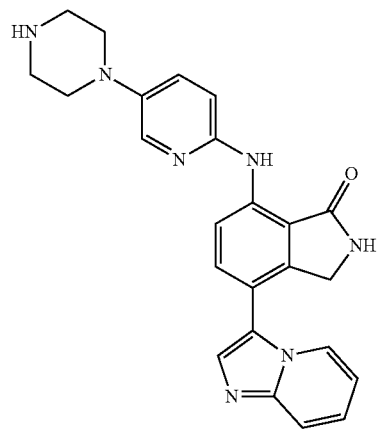 |
| I-61 | 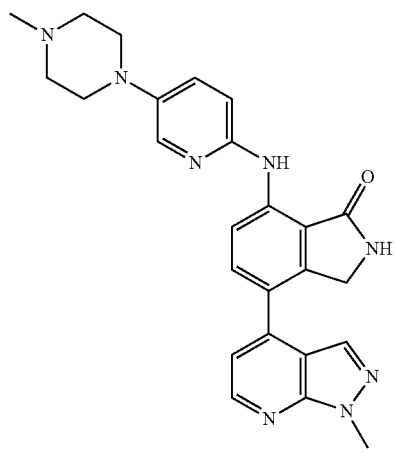 [SMILES: CN1CCN(c2ccc(Nc3ccc(-c4ccnc5c4cnn5C)c4c3C(=O)NC4)nc2)CC1] |

TABLE 1-continued
Selected Compounds
| # | Structure |
|---|---|
| I-62 | 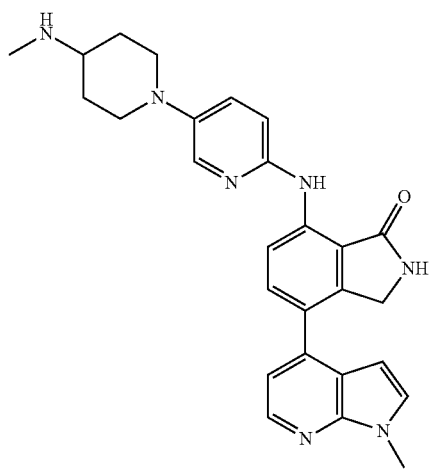 [SMILES: CNC1CCN(c2ccc(Nc3ccc(-c4ccnc5c4ccn5C)c4c3C(=O)NC4)nc2)CC1] |
| I-63 | 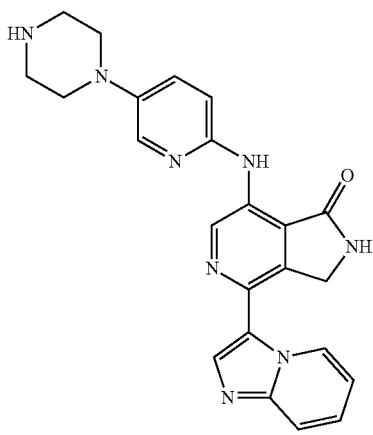 [SMILES: O=C1NCc2c(-c3cnc4ccccn34)ncc(Nc3ccc(N4CCNCC4)cn3)c21] |
| I-64 | 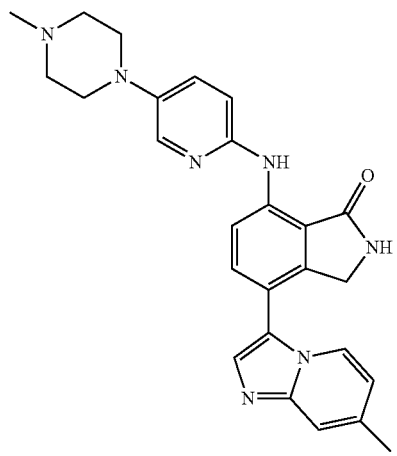 |

TABLE 1-continued
Selected Compounds
| # | Structure |
|---|---|
| I-65 | 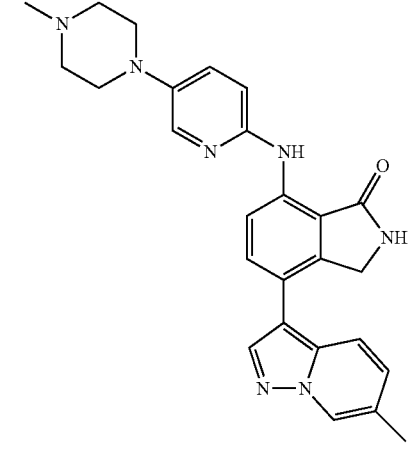 |
| I-66 | 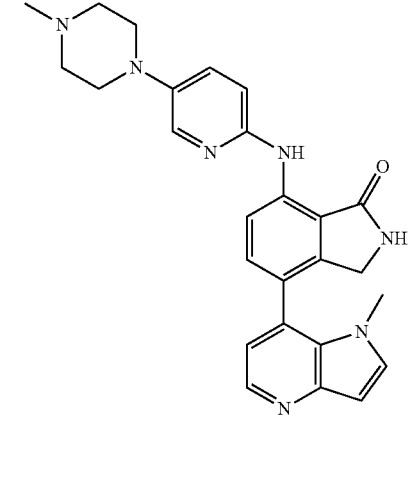 [SMILES: CN1CCN(c2ccc(Nc3ccc(-c4ccnc5ccn(C)c45)c4c3C(=O)NC4)nc2)CC1] |
| I-67 | 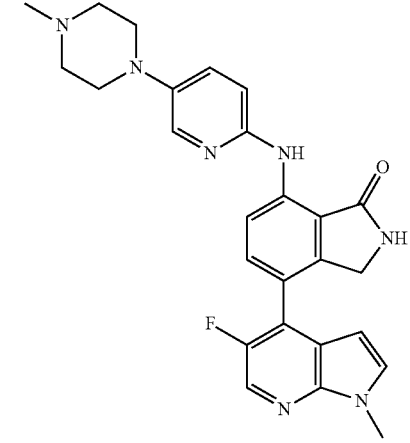 [SMILES: CN1CCN(c2ccc(Nc3ccc(-c4c(F)cnc5c4ccn5C)c4c3C(=O)NC4)nc2)CC1] |

TABLE 1-continued
Selected Compounds
| # | Structure |
|---|---|
| I-68 | 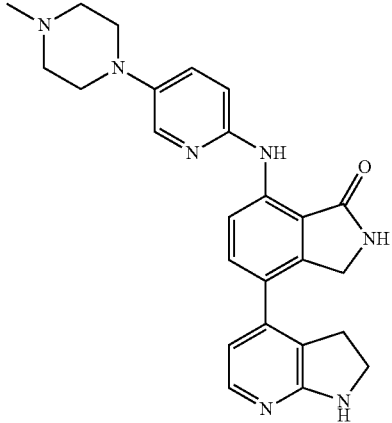 [SMILES: CN1CCN(c2ccc(Nc3ccc(-c4ccnc5c4CCN5)c4c3C(=O)NC4)nc2)CC1] |
| I-69 | 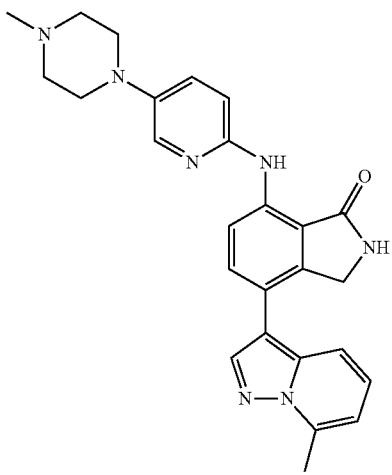 [SMILES: Cc1cccc2c(-c3ccc(Nc4ccc(N5CCN(C)CC5)cn4)c4c3CNC4=O)cnn12] |
| I-70 | 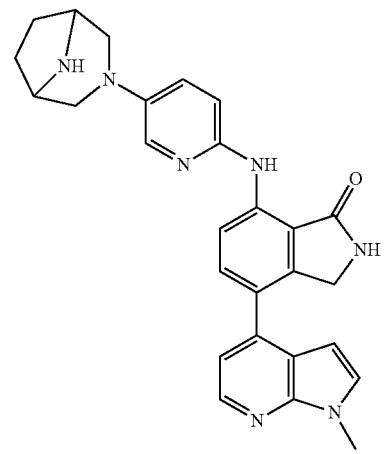 [SMILES: Cn1ccc2c(-c3ccc(Nc4ccc(N5CC6CCC(C5)N6)cn4)c4c3CNC4=O)ccnc21] |

TABLE 1-continued
| Selected Compounds | |
|---|---|
| # | Structure |
| I-71 | 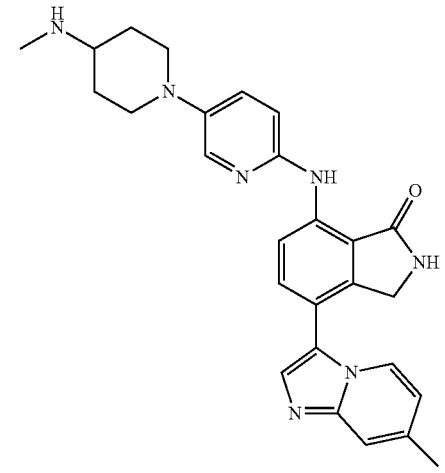 |
| I-72 | 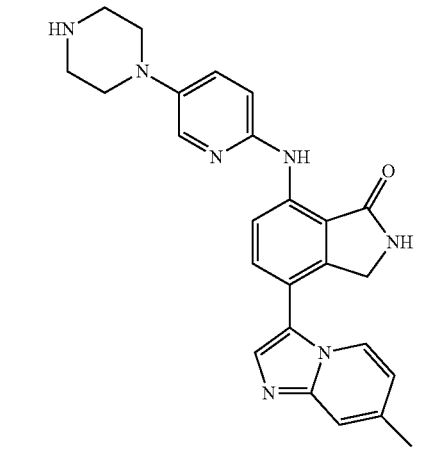 [SMILES: Cc1ccn2c(-c3ccc(Nc4ccc(N5CCNCC5)cn4)c4c3CNC4=O)cnc2c1] |
| I-73 | 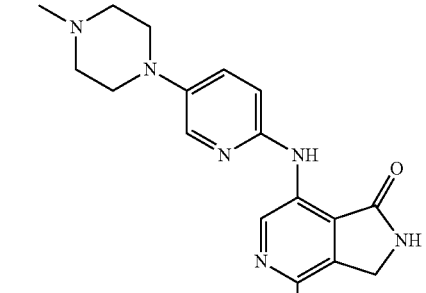 |

TABLE 1-continued
| # | Structure |
|---|---|
| I-74 | 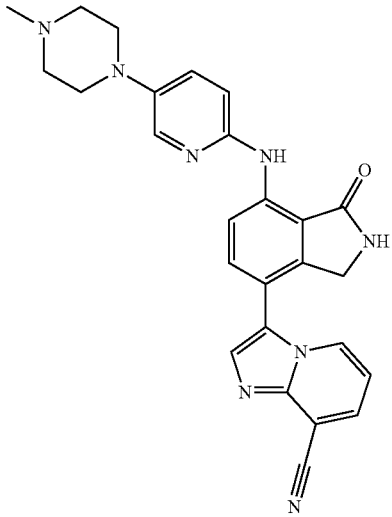 [SMILES: CN1CCN(c2ccc(Nc3ccc(-c4cnc5c(C#N)cccn45)c4c3C(=O)NC4)nc2)CC1] |
| I-75 | 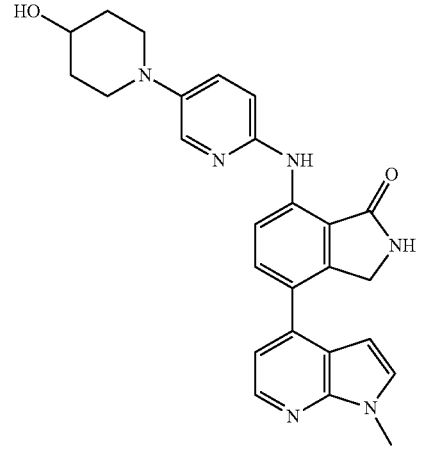 |
| I-76 | 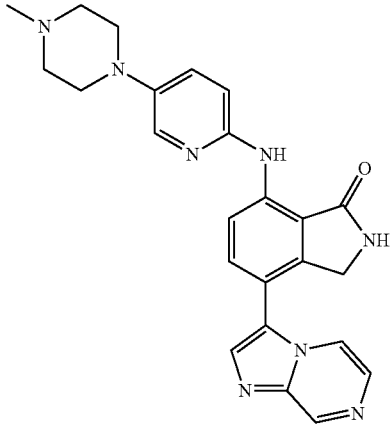 [SMILES: CN1CCN(c2ccc(Nc3ccc(-c4cnc5cnccn45)c4c3C(=O)NC4)nc2)CC1] |

TABLE 1-continued
Selected Compounds
| # | Structure |
|---|---|
| I-77 | 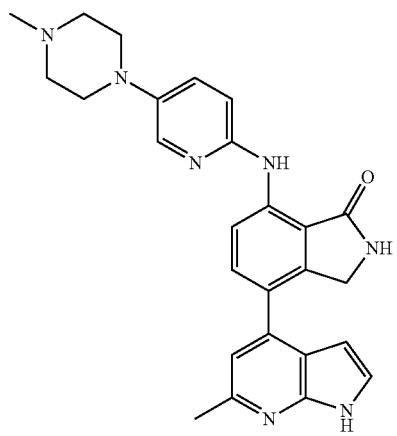 [SMILES: Cc1cc(-c2ccc(Nc3ccc(N4CCN(C)CC4)cn3)c3c2CNC3=O)c2cc[nH]c2n1] |
| I-78 | 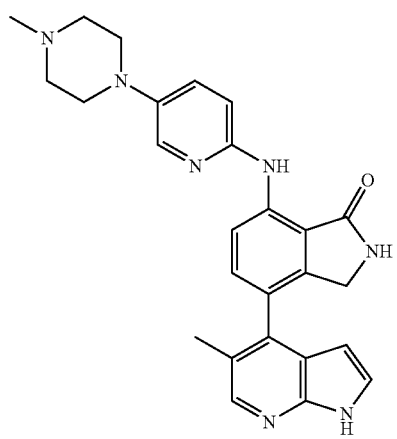 [SMILES: Cc1cnc2[nH]ccc2c1-c1ccc(Nc2ccc(N3CCN(C)CC3)cn2)c2c1CNC2=O] |
| I-79 | 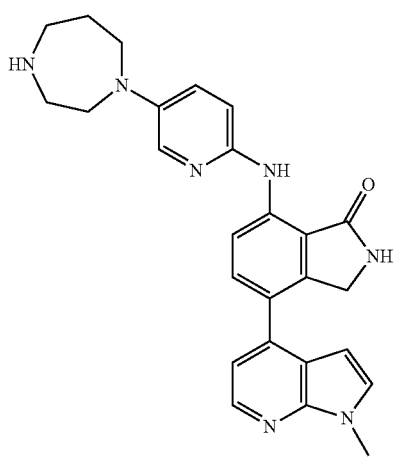 [SMILES: Cn1ccc2c(-c3ccc(Nc4ccc(N5CCCNCC5)cn4)c4c3CNC4=O)ccnc21] |

TABLE 1-continued
Selected Compounds
| # | Structure |
|---|---|
| I-80 | 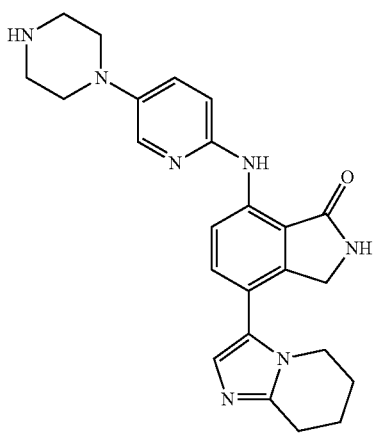 [SMILES: O=C1NCc2c(-c3cnc4n3CCCC4)ccc(Nc3ccc(N4CCNCC4)cn3)c21] |
| I-81 | 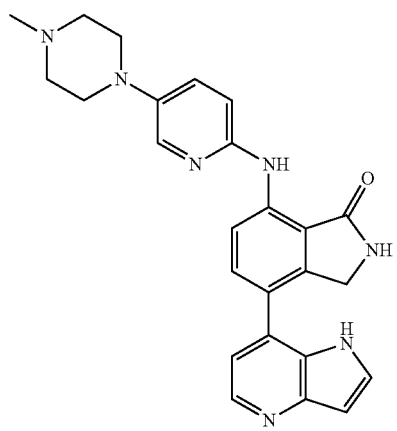 [SMILES: CN1CCN(c2ccc(Nc3ccc(-c4ccnc5cc[nH]c45)c4c3C(=O)NC4)nc2)CC1] |
| I-82 | 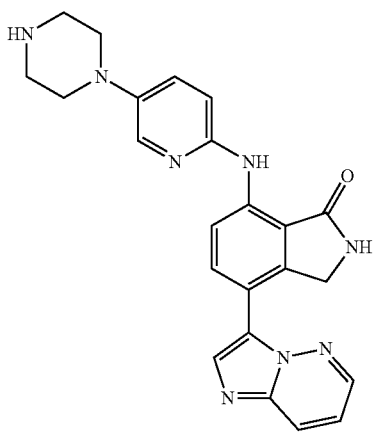 [SMILES: O=C1NCc2c(-c3cnc4cccnn34)ccc(Nc3ccc(N4CCNCC4)cn3)c21] |

TABLE 1-continued
Selected Compounds
| # | Structure |
|---|---|
| I-83 | 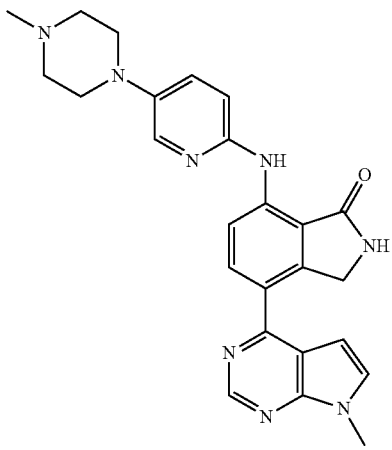 [SMILES: CN1CCN(c2ccc(Nc3ccc(-c4ncnc5c4ccn5C)c4c3C(=O)NC4)nc2)CC1] |
| I-84 | 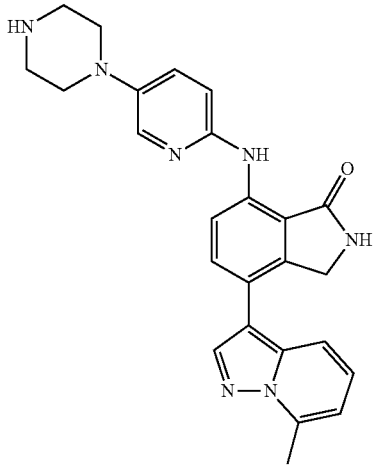 [SMILES: Cc1cccc2c(-c3ccc(Nc4ccc(N5CCNCC5)cn4)c4c3CNC4=O)cnn12] |
| I-85 | 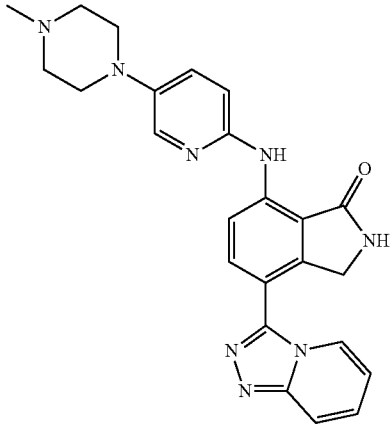 [SMILES: CN1CCN(c2ccc(Nc3ccc(-c4nnc5ccccn45)c4c3C(=O)NC4)nc2)CC1] |

TABLE 1-continued
Selected Compounds
| # | Structure |
|---|---|
| I-86 | 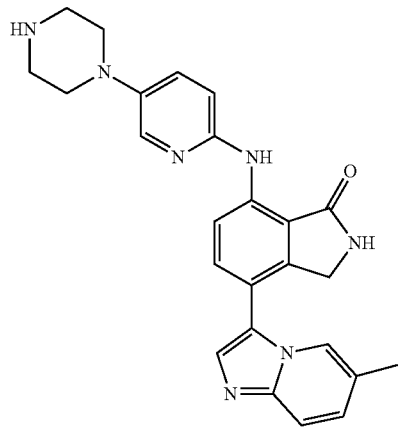 [SMILES: Cc1ccc2ncc(-c3ccc(Nc4ccc(N5CCNCC5)cn4)c4c3CNC4=O)n2c1] |
| I-87 | 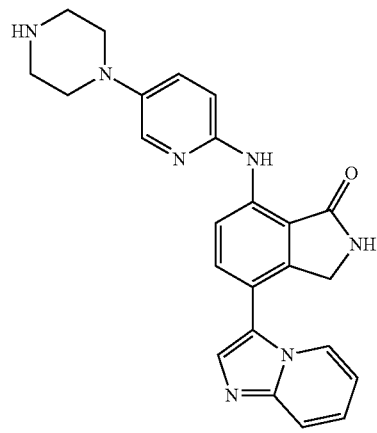 |
| I-88 | 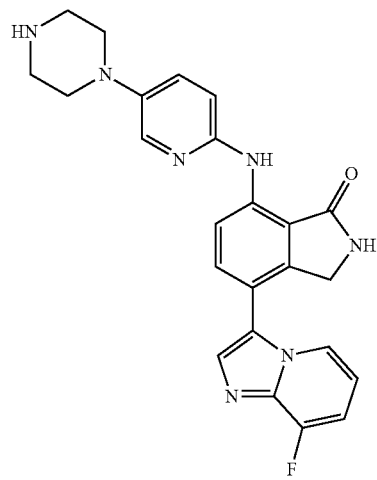 [SMILES: O=C1NCc2c(-c3cnc4c(F)cccn34)ccc(Nc3ccc(N4CCNCC4)cn3)c21] |

TABLE 1-continued
Selected Compounds
| # | Structure |
|---|---|
| I-89 | 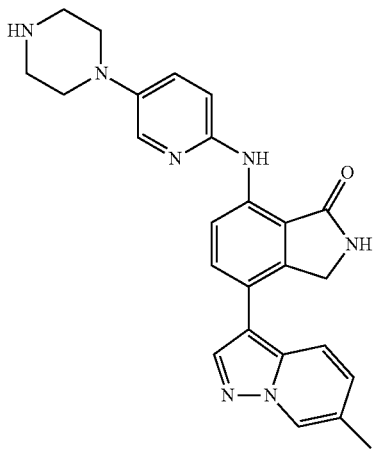 [SMILES: Cc1ccc2c(-c3ccc(Nc4ccc(N5CCNCC5)cn4)c4c3CNC4=O)cnn2c1] |
| I-90 | 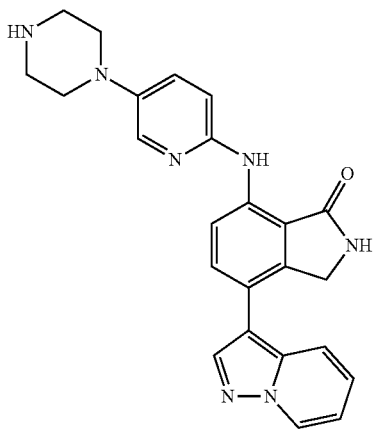 [SMILES: O=C1NCc2c(-c3cnn4ccccc34)ccc(Nc3ccc(N4CCNCC4)cn3)c21] |
| I-91 | 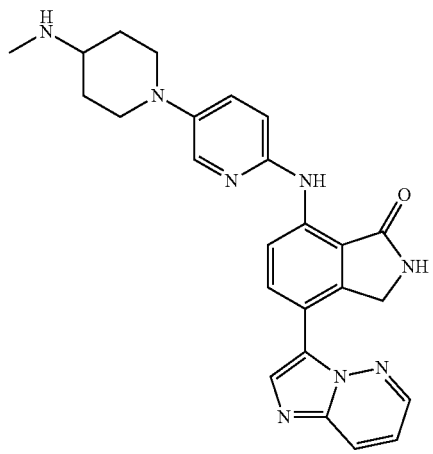 [SMILES: CNC1CCN(c2ccc(Nc3ccc(-c4cnc5cccnn45)c4c3C(=O)NC4)nc2)CC1] |

TABLE 1-continued
Selected Compounds
| # | Structure |
|---|---|
| I-92 | 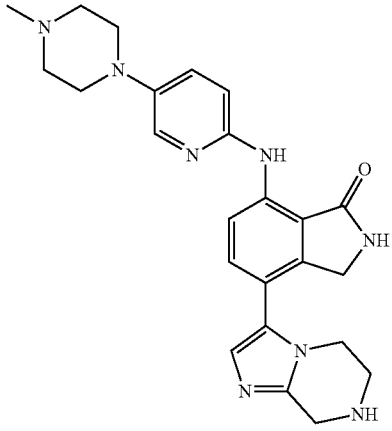 [SMILES: CN1CCN(c2ccc(Nc3ccc(-c4cnc5n4CCNC5)c4c3C(=O)NC4)nc2)CC1] |
| I-93 | 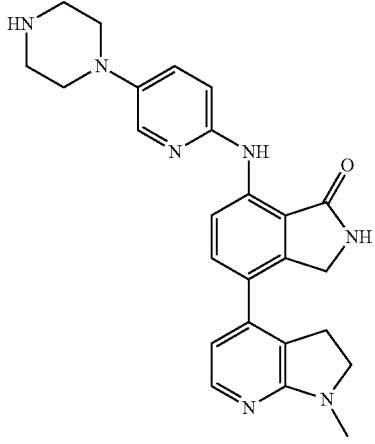 [SMILES: CN1CCc2c(-c3ccc(Nc4ccc(N5CCNCC5)cn4)c4c3CNC4=O)ccnc21] |
| I-94 | 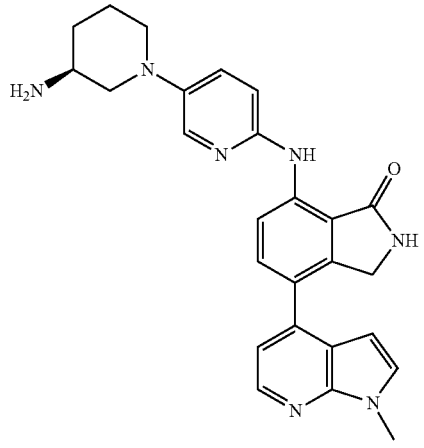 [SMILES: Cn1ccc2c(-c3ccc(Nc4ccc(N5CCC[C@H](N)C5)cn4)c4c3CNC4=O)ccnc21] |

TABLE 1-continued
Selected Compounds
| # | Structure |
|---|---|
| I-95 | 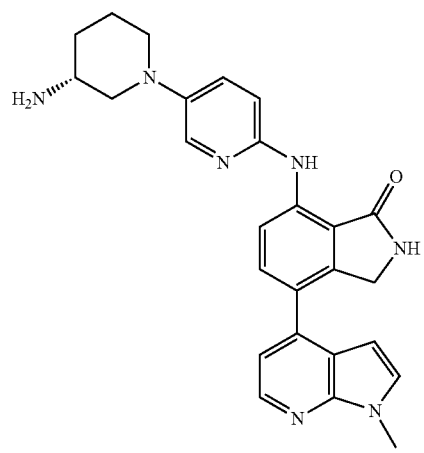 [SMILES: Cn1ccc2c(-c3ccc(Nc4ccc(N5CCC[C@@H](N)C5)cn4)c4c3CNC4=O)ccnc21] |
| I-96 | 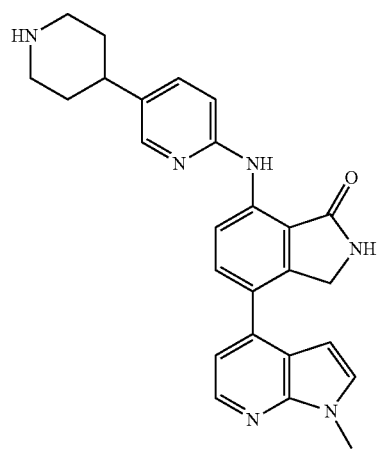 [SMILES: Cn1ccc2c(-c3ccc(Nc4ccc(C5CCNCC5)cn4)c4c3CNC4=O)ccnc21] |
| I-97 | 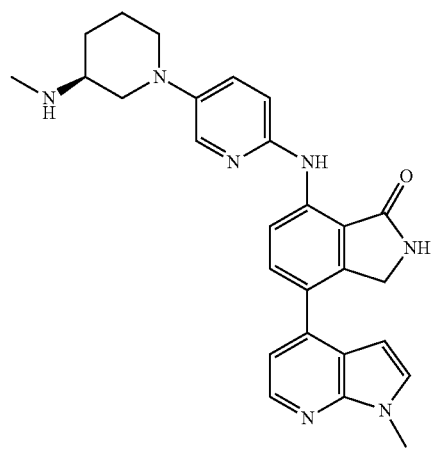 [SMILES: CN[C@H]1CCCN(c2ccc(Nc3ccc(-c4ccnc5c4ccn5C)c4c3C(=O)NC4)nc2)C1] |

TABLE 1-continued
Selected Compounds
| # | Structure |
|---|---|
| I-98 | 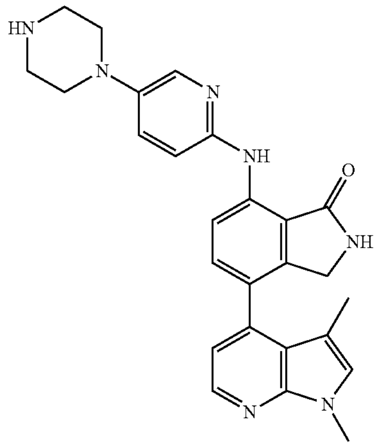 [SMILES: Cc1cn(C)c2nccc(-c3ccc(Nc4ccc(N5CCNCC5)cn4)c4c3CNC4=O)c12] |
| I-99 | 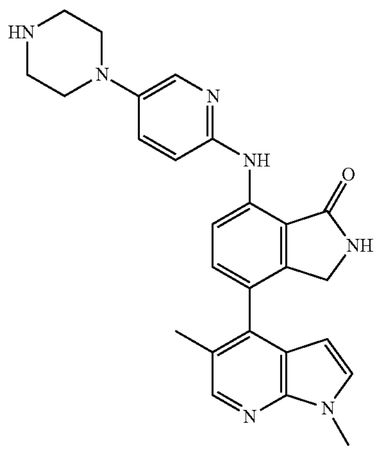 [SMILES: Cc1cnc2c(ccn2C)c1-c1ccc(Nc2ccc(N3CCNCC3)cn2)c2c1CNC2=O] |
| I-100 | 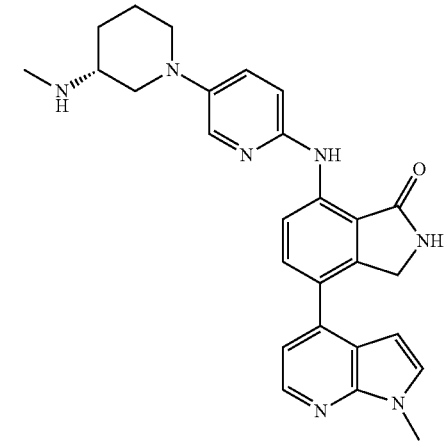 [SMILES: CN[C@@H]1CCCN(c2ccc(Nc3ccc(-c4ccnc5c4ccn5C)c4c3C(=O)NC4)nc2)C1] |

TABLE 1-continued
Selected Compounds
| # | Structure |
|---|---|
| I-101 | 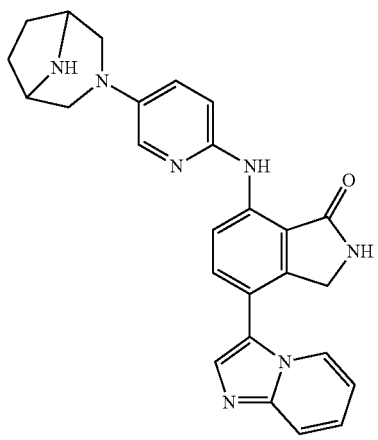 [SMILES: O=C1NCc2c(-c3cnc4ccccn34)ccc(Nc3ccc(N4CC5CCC(C4)N5)cn3)c21] |
| I-102 | 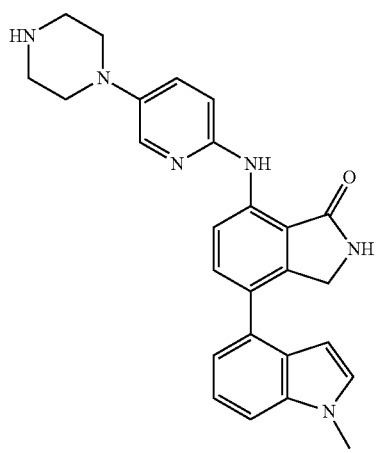 [SMILES: Cn1ccc2c(-c3ccc(Nc4ccc(N5CCNCC5)cn4)c4c3CNC4=O)cccc21] |
| I-103 | 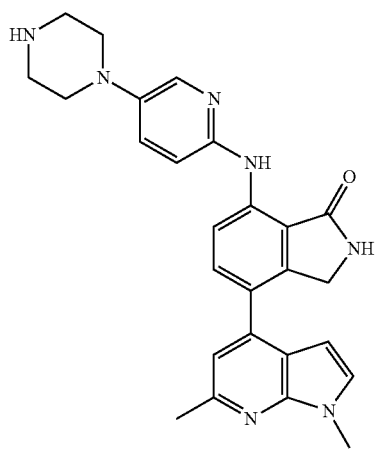 [SMILES: Cc1cc(-c2ccc(Nc3ccc(N4CCNCC4)cn3)c3c2CNC3=O)c2ccn(C)c2n1] |

TABLE 1-continued
Selected Compounds
| # | Structure |
|---|---|
| I-104 | 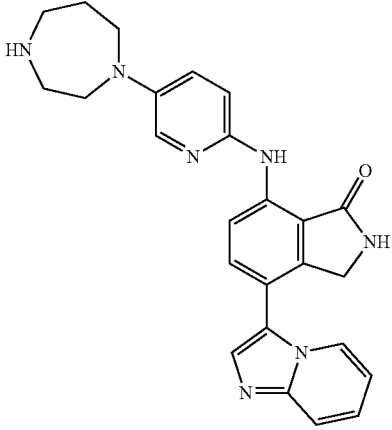 [SMILES: O=C1NCc2c(-c3cnc4ccccn34)ccc(Nc3ccc(N4CCCNCC4)cn3)c21] |
| I-105 | 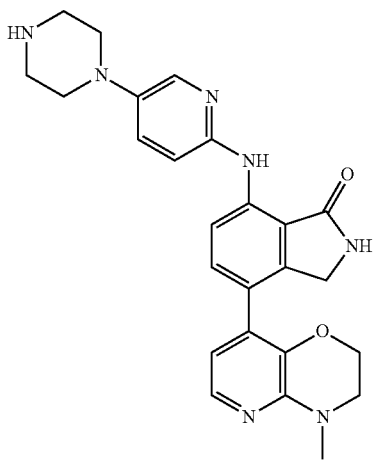 [SMILES: CN1CCOc2c(-c3ccc(Nc4ccc(N5CCNCC5)cn4)c4c3CNC4=O)ccnc21] |
| I-106 | 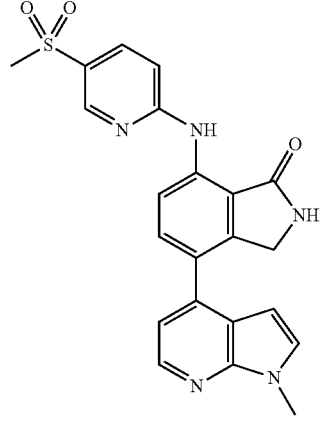 [SMILES: Cn1ccc2c(-c3ccc(Nc4ccc(S(C)(=O)=O)cn4)c4c3CNC4=O)ccnc21] |

TABLE 1-continued
Selected Compounds
| # | Structure |
|---|---|
| I-107 | 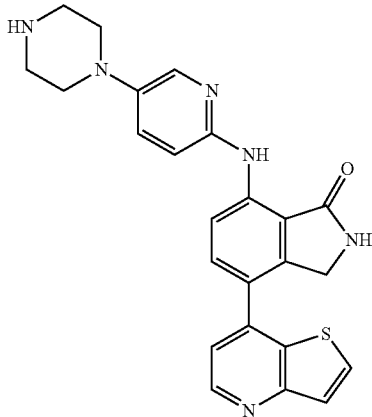 [SMILES: O=C1NCc2c(-c3ccnc4ccsc34)ccc(Nc3ccc(N4CCNCC4)cn3)c21] |
| I-108 | 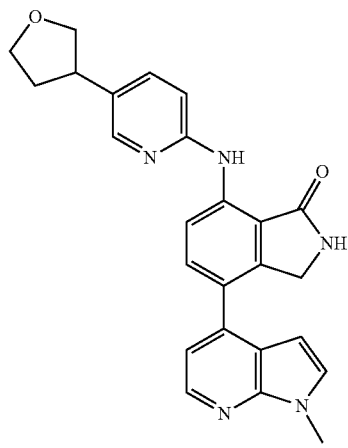 [SMILES: Cn1ccc2c(-c3ccc(Nc4ccc(C5CCOC5)cn4)c4c3CNC4=O)ccnc21] |
| I-109 | 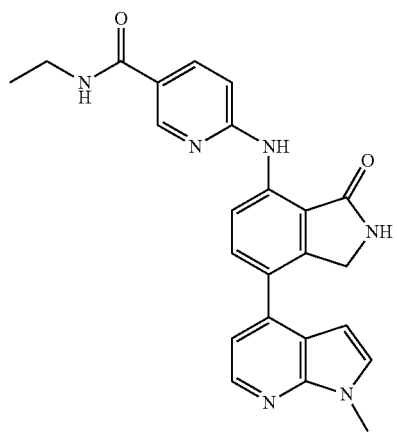 [SMILES: CCNC(=O)c1ccc(Nc2ccc(-c3ccnc4c3ccn4C)c3c2C(=O)NC3)nc1] |

TABLE 1-continued
Selected Compounds
| # | Structure |
|---|---|
| I-110 | 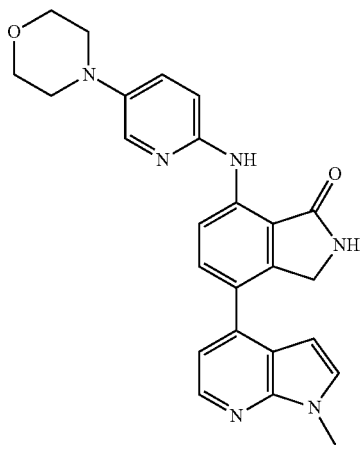 [SMILES: Cn1ccc2c(-c3ccc(Nc4ccc(N5CCOCC5)cn4)c4c3CNC4=O)ccnc21] |
| I-111 | 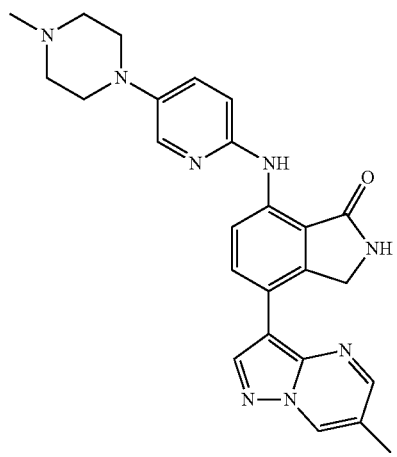 |
| I-112 | 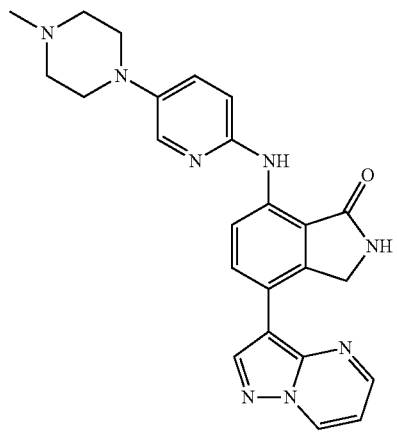 [SMILES: CN1CCN(c2ccc(Nc3ccc(-c4cnn5cccnc45)c4c3C(=O)NC4)nc2)CC1] |

TABLE 1-continued

Selected Compounds

| # | Structure |
|---|---|
| I-113 | 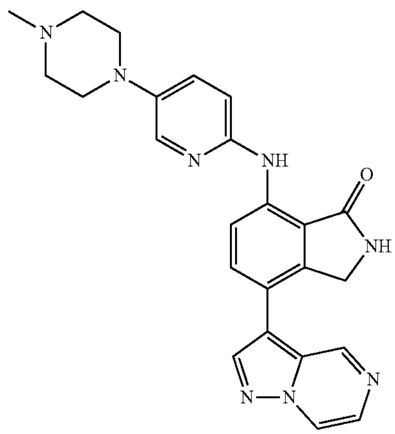 [SMILES: CN1CCN(c2ccc(Nc3ccc(-c4cnn5ccncc45)c4c3C(=O)NC4)nc2)CC1] |
| I-114 | 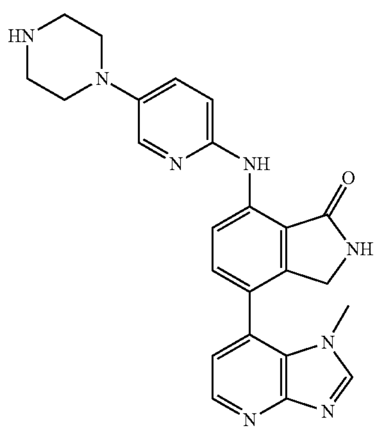 [SMILES: Cn1cnc2nccc(-c3ccc(Nc4ccc(N5CCNCC5)cn4)c4c3CNC4=O)c21] |
| I-115 | 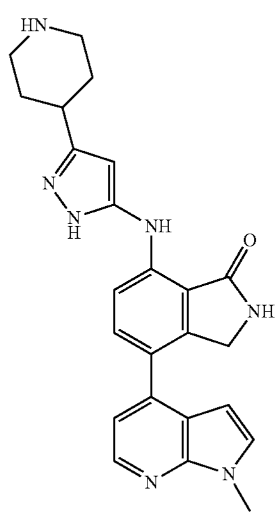 [SMILES: Cn1ccc2c(-c3ccc(Nc4cc(C5CCNCC5)n[nH]4)c4c3CNC4=O)ccnc21] |

TABLE 1-continued
Selected Compounds
| # | Structure |
|---|---|
| I-116 | 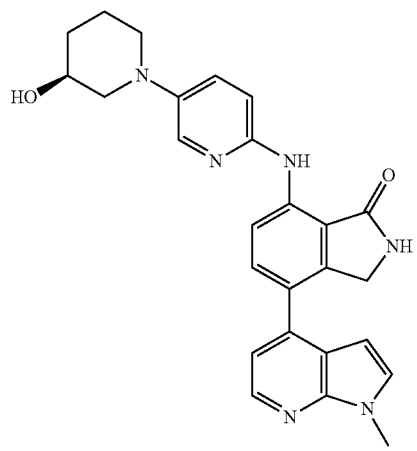 [SMILES: Cn1ccc2c(-c3ccc(Nc4ccc(N5CCC[C@H](O)C5)cn4)c4c3CNC4=O)ccnc21] |
| I-117 | 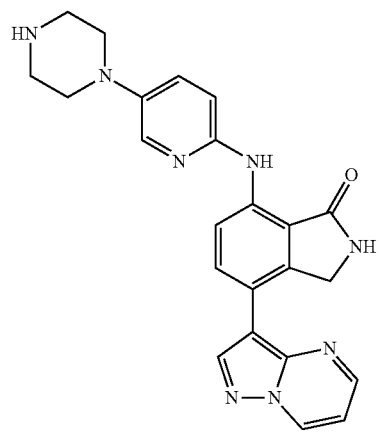 [SMILES: O=C1NCc2c(-c3cnn4cccnc34)ccc(Nc3ccc(N4CCNCC4)cn3)c21] |
| I-118 | 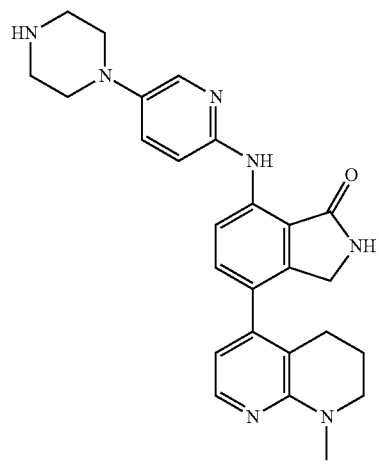 [SMILES: CN1CCCc2c(-c3ccc(Nc4ccc(N5CCNCC5)cn4)c4c3CNC4=O)ccnc21] |

TABLE 1-continued
Selected Compounds
| # | Structure |
|---|---|
| I-119 | 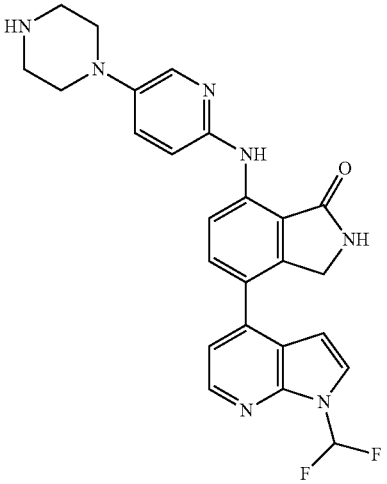 [SMILES: O=C1NCc2c(-c3ccnc4c3ccn4C(F)F)ccc(Nc3ccc(N4CCNCC4)cn3)c21] |
| I-120 | 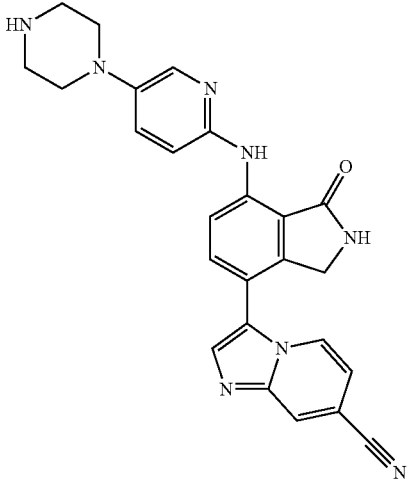 [SMILES: N#Cc1ccn2c(-c3ccc(Nc4ccc(N5CCNCC5)cn4)c4c3CNC4=O)cnc2c1] |
| I-121 | 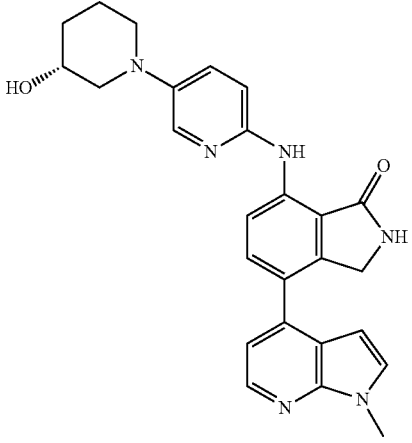 [SMILES: Cn1ccc2c(-c3ccc(Nc4ccc(N5CCC[C@@H](O)C5)cn4)c4c3CNC4=O)ccnc21] |

TABLE 1-continued
Selected Compounds
| # | Structure |
|---|---|
| I-122 | 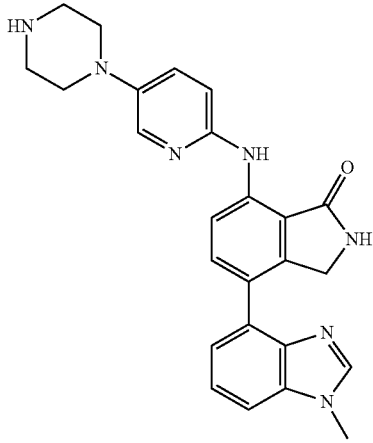 [SMILES: Cn1cnc2c(-c3ccc(Nc4ccc(N5CCNCC5)cn4)c4c3CNC4=O)cccc21] |
| I-123 | 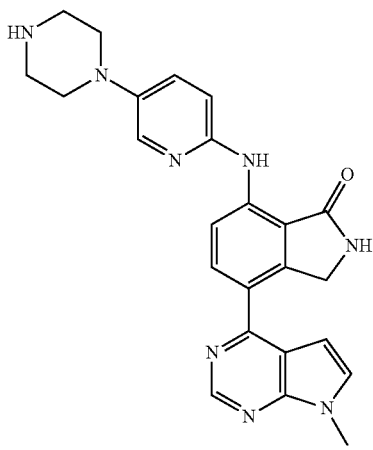 [SMILES: Cn1ccc2c(-c3ccc(Nc4ccc(N5CCNCC5)cn4)c4c3CNC4=O)ncnc21] |
| I-124 | 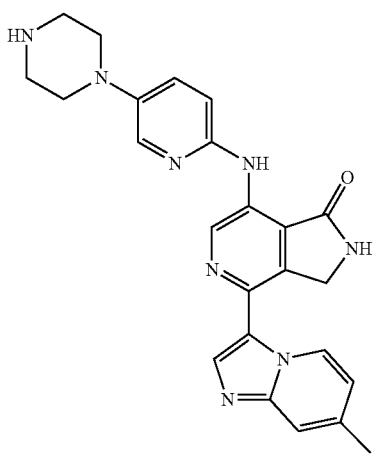 [SMILES: Cc1ccn2c(-c3ncc(Nc4ccc(N5CCNCC5)cn4)c4c3CNC4=O)cnc2c1] |

TABLE 1-continued
| Selected Compounds | |
|---|---|
| # | Structure |
I-125
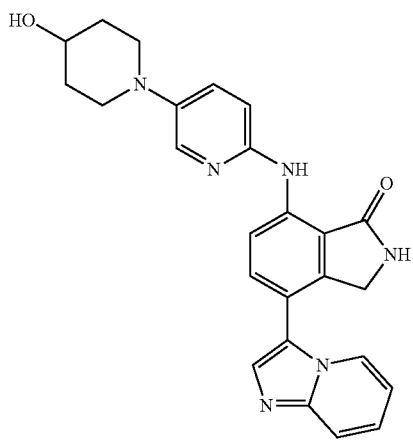 [SMILES: O=C1NCc2c(-c3cnc4ccccn34)ccc(Nc3ccc(N4CCC(O)CC4)cn3)c21]
I-126
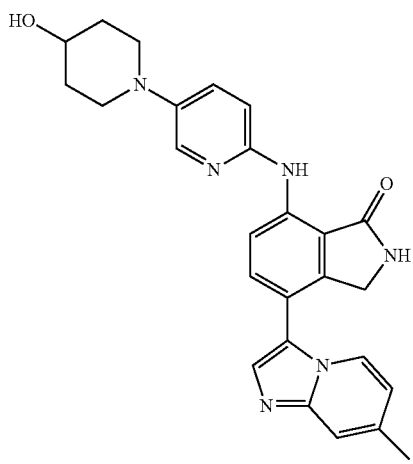 [SMILES: Cc1ccn2c(-c3ccc(Nc4ccc(N5CCC(O)CC5)cn4)c4c3CNC4=O)cnc2c1]
I-127
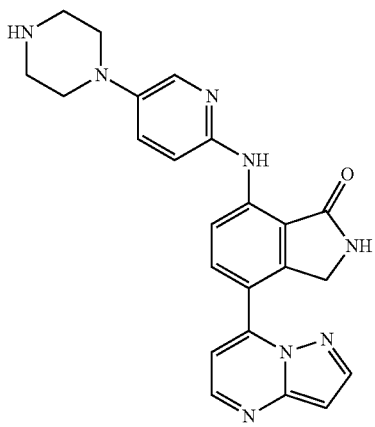 [SMILES: O=C1NCc2c(-c3ccnc4ccnn34)ccc(Nc3ccc(N4CCNCC4)cn3)c21]

TABLE 1-continued
Selected Compounds
| # | Structure |
|---|---|
| I-128 | 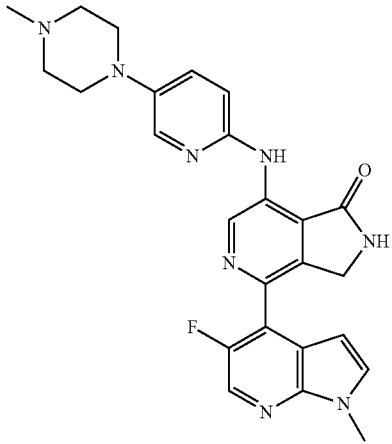 [SMILES: CN1CCN(c2ccc(Nc3cnc(-c4c(F)cnc5c4ccn5C)c4c3C(=O)NC4)nc2)CC1] |
| I-129 | 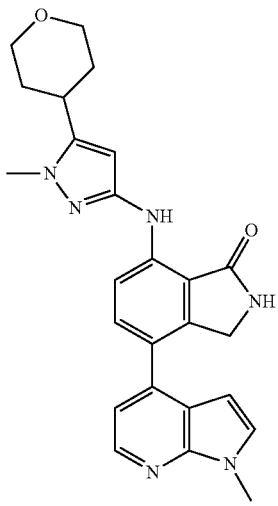 [SMILES: Cn1nc(Nc2ccc(-c3ccnc4c3ccn4C)c3c2C(=O)NC3)cc1C1CCOCC1] |
| I-130 | 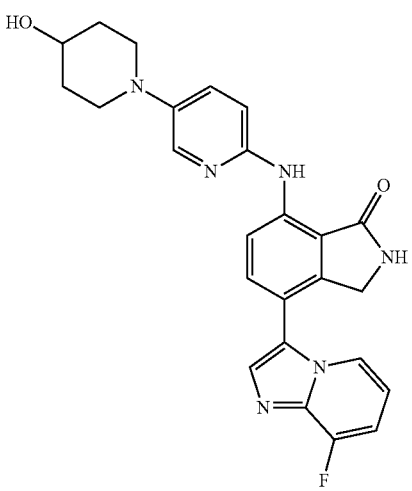 [SMILES: O=C1NCc2c(-c3cnc4c(F)cccn34)ccc(Nc3ccc(N4CCC(O)CC4)cn3)c21] |

TABLE 1-continued
| Selected Compounds | |
|---|---|
| # | Structure |
| I-131 | 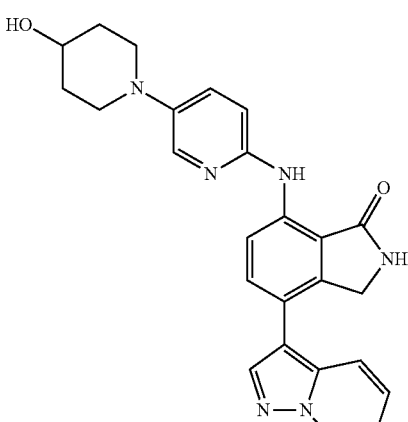 |
| I-132 | 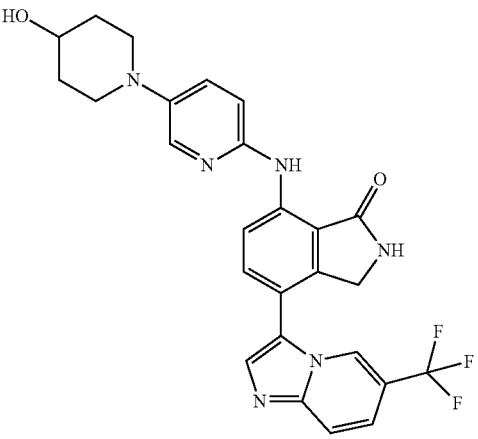 [SMILES: O=C1NCc2c(-c3cnc4ccc(C(F)(F)F)cn34)ccc(Nc3ccc(N4CCC(O)CC4)cn3)c21] |
| I-133 | 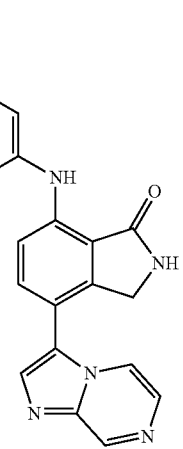 |

TABLE 1-continued
| Selected Compounds | |
|---|---|
| # | Structure |
| I-134 | 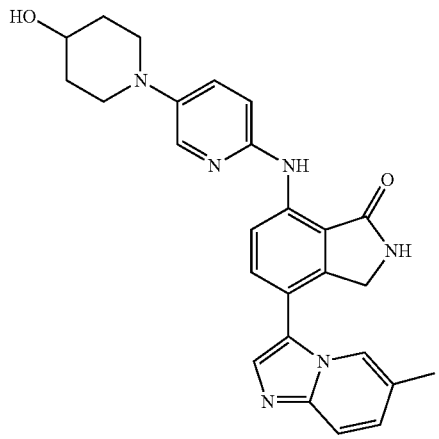 [SMILES: Cc1ccc2ncc(-c3ccc(Nc4ccc(N5CCC(O)CC5)cn4)c4c3CNC4=O)n2c1] |
| I-135 | 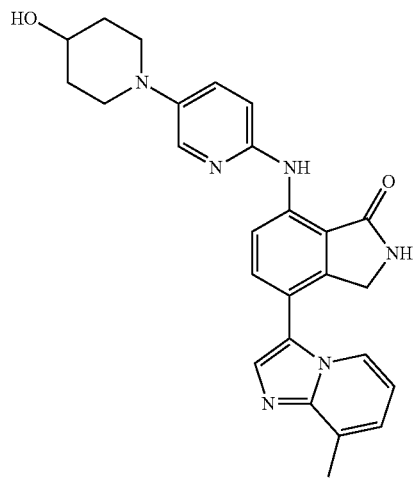 [SMILES: Cc1cccn2c(-c3ccc(Nc4ccc(N5CCC(O)CC5)cn4)c4c3CNC4=O)cnc12] |
| I-136 | 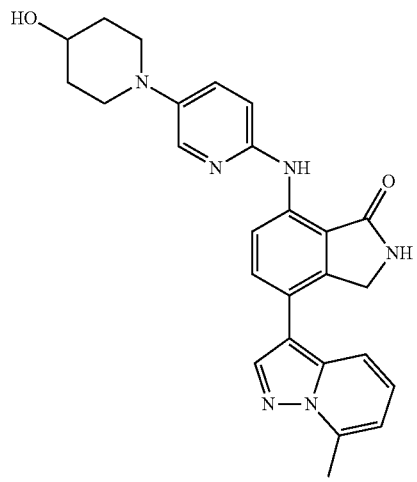 [SMILES: Cc1cccc2c(-c3ccc(Nc4ccc(N5CCC(O)CC5)cn4)c4c3CNC4=O)cnn12] |

TABLE 1-continued
Selected Compounds
| # | Structure |
|---|---|
| I-137 | 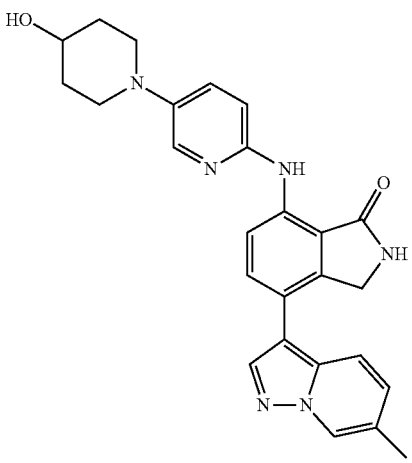 [SMILES: Cc1ccc2c(-c3ccc(Nc4ccc(N5CCC(O)CC5)cn4)c4c3CNC4=O)cnn2c1] |
| I-138 | 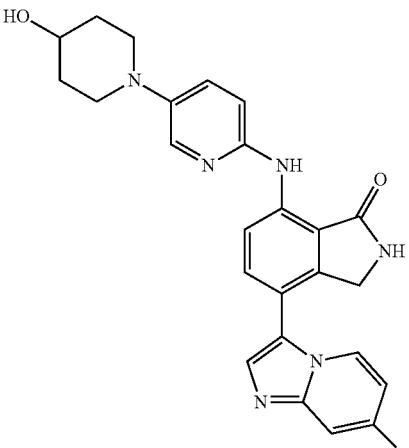 |
| I-139 | 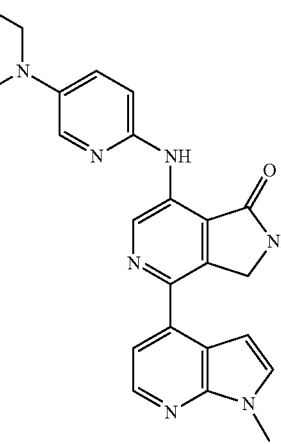 |

TABLE 1-continued
Selected Compounds
| # | Structure |
|---|---|
| I-140 | 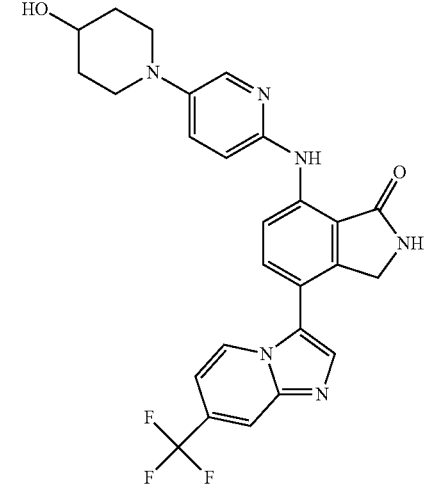 [SMILES: O=C1NCc2c(-c3cnc4cc(C(F)(F)F)ccn34)ccc(Nc3ccc(N4CCC(O)CC4)cn3)c21] |
| I-141 | 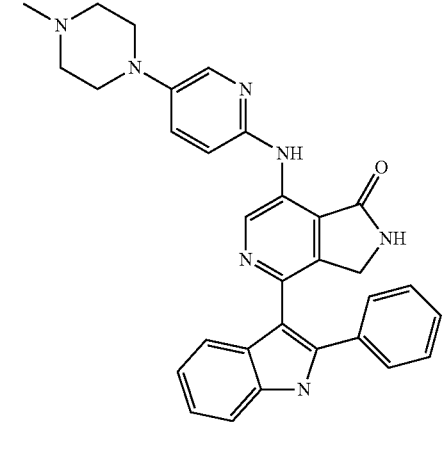 [SMILES: CN1CCN(c2ccc(Nc3cnc(-c4c(-c5ccccc5)[nH]c5ccccc45)c4c3C(=O)NC4)nc2)CC1] |
| I-142 | 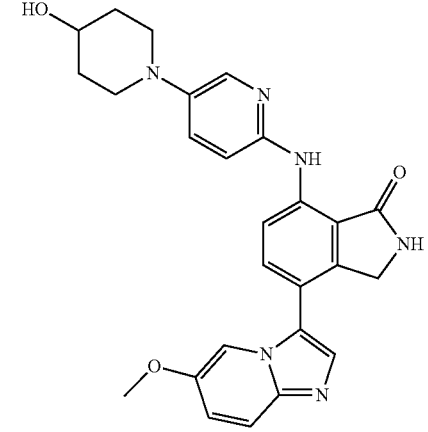 [SMILES: COc1ccc2ncc(-c3ccc(Nc4ccc(N5CCC(O)CC5)cn4)c4c3CNC4=O)n2c1] |

TABLE 1-continued
Selected Compounds
| # | Structure |
|---|---|
| I-143 | 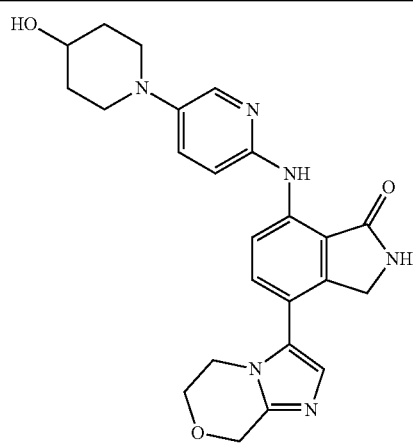 |
| I-144 | 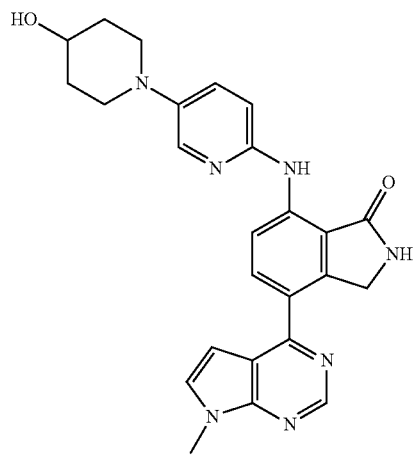 [SMILES: Cn1ccc2c(-c3ccc(Nc4ccc(N5CCC(O)CC5)cn4)c4c3CNC4=O)ncnc21] |
| I-145 | 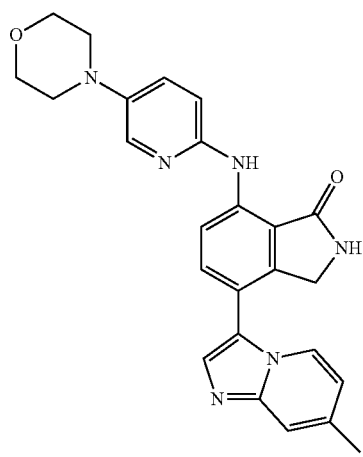 [SMILES: Cc1ccn2c(-c3ccc(Nc4ccc(N5CCOCC5)cn4)c4c3CNC4=O)cnc2c1] |

TABLE 1-continued
Selected Compounds
| # | Structure |
|---|---|
| I-146 | 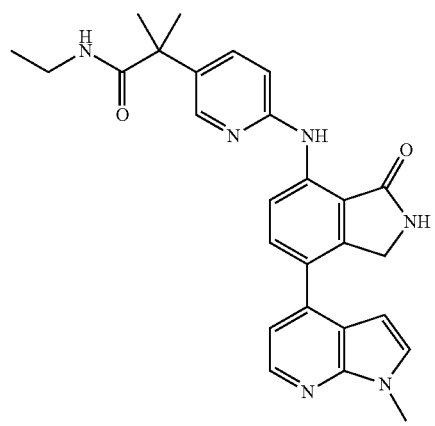 [SMILES: CCNC(=O)C(C)(C)c1ccc(Nc2ccc(-c3ccnc4c3ccn4C)c3c2C(=O)NC3)nc1] |
| I-147 | 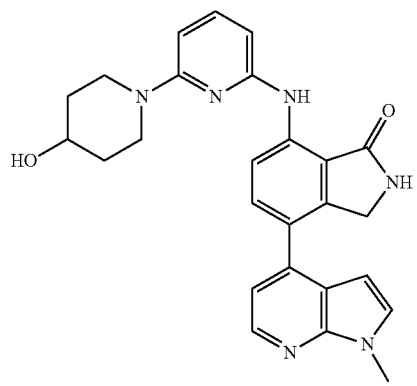 [SMILES: Cn1ccc2c(-c3ccc(Nc4cccc(N5CCC(O)CC5)n4)c4c3CNC4=O)ccnc21] |
| I-148 | 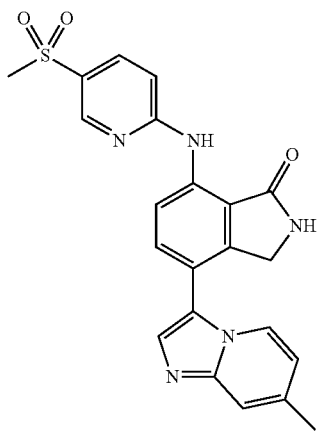 |

TABLE 1-continued

Selected Compounds

| # | Structure |
|---|---|
| I-149 | (4-hydroxypiperidinyl-pyridinyl-NH-isoindolinone-imidazopyridine-CF₃) |
| I-150 | (4-hydroxypiperidinyl-pyridinyl-NH-isoindolinone-tetrahydropyrazolopyridine-C(O)NH-cyclopropyl) |
| I-151 | (4-hydroxypiperidinyl-pyridinyl-NH-isoindolinone-imidazopyridine-methyl-F) |

TABLE 1-continued
Selected Compounds
| # | Structure |
|---|---|
| I-152 | 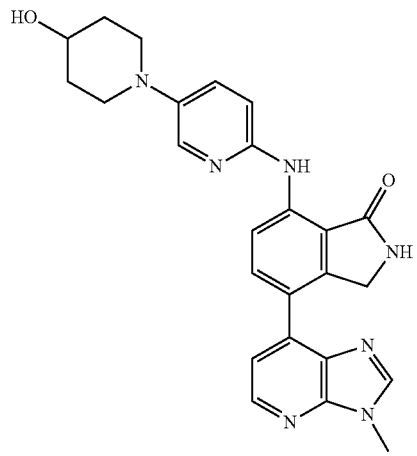 [SMILES: Cn1cnc2c(-c3ccc(Nc4ccc(N5CCC(O)CC5)cn4)c4c3CNC4=O)ccnc21] |
| I-153 | 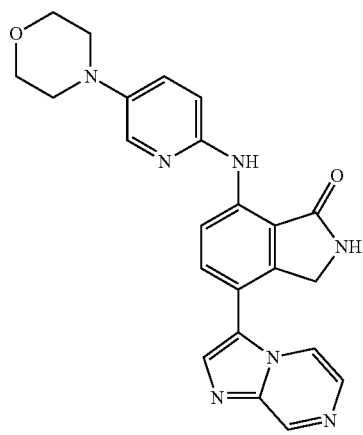 [SMILES: O=C1NCc2c(-c3cnc4cnccn34)ccc(Nc3ccc(N4CCOCC4)cn3)c21] |
| I-154 | 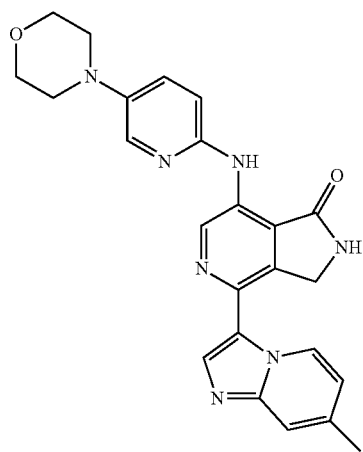 [SMILES: Cc1ccn2c(-c3ncc(Nc4ccc(N5CCOCC5)cn4)c4c3CNC4=O)cnc2c1] |

TABLE 1-continued
| Selected Compounds | |
|---|---|
| # | Structure |
| I-155 | 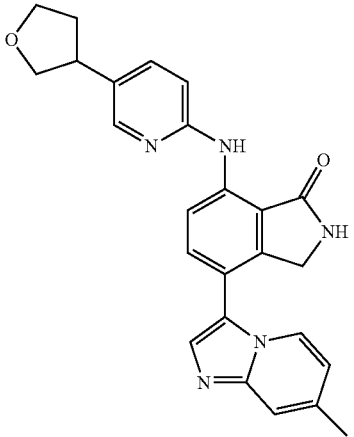 [SMILES: Cc1ccn2c(-c3ccc(Nc4ccc(C5CCOC5)cn4)c4c3CNC4=O)cnc2c1] |
| I-156 | 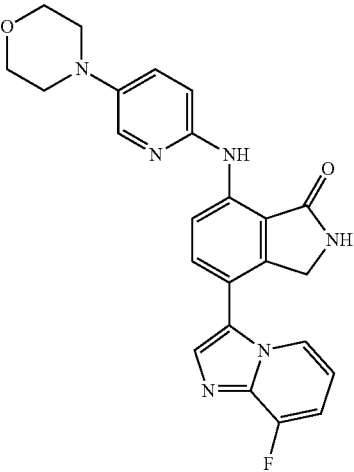 [SMILES: O=C1NCc2c(-c3cnc4c(F)cccn34)ccc(Nc3ccc(N4CCOCC4)cn3)c21] |
| I-157 | 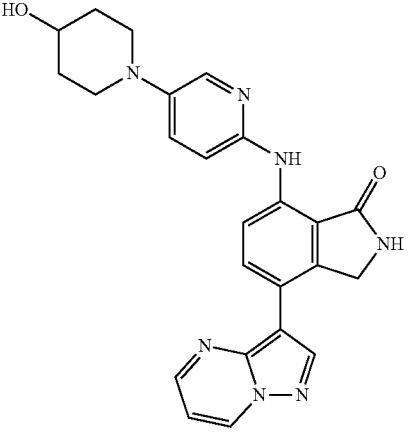 [SMILES: O=C1NCc2c(-c3cnn4cccnc34)ccc(Nc3ccc(N4CCC(O)CC4)cn3)c21] |

TABLE 1-continued
| Selected Compounds | |
|---|---|
| # | Structure |
| I-158 | 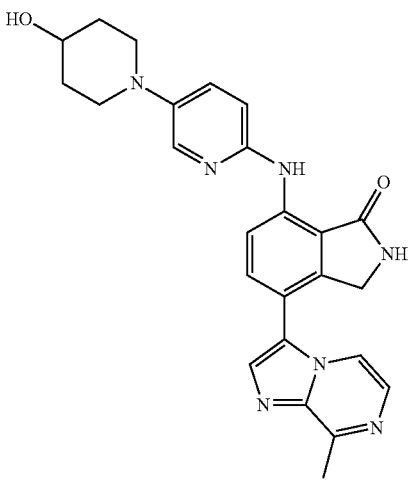 [SMILES: Cc1nccn2c(-c3ccc(Nc4ccc(N5CCC(O)CC5)cn4)c4c3CNC4=O)cnc12] |
| I-159 | 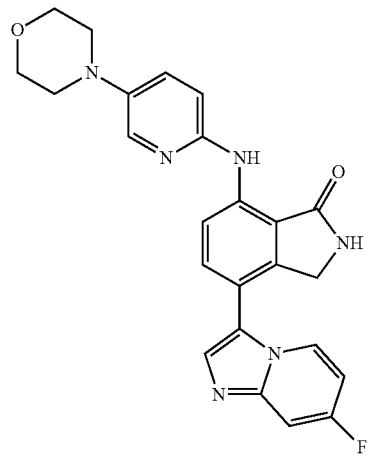 [SMILES: O=C1NCc2c(-c3cnc4cc(F)ccn34)ccc(Nc3ccc(N4CCOCC4)cn3)c21] |
| I-160 | 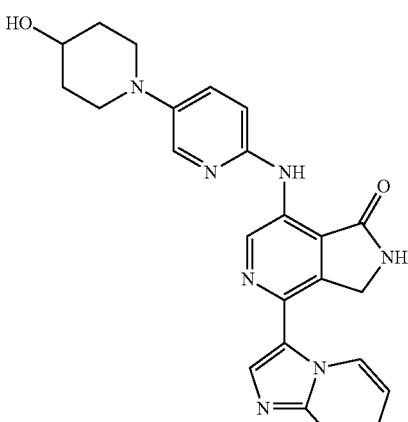 |

TABLE 1-continued
Selected Compounds
| # | Structure |
|---|---|
| I-161 | 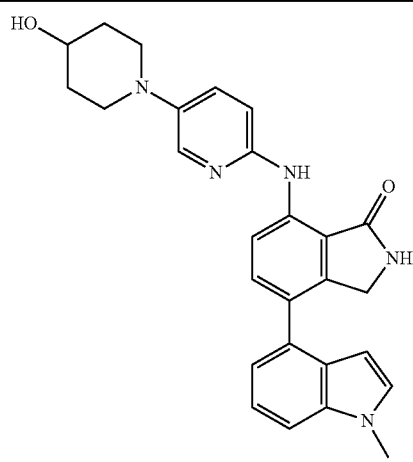 |
| I-162 | 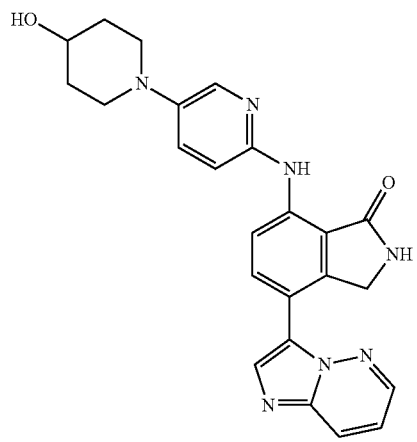 [SMILES: O=C1NCc2c(-c3cnc4cccnn34)ccc(Nc3ccc(N4CCC(O)CC4)cn3)c21] |
| I-163 | 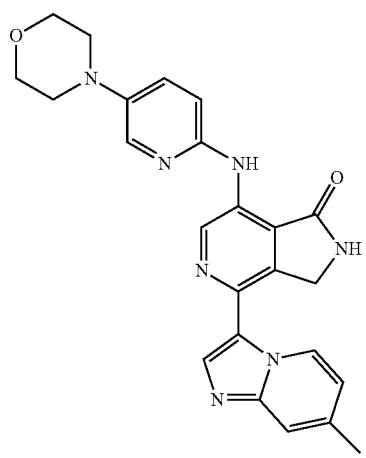 [SMILES: Cc1ccn2c(-c3ncc(Nc4ccc(N5CCOCC5)cn4)c4c3CNC4=O)cnc2c1] |

TABLE 1-continued
Selected Compounds
| # | Structure |
|---|---|
| I-164 | 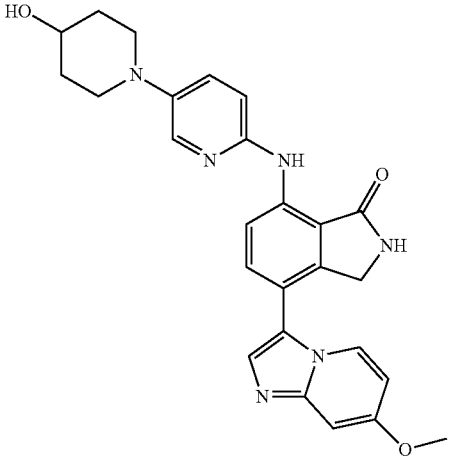 [SMILES: COc1ccn2c(-c3ccc(Nc4ccc(N5CCC(O)CC5)cn4)c4c3CNC4=O)cnc2c1] |
| I-165 | 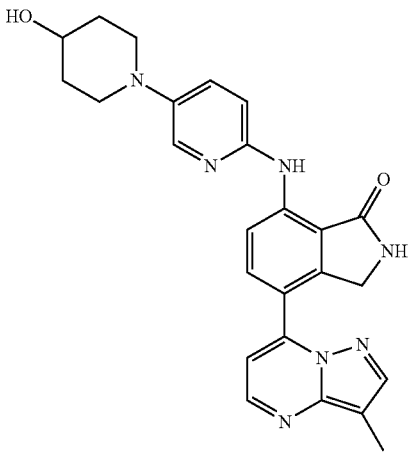 [SMILES: Cc1cnn2c(-c3ccc(Nc4ccc(N5CCC(O)CC5)cn4)c4c3CNC4=O)ccnc12] |
| I-166 | 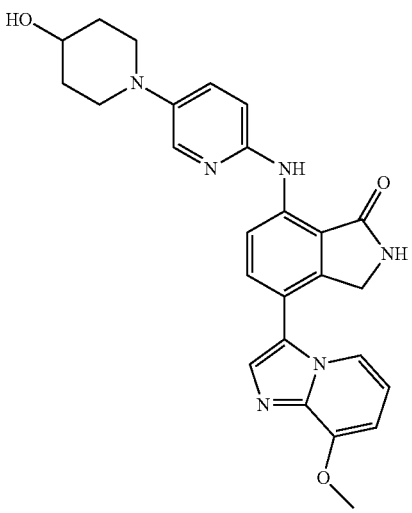 [SMILES: COc1cccn2c(-c3ccc(Nc4ccc(N5CCC(O)CC5)cn4)c4c3CNC4=O)cnc12] |

TABLE 1-continued
Selected Compounds
| # | Structure |
|---|---|
| I-167 | 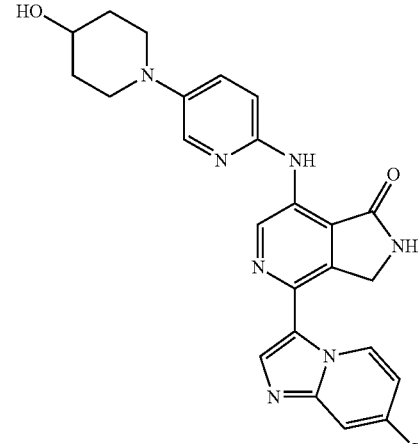 |
| I-168 | 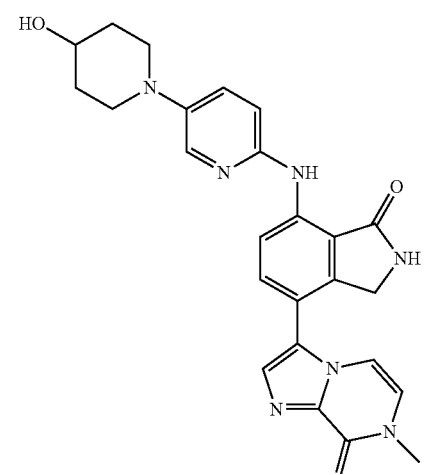 |
| I-169 | 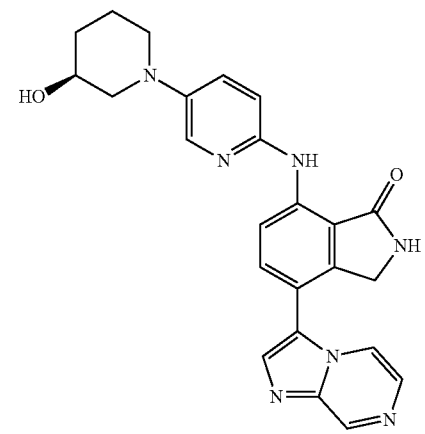 [SMILES: O=C1NCc2c(-c3cnc4cnccn34)ccc(Nc3ccc(N4CCC[C@H](O)C4)cn3)c21] |

TABLE 1-continued
Selected Compounds
| # | Structure |
|---|---|
| I-170 | 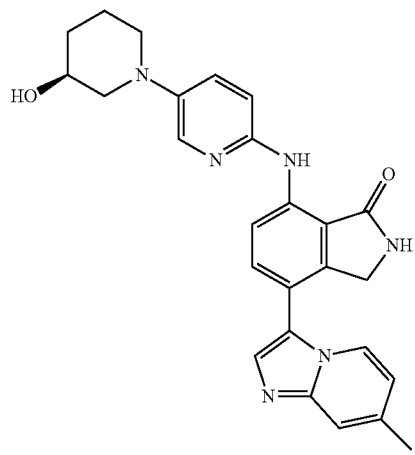 [SMILES: Cc1ccn2c(-c3ccc(Nc4ccc(N5CCC[C@H](O)C5)cn4)c4c3CNC4=O)cnc2c1] |
| I-171 | 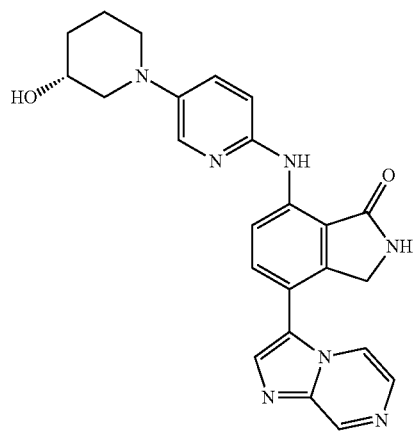 [SMILES: O=C1NCc2c(-c3cnc4cnccn34)ccc(Nc3ccc(N4CCC[C@@H](O)C4)cn3)c21] |
| I-172 | 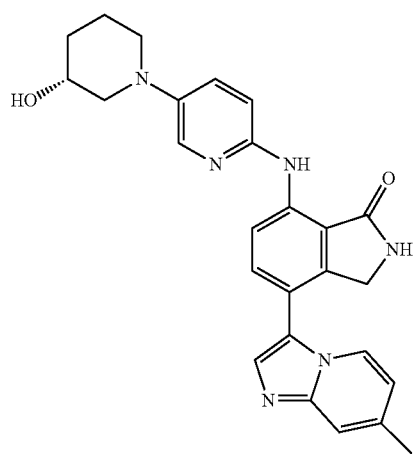 [SMILES: Cc1ccn2c(-c3ccc(Nc4ccc(N5CCC[C@@H](O)C5)cn4)c4c3CNC4=O)cnc2c1] |

TABLE 1-continued
Selected Compounds
| # | Structure |
|---|---|
| I-173 | 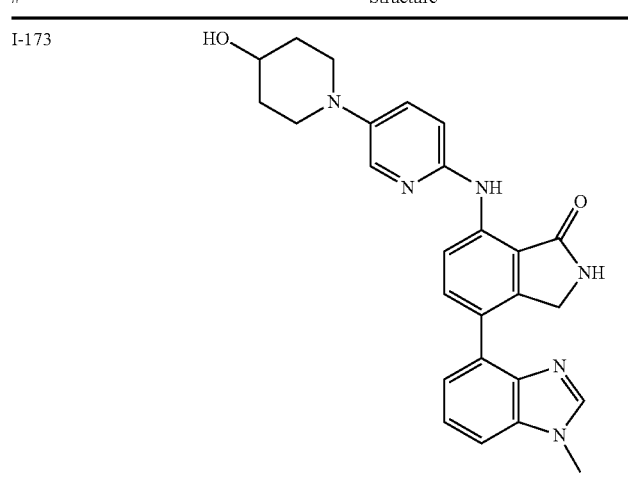 |
| I-174 | 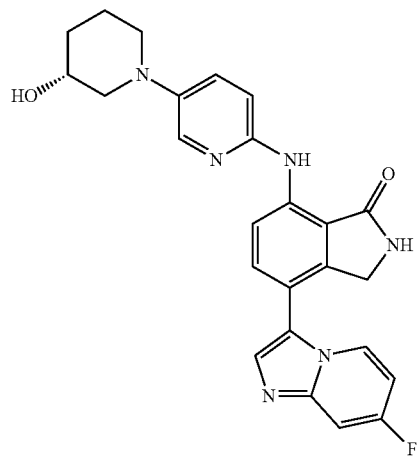 [SMILES: O=C1NCc2c(-c3cnc4cc(F)ccn34)ccc(Nc3ccc(N4CCC[C@@H](O)C4)cn3)c21] |
| I-175 | 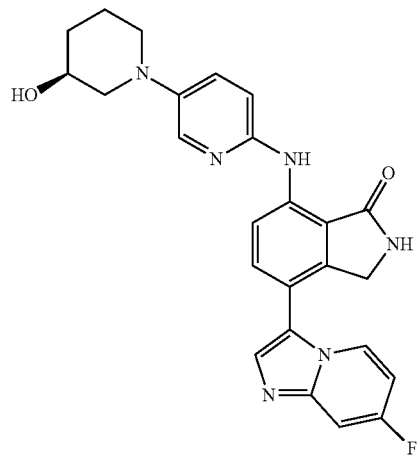 [SMILES: O=C1NCc2c(-c3cnc4cc(F)ccn34)ccc(Nc3ccc(N4CCC[C@H](O)C4)cn3)c21] |

259 260
TABLE 1-continued
Selected Compounds
| # | Structure |
|---|---|
| I-176 | 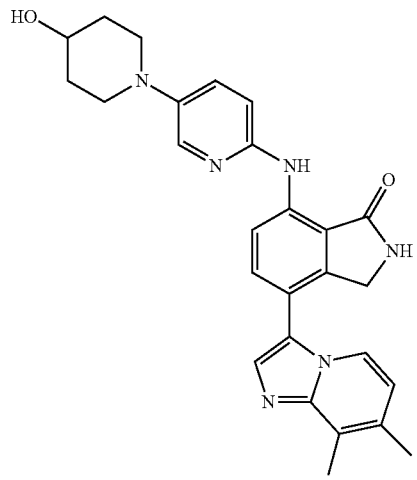 [SMILES: Cc1ccn2c(-c3ccc(Nc4ccc(N5CCC(O)CC5)cn4)c4c3CNC4=O)cnc2c1C] |
| I-177 | 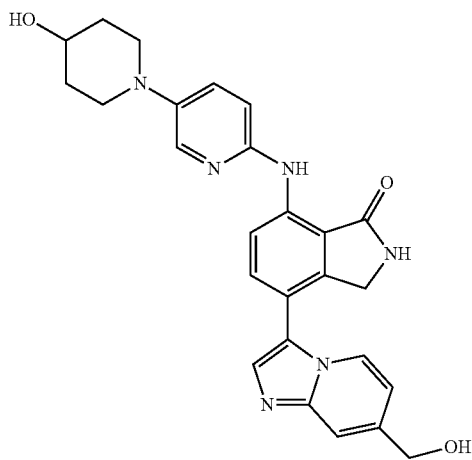 [SMILES: O=C1NCc2c(-c3cnc4cc(CO)ccn34)ccc(Nc3ccc(N4CCC(O)CC4)cn3)c21] |
| I-178 | 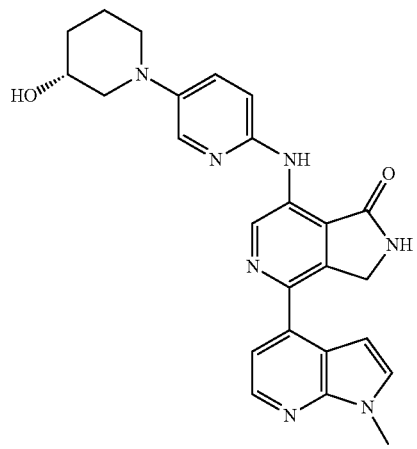 [SMILES: Cn1ccc2c(-c3ncc(Nc4ccc(N5CCC[C@@H](O)C5)cn4)c4c3CNC4=O)ccnc21] |

TABLE 1-continued

Selected Compounds

| # | Structure |
|---|---|
| I-179 | 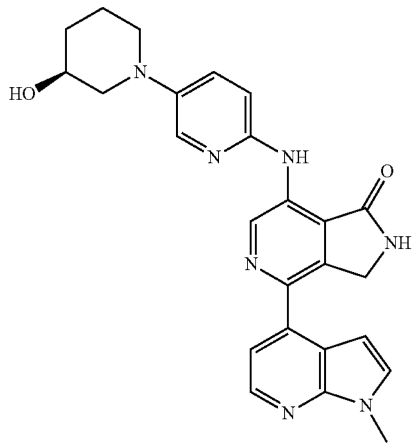 [SMILES: Cn1ccc2c(-c3ncc(Nc4ccc(N5CCC[C@H](O)C5)cn4)c4c3CNC4=O)ccnc21] |
| I-180 | 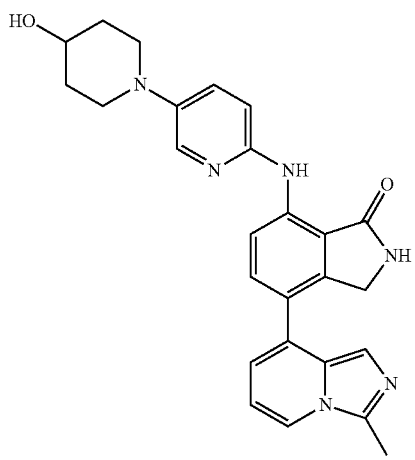 [SMILES: Cc1ncc2c(-c3ccc(Nc4ccc(N5CCC(O)CC5)cn4)c4c3CNC4=O)cccn12] |
| I-181 | 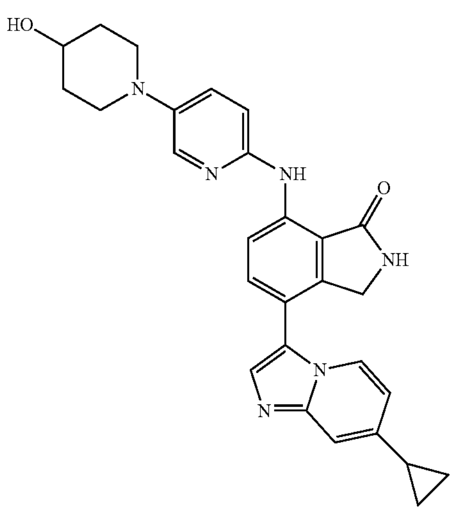 [SMILES: O=C1NCc2c(-c3cnc4cc(C5CC5)ccn34)ccc(Nc3ccc(N4CCC(O)CC4)cn3)c21] |

TABLE 1-continued
Selected Compounds
| # | Structure |
|---|---|
| I-182 | 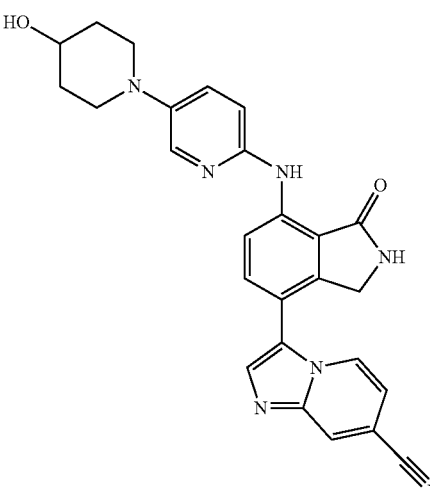 |
| I-183 | 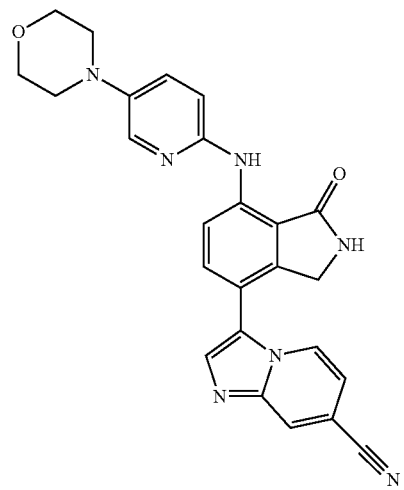 [SMILES: N#Cc1ccn2c(-c3ccc(Nc4ccc(N5CCOCC5)cn4)c4c3CNC4=O)cnc2c1] |
| I-184 | 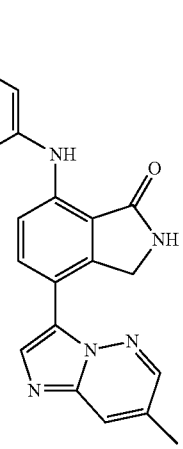 |

TABLE 1-continued
Selected Compounds
| # | Structure |
|---|---|
| I-185 | 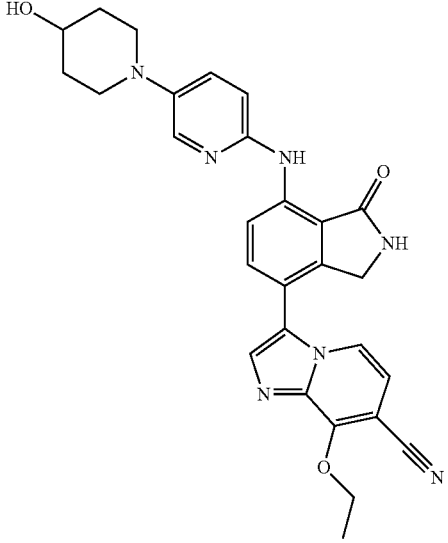 [SMILES: CCOc1c(C#N)ccn2c(-c3ccc(Nc4ccc(N5CCC(O)CC5)cn4)c4c3CNC4=O)cnc12] |
| I-186 | 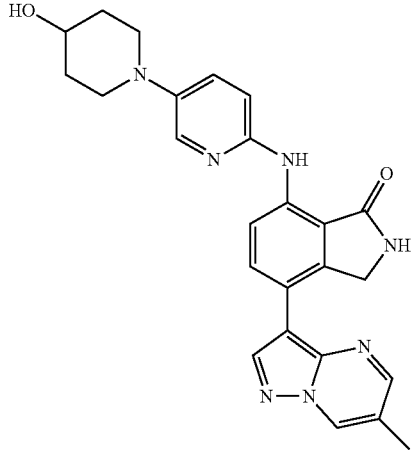 [SMILES: Cc1cnc2c(-c3ccc(Nc4ccc(N5CCC(O)CC5)cn4)c4c3CNC4=O)cnn2c1] |
| I-187 | 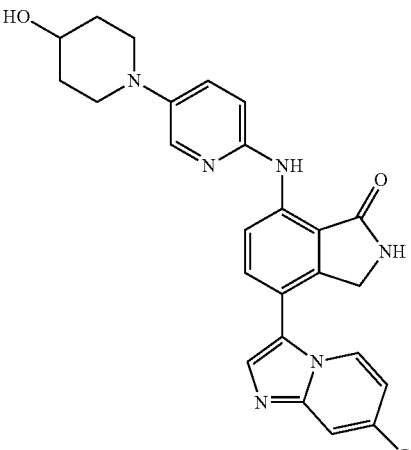 |

TABLE 1-continued
| Selected Compounds | |
|---|---|
| # | Structure |
| I-188 | 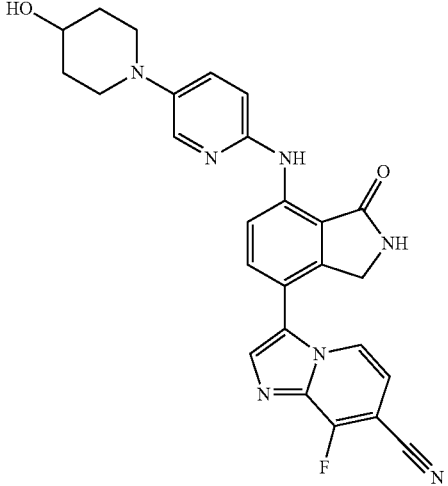 [SMILES: N#Cc1ccn2c(-c3ccc(Nc4ccc(N5CCC(O)CC5)cn4)c4c3CNC4=O)cnc2c1F] |
| I-189 | 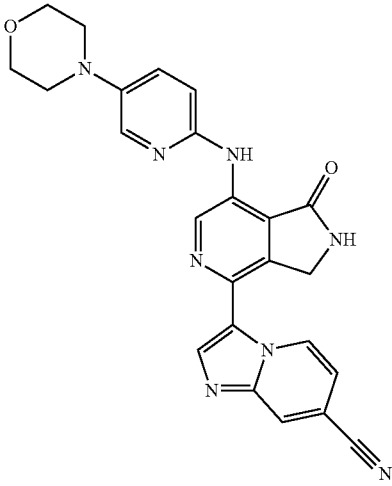 [SMILES: N#Cc1ccn2c(-c3ncc(Nc4ccc(N5CCOCC5)cn4)c4c3CNC4=O)cnc2c1] |
| I-190 | 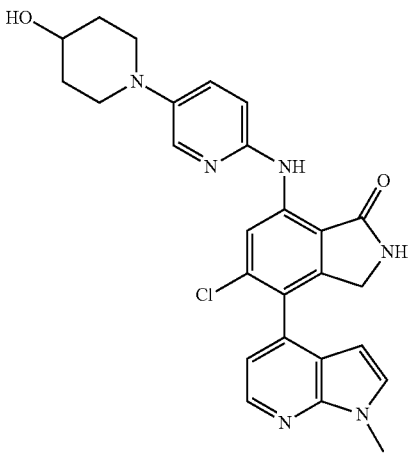 [SMILES: Cn1ccc2c(-c3c(Cl)cc(Nc4ccc(N5CCC(O)CC5)cn4)c4c3CNC4=O)ccnc21] |

TABLE 1-continued
Selected Compounds
| # | Structure |
|---|---|
| I-191 | 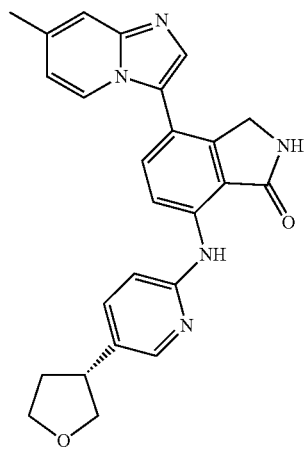 [SMILES: Cc1ccn2c(-c3ccc(Nc4ccc([C@H]5CCOC5)cn4)c4c3CNC4=O)cnc2c1] |
| I-192 | 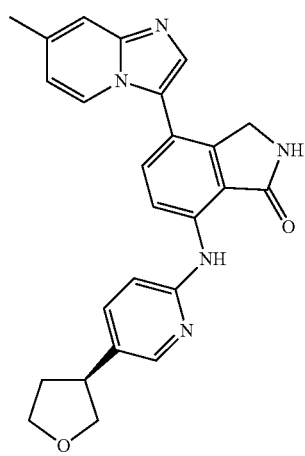 [SMILES: Cc1ccn2c(-c3ccc(Nc4ccc([C@@H]5CCOC5)cn4)c4c3CNC4=O)cnc2c1] |
| I-193 | 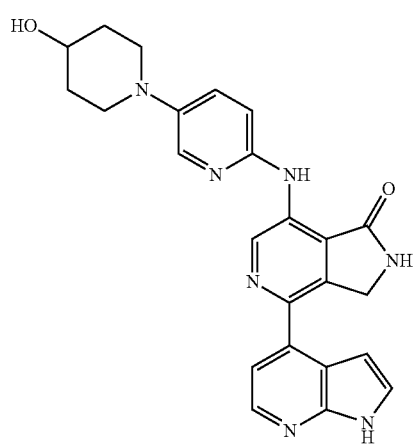 [SMILES: O=C1NCc2c(-c3ccnc4[nH]ccc34)ncc(Nc3ccc(N4CCC(O)CC4)cn3)c21] |

TABLE 1-continued

Selected Compounds

| # | Structure |
|---|---|
| I-194 | (structure) |
| I-195 | (structure) |
| I-196 | (structure) |

TABLE 1-continued

| # | Structure |
|---|---|
| I-197 | 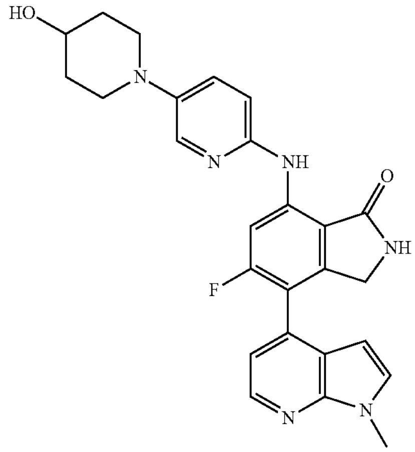 [SMILES: Cn1ccc2c(-c3c(F)cc(Nc4ccc(N5CCC(O)CC5)cn4)c4c3CNC4=O)ccnc21] |
| I-198 | 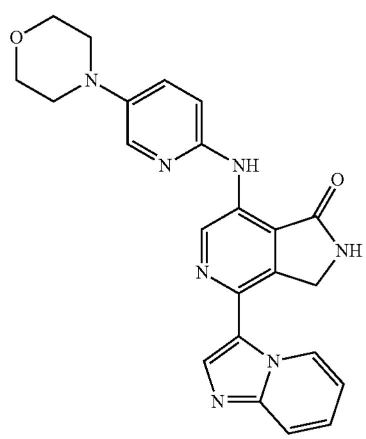 [SMILES: O=C1NCc2c(-c3cnc4ccccn34)ncc(Nc3ccc(N4CCOCC4)cn3)c21] |
| I-199 | 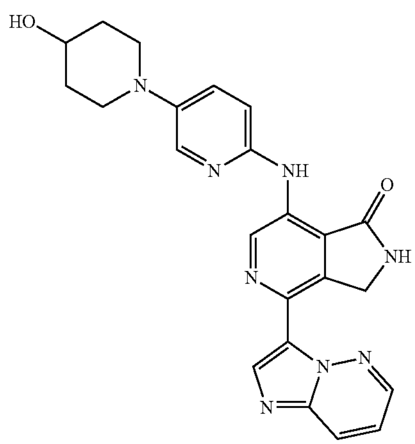 [SMILES: O=C1NCc2c(-c3cnc4cccnn34)ncc(Nc3ccc(N4CCC(O)CC4)cn3)c21] |

TABLE 1-continued

Selected Compounds

| # | Structure |
|---|-----------|
| I-200 | 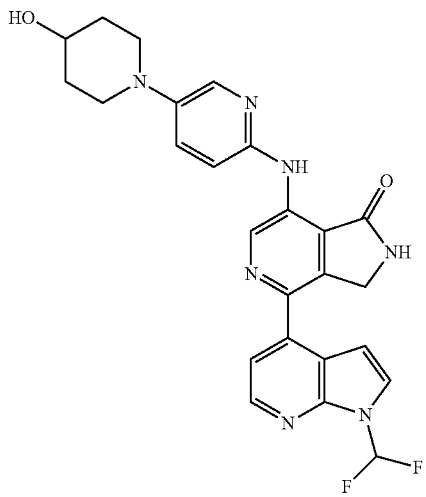 [SMILES: O=C1NCc2c(-c3ccnc4c3ccn4C(F)F)ncc(Nc3ccc(N4CCC(O)CC4)cn3)c21] |
| I-201 | 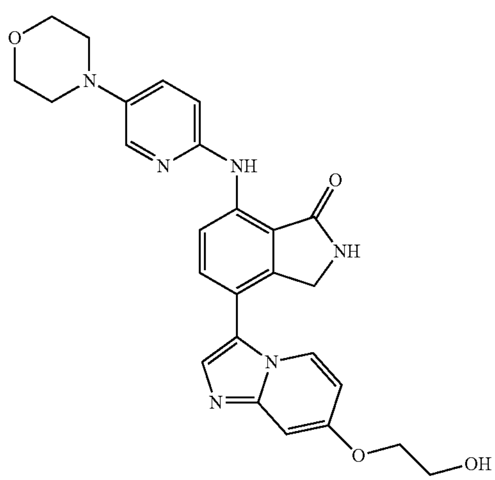 [SMILES: O=C1NCc2c(-c3cnc4cc(OCCO)ccn34)ccc(Nc3ccc(N4CCOCC4)cn3)c21] |
| I-202 | 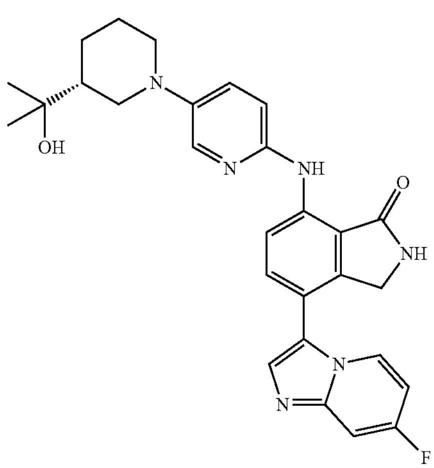 [SMILES: CC(C)(O)[C@@H]1CCCN(c2ccc(Nc3ccc(-c4cnc5cc(F)ccn45)c4c3C(=O)NC4)nc2)C1] |

TABLE 1-continued
Selected Compounds
| # | Structure |
|---|---|
| I-203 | 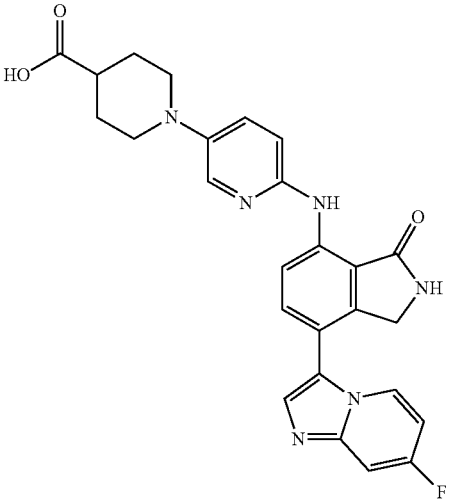 [SMILES: O=C1NCc2c(-c3cnc4cc(F)ccn34)ccc(Nc3ccc(N4CCC(C(=O)O)CC4)cn3)c21] |
| I-204 | 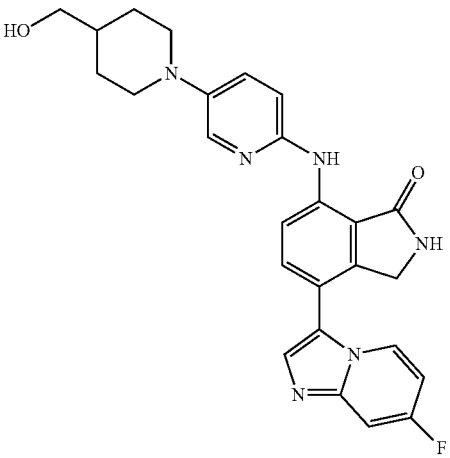 [SMILES: O=C1NCc2c(-c3cnc4cc(F)ccn34)ccc(Nc3ccc(N4CCC(CO)CC4)cn3)c21] |
| I-205 | 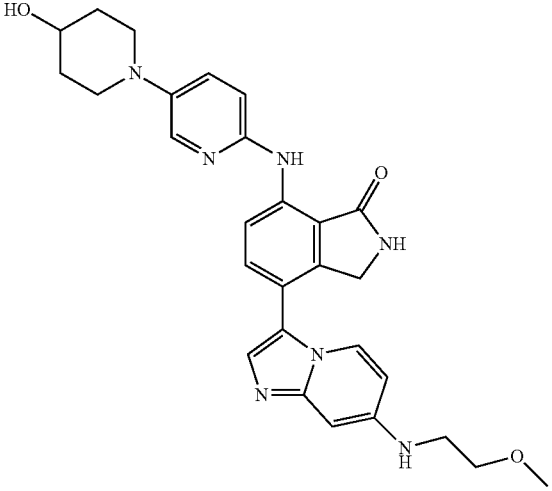 [SMILES: COCCNc1ccn2c(-c3ccc(Nc4ccc(N5CCC(O)CC5)cn4)c4c3CNC4=O)cnc2c1] |

TABLE 1-continued
Selected Compounds
| # | Structure |
|---|---|
| I-206 | 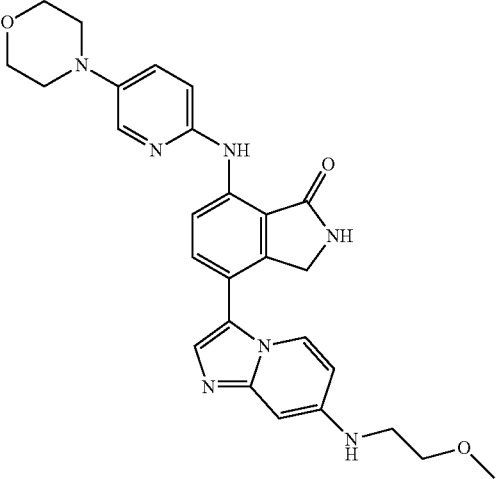 [SMILES: COCCNc1ccn2c(-c3ccc(Nc4ccc(N5CCOCC5)cn4)c4c3CNC4=O)cnc2c1] |
| I-207 | 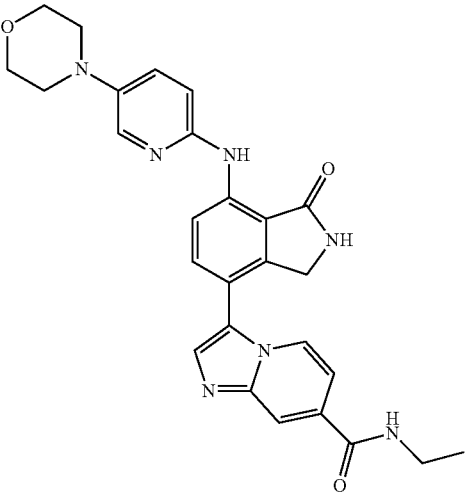 [SMILES: CCNC(=O)c1ccn2c(-c3ccc(Nc4ccc(N5CCOCC5)cn4)c4c3CNC4=O)cnc2c1] |
| I-208 | 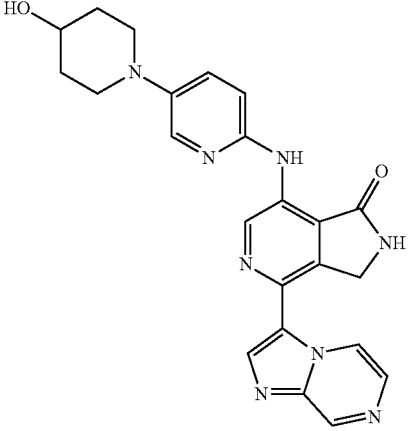 [SMILES: O=C1NCc2c(-c3cnc4cnccn34)ncc(Nc3ccc(N4CCC(O)CC4)cn3)c21] |

TABLE 1-continued

Selected Compounds

| # | Structure |
|---|---|
| I-209 | 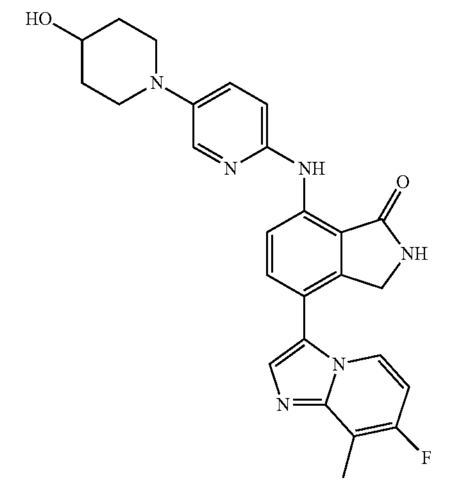 [SMILES: Cc1c(F)ccn2c(-c3ccc(Nc4ccc(N5CCC(O)CC5)cn4)c4c3CNC4=O)cnc12] |
| I-210 | 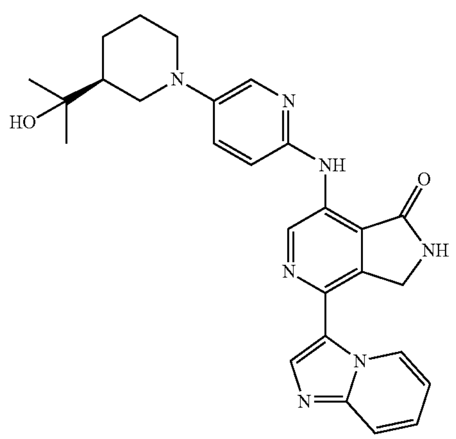 [SMILES: CC(C)(O)[C@H]1CCCN(c2ccc(Nc3cnc(-c4cnc5ccccn45)c4c3C(=O)NC4)nc2)C1] |
| I-211 | 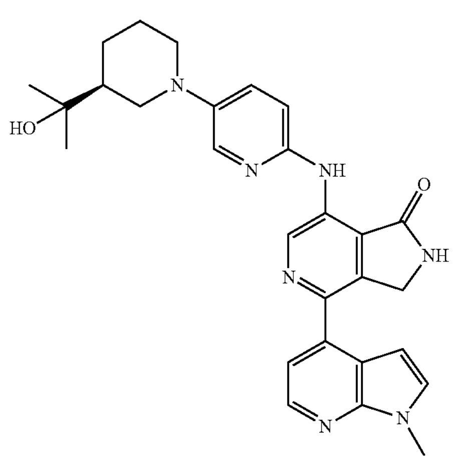 [SMILES: Cn1ccc2c(-c3ncc(Nc4ccc(N5CCC[C@H](C(C)(C)O)C5)cn4)c4c3CNC4=O)ccnc21] |

TABLE 1-continued
Selected Compounds
| # | Structure |
|---|---|
| I-212 | 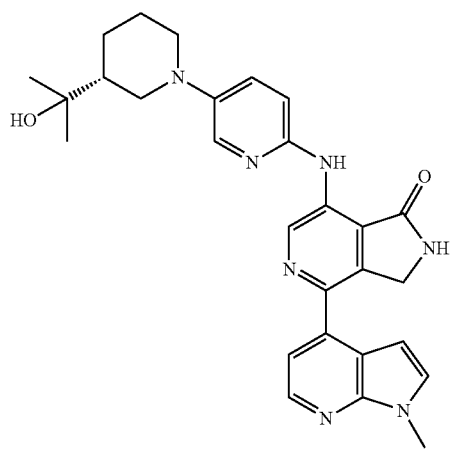 [SMILES: Cn1ccc2c(-c3ncc(Nc4ccc(N5CCC[C@@H](C(C)(C)O)C5)cn4)c4c3CNC4=O)ccnc21] |
| I-213 | 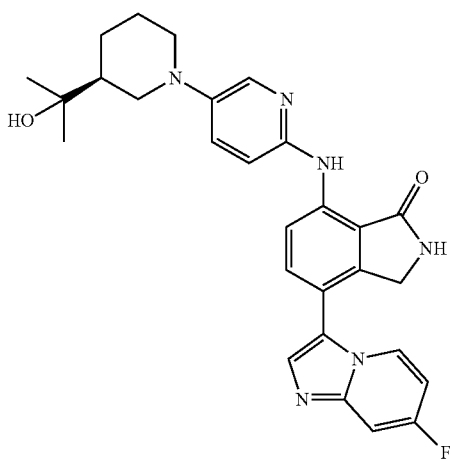 [SMILES: CC(C)(O)[C@H]1CCCN(c2ccc(Nc3ccc(-c4cnc5cc(F)ccn45)c4c3C(=O)NC4)nc2)C1] |
| I-214 | 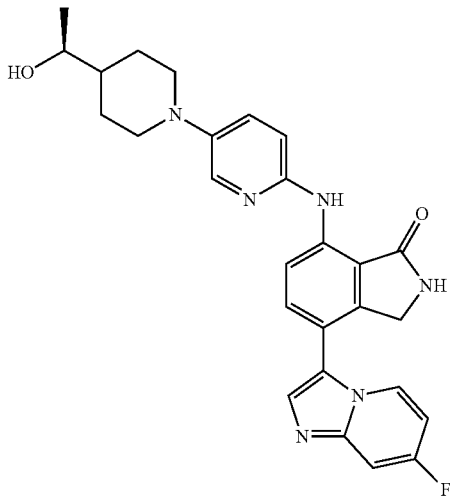 [SMILES: C[C@H](O)C1CCN(c2ccc(Nc3ccc(-c4cnc5cc(F)ccn45)c4c3C(=O)NC4)nc2)CC1] |

TABLE 1-continued
Selected Compounds
| # | Structure |
|---|---|
| I-215 | 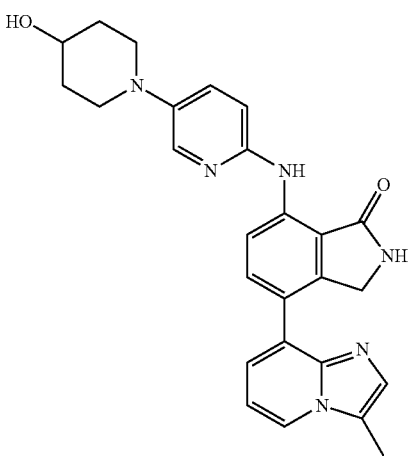 [SMILES: Cc1cnc2c(-c3ccc(Nc4ccc(N5CCC(O)CC5)cn4)c4c3CNC4=O)cccn12] |
| I-216 | 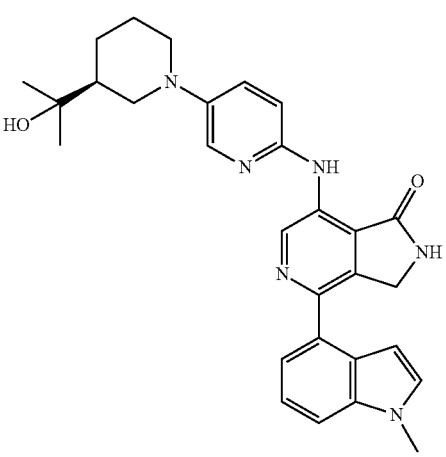 [SMILES: Cn1ccc2c(-c3ncc(Nc4ccc(N5CCC[C@H](C(C)(C)O)C5)cn4)c4c3CNC4=O)cccc21] |
| I-217 | 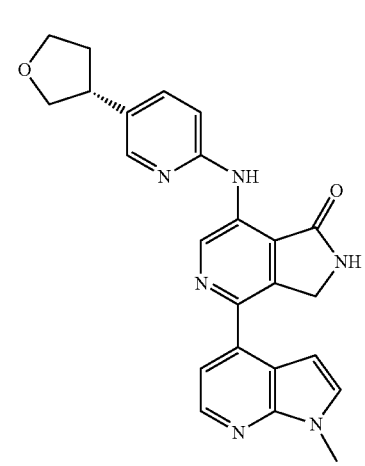 [SMILES: Cn1ccc2c(-c3ncc(Nc4ccc([C@H]5CCOC5)cn4)c4c3CNC4=O)ccnc21] |

TABLE 1-continued

Selected Compounds

| # | Structure |
|---|---|
| I-218 | 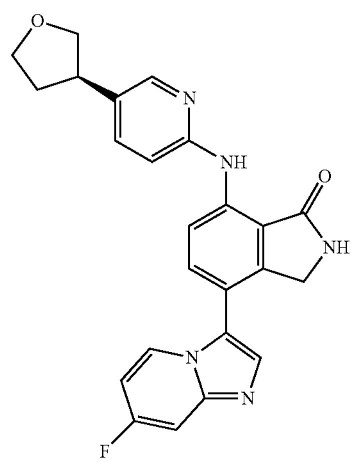 [SMILES: O=C1NCc2c(-c3cnc4cc(F)ccn34)ccc(Nc3ccc([C@H]4CCOC4)cn3)c21] |
| I-219 | 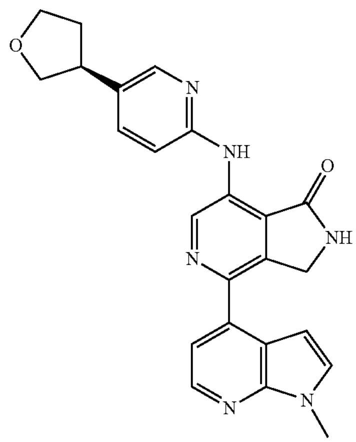 [SMILES: Cn1ccc2c(-c3ncc(Nc4ccc([C@@H]5CCOC5)cn4)c4c3CNC4=O)ccnc21] |
| I-220 | 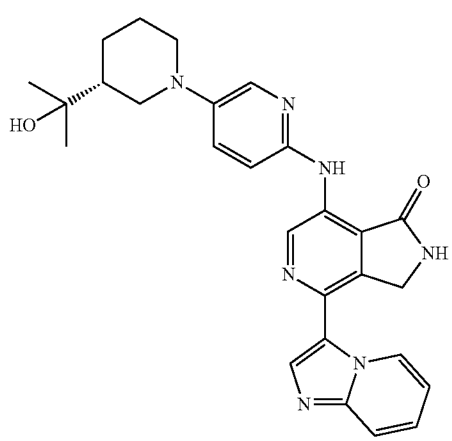 |

TABLE 1-continued

Selected Compounds

| # | Structure |
|---|---|
| I-221 | 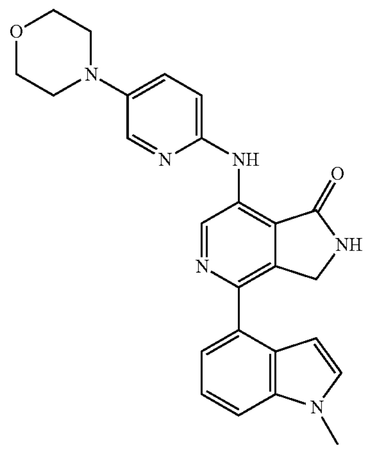 [SMILES: Cn1ccc2c(-c3ncc(Nc4ccc(N5CCOCC5)cn4)c4c3CNC4=O)cccc21] |
| I-222 | 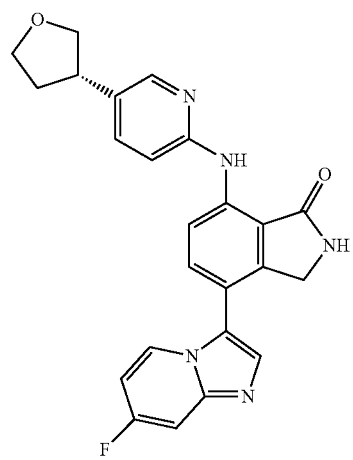 [SMILES: O=C1NCc2c(-c3cnc4cc(F)ccn34)ccc(Nc3ccc([C@@H]4CCOC4)cn3)c21] |
| I-223 | 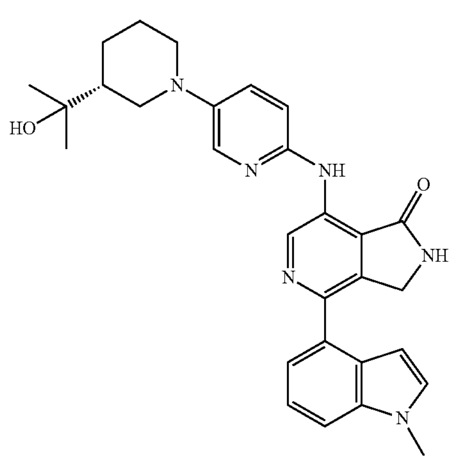 [SMILES: Cn1ccc2c(-c3ncc(Nc4ccc(N5CCC[C@@H](C(C)(C)O)C5)cn4)c4c3CNC4=O)cccc21] |

TABLE 1-continued
Selected Compounds
| # | Structure |
|---|---|
| I-224 | 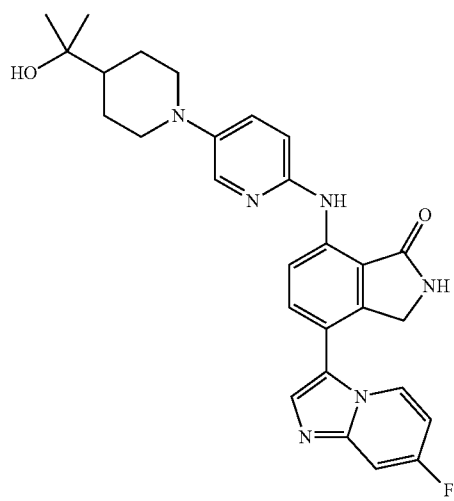 [SMILES: CC(C)(O)C1CCN(c2ccc(Nc3ccc(-c4cnc5cc(F)ccn45)c4c3C(=O)NC4)nc2)CC1] |
| I-225 | 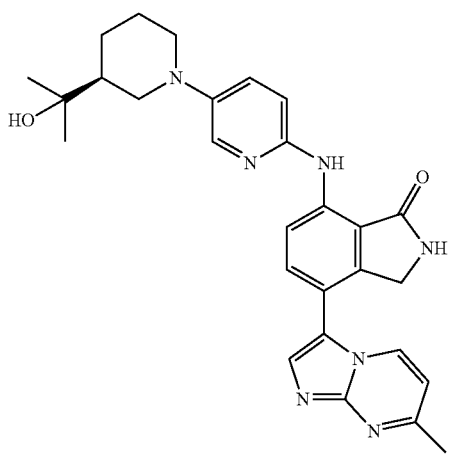 [SMILES: Cc1ccn2c(-c3ccc(Nc4ccc(N5CCC[C@H](C(C)(C)O)C5)cn4)c4c3CNC4=O)cnc2n1] |
| I-226 | 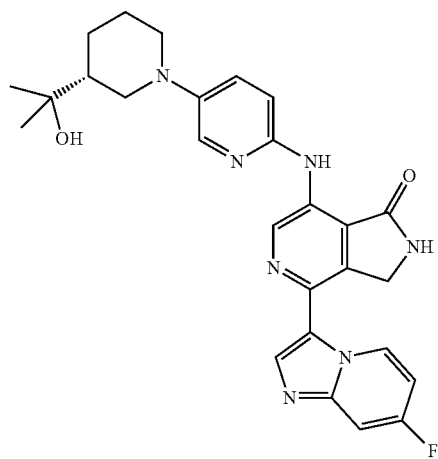 [SMILES: CC(C)(O)[C@@H]1CCCN(c2ccc(Nc3cnc(-c4cnc5cc(F)ccn45)c4c3C(=O)NC4)nc2)C1] |

TABLE 1-continued
Selected Compounds
| # | Structure |
|---|---|
| I-227 | 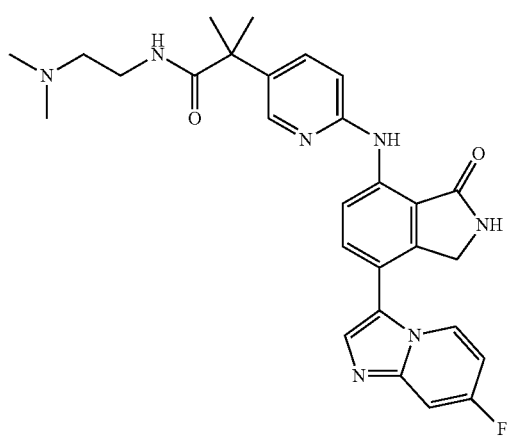 [SMILES: CN(C)CCNC(=O)C(C)(C)c1ccc(Nc2ccc(-c3cnc4cc(F)ccn34)c3c2C(=O)NC3)nc1] |
| I-228 | 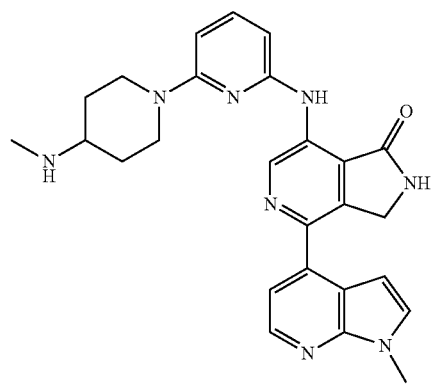 [SMILES: CNC1CCN(c2cccc(Nc3cnc(-c4ccnc5c4ccn5C)c4c3C(=O)NC4)n2)CC1] |
| I-229 | 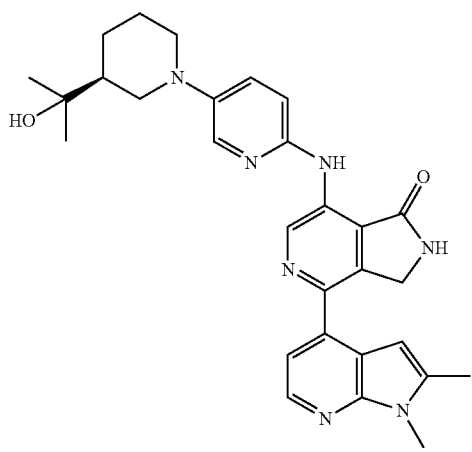 [SMILES: Cc1cc2c(-c3ncc(Nc4ccc(N5CCC[C@H](C(C)(C)O)C5)cn4)c4c3CNC4=O)ccnc2n1C] |

TABLE 1-continued
| | Selected Compounds |
|---|---|
| # | Structure |
I-230
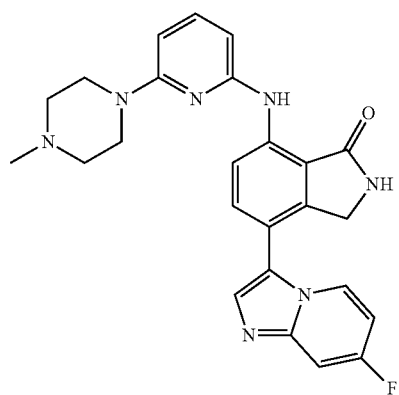 [SMILES: CN1CCN(c2cccc(Nc3ccc(-c4cnc5cc(F)ccn45)c4c3C(=O)NC4)n2)CC1]
I-231
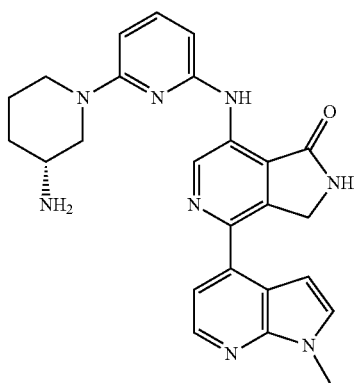 [SMILES: Cn1ccc2c(-c3ncc(Nc4cccc(N5CCC[C@@H](N)C5)n4)c4c3CNC4=O)ccnc21]
I-232
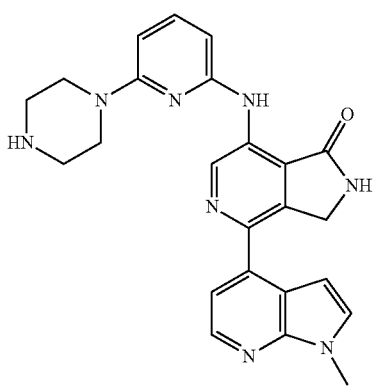 [SMILES: Cn1ccc2c(-c3ncc(Nc4cccc(N5CCNCC5)n4)c4c3CNC4=O)ccnc21]

TABLE 1-continued
Selected Compounds
| # | Structure |
|---|---|
| I-233 | 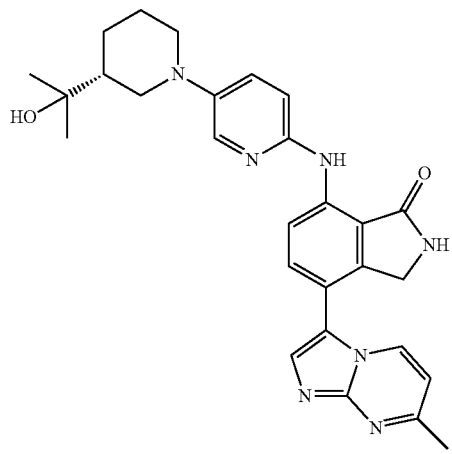 [SMILES: Cc1ccn2c(-c3ccc(Nc4ccc(N5CCC[C@@H](C(C)(C)O)C5)cn4)c4c3CNC4=O)cnc2n1] |
| I-234 | 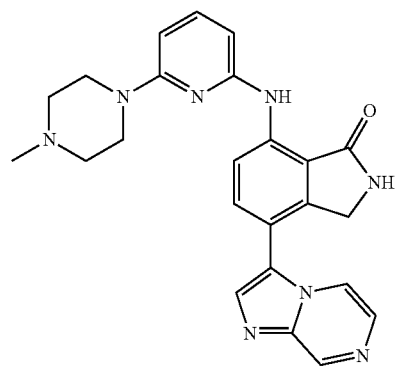 [SMILES: CN1CCN(c2cccc(Nc3ccc(-c4cnc5cnccn45)c4c3C(=O)NC4)n2)CC1] |
| I-235 | 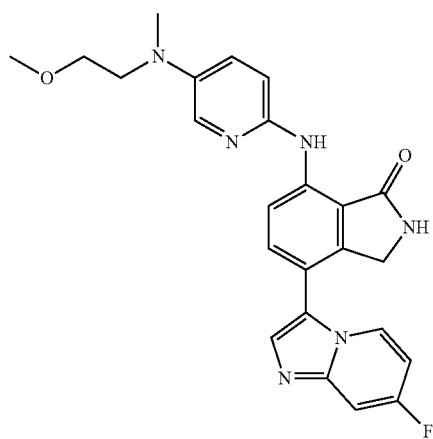 [SMILES: COCCN(C)c1ccc(Nc2ccc(-c3cnc4cc(F)ccn34)c3c2C(=O)NC3)nc1] |

TABLE 1-continued
Selected Compounds
| # | Structure |
|---|---|
| I-236 | 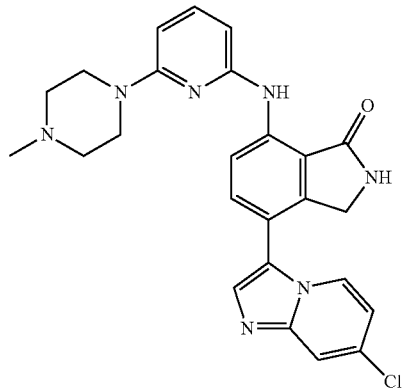 [SMILES: CN1CCN(c2cccc(Nc3ccc(-c4cnc5cc(Cl)ccn45)c4c3C(=O)NC4)n2)CC1] |
| I-237 | 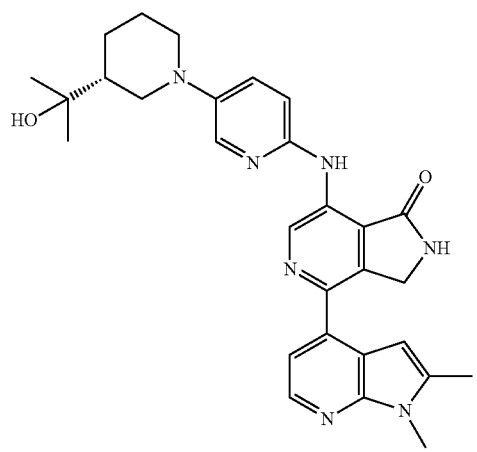 [SMILES: Cc1cc2c(-c3ncc(Nc4ccc(N5CCC[C@@H](C(C)(C)O)C5)cn4)c4c3CNC4=O)ccnc2n1C] |
| I-238 | 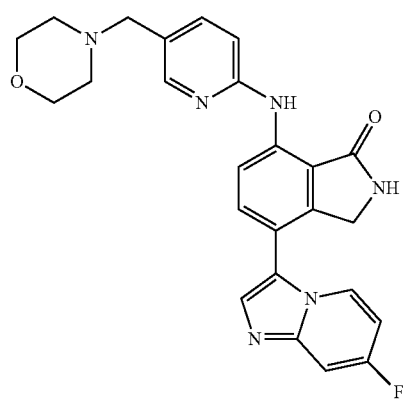 [SMILES: O=C1NCc2c(-c3cnc4cc(F)ccn34)ccc(Nc3ccc(CN4CCOCC4)cn3)c21] |

TABLE 1-continued
Selected Compounds
| # | Structure |
|---|---|
| I-239 | 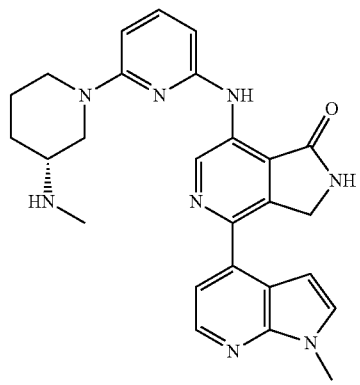 [SMILES: CN[C@@H]1CCCN(c2cccc(Nc3cnc(-c4ccnc5c4ccn5C)c4c3C(=O)NC4)n2)C1] |
| I-240 | 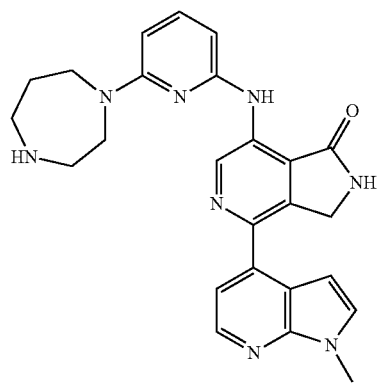 [SMILES: Cn1ccc2c(-c3ncc(Nc4cccc(N5CCCNCC5)n4)c4c3CNC4=O)ccnc21] |
| I-241 | 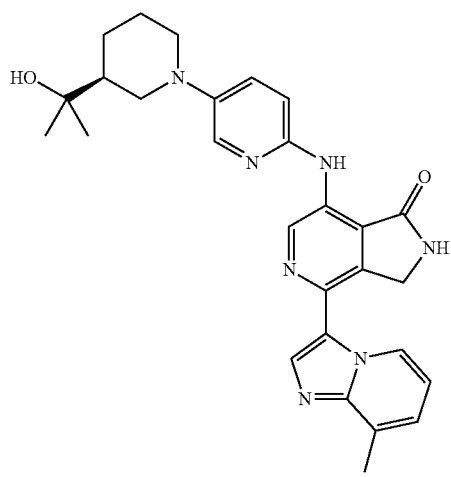 [SMILES: Cc1cccn2c(-c3ncc(Nc4ccc(N5CCC[C@H](C(C)(C)O)C5)cn4)c4c3CNC4=O)cnc12] |

TABLE 1-continued
Selected Compounds
| # | Structure |
|---|---|
| I-242 | 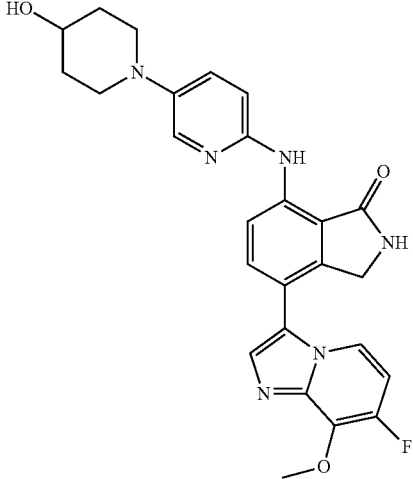 [SMILES: COc1c(F)ccn2c(-c3ccc(Nc4ccc(N5CCC(O)CC5)cn4)c4c3CNC4=O)cnc12] |
| I-243 | 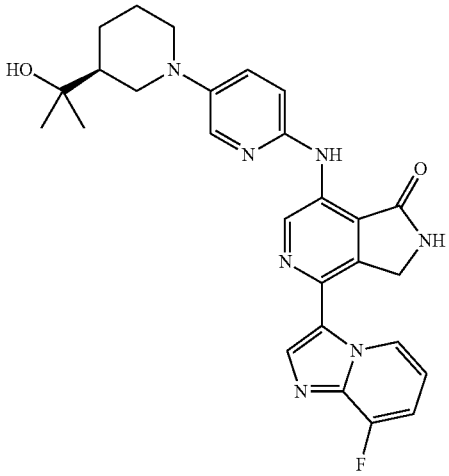 [SMILES: CC(C)(O)[C@H]1CCCN(c2ccc(Nc3cnc(-c4cnc5c(F)cccn45)c4c3C(=O)NC4)nc2)C1] |
| I-244 | 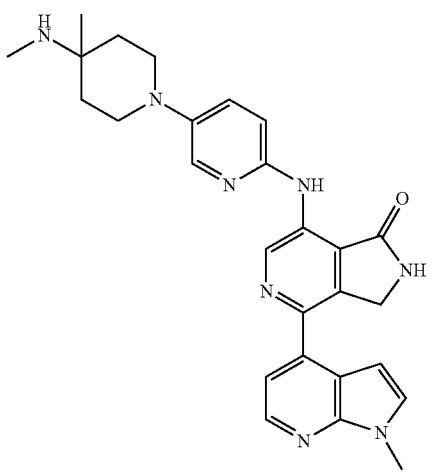 [SMILES: CNC1(C)CCN(c2ccc(Nc3cnc(-c4ccnc5c4ccn5C)c4c3C(=O)NC4)nc2)CC1] |

TABLE 1-continued
Selected Compounds
| # | Structure |
|---|---|
| I-245 | 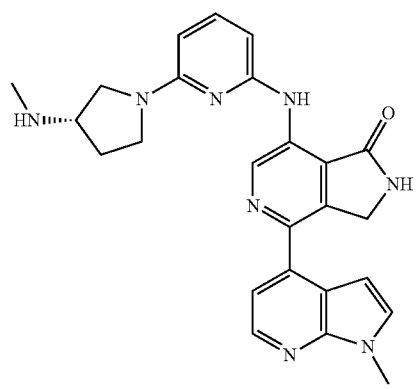 [SMILES: CN[C@H]1CCN(c2cccc(Nc3cnc(-c4ccnc5c4ccn5C)c4c3C(=O)NC4)n2)C1] |
| I-246 | 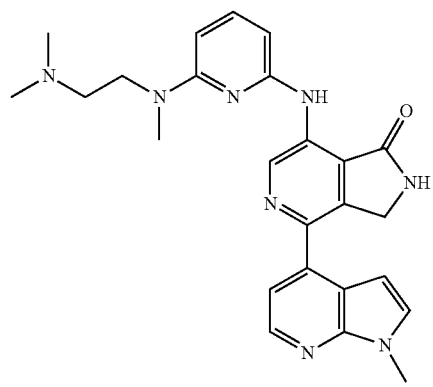 [SMILES: CN(C)CCN(C)c1cccc(Nc2cnc(-c3ccnc4c3ccn4C)c3c2C(=O)NC3)n1] |
| I-247 | 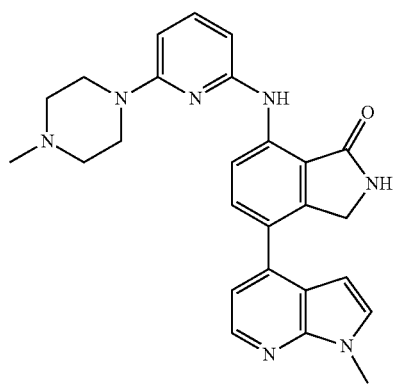 [SMILES: CN1CCN(c2cccc(Nc3ccc(-c4ccnc5c4ccn5C)c4c3C(=O)NC4)n2)CC1] |

TABLE 1-continued
Selected Compounds
| # | Structure |
|---|---|
| I-248 | 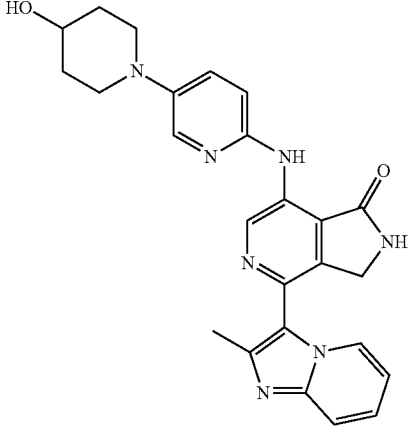 [SMILES: Cc1nc2ccccn2c1-c1ncc(Nc2ccc(N3CCC(O)CC3)cn2)c2c1CNC2=O] |
| I-249 | 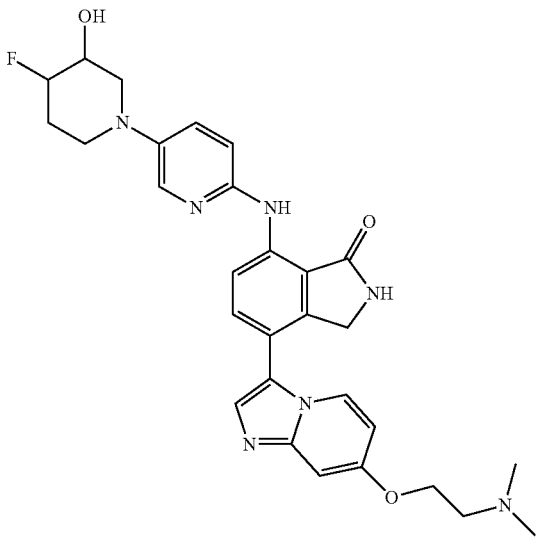 [SMILES: CN(C)CCOc1ccn2c(-c3ccc(Nc4ccc(N5CCC(F)C(O)C5)cn4)c4c3CNC4=O)cnc2c1] |
| I-250 | 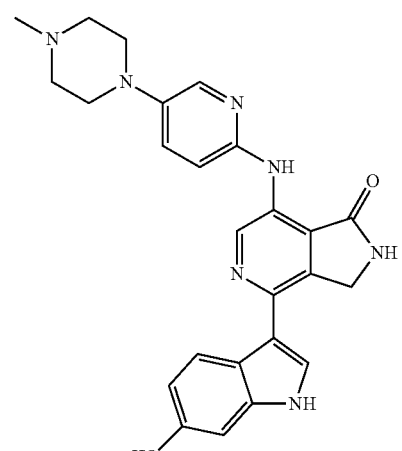 |

TABLE 1-continued
| Selected Compounds | |
|---|---|
| # | Structure |
| I-251 | 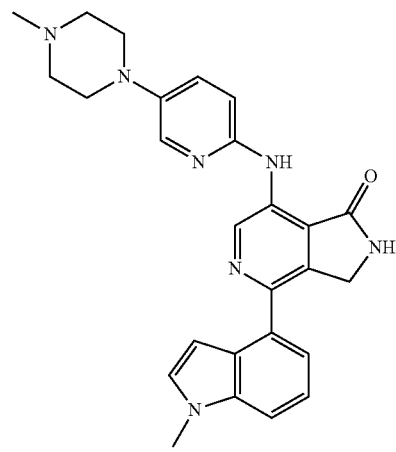 [SMILES: CN1CCN(c2ccc(Nc3cnc(-c4cccc5c4ccn5C)c4c3C(=O)NC4)nc2)CC1] |
| I-252 | 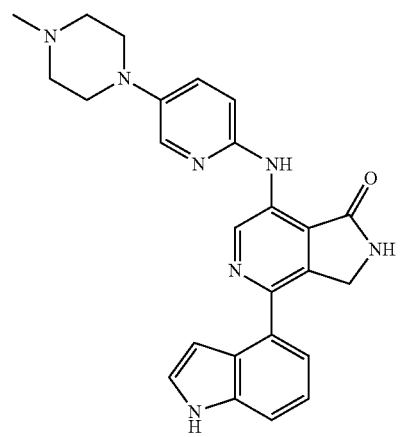 [SMILES: CN1CCN(c2ccc(Nc3cnc(-c4cccc5[nH]ccc45)c4c3C(=O)NC4)nc2)CC1] |
| I-253 | 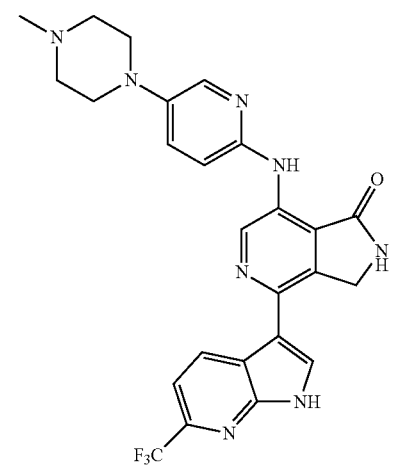 [SMILES: CN1CCN(c2ccc(Nc3cnc(-c4c[nH]c5nc(C(F)(F)F)ccc45)c4c3C(=O)NC4)nc2)CC1] |

TABLE 1-continued
Selected Compounds
| # | Structure |
|---|---|
| I-254 | 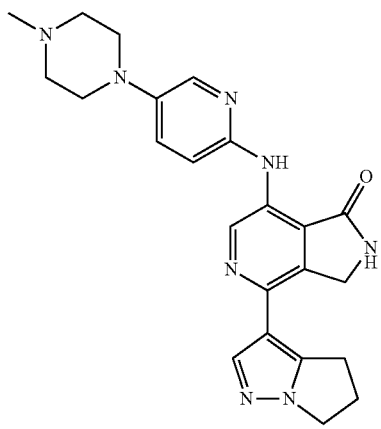 [SMILES: CN1CCN(c2ccc(Nc3cnc(-c4cnn5c4CCC5)c4c3C(=O)NC4)nc2)CC1] |
| I-255 | 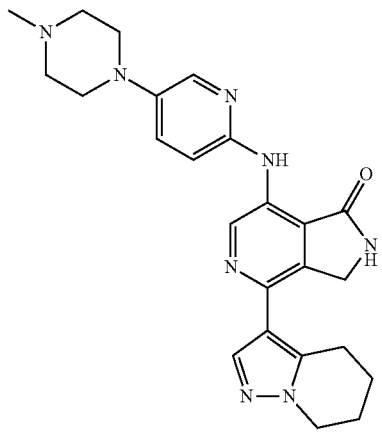 [SMILES: CN1CCN(c2ccc(Nc3cnc(-c4cnn5c4CCCC5)c4c3C(=O)NC4)nc2)CC1] |
| I-256 | 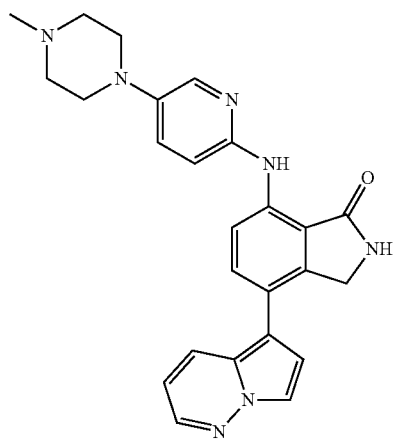 [SMILES: CN1CCN(c2ccc(Nc3ccc(-c4ccn5ncccc45)c4c3C(=O)NC4)nc2)CC1] |

TABLE 1-continued

Selected Compounds

| # | Structure |
|---|---|
| I-257 | 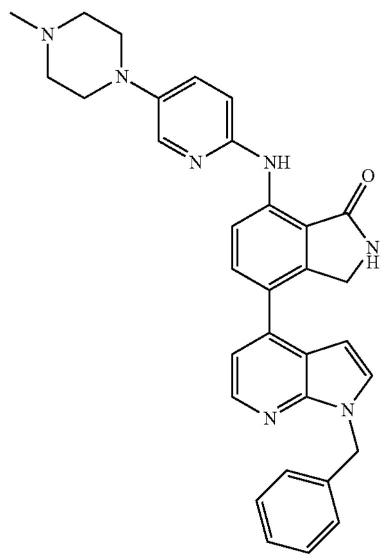 [SMILES: CN1CCN(c2ccc(Nc3ccc(-c4ccnc5c4ccn5Cc4ccccc4)c4c3C(=O)NC4)nc2)CC1] |
| I-258 | 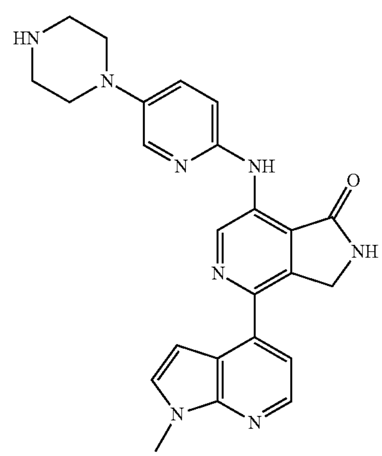 |
| I-259 | 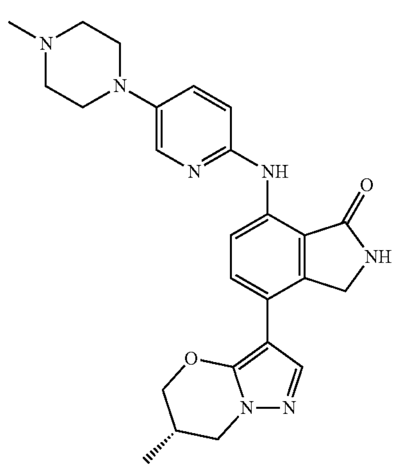 [SMILES: C[C@@H]1COc2c(-c3ccc(Nc4ccc(N5CCN(C)CC5)cn4)c4c3CNC4=O)cnn2C1] |

TABLE 1-continued
Selected Compounds
| # | Structure |
|---|---|
| I-260 | 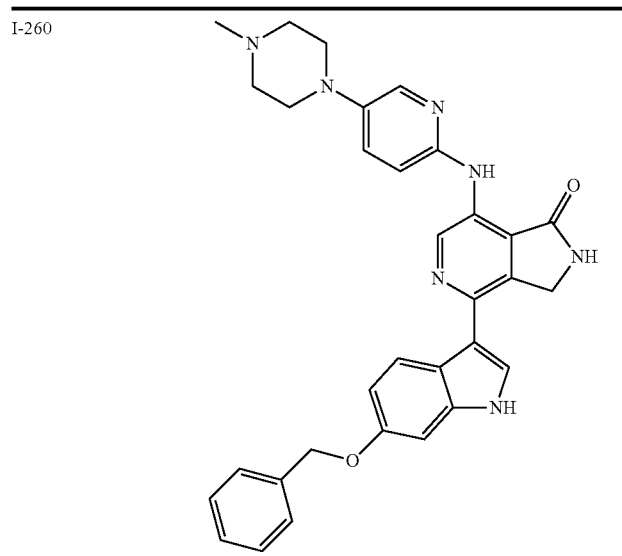 |
| I-261 | 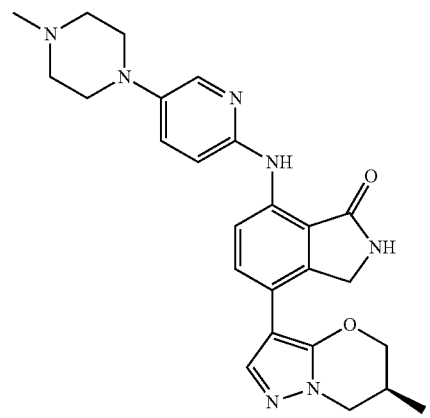 |
| I-262 | 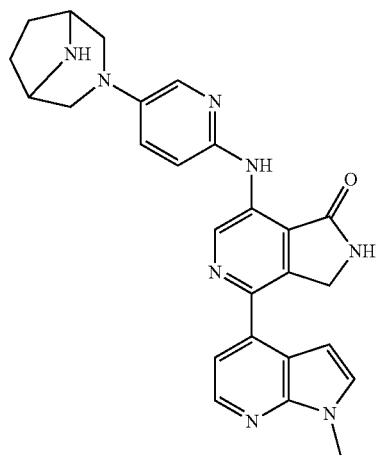 [SMILES: Cn1ccc2c(-c3ncc(Nc4ccc(N5CC6CCC(C5)N6)cn4)c4c3CNC4=O)ccnc21] |

TABLE 1-continued
Selected Compounds
| # | Structure |
|---|---|
| I-263 | 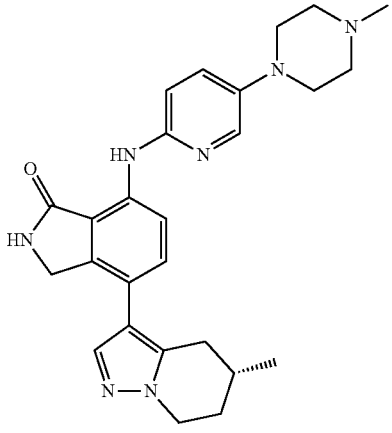 [SMILES: C[C@@H]1CCn2ncc(-c3ccc(Nc4ccc(N5CCN(C)CC5)cn4)c4c3CNC4=O)c2C1] |
| I-264 | 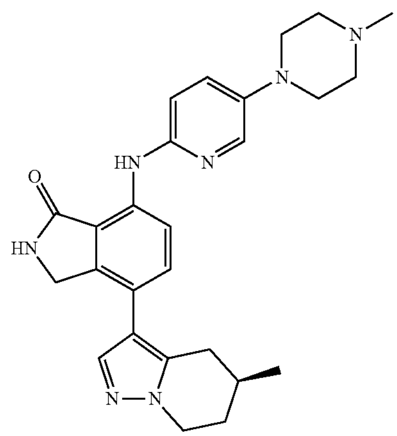 [SMILES: C[C@H]1CCn2ncc(-c3ccc(Nc4ccc(N5CCN(C)CC5)cn4)c4c3CNC4=O)c2C1] |
| I-265 | 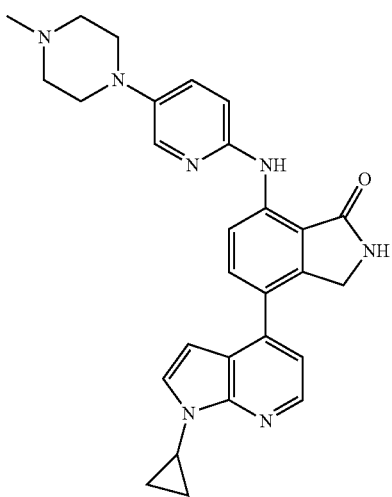 [SMILES: CN1CCN(c2ccc(Nc3ccc(-c4ccnc5c4ccn5C4CC4)c4c3C(=O)NC4)nc2)CC1] |

TABLE 1-continued
Selected Compounds
| # | Structure |
|---|---|
| I-266 | 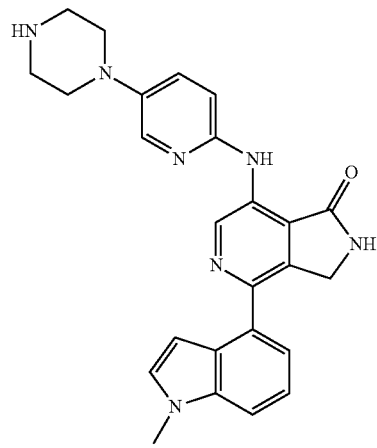 [SMILES: Cn1ccc2c(-c3ncc(Nc4ccc(N5CCNCC5)cn4)c4c3CNC4=O)cccc21] |
| I-267 | 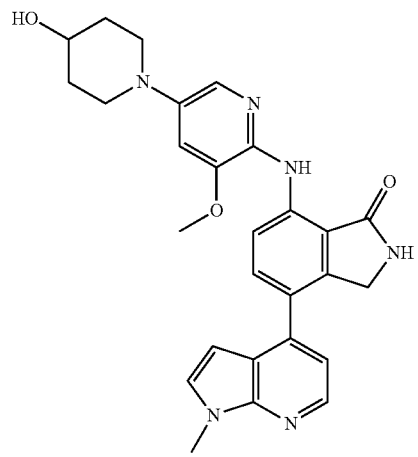 [SMILES: COc1cc(N2CCC(O)CC2)cnc1Nc1ccc(-c2ccnc3c2ccn3C)c2c1C(=O)NC2] |
| I-268 | 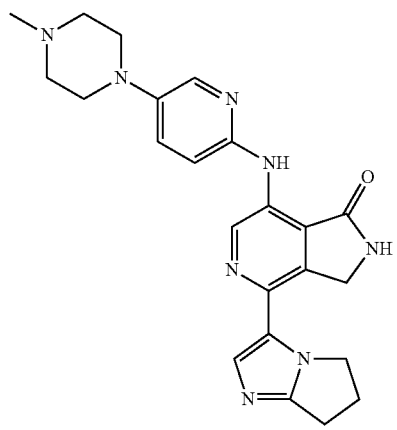 [SMILES: CN1CCN(c2ccc(Nc3cnc(-c4cnc5n4CCC5)c4c3C(=O)NC4)nc2)CC1] |

TABLE 1-continued

Selected Compounds

| # | Structure |
|---|---|
| I-269 | 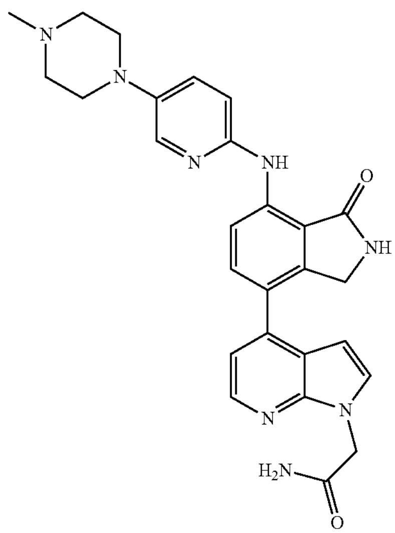 [SMILES: CN1CCN(c2ccc(Nc3ccc(-c4ccnc5c4ccn5CC(N)=O)c4c3C(=O)NC4)nc2)CC1] |
| I-270 | 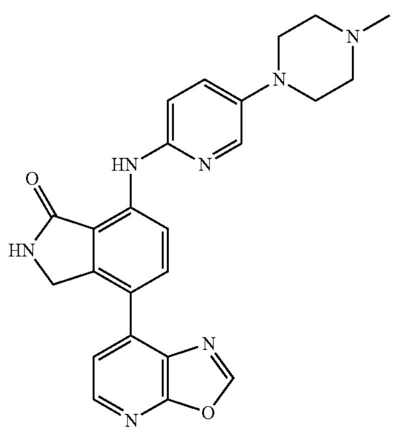 [SMILES: CN1CCN(c2ccc(Nc3ccc(-c4ccnc5ocnc45)c4c3C(=O)NC4)nc2)CC1] |
| I-271 | 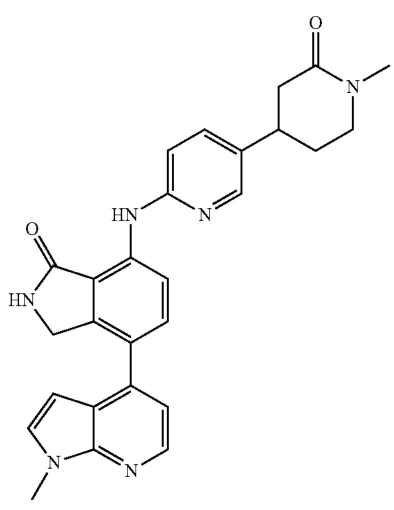 [SMILES: CN1CCC(c2ccc(Nc3ccc(-c4ccnc5c4ccn5C)c4c3C(=O)NC4)nc2)CC1=O] |

TABLE 1-continued
| Selected Compounds | |
|---|---|
| # | Structure |
I-272 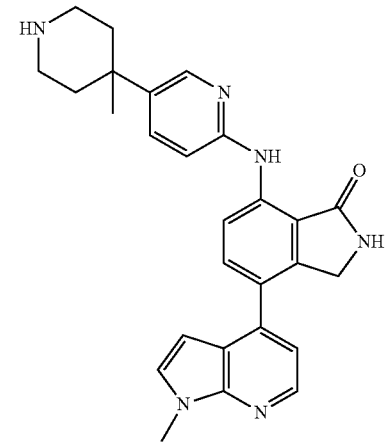 [SMILES: Cn1ccc2c(-c3ccc(Nc4ccc(C5(C)CCNCC5)cn4)c4c3CNC4=O)ccnc21]
I-273 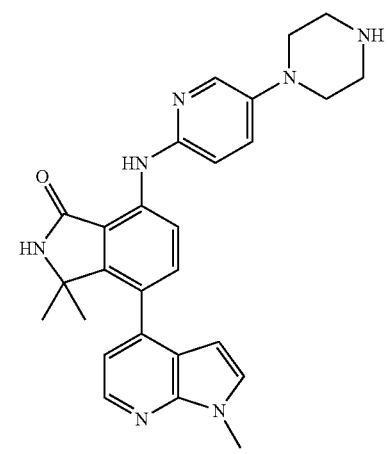 [SMILES: Cn1ccc2c(-c3ccc(Nc4ccc(N5CCNCC5)cn4)c4c3C(C)(C)NC4=O)ccnc21]
I-274 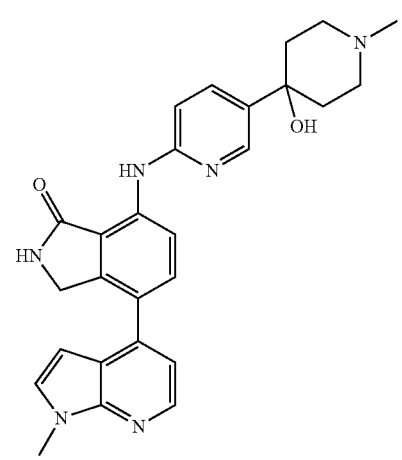 [SMILES: CN1CCC(O)(c2ccc(Nc3ccc(-c4ccnc5c4ccn5C)c4c3C(=O)NC4)nc2)CC1]

TABLE 1-continued
Selected Compounds
| # | Structure |
|---|---|
| I-275 | 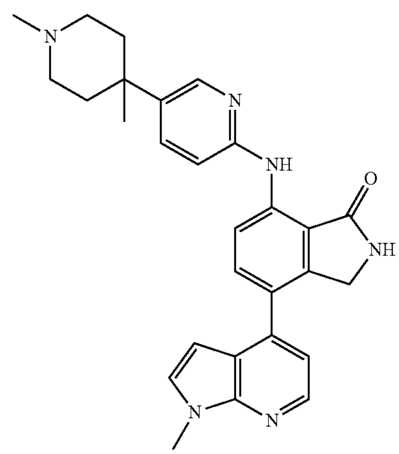 [SMILES: CN1CCC(C)(c2ccc(Nc3ccc(-c4ccnc5c4ccn5C)c4c3C(=O)NC4)nc2)CC1] |
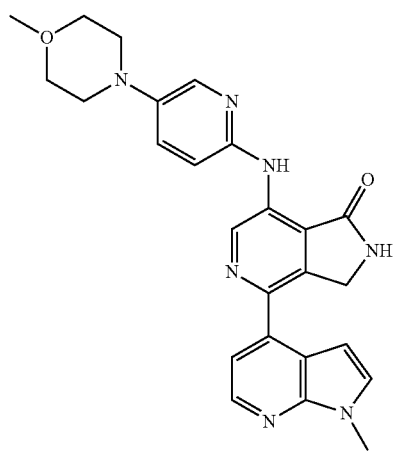
I-276
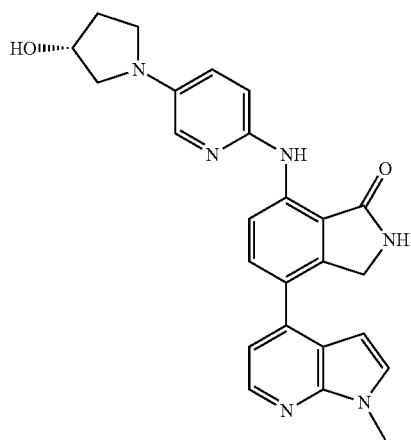 [SMILES: Cn1ccc2c(-c3ccc(Nc4ccc(N5CC[C@@H](O)C5)cn4)c4c3CNC4=O)ccnc21]
I-278

TABLE 1-continued
| Selected Compounds | |
|---|---|
| # | Structure |
| I-279 | 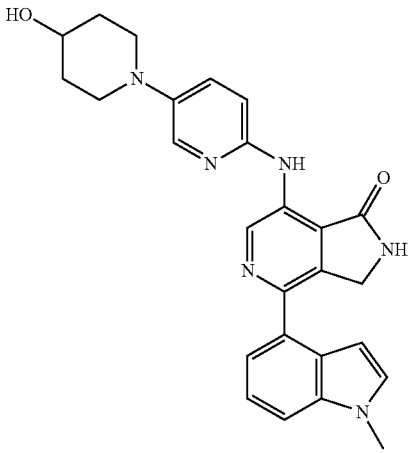 [SMILES: Cn1ccc2c(-c3ncc(Nc4ccc(N5CCC(O)CC5)cn4)c4c3CNC4=O)cccc21] |
| I-280 | 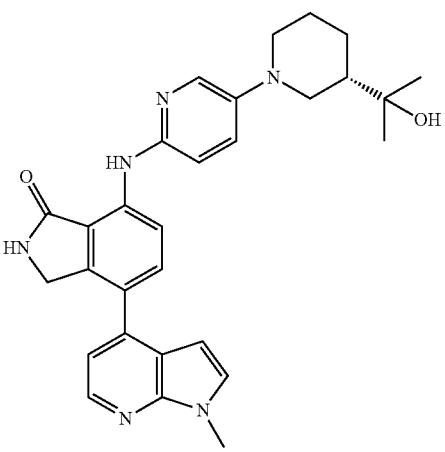 [SMILES: Cn1ccc2c(-c3ccc(Nc4ccc(N5CCC[C@H](C(C)(C)O)C5)cn4)c4c3CNC4=O)ccnc21] |
| I-281 | 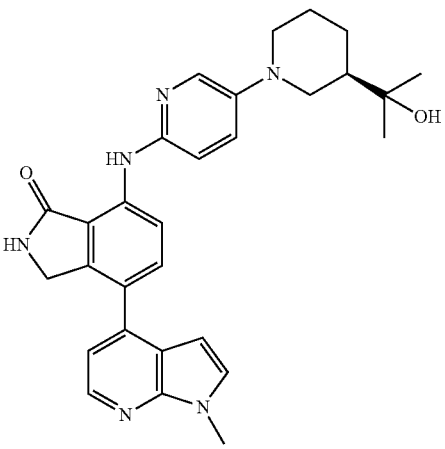 [SMILES: Cn1ccc2c(-c3ccc(Nc4ccc(N5CCC[C@@H](C(C)(C)O)C5)cn4)c4c3CNC4=O)ccnc21] |

TABLE 1-continued
Selected Compounds
| # | Structure |
|---|---|
| I-282 | 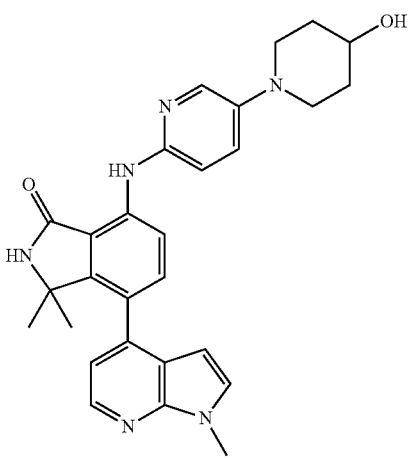 [SMILES: Cn1ccc2c(-c3ccc(Nc4ccc(N5CCC(O)CC5)cn4)c4c3C(C)(C)NC4=O)ccnc21] |
| I-283 | 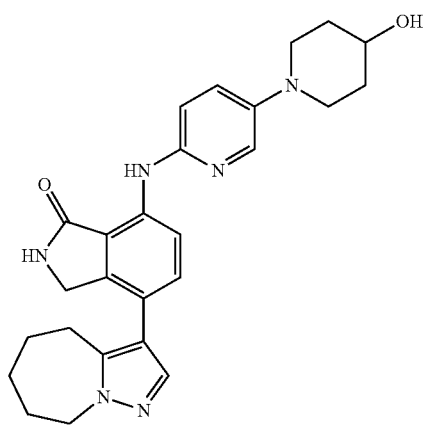 [SMILES: O=C1NCc2c(-c3cnn4c3CCCCC4)ccc(Nc3ccc(N4CCC(O)CC4)cn3)c21] |
| I-284 | 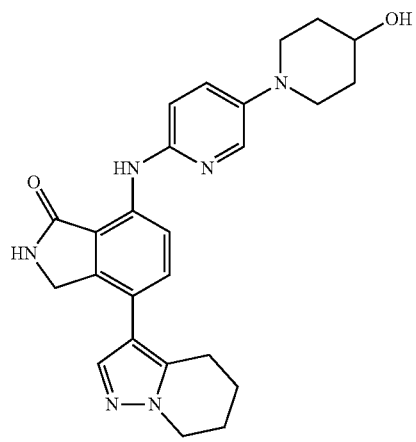 |

TABLE 1-continued
Selected Compounds
| # | Structure |
|---|---|
| I-285 | 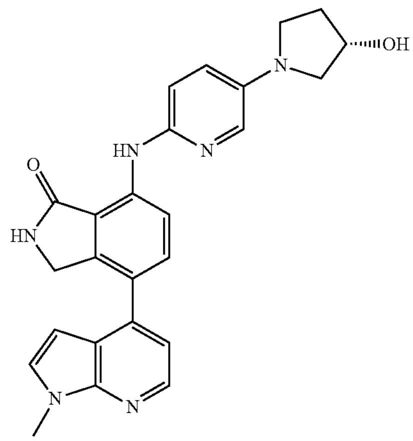 [SMILES: Cn1ccc2c(-c3ccc(Nc4ccc(N5CC[C@H](O)C5)cn4)c4c3CNC4=O)ccnc21] |

I-286
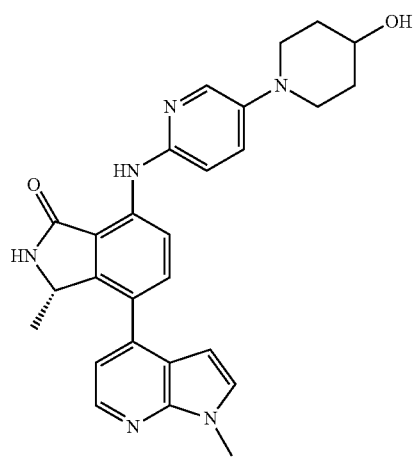 [SMILES: C[C@@H]1NC(=O)c2c(Nc3ccc(N4CCC(O)CC4)cn3)ccc(-c3ccnc4c3ccn4C)c21]
I-287

TABLE 1-continued
| Selected Compounds | |
|---|---|
| # | Structure |
| I-288 | 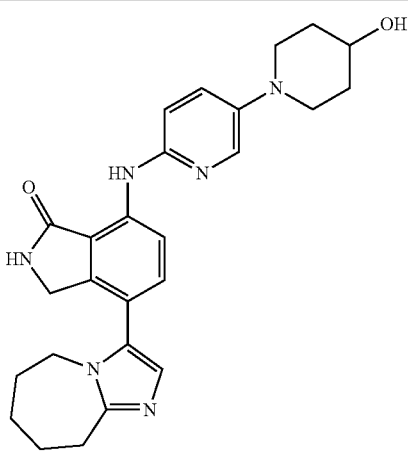 [SMILES: O=C1NCc2c(-c3cnc4n3CCCCC4)ccc(Nc3ccc(N4CCC(O)CC4)cn3)c21] |
| I-289 | 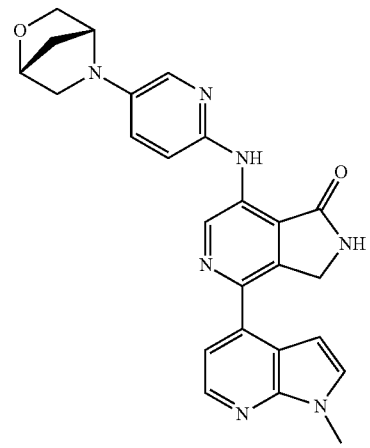 [SMILES: Cn1ccc2c(-c3ncc(Nc4ccc(N5C[C@H]6C[C@@H]5CO6)cn4)c4c3CNC4=O)ccnc21] |
| I-290 | 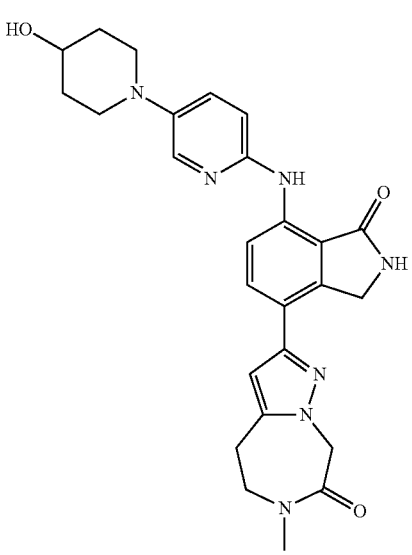 [SMILES: CN1CCc2cc(-c3ccc(Nc4ccc(N5CCC(O)CC5)cn4)c4c3CNC4=O)nn2CC1=O] |

TABLE 1-continued
Selected Compounds
| # | Structure |
|---|---|
| I-291 | 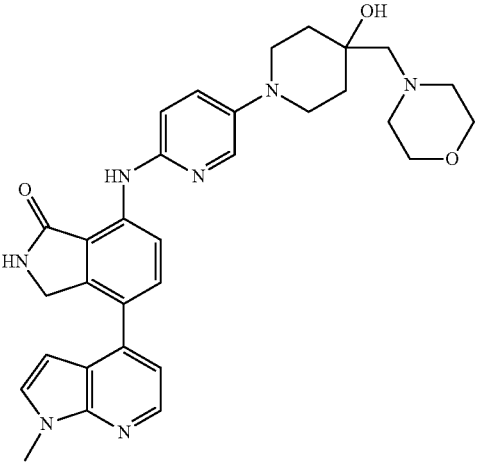 [SMILES: Cn1ccc2c(-c3ccc(Nc4ccc(N5CCC(O)(CN6CCOCC6)CC5)cn4)c4c3CNC4=O)ccnc21] |
| I-292 | 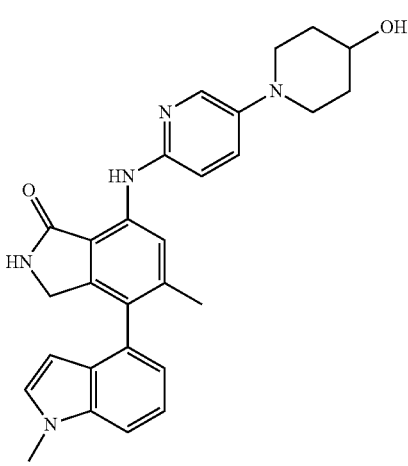 [SMILES: Cc1cc(Nc2ccc(N3CCC(O)CC3)cn2)c2c(c1-c1cccc3c1ccn3C)CNC2=O] |
| I-293 | 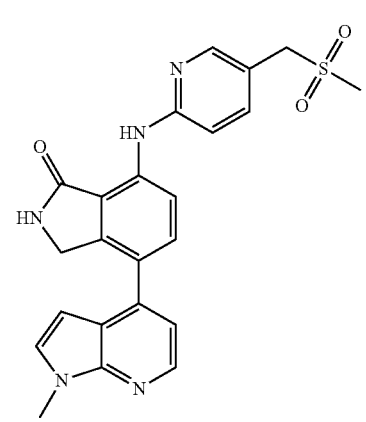 [SMILES: Cn1ccc2c(-c3ccc(Nc4ccc(CS(C)(=O)=O)cn4)c4c3CNC4=O)ccnc21] |

TABLE 1-continued

Selected Compounds

| # | Structure |
|---|---|
| I-294 | 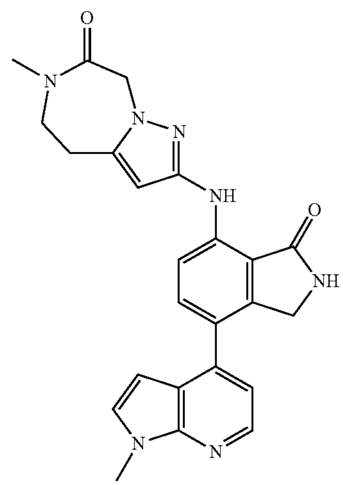 [SMILES: CN1CCc2cc(Nc3ccc(-c4ccnc5c4ccn5C)c4c3C(=O)NC4)nn2CC1=O] |
| I-295 | 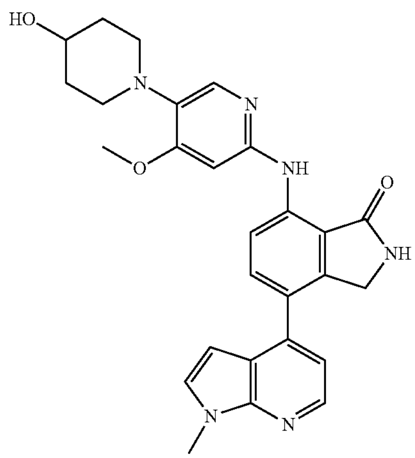 [SMILES: COc1cc(Nc2ccc(-c3ccnc4c3ccn4C)c3c2C(=O)NC3)ncc1N1CCC(O)CC1] |
| I-296 | 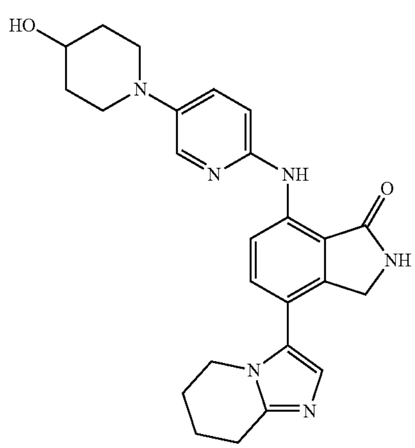 [SMILES: O=C1NCc2c(-c3cnc4n3CCCC4)ccc(Nc3ccc(N4CCC(O)CC4)cn3)c21] |

TABLE 1-continued
Selected Compounds
| # | Structure |
|---|---|
| I-297 | 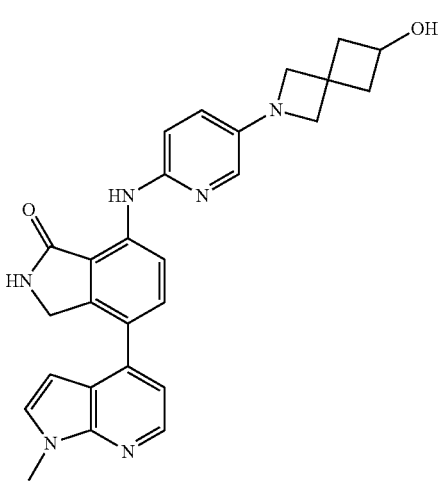 [SMILES: Cn1ccc2c(-c3ccc(Nc4ccc(N5CC6(CC(O)C6)C5)cn4)c4c3CNC4=O)ccnc21] |
| I-298 | 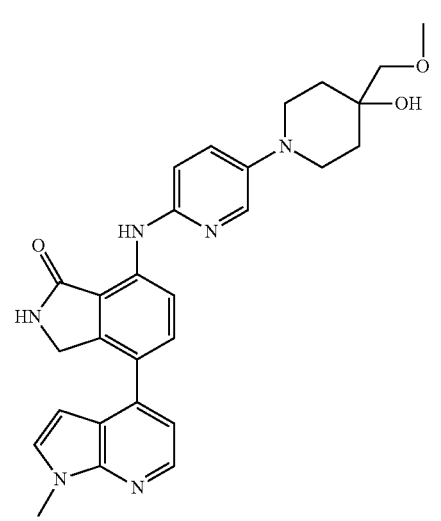 [SMILES: COCC1(O)CCN(c2ccc(Nc3ccc(-c4ccnc5c4ccn5C)c4c3C(=O)NC4)nc2)CC1] |
| I-299 | 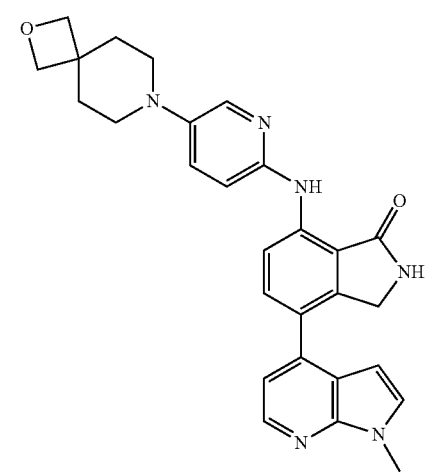 [SMILES: Cn1ccc2c(-c3ccc(Nc4ccc(N5CCC6(CC5)COC6)cn4)c4c3CNC4=O)ccnc21] |

TABLE 1-continued
Selected Compounds
| # | Structure |
|---|---|
| I-300 | 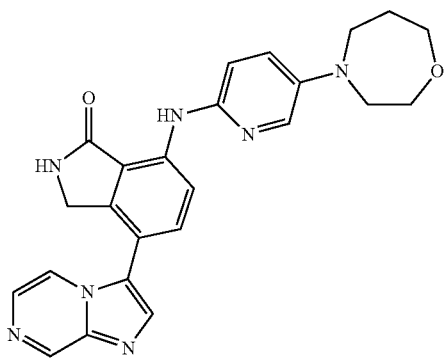 [SMILES: O=C1NCc2c(-c3cnc4cnccn34)ccc(Nc3ccc(N4CCCOCC4)cn3)c21] |
| I-301 | 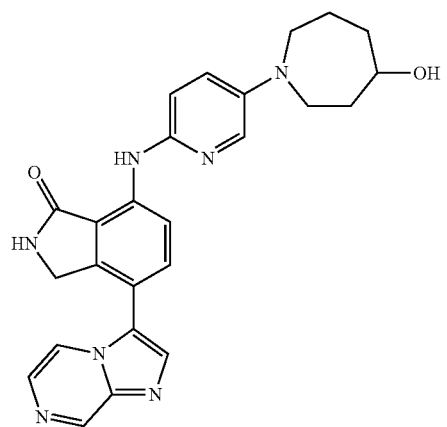 [SMILES: O=C1NCc2c(-c3cnc4cnccn34)ccc(Nc3ccc(N4CCCC(O)CC4)cn3)c21] |
| I-302 | 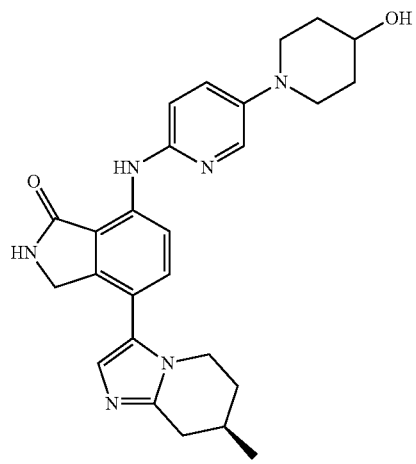 [SMILES: C[C@@H]1CCn2c(-c3ccc(Nc4ccc(N5CCC(O)CC5)cn4)c4c3CNC4=O)cnc2C1] |

TABLE 1-continued
Selected Compounds
| # | Structure |
|---|---|
| I-303 | 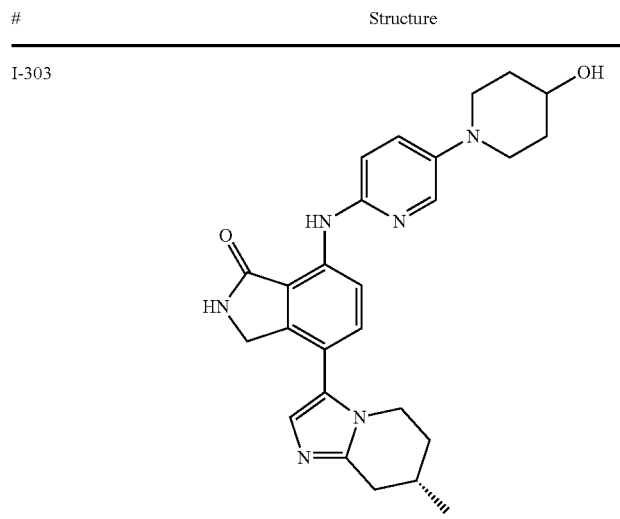 |
| I-304 | 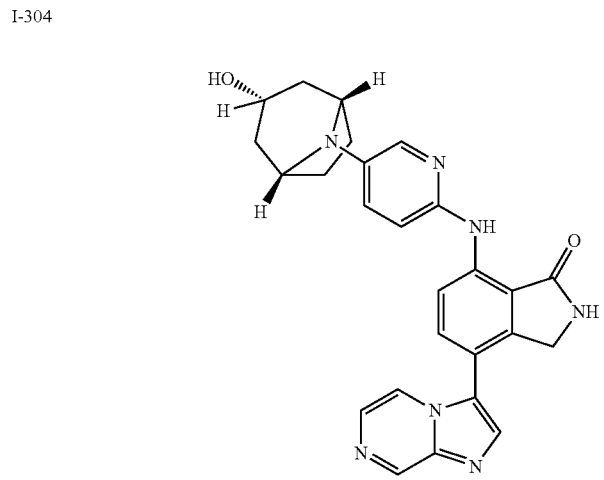 |
| I-305 | 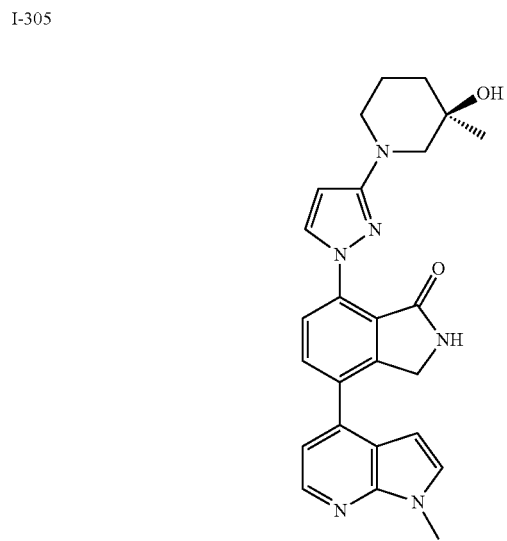 |

TABLE 1-continued

Selected Compounds

| # | Structure |
|---|---|
| I-306 | 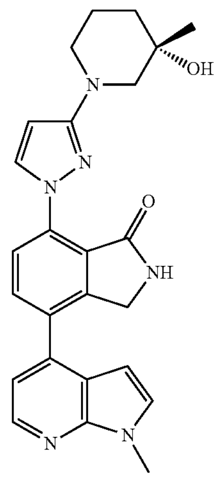 [SMILES: Cn1ccc2c(-c3ccc(-n4ccc(N5CCC[C@](C)(O)C5)n4)c4c3CNC4=O)ccnc21] |
| I-307 | 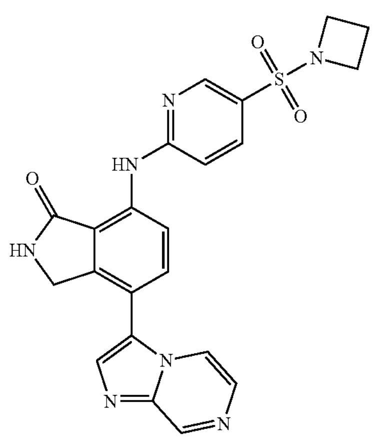 [SMILES: O=C1NCc2c(-c3cnc4cnccn34)ccc(Nc3ccc(S(=O)(=O)N4CCC4)cn3)c21] |
| I-308 | 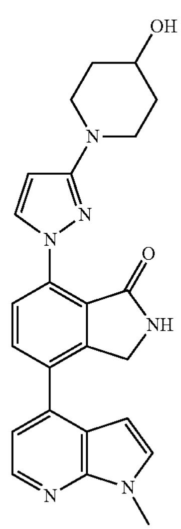 [SMILES: Cn1ccc2c(-c3ccc(-n4ccc(N5CCC(O)CC5)n4)c4c3CNC4=O)ccnc21] |

TABLE 1-continued
Selected Compounds
| # | Structure |
|---|---|
| I-309 | 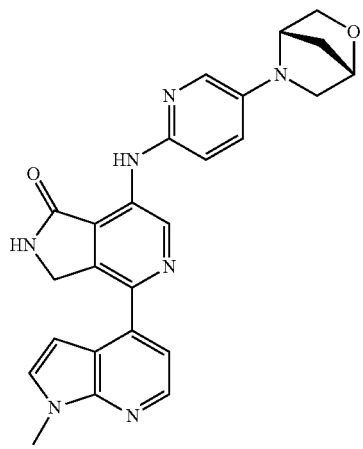 [SMILES: Cn1ccc2c(-c3ncc(Nc4ccc(N5C[C@@H]6C[C@H]5CO6)cn4)c4c3CNC4=O)ccnc21] |
| I-310 | 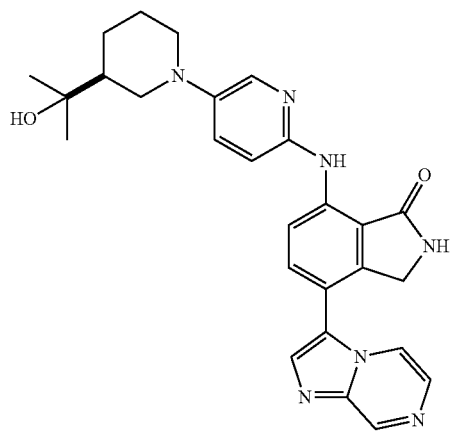 [SMILES: CC(C)(O)[C@H]1CCCN(c2ccc(Nc3ccc(-c4cnc5cnccn45)c4c3C(=O)NC4)nc2)C1] |
| I-311 | 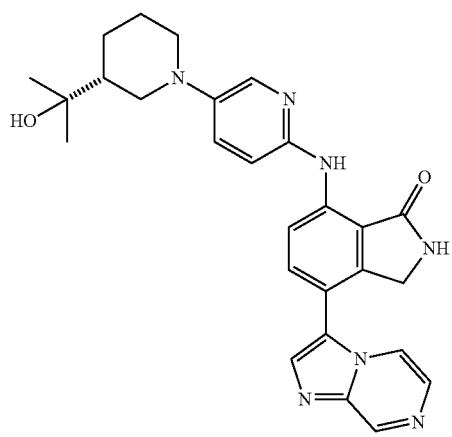 [SMILES: CC(C)(O)[C@@H]1CCCN(c2ccc(Nc3ccc(-c4cnc5cnccn45)c4c3C(=O)NC4)nc2)C1] |

TABLE 1-continued
Selected Compounds
| # | Structure |
|---|---|
| I-312 | 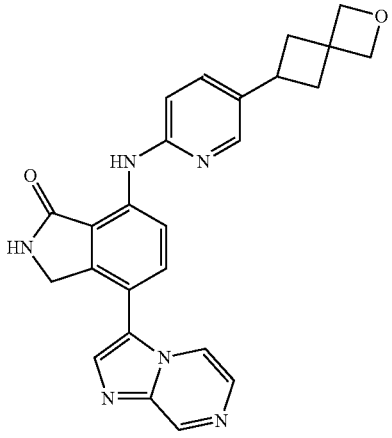 [SMILES: O=C1NCc2c(-c3cnc4cnccn34)ccc(Nc3ccc(C4CC5(COC5)C4)cn3)c21] |
| I-313 | 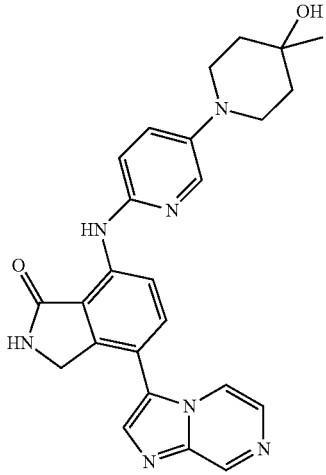 [SMILES: CC1(O)CCN(c2ccc(Nc3ccc(-c4cnc5cnccn45)c4c3C(=O)NC4)nc2)CC1] |
| I-314 | 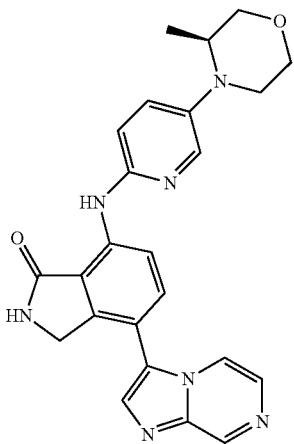 [SMILES: C[C@H]1COCCN1c1ccc(Nc2ccc(-c3cnc4cnccn34)c3c2C(=O)NC3)nc1] |

TABLE 1-continued
Selected Compounds
| # | Structure |
|---|---|
| I-315 | 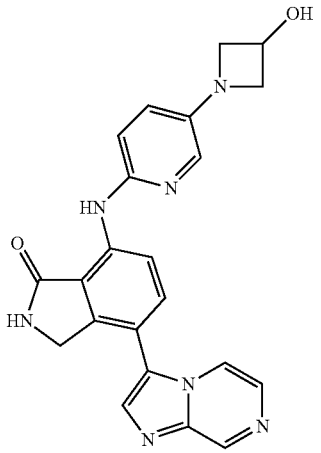 [SMILES: O=C1NCc2c(-c3cnc4cnccn34)ccc(Nc3ccc(N4CC(O)C4)cn3)c21] |
| I-316 | 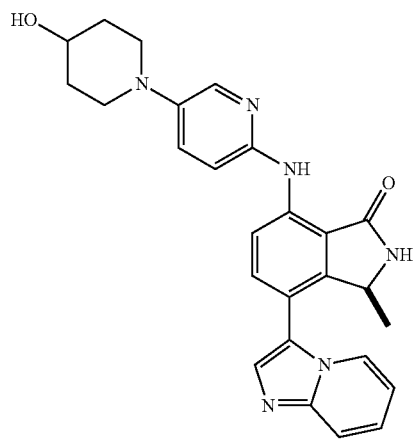 [SMILES: C[C@@H]1NC(=O)c2c(Nc3ccc(N4CCC(O)CC4)cn3)ccc(-c3cnc4ccccn34)c21] |
| I-317 | 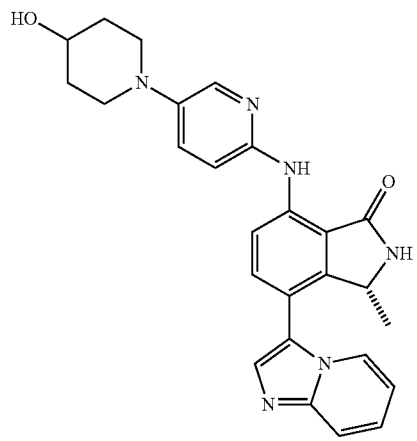 [SMILES: C[C@H]1NC(=O)c2c(Nc3ccc(N4CCC(O)CC4)cn3)ccc(-c3cnc4ccccn34)c21] |

TABLE 1-continued

Selected Compounds

| # | Structure |
|---|---|
| I-318 | 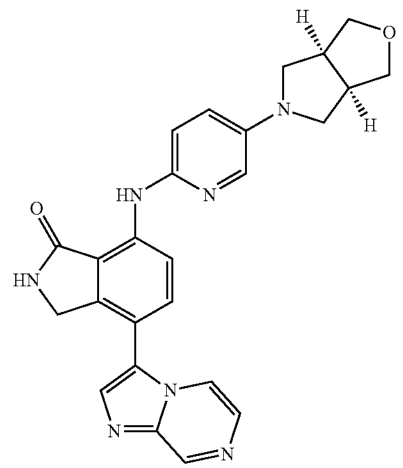 [SMILES: O=C1NCc2c(-c3cnc4cnccn34)ccc(Nc3ccc(N4C[C@H]5COC[C@H]5C4)cn3)c21] |
| I-319 | 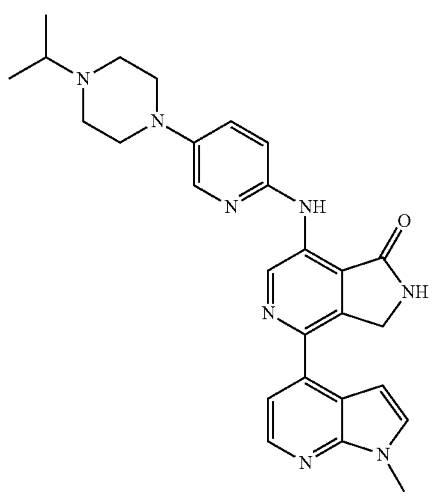 [SMILES: CC(C)N1CCN(c2ccc(Nc3cnc(-c4ccnc5c4ccn5C)c4c3C(=O)NC4)nc2)CC1] |
| I-320 | 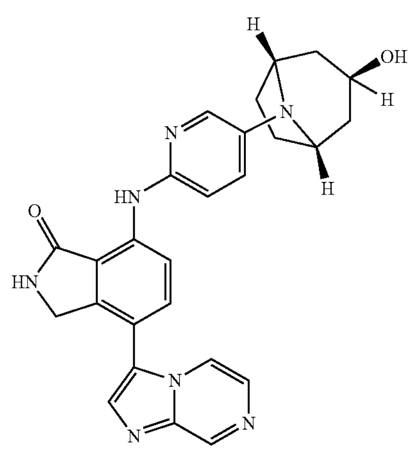 [SMILES: O=C1NCc2c(-c3cnc4cnccn34)ccc(Nc3ccc(N4[C@@H]5CC[C@H]4C[C@H](O)C5)cn3)c21] |

TABLE 1-continued
Selected Compounds
| # | Structure |
|---|---|
| I-321 | 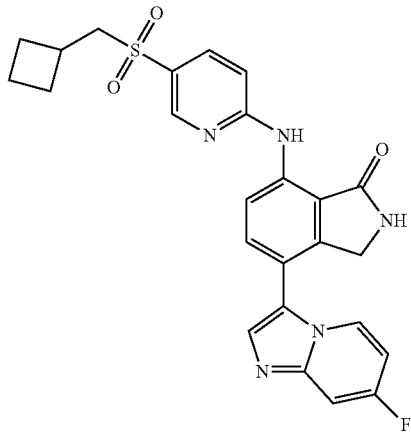 [SMILES: O=C1NCc2c(-c3cnc4cc(F)ccn34)ccc(Nc3ccc(S(=O)(=O)CC4CCC4)cn3)c21] |
| I-322 | 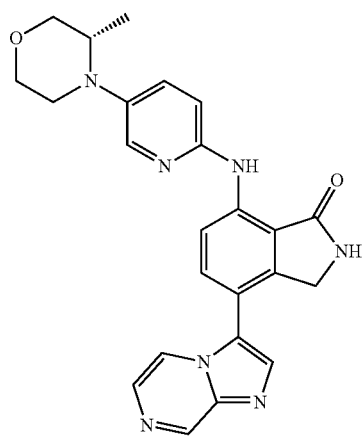 [SMILES: C[C@H]1COCCN1c1ccc(Nc2ccc(-c3cnc4cnccn34)c3c2C(=O)NC3)nc1] |
| I-323 | 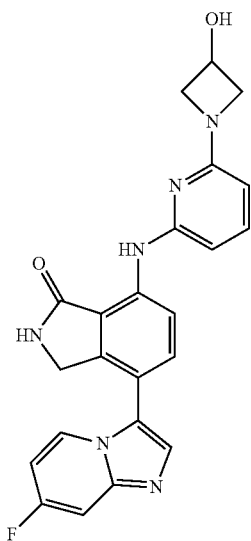 [SMILES: O=C1NCc2c(-c3cnc4cc(F)ccn34)ccc(Nc3cccc(N4CC(O)C4)n3)c21] |

TABLE 1-continued
| Selected Compounds | |
|---|---|
| # | Structure |
| I-324 | 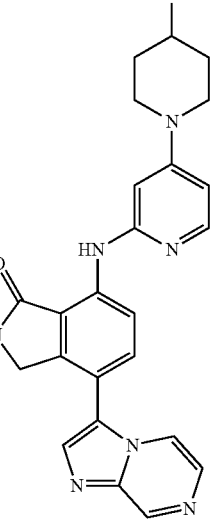 |
| I-325 | 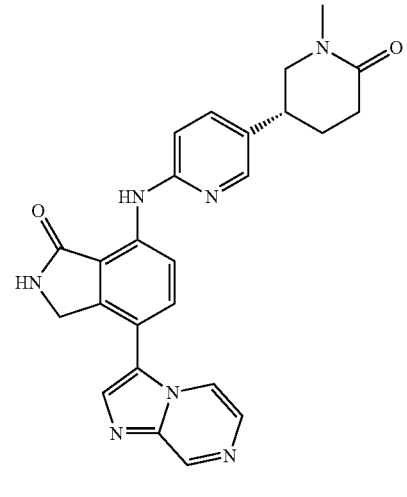 [SMILES: CN1C[C@@H](c2ccc(Nc3ccc(-c4cnc5cnccn45)c4c3C(=O)NC4)nc2)CCC1=O] |
| I-326 | 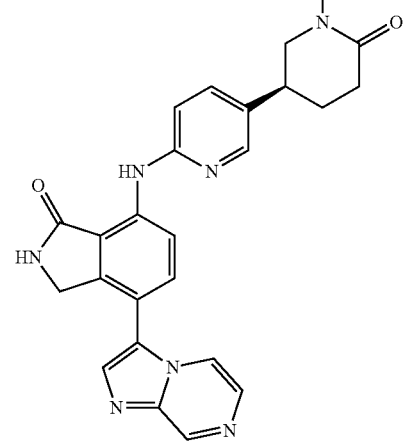 |

TABLE 1-continued
Selected Compounds
| # | Structure |
|---|---|
| I-327 | 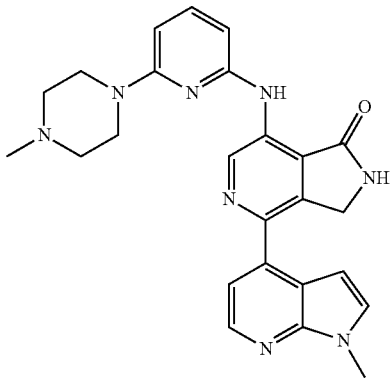 [SMILES: CN1CCN(c2cccc(Nc3cnc(-c4ccnc5c4ccn5C)c4c3C(=O)NC4)n2)CC1] |
| I-328 | 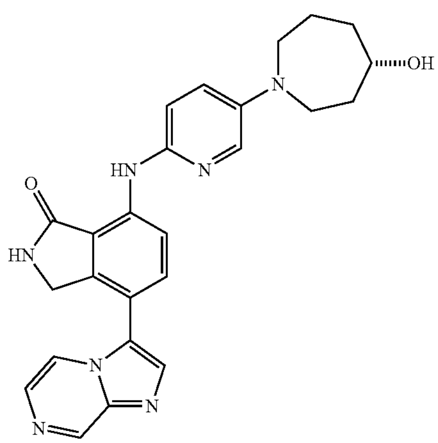 [SMILES: O=C1NCc2c(-c3cnc4cnccn34)ccc(Nc3ccc(N4CCC[C@H](O)CC4)cn3)c21] |
| I-329 | 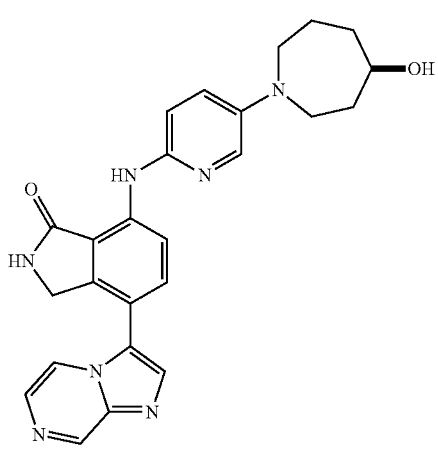 [SMILES: O=C1NCc2c(-c3cnc4cnccn34)ccc(Nc3ccc(N4CCC[C@@H](O)CC4)cn3)c21] |

TABLE 1-continued
Selected Compounds
| # | Structure |
|---|---|
| I-330 | 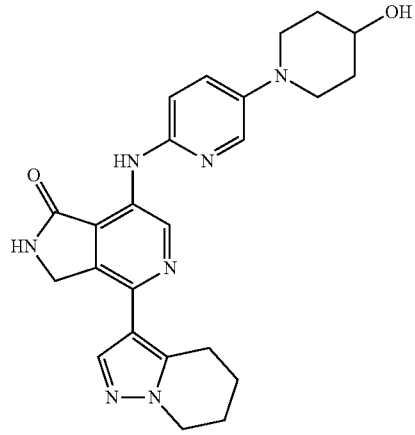 [SMILES: O=C1NCc2c(-c3cnn4c3CCCC4)ncc(Nc3ccc(N4CCC(O)CC4)cn3)c21] |
| I-331 | 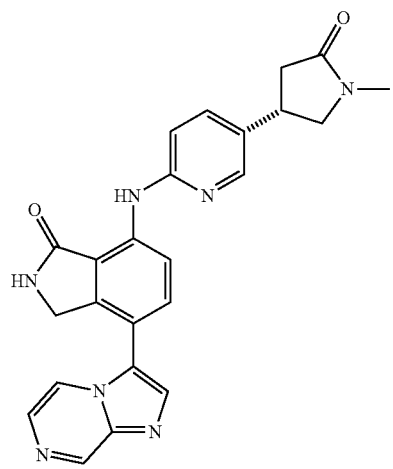 |
| I-332 | 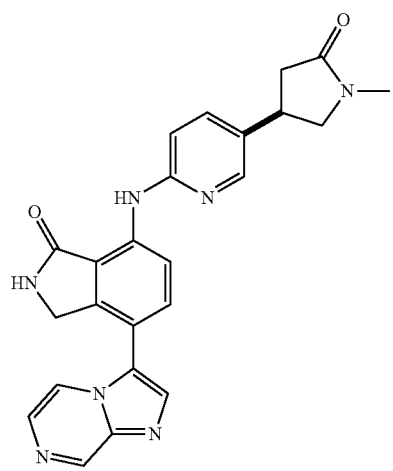 |

TABLE 1-continued
Selected Compounds
| # | Structure |
|---|---|
| I-333 | 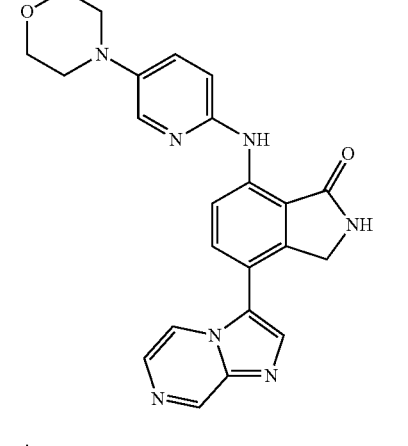 |
| I-334 | 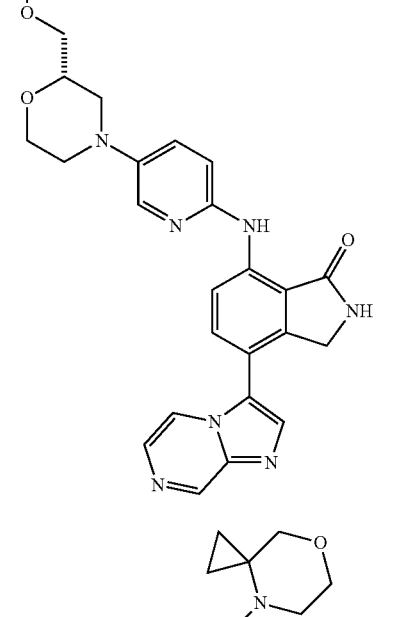 |
| I-335 | 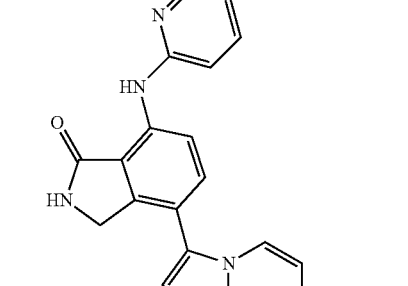 |

TABLE 1-continued

Selected Compounds

| # | Structure |
|---|-----------|
| I-336 | 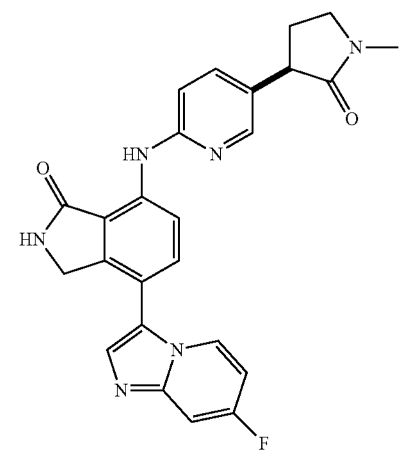 |
| I-338 | 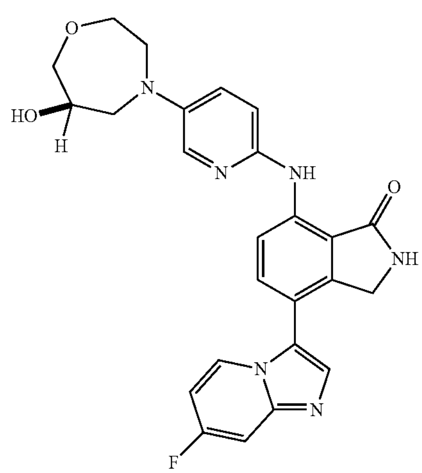 [SMILES: O=C1NCc2c(-c3cnc4cc(F)ccn34)ccc(Nc3ccc(N4CCOC[C@H](O)C4)cn3)c21] |
| I-339 | 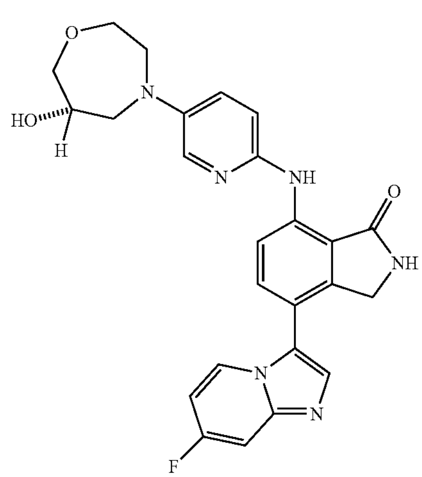 [SMILES: O=C1NCc2c(-c3cnc4cc(F)ccn34)ccc(Nc3ccc(N4CCOC[C@@H](O)C4)cn3)c21] |

TABLE 1-continued
Selected Compounds
| # | Structure |
|---|---|
| I-340 | 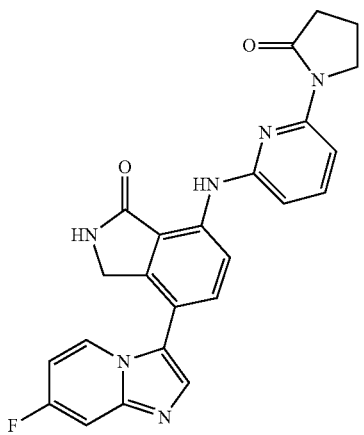 [SMILES: O=C1NCc2c(-c3cnc4cc(F)ccn34)ccc(Nc3cccc(N4CCCC4=O)n3)c21] |
| I-341 | 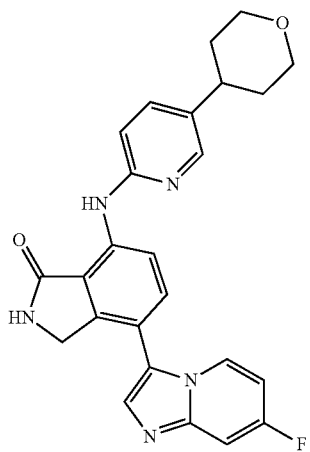 [SMILES: O=C1NCc2c(-c3cnc4cc(F)ccn34)ccc(Nc3ccc(C4CCOCC4)cn3)c21] |
| I-342 | 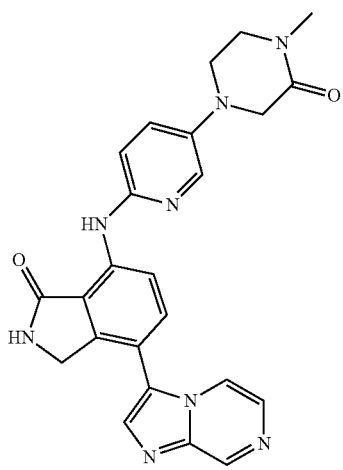 [SMILES: CN1CCN(c2ccc(Nc3ccc(-c4cnc5cnccn45)c4c3C(=O)NC4)nc2)CC1=O] |

TABLE 1-continued
Selected Compounds
| # | Structure |
|---|---|
| I-343 | 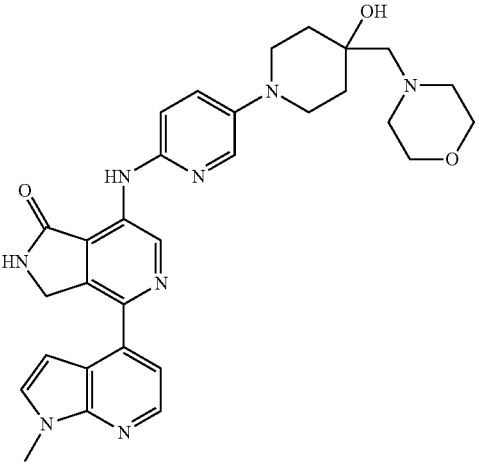 [SMILES: Cn1ccc2c(-c3ncc(Nc4ccc(N5CCC(O)(CN6CCOCC6)CC5)cn4)c4c3CNC4=O)ccnc21] |
| I-344 | 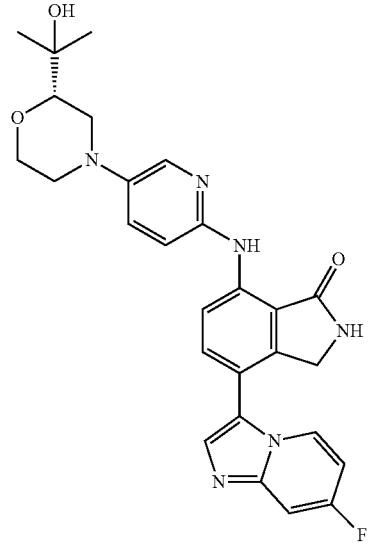 [SMILES: CC(C)(O)[C@@H]1CN(c2ccc(Nc3ccc(-c4cnc5cc(F)ccn45)c4c3C(=O)NC4)nc2)CCO1] |
| I-345 | 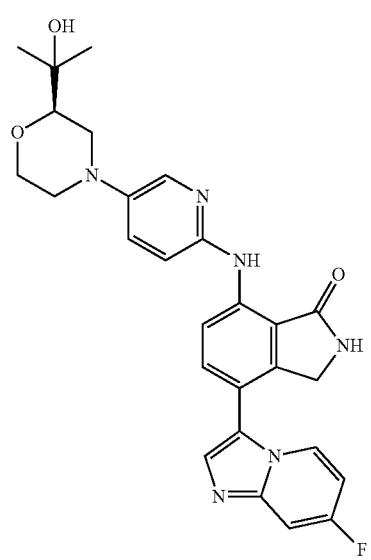 [SMILES: CC(C)(O)[C@H]1CN(c2ccc(Nc3ccc(-c4cnc5cc(F)ccn45)c4c3C(=O)NC4)nc2)CCO1] |

TABLE 1-continued
Selected Compounds
| # | Structure |
|---|---|
| I-346 | 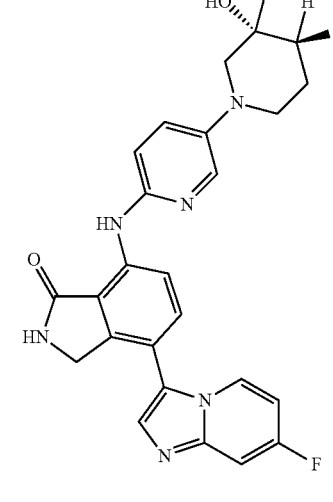 |
| I-347 | 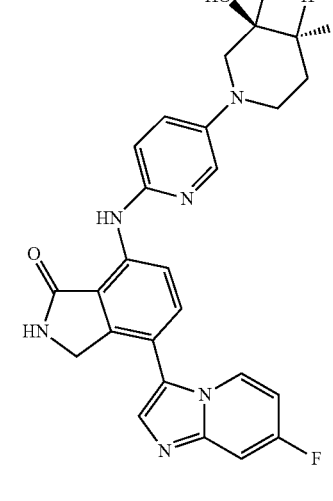 |
| I-348 | 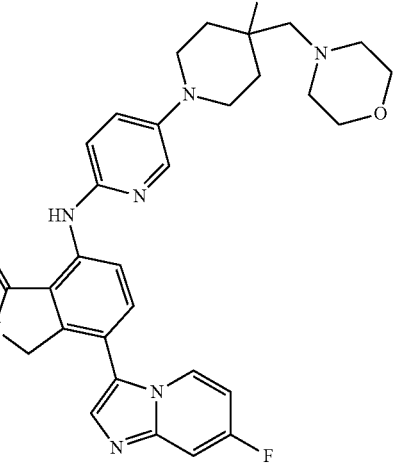 |

TABLE 1-continued
Selected Compounds
| # | Structure |
|---|---|
| I-349 | 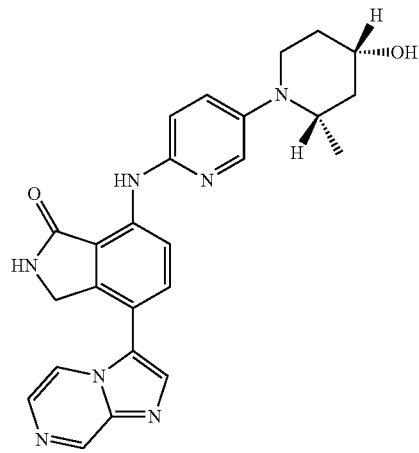 [SMILES: C[C@H]1C[C@@H](O)CCN1c1ccc(Nc2ccc(-c3cnc4cnccn34)c3c2C(=O)NC3)nc1] |
| I-350 | 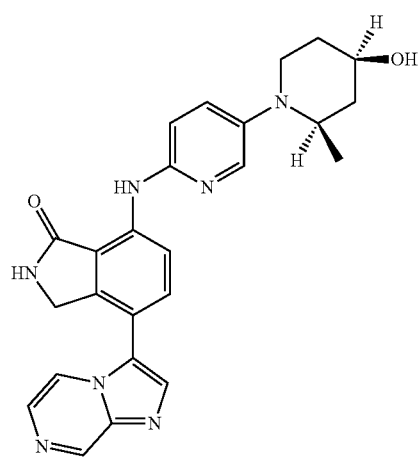 [SMILES: C[C@@H]1C[C@H](O)CCN1c1ccc(Nc2ccc(-c3cnc4cnccn34)c3c2C(=O)NC3)nc1] |
| I-351 | 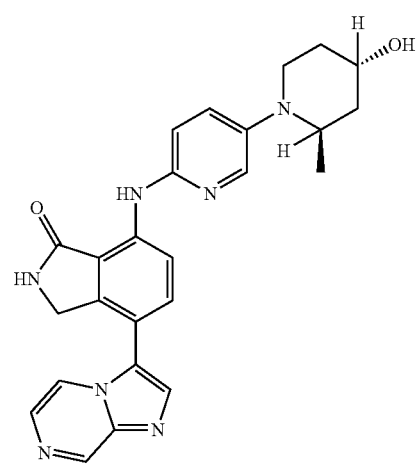 [SMILES: C[C@@H]1C[C@@H](O)CCN1c1ccc(Nc2ccc(-c3cnc4cnccn34)c3c2C(=O)NC3)nc1] |

TABLE 1-continued
Selected Compounds
| # | Structure |
|---|---|
| I-352 | 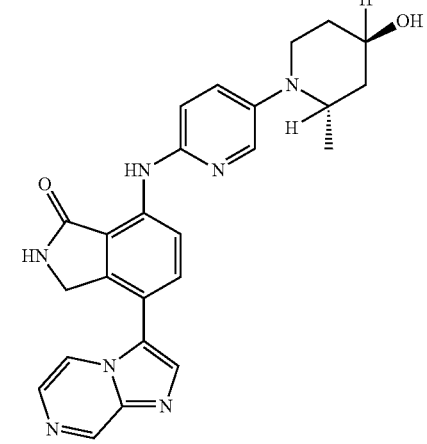 |
| I-353 | 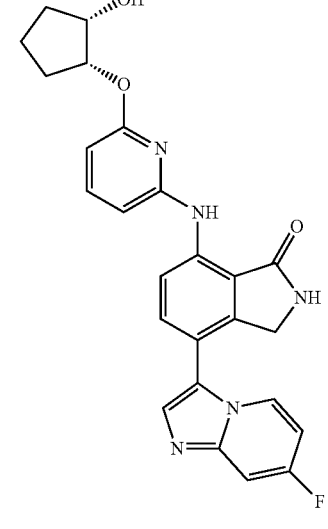 |
| I-354 | 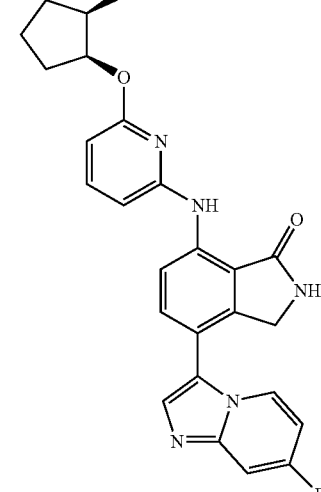 |

TABLE 1-continued
Selected Compounds
| # | Structure |
|---|---|
| I-355 | 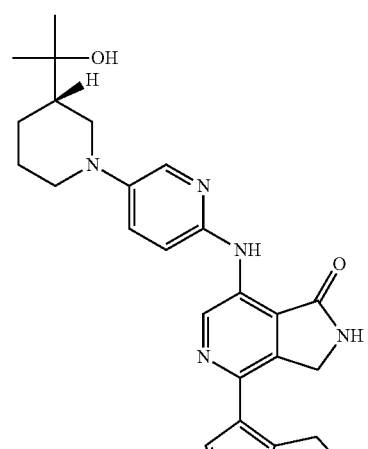 |
| I-356 | 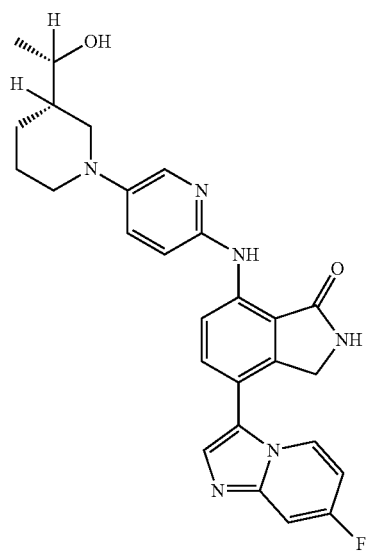 [SMILES: C[C@H](O)[C@H]1CCCN(c2ccc(Nc3ccc(-c4cnc5cc(F)ccn45)c4c3C(=O)NC4)nc2)C1] |

TABLE 1-continued
Selected Compounds
| # | Structure |
|---|---|
| I-357 | 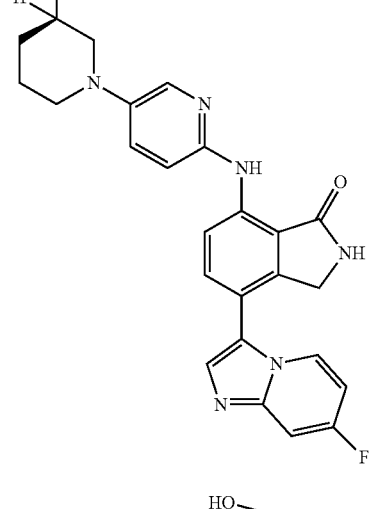 |
| I-358 | 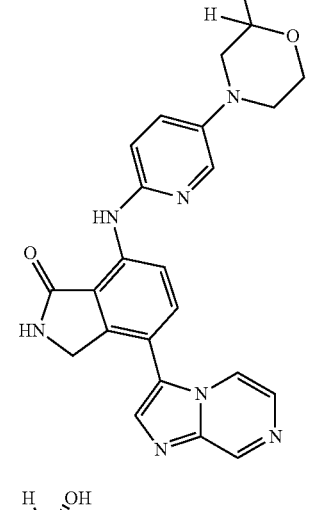 |
| I-359 | 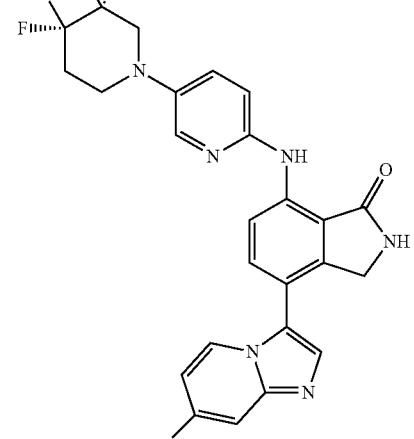 |

TABLE 1-continued
| Selected Compounds | |
|---|---|
| # | Structure |
| I-360 | 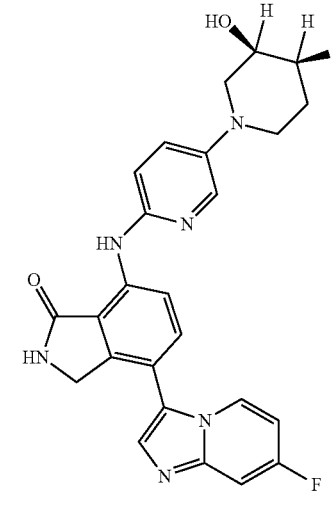 |
| I-361 | 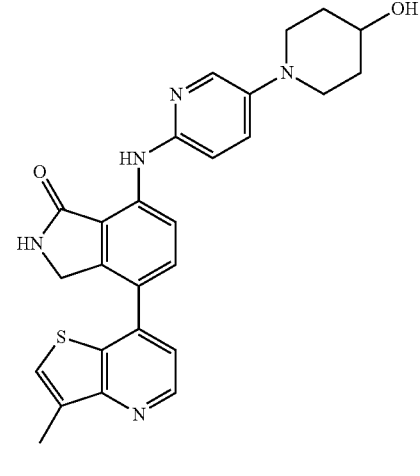 [SMILES: Cc1csc2c(-c3ccc(Nc4ccc(N5CCC(O)CC5)cn4)c4c3CNC4=O)ccnc12] |
| I-362 | 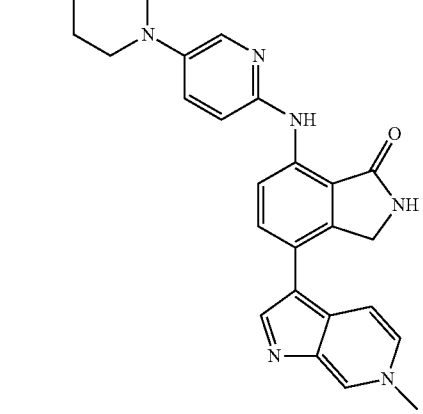 |

TABLE 1-continued

Selected Compounds

| # | Structure |
|---|---|
| I-363 | 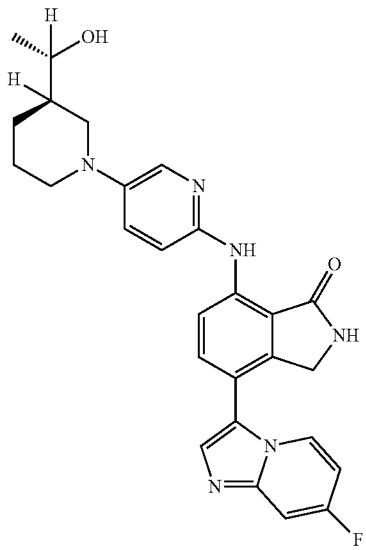 [SMILES: C[C@H](O)[C@@H]1CCCN(c2ccc(Nc3ccc(-c4cnc5cc(F)ccn45)c4c3C(=O)NC4)nc2)C1] |
| I-364 | 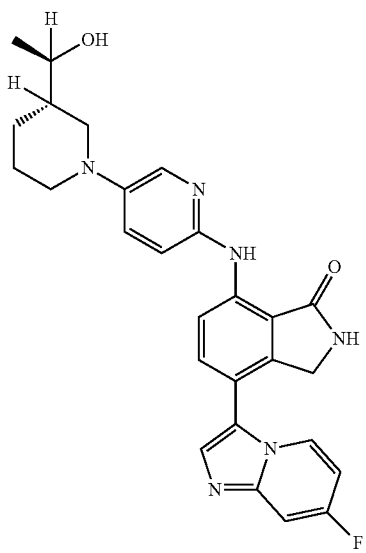 [SMILES: C[C@@H](O)[C@H]1CCCN(c2ccc(Nc3ccc(-c4cnc5cc(F)ccn45)c4c3C(=O)NC4)nc2)C1] |
| I-365 | 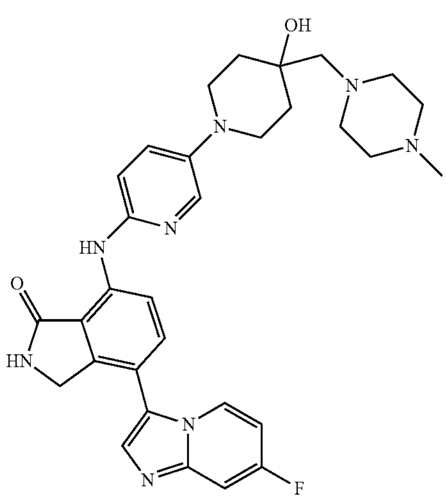 [SMILES: CN1CCN(CC2(O)CCN(c3ccc(Nc4ccc(-c5cnc6cc(F)ccn56)c5c4C(=O)NC5)nc3)CC2)CC1] |

TABLE 1-continued
Selected Compounds
| # | Structure |
|---|---|
| I-366 | 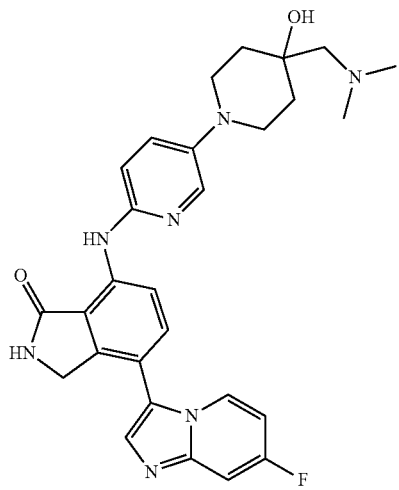 [SMILES: CN(C)CC1(O)CCN(c2ccc(Nc3ccc(-c4cnc5cc(F)ccn45)c4c3C(=O)NC4)nc2)CC1] |
| I-367 | 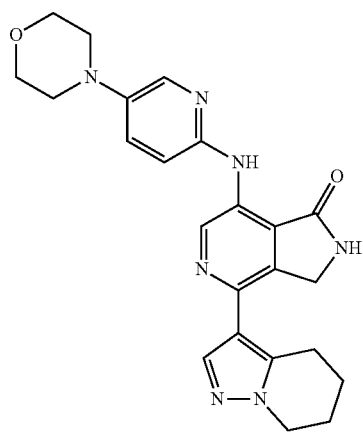 [SMILES: O=C1NCc2c(-c3cnn4c3CCCC4)ncc(Nc3ccc(N4CCOCC4)cn3)c21] |
| I-368 | 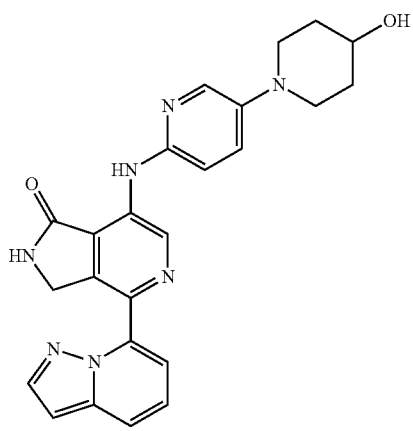 [SMILES: O=C1NCc2c(-c3cccc4ccnn34)ncc(Nc3ccc(N4CCC(O)CC4)cn3)c21] |

TABLE 1-continued
Selected Compounds
| # | Structure |
|---|---|
| I-369 | 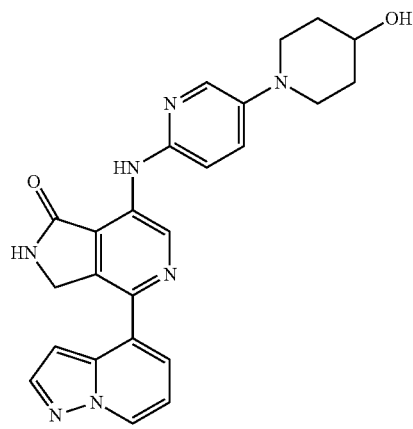 [SMILES: O=C1NCc2c(-c3cccn4nccc34)ncc(Nc3ccc(N4CCC(O)CC4)cn3)c21] |
| I-370 | 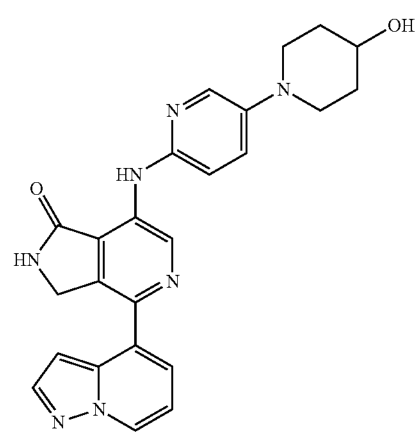 |
| I-371 | 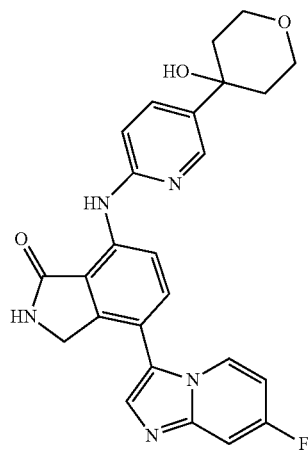 [SMILES: O=C1NCc2c(-c3cnc4cc(F)ccn34)ccc(Nc3ccc(C4(O)CCOCC4)cn3)c21] |

TABLE 1-continued
Selected Compounds
| # | Structure |
|---|---|
| I-372 | 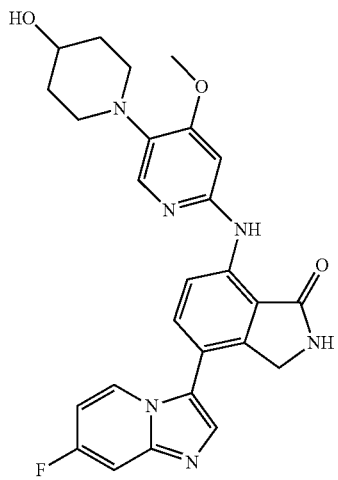 [SMILES: COc1cc(Nc2ccc(-c3cnc4cc(F)ccn34)c3c2C(=O)NC3)ncc1N1CCC(O)CC1] |
| I-373 | 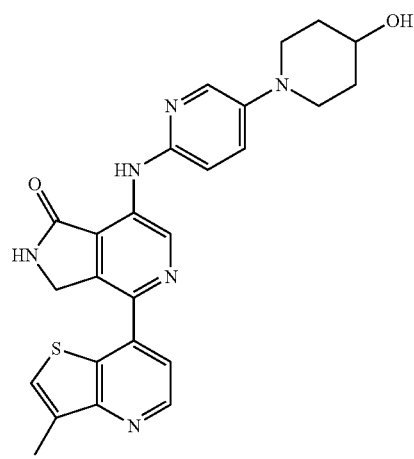 [SMILES: Cc1csc2c(-c3ncc(Nc4ccc(N5CCC(O)CC5)cn4)c4c3CNC4=O)ccnc12] |
| I-374 | 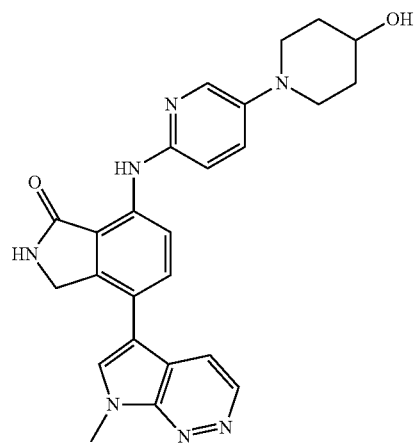 [SMILES: Cn1cc(-c2ccc(Nc3ccc(N4CCC(O)CC4)cn3)c3c2CNC3=O)c2ccnnc21] |

TABLE 1-continued
Selected Compounds
| # | Structure |
|---|---|
| I-375 | 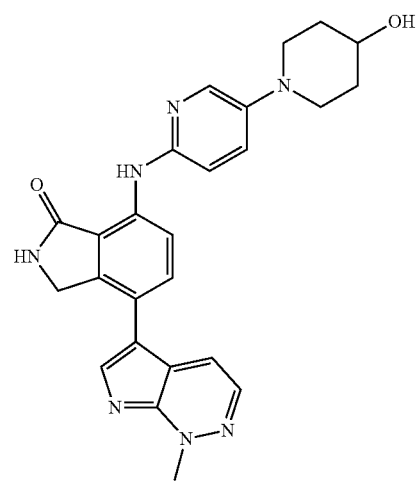 [SMILES: Cn1nccc2c(-c3ccc(Nc4ccc(N5CCC(O)CC5)cn4)c4c3CNC4=O)cnc1-2] |
| I-376 | 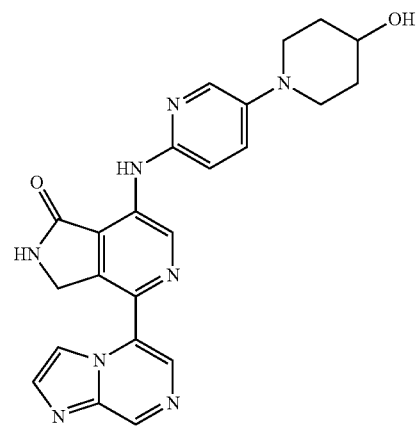 [SMILES: O=C1NCc2c(-c3cncc4nccn34)ncc(Nc3ccc(N4CCC(O)CC4)cn3)c21] |
| I-377 | 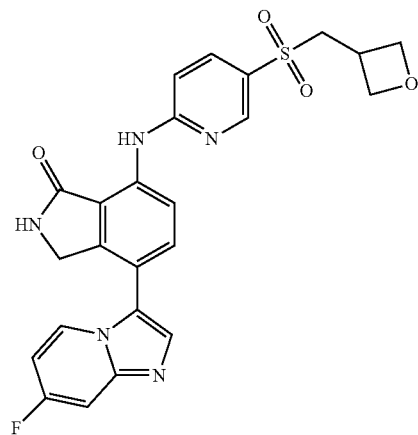 [SMILES: O=C1NCc2c(-c3cnc4cc(F)ccn34)ccc(Nc3ccc(S(=O)(=O)CC4COC4)cn3)c21] |

TABLE 1-continued
Selected Compounds
| # | Structure |
|---|---|
| I-378 | 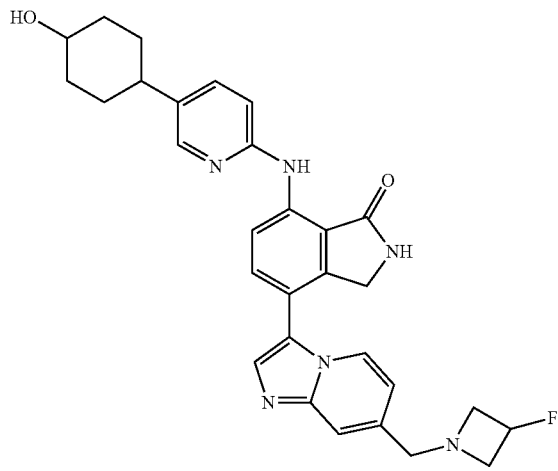 [SMILES: O=C1NCc2c(-c3cnc4cc(CN5CC(F)C5)ccn34)ccc(Nc3ccc(C4CCC(O)CC4)cn3)c21] |
| I-379 | 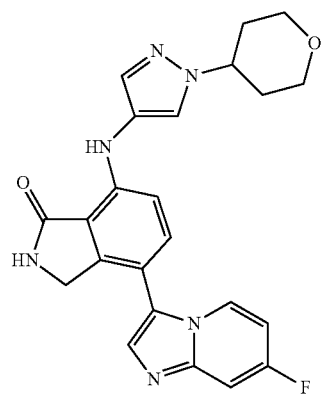 [SMILES: O=C1NCc2c(-c3cnc4cc(F)ccn34)ccc(Nc3cnn(C4CCOCC4)c3)c21] |
| I-380 | 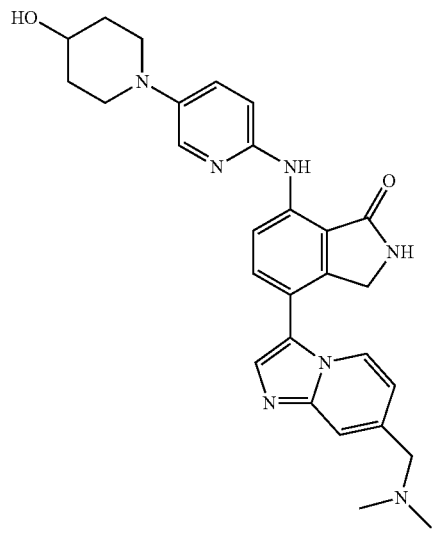 [SMILES: CN(C)Cc1ccn2c(-c3ccc(Nc4ccc(N5CCC(O)CC5)cn4)c4c3CNC4=O)cnc2c1] |

TABLE 1-continued
Selected Compounds
| # | Structure |
|---|---|
| I-381 | 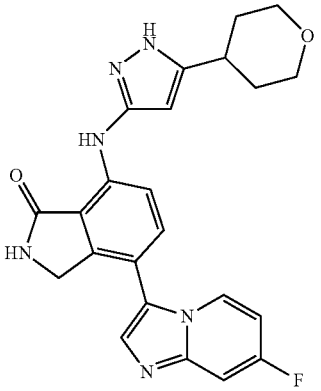 [SMILES: O=C1NCc2c(-c3cnc4cc(F)ccn34)ccc(Nc3cc(C4CCOCC4)[nH]n3)c21] |
| I-382 | 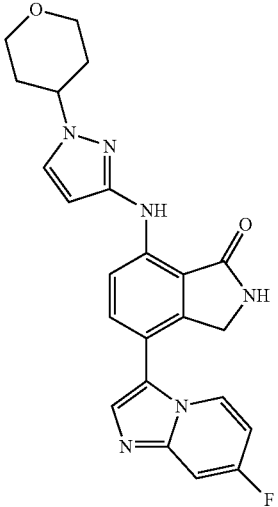 [SMILES: O=C1NCc2c(-c3cnc4cc(F)ccn34)ccc(Nc3ccn(C4CCOCC4)n3)c21] |
| I-383 | 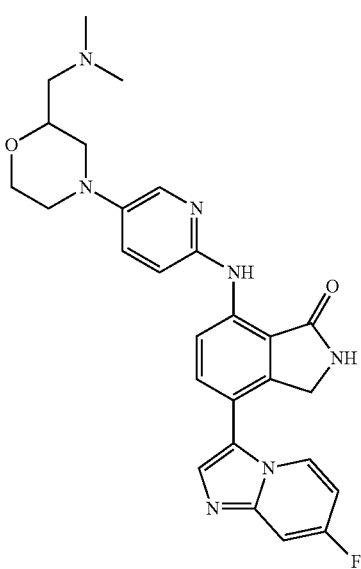 [SMILES: CN(C)CC1CN(c2ccc(Nc3ccc(-c4cnc5cc(F)ccn45)c4c3C(=O)NC4)nc2)CCO1] |

TABLE 1-continued
Selected Compounds
| # | Structure |
|---|---|
| I-384 | 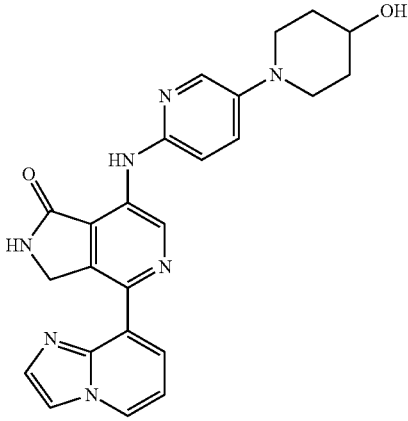 [SMILES: O=C1NCc2c(-c3cccn4ccnc34)ncc(Nc3ccc(N4CCC(O)CC4)cn3)c21] |
| I-385 | 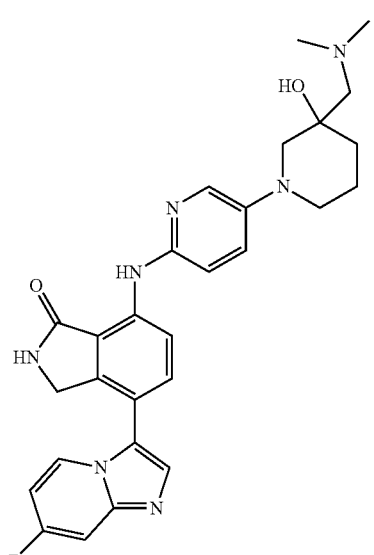 |
| I-386 | 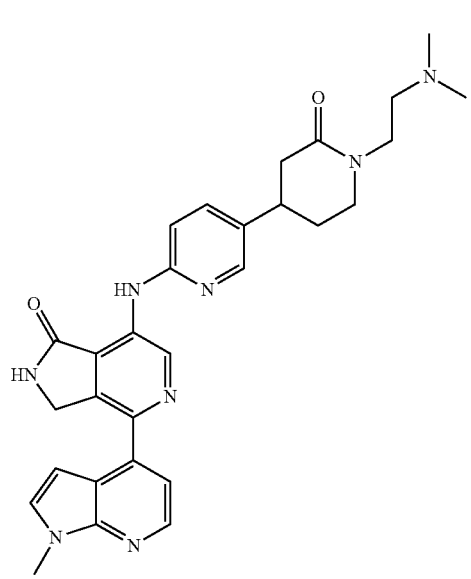 [SMILES: CN(C)CCN1CCC(c2ccc(Nc3cnc(-c4ccnc5c4ccn5C)c4c3C(=O)NC4)nc2)CC1=O] |

TABLE 1-continued
Selected Compounds
| # | Structure |
|---|---|
| I-387 | 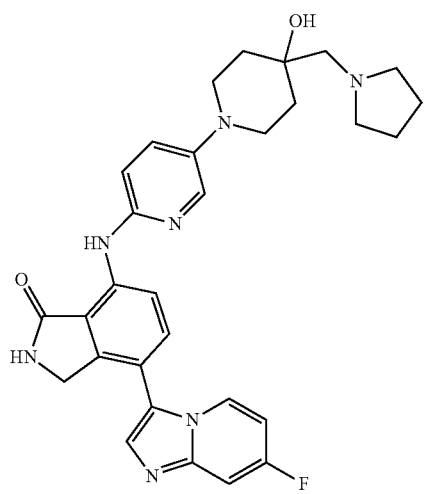 [SMILES: O=C1NCc2c(-c3cnc4cc(F)ccn34)ccc(Nc3ccc(N4CCC(O)(CN5CCCC5)CC4)cn3)c21] |
| I-388 | 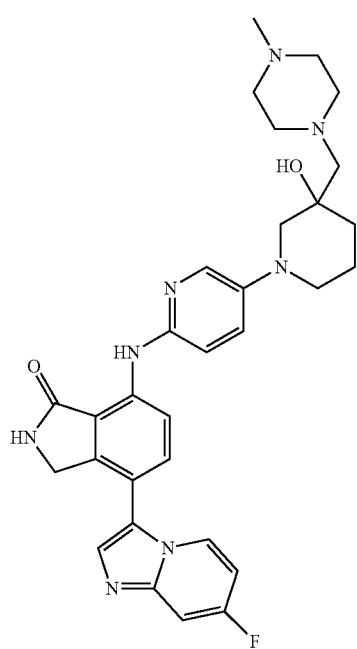 [SMILES: CN1CCN(CC2(O)CCCN(c3ccc(Nc4ccc(-c5cnc6cc(F)ccn56)c5c4C(=O)NC5)nc3)C2)CC1] |

TABLE 1-continued
Selected Compounds
| # | Structure |
|---|---|
| I-389 | 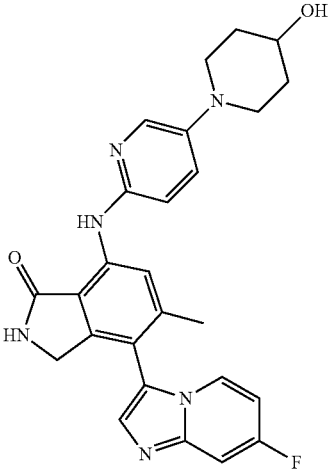 [SMILES: Cc1cc(Nc2ccc(N3CCC(O)CC3)cn2)c2c(c1-c1cnc3cc(F)ccn13)CNC2=O] |
| I-390 | 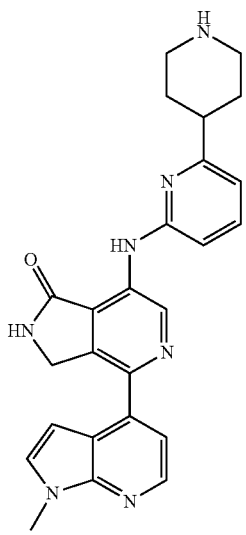 [SMILES: Cn1ccc2c(-c3ncc(Nc4cccc(C5CCNCC5)n4)c4c3CNC4=O)ccnc21] |
| I-391 | 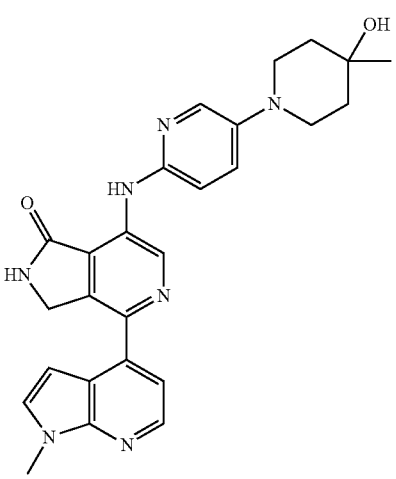 [SMILES: Cn1ccc2c(-c3ncc(Nc4ccc(N5CCC(C)(O)CC5)cn4)c4c3CNC4=O)ccnc21] |

TABLE 1-continued
Selected Compounds
| # | Structure |
|---|---|
| I-392 | 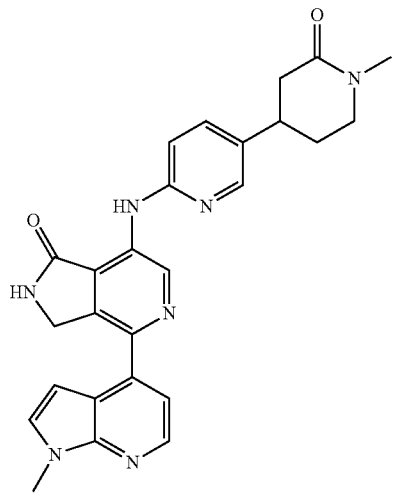 |
| I-393 | 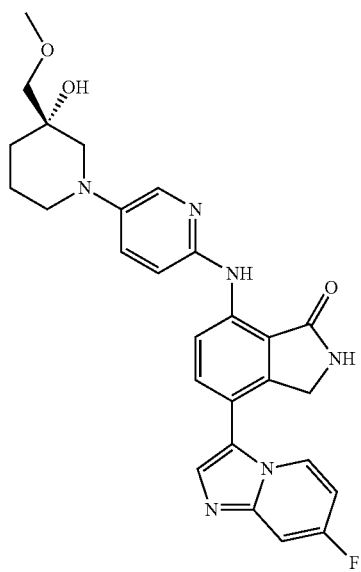 [SMILES: COC[C@]1(O)CCCN(c2ccc(Nc3ccc(-c4cnc5cc(F)ccn45)c4c3C(=O)NC4)nc2)C1] |

TABLE 1-continued
Selected Compounds
| # | Structure |
|---|---|
| I-394 | 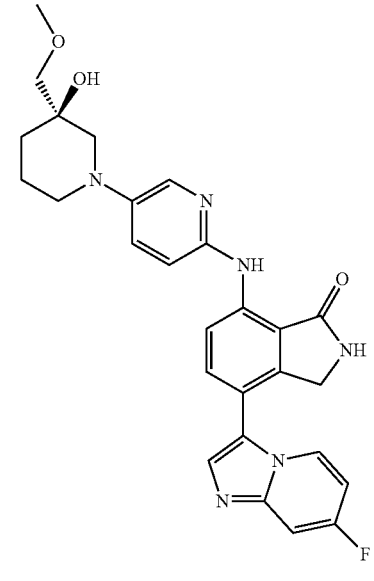 [SMILES: COC[C@@]1(O)CCCN(c2ccc(Nc3ccc(-c4cnc5cc(F)ccn45)c4c3C(=O)NC4)nc2)C1] |
| I-395 | 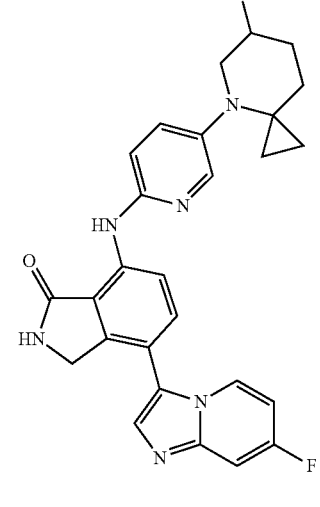 |
| I-396 | 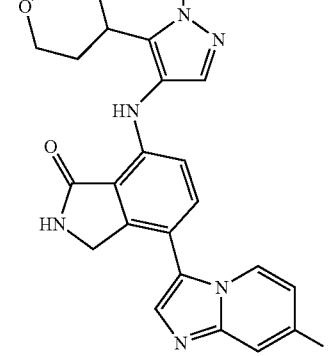 |

TABLE 1-continued

Selected Compounds

| # | Structure |
|---|---|
| I-397 | 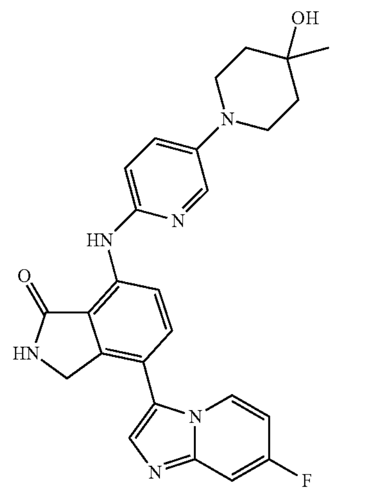 [SMILES: CC1(O)CCN(c2ccc(Nc3ccc(-c4cnc5cc(F)ccn45)c4c3C(=O)NC4)nc2)CC1] |
| I-398 | 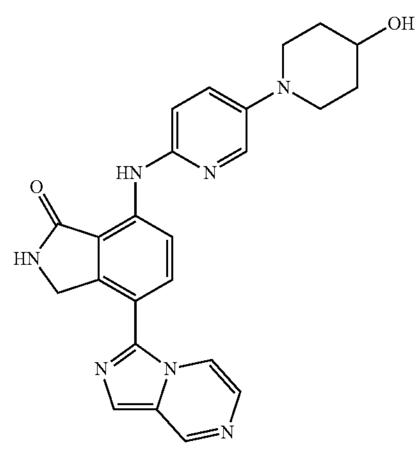 [SMILES: O=C1NCc2c(-c3ncc4cnccn34)ccc(Nc3ccc(N4CCC(O)CC4)cn3)c21] |
| I-399 | 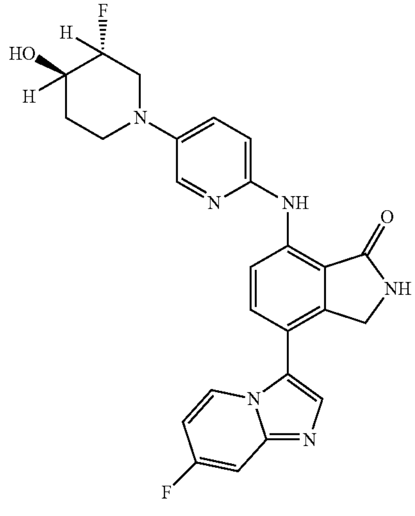 [SMILES: O=C1NCc2c(-c3cnc4cc(F)ccn34)ccc(Nc3ccc(N4CC[C@@H](O)[C@H](F)C4)cn3)c21] |

TABLE 1-continued
Selected Compounds
| # | Structure |
|---|---|
| I-400 | 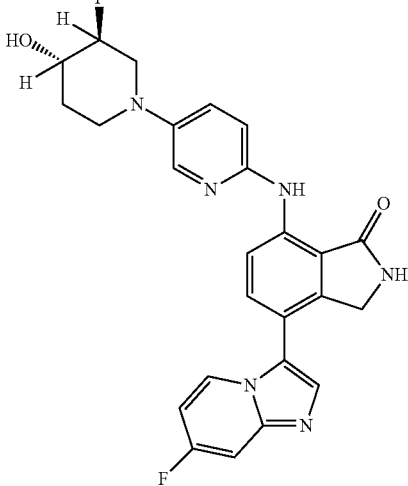 |
| I-401 | 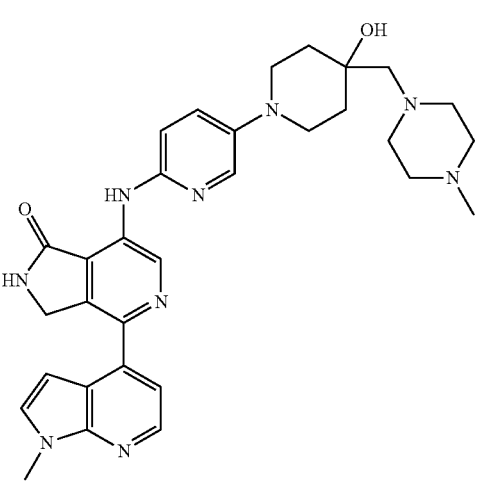 [SMILES: CN1CCN(CC2(O)CCN(c3ccc(Nc4cnc(-c5ccnc6c5ccn6C)c5c4C(=O)NC5)nc3)CC2)CC1] |
| I-402 | 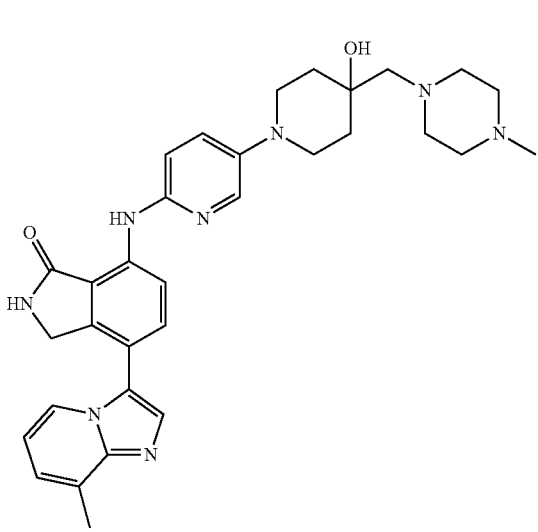 [SMILES: Cc1cccn2c(-c3ccc(Nc4ccc(N5CCC(O)(CN6CCN(C)CC6)CC5)cn4)c4c3CNC4=O)cnc12] |

TABLE 1-continued
| Selected Compounds | |
|---|---|
| # | Structure |
| I-403 | |
| I-404 | 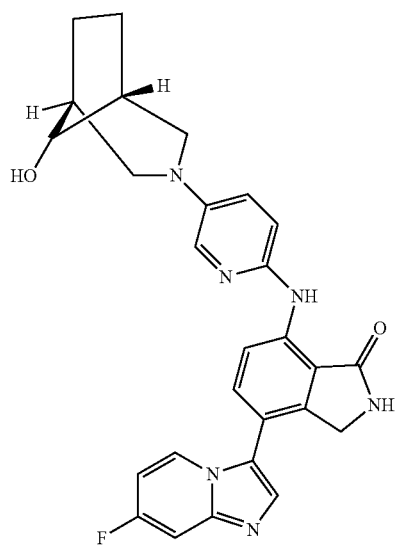 [SMILES: O=C1NCc2c(-c3cnc4cc(F)ccn34)ccc(Nc3ccc(N4C[C@H]5CC[C@@H](C4)C5O)cn3)c21] |

TABLE 1-continued
| Selected Compounds | |
|---|---|
| # | Structure |
| I-405 | 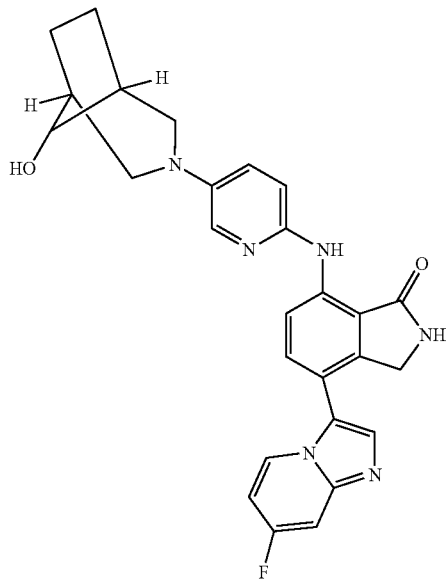 [SMILES: O=C1NCc2c(-c3cnc4cc(F)ccn34)ccc(Nc3ccc(N4CC5CCC(C4)C5O)cn3)c21] |
| I-406 | 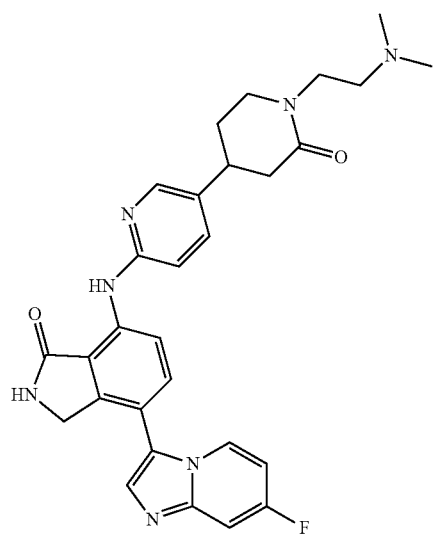 [SMILES: CN(C)CCN1CCC(c2ccc(Nc3ccc(-c4cnc5cc(F)ccn45)c4c3C(=O)NC4)nc2)CC1=O] |

TABLE 1-continued
| Selected Compounds | |
|---|---|
| # | Structure |
| I-407 | 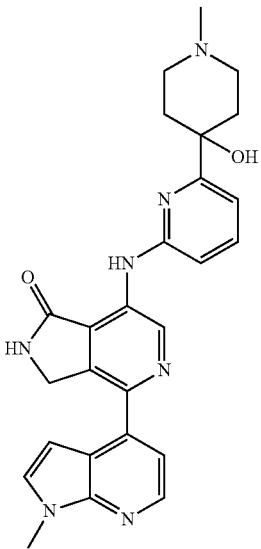 [SMILES: CN1CCC(O)(c2cccc(Nc3cnc(-c4ccnc5c4ccn5C)c4c3C(=O)NC4)n2)CC1] |
| I-408 | 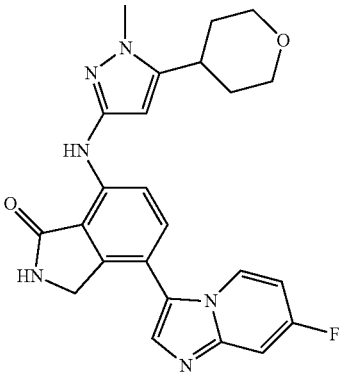 [SMILES: Cn1nc(Nc2ccc(-c3cnc4cc(F)ccn34)c3c2C(=O)NC3)cc1C1CCOCC1] |
| I-411 | 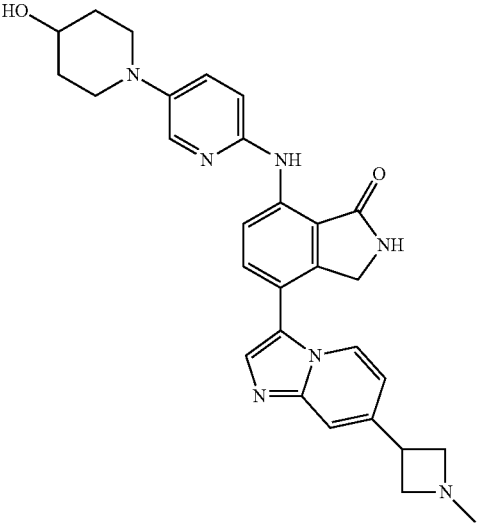 [SMILES: CN1CC(c2ccn3c(-c4ccc(Nc5ccc(N6CCC(O)CC6)cn5)c5c4CNC5=O)cnc3c2)C1] |

TABLE 1-continued
Selected Compounds
| # | Structure |
|---|---|
| I-412 | 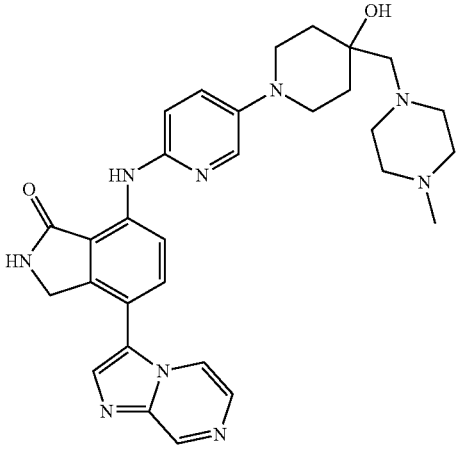 [SMILES: CN1CCN(CC2(O)CCN(c3ccc(Nc4ccc(-c5cnc6cnccn56)c5c4C(=O)NC5)nc3)CC2)CC1] |
| I-413 | 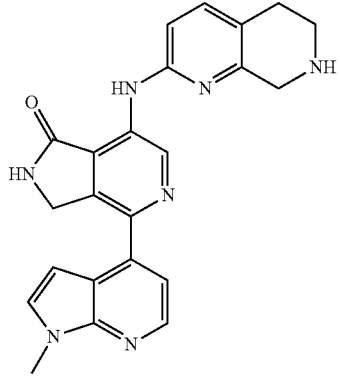 [SMILES: Cn1ccc2c(-c3ncc(Nc4ccc5c(n4)CNCC5)c4c3CNC4=O)ccnc21] |
| I-414 | 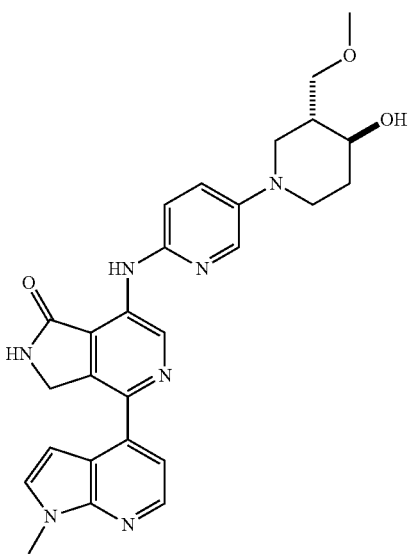 [SMILES: COC[C@H]1CN(c2ccc(Nc3cnc(-c4ccnc5c4ccn5C)c4c3C(=O)NC4)nc2)CC[C@@H]1O] |

TABLE 1-continued
| Selected Compounds |
|---|
| # | Structure |
I-415 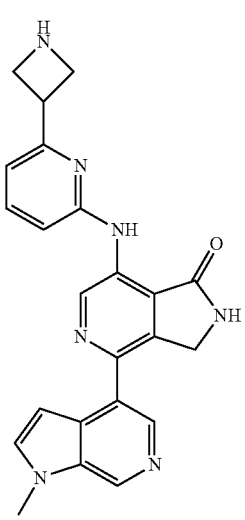 [SMILES: Cn1ccc2c(-c3ncc(Nc4cccc(C5CNC5)n4)c4c3CNC4=O)cncc21]
I-416 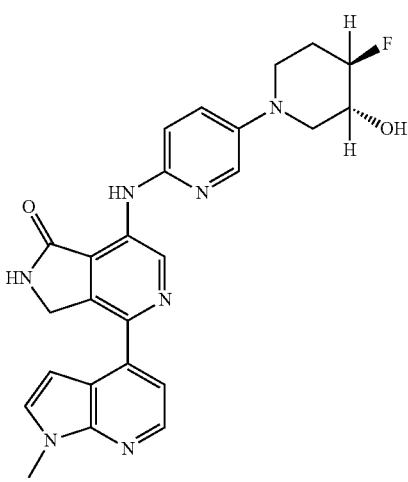 [SMILES: Cn1ccc2c(-c3ncc(Nc4ccc(N5CC[C@@H](F)[C@H](O)C5)cn4)c4c3CNC4=O)ccnc21]
I-417 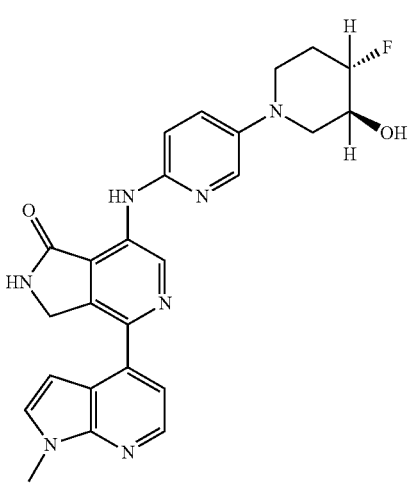 [SMILES: Cn1ccc2c(-c3ncc(Nc4ccc(N5CC[C@H](F)[C@@H](O)C5)cn4)c4c3CNC4=O)ccnc21]

TABLE 1-continued
| Selected Compounds | |
|---|---|
| # | Structure |
| I-418 | 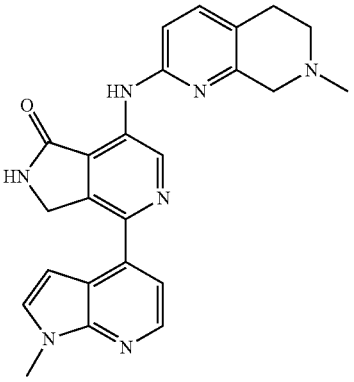 [SMILES: CN1CCc2ccc(Nc3cnc(-c4ccnc5c4ccn5C)c4c3C(=O)NC4)nc2C1] |
| I-419 | 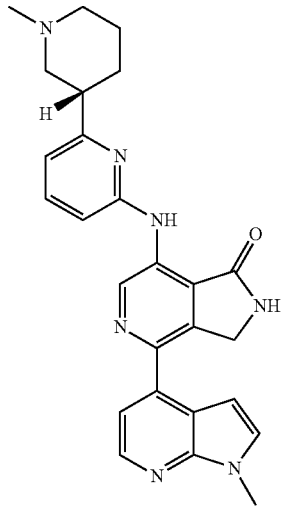 [SMILES: CN1CCC[C@H](c2cccc(Nc3cnc(-c4ccnc5c4ccn5C)c4c3C(=O)NC4)n2)C1] |
| I-420 | 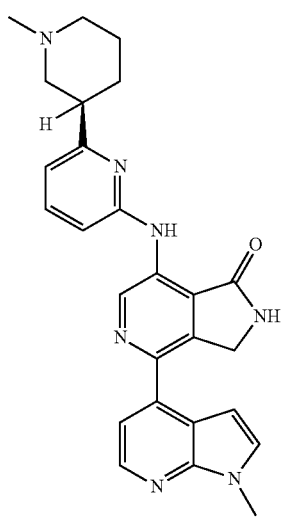 [SMILES: CN1CCC[C@@H](c2cccc(Nc3cnc(-c4ccnc5c4ccn5C)c4c3C(=O)NC4)n2)C1] |

TABLE 1-continued
Selected Compounds
| # | Structure |
|---|---|
| I-421 | 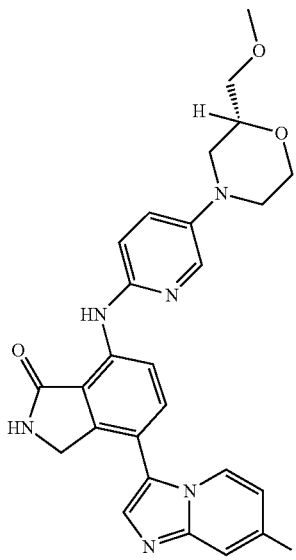 |
| I-422 | 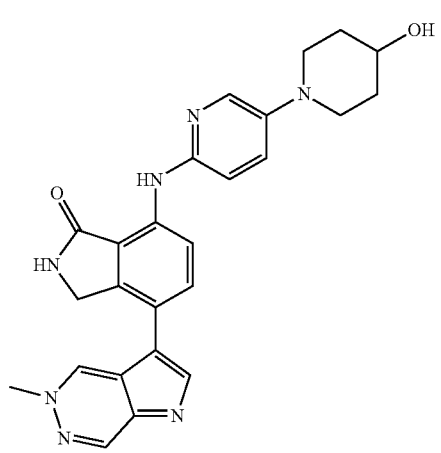 [SMILES: Cn1cc2c(-c3ccc(Nc4ccc(N5CCC(O)CC5)cn4)c4c3CNC4=O)cnc-2cn1] |
| I-423 | 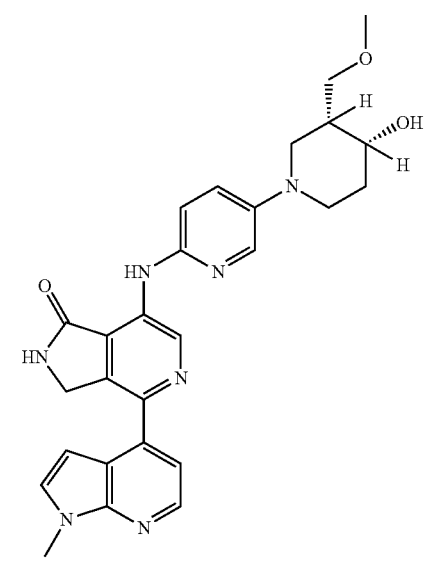 [SMILES: COC[C@H]1CN(c2ccc(Nc3cnc(-c4ccnc5c4ccn5C)c4c3C(=O)NC4)nc2)CC[C@H]1O] |

TABLE 1-continued
Selected Compounds
| # | Structure |
|---|---|
| I-424 | 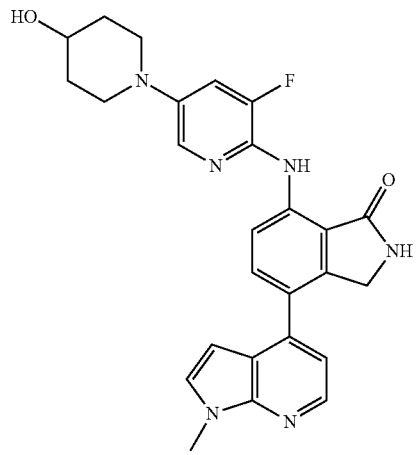 [SMILES: Cn1ccc2c(-c3ccc(Nc4ncc(N5CCC(O)CC5)cc4F)c4c3CNC4=O)ccnc21] |
| I-425 | 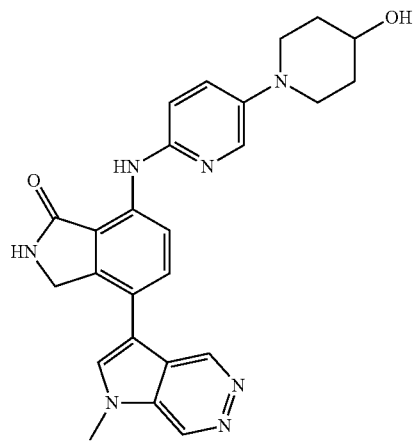 [SMILES: Cn1cc(-c2ccc(Nc3ccc(N4CCC(O)CC4)cn3)c3c2CNC3=O)c2cnncc21] |
| I-426 | 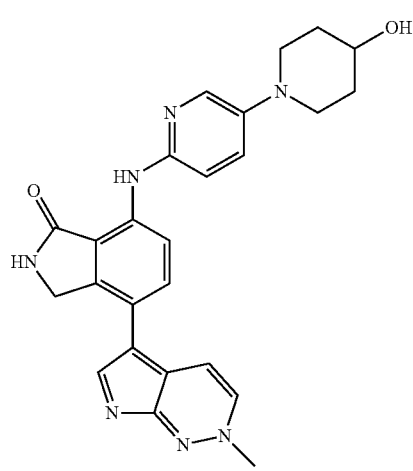 [SMILES: Cn1ccc2c(-c3ccc(Nc4ccc(N5CCC(O)CC5)cn4)c4c3CNC4=O)cnc-2n1] |

TABLE 1-continued

| # | Structure |
|---|---|
| I-427 | 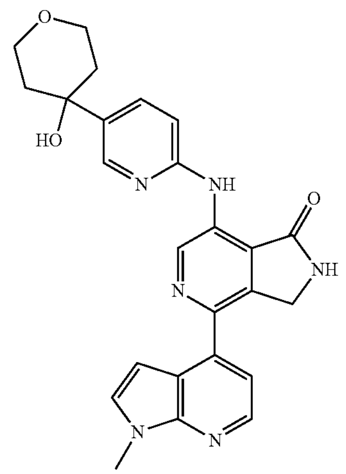 [SMILES: Cn1ccc2c(-c3ncc(Nc4ccc(C5(O)CCOCC5)cn4)c4c3CNC4=O)ccnc21] |
| I-428 | 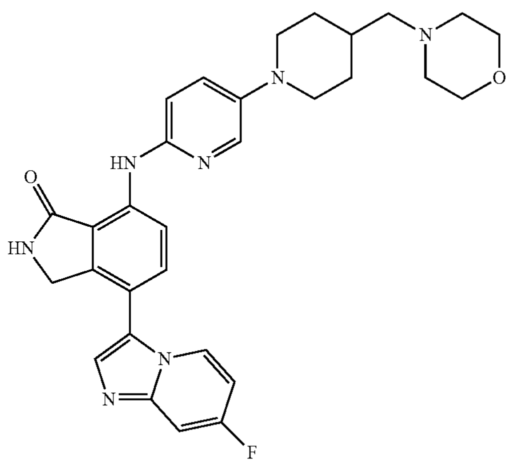 [SMILES: O=C1NCc2c(-c3cnc4cc(F)ccn34)ccc(Nc3ccc(N4CCC(CN5CCOCC5)CC4)cn3)c21] |
| I-429 | 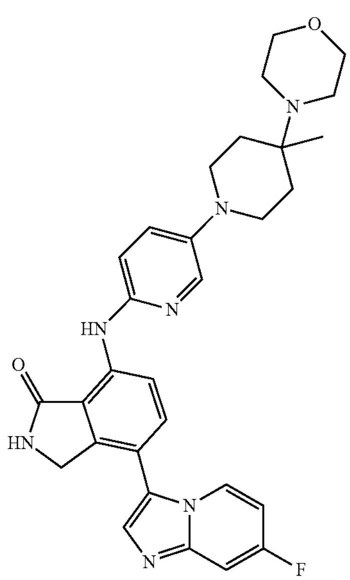 [SMILES: CC1(N2CCOCC2)CCN(c2ccc(Nc3ccc(-c4cnc5cc(F)ccn45)c4c3C(=O)NC4)nc2)CC1] |

TABLE 1-continued
| Selected Compounds | |
|---|---|
| # | Structure |
| I-430 | 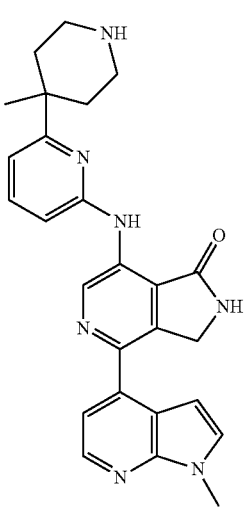 [SMILES: Cn1ccc2c(-c3ncc(Nc4cccc(C5(C)CCNCC5)n4)c4c3CNC4=O)ccnc21] |
| I-431 | 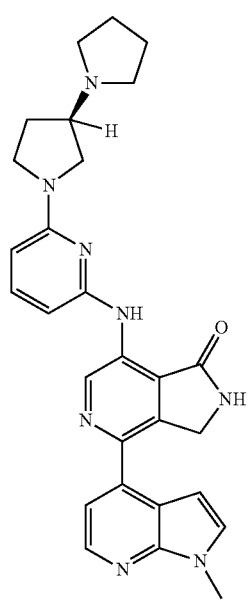 [SMILES: Cn1ccc2c(-c3ncc(Nc4cccc(N5CC[C@@H](N6CCCC6)C5)n4)c4c3CNC4=O)ccnc21] |

TABLE 1-continued
Selected Compounds
| # | Structure |
|---|---|
| I-432 | 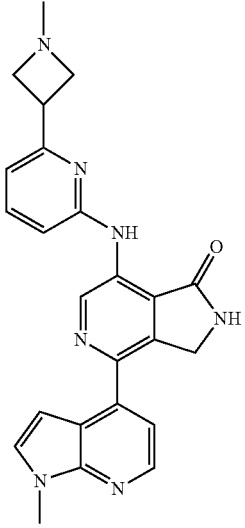 [SMILES: CN1CC(c2cccc(Nc3cnc(-c4ccnc5c4ccn5C)c4c3C(=O)NC4)n2)C1] |
| I-433 | 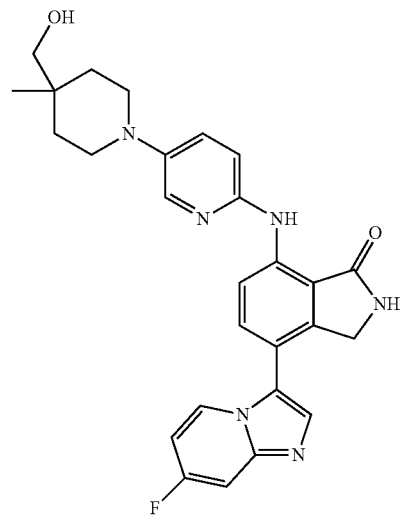 [SMILES: CC1(CO)CCN(c2ccc(Nc3ccc(-c4cnc5cc(F)ccn45)c4c3C(=O)NC4)nc2)CC1] |
| I-434 | 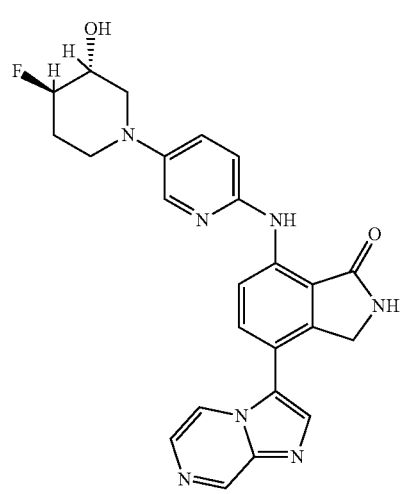 [SMILES: O=C1NCc2c(-c3cnc4cnccn34)ccc(Nc3ccc(N4CC[C@@H](F)[C@H](O)C4)cn3)c21] |

TABLE 1-continued
| Selected Compounds | |
|---|---|
| # | Structure |
I-435
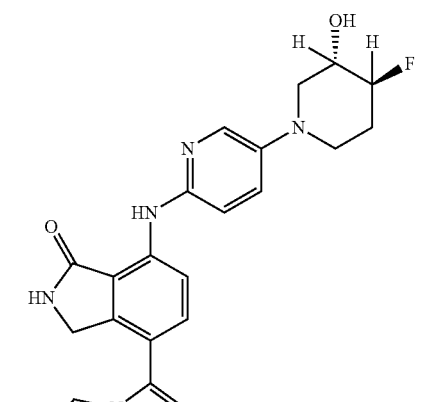
I-436
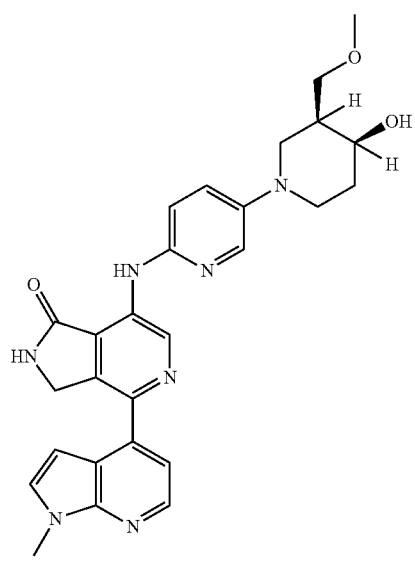 [SMILES: COC[C@@H]1CN(c2ccc(Nc3cnc(-c4ccnc5c4ccn5C)c4c3C(=O)NC4)nc2)CC[C@@H]1O]

TABLE 1-continued
Selected Compounds
| # | Structure |
|---|---|
| I-437 | 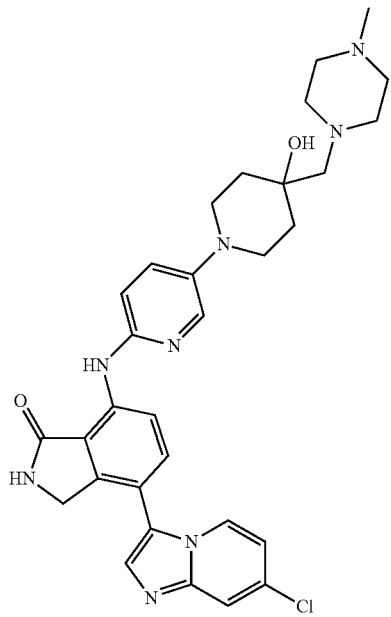 [SMILES: CN1CCN(CC2(O)CCN(c3ccc(Nc4ccc(-c5cnc6cc(Cl)ccn56)c5c4C(=O)NC5)nc3)CC2)CC1] |
| I-438 | 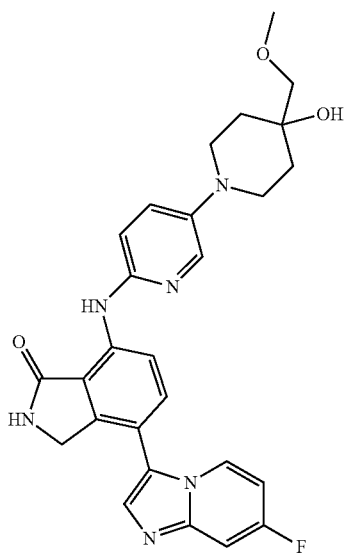 [SMILES: COCC1(O)CCN(c2ccc(Nc3ccc(-c4cnc5cc(F)ccn45)c4c3C(=O)NC4)nc2)CC1] |

437
TABLE 1-continued
| Selected Compounds | |
|---|---|
| # | Structure |
I-439
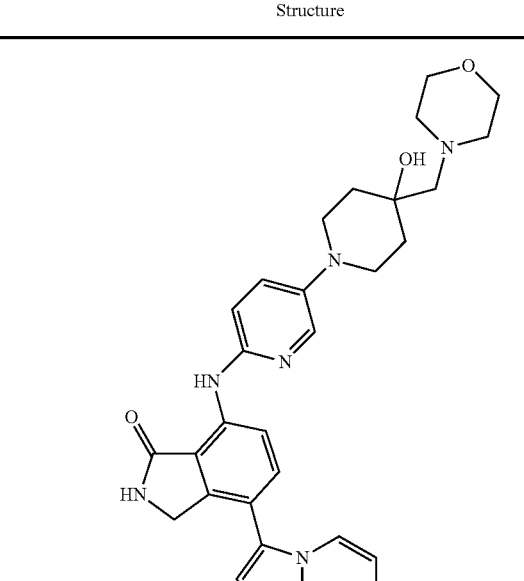
I-440
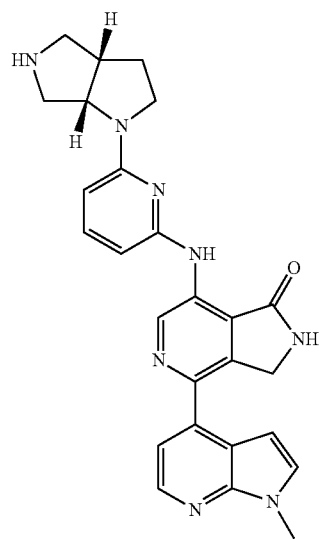 [SMILES: Cn1ccc2c(-c3ncc(Nc4cccc(N5CC[C@H]6CNC[C@H]65)n4)c4c3CNC4=O)ccnc21]

TABLE 1-continued
Selected Compounds
| # | Structure |
|---|---|
| I-441 | 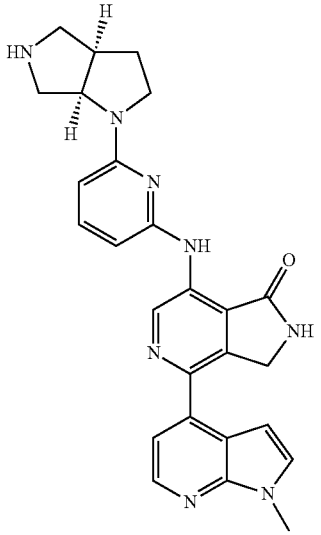 [SMILES: Cn1ccc2c(-c3ncc(Nc4cccc(N5CC[C@@H]6CNC[C@@H]65)n4)c4c3CNC4=O)ccnc21] |
| I-442 | 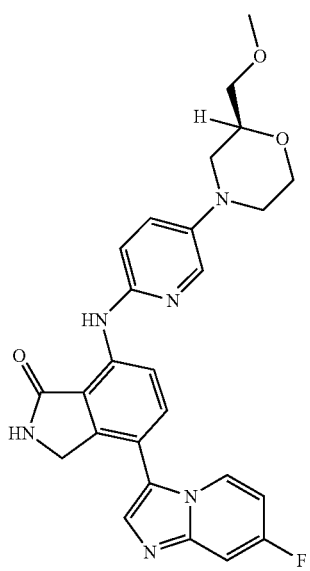 [SMILES: COC[C@@H]1CN(c2ccc(Nc3ccc(-c4cnc5cc(F)ccn45)c4c3C(=O)NC4)nc2)CCO1] |

TABLE 1-continued
Selected Compounds
| # | Structure |
|---|---|
| I-443 | 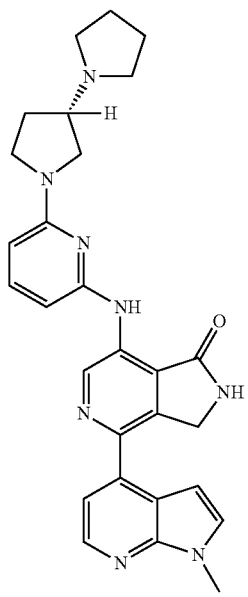 [SMILES: Cn1ccc2c(-c3ncc(Nc4cccc(N5CC[C@H](N6CCCC6)C5)n4)c4c3CNC4=O)ccnc21] |
| I-444 | 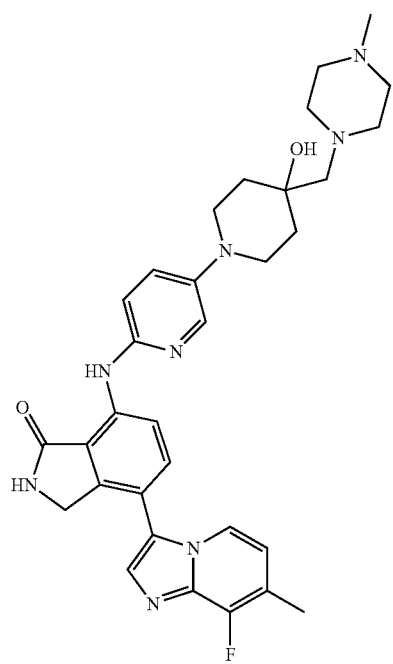 [SMILES: Cc1ccn2c(-c3ccc(Nc4ccc(N5CCC(O)(CN6CCN(C)CC6)CC5)cn4)c4c3CNC4=O)cnc2c1F] |

TABLE 1-continued
Selected Compounds
| # | Structure |
|---|---|
| I-445 | 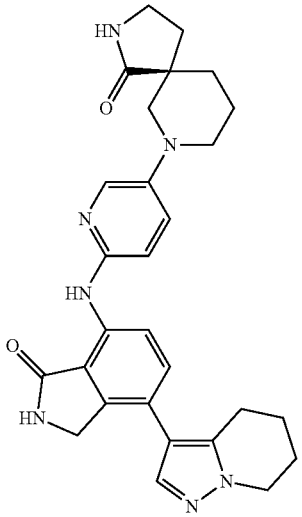 [SMILES: O=C1NCc2c(-c3cnn4c3CCCC4)ccc(Nc3ccc(N4CCC[C@@]5(CCNC5=O)C4)cn3)c21] |
| I-446 | 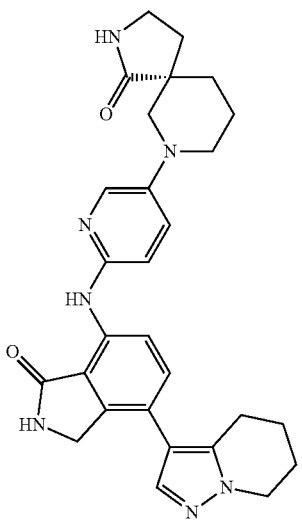 [SMILES: O=C1NCc2c(-c3cnn4c3CCCC4)ccc(Nc3ccc(N4CCC[C@]5(CCNC5=O)C4)cn3)c21] |

TABLE 1-continued
Selected Compounds
| # | Structure |
|---|---|
| I-447 | 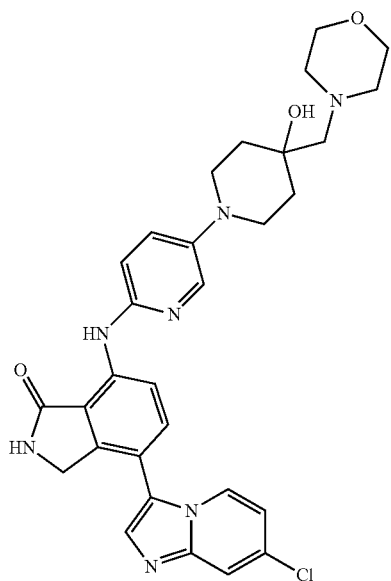 [SMILES: O=C1NCc2c(-c3cnc4cc(Cl)ccn34)ccc(Nc3ccc(N4CCC(O)(CN5CCOCC5)CC4)cn3)c21] |
| I-448 | 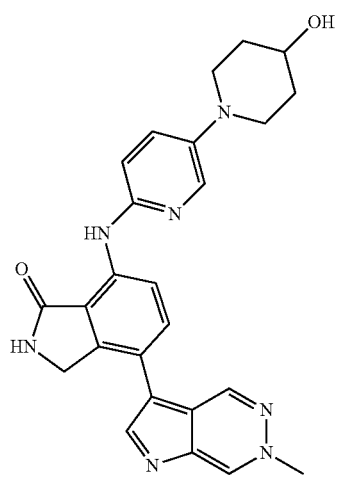 [SMILES: Cn1cc2ncc(-c3ccc(Nc4ccc(N5CCC(O)CC5)cn4)c4c3CNC4=O)c-2cn1] |
| I-449 | 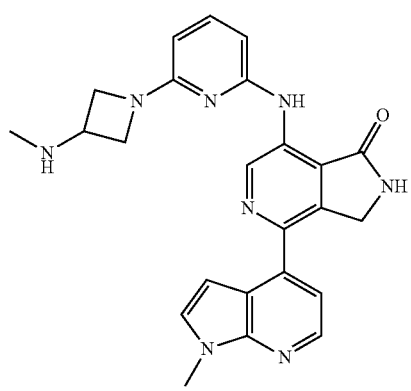 [SMILES: CNC1CN(c2cccc(Nc3cnc(-c4ccnc5c4ccn5C)c4c3C(=O)NC4)n2)C1] |

TABLE 1-continued
Selected Compounds
| # | Structure |
|---|---|
| I-450 | 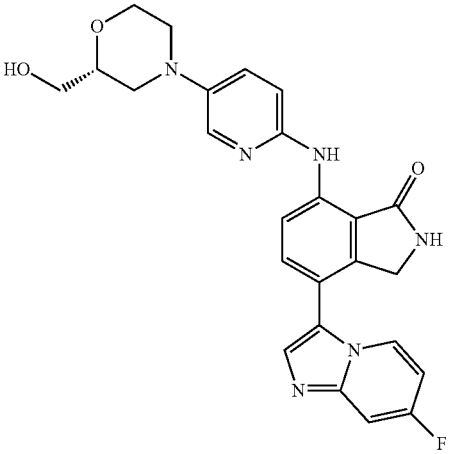 [SMILES: O=C1NCc2c(-c3cnc4cc(F)ccn34)ccc(Nc3ccc(N4CCO[C@@H](CO)C4)cn3)c21] |
| I-451 | 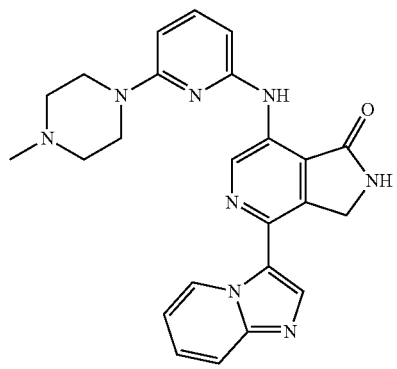 [SMILES: CN1CCN(c2cccc(Nc3cnc(-c4cnc5ccccn45)c4c3C(=O)NC4)n2)CC1] |
| I-452 | 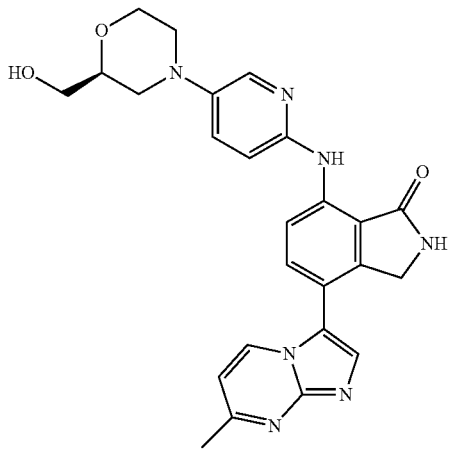 [SMILES: Cc1ccn2c(-c3ccc(Nc4ccc(N5CCO[C@H](CO)C5)cn4)c4c3CNC4=O)cnc2n1] |

TABLE 1-continued
Selected Compounds
| # | Structure |
|---|---|
| I-453 | 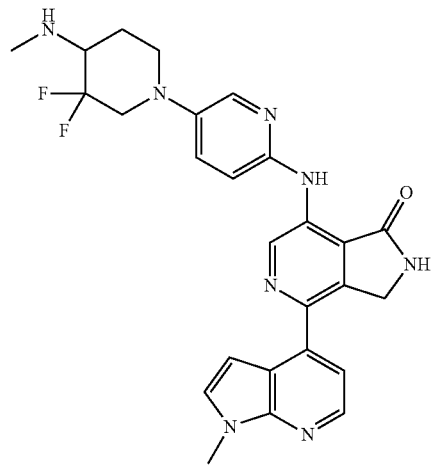 [SMILES: CNC1CCN(c2ccc(Nc3cnc(-c4ccnc5c4ccn5C)c4c3C(=O)NC4)nc2)CC1(F)F] |
| I-454 | 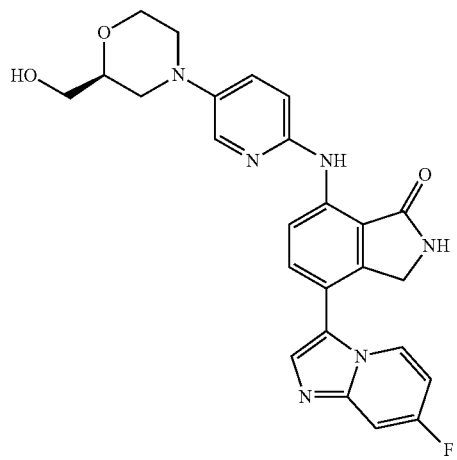 [SMILES: O=C1NCc2c(-c3cnc4cc(F)ccn34)ccc(Nc3ccc(N4CCO[C@H](CO)C4)cn3)c21] |
| I-455 | 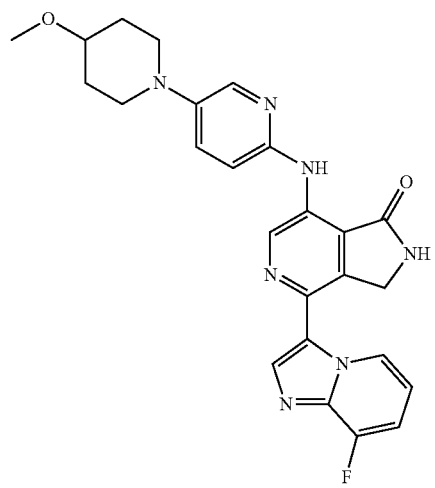 [SMILES: COC1CCN(c2ccc(Nc3cnc(-c4cnc5c(F)cccn45)c4c3C(=O)NC4)nc2)CC1] |

TABLE 1-continued
Selected Compounds
| # | Structure |
|---|---|
| I-456 | 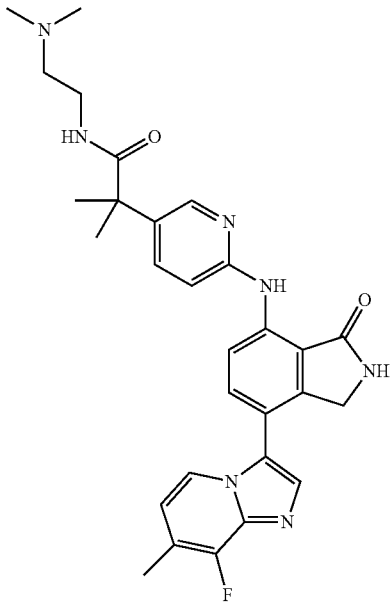 [SMILES: Cc1ccn2c(-c3ccc(Nc4ccc(C(C)(C)C(=O)NCCN(C)C)cn4)c4c3CNC4=O)cnc2c1F] |
| I-457 | 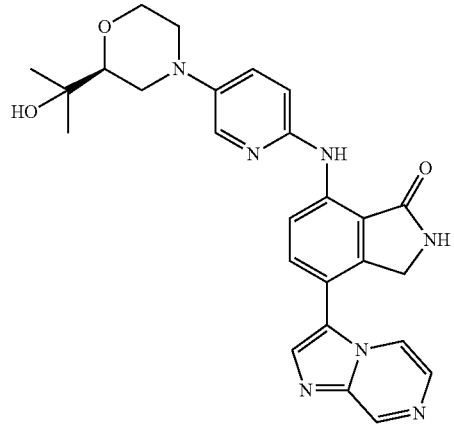 [SMILES: CC(C)(O)[C@@H]1CN(c2ccc(Nc3ccc(-c4cnc5cnccn45)c4c3C(=O)NC4)nc2)CCO1] |
| I-458 | 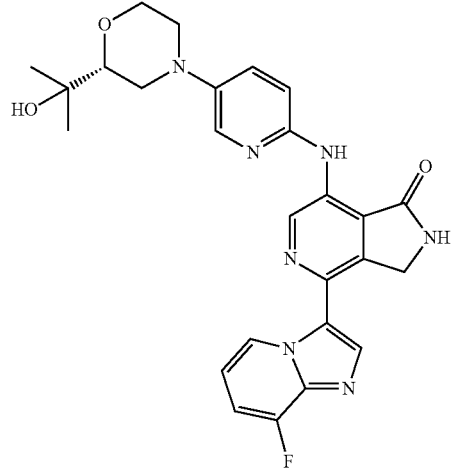 [SMILES: CC(C)(O)[C@H]1CN(c2ccc(Nc3cnc(-c4cnc5c(F)cccn45)c4c3C(=O)NC4)nc2)CCO1] |

TABLE 1-continued

Selected Compounds

| # | Structure |
|---|---|
| I-459 | 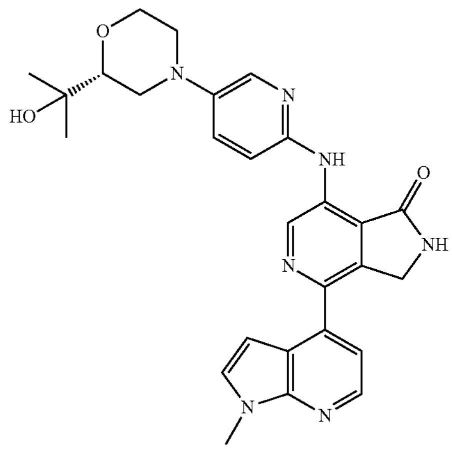 [SMILES: Cn1ccc2c(-c3ncc(Nc4ccc(N5CCO[C@@H](C(C)(C)O)C5)cn4)c4c3CNC4=O)ccnc21] |
| I-460 | 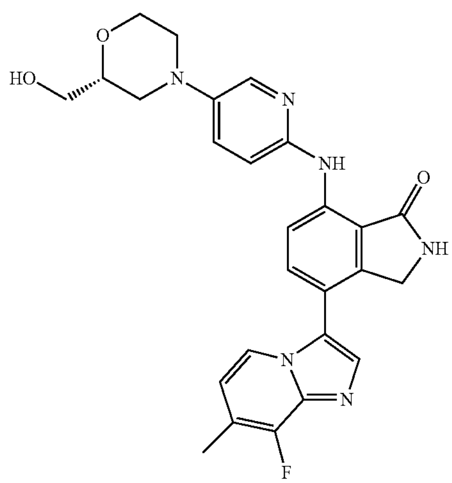 [SMILES: Cc1ccn2c(-c3ccc(Nc4ccc(N5CCO[C@@H](CO)C5)cn4)c4c3CNC4=O)cnc2c1F] |
| I-461 | 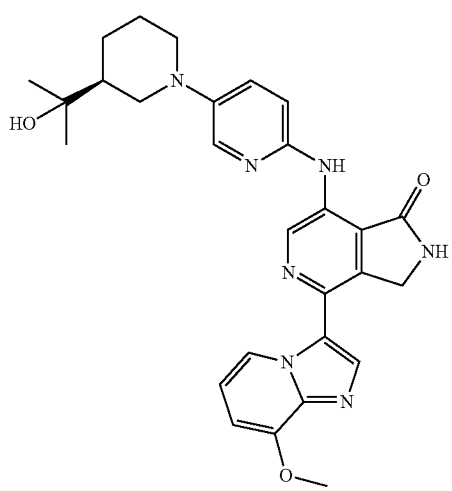 [SMILES: COc1cccn2c(-c3ncc(Nc4ccc(N5CCC[C@H](C(C)(C)O)C5)cn4)c4c3CNC4=O)cnc12] |

455
TABLE 1-continued
Selected Compounds
| # | Structure |
|---|---|
| I-462 | 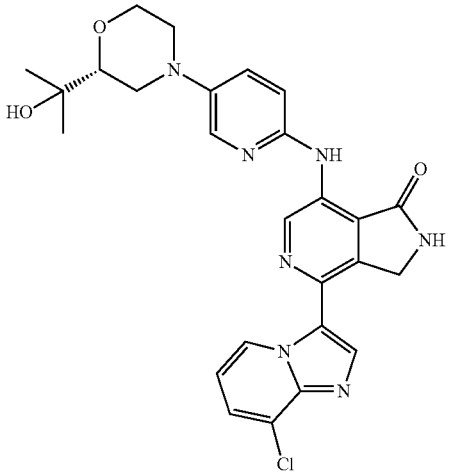 [SMILES: CC(C)(O)[C@H]1CN(c2ccc(Nc3cnc(-c4cnc5c(Cl)cccn45)c4c3C(=O)NC4)nc2)CCO1] |
| I-463 | 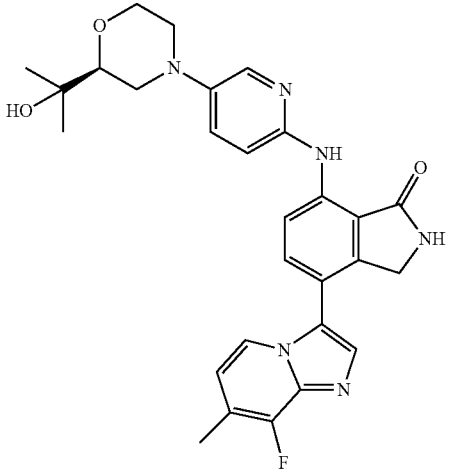 [SMILES: Cc1ccn2c(-c3ccc(Nc4ccc(N5CCO[C@H](C(C)(C)O)C5)cn4)c4c3CNC4=O)cnc2c1F] |
| I-464 | 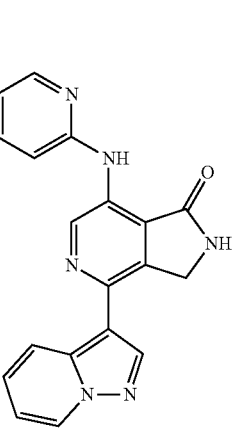 |

TABLE 1-continued
Selected Compounds
| # | Structure |
|---|---|
| I-465 | 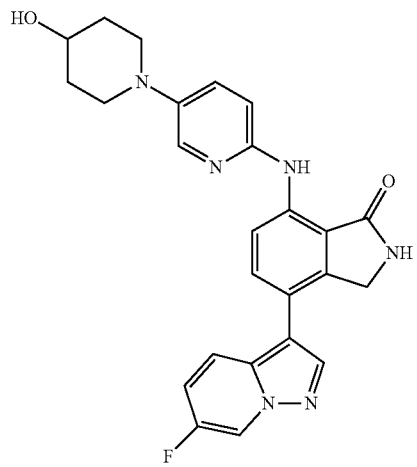 [SMILES: O=C1NCc2c(-c3cnn4cc(F)ccc34)ccc(Nc3ccc(N4CCC(O)CC4)cn3)c21] |
| I-467 | 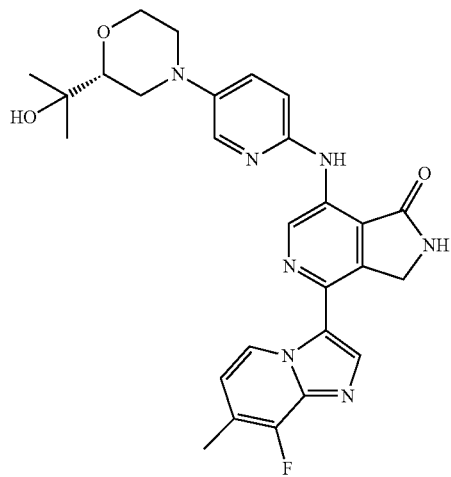 [SMILES: Cc1ccn2c(-c3ncc(Nc4ccc(N5CCO[C@@H](C(C)(C)O)C5)cn4)c4c3CNC4=O)cnc2c1F] |
| I-468 | 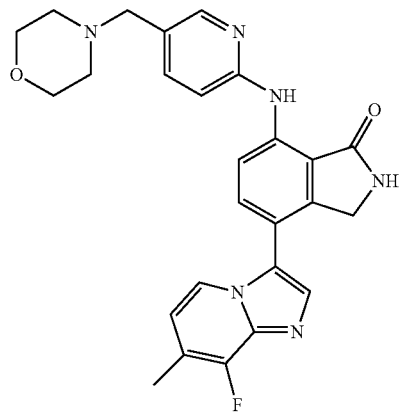 [SMILES: Cc1ccn2c(-c3ccc(Nc4ccc(CN5CCOCC5)cn4)c4c3CNC4=O)cnc2c1F] |

TABLE 1-continued
| Selected Compounds | |
|---|---|
| # | Structure |
I-469
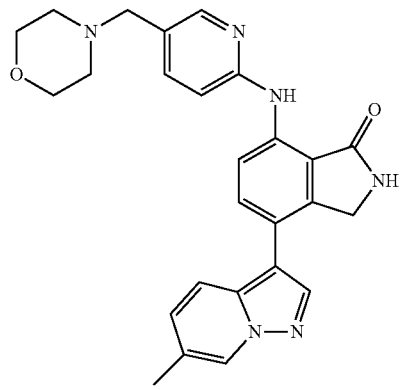 [SMILES: Cc1ccc2c(-c3ccc(Nc4ccc(CN5CCOCC5)cn4)c4c3CNC4=O)cnn2c1]
I-470
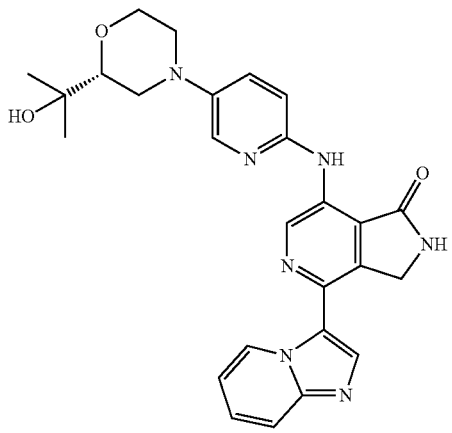 [SMILES: CC(C)(O)[C@H]1CN(c2ccc(Nc3cnc(-c4cnc5ccccn45)c4c3C(=O)NC4)nc2)CCO1]
I-471
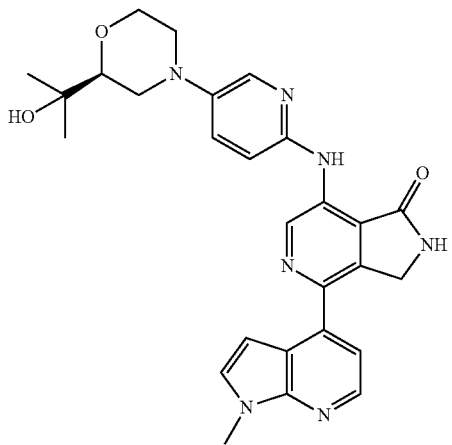 [SMILES: Cn1ccc2c(-c3ncc(Nc4ccc(N5CCO[C@H](C(C)(C)O)C5)cn4)c4c3CNC4=O)ccnc21]

TABLE 1-continued
Selected Compounds
| # | Structure |
|---|-----------|
| I-472 | 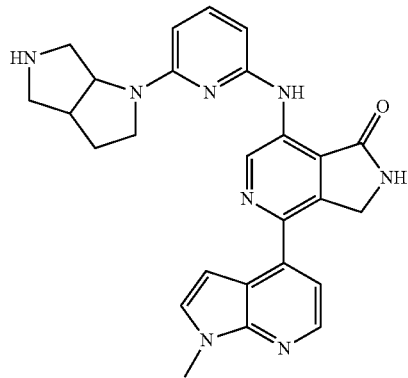 [SMILES: Cn1ccc2c(-c3ncc(Nc4cccc(N5CCC6CNCC65)n4)c4c3CNC4=O)ccnc21] |
| I-473 | 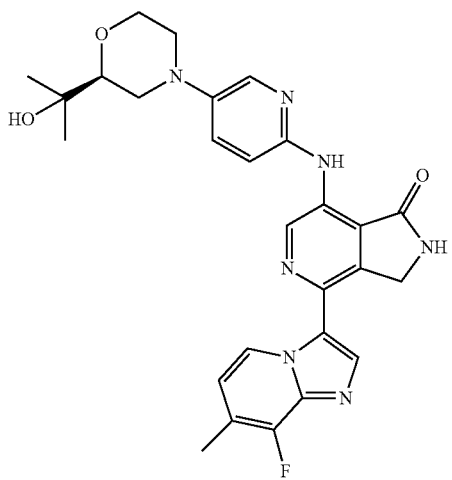 [SMILES: Cc1ccn2c(-c3ncc(Nc4ccc(N5CCO[C@H](C(C)(C)O)C5)cn4)c4c3CNC4=O)cnc2c1F] |
| I-474 | 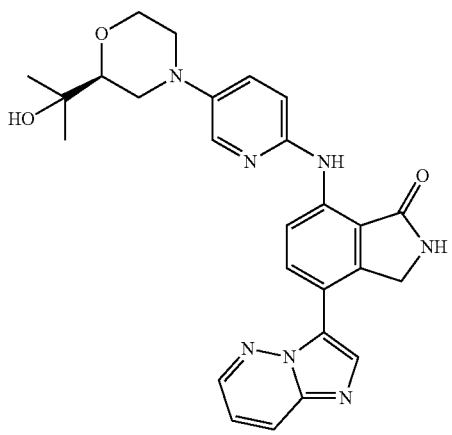 [SMILES: CC(C)(O)[C@@H]1CN(c2ccc(Nc3ccc(-c4cnc5cccnn45)c4c3C(=O)NC4)nc2)CCO1] |

TABLE 1-continued

| Selected Compounds | |
|---|---|
| # | Structure |

I-475

I-476

I-477

TABLE 1-continued
| Selected Compounds | |
|---|---|
| # | Structure |
I-478
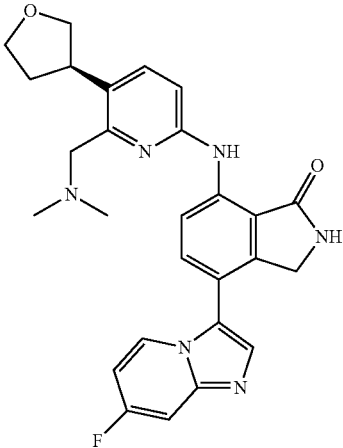 [SMILES: CN(C)Cc1nc(Nc2ccc(-c3cnc4cc(F)ccn34)c3c2C(=O)NC3)ccc1[C@H]1CCOC1]
I-479
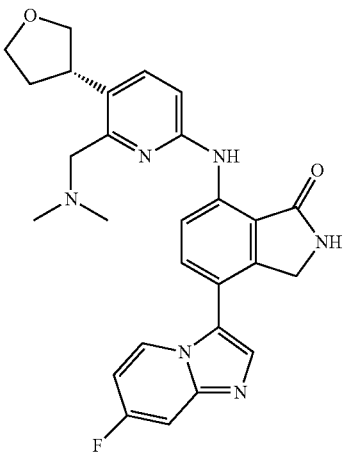 [SMILES: CN(C)Cc1nc(Nc2ccc(-c3cnc4cc(F)ccn34)c3c2C(=O)NC3)ccc1[C@@H]1CCOC1]
I-480
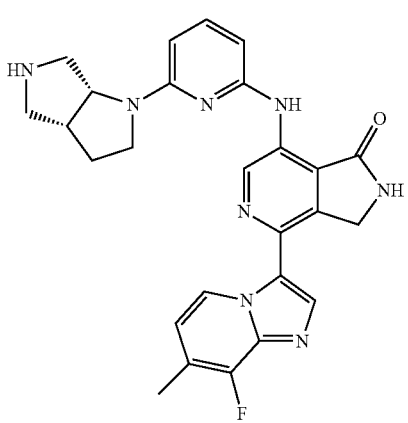 [SMILES: Cc1ccn2c(-c3ncc(Nc4cccc(N5CC[C@@H]6CNC[C@@H]65)n4)c4c3CNC4=O)cnc2c1F]

TABLE 1-continued
Selected Compounds
| # | Structure |
|---|---|
| I-481 | 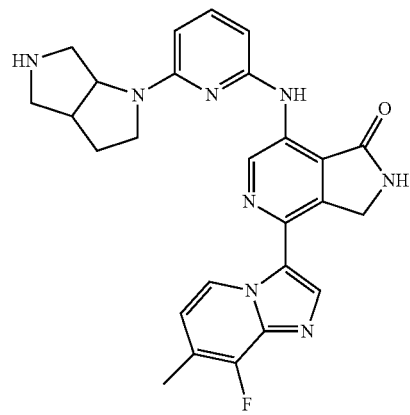 [SMILES: Cc1ccn2c(-c3ncc(Nc4cccc(N5CCC6CNCC65)n4)c4c3CNC4=O)cnc2c1F] |
| I-482 | 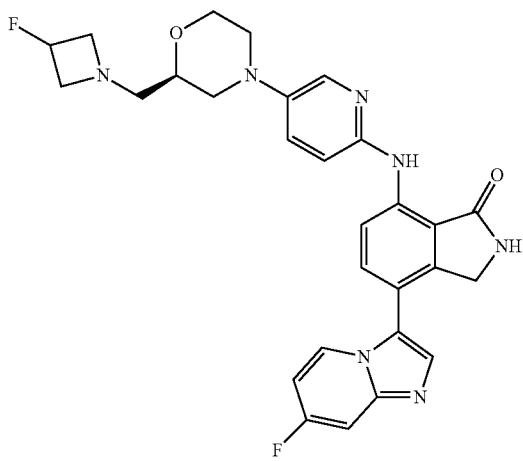 [SMILES: O=C1NCc2c(-c3cnc4cc(F)ccn34)ccc(Nc3ccc(N4CCO[C@H](CN5CC(F)C5)C4)cn3)c21] |
| I-483 | 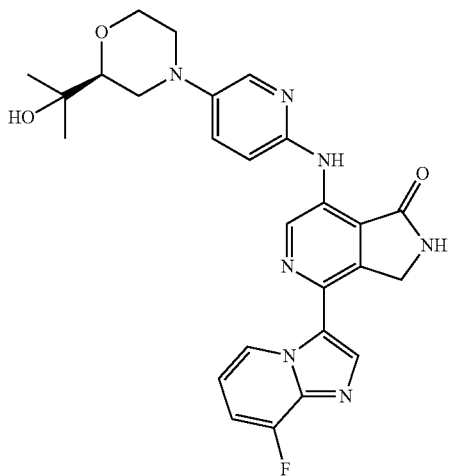 [SMILES: CC(C)(O)[C@@H]1CN(c2ccc(Nc3cnc(-c4cnc5c(F)cccn45)c4c3C(=O)NC4)nc2)CCO1] |

TABLE 1-continued
| Selected Compounds | |
|---|---|
| # | Structure |
I-484
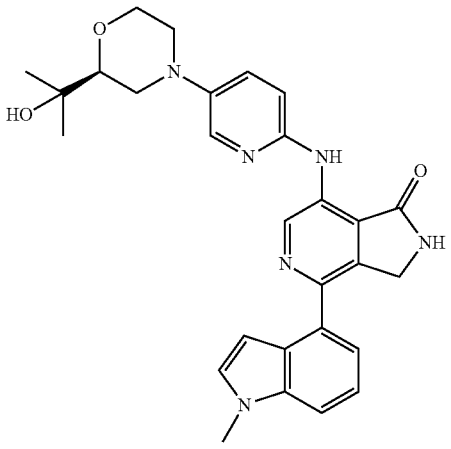 [SMILES: Cn1ccc2c(-c3ncc(Nc4ccc(N5CCO[C@H](C(C)(C)O)C5)cn4)c4c3CNC4=O)cccc21]
I-485
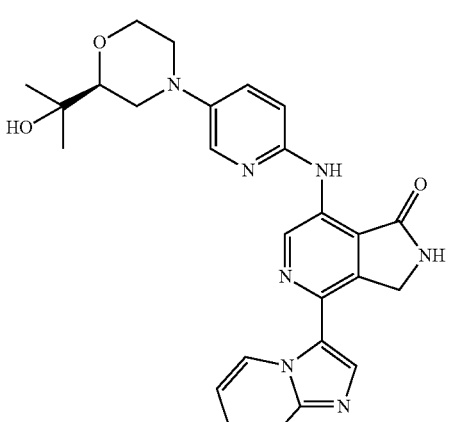
I-486
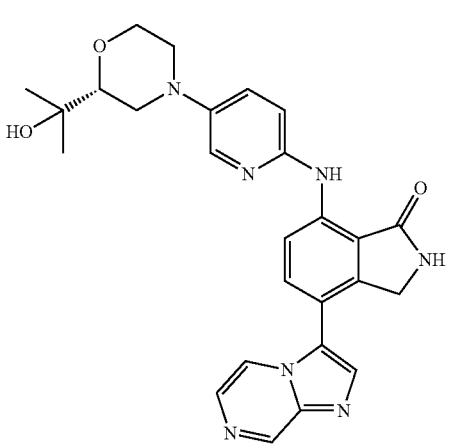 [SMILES: CC(C)(O)[C@H]1CN(c2ccc(Nc3ccc(-c4cnc5cnccn45)c4c3C(=O)NC4)nc2)CCO1]

TABLE 1-continued

| Selected Compounds | |
|---|---|
| # | Structure |ിക

I-487

I-488

I-489

TABLE 1-continued
Selected Compounds
| # | Structure |
|---|---|
| I-490 | 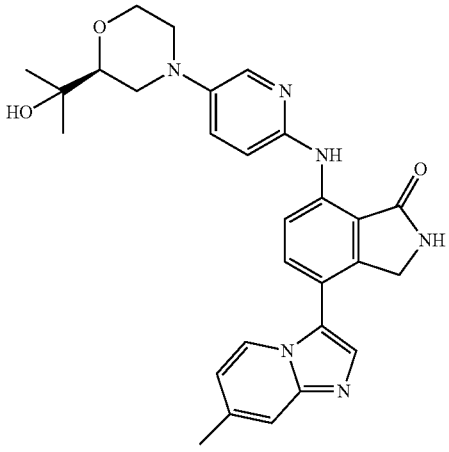 [SMILES: Cc1ccn2c(-c3ccc(Nc4ccc(N5CCO[C@H](C(C)(C)O)C5)cn4)c4c3CNC4=O)cnc2c1] |
| I-491 | 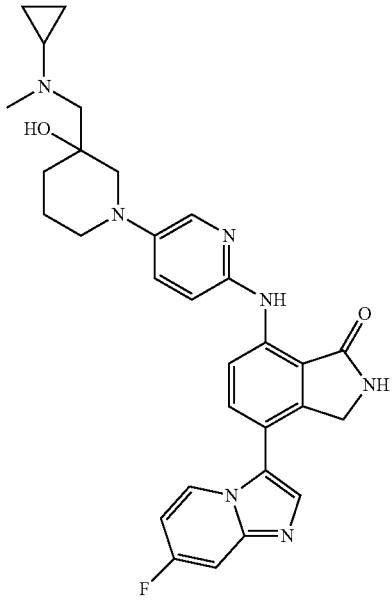 [SMILES: CN(CC1(O)CCCN(c2ccc(Nc3ccc(-c4cnc5cc(F)ccn45)c4c3C(=O)NC4)nc2)C1)C1CC1] |
| I-492 | 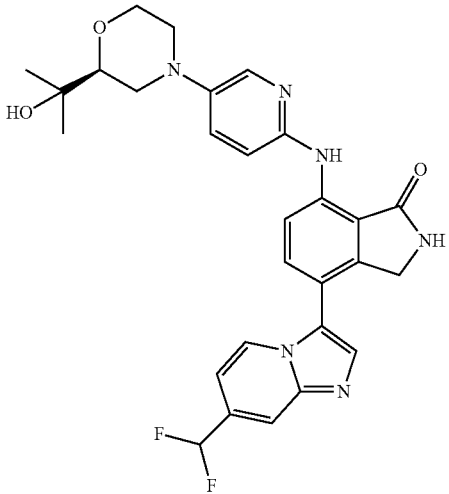 [SMILES: CC(C)(O)[C@@H]1CN(c2ccc(Nc3ccc(-c4cnc5cc(C(F)F)ccn45)c4c3C(=O)NC4)nc2)CCO1] |

TABLE 1-continued
| Selected Compounds | |
|---|---|
| # | Structure |
I-493
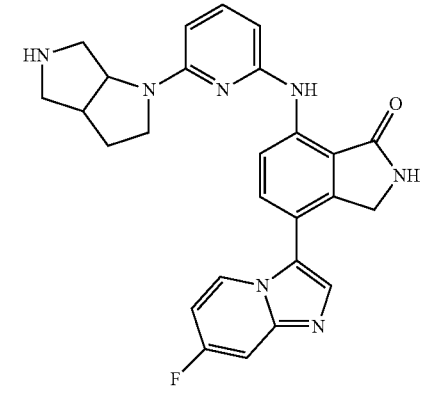 [SMILES: O=C1NCc2c(-c3cnc4cc(F)ccn34)ccc(Nc3cccc(N4CCC5CNCC54)n3)c21]
I-494
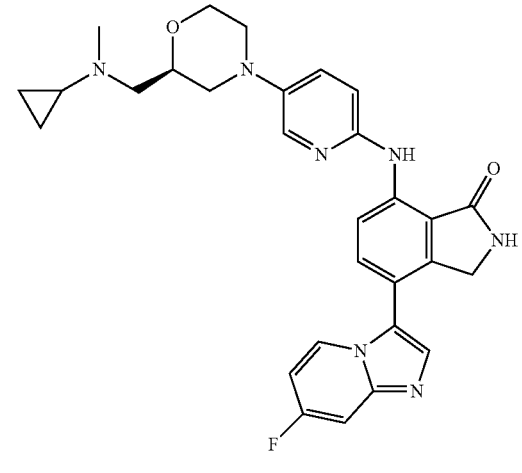 [SMILES: CN(C[C@@H]1CN(c2ccc(Nc3ccc(-c4cnc5cc(F)ccn45)c4c3C(=O)NC4)nc2)CCO1)C1CC1]
I-495
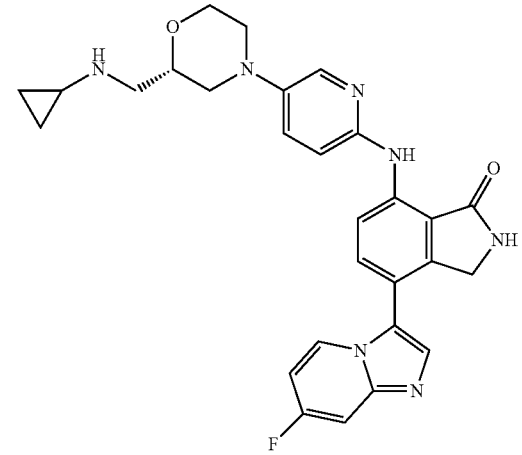 [SMILES: O=C1NCc2c(-c3cnc4cc(F)ccn34)ccc(Nc3ccc(N4CCO[C@@H](CNC5CC5)C4)cn3)c21]

TABLE 1-continued
Selected Compounds
| # | Structure |
|---|---|
| I-496 | 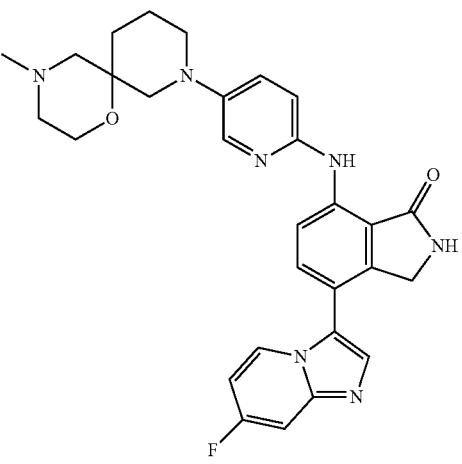 [SMILES: CN1CCOC2(CCCN(c3ccc(Nc4ccc(-c5cnc6cc(F)ccn56)c5c4C(=O)NC5)nc3)C2)C1] |
| I-497 | 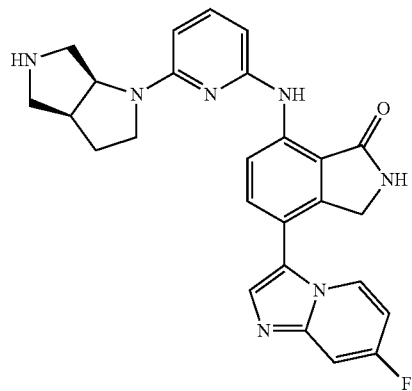 [SMILES: O=C1NCc2c(-c3cnc4cc(F)ccn34)ccc(Nc3cccc(N4CC[C@H]5CNC[C@H]54)n3)c21] |
| I-498 | 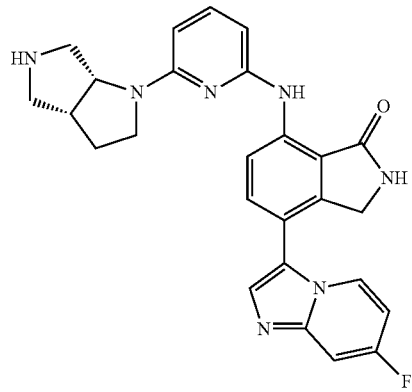 [SMILES: O=C1NCc2c(-c3cnc4cc(F)ccn34)ccc(Nc3cccc(N4CC[C@@H]5CNC[C@@H]54)n3)c21] |

TABLE 1-continued
Selected Compounds
| # | Structure |
|---|---|
| I-499 | 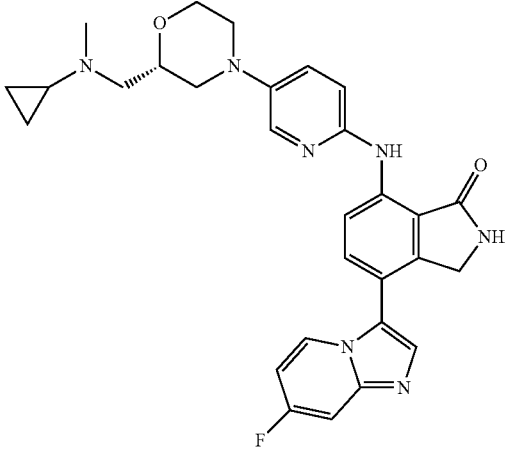 [SMILES: CN(C[C@H]1CN(c2ccc(Nc3ccc(-c4cnc5cc(F)ccn45)c4c3C(=O)NC4)nc2)CCO1)C1CC1] |
| I-500 | 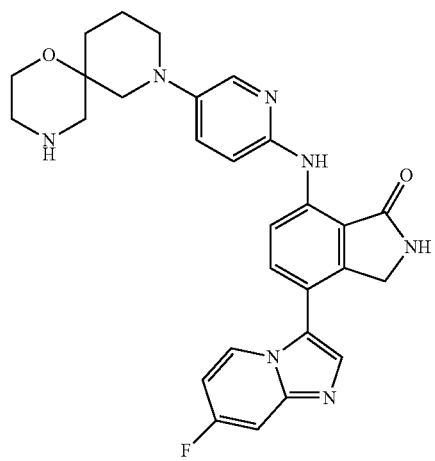 [SMILES: O=C1NCc2c(-c3cnc4cc(F)ccn34)ccc(Nc3ccc(N4CCCC5(CNCCO5)C4)cn3)c21] |
| I-501 | 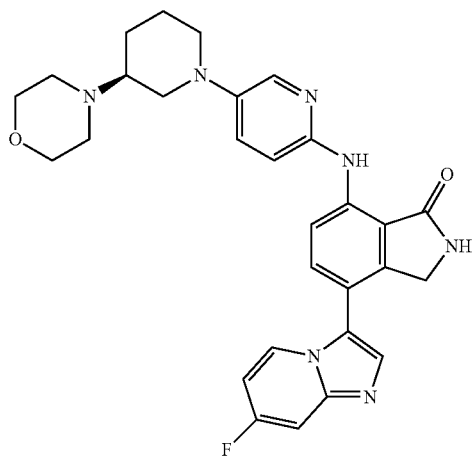 [SMILES: O=C1NCc2c(-c3cnc4cc(F)ccn34)ccc(Nc3ccc(N4CCC[C@H](N5CCOCC5)C4)cn3)c21] |

481 482
TABLE 1-continued
Selected Compounds
| # | Structure |
|---|---|
| I-502 | 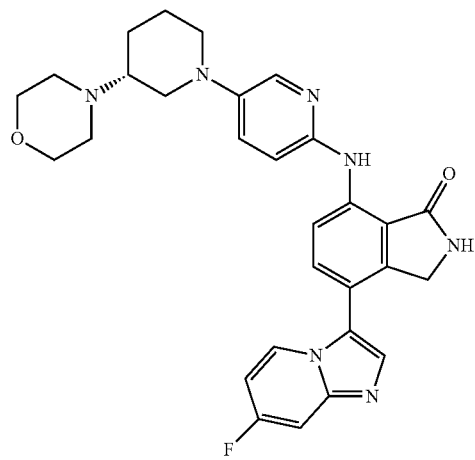 [SMILES: O=C1NCc2c(-c3cnc4cc(F)ccn34)ccc(Nc3ccc(N4CCC[C@@H](N5CCOCC5)C4)cn3)c21] |
| I-503 | 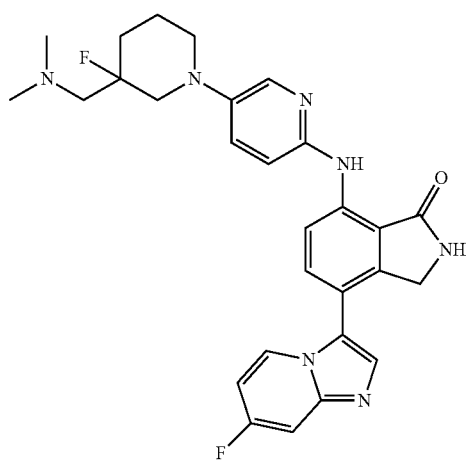 [SMILES: CN(C)CC1(F)CCCN(c2ccc(Nc3ccc(-c4cnc5cc(F)ccn45)c4c3C(=O)NC4)nc2)C1] |
| I-504 | 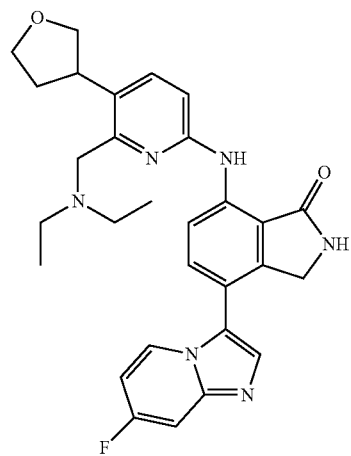 [SMILES: CCN(CC)Cc1nc(Nc2ccc(-c3cnc4cc(F)ccn34)c3c2C(=O)NC3)ccc1C1CCOC1] |

TABLE 1-continued
Selected Compounds
| # | Structure |
|---|---|
| I-505 | 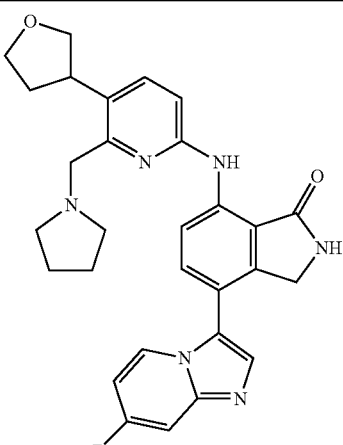 |
| I-506a | 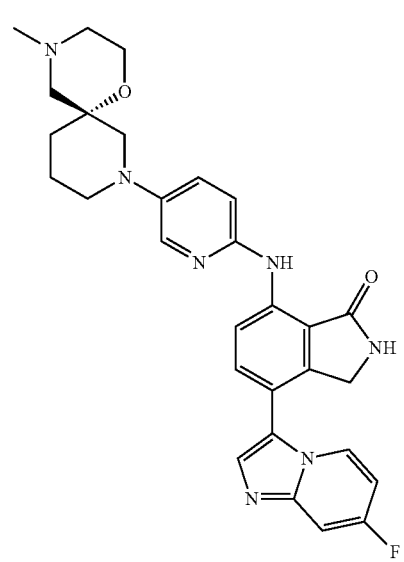 [SMILES: CN1CCO[C@]2(CCCN(c3ccc(Nc4ccc(-c5cnc6cc(F)ccn56)c5c4C(=O)NC5)nc3)C2)C1] |
| I-506 | 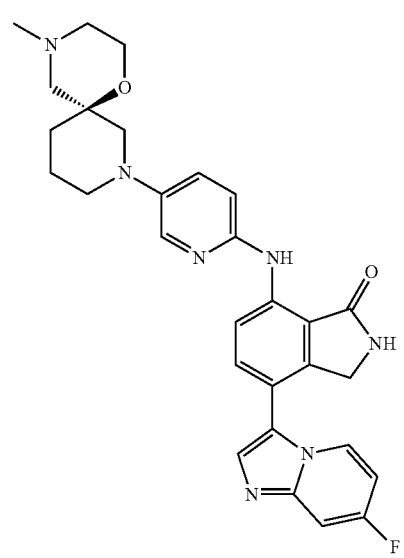 [SMILES: CN1CCO[C@@]2(CCCN(c3ccc(Nc4ccc(-c5cnc6cc(F)ccn56)c5c4C(=O)NC5)nc3)C2)C1] |

TABLE 1-continued
Selected Compounds
| # | Structure |
|---|---|
| I-507 | 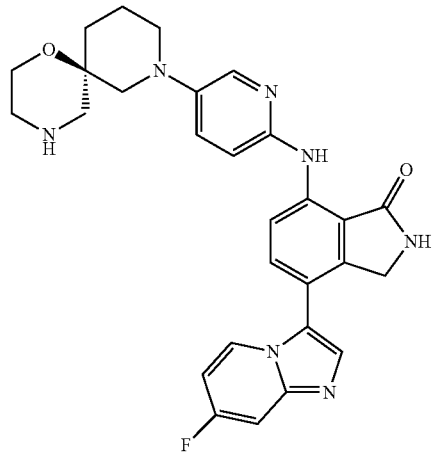 [SMILES: O=C1NCc2c(-c3cnc4cc(F)ccn34)ccc(Nc3ccc(N4CCC[C@@]5(CNCCO5)C4)cn3)c21] |
| I-508 | 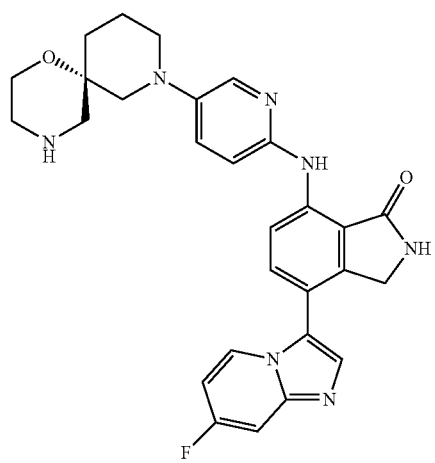 [SMILES: O=C1NCc2c(-c3cnc4cc(F)ccn34)ccc(Nc3ccc(N4CCC[C@]5(CNCCO5)C4)cn3)c21] |
| I-509 | 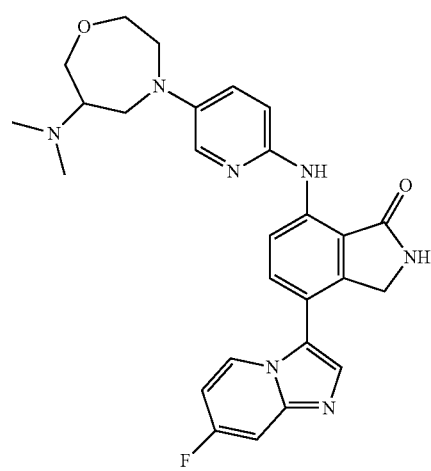 [SMILES: CN(C)C1COCCN(c2ccc(Nc3ccc(-c4cnc5cc(F)ccn45)c4c3C(=O)NC4)nc2)C1] |

TABLE 1-continued
Selected Compounds
| # | Structure |
|---|---|
| I-510 | 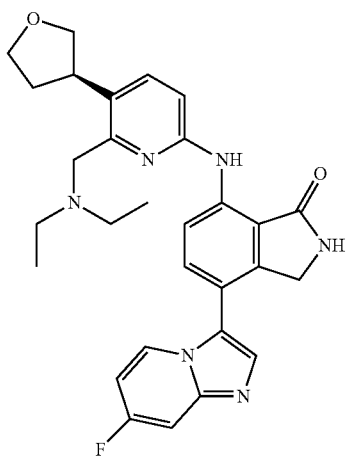 [SMILES: CCN(CC)Cc1nc(Nc2ccc(-c3cnc4cc(F)ccn34)c3c2C(=O)NC3)ccc1[C@H]1CCOC1] |
| I-511 | 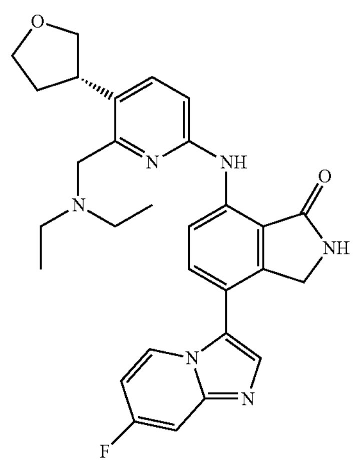 [SMILES: CCN(CC)Cc1nc(Nc2ccc(-c3cnc4cc(F)ccn34)c3c2C(=O)NC3)ccc1[C@@H]1CCOC1] |
| I-512 | 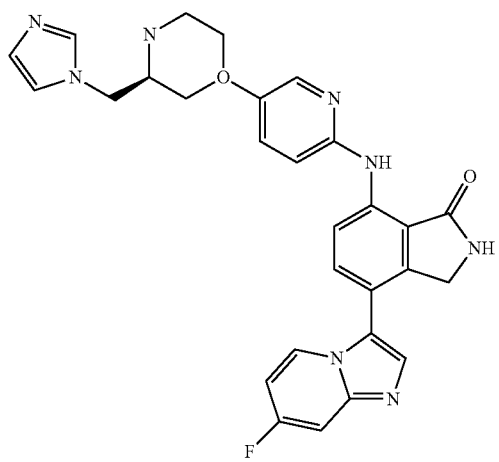 |

TABLE 1-continued
Selected Compounds
| # | Structure |
|---|---|
| I-513 | 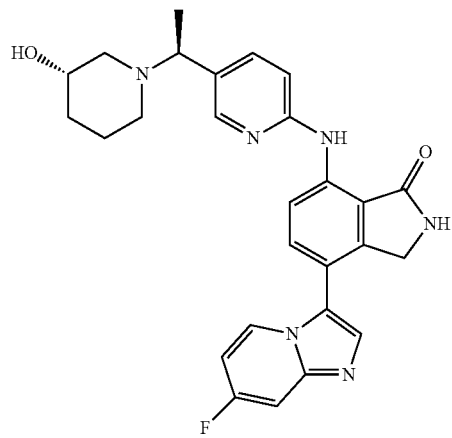 [SMILES: C[C@@H](c1ccc(Nc2ccc(-c3cnc4cc(F)ccn34)c3c2C(=O)NC3)nc1)N1CCC[C@H](O)C1] |
| I-514 | 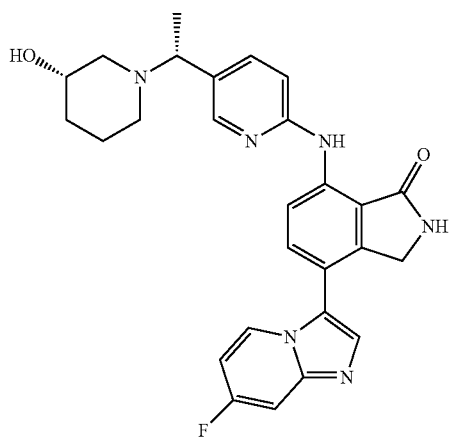 [SMILES: C[C@H](c1ccc(Nc2ccc(-c3cnc4cc(F)ccn34)c3c2C(=O)NC3)nc1)N1CCC[C@H](O)C1] |
| I-515 | 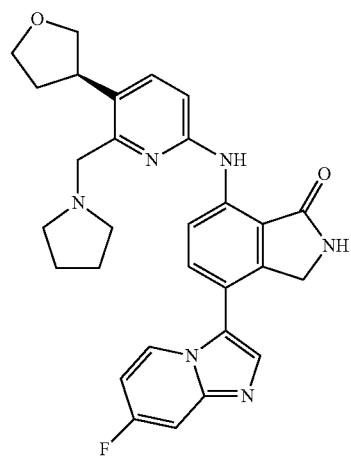 [SMILES: O=C1NCc2c(-c3cnc4cc(F)ccn34)ccc(Nc3ccc([C@H]4CCOC4)c(CN4CCCC4)n3)c21] |

TABLE 1-continued
Selected Compounds
| # | Structure |
|---|---|
| I-516 | 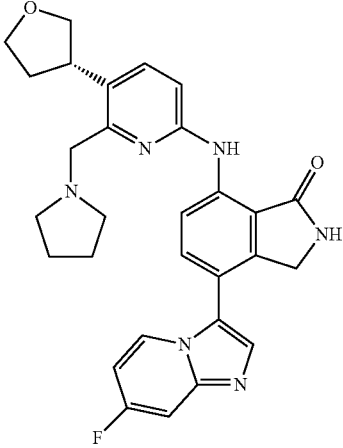 [SMILES: O=C1NCc2c(-c3cnc4cc(F)ccn34)ccc(Nc3ccc([C@@H]4CCOC4)c(CN4CCCC4)n3)c21] |
| I-517 | 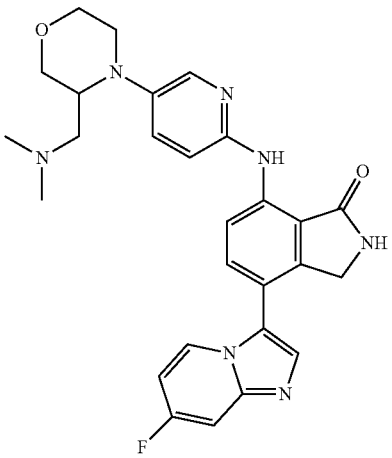 [SMILES: CN(C)CC1COCCN1c1ccc(Nc2ccc(-c3cnc4cc(F)ccn34)c3c2C(=O)NC3)nc1] |
| I-518 | 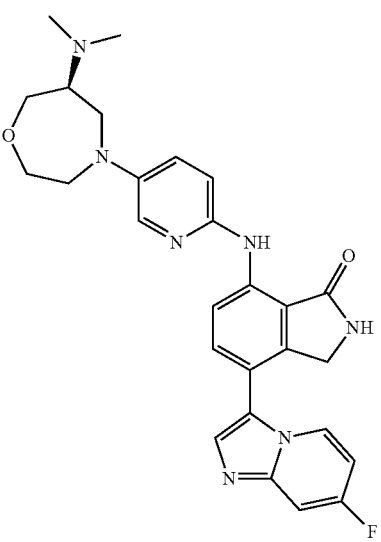 [SMILES: CN(C)[C@@H]1COCCN(c2ccc(Nc3ccc(-c4cnc5cc(F)ccn45)c4c3C(=O)NC4)nc2)C1] |

TABLE 1-continued
| Selected Compounds | |
|---|---|
| # | Structure |
| I-519 | 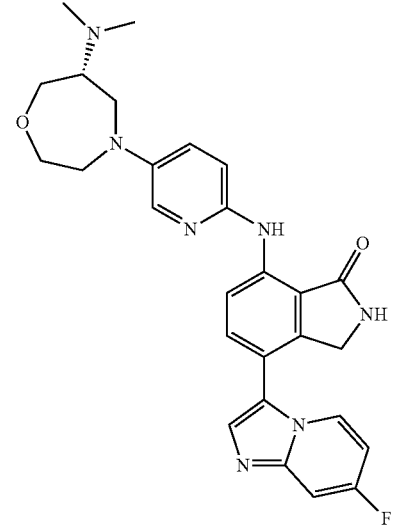 [SMILES: CN(C)[C@H]1COCCN(c2ccc(Nc3ccc(-c4cnc5cc(F)ccn45)c4c3C(=O)NC4)nc2)C1] |
| I-520 | 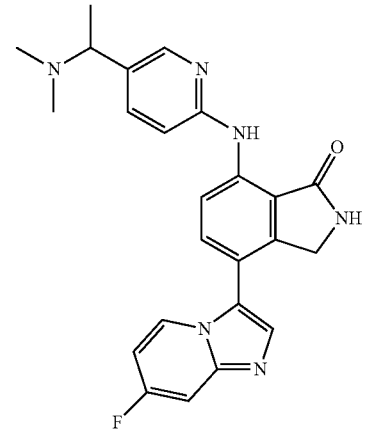 [SMILES: CC(c1ccc(Nc2ccc(-c3cnc4cc(F)ccn34)c3c2C(=O)NC3)nc1)N(C)C] |
| I-521 | 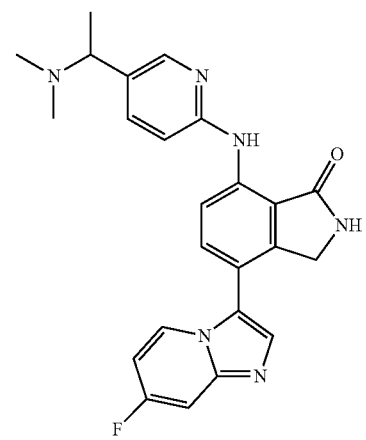 [SMILES: CC(c1ccc(Nc2ccc(-c3cnc4cc(F)ccn34)c3c2C(=O)NC3)nc1)N(C)C] |

495
496
TABLE 1-continued
Selected Compounds
| # | Structure |
|---|---|
| I-522 | 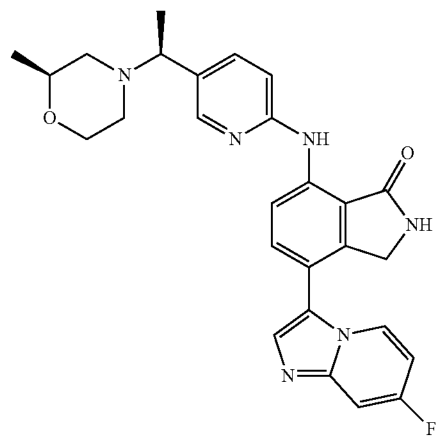 [SMILES: C[C@H]1CN([C@@H](C)c2ccc(Nc3ccc(-c4cnc5cc(F)ccn45)c4c3C(=O)NC4)nc2)CCO1] |
| I-523 | 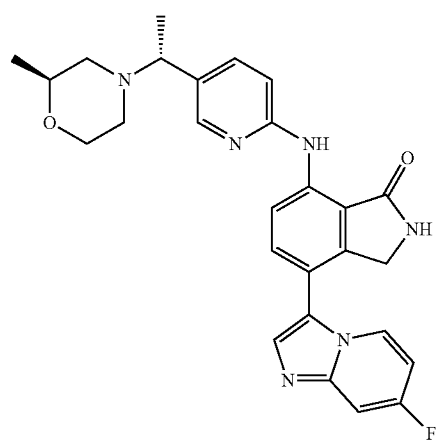 [SMILES: C[C@H](c1ccc(Nc2ccc(-c3cnc4cc(F)ccn34)c3c2C(=O)NC3)nc1)N1CCO[C@@H](C)C1] |
| I-524 | 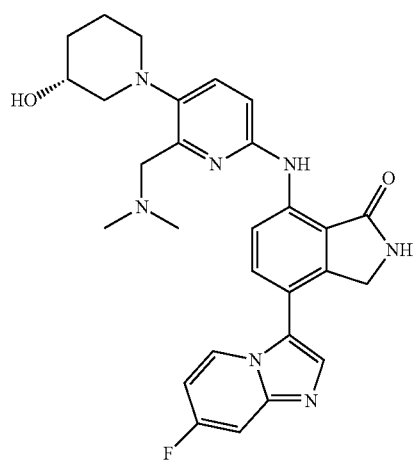 [SMILES: CN(C)Cc1nc(Nc2ccc(-c3cnc4cc(F)ccn34)c3c2C(=O)NC3)ccc1N1CCC[C@@H](O)C1] |

TABLE 1-continued
| Selected Compounds | |
|---|---|
| # | Structure |
I-525
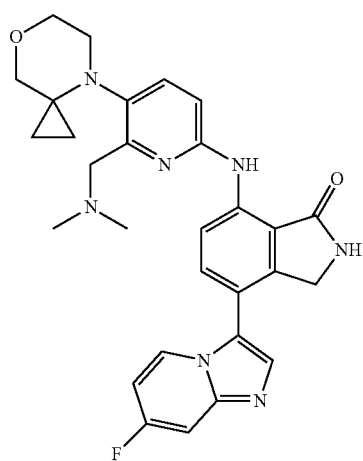 [SMILES: CN(C)Cc1nc(Nc2ccc(-c3cnc4cc(F)ccn34)c3c2C(=O)NC3)ccc1N1CCOCC12CC2]
I-526
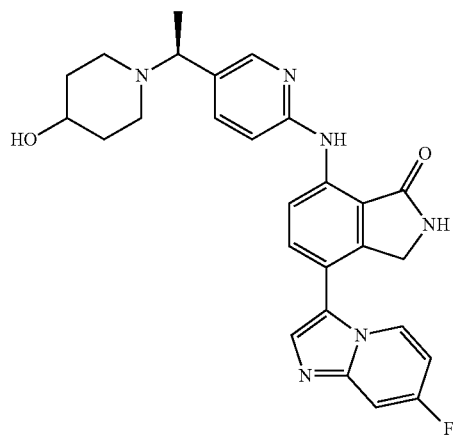 [SMILES: C[C@@H](c1ccc(Nc2ccc(-c3cnc4cc(F)ccn34)c3c2C(=O)NC3)nc1)N1CCC(O)CC1]
I-527
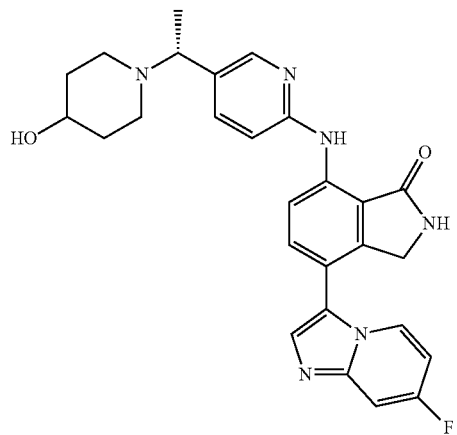 [SMILES: C[C@H](c1ccc(Nc2ccc(-c3cnc4cc(F)ccn34)c3c2C(=O)NC3)nc1)N1CCC(O)CC1]

TABLE 1-continued
Selected Compounds
| # | Structure |
|---|---|
| I-528 | 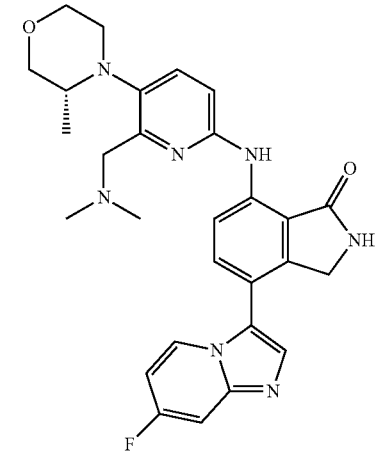 [SMILES: C[C@@H]1COCCN1c1ccc(Nc2ccc(-c3cnc4cc(F)ccn34)c3c2C(=O)NC3)nc1CN(C)C] |
| I-529 | 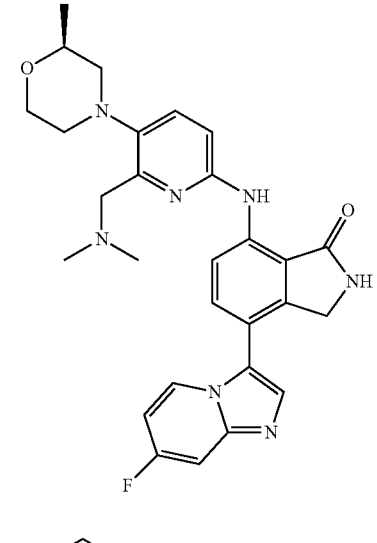 |
| I-530 | 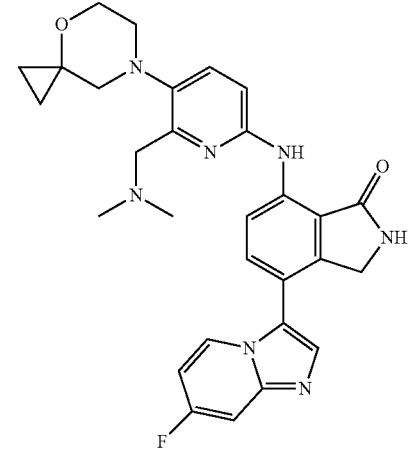 [SMILES: CN(C)Cc1nc(Nc2ccc(-c3cnc4cc(F)ccn34)c3c2C(=O)NC3)ccc1N1CCOC2(CC2)C1] |

TABLE 1-continued
Selected Compounds
| # | Structure |
|---|---|
| I-531 | 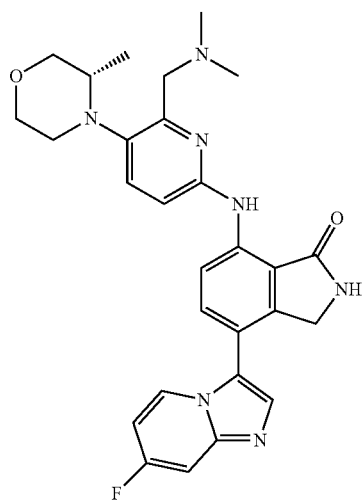 [SMILES: C[C@H]1COCCN1c1ccc(Nc2ccc(-c3cnc4cc(F)ccn34)c3c2C(=O)NC3)nc1CN(C)C] |
| I-532 | 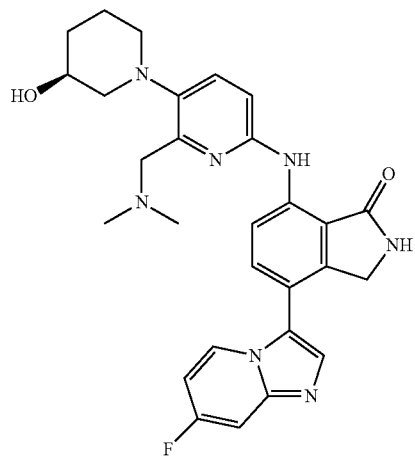 [SMILES: CN(C)Cc1nc(Nc2ccc(-c3cnc4cc(F)ccn34)c3c2C(=O)NC3)ccc1N1CCC[C@H](O)C1] |
| I-533 | 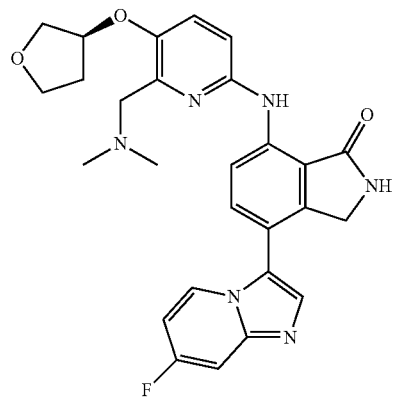 [SMILES: CN(C)Cc1nc(Nc2ccc(-c3cnc4cc(F)ccn34)c3c2C(=O)NC3)ccc1O[C@H]1CCOC1] |

TABLE 1-continued
Selected Compounds
| # | Structure |
|---|---|
| I-534 | 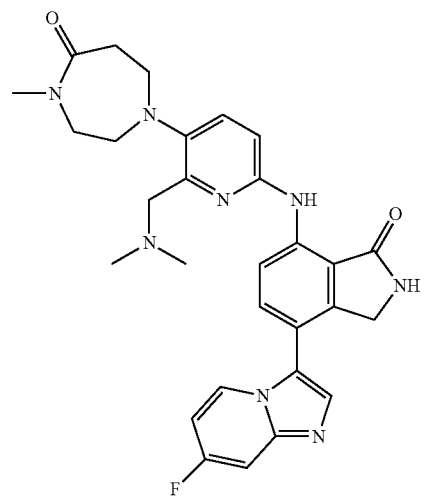 [SMILES: CN(C)Cc1nc(Nc2ccc(-c3cnc4cc(F)ccn34)c3c2C(=O)NC3)ccc1N1CCC(=O)N(C)CC1] |
| I-535 | 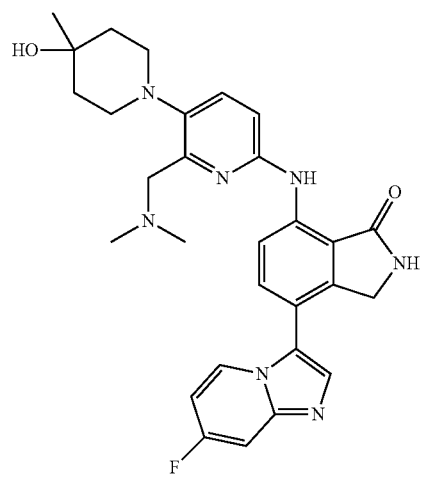 [SMILES: CN(C)Cc1nc(Nc2ccc(-c3cnc4cc(F)ccn34)c3c2C(=O)NC3)ccc1N1CCC(C)(O)CC1] |
| I-536 | 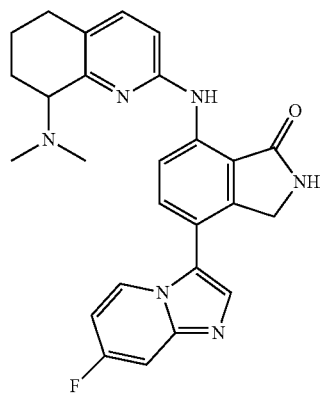 [SMILES: CN(C)C1CCCc2ccc(Nc3ccc(-c4cnc5cc(F)ccn45)c4c3C(=O)NC4)nc21] |

TABLE 1-continued
Selected Compounds
| # | Structure |
|---|---|
| I-537 | 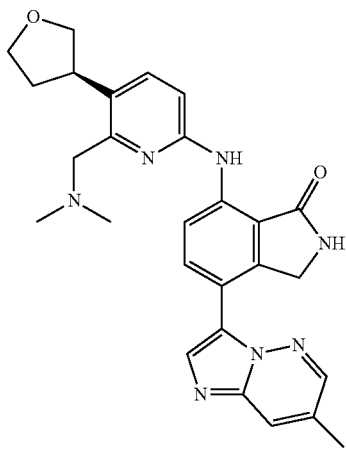 [SMILES: Cc1cnn2c(-c3ccc(Nc4ccc([C@H]5CCOC5)c(CN(C)C)n4)c4c3CNC4=O)cnc2c1] |
| I-538 | 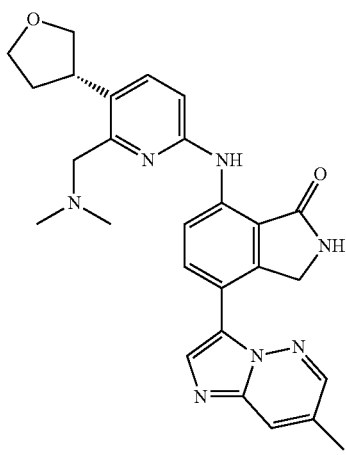 [SMILES: Cc1cnn2c(-c3ccc(Nc4ccc([C@@H]5CCOC5)c(CN(C)C)n4)c4c3CNC4=O)cnc2c1] |
| I-539 | 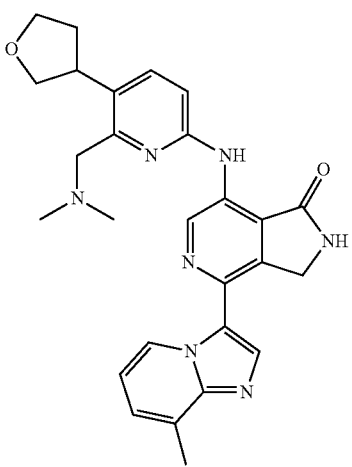 [SMILES: Cc1cccn2c(-c3ncc(Nc4ccc(C5CCOC5)c(CN(C)C)n4)c4c3CNC4=O)cnc12] |

TABLE 1-continued
Selected Compounds
| # | Structure |
|---|---|
| I-540 | 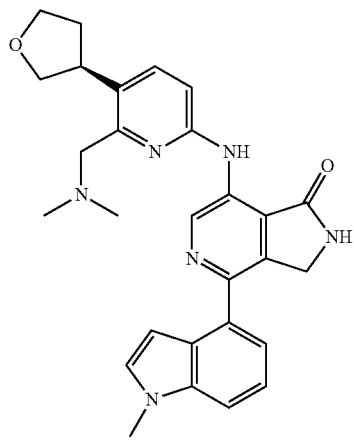 [SMILES: CN(C)Cc1nc(Nc2cnc(-c3cccc4c3ccn4C)c3c2C(=O)NC3)ccc1[C@@H]1CCOC1] |
| I-541 | 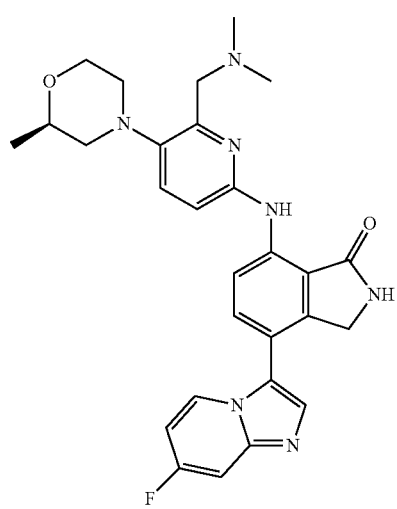 [SMILES: C[C@@H]1CN(c2ccc(Nc3ccc(-c4cnc5cc(F)ccn45)c4c3C(=O)NC4)nc2CN(C)C)CCO1] |
| I-542 | 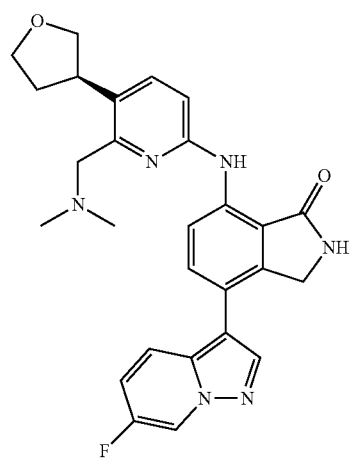 [SMILES: CN(C)Cc1nc(Nc2ccc(-c3cnn4cc(F)ccc34)c3c2C(=O)NC3)ccc1[C@H]1CCOC1] |

TABLE 1-continued
| Selected Compounds | |
|---|---|
| # | Structure |
I-543
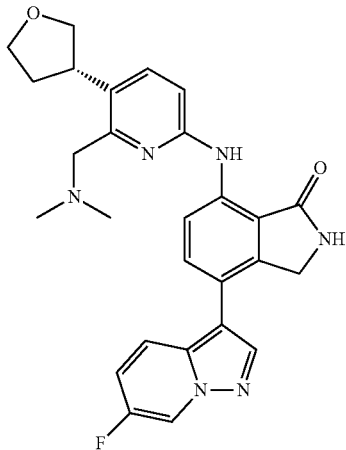 [SMILES: CN(C)Cc1nc(Nc2ccc(-c3cnn4cc(F)ccc34)c3c2C(=O)NC3)ccc1[C@@H]1CCOC1]
I-544
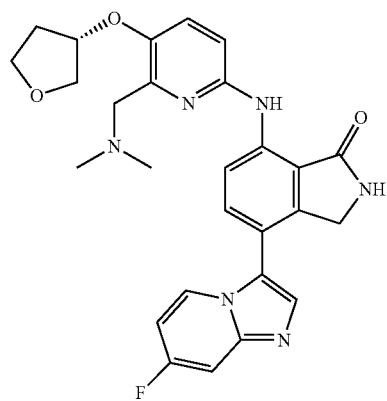 [SMILES: CN(C)Cc1nc(Nc2ccc(-c3cnc4cc(F)ccn34)c3c2C(=O)NC3)ccc1O[C@H]1CCOC1]
I-545
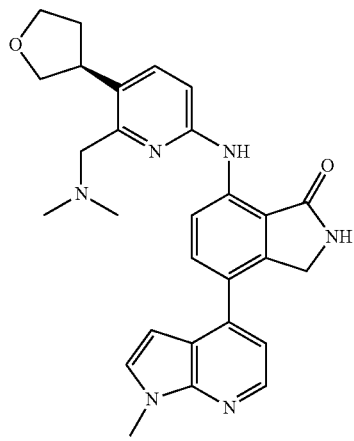 [SMILES: CN(C)Cc1nc(Nc2ccc(-c3ccnc4c3ccn4C)c3c2C(=O)NC3)ccc1[C@@H]1CCOC1]

TABLE 1-continued

Selected Compounds

| # | Structure |
|---|---|
| I-546 | 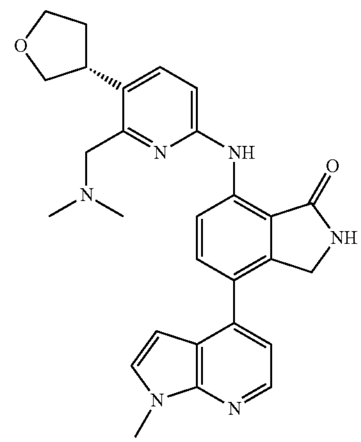 [SMILES: CN(C)Cc1nc(Nc2ccc(-c3ccnc4c3ccn4C)c3c2C(=O)NC3)ccc1[C@H]1CCOC1] |
| I-547 | 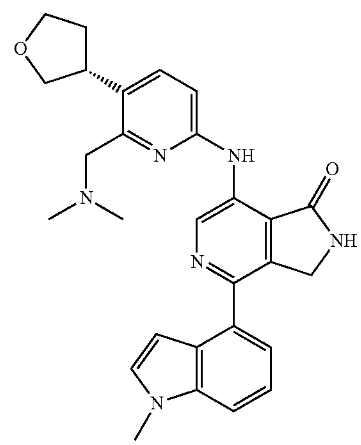 [SMILES: CN(C)Cc1nc(Nc2cnc(-c3cccc4c3ccn4C)c3c2C(=O)NC3)ccc1[C@H]1CCOC1] |
| I-548 | 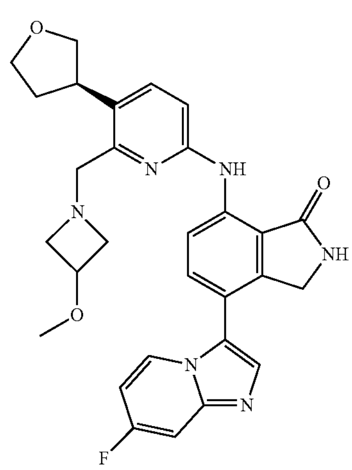 [SMILES: COC1CN(Cc2nc(Nc3ccc(-c4cnc5cc(F)ccn45)c4c3C(=O)NC4)ccc2[C@H]2CCOC2)C1] |

TABLE 1-continued
Selected Compounds
| # | Structure |
|---|---|
| I-549 | 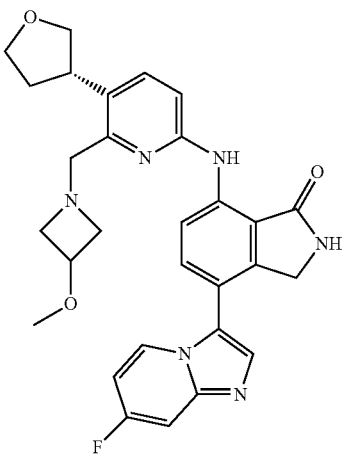 [SMILES: COC1CN(Cc2nc(Nc3ccc(-c4cnc5cc(F)ccn45)c4c3C(=O)NC4)ccc2[C@@H]2CCOC2)C1] |
| I-550 | 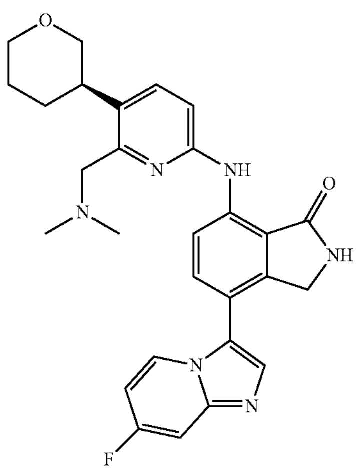 [SMILES: CN(C)Cc1nc(Nc2ccc(-c3cnc4cc(F)ccn34)c3c2C(=O)NC3)ccc1[C@H]1CCCOC1] |
| I-551 | 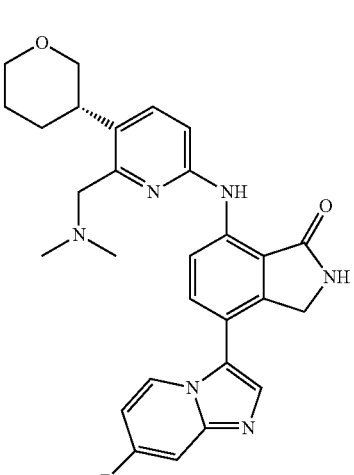 |

TABLE 1-continued
| # | Structure |
|---|---|
| I-552 | 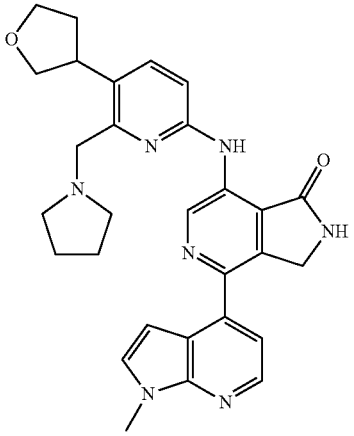 [SMILES: Cn1ccc2c(-c3ncc(Nc4ccc(C5CCOC5)c(CN5CCCC5)n4)c4c3CNC4=O)ccnc21] |
| I-553 | 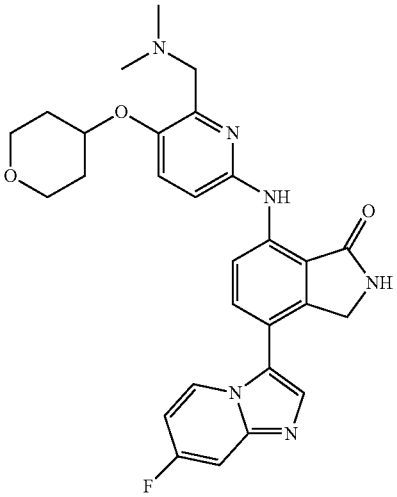 [SMILES: CN(C)Cc1nc(Nc2ccc(-c3cnc4cc(F)ccn34)c3c2C(=O)NC3)ccc1OC1CCOCC1] |
| I-554 | 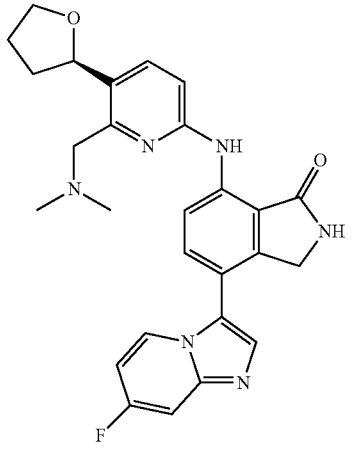 [SMILES: CN(C)Cc1nc(Nc2ccc(-c3cnc4cc(F)ccn34)c3c2C(=O)NC3)ccc1[C@H]1CCCO1] |

TABLE 1-continued
Selected Compounds
| # | Structure |
|---|---|
| I-555 | 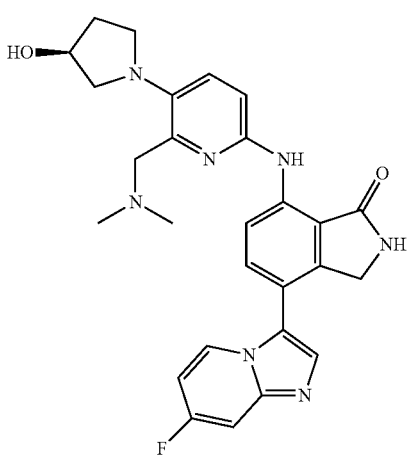 [SMILES: CN(C)Cc1nc(Nc2ccc(-c3cnc4cc(F)ccn34)c3c2C(=O)NC3)ccc1N1CC[C@H](O)C1] |
| I-556 | 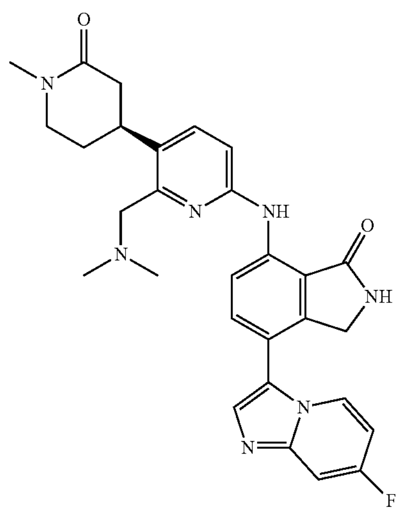 [SMILES: CN(C)Cc1nc(Nc2ccc(-c3cnc4cc(F)ccn34)c3c2C(=O)NC3)ccc1[C@H]1CCN(C)C(=O)C1] |
| I-557 | 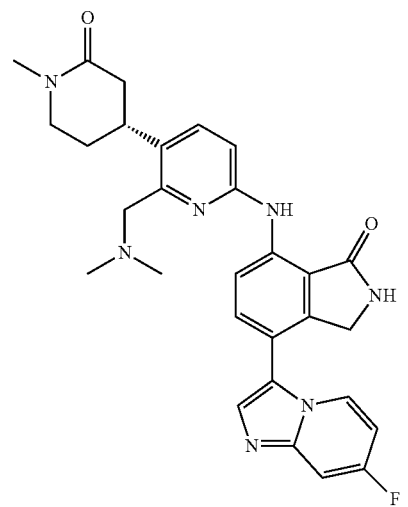 [SMILES: CN(C)Cc1nc(Nc2ccc(-c3cnc4cc(F)ccn34)c3c2C(=O)NC3)ccc1[C@@H]1CCN(C)C(=O)C1] |

TABLE 1-continued
Selected Compounds
| # | Structure |
|---|---|
| I-558 | 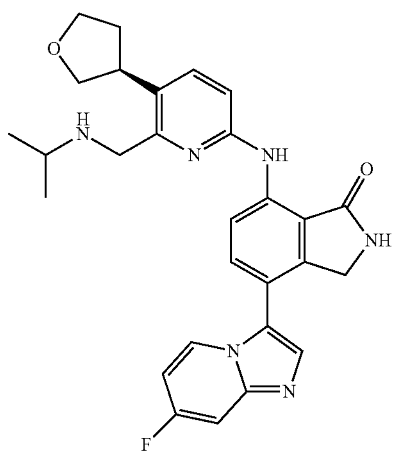 [SMILES: CC(C)NCc1nc(Nc2ccc(-c3cnc4cc(F)ccn34)c3c2C(=O)NC3)ccc1[C@@H]1CCOC1] |
| I-559 | 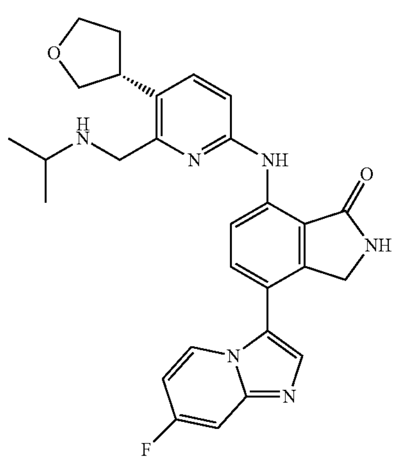 [SMILES: CC(C)NCc1nc(Nc2ccc(-c3cnc4cc(F)ccn34)c3c2C(=O)NC3)ccc1[C@H]1CCOC1] |
| I-560 | 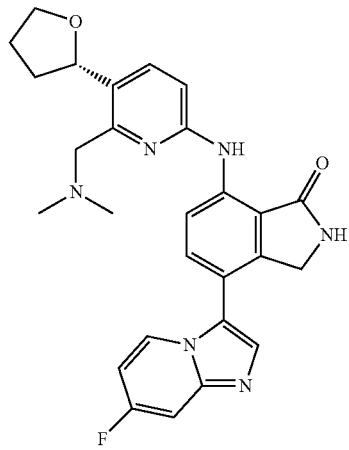 [SMILES: CN(C)Cc1nc(Nc2ccc(-c3cnc4cc(F)ccn34)c3c2C(=O)NC3)ccc1[C@@H]1CCCO1] |

TABLE 1-continued
Selected Compounds
| # | Structure |
|---|---|
| I-561 | 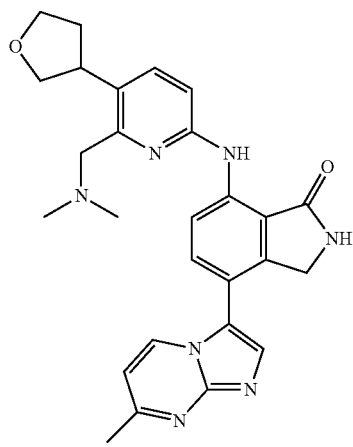 [SMILES: Cc1ccn2c(-c3ccc(Nc4ccc(C5CCOC5)c(CN(C)C)n4)c4c3CNC4=O)cnc2n1] |
| I-562 | 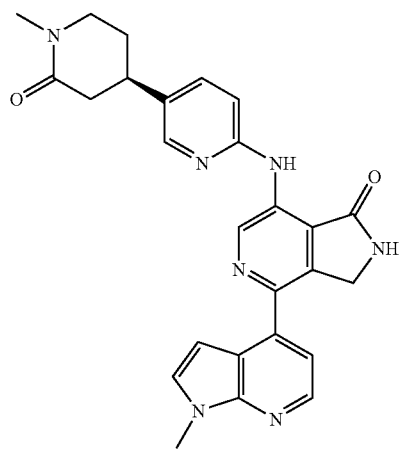 [SMILES: CN1CC[C@@H](c2ccc(Nc3cnc(-c4ccnc5c4ccn5C)c4c3C(=O)NC4)nc2)CC1=O] |
| I-563 | 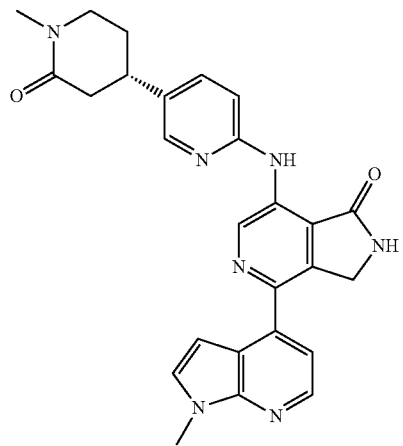 [SMILES: CN1CC[C@H](c2ccc(Nc3cnc(-c4ccnc5c4ccn5C)c4c3C(=O)NC4)nc2)CC1=O] |

TABLE 1-continued
Selected Compounds
| # | Structure |
|---|---|
| I-564 | 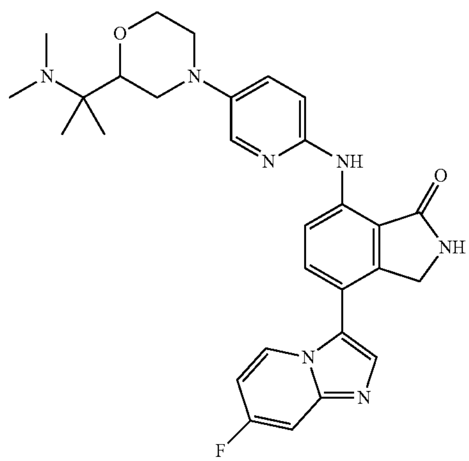 [SMILES: CN(C)C(C)(C)C1CN(c2ccc(Nc3ccc(-c4cnc5cc(F)ccn45)c4c3C(=O)NC4)nc2)CCO1] |
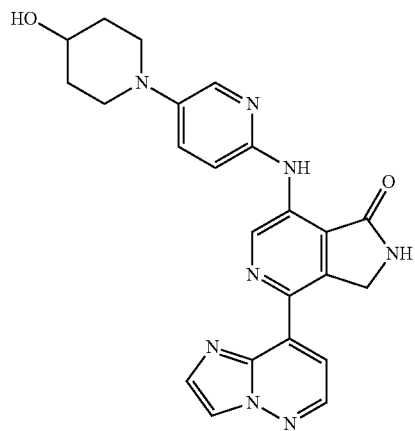 [SMILES: O=C1NCc2c(-c3ccnn4ccnc34)ncc(Nc3ccc(N4CCC(O)CC4)cn3)c21]
| I-565 | |
| I-566 | |
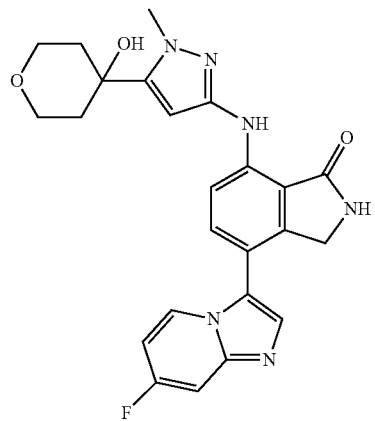 [SMILES: Cn1nc(Nc2ccc(-c3cnc4cc(F)ccn34)c3c2C(=O)NC3)cc1C1(O)CCOCC1]

TABLE 1-continued
| # | Structure |
|---|---|
| I-567 | 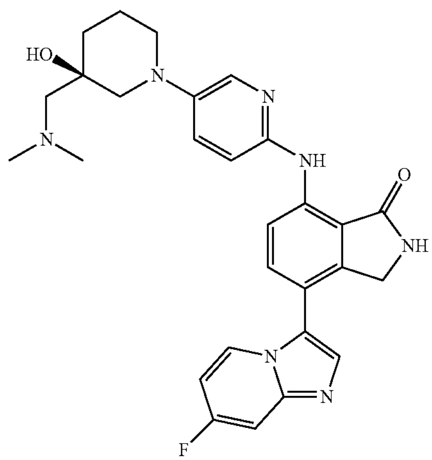 [SMILES: CN(C)C[C@]1(O)CCCN(c2ccc(Nc3ccc(-c4cnc5cc(F)ccn45)c4c3C(=O)NC4)nc2)C1] |
| I-568 | 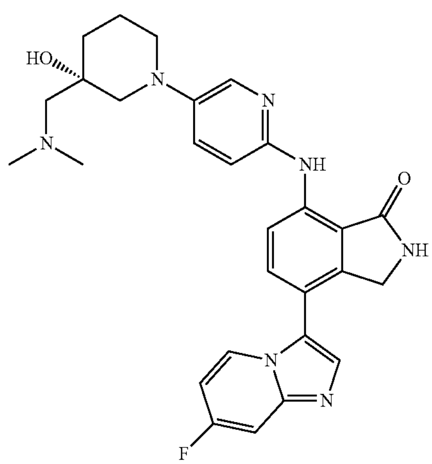 [SMILES: CN(C)C[C@@]1(O)CCCN(c2ccc(Nc3ccc(-c4cnc5cc(F)ccn45)c4c3C(=O)NC4)nc2)C1] |
| I-569 | 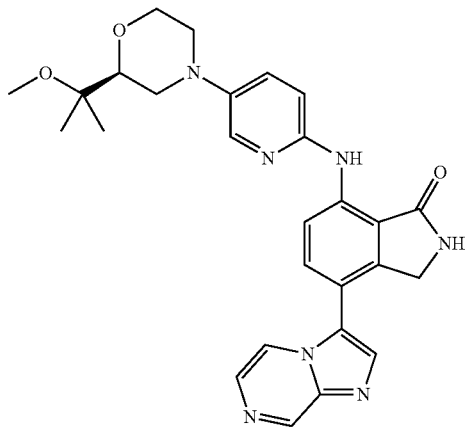 [SMILES: COC(C)(C)[C@@H]1CN(c2ccc(Nc3ccc(-c4cnc5cnccn45)c4c3C(=O)NC4)nc2)CCO1] |

TABLE 1-continued
| # | Structure |
|---|---|
| I-570 | 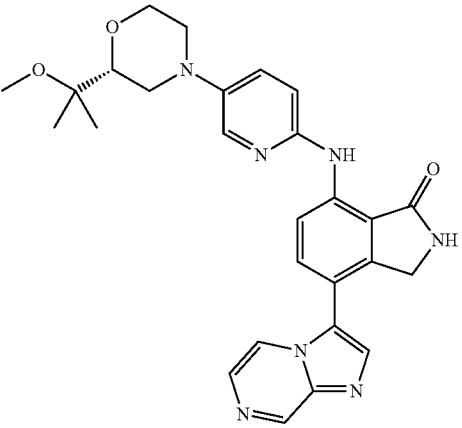 [SMILES: COC(C)(C)[C@H]1CN(c2ccc(Nc3ccc(-c4cnc5cnccn45)c4c3C(=O)NC4)nc2)CCO1] |
| I-571 | 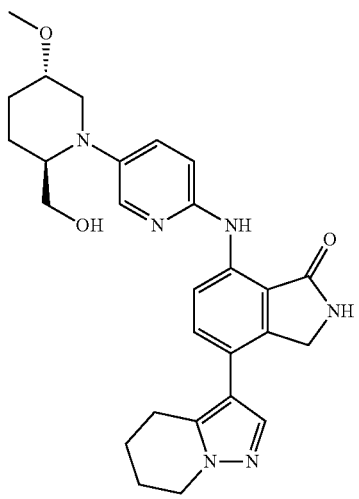 [SMILES: CO[C@H]1CC[C@H](CO)N(c2ccc(Nc3ccc(-c4cnn5c4CCCC5)c4c3C(=O)NC4)nc2)C1] |
| I-572 | 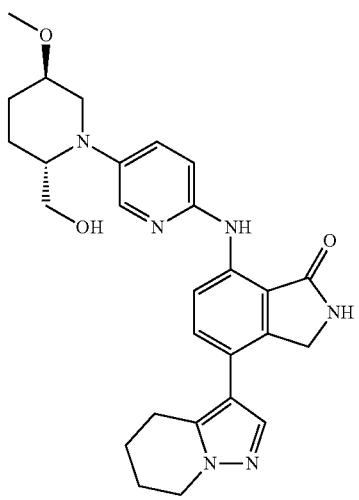 [SMILES: CO[C@@H]1CC[C@@H](CO)N(c2ccc(Nc3ccc(-c4cnn5c4CCCC5)c4c3C(=O)NC4)nc2)C1] |

TABLE 1-continued
| Selected Compounds | |
|---|---|
| # | Structure |
I-573
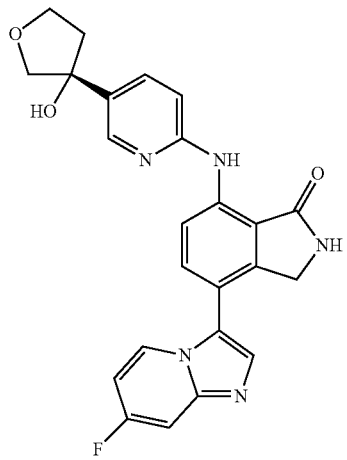 [SMILES: O=C1NCc2c(-c3cnc4cc(F)ccn34)ccc(Nc3ccc([C@]4(O)CCOC4)cn3)c21]
I-574
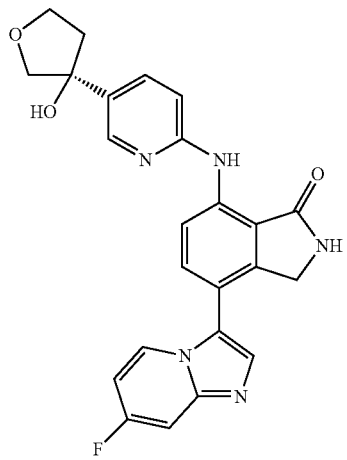 [SMILES: O=C1NCc2c(-c3cnc4cc(F)ccn34)ccc(Nc3ccc([C@@]4(O)CCOC4)cn3)c21]
I-575
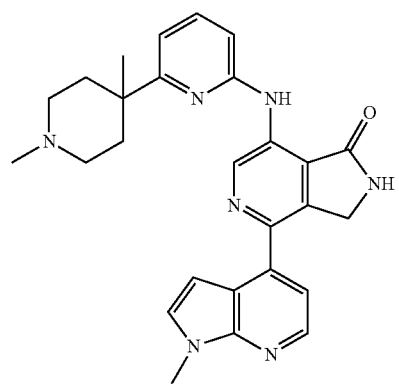 [SMILES: CN1CCC(C)(c2cccc(Nc3cnc(-c4ccnc5c4ccn5C)c4c3C(=O)NC4)n2)CC1]

TABLE 1-continued
Selected Compounds
| # | Structure |
|---|---|
| I-576 | 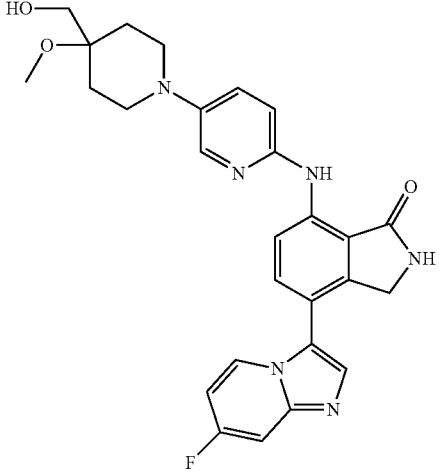 [SMILES: COC1(CO)CCN(c2ccc(Nc3ccc(-c4cnc5cc(F)ccn45)c4c3C(=O)NC4)nc2)CC1] |
| I-577 | 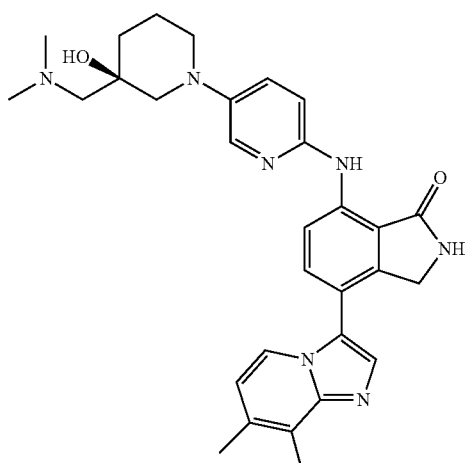 |
| I-578 | 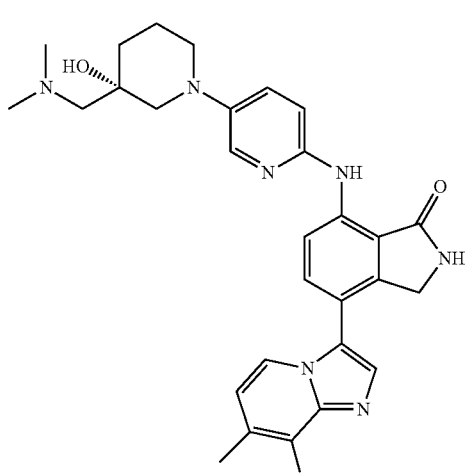 |

TABLE 1-continued
Selected Compounds
| # | Structure |
|---|---|
| I-579 | 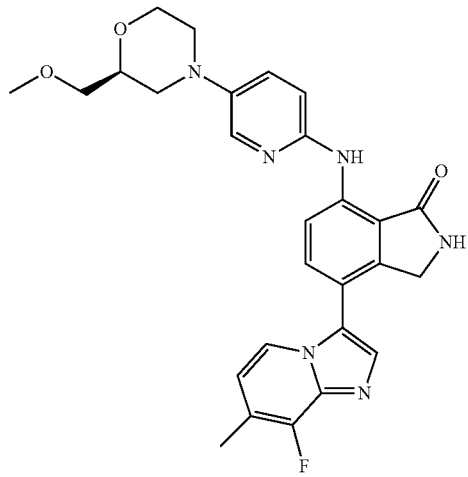 [SMILES: COC[C@@H]1CN(c2ccc(Nc3ccc(-c4cnc5c(F)c(C)ccn45)c4c3C(=O)NC4)nc2)CCO1] |
| I-580 | 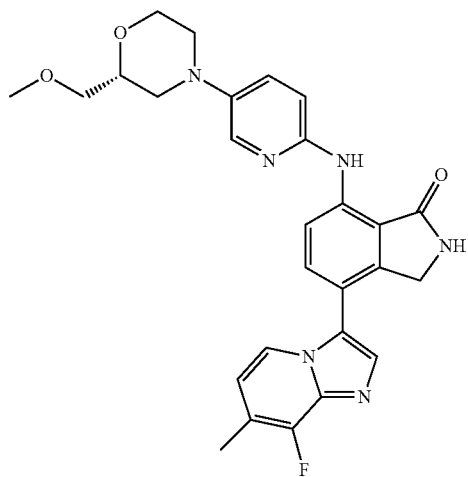 [SMILES: COC[C@H]1CN(c2ccc(Nc3ccc(-c4cnc5c(F)c(C)ccn45)c4c3C(=O)NC4)nc2)CCO1] |
| I-581 | 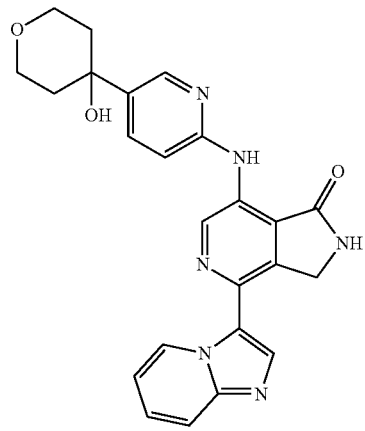 [SMILES: O=C1NCc2c(-c3cnc4ccccn34)ncc(Nc3ccc(C4(O)CCOCC4)cn3)c21] |

TABLE 1-continued
Selected Compounds
| # | Structure |
|---|---|
| I-582 | 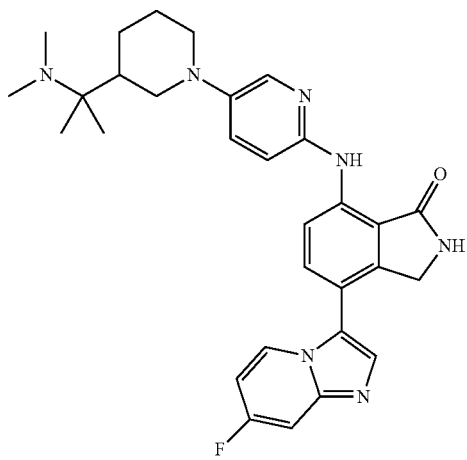 [SMILES: CN(C)C(C)(C)C1CCCN(c2ccc(Nc3ccc(-c4cnc5cc(F)ccn45)c4c3C(=O)NC4)nc2)C1] |
| I-583 | 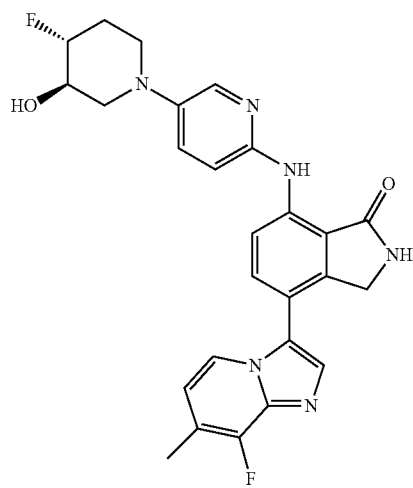 [SMILES: Cc1ccn2c(-c3ccc(Nc4ccc(N5CC[C@@H](F)[C@H](O)C5)cn4)c4c3CNC4=O)cnc2c1F] |
| I-584 | 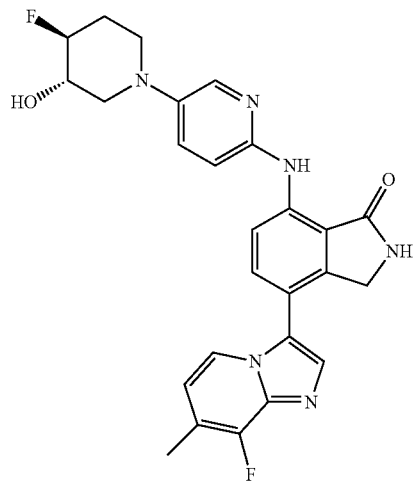 [SMILES: Cc1ccn2c(-c3ccc(Nc4ccc(N5CC[C@H](F)[C@@H](O)C5)cn4)c4c3CNC4=O)cnc2c1F] |

TABLE 1-continued
| Selected Compounds | |
|---|---|
| # | Structure |
I-585
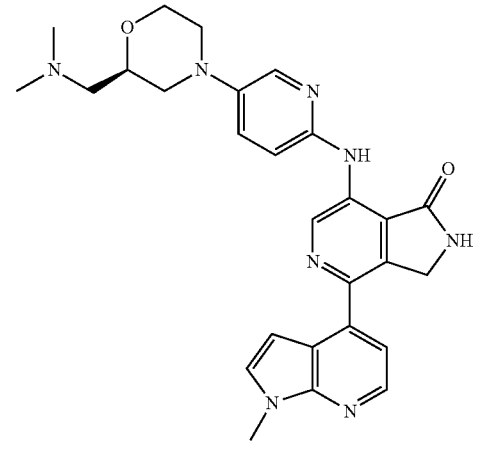 [SMILES: CN(C)C[C@@H]1CN(c2ccc(Nc3cnc(-c4ccnc5c4ccn5C)c4c3C(=O)NC4)nc2)CCO1]
I-586
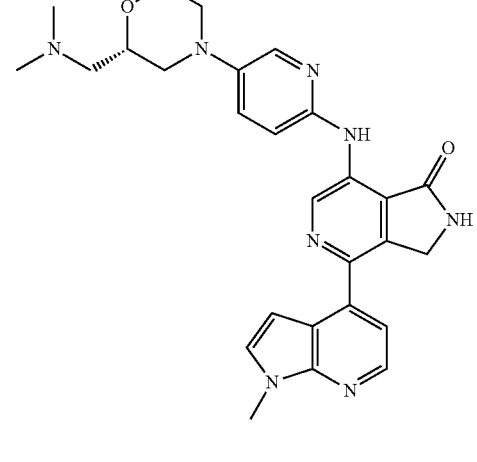
I-587
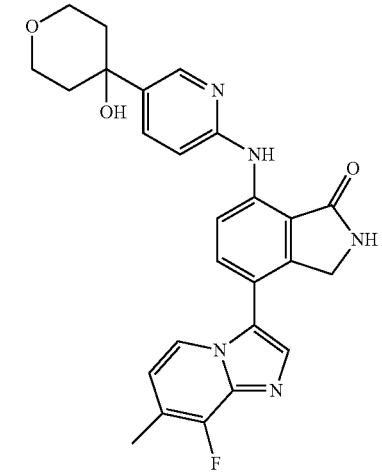 [SMILES: Cc1ccn2c(-c3ccc(Nc4ccc(C5(O)CCOCC5)cn4)c4c3CNC4=O)cnc2c1F]

TABLE 1-continued
| Selected Compounds | |
|---|---|
| # | Structure |
| I-588 | 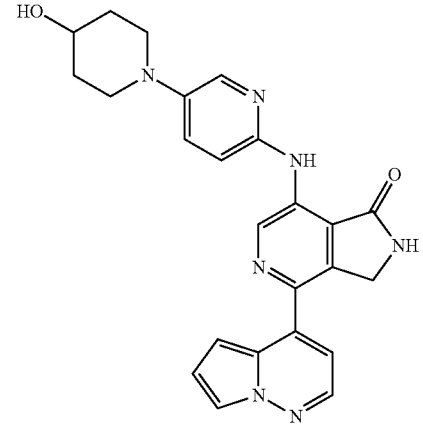 [SMILES: O=C1NCc2c(-c3ccnn4cccc34)ncc(Nc3ccc(N4CCC(O)CC4)cn3)c21] |
| I-589 | 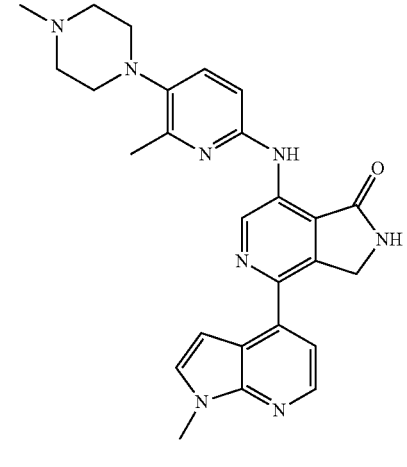 [SMILES: Cc1nc(Nc2cnc(-c3ccnc4c3ccn4C)c3c2C(=O)NC3)ccc1N1CCN(C)CC1] |
| I-590 | 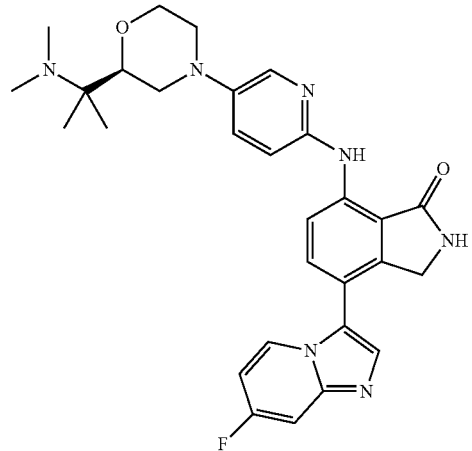 [SMILES: CN(C)C(C)(C)[C@@H]1CN(c2ccc(Nc3ccc(-c4cnc5cc(F)ccn45)c4c3C(=O)NC4)nc2)CCO1] |

TABLE 1-continued
| Selected Compounds | |
|---|---|
| # | Structure |ами
I-591
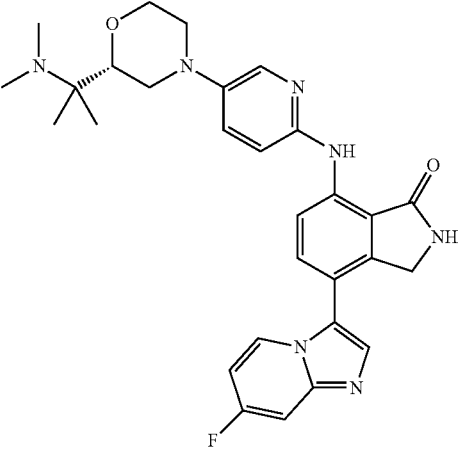
I-592
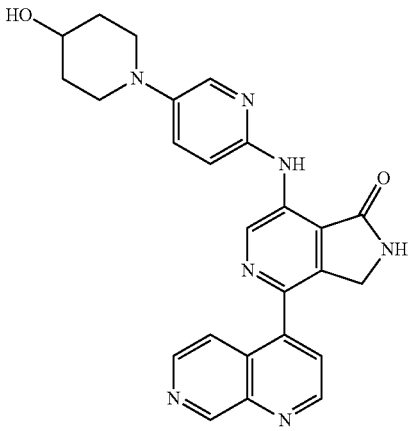 [SMILES: O=C1NCc2c(-c3ccnc4cnccc34)ncc(Nc3ccc(N4CCC(O)CC4)cn3)c21]
I-593
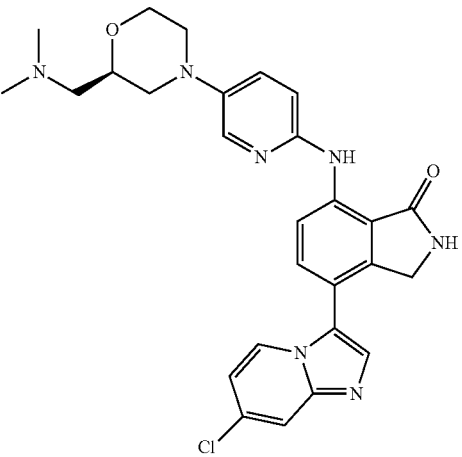 [SMILES: CN(C)C[C@@H]1CN(c2ccc(Nc3ccc(-c4cnc5cc(Cl)ccn45)c4c3C(=O)NC4)nc2)CCO1]

TABLE 1-continued
Selected Compounds
| # | Structure |
|---|---|
| I-594 | 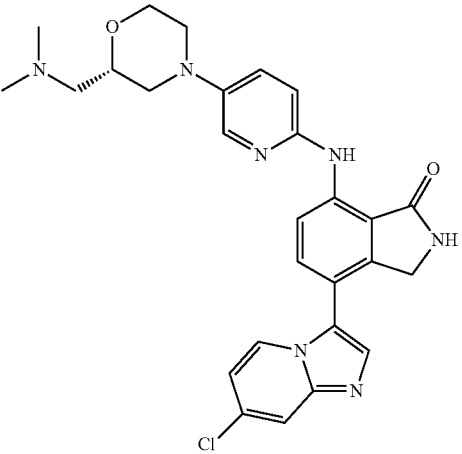 [SMILES: CN(C)C[C@H]1CN(c2ccc(Nc3ccc(-c4cnc5cc(Cl)ccn45)c4c3C(=O)NC4)nc2)CCO1] |
| I-595 | 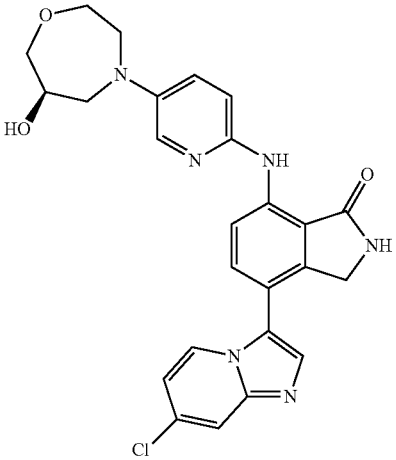 [SMILES: O=C1NCc2c(-c3cnc4cc(Cl)ccn34)ccc(Nc3ccc(N4CCOC[C@H](O)C4)cn3)c21] |
| I-596 | 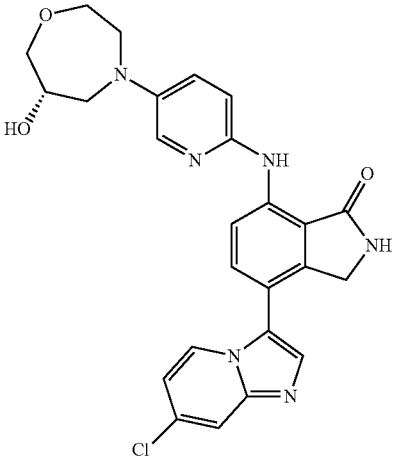 [SMILES: O=C1NCc2c(-c3cnc4cc(Cl)ccn34)ccc(Nc3ccc(N4CCOC[C@@H](O)C4)cn3)c21] |

TABLE 1-continued
Selected Compounds
| # | Structure |
|---|---|
| I-597 | 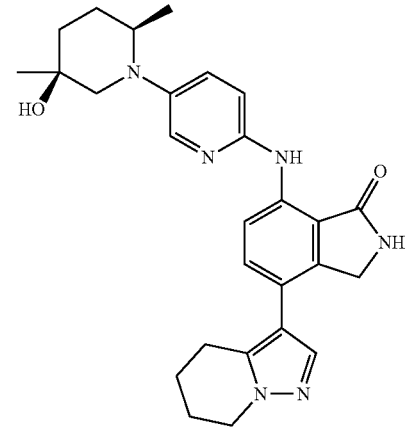 [SMILES: C[C@@H]1CC[C@](C)(O)CN1c1ccc(Nc2ccc(-c3cnn4c3CCCC4)c3c2C(=O)NC3)nc1] |
| I-598 | 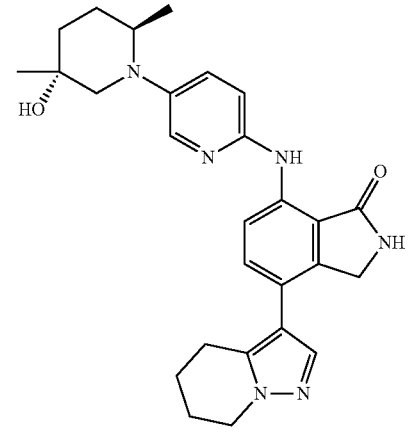 [SMILES: C[C@@H]1CC[C@@](C)(O)CN1c1ccc(Nc2ccc(-c3cnn4c3CCCC4)c3c2C(=O)NC3)nc1] |
| I-599 | 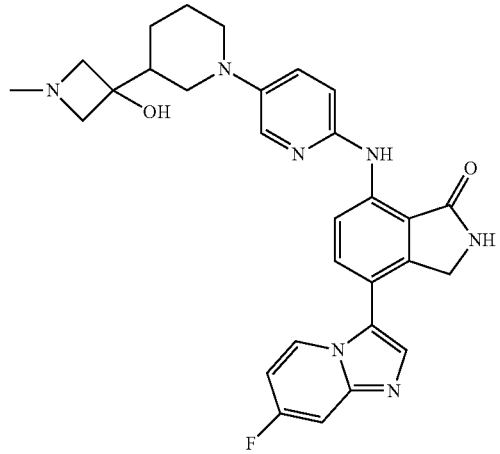 [SMILES: CN1CC(O)(C2CCCN(c3ccc(Nc4ccc(-c5cnc6cc(F)ccn56)c5c4C(=O)NC5)nc3)C2)C1] |

547                                                                 548
TABLE 1-continued
Selected Compounds
| # | Structure |
|---|-----------|
| I-600 | 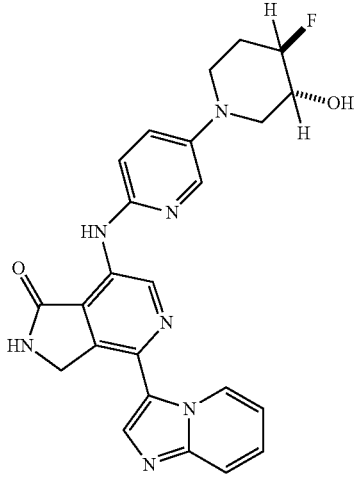 [SMILES: O=C1NCc2c(-c3cnc4ccccn34)ncc(Nc3ccc(N4CC[C@@H](F)[C@H](O)C4)cn3)c21] |
| I-601 | 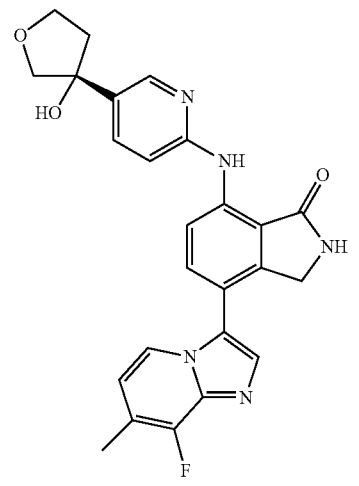 [SMILES: Cc1ccn2c(-c3ccc(Nc4ccc([C@]5(O)CCOC5)cn4)c4c3CNC4=O)cnc2c1F] |
| I-602 | 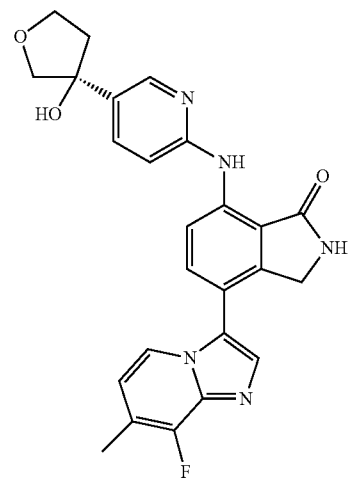 [SMILES: Cc1ccn2c(-c3ccc(Nc4ccc([C@@]5(O)CCOC5)cn4)c4c3CNC4=O)cnc2c1F] |

TABLE 1-continued
Selected Compounds
| # | Structure |
|---|---|
| I-603 | 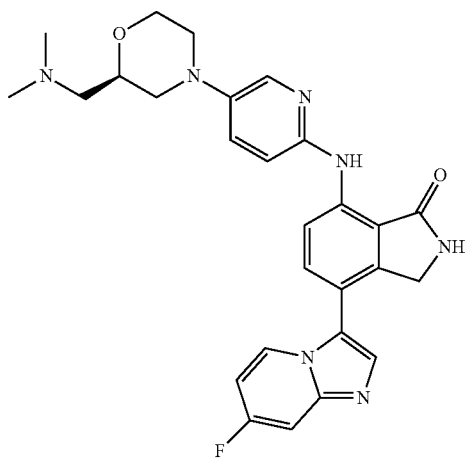 [SMILES: CN(C)C[C@@H]1CN(c2ccc(Nc3ccc(-c4cnc5cc(F)ccn45)c4c3C(=O)NC4)nc2)CCO1] |
| I-604 | 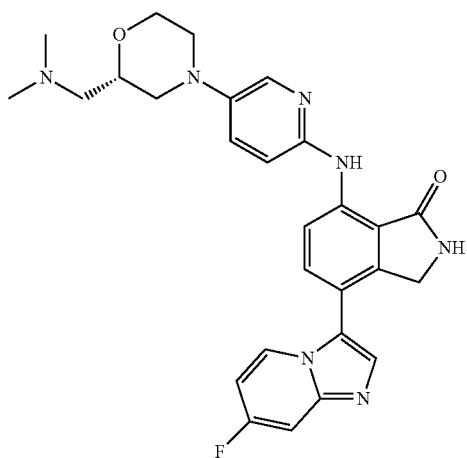 [SMILES: CN(C)C[C@H]1CN(c2ccc(Nc3ccc(-c4cnc5cc(F)ccn45)c4c3C(=O)NC4)nc2)CCO1] |
| I-605 | 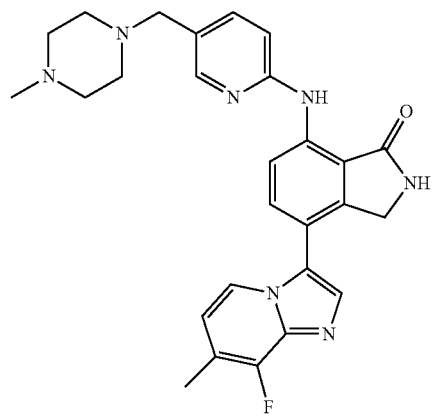 [SMILES: Cc1ccn2c(-c3ccc(Nc4ccc(CN5CCN(C)CC5)cn4)c4c3CNC4=O)cnc2c1F] |

TABLE 1-continued
| Selected Compounds | |
|---|---|
| # | Structure |
| I-606 | 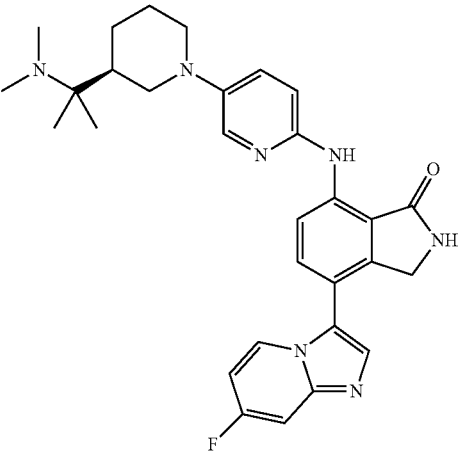 [SMILES: CN(C)C(C)(C)[C@H]1CCCN(c2ccc(Nc3ccc(-c4cnc5cc(F)ccn45)c4c3C(=O)NC4)nc2)C1] |
| I-607 | 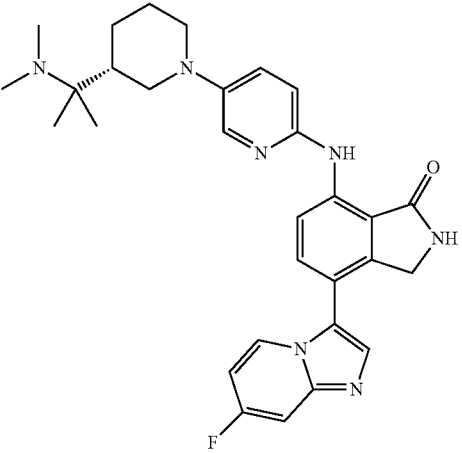 [SMILES: CN(C)C(C)(C)[C@@H]1CCCN(c2ccc(Nc3ccc(-c4cnc5cc(F)ccn45)c4c3C(=O)NC4)nc2)C1] |
| I-608 | 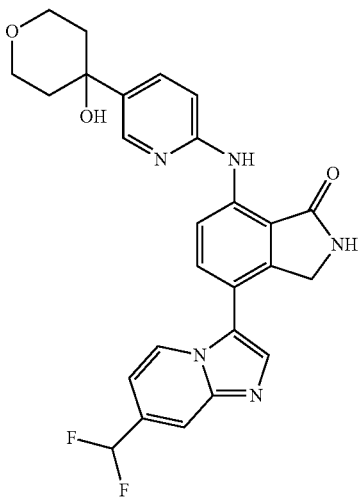 [SMILES: O=C1NCc2c(-c3cnc4cc(C(F)F)ccn34)ccc(Nc3ccc(C4(O)CCOCC4)cn3)c21] |

TABLE 1-continued
| Selected Compounds | |
|---|---|
| # | Structure |
I-609 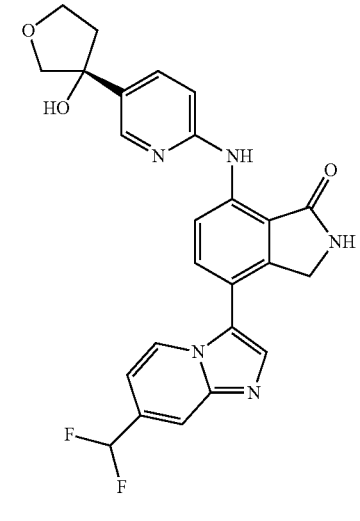 [SMILES: O=C1NCc2c(-c3cnc4cc(C(F)F)ccn34)ccc(Nc3ccc([C@]4(O)CCOC4)cn3)c21]
I-610 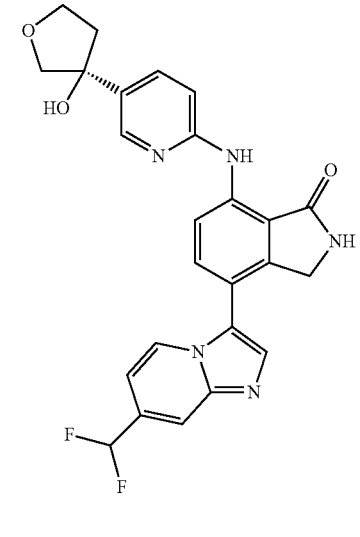 [SMILES: O=C1NCc2c(-c3cnc4cc(C(F)F)ccn34)ccc(Nc3ccc([C@@]4(O)CCOC4)cn3)c21]
I-611 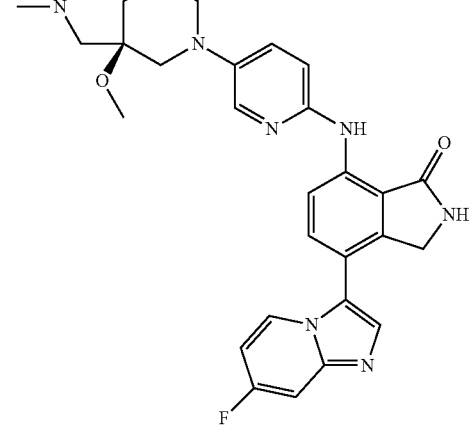

TABLE 1-continued

Selected Compounds

| # | Structure |
|---|---|
| I-612 | 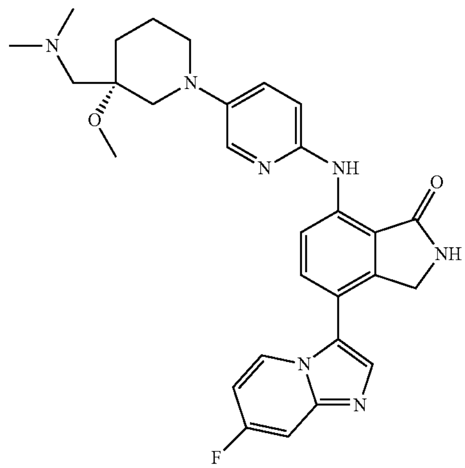 [SMILES: CO[C@]1(CN(C)C)CCCN(c2ccc(Nc3ccc(-c4cnc5cc(F)ccn45)c4c3C(=O)NC4)nc2)C1] |
| I-613 | 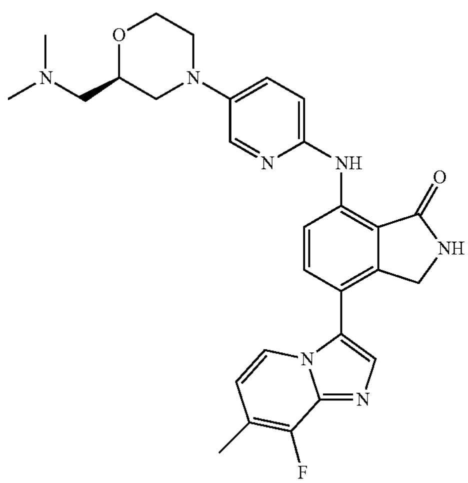 [SMILES: Cc1ccn2c(-c3ccc(Nc4ccc(N5CCO[C@H](CN(C)C)C5)cn4)c4c3CNC4=O)cnc2c1F] |
| I-614 | 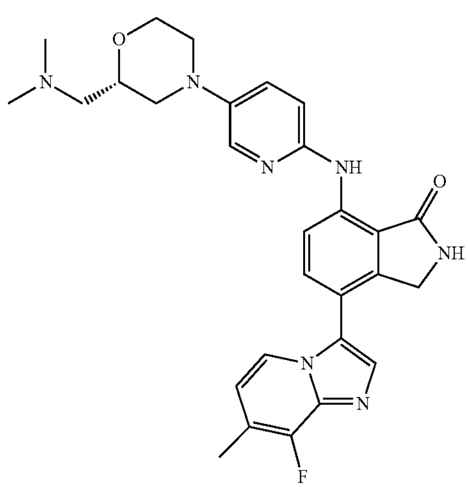 [SMILES: Cc1ccn2c(-c3ccc(Nc4ccc(N5CCO[C@@H](CN(C)C)C5)cn4)c4c3CNC4=O)cnc2c1F] |

TABLE 1-continued
Selected Compounds
| # | Structure |
|---|---|
| I-615 | 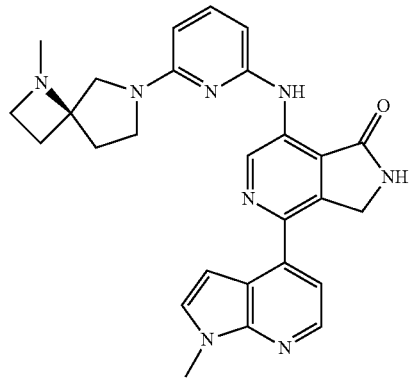 [SMILES: CN1CC[C@]12CCN(c1cccc(Nc3cnc(-c4ccnc5c4ccn5C)c4c3C(=O)NC4)n1)C2] |
| I-616 | 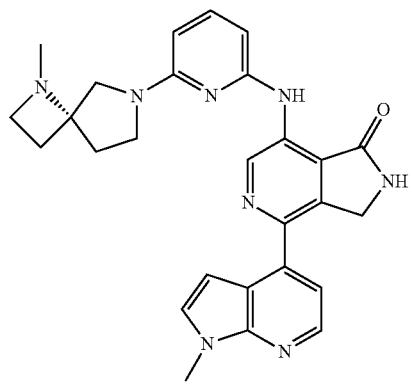 [SMILES: CN1CC[C@@]12CCN(c1cccc(Nc3cnc(-c4ccnc5c4ccn5C)c4c3C(=O)NC4)n1)C2] |
| I-617 | 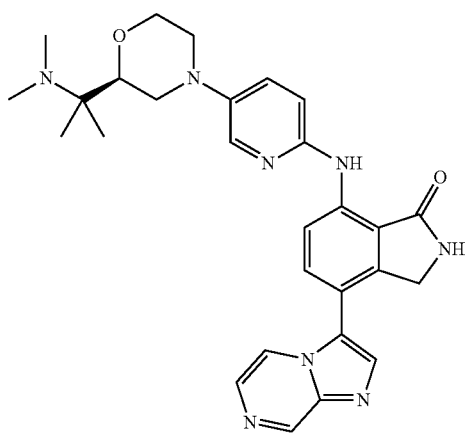 [SMILES: CN(C)C(C)(C)[C@@H]1CN(c2ccc(Nc3ccc(-c4cnc5cnccn45)c4c3C(=O)NC4)nc2)CCO1] |

TABLE 1-continued
Selected Compounds
| # | Structure |
|---|---|
| I-618 | 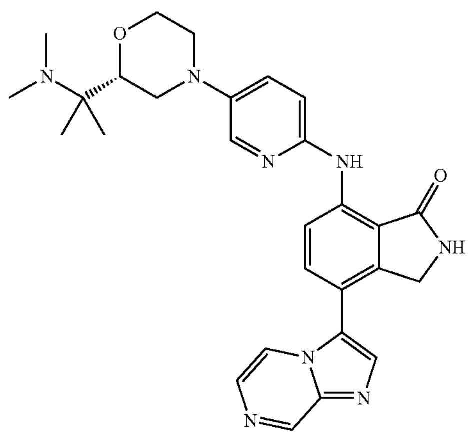 [SMILES: CN(C)C(C)(C)[C@H]1CN(c2ccc(Nc3ccc(-c4cnc5cnccn45)c4c3C(=O)NC4)nc2)CCO1] |
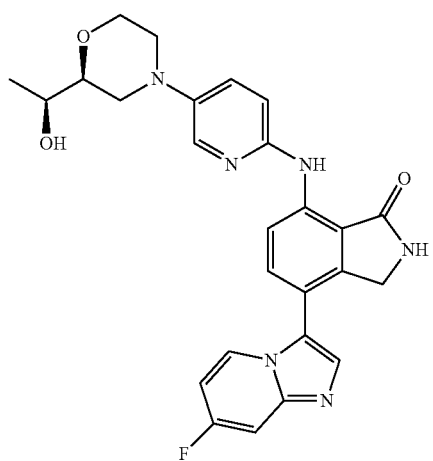 [SMILES: C[C@H](O)[C@@H]1CN(c2ccc(Nc3ccc(-c4cnc5cc(F)ccn45)c4c3C(=O)NC4)nc2)CCO1]
I-619
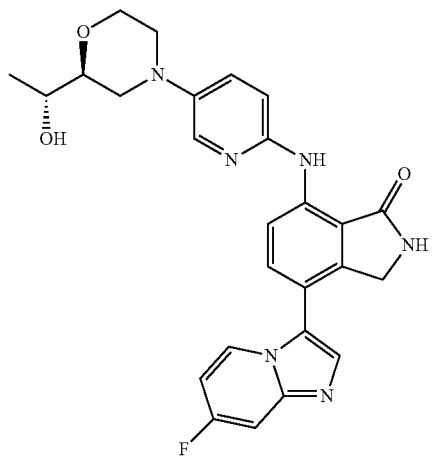 [SMILES: C[C@@H](O)[C@@H]1CN(c2ccc(Nc3ccc(-c4cnc5cc(F)ccn45)c4c3C(=O)NC4)nc2)CCO1]
I-620

TABLE 1-continued
Selected Compounds
| # | Structure |
|---|---|
| I-621 | 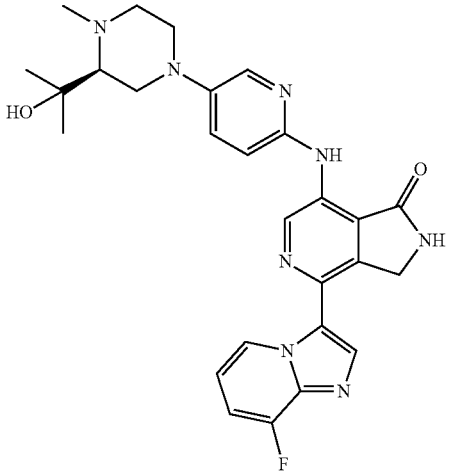 [SMILES: CN1CCN(c2ccc(Nc3cnc(-c4cnc5c(F)cccn45)c4c3C(=O)NC4)nc2)C[C@H]1C(C)(C)O] |
| I-622 | 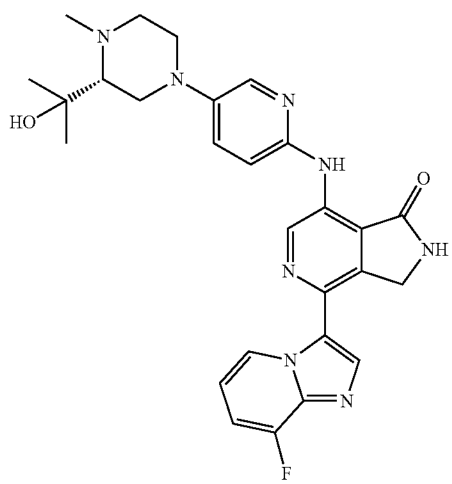 [SMILES: CN1CCN(c2ccc(Nc3cnc(-c4cnc5c(F)cccn45)c4c3C(=O)NC4)nc2)C[C@@H]1C(C)(C)O] |
| I-623 | 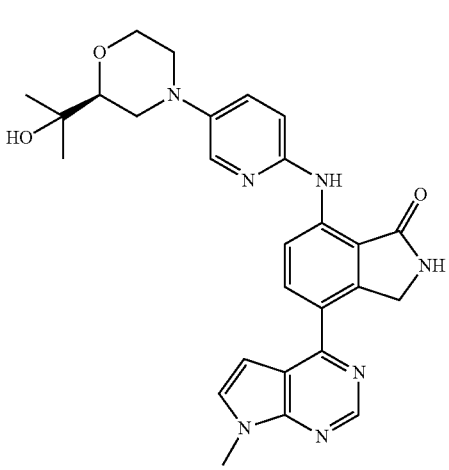 [SMILES: Cn1ccc2c(-c3ccc(Nc4ccc(N5CCO[C@H](C(C)(C)O)C5)cn4)c4c3CNC4=O)ncnc21] |

TABLE 1-continued
Selected Compounds
| # | Structure |
|---|---|
| I-624 | 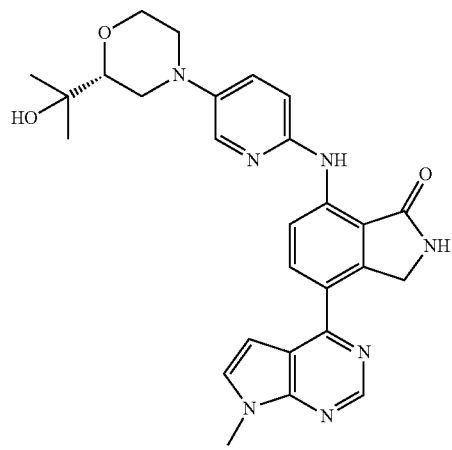 [SMILES: Cn1ccc2c(-c3ccc(Nc4ccc(N5CCO[C@@H](C(C)(C)O)C5)cn4)c4c3CNC4=O)ncnc21] |
| I-626 | 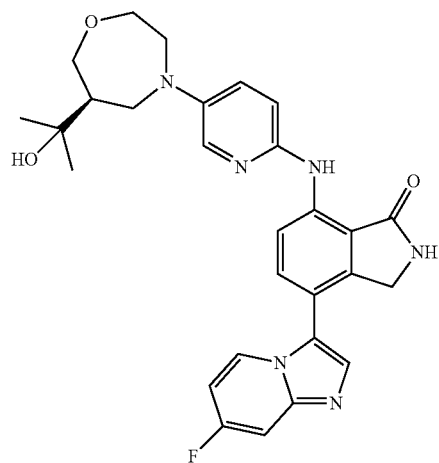 [SMILES: CC(C)(O)[C@H]1COCCN(c2ccc(Nc3ccc(-c4cnc5cc(F)ccn45)c4c3C(=O)NC4)nc2)C1] |
| I-627 | 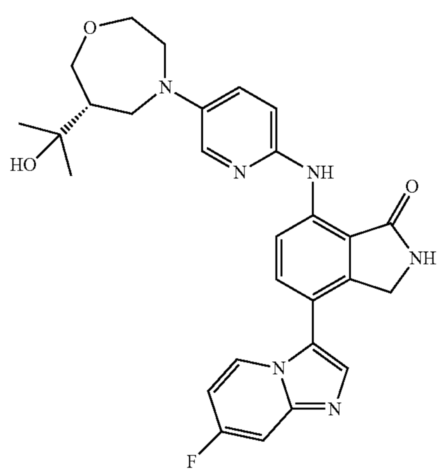 [SMILES: CC(C)(O)[C@@H]1COCCN(c2ccc(Nc3ccc(-c4cnc5cc(F)ccn45)c4c3C(=O)NC4)nc2)C1] |

TABLE 1-continued
Selected Compounds
| # | Structure |
|---|---|
| I-628 | 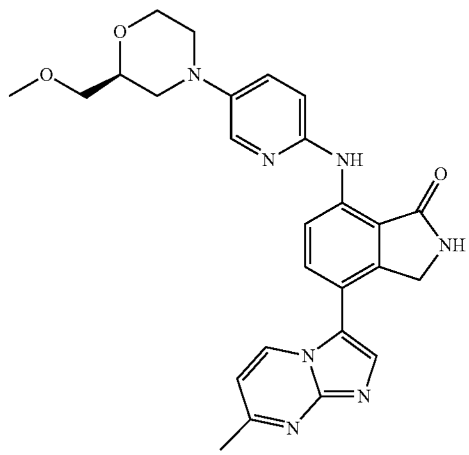 [SMILES: COC[C@@H]1CN(c2ccc(Nc3ccc(-c4cnc5nc(C)ccn45)c4c3C(=O)NC4)nc2)CCO1] |
| I-629 | 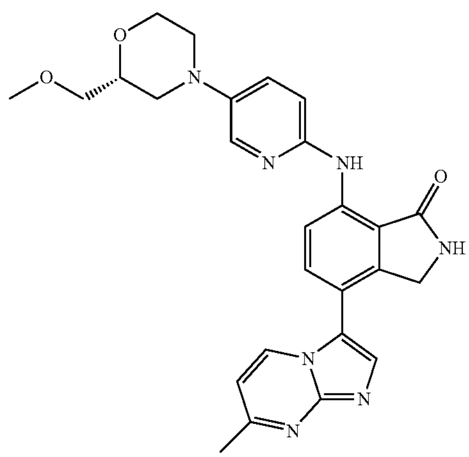 [SMILES: COC[C@H]1CN(c2ccc(Nc3ccc(-c4cnc5nc(C)ccn45)c4c3C(=O)NC4)nc2)CCO1] |
| I-630 | 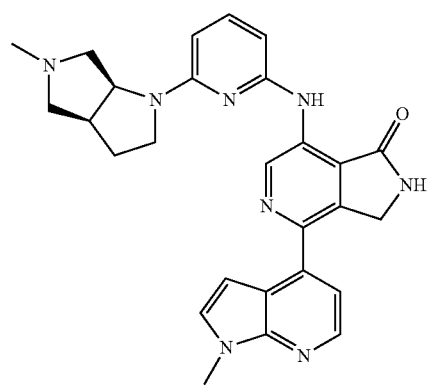 [SMILES: CN1C[C@@H]2CCN(c3cccc(Nc4cnc(-c5ccnc6c5ccn6C)c5c4C(=O)NC5)n3)[C@@H]2C1] |

TABLE 1-continued
Selected Compounds
| # | Structure |
|---|---|
| I-631 | 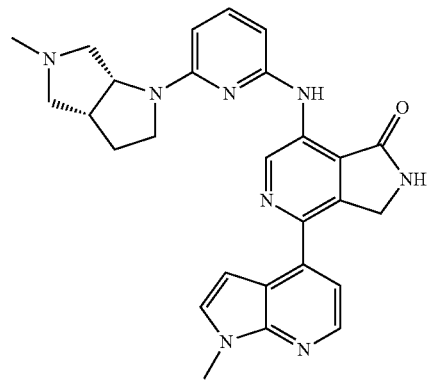 [SMILES: CN1C[C@H]2CCN(c3cccc(Nc4cnc(-c5ccnc6c5ccn6C)c5c4C(=O)NC5)n3)[C@H]2C1] |
| I-632 | 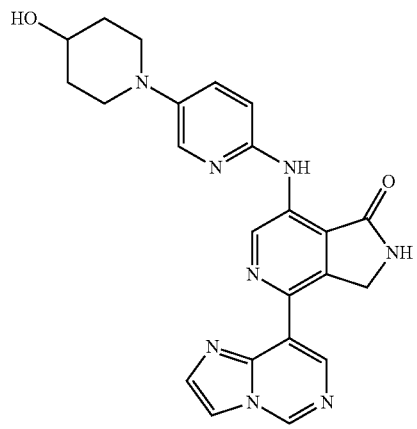 [SMILES: O=C1NCc2c(-c3cncn4ccnc34)ncc(Nc3ccc(N4CCC(O)CC4)cn3)c21] |
| I-633 | 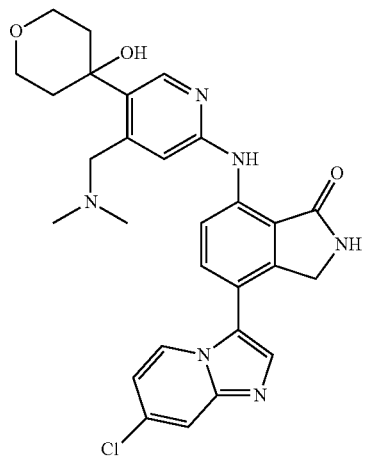 [SMILES: CN(C)Cc1cc(Nc2ccc(-c3cnc4cc(Cl)ccn34)c3c2C(=O)NC3)ncc1C1(O)CCOCC1] |

TABLE 1-continued
Selected Compounds
| # | Structure |
|---|---|
| I-634 | 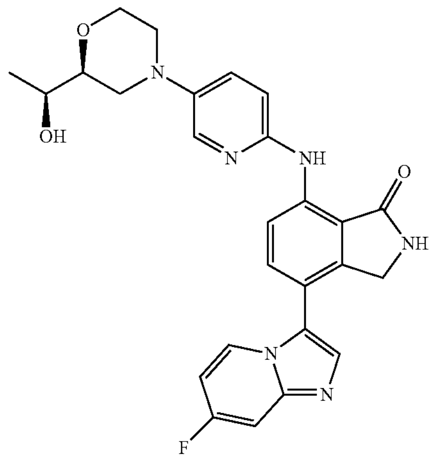 [SMILES: C[C@H](O)[C@@H]1CN(c2ccc(Nc3ccc(-c4cnc5cc(F)ccn45)c4c3C(=O)NC4)nc2)CCO1] |
| I-635 | 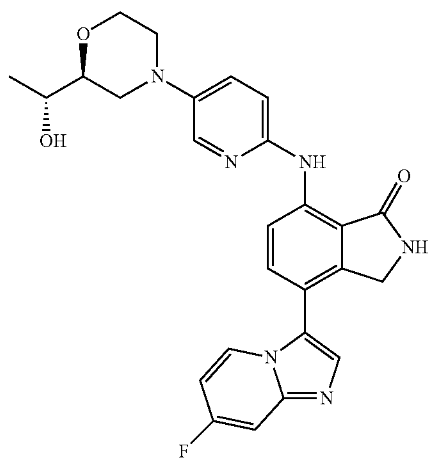 [SMILES: C[C@@H](O)[C@@H]1CN(c2ccc(Nc3ccc(-c4cnc5cc(F)ccn45)c4c3C(=O)NC4)nc2)CCO1] |
| I-639 | 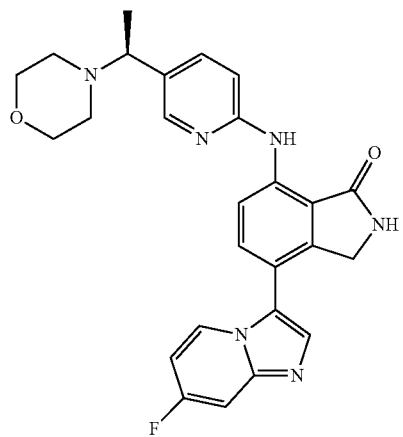 [SMILES: C[C@@H](c1ccc(Nc2ccc(-c3cnc4cc(F)ccn34)c3c2C(=O)NC3)nc1)N1CCOCC1] |

TABLE 1-continued
Selected Compounds
| # | Structure |
|---|---|
| I-640 | 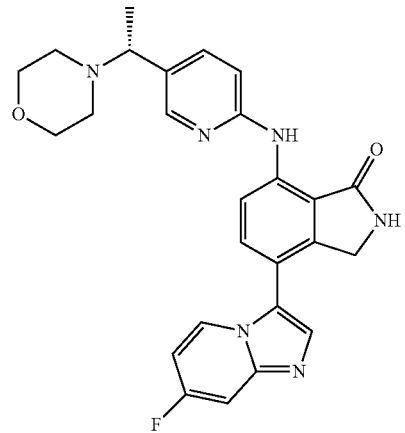 [SMILES: C[C@H](c1ccc(Nc2ccc(-c3cnc4cc(F)ccn34)c3c2C(=O)NC3)nc1)N1CCOCC1] |
| I-641 | 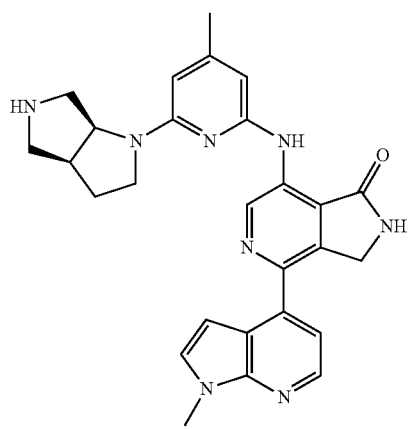 [SMILES: Cc1cc(Nc2cnc(-c3ccnc4c3ccn4C)c3c2C(=O)NC3)nc(N2CC[C@H]3CNC[C@H]32)c1] |
| I-642 | 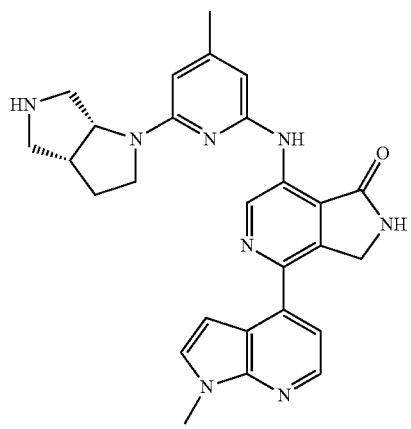 [SMILES: Cc1cc(Nc2cnc(-c3ccnc4c3ccn4C)c3c2C(=O)NC3)nc(N2CC[C@@H]3CNC[C@@H]32)c1] |

TABLE 1-continued
| Selected Compounds | |
|---|---|
| # | Structure |
I-643
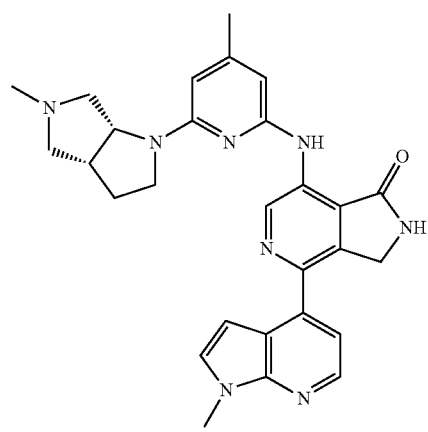 [SMILES: Cc1cc(Nc2cnc(-c3ccnc4c3ccn4C)c3c2C(=O)NC3)nc(N2CC[C@@H]3CN(C)C[C@@H]32)c1]
I-644
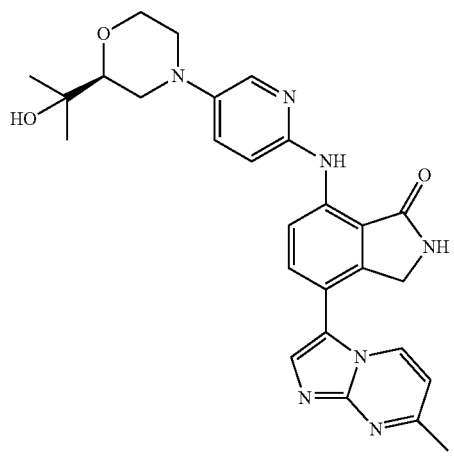 [SMILES: Cc1ccn2c(-c3ccc(Nc4ccc(N5CCO[C@H](C(C)(C)O)C5)cn4)c4c3CNC4=O)cnc2n1]
I-645

TABLE 1-continued
Selected Compounds
| # | Structure |
|---|-----------|
| I-646 | 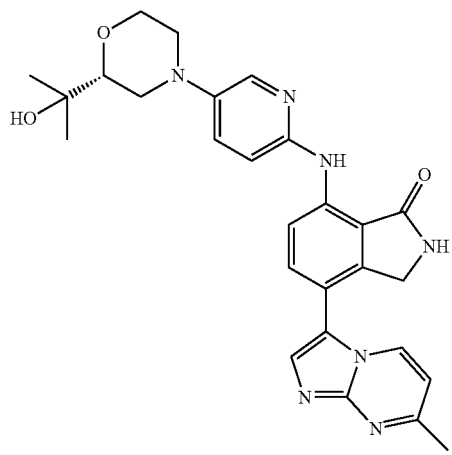 [SMILES: Cc1ccn2c(-c3ccc(Nc4ccc(N5CCO[C@@H](C(C)(C)O)C5)cn4)c4c3CNC4=O)cnc2n1] |
| I-648 | 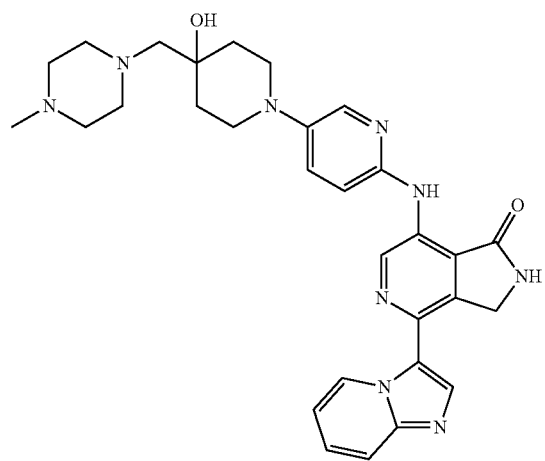 [SMILES: CN1CCN(CC2(O)CCN(c3ccc(Nc4cnc(-c5cnc6ccccn56)c5c4C(=O)NC5)nc3)CC2)CC1] |
| I-649 | 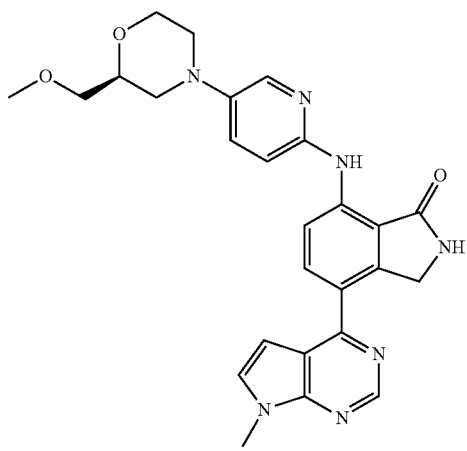 [SMILES: COC[C@@H]1CN(c2ccc(Nc3ccc(-c4ncnc5c4ccn5C)c4c3C(=O)NC4)nc2)CCO1] |

TABLE 1-continued
Selected Compounds
| # | Structure |
|---|---|
| I-650 | 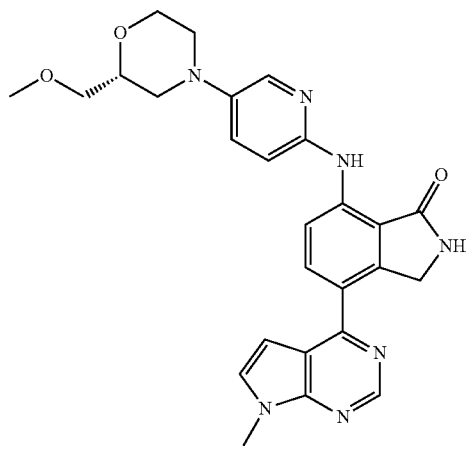 [SMILES: COC[C@H]1CN(c2ccc(Nc3ccc(-c4ncnc5c4ccn5C)c4c3C(=O)NC4)nc2)CCO1] |
| I-651 | 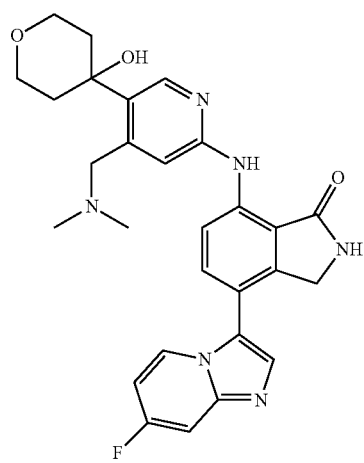 [SMILES: CN(C)Cc1cc(Nc2ccc(-c3cnc4cc(F)ccn34)c3c2C(=O)NC3)ncc1C1(O)CCOCC1] |
| I-652 | 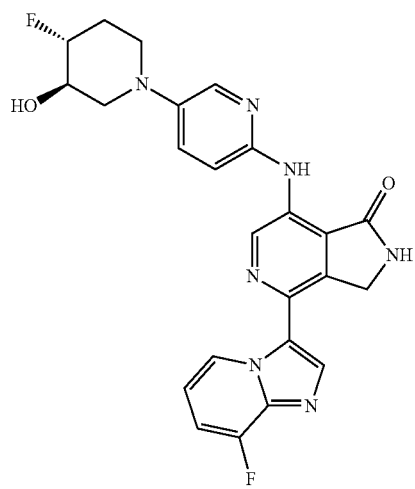 [SMILES: O=C1NCc2c(-c3cnc4c(F)cccn34)ncc(Nc3ccc(N4CC[C@@H](F)[C@H](O)C4)cn3)c21] |

TABLE 1-continued
Selected Compounds
| # | Structure |
|---|---|
| I-653 | 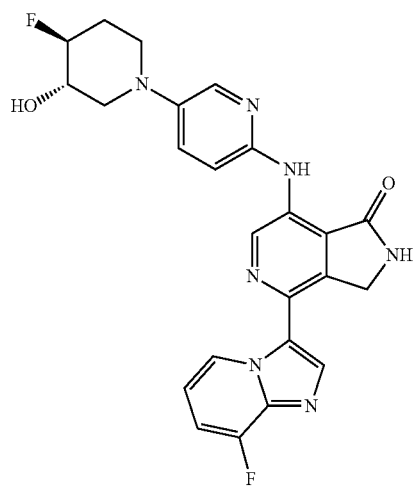 [SMILES: O=C1NCc2c(-c3cnc4c(F)cccn34)ncc(Nc3ccc(N4CC[C@H](F)[C@@H](O)C4)cn3)c21] |
| I-654 | 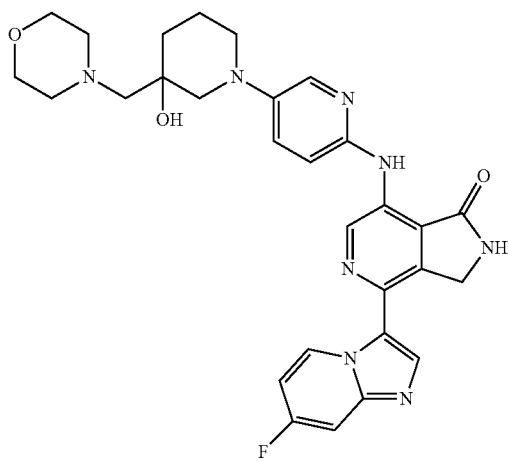 [SMILES: O=C1NCc2c(-c3cnc4cc(F)ccn34)ncc(Nc3ccc(N4CCCC(O)(CN5CCOCC5)C4)cn3)c21] |
| I-655 | 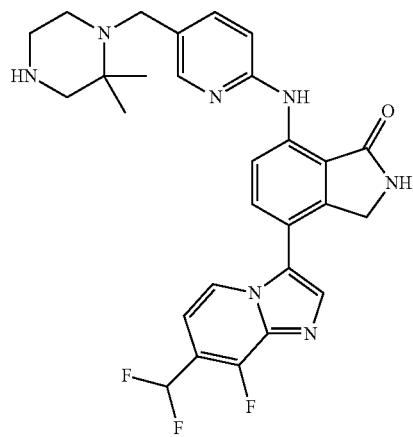 [SMILES: CC1(C)CNCCN1Cc1ccc(Nc2ccc(-c3cnc4c(F)c(C(F)F)ccn34)c3c2C(=O)NC3)nc1] |

TABLE 1-continued
Selected Compounds
| # | Structure |
|---|---|
| I-656 | 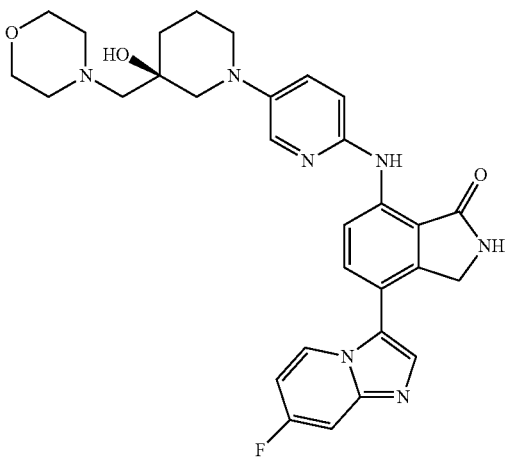 [SMILES: O=C1NCc2c(-c3cnc4cc(F)ccn34)ccc(Nc3ccc(N4CCC[C@@](O)(CN5CCOCC5)C4)cn3)c21] |
| I-657 | 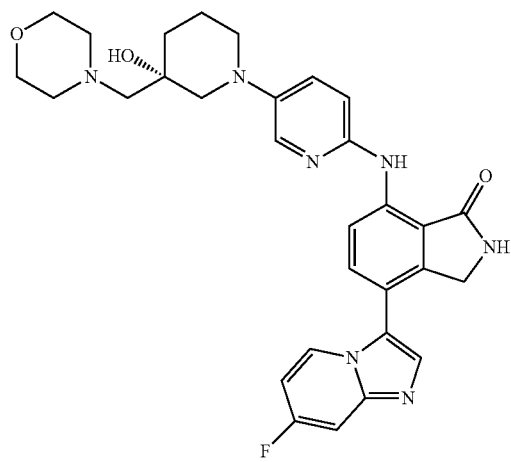 [SMILES: O=C1NCc2c(-c3cnc4cc(F)ccn34)ccc(Nc3ccc(N4CCC[C@](O)(CN5CCOCC5)C4)cn3)c21] |
| I-658 | 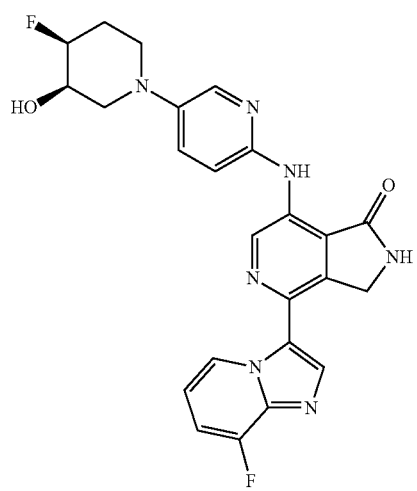 [SMILES: O=C1NCc2c(-c3cnc4c(F)cccn34)ncc(Nc3ccc(N4CC[C@H](F)[C@H](O)C4)cn3)c21] |

TABLE 1-continued
Selected Compounds
| # | Structure |
|---|---|
| I-659 | 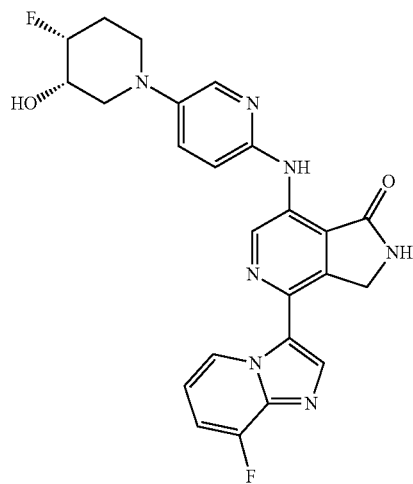 [SMILES: O=C1NCc2c(-c3cnc4c(F)cccn34)ncc(Nc3ccc(N4CC[C@@H](F)[C@@H](O)C4)cn3)c21] |
| I-660 | 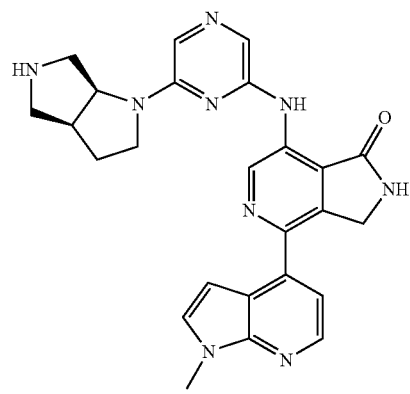 [SMILES: Cn1ccc2c(-c3ncc(Nc4cncc(N5CC[C@H]6CNC[C@H]65)n4)c4c3CNC4=O)ccnc21] |
| I-661 | 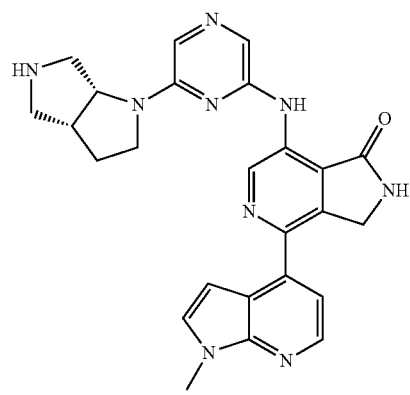 [SMILES: Cn1ccc2c(-c3ncc(Nc4cncc(N5CC[C@@H]6CNC[C@@H]65)n4)c4c3CNC4=O)ccnc21] |

TABLE 1-continued
Selected Compounds
| # | Structure |
|---|---|
| I-662 | 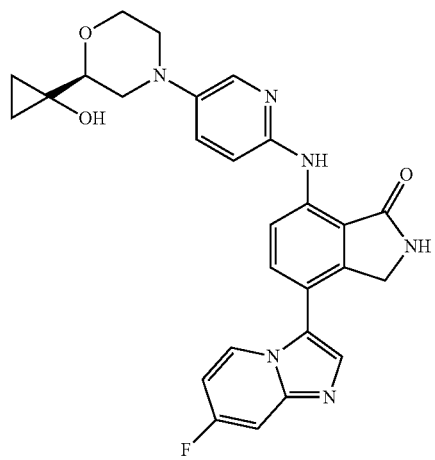 [SMILES: O=C1NCc2c(-c3cnc4cc(F)ccn34)ccc(Nc3ccc(N4CCO[C@H](C5(O)CC5)C4)cn3)c21] |
| I-663 | 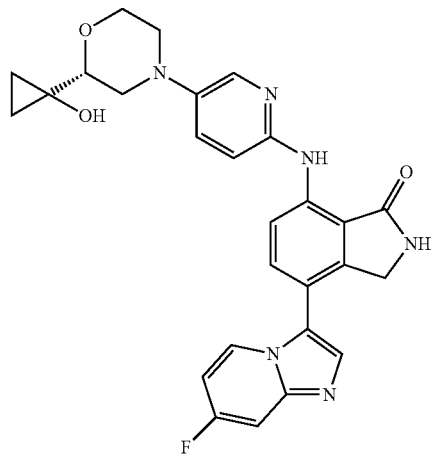 [SMILES: O=C1NCc2c(-c3cnc4cc(F)ccn34)ccc(Nc3ccc(N4CCO[C@@H](C5(O)CC5)C4)cn3)c21] |
| I-667 | 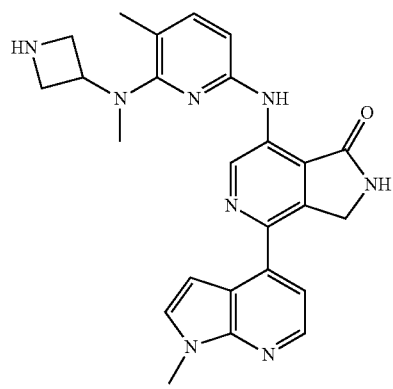 [SMILES: Cc1ccc(Nc2cnc(-c3ccnc4c3ccn4C)c3c2C(=O)NC3)nc1N(C)C1CNC1] |

TABLE 1-continued
Selected Compounds
| # | Structure |
|---|---|
| I-668 | 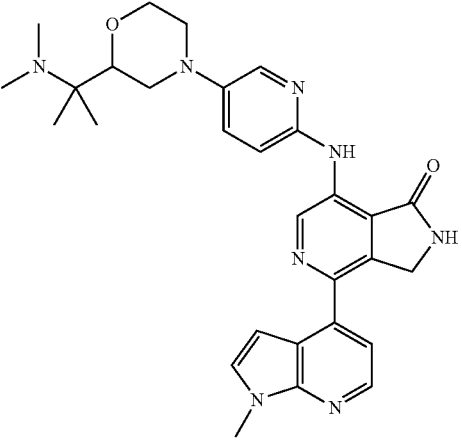 [SMILES: CN(C)C(C)(C)C1CN(c2ccc(Nc3cnc(-c4ccnc5c4ccn5C)c4c3C(=O)NC4)nc2)CCO1] |
| I-669 | 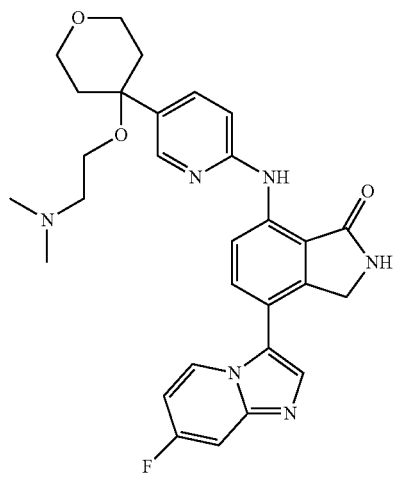 [SMILES: CN(C)CCOC1(c2ccc(Nc3ccc(-c4cnc5cc(F)ccn45)c4c3C(=O)NC4)nc2)CCOCC1] |
| I-670 | 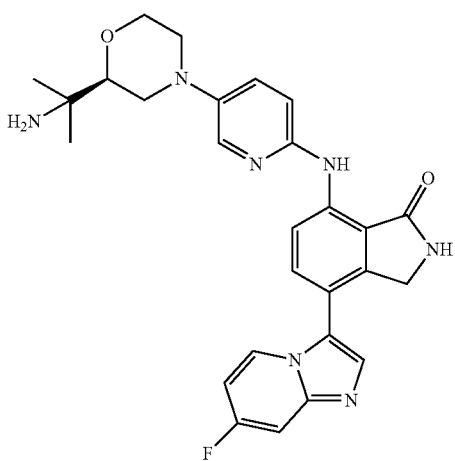 [SMILES: CC(C)(N)[C@@H]1CN(c2ccc(Nc3ccc(-c4cnc5cc(F)ccn45)c4c3C(=O)NC4)nc2)CCO1] |

TABLE 1-continued
| Selected Compounds | |
|---|---|
| # | Structure |
| I-671 | 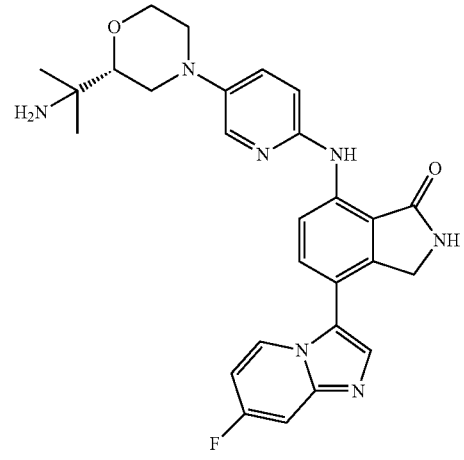 [SMILES: CC(C)(N)[C@H]1CN(c2ccc(Nc3ccc(-c4cnc5cc(F)ccn45)c4c3C(=O)NC4)nc2)CCO1] |
| I-672 | 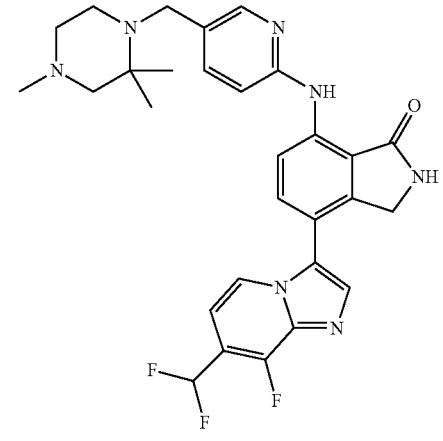 [SMILES: CN1CCN(Cc2ccc(Nc3ccc(-c4cnc5c(F)c(C(F)F)ccn45)c4c3C(=O)NC4)nc2)C(C)(C)C1] |
| I-673 | 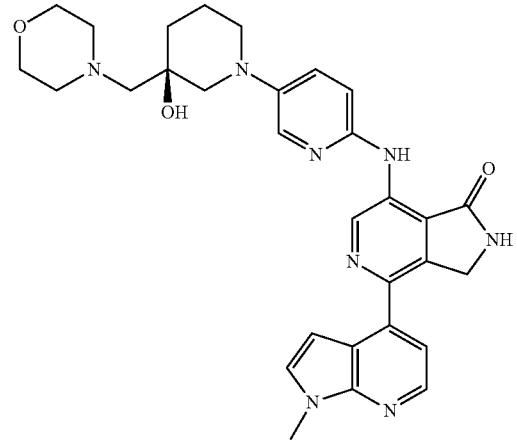 [SMILES: Cn1ccc2c(-c3ncc(Nc4ccc(N5CCC[C@@](O)(CN6CCOCC6)C5)cn4)c4c3CNC4=O)ccnc21] |

TABLE 1-continued
Selected Compounds
| # | Structure |
|---|---|
| I-674 | 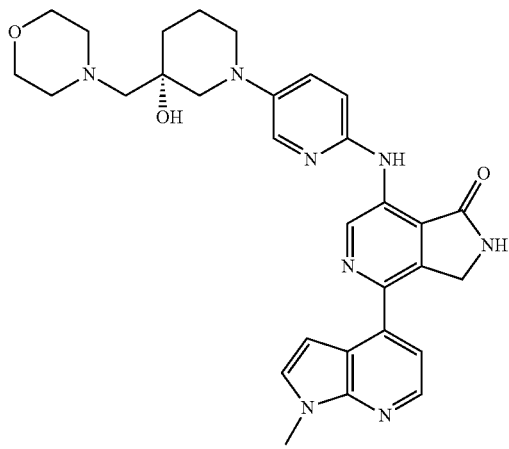 [SMILES: Cn1ccc2c(-c3ncc(Nc4ccc(N5CCC[C@](O)(CN6CCOCC6)C5)cn4)c4c3CNC4=O)ccnc21] |
| I-675 | 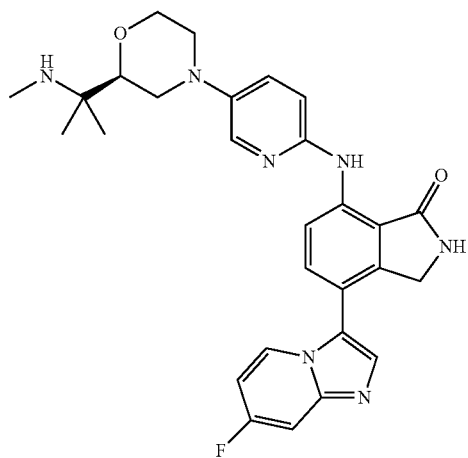 [SMILES: CNC(C)(C)[C@@H]1CN(c2ccc(Nc3ccc(-c4cnc5cc(F)ccn45)c4c3C(=O)NC4)nc2)CCO1] |
| I-676 | 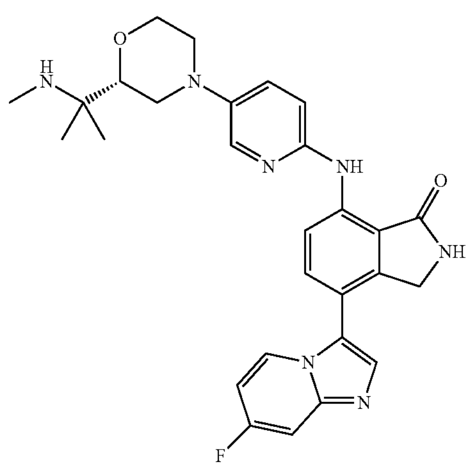 [SMILES: CNC(C)(C)[C@H]1CN(c2ccc(Nc3ccc(-c4cnc5cc(F)ccn45)c4c3C(=O)NC4)nc2)CCO1] |

TABLE 1-continued

Selected Compounds

| # | Structure |
|---|-----------|
| I-677 | 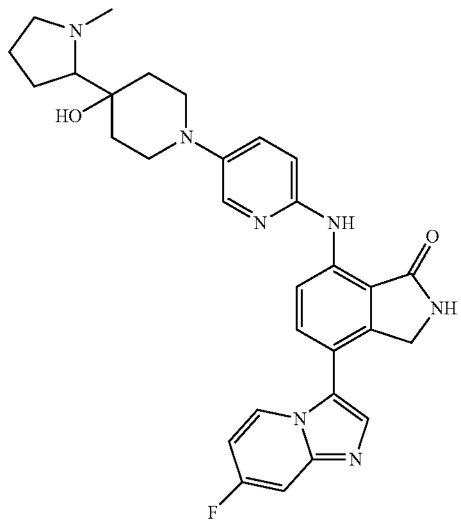 [SMILES: CN1CCCC1C1(O)CCN(c2ccc(Nc3ccc(-c4cnc5cc(F)ccn45)c4c3C(=O)NC4)nc2)CC1] |
| I-678 | 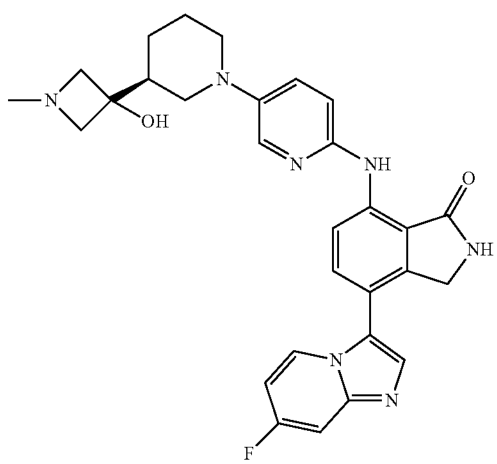 [SMILES: CN1CC(O)([C@H]2CCCN(c3ccc(Nc4ccc(-c5cnc6cc(F)ccn56)c5c4C(=O)NC5)nc3)C2)C1] |
| I-679 | 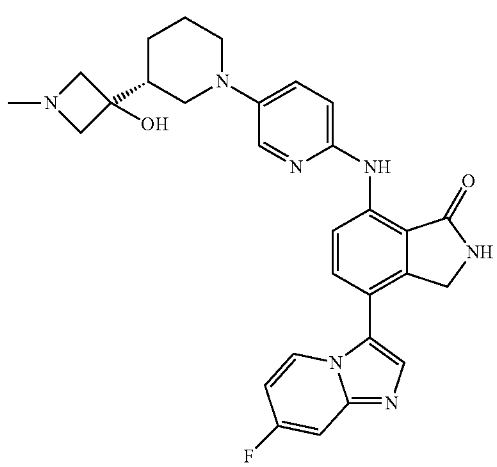 [SMILES: CN1CC(O)([C@@H]2CCCN(c3ccc(Nc4ccc(-c5cnc6cc(F)ccn56)c5c4C(=O)NC5)nc3)C2)C1] |

TABLE 1-continued
Selected Compounds
| # | Structure |
|---|---|
| I-680 | 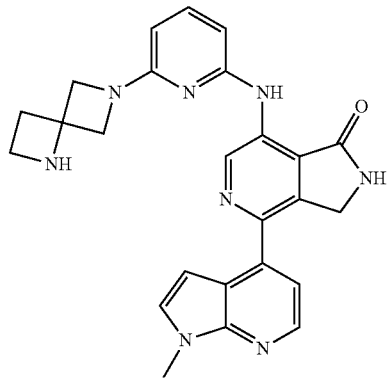 [SMILES: Cn1ccc2c(-c3ncc(Nc4cccc(N5CC6(CCN6)C5)n4)c4c3CNC4=O)ccnc21] |
| I-681 | 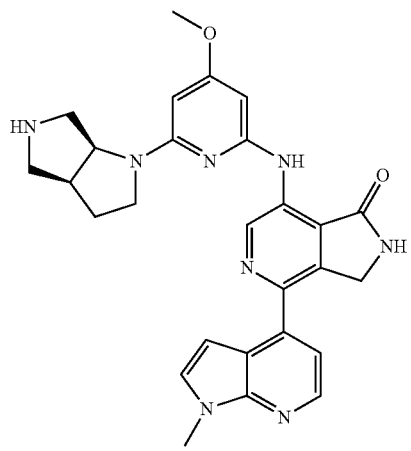 [SMILES: COc1cc(Nc2cnc(-c3ccnc4c3ccn4C)c3c2C(=O)NC3)nc(N2CC[C@H]3CNC[C@H]32)c1] |
| I-682 | 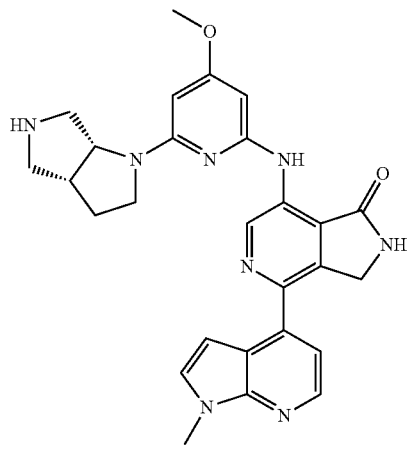 [SMILES: COc1cc(Nc2cnc(-c3ccnc4c3ccn4C)c3c2C(=O)NC3)nc(N2CC[C@@H]3CNC[C@@H]32)c1] |

TABLE 1-continued
Selected Compounds
| # | Structure |
|---|---|
| I-683 | 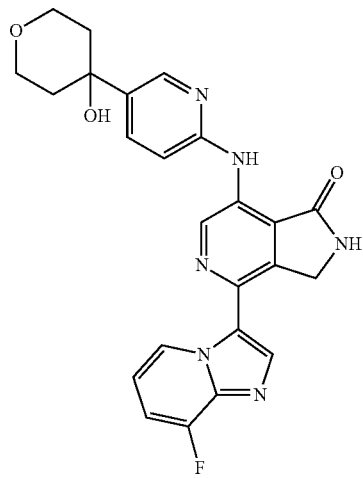 [SMILES: O=C1NCc2c(-c3cnc4c(F)cccn34)ncc(Nc3ccc(C4(O)CCOCC4)cn3)c21] |
| I-684 | 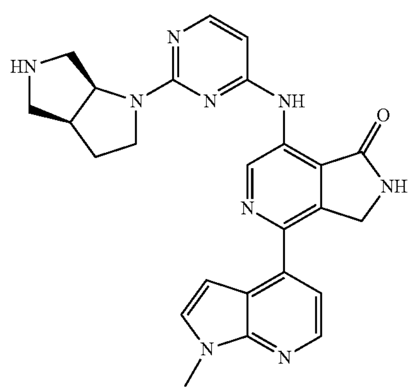 [SMILES: Cn1ccc2c(-c3ncc(Nc4ccnc(N5CC[C@H]6CNC[C@H]65)n4)c4c3CNC4=O)ccnc21] |
| I-685 | 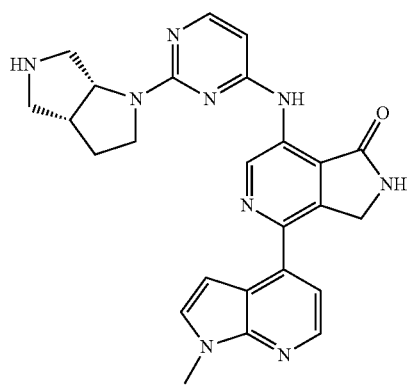 [SMILES: Cn1ccc2c(-c3ncc(Nc4ccnc(N5CC[C@@H]6CNC[C@@H]65)n4)c4c3CNC4=O)ccnc21] |

US 12,215,105 B2
599
600
TABLE 1-continued
| Selected Compounds | |
|---|---|
| # | Structure |
I-686
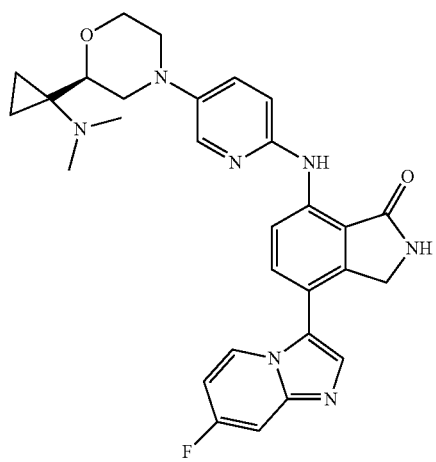 [SMILES: CN(C)C1([C@@H]2CN(c3ccc(Nc4ccc(-c5cnc6cc(F)ccn56)c5c4C(=O)NC5)nc3)CCO2)CC1]
I-687
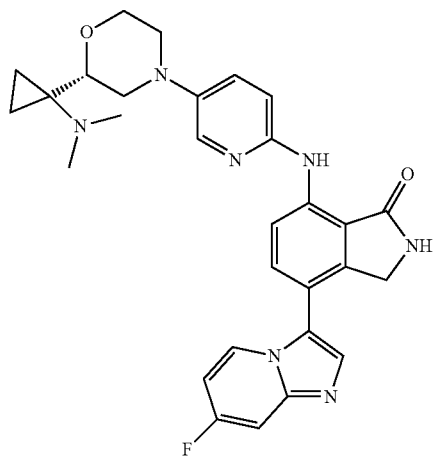 [SMILES: CN(C)C1([C@H]2CN(c3ccc(Nc4ccc(-c5cnc6cc(F)ccn56)c5c4C(=O)NC5)nc3)CCO2)CC1]
I-688
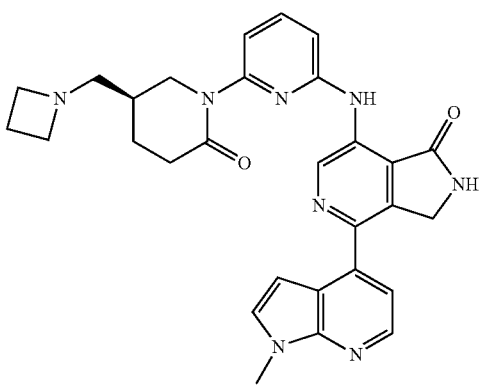 [SMILES: Cn1ccc2c(-c3ncc(Nc4cccc(N5C[C@H](CN6CCC6)CCC5=O)n4)c4c3CNC4=O)ccnc21]

TABLE 1-continued
Selected Compounds
| # | Structure |
|---|---|
| I-689 | 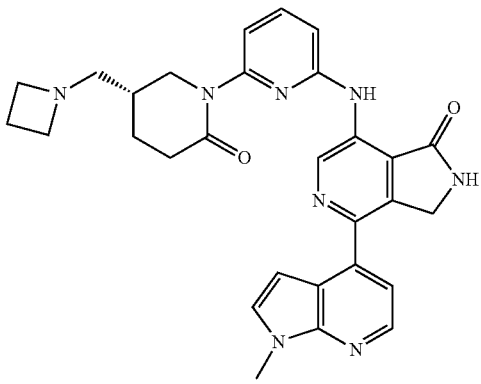 [SMILES: Cn1ccc2c(-c3ncc(Nc4cccc(N5C[C@@H](CN6CCC6)CCC5=O)n4)c4c3CNC4=O)ccnc21] |
| I-690 | 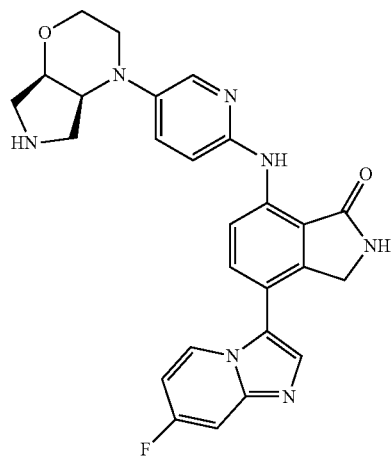 [SMILES: O=C1NCc2c(-c3cnc4cc(F)ccn34)ccc(Nc3ccc(N4CCO[C@@H]5CNC[C@@H]54)cn3)c21] |
| I-691 | 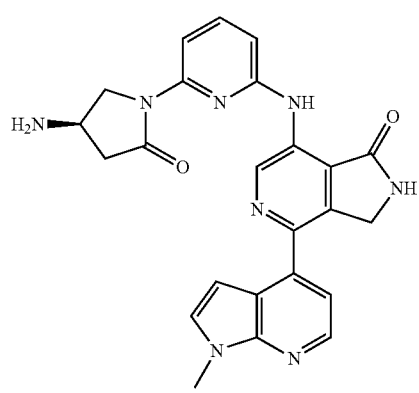 [SMILES: Cn1ccc2c(-c3ncc(Nc4cccc(N5C[C@H](N)CC5=O)n4)c4c3CNC4=O)ccnc21] |

TABLE 1-continued
| Selected Compounds | |
|---|---|
| # | Structure |
I-692
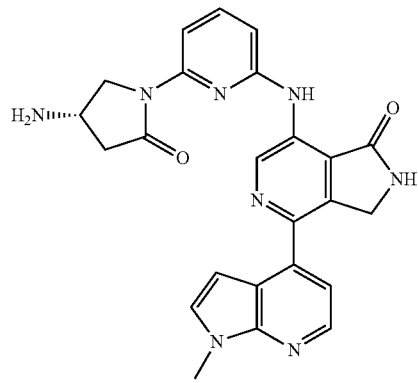 [SMILES: Cn1ccc2c(-c3ncc(Nc4cccc(N5C[C@@H](N)CC5=O)n4)c4c3CNC4=O)ccnc21]
I-693
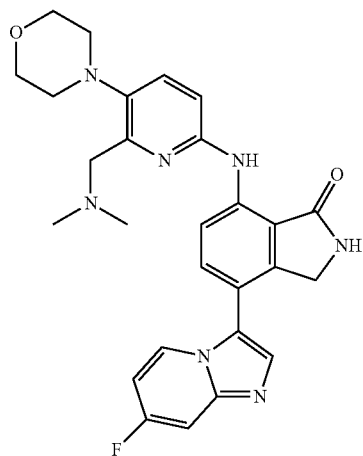 [SMILES: CN(C)Cc1nc(Nc2ccc(-c3cnc4cc(F)ccn34)c3c2C(=O)NC3)ccc1N1CCOCC1]
I-694
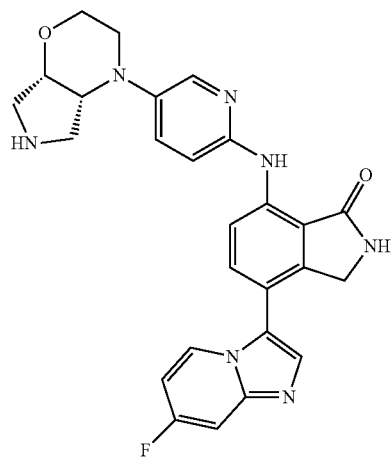 [SMILES: O=C1NCc2c(-c3cnc4cc(F)ccn34)ccc(Nc3ccc(N4CCO[C@H]5CNC[C@H]54)cn3)c21]

TABLE 1-continued
Selected Compounds
| # | Structure |
|---|---|
| I-695 | 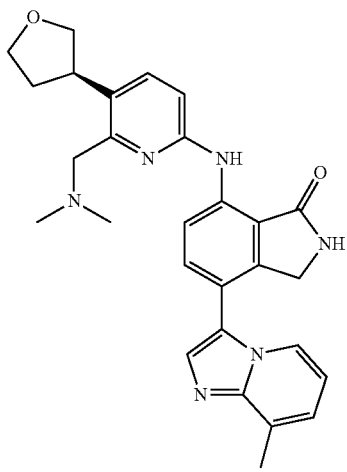 [SMILES: Cc1cccn2c(-c3ccc(Nc4ccc([C@H]5CCOC5)c(CN(C)C)n4)c4c3CNC4=O)cnc12] |
| I-696 | 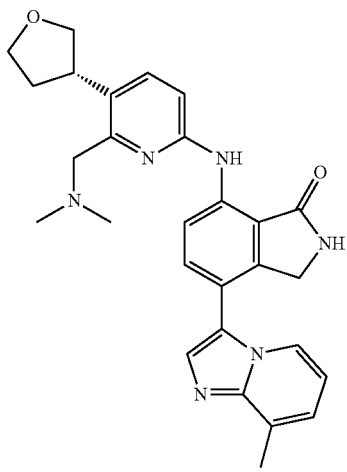 [SMILES: Cc1cccn2c(-c3ccc(Nc4ccc([C@@H]5CCOC5)c(CN(C)C)n4)c4c3CNC4=O)cnc12] |
| I-697 | 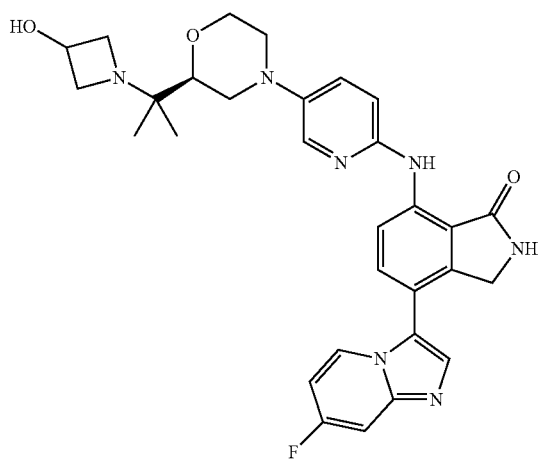 [SMILES: CC(C)([C@@H]1CN(c2ccc(Nc3ccc(-c4cnc5cc(F)ccn45)c4c3C(=O)NC4)nc2)CCO1)N1CC(O)C1] |

TABLE 1-continued
Selected Compounds
| # | Structure |
|---|---|
| I-698 | 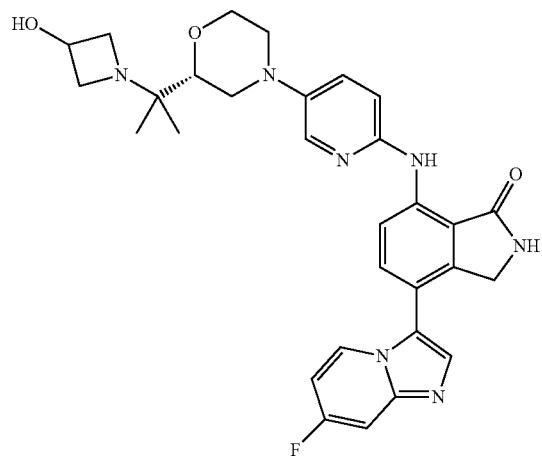 [SMILES: CC(C)([C@H]1CN(c2ccc(Nc3ccc(-c4cnc5cc(F)ccn45)c4c3C(=O)NC4)nc2)CCO1)N1CC(O)C1] |
| I-699 | 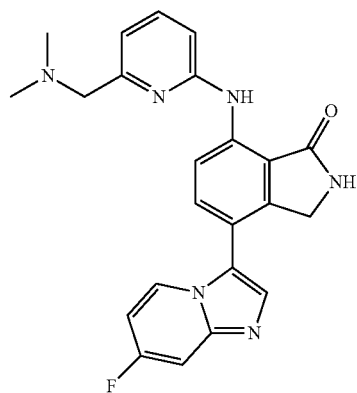 [SMILES: CN(C)Cc1cccc(Nc2ccc(-c3cnc4cc(F)ccn34)c3c2C(=O)NC3)n1] |
| I-700 | 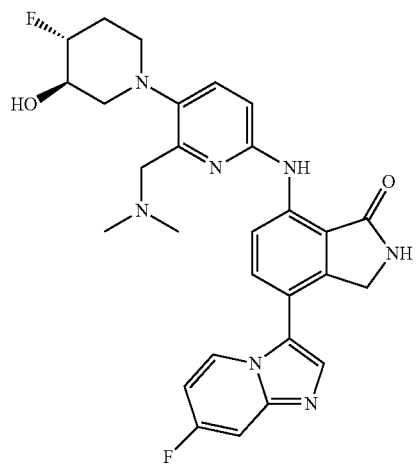 [SMILES: CN(C)Cc1nc(Nc2ccc(-c3cnc4cc(F)ccn34)c3c2C(=O)NC3)ccc1N1CC[C@@H](F)[C@H](O)C1] |

TABLE 1-continued
Selected Compounds
| # | Structure |
|---|---|
I-701
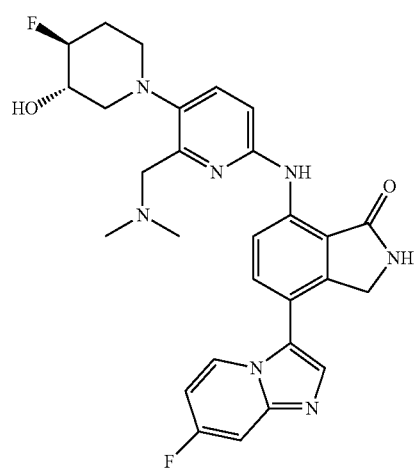 [SMILES: CN(C)Cc1nc(Nc2ccc(-c3cnc4cc(F)ccn34)c3c2C(=O)NC3)ccc1N1CC[C@H](F)[C@@H](O)C1]
I-702
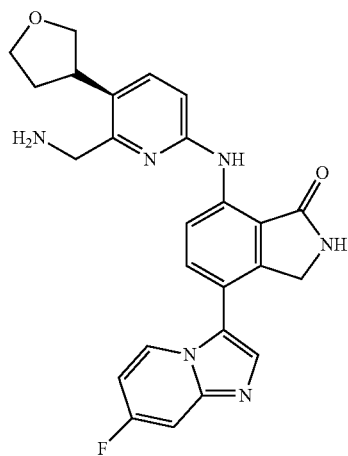
I-703
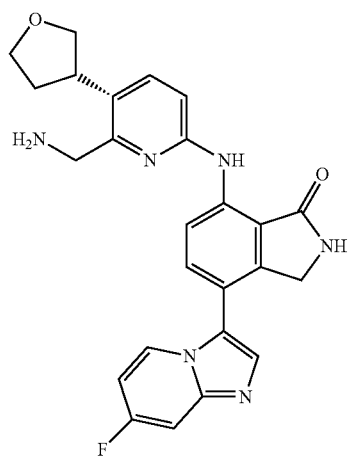

TABLE 1-continued
| Selected Compounds | |
|---|---|
| # | Structure |
| I-704 | 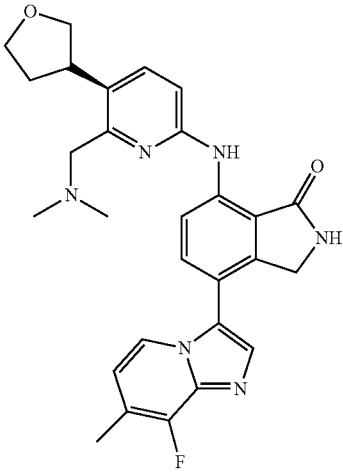 |
| I-705 | 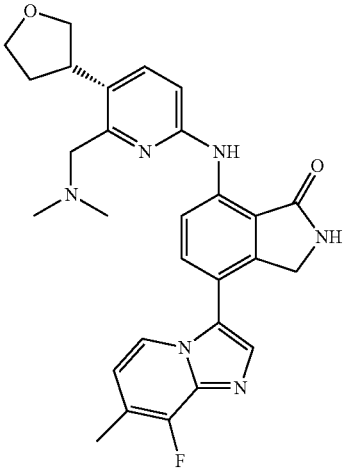 |
| I-706 | 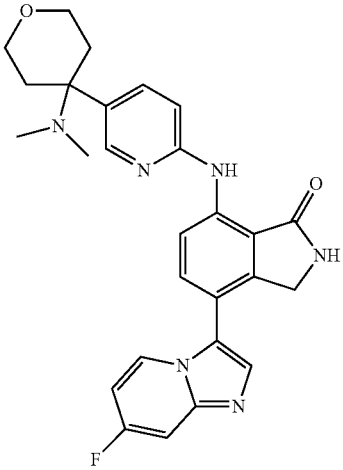 [SMILES: CN(C)C1(c2ccc(Nc3ccc(-c4cnc5cc(F)ccn45)c4c3C(=O)NC4)nc2)CCOCC1] |

TABLE 1-continued

| Selected Compounds | |
|---|---|
| # | Structure |

I-707

I-708

I-709

TABLE 1-continued
Selected Compounds
| # | Structure |
|---|---|
| I-710 | 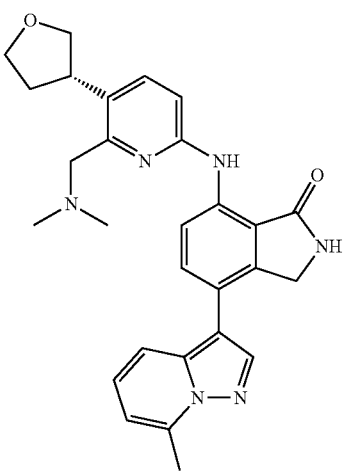 [SMILES: Cc1cccc2c(-c3ccc(Nc4ccc([C@@H]5CCOC5)c(CN(C)C)n4)c4c3CNC4=O)cnn12] |
| I-711 | 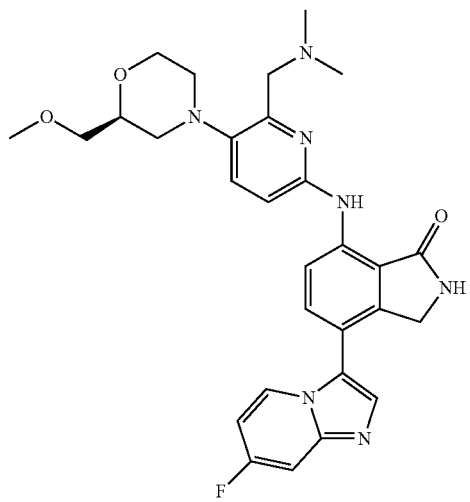 [SMILES: COC[C@@H]1CN(c2ccc(Nc3ccc(-c4cnc5cc(F)ccn45)c4c3C(=O)NC4)nc2CN(C)C)CCO1] |
| I-712 | 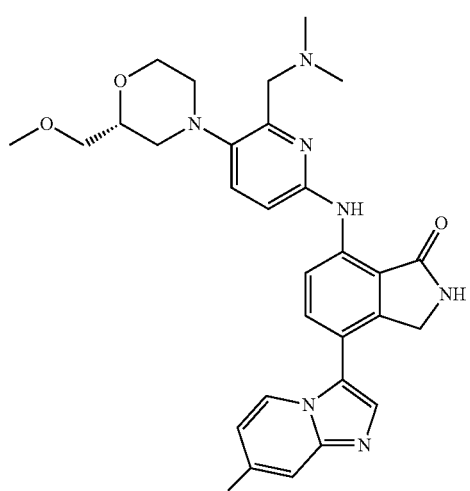 |

TABLE 1-continued
Selected Compounds
| # | Structure |
|---|---|
| I-713 | 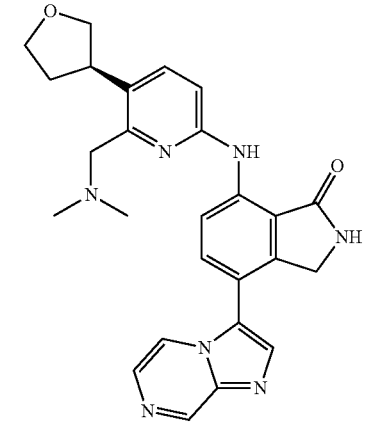 [SMILES: CN(C)Cc1nc(Nc2ccc(-c3cnc4cnccn34)c3c2C(=O)NC3)ccc1[C@H]1CCOC1] |
| I-714 | 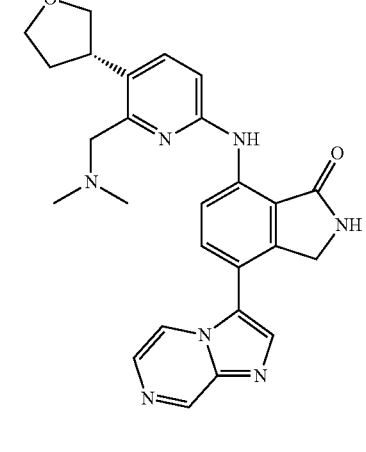 |
| I-715 | 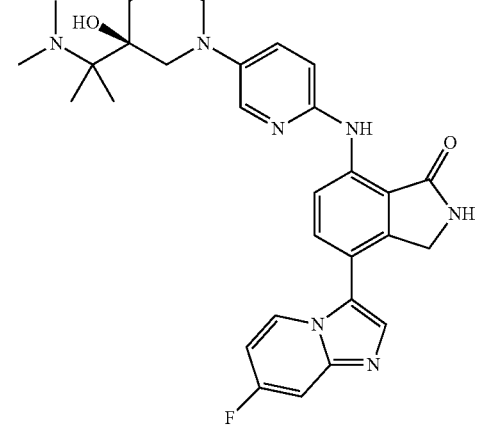 |

TABLE 1-continued
Selected Compounds
| # | Structure |
|---|---|
| I-716 | 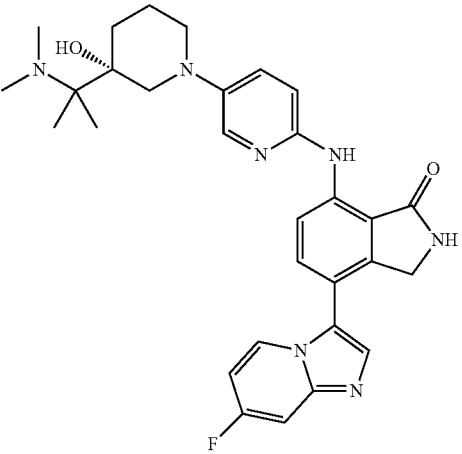 [SMILES: CN(C)C(C)(C)[C@@]1(O)CCCN(c2ccc(Nc3ccc(-c4cnc5cc(F)ccn45)c4c3C(=O)NC4)nc2)C1] |
| I-717 | 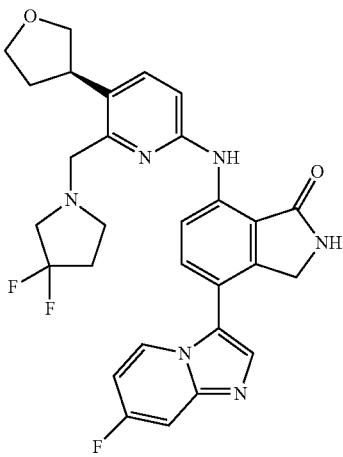 [SMILES: O=C1NCc2c(-c3cnc4cc(F)ccn34)ccc(Nc3ccc([C@H]4CCOC4)c(CN4CCC(F)(F)C4)n3)c21] |
| I-718 | 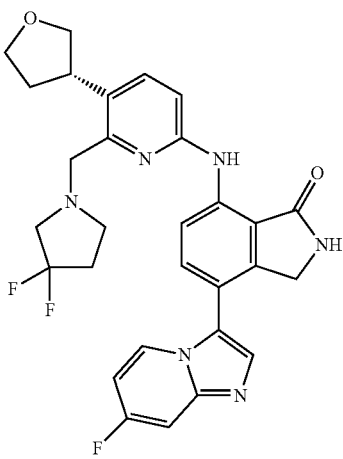 [SMILES: O=C1NCc2c(-c3cnc4cc(F)ccn34)ccc(Nc3ccc([C@@H]4CCOC4)c(CN4CCC(F)(F)C4)n3)c21] |

TABLE 1-continued
Selected Compounds
| # | Structure |
|---|---|
| I-719 | 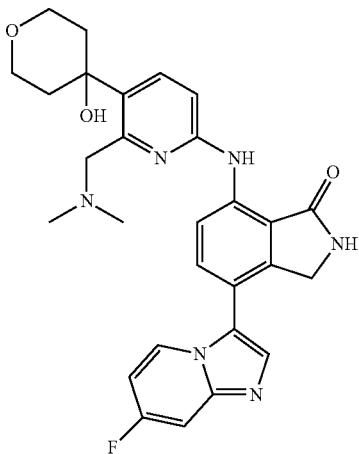 [SMILES: CN(C)Cc1nc(Nc2ccc(-c3cnc4cc(F)ccn34)c3c2C(=O)NC3)ccc1C1(O)CCOCC1] |
| I-720 | 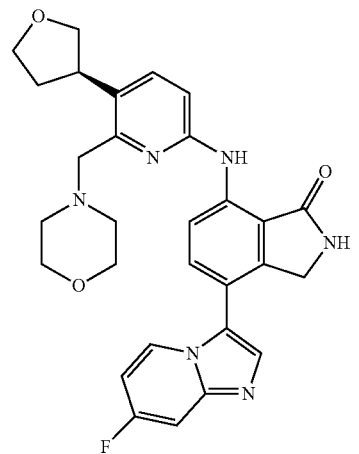 [SMILES: O=C1NCc2c(-c3cnc4cc(F)ccn34)ccc(Nc3ccc([C@H]4CCOC4)c(CN4CCOCC4)n3)c21] |
| I-721 | 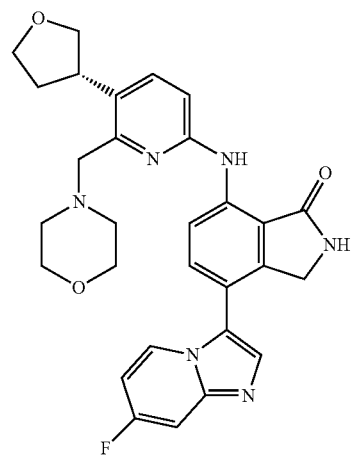 [SMILES: O=C1NCc2c(-c3cnc4cc(F)ccn34)ccc(Nc3ccc([C@@H]4CCOC4)c(CN4CCOCC4)n3)c21] |

TABLE 1-continued
Selected Compounds
| # | Structure |
|---|---|
| I-722 | 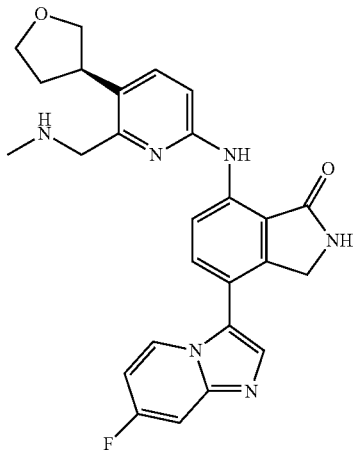 [SMILES: CNCc1nc(Nc2ccc(-c3cnc4cc(F)ccn34)c3c2C(=O)NC3)ccc1[C@H]1CCOC1] |
| I-723 | 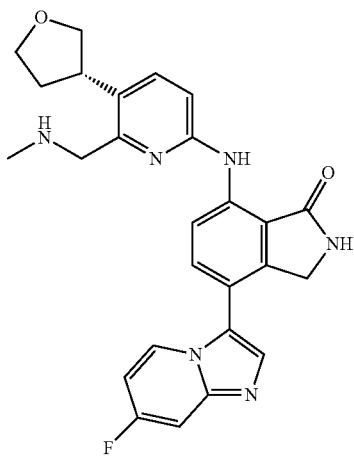 [SMILES: CNCc1nc(Nc2ccc(-c3cnc4cc(F)ccn34)c3c2C(=O)NC3)ccc1[C@@H]1CCOC1] |
| I-724 | 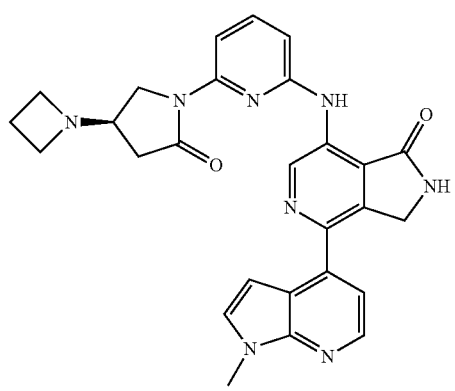 [SMILES: Cn1ccc2c(-c3ncc(Nc4cccc(N5C[C@H](N6CCC6)CC5=O)n4)c4c3CNC4=O)ccnc21] |

TABLE 1-continued
Selected Compounds
| # | Structure |
|---|---|
| I-725 | 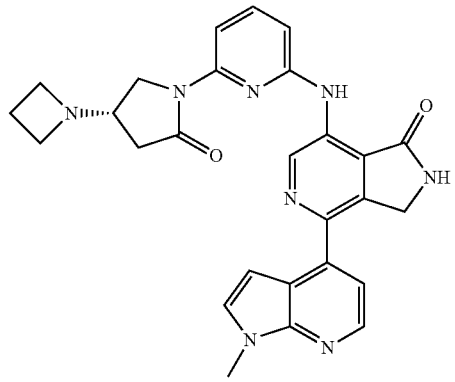 [SMILES: Cn1ccc2c(-c3ncc(Nc4cccc(N5C[C@@H](N6CCC6)CC5=O)n4)c4c3CNC4=O)ccnc21] |
| I-726 | 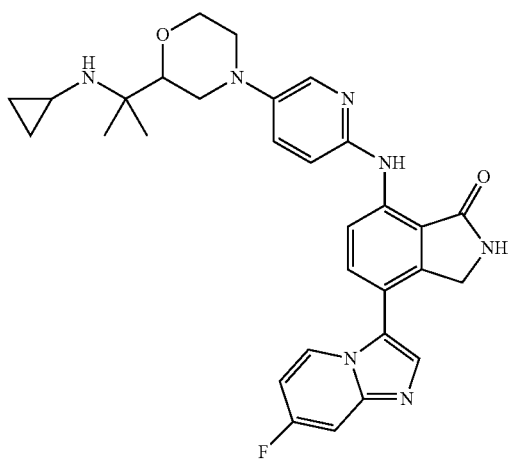 [SMILES: CC(C)(NC1CC1)C1CN(c2ccc(Nc3ccc(-c4cnc5cc(F)ccn45)c4c3C(=O)NC4)nc2)CCO1] |
| I-727 | 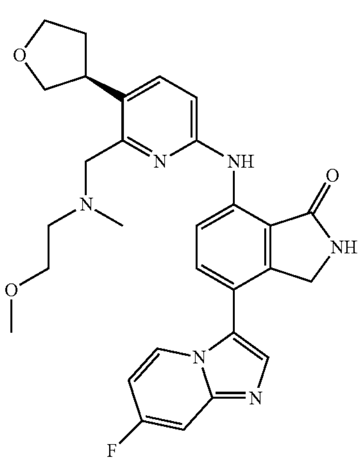 [SMILES: COCCN(C)Cc1nc(Nc2ccc(-c3cnc4cc(F)ccn34)c3c2C(=O)NC3)ccc1[C@@H]1CCOC1] |

TABLE 1-continued
Selected Compounds
| # | Structure |
|---|-----------|
| I-728 | 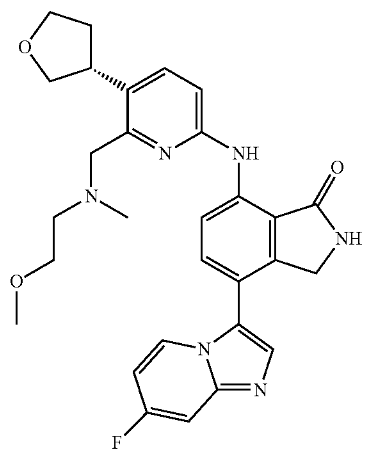 [SMILES: COCCN(C)Cc1nc(Nc2ccc(-c3cnc4cc(F)ccn34)c3c2C(=O)NC3)ccc1[C@H]1CCOC1] |
| I-729 | 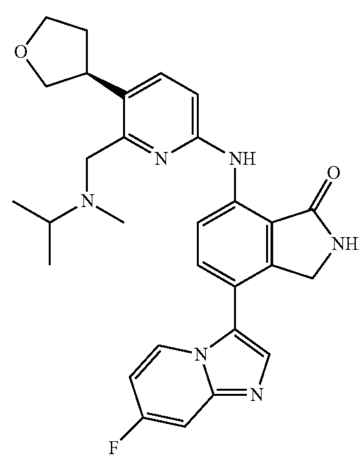 [SMILES: CC(C)N(C)Cc1nc(Nc2ccc(-c3cnc4cc(F)ccn34)c3c2C(=O)NC3)ccc1[C@@H]1CCOC1] |
| I-730 | 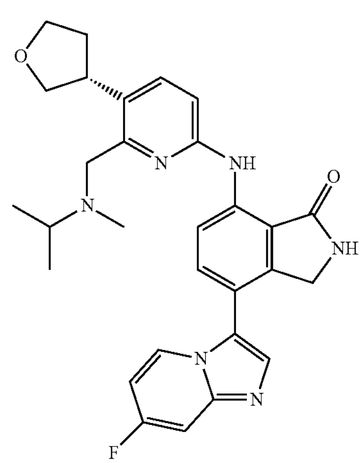 [SMILES: CC(C)N(C)Cc1nc(Nc2ccc(-c3cnc4cc(F)ccn34)c3c2C(=O)NC3)ccc1[C@H]1CCOC1] |

TABLE 1-continued
Selected Compounds
| # | Structure |
|---|---|
| I-731 | 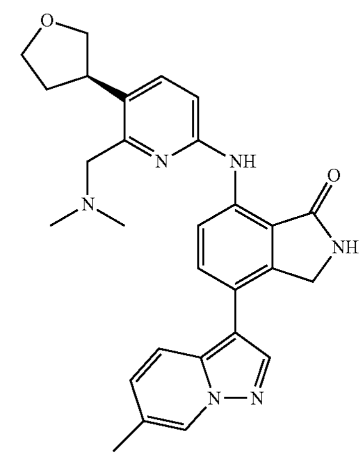 [SMILES: Cc1ccc2c(-c3ccc(Nc4ccc([C@H]5CCOC5)c(CN(C)C)n4)c4c3CNC4=O)cnn2c1] |
| I-732 | 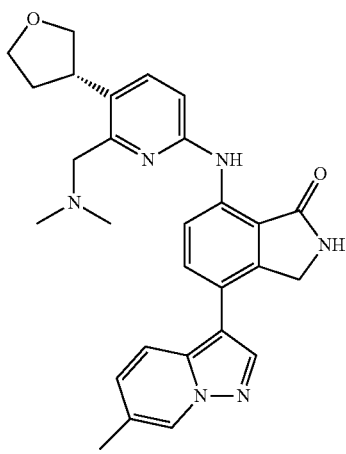 [SMILES: Cc1ccc2c(-c3ccc(Nc4ccc([C@@H]5CCOC5)c(CN(C)C)n4)c4c3CNC4=O)cnn2c1] |
| I-733 | 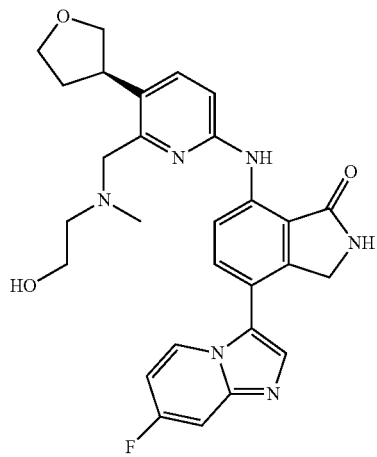 [SMILES: CN(CCO)Cc1nc(Nc2ccc(-c3cnc4cc(F)ccn34)c3c2C(=O)NC3)ccc1[C@H]1CCOC1] |

TABLE 1-continued
Selected Compounds
| # | Structure |
|---|---|
| I-734 | 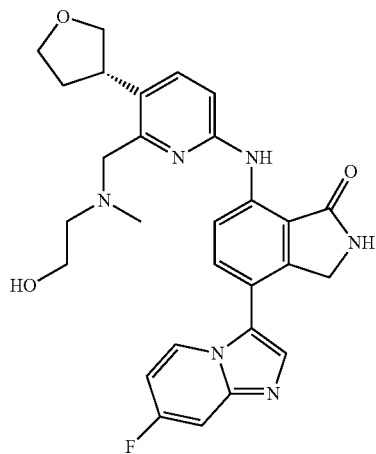 [SMILES: CN(CCO)Cc1nc(Nc2ccc(-c3cnc4cc(F)ccn34)c3c2C(=O)NC3)ccc1[C@@H]1CCOC1] |
| I-735 | 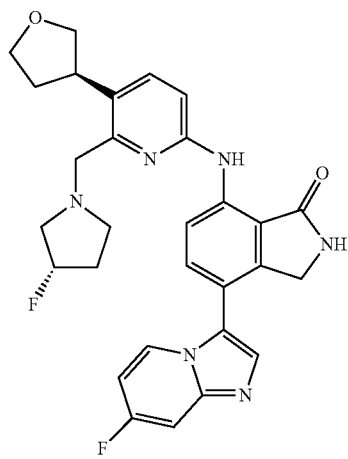 [SMILES: O=C1NCc2c(-c3cnc4cc(F)ccn34)ccc(Nc3ccc([C@H]4CCOC4)c(CN4CC[C@H](F)C4)n3)c21] |
| I-736 | 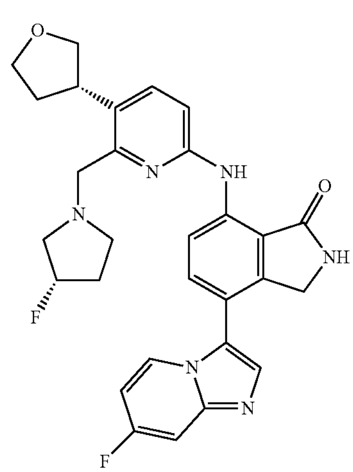 [SMILES: O=C1NCc2c(-c3cnc4cc(F)ccn34)ccc(Nc3ccc([C@@H]4CCOC4)c(CN4CC[C@H](F)C4)n3)c21] |

TABLE 1-continued
Selected Compounds
| # | Structure |
|---|---|
| I-737 | 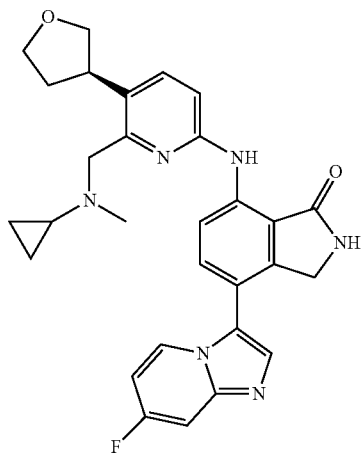 [SMILES: CN(Cc1nc(Nc2ccc(-c3cnc4cc(F)ccn34)c3c2C(=O)NC3)ccc1[C@H]1CCOC1)C1CC1] |
| I-738 | 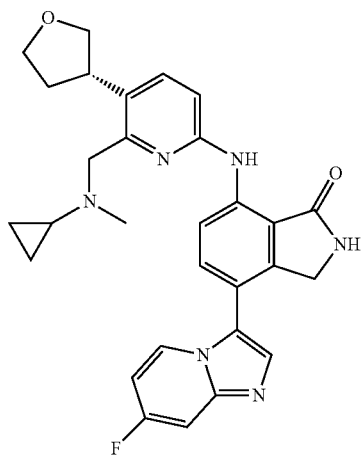 [SMILES: CN(Cc1nc(Nc2ccc(-c3cnc4cc(F)ccn34)c3c2C(=O)NC3)ccc1[C@@H]1CCOC1)C1CC1] |
| I-739 | 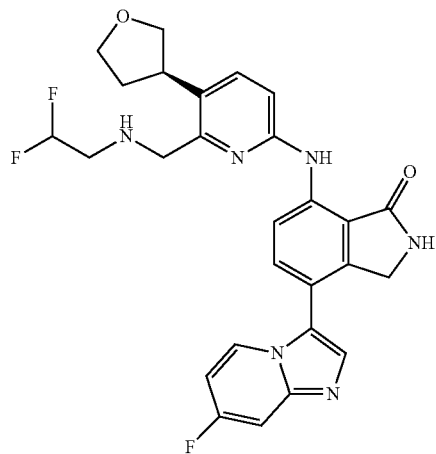 [SMILES: O=C1NCc2c(-c3cnc4cc(F)ccn34)ccc(Nc3ccc([C@H]4CCOC4)c(CNCC(F)F)n3)c21] |

TABLE 1-continued
Selected Compounds
| # | Structure |
|---|---|
| I-740 | 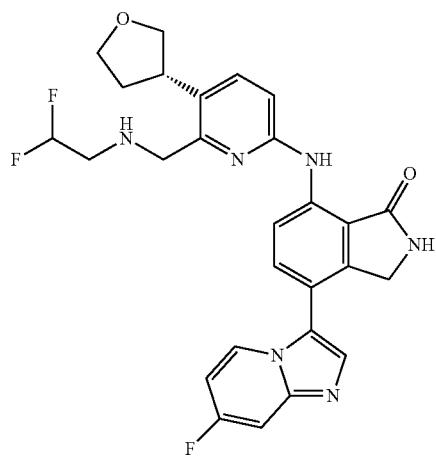 [SMILES: O=C1NCc2c(-c3cnc4cc(F)ccn34)ccc(Nc3ccc([C@@H]4CCOC4)c(CNCC(F)F)n3)c21] |
| I-741 | 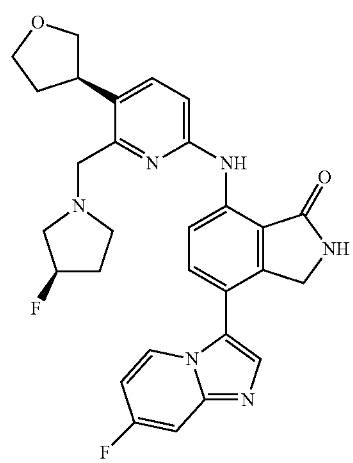 [SMILES: O=C1NCc2c(-c3cnc4cc(F)ccn34)ccc(Nc3ccc([C@H]4CCOC4)c(CN4CC[C@@H](F)C4)n3)c21] |
| I-742 | 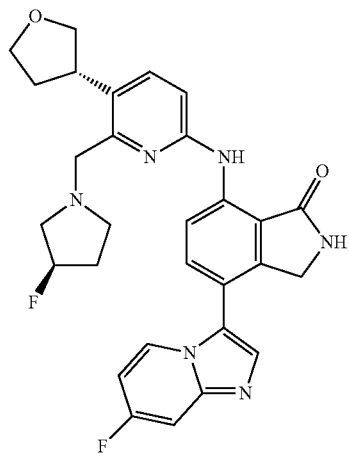 [SMILES: O=C1NCc2c(-c3cnc4cc(F)ccn34)ccc(Nc3ccc([C@@H]4CCOC4)c(CN4CC[C@@H](F)C4)n3)c21] |

TABLE 1-continued
Selected Compounds
| # | Structure |
|---|---|
| I-743 | 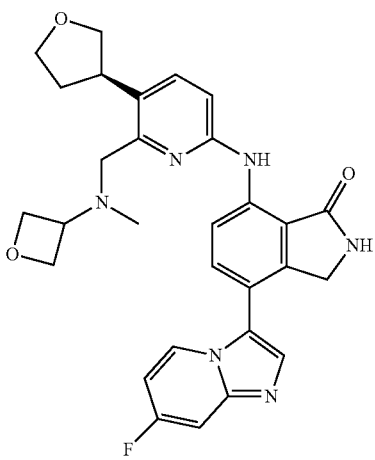 [SMILES: CN(Cc1nc(Nc2ccc(-c3cnc4cc(F)ccn34)c3c2C(=O)NC3)ccc1[C@H]1CCOC1)C1COC1] |
| I-744 | 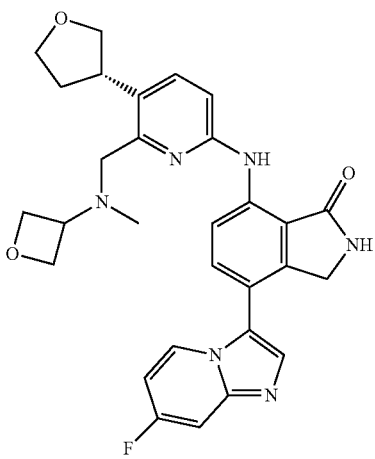 [SMILES: CN(Cc1nc(Nc2ccc(-c3cnc4cc(F)ccn34)c3c2C(=O)NC3)ccc1[C@@H]1CCOC1)C1COC1] |
| I-745 | 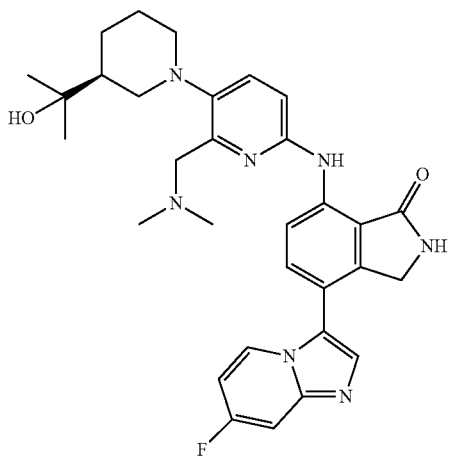 [SMILES: CN(C)Cc1nc(Nc2ccc(-c3cnc4cc(F)ccn34)c3c2C(=O)NC3)ccc1N1CCC[C@H](C(C)(C)O)C1] |

TABLE 1-continued
| Selected Compounds | |
|---|---|
| # | Structure |
I-746
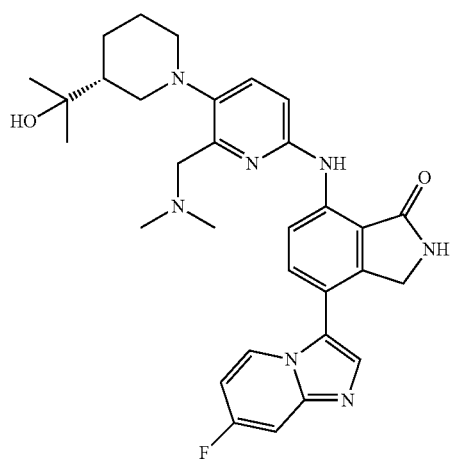 [SMILES: CN(C)Cc1nc(Nc2ccc(-c3cnc4cc(F)ccn34)c3c2C(=O)NC3)ccc1N1CCC[C@@H](C(C)(C)O)C1]
I-747
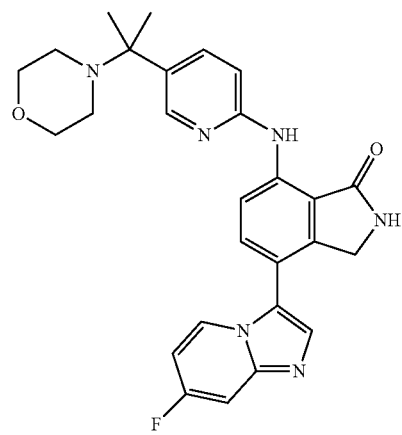 [SMILES: CC(C)(c1ccc(Nc2ccc(-c3cnc4cc(F)ccn34)c3c2C(=O)NC3)nc1)N1CCOCC1]
I-748
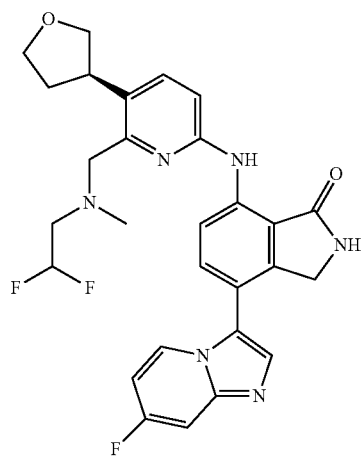 [SMILES: CN(Cc1nc(Nc2ccc(-c3cnc4cc(F)ccn34)c3c2C(=O)NC3)ccc1[C@H]1CCOC1)CC(F)F]

TABLE 1-continued
Selected Compounds
| # | Structure |
|---|---|
| I-749 | 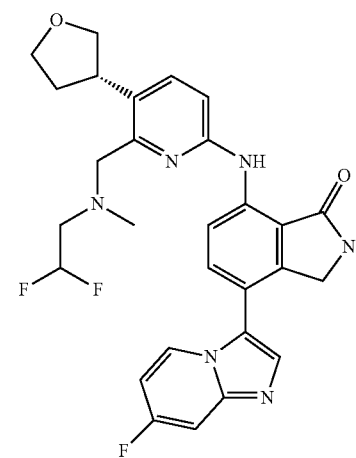 |
| I-750 | 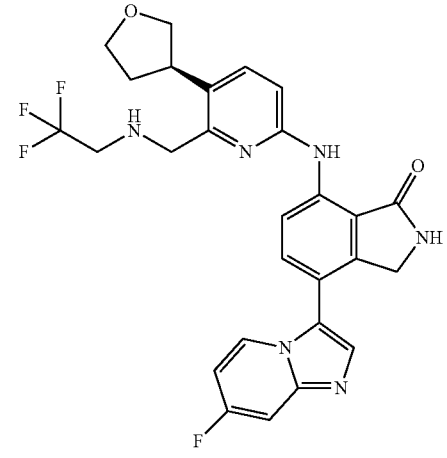 [SMILES: O=C1NCc2c(-c3cnc4cc(F)ccn34)ccc(Nc3ccc([C@H]4CCOC4)c(CNCC(F)(F)F)n3)c21] |
| I-751 | 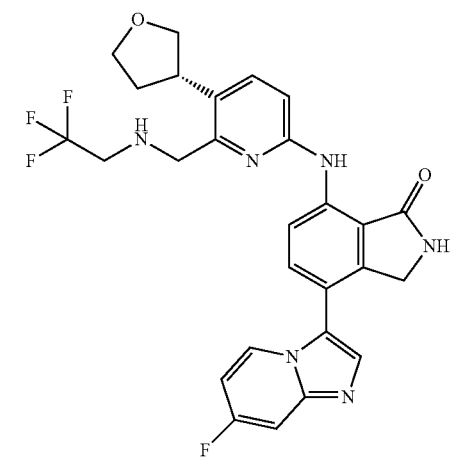 [SMILES: O=C1NCc2c(-c3cnc4cc(F)ccn34)ccc(Nc3ccc([C@@H]4CCOC4)c(CNCC(F)(F)F)n3)c21] |

TABLE 1-continued
Selected Compounds
| # | Structure |
|---|---|
| I-752 | 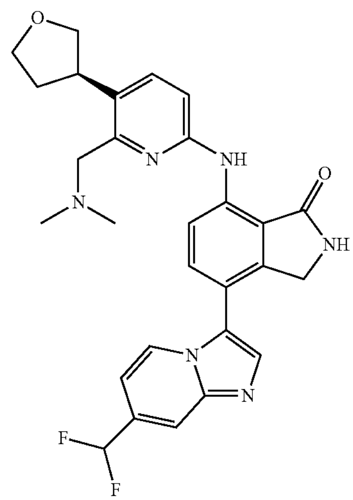 [SMILES: CN(C)Cc1nc(Nc2ccc(-c3cnc4cc(C(F)F)ccn34)c3c2C(=O)NC3)ccc1[C@H]1CCOC1] |
| I-753 | 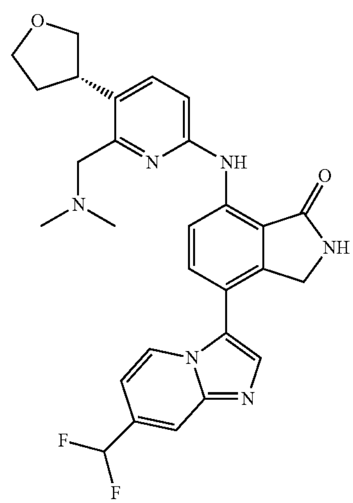 [SMILES: CN(C)Cc1nc(Nc2ccc(-c3cnc4cc(C(F)F)ccn34)c3c2C(=O)NC3)ccc1[C@@H]1CCOC1] |
| I-754 | 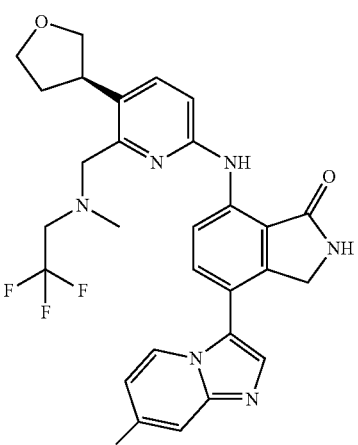 |

TABLE 1-continued
Selected Compounds
| # | Structure |
|---|---|
| I-755 | 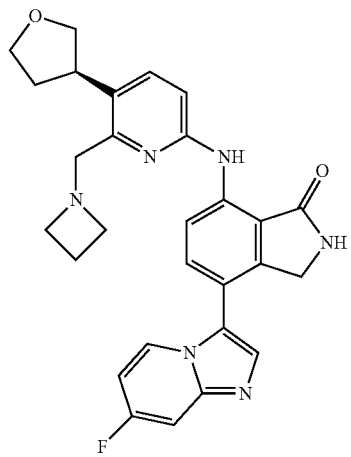 [SMILES: O=C1NCc2c(-c3cnc4cc(F)ccn34)ccc(Nc3ccc([C@H]4CCOC4)c(CN4CCC4)n3)c21] |
| I-756 | 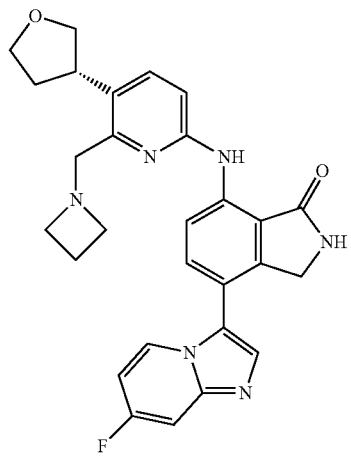 [SMILES: O=C1NCc2c(-c3cnc4cc(F)ccn34)ccc(Nc3ccc([C@@H]4CCOC4)c(CN4CCC4)n3)c21] |
| I-757 | 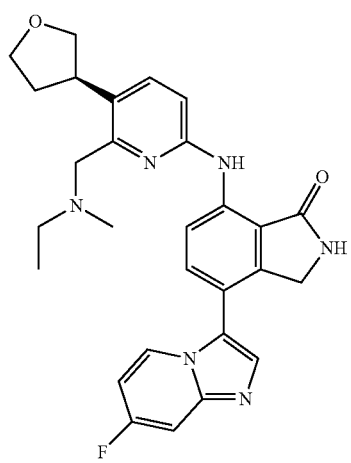 [SMILES: CCN(C)Cc1nc(Nc2ccc(-c3cnc4cc(F)ccn34)c3c2C(=O)NC3)ccc1[C@H]1CCOC1] |

TABLE 1-continued
Selected Compounds
| # | Structure |
|---|---|
| I-758 | 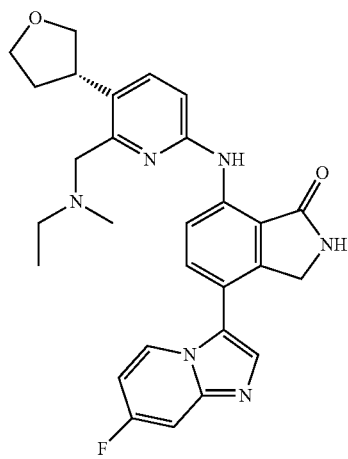 [SMILES: CCN(C)Cc1nc(Nc2ccc(-c3cnc4cc(F)ccn34)c3c2C(=O)NC3)ccc1[C@@H]1CCOC1] |
| I-759 | 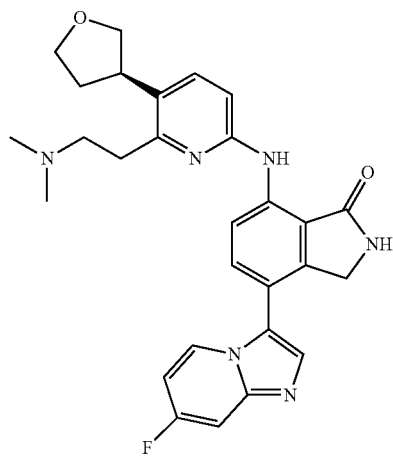 [SMILES: CN(C)CCc1nc(Nc2ccc(-c3cnc4cc(F)ccn34)c3c2C(=O)NC3)ccc1[C@H]1CCOC1] |
| I-760 | 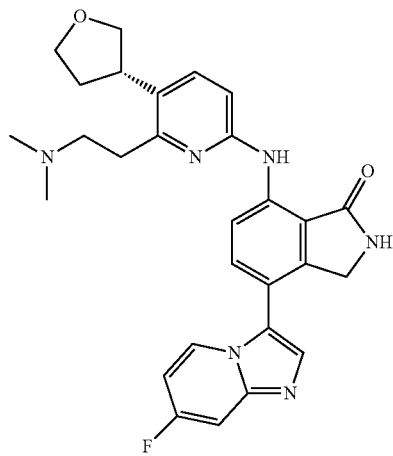 [SMILES: CN(C)CCc1nc(Nc2ccc(-c3cnc4cc(F)ccn34)c3c2C(=O)NC3)ccc1[C@@H]1CCOC1] |

TABLE 1-continued
Selected Compounds
| # | Structure |
|---|---|
| I-761 | 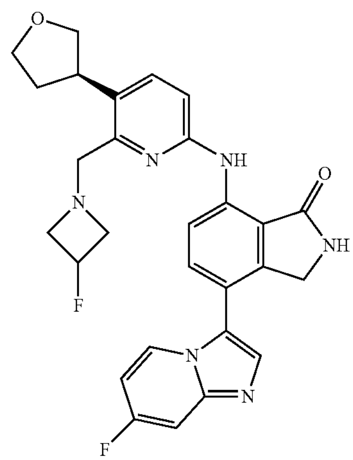 [SMILES: O=C1NCc2c(-c3cnc4cc(F)ccn34)ccc(Nc3ccc([C@H]4CCOC4)c(CN4CC(F)C4)n3)c21] |
| I-762 | 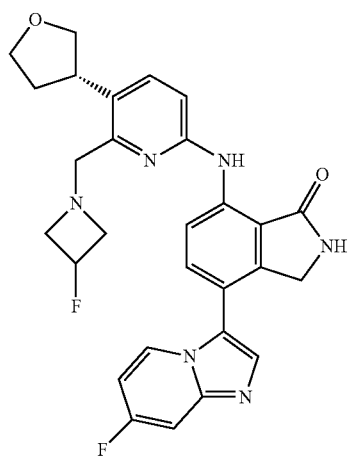 [SMILES: O=C1NCc2c(-c3cnc4cc(F)ccn34)ccc(Nc3ccc([C@@H]4CCOC4)c(CN4CC(F)C4)n3)c21] |
| I-763 | 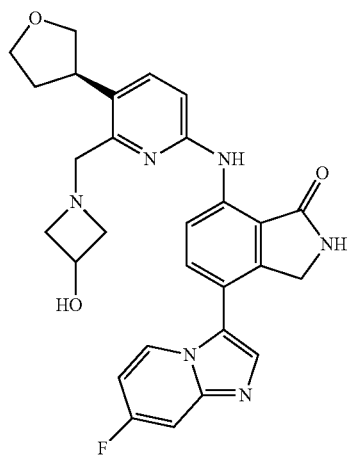 [SMILES: O=C1NCc2c(-c3cnc4cc(F)ccn34)ccc(Nc3ccc([C@H]4CCOC4)c(CN4CC(O)C4)n3)c21] |

TABLE 1-continued
Selected Compounds
| # | Structure |
|---|---|
| I-764 | 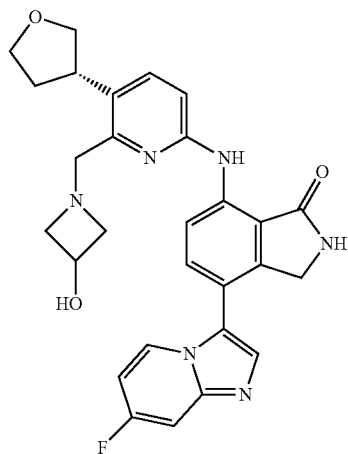 [SMILES: O=C1NCc2c(-c3cnc4cc(F)ccn34)ccc(Nc3ccc([C@@H]4CCOC4)c(CN4CC(O)C4)n3)c21] |
| I-765 | 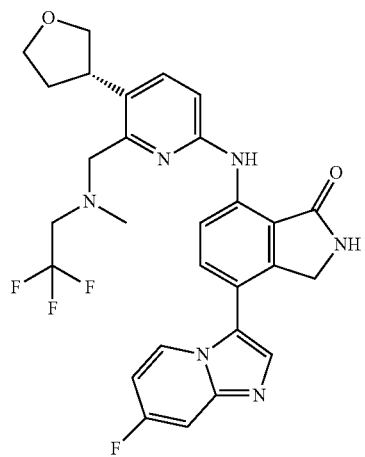 [SMILES: CN(Cc1nc(Nc2ccc(-c3cnc4cc(F)ccn34)c3c2C(=O)NC3)ccc1[C@@H]1CCOC1)CC(F)(F)F] |
| I-766 | 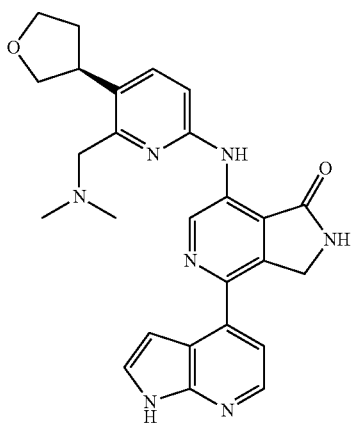 [SMILES: CN(C)Cc1nc(Nc2cnc(-c3ccnc4[nH]ccc34)c3c2C(=O)NC3)ccc1[C@@H]1CCOC1] |

TABLE 1-continued
| Selected Compounds | |
|---|---|
| # | Structure |
I-767
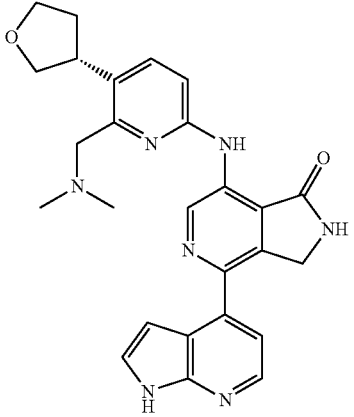 [SMILES: CN(C)Cc1nc(Nc2cnc(-c3ccnc4[nH]ccc34)c3c2C(=O)NC3)ccc1[C@H]1CCOC1]
I-768
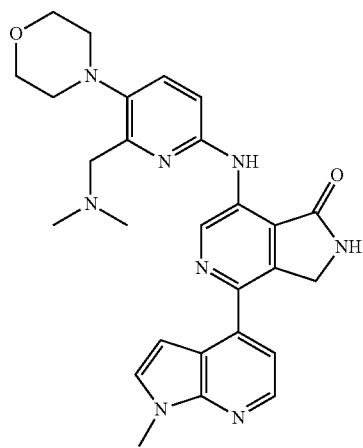 [SMILES: CN(C)Cc1nc(Nc2cnc(-c3ccnc4c3ccn4C)c3c2C(=O)NC3)ccc1N1CCOCC1]
I-769
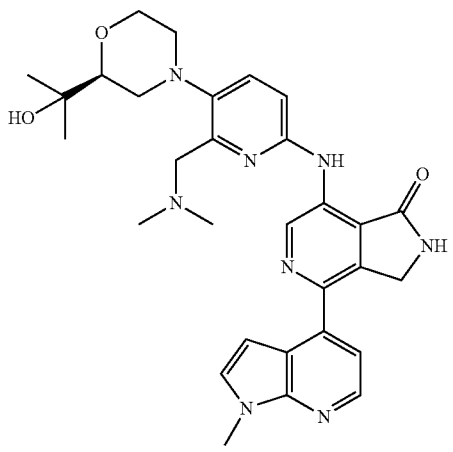 [SMILES: CN(C)Cc1nc(Nc2cnc(-c3ccnc4c3ccn4C)c3c2C(=O)NC3)ccc1N1CCO[C@H](C(C)(C)O)C1]

TABLE 1-continued
Selected Compounds
| # | Structure |
|---|---|
| I-770 | 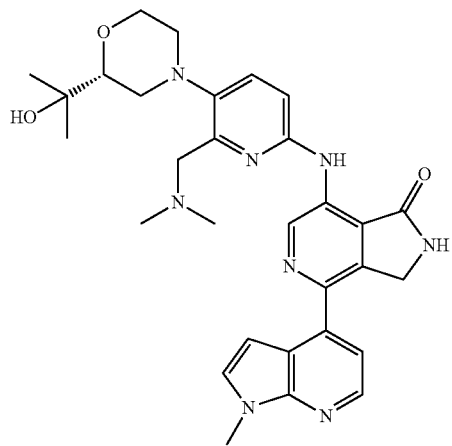 [SMILES: CN(C)Cc1nc(Nc2cnc(-c3ccnc4c3ccn4C)c3c2C(=O)NC3)ccc1N1CCO[C@@H](C(C)(C)O)C1] |
| I-771 | 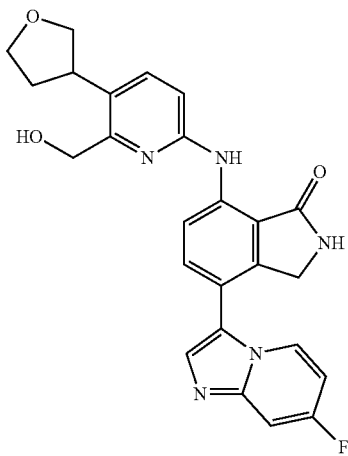 [SMILES: O=C1NCc2c(-c3cnc4cc(F)ccn34)ccc(Nc3ccc(C4CCOC4)c(CO)n3)c21] |
| I-772 | 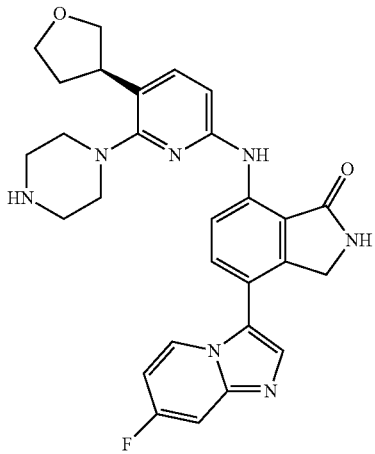 [SMILES: O=C1NCc2c(-c3cnc4cc(F)ccn34)ccc(Nc3ccc([C@H]4CCOC4)c(N4CCNCC4)n3)c21] |

TABLE 1-continued
Selected Compounds
| # | Structure |
|---|---|
| I-773 | 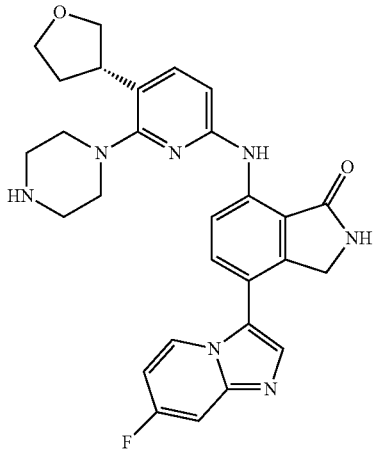 [SMILES: O=C1NCc2c(-c3cnc4cc(F)ccn34)ccc(Nc3ccc([C@@H]4CCOC4)c(N4CCNCC4)n3)c21] |
| I-774 | 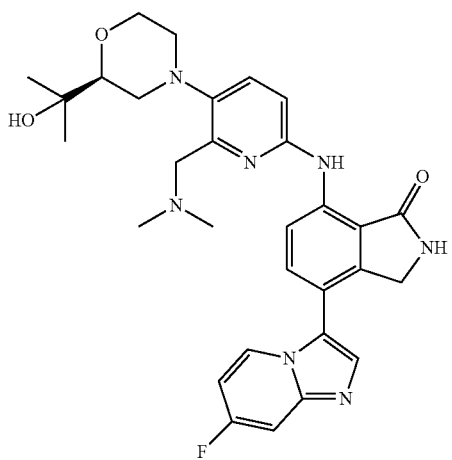 [SMILES: CN(C)Cc1nc(Nc2ccc(-c3cnc4cc(F)ccn34)c3c2C(=O)NC3)ccc1N1CCO[C@H](C(C)(C)O)C1] |
| I-775 | 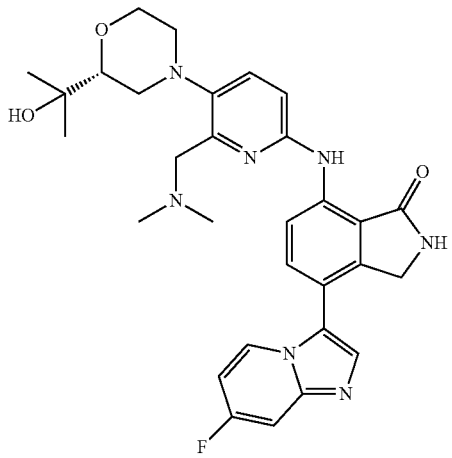 [SMILES: CN(C)Cc1nc(Nc2ccc(-c3cnc4cc(F)ccn34)c3c2C(=O)NC3)ccc1N1CCO[C@@H](C(C)(C)O)C1] |

TABLE 1-continued
Selected Compounds
| # | Structure |
|---|---|
| I-776 | 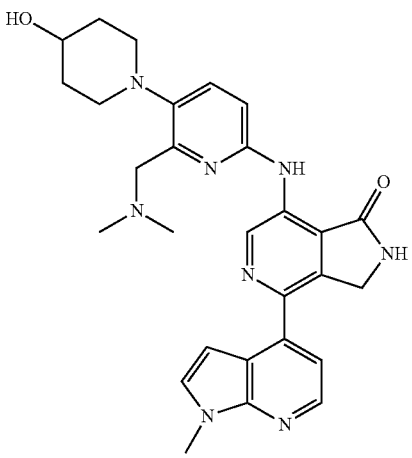 [SMILES: CN(C)Cc1nc(Nc2cnc(-c3ccnc4c3ccn4C)c3c2C(=O)NC3)ccc1N1CCC(O)CC1] |
| I-777 | 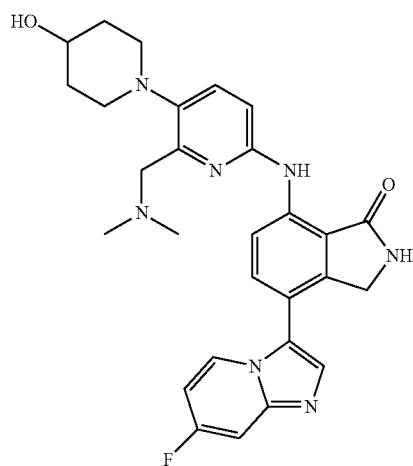 [SMILES: CN(C)Cc1nc(Nc2ccc(-c3cnc4cc(F)ccn34)c3c2C(=O)NC3)ccc1N1CCC(O)CC1] |
| I-778 | 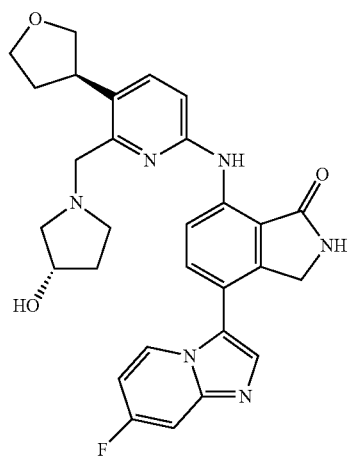 [SMILES: O=C1NCc2c(-c3cnc4cc(F)ccn34)ccc(Nc3ccc([C@H]4CCOC4)c(CN4CC[C@H](O)C4)n3)c21] |

661
662
TABLE 1-continued
Selected Compounds
| # | Structure |
|---|---|
| I-779 | 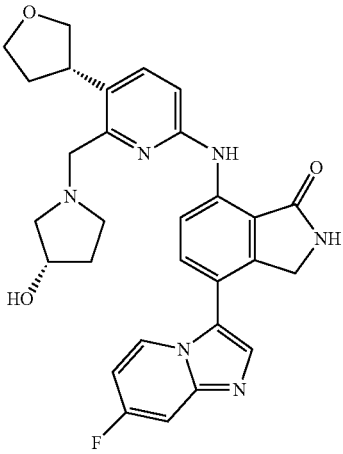 [SMILES: O=C1NCc2c(-c3cnc4cc(F)ccn34)ccc(Nc3ccc([C@@H]4CCOC4)c(CN4CC[C@H](O)C4)n3)c21] |
| I-780 | 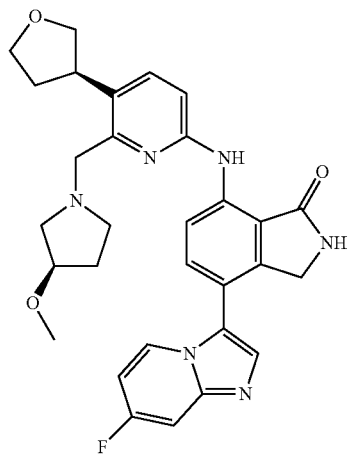 [SMILES: CO[C@@H]1CCN(Cc2nc(Nc3ccc(-c4cnc5cc(F)ccn45)c4c3C(=O)NC4)ccc2[C@H]2CCOC2)C1] |
| I-781 | 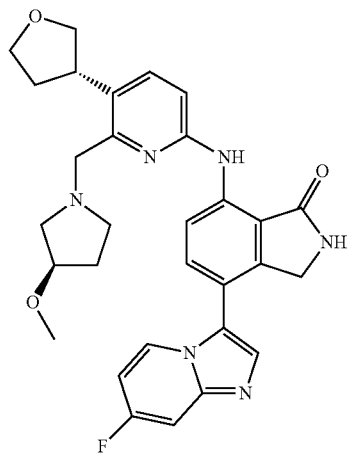 [SMILES: CO[C@@H]1CCN(Cc2nc(Nc3ccc(-c4cnc5cc(F)ccn45)c4c3C(=O)NC4)ccc2[C@@H]2CCOC2)C1] |

TABLE 1-continued
Selected Compounds
| # | Structure |
|---|---|
| I-782 | 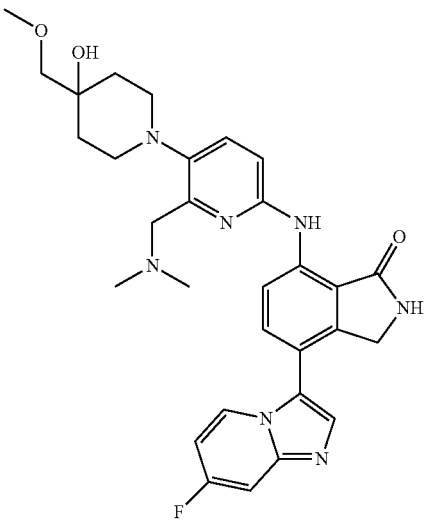 [SMILES: COCC1(O)CCN(c2ccc(Nc3ccc(-c4cnc5cc(F)ccn45)c4c3C(=O)NC4)nc2CN(C)C)CC1] |
| I-783 | 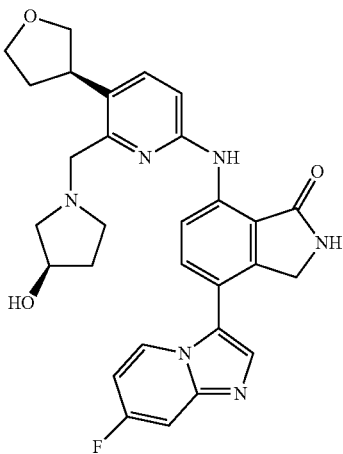 [SMILES: O=C1NCc2c(-c3cnc4cc(F)ccn34)ccc(Nc3ccc([C@H]4CCOC4)c(CN4CC[C@@H](O)C4)n3)c21] |
| I-784 | 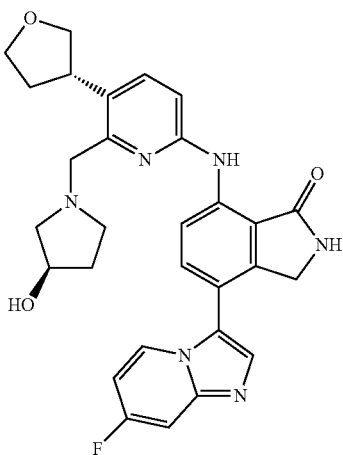 [SMILES: O=C1NCc2c(-c3cnc4cc(F)ccn34)ccc(Nc3ccc([C@@H]4CCOC4)c(CN4CC[C@@H](O)C4)n3)c21] |

TABLE 1-continued
Selected Compounds
| # | Structure |
|---|---|
| I-785 | 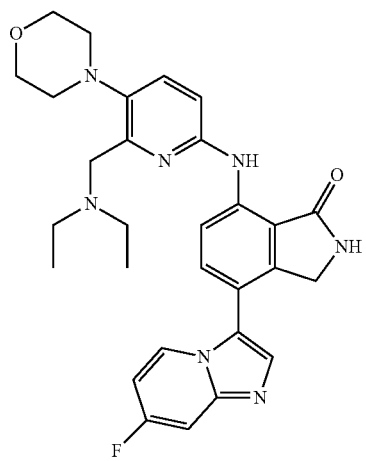 [SMILES: CCN(CC)Cc1nc(Nc2ccc(-c3cnc4cc(F)ccn34)c3c2C(=O)NC3)ccc1N1CCOCC1] |
| I-786 | 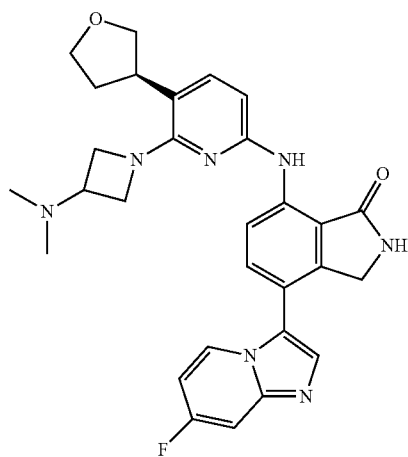 [SMILES: CN(C)C1CN(c2nc(Nc3ccc(-c4cnc5cc(F)ccn45)c4c3C(=O)NC4)ccc2[C@H]2CCOC2)C1] |
| I-787 | 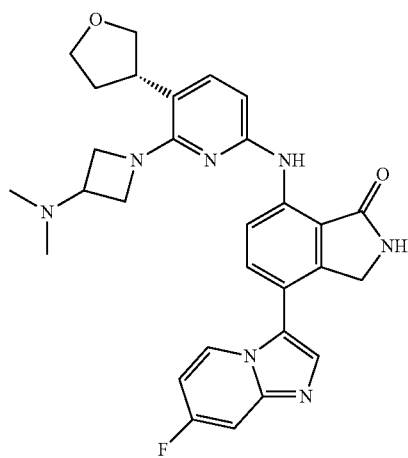 [SMILES: CN(C)C1CN(c2nc(Nc3ccc(-c4cnc5cc(F)ccn45)c4c3C(=O)NC4)ccc2[C@@H]2CCOC2)C1] |

TABLE 1-continued
Selected Compounds
| # | Structure |
|---|---|
| I-788 | 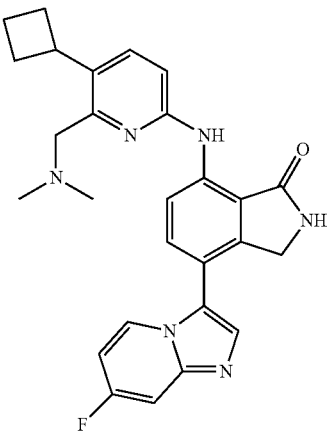 [SMILES: CN(C)Cc1nc(Nc2ccc(-c3cnc4cc(F)ccn34)c3c2C(=O)NC3)ccc1C1CCC1] |
| I-789 | 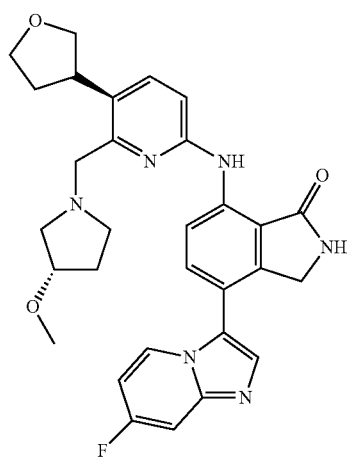 |
| I-790 | 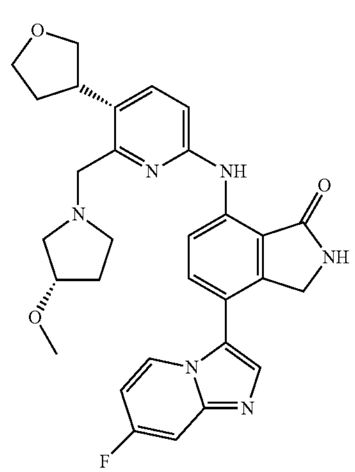 |

TABLE 1-continued
Selected Compounds
| # | Structure |
|---|---|
| I-791 | 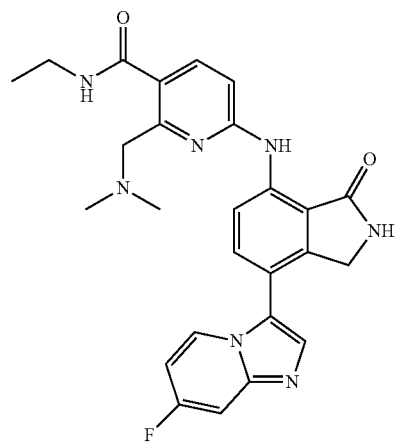 [SMILES: CCNC(=O)c1ccc(Nc2ccc(-c3cnc4cc(F)ccn34)c3c2C(=O)NC3)nc1CN(C)C] |
| I-792 | 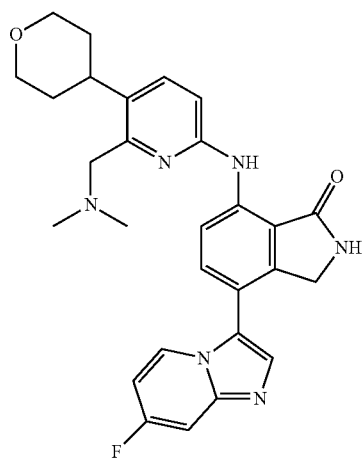 [SMILES: CN(C)Cc1nc(Nc2ccc(-c3cnc4cc(F)ccn34)c3c2C(=O)NC3)ccc1C1CCOCC1] |
| I-793 | 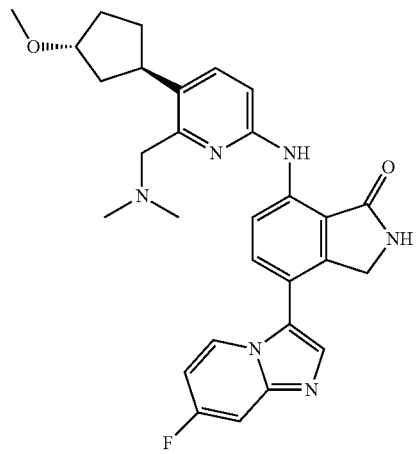 [SMILES: CO[C@@H]1CC[C@@H](c2ccc(Nc3ccc(-c4cnc5cc(F)ccn45)c4c3C(=O)NC4)nc2CN(C)C)C1] |

TABLE 1-continued
Selected Compounds
| # | Structure |
|---|---|
| I-794 | 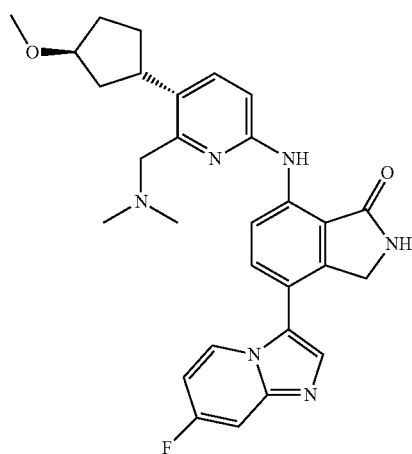 |
| I-795 | 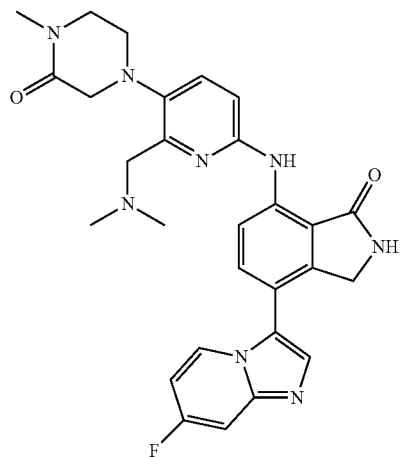 [SMILES: CN(C)Cc1nc(Nc2ccc(-c3cnc4cc(F)ccn34)c3c2C(=O)NC3)ccc1N1CCN(C)C(=O)C1] |
| I-796 | 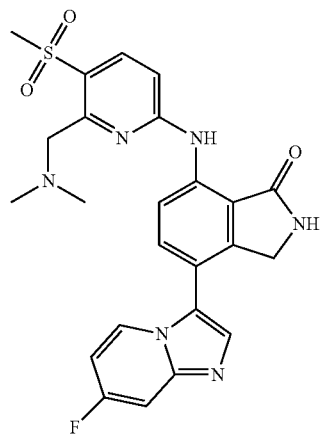 [SMILES: CN(C)Cc1nc(Nc2ccc(-c3cnc4cc(F)ccn34)c3c2C(=O)NC3)ccc1S(C)(=O)=O] |

673
674
TABLE 1-continued
Selected Compounds
| # | Structure |
|---|---|
| I-797 | 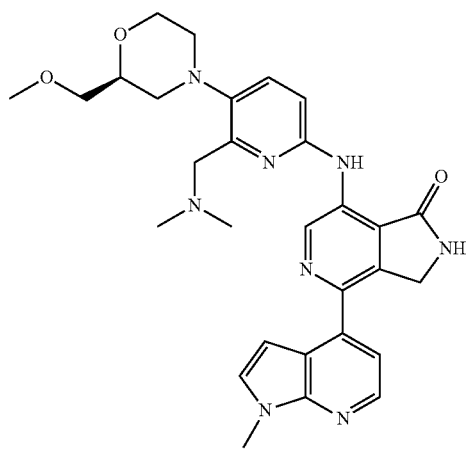 [SMILES: COC[C@@H]1CN(c2ccc(Nc3cnc(-c4ccnc5c4ccn5C)c4c3C(=O)NC4)nc2CN(C)C)CCO1] |
| I-798 | 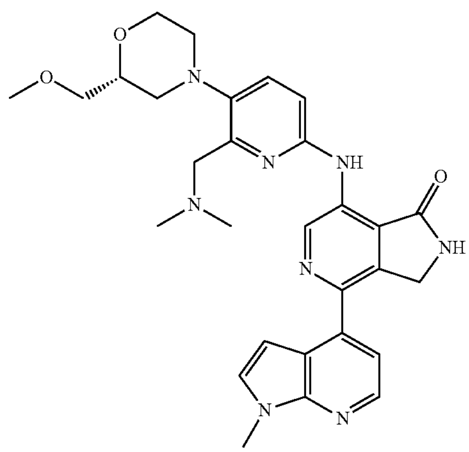 [SMILES: COC[C@H]1CN(c2ccc(Nc3cnc(-c4ccnc5c4ccn5C)c4c3C(=O)NC4)nc2CN(C)C)CCO1] |
| I-799 | 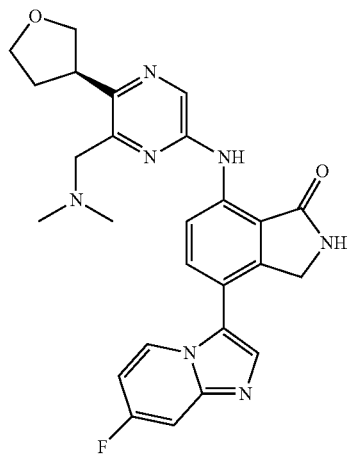 [SMILES: CN(C)Cc1nc(Nc2ccc(-c3cnc4cc(F)ccn34)c3c2C(=O)NC3)cnc1[C@H]1CCOC1] |

TABLE 1-continued
Selected Compounds
| # | Structure |
|---|---|
| I-800 | 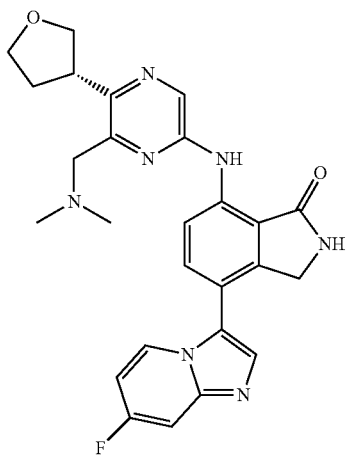 [SMILES: CN(C)Cc1nc(Nc2ccc(-c3cnc4cc(F)ccn34)c3c2C(=O)NC3)cnc1[C@@H]1CCOC1] |
| I-801 | 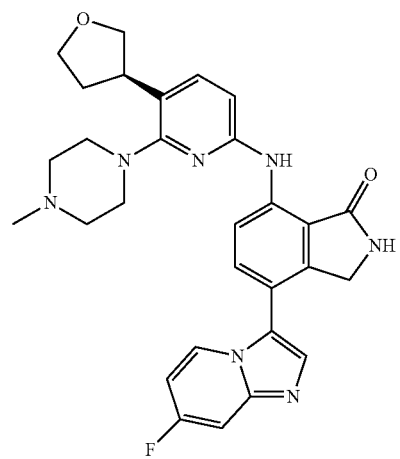 [SMILES: CN1CCN(c2nc(Nc3ccc(-c4cnc5cc(F)ccn45)c4c3C(=O)NC4)ccc2[C@H]2CCOC2)CC1] |
| I-802 | 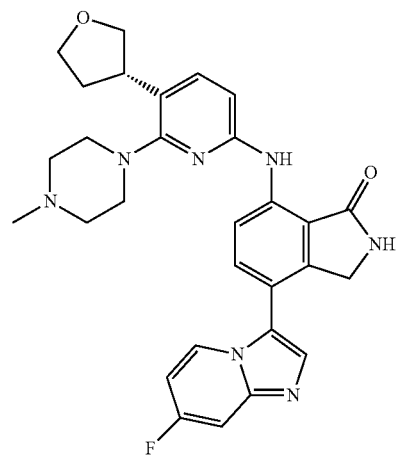 [SMILES: CN1CCN(c2nc(Nc3ccc(-c4cnc5cc(F)ccn45)c4c3C(=O)NC4)ccc2[C@@H]2CCOC2)CC1] |

677 678
TABLE 1-continued
Selected Compounds
| # | Structure |
|---|---|
| I-803 | 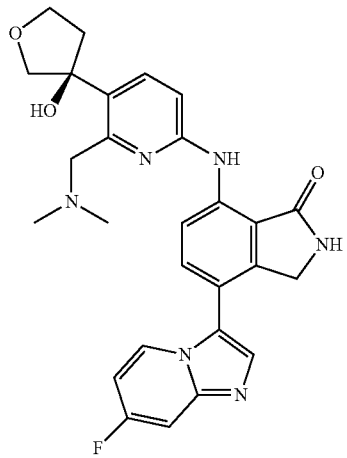 [SMILES: CN(C)Cc1nc(Nc2ccc(-c3cnc4cc(F)ccn34)c3c2C(=O)NC3)ccc1[C@@]1(O)CCOC1] |
| I-804 | 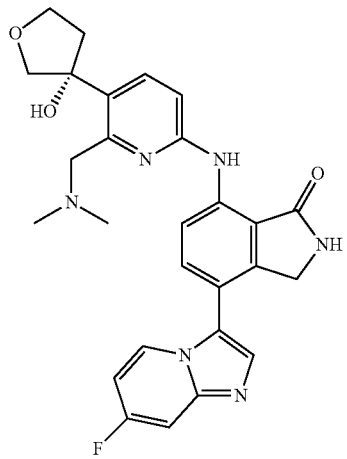 [SMILES: CN(C)Cc1nc(Nc2ccc(-c3cnc4cc(F)ccn34)c3c2C(=O)NC3)ccc1[C@]1(O)CCOC1] |
| I-805 | 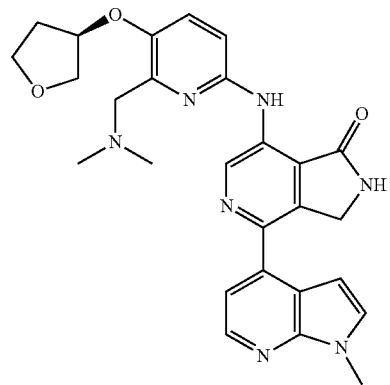 [SMILES: CN(C)Cc1nc(Nc2cnc(-c3ccnc4c3ccn4C)c3c2C(=O)NC3)ccc1O[C@@H]1CCOC1] |

TABLE 1-continued
Selected Compounds
| # | Structure |
|---|---|
| I-806 | 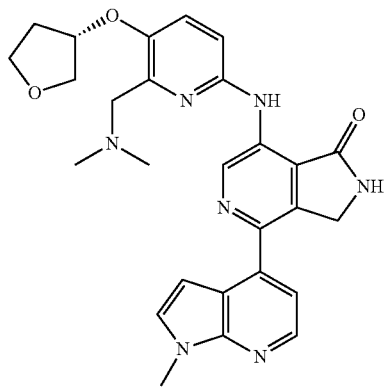 [SMILES: CN(C)Cc1nc(Nc2cnc(-c3ccnc4c3ccn4C)c3c2C(=O)NC3)ccc1O[C@H]1CCOC1] |
| I-807 | 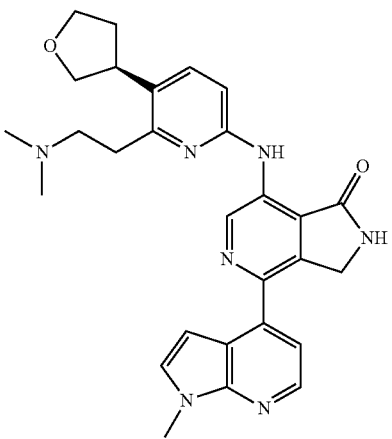 [SMILES: CN(C)CCc1nc(Nc2cnc(-c3ccnc4c3ccn4C)c3c2C(=O)NC3)ccc1[C@@H]1CCOC1] |
| I-808 | 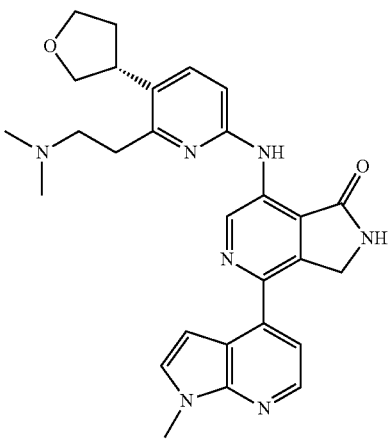 [SMILES: CN(C)CCc1nc(Nc2cnc(-c3ccnc4c3ccn4C)c3c2C(=O)NC3)ccc1[C@H]1CCOC1] |

TABLE 1-continued

Selected Compounds

| # | Structure |
|---|---|
| I-809 | 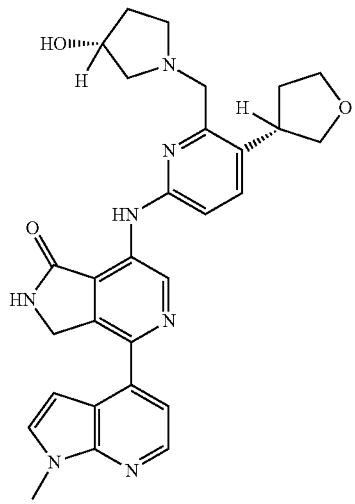 [SMILES: Cn1ccc2c(-c3ncc(Nc4ccc([C@@H]5CCOC5)c(CN5CC[C@@H](O)C5)n4)c4c3CNC4=O)ccnc21] |
| I-810 | 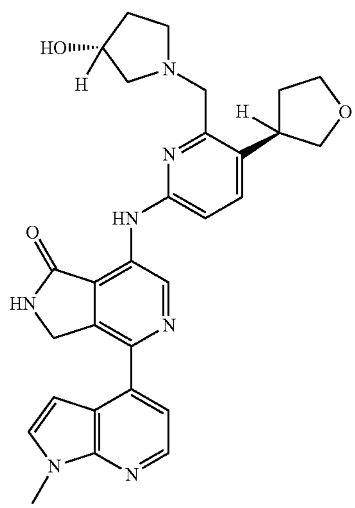 [SMILES: Cn1ccc2c(-c3ncc(Nc4ccc([C@H]5CCOC5)c(CN5CC[C@@H](O)C5)n4)c4c3CNC4=O)ccnc21] |
| I-811 | 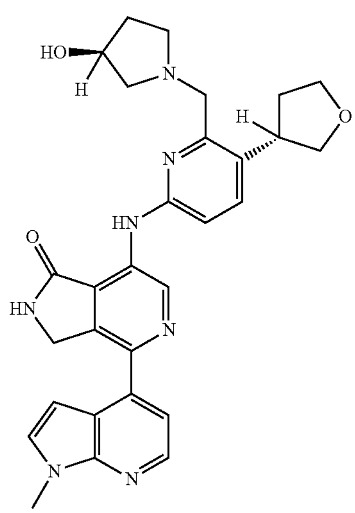 [SMILES: Cn1ccc2c(-c3ncc(Nc4ccc([C@@H]5CCOC5)c(CN5CC[C@H](O)C5)n4)c4c3CNC4=O)ccnc21] |

TABLE 1-continued

Selected Compounds

| # | Structure |
|---|---|
| I-812 | 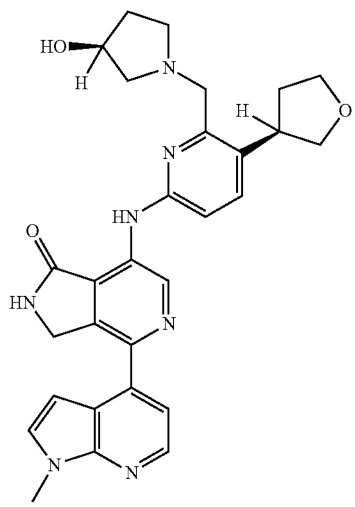 [SMILES: Cn1ccc2c(-c3ncc(Nc4ccc([C@H]5CCOC5)c(CN5CC[C@H](O)C5)n4)c4c3CNC4=O)ccnc21] |
| I-813 | 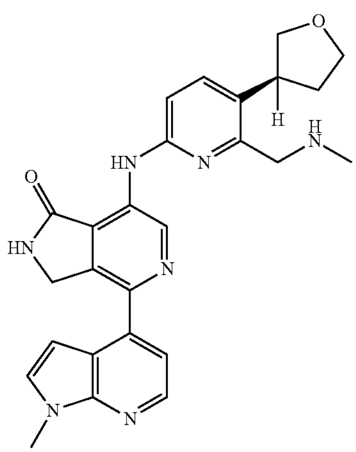 [SMILES: CNCc1nc(Nc2cnc(-c3ccnc4c3ccn4C)c3c2C(=O)NC3)ccc1[C@@H]1CCOC1] |
| I-814 | 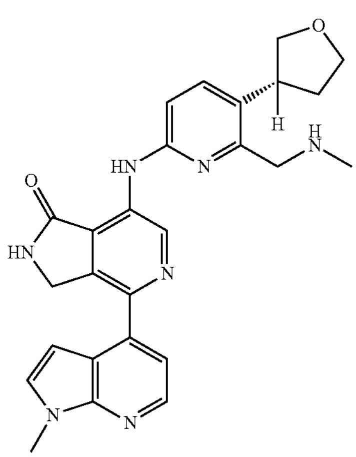 [SMILES: CNCc1nc(Nc2cnc(-c3ccnc4c3ccn4C)c3c2C(=O)NC3)ccc1[C@H]1CCOC1] |

TABLE 1-continued

| Selected Compounds | |
|---|---|
| # | Structure |
| I-815 | |
| I-816 | |
| I-817 | |

TABLE 1-continued

Selected Compounds

| # | Structure |
|---|---|
| I-818 | 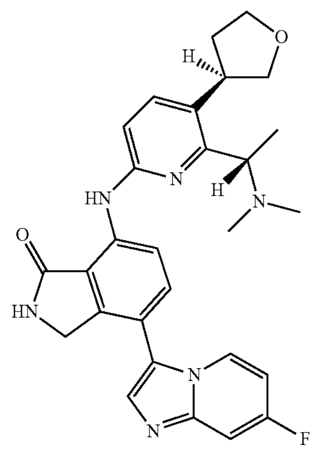 [SMILES: C[C@@H](c1nc(Nc2ccc(-c3cnc4cc(F)ccn34)c3c2C(=O)NC3)ccc1[C@H]1CCOC1)N(C)C] |
| I-819 | 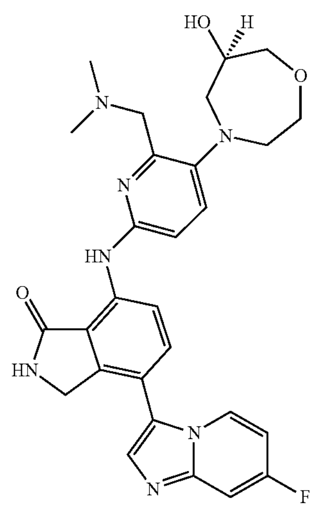 [SMILES: CN(C)Cc1nc(Nc2ccc(-c3cnc4cc(F)ccn34)c3c2C(=O)NC3)ccc1N1CCOC[C@H](O)C1] |
| I-820 | 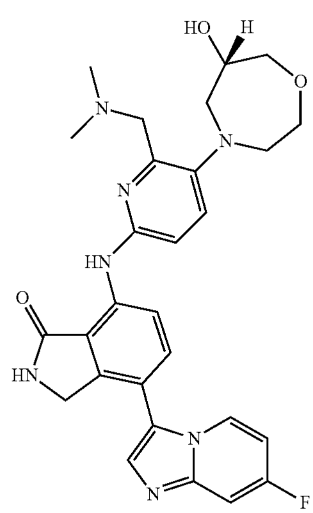 [SMILES: CN(C)Cc1nc(Nc2ccc(-c3cnc4cc(F)ccn34)c3c2C(=O)NC3)ccc1N1CCOC[C@@H](O)C1] |

TABLE 1-continued
Selected Compounds
| # | Structure |
|---|---|
| I-821 | 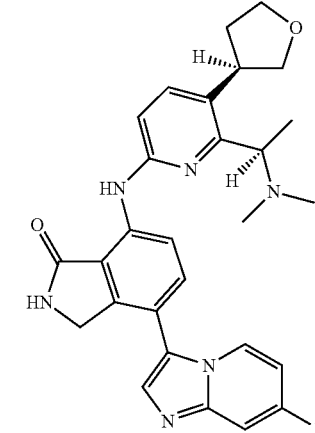 |
| I-822 | 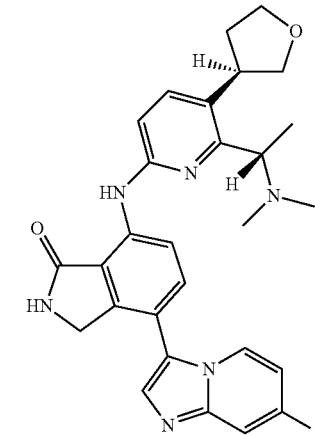 |
| I-823 | 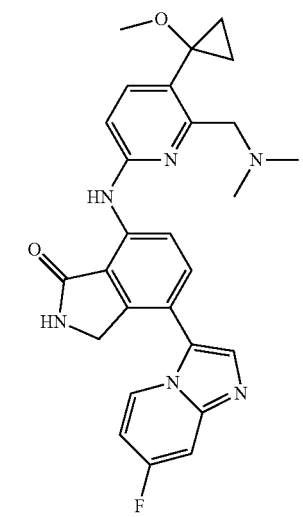 [SMILES: COC1(c2ccc(Nc3ccc(-c4cnc5cc(F)ccn45)c4c3C(=O)NC4)nc2CN(C)C)CC1] |

TABLE 1-continued

Selected Compounds

| # | Structure |
|---|---|
| I-824 | 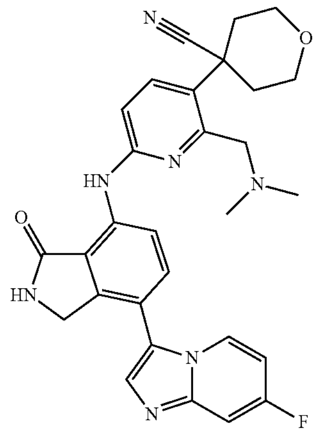 [SMILES: CN(C)Cc1nc(Nc2ccc(-c3cnc4cc(F)ccn34)c3c2C(=O)NC3)ccc1C1(C#N)CCOCC1] |
| I-825 | 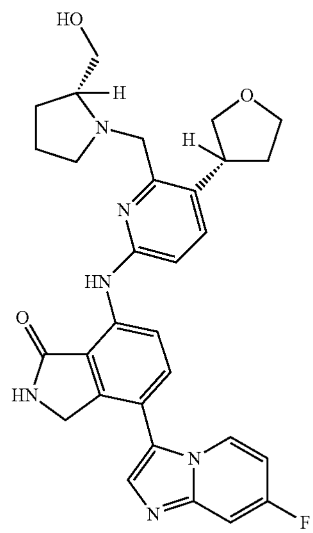 [SMILES: O=C1NCc2c(-c3cnc4cc(F)ccn34)ccc(Nc3ccc([C@H]4CCOC4)c(CN4CCC[C@@H]4CO)n3)c21] |
| I-826 | 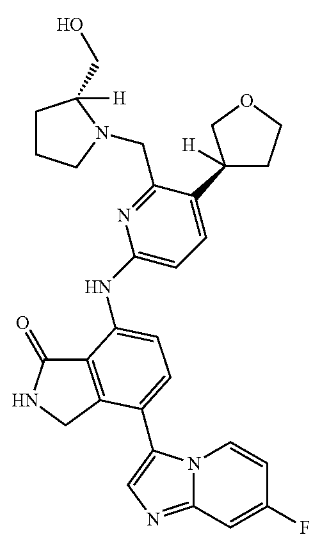 [SMILES: O=C1NCc2c(-c3cnc4cc(F)ccn34)ccc(Nc3ccc([C@@H]4CCOC4)c(CN4CCC[C@@H]4CO)n3)c21] |

TABLE 1-continued
| Selected Compounds | |
|---|---|
| # | Structure |
| I-827 | 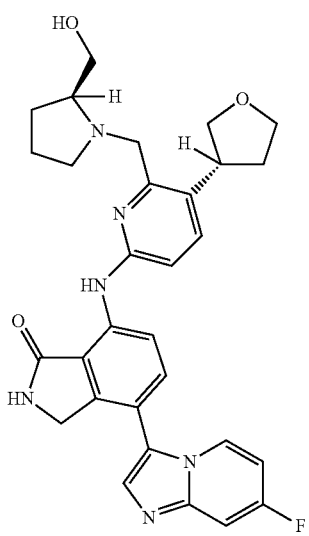 [SMILES: O=C1NCc2c(-c3cnc4cc(F)ccn34)ccc(Nc3ccc([C@H]4CCOC4)c(CN4CCC[C@H]4CO)n3)c21] |
| I-828 | 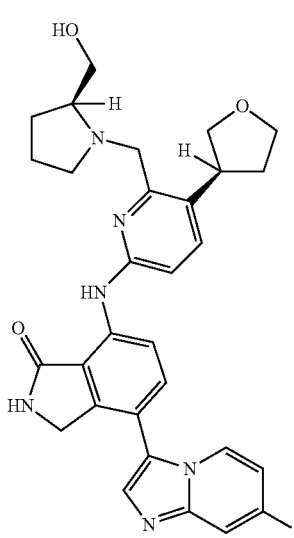 |
| I-829 | 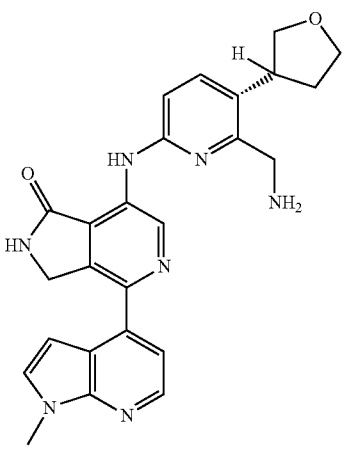 |

TABLE 1-continued
Selected Compounds
| # | Structure |
|---|---|
| I-830 | 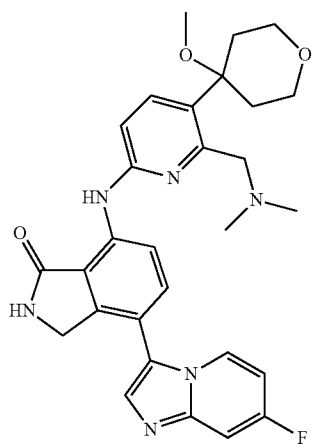 [SMILES: COC1(c2ccc(Nc3ccc(-c4cnc5cc(F)ccn45)c4c3C(=O)NC4)nc2CN(C)C)CCOCC1] |
| I-831 | 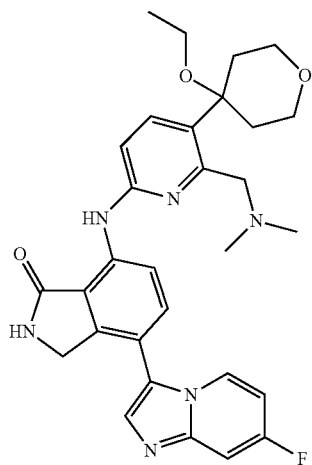 [SMILES: CCOC1(c2ccc(Nc3ccc(-c4cnc5cc(F)ccn45)c4c3C(=O)NC4)nc2CN(C)C)CCOCC1] |
| I-832 | 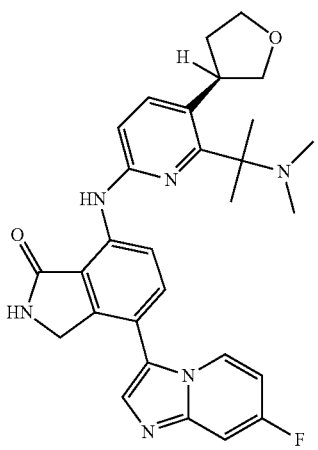 [SMILES: CN(C)C(C)(C)c1nc(Nc2ccc(-c3cnc4cc(F)ccn34)c3c2C(=O)NC3)ccc1[C@H]1CCOC1] |

TABLE 1-continued
Selected Compounds
| # | Structure |
|---|---|
| I-833 | 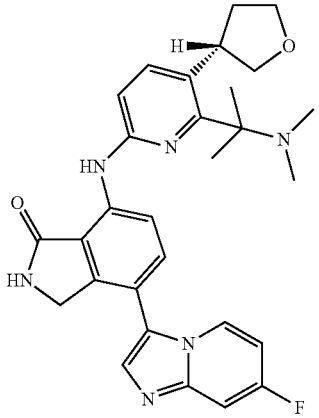 [SMILES: CN(C)C(C)(C)c1nc(Nc2ccc(-c3cnc4cc(F)ccn34)c3c2C(=O)NC3)ccc1[C@@H]1CCOC1] |
| I-834 | 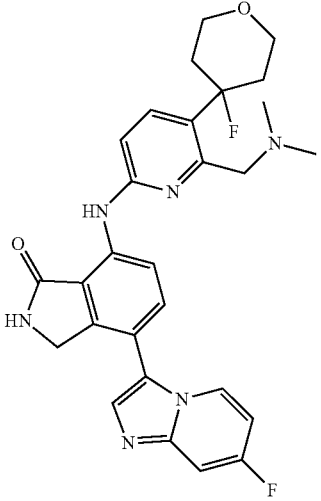 [SMILES: CN(C)Cc1nc(Nc2ccc(-c3cnc4cc(F)ccn34)c3c2C(=O)NC3)ccc1C1(F)CCOCC1] |
| I-835 | 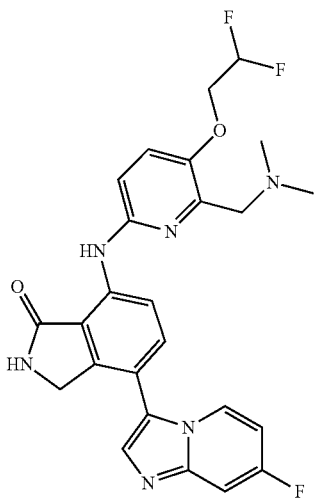 [SMILES: CN(C)Cc1nc(Nc2ccc(-c3cnc4cc(F)ccn34)c3c2C(=O)NC3)ccc1OCC(F)F] |

TABLE 1-continued
Selected Compounds
| # | Structure |
|---|---|
| I-836 | 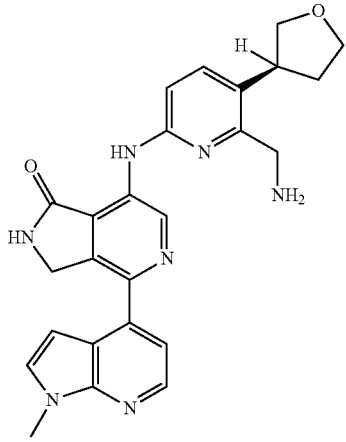 [SMILES: Cn1ccc2c(-c3ncc(Nc4ccc([C@@H]5CCOC5)c(CN)n4)c4c3CNC4=O)ccnc21] |
| I-837 | 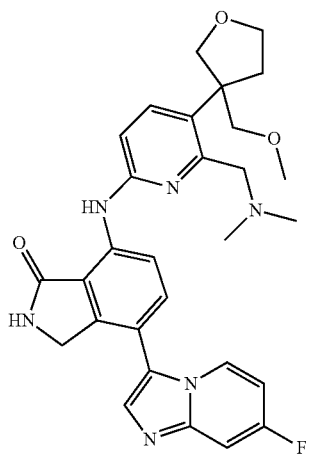 [SMILES: COCC1(c2ccc(Nc3ccc(-c4cnc5cc(F)ccn45)c4c3C(=O)NC4)nc2CN(C)C)CCOC1] |
| I-838 | 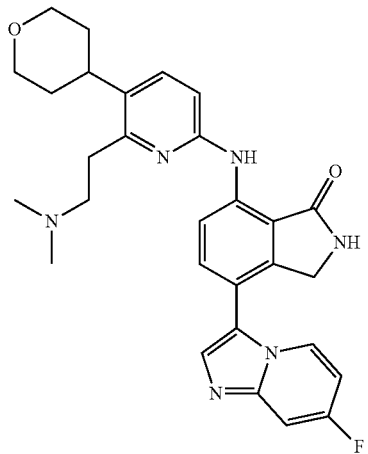 [SMILES: CN(C)CCc1nc(Nc2ccc(-c3cnc4cc(F)ccn34)c3c2C(=O)NC3)ccc1C1CCOCC1] |

TABLE 1-continued

Selected Compounds

| # | Structure |
|---|---|
| I-839 | 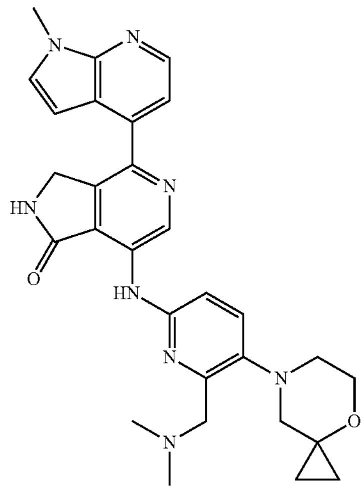 [SMILES: CN(C)Cc1nc(Nc2cnc(-c3ccnc4c3ccn4C)c3c2C(=O)NC3)ccc1N1CCOC2(CC2)C1] |
| I-840 | 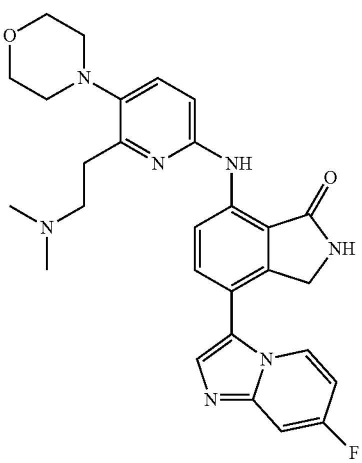 [SMILES: CN(C)CCc1nc(Nc2ccc(-c3cnc4cc(F)ccn34)c3c2C(=O)NC3)ccc1N1CCOCC1] |
| I-841 | 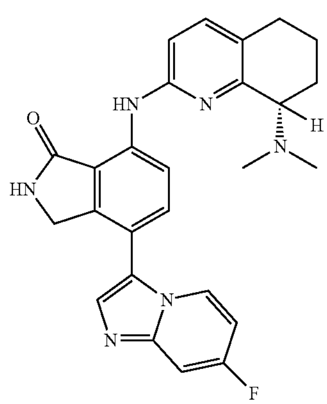 [SMILES: CN(C)[C@H]1CCCc2ccc(Nc3ccc(-c4cnc5cc(F)ccn45)c4c3C(=O)NC4)nc21] |

TABLE 1-continued
Selected Compounds
| # | Structure |
|---|---|
| I-842 | 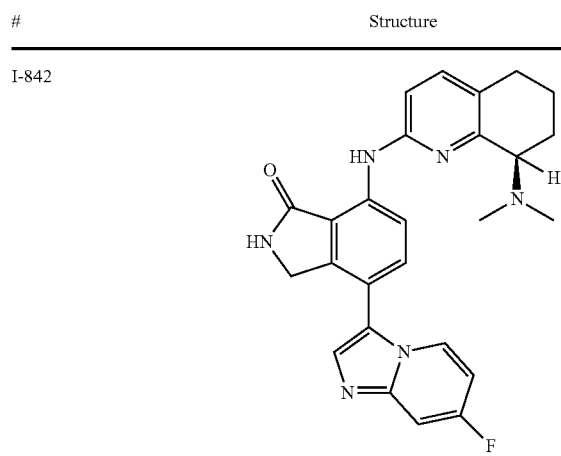 |
| I-843 | 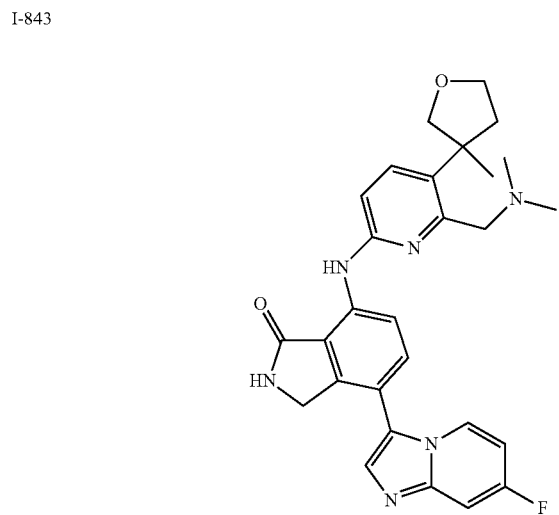 |
| I-844 | 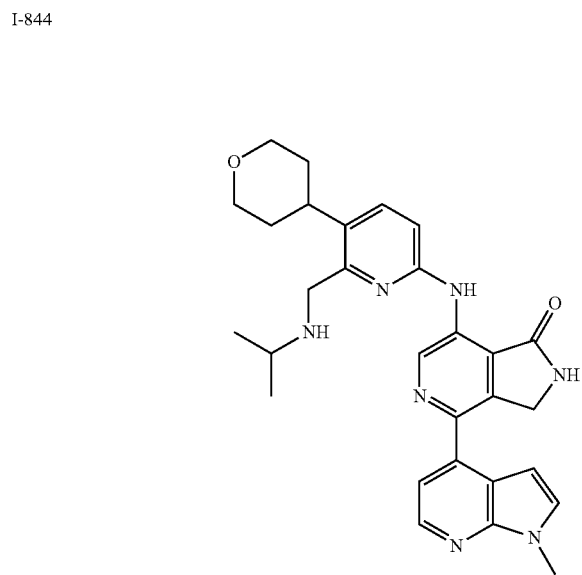 |

TABLE 1-continued
Selected Compounds
| # | Structure |
|---|---|
| I-845 | 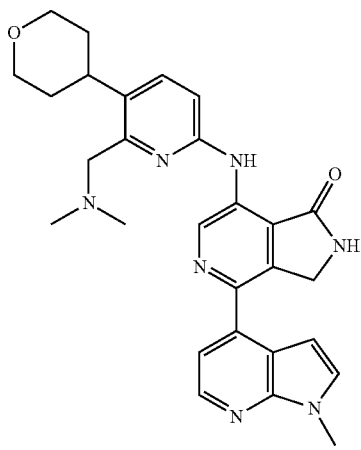 [SMILES: CN(C)Cc1nc(Nc2cnc(-c3ccnc4c3ccn4C)c3c2C(=O)NC3)ccc1C1CCOCC1] |
| I-846 | 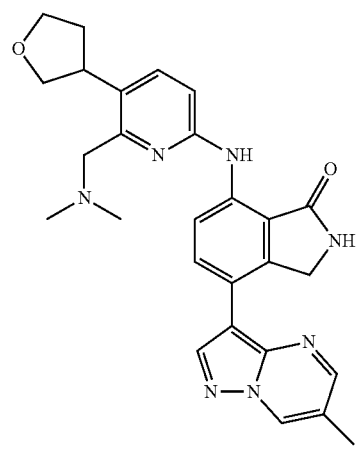 [SMILES: Cc1cnc2c(-c3ccc(Nc4ccc(C5CCOC5)c(CN(C)C)n4)c4c3CNC4=O)cnn2c1] |
| I-847 | 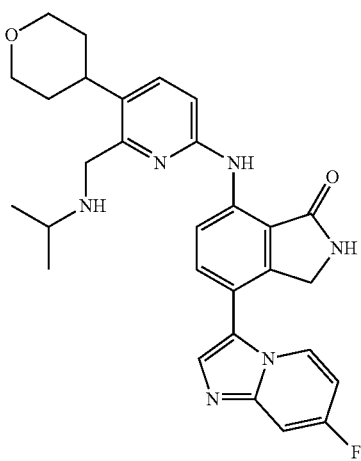 [SMILES: CC(C)NCc1nc(Nc2ccc(-c3cnc4cc(F)ccn34)c3c2C(=O)NC3)ccc1C1CCOCC1] |

TABLE 1-continued
Selected Compounds
| # | Structure |
|---|---|
| I-848 | 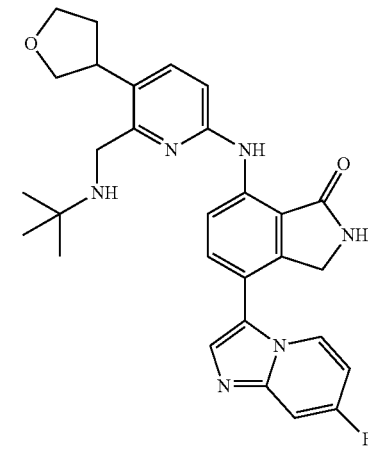 [SMILES: CC(C)(C)NCc1nc(Nc2ccc(-c3cnc4cc(F)ccn34)c3c2C(=O)NC3)ccc1C1CCOC1] |
| I-849 | 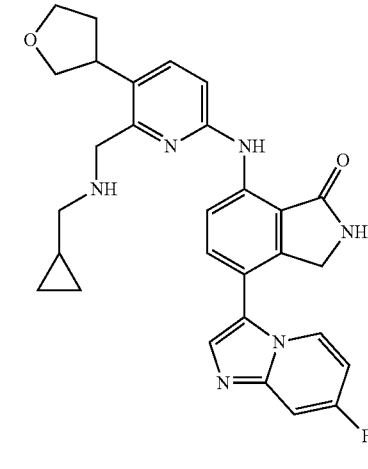 [SMILES: O=C1NCc2c(-c3cnc4cc(F)ccn34)ccc(Nc3ccc(C4CCOC4)c(CNCC4CC4)n3)c21] |
| I-850 | 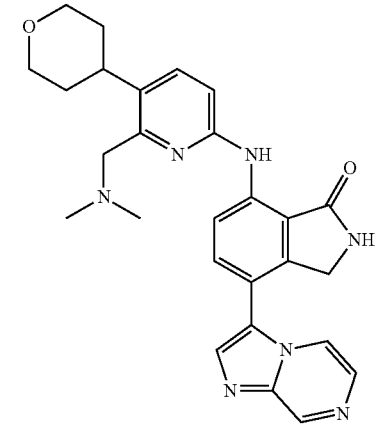 [SMILES: CN(C)Cc1nc(Nc2ccc(-c3cnc4cnccn34)c3c2C(=O)NC3)ccc1C1CCOCC1] |

TABLE 1-continued
Selected Compounds
| # | Structure |
|---|---|
| I-851 | 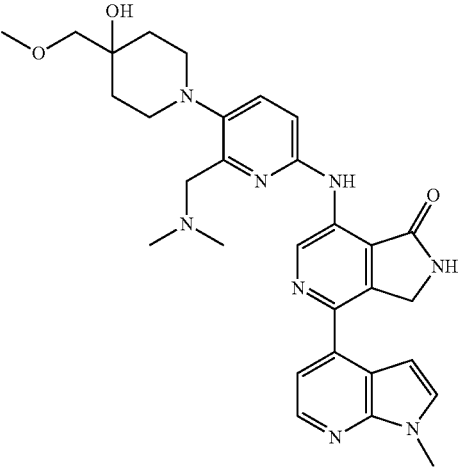 [SMILES: COCC1(O)CCN(c2ccc(Nc3cnc(-c4ccnc5c4ccn5C)c4c3C(=O)NC4)nc2CN(C)C)CC1] |
| I-852 | 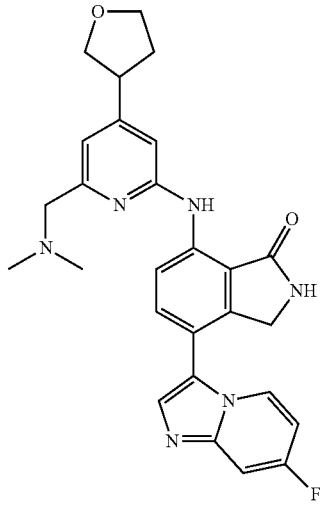 [SMILES: CN(C)Cc1cc(C2CCOC2)cc(Nc2ccc(-c3cnc4cc(F)ccn34)c3c2C(=O)NC3)n1] |
| I-853 | 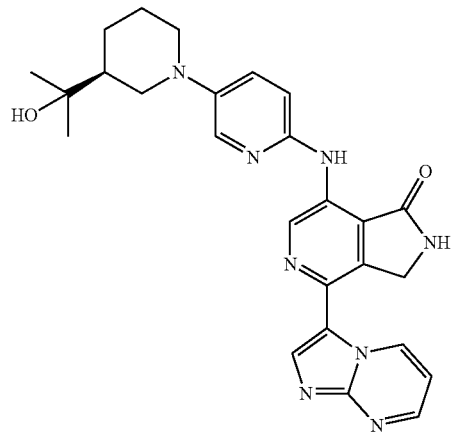 [SMILES: CC(C)(O)[C@H]1CCCN(c2ccc(Nc3cnc(-c4cnc5ncccn45)c4c3C(=O)NC4)nc2)C1] |

TABLE 1-continued

Selected Compounds

| # | Structure |
|---|-----------|
| I-854 | 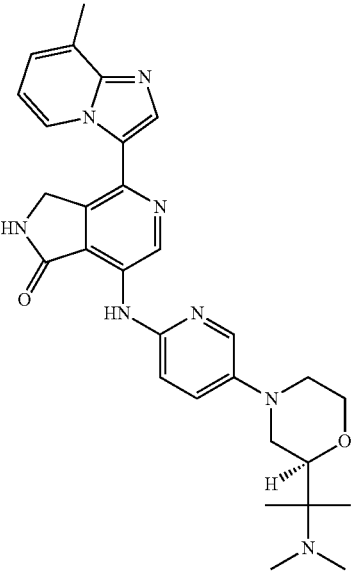 [SMILES: Cc1cccn2c(-c3ncc(Nc4ccc(N5CCO[C@@H](C(C)(C)N(C)C)C5)cn4)c4c3CNC4=O)cnc12] |
| I-855 | 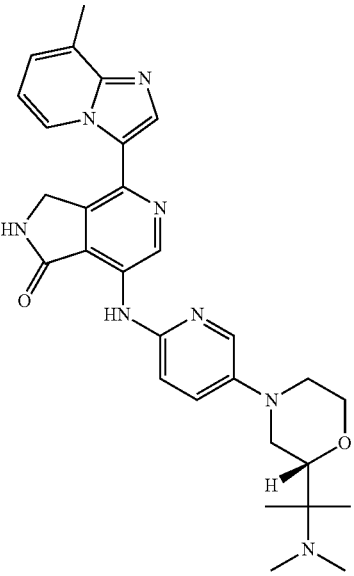 [SMILES: Cc1cccn2c(-c3ncc(Nc4ccc(N5CCO[C@H](C(C)(C)N(C)C)C5)cn4)c4c3CNC4=O)cnc12] |

In some embodiments, the present invention provides a compound set forth in Table 1, above, or a pharmaceutically acceptable salt thereof. In some embodiments, the present invention provides a compound set forth in Table 1, above. In some embodiments, the present invention provides a pharmaceutical composition comprising a compound set forth in Table 1 above, or a pharmaceutically acceptable salt thereof, together with a pharmaceutically acceptable carrier, excipient, or diluent.

In some embodiments, the present invention provides a compound of formula I as defined above, or a pharmaceutically acceptable salt thereof, or a pharmaceutical composition comprising a compound of formula I as defined above, or a pharmaceutically acceptable salt thereof, and a pharmaceutically acceptable carrier, adjuvant, or vehicle for use as a medicament.

In some embodiments, the invention also provides compounds of formula I described herein or pharmaceutical compositions described herein for use in a method for inhibiting HPK1 as described herein, in a method for enhancing an immune response in a subject in need thereof as described herein and/or in a method for treating a HPK1-dependent disorder as described herein.

In some embodiments, the invention also provides compounds of formula I described herein or pharmaceutical compositions described herein for use in a method for inhibiting HPK1 as described herein.

In some embodiments, the invention also provides compounds of formula I described herein or pharmaceutical compositions described herein for use in a method for enhancing an immune response in a subject in need thereof as described herein.

In some embodiments, the invention also provides compounds of formula I described herein or pharmaceutical compositions described herein for use in a method for treating a HPK1-dependent disorder as described herein.

In some embodiments, the invention also provides the use of a compound of formula I described herein or a pharmaceutical composition described herein for the manufacture of a medicament for inhibiting HPK1, a medicament for enhancing an immune response in a subject in need thereof and/or a medicament for treating a HPK1-dependent disorder.

In some embodiments, the invention also provides the use of a compound of formula I described herein or a pharmaceutical composition described herein for the manufacture of a medicament for inhibiting HPK1.

In some embodiments, the invention also provides the use of a compound of formula I described herein or a pharmaceutical composition described herein for the manufacture of a medicament for enhancing an immune response in a subject in need thereof.

In some embodiments, the invention also provides the use of a compound of formula I described herein or a pharmaceutical composition described herein for the manufacture of a medicament treating a HPK1-dependent disorder.

In some embodiments, the invention also provides the use of compounds of formula I described herein or pharmaceutical compositions described herein in a method for inhibiting HPK1 as described herein, in a method for enhancing an immune response in a subject in need thereof as described herein and/or in a method for treating a HPK1-dependent disorder as described herein.

In some embodiments, the invention also provides the use of compounds of formula I described herein or pharmaceutical compositions described herein in a method for inhibiting HPK1 as described herein.

In some embodiments, the invention also provides the use of compounds of formula I described herein or pharmaceutical compositions described herein in a method for enhancing an immune response in a subject in need thereof as described herein.

In some embodiments, the invention also provides the use of compounds of formula I described herein or pharmaceutical compositions described herein in a method for treating a HPK1-dependent disorder as described herein.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably inhibit HPK1, or a mutant thereof, in a biological sample or in a patient. In certain embodiments, the amount of compound in compositions of this invention is such that is effective to measurably inhibit HPK1, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily active metabolite or residue thereof.

As used herein, the term "inhibitorily active metabolite or residue thereof" means that a metabolite or residue thereof is also an inhibitor of HPK1, or a mutant thereof.

The subject matter disclosed herein includes prodrugs, metabolites, derivatives, and pharmaceutically acceptable salts of compounds of the invention. Metabolites include compounds produced by a process comprising contacting a compound of the invention with a mammal for a period of time sufficient to yield a metabolic product thereof. If the compound of the invention is a base, the desired pharmaceutically acceptable salt may be prepared by any suitable method available in the art, for example, treatment of the free base with an inorganic acid, such as hydrochloric acid, hydrobromic acid, sulfuric acid, nitric acid, methanesulfonic acid, phosphoric acid and the like, or with an organic acid, such as acetic acid, maleic acid, succinic acid, mandelic acid, fumaric acid, malonic acid, pyruvic acid, oxalic acid, glycolic acid, salicylic acid, a pyranosidyl acid, such as glucuronic acid or galacturonic acid, an alpha hydroxy acid, such as citric acid or tartaric acid, an amino acid, such as aspartic acid or glutamic acid, an aromatic acid, such as benzoic acid or cinnamic acid, a sulfonic acid, such as p-toluenesulfonic acid or ethanesulfonic acid, or the like. If the compound of the invention is an acid, the desired pharmaceutically acceptable salt may be prepared by any suitable method, for example, treatment of the free acid with an inorganic or organic base, such as an amine (primary, secondary or tertiary), an alkali metal hydroxide or alkaline earth metal hydroxide, or the like. Illustrative examples of suitable salts include, but are not limited to, organic salts derived from amino acids, such as glycine and arginine, ammonia, primary, secondary, and tertiary amines, and cyclic amines, such as piperidine, morpholine and piperazine, and inorganic salts derived from sodium, calcium, potassium, magnesium, manganese, iron, copper, zinc, aluminum and lithium.

A compound of the invention can be in the form of a "prodrug," which includes compounds with moieties which can be metabolized in vivo. Generally, the prodrugs are metabolized in vivo by esterases or by other mechanisms to active drugs. Examples of prodrugs and their uses are well known in the art (See, e.g., Berge et al. (1977) "Pharmaceutical Salts", J. Pharm. Sci. 66:1-19). The prodrugs can be prepared in situ during the final isolation and purification of the compounds, or by separately reacting the purified compound in its free acid form or hydroxyl with a suitable esterifying agent. Hydroxyl groups can be converted into esters via treatment with a carboxylic acid. Examples of prodrug moieties include substituted and unsubstituted, branch or unbranched lower alkyl ester moieties, (e.g., propionic acid esters), lower alkenyl esters, di-lower alkyl-amino lower-alkyl esters (e.g., dimethylaminoethyl ester), acylamino lower alkyl esters (e.g., acetyloxymethyl ester), acyloxy lower alkyl esters (e.g., pivaloyloxymethyl ester), aryl esters (phenyl ester), aryl-lower alkyl esters (e.g., benzyl ester), substituted (e.g., with methyl, halo, or methoxy substituents) aryl and aryl-lower alkyl esters, amides, lower-alkyl amides, di-lower alkyl amides, and hydroxy amides. Prodrugs which are converted to active forms through other mechanisms in vivo are also included. In aspects, the compounds of the invention are prodrugs of any of the formulae herein.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

The compounds and compositions described herein are generally useful for the inhibition of kinase activity of one or more enzymes. In some embodiments the kinase inhibited by the compounds and methods of the invention is HPK1.

The presently disclosed compounds find use in inhibiting the activity of the enzyme HPK1. HPK1 is a member of the germinal center kinase subfamily of Ste20-related serine/threonine kinases. HPK1 functions as a MAP4K by phosphorylating and activating MAP3K proteins, including MEKK1, MLK3 and TAK1, leading to the activation of the MAPK Jnk.

In one embodiment, the subject matter disclosed herein is directed to a method of inhibiting HPK1, the method comprising contacting HPK1 with an effective amount of a compound of the invention or a pharmaceutical composition described herein.

In certain embodiments, the subject matter disclosed herein is directed to a method for enhancing an immune response in a subject in need thereof, wherein the method comprises administering to the subject an effective amount of a compound of the invention or a pharmaceutical composition described herein. In certain aspects of this embodiment, the T cells in the subject have at least one of enhanced priming, enhanced activation, enhanced migration, enhanced proliferation, enhanced survival, and enhanced cytolytic activity relative to prior to the administration of the compound or pharmaceutical composition. In certain aspects of this embodiment, the T cell activation is characterized by an elevated frequency of γ-IFN+CD8 T cells or enhanced levels of IL-2 or granzyme B production by T cells relative to prior to administration of the compound or pharmaceutical composition. In certain aspects of this embodiment, the number of T cells is elevated relative to prior to administration of the compound or pharmaceutical composition. In certain aspects of this embodiment, the T cell is an antigen-specific CD8 T cell. In certain aspects of this embodiment, the antigen presenting cells in the subject have enhanced maturation and activation relative prior to the administration of the compound or pharmaceutical composition. In certain aspects of this embodiment, the antigen presenting cells are dendritic cells. In certain aspects of this embodiment, the maturation of the antigen presenting cells is characterized by increased frequency of CD83+ dendritic cells. In certain aspects of this embodiment, the activation of the antigen presenting cells is characterized by elevated expression of CD80 and CD86 on dendritic cells.

The presently disclosed compounds bind directly to HPK1 and inhibit its kinase activity. In some embodiments, the presently disclosed compounds reduce, inhibit, or otherwise diminish the HPK1-mediated phosphorylation of SLP76 and/or Gads.

The presently disclosed compounds may or may not be a specific HPK1 antagonist. A specific HPK1 antagonist reduces the biological activity of HPK1 by an amount that is statistically greater than the inhibitory effect of the antagonist on any other protein (e.g., other serine/threonine kinases). In certain embodiments, the presently disclosed compounds specifically inhibit the serine/threonine kinase activity of HPK1. In some of these embodiments, the $IC_{50}$ of the HPK1 antagonist for HPK1 is about 90%, 80%, 70%, 60%, 50%, 40%, 30%, 20%, 10%, 0.1%, 0.01%, 0.001%, or less of the $IC_{50}$ of the HPK1 antagonist for another serine/threonine kinase or other type of kinase (e.g., tyrosine kinase).

The presently disclosed compounds can be used in a method for inhibiting HPK1. Such methods comprise contacting HPK1 with an effective amount of a presently disclosed compound. By "contact" is intended bringing the compound within close enough proximity to an isolated HPK1 enzyme or a cell expressing HPK1 (e.g., T cell, B cell, dendritic cell) such that the compound is able to bind to and inhibit the activity of HPK1. The compound can be contacted with HPK1 in vitro or in vivo via administration of the compound to a subject.

Any method known in the art to measure the kinase activity of HPK1 may be used to determine if HPK1 has been inhibited, including in vitro kinase assays, immunoblots with antibodies specific for phosphorylated targets of HPK1, such as SLP76 and Gads, or the measurement of a downstream biological effect of HPK1 kinase activity, such as the recruitment of 14-3-3 proteins to phosphorylated SLP7 and Gads, release of the SLP76-Gads-14-3-3 complex from LAT-containing microclusters, or T or B cell activation.

The presently disclosed compounds can be used to treat a HPK1-dependent disorder. As used herein, a "HPK1-dependent disorder" is a pathological condition in which HPK1 activity is necessary for the genesis or maintenance of the pathological condition. In some embodiments, the HPK1-dependent disorder is cancer.

The presently disclosed compounds also find use in enhancing an immune response in a subject in need thereof. Such methods comprise administering an effective amount of a compound of the invention.

As used herein, "enhancing an immune response" refers to an improvement in any immunogenic response to an antigen. Non-limiting examples of improvements in an immunogenic response to an antigen include enhanced maturation or migration of dendritic cells, enhanced activation of T cells (e.g., CD4 T cells, CD8 T cells), enhanced T cell (e.g., CD4 T cell, CD8 T cell) proliferation, enhanced B cell proliferation, increased survival of T cells and/or B cells, improved antigen presentation by antigen presenting cells (e.g., dendritic cells), improved antigen clearance, increase in production of cytokines by T cells (e.g., interleukin-2), increased resistance to prostaglandin E2-induced immune suppression, and enhanced priming and/or cytolytic activity of CD8 T cells.

In some embodiments, the CD8 T cells in the subject have enhanced priming, activation, proliferation and/or cytolytic activity relative to prior to the administration of the compound of the invention or a pharmaceutically acceptable salt, prodrug, metabolite, or derivative thereof. In some embodiments, the CD8 T cell priming is characterized by elevated CD44 expression and/or enhanced cytolytic activity in CD8

T cells. In some embodiments, the CD8 T cell activation is characterized by an elevated frequency of γ-IFN$^+$ CD8 T cells. In some embodiments, the CD8 T cell is an antigen-specific T-cell.

In some embodiments, the antigen presenting cells in the subject have enhanced maturation and activation relative to prior to the administration of the compound of the invention or a pharmaceutically acceptable salt, prodrug, metabolite, or derivative thereof. In some embodiments, the antigen presenting cells are dendritic cells. In some embodiments, the maturation of the antigen presenting cells is characterized by an increased frequency of CD83$^+$ dendritic cells. In some embodiments, the activation of the antigen presenting cells is characterized by elevated expression of CD80 and CD86 on dendritic cells.

In some embodiments, the serum levels of cytokine IL-10 and/or chemokine IL-8, a human homolog of murine KC, in the subject are reduced relative to prior to the administration of the compound of Formula I or Ia or a pharmaceutically acceptable salt, prodrug, metabolite, or derivative thereof.

Engagement of the TCR leads to HPK1 activation, which functions as a negative regulator of TCR-induced AP-1 response pathway. It is believed that HPK1 negatively regulates T cell activation by reducing the persistence of signaling microclusters by phosphorylating SLP76 at Ser376 (Di Bartolo et al. (2007) JEM 204:681-691) and Gads at Thr254, which leads to the recruitment of 14-3-3 proteins that bind to the phosphorylated SLP76 and Gads, releasing the SLP76-Gads-14-3-3 complex from LAT-containing microclusters, which leads to T cell dysfunction, including anergy and exhaustion (Lasserre et al. (2011) J Cell Biol 195(5):839-853).

In some embodiments, administration of a compound of the invention or a pharmaceutically acceptable salt, prodrug, metabolite, or derivative thereof to a subject results in an enhancement of T cell function.

Accordingly, the presently disclosed compounds of the invention or pharmaceutically acceptable salts, prodrugs, metabolites, or derivatives thereof are useful in treating T cell dysfunctional disorders. A "T cell dysfunctional disorder" is a disorder or condition of T cells characterized by decreased responsiveness to antigenic stimulation. In a particular embodiment, a T cell dysfunctional disorder is a disorder that is specifically associated with increased kinase activity of HPK1. In another embodiment, a T cell dysfunctional disorder is one in which T cells are anergic or have decreased ability to secrete cytokines, proliferate, or execute cytolytic activity. In a specific aspect, the decreased responsiveness results in ineffective control of a pathogen or tumor expressing an immunogen. Examples of T cell dysfunctional disorders characterized by T-cell dysfunction include unresolved acute infection, chronic infection and tumor immunity.

Thus, the presently disclosed compounds can be used in treating conditions where enhanced immunogenicity is desired, such as increasing tumor immunogenicity for the treatment of cancer.

The term "dysfunction" in the context of immune dysfunction, refers to a state of reduced immune responsiveness to antigenic stimulation. The term includes the common elements of both exhaustion and/or anergy in which antigen recognition may occur, but the ensuing immune response is ineffective to control infection or tumor growth.

The term "dysfunctional", as used herein, also includes refractory or unresponsive to antigen recognition, specifically, impaired capacity to translate antigen recognition into downstream T-cell effector functions, such as proliferation, cytokine production (e.g., IL-2, γ-IFN) and/or target cell killing.

The term "anergy" refers to the state of unresponsiveness to antigen stimulation resulting from incomplete or insufficient signals delivered through the T-cell receptor (e.g. increase in intracellular Ca' in the absence of ras-activation). T cell anergy can also result upon stimulation with antigen in the absence of co-stimulation, resulting in the cell becoming refractory to subsequent activation by the antigen even in the context of costimulation. The unresponsive state can often be overridden by the presence of Interleukin-2. Anergic T-cells do not undergo clonal expansion and/or acquire effector functions.

The term "exhaustion" refers to T cell exhaustion as a state of T cell dysfunction that arises from sustained TCR signaling that occurs during many chronic infections and cancer. It is distinguished from anergy in that it arises not through incomplete or deficient signaling, but from sustained signaling. It is defined by poor effector function, sustained expression of inhibitory receptors and a transcriptional state distinct from that of functional effector or memory T cells. Exhaustion prevents optimal control of infection and tumors. Exhaustion can result from both extrinsic negative regulatory pathways (e.g., immunoregulatory cytokines) as well as cell intrinsic negative regulatory (costimulatory) pathways (PD-1, B7-H3, B7-H4, etc.).

"Immunogenecity" refers to the ability of a particular substance to provoke an immune response. Tumors are immunogenic and enhancing tumor immunogenicity aids in the clearance of the tumor cells by the immune response.

"Enhancing T cell function" means to induce, cause or stimulate a T cell to have a sustained or amplified biological function, or renew or reactivate exhausted or inactive T cells. Examples of enhancing T cell function include: increased secretion of cytokines (e.g., γ-interferon, IL-2, IL-12, and TNFα), increased proliferation, increased antigen responsiveness (e.g., viral, pathogen, or tumor clearance) relative to such levels before the intervention, and increased effector granule production by CD8 T cells, such as granzyme B. In one embodiment, the level of enhancement is as least 50%, alternatively 60%, 70%, 80%, 90%, 100%, 120%, 150%, 200%. The manner of measuring this enhancement is known to one of ordinary skill in the art.

"Tumor immunity" refers to the process in which tumors evade immune recognition and clearance. Thus, as a therapeutic concept, tumor immunity is "treated" when such evasion is attenuated, and the tumors are recognized and attacked by the immune system. Examples of tumor recognition include tumor binding, tumor shrinkage and tumor clearance.

The present disclosure provides methods of modulating (e.g., inhibiting) HPK1 activity, said method comprising administering to a patient a compound provided herein, or a pharmaceutically acceptable salt thereof.

In one aspect, provided herein is a method for treating of cancer in a subject in need thereof comprising administering to the subject an effective amount of a compound of the invention or a pharmaceutically acceptable salt, prodrug, metabolite, or derivative thereof.

In the methods described herein, a compound of the invention or a pharmaceutical composition thereof is administered to a subject that has cancer.

In certain embodiments, the subject matter disclosed herein is directed to a method for treating a HPK1-dependent disorder, the method comprising administering to a subject in need thereof an effective amount of a compound of the invention or a pharmaceutical composition described herein. In certain aspects of this embodiment, the HPK1-dependent disorder is a cancer. In certain aspects of this embodiment, the cancer comprises at least one cancer selected from the group consisting of colorectal cancer, melanoma, non-small cell lung cancer, ovarian cancer, breast cancer, pancreatic cancer, a hematological malignancy, and a renal cell carcinoma. In certain aspects of this embodiment, the cancer has elevated levels of T-cell infiltration. In certain aspects of this embodiment, the cancer cells in the subject selectively have elevated expression of MHC class I antigen expression relative to prior to the administration of the compound or composition.

In some embodiments, the subject matter disclosed herein is directed to a method for treatment of chronic viral infections. In some embodiments, the subject matter disclosed herein is directed to the use of an HPK1 inhibitor as an adjuvant treatment for increasing the efficacy of vaccination.

In some embodiments, the invention provides a pharmaceutical composition comprising an effective amount of a compound of the invention, or a pharmaceutically acceptable salt, hydrate, solvate, or prodrug thereof, and a pharmaceutically acceptable carrier.

In certain aspects, the invention provides a method of treating cell proliferation disorders, including cancers, benign papillomatosis, gestational trophoblastic diseases, and benign neoplastic diseases, such as skin papilloma (warts) and genital papilloma.

In one aspect, the invention provides a method of treating a cell proliferation disorder in a subject, comprising administering a therapeutically effective amount of a compound of the invention, or a pharmaceutically acceptable salt, hydrate, solvate, or prodrug thereof, to the subject.

In certain embodiments, the cell proliferation disorder is cancer.

Examples of cancers that are treatable using the compounds of the present disclosure include, but are not limited to, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, endometrial cancer, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or urethra, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and combinations of said cancers.

In some embodiments, cancers that are treatable using the compounds of the present disclosure include, but are not limited to, solid tumors (e.g., prostate cancer, colon cancer, esophageal cancer, endometrial cancer, ovarian cancer, uterine cancer, renal cancer, hepatic cancer, pancreatic cancer, gastric cancer, breast cancer, lung cancer, cancers of the head and neck, thyroid cancer, glioblastoma, sarcoma, bladder cancer, etc.), hematological cancers (e.g., lymphoma, leukemia such as acute lymphoblastic leukemia (ALL), acute myelogenous leukemia (AML), chronic lymphocytic leukemia (CLL), chronic myelogenous leukemia (CML), DLBCL, mantle cell lymphoma, Non-Hodgkin lymphoma (including relapsed or refractory NHL and recurrent follicular), Hodgkin lymphoma or multiple myeloma) and combinations of said cancers.

In certain embodiments, the cancer is brain cancer, leukemia, skin cancer, prostate cancer, thyroid cancer, colon cancer, lung cancer or sarcoma. In another embodiment the cancer is selected from the group consisting of glioma, glioblastoma multiforme, paraganglioma, suprantentorial primordial neuroectodermal tumors, acute myeloid leukemia, myelodysplastic syndrome, chronic myelogenous leukemia, melanoma, breast, prostate, thyroid, colon, lung, central chondrosarcoma, central and periosteal chondroma tumors, fibrosarcoma, and cholangiocarcinoma.

In certain embodiments, the cancer is selected from brain and spinal cancers, cancers of the head and neck, leukemia and cancers of the blood, skin cancers, cancers of the reproductive system, cancers of the gastrointestinal system, liver and bile duct cancers, kidney and bladder cancers, bone cancers, lung cancers, malignant mesothelioma, sarcomas, lymphomas, glandular cancers, thyroid cancers, heart tumors, germ cell tumors, malignant neuroendocrine (carcinoid) tumors, midline tract cancers, and cancers of unknown primary (cancers in which a metastasized cancer is found but the original cancer site is not known). In particular embodiments, the cancer is present in an adult patient; in additional embodiments, the cancer is present in a pediatric patient. In particular embodiments, the cancer is AIDS-related.

In a further embodiment, the cancer is selected from brain and spinal cancers. In particular embodiments, the cancer is selected from the group consisting of anaplastic astrocytomas, glioblastomas, astrocytomas, and estheosioneuroblastomas (olfactory blastomas). In particular embodiments, the brain cancer is selected from the group consisting of astrocytic tumor (e.g., pilocytic astrocytoma, subependymal giant-cell astrocytoma, diffuse astrocytoma, pleomorphic xanthoastrocytoma, anaplastic astrocytoma, astrocytoma, giant cell glioblastoma, glioblastoma, secondary glioblastoma, primary adult glioblastoma, and primary pediatric glioblastoma), oligodendroglial tumor (e.g., oligodendroglioma, and anaplastic oligodendroglioma), oligoastrocytic tumor (e.g., oligoastrocytoma, and anaplastic oligoastrocytoma), ependymoma (e.g., myxopapillary ependymoma, and anaplastic ependymoma); medulloblastoma, primitive neuroectodermal tumor, schwannoma, meningioma, atypical meningioma, anaplastic meningioma, pituitary adenoma, brain stem glioma, cerebellar astrocytoma, cerebral astorcytoma/malignant glioma, visual pathway and hypothalmic glioma, and primary central nervous system lymphoma. In specific instances of these embodiments, the brain cancer is selected from the group consisting of glioma, glioblastoma multiforme, paraganglioma, and suprantentorial primordial neuroectodermal tumors (sPNET).

In specific embodiments, the cancer is selected from cancers of the head and neck, including nasopharyngeal cancers, nasal cavity and paranasal sinus cancers, hypopharyngeal cancers, oral cavity cancers (e.g., squamous cell carcinomas, lymphomas, and sarcomas), lip cancers, oropharyngeal cancers, salivary gland tumors, cancers of the larynx (e.g., laryngeal squamous cell carcinomas, rhabdomyosarcomas), and cancers of the eye or ocular cancers.

In particular embodiments, the ocular cancer is selected from the group consisting of intraocular melanoma and retinoblastoma.

In specific embodiments, the cancer is selected from leukemia and cancers of the blood. In particular embodiments, the cancer is selected from the group consisting of myeloproliferative neoplasms, myelodysplastic syndromes, myelodysplastic/myeloproliferative neoplasms, acute myeloid leukemia (AML), myelodysplastic syndrome (MDS), chronic myelogenous leukemia (CML), myeloproliferative neoplasm (MPN), post-MPN AML, post-MDS AML, del(5q)-associated high risk MDS or AML, blast-phase chronic myelogenous leukemia, angioimmunoblastic lymphoma, acute lymphoblastic leukemia, Langerans cell histiocytosis, hairy cell leukemia, and plasma cell neoplasms including plasmacytomas and multiple myelomas. Leukemias referenced herein may be acute or chronic.

In specific embodiments, the cancer is selected from skin cancers. In particular embodiments, the skin cancer is selected from the group consisting of melanoma, squamous cell cancers, and basal cell cancers.

In specific embodiments, the cancer is selected from cancers of the reproductive system. In particular embodiments, the cancer is selected from the group consisting of breast cancers, cervical cancers, vaginal cancers, ovarian cancers, prostate cancers, penile cancers, and testicular cancers. In specific instances of these embodiments, the cancer is a breast cancer selected from the group consisting of ductal carcinomas and phyllodes tumors. In specific instances of these embodiments, the breast cancer may be male breast cancer or female breast cancer. In specific instances of these embodiments, the cancer is a cervical cancer selected from the group consisting of squamous cell carcinomas and adenocarcinomas. In specific instances of these embodiments, the cancer is an ovarian cancer selected from the group consisting of epithelial cancers.

In specific embodiments, the cancer is selected from cancers of the gastrointestinal system. In particular embodiments, the cancer is selected from the group consisting of esophageal cancers, gastric cancers (also known as stomach cancers), gastrointestinal carcinoid tumors, pancreatic cancers, gallbladder cancers, colorectal cancers, and anal cancer. In instances of these embodiments, the cancer is selected from the group consisting of esophageal squamous cell carcinomas, esophageal adenocarcinomas, gastric adenocarcinomas, gastrointestinal carcinoid tumors, gastrointestinal stromal tumors, gastric lymphomas, gastrointestinal lymphomas, solid pseudopapillary tumors of the pancreas, pancreatoblastoma, islet cell tumors, pancreatic carcinomas including acinar cell carcinomas and ductal adenocarcinomas, gallbladder adenocarcinomas, colorectal adenocarcinomas, and anal squamous cell carcinomas.

In specific embodiments, the cancer is selected from liver and bile duct cancers. In particular embodiments, the cancer is liver cancer (hepatocellular carcinoma). In particular embodiments, the cancer is bile duct cancer (cholangiocarcinoma); in instances of these embodiments, the bile duct cancer is selected from the group consisting of intrahepatic cholangiocarcinoma and extrahepatic cholangiocarcinoma.

In specific embodiments, the cancer is selected from kidney and bladder cancers. In particular embodiments, the cancer is a kidney cancer selected from the group consisting of renal cell cancer, Wilms tumors, and transitional cell cancers. In particular embodiments, the cancer is a bladder cancer selected from the group consisting of urethelial carcinoma (a transitional cell carcinoma), squamous cell carcinomas, and adenocarcinomas.

In specific embodiments, the cancer is selected from bone cancers. In particular embodiments, the bone cancer is selected from the group consisting of osteosarcoma, malignant fibrous histiocytoma of bone, Ewing sarcoma, and chordoma.

In specific embodiments, the cancer is selected from lung cancers. In particular embodiments, the lung cancer is selected from the group consisting of non-small cell lung cancer, small cell lung cancers, bronchial tumors, and pleuropulmonary blastomas.

In specific embodiments, the cancer is selected from malignant mesothelioma. In particular embodiments, the cancer is selected from the group consisting of epithelial mesothelioma and sarcomatoids.

In specific embodiments, the cancer is selected from sarcomas. In particular embodiments, the sarcoma is selected from the group consisting of central chondrosarcoma, central and periosteal chondroma, fibrosarcoma, clear cell sarcoma of tendon sheaths, and Kaposi's sarcoma.

In specific embodiments, the cancer is selected from lymphomas. In particular embodiments, the cancer is selected from the group consisting of Hodgkin lymphoma (e.g., Reed-Sternberg cells), non-Hodgkin lymphoma (e.g., diffuse large B-cell lymphoma, follicular lymphoma, mycosis fungoides, Sezary syndrome, primary central nervous system lymphoma), cutaneous T-cell lymphomas, and primary central nervous system lymphomas.

In specific embodiments, the cancer is selected from glandular cancers. In particular embodiments, the cancer is selected from the group consisting of adrenocortical cancer, pheochromocytomas, paragangliomas, pituitary tumors, thymoma, and thymic carcinomas.

In specific embodiments, the cancer is selected from thyroid cancers. In particular embodiments, the thyroid cancer is selected from the group consisting of medullary thyroid carcinomas, papillary thyroid carcinomas, and follicular thyroid carcinomas.

In specific embodiments, the cancer is selected from germ cell tumors. In particular embodiments, the cancer is selected from the group consisting of malignant extracranial germ cell tumors and malignant extragonadal germ cell tumors. In specific instances of these embodiments, the malignant extragonadal germ cell tumors are selected from the group consisting of nonseminomas and seminomas.

In specific embodiments, the cancer is selected from heart tumors. In particular embodiments, the heart tumor is selected from the group consisting of malignant teratoma, lymphoma, rhabdomyosacroma, angiosarcoma, chondrosarcoma, infantile fibrosarcoma, and synovial sarcoma.

In specific embodiments, the cell-proliferation disorder is selected from benign papillomatosis, benign neoplastic diseases and gestational trophoblastic diseases. In particular embodiments, the benign neoplastic disease is selected from skin papilloma (warts) and genital papilloma. In particular embodiments, the gestational trophoblastic disease is selected from the group consisting of hydatidiform moles, and gestational trophoblastic neoplasia (e.g., invasive moles, choriocarcinomas, placental-site trophoblastic tumors, and epithelioid trophoblastic tumors).

In some embodiments, the subject has melanoma. The melanoma may be at early stage or at late stage. In some embodiments, the subject has colorectal cancer. The colorectal cancer may be at early stage or at late stage. In some embodiments, the subject has non-small cell lung cancer. The non-small cell lung cancer may be at early stage or at late stage. In some embodiments, the subject has pancreatic cancer. The pancreatic cancer may be at early stage or late state. In some embodiments, the subject has a hematological malignancy. The hematological malignancy may be at early stage or late stage. In some embodiments, the subject has ovarian cancer. The ovarian cancer may be at early stage or at late stage. In some embodiments, the subject has breast cancer. The breast cancer may be at early stage or at late stage. In some embodiments, the subject has renal cell carcinoma. The renal cell carcinoma may be at early stage or at late stage. In some embodiments, the cancer has elevated levels of T-cell infiltration.

In some embodiments, cancers treatable with compounds of the present disclosure include melanoma (e.g., metastatic malignant melanoma), renal cancer (e.g. clear cell carcinoma), prostate cancer (e.g. hormone refractory prostate adenocarcinoma), breast cancer, triple-negative breast cancer, colon cancer and lung cancer (e.g. non-small cell lung cancer and small cell lung cancer). Additionally, the disclosure includes refractory or recurrent malignancies whose growth may be inhibited using the compounds of the disclosure.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET)), myelodysplasia syndrome (MDS), T-cell acute lymphoblastic lymphoma (T-ALL), multiple myeloma, cutaneous T-cell lymphoma, Waldenstrom's Macroglubulinemia, hairy cell lymphoma, chronic myelogenic lymphoma and Burkitt's lymphoma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, and mesothelioma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), and colorectal cancer.

Exemplary genitourinary tract cancers include cancers of the kidney (adenocarcinoma, Wilm's tumor [nephroblastoma]), bladder and urethra (squamous cell carcinoma, transitional cell carcinoma, adenocarcinoma), prostate (adenocarcinoma, sarcoma), and testis (seminoma, teratoma, embryonal carcinoma, teratocarcinoma, choriocarcinoma, sarcoma, interstitial cell carcinoma, fibroma, fibroadenoma, adenomatoid tumors, lipoma).

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors), and spinal cord (neurofibroma, meningioma, glioma, sarcoma), as well as neuroblastoma and Lhermitte-Duclos disease.

Exemplary gynecological cancers include cancers of the uterus (endometrial carcinoma), cervix (cervical carcinoma, pre-tumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids. In some embodiments, diseases and indications that are treatable using the compounds of the present disclosure include, but are not limited to, sickle cell disease (e.g., sickle cell anemia), triple-negative breast cancer (TNBC), myelodysplastic syndromes, testicular cancer, bile duct cancer, esophageal cancer, and urothelial carcinoma.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers.

In some embodiments, HPK1 inhibitors may be used to treat tumors producing PGE2 (e.g. Cox-2 overexpressing tumors) and/or adenosine (CD73 and CD39 over-expressing tumors). Overexpression of Cox-2 has been detected in a number of tumors, such as colorectal, breast, pancreatic and lung cancers, where it correlates with a poor prognosis. Overexpression of COX-2 has been reported in hematological cancer models such as RAJI (Burkitt's lymphoma) and U937 (acute promonocytic leukemia) as well as in patient's blast cells. CD73 is up-regulated in various human carcinomas including those of colon, lung, pancreas and ovary. Importantly, higher expression levels of CD73 are associated with tumor neovascularization, invasiveness, and metastasis and with shorter patient survival time in breast cancer.

In some embodiments, the compounds of the invention are useful in preventing or reducing the risk of developing any of the diseases referred to herein; e.g., preventing or reducing the risk of developing a disease, condition or disorder in an individual who may be predisposed to the disease, condition or disorder but does not yet experience or display the pathology or symptomatology of the disease.

The presently disclosed compounds may be administered in any suitable manner known in the art. In some embodiments, the compound of the invention or a pharmaceutically acceptable salt, prodrug, metabolite, or derivative thereof is administered intravenously, intramuscularly, subcutaneously, topically, orally, transdermally, intraperitoneally, intraorbitally, by implantation, by inhalation, intrathecally, intraventricularly, intratumorally, or intranasally.

In some embodiments, the HPK1 antagonist is administered continuously. In other embodiments, the HPK1 antagonist is administered intermittently. Moreover, treatment of a subject with an effective amount of a HPK1 antagonist can include a single treatment or can include a series of treatments.

It is understood that appropriate doses of the active compound depends upon a number of factors within the knowledge of the ordinarily skilled physician or veterinarian. The dose(s) of the active compound will vary, for example, depending upon the age, body weight, general health, gender, and diet of the subject, the time of administration, the route of administration, the rate of excretion, and any drug combination.

It will also be appreciated that the effective dosage of a compound of the invention or a pharmaceutically acceptable salt, prodrug, metabolite, or derivative thereof used for treatment may increase or decrease over the course of a particular treatment. Changes in dosage may result and become apparent from the results of diagnostic assays.

In some embodiments, the HPK1 antagonist is administered to the subject at a dose of between about 0.001 µg/kg and about 1000 mg/kg, including but not limited to about 0.001 µg/kg, 0.01 µg/kg, 0.05 µg/kg, 0.1 µg/kg, 0.5 µg/kg, 1 µg/kg, 10 µg/kg, 25 µg/kg, 50 µg/kg, 100 µg/kg, 250 µg/kg, 500 µg/kg, 1 mg/kg, 5 mg/kg, 10 mg/kg, 25 mg/kg, 50 mg/kg, 100 mg/kg, and 200 mg/kg.

In the methods described herein, the method can further comprise administering a chemotherapeutic agent to the subject. In certain aspects of this embodiment, the chemotherapeutic agent is administered to the subject simultaneously with the compound or the composition. In certain aspects of this embodiment, the chemotherapeutic agent is administered to the subject prior to administration of the compound or the composition. In certain aspects of this embodiment, the chemotherapeutic agent is administered to the subject after administration of the compound or the composition.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

The term "administration" or "administering" includes routes of introducing the compound(s) to a subject to perform their intended function. Examples of routes of administration which can be used include injection (subcutaneous, intravenous, parenterally, intraperitoneally, intrathecal), topical, oral, inhalation, rectal and transdermal.

The term "effective amount" includes an amount effective, at dosages and for periods of time necessary, to achieve the desired result. An effective amount of compound may vary according to factors such as the disease state, age, and weight of the subject, and the ability of the compound to elicit a desired response in the subject. Dosage regimens may be adjusted to provide the optimum therapeutic response.

The phrases "systemic administration," "administered systemically", "peripheral administration" and "administered peripherally" as used herein mean the administration of a compound(s), drug or other material, such that it enters the patient's system and, thus, is subject to metabolism and other like processes.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein. In the case of cancer, the therapeutically effective amount of the drug may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. To the extent the drug may prevent growth and/or kill existing cancer cells, it may be cytostatic and/or cytotoxic. For cancer therapy, efficacy can be measured, for example, by assessing the time to disease progression (TTP) and/or determining the response rate (RR).

The term "subject" refers to animals such as mammals, including, but not limited to, primates (e.g., humans), cows, sheep, goats, horses, dogs, cats, rabbits, rats, mice and the like. In certain embodiments, the subject is a human.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

In one embodiment, the present invention provides a composition comprising a compound of formula I and one or more additional therapeutic agents. The therapeutic agent may be administered together with a compound of formula I, or may be administered prior to or following administration of a compound of formula I. Suitable therapeutic agents are described in further detail below. In certain embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a compound of formula I may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a compound of formula I and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating rheumatoid arthritis comprising administering to a patient in need thereof a compound of formula I and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating cutaneous lupus erythematosus or systemic lupus erythematosus comprising administering to a patient in need thereof a compound of formula I and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating Crohn's disease, ulcerative colitis, or inflammatory bowel disease comprising administering to a patient in need thereof a compound of formula I and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a compound of formula I and one or more additional therapeutic agents selected from Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-bid®, Uniphyl®, Theo-24®) and aminophylline, and IgE antibodies such as omalizumab (Xolair®).

In some embodiments, the present invention provides a method of treating COPD comprising administering to a patient in need thereof a compound of formula I and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In another embodiment, the present invention provides a method of treating a hematological malignancy comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a solid tumor comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a PI3K inhibitor, a SYK inhibitor, and combinations thereof.

In another embodiment, the present invention provides a method of treating a hematological malignancy comprising administering to a patient in need thereof a compound of formula I and a Hedgehog (Hh) signaling pathway inhibitor. In some embodiments, the hematological malignancy is DLBCL (Ramirez et al "Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a compound of formula I and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In another embodiment, the present invention provides a method of treating multiple myeloma comprising administering to a patient in need thereof a compound of formula I and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating or lessening the severity of a disease comprising administering to a patient in need thereof a compound of formula I and a BTK inhibitor, wherein the disease is selected from inflammatory bowel disease, arthritis, cutaneous lupus erythematosus, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, cutaneous lupus erythematosus, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a compound of formula I and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a compound of formula I and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), cutaneous lupus erythematosus, systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments the present invention provides a method of treating or lessening the severity of a disease comprising administering to a patient in need thereof a compound of formula I and a Bcl-2 inhibitor, wherein the disease is an inflammatory disorder, an autoimmune disorder, a proliferative disorder, an endocrine disorder, a neurological disorder, or a disorder associated with transplantation. In some embodiments, the disorder is a proliferative disorder, lupus, or lupus nephritis. In some embodiments, the proliferative disorder is chronic lymphocytic leukemia, diffuse large B-cell lymphoma, Hodgkin's disease, small-cell lung cancer, non-small-cell lung cancer, myelodysplastic syndrome, lymphoma, a hematological neoplasm, or solid tumor.

In some embodiments, the disease is an autoimmune disorder, an inflammatory disorder, a proliferative disorder, an endocrine disorder, a neurological disorder, or a disorder associated with transplantation. In some embodiments the JH2 binding compound is a compound of formula I. Other suitable JH2 domain binding compounds include those described in WO2014074660A1, WO2014074661A1, WO2015089143A1, the entirety of each of which is incorporated herein by reference. Suitable JH1 domain binding compounds include those described in WO2015131080A1, the entirety of which is incorporated herein by reference.

The compounds and compositions, according to the method of the present invention, may be administered using any amount and any route of administration effective for treating or lessening the severity of an autoimmune disorder, an inflammatory disorder, a proliferative disorder, an endocrine disorder, a neurological disorder, or a disorder associated with transplantation. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity in a biological sample comprising the step of contacting said biological sample with a compound of this invention, or a composition comprising said compound.

According to another embodiment, the invention relates to a method of inhibiting HPK1, or a mutant thereof, activity in a biological sample comprising the step of contacting said biological sample with a compound of this invention, or a composition comprising said compound. In certain embodiments, the invention relates to a method of irreversibly inhibiting HPK1, or a mutant thereof, activity in a biological sample comprising the step of contacting said biological sample with a compound of this invention, or a composition comprising said compound.

The term "biological sample", as used herein, includes, without limitation, cell cultures or extracts thereof biopsied material obtained from a mammal or extracts thereof; and blood, saliva, urine, feces, semen, tears, or other body fluids or extracts thereof.

Inhibition of HPK1 (or a mutant thereof) activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of inhibiting protein kinase activity in a patient comprising the step of administering to said patient a compound of the present invention, or a composition comprising said compound.

According to another embodiment, the invention relates to a method of inhibiting activity of HPK1, or a mutant thereof, in a patient comprising the step of administering to said patient a compound of the present invention, or a composition comprising said compound. According to certain embodiments, the invention relates to a method of reversibly or irreversibly inhibiting one or more of HPK1, or a mutant thereof, activity in a patient comprising the step of administering to said patient a compound of the present invention, or a composition comprising said compound. In other embodiments, the present invention provides a method for treating a disorder mediated by HPK1, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other therapeutic compounds. In some embodiments, the other therapeutic compounds are antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin. The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketokonazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an anti estrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™) daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; vinca alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the AxI receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/pan-JAK, FAK, PDK1, PKB/Akt, Ras/MAPK, PI3K, SYK, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a P13K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); l) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, C1-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO2008118802), navitoclax (and analogs thereof, see U.S. Pat. No. 7,390,799), NH-1 (Shenayng Pharmaceutical University), obatoclax (and analogs thereof, see WO2004106328), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

Further examples of BTK inhibitory compounds, and conditions treatable by such compounds in combination with compounds of this invention can be found in WO2008039218 and WO2011090760, the entirety of which are incorporated herein by reference.

Further examples of SYK inhibitory compounds, and conditions treatable by such compounds in combination with compounds of this invention can be found in WO2003063794, WO2005007623, and WO2006078846, the entirety of which are incorporated herein by reference.

Further examples of PI3K inhibitory compounds, and conditions treatable by such compounds in combination with compounds of this invention can be found in WO2004019973, WO2004089925, WO2007016176, U.S. Pat. No. 8,138,347, WO2002088112, WO2007084786, WO2007129161, WO2006122806, WO2005113554, and WO2007044729 the entirety of which are incorporated herein by reference.

Further examples of JAK inhibitory compounds, and conditions treatable by such compounds in combination with compounds of this invention can be found in WO2009114512, WO2008109943, WO2007053452, WO2000142246, and WO2007070514, the entirety of which are incorporated herein by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC125, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™) and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; ALK inhibitors, which are compounds which target, decrease or inhibit anaplastic lymphoma kinase, and Bcl-2 inhibitors.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino,17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PRO64553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412. In some embodiments, the present invention provides a method of treating AML associated with an ITD and/or D835Y mutation, comprising administering a compound of the present invention together with a one or more FLT3 inhibitors. In some embodiments, the FLT3 inhibitors are selected from quizartinib (AC220), a staurosporine derivative (e.g. midostaurin or lestaurtinib), sorafenib, tandutinib, LY-2401401, LS-104, EB-10, famitinib, NOV-110302, NMS-P948, AST-487, G-749, SB-1317, S-209, SC-110219, AKN-028, fedratinib, tozasertib, and sunitinib. In some embodiments, the FLT3 inhibitors are selected from quizartinib, midostaurin, lestaurtinib, sorafenib, and sunitinib.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]phenyl]-2E-2-propenamide, or a pharmaceutically acceptable salt thereof and N-hydroxy-3-[4-[(2-hydroxyethyl) 2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™)

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fn14, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIRL TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonist of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO11/70024, WO11/107553, WO11/131407, WO13/87699, WO13/119716, WO13/132044) or FPA-008 (WO11/140249; WO13169264; WO14/036357).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO2010/077634), durvalumab (MEDI4736), BMS-936559 (WO2007/005874), and MSB0010718C (WO2013/79174).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO10/19570, WO14/08218), or IMP-731 or IMP-321 (WO08/132601, WO009/44273).

In some embodiments, an immuno-oncology agent is a CD137 (4-1BB) agonist. In some embodiments, a CD137 (4-1BB) agonist is an agonistic CD137 antibody. In some embodiments, a CD137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO006/105021, WO009/009116), or MK-4166 (WO11/028683).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); an enzyme that breaks down kynurenine (Kynase, Ikena Oncology, formerly known as Kyn Therapeutics); and NLG-919 (WO09/73620, WO009/1156652, WO11/56652, WO12/142237).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO06/029879).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO11/109400).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (OPDIVO®, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (POMALYST®, Celgene); lenalidomide (REVLIMID®, Celgene); ingenol mebutate (PICATO®, LEO Pharma).

In some embodiments, an immuno-oncology agent is a cancer vaccine. In some embodiments, the cancer vaccine is selected from sipuleucel-T (PROVENGE®, Dendreon/Valeant Pharmaceuticals), which has been approved for treatment of asymptomatic, or minimally symptomatic metastatic castrate-resistant (hormone-refractory) prostate cancer; and talimogene laherparepvec (IMLYGIC®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (REOLYSIN®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific $CD8^+$ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682 (June et al.; hereby incorporated by reference in its entirety), which discloses CAR-T cells engineered to comprise an extracellular domain having an antigen binding domain (such as a domain that binds to CD19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+ (Th17) and CD8+(Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that can be used in the present invention include urelumab (BMS-663513, Bristol-Myers Squibb), an anti-CD137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those descripted in Jerry L. Adams et al., "Big opportunities for small molecules in immuno-oncology," Cancer Therapy 2015, Vol. 14, pages 603-622, the content of which is incorporated herein by reference in its entirety. In some embodiments, an immuno-oncology agent is selected from the examples described in Table 1 of Jerry L. Adams et al. In some embodiments, an immuno-oncology agent is a small molecule targeting an immuno-oncology target selected from those listed in Table 2 of Jerry L. Adams et al. In some embodiments, an immuno-oncology agent is a small molecule agent selected from those listed in Table 2 of Jerry L. Adams et al.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BITE®) antibody constructs can mediate bystander tumor cell killing", PLoS ONE 12(8): e0183390, the content of which is incorporated herein by reference in its entirety. In some embodiments, an immuno-oncology agent is a bispecific T cell engager (BITE®) antibody construct. In some embodiments, a bispecific T cell engager (BITE®) antibody construct is a CD19/CD3 bispecific antibody construct. In some embodiments, a bispecific T cell engager (BITE®) antibody construct is an EGFR/CD3 bispecific antibody construct. In some embodiments, a bispecific T cell engager (BITE®) antibody construct activates T cells. In some embodiments, a bispecific T cell engager (BITE®) antibody construct activates T cells, which release cytokines inducing upregulation of intercellular adhesion molecule 1 (ICAM-1) and FAS on bystander cells. In some embodiments, a bispecific T cell engager (BITE®) antibody construct activates T cells which result in induced bystander cell lysis. In some embodiments, the bystander cells are in solid tumors. In some embodiments, the bystander cells being lysed are in proximity to the BITE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In some embodiments, the checkpoint inhibitor is a biologic therapeutic or a small molecule. In some embodiments, the checkpoint inhibitor is a monoclonal antibody, a humanized antibody, a fully human antibody, a fusion protein or a combination thereof. In some embodiments, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In some embodiments, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In some embodiments, the checkpoint inhibitor is an immunostimulatory agent, a T cell growth factor, an interleukin, an antibody, a vaccine or a combination thereof. In some embodiments, the interleukin is IL-7 or IL-15. In some embodiments, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors can include small molecule inhibitors or can include antibodies, or antigen binding fragments thereof, that bind to and block or inhibit immune checkpoint receptors or antibodies that bind to and block or inhibit immune checkpoint receptor ligands. Illustrative checkpoint molecules that can be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory $CD8^+$ ($\alpha\beta$) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GALS, LAG3, VISTA, KIR, 2B4, CD 160 and CGEN-15049. Illustrative immune checkpoint inhibitors include, but are not limited to, Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (OPDIVO®), ipilimumab (YERVOY®), and pembrolizumab (KEYTRUDA®). In some embodiments, the checkpoint inhibitor is selected from nivolumab (anti-PD-1 antibody, OPDIVO®, Bristol-Myers Squibb); pembrolizumab (anti-PD-1 antibody, KEYTRUDA®, Merck); ipilimumab (anti-CTLA-4 antibody, YERVOY®, Bristol-Myers Squibb); durvalumab (anti-PD-L1 antibody, IMFINZI®, AstraZeneca); and atezolizumab (anti-PD-L1 antibody, TECENTRIQ®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (KEYTRUDA®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (BAVENCIO®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that can be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that can be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981); and CTX-471 (Compass Therapeutics), an agonistic anti-CD137 antibody in metastatic or locally advanced malignancies (NCT03881488).

Checkpoint inhibitors that can be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that can be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Checkpoint inhibitors that can be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that can be used in the present invention include killer IgG-like receptor (KIR) inhibitors.

KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that can be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, Trillium Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that can be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that can be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that can be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that can be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein. Additional compounds of the invention were prepared by methods substantially similar to those described herein in the Examples and methods known to one skilled in the art.

Synthesis of Intermediates

Synthesis of Tert-Butyl 4-(6-aminopyridin-3-yl)piperazine-1-carboxylate (Intermediate AA1)

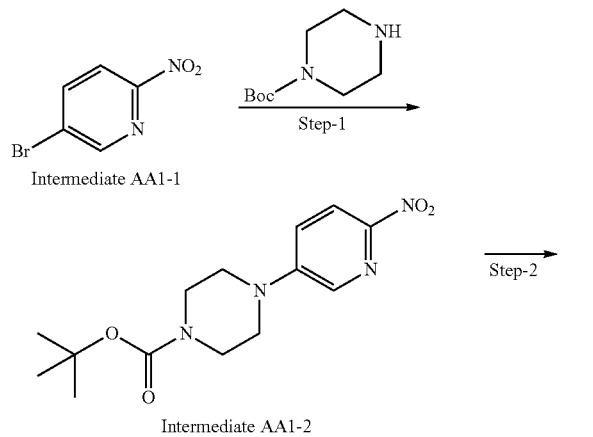

Step-1 Synthesis of Tert-Butyl 4-(6-nitropyridin-3-yl)piperazine-1-carboxylate (Intermediate AA1-1)

To a solution of 5-bromo-2-nitropyridine (3.0 g 14.76 mmol, 1.0 eq.) and tert-butyl piperazine-1-carboxylate (4.2 g 22.58 mmol, 1.5 eq.) in dry DMSO (10.0 mL) was added triethylamine (2.25 g, 22.27 mmol, 1.5 eq.) and lithium chloride (0.63 g, 14.76 mmol, 1.0 eq.) at RT. The reaction mixture was heated at 70° C. for 20 h. After completion of reaction, the reaction mixture was poured into ice water and solid product was collected by filtration. Solid was triturated with n-pentane to afford Intermediate AA1-1 (3.0 g, 65.84%) MS (ES) m/z 309.33 (M+H)$^+$.

Step-2 Synthesis of Tert-Butyl 4-(6-aminopyridin-3-yl)piperazine-1-carboxylate. (Intermediate AA1)

To a suspension of 10% Pd/C (2.2 g) in methanol (50 mL) was added a solution of Intermediate AA1-1 (4.0 g, 12.98 mmol) in methanol (10 mL) under nitrogen atmosphere. H$_2$ (gas) was bubbled into the reaction mixture for 3 h. After completion of reaction, the reaction mixture was filtered through celite and washed with methanol. The filtrate was concentrated under reduced pressure to give Intermediate AA1 (2.4 g, 55.39%). MS (ES): m/z 279.24 [M+H]$^+$.

Synthesis of 5-(4-methylpiperazin-1-yl)pyridin-2-amine (Intermediate AA2)

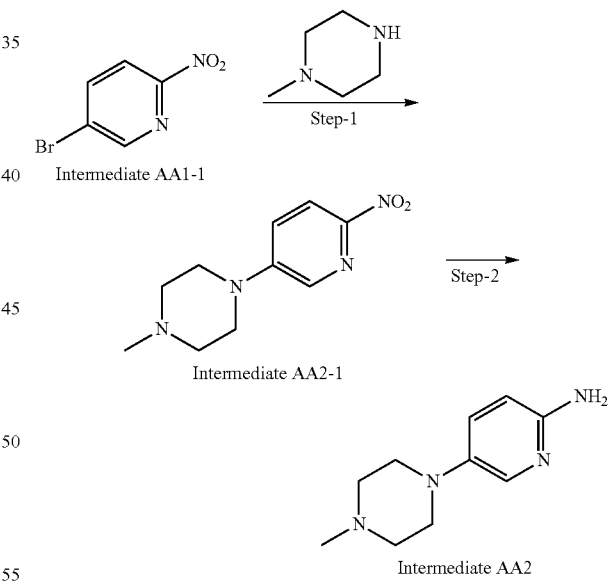

Step-1 Synthesis of 5-(4-methylpiperazin-1-yl)pyridin-2-amine (Intermediate AA2)

5-(4-methylpiperazin-1-yl)pyridin-2-amine (Intermediate AA2) was prepared from 5-bromo-2-nitropyridine (Intermediate AA1-1) and 1-methylpiperazine in a similar fashion to that described in tert-butyl 4-(6-aminopyridin-3-yl)piperazine-1-carboxylate. (General process Intermediate AA1) (1.0 g, 70.84%) MS (ES) m/z 193.2 (M+H)$^+$.

Synthesis of 5-morpholinopyridin-2-amine (Intermediate AA3)

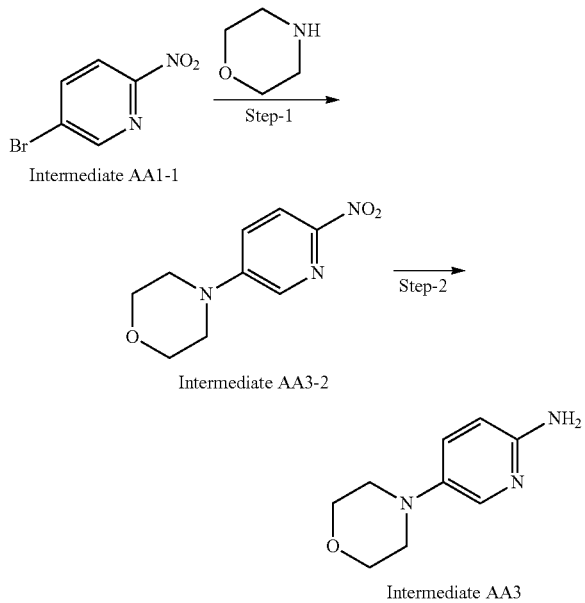

Step-1 Synthesis of 5-morpholinopyridin-2-amine (Intermediate AA3)

5-morpholinopyridin-2-amine (Intermediate AA3) was prepared from 5-bromo-2-nitropyridine (Intermediate AA3-1) and morpholine in a similar fashion to that described in tert-butyl 4-(6-aminopyridin-3-yl) piperazine-1-carboxylate. (General process Intermediate AA1). (1.0 g, 64.84%) MS (ES) m/z 180.33 (M+H)$^+$.

Synthesis of Tert-Butyl 3-(6-aminopyridin-3-yl)-3,8-diazabicyclo[3.2.1]octane-8-carboxylate (Intermediate AA6)

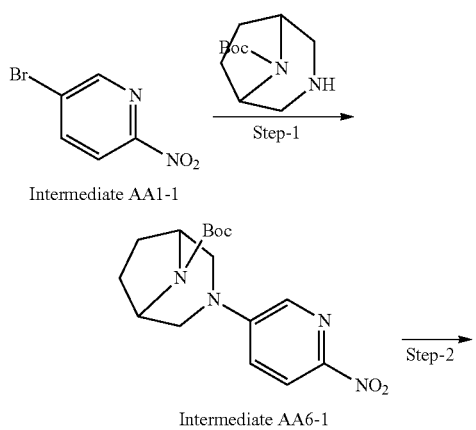

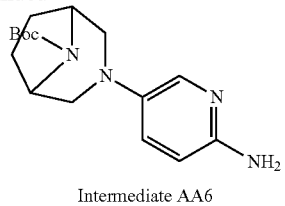

Step-1 Synthesis of Tert-Butyl 3-(6-nitropyridin-3-yl)-3,8-diazabicyclo[3.2.1]octane-8-Carboxylate. (Intermediate AA6-1)

To a solution of 5-bromo-2-nitropyridine (Intermediate AA1-1) (1.0 g 4.9 mmol, 1.0 eq.) in 1,4-dioxane (13.0 mL) were added tert-butyl 3,8-diazabicyclo[3.2.1]octane-8-carboxylate (1.05 g, 4.9 mmol, 1.0 eq.) and tripotassium phosphate (2.03 g, 14.7 mmol, 3.0 eq.) at RT. After degassing with argon for 20 min, Pd$_2$dba$_3$ (0.45 g, 0.49 mmol, 0.1 eq.) and xantphos (0.57 g, 0.98 mmol, 0.2 eq.) were added to the reaction mixture. After heating at 120° C. for 3 h, the reaction mixture was poured into water (100 mL) and extracted with ethyl acetate (100 mL×3). The organic layer was washed with brine (100 mL) solution, dried over sodium sulfate, and concentrated under reduced pressure which. The crude compound was purified by column chromatography (0-40% gradient elution EtOAc in Hexanes) to afford the title compound (Intermediate AA6-1) (0.500 g, 30.35%). MS (ES): m/z 334.3 (M+H)$^+$.

Step-2 Synthesis of Tert-Butyl 3-(6-aminopyridin-3-yl)-3,8-diazabicyclo[3.2.1]octane-8-carboxylate (Intermediate AA6)

tert-butyl 3-(6-aminopyridin-3-yl)-3,8-diazabicyclo[3.2.1]octane-8-carboxylate (Intermediate AA6) in a similar fashion to that described tert-butyl 4-(6-aminopyridin-3-yl) piperazine-1-carboxylate. (General process Intermediate AA1) (0.430 g, 94.4%). MS (ES): m/z 304 (M+H)$^+$.

Synthesis of 1-(6-amino-5-methoxypyridin-3-yl) piperidin-4-ol (Intermediate AA7)

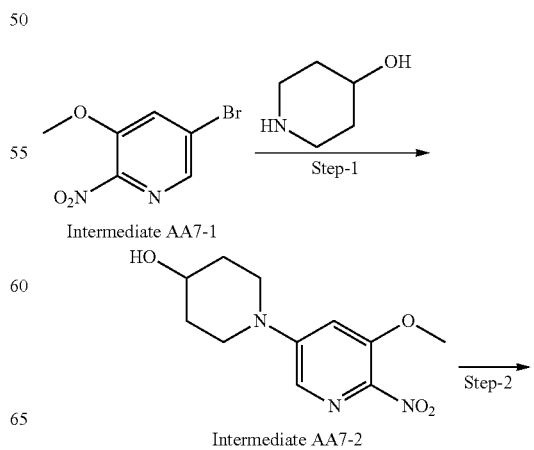

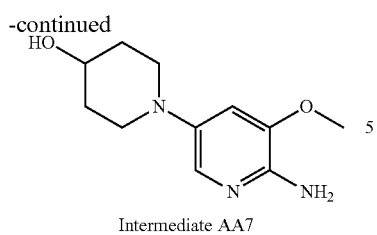

Intermediate AA7

Step-1 Synthesis of 1-(5-methoxy-6-nitropyridin-3-yl)piperidin-4-ol (Intermediate AA7-2)

To a solution of 5-bromo-3-methoxy-2-nitropyridine (Intermediate AA7-1) (0.5 g 2.1 mmol, 1.0 eq.) in dry DMSO (6 mL) was added piperidin-4-ol (0.35 g, 2.6 mmol, 1.2 eq.), potassium carbonate (1.7 g, 12.0 mmol, 6.0 eq.) and tetrabutylammonium iodide (0.22 g, 0.6 mmol, 0.3 eq.) at RT. After heating at 90° C. for 2 h, the reaction mixture was poured into water (100 mL) and extracted with ethyl acetate (100×3). The organic layer was washed with brine (100 mL) solution, dried over sodium sulfate, and concentrated under reduced pressure. The crude compound was purified by column chromatography (0-40% gradient elution EtOAc in Hexanes) to afford the title compound (Intermediate AA7-1) (0.3 g, 56.24%). MS (ES): m/z 254.2 (M+H)⁻.

Step-2 Synthesis of 1-(6-amino-5-methoxypyridin-3-yl)piperidin-4-ol (Intermediate AA7)

1-(6-amino-5-methoxypyridin-3-yl)piperidin-4-ol (Intermediate AA7) was prepared in a similar fashion to that described tert-butyl 4-(6-aminopyridin-3-yl)piperazine-1-carboxylate. (General process Intermediate AA1). (0.2 g, 74.73%). MS (ES): m/z 224.2 (M+H)⁺.

Synthesis of Tert-Butyl 4-(6-aminopyridin-3-yl)-4-methylpiperidine-1-carboxylate (Intermediate AA9)

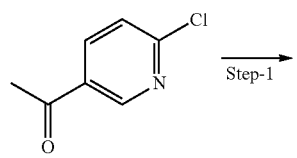

Intermediate AA9-1

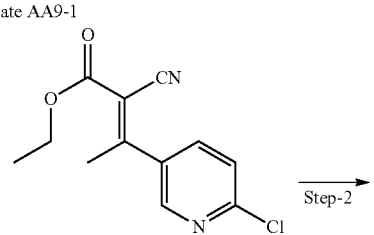

Intermediate AA9-2

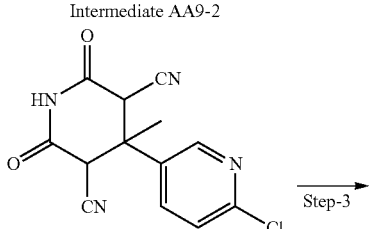

Intermediate AA9-3

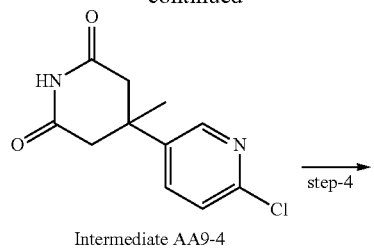

Intermediate AA9-4

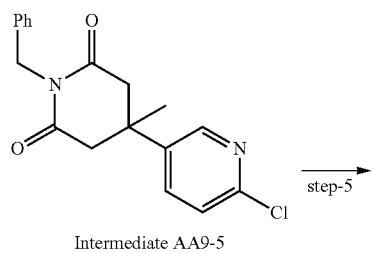

Intermediate AA9-5

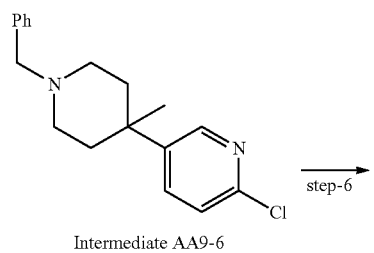

Intermediate AA9-6

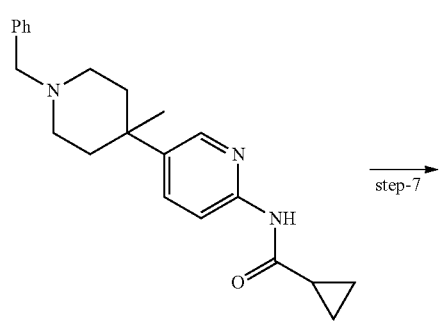

Intermediate AA9-7

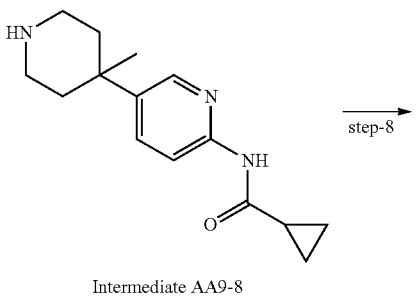

Intermediate AA9-8

-continued

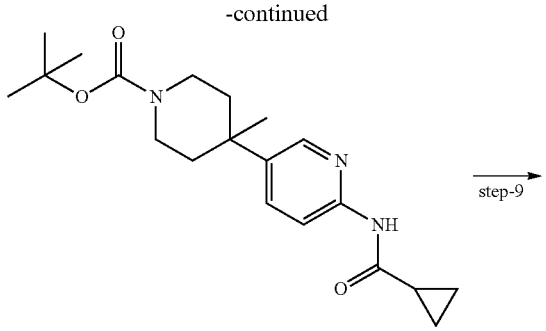

Intermediate AA9-9

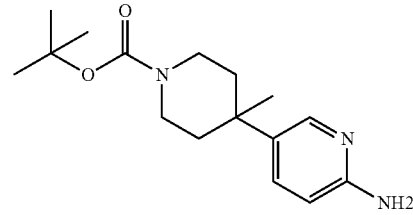

Intermediate AA9

Step-1 Synthesis of Ethyl (E)-3-(6-chloropyridin-3-yl)-2-cyanobut-2-enoate (Intermediate AA9-2)

To a solution of 1-(6-chloropyridin-3-yl)ethan-1-one (10.0 g 64.51 mmol, 1.0 eq.) and ethyl 2-cyanoacetate (7.2 g 64.51 mmol, 1.0 eq.) in toluene (35 mL) were added ammonium acetate (1.0 g, 12.90 mmol, 0.2 eq) and acetic acid (4 mL). After stirring at 140° C. for 6 h in dean stark assembly, the reaction mixture was diluted with sodium bicarbonate solution (150 mL) and extracted with ethyl acetate (2×100 mL). The combined organic extracts were washed with brine (200 mL), dried over $Na_2SO_4$, filtered, and concentrated under reduced pressure to afford crude material. This material was used in next Step without purification. Intermediate AA9-2 (15.0 g, 96.09%) MS (ES) m/z 251.05 $(M+H)^+$.

Step-2 Synthesis of 4-(6-chloropyridin-3-yl)-4-methyl-2,6-dioxopiperidine-3,5-dicarbonitrile (Intermediate AA9-3)

To a solution of Intermediate AA9-2 (14.9 g, 59.6 mmol) and 2-cyanoacetamide (6.0 g, 71.52 mmol, 1.2 eq) in ethanol (130 mL) was added sodium hydroxide (2.86 g, 71.52 mmol, 1.2 eq). The reaction mixture was stirred at RT for 1 h. After completion of reaction, 1M of potassium bisulfate solution was added to the reaction mixture. After stirring at 10° C., a solid precipitated from solution. The solid was filtered and dried under high vacuum to afford Intermediate AA9-3 which was used in next Step without purification. (20.0 g, 98.12%). MS (ES): m/z 289.04 $[M+H]^+$.

Step-3 Synthesis of 4-(6-chloropyridin-3-yl)-4-methylpiperidine-2,6-dione (Intermediate AA9-4)

To a solution of Intermediate AA9-3 (20.0 g, 69.44 mmol) in Water (12 mL) was added dropwise sulfuric acid (12 mL) at 10° C. After stirring at 110° C. for 7 h, solid sodium hydroxide was added at 0° C. The reaction mixture was filtered and washed with 10% methanol in DCM. The combined organic layer was dried over sodium sulfate and concentrated under reduced pressure to afford liquid material. Urea (40 g) was added to this crude material and stirred at 140° C. for 2 h. The reaction mixture was diluted with ethyl acetate (1 L) and saturated sodium bicarbonate solution (500 mL). The organic layer was collected, washed with brine solution (300 mL), dried over sodium sulfate and concentrated under reduced pressure to afford Intermediate AA9-4 which was used in next Step without purification. (2.2 g, 13.31%). MS (ES): m/z 239.05 $[M+H]^+$.

Step-4 Synthesis of 1-benzyl-4-(6-chloropyridin-3-yl)-4-methylpiperidine-2,6-dione (Intermediate AA9-5)

To a solution of Intermediate AA9-4 (1.2 g, 5.02 mmol) in acetone (50 mL) was added potassium carbonate (1.38 g, 10.04 mmol, 2.0 eq) and stirred at 0° C. Benzyl bromide (0.94 g, 5.52 mmol, 1.1 eq) was added into the reaction mixture and then stirred at 70° C. for 2 h. After completion of reaction, the reaction mixture distilled out to remove acetone. The residue was diluted with water (150 mL) and extracted with ethyl acetate (70 mL×3). The combined organic layer washed with brine solution, dried over sodium sulfate, and concentrated under reduced pressure to afford crude material. The residue was purified by column chromatography eluting with 25% ethyl acetate in hexane to afford Intermediate AA9-5. (1.5 g, 90.74%). MS (ES): m/z 329.10 $[M+H]^+$.

Step-5 Synthesis of 5-(1-benzyl-4-methylpiperidin-4-yl)-2-chloropyridine (Intermediate AA9-6)

To a solution of Intermediate AA9-5 (1.2 g, 3.65 mmol) in dry THF (20 mL) was added lithium aluminum hydride (1.0M in THF) (14 mL, 14.06 mmol, 4.0 eq) at −5° C. After stirring at 70° C. for 1 h, reaction mixture was concentrated. The reside was diluted with water (100 mL) and extracted with ethyl acetate (50 mL×3). The combined organic layer washed with brine solution, dried over sodium sulfate, and concentrated under reduced pressure to afford crude material. This material was purified by column chromatography eluting with 1.2% ethyl acetate in hexane to afford Intermediate AA9-6. (0.4 g, 36.43%). MS (ES): m/z 301.2 $[M+H]^+$.

Step-6 Synthesis of N-(5-(1-benzyl-4-methylpiperidin-4-yl)pyridin-2-yl)cyclopropanecarboxamide (Intermediate AA9-7)

A solution of Intermediate AA9-6. (1.6 g, 5.33 mmol) cyclopropanecarboxamide (0.679 g, 7.99 mmol, 1.5 eq), and cesium carbonate (5.1 g, 15.99 mmol, 3.0 eq) in 1,4-dioxane (20 mL) was degassed under $N_2$ stream. After 15 min, Xantphos (0.308 g, 0.53 mmol, 0.1 eq) and $Pd_2(dba)_3$ (0.487 g, 0.53 mmol, 0.1 eq) added. After stirring at 120° C. for 16 h, the reaction mixture was cooled to RT, diluted water (100 mL) and extracted with ethyl acetate (3×50 mL). The combined organic extracts were washed with brine (100 mL), dried over $Na_2SO_4$, filtered, and concentrated under reduced pressure. The residue was purified by column chromatography eluting with 2.5% gradient of methanol in DCM to afford Intermediate AA9-7 (1.6 g, 69.94%) as a brown solid. MS (ES): m/z=350.2 $[M+H]^+$.

Step-7 Synthesis of N-(5-(4-methylpiperidin-4-yl)pyridin-2-yl)cyclopropanecarboxamide (Intermediate AA9-8)

To a solution of Intermediate AA9-7 (0.5 g, 1.43 mmol) in methanol (10 mL) was added 10% Pd/C (0.250 g was hydrogenated at atmospheric pressure for 6 h at RT. After completion of reaction, the reaction mixture was filtered through celite-bed and washed with methanol. The filtrate was concentrated under reduced pressure to afford crude material which was used in next Step without purification. Intermediate AA9-8 (0.450 g, 94.32%). MS (ES): m/z 260.1 [M+H]+, Step-8 Synthesis of Tert-Butyl 4-(6-(cyclopropanecarboxamido)pyridin-3-yl)-4-methylpiperidine-1-carboxylate (Intermediate AA9-9)

To a solution of Intermediate AA9-8 (0.450 g, 1.73 mmol) in DCM (20 mL) were added trimethylamine (0.524, 5.19 mmol, 3.0 eq) and DMAP (0.021 g, 0.173 mmol, 0.1 eq). Di-tert-butyl dicarbonate (0.754, 3.46 mmol, 2.0 eq) was then added dropwise into the reaction mixture. After stirring at RT for 2 h, the reaction mixture concentrated, diluted with water (50 mL), and extracted with ethyl acetate (30 mL×3). The combined organic layer washed with brine solution, dried over sodium sulfate, and concentrated under reduced pressure to afford crude material. The residue was purified by column chromatography eluting with 2.5% methanol in DCM to afford Intermediate AA9-9. (0.450 g, 72.15%). MS (ES): m/z 360.2 [M+H]+.

Step-9 Synthesis of Tert-Butyl 4-(6-aminopyridin-3-yl)-4-methylpiperidine-1-carboxylate (Intermediate-AA9)

To a solution of Intermediate AA9-9 (0.450 g, 1.25 mmol) in methanol (10 mL) was added sodium hydroxide (0.5 g, 12.5 mmol, 10.0 eq). After stirring at 50° C. for 16 h, the reaction mixture was poured in water (70 mL) and extracted with DCM (40 mL×3). The combined organic layer washed with brine solution, dried over sodium sulfate, and concentrated under reduced pressure to afford crude material. The residue was purified by column chromatography eluting with 4.0% methanol in DCM to afford Intermediate-AA9 (0.210 g, 57.57%). MS (ES): m/z 292.2 [M+H]+

Synthesis of 2-(1-(6-aminopyridin-3-yl)piperidin-3-yl)propan-2-ol (Intermediate AA13)

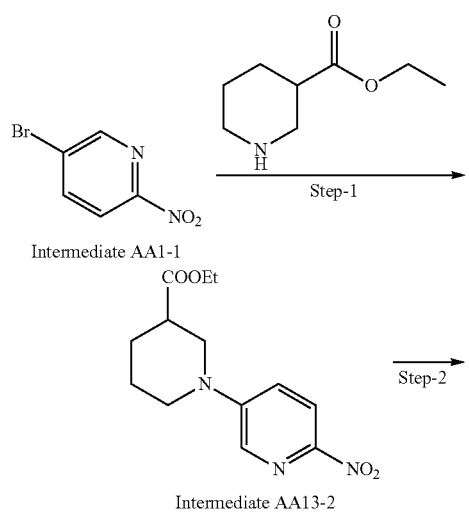

Intermediate AA1-1

Intermediate AA13-2

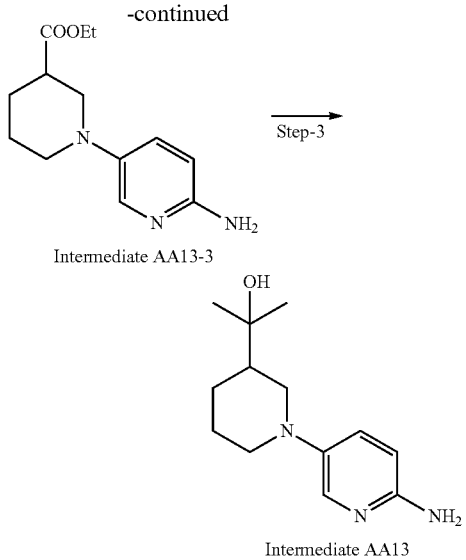

Intermediate AA13-3

Intermediate AA13

Step-1 Synthesis of Ethyl 1-(6-nitropyridin-3-yl) piperidine-3-carboxylate (Intermediate AA13-2)

Ethyl 1-(6-nitropyridin-3-yl)piperidine-3-carboxylate (Intermediate AA13-2) was prepared from 5-bromo-2-nitropyridine (Intermediate AA2-1) and 1-ethyl piperidine-3-carboxylate in a similar fashion to that described tert-butyl 4-(6-nitropyridin-3-yl)piperazine-1-carboxylate (General process Intermediate AA1). (1.5 g, 36.34%) MS (ES): m/z 280.14 [M+H]+

Step-2 Synthesis of Ethyl 1-(6-aminopyridin-3-yl) piperidine-3-carboxylate (Intermediate AA13-3)

Ethyl 1-(6-aminopyridin-3-yl)piperidine-3-carboxylate (Intermediate AA13-3) was prepared from ethyl 1-(6-nitropyridin-3-yl)piperidine-3-carboxylate (Intermediate AA13-2) in a similar fashion to that described tert-butyl 4-(6-aminopyridin-3-yl)piperazine-1-carboxylate. (General process Intermediate AA1) (1.2 g, 89.62%). MS (ES): m/z 250.15 [M+H]+

Step-3 Synthesis of 2-(1-(6-aminopyridin-3-yl)piperidin-3-yl)propan-2-ol (Intermediate AA13)

To a solution of ethyl 1-(6-aminopyridin-3-yl)piperidine-3-carboxylate (Intermediate AA13-3) (2.0 g, 8.03 mmol) in THF (15 mL) was added a 3N solution of methyl magnesium bromide (3N in THF) (20 mL) dropwise at 0° C. After stirring at RT for 1 h, the reaction mixture was quenched with ice cool water (100 mL) and filtered on celite bed. The filtrate was extracted with ethyl acetate (100 mL×3). The combine organic layer washed with brine (100 mL) and concentrated under reduced. The crude compound was purified by column chromatography (0-80% gradient elution EtOAc in hexanes) to afford the title compound (Intermediate AA13) (0.200 g, 10.60%). MS (ES): m/z 236.17 [M+H]+

Synthesis of 5-((1R,4R)-2-oxa-5-azabicyclo[2.2.1]heptan-5-yl)pyridin-2-amine (Intermediate AA14)

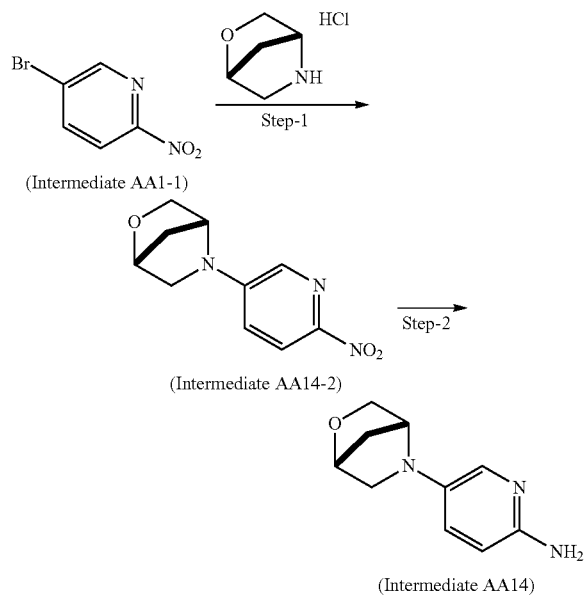

Step-1 Synthesis of 5-((1R,4R)-2-oxa-5-azabicyclo[2.2.1]heptan-5-yl)pyridin-2-amine (Intermediate AA14)

5-((1R,4R)-2-oxa-5-azabicyclo[2.2.1]heptan-5-yl)pyridin-2-amine (Intermediate AA14) was prepared from 5-bromo-2-nitropyridine (Intermediate AA1-1) and (1R,4R)-2-oxa-5-azabicyclo[2.2.1]heptane in a similar fashion to that described tert-butyl 4-(6-nitropyridin-3-yl)piperazine-1-carboxylate (General process Intermediate AA1). (0.330 g, Quantitative yield). MS (ES): m/z 192.5 [M+H]$^+$.

Synthesis of 1-(6-bromopyridin-3-yl)-4-(morpholinomethyl)piperidin-4-ol (Intermediate AA15)

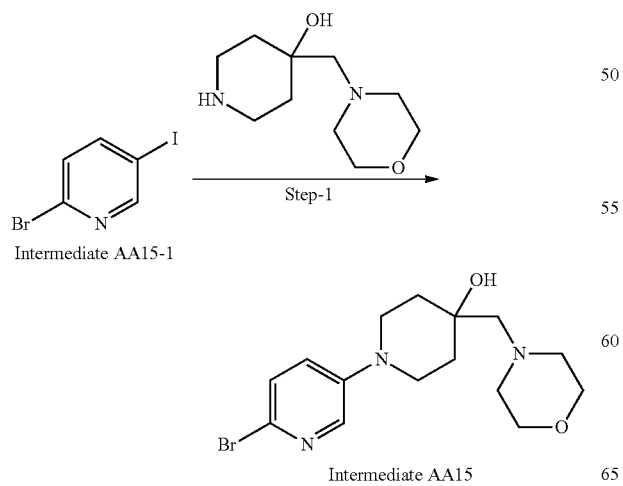

Step-1 Synthesis of 1-(6-bromopyridin-3-yl)-4-(morpholinomethyl)piperidin-4-ol (Intermediate AA15)

To a solution of 2-bromo-5-iodopyridine (0.6 g, 2.0 mmol) in 1,4-dioxane (6 mL) were added 4-(morpholinomethyl)piperidin-4-ol (0.64 g, 3.0 mmol, 1.5 eq) and cesium carbonate (2.1, 6.0 mmol, 3.0 eq). After degassing with nitrogen gas for 10 min, 4,5-bis(diphenylphosphino)-9,9-dimethylxanthene (0.125 g, 0.02 mmol, 0.1 eq) and tris(dibenzylideneacetone)dipalladium (0.2 g, 0.2 mmol, 0.1 eq) were added under nitrogen gas atmosphere. The reaction mixture was heated to 120° c. for 3 h. The reaction mixture was diluted with water (50 mL) and extracted with ethyl acetate (50 mL×3). The combined organic layer was washed with brine (50 mL) solution, dried over sodium sulfate and concentrated under reduced pressure to afford crude material which was purified using combi-flash silica eluting with 4% methanol/DCM to afford Intermediate AA15 (0.2 g, 26.56%) MS (ES): m/z 357.26 [M+H]$^+$

Synthesis of 1-(6-chloro-4-methoxypyridin-3-yl)piperidin-4-ol (Intermediate AA18)

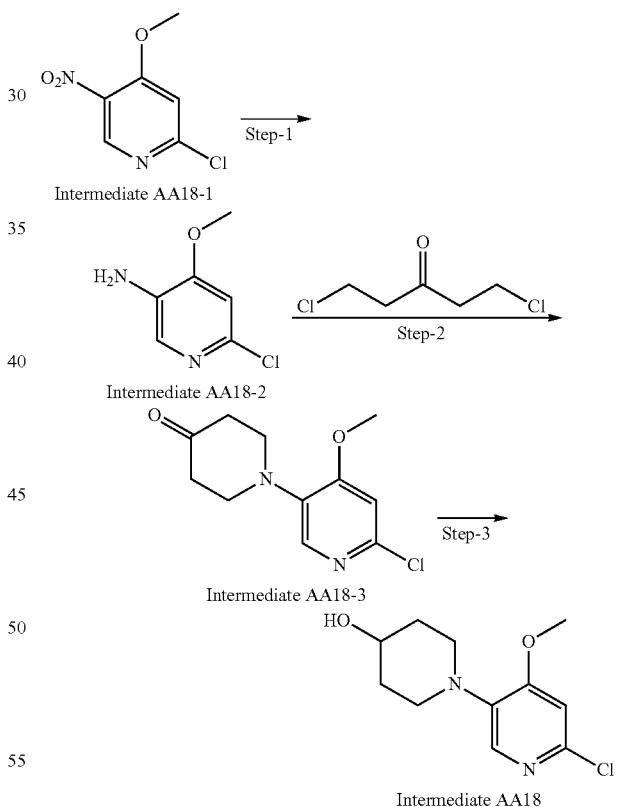

Step-1 Synthesis of 6-chloro-4-methoxypyridin-3-amine (Intermediate AA18-2)

To a solution of 2-chloro-4-methoxy-5-nitropyridine (Intermediate AA18-1) (2.0 g, 10.6 mmol) in ethanol (8 mL),) was added SnCl$_2$·2H$_2$O (9.6 g, 63.8 mmol, 6.0 eq). After stirring at 90° C. for 30 mins, the reaction mixture was quenched with e 3M NaOH solution (100 mL) and extracted with DCM (100 mL). The combined organic layer was washed with brine solution (100 mL), dried over sodium sulfate and concentrated under reduced pressure to afford crude material. The residue was purified by column chromatography eluting with 15-20% ethyl acetate in hexane to afford Intermediate AA18-2. LCMS purity 100%, MS (ES): m/z 159.03 [M+H]$^+$ Step-2 Synthesis of 1-(6-chloro-4-methoxypyridin-3-yl)piperidin-4-one (Intermediate AA18-3)

To a refluxing slurry of sodium carbonate (1.51 g, 14 mmol, 1.5 eq) in MeOH (8 mL) was added a solution of Intermediate AA18-2 (1.5 g, 9.5 mmol) in MeOH (2 mL) and 1,5-dichloropentan-3-one (1.6 g, 9.5 mmol, 1.0 eq). After stirring at 50° C. for 16 h, the reaction mixture was concentrated under vacuum to give crude material that was purified by column chromatography eluting with 20-25% ethyl acetate in hexane to afford Intermediate AA18-3. (1.2 g, 80.01%) MS (ES): 241.07 m/z [M+H]$^+$.

Step-3 Synthesis of 1-(6-chloro-4-methoxypyridin-3-yl)piperidin-4-ol (Intermediate AA18)

To a solution of Intermediate AA18-3 (1.2 g, 5 mmol) in MeOH (12 mL) was added NaBH$_4$ (0.228 g, 6 mmol, 1.2 eq). After stirring for 30 mins, the reaction mixture was diluted with water (50 mL) and extracted with ethyl acetate (50 mL×3). The combined organic layer was washed with brine (50 mL) solution, dried over sodium sulfate, and concentrated under reduced pressure to afford crude material which was purified using combi-flash silica eluting with 15-20% ethyl acetate in hexane to afford Intermediate AA18. MS (ES): 243 m/z [M+H]+.

Synthesis of 2-(6-aminopyridin-3-yl)-2-azaspiro[3.3]heptan-6-ol (Intermediate AA19)

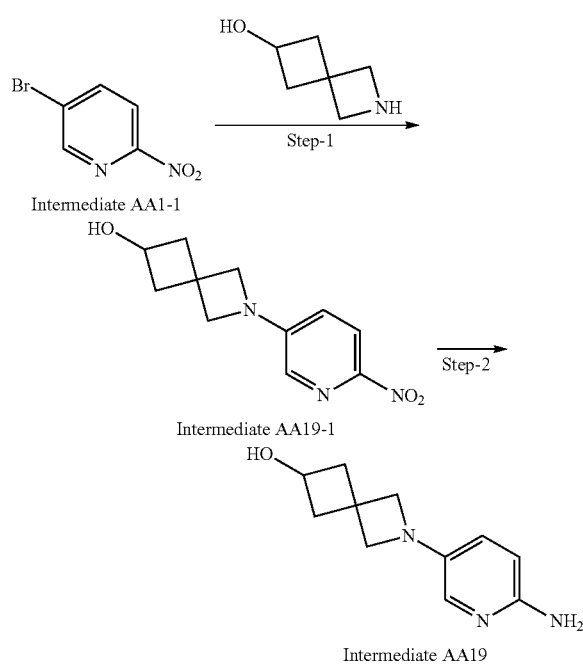

Step-1 Synthesis of 2-(6-aminopyridin-3-yl)-2-azaspiro[3.3]heptan-6-ol (Intermediate AA19)

2-(6-aminopyridin-3-yl)-2-azaspiro[3.3]heptan-6-ol (Intermediate AA19) was prepared from 5-bromo-2-nitropyridine (Intermediate AA1-1) and 2-azaspiro[3.3]heptan-6-ol in a similar fashion to that described tert-butyl 4-(6-nitropyridin-3-yl)piperazine-1-carboxylate (General process intermediate AA1). 0.600 g, 98.23%). MS (ES): m/z 206.12 [M+H]$^+$.

Synthesis of 1-(6-aminopyridin-3-yl)-4-(methoxymethyl)piperidin-4-ol (Intermediate AA20)

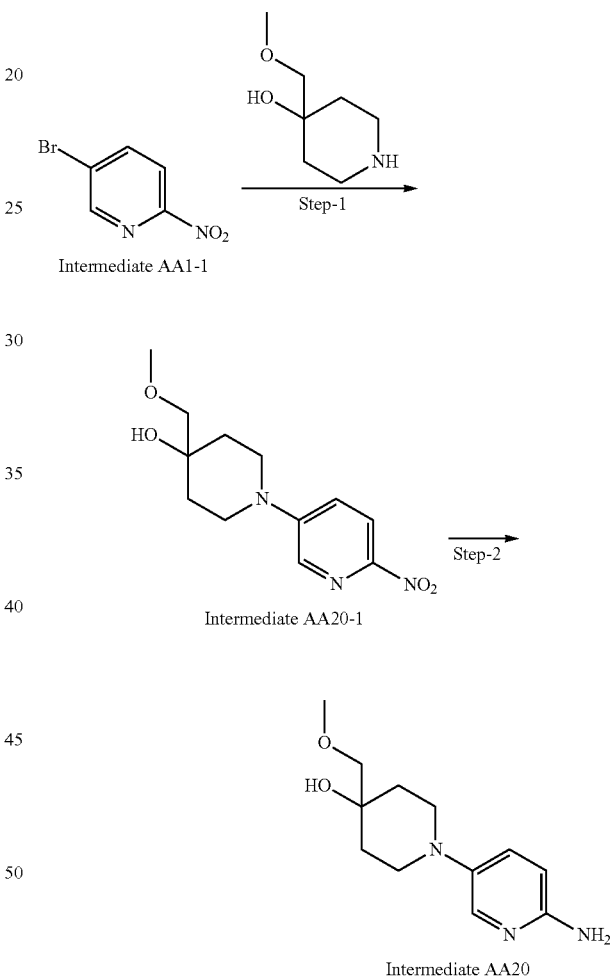

Step-1 Synthesis of 1-(6-aminopyridin-3-yl)-4-(methoxymethyl)piperidin-4-ol (Intermediate AA20)

1-(6-aminopyridin-3-yl)-4-(methoxymethyl)piperidin-4-ol (Intermediate AA20) was prepared from 5-bromo-2-nitropyridine (Intermediate AA1-1) and 4-(methoxymethyl)piperidin-4-ol in a similar fashion to that described tert-butyl 4-(6-aminopyridin-3-yl)piperazine-1-carboxylate. (General process intermediate AA1). (0.600 g, 96.54%). MS (ES): m/z 238.12 [M+H]$^+$

Synthesis of 5-(2-oxa-7-azaspiro[3.5]nonan-7-yl)pyridin-2-amine (Intermediate AA21)

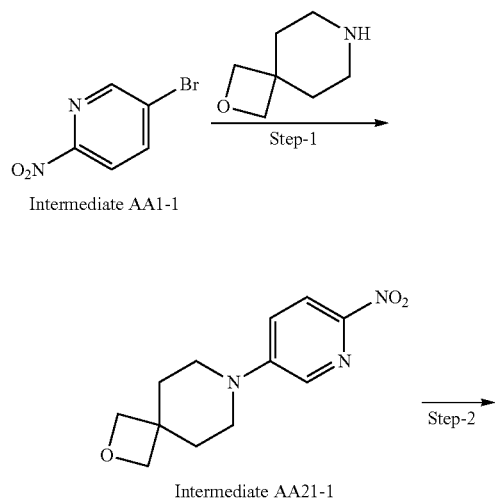

5-(2-oxa-7-azaspiro[3.5]nonan-7-yl)pyridin-2-amine (Intermediate AA21) was prepared from 5-bromo-2-nitropyridine (Intermediate AA1-1) and 2-oxa-7-azaspiro[3.5]nonane in a similar fashion to that described tert-butyl 4-(6-aminopyridin-3-yl)piperazine-1-carboxylate. (General process intermediate AA1). (0.3 g, 75.76%). MS (ES): m/z 220.2 (M+H)⁺.

Synthesis of 5-(1,4-oxazepan-4-yl)pyridin-2-amine (Intermediate AA22)

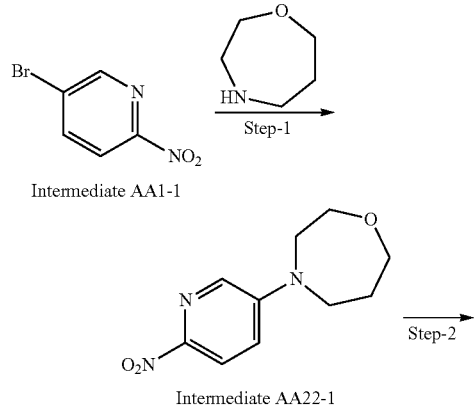

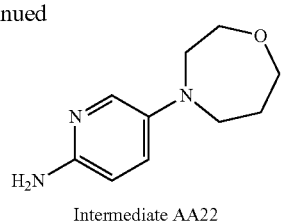

5-(1,4-oxazepan-4-yl)pyridin-2-amine (Intermediate AA22) was prepared from 5-bromo-2-nitropyridine (Intermediate AA1-1) and 1,4-oxazepane in a similar fashion to that described tert-butyl 4-(6-aminopyridin-3-yl)piperazine-1-carboxylate. (General process intermediate AA1). (0.300 g, 57.76%). MS (ES): m/z 194.15 [M+H]⁺

Synthesis of (1R,3r,5S)-8-(6-aminopyridin-3-yl)-8-azabicyclo[3.2.1]octan-3-ol (Intermediate AA23)

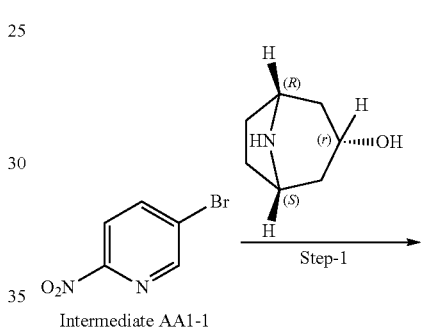

(1R,3r,5S)-8-(6-aminopyridin-3-yl)-8-azabicyclo[3.2.1]octan-3-ol (Intermediate AA23) was prepared from 5-bromo-2-nitropyridine (Intermediate AA1-1) and (1R,3r,5S)-8-azabicyclo[3.2.1]octan-3-ol in a similar fashion to that described tert-butyl 4-(6-aminopyridin-3-yl)piperazine-1-carboxylate. (General process intermediate AA1) (1.8 g, 94.7%). MS (ES): m/z 219.2 (M+H)⁺.

Synthesis of 5-(azetidin-1-ylsulfonyl)-2-chloropyridine (Intermediate AA25)

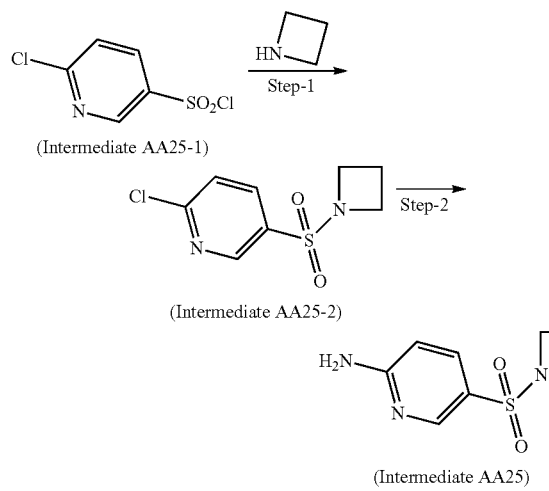

Step-1 Synthesis of Intermediate AA25-2

Prepared as described in WO2020/89026.

Step-2 Synthesis of 5-(azetidin-1-ylsulfonyl)-2-chloropyridine (Intermediate AA25)

A solution of 5-(azetidin-1-ylsulfonyl)-2-chloropyridine (Intermediate AA25-2) (400 mg, 1.51 mol) in ammonia solution in water (3000 mL) was allowed to stir at 80° C. for 16 h. After completion of reaction, the reaction was concentrated under vacuum to afforded title compound as white solid (Intermediate AA25) (200 mg, 78.74%). MS (ES): m/z 214.59 [M+H]$^+$

Synthesis of 5-((3aR,6aS)-tetrahydro-1H-furo[3,4-c]pyrrol-5(3H)-yl)pyridin-2-amine (Intermediate AA30)

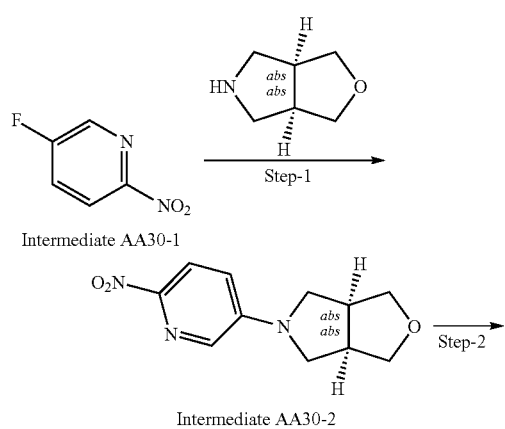

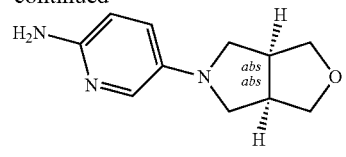

Intermediate AA30

Step-1: Synthesis of (3aR,6aS)-5-(6-nitropyridin-3-yl)hexahydro-1H-furo[3,4-c]pyrrole (Intermediate AA30-2)

To a solution of 5-fluoro-2-nitro pyridine (1.0 g 7.04 mmol, 1.0 eq.) in dimethyl sulfoxide (13.0 mL) were added (3aR, 6aS)-rel-hexahydro-1H-furo[3,4-c]pyrrole hydrochloride (1.05 g, 7.04 mmol, 1.0 eq.) and N,N-diisopropylethylamine (10 eq, 70.4 mmol.) at RT. After stirring at 120° C. for 1 h, the reaction mixture was poured into water and extracted with ethyl acetate (100 mL×3). The organic layer was washed with brine (100 mL×3) solution. The combined organic layer was concentrated under reduced pressure at 45° C. to afford Intermediate AA30-2 (2 g, 172.5%). MS (ES): m/z 236.33 (M+H)$^+$.

Step-2 Synthesis of 5-((3aR,6aS)-tetrahydro-1H-furo[3,4-c]pyrrol-5(3H)-yl)pyridin-2-amine (Intermediate AA30)

Synthesis of 5-((3aR,6aS)-tetrahydro-1H-furo[3,4-c]pyrrol-5(3H)-yl)pyridin-2-amine (Intermediate AA30) was prepared from (3aR,6aS)-5-(6-nitropyridin-3-yl)hexahydro-1H-furo[3,4-c]pyrrole (Intermediate AA30-2) in a similar fashion to that described tert-butyl 4-(6-aminopyridin-3-yl) piperazine-1-carboxylate. (General process intermediate AA1). (0.600 g, 96.54%). MS (ES): m/z 238.12 [M+H]$^+$

Synthesis of 5-(((cyclobutylmethyl)sulfonyl)pyridin-2-amine (Intermediate AA32)

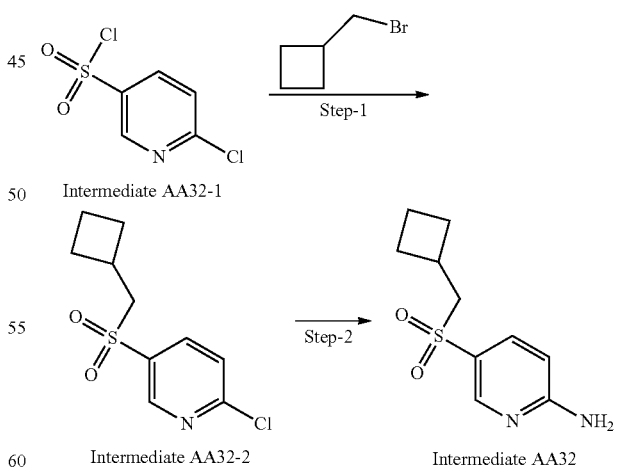

Step-1 Synthesis of 2-chloro-5-((cyclobutylmethyl)sulfonyl)pyridine (Intermediate AA32-2)

To a solution of 6-chloropyridine-3-sulfonyl chloride (2.0 g, 9.43 mmol) in water (40 mL) were added sodium bicarbonate (1.73 g, 9.43 mmol) and sodium sulphite (1.18 g, 9.43 mmo). After stirring at 40° C. for 1 h, the reaction mixture was concentrated by high vacuum to give a solid. To a solution of the solid in N'N-DMF (20 mL) were added (bromomethyl)cyclobutane (1.68 g, 11.3 mmo, 1.2 eq) and pyridine (0.679 g, 11.3 mmo). After stirring at RT for 16 h, the reaction was concentrated, diluted with water, and extracted with ethyl acetate (100 mL×3). The combined organic layer was washed with brine solution, dried over sodium sulfate and concentrated under reduced pressure to afford crude material which was purified using Column chromatography eluting with 15% ethyl acetate/hexane to afford Intermediate AA32-2 (0.900 g, 27.29%) MS (ES): m/z 246.03 [M+H]⁺

Step-2 Synthesis of
5-((cyclobutylmethyl)sulfonyl)pyridin-2-amine
(Intermediate AA32)

To a solution of methanolic ammonia (5 mL) was added 2-chloro-5-((cyclobutylmethyl)sulfonyl)pyridine (0.900 g, 3.65 mmol). After stirring at RT for 16 h, the reaction mixture was diluted in water and extracted with ethyl acetate. The combined organic solution was concentrated under reduced pressure to give crude material. The residue was purified by column chromatography eluting with 30% ethyl acetate in hexane to give Intermediate AA32 (0.100 g, 12.06%). MS (ES): m/z 227.12 [M+H]⁺.

Synthesis of 1-(2-aminopyridin-4-yl)piperidin-4-ol
(Intermediate AA34)

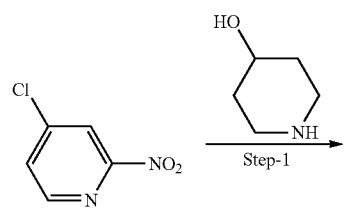

Intermediate AA34-1

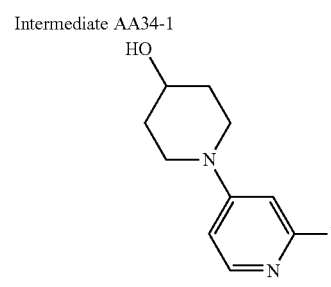

Intermediate AA34-2

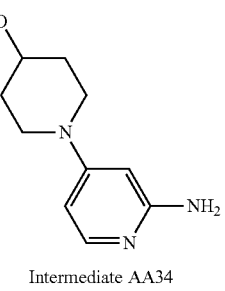

Intermediate AA34

1-(2-aminopyridin-4-yl)piperidin-4-ol (Intermediate AA34) was prepared from 4-chloro-2-nitropyridine (Intermediate AA34-1) and piperidin-4-ol in a similar fashion to that described 1-(6-amino-5-methoxypyridin-3-yl)piperidin-4-ol (General process Intermediate AA7). 1.37 g, 83.29%). MS (ES): m/z 194.12 [M+H]⁺

Synthesis of 1-(6-aminopyridin-3-yl)azepan-4-ol
(Intermediate AA37)

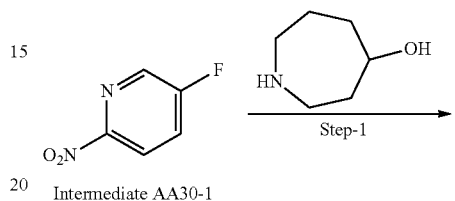

Intermediate AA30-1

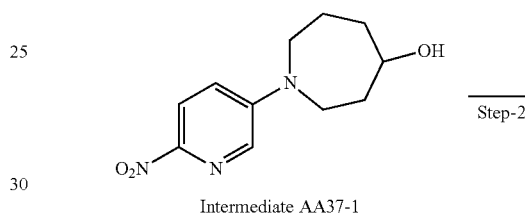

Intermediate AA37-1

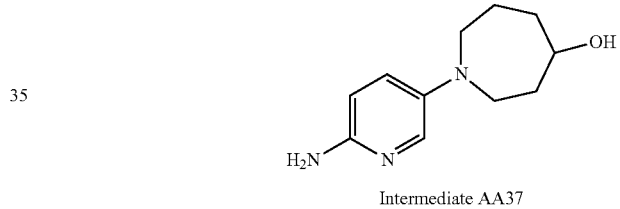

Intermediate AA37

1-(6-aminopyridin-3-yl)azepan-4-ol (Intermediate AA37) was prepared from 5-fluoro-2-nitropyridine (Intermediate AA30-1) and azepan-4-ol in a similar fashion to that described in 5-((3aR,6aS)-tetrahydro-1H-furo[3,4-c]pyrrol-5(3H)-yl)pyridin-2-amine (General process Intermediate AA30) (0.500 g, 81.76%). MS (ES): m/z 208.14 [M+H]⁺

Synthesis of
5-(2-(methoxymethyl)morpholino)pyridin-2-amine
(Intermediate AA39)

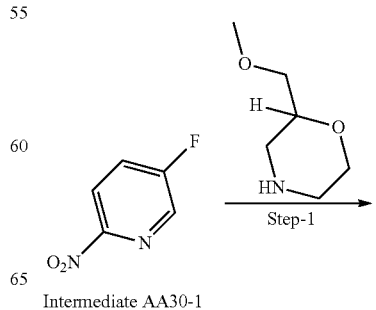

Intermediate AA30-1

779
-continued

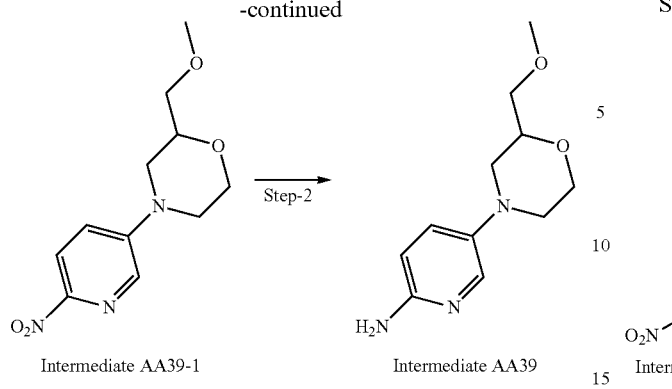

Intermediate AA39-1 → Intermediate AA39

5-(2-(methoxymethyl)morpholino)pyridin-2-amine (Intermediate AA37) was prepared from 5-fluoro-2-nitropyridine (Intermediate AA30-1) and 2-(methoxymethyl)morpholine in a similar fashion to that described in 5-(3aR,6aS)-5-(6-nitropyridin-3-yl)hexahydro-1H-furo[3,4-c]pyrrole (General process Intermediate AA30). (0.700 g, 79.4%). MS (ES): m/z 224.14 [M+H]$^+$ Synthesis of 4-(6-aminopyridin-3-yl)-1,4-oxazepan-6-ol (Intermediate AA43)

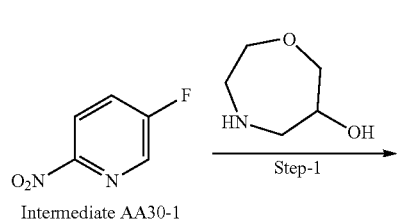

Intermediate AA30-1

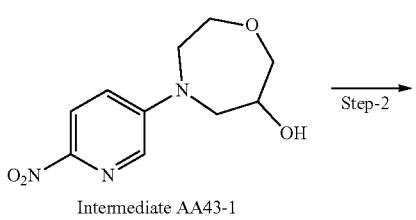

Intermediate AA43-1

Intermediate AA43

4-(6-aminopyridin-3-yl)-1,4-oxazepan-6-ol (Intermediate AA43) was prepared from 5-fluoro-2-nitropyridine (Intermediate AA30-1) and 1,4-oxazepan-6-ol in a similar fashion to that described in 5-(3 aR,6aS)-5-(6-nitropyridin-3-yl) hexahydro-1H-furo[3,4-c]pyrrole (General process Intermediate AA30). (0.7 g, 61.56%). MS (ES): m/z 210.26 [M+H]$^+$

780

Synthesis of (S)-2-(4-(6-aminopyridin-3-yl)morpholin-2-yl)propan-2-ol (Intermediate AA48)

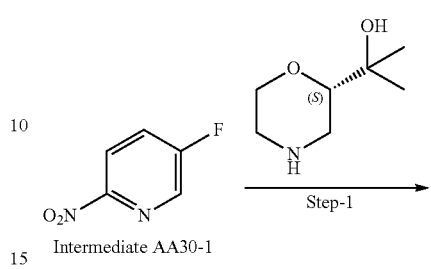

Intermediate AA30-1

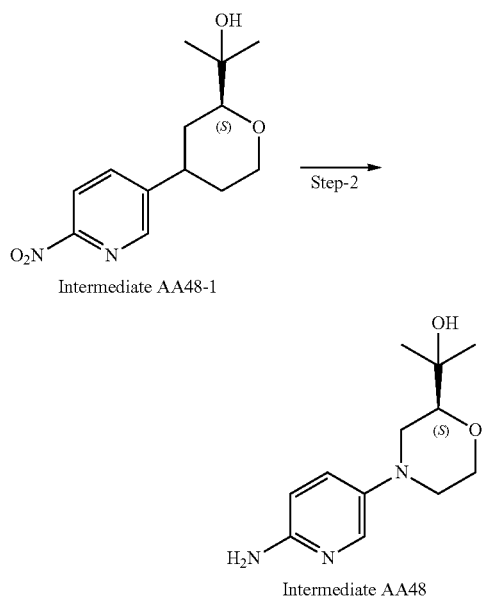

Intermediate AA48-1

Intermediate AA48

(S)-2-(4-(6-aminopyridin-3-yl)morpholin-2-yl)propan-2-ol (Intermediate AA43) was prepared from 5-fluoro-2-nitropyridine (Intermediate AA30-1) and (S)-2-(morpholin-2-yl) propan-2-ol in a similar fashion to that described in 5-(3aR, 6aS)-5-(6-nitropyridin-3-yl)hexahydro-1H-furo[3,4-c] pyrrole (General process intermediate AA30). (0.7 g, 61.56%). (4 g, 75%). MS (ES): m/z 237.15 [M+H]$^+$ Synthesis of ((3R,4R)-1-(6-aminopyridin-3-yl)-4-fluoropiperidin-3-ol (Intermediate AA49)

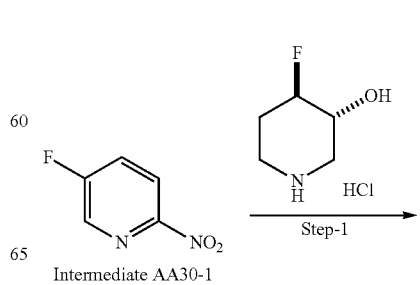

Intermediate AA30-1

-continued

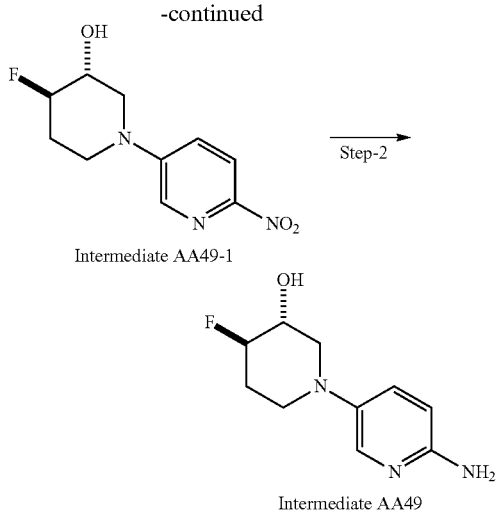

Intermediate AA49-1

Intermediate AA49

((3R,4R)-1-(6-aminopyridin-3-yl)-4-fluoropiperidin-3-ol (Intermediate AA49) was prepared from 5-fluoro-2-nitropyridine (Intermediate AA30-1) and (3R,4R)-4-fluoropiperidin-3-ol in a similar fashion to that described in 5-(3aR, 6aS)-5-(6-nitropyridin-3-yl)hexahydro-1H-furo[3,4-c]pyrrole (General process intermediate AA30). (0.500 g, 63.44%). MS (ES): m/z 212.11 [M+H]$^+$ Synthesis of 1-(6-aminopyridin-3-yl)-2-methylpiperidin-4-ol (Intermediate AA50)

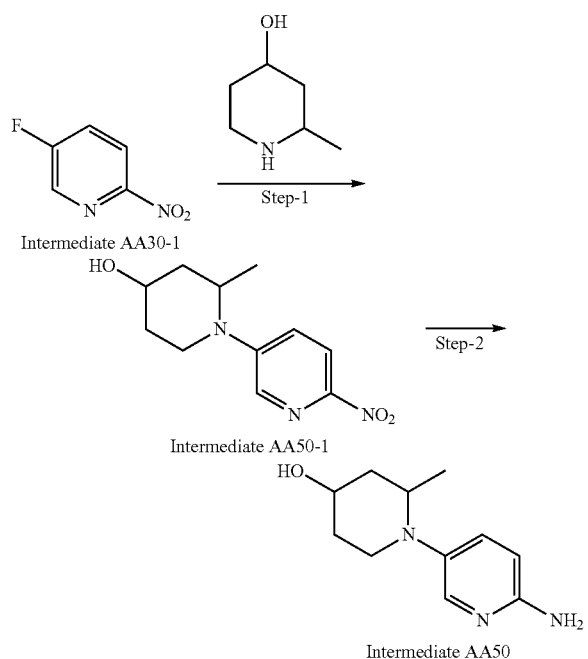

1-(6-aminopyridin-3-yl)-2-methylpiperidin-4-ol (Intermediate AA50) was prepared from 5-fluoro-2-nitropyridine (Intermediate AA30-1) and 2-methylpiperidin-4-ol in a similar fashion to that described in 5-(3aR,6aS)-5-(6-nitropyridin-3-yl)hexahydro-1H-furo[3,4-c]pyrrole (General process intermediate AA30). (0.900 gm, 93.75%) MS (ES): m/z 207 [M+H]$^+$ Synthesis of (1R,2S)-2-((6-aminopyridin-2-yl)oxy)cyclopentan-1-ol (Intermediate AA51)

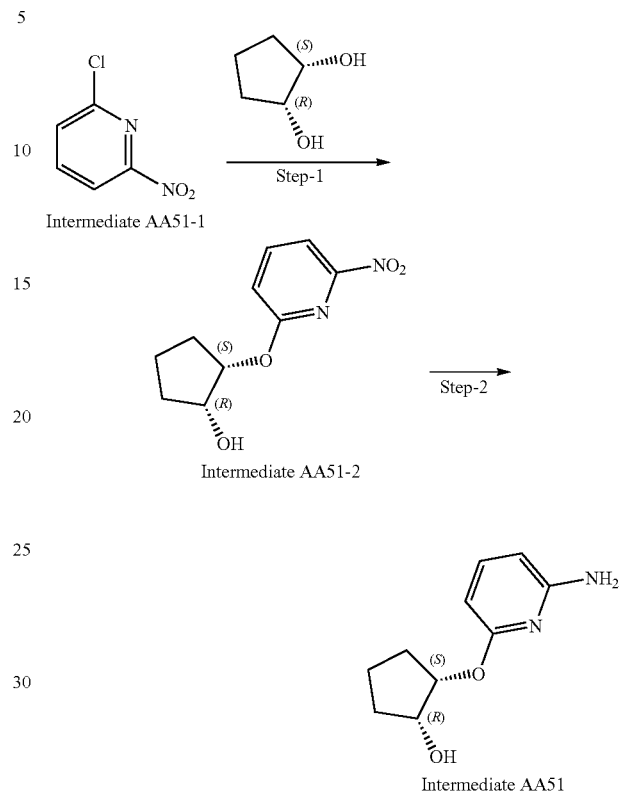

Step-1 Synthesis of (1R,2S)-2((6-nitropyridin-2-yl)oxy)cyclopentan-1-ol (Intermediate AA51-2)

To a solution of 2-chloro-6-nitropyridine (3.0 g 18.98 mmol, 1.0 eq.) and (1R,2S)-cyclopentane-1,2-diol (2.3 g 22.77 mmol, 1.2 eq.) in dry DMF (36 mL) was added potassium carbonate (7.8 g, 56.94 mmol, 3.0 eq) at RT. After stirring at 120° C. for 16 h, the reaction mixture was poured into ice water and extracted with ethyl acetate (2×120 mL). The combined organic extracts were washed with brine (100 mL), dried over Na$_2$SO$_4$, filtered, and concentrated under reduced pressure to afford crude material. The residue was purified by column chromatography eluting with 3.0% ethyl acetate gradient in hexane to afford Intermediate AA51-2 (0.330 g, 8.0%) MS (ES) m/z 225.08 (M+H)$^+$.

Step-2 Synthesis of (1R,2S)-2-((6-aminopyridin-2-yl)oxy)cyclopentan-1-ol (Intermediate AA51)

To a suspension of Intermediate AA51-2 (0.3 g, 1.33 mmol) in methanol (10 mL) was added 10% Pd/C (0.250 g) was hydrogenated at atmospheric pressure for 6 h at RT. After completion of reaction, the reaction mixture was filtered through celite-bed and washed with methanol. The filtrate was concentrated under reduced pressure to afford crude material which was used in next Step without purification. Intermediate AA51 (0.268 g, 98.12%). MS (ES): m/z 195.1 [M+H]$^+$,

Synthesis of 1-(1-(6-aminopyridin-3-yl)piperidin-3-yl)ethan-1-ol (Intermediate AA52)

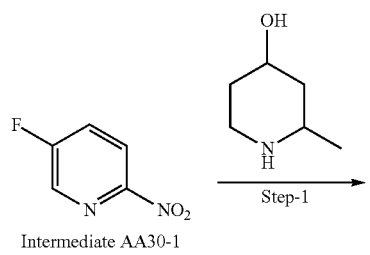

Intermediate AA52-1

Intermediate AA52

1-(1-(6-aminopyridin-3-yl)piperidin-3-yl)ethan-1-ol (Intermediate AA52) was prepared from 5-fluoro-2-nitropyridine (Intermediate AA30-1) and 2-methylpiperidin-4-ol in a similar fashion to that described in 5-(3aR,6aS)-5-(6-nitropyridin-3-yl)hexahydro-1H-furo[3,4-c]pyrrole (General process intermediate AA30). (1.1 gm, 78.6%) MS (ES): m/z 222.1 [M+H]$^+$

Synthesis of (3R,4S)-1-(6-aminopyridin-3-yl)-4-fluoropiperidin-3-ol (Intermediate AA54)

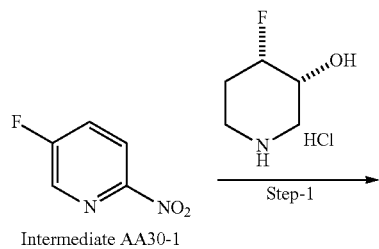

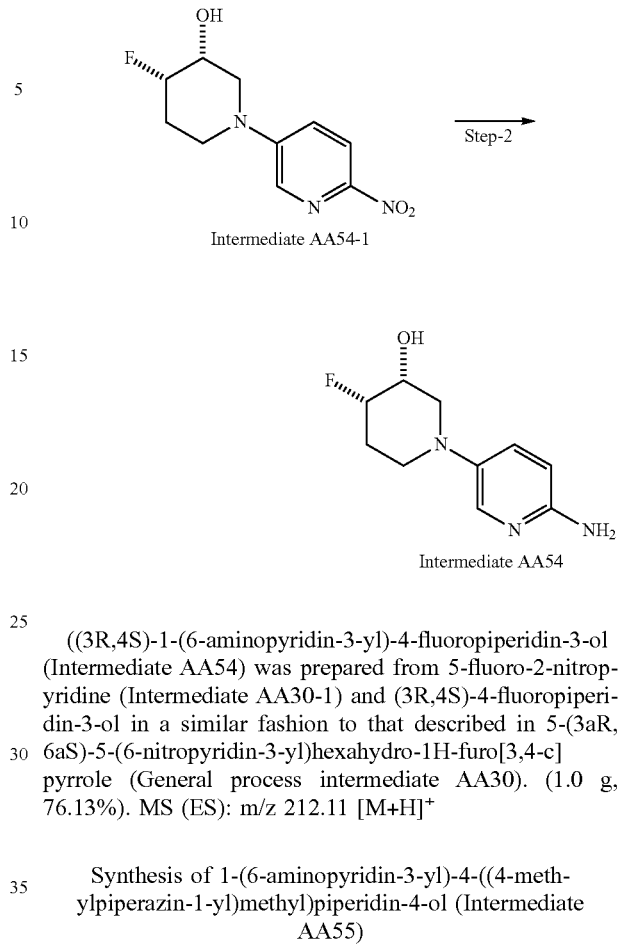

Intermediate AA54-1

Intermediate AA54

((3R,4S)-1-(6-aminopyridin-3-yl)-4-fluoropiperidin-3-ol (Intermediate AA54) was prepared from 5-fluoro-2-nitropyridine (Intermediate AA30-1) and (3R,4S)-4-fluoropiperidin-3-ol in a similar fashion to that described in 5-(3aR,6aS)-5-(6-nitropyridin-3-yl)hexahydro-1H-furo[3,4-c]pyrrole (General process intermediate AA30). (1.0 g, 76.13%). MS (ES): m/z 212.11 [M+H]$^+$

Synthesis of 1-(6-aminopyridin-3-yl)-4-((4-methylpiperazin-1-yl)methyl)piperidin-4-ol (Intermediate AA55)

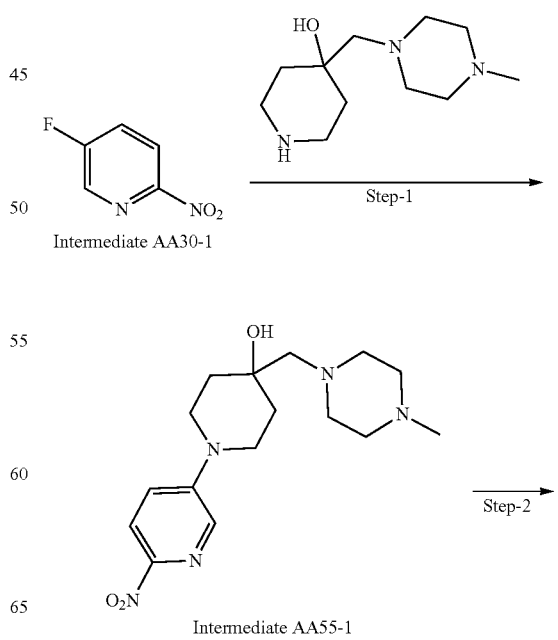

Intermediate AA55-1

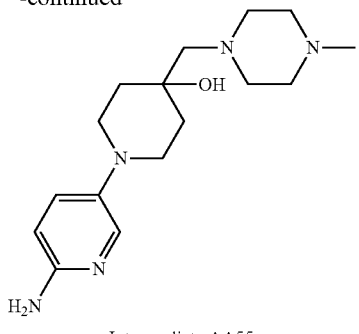

Intermediate AA55

1-(6-aminopyridin-3-yl)-4-(4-methylpiperazin-1-yl)
methyl)piperidin-4-ol (Intermediate AA55) was prepared
from 5-fluoro-2-nitropyridine (Intermediate AA30-1) and
4-((4-methylpiperazin-1-yl)methyl)piperidin-4-ol in a similar fashion to that described in 5-(3aR,6aS)-5-(6-nitropyridin-3-yl)hexahydro-1H-furo[3,4-c]pyrrole (General process intermediate AA30). (0.8 g, 87.75%). MS (ES): m/z 306.2 [M+H]$^+$ Synthesis of 1-(6-aminopyridin-3-yl)-4-((dimethylamino)methyl)piperidin-4-ol (Intermediate AA56)

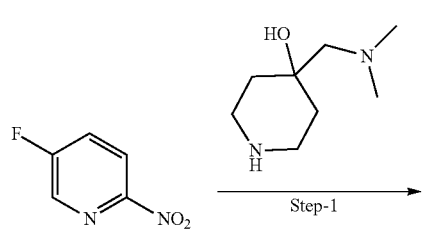

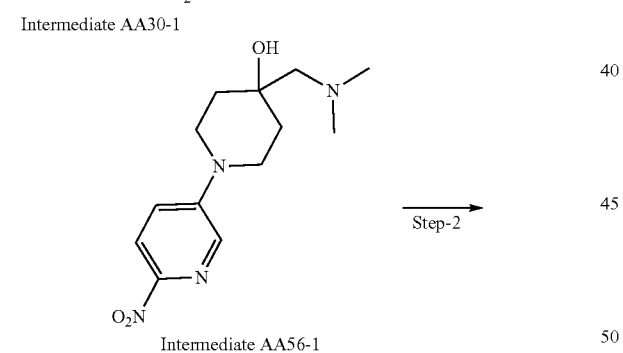

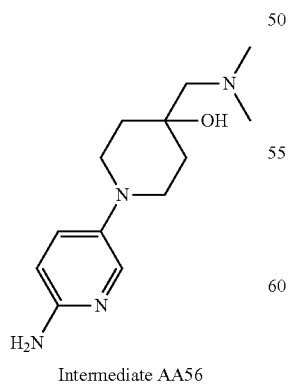

Intermediate AA56

1-(6-aminopyridin-3-yl)-4-((dimethylamino)methyl)piperidin-4-ol (Intermediate AA56) was prepared from 5-fluoro-2-nitropyridine (Intermediate AA30-1) and 4-((dimethylamino)methyl)piperidin-4-ol in a similar fashion to that described in 5-(3aR,6aS)-5-(6-nitropyridin-3-yl)hexahydro-1H-furo[3,4-c]pyrrole (General process intermediate AA30). (0.85 g, 86.53%). MS (ES): m/z 251.4 [M+H]$^+$ Synthesis of 1-(6-aminopyridin-3-yl)-4-morpholinopiperidin-4-ol (Intermediate AA58)

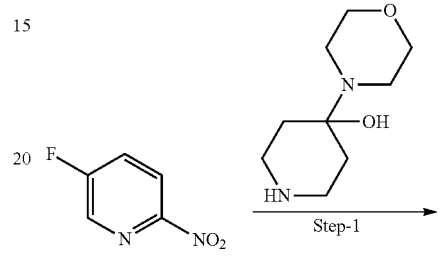

Intermediate AA30-1

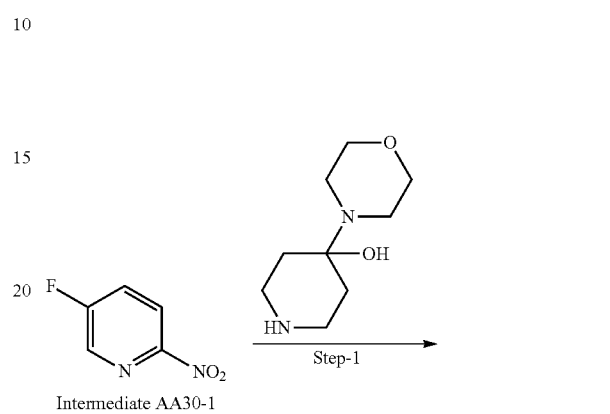

Intermediate AA58-1

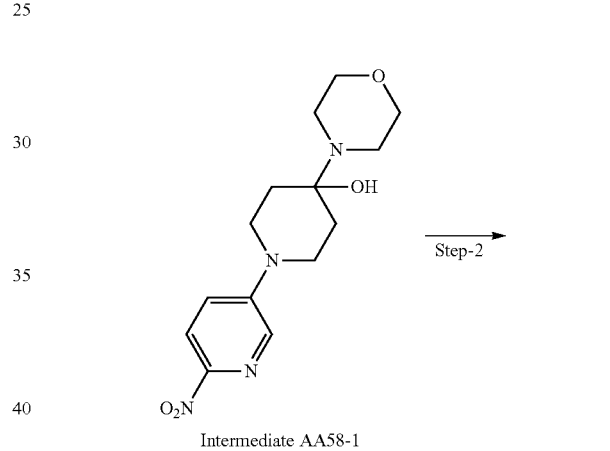

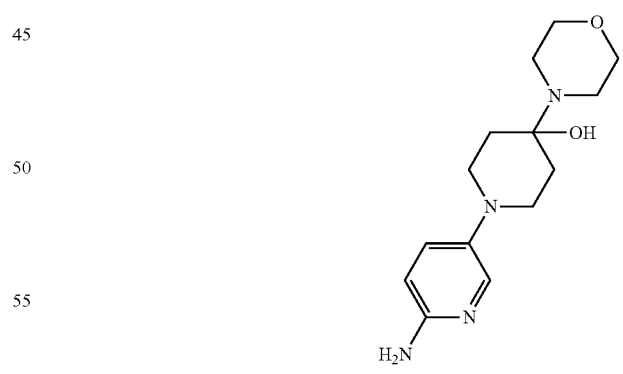

Intermediate AA58

1-(6-aminopyridin-3-yl)-4-morpholinopiperidin-4-ol (Intermediate AA58) was prepared from 5-fluoro-2-nitropyridine (Intermediate AA30-1) and 4-morpholinopiperidin-4-ol in a similar fashion to that described in 5-(3aR,6aS)-5-(6-nitropyridin-3-yl)hexahydro-1H-furo[3,4-c]pyrrole (General process intermediate AA30). (0.40 g, 44.34%). MS (ES): m/z 277.4 [M+H]$^+$

Synthesis of 5-((oxetan-3-ylmethyl)sulfonyl)pyridin-2-amine (Intermediate AA59)

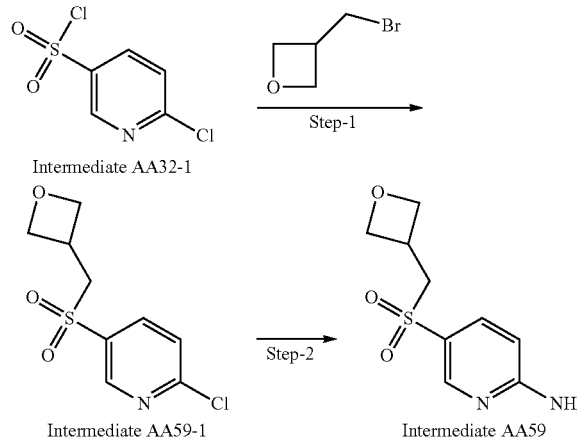

5-((oxetan-3-ylmethyl)sulfonyl)pyridin-2-amine (Intermediate AA59) was prepared from 6-chloropyridine-3-sulfonyl chloride (Intermediate AA32-1) and 3-(bromomethyl)oxetane in a similar fashion to that described in 5-((cyclobutylmethyl)sulfonyl)pyridin-2-amine (General process intermediate AA32). (0.19 g, 89.94%). MS (ES): m/z 277.4 [M+H]$^+$

Synthesis of 5-(2-((dimethylamino)methyl)morpholino)pyridin-2-amine (Intermediate AA63)

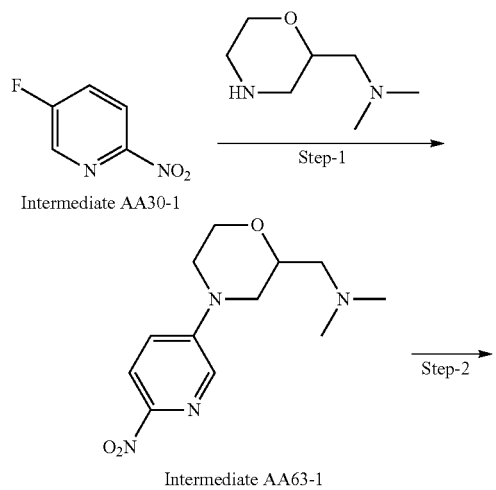

5-(2-((dimethylamino)methyl)morpholino)pyridin-2-amine (Intermediate AA63) was prepared from 5-fluoro-2-nitropyridine (Intermediate AA30-1) and N,N-dimethyl-1-(morpholin-2-yl)methanamine in a similar fashion to that described in 5-(3aR,6aS)-5-(6-nitropyridin-3-yl)hexahydro-1H-furo[3,4-c]pyrrole (General process intermediate AA30). (0.60 g, 74.34%). MS (ES): m/z 237.4 [M+H]$^+$

Synthesis of 1-(6-aminopyridin-3-yl)-3-((dimethylamino)methyl)piperidin-3-ol (Intermediate AA64)

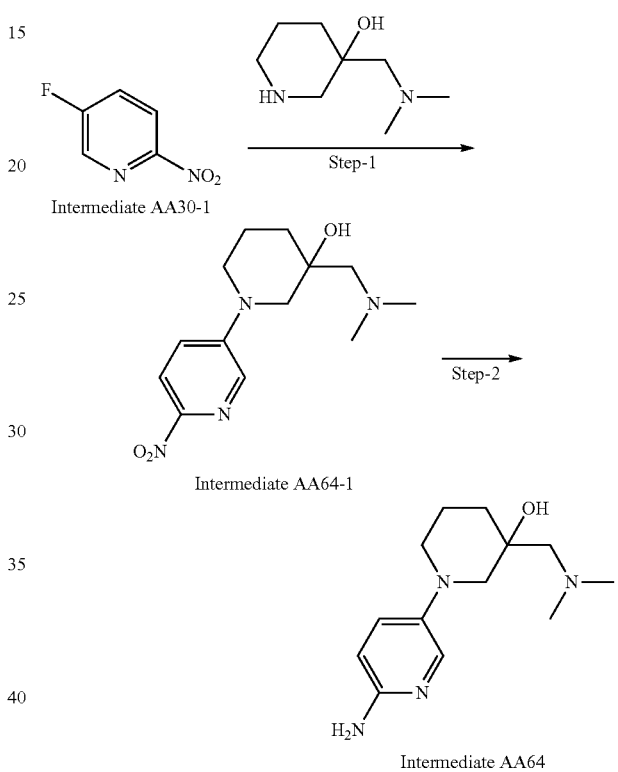

1-(6-aminopyridin-3-yl)-3-((dimethylamino)methyl)piperidin-3-ol (Intermediate AA64) was prepared from 5-fluoro-2-nitropyridine (Intermediate AA30-1) and 3-((dimethylamino)methyl)piperidin-3-ol in a similar fashion to that described in 5-(3aR,6aS)-5-(6-nitropyridin-3-yl)hexahydro-1H-furo[3,4-c]pyrrole (General process intermediate AA30). (0.60 g, 78%). MS (ES): m/z 251.4 [M+H]$^+$

Synthesis of 4-(6-aminopyridin-3-yl)-1-(2-(dimethylamino)ethyl)piperidin-2-one (Intermediate AA65)

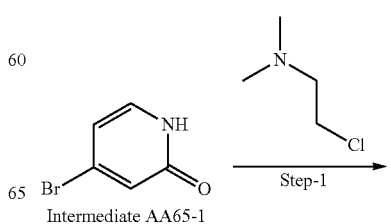

789
-continued

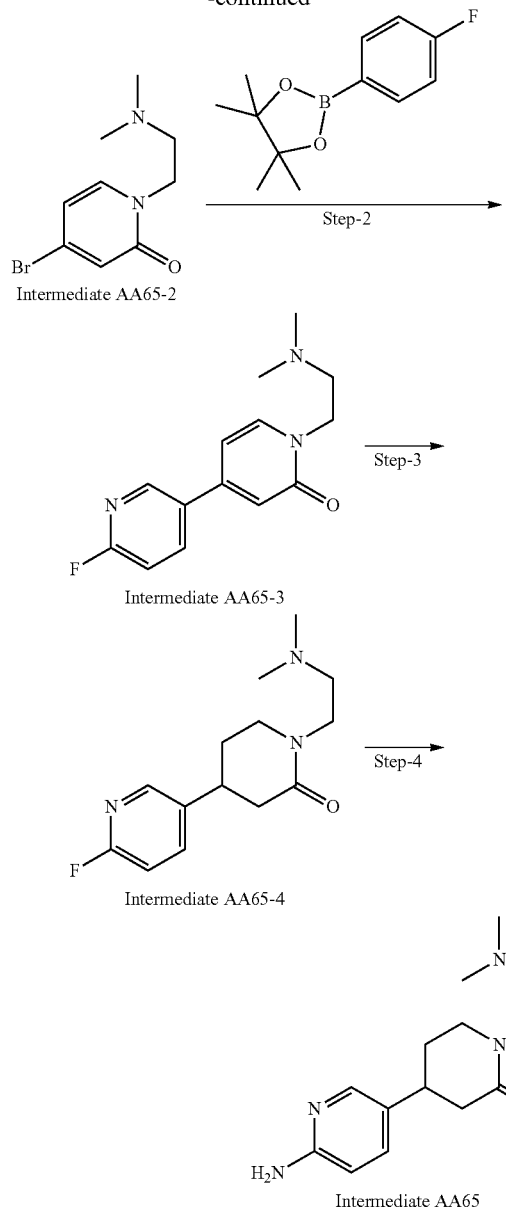

Step-1 Synthesis of 4-bromo-1-(2-(dimethylamino)ethyl)pyridin-2(1H)-one (Intermediate AA65-1)

Prepared as described in WO2009/74812 A1.

Step-2, 3, 4 Synthesis of 4-(6-aminopyridin-3-yl)-1-(2-(dimethylamino)ethyl)piperidin-2-one (Intermediate AA65)

4-(6-aminopyridin-3-yl)-1-(2-(dimethylamino)ethyl)piperidin-2-one (Intermediate AA65) was prepared from 4-bromo-1-(2-(dimethylamino)ethyl)pyridin-2(1H)-one (Intermediate AA65-1) and 2-fluoro-5-(4,4,5,5-tetramethyl-1,3,2-dioxaborolan-2-yl)pyridine in a similar fashion to that described in 4-(6-aminopyridin-3-yl)-1-methylpiperidin-2-one (Intermediate AA8) (1 g, 65.65%). MS (ES): m/z 266.4 [M+H]$^+$

790
Synthesis of 1-(6-aminopyridin-3-yl)-4-(pyrrolidin-1-ylmethyl)piperidin-4-ol (Intermediate AA66)

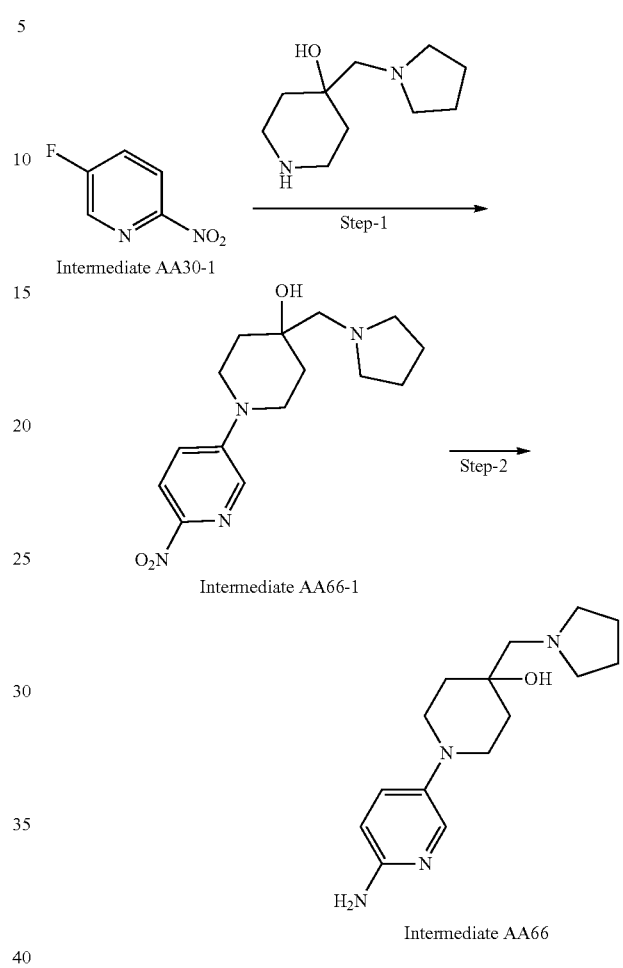

1-(6-aminopyridin-3-yl)-4-(pyrrolidin-1-ylmethyl)piperidin-4-ol (Intermediate AA66) was prepared from 5-fluoro-2-nitropyridine (Intermediate AA30-1) 4-(pyrrolidin-1-ylmethyl)piperidin-4-ol in a similar fashion to that described in 5-(3aR,6aS)-5-(6-nitropyridin-3-yl)hexahydro-1H-furo[3,4-c]pyrrole (General process intermediate AA30). (1.5 gm, 90.90%) MS (ES): m/z 277.3 [M+H]$^+$ Synthesis of 1-(6-aminopyridin-3-yl)-3-((4-methylpiperazin-1-yl)methyl)piperidin-3-ol (Intermediate AA67)

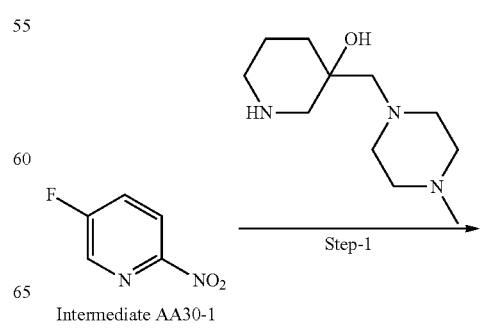

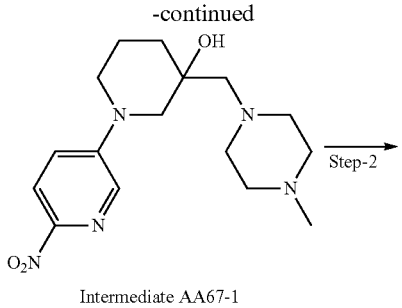

Intermediate AA67-1

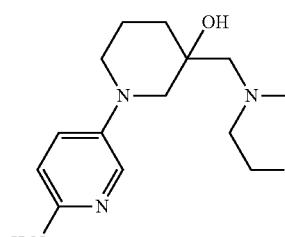

Intermediate AA67

1-(6-aminopyridin-3-yl)-3-((4-methylpiperazin-1-yl)methyl)piperidin-3-ol (Intermediate AA67) was prepared from 5-fluoro-2-nitropyridine (Intermediate AA30-1) and 3-((4-methylpiperazin-1-yl)methyl)piperidin-3-ol in a similar fashion to that described in 5-(3aR,6aS)-5-(6-nitropyridin-3-yl)hexahydro-1H-furo[3,4-c]pyrrole (General process intermediate AA30). (0.80 g, 79%). MS (ES): m/z 306.4 [M+H]$^+$ Synthesis of 1-(6-aminopyridin-3-yl)-3-(methoxymethyl)piperidin-3-ol (Intermediate AA69)

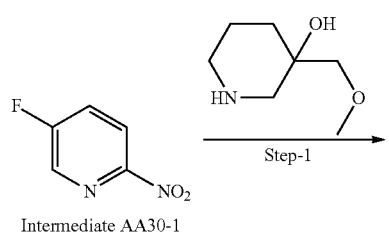

Intermediate AA69-1

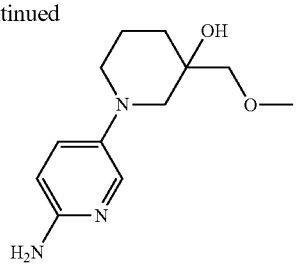

Intermediate AA69

1-(6-aminopyridin-3-yl)-3-(methoxymethyl)piperidin-3-ol (Intermediate AA69) was prepared from 5-fluoro-2-nitropyridine (Intermediate AA30-1) and 3-(methoxymethyl)piperidin-3-ol in a similar fashion to that described in 5-(3aR,6aS)-5-(6-nitropyridin-3-yl)hexahydro-1H-furo[3,4-c]pyrrole (General process intermediate AA30). (0.9 g, 84%). MS (ES): m/z 238.4 [M+H]$^+$ Synthesis of 4-(6-aminopyridin-3-yl)-4-azaspiro[2.5]octan-6-ol (Intermediate AA70)

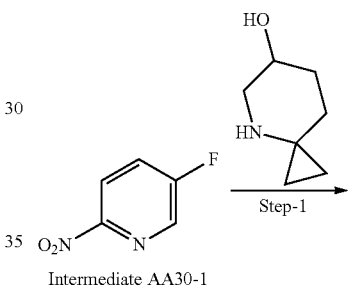

Intermediate AA30-1

Intermediate AA70-1

Intermediate AA70

4-(6-aminopyridin-3-yl)-4-azaspiro[2.5]octan-6-ol (Intermediate AA70) was prepared from 5-fluoro-2-nitropyridine (Intermediate AA30-1) and 4-azaspiro[2.5]octan-6-ol in a similar fashion to that described in 5-(3aR,6aS)-5-(6-nitropyridin-3-yl)hexahydro-1H-furo[3,4-c]pyrrole (General process intermediate AA30). (0.17 g, 94%). MS (ES): m/z 220.4 [M+H]$^+$

Synthesis of (3S,4S)-1-(6-aminopyridin-3-yl)-3-fluoropiperidin-4-ol (Intermediate AA72)

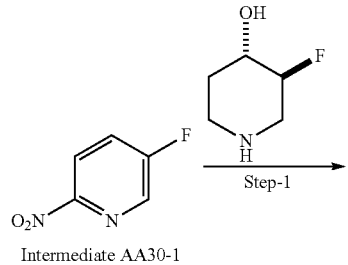

Intermediate AA30-1

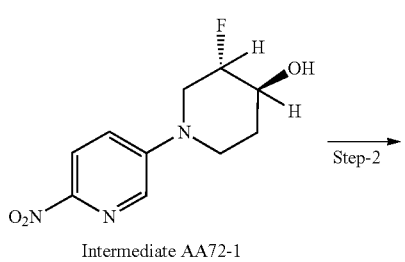

Intermediate AA72-1

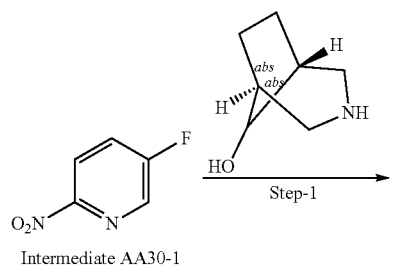

Intermediate AA72

(3S,4S)-1-(6-aminopyridin-3-yl)-3-fluoropiperidin-4-ol (Intermediate AA72) was prepared from 5-fluoro-2-nitropyridine (Intermediate AA30-1) and (3S,4S)-3-fluoropiperidin-4-ol in a similar fashion to that described in 5-(3aR,6aS)-5-(6-nitropyridin-3-yl)hexahydro-1H-furo[3,4-c]pyrrole (General process intermediate AA30). (2.5 g, 52%). MS (ES): m/z 212.2 [M+H]$^+$

Synthesis of ((1R,5S)-3-(6-aminopyridin-3-yl)-3-azabicyclo[3.2.1]octan-8-ol (Intermediate AA73)

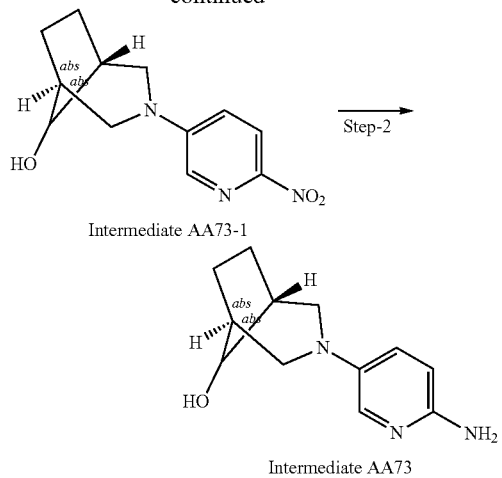

Intermediate AA73-1

Intermediate AA73

(1R,5S)-3-(6-aminopyridin-3-yl)-3-azabicyclo[3.2.1]octan-8-ol (Intermediate AA73) was prepared from 5-fluoro-2-nitropyridine (Intermediate AA30-1) (1R,5S)-3-azabicyclo[3.2.1]octan-8-ol in a similar fashion to that described in 5-(3aR,6aS)-5-(6-nitropyridin-3-yl)hexahydro-1H-furo[3,4-c]pyrrole (General process intermediate AA30). (0.9 g, 93%). MS (ES): m/z 220.2 [M+H]$^+$

Synthesis of 4-(6-aminopyridin-2-yl)-1-methylpiperidin-4-ol (Intermediate AA74)

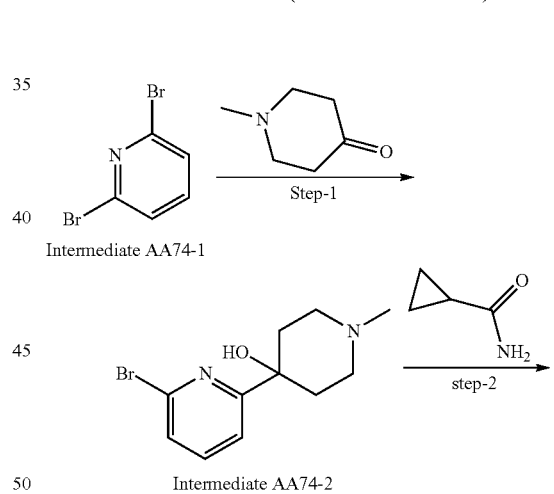

Intermediate AA74-1

Intermediate AA74-2

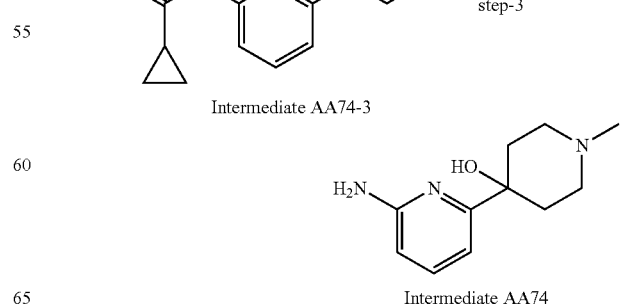

Intermediate AA74-3

Intermediate AA74

Step-1 Synthesis of 4-(6-bromopyridin-2-yl)-1-methylpiperidin-4-ol (Intermediate AA74-2)

To Intermediate AA74-1 (7.5 g 31.77 mmol) dissolved in THF (25 mL) was added at −78° C. a solution of n-butyllithium (19 mL, 1.59 mmol, 1.5 eq) in diethyl ether (35 mL). After stirring at −78° C. for 30 min, 1-methylpiperidin-4-one (3.6 g 31.77 mmol) was added. After stirring for 45 min at −78° C., the reaction mixture was diluted with sodium bicarbonate solution (200 mL) and extracted with ethyl acetate (3×150 mL). The combined organic extracts were washed with brine (200 mL), dried over $Na_2SO_4$, filtered, and concentrated under reduced pressure. The residue was purified by trituration with diethyl ether to afford Intermediate AA74-2 (3 g, 34.91%) MS (ES) m/z 272.2 $(M+H)_+$

Step-2 Synthesis of N-(6-(4-hydroxy-1-methylpiperidin-4-yl)pyridin-2-yl)cyclopropanecarboxamide (Intermediate AA74-3)

To a solution of Intermediate AA74-2 (1.7 g, 6.29 mmol) in 1,4-dioxane (20 mL) were added cyclopropanecarboxamide (0.641 g, 7.54 mmol, 1.2 eq) and $CS_2CO_3$ (6.1 g, 18.87 mmol, 3.0 eq). After degassing under $N_2$ stream for 15 min, Xantphos (0.363 g, 0.62 mmol, 0.1 eq) and $Pd_2(dba)_3$ (0.567 g, 0.62 mmol, 0.1 eq) were added. After stirring at 110° C. for 2 h, the reaction mixture was cooled to RT, diluted with water (90 mL), and extracted with ethyl acetate (3×50 mL). The combined organic extracts were washed with brine (100 mL), dried over $Na_2SO_4$, filtered, and concentrated under reduced pressure. The residue was purified by silica gel chromatography eluting with 2.0% methanol in DCM to afford Intermediate AA74-3 (1.7 g, 98.48%), MS (ES): m/z=276.2 $(M+H)^+$

Step-3 Synthesis of 4-(6-aminopyridin-2-yl)-1-methylpiperidin-4-ol (Intermediate AA74)

To a solution of Intermediate AA74-3 (1.7 g, 6.18 mmol) in methanol:water (30 mL:5 mL) was added sodium hydroxide (2.47 g, 61.8 mmol, 10 eq). After stirring for 16 h at 80° C., the reaction mixture was concentrated under reduced pressure. The residue was diluted with water (30 mL) at 10° C. and acidified with 1N hydrochloric acid adjusting pH-6-6.5. The solution was extracted with DCM (3×30 mL). The combined organic layer was washed with brine solution, dried over sodium sulfate, and concentrated under reduced pressure to obtain crude material which was used in next Step without purification. Intermediate AA74 (0.750 g, 58.61%) MS (ES): m/z=208.2 $(M+H)^-$

Synthesis of 1-(6-aminopyridin-3-yl)-3-(methoxymethyl)piperidin-4-ol (Intermediate AA77)

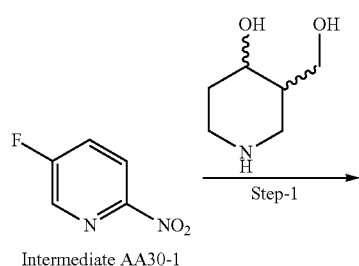

Intermediate AA30-1

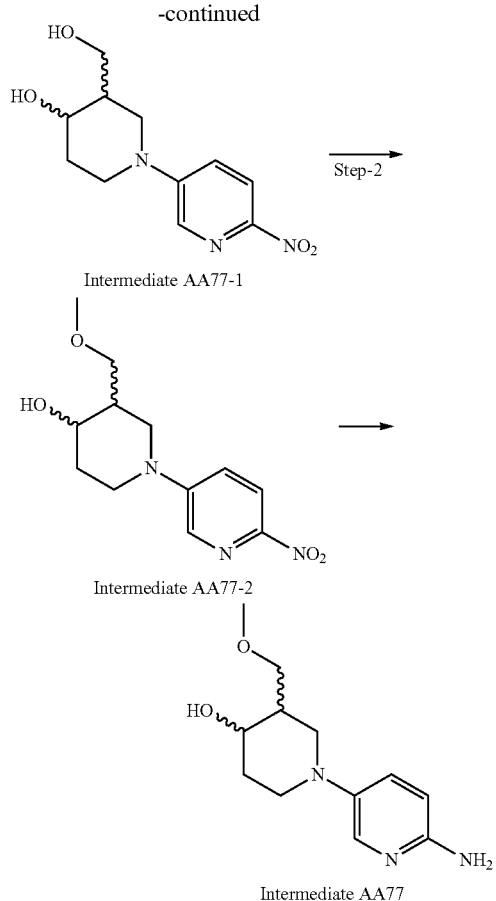

Intermediate AA77-1

Intermediate AA77-2

Intermediate AA77

Step-1 Synthesis of 3-(hydroxymethyl)-1-(6-nitropyridin-3-yl)piperidin-4-ol (Intermediate AA77-1)

3-(hydroxymethyl)-1-(6-nitropyridin-3-yl)piperidin-4-ol (Intermediate AA77-1) was prepared from 5-fluoro-2-nitropyridine (Intermediate AA30-1) and 3-(hydroxymethyl)piperidin-4-ol in a similar fashion to that described in (3aR, 6aS)-5-(6-nitropyridin-3-yl)hexahydro-1H-furo[3,4-c]pyrrole (Intermediate AA30-2). (2.1 g, 59%). MS (ES): m/z 254.2 $[M+H]^+$

Step-2 Synthesis of 3-(methoxymethyl)-1-(6-nitropyridin-3-yl)piperidin-4-ol (Intermediate AA77-2)

To a solution of 3-(hydroxymethyl)-1-(6-nitropyridin-3-yl)piperidin-4-ol (Intermediate AA77-1) (1.0 g, 3.9 mmol) in THF (25 mL), and sodium hydride (60%)(0.189 g, 7.9 mmol, 2 eq) was added MeI (0.2 mL, 4.6 mmol, 1.2 eq) at 0° C. After stirring at RT for 10 min, the reaction mixture was diluted with ice cool water (50 mL) and extracted into ethyl acetate (100 mL×3). The combined organic layers were washed with brine solution, dried over sodium sulfate, and concentrated under reduced pressure. The residue was purified using Column chromatography eluting with 50% ethyl acetate in hexane to afford Intermediate AA77-2 (0.600 g, 55%) MS (ES): m/z 267.2 $[M+H]^+$

Step-3 Synthesis of 1-(6-aminopyridin-3-yl)-3-(methoxymethyl)piperidin-4-ol (Intermediate AA77)

1-(6-aminopyridin-3-yl)-3-(methoxymethyl)piperidin-4-ol (Intermediate AA77) was prepared from 3-(methoxymethyl)-1-(6-nitropyridin-3-yl)piperidin-4-ol (Intermediate AA77-2) in a similar fashion to that described in (3aR,6aS)-5-(6-nitropyridin-3-yl)hexahydro-1H-furo[3,4-c]pyrrole (Intermediate AA30-2). (0.9 g, 92%). MS (ES): m/z 238.2 [M+H]⁺

Synthesis of Tert-Butyl 3-(6-chloropyridin-2-yl)azetidine-1-carboxylate (Intermediate AA78)

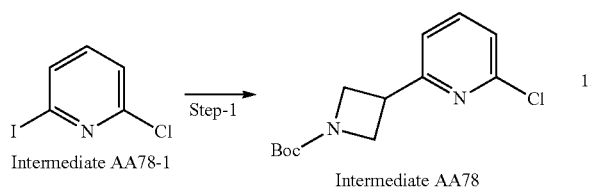

Intermediate AA78-1

Intermediate AA78

Step-1 Synthesis of Tert-Butyl 3-(6-chloropyridin-2-yl)azetidine-1-carboxylate (Intermediate AA78)

To a solution of Zn dust (0.830 g 12.72 mmol, 1.2 eq) in dry THF (25 mL) was added 1,2-dibromoethane (0.298 g, 1.59 mmol, 0.15 eq) at RT under N₂ atmosphere. After stirring at 80° C. for 10 min, the reaction mixture was cooled and trimethylsilyl chloride (0.16 g 1.48 mmol, 0.14 eq) dissolved in THF was added. After stirring for 45 min at RT, a solution of tert-butyl 3-iodoazetidine-1-carboxylate (3.0 g 10.60 mmol) in THF was added. After stirring for 2 h at RT, a solution of tris(dibenzylideneacetone)dipalladium(O) (0.096 g 0.106 mmol, 0.01 eq), tri(2-furyl)phosphine (0.123 g 0.53 mmol, 0.05 eq) and Intermediate AA78-1 (2.76 g 11.55 mmol, 1.09 eq) in THF were added. After stirring at 60° C. for 16 h, the reaction mixture was diluted with water (500 mL) and extracted with ethyl acetate (3×150 mL). The combined organic extracts were washed with brine (300 mL), dried over Na₂SO₄, filtered, and concentrated under reduced. The residue was purified by column chromatography eluting with 20% ethyl acetate in hexane to afford Intermediate AA78 (1.2 g, 42.14%) MS (ES) m/z 269.2 (M+H)⁺

Synthesis of 6-(1-methylpiperidin-3-yl)pyridin-2-amine (Intermediate AA80)

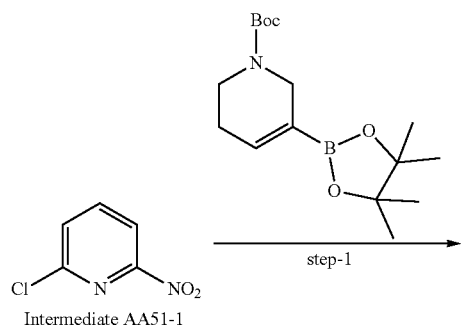

Intermediate AA51-1

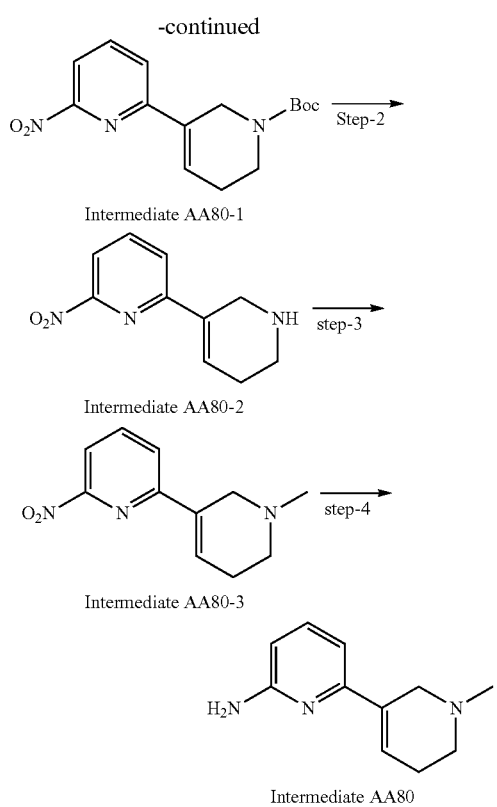

Intermediate AA80-1

Intermediate AA80-2

Intermediate AA80-3

Intermediate AA80

Step-1 Synthesis of Tert-Butyl 6-nitro-5',6'-dihydro-[2,3'-bipyridine]-1'(2'H)-carboxylate (Intermediate AA80-1)

A 100 mL seal tube was charged 2-chloro-6-nitropyridine (Intermediate AA51-1) (2 g, 12.61 mmol, 1.0 eq), tert-butyl5-(4,4,5,5-tetramethyl-1,3,2-dioxaborolan-2-yl)-3,6-dihydropyridine-1(2H)-carboxylate (4.67 g, 15.13 mmol, 1.2 eq), K₂CO₃ (5.26 g, 37.8 mmol), 1,4-dioxane (32 mL) and water (8 mL). The mixture was degassed and purged with argon for 10 min. The reaction mixture was treated with Pdcl2(dppf)DCM (0.51 g, 0.635 mmol 0.05 eq), purged with argon for 5 min, and heated at 100° C. for 3 h. After cooling to RT, the reaction mixture was diluted ethyl acetate (200 mL) and water (200 mL). The organic layer was collected and the aqueous phase was extracted with ethyl acetate (200 mL×2), combined organic extracts were washed with brine (100 mL) and dried over sodium sulfate, filtered and concentrated under reduced pressure to afford crude material which was purified using Column chromatography eluting with 50% ethyl acetate in hexane to afford Intermediate AA80-1) (2.4 g, 62%) MS (ES): m/z 306.2 [M+H]⁺

Step-2 Synthesis of 6-nitro-1',2',5',6'-tetrahydro-2,3'-bipyridine (Intermediate AA80-2)

To a solution of tert-butyl-6-nitro-5,6-dihydro-[2,3-bipyridine]-1'(2H)'-carboxylate (AA80-1) (2.4 g, 7.86 mmol) in DCM (40 mL) at 0° C. was added trifluoracetic acid (8 mL) dropwise at RT. After stirring for 1 h, the reaction mixture quenched with saturated sodium bicarbonate (200 mL) solution and extracted in DCM (100 mL×3). The combined organic extracts were washed with brine (100 mL) and dried over sodium sulfate, filtered and concentrated under reduced pressure to afford crude material which was purified using Column chromatography eluting with 50% ethyl acetate in hexane to afford Intermediate AA80-2) (1.6 g, 99%). MS (ES): m/z 206.10 [M+H]$^+$ Step-3 Synthesis of 1'-methyl-6-nitro-1',2',5',6'-tetrahydro-2,3'-bipyridine (Intermediate AA80-3)

A solution of 6-nitro-1',2',5',6'-tetrahydro-2',3'-bipyridine (Intermediate AA80-2) (1.6 g, 7.84 mmol, 1.0 eq), in DMF (20 mL) were added K$_2$CO$_3$ (3.24 g, 23.52 mmol 3.0 eq) and methyl iodide (3.3 g, 23.52 mmol 3.0 eq) at RT. After stirring for 4 h, the reaction mixture was diluted ethyl acetate (200 mL) and water (200 mL). The organic layer was collected, and the aqueous phase was extracted with ethyl acetate (200 mL×2). The combined organic extracts were washed with brine (100 mL) and dried over sodium sulfate, filtered and concentrated under reduced pressure to afford crude material which was purified using Column chromatography eluting with 40% ethyl acetate in Hexane to afford material (Intermediate AA80-3) (1.4 g, 81%). MS (ES): m/z 220.19 [M+H]$^+$ Step-4 Synthesis of 6-(1-methylpiperidin-3-yl)pyridin-2-amine (Intermediate AA80)

6-(1-methylpiperidin-3-yl)pyridin-2-amine (Intermediate AA80) was prepared from 1'-methyl-6-nitro-1',2',5',6'-tetrahydro-2,3'-bipyridine (Intermediate AA80-3) in a similar fashion to that described in (3aR,6aS)-5-(6-nitropyridin-3-yl)hexahydro-1H-furo[3,4-c]pyrrole (General process Intermediate AA30-2). (1 g, 90%). MS (ES): m/z 192.2 [M+H]$^+$ Synthesis of 5-(8-oxa-3-azabicyclo[3.2.1]octan-3-yl)pyridin-2-amine (Intermediate AA81)

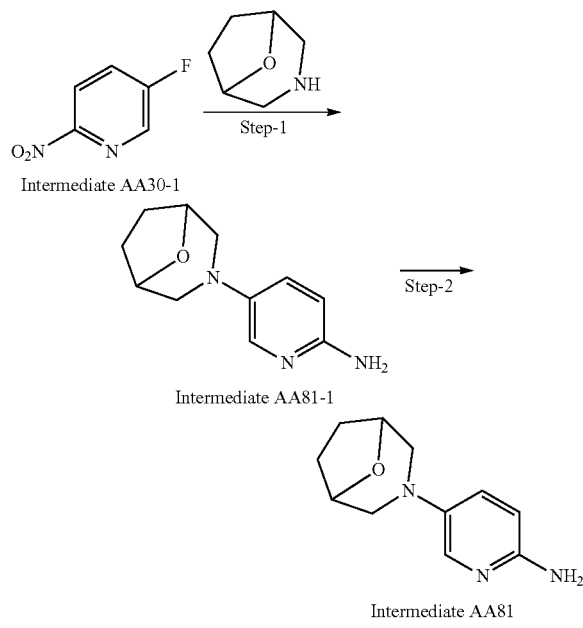

Step-1 Synthesis of 5-(8-oxa-3-azabicyclo[3.2.1]octan-3-yl)pyridin-2-amine (Intermediate AA81)

5-(8-oxa-3-azabicyclo[3.2.1]octan-3-yl)pyridin-2-amine (Intermediate AA81) was prepared from 5-fluoro-2-nitropyridine (Intermediate AA30-1) and 8-oxa-3-azabicyclo[3.2.1]octane in a similar fashion to that described in 5-(3aR,6aS)-5-(6-nitropyridin-3-yl)hexahydro-1H-furo[3,4-c]pyrrole (General process intermediate AA30). (0.9 g, 93%). MS (ES): m/z 206.2 [M+H]$^+$ Synthesis of 6-([1,3'-bipyrrolidin]-1'-yl)pyridin-2-amine (Intermediate AA83)

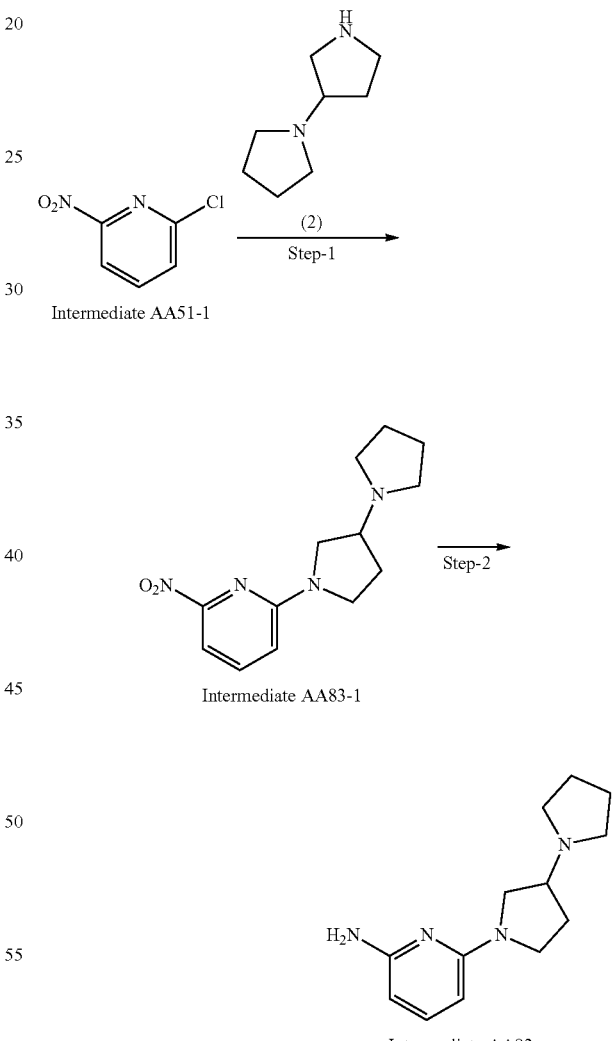

5-(8-oxa-3-azabicyclo[3.2.1]octan-3-yl)pyridin-2-amine (Intermediate AA83) was prepared from 2-chloro-6-nitropyridine (Intermediate AA51-1) and 1,3'-bipyrrolidine in a similar fashion to that described in tert-butyl 3-(6-aminopyridin-3-yl)-3,8-diazabicyclo[3.2.1]octane-8-carboxylate (General process intermediate AA6). (0.6 g, 93%). MS (ES): m/z 233.2 [M+H]$^+$

801
Synthesis of 5-(4-methyl-4-morpholinopiperidin-1-yl)pyridin-2-amine (Intermediate AA84)

802
Synthesis of (1-(6-aminopyridin-3-yl)-4-methylpiperidin-4-yl)methanol (Intermediate AA85)

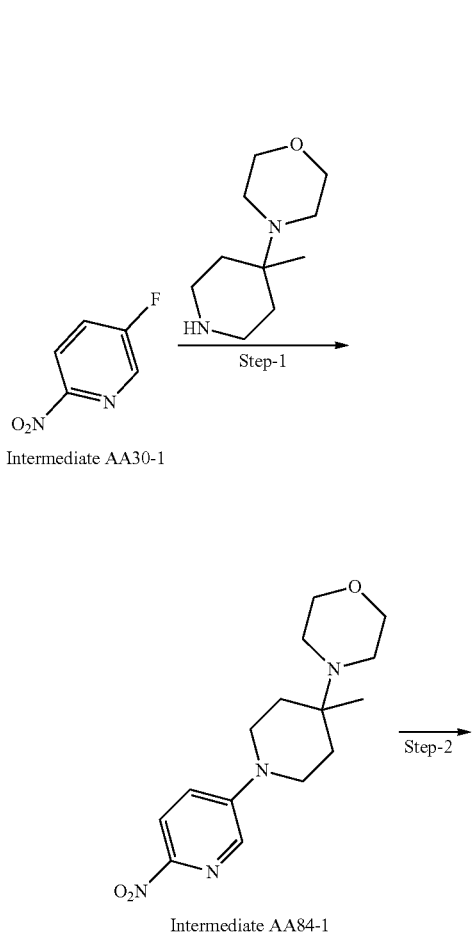

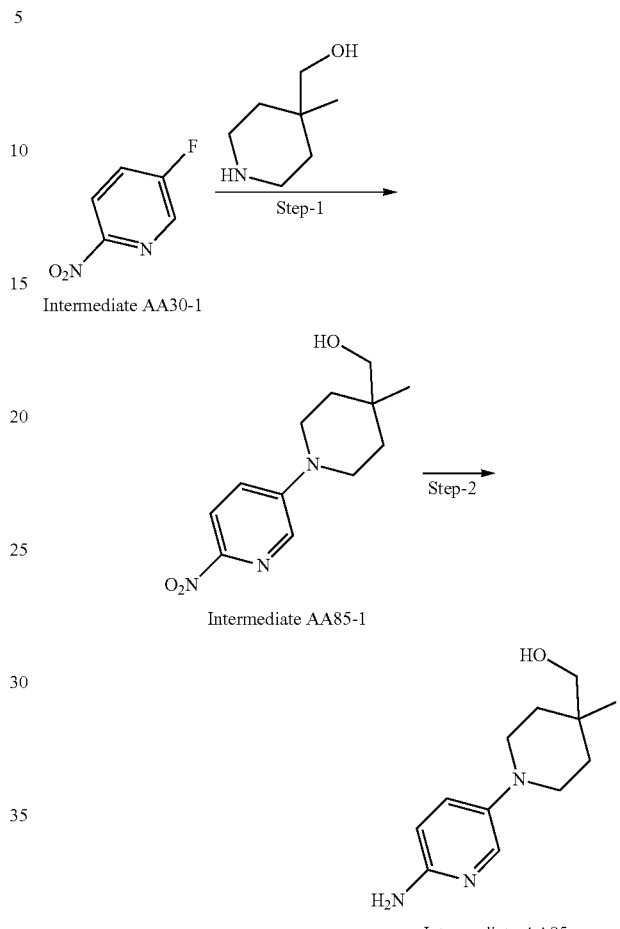

5-(4-methyl-4-morpholinopiperidin-1-yl)pyridin-2-amine (Intermediate AA84) was prepared from 5-fluoro-2-nitropyridine (Intermediate AA30-1) and 4-(4-methylpiperidin-4-yl)morpholine in a similar fashion to that described in 5-(3aR,6aS)-5-(6-nitropyridin-3-yl)hexahydro-1H-furo[3,4-c]pyrrole (General process intermediate AA30). (0.7 g, 91%). MS (ES): m/z 277.3 [M+H]$^+$ (1-(6-aminopyridin-3-yl)-4-methylpiperidin-4-yl)methanol (Intermediate AA85) was prepared from 5-fluoro-2-nitropyridine (Intermediate AA30-1) and 4-(4-methylpiperidin-4-yl)morpholine in a similar fashion to that described in 5-(3aR,6aS)-5-(6-nitropyridin-3-yl)hexahydro-1H-furo[3,4-c]pyrrole (General process intermediate AA30). (0.5 g, 92%). MS (ES): m/z 222.3 [M+H]$^+$.

Synthesis of Tert-Butyl 1-(6-aminopyridin-2-yl)hexahydropyrrolo[3,4-b]pyrrole-5(1H)-carboxylate (Intermediate AA86)

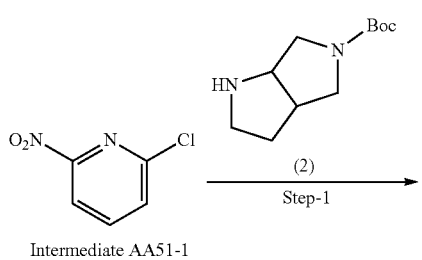

Intermediate AA51-1

-continued

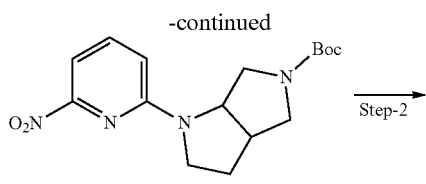

Intermediate AA86-1

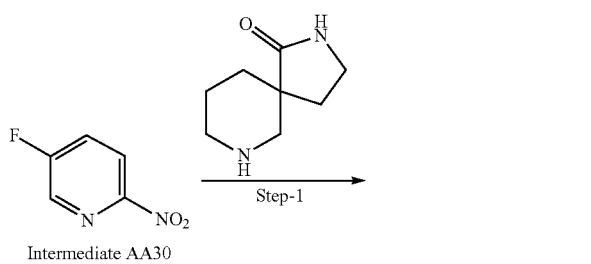

Intermediate AA86 tert-butyl 1-(6-aminopyridin-2-yl)hexahydropyrrolo[3,4-b]pyrrole-5(1H)-carboxylate (Intermediate AA86) was prepared from 2-chloro-6-nitropyridine (Intermediate AA51-1) and tert-butyl hexahydropyrrolo[3,4-b]pyrrole-5(1H)-carboxylate in a similar fashion to that described in tert-butyl 3-(6-aminopyridin-3-yl)-3,8-di azabicyclo[3.2.1]octane-8-carboxylate (General process intermediate AA6). (1.1 g, 89%). MS (ES): m/z 305.2 [M+H]$^+$ Synthesis of 7-(6-aminopyridin-3-yl)-2,7-diazaspiro[4.5]decan-1-one (Intermediate AA86)

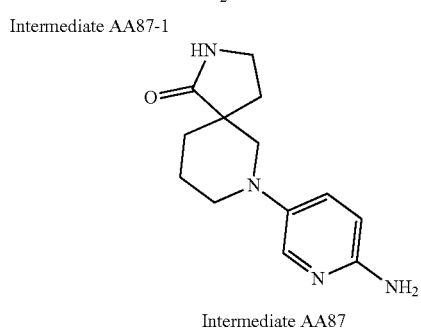

Intermediate AA87

7-(6-nitropyridin-3-yl)-2,7-diazaspiro[4.5]decan-1-one (Intermediate AA87-1) was prepared from 5-fluoro-2-nitropyridine (Intermediate AA30-1) and 2,7-diazaspiro[4.5]decan-1-one in a similar fashion to that described in 5-(3aR,6aS)-5-(6-nitropyridin-3-yl)hexahydro-1H-furo[3,4-c]pyrrole pyrrole (General process intermediate AA30). (1.0 g, 89%). MS (ES): m/z 347.3 [M+H]$^+$.

Synthesis of 1-(6-chloro-5-fluoropyridin-3-yl)piperidin-4-ol (Intermediate AA88)

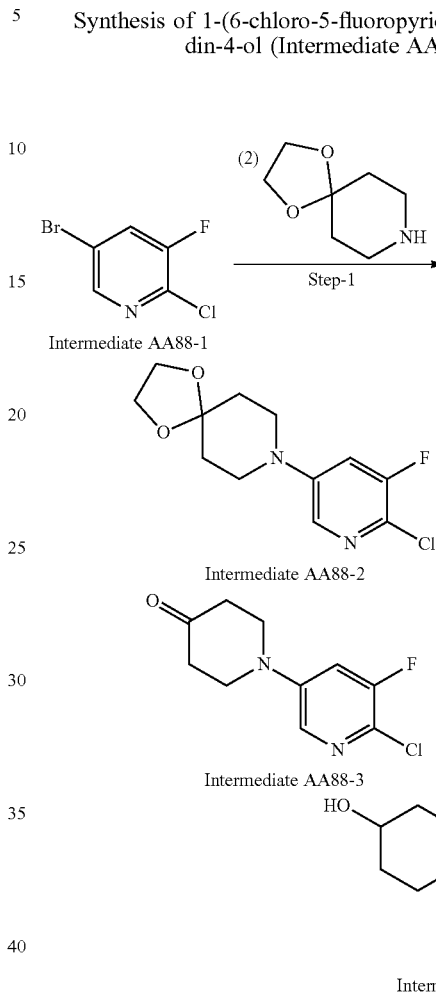

Step-1 Synthesis of 8-(6-chloro-5-fluoropyridin-3-yl)-1,4-dioxa-8-azaspiro[4.5]decane (Intermediate AA88-2)

A solution of Intermediate AA88-1 (1.0 g, 4.80 mmol), 1,4-dioxa-8-azaspiro[4.5]decane (0.755 g, 5.28 mmol, 1.1 eq) and K$_2$CO$_3$ (2.0 g, 14.4 mmol, 3.0 eq) in toluene (10 mL) was degassed under N$_2$ stream. After 15 min, Xantphos (0.552 g, 0.96 mmol, 0.2 eq) and Pd$_2$(dba)$_3$ (0.439 g, 0.48 mmol, 0.1 eq) were added. After stirring at 110° C. for 2 h, the reaction mixture was cooled to RT, diluted with water (80 mL), and extracted with ethyl acetate (3×50 mL). The combined organic extracts were washed with brine (80 mL), dried over Na$_2$SO$_4$, filtered, and concentrated under reduced pressure. The residue was purified by silica gel chromatography eluting with 15% ethyl acetate in hexane to afford Intermediate AA88-2 (0.7 g, 54.01%) MS (ES): m/z=273.2 (M+H)$^+$ Step-2 Synthesis of 1-(6-chloro-5-fluoropyridin-3-yl)piperidin-4-one (Intermediate AA88-3)

A solution of Intermediate AA88-2 (0.7 g, 2.57 mmol) in 50% HCl (35 mL) was stirred at RT for 30 min. After completion of reaction, the reaction mixture was quenched with water (70 mL) and extracted with ethyl acetate (3×40 mL). The combined organic extracts were washed with brine (50 mL), dried over Na$_2$SO$_4$, filtered, and concentrated under reduced pressure. The residue was used in next Step without purification. Intermediate AA88-3 (0.6 g, 95.41%). MS (ES): m/z=229.05 (M+H)$^+$ Step-3 Synthesis of 1-(6-chloro-5-fluoropyridin-3-yl)piperidin-4-ol (Intermediate AA88)

To a solution of Intermediate AA88-3 (0.6 g, 2.63 mmol) in THF (15 mL) was added portion wise sodium borohydride (0.150 g, 3.94 mmol, 1.5 eq) at RT. After stirring at RT and for 30 min, the reaction mixture was quenched in water (40 mL) and extracted with ethyl acetate (3×20 mL). The combined organic extracts were washed with brine (50 mL), dried over Na$_2$SO$_4$, filtered, and concentrated under reduced pressure. The residue was purified by silica gel chromatography eluting with 40% ethyl acetate in hexane to afford Intermediate AA88 (0.5 g, 82.61%) MS (ES): m/z=231.2 (M+H)$^+$ Synthesis of 5-(4-(morpholinomethyl)piperidin-1-yl)pyridin-2-amine (Intermediate AA89)

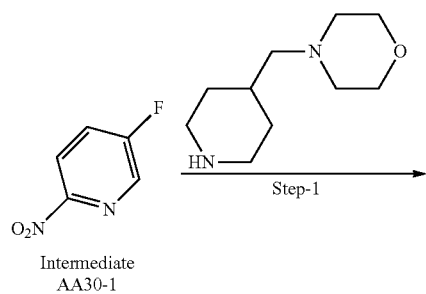

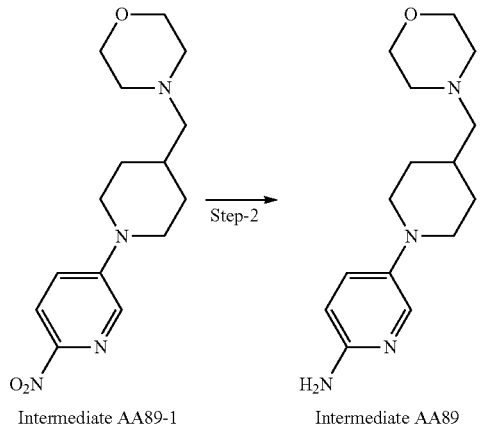

5-(4-(morpholinomethyl)piperidin-1-yl)pyridin-2-amine (Intermediate AA89) was prepared from 5-fluoro-2-nitropyridine (Intermediate AA30-1) and 4-(piperidin-4-ylmethyl)morpholine in a similar fashion to that described in 5-(3aR,6aS)-5-(6-nitropyridin-3-yl)hexahydro-1H-furo[3,4-c]pyrrole (General process intermediate AA30). (0.5 g, 92%). MS (ES): m/z 277.3 [M+H]$^+$ Synthesis of Tert-Butyl 4-(6-bromopyridin-2-yl)-4-methylpiperidine-1-carboxylate (Intermediate AA90)

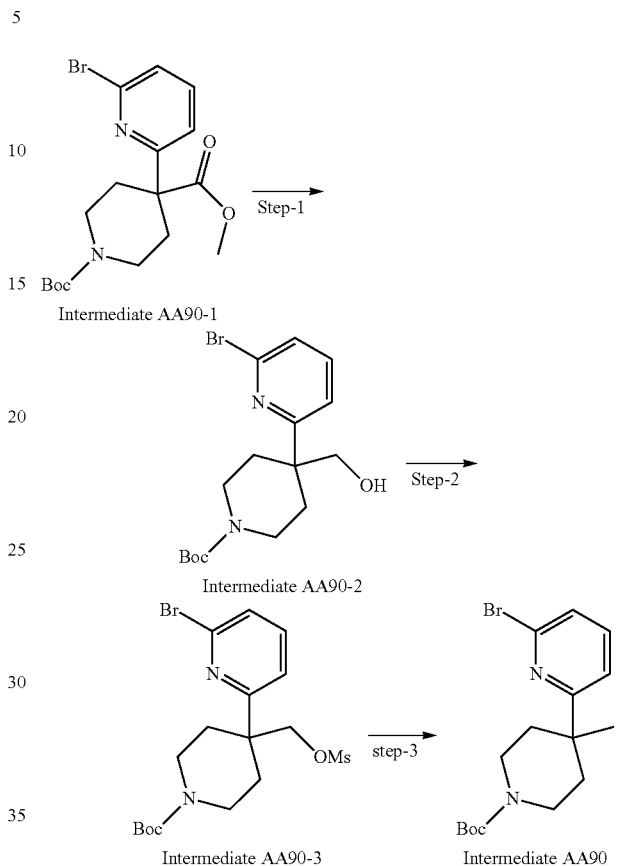

1-(tert-butyl) 4-methyl 4-(6-bromopyridin-2-yl)piperidine-1,4-dicarboxylate (Intermediate AA90-1) Synthesized as described in CA 2988721 A1

Step-1 Synthesis of Tert-Butyl 4-(6-bromopyridin-2-yl)-4-(hydroxymethyl)piperidine-1-carboxylate (Intermediate AA90-2)

To a solution of Intermediate AA90-1 (1.2 g, 3.00 mmol) in THF (15 mL) was added dropwise lithium aluminum hydride (2M in THF) (4.5 mL, 9.0 mmol, 3.0 eq) at 0° C. After stirring at 70° C. for 1 h, the reaction mixture was quenched in water (120 mL) and extracted with ethyl acetate (3×70 mL). The combined organic extracts were washed with brine (100 mL), dried over Na$_2$SO$_4$, filtered, and concentrated under reduced pressure. The residue was purified by silica gel chromatography using 10% ethyl acetate in hexane to afford Intermediate AA90-2 (1.0 g, 89.62%) MS (ES): m/z=371.2 (M+H)$^+$ Step-2 Synthesis of Tert-Butyl 4-(6-bromopyridin-2-yl)-4-(((methylsulfonyl)oxy)methyl)piperidine-1-carboxylate (Intermediate AA90-3)

To a solution of Intermediate AA90-2 (1.0 g, 2.70 mmol) in DCM (10 mL) was added trimethylamine (0.5 mL, 4.05 mmol, 1.5 eq) and DMAP (10 mg). At 0° C. Methanesulfonyl chloride (0.22 mL, 2.97 mmol, 1.1 eq) was added dropwise into the reaction mixture and stirred it at RT for 2 h. After completion of reaction, the reaction mixture was quenched in water (90 mL) and extracted with ethyl acetate (2×70 mL). The combined organic extracts were washed with brine (50 mL), dried over Na$_2$SO$_4$, filtered, and concentrated under reduced pressure. The residue was used in next Step without purification. Intermediate AA90-6 (1.0 g, 82.62%) MS (ES): m/z=450.2 (M+H)$^+$ Step-3 Synthesis of Tert-Butyl 4-(6-bromopyridin-2-yl)-4-methylpiperidine-1-carboxylate (Intermediate AA90)

To a solution of Intermediate AA90-3 (1.0 g, 2.22 mmol) in DMF (30 mL) were add sodium iodide (0.661 g, 4.44 mmol, 2.0 eq) and zinc powder (0.725 g, 11.1 mmol, 5.0 eq). After stirring at 110° C. for 40 h, the reaction mixture was filtered. The filtrate was diluted with water (100 mL) and extracted with ethyl acetate (100 mL×3). The combined organic solution was dried, filtered, and concentrated. The residue was purified by silica gel chromatography using 10% ethyl acetate in DCM to afford Intermediate AA90 (0.2 g, 25.30%) MS (ES): m/z=355.2 (M+H)$^+$ Synthesis of 2-(1-(4-aminophenyl)piperidin-3-yl)propan-2-ol (Intermediate AA91)

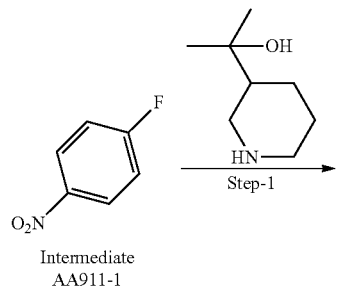

Intermediate AA911-1

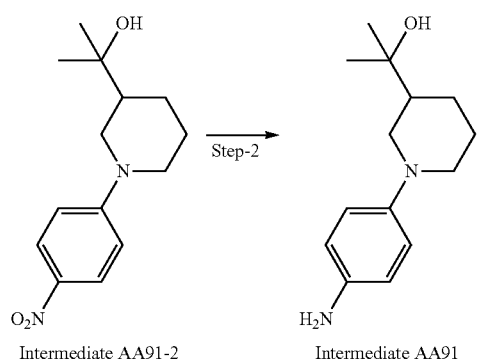

Intermediate AA91-2  Intermediate AA91

2-(1-(4-aminophenyl)piperidin-3-yl)propan-2-ol (Intermediate AA91) was prepared from 1-fluoro-4-nitrobenzene (Intermediate AA91-1) and 2-(piperidin-3-yl)propan-2-ol in a similar fashion to that described in 5-(3aR,6aS)-5-(6-nitropyridin-3-yl)hexahydro-1H-furo[3,4-c]pyrrole (General process intermediate AA30). (0.6 g, 92%). MS (ES): m/z 2235.3 [M+H]$^+$ Synthesis of 2-chloro-6-(1-methylazetidin-3-yl)pyridine (Intermediate AA92)

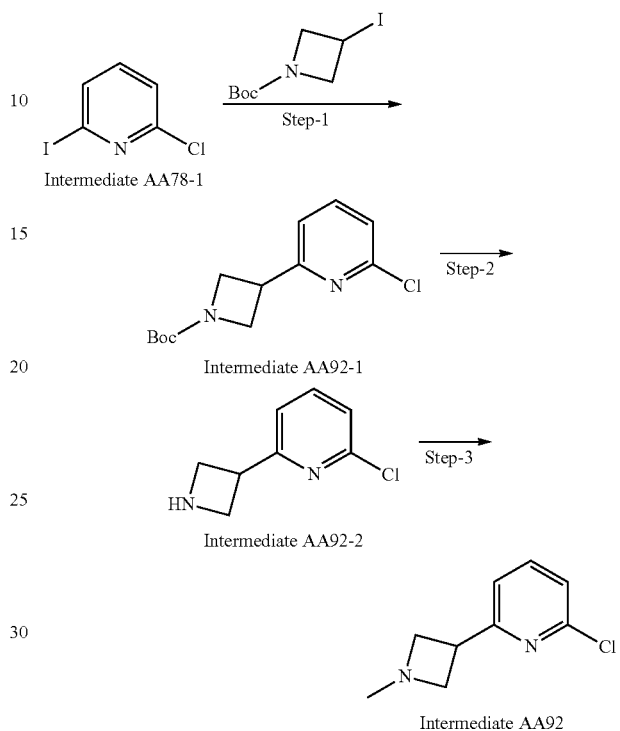

Step-1 Synthesis of Tert-Butyl 3-(6-chloropyridin-2-yl)azetidine-1-carboxylate (Intermediate AA92-1)

To a solution of Zn dust (407 mg, 6.2 mmol, 1.2 eq) in THF (10 mL) was added 1,2-dibromoethane (146 mg, 0.78 mmol, 0.15 eq) under N$_2$ atmosphere. After stirring at 80° C. for 10 min, the reaction was cool at RT and TMS-Cl (79 mg, 0.72, 0.14 eq) and tert-butyl 3-iodoazetidine-1-carboxylate (1.38 g, 5.7 mmol, 1 eq) in THF (5 mL) were added. After stirring at RT for 2 h, Intermediate-AA78-1 (1.5 g, 5.2 mmol, 1 eq), Pd$_2$(dba)$_3$ (47 mg, 0.052 mmol, 0.01 eq) and tri(2-furyl)phosphine (60 mg, 0.26 mmol, 0.05 eq) were added. After stirring at 55° C. for 16 h, the reaction mixture was quenched with water (50 mL) and extracted with ethyl acetate (2×20 mL). The combined organic extracts were washed with brine (50 mL), dried over Na$_2$SO$_4$, filtered, and concentrated under reduced pressure to afford crude product which was purified by silica gel chromatography eluting with 10% ethyl acetate in hexane to afford Intermediate AA92-1 (390 mg, 29.62%) MS (ES): m/z=269.26 (M+H)$^+$ Step-2 Synthesis of 2-(azetidin-3-yl)-6-chloropyridine (Intermediate AA92-2)

2-(azetidin-3-yl)-6-chloropyridine (Intermediate AA92-2) was prepared from tert-butyl 3-(6-chloropyridin-2-yl)azetidine-1-carboxylate (Intermediate AA92-1) in a similar fashion to that described in step-2 of Intermediate AA80-2 (155 g, 88%). MS (ES): m/z 169.7 [M+H]$^+$

Step-3 Synthesis of 2-chloro-6-(1-methylazetidin-3-yl)pyridine (Intermediate AA92)

2-chloro-6-(1-methylazetidin-3-yl)pyridine (Intermediate AA92) was prepared from 2-(azetidin-3-yl)-6-chloropyridine (Intermediate AA92-1) in a similar fashion to that described in step-3 of Intermediate AA80-3 (120 mg, 78%). MS (ES): m/z 184.5 [M+H]$^+$.

Synthesis of 5-(2-(2-(dimethylamino)propan-2-yl)morpholino)pyridin-2-amine (Intermediate-AA93)

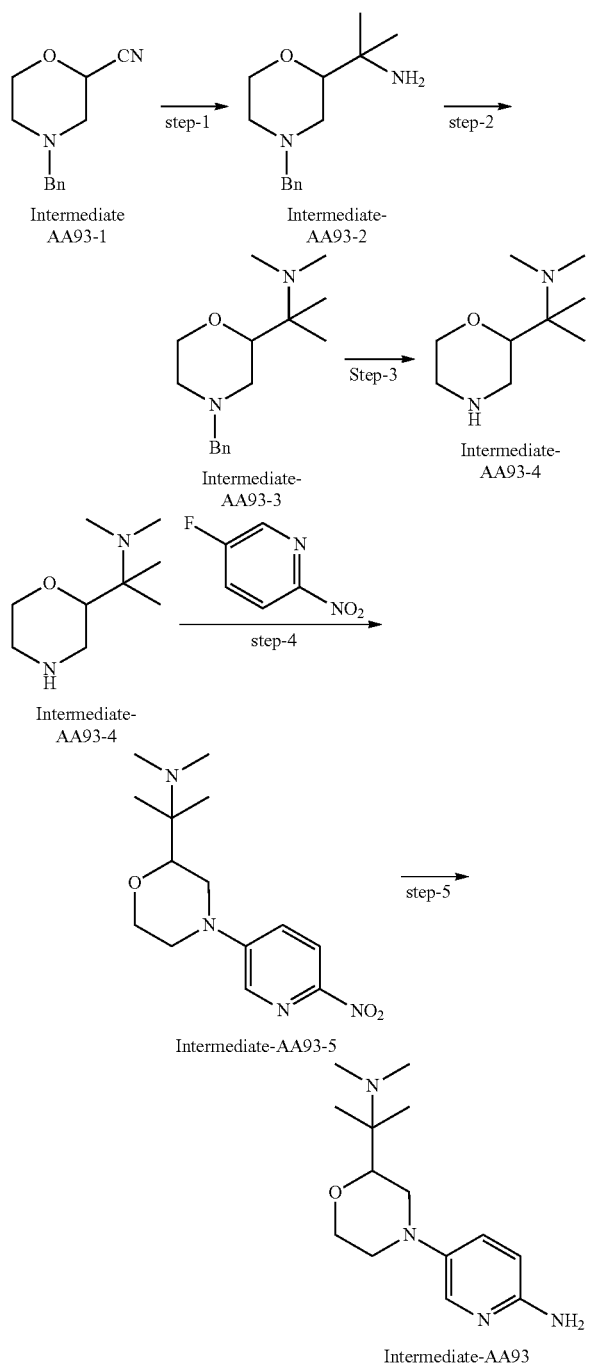

Step-1 Synthesis of 2-(4-benzylmorpholin-2-yl)propan-2-amine (Intermediate-AA93-2)

A solution of Ce(VI)Cl (36.6 g, 148.51 mmol, 2.0 eq) in dry THF (150 mL) was stirred at 45° C. for 2 h. The reaction mixture was cooled to RT and Intermediate-AA93-1 (15.0, 74.25 mmol) was added. The reaction mixture then cooled to −10° C. and methyl lithium (3M) (61.0 mL, 185.62 mmol, 2.5 eq) was added. After stirring for 30 min, the reaction mixture was filtered through celite-bed, diluted with water (100 mL), and extracted with DCM (3×70 mL). The combined organic extracts were washed with brine (60 mL), dried over Na$_2$SO$_4$, filtered, and concentrated under reduced pressure to obtain crude material which was used in the next step without further purification. (Intermediate-AA93-2) (10.0 g, 57.54%) as a brown solid. MS (ES): m/z=235.18 [M+H]$^+$.

Step-2 Synthesis of 2-(4-benzylmorpholin-2-yl)-N,N-dimethylpropan-2-amine (Intermediate-AA93-3)

To a solution of Intermediate-AA93-2 (10.0 g, 42.73 mmol) and formaldehyde (2.56 g, 85.46 mmol, 2.0 eq) in dichloroethane (100 mL) was added trimethylamine (12 mL, 85.46 mmol, 2.0 eq). After stirring at RT for 1 h. sodium triacetoxyborohydride (18.1 g, 85.46 mmol, 2.0 eq) was added in portion. After stirring for 16 h at RT, reaction mixture was diluted with water (200 mL) and sodium bicarbonate-solution (100 mL) and extracted with DCM (3×80 mL). The combined organic extracts were washed with brine (150 mL), dried over Na$_2$SO$_4$, filtered, and concentrated under reduced pressure. The residue was purified by column chromatography eluting with 3.2% methanol gradient in DCM to afford Intermediate-AA93-3 (4.0 g, 35.72%) as a brown solid. MS (ES): m/z=263.2 [M+H]$^+$.

Step-3 Synthesis of N,N-dimethyl-2-(morpholin-2-yl)propan-2-amine (Intermediate-AA93-4)

To a suspension of 20% palladium hydroxide on carbon (2.0 g) in methanol (20 mL), was added Intermediate-AA93-3 (4.0 g, 15.26 mmol). After hydrogenating at atmospheric pressure at RT for 16 h, the reaction mixture was filtered through celite-bed and washed with methanol. The filtrate was concentrated under reduced pressure to obtain Intermediate-AA93-4 (1.8 g, quantitative). MS (ES): m/z 173.16 [M+H]$^+$

Step-4 Synthesis of N, N-dimethyl-2-(4-(6-nitropyridin-3-yl) morpholin-2-yl) propan-2-amine (Intermediate-AA93-5)

To a solution of Intermediate-AA93-4 (1.8 g, 10.46 mmol) and Intermediate-AA30-1 (0.890 g, 6.27 mmol, 0.6 eq) in DMSO (20 mL) was added dropwise N-ethyl-N-isopropylpropan-2-amine (7.1 mL, 41.84 mmol, 3.0 eq). After stirring at 120° C. for 2 h, reaction mixture was diluted with water (100 mL) and extracted with ethyl acetate (3×80 mL). The combined organic extracts were washed with brine (100 mL), dried over Na$_2$SO$_4$, filtered, and concentrated under reduced pressure. The residue was purified by column chromatography eluting with 2.3% methanol gradient in DCM to afford Intermediate-AA93-5 (1.4 g, 45.52%). MS (ES): m/z=295.17 [M+H]$^+$

Step-5 Synthesis of N,N-dimethyl-2-(morpholin-2-yl)propan-2-amine (Intermediate-AA93)

To a suspension of 10% palladium on carbon (0.7 g) in methanol (15 mL) was added Intermediate-AA93-5 (1.4 g, 4.76 mmol). After hydrogenating at atmospheric pressure at RT for 4 h, reaction mixture was filtered through Celite-bed and washed with methanol. The filtrate was concentrated under reduced pressure to obtain crude which was used in the next step without further purification (Intermediate-AA93) (1.2 g, quantitative). MS (ES): m/z 265.2 [M+H]$^+$ Synthesis of 3-((dimethylamino) methyl)-1-(6-nitro-pyridin-3-yl) piperidin-3-ol (Intermediate-AA94)

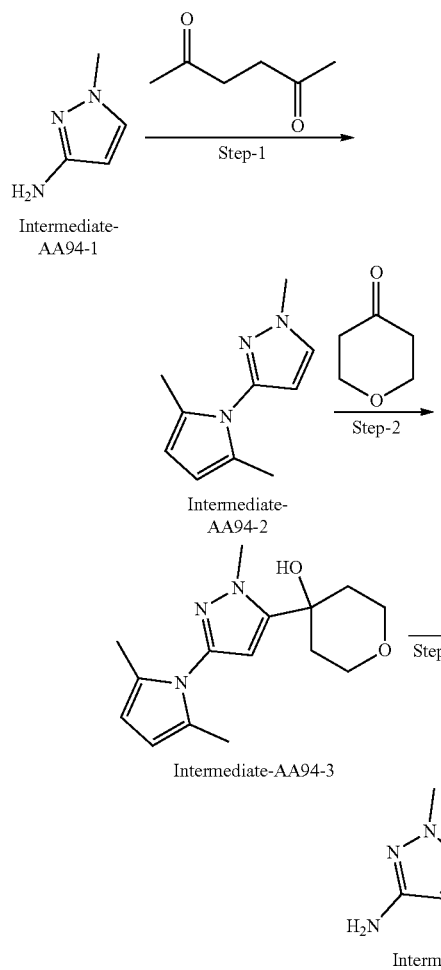

Step-1 Synthesis of Tert-Butyl 1-oxa-5-azaspiro [2.5]octane-5-carboxylate (AA95-2)

To a solution of Intermediate-AA94-1 (1 g, 10.3 mmol, 1 eq) in toluene (25 mL) were added hexane-2,5-dione (1.17 g, 10.3 mmol, 1 eq) and acetic acid (0.7 mL, 3.0 mmol, 0.3 eq). After stirring at 125° C. for 12 h, the reaction mixture was diluted with water (30 mL) and extracted with ethyl acetate (2×90 mL). The combined organic layer was washed with brine (30 mL), concentrated under reduced pressure to afford Intermediate-AA94-2 (1 g). MS (ES): m/z 175.11 [M+H]$^+$ Step-2 Synthesis of Tert-Butyl 3-((dimethylamino) methyl)-3-hydroxypiperidine-1-carboxylate (Intermediate-AA94-3)

To a solution of Intermediate-AA94-2 (5 g, 28.5 mmol, 1 eq) in THF (50 mL) at −78° C. was added n-BuLi (34 mL, 85.7 mmol, 3 eq). After stirring for 30 min. tetrahydro-4H-pyran-4-one (5.71 g, 57.1 mmol, 1 eq) was added. After stirring at −78° C. for 20 min and then at 1 hr at RT, the reaction mixture was diluted with water (35 mL) and extracted with ethyl acetate (2×50 mL). The combined organic solution was concentrated under reduced pressure to afford Intermediate-AA94-3 (420 mg, 44%). MS (ES): m/z 275.16 [M+H]$^+$.

Step-3 Synthesis of 4-(3-amino-1-methyl-1H-pyrazol-5-yl)tetrahydro-2H-pyran-4-ol (Intermediate AA94)

To a stirred solution of Intermediate-AA94-3 (2 g, 7.2 mmol, 1 eq) in ethanol (30 mL) and water (15 mL) were added NH$_2$OH HCl (2.4 g, 33.4 mmol, 4.6 eq) and KOH (1.2 g, 21.2, 3 eq). After stirring at RT for 2 h, the reaction mixture was concentrated under reduced pressure to afford Intermediate-AA94 (2 g, quantitative). MS (ES): m/z 197.12 [M+H]$^+$ Synthesis of 3-((dimethylamino)methyl)-1-(6-nitro-pyridin-3-yl)piperidin-3-ol (Intermediate-AA95)

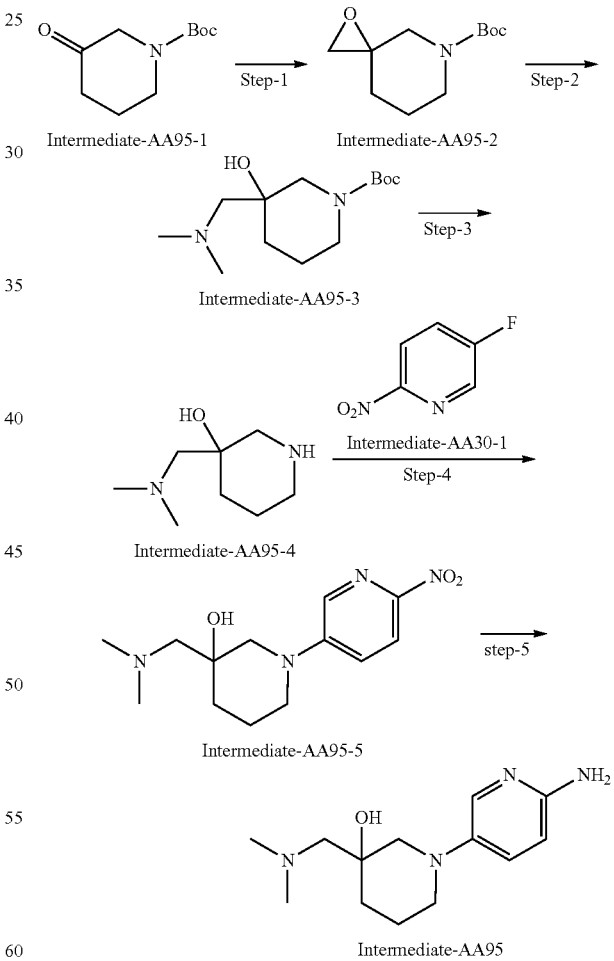

Step-1 tert-butyl 1-oxa-5-azaspiro[2.5]octane-5-carboxylate (Intermediate-AA95-2)

To a suspension of potassium tert butoxide (7.2 g, 65.4 mmol, 1 eq) in DMSO (70 mL), was added trimethyl sulphonium iodide (14.4 g, 65.4 mmol, 1 eq) dropwise. After stirring for 1.5 h, Intermediate-AA95-1 (9.1 g, 45.8 mmol, 1 eq) and DME (15 mL) was added at RT. After stirring for 1 h, the reaction mixture was diluted with water (30 mL) and extracted with ethyl acetate (2×90 mL). The combined organic layer was washed with brine (30 mL) and concentrated under reduced pressure to afford Intermediate-AA95-2 (7.4 g, 75%). MS (ES): m/z 213.14 [M+H]$^+$ Step-2 Synthesis of Tert-Butyl 3-((dimethylamino)methyl)-3-hydroxypiperidine-1-carboxylate (Intermediate-AA95-3)

To a suspension of Intermediate-AA95-2 (7.5 g, 35.2 mmol, 1 eq) was added dimethyl amine (75 mL, 10V). After stirring at RT for 2 h, the reaction was diluted with water (120 mL) and extracted with ethyl acetate (2×100 mL). The combined organic solution was concentrated under reduced pressure to afford Intermediate-AA95-3 (7 g, 77%). MS (ES): m/z 258.19 [M+H]$_+$.

Step-3 Synthesis of 3-((dimethylamino)methyl)piperidin-3-ol (Intermediate AA95-4)

To a stirred solution of Intermediate-AA95-4 (5 g, 19.3 mmol, 1 eq) in DCM (50 mL), was added, TFA (12 mL). After stirring at RT for 2 h, the reaction mixture was concentrated under reduced pressure to afford Intermediate-AA95-4 (2.9 g). MS (ES): m/z 158.25 [M+H]$^+$ Step-4 Synthesis of 3-((dimethylamino)methyl)-1-(6-nitropyridin-3-yl)piperidin-3-ol (Intermediate-AA95-5)

To a stirred solution of Intermediate-AA95-4 (2.8 g, 17.7 mmol, 1 eq) in DMSO (21 mL) were added DIPEA (21.1 mL, 123 mmol, 7 eq) and 5-fluoro-2-nitropyridine (2 g, 14.1 mmol, 1.5 eq). After stirring at 120° C. for 4 h, the reaction mixture was diluted with water (100 mL) and extracted with ethyl acetate (3×70 mL). The combined organic layer wash with brine (100 mL), concentrated under reduced pressure. The residue was purified by column chromatography to afford Intermediate-AA95-5 (1.5 g, 40%). MS (ES): m/z 159.31 [M+H]$^+$ Step-5 Synthesis of 5-(2-(2-methoxypropan-2-yl)morpholino) pyridin-2-amine (Intermediate-AA95)

To a suspension of 10% Pd/C (1.0 g) in methanol was added Intermediate-AA95-5 (2 g). After hydrogenating at atmospheric pressure for 2 h, the reaction was filtered through celite bed and washed with methanol. The filtrate was concentrated under reduced pressure to afford Intermediate-AA95 (1.6 g, 89.58%). MS (ES): m/z 250.35 [M+H]$^+$.

Synthesis of 1-(6-aminopyridin-3-yl)-4-cyclopropylpiperidin-4-ol (Intermediate-AA96)

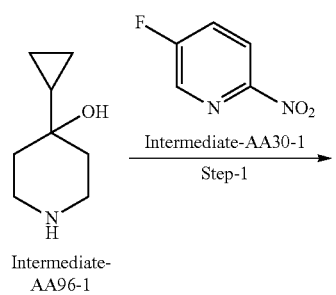

Intermediate-AA96-1

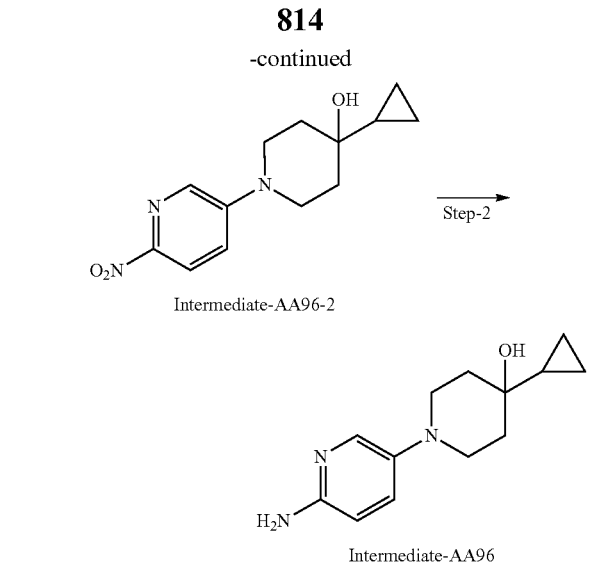

Intermediate-AA96-2

Intermediate-AA96

Step-1 Synthesis of 4-cyclopropyl-1-(6-nitropyridin-3-yl)piperidin-4-ol (Intermediate-AA96-2)

To a stirred solution of Intermediate-AA96-1 (500 mg, 3.5 mmol, 1 eq) in DMF (7 mL), were added K$_2$CO$_3$ (1.46 g, 10.5 mmol, 3 eq), Intermediate-AA30-1 (500 mg, 3.5 mmol, 1 eq) and TBAI (260 mg, 0.7 mmol, 0.2 eq). After stirring at 110° C. for 2 h, the reaction mixture was diluted with water (30 mL) and extracted with ethyl acetate (2×40 mL). The combined organic layers were wash with brine (30 mL) and concentrated under reduced pressure. The residue was purified by column chromatography to afford Intermediate-AA96-2 (0.600 g, 64.36%). MS (ES): m/z 263.30 [M+H]$^+$ Step-2 Synthesis of 1-(6-aminopyridin-3-yl)-4-cyclopropylpiperidin-4-ol (Intermediate-AA96)

To a suspension of 10% Pd/C (0.440 g) in methanol (10 mL) was added Intermediate-AA96-) (0.9 g, 9.4 mmol, 1 eq). After hydrogenating at atmospheric pressure for 2 hr, the reaction was filtered through celite bed and washed with methanol. The filtrate was concentrated under reduced pressure to afford Intermediate-AA96 (600 mg, 75.23%). MS (ES): m/z 233.32 [M+H]$^+$ Synthesis of 5-(2-(2-methoxypropan-2-yl)morpholino)pyridin-2-amine (Intermediate-AA97)

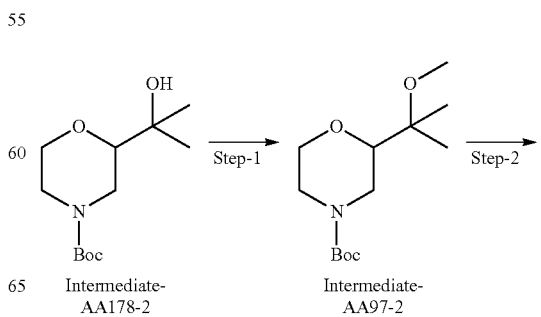

Intermediate-AA178-2

Intermediate-AA97-2

Step-4 Synthesis of 5-(2-(2-methoxypropan-2-yl)morpholino) pyridin-2-amine (Intermediate-AA97)

To a suspension of 10% Pd/C (0.8 g) in methanol was added Intermediate-AA97-4 (0.8 g). After hydrogenating at atmospheric pressure for 2 h, the reaction mixture was filtered through celite bed and washed with methanol. The filtrate was concentrated under reduced pressure to afford Intermediate-AA97 (1.5 g, 40%). MS (ES): m/z 159.31 [M+H]$^+$

Synthesis of (1-(6-aminopyridin-3-yl)-5-methoxypiperidin-2-yl)methanol (Intermediate-AA98)

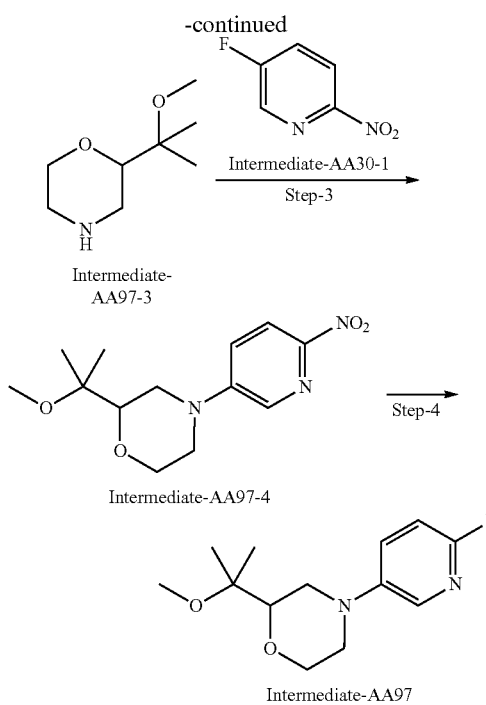

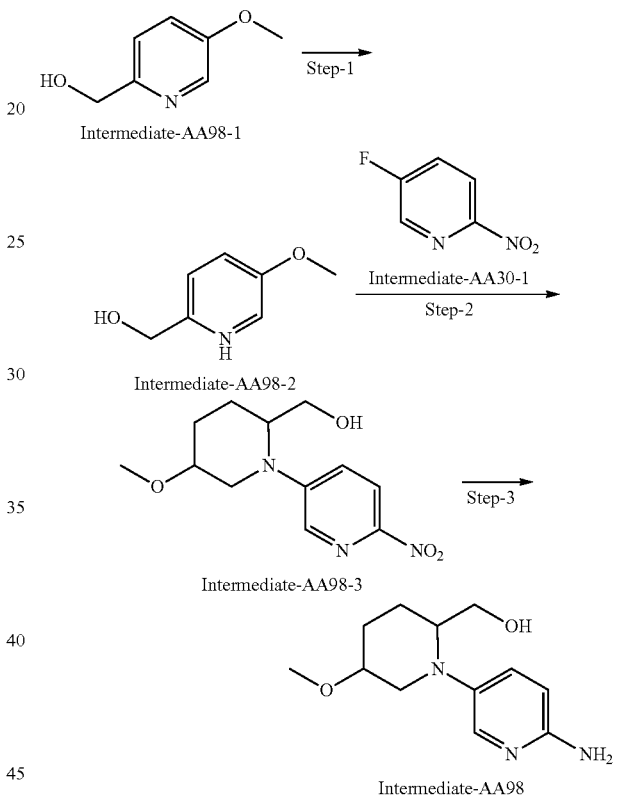

Step-1 Synthesis of Tert-Butyl 2-(2-methoxypropan-2-yl)morpholine-4-carboxylate. Intermediate (Intermediate-AA97-2)

To a stirred solution of Intermediate-AA178-2 (1 g, 4.08 mmol, 1 eq) in DMF (10 mL) at 0° C. was added sodium hydride (423 mg, 4.2 mmol, 1.2 eq). After stirring for 15 min. CH$_3$I (1.76 g, 12.24 mmol, 3 eq) was added. After stirring for 2 h. at RT, the reaction was diluted with water (100 mL) and extracted with ethyl acetate (3×70 mL). The combined organic layers were dried over Na$_2$SO$_4$, filtered, and concentrated under reduced pressure. The residue was purified by column chromatography eluting with at 2 to 3% methanol in DCM to afford Intermediate-AA97-2 (0.600 mg, 56.75%). MS (ES): m/z 259.12 [M+H]$^+$

Step-2 Synthesis of 2-(2-methoxypropan-2-yl)morpholine (Intermediate AA97-3)

To a stirred solution of Intermediate-AA97-2 (3 g, 11.53 mmol, 1 eq) in DCM (30 mL) was added TFA (4 mL). After stirring at RT for 2 h, the reaction mixture was concentrated under reduced pressure to afford Intermediate-AA57-3 (2.5 g). MS (ES): m/z 159.31 [M+H]$^+$

Step-3 Synthesis of 2-(2-methoxypropan-2-yl)-4-(6-nitropyridin-3-yl)morpholine (Intermediate-AA97-4)

To a stirred solution of Intermediate-AA97-3 (2.1 g, 13.18 mmol, 1 eq) in DMSO (21 mL) were added DIPEA (20.2 mL, 118.2 mmol, 8 eq) and 5-fluoro-2-nitropyridine (3.5 g, 19.78 mmol, 1.5 eq). After stirring at 120° C. for 3, the reaction mixture was diluted with water (100 mL) and extracted with ethyl acetate (3×70 mL). The combined organic layers were wash with brine (100 mL) and concentrated under reduced pressure. The residue was purified by column chromatography to afford Intermediate-AA97-4 (1.5 g, 40%). MS (ES): m/z 159.31 [M+H]$^+$

Step-1 Synthesis of (5-methoxypiperidin-2-yl)methanol (Intermediate-AA98-2)

To a solution of Intermediate-AA98-1 (1.5 g, 1.79 mmol, 1 eq) in MeOH (15 mL) was added Rh/Al2O3 (2 g, 1.29 mmol, 0.12 eq). After hydrogenating at 50 psi at RT for 24 h, the reaction mixture was filter through Celite-bed and washed with 10% methanol in DCM. The filtrate was concentrated under reduced pressure to obtain crude product which was use in the next step without further purification (Intermediate-AA98-2). (1 g, 63%). MS (ES): m/z=145.6 [M+H]$^+$.

Step-2 Synthesis of (5-methoxy-1-(6-nitropyridin-3-yl)piperidin-2-yl)methanol (Intermediate-AA98-3)

To a solution of Intermediate-AA98-2 (1 g, 7.04 mmol, 1 eq) in DMSO (10 mL) were added DIPEA (4.54 g, 35.21 mmol, 5 eq) and 5-fluoro-2-nitropyridine (1.22 g, 8.45 mmol, 1.2 eq). After stirring at 110° C. for 4 h, the reaction mixture was diluted with water (30 mL) and extracted with DCM (3×30 mL). The combined organic extracts were wash with brine (30 mL), dried over Na$_2$SO$_4$, filtered, and concentrated under reduced pressure. The residue was purified by column chromatography to afford Intermediate-AA98-3. (1.5 g, 81.49%) MS (ES): m/z=268.1 [M+H]$^+$.

Step-3 Synthesis of (1-(6-aminopyridin-3-yl)-5-methoxypiperidin-2-yl)methanol (Intermediate-AA98)

To a suspension of 10% palladium on carbon (0.800 g) in methanol (20 mL) was added Intermediate-AA98-3 (1.4 g). After hydrogenating at atmospheric pressure for 3 h, the reaction mixture was filter through Celite-bed and washed with methanol. The filtrate was concentrated under reduced pressure to obtain product which was used in the next step without further purification (Intermediate-AA98). (0.900 g, 72.6%). MS (ES): m/z=237 [M+H]$^+$ Synthesis of 3-(6-chloropyridin-3-yl)THF-3-ol (Intermediate-AA99)

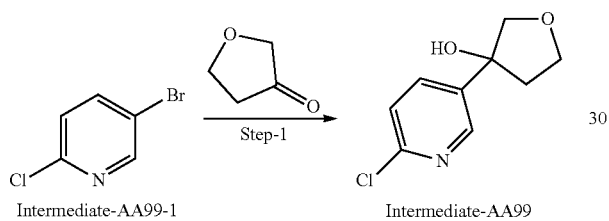

Intermediate-AA99-1   Intermediate-AA99

Step-1 Synthesis of 3-(6-chloropyridin-3-yl)THF-3-ol (Intermediate-AA99)

To a solution of Intermediate-AA99-1 (10 g, 52.63 mmol, 1 eq) in THF (100 mL) at −78° C. was added n-BuLi (1.6M) (65 mL, 105.2 mmol, 2 eq). After stirring for 1 h, Intermediate AA99-2 (6.78 g, 105.26 mmol, 2 eq) was added. After stirring at RT for 2 h, the reaction was diluted water (100 mL) and extract with ethyl acetate (2×200 mL). The combined organic extracts were washed with brine (250 mL), dried over Na$_2$SO$_4$, filtered, and concentrated under reduced pressure. The residue was purified by column chromatography (0-15% gradient elution EtOAc in hexane) to afford Intermediate-AA99 (7 g, 67.40%). MS (ES): m/z=304 [M+1]+.

Synthesis of Tert-Butyl 4-(6-bromopyridin-2-yl)-4-methylpiperidine-1-carboxylate (Intermediate-AA100)

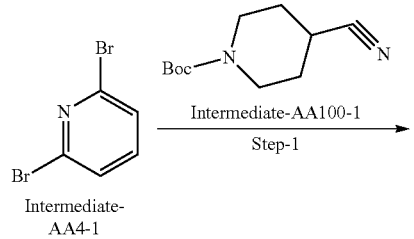

Intermediate-AA4-1

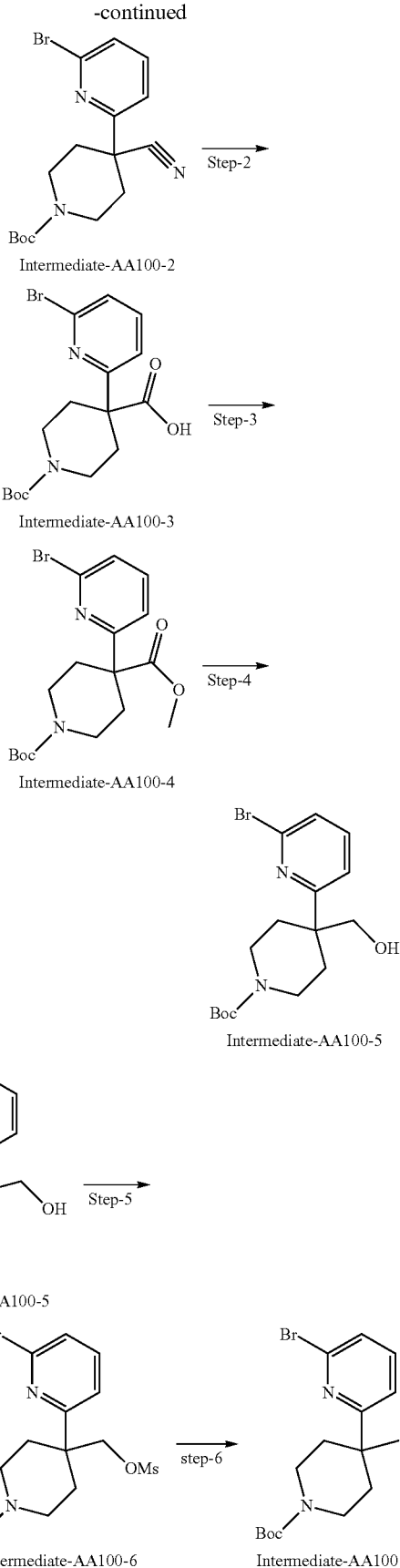

Step-1 Synthesis of Tert-Butyl 4-(6-bromopyridin-2-yl)-4-cyanopiperidine-1-carboxylate (AA100-2)

To a solution of tert-butyl 4-cyanopiperidine-1-carboxylate (5.38 g, 25.05 mmol, 2 eq) in toluene (30 mL) was added LiHMDS (3.07 g, 19.02 mmol, 1.5 eq) at 0° C. Intermediate-AA74-1 (3 g, 12.8 mmol, 1 eq) and $Pd_2(dba)3$ (0.117 g, 0.12 mmol, 0.1 eq) were then added. After stirring at RT for 16 h, the reaction mixture was quench with aq $NaHCO_3$ solution (50 mL) and extracted with ethyl acetate (3×80 mL). The combined organic extracts were washed with brine (60 mL), dried over $Na_2SO_4$, filtered, and concentrated under reduced pressure. The residue was purified by column chromatography eluting with 0-50% ethyl acetate in hexane to afford Intermediate-AA100-2. (4.2 g, 90%) MS (ES): m/z=366 $[M+H]^+$.

Step-2 Synthesis of 4-(6-bromopyridin-2-yl)-1-(tert-butoxycarbonyl)piperidine-4-carboxylic acid (Intermediate-AA100-3)

To a solution of Intermediate-AA100-2 (4 g, 10.95, 1 eq), in EtOH (40 mL) at 0° C. was added NaOH (2.191 g, 54.79 mmol, 5 eq). After stirring at 80° C. for 16 h, the reaction mixture with water (50 mL) and extracted with ethyl acetate (3×50 mL). The combined organic extracts were washed with brine (60 mL), dried over $Na_2SO_4$, filtered, and concentrated under reduced pressure. The residue was purified by column chromatography eluting with 0-50% ethyl acetate in hexane to afford Intermediate-AA100-2. (2.5 g, 69.42%) MS (ES): m/z=385.3 $[M+H]^+$.

Step-3 Synthesis of 1-(tert-butyl) 4-methyl 4-(6-bromopyridin-2-yl)piperidine-1,4-dicarboxylate (Intermediate-AA100-4)

To a solution of Intermediate-AA100-3 (2 g, 10.95, 1 eq) in DMF (20 mL) were added $K_2CO_3$ (1.43 g, 10.38 mmol, 2 eq) and MeI (0.878 g, 6.22 mmol, 1.2 eq). After stirring for 30 min, the reaction mixture was diluted with water (30 mL) and extracted with ethyl acetate (3×40 mL). The combined organic extracts were wash with brine (50 mL), dried over $Na_2SO_4$, filtered, and concentrated under reduced pressure. The residue was purified by column chromatography by 10-40% ethyl acetate gradient in hexane to afford Intermediate-AA100-4. (1.8 g, 86.84%) MS (ES): m/z=399.3 $[M+H]^+$.

Step-4 Synthesis of Tert-Butyl 4-(6-bromopyridin-2-yl)-4-(hydroxymethyl) piperidine-1-carboxylate (Intermediate-AA100-5)

To a solution of Intermediate-AA100-4 (1.5 g, 3.759, 1 eq) in EtOH (20 mL) at 0° C. was added $NaBH_4$ (0.278 g, 7.51 mmol, 2 eq). After stirring at RT for 2 h, the reaction was concentrated under reduced pressure, diluted with water (50 mL), and extracted with ethyl acetate (3×40 mL). The combined organic extracts were washed with brine (50 mL), dried over $Na_2SO_4$, filtered, and concentrated under reduced pressure to afford Intermediate-AA100-5. (1.1 g, 91%) MS (ES): m/z=371.28 $[M+H]^+$.

Step-5 Synthesis of Tert-Butyl 4-(6-bromopyridin-2-yl)-4-(((methylsulfonyl)oxy)methyl)piperidine-1-carboxylate (Intermediate-AA100-6)

To a solution of Intermediate-AA100-5 (1 g, 3.759, 1 eq) in DCM (10 mL) at 0° C. was added DIPEA (12.145 g, 9.41 mmol, 3.5 eq) and methanesulfonyl chloride (0.460 g, 4.04 mmol, 1.5 eq) were added. After stirring at 0° C. for 30 min, the reaction mixture was diluted with water (50 mL) and extracted with ethyl acetate (3×40 mL). The combined organic extracts were wash with brine (50 mL), dried over $Na_2SO_4$, filtered, and concentrated under reduced pressure to afford Intermediate-AA100-6. (1.2 g, 99%) MS (ES): m/z=449.5 $[M+H]^+$.

Step-6 Synthesis of Tert-Butyl 4-(6-bromopyridin-2-yl)-4-methylpiperidine-1-carboxylate (Intermediate-AA100)

To a solution of Intermediate AA100-6 (0.500 g, 1.1 mmol, 1 eq) in DMF (10 mL) were added NaI (0.829 g, 5.56 mmol, 2 eq) and Zn dust (0.144, 2.22 mmol, 5 eq). After stirring at 100° C. for 24 h, the reaction mixture was filter through Celite-bed and washed with ethyl acetate. The filtrate was concentrated under reduced pressure. The residue was purified by column chromatography eluting with 0-10% gradient elution MeOH in DCM to afford Intermediate-AA100. (0.140 g, 35.41%) MS (ES): m/z=355 $[M+H]^+$ Synthesis of (1-(6-aminopyridin-3-yl)-4-methoxypiperidin-4-yl)methanol (Intermediate-AA101)

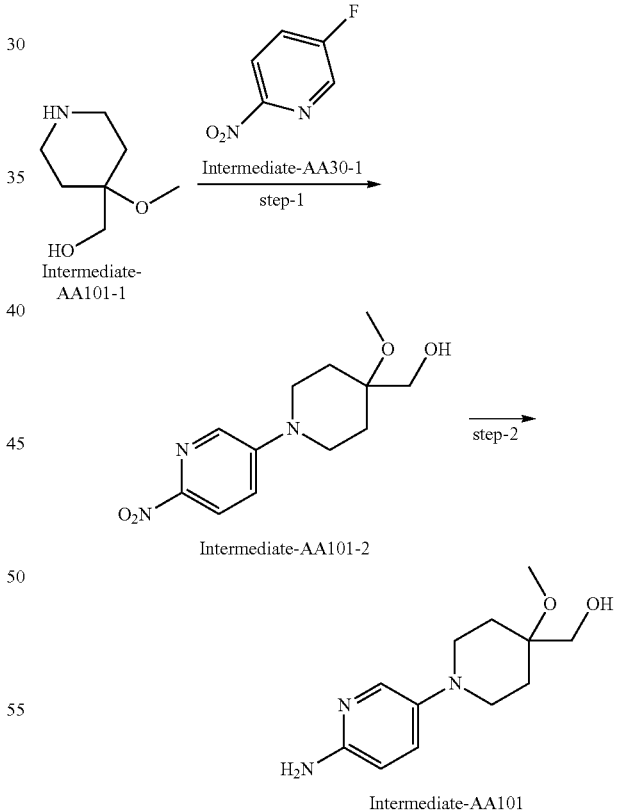

Step-1 Synthesis of (4-methoxy-1-(6-nitropyridin-3-yl)piperidin-4-yl)methanol (Intermediate-AA101-2)

To a solution of Intermediate AA101-1 (3 g, 1.93 mmol, 1 eq) in DMSO (30 mL) were added Intermediate-AA30-1 (2.7 g, 1.93 mmol, 1 eq) and DIPEA (16 mL, 9.6 mmol, 5 eq). After stirring at 110° C. for 3 h, the reaction mixture was diluted with water (30 mL) and extracted with DCM (3×30 mL). The combined organic extracts were wash with brine (30 mL), dried over Na$_2$SO$_4$, filtered, and concentrated under reduced pressure. The residue was purified by column chromatography eluting with 0-10% MeOH in DCM to afford Intermediate-AA101-2. (3.1 g, 54%), MS (ES): m/z=267.1 [M+H]$^+$.

Step-2 (1-(6-aminopyridin-3-yl)-4-methoxypiperidin-4-yl)methanol (Intermediate-AA101)

To a suspension of 10% palladium on carbon (1.5 g) in methanol (30 mL) was added Intermediate-AA54-5 (3 g). After hydrogenating at atmospheric pressure for 3 h, the reaction mixture was filter through Celite-bed and washed with methanol. The filtrate was concentrated under reduced pressure to obtain crude product which was use in the next step without further purification (Intermediate-AA101). (2.2 g, 82%). MS (ES): m/z=237 [M+H]$^+$ Synthesis of 6-(2-(dimethylamino)ethyl)-5-(tetrahydro-2H-pyran-4-yl)pyridin-2-amine (Intermediate-AA102)

extracted with ethyl acetate (2×40 mL). The combined organic extracts were washed with brine (50 mL), dried over Na$_2$SO$_4$, filtered, and concentrated under reduced pressure. The residue was purified by column chromatography eluting with 3.7% methanol gradient in DCM to obtain Intermediate AA102-1 (2.0 g, 98.70%), MS (ES): m/z: 248.17 [M+H]$^+$.

Step-2 Synthesis of 6-(2-(dimethylamino)ethyl)-5-(tetrahydro-2H-pyran-4-yl)pyridin-2-amine (Intermediate AA102)

To a solution of Intermediate AA102-1 (2.0 g, 8.09 mmol) in methanol (20 mL) and THF (10 mL) were added ammonium format (2.0 g, 32.36 mmol, 4.0 eq), acetic acid (1.4 mL, 0.7V) and 20% wet palladium hydroxide on carbon (1 g). After stirring under an atmosphere of hydrogen gas for 24 h at RT, the reaction mixture was filtered through Celite bed. The filtrate was concentrated under reduced pressure, diluted with sat. NaHCO$_3$ solution and extracted by DCM. The organic solution was concentrated to afford Intermediate AA102 (1.3 g, 64.47%). MS (ES): m/z 250.1 [M+H]$^+$ Synthesis of 5-(3-(2-(dimethylamino)propan-2-yl)piperidin-1-yl)pyridin-2-amine (Intermediate-AA103)

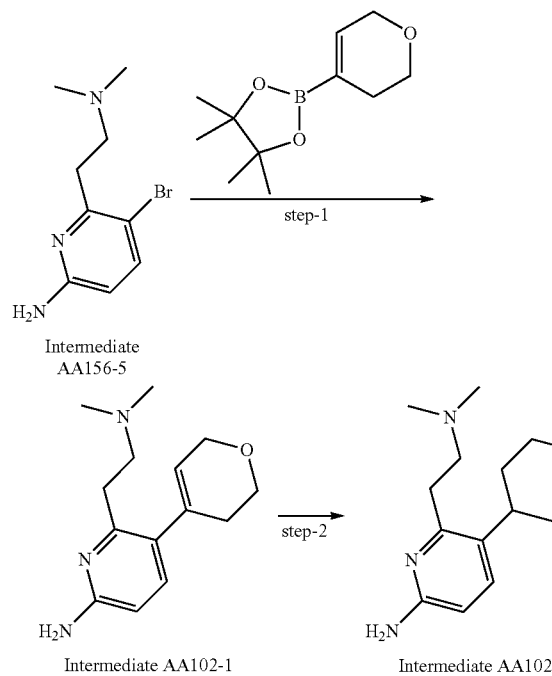

Intermediate AA102-1    Intermediate AA102

Step-1 Synthesis of 5-(3,6-dihydro-2H-pyran-4-yl)-6-(2-(dimethylamino)ethyl)pyridin-2-amine (Intermediate AA102-1)

A solution of Intermediate AA156-5 (1.5, 6.14 mmol), 2-(3,6-dihydro-2H-pyran-4-yl)-4,4,5,5-tetramethyl-1,3,2-dioxaborolane (2.5 g, 12.28 mmol, 2.0 eq), potassium phosphate tribasic (3.9 g, 18.42 mmol, 3.0 eq) in 1,4-Dioxane:water (15 mL:4 mL) was degassed and purged with N$_2$ for 15 min. X-Phos Pd G3 (0.519 g, 0.61 mmol, 0.1 eq) was then added. After stirring at 100° C. for 20 min, the reaction mixture was cooled to RT, diluted with water (80 mL), and

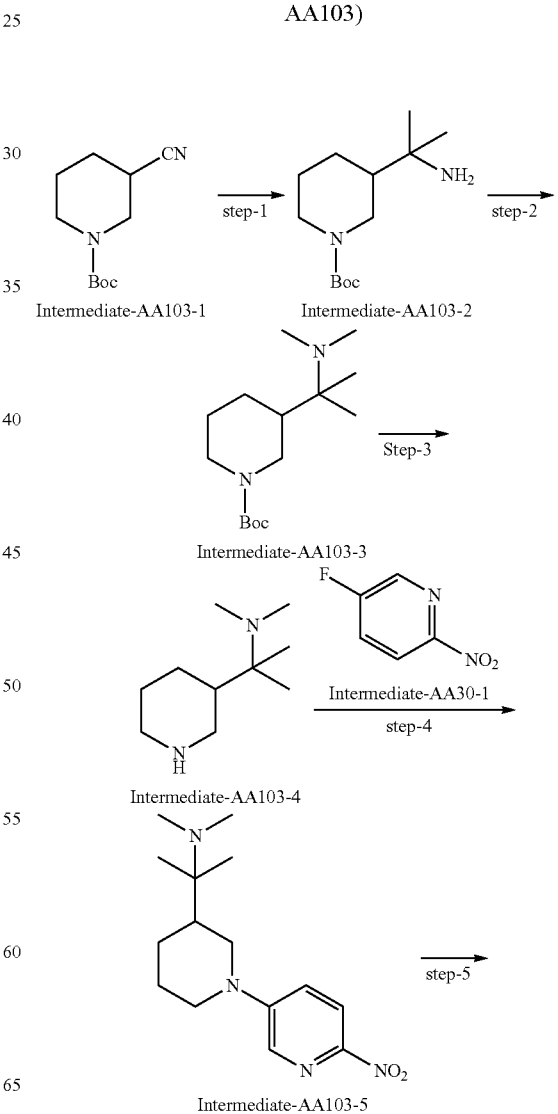

-continued

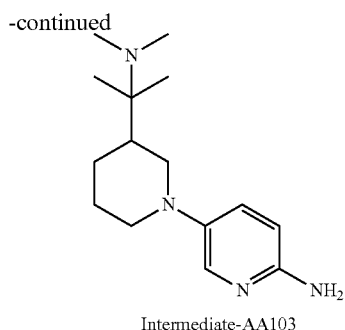

Intermediate-AA103

Step-1 Synthesis of Tert-Butyl 3-(2-aminopropan-2-yl)piperidine-1-carboxylate (Intermediate AA103-2)

To a solution of the $CeCl_3$ (12.2 g, 47.6 mmol, 2.0 eq) in THF (50 mL) stirred at 45° C. for 2 h was added Intermediate AA103-1 (5 g, 23.8 mmol) at RT. After cooling to −10° C., $CH_3Li$ (20 mL, 60 mmol, 2.5 eq) was added dropwise. After stirring for 30 min at RT, the reaction mixture was diluted with DCM (300 mL) and water (500 mL). The organic layer was collected, and the aqueous phase was extracted with DCM (2×300 mL). The combined organic extracts were washed with brine (10 mL), dried over $Na_2SO_4$, filtered, and concentrated under reduced pressure to obtain Intermediate AA103-2 (3.5 g, 60%) MS (ES): m/z=243.36 $[M+H]^+$

Step-2 Synthesis of Tert-Butyl 3-(2-(dimethylamino)propan-2-yl)piperidine-1-carboxylate (Intermediate-AA103-3)

To a solution of Intermediate-AA103-2 (8.0 g, 32.8 mmol) and formaldehyde (1.5 g, 49.2 mmol, 1.5 eq) in methanol (100 mL) was added acetic acid (0.4 g, 8.2 mmol, 0.25 eq). After stirring at RT for 1 h, sodium cyanoborohydride (2.0 g, 39.36 mmol, 1.2 eq) was added portion wise. After stirring for 45 min at RT, the reaction mixture was concentrated. The residue was diluted with water (100 mL) and the resulting solid collected by filtration. The solid was purified by column chromatography eluting with 5.0% ethyl acetate gradient in hexanes to afford Intermediate-AA103-3) (2.6 g, 29.74%). MS (ES): m/z=271.1 $[M+H]^+$.

Step-3 Synthesis of N,N-dimethyl-2-(piperidin-3-yl)propan-2-amine (Intermediate-AA103-4)

To a solution of (Intermediate-AA103-3) (3 g) in DCM (30 mL), TFA (12 mL) was added at 0° C. Reaction mixture was stirred at RT for 30 min. Reaction mixture was concentrate under reduced pressure to obtain crude to give the title compound Intermediate-AA103-4 (1.5 g, 79.8%). MS (ES): m/z=171.3 (M+H).

Step-4 Synthesis of N,N-dimethyl-2-(1-(6-nitropyridin-3-yl)piperidin-3-yl)propan-2-amine (AA103-5)

To a solution of (Intermediate-AA103-4) (1.4 g, 8.2 mmol, 1 eq) and 5-fluoro-2-nitropyridine (0.8 g, 9.84 mmol, 1.2 eq), DIPEA (5.2 mL, 41 mmol, 5 eq) in DMSO (15 mL) and the reaction was heated at 90° C. for 1 h. Reaction mixture was cooled at RT and then diluted with water (50 mL) and ethyl acetate (100 mL). The organic layer was collected, and the aqueous phase was extract with ethyl acetate (300 mL). The combined organic extracts were washed with brine (200 mL), dried over $Na_2SO_4$, filtered, and concentrated under reduced pressure. The residue was purified by column to afford the title compound (Intermediate-AA103-5) (1.5 g, 62.19%). MS (ES): m/z=293.38 $[M+1]^+$

Step-5 Synthesis of 5-(3-(2-(dimethylamino)propan-2-yl)piperidin-1-yl)pyridin-2-amine (Intermediate-AA103)

To a suspension of 10% Pd/c (500 mg) in MeOH (20 mL), was added (AA111-3) (1 g) and Reaction mixture was stirred at RT for 1 h with given H2 gas atmospheric pressure. The reaction mixture was filtrate through celite bed and organic layer was evaporate in vacuum to obtain crude (Intermediate-AA103) (600 mg, 66%), Used in the next step without purification MS (ES): m/z=263.40 $[M+H]^+$.

Synthesis of Tert-Butyl 4-((6-chloropyridin-3-yl)methyl)-3,3-dimethylpiperazine-1-carboxylate (AA104)

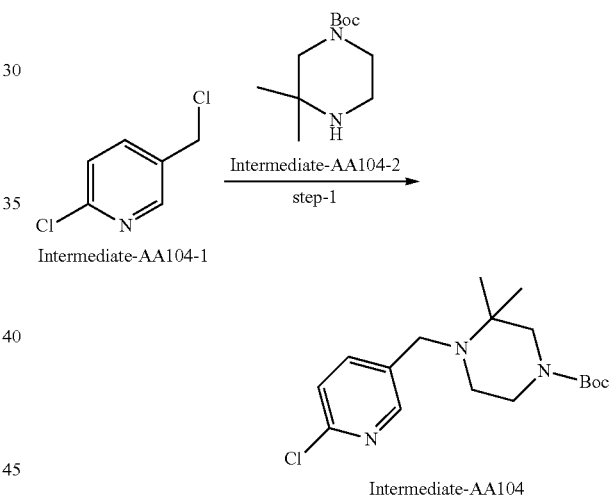

Intermediate-AA104

Step-1 tert-butyl 4-((6-chloropyridin-3-yl)methyl)-3,3-dimethylpiperazine-1-carboxylate (Intermediate-AA104)

A solution of Intermediate-AA104-1 (1.0 gm, 6017 mmol, 1.0 eq) in Acetonitrile (10 mL), were add Intermediate-AA104-2 (1.58 gm, 7.4 mmol, 1.2 eq) and $K_2CO_3$ (2.55 gm, 18.5 mmol, 3.0 eq). Reaction mixture was heated 80° C. for 2 h. After completion of reaction, the reaction mixture washed with water (50 mL) and extracted with DCM (3×30 mL). The combined organic extracts were washed with brine (60 mL), dried over $Na_2SO_4$, filtered, and concentrated under reduced pressure to obtain crude. The residue was used in the next step without further purification. (Intermediate-AA104) (1.5 g, 71.50%), MS (ES): m/z=340.17 $[M+H]^+$

Synthesis of 6-methyl-5-(4-methylpiperazin-1-yl)pyridin-2-amine (Intermediate-AA105)

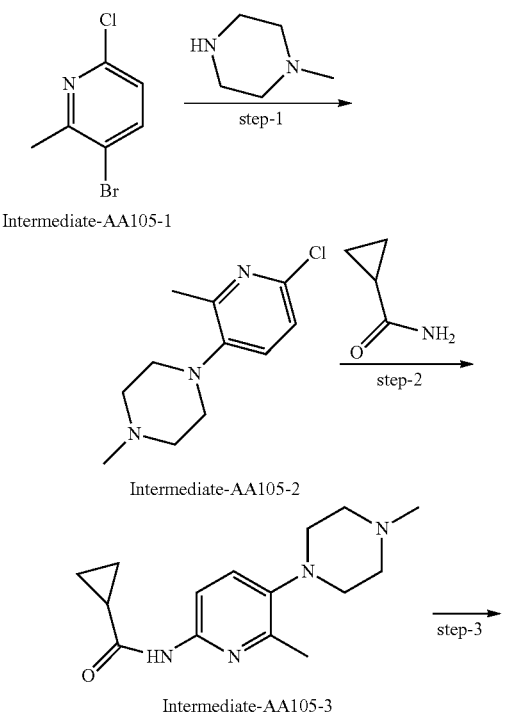

Step-1 Synthesis of Tert-Butyl (5-bromo-4-cyano-pyridin-2-yl)carbamate (Intermediate-AA105-2)

A solution of (Intermediate-AA105-1) (4.0 g, 19.41 mmol) and 1-methylpiperazine (1.7 g, 17.08 mmol, 0.88 eq), sodium tert-butoxide (3.7 g, 38.82 mmol, 2.0 eq) in toluene (40 mL) degassed under $N_2$ stream. After 15 min Xantphos (2.2 g, 3.88 mmol, 0.2 eq) and $Pd_2(dba)_3$ (1.7 g, 1.94 mmol, 0.1 eq) added and the reaction was stirred at 100° C. for 16 h. The reaction mixture was cooled to RT and then diluted water (150 mL) and extracted with ethyl acetate (3×50 mL). The combined organic extracts were washed with brine (100 mL), dried over $Na_2SO_4$, filtered, and concentrated under reduced pressure. The residue was purified by column chromatography eluting with 0-50% ethyl acetate in hexane to afford Intermediate-AA105-2 (2.0 g, 45.74%) as a brown solid. MS (ES): m/z=226.1 $[M+H]^+$.

Step-2 Synthesis of N-(6-methyl-5-(4-methylpiperazin-1-yl)pyridin-2-yl)cyclopropanecarboxamide (Intermediate-AA105-3)

A solution of Intermediate-AA105-2 (2.0 g, 8.88 mmol), 1-cyclopropanecarboxamide (1.5 g, 17.76 mmol, 2.0 eq) and $CS_2CO_3$ (8.6 g, 26.64 mmol, 3.0 eq) in 1,4-dioxane (20 mL) was degassed under $N_2$ stream. After 15 min, Xantphos (0.5 g, 0.88 mmol, 0.1 eq) and $Pd_2(dba)_3$ (0.8 g, 0.88 mmol, 0.1 eq) were added. After stirring at 120° C. for 16 h, the reaction mixture was cooled to RT, diluted water (80 mL) and extracted with ethyl acetate (3×50 mL). The combined organic extracts were washed with brine (80 mL), dried over $Na_2SO_4$, filtered, and concentrated under reduced pressure. The residue was purified by column chromatography eluting with 2.5-3.0% methanol gradient in DCM to afford Intermediate-AA105-3 (1.3 g, 53.47%) MS (ES): m/z=275.18 $[M+H]^+$.

Step-3 Synthesis of 6-methyl-5-(4-methylpiperazin-1-yl)pyridin-2-amine (Intermediate-AA105)

To a solution of Intermediate-AA105-3 (1.2 g, 4.37 mmol) in methanol (20 mL) and water (5 mL) was added sodium hydroxide (1.7 g, 43.7 mmol, 10.0 eq). After stirring at 70-80° for 16 h, the reaction mixture concentrated under reduced pressure. The residue was extracted with 10% methanol in DCM (3×70 mL). The combined organic extracts were washed with brine (80 mL), dried over $Na_2SO_4$, filtered, and concentrated under reduced pressure. The residue was used in the next step without further purification (Intermediate-AA105) (8.0 g, quantitative %), MS (ES): m/z 207.16 $[M+H]_+$

Synthesis of 1-(6-aminopyridin-3-yl)-3,6-dimethylpiperidin-3-ol (Intermediate-AA106)

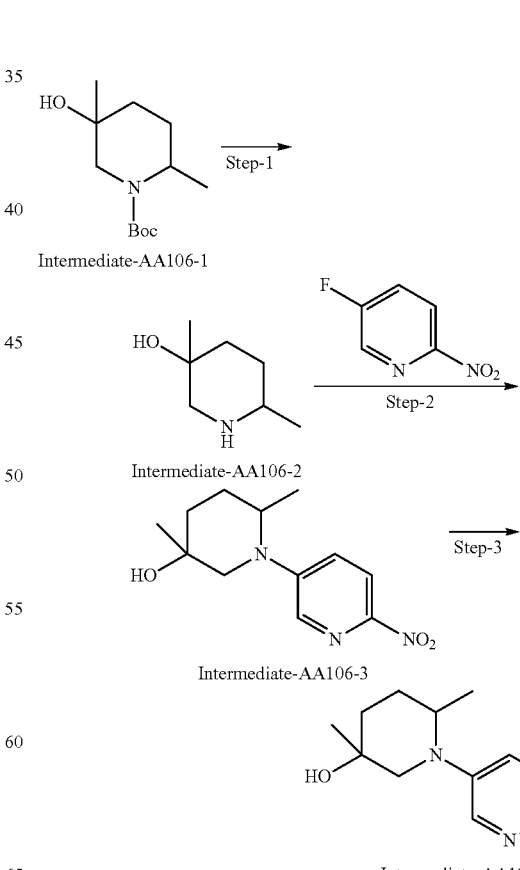

Step-1 Synthesis of 3,6-dimethylpiperidin-3-ol (Intermediate-AA106-2)

To a solution of Intermediate-AA106-1 (2 g) in DCM (20 mL) was added TFA (6 mL) at 0° C. After stirring at RT for 30 min, the reaction mixture was concentrated under reduced pressure to obtain the title compound Intermediate-AA106-2 (1 g, 88.74%). MS (ES): m/z=130.2 (M+1)+

Step-2 Synthesis of 3,6-dimethyl-1-(6-nitropyridin-3-yl)piperidin-3-ol (AA106-3)

To a solution of Intermediate-AA106-2 (1.4 g, 10.7 mmol, 1 eq) in DMSO (15 mL) were added 5-fluoro-2-nitropyridine (1 g, 12.84 mmol, 1.2 eq) and DIPEA (6 mL, 53.5 mmol, 5 eq). After stirring at 90° C. for 1 h, the reaction mixture was cooled to RT and diluted with water (50 mL) and ethyl acetate (100 mL). The organic layer was collected, and the aqueous phase was extract with ethyl acetate (300 mL). The combined organic extracts were washed with brine (200 mL), dried over Na$_2$SO$_4$, filtered, and concentrated under reduced pressure. The residue was purified by column to afford the title compound (Intermediate-AA106-2) (1.4 g, 55%). MS (ES): m/z=252.29 [M+1]+

Step-3 Synthesis of 1-(6-aminopyridin-3-yl)-3,6-dimethylpiperidin-3-ol (Intermediate-AA106)

To a suspension of 10% Pd/c (2.5 g) in MeOH (20 mL) was added Intermediate AA156-3 (5 g). After stirring at RT for 1 h with H$_2$ gas at atmospheric pressure, the reaction mixture was filtered through celite bed and filtrate was evaporated in vacuum to obtain Intermediate-AA106 (4 g, 90.74%) which was used in the next step without purification MS (ES): m/z=221.30 [M+H]$^+$.

Synthesis of 1-((6-chloropyridin-3-yl)methyl)-4-methylpiperazine (Intermediate-AA108)

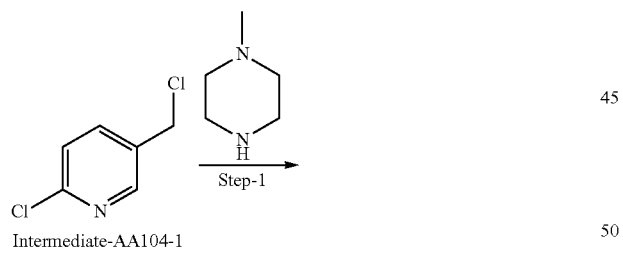

Step-1 Synthesis of 1-((6-chloropyridin-3-yl)methyl)-4-methylpiperazine (Intermediate-AA108)

To a solution of Intermediate-AA104-1 (2 g, 12.5 mmol, 1 eq) in DMSO (20 mL) were added 1-methylpiperazine (1.5 g, 15 mmol, 1.2 eq) and K$_2$CO$_3$ (5.17 g, 37.5 mmol, 3 eq). After stirring at 90° C. for 4 h, the reaction mixture was cooled at RT, diluted with water (50 mL), and extracted with ethyl acetate (100 mL). The organic layer was collected, and the aqueous phase was extract with ethyl acetate (200 mL). The combined organic extracts were washed with brine (100 mL), dried over Na$_2$SO$_4$, filtered, and concentrated under reduced pressure. The residue was purified by column to afford the title compound (Intermediate-AA108) (1.4 g, 50.24%). MS (ES): m/z=226.72 [M+1]+.

Synthesis of 5-(3-((dimethylamino)methyl)-3-methoxypiperidin-1-yl)pyridin-2-amine (Intermediate-AA109)

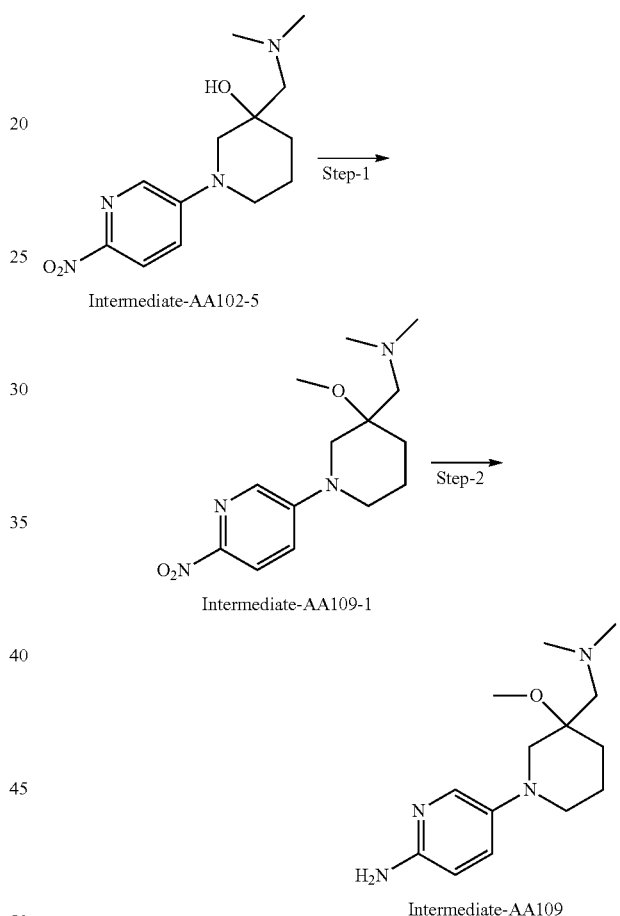

Step-1 Synthesis of 1-(3-methoxy-1-(6-nitropyridin-3-yl)piperidin-3-yl)-N,N-dimethylmethanamine (Intermediate-AA109-1)

To a solution of Intermediate-AA102-5 (1 g, 3.5 mmol, 1 eq) in THF (10 mL) was added NaH (0.257 g, 10.7 mmol, 3 eq) at 0° C. After stirring for 30 min, CH$_3$I (0.294 g, 7 mmol, 2 eq) was added. After stirring at RT for 1 h, the reaction mixture was diluted with water (50 mL) and extracted with ethyl acetate (50 mL). The combined organic extracts were washed with brine (60 mL), dried over Na$_2$SO$_4$, filtered, and concentrated under reduced pressure. The residue was purified by column chromatography to afford Intermediate-AA109-1 (600 mg, 57%). MS (ES): m/z=294.17 [M+1]+

Step-2 Synthesis of 5-(3-((dimethylamino)methyl)-3-methoxypiperidin-1-yl)pyridin-2-(Intermediate-AA109)

To a suspension of 10% palladium on charcoal (0.385 g) in methanol (10 mL) was added Intermediate-AA109-1 (0.600 g, 2.04 mmol). After hydrogenating for 3 h at atmospheric pressure, the reaction mixture was filtered through celite-bed and washed with methanol. The filtrate was concentrated under reduced pressure to obtain Intermediate-AA109 which was used in the next step without further purification. (500 mg, 92%). MS (ES): m/z 264.37 [M+H]$^+$.

Synthesis of 6-(1-methyl-1,6-diazaspiro [3.4] octan-6-yl) pyridin-2-amine (Intermediate-AA110)

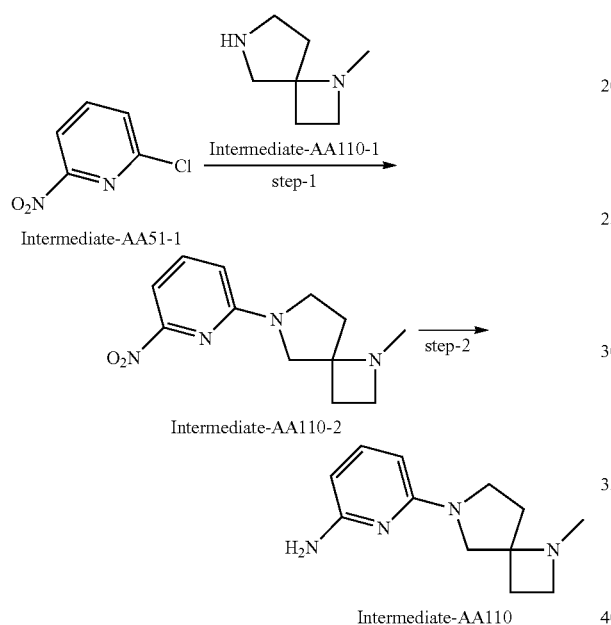

Step-1 Synthesis of 1-methyl-6-(6-nitropyridin-2-yl)-1,6-diazaspiro[3.4]octane (Intermediate-AA110-2)

To a solution of Intermediate-AA110-1 (0.100 g, 0.793 mmol), in dioxane were added 1-methyl-1,6-diazaspiro[3.4] octane (0.150 g, 0.952 mmol, 1.2 eq) and K$_3$PO$_4$ (0.336 g, 1.58 mmol, 2 eq). After degassing under N$_2$ stream for 20 min, Pd$_2$(dba)$_3$ (0.072 g, 0.079 mmol, 0.1 eq) and Xantphos (0.045 g, 0.079 mmol, 0.1 eq) were added After stirring at 100° C. for 1 h, the reaction mixture was cooled at RT and filtered through celite bed. The filtrate was diluted with ethyl acetate (20 mL) and water (20 mL). The organic layer was collected, and the aqueous phase was extracted with ethyl acetate (2×20 mL). The combined organic extracts were wash with brine (20 mL), dried over Na$_2$SO$_4$, filtered, and concentrated under reduced pressure. The residue was purified by column chromatography (0-2% gradient elution MeOH in DCM) to afford Intermediate-AA110-2 (0.130 g, 83%). MS (ES): m/z=248.13 [M+H]$^+$.

Step-2 Synthesis of 6-(1-methyl-1,6-diazaspiro[3.4]octan-6-yl)pyridin-2-amine (Intermediate-AA110)

To a suspension of palladium on charcoal (0.300 g) in methanol (5 mL), was added Intermediate-AA110-2 (0.300 g). After hydrogenating for 2 h, the reaction was filter through celite-bed and washed with methanol. The filtrate was concentrated under reduced pressure to obtain Intermediate-AA110 which was used in the next step without further purification. (0.210 g, 79%). MS (ES): m/z=218.15 [M+H]$^+$ Synthesis of 1-(4-(6-aminopyridin-3-yl)morpholin-2-yl)ethan-1-ol (Intermediate-AA111)

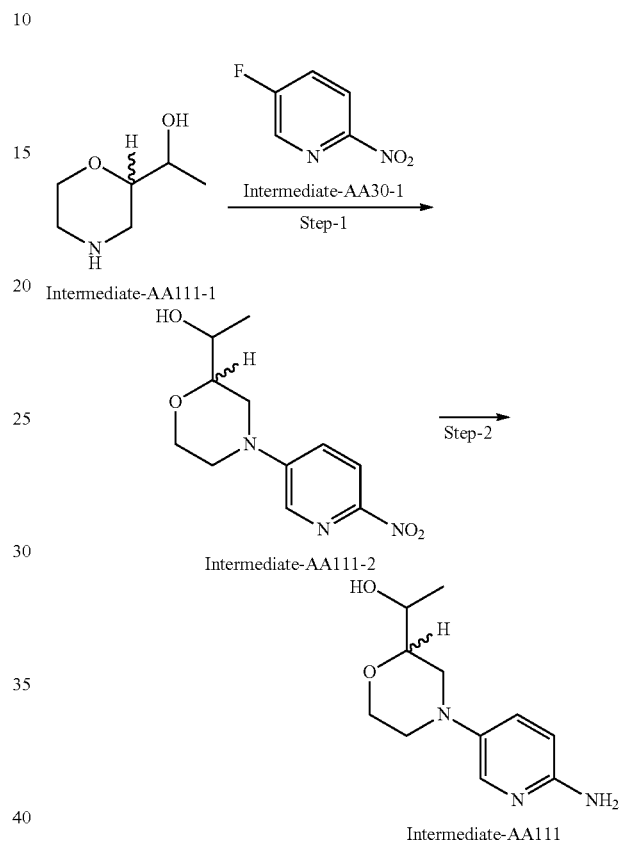

Step-1 Synthesis of 1-(4-(6-nitropyridin-3-yl)morpholin-2-yl)ethan-1-ol (Intermediate AA111-2)

To a solution of Intermediate-AA111-1 (1.4 g, 11.1 mmol, 2.0 eq) in DMSO (15 mL) were added Intermediate-AA30-1 (0.8 g, 5.5 mmol) and DIPEA (4.8 mL, 27.7 mmol, 5 eq). After stirring at 90° C. for 1 h, the reaction mixture was cooled at RT and diluted with water (50 mL) and ethyl acetate (100 mL). The organic layer was collected, and the aqueous phase was extract with ethyl acetate (300 mL). The combined organic extracts were washed with brine (200 mL), dried over Na$_2$SO$_4$, filtered, and concentrated under reduced pressure. The residue was purified by column chromatography (1% gradient elution MeOH in DCM). The purified solid was triturated with diethyl ether and the resulting solid was collected by filtration to afford the title compound (Intermediate-AA111-2) (1.8 g, 66.5%). MS (ES): m/z=253.2 [M+H]+

Step-2 Synthesis of 1-(4-(6-aminopyridin-3-yl)morpholin-2-yl)ethan-1-ol (Intermediate-AA111)

To a suspension of 10% Pd/c (1.8 g) in MeOH (20 mL) was added Intermediate AA111-2 (1.8 g). After hydrogenating for 1 h, the reaction mixture was filtrate through celite bed and organic layer was evaporate in vacuum to obtain Intermediate-AA111 (1.7 g, quantitative) which was used in the next step without purification MS (ES): m/z=223.2 [M+H]$^+$.

Synthesis of 2-(4-(6-aminopyridin-3-yl)-1-methylpiperazin-2-yl)propan-2-ol (Intermediate-AA112)

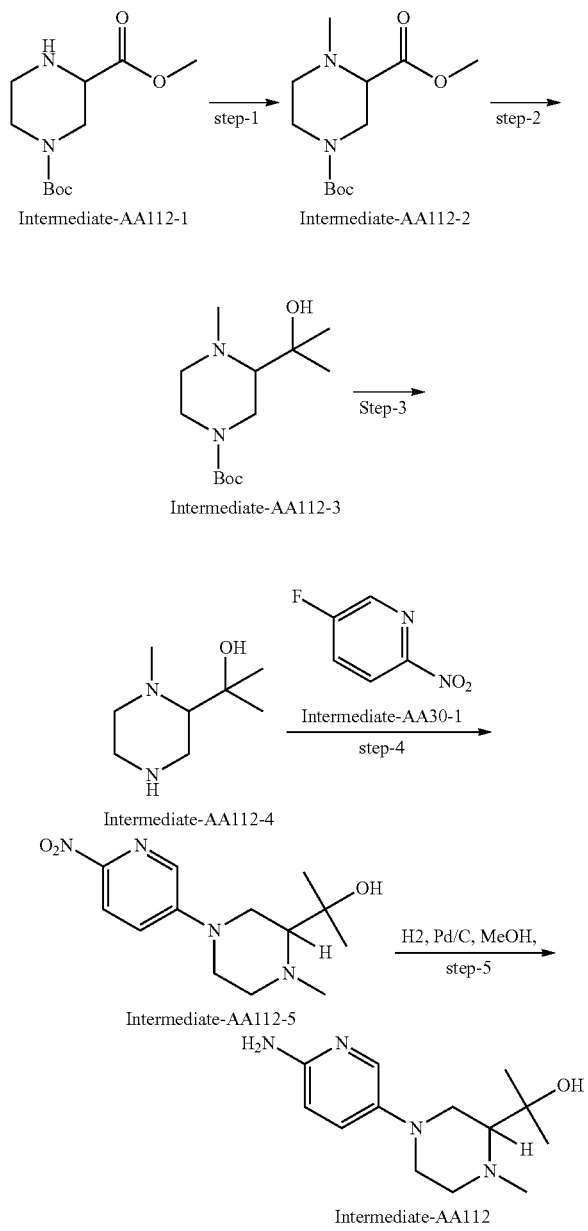

Step-1 Synthesis of 1-(tert-butyl) 3-methyl 4-methylpiperazine-1,3-dicarboxylate (Intermediate Intermediate-AA112-2)

To a solution of the Intermediate-AA112-1 (5 g, 20.4 mmol), in THF (80 mL) was added DIPEA (3.2 g, 24.5 mmol, 1.2 eq). After stirring at RT for 30 min, MeI (5.8 g, 41.0 mmol, 2 eq) was added. After stirring at 60° C. for 4 h, the reaction was quenched with water (100 mL) and extracted in ethyl acetate (3×40 mL). The combined organic layer was washed with brine, passed through a hydrophobic filter, and evaporated in vacuum. The residue was purified by column chromatography eluting with 25 to 50% ethyl acetate in hexane to give the title compound Intermediate-AA112-2 (2.5 g, 47.2%). MS (ES): m/z 258.3 [M+1]$^+$ Step-2 Synthesis of Tert-Butyl 3-(2-hydroxypropan-2-yl)-4-methylpiperazine-1-carboxylate (Intermediate-AA112-3)

To a solution of Intermediate-AA112-2 (9 g, 68 mmol) in chloroform (100 mL), at −78° C. was added MeMgBr (13.3 g, 74 mmol, 1.1 eq). After stirring at −78° C. to 0° C. over 4 h, the reaction was quenched with HCl to ~pH-7, diluted with water (100 mL) and extracted with ethyl acetate (3×40 mL). The combined organic layers were washed with brine, passed through a hydrophobic filter, and evaporated in vacuum. The residue was purified by column chromatography eluting with 25 to 30% ethyl acetate in hexane to give the title compound Intermediate-AA112-3 (1 g, 40%). MS (ES): m/z 258.3 [M+1]$^+$ Step-3 Synthesis of 2-(1-methylpiperazin-2-yl) propan-2-ol (Intermediate-AA112-4)

To a solution of Intermediate-AA112-3 (1 g, 3.9 mmol) in DCM (5 mL) at 0° C. was added HCl in dioxane (10 mL). After stirring at RT for 2 h, the reaction was concentrated under reduced pressure to afford the title compound which was used in the next step without purification. Intermediate-AA112-4 (0.500 g, 81.63%). MS (ES): m/z 158.2 [M+1]$^+$ Step-4 Synthesis of 2-(1-methyl-4-(6-nitropyridin-3-yl) piperazin-2-yl)propan-2-ol (Intermediate-AA112-5)

To a solution of the Intermediate-AA112-4 (0.8 g, 5.6 mmol) 5-fluoro-2-nitropyridine (Intermediate AA30-1) (1.0 g, 6.7 mmol, 1.2 eq) in DMSO (8 mL) were added TBAI (0.21 gm, 0.5 mmol, 0.1 eq) and K$_2$CO$_3$ (1.5 g, 11.6 mmol, 0.2 eq). After stirring at 100° C. for 3 h, the reaction mixture was cooled at RT, diluted with water, and extracted with ethyl acetate (20 mL). The organic layer was collected, and the aqueous phase was extracted with ethyl acetate (2×30 mL). The combined organic extracts were washed with brine (10 mL), dried over Na$_2$SO$_4$, filtered, and concentrated under reduced pressure. The residue was purified by column chromatography to give the title compound Intermediate-AA112-5 (0.8 g, 56.4%). MS (ES): m/z 283.3 [M+1]$^+$ Step-5 Synthesis of 2-(4-(6-aminopyridin-3-yl)-1-methylpiperazin-2-yl) propan-2-ol (Intermediate-AA112)

To a suspension of 10% Pd/C (0.6 g) in methanol (25 mL) was added Intermediate-AA112 (0.8 g). After hydrogenating at atmospheric pressure for 2 h, the reaction mixture was filtrate through celite bed. The filtrate was evaporated in vacuum to obtain Intermediate-AA112 (0.8 g, quantitative) which used in the next step without purification. MS (ES): m/z 250 [M+H]$^+$.

Synthesis of 2-(4-(6-aminopyridin-3-yl)-1,4-oxazepan-6-yl)propan-2-ol (Intermediate-AA113)

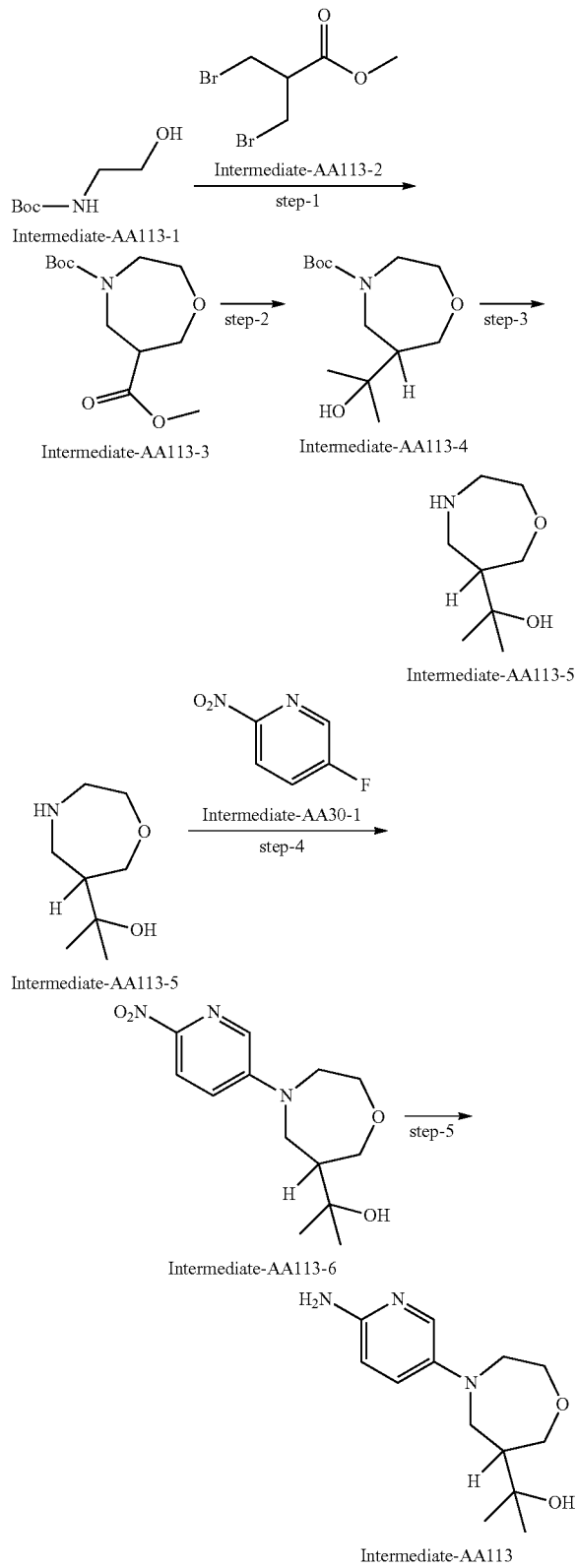

Step-1 Synthesis of 4-(tert-butyl) 6-methyl 1,4-oxazepane-4,6-dicarboxylate (Intermediate-AA113-3)

To a solution of Intermediate-AA113-1 (1 g, 6.2 mmol) in acetone was added $K_2CO_3$ (2.57 g, 18.6 mmol, 3.0 eq). After stirring at RT for 5 min, Intermediate-AA113-2 (1.6 mL, 6.2 mmol) was added dropwise. After stirring at reflux for 1 h, the reaction mixture was cooled at RT and diluted with ethyl acetate (20 mL) and water (20 mL). The organic layer was collected, and the aqueous phase was extracted with ethyl acetate (2×30 mL). The combined organic extracts were washed with brine (20 mL), dried over $Na_2SO_4$, filtered, and concentrated under reduced pressure to afford Intermediate-AA113-3 (0.7 g, 43.52%), MS (ES): m/z=259 [M+H]$^+$

Step-2 Synthesis tert-butyl 6-(2-hydroxypropan-2-yl)-1,4-oxazepane-4-carboxylate (Intermediate-AA113-4)

To a solution of Intermediate-AA113-3 (0.5 g, 26.7 mmol), in THF (5 mL) at 0° C. was added MeMgCl (4 mL) dropwise. After stirring at RT for 30 min, the reaction was quench with water (100 mL) and extracted in ethyl acetate (3×40 mL). The combined organic layer was wash with brine, passed through a hydrophobic filter, and evaporated in vacuum to obtain Intermediate-AA113-4 (0.5 g, 79.88%) which was used in the next step without purification. MS (ES): m/z=259 [M+1]$^+$

Step-3 Synthesis 2-(1,4-oxazepan-6-yl)propan-2-ol (Intermediate-AA113-5)

To a solution of Intermediate-AA113-4 (0.5 g) into DCM (5 mL) at 0° C. was added TFA (3.5 mL). After stirring at RT for 30 min, the reaction mixture was concentrated under reduced pressure to obtain to give the title compound Intermediate-AA113-5 (0.30 g, 97.73%). MS (ES): m/z=159 (M+H).

Step-4 Synthesis of 2-(4-(6-nitropyridin-3-yl)-1,4-oxazepan-6-yl)propan-2-ol (AA113-6)

To a solution of the Intermediate-AA113-5 (1.6 g, 5.6 mmol) in DMSO (40 mL) with DIPEA (1.4 gm, 6.7 mmol, 1.2 eq) at RT was added dropwise 5-fluoro-2-nitropyridine (1.6 g, 5.6 mmol). After stirring for 1 h at 100° C., the reaction mixture was cooled at RT and diluted with ethyl acetate (20 mL) and water (15 mL). The organic layer was collected, and the aqueous phase was extracted with ethyl acetate (2×30 mL). The combined organic extracts were washed with brine (10 mL), dried over $Na_2SO_4$, filtered, and concentrated under reduced pressure. The residue was purified by column chromatography eluting with 0.5% methanol gradient in DCM to give title compound (Intermediate-AA113-6) (0.3 g, 57%), MS (ES): m/z=281 [M+H]$^+$.

Step-5 Synthesis of 2-(4-(6-aminopyridin-3-yl)-1,4-oxazepan-6-yl)propan-2-ol (Intermediate-AA113)

To a suspension of 10% Pd/c (0.150 g) in MeOH (6 mL) was added Intermediate-AA113-6 (0.3 g). After stirring at RT with $H_2$ gas atmospheric pressure, the reaction mixture was filtered through a celite bed. The organic solution was evaporated in vacuum to afford Intermediate-AA113 (0.256 g, quantitative) which was used in the next step without purification. MS (ES): m/z=251 [M+1]+

Synthesis of Tert-Butyl 1-(6-aminopyridin-2-yl)hexahydropyrrolo[3,4-b]pyrrole-5(1H)-carboxylate (Intermediate-AA114)

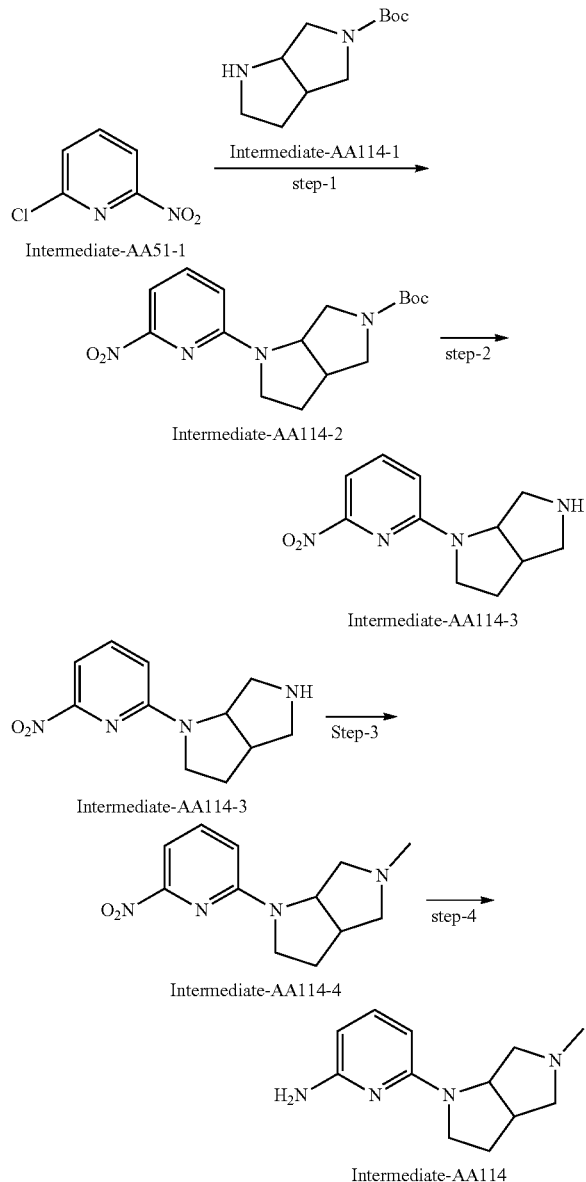

Step-1 Synthesis of Tert-Butyl 1-(6-aminopyridin-2-yl)hexahydropyrrolo[3,4-b]pyrrole-5(1H)-carboxylate (Intermediate-AA114-2)

To a solution of Intermediate-AA114-1 (1 g, 6.3 mmol, 1 eq) in dioxane (10 mL) were added tert-butyl hexahydropyrrolo[3,4-b]pyrrole-5(1H)-carboxylate (1.6 g, 7.5 mmol, 1.2 eq) and $K_2CO_3$ (1.7 g, 12.6 mmol, 2 eq). After degassing under $N_2$ stream for 20 min, $Pd_2(dba)_3$ (0.57 g, 0.63 mmol, 0.1 eq) and Xantphos (0.36 g, 0.63 mmol, 0.1 eq) were added. After stirring at 100° C. for 1 h, the reaction mixture was cooled at RT and filtered through celite bed. The filtrate was diluted with ethyl acetate (50 mL) and water (50 mL). The organic layer was collected, and the aqueous phase was extract with ethyl acetate (2×30 mL). The combined organic extracts were washed with brine (20 mL), dried over $Na_2SO_4$, filtered, and concentrated under reduced pressure. The residue was purified by column chromatography eluting with 0-15% gradient elution EtOAc in hexane to afford Intermediate-AA114-2 (1.8 g, 93.85%). MS (ES): m/z=304 [M+1]+

Step-2 Synthesis of 1-(6-nitropyridin-2-yl)octahydropyrrolo[3,4-b]pyrrole (Intermediate-AA114-3)

To a solution of Intermediate-AA114-2 (1.3 g, 3.88 mmol, 1 eq) in DCM, was added TFA (6.5 mL). After stirring at RT for 1 h, the reaction was neutralized using saturated sodium bicarbonate solution. The solution was extracted with DCM (3×40 mL) and the combined organic layer were concentrated under reduced pressure to afford Intermediate-AA114-3 (0.750 g, 94.85%). MS (ES): m/z=204 [M+1]+

Step-3 Synthesis of 5-methyl-1-(6-nitropyridin-2-yl)octahydropyrrolo[3,4-b]pyrrole (Intermediate-AA114-4)

To a solution of Intermediate-AA114-3 (0.485 g, 2.07 mmol, 1 eq) in THF at 0° C. was added NaH (0.033 g, 4.14 mmol, 2 eq). After stirring at RT for 15 min, MeI (0.440 g, 3.10 mmol, 1.5 eq) was added. After stirring for 2 h, the reaction was diluted ethyl acetate (200 mL) and water (20 mL). The organic layer was collected, and the aqueous phase was extracted with ethyl acetate (2×30 mL). The combined organic extracts were washed with brine (20 mL), dried over $Na_2SO_4$, filtered, and concentrated under reduced pressure to afford Intermediate-AA114-4 (0.510 g, 86.52%). MS (ES): m/z=248 [M+1]+.

Step-4 Synthesis of 6-(5-methylhexahydropyrrolo[3,4-b]pyrrol-1(2H)-yl)pyridin-2-amine (Intermediate-AA114)

To a suspension of 10% palladium on charcoal (0.385 g) in methanol (10 mL) was added Intermediate-AA114-4 (0.770 g, 3.101 mmol). After stirring under hydrogen gas at atmospheric pressure for 3 h at RT, the reaction mixture was filtered through celite-bed and washed with methanol. The filtrate was concentrated under reduced pressure to obtain Intermediate-AA114 which was used in the next step without further purification. (0.250 g, 36%). MS (ES): m/z 218.2 $[M+H]^+$ Synthesis of 4-(6-amino-4-((dimethylamino)methyl)pyridin-3-yl)tetrahydro-2H-pyran-4-ol (Intermediate-AA115)

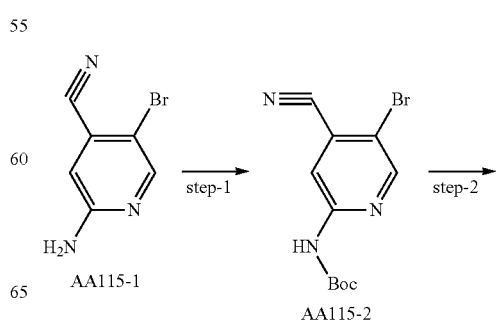

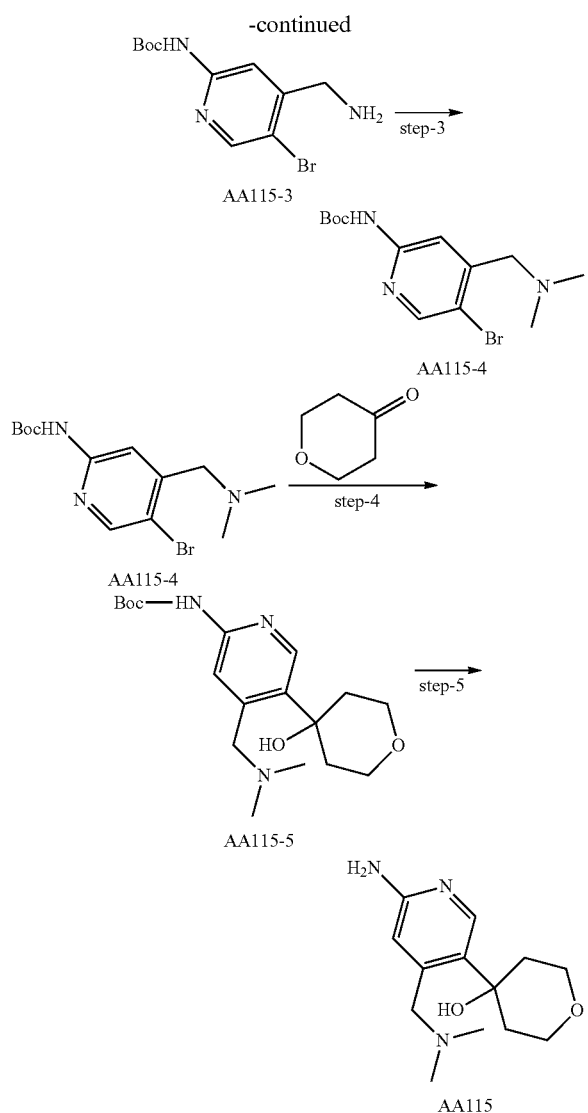

Step-1 Synthesis of Tert-Butyl (5-bromo-4-cyano-pyridin-2-yl)carbamate (Intermediate-AA115-2)

To a solution of Intermediate-AA115-1 (25.0 g, 126.26 mmol) in DCM (250 mL) were added DMAP (3.0 g, 25.25 mmol, 0.2 eq) and triethylamine (53 mL, 378.78 mmol, 3.0 eq) at 0° C. After 20 min, di-tert-butyl dicarbonate (35 mL, 151.51 mmol, 1.2 eq) was added dropwise. After stirring at RT for 16 h. the reaction mixture poured into ice cold water whereby a solid precipitated. The solid was collected and purified by column chromatography eluting with 10% gradient of ethyl acetate in hexane to afford Intermediate-AA115-2 (15.0 g, 39.85%), MS (ES): m/z 298.01 [M+H]$^+$.

Step-2 Synthesis of Tert-Butyl (4-(aminomethyl)-5-bromopyridin-2-yl)carbamate (Intermediate-AA115-3)

To a suspension of Raney Ni (pre-washed with methanol) (5 g) in Methanolic ammonia (13% w/w in methanol) (100 ml) was added Intermediate-AA115-2 (15.0 g, 50.33 mmol, 1.0 eq) in THF (50 mL). After stirring under hydrogen atmosphere at RT for 4 h, the reaction mixture was filtered through celite bed and washed with methanol. The filtrate was concentrated under reduced pressure. The residue was purified by column chromatography eluting with 25% ethyl acetate gradient in hexane to afford Intermediate-AA115-3 (10.0 g, 65.78%), MS (ES): m/z 303.04 [M+H]$^+$.

Step-3 Synthesis of Tert-Butyl (5-bromo-4-((dimethylamino)methyl)pyridin-2-yl)carbamate (Intermediate-AA115-4)

To a solution of Intermediate-AA115-3 (10.0 g, 33.11 mmol) in methanol (100 mL) were added formaldehyde (1.8 mL, 49.66 mmol, 1.5 eq) and acetic acid (0.4 mL, 8.27 mmol, 0.25 eq). After 30 min, sodium cyanoborohydride (2.4 g, 39.73 mmol, 1.2 eq) was added portion wise. After stirring at RT for 1 h, the reaction mixture was concentrated under reduced pressure to remove methanol to get solid precipitate which was purified by column chromatography eluting with 10% ethyl acetate gradient in hexane to afford Intermediate-AA115-4 (8.0 g, 73.20%), MS (ES): m/z 330.08 [M+H]$^+$

Step-4 Synthesis of Tert-Butyl (4-((dimethylamino)methyl)-5-(4-hydroxytetrahydro-2H-pyran-4-yl)pyridin-2-yl)carbamate (Intermediate-AA115-5)

To a solution of Intermediate-AA115-4 (8.0 g, 24.24 mmol) in dry THF (80 mL) at −76° C. added slowly dropwise n-butyllithium 2.5M in hexane (24 mLg, 60.6 mmol, 2.5 eq). After stirring for 1 h at −76° C., tetrahydro-4H-pyran-4-one (4.1 g, 41.20 mmol, 1.7 eq) was added. After stirring for 1 h, the reaction mixture transferred into ice cold water (200 mL) and extracted with ethyl acetate (2×100 mL). The combined organic extracts were washed with brine (100 mL), dried over Na$_2$SO$_4$, filtered, and concentrated under reduced pressure. The residue was purified by column chromatography eluting with 1% methanol gradient in DCM to afford Intermediate-AA115-5 (0.8 g, 10.40%), MS (ES): m/z 352.2 [M+H]$^+$.

Step-5 Synthesis of 4-(6-amino-4-((dimethylamino)methyl)pyridin-3-yl)tetrahydro-2H-pyran-4-ol (Intermediate-AA115)

To a solution of Intermediate-AA115-4 (0.8 g, 2.27 mmol) in DCM (8 mL) at 0° C. was added 4M HCl in dioxane (3 mL). After stirring at RT for 1 h, the reaction mixture was neutralized with saturated sodium bicarbonate solution and extracted with 10% methanol in DCM (3×30 mL). The combine organic layer was concentrated under reduced pressure. The residue was purified by column chromatography eluting with 100% DCM to afford Intermediate-AA115 (0.450 g, 78.66%), MS (ES): m/z 252.17 [M+H]$^+$

Synthesis of 1-(4-aminophenyl)piperidin-4-ol (Intermediate-AA116)

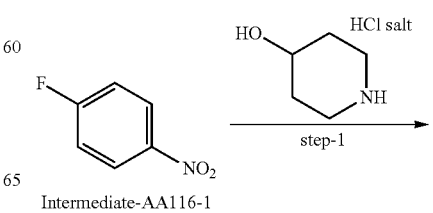

Intermediate-AA116-1

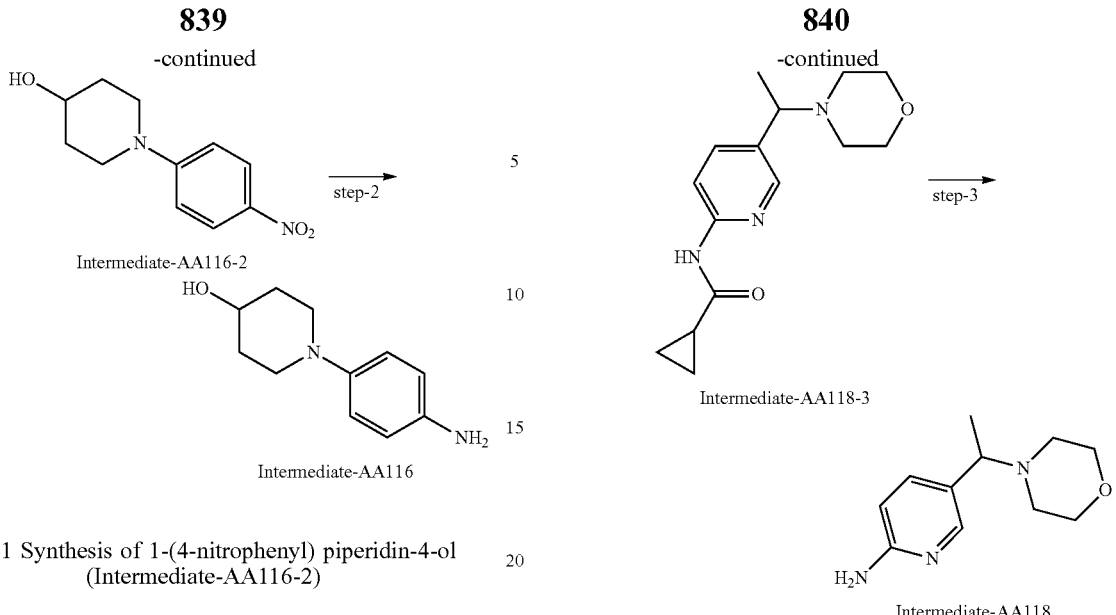

Step-1 Synthesis of 1-(4-nitrophenyl) piperidin-4-ol (Intermediate-AA116-2)

To a solution of piperidin-4-ol-HCl salt (1.07 g, 10.63 mmol, 1.5 eq) in DMF (15 mL) was added $K_2CO_3$ (2.93 g, 21.27 mmol, 3.0 eq). After stirring for 30 min, 1-fluoro-4-nitrobenzene (1 g, 7.09 mmol) was added. After stirring at 80° C. for 1 h, the reaction mixture was diluted with water (70 mL) and extracted with DCM (100 mL×2). The combined organic layer was dried over sodium sulfate and concentrated under reduced pressure. The residue was purified by column chromatography to obtain Intermediate-AA116-2 (700 mg, 44.44%). MS (ES): m/z 222 $[M+H]^+$ Step-2 Synthesis of 1-(4-aminophenyl)piperidin-4-ol (Intermediate-AA116)

To a suspension of Pd/C (350 mg) in methanol (5 mL), was added Intermediate-AA16-3 (700 mg). After hydrogenating at atmospheric pressure at RT for 4 h, the reaction mixture was filtered through celite-bed and washed with methanol. The filtrate was concentrated under reduced pressure to obtain Intermediate-AA116 (450 mg, 69.36%). MS (ES): m/z=192 $[M+H]^+$ Synthesis of 5-(1-morpholinoethyl)pyridin-2-amine (Intermediate-AA118)

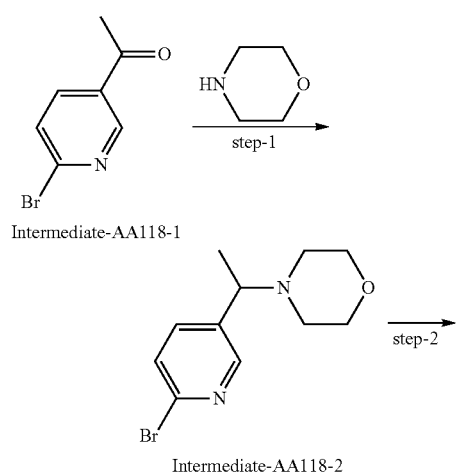

Step-1 Synthesis of 4-(1-(6-bromopyridin-3-yl) ethyl)morpholine (Intermediate-AA118-2)

To a solution of Intermediate-AA118-1 (1.0 g, 5.0 mmol), morpholine (0.783 g, 9.0 mmol, 1.8 eq) and triethylamine (1.0 mL, 7.5 mmol, 1.5 eq) in dichloroethane (10 mL) was added sodium triacetoxyborohydride (1.6 g, 8.0 mmol, 1.6 eq) portion wise. After stirring at RT for 16 h, the reaction was quenched with water (100 mL) and extracted into DCM (3×40 mL). The combined organic layer was washed with brine (50 mL), dried over $Na_2SO_4$, filtered, and concentrated under reduced pressure. The residue was purified by column chromatography 25% ethyl acetate gradient in hexane to afford Intermediate-AA118-2 (0.7 g, 51.64%) as a yellow oil. MS (ES): m/z 272.03 $[M+H]^+$ Step-2 Synthesis of N-(5-(1-morpholinoethyl)pyridin-2-yl)cyclopropanecarboxamide (Intermediate-AA118-3)

To a solution of Intermediate-AA118-2 (0.7 g, 2.58 mmol) in toluene (10 mL) were added cyclopropanecarboxamide (0.263 g, 3.0 mmol, 1.2 eq) and $Cs_2CO_3$ (2.0 g, 6.45 mmol, 2.5 eq). After degassing under $N_2$ stream for 15 min, Xantphos (0.149 g, 0.258 mmol, 0.1 eq) and $Pd_2(dba)_3$ (0.118 g, 0.129 mmol, 0.05 eq) were added. After stirring at 100° C. for 1 h, the reaction mixture was cooled to RT, diluted with water (50 mL), and extracted with ethyl acetate (3×30 mL). The combined organic extracts were washed with brine (50 mL), dried over $Na_2SO_4$, filtered, and concentrated under reduced pressure. The residue was purified by column chromatography eluting with 4% MeOH gradient in DCM to afford Intermediate-AA118-3 (0.6 g, 84.81%) as a brown solid. MS (ES): m/z=276.17 $[M+H]^+$.

Step-3 Synthesis of 5-(1-morpholinoethyl)pyridin-2-amine (Intermediate-AA118)

To a solution of Intermediate-AA118-3 (0.6 g, 2.17 mmol) in 1:1 methanol:water (8 mL) was added sodium hydroxide (0.868 g, 21.7 mmol, 10 eq). After stirring at reflux for 6 h, the reaction mixture was cooled to RT and concentrated under reduced pressure. The residue was purified by column chromatography eluting with 5% methanol in DCM to afford Intermediate-AA118 (0.280 g, 61.99%) as a brown solid. MS (ES): m/z=208.14 [M+H]$^+$ Synthesis of Tert-Butyl 1-(6-amino-4-methylpyridin-2-yl)hexahydropyrrolo[3,4-b]pyrrole-5(1H)-carboxylate (Intermediate-AA119)

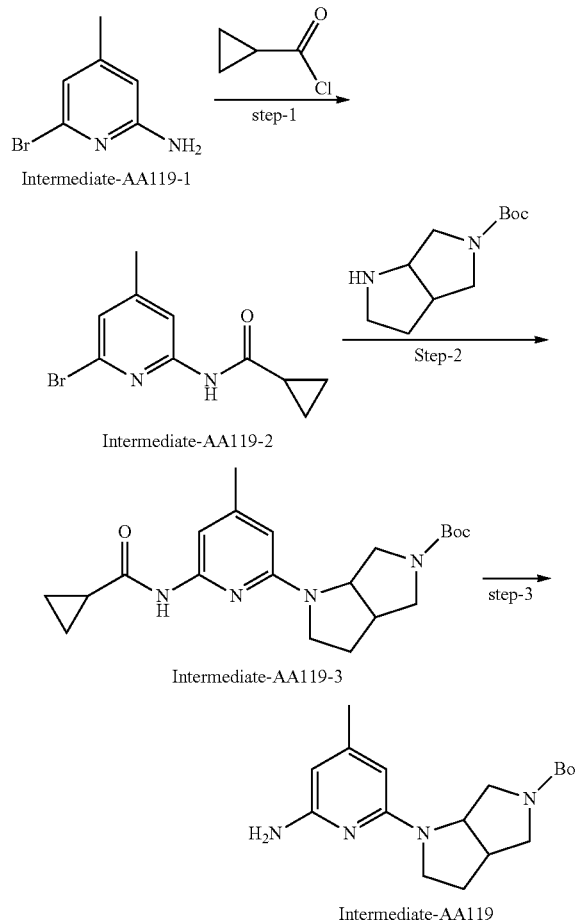

Step-1 Synthesis of N-(6-bromo-4-methylpyridin-2-yl)cyclopropanecarboxamide (Intermediate-AA119-2)

To a solution of Intermediate AA119-1 (2 g, 10.8 mmol) in DCM (40 mL) with trimethylamine (3.27 g, 32.43 mmol, 3.0 eq) at 0° C. was added cyclopropane carbonyl chloride (3.67 g, 43.2 mmol, 4 eq) dropwise. After stirring at RT for 2 h, the reaction was diluted with water (150 mL) and extracted with ethyl acetate (3×70 mL). The combined organic layer was washed with brine (150 mL), dried over Na$_2$SO$_4$, filtered, and concentrated under reduced pressure. The residue was purified by column chromatography to afford Intermediate-AA119-2 (1 g, 73%). MS (ES): m/z 255.2 [M+H]$^+$ Step-2 Synthesis of Tert-Butyl 1-(6-(cyclopropanecarboxamido)-4-methylpyridin-2-yl)hexahydropyrrolo[3,4-b]pyrrole-5(1H)-carboxylate (Intermediate AA119-3)

To a solution of Intermediate-AA119-2 (1.5 g, 5.9 mmol) in dioxane (15 mL) were added Intermediate AA119-4 (1.5 g, 7.08 mmol, 1.2 eq) and potassium carbonate (2.44 g, 17.7 mmol, 3.0 eq). After degassing with nitrogen for 20 min, Pd$_2$(dba)$_3$ (538 mg, 0.59 mmol, 0.1 eq) and Xantphos (341 mg, 0.59 mmol, 0.1 eq) were added. After stirring at 100° C. for 4 h, the reaction was diluted with water (100 mL) and extracted with ethyl acetate (3×80 mL). The combined organic layer was wash with brine (100 mL), dried over Na$_2$SO$_4$, filtered, and concentrated under reduced pressure. The residue was purified by column chromatography to afford Intermediate-AA119-3 (1 g, 44%). MS (ES): m/z 387.23 [M+H]$^+$ Step-3 Synthesis of Tert-Butyl 1-(6-amino-4-methylpyridin-2-yl)hexahydropyrrolo[3,4-b]pyrrole-5(1H)-carboxylate (Intermediate AA119)

To a solution of Intermediate-AA119-3 (0.850 g, 2.1 mmol) in methanol (10 mL) and water (3 mL) was added sodium hydroxide (0.878 g, 21 mmol, 10.0 eq). After stirring at 60° for 16 h, the reaction mixture was concentrated under reduced pressure and extracted with 10% methanol in DCM (3×90 mL). The combined organic layers were washed with brine (80 mL), dried over Na$_2$SO$_4$, filtered, concentrated under reduced pressure to afford Intermediate-AA119 which was used in the next step without further purification (0.6 g, 85%), MS (ES): m/z 318.20 [M+H]$^+$ Synthesis of 4-(6-amino-4-((dimethylamino)methyl)pyridin-3-yl)tetrahydro-2H-pyran-4-ol (Intermediate-AA122)

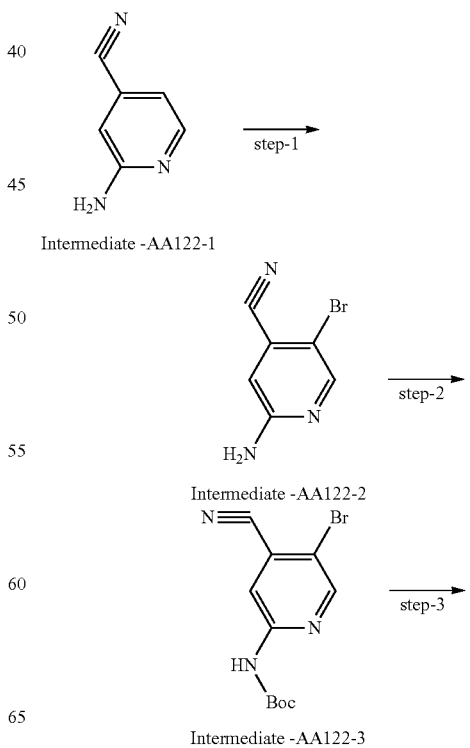

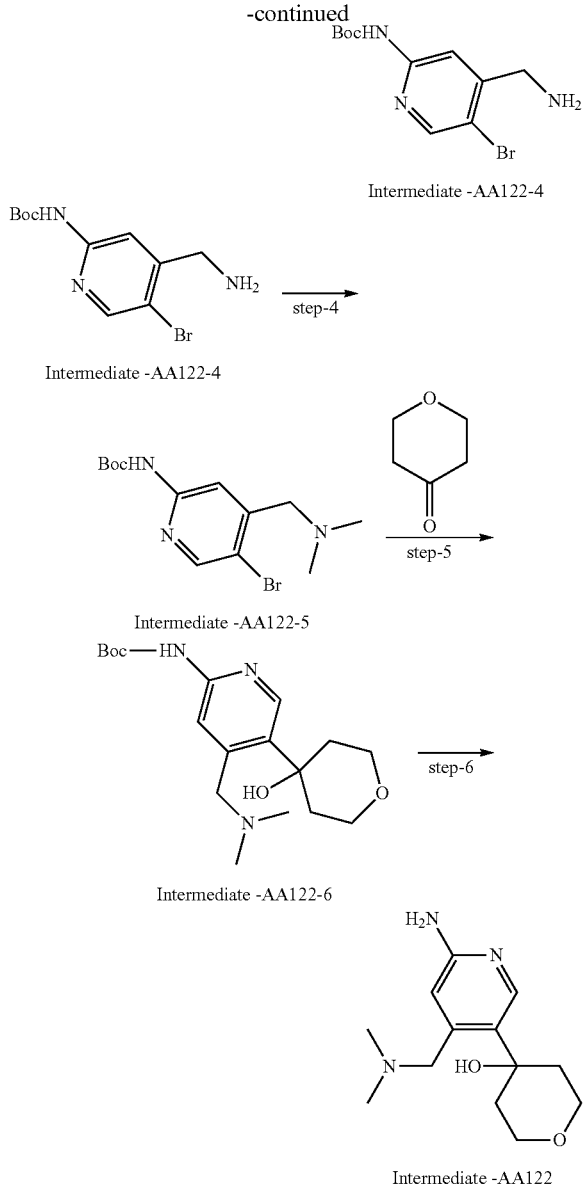

Step-1 Synthesis of 2-amino-5-bromoisonicotinonitrile (Intermediate-AA122-2)

To a solution of Intermediate-AA122-1 (20.0 g, 167.8 mmol) and N-bromo succinimide (Crystalline) (29.9 g, 167.8 mmol) in acetonitrile (400 mL) was stirred at RT for 2 h. After completion of reaction, the reaction mixture was diluted with sodium thiosulfate solution (1.0 L) and extracted with ethyl acetate (1 L×3). The combined organic layer was dried over sodium sulfate and concentrated under reduced pressure. The residue was purified by column chromatography eluting with 20% ethyl acetate in hexane to afford Intermediate-AA122-2 (20.0 g, 60.16%) as a yellow solid. MS (ES): m/z=196.96 [M+H]$^+$.

Step-2 Synthesis of Tert-Butyl (5-bromo-4-cyano-pyridin-2-yl) carbamate (Intermediate-AA122-3)

To a solution of Intermediate-AA122-2 (16.5 g, 82.9 mmol) and DMAP (2.0 g, 16.0 mmol, 0.2 eq) in THF (200 mL) and triethylamine (33 mL, 248.0 mmol, 3.0 eq) at 0° C. was added di-tert-butyl dicarbonate (21.6 g, 99.4 mmol, 1.2 eq). After stirring for 16 h at RT, the reaction mixture was diluted with water (500 mL) and extracted with ethyl acetate (3×200 mL). The combined organic extracts were washed with brine (150 mL), dried over Na$_2$SO$_4$, filtered, and concentrated under reduced pressure. The residue was purified by column chromatography eluting with 10% ethyl acetate gradient in hexanes to afford Intermediate-AA122-3 (10.0 g, 40.25%) as a white solid. MS (ES): m/z=297.1 [M+H]$^+$.

Step-3 Synthesis of Tert-Butyl (4-(aminomethyl)-5-bromopyridin-2-yl) carbamate (Intermediate-AA122-4)

To a suspension of Raney Ni (4 mL) in THF (150 mL) was added Intermediate-AA122-3 (10.0 g, 33.55 mmol) followed by ammonia solution (18 mL). After hydrogenating at atmospheric atmosphere for 4 h, the reaction mixture was filtered through celite-bed and washed with methanol. The filtrate was concentrated under reduced pressure to obtain Intermediate-AA122-4 (8.0 g, 78.93%). MS (ES): m/z 303.04 [M+H]$^+$ Step-4 Synthesis of Tert-Butyl (5-bromo-4-((dimethylamino)methyl)pyridin-2-yl)carbamate (Intermediate-AA122-5)

To a solution of Intermediate-AA122-4 (8.0 g, 26.57 mmol) and formaldehyde (3.0 g, 99.0 mmol, 1.5 eq) in methanol (100 mL) was added acetic acid (0.398 g, 6.64 mmol, 0.25 eq). After stirring at RT for 1 h, sodium cyanoborohydride (2.0 g, 318.2 mmol, 1.2 eq) was added portion wise. After stirring for 45 min at RT, the reaction mixture was concentrated, and the residue was suspended in water (100 mL). The resulting solid was collected by filtration and further purified by column chromatography eluting with 5% ethyl acetate gradient in hexanes to afford Intermediate-AA122-5 (2.6 g, 29.74%). MS (ES): m/z=331.07 [M+H]$^+$.

Step-5 Synthesis of Tert-Butyl (4-((dimethylamino)methyl)-5-(4-hydroxytetrahydro-2H-pyran-4-yl)pyridin-2-yl)carbamate (Intermediate-AA122-6)

To a suspension of Intermediate-AA122-5 (0.5 g, 1.51 mmol) in THF (5 mL) at −78° C. under argon was added n-butyllithium (1.6M) (1.51 mL, 3.78 mmol, 2.5 eq). After stirring at −78° C. for 1 h, tetrahydro-4H-pyran-4-one (0.257 g, 2.57 mmol, 1.7 eq) was added. After stirring −78° C. for 1 h, the reaction mixture was diluted with water (50 mL) and extracted with ethyl acetate (3×20 mL). The combined organic extracts were washed with brine (50 mL), dried over Na$_2$SO$_4$, filtered, and concentrated under reduced pressure. The residue was purified by column chromatography eluting with 1% MeOH gradient in DCM to afford Intermediate-AA129-6, (0.15 g, 28.19%). MS (ES): m/z 352.22 [M+H]$^+$ Step-6 Synthesis of 4-(6-amino-4-((dimethylamino)methyl) pyridin-3-yl) tetrahydro-2H-pyran-4-ol (Intermediate-AA122)

To a solution of Intermediate-AA122-6 (0.3 g, 0.85 mmol) in DCM (3 mL) was added 4 M HCl in dioxane (3.0 mL) at RT. After stirring at RT for 16 h, the reaction was diluted with water (30 mL), neutralized with NaHCO$_3$, and extracted with ethyl acetate (3×30 mL). The combined organic layers were dried over Na$_2$SO$_4$, filtered, and concentrated under reduced pressure to obtain Intermediate-AA122 (0.15 g, 69.92%): m/z=252.17 [M+H]$^+$ Synthesis of 1-(6-aminopyridin-3-yl)-3-(morpholinomethyl)piperidin-3-ol (Intermediate-AA123)

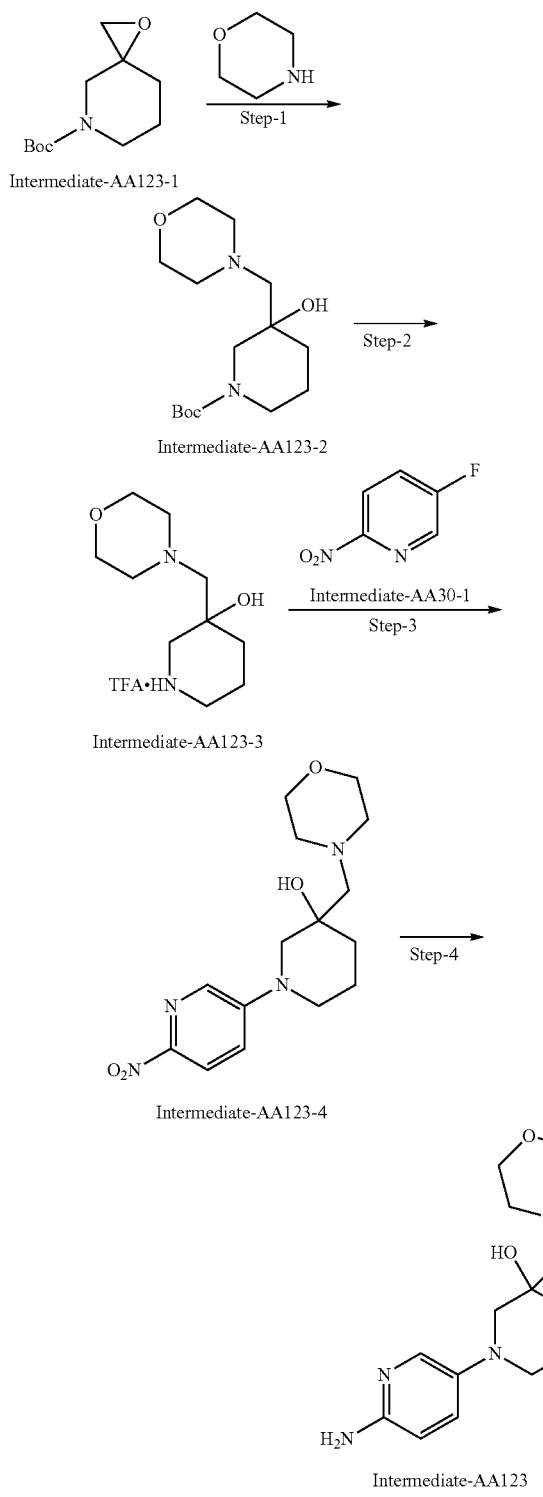

Step-1 Synthesis of Tert-Butyl 3-hydroxy-3-(morpholinomethyl)piperidine-1-carboxylate (Intermediate-AA123-2)

A solution of Intermediate-AA123-1 (1.7 gm, 7098 mmol, 1.0 eq) in ethanol (20 mL), was added morpholine (1.38 gm, 15.9 mmol, 2.0 eq). After stirring at 80° C. for 2 h, the reaction mixture was diluted with water (50 mL) and extracted with DCM (3×30 mL). The combined organic extracts were washed with brine (60 mL), dried over Na$_2$SO$_4$, filtered, and concentrated under reduced pressure affording Intermediate-AA123-2 (1.7 g, 71.1%) which was used in the next step without further purification. MS (ES): m/z=301.5 [M+H]$^+$.

Step-2 Synthesis 2,2,2-trifluoro-1-(3-hydroxy-3-(morpholinomethyl)-114-piperidin-1-yl)ethan-1-one (Intermediate-AA123-3)

To a solution of Intermediate-AA123-2 (5.0 g, 16.66 mmol) in DCM (50 mL), at 0° C. was added dropwise TFA (15 mL). After stirring at same temperature. Reaction mixture was stirred at RT for 1 h, the reaction mixture was diluted with water (80 mL) and sodium bicarbonate solution (50 mL) and extracted with DCM (3×80 mL). The combined organic extracts were washed with brine (150 mL), dried over Na$_2$SO$_4$, filtered, and concentrated under reduced pressure. The residue was triturated by ether and methanol to afford Intermediate-AA123-3 (6.0 g, 89%). MS (ES): m/z=298.3 [M+H]$^+$.

Step-3 Synthesis of 3-(morpholinomethyl)-1-(6-nitropyridin-3-yl)piperidin-3-ol (Intermediate-AA123-4)

To a solution of Intermediate-AA123-3 (1.7 gm, 52.28 mmol, 3.0 eq) in DMSO were added Intermediate-AA30-1 (2.5 gm, 17.6 mmol) and DIPEA (22.0 ML, 211 mmol, 7.0 eq). After stirring at 110° C. for 4 h, the reaction mixture was diluted with water (100 mL) and extracted with ethyl acetate (3×80 mL). The combined organic extracts were washed with brine (100 mL), dried over Na$_2$SO$_4$, filtered, and concentrated under reduced pressure. The residue was purified by column chromatography eluting with 2 to 3% methanol gradient in DCM to afford Intermediate-AA123-6 (4.0 g, 70.22%). MS (ES): m/z=323.1 [M+H]$^+$.

Step-4 Synthesis of 1-(6-aminopyridin-3-yl)-3-(morpholinomethyl)piperidin-3-ol (Intermediate-AA123)

To a suspension of 10% palladium on carbon (0.7 g) in methanol (15 mL) was added Intermediate-AA123-4 (1.4 g, 4.76 mmol). After stirring under hydrogen at atmospheric pressure for 4 h. the reaction mixture was filtered through Celite-bed and washed with methanol. The filtrate was concentrated under reduced pressure to obtain Intermediate-AA123 (1.2 g, 86.76%) which was used in the next step without further. MS (ES): m/z 293.19 [M+H]$^+$

Synthesis of Tert-Butyl 1-(6-aminopyrazin-2-yl)hexahydropyrrolo[3,4-b]pyrrole-5(1H)-carboxylate (Intermediate-AA124)

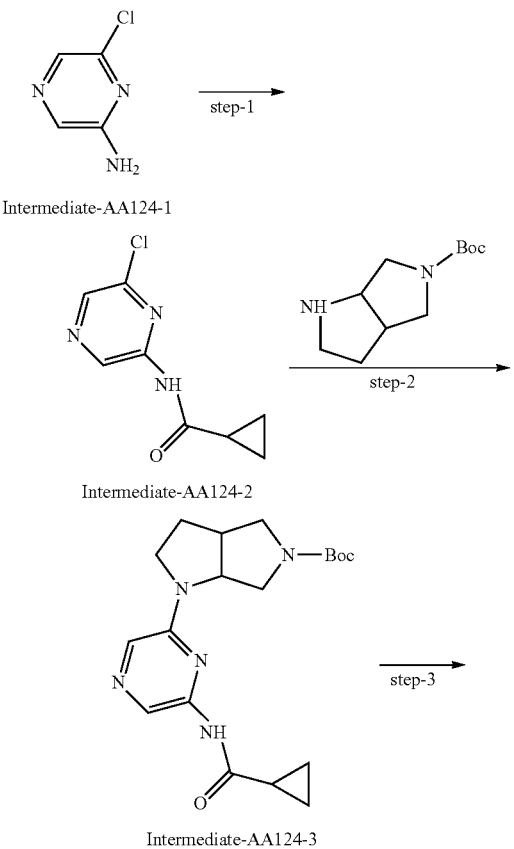

Step-1 Synthesis of N-(6-chloropyrazin-2-yl)cyclopropanecarboxamide (AA124-2)

To a solution of Intermediate-AA124-1 (2 g, 1.54 mmol) in DCM (16 mL) and trimethylamine (6.43 mL, 4.620 mmol, 3 eq) was added cyclopropane carbonyl chloride (6.4 g, 6.17 mmol, 4 eq). After stirring at RT for 2 h, the reaction mixture was diluted with water (30 mL) and extracted with DCM (3×80 mL). The combined organic extracts were washed with brine (50 mL), dried over Na$_2$SO$_4$, filtered, and concentrated under reduced pressure to afford Intermediate-AA124-2 which was use as such for next step. (1.5 g, 49.16%) MS (ES): m/z=197 [M+H]$^+$.

Step-2 Synthesis of tert-butyl1-(6-(cyclopropanecarboxamido)pyrazin-2-yl)hexahydropyrrolo[3,4-b]pyrrole-5(1H)-carboxylate (Intermediate-AA124-3)

To a solution of tert-butyl hexahydropyrrolo[3,4-b] pyrrole-5(1H)-carboxylate (1 g) in DMSO (15 mL), were added K$_2$CO$_3$ (2.93 g, 21.02 mmol, 3 eq) followed by TBAI (0.387 g, 2.12 mmol, 0.3 eq). After stirring at RT for 15 min, Intermediate-AA124-2 (1.4 g, 7.08 mmol, 1 eq) was added. After stirring at 100° C. for 16 h, the reaction mixture was diluted with water (30 mL) and extracted with ethyl acetate (3×40 mL). The combined organic extracts were wash with brine (50 mL), dried over Na$_2$SO$_4$, filtered, and concentrated under reduced pressure. The residue was purified by column chromatography eluting with 0-50% ethyl acetate gradient in hexane to afford Intermediate-AA124-3 (850 mg, 44.98%). MS (ES): m/z=373.4 [M+H]$^+$.

Step-3 Synthesis of Tert-Butyl 1-(6-aminopyrazin-2-yl)hexahydropyrrolo[3,4-b]pyrrole-5(1H)-carboxylate (Intermediate-AA124)

To a solution of Intermediate-AA124-3 (0.500 g, 1.33 mmol, 1 eq) in MeOH (5 mL), was added a solution of NaOH (1.07 g, 26.70 mmol, 20 eq) in water (4 mL). After stirring at 80° C. for 16 h, the reaction mixture was diluted with water (40 mL) and extracted with ethyl acetate (3×40 mL). The combined organic extracts were washed with brine (50 mL), dried over Na$_2$SO$_4$, filtered, and concentrated under reduced pressure. The residue was purified by column chromatography eluting with 0-50% ethyl acetate gradient in hexane to afford Intermediate-AA124 (320 mg, 78%). MS (ES): m/z=305.4 [M+H]+.

Synthesis of 1-(4-(6-aminopyridin-3-yl)morpholin-2-yl)cyclopropan-1-ol (Intermediate-AA125)

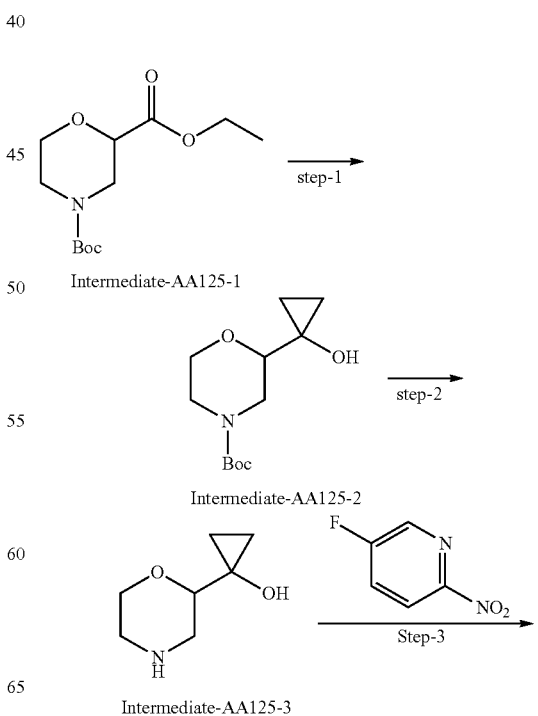

849

-continued

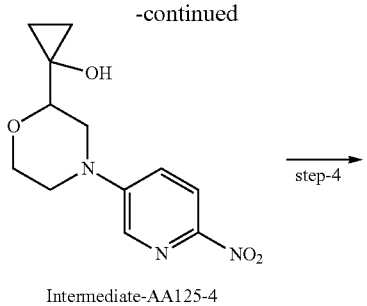

Intermediate-AA125-4

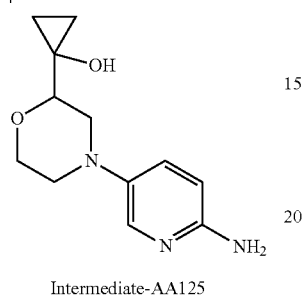

Intermediate-AA125

Step-1 Synthesis of Tert-Butyl 2-(1-hydroxycyclopropyl) morpholine-4-carboxylate (Intermediate-AA125-2)

To a solution of Intermediate-AA125-1 (10 g, 38.61 mmol) in THF (100 mL) at RT were added titanium(IV) isopropoxide (16 mL, 54.05 mmol, 1.4 eq) and EtMgBr (3M) (39 mL, 2.8 eq) dropwise. After stirring at RT for 1 h, the reaction mixture was quenched with aq NH$_4$Cl solution (100 mL) and extracted with ethyl acetate (3×80 mL). The combined organic extracts were washed with brine (100 mL) and dried over Na$_2$SO$_4$, filtered, and concentrated under reduced pressure. The residue was purified by column chromatography eluting with 0-14% ethyl acetate gradient in hexane to afford Intermediate-AA125-2 (1.2 g) MS (ES): m/z=243 [M+H]$^+$.

Step-2 Synthesis of 1-(morpholin-2-yl)cyclopropan-1-ol (Intermediate-AA125-3)

To a solution of Intermediate-AA125-2 (2.5 g, 10.28 mmol) in DCM (25 mL) was added TFA (3.9 mL, 51.44 mmol, 5 eq) dropwise. After stirring at RT for 30 min, the reaction was concentrated to afford Intermediate-AA125-3 which was used as such for next step. (2.1 g) MS (ES): m/z=143 [M+H]$^+$

Step-3 Synthesis of 1-(4-(6-nitropyridin-3-yl)morpholin-2-yl)cyclopropan-1-ol (Intermediate-AA125-4)

To a solution of Intermediate-AA125-3 (2 g, 13.98 mmol, 1 eq) in DMSO (20 mL) was added 5-fluoro-2-nitropyridine (2.9 g, 20.97 mmol, 1.5 eq) and DIPEA (9.416 mL, 69.9 mmol, 5 eq). After stirring at 100° C. for 2 h, the reaction mixture was diluted with water (20 mL) and extracted with ethyl acetate (3×30 mL). The combined organic extracts were washed with brine (30 mL), dried over Na$_2$SO$_4$, filtered, and concentrated under reduced pressure. The residue was purified by column chromatography eluting with

850

0-4% methanol gradient in DCM to afford Intermediate-AA125-4. (1.7 g). MS (ES): m/z=265 [M+H]$^+$.

Step-4 Synthesis of 1-(4-(6-aminopyridin-3-yl)morpholin-2-yl)cyclopropan-1-ol (Intermediate-AA125)

To a suspension of 10% palladium on carbon (0.9 g) in methanol (10 mL) was added Intermediate-AA125-4 (1.8 g, 6.79 mmol). After stirring under hydrogen gas at atmospheric pressure at RT for 3 h, the reaction mixture was filtered through Celite-bed and washed with methanol. The filtrate was concentrated under reduced pressure to afford Intermediate-AA125 (1.9 g) as a brown solid which was use in the next step without further purification. MS (ES): m/z=235.2 [M+H]$^+$

Synthesis of 1-(6-aminopyridin-3-yl)-4-methoxypiperidin-4-yl)methanol (Intermediate-AA126)

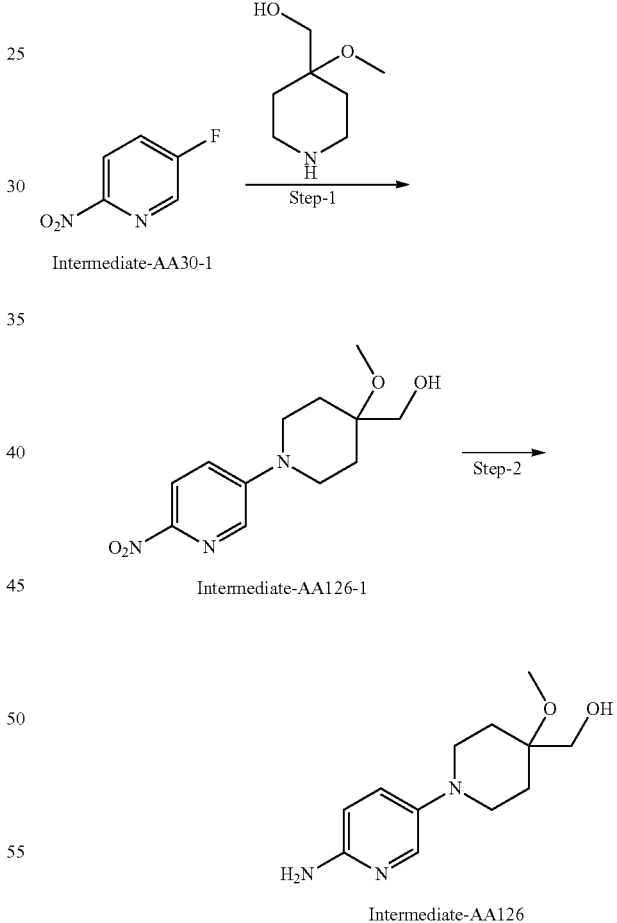

(1-(6-aminopyridin-3-yl)-4-methoxypiperidin-4-yl) methanol (Intermediate AA126) was prepared from commercial 5-Flouro-2-nitropyridine (Intermediate AA30-1) and (4-methoxypiperidin-4-yl)methanol in a similar fashion to that described 5-((3aR,6aS)-tetrahydro-1H-furo[3,4-c] pyrrol-5(3H)-yl)pyridin-2-amine (Intermediate AA30) (General process intermediate AA30) (0.300 g, 67%). MS (ES): m/z 239.23 [M+H]$^+$

Synthesis of Tert-Butyl 3-((6-amino-3-methylpyridin-2-yl)(methyl)amino)azetidine-1-carboxylate (Intermediate-AA128)

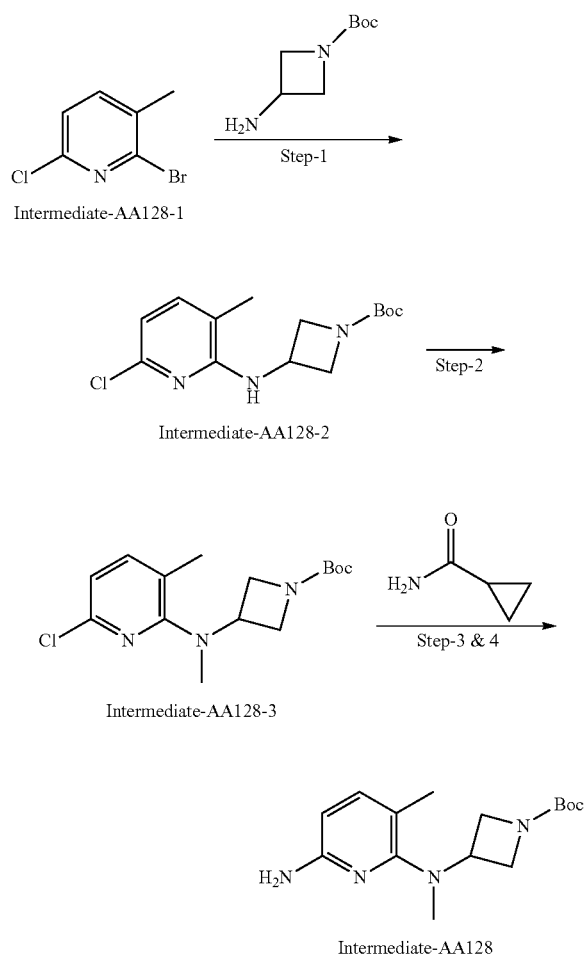

Step-1 Synthesis of Tert-Butyl 3-((6-chloro-3-methylpyridin-2-yl)amino)azetidine-1-carboxylate (Intermediate-AA128-2)

To a solution of Intermediate-AA128-1 (0.5 g, 2.42 mmol) in dioxane (6 mL) were added tert-butyl 3-aminoazetidine-1-carboxylate (0.417 g, 2.42 mmol, 1 eq) and $Cs_2CO_3$ (1.56 g, 4.84 mol, 3.0 eq). After degassing under $N_2$ stream for 20 min, $Pd_2(dba)_3$ (0.111 g, 0.121 mmol, 0.05 eq) and Xantphos (0.140 g, 0.242 mmol, 0.1 eq) were added. After stirring at 100° C. and for 1 h, the reaction mixture was cooled at RT and diluted ethyl acetate (100 mL) and water (50 mL). The organic layer was collected, and the aqueous phase was extracted with ethyl acetate (2×30 mL). The combined organic extracts were washed with brine (20 mL), dried over $Na_2SO_4$, filtered, and concentrated under reduced pressure. The residue was purified by column chromatography (0-50% gradient elution EtOAc in hexane). The isolated solid was triturated with diethyl ether and the resulting solid was collected by filtration to afford the title compound Intermediate-AA128-2 (240 mg, 34.5%). MS (ES): m/z=297.12 [M+1]+

Step-2 Synthesis of Tert-Butyl 3-((6-chloro-3-methylpyridin-2-yl)(methyl)amino)azetidine-1-carboxylate)(Intermediate-AA128-3)

To a solution of Intermediate-AA128-2 (0.2 g, 0.67 mmol, 1 eq.) in DMF (30 mL) was added sodium hydride (77 mg, 3.3 mmol, 5 eq). After stirring for 1 h, methyl iodide (113 mg, 0.80 mmol, 1.2 eq) was added dropwise over a 30 min period. After stirring for 1 h at RT, the reaction was quenched with water (30 mL) and extracted into DCM (3×40 mL). The combined organic layer was washed with brine, passed through a hydrophobic filter, and evaporated under reduced pressure. The residue was purified by silica gel chromatography using 30% EtOAc:Hexane to afford Intermediate-AA128-3 (120 mg, 47%). MS (ES): m/z 311.1 [M+H]+.

Step-3 & Step-4. Synthesis of Tert-Butyl 3-((6-amino-3-methylpyridin-2-yl)(methyl)amino)azetidine-1-carboxylate (Intermediate-AA128)

To a solution of Intermediate-AA128-3 (200 mg, 0.60 mmol) in dioxane were added cyclopropanecarboxamide (102 mg, 10.3 mmol, 2 eq) and $Cs_2CO_3$ (580 mg, 1.8 mmol, 3.0 eq). After degassing under $N_2$ stream for 20 min, $Pd_2(dba)_3$ (54 mg, 0.06 mmol, 0.1 eq) and Xantphos (35 mg, 0.06 mmol, 0.1 eq) were added. After stirring at 100° C. for 12 h, the reaction mixture was cooled at RT and diluted DCM (100 mL) and water (50 mL). The organic layer was collected, and the aqueous phase was extract with DCM (2×80 mL). The combined organic extracts were washed with brine (20 mL), dried over $Na_2SO_4$, filtered, and concentrated under reduced pressure. The residue was purified by column chromatography (10% gradient elution DCM in MeOH). The residue obtained was then triturated with diethyl ether and the resulting solid was collected by filtration to afford the compound tert-butyl 3-((6-(cyclopropanecarboxamido)-3-methylpyridin-2-yl)(methyl)amino)azetidine-1-carboxylate (200 mg). To a solution of tert-butyl 3-((6-(cyclopropanecarboxamido)-3-methylpyridin-2-yl)(methyl)amino)azetidine-1-carboxylate (200 mg, 0.55 mmol, 1 eq.) in methanol: $H_2O$ (2:1 mL) was added solution of NaOH (111 mg, 2.77 mmol, 5 eq.). After stirring for 2.5 h at 70° C., the reaction mixture was evaporated, diluted with water, and extracted with DCM (100 mL×3). The combined organic layers were evaporated to afford the title compound (Intermediate-AA128) as a white solid which was used as is. (650 mg, 59%). MS (ES): m/z 265.3 [M+H]+

Synthesis of 5-(4-(2-(dimethylamino)ethoxy)tetrahydro-2H-pyran-4-yl)pyridin-2-amine (Intermediate-AA129)

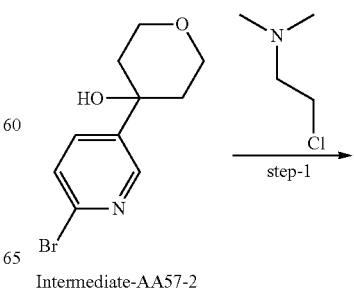

Intermediate-AA57-2

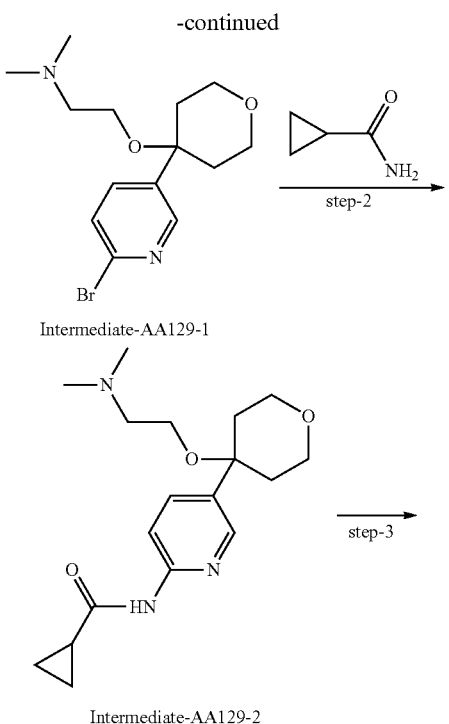

Intermediate-AA129-1

Intermediate-AA129-2

Intermediate-AA129

Step-1 Synthesis of 2-((4-(6-bromopyridin-3-yl) tetrahydro-2H-pyran-4-yl)oxy)-N,N-dimethylethan-1-amine (Intermediate-AA129-1)

To a solution of Intermediate AA57-2 (4 g, 15 mmol, 1 eq.) in DMF (30 mL) was added sodium hydride (1.86 g, 75 mmol, 5 eq). After stirring at RT for 1 h, 2-chloro-N,N-dimethylethan-1-amine (4.32 g, 30 mmol, 2 eq) was added dropwise over a 30 min period. After stirring for 12 h at RT, the reaction was quenched with water (300 mL) and extracted into DCM (3×400 mL). The combined organic layer was washed with brine, passed through a hydrophobic filter, and evaporated in vacuum. The residue was purified by silica gel chromatography using 10% MeOH: DCM to afford Intermediate-AA129-1 (1.1 g, 19.6%). MS (ES): m/z 328.03 [M+H]$^+$

Step-2 Synthesis of N-(5-(4-(2-(dimethylamino) ethoxy)tetrahydro-2H-pyran-4-yl)pyridin-2-yl)cyclopropanecarboxamide (Intermediate-AA129-2)

To a solution of Intermediate-AA129-1 (1.4 g, 4.2 mmol) in dioxane were added cyclopropanecarboxamide (0.72 g, 8.4 mmol, 2 eq), and Cs$_2$CO$_3$ (3 g, 7.5 mol, 3.0 eq). After degassing under N$_2$ stream for 15 min, Pd$_2$(dba)$_3$ (0.380 g, 0.42 mmol, 3 eq) and Xantphos (0.242 g, 0.42 mmol, 0.1 eq) were added. After stirring at 100° C. for 12 h, the reaction mixture was cooled to RT and diluted with DCM (100 mL) and water (50 mL). The organic layer was collected, and the aqueous phase was extract with DCM (2×80 mL). The combined organic extracts were washed with brine (20 mL), dried over Na$_2$SO$_4$, filtered, and concentrated under reduced pressure. The residue was purified by column chromatography (10% gradient elution DCM in MeOH). The residue obtained was then triturated with diethyl ether and the resulting solid was collected by filtration to afford the title compound Intermediate-AA129-2 (1.4 g, 98.74%). MS (ES): m/z 333.43 [M+H]$^+$

Step-3 Synthesis of 5-(4-(2-(dimethylamino)ethoxy) tetrahydro-2H-pyran-4-yl)pyridin-2-amine (Intermediate-AA129)

To a solution of Intermediate-AA129-2 (1.4 g, 4.2 mmol, 1 eq.) in methanol:H$_2$O (20:10 mL) was added solution of NaOH (3.3 g, 80 mmol, 20 eq.). After stirring for 2.5 h at 70° C., the reaction solvent was evaporated, diluted with water (100 mL), and extracted with DCM (100 mL×3). The organic phase was evaporated and dried over Na$_2$SO$_4$ to afford Intermediate-AA129 (650 mg, 59%) as a white solid. MS (ES): m/z 265.2 [M+H]$^+$

Synthesis of Tert-Butyl (2-(4-(6-aminopyridin-3-yl) morpholin-2-yl)propan-2-yl)carbamate (Intermediate-AA130)

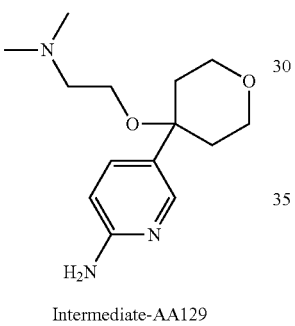

Intermediate-AA93-2

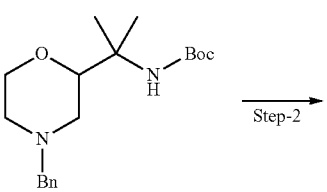

Intermediate-AA130-1

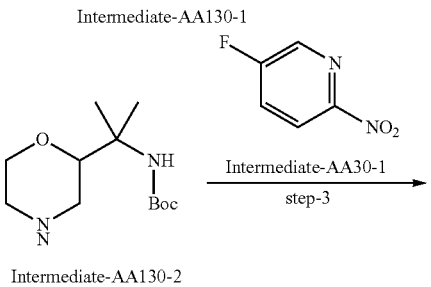

Intermediate-AA130-2

-continued

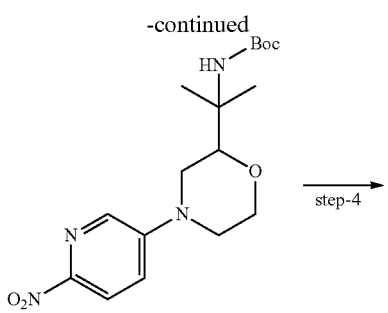

Intermediate-AA130-3

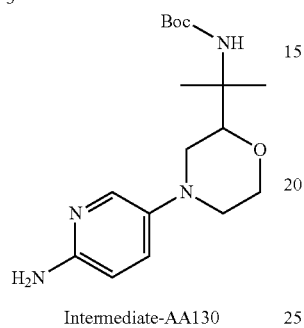

Intermediate-AA130

Step-1 Synthesis of Tert-Butyl (2-(4-benzylmorpholin-2-yl)propan-2-yl)carbamate (Intermediate AA130-1)

To a solution of Intermediate-AA93-2 (8 g, 34 mol) in THF:MeOH (80:20 mL) were added triethyl amine (5.1 g, 51 mol, 1.5 eq) and Boc-anhydride (8.1 g, 37.4 mol, 1.1 eq) in portions. After stirring at RT for 12 h, the reaction was quenched with water (300 mL) and extracted into ethyl acetate (3×400 mL). The combined organic layer was washed with brine, passed through a hydrophobic filter, and evaporated in vacuum. The residue was purified by silica gel chromatography using 1% EtOAc:hexane to afford Intermediate-AA130-1 (2.2 g, 19.6%). MS (ES): m/z 334.23 [M+H]$^+$

Step-2 Synthesis of Tert-Butyl (2-(morpholin-2-yl)propan-2-yl)carbamate (Intermediate AA130-2)

To a suspension of palladium hydroxide (2.1 g) in methanol (30 mL) was added Intermediate-AA130-1 (2.1 g, 6 mol). After stirring under hydrogen atmosphere at 70° C. for 10 h in autoclave under 20 psi, the reaction mixture was cooled at RT, filtered using celite bed and concentrated. The residue was used for next step without purification affording Intermediate-AA130-2 (1.2 g, 78%), MS (ES): m/z 244.3 [M+H]+

Step-3 Synthesis of Tert-Butyl (2-(4-(6-nitropyridin-3-yl)morpholin-2-yl)propan-2-yl)carbamate (Intermediate-AA130-3)

To a solution of Intermediate-AA130-2 (1.2 g, 4.8 mmol) in DMSO: DIPEA (10:5 mL) was added 5-fluoro-2-nitropyridine (0.69 g, 4.8 mmol, 1 eq). After stirring at 120° C. for 2 h, the reaction mixture was cooled at RT and diluted with ethyl acetate (100 mL) and water (50 mL). The organic layer was collected, and the aqueous phase was extract with ethyl acetate (2×30 mL). The combined organic extracts were washed with brine (20 mL), dried over Na$_2$SO$_4$, filtered, and concentrated under reduced pressure. The residue was purified by column chromatography (50% gradient of EtOAc hexane). The residue obtained was then triturated with diethyl ether and the resulting solid was collected by filtration to afford the title compound (Intermediate-AA130-3) (1.1 g, 61%). MS (ES): m/z=366.42 [M+1]+

Step-4 tert-butyl (2-(4-(6-aminopyridin-3-yl) morpholin-2-yl) propan-2-yl) carbamate. (Intermediate-AA130)

To a solution of Pd(C) (1.1 g) in methanol (15 mL) was added Intermediate-AA130-3 (1.1 g, 29 mmol). After stirring at RT for 12 h in H$_2$ gas atmospheric pressure at atmospheric pressure, the reaction mixture was filtered through celite bed. The organic layer was evaporated in vacuum to afford Intermediate-AA130 (900 mg, 88%) which was used as is, MS (ES): m/z=336.42 [M+1]+

Synthesis of 1-(6-aminopyridin-3-yl)-3-(morpholinomethyl)piperidin-3-ol (Intermediate-AA132)

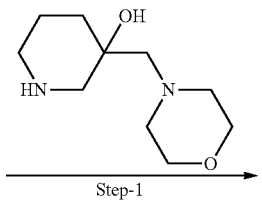

Intermediate AA30-1

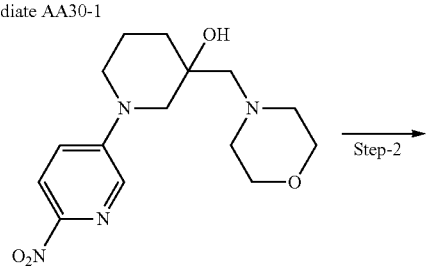

Intermediate AA132-1

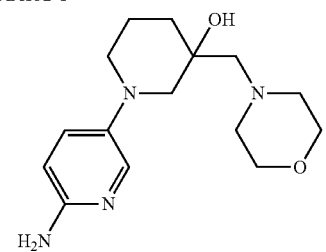

Intermediate AA132

Step-1 Synthesis of N,N-dimethyl-1-(4-(6-nitropyridin-3-yl)morpholin-2-yl)methanamine (Intermediate-AA132-1)

To a stirred solution of 3-(morpholinomethyl)piperidin-3-ol (500 mg, 3.47 mmol, 1 eq) in DMSO (6 mL) were added DIPEA (5 mL, 27.7 mmol, 8 eq) and 5-fluoro-2-nitropyridine (0.739 g, 5.2 mmol, 1.5 eq). After stirring at 120° C. for 4 h, the reaction was diluted with water (35 mL) and extracted with ethyl acetate (3×30 mL). The combined organic layer was washed with brine (40 mL), dried with sodium sulfate, and concentrated under reduced pressure. The residue was purified by column chromatography to afford Intermediate-AA132-1) (500 mg, 54.16%). MS (ES): m/z 322.20 [M+H]$^+$ Step-2 Synthesis of 1-(6-aminopyridin-3-yl)-3-(morpholinomethyl)piperidin-3-ol (Intermediate-AA132)

To a suspension of 10% Pd/C (0.3 g) in methanol was added Intermediate-AA132-1 (0.5 g). After stirring under hydrogen gas at atmospheric pressure for 2 h, the reaction was filtered through celite bed and washed with methanol. The solvent was concentrated under reduced pressure to afford Intermediate-AA132 (300 mg, 67%). MS (ES): m/z 293.38 [M+H]$^+$.

Synthesis of Tert-Butyl (2-(4-(6-aminopyridin-3-yl)morpholin-2-yl)propan-2-yl)(methyl)carbamate (Intermediate-AA133)

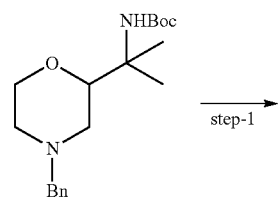

Intermediate AA130-1

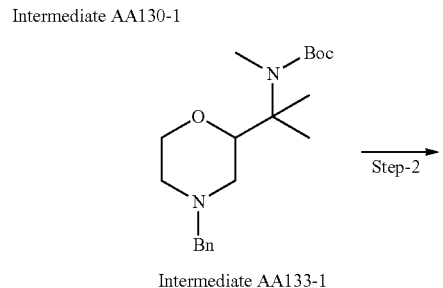

Intermediate AA133-1

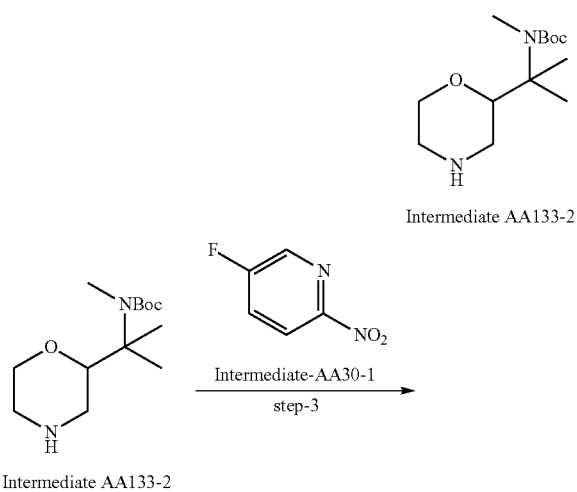

Intermediate AA133-2

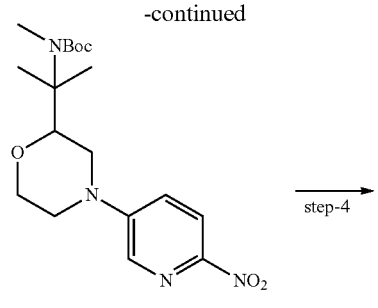

Intermediate AA133-3

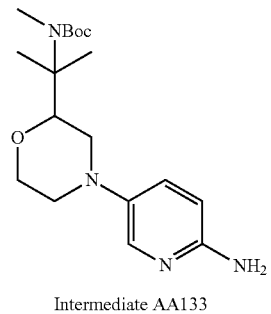 [SMILES: CN(C(=O)OC(C)(C)C)C(C)(C)C1CN(c2ccc(N)nc2)CCO1]

Intermediate AA133

Step-1 Synthesis of Tert-Butyl (2-(4-benzylmorpholin-2-yl)propan-2-yl)(methyl)carbamate (Intermediate-AA133-1)

To a solution of Intermediate-AA130-1 (10.0 g) and formaldehyde (2.56 g, 2.0 eq) in dichloroethane (100 mL) was added trimethylamine (12 mL, 85.46 mmol, 2.0 eq). After stirring at RT for 1 h. sodium triacetoxyborohydride (18.1 g, 85.46 mmol, 2.0 eq) was added in portion. After stirring for 16 h at RT, the reaction mixture was diluted with water (200 mL) and sodium bicarbonate solution (100 mL) and extracted with DCM (3×80 mL). The combined organic extracts were washed with brine (150 mL), dried over Na$_2$SO$_4$, filtered, and concentrated under reduced pressure. The residue was purified by column chromatography eluting with 3% methanol gradient in DCM to afford Intermediate-AA133-1) (4.0 g, 35.72%) MS (ES): m/z=349.5 [M+H]$^+$ Step-2 Synthesis of tert-butyl methyl(2-(morpholin-2-yl)propan-2-yl)carbamate (Intermediate-AA133-2)

To a suspension of 20% palladium hydroxide on carbon (2.0 g) in methanol (20 mL) was added Intermediate-AA133-1 (4.0 g). After stirring under hydrogen gas at atmospheric pressure at RT for 16 h, the reaction mixture was filtered through celite-bed and washed with methanol. The filtrate was concentrated under reduced pressure to afford Intermediate-AA133-2 (1.8 g, quantitative). MS (ES): m/z 258.36 [M+H]$^+$ Step-3 Synthesis of tert-butyl methyl(2-(4-(6-nitropyridin-3-yl)morpholin-2-yl)propan-2-yl)carbamate (Intermediate-AA133-3)

To a solution of Intermediate-AA133-2 (1.8 g, 10.46 mmol) and 5-fluoro-2-nitropyridine (0.890 g, 6.27 mmol, 0.6 eq) in DMSO (20 mL) was added dropwise N-ethyl-N-isopropylpropan-2-amine (7.1 mL, 41.84 mmol, 3.0 eq). After stirring at 120° C. for 2 h, the reaction mixture was diluted with water (100 mL) and extracted with ethyl acetate (3×80 mL). The combined organic extracts were washed with brine (100 mL), dried over $Na_2SO_4$, filtered, and concentrated under reduced pressure. The residue was purified by column chromatography eluting with 2% methanol in DCM to afford Intermediate-AA133-3 (1.4 g, 45.52%). MS (ES): m/z=381.2 $[M+H]^+$ Step-4 Synthesis of Tert-Butyl (2-(4-(6-aminopyridin-3-yl)morpholin-2-yl)propan-2-yl)(methyl)carbamate (Intermediate-AA133)

To a suspension of 10% palladium on carbon (0.7 g) in methanol (15 mL) was added Intermediate-AA133-3 (1.4 g, 4.76 mmol). After stirring under hydrogen gas at atmospheric pressure at RT for 4 h, the reaction mixture was filtered through Celite-bed and washed with methanol. The filtrate was concentrated under reduced pressure to afford Intermediate-AA133. which was used in the next step without further purification. (1.2 g, quantitative yield). MS (ES): m/z 351.2 $[M+H]^+$ Synthesis of 1-(6-aminopyridin-3-yl)-4-(1-methylpyrrolidin-2-yl) piperidin-4-ol (Intermediate-AA134)

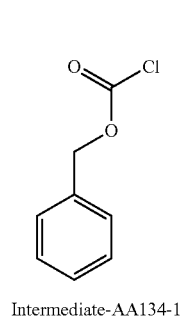

Intermediate-AA134-1

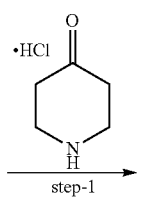

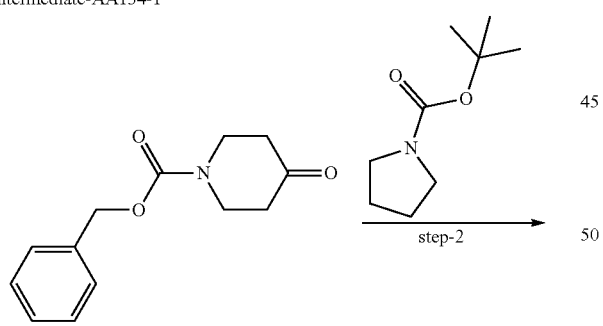

Intermediate-AA134-3

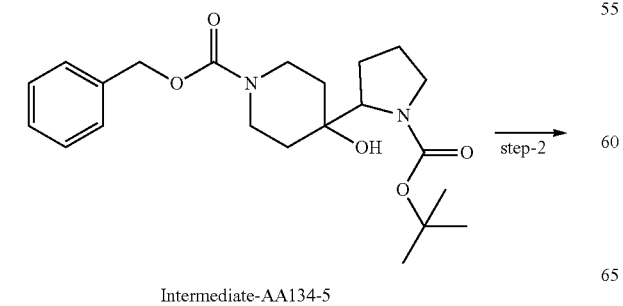

Intermediate-AA134-5

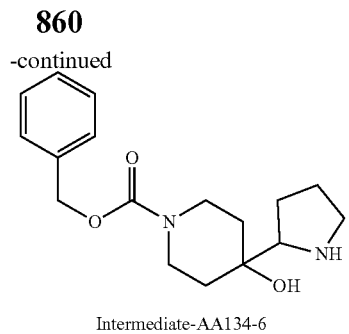

Intermediate-AA134-6

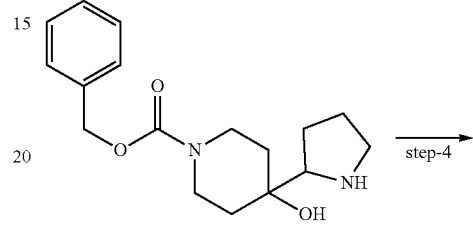

Intermediate-AA134-7

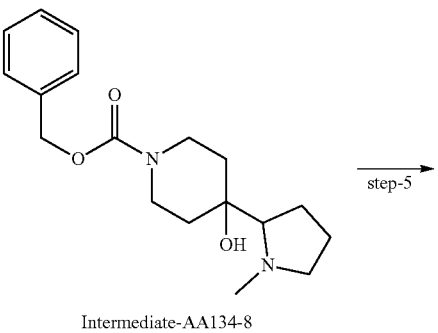

Intermediate-AA134-8

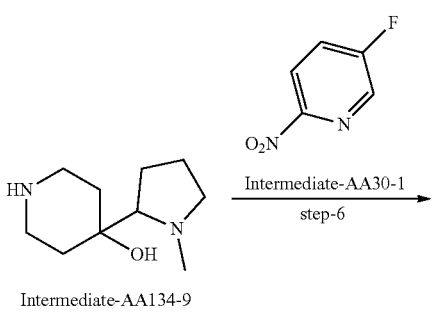

Intermediate-AA134-9

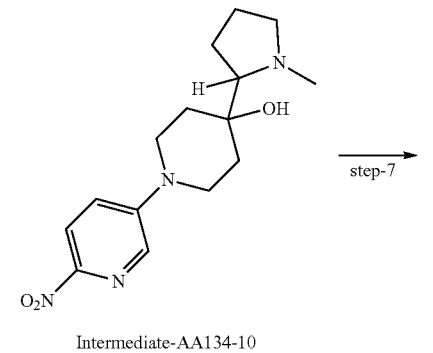

Intermediate-AA134-10

-continued

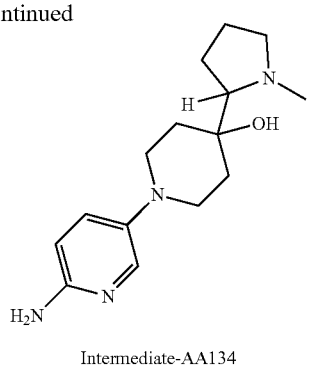

Intermediate-AA134

Step-1 Synthesis of benzyl 4-oxopiperidine-1-carboxylate (Intermediate AA134-3)

To a solution of piperidin-4-one (25.0 g, 185.18 mmol) and benzyl carbonochloridate (35 mL, 222.22 mmol, 1.2 eq) in 1,4-dioxane (200 mL) was added sodium bicarbonate (46.6 g, 555.54 mmol, 3.0 eq) and water (170 mL). After stirring at RT for 3 h, the reaction mixture was diluted with water (1000 mL) and extracted with ethyl acetate (3×150 mL)/The combined organic extracts were washed with brine (500 mL), dried over $Na_2SO_4$, filtered, and concentrated under reduced pressure. The residue was purified by column chromatography eluting with 40% ethyl acetate gradient in hexane to afford Intermediate-AA134-3 (20.0 g, 34.00%), MS (ES): m/z 234.1 $[M+H]^+$.

Step-2 Synthesis of benzyl 4-(1-(tert-butoxycarbonyl)pyrrolidin-2-yl)-4-hydroxypiperidine-1-carboxylate (Intermediate AA134-5)

To a solution of tert-butyl pyrrolidine-1-carboxylate (12.0 g, 70.17 mmol) in THF (400 mL) at −78° C. was added sec-Butyl lithium (1.3M in cyclohexane) (65 mL, 84.20 mmol, 1.2 eq). After stirring at −78° C. for 3 h, Intermediate AA143-3 (16.3 g, 70.17 mmol) in THF was added dropwise into the reaction mixture at −78° C. After stirring for 2 h at −78° C. and for 16 hr at RT, the reaction mixture was diluted with water (700 mL) and extracted with ethyl acetate (3×200 mL). The combined organic extracts were washed with brine (500 mL), dried over $Na_2SO_4$, filtered, and concentrated under reduced pressure. The residue was purified by column chromatography eluting with 20% ethyl acetate gradient in hexane to afford Intermediate-AA134-5 (6.7 g, 23.64%), MS (ES): m/z 405.2 $[M+H]^+$.

Step-3 Synthesis of benzyl 4-hydroxy-4-(pyrrolidin-2-yl)piperidine-1-carboxylate (Intermediate AA134-6)

To a solution of Intermediate-AA134-5) (6.7 g, 16.58 mmol) in DCM (70 mL) at 0° C. was added HCl in dioxane (35 mL). After stirring at RT for 1 h, the reaction was neutralized with saturated sodium bicarbonate solution and extracted with DCM (3×150 mL). The combined organic layer was concentrated under reduced pressure. The residue was purified by column chromatography eluting with 6% gradient elution in DCM to afford Intermediate-AA134-6 (1.09 g, 19.83%), MS (ES): m/z 305.1 $[M+H]^+$

Step-4 Synthesis of benzyl 4-hydroxy-4-(1-methylpyrrolidin-2-yl)piperidine-1-carboxylate (Intermediate AA134-8)

To a solution of Intermediate-AA134-6 (1.0 g, 3.28 mmol) in methanol (10 mL), were added formaldehyde (10 mL) and acetic acid (5 mL). After stirring for 1 h at RT, sodium cyanoborohydride (0.247 g, 3.93 mmol, 1.2 eq) was added. After stirring for 16 h at RT, the reaction mixture was concentrated under reduced pressure, diluted with water (80 mL), and extracted with 10% methanol in DCM (3×30 mL). The combined organic extracts were washed with brine (80 mL), dried over $Na_2SO_4$, filtered, and concentrated under reduced pressure. Thee residue was purified by column chromatography eluting with 3% methanol gradient in DCM to afford Intermediate-AA134-8 (0.7 g, 66.92%), MS (ES): m/z 319.2 $[M+H]^+$

Step-5 Synthesis of 4-(1-methylpyrrolidin-2-yl)piperidin-4-ol (Intermediate-AA134-9)

To a solution of Intermediate-AA134-8 (0.630 g, 2.20 mmol) in methanol (10 mL) was added 10% palladium on charcoal (0.3 g). After stirring under hydrogen at atmospheric pressure for 16 h at RT, the reaction mixture was filtered through celite-bed and washed with methanol. The filtrate was concentrated under reduced pressure to obtain Intermediate-AA134-9 which was used in the next step without further purification. (0.450 g, quantitative). MS (ES): m/z 185.1 $[M+H]^+$.

Step-6 Synthesis of 4-(1-methylpyrrolidin-2-yl)-1-(6-nitropyridin-3-yl)piperidin-4-ol (Intermediate-AA134-10)

To a solution of 5-fluoro-2-nitropyridine (0.6 g, 4.22 mmol) and Intermediate-AA134-9 (0.78 g, 4.22 mmol) in DMSO (6 mL), were added potassium carbonate (1.7 g, 12.66 mmol, 3.0 eq) and tetrabutylammonium iodide (0.155 g, 0.422 mmol, 0.1 eq). After stirring at 120° C. for 3 h, the reaction mixture was diluted with water (50 mL) and extracted with 10% methanol in DCM (3×30 mL). The combined organic extracts were washed with brine (50 mL), dried over $Na_2SO_4$, filtered, and concentrated under reduced pressure. The residue was purified by column chromatography eluting with 3% methanol gradient in DCM to afford Intermediate-AA134-10 (0.3 g, 38.65%), MS (ES): m/z 307.1 $[M+H]^+$

Step-7 Synthesis of 1-(6-aminopyridin-3-yl)-4-(1-methylpyrrolidin-2-yl)piperidin-4-ol (Intermediate-AA134)

To a solution of Intermediate AA134-10 (0.3 g, 0.98 mmol) in methanol (5 mL) was added 10% palladium on charcoal (0.15 g). After stirring under hydrogen gas at atmospheric pressure for 16 h at RT, the reaction mixture was filtered through celite-bed and washed with methanol. The filtrate was concentrated under reduced pressure to afford Intermediate-AA134 which was used in the next step without further purification. (0.250 g, quantitative). MS (ES): m/z 277.2 $[M+H]^+$.

Synthesis of 6-((dimethylamino)methyl)-5-(4-oxa-7-azaspiro[2.5]octan-7-yl)pyridin-2-amine (Intermediate-AA135)

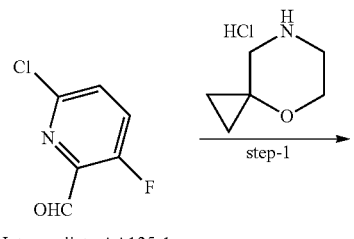

Intermediate AA135-1

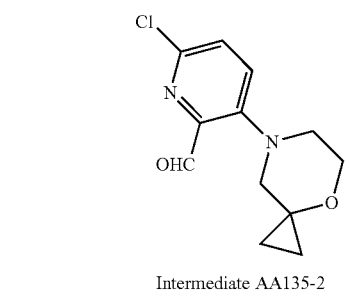

Intermediate AA135-2

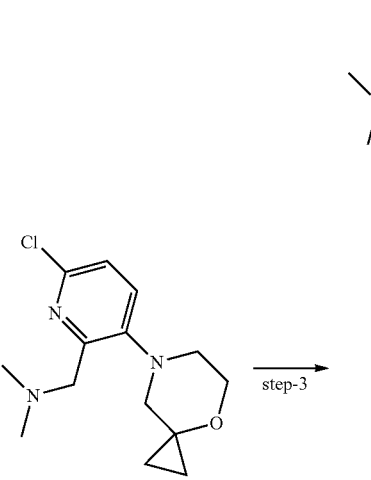

Intermediate AA135-3

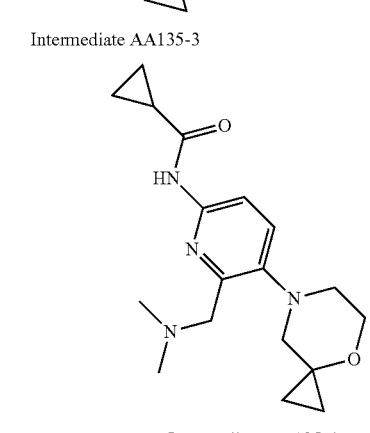

Intermediate AA135-4

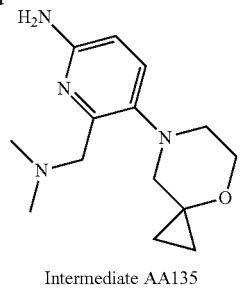

Intermediate AA135

Step-1 Synthesis of 6-chloro-3-(4-oxa-7-azaspiro[2.5]octan-7-yl)picolinaldehyde (Intermediate AA135-2)

To a solution of Intermediate AA135-1 (0.9 g, 5.66 mmol) and 4-oxa-7-azaspiro[2.5]octane (0.843 g, 5.66 mmol) in DMF (10 mL) was added potassium carbonate (2.3 g, 16.98 mmol, 3.0 eq). After stirring at 100° C. for 1 h, the reaction mixture was cooled to RT, diluted with ice cold water (50 mL) and extracted with ethyl acetate (3×20 mL). The combined organic extracts were washed with brine, dried over $Na_2SO_4$, filtered, and concentrated under reduced pressure. The residue was purified by column chromatography eluting with 20% ethyl acetate gradient in hexane to obtain Intermediate AA135-2 (1.0 g, 70.15%), MS (ES): m/z 253.07 [M+H]$^+$ Step-2 Synthesis of 1-(6-chloro-3-(4-oxa-7-azaspiro[2.5]octan-7-yl)pyridin-2-yl)-N,N-dimethylmethanamine (Intermediate AA135-3)

To a solution of Intermediate AA135-2 (1.0 g, 3.96 mmol) in methanol (10 mL) were add dimethylamine (2M in THF) (38.5 mL) and acetic acid (3.5 mL) dropwise at RT. After stirring at RT for 1 h, the reaction mixture was cooled to 0° C. and sodium triacetoxyborohydride (1.67 g, 7.92 mmol, 2.0 eq) was added portion wise. After stirring at RT for 20 min, the reaction mixture was diluted with water (100 mL) and extracted with 10% methanol in DCM (3×40 mL). The combined organic extracts were washed with brine, dried over $Na_2SO_4$, filtered, and concentrated under reduced pressure to afford Intermediate AA135-3 (0.710 g, 63.67%), MS (ES): m/z 282.13 [M+H]$^+$ Step-3 Synthesis of N-(6-((dimethylamino)methyl)-5-(4-oxa-7-azaspiro[2.5]octan-7-yl)pyridin-2-yl)cyclopropanecarboxamide (Intermediate AA135-4)

To a solution of Intermediate AA135-3 (0.5 g, 1.77 mmol) in 1,4-Dioxane (5 mL) were added $K_2CO_3$ (0.732 g, 5.31 mmol, 3.0 eq) and cyclopropanecarboxamide (0.453 g, 5.33 mmol, 3.0 eq). After degassing under $N_2$ stream for 15 min, Xantphos (0.098 g, 0.17 mmol, 0.1 eq) and $Pd_2(dba)_3$ (0.155 g, 0.17 mmol, 0.1 eq) were added. After stirring at 110° C. for 16 h, the reaction mixture was cooled to RT, diluted with water (50 mL), and extracted with ethyl acetate (3×20 mL). The combined organic extracts were washed with brine (50 mL), dried over $Na_2SO_4$, filtered, and concentrated under reduced pressure. The residue was purified by column chromatography eluting with 7% methanol gradient in DCM to afford Intermediate AA135-4 (0.350 g, 59.69%), m/z=331.2 [M+1]$^+$

Step-4 Synthesis of 6-((dimethylamino)methyl)-5-(4-oxa-7-azaspiro[2.5]octan-7-yl)pyridin-2-amine (Intermediate AA135)

To a solution of Intermediate AA135-4 (0.350 g, 1.06 mmol) in methanol (8 mL) and water (2 mL) was added sodium hydroxide (0.424 g, 10.6 mmol, 10.0 eq). After stirring at RT for 16 h, the reaction mixture was diluted with water (25 mL) and extracted with DCM (4×15 mL). The combined organic extracts were washed with brine, dried over Na$_2$SO$_4$, filtered, and concentrated under reduced pressure. The residue was purified by column chromatography eluting with 3% methanol gradient in DCM to afford Intermediate AA135 (0.170 g, 61.17%), m/z=263.1 [M+1]$^+$

Synthesis of 3-(1-(6-aminopyridin-3-yl)piperidin-3-yl)-1-methylazetidin-3-ol (Intermediate-AA136)

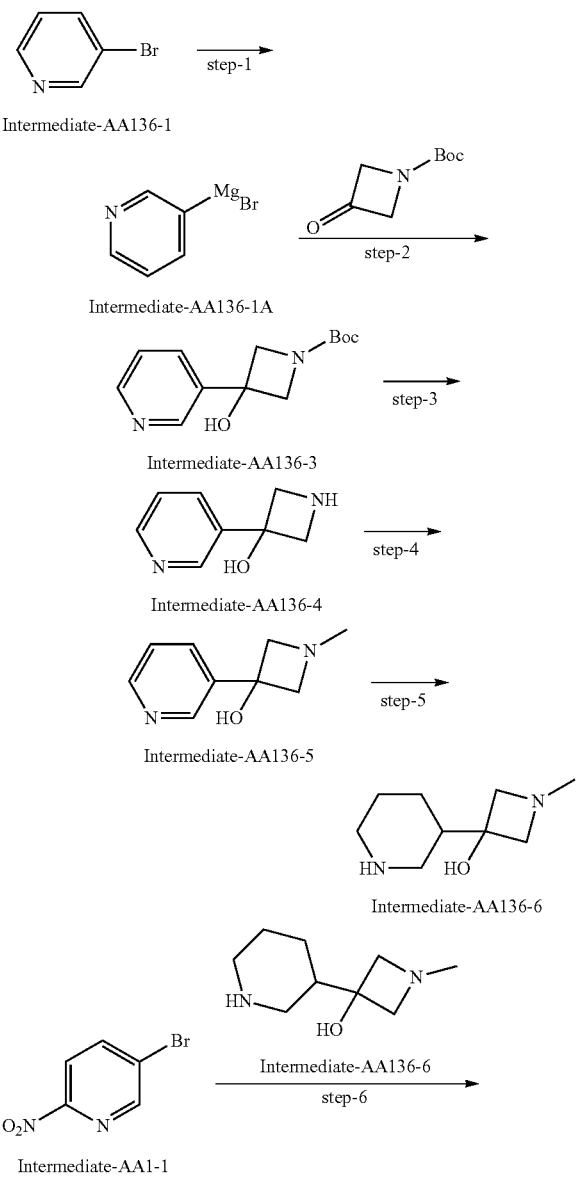

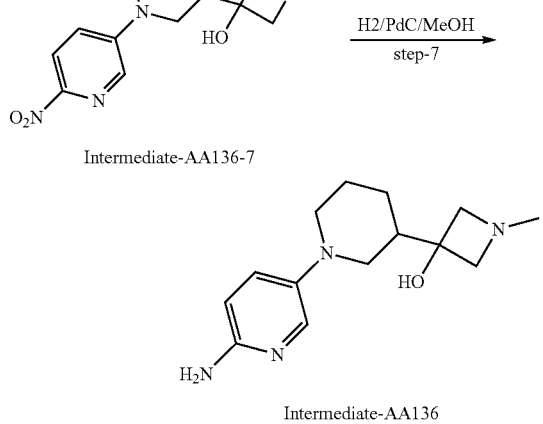

Intermediate-AA136-7

Intermediate-AA136

Step-1 & Step-2 Synthesis of Tert-Butyl 3-hydroxy-3-(pyridin-3-yl) azetidine-1-carboxylate (Intermediate-AA136-3)

To magnesium metal (1.5 g, 63.29 mmol, 5 eq) in THF (8 mL) heated for 2 min were added 1, 2 di-bromoethane (0.5 mL) and then Intermediate-AA136-1 (2 g, 12.65 mmol) dropwise. After cooling to RT, tert-butyl 3-oxoazetidine-1-carboxylate (0.861 g, 5.06 mmol, 0.4 eq) was added. After stirring for 2 hr, the reaction was diluted with water (100 mL), extracted with ethyl acetate, and concentrated in vacuo. The residue was purified by column chromatography to afford Intermediate-AA136-3 (1.3 g, 41%), MS (ES): m/z 250.30 [M+H]$^+$.

Step-3 Synthesis of 3-(pyridin-3-yl) azetidin-3-ol (Intermediate AA136-4)

To a solution of Intermediate-AA136-3 (3.8 g, 15.18 mmol) in DCM (40 mL) was added 4M Dioxane HCl (15 mL, 4 eq) at 0° C. After stirring at RT for 2 h, the residue was quenched in sodium bicarbonate (100 mL) and extracted with DCM (3×100 mL) to afford Intermediate-AA136-4 (2 g, 87.72%) which was used as is, MS (ES): m/z 250.30 [M+H]$^+$

Step-4 Synthesis of 1-methyl-3-(pyridin-3-yl)azetidin-3-ol (Intermediate AA136-5)

To a solution of Intermediate-AA136-4 (3 g, 2.1 mmol, 1 eq) in methanol (30 mL) was added formaldehyde (2 mL, 3.9 mmol, 1.9 eq). After stirring at RT for 30 min, acetic acid (3 mL, 1V) and NaCN(BH)3 (2.5 g, 4.2 mmol, 2 eq) were added. After stirring at 50° C. for 2 h, the solvent was evaporated. The residue was purified by column chromatography eluted with 7% methanol in DCM to afford Intermediate-AA136-5. (2.1 g, 60.97%), MS (ES): m/z 165.21 [M+H]$^+$

Step-5 Synthesis of 1-methyl-3-(piperidin-3-yl)azetidin-3-ol (Intermediate AA136-6)

To a suspension of PtO2 (1 g) in acetic acid (10 mL) was added Intermediate AA136-5 (2.1 g, 12.71 mmol, 1 eq). After stirring in autoclave at 20 psi hydrogen pressure at RT for 24 h, the reaction was filtered through celite and the bed washed with EtOAc. The filtrate was evaporated under reduced pressure to afford Intermediate-AA136-6 (1.6 g, 73.48%) which was used as is, MS (ES): m/z 170.14 [M+H]$^+$ Step-6 Synthesis of 1-methyl-3-(1-(6-nitropyridin-3-yl)piperidin-3-yl)azetidin-3-ol (Intermediate AA136-7)

To a solution of 5-bromo-2-nitro pyridine (1 g, 4.9 mmol, 1 eq) in dioxane (10 mL) were added Intermediate-AA136-6 (837 mg, 4.9 mmol, 1 eq) and Cs$_2$CO$_3$(4.79 g, 14.76 mmol, 3 eq). After degassing with N$_2$ stream for 20 min, Pd$_2$(dba)$_3$ (0.450 mg, 0.4 mmol, 0.1 eq) and xantphos (0.560 mg, 0.9 mmol, 0.2 eq) were added. After stirring at 110° C. for 2 h, the reaction was diluted with water and extracted with ethyl acetate. The combined organic solution was dried over Na$_2$SO$_4$, filtered, and concentrated under reduced pressure. The residue was purified by column chromatography eluting with 10% methanol in DCM to afford Intermediate-AA136-7) (360 mg, 25%) as a yellow solid. MS (ES): m/z 292.34 [M+H]$^+$ Step-7 Synthesis of 3-(1-(6-aminopyridin-3-yl)piperidin-3-yl)-1-methylazetidin-3-ol (Intermediate-AA136)

To a solution of Intermediate-AA136-7 (0.270 g, 0.923 mmol, 1.0 eq) in methanol (3 mL) was added 10% palladium on charcoal (130 mg). After stirring with hydrogen gas at atmospheric pressure for 4 h at RT, the reaction mixture was filtered through celite-bed and washed with methanol. The filtrate was concentrated under reduced pressure to afford Intermediate-AA136 which was used in the next step without further purification. (200 mg, quantitative). MS (ES): m/z 262.36 [M+H]$^+$.

Synthesis of Tert-Butyl 6-(6-aminopyridin-2-yl)-1,6-diazaspiro[3.3]heptane-1-carboxylate (Intermediate-AA137)

Step-1 Synthesis of Tert-Butyl 6-(6-nitropyridin-2-yl)-1,6-diazaspiro[3.3]heptane-1-carboxylate (Intermediate-AA137-1)

To a stirred solution of 2-chloro-6-nitropyridine (500 mg, 2.5 mmol, 1 eq) in dioxane (5 mL) were added tert-butyl 1,6-diazaspiro[3.3]heptane-1-carboxylate oxalate salt (480 mg, 3 mmol, 1.2 eq) and NaOtBu (0.726 g, 7.5 mmol, 3 eq). After degassing with N$_2$ gas for 20 min, Pd$_2$(dba)$_3$ (0.230 mg, 0.25 mmol, 0.1 eq) and Ruphose (0.117 mg, 0.25 mmol, 0.1 eq) were added. After stirring at 110° C. for 2 h, the reaction was diluted with water and extracted with ethyl acetate. The organic layer was collected and dried over Na$_2$SO$_4$, filtered, and concentrated under reduced pressure. The residue was purified by column chromatography eluting with 2% methanol in DCM to afford Intermediate-AA137-1 (0.360 g, 35.20%) as a brown solid. MS (ES): m/z 320.35 [M+H]$^+$ Step-2 Synthesis of Tert-Butyl 6-(6-aminopyridin-2-yl)-1,6-diazaspiro[3.3]heptane-1-carboxylate (Intermediate AA137)

To a solution of Intermediate-AA37-1 (0.080 g, 0.25 mmol) in methanol (3 mL) was added 10% palladium on charcoal (30 mg). After stirring under hydrogen gas at atmospheric pressure for 4 h at RT, the reaction mixture was filtered through celite-bed and washed with methanol. The filtrate was concentrated under reduced pressure to afford Intermediate-AA137 which was used in the next step without further purification. (60 mg, quantitative). MS (ES): m/z 290.37 [M+H]$^+$.

Synthesis of Tert-Butyl 1-(6-aminopyrazin-2-yl)hexahydropyrrolo[3,4-b]pyrrole-5(1H)-carboxylate (Intermediate-AA138)

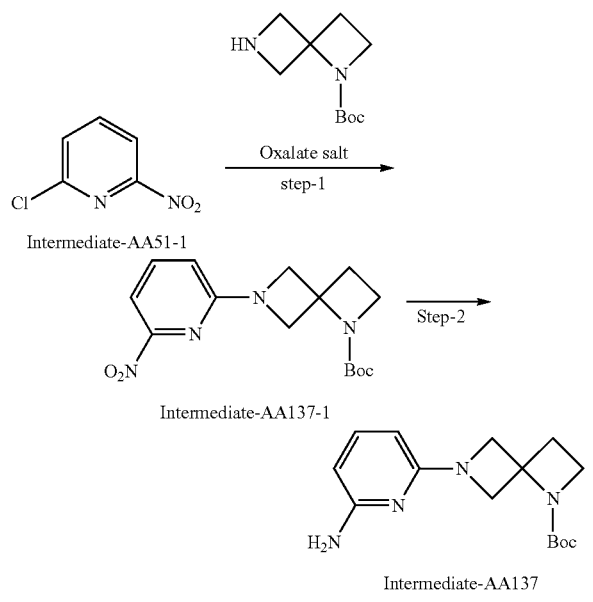

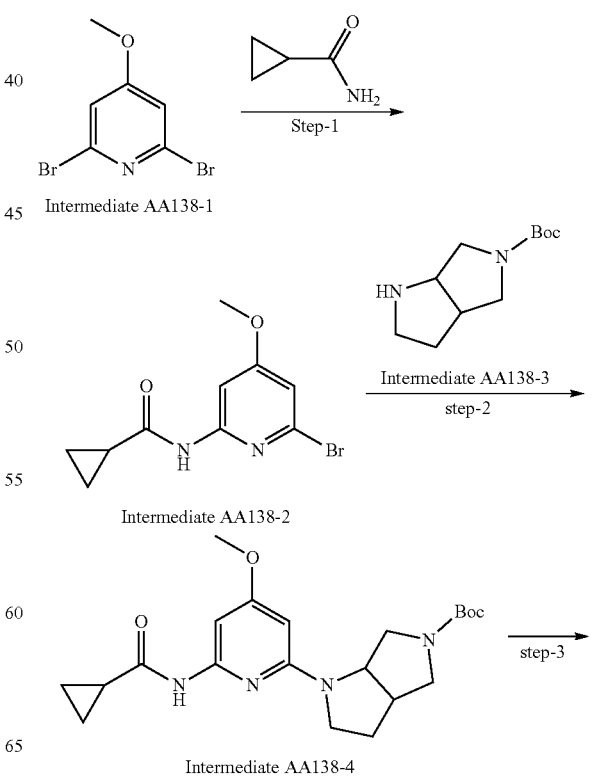

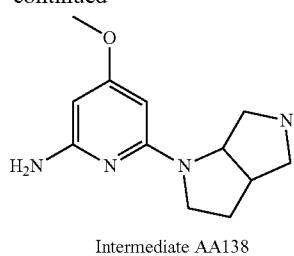

Intermediate AA138

Step-1 Synthesis of N-(6-bromo-4-methoxypyridin-2-yl)cyclopropanecarboxamide Intermediate (Intermediate-AA138-2)

To a solution of Intermediate-AA138-1 (4.0 g, 31.00 mmol) in DCM (40 mL) trimethylamine (13 mL, 93 mmol, 3.0 eq) at 0° C. was added cyclopropane carbonyl chloride (12.8 g, 124 mmol, 4 eq) dropwise. After stirring at RT for 2 h, the reaction was diluted with water (200 mL) and extracted with ethyl acetate (3×70 mL). The combined organic layer was washed with brine (200 mL), dried over $Na_2SO_4$, filtered, and concentrated under reduced pressure. The residue was purified by column chromatography eluting with 10% ethyl acetate gradient in hexane to afford Intermediate-AA138-2 (3.5 g, 57.36%) as a yellow oil. MS (ES): m/z 271 $[M+H]^+$

Step-2 Synthesis of Tert-Butyl 1-(6-(cyclopropanecarboxamido)-4-methoxypyridin-2-yl)hexahydropyrrolo[3,4-b]pyrrole-5(1H)-carboxylate (Intermediate AA138-4)

To a solution of Intermediate-AA138-3 (1.5 g, 7.10 mmol) in DMSO (15 mL) were added tetra butyl ammonium iodide (0.785 g, 2.13 mmol, 0.3 eq) and potassium carbonate (2.9 g, 21.3 mmol, 3.0 eq). After 15 min, Intermediate-AA139-2 (1.4 g, 7.10 mmol, 1.0 eq) was added. After stirring at 100° C. for 16 h, the reaction was diluted with water (100 mL) and extracted with ethyl acetate (3×40 mL). The combined organic layer was washed with brine (100 mL), dried over $Na_2SO_4$, filtered, and concentrated under reduced pressure. The residue was purified by column chromatography to afford Intermediate-AA138-4 (0.850 g, 32.13%) as a yellow oil. MS (ES): m/z 402.23 $[M+H]^+$

Step-3 Synthesis of Tert-Butyl 1-(6-amino-4-methoxypyridin-2-yl)hexahydropyrrolo[3,4-b]pyrrole-5(1H)-carboxylate (Intermediate AA138)

To a solution of Intermediate-AA138-4 (0.850 g, 2.27 mmol) in methanol (10 mL) and water (3 mL) was added sodium hydroxide (0.9 g, 22.7 mmol, 10.0 eq). After stirring at 60° for 16 h, the reaction mixture was concentrated under reduced pressure to remove methanol and extracted with 10% methanol in DCM (3×70 mL). The combined organic layers were washed with brine (80 mL), dried over $Na_2SO_4$, filtered, and concentrated under reduced pressure to afford Intermediate-AA138 which was used as is (0.6 g), MS (ES): m/z 306.19 $[M+H]^+$

Synthesis of Tert-Butyl 1-(6-aminopyrazin-2-yl)hexahydropyrrolo[3,4-b]pyrrole-5(1H)-carboxylate (Intermediate-AA139)

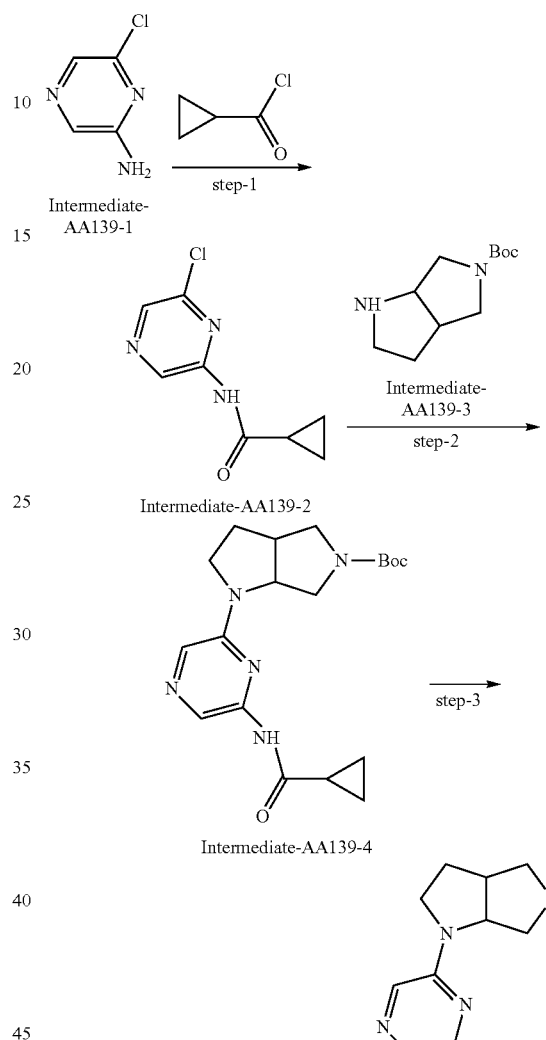

Step-1 Synthesis of N-(6-chloropyrazin-2-yl)cyclopropanecarboxamide (Intermediate-AA139-2)

To a solution of Intermediate-AA139-1 (4.0 g, 31.00 mmol) in DCM (40 mL) and trimethylamine (13 mL, 93.0 mmol, 3.0 eq) at 0° C. was added cyclopropane carbonyl chloride (12.8 g, 124 mmol, 4.0 eq) dropwise. After stirring at RT for 2 h, the reaction was diluted with water (200 mL) and extracted with ethyl acetate (3×70 mL). The combined organic layer was washed with brine (200 mL), dried over $Na_2SO_4$, filtered, and concentrated under reduced pressure. The residue was purified by column chromatography 10% ethyl acetate gradient in hexane to afford Intermediate-AA139-1 (3.5 g, 57.36%) as a yellow oil. MS (ES): m/z 198.04 $[M+H]^+$

Step-2 Synthesis of Tert-Butyl 1-(6-(cyclopropanecarboxamido)pyrazin-2-yl)hexahydropyrrolo[3,4-b]pyrrole-5(1H)-carboxylate (Intermediate AA139-4)

To a solution of Intermediate-AA139-3 (1.5 g, 7.10 mmol) in DMSO (15 mL) were added tetra butyl ammonium iodide (0.785 g, 2.13 mmol, 0.3 eq) and potassium carbonate (2.9 g, 21.3 mmol, and 3.0 eq). After 15 min, Intermediate-AA139-2 (1.4 g, 7.10 mmol) was added. After stirring at 100° C. for 16 h, the reaction was diluted with water (100 mL) and extracted with ethyl acetate (3×40 mL). The combined organic layer was washed with brine (100 mL), dried over $Na_2SO_4$, filtered, and concentrated under reduced pressure. The residue was purified by column chromatography 50% ethyl acetate gradient in hexane to afford Intermediate-AA139-4) (0.850 g, 32.13%) as a yellow oil. MS (ES): m/z 374.2 $[M+H]^+$

Step-3 Synthesis of Tert-Butyl 1-(6-aminopyrazin-2-yl)hexahydropyrrolo[3,4-b]pyrrole-5(1H)-carboxylate (Intermediate AA139)

To a solution of Intermediate-AA139-4 (0.850 g, 2.27 mmol) in methanol (10 mL) and water (3 mL) was added sodium hydroxide (0.9 g, 22.7 mmol, 10.0 eq). After stirring at 60° for 16 h, the reaction mixture concentrated under reduced pressure to remove methanol and extracted with 10% methanol in DCM (3×70 mL). The combined organic layers were washed with brine (80 mL), dried over $Na_2SO_4$, filtered, and concentrated under reduced pressure to afford Intermediate-AA139 (0.6 g) which was used as is. MS (ES): m/z 306.19 $[M+H]^+$

Synthesis of 5-(2-(1-(dimethylamino)cyclopropyl)morpholino)pyridin-2-amine (Intermediate-AA140)

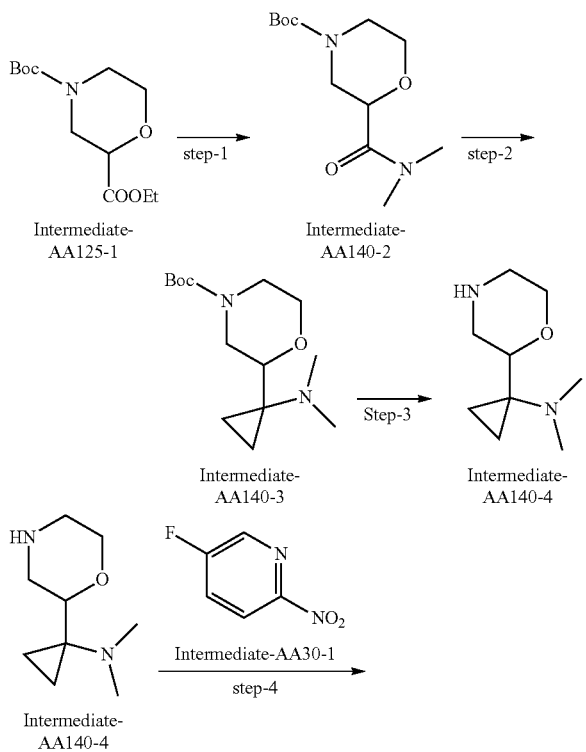
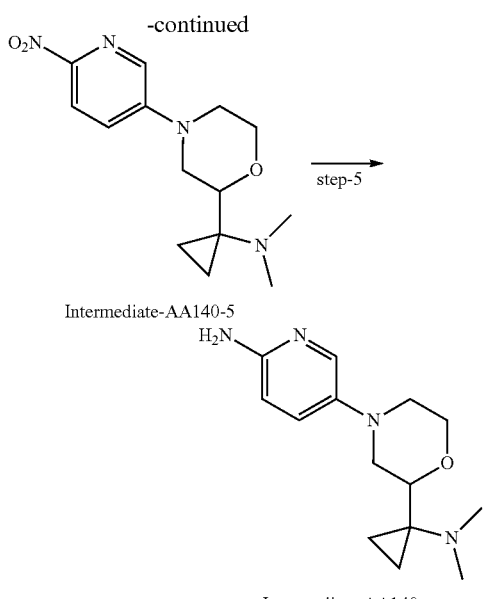

Intermediate-AA140

Step-1 tert-butyl 2-(dimethylcarbamoyl)morpholine-4-carboxylate. Intermediate (AA140-2)

To a solution of Intermediate-AA125-1 (10.0 g, 38.61 mmol) and dry THF (100 mL) were added dimethyl amine (2M in THF) (23 mLg, 46.33 mmol, 1.2 eq) and trimethylaluminum (2M in THF) (28 mg, 57.91 mmol, 1.5 eq). After stirring at 70° C. for 16 h, the reaction mixture was cooled to RT, diluted with water (150 mL), and extracted with ethyl acetate (3×80 mL). The combined organic layers were washed with brine (80 mL), dried over $Na_2SO_4$, filtered, and concentrated under reduced pressure. The residue was purified by column chromatography eluting with 25% ethyl acetate gradient in hexane to afford Intermediate-AA140-2 (6.5 g, 65.25%) as a brown solid. MS (ES): m/z=259.16 $[M+H]^+$.

Step-2 Synthesis of Tert-Butyl 2-(1-(dimethylamino)cyclopropyl)morpholine-4-carboxylate (Intermediate AA140-3)

To a solution of ethyl magnesium bromide solution (1.0M in THF) (62 mL, 62.98 mmol, 2.5 eq) in THF (70 mL) at −78° C. was added dropwise titanium isopropoxide (7.6 mL, 25.19 mmol). After 5 min, Intermediate-AA140-2 (6.5 g, 25.19 mmol) was added/After stirring at 70° C. for 1 h, the reaction mixture cooled to RT, diluted with water (80 mL), and extracted with ethyl acetate (3×40 mL). The combined organic extracts were washed with brine (90 mL), dried over $Na_2SO_4$, filtered, and concentrated under reduced pressure. The residue was purified by column chromatography eluting with 25% ethyl acetate gradient in hexane to afford Intermediate-AA140-3 (1.5 g, 22.05%) MS (ES): m/z=271.2 $[M+H]^+$

Step-3 Synthesis of N,N-dimethyl-1-(morpholin-2-yl)cyclopropan-1-amine (Intermediate AA140-4)

To a solution of Intermediate-AA140-3 (1.5 g, 5.55 mmol) in DCM (15 mL) was added 4 M HCl in dioxane (10 mL) at 0° C. After stirring at RT for 30 min, the reaction was diluted with water (30 mL) and extracted with 30% propane 2-ol in chloroform (4×30 mL). The combined organic layer was dried over Na$_2$SO$_4$, filtered, and concentrated under reduced pressure to afford Intermediate-AA140-4 (0.8 g): m/z=171.15 [M+H]$^+$.

Step-4 Synthesis of N,N-dimethyl-1-(4-(6-nitropyridin-3-yl)morpholin-2-yl)cyclopropan-1-amine (Intermediate AA140-5)

To a solution of Intermediate-AA140-4 (0.8 g, 4.70 mmol) and 5-fluoro-2-nitropyridine (0.668 g, 4.70 mmol) in DMSO (8 mL), were added N, N-diisopropylethylamine (2.4 mL, 14.1 mmol, 3.0 eq) and tetrabutylammonium iodide (0.173, 0.47 mmol, 0.1 eq). After stirring at 120° C. for 2 h, the reaction mixture cooled to RT and diluted with ice cold water whereby a solid material precipitated from solution. The solid was filtered and dried under high vacuum to afford Intermediate-AA140-5 (0.630 g, 45.86%) as a brown solid. MS (ES): m/z=293.16 [M+H]$^+$ Step-5 Synthesis of 5-(2-(1-(dimethylamino)cyclopropyl)morpholino)pyridin-2-amine (Intermediate-AA140)

To a solution of Intermediate-AA140-5 (0.630 g, 2.15 mmol) in methanol (7 mL) was added 10% palladium on charcoal (0.3 g). After stirring under hydrogen gas at atmospheric pressure for 4 h at RT, the reaction mixture was filtered through celite-bed and washed with methanol. The filtrate was concentrated under reduced pressure to afford Intermediate-AA140 which was used in the next step without further purification. (0.520 g). MS (ES): m/z 263.18 [M+H]$^+$ Synthesis of 1-(6-aminopyridin-2-yl)-5-(azetidin-1-ylmethyl) piperidin-2-one (Intermediate-AA141)

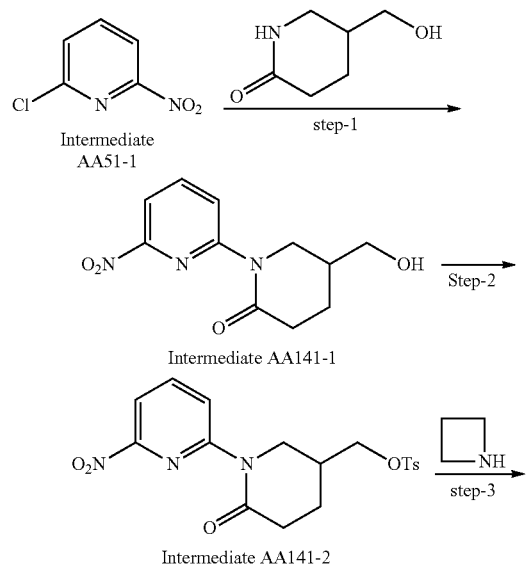

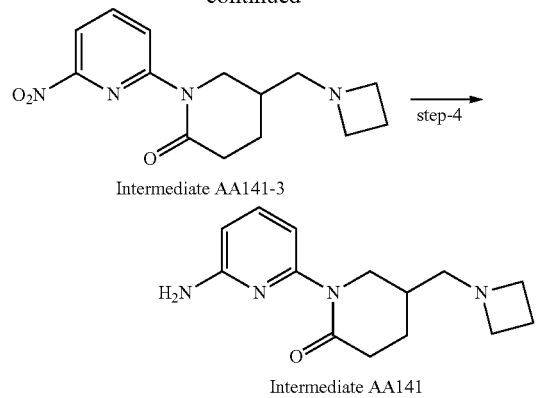

Step-1 Synthesis of 5-(hydroxymethyl)-1-(6-nitropyridin-2-yl)piperidin-2-one (Intermediate AA141-1)

To a solution of Intermediate-AA51-1 (500 mg, 1.76 mmol) in dioxane (5 mL), were added 5-(hydroxymethyl) piperidin-2-one (334 mg, 2.1 mmol, 1.2 eq) and K$_2$CO$_3$ (729 mg, 5.2 mmol, 3 eq). After degassing under N$_2$ stream for 20 min, Xantphos (0.090 g, 0.17 mmol, 0.1 eq) and Pd$_2$(dba)$_3$ (0.161 g, 0.17 mmol, 0.1 eq) were added. After stirring at 100° C. for 1 h, the reaction mixture was cooled to RT, diluted with water (80 mL), and extracted with ethyl acetate (3×30 mL). The combined organic extracts were washed with brine (90 mL), dried over Na$_2$SO$_4$, filtered, and concentrated under reduced pressure. The residue was purified by column chromatography to afford Intermediate-AA141-1 (0.300 g, 37.23%). MS (ES): m/z=251.09 [M+H]$^+$.

Step-2 Synthesis of 1-(6-nitropyridin-2-yl)-6-oxopiperidin-3-yl)methyl 4-methylbenzenesulfonate (Intermediate AA141-2)

To a solution of Intermediate-AA141-2 (400 mg, 1.58 mmol) in DCM (4 mL) were added triethylamine (0.66 mL, 4.76 mmol, 3 eq) and 4-toluenesulfonyl chloride (0.904 m, 4.76 mmol, 3 eq). After stirring at RT for 5 h, the reaction diluted with water (40 mL) and extracted with ethyl acetate (3×50 mL). The combined organic layers were washed with brine (50 mL), dried over Na$_2$SO$_4$, filtered, and concentrated under reduced pressure. The residue was purified by column chromatography to afford Intermediate-AA141-2 (300 mg, 46%). MS (ES): m/z 405.43 [M+H]$^+$ Step-3 Synthesis of 5-(azetidin-1-ylmethyl)-1-(6-nitropyridin-2-yl)piperidin-2-one (Intermediate AA141-3)

A solution of Intermediate-AA141-2 (200 mg, 49.2 mmol) in acetonitrile (3 mL), were added K$_2$CO$_3$ (271 mg, 1.9 mmol, 4.0 eq), and azetidine (56 mg, 98.5 mmol, 2 eq). After stirring at 90° C. for 2 h, the reaction was diluted with water (20 mL) and extracted with ethyl acetate (2×50 mL). The combined organic layer was wash with brine (50 mL), dried over Na$_2$SO$_4$, filtered, and concentrated under reduced pressure. The residue was purified by column chromatography to afford Intermediate-AA141-3 (200 mg, 50%) as a yellow oil. MS (ES): m/z 290.14 [M+H]+

Step-4 Synthesis of 1-(6-aminopyridin-2-yl)-5-(azetidin-1-ylmethyl)piperidin-2-one (Intermediate-AA141)

To a suspension of 10% palladium on charcoal (0.300 g) was added Intermediate-AA141-3) (600 mg). After stirring with hydrogen gas at atmospheric pressure for 2 h at RT, the reaction mixture was filtered through celite-bed and washed with methanol. The filtrate was concentrated under reduced pressure afford Intermediate-AA141 (200 mg, 74.34%). MS (ES): m/z 260.34 [M+H]+

Synthesis of Tert-Butyl 4-(6-aminopyridin-3-yl)hexahydropyrrolo[3,4-b][1,4]oxazine-6(2H)-carboxylate (Intermediate-AA142)

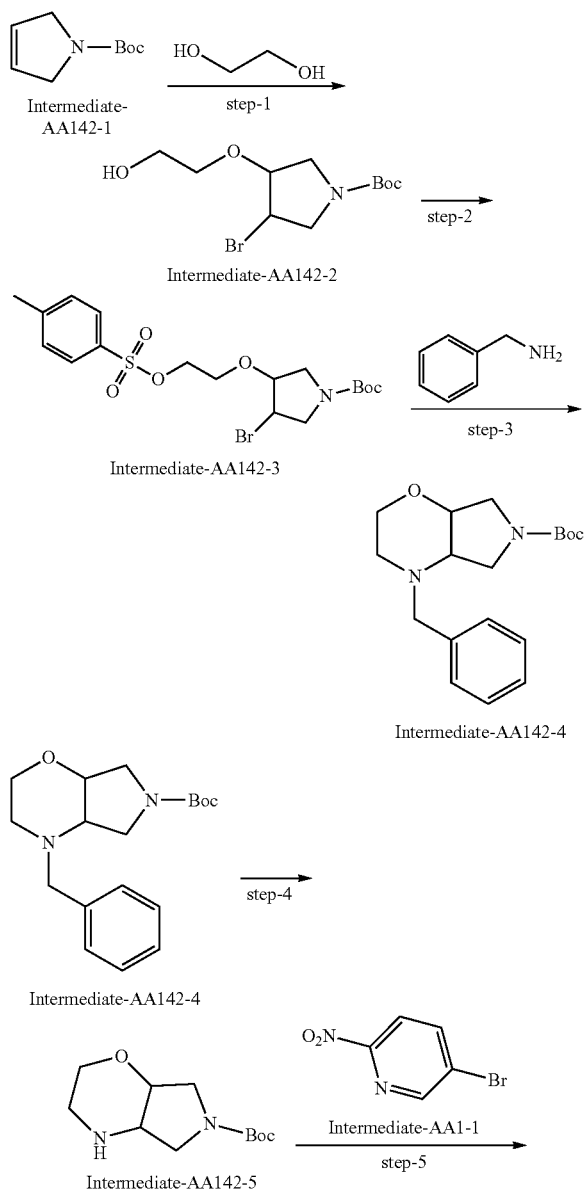

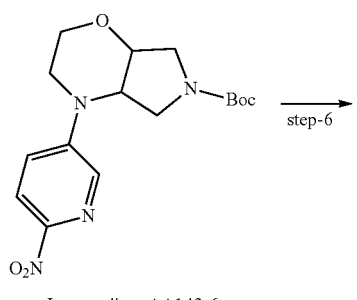

Intermediate-AA142-6

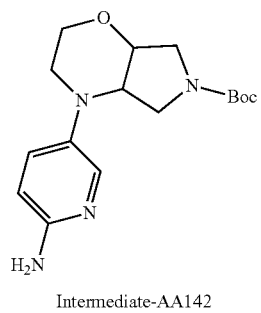

Intermediate-AA142

Step-1 Synthesis of Tert-Butyl 3-bromo-4-(2-hydroxyethoxy)pyrrolidine-1-carboxylate (Intermediate AA142-2)

To a solution of Intermediate-AA-141 (3.0 g, 17.75 mmol) in ethylene glycol (30 mL) was added N-Bromosuccinimide (3.2 g, 18.28 mmol, 1.03 eq). After stirring at RT for 16 h, the reaction was quenched with water (150 mL) and extracted with ethyl acetate (3×50 mL). The combined organic layer was washed with brine (80 mL), dried over Na₂SO₄, filtered, and concentrated under reduced pressure. The residue was purified by column chromatography 1% methanol gradient in DCM to afford Intermediate-AA142-1 (4.9 g, 89.11%) as a yellow oil. MS (ES): m/z 310.19 [M+H]+

Step-2 Synthesis of Tert-Butyl 3-bromo-4-(2-(tosyloxy)ethoxy)pyrrolidine-1-carboxylate (Intermediate AA142-3)

To a solution of Intermediate-AA142-2 (4.9 g, 15.80 mmol) in toluene (30 mL) with triethylamine (2.6 mL, 18.96 mmol, 1.2 eq) and DMAP (0.038 g, 0.316 mmol, 0.02 eq) at 0° C. was added 4-toluenesulfonyl chloride (2.78 mL, 18.96 mmol, 1.2 eq) dropwise. After stirring at RT for 16 h, the reaction was quenched with water (200 mL) and extracted with ethyl acetate (3×80 mL). The combined organic layer was washed with brine (100 mL), dried over Na₂SO₄, filtered, and concentrated under reduced pressure. The residue was purified by column chromatography eluting with 25% ethyl acetate gradient in hexane to afford Intermediate-AA142-3 (5.5 g, 74.98%) as a yellow oil. MS (ES): m/z 465.06 [M+H]+

Step-3 Synthesis of Tert-Butyl 4-benzylhexahydropyrrolo[3,4-b][1,4]oxazine-6(2H)-carboxylate (Intermediate AA142-4)

To a solution of Intermediate-AA142-3 (5.5 g, 11.82 mmol) in xylene (60 mL) was added phenylmethanamine (3.7 g, 35.46 mmol, 3.0 eq). After stirring at 140° C. for 16 h, the reaction mixture was cooled to RT and concentrated under reduced pressure. The residue diluted with water (150 mL) and extracted with ethyl acetate (3×50 mL). The combined organic layer was washed with brine (100 mL), dried over $Na_2SO_4$, filtered, and concentrated under reduced pressure. The residue was purified by column chromatography 20% ethyl acetate gradient in hexane to afford Intermediate-AA142-4 (4.1 g, 95.46%) as a yellow oil. MS (ES): m/z 319.20 $[M+H]^+$

Step-4 Synthesis of tert-butyl hexahydropyrrolo[3,4-b][1,4]oxazine-6(2H)-carboxylate (Intermediate AA142-5)

To a solution of Intermediate-AA142-4 (4.0 g, 12.57 mmol) in methanol (40 mL) was added 10% palladium on charcoal (2.0 g). After stirring under hydrogen gas at atmospheric pressure for 16 h at RT, the reaction mixture was filtered through celite-bed and washed with methanol. The filtrate was concentrated under reduced pressure. The residue was purified by column chromatography eluting with 5% methanol gradient in DCM to afford Intermediate-AA142-5 (1.7 g, 59.28%). MS (ES): m/z 229.15 $[M+H]^+$.

Step-5 Synthesis of Tert-Butyl 4-(6-nitropyridin-3-yl)hexahydropyrrolo[3,4-b][1,4]oxazine-6(2H)-carboxylate (Intermediate-AA142-6)

To a solution of 5-bromo-2-nitropyridine (1.6 g, 7.88 mmol) and Intermediate-AA142-5 (2.1 g, 9.45 mmol, 1.2 eq) in toluene (20 mL) was added $Cs_2CO_3$ (5.1 g, 15.76 mmol, 2.0 eq). After degassing under $N_2$ stream for 15 min, Xantphos (0.45 g, 0.78 mmol, 0.1 eq) and $Pd_2(dba)_3$ (0.360 g, 0.394 mmol, 0.05 eq) were added. After stirring at 100° C. for 1 h, the reaction mixture was cooled to RT, diluted with water (80 mL), and extracted with ethyl acetate (3×30 mL). The combined organic extracts were washed with brine (90 mL), dried over $Na_2SO_4$, filtered, and concentrated under reduced pressure. The residue was purified by column chromatography eluting with 3% methanol gradient in DCM to afford Intermediate-AA142-6 (1.7 g, 69.23%) as a brown solid. MS (ES): m/z=351.16 $[M+H]^+$.

Step-6 Synthesis of Tert-Butyl 4-(6-aminopyridin-3-yl)hexahydropyrrolo[3,4-b][1,4]oxazine-6(2H)-carboxylate (Intermediate-AA142)

To a solution of Intermediate-AA142-6 (1.7 g, 4.85 mmol) in methanol (20 mL), was added 10% palladium on charcoal (0.8 g). After stirring under hydrogen gas at atmospheric pressure for 2 h at RT, the reaction mixture was filtered through celite-bed and washed with methanol. The filtrate was concentrated under reduced pressure. The residue was purified by trituration with diethyl ether to afford Intermediate-AA142 (1.3 g, 83.63%). MS (ES): m/z 321.19 $[M+H]^+$

Tert-Butyl (1-(6-aminopyridin-2-yl)-5-oxopyrrolidin-3-yl)carbamate (Intermediate-AA143)

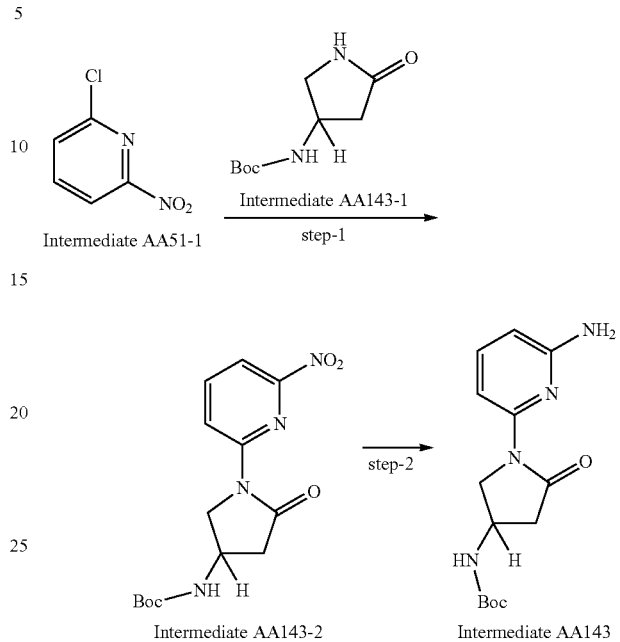

Step-1 synthesis of tert-butyl (1-(6-nitropyridin-2-yl)-5-oxopyrrolidin-3-yl)carbamate (Intermediate AA143-2)

To a solution of Intermediate AA51-1 (4 g, 25.31 mmol) and Intermediate AA143-1 (6.0 g, 30.37 mmol, 1.2 eq) in DMF (40 mL) was added potassium phosphate tribasic (16.0 g, 75.93 mmol, 3.0 eq). After degassing under $N_2$ stream for 15 min. Brett Phos (1.3 g, 2.53 mmol, 0.1 eq) and Brett Phos Pd G3 (1.8 g, 2.02 mmol, 0.08 eq) were added. After stirring at 110° C. and for 1 h, the reaction mixture was cooled to RT, diluted water (200 mL) and extracted with ethyl acetate (3×70 mL). The combined organic extracts were washed with brine (200 mL), dried over $Na_2SO_4$, filtered, and concentrated under reduced pressure. The residue was purified by column chromatography eluting with 20-25% ethyl acetate gradient in hexane to afford Intermediate-AA143-2 (6.0 g, 73.78%) as a brown solid. MS (ES): m/z=323.1 $[M+H]^+$.

Step-2 Synthesis of Tert-Butyl (1-(6-aminopyridin-2-yl)-5-oxopyrrolidin-3-yl)carbamate (Intermediate-AA143)

To a solution of Intermediate-AA143-2 (2.0 g, 6.21 mmol) in methanol (20 mL), was added 10% palladium on charcoal (1.0 g). After stirring under hydrogen gas at atmospheric pressure for 4 h at RT, the reaction mixture was filtered through celite-bed and washed with methanol. The filtrate was concentrated under reduced pressure to afford Intermediate-AA143 which was used in the next step without further purification. (1.9 g, quantitative). MS (ES): m/z 293.1 $[M+H]^+$.

879
Synthesis of 1-(6-chloro-3-morpholinopyridin-2-yl)-N,N-dimethylmethanamine (Intermediate-AA144)

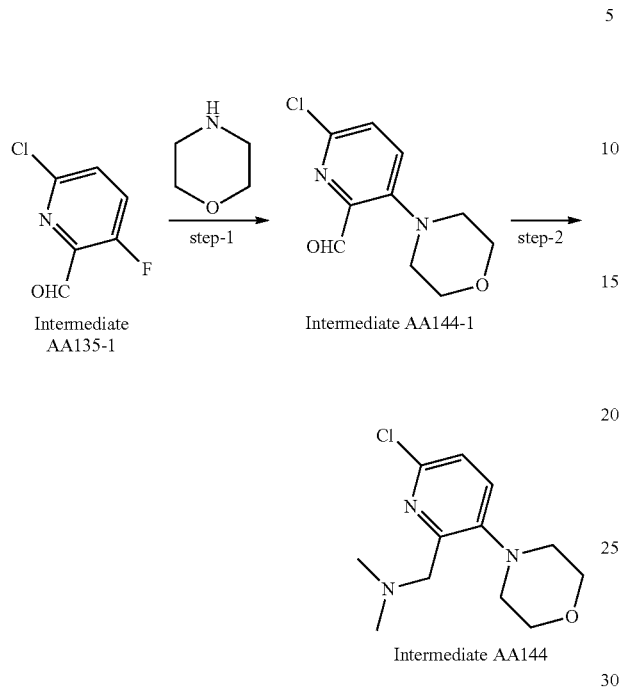

Step-1 synthesis of 6-chloro-3-morpholinopicolinaldehyde (Intermediate AA144-1)

To a solution of Intermediate-AA135-1 (7.5 g 31.77 mmol) in THF (25 mL) at −78° C. was added to the solution of n-butyllithium (19 mL, 1.59 mmol, 1.5 eq) in diethyl ether (35 mL). After stirring at −78° C. for 30 min, 1-methylpiperidin-4-one (3.6 g 31.77 mmol) was added. After stirring for 45 min at −78° C., the reaction mixture was diluted with sodium bicarbonate solution (200 mL) and extracted with ethyl acetate (3×150 mL). The combined organic extracts were washed with brine (200 mL), dried over $Na_2SO_4$, filtered, and concentrated under reduced pressure. The residue was purified by trituration with diethyl ether to obtain Intermediate AA144-1 (3 g, 34.91%) MS (ES) m/z 227.66 $(M+H)^+$

Step-2 Synthesis of 1-(6-chloro-3-morpholinopyridin-2-yl)-N,N-dimethylmethanamine (Intermediate-AA144)

To a solution of Intermediate-AA144-1 (1 g) in methanol (10 mL) with acetic acid (0.1 mL) at 0° C. was added NaCN(BH3) (0.5 g, 4 eq). After stirring for 2 h, the reaction was diluted with water (90 mL) and extracted with ethyl acetate (3×50 mL). The combined organic extracts were washed with brine (100 mL), dried over $Na_2SO_4$, filtered, and concentrated under reduced pressure. The residue was purified by silica gel chromatography to afford Intermediate AA144 (600 mg, 53%). MS (ES): m/z=256.3 (M+H)+.

880
Synthesis of 5-cyclopentyl-6-((dimethylamino)methyl)pyridin-2-amine (Intermediate AA145)

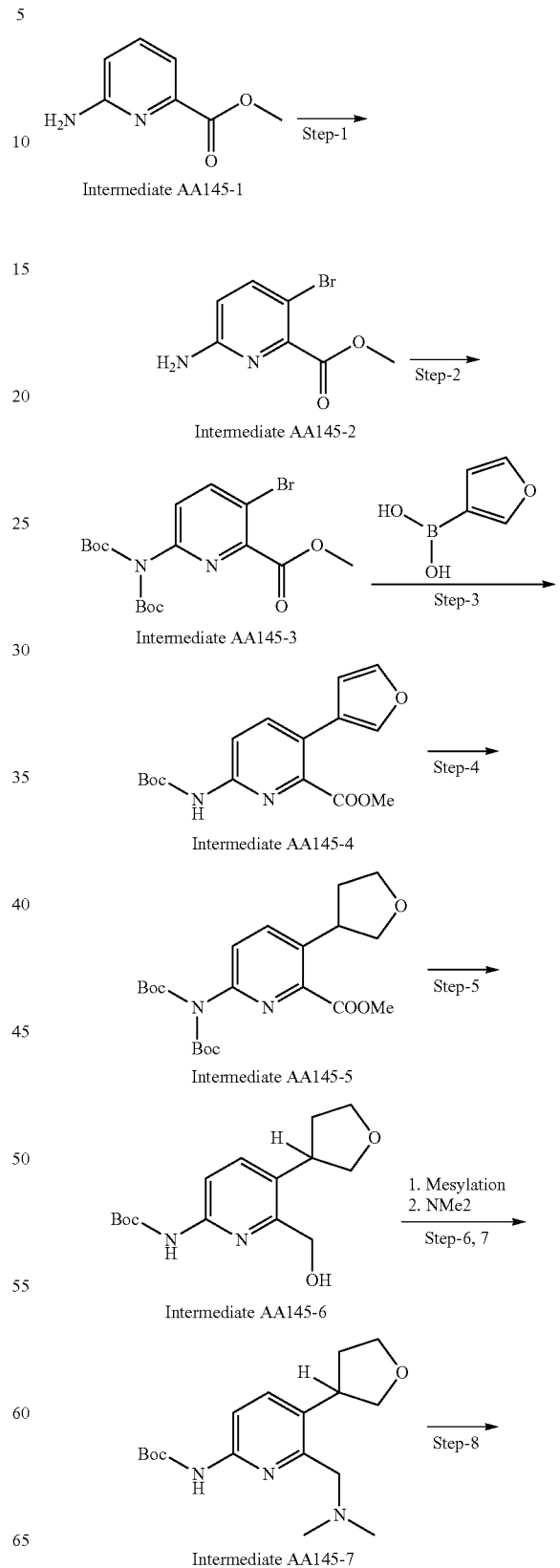

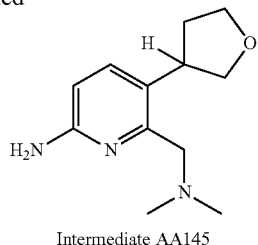

Intermediate AA145

Step-1 Synthesis of methyl 6-amino-3-bromopicolinate (Intermediate-AA145-2)

To a solution of Intermediate-AA145-1 (500 g, 3289.4 mmol) in acetonitrile (12.5 L) was portion wise added N-bromo succinimide (644 g, 3618.4 mmol, 1.1 eq) at RT over 30 min. After stirring at RT for 30 min, the reaction mixture was quenched with 10% $Na_2S_2O_3$ solution in water (3.0 L) and the reaction mixture was evaporated to remove ACN. The residue was diluted with 10% $Na_2S_2O_3$ solution in water (20 L) and extracted with 50% ethyl acetate in hexanes (10 L×5). The combined organic layer was dried over sodium sulfate and concentrated under reduced pressure. The crude material was triturated with 25% ethyl acetate in hexanes to afford Intermediate-AA145. MS (ES): m/z 231-233 $[M+2]^+$, $^1$H NMR (400 MHz, CDCL3): δ 7.66 (d, 1H), 6.53 (d, 1H), 4.68 (S, 2H), 3.98 (s, 3H). The other region isomer (methyl 6-amino-5-bromopicolinate) also formed and it is separated via silica purification. Desired regioisomer confirm by $^1$H NMR and NOE analysis.

Step-2 Synthesis of methyl 3-bromo-6-(bis(tert-butoxycarbonyl)amino)picolinate (Intermediate-AA145-3)

To a solution of Intermediate-AA145-2 (1100 g, 4782.6 mmol) in THF (20 L) were added DMAP (116.7 g, 956.5 mmol, 0.2 eq) and Boc anhydride (2502 g, 11478.2 mmol, 2.4 eq). After stirring at 75° C. for 1.5 h, the solvent was evaporated and then residue diluted in brine solution and extracted by ethyl acetate (2×10 L). The combined organic layer was dried over sodium sulfate and concentrated under vacuum. The residue was purified by Colum chromatography eluting with 5% ethyl acetate in hexane. The desired material was further purified by trituration with hexanes (4 L) to afford Intermediate-AA145-3 (1700 g, 82.79%) as white solid. MS (ES): m/z 431-433 $[M+2]^+$. $^1$H NMR (400 MHz, DMSO): δ 8.32 (d, 1H), 7.61 (d, 1H), 3.90 (s, 3H), 1.40 (s, 18H).

Step-3 Synthesis of methyl 6-(bis(tert-butoxycarbonyl)amino)-3-(furan-3-yl)picolinate Intermediate-AA145-4

To a solution of the Intermediate-AA145-3 (730 g, 1693.7 mmol) and furan boronic acid 3 (379 g, 3387.4 mmol, 2 eq) in 1-4 dioxane (5.85 L) and water (1.46 L) was added potassium phosphate tribasic (Sigma, 1078.3 g, 5086.2 mmol, 3.0 eq). After degassing with flow of nitrogen for 20 min, bis(triphenylphosphine)palladium(II) dichloride (59.5 g, 84.8 mmol, 0.05 eq) was added (Note: exothermicity was observe). After stirring at 120° C. for 15 min, the reaction was cooled to RT and the water layer was separated from reaction mixture. The organic layer was filtered through celite bed and concentrated under reduced pressure. The residue was purified by silica gel chromatography eluting with 6 to 10% ethyl acetate/hexanes. The collected material was triturated with n-pentane to afford Intermediate-AA145-4 as a cream colored solid. MS (ES): m/z 418 $[M+1]^+$ $^1$H NMR (400 MHz, DMSO): δ 8.12 (d, 1H), 8.00 (d, 1H), 7.81 (s, 1H), 7.61 (s, 1H), 6.70 (S, 1H), 3.83 (S, 3H), 1.41 (s, 18H).

Step-4 Synthesis of methyl 6-(bis(tert-butoxycarbonyl)amino)-3-(furan-3-yl)picolinate Intermediate-AA145-5

To a solution of Intermediate-AA145-4 (191 g, 456.9 mmol) in methanol (1140 mL) and THF (955 mL) were added with ammonium formate (115.1 g, 182.5 mmol, 4.0 eq), acetic acid (133.7 mL, 0.7V) and 20% WET palladium hydroxide on carbon (133.7 g, 1:0.7 W/W). After stirring under an atmosphere of hydrogen gas for 24 h at RT, the reaction mixture was combined with 6 other batches on the same scale prepared by an identical method. The reaction mixture was then filtered through Celite bed, and the filtrate was concentrated under reduced pressure. The residue was neutralized with sat. $NaHCO_3$(10 L) solution and extracted by DCM (10 L×3) to afford Intermediate-AA145-5 (1251 g, and 92.6%). MS (ES): m/z 423 $[M+1]^+$ $^1$H NMR (400 MHz, DMSO): δ 8.01 (d, 1H), 7.58 (d, 1H), 3.99 (t, 2H), 3.87 (S, 3H), 3.71 (m, 2H), 3.60 (m, 1H), 2.31 (m, 1H) 1.91 (d, 1H), 1.4 (s, 18H).

Step-5 Synthesis of compound tert-butyl (6-(hydroxymethyl)-5-(THF-3-yl)pyridin-2-yl)carbamate (Intermediate-AA145-6)

To a solution of Intermediate-AA145-5 (250 g, 592.4 mmol) in ethanol (2500 mL) was treated portion wise with sodium borohydride (135 g, 355.4 mmol, 6 eq). After stirring at 60° C. for 2 h, the reaction was evaporated under reduced pressure, diluted with water (10 L), and extracted by DCM (4×10 L). The combined organic layer was washed with brine (10 L), passed through a $Na_2SO_4$, and concentrated under reduced pressure to afford Intermediate-AA145-6. The product was combined with 4 other batches on the same scale prepared by an identical method. (640 g, 73.49%), as colorless gummy liquid which turned into white solid at RT after 2 days. MS (ES): m/z 295.0 $[M+1]^+$ $^1$H NMR (400 MHz, DMSO): δ 7.81 (d, 1H), 7.67 (d, 1H), 7.2 (d, 1H), 5.22 (d, 1H), 4.55 (t, 1H), 3.99 (s, 3H), 3.77 (m, 3H), 3.55 (m, 2H), 2.28 (d, 2H), 1.87 (d, 1H), 1.41 (s, 9H)

Step-6, 7 Synthesis of Tert-Butyl (6-((dimethylamino)methyl)-5-(THF-3-yl)pyridin-2-yl)carbamate (Intermediate-AA145-7)

To a solution of Intermediate-AA145-6 (440 g, 149.6 mmol) in DCM (6.5 L) was added dropwise DIPEA (581.4 g, 448.9 mmol, 3.0 eq) at 0° C. After stirring for 20 min, mesyl chloride (257.04 g, 2244 mmol, 1.5 eq) was added dropwise at 0° C. After stirring at 0° C. to RT for 2 h, the reaction mixture was quenched with Water (1 L) and extracted by DCM (3×2 L). The combined organic layer was washed with brine (10 L), passed through a $Na_2SO_4$, and concentrated under reduced pressure to afford mesylated intermediate. This product was combined with 1 other batches on the 200 g scale prepared by an identical method. (700 g-crude, 86.44%), as light yellow liquid. MS (ES): m/z 373.35 $[M+1]^+$. To a solution of mesylated product above (350 g, 940.0 mmol) in MeCN (3.5 L) was added dropwise DIPEA (529.23 g, 423.0 mmol, 4.5 eq) followed by dimethylamine hydrochloride (152.41 g, 1880.0 mmol, 2.0 eq) at RT. After stirring at 90° C. for 3 h, the reaction mixture was evaporated to remove ACN. The residue was quenched in Water (1500 mL) and extracted by DCM (3×3 L). The combined organic layer was washed with brine (10 L), dried with Na$_2$SO$_4$, and concentrated under reduced pressure to afford Intermediate-AA145-7. The product was combined with 1 other batches on the same scale prepared by an identical method. (700 g, quantitative yield), as brown semi solid. MS (ES): m/z 322.39 [M+1]$^+$, $^1$H NMR (400 MHz, DMSO): δ 9.61 (S, 1H), 7.67 (S, 2H),3.96-3.94 (t, 2H, J=7.6), 3.78-3.77 (d, 2H, J=4 HZ), 3.57 (S, 1H), 3.54 (s, 1H), 2.26-2.25 (t, 1H), 2.1 (S, 6H), 1.86 (S, 1H), 1.45 (s, 9H).

Step-8 Synthesis of compound 5-cyclopentyl-6-((dimethylamino)methyl)pyridin-2-amine (Intermediate-AA145)

To a solution of Intermediate-AA145-7 (700 g, 2180.7 mmol) in DCM (5.0 L) was added TFA (2.1 L, 3 v) at 0° C. After stirring at 70° C. for 2 h, the reaction mixture was evaporated. The residue was diluted in Water (2 L) and extracted with heptane. The heptane layer was discarded. The aqueous layer was neutralized with 10% NaOH solution and extracted by 15% MeOH in DCM (4×3 L). The combined organic layer was dried over sodium sulfate and concentrated under reduced pressure. The residue was triturated with 20% ethyl acetate in hexanes and then diethyl ether to afford Intermediate-AA145 as light brown solid. (330 g, 68.47%). MS (ES): m/z 222.30 [M+1]$^+$, 1H NMR (400 MHz, DMSO-d6) δ 7.33 (d, J=8.4 Hz, 1H), 6.36 (d, J=8.5 Hz, 1H), 5.71 (s, 1H), 3.96-3.85 (m, 1H), 3.72 (dq, J=31.0, 7.7 Hz, 1H), 3.46-3.34 (m, 1H), 3.35 (s, 1H), 3.30 (d, J=11.9 Hz, 0H), 2.19 (td, J=7.8, 4.2 Hz, 0H), 2.14 (s, 3H), 1.79 (dq, J=12.2, 8.0 Hz, 1H).

Synthesis of 1-(2-(4-(6-aminopyridin-3-yl)morpholin-2-yl)propan-2-yl)azetidin-3-ol (Intermediate-AA146)

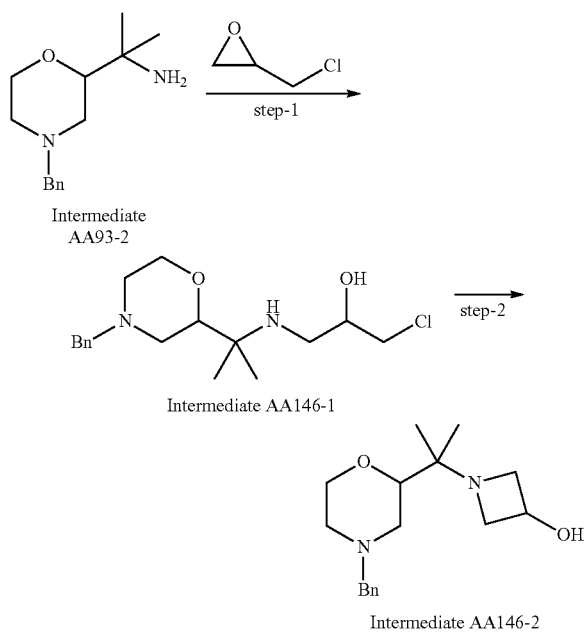
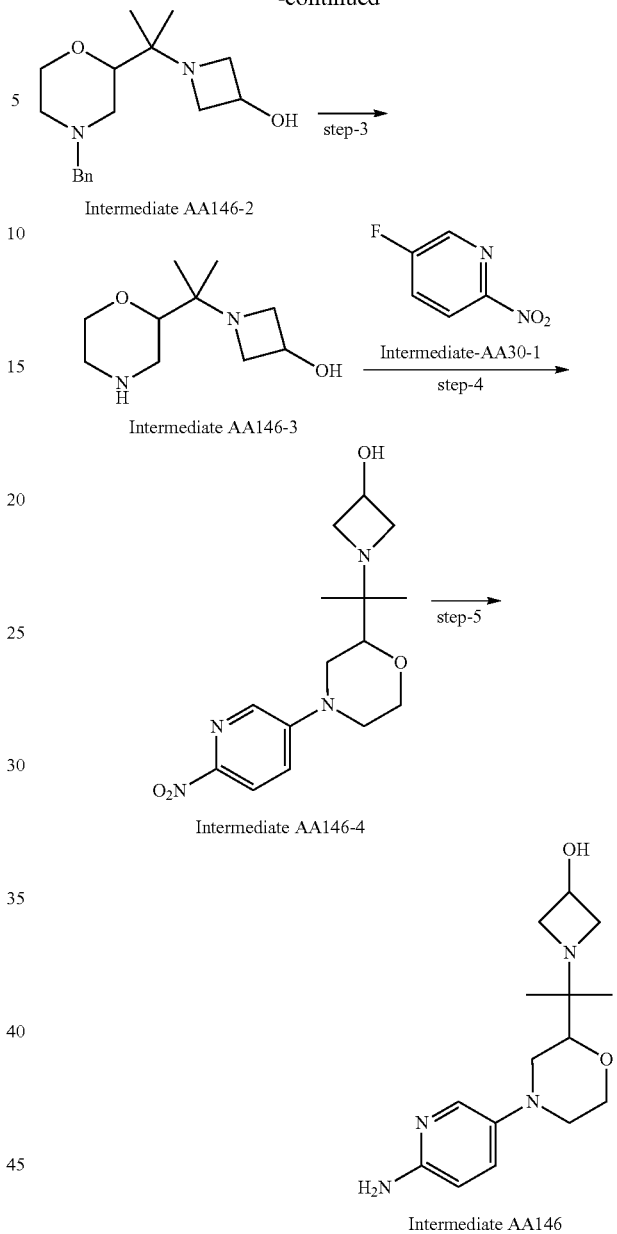

Step 1 Synthesis of 1-((2-(4-benzylmorpholin-2-yl)propan-2-yl)amino)-3-chloropropan-2-ol (Intermediate AA146-1)

To a solution of Intermediate AA93-2 (5 g, 26.7 mmol, 1.0 eq) in IPA was added 2-(chloromethyl) oxirane (3.5 g, 26.7 mmol, 1.5 eq). After stirring at RT for 16 h, the reaction mixture was concentrated under reduced pressure. The residue was purified by column chromatography (3.5% methanol gradient in DCM) to afford Intermediate AA146-1 (0.4 g, 6%), MS (ES): m/z=326 [M+H]$^+$ Step 2 Synthesis of 1-(2-(4-benzylmorpholin-2-yl)propan-2-yl)azetidin-3-ol (Intermediate AA146-2)

To a solution of Intermediate AA146-1 (1.9 g, 5.5 mmol), in acetonitrile was added TEA (1.2 mL, 8.2 mmol, 1.5 eq).

After stirring at 80° C. for 16 h, the reaction mixture was concentrated under reduced pressure. The residue was purified by column chromatography to afford the title compound (Intermediate AA146-2) (1.30 g, 77%). MS (ES): m/z=290 (M+H).

Step-3 synthesis of 2-(4-(6-nitropyridin-3-yl)-1,4-oxazepan-6-yl)propan-2-ol (Intermediate AA146-3)

To a solution of Intermediate AA146-2 (2.5 g) in EtOH (15 mL) were added 10% Pd/C (0.50 g) and (0.5 g) Pd(OH)$_2$. After stirring under H$_2$ gas at atmospheric pressure for 16 h in autoclave, the reaction mixture was filtrate through celite bed. The organic layer was evaporated in vacuum to afford Intermediate AA146-3 (1.8 g, quantitative) which was used in the next step without purification. MS (ES): m/z=200 [M+1]+

Step-4 synthesis of 1-(2-(4-(6-nitropyridin-3-yl)morpholin-2-yl)propan-2-yl)azetidin-3-ol (Intermediate AA146-4)

To a solution of Intermediate AA146-3 (1.8 g, 9 mmol) in DMSO (15 mL) were added dropwise DIPEA (10 mL) and then dropwise 5-fluoro-2-nitropyridine (1.9 g, 13 mmol, 1.5 eq). After stirring for 45 min at 120° C., the reaction mixture was cooled at RT and diluted with ethyl acetate (20 mL) and water (15 mL). The organic layer was collected, and the aqueous phase was extracted with ethyl acetate (2×30 mL). The combined organic extracts were washed with brine (10 mL), dried over Na$_2$SO$_4$, filtered, and concentrated under reduced pressure. The residue was purified by column chromatography (3.5% methanol gradient in DCM) to afford the title compound Intermediate AA146-4 (0.8 g, 27%), MS (ES): m/z=322 [M+H]$^+$ Step-5 synthesis of 1-(2-(4-(6-aminopyridin-3-yl)morpholin-2-yl)propan-2-yl)azetidin-3-ol (Intermediate AA146)

To a solution of Intermediate AA146-4 (0.8 g) in MeOH (10 mL) was treated with 10% Pd/c (0.150 g). After stirring at RT for 2 h with H$_2$ gas at atmospheric pressure, the reaction mixture was filtered through celite bed. The organic solution was evaporated in vacuum to afford Intermediate AA146 (0.7 g, quantitative) which was used in the next step without purification. MS (ES): m/z=292 [M+1]$^+$ Synthesis of 1-(6-bromopyridin-2-yl)-N,N-dimethylmethanamine (Intermediate-AA147)

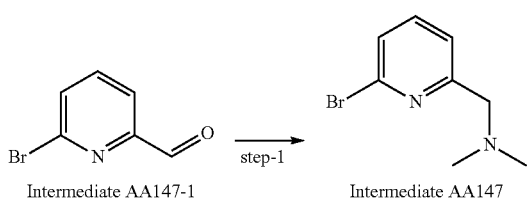

Intermediate AA147-1        Intermediate AA147

Step-1 Synthesis of 1-(6-bromopyridin-2-yl)-N,N-dimethylmethanamine (Intermediate AA147)

To a solution of Intermediate AA147-1 (0.700 g, 0.3 mmol) and sodium triacetoxy borohydride (8 g) in DCE (6 mL) was added glacial acetic acid (0.8 mL). After degassing using nitrogen gas for 20 min, dimethylamine (10 mL) was added. After stirring overnight, the reaction mixture was diluted with water and extracted with ethyl acetate. The combined organic layer was washed with brine solution, dried over sodium sulfate, and concentrated under reduced pressure. The residue was purified by silica gel eluting with 2-4% MeOH/DCM to afford Intermediate AA147 (0.189 g, 25.43%), LCMS: 95%, MS (ES): m/z 215.2 [M+H]$^+$ Synthesis of 3R,4R)-1-(6-chloro-2-((dimethylamino)methyl)pyridin-3-yl)-4-fluoropiperidin-3-ol (Intermediate-AA148)

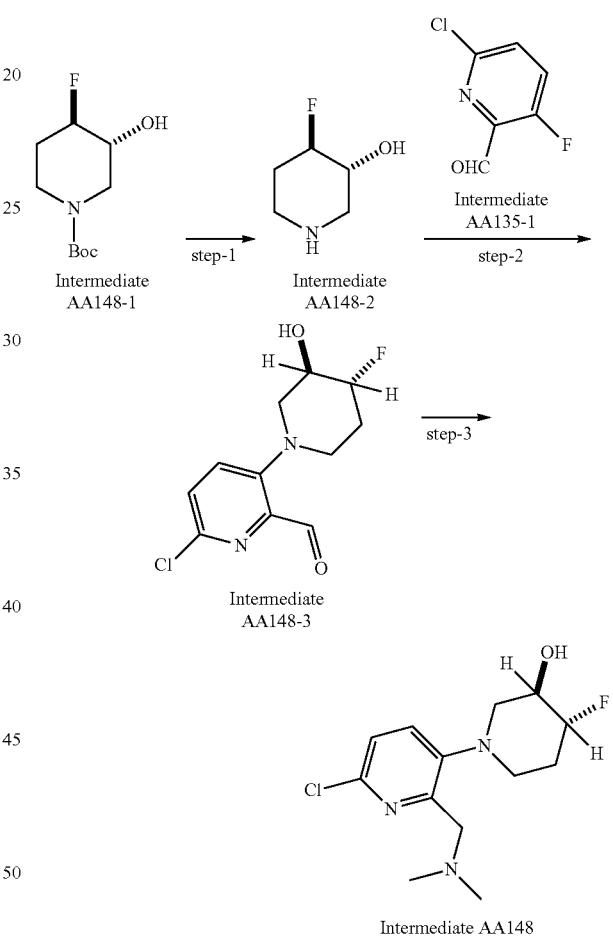

Step-1 Synthesis of 3R,4R)-4-fluoropiperidin-3-ol (Intermediate AA148-2)

To a solution of Intermediate AA148-1(2.2 g, 10.04 mmol) in DCM (20 mL) was added dropwise 4 M HCl in dioxane (20 mL) at RT. After stirring at RT for 2 h, the reaction mixture was concentrated under reduced pressure. The residue was purified by trituration with diethyl ether to afford Intermediate AA148-2 (1.7 g, quantitative) which was used in the next step without purification, MS (ES): m/z=120.2 [M+H]$^+$.

Step-2 Synthesis of 6-chloro-3-((3R,4R)-4-fluoro-3-hydroxypiperidin-1-yl)picolinaldehyde (Intermediate AA148-3)

To a solution of 6-chloro-3-fluoropicolinaldehyde (1.7 g, 10.69 mmol) and Intermediate AA148-2 (2.5 g, 21.38 mmol, 2.0 eq) in DMF (20 mL) was added dry potassium carbonate (7.3 g, 53.45 mmol, 5.0 eq). After stirring for 1 h at 100° C., the reaction mixture was cooled at RT and diluted with water (150 mL). The organic layer was collected, and the aqueous phase was extracted with ethyl acetate (3×50 mL). The combined organic extracts were washed with brine (100 mL), dried over Na$_2$SO$_4$, filtered, and concentrated under reduced pressure. The residue was purified by column chromatography (20% ethyl acetate gradient in hexane) to afford Intermediate AA148-3 (1.3 g, 47.16%), MS (ES): m/z=259.3 [M+H]$^+$.

Step-3 Synthesis of 3R,4R)-1-(6-chloro-2-((dimethylamino)methyl)pyridin-3-yl)-4-fluoropiperidin-3-ol (Intermediate AA148)

To a solution of Intermediate AA148-3 (1.3 g, 5.03 mmol) in methanol: DCM (10 mL:10 mL) was added dimethylamine solution (2M in THF) (3.7 mL, 7.54 mmol, 1.5 eq). After stirring for 30 min at RT, acetic acid (0.3 mL) and sodium cyanoborohydride (0.63 g, 10.06 mmol, 2.0 eq) were added. After stirring for 30 min at RT, the reaction mixture was diluted with sodium bicarbonate solution (100 mL) and extracted with DCM (3×50 mL). The combined organic extracts were washed with brine (100 mL), dried over Na$_2$SO$_4$, filtered, and concentrated under reduced pressure. The residue was purified by column chromatography (0.5% methanol gradient in DCM) to afford Intermediate AA148 (0.9 g, 62.23%), MS (ES): m/z=288.2 [M+H]$^+$

Synthesis of Tert-Butyl ((6-amino-3-(THF-3-yl)pyridin-2-yl)methyl)carbamate (Intermediate-AA149)

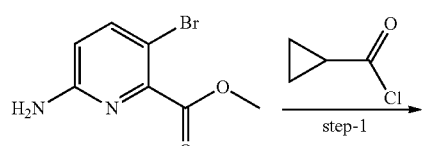

Intermediate AA145-2

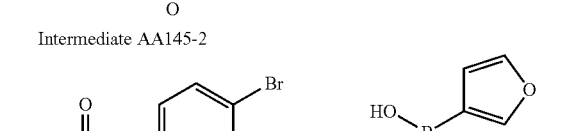

Intermediate AA149-1

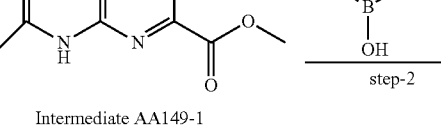

IntermediateAA149-2

-continued

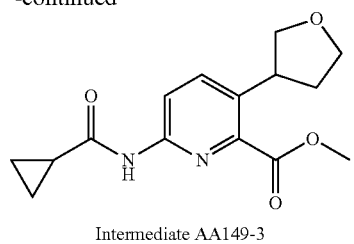

Intermediate AA149-3

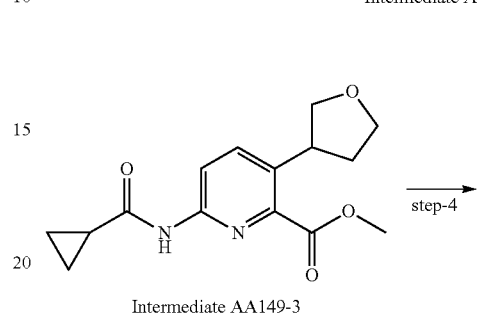

Intermediate AA149-3

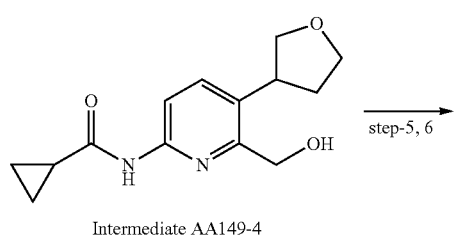

Intermediate AA149-4

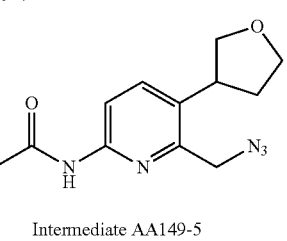

Intermediate AA149-5

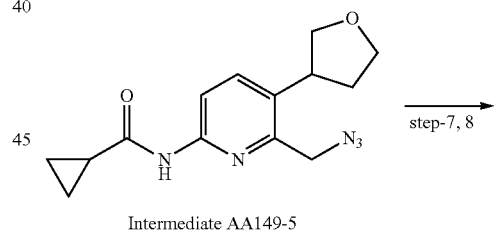

Intermediate AA149-5

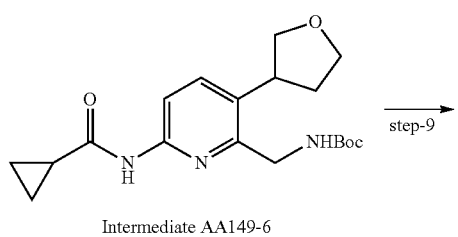

Intermediate AA149-6

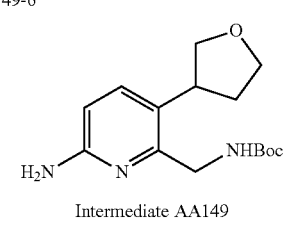

Intermediate AA149

Step-1 Synthesis of methyl 3-bromo-6-(cyclopropanecarboxamido)picolinate (Intermediate AA149-1)

To a solution of Intermediate AA145-2 (4.0 g, 17.46 mmol) in DCM (40 mL) at 0° C. were added triethylamine (7.3 mL, 52.38 mmol, 3.0 eq) and cyclopropanecarbonyl chloride (7.2 g, 69.84 mmol, 4.0 eq). After stirring at RT for 2 h, the reaction mixture was diluted with water (150 mL) and extracted with DCM (3×70 mL). The combined organic extracts were washed with brine (200 mL), dried over Na$_2$SO$_4$, filtered, and concentrated under reduced pressure. The residue was purified by column chromatography (18% ethyl acetate gradient in hexane) to afford Intermediate AA149-1 (4.8 g, 92.69%) MS (ES): m/z=299.2 [M+H]$^+$.

Step-2 Synthesis of methyl 6-(cyclopropanecarboxamido)-3-(furan-3-yl)picolinate (Intermediate AA149-2)

To a solution of Intermediate AA149-1 (4.0 g, 13.37 mmol) in dioxane (35 mL) and water (6 mL) were added furan-3-ylboronic acid (1.8 g, 16.04 mmol, 1.2 eq) and potassium phosphate tribasic (8.5 g, 40.11 mmol, 3.0 eq). After degassing with N$_2$ for 15 min, bis(triphenylphosphine) palladium(II) dichloride (0.463 g, 0.66 mmol, 0.05 eq) was added. After stirring at 110° C. for 2 h, the reaction mixture was cooled to RT, diluted water (150 mL) and extracted with ethyl acetate (3×100 mL). The combined organic extracts were washed with brine (200 mL), dried over Na$_2$SO$_4$, filtered, and concentrated under reduced pressure. The residue was purified by column chromatography eluting with 20% ethyl acetate gradient in hexane to afford Intermediate AA149-2 (3.5 g, 91.42%), MS (ES): m/z 287.2 [M+H]$^+$

Step-3 Synthesis of methyl 6-(cyclopropanecarboxamido)-3-(THF-3-yl)picolinate (Intermediate AA149-3)

In autoclave, a solution of Intermediate AA149-2 (3.5 g, 12.23 mmol) in methanol (35 mL) were added ammonium formate (1.5 g, 24.46 mmol, 2.0 eq), acetic acid (3 mL). and palladium hydroxide on carbon (20%) (2.2 g). After stirring at 20 psi hydrogen atmosphere for 16 h, the reaction mixture was filtered through celite-bed and washed with methanol. The filtrate was concentrated under reduced pressure. The residue was purified by column chromatography eluting with 25% ethyl acetate gradient in hexane to afford Intermediate AA149-3 (2.5 g, 70.44%). MS (ES): m/z 291.2 [M+H]$^+$.

Step-4 Synthesis of N-(6-(hydroxymethyl)-5-(THF-3-yl)pyridin-2-yl)cyclopropanecarboxamide (Intermediate AA149-4)

To a cooled solution of Intermediate AA149-3 (2.5 g, 8.62 mmol) in ethanol at 0° C. (25 mL) was added portion wise sodium borohydride (1.3 g, 34.48 mmol, 4.0 eq). Reaction mixture stirred at RT for 1 h, the reaction mixture was concentrated under reduced pressure, diluted with water (70 mL), and extracted with DCM (3×40 mL). The combined organic extracts were washed with brine (80 mL), dried over Na$_2$SO$_4$, filtered, and concentrated under reduced pressure. The residue was purified by column chromatography eluting with 30% ethyl acetate gradient in hexane to afford Intermediate AA149-4 (1.4 g, 61.98%), MS (ES): m/z 263.2 [M+H]$^+$

Step-5,6 Synthesis of N-(6-(azidomethyl)-5-(THF-3-yl)pyridin-2-yl)cyclopropanecarboxamide (Intermediate AA149-5)

To a solution of Intermediate AA149-4 (1.3 g, 4.96 mmol) in DCM (15 mL) with triethylamine (1.7 mL, 11.70 mmol, 2.36 eq) at 0° C. was added methane sulfonyl chloride (0.7 mL, 9.92 mmol, 2.0 eq) dropwise. After stirring at 0° C. for 1 h, the reaction mixture was diluted with water (80 mL), washed with sodium bicarbonate solution, and extracted with DCM (3×40 mL). The combined organic extracts were washed with brine (80 mL), dried over Na$_2$SO$_4$, filtered, and concentrated under reduced pressure (2 g). The residue (2.0 g, 5.88 mmol) was added a solution of sodium azide (0.764 g, 11.76 mmol, 2.0 eq) and 18-Crown-6 (0.062 g, 0.23 mmol, 0.04 eq) in acetonitrile (20 mL). After stirring at RT for 2 h, the reaction mixture was filtered through celite-bed. The filtrate was concentrated under reduced pressure to afford Intermediate AA149-5 (0.8 g, 56.18%), MS (ES): m/z 288.1 [M+H]$^+$.

Step-7, 8 Synthesis of Tert-Butyl ((6-(cyclopropanecarboxamido)-3-(THF-3-yl)pyridin-2-yl)methyl)carbamate (Intermediate AA149-6)

To a solution of Intermediate AA149-5 (0.8 g, 2.78 mmol) in ethanol (10 mL) was added. palladium on charcoal (0.4 g). After stirring under hydrogen gas at atmospheric pressure for 4 h at RT, the reaction mixture was filtered through celite-bed and washed with methanol. The filtrate was concentrated under reduced pressure (0.68 g). The residue (0.68 g, 2.60 mmol) was dissolve in DCM (6 mL) with trimethylamine (1.8 mL, 7.8 mmol, 3.0 eq). The reaction mixture was cooled to 0° C. and di-tert-butyl dicarbonate (0.68 g, 7.8 mmol, 3.0 eq) was added. After stirring at RT for 30 min, the reaction mixture was filtered through celite-bed. The filtrate was concentrated under reduced pressure to afford Intermediate AA149-6 (0.7 g, 69.56%), MS (ES): m/z 362.2 [M+H]$^+$

Step 9. Tert-Butyl ((6-amino-3-(THF-3-yl)pyridin-2-yl)methyl)carbamate (Intermediate AA149)

To a solution of Intermediate AA149-6 (0.7 g, 1.93 mmol) in methanol (7 mL) and water (2 mL) was added sodium hydroxide (0.9 g, 23.16 mmol, 12.0 eq). After stirring at 40° C. for 10 h, the reaction mixture was cooled to RT, concentrated under reduced pressure, diluted water (70 mL) and extracted with ethyl acetate (3×40 mL). The combined organic extracts were washed with brine (60 mL), dried over Na$_2$SO$_4$, filtered, and concentrated under reduced pressure to afford Intermediate AA149 (0.5 g, 88.00%), MS (ES): m/z 294.2 [M+H]$^+$

Synthesis of 4-(6-chloropyridin-3-yl)-N,N-dimethyl-tetrahydro-2H-pyran-4-amine (Intermediate-AA150)

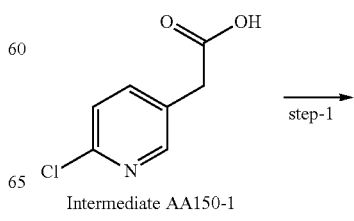

Intermediate AA150-1

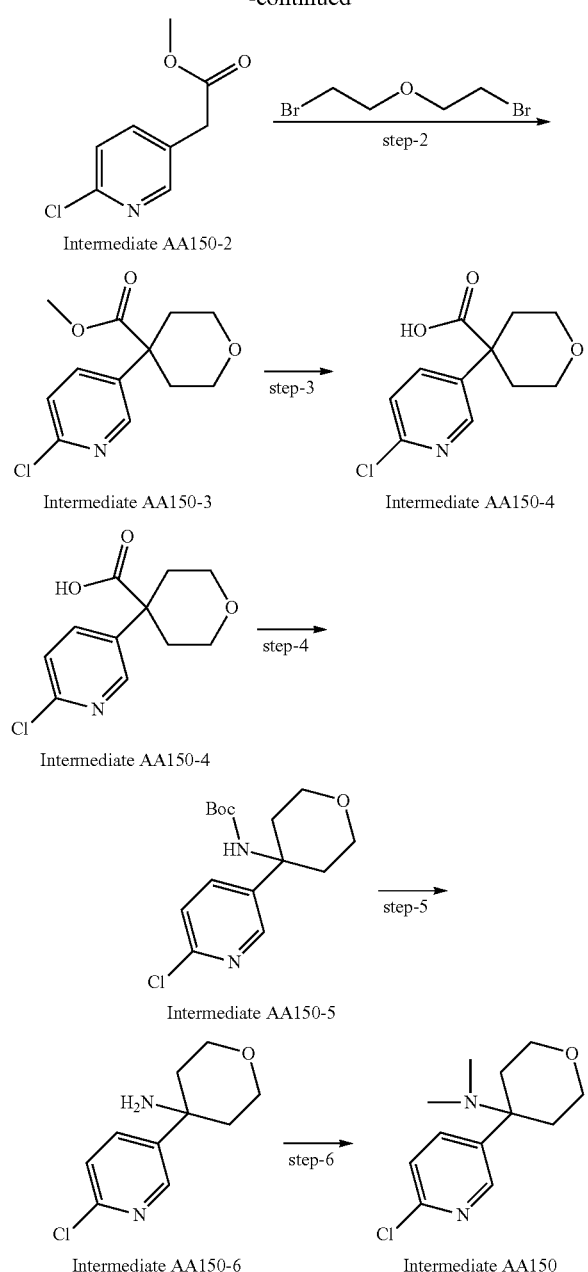

Step-1 Synthesis of methyl 2-(6-chloropyridin-3-yl)acetate (Intermediate AA150-2)

To a solution of Intermediate AA150-1 (2.5 g, 14.61 mmol) in methanol (25 mL) was added concentrated sulfuric acid (1 mL) at RT. After stirring at RT for 1 h, the reaction mixture was neutralized with sodium bicarbonate solution and extracted with ethyl acetate (3×60 mL). The combined organic extracts were washed with brine (100 mL), dried over $Na_2SO_4$, filtered, and concentrated under reduced pressure to afford Intermediate AA150-2 (2.4 g, 88.74%) which was used in the next step without purification. MS (ES): m/z=186.2 $[M+H]^+$.

Step-2 Synthesis of methyl 4-(6-chloropyridin-3-yl) tetrahydro-2H-pyran-4-carboxylate (Intermediate AA150-3)

To a cooled solution of Intermediate AA150-2 (2.4 g, 12.97 mmol) and 1-bromo-2-(2-bromoethoxy)ethane (1.8 g, 7.78 mmol, 0.6 eq) in THF (80 mL) at 0° C. was added dropwise lithium bis(trimethylsilyl)amide (1M in THF) (9.5 mL) under $N^2$ atmosphere. After stirring for 2 h at RT, lithium bis(trimethylsilyl)amide (9.5 mL) was added. After stirring for 16 h at RT, the reaction mixture was quenched with brine solution (80 mL) and extracted with ethyl acetate (3×50 mL). The combined organic solution was dried over $Na_2SO_4$, filtered, and concentrated under reduced pressure to afford Intermediate AA150-3 (2.4 g, 72.59%), which was used in next step without purification. MS (ES): m/z=256.2 $[M+H]^+$ Step-3 Synthesis of 4-(6-chloropyridin-3-yl)tetrahydro-2H-pyran-4-carboxylic Acid (Intermediate AA150-4)

To a solution of Intermediate AA150-3 (2.4 g, 9.41 mmol) in methanol (25 mL) was added 6N NaOH solution (10 mL). After stirring at 70° C. for 2 h, 4M HCl in dioxane was added. After stirring for 10 min, the reaction mixture was concentrated under reduced pressure. The residue was purified by column chromatography (7% methanol gradient in DCM) to afford Intermediate AA150-4 (2.0 g, 88.17%) MS (ES): m/z=242.2 $[M+H]^+$.

Step-4 Synthesis of Tert-Butyl (4-(6-chloropyridin-3-yl)tetrahydro-2H-pyran-4-yl)carbamate (Intermediate AA150-5)

To a solution of Intermediate AA150-4 (2.0 g, 8.29 mmol) with 4 å molecular sieve under $N_2$ gas atmosphere in tert-Butyl alcohol (20 mL) were added diphenylphosphoryl azide (2.5 mL) and triethylamine (2.5 mL) dropwise to reaction mixture. After stirring at RT for 1 h then for 16 h at 70° C., the reaction mixture was filtered, and filtrate was concentrated under reduced pressure. The residue was purified by column chromatography (25% ethyl acetate gradient in hexane) to afford Intermediate AA150-5 (1.4 g, 54.08%) MS (ES): m/z=313.2 $[M+H]^+$.

Step-5 Synthesis of 4-(6-chloropyridin-3-yl)tetrahydro-2H-pyran-4-amine (Intermediate AA150-6)

To a solution of Intermediate AA150-5 (1.4 g, 4.48 mmol, 1 eq) in DCM (20 mL) at 0° C. was dropwise added 4N hydrochloric acid in dioxane (15 mL). After stirring at RT for 3 h., the reaction mixture was neutralized with sodium bicarbonate solution and extracted with ethyl acetate (3×50 mL). The combined organic layer was dried over $Na_2SO_4$, filtered, and concentrated under reduced pressure to afford Intermediate AA150-6 (1.0 g, 94.55%). MS (ES): m/z 213.07 $[M+H]^+$ Step-6 Synthesis of 4-(6-chloropyridin-3-yl)-N,N-dimethyltetrahydro-2H-pyran-4-amine (Intermediate AA150)

To a solution of Intermediate AA150-6 (1.0 g, 4.71 mmol) in methanol (10 mL) added Formaldehyde (0.282 g, 9.42 mmol, 2.0 eq) and stirred reaction mixture for 30 min. Then added acetic acid (3.3 mL) and portion wise sodium cyanoborohydride (0.741 g, 11.77 mmol, 2.5 eq) at 0° C. The reaction mixture stirred for 3 h at 60° C. After completion of reaction, the reaction mixture was concentrated under reduced pressure. The residue was purified by column chromatography (3.0% methanol gradient in DCM) Intermediate AA150 (0.9 g, 79.51%), MS (ES): m/z=241.3 [M+H]⁺

Synthesis of 6-((dimethylamino)methyl)-5-(2-(methoxymethyl)morpholino)pyridin-2-amine (Intermediate AA151)

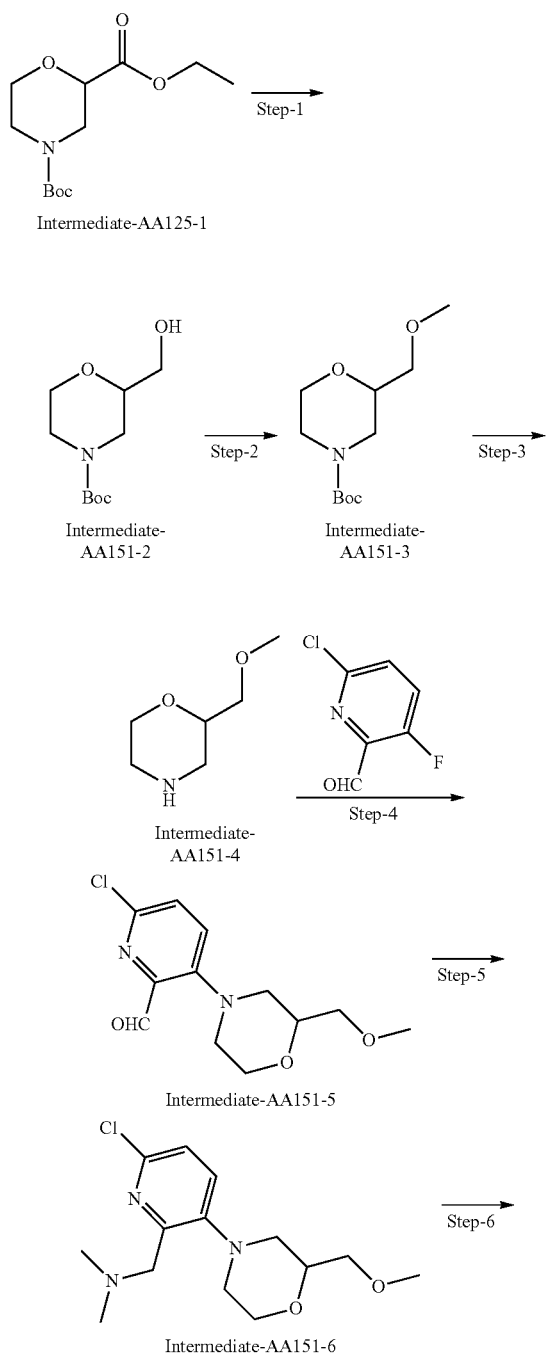

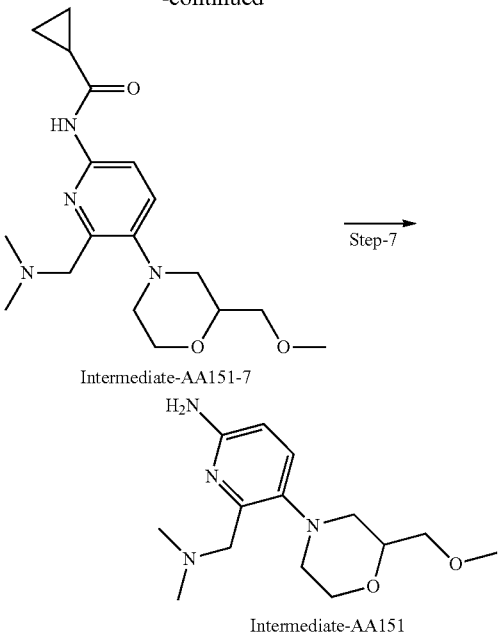

Step-1 Synthesis of Tert-Butyl 2-(hydroxymethyl)morpholine-4-carboxylate (Intermediate AA151-2)

To a solution of the Intermediate AA125-1 (10 g, 38.6 mmol) in methanol (100 mL) at 0° C. was added NaBH$_4$ (4 g, 115.8 mmol, 3 eq) portion wise. After stirring at RT for 3 h, the reaction was quenched with water (100 mL) and extracted with ethyl acetate (3×40 mL). The combined organic layer was washed with brine, passed through a hydrophobic filter, and evaporated in vacuum to afford Intermediate AA151-2 (8 g, 95.48%) which was used in the next step without purification MS (ES): m/z 218.1 [M+H]⁺.

Step-2 Synthesis of Tert-Butyl 2-(methoxymethyl)morpholine-4-carboxylate (Intermediate-AA151-3)

A solution of Intermediate-AA151-2 (8 g, 36.6, 1 eq), in DMF (80 mL) was added NaH (2.93 g, 73.3 mmol, 2 eq) and MeI (4.1 g, 43.92 mmol, 1.2 eq). After stirring for 4 h, the reaction mixture was diluted with water (150 mL) and extracted with ethyl acetate (3×100 mL). The combined organic extracts were wash with brine (150 mL), dried over Na$_2$SO$_4$, filtered, and concentrated under reduced pressure. The residue was purified by column chromatography to afford Intermediate-AA151-3) (7.5 g, 88.06%) MS (ES): m/z=232.29 [M+H]⁺.

Step-3 Synthesis of 2-(methoxymethyl)morpholine (Intermediate-AA151-4)

To a solution of Intermediate AA151-3 (7.5 g) into DCM (75 mL) at 0° C. was added 4 M HCl in dioxane (32 mL). After stirring at RT for 1 h, the reaction mixture was neutralized using saturated sodium bicarbonate solution and extracted with DCM to get pure title compound (Intermediate AA151-3) (4 g, 94.05%) MS (ES): m/z 132.6 (M+H)+.

Step-4 Synthesis of 6-chloro-3-(2-(methoxymethyl) morpholino)picolinaldehyde (Intermediate-AA151-5)

To a solution of Intermediate-AA151-4 (7.5 g, 57.2 mmol) in DMF (75 mL) were added $K_2CO_3$ (23.7 g, 171.7 mmol, 3 eq) and 6-chloro-3-fluoropicolinaldehyde (11.74 g, 74.36 mmol, 1.3 eq). After stirring at 100° C. for 4 h, the reaction mixture was quenched in water (100 mL) and extracted with ethyl acetate (100 mL×3). The organic layer was combined and dried over sodium sulfate and concentrated under reduced pressure. The residue was purified by column chromatography to afford Intermediate-AA151-5 (6 g, 38.21%). MS (ES): m/z 271.71 [M+H]$^+$.

Step-5 synthesis of 1-(6-chloro-3-(2-(methoxymethyl)morpholino)pyridin-2-yl)-N,N-dimethylmethanamine (Intermediate-AA151-6)

To a solution of Intermediate Intermediate-AA151-4 (5 g, 18.4 mmol) in methanol (50 mL) at 0° C. were added acetic acid (5 mL) and dimethyl amine (1.3 g, 27.6 mmol, 1.5 eq). After stirring at RT for 45 min, NaCN(BH3) (73.6 mmol, 4 eq) was added. After stirring for 2 h, the reaction was diluted with water (90 mL) and extracted with ethyl acetate (3×50 mL). The combined organic extracts were washed with brine (100 mL), dried over $Na_2SO_4$, filtered, and concentrated under reduced pressure. The residue was purified by silica gel chromatography to afford Intermediate AA151-6 (3.5 g, 61%). MS (ES): m/z=300.8 (M+H)+.

Step-6 synthesis of N-(6-((dimethylamino)methyl)-5-(2-(methoxymethyl)morpholino)pyridin-2-yl)cyclopropanecarboxamide (Intermediate AA151-7)

To a solution of Intermediate AA151-6 (1 g, 3.3 mmol) and 1-cyclopropanecarboxamide (0.5 g, 6.0 mmol, 1.8 eq) in 1,4-dioxane (10 mL) was added potassium carbonate (1.3 g, 9.9 mmol, 3.0 eq). After degassing under $N_2$ stream for 15 min, Xantphos (0.382 g, 1.59 mmol, 0.66 eq) and $Pd_2(dba)_3$ (0.274 g, 0.3 mmol, 0.1 eq) added. After stirring at 110° C. for 1 h, the reaction mixture was cooled to RT, diluted water (70 mL) and extracted with ethyl acetate (2×50 mL). The combined organic extracts were washed with brine (80 mL), dried over $Na_2SO_4$, filtered, and concentrated under reduced pressure. The residue was purified by column chromatography to afford Intermediate AA1151-7 (0.800 g, 68%) MS (ES): m/z=349.45 [M+H]$^+$

Step-7 synthesis of 6-((dimethylamino)methyl)-5-(2-(methoxymethyl)morpholino)pyridin-2-amine (Intermediate AA151)

To a solution of Intermediate AA151-7 (0.800 g, 2.2 mmol) in methanol:water (20 mL:5 mL) was added sodium hydroxide (0.91 g, 22 mmol, 10 eq). After stirring at RT for 16 h, the reaction mixture was concentrated under reduced pressure. The residue was diluted with water (50 mL) at 10° C. and neutralized with 1N hydrochloric acid to pH-6-6.5. Product was extracted with DCM (3×40 mL). The combined organic layers were washed with brine solution, dried over sodium sulfate, and concentrated under reduced pressure to afford Intermediate AA151 (0.4 g, 62%). MS (ES): m/z 281.37 [M+H]$^+$

Synthesis of 1-(6-aminopyridin-3-yl)-3-(2-(dimethylamino)propan-2-yl)piperidin-3-ol (Intermediate-AA152)

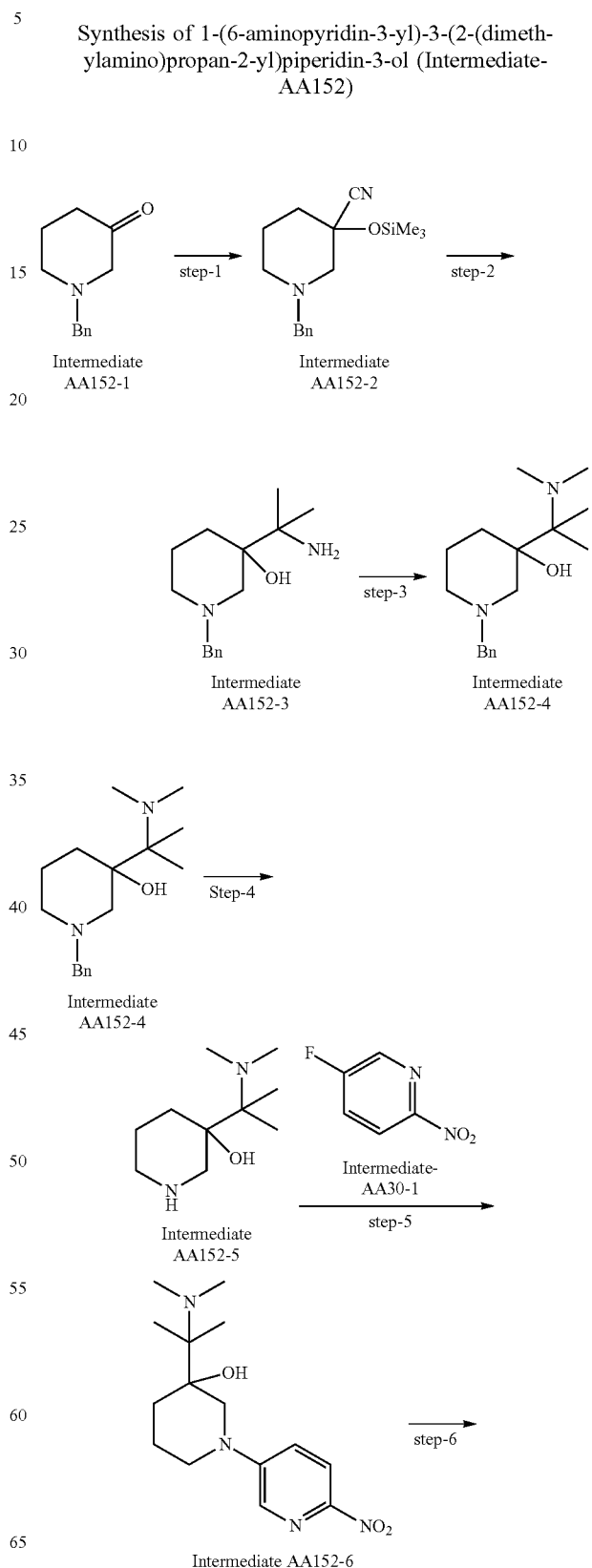

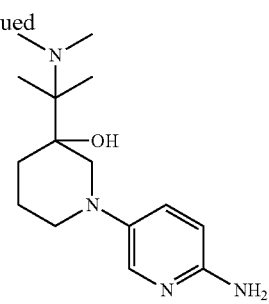

Intermediate AA152

Step-1 Synthesis of 1-benzyl-3-((trimethylsilyl)oxy) piperidine-3-carbonitrile (Intermediate AA152-2)

To a solution of Intermediate AA152-1 (15.0 g, 79.36 mmol) in dry DCM were added trimethylsilyl cyanide (12.95 mL, 103.16 mmol, 1.3 eq) and zinc iodide (2.5 g, 7.93 mmol, 0.1 eq) (25 mL). After stirring at reflux for 2 h, the reaction mixture was cooled to RT, diluted with water (200 mL), and extracted with ethyl acetate (3×120 mL). The combined organic extracts were washed with brine (200 mL), dried over $Na_2SO_4$, filtered, and concentrated under reduced pressure. The residue was purified by column chromatography (10-15% ethyl acetate gradient in hexane) to afford Intermediate AA152-2 (14.4 g, 62.98%) MS (ES): m/z=289.1 $[M+H]^+$

Step-2 Synthesis of 3-(2-aminopropan-2-yl)-1-benzylpiperidin-3-ol (Intermediate AA152-3)

After stirring a solution of cerium (III) chloride (17.11 g, 69.44 mmol, 2.0 eq) in THF (100 mL) at 45° C. for 2 h, Intermediate AA152-2 (10.0 g, 34.72 mmol) and methyllithium solution (1.6M in diethyl ether) (54 mL, 86.8 mmol, 2.5 eq) were added dropwise at 0° C. After stirring for 30 min at RT, the reaction mixture was quenched with cold water (500 mL) and extracted with 10% methanol in DCM (3×200 mL). The combined organic extracts were washed with brine (400 mL), dried over $Na_2SO_4$, filtered, and concentrated under reduced pressure. The residue was purified by column chromatography (2% methanol gradient in DCM) to afford Intermediate AA152-3 (2.0 g, 23.23%) MS (ES): m/z=249.1 $[M+H]^+$.

Step-3 Synthesis of 1-benzyl-3-(2-(dimethylamino) propan-2-yl)piperidin-3-ol (Intermediate AA152-4)

To a solution of Intermediate AA152-3 (1.2 g, 4.83 mmol) in methanol (15 mL) were add formaldehyde (1.2 g) and trimethylamine (1.0 mL, 7.24 mmol, 1.5 eq). After stirring at RT for 1 h, sodium cyanoborohydride (0.6 g, 9.66 mmol, 2.0 eq) was added. After stirring at RT for 16 h, the reaction mixture was quenched with water (100 mL) and extracted with ethyl acetate (3×40 mL). The combined organic extracts were washed with brine (90 mL), dried over $Na_2SO_4$, filtered, and concentrated under reduced pressure. The residue was purified by column chromatography (3% methanol gradient in DCM) to afford Intermediate AA152-4 (1.0 g, 74.88%) MS (ES): m/z=277.2 $[M+H]^+$.

Step-4 Synthesis of 3-(2-(dimethylamino)propan-2-yl)piperidin-3-ol (Intermediate AA152-5)

To a solution of Intermediate AA152-4 (1.1 g, 3.97 mmol) in methanol (15 mL) and concentrated HCl (0.5 mL) was added palladium hydroxide on carbon (20%, 0.5 g) under $N_2$ atmosphere. After stirring under hydrogen gas at atmospheric pressure for 2 h at RT, the reaction mixture was filtered through celite-bed and washed with methanol. The filtrate was concentrated under reduced pressure to afford Intermediate AA152-5 (0.8 g, quantitative yield) MS (ES): m/z=187.1 $[M+H]^+$

Step-5 Synthesis of 3-(2-(dimethylamino)propan-2-yl)-1-(6-nitropyridin-3-yl)piperidin-3-ol (Intermediate AA152-6)

To a solution of Intermediate AA30-1 (0.5 g, 3.52 mmol) and Intermediate AA152-5 (0.98 g, 5.28 mmol, 1.5 eq) in DMSO (5 mL) was added N, N-diisopropylethylamine (2.4 mL, 14.08 mmol, 4.0 eq). After stirring at 110° C. for 4 h, the reaction mixture was diluted with water (80 mL) and extracted with DCM (3×40 mL). The combined organic extracts were washed with brine (90 mL), dried over $Na_2SO_4$, filtered, and concentrated under reduced pressure. The residue was purified by column chromatography (2% methanol gradient in DCM) to afford Intermediate AA152-6 (0.350 g, 32.25%) MS (ES): m/z=309.2 $[M+H]^+$

Step 6 Synthesis of 1-(6-aminopyridin-3-yl)-3-(2-(dimethylamino)propan-2-yl)piperidin-3-ol (Intermediate AA152)

To a solution of Intermediate AA152-6 (0.350 g, 1.13 mmol) in methanol (5 mL) was added palladium on charcoal (0.170 g). After stirring under hydrogen gas at atmospheric pressure for 4 h at RT, the reaction mixture was filtered through celite-bed and washed with methanol. The filtrate was concentrated under reduced pressure to afford Intermediate AA152 (0.240 g, 75.96%) which was used in next step without purification. MS (ES): m/z 279.2 $[M+H]^+$

Synthesis of 6-((3,3-difluoropyrrolidin-1-yl) methyl)-5-(THF-3-yl)pyridin-2-amine (Intermediate-AA153)

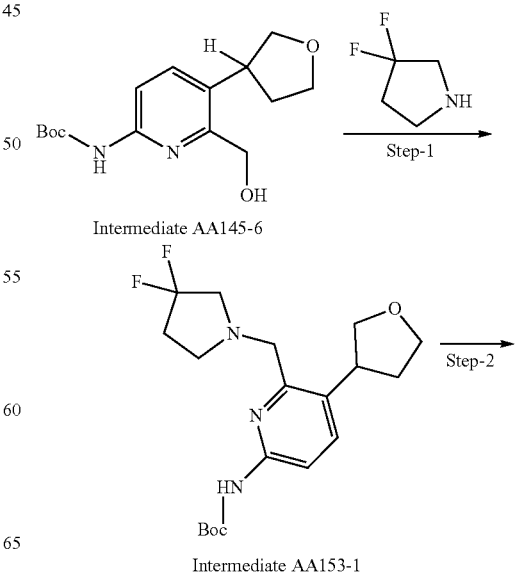

Intermediate AA153-1

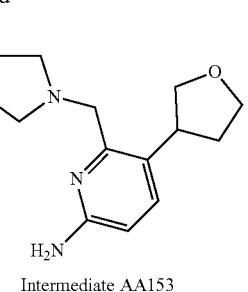

Intermediate AA153

6-((3,3-difluoropyrrolidin-1-yl)methyl)-5-(THF-3-yl)pyridin-2-amine (Intermediate AA153) was prepared from tert-butyl (6-(hydroxymethyl)-5-(THF-3-yl)pyridin-2-yl)carbamate (Intermediate AA145-6) and 3,3-difluoropyrrolidine in a similar fashion to that procedure of step-6, step-7 and step-8 described in synthesis of 5-cyclopentyl-6-((dimethylamino)methyl)pyridin-2-amine (Intermediate AA145) (0.8 g, 90.22%). m/z 284.15 [M+H]$^+$.

Synthesis of 4-(6-chloro-2-((dimethylamino)methyl)pyridin-3-yl)tetrahydro-2H-pyran-4-ol (Intermediate-AA154)

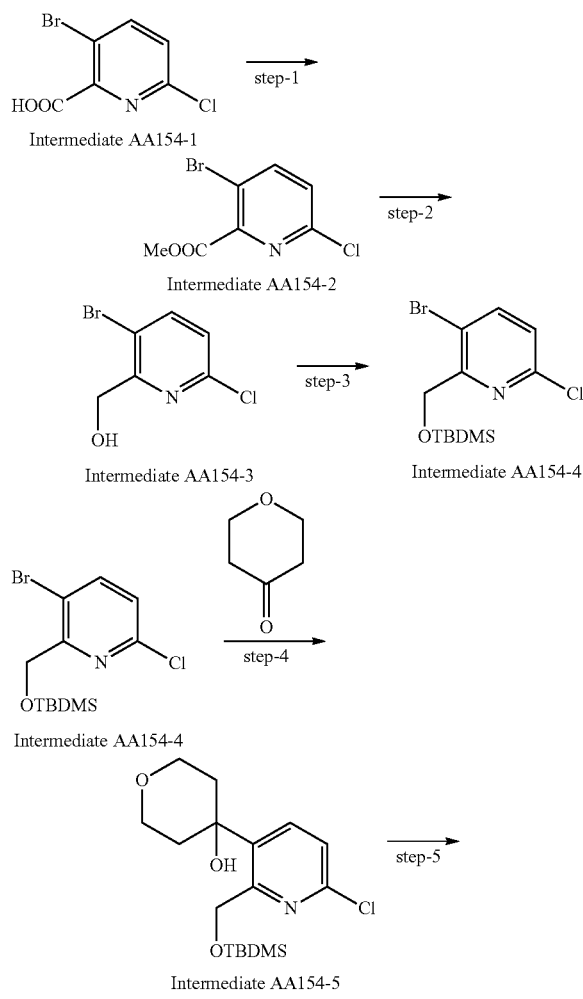

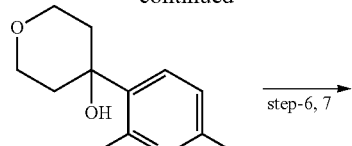

Intermediate AA154-6

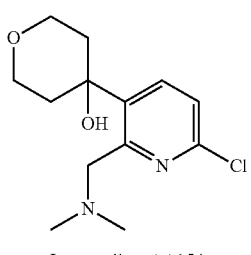

Intermediate AA154

Step-1 Synthesis of methyl 3-bromo-6-chloropicolinate (Intermediate AA154-2)

To a solution of Intermediate AA154-1 (8.0 g, 34.18 mmol) in DMF (80 mL) at 0° C. with added potassium carbonate (18.86 g, 136.72 mmol, 4.0 eq) was added methyl iodide (8.5 mL, 136.72 mmol, 4.0 eq) dropwise. After stirring for 2 h at RT, the reaction mixture was diluted with ice cold water (400 mL) and extracted with ethyl acetate (3×150 mL). The combined organic extracts were washed with brine (2×200 mL), dried over Na$_2$SO$_4$, filtered, and concentrated under reduced pressure. The residue was purified by column chromatography (35% ethyl acetate gradient in hexane) to afford Intermediate AA154-2 (3.5 g, 41.30%) MS (ES): m/z=250.9 [M+H]$^+$.

Step-2 Synthesis of 3-bromo-6-chloropyridin-2-yl)methanol (Intermediate AA154-3)

To a solution of Intermediate AA154-2 (8.0 g, 32.00 mmol) in ethanol (80 mL) at 0° C. was added sodium borohydride (4.8 g, 128 mmol, 4.0 eq) portion wise. After completion of reaction, the reaction mixture was quenched with water (300 mL) and extracted with DCM (3×100 mL). The combined organic extracts were washed with brine (2×100 mL), dried over Na$_2$SO$_4$, filtered, and concentrated under reduced pressure. The residue was purified by column chromatography (0.7% methanol gradient in DCM) to afford Intermediate AA154-3 (3.5 g, 49.26%) MS (ES): m/z=222.9 [M+H]$^+$.

Step-3 Synthesis of 3-bromo-2-(((tert-butyldimethylsilyl)oxy)methyl)-6-chloropyridine (Intermediate AA154-4)

To a solution of Intermediate AA154-3 (7.0 g, 31.53 mmol) in DCM (70 mL) were added DMAP (0.769 g, 6.30 mmol, 0.2 eq), imidazole (2.7 g, 40.67 mmol, 1.29 eq) and tert-butyldimethylsilyl chloride (5.6 g, 37.83 mmol, 1.2 eq) portion wise. After stirring at RT for 16 h, the reaction mixture was diluted with water (400 mL) and extracted with DCM (3×150 mL). The combined organic extracts were washed with brine (150 mL), dried over Na$_2$SO$_4$, filtered, and concentrated under reduced pressure. The residue was purified by column chromatography (20% ethyl acetate gradient in hexane) to afford Intermediate AA154-4 (4.0 g, 37.75%) MS (ES): m/z=336.2 [M+H]⁺.

Step-4 Synthesis of 4-(2-(((tert-butyldimethylsilyl)oxy)methyl)-6-chloropyridin-3-yl)tetrahydro-2H-pyran-4-ol (Intermediate AA154-5)

To a solution of Intermediate AA154-4 (8.0 g, 23.88 mmol) in THF (80 mL) at −78° C. was added n-butyllithium (2.5M in hexane) (11.5 mL, 28.65 mmol, 1.2 eq). After stirring for 30 min, tetrahydro-4H-pyran-4-one (4.7 g, 47.76 mmol, 2.0 eq) was added. After stirring at RT for 30 min, the reaction mixture was diluted with water (500 mL) and extracted with DCM (3×200 mL). The combined organic extracts were washed with brine (300 mL), dried over Na$_2$SO$_4$, filtered, and concentrated under reduced pressure. The residue was purified by column chromatography (20% ethyl acetate gradient in hexane) to afford Intermediate AA154-5 (5.0 g, 58.79%) MS (ES): m/z=358.2 [M+H]⁺.

Step-5 Synthesis of 4-(6-chloro-2-(hydroxymethyl)pyridin-3-yl)tetrahydro-2H-pyran-4-ol (Intermediate AA154-6)

To a solution of Intermediate AA154-5 (5.0 g, 13.96 mmol) in THF (50 mL) at 0° C. was added dropwise tetra-n-butylammonium fluoride (20 mL, 69.8 mmol, 5.0 eq). After stirring at RT for 1 h, the reaction mixture was diluted with water (150 mL) and extracted with ethyl acetate (3×40 mL). The combined organic extracts were washed with brine (200 mL), dried over Na$_2$SO$_4$, filtered, and concentrated under reduced pressure. The residue was purified by column chromatography (40% ethyl acetate gradient in hexane) to afford Intermediate AA154-6 (2.5 g, 73.44%) MS (ES): m/z=244.07 [M+H]⁺

Step-6, 7 Synthesis of 4-(6-chloro-2-((dimethylamino)methyl)pyridin-3-yl)tetrahydro-2H-pyran-4-ol (Intermediate AA154)

To a solution of Intermediate AA154-6 (2.5 g, 10.28 mmol) in DCM (25 mL) at 0° C. were added triethylamine (4.3 mL, 30.84 mmol, 3.0 eq) and methane sulfonyl chloride (1.6 mL, 20.56 mmol, 2.0 eq). After completion of reaction, the reaction mixture was diluted with water (50 mL) and extracted with ethyl acetate (3×30 mL). The combined organic extracts were washed with brine (40 mL), dried over Na$_2$SO$_4$, filtered, and concentrated under reduced pressure (6 g). To a solution of mesylate intermediate (6.0 g, 18.69 mmol) in acetonitrile (30 mL) with potassium carbonate (10.3 g, 74.76 mmol, 4.0 eq) was added dimethylamine hydrochloride (15 g, 186.9 mmol, 10 eq) portion wise. After stirring at 100° C. for 2 h, the reaction mixture was diluted with water (200 mL) and extracted with DCM (3×100 mL). The combined organic extracts were washed with brine (200 mL), dried over Na$_2$SO$_4$, filtered, and concentrated under reduced pressure. The residue was purified by column chromatography (25% ethyl acetate gradient in hexane) to afford Intermediate AA154 (1.0 g, 36.00%) MS (ES): m/z=271.2 [M+H]⁺

Synthesis of 6-(morpholinomethyl)-5-(THF-3-yl)pyridin-2-amine (Intermediate-AA155)

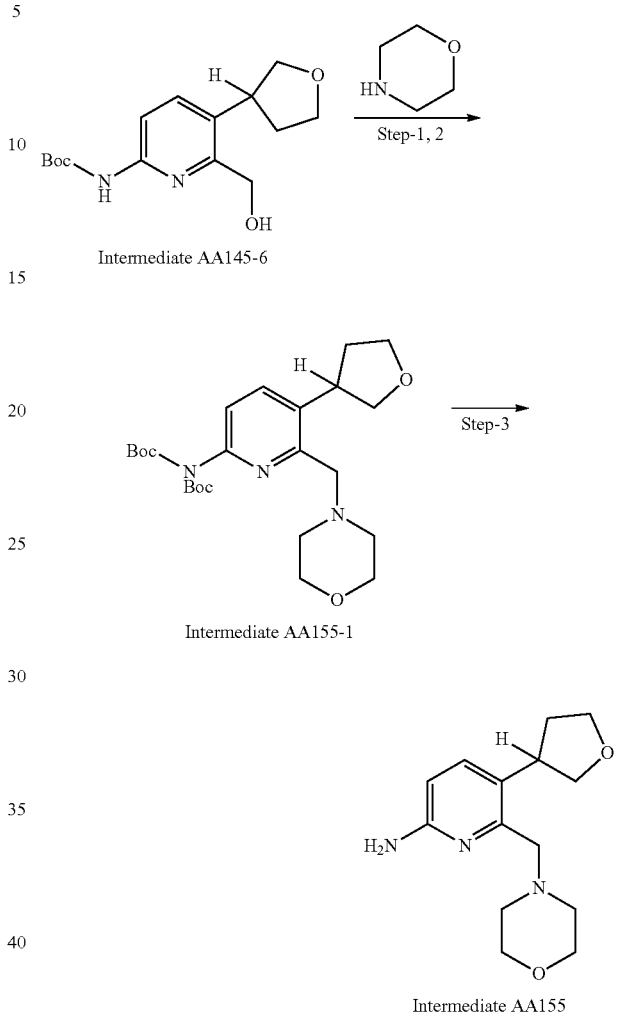

6-(morpholinomethyl)-5-(THF-3-yl)pyridin-2-amine (Intermediate-AA155) was prepared from tert-butyl (6-(hydroxymethyl)-5-(THF-3-yl)pyridin-2-yl)carbamate (Intermediate AA145-6) and morpholine in a similar fashion to that procedure of step-6, step-7 and step-8 described in synthesis of 5-cyclopentyl-6-((dimethylamino)methyl)pyridin-2-amine (Intermediate AA145) (quantitative %). m/z 264.1 [M+H]⁺

Synthesis of 6-(2-(dimethylamino)ethyl)-5-morpholinopyridin-2-amine (Intermediate-AA156)

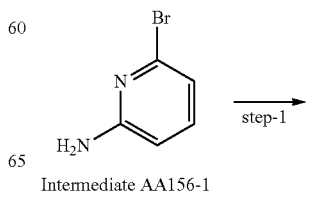

Intermediate AA156-1

-continued

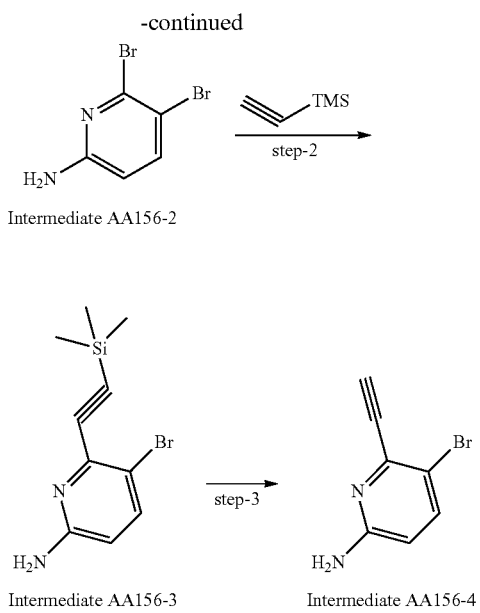

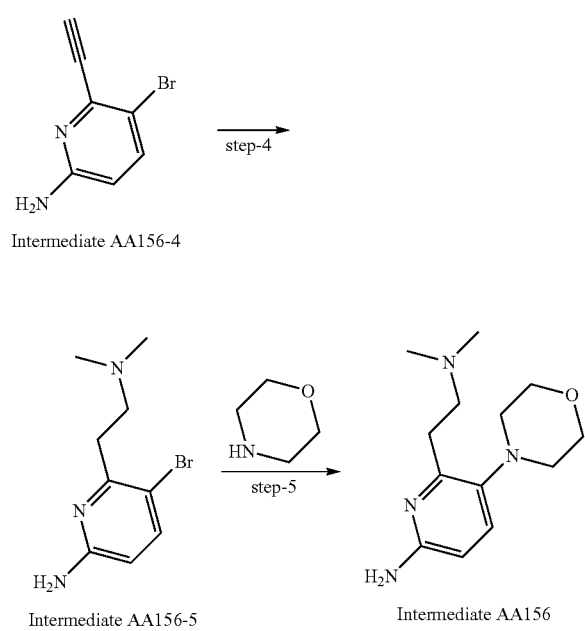

Step-1 Synthesis of 5,6-dibromopyridin-2-amine (Intermediate AA156-2)

To a cooled solution of Intermediate AA156-1 (10.0 g, 57.80 mmol) in DMF (50 mL) was added slowly N-Bromosuccinimide (11.3 g, 63.58 mmol, 1.1 eq). After stirring at RT for 16 h, the reaction mixture was diluted with water (300 mL) and extracted with ethyl acetate (3×90 mL). The combined organic extracts were washed with brine (250 mL), dried over $Na_2SO_4$, filtered, and concentrated under reduced pressure. The residue was purified by column chromatography eluting with 5-8% elution ethyl acetate in hexane to afford the title compound Intermediate AA156-2 (7.0 g, 48.08%) MS (ES): m/z=251.8 $[M+H]^+$

Step-2 Synthesis of 5-bromo-6-((trimethylsilyl)ethynyl)pyridin-2-amine (Intermediate AA156-3)

To a solution of Intermediate AA156-2 (7.0 g, 27.88 mmol) and ethynyltrimethylsilane (3.2 g, 33.45 mmol, 1.2 eq) in toluene (70 mL) was added triethylamine (11.7 mL, 83.64 mmol, 3.0 eq). After purging with nitrogen for 10-15 min, Copper (I) iodide (0.530 g, 2.78 mmol, 0.1 eq) and Bis (triphenylphosphine) palladium (II) dichloride (1.9 g, 2.78 mmol, 0.1 eq) were added. After stirring at 120° C. for 16 h, the reaction mixture was diluted with water (350 mL) and extracted with ethyl acetate (3×100 mL). The combined organic extracts were washed with brine (270 mL), dried over $Na_2SO_4$, filtered, and concentrated under reduced pressure. The residue was purified by column chromatography eluting with 22% elution ethyl acetate in hexane to afford Intermediate AA156-3 (2.5 g, 33.42%) MS (ES): m/z=270.0 $[M+H]^+$

Step-3 Synthesis of 5-bromo-6-ethynylpyridin-2-amine (Intermediate AA156-4)

To a solution of Intermediate AA156-3 (4.0 g, 14.81 mmol) in methanol (5 mL) was added slowly aqueous 2N potassium hydroxide solution (40 mL). After stirring at RT for 3 h, the reaction mixture was diluted with ice cold water (200 mL) and extracted with DCM (3×90 mL). The combined organic extracts were washed with brine, dried over $Na_2SO_4$, filtered, and concentrated under reduced pressure. The residue was purified by column chromatography eluting with 17% elution ethyl acetate in hexane to afford the title compound Intermediate AA156-4 (1.6 g, 54.65%) MS (ES): m/z=197.04 $[M+H]^+$

Step-4 Synthesis of 5-bromo-6-(2-(dimethylamino) ethyl)pyridin-2-amine (Intermediate AA156-5)

To a solution of Intermediate AA156-4 (4.5 g, 22.84 mmol) and dimethylamine (9.0 g, 114.2 mmol, 5.0 eq) in ethanol (45 mL) was added sodium cyanoborohydride (2.1 g, 34.26 mmol, 1.5 eq). After stirring at 110° C. for 16 h, the reaction mixture was concentrated under reduced pressure to afford residue which was diluted with DCM and water. The aqueous layer was basified with sodium hydroxide solution and extracted with 20% methanol in DCM (3×80 mL). The combined organic extracts were washed with brine, dried over $Na_2SO_4$, filtered, and concentrated under reduced pressure to afford Intermediate AA156-5 (4.0 g, 71.74%) MS (ES): m/z=245.04 $[M+H]^+$

Step-5 Synthesis of 6-(2-(dimethylamino) ethyl)-5-morpholinopyridin-2-amine (Intermediate AA156)

To a solution of Intermediate AA156-5 (2.0 g, 8.19 mmol) and morpholine (1.0 g, 12.29 mmol, 1.5 eq) in THF (20 mL) was added lithium bis(trimethylsilyl)amide (4.7 mL, 24.57 mmol, 3.0 eq). After purging with nitrogen gas for 10 min. $Pd_2(dba)_3$ (0.150 g, 0.16 mmol, 0.02 eq) and Xantphos (0.378 g, 0.655 mmol, 0.08 eq) were added. After stirring at 70° C. for 16 h, the reaction mixture was filtered through celite-bed. The filtrate was concentrated under reduced pressure. The residue was purified by column chromatography eluting with 10% ethyl acetate in hexane to afford the title compound Intermediate AA156 (0.9 g, 43.88%) MS (ES): m/z=251.9 $[M+H]^+$

Synthesis of Tert-Butyl ((6-amino-3-(THF-3-yl)pyridin-2-yl)methyl)(methyl)carbamate (Intermediate-AA157)

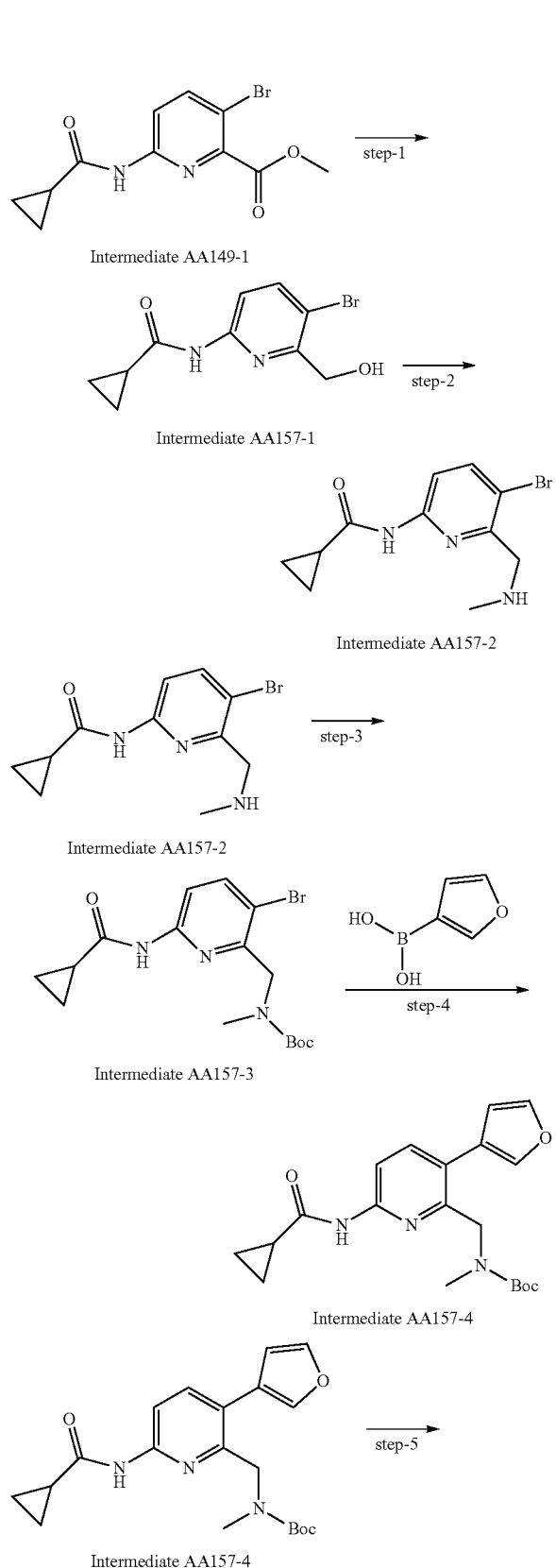

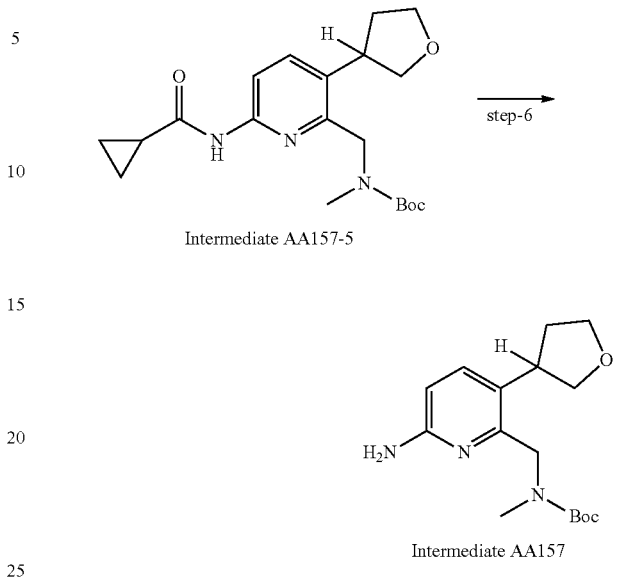

Step-1 Synthesis of N-(5-bromo-6-(hydroxymethyl)pyridin-2-yl)cyclopropanecarboxamide (Intermediate AA157-1)

To a solution of the Intermediate AA149-1 (8 g, 26.7 mmol) in ethanol (60 mL) at 0° C. was added NaBH$_4$ (3 g, 80.2 mmol, 3 eq) portion wise. After stirring at RT for 3 h, the reaction was quenched with water (100 mL) and extracted into ethyl acetate (3×40 mL). The combined organic layer was washed with brine, passed through a hydrophobic filter, and evaporated in vacuum to afford Intermediate AA157-1 (3.4 g, quantitative) which was used in the next step without purification. MS (ES): m/z 271.1 [M+1]$^+$

Step-2 Synthesis of N-(5-bromo-6-((methylamino)methyl)pyridin-2-yl)cyclopropanecarboxamide (Intermediate AA157-2)

To a solution of the Intermediate AA157-1 (3.4 g, 12.5 mmol) and N—N diisopropyl ethylamine (7.5 mL, 43.9 mmol, 3.5 eq) in acetonitrile (40 mL) at 0° C. was added methane sulfonyl chloride (1.7 mL, 21.2 mmol, 1.7 eq). After stirring for 20 min at 0° C. and then warming to RT for 40 min, the reaction was quenched with water (100 mL) and extracted into DCM (3×40 mL). The combined organic layer was washed with brine, passed through a hydrophobic filter, and concentrated under reduced pressure. The residue dissolved in acetonitrile (40 mL) was treated with monomethyl amine hydrochloride (66 mL, 133 mmol, 10.0 eq) and potassium carbonate (18 g, 133 mmol, 10.0 eq). After stirring at 80° C. for 2 h, the reaction was quenched with water (100 mL) and extracted into DCM (3×40 mL). The combined organic layer was washed with brine, passed through a hydrophobic filter, and evaporated in vacuum. The residue was purified by silica gel chromatography eluting with 30% ethyl acetate/hexane to afford Intermediate AA157-2 (2.0 g, 56.12%). MS (ES): m/z 284.1 [M+H]$^+$

Step-3 Synthesis of Tert-Butyl ((3-bromo-6-(cyclo-propanecarboxamido)pyridin-2-yl)methyl)(methyl) carbamate (Intermediate AA157-3)

To a solution of Intermediate AA157-2 (1.6 g, 5.6 mmol) in DCM (40 mL) at 0° C. was treated with di-tert-butyl dicarbonate (1.4 gm, 6.7 mmol, 1.2 eq) and DMAP (0.14 g, 1.1 mmol, 0.2 eq). After stirring at RT for 16 h, the reaction mixture was diluted ethyl acetate (20 mL) and water (15 mL). The organic layer was collected, and the aqueous phase was extracted with ethyl acetate (2×30 mL). The combined organic extracts were washed with brine (10 mL), dried over $Na_2SO_4$, filtered, and concentrated under reduced pressure to afford Intermediate AA157-3 (2.2 g, quantitative) which was used in the next step without purification, MS (ES): m/z 384.2 $[M+H]^+$

Step-4 Synthesis of Tert-Butyl ((6-(cyclopropanecarboxamido)-3-(furan-3-yl)pyridin-2-yl)methyl)(methyl)carbamate (Intermediate AA157-4)

To a solution of Intermediate AA157-3 (2.2 g, 5.7 mmol) in dioxane (20 mL) and water (5 mL) were added furan-3-ylboronic acid (0.766 g, 6.8 mmol, 1.2 eq) and potassium phosphate tribasic (3.6 g, 17.1 mmol, 3.0 eq). After degassing with $N_2$ for 15 min, X-Phos Pd G2 (0.45 g, 0.57 mmol, 0.1 eq) was added. After stirring at 100° C. for 2 h, the reaction mixture was cooled at RT and diluted with ethyl acetate (20 mL) and water (20 mL). The organic layer was collected, and the aqueous phase was extracted with ethyl acetate (2×30 mL) The combined organic extracts were washed with brine (20 mL), dried over $Na_2SO_4$, filtered, and concentrated under reduced pressure. The residue was purified by column chromatography eluting with 35% ethyl acetate gradient in hexane to afford Intermediate AA157-4 (2 g, 94%), MS (ES): m/z 371.4 $[M+H]^+$

Step-5 Synthesis of Tert-Butyl ((6-(cyclopropanecarboxamido)-3-(THF-3-yl)pyridin-2-yl)methyl)(methyl)carbamate (Intermediate AA157-5)

To a solution of Intermediate AA157-4 (2 g, 5.31 mmol) in MeOH:THF (15:15 mL) at RT was added Pd(OH)$_2$(1.5 g), ammonium formate (1.4 g, 21.5 mmol, 4.0 eq), and acetic acid (0.5 mL). After stirring at RT for 3 h with $H_2$ gas at atmospheric pressure, the reaction mixture was filtrate through celite bed. The organic layer was evaporated in vacuum to afford Intermediate AA157-5 (3 g, quantitative) which was used in the next step without purification. MS (ES): m/z 375.4 [M+1]+

Step-6 Synthesis of Tert-Butyl ((6-amino-3-(THF-3-yl)pyridin-2-yl)methyl)(methyl)carbamate (Intermediate AA157)

To a solution Intermediate AA157-5 (3 g, 8 mmol) in MeOH (15 mL) and $H_2O$ (15 mL) was added NaOH (3.2 g, 8 mmol). After stirring at 70° C. for 2 h, the reaction mixture was evaporated in vacuum, quenched with water (30 mL), and extracted by ethyl acetate (3×40 mL). The combined organic layer was evaporated in vacuum to afford Intermediate AA157 (1.5 g, quantitative) which was used in the next step without purification. MS (ES): m/z 307.19 [M+1]+

Synthesis of 1-(6-aminopyridin-2-yl)-4-(azetidin-1-yl)pyrrolidin-2-one (Intermediate AA158)

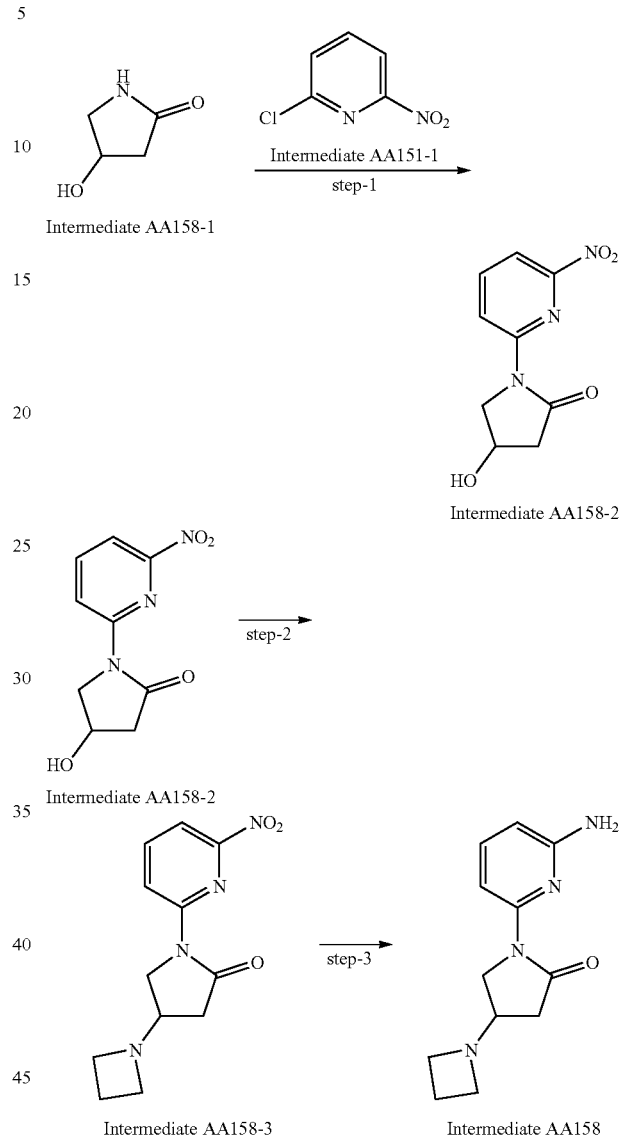

Step-1 Synthesis of 4-hydroxy-1-(6-nitropyridin-2-yl)pyrrolidin-2-one (Intermediate AA158-2)

To a solution of Intermediate AA158-1 (4 g, 39.5 mmol) and Intermediate-AA51-1 (6.3 g, 39.5 mmol) in 1, 4-dioxane (100 mL) was added $Cs_2CO_3$ (19.4 g, 59.3 mmol, 1.5 eq). After degassing under $N_2$ stream for 15 min, Pd$_2$(dba)$_3$ (1.8 g, 1.9 mmol, 0.05 eq) and Xantphos (2.3 g, 3.9 mmol, 0.1 eq) were added. After stirring at 100° C. and for 4 h, the reaction mixture was cooled at RT and diluted with water (50 mL) and 10% MeOH in DCM (100 mL). The organic layer was collected, and the aqueous phase was extract with 10% MeOH in DCM (300 mL). The combined organic extracts were washed with brine (200 mL), dried over $Na_2SO_4$, filtered, and concentrated under reduced pressure. The residue was purified by column chromatography (70% ethyl acetate gradient in hexane). The residue obtained was then triturated with diethyl ether and the resulting solid was collected by filtration to afford the title compound Intermediate AA158-2 (1 g, 11%). MS (ES): m/z=223.1 [M+2]+

Step-2 Synthesis of 4-(azetidin-1-yl)-1-(6-nitropyridin-2-yl)pyrrolidin-2-one (Intermediate AA158-3)

To a solution of the Intermediate AA158-2 (1 g, 4.5 mmol) and N—N diisopropyl ethylamine (0.59 g, 5.8 mmol, 1.3 eq) in DCM (10 mL) at 0° C. was added methane sulfonyl chloride (0.67 g, 5.6 mmol, 1.3 eq). After stirring at RT stirred for 4 h, the reaction was quenched with water (100 mL) and extracted into DCM (3×40 mL). The combined organic layer was washed with brine, passed through a hydrophobic filter, and concentrated under reduced pressure. The residue was then dissolved in DMF (6 mL), and treated with azetidine (0.4 g, 6.9 mmol, 1.5 eq). After stirring at 130° C. for 4 h in microwave, the reaction was quenched with water (100 mL) and extracted into ethyl acetate (3×40 mL). The combined organic layer was washed with brine, passed through a hydrophobic filter, and concentrated under reduced pressure. The residue was purified by silica gel chromatography using 30% ethyl acetate gradient in hexane to afford Intermediate AA158-3 (0.180 g, 12%). MS (ES): m/z 262 [M+H]$^+$ Step-3 Synthesis of 1-(6-aminopyridin-2-yl)-4-(azetidin-1-yl)pyrrolidin-2-one (Intermediate AA158)

To a solution of Intermediate AA158-3 (0.18 g) in THF (8 mL) was added 10% Pd/c (0.05 g). After stirring at RT for 16 h with H$_2$ gas at atmospheric pressure, the reaction mixture was filtered through celite bed. The organic layer was evaporated in vacuum to afford Intermediate AA158 (0.18 g, quantitative) which was used in the next step without purification. MS (ES): m/z 232 [M+1]$^+$ Synthesis of 5-(2-(2-(cyclopropylamino)propan-2-yl)morpholino)pyridin-2-amine (Intermediate AA159)

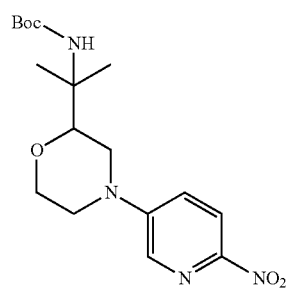

Intermediate AA130-3

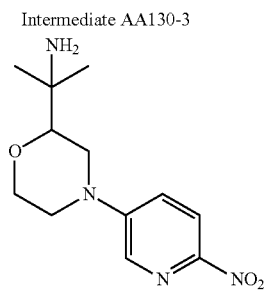

Intermediate AA159-1

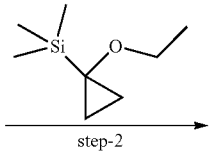

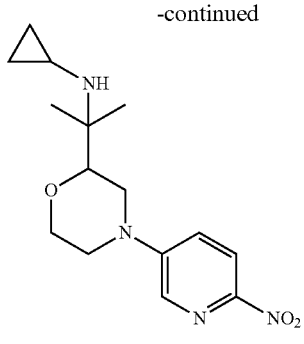

Intermediate AA159-2

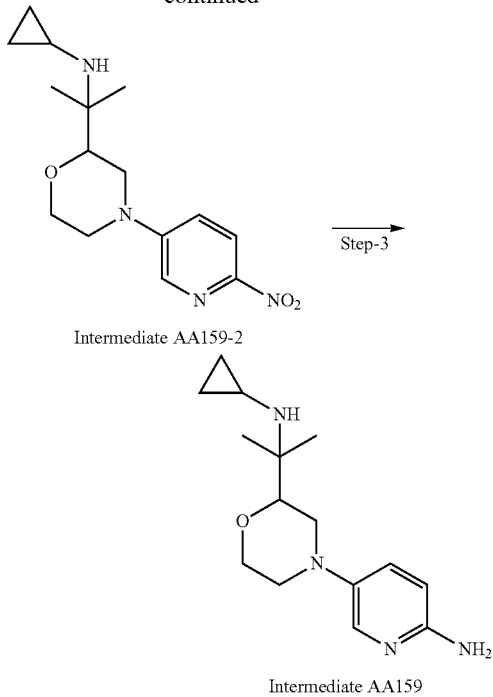

Intermediate AA159

Step-1 Synthesis of 2-(4-(6-nitropyridin-3-yl)morpholin-2-yl)propan-2-amine (Intermediate AA159-1)

To a solution of Intermediate AA130-3 (2.5 g, 6.62 mmol) in DCM (20 mL) was added 4M HCL in dioxane (2 mL). After stirring at RT for 30 min, the reaction mixture was diluted with ice water (50 mL) and extracted with ethyl acetate (3×30 mL). The combined organic layer was washed with brine solution, dried over sodium sulfate, and concentrated under reduced pressure. The residue was purified by trituration using diethyl ether and pentane to afford Intermediate AA159-1 (1.5 g, 82%). MS (ES): m/z 267.1 [M+H]$^+$.

Step-2 Synthesis of N-(2-(4-(6-nitropyridin-3-yl)morpholin-2-yl)propan-2-yl)cyclopropanamine (Intermediate AA159-2)

To a solution of Intermediate AA159-1 (1.4 g, 5.26 mmol) in methanol (20 mL) with acetic acid (0.28 mL) and (1-ethoxycyclopropoxy)trimethylsilane (1.1 mL, 5.78 mmol, 1.1 eq). at 0° C. was added sodium cyanoborohydride added portion wise (1.65 g, 26.3 mmol, 5.0 eq). After stirring at 60° C. for 16 h, the reaction mixture was quenched with sodium bicarbonate solution and extracted with DCM (3×50 mL). The combined organic layer was washed with brine solution, dried over sodium sulfate, and concentrated under reduced pressure. The residue was purified by column chromatography eluting with 1.5% methanol in DCM to afford Intermediate AA159-2 (1.2 g, 74.51%). MS (ES): m/z 307.1 [M+H]$^+$.

Step-3. 5-(2-(2-(cyclopropylamino)propan-2-yl)morpholino)pyridin-2-amine (Intermediate AA159)

To a solution of Intermediate AA159-2 (1.4 g, 3.92 mmol) in methanol (20 mL). was added 10% Pd/c (0.7 g) After stirring at RT for 1 h with H₂ gas at atmospheric pressure, the reaction mixture was filtered through celite-bed and washed with 10% methanol DCM. The filtrate was concentrated under reduced pressure to afford Intermediate AA159 (1.0 g, 92.37%). MS (ES): m/z 277.2 [M+H]⁺

Synthesis of 6-(((2-methoxyethyl)(methyl)amino) methyl)-5-(THF-3-yl)pyridin-2-amine (Intermediate-AA160)

Synthesis of 6-((isopropyl(methyl)amino)methyl)-5-(THF-3-yl)pyridin-2-amine (Intermediate-AA161)

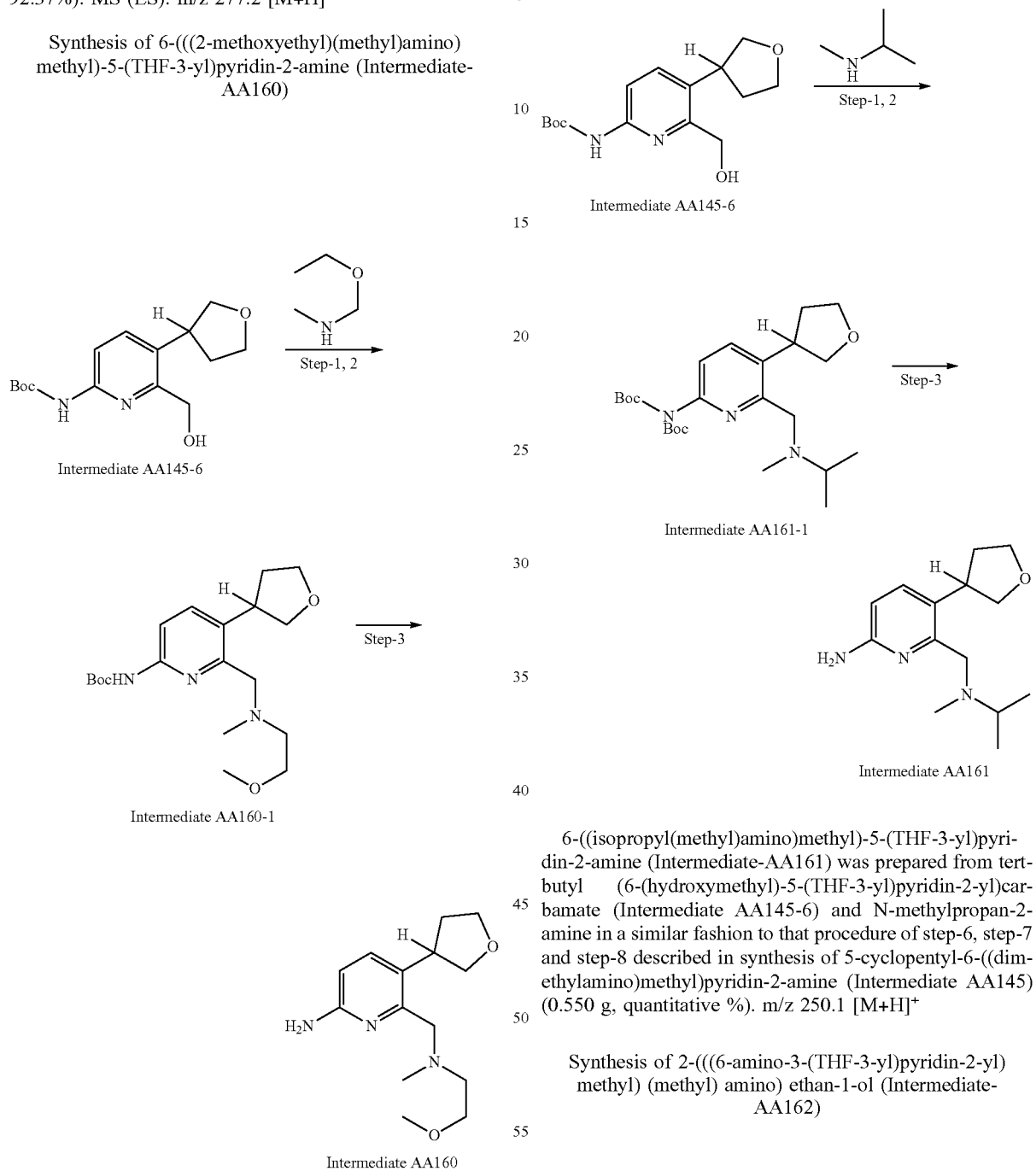

6-(((2-methoxyethyl)(methyl)amino)methyl)-5-(THF-3-yl)pyridin-2-amine (Intermediate-AA160) was prepared from tert-butyl (6-(hydroxymethyl)-5-(THF-3-yl)pyridin-2-yl)carbamate (Intermediate AA145-6) and 2-methoxy-N-methylethan-1-amine in a similar fashion to that procedure of step-6, step-7 and step-8 described in synthesis of 5-cyclopentyl-6-((dimethylamino)methyl)pyridin-2-amine (Intermediate AA145) (0.550 g, quantitative %). m/z 266.1 [M+H]⁺

6-((isopropyl(methyl)amino)methyl)-5-(THF-3-yl)pyridin-2-amine (Intermediate-AA161) was prepared from tert-butyl (6-(hydroxymethyl)-5-(THF-3-yl)pyridin-2-yl)carbamate (Intermediate AA145-6) and N-methylpropan-2-amine in a similar fashion to that procedure of step-6, step-7 and step-8 described in synthesis of 5-cyclopentyl-6-((dimethylamino)methyl)pyridin-2-amine (Intermediate AA145) (0.550 g, quantitative %). m/z 250.1 [M+H]⁺

Synthesis of 2-(((6-amino-3-(THF-3-yl)pyridin-2-yl) methyl) (methyl) amino) ethan-1-ol (Intermediate-AA162)

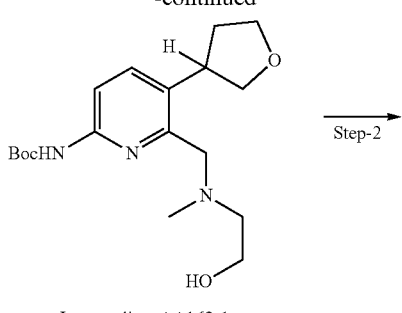

Intermediate AA162-1

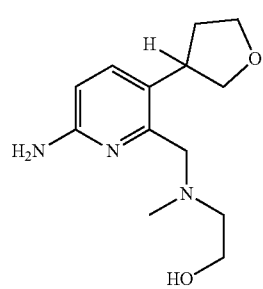

Intermediate AA162

2-(((6-amino-3-(THF-3-yl)pyridin-2-yl)methyl)(methyl) amino)ethan-1-ol (Intermediate-AA162) was prepared from tert-butyl (6-(hydroxymethyl)-5-(THF-3-yl)pyridin-2-yl) carbamate (Intermediate AA145-6) and 2-(methylamino) ethan-1-ol in a similar fashion to that procedure of step-6, step-7 and step-8 described in synthesis of 5-cyclopentyl-6-((dimethylamino)methyl)pyridin-2-amine (Intermediate AA145) (0.8 g, quantitative %). m/z 252.1 [M+H]$^+$ Synthesis of 6-(((S)-3-fluoropyrrolidin-1-yl) methyl)-5-(THF-3-yl)pyridin-2-amine (Intermediate-AA163)

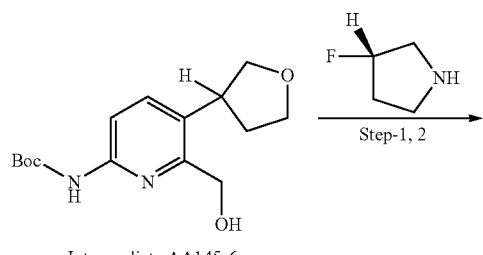

Intermediate AA145-6

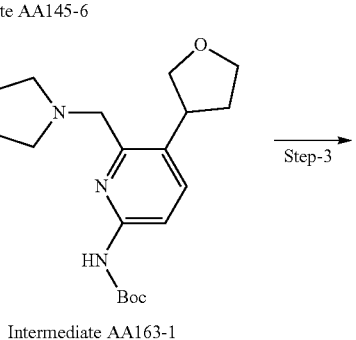

Intermediate AA163-1

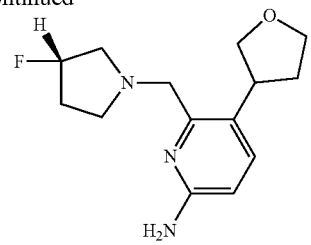

Intermediate AA163

6-(((S)-3-fluoropyrrolidin-1-yl)methyl)-5-(THF-3-yl) pyridin-2-amine (Intermediate-AA163) was prepared from tert-butyl (6-(hydroxymethyl)-5-(THF-3-yl)pyridin-2-yl) carbamate (Intermediate AA145-6) and (S)-3-fluoropyrrolidine in a similar fashion to that procedure of step-6, step-7 and step-8 described in synthesis of 5-cyclopentyl-6-((dimethylamino)methyl)pyridin-2-amine (Intermediate AA145) (0.8 g, quantitative %). m/z 265.3 [M+H]$^+$ Synthesis of 6-((cyclopropyl(methyl)amino)methyl)-5-(THF-3-yl)pyridin-2-amine (Intermediate-AA164)

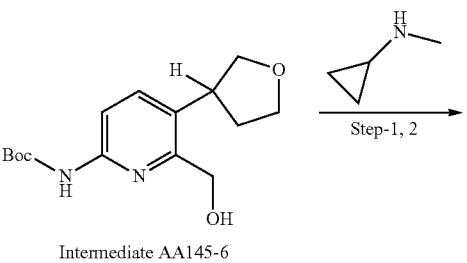

Intermediate AA145-6

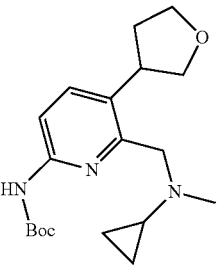

Intermediate AA164-1

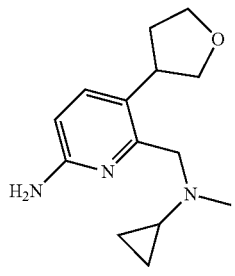

Intermediate AA164

6-((cyclopropyl(methyl)amino)methyl)-5-(THF-3-yl) pyridin-2-amine (Intermediate-AA164) was prepared from tert-butyl (6-(hydroxymethyl)-5-(THF-3-yl)pyridin-2-yl) carbamate (Intermediate AA145-6) and N-methylcyclopropanamine in a similar fashion to that procedure of step-6, step-7 and step-8 described in synthesis of 5-cyclopentyl- 6-((dimethyl amino)methyl)pyridin-2-amine (Intermediate AA145) (0.75 g, 78.42%). m/z 248.1 [M+H]⁺

Synthesis of Tert-Butyl ((6-amino-3-(THF-3-yl)
pyridin-2-yl)methyl)(2,2-difluoroethyl)carbamate
(Intermediate-AA165)

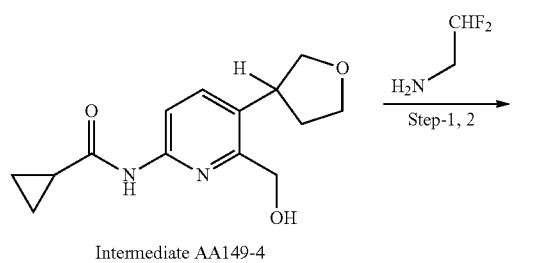

Intermediate AA149-4

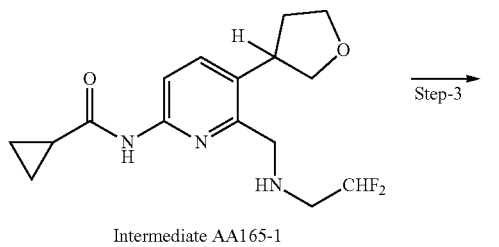

Intermediate AA165-1

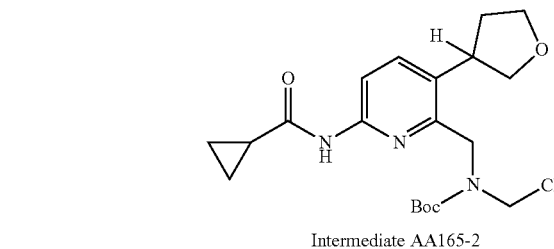

Intermediate AA165-2

Step-1,2 Synthesis of N-(6-(((2,2-difluoroethyl)
amino)methyl)-5-(THF-3-yl)pyridin-2-yl)cyclopropanecarboxamide (Intermediate AA165-1)

To a solution of the Intermediate AA149-4 (4 g, 15.2 mmol) and N—N diisopropyl ethylamine (7.8 mL, 45.78 mmol, 3.0 eq) in acetonitrile (40 mL) at 0° C. was added methane sulfonyl chloride (1.7 mL, 22.89 mmol, 1.5 eq). After stirring for 20 min warming to RT and then stirring for 40 min, the reaction was quenched with water (300 mL) and extracted with DCM (3×100 mL). The combined organic layer was washed with brine, passed through a hydrophobic filter, and concentrated under reduced pressure. To the residue dissolved in acetonitrile (40 mL) were added 2,2-difluoroethan-1-amine (6.1 g, 76.3 mmol, 5.0 eq) and potassium carbonate (16.8 g, 122.08 mmol, 8.0 eq). After stirring at 80° C. for 16 h, the reaction mixture was filtered through a celite bed, and the filtrate was concentrated under reduced pressure. The residue was purified by silica gel chromatography eluting with 15% ethyl acetate in hexane to afford Intermediate AA165-1 (2.2 g, 44.34%) as a yellow oil. MS (ES): m/z 326.2 [M+H]⁺

Step-3 Synthesis of Tert-Butyl ((6-(cyclopropanecarboxamido)-3-(THF-3-yl)pyridin-2-yl)methyl)(2,2-difluoroethyl)carbamate (Intermediate AA165-2)

To a solution of Intermediate AA165-1 (2.4 g, 6.76 mmol) in DCM (25 mL) with triethylamine (2.8 g, 20.3 mmol, 3.0 eq) at 0° C. was added di-tert-butyl dicarbonate (4.4 g, 20.28 mmol, 3.0 eq). After stirring at RT for 5 h, the reaction mixture was diluted with ethyl acetate (100 mL) and water (50 mL). The organic layer was collected, and the aqueous phase was extracted with ethyl acetate (3×50 mL). The combined organic extracts were washed with brine (40 mL), dried over Na₂SO₄, filtered, and concentrated under reduced pressure. The residue was purified by column chromatography eluting with 20% ethyl acetate in hexane to afford the title compound Intermediate AA165-2 (1.5 g, 52.14%) as a brown solid. MS (ES): m/z=426.2 [M+H]⁺.

Step-4 Synthesis of Tert-Butyl ((6-amino-3-(THF-3-yl)pyridin-2-yl)methyl)(2,2-difluoroethyl)carbamate (Intermediate AA165)

To a solution of Intermediate AA165-2 (1.5 g, 3.52 mmol) in methanol: water (20 mL:5 mL) was added sodium hydroxide (1.6 g, 42.25 mmol, 12 eq). After stirring at RT for 16 h, the reaction mixture was concentrated under reduced pressure. The residue was treated with water (30 mL), neutralized with 1N hydrochloric acid to pH-6-6.5 at 10° C. and extracted with DCM (3×30 mL). The combined organic layer was washed with brine solution, dried over sodium sulfate, and concentrated under reduced pressure to afford Intermediate AA165 (1.2 g, quantitative). MS (ES): m/z 358.3 [M+H]⁺

Synthesis of 6-(((R)-3-fluoropyrrolidin-1-yl)
methyl)-5-(THF-3-yl)pyridin-2-amine (Intermediate-AA166)

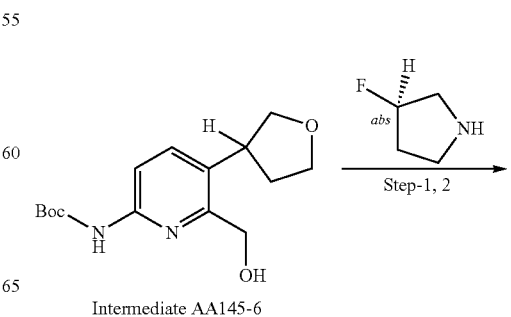

Intermediate AA145-6

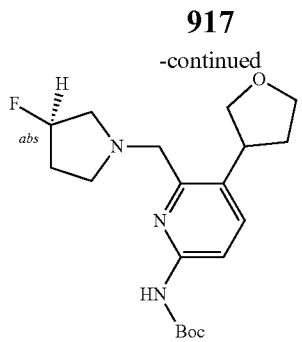

Intermediate AA166-1

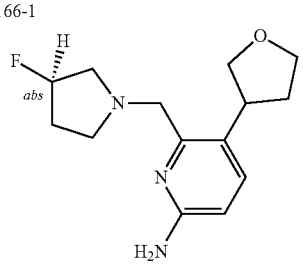

Intermediate AA166

6-(((R)-3-fluoropyrrolidin-1-yl)methyl)-5-(THF-3-yl) pyridin-2-amine (Intermediate-AA166) was prepared from tert-butyl (6-(hydroxymethyl)-5-(THF-3-yl)pyridin-2-yl) carbamate (Intermediate AA145-6) and (R)-3-fluoropyrrolidine in a similar fashion to that procedure of step-6, step-7 and step-8 described in synthesis of 5-cyclopentyl-6-((dimethylamino)methyl)pyridin-2-amine (Intermediate AA145) (0.75 g, quantitative %). m/z 266.1 [M+H]⁺

Synthesis of 6-((methyl(oxetan-3-yl)amino)methyl)-5-(THF-3-yl)pyridin-2-amine (Intermediate-AA167)

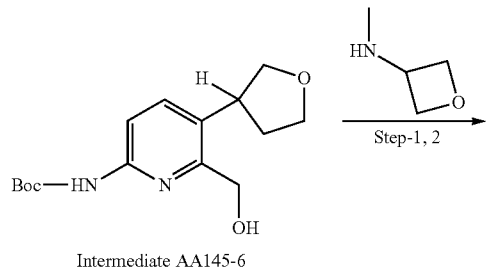

Intermediate AA145-6

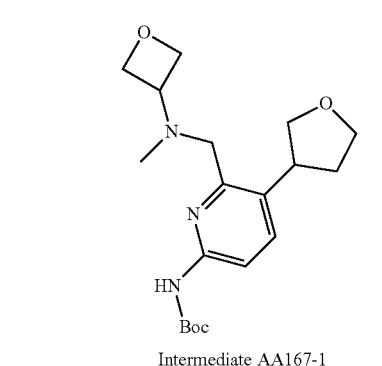

Intermediate AA167-1

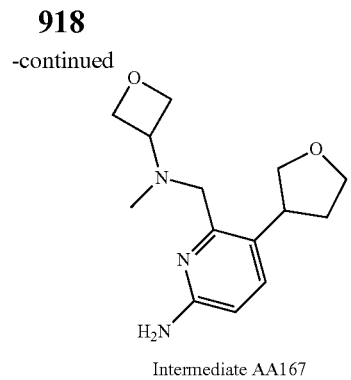

Intermediate AA167

6-((methyl(oxetan-3-yl)amino)methyl)-5-(THF-3-yl) pyridin-2-amine (Intermediate-AA167) was prepared from tert-butyl (6-(hydroxymethyl)-5-(THF-3-yl)pyridin-2-yl) carbamate (Intermediate AA145-6) and N-methyloxetan-3-amine in a similar fashion to that procedure of step-6, step-7 and step-8 described in synthesis of 5-cyclopentyl-6-((dimethylamino)methyl)pyridin-2-amine (Intermediate AA145) (0.650 g, quantitative %). m/z 264.1 [M+H]⁺

Synthesis of 2-(1-(6-chloro-2-((dimethylamino) methyl)pyridin-3-yl)piperidin-3-yl)propan-2-ol (Intermediate AA168)

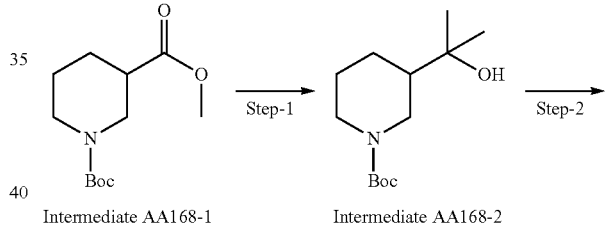

Intermediate AA168-1    Intermediate AA168-2

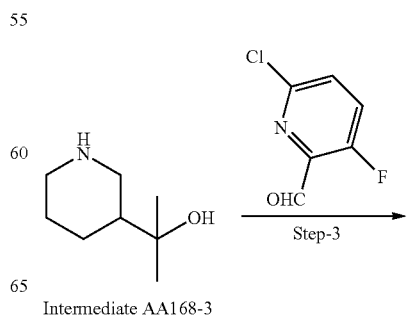

Intermediate AA168-3

Intermediate AA168-3

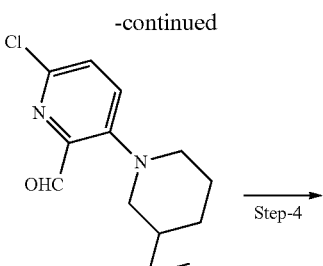

Intermediate AA168-4

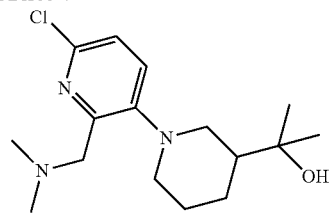

Intermediate AA168

Step-1 Synthesis of Tert-Butyl 3-(2-hydroxypropan-2-yl)piperidine-1-carboxylate (Intermediate AA168-2)

To a solution of Intermediate AA168-1 (5.0 g, 20.57 mmol) in THF (50 mL) at 0° C. was added methyl magnesium bromide 3M solution in diethyl ether (50 mL). After stirring at 0° C. for 15-20 min, the reaction mixture was quenched slowly in water (200 mL) and extracted with ethyl acetate (3×70 mL). The combined organic layer was washed with brine solution, dried over sodium sulfate, and concentrated under reduced pressure. The residue was purified by column chromatography eluting with 30% ethyl acetate in hexane to afford Intermediate AA168-2 (5.0 g, 99.98%). MS (ES): m/z 244.1 [M+H]$^+$.

Step-2 Synthesis of 2-(piperidin-3-yl)propan-2-ol (Intermediate AA168-3)

To a solution of Intermediate AA168-2 (5.0 g, 20.57 mmol) in DCM (50 mL) was added trifluoroacetic acid (5 mL). After stirring at RT for 1 h, the reaction mixture was concentrated under reduced pressure, diluted with sodium bicarbonate solution, and extracted with ethyl acetate (3×40 mL). The combined organic layer was washed with brine solution, dried over sodium sulfate, and concentrated under reduced pressure to afford Intermediate AA168-3 (5.0 g, quantitative %). MS (ES): m/z 144.1 [M+H]$^+$.

Step-3 Synthesis of 5-chloro-2-(3-(2-hydroxypropan-2-yl)piperidin-1-yl)benzaldehyde (Intermediate AA168-4)

To a solution of 6-chloro-3-fluoropicolinaldehyde (1.0 g, 6.28 mmol) and Intermediate AA168-3 (2.6 g, 18.84 mmol, 3.0 eq) and in DMF (10 mL) was added potassium carbonate (4.3 g, 31.4 mmol, 5.0 eq). After stirring at 100° C. for 1 h, the reaction mixture was cooled to RT, diluted with ice cold water (80 mL) and extracted with ethyl acetate (3×40 mL). The combined organic layer was washed with brine solution, dried over sodium sulfate, and concentrated under reduced pressure. The residue was purified by column chromatography eluting with 20% ethyl acetate in hexane to afford Intermediate AA168-4 (1.5 g, 84.63%). MS (ES): m/z 282.1 [M+H]$^+$.

Step-4 Synthesis of 2-(1-(6-chloro-2-((dimethylamino)methyl)pyridin-3-yl)piperidin-3-yl)propan-2-ol (Intermediate AA168)

To a solution of Intermediate AA168-4 (1.5 g, 5.33 mmol) in 1, 2-dichloroethane (20 mL) was added acetic acid (2 mL) at 0° C. Dimethylamine gas was purged in reaction mixture for 1 h. Then Sodium triacetoxyborohydride (10.0 g) was added portion wise into the reaction mixture. After stirring at RT for 16 h, the reaction mixture was diluted with water (100 mL) and extracted with DCM (3×50 mL). The combined organic layer was washed with brine solution, dried over sodium sulfate, and concentrated under reduced pressure. The residue was purified by column chromatography eluting with 6% ethyl acetate in hexane to afford Intermediate AA168 (0.9 g, 54.40%). MS (ES): m/z 312.2 [M+H]$^+$ Synthesis of 4-(2-(6-chloropyridin-3-yl)propan-2-yl)morpholine (Intermediate AA169)

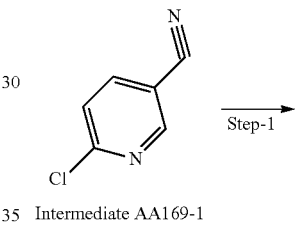

Intermediate AA169-1

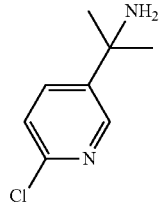 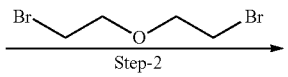

Intermediate AA169-2

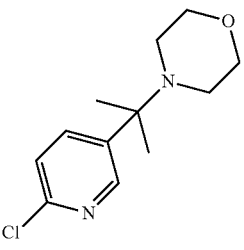

Intermediate AA169

Step-1 Synthesis of 2-(6-chloropyridin-3-yl)propan-2-amine (Intermediate AA169-2)

To freshly dried cerium (III) chloride (35.6 g) (dried at 140° C. for 4 h under vacuum) was added at RT dry THF (450 mL) under argon. After stirring at RT for 16 h, the reaction mixture was cool at −78° C. and MeLi (120 mL) was added dropwise. After stirring at −78° C. for 2 h, 6-chloronicotinonitrile (2 g) in THF was added at −78° C. After stirring at −78° C. for 2 h, the reaction mixture was diluted with water (50 mL) and 10% MeOH in DCM (100 mL). The organic layer was collected, and the aqueous phase was extract with 10% MeOH in DCM (300 mL). The combined organic extracts were washed with brine (200 mL), dried over Na$_2$SO$_4$, filtered, and concentrated under reduced pressure. The residue was purified by column chromatography (2% MeOH gradient in DCM) to afford Intermediate AA169-2 (1.5 g, 61%). MS (ES): m/z=170.6 [M+2]$^+$ Step-2 Synthesis of 4-(2-(6-chloropyridin-3-yl)propan-2-yl)morpholine (Intermediate AA169)

To a solution of Intermediate AA169-2 (1.5 g, 8.7 mmol)) in DMF (10 mL) were added 1-bromo-2-(2-bromoethoxy) ethane (3.5 g, 14.9 mmol, 1.7 eq) and N—N diisopropyl ethylamine (3.4 g, 26.3 mmol, 3 eq). After stirring at 120° C. for 16 h, the reaction was quenched with water (100 mL) and extracted into ethyl acetate (3×40 mL). The combined organic layer was washed with brine, passed through a hydrophobic filter, and concentrated under reduced pressure. The residue was purified by silica gel chromatography using 100% DCM to afford Intermediate AA169 (1.2 g, 56%). MS (ES): m/z 240.7 [M+H]$^+$ Synthesis of Tert-Butyl ((6-amino-3-(THF-3-yl) pyridin-2-yl)methyl)(2,2,2-trifluoroethyl)carbamate (Intermediate-AA171)

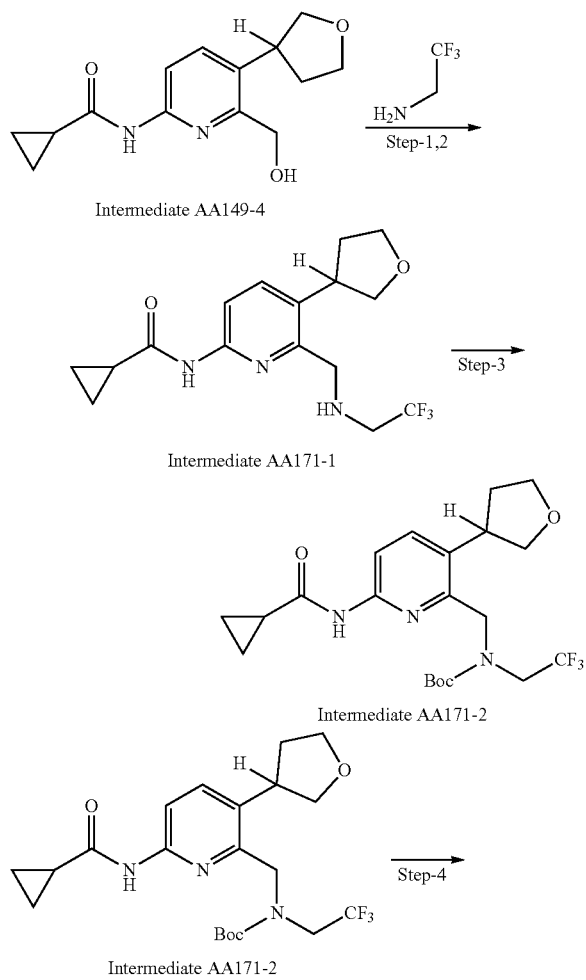

Intermediate AA149-4

Intermediate AA171-1

Intermediate AA171-2

Intermediate AA171-2

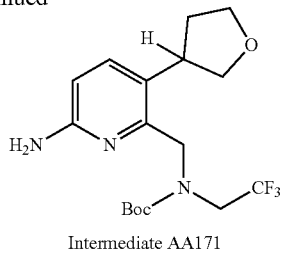

Intermediate AA171

Step-1, 2 Synthesis of N-(5-(THF-3-yl)-6-4(2,2,2-trifluoroethyl)amino)methyl)pyridin-2-yl)cyclopropanecarboxamide (Intermediate AA171-1)

To a solution of Intermediate AA145-6 (4 g, 15.2 mmol) and N—N diisopropyl ethylamine (7.8 mL, 45.78 mmol, 3.0 eq) in acetonitrile (40 mL) at 0° C. was added methane sulfonyl chloride (1.7 mL, 22.89 mmol, 1.5 eq). After stirring for 20 min warming to RT and stirring for 40 min at RT, the reaction was quenched with water (300 mL) and extracted into DCM (3×100 mL). The combined organic layer was washed with brine, passed through a hydrophobic filter, and concentrated under reduced pressure. The residue was then dissolved in acetonitrile (40 mL), and treated with 2,2,2-trifluoroethan-1-amine (7.5 g, 76.3 mmol, 5.0 eq) and potassium carbonate (16.8 g, 122.08 mmol, 8.0 eq). After stirring at 80° C. for 16 h, the reaction mixture was filtered through a celite bed, and the filtrate was concentrated under reduced pressure. The residue was purified by silica gel chromatography using 15% ethyl acetate in hexane to afford Intermediate AA171-1 (2.4 g, 45.84%) as a yellow oil. MS (ES): m/z 344.2 [M+H]$^+$ Step-3 synthesis of tert-butyl ((6-(cyclopropanecarboxamido)-3-(THF-3-yl)pyridin-2-yl)methyl)(2,2,2-trifluoroethyl)carbamate (Intermediate AA171-2)

To a solution of Intermediate AA171-1 (2.4 g, 6.97 mmol) in DCM (25 mL) with triethylamine (2.9 g, 20.91 mmol, 3.0 eq) at 0° C. was added di-tert-butyl dicarbonate (4.5 g, 20.9 mmol, 3.0 eq). After stirring at RT for 5 h, the reaction mixture was diluted with ethyl acetate (100 mL) and water (50 mL). The organic layer was collected, and the aqueous phase was extracted with ethyl acetate (3×50 mL). The combined organic extracts were washed with brine (40 mL), dried over Na$_2$SO$_4$, filtered, and concentrated under reduced pressure. The residue was purified by column chromatography eluting with 25% ethyl acetate in hexane to afford the title compound Intermediate AA171-2 (1.5 g, 48.39%) as a brown solid. MS (ES): m/z=444.3 [M+H]$^+$.

Step-4 Synthesis of Tert-Butyl ((6-amino-3-(THF-3-yl)pyridin-2-yl)methyl)(2,2,2-trifluoroethyl)carbamate (Intermediate AA171)

To a solution of Intermediate AA171-2 (1.2 g, 2.70 mmol) in methanol:water (20 mL:5 mL) was added sodium hydroxide (1.3 g, 32.50 mmol, 12 eq). After stirring at RT for 16 h, the reaction mixture was concentrated under reduced pressure. The residue was dissolved in water (30 mL), neutralized with 1N hydrochloric acid to pH-6.5 and extracted with DCM (3×30 mL). The combined organic layer was washed with brine solution, dried over sodium sulfate, and concentrated under reduced pressure to afford Intermediate AA171 (1.3 g, quantitative %). MS (ES): m/z 376.4 [M+H]⁺

Synthesis of 6-(azetidin-1-ylmethyl)-5-(THF-3-yl) pyridin-2-amine (Intermediate-AA173)

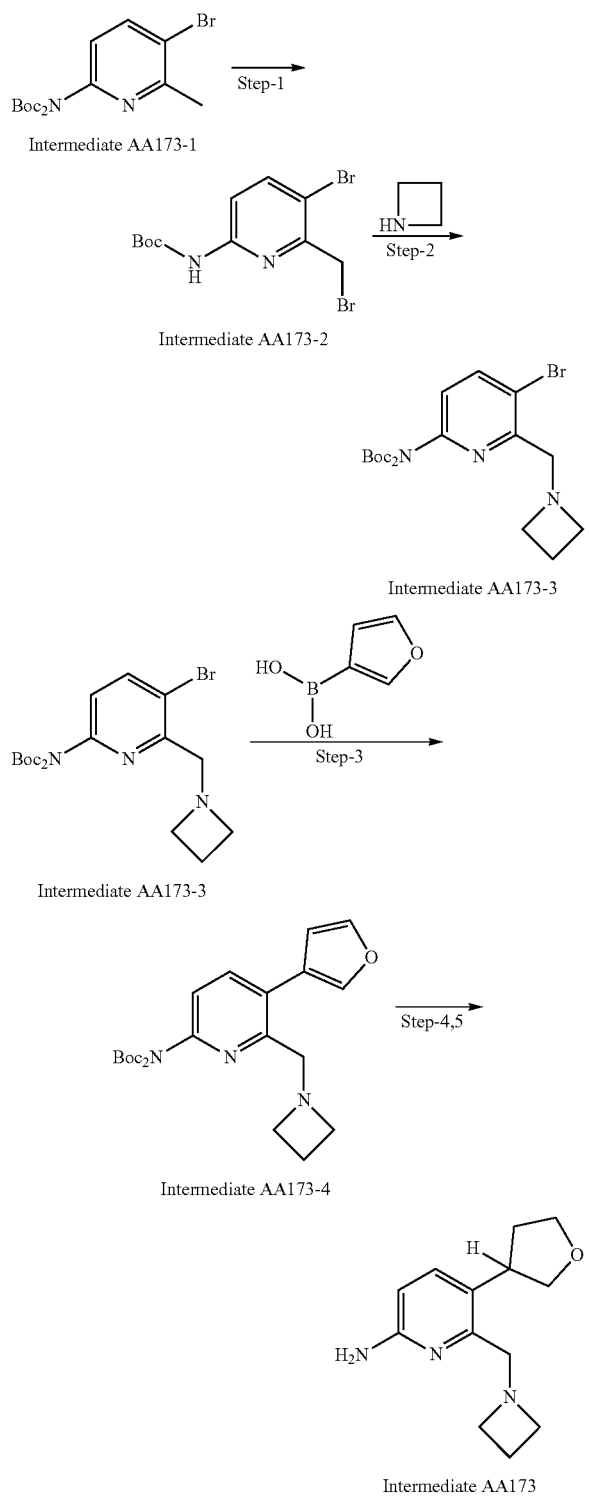

Step-1 Synthesis of Tert-Butyl (5-bromo-6-(bromomethyl)pyridin-2-yl)carbamate (Intermediate AA173-2)

To a solution of the Intermediate-AA173-1 (12 g, 31.08 mmol) in carbon tetrachloride (20 mL) were added N-bromosuccinimide (6.6 g, 37.29 mmol, 1.2 eq) and benzoyl peroxide (0.752 g, 3.10 mmol, 0.1 eq). After stirring at 100° C. for 3 h, the reaction mixture was cooled to RT, diluted with water (500 mL), and extracted into DCM (4×100 mL). The combined organic extracts were washed with brine (200 mL), dried over $Na_2SO_4$, filtered, and concentrated under reduced pressure to afford Intermediate AA173-2 (5 g, quantitative %) which was used in the next step without further purification as a yellow oil. MS (ES): m/z 367.94 [M+H]⁺

Step-2 Synthesis of Tert-Butyl (6-(azetidin-1-ylmethyl)-5-bromopyridin-2-yl) carbamate (Intermediate AA173-3)

To a solution of Intermediate AA173-2 (5.0 g, 8.19 mmol) in DMF (30 mL) were added azetidine (1.1 g, 20.47 mmol, 2.5 eq) and potassium carbonate (3.3 g, 24.57 mmol, 3.0 eq). After stirring at 100° C. for 2 h, reaction mixture was cooled to RT, diluted with ice cold water (250 mL) and extracted into DCM (3×100 mL). The combined organic extracts were washed with brine (100 mL), dried over $Na_2SO_4$, filtered, and concentrated under reduced pressure. The residue was purified by column chromatography eluting with 3% elution methanol in DCM to afford Intermediate AA173-3 (3.5 g, 73.77%) MS (ES): m/z 341.07 [M+H]⁺.

Step-3 synthesis of tert-butyl (6-(azetidin-1-ylmethyl)-5-(furan-3-yl)pyridin-2-yl)carbamate (Intermediate AA173-4)

To a solution of Intermediate AA173-3 (3.5 g, 7.91 mmol) in 1, 4-dioxane: water (35 mL: 7 mL) was added furan-3-ylboronic acid (1.3 g, 11.86 mmol, 1.5 eq), $Cs_2CO_3$ (1.5 g, 4.74 mmol, 3.0 eq) and potassium phosphate tribasic (5.0 g, 23.73 mmol, 3.0 eq). After degassing under $N_2$ stream for 15 min, Xphose PdG2, (0.621 g, 0.791 mmol, 0.1 eq) was added. After stirring at 100° C. for 30 min microwave, the reaction mixture was cooled to RT, diluted water (100 mL) and extracted with ethyl acetate (40 mL). The organic layer was collected, and the aqueous phase was extracted with ethyl acetate (2×40 mL). The combined organic extracts were washed with brine (50 mL), dried over $Na_2SO_4$, filtered, and concentrated under reduced pressure. The residue was purified by column chromatography eluting with 7% methanol in DCM to afford the title compound Intermediate AA173-4 (2.2 g, 64.74%) as a brown solid. MS (ES): m/z=430.23 [M+2]⁺

Step-4, 5 Synthesis of 6-(azetidin-1-ylmethyl)-5-(THF-3-yl)pyridin-2-amine (Intermediate AA173)

To a solution of Intermediate AA173-4 (2.2 g, 5.12 mmol) in methanol (15 mL) and THF (7 mL) were added ammonium formate (1.2 g, 20.48 mmol, 4.0 eq), acetic acid (1.1 mL, 0.5 v) and 10% palladium hydroxide on carbon (2.2 g). After stirring at 60° C. for 16 h with 20 psi pressure in hydrogenator, the reaction mixture was filtered through Celite bed, and the filtrate was concentrated under reduced pressure. The residue was purified by combi-flash Colum chromatography eluting with 7% methanol/DCM to afford intermediate.

To this intermediate dissolved in DCM (20 mL) was added trifluoroacetic acid (10 mL). After stirring at RT at 30 min, the reaction mixture was diluted with sat. NaHCO₃ (15 mL) and the aqueous phase was extracted with 10% methanol/DCM with ammonia (3×50 mL). The combined organic extracts were washed with brine (50 mL), dried over Na₂SO₄ and concentrated under reduced to afford Intermediate AA173 (0.8 g, 66.99%) which was used in the next step without further purification. MS (ES): m/z 234.1 [M+1]⁺

Synthesis of 6-((ethyl(methyl)amino)methyl)-5-(THF-3-yl)pyridin-2-amine (Intermediate-AA174)

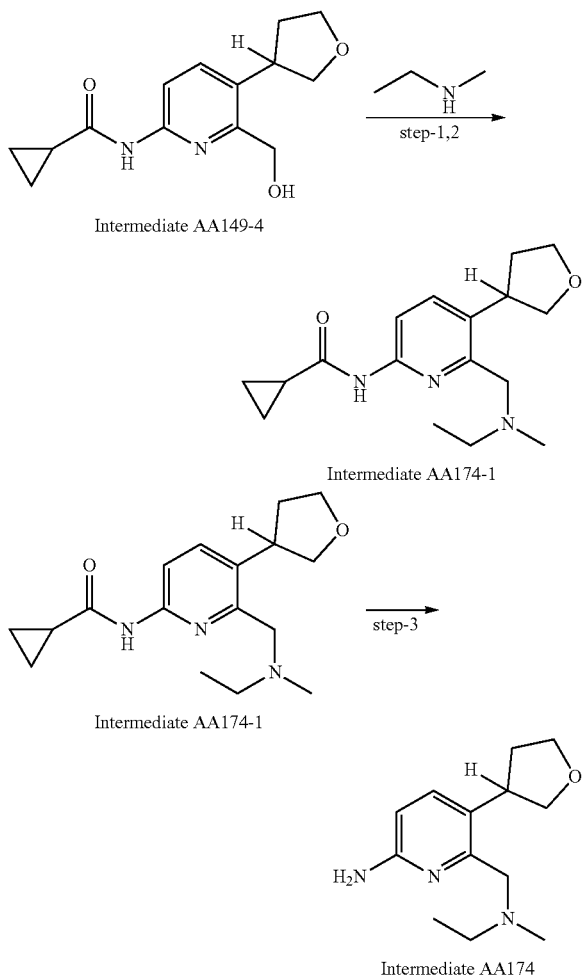

Step-1 & Step-2 synthesis of N-(6-((ethyl(methyl) amino)methyl)-5-(THF-3-yl)pyridin-2-yl)cyclopropanecarboxamide (Intermediate AA174-1)

To a solution of Intermediate AA149-4 (1.8 g, 6.87 mmol) in DCM (20 mL) at 0° C. with triethylamine (2.3 mL, 16.48 mmol, 2.4 eq) was added methane sulfonyl chloride (1.0 mL, 13.74 mmol, 2.0 eq) dropwise. After stirring at RT for 3 h, the reaction mixture was diluted with water (50 mL), washed with sodium bicarbonate solution, and extracted with DCM (3×20 mL). The combined organic extracts were washed with brine (50 mL), dried over Na₂SO₄, filtered, and concentrated under reduced pressure (2.3 g). To the mesylate intermediate (2.3 g, 6.76 mmol) in acetonitrile (20 mL) was added potassium carbonate (9.3 g, 67.6 mmol, 10.0 eq) and N-methylethanamine (2.0 g, 33.8 mmol, 5.0 eq). After stirring at RT for 10 h at 70° C., the reaction mixture was diluted with water (80 mL) and extracted with DCM (3×30 mL). The combined organic extracts were washed with brine, dried over Na₂SO₄, filtered, and concentrated under reduced pressure to afford Intermediate AA174-1 which was used in next step without purification. (1.5 g, 93.49%), MS (ES): m/z 304.2 [M+H]⁺.

Step-3 synthesis of 6-((ethyl(methyl)amino)methyl)-5-(THF-3-yl)pyridin-2-amine (Intermediate AA174)

To a solution of Intermediate AA174 (1.5 g, 4.95 mmol) in methanol (20 mL) and water (5 mL) was added sodium hydroxide (2.0 g, 49.5 mmol, 10.0 eq). After stirring at 50° C. for 12 h, the reaction mixture was cooled to RT, concentrated under reduced pressure to remove methanol, diluted in water (50 mL), and extracted with 5% methanol in DCM (3×20 mL). The combined organic extracts were washed with brine (60 mL), dried over Na₂SO₄, filtered, and concentrated under reduced pressure to afford Intermediate AA174 (1.2 g, quantitative %), MS (ES): m/z 236.1 [M+H]⁺

Synthesis of 6-(2-(dimethylamino)ethyl)-5-(THF-3-yl)pyridin-2-amine (Intermediate-AA175)

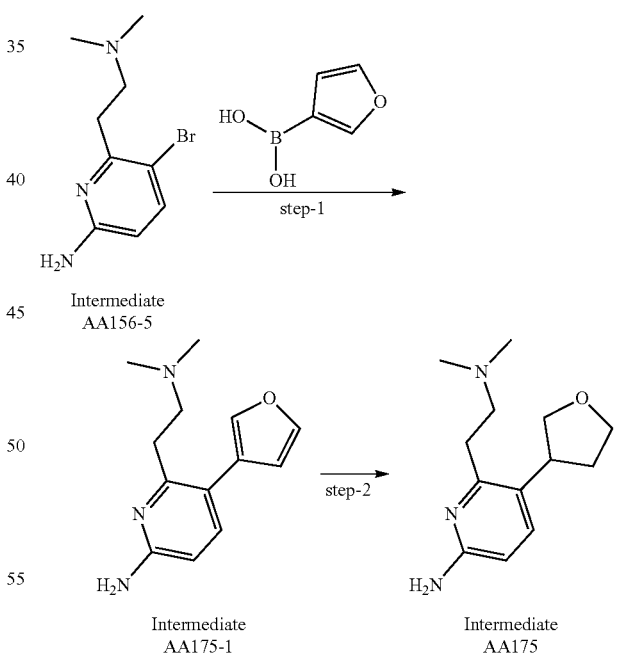

Step-1 Synthesis of 6-(2-(dimethylamino)ethyl)-5-(furan-3-yl)pyridin-2-amine (Intermediate AA175-1)

To a solution of Intermediate AA156-5 (2.0 g, 8.1 mmol)) in dioxane (30 mL) and water (10 mL) were added furan-3-ylboronic acid (0.766 g, 9.8 mmol, 1.2 eq) and potassium phosphate tribasic (5.5 g, 26 mmol, 3.2 eq. After degassing with $N_2$ for 15 min, $PdCl_2(dppf)DCM$ (0.66 g, 0.81 mmol, 0.1 eq) was added. After stirring at 120° C. for 1 h, the reaction mixture was cooled at RT and diluted with ethyl acetate (20 mL) and water (20 mL). The organic layer was collected, and the aqueous phase was extracted with ethyl acetate (2×30 mL). The combined organic extracts were washed with brine (20 mL), dried over $Na_2SO_4$, filtered, and concentrated under reduced pressure. The residue was purified by column chromatography to afford Intermediate AA175-1 (1 g, 52.7%), MS (ES): m/z 231.3 [M+H]+

Step-2 Synthesis of 6-(2-(dimethylamino)ethyl)-5-(THF-3-yl)pyridin-2-amine (Intermediate AA175)

To a solution of Intermediate AA175-1 (2 g, 43 mmol) in methanol: THF (30 mL: 10 mL) was added $Pd(OH)_2$ (1.0 g), ammonium format (1.1 g), and acetic acid (1 mL). After stirring at RT for 12 h with $H_2$ gas at atmospheric pressure, the reaction mixture was filtrate through celite bed, and the filtrate was evaporating in vacuum. The residue was purified by silica gel chromatography eluting with 10% $Et_3N$/ethyl acetate to afford Intermediate AA175 (0.8 g, 78%) MS (ES): m/z 235.3 $[M+H]^+$ Synthesis of 6-((3-fluoroazetidin-1-yl)methyl)-5-(THF-3-yl)pyridin-2-amine (Intermediate-AA176)

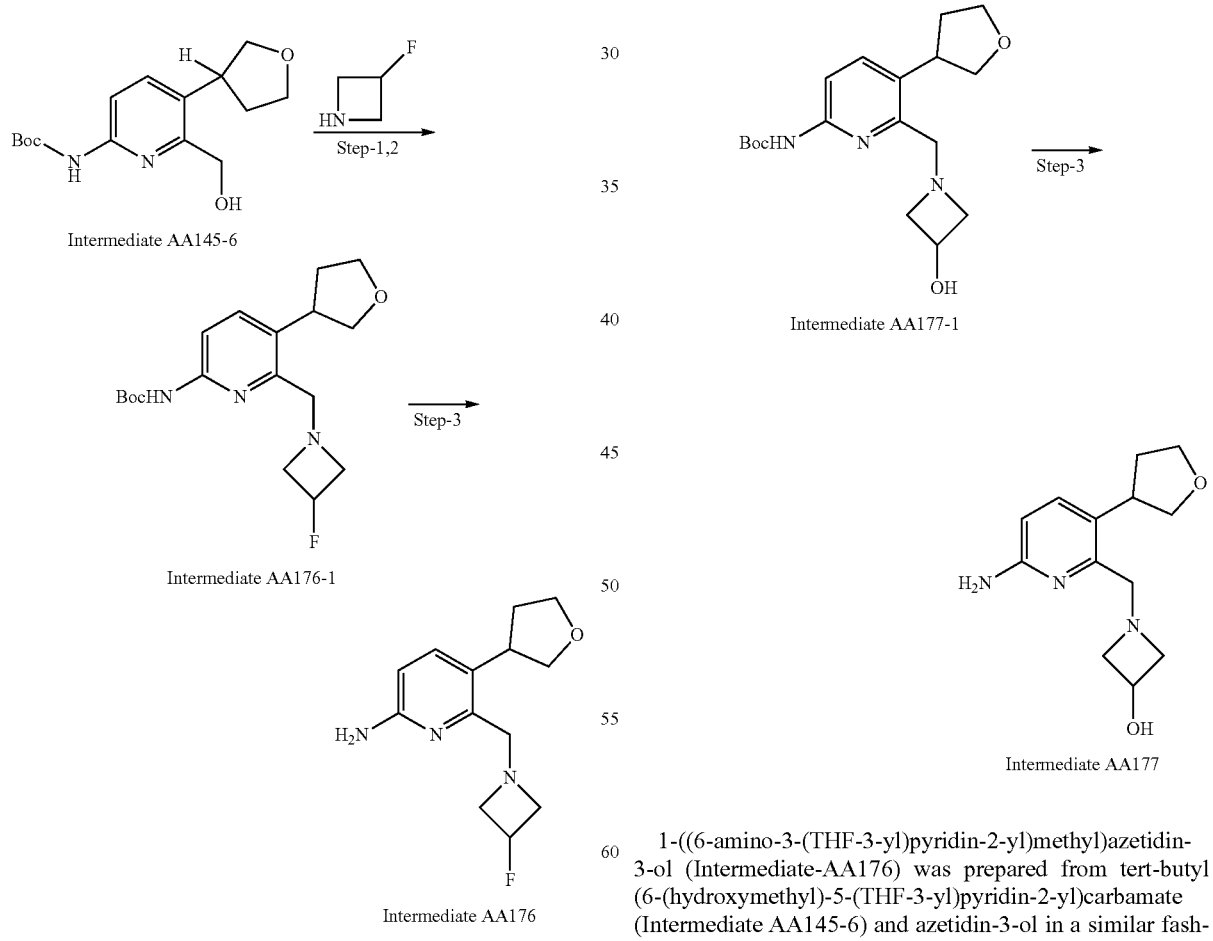

Intermediate AA145-6

Intermediate AA176-1

Intermediate AA176

6-((3-fluoroazetidin-1-yl)methyl)-5-(THF-3-yl)pyridin-2-amine (Intermediate-AA176) was prepared from tert-butyl (6-(hydroxymethyl)-5-(THF-3-yl)pyridin-2-yl)carbamate (Intermediate AA145-6) and 3-fluoroazetidine in a similar fashion to that procedure of step-6, step-7 and step-8 described in synthesis of 5-cyclopentyl-6-((dimethylamino)methyl)pyridin-2-amine (Intermediate AA145) (0.750 g, quantitative %). m/z 251.2 $[M+H]^+$ Synthesis of 1-((6-amino-3-(THF-3-yl)pyridin-2-yl)methyl)azetidin-3-ol (Intermediate-AA177)

Intermediate AA145-6

Intermediate AA177-1

Intermediate AA177

1-((6-amino-3-(THF-3-yl)pyridin-2-yl)methyl)azetidin-3-ol (Intermediate-AA176) was prepared from tert-butyl (6-(hydroxymethyl)-5-(THF-3-yl)pyridin-2-yl)carbamate (Intermediate AA145-6) and azetidin-3-ol in a similar fashion to that procedure of step-6, step-7 and step-8 described in synthesis of 5-cyclopentyl-6-((dimethylamino)methyl)pyridin-2-amine (Intermediate AA145) (0.750 g, quantitative %). m/z 249.2 $[M+H]^+$ Synthesis of 2-(4-(6-amino-2-((dimethylamino)methyl)pyridin-3-yl)morpholin-2-yl)propan-2-ol (Intermediate-AA178)

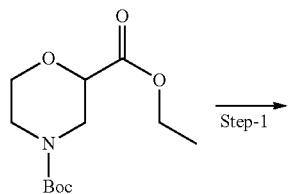

Intermediate AA125-1

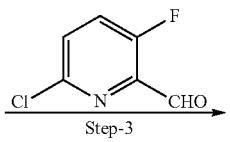

Intaermediate AA178-2    Intermediate AA178-3

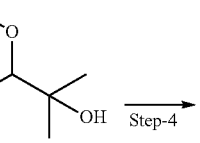

Intermediate AA178-3

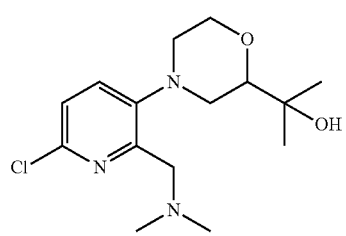

Intermediate AA178-4

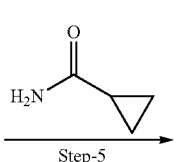

Intermediate AA178-5

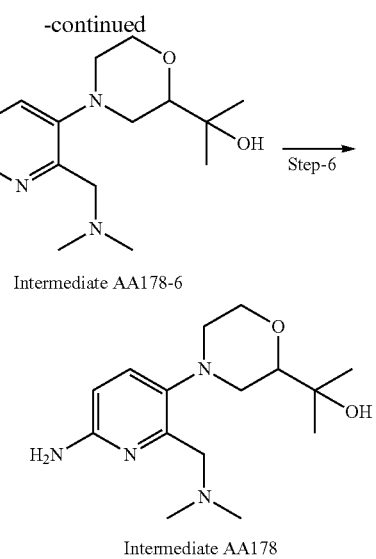

Intermediate AA178-6

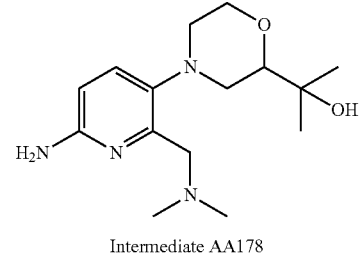 [SMILES: CN(C)Cc1nc(N)ccc1N1CCOC(C(C)(C)O)C1]

Intermediate AA178

Step-1 Synthesis of Tert-Butyl 2-(2-hydroxypropan-2-yl)morpholine-4-carboxylate (Intermediate AA178-2)

A solution of Intermediate AA125-1 (10 g, 38.61 mmol) in THF (100 mL) at 0° C. was added dropwise methyl magnesium bromide solution (3.0M in diethyl ether) (100 mL) in to the reaction mixture at 0° C. and stirred for 15 min at RT. The reaction mixture was quenched in water (500 mL) and extracted with ethyl acetate (3×100 mL). The combined organic extracts were washed with brine (200 mL), dried over Na$_2$SO$_4$, filtered, and concentrated under reduced pressure to afford Intermediate AA178-2 (12.0 g, quantitative %) which was used in the next step without further purification. MS (ES): m/z 245.3 [M+H]$^+$ Step-2 Synthesis of 2-(morpholin-2-yl)propan-2-ol (Intermediate AA178-3)

To a solution of Intermediate AA178-2 (10.0 g, 40.81 mmol) in DCM (100 mL) at 0° C. was added dropwise TFA (35 mL). After stirring at RT for 30 min, the reaction mixture was concentrated under reduced pressure and then extracted with DCM (250 mL). The organic layer was concentrated under reduced pressure to afford Intermediate AA178-3 (13 g, quantitative %) which was used in the next step without further purification. MS (ES): m/z 146.1 [M+H]$^+$ Step-3 Synthesis of 6-chloro-3-(2-(2-hydroxypropan-2-yl)morpholino)picolinaldehyde (Intermediate AA178-4)

To a solution of the Intermediate AA178-3 (9.0 g, 61.64 mmol) and 6-chloro-3-fluoropicolinaldehyde (10.78 g, 67.80 mmol, 1.3 eq) in DMF (90 mL) was added potassium carbonate (25.51 g, 184.92 mmol, 3.0 eq). After stirring for 4 h at 100° C., the reaction mixture was quenched with water (500 mL) and extracted with ethyl acetate (3×150 mL). The combined organic extracts were washed with brine (250 mL), dried over Na$_2$SO$_4$, filtered, and concentrated under reduced pressure. The residue was purified by column chromatography eluting with 1.2% elution methanol in DCM to afford Intermediate AA178-4 (8.0 g, 45.33%) MS (ES): m/z 285.1 [M+H]$^+$

Step-4 Synthesis of 2-(4-(6-chloro-2-((dimethylamino)methyl)pyridin-3-yl)morpholin-2-yl)propan-2-ol (Intermediate AA178-5)

To a solution of Intermediate AA178-4 (3.1 g, 10.95 mmol) in 1,2-dichloroethane (35 mL) was added acetic acid (2 mL) at RT. After bubbling dimethylamine gas in the reaction mixture for 45 min, sodium triacetoxyborohydride (16.1 g, 76.65 mmol, 7.0 eq) was added portion wise. After stirring at RT for 16 h, the reaction mixture was quenched in water (100 mL) and extracted with DCM (3×40 mL). The combined organic extracts were washed with brine (100 mL), dried over $Na_2SO_4$, filtered, and concentrated under reduced pressure. The residue was purified by column chromatography eluting with 50% ethyl acetate in hexane to afford Intermediate AA178-5 (2.5 g, 73.17%) MS (ES): m/z 314.1 $[M+H]^+$

Step-5 Synthesis of N-(6-((dimethylamino)methyl)-5-(2-(2-hydroxypropan-2-yl)morpholino)pyridin-2-yl)cyclopropanecarboxamide (Intermediate AA178-6)

To a solution of Intermediate AA178-5 (2.5 g, 7.98 mmol) in 1,4-dioxane (20 mL) were added 1-cyclopropanecarboxamide (1.2 g, 14.37 mmol, 1.8 eq) and potassium carbonate (3.3 g, 23.94 mmol, 3.0 eq). After degassing under $N_2$ stream for 15 min, Xantphos (0.922 g, 1.59 mmol, 0.2 eq) and $Pd_2(dba)_3$ (0.730 g, 0.79 mmol, 0.1 eq) were added. After stirring at 110° C. for 1 h, the reaction mixture was cooled to RT, diluted water (70 mL) and extracted with ethyl acetate (2×40 mL). The combined organic extracts were washed with brine (80 mL), dried over $Na_2SO_4$, filtered, and concentrated under reduced pressure. The residue was purified by column chromatography eluting with 2% methanol gradient in DCM to afford Intermediate AA178-6 (2.0 g, 69.26%) MS (ES): m/z=363.2 $[M+H]^+$.

Step-6 synthesis of 2-(4-(6-amino-2-((dimethylamino)methyl) pyridin-3-yl) morpholin-2-yl)propan-2-ol (Intermediate AA178)

To a solution of Intermediate AA178-6 (1.9 g, 5.24 mmol) in methanol: water (20 mL:5 mL) was added sodium hydroxide (2.0 g, 52.4 mmol, 10 eq). After stirring at RT for 16 h, the reaction mixture was concentrated under reduced pressure. The residue was diluted with water (30 mL), neutralized with 1N hydrochloric acid to pH-6.5 and extracted with DCM (3×30 mL). The combined organic layer was washed with brine solution, dried over sodium sulfate, and concentrated under reduced pressure to afford Intermediate AA178 (1.2 g, quantitative %). MS (ES): m/z 295.2 $[M+H]^+$

Synthesis of 2-chloro-N,N-dimethyl-5,6,7,8-tetrahydroquinolin-8-amine (Intermediate-AA179)

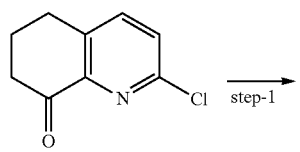

Intermediate AA179-1

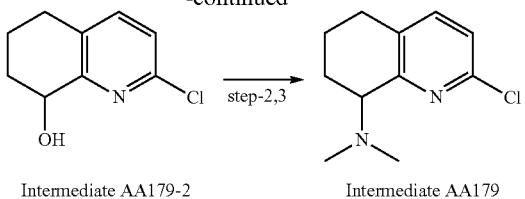

Intermediate AA179-2　　Intermediate AA179

Step-1 synthesis of 2-chloro-5,6,7,8-tetrahydroquinolin-8-ol (Intermediate AA179-2)

To a solution of Intermediate AA179-1 (1.0 g, 5.52 mmol) in ethanol (10 mL) was added portion wise sodium borohydride (0.626 g, 16.56 mmol, 3.0 eq). After stirring at 60° C. for 30 min, the reaction was diluted with ice cold water (80 mL) and extracted into ethyl acetate (3×35 mL). The combined organic layer was washed with brine, filtered, and concentrated under reduced pressure. The residue was purified by silica gel chromatography eluting with 30% ethyl acetate in hexane to afford Intermediate AA179-2 (0.8 g, 79.12%). MS (ES): m/z 184.05 $[M+H]^+$.

Step-2 synthesis of 2-chloro-N,N-dimethyl-5,6,7,8-tetrahydroquinolin-8-amine (Intermediate AA179)

To a solution of Intermediate AA179 (0.8 g, 4.37 mmol) in DCM (8 mL) at 0° C. with N, N-Diisopropylethylamine (2.6 mL, 15.29 mmol, 3.5 eq) was added methane sulfonyl chloride (0.5 mL, 6.55 mmol, 1.5 eq) dropwise. After stirring at RT for 30 min, the reaction mixture was diluted with water (40 mL), washed with sodium bicarbonate solution, and extracted with DCM (3×20 mL). The combined organic extracts were washed with brine, dried over $Na_2SO_4$, filtered, and concentrated under reduced pressure (0.65 g). To the mesylate intermediate (0.65 g, 2.49 mmol) dissolved in acetonitrile (7 mL) was added N,N-diisopropylethylamine (1.3 mL, 7.47 mmol, 3.0 eq) and N-methylethanamine (1.0 g, 12.45 mmol, 5.0 eq). After stirring at RT for 6 h at 90° C., the reaction mixture was diluted with ice cold water (10 mL) and extracted with DCM (3×25 mL). The combined organic extracts were washed with brine, dried over $Na_2SO_4$, filtered, and concentrated under reduced pressure. The residue was purified by silica gel chromatography eluting with 4% methanol in DCM to afford Intermediate AA179 (1.0 g, 92.05%) as a yellow oil. MS (ES): m/z 211.1 $[M+H]^+$

Synthesis of 6-amino-3-(THF-3-yl)pyridin-2-yl) methanol (Intermediate-AA180)

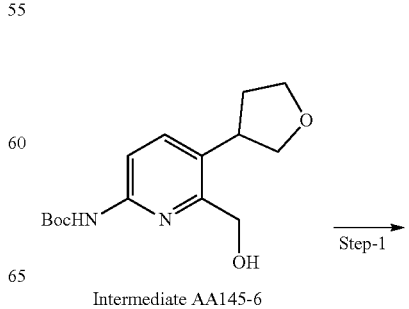

Intermediate AA145-6

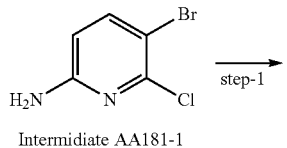

Intermidiate AA180

Step-1 synthesis of 6-amino-3-(THF-3-yl)pyridin-2-yl)methanol (Intermediate AA180)

To a solution of Intermediate AA145-6 (1.0 g, 5.15 mmol) in DCM (15 mL) at 0° C. was added TFA (8 mL). After stirring at RT for 1 h, the reaction mixture was evaporated in vacuum to afford Intermediate AA180 (0.750 g, quantitative) which was used in the next step without further purification. MS (ES): m/z 194 [M+1]$^+$

Synthesis of Tert-Butyl 4-(6-amino-3-(THF-3-yl)pyridin-2-yl)piperazine-1-carboxylate (Intermediate-AA181)

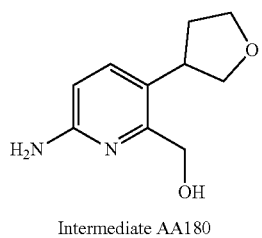

Intermidiate AA181-1

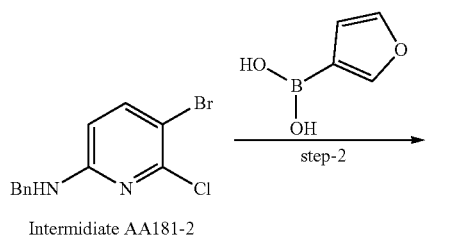

Intermidiate AA181-2

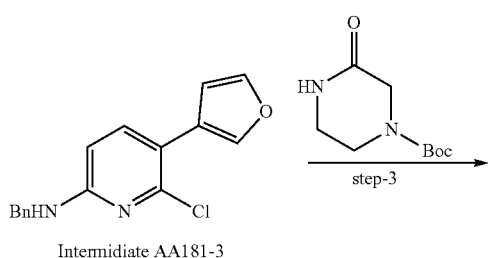

Intermidiate AA181-3

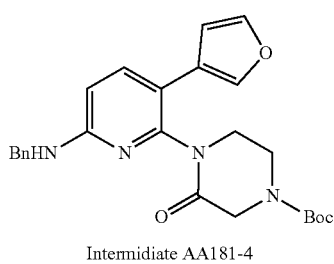

Intermidiate AA181-4

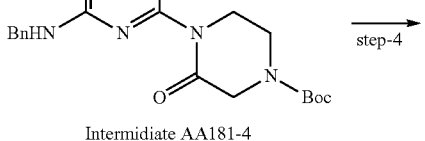

Intermidiate AA181-4

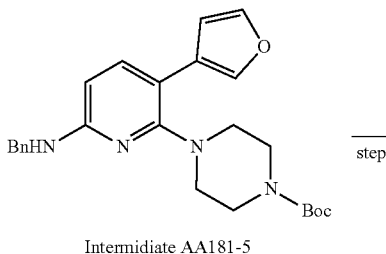

Intermidiate AA181-5

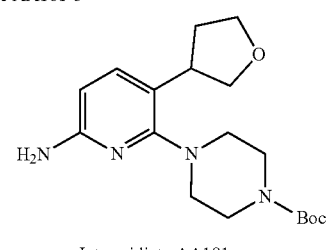

Intermidiate AA181

Step-1 Synthesis of N-benzyl-5-bromo-6-chloro-pyridin-2-amine (Intermediate AA181-2)

To a solution of Intermediate AA181-1 (15 g, 72.3 mmol) was added benzaldehyde (11.5 g, 10.84 mmol, 1.5 eq) in acetic acid (15 mL) and DCE (300 mL). After stirring at RT for 2 h, sodium triacetoxyborohydride (61.3 g, 139.5 mmol, 6.0 eq) was added portion wise. After stirring overnight, the reaction mixture was quenched with water (300 mL) and extracted by EtOAc (2×100 mL). The combined organic layer was washed with brine (100 mL), dried with Na$_2$SO$_4$, and concentrated under reduced pressure. The residue was purified by column chromatography (5-10% gradient elution with ethyl acetate in Hexane) to afford Intermediate-AA181-2. (15 g, 98%), MS (ES): m/z 297 [M+1]$^+$

Step-2 Synthesis of N-benzyl-6-chloro-5-(furan-3-yl)pyridin-2-amine (Intermediate AA181-3)

To a solution of Intermediate AA181-2 (5 g, 16.80 mmol) and furan-3-ylboronic acid (11.5 g, 10.84 mmol, 1.5 eq) in dioxane (80 mL) and water (20 mL) was added K$_3$PO$_4$ (8.9 g, 43.0 mmol, 2.5 eq). After degassing under argon gas atmosphere for 10 min, Pd(dppf)C12 (1.37 g, 16.82 mmol, 0.1 eq) was added. After stirring at 100° C. for 2 h, the reaction mixture was quenched with water (300 mL) and extracted by EtOAc (2×100 mL). The combined organic layer was washed with brine (100 mL), dried with Na$_2$SO$_4$, filtered, and concentrated under reduced pressure to afford Intermediate AA181-3 (2.1 g, 90%), MS (ES): m/z 284 [M+1]$^+$

Step-3 Synthesis of Tert-Butyl 4-(6-(benzylamino)-3-(furan-3-yl)pyridin-2-yl)-3-oxopiperazine-1-carboxylate (Intermediate AA181-4)

To a solution of Intermediate AA181-3 (0.520 g, 18.30 mmol) and tert-butyl 3-oxopiperazine-1-carboxylate (0.733 g, 36.55 mmol, 2 eq) in dioxane (10 mL) was added $K_2CO_3$ (0.758 g, 35.44 mmol, 3 eq). After stirring under argon gas atmosphere for 10 min, CuI (0.697 g, 36.55 mmol, 0.1 eq) and DMEDA (0.4 mL) were added. After stirring at 120° C. for 48 h, the reaction mixture was quenched with water (300 mL) and extracted by EtOAc (2×100 mL). The combined organic layer was washed with brine (100 mL), dried with $Na_2SO_4$, filtered, and concentrated under reduced pressure. The residue was purified by column chromatography (23% gradient elution Ethyl acetate in Hexane) to afford Intermediate-AA181-4 (0.140 g crude, 95%), MS (ES): m/z 448 $[M+1]^+$

Step-4 Synthesis of Tert-Butyl 4-(6-(benzylamino)-3-(furan-3-yl)pyridin-2-yl)piperazine-1-carboxylate (Intermediate AA181-5)

To a solution of Intermediate AA181-4 (0.578 g, 12.70 mmol, 1.0 eq) in THF (20 mL) was added DMS-Borane complex (0.965 g, 12.70 mmol, 10.0 eq). The reaction mixture was stirred at 20-25° C. for 3 h. After completion of reaction, diluted with sodium bicarbonate solution added slowly exothermicity compound and extracted into ethyl acetate and the combined organic extracts were washed with brine, dried over $Na_2SO_4$, filtered, and concentrated under reduced pressure. The residue was purified by column chromatography (20% ethyl acetate gradient in hexane) to afford Intermediate AA181-5 (0.580 g, 98%), MS (ES): m/z 434 $[M+1]^+$

Step-5 synthesis of tert-butyl4-(6-amino-3-(THF-3-yl)pyridin-2-yl)piperazine-1-carboxylate (Intermediate AA181)

To a solution of Intermediate AA181-5 (0.580 g, 13.30 mmol) in THF (5.8 mL) with acetic acid (0.4 mL) and ammonium formate (0.169 g, 26.7 mmol, 2.0 eq) was added palladium hydroxide (1.0 g) in autoclave reaction at 20 psi. After stirring overnight at RT for, the reaction mixture filtered through celite bed. The filtrate was concentrated and purified by column chromatography (2% methanol gradient in DCM) to afford Intermediate AA181 (0.120 g, 94%). MS (ES): m/z=348 $[M+H]^+$

Synthesis of 1-(6-chloro-2-((dimethylamino)methyl)pyridin-3-yl)piperidin-4-ol (Intermediate-AA182)

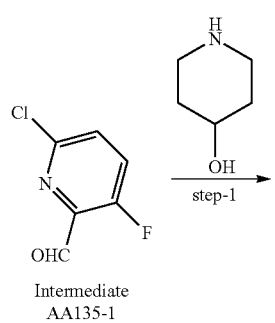

Intermediate AA135-1

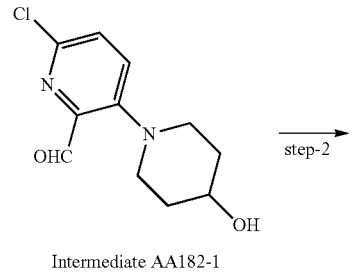

Intermediate AA182-1

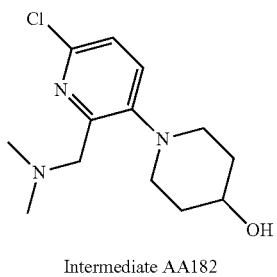

Intermediate AA182

Step-1 Synthesis of 6-chloro-3-(4-hydroxypiperidin-1-yl)picolinaldehyde (Intermediate AA182-1)

To a solution of Intermediate AA135-1 (1.0 g, 6.28 mmol) and piperidin-4-ol (1.0 g, 10.04 mmol, 1.6 eq) in DMF (10 mL) was added potassium carbonate (2.6 g, 18.84 mmol, 3.0 eq). After stirring at 100° C. for 1 h, the reaction mixture was cooled to RT, diluted with ice cold water (100 mL) and extracted with ethyl acetate (3×40 mL). The combined organic extracts were washed with brine (80 mL), dried over $Na_2SO_4$, filtered, and concentrated under reduced pressure. The residue was purified by column chromatography 30% ethyl acetate gradient in hexane to afford Intermediate AA182-1 (1.2 g, 79.54%), MS (ES): m/z 241.07 $[M+H]^+$

Step-2 Synthesis of 1-(6-chloro-2-((dimethylamino)methyl)pyridin-3-yl)piperidin-4-ol (Intermediate AA182)

To a cooled solution of Intermediate AA182-1 (1.2 g, 5.00 mmol) in 1,2-dichloroethane (20 mL) was added acetic acid (2.4 mL) at 0° C. After bubbling dimethylamine gas for 30 min, sodium triacetoxyborohydride (7.4 g, 35 mmol, 7.0 eq) was added portion wise. After stirring at RT for 16 h, the reaction mixture was diluted with ice cold water (100 mL) and extracted with DCM (4×40 mL). The combined organic extracts were washed with brine (90 mL), dried over $Na_2SO_4$, filtered, and concentrated under reduced pressure. The residue was purified by column chromatography 3% methanol gradient in DCM to afford Intermediate AA182 (0.450 g, 33.46%), MS (ES): m/z 270.2 $[M+H]^+$

937

Synthesis of S)-1-((6-amino-3-((R)-THF-3-yl)pyridin-2-yl)methyl)pyrrolidin-3-ol (Intermediate-AA183)

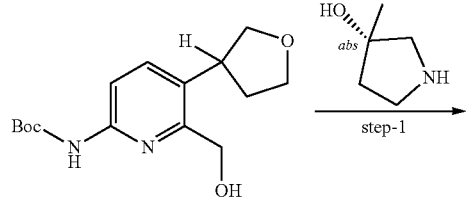
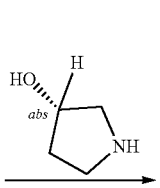

Intermediate AA145-6

Intermediate AA183-1

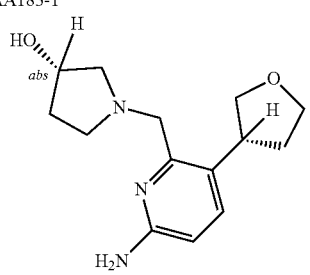

Intermediate AA183

(S)-1-((6-amino-3-((R)-THF-3-yl)pyridin-2-yl)methyl)pyrrolidin-3-ol (Intermediate-AA183) was prepared from tert-butyl (6-(hydroxymethyl)-5-(THF-3-yl)pyridin-2-yl)carbamate (Intermediate AA145-6) and (S)-pyrrolidin-3-ol in a similar fashion to that procedure of step-6, step-7 and step-8 described in synthesis of 5-cyclopentyl-6-((dimethylamino)methyl)pyridin-2-amine (Intermediate AA145) (0.5 g). m/z 278.1 [M+H]⁺

Synthesis of 6-4(R)-3-methoxypyrrolidin-1-yl)methyl)-5-(THF-3-yl)pyridin-2-amine (Intermediate-AA184)

938

-continued

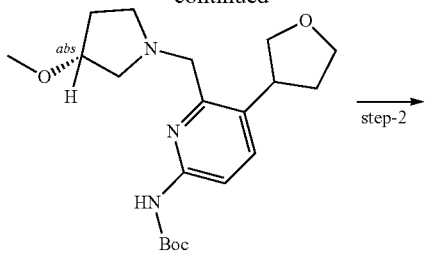

Intermediate AA184-1

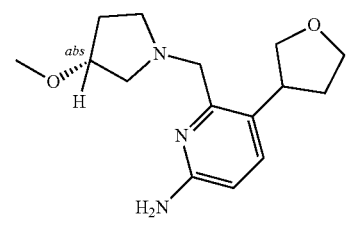

Intermediate AA184

6-(((R)-3-methoxypyrrolidin-1-yl)methyl)-5-(THF-3-yl)pyridin-2-amine (Intermediate-AA184) was prepared from tert-butyl (6-(hydroxymethyl)-5-(THF-3-yl)pyridin-2-yl)carbamate (Intermediate AA145-6) and (R)-3-methoxypyrrolidine in a similar fashion to that procedure of step-6, step-7 and step-8 described in synthesis of 5-cyclopentyl-6-((dimethylamino)methyl)pyridin-2-amine (Intermediate AA145) (0.6 g, quantitative %). m/z 278.1 [M+H]⁺

Synthesis of 1-(6-chloro-2-((dimethylamino)methyl)pyridin-3-yl)-4-(methoxymethyl)piperidin-4-ol (Intermediate-AA185)

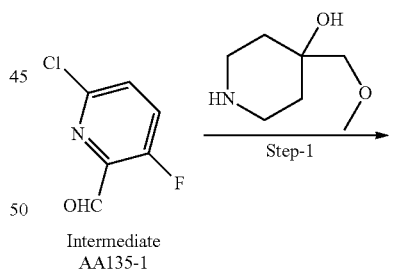

Intermediate AA135-1

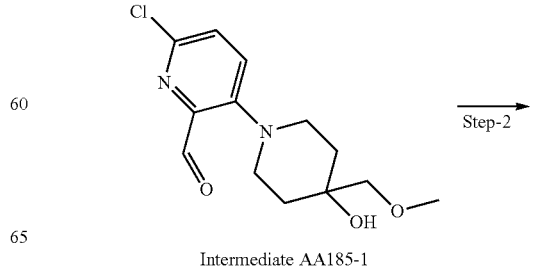

Intermediate AA185-1

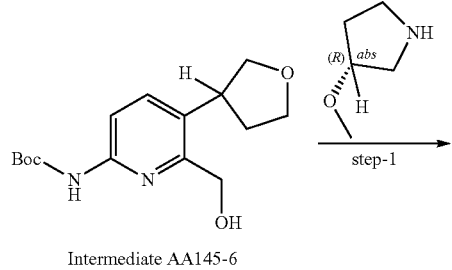
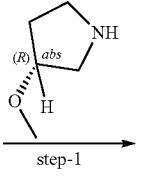

Intermediate AA145-6

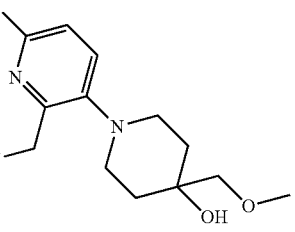

Intermediate AA185

Step-1 Synthesis of 6-chloro-3-(4-hydroxy-4-(methoxymethyl)piperidin-1-yl)picolinaldehyde (Intermediate AA185-1)

To a solution of Intermediate AA135-1 (2.5 g, 15.72 mmol) and 4-(methoxymethyl)piperidin-4-ol (3.2 g, 22.01 mmol, 1.4 eq)) in DMF (25 mL) was added potassium carbonate (4.3 g, 31.44 mmol, 2.0 eq). After stirring at 80° C. for 1 h, the reaction mixture was cooled to RT, diluted water (150 mL) and extracted with ethyl acetate (3×60 mL). The combined organic extracts were washed with brine (180 mL), dried over $Na_2SO_4$, filtered, and concentrated under reduced pressure. The residue was purified by column chromatography eluting with 35% ethyl acetate gradient in hexane to afford Intermediate AA185-1) (3.0 g, 67.24%), MS (ES): m/z 285.1 $[M+H]^+$

Step-2 Synthesis of 1-(6-chloro-2-((dimethylamino)methyl)pyridin-3-yl)-4-(methoxymethyl)piperidin-4-ol (Intermediate AA185)

To a solution of Intermediate AA185-1 (3.0 g, 10.56 mmol) in 1,2-dichloroethane (30 mL) at 0° C. was added acetic acid (6 mL). After bubbling dimethylamine gas for 30 min, sodium triacetoxyborohydride (15.6 g, 73.92 mmol, 7.0 eq) was added portion wise. After stirring at RT for 16 h, the reaction mixture was diluted with ice cold water (250 mL) and extracted with DCM (4×40 mL). The combined organic extracts were washed with brine (90 mL), dried over $Na_2SO_4$, filtered, and concentrated under reduced pressure. The residue was purified by column chromatography 27% ethyl acetate gradient in hexane to afford Intermediate AA185 (2.4 g, 72.59%), MS (ES): m/z 314.1 $[M+H]^+$

Synthesis of N-((6-chloro-3-morpholinopyridin-2-yl)methyl)-N-ethylethanamine (Intermediate-AA186)

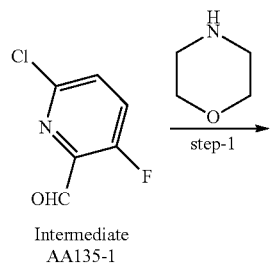

Intermediate AA135-1

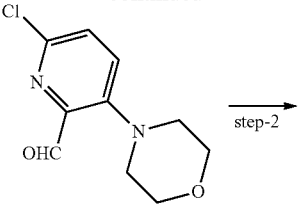

Intermediate AA186-1

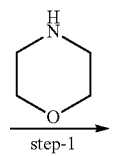

Intermediate AA186

Step-1 Synthesis of 6-chloro-3-morpholinopicolinaldehyde (Intermediate AA186-1)

To a solution of Intermediate AA135-1 (1.0 g, 6.28 mmol) and morpholine (1.0 g, 12.56 mmol, 2.0 eq) in DMF (10 mL) was added potassium carbonate (2.6 g, 18.84 mmol, 3.0 eq). After stirring at 100° C. for 1 h, the reaction mixture was cooled to RT, diluted with ice cold water (100 mL) and extracted with ethyl acetate (3×40 mL). The combined organic extracts were washed with brine (80 mL), dried over $Na_2SO_4$, filtered, and concentrated under reduced pressure. The residue was purified by column chromatography 30% ethyl acetate gradient in hexane to afford Intermediate AA186-1 (1.3 g, 91.51%), MS (ES): m/z 227.05 $[M+H]^+$

Step-2 synthesis of N-((6-chloro-3-morpholinopyridin-2-yl)methyl)-N-ethylethanamine (Intermediate AA186)

To a solution of Intermediate AA186-1 (1.3 g, 5.75 mmol) in methanol (15 mL) were added diethylamine (0.841 g, 11.5 mmol, 2.0 eq) and acetic acid (3.3 mL). After stirring at RT for 30 min, sodium cyanoborohydride (0.903 g, 14.37 mmol, 2.5 eq) was added in portions at 0° C. After stirring for 3 h at 60° C., the reaction mixture was concentrated under reduced pressure. The residue was purified by column chromatography (3.0% methanol gradient in DCM) to afford Intermediate AA186 (1.5 g, 92.15%), MS (ES): m/z=284.1 $[M+H]^+$

Synthesis of 6-(3-(dimethylamino)azetidin-1-yl)-5-(THF-3-yl)pyridin-2-amine (Intermediate-AA187)

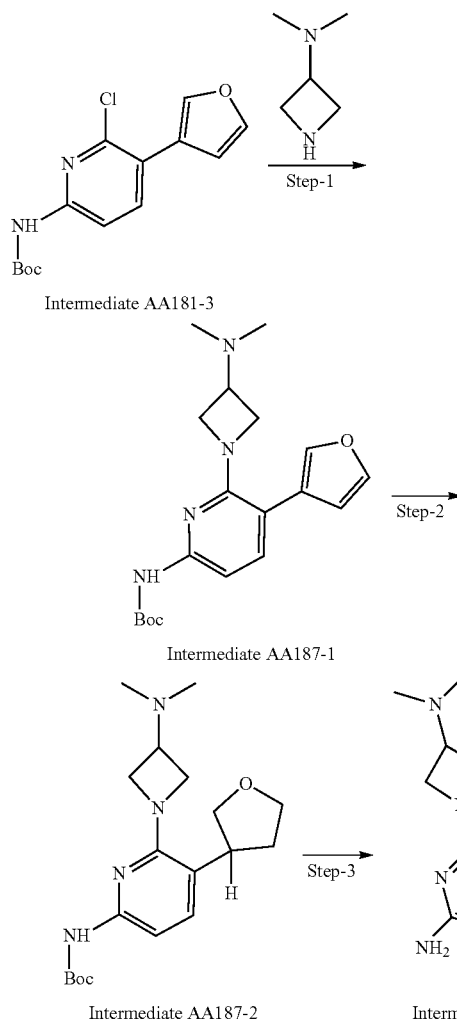

Step-1 Synthesis of Tert-Butyl (6-(3-(dimethylamino)azetidin-1-yl)-5-(furan-3-yl)pyridin-2-yl)carbamate (Intermediate AA187-1)

To a solution of Intermediate AA186-3 (0.350 g, 1.19 mmol) and N,N-dimethylazetidin-3-amine (0.32 g, 2.38 mmol, 1.2 eq) in 1,4-dioxane (4 mL) was added Cs$_2$CO$_3$ (1.1 g, 3.57 mmol, 2.0 eq). After degassing under N$_2$ stream for 15 min, Xantphos (0.068 g, 0.119 mmol, 0.1 eq) and Pd$_2$(dba)$_3$ (0.1 g, 0.119 mmol, 0.1 eq) were added. After stirring at 100° C. for 5 h, the reaction mixture was cooled to RT, diluted water (50 mL) and extracted with ethyl acetate (3×30 mL). The combined organic extracts were washed with brine (90 mL), dried over Na$_2$SO$_4$, filtered, and concentrated under reduced pressure. The residue was purified by column chromatography eluting with 45% ethyl acetate gradient in hexane to afford Intermediate AA187-1 (0.440 g, 24.12%) as a brown solid. MS (ES): m/z=359.20 [M+H]$^+$.

Step-2 Synthesis of Tert-Butyl (6-(3-(dimethylamino)azetidin-1-yl)-5-(THF-3-yl)pyridin-2-yl)carbamate (Intermediate AA187-2)

To a solution of Intermediate AA187-1 (0.440 g, 1.22 mmol) in methanol: THF (6 mL:2 mL) were added Pd(OH)$_2$ (0.4 g), ammonium formate (0.3 g, 4.88 mmol, 4.0 eq) and acetic acid (0.4 mL). After stirring under hydrogen gas at atmospheric pressure for 16 h at RT, the reaction mixture was filtered through celite-bed and washed with methanol. The filtrate was concentrated under reduced pressure. The residue was neutralized with sodium bicarbonate solution and extracted with ethyl acetate (3×30 mL). The combined organic layer was washed with brine (50 mL), dried over Na$_2$SO$_4$, filtered, and concentrated under reduced pressure. The residue was purified by column chromatography 2.5% methanol gradient in DCM to afford Intermediate AA187-7 (0.3 g, 67.42%). MS (ES): m/z 363.24 [M+H]$^+$

Step-3 Synthesis of 6-(3-(dimethylamino)azetidin-1-yl)-5-(THF-3-yl)pyridin-2-amine (Intermediate AA187)

To a solution of Intermediate AA187-2 (0.3 g, 0.82 mmol) in DCM (3 mL) at 0° C. was added dropwise TFA (1 mL). After stirring at RT for 30 min, the reaction mixture was transferred into cold water, neutralized using saturated sodium bicarbonate solution, and extracted with DCM (3×20 mL). The combine organic layer was concentrated under reduced pressure to afford Intermediate AA187 (0.270 g, quantitative %). MS (ES): m/z 263.18 [M+H]$^+$

Synthesis of 5-cyclobutyl-6-((dimethylamino)methyl)pyridin-2-amine (Intermediate-AA188)

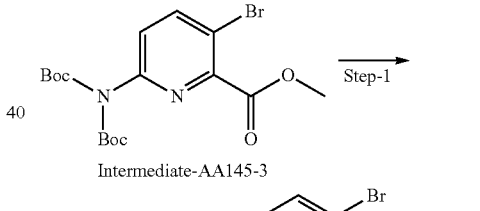

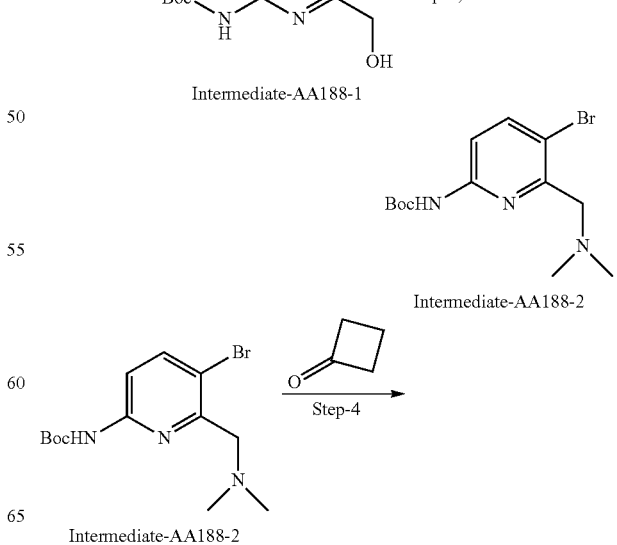

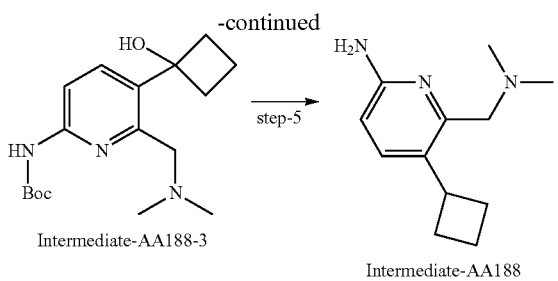

Step-1 Synthesis of Tert-Butyl (5-bromo-6-(hydroxymethyl)pyridin-2-yl)carbamate (Intermediate-AA188-1)

To a solution of Intermediate AA146-3 (50 g, 116.27 mmol) in ethanol (200 mL) was treated portion wise with sodium borohydride (26.3 g, 697.6 mmol, 6 eq). After stirring at 70° C. for 2 h, the reaction mixture was concentrated under reduced pressure, quenched dropwise with water (200 mL) and extracted into DCM (3×150 mL). The combined organic layer was washed with brine (100 mL), passed through a hydrophobic filter, and concentrated under reduced pressure to afford Intermediate-AA188-1 (27 g, 79%), as white solid. MS (ES): m/z 395 [M+1]$^+$ $^1$H NMR (400 MHz, DMSO): δ 7.81 (d, 1H), 7.67 (d, 1H), 7.2 (d, 1H), 5.22 (d, 1H), 4.55 (t, 1H), 3.99 (s, 3H), 3.77 (m, 3H), 3.55 (m, 2H), 2.28 (d, 2H), 1.87 (d, 1H), 1.41 (s, 19H)

Step-2, 3 Synthesis of Tert-Butyl (5-bromo-6-((dimethylamino)methyl)pyridin-2-yl)carbamate (Intermediate-AA188-2)

To a solution of the Intermediate-AA188-1 (22.2 g, 73.2 mmol) and N—N diisopropyl ethylamine (33.3 g, 256.3 mmol, 3.5 eq) in DCM (200 mL) at 0° C. was added methane sulfonyl chloride (12.5 g, 109.8 mmol, 1.5 eq). After stirring for 30 min, the reaction was diluted with water (100 mL) and extracted with ethyl acetate (3×40 mL). The combined organic layer was washed with brine, passed through a hydrophobic filter, and concentrated under reduced pressure. To the residue dissolved in acetonitrile (200 mL) were added dimethyl amine (15 g, 183.0 mmol, 2.5 eq) and N—N diisopropyl ethylamine (33.3 g, 256.3 mmol, 3.5 eq). After stirring at 70° C. for 1 h, the reaction was quenched with water (100 mL) and extracted into ethyl acetate (3×40 mL). The combined organic layer was washed with brine, passed through a hydrophobic filter, and concentrated under reduced pressure. The residue was purified by silica gel chromatography eluting with 50% ethyl acetate/hexane to afford Intermediate-AA188-2 (17.0 g, 94.3%). MS (ES): m/z 330 [M+H]$^+$ Step-4 Synthesis of Tert-Butyl (6-((dimethylamino)methyl)-5-(1-hydroxycyclobutyl)pyridin-2-yl)carbamate (Intermediate AA188-3)

To a solution of Intermediate-AA188-2 (1.0 g, 3.02 mmol) in THF (20 mL) at −78° C. was added n-BuLi (2.6 mL, 9.0 mmol, 3 eq). After stirring at −78° C. for 1 h, cyclobutanone (0.420 g, 6.0 mmol, 2.0 eq) was added dropwise. After complication of addition, the reaction mixture was stirred at RT for 16 h. After complication the reaction, the reaction mixture was combined with four other batches at the same scale, quenched with NaHCO$_3$ and extracted with ethyl acetate (2×30 mL). The combined organic extracts were washed with brine (20 mL), dried over Na$_2$SO$_4$, filtered, and concentrated under reduced pressure. The residue was purified by column chromatography (2% methanol gradient in DCM) to afford Intermediate AA188-3 (1.8 g, 29%). MS (ES): m/z=321.1 [M+1]$^+$ Step-5 Synthesis of 5-cyclobutyl-6-((dimethylamino)methyl)pyridin-2-amine (Intermediate AA188)

To a solution of Intermediate AA188-3 (1.3 g, 4.0 mmol) in DCE (15 mL) was added triethyl silane (6.5 mL, 40.85 mmol, 10 eq). After stirring at RT for 15 min, trifluoro acetic acid (6.5 mL, 5 vol) was added dropwise at RT. After stirring at 60° C. for 1 h, the reaction mixture was quenched with NaHCO$_3$ and extracted with ethyl acetate (2×30 mL). The combined organic extracts were washed with brine (20 mL), dried over Na$_2$SO$_4$, filtered, and concentrated under reduced pressure. The residue was purified by column chromatography (7% methanol gradient in DCM) and reversed phase prep HPLC purification to afford Intermediate AA188 (175 mg, 21%). MS (ES): m/z=206.2 [M+1]$^+$ Synthesis of 6-(((S)-3-methoxypyrrolidin-1-yl)methyl)-5-(THF-3-yl)pyridin-2-amine (Intermediate-AA189)

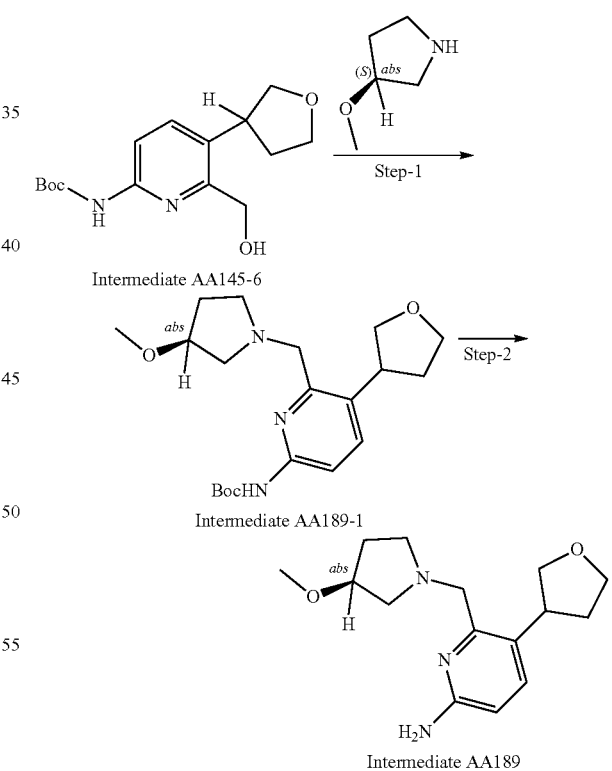

6-(((S)-3-methoxypyrrolidin-1-yl)methyl)-5-(THF-3-yl)pyridin-2-amine (Intermediate-AA189) was prepared from tert-butyl (6-(hydroxymethyl)-5-(THF-3-yl)pyridin-2-yl)carbamate (Intermediate AA145-6) and (S)-3-methoxypyrrolidine in a similar fashion to that procedure of step-6, step-7 and step-8 described in synthesis of 5-cyclopentyl- 6-((dimethyl amino)methyl)pyridin-2-amine (Intermediate AA145) (1.2 g, quantitative %). m/z 278.1 [M+H]+

Synthesis of 6-amino-2-((dimethylamino)methyl)-N-ethylnicotinamide (Intermediate-AA190)

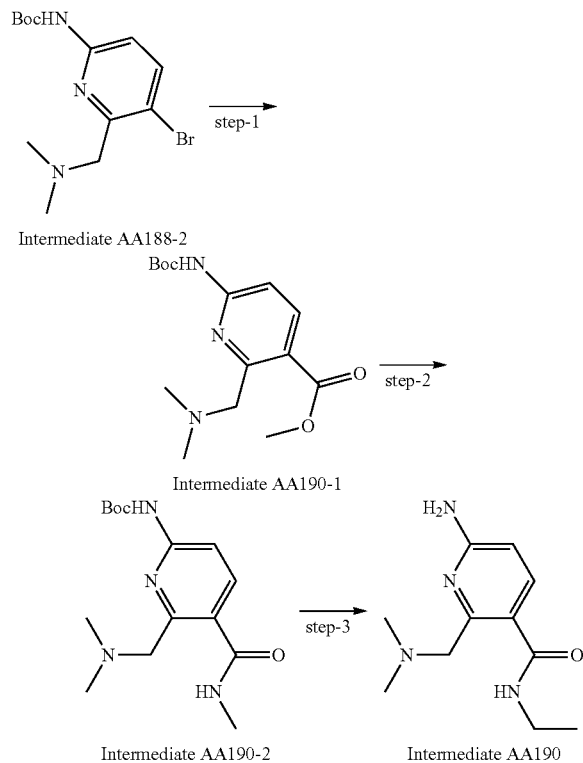

Step-1 Synthesis of methyl 6-((tert-butoxycarbonyl)amino)-2-((dimethylamino)methyl)nicotinate (Intermediate AA190-4)

To a solution of Intermediate AA188-2 (2.0 g, 6.04 mmol, 1.0 eq) in DCM (20 mL) was added triethylamine (2.5 mL, 18.12 mmol, 3.0 eq). After purging carbon monoxide for 15 min, [1,1'-Bis(diphenylphosphino)ferrocene]dichloropalladium(II), complex with DCM (2.5 mL, 0.5 mmol, 0.1 eq) was added. After stirring at 90° C. for 3 h, the reaction mixture was cooled to RT, diluted with water (100 mL), and extracted into DCM (3×40 mL). The combined organic extracts were washed with brine, dried over Na₂SO₄, filtered, and concentrated under reduced pressure. The residue was purified by column chromatography (2.5% methanol gradient in DCM) to afford Intermediate AA190-1 (1.2 g, 64.05%), MS (ES): m/z 310.1 [M+1]+

Step-2 Synthesis of Tert-Butyl (6-((dimethylamino)methyl)-5-(ethylcarbamoyl)pyridin-2-yl)carbamate (Intermediate AA190-2)

To a solution of Intermediate AA190-1 (1.1 g, 3.55 mmol) in toluene (11 mL) were added dropwise ethylamine (0.48 g, 10.65 mmol, 3.0 eq) and triazabicyclodecene (0.740 g, 5.32 mmol, 1.5 eq). After stirring at 110° C. for 4 h, the reaction was quenched with water (200 mL) and extracted into ethyl acetate (3×80 mL). The combined organic extracts were washed with brine, dried over Na₂SO₄, filtered, and concentrated under reduced pressure. The residue was purified by column chromatography (2% methanol gradient in DCM) to afford Intermediate AA190-2 (0.445 g, 38.82%). MS (ES): m/z=323.2 [M+H]+

Step-3 Synthesis of 6-amino-2-((dimethylamino)methyl)-N-ethylnicotinamide (Intermediate AA190)

To a solution of Intermediate AA190-2 (0.445 g, 1.38 mmol) in DCM (5 mL) was added dropwise TFA (2 mL). After stirring at RT for 30 min, the reaction mixture was neutralized using sodium bicarbonate solution and extracted into DCM (3×20 mL). The combined organic extracts were washed with brine, dried over Na₂SO₄, filtered, and concentrated under reduced pressure to afford Intermediate AA190 (0.250 g, quantitative). MS (ES): m/z=223.1 [M+H]+

Synthesis of 6-((dimethylamino)methyl)-5-(tetrahydro-2H-pyran-4-yl)pyridin-2-amine (Intermediate-AA191)

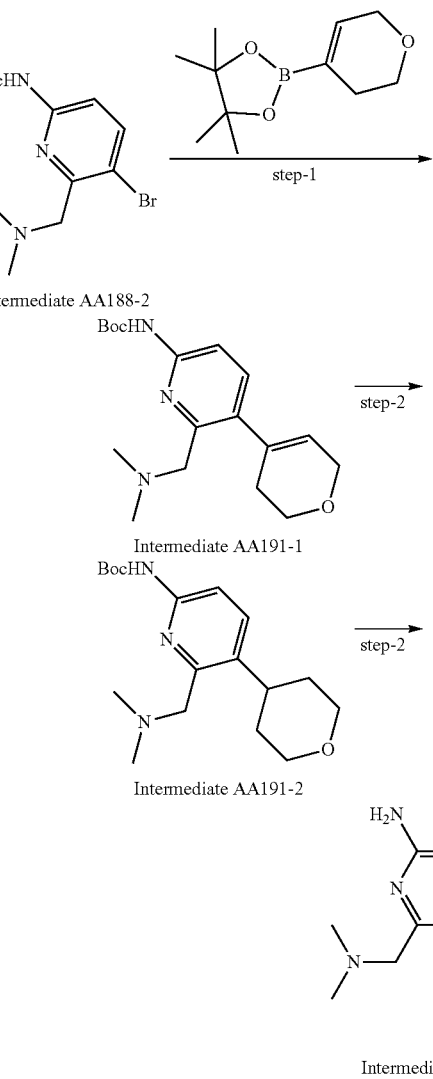

Step-1 Synthesis of Tert-Butyl (5-(3,6-dihydro-2H-pyran-4-yl)-6-((dimethylamino)methyl)pyridin-2-yl) carbamate (Intermediate AA191-1)

To a solution of Intermediate AA188-2 (50 g, 151.5 mmol) in 1,4-dioxane:water (400 mL:100 mL) were add 2-(3,6-dihydro-2H-pyran-4-yl)-4,4,5,5-tetramethyl-1,3,2-dioxaborolane (47.7 g, 227.2 mmol, 1.5 eq) and potassium phosphate tribasic (96.3 g, 454.5 mmol, 3.0 eq). After degassing with N$_2$ for 15 min, X-phosPdG2 (11.9 g, 15.1 mmol, 0.1 eq) was added. After stirring at 140° C. for 4 h, the reaction mixture was cooled to RT, diluted with water (1 L), and extracted with ethyl acetate (2×2 L). The combined organic extracts were wash with brine (1 L), dried over Na$_2$SO$_4$, filtered, and concentrated under reduced pressure. The residue was purified by column chromatography eluting with 2% methanol gradient in DCM to afford Intermediate AA191-1 (40 g, 79%), MS (ES): m/z 334.2 [M+H]$^+$

Step-2 Synthesis of Tert-Butyl (6-((dimethylamino)methyl)-5-(tetrahydro-2H-pyran-4-yl)pyridin-2-yl) carbamate (Intermediate AA191-2)

To a suspension of palladium hydroxide (130 g) in methanol (600 mL) and THF (40 mL) was added Intermediate AA191-1 (130 g). After stirring under hydrogen gas at atmospheric pressure for 4 h at RT, the reaction mixture was filtered through celite-bed and washed with methanol. The filtrate was concentrated under reduced pressure to afford Intermediate AA191-2 (120 g, 91.75%). MS (ES): m/z 336.2 [M+H]$^+$

Step-3 Synthesis of 6-((dimethylamino)methyl)-5-(tetrahydro-2H-pyran-4-yl)pyridin-2-amine (Intermediate AA191)

To a solution of Intermediate AA191-2 (120 g, 356.9 mmol, 1.0 eq) in DCM (1.2 L) was added TFA (360 mL) dropwise. After stirring at 55° C. for 2 h, the reaction mixture was neutralized using saturated sodium hydroxide solution and extracted with 10% methanol in DCM (4×10 L). The combine organic layer was concentrated under reduced pressure to afford Intermediate AA191 (66 g, 78.40%). MS (ES): m/z 236.1 [M+H]$^+$

Synthesis of 6-((dimethylamino)methyl)-5-(3-methoxycyclopentyl)pyridin-2-amine (Intermediate-AA192)

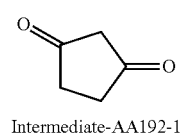
Intermediate-AA192-1

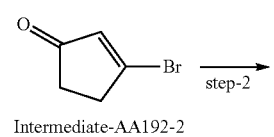
Intermediate-AA192-2

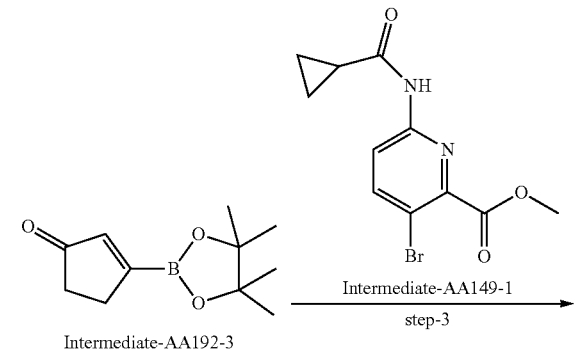
Intermediate-AA192-3 + Intermediate-AA149-1

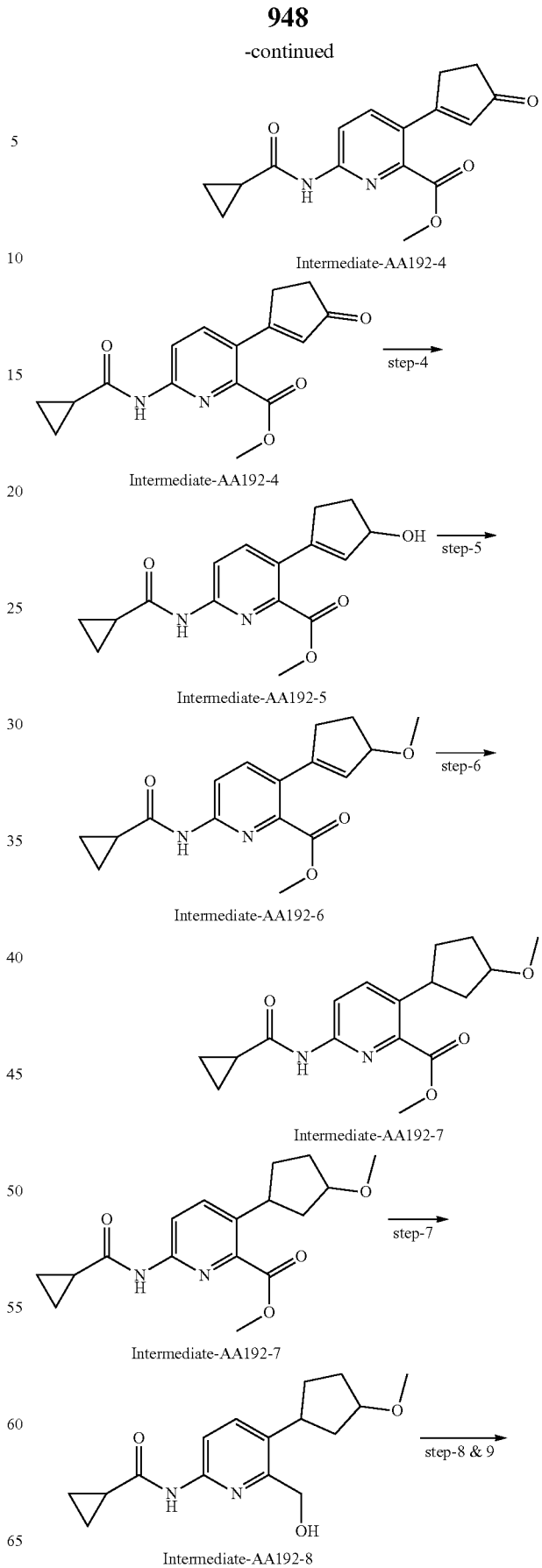

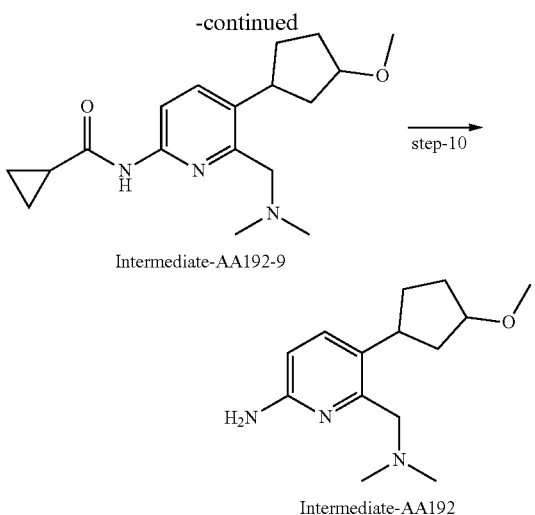

Intermediate-AA192-9

Intermediate-AA192

Step-1 Synthesis of 3-bromocyclopent-2-en-1-one (Intermediate AA192-2)

To a solution of Intermediate AA192-1 (10 g, 10.19 mmol) in DCM (240 mL) was treated portion wise with triphenylphosphine (29.1 g, 11.11 mmol). After stirring at 0° C. for 30 mins, triethylamine (17 mL, 14.12 mmol, 2.0 eq) and then bromine (5.7 mL, 11.11 mmol, 1.1 eq) were added. After stirring at RT for 20 min, the reaction was concentrated under reduced pressure, diluted with water (500 mL), and extracted by ethyl acetate. The combined organic layer was washed with brine, dried over $Na_2SO_4$, and concentrated under reduced pressure. The residue was purified by column chromatography (2% gradient of ethyl acetate in hexane) to afford Intermediate AA192-2 (10 g, 96.88%), MS (ES): m/z 303 $[M+1]^+$

Step-2 Synthesis of 3-(4,4,5,5-tetramethyl-1,3,2-dioxaborolan-2-yl)cyclopent-2-en-1-one (Intermediate AA192-3)

To a solution of Intermediate AA192-2 (1.5 g, 46.55 mmol) in dioxane (15 mL) was added potassium acetate (2.6 g, 39.65 mmol, 4 eq) followed by dropwise addition of bispinacoline diborane (2.98 g, 40.55 mmol, 3.0 eq). After degassing with argon for 10 mins, $PdCl_2(dppf)_2$ (0.702 g, 32.74 mmol, 0.07 eq) was added. After stirring at 120° C. for 30 mins, the reaction was quenched with water (500 mL) and extracted by ethyl acetate. The combined organic layer was washed with brine, dried over $Na_2SO_4$, and concentrated under reduced pressure. The residue was purified by column chromatography (10% gradient of ethyl acetate in hexane) to afford Intermediate AA192-3 (1.2 g, 96%), MS (ES): m/z 299 [M+1]+

Step-3 Synthesis of methyl 6-(cyclopropanecarbox-amido)-3-(3-oxocyclopent-1-en-1-yl)picolinate (Intermediate AA192-4)

To a solution of Intermediate AA149-1 (1 g, 12.94 mmol) in dioxane (15 mL) was added potassium phosphate (2.2 g, 39.65 mmol, 3 eq) followed by dropwise addition of Intermediate AA192-3 (0.900 g, 40.55 mmol, 2.0 eq). After degassing with argon for 10 min, X-phose PdG2 (0.302 g, 32.74 mmol, 0.05 eq) was added. After stirring at 80° C. for 1 h, the reaction was diluted with water (500 mL) and extracted by ethyl acetate. The combined organic layer was washed with brine, dried over $Na_2SO_4$, and concentrated under reduced pressure. The residue was purified by column chromatography (12-15% gradient of ethyl acetate in hexane) to afford Intermediate AA192-4 (0.820 g, 95%), MS (ES): m/z 300 $[M+1]^+$

Step-4 synthesis of methyl 6-(cyclopropanecarbox-amido)-3-(3-hydroxycyclopent-1-en-1-yl)picolinate (Intermediate AA192-5)

To a solution of Intermediate AA192-4 (1 g, 33.89 mmol) in methanol (20 mL) was treated portion wise with sodium borohydride (0.380 g, 16.9 mmol, 3.0 eq) and followed by cesium chloride (0.5 mL). After stirring at rt for 1 h, the reaction was quenched with water (200 mL) and extracted into ethyl acetate (3×80 mL). The combined organic extracts were washed with brine, dried over $Na_2SO_4$, filtered, and concentrated under reduced pressure. The residue was purified by column chromatography (20-30% gradient of ethyl acetate in hexane) to afford Intermediate AA192-5 (0.700 g, 100%). MS (ES): m/z=302 $[M+H]^+$.

Step-5 synthesis of tert-butyl 4-(6-(benzylamino)-3-(furan-3-yl)pyridin-2-yl)piperazine-1-carboxylate (Intermediate AA192-6)

To a solution of Intermediate AA192-5 (0.700 g, 12.70 mmol, 1.0 eq) in THF (20 mL) and methanol (3 mL) was added TMS-diazomethane complex (0.965 g, 12.70 mmol, 5.0 eq). After stirring at RT for 3 h, the reaction was diluted with sodium bicarbonate solution slowly and extracted into ethyl acetate. The combined organic extracts were washed with brine, dried over $Na_2SO_4$, filtered, and concentrated under reduced pressure. The residue was purified by column chromatography (20% gradient of ethyl acetate in hexane) to afford Intermediate AA192-6 (0.580 g, 98%), MS (ES): m/z 316 $[M+1]^+$

Step-6 synthesis of methyl 6-(cyclopropanecarbox-amido)-3-(3-methoxycyclopentyl) picolinate (Intermediate AA192-7)

To a solution of Intermediate AA192-6 (0.580 g, 13.30 mmol) in THF (5.8 mL) with acetic acid (0.4 mL) and ammonium formate (0.169 g, 26.7 mmol, 2.0 eq) was added palladium hydroxide (1.0 g) in autoclave. After stirring at RT overnight with 20 psi hydrogen gas, the reaction mixture was filtered through Celite bed. The filtrate was concentrated, and the residue was purified by column chromatography (2% methanol gradient in DCM) to afford Intermediate AA192-7 (0.410 g, 94%). MS (ES): m/z=318 $[M+H]^+$

Step-7 Synthesis of N-(6-(hydroxymethyl)-5-(3-methoxycyclopentyl)pyridin-2-yl) cyclopropane carboxamide (Intermediate AA192-8)

To a solution of Intermediate AA192-7 (0.580 g, 37.27 mmol) in ethanol (7 mL) was treated portion wise with sodium borohydride (0.320 g, 23.62 mmol, 6.0 eq). After stirring at 70° C. for 30 mins, the reaction was concentrated under reduced pressure, diluted with water (500 mL), and extracted with ethyl acetate. The combined organic layer was washed with brine, dried over $Na_2SO_4$, and concentrated under reduced pressure. The residue was purified by

Step-8 & 9 synthesis of N-(6-((dimethylamino)methyl)-5-(3-methoxycyclopentyl)pyridin-2-yl)cyclopropanecarboxamide (Intermediate AA192-9)

To a solution of Intermediate AA192-8 (0.450 g, 37.02 mmol) in DCM (5 mL) at 0° C. with diisopropylethylamine (0.240 g, 20.55 mmol, 1.5 eq was added mesyl chloride (0.530 g, 11.06 mmol, 3.0 eq). After stirring at 0° C. to RT for 15 mins, the reaction mixture was quenched with water (300 mL) and extracted by DCM (2×100 mL). The combined organic layer was washed with brine (100 mL), passed through a Na$_2$SO$_4$, and concentrated under reduced pressure. (0.420 g, 74%), MS (ES): m/z 482 [M+1]$^+$ To a solution of mesylated intermediate (0.420 g, 17.22 mmol) in acetonitrile (14 mL) was portion wise potassium carbonate (0.780 g, 33.22 mmol, 6.0 eq) and dimethylamine·hydrochloride (0.362 g, 51.66 mmol, 3.0 eq) dropwise. After stirring at 70° C. for 2 h., the reaction mixture was quenched with water (300 mL) and extracted by ethyl acetate. The combined organic layer was washed with brine (100 mL), passed through a Na$_2$SO$_4$, and concentrated under reduced pressure. The residue was purified by column chromatography (5% methanol gradient in DCM) to afford Intermediate AA212-9 (0.290 g, 81.92%), MS (ES): m/z 317 [M+1]$^+$

Step-10 Synthesis of 6-((dimethylamino)methyl)-5-(3-methoxycyclopentyl)pyridin-2-amine (Intermediate AA192)

To a solution of Intermediate AA192-9 (0.290 g, 33.89 mmol) in methanol (5 mL) and water (1 mL) was treated portion wise with sodium hydride (0.320 g, 16.9 mmol, 3.0 eq) After stirring at rt for 1 h, the reaction was quenched with water (200 mL) and extracted into ethyl acetate (3×80 mL). The combined organic extracts were washed with brine, dried over Na$_2$SO$_4$, filtered, and concentrated under reduced pressure. The residue was purified by column chromatography (20-30% gradient elution ethyl acetate in hexane) to afford Intermediate AA192 (0.120 g, 93%). MS (ES): m/z=249 [M+H]$^+$.

Synthesis of 4-(6-chloro-2-((dimethylamino)methyl)pyridin-3-yl)-1-methylpiperazin-2-one (Intermediate AA193)

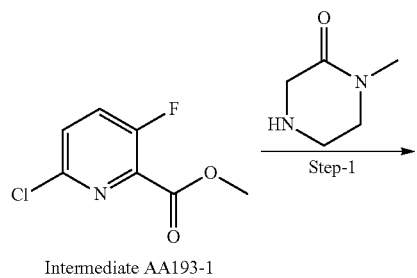

Intermediate AA193-1

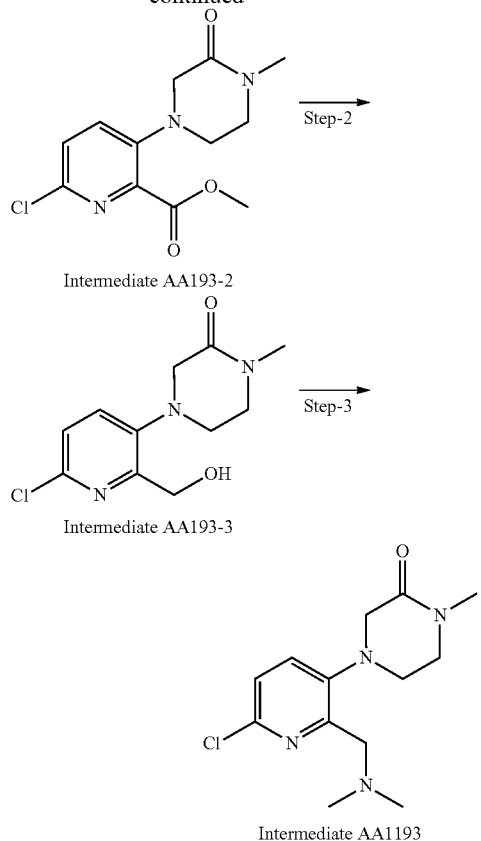

Step-1 Synthesis of methyl 6-chloro-3-(4-methyl-3-oxopiperazin-1-yl)picolinate (Intermediate-AA193-2)

To a solution of Intermediate-AA193-1(1.2 g, 6.36 mmol) in DMF (12.5 L) were added K$_2$CO$_3$ (2.6 g, 18.9 mmol, 3 eq) and 1-methylpiperazin-2-one (0.935 g, 6.8 mmol, 1.3 eq). After stirring at 80° C. for 12 h, the reaction mixture was quenched in water (100 mL) and extracted with ethyl acetate (100 mL×3). The combined organic layer was dried over sodium sulfate and concentrated under reduced pressure. The residue was purified by column chromatography to afford Intermediate-AA193-2. (0.815 g, 47.33%). MS (ES): m/z 283.71 [M+H]$^+$

Step-2 Synthesis of 4-(6-chloro-2-(hydroxymethyl)pyridin-3-yl)-1-methylpiperazin-2-one (Intermediate-AA193-3)

To a solution of Intermediate-AA193-2 (0.700 g, 2.4 mmol) in ethanol (10 mL) was treated portion wise with sodium borohydride (0.289 g, 12.04 mmol, 5 eq). After stirring at 60° C. for 2 h, the reaction was concentrated under reduced pressure, quenched slowly with water (80 mL), and extracted by DCM (3×50 mL). The combined organic layer was washed with brine (80 mL), passed through a Na$_2$SO$_4$, and concentrated under reduced pressure to afford Intermediate-AA193-3. (400 mg, 63.40%). MS (ES): m/z 256.70 [M+1]$^+$

Step-3 Synthesis of 4-(6-chloro-2-((dimethylamino) methyl)pyridin-3-yl)-1-methylpiperazin-2-one (Intermediate AA193)

To a solution of Intermediate-AA193-3 (0.480 g, 1.8 mmol) in DCM (5 mL) with TEA (0.570 g, 56.4 mmol, 3.0 eq) at 0° C. was added mesyl chloride (0.429 g, 3.76 mmol, 2 eq). After stirring at RT for 2 h, the reaction mixture was quenched with water (70 mL) and extracted by DCM (3×30 ML). The combined organic layer was washed with brine (50 mL), passed through a $Na_2SO_4$, and concentrated under reduced pressure to afford mesylated intermediate. (665 mg-crude).

To a solution of Mesylated above product (0.665 g, 1.99 mmol) in acetonitrile (6 mL) were added DIPEA (1.10 g, 8.5 mmol, 4.3 eq) and dimethylamine hydrochloride (0.501 g, 6.19 mmol, 3.1 eq) at RT. After stirring at 90° C. for 3 h, the reaction mixture was evaporated, quenched in water (70 mL), and extracted by DCM (3×30 mL). The combined organic layer was washed with brine (60 mL), dried with $Na_2SO_4$, and concentrated under reduced pressure. The residue was purified by column chromatography eluting with 1-5% MeOH in DCM to afford Intermediate-AA193. (0.370 g, quantitative yield). MS (ES): m/z 282.12 [M+1]$^+$

Synthesis of 6-((dimethylamino)methyl)-5-(methylsulfonyl)pyridin-2-amine (Intermediate AA194)

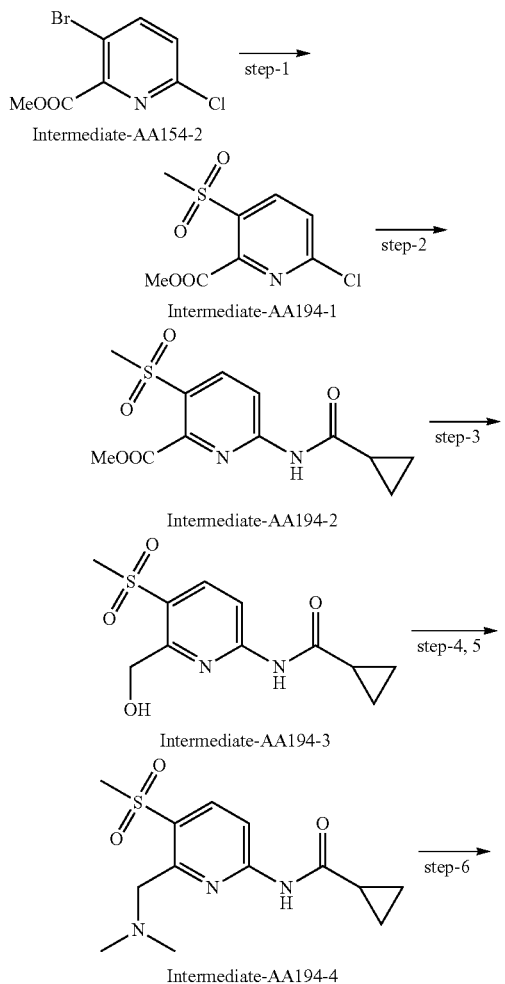

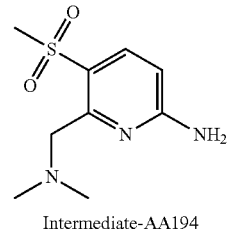

Intermediate-AA194

Step-1 Synthesis of 4-(6-chloro-2-(hydroxymethyl) pyridin-3-yl)-1-methylpiperazin-2-one (Intermediate-AA194-1)

To a solution of Intermediate-AA154-2 (1 g) in THF (10 mL) was added sodium methythionide (0.418 g, 5 eq). After stirring at 60° C. for 12 h, solvent evaporated under reduced pressure and purified by column chromatography to afford thioether intermediate (400 mg).

To a solution of thioether intermediate (400 mg) in DCM (5 mL) was added mCPBA (1 g, 5 eq). After stirring overnight. the solvent was removed, the residue was purified by column chromatography to afford Intermediate-AA194-1 (300 mg, 30%), MS (ES): m/z 250.67 [M+1]$^+$

Step-2 Synthesis of methyl 6-(cyclopropanecarboxamido)-3-(methylsulfonyl)picolinate (Intermediate AA194-2)

To a solution of Intermediate AA194-1) (0.6 g) in 1,4-dioxane (8 mL) were added cyclopropyl carboxamide (0.3 g, 1.2 eq) and $Cs_2CO_3$ (0.71 g, 3.0 eq). After degassing under $N_2$ stream for 15 min, Xantphos (0.2 g, 0.2 eq) and $Pd_2(dba)_3$ (0.157, 0.1 eq) were added. After stirring at 110° C. for 2 h, the reaction mixture was cooled to RT, diluted water (50 mL) and extracted with ethyl acetate (3×20 mL). The combined organic extracts were washed with brine (50 mL), dried over $Na_2SO_4$, filtered, and concentrated under reduced pressure. The residue was purified by column chromatography to afford Intermediate AA194-2 (0.4 g, 55%). MS (ES): m/z=299.31 [M+H]$^+$.

Step-3 Synthesis of N-(6-(hydroxymethyl)-5-(methylsulfonyl)pyridin-2-yl)cyclopropanecarboxamide (Intermediate AA194-3)

To a solution of Intermediate AA194-2 (1.5 g) in ethanol (15 mL) was treated portion wise with sodium borohydride (6 eq). After stirring at 60° C. for 2 h, the reaction was concentrated under reduced pressure, diluted slowly with water (100 mL), and extracted by DCM (4×50 mL). The combined organic layer was washed with brine (100 mL), passed through a $Na_2SO_4$, and concentrated under reduced pressure to afford Intermediate AA194-3 (800 g), MS (ES): m/z=270.31 [M+H]$^+$.

Step-4 & Step-5 Synthesis of N-(6-((dimethylamino)methyl)-5-(methylsulfonyl)pyridin-2-yl)cyclopropanecarboxamide (Intermediate AA194-4)

To a solution of Intermediate AA194-3 (1 g, 3.7 mmol) in DCM (15 mL) with diisopropylethylamine (1.8 mL, 11.11 mmol, 3.0 eq) at 0° C. was added mesyl chloride (0.446 g, 5.55 mmol, 1.5 eq). After stirring at RT for 30 mins, the reaction mixture was quenched with water (300 mL) and extracted by DCM (2×100). The combined organic layer was washed with brine (100 mL), passed through a $Na_2SO_4$, and concentrated under reduced pressure to afford mesylated intermediate (1 g), MS (ES): m/z 349 [M+1]$^+$ To a solution of mesylated intermediate (1 g, 2.8 mmol) in acetonitrile (14 mL) was added dropwise diisopropylethylamine (1.2, 9.8 mmol, 3.5 eq) at RT. After heating to 100° C., Dimethylamine (0.4 g, 5.6 mmol, 2 eq) was added at 100° C. After stirring at same temperature for 2 h, the reaction mixture was cooled to RT, quenched with water (50 mL) and extracted by 10% methanol in DCM (2×500). The combined organic layer was washed with brine (80 mL), dried over $Na_2SO_4$, filtered, and concentrated under reduced pressure to afford Intermediate AA194-4 (0.5 g), MS (ES): m/z 297.3 [M+1]$^+$ Step-6 Synthesis of 6-((dimethylamino)methyl)-5-(methylsulfonyl)pyridin-2-amine (Intermediate AA194)

To a solution of Intermediate AA194-4 (0.5 g, 1.6 mmol) in methanol: water (20 mL:5 mL) was added sodium hydroxide (0.673 g, 16.8 mmol, 10 eq). After stirring at RT for 16 h, the reaction mixture was concentrated under reduced pressure, diluted with water (30 mL), neutralized with 1N hydrochloric acid to pH-6.5 and extracted with DCM (3×30 mL). The combined organic layer was washed with brine solution, dried over sodium sulfate, and concentrated under reduced pressure to afford Intermediate AA194 (03 g, 64%). MS (ES): m/z 229.3 [M+H]$^+$.

Synthesis of 6-((dimethylamino)methyl)-5-(THF-3-yl)pyrazin-2-amine (Intermediate-AA195)

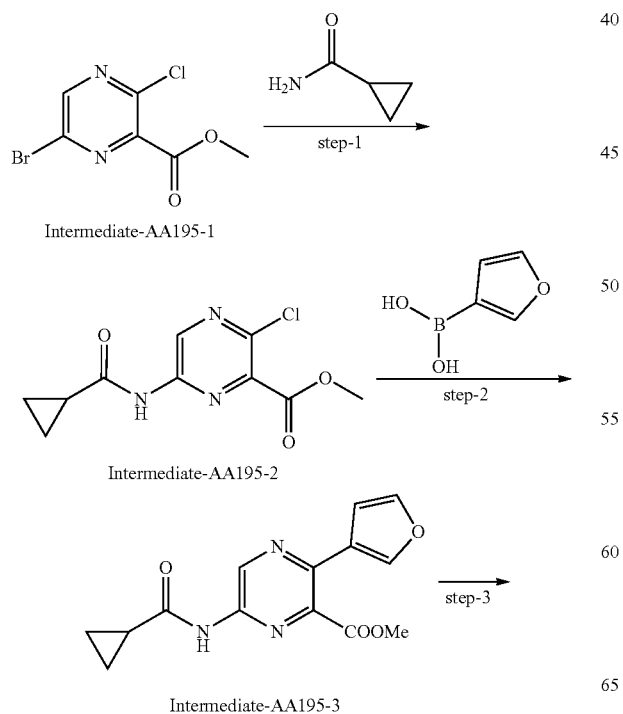

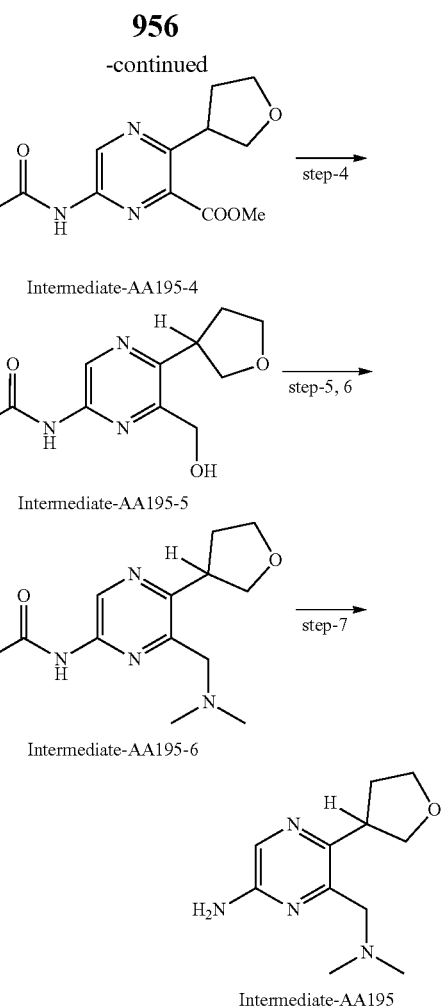

Synthesis of 6-((dimethylamino)methyl)-5-(THF-3-yl)pyrazin-2-amine (Intermediate AA195) was prepared from methyl 3-chloro-6-(cyclopropanecarboxamido)pyrazine-2-carboxylate (Intermediate AA195-2) in a similar fashion to that procedure describe in synthesis of tert-butyl ((6-amino-3-(THF-3-yl)pyridin-2-yl)methyl)carbamate (Intermediate AA149) (1.2 g, 87%). MS (ES) m/z 223.1 [M+H]$^+$ and Intermediate AA195-2 was synthesized according to similar process of Intermediate AA138-2.

Synthesis of 6-(4-methylpiperazin-1-yl)-5-(THF-3-yl)pyridin-2-amine (Intermediate-AA196)

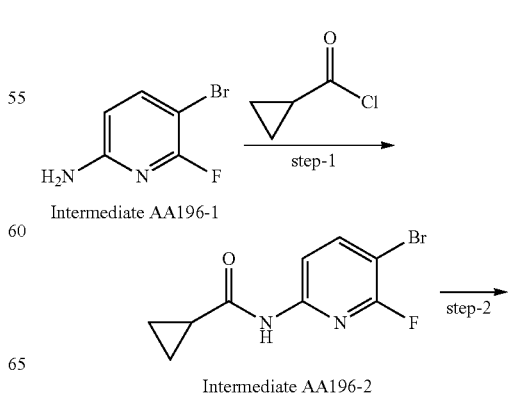

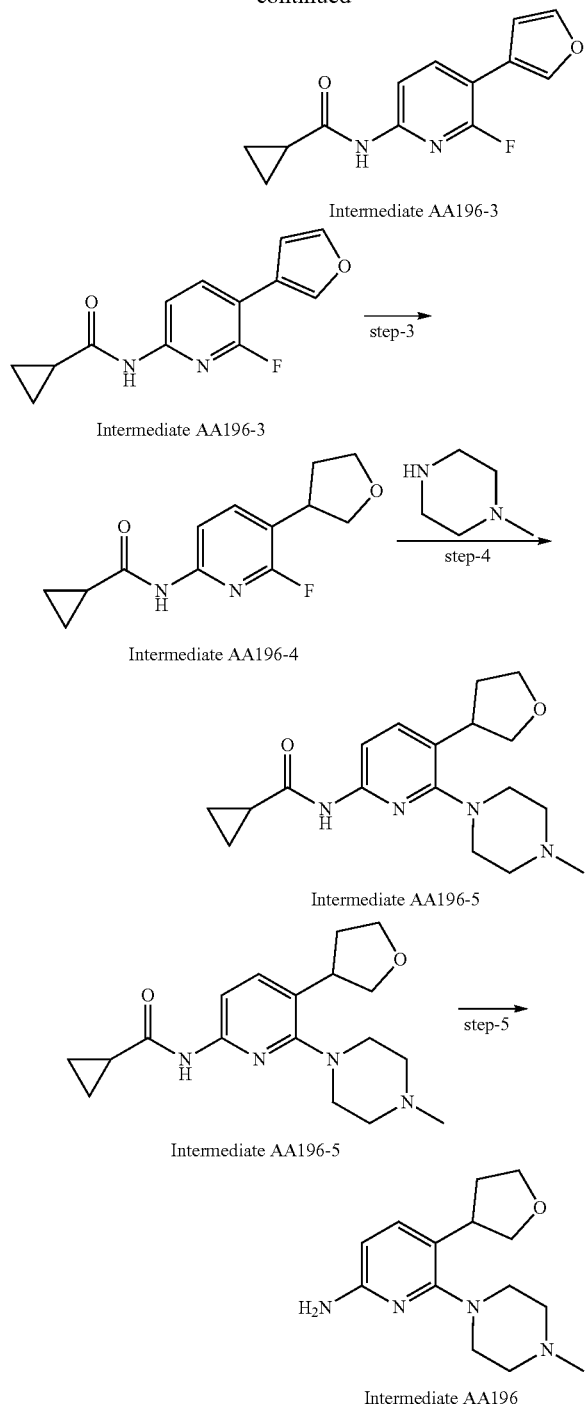

Step-1 Synthesis of N-(5-bromo-6-fluoropyridin-2-yl)cyclopropanecarboxamide (Intermediate AA196-2)

To a solution of Intermediate AA196-1 (5.0 g, 26.17 mmol) in DCM (50 mL) at 0° C. were added triethylamine (11.0 mL, 78.51 mmol, 3.0 eq) and cyclopropanecarbonyl chloride (10.8 g, 104.68 mmol, 4.0 eq). After stirring at RT for 2 h, the reaction mixture was diluted with water (150 mL) and extracted with DCM (3×70 mL). The combined organic extracts were washed with brine (200 mL), dried over Na$_2$SO$_4$, filtered, and concentrated under reduced pressure. The residue was purified by column chromatography (15-20% ethyl acetate gradient in hexane) to afford Intermediate AA196-2 (8.0 g, 95.84%) MS (ES): m/z=259.9 [M+H]$^+$.

Step-2 Synthesis of N-(6-fluoro-5-(furan-3-yl)pyridin-2-yl)cyclopropanecarboxamide (Intermediate AA196-3)

To a solution of Intermediate AA196-2 (4.0 g, 15.44 mmol) in dioxane (86 mL) and water (22 mL) were added furan-3-ylboronic acid (2.5 g, 23.16 mmol, 1.5 eq) and potassium phosphate tribasic (8.1 g, 38.6 mmol, 2.5 eq). After degassing with N$_2$ for 15 min. [1,1'-Bis(diphenylphosphino)ferrocene]dichloropalladium(II), complex with DCM (1.2 g, 1.54 mmol, 0.1 eq) was added. After stirring at 100° C. for 2 h, the reaction mixture was cooled to RT, diluted water (300 mL) and extracted with ethyl acetate (2×150 mL). The combined organic extracts were washed with brine (200 mL), dried over Na$_2$SO$_4$, filtered, and concentrated under reduced pressure. The residue was purified by column chromatography eluting with 34-37% ethyl acetate gradient in hexane to afford Intermediate AA196-3 (3.1 g, 81.54%), MS (ES): m/z 247.08 [M+H]+

Step-3 synthesis of N-(6-fluoro-5-(THF-3-yl)pyridin-2-yl)cyclopropanecarboxamide (Intermediate AA196-4)

To a solution of Intermediate AA196-3 (3.1 g, 12.60 mmol) in methanol (30 mL) and THF (10 mL) were added ammonium formate (1.5 g, 25.2 mmol, 2.0 eq), acetic acid (2.1 mL, 0.7V) and 20% wet palladium hydroxide on carbon (2.5 g). After stirring under atmosphere of hydrogen gas for 24 h at RT, the reaction mixture was filtered through Celite bed, and the filtrate was concentrated under reduced pressure. The residue was diluted with sat. NaHCO$_3$ solution and extracted by DCM. The organic solution was concentrated to afford Intermediate AA196-4 (2.6 g, 82.52%). MS (ES): m/z 251.1 [M+H]$^+$ Step-4 Synthesis of N-(6-(4-methylpiperazin-1-yl)-5-(THF-3-yl)pyridin-2-yl)cyclopropanecarboxamide (Intermediate AA196-5)

To a cooled solution of Intermediate AA196-4 (2.5 g, 10.00 mmol) in THF (50 mL) was added dropwise n-butyllithium (1.6M in hexane) (12.5 mL, 20 mmol, 2.0 eq) at 0° C. After stirring for 30 min at 0° C. 1-methylpiperazine (2.0 g, 20 mmol, 2.0 eq) dissolved in THF (10 mL) was added. After stirring for 2 h at RT, the reaction mixture was quenched with water (150 mL) and extracted by ethyl acetate (2×60 mL). The combined organic layer was washed with brine (100 mL), passed through a Na$_2$SO$_4$, and concentrated under reduced pressure. The residue was purified by column chromatography eluting 2.5% methanol gradient in DCM to afford Intermediate AA196-5 (1.5 g, 45.44%), MS (ES): m/z 331.2 [M+H]$^+$ Step-5 synthesis of 6-(4-methylpiperazin-1-yl)-5-(THF-3-yl)pyridin-2-amine (Intermediate AA196)

To a solution of Intermediate AA196-5 (0.350 g, 4.54 mmol) in methanol (6 mL) and water (2 mL) was added sodium hydroxide (1.8 g, 45.4 mmol, 10.0 eq). After stirring at 70° C. for 16 h, the reaction mixture was diluted with water (25 mL) and extracted with DCM (4×15 mL). The combined organic extracts were washed with brine, dried over Na$_2$SO$_4$, filtered, and concentrated under reduced pressure. The residue was purified by column chromatography eluting with 3% methanol gradient in DCM to afford Intermediate AA196 (0.9 g, 75.57%), m/z=263.1 [M+H]$^+$ Synthesis of 3-(6-amino-2-((dimethylamino)methyl) pyridin-3-yl)THF-3-ol (Intermediate-AA197)

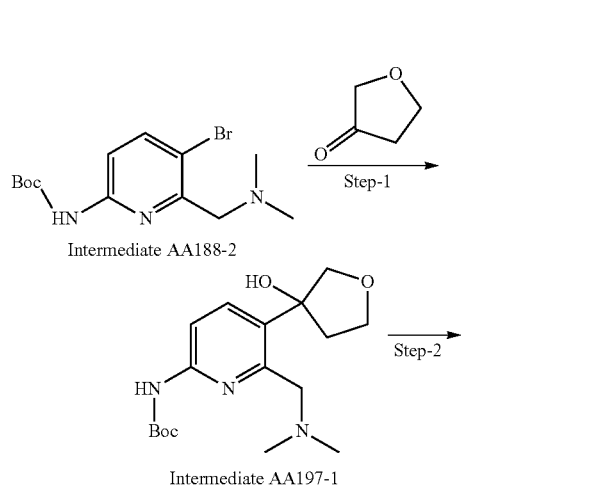

Step-1 Synthesis of Tert-Butyl (6-((dimethylamino) methyl)-5-(3-hydroxyTHF-3-yl)pyridin-2-yl)carbamate (Intermediate AA197-1)

To a solution of Intermediate AA188-2 (7.0 g, 21.21 mmol) in THF (70 mL) was added n-butyl lithium at −78° C. After stirring for 1 h at at −78° C., dihydrofuran-3(2H)-one (3.64 g, 42.42 mmol, 2.0 eq) dissolved in THF (10 mL) was added slowly dropwise. After stirring for 2 h at 78° C. warming to RT, the reaction mixture was quenched with ice cold water (500 mL) and extracted with ethyl acetate (3×100 mL). The combined organic extracts were washed with brine (250 mL), dried over Na$_2$SO$_4$, filtered, and concentrated under reduced pressure. The residue was purified by column chromatography eluting with 30% ethyl acetate gradient in hexane to afford Intermediate AA197-1 (3.7 g, 51.73%), MS (ES): m/z 338.2 [M+H]$^+$ Step-2 Synthesis of 3-(6-amino-2-((dimethylamino) methyl)pyridin-3-yl)THF-3-ol (Intermediate AA197)

The compound Intermediate AA197-1 (1.5 g, 4.45 mmol) in DCM (20 mL) was added trifluoroacetic acid (3 mL). After stirring at 50° C. for 2 h, the reaction mixture was quenched with saturated bicarbonate solution and extracted with DCM. The combined organic layer was dried over sodium sulfate, filtered, and concentrated under reduced pressure. The residue was purified by trituration with diethyl ether to afford Intermediate AA197 (0.75 g, 71.09%). MS (ES): m/z 238.1 [M+H]$^+$ Synthesis of R)-6-((dimethylamino)methyl)-5-((THF-3-yl)oxy)pyridin-2-amine (Intermediate-AA198)

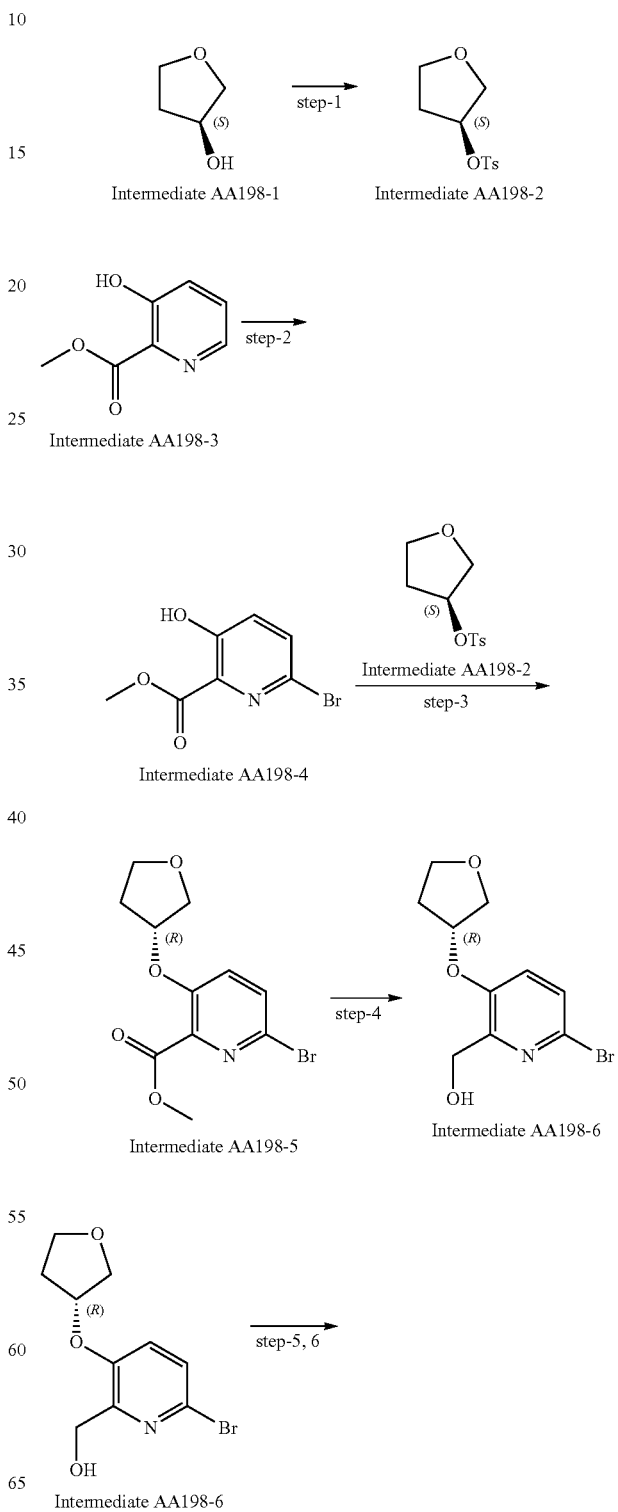

-continued

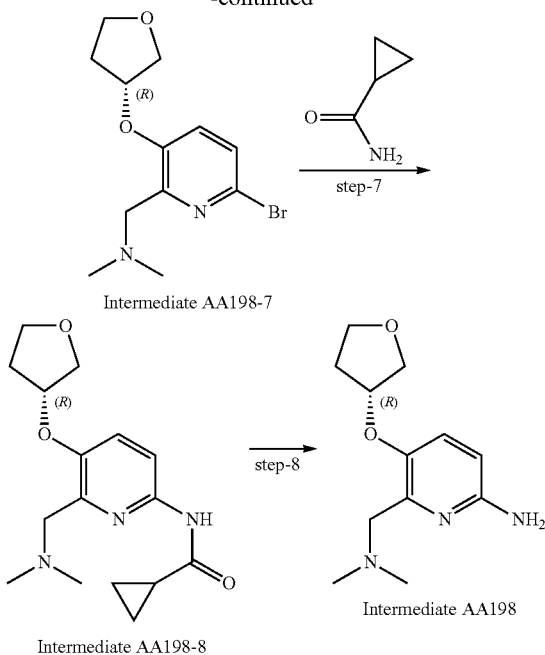

Intermediate AA198-7

Intermediate AA198-8

Intermediate AA198

Step-1 synthesis of S)-THF-3-yl 4-methylbenzenesulfonate (Intermediate AA198-2)

To a solution of the Intermediate AA198-1 (4.0 g, 45.45 mmol, 1.0 eq) in DCM (40 mL) at 0° C. were added trimethylamine (6.3 mL, 45.45 mmol) and DMAP (1.6 g, 13.63 mmol, 0.3 eq). After stirring for 10 min at 0° C., 4-toluenesulfonyl chloride (6.4 mL, 45.45 mmol) was added dropwise. After stirring for 30 min at RT and at 55° C. for 1 h, the reaction was diluted with 1N HCl (80 mL) and extracted into DCM (3×40 mL). The combined organic layer was washed with brine, filtered, and concentrated under reduced pressure. The residue was purified by silica gel chromatography eluting with 30% ethyl acetate in hexane to afford Intermediate AA198-2 (3.5 g, 31.82%) as a yellow oil. MS (ES): m/z 243.06 $[M+H]^+$

Step-2 synthesis of methyl 6-bromo-3-hydroxypicolinate (Intermediate AA198-4)

To a solution of Intermediate AA198-3 (5.0 g, 32.67 mmol) in water (50 mL) at 0° C. was added slowly dropwise bromine (2.0 mL, 39.20 mmol, 1.2 eq). After stirring for 2 h, the reaction mixture was extracted with DCM (3×80 mL). The combined organic extracts were washed with brine (250 mL), dried over $Na_2SO_4$, filtered, and concentrated under reduced pressure to afford Intermediate AA198-4 (4.0 g, 52.80%), MS (ES): m/z 232.9 $[M+H]^+$

Step-3 Synthesis of Methyl (R)-6-bromo-3-((THF-3-yl)oxy)picolinate (Intermediate AA198-5)

To a solution of Intermediate AA198-4 (4.0 g, 17.24 mmol) and Intermediate AA198-2 (5.4 g, 22.41 mmol, 1.5 eq) in DMF (20 mL) was added potassium carbonate (7.1 g, 51.72 mmol, 3.0 eq). After stirring at 90° C. for 16 h, the reaction was diluted with ice cold water (250 mL) and extracted into ethyl acetate (3×80 mL). The combined organic layer was washed with brine, filtered, and concentrated under reduced pressure. The residue was purified by silica gel chromatography eluting with 17% ethyl acetate in hexane to afford Intermediate AA198-5 (3.5 g, 67.20%) as a yellow oil. MS (ES): m/z 302.9 $[M+H]^+$.

Step-4 Synthesis of R)-(6-bromo-3-((THF-3-yl)oxy)pyridin-2-yl)methanol (Intermediate AA198-6)

To a solution of Intermediate AA198-5 (3.5 g, 11.58 mmol) in ethanol (35 mL) was added portion wise sodium borohydride (0.717 g, 23.16 mmol, 2.0 eq). After stirring at 60° C. for 30 min, the reaction was diluted with ice cold water (200 mL) and extracted into ethyl acetate (3×60 mL). The combined organic layer was washed with brine, filtered, and concentrated under reduced pressure. The residue was purified by silica gel chromatography eluting with 35% ethyl acetate in hexane to afford Intermediate AA198-6 (2.2 g, 69.28%). MS (ES): m/z 275.0 $[M+H]^+$.

Step-5, 6 Synthesis of R)-1-(6-bromo-3-((THF-3-yl)oxy)pyridin-2-yl)-N,N-dimethylmethanamine (Intermediate AA198-7)

To a cooled solution of Intermediate AA198-6 (3.0 g, 10.98 mmol) in DCM (20 mL) with N, N-Diisopropylethylamine (6.7 mL, 38.43 mmol, 3.5 eq) at 0° C. was added methane sulfonyl chloride (1.28 mL, 16.47 mmol, 1.5 eq) dropwise. After stirring at RT for 30 min, the reaction mixture was diluted with water (100 mL), washed with sodium bicarbonate solution, and extracted with DCM (3×30 mL). The combined organic extracts were washed with brine, dried over $Na_2SO_4$, filtered, and concentrated under reduced pressure (1.61 g).

To a solution of mesylated intermediate (1.9 g, 5.39) in acetonitrile (20 mL) was added N,N-Diisopropylethylamine (2.8 mL, 16.17 mmol, 3.0 eq) and N-methylethanamine (2.1 g, 26.95 mmol, 5.0 eq) at RT. After stirring 6 h at 90° C., the reaction mixture was diluted with ice cold water (150 mL) and extracted with DCM (3×40 mL). The combined organic extracts were washed with brine, dried over $Na_2SO_4$, filtered, and concentrated under reduced pressure. The residue was purified by silica gel chromatography eluting with 4.5% methanol in DCM to afford Intermediate AA198-7 (1.8 g, 74.46%) as a yellow oil. MS (ES): m/z 302.05 $[M+H]^+$.

Step-7 Synthesis of R)—N-(6-((dimethylamino)methyl)-5-((THF-3-yl)oxy)pyridin-2-yl)cyclopropanecarboxamide (Intermediate AA198-8)

To a solution of Intermediate AA198-7 (2.0 g, 6.64 mmol) in 1,4-dioxane (20 mL) were added cyclopropanecarboxamide (1.24 g, 14.61 mmol, 2.2 eq) and $K_2CO_3$ (2.74 g, 19.92 mmol, 3.0 eq). After degassing under $N_2$ stream for 15 min, Xantphos (0.383 g, 0.66 mmol, 0.1 eq) and $Pd_2(dba)_3$ (0.603 g, 0.66 mmol, 0.1 eq) were added. After stirring at 100° C. for 2 h, the reaction mixture was cooled to RT, diluted with water (150 mL), and extracted with ethyl acetate (3×70 mL). The combined organic extracts were washed with brine (100 mL), dried over $Na_2SO_4$, filtered, and concentrated under reduced pressure. The residue was purified by column chromatography eluting with 2-4% methanol gradient in DCM to afford Intermediate AA198-8 (1.8 g, 88.76%), m/z=306.18 $[M+H]^+$

Step-8 Synthesis of R)-6-((dimethylamino)methyl)-5-((THF-3-yl)oxy)pyridin-2-amine (Intermediate AA198)

To a solution of Intermediate AA198-8 (1.8 g, 5.90 mmol) in methanol (20 mL) and water (4 mL) was added sodium hydroxide (2.3 g, 59.0 mmol, 10.0 eq). After stirring at 90° C. for 16 h, the reaction mixture was cooled to RT, concentrated under reduced pressure, diluted with water (100 mL), and extracted with DCM (3×40 mL). The combined organic extracts were washed with brine (60 mL), dried over Na$_2$SO$_4$, filtered, and concentrated under reduced pressure. The residue was purified by trituration with hexane to afford Intermediate AA198 (0.9 g, 57.19%), MS (ES): m/z 238.1 [M+H]$^+$ Synthesis of R)-1-((6-amino-3-((R)-THF-3-yl)pyridin-2-yl)methyl)pyrrolidin-3-ol (Intermediate-AA199)

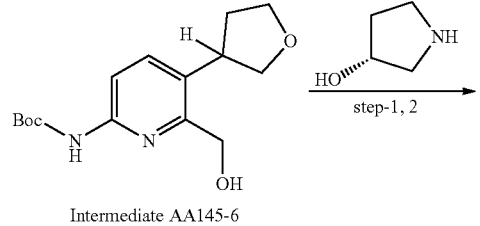

Intermediate AA145-6

(R)-1-((6-amino-3-((R)-THF-3-yl)pyridin-2-yl)methyl) pyrrolidin-3-ol (Intermediate-AA199) was prepared from tert-butyl (6-(hydroxymethyl)-5-(THF-3-yl)pyridin-2-yl) carbamate (Intermediate AA145-6) and (R)-pyrrolidin-3-ol in a similar fashion to that procedure of step-6, step-7 and step-8 described in synthesis of 5-cyclopentyl-6-((dimethylamino)methyl)pyridin-2-amine (Intermediate AA145) (0.8 g, quantitative %). m/z 264.1 [M+H]$^+$ Synthesis of 6-((1-methylazetidin-3-yl)oxy)-5-(THF-3-yl)pyridin-2-amine (Intermediate-AA200)

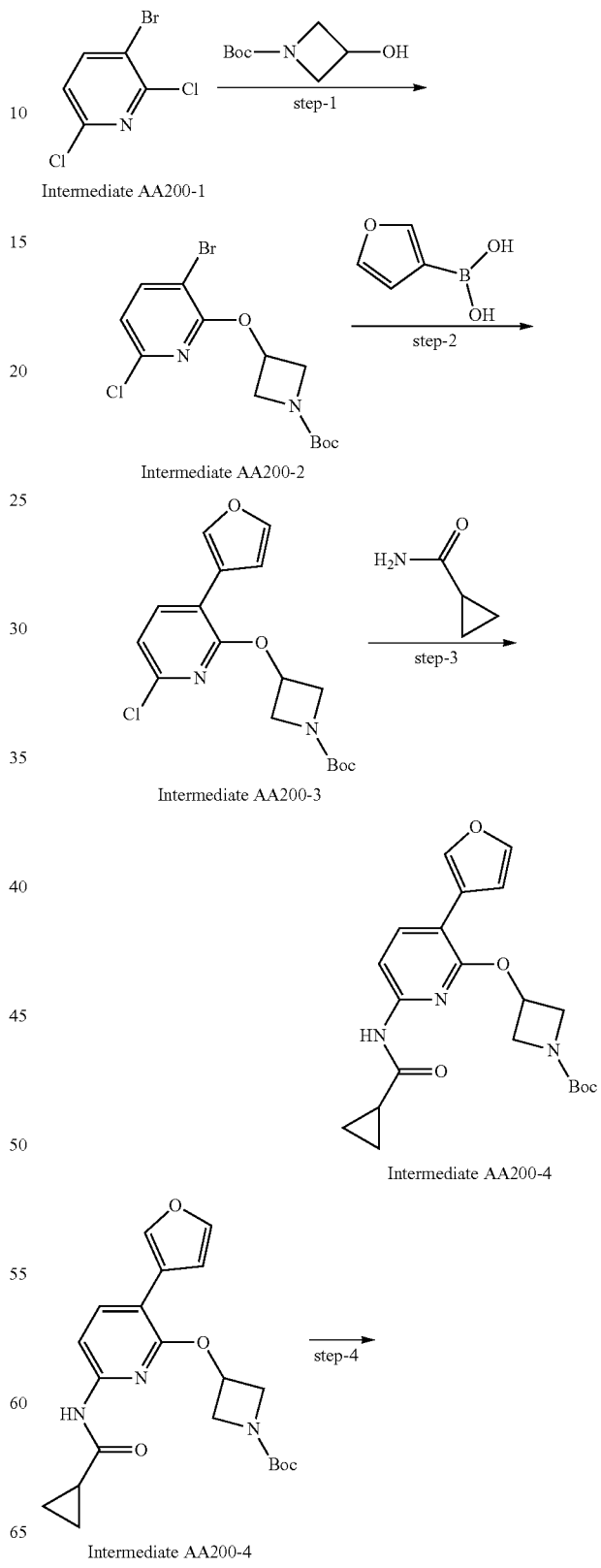

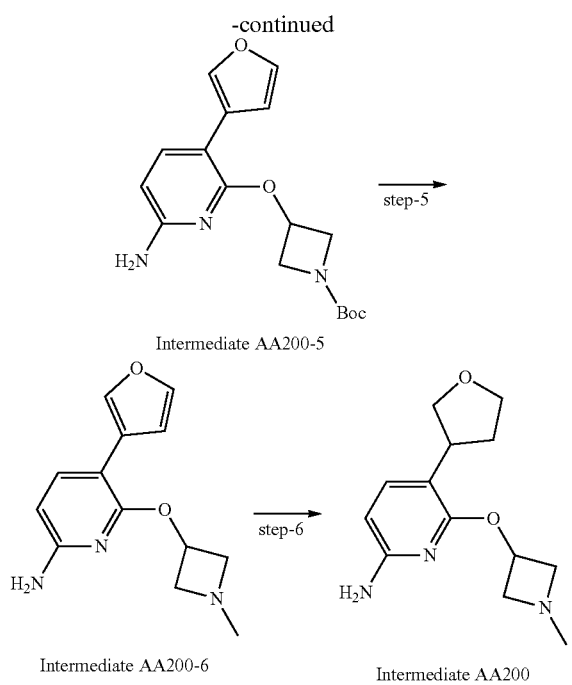

Step-1 Synthesis of Tert-Butyl 3-((3-bromo-6-chloropyridin-2-yl)oxy)azetidine-1-carboxylate (Intermediate AA200-2)

To a solution of Intermediate AA200-1 (15.0 g, 66.37 mmol) and tert-butyl 3-hydroxyazetidine-1-carboxylate (17.22 g, 99.55 mmol, 1.5 eq) in acetonitrile (150 mL) was added cesium carbonate (43.1 g, 132.74 mmol, 3.0 eq). After stirring at RT for 16 h, the reaction mixture was diluted with water (500 mL) and extracted with ethyl acetate (3×200 mL). The combined organic extracts were washed with brine (250 mL), dried over $Na_2SO_4$, filtered, and concentrated under reduced pressure. The residue was purified by column chromatography eluting with 1-3% gradient of ethyl acetate in hexane to afford Intermediate AA200-2 (14.0 g, 58.23%), MS (ES): m/z 364.00 [M+H]$^+$

Step-2 Synthesis of Tert-Butyl 3-((6-chloro-3-(furan-3-yl)pyridin-2-yl)oxy)azetidine-1-carboxylate (Intermediate AA200-3)

A solution of Intermediate AA200-2 (14.0 g, 38.56 mmol) in 1,4-Dioxane:water (140 mL:30 mL) were added furan-3-ylboronic acid (8.63 g, 77.12 mmol, 2.0 eq) and sodium carbonate (8.1 g, 77.12 mmol, 2.0 eq). After degassing under $N_2$ stream for 15 min [1,1'-Bis(diphenylphosphino)ferrocene]dichloropalladium(II), complex with DCM (3.1 g, 3.85 mmol, 0.1 eq) was added. After stirring at 80° C. 16 h, the reaction mixture was filtered through celite-bed. The filtrate was diluted with water (400 mL) and extracted with ethyl acetate (3×200 mL). The combined organic extracts were washed with brine (250 mL), dried over $Na_2SO_4$, filtered, and concentrated under reduced pressure. The residue was purified by column chromatography eluting with 30% ethyl acetate gradient in hexane to afford Intermediate AA200-3 (9.0 g, 66.64%) as a brown solid. MS (ES): m/z=351.1 [M+H]$^+$

Step-3 synthesis of tert-butyl 3-((6-(cyclopropanecarboxamido)-3-(furan-3-yl)pyridin-2-yl)oxy)azetidine-1-carboxylate (Intermediate AA200-4)

To a solution of Intermediate AA200-3 (9.0 g, 25.71 mmol) in 1,4-dioxane (90 mL) were added cyclopropanecarboxamide (4.37 g, 51.42 mmol, 2.0 eq) and $K_2CO_3$ (10.64 g, 77.13 mmol, 3.0 eq). After degassing under $N_2$ stream for 15 min, Xantphos (1.48 g, 2.57 mmol, 0.1 eq) and $Pd_2(dba)_3$ (2.3 g, 2.57 mmol, 0.1 eq) were added. After stirring at 110° C. for 16 h, the reaction mixture was cooled to RT, diluted water (500 mL) and extracted with ethyl acetate (3×200 mL). The combined organic extracts were washed with brine (200 mL), dried over $Na_2SO_4$, filtered, and concentrated under reduced pressure. The residue was purified by column chromatography eluting with 25-30% ethyl acetate gradient in hexane to afford Intermediate AA200-4 (6.5 g, 63.43%), m/z=400.18 [M+H]$^+$.

Step-4 Synthesis of Tert-Butyl 3-((6-amino-3-(furan-3-yl)pyridin-2-yl)oxy)azetidine-1-carboxylate (Intermediate AA200-5)

To a solution of Intermediate AA200-4 (6.5 g, 16.29 mmol) in methanol (70 mL) and water (20 mL) was added sodium hydroxide (6.51 g, 162.9 mmol, 10.0 eq). After stirring at 80° C. for 16 h, the reaction mixture was quenched with ice cold water, neutralized with 2N HCl solution, and extracted with ethyl acetate (3×100 mL). The combined organic extracts were washed with brine (150 mL), dried over $Na_2SO_4$, filtered, and concentrated under reduced pressure The residue was purified by column chromatography eluting with 20-30% ethyl acetate gradient in hexane to afford Intermediate AA200-5 (2.8 g, 51.93%), MS (ES): m/z 332.16 [M+H]$^+$.

Step-5 Synthesis of 5-(furan-3-yl)-6-((1-methylazetidin-3-yl)oxy)pyridin-2-amine (Intermediate AA200-6)

To a cooled solution of Intermediate AA200-5 (2.8 g, 8.45 mmol) in THF (30 mL) at −10° C. was added lithium aluminum hydride (1.0 mL, 25.35 mmol, 3.0 eq). After stirring at RT for 2 h, the reaction mixture was quenched with ice cold water and ethyl acetate and filtered through celite-bed. The aqueous layer was extracted with ethyl acetate (3×80 mL). The combined organic extracts were washed with brine (150 mL), dried over $Na_2SO_4$, filtered, and concentrated under reduced pressure The residue was purified by column chromatography eluting with 0-10% methanol gradient in DCM to afford Intermediate AA200-6 (1.2 g, 57.90%), MS (ES): m/z 246.1 [M+H]$^+$.

Step-6 Synthesis of 6-((1-methylazetidin-3-yl)oxy)-5-(THF-3-yl)pyridin-2-amine (Intermediate AA200)

To a solution of Intermediate AA200-6 (1.2 g, 4.89 mmol) in methanol: THF (10 mL:2 mL) were added acetic acid (0.8 mL), palladium hydroxide on carbon (0.6 g) and ammonium format (1.2 g, 19.56 mmol, 4.0 eq). After stirring under hydrogen gas at atmospheric pressure for 16 h at RT, the reaction mixture was filtered through celite-bed and washed with methanol. The filtrate was concentrated under reduced pressure. The residue was purified by trituration with n-pentane to afford Intermediate AA200 (0.9 g, 73.79%). MS (ES): m/z 250.15 [M+H]$^+$

Synthesis of 6-(1-(dimethylamino)ethyl)-5-(THF-3-yl)pyridin-2-amine (Intermediate-AA201)

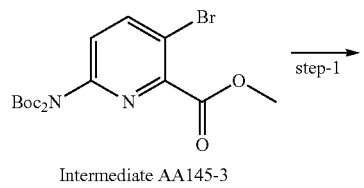

Intermediate AA145-3

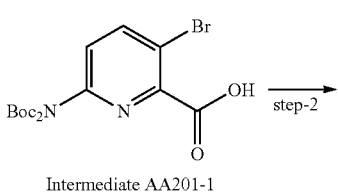

Intermediate AA201-1

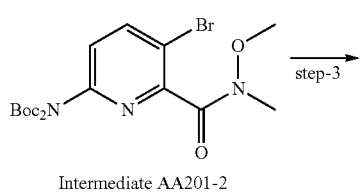

Intermediate AA201-2

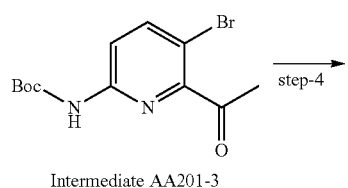

Intermediate AA201-3

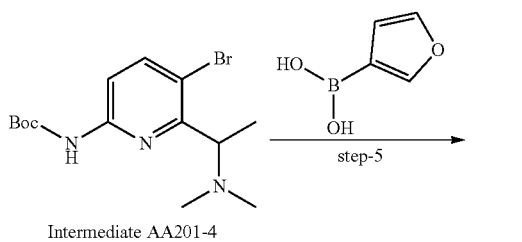

Intermediate AA201-4

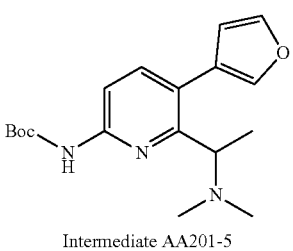

Intermediate AA201-5

-continued

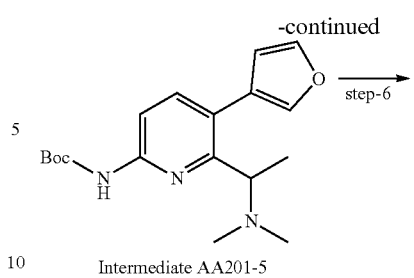

Intermediate AA201-5

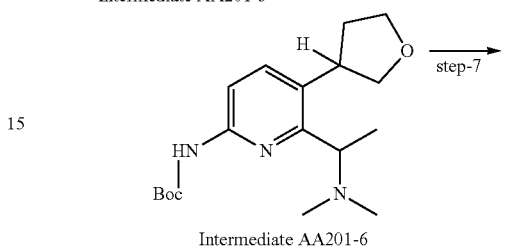

Intermediate AA201-6

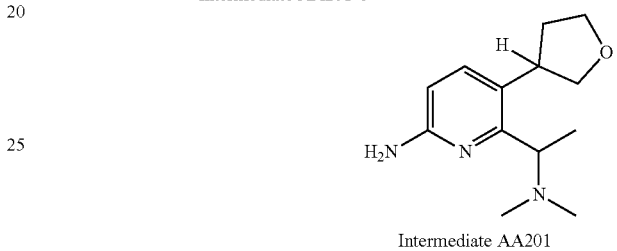

Intermediate AA201

Step-1 Synthesis of 3-bromo-6-((tert-butoxycarbonyl)amino)picolinic acid (Intermediate AA201-1)

To a solution of Intermediate AA145-3 (20.0 g, 46.51 mmol) in THF: methanol:water (200 mL:200 mL:30 mL) was added sodium hydroxide (9.3 g, 232.55 mmol, 5.0 eq). After stirring at RT for 16 h, the reaction mixture was concentrated under reduced pressure. The residue was neutralized with citric acid solution whereby a solid precipitate from solution. The solid was filtered and dried under high vacuum to afford Intermediate AA201-1 (13.6 g, 70.29%), MS (ES): m/z 418.06 [M+H]$^+$

Step-2 Synthesis of Tert-Butyl (5-bromo-6-(methoxy(methyl)carbamoyl)pyridin-2-yl)carbamate (Intermediate AA201-2)

To a solution of Intermediate AA201-1 (5.0 g, 11.96 mmol) in DMF (50 mL) were added N,O-dimethylhydroxylamine hydrochloride (1.4 g, 14.35 mmol, 1.2 eq), hydroxybenzotriazole (2.4 g, 17.94 mmol, 1.5 eq), 1-(3-dimethylaminopropyl)-3-ethylcarbodiimide hydrochloride (5.7 g, 29.9 mmol, 2.5 eq) and triethylamine (5.0 mL, 35.88 mmol, 3.0 eq). After stirring at RT for 8 h, the reaction mixture was transferred into water (200 mL) and extracted with ethyl acetate (3×60 mL). The combined organic layer was washed with brine solution, dried over sodium sulfate, and concentrated under reduced pressure. The residue was purified by column chromatography eluting with 20% ethyl acetate in hexane to afford Intermediate AA201-2 (4.6 g, 83.39%). MS (ES): m/z 461.1 [M+H]$^+$

Step-3 Synthesis of Tert-Butyl (6-acetyl-5-bromopyridin-2-yl)carbamate (Intermediate AA201-3)

To a solution of Intermediate AA201-2 (4.6 g, 10.00 mmol) in THF (50 mL)) at 0° C. was added dropwise 3M methyl magnesium bromide solution (1.48 g, 2.57 mmol, 0.1 eq). After stirring at RT for 6 h, the reaction mixture was diluted with sodium bicarbonate solution (80 mL), extracted with ethyl acetate (3×30 mL) and filtered through celite-bed. The combined organic extracts were concentrated under reduced pressure. The residue was purified by column chromatography eluting with 20-25% ethyl acetate gradient in hexane to afford Intermediate AA201-3 (3.1 g, 98.43%), m/z=316.02 [M+H]$^+$.

Step-4 Synthesis of Tert-Butyl (5-bromo-6-(1-(dimethylamino)ethyl)pyridin-2-yl)carbamate (Intermediate AA201-4)

To a solution of Intermediate AA201-3 (2.8 g, 9.84 mmol) in methanol (30 mL) were added acetic acid (2.8 mL) and dimethylamine solution (2M in THF). After stirring at RT for 1 h, sodium cyanoborohydride (3.0 g, 49.2 mmol, 5.0 eq) was added portion wise. After stirring at 70° C. for 2 h, the reaction mixture was diluted with water (100 mL) and extracted with ethyl acetate (3×70 mL). The combined organic extracts were washed with brine (150 mL), dried over Na$_2$SO$_4$, filtered, and concentrated under reduced pressure The residue was purified by column chromatography eluting with 1-5% methanol gradient in DCM to afford Intermediate AA201-4 (1.9 g, 56.11%), MS (ES): m/z 345.09 [M+H]$^+$.

Step-5 Synthesis of Tert-Butyl (6-(1-(dimethylamino)ethyl)-5-(furan-3-yl)pyridin-2-yl)carbamate (Intermediate AA201-5)

To a solution of Intermediate AA201-4 (1.9 g, 5.53 mmol) and furan-3-ylboronic acid (0.93 g, 8.29 mmol, 1.5 eq) in 1,4-dioxane:water (20 mL:4 mL) was added potassium phosphate tribasic (3.5 g, 16.59 mmol, 3.0 eq). After degassing under N$_2$ stream for 15 min, Xphose PdG2 (0.434 g, 0.55 mmol, 0.1 eq) was added. After stirring at 120° C. for 20 min, the reaction mixture was diluted with water (50 mL) and extracted with ethyl acetate (3×25 mL). The combined organic extracts were washed with brine (80 mL), dried over Na$_2$SO$_4$, filtered, and concentrated under reduced pressure The residue was purified by column chromatography eluting with 3% methanol gradient in DCM to afford Intermediate AA201-5 (1.1 g, 60.14%), MS (ES): m/z 332.1 [M+H]$^+$ Step-6 Synthesis of Tert-Butyl (6-(1-(dimethylamino)ethyl)-5-(THF-3-yl)pyridin-2-yl)carbamate (Intermediate AA201-6)

To a solution of Intermediate AA201-5 (1.1 g, 3.32 mmol) in methanol: THF (10 mL:2 mL) were added acetic acid (0.8 mL), palladium hydroxide on carbon (0.6 g) and ammonium format (1.2 g, 19.92 mmol, 6.0 eq). After stirring under hydrogen gas at atmospheric pressure for 16 h at RT, the reaction mixture was filtered through celite-bed and washed with methanol. The filtrate was concentrated under reduced pressure. The residue was purified by trituration with n-pentane to afford Intermediate AA201-6 (1.0 g, 89.82%). MS (ES): m/z 336.22 [M+H]$^+$ Step-7 Synthesis of 6-(1-(dimethylamino)ethyl)-5-(THF-3-yl)pyridin-2-amine (Intermediate AA201)

To a solution compound Intermediate AA201-6 (1.5 g, 2.98 mmol) in DCM (15 mL) was added trifluoroacetic acid (4 mL). After stirring at RT for 1 h, the reaction mixture concentrated under reduced pressure. The residue was diluted with water (30 mL) and DCM (15 mL). The aqueous layer was collected, neutralized by 1N NaOH solution and extracted with 10% methanol in DCM (3×25 mL). The combined organic extracts were washed with brine (40 mL), dried over Na$_2$SO$_4$, filtered, and concentrated under reduced pressure to afford Intermediate AA201 (0.560 g, 79.82%). MS (ES): m/z 236.1 [M+H]$^+$ Synthesis of 4-(6-chloro-2-((dimethylamino)methyl)pyridin-3-yl)-1,4-oxazepan-6-ol (Intermediate-AA202)

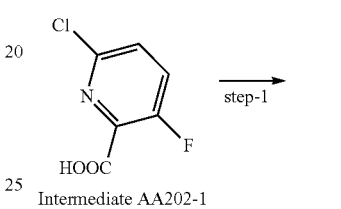

Intermediate AA202-1

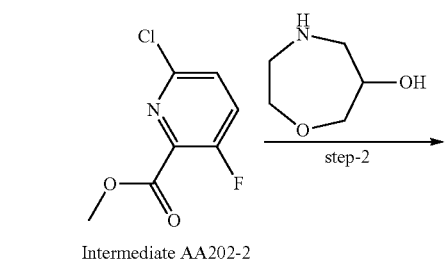

Intermediate AA202-2

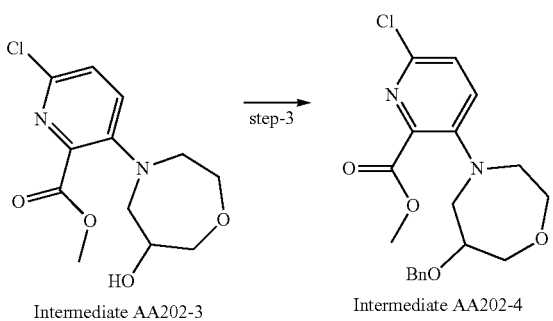

Intermediate AA202-3    Intermediate AA202-4

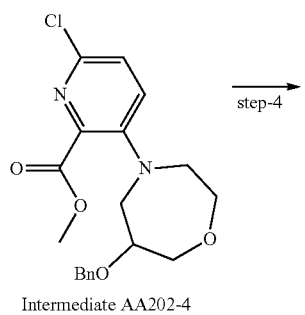

Intermediate AA202-4

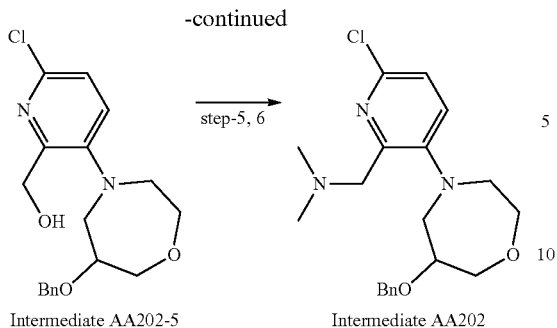

Intermediate AA202-5 → Intermediate AA202

Step-1 Synthesis of methyl 6-chloro-3-fluoropicolinate (Intermediate AA202-1)

To a solution of Intermediate AA202-1 (4.0 g, 22.85 mmol) in DMF (40 mL) with potassium carbonate (15.7 g, 114.25 mmol, 5.0 eq) at 0° C. was added methyl iodide (4.2 mL, 68.55 mmol, 3.0 eq) dropwise. After stirring from 0-RT for 1 h, the reaction mixture was diluted with water (250 mL) and extracted with ethyl acetate (3×80 mL). The combined organic extracts were washed with brine (120 mL), dried over $Na_2SO_4$, filtered, and concentrated under reduced pressure to afford Intermediate AA202-1 (2.58 g, 59.73%), MS (ES): m/z 190.0 $[M+H]^+$

Step-2 Synthesis of methyl 6-chloro-3-(6-hydroxy-1,4-oxazepan-4-yl)picolinate (Intermediate AA202-2)

To a solution of Intermediate AA202-1 (2.5 g, 13.22 mmol) and 1,4-oxazepan-6-ol (3.0 g, 26.45 mmol, 2.0 eq) in DMF (25 mL) was added N, N-Diisopropylethylamine (11.5 mL, 66.1 mmol, 5.0 eq). After stirring at 80° C. for 16 h, the reaction mixture was cooled to RT, diluted with ice cold water (80 mL) and extracted with ethyl acetate (3×30 mL). The combined organic extracts were washed with brine (60 mL), dried over $Na_2SO_4$, filtered, and concentrated under reduced pressure. The residue was purified by column chromatography eluting with 40-45% ethyl acetate gradient in hexane to afford Intermediate AA202-2 (1.5 g, 39.67%), MS (ES): m/z 287.08 $[M+H]^+$

Step-3 Synthesis of methyl 3-(6-(benzyloxy)-1,4-oxazepan-4-yl)-6-chloropicolinate (Intermediate AA202-4)

To a solution of Intermediate AA202-2 (0.9 g, 3.14 mmol) in DMF (10 mL) at 0° C. was added portion wise 60% sodium hydride (0.376 g, 9.42 mmol, 3.0 eq). After stirring for 30 min at 0° C., benzyl bromide (0.5 mL, 4.71 mmol, 1.5 eq) was added dropwise. After stirring for 1 h, the reaction mixture was quenched with ice cold water (30 mL) and extracted with ethyl acetate (3×30 mL). The combined organic extracts were washed with brine (60 mL), dried over $Na_2SO_4$, filtered, and concentrated under reduced pressure. The residue was purified by column chromatography eluting with 2% methanol gradient in DCM to afford Intermediate AA202-4 (0.750 g, 63.40%), m/z=377.1 $[M+H]^+$.

Step-4 Synthesis of 3-(6-(benzyloxy)-1,4-oxazepan-4-yl)-6-chloropyridin-2-yl)methanol (Intermediate AA202-5)

To a solution of Intermediate AA202-4 (0.750 g, 1.99 mmol) in ethanol (8 mL) at 0° C. was added portion wise sodium borohydride (0.376 g, 9.95 mmol, 5.0 eq). After stirring at RT for 2 h, the reaction was diluted with ice cold water (80 mL) and extracted into ethyl acetate (3×30 mL). The combined organic layer was washed with brine, dried over sodium sulfate, filtered, and concentrated under reduced pressure. The residue was purified by silica gel chromatography eluting with 20% ethyl acetate in hexane to afford Intermediate AA202-5 (0.5 g, 72.02%). MS (ES): m/z 349.12 $[M+H]^+$.

Step-5,6 Synthesis of 1-(3-(6-(benzyloxy)-1,4-oxazepan-4-yl)-6-chloropyridin-2-yl)-N,N-dimethyl-methanamine (Intermediate AA202)

To a solution of Intermediate AA202-5 (0.5 g, 1.43 mmol) in DCM at 0° C. (5 mL) with triethylamine (1.0 mL, 7.15 mmol, 5.0 eq) was added methane sulfonyl chloride (0.33 mL, 4.29 mmol, 3.0 eq) dropwise. After stirring at RT for 30 min, the reaction mixture was diluted with water (50 mL), washed with sodium bicarbonate solution, and extracted with DCM (3×20 mL). The combined organic extracts were washed with brine, dried over $Na_2SO_4$, filtered, and concentrated under reduced pressure to afford mesylate intermediate (0.39 g).

To the mesylate intermediate (0.39 g, 0.91 mmol) in acetonitrile (5 mL) were added N,N-diisopropylethylamine (1.56 mL, 9.1 mmol, 10 eq) and N-methylethanamine (0.773 g, 9.1 mmol, 10.0 eq) at RT. After stirring for 6 h at 90° C., the reaction mixture was diluted with ice cold water (150 mL) and extracted with DCM (3×40 mL) The combined organic extracts were washed with brine, dried over $Na_2SO_4$, filtered, and concentrated under reduced pressure. The residue was purified by silica gel chromatography eluting with 4.5% methanol in DCM to afford Intermediate AA202 (1.8 g, 63.10%). MS (ES): m/z 376.17 $[M+H]^+$

Synthesis of 1-(6-chloro-3-(1-methoxycyclopropyl)pyridin-2-yl)-N,N-dimethylmethanamine (Intermediate AA203)

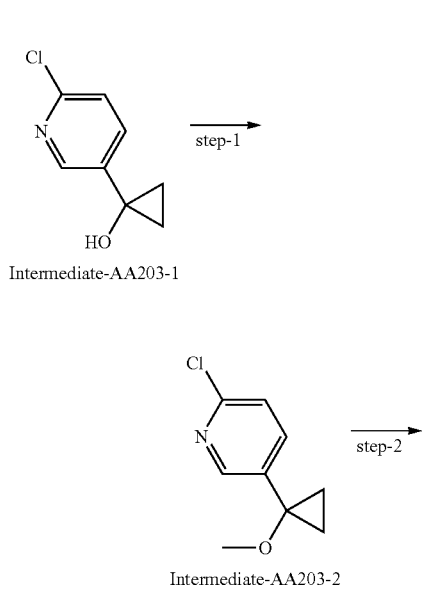

Intermediate-AA203-1

Intermediate-AA203-2

-continued

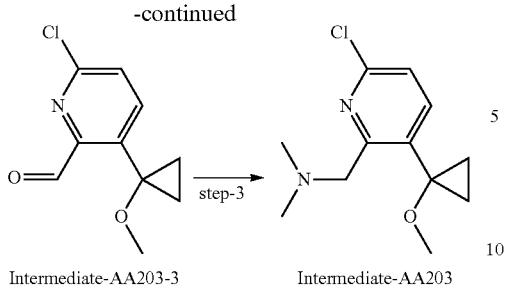

Intermediate-AA203-3 → Intermediate-AA203
step-3

Intermediate-AA203-1 was synthesize using the procedure of WO2008/110611.

Step-1 Synthesis of 2-chloro-5-(1-methoxycyclopropyl)pyridine (Intermediate-AA203-2)

To a solution of Intermediate-AA203-1 (1.5 g, 3.09 mmol, 1 eq) in THF at 0° C. was added NaH (0.123 g, 6.1 mmol, 2 eq). After stirring at RT for 15 min, MeI (0.5 g, 4.6 mmol, 1.5 eq) was added. After stirring for 2 h, the reaction was diluted ethyl acetate (70 mL) and water (20 mL). The organic layer was collected, and the aqueous phase was extract with ethyl acetate (2×30 mL). The combined organic extracts were washed with brine (50 mL), dried over $Na_2SO_4$, filtered, and concentrated under reduced pressure to afford Intermediate-AA203-1 (1.2 g, 73.5%). MS (ES): m/z=183.64 [M+1]+.

Step-2 Synthesis of 2-chloro-5-(1-methoxycyclopropyl)pyridine 1-oxide (Intermediate-AA203-3) and Step-3 Synthesis of 1-(6-chloro-3-(1-methoxycyclopropyl)pyridin-2-yl)-N,N-dimethylmethanamine (Intermediate-AA203)

2-chloro-5-(1-methoxycyclopropyl)pyridine 1-oxide (Intermediate-AA203-3) and 1-(6-chloro-3-(1-methoxycyclopropyl)pyridin-2-yl)-N,N-dimethylmethanamine (Intermediate AA202) were prepared from Intermediate AA203-2 in a similar fashion to that procedure of step-4, step-5 described in synthesis of 6-chloro-3-(4-(methoxymethyl)tetrahydro-2H-pyran-4-yl)picolinonitrile (Intermediate AA208) (150 mg, 33% overall two step). MS (ES): m/z=241.73 (M+H)+.

Synthesis of 4-(6-chloro-2-((dimethylamino)methyl)pyridin-3-yl)tetrahydro-2H-pyran-4-carbonitrile (Intermediate AA204)

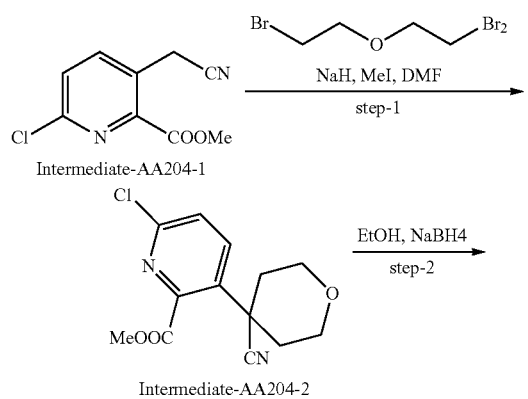

Intermediate-AA204-1
Intermediate-AA204-2

-continued

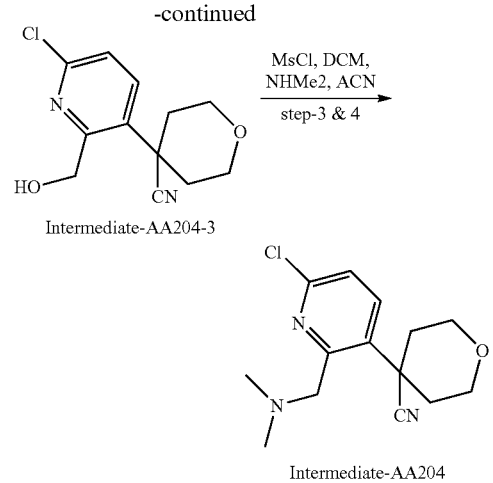

Intermediate-AA204-3 → Intermediate-AA204

Intermediate-AA204-1 was synthesized using the procedure of WO2015/94912, 2015, A1

Step-1 Synthesis of Methyl 6-chloro-3-(4-cyanotetrahydro-2H-pyran-4-yl)picolinate (Intermediate-AA204-2)

To a solution of Intermediate-AA204-1) (1 g, 4.7 mmol, 1 eq), in THF (10 mL) at 0° C. was added NAH (0.571 g, 14.2 mmol, 3 eq). After stirring at 0° C. for 30 min, 1-bromo-2-(2-bromoethoxy)ethane (2.15 g, 9.4 mmol, 2 eq) was added. After stirring at RT for 1 h, the reaction mixture was diluted with water (50 mL) and extracted with ethyl acetate (50 mL). The combined organic extracts were washed with brine (60 mL), dried over $Na_2SO_4$, filtered, and concentrated under reduced pressure. The residue was purified by column chromatography to afford Intermediate-AA204-2 (600 mg, 45%). MS (ES): m/z=280.71 [M+1]+

Step-2 Synthesis of 4-(6-chloro-2-(hydroxymethyl)pyridin-3-yl)tetrahydro-2H-pyran-4-carbonitrile (Intermediate-AA204-3)

To a solution of Intermediate-AA204-2 (1.5 g, 5.3 mmol, 1 eq) in EtOH (20 mL) at 0° C. was added $NaBH_4$ (0.5 g, 10.6 mmol, 2 eq). After stirring at RT for 2 h, the reaction was concentrated, diluted with water (50 mL), and extracted with ethyl acetate (3×40 mL). The combined organic extracts were wash with brine (50 mL), dried over $Na_2SO_4$, filtered, and concentrated under reduced pressure to afford Intermediate-AA204-2. (1.1 g, 81%) MS (ES): m/z=253.5 $[M+H]^+$.

Step-3 & Step-4 Synthesis of 4-(6-chloro-2-((dimethylamino)methyl)pyridin-3-yl)tetrahydro-2H-pyran-4-carbonitrile (Intermediate-AA204)

To a solution of Intermediate-AA204-2 (1 g, 4.7, 1 eq) in DCM (10 mL) at 0° C. were added DIPEA (2.12 g, 16.45 mmol, 3.5 eq) and methane sulfonyl chloride (0.4 g, 7.05 mmol, 1.5 eq). After stirring at 0° C. for 30 min, the reaction mixture was diluted with water (50 mL) and extracted with ethyl acetate (3×40 mL). The combined organic extracts were wash with brine (50 mL), dried over $Na_2SO_4$, filtered, and concentrated under reduced pressure to afford mesylate intermediate (1.2 g) MS (ES): m/z=331.5 $[M+H]^+$.

To a solution of mesylated intermediate (1.2 g, 3.6 mmol) in MeCN (12 mL) was added dropwise DIPEA (2.1 g, 16.3 mmol, 4.5 eq) and dimethylamine hydrochloride (0.8 g, 7.2 mmol, 2.0 eq) at RT. After stirring at 90° C. for 3 h, the reaction mixture was concentrated, quenched in water (55 mL), and extracted by DCM (3×30 L). The combined organic layer was washed with brine (80 mL), dried with Na$_2$SO$_4$, and concentrated under reduced pressure to afford Intermediate-AA204 (600 mg, quantitative yield), as brown semi solid. MS (ES): m/z 280.39 [M+1]$^+$.

Synthesis of (2R)-1-((6-amino-3-(THF-3-yl)pyridin-2-yl)methyl)pyrrolidin-2-yl)methanol (Intermediate-AA205)

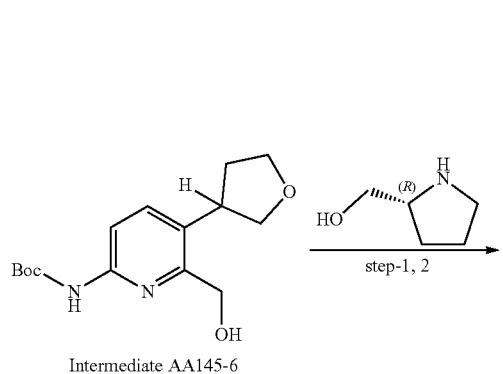

((2R)-1-((6-amino-3-(THF-3-yl)pyridin-2-yl)methyl)pyrrolidin-2-yl)methanol (Intermediate-AA205) was prepared from tert-butyl (6-(hydroxymethyl)-5-(THF-3-yl)pyridin-2-yl)carbamate (Intermediate AA145-6) and (R)-pyrrolidin-2-ylmethanol in a similar fashion to that procedure of step-6, step-7 and step-8 described in synthesis of 5-cyclopentyl-6-((dimethylamino)methyl)pyridin-2-amine (Intermediate AA145) (0.85 g, quantitative %). m/z 278.1 [M+H]$^+$ Synthesis of (2S)-1-((6-amino-3-(THF-3-yl)pyridin-2-yl)methyl)pyrrolidin-2-yl)methanol (Intermediate-AA206)

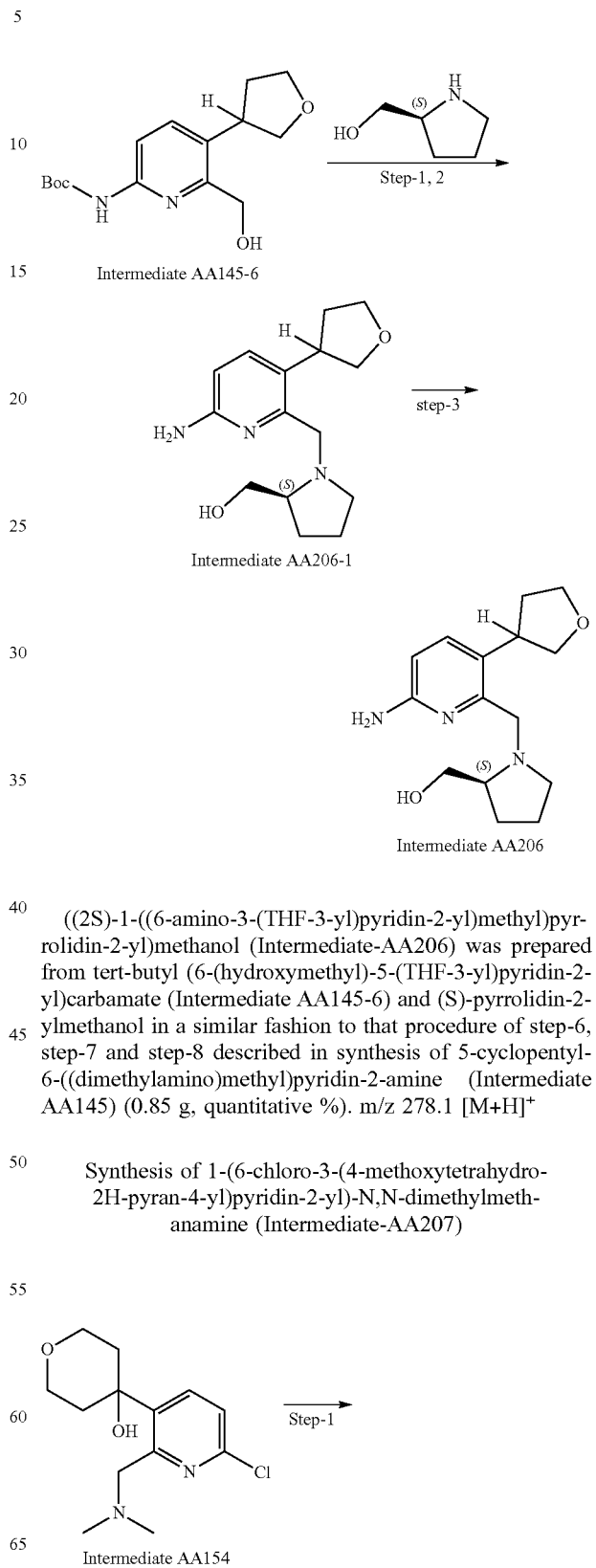

((2S)-1-((6-amino-3-(THF-3-yl)pyridin-2-yl)methyl)pyrrolidin-2-yl)methanol (Intermediate-AA206) was prepared from tert-butyl (6-(hydroxymethyl)-5-(THF-3-yl)pyridin-2-yl)carbamate (Intermediate AA145-6) and (S)-pyrrolidin-2-ylmethanol in a similar fashion to that procedure of step-6, step-7 and step-8 described in synthesis of 5-cyclopentyl-6-((dimethylamino)methyl)pyridin-2-amine (Intermediate AA145) (0.85 g, quantitative %). m/z 278.1 [M+H]$^+$ Synthesis of 1-(6-chloro-3-(4-methoxytetrahydro-2H-pyran-4-yl)pyridin-2-yl)-N,N-dimethylmethanamine (Intermediate-AA207)

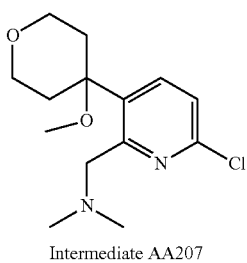

Intermediate AA207

Step-1 synthesis of 1-(6-chloro-3-(4-methoxytetrahydro-2H-pyran-4-yl)pyridin-2-yl)-N,N-dimethylmethanamine (Intermediate AA207)

To a solution of Intermediate AA154 (0.5 g, 1.85 mmol) in THF (5 mL) at 0° C. was added sodium hydride (60%) (0.22 g, 5.55 mmol, 3.0 eq) and then methyl iodide (0.315 g, 2.22 mmol, 1.2 eq). After stirring at RT for 2 h, the reaction mixture was diluted with cold water (30 mL) and extracted with ethyl acetate (3×20 mL). The combined organic extracts were washed with brine, dried over Na$_2$SO$_4$, filtered, and concentrated under reduced pressure to afford Intermediate AA207 (0.220 g, 41.83%) MS (ES): m/z=285.1 [M+H]$^+$

Synthesis of 6-chloro-3-(4-(methoxymethyl)tetrahydro-2H-pyran-4-yl)picolinonitrile (Intermediate-AA208)

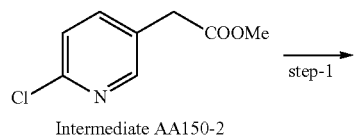

Intermediate AA150-2

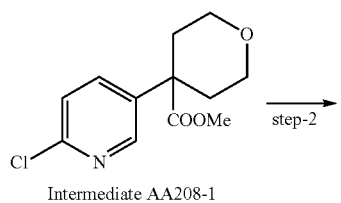

Intermediate AA208-1

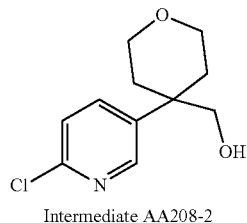

Intermediate AA208-2

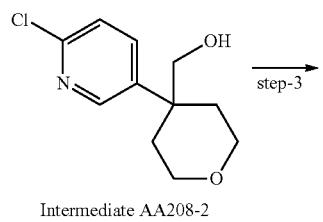

Intermediate AA208-2

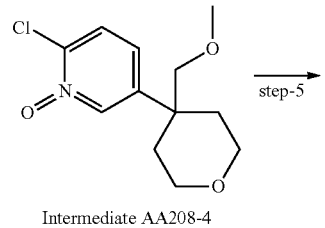

Intermediate AA208-3

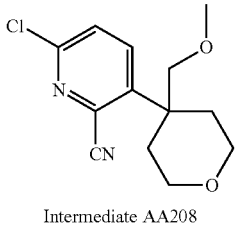

Intermediate AA208-4

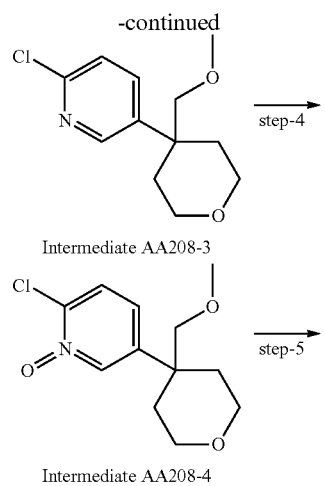

Intermediate AA208

Step-1 Synthesis of Methyl 4-(6-chloropyridin-3-yl)tetrahydro-2H-pyran-4-carboxylate (Intermediate AA208-1)

To a solution of the Intermediate AA150-2 (3 g, 16.21 mmol) in DMF (30 mL) at 0° C. was added sodium hydride (1.6 g, 40.52 mmol, 2.5 eq). After 15 min, 1-bromo-2-(2-bromoethoxy) ethane (7.5 g, 32.42 mmol, 2.0 eq) was added. After stirring at RT for 1 h, the reaction mixture was quenched in ice cold water (100 mL) and extracted with ethyl acetate (3×30 mL). The combined organic extracts were washed with brine (90 mL), dried over Na$_2$SO$_4$, filtered, and concentrated under reduced pressure to afford Intermediate AA208-2 (2.1 g, 50.81%) MS (ES): m/z 256.07 [M+H]$^+$

Step-2 Synthesis of 4-(6-chloropyridin-3-yl)tetrahydro-2H-pyran-4-yl)methanol (Intermediate AA208-2)

To a solution of Intermediate AA208-1 (2.1 g, 8.23 mmol) in methanol (100 mL) at 0° C. was added portion wise sodium borohydride (1.8 g, 49.38 mmol, 6.0 eq). After stirring at RT for 1 h, the reaction mixture was concentrated under reduced pressure and extracted with ethyl acetate (80 mL). The organic layer was concentrated under reduced pressure to afford Intermediate AA208-2 (1.5 g, 80.22%) MS (ES): m/z 228.07 [M+H]$^+$

Step-3 Synthesis of 2-chloro-5-(4-(methoxymethyl)tetrahydro-2H-pyran-4-yl)pyridine (Intermediate AA208-3)

To a cooled solution of Intermediate AA208-2 (0.5 g, 2.20 mmol) in DMF (5 mL) at 0° C. was added sodium hydride (0.220 g, 5.5 mmol, 2.5 eq). After 15 min methyl iodide (0.27 mL, 4.4 mmol, 2.0 eq) was added. After stirring at RT for 1 h, the reaction mixture was quenched in ice cold water (50 mL) and extracted with ethyl acetate (3×15 mL). The combined organic extracts were washed with brine (40 mL), dried over Na₂SO₄, filtered, and concentrated under reduced pressure to afford Intermediate AA208-3 (0.450 g, 84.78%) MS (ES): m/z 242.09 [M+H]⁺

Step-4 Synthesis of 2-chloro-5-(4-(methoxymethyl) tetrahydro-2H-pyran-4-yl)pyridine 1-oxide (Intermediate AA208-4)

To a solution of the Intermediate AA208-4 (0.485 g, 1.86 mmol) in DCM (5 mL) at 0° C. was added urea H₂O₂ (0.524 g, 5.58 mmol, 3.0 eq, cas no: 124-43-6). After stirring for 15 min at 0° C., trifluoroacetic anhydride (1.1 g, 5.58 mmol, 3.0 eq) was added at 0° C. After stirring at RT for 1 h, the reaction mixture was quenched in water (60 mL) and extracted with DCM (3×20 mL). The combined organic extracts were washed with brine (50 mL), dried over Na₂SO₄, filtered, and concentrated under reduced pressure. The residue was purified by column chromatography eluting with 2% elution methanol in DCM to afford Intermediate AA208-4 (0.420 g, 87.54%) MS (ES): m/z 258.09 [M+H]⁺

Step-5 Synthesis of 6-chloro-3-(4-(methoxymethyl) tetrahydro-2H-pyran-4-yl)picolinonitrile (Intermediate AA208)

To a solution of Intermediate AA208-4 (0.420 g, 1.63 mmol) in acetonitrile (5 mL) were added trimethylamine (0.6 mLg, 4.89 mmol, 3.0 eq) and trimethylsilyl cyanide (0.6 mL, 4.89 mmol, 3.0 eq). After stirring at 120° C. for 16 h, the reaction mixture was quenched in water (50 mL) and extracted with ethyl acetate (3×20 mL). The combined organic extracts were washed with brine (40 mL), dried over Na₂SO₄, filtered, and concentrated under reduced pressure. The residue was purified by column chromatography eluting with 1% elution methanol in DCM to afford Intermediate AA208 (0.250 g, 57.51%) MS (ES): m/z 267.02 [M+H]⁺

Synthesis of N-(2-(6-amino-3-(THF-3-yl)pyridin-2-yl)propan-2-yl)acetamide (Intermediate-AA209)

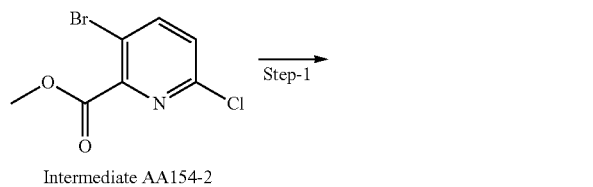

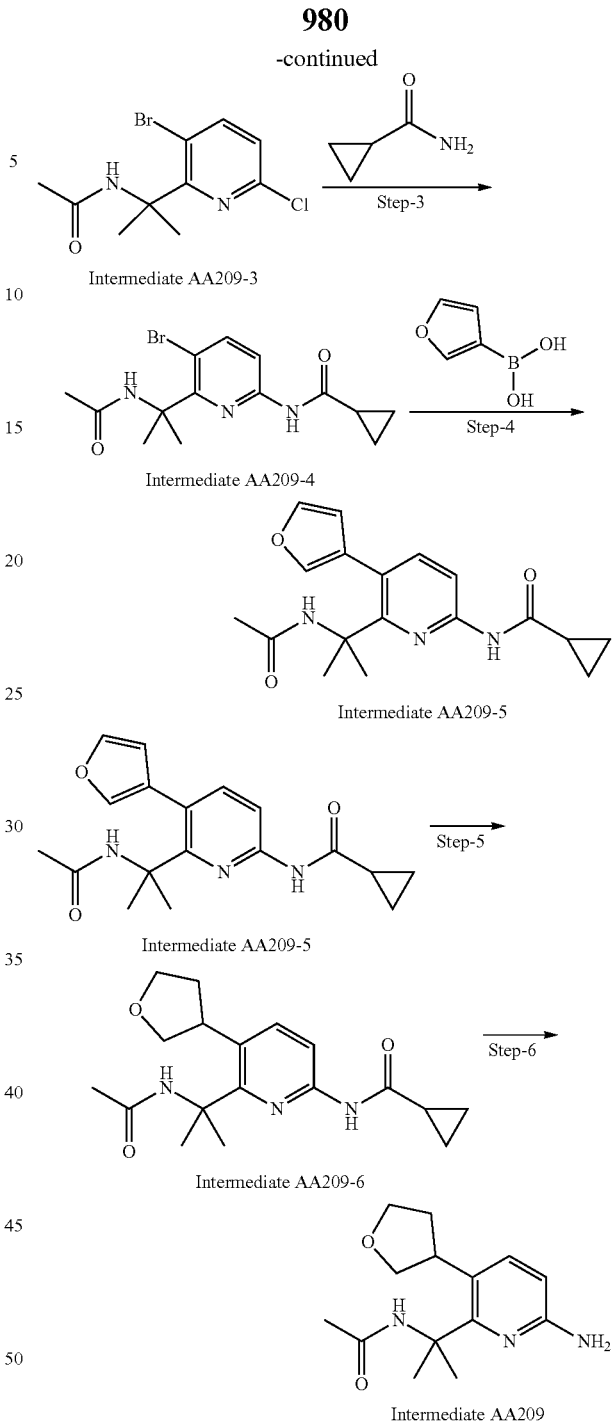

Step-1 Synthesis of 2-(3-bromo-6-chloropyridin-2-yl)propan-2-ol (Intermediate AA209-2)

To a solution of Intermediate AA154-2 (10 g, 40.32 mmol) in THF (100 mL) at 0° C. was added dropwise methyl magnesium bromide solution (3.0M in diethyl ether) (100 mL). After stirring at 0° C. for 1 h and for 15 min at RT, the reaction mixture was quenched in water (500 mL) and extracted with ethyl acetate (3×100 mL). The combined organic extracts were washed with brine (200 mL), dried over Na₂SO₄, filtered, and concentrated under reduced pressure to afford Intermediate AA209-2 (7.0 g, quantitative %) which was used in the next step without further purification. MS (ES): m/z 250.9 [M+H]⁺

Step-2 Synthesis of N-(2-(3-bromo-6-chloropyridin-2-yl)propan-2-yl)acetamide (Intermediate AA209-3)

To a solution of sulfuric acid (100 mL) in acetonitrile (25 mL) at 0° C. was added dropwise in solution of Intermediate AA209-2 (5.5 g, 22.00 mmol) in acetonitrile (60 mL). After stirring at 55° C. for 4 h, the reaction mixture was quenched in ice cold water and sodium bicarbonate solution and extracted with ethyl acetate (3×100 mL). The combined organic extracts were washed with brine, dried over Na$_2$SO$_4$, filtered, and concentrated under reduced pressure. The residue was purified by column chromatography eluting with 30% elution ethyl acetate in hexane to afford Intermediate AA209-3 (2.5 g, 39.05%) MS (ES): m/z=291.1 [M+H]⁺

Step-3 Synthesis of N-(6-(2-acetamidopropan-2-yl)-5-bromopyridin-2-yl)cyclopropanecarboxamide (Intermediate AA209-4)

To a solution of Intermediate AA209-3 (3.6 g, 12.37 mmol) and cyclopropanecarboxamide (3.1 g, 37.11 mmol, 3.0 eq) in 1,4-dioxane (36 mL) was added K$_2$CO$_3$ (5.1 g, 37.11 mmol, 3.0 eq). After degassing under N$_2$ stream for 15 min, Xantphos (1.4 g, 2.47 mmol, 0.2 eq) and Pd$_2$(dba)$_3$ (1.1 g, 1.23 mmol, 0.1 eq) were added. After stirring at 100° C. for 5 h, the reaction mixture was cooled to RT, diluted water (150 mL) and extracted with ethyl acetate (3×60 mL). The combined organic extracts were washed with brine (70 mL), dried over Na$_2$SO$_4$, filtered, and concentrated under reduced pressure. The residue was purified by column chromatography eluting with 40-45% ethyl acetate gradient in hexane to afford Intermediate AA209-4 (2.5 g, 59.51%), m/z=341.06 [M+2]⁺

Step-4 Synthesis of N-(6-(2-acetamidopropan-2-yl)-5-(furan-3-yl)pyridin-2-yl)cyclopropanecarboxamide (Intermediate AA209-5)

To a solution of Intermediate AA209-4 (2.5 g, 7.30 mmol) in 1,4-dioxane:water (25 mL:5 mL) were added furan-3-ylboronic acid (2.0 g, 18.27 mmol, 2.5 eq), and potassium phosphate tribasic (4.64 g, 21.9 mmol, 3.0 eq). After degassing with N$_2$ for 15 min, X-Phos pd G2 (0.573 g, 0.73 mmol, 0.1 eq) was added. After stirring at 100° C. for 1 h, the reaction mixture was diluted with water (120 mL) and extracted with ethyl acetate (2×50 mL). The combined organic extracts were washed with brine (130 mL), dried over Na$_2$SO$_4$, filtered, and concentrated under reduced pressure. The residue was purified by column chromatography eluting with 40-45% ethyl acetate gradient in hexane to afford Intermediate AA209-5 (1.7 g, 70.67%), MS (ES): m/z 328.1 [M+H]⁺.

Step-5 Synthesis of N-(6-(2-acetamidopropan-2-yl)-5-(THF-3-yl)pyridin-2-yl)cyclopropanecarboxamide (Intermediate AA209-6)

To a solution of Intermediate AA209-5 (0.9 g, 2.75 mmol) in methanol (10 mL) was added Rhodium on alumina (0.9 g). After stirring at RT for 16 h, the reaction mixture was filtered through celite-bed and washed with 10% methanol in DCM. The filtrate was concentrated under reduced pressure. The residue was purified by column chromatography eluting with 60% ethyl acetate gradient in hexane to afford Intermediate AA209-6 (0.6 g, 65.86%), m/z=332.1 [M+H]⁺

Step-6 Synthesis of N-(2-(6-amino-3-(THF-3-yl) pyridin-2-yl)propan-2-yl)acetamide (Intermediate AA209)

To a solution of Intermediate AA209-6 (0.6 g, 1.81 mmol) in methanol (8 mL) and water (2 mL) was added sodium hydroxide (0.868 g, 21.72 mmol, 12.0 eq). After stirring at 80° C. for 16 h, the reaction mixture was diluted with water (30 mL) and extracted with DCM (4×15 mL). The combined organic extracts were washed with brine, dried over Na$_2$SO$_4$, filtered, and concentrated under reduced pressure to afford Intermediate AA209 (0.400 g, 83.90%), MS (ES) m/z=264.1 [M+H]⁺

Synthesis of 1-(6-chloro-3-(4-fluorotetrahydro-2H-pyran-4-yl)pyridin-2-yl)-N,N-dimethylmethanamine (Intermediate-AA210)

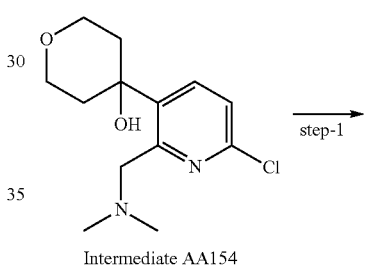

Intermediate AA154

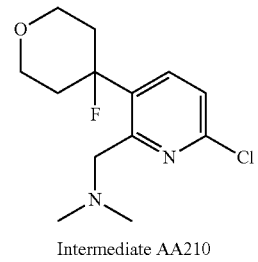

Intermediate AA210

Step-1 Synthesis of 1-(6-chloro-3-(4-fluorotetrahydro-2H-pyran-4-yl)pyridin-2-yl)-N,N-dimethylmethanamine (Intermediate AA210)

To a solution of Intermediate AA154 (0.250 g, 0.92 mmol) in DCM (5 mL) at −15° C. was added dropwise diethylaminosulfur trifluoride (0.296 g, 1.84 mmol, 2.0 eq) diluted in DCM. After stirring at −15° C. for 15 min, the reaction mixture was diluted with cold water (30 mL), quenched by sodium bicarbonate solution and extracted with DCM (3×20 mL). The combined organic extracts were washed with brine, dried over Na$_2$SO$_4$, filtered, and concentrated under reduced pressure to afford Intermediate AA210 (0.150 g, 59.56%) MS (ES): m/z=273.1 [M+H]⁺

Synthesis of 1-(6-bromo-3-(2,2-difluoroethoxy)pyridin-2-yl)-N,N-dimethylmethanamine (Intermediate-AA211)

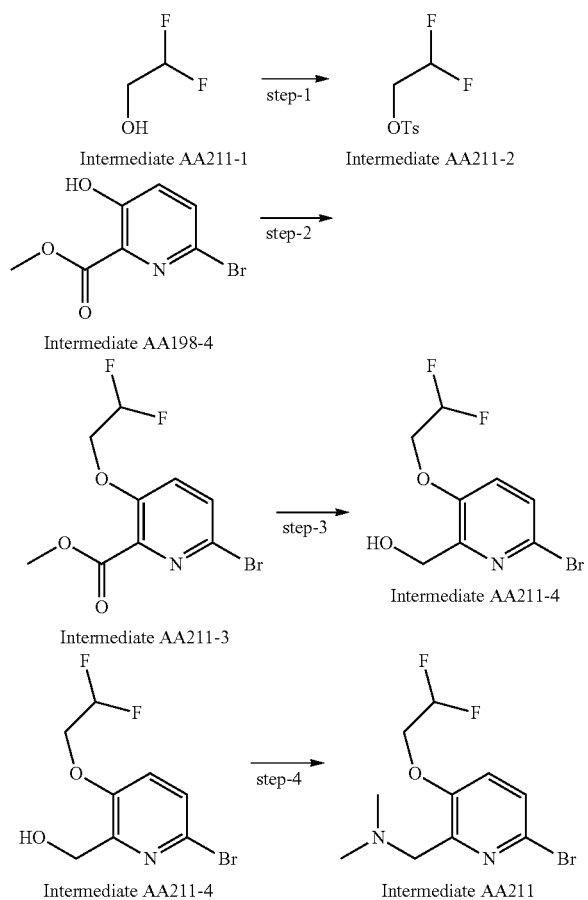

Step-1 Synthesis of 2,2-difluoroethyl 4-methylbenzenesulfonatemethyl6-bromo-3-(2,2-difluoroethoxy) picolinate (Intermediate AA211-2)

To a solution of Intermediate AA211-1 (3.1 g, 37.80 mmol) in DCM (30 mL) were added triethylamine (3.81 g/5.2 ml, 37.80 mmol, 1 eq) dropwise, DMAP (1.38 g, 11.3 mmol, 0.3 eq) and tosyl chloride (7.18 g, 37.80 mmol, 1 eq) at RT. After stirring at 60° C. and for 1 h, the reaction mixture was quenched with water (300 mL) and extracted by EtOAc (2×100). The combined organic layer was washed with brine (100 mL), passed through a Na$_2$SO$_4$, and concentrated under reduced pressure. The residue was purified by column chromatography (5-10% gradient with ethyl acetate in hexane) to afford Intermediate-AA211-2. (7.4 g, 100%) MS (ES): m/z 236 [M+1]$^+$

Step-2 Synthesis of methyl6-bromo-3-(2,2-difluoroethoxy)picolinate (Intermediate AA211-3)

To a solution of Intermediate AA198-4 (1.5 g, 46.55 mmol) in DMF (15 mL) were added potassium carbonate (2.6 g, 39.65 mmol, 3 eq) and dropwise Intermediate-AA211-2 (1.98 g, 40.55 mmol, 0.3 eq). After stirring at 100° C. and for 2 h, the reaction mixture was quenched with water (300 mL) and extracted by EtOAc (2×100). The combined organic layer was washed with brine (100 mL), passed through a Na$_2$SO$_4$, and concentrated under reduced pressure. The residue was purified by column chromatography (5-10% gradient with ethyl acetate in hexane) to afford Intermediate AA211-3 (1.2 g, 98%), MS (ES): m/z 295 [M+1]$^+$.

Step-3 Synthesis of 6-bromo-3-(2,2-difluoroethoxy)pyridin-2-yl)methanol (Intermediate AA211-4)

To a solution of Intermediate AA211-3 (1 g, 33.89 mmol) in ethanol (20 mL) was treated portion wise with sodium borohydride (0.380 g, 16.9 mmol, 3.0 eq). After stirring at 80° C. for 1 h, the reaction was quenched with water (200 mL) and extracted into ethyl acetate (3×80 mL). The combined organic extracts were washed with brine, dried over Na$_2$SO$_4$, filtered, and concentrated under reduced pressure. The residue was purified by column chromatography (20-30% gradient with ethyl acetate in hexane) to afford Intermediate AA211-4 (0.700 g, 100%). MS (ES): m/z=268 [M+H]$^+$.

Step-4 Synthesis of 1-(6-bromo-3-(2,2-difluoroethoxy)pyridin-2-yl)-N, N dimethyl Methanamine (Intermediate AA211)

To a solution of Intermediate AA211-4 (0.700 g, 26.11 mmol) in DCM (15 mL) with diisopropylethylamine (1.0 mL, 35.73 mmol, 3.0 eq) at 0° C. was added mesyl chloride (0.446 g, 39.17 mmol, 1.5 eq). After stirring at 0° C. to RT for 30 mins, the reaction mixture was quenched with water (300 mL) and extracted by DCM (2×100 mL). The combined organic layer was washed with brine (100 mL), passed through a Na$_2$SO$_4$, and concentrated under reduced to afford mesylate intermediate. (0.6 g, quantitative %), MS (ES): m/z 346 [M+1]$^+$ To a solution of mesylate intermediate (0.600 g, 73.4 mmol) in acetonitrile (14 mL) was added dropwise diisopropylethylamine (0.7 mL, 69.3 mmol, 3.5 eq). After stirring at 100° C. for 2 h, dimethylamine (0.280 g, 34.68 mmol, 2 eq) was added. After stirring at 100° C. for 2 h, the reaction mixture was quenched with water (300 mL) and extracted by 10% methanol in DCM (2×100). The combined organic layer was washed with brine (100 mL), passed through a Na$_2$SO$_4$, and concentrated under reduced pressure to afford Intermediate AA211 (035 g, 96%) which was used as is, MS (ES): m/z 294 [M+1]$^+$

Synthesis of 6-((dimethylamino)methyl)-5-(3-(methoxymethyl)THF-3-yl)pyridin-2-amine (Intermediate-AA212)

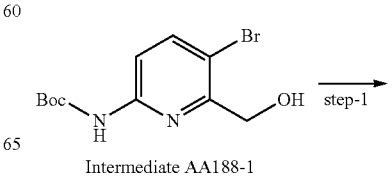

Intermediate AA188-1

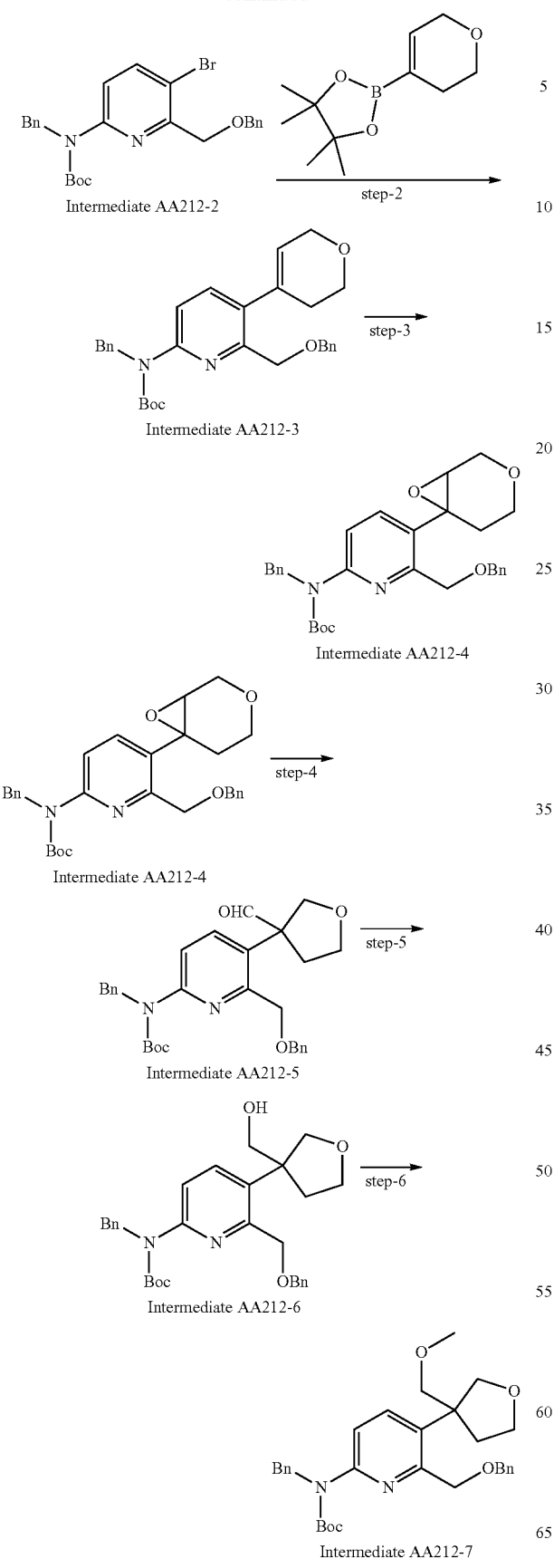
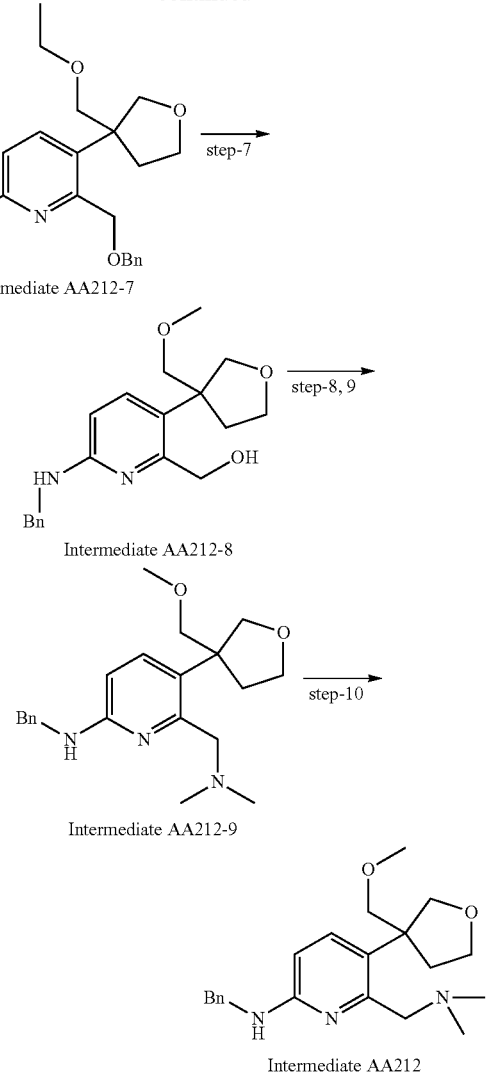

Step-1 Synthesis of tert-butylbenzyl(6-((benzyloxy)methyl)-5-bromopyridin-2-yl)carbamate (Intermediate AA212-2)

To a solution of Intermediate AA188-1 (10 g, 33.00 mmol) in DMF (100 mL) at 0° C. was treated portion wise with sodium hydride (1.98 g, 25.08 mmol, 2.5 eq). After stirring for 20 min at 0° C., mesyl chloride (2.75 mL, 35.64 mmol, 1.5 eq) was added dropwise. After stirring at 0° C. to RT for 10 min, benzyl bromide (16.9 g, 99.00 mmol, 3.0 eq) was added. After stirring at rt for 3 h, the reaction mixture was quenched with sodium bicarbonate solution and extracted by EtOAc. The combined organic layer was washed with brine (100 mL), passed through a $Na_2SO_4$, and concentrated under reduced pressure. The residue was purified by column chromatography (1-2% gradient of ethyl acetate in hexane) to afford Intermediate AA212-2 (9.3 g, 88%), MS (ES): m/z 483.41 $[M+1]^+$ Step-2 Synthesis of Tert-Butyl benzyl(6-((benzyloxy)methyl)-5-(3,6-dihydro-2H-pyran-4-yl)pyridin-2-yl)carbamate (Intermediate AA212-3)

To a solution of Intermediate AA212-2 (5 g, 68.60 mmol, 1.0 eq) in dioxane (100 mL) and water (50 mL) were added 2-(3,6-dihydro-2H-pyran-4-yl)-4,4,5,5-tetramethyl-1,3,2-dioxaborolane (4.7 g, 27.54 mmol, 1.1 eq) and add $K_3PO_4$ (13.15 g, 58.90 mmol, 3.0 eq). After degassing with argon for 10 mins, bis(triphenylphosphine)palladium(II) dichloride (1.45 g, 20.58 mmol, 0.1 eq) was added. After stirring at 80° C. for 1 h, the reaction mixture was quenched with water and extracted by EtOAc. The combined organic layer was washed with brine (100 mL), passed through a $Na_2SO_4$, and concentrated under reduced pressure. The residue was purified by column chromatography (12% gradient of ethyl acetate in hexane) to afford Intermediate AA212-3 (9.0 g, 99.38%), MS (ES): m/z 486 $[M+1]^+$ Step-3 Synthesis of Tert-Butyl benzyl(6-((benzyloxy)methyl)-5-(3,6-dihydro-2H-pyran-4-yl)pyridin-2-yl)carbamate (Intermediate AA212-4)

To a solution of Intermediate AA212-3 (10 g, 57.61 mmol) in DCM (125 mL) was treated portion wise with meta chloro per benzoic acid (8.89 g, 40.20 mmol, 2.5 eq). After stirring at RT for 48 h, the reaction mixture was cooled to RT, diluted with $NaHCO_3$ solution, and extracted into DCM (3×40 mL). The combined organic extracts were washed with brine, dried over $Na_2SO_4$, filtered, and concentrated under reduced pressure. The residue was purified by column chromatography (10% gradient of EtOAc in Hexane) to afford Intermediate AA212-4 (5 g, 89.73%), MS (ES): m/z 502 $[M+1]^+$ Step-4 Synthesis of tert-butylbenzyl(6-((benzyloxy)methyl)-5-(3-formyl THF-3-yl)pyridin-2-yl) carbamate (Intermediate AA212-5)

To a solution of Intermediate AA212-4 (10 g, 20.33 mmol) in dioxane (25 mL) was treated portion wise with scandium(III) triflate (0.980 g, 19.92 mmol, 0.1 eq). After stirring at 80° C. for 10 mins, the reaction mixture was cooled to RT, diluted with $NaHCO_3$ solution, and extracted into ethyl acetate. The combined organic extracts were washed with brine, dried over $Na_2SO_4$, filtered, and concentrated under reduced pressure. The residue was purified by column chromatography (12% gradient of EtOAc in hexane) to afford Intermediate AA212-5 (4.6 g, 80%), MS (ES): m/z 502 $[M+1]^+$ Step-5 Synthesis of tert-butyl benzyl (6-((benzyloxy)methyl)-5-(3-(hydroxymethyl) THF-3-yl)pyridin-2-yl)carbamate (Intermediate AA212-6)

To a solution of Intermediate AA212-5 (6 g, 19.52 mmol) in ethanol (25 mL) at 0° C. was treated portion wise with sodium borohydride (1.36 g, 58.56 mmol, 3.0 eq). After stirring for 10 mins, the reaction was concentrated under reduced pressure, quenched slowly with water (500 mL), and extracted by DCM. The combined organic layer was washed with brine dried over $Na_2SO_4$ and concentrated under reduced pressure. The residue was purified by column chromatography (18% gradient of ethyl acetate in hexane) to afford Intermediate AA212-6 (3 g, 95%), MS (ES): m/z 504 $[M+1]^+$ Step-6 Synthesis of Tert-Butyl benzyl(6-((benzyloxy)methyl)-5-(3-(methoxymethyl) THF-3-yl)pyridin-2-yl)carbamate (Intermediate AA212-7)

To a solution of Intermediate AA212-6 (1 g, 19.81 mmol) in THF (10 mL) and methanol (0.4 mL) at 0° C. was added sodium hydride (0.143 g, 59.94 mmol, 3.0 eq). After stirring for 15 min, methyl iodide (0.42 g, 2.97 mmol, 1.5 eq) was added. After stirring for 6 h, the reaction mixture was quenched with water (300 mL) and extracted by ethyl acetate (2×100 mL). The combined organic layer was washed with brine (100 mL), passed through a $Na_2SO_4$, and concentrated under reduced pressure. The residue was purified by column chromatography (10% gradient of EtOAc in hexane) to afford Intermediate AA212-7 (0.900 g, 90%), MS (ES): m/z 515.65 $[M+1]^+$ Step-7 Synthesis of 6-(benzylamino)-3-(3-(methoxymethyl) THF-3-yl) pyridine-2-yl) methanol (Intermediate AA212-8)

To a solution of Intermediate AA212-7 (0.500 g, 9.64 mmol) in DCM (5 mL) at 0° C. was added dropwise triflic acid (0.3 mL). After stirring for 1 h, the reaction mixture was quenched with sodium bicarbonate solution (300 mL) and extracted by DCM (2×100 mL). The combined organic layer was washed with brine (100 mL), passed through a $Na_2SO_4$, and concentrated under reduced pressure. The residue was purified by column chromatography (3% methanol gradient in DCM) to afford Intermediate AA212-8 (0.450 g, 81.92%), MS (ES): m/z 328.41 $[M+1]^+$ Step-8 & 9 Synthesis of N-benzyl-6-((dimethylamino)methyl)-5-(3-(methoxymethyl) THF-3-yl) pyridin-2-amine (Intermediate AA212-9)

To a solution of Intermediate AA211-8 (0.450 g, 37.02 mmol) in DCM (5 mL) with diisopropylethylamine (0.240 g, 20.55 mmol, 1.5 eq) at 0° C. was added mesyl chloride (0.530 g, 11.06 mmol, 3.0 eq). After stirring at 0° C. to RT for 15 mins, the reaction mixture was quenched with water (300 mL) and extracted by DCM (2×100). The combined organic layer was washed with brine (100 mL), passed through a $Na_2SO_4$, and concentrated under reduced pressure to afford mesylated intermediate. (0.700 g, 74%), MS (ES): m/z 906.5 $[M+1]^+$ To a solution of mesylated intermediate (0.7 g, 17.22 mmol) in acetonitrile (14 mL) was added dropwise diisopropylethylamine (1.33 g, 33.22 mmol, 6.0 eq) and dimethylamine·hydrochloride (0.420 g, 51.66 mmol, 3.0 eq). After stirring at 70° C. for 2 h, the reaction mixture was cooled to RT, quenched with water (300 mL) and extracted by ethyl acetate. The combined organic layer was washed with brine (100 mL), passed through a $Na_2SO_4$, and concentrated under reduced pressure. The residue was purified by column chromatography (5% methanol gradient in DCM) to afford Intermediate AA212-9 (0.450 g, 81.92%), MS (ES): m/z 365.47 $[M+1]^+$ Step-10 Synthesis of 6-((dimethylamino)methyl)-5-(3-(methoxymethyl) THF-3-yl) pyridin-2-amine (Intermediate AA212)

To a solution of Intermediate AA212-9 (0.400 g, 9.64 mmol) in DCM (1 mL) was added dropwise triflic acid (0.1 mL) at 0° C. After stirring for 20 min, the reaction mixture was quenched with sodium bicarbonate solution (300 mL) and extracted by DCM (2×100 mL). The combined organic layer was washed with brine (100 mL), passed through a $Na_2SO_4$, and concentrated under reduced pressure. The residue was purified by column chromatography (3-4% methanol gradient in DCM) to afford Intermediate AA212 (0.190 g, 92%), MS (ES): m/z 265.36 [M+1]+

Synthesis of 6-((dimethylamino)methyl)-5-(3-methylTHF-3-yl)pyridin-2-amine (Intermediate-AA213)

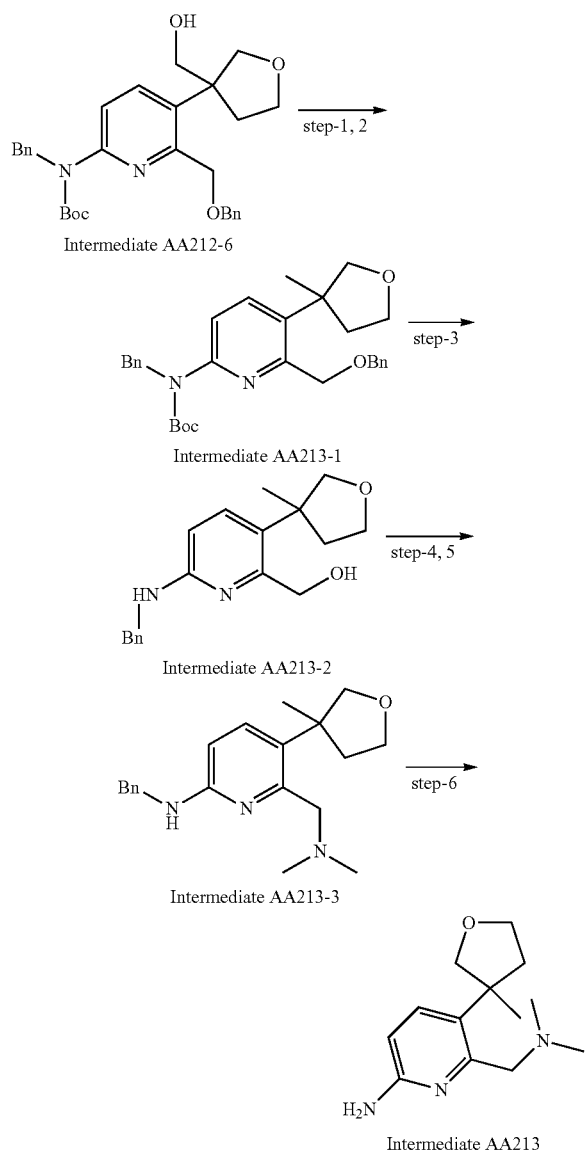

Step-1 & 2 Synthesis of Tert-Butyl benzyl(6-((benzyloxy)methyl)-5-(3-methyl THF-3-yl) pyridin-2-yl) carbamate (Intermediate AA213-1)

To a solution of Intermediate AA212-6 (1.2 g, 20.68 mmol) in DCM (10 mL) at 0° C. with diisopropylethylamine (0.767 g, 59.52 mmol, 1.5 eq) was added mesyl chloride (0.339 g, 29.76 mmol, 3 eq). After stirring from 0° C. to RT for 15 min, the reaction mixture was quenched with water (300 mL) and extracted by DCM (2×100). The combined organic layer was washed with brine (100 mL), passed through $Na_2SO_4$, and concentrated under reduced pressure to afford mesylated intermediate. (1.2 g, 80%), MS (ES): m/z 582 [M+1]+ which was directly used for next step.

To a solution of mesylate intermediate (1.2 g, 20.68 mmol) in DMF (14 mL) was added portion wise sodium iodide (1.53 g, 30.99 mmol, 5.0 eq) and portion wise zinc dust (2.0 g, 30.92 mmol, 15 eq). After stirring at 130° C. for overnight, the reaction mixture was cooled to RT, quenched with water (300 mL) and extracted by ethyl acetate. The combined organic layer was washed with brine (100 mL), passed through a $Na_2SO_4$, and concentrated under reduced pressure. The residue was purified by column chromatography (6.4% gradient of ethyl acetate in hexane) to afford Intermediate AA213-1 (0.300 g, 81%), MS (ES): m/z 488 [M+1]+

Step-3 Synthesis of 6-(benzylamino)-3-(3-methyl-THF-3-yl)pyridin-2-yl)methanol (Intermediate AA213-2)

To a solution of Intermediate AA213-1 (0.500 g, 9.64 mmol) in DCM (5 mL) at 0° C. was added dropwise triflic acid (0.3 mL). After stirring for 1 h, the reaction mixture was quenched with sodium bicarbonate solution (300 mL) and extracted by DCM (2×100). The combined organic layer was washed with brine (100 mL), passed through a $Na_2SO_4$, and concentrated under reduced pressure. The residue was purified by column chromatography (3% methanol gradient in DCM) to afford Intermediate AA213-2 (0.270 g, 81.92%), MS (ES): m/z 298 [M+1]+

Step-4 & 5 Synthesis of N-benzyl-6-((dimethylamino)methyl)-5-(3-methyl tetrahydrofuran-3-yl) pyridin-2-amine (Intermediate AA213-3)

To a solution of Intermediate AA213-2 (0.270 g, 37.02 mmol) in DCM (5 mL) at 0° C. with Diisopropylethylamine (0.350 g, 20.55 mmol, 1.5 eq) was added mesyl chloride (0.154 g, 11.06 mmol, 3.0 eq). After stirring at 0° C. to RT for 15 mins, the reaction mixture was quenched with water (300 mL) and extracted by DCM (2×100). The combined organic layer was washed with brine (100 mL), passed through a $Na_2SO_4$, and concentrated under reduced pressure to afford mesylate intermediate (0.334 g, 72%), MS (ES): m/z 377 [M+1]+

To a solution of mesylate intermediate (0.334 g, 17.22 mmol) in acetonitrile (14 mL) was added dropwise diisopropylethylamine (0.685 g, 33.22 mmol, 6.0 eq) and dropwise dimethylamine·hydrochloride (0.216 g, 51.66 mmol, 3.0 eq). After stirring at 70° C. for 2 h, the reaction mixture was cooled to RT, quenched with water (300 mL) and extracted by ethyl acetate. The combined organic layer was washed with brine (100 mL), passed through a $Na_2SO_4$, and concentrated under reduced pressure. The residue was purified by column chromatography (5% methanol gradient in DCM) to afford Intermediate AA213-3 (0.260 g, 81%), MS (ES): m/z 325 [M+1]+

Step-6 Synthesis of 6-((dimethylamino)methyl)-5-(3-methylTHF-3-yl)pyridin-2-amine (Intermediate AA213)

To a solution of Intermediate AA213-3 (0.400 g, 9.64 mmol) in DCM (1 mL) at 0° C. was added dropwise triflic acid (2 mL). After stirring for 20 mins, the reaction mixture was quenched with sodium bicarbonate solution (300 mL) and extracted with DCM (2×100 mL). The combined organic layer was washed with brine (100 mL), dried with $Na_2SO_4$, and concentrated under reduced pressure. The residue was purified by column chromatography (3-4% methanol gradient in DCM) to afford Intermediate AA213 (0.190 g, 95%), MS (ES): m/z 235 [M+1]+

The following intermediates in Table 2 were available commercially or prepared by known literature routes.

TABLE 2

Intermediates prepared by known literature routes or commercially available.

| # | Structure |
| --- | --- |
| AA4 | 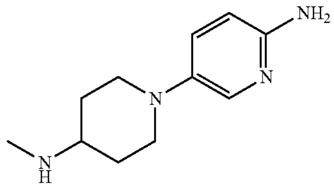 |
| AA5 | 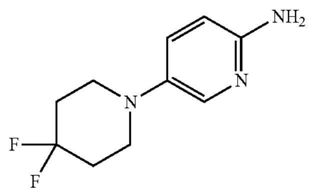 [SMILES: Nc1ccc(N2CCC(F)(F)CC2)cn1] |
| AA8 | 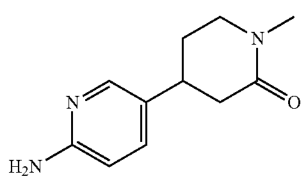 |
| AA11 | 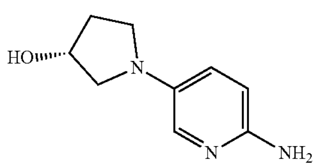 [SMILES: Nc1ccc(N2CC[C@@H](O)C2)cn1] |
| AA12 | 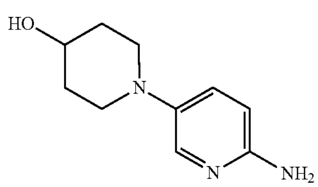 [SMILES: Nc1ccc(N2CCC(O)CC2)cn1] |
| AA16 | 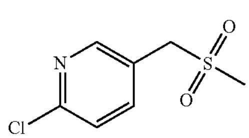 |
| AA17 | 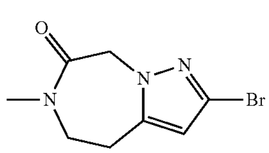 |

TABLE 2-continued

Intermediates prepared by known literature routes or commercially available.

| # | Structure |
| --- | --- |
| AA24 | 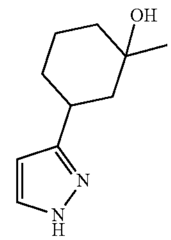 |
| AA26 | 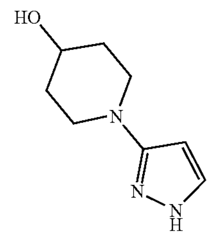 [SMILES: OC1CCN(c2cc[nH]n2)CC1] |
| AA27 | 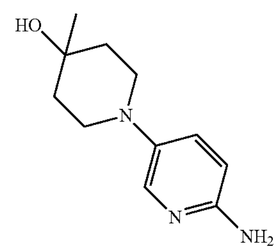 |
| AA28 | 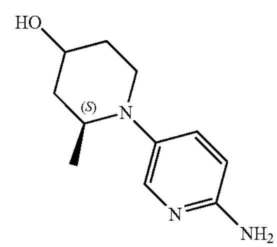 |
| AA29 | 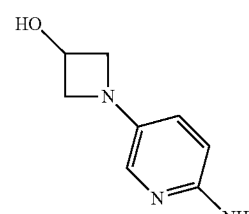 |
| AA31 | 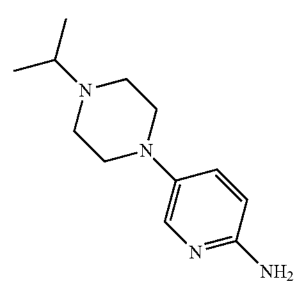 [SMILES: CC(C)N1CCN(c2ccc(N)nc2)CC1] |

TABLE 2-continued

Intermediates prepared by known literature routes or commercially available.

| # | Structure |
|---|---|
| AA33 | 1-(6-aminopyridin-2-yl)azetidin-3-ol |
| AA35 | 1-methyl-5-(6-aminopyridin-3-yl)piperidin-2-one |
| AA36 | 6-(4-methylpiperazin-1-yl)pyridin-2-amine |
| AA38 | 4-(6-aminopyridin-3-yl)-1-methylpyrrolidin-2-one |
| AA40 | 5-(7-oxa-4-azaspiro[2.5]octan-4-yl)pyridin-2-amine |
| AA41 | 3-(6-aminopyridin-3-yl)-1-methylpyrrolidin-2-one |
| AA42 | 1-(5-aminopyridin-2-yl)piperidin-4-ol |
| AA44 | 1-(6-aminopyridin-2-yl)pyrrolidin-2-one |
| AA45 | 5-(tetrahydro-2H-pyran-4-yl)pyridin-2-amine |
| AA46 | 4-(6-aminopyridin-3-yl)-1-methylpiperazin-2-one |
| AA47 | 5-(2-oxa-6-azaspiro[3.3]heptan-6-yl)pyridin-2-amine |
| AA53 | (4-(6-aminopyridin-3-yl)morpholin-2-yl)methanol |
| AA57 | 4-(6-aminopyridin-3-yl)tetrahydro-2H-pyran-4-ol |
| AA60 | 1-(tetrahydro-2H-pyran-4-yl)-1H-pyrazol-4-amine |

TABLE 2-continued

Intermediates prepared by known literature routes or commercially available.

| # | Structure |
|---|---|
| AA61 | 3-amino-5-(tetrahydropyran-4-yl)-1H-pyrazole |
| AA62 | 1-(tetrahydropyran-4-yl)-1H-pyrazol-3-amine |
| AA63 | 6-(piperidin-4-yl)pyridin-2-amine |
| AA71 | 1-methyl-5-(tetrahydropyran-4-yl)-1H-pyrazol-4-amine |
| AA75 | 1-methyl-5-(tetrahydropyran-4-yl)-1H-pyrazol-3-amine |
| AA76 | 5,6,7,8-tetrahydro-1,7-naphthyridin-2-amine |
| AA79 | 2-chloro-7-methyl-5,6,7,8-tetrahydro-1,7-naphthyridine |
| AA82 | 4-(6-aminopyridin-3-yl)-1-methylpiperidin-4-ol |

Synthesis of Tert-Butyl (R)-(1-(6-aminopyridin-3-yl)piperidin-3-yl)(methyl)carbamate (Intermediate AB1) (Method A1)

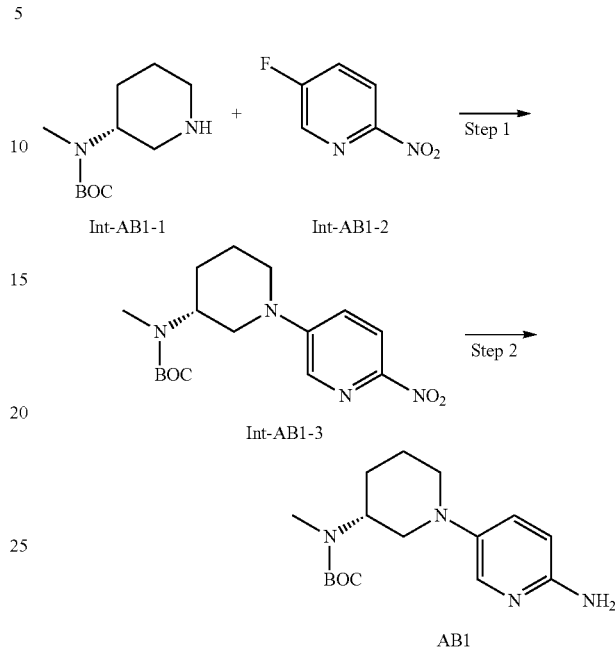

Step 1: Tert-Butyl (R)-methyl(1-(6-nitropyridin-3-yl)piperidin-3-yl)carbamate (Intermediate AB1-3)

A mixture of R)-tert-butyl-methyl(piperidin-3-yl)carbamate (Intermediate AB1-1) (1.00 g, 4.67 mmol) mmol), 5-fluoro-2-nitro-pyridine (Intermediate AB1-2) (660 mg, 4.67 mmol) and N,N-diisopropylethylamine (8.1 mL, 46.66 mmol) in DMSO (12 mL) was vigorously stirred and heated at 120° C. for 1.5 h. The cooled mixture was diluted with water (50 mL) and extracted with EtOAc. The organic phase was dried by phase separator and concentrated in vacuo. The residue was purified by column chromatography (0-100% gradient elution EtOAc in cyclohexane) to afford the title compound Intermediate AB1-3 (1.35 g, 86%) as a yellow oil.

$^1$H NMR (400 MHz, DMSO): δ 8.27 (d, J=3.0 Hz, 1H), 8.16 (d, J=9.3 Hz, 1H), 7.50 (dd, J=3.1, 9.3 Hz, 1H), 4.11 (d, J=14.0 Hz, 1H), 3.97-3.74 (m, 2H), 3.16 (dd, J=12.1, 12.1 Hz, 1H), 3.01-2.92 (m, 1H), 2.79 (s, 3H), 1.88-1.77 (m, 3H), 1.62-1.55 (m, 1H), 1.43 (s, 9H).

Step 2: Tert-Butyl (R)-(1-(6-aminopyridin-3-yl)piperidin-3-yl)(methyl)carbamate (AB1)

A solution of tert-butyl (R)-methyl(1-(6-nitropyridin-3-yl)piperidin-3-yl)carbamate (Intermediate AB1-3) (1.35 g, 4.01 mmol) in methanol (40 mL) was treated with 10% palladium on activated carbon (140 mg, 0.13 mmol). After stirring under a hydrogen atmosphere for 18 h, the mixture was filtered through Celite® washing with methanol and concentrated in vacuo azeotroping with DCM/Et$_2$O (1:1) to afford the title compound (Intermediate AB1) (1.29 g, quant.) as an orange glass solid.

$^1$H NMR (400 MHz, DMSO): δ 7.63 (d, J=2.6 Hz, 1H), 7.17 (dd, J=3.0, 8.8 Hz, 1H), 6.40 (d, J=8.8 Hz, 1H), 5.41 (s, 2H), 3.97-3.97 (m, 1H), 3.28 (d, J=12.0 Hz, 1H), 3.17 (s,

1H), 2.75 (s, 3H), 2.71-2.57 (m, 1H), 2.49-2.41 (m, 1H), 1.79-1.54 (m, 4H), 1.42 (s, 9H).

Synthesis of Tert-Butyl methyl(4-methyl-1-(6-nitropyridin-3-yl)piperidin-4-yl)carbamate (Intermediate AB2)-Method B1

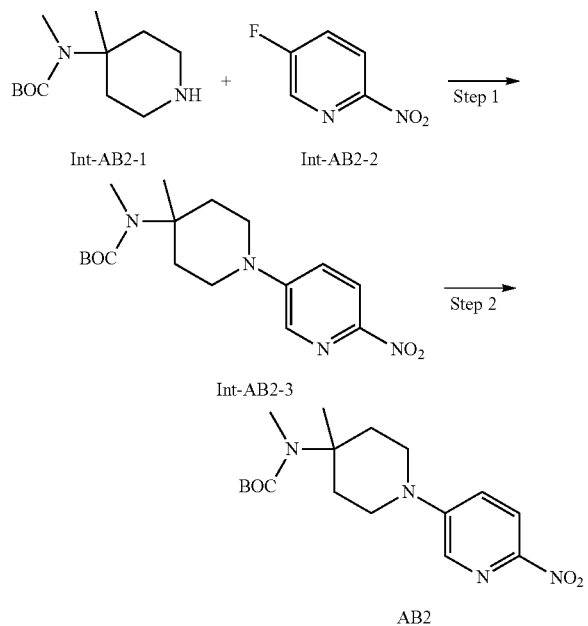

Step 1: Tert-Butyl methyl(4-methyl-1-(6-nitropyridin-3-yl)piperidin-4-yl)carbamate (Intermediate AB2-3)

Reaction performed analogous to the preparation of Intermediate AB1-3 replacing N,N-diisopropylethylamine with 2.2 equivalents potassium carbonate. Intermediate AB2-3: ¹H NMR (400 MHz, CDCl3): δ 8.16 (d, J=9.0 Hz, 1H), 8.13 (d, J=3.0 Hz, 1H), 7.18 (dd, J=3.1, 9.2 Hz, 1H), 3.62-3.54 (m, 2H), 3.30-3.22 (m, 2H), 2.88 (s, 3H), 2.64-2.57 (m, 2H), 1.86-1.78 (m, 2H), 1.55 (s, 3H), 1.47 (s, 9H).

Step 2: Tert-Butyl methyl(4-methyl-1-(6-nitropyridin-3-yl)piperidin-4-yl)carbamate (AB2)

Step 2 was carried out following the representative procedure described in Intermediate AB1-Method A1, Step 2. Intermediate AB2: ¹H NMR (400 MHz, CDCl3): δ 7.78 (d, J=2.6 Hz, 1H), 7.18 (dd, J=2.9, 8.8 Hz, 1H), 6.48 (d, J=8.8 Hz, 1H), 4.17-4.11 (m, 2H), 3.11-3.04 (m, 2H), 2.98-2.90 (m, 2H), 2.86 (s, 3H), 2.49-2.41 (m, 2H), 1.93-1.85 (m, 2H), 1.30 (s, 3H).

Synthesis of S)-1-(1-(6-aminopyridin-3-yl)piperidin-4-yl)ethan-1-ol (Intermediate AB3) Method C1

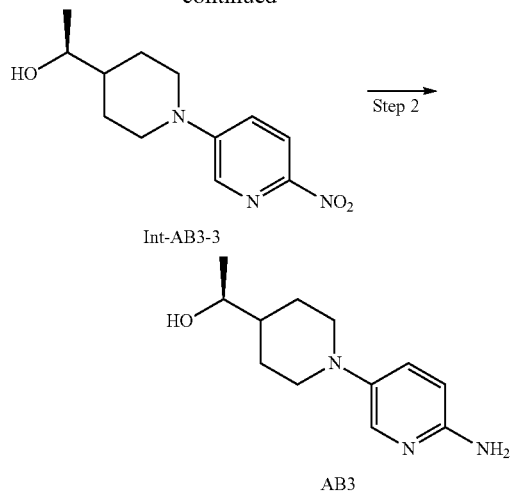

Step 1: (S)-1-(1-(6-nitropyridin-3-yl)piperidin-4-yl)ethan-1-ol (Intermediate AB3-3)

A mixture of S)-1-(piperidin-4-yl)ethan-1-ol hydrochloride (Intermediate AB3-1) (0.82 g, 4.9 mmol) mmol), 5-bromo-2-nitro-pyridine (Intermediate AB3-2) (1.0 g, 4.9 mmol), tetrabutylammonium iodide (0.36 g, 9.8 mmol) and potassium carbonate (2.0 g, 14.7 mmol) in DMSO (10 mL) was heated at 120° C. for 1 h. The cooled mixture was diluted with water (50 mL) and extracted with EtOAc (2×50 mL). The organic phase was dried over MgSO4, filtered, and concentrated in vacuo. The residue was purified by column chromatography (0-100% gradient elution EtOAc in cyclohexane) to afford the title compound (Intermediate AB3-3) (0.91 g, 73%) as an orange solid.

¹H NMR (400 MHz, DMSO): δ 8.23 (d, J=3.3 Hz, 1H), 8.12 (d, J=9.1 Hz, 1H), 7.44 (dd, J=3.0, 9.3 Hz, 1H), 4.43 (d, J=5.1 Hz, 1H), 4.16-4.11 (m, 2H), 3.39 (dd, J=7.1, 11.4 Hz, 1H), 3.00-2.89 (m, 2H), 1.87 (d, J=13.1 Hz, 1H), 1.65 (d, J=12.6 Hz, 1H), 1.53-1.42 (m, 1H), 1.35-1.17 (m, 2H), 1.04 (d, J=6.3 Hz, 3H).

Step 2: (S)-1-(1-(6-aminopyridin-3-yl)piperidin-4-yl)ethan-1-ol (AB3)

Step 2 was carried out following the representative procedure described in Intermediate AB1, Step 2. AB3: ¹H NMR (400 MHz, DMSO): δ 7.59 (d, J=2.8 Hz, 1H), 7.14 (dd, J=3.0, 8.8 Hz, 1H), 6.38 (d, J=8.8 Hz, 1H), 5.33 (s, 2H), 4.36 (d, J=4.5 Hz, 1H), 3.42-3.35 (m, 3H), 2.48-2.39 (m, 2H), 1.86-1.80 (m, 1H), 1.64-1.57 (m, 1H), 1.39-1.18 (m, 3H), 1.04 (d, J=6.3 Hz, 3H).

Synthesis of 2-(6-aminopyridin-3-yl)-N-ethyl-2-methylpropanamide (Intermediate AB4)-Method D1

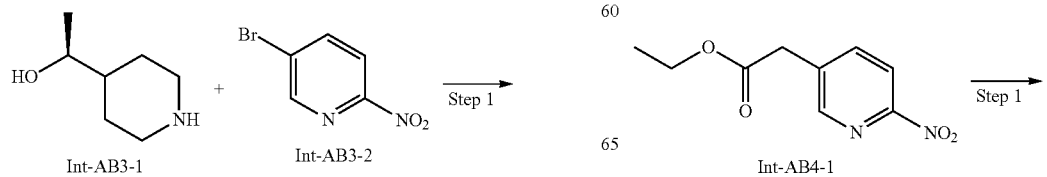

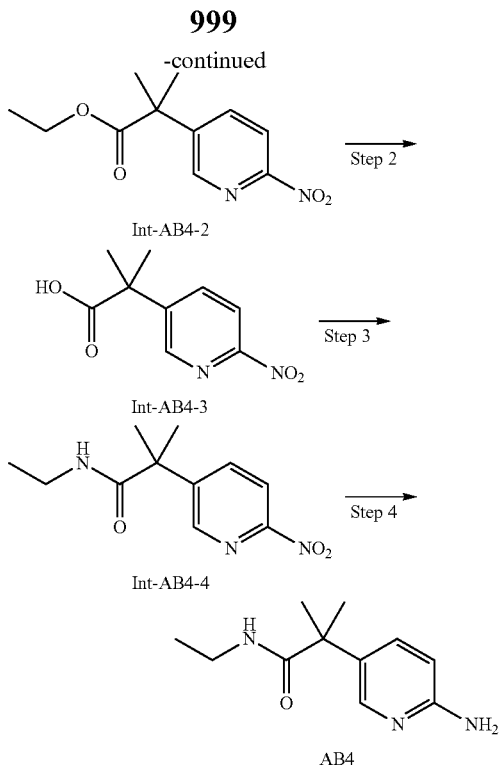

Step 1: Ethyl 2-methyl-2-(6-nitropyridin-3-yl)propanoate (Intermediate AB4-2)

A solution of ethyl-2-(6-nitropyridin-3-yl)acetate (Intermediate AB4-1) (980 mg, 4.6 mmol) in DMF (20 mL) at 0° C. was treated with sodium hydride (60% dispersion in mineral oil, 196 mg, 4.8 mmol). The mixture was stirred for 5 min, and then iodomethane (0.316 mL, 5.0 mmol) was added dropwise. After 2 h, an additional portion of sodium hydride (60% dispersion in mineral oil, 196 mg, 4.8 mmol) was added, followed by iodomethane (0.316 mL, 5.0 mmol) 5 min later. The mixture was stirred at RT for 18 h, quenched with water (30 mL) and extracted into EtOAc (2×30 mL). The combined extracts were washed with brine (30 mL), dried over $Na_2SO_4$, filtered, and concentrated in vacuo. The residue was purified by column chromatography (0-50% gradient elution EtOAc in cyclohexane) to afford the title compound (Intermediate AB4-2) (758 mg, 68%) as a yellow oil.

$^1$H NMR (400 MHz, CDCl3): δ 8.63 (s, 1H), 8.22 (d, J=8.4 Hz, 1H), 7.99 (d, J=8.2 Hz, 1H), 4.16 (q, J=7.2 Hz, 2H), 1.67 (s, 6H), 1.20 (t, J=7.2 Hz, 3H)

Step 2: 2-Methyl-2-(6-nitropyridin-3-yl)propanoic acid (Intermediate AB4-3)

A solution of ethyl 2-methyl-2-(6-nitropyridin-3-yl)propanoate (Intermediate AB4-2) (750 mg, 3.1 mmol) in methanol:water (14 mL, 1:1) was treated with lithium hydroxide monohydrate (198 mg, 4.7 mmol). After stirring at RT overnight, the pH was adjusted to −5 using 1M aqueous HCl solution and extracted with 9:1 DCM-MeOH (3×25 mL). The combined organic extracts were dried over $Na_2SO_4$, filtered, and concentrated in vacuo to afford the title compound as a crude, off white solid (Intermediate AB4-2) (423 mg, 63%).

$^1$H NMR (400 MHz, DMSO): δ 12.87 (s, 1H), 8.67 (d, J=1.8 Hz, 1H), 8.28 (d, J=8.6 Hz, 1H), 8.19 (dd, J=2.4, 8.5 Hz, 1H), 1.59 (s, 6H).

Step 3: N-Ethyl-2-methyl-2-(6-nitropyridin-3-yl)propenamide (Intermediate AB4-4)

To a suspension of 2-methyl-2-(6-nitropyridin-3-yl)propanoic acid (Intermediate AB4-3) (430 mg, 2.0 mmol) in THF (5 mL) were added 1-hydroxybenzotriazole (359 mg, 2.6 mmol) and N-(3-Dimethylaminopropyl)-N'-ethylcarbodiimide hydrochloride (510 mg, 2.6 mmol). After stirring for 10 min at RT, DIPEA (1.069 mL, 6.1 mmol) and ethylamine (2M solution in THF, 2.04 mL, 4.0 mmol) were added. After stirring overnight at RT, the reaction was diluted with EtOAc (20 mL). The organic phase was washed with water (15 mL) and brine (15 mL), dried ($MgSO_4$), filtered and concentrated in vacuo. The residue was purified by column chromatography (0-100% gradient elution EtOAc in cyclohexane) to afford the title compound (Intermediate AB4-4) (375 mg, 77%) as a pale yellow oil.

$^1$H NMR (400 MHz, DMSO): δ 8.58 (d, J=2.0 Hz, 1H), 8.27 (d, J=7.8 Hz, 1H), 8.10 (dd, J=2.4, 8.5 Hz, 1H), 7.60 (dd, J=6.2, 6.2 Hz, 1H), 3.11-3.03 (m, 2H), 1.53 (s, 6H), 0.97 (dd, J=7.2, 7.2 Hz, 3H).

Step 4: 2-(6-Aminopyridin-3-yl)-N-ethyl-2-methyl-propanamide (AB4)

Step 4 was carried out following the representative procedure described in Intermediate AB1, Step 2.

$^1$H NMR (400 MHz, DMSO): δ 7.83 (d, J=2.0 Hz, 1H), 7.26 (dd, J=2.5, 8.6 Hz, 2H), 6.38 (d, J=8.1 Hz, 1H), 5.74 (s, 2H), 3.05-3.01 (m, 2H), 1.36 (s, 6H), 0.93 (t, J=7.0 Hz, 3H).

Synthesis of Tert-Butyl (1-(6-aminopyridin-2-yl)piperidin-4-yl)(methyl)carbamate (Intermediate AB5) Method E1

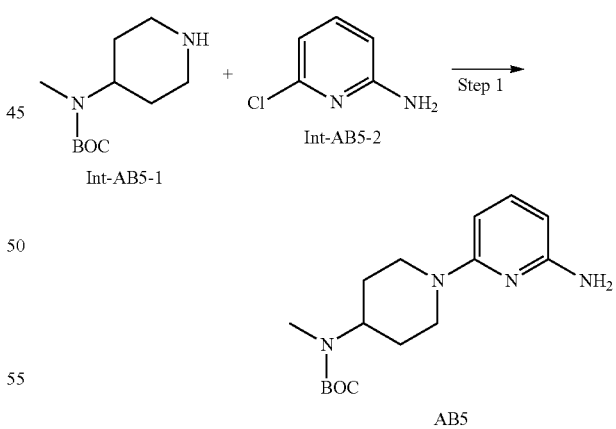

Step 1: Tert-Butyl (1-(6-aminopyridin-2-yl)piperidin-4-yl)(methyl)carbamate (Intermediate AB5)

A mixture of tert-butyl methyl(piperidin-4-yl)carbamate (Intermediate AB31-1) (3.33 g, 15.56 mmol) and 6-chloro-2-amino-pyridine (Intermediate AB5-2) (1.00 g, 7.78 mmol) were heated neat at 140° C. for 18 h. The cooled mixture was diluted with EtOAc and concentrated in vacuo. The residue was purified by column chromatography (0-10% gradient elution MeOH in DCM) to afford the title compound (Intermediate AB5) (612 mg, 26%) as a red oil.

$^1$H NMR (400 MHz, CDCl$_3$): δ, 7.25-7.23 (m, 1H), 6.02 (d, J=8.1 Hz, 1H), 5.85 (d, J=7.6 Hz, 1H), 5.30 (s, 2H), 4.35 (d, J=12.6 Hz, 2H), 4.18 (d, J=16.2 Hz, 2H), 2.81-2.76 (m, 1H), 2.71 (s, 3H), 1.69 (s, 9H), 1.57 (s, 4H).

Synthesis of Tert-Butyl (S)-(1-(6-aminopyridin-2-yl)pyrrolidin-3-yl)(methyl)carbamate (Intermediate AB6)-Method F1

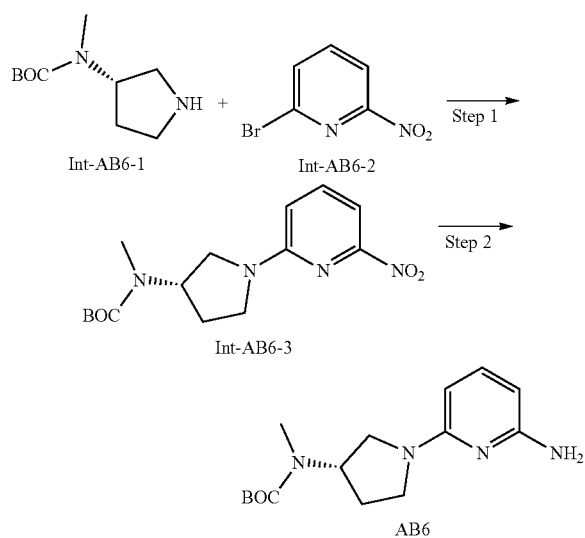

Step 1: Tert-Butyl (S)-methyl(1-(6-nitropyridin-2-yl)pyrrolidin-3-yl)carbamate (Intermediate AB6-3)

A mixture of 2-bromo-6-nitro-pyridine (Intermediate AB6-2) (1.00 g, 4.93 mmol), tert-butyl-(S)-methyl(pyrrolidin-3-yl) carbamate (Intermediate AB6-1) (1.09 g, 5.42 mmol), XantPhos (0.29 g, 0.493 mmol), Pd$_2$(dba)$_3$ (0.36 g, 0.394 mmol) and cesium carbonate (3.21 g, 9.85 mmol) in toluene (40 mL) was degassed with nitrogen and heated at 95° C. for 4 h. The cooled reaction mixture was concentrated in vacuo and the residue partitioned between EtOAc and water. The aqueous layer was further extracted with EtOAc (2×). The combined extracts were dried over MgSO$_4$ and concentrated in vacuo. The residue was purified by column chromatography (0-75% gradient elution EtOAc in cyclohexane) to afford the title compound (Intermediate AB6-3) (523 mg, 33%) as a yellow oil.

$^1$H NMR (400 MHz, CDCl$_3$): δ 7.67 (t, J=7.9 Hz, 1H), 7.43 (d, J=7.0 Hz, 1H), 6.64 (d, J=8.8 Hz, 1H), 4.92 (s, 1H), 3.75 (t, J=10.2 Hz, 2H), 3.50 (dd, J=8.2, 19.3 Hz, 1H), 3.41 (dd, J=8.5, 10.8 Hz, 1H), 2.83 (s, 3H), 2.27-2.14 (m, 2H), 1.48 (s, 9H).

Step 2: Tert-Butyl (S)-(1-(6-aminopyridin-2-yl)pyrrolidin-3-yl)(methyl)carbamate (Intermediate AB6)

Step 2 was carried out following the representative procedure described in Intermediate AB1-Method A1, Step 2. AB6: $^1$H NMR (400 MHz, CDCl$_3$): δ 7.24 (t, J=8.0 Hz, 1H), 5.81 (d, J=7.7 Hz, 1H), 5.74 (d, J=8.0 Hz, 1H), 4.85 (s, 1H), 4.19 (s, 2H), 3.64-3.55 (m, 2H), 3.37-3.34 (m, 1H), 3.33-3.27 (m, 1H), 2.80 (s, 3H), 2.19-2.09 (m, 1H), 2.07-1.98 (m, 1H), 1.48 (s, 9H).

Synthesis of N$^2$-(2-(dimethylamino)ethyl)-N$^2$-methylpyridine-2,6-diamine (Intermediate AB7)

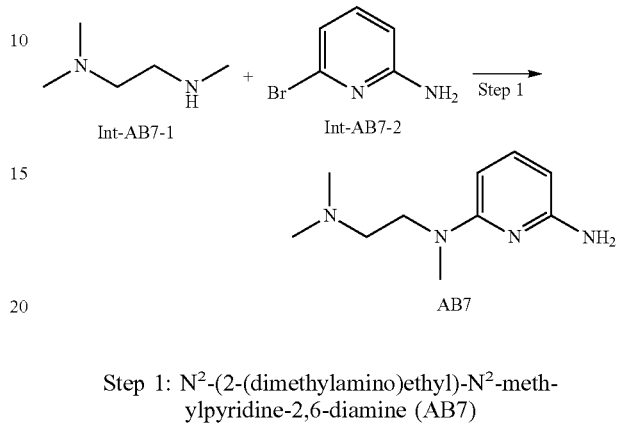

Step 1: N$^2$-(2-(dimethylamino)ethyl)-N$^2$-methylpyridine-2,6-diamine (AB7)

A mixture of 6-bromo-2-amino-pyridine (Intermediate AB7-2) (500 mg, 2.89 mmol), N, N, N'-trimethylethylenediamine (Intermediate AB7-1) (591 mg, 5.78 mmol) and cesium carbonate (1.41 g, 4.33 mmol) in NMP (10 mL) was heated at 200° C. for 20 min using microwave irradiation (Biotage Initiator®). The mixture was poured onto water and extracted into EtOAc (3×). The combined organic layers were dried over Na$_2$SO$_4$ and concentrated in vacuo. The residue was purified by column chromatography (0-20% gradient elution with MeOH in DCM followed by 1:1 7N methanolic ammonia in DCM) to afford the title compound (Intermediate AB7) (581 mg, quant.) as a red/orange residue.

$^1$H NMR (400 MHz, CDCl$_3$) 7.22 (t, J=7.8 Hz, 1H), 5.85 (d, J=8.8 Hz, 1H), 5.77 (d, J=7.9 Hz, 1H), 4.20 (s, 2H), 3.61 (t, J=7.6 Hz, 2H), 2.98 (s, 3H), 2.46 (t, J=7.5 Hz, 2H), 2.29 (s, 6H)

Synthesis of Tert-Butyl (1-(6-aminopyridin-3-yl)-3,3-difluoropiperidin-4-yl)(methyl)carbamate (Intermediate AB48)-Method H1

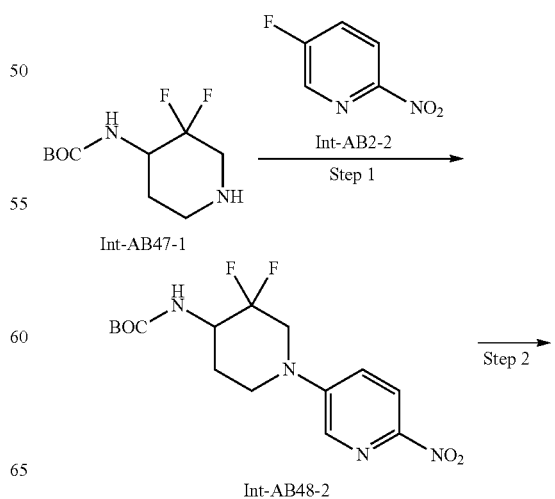

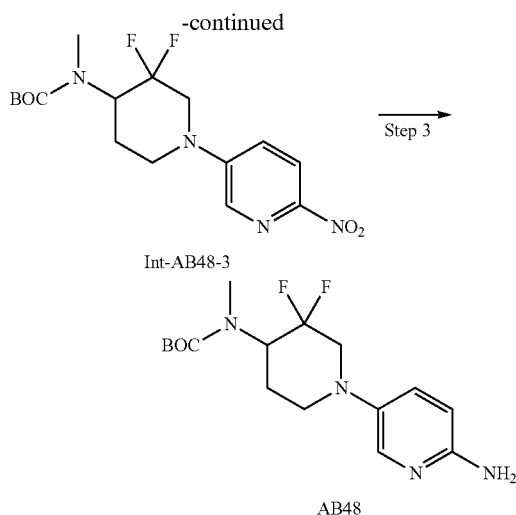

Int-AB48-3

AB48

Step 1: Tert-Butyl (3,3-difluoro-1-(6-nitropyridin-3-yl)piperidin-4-yl)carbamate (Intermediate AB48-2)

Step 1 was carried out following the representative procedure described in Intermediate AB1-Method A1, Step 1 using 4-(Boc-amino)-3,3-difluoropiperidine (Intermediate AB48-1) to afford the title compound (Intermediate AB48-2) as a yellow solid.

$^1$H NMR (400 MHz, CDCl$_3$): δ 8.20-8.16 (m, 2H), 7.28 (dd, J=2.1, 8.3 Hz, 1H), 4.80 (s, 1H), 4.23-4.16 (m, 1H), 4.02 (dd, J=2.3, 13.7 Hz, 1H), 3.39-3.27 (m, 1H), 3.24-3.16 (m, 1H), 2.22-2.14 (m, 1H), 1.79 (ddt, J=4.1, 12.7, 12.5 Hz, 1H).

Step 2: Tert-Butyl (3,3-difluoro-1-(6-nitropyridin-3-yl)piperidin-4-yl)(methyl)carbamate (Intermediate AB48-3)

A solution of tert-butyl (3,3-difluoro-1-(6-nitropyridin-3-yl)piperidin-4-yl)carbamate (Intermediate AB48-2) (370 mg, 1.03 mmol) and iodomethane (161 mg, 1.14 mmol) in DMF (3 mL) was treated with sodium hydride (60% dispersion in mineral oil, 45 mg, 1.14 mmol). After stirring and stirred at RT for 1.5 h, the reaction was quenched with a saturated NaHCO$_3$ solution and extracted into EtOAc (2×). The combined extracts were dried over MgSO$_4$ and concentrated in vacuo. The residue was purified by column chromatography (10-70% gradient elution EtOAc in cyclohexane) to afford the title compound (Intermediate AB48-3) (274 mg, 71%) as a yellow solid.

$^1$H NMR (400 MHz, CDCl$_3$): δ 8.20-8.17 (m, 2H), 7.31-7.27 (m, 1H), 4.78-4.77 (m, 1H), 3.36-3.19 (m, 2H), 2.88 (s, 3H), 2.23-2.16 (m, 1H), 1.94-1.93 (m, 1H), 1.59 (s, 1H).

Step 3: Tert-Butyl (1-(6-aminopyridin-3-yl)-3,3-difluoropiperidin-4-yl)(methyl)carbamate (AB48)

Step 3 was carried out following the representative procedure described in Intermediate AB1-Method A, Step 2 to afford the title compound (AB48) (258 mg) as a yellow residue which was used crude in subsequent reactions.

Synthesis of 6-((dimethylamino)methyl)-5-(THF-3-yl)pyridin-2-amine (Intermediate AB50)-Method I1

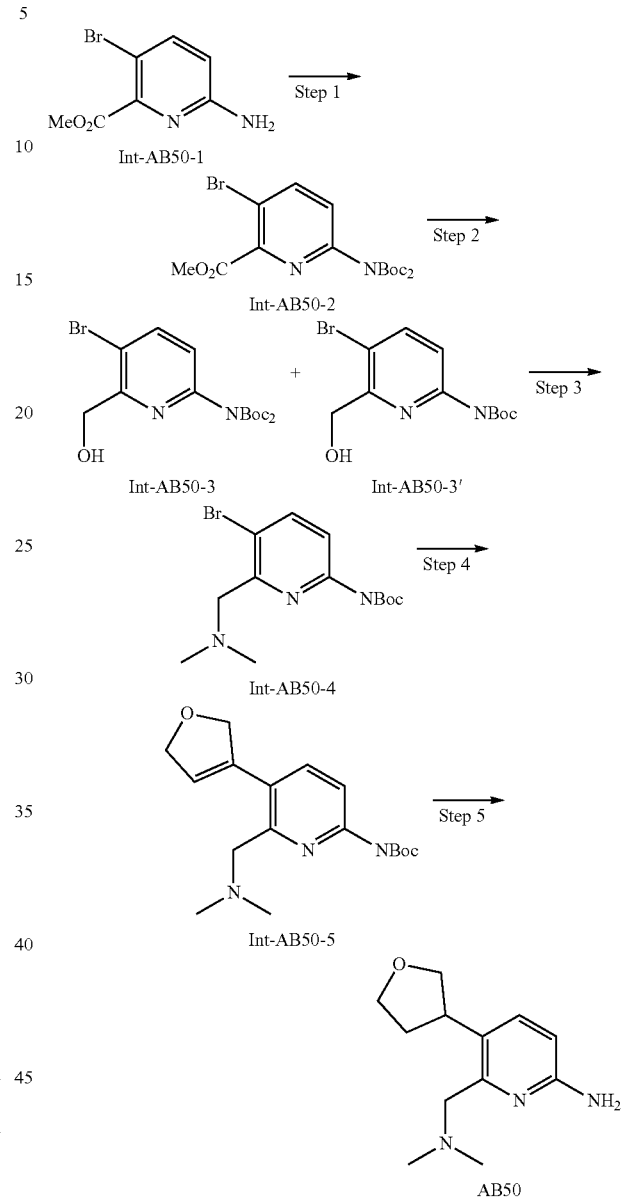

Step 1: Methyl 6-(bis(tert-butoxycarbonyl)amino)-3-bromopicolinate (Intermediate AB50-2)

A solution of methyl 6-amino-3-bromopicolinate (Intermediate AB50-1) (2.00 g, 8.7 mmol) and DMAP (0.21 g, 1.7 mmol) in THF (50 mL) was cooled to 0° C., treated portion wise with di-tert-butyl dicarbonate (2.27 g, 10.4 mmol), and then heated at 60° C. for 16 h. The reaction was cooled to RT, then treated portion wise with further di-tert-butyl dicarbonate (2.27 g, 10.4 mmol) and heated at 60° C. for 5 h. After cooling to RT, the solvent was removed in vacuo and the residue partitioned between EtOAc (3×30 mL) and saturated aqueous sodium bicarbonate (20 mL). The combined organic phase was washed with brine (20 mL), passed through a hydrophobic filter and concentrated in vacuo. The residue was purified by column chromatography (0-30% gradient elution EtOAc in cyclohexane) to afford the title compound (Intermediate AB50-2) (3.37 g, 7.8 mmol, 90%) as a colourless oil, which solidified on standing to a white solid.

$^1$H NMR (400 MHz, CDCl$_3$): δ 7.98 (d, J=8.5 Hz, 1H), 7.33 (d, J=8.3 Hz, 1H), 3.96 (s, 3H), 1.46 (s, 18H).

Step 2: Tert-Butyl (5-bromo-6-(hydroxymethyl) pyridin-2-yl)(tert-butoxycarbonyl)carbamate (Intermediate AB50-3) and Tert-Butyl (5-bromo-6-(hydroxymethyl)pyridin-2-yl)carbamate (Intermediate AB50-3')

A solution of Intermediate AB50-2 (3.37 g, 7.8 mmol) in ethanol (40 mL) was treated portion wise with sodium borohydride (0.89 g, 23.4 mmol). After stirring at RT for 16 h, the reaction was quenched dropwise with water (10 mL), and the ethanol removed in vacuo. The residue was extracted into EtOAc (3×20 mL). The combined organic phases were washed with brine (10 mL), passed through a hydrophobic filter, and concentrated in vacuo. The residue was purified by column chromatography (0-50% gradient elution EtOAc in cyclohexane) affording a 1:1 inseparable mixture of Intermediate AB50-3) and (Intermediate AB50-3') (1.86 g) as an oily white solid.

$^1$H NMR (400 MHz, CDCl$_3$): δ 7.87 (d, J=8.3 Hz, 1H), 7.82-7.76 (m, 2H), 7.23 (s, 1H), 7.19 (d, J=8.5 Hz, 1H), 4.72 (d, J=4.4 Hz, 2H), 4.66 (d, J=4.6 Hz, 2H), 3.88 (t, J=4.8 Hz, 1H), 3.86 (t, J=4.9 Hz, 1H), 1.53 (s, 9H), 1.48 (s, 18H)-1:1 mixture of di-Boc and mono-Boc Step 3: Tert-Butyl (5-bromo-6-((dimethylamino) methyl)pyridin-2-yl)carbamate (Intermediate AB50-4)

To a solution of Intermediate AB50-3 and Intermediate AB50-3' mixture (1.77 g, 4.9 mmol) in acetonitrile (35 mL) at 0° C. were added DIPEA (3.1 mL, 17.6 mmol) and methane sulfonyl chloride (0.68 mL, 8.8 mmol). After stirring for 20 min at 0° C., then warming to RT for 1.5 h, the reaction was quenched with water (40 mL) and extracted into DCM (3×40 mL). The combined organic phases were washed with brine, passed through a hydrophobic filter, and concentrated in vacuo. The residue was dissolved in acetonitrile (35 mL), treated with dimethylamine hydrochloride (4.29 g, 52.7 mmol) and potassium carbonate (7.28 g, 52.7 mmol) and heated at reflux for 16 h. The reaction mixture was filtered and concentrated in vacuo. The residue was purified by column chromatography (0-100% gradient elution EtOAc in cyclohexane followed by 0-10% 7N methanolic ammonia in EtOAc) to afford the title compound (Intermediate AB50-4) (1.16 g, 71%) as a yellow oil.

$^1$H NMR (400 MHz, CDCl$_3$): δ 7.76 (d, J=8.6 Hz, 1H), 7.72 (d, J=8.6 Hz, 1H), 7.37 (s, 1H), 3.60 (s, 2H), 2.33 (s, 6H), 1.51 (s, 9H).

Step 4: Tert-Butyl (5-(2,5-dihydrofuran-3-yl)-6-((dimethylamino)methyl)pyridin-2-yl)carbamate (Intermediate AB50-5)

A mixture of Intermediate AB50-4 (1.16 g, 3.5 mmol), 2-(2,5-dihydrofuran-3-yl)-4,4,5,5-tetramethyl-1,3,2-dioxaborolane (0.76 g, 3.9 mmol), XPhos-Pd-Gen4 (0.30 g, 0.35 mmol), XPhos (0.17 g, 0.35 mmol) and potassium phosphate tribasic (1.49 g, 7.0 mmol) was suspended in 1,4-dioxane (17 mL) and water (2 mL), degassed with nitrogen. After heating at 110° C. using microwave irradiation (Biotage Initiator®) for 1 h, the cooled mixture was diluted with water (30 mL) and extracted into EtOAc (3×50 mL). The combined extracts were washed with brine (40 mL), passed through a hydrophobic filter and concentrated in vacuo. The residue was purified by column chromatography (0-20% gradient elution 7N methanolic ammonia in EtOAc) to afford the title compound (Intermediate AB50-5) (737 mg, 66%) as a yellow oil.

$^1$H NMR (400 MHz, CDCl$_3$): δ 7.80 (d, J=8.3 Hz, 1H), 7.45 (d, J=8.5 Hz, 1H), 7.36 (s, 1H), 6.10 (s, 1H), 4.88 (s, 4H), 3.47 (s, 2H), 2.26 (s, 6H), 1.51 (s, 9H).

Step 5: 6-((Dimethylamino)methyl)-5-(THF-3-yl) pyridin-2-amine (AB50)

A solution of Intermediate AB50-5 (470 mg, 1.5 mmol) in methanol (5 mL) and ethanol (15 mL) was treated with 10% palladium on carbon (157 mg, 10 mol %). After stirring under an atmosphere of hydrogen gas at RT for 36 h, the reaction mixture was filtered through Celite® and concentrated in vacuo. The crude product was dissolved in DCM (5 mL), treated dropwise with trifluoroacetic acid (3.0 mL, 39.2 mmol) and stirred at RT for 3 h. The solvent was removed in vacuo and The residue purified by Isolute® SCX-2 cartridge eluting with 0-10% methanol/DCM followed by 10% 7N methanolic ammonia in DCM to afford the title compound (AB50) (276 mg, 85%) as an off-white solid.

$^1$H NMR (400 MHz, CDCl$_3$): δ 7.40 (d, J=8.5 Hz, 1H), 6.43 (d, J=8.1 Hz, 1H), 4.34 (s, 2H), 4.08-4.00 (m, 2H), 3.90 (td, J=7.6, 8.6 Hz, 1H), 3.81-3.73 (m, 1H), 3.62 (dd, J=6.6, 8.3 Hz, 1H), 3.51 (d, J=12.4 Hz, 1H), 3.42 (d, J=12.4 Hz, 1H), 2.36-2.26 (m, 1H), 2.25 (s, 6H), 1.91-1.81 (m, 1H).

Synthesis of Tert-Butyl (S)-((4-(6-aminopyridin-3-yl)morpholin-2-yl)methyl)(cyclopropyl)carbamate (Intermediate AB53)-Method J1

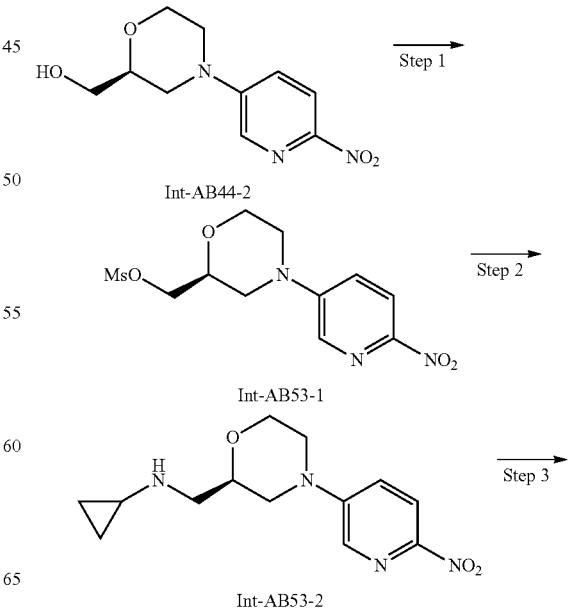

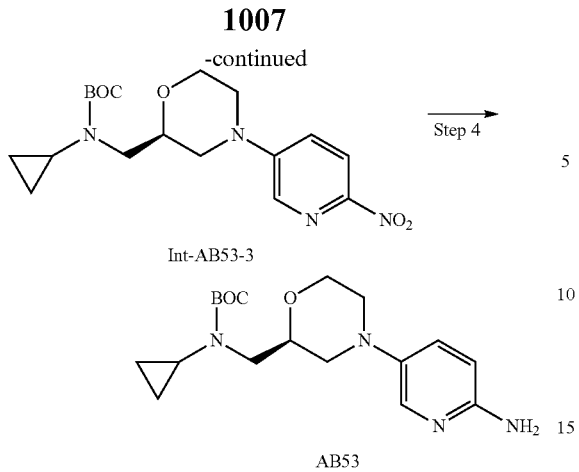

Intermediate AB45-2 was prepared following analogous procedure to Intermediate AB1-Method A1, Step 1 using (S)-morpholin-2-ylmethanol.

Step 1: (S)-(4-(6-Nitropyridin-3-yl)morpholin-2-yl) methyl Methanesulfonate (Intermediate AB53-1)

A solution of S)-(4-(6-nitropyridin-3-yl)morpholin-2-yl)methanol (Intermediate AB44-2) (600 mg, 2.51 mmol) and N,N-diisopropylethylamine (2.2 mL, 12.54 mmol) in acetonitrile (25 mL) at 0° C. was treated dropwise with methanesulfonyl chloride (0.58 mL, 7.52 mmol). After 1.5 h, the reaction was quenched with water and extracted into EtOAc (3×). The combined extracts were dried over MgSO$_4$ and concentrated in vacuo to afford the title compound (Intermediate AB53-1) (700 mg, 88%) as an orange solid which was used as is in subsequent reactions.

Step 2: (R)—N-((4-(6-Nitropyridin-3-yl)morpholin-2-yl)methyl)cyclopropanamine (Intermediate AB53-2)

A mixture of S)-(4-(6-nitropyridin-3-yl)morpholin-2-yl) methyl methanesulfonate (Intermediate AB53-1) (700 mg, 2.21 mmol), cyclopropylamine (0.76 mL, 11.03 mmol) and potassium carbonate (915 mg, 6.62 mmol) in acetonitrile (10 mL). After stirring at 80° C. for 16 h, the cooled reaction mixture was filtered, concentrated in vacuo and purified by column chromatography (0-20% methanol gradient in DCM) to afford the title compound (Intermediate AB53-2) (720 mg, quant.) as a yellow oil.
$^1$H NMR (400 MHz, DMSO): δ 8.32 (d, J=3.6 Hz, 1H), 8.23 (d, J=8.8 Hz, 1H), 7.54 (dd, J=3.4, 9.2 Hz, 1H), 4.05 (d, J=11.9 Hz, 2H), 3.94 (d, J=12.1 Hz, 1H), 3.70-3.63 (m, 2H), 3.06 (ddd, J=12.2, 12.2, 4.2 Hz, 1H), 2.82-2.76 (m, 3H), 2.17 (ddd, J=3.5, 6.5, 10.0 Hz, 1H), 0.42 (ddd, J=6.4, 6.4, 4.4 Hz, 2H), 0.28 (ddd, J=3.6, 3.6, 6.2 Hz, 2H).

Step 3: Tert-Butyl (S)-cyclopropyl((4-(6-nitropyridin-3-yl)morpholin-2-yl)methyl)carbamate (Intermediate AB53-3)

A solution of R)—N-((4-(6-nitropyridin-3-yl)morpholin-2-yl)methyl)cyclopropanamine (Intermediate AB53-2) (800 mg, 2.87 mmol), di-tert-butyl dicarbonate (721 mg, 3.31 mmol), DMAP (35 mg, 0.287 mmol) and triethylamine (0.76 mL, 8.62 mmol) in DCM (30 mL) was stirred at RT for 16 h. The mixture was washed with a saturated NaHCO$_3$ solution, the organic phase dried over MgSO$_4$ and concentrated in vacuo. The residue was purified by Isolute SCX-2 cartridge eluting with DCM to afford the title compound (Intermediate AB53-3) (907 mg, quant.) as a yellow oil.
$^1$H NMR (400 MHz, DMSO): δ 8.30 (d, J=2.9 Hz, 1H), 8.24 (d, J=9.3 Hz, 1H), 7.55 (dd, J=3.2, 9.5 Hz, 1H), 4.06 (dd, J=12.1, 20.8 Hz, 2H), 3.96-3.91 (m, 2H), 3.83 (d, J=8.7 Hz, 1H), 3.67 (t, J=11.1 Hz, 2H), 3.15-3.05 (m, 1H), 2.82 (dd, J=11.7, 11.7 Hz, 1H), 2.66-2.61 (m, 1H), 1.46 (s, 9H), 0.75 (d, J=5.4 Hz, 2H), 0.70-0.67 (m, 1H), 0.62-0.59 (m, 1H).

Step 4: Tert-Butyl (S)-((4-(6-aminopyridin-3-yl) morpholin-2-yl)methyl)(cyclopropyl)carbamate (AB53)

Step 4 was carried out following the representative procedure described in Intermediate AB1-Method A1, Step 2.
$^1$H NMR (400 MHz, DMSO): δ 7.64 (d, J=3.1 Hz, 1H), 7.22 (dd, J=3.3, 8.9 Hz, 1H), 6.47 (d, J=8.5 Hz, 1H), 5.49 (s, 2H), 3.97-3.91 (m, 3H), 3.83-3.78 (m, 1H), 3.71-3.61 (m, 2H), 3.33-3.28 (m, 2H), 2.64 (ddd, J=11.4, 11.4, 3.7 Hz, 1H), 2.37 (t, J=9.3 Hz, 1H), 1.46 (s, 9H), 0.74 (d, J=8.5 Hz, 2H), 0.67-0.63 (m, 1H), 0.60-0.57 (m, 1H).

Synthesis of 1-(6-aminopyridin-3-yl)-3-((3-fluoroazetidin-1-yl)methyl)piperidin-3-ol (Intermediate AB59)-Method K1

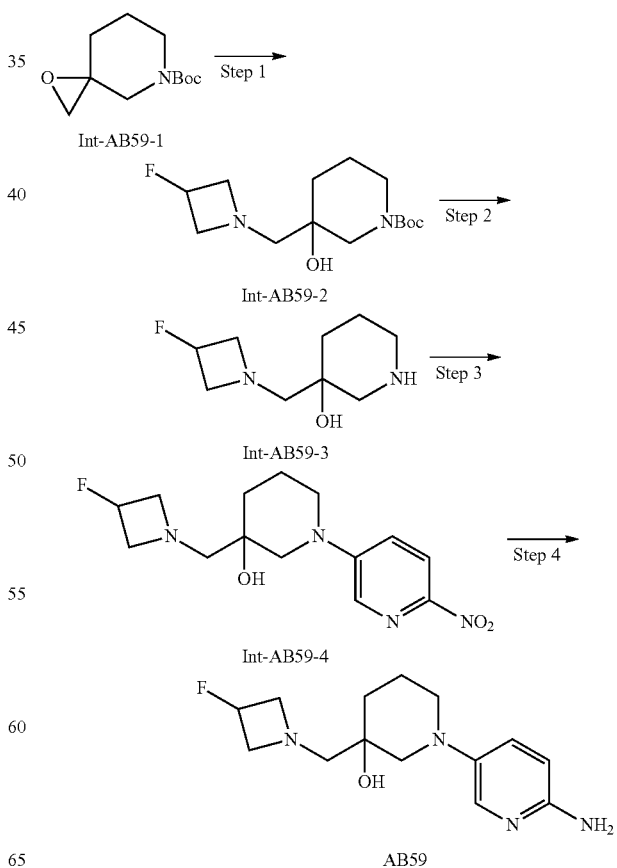

Step 1: Tert-Butyl 3-((3-fluoroazetidin-1-yl)methyl)-3-hydroxypiperidine-1-carboxylate (Intermediate AB59-2)

To a solution of tert-butyl 1-oxa-5-azaspiro[2.5]octane-5-carboxylate (1.0 g, 4.6 mmol) and 3-fluoroazetidine hydrochloride (1.05 g, 9.3 mmol) in ethanol (15 mL) and water (1.7 mL) was added triethylamine (2 mL, 14.0 mmol). After heating at 100° C. using microwave irradiation (Biotage Initiator®) for 3 h, the mixture was concentrated in vacuo. The residue was purified by column chromatography (0-10% gradient elution 7N methanolic ammonia in EtOAc/cyclohexane) to afford the title compound (Intermediate AB59-2) (1.08 g, 80%) as a pale yellow oil.

$^1$H NMR (400 MHz, CDCl$_3$): δ 5.22-5.00 (m, 1H), 3.86-3.72 (m, 2H), 3.42-3.39 (m, 1H), 3.33 (ddd, J=4.1, 6.7, 9.7 Hz, 2H), 3.27-3.22 (m, 1H), 3.11 (s, 2H), 2.60 (d, J=12.9 Hz, 1H), 2.46 (d, J=13.3 Hz, 1H), 1.77-1.71 (m, 2H), 1.62-1.54 (m, 2H).

Step 2: 3-((3-fluoroazetidin-1-yl)methyl)piperidin-3-ol (Intermediate AB59-3)

To a stirred solution of tert-butyl 3-((3-fluoroazetidin-1-yl)methyl)-3-hydroxypiperidine-1-carboxylate (Intermediate AB59-2) (1.28 g, 4.4 mmol) in DCM (11 mL) at 0° C. was added trifluoroacetic acid (4 mL). After stirring for 4 h allowing warming to RT, the mixture was concentrated in vacuo. The residue was purified by Isolute® SCX-2 cartridge eluting with 20% 7N methanolic ammonia in DCM to afford the title compound (Intermediate AB59-3) (790 mg, 94%) as a yellow oil.

$^1$H NMR (400 MHz, CDCl$_3$): δ 5.21-5.00 (m, 1H), 3.79-3.69 (m, 2H), 3.48 (s, 1H), 3.38-3.25 (m, 2H), 2.97 (d, J=12.4 Hz, 1H), 2.77 (d, J=12.4 Hz, 1H), 2.60-2.51 (m, 2H), 2.50 (d, J=2.9 Hz, 2H), 1.79 (ddd, J=7.9, 3.7, 25.1 Hz, 1H), 1.63-1.55 (m, 1H), 1.54-1.46 (m, 1H), 1.39-1.30 (m, 1H).

Step 3: 3-((3-fluoroazetidin-1-yl)methyl)-1-(6-nitropyridin-3-yl)piperidin-3-ol (Intermediate AB59-4)

Step 3 was carried out following the representative procedure described in Intermediate AB2-Method B1, Step 1.

$^1$H NMR (400 MHz, CDCl$_3$): δ 8.14 (dd, J=3.0, 6.1 Hz, 2H), 7.20 (dd, J=3.2, 9.2 Hz, 1H), 5.25-5.05 (m, 1H), 3.85-3.74 (m, 2H), 3.69-3.61 (m, 1H), 3.50-3.35 (m, 3H), 3.26-3.14 (m, 2H), 2.89 (s, 1H), 2.65 (d, J=13.1 Hz, 1H), 2.55 (d, J=13.1 Hz, 1H), 2.03-1.92 (m, 1H), 1.73-1.66 (m, 2H).

Step 4: Synthesis of 1-(6-aminopyridin-3-yl)-34(3-fluoroazetidin-1-yl)methyl)piperidin-3-ol (AB59)

Step 4 was carried out following the representative procedure described in Intermediate AB1-Method A1, Step 2.

$^1$H NMR (400 MHz, CDCl$_3$): δ 8.16-8.12 (m, 2H), 7.25-7.20 (m, 1H), 5.26-5.07 (m, 1H), 3.68-3.61 (m, 1H), 3.54 (d, J=13.1 Hz, 1H), 3.28-3.21 (m, 2H), 3.11-2.94 (m, 4H), 2.74-2.69 (m, 2H), 2.59 (dd, J=1.5, 13.6 Hz, 1H), 2.18-1.96 (m, 3H), 1.80-1.61 (m, 3H).

Synthesis of 3S)-1-(1-(6-aminopyridin-3-yl)ethyl)piperidin-3-ol (Intermediate AB71)-Method L1

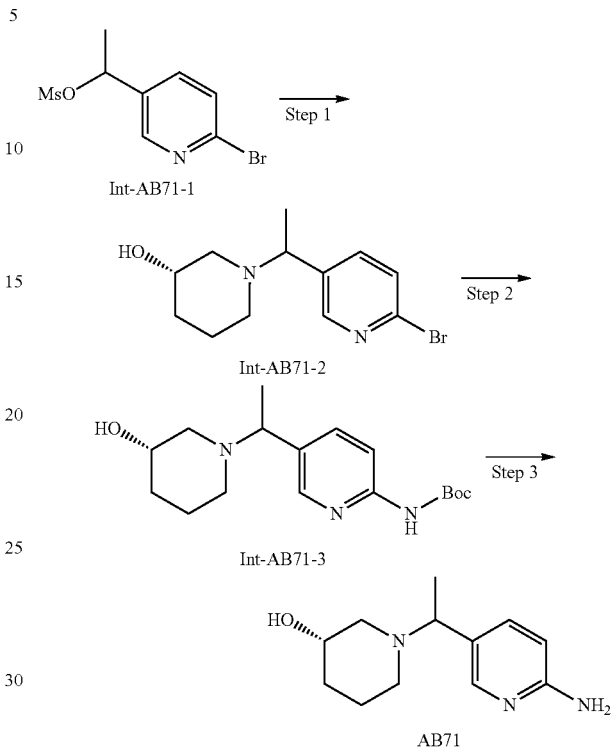

1-(6-bromopyridin-3-yl)ethyl methanesulfonate (Intermediate AB71-1) was prepared as described in US20200038378.

Step 1: (3S)-1-(1-(6-bromopyridin-3-yl)ethyl)piperidin-3-ol (Intermediate AB71-2)

Step 1 was performed according to the procedure described in Intermediate AB53-Method J1, Step 2 using (S)-piperidin-3-ol.

$^1$H NMR (400 MHz, DMSO): δ 8.31 (s, 1H), 7.68 (dd, J=2.5, 8.2 Hz, 1H), 7.60 (dd, J=2.6, 8.0 Hz, 1H), 4.54 (dd, J=5.1, 9.5 Hz, 1H), 3.60 (ddd, J=6.7, 13.6, 18.7 Hz, 1H), 3.47-3.36 (m, 1H), 2.76 (ddd, J=11.9, 11.9, 4.0 Hz, 1H), 2.69 (dd, J=3.7, 10.0 Hz, 1H), 2.56 (d, J=11.2 Hz, 1H), 1.85-1.71 (m, 1H), 1.66-1.58 (m, 1H), 1.38 (td, J=3.1, 11.2 Hz, 1H), 1.28 (d, J=6.9 Hz, 3H), 1.05-0.91 (m, 1H).

Step 2: Tert-Butyl (5-(1-((S)-3-hydroxypiperidin-1-yl)ethyl)pyridin-2-yl)carbamate (Intermediate AB71-3)

Step 2 was performed according to the procedure described in Intermediate AB6-Method F1, Step 1 using tert-butyl carbamate.

$^1$H NMR (400 MHz, DMSO): δ 9.68 (s, 1H), 8.12 (dd, J=2.4, 2.4 Hz, 1H), 7.73 (d, J=8.9 Hz, 1H), 7.63 (td, J=2.1, 8.9 Hz, 1H), 4.56-4.49 (m, 1H), 3.56-3.49 (m, 1H), 3.44-3.37 (m, 1H), 2.77-2.67 (m, 2H), 2.59 (d, J=10.5 Hz, 1H), 1.79-1.73 (m, 2H), 1.63-1.56 (m, 2H), 1.46 (s, 9H), 1.28 (d, J=6.7 Hz, 6H).

Step 3: (3S)-1-(1-(6-aminopyridin-3-yl)ethyl)piperidin-3-ol (AB71)

Step 3 was performed according to the procedure described in Intermediate AB50-Method I1, Step 5 [TFA/DCM treatment only] to afford the title compound (AB71) as a yellow residue which was used crude in subsequent reactions.

Synthesis of (R)-1-(6-bromo-3-((THF-3-yl)oxy)pyridin-2-yl)-N,N-dimethylmethanamine (Intermediate AB84)-Method M1

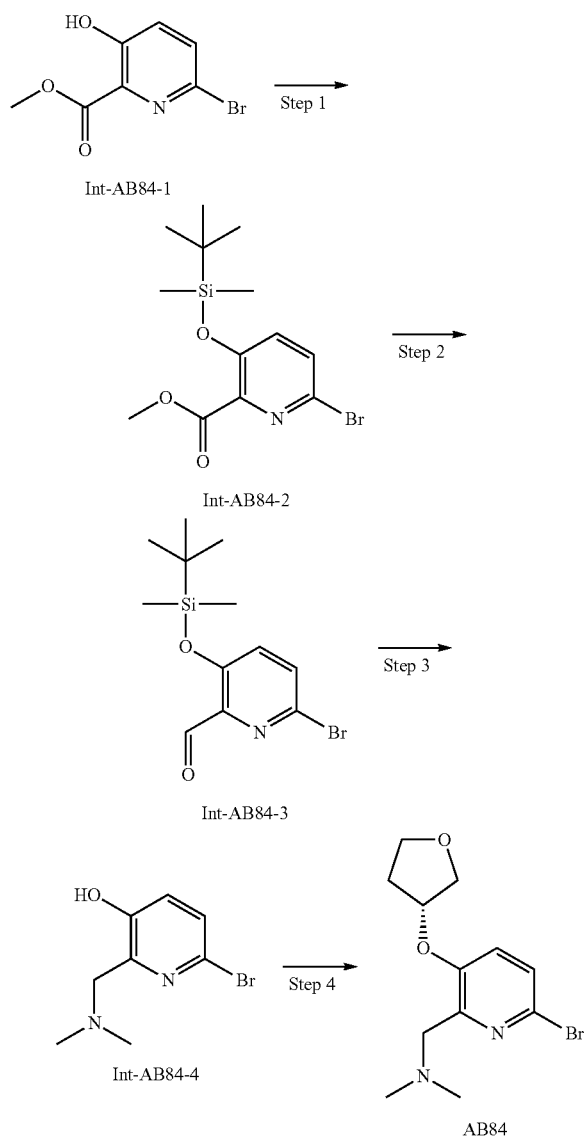

Step 1: Methyl 6-bromo-3-((tert-butyldimethylsilyl)oxy)picolinate (Intermediate AB84-2)

A mixture of methyl-6-bromo-3-hydroxypyridine-2-carboxylate (Intermediate AB84-1) (2.50 g, 10 77 mmol), TBDMSCl (2.44 g, 16.16 mmol) and imidazole (1.10 g, 16.16 mmol) in DCM (30 mL) was stirred at RT for 18 h. The reaction was diluted with DCM and washed with water. The organic solution was washed with brine, dried over $Na_2SO_4$, and concentrated in vacuo to leave the title compound (Intermediate AB84-2) (3.21 g, 9.27 mmol) as a pale yellow oil which was used crude in subsequent reactions.

Step 2: 6-Bromo-3-((tert-butyldimethylsilyl)oxy)picolinaldehyde (Intermediate AB84-3)

A solution of methyl 6-bromo-3-((tert-butyldimethylsilyl)oxy)picolinate (Intermediate AB84-2) (3.20 g, 9.24 mmol) in DCM (30 mL) at −78° C. under a nitrogen atmosphere was treated dropwise with DIBAL-H (1.5M solution in toluene, 13.6 mL, 20.33 mmol). After stirring cold for 3 h, the reaction was quenched with Rochelle's salt (saturated solution), diluted with DCM and stirred at RT for 20 min. The gel was removed by filtering through Celite® and the filtrate was separated. The organic phase was dried over $Na_2SO_4$ and concentrated in vacuo to leave the title compound (Intermediate AB84-3) as a mixture of desired product and some product with loss of TBS-protecting group (3.01 g). Carried forward into the next step as a mixture.

Step 3: 6-Bromo-2-((dimethylamino)methyl)pyridin-3-ol (Intermediate AB84-4)

A solution of 6-bromo-3-((tert-butyldimethylsilyl)oxy)picolinaldehyde (Intermediate AB84-3) (3.00 g, 9.49 mmol) and dimethylamine (2M solution in THF, 9.5 mL, 18.97 mmol) in DCM/MeOH (6:1, 35 mL), with $MgSO_4$ drying agent added, was treated with sodium triacetoxyborohydride (3.02 g, 14.23 mmol). After stirring at RT for 18 h, the reaction mixture was dry-loaded onto ISOLUTE® HM-N disposable liquid-liquid extraction columns and purified by column (gradient elution: 0-10% 7N methanolic ammonia in DCM) to afford the title compound (Intermediate AB84-4) (1.14 g, 4.94 mmol) as an orange oil. $^1$H NMR (400 MHz, $CDCl_3$): δ 7.24 (d, J=8.7 Hz, 1H), 6.99 (d, J=8.4 Hz, 1H), 3.84 (s, 2H), 2.38 (s, 6H).

Step 4: (R)-1-(6-Bromo-3-((THF-3-yl)oxy)pyridin-2-yl)-N,N-dimethylmethanamine (AB84)

A solution of 6-bromo-2-((dimethylamino)methyl)pyridin-3-ol (Intermediate AB84-4) (350 mg, 1.51 mmol) and (R)-(−)-3-hydroxy-THF (200 mg, 2.27 mmol) in THF (10 mL) under a nitrogen atmosphere was treated with triphenyl phosphine (675 mg, 2.57 mmol), followed by diethyl azodicarboxylate (528 mg, 3.03 mmol) dropwise. After stirring at RT for 4 h, a solution of 2N sodium hydroxide was added. After stirring for 30 min, the mixture was diluted with water and extracted into EtOAc (2×). The combined extracts were washed with brine, dried over $Na_2SO_4$, and concentrated in vacuo. The residue was purified by column chromatography (gradient elution: 0-10% 7N methanolic ammonia in DCM) to afford an orange oil and then with an Isolute® SCX-2 cartridge eluting with MeOH followed by 7N methanolic ammonia in DCM (1:1) to afford the title compound (AB84) (370 mg, 1.23 mmol) as a yellow oil. $^1$H NMR (400 MHz, $CDCl_3$): δ 7.32 (d, J=8.5 Hz, 1H), 7.00 (d, J=8.5 Hz, 1H), 4.93 (ddd, J=2.0, 4.2, 8.2 Hz, 1H), 4.04-3.92 (m, 4H), 3.59 (s, 2H), 2.34 (s, 6H), 2.32-2.10 (m, 2H).

Synthesis of 6-((dimethylamino)methyl)-4-(tetrahydrofuran-3-yl)pyridin-2-amine (Intermediate AB85)

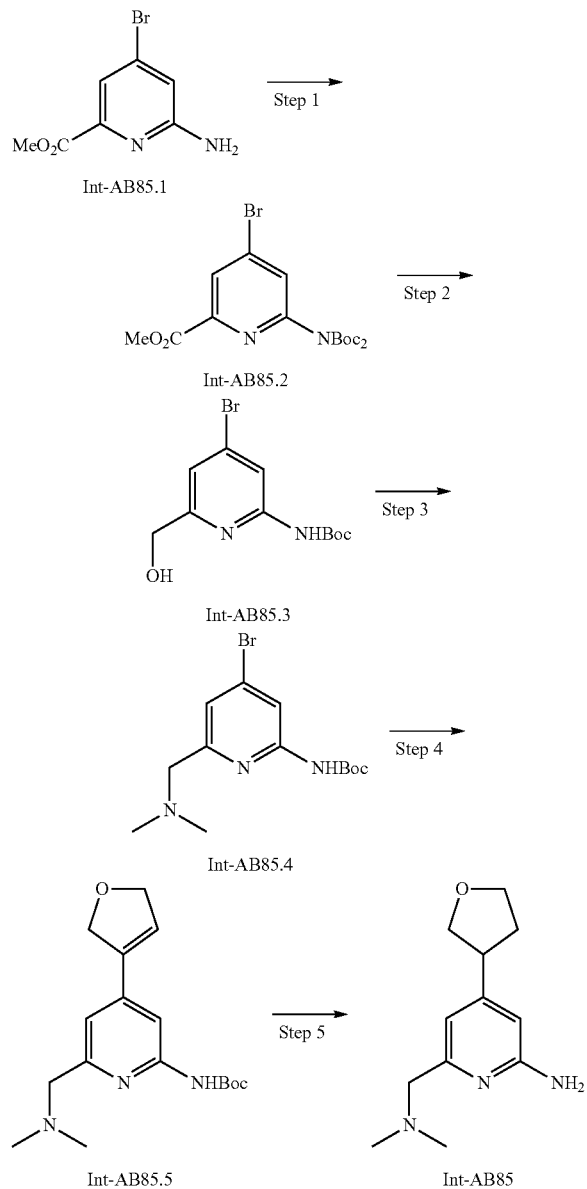

Step 1: methyl 6-(bis(tert-butoxycarbonyl)amino)-4-bromopicolinate (Int-AB85.2)

To a solution of methyl 6-amino-4-bromo-pyridine-2-carboxylate (2.00 g, 8.66 mmol, 1.00 eq)-(Int-AB85.1) in THF (60.00 mL) at 0° C. were added triethylamine (3.0 mL, 21.6 mmol, 2.50 eq), Di-tert-butyl decarbonate (4.0 mL, 17.3 mmol, 2.00 eq) and DMAP (0.21 g, 1.73 mmol, 0.200 eq). After stirring at 0° C. for 30 min and then at RT 4 h, the solvent was removed in vacuo and the crude residue purified by column chromatography (0-5% gradient eluting with 7N methanolic ammonia in DCM) to afford the title compound (Int-AB85.2) (3.51 g, 8.13 mmol, 94%) as an off white solid. $^1$H NMR (400 MHz, DMSO): δ 8.20 (d, J=2.2 Hz, 1H), 8.18 (d, J=2.2 Hz, 1H), 3.94 (s, 3H), 1.46 (s, 18H).

Step 2: Tert-Butyl (4-bromo-6-(hydroxymethyl) pyridin-2-yl)carbamate (Int-AB85.3)

A solution of Int-AB85.2 (3.51 g, 8.13 mmol) in ethanol (80 mL) was treated portion-wise with sodium borohydride (1.22 g, 32.5 mmol). After stirring for 15 min and then stirring at 70° C. for 2 h, the cooled reaction mixture was quenched with dropwise addition of water (30 mL), and the ethanol removed in vacuo. The residue was extracted into EtOAc (3×40 mL). The combined organic phases were washed with brine (20 mL), dried over magnesium sulfate, filtered, and concentrated in vacuo to afford the title compound (Int-AB85.3) (2.34 g, 7.71 mmol, 95%) as a yellow oil. $^1$H NMR (400 MHz, DMSO): δ 10.10 (s, 1H), 7.95 (d, J=1.3 Hz, 1H), 7.33 (d, J=2.2 Hz, 1H), 5.56 (t, J=5.9 Hz, 1H), 4.50 (d, J=5.7 Hz, 2H), 1.51 (s, 9H).

Step 3: Tert-Butyl (4-bromo-6-((dimethylamino) methyl)pyridin-2-yl)carbamate (Int-AB85.4)

To a solution of Int-AB85.3 (2.34 g, 7.72 mmol) and DIPEA (5.4 mL, 30.9 mmol) in acetonitrile (60 mL) at 0° C. was added methanesulfonyl chloride (1.2 mL, 15.4 mmol). After stirring for 20 minutes at 0° C. and then at RT for 1.5 h, the reaction was quenched with water (40 mL) and extracted with ethyl acetate (3×40 mL). The combined organic phases were washed with brine, passed through a hydrophobic filter, and concentrated in vacuo.

To the residue dissolved in acetonitrile (60 mL) were added dimethylamine (2M solution in THF, 11.5 mL, 23.157 mmol) and potassium carbonate (3.2 g, 23.157 mmol). After stirring at reflux for 3 h, the reaction was cooled, diluted with water (50 mL) and extracted with ethyl acetate (3×40 mL). The combined organic phases were dried over magnesium sulfate, filtered, and concentrated in vacuo. The residue was purified by column chromatography (0-20% gradient elution with 7N methanolic ammonia in DCM to afford the title compound Int-AB85.4 (1.37 g, 54%) as a brown solid. $^1$H NMR (400 MHz, DMSO): δ 10.12 (s, 1H), 7.96 (d, J=1.8 Hz, 1H), 7.31 (d, J=1.6 Hz, 1H), 3.46 (s, 2H), 2.24 (s, 6H), 1.51 (s, 9H).

Step 4: Tert-Butyl (4-(2,5-dihydrofuran-3-yl)-6-((dimethylamino)methyl)pyridin-2-yl)carbamate (Int-AB85.5)

To a mixture of Int-AB85.4 (1.37 g, 4.15 mmol) in 1,4-dioxane (25.0 mL) and water (4 mL) were added 2-(2,5-di hydrofuran-3-yl)-4,4,5,5-tetramethyl-1,3,2-dioxaborolane (0.89 g, 4.56 mmol), XPhos-Pd-Gen2 (0.32 g, 0.415 mmol), XPhos (0.20 g, 0.415 mmol) and potassium phosphate tribasic (2.64 g, 12.4 mmol). After degassing with nitrogen and stirring at 80° C. for 3 h, the cooled mixture was diluted with water (30 mL) and extracted into EtOAc (3×40 mL). The combined extracts were washed with brine (50 mL) dried over magnesium sulfate, filtered, and concentrated in vacuo. The residue was purified by column chromatography (0-100% gradient elution with EtOAc in cyclohexane followed by 0-10% 7N methanolic ammonia in EtOAc) to afford the title compound Int-AB85.5 (1.12 g, 3.51 mmol, 85%) as an orange oil.

$^1$H NMR (400 MHz, DMSO): δ 9.81 (s, 1H), 7.66 (s, 1H), 7.14 (s, 1H), 6.77 (t, J=2.0 Hz, 1H), 4.97-4.92 (m, 2H), 4.83-4.77 (m, 2H), 3.45 (s, 2H), 2.23 (s, 6H), 1.51 (s, 9H).

Step 5: 6-((dimethylamino)methyl)-4-(tetrahydrofuran-3-yl)pyridin-2-amine (AB85)

To a solution of Int-AB85.5 (1.12 g, 3.51 mmol) in methanol (5 mL) and ethanol (15 mL) was added 10% palladium on carbon (373 mg, 10 mol %). After stirring under an atmosphere of hydrogen gas at room temperature for 16 h, the reaction mixture was filtered through Celite® and concentrated in vacuo.

To a solution of the reduced product in DCM (15 mL) was added dropwise trifluoroacetic acid (2.7 mL, 35.1 mmol). After stirring at RT for 3 h, the solvent was removed in vacuo and the crude residue purified by Isolute® SCX-2 cartridge eluting with 0-10% methanol/DCM followed by 10% 7N methanolic ammonia in DCM. The residue was purified further by column chromatography (0-10% gradient elution 7N methanolic ammonia in DCM) to afford the title compound (AB85) (354 mg, 1.59 mmol 45%) as an orange oil. $^1$H NMR (400 MHz, DMSO): δ 6.50 (s, 1H), 6.24 (s, 1H), 5.81 (s, 2H), 4.02 (t, J=7.4 Hz, 1H), 3.98-3.92 (m, 1H), 3.84-3.77 (m, 1H), 3.57 (t, J=7.4 Hz, 1H), 3.28 (s, 2H), 3.25-3.22 (m, 1H), 2.35-2.27 (m, 1H), 2.21 (s, 6H), 1.94-1.87 (m, 1H).

The following intermediates were available commercially or prepared by known literature routes.

TABLE 3

Additional intermediates that were commercially available or prepared by known literature routes.

| # | STRUCTURE |
|---|---|
| AC8 | 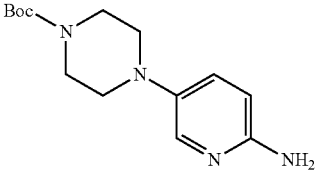 [SMILES: CC(C)(C)OC(=O)N1CCN(c2ccc(N)nc2)CC1] |
| AC9 | 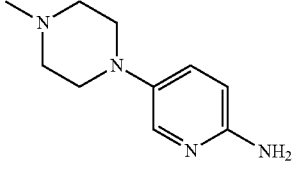 |
| AC10 | 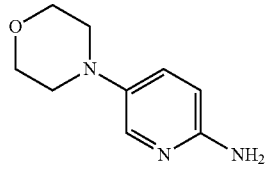 [SMILES: Nc1ccc(N2CCOCC2)cn1] |
| AC11 | 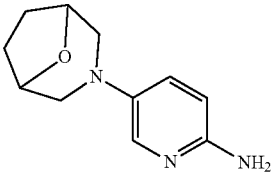 [SMILES: Nc1ccc(N2CC3CCC(C2)O3)cn1] |
| AC12 | 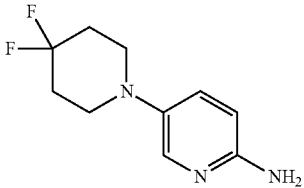 [SMILES: Nc1ccc(N2CCC(F)(F)CC2)cn1] |

TABLE 3-continued

Additional intermediates that were commercially available or prepared by known literature routes.

| # | STRUCTURE |
|---|---|
| AC14 | 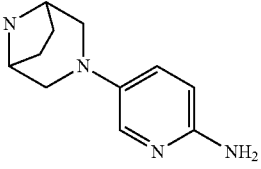 |
| AC15 | 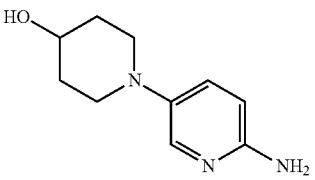 |
| AC16 | 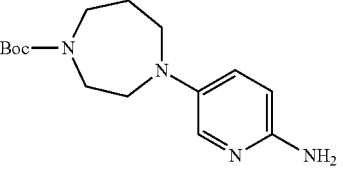 [SMILES: CC(C)(C)OC(=O)N1CCCN(c2ccc(N)nc2)CC1] |
| AC17 | 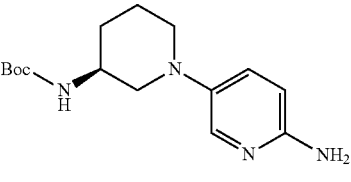 [SMILES: CC(C)(C)OC(=O)N[C@H]1CCCN(c2ccc(N)nc2)C1] |
| AC18 | 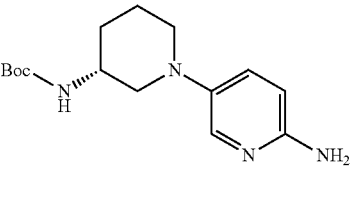 [SMILES: CC(C)(C)OC(=O)N[C@@H]1CCCN(c2ccc(N)nc2)C1] |
| AC19 | 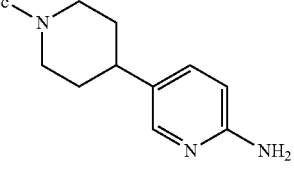 |
| AC21 | 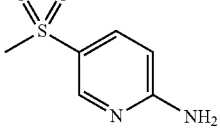 |
| AC22 | 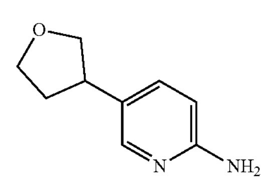 [SMILES: Nc1ccc(C2CCOC2)cn1] |

TABLE 3-continued

Additional intermediates that were commercially available or prepared by known literature routes.

| # | STRUCTURE |
|---|---|
| AC23 | ethyl 6-aminonicotinamide structure |
| AC24 | Boc-piperidinyl pyrazole amine structure |
| AC25 | (S)-3-hydroxypiperidinyl aminopyridine structure |
| AC26 | (R)-3-hydroxypiperidinyl aminopyridine structure |
| AC27 | tetrahydropyranyl-methylpyrazole amine structure |
| AC32 | 4-(hydroxymethyl)piperidinyl aminopyridine structure |
| AC35 | N-methylpiperazinyl aminopyridine structure |
| AC38 | morpholinomethyl aminopyridine structure |
| AC44 | (hydroxymethyl)morpholinyl aminopyridine structure |
| AC49 | 4-methoxypiperidinyl aminopyridine structure |

The following intermediates were prepared according to Intermediate Methods A1 to M1 as described above.

TABLE 4

Intermediates prepared according to Intermediate Methods A1 to M1.

| # | STRUCTURE | |
|---|---|---|
| AC1 | 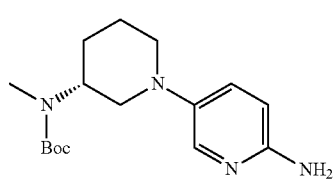 [SMILES: CN(C(=O)OC(C)(C)C)[C@@H]1CCCN(c2ccc(N)nc2)C1] | Method A1 using (R)-tert-butyl-methyl(piperidin-3-yl)carbamate |

TABLE 4-continued

Intermediates prepared according to Intermediate Methods A1 to M1.

| # | STRUCTURE | |
|---|---|---|
| AC2 | [structure] | Method B1 using tert-butyl methyl(4-methyl-piperidin-4-yl)carbamate |
| AC3 | [structure] | Method C1 using (R)-1-(piperidin-4-yl)ethanol |
| AC4 | [structure] | Method D1 using ethylamine |
| AC5 | [structure] | Method E1 using tert-butyl methyl(4-piperidinyl)carbamate |
| AC6 | [structure] | Method F1 using tert-butyl-(S)-methyl(pyrrolidin-3-yl)carbamate |
| AC7 | [structure] | Method G1 using N, N, N'-trimethylethylenediamine |
| AC13 | [structure] | Method A1 using tert-butyl methyl(4-piperidinyl)carbamate |
| AC20 | [structure] | Method A1 using (S)-tert-butyl-methyl(piperidin-3-yl)carbamate |

TABLE 4-continued

Intermediates prepared according to Intermediate Methods A1 to M1.

| # | STRUCTURE | |
|---|---|---|
| AC28 | [structure: 4-hydroxypiperidine linked to 6-aminopyridine] | Method E1 using 4-hydroxy-piperidine |
| AC29 | [structure: (R)-3-(2-hydroxypropan-2-yl)piperidine linked to 6-aminopyridine] | Method C1 using (R)-2-(piperidin-3-yl)propan-2-ol |
| AC30 | [structure: (S)-3-(2-hydroxypropan-2-yl)piperidine linked to 6-aminopyridine] | Method C1 using (S)-2-(piperidin-3-yl)propan-2-ol |
| AC31 | [structure: tert-butyl piperidine-4-carboxylate linked to 6-aminopyridine] | Method C1 using tert-butyl piperidine-4-carboxylate |
| AC33 | [structure: 4-(2-hydroxypropan-2-yl)piperidine linked to 6-aminopyridine] | Method C1 using 2-(piperidin-4-yl)propan-2-ol |
| AC34 | [structure: N,N-dimethylethylenediamine amide linked to 6-aminopyridine] | Method D1 using N,N-dimethylethylene-diamine |
| AC36 | [structure: (R)-3-(Boc-amino)piperidine linked to 6-aminopyridine] | Method E1 using tert-butyl (R)-piperidin-3-ylcarbamate |
| AC37 | [structure: Boc-piperazine linked to 6-aminopyridine] | Method E1 using tert-butyl (R)-piperidin-3-ylcarbamate |

TABLE 4-continued

Intermediates prepared according to Intermediate Methods A1 to M1.

| # | STRUCTURE | |
|---|---|---|
| AC39 | 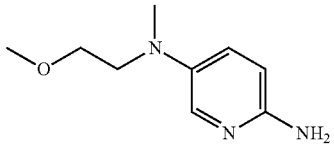 | Method A1 using 2-methoxy-N-methylethan-1-amine |
| AC40 | 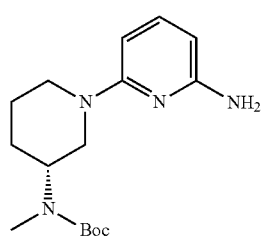 [SMILES: CN(C(=O)OC(C)(C)C)[C@@H]1CCCN(c2cccc(N)n2)C1] | Method E1 using tert-butyl (R)-methyl(piperidin-3-yl)carbamate |
| AC41 | 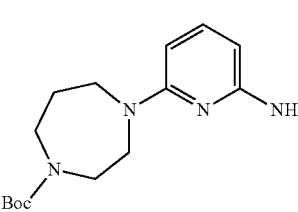 | Method F1 using tert-butyl 1,4-diazepane-1-carboxylate |
| AC42 | 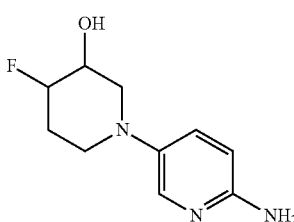 | synthesis of Intermediate AA49 using trans-4-fluoro-3-hydroxypiperidine |
| AC43 | 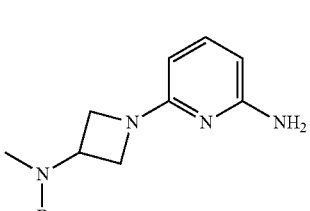 | Method F1 using tert-butyl azetidine-3-yl(methyl)carbamate hydrochloride |
| AC45 | 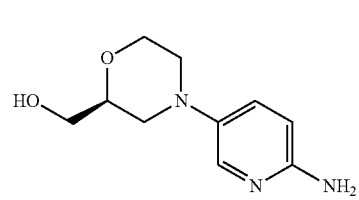 [SMILES: Nc1ccc(N2CCO[C@H](CO)C2)cn1] | Method A1 using (S)-morpholin-2-ylmethanol |
| AC46 | 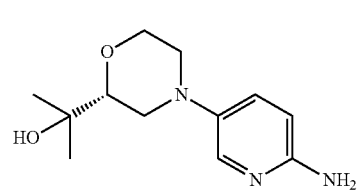 | Method A1 using (R)-2-(morpholin-2-yl)propan-2-ol |

TABLE 4-continued

Intermediates prepared according to Intermediate Methods A1 to M1.

| # | STRUCTURE | |
|---|---|---|
| AC47 | (structure) | Method A1 using (S)-2-(morpholin-2-yl)propan-2-ol |
| AC48 | (structure) | Method H1 using 4-(Boc-amino)-3,3-difluoropiperidine |
| AC50 | (structure) | Method I1 Using dimethylamine |
| AC51 | (structure) | Method F1 using tert-butyl hexahydropyrrolo[3,4- |
| AC52 | (structure) | Method A1 using 4-(piperidin-3-yl)morpholine |
| AC53 | (structure) | Method J1 using cyclopropyl amine |
| AC54 | (structure) | Method F1 using (3aR,6aR)-tert-butyl hexahydropyrrolo[3,4-b]pyrrole-5(1H)-carboxylate |
| AC55 | (structure) | Method J1 using 3-fluoroazetidine |

TABLE 4-continued

Intermediates prepared according to Intermediate Methods A1 to M1.

| # | STRUCTURE | |
|---|---|---|
| AC56 | (structure) | Method A1 using 4-(piperidin-4-yl)morpholine |
| AC57 | (structure) | Method K1 using (S)-3-fluoropyrrolidine hydrochloride |
| AC58 | (structure) | Method K1 using N-methylcyclopropanamine |
| AC59 | (structure) | Method K1 using 3-fluoroazetidine hydrochloride |
| AC60 | (structure) | Method J1 using N-methyl-cyclopropanamine |
| AC61 | (structure) | Method J1 using cyclopropanamine |
| AC62 | (structure) | Method F1 using (3aS,6aS)-tert-butyl hexahydropyrrolo[3,4-b]pyrrole-5(1H)-carboxylate |
| AC63 | (structure) | Method A1 using 4-methyl-1-oxa-4,8-diazaspiro[5.5]undecane |

TABLE 4-continued

Intermediates prepared according to Intermediate Methods A1 to M1.

| # | STRUCTURE | |
|---|---|---|
| AC64 | 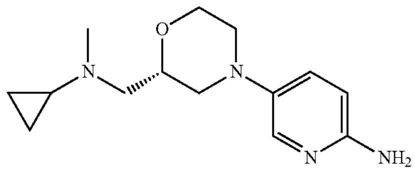 [SMILES: CN(C[C@H]1CN(c2ccc(N)nc2)CCO1)C1CC1] | Method J1 using N-methylcyclopropanamine |
| AC65 | 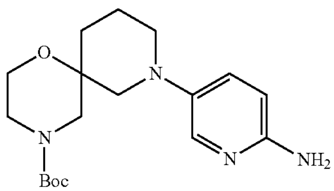 [SMILES: CC(C)(C)OC(=O)N1CCOC2(CCCN(c3ccc(N)nc3)C2)C1] | Method A1 using 4-Boc-1-oxa-4,8-diazaspiro[5.5]undecane |
| AC66 | 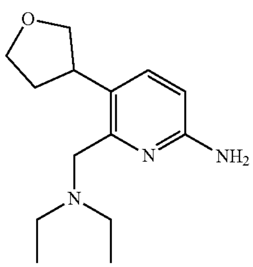 [SMILES: CCN(CC)Cc1nc(N)ccc1C1CCOC1] | Method I1 using diethylamine |
| AC67 | 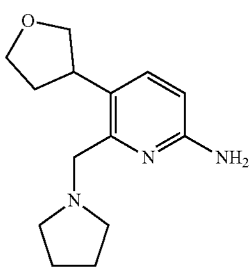 [SMILES: Nc1ccc(C2CCOC2)c(CN2CCCC2)n1] | Method I1 using pyrrolidine |
| AC68 | 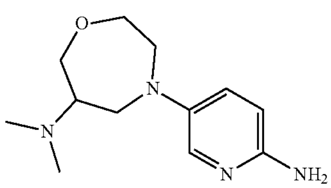 [SMILES: CN(C)C1COCCN(c2ccc(N)nc2)C1] | Method A1 using N,N-dimethyl-1,4-oxazepan-6-amine |
| AC69 | 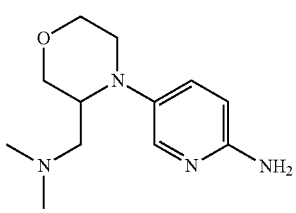 [SMILES: CN(C)CC1COCCN1c1ccc(N)nc1] | Method A1 using N,N-dimethyl(3-morpholinyl)methanamine |
| AC70 | 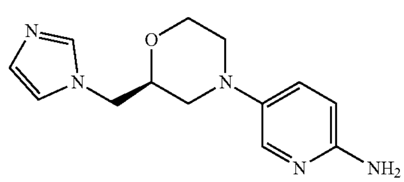 [SMILES: Nc1ccc(N2CCO[C@H](Cn3ccnc3)C2)cn1] | Method J1 using imidazole |

TABLE 4-continued

Intermediates prepared according to Intermediate Methods A1 to M1.

| # | STRUCTURE | |
|---|---|---|
| AC71 | (structure) | Method L1 using (S)-piperidin-3-ol |
| AC72 | (structure) | Method A1, Step 1 using (3-fluoropiperidin-3-yl)methanol followed by Method J1 using dimethylamine |
| AC73 | (structure) | Method L1 using dimethylamine |
| AC74 | (structure) | Method L1 using (S)-2-methylmorpholine |
| AC75 | (structure) | See synthesis procedure for Intermediate AA144 using (R)-piperidin-3-ol |
| AC76 | (structure) | See synthesis procedure for Interemediate AA144 using 7-oxo-4-azaspiro[2.5]octane |
| AC77 | (structure) | Method L1 using 4-hydroxy-piperidine |
| AC78 | (structure) | See synthesis procedure for Intermediate AA144 using (R)-3-methylmorpholine |

TABLE 4-continued

Intermediates prepared according to Intermediate Methods A1 to M1.

| # | STRUCTURE | |
|---|---|---|
| AC79 | 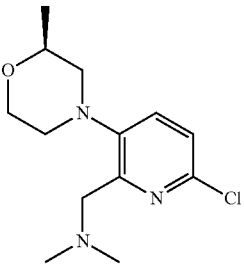 [SMILES: C[C@H]1CN(c2ccc(Cl)nc2CN(C)C)CCO1] | See synthesis procedure for Intermediate AA144 using (S)-2-methylmorpholine |
| AC80 | 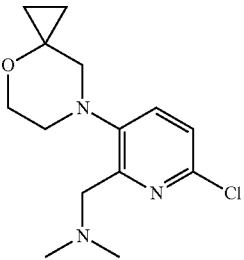 [SMILES: CN(C)Cc1nc(Cl)ccc1N1CCOC2(CC2)C1] | See synthesis procedure for Intermediate AA144 using 4-oxa-7-azaspiro[2.5]octane |
| AC81 | 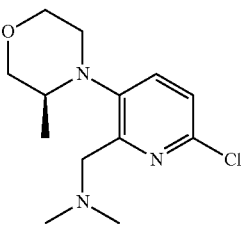 [SMILES: C[C@H]1COCCN1c1ccc(Cl)nc1CN(C)C] | See synthesis procedure for Intermediate AA144 using (S)-3-methylmorpholine |
| AC82 | 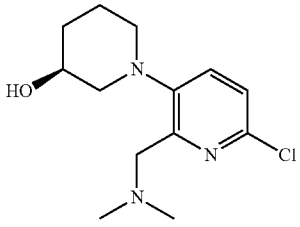 [SMILES: CN(C)Cc1nc(Cl)ccc1N1CCC[C@H](O)C1] | See synthesis procedure for Intermediate AA144 using (S)-piperidin-3-ol |
| AC83 | 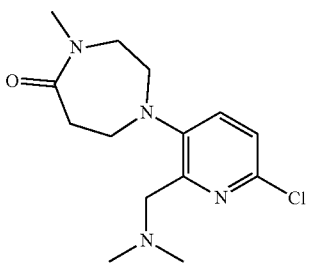 [SMILES: CN(C)Cc1nc(Cl)ccc1N1CCC(=O)N(C)CC1] | See synthesis procedure for Intermediate AA144 using 4-methyl-1,4-diazepan-5-one |

TABLE 4-continued

Intermediates prepared according to Intermediate Methods A1 to M1.

| # | STRUCTURE | |
|---|---|---|
| AC84 | (structure) | Method M1 using (R)-(−)-3-hydroxy-THF |
| AC85 | (structure) | See synthesis procedure for Intermediate AA144 using 4-methyl-piperidin-4-ol |
| AC86 | (structure) | Method I1, step 3 using 2-Chloro-5,6,7,8-tetrahydro-quinolin-8-ol |
| AC87 | (structure) | See synthesis procedure for Intermediate AA144 using (R)-2-methylmorpholine |
| AC88 | (structure) | Method M1 using (S)-(−)-3-hydroxy-THF |

TABLE 4-continued

Intermediates prepared according to Intermediate Methods A1 to M1.

| # | STRUCTURE | |
|---|---|---|
| AC89 | [structure] | Method I1 using 3-methoxyazetidine |
| AC90 | [structure] | Method I1 using 2-(5,6-dihydro-2H-pyran-3-yl)-4,4,5,5-tetramethyl-1,3,2-dioxaborolane |
| AC91 | [structure] | Method M1 using tetrahydro-2H-pyran-4-ol |
| AC92 | [structure] | Method I1 using tributyl(4,5-dihydrofuran-2-yl)stannane (step 4 was perfomed following protocol described in WO2013086397) |
| AC93 | [structure] | See synthesis procedure for Intermediate AA144 using (S)-pyrrolidin-3-ol |
| AC94 | [structure] | Method I1 using 1-Methyl-4-(4,4,5,5-tetramethyl-1,3,2-dioxaborolan-2-yl)-1,2,5,6-tetrahydropyrrolidin-2-one |

TABLE 4-continued

Intermediates prepared according to Intermediate Methods A1 to M1.

| # | STRUCTURE | |
|---|---|---|
| AC95 | 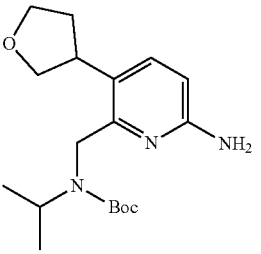 [SMILES: CC(C)N(Cc1nc(N)ccc1C1CCOC1)C(=O)OC(C)(C)C] | See synthesis procedure for Intermediate AA157 using propane-2-amine |
| AC96 | 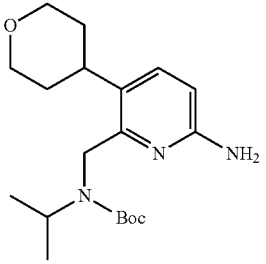 [SMILES: CC(C)N(Cc1nc(N)ccc1C1CCOCC1)C(=O)OC(C)(C)C] | See synthesis procedure for Intermediate AA157 using propan-2-amine and 3,4-dihydro-2H-pyran-5-ylboronic acid, pinacol ester |
| AC97 | 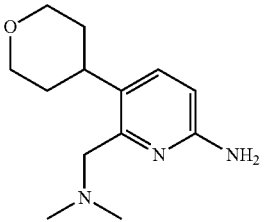 [SMILES: CN(C)Cc1nc(N)ccc1C1CCOCC1] | Method I1 using 3,4-dihydro-2H-pyran-5-ylboronic acid, pinacol ester |
| AC98 | 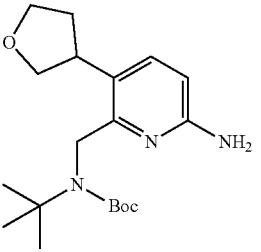 [SMILES: CC(C)(C)OC(=O)N(Cc1nc(N)ccc1C1CCOC1)C(C)(C)C] | See synthesis procedure for Intermediate AA157 using 2-methylpropan-2-amine |
| AC99 | 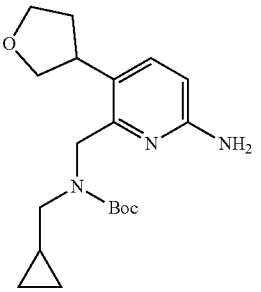 [SMILES: CC(C)(C)OC(=O)N(Cc1nc(N)ccc1C1CCOC1)CC1CC1] | See synthesis procedure for Intermediate AA157 using cyclopropyl methanamine |

TABLE 4-continued

Intermediates prepared according to Intermediate Methods A1 to M1.

| # | STRUCTURE | |
|---|---|---|
| AC100 | 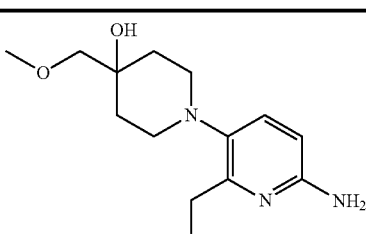 | See synthesis procedure for Intermediate AA144 using 4-(methoxymethyl)piperidin-4-ol |

Synthesis of Tert-Butyl 2-methyl-3-(4,4,5,5-tetramethyl-1,3,2-dioxaborolan-2-yl)-1H-pyrrolo[2,3-b]pyridine-1-carboxylate (Intermediate BB11)

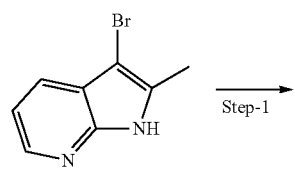

Intermediate BB11-1

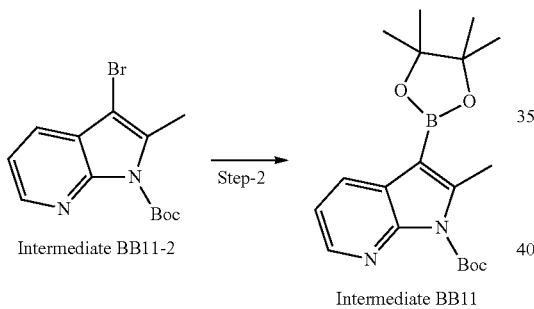

Step-1 Synthesis of Tert-Butyl 3-bromo-2-methyl-1H-pyrrolo[2,3-b]pyridine-1-carboxylate (Intermediate BB11-2)

To a solution of Intermediate BB11-1 (1.5 g, 7.11 mmol) in DCM (15 mL) were added trimethylamine (2.154 g, 21.32 mmol, 3.0 eq), N,N-DMAP (0.086 g, 0.71 mmol, 0.1 eq) and Boc-anhydride (2.324 g, 10.66 mmol, 1.5 eq) at RT. After stirring at RT for 1 h, the reaction mixture was poured into ice cold water (200 mL) and extracted with ethyl acetate (100 mL×3). The combined organic layer was dried over sodium sulfate and concentrated under reduced pressure. The residue was purified by column chromatography eluting with 15% ethyl acetate in hexane to afford Intermediate BB11-2 (1.6 g, 72.35%). MS (ES): m/z 312.15 [M+H]$^+$

Step-2 Synthesis of Tert-Butyl 2-methyl-3-(4,4,5,5-tetramethyl-1,3,2-dioxaborolan-2-yl)-1H-pyrrolo[2,3-b]pyridine-1-carboxylate (Intermediate BB11)

To a solution of Intermediate BB11-2 (1.0 g, 3.21 mmol) and 4,4,4',4',5,5,5',5'-Octamethyl-2,2'-bi-(1,3,2-dioxaborolane) (1.8 g, 7.06 mmol, 2.2 eq) in 1,4-dioxane (10 mL) was added potassium acetate (0.63 g, 6.42 mmol, 2.0 eq) at RT. After degassing using argon gas for 20 mins, tris(dibenzylideneacetone)dipalladium(O) (0.147 g, 0.16 mmol, 0.05 eq) and tricyclohexylphosphine (0.1 g, 0.38 mmol, 0.12 eq) were added to the reaction mixture. After stirring at 110° C. for 16 h, the reaction mixture was poured into water (100 mL) and extracted with ethyl acetate (100 mL×3). The combined organic layer was washed with brine solution (100 mL), dried over sodium sulfate and concentrated under reduced pressure. The residue was purified by column chromatography eluting with 50% ethyl acetate in hexane to afford Intermediate BB11 (1.0 g, quantitative yield). MS (ES): m/z 359.39 [M+H]$^+$.

Synthesis of Tert-Butyl 6-methyl-3-(4,4,5,5-tetramethyl-1,3,2-dioxaborolan-2-yl)-1H-pyrrolo[2,3-b]pyridine-1-carboxylate (Intermediate BB12)

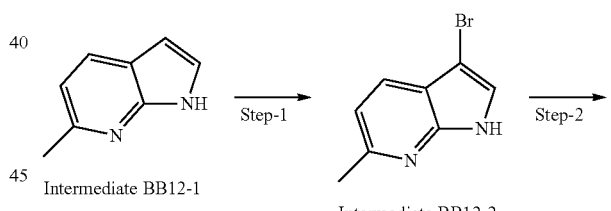

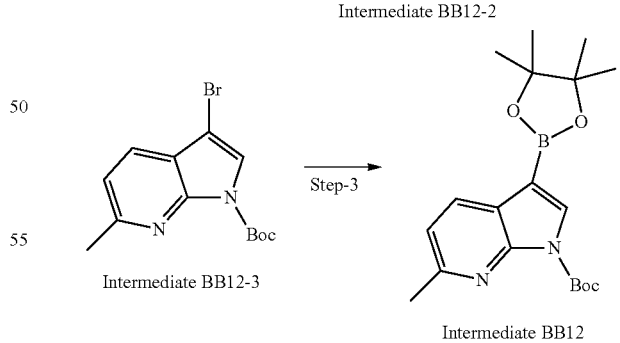

Step-1 Synthesis of 3-bromo-6-methyl-1H-pyrrolo[2,3-b]pyridine (Intermediate BB12-2)

To a solution of Intermediate BB12-2 (1.0 g, 7.57 mmol) in THF (10 mL) were added N-bromosuccinimide (2.021 g, 11.35 mmol, 1.5 eq) and then hydrochloric acid at RT. After stirring at RT for 2 days, the reaction mixture was neutralized using saturated sodium bicarbonate (100 mL) and extracted with ethyl acetate (100×3). The combined organic layer was dried over sodium sulfate and concentrated under reduced pressure to afford crude material. The residue was purified by column chromatography eluting with 35% ethyl acetate in hexane to afford Intermediate BB12-2 (1.5 g, 93.93%), MS (ES): m/z 211.75 [M+H]$^+$.

Step-2, 3 Synthesis of Tert-Butyl 6-methyl-3-(4,4,5,5-tetramethyl-1,3,2-dioxaborolan-2-yl)-1H-pyrrolo[2,3-b]pyridine-1-carboxylate (Intermediate BB12)

tert-butyl 6-methyl-3-(4,4,5,5-tetramethyl-1,3,2-dioxaborolan-2-yl)-1H-pyrrolo[2,3-b]pyridine-1-carboxylate (Intermediate BB12) was prepared from 3-bromo-6-methyl-1H-pyrrolo[2,3-b]pyridine (Intermediate BB12-2) in a similar fashion to that described in tert-butyl 2-methyl-3-(4,4,5,5-tetramethyl-1,3,2-dioxaborolan-2-yl)-1H-pyrrolo[2,3-b]pyridine-1-carboxylate (General process intermediate BB11). (0.750 g, quantitative yield). MS (ES): m/z 359.74 [M+H]$^+$ Synthesis of Tert-Butyl 2,6-dimethyl-3-(4,4,5,5-tetramethyl-1,3,2-dioxaborolan-2-yl)-1H-pyrrolo[2,3-b]pyridine-1-carboxylate (Intermediate BB13)

reduced pressure. The residue was purified by column chromatography eluting with 50% ethyl acetate in hexane to afford Intermediate BB13-2 (6.7 g, 87.63%) MS (ES): m/z 227 [M+2]$^+$ Step-2 3 Synthesis of Tert-Butyl 2,6-dimethyl-3-(4,4,5,5-tetramethyl-1,3,2-dioxaborolan-2-yl)-1H-pyrrolo[2,3-b]pyridine-1-carboxylate (Intermediate BB13)

tert-butyl 2,6-dimethyl-3-(4,4,5,5-tetramethyl-1,3,2-dioxaborolan-2-yl)-1H-pyrrolo[2,3-b]pyridine-1-carboxylate (Intermediate BB13) was prepared from 2,6-dimethyl-1H-pyrrolo[2,3-b]pyridine (Intermediate BB13-1) in a similar fashion to that described in tert-butyl 6-methyl-3-(4,4,5,5-tetramethyl-1,3,2-dioxaborolan-2-yl)-1H-pyrrolo[2,3-b]pyridine-1-carboxylate (General process intermediate BB12). (0.16 g, 46.59%). MS (ES):71% m/z 191.5 [M−100]$^+$ (Boronic ester)+25% m/z 317.7 [M−56]$^+$ (Boronic acid).

Synthesis of 1-methyl-4-(4,4,5,5-tetramethyl-1,3,2-dioxaborolan-2-yl)-1H-pyrrolo[2,3-b]pyridine (Intermediate BB14)

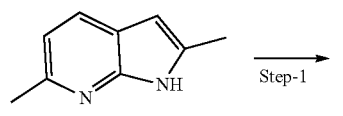

Intermediate BB13-1

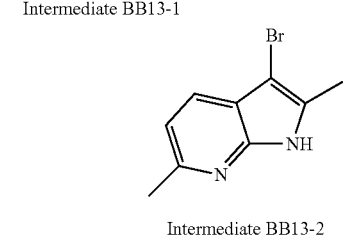

Intermediate BB13-2

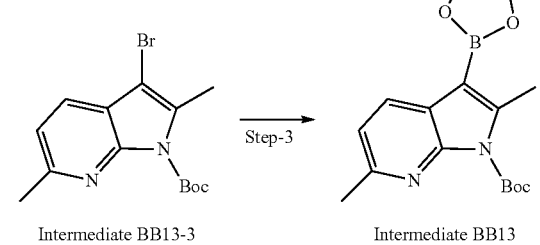

Intermediate BB13-3   Intermediate BB13

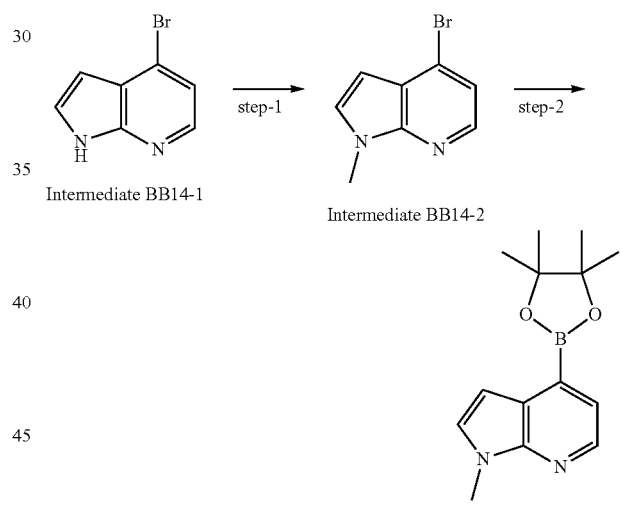

Step-1 Synthesis of 3-bromo-2,6-dimethyl-1H-pyrrolo[2,3-b]pyridine (Intermediate BB13-2)

To a solution of Intermediate BB13-1 (5.0 g, 34.240 mmol) in tert-butanol (200 mL) was added pyridinium tribromide (12.0 g, 37.670 mmol, 1.1 eq) at RT. After stirring for 4 h, the reaction mixture was quenched with water (500 mL) and extracted with ethyl acetate (250 mL×3). The combined organic layer was washed with brine solution (300 mL), dried over sodium sulfate and concentrated under Step 1 synthesis of 4-bromo-1-methyl-1H-pyrrolo[2,3-b]pyridine (Intermediate BB14-2)

To a solution of 60% sodium hydride (8.12 g, 0.2030 mol, 2.0 eq) in DMF (100 mL) at 0° C. under nitrogen was added a solution of Intermediate BB14-1 (20.0 g, 0.0473 mol) in DMF (50 mL). After stirring at 0° C. for 30 min, methyl iodide (7.58 mL, 0.121 mol, 1.2 eq) was added. After stirring at RT for 30 min, the reaction mixture was poured into an ice cold water and extracted with ethyl acetate (300 mL×3). The combined organic layers were dried over sodium sulfate and concentrated under reduced pressure to afford Intermediate BB14-2 (20 g, quantitative yield). MS (ES): m/z 211.50 [M+H]$^+$. $^1$H NMR (400 MHz, DMSO): δ 8.15 (d, 1H), 7.67 (d, 1H), 7.38 (d, 1H), 6.45 (d, 1H), 3.90 (s, 3H).

Step 2 Synthesis of 1-methyl-4-(4,4,5,5-tetramethyl-1,3,2-dioxaborolan-2-yl)-1H-pyrrolo[2,3-b]pyridine (Intermediate BB14)

To a solution of Intermediate BB14-2 (10.0 g, 0.047 mol) and 4,4,4',4',5,5,5',5'-octamethyl-2,2'-bi-(1,3,2-dioxaborolane) (11.99 g, 0.0473 mol) in 1,4-dioxane (100 mL) was added potassium acetate (13.09 g, 0.141 mol, 3.0 eq) at RT. After degassing with argon gas for 20 min, [1,1'-Bis(diphenylphosphino) ferrocene] dichloro palladium(II) DCM complex (3.85 g, 3.85 mol, 0.1 eq) was added. After stirring at 90° C. for 2.5 h, the reaction mixture was poured into water and extracted with ethyl acetate (250 mL×3). The combined organic layer washed with brine solution, dried over sodium sulfate, and concentrated under reduced pressure to afford crude material. The residue was purified via column chromatography eluting with 15% ethyl acetate in hexane to afford Intermediate BB14 (10.5 g, 82%). m/z 258.5 (M+H)$^+$ 1H NMR (400 MHz, DMSO): δ 8.32 (d, 1H), 7.61 (d, 1H), 7.36 (d, 1H), 6.71 (d, 1H), 3.87 (s, 3H), 1.39 (m, 12H).

Synthesis of Tert-Butyl 3-methyl-4-(4,4,5,5-tetramethyl-1,3,2-dioxaborolan-2-yl)-1H-pyrrolo[2,3-b]pyridine-1-carboxylate (Intermediate BB15)

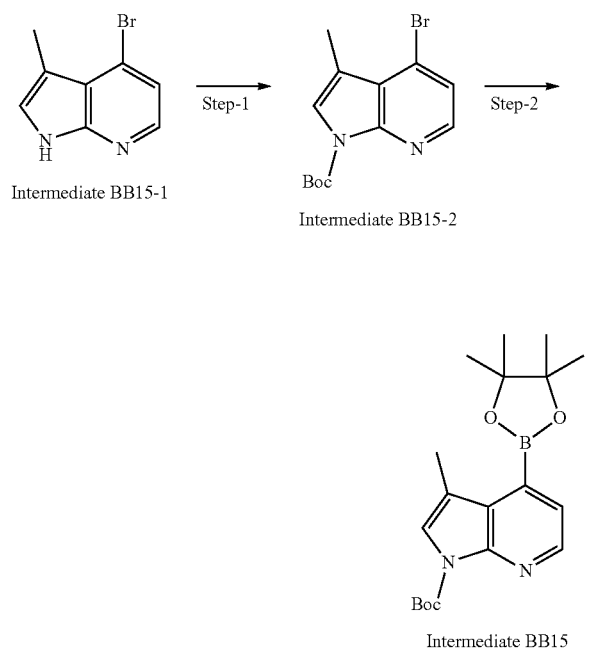

tert-butyl 3-methyl-4-(4,4,5,5-tetramethyl-1,3,2-dioxaborolan-2-yl)-1H-pyrrolo[2,3-b]pyridine-1-carboxylate (Intermediate BB15) was prepared from 4-bromo-3-methyl-1H-pyrrolo[2,3-b]pyridine (Intermediate BB15-1) in a similar fashion to that described in tert-butyl 2-methyl-3-(4,4,5,5-tetramethyl-1,3,2-dioxaborolan-2-yl)-1H-pyrrolo[2,3-b]pyridine-1-carboxylate (Intermediate BB11). (0.165 g, 19.85%). MS (ES): m/z 359.4 [M+H]$^+$.

Synthesis of Tert-Butyl 3-(tributylstannyl)-1H-pyrrolo[2,3-c]pyridine-1-carboxylate (Intermediate BB38)

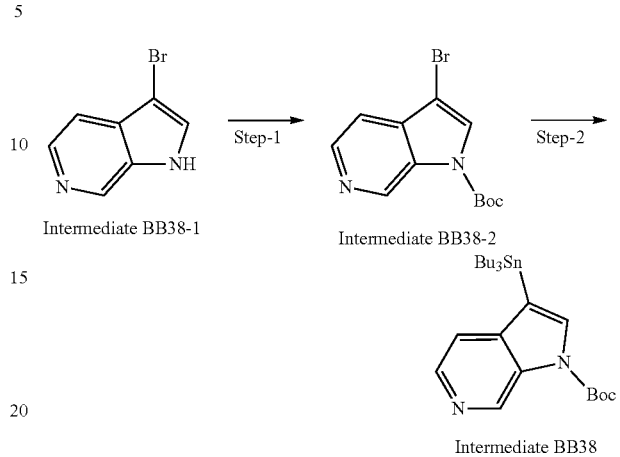

Step-1 Synthesis of Tert-Butyl 3-bromo-1H-pyrrolo[2,3-c]pyridine-1-carboxylate (Intermediate BB38-2)

tert-butyl 3-bromo-1H-pyrrolo[2,3-c]pyridine-1-carboxylate (Intermediate BB38-2) was prepared from 3-bromo-1H-pyrrolo[2,3-c]pyridine (Intermediate BB38-1) in a similar fashion to that described in tert-butyl 3-bromo-2-methyl-1H-pyrrolo[2,3-b]pyridine-1-carboxylate (General process Intermediate BB11-2). (0.7 g, 61.56%). (4 g, 75%). MS (ES): m/z 237.15 [M+H]$^+$

Step-2 Synthesis of Tert-Butyl 3-(tributylstannyl)-1H-pyrrolo[2,3-c]pyridine-1-carboxylate (Intermediate BB38)

To a solution of Intermediate BB38-2 (0.5 g, 1.79 mmol) in THF (10 mL) was added n-butyllithium solution (0.8 mL, 1.97 mmol, 1.1 eq) at −78° C. under argon. After stirring for 20 mins, tributyltin chloride (0.58 g, 1.79 mmol) was added. After stirring at −78° C. for 10 min, the reaction mixture was quenched with saturated NH$_4$Cl solution (100 mL) and extracted with ethyl acetate (100 mL×3). The combined organic layers were washed with brine solution (100 mL), dried over sodium sulfate and concentrated under reduced pressure. The residue was purified by column chromatography eluting with 2-5% ethyl acetate in hexane to afford Intermediate BB38 (0.25 g, 29.29%). MS (ES): m/z 507.9 [M+H]$^+$.

Synthesis of Tert-Butyl 3-(4,4,5,5-tetramethyl-1,3,2-dioxaborolan-2-yl)-6-(trifluoromethyl)-1H-pyrrolo[2,3-b]pyridine-1-carboxylate (Intermediate BB44)

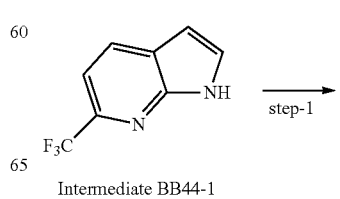

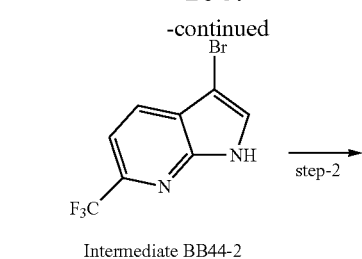

Intermediate BB44-2

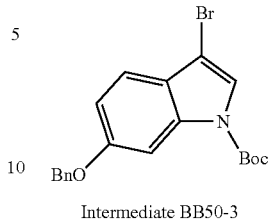

Intermediate BB44-3

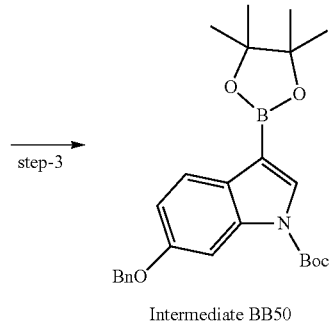

Intermediate BB44 tert-butyl 3-(4,4,5,5-tetramethyl-1,3,2-dioxaborolan-2-yl)-6-(trifluoromethyl)-1H-pyrrolo[2,3-b]pyridine-1-carboxylate (Intermediate BB44) was prepared from 2,6-dimethyl-1H-pyrrolo[2,3-b]pyridine (Intermediate BB44-1) in a similar fashion to that described in tert-butyl 2,6-dimethyl-3-(4,4,5,5-tetramethyl-1,3,2-dioxaborolan-2-yl)-1H-pyrrolo[2,3-b]pyridine-1-carboxylate (General process Intermediate BB13). (0.16 g, 46.59%). MS (ES):71% m/z 191.5 [M−100]$^+$ (Boronic ester)+25% m/z 317.7 [M−56]$^+$ (Boronic acid).

Synthesis of Tert-Butyl 6-(benzyloxy)-3-(4,4,5,5-tetramethyl-1,3,2-dioxaborolan-2-yl)-1H-indole-1-carboxylate (Intermediate BB50)

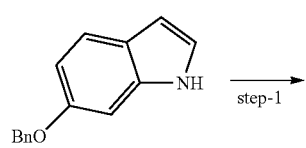

Intermediate BB50-1

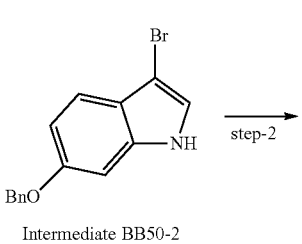

Intermediate BB50-2

Intermediate BB50-3

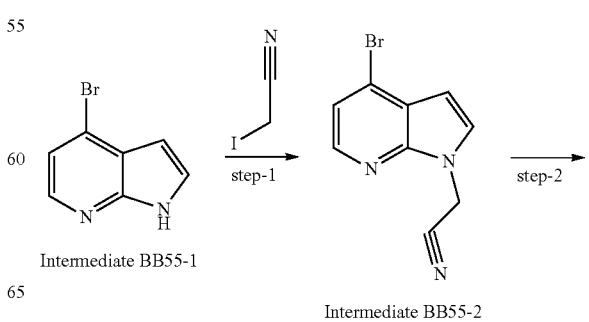

Intermediate BB50

Step-1 Synthesis of 6-(benzyloxy)-3-bromo-1H-indole (Intermediate BB50-2)

To a solution of Intermediate BB50-1 (3.0 g 13.4 mmol, 1.0 eq.) in DMF (25.0 mL) was added bromine (2.57 g, 16.1 mmol, 1.2 eq.) at 0° C. After stirring at RT for 1 h, the reaction mixture was poured into water (100 mL) and extracted with ethyl acetate (100 mL×3). The combined organic layers were washed with brine (100 mL) solution, dried over sodium sulfate, and concentrated under reduced pressure 25° C. to afford Intermediate BB50-2 (2 g, 49.2%). MS (ES): m/z 302 (M+H)$^+$

Step-2, 3 Synthesis of Tert-Butyl 6-(benzyloxy)-3-(4,4,5,5-tetramethyl-1,3,2-dioxaborolan-2-yl)-1H-indole-1-carboxylate (Intermediate BB50)

tert-butyl 6-(benzyloxy)-3-(4,4,5,5-tetramethyl-1,3,2-dioxaborolan-2-yl)-1H-indole-1-carboxylate (Intermediate BB50) was prepared from 6-(benzyloxy)-3-bromo-1H-indole (Intermediate BB50-2) in a similar fashion to that described in tert-butyl 2,6-dimethyl-3-(4,4,5,5-tetramethyl-1,3,2-dioxaborolan-2-yl)-1H-pyrrolo[2,3-b]pyridine-1-carboxylate (General process Intermediate BB13). (0.450 g, 49.2%). MS (ES): m/z 449 (M+H)$^+$.

Synthesis 2-(4-bromo-1H-pyrrolo[2,3-b]pyridin-1-yl)acetamide (Intermediate BB55)

Intermediate BB55-1

Intermediate BB55-2

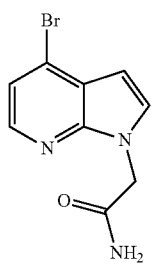

Intermediate BB55

Step-1 Synthesis of 2-(4-bromo-1H-pyrrolo[2,3-b]pyridin-1-yl)acetonitrile (Intermediate BB55-2)

To a solution of Intermediate BB55-1 (2.0 g 10.1 mmol, 1.0 eq.) in DMF (15.0 mL) were added sodium hydride (0.49 g 20.3 mmol, 2.0 eq.) at 0° C. After stirring at RT for 20 mins, 2-iodoacetonitrile (2.3 g, 12.1 mmol, 1.5 eq.) was added. After stirring at RT for 1 h, the reaction mixture was poured into water (100 mL) and extracted with ethyl acetate (100 mL×3). The combined organic layer was washed with brine (100 mL) solution, dried over sodium sulfate, and concentrated under reduced pressure to afford Intermediate BB55-2 (1.7 g, 70.9%). MS (ES): m/z 236 (M+H)$^+$.

Step-2 Synthesis of 2-(4-bromo-1H-pyrrolo[2,3-b]pyridin-1-yl)acetamide (Intermediate BB55)

To a solution of Intermediate BB55-2 (1.5 g 6.3 mmol, 1.0 eq.) in dimethyl sulfoxide (15.0 mL) were added potassium carbonate (2.6 g, 19.0 mmol, 3.0 eq.). After stirring at 60° C. for 20 min, hydrogen peroxide (1.08 g, 31.7 mmol, 5.0 eq.) was added. After stirring at 60° C. for 20 min, the reaction mixture was poured into water (100 mL) and extracted with ethyl acetate (100 mL×3). The combined organic layer was washed with brine (100 mL) solution, dried over sodium sulfate, and concentrated under reduced pressure to afford Intermediate BB55 (1.7 g, 105.30%). MS (ES): m/z 254 (M+H)$^+$.

Synthesis of 7-bromooxazolo[5,4-b]pyridine (Intermediate BB56)

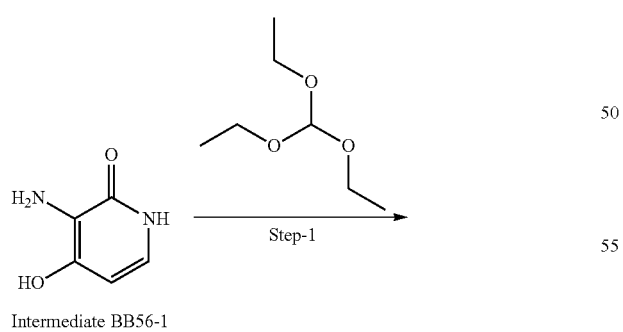

Step-1 Synthesis of oxazolo[5,4-b]pyridin-7-ol (Intermediate BB56-2)

Prepared as described in WO2016106106.

Step-2 Synthesis of 7-bromooxazolo[5,4-b]pyridine (Intermediate BB56)

To a solution Intermediate BB56-2 (0.130 g, 0.95 mmol) in DMF (2 mL) was added phosphoryl bromide (0.320 g, 1.14 mmol, 1.2 eq) at 0° C. After stirring at 100° C. for 2 h, the reaction mixture was quenched with sodium bicarbonate solution in water (100 mL) and extracted into ethyl acetate (100 mL×3). The combined organic layers were washed with brine solution (100 mL), dried over sodium sulfate and concentrated under reduced pressure. The residue was purified using combi-flash silica eluting with 1-2% methanol in DCM to afford Intermediate BB56 (0.150 g, 78.92%) MS (ES): m/z 199.94 [M+H]$^+$ Synthesis of 3-iodo-7-methyl-5,6,7,8-tetrahydroimidazo[1,2-a]pyridine (Intermediate BB62)

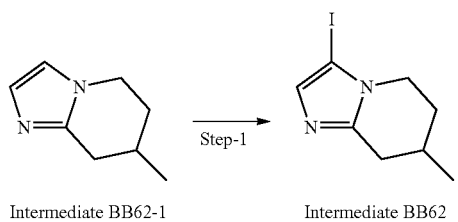

Step-1 Synthesis of 3-iodo-7-methyl-5,6,7,8-tetrahydroimidazo[1,2-a]pyridine (Intermediate BB62)

To a solution of Intermediate BB62-1 (1.8 gm, 1.32 mmol, 1 eq) in acetonitrile was added N-Iodosuccinimide (3.8 gm, 41.8 mmol, 5 eq). After stirring at RT for 90 min, the reaction mixture was poured into water (100 mL) and extracted with ethyl acetate (100 mL×3). The combined organic layer was washed with brine (100 mL) solution, dried over sodium sulfate, and concentrated under reduced pressure to afford Intermediate BB62. (0.700 gm, 20.21%): m/z 263.03 [M+H]$^+$ Synthesis of 7-fluoro-3-iodoimidazo[1,2-a]pyridine (Intermediate BB63)

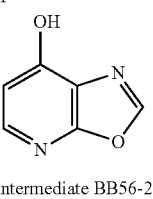

Step-1 Synthesis of 7-fluoroimidazo[1,2-a]pyridine (Intermediate BB63-2)

To a solution of 4-fluoropyridin-2-amine (50 g, 0.44 mol) in ethanol (450 mL) was added chloro acetaldehyde (50% in Water) (300 mL, 6 vol) and sodium bicarbonate (74.9 g, 0.89 mol, 2.0 eq). After stirring at 60° C. for 4 h, the reaction mixture was concentrated under vacuum. The crude material was purified via column chromatography eluting with 35% ethyl acetate in hexane to afford Intermediate BB63-2 (50 g, 82.35%) MS (ES): m/z 137.16 [M+H]$^+$, 1H NMR (400 MHz, DMSO): δ 8.62 (t, 1H), 7.93 (s, 1H), 7.54 (s, 1H), 7.39 (d, 1H), 6.96 (t, 1H).

Step-2 Synthesis of 7-fluoro-3-iodoimidazo[1,2-a]pyridine (Intermediate BB63)

To a solution 7-fluoroimidazo[1,2-a]pyridine (28 g, 0.20 mol) in chloroform (300 mL) was added N-iodosuccinimide (50.65.g, 0.22 mol, 1.1 eq). After stirring at RT for 3 h, the reaction mixture was quenched with solution of sodium thiosulfate (1000 mL) and extracted with ethyl acetate (600 mL×3). The combined organic solution was dried over sodium sulfate and concentrated in vacuum. The crude material was purified via column chromatography eluting with 18% ethyl acetate in hexane to afford Intermediate BB63. (30 g, 56.6%) MS (ES): m/z 262.94 [M+H]$^+$ 1H NMR (400 MHz, DMSO): δ 7.11 (m, 1H), 7.54 (d, 1H), 7.69 (s, 1H), 8.36-8.39 (t, 1H).

Synthesis of 4-(4,4,5,5-tetramethyl-1,3,2-dioxaborolan-2-yl)pyrazolo[1,5-a]pyridine (Intermediate BB68)

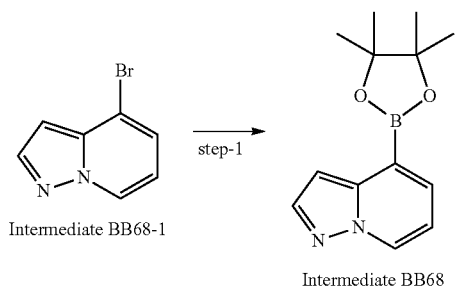 [SMILES: Brc1cccn2nccc12 ; CC1(C)OB(c2cccn3nccc23)OC1(C)C]

Intermediate BB68-1 → Intermediate BB68

To a solution of the 4-bromopyrazolo[1,5-a]pyridine Intermediate (BB68-1) (0.25 g, 1.27 mmol) in 1-4 dioxane (580 mL) were added bis(pinacolato)diboron (0.991 g, 3.83 mmol, 3.0 eq) and potassium acetate (0.375 g, 3.83 mmol, 3.0 eq). After degassing with flow of argon for 20 min, XPhos Pd G2 (0.05 g, 0.063 mmol, 0.05 eq) was added and again degassed for 10 min. After stirring at 100° C. for 2 h, the reaction was cooled to RT, filtered through celite, and washed with ethyl acetate (50 mL×3). The combined organic layer was washed with Water (50 mL), dried over Na$_2$SO$_4$, and concentrated under reduced pressure. The residue was purified by silica gel chromatography eluting with 2.0% MeOH/DCM to afford Intermediate BB68 (0.2 g, 64%). MS (ES): m/z 245.3 [M+H]$^+$.

Synthesis of 5-iodo-7-methyl-7H-pyrrolo[2,3-c]pyridazine (Intermediate BB69), 5-iodo-7-methyl-7H-pyrrolo[2,3-c]pyridazine (Intermediate BB70) and 5-iodo-2-methyl-2H-pyrrolo[2,3-c]pyridazine ((Intermediate BB78)

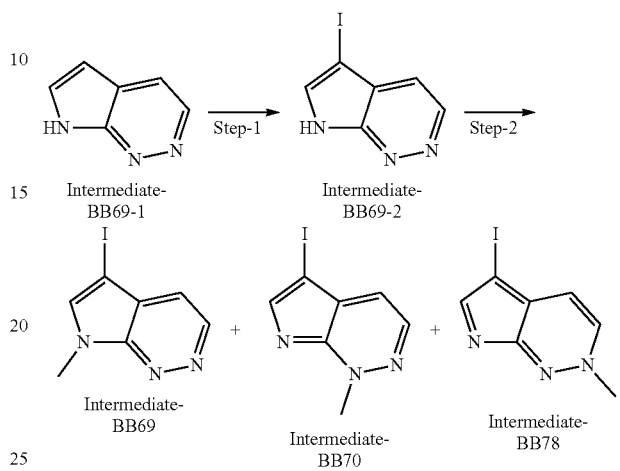

5-iodo-7-methyl-7H-pyrrolo[2,3-c]pyridazine (Intermediate BB69) and 5-iodo-7-methyl-7H-pyrrolo[2,3-c]pyridazine (Intermediate BB70) was prepared from 7H-pyrrolo[2,3-c]pyridazine in a similar fashion to that described in 3-iodo-6-methyl-6H-pyrrolo[2,3-d]pyridazine (Intermediate BB43). Intermediate BB69 (0.1 g, 20%). MS (ES): m/z 260.1 (M+H)$^+$. Intermediate BB70 (0.05 g, 10%). MS (ES): m/z 260.1 (M+H)$^+$. Intermediate BB78 (0.1 g, 20%). MS (ES): m/z 260.1 (M+H)$^+$.

Synthesis of 7-((3-fluoroazetidin-1-yl)methyl)-3-iodoimidazo[1,2-a]pyridine (Intermediate BB71)

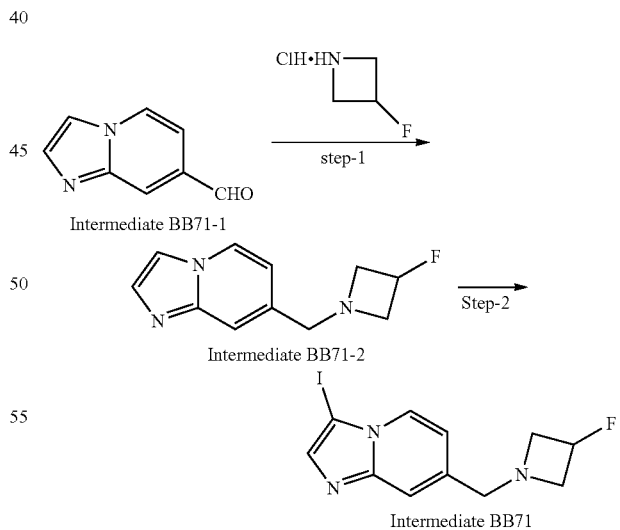

Step-1 Synthesis of imidazo[1,2-a]pyridine-7-carbaldehyde (Intermediate BB71-2)

To a solution of imidazo[1,2-a]pyridine-7-carbaldehyde (1 g, 6.84 mmol) in methanol (10 mL) was added 3-fluoroazetidine hydrochloride (2.3 g, 20.5 mmol, 3.0 eq), trimethylamine (2 mL, 13.6 mol, 2.0 eq) at 0° C. and stirred for 15 min. Sodium cyanoborohydride (5.8 g, 27.3 mol, 4.0 eq) was added portion wise. After stirring at rt for 16 h, the reaction mixture was quenched with water (100 mL) and extracted with ethyl acetate (50 mL×3). The combined organic layers were dried over sodium sulfate and concentrated on vacuum. The crude material purified via column chromatography eluting with 40% ethyl acetate in hexane to afford Intermediate BB71-2 (1.1 g, 78%) MS (ES): m/z 206.16 [M+H]⁺.

Step-2 Synthesis of 7-((3-fluoroazetidin-1-yl)methyl)-3-iodoimidazo[1,2-a]pyridine (Intermediate BB71)

7-((3-fluoroazetidin-1-yl)methyl)-3-iodoimidazo[1,2-a]pyridine (Intermediate BB71) was prepared from 7-((3-fluoroazetidin-1-yl)methyl)imidazo[1,2-a]pyridine in a similar fashion to that described in 7-fluoro-3-iodoimidazo[1,2-a]pyridine (General process Intermediate BB63). (0.8 g, 60%). MS (ES): m/z 332 (M+H)⁺.

Synthesis of 1-(3-iodoimidazo[1,2-a]pyridin-7-yl)-N,N-dimethylmethanamine (Intermediate BB72)

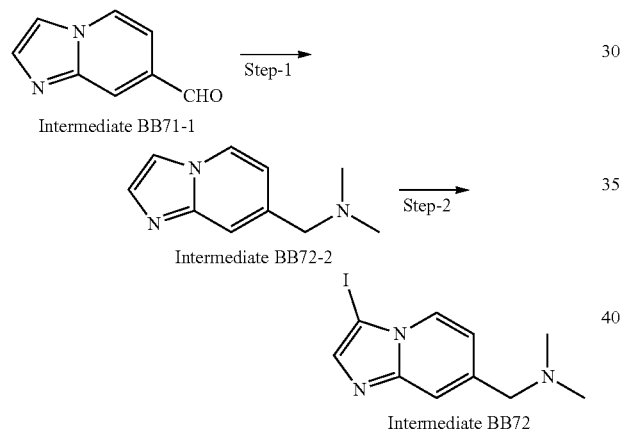

1-(3-iodoimidazo[1,2-a]pyridin-7-yl)-N,N-dimethylmethanamine (Intermediate BB72) was prepared from imidazo[1,2-a]pyridine-7-carbaldehyde in a similar fashion to that described in 7-((3-fluoroazetidin-1-yl)methyl)-3-iodoimidazo[1,2-a]pyridine (Intermediate BB71) (General process Intermediate BB71). (0.7 g, 60%). MS (ES): m/z 302.6 (M+H)⁺.

Synthesis of 3-iodo-7-(1-methylazetidin-3-yl)imidazo[1,2-a]pyridine (Intermediate-BB75)

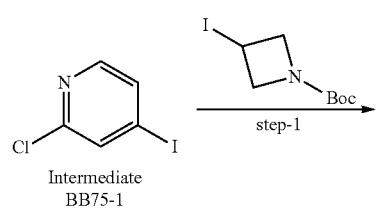

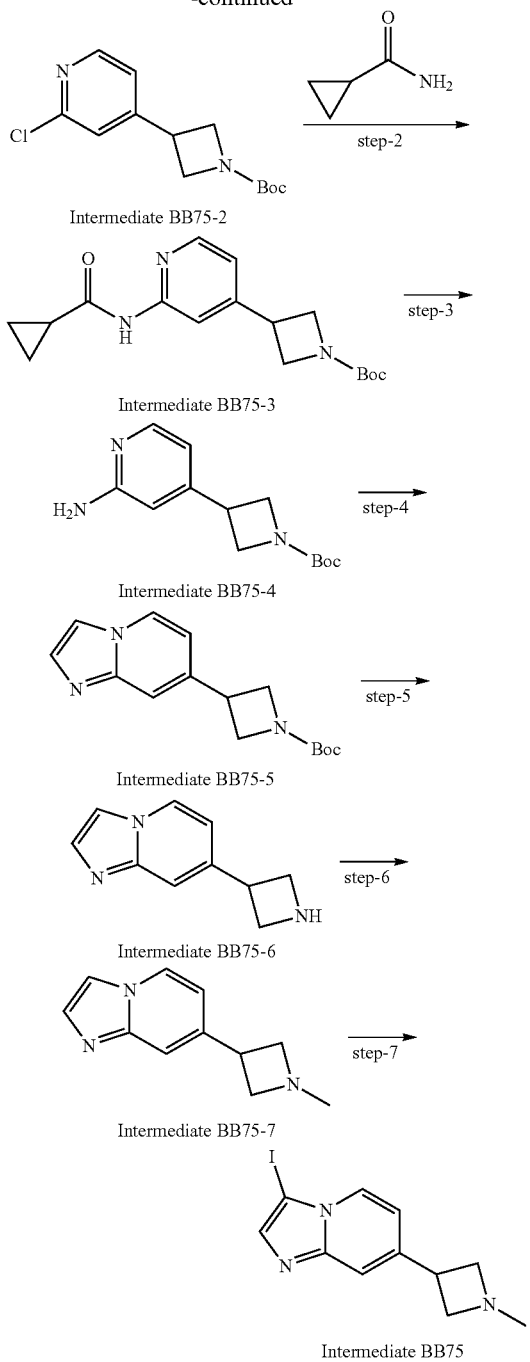

Step-1 Synthesis of Tert-Butyl 3-(2-chloropyridin-4-yl)azetidine-1-carboxylate (Intermediate BB75-2)

To a degassed solution of Zn dust (9.5 g, 147.03 mmol, 3.5 eq) in dimethylacetamide (50 mL) were added dropwise trimethylsilyl chloride (1.3 mL, 10.50 mmol, 0.25 eq) and 1,2 dibromoethane (1.57 g, 8.40 mmol, 0.2 eq). In a separate flask, to a degassed mixture [1,1'- of bis(diphenylphosphino)ferrocene]dichloropalladium(II) complexed with DCM (6.8 g, 8.40 mmol, 0.2 eq) and Copper(I) iodide (1.6 g, 8.40 mmol, 0.2 eq) was added a solution of Intermediate BB75-1 (10 g, 42.01 mmol) in dimethylacetamide (50 mL).

After stirring at RT for 15 min, both reaction mixtures were mixed. After stirring at 80° C. for 2 h, the reaction mixture was cooled at RT, diluted with water (500 mL), and extracted with ethyl acetate (3×200 mL). The combined organic extracts were washed with brine (300 mL), dried over Na$_2$SO$_4$, filtered, and concentrated under reduced pressure. The residue was purified by column chromatography eluting with 10% ethyl acetate gradient in hexane to afford Intermediate BB75-2 (6.0 g, 53.46%), MS (ES): m/z=269.2 [M+H]$^+$.

Step-2 Synthesis of Tert-Butyl 3-(2-(cyclopropanecarboxamido)pyridin-4-yl)azetidine-1-carboxylate (Intermediate BB75-3)

A solution of Intermediate BB75-2 (6.0 g, 22.38 mmol) and cyclopropanecarboxamide (2.2 g, 26.85 mmol, 1.2 eq), Cs$_2$CO$_3$ (14.5 g, 44.76 mmol, 2.0 eq) in 1,4-Dioxane (50 mL) was degassed under N$_2$ stream. After 15 min, Xantphos (1.3 g, 2.23 mmol, 0.1 eq) and Pd$_2$(dba)$_3$ (1.0 g, 1.11 mmol, 0.05 eq) were added. After stirring at 100° C. for 16 h, the reaction mixture was cooled to RT, diluted with water (200 mL), and extracted with ethyl acetate (3×100 mL). The combined organic extracts were washed with brine (200 mL), dried over Na$_2$SO$_4$, filtered, and concentrated under reduced pressure. The residue was purified by column chromatography eluting with 30% ethyl acetate gradient in hexane to afford Intermediate BB75-3 (5.0 g, 70.56%). MS (ES): m/z=318.2 [M+H]$^+$.

Step-3 Synthesis of Tert-Butyl 3-(2-aminopyridin-4-yl)azetidine-1-carboxylate (Intermediate BB75-4)

To a solution of Intermediate BB75-3 (5.0 g, 15.77 mmol) in methanol (50 mL) and water (15 mL) was added sodium hydroxide (6.3 g, 157.7 mmol, 10.0 eq). After stirring 4 h at 80° C., the reaction mixture was diluted with ice cold water (100 mL) and extracted with ethyl acetate (3×50 mL). The combined organic extracts were washed with brine (100 mL), dried over Na$_2$SO$_4$, filtered, and concentrated under reduced pressure to afford crude material which was used in next Step without purification. Intermediate BB75-4 (5.0 g, quantitative %), MS (ES): m/z=250.3 [M+H]$^+$.

Step-4 Synthesis of Tert-Butyl 3-(imidazo[1,2-a]pyridin-7-yl)azetidine-1-carboxylate (Intermediate BB75-5)

To a solution of Intermediate BB75-4 (5.0 g, 20.08 mmol) in ethanol (50 mL) was added aqueous sodium bicarbonate (3.4 g, 40.16 mmol, 2.0 eq). After stirring for 10 min at RT, chloroacetaldehyde (55% solution in water) (2.0 g, 26.10 mmol, 1.3 eq) was added into the reaction mixture. After stirring at 80° C. for 2 h, the reaction mixture was diluted with ice cold water (80 mL) and extracted with ethyl acetate (3×40 mL). The combined organic extracts were washed with brine (100 mL), dried over Na$_2$SO$_4$, filtered, and concentrated under reduced pressure to afford crude material which was used in next Step without purification. Intermediate BB75-5 (2.5 g, 45.61%), MS (ES): m/z=274.1 [M+H]$^+$ Step-5 Synthesis of 7-(azetidin-3-yl)imidazo[1,2-a]pyridine (Intermediate BB75-6)

To a solution of Intermediate BB75-5 (2.5 g, 9.15 mmol, 1.0 eq) in DCM:methanol (25 mL:8 mL) at 0° C. was added 4M HCl in dioxane (25 mL). After stirring for 12 h at RT, the reaction mixture was concentrated under reduced pressure. The residue was dissolved in DCM, diluted with sodium carbonate solution (20 mL) and stirred at RT for 2 h. The organic layer was concentrated under reduced pressure to afford crude material which was used in next Step without purification. Intermediate BB75-6 (1.9 g, quantitative %), MS (ES): m/z=174.2 [M+H]$^+$ Step-6 Synthesis of 7-(1-methylazetidin-3-yl)imidazo[1,2-a]pyridine (Intermediate BB75-7)

To a solution of Intermediate BB75-6 (1.9 g, 10.98 mmol) in methanol (20 mL) was added formaldehyde (0.4 g, 13.17 mmol, 1.2 eq). After stirring for 30 min at RT, acetic acid (0.15 mL 2.74 mmol, 0.25 eq) and sodium borocyanohydride (0.827 g, 13.17 mmol, 1.2 eq) were added into the reaction mixture. After stirring at 50° C. for 16 h, the reaction mixture was cooled to RT, neutralized with NaHCO$_3$ solution, and extracted with ethyl acetate (3×60 mL). The combined organic extracts were washed with brine (100 mL), dried over Na$_2$SO$_4$, filtered, and concentrated under reduced pressure to afford crude material which was used in next Step without purification. Intermediate BB75-7 (1.2 g, 58.43%), MS (ES): m/z=188.2 [M+H]$^+$ Step-7 Synthesis of 3-iodo-7-(1-methylazetidin-3-yl)imidazo[1,2-a]pyridine (Intermediate BB75)

To a solution of Intermediate BB75-7 (1.2 g, 6.41 mmol) in chloroform (60 mL) was added portion wise N-Iodosuccinimide (1.7 g, 7.69 mmol, 1.2 eq). After stirring for 1 h at RT, the reaction mixture was concentrated under reduced pressure. The residue was purified by column chromatography eluting with 10% methanol gradient in DCM (1.0% hydroxylamine) to afford Intermediate BB75 (0.7 g, 34.88%) as a yellow crystalline solid. MS (ES): m/z=314.2 [M+H]$^+$ Synthesis of 3-iodo-6-methyl-6 11-pyrrolo[2,3-d]pyridazine (Intermediate BB43),3-iodo-5-methyl-5 11-pyrrolo[2,3-d]pyridazine (Intermediate BB76) and 3-iodo-1-methyl-1H-pyrrolo[2,3-d]pyridazine (Intermediate BB77)

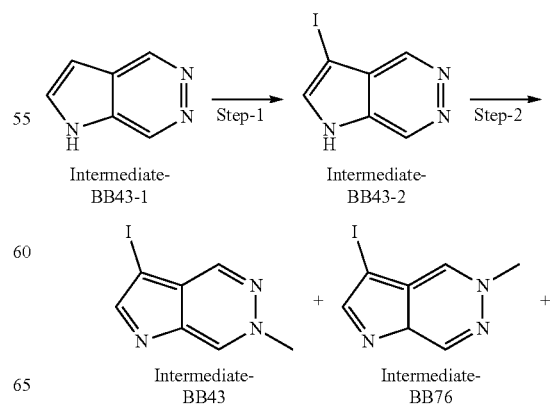

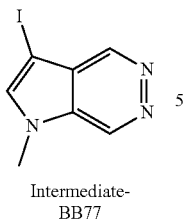

Intermediate-BB77

Step-1 Synthesis of Synthesis of 3-iodo-1H-pyrrolo[2,3-d]pyridazine (Intermediate BB43-2)

To a solution of Intermediate BB43-1 (0.98 g 8.22 mmol, 1.0 eq.) in DMF (13.0 mL) at 0° C. was added N-Iodosuccinimide (2.3 g, 9.04 mmol, 1.1 eq.). After stirring at RT for 1 h, the reaction mixture was poured into water (50 mL) and extracted using ethyl acetate (50 mL×3). The combined organic layer was wash with brine (40 mL) solution and concentrated under reduced pressure at 45° C. to afford Intermediate-BB43-2 (1.8 gm, 48.15%), MS (ES): m/z 246.3. [M+H]$^+$, LCMS purity 95%.

Step-2 Synthesis of 3-iodo-6-methyl-6H-pyrrolo[2,3-d]pyridazine (Intermediate BB43), 3-iodo-5-methyl-5H-pyrrolo[2,3-d]pyridazine (Intermediate BB76) and 3-iodo-1-methyl-1H-pyrrolo[2,3-d]pyridazine (Intermediate BB77)

To a solution of Intermediate BB43-2 (0.8 g 3.2 mmol, 1.0 eq.) and CS$_2$CO$_3$ (3.1 g, 9.72 mmol, 3 eq.) in DMF (13.0 mL) was added methyl iodide (0.92 g, 6.53 mmol, 2 eq.) in DMF (1 mL) dropwise. After stirring at RT for 30 min, the reaction mixture was poured into water (60 mL) and extracted using ethyl acetate (30 mL×3). The organic layer was wash with brine (40 mL) solution and concentrated under reduced pressure at 45° C. to afford crude material. The residue was purified by column chromatography eluting with 7% MeOH in DCM to afford Intermediate BB43. (110 mg, LCMS: 95%, MS (ES): m/z 259.2 (M+H)$^+$. $^1$H NMR (400 MHz, DMSO-d6) δ 8.53 (d, J=5.2 Hz, 1H), 8.14 (s, 1H), 8.94 (d, J=4.8 Hz, 1H), 4.51 (s, 3H). Intermediate BB76 (80 mg, LCMS: 97%, MS (ES): m/z 259.5 (M+H)$^+$. $^1$H NMR (400 MHz, DMSO-d6) δ 8.61 (d, J=5.1 Hz, 1H), 8.46 (s, 1H), 8.75 (d, J=4.9 Hz, 1H), 4.42 (s, 3H). Intermediate BB77 (70 mg, LCMS: 95%, MS (ES): m/z 259.2 (M+H)$^+$. $^1$H NMR (400 MHz, DMSO-d6) δ 8.53 (d, J=5.5 Hz, 1H), 8.10 (s, 1H), 8.98 (d, J=4.9 Hz, 1H), 4.56 (s, 3H).

Synthesis of 7-fluoro-3-iodo-8-methylimidazo[1,2-a]pyridine (Intermediate BB80)

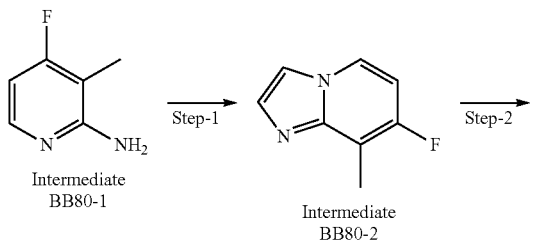

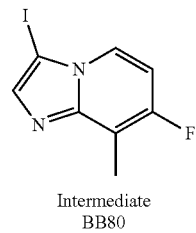

Intermediate BB80

7-fluoro-3-iodo-8-methylimidazo[1,2-a]pyridine (Intermediate BB80) was prepared from 4-fluoro-3-methylpyridin-2-amine in a similar fashion to that described in 7-fluoro-3-iodoimidazo[1,2-a]pyridine (General process Intermediate BB63). (0.7 g, 60%). MS (ES): m/z 276.6 (M+H)$^+$.

Synthesis of 8-fluoro-3-(4,4,5,5-tetramethyl-1,3,2-dioxaborolan-2-yl)imidazo[1,2-a]pyridine (Intermediate BB81)

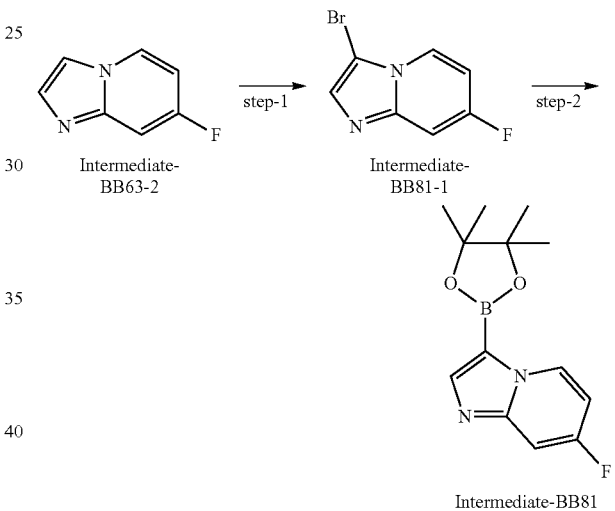

Step-1 Synthesis of 7-fluoro-3-bromoimidazo[1,2-a]pyridine (Intermediate BB63-1)

To a solution 7-fluoroimidazo[1,2-a]pyridine (20 g, 0.147 mol) in DCM (200 mL) was added N-bromosuccinimide (28.7.g, 0.161 mol, 1.1 eq). After stirring at RT for 30 min, the reaction mixture was quenched with solution of sodium thiosulfate (1000 mL) and extracted with DCM (600 mL×3). The combined organic washes were dried over sodium sulfate and concentrated on vacuum. The residue was purified via column chromatography eluting with 15% ethyl acetate in hexane to afford Intermediate BB81-1. (15 g, 48%) MS (ES): m/z 215.5 217.3 [M]$^+$, [M+2]$^+$ 1H NMR (400 MHz, DMSO): δ 7.11 (m, 1H), 7.54 (d, 1H), 7.69 (s, 1H), 8.36-8.39 (t, 1H).

Step-2 Synthesis of 7-fluoro-3-(4,4,5,5-tetramethyl-1,3,2-dioxaborolan-2-yl)imidazo[1,2-a]pyridine (Intermediate BB81)

To a solution of 3-bromo-7-fluoroimidazo[1,2-a]pyridine (0.5 g, 2.32 mmol) and isopropoxy boronic acid pinacol ester (1.3 g, 6.97 mmol, 3.0 eq) in THF (10 mL) at 0° C. was added dropwise iso-propyl magnesium chloride lithium chloride complex (3.4 mL, 4.65 mmol, 2.0 eq). After stirring at 0° C. for 2 h, the reaction mixture was diluted with water (25 mL) and extracted with ethyl acetate (10 mL×3). The combined organic layer was dried over sodium sulfate and concentrated under reduced pressure to afford Intermediate BB81 (0.25 g, 59.75%). MS (ES): m/z 180 [M+1]$^+$ which was used for next step without further purification.

Synthesis of 8-bromo-6-chloroimidazo[1,2-b]pyridazine (Intermediate BB82)

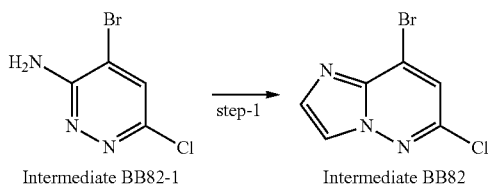 [SMILES: Nc1nnc(Cl)cc1Br ; Clc1cc(Br)c2nccn2n1]

Intermediate BB82-1    Intermediate BB82

Step-1 Synthesis of 8-bromo-6-chloroimidazo[1,2-b]pyridazine (Intermediate BB82)

To a solution of Intermediate-BB82-1 (1.2 g 5.7 mmol, 1.0 eq.) in isopropyl alcohol (13.0 mL) were added 2-chloro-1,1-diethoxyethane (1.05 g, 6.9 mmol, 1.2 eq.) and p-toluenesulphonic acid (1.3 g, 6.9 mmol, 1.2 eq.) at RT. After stirring at 80° C. for 16 h, the reaction mixture was poured into sat·NaHCO$_3$(50 mL) and extracted using DCM (50 mL×3). The combined organic layer was washed with brine (50 mL), dried with sodium sulfate, filtered, and concentrated under reduced pressure. The residue was purified by column chromatography eluting with 70% ethyl acetate in hexane (700 mg). The compound was further purified by preparative HPLC method using (a) 0.1% formic acid in water and (b); 100% acetonitrile as mobile phase solvents to afford Intermediate-BB82 (200 mg, Yield: 15%), MS (ES): m/z 233.9. [M+H]$^+$, LCMS purity 100%.

Synthesis of 7-(difluoromethyl)-3-iodoimidazo[1,2-a]pyridine (Intermediate BB84)

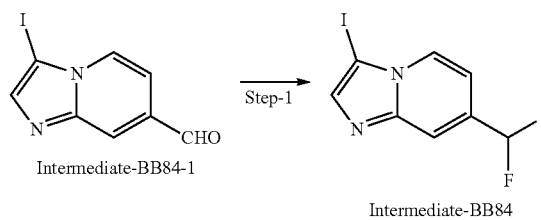

Intermediate-BB84-1

Intermediate-BB84

Step-1 Synthesis of 7-(difluoromethyl)-3-iodoimidazo[1,2-a]pyridine (Intermediate-BB84)

To a solution of 3-iodoimidazo[1,2-a]pyridine-7-carbaldehyde (2 g, 7.35 mmol, 1 eq) in DCM (20 mL) at 0° C. was added diethylaminosulfur trifluoride (3.5 g, 22.05 mmol, 3 eq). After warming to RT and stirring for 45 min, the reaction mixture was quenched with saturated sodium bicarbonate solution (100 mL) and extracted with ethyl acetate (100 mL×3). The combined extract was dried over sodium sulfate and concentrated under reduced pressure to afford 7-(difluoromethyl)-3-iodoimidazo[1,2-a]pyridine (Intermediate-BB84) (0.6 g, 27.76%) MS (ES): m/z 295.1 [M+H]$^+$ Synthesis of 8-fluoro-3-(4,4,5,5-tetramethyl-1,3,2-dioxaborolan-2-yl)imidazo[1,2-a]pyridine (Intermediate BB87)

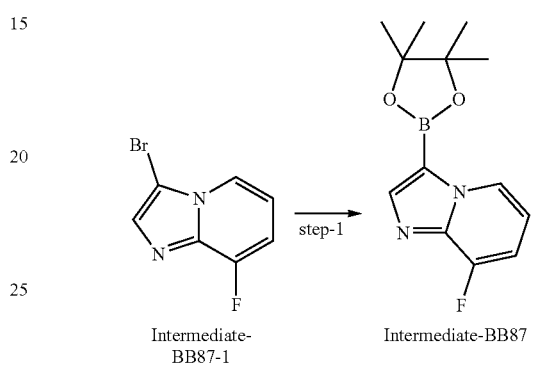

Intermediate-BB87-1    Intermediate-BB87

Step-1 Synthesis of 8-fluoro-3-(4,4,5,5-tetramethyl-1,3,2-dioxaborolan-2-yl)imidazo[1,2-a]pyridine (Intermediate BB87)

To a solution of 3-bromo-8-fluoroimidazo[1,2-a]pyridine (Intermediate BB87-1) (1.0 g 4.67 mmol, 1.0 eq.) and isopropyl boronic ester (4.3 g 23.0 mmol, Seq.) in THF (10.0 mL) was added isopropyl MgCl·LiCl (Turbo Grignard) (10.1 mL, 2.2 eq.) at RT. After stirring at RT for 20 min, the reaction mixture of Intermediate BB87 was use as such without aqueous workup and purification. MS (ES): m/z 263.4 (M+H)$^+$.

Synthesis of 8-bromoimidazo[1,2-c]pyrimidine (Intermediate BB88)

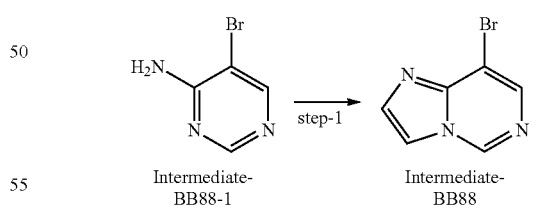

Intermediate-BB88-1    Intermediate-BB88

Step-1. Synthesis of 8-bromoimidazo[1,2-c]pyrimidine (Intermediate BB88)

To a solution of Intermediate BB88-1 (0.350 g, 2 mmol) in acetonitrile (5 mL) were added KHSO$_4$ (685 mg, 5.02 mmol, 2.5 eq) and bromo acetaldehyde diethyl acetal (0.4 g, 5.02 mmol, 2.5 eq). After stirring at 100° C. for 16 h, the reaction mixture was poured into water and extracted using 10% MeOH/DCM. The organic layer was washed with brine solution, dried over sodium sulfate, and concentrated under reduced pressure (0.3.5 g). The residue was purified by silica get chromatography eluting with 2.5% MeOH in DCM to afford Intermediate-BB88 (0.180 g, 7.1%). MS (ES): m/z 199.5 (M+H)⁺.

Synthesis of 7-(difluoromethyl)-8-fluoro-3-iodoimidazo[1,2-a]pyridine (Intermediate BB89)

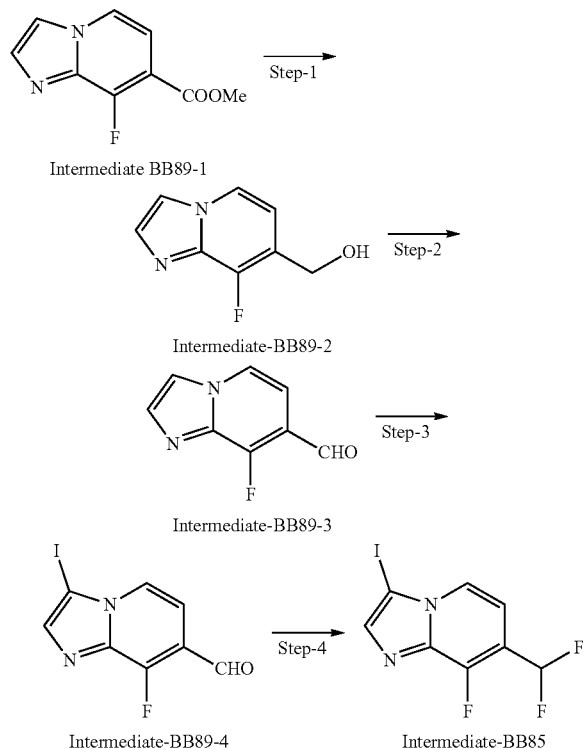

Step-1 Synthesis of (8-fluoroimidazo[1,2-a]pyridin-7-yl)methanol (Intermediate-BB89-2)

To a solution of methyl 8-fluoroimidazo[1,2-a]pyridine-7-carboxylate (5 g, 25.75 mmol, 1 eq) in THF (50 mL) at 0° C. was added LAH (1.7 g, 51.4 mmol, 2 eq). After warming to RT and stirring for 90 min, the reaction mixture was poured into sodium sulfate decahydrate and diluted with ethyl acetate (100 mL). The organic layer was filtered and concentrated under reduced pressure to afford Intermediate-BB89-2 (4 g, 93%) MS (ES): m/z 167.1 [M+H]⁺

Step-2 Synthesis of 8-fluoroimidazo[1,2-a]pyridine-7-carbaldehyde (Intermediate-BB89-3)

To a solution of Intermediate-BB89-2 (4 g, 24.07 mmol, 1 eq) in DCM (20 mL) at 0° C. was added Dess Martin periodinane (30 g, 72.21 mmol, 3 eq) portion wise. After warming to RT and stirring for 45 min, the reaction mixture was quenched with saturated sodium bicarbonate solution (250 mL) and extracted with ethyl acetate (100 mL×3). The combined extract was dried over sodium sulfate and concentrated under reduced pressure to afford Intermediate-BB89-3 (3.2 g, 80%) MS (ES): m/z 165.2 [M+H]⁺

Step-3 Synthesis of 8-fluoro-3-iodoimidazo[1,2-a]pyridine-7-carbaldehyde (Intermediate-BB89-4)

8-fluoro-3-iodoimidazo[1,2-a]pyridine-7-carbaldehyde (Intermediate-BB89-4) were carried out following representative procedures described in step-1 of Intermediate-BB81 (1.5 g, 60.6%) MS (ES): m/z 313.6 [M+H]⁺

Step-4 Synthesis of 7-(difluoromethyl)-8-fluoro-3-iodoimidazo[1,2-a]pyridine (Intermediate-BB89)

7-(difluoromethyl)-8-fluoro-3-iodoimidazo[1,2-a]pyridine (Intermediate-BB89) were carried out following representative procedures described in Intermediate-BB84 (0.5 g, 30.98%) MS (ES): m/z 313.6 [M+H]⁺

Synthesis of 3-bromo-7-methylpyrazolo[1,5-a]pyridine (Intermediate BB90)

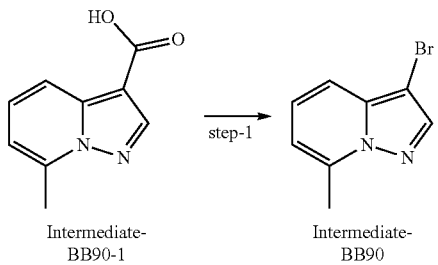

Step-1 Synthesis of 3-bromo-7-methylpyrazolo[1,5-a]pyridine (Intermediate BB90)

To a solution of Intermediate BB90-1 (0.500 g, 2.8 mmol) in DMF (15 mL) were added NaHCO₃ (715 mg, 8.51 mmol, 3 eq) and NBS (0.498 g, 2.8 mmol, 1 eq). After stirring at RT for 30 min, the reaction mixture was poured into water and extracted with EtOAc (20 mL×3). The combined organic layer was washed with brine solution, dried over sodium sulfate, and concentrated under reduced pressure. The residue was purified by silica get chromatography eluting with 5% EtOAc in hexane to afford Intermediate BB90 (0.470 g, 74.5%). MS (ES): m/z 211.3 (M+H)⁺.

Synthesis of 3-bromo-6-methylpyrazolo[1,5-a]pyridine (Intermediate BB91)

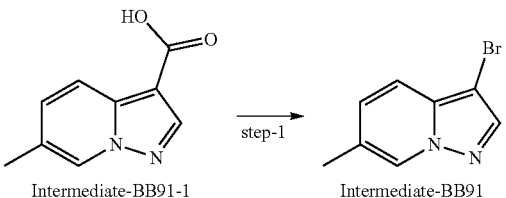

Intermediate BB91 was synthesize using same identical method as Intermediate-BB90 starting with Intermediate BB91-1

Synthesis of pyrrolo[1,2-b]pyridazin-4-yl 4-methylbenzenesulfonate (Intermediate BB92)

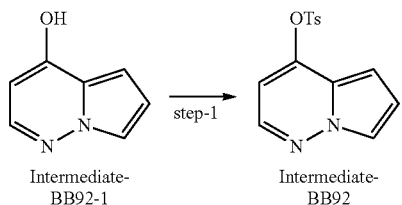 [SMILES: Oc1ccnn2cccc12 ; Cc1ccc(S(=O)(=O)Oc2ccnn3cccc23)cc1]

Step-1 Synthesis of pyrrolo[1,2-b]pyridazin-4-yl 4-methylbenzenesulfonate (Intermediate BB92)

To a solution of Intermediate-BB92-1 (0.600 g, 4.46 mmol) in DCM (10 mL) at 0° C. with TEA (1.9 mL, 13.43 mmol, 3 eq) was added 4-toluenesulfonyl chloride (1.56 g, 5.35 mmol, 1.2 eq). After stirring at RT for 1.5 h, the reaction mixture was poured into water and extracted with EtOAc (30 mL×3). The organic layer was washed with brine solution, dried over sodium sulfate, and concentrated under reduced pressure. The residue was purified by silica gel chromatography eluting with 8% EtOAc in hexane to afford Intermediate-BB92 (0.6 g, 46.5%). MS (ES): m/z 289.6 (M+H)$^+$.

The following intermediates were available commercially or prepared by known literature routes.

TABLE 5

Commercially available intermediates or intermediates prepared by known literature routes.

| # | Structure |
|---|---|
| BB9 | |
| BB10 | |
| BB17 | |
| BB39 | 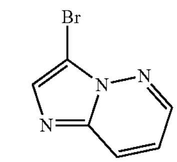 |
| BB40 | 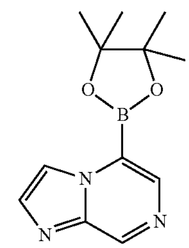 [SMILES: CC1(C)OB(c2cncc3nccn23)OC1(C)C] |
| BB41 | 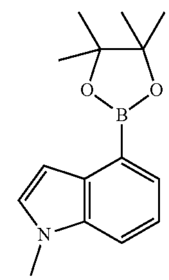 [SMILES: Cn1ccc2c(B3OC(C)(C)C(C)(C)O3)cccc21] |
| BB42 | 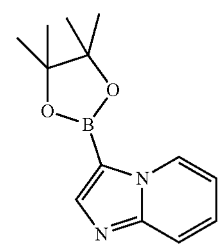 [SMILES: CC1(C)OB(c2cnc3ccccn23)OC1(C)C] |
| BB45 | 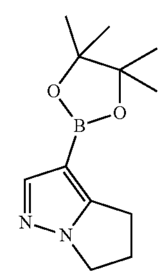 [SMILES: CC1(C)OB(c2cnn3c2CCC3)OC1(C)C] |
| BB46 | 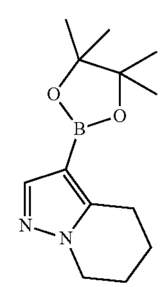 [SMILES: CC1(C)OB(c2cnn3c2CCCC3)OC1(C)C] |

TABLE 5-continued
Commercially available intermediates or intermediates prepared by known literature routes.
| # | Structure |
|---|---|
| BB47 | 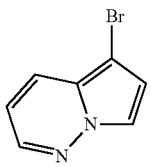 |
| BB48 | 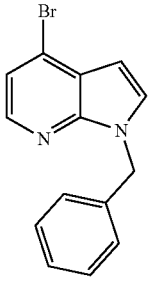 [SMILES: Brc1ccnc2c1ccn2Cc1ccccc1] |
| BB49 | 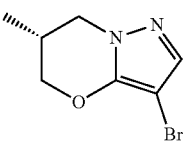 |
| BB51 | 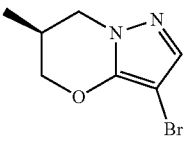 |
| BB52 | 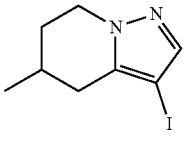 |
| BB53 | 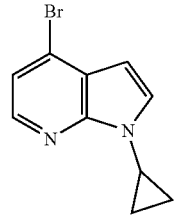 [SMILES: Brc1ccnc2c1ccn2C1CC1] |
| BB54 | 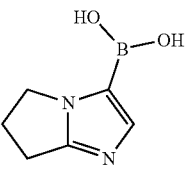 [SMILES: OB(O)c1cnc2n1CCC2] |
| BB57 | 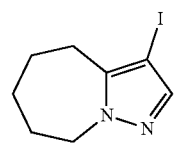 [SMILES: Ic1cnn2c1CCCCC2] |
| BB58 | 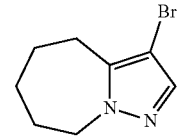 [SMILES: Brc1cnn2c1CCCCC2] |
| BB59 | 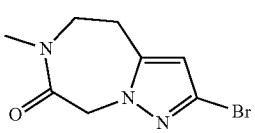 |
| BB60 | 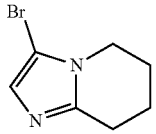 |
| BB61 | 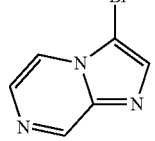 |
| BB64 | 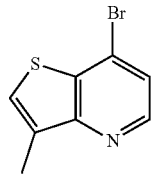 |
| BB65 | 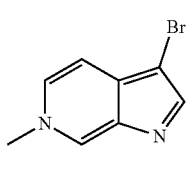 |
| BB66 | 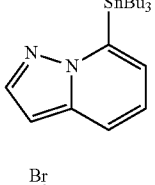 |
| BB67 | 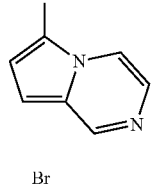 |
| BB73 | 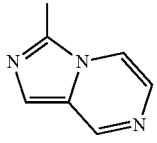 |

TABLE 5-continued

Commercially available intermediates or intermediates prepared by known literature routes.

| # | Structure |
|---|---|
| BB74 | 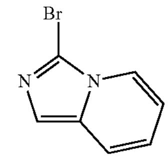 |
| BB79 | 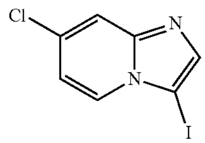 [SMILES: Clc1ccn2c(I)cnc2c1] |
| BB83 | 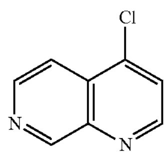 [SMILES: Clc1ccnc2cnccc12] |
| BB85 | 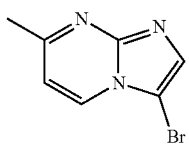 |
| BB86 | 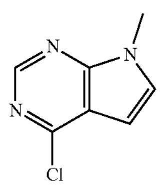 |
| BB16 | 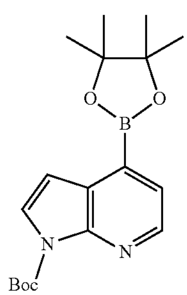 [SMILES: CC(C)(C)OC(=O)n1ccc2c(B3OC(C)(C)C(C)(C)O3)ccnc21] |

Synthesis of Tert-Butyl 3-bromo-2-ethyl-1H-indole-1-carboxylate (Intermediate BC1)-Method A2

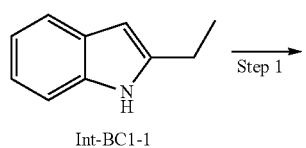

Int-BC1-1

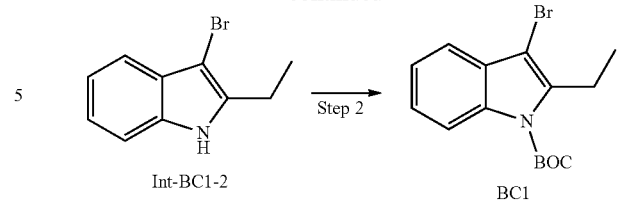

Int-BC1-2 → BC1

Step 1: 3-Bromo-2-ethyl-1H-indole (Intermediate BC1-2)

N-Bromosuccinimide (613 mg, 3.44 mmol) was added portion wise to a solution of 2-ethyl-1H-indole (500 mg, 4.33 mmol) in DMF (10 mL). After stirring at RT for 16 h, the reaction was quenched with a saturated NaHCO$_3$ solution and extracted into EtOAc (3×). The combined extracts were washed with brine, dried over MgSO$_4$, and concentrated in vacuo to afford the title compound (Intermediate BC1-2) (927 mg, quant) as a purple oil. $^1$H NMR (400 MHz, CDCl$_3$): δ 8.03 (s, 1H), 7.51-7.46 (m, 1H), 7.31-7.26 (m, 1H), 7.15 (t, J=3.7 Hz, 2H), 2.82 (q, J=7.7 Hz, 2H), 1.30 (t, J=7.8 Hz, 3H).

Step 2: Tert-Butyl 3-bromo-2-ethyl-1H-indole-1-carboxylate (BC1)

A solution of 3-bromo-2-ethyl-1H-indole (Intermediate BC1-2) (772 mg, 3.44 mmol) in DCM (20 mL) was treated with triethylamine (0.53 mL, 3.79 mmol), 4-(dimethylamino)pyridine (63 mg, 0.517 mmol) and di-tert-butyl carbonate (902 mg, 4.13 mmol). After stirring at RT for 16 h, the reaction was quenched with a saturated NaHCO$_3$ solution. The organic phase was washed with brine, dried by phase separator, and concentrated in vacuo to afford the title compound (Intermediate BC1) (1.14 g, quant) as a purple oil. $^1$H NMR (400 MHz, CDCl$_3$): δ 8.10 (d, J=7.3 Hz, 1H), 7.47 (d, J=7.7 Hz, 1H), 7.31-7.26 (m, 2H), 3.14 (q, J=7.2 Hz, 2H), 1.69 (s, 9H), 1.24 (t, J=7.7 Hz, 3H).

Synthesis of Tert-Butyl 3-(4,4,5,5-tetramethyl-1,3,2-dioxaborolan-2-yl)-1H-pyrrolo[3,2-b]pyridine-1-carboxylate (Intermediate BC2)-Method B2

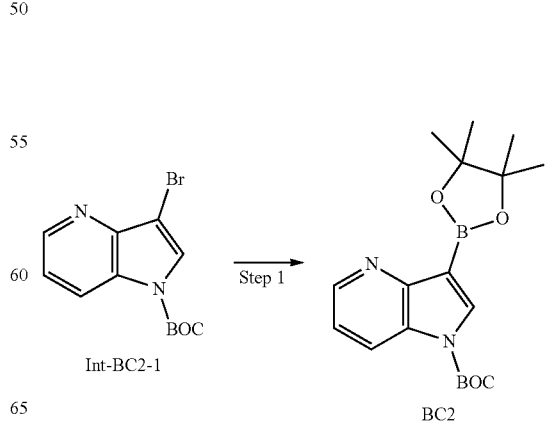

Int-BC2-1 → BC2

Step 1: tert-Butyl 3-(4,4,5,5-tetramethyl-1,3,2-dioxaborolan-2-yl)-1H-pyrrolo[3,2-b]pyridine-1-carboxylate (Intermediate BC2)

To a degassed solution of tert-butyl 3-bromo-1H-pyrrolo[3,2-b]pyridine-1-carboxylate (Intermediate BC2-1) (300 mg, 1.01 mmol) in 1,4-dioxane (6 mL) were added KOAc (297 mg, 3.03 mmol) and bis(pinacolato)diboron (282 mg, 1.11 mmol). The solution was purged with a $N_2$ stream for 30 min before Pd(dppf)Cl2 (37 mg, 0.051 mmol) was added. After stirring in a sealed tube at 125° C. overnight, the reaction mixture was cooled to RT and diluted ethyl acetate (25 mL) and water (20 mL). The organic phase was separated, and the aqueous phase extracted with ethyl acetate (2×25 mL). The combined organic phases were washed with brine (10 mL), passed through a hydrophobic frit and concentrated in vacuo. The crude compound (BC2) was taken forwards to the next step without further purification.

Synthesis of 1-(2-methoxyethyl)-4-(4,4,5,5-tetramethyl-1,3-dioxolan-2-yl)-1H-pyrrolo[2,3-b]pyridine (Intermediate BC3)-Method C2

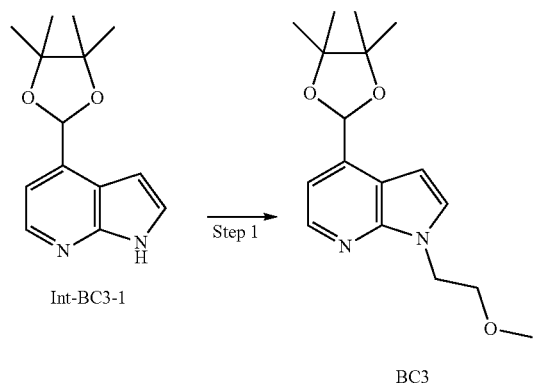

Step 1: 1-(2-methoxyethyl)-4-(4,4,5,5-tetramethyl-1,3-dioxolan-2-yl)-1H-pyrrolo[2,3-b]pyridine (Intermediate BC2)

A solution of 4-(4,4,5,5-tetramethyl-1,3-dioxolan-2-yl)-1H-pyrrolo[2,3-b]pyridine (Intermediate BC3-1) (200 mg, 0.819 mmol) in DMF (2 mL) at 0° C. was treated with sodium hydride (60% dispersion in mineral oil, 72 mg, 1.64 mmol). After 30 min at 0° C., 1-bromo-2-methoxy-ethane (228 mg, 1.64 mmol) was added. After the reaction was compete, the mixture was poured onto ice/water and extracted into EtOAc (5×). The organic phase was dried by phase separator and concentrated in vacuo to provide the title compound (Intermediate BC3) as a crude residue which was used as is.

Synthesis of 7-methyl-3-(4,4,5,5-tetramethyl-1,3,2-dioxaborolan-2-yl)imidazo[1,2-a]pyridine (Intermediate BC4)-Method D2

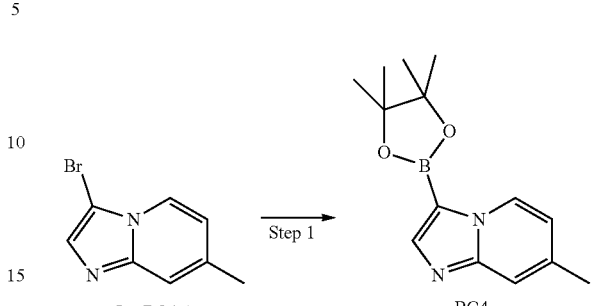

Step 1: 7-Methyl-3-(4,4,5,5-tetramethyl-1,3,2-dioxaborolan-2-yl)imidazo[1,2-a]pyridine (Intermediate BC4)

A solution of 3-bromo-7-methyl-imidazo[1,2-a]pyridine (Intermediate BC4-1) (530 mg, 2.51 mmol) and 2-isopropoxy-4,4,5,5-tetramethyl-1,3,2-dioxaborolane (748 mg, 4.02 mmol) in anhydrous THF (7 mL) at −15° C. under a nitrogen atmosphere was treated dropwise with isopropylmagnesium chloride lithium chloride complex solution (1.3 M in THF, 2.5 mL, 3.26 mmol). After stirring at −15° C. for 1.5 h, the reaction was quenched with a saturated $NH_4Cl$ solution and extracted into EtOAc (2×). The combined extracts were washed with brine, dried over $Na_2SO_4$, and concentrated in vacuo to leave the title compound (BC4) (731 mg, quant.) as an off-white solid which was used as is.

Synthesis of 3-iodo-7,8-dimethylimidazo[1,2-a]pyridine (Intermediate BC5)-Method E2

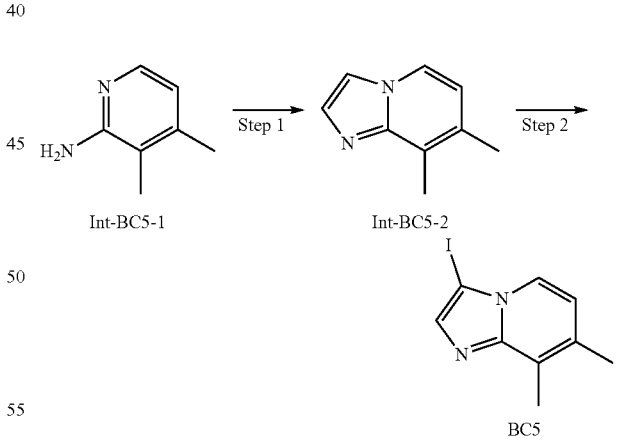

Step 1: 7,8-Dimethylimidazo[1,2-a]pyridine (Intermediate BC5-2)

3,4-Dimethylpyridin-2-amine (500 mg, 4.09 mmol) was dissolved in ethanol (10 mL) was treated with chloroacetaldehyde (50% in water, 1.0 mL, 8.19 mmol). After stirring at 100° C. in a sealed tube for 18 h, the solvent was removed in vacuo and the residue purified by column chromatography (0-10% gradient elution with 7N methanolic ammonia in DCM) to afford the title compound (Intermediate BC5-2) (487 mg, 81%) as a yellow solid. $^1$H NMR (400 MHz, DMSO): δ 8.33 (d, J=7.1 Hz, 1H), 7.87 (d, J=1.0 Hz, 1H), 7.50 (d, J=1.0 Hz, 1H), 6.75 (d, J=6.8 Hz, 1H), 2.48 (s, 3H), 2.33 (s, 3H).

Step 2: 3-Iodo-7,8-dimethylimidazo[1,2-a]pyridine (BC5)

A solution of 7,8-dimethylimidazo[1,2-a]pyridine (Intermediate BC5-2) (486 mg, 3.65 mmol) in chloroform (10 mL) was treated with N-iodosuccinimide (936 mg, 4.16 mmol). After stirring at RT for 18 h, the solvent was removed in vacuo and the residue purified by column chromatography (0-100% gradient elution EtOAc in cyclohexane) to afford the title compound (Intermediate BC5) (178 mg, 19%) as an off-white solid. $^1$H NMR (400 MHz, CDCl3): δ 8.30 (d, J=2.0 Hz, 1H), 7.77 (s, 1H), 7.67 (d, J=0.8 Hz, 1H), 2.68 (s, 3H), 2.40 (s, 3H).

Synthesis of N-cyclopropyl-3-iodo-4,5,6,7-tetrahydropyrazolo[1,5-a]pyridine-6-carboxamide (Intermediate BC6)-Method F2

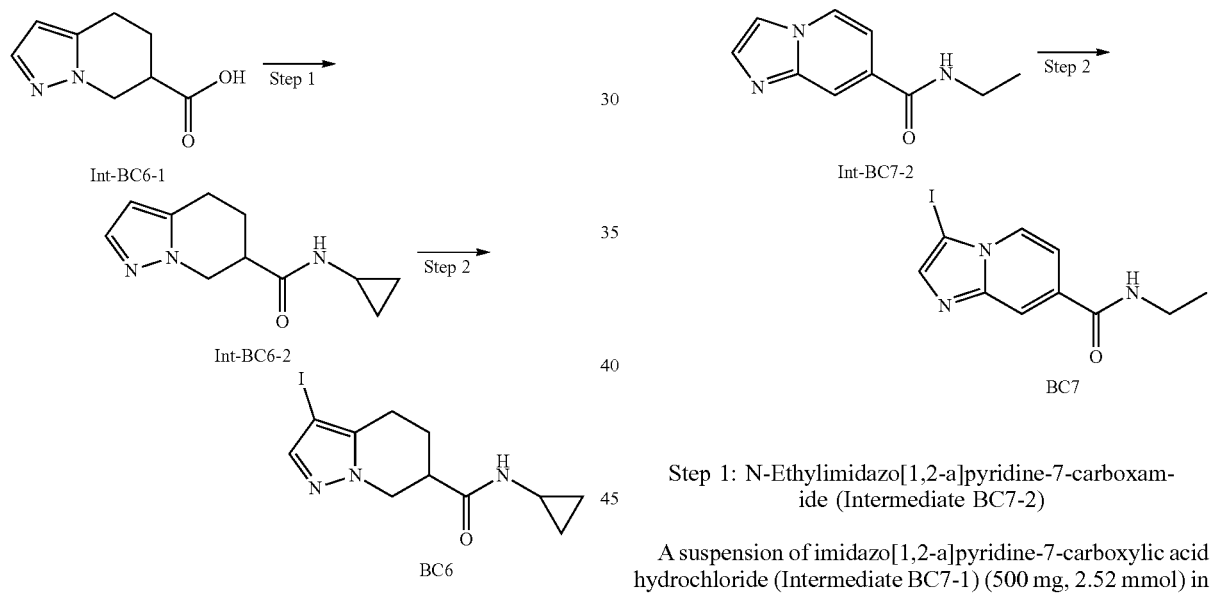

Step 1: N-cyclopropyl-4,5,6,7-tetrahydropyrazolo[1,5-a]pyridine-6-carboxamide (Intermediate BC6-2)

A suspension of 4,5,6,7-tetrahydropyrazolo[1,5-a]pyridine-6-carboxylic acid (Intermediate BC6-1) (410 mg, 2.47 mmol) in DCM (10 mL) was treated dropwise with oxalyl chloride (0.25 mL, 2.96 mmol). After stirring at RT for 30 min until homogeneous, the solvent was removed in vacuo. The residue was re-suspended in DCM (10 mL) at 0° C. and treated with triethylamine (1.2 mL, 8.61 mmol) followed by cyclopropylamine (0.21 mL, 2.96 mmol). After warming to RT and stirring for 16 h, the reaction was quenched with water. The organic phase washed with a saturated NaHCO$_3$ solution, dried by phase separator, and concentrated in vacuo to afford the title compound (Intermediate BC6-2) (286 mg, 57%) as a grey solid. $^1$H NMR (400 MHz, DMSO): δ 7.96 (d, J=3.2 Hz, 1H), 7.18 (d, J=1.8 Hz, 1H), 5.81 (t, J=0.8 Hz, 1H), 4.03 (dd, J=5.2, 12.7 Hz, 1H), 3.83 (dd, J=10.1, 12.6 Hz, 1H), 2.72-2.65 (m, 2H), 2.51-2.47 (m, 2H), 1.90-1.81 (m, 1H), 1.67-1.55 (m, 1H), 0.49-0.44 (m, 2H), 0.28-0.23 (m, 2H).

Step 2: N-cyclopropyl-3-iodo-4,5,6,7-tetrahydropyrazolo[1,5-a]pyridine-6-carboxamide (BC6)

Step 2 was carried out following the representative procedure described in Intermediate BC5-Method E2, Step 2 using DMF as solvent. The crude product was used directly in subsequent reactions.

Synthesis of N-cyclopropyl-3-iodo-5,6,7,8-tetrahydroimidazo[1,2-a]pyridine-7-carboxamide (Intermediate BC7)-Method G2

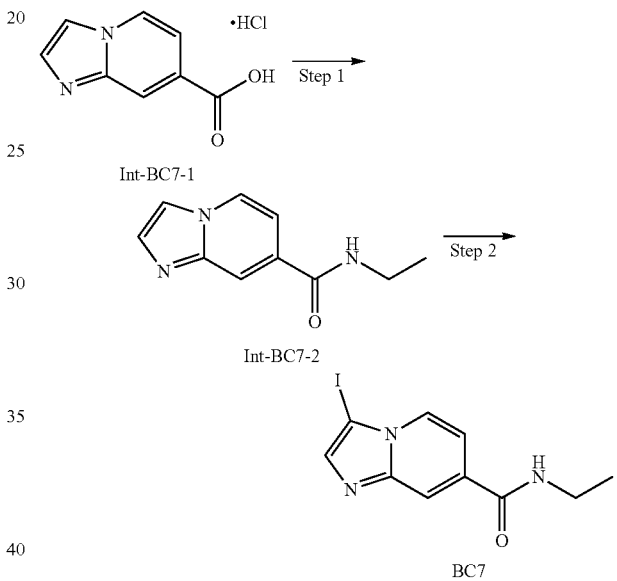

Step 1: N-Ethylimidazo[1,2-a]pyridine-7-carboxamide (Intermediate BC7-2)

A suspension of imidazo[1,2-a]pyridine-7-carboxylic acid hydrochloride (Intermediate BC7-1) (500 mg, 2.52 mmol) in acetonitrile (5.0 mL) and THF (1.5 mL) was treated with ethylamine (2M in THF, 1.5 mL, 3.02 mmol), 1-methylimidazole (723 mg, 8.81 mmol) followed by chloro-N,N,N',N'-tetramethylformamidinium hexafluorophosphate (848 mg, 3.02 mmol). After stirring at RT for 18 h, the solvent was removed in vacuo and the residue purified by column chromatography (0-10% methanol gradient in DCM). Trituration with acetonitrile afforded the title compound (Intermediate BC7-2) (132 mg, 28%) as an off-white solid. $^1$H NMR (400 MHz, DMSO): δ 8.69 (t, J=5.4 Hz, 1H), 8.65 (dd, J=0.9, 7.0 Hz, 1H), 8.17 (s, 1H), 8.10 (s, 1H), 7.76 (d, J=0.9 Hz, 1H), 7.36 (dd, J=1.9, 7.4 Hz, 1H), 3.35 (m, 2H), 1.20 (t, J=7.2 Hz, 3H).

Step 2: N-Cyclopropyl-3-iodo-5,6,7,8-tetrahydroimidazo[1,2-a]pyridine-7-carboxamide (BC7)

Step 2 was carried out following the representative procedure described in Intermediate BC5-Method E2, Step 2 to afford the title compound (Intermediate BC7) (220 mg, 88%) as a light brown solid. ¹H NMR (400 MHz, DMSO): δ 8.77 (t, J=5.5 Hz, 1H), 8.44 (dd, J=0.8, 7.1 Hz, 1H), 8.20 (dd, J=0.9, 1.6 Hz, 1H), 7.90 (s, 1H), 7.53 (dd, J=1.8, 7.4 Hz, 1H), 3.35 (m, 2H), 1.21 (t, J=7.3 Hz, 3H).

Synthesis of 3-iodo-N-(2-methoxyethyl)imidazo[1,2-a]pyridin-7-amine (Intermediate BC8)-Method 112

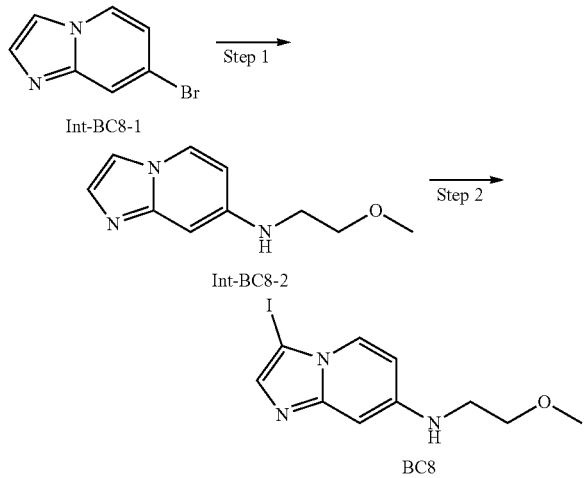

Step 1: N-(2-methoxyethyl)imidazo[1,2-a]pyridin-7-amine (Intermediate BC8-2)

A mixture of 7-bromoimidazo[1,2-a]pyridine (Intermediate BC8-1) (800 mg, 4.06 mmol), 2-methoxyethylamine (335 mg, 4.47 mmol), t-BuXPhos (122 mg, 0.812 mmol), Pd₂(dba)₃ (372 mg, 0.406 mmol) and sodium tert-butoxide (975 mg, 10.15 mmol) in toluene (40 mL) was degassed, purged with nitrogen and heated at 110° C. for 18 h. The solvent was removed in vacuo and the residue purified by column chromatography (0-10% methanol gradient in DCM) to afford the title compound (Intermediate BC8-2) (407 mg, 52%) as a brown oil which was used directly in subsequent reactions.

Step 2: 3-iodo-N-(2-methoxyethyl)imidazo[1,2-a]pyridin-7-amine (BC8)

Step 2 was carried out following the representative procedure described in Intermediate BC5-Method E2, Step 2 to afford the title compound (Intermediate BC8) (610 mg, 92%) as a light brown residue which was used crude in subsequent reactions.

Synthesis of 7-fluoro-3-(tributylstannyl)imidazo[1,2-a]pyridine (Intermediate BC9)-Method 12

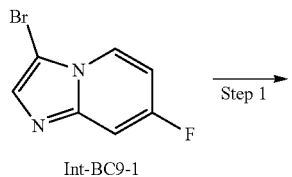

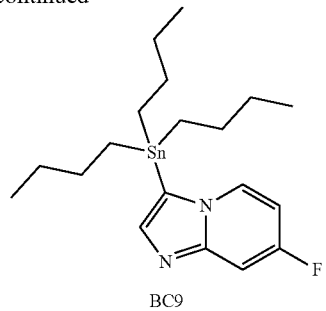

A solution of 3-bromo-7-fluoroimidazo[1,2-a]pyridine (Intermediate BC9-1) (400 mg, 1.86 mmol) in anhydrous THF (15 mL) at −15° C. under a nitrogen atmosphere was treated dropwise with isopropylmagnesium chloride lithium chloride complex solution (1.3 M in THF, 1.5 mL, 2.05 mmol). After stirring for 15 min, tributyltin chloride (0.53 mL, 1.95 mmol) was added. After warming to RT and stirring for 1 h, the reaction was quenched with a saturated NH₄Cl solution and extracted into EtOAc (2×). The combined extracts were dried over MgSO4 and concentrated in vacuo to afford the title compound (Intermediate BC9) (617 mg, 78%) as a yellow oil which was used crude in subsequent reactions.

The following BC intermediates were prepared according to any of Intermediate Methods A2-I2 as described above.

TABLE 6

BC intermediates prepared according to any of Intermediate Methods A2-I2.

| # | STRUCTURE | Method |
|---|---|---|
| BC22 | 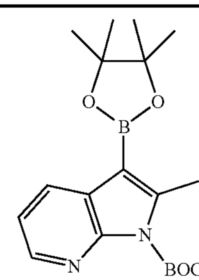 | Method A2 (Step 2) and Intermediate BC1-Method A2 (Step 1) starting with 3-bromo-2-methyl-1H-pyrrolo[2,3-b]pyridine |
| BC29 | 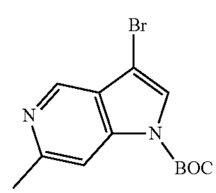 [SMILES: Cc1cc2c(cn1)c(Br)cn2C(=O)OC(C)(C)C] | Method A2, Step 2 starting from 3-bromo-6-methyl-5-azaindole |
| BC37 | 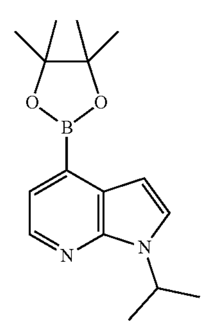 [SMILES: CC(C)n1ccc2c(B3OC(C)(C)C(C)(C)O3)ccnc21] | Method C2 using isopropyl iodide |

TABLE 6-continued

BC intermediates prepared according to any of Intermediate Methods A2-I2.

| # | STRUCTURE | Method |
|---|---|---|
| BC38 | | Method C2 using bromoethane |
| BC44 | | Method B2 using 4-bromo-1-methyl-1H-pyrazolo[3,4-b]pyridine |
| BC48 | | Method C2 followed by Intermediate BC2-Method B2 using 4-bromo-5-fluoro-1H-pyrrolo[2,3-b]pyridine and iodomethane |
| BC53 | | Method A2, Step 2 using 4-bromo-6-methyl-1H-pyrrolo[2,3-b]pyridine |
| BC54 | | Method A2, Step 2 using 4-bromo-5-methyl-1H-pyrrolo[2,3-b]pyridine |
| BC55 | | Method D2 using 3-bromo-5,6,7,8-tetrahydroimidazo[1,2-a]pyridine |
| BC57 | 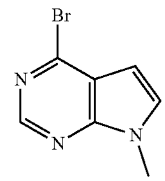 | Method C2 using 4-bromo-7H-pyrrolo[2,3-d]pyrimidine and iodomethane |
| BC65 | 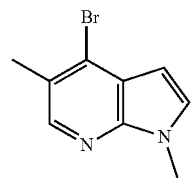 | Method C2 using 4-bromo-5-methyl-1H-pyrrolo[2,3-b]pyridine and iodomethane |
| BC67 | 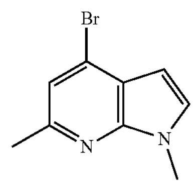 | Method C2 using 4-bromo-6-methyl-1H-pyrrolo[2,3-b]pyridine and iodomethane |
| BC68 | 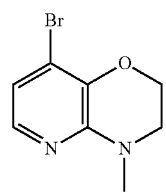 | Method C2 using 8-bromo-3,4-dihydro-2H-pyrido[3,2-b][1,4]oxazine and iodomethane |
| BC73 | 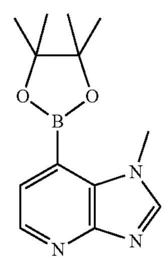 [SMILES: Cn1cnc2nccc(B3OC(C)(C)C(C)(C)O3)c21] | Method D using 7-bromo-1-methyl-1H-imidazo[4,5-b]pyridine |
| BC74 | 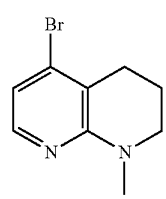 | Method C2 using 5-bromo-1,2,3,4-tetrahydro-1,8-naphthyridine and iodomethane |
| BC75 | 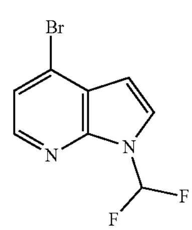 [SMILES: FC(F)n1ccc2c(Br)ccnc21] | Method C2 using 4-bromo-7-aza-indole and sodium bromo-difluoro-acetate |

TABLE 6-continued

BC intermediates prepared according to any of Intermediate Methods A2-I2.

| # | STRUCTURE | Method |
|---|---|---|
| BC87 | 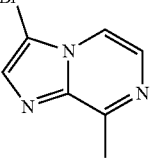 | Method E2 using 3-methyl-pyrazin-2-amine |
| BC91 | 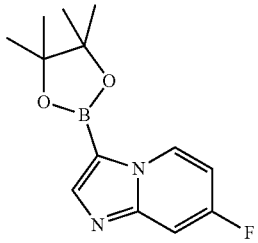 [SMILES: CC1(C)OB(c2cnc3cc(F)ccn23)OC1(C)C] | Method D2 using 7-fluoro-3-iodoimidazo[1,2-a]pyridine |
| BC97 | 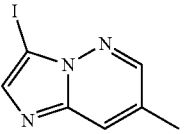 | Method E2 starting with 5-methyl-pyridazin-3-amine |
| BC98 | 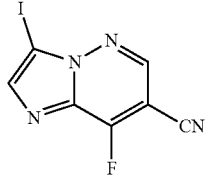 [SMILES: N#Cc1cnn2c(I)cnc2c1F] | Method E2 using 2-amino-3-fluoroisonicotinonitrile |
| BC100 | 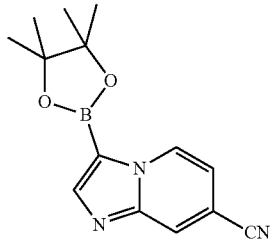 [SMILES: CC1(C)OB(c2cnc3cc(C#N)ccn23)OC1(C)C] | Method D2 using 7-cyano-3-iodoimidazo[1,2-a]pyridine |
| BC102 | 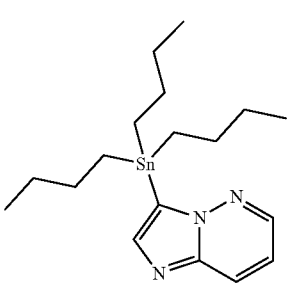 [SMILES: CCC[CH2][Sn]([CH2]CCC)([CH2]CCC)[c]1cnc2cccnn12] | Method I2 using 3-bromoimidazo[1,2-b]pyridazine |
| BC103 | 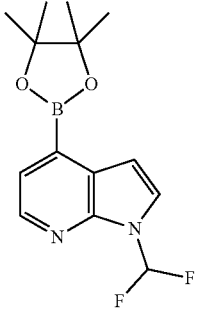 [SMILES: CC1(C)OB(c2ccnc3c2ccn3C(F)F)OC1(C)C] | Method B2 using BC75 |
| BC104 | 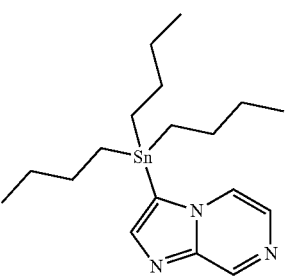 [SMILES: CCC[CH2][Sn]([CH2]CCC)([CH2]CCC)[c]1cnc2cnccn12] | Method I2 using 3-bromoimidazo[1,2-a]pyrazine |
| BC105 | 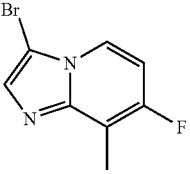 | Method E2 using 3-fluoro-4-methylpyridin-2-amine |
| BC107 | 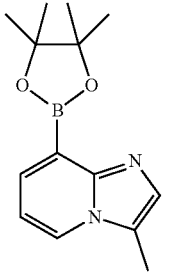 [SMILES: Cc1cnc2c(B3OC(C)(C)C(C)(C)O3)cccn12] | Method B2 using 8-bromo-3-methylimidazo[1,2-a]pyridine |
| BC110 | 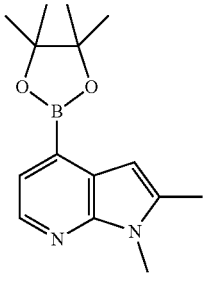 | Method B2 using 4-bromo-1,2-dimethyl-1H-pyrrolo[2,3-b]pyridine |

TABLE 6-continued

BC intermediates prepared according to any of Intermediate Methods A2-I2.

| # | STRUCTURE | Method |
|---|---|---|
| BC111 | 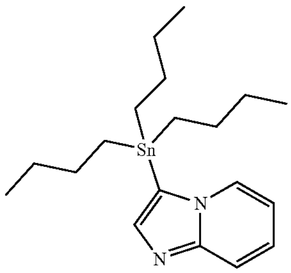 [SMILES: CCC[CH2][Sn]([CH2]CCC)([CH2]CCC)[c]1cnc2ccccn12] | Method I2 using 3-bromo-imidazo[1,2-a]pyridine |
| BC112 | 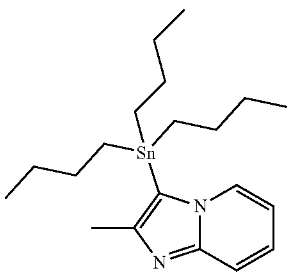 [SMILES: CCC[CH2][Sn]([CH2]CCC)([CH2]CCC)[c]1c(C)nc2ccccn12] | Method I2 using 3-bromo-2-methylimidazo[1,2-a]pyridine |
| BC113 | 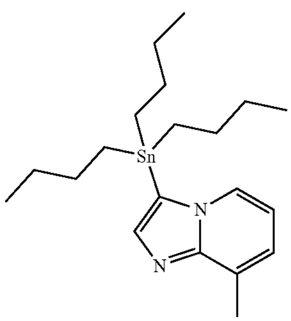 [SMILES: CCC[CH2][Sn]([CH2]CCC)([CH2]CCC)[c]1cnc2c(C)cccn12] | Method I2 using 3-bromo-8-methylimidazo[1,2-a]pyridine |
| BC114 | 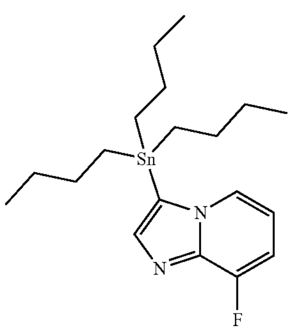 [SMILES: CCC[CH2][Sn]([CH2]CCC)([CH2]CCC)[c]1cnc2c(F)cccn12] | Method I2 using 3-bromo-8-fluoroimidazo[1,2-a]pyridine |
| BC115 | 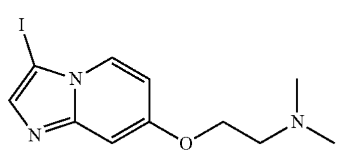 [SMILES: CN(C)CCOc1ccn2c(I)cnc2c1] | Method E2, Step 2 using 2-(imidazo[1,2-a]pyridin-7-yloxy)-N,N-dimethyl-ethan-1-amine |
| BC116 | | Method E2 using 4-fluoro-3-methoxypyridin-2-amine |
| BC117 | | Method E2 using 4-fluoro-3-methylpyridin-2-amine |
| BC118 | | Method D2 using 3-bromo-8-fluoroimidazo[1,2-a]pyridine |
| BC119 | | Method E2 using 3-(difluoromethyl)pyridin-2-amine |
| BC120 | | Method I2 using 8-(difluoromethyl)-3-iodoimidazo[1,2-a]pyridine |

TABLE 6-continued

BC intermediates prepared according to any of Intermediate Methods A2-I2.

| # | STRUCTURE | Method |
|---|---|---|
| BC123 | (3-tributylstannyl-7-methyl-8-fluoroimidazo[1,2-a]pyridine) | Method I2 using BC117 |
| BC124 | (3-(pinacolboronate)-8-methoxyimidazo[1,2-a]pyridine) | Method D2 using 8-methoxy-3-iodoimidazo[1,2-a]pyridine |
| BC125 | (3-bromo-2-phenyl-1-BOC-indole) | Method A2 using 2-Phenyl-1H-indole |
| BC126 | (3-tributylstannylimidazo[1,2-a]pyrimidine) | Method I2 using 3-bromoimidazo[1,2-a]pyrimidine |
| BC127 | (3-(pinacolboronate)-8-chloroimidazo[1,2-a]pyridine) | Method D2 using 8-chloro-3-iodoimidazo[1,2-a]pyridine |

The following intermediates were available commercially or prepared by known literature routes.

TABLE 7

Intermediates available commercially or prepared by known literature routes.

| # | Structure |
|---|---|
| BC10 | (1-BOC-indole-3-boronic acid) |
| BC11 | (1-BOC-6-methoxyindole-3-boronic acid pinacol ester) |
| BC12 | (1-BOC-7-methylindole-3-boronic acid pinacol ester) |
| BC13 | (1-BOC-7-azaindole-3-boronic acid pinacol ester) |
| BC14 | (1-BOC-7-methoxyindole-3-boronic acid pinacol ester) |

TABLE 7-continued
Intermediates available commercially or prepared by known literature routes.
| # | Structure |
|---|---|
| BC15 | 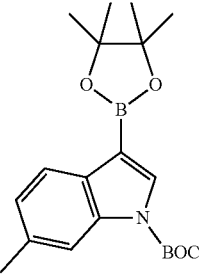 |
| BC16 | 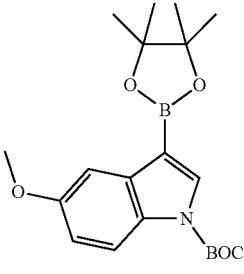 |
| BC17 | 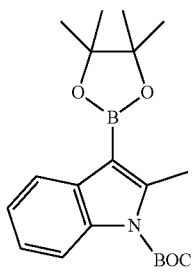 [SMILES: Cc1c(B2OC(C)(C)C(C)(C)O2)c2ccccc2n1C(=O)OC(C)(C)C] |
| BC18 | 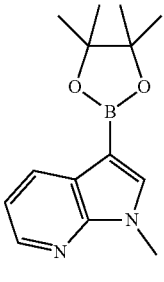 [SMILES: Cn1cc(B2OC(C)(C)C(C)(C)O2)c2cccnc21] |
| BC19 | 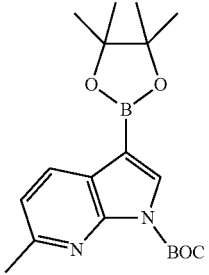 |
| BC20 | 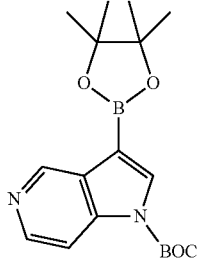 [SMILES: CC(C)(C)OC(=O)n1cc(B2OC(C)(C)C(C)(C)O2)c2cnccc21] |
| BC21 | 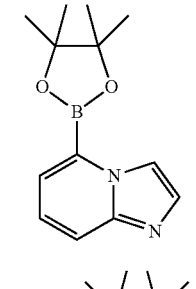 |
| BC23 | 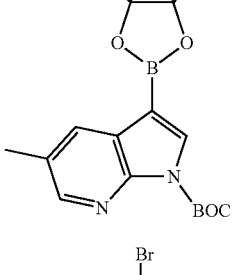 |
| BC24 | 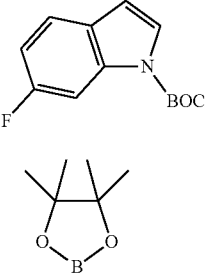 |
| BC25 | 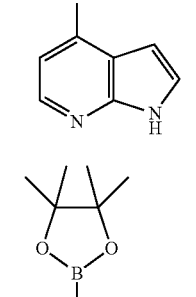 |
| BC26 | 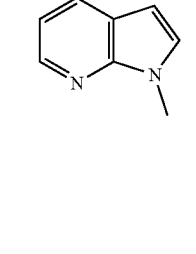 |

TABLE 7-continued
Intermediates available commercially or prepared by known literature routes.
| # | Structure |
|---|---|
| BC27 | 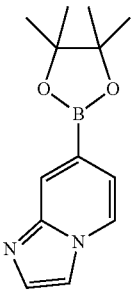 |
| BC28 | 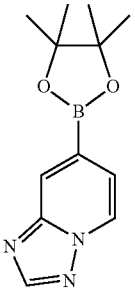 [SMILES: CC1(C)OB(c2ccn3ncnc3c2)OC1(C)C] |
| BC30 | 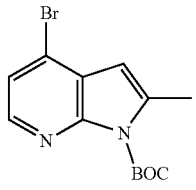 [SMILES: Cc1cc2c(Br)ccnc2n1C(=O)OC(C)(C)C] |
| BC31 | 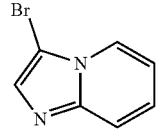 |
| BC32 | 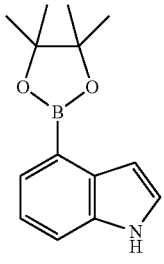 [SMILES: CC1(C)OB(c2cccc3[nH]ccc23)OC1(C)C] |
| BC33 |  |
| BC34 | 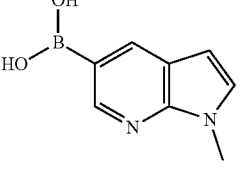 |
| BC35 | 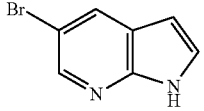 |
| BC36 | 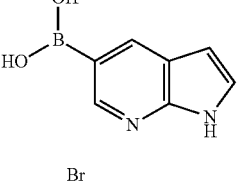 |
| BC39 | 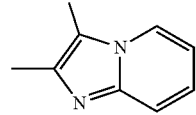 |
| BC40 | 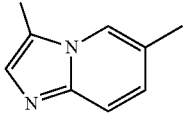 |
| BC41 | 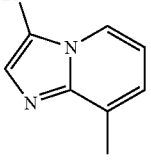 |
| BC42 | 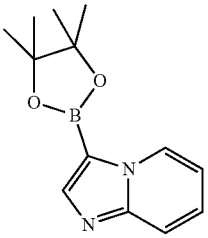 |
| BC43 | 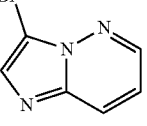 |
| BC45 | 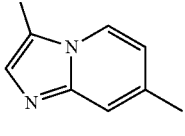 |

TABLE 7-continued

Intermediates available commercially or prepared by known literature routes.

| # | Structure |
|---|---|
| BC46 | 3-bromo-6-methylpyrazolo[1,5-a]pyridine |
| BC47 | 4-bromo-1-methyl-1H-pyrrolo[3,2-b]pyridine |
| BC49 | 4-bromo-1-Boc-2,3-dihydro-1H-pyrrolo[2,3-b]pyridine |
| BC50 | 3-bromo-7-methylpyrazolo[1,5-a]pyridine |
| BC51 | 3-bromoimidazo[1,2-a]pyridine-8-carbonitrile |
| BC52 | 3-bromoimidazo[1,2-a]pyrazine |
| BC56 | 7-(4,4,5,5-tetramethyl-1,3,2-dioxaborolan-2-yl)-1H-pyrrolo[3,2-b]pyridine |
| BC58 | 3-bromo-[1,2,4]triazolo[4,3-a]pyridine |
| BC59 | 3-bromoimidazo[1,2-a]pyrimidine |
| BC60 | 3-bromo-8-fluoroimidazo[1,2-a]pyridine |
| BC61 | 3-bromopyrazolo[1,5-a]pyridine |
| BC62 | 3-bromo-7-Boc-5,6,7,8-tetrahydroimidazo[1,2-a]pyrazine |
| BC63 | 4-bromo-1-methyl-2,3-dihydro-1H-pyrrolo[2,3-b]pyridine |
| BC64 | 4-bromo-1,3-dimethyl-1H-pyrrolo[2,3-b]pyridine |
| BC66 | 4-bromo-1-methyl-1H-indole |
| B69 | 7-bromothieno[3,2-b]pyridine |
| BC70 | 3-bromo-6-methylpyrazolo[1,5-a]pyrimidine |

TABLE 7-continued
Intermediates available commercially or prepared by known literature routes.
| # | Structure |
|---|---|
| BC71 | 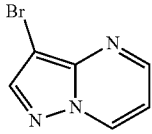 |
| BC72 | 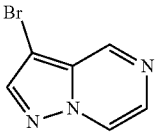 |
| BC76 | 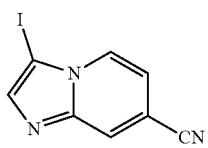 [SMILES: N#Cc1ccn2c(I)cnc2c1] |
| BC77 | 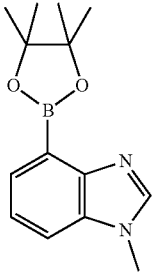 [SMILES: Cn1cnc2c(B3OC(C)(C)C(C)(C)O3)cccc21] |
| BC78 | 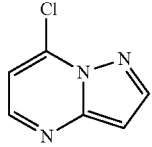 |
| BC79 | 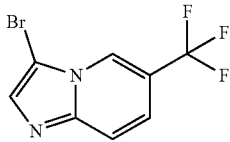 [SMILES: FC(F)(F)c1ccc2ncc(Br)n2c1] |
| BC80 | 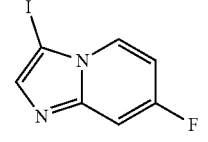 [SMILES: Fc1ccn2c(I)cnc2c1] |
| BC81 | 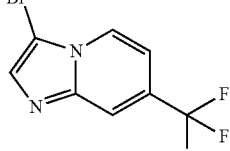 |
| BC82 | 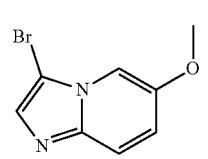 |
| BC83 | 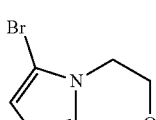 |
| BC84 | 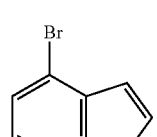 |
| BC85 | 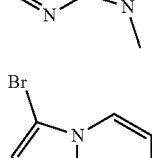 |
| BC86 | 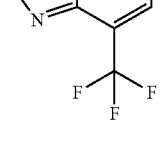 |
| BC88 | 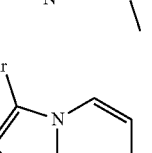 |
| BC89 | 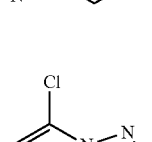 |
| BC90 | 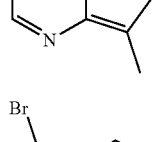 |
| BC92 | 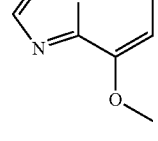 |

TABLE 7-continued

Intermediates available commercially or prepared by known literature routes.

| # | Structure |
|---|---|
| BC93 | 4-bromo-1-methyl-1H-benzimidazole |
| BC94 | (3-iodoimidazo[1,2-a]pyridin-7-yl)methanol |
| BC95 | 8-bromo-3-methylimidazo[1,5-a]pyridine |
| BC96 | 7-cyclopropyl-3-iodoimidazo[1,2-a]pyridine |
| BC99 | 3-bromo-7-chloroimidazo[1,2-a]pyridine |
| BC101 | 3-bromo-7-(difluoromethyl)imidazo[1,2-a]pyridine |
| BC106 | 3-iodo-7-(2-((tetrahydro-2H-pyran-2-yl)oxy)ethoxy)imidazo[1,2-a]pyridine |
| BC108 | 1-methyl-4-(4,4,5,5-tetramethyl-1,3,2-dioxaborolan-2-yl)-1H-indole |
| BC109 | 3-bromo-6-methylimidazo[1,2-a]pyrimidine |
| BC121 | 3-(4,4,5,5-tetramethyl-1,3,2-dioxaborolan-2-yl)pyrazolo[1,5-a]pyridine |
| BC122 | 6-fluoro-3-iodopyrazolo[1,5-a]pyridine |

Example 1. Method A

Synthesis of 7-((5-(4-Methylpiperazin-1-yl)pyridin-2-yl)amino)-4-(1H-pyrrolo[2,3-b]pyridin-3-yl)-2,3-dihydro-1H-pyrrolo[3,4-c]pyridin-1-one (I-6)

1.1 → Step 1 → 1.2 → Step 2 →

-continued

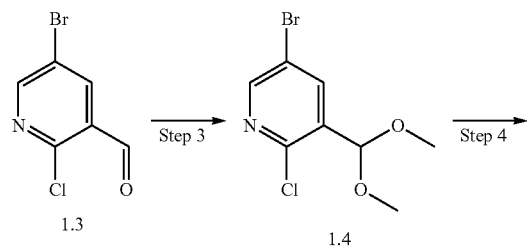

1.3    1.4

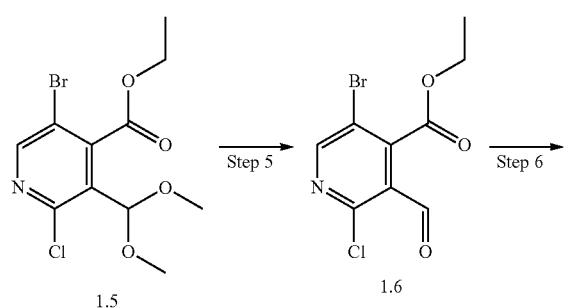

1.5    1.6

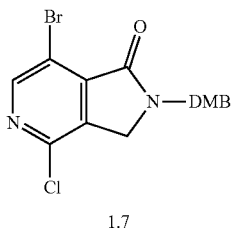

1.7

Step 1.
5-Bromo-2-chloro-N-methoxy-N-methylnicotinamide (1.2)

A mixture of 5-bromo-2-chloronicotinic acid (1.1) (4.00 g, 16.92 mmol) in thionyl chloride (20 mL) was heated at 80° C. for 2 h. Concentrated in vacuo and azeotroped with toluene (2×10 mL). The residue was taken up in DCM and cooled to 0° C. The mixture was treated with N, O-dimethylhydroxylamine hydrochloride (2.06 g, 21.15 mmol) followed by trimethylamine (7.1 mL, 50.75 mmol) and stirred for 1 h. The mixture was diluted with DCM, washed with 10% citric acid solution, saturated aqueous $NaHCO_3$ solution, water and brine, dried over $Na_2SO_4$, and concentrated in vacuo to leave the title compound (1.2) (3.81 g, 81%) as a pale orange solid. m/z=280.9 $[M+H]^+$, $^1$H NMR (400 MHz, $CDCl_3$): δ 8.50 (d, J=2.0 Hz, 1H), 7.83-7.78 (m, 1H), 3.53 (s, 3H), 3.39 (s, 3H).

Step 2. 5-Bromo-2-chloronicotinaldehyde (1.3)

A solution of 5-bromo-2-chloro-N-methoxy-N-methylnicotinamide (1.2) (3.80 g, 13.59 mmol) in dry THF (30 mL) at −10° C. under a nitrogen atmosphere was treated dropwise with $LiAlH_4$ (1M solution in THF, 5.4 mL, 5.44 mmol). After the addition, the mixture was allowed to warm to RT and stirred for 18 h. The reaction was cooled to back down to 0° C., quenched with careful addition of 1M $KHSO_4$ solution, and extracted into EtOAc (3×20 mL). The combined extracts were washed with brine, dried over $Na_2SO_4$, and concentrated in vacuo. The residue was purified by silica gel chromatography (0-25% gradient elution EtOAc in iso-hexane) to leave the title compound (1.3) (2.31 g, 77%) as a white solid. m/z=220.9 $[M+H]^+$, $^1$H NMR (400 MHz, $CDCl_3$): δ 10.37 (s, 1H), 8.66 (d, J=2.6 Hz, 1H), 8.33 (d, J=2.6 Hz, 1H).

Step 3.
5-Bromo-2-chloro-3-(dimethoxymethyl)pyridine (1.4)

A solution of 5-bromo-2-chloronicotinaldehyde (1.3) (18.66 g, 84.6 mmol) in MeOH (50 mL) was treated with p-toluenesulfonic acid (1.61 g, 0.85 mmol), followed by trimethyl orthoformate (37 mL, 338.4 mmol). The resulting mixture was heated to reflux for 2 h. The solvent was then removed in vacuo and the residue was taken up in EtOAc (100 mL) and washed with saturated aqueous $NaHCO_3$(2× 100 mL), water (100 mL) and brine (100 mL), dried with $MgSO_4$, filtered and the solvent removed in vacuo to yield the title compound (1.4) (16 g, 70%) as a clear oil. m/z=267.5 $[M+H]^+$, $^1$H NMR (400 MHz, $CDCl_3$) δ 8.42 (d, 1H), 8.08 (d, 1H), 5.53 (s, 1H), 3.41 (s, 6H).

Step 4. Ethyl 5-bromo-2-chloro-3-(dimethoxymethyl)isonicotinate (1.5)

A degassed solution of LDA (2 M in THF/Heptane/Ethylbenzene, 5.16 mL, 10.32 mmol) in dry THF (25 mL) was cooled down to −78° C. before a solution of 5-bromo-2-chloro-3-(dimethoxymethyl)pyridine (1.4) (2.5 g, 9.38 mmol) in dry and degassed THF (10 mL) was added dropwise. After 30 min, ethyl chloroformate (2.68 mL, 28.14 mmol) was added dropwise and the reaction stirred at −50° C. for 40 min. The reaction was quenched with saturated aqueous $NaHCO_3$ (25 mL) and allowed to warm to RT. The mixture was extracted with ethyl acetate (2×25 mL) and the combined organic phases were washed with brine (20 mL), dried with $MgSO_4$, filtered, and then concentrated in vacuo. The residue was purified by column chromatography (0-50% gradient elution EtOAc in iso-hexane) to afford the title compound (1.5) (2.01 g, 63%) as a yellow oil. m/z=339.7 $[M+H]^+$, $^1$H NMR (400 MHz, $CDCl_3$) δ 8.52 (s, 1H), 5.53 (s, 1H), 4.43 (q, 2H), 3.41 (s, 6H), 1.41 (t, 3H)

Step 5. Ethyl 5-bromo-2-chloro-3-formylisonicotinate (1.6)

A solution of ethyl 5-bromo-2-chloro-3-(dimethoxymethyl)isonicotinate (5) (6.9 g, 20.4 mmol) in MeCN (200 mL) and $H_2O$ (4 mL) was treated with lithium tetrafluoroborate (1M in MeCN, 20.4 mL, 20.4 mmol) and stirred at 90° C. for 16 h. After that time, volatiles were eliminated, the residue taken up in DCM and washed with $H_2O$ (2×30 mL). Solvent was removed in vacuo to afford the title compound (1.6) (5.8 g, 97%) as an orange oil. m/z=293.6 $[M+H]^+$, $^1$H NMR (400 MHz, $CDCl_3$) δ 10.35 (s, 1H), 8.73 (s, 1H), 4.53 (q, 2H), 3.41 (s, 6H), 1.44 (t, 3H).

Step 6. 7-Bromo-4-chloro-2-(2,4-dimethoxybenzyl)-2,3-dihydro-1H-pyrrolo[3,4-c]pyridin-1-one (1.7)

A solution of ethyl 5-bromo-2-chloro-3-(dimethoxymethyl)isonicotinate (1.6) (5.8 g, 19.83 mmol) in DCM (40 mL) was treated with acetic acid (3.4 mL, 59.48 mmol) and stirred at RT for a few min before 2,4-dimethoxybenzylamine (3.28 mL, 21.81 mmol) was added dropwise. After 3 h sodium cyanoborohydride (1.87 g, 29.74 mmol) was added portion wise and the reaction stirred at RT. The mixture was then filtered through a pad of Celite, the solvent was removed in vacuo and the residue was purified by column chromatography (0-60% gradient elution EtOAc in isohexane) to afford the desired compound (1.7) (3.5 g, 44%) as a yellow oil. m/z=366.5 [M+H]$^+$, $^1$H NMR (400 MHz, CDCl$_3$) δ 8.53 (s, 1H), 7.28 (d, J=7.7 Hz, 1H), 6.49-6.42 (m, 2H), 4.75 (s, 2H), 4.28 (s, 2H), 3.86 (s, 3H), 3.80 (s, 3H).

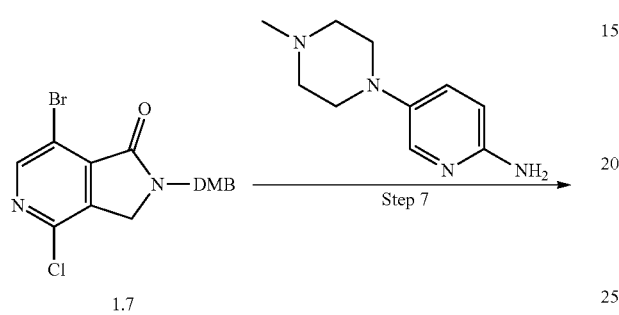

Step 7. 4-Chloro-2-(2,4-dimethoxybenzyl)-7-((5-(4-methylpiperazin-1-yl)pyridin-2-yl)amino)-2,3-dihydro-1H-pyrrolo[3,4-c]pyridin-1-one (1.8)

To a solution of 7-bromo-4-chloro-2-(2,4-dimethoxybenzyl)-2,3-dihydro-1H-pyrrolo[3,4-c]pyridin-1-one (1.7) (2 g, 5.03 mmol) in dry 1,4-dioxane (60 mL) was added Cs$_2$CO$_3$ (3.27 g, 10.06 mmol) followed by 5-(4-methylpiperazin-1-yl)pyridin-2-amine (AA2) (preparation described in WO2015131080, 1.06 g, 5.54 mmol). The mixture was purged with a N$_2$ stream for 10 min before Xantphos (350 mg, 0.604 mmol) and Pd$_2$(dba)$_3$ (461 mg, 0.503 mmol) were added. The mixture was degassed for 10 more min. The reaction was then stirred at 120° C. for 2 h. After cooling to RT, the reaction mixture was poured into saturated aqueous NH$_4$Cl solution (30 mL) and filtered through a Celite Pad. The mixture was extracted with ethyl acetate (2×25 mL). The combined organic phases were washed with brine (25 mL), dried over Na$_2$SO$_4$, filtered, and concentrated under reduced pressure. The crude product was purified by column chromatography (0-100% gradient elution EtOAc in isohexane) to afford the desired compound (1.8) (1.6 g, 62%) as a dark orange solid. m/z=478.1 [M+H]$^+$, $^1$H NMR (400 MHz, DMSO): δ 9.41-9.38 (m, 1H), 8.53 (d, J=9.1 Hz, 1H), 8.05-8.02 (m, 1H), 7.52-7.46 (m, 1H), 7.08 (d, J=8.8 Hz, 1H), 4.75 (s, 2H), 3.19-3.13 (m, 4H), 2.53-2.47 (m, 4H), 2.28 (s, 3H), 1.59 (s, 9H).

Step 8. tert-Butyl 3-(2-(2,4-dimethoxybenzyl)-7-((5-(4-methylpiperazin-1-yl)pyridin-2-yl)amino)-1-oxo-2,3-dihydro-1H-pyrrolo[3,4-c]pyridin-4-yl)-1H-pyrrolo[2,3-b]pyridine-1-carboxylate (1.9)

A mixture of 4-chloro-2-(2,4-dimethoxybenzyl)-7-((5-(4-methylpiperazin-1-yl)pyridin-2-yl)amino)-2,3-dihydro-1H-pyrrolo[3,4-c]pyridin-1-one (1.8) (250 mg, 0.491 mmol), 1-BOC-7-azaindole-3-boronic acid pinacol ester (203 mg, 0.589 mmol), Pd(dppf)Cl$_2$ 1:1 DCM complex (20 mg, 5 mol %) and Cs$_2$CO$_3$ (2M solution, 614 µL, 1.23 mmol) in 1,4-dioxane (5 mL) was degassed, purged with nitrogen and heated at 100° C. for 6 h. The reaction mixture was diluted with EtOAc (20 mL), washed with water (15 mL) and brine (15 mL), dried over Na$_2$SO$_4$, and concentrated in vacuo. The residue was purified by silica gel chromatography (0-10% gradient elution MeOH in DCM) to leave the title compound (1.9) (290 mg, 85%) as an orange residue which was used directly in next step.

Step 9. 7-((5-(4-Methylpiperazin-1-yl)pyridin-2-yl)amino)-4-(1H-pyrrolo[2,3-b]pyridin-3-yl)-2,3-dihydro-1H-pyrrolo[3,4-c]pyridin-1-one (I-6)

A 5 mL microwave vial was charged with tert-butyl 3-(2-(2,4-dimethoxybenzyl)-7-((5-(4-methylpiperazin-1-yl)pyridin-2-yl)amino)-1-oxo-2,3-dihydro-1H-pyrrolo[3,4-c]pyridin-4-yl)-1H-pyrrolo[2,3-b]pyridine-1-carboxylate (1.9) (289 mg, 0.418 mmol) and TFA (5 mL) and heated at 160° C. for 10 mins in a Biotage Initiator® microwave. The mixture was concentrated under vacuum and triturated with NH$_4$OH. The precipitate was collected by filtration, washed with water and air dried. The crude product was purified by preparative HPLC to afford the title compound (I-6) (92 mg, 50%) as an orange solid. m/z=441.2 [M+H]$^+$, $^1$H NMR (400 MHz, DMSO): δ 12.11-12.06 (m, 1H), 9.87 (s, 1H), 9.34 (s, 1H), 9.21 (s, 1H), 8.94 (d, J=7.1 Hz, 1H), 8.35 (d, J=3.0 Hz, 1H), 8.08 (d, J=2.8 Hz, 1H), 7.89 (d, J=2.3 Hz, 1H), 7.50 (dd, J=2.8, 8.8 Hz, 1H), 7.23 (dd, J=4.5, 7.8 Hz, 1H), 7.05 (d, J=8.8 Hz, 1H), 4.78 (s, 2H), 3.21 (dd, J=6.4, 6.4 Hz, 4H), 2.70-2.63 (m, 4H), 2.38 (s, 3H).

Example 2. Method C

Synthesis of 4-(Imidazo[1,2-a]pyridin-3-yl)-7-((5-(4-methylpiperazin-1-yl)pyridin-2-yl)amino)-2,3-dihydro-1H-pyrrolo[3,4-c]pyridin-1-one (I-56)

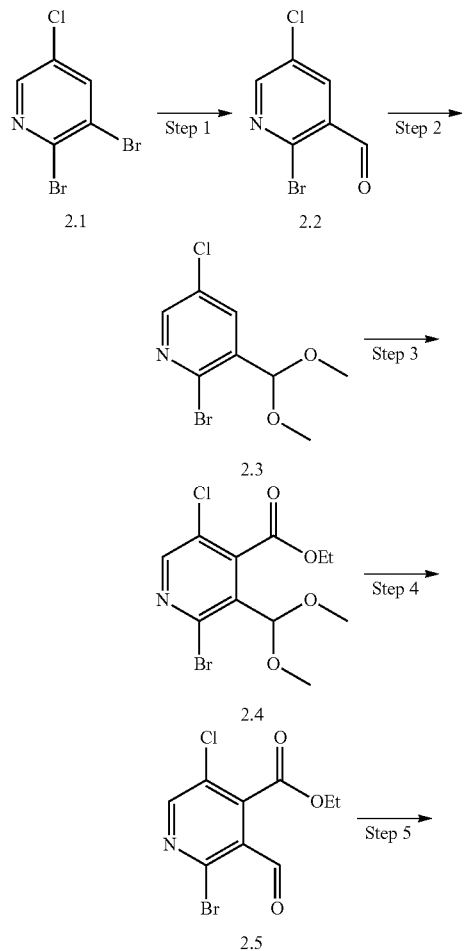

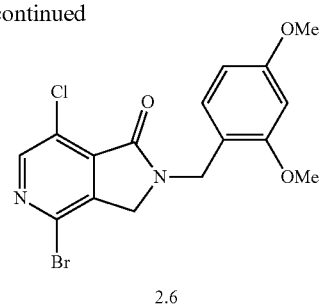

Step 1. 2-Bromo-5-chloronicotinaldehyde (2.2)

A solution of 2,3-dibromo-5-chloropyridine (2.1) (25.29 g, 93.21 mmol) in THF (200 mL) at −40° C. under a nitrogen atmosphere was treated dropwise with isopropyl magnesium chloride (2M in THF, 50.8 mL, 101.59 mmol) and stirred for 1 h. DMF (21.1 mL, 272.20 mmol) was added dropwise and the mixture allowed to warm to RT over 30 min. The reaction was quenched with 1M HCl and extracted into tert-butyl methyl ether (3×). The combined extracts were washed with saturated aqueous NaHCO$_3$ solution, water, and brine, dried over Na$_2$SO$_4$, filtered, and concentrated in vacuo to afford the title compound (2.2) (20.35 g, 99%) as a beige solid. m/z=221.2 [M+H]$^+$, $^1$H NMR (400 MHz, CDCl$_3$): δ 10.29 (s, 1H), 8.54 (d, J=2.8 Hz, 1H), 8.13 (d, J=2.8 Hz, 1H).

Step 2. 2-Bromo-5-chloronicotinaldehyde (2.3)

A mixture of 2-bromo-5-chloronicotinaldehyde (2.2) (25.40 g, 115.22 mmol), triethyl orthoformate (37.8 mL, 345.66 mmol) and p-toluene sulfonic acid monohydrate (2.19 g, 11.52 mmol) in methanol (300 mL) was heated at reflux for 18 h. The cooled mixture was concentrated in vacuo and passed through a silica pad eluting with 20% EtOAc in iso-hexane to leave the title compound (2.3) (28.61 g, 93%) as a yellow oil. m/z=267.2 [M+H]$^+$, $^1$H NMR (400 MHz, CDCl$_3$): δ 8.32 (d, J=2.5 Hz, 1H), 7.89 (d, J=2.5 Hz, 1H), 5.47 (s, 1H), 3.41 (s, 6H).

Step 3. Ethyl 2-bromo-5-chloro-3-(dimethoxymethyl)isonicotinate (2.4)

A solution of LDA (2M in THF/heptane/ethylbenzene, 69.8 mL, 139.5 mmol) in dry THF (130 mL) at −50° C. under a nitrogen atmosphere was treated dropwise with a solution of 2-bromo-5-chloro-3-(dimethoxymethyl)pyridine (2.3) (28.60 g, 107.31 mmol) in dry THF (70 mL) over 40 min. After the addition, the mixture was stirred for an additional 40 min. Ethyl chloroformate (30.7 mL, 321.93 mmol) was added dropwise and stirring continued at −50° C. for 40 min. The reaction was quenched with saturated aqueous NaHCO$_3$ solution and extracted into EtOAc (3×). The combined extracts were washed with brine, dried over Na$_2$SO$_4$, filtered, and concentrated in vacuo. The residue was purified by silica gel chromatography (0-30% gradient elution EtOAc in iso-hexane) to afford the title compound (2.4) (26.51 g, 73%) as a pale yellow oil. m/z=339.6 [M+H]$^+$, $^1$H NMR (400 MHz, CDCl$_3$): δ 8.38 (s, 1H), 5.50-5.49 (m, 1H), 4.42 (q, J=7.2 Hz, 2H), 3.43-3.42 (m, 6H), 1.40 (dd, J=7.2, 7.2 Hz, 3H).

Step 4. Ethyl 2-bromo-5-chloro-3-formylisonicotinate (2.5)

A mixture of ethyl 2-bromo-5-chloro-3-(dimethoxymethyl)isonicotinate (2.4) (26.50 g, 78.27 mmol) and lithium tetrafluoroborate (10.27 g, 109.57 mmol) acetonitrile (250 mL) and water (15 mL) was heated at 75° C. for 18 h. The cooled mixture was concentrated in vacuo, taken up in EtOAc, washed with saturated aqueous NaHCO$_3$ solution, water, and brine, dried over Na$_2$SO$_4$, filtered, and concentrated in vacuo. The residue was purified by silica gel chromatography (0-30% gradient elution EtOAc in isohexane) to afford the title compound (15) (13.94 g, 61%) as a yellow oil. m/z=293.5 [M+H]$^+$, $^1$H NMR (400 MHz, DMSO): δ 8.62 (s, 1H), 7.21 (d, J=8.3 Hz, 1H), 4.68 (s, 2H), 3.87 (s, 3H).

Step 5. 4-Bromo-7-chloro-2-(2,4-dimethoxybenzyl)-2,3-dihydro-1H-pyrrolo[3,4-c]pyridin-1-one (2.6)

To a solution of ethyl 2-bromo-5-chloro-3-formylisonicotinate (2.5) (13.93 g, 47.62 mmol) and acetic acid (8.18 mL, 142.87 mmol) in DCM (200 mL) was added MgSO$_4$ followed by 2,4-dimethoxybenzylamine (7.87 mL, 52.38 mmol) and the mixture stirred at RT for 18 h. Sodium borohydride (2.70 g, 71.43 mmol) was added portion wise and the reaction was stirred for 2 h. The mixture was diluted with DCM, washed with saturated aqueous NaHCO$_3$ solution, water, and brine, dried over Na$_2$SO$_4$, filtered, and concentrated in vacuo. The residue was purified by silica gel chromatography (0-50% gradient elution EtOAc in DCM). The yellow residue obtained was triturated with diethyl ether to leave the title compound (2.6) (7.12 g, 38%) as a white solid. m/z=398.6 [M+H]$^+$, $^1$H NMR (400 MHz, DMSO): δ 8.61 (s, 1H), 7.20 (d, J=8.3 Hz, 1H), 6.64 (d, J=2.3 Hz, 1H), 6.54 (dd, J=2.1, 8.2 Hz, 1H), 4.67 (s, 2H), 4.36 (s, 2H), 3.87 (s, 3H), 3.81 (s, 3H).

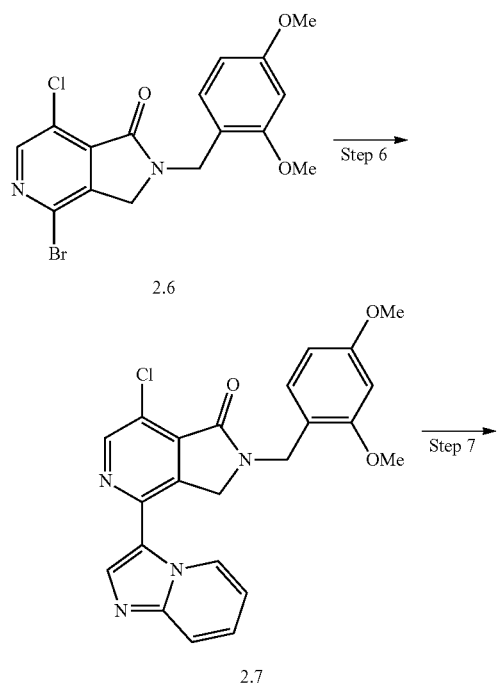

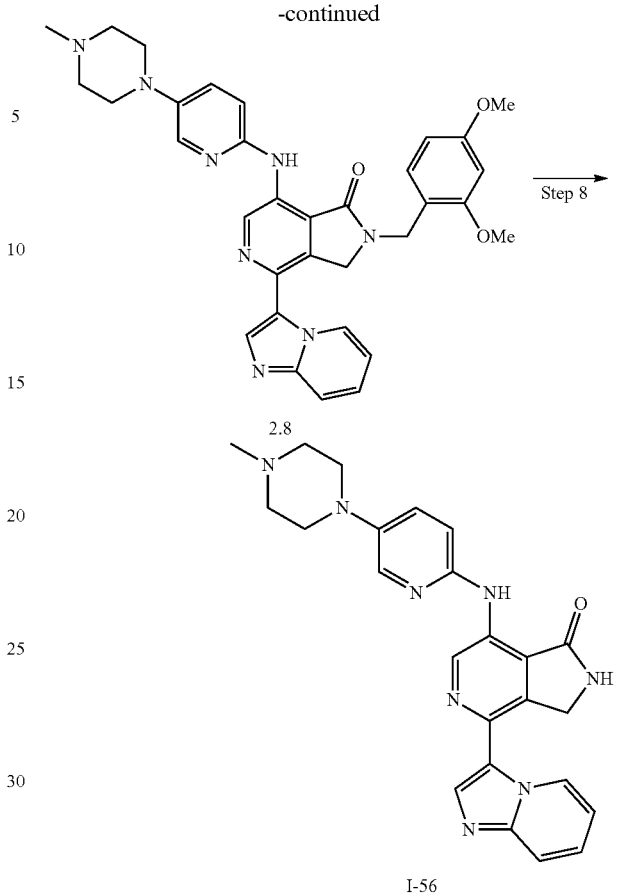

Step 6: 7-chloro-2-(2,4-dimethoxybenzyl)-4-(imidazo[1,2-a]pyridin-3-yl)-2,3-dihydro-1H-pyrrolo[3,4-c]pyridin-1-one (2.7)

A mixture of 4-bromo-7-chloro-2-(2,4-dimethoxybenzyl)-2,3-dihydro-1H-pyrrolo[3,4-c]pyridin-1-one (2.6) (300 mg, 0.756 mmol), 3-(4,4,5,5-tetramethyl-1,3,2-dioxaborolan-2-yl)imidazo[1,2-a]pyridine (369 mg, 7.57 mmol), Pd(dppf)Cl$_2$ 1:1 DCM complex (62 mg, 10 mol %) and Cs$_2$CO$_3$ (2M solution, 950 1.89 mmol) in 1,4-dioxane (10 mL) was degassed, purged with nitrogen and heated at 100° C. for 4 h. The reaction mixture was diluted with EtOAc, washed with water and brine, dried over Na$_2$SO$_4$, and concentrated in vacuo. The residue was purified by silica gel chromatography (0-100% gradient elution EtOAc in DCM) to leave the title compound (2.7) (168 mg, 51%) as a light brown solid.

Alternatively, Step 6 was carried out using the procedure described below:

A mixture of 4-bromo-7-chloro-2-(2,4-dimethoxybenzyl)-2,3-dihydro-1H-pyrrolo[3,4-c]pyridin-1-one (2.6) (500 mg, 1.26 mmol), 3-(tributylstannyl)imidazo[1,2-a]pyridine (399 mg, 1.64 mmol) and Pd(PPh$_3$)$_4$ (73 mg, 0.063 mmol) in 1,4-dioxane (10 mL) was degassed, purged with nitrogen and heated at 90° C. for 4 h. The precipitate was collected from the cooled reaction mixture, washed with diethyl ether, and dried to leave the title compound (2.7) (298 mg, 54%) as an off-white solid. $^1$H NMR (400 MHz, DMSO): δ 9.79 (d, J=6.9 Hz, 1H), 8.83 (s, 1H), 8.18-8.14 (m, 1H), 7.81-7.75 (m, 1H), 7.54-7.46 (m, 1H), 7.19-7.13 (m, 2H), 6.61 (s, 1H), 6.53-6.48 (m, 1H), 4.77 (s, 2H), 4.69 (s, 2H), 3.85 (s, 3H), 3.77 (s, 3H).

Step 7 and 8 were carried out following representative procedures described in Example 1, and characterization of 1-56 is provided in Example 21.

Example 3. Method D

Synthesis of 7-((5-(4-methylpiperazin-1-yl)pyridin-2-yl)amino)-4-(1H-pyrrolo[3,2-b]pyridin-3-yl)isoindolin-1-one (I-26)

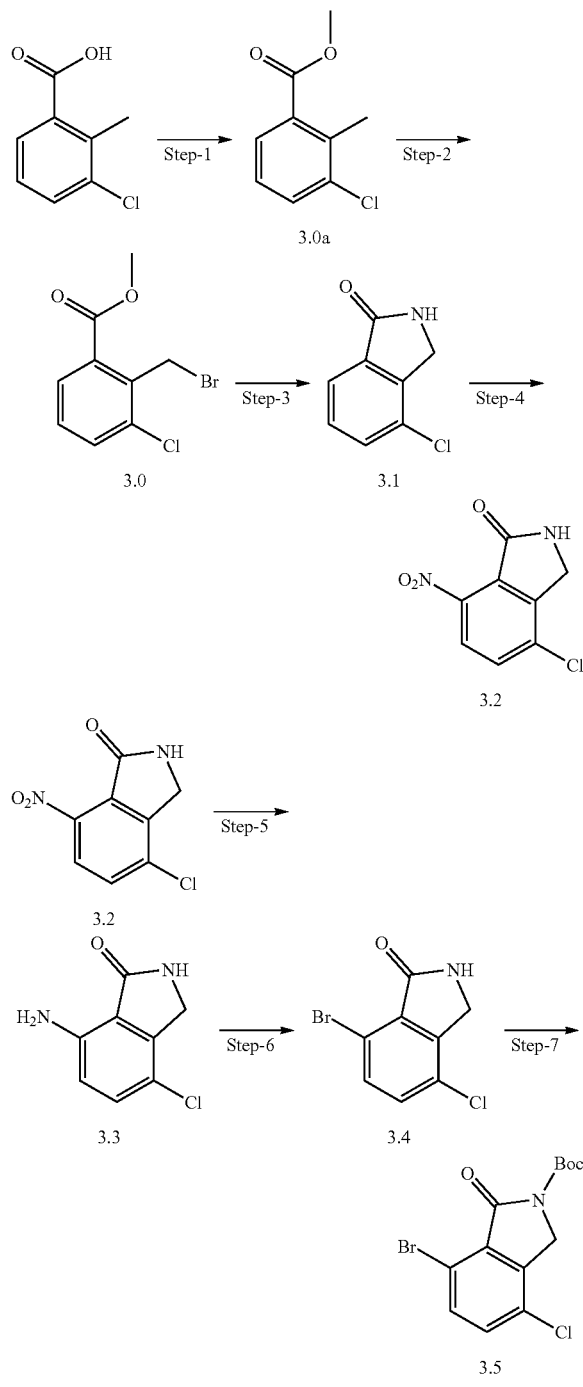

Step-1 Synthesis of Methyl 3-chloro-2-methylbenzoate (3.0a)

To a mixture of 3-chloro-2-methylbenzoic acid (300 g, 1.75 mol) and potassium carbonate (606 g, 4.39 mol) in DMF (2500 mL) were added iodomethane (275 g, 1.93 mol). After stirring at RT for 16 h, the reaction was quenched with water and extracted with ethyl acetate. The combined extracts were washed with brine, dried over sodium sulfate, and concentrated under vacuum to afford title compound as light brown liquid (3.0a) (320 g, yield: 98.16%). MS (ES): m/z 185.7 [M+1]$^+$ Step-2 Synthesis of Methyl 2-(bromomethyl)-3-chlorobenzoate (3.0)

To a solution of methyl 3-chloro-2-methylbenzoate (3.0a) (320 g, 1.72 mol) in carbon tetrachloride (3000 mL) were added N-bromosuccinimide (336.2 g, 1.88 mol) and benzoyl peroxide (0.798 g, 0.0032 mol) at RT. After stirring at 90° C. for 4 h, the reaction was poured into ice/water (~5000 mL) water and extracted with ethyl acetate. The combined extracts were washed with brine, dried over sodium sulfate, and concentrated under vacuum to afford title compound as light brown liquid (3.0) (400 g, yield: 87.71%). MS (ES): m/z 263.5, 265.6 [M]$^+$, [M+2]$^+$ Step-3 Synthesis of 4-chloroisoindolin-1-one (3.1)

To a solution of methyl 2-(bromomethyl)-3-chlorobenzoate (3.0) (400 g, 1.51 mol), in methanol (3000 mL) was bubbled NH$_3$ for 1 h at 0° C. After stirring at RT for 16 h, the reaction was concentrated under vacuum and diluted with water. The resulting solid compound was filtered and dried under vacuum to obtained title compound as of white solid (3.1) (200 g, 78.74%). MS (ES): m/z 168.6 [M+1]$^+$ Step-4 Synthesis of 4-Chloro-7-nitroisoindolin-1-one (3.2)

To a solution of 4-chloro-isoindolin-1-one (3.1) (200 g, 1.19 mol) in c·H$_2$SO$_4$ (1200 mL) at −10° C. was added dropwise with HNO$_3$ (69-72% aq) (120 mL). After stirring cold for 2 h then warming to ambient temperature for 2 h, the reaction was poured onto ice water (~4000 mL). The precipitate was collected by filtration, washed with water, and dried to afford a pale yellow solid (3.2) (245 g, 96.84%). m/z=213.5 [M+H]$^+$, $^1$H NMR (400 MHz, DMSO): δ 9.17 (s, 1H), 7.98-7.90 (m, 2H), 4.47-4.46 (m, 2H).

Step-5 Synthesis of 7-Amino-4-chloroisoindolin-1-one (3.3)

To a solution of 4-chloro-7-nitroisoindolin-1-one 2 (3.2) (245 g, 1.15 mol) in EtOH (2500 mL) and water (500 mL) were added iron powder (322 g, 5.75 mol) and ammonium chloride (372.67 g, 6.90 mol). After mechanically stirring at reflux for 2 h, the mixture was filtered through Celite washing the filter cake with EtOAc and DCM (~5 L). The filtrate was concentrated under vacuum to low volume whereby a solid precipitated from solution. The precipitate was collected by filtration, washed with water, and dried under vacuum to afford the title compound as a brown solid (3.3) (200 g, 95.23%). m/z=183.2 [M+H]$^+$, $^1$H NMR (400 MHz, DMSO): δ 8.38 (s, 1H), 7.24-7.21 (m, 1H), 6.63-6.59 (m, 1H), 6.18 (s, 2H), 4.23 (s, 2H).

Step-6 Synthesis of 4-Chloro-7-bromoisoindolin-1-one (3.4)

To a suspension of 7-amino-4-chloroisoindolin-1-one (3.3) (100 g, 0.547 mol) in HBr (47%, 500 mL) at −10° C. was added a solution of sodium nitrite (75.5 g, 1.09 mol) in water (500 mL). After stirring cold for 60 min, copper (I) bromide (86.04 g, 0.60 mol) was added. After stirring at 80° C. for 40 min, the reaction mixture was poured onto ice water. The precipitate collected by filtration, washed with water, and dried under vacuum to afford the title compound as a light brown solid (3.4) (120 g, 89.55%). m/z=247.5 [M+H]$^+$, $^1$H NMR (400 MHz, DMSO): δ 9.02-8.96 (m, 1H), 7.76-7.71 (m, 1H), 7.66-7.62 (m, 1H), 4.39-4.37 (m, 2H).

Step-7 Synthesis of tert-Butyl 7-bromo-4-chloro-1-oxoisoindoline-2-carboxylate (3.5)

To a solution of 4-chloro-7-bromoisoindolin-1-one (3.4) (120 g, 0.487 mol) in THF at 0° C. (1500 mL) were added di-tert-butyl dicarbonate (159 g, 0.731 mol) and DMAP (74 g, 0.60 mol). After stirring at RT for 4 h, the mixture was diluted with EtOAc, washed with water and brine dried over Na$_2$SO$_4$, and concentrated in vacuum. The residue was purified by silica gel chromatography (gradient: 0-2% EtOAc in DCM) to afford the title compound as a white solid (3.5) (130 g, 77.38%). MS (ES): m/z 346.6, 348.6 [M]$^+$, [M+2]$^+$, $^1$H NMR (400 MHz, CDCl$_3$): δ 7.62-7.58 (m, 1H), 7.45-7.41 (m, 1H), 4.68 (s, 2H), 1.16 (s, 9H).

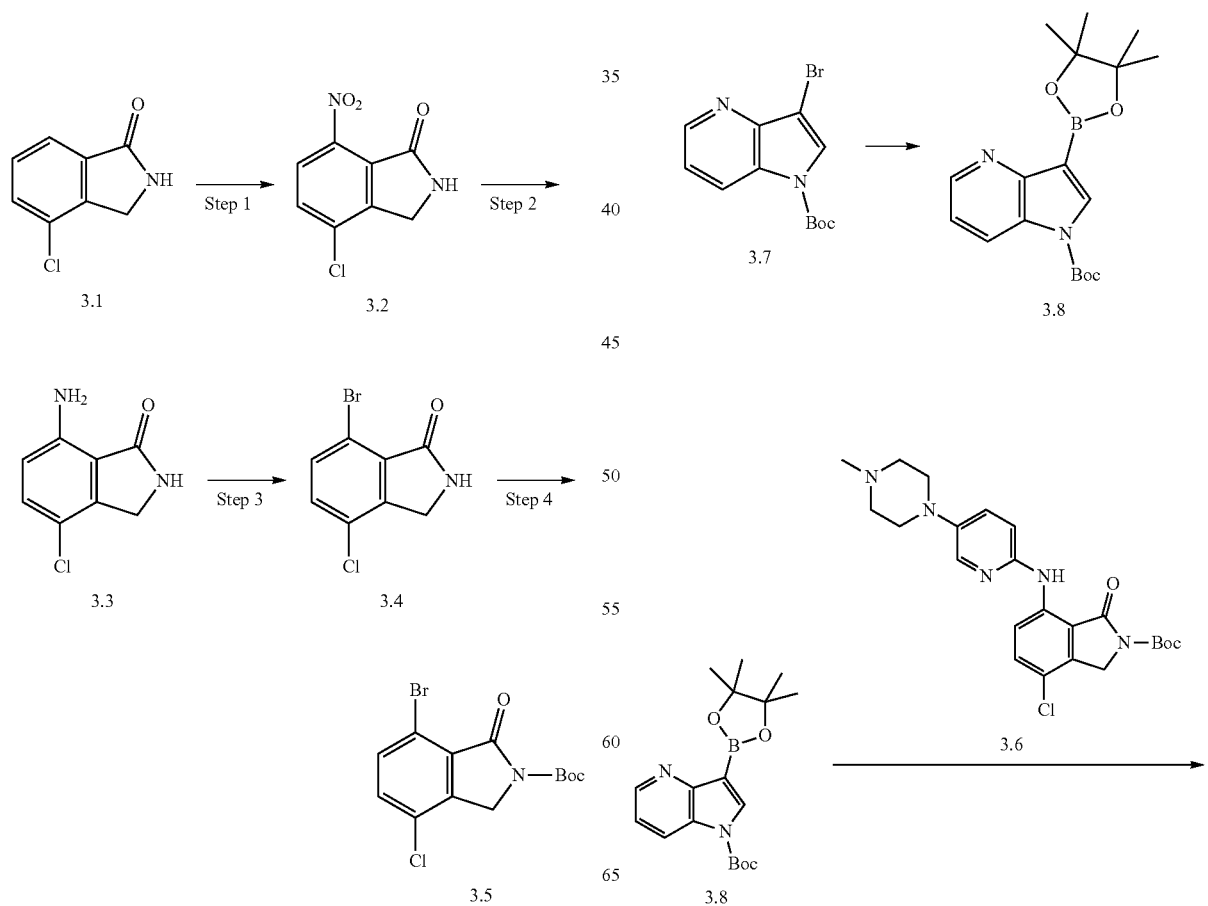

-continued

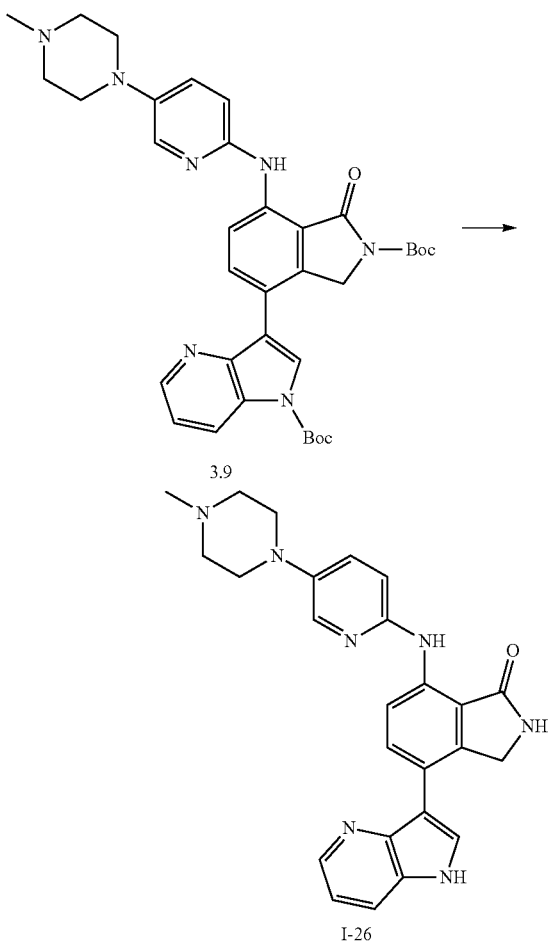

Step 5. Tert-Butyl 4-chloro-7-((5-(4-methylpiperazin-1-yl)pyridin-2-yl)amino)-1-oxoisoindoline-2-carboxylate (3.6)

A mixture of tert-butyl 7-bromo-4-chloro-1-oxoisoindoline-2-carboxylate (3.5) (2 g, 5.77 mmol), tert-butyl 4-(6-aminopyridin-3-yl)piperazine-1-carboxylate (preparation described in WO2015131080, 1.39 g, 7.21 mmol), $Cs_2CO_3$ (5.64 g, 17.31 mmol) and Xantphos (0.40 g, 0.692 mmol) was stirred in dry 1,4-dioxane (8 mL) and degassed under $N_2$ stream. After 15 mins $Pd_2(dba)_3$ (0.53 g, 0.577 mmol) was added and the reaction was heated at 110° C. and stirred for 6 h. The reaction mixture was cooled to RT and then diluted ethyl acetate (25 mL) and water (20 mL). The organic layer was collected, and the aqueous phase was extracted with ethyl acetate (2×25 mL), and the combined organic extracts were washed with brine (20 mL), dried over $Na_2SO_4$, filtered, and concentrated under reduced pressure. The residue was purified by column chromatography (0-20% gradient elution MeOH in DCM). The residue obtained was then triturated with diethyl ether and the resulting solid was collected by filtration to afford the title compound (3.6) (2.09 g, 79%) as a beige solid. m/z=458.2 [M+H]$^+$, $^1$H NMR (400 MHz, DMSO): δ 9.41-9.38 (m, 1H), 8.53 (d, J=9.1 Hz, 1H), 8.05-8.02 (m, 1H), 7.66-7.61 (m, 1H), 7.52-7.46 (m, 1H), 7.08 (d, J=8.8 Hz, 1H), 4.75 (s, 2H), 3.19-3.13 (m, 4H), 2.53-2.47 (m, 4H), 2.28 (s, 3H), 1.59 (s, 9H).

Step 6. tert-butyl 3-(4,4,5,5-tetramethyl-1,3,2-dioxaborolan-2-yl)-1H-pyrrolo[3,2-b]pyridine-1-carboxylate (3.8)

To a degassed solution of tert-butyl 3-bromo-1H-pyrrolo[3,2-b]pyridine-1-carboxylate (3.7) (300 mg, 1.01 mmol) in 1,4-dioxane (6 mL) was added KOAc (297 mg, 3.03 mmol) and bis(pinacolato)diboron (282 mg, 1.11 mmol). The solution was purged with a $N_2$ stream for 30 min before Pd(dppf)$Cl_2$ (37 mg, 0.051 mmol) was added, and the reaction was then stirred in a sealed tube at 125° C. overnight. The reaction mixture was cooled to RT and then diluted ethyl acetate (25 mL) and water (20 mL). The organic layer was collected, and the aqueous phase was extracted with ethyl acetate (2×25 mL). The combined organic layers were washed with brine (10 mL), then passed through a hydrophobic frit and concentrated under reduced pressure. The crude compound (3.8) was taken forwards to the next step without purification.

Step 7. Tert-Butyl 3-(2-(tert-butoxycarbonyl)-7-((5-(4-methylpiperazin-1-yl)pyridin-2-yl)amino)-1-oxoisoindolin-4-yl)-1H-pyrrolo[3,2-b]pyridine-1-carboxylate (3.9)

A microwave vial was charged with tert-butyl 4-chloro-7-((5-(4-methylpiperazin-1-yl)pyridin-2-yl)amino)-1-oxoisoindoline-2-carboxylate (3.6) (100 mg, 0.218 mmol), tert-butyl 3-(4,4,5,5-tetramethyl-1,3,2-dioxaborolan-2-yl)-1H-pyrrolo[3,2-b]pyridine-1-carboxylate (3.8) (113 mg, 0.328 mmol) and 1,4-dioxane/water (3 mL, 5:1 solution). $K_3PO_4·H_2O$ (185 mg, 0.873 mmol) was added and the mixture was stirred at RT and purged with $N_2$ for 15 mins before the catalyst XPhos Pd G2 (3.4 mg, 10% mmol) was added. The reaction was heated at 150° C. for 15 mins in a Biotage Initiator® microwave. The mixture was diluted with EtOAc (10 mL) and washed with water (10 mL), saturated aqueous NaHCO$_3$ solution (10 mL) and brine (10 mL), dried over MgSO$_4$, filtered, and concentrated under reduced pressure. The crude compound (3.9) was taken forwards to the next step without purification.

Step 8. 7-((5-(4-methylpiperazin-1-yl)pyridin-2-yl)amino)-4-(1H-pyrrolo[3,2-b]pyridin-3-yl)isoindolin-1-one (I-26)

The residue (3.9) was dissolved in DCM (3 mL) and treated with TFA (100 eq., 1.5 mL). The reaction was stirred for 30 mins at RT, and then concentrated under vacuum and triturated with 7N methanolic ammonia (2×3 mL). The crude product was purified by preparative HPLC to afford the desired compound (I-26) (10 mg, 15%) as a pale yellow solid. m/z=440.5 [M+H]$^+$, $^1$H NMR (400 MHz, DMSO): δ 11.60 (d, J=2.5 Hz, 1H), 9.81 (s, 1H), 8.75 (s, 1H), 8.49-8.41 (m, 3H), 8.01 (d, J=2.9 Hz, 1H), 7.91-7.84 (m, 2H), 7.45 (dd, J=3.0, 8.9 Hz, 1H), 7.20 (dd, J=4.5, 8.2 Hz, 1H), 6.98-6.94 (m, 1H), 4.63 (s, 2H), 3.20-3.14 (m, 4H), 2.71-2.68 (m, 4H), 2.40 (s, 3H).

Example 4. Method E

Synthesis of 7-((5-(4-methylpiperazin-1-yl)pyridin-2-yl)amino)-4-(1H-pyrrolo[3,2-c]pyridin-3-yl)isoindolin-1-one (I-24)

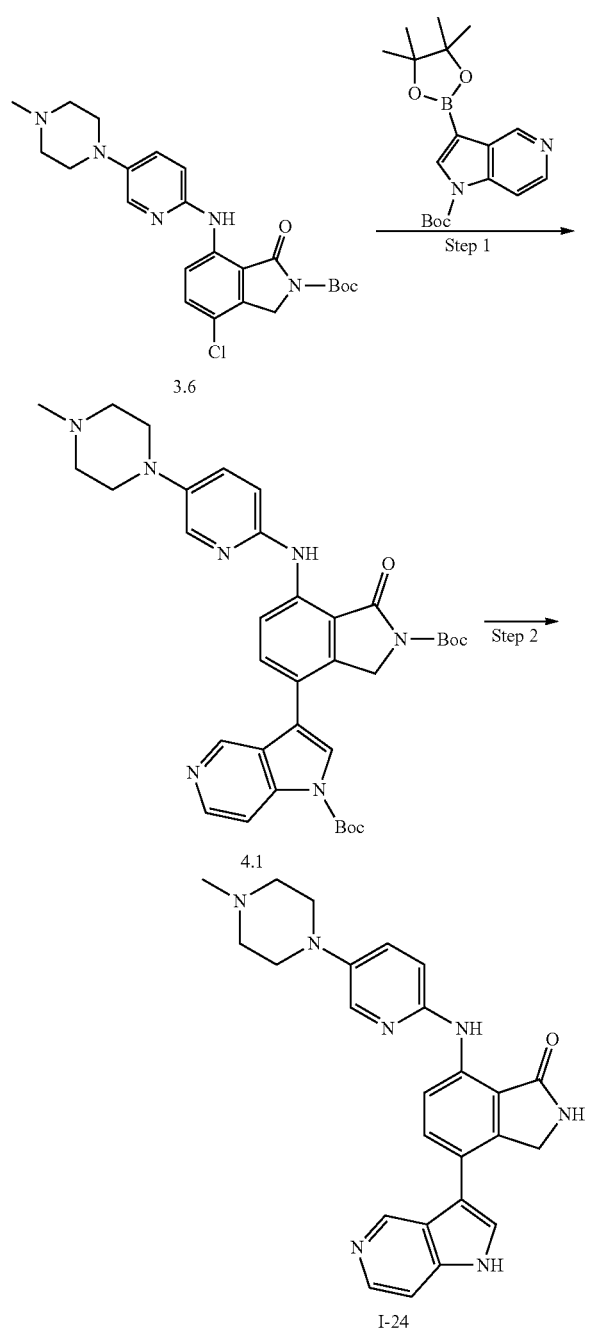

Step 1: Tert-Butyl 3-(2-(tert-butoxycarbonyl)-7-((5-(4-methylpiperazin-1-yl)pyridin-2-yl)amino)-1-oxoisoindolin-4-yl)-1H-pyrrolo[3,2-c]pyridine-1-carboxylate (4.1)

tert-Butyl 3-(2-(tert-butoxycarbonyl)-7-((5-(4-methylpiperazin-1-yl)pyridin-2-yl)amino)-1-oxoisoindolin-4-yl)-1H-pyrrolo[3,2-c]pyridine-1-carboxylate (4.1) was prepared from tert-butyl 4-chloro-7-((5-(4-methylpiperazin-1-yl)pyridin-2-yl)amino)-1-oxoisoindoline-2-carboxylate (3.6) and tert-butyl 3-(4,4,5,5-tetramethyl-1,3,2-dioxaborolan-2-yl)-1H-pyrrolo[3,2-c]pyridine-1-carboxylate in a similar fashion to that described for 7-((5-(4-methylpiperazin-1-yl)pyridin-2-yl)amino)-4-(1H-pyrrolo[3,2-b]pyridin-3-yl)isoindolin-1-one (I-26).

Step 2: 7-((5-(4-methylpiperazin-1-yl)pyridin-2-yl)amino)-4-(1H-pyrrolo[3,2-c]pyridin-3-yl)isoindolin-1-one (I-24)

Compound 4.1 was diluted with DCM and treated with TFA (100 eq.). The reaction was stirred for 30 mins at rt before the mixture was concentrated under vacuum and triturated with methanolic ammonia. Purified by prep. HPLC to afford the desired compound I-24. m/z=440 [M+H]$^+$, $^1$H NMR (400 MHz, DMSO): δ 12.16-12.08 (m, 1H), 9.86 (s, 1H), 8.80 (s, 1H), 8.57-8.54 (m, 1H), 8.31 (d, J=6.0 Hz, 1H), 8.15 (s, 1H), 8.05 (d, J=2.9 Hz, 1H), 7.89-7.82 (m, 2H), 7.61 (d, J=5.9 Hz, 1H), 7.49 (dd, J=3.0, 9.0 Hz, 1H), 7.00-6.97 (m, 1H), 4.56-4.54 (m, 2H), 3.20-3.14 (m, 4H), 2.71-2.68 (m, 4H), 2.62 (s, 3H).

Example 5. Method F

Synthesis of 4-(imidazo[1,2-a]pyridin-3-yl)-7-((5-(4-methylpiperazin-1-yl)pyridin-2-yl)amino)isoindolin-1-one (I-39)

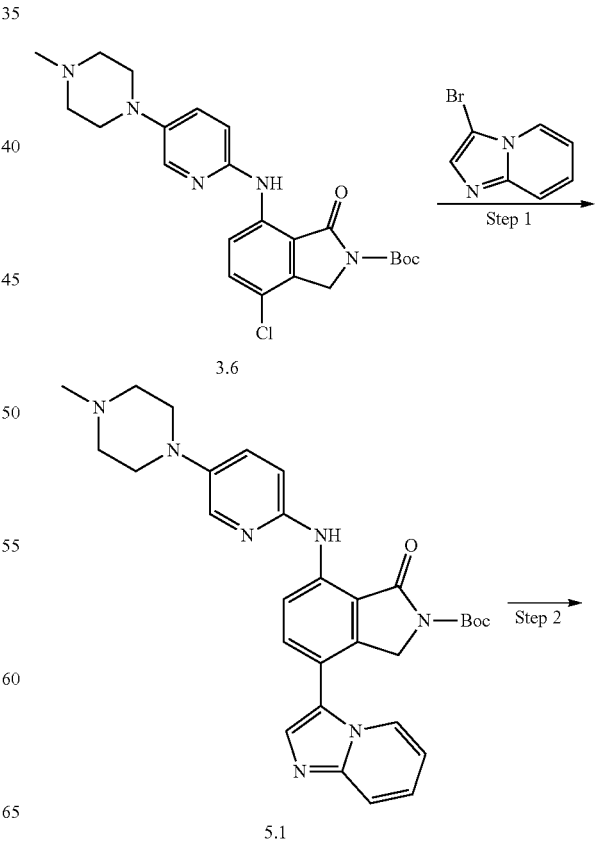

-continued

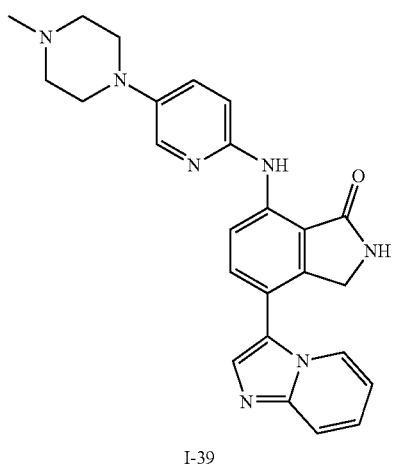

I-39

Step 1: Tert-Butyl 4-(imidazo[1,2-a]pyridin-3-yl)-7-((5-(4-methylpiperazin-1-yl)pyridin-2-yl)amino)-1-oxoisoindoline-2-carboxylate (5.1)

A 20 mL microwave vial was charged with 3.6 (150 mg, 0.328 mmol), bis(pinacolato)diboron (108 mg, 0.426 mmol), XPhos Pd G2 (2.6 mg, 0.003 mmol), XPhos (1.55 mg, 0.003 mmol), solid K$_3$PO$_4$ (190 mg, 0.893 mmol) and EtOH (12 mL). The mixture was degassed, purged with N$_2$, and stirred at RT overnight. 3-Bromoimidazo[1,2-b]pyridine, 3M K$_3$PO$_4$ (330 mL, 0.983 mmol) and a portion of XPhos Pd G2 (2.6 mg, 0.003 mmol) and XPhos (1.55 mg, 0.003 mmol) were added. The mixture degassed, purged with N$_2$, and heated at 40° C. overnight. Loaded onto Biotage-ISO-LUTE® HM-N and purified by silica gel chromatography (0-25% gradient elution MeOH in DCM) to afford 5.1 as a yellow solid which was used in the next reaction without analysis.

Step 2: 4-(imidazo[1,2-a]pyridin-3-yl)-7-((5-(4-methylpiperazin-1-yl)pyridin-2-yl)amino)isoindolin-1-one (I-39)

tert-butyl 4-(imidazo[1,2-a]pyridin-3-yl)-7-((5-(4-methylpiperazin-1-yl)pyridin-2-yl)amino)-1-oxoisoindoline-2-carboxylate (5.1) was diluted with DCM (5 mL) and treated with TFA (100 eq., 1.8 mL). The reaction was stirred for 30 mins at RT, and then concentrated under vacuum and triturated with 7N methanolic ammonia (2×3 mL). The residue was purified by preparative HPLC to afford the desired compound (I-39) (41.3 mg, 89%). m/z=440.2 [M+H]$^+$, $^1$H NMR (400 MHz, DMSO): δ 9.86 (s, 1H), 8.77 (s, 1H), 8.57 (d, J=8.5 Hz, 1H), 8.39 (d, J=6.9 Hz, 1H), 8.01 (d, J=3.0 Hz, 1H), 7.84 (s, 1H), 7.69 (dd, J=8.8, 15.1 Hz, 2H), 7.45 (dd, J=3.1, 9.0 Hz, 1H), 7.33-7.29 (m, 1H), 6.99-6.92 (m, 2H), 4.39 (s, 2H), 3.12 (dd, J=4.9, 4.9 Hz, 4H), 2.48 (dd, J=4.9, 4.9 Hz, 4H), 2.24 (s, 3H).

Example 6. Method G

Synthesis of 7-[[5-(4-methylpiperazin-1-yl)-2-pyridyl]amino]-4-(2-phenyl-1H-indol-3-yl)-2,3-dihydropyrrolo[3,4-c]pyridin-1-one (I-141)

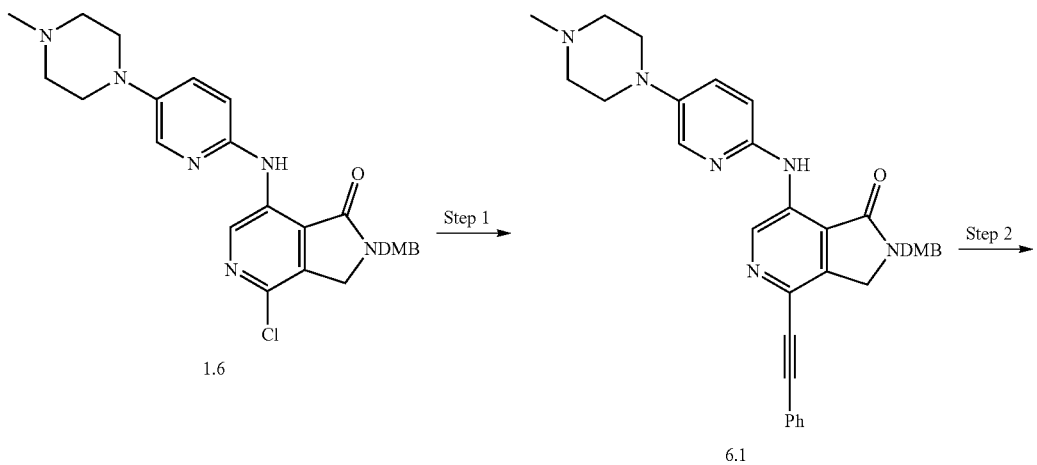

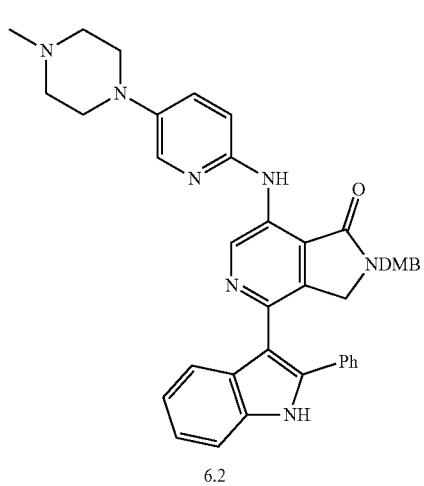

6.2

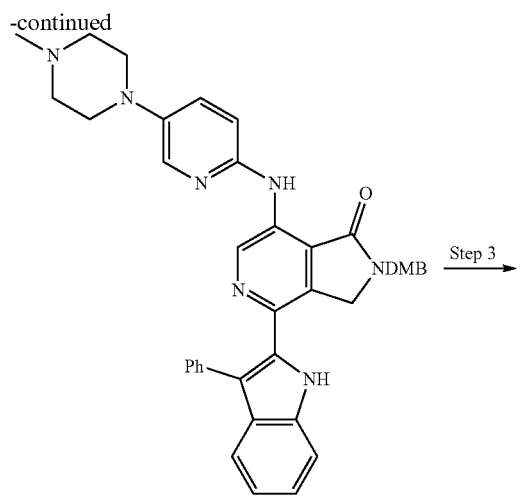

6.3

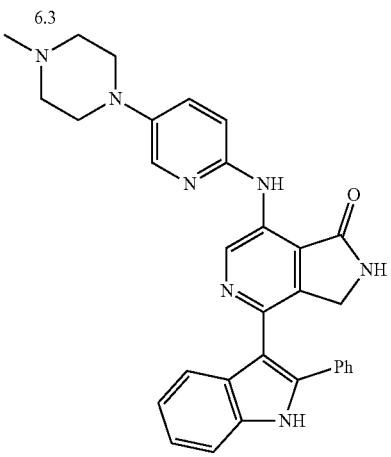

I-141

Step 1: 2-(2,4-dimethoxybenzyl)-7-((5-(4-methylpiperazin-1-yl)pyridin-2-yl)amino)-4-(phenylethynyl)-2,3-dihydro-1H-pyrrolo[3,4-c]pyridin-1-one (6.1)

A mixture of 1.6 (350 mg, 0.69 mmol), bis(triphenylphosphine)palladium(II) chloride (48 mg, 0.07 mmol) and copper (I) iodide (13 mg, 0.07 mmol) were placed under an atmosphere of nitrogen, then suspended in THF (1 mL) and acetonitrile (2 mL). The mixture was treated with phenylacetylene (0.17 mL, 1.6 mmol) and trimethylamine (0.24 mL, 1.8 mmol), and heated at 90° C. for 16 h. The reaction was cooled to RT, charged with phenylacetylene (0.17 mL, 1.6 mmol), bis(triphenylphosphine)palladium(II) chloride (48 mg, 0.07 mmol) and copper(I) iodide (13 mg, 0.07 mmol), and degassed with nitrogen. The reaction was then heated at 90° C. for 6.5 h, then cooled to RT, quenched with water (15 mL), and extracted into DCM (4×20 mL). The combined organic layer was washed with brine (20 mL), passed through a hydrophobic frit, and concentrated under reduced pressure. The crude material was purified by silica gel chromatography eluting with 0-20% 7N $NH_3$ in MeOH/EtOAc to afford 6.1 (280 mg).

Step 2: 2-(2,4-dimethoxybenzyl)-7-((5-(4-methylpiperazin-1-yl)pyridin-2-yl)amino)-4-(2-phenyl-1H-indol-3-yl)-2,3-dihydro-1H-pyrrolo[3,4-c]pyridin-1-one (6.2) and 2-(2,4-dimethoxybenzyl)-7-((5-(4-methylpiperazin-1-yl)pyridin-2-yl)amino)-4-(3-phenyl-1H-indol-2-yl)-2,3-dihydro-1H-pyrrolo[3,4-c]pyridin-1-one (6.3)

A mixture of 2-iodoaniline (71 mg, 0.33 mmol), 6.1 (280 mg, 0.49 mmol), palladium(II) acetate (7 mg, 0.03 mmol), 1,1'-bis(diphenylphosphino)ferrocene (27 mg, 0.05 mmol), potassium acetate (159 mg, 1.6 mmol) and lithium chloride (14 mg, 0.33 mmol) was placed under an atmosphere of nitrogen. The mixture was dissolved in N-methyl-2-pyrrolidone (5 mL), and heated at 140° C. After 2 h, the reaction was charged with 2-iodoaniline (71 mg, 0.33 mmol) and heating continued at 140° C. After 1.5 h, the reaction was charged with palladium(II) acetate (7 mg, 0.03 mmol) and 1,1'-bis(diphenylphosphino)ferrocene (27 mg, 0.05 mmol) and heating continued at 140° C. After 45 min, the reaction was cooled to RT, and the reaction mixture filtered through Celite®, washed with 5% MeOH/EtOAc, and the filtrate was partitioned between 4% aqueous lithium chloride (100 mL) and 5% MeOH/EtOAc (3×75 mL). The combined organic layer was washed with brine (2×100 mL), passed through a hydrophobic filter and concentrated under reduced pressure. The residue was purified by silica gel chromatography eluting with 0-100% EtOAc/hexane, then 0-20% (7N NH₃ in MeOH)/EtOAc to afford 6.2 and 6.3 as a 1:1 mixture of inseparable regioisomers.

Step 3: 7-((5-(4-Methylpiperazin-1-yl)pyridin-2-yl) amino)-4-(2-phenyl-1H-indol-3-yl)-2,3-dihydro-1H-pyrrolo[3,4-c]pyridin-1-one (I-141)

A solution of the mixture of 6.1 and 6.2 (181 mg, 0.14 mmol) in TFA (3 mL) was heated by microwave at 150° C. for 15 min. The solvent was removed under reduced pressure, and the crude material was purified by preparative HPLC to afford I-141 (5 mg, 8%) as a solid. m/z 516.4 [M+H]⁺. ¹H NMR (400 MHz, DMSO): δ 11.67 (s, 1H), 9.85 (s, 1H), 9.25 (s, 1H), 8.70 (s, 1H), 8.04 (d, J=3.3 Hz, 1H), 7.53-7.37 (m, 7H), 7.33 (tt, J=1.9, 7.0 Hz, 1H), 7.17 (dt, J=1.2, 7.6 Hz, 1H), 7.06-7.01 (m, 2H), 3.66 (s, 2H), 3.24-3.17 (m, 4H), 2.81-2.72 (m, 4H), 2.43 (s, 3H).

Example 7. Method H

Synthesis of 5-chloro-7-[[5-(4-hydroxy-1-piperidyl)-2-pyridyl]amino]-4-(1-methylpyrrolo[2,3-b]pyridin-4-yl)isoindolin-1-one (I-190)

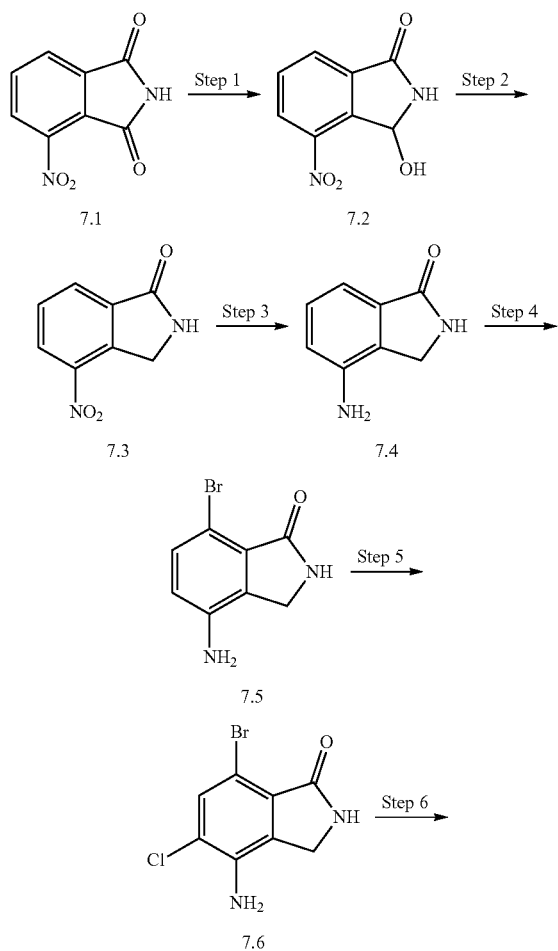

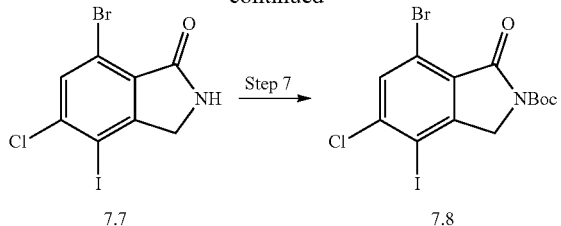

Step 1: 3-Hydroxy-4-nitroisoindolin-1-one (7.2)

A solution of 3-nitrophthalimide (7.1) (5.00 g, 26 mmol) in methanol (50 mL) and DCM (50 mL) was treated portion wise with sodium borohydride (0.98 g, 26 mmol), and the reaction was stirred at RT for 4 h. The reaction was quenched with saturated aqueous sodium bicarbonate (40 mL), stirred for 20 min, then the organic phase was separated. The aqueous phase was extracted with EtOAc (2×50 mL). The combine organic layer was washed with brine (50 mL), dried over MgSO₄, filtered, and concentrated under reduced pressure to afford 7.2 (3.51 g, 70%) as a yellow solid. Material used in next step without purification.

Step 2: 4-Nitroisoindolin-1-one (7.3)

A suspension of 7.2 (3.51 g, 18 mmol) in DCM (60 mL) was treated with TFA (12.5 mL, 163 mmol), and the resulting solution was stirred at RT for 10 min, followed by dropwise addition of triethylsilane (4.3 mL, 27 mmol), and the reaction was stirred at RT for 4 h. The solvent was removed under reduced pressure, and the residue taken up in MeOH, basified with 7N NH₃ in MeOH, and the solvent was again removed under reduced pressure. The crude material was purified by silica gel chromatography eluting with 0-100% EtOAc/hexane, and then 0-25% MeOH/EtOAc to afford 7.3 (5.46 g.). ¹H NMR (400 MHz, DMSO): δ 9.05 (s, 1H), 8.49 (dd, J=0.8, 8.1 Hz, 1H), 8.17 (dd, J=0.7, 7.5 Hz, 1H), 7.86 (t, J=7.8 Hz, 1H), 4.85 (s, 2H), 1.30-1.12 (m, OH).

Step 3: 4-Aminoisoindolin-1-one (7.4)

A solution of 7.3 (5.46 g, 31 mmol) in degassed ethanol (100 mL) was treated with 10% Pd/C (33 mg, 0.31 mmol), placed under an atmosphere of hydrogen, and stirred at RT for 4 h. The reaction mixture was then filtered over Celite® and the filtrate was concentrated under reduced pressure. The crude material was purified by silica gel chromatography eluting with 0-20% (7N NH₃ in MeOH)/EtOAc to afford 7.4 (1.57 g, 35%) as a yellow solid. ¹H NMR (400 MHz, DMSO): δ 8.35 (s, 1H), 7.16 (t, J=7.6 Hz, 1H), 6.86 (dd, J=0.9, 7.5 Hz, 1H), 6.76 (dd, J=1.0, 7.8 Hz, 1H), 5.38 (s, 2H), 4.13 (s, 2H).

Step 4: 4-Amino-7-bromoisoindolin-1-one (7.5)

A solution of 7.4 (1.57 g, 11 mmol) in methanol (25 mL) and THF (30 mL) was treated portion wise with N-bromosuccinimide (1.89 g, 11 mmol), and the reaction was stirred at RT for 1.5 h. The reaction was quenched with water (50 mL), then the organic solvent was removed under reduced pressure. The resulting precipitate was collected by filtration, washed with water, then azeotroped with toluene (20 mL). The crude material was purified by reverse phase chromatography using 0-50% Acetonitrile/(10 mM aqueous ammonium bicarbonate to afford 7.5 (735 mg, 31%) as an off-white solid.

Step 5: 4-Amino-7-bromo-5-chloroisoindolin-1-one (7.6)

A solution of 7.5 (735 mg, 3.2 mmol) in methanol (8 mL) and THF (9 mL) was treated portion wise with N-chlorosuccinimide (454 mg, 3.4 mmol), and the reaction was stirred at RT for 1 h, then heated at reflux for 1.5 h. The reaction was cooled to RT, and quenched with water (10 mL), then the organic solvent was removed under reduced pressure. The solids were collected by filtration, washed with water, then dissolved in 25% MeOH/EtOAc, dried over $MgSO_4$, filtered, and concentrated under reduced pressure to afford 7.6 (966 mg) as a black solid. $^1$H NMR (400 MHz, DMSO): δ 8.67 (s, 1H), 7.52 (s, 1H), 5.85 (s, 2H), 4.18 (s, 2H).

Step 6: 7-Bromo-5-chloro-4-iodoisoindolin-1-one (7.7)

A mixture of 7.6 (966 mg, 3.7 mmol) in conc. hydrochloric acid (0.4 mL, 13 mmol) and water (10 mL) was cooled to 0° C., and treated carefully with sulfuric acid (5 mL, 94 mmol). The resulting slurry was stirred at 0° C. and treated dropwise over 10 min with a solution of sodium nitrite (280 mg, 4.1 mmol) in water (5 mL). The reaction was stirred at 0° C. for 1 h, then treated dropwise with a solution of potassium iodide (1230 mg, 7.4 mmol) in water (5 mL). The reaction was allowed to stir and warm to RT for 1.5 h, then the reaction mixture was poured onto an ice/water mix, and the solids collected by filtration. The solid was dissolved in 25% MeOH/EtOAc, dried over MgSO4, filtered, and concentrated under reduced pressure to afford 7.7 (600 mg, 43%) as a black solid. $^1$H NMR (400 MHz, DMSO): δ 9.02 (s, 1H), 7.97 (s, 1H), 4.23 (s, 2H).

Step 7: Tert-Butyl 7-bromo-5-chloro-4-iodo-1-oxoisoindoline-2-carboxylate (7.8)

A mixture of 7.7 (600 mg, 1.6 mmol) and DMAP (256 mg, 2.1 mmol) in THF (10 mL) was treated with di-tert-butyl dicarbonate (0.4 mL, 1.7 mmol) and stirred at RT for 4 h. The reaction was quenched with saturated aqueous sodium bicarbonate (20 mL) and extracted into EtOAc (3×40 mL). The combined organic layer was washed with brine (40 mL), passed through a hydrophobic filter and concentrated under reduced pressure. The crude material was dissolved in minimal MeOH, triturated with diethyl ether, and the solids were collected by filtration to afford 7.8 (389 mg, 51%) as a black solid. $^1$H NMR (400 MHz, DMSO): δ 8.06 (s, 1H), 4.57 (s, 2H), 1.59 (s, 9H).

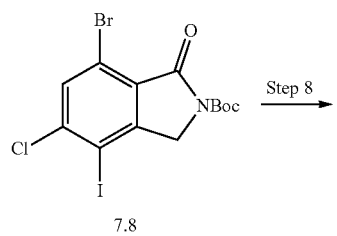

7.8

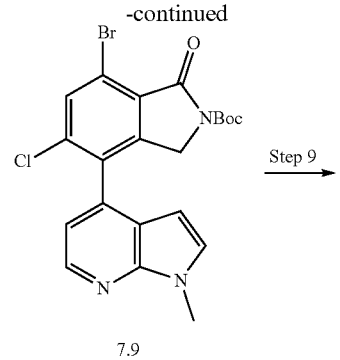

7.9

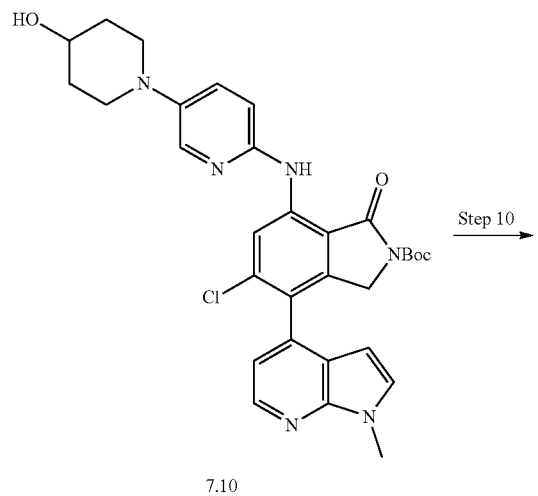

7.10

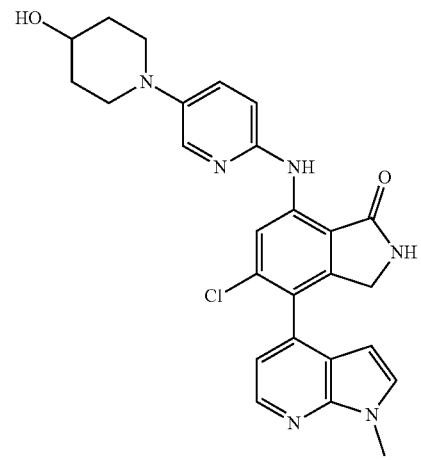

1-190

Step 8, 9 and 10 were carried out following representative procedures described in Example 2 and Example 3 to afford I-190 (4 mg, 16%) as an off-white solid. m/z 489.3 ($^{35}$Cl), 491.4 ($^{37}$Cl) [M+H]$^+$. $^1$H NMR (400 MHz, DMSO): δ 9.78 (s, 1H), 8.74 (s, 2H), 8.36 (d, J=4.9 Hz, 1H), 8.07 (d, J=3.1 Hz, 1H), 7.57 (d, J=3.1 Hz, 1H), 7.46 (dd, J=3.1, 9.0 Hz, 1H), 7.14 (d, J=4.9 Hz, 1H), 6.97-6.94 (m, 1H), 6.21 (d, J=3.5 Hz, 1H), 4.71 (d, J=3.6 Hz, 1H), 4.20 (d, J=18.2 Hz, 1H), 3.95 (d, J=18.0 Hz, 1H), 3.88 (s, 3H), 3.68-3.60 (m, 1H), 3.50 (td, J=4.4, 12.2 Hz, 2H), 2.85 (ddd, J=2.8, 10.0, 12.5 Hz, 2H), 1.88-1.81 (m, 2H), 1.61-1.46 (m, 2H).

Example 8. Method I

Synthesis of 5-fluoro-7-[[5-(4-hydroxy-1-piperidyl)-2-pyridyl]amino]-4-(1-methylpyrrolo[2,3-b]pyridin-4-yl)isoindolin-1-one (I-197)

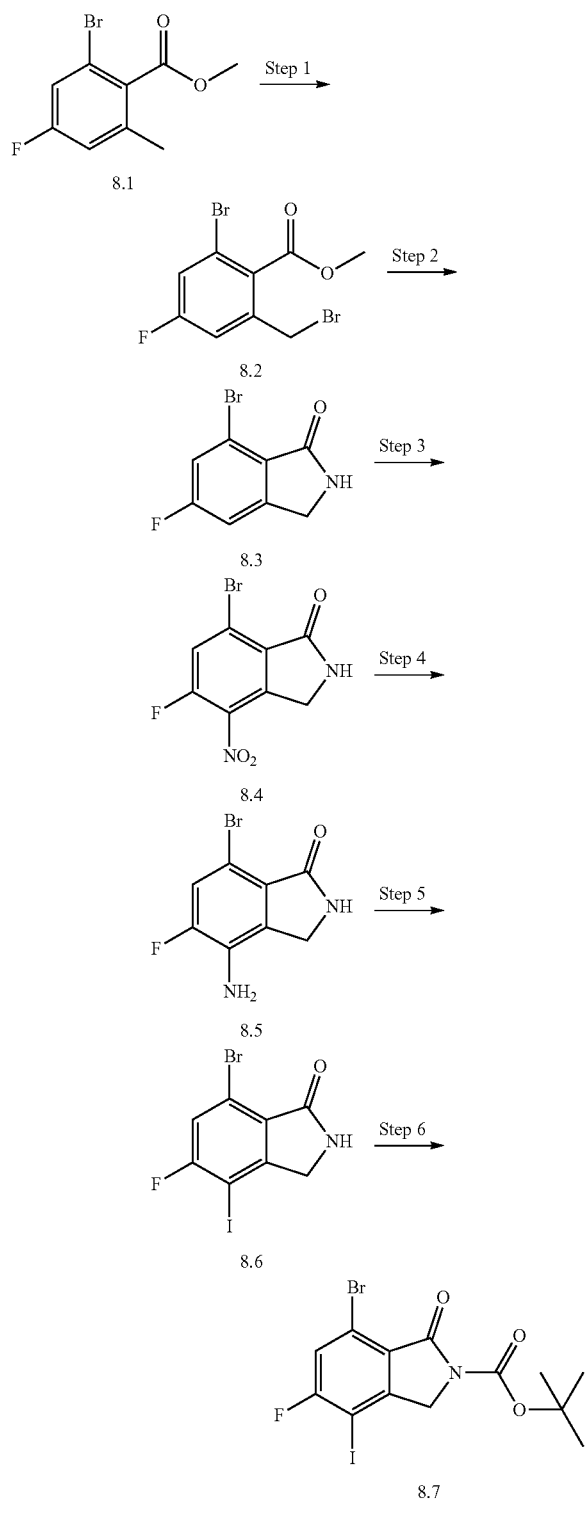

Step 1: Methyl 2-bromo-6-(bromomethyl)-4-fluorobenzoate (8.2)

A mixture of methyl 2-bromo-4-fluoro-6-methylbenzoate 8.1 (1.00 g, 4.05 mmol), NBS (0.94 g, 5.26 mmol and benzoyl peroxide (98 mg, 0.405 mmol) in $CCl_4$ (5 mL) was heated at 75° C. in a sealed tube overnight. The mixture was filtered through Celite washing with DCM and concentrated under vacuum. Purified by silica gel chromatography eluting with 0-25% EtOAc in cyclohexane to afford the title compound 8.2 (1.32 g, quant.) as a pale yellow oil.

Step 2: 7-Bromo-5-fluoroisoindolin-1-one (8.3)

A solution of methyl 2-bromo-6-(bromomethyl)-4-fluorobenzoate 8.2 (1.32 g, 4.05 mmol) in 7N $NH_3$/MeOH (10 mL) was stirred at RT for 3 h. The mixture was concentrated in vacuo and the residue triturated with $Et_2O$ to leave the title compound 8.3 (711 mg, 75%) as a white solid. $^1$H NMR (400 MHz, DMSO): δ 8.74 (s, 1H), 7.64-7.61 (m, 1H), 7.53-7.49 (m, 1H), 4.35 (s, 2H).

Step 3: 7-Bromo-5-fluoro-4-nitroisoindolin-1-one (8.4)

A solution of 7-bromo-5-fluoroisoindolin-1-one 8.3 (460 mg, 2.00 mmol) in c·$H_2SO_4$ (3 mL) at 0° C. was treated with potassium nitrate (138 mg, 3.00 mmol). Stirred cold for 1 h then allowed to warm to RT overnight. The mixture was poured onto ice/water and the precipitate collected by filtration washing with water to leave the title compound 8.4 (438 mg, 80%) as a pale yellow solid.

Step 4: 4-Amino-7-bromo-5-fluoroisoindolin-1-one (8.5)

A mixture of 7-bromo-5-fluoro-4-nitroisoindolin-1-one 8.4 (530 mg, 1.93 mmol), iron powder (323 mg, 5.78 mmol) and ammonium chloride (515 mg, 9.64 mmol) in EtOH (10 mL) and water (2 mL) was heated at reflux for 2 h. The hot mixture was filtered through Celite washing with 25% MeOH in DCM. The filtrate was concentrated under vacuum and triturated with water. Collected by filtration washing with water. The residue was loaded onto HMN and purified by silica gel chromatography eluting with 50-100% EtOAc in DCM to afford the title compound 8.5 (176 mg, 37%) as a cream coloured solid. $^1$H NMR (400 MHz, DMSO): δ 8.58-8.55 (m, 2H), 7.35 (d, J=11.0 Hz, 2H), 5.63 (s, 4H), 4.13-4.12 (m, 4H), 3.18 (d, J=5.3 Hz, 1H).

Step 5: 4-Iodo-7-bromo-5-fluoroisoindolin-1-one (8.6)

A solution of 4-amino-7-bromo-5-fluoroisoindolin-1-one 8.5 (300 mg, 1.22 mmol) in 20% sulfuric acid (5 mL) was cooled to 0° C., treated dropwise with a solution of sodium nitrite (169 mg, 2.45 mmol) in water (1 mL) and stirred cold for 1 h. A solution of potassium iodide (406 mg, 2.45 mmol) in water (1 mL) was added dropwise. After the addition, the mixture was stirred at RT for 1 h. Poured onto ice/water and the precipitate was collected by filtration. Washed with water and dried to leave the title compound 8.6 (137 mg, 31%) as an orange solid. The aqueous phase was extracted with EtOAc (3×), dried over $Na_2SO_4$ and concentrated in vacuo to leave additional title compound 8.6 (207 mg, 47%)

as an orange solid. ¹H NMR (400 MHz, DMSO): δ 8.93 (s, 1H), 7.70-7.67 (m, 1H), 4.19 (s, 2H)

Step 6: Tert-Butyl 7-bromo-5-fluoro-4-iodo-1-oxoi-soindoline-2-carboxylate (8.7)

A solution of 4-iodo-7-bromo-5-fluoroisoindolin-1-one 8.6 (340 mg, 0.955 mmol) in THF (10 mL) was treated with di-tert-butyl dicarbonate (240 mg, 1.10 mmol) and DMAP (140 mg, 1.15 mmol) was stirred at RT for 18 h. The mixture was diluted with EtOAc, washed with water and brine, dried over Na₂SO₄, and concentrated in vacuo. Purified by silica gel chromatography (gradient: 0-80% EtOAc in cyclohexane) afforded the title compound 8.7 (344 mg, 79%) as an off-white solid. ¹H NMR (400 MHz, CDCl₃): δ 7.38 (d, J=7.7 Hz, 1H), 4.54 (s, 2H), 1.62 (s, 9H).

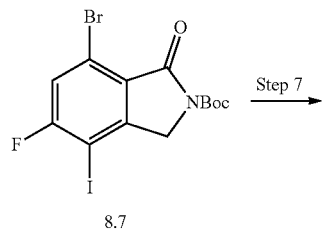

8.7

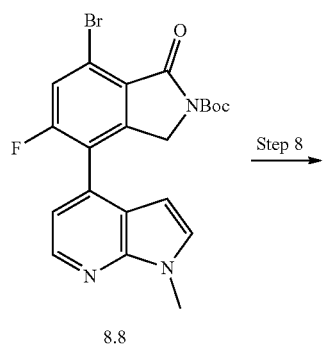

8.8

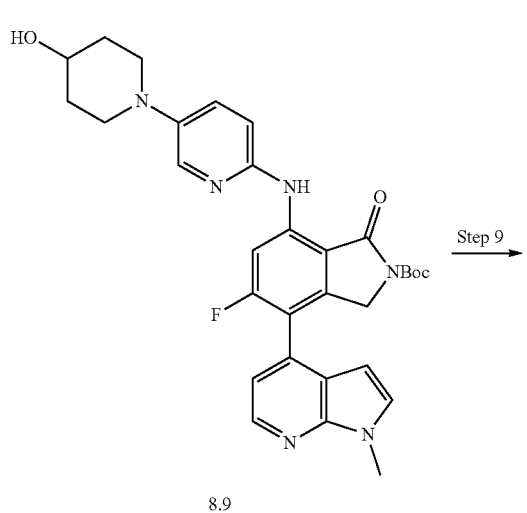

8.9

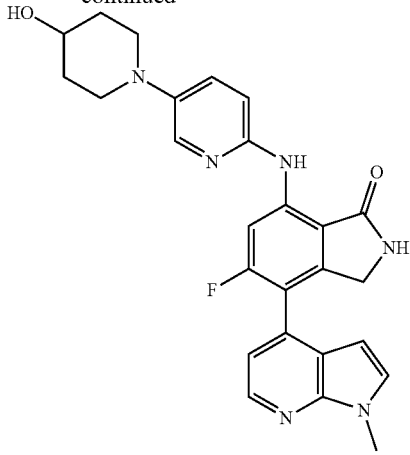

I-197

Step 7, 8 and 9 were carried out following representative procedures described in Example 2 and Example 3 to afford I-197 (40 mg, 71%) as a pale yellow solid. m/z=473 [M+H]⁺. ¹H NMR (400 MHz, DMSO): δ 9.91 (d, J=1.3 Hz, 1H), 8.72 (s, 1H), 8.46 (d, J=14.1 Hz, 1H), 8.35-8.33 (m, 1H), 8.05 (d, J=3.0 Hz, 1H), 7.57 (d, J=3.5 Hz, 1H), 7.46 (dd, J=3.0, 9.0 Hz, 1H), 7.24 (d, J=4.9 Hz, 1H), 6.98-6.95 (m, 1H), 6.29 (dd, J=2.5, 3.4 Hz, 1H), 4.71 (d, J=4.2 Hz, 1H), 4.29 (br s, 2H), 3.87 (s, 3H), 3.71-3.59 (m, 1H), 3.53-3.44 (m, 2H), 2.88-2.80 (m, 2H), 1.89-1.81 (m, 2H), 1.58-1.47 (m, 2H).

Example 9. Method J

Synthesis of S)-4-(7-fluoroimidazo[1,2-a]pyridin-3-yl)-7-((5-(2-(2-hydroxypropan-2-yl)morpholino)pyridin-2-yl)amino)isoindolin-1-one (I-344) & (R)-4-(7-fluoroimidazo[1,2-a]pyridin-3-yl)-7-((5-(2-(2-hydroxypropan-2-yl)morpholino)pyridin-2-yl)amino)isoindolin-1-one (I-345)

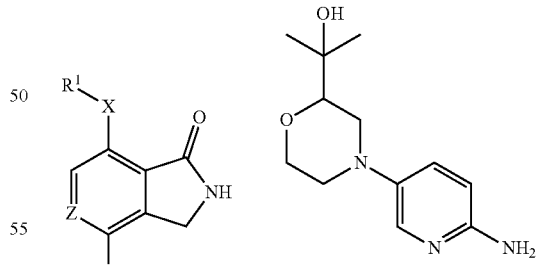

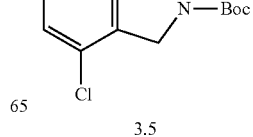

3.5

1121
-continued
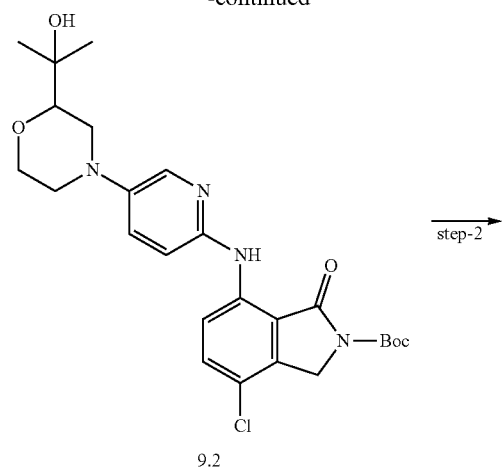
9.2
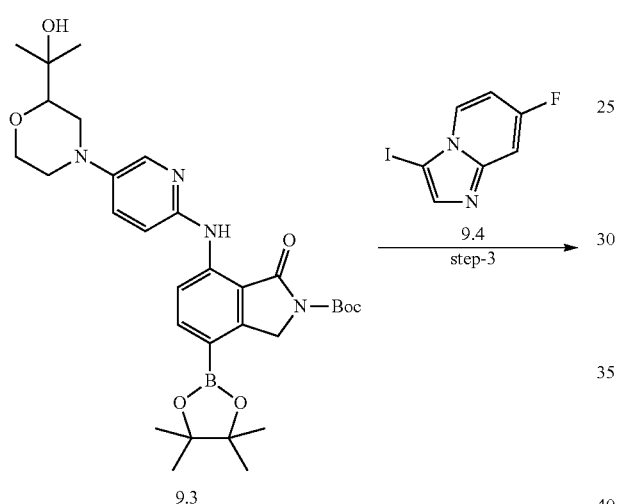
9.3
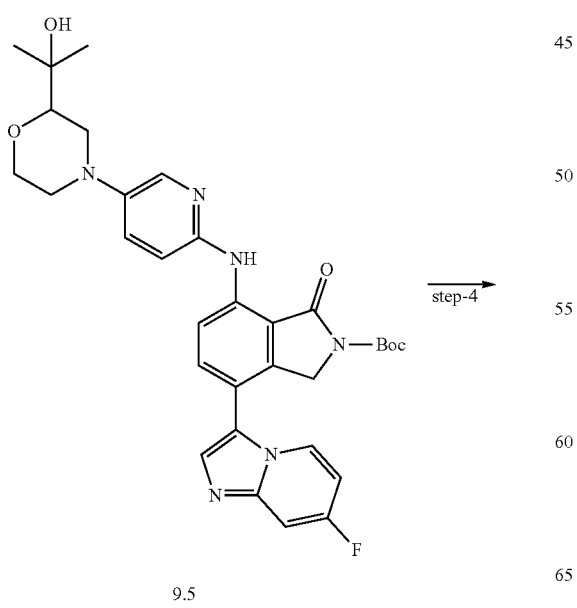
9.5
1122
-continued
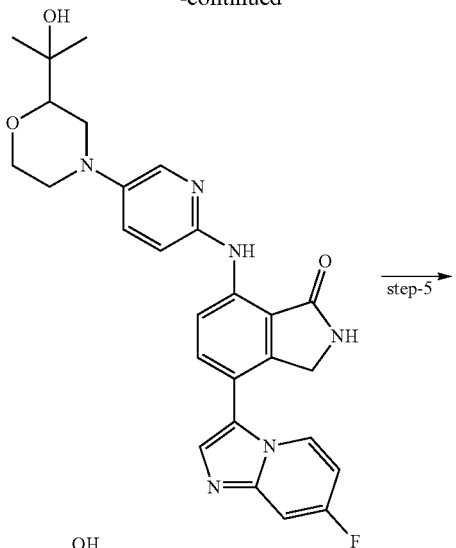
9.6
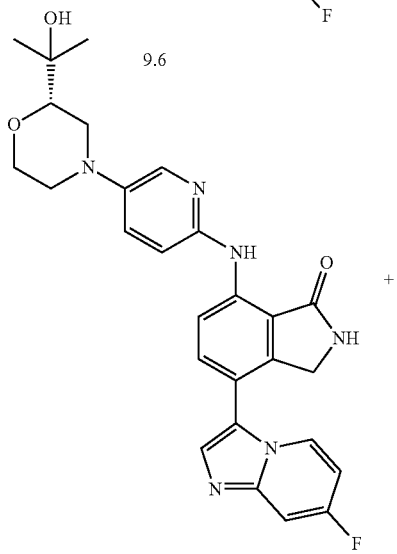
I-344
+
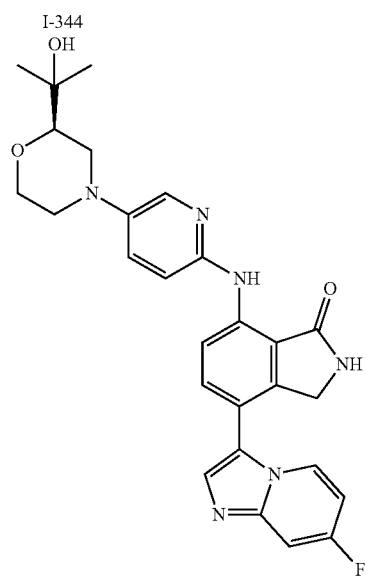
I-345

Step 1: Tert-Butyl 4-chloro-7-((5-(2-(2-hydroxypropan-2-yl)morpholino)pyridin-2-yl)amino)-1-oxoisoindoline-2-carboxylate (9.2)

tert-butyl 4-chloro-7-((5-(2-(2-hydroxypropan-2-yl)morpholino)pyridin-2-yl)amino)-1-oxoisoindoline-2-carboxylate (9.2) was prepared from tert-butyl 7-bromo-4-chloro-1-oxoisoindoline-2-carboxylate (3.5) and 2-(4-(6-aminopyridin-3-yl)morpholin-2-yl)propan-2-ol (9.1) in a similar fashion to that described tert-butyl 4-chloro-7-((5-(4-methylpiperazin-1-yl)pyridin-2-yl)amino)-1-oxoisoindoline-2-carboxylate (3.6).

Step 2. Tert-Butyl 7-((5-(2-(2-hydroxypropan-2-yl)morpholino)pyridin-2-yl)amino)-1-oxo-4-(4,4,5,5-tetramethyl-1,3,2-dioxaborolan-2-yl)isoindoline-2-carboxylate (9.3)

A 30 mL microwave vial was charged with 9.2 (800 mg, 1.38 mmol), bis(pinacolato)diboron (1.4 g, 5.54 mmol), XPhos Pd G2 (120 mg, 0.13 mmol), XPhos (80 mg, 0.13 mmol), solid $K_3PO_4$ (587 mg, 2.6 mmol) and Dioxane (12 mL). The mixture was degassed, purged with $N_2$, and stirred at 100° C. for 3 h. The reaction mixture was cooled to RT and then diluted ethyl acetate (100 mL) and water (100 mL). The organic layer was collected, and the aqueous phase was extracted with ethyl acetate (2×100 mL), and the combined organic extracts were washed with brine (100 mL), dried over $Na_2SO_4$, filtered, and concentrated under reduced pressure. The residue was purified by column chromatography (0-20% gradient elution MeOH in DCM). The residue obtained was then triturated with pentane and the resulting solid was collected by filtration to afford the title compound 9.3 (700 mg, 74%)

Step 3. Tert-Butyl 4-(7-fluoroimidazo[1,2-a]pyridin-3-yl)-7-((5-(2-(2-hydroxypropan-2-yl)morpholino)pyridin-2-yl)amino)-1-oxoisoindoline-2-carboxylate (9.5)

A 30 mL microwave vial was charged with 9.3 (500 mg, 0.84 mmol), 7-fluoro-3-iodoimidazo[1,2-a]pyridine (9.4) (330 mg, 1.26 mmol), XPhos Pd G2 (40 mg, 0.08 mmol), XPhos (66 mg, 0.08 mmol), solid $K_3PO_4$ (356 mg, 1.6 mmol), dioxane (10 mL) and water (2 mL). The mixture was degassed, purged with $N_2$, and stirred at 100° C. for 3 h. The reaction mixture was cooled to RT and then diluted ethyl acetate (50 mL) and water (50 mL). The organic layer was collected, and the aqueous phase was extracted with ethyl acetate (2×50 mL), and the combined organic extracts were washed with brine (50 mL), dried over $Na_2SO_4$, filtered, and concentrated under reduced pressure. The residue was purified by column chromatography (0-5% gradient elution MeOH in DCM). The residue obtained was then triturated with pentane and the resulting solid was collected by filtration to afford the title compound (9.5) (240 mg, 47%)

Step 4. 4-(7-fluoroimidazo[1,2-a]pyridin-3-yl)-7-((5-(2-(2-hydroxypropan-2-yl)morpholino)pyridin-2-yl)amino)isoindolin-1-one (9.6)

tert-butyl 4-(imidazo[1,2-a]pyridin-3-yl)-7-((5-(4-methylpiperazin-1-yl)pyridin-2-yl)amino)-1-oxoisoindoline-2-carboxylate (9.5) (250 mg, 0.41 mmol) was diluted with DCM (5 mL) and treated with TFA (100 eq., 3.3 mL). The reaction was stirred for 30 mins at RT, and The reaction mixture was transferred into saturated sodium bicarbonate solution (100 mL), extracted with DCM (2×50 mL) the combined organic layer was washed with brine (50 mL), dried with $MgSO_4$ and then concentrated in vacuo. The residue was purified by preparative HPLC to afford the desired compound (9.6) (100 mg, 48%). m/z=440.2 $[M+H]^+$.

Step 5. S)-4-(7-fluoroimidazo[1,2-a]pyridin-3-yl)-7-((5-(2-(2-hydroxypropan-2-yl)morpholino)pyridin-2-yl)amino)isoindolin-1-one (I-344) & (R)-4-(7-fluoroimidazo[1,2-a]pyridin-3-yl)-7-((5-(2-(2-hydroxypropan-2-yl)morpholino)pyridin-2-yl)amino)isoindolin-1-one (I-345)

9.6 was separated on Shimadzu LC-20AP and UV detector. The column used was CHIRALPAK IBN-5 (250*21.0) mm, 5 micron, column flow was 18.0 mL/min. Mobile phase were used (A) 0.1% DEA IN Acetonitrile (B) 0.1% DEA IN Methanol. The UV spectra were recorded at 308 nm Lambda max by Chiral SFC to afford compounds I-344 (23 mg) and I-345 (24 mg).

I-344: $^1H$ NMR (400 MHz, DMSO): δ 9.87 (s, 1H), 8.80 (s, 1H), 8.58-8.55 (m, 1H), 8.42 (s, 1H), 8.00 (s, 1H), 7.81-7.86 (m, 1H), 7.70-7.67 (m, 1H), 7.53-7.43 (m, 2H), 6.99-6.96 (m, 2H), 4.50 (s, 1H), 4.37 (s, 2H), 4.00-3.98 (d, J=10.8 Hz, 1H), 3.67-3.57 (m, 2H), 3.46 (m, 2H), 3.39-3.33 (m, 3H), 1.21-1.09 (m, 6H)

I-345: $^1H$ NMR (400 MHz, DMSO): δ 9.87 (s, 1H), 8.80 (s, 1H), 8.58-8.56 (d, J=8.8 Hz, 1H), 8.44-8.40 (t, J=16, 1H), 8.01 (s, 1H), 7.81 (s, 1H), 7.70-7.68 (d, J=8.8, 1H), 7.54-7.51 (d, J=9.6 Hz, 1H), 7.46-7.44 (m, 1H), 6.99-6.95 (m, 2H), 4.51 (s, 1H), 4.37 (s, 2H), 4.00-3.98 (d, J=10.8 Hz, 1H), 3.67-3.57 (m, 2H), 3.46-3.44 (m, 2H), 3.34-3.19 (m, 3H), 1.23-1.06 (m, 6H).

Example 10. Method K

Synthesis of 3,3-dimethyl-4-(1-methyl-1H-pyrrolo[2,3-b]pyridin-4-yl)-7-((5-(piperazin-1-yl)pyridin-2-yl)amino)isoindolin-1-one (I-273)

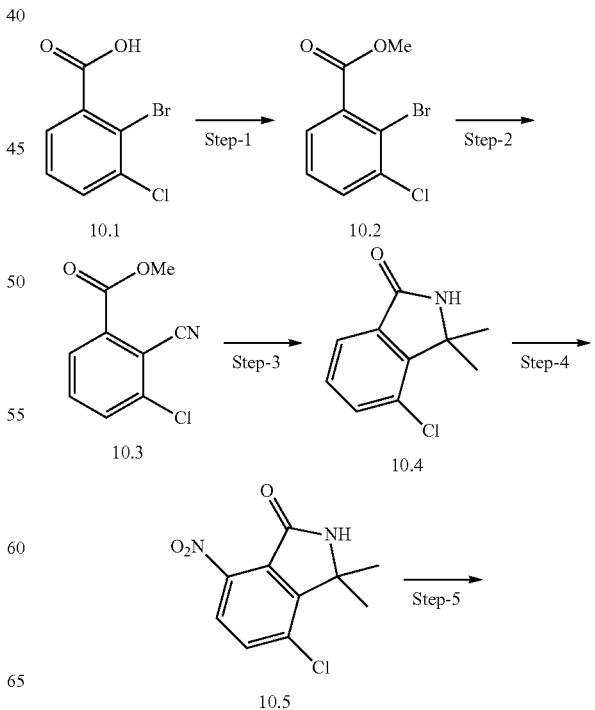

-continued

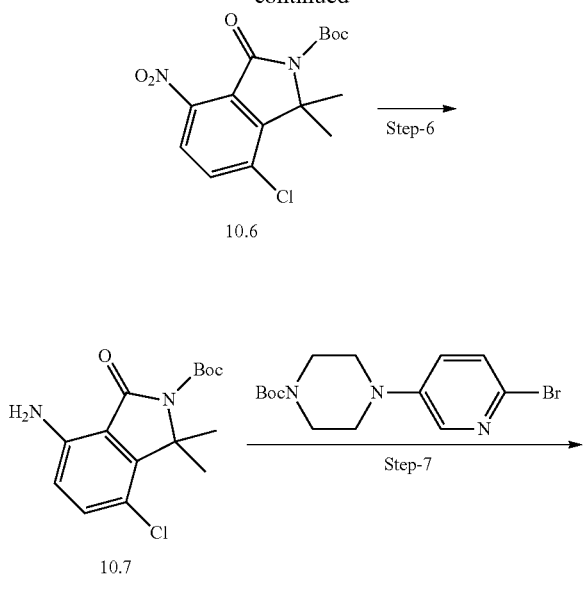

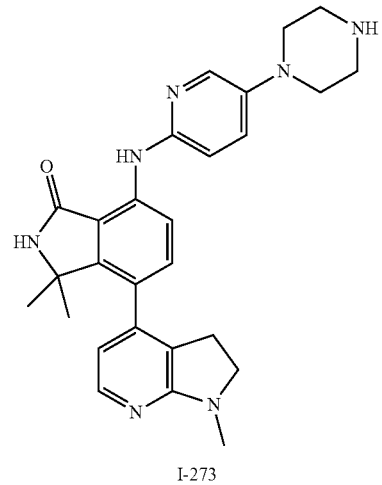

Step 1. Methyl 2-bromo-3-chlorobenzoate (10.2)

A mixture of 2-bromo-3-chlorobenzoic acid (10.1) (10.0 g, 42.9 mmol) in DMF (100 mL) were added $K_2CO_3$ (11.8 g, 85.8 mmol) and $CH_3I$ (3.96 mL, 63.0 mmol) and stirred at RT for 2 h. The reaction mixture was transferred into water (500 mL) and extracted with ethyl acetate (2×500 mL) and the combined organic phases were washed with brine (500 mL), dried with $MgSO_4$, filtered, and then concentrated in vacuo. The residue was purified by column chromatography (0-50% gradient elution EtOAc in iso-hexane) to afford the title compound 10.2 (10 g, 95.14%). m/z 247.1 $[M+H]^+$.

Step 2. Methyl 3-chloro-2-cyanobenzoate (10.3)

A solution of methyl 2-bromo-3-chlorobenzoate (10.2) (0.5 g, 2.008 mmol) in DMF (5 mL) were added CuCN (0.197 g, 2.2 mmol) and reaction mixture were heated at 90° C. temperature for 1.2 h. The reaction mixture was transferred into water (50 mL) and extracted with ethyl acetate (2×50 mL) and the combined organic phases were washed with brine (50 mL), dried with $MgSO_4$, filtered, and then concentrated in vacuo. The residue was purified by column chromatography (0-50% gradient elution EtOAc in iso-hexane) to afford the title compound 10.3 (0.25 g, 63.61%). m/z 195 $[M+H]_+$.

Step 3. 4-chloro-3,3-dimethylisoindolin-1-one (10.4)

A solution of methyl 3-chloro-2-cyanobenzoate (10.3) (0.60 g, 3.07 mmol) in dry THF (10 mL) at −78° C. under a nitrogen atmosphere was treated dropwise with $CH_3Li$ (1M solution in THF, 12.3 mL, 12.3 mmol). After the addition, the mixture was allowed to warm to RT and stirred for 2 h. The reaction mixture was transferred into water (100 mL), extracted with ethyl acetate (2×50 mL) the combined organic layer was washed with brine (50 mL), dried with MgSO4, and then concentrated in vacuo. The residue was purified by column chromatography (0-70% gradient elution EtOAc in iso-hexane) to afford the title compound 10.4 (0.5 g 83.33%). m/z 196 [M+H]$^+$.

Step 4.
4-chloro-3,3-dimethyl-7-nitroisoindolin-1-one (10.5)

4-chloro-3,3-dimethyl-7-nitroisoindolin-1-one (10.5) was prepared from 4-chloro-3,3-dimethylisoindolin-1-one (10.4) in a similar fashion to that described 4-Chloro-7-nitroisoindolin-1-one (3.2) (400 mg, 59.17%). m/z 241 [M+H]$^+$.

Step 5. Tert-Butyl 7-chloro-1,1-dimethyl-4-nitro-3-oxoisoindoline-2-carboxylate (10.6)

To a solution of 4-chloro-3,3-dimethyl-7-nitroisoindolin-1-one (10.5) (0.5 g, 2.08 mmol) in THF (20 mL) was added di-tert-butyl dicarbonate (681 mg, 3.1 mmol) and DMAP (254 mg, 2.08 mmol) at 0° C. The reaction was stirred at RT for 1 h. The solution was diluted with ethyl acetate (50 mL) and water (25 mL). The organic phase was collected, and the aqueous phase was extracted with ethyl acetate (2×50 mL). The combined organic layers were washed with brine (30 mL), dried over MgSO$_4$, filtered, and concentrated under reduced pressure. The crude compound was purified by column chromatography (0-50% gradient elution EtOAc in iso-hexanes) to afford the title compound 10.6 (49 mg, 69.20%). m/z 341 [M+H]$^+$.

Step 6. Tert-Butyl 4-amino-7-chloro-1,1-dimethyl-3-oxoisoindoline-2-carboxylate (10.7)

A solution tert-butyl 7-chloro-1,1-dimethyl-4-nitro-3-oxoisoindoline-2-carboxylate (10.6) (0.5 g, 1.46 mmol) in THF (5 mL) was treated with Raney nickel (100 mg) under hydrogen atmosphere and stirred at RT for 30 min. Reaction mass was filter through celite bed, and washed with ethyl acetate (2×50 mL). The combined organic solvent was removed in vacuo to afford the title compound (10.7) (400 mg, 87.91%). m/z 310 [M+H]$^+$.

Step 7. Tert-Butyl 4-((5-(4-(tert-butoxycarbonyl) piperazin-1-yl)pyridin-2-yl)amino)-7-chloro-1,1-dimethyl-3-oxoisoindoline-2-carboxylate (10.8)

To a solution of tert-butyl 4-amino-7-chloro-1,1-dimethyl-3-oxoisoindoline-2-carboxylate (10.7) (462 mg, 1.49 mmol) in 1,4-dioxane (10 mL) was added tert-butyl 4-(6-bromopyridin-3-yl)piperazine-1-carboxylate (509 mg, 1.49 mmol) and CS$_2$CO$_3$ (971 mg, 2.98 mmol). The reaction mixture was degassed under argon for 20 min, and Pd$_2$(dba)$_3$ (136 mg, 0.14 mmol,) and Xanthphos (172 mg, 0.29 mmol) was added and then heated at 100° C. for 2 h. The solution was diluted with ethyl acetate (50 mL) and water (50 mL). The organic phase was collected, and the aqueous phase was extracted with ethyl acetate (2×50 mL). The combined organic layers were washed with brine (30 mL), dried over MgSO$_4$, filtered, and concentrated under reduced pressure. The crude compound was purified by column chromatography (0-70% gradient elution EtOAc in iso-hexanes) to afford the title compound 10.8 (210 mg, 38.57%). m/z 572.3 [M+H]$^+$.

Step 8. tert-butyl 4-((5-(4-(tert-butoxycarbonyl) piperazin-1-yl)pyridin-2-yl)amino)-1,1-dimethyl-7-(1-methyl-1H-pyrrolo[2,3-b]pyridin-4-yl)-3-oxoisoindoline-2-carboxylate (10.9)

To a solution of tert-butyl 4-((5-(4-(tert-butoxycarbonyl) piperazin-1-yl)pyridin-2-yl)amino)-7-chloro-1,1-dimethyl-3-oxoisoindoline-2-carboxylate (10.8) (60 mg, 0.10 mmol) in 1,4-dioxane (2 mL) was added 1-methyl-4-(4,4,5,5-tetramethyl-1,3,2-dioxaborolan-2-yl)-1H-pyrrolo[2,3-b]pyridine (35 mg, 0.136 mmol) and K$_3$PO$_4$ (44 mg, 0.21 mmol) was added. The reaction mixture was degassed under argon for 20 min, and Xphos (8 mg, 0.015 mmol) and XphosPdG2 (13 mg, 0.0157 mmol) were added and then heated at 110° C. for 1 h. The solution was diluted with ethyl acetate (25 mL) and water (25 mL). The organic phase was collected, and the aqueous phase was extracted with ethyl acetate (2×25 mL). The combined organic layers were washed with brine (20 mL), dried over MgSO$_4$, filtered, and concentrated under reduced pressure. The crude compound was purified by column chromatography (0-70% gradient elution EtOAc in iso-hexanes) to afford the title compound 10.9 (36 mg, 51.42%), m/z 668.4 [M+H]$^+$.

Step 9. 3,3-dimethyl-4-(1-methyl-1H-pyrrolo[2,3-b] pyridin-4-yl)-7-((5-(piperazin-1-yl)pyridin-2-yl) amino)isoindolin-1-one (I-273)

tert-butyl 4-((5-(4-(tert-butoxycarbonyl)piperazin-1-yl) pyridin-2-yl)amino)-1,1-dimethyl-7-(1-methyl-1H-pyrrolo [2,3-b]pyridin-4-yl)-3-oxoisoindoline-2-carboxylate (10.9) (36 mg, 0.41 mmol) was diluted with DCM (5 mL) and treated with TFA (100 eq., 3.3 mL). The reaction was stirred for 30 mins at RT, and then concentrated under vacuum and triturated with 7N methanolic ammonia (2×3 mL). The residue was purified by preparative HPLC to afford the desired compound (I-273) (20 mg, 79%), m/z 468.2 [M+H]+]+, $^1$H NMR (400 MHz, DMSO): δ 9.98 (s, 1H), 8.77 (s, 1H), 8.44-8.42 (d, J=8 Hz, 1H), 8.31-8.27 (m, 2H), 7.98-7.97 (s, 1H), 7.51-7.50 (m, 1H), 7.44-7.42 (d, J=8 Hz, 1H), 7.22-7.20 (d, J=8 Hz, 1H), 7.01-7.00 (d, J=4 Hz, 1H), 6.95-6.93 (d, J=8 Hz, 1H), 6.05-6.04 (m, 1H), 3.86 (s, 1H), 3.098 (s, 1H), 2.97 (s, 1H), 1.14 (s, 6H).

Example 11. Method L
Synthesis of S)-7-((5-(4-hydroxypiperidin-1-yl)pyridin-2-yl)amino)-3-methyl-4-(1-methyl-1H-pyrrolo[2,3-b]pyridin-4-yl)isoindolin-1-one (I-286) and ((R)-7-((5-(4-hydroxypiperidin-1-yl)pyridin-2-yl)amino)-3-methyl-4-(1-methyl-1H-pyrrolo[2,3-b]pyridin-4-yl)isoindolin-1-one (I-287)
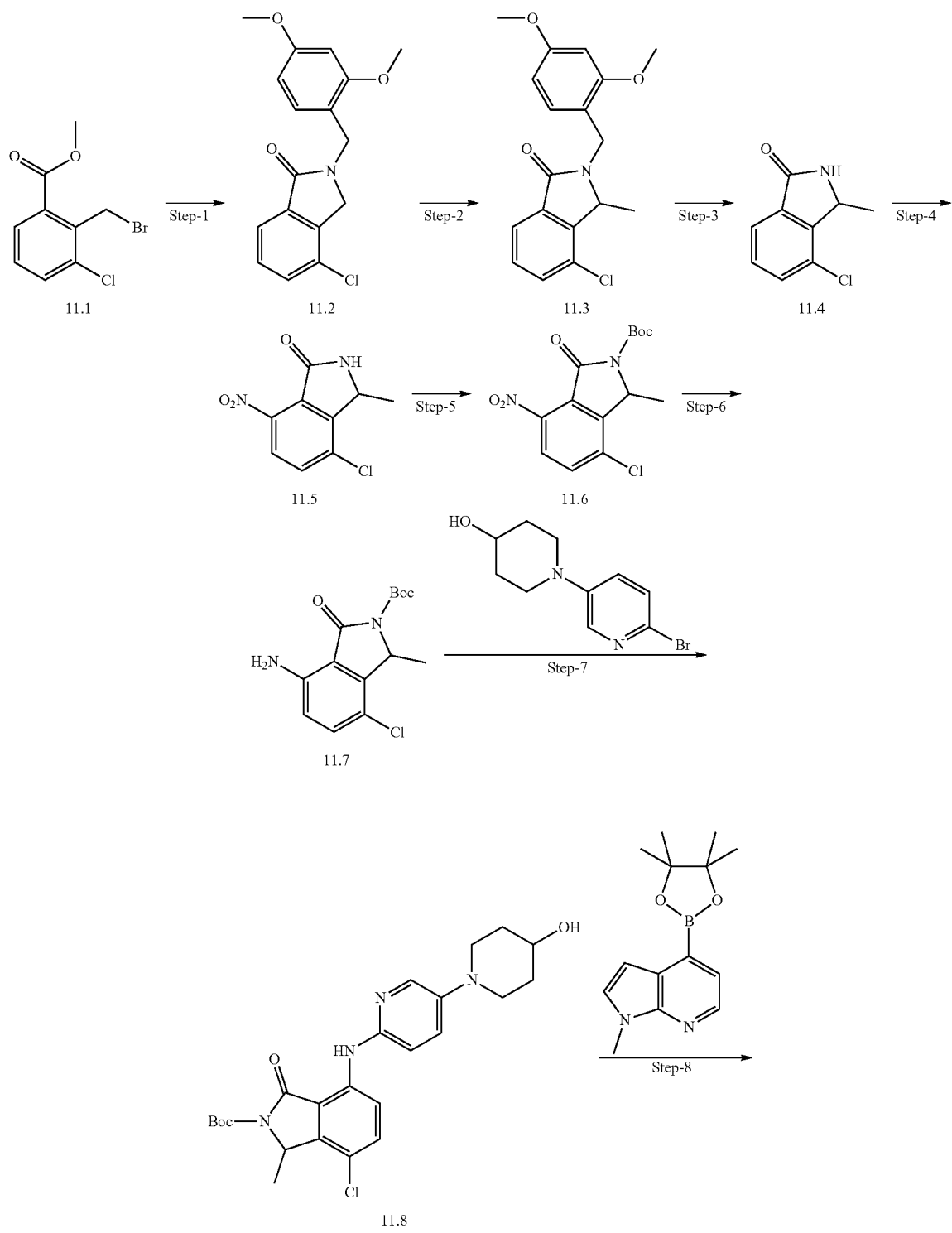

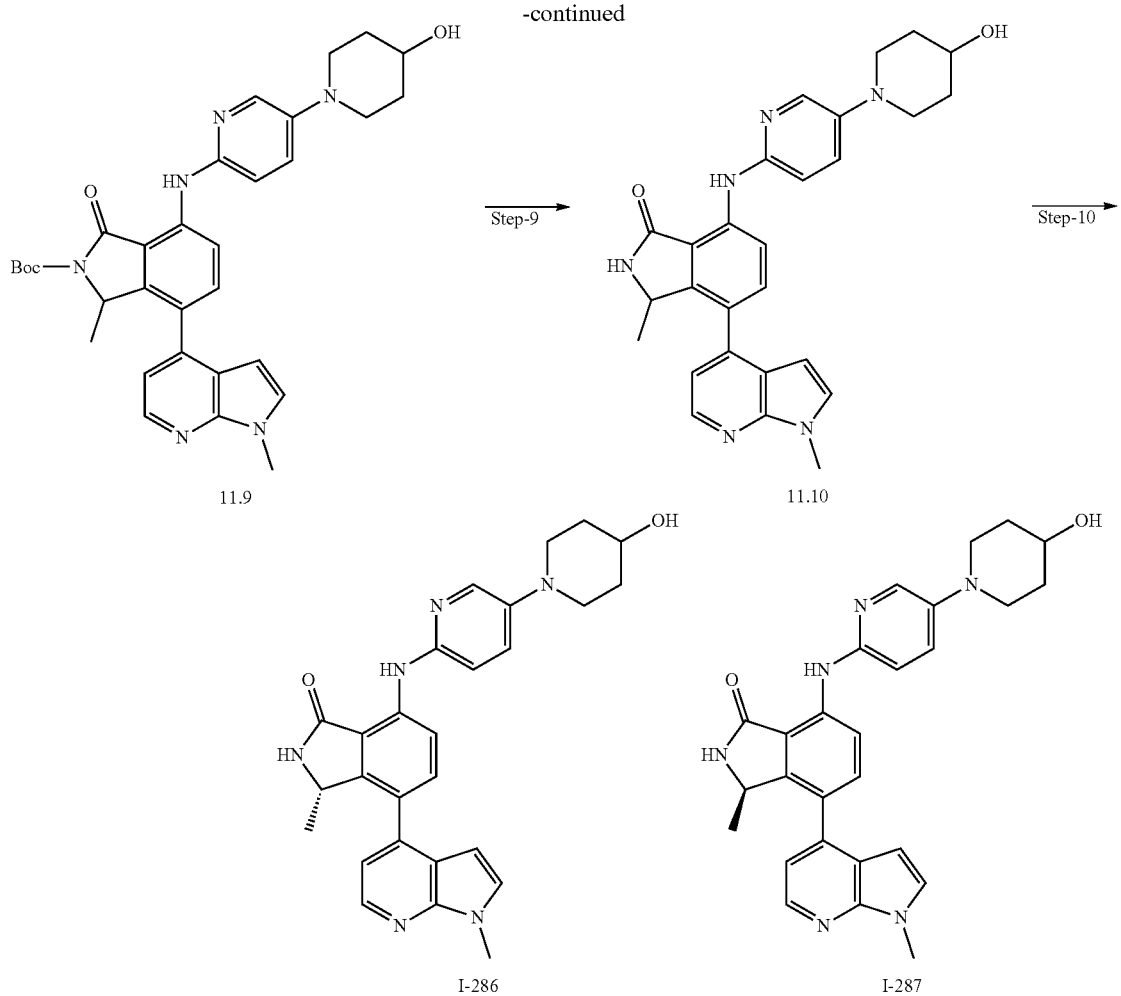

Step 1. 4-chloro-2-(2,4-dimethoxybenzyl)isoindolin-1-one (11.2)

To a solution of methyl 2-(bromomethyl)-3-chlorobenzoate (11.1) (10 g, 37.1 mmol) in methanol (100 mL) was added 2,4-dimethoxybenzylamine (7.6 g, 45.53 mmol) and N,N-Diisopropylethylamine (14.6 g, 113.84 mmol) at 0° C. The reaction mixture was stirred at RT for 1 h. The solution was diluted with ethyl acetate (500 mL) and water (500 mL). The organic phase was collected, and the aqueous phase was extracted with ethyl acetate (2×500 mL). The combined organic layers were washed with brine (500 mL), dried over MgSO$_4$, filtered, and concentrated under reduced pressure. The crude compound was purified by column chromatography (0-20% gradient elution EtOAc in iso-hexanes) to afford the title compound 11.2 (11.g, 91.22%), m/z 318.7 [M+H]$^+$.

Step 2. 4-chloro-2-(2,4-dimethoxybenzyl)-3-methylisoindolin-1-one (11.3)

To a solution of 4-chloro-2-(2,4-dimethoxybenzyl)isoindolin-1-one (11.2) (8 g, 25.2 mmol) in N, N'-DMF (100 mL) was added sodium hydride (60% dispersion in mineral oil, 1.2 g, 30.28 mmol,) at 0° C. and stirred at same temperature for 15 min. Then methyl iodide (3.9 g, 27.76 mmol) was added dropwise over 15 min. The reaction mixture was stirred at RT for 1 h. The solution was poured onto ice-cold water (500 mL) and the precipitate was collected by filtration. The solid was washed with water and dried in vacuo to afford the title compound 11.3 (8.0 g, 95.77%). m/z 332.8 [M+H]$^+$.

Step 3. 4-chloro-3-methylisoindolin-1-one (11.4)

A solution of compound 4-chloro-2-(2,4-dimethoxybenzyl)-3-methylisoindolin-1-one (11.3) (8.0 g, 24.11 mmol) and trifluoroacetic acid (80 mL) heated at 60° C. for 1 h. The reaction mixture was quenched with saturated solution of sodium bicarbonate (500 mL) and extracted with Ethyl acetate (3×500 mL). The combined organic layer was washed with brine solution, and the combined organic layers were washed with brine (500 mL), dried over MgSO$_4$, filtered, and concentrated under reduced pressure. The crude compound was purified by column chromatography (0-60% gradient elution EtOAc in iso-hexanes) to afford the title compound 11.4 (4 g, 91.34%). m/z 182.5 [M+H]$^+$.

Step 4. 4-chloro-3-methyl-7-nitroisoindolin-1-one (11.5)

4-chloro-3-methyl-7-nitroisoindolin-1-one (11.5) was prepared from 4-chloro-3-methylisoindolin-1-one (11.4) in a similar fashion to that described 4-Chloro-7-nitroisoindolin-1-one (3.2). (3.4 g, 68.12%). m/z 227.5 [M+H]$^+$.

Step 5. tert-butyl 4-chloro-3-methyl-7-nitro-1-oxoisoindoline-2-carboxylate (11.6)

tert-butyl 4-chloro-3-methyl-7-nitro-1-oxoisoindoline-2-carboxylate (11.6) was prepared from 4-chloro-3-methyl-7-nitroisoindolin-1-one (11.5) in a similar fashion to that described tert-butyl 7-chloro-1,1-dimethyl-4-nitro-3-oxoisoindoline-2-carboxylate (10.6) (3.2 g, 65.28%). m/z 327.6 [M+H]$^+$.

Step 6. tert-butyl 4-amino-7-chloro-1-methyl-3-oxoisoindoline-2-carboxylate (11.7)

tert-butyl 4-amino-7-chloro-1-methyl-3-oxoisoindoline-2-carboxylate (11.7) was prepared from tert-butyl 4-chloro-3-methyl-7-nitro-1-oxoisoindoline-2-carboxylate (11.6) in a similar fashion to that described tert-butyl 4-amino-7-chloro-1,1-dimethyl-3-oxoisoindoline-2-carboxylate (10.7) (2.3 g 79.14%). m/z 297.6 [M+H]$^+$.

Step 7. Tert-Butyl 4-chloro-7-((5-(4-hydroxypiperidin-1-yl)pyridin-2-yl)amino)-3-methyl-1-oxoisoindoline-2-carboxylate (11.8)

tert-butyl 4-chloro-7-((5-(4-hydroxypiperidin-1-yl)pyridin-2-yl)amino)-3-methyl-1-oxoisoindoline-2-carboxylate (11.8) was prepared from tert-butyl 4-amino-7-chloro-1-methyl-3-oxoisoindoline-2-carboxylate (11.7) and 1-(6-bromopyridin-3-yl)piperidin-4-ol in a similar fashion to that described tert-butyl 4-((5-(4-(tert-butoxycarbonyl)piperazin-1-yl)pyridin-2-yl)amino)-7-chloro-1,1-dimethyl-3-oxoisoindoline-2-carboxylate (10.9) (1.5 g, 47%). m/z 473.4 [M+H]$^+$.

Step 8. Tert-Butyl 4-((5-(4-hydroxypiperidin-1-yl)pyridin-2-yl)amino)-1-methyl-7-(1-methyl-1H-pyrrolo[2,3-b]pyridin-4-yl)-3-oxoisoindoline-2-carboxylate (11.9)

tert-butyl 4-((5-(4-hydroxypiperidin-1-yl)pyridin-2-yl)amino)-1-methyl-7-(1-methyl-1H-pyrrolo[2,3-b]pyridin-4-yl)-3-oxoisoindoline-2-carboxylate (11.9) was prepared from tert-butyl 4-chloro-7-((5-(4-hydroxypiperidin-1-yl)pyridin-2-yl)amino)-3-methyl-1-oxoisoindoline-2-carboxylate (11.8) and 1-methyl-4-(4,4,5,5-tetramethyl-1,3,2-dioxaborolan-2-yl)-1H-pyrrolo[2,3-b]pyridine in a similar fashion to that described tert-butyl 4-((5-(4-(tert-butoxycarbonyl)piperazin-1-yl)pyridin-2-yl)amino)-1,1-dimethyl-7-(1-methyl-1H-pyrrolo[2,3-b]pyridin-4-yl)-3-oxoisoindoline-2-carboxylate (10.11) (0.3 g, Yield: 55.45%). m/z 569.5 [M+H]$^+$.

Step 9. 7-((5-(4-hydroxypiperidin-1-yl)pyridin-2-yl)amino)-3-methyl-4-(1-methyl-1H-pyrrolo[2,3-b]pyridin-4-yl)isoindolin-1-one (11.10)

7-((5-(4-hydroxypiperidin-1-yl)pyridin-2-yl)amino)-3-methyl-4-(1-methyl-1H-pyrrolo[2,3-b]pyridin-4-yl)isoindolin-1-one (11.10) was prepared from tert-butyl 4-((5-(4-hydroxypiperidin-1-yl)pyridin-2-yl)amino)-1-methyl-7-(1-methyl-1H-pyrrolo[2,3-b]pyridin-4-yl)-3-oxoisoindoline-2-carboxylate (11.9) in a similar fashion to that described 3,3-dimethyl-4-(1-methyl-1H-pyrrolo[2,3-b]pyridin-4-yl)-7-((5-(piperazin-1-yl)pyridin-2-yl)amino)isoindolin-1-one (1-273) (0.13 g, Yield: 65.74%). m/z 469.7 [M+H]$^+$.

Step 10. (S)-7-((5-(4-hydroxypiperidin-1-yl)pyridin-2-yl)amino)-3-methyl-4-(1-methyl-1H-pyrrolo[2,3-b]pyridin-4-yl)isoindolin-1-one (I-286) and ((R)-7-((5-(4-hydroxypiperidin-1-yl)pyridin-2-yl)amino)-3-methyl-4-(1-methyl-1H-pyrrolo[2,3-b]pyridin-4-yl)isoindolin-1-one (1-287)

11.10 was separated on Waters SFC 200 and UV detector. The column was used CHIRALCEL 0 J-H (250*21.0) mm, 5 micron, column flow was 80.0 mL/min and ABPR was 100 bar. Mobile phase were used (A) Liquid Carbon dioxide (Liq. CO2) and (B) 0.1% DEA In propanol:acetonitrile (50:50) to provide compounds I-286 (35 mg) and 1-287 (35 mg).

I-286: m/z 469.7 [M+H]$^+$. $^1$H NMR (400 MHz, DMSO): δ 9.905 (s, 1H), 8.809 (s, 1H), 8.51-8.49 (d, J=8 Hz, 1H), 8.32-8.30 (m, 1H), 8.00 (s, 1H), 7.60-7.57 (m, 2H), 7.45-7.43 (m, 1H), 7.25-7.24 (m, 1H), 6.95-6.93 (d, J=8, 1H), 6.42-6.41 (m, 1H), 5.05-5.04 (m, 1H), 4.724 (s, 1H), 3.882 (s, 3H), 3.628 (s, 1H), 3.47-3.44 (m, 3H), 2.84-2.79 (t, J=20, 2H), 1.86-1.83 (m, 2H), 1.55-1.51 (m, 2H), 0.80-0.78 (m, 3H)

I-287: m/z 469.7 [M+H]$^+$. $^1$H NMR (400 MHz, DMSO): δ 9.90 (s, 1H), 8.80 (s, 1H), 8.51-8.49 (d, J=8 Hz, 1H), 8.32-8.31 (m, 1H), 8.01 (s, 1H), 7.60-7.57 (m, 2H), 7.45-7.43 (m, 1H), 7.25-7.24 (m, 1H), 6.95-6.93 (d, J=8, 1H), 6.42-6.41 (m, 1H), 5.05-5.04 (m, 1H), 4.72 (s, 1H), 3.88 (s, 3H), 3.63 (s, 1H), 3.47-3.44 (m, 3H), 2.84-2.79 (t, J=20, 2H), 1.86-1.84 (m, 2H), 1.53-1.51 (m, 2H), 0.80-0.79 (m, 3H).

Example 12. Method M

Synthesis of -((5-(4-hydroxypiperidin-1-yl)pyridin-2-yl)amino)-5-methyl-4-(1-methyl-1H-pyrrolo[2,3-b]pyridin-4-yl)isoindolin-1-one: (I-292)

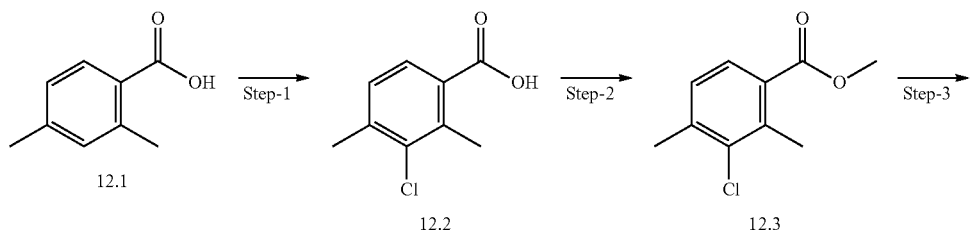

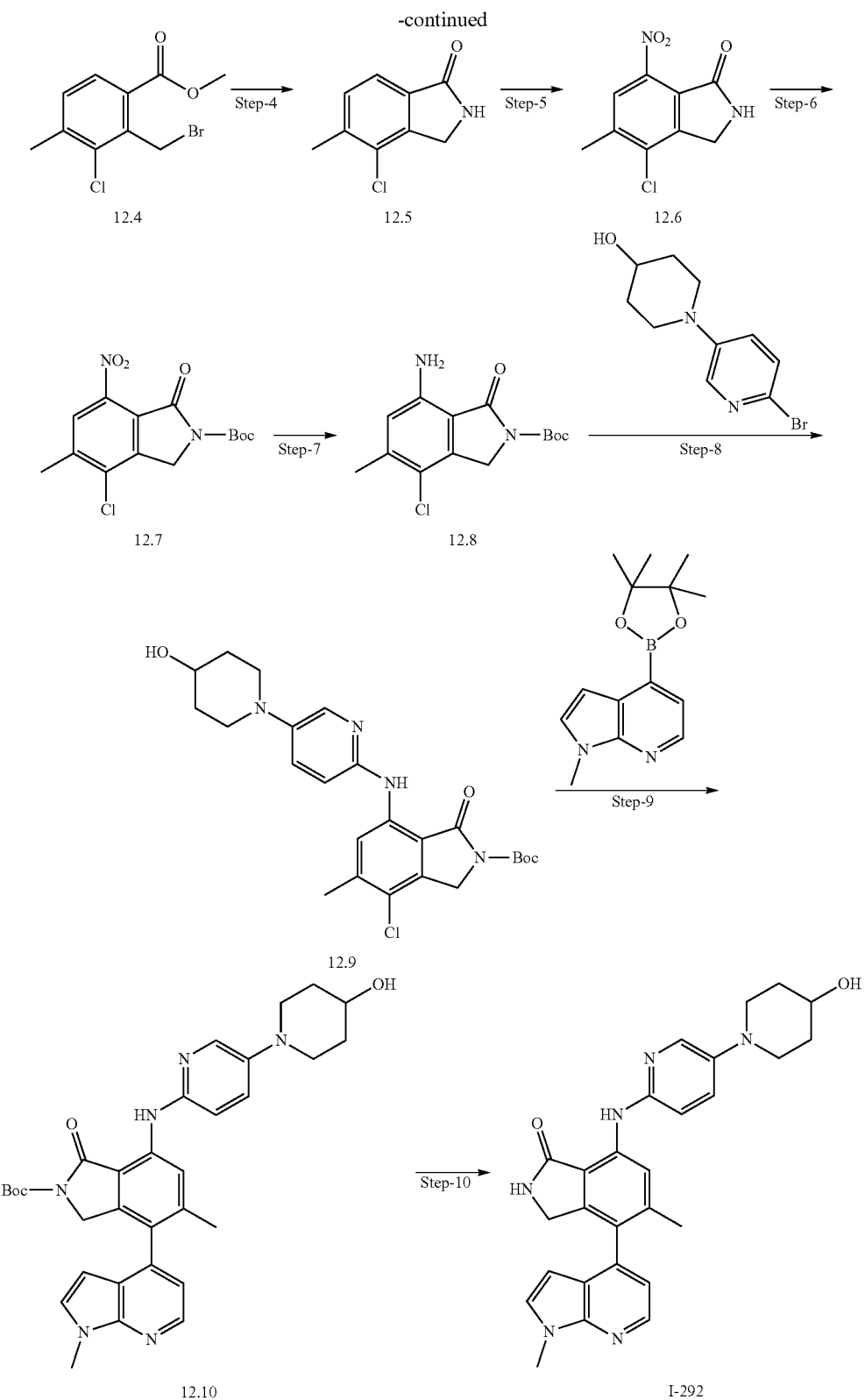
Step 1. 3-chloro-2,4-dimethylbenzoic Acid (12.2)
To a solution of 2,4-dimethylbenzoic acid (12.1) (20 g, 133.17 mmol) in TFA (400 mL) was added NCS (26.67 g, 199.73 mmol, 1.5 eq), and stirred at 50° C. for 16 h. The reaction mixture was quenched with saturated solution of sodium bicarbonate (1000 mL) and extracted with Ethyl acetate (3×500 mL). The combined organic layer was washed with brine solution (500 mL), dried over MgSO₄, filtered, and concentrated under reduced pressure. The crude compound was purified by column chromatography (0-60% gradient elution EtOAc in iso-hexanes) to afford the title compound (12.2) (7 g, 48.37%). m/z 185.2 [M+H]⁺.

Step 2. methyl 3-chloro-2,4-dimethylbenzoate (12.3)

To a solution of 3-chloro-2,4-dimethylbenzoic acid (12.2) (12 g, 65.21 mmol) in DMF (120 mL) was added K₂CO₃ (22.4 g, 163.0 mmol), and methyl iodide (13.8 g, 163.0 mmol). The reaction was stirred at RT for 3 h. The solution was diluted with ethyl acetate (500 mL) and water (500 mL). The organic phase was collected, and the aqueous phase was extracted with ethyl acetate (2×500 mL). The combined organic layers were washed with brine (500 mL), dried over MgSO₄, filtered, and concentrated under reduced pressure. The crude compound was purified by column chromatography (0-20% gradient elution EtOAc in iso-hexanes) to afford the title compound 12.3 (11 g, 85.27%). m/z 199.7 [M+H]⁺

Step 3. methyl 2-(bromomethyl)-3-chloro-4-methylbenzoate (12.4)

To a solution of methyl 3-chloro-2,4-dimethylbenzoate (12.3) (11 g, 55.55 mmol) in CCl₄ (110 mL) was added NBS (9.88 g, 55.5 mmol), and DPPO (124 mg, 0.55 mmol). The reaction was stirred at 90° C. for 5 h. The solution was diluted with ethyl acetate (500 mL) and water (500 mL). The organic phase was collected, and the aqueous phase was extracted with ethyl acetate (2×500 mL). The combined organic layers were washed with brine (500 mL), dried over MgSO₄, filtered, and concentrated under reduced pressure to afford the title compound 12.4 (14 g). The crude compound was used as such for next step.

Step 4. 4-chloro-5-methylisoindolin-1-one (12.5)

To a solution of methyl 2-(bromomethyl)-3-chloro-4-methylbenzoate (12.4) (14 g, 50.73 mmol) in methanol was added ammonia (7N in methanol, 500 mL) at 0° C., and the reaction was stirred at RT for 16 h. After completion of reaction, solvent was evaporated under vacuum to afford crude material. Crude material which was purified by trituration using pentane and hexane to provide compound 4-chloro-5-methylisoindolin-1-one (12.5) (8 g) m/z 182 [M+H]⁺.

Step 6 to Step 10 were carried out following representative procedures described in Example 5. 1-292 (40 mg) m/z 467.6 ¹H NMR (400 MHz, DMSO): δ 9.55 (s, 1H), 8.35-8.34 (d, J=4.8 Hz, 1H), 8.26 (s, 1H), 8.19 (s, 1H), 8.03-8.03 (s, 1H), 7.49-7.49 (d, J=3.2 Hz, 1H), 7.43-7.40 (m, 1H), 7.04-7.03 (m, 1H), 6.96-6.94 (m, 1H), 6.12-6.11 (m, 1H), 4.44 (s, 1H), 4.10-4.06 (d, J=18 Hz, 1H), 3.89 (s, 3H), 3.63 (s, 1H), 3.84 (s, 1H), 3.67 (s, 1H), 3.48-3.45 (m, 2H), 2.90-2.86 (t, J=19.2, 2H), 2.15 (s, 3H), 1.87 (s, 2H), 1.57-1.55 (m, 2H).

Example 14. Method O

Synthesis of 4-(1-methyl-1H-pyrrolo[2,3-b]pyridin-4-yl)-7-((5-((methylsulfonyl)methyl)pyridin-2-yl)amino)isoindolin-1-one (I-293)

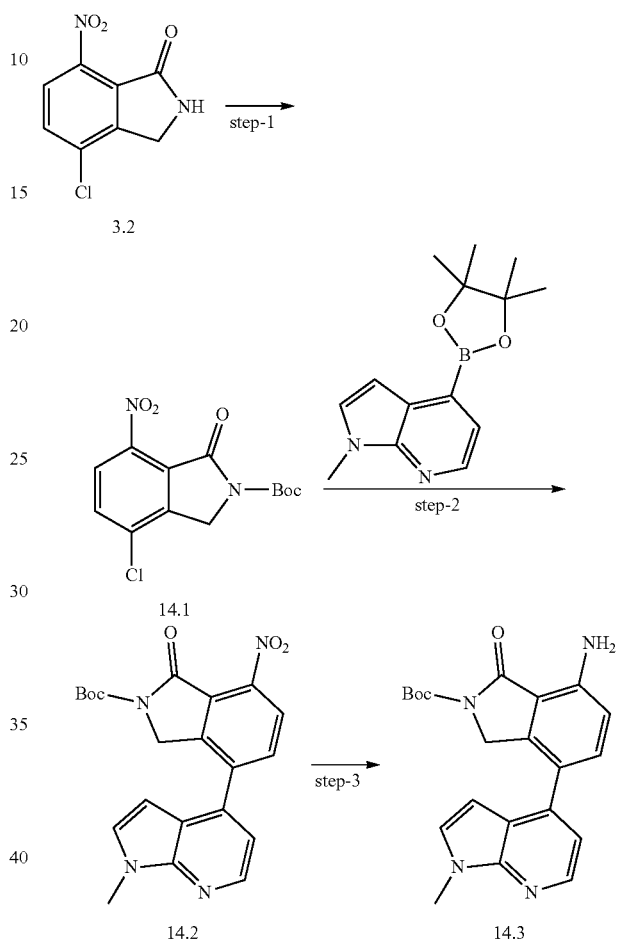

Step 1. Tert-Butyl 4-chloro-7-nitro-1-oxoisoindoline-2-carboxylate (14.1)

A mixture of 4-chloro-7-nitroisoindolin-1-one (3.2) (5.00 g, 23.53 mmol) in 1,4-dioxane (50 mL) was added Boc-anhydride (7.69 g, 35.29 mmol), TEA (7.1 g 9.8 mL, 70.58 mmol) and DMAP (0.28 g, 2.35 mmol) at rt. The reaction was stirred for 30 min at rt. The reaction mixture was diluted with Water (300 mL). The mixture was extracted with ethyl acetate (3×250 mL) and the combined organic phases were washed with brine (100 mL), dried with Na₂SO₄, filtered, and then concentrated in vacuo. The residue was triturated with hexanes and n-pentane to afford the title compound (14.1) (7.3 g, 99.2%) as off white solid. m/z=313.5 [M+H]⁺, Step 2. Tert-Butyl 4-(1-methyl-1H-pyrrolo[2,3-b]pyridin-4-yl)-7-nitro-1-oxoisoindoline-2-carboxylate (14.2)

A solution of tert-butyl 4-chloro-7-nitro-1-oxoisoindoline-2-carboxylate (14.1) (1.0 g, 3.2 mmol) and 1-methyl- 4-(4,4,5,5-tetramethyl-1,3,2-dioxaborolan-2-yl)-1H-pyrrolo[2,3-b]pyridine (0.9 g, 3.52 mmol) in 1,4-dioxane:Water (9:1) (25 mL) was added tribasic potassium phosphate (2.0 g, 9.60 mmol). The reaction mixture was degassed with argon gas for 10 min. X-phos Pd G2 (0.13 g, 0.16 mmol) was added into reaction mixture the reaction was stirred for 30 min at 110° C. The reaction mixture was diluted with Water (80 mL). The mixture was extracted with ethyl acetate (3×100 mL) and the combined organic phases were washed with brine (80 mL), dried with $Na_2SO_4$, filtered, and then concentrated in vacuo. The residue was purified by column chromatography (0-10% gradient elution EtOAc in Hexanes) to afford the title compound 14.2 (0.91 g, 68.9%) as light yellow solid. m/z=409.3 $[M+H]^+$, Step 3. Tert-Butyl 7-amino-4-(1-methyl-1H-pyrrolo[2,3-b]pyridin-4-yl)-1-oxoisoindoline-2-carboxylate (14.3)

To a solution of tert-butyl 4-(1-methyl-1H-pyrrolo[2,3-b]pyridin-4-yl)-7-nitro-1-oxoisoindoline-2-carboxylate (14.2) (0.8 g, 1.96 mmol) in THF (30 mL) was added Raney nickel (0.4 g, 50% w/w). The reaction was purged with $H_2$ gas for 2 h. The slurry was filtered off under vacuum filtration and celite bed was washed with methanol (80 mL). The solvent was removed in vacuo to yield the title compound (14.3) (0.7 g, 94.43%) as an off white solid. m/z=379.2 $[M+H]^+$

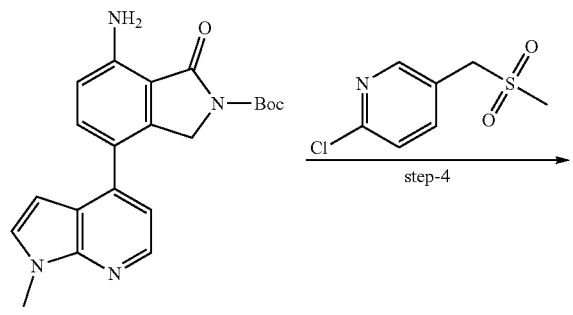

14.3

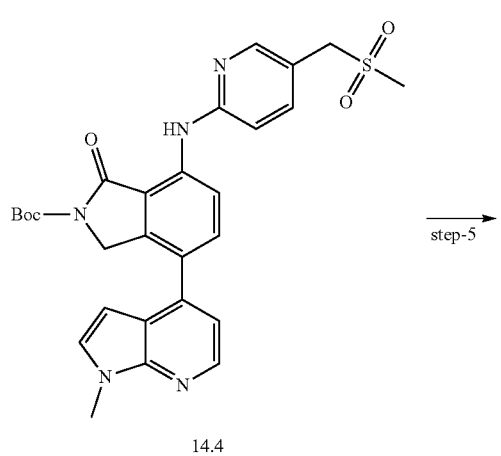

14.4

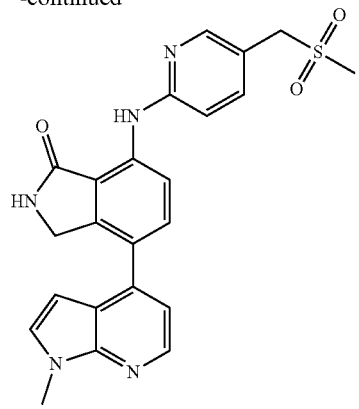

I-293

Step 4. Tert-Butyl 4-(1-methyl-1H-pyrrolo[2,3-b]pyridin-4-yl)-7-((5-((methylsulfonyl)methyl)pyridin-2-yl)amino)-1-oxoisoindoline-2-carboxylate (14.4)

To a solution of tert-butyl 7-amino-4-(1-methyl-1H-pyrrolo[2,3-b]pyridin-4-yl)-1-oxoisoindoline-2-carboxylate (14.3) (0.5 g, 1.32 mmol) in dry 1,4-dioxane (10 mL) was added $Cs_2CO_3$ (0.85 g, 2.64 mmol) followed by 2-chloro-5-((methylsulfonyl)methyl)pyridine (0.27 g, 1.32 mmol). The mixture was purged with an argon stream for 10 min before Xantphos (76 mg, 0.132 mmol) and $Pd_2(dba)_3$ (121 mg, 0.132 mmol) were added. The mixture was degassed for 10 more min. The reaction was then stirred at 120° C. for 4 h. After cooling to RT, the reaction mixture was poured into saturated Water (80 mL). The mixture was extracted with ethyl acetate (2×80 mL). The combined organic phases were washed with brine (25 mL), dried over $Na_2SO_4$, filtered, and concentrated under reduced pressure. The crude product was purified by column chromatography (0-25% gradient elution EtOAc in Hexanes) to afford the desired compound 14.4 (0.22 g, 30.4%) as a yellow solid. m/z=548.5 $[M+H]^+$ Step 5. Synthesis of 4-(1-methyl-1H-pyrrolo[2,3-b]pyridin-4-yl)-7-((5-((methylsulfonyl)methyl)pyridin-2-yl)amino)isoindolin-1-one (I-293)

A solution of tert-butyl 4-(1-methyl-1H-pyrrolo[2,3-b]pyridin-4-yl)-7-((5-((methyl sulfonyl)methyl)pyridin-2-yl)amino)-1-oxoisoindoline-2-carboxylate (14.4) (0.135 g, 0.2 mmol) was dissolved in DCM (2.0 mL) and 4M HCl in dioxane (1 mL) added under nitrogen atmosphere. The reaction mixture was stirred at RT for 30 min. After completion of reaction, the reaction mixture was diluted with water and basified using saturated sodium bicarbonate solution then extracted with DCM (3×30 mL). The combine organic layer washed with brine solution, dried over sodium sulfate, and concentrated under reduced pressure to afford crude material. The residue was purified by column chromatography eluting with 3-4% MeOH in DCM to afford I-293 (0.045 g, 33.33%) MS (ES): 448 m/z $[M+H]+$, $^1H$ NMR (400 MHz, DMSO): δ 10.298 (s, 1H), 8.872 (s, 1H), 8.74-8.72 (d, J=8.6 Hz, 1H), 8.33 (s, 2H), 7.80-7.73 (m, 2H), 7.60 (s, 1H), 7.29-7.28 (m, 1H), 7.10-7.07 (d, J=8.6 Hz, 1H), 6.49 (s, 1H), 4.49 (s, 1H), 3.88 (s, 1H), 2.96 (s, 3H).

Example 16. Method Q

Synthesis of 7-bromo-4-chloro-2-(2,4-dimethoxy-benzyl)-2,3-dihydro-1H-pyrrolo[3,4c]pyridin-1-one (I-289)

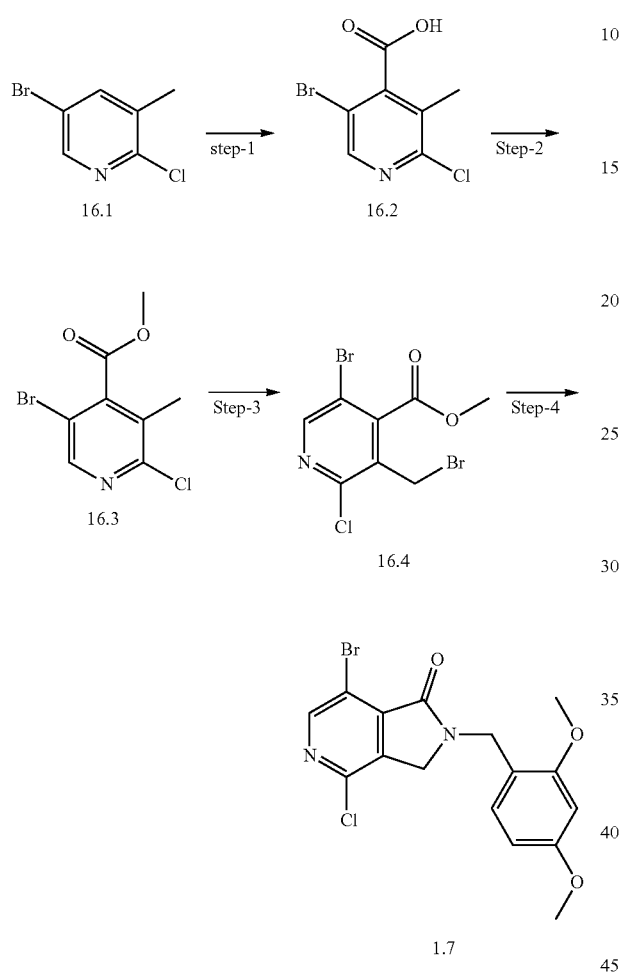

Step 1. 5-bromo-2-chloro-3-methylisonicotinic Acid (16.2)

A solution of 5-bromo-2-chloro-3-methylpyridine (16.1) (2.5 g, 12.135 mmol) in THF (20 mL) was cooled at −78° C. under a nitrogen atmosphere, and was treated dropwise with lithium diisopropyl amide (2M solution in THF, 6.6 mL, 13.34 mmol). After the addition, the mixture was stirred for 30 min. then purged with CO2 gas for 30 min. The mixture was allowed to warm to RT and stirred for 45 min. The reaction mixture was combined with 48 other batch on the same scale prepared by an identical method. The mixture was quenched with saturated NaHCO₃ solution (25 mL) and extracted EtOAc (3×20 mL). Aqueous layer wash was neutralized by Hydrochloric acid till PH-4 and extracted by 30% isopropyl alcohol in chloroform. The combined extract was dried over sodium sulfate and concentrated under vacuum to leave the title compound 16.2 (79.87 g, 53.7%) as white solid material. m/z 250.5 [M+H]⁺

Step 2. Methyl 5-bromo-2-chloro-3-methylisonicotinate (16.3)

To a solution of 5-bromo-2-chloro-3-methylisonicotinic acid (16.2) (20 g, 80.0 mmol) in dry DMF (200 mL) at RT under a nitrogen atmosphere was added potassium carbonate (22.08 g, 160.0 mmol) and methyl Iodide (17.02 g, 120.0 mmol) dropwise. After the addition, the mixture was stirred at RT for 16 h. The reaction mixture was combined with 3 other batches on the same scale prepared by an identical method. The mixture was quenched with water and extracted with ethyl acetate (2×25 mL) and the combined organic phases were washed with brine (20 mL), dried with MgSO4, filtered, and then concentrated in vacuo. The residue was purified by column chromatography (0-2% gradient elution EtOAc in iso-hexane) to afford the title compound 16.3 (65 g, 76.94%) as colorless oil. m/z 265.5 [M+H]⁺

Step 3. methyl 5-bromo-3-(bromomethyl)-2-chloroisonicotinate (16.4)

A solution of methyl 5-bromo-2-chloro-3-methylisonicotinate (16.3) (10 g, 37.87 mmol) in carbon tetrachloride (90 mL) was treated with N-bromo succinimide (13.4 g, 75.75 mmol), followed by azobisisobutyronitrile (0.62 g, 3.787 mmol). The resulting mixture was heated at 80° C. for 16 h. The reaction mixture was combined with 5 other batches on the same scale prepared by an identical method. After completion of reaction the solvent was eliminated under vacuum and the residue was purified by column chromatography (0-2% gradient elution EtOAc in iso-hexane) to afford the title compound 16.4 (75 g, 96.28%) as white solid. m/z 344 [M+H]⁺.

Step 4. 7-bromo-4-chloro-2-(2,4-dimethoxybenzyl)-2,3-dihydro-1H-pyrrolo[3,4-c]pyridin-1-one Synthesis of Compound (1.7)

To a solution of methyl 5-bromo-3-(bromomethyl)-2-chloroisonicotinate 16.4 (18 g, 61.64 mmol) in methanol (70 mL) was added N, N-Diisopropylethylamine (35.2 g, 272.7 mmol) and 2,4-Dimethoxybenzylamine (12 g, 74.99 mmol). The reaction mixture stirred at RT for 30 min. The reaction mixture was combined with 3 other batches on the same scale prepared by an identical method. The reaction was filtered, and the residue was washed with methanol and dried under vacuum to afford the title compound 1.7 (80 g, 95.95%) as a white solid m/z 397 [M+1]⁺.

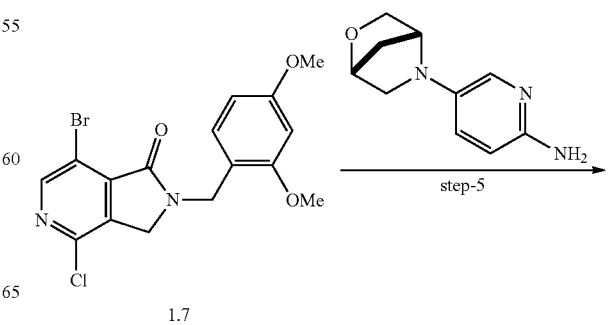

-continued

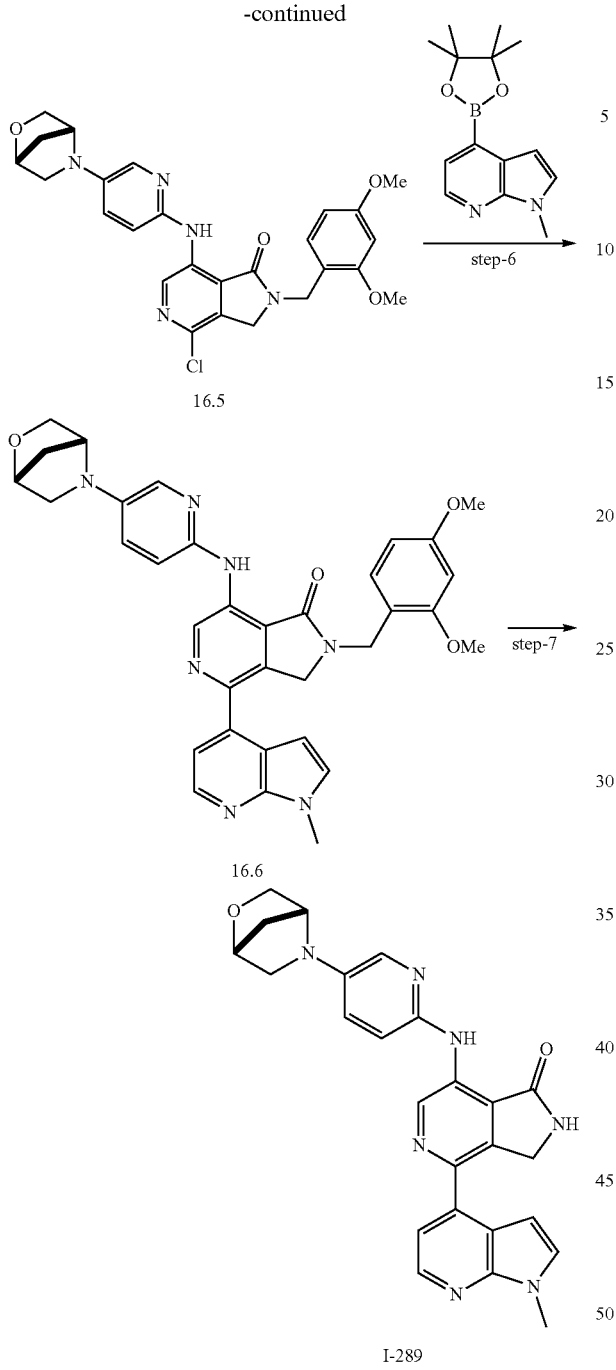

16.5

16.6

I-289

Synthesis of 7-((5-((1R,4R)-2-oxa-5-azabicyclo [2.2.1]heptan-5-yl)pyridin-2-yl)amino)-4-(1-methyl-1H-pyrrolo[2,3-b]pyridin-4-yl)-2,3-dihydro-1H-pyrrolo[3,4-c]pyridin-1-one (I-289)

Step 5, 6 and 7 were carried out following representative procedures described in Example 1. (45 mg), m/z 453.5, $^1$H NMR (400 MHz, DMSO): δ 9.86 (s, 1H), 9.42 (s, 1H), 9.14 (s, 1H), 8.36-8.34 (m, 1H), 7.84 (s, 1H), 7.57-7.56 (m, 1H), 7.38-7.37 (m, 1H), 7.20-7.17 (m, 1H), 7.07-7.05 (d, J=8 Hz, 1H), 6.92-6.92 (m, 1H), 4.72 (s, 2H), 4.64-4.61 (d, J=12 Hz, 2H), 3.88 (s, 3H), 3.77-3.70 (dd, J=22.5 Hz, 2H), 3.57-3.55 (d, J=8 Hz, 1H), 3.00-2.98 (d, J=8 Hz, 1H), 1.97-1.94 (d, J=12 Hz, 1H), 1.88-1.86 (d, J=8 Hz, 1H).

Example 17. Method R

Synthesis of 7-((5-((1S,4S)-2-oxa-5-azabicyclo [2.2.1]heptan-5-yl)pyridin-2-yl)amino)-4-(1-methyl-1H-pyrrolo[2,3-b]pyridin-4-yl)-2,3-dihydro-1H-pyrrolo[3,4-c]pyridin-1-one (I-309)

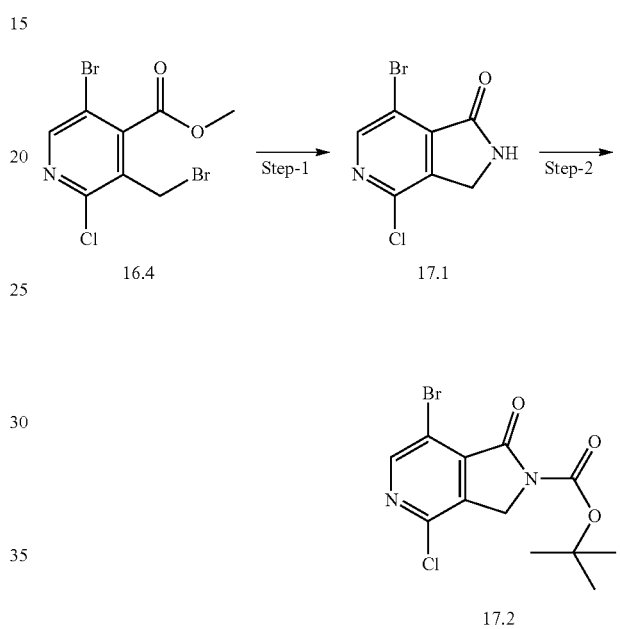

16.4

17.1

17.2

Step 1. 7-bromo-4-chloro-2,3-dihydro-1H-pyrrolo[3,4-c]pyridin-1-one (17.1)

To a stirred solution of methyl 5-bromo-3-(bromomethyl)-2-chloroisonicotinate (16.4) (18 g, 61.64 mmol) in methanol (70 mL) was purged ammonia gas at 0° C. After 1 h solid precipitate was observed in the reaction mixture. The reaction mixture was combined with 3 other batches on the same scale prepared by an identical method. The reaction mixture was filtered. The residue was wash with methanol and dried under vacuum to afford 17.1 (36 g, 69.38%) as brown solid. MS (ES) m/z 247-249 [M+2]$^+$ Step 2. tert-butyl 7-bromo-4-chloro-1-oxo-1,3-dihydro-2H-pyrrolo[3,4-c]pyridine-2-carboxylate (17.2)

To a solution of 7-bromo-4-chloro-2,3-dihydro-1H-pyrrolo[3,4-c]pyridin-1-one (17.1) (5 g, 20.24 mmol) in dioxane (250 mL) were added Dimethyl amino pyridine (0.24 g, 2.024 mmol) and Boc anhydride (5.0 g, 23.27 mmol) at RT. The reaction mixture stirred at RT for 1 h. Solid precipitate was dissolve in reaction mixture. The reaction mixture was combined with 13 other batches on the same scale prepared by an identical method. The reaction was diluted with water (750 mL) and extracted by ethyl acetate (3×500 mL). The combined organic layer dried over sodium sulfate and concentrate under vacuum to afford residue was purified by column chromatography (0-5% gradient elution EtOAc in iso-hexane) to afford the title compound 17.2 (40 g, 79.11%) as a white solid MS (ES): m/z 347-349 [M+2]⁺.

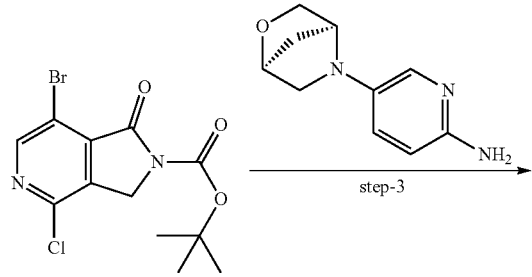
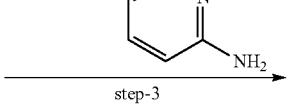

17.2

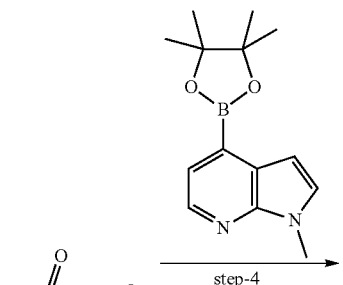

17.3

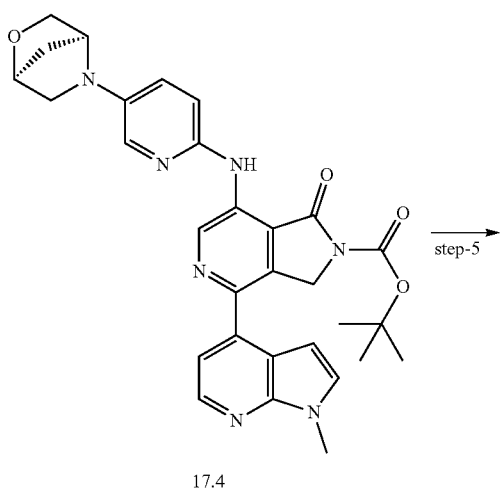
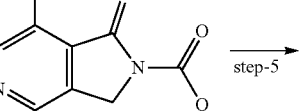

17.4

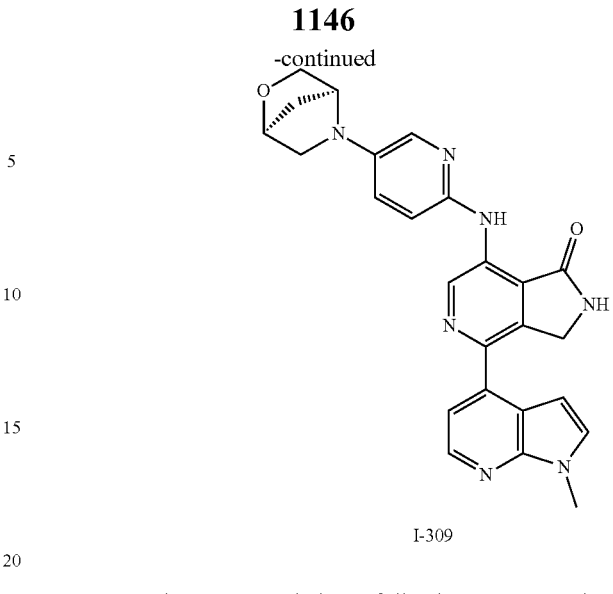

I-309

Step 3 and 4 were carried out following representative procedures described in Example 1 to afford 17.4.

Step 5. 7-((5-((1S,4S)-2-oxa-5-azabicyclo[2.2.1]heptan-5-yl)pyridin-2-yl)amino)-4-(1-methyl-1H-pyrrolo[2,3-b]pyridin-4-yl)-2,3-dihydro-1H-pyrrolo[3,4-c]pyridin-1-one (I-309)

To a solution of tert-butyl 7-((5-((1S,4S)-2-oxa-5-azabicyclo[2.2.1]heptan-5-yl)pyridin-2-yl)amino)-4-(1-methyl-1H-pyrrolo[2,3-b]pyridin-4-yl)-1-oxo-1,3-dihydro-2H-pyrrolo[3,4-c]pyridine-2-carboxylate 17.4 (0.120 g, 0.2 mmol) into DCM (3 mL) was added HCl in dioxane (3 mL) at 0° C. The reaction mixture was stirred at RT for 1 h. After completion of reaction, the reaction mixture was concentrated under reduced pressure to afford crude which was purified by column chromatography to afford the title compound I-309 (0.056 g, 56.98%) as a white solid. MS (ES): m/z 454.52 (M+H). ¹H NMR (400 MHz, DMSO): δ 9.85 (s, 1H), 9.41 (s, 1H), 9.13 (s, 1H), 8.34-8.33 (m, 1H), 7.83-7.82 (m, 1H), 7.56-7.55 (m, 1H), 7.37-7.35 (m, 1H), 7.19-7.16 (m, 1H), 7.05-7.03 (d, J=8 Hz, 1H), 6.91-6.90 (m, 1H), 4.70 (s, 2H), 4.62-4.59 (d, J=12 Hz, 2H), 3.86 (s, 3H), 3.76-3.74 (d, J=8 Hz, 1H), 3.70-3.68 (d, J=8 Hz, 1H), 3.55-3.53 (d, J=8 Hz, 1H), 2.98-2.96 (d, J=8 Hz, 1H), 1.95-1.93 (d, J=8 Hz, 1H) 1.87-1.84 (d, J=12 Hz, 1H).

Example 18. Method S

Synthesis of 7-((5-(4-hydroxypiperidin-1-yl)pyridin-2-yl)amino)-4-(imidazo[1,2-a]pyrazin-5-yl)-2,3-dihydro-1H-pyrrolo[3,4-c]pyridin-1-one (I-376)

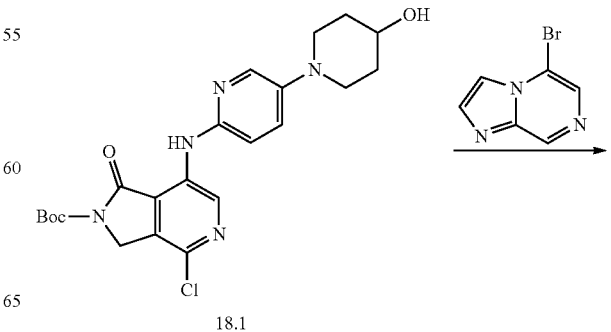

18.1

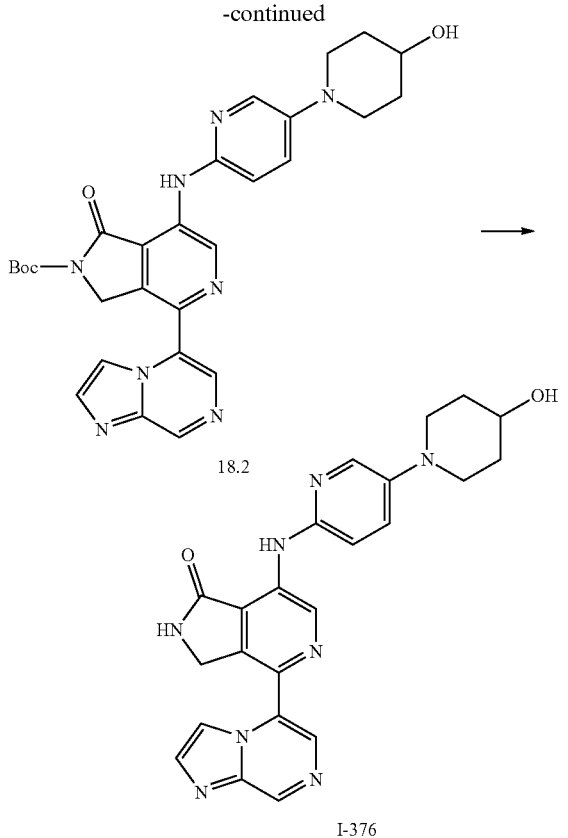

Step 1. Tert-Butyl 7-((5-(4-hydroxypiperidin-1-yl)pyridin-2-yl)amino)-4-(imidazo[1,2-a]pyrazin-5-yl)-1-oxo-1,3-dihydro-2H-pyrrolo[3,4-c]pyridine-2-carboxylate (18.2)

To a mixture of tert-butyl 4-chloro-7-((5-(4-hydroxypiperidin-1-yl)pyridin-2-yl)amino)-1-oxo-1,3-dihydro-2H-pyrrolo[3,4-c]pyridine-2-carboxylate (18.1) (prepared according to Example 1) (0.500 g, 1.0 mmol) and 5-bromoimidazo[1,2-a]pyrazine (0.256 g, 1.3 mmol) in 1,4-dioxane (20 mL) was added hexametyldititin (0.534 g, 1.6 mmol, 1.5 eq) at RT. The reaction mixture was degassed using nitrogen gas for 20 mins. tetrakis(triphenylphosphine)-palladium(O) (0.062 g, 0.05 mmol, 0.05 eq) was added to the reaction mixture and stirred at 100° C. for 48 h. The reaction mixture was diluted with Water (60 mL). The mixture was extracted with ethyl acetate (3×80 mL) and the combined organic phases were washed with brine (80 mL), dried with $Na_2SO_4$, filtered, and then concentrated in vacuo. The residue was purified by column chromatography (0-4% methanol gradient in DCM) and then was purified by prep HPLC to afford to afford the title compound (18.2) (0.04 g, 6.78%) as off white solid. LCMS: 100% m/z=542 [M+H]$^+$ Step 2. 7-((5-(4-hydroxypiperidin-1-yl)pyridin-2-yl)amino)-4-(imidazo[1,2-a]pyrazin-5-yl)-2,3-dihydro-1H-pyrrolo[3,4-c]pyridin-1-one (I-376)

To a solution of tert-butyl 7-((5-(4-hydroxypiperidin-1-yl)pyridin-2-yl)amino)-4-(imidazo[1,2-a]pyrazin-5-yl)-1-oxo-1,3-dihydro-2H-pyrrolo[3,4-c]pyridine-2-carboxylate (18.2) (0.040 g, 0.07 mmol) in DCM (3 mL) was added TFA (1.0 mL). The reaction was stirred for 1 h at RT. After completion of reaction, the reaction mixture was diluted with water and basified using saturated sodium bicarbonate solution, then extracted with DCM (3×30 mL). The combined organic layer was washed with brine solution, dried over sodium sulfate and the solvent was removed in vacuo. The residue was purified via prep HPLC (0.1% TFA in water and 100% acetonitrile) to afford I-376 (0.015 g, 31.79%) MS (ES): 442 m/z [M+H]+, $^1$H NMR (400 MHz, DMSO): δ 9.94 (s, 1H), 9.76-9.75 (m, 1H), 9.44 (s, 1H), 9.30 (s, 1H), 9.21 (s, 1H), 8.29 (s, 1H), 8.07-8.05 (m, 2H), 7.48-7.45 (m, 1H), 7.04-7.02 (d, J=8 Hz, 1H), 4.80 (s, 2H), 4.72-4.70 (m, 1H), 3.63 (s, 1H), 3.46-3.38 (m, 2H), 2.86-2.81 (t, J=8 Hz, 2H), 1.84 (s, 2H), 1.53-1.51 (m, 2H).

Example 19. Method T

Synthesis of 7-((4-((3R,4R)-4-fluoro-3-hydroxypiperidin-1-yl)pyridin-2-yl)amino)-4-(imidazo[1,2-a]pyrazin-3-yl)isoindolin-1-one (I-434) & 7-((4-((3S,4S)-4-fluoro-3-hydroxypiperidin-1-yl)pyridin-2-yl)amino)-4-(imidazo[1,2-a]pyrazin-3-yl)isoindolin-1-one (I-435)

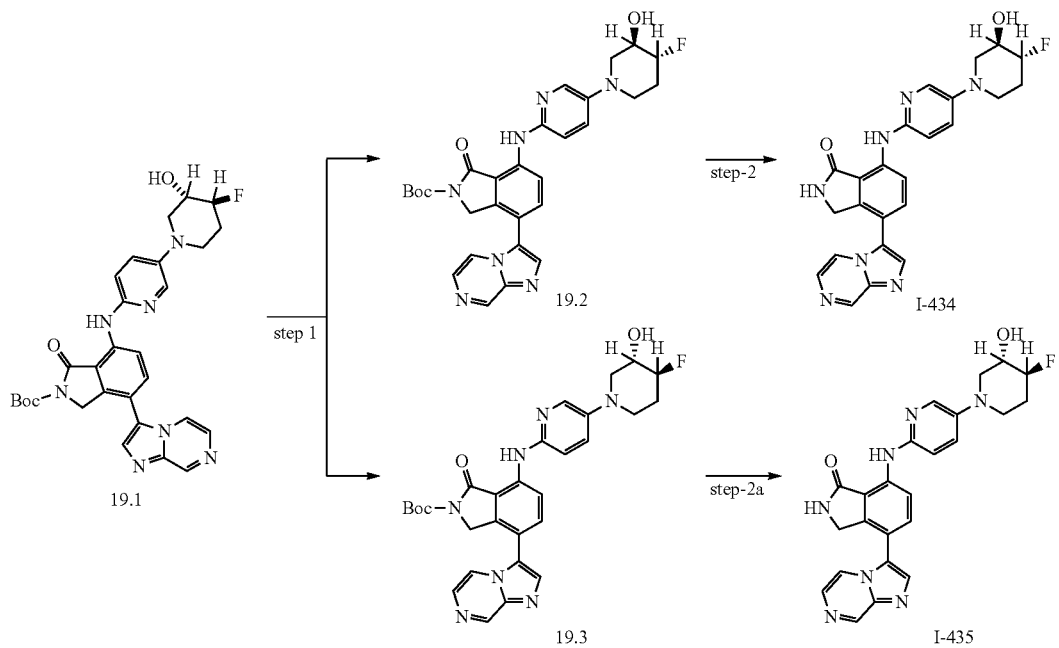

Racemic Tert-Butyl 7-((5-((3,4)-4-fluoro-3-hydroxypiperidin-1-yl)pyridin-2-yl)amino)-4-(imidazo [1,2-a]pyrazin-3-yl)-1-oxoisoindoline-2-carboxylate (19.1)

Compound 19.1 was synthesized in a similar fashion to that described in Example 9.

Step 1 Synthesis of Tert-Butyl 7-((5-((3r,4r)-4-fluoro-3-hydroxypiperidin-1-yl)pyridin-2-yl)amino)-4-(imidazo[1,2-a]pyrazin-3-yl)-1-oxoisoindoline-2-carboxylate (19.2) and Tert-Butyl 7-((5-((3s,4s)-4-fluoro-3-hydroxypiperidin-1-yl)pyridin-2-yl)amino)-4-(imidazo[1,2-a]pyrazin-3-yl)-1-oxoisoindoline-2-carboxylate (19.3)

19.1 (250 mg) were separated by Chiral SFC-Shimadzu LC-20AP and UV detector. The column used was CHIRALPAK IC (250*21.0) mm, 5 micron, column flow was 20 mL/min. Mobile phase used: (A) 0.1% DEA IN n-Hexane, (B) 0.1% DEA In propanol:acetonitrile (70:30), to provide compounds 19.2 (100 mg) and 19.3 (110 mg).

Step 2: 7-((5-((3R,4R)-4-fluoro-3-hydroxypiperidin-1-yl)pyridin-2-yl)amino)-4-(imidazo[1,2-a]pyrazin-3-yl)isoindolin-1-one (I-434)

To a solution of tert-butyl 7-((5-((3R,4R)-4-fluoro-3-hydroxypiperidin-1-yl)pyridin-2-yl)amino)-4-(imidazo[1,2-a]pyrazin-3-yl)-1-oxoisoindoline-2-carboxylate (19.2) (0.100 g, 0.1 mmol) in DCM (3 mL) was added HCl in dioxane (3 mL) at 0° C. The reaction mixture was stirred at RT for 1 h. The reaction mixture was neutralized using saturated sodium bicarbonate solution, then extracted with 10% methanol in DCM (3×30 mL) and the combined organic layers were concentrated under reduced pressure to afford crude, which was purified by column chromatography to provide the title compound I-434 (0.030 g, 36.54%) as a white solid. MS (ES): m/z 460.52 (M+H). $^1$H NMR (400 MHz, DMSO): δ 9.90 (s, 1H), 9.15-9.15 (m, 1H), 8.82 (s, 1H), 8.60-8.58 (d, J=8 Hz, 1H), 8.48-8.46 (m, 1H), 8.12 (s, 1H), 8.04-8.03 (d, J=4 Hz, 1H), 7.93-7.91 (d, J=8 Hz, 1H), 7.78-7.76 (d, J=8 Hz, 1H), 7.49-7.46 (dd, J=8.8 Hz, 12 Hz, 1H), 6.99-6.97 (d, J=8 Hz, 1H), 5.43 (s, 1H), 4.53-4.34 (m, 3H), 3.71-3.64 (m, 1H), 3.61-3.52 (m, 2H), 2.86-2.81 (m, 1H), 2.69-2.63 (m, 1H), 2.16-2.10 (m, 1H) 1.78-1.74 (m, 1H).

Step 2a: 7-((5-((3S,4S)-4-fluoro-3-hydroxypiperidin-1-yl)pyridin-2-yl)amino)-4-(imidazo[1,2-a]pyrazin-3-yl)isoindolin-1-one (I-435)

To a solution of tert-butyl 7-((5-((3S,4S)-4-fluoro-3-hydroxypiperidin-1-yl)pyridin-2-yl) amino)-4-(imidazo[1,2-a]pyrazin-3-yl)-1-oxoisoindoline-2-carboxylate (19.3) (0.100 g, 0.1 mmol) into DCM (3 mL) was added HCl in dioxane (3 mL) at 0° C. The reaction mixture was stirred at RT for 1 h. The reaction mixture was neutralized using saturated sodium bicarbonate solution, then extracted with DCM (3×30 mL) and the combined organic layers were concentrated under reduced pressure to afford crude which was purified by column chromatography to provide the title compound I-435 (0.042 g, yield-5154%) as a white solid. MS (ES): m/z 460.52 (M+H). $^1$H NMR (400 MHz, DMSO): δ 9.91 (s, 1H), 9.15 (s, 1H), 8.83 (s, 1H), 8.60-8.58 (d, J=8 Hz, 1H), 8.48-8.46 (m, 1H), 8.16 (s, 1H), 8.12-8.10 (d, J=8 Hz, 1H), 8.04-8.03 (d, J=4 Hz, 1H), 7.93-7.91 (d, J=8 Hz, 1H), 7.78-7.76 (d, J=8 Hz, 1H), 7.49-7.46 (dd, J=8 Hz, 8 Hz, 1H), 4.51 (s, 1H), 4.510-4.35 (m, 3H), 3.71-3.64 (m, 1H), 3.60-3.53 (m, 2H), 2.86-2.81 (m, 1H), 2.68-2.63 (m, 1H), 2.15-2.09 (m, 1H) 1.78-1.74 (m, 1H).

Example 20. Method U

Synthesis of 4-(1-methyl-1H-pyrrolo[2,3-b]pyridin-4-yl)-7-((7-methyl-5,6,7,8-tetrahydro-1,7-naphthyridin-2-yl)amino)-2,3-dihydro-1H-pyrrolo[3,4-c]pyridin-1-one (I-418)

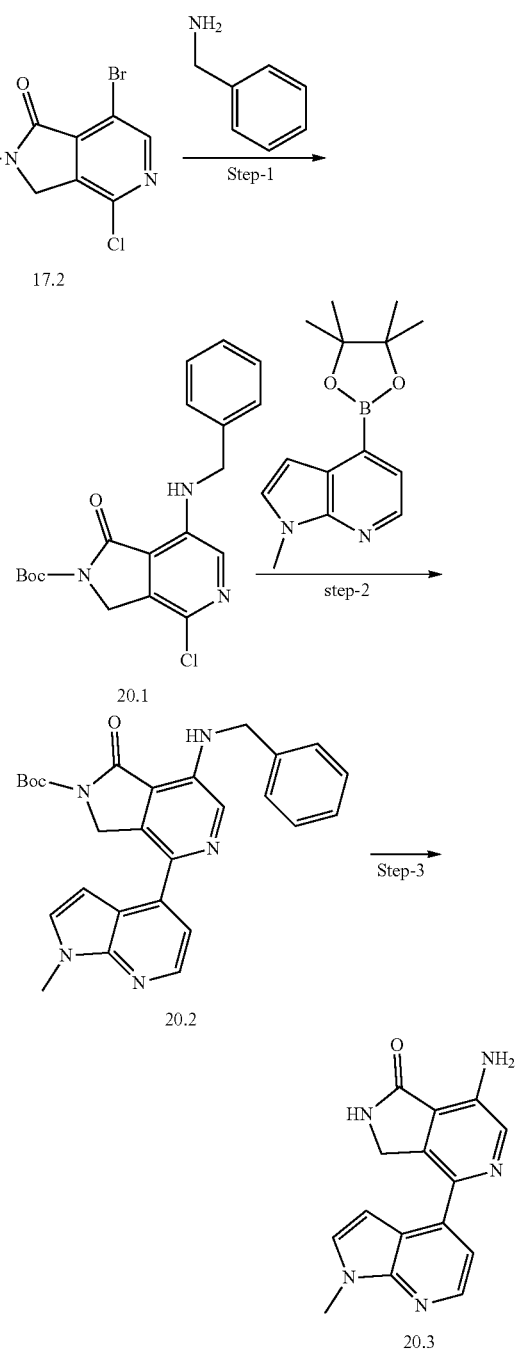

Step 1. Tert-Butyl 7-(benzylamino)-4-chloro-1-oxo-1,3-dihydro-2H-pyrrolo[3,4-c]pyridine-2-carboxylate (20.1)

To a solution of tert-butyl 7-bromo-4-chloro-1-oxo-1,3-dihydro-2H-pyrrolo[3,4-c]pyridine-2-carboxylate (17.2) (3 g, 8.6 mmol) in dry toluene (40 mL) was added $K_2CO_3$ (3.7 g, 26.06 mmol) followed by phenylmethanamine (1.02 g, 9.54 mmol). The mixture was purged with a $N_2$ stream for 10 min before Xantphos (1.0 g, 1.704 mmol) and $Pd_2(dba)_3$ (0.794 g, 0.86 mmol) were added. The mixture was degassed for 10 more min. The reaction was then stirred at 120° C. for 2 h. After cooling to RT, the reaction mixture was poured into saturated aqueous $NH_4Cl$ solution (30 mL) and filtered through a Celite Pad. The mixture was extracted with ethyl acetate (2×25 mL). The combined organic phases were washed with brine (25 mL), dried over $Na_2SO_4$, filtered, and concentrated under reduced pressure. The crude product was purified by column chromatography (0-10% gradient elution EtOAc in iso-hexane) to afford the desired compound (20.1) (1.8 g, 46.49%) as a white solid. m/z=374.1 $[M+H]^+$.

Step 2. Tert-Butyl 7-(benzylamino)-4-(1-methyl-1H-pyrrolo[2,3-b]pyridin-4-yl)-1-oxo-1,3-dihydro-2H-pyrrolo[3,4-c]pyridine-2-carboxylate (20.2)

To a solution of tert-butyl 7-(benzylamino)-4-chloro-1-oxo-1,3-dihydro-2H-pyrrolo[3,4-c]pyridine-2-carboxylate (20.1) (1.8 g, 4.9 mmol) and 1-methyl-4-(4,4,5,5-tetramethyl-1,3,2-dioxaborolan-2-yl)-1H-pyrrolo[2,3-b]pyridine (1.9 g, 7.4 mmol) in 1,4-dioxane:Water (9:1) (25 mL) was added tribasic potassium phosphate (3.14 g, 14.80 mmol). The reaction mixture was degassed with argon gas for 10 min. X-phos Pd G2 (0.194 g, 0.26 mmol) was added into reaction mixture. The reaction was stirred for 30 min at 110° C. The reaction mixture was diluted with Water (80 mL). The mixture was extracted with ethyl acetate (3×100 mL) and the combined organic phases were washed with brine (80 mL), dried with $Na_2SO_4$, filtered, and then concentrated in vacuo. The residue was purified by column chromatography (0-10% methanol gradient in DCM) to afford the title compound 20.2 (1.5 g, 66.7%) as light yellow solid. m/z=470.3 $[M+H]^+$.

Step 3. 7-amino-4-(1-methyl-1H-pyrrolo[2,3-b]pyridin-4-yl)-2,3-dihydro-1H-pyrrolo[3,4-c]pyridin-1-one (20.3)

A solution of compound tert-butyl 7-(benzylamino)-4-(1-methyl-1H-pyrrolo[2,3-b]pyridin-4-yl)-1-oxo-1,3-dihydro-2H-pyrrolo[3,4-c]pyridine-2-carboxylate (20.2) (1.5 g, 3.11 mmol) in DCM (10 mL) and trifluoroacetic acid (5 mL) was added at 0° C. The reaction mixture was stirred at RT for 1 h. The reaction mixture was quenched with saturated solution of sodium bicarbonate (200 mL) and the precipitate was collected by filtration. The solid was washed with water and dried in vacuo to afford the title compound 20.3 (0.6 g, 67.54%). m/z 280.30 $[M+H]^+$.

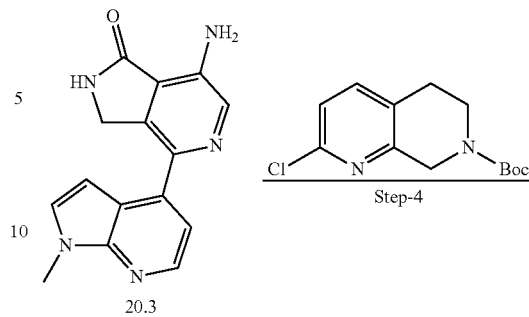

20.3

Step-4

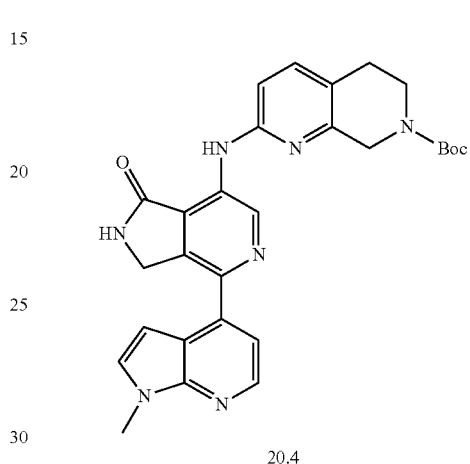

20.4

Step-5

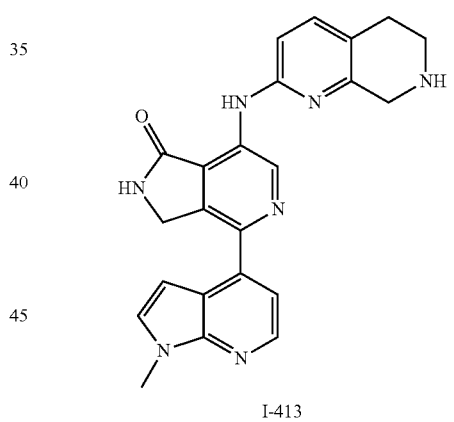

I-413

Step-6

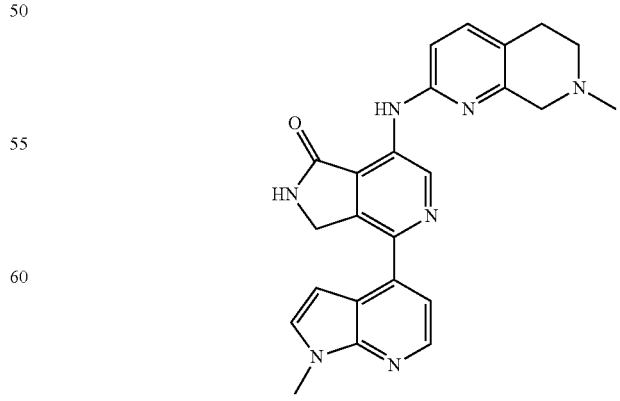

I-418

Step 4. Tert-Butyl 2-((4-(1-methyl-1H-pyrrolo[2,3-b]pyridin-4-yl)-1-oxo-2,3-dihydro-1H-pyrrolo[3,4-c]pyridin-7-yl)amino)-5,8-dihydro-1,7-naphthyridine-7(6H)-carboxylate (20.4)

To a solution of 7-amino-4-(1-methyl-1H-pyrrolo[2,3-b]pyridin-4-yl)-2,3-dihydro-1H-pyrrolo[3,4-c]pyridin-1-one (20.3) (0.6 g, 2.15 mmol) in dry DMF (18 mL) was added K$_3$PO$_4$ (1.3 g, 6.40 mmol) followed by tert-butyl 2-chloro-5,8-dihydro-1,7-naphthyridine-7(6H)-carboxylate (0.690 g, 2.54 mmol). The mixture was purged with a N$_2$ stream for 10 min then BrettPhos Pd G3 (0.136 g, 0.150 mmol) was added into reaction mixture. The mixture was degassed for 10 more min. The reaction was then stirred at 120° C. for 2 h. After cooling to RT, the reaction mixture was poured into saturated aqueous NH$_4$Cl solution (30 mL) and filtered through a Celite Pad. The mixture was extracted with ethyl acetate (2×25 mL). The combined organic phases were washed with brine (25 mL), dried over Na$_2$SO$_4$, filtered, and concentrated under reduced pressure. The crude product was purified by column chromatography (0-10% gradient elution EtOAc in iso-hexane) to afford the desired compound 20.4 (0.25 g, 22.7%) as a white solid. m/z=512.1 [M+H]$^+$,

Step 5. Tert-Butyl 2-((4-(1-methyl-1H-pyrrolo[2,3-b]pyridin-4-yl)-1-oxo-2,3-dihydro-1H-pyrrolo[3,4-c]pyridin-7-yl)amino)-5,8-dihydro-1,7-naphthyridine-7(6H)-carboxylate (I-413)

To a solution of tert-butyl 2-((4-(1-methyl-1H-pyrrolo[2,3-b]pyridin-4-yl)-1-oxo-2,3-dihydro-1H-pyrrolo[3,4-c]pyridin-7-yl)amino)-5,8-dihydro-1,7-naphthyridine-7(6H)-carboxylate (20.4) (0.250 g, 0.48 mmol) into DCM (3 mL) was added HCl in dioxane (3 mL) at 0° C. The reaction mixture was stirred at RT for 1 h. The reaction mixture was quenched with saturated solution of sodium bicarbonate (200 mL) and the precipitate was collected by filtration. The solid was washed with water and dried in vacuo to afford residue which was purified by column chromatography (0-2% methanol gradient in DCM) to afford the title compound I-413 (0.125 g, yield-62.54%) as a white solid. MS (ES): m/z 460.52 (M+H). $^1$H NMR (400 MHz, DMSO): δ 8.38-8.24 (m, 3H), 7.59-7.54 (m, 2H), 7.33-7.32 (d, J=4 Hz, 1H), 6.79 (s, 1H), 6.66 (s, 2H), 5.16 (s, 2H), 3.87-3.81 (m, 5H), 2.95 (s, 2H), 2.70 (s, 2H).

Step 6. 4-(1-methyl-1H-pyrrolo[2,3-b]pyridin-4-yl)-7-((7-methyl-5,6,7,8-tetrahydro-1,7-naphthyridin-2-yl)amino)-2,3-dihydro-1H-pyrrolo[3,4-c]pyridin-1-one (I-418)

To a solution of tert-butyl 2-((4-(1-methyl-1H-pyrrolo[2,3-b]pyridin-4-yl)-1-oxo-2,3-dihydro-1H-pyrrolo[3,4-c]pyridin-7-yl)amino)-5,8-dihydro-1,7-naphthyridine-7(6H)-carboxylate (I-413) (0.1 g, 3.11 mmol) in methanol (10 mL) was added formaldehyde (3.7 g, 26.06 mmol). The mixture was stirred for 30 min. Acetic acid (1.0 g, 1.704 mmol) and sodium cyanoborohydride (0.794 g, 0.86 mmol) were added. The reaction was then stirred at RT for 30 min. The reaction mixture was neutralized using saturated sodium bicarbonate solution then extracted with DCM (3×30 mL), and the combined organic layers were concentrated under reduced pressure to afford the residue, which was purified by column chromatography (0-2% methanol gradient in DCM) to afford the title compound I-418 (0.03 g, 30.1%) as white solid. m/z=426.3 [M+H]$^+$, $^1$H NMR (400 MHz, DMSO): δ 8.39-8.38 (d, J=4 Hz, 1H), 8.32-8.30 (m, 2H), 7.67-7.65 (d, J=8 Hz, 1H), 7.56-7.55 (d, J=4 Hz, 1H), 7.33-7.32 (d, J=4 Hz, 1H), 6.81-6.80 (d, J=4 Hz, 1H), 6.69 (s, 2H), 5.17 (s, 2H), 3.88 (s, 3H), 3.64 (s, 2H), 2.85-2.84 (m, 2H), 2.77 (s, 2H), 2.47 (s, 3H).

Example 21. Method Sp

Synthesis of R)-7-((6-((dimethylamino)methyl)-5-(tetrahydrofuran-3-yl)pyridin-2-yl)amino)-4-(7-fluoroimidazo[1,2-a]pyridin-3-yl)isoindolin-1-one (I-478) and (S)-7-((6-((dimethylamino)methyl)-5-(tetrahydrofuran-3-yl)pyridin-2-yl)amino)-4-(7-fluoroimidazo[1,2-a]pyridin-3-yl)isoindolin-1-one (I-479)

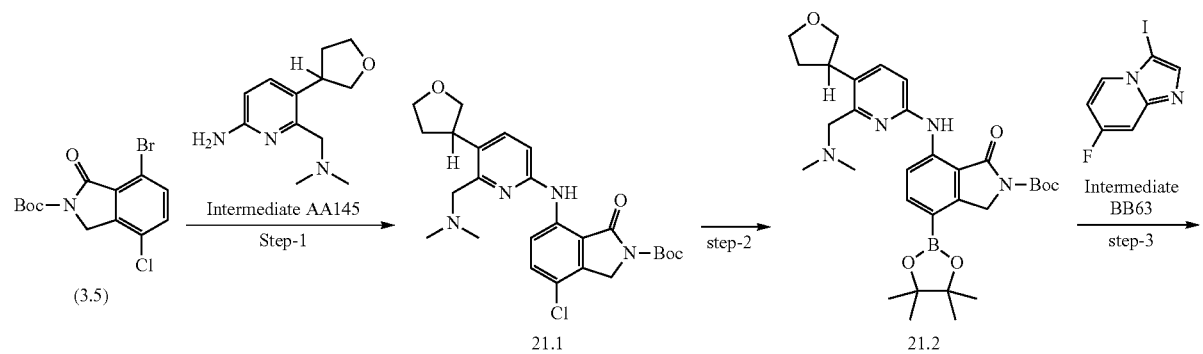

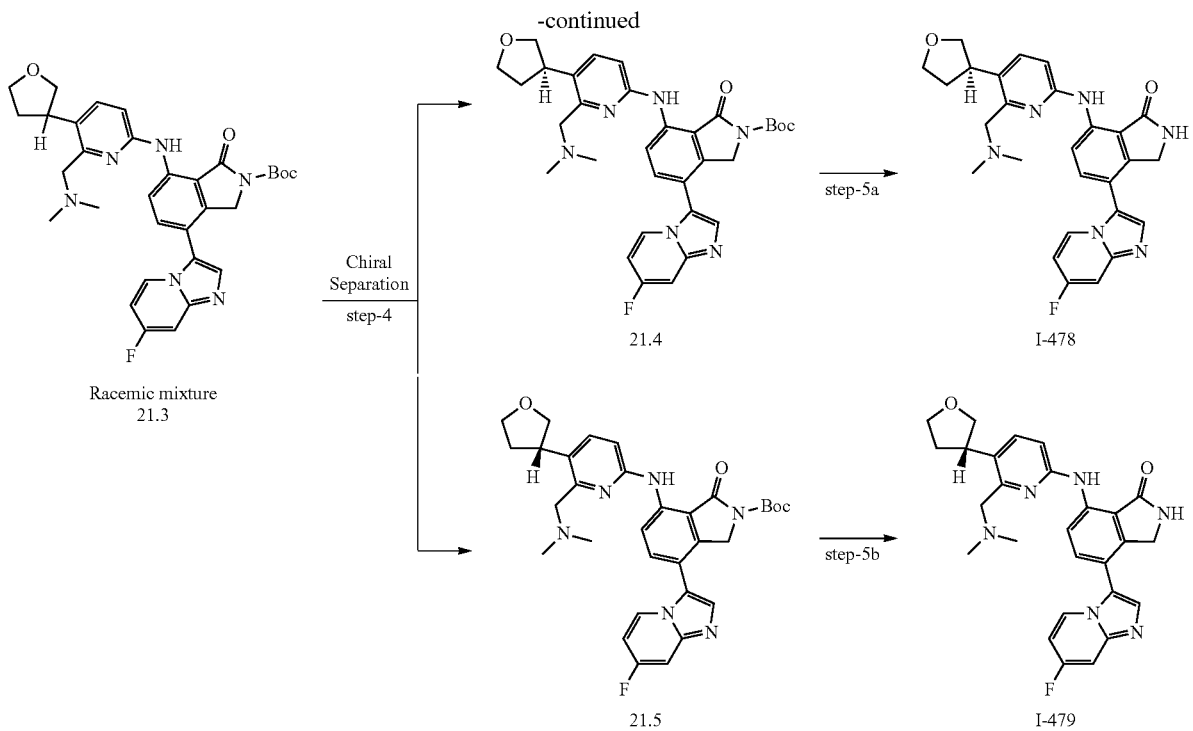

Step-1 Synthesis of Compound Tert-Butyl 4-chloro-7-((6-((dimethylamino)methyl)-5-(tetrahydrofuran-3-yl)pyridin-2-yl)amino)-1-oxoisoindoline-2-carboxylate (21.1)

To a solution of tert-butyl 7-bromo-4-chloro-1-oxoisoindoline-2-carboxylate (3.5) (100 g, 289.0 mmol) in 1-4 dioxane (1000 mL) were added Intermediate AA145 (63.95 g, 289.0 mmol) and cesium carbonate (281 g, 867.0 mmol, 3.0 eq) at RT. After degassing with flow of nitrogen for 20 min, 4,5-bis(diphenylphosphino)-9,9-dimethylxanthene (33.46 g, 57.0 mmol, 0.2 eq) and tris(dibenzylideneacetone)dipalladium(O) (26.44 g, 28.0 mmol, 0.1 eq) were added. After stirring at 90° C. for 2 h, the reaction was cooled to RT; filtered through celite bed and washed with ethyl acetate (700 mL). The organic layer was washed with water (500 mL), dried over $Na_2SO_4$. and concentrated under reduced pressure. The residue was purified by silica gel chromatography eluting with 1.5% to 2.7% MeOH/DCM to afford 21.1 (69 g, 49.03%) as orange solid. MS (ES): m/z 487.52 $[M+1]^+$, 1H NMR (400 MHz, DMSO-d6) δ 7.34-7.31 (d, J=8.4 Hz, 1H), 6.37-6.35 (d, J=8 Hz, 1H), 5.71 (s, 2H), 3.97-3.85 (m, 2H), 3.76-367 (m, 2H), 3.42-3.36 (m, 2H), 2.12 (s, 8H), 1.83-1.74 (m, 1H).

Step-2 Synthesis of Compound Tert-Butyl 7-((6-((dimethylamino)methyl)-5-(tetrahydrofuran-3-yl)pyridin-2-yl)amino)-1-oxo-4-(4,4,5,5-tetramethyl-1,3,2-dioxaborolan-2-yl)isoindoline-2-carboxylate 21.2

To a solution of the 21.1 (58 g, 119.0 mmol) suspended in 1-4 dioxane (580 mL) was added bis(pinacolato)diboron (60.50 g, 238.0 mmol, 2.0 eq) and potassium acetate (35.01 g, 357.0 mmol, 3.0 eq). After degassing with flow of nitrogen for 20 min, XPhos PdG2 (9.36 g, 11.0 mmol, 0.1 eq) was added. After stirring at 90° C. for 2 h, the reaction was cooled to RT, filtered through celite and the celite bed was washed with ethyl acetate (2 L). The combined organic layer was washed with water (500 mL), dried over $Na_2SO_4$ and concentrated under reduced pressure. The residue was purified by silica gel chromatography eluting with 3.0% to 15% MeOH/DCM. The material was then triturated by hexanes to afford 21.2 (54 g, 78.37%) as brown solid. MS (ES): m/z 579.54 $[M+1]^+$.

Step-3 Synthesis of Compound Tert-Butyl 7-((6-((dimethylamino)methyl)-5-(tetrahydrofuran-3-yl)pyridin-2-yl)amino)-4-(7-fluoroimidazo[1,2-a]pyridin-3-yl)-1-oxoisoindoline-2-carboxylate 21.3

To a solution of the 21.2 (45 g, 77.0 mmol) and 7-fluoro-3-iodoimidazo[1,2-a]pyridine Intermediate BB63 (24.47 g, 93.0 mmol, 1.2 eq) in 1-4 dioxane (360 mL) and water (90 mL) was added potassium phosphate tribasic (49.51 g, 233.0 mmol, 3.0 eq). After degassing with flow of nitrogen for 20 min, XPhos PdG2 (6.11 g, 7.7 mmol, 0.1 eq) and 2-dicyclohexylphosphino-2',4',6'-triisopropylbiphenyl (1.85 g, 3.8 mmol, 0.05 eq) were added. After stirring at 100° C. for 3 h, the reaction was cooled to RT, filtered through celite bed and the celite bed was washed with ethyl acetate (300 mL). The organic layer was separated and concentrated under reduced pressure. The residue was purified by silica gel chromatography eluting with 2% to 3% MeOH/DCM. The isolated material was then triturated with diethyl ether to afford 21.3 (26.66 g, 58.42%) as light yellow solid. MS (ES): m/z 587.20 $[M+1]^+$, 1H NMR (400 MHz, DMSO-d6) δ 9.76 (S, 1H), 8.83-8.81 (d, J=8.4 Hz, 1H), 8.42-8.39 (t, J=12.8 Hz, 1H), 7.83-7.80 (d, J=12 Hz, 2H), 7.70-7.68 (d, J=8.8 Hz, 1H), 7.08-7.06 (d, J=8.4 Hz, 1H), 7.00-6.98 (t, J=8 Hz, 1H), 4.73 (S, 2H), 3.96 (m, 2H), 3.82-3.80 (t, J=7.6 Hz, 2H), 3.66-3.50 (m, 3H), 3.17-3.16 (d, J=5.2 Hz, 2H), 2.3 (S, 6H), 1.92-1.87 (m, 1H), 1.51 (S, 9H).

Step-4 Chiral Separation 21.3 (30 g racemic) were separated on Shimadzu LC-20AP and UV detector using Chiralpak IC (250*21.0) mm, 5 micron, at 20.0 mL/min. Mobile phases were (A) 0.1% Diethylamine in n-Hexane (B) 0.1% Diethylamine in Propane-2-ol:Acetonitrile (70:30). to afford compounds 21.4 (10 g) and 21.5 (9 g). Stereochemistry arbitrary assign.

Step-5a Synthesis of R)-7-((6-((dimethylamino)methyl)-5-(tetrahydrofuran-3-yl)pyridin-2-yl)amino)-4-(7-fluoroimidazo[1,2-a]pyridin-3-yl)isoindolin-1-one (I-478)

To a solution of 21.4 (10 g, 17.15 mmol) in DCM (100 mL) was added 4M hydrochloric acid in 1-4 dioxane (40 mL) at RT. After stirring at 50° C. for 2 h, the reaction mixture was evaporated in vacuum and pH adjust with NaHCO$_3$ solution to neutral. The aqueous layer was extracted with 15% MeOH/DCM. The solvent was evaporated under reduced pressure and material was triturated with diethyl ether to afford I-478 (7.3 g, 88.02%) as light yellow solid. MS (ES): m/z 486.55. [M+1]$^+$. 1H NMR (400 MHz, DMSO-d6) δ 10.05 (S, 1H), 8.77-8.75 (d, J=8.8 Hz, 2H), 8.47-8.43 (t, J=13.2 Hz, 1H), 7.82 (S, 1H), 7.74-7.72 (dd, J=28 Hz 2H), 6.99-6.93 (dd, J=8 Hz 2H), 4.39 (S, 2H), 4.01-3.97 (m, 2H), 3.83-3.78 (m, 2H), 3.64 (S, 3H), 3.54-3.50 (m, 4H), 2.29 (S, 6H), 1.91-1.86 (m, 1H).

Step-5b Synthesis of S)-7-((6-((dimethylamino)methyl)-5-(tetrahydrofuran-3-yl)pyridin-2-yl)amino)-4-(7-fluoroimidazo[1,2-a]pyridin-3-yl)isoindolin-1-one (I-479)

To a solution of 21.5 (1 g, 17.15 mmol) in DCM (10 mL) was added 4M hydrochloric acid in 1-4 dioxane (4 mL) at RT. After stirring at 50° C. for 2 h, the reaction mixture was evaporated in vacuum and pH adjust to neutral using NaHCO$_3$ solution. The aqueous layer was extracted by 15% MeOH/DCM. The organic extracts were evaporated under reduced pressure and the residue triturated with diethyl ether to afford I-479 (500 mg, 60.29%) as light yellow solid. MS (ES): m/z 486.55. [M+1]$^+$. 1H NMR (400 MHz, DMSO-d6) δ 10.05 (S, 1H), 8.85 (S, 1H), 8.78-8.76 (d, J=8.8 Hz, 1H), 8.47-8.44 (t, J=13.2 Hz, 1H), 7.83 (S, 1H), 7.74-7.65 (dd, J=28 Hz 2H), 7.55-7.52 (dd, J=12 Hz, 1H), 6.99-6.93 (m, 2H), 4.39 (S, 2H), 4.01-3.94 (m, 2H), 3.85-3.78 (m, 2H), 3.67-3.64 (m, 1H), 3.55-3.50 (m, 2H), 2.33-2.26 (m, 1H) 2.22 (S, 6H), 1.93-1.84 (m, 1H).

Example 22. Method Up

Synthesis of S)-7-((6-((dimethylamino)methyl)-5-(tetrahydrofuran-3-yl)pyridin-2-yl)amino)-4-(1-methyl-1H-pyrrolo[2,3-b]pyridin-4-yl)-2,3-dihydro-1H-pyrrolo[3,4-c]pyridin-1-one, (I-707), and (R)-7-((6-((dimethylamino)methyl)-5-(tetrahydrofuran-3-yl)pyridin-2-yl)amino)-4-(1-methyl-1H-pyrrolo[2,3-b]pyridin-4-yl)-2,3-dihydro-1H-pyrrolo[3,4-c]pyridin-1-one, (I-708)

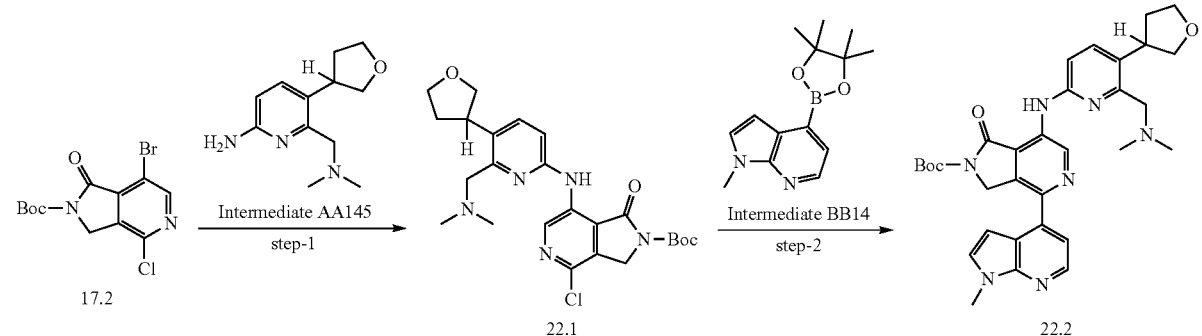

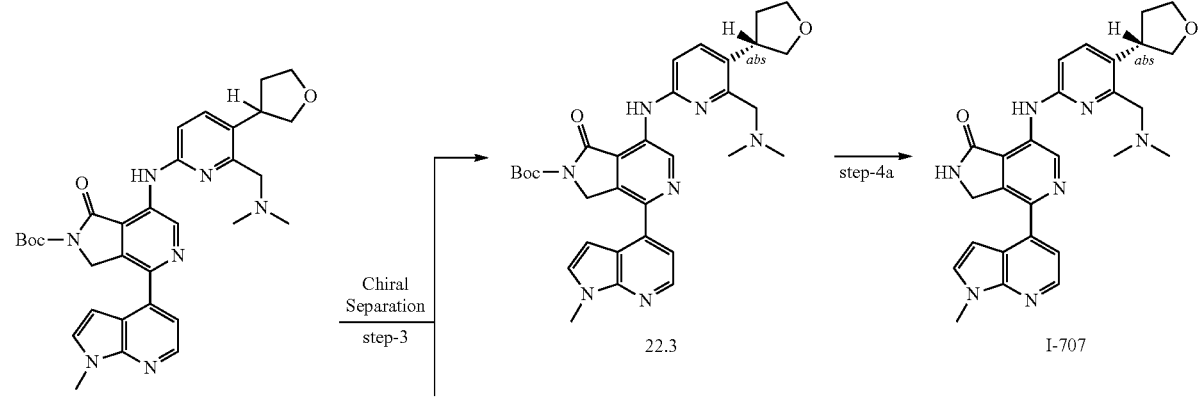

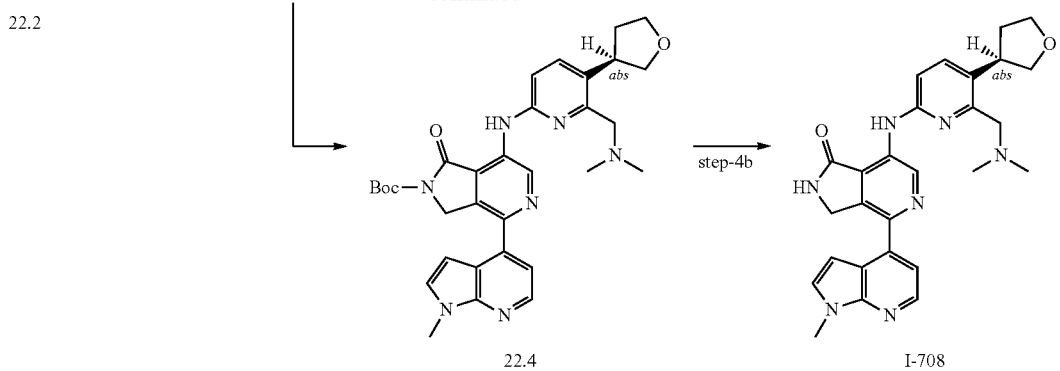

Step-1 Synthesis of Compound Tert-Butyl 4-chloro-7-((6-((dimethylamino)methyl)-5-(tetrahydrofuran-3-yl)pyridin-2-yl)amino)-1-oxo-1,3-dihydro-2H-pyrrolo[3,4-c]pyridine-2-carboxylate (22.1)

To a solution of tert-butyl 7-bromo-4-chloro-1-oxo-1,3-dihydro-2H-pyrrolo[3,4-c]pyridine-2-carboxylate (17.2) (48 g, 138 mmol) in toluene (480 mL) were added Intermediate AA145 (30.57 g, 138 mmol) and potassium carbonate (57.26 g, 414 mmol, 3.0 eq). After degassing with nitrogen for 20 min, 4,5-bis(diphenylphosphino)-9,9-dimethylxanthene (7.99 g, 13.8 mmol, 0.1 eq) and tris(dibenzylideneacetone)dipalladium(O) (6.33 g, 6 mmol, 0.05 eq) were added. After stirring at 90° C. for 2 h, the reaction was cooled to RT, filtered through celite bed and washed with ethyl acetate (500 mL). The organic layer was washed with water (500 mL), dried over $Na_2SO_4$, and concentrated under reduced pressure. The residue was purified by silica gel chromatography eluting with 1.5% to 2.1% MeOH/DCM to afford 22.1 (24 g, 36.03%) as orange solid. MS (ES): m/z 487.52 $[M+1]^+$ $^1$H NMR (400 MHz, DMSO-d6) δ 9.81 (S, 1H), 9.15 (s, 1H), 7.70 (d, J=8 Hz, 1H), 7.13 (d, J=8 Hz, 1H), 4.75 (s, 2H), 4.01-3.94 (m, 2H), 3.84-3.77 (m, 2H), 3.62 (d, J=12.1 Hz, 1H), 3.54-3.48 (m, 2H), 2.33-2.28 (m, 1H), 2.20 (s, 6H), 1.94-1.87 (m, 1H), 1.55 (s, 9H).

Step-2 Synthesis of Compound Tert-Butyl 7-((6-((dimethylamino)methyl)-5-(tetrahydrofuran-3-yl)pyridin-2-yl)amino)-4-(1-methyl-1H-pyrrolo[2,3-b]pyridin-4-yl)-1-oxo-1,3-dihydro-2H-pyrrolo[3,4-c]pyridine-2-carboxylate (22.2)

To a solution of 22.1 (24 g, 49.0 mmol) and 1-methyl-4-(4,4,5,5-tetramethyl-1,3,2-dioxaborolan-2-yl)-1H-pyrrolo[2,3-b]pyridine (19.4 g, 74 mmol, 1.5 eq) in 1-4 dioxane (192 mL), water (48 mL) was added potassium phosphate tribasic (31.40 g, 148 mmol, 3.0 eq). After degassing with nitrogen for 20 min, XPhos pdG2 (3.88 g, 4.9 mmol, 0.1 eq) was added. After stirring at 100° C. for 3 h, the reaction was cooled to RT, filtered through celite bed and celite bed washed by ethyl acetate (250 mL). The organic layer was collected and concentrated under reduced pressure. The residue was purified by silica gel chromatography eluting with 2.0% to 3.5% MeOH/DCM. The product was then triturated with hexane to afford 22.2 (21 g, 73%) as light yellow solid. MS (ES): m/z 587.20 $[M+1]^+$

Step-3 Chiral Separation 22.2 (22 g racemic) was separated on Shimadzu LC-20AP and UV detector using Chiralcel OX-H (250*21.0) mm, 5 micron, at 20.0 mL/min with mobile phase were (A) 0.1% Diethylamine in n-Hexane (B) 0.1% diethylamine in propane-2-ol: acetonitrile (70:30) to afford 22.3 (8.5 g) and 22.4 (7 g). Stereochemistry arbitrary assign.

1H NMR (400 MHz, DMSO-d6)_Isomer-1-(22.3): δ 10.17 (S, 1H), 9.46 (s, 1H), 8.39 (d, J=8 Hz, 1H), 7.72 (d, J=8 Hz, 1H), 7.60 (s, 1H), 7.35 (d, J=8 Hz, 1H), 7.16 (d, J=8 Hz, 1H), 6.82 (d, J=6 Hz, 1H), 4.96 (s, 2H), 4.03-3.96 (m, 2H), 3.89 (s, 3H), 3.84-3.80 (m, 2H), 3.65 (d, 1H), 3.56 (t, 1H), 2.34-2.30 (m, 1H), 2.23 (s, 6H), 1.94-1.89 (m, 1H), 1.55 (s, 9H).

1H NMR (400 MHz, DMSO-d6)_Isomer-2 (22.4): δ 10.16 (S, 1H), 9.46 (s, 1H), 8.40 (d, J=8 Hz, 1H), 7.72 (d, J=8 Hz, 1H), 7.61 (s, 1H), 7.37 (d, J=8 Hz, 1H), 7.14 (d, J=8 Hz, 1H), 6.80 (d, J=6 Hz, 1H), 4.98 (s, 2H), 4.02-3.96 (m, 2H), 3.89 (s, 3H), 3.85-3.79 (m, 2H), 3.65 (d, 1H), 3.56 (t, 1H), 2.34-2.30 (m, 1H), 2.23 (s, 6H), 1.93-1.90 (m, 1H), 1.56 (s, 9H).

Step-4a Synthesis of S)-7-((6-((dimethylamino)methyl)-5-(tetrahydrofuran-3-yl)pyridin-2-yl)amino)-4-(1-methyl-1H-pyrrolo[2,3-b]pyridin-4-yl)-2,3-dihydro-1H-pyrrolo[3,4-c]pyridin-1-one, (I-707)

To a solution of 22.3 (8.5 g, 17.56 mmol) in DCM (90 mL) was added 4M hydrochloric acid in 1,4 dioxane (50 mL) at RT. After stirring at 55° C. for 2 h, the reaction mixture was evaporated in vacuum. The crude product was poured in to sat $NaHCO_3$ solution and extracted with 15% MeOH/DCM. The organic layer was separated, dried with $Na_2SO_4$, and concentrated under reduced pressure and triturated with diethyl ether to afford I-707 (5.7 g, 81%) MS (ES): m/z 487 $[M+H]^+$. 1H NMR (400 MHz, DMSO-d6) δ 10.12 (S, 1H), 9.7 (s, 1H), 9.22 (S, 1H), 8.36-8.35 (d, J=4 Hz, 1H), 7.70-7.68 (d, J=8 Hz, 1H), 7.59-7.58 (d, J=3.6 Hz, 1H), 7.39-7.38 (d, J=5.2 Hz, 1H), 7.04-7.02 (d, J=8.4 Hz, 1H), 6.90-6.89 (d, J=3.6 Hz, 1H), 4.70 (s, 2H), 4.02-3.99 (m, 2H), 3.85-3.84 (d, J=2 Hz, 2H), 3.81-3.79 (m, 2H), 3.65 (S, J=1H, 2H), 2.52-2.51 (t, J=3.6 Hz, 2H), 2.23 (s, 5H), 1.93-1.88 (m, 1H).

Step-4b Synthesis of R)-7-((6-((dimethylamino)methyl)-5-(tetrahydrofuran-3-yl)pyridin-2-yl)amino)-4-(1-methyl-1H-pyrrolo[2,3-b]pyridin-4-yl)-2,3-dihydro-1H-pyrrolo[3,4-c]pyridin-1-one, (I-708)

To a solution of 22.4 (1 g, 17.12 mmol) in DCM (10 mL) was added 4M hydrochloric acid in 1-4 dioxane (4 mL) at RT. After stirring at 55° C. for 2 h, the reaction mixture was evaporated in vacuum. The crude product was poured in to sat NaHCO₃ solution and extracted with 15% MeOH/DCM. The organic layer was separated, dried with Na₂SO₄, and concentrated under reduced pressure and triturated with diethyl ether to afford I-708 (550 mg, 66.39%) MS (ES): m/z 487 [M+H]⁺. 1H NMR (400 MHz, DMSO-d6) δ 10.11 (S, 1H), 9.69 (s, 1H), 9.22 (S, 1H), 8.36-8.35 (d, J=4.4 Hz, 1H), 7.70-7.68 (d, J=8 Hz, 2H), 7.59 (S, 1H), 7.39-7.38 (d, J=4.4 Hz, 2H), 7.05-7.03 (d, J=8 Hz, 1H), 6.88 (S, 1H), 4.70 (s, 2H), 4.00-3.98 (d, J=8 Hz, 2H), 3.87 (S, 3H), 3.84-3.80 (s, J=16 Hz, 2H), 3.67 (S, 1H), 3.55-3.51 (m, 2H), 2.24 (s, 6H), 1.92-1.91 (d, J=6.8 Hz, 1H).

Example 23. Method Vp

Synthesis of 4-(7-fluoroimidazo[1,2-a]pyridin-3-yl)-7-((6-(((S)-3-hydroxypyrrolidin-1-yl)methyl)-5-((R)-tetrahydrofuran-3-yl)pyridin-2-yl)amino)isoindolin-1-one (I-778) and 4-(7-fluoroimidazo[1,2-a]pyridin-3-yl)-7-((6-4(S)-3-hydroxypyrrolidin-1-yl)methyl)-5-((S)-tetrahydrofuran-3-yl)pyridin-2-yl)amino) isoindolin-1-one (I-779)

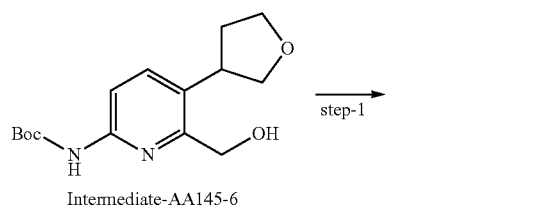

Intermediate-AA145-6

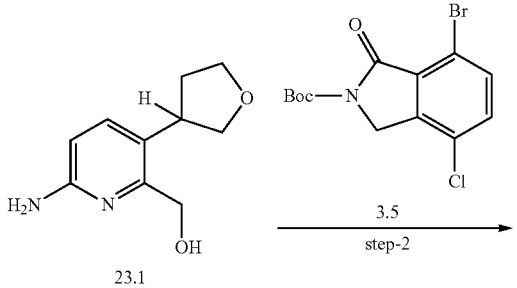

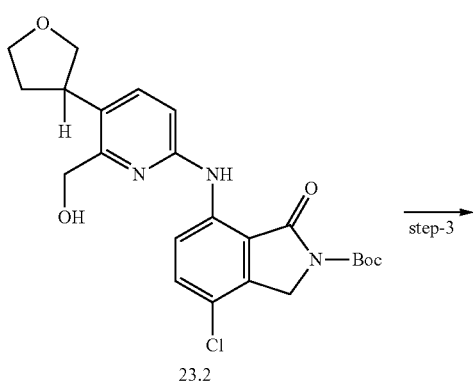

23.2

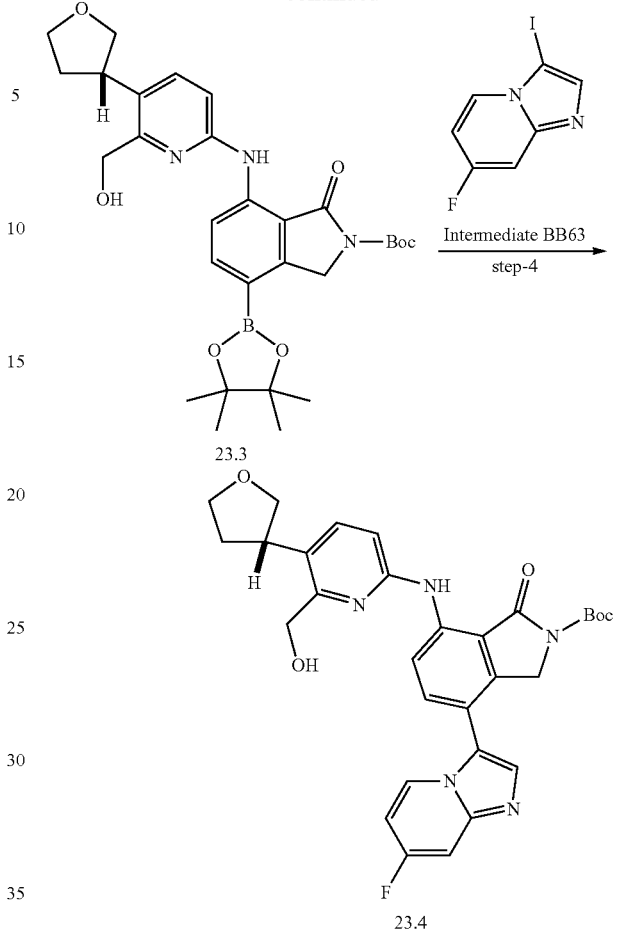

Step-1 Synthesis of (6-amino-3-(tetrahydrofuran-3-yl)pyridin-2-yl)methanol (23.1)

To a solution of Intermediate-AA145-6 (1.0 g, 5.15 mmol) in DCM (5.0 L) at 0° C. was added TFA (2.1 L). After stirring at 70° C. for 2 h, the reaction mixture was evaporated, diluted in water (2 L), and extracted with heptane. The aqueous layer was neutralized with 10% NaOH solution and extracted by 15% MeOH in DCM (4×3 L). The combined organic layer was dried over sodium sulfate and concentrated under reduced pressure. The residue was triturated with 20% ethyl acetate in hexanes and then diethyl ether to afford 23.1 as light brown solid. (330 g, 68.47%). MS (ES): m/z 222.30 [M+1]⁺, 1H NMR (400 MHz, DMSO-d6) δ 7.33 (d, J=8.4 Hz, 1H), 6.36 (d, J=8.5 Hz, 1H), 5.71 (s, 1H), 3.96-3.85 (m, 1H), 3.72 (dq, J=31.0, 7.7 Hz, 1H), 3.46-3.34 (m, 1H), 3.35 (s, 1H), 3.30 (d, J=11.9 Hz, 0H), 2.19 (td, J=7.8, 4.2 Hz, 0H), 2.14 (s, 3H), 1.79 (dq, J=12.2, 8.0 Hz, 1H).

Step-2 Synthesis of Tert-Butyl 4-chloro-7-((6-(hydroxymethyl)-5-(tetrahydrofuran-3-yl)pyridin-2-yl) amino)-1-oxoisoindoline-2-carboxylate (23.2)

tert-butyl 4-chloro-7-((6-(hydroxymethyl)-5-(tetrahydrofuran-3-yl)pyridin-2-yl)amino)-1-oxoisoindoline-2-carboxylate 23.2 was prepared from tert-butyl (6-(hydroxymethyl)-5-(tetrahydrofuran-3-yl)pyridin-2-yl)carbamate (23.1) in a similar fashion to that described in tert-butyl 4-chloro-7-((6-((dimethylamino)methyl)-5-(tetrahydrofuran-3-yl)pyridin-2-yl)amino)-1-oxoisoindoline-2-carboxylate (21.1) (0.930 g, 41.3%) m/z 460.16 [M+H]+

Step-3 Synthesis of Tert-Butyl (S)-7-((6-(hydroxymethyl)-5-(tetrahydrofuran-3-yl)pyridin-2-yl)amino)-1-oxo-4-(4,4,5,5-tetramethyl-1,3,2-dioxaborolan-2-yl)isoindoline-2-carboxylate (23.3)

tert-butyl (S)-7-((6-(hydroxymethyl)-5-(tetrahydrofuran-3-yl)pyridin-2-yl)amino)-1-oxo-4-(4,4,5,5-tetramethyl-1,3,2-dioxaborolan-2-yl)isoindoline-2-carboxylate (23.3) was synthesize from tert-butyl 4-chloro-7-((6-(hydroxymethyl)-5-(THF-3-yl)pyridin-2-yl)amino)-1-oxoisoindoline-2-carboxylate (23.2) in a similar fashion to that described in tert-butyl 7-((6-((dimethylamino)methyl)-5-(tetrahydrofuran-3-yl)pyridin-2-yl)amino)-1-oxo-4-(4,4,5,5-tetramethyl-1,3,2-dioxaborolan-2-yl)isoindoline-2-carboxylate (19.2) (0.700 g, 62.7%), m/z 552.4 [M+H]+.

Step-4 Synthesis of Tert-Butyl (S)-4-(7-fluoroimidazo[1,2-a]pyridin-3-yl)-7-((6-(hydroxymethyl)-5-(tetrahydrofuran-3-yl)pyridin-2-yl)amino)-1-oxoisoindoline-2-carboxylate (23.4)

tert-butyl (S)-4-(7-fluoroimidazo[1,2-a]pyridin-3-yl)-7-((6-(hydroxymethyl)-5-(THF-3-yl)pyridin-2-yl)amino)-1-oxoisoindoline-2-carboxylate (23.4) was synthesize from tert-butyl (S)-7-((6-(hydroxymethyl)-5-(tetrahydrofuran-3-yl)pyridin-2-yl)amino)-1-oxo-4-(4,4,5,5-tetramethyl-1,3,2-dioxaborolan-2-yl)isoindoline-2-carboxylate (23.3) in a similar fashion to that described in tert-butyl 7-((6-((dimethylamino)methyl)-5-(tetrahydrofuran-3-yl)pyridin-2-yl)amino)-4-(7-fluoroimidazo[1,2-a]pyridin-3-yl)-1-oxoisoindoline-2-carboxylate (21.3) (0.4 g, 56.3%). m/z 559.6 [M+H]+.

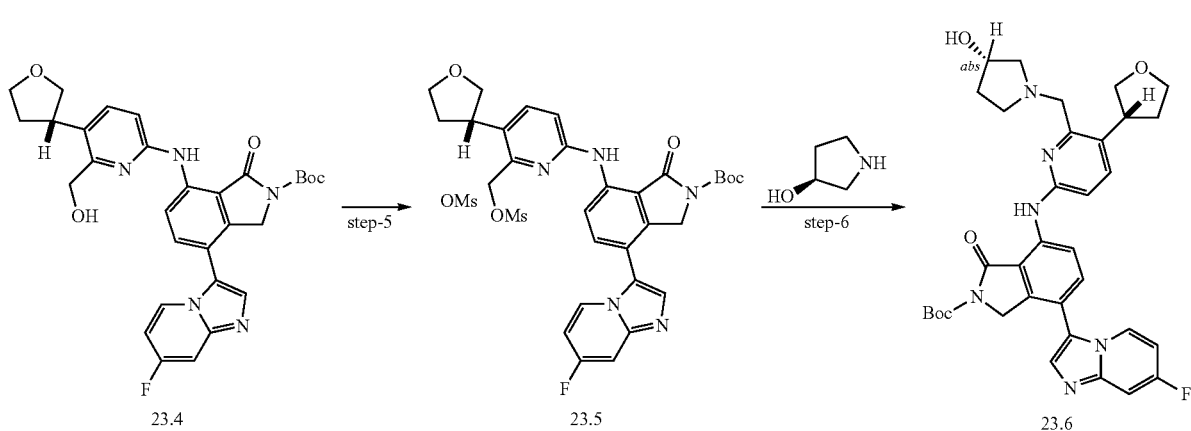

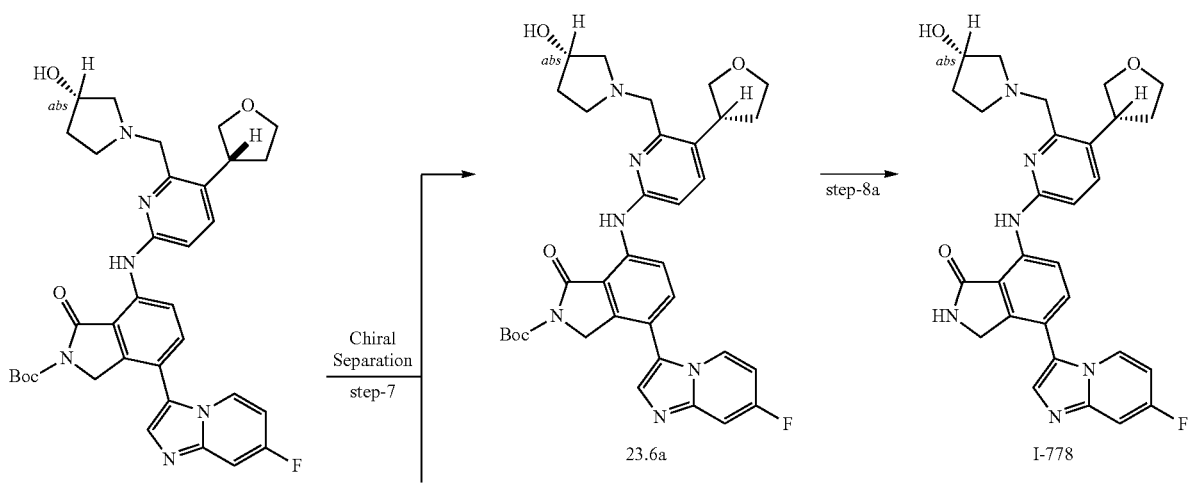

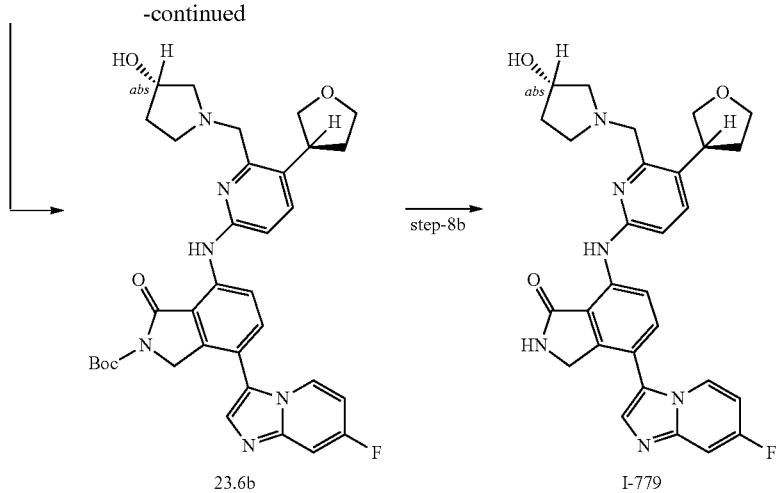

23.6b → step-8b → I-779

Step-5 & Step-6 Synthesis of Tert-Butyl (S)-4-(7-fluoroimidazo[1,2-a]pyridin-3-yl)-7-((6-(((methyl-sulfonyl)oxy)methyl)-5-(tetrahydrofuran-3-yl)pyridin-2-yl)amino)-1-oxoisoindoline-2-carboxylate (23.6)

tert-butyl (S)-4-(7-fluoroimidazo[1,2-a]pyridin-3-yl)-7-((6-(((methyl sulfonyl)oxy)methyl)-5-(THF-3-yl)pyridin-2-yl)amino)-1-oxoisoindoline-2-carboxylate (23.6) was synthesize from 23.4 & 23.5 in a similar fashion to that described in (step-2, 3) tert-butyl (R)-(6-((dimethylamino)methyl)-5-(tetrahydrofuran-3-yl)pyridin-2-yl)carbamate (20.2). (0.170 g, 37.8%). m/z 628.7 [M+H]$^+$.

Step-7 Chiral Separation 23.6 (0.17 gm) was separated on Shimadzu LC-20AP and UV detector using CHIRALPAK IC (250*21.0) mm, 5 micron, at 20.0 mL/min with mobile phase (A) 0.1% DEA IN n-Hexane, (B) 0.1% DEA in propane-2-ol:acetonitrile (70:30) to afford 23.6a (58 mg) and 23.6b (65 mg). Stereochemistry arbitrary assign

Step-8a Synthesis of 4-(7-fluoroimidazo[1,2-a]pyridin-3-yl)-7-((6-(((S)-3-hydroxypyrrolidin-1-yl)methyl)-5-((R)-tetrahydrofuran-3-yl)pyridin-2-yl)amino)isoindolin-1-one (I-778)

4-(7-fluoroimidazo[1,2-a]pyridin-3-yl)-7-((6-(((S)-3-hydroxypyrrolidin-1-yl)methyl)-5-((R)-tetrahydrofuran-3-yl)pyridin-2-yl)amino)isoindolin-1-one (I-778) was synthesize from 23.6a in a similar fashion to that described in step-5a (R)-7-((6-((dimethylamino)methyl)-5-(tetrahydrofuran-3-yl)pyridin-2-yl)amino)-4-(7-fluoroimidazo[1,2-a]pyridin-3-yl)isoindolin-1-one (I-478) in Example 21.

(30 mg, 61.52%). MS (ES): m/z 529 [M+1]$^+$, $^1$H NMR (400 MHz, DMSO-d6) δ 10.05 (s, 1H), 8.83-8.80 (d, J=4 Hz 2H), 8.46-8.43 (t, J=6.7 Hz, 1H), 7.83 (s, 1H), 7.69 (dd, J=33.0, 8.5 Hz, 1H), 7.54-7.51 (dd, J=10.1, 2.6 Hz, 2H), 7.02-6.89 (m, 2H), 4.65 (d, J=4.2 Hz, 1H), 4.39 (s, 1H), 4.19 (tt, J=7.7, 3.8 Hz, 2H), 4.05-3.87 (m, 1H), 3.89-3.71 (m, 2H), 3.67 (d, J=12.1 Hz, 1H), 3.60-3.48 (m, 2H), 3.31 (s, 1H), 2.76 (dd, J=9.7, 6.3 Hz, 2H), 2.65 (t, J=7.9 Hz, 1H), 2.50-2.42 (m, 2H), 2.40-2.22 (m, 1H), 2.05-1.82 (m, 1H), 1.54 (s, 1H).

Step-8b Synthesis of 4-(7-fluoroimidazo[1,2-a]pyridin-3-yl)-7-((6-(((S)-3-hydroxypyrrolidin-1-yl)methyl)-5-((S)-tetrahydrofuran-3-yl)pyridin-2-yl)amino)isoindolin-1-one (I-779)

4-(7-fluoroimidazo[1,2-a]pyridin-3-yl)-7-((6-(((S)-3-hydroxypyrrolidin-1-yl)methyl)-5-((S)-tetrahydrofuran-3-yl)pyridin-2-yl)amino)isoindolin-1-one (I-779) was synthesize from 23.6b in a similar fashion to that described in step-5b (S)-7-((6-((dimethylamino)methyl)-5-(tetrahydrofuran-3-yl)pyridin-2-yl)amino)-4-(7-fluoroimidazo[1,2-a]pyridin-3-yl)isoindolin-1-one (I-479) in Example 21. (30 mg, 61.52%). MS (ES): m/z 529 [M+1]$^+$, $^1$H NMR (400 MHz, DMSO-d6) δ 10.05 (s, 1H), 8.83-8.80 (d, J=12 Hz, 2H), 8.47-8.43 (t, J=12 Hz, 1H), 7.83 (s, 1H), 7.74-7.71 (d, J=12 Hz, 1H), 7.65-7.63 (d, J=8.5 Hz, 1H), 7.53 (dd, J=10.0, 2.7 Hz, 1H), 7.02-6.89 (m, 2H), 4.67 (d, J=4.2 Hz, 1H), 4.39 (s, 1H), 4.19 (s, 1H), 4.04-3.90 (m, 2H), 3.83-3.68 (m, 2H), 3.60-3.48 (m, 2H), 3.34 (s, 2H), 2.73 (dd, J=9.6, 6.2 Hz, 1H), 2.62 (q, J=7.7 Hz, 1H), 2.48 (s, 1H), 2.39 (dd, J=9.6, 3.8 Hz, 1H), 2.28 (dd, J=12.6, 8.4, 4.9 Hz, 2H), 2.05-1.83 (m, 1H), 1.56-1.44 (m, 1H)

Example 24. Method Wp

Synthesis of (S)-7-((6-(aminomethyl)-5-(THF-3-yl)pyridin-2-yl)amino)-4-(1-methyl-1H-pyrrolo[2,3-b]pyridin-4-yl)-2,3-dihydro-1H-pyrrolo[3,4-c]pyridin-1-one (I-836) and (R)-7-((6-(aminomethyl)-5-(THF-3-yl)pyridin-2-yl)amino)-4-(1-methyl-1H-pyrrolo[2,3-b]pyridin-4-yl)-2,3-dihydro-1H-pyrrolo[3,4-c]pyridin-1-one (I-829)

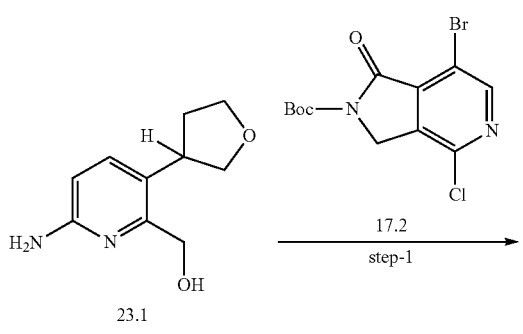

23.1 + 17.2 → step-1

1167

-continued

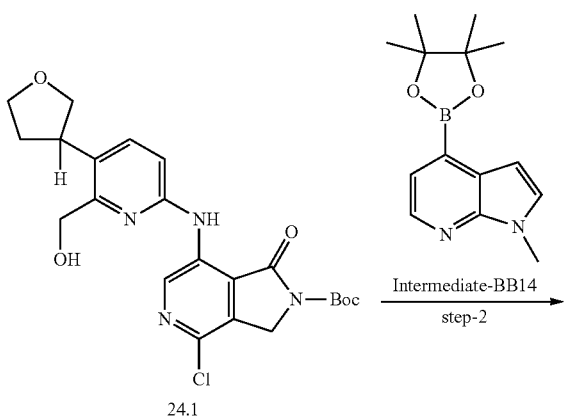

24.1

24.2

1168

Step-1 Synthesis of Tert-Butyl 4-chloro-7-((6-(hydroxymethyl)-5-(THF-3-yl)pyridin-2-yl)amino)-1-oxo-1,3-dihydro-2H-pyrrolo[3,4-c]pyridine-2-carboxylate (24.1)

tert-butyl 4-chloro-7-((6-(hydroxymethyl)-5-(tetrahydrofuran-3-yl)pyridin-2-yl)amino)-1-oxo-1,3-dihydro-2H-pyrrolo[3,4-c]pyridine-2-carboxylate (24.1) was prepared from tert-butyl (6-(hydroxymethyl)-5-(tetrahydrofuran-3-yl)pyridin-2-yl)carbamate (23.1) and tert-butyl 7-bromo-4-chloro-1-oxo-1,3-dihydro-2H-pyrrolo[3,4-c]pyridine-2-carboxylate (17.2) in a similar fashion to that described in tert-butyl 4-chloro-7-((6-((dimethylamino)methyl)-5-(tetrahydrofuran-3-yl)pyridin-2-yl)amino)-1-oxoisoindoline-2-carboxylate (21.1) (10 g, 35%). m/z 460.15 [M+H]$^+$.

Step-2 Synthesis of Tert-Butyl (S)-7-((6-(hydroxymethyl)-5-(THF-3-yl)pyridin-2-yl)amino)-4-(1-methyl-1H-pyrrolo[2,3-b]pyridin-4-yl)-1-oxo-1,3-dihydro-2H-pyrrolo[3,4-c]pyridine-2-carboxylate (24.2)

tert-butyl (S)-7-((6-(hydroxymethyl)-5-(tetrahydrofuran-3-yl)pyridin-2-yl)amino)-4-41-methyl-1H-pyrrolo[2,3-b]pyridin-4-yl)-1-oxo-1,3-dihydro-2H-pyrrolo[3,4-c]pyridine-2-carboxylate (24.2) was prepared from tert-butyl 4-chloro-7-((6-(hydroxymethyl)-5-(tetrahydrofuran-3-yl)pyridin-2-yl)amino)-1-oxo-1,3-dihydro-2H-pyrrolo[3,4-c]pyridine-2-carboxylate 24.1 and Intermediate BB14 in a similar fashion to that described in step-2 tert-butyl 7-((6-((dimethylamino)methyl)-5-(tetrahydrofuran-3-yl)pyridin-2-yl)amino)-4-(1-methyl-1H-pyrrolo[2,3-b]pyridin-4-yl)-1-oxo-1,3-dihydro-2H-pyrrolo[3,4-c]pyridine-2-carboxylate (22.2). (3.5 g, 72.21%). m/z 557.24 [M+H]$^+$.

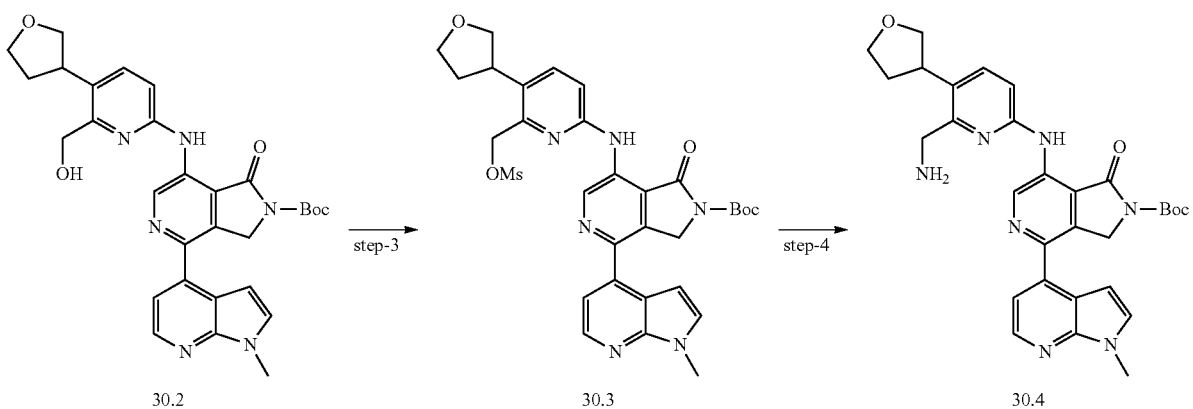

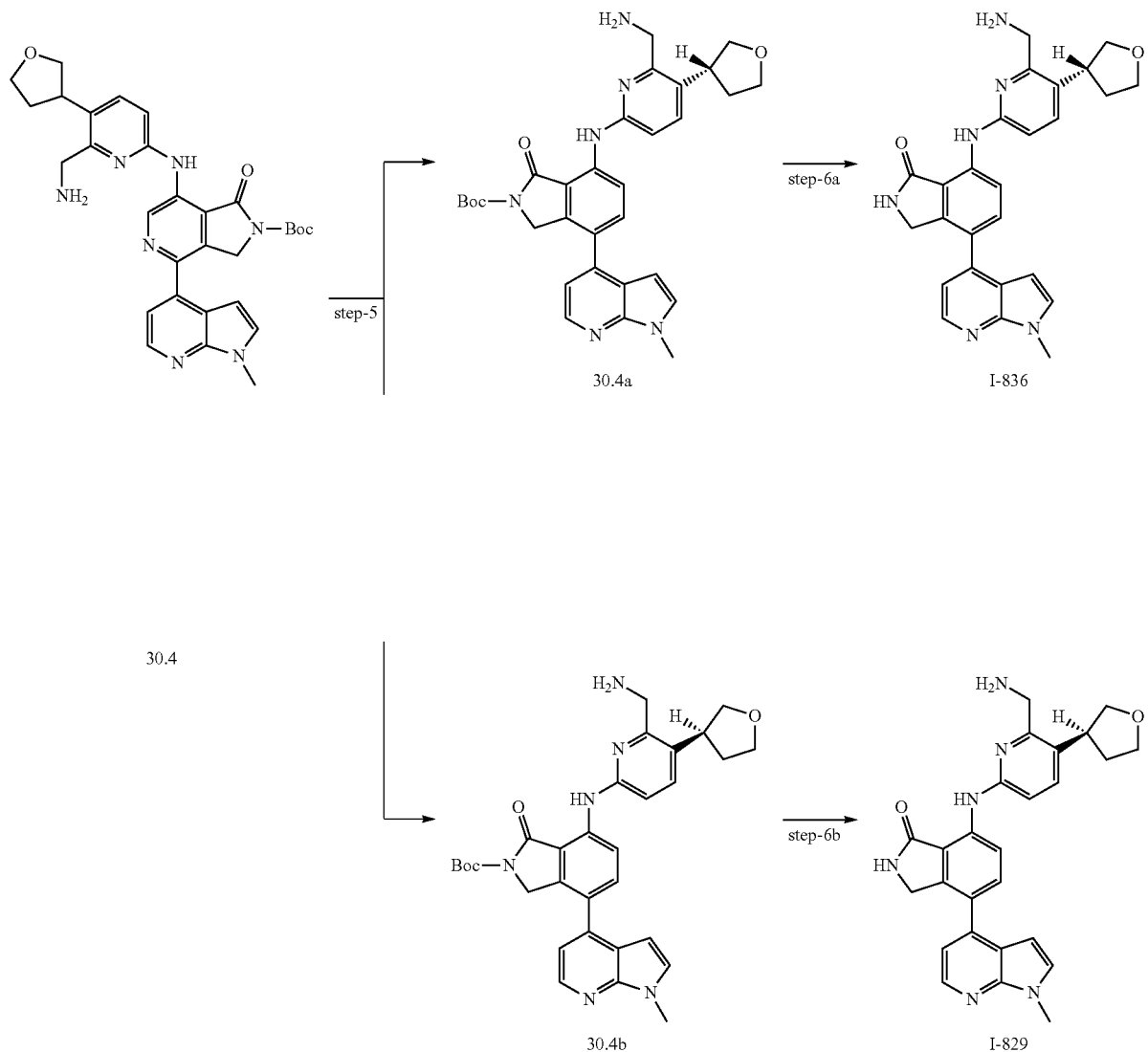

Step 3 to Step 6a, 6b were carried out following representative procedures described in Example 22 to afford I-829 and I-836.

I-829 (35 mg) m/z=456.0 [M+H]+ $^1$H NMR (400 MHz, DMSO): δ 9.92 (s, 1H), 9.77 (s, 1H), 9.30 (s, 1H), 8.46 (bs, 3H), 8.40-8.39 (d, J=4.8 Hz, 1H), 7.77-7.75 (d, J=8.4 Hz, 1H), 7.44-7.43 (d, J=4.8 Hz, 1H), 7.18-7.16 (d, J=8.8 Hz, 1H), 6.97-6.96 (d, J=3.6 Hz, 1H), 4.75 (bs, 2H), 4.36-4.35 (d, J=5.2 Hz, 2H), 3.99-3.95 (m, 3H), 3.86 (s, 4H), 3.44-3.40 (m, 2H), 2.37-2.34 (m, 1H).

I-836 (9 mg) m/z=456.0 [M+H]+ $^1$H NMR (400 MHz, DMSO): δ 10.09 (bs, 1H), 9.67 (bs, 2H), 9.23 (bs, 1H), 8.36-8.35 (d, J=5.2 Hz, 1H), 7.66-7.56 (m, 2H), 7.40-7.37 (t, J=5.2 Hz, 1H), 6.99 (s, 1H), 6.91-6.90 (d, J=2.8 Hz, 2H), 4.72 (bs, 2H), 4.34 (bs, 1H), 3.95-3.87 (m, 3H), 3.82 (s, 4H), 3.64-3.57 (m, 2H), 2.33-2.29 (m, 1H), 1.87 (bs, 1H).

Example 25. Method Xp

Synthesis of 7-((6-((dimethylamino)methyl)-5-(tetrahydro-2H-pyran-4-yl)pyridin-2-yl)amino)-4-(7-fluoroimidazo[1,2-a]pyridin-3-yl)isoindolin-1-one (I-792)

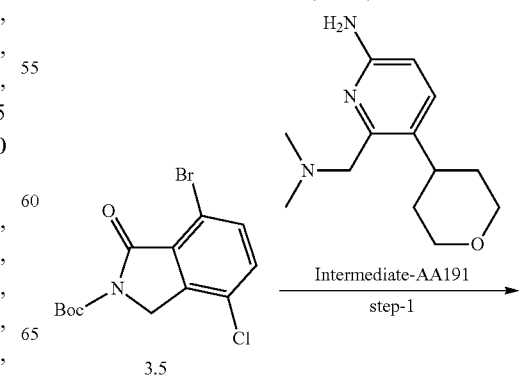

-continued

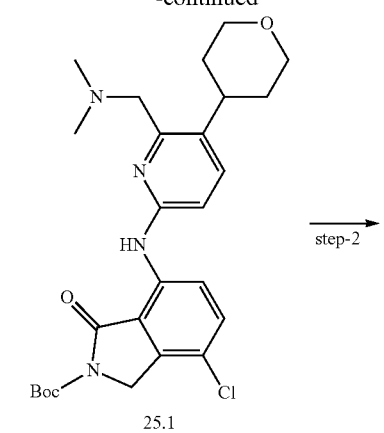

25.1

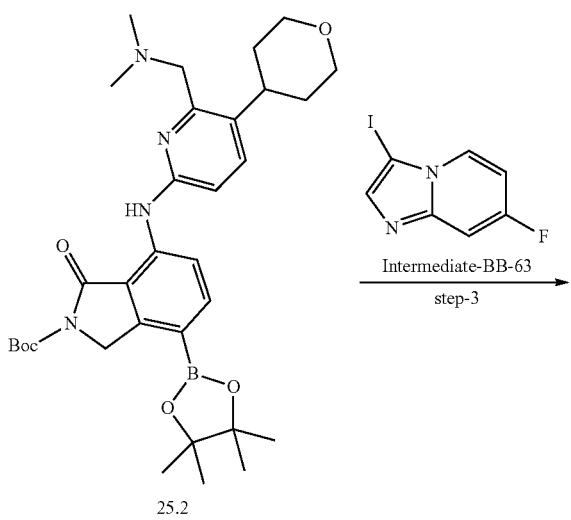

25.2

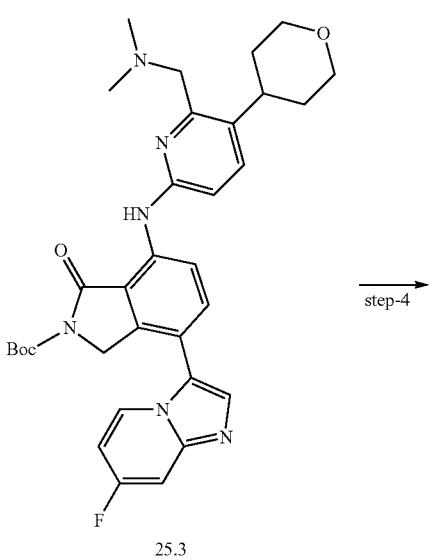

25.3

-continued

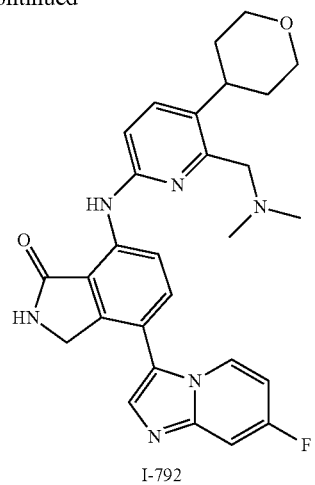

I-792

Step-1 Synthesis of Tert-Butyl 4-chloro-7-((6-((dimethylamino)methyl)-5-(tetrahydro-2H-pyran-4-yl)pyridin-2-yl)amino)-1-oxoisoindoline-2-carboxylate (25.1)

To a solution of 3.5 (75 g, 216.7 mmol) in 1-4 dioxane (750 mL) were added Intermediate AA191 (51.14 g, 216.7 mmol) and cesium carbonate (211.28 g, 650.1 mmol, 3.0 eq). After degassing with nitrogen for 20 min, 4,5-bis(diphenylphosphino)-9,9-dimethylxanthene (25.09 g, 43.34 mmol, 0.2 eq) and tris(dibenzylideneacetone)dipalladium (O) (19.82 g, 21.67 mmol, 0.1 eq) were added. After stirring at 90° C. for 2 h, the reaction was cool to RT, filtered through celite bed and the celite bed was washed with ethyl acetate (2.5 L). The combined organic layer was washed with water (2 L), dried over Na$_2$SO$_4$, filtered, and concentrated under reduced pressure. The residue was purified by silica gel chromatography eluting with 1-6% methanol/DCM to afford 25.1. (60 g, 56%) as orange solid. MS (ES): m/z 502.02 [M+1]$^+$ Step-2 Synthesis of Tert-Butyl 7-((6-((dimethylamino)methyl)-5-(tetrahydro-2H-pyran-4-yl)pyridin-2-yl)amino)-1-oxo-4-(4,4,5,5-tetramethyl-1,3,2-dioxaborolan-2-yl) iso indoline-2-carboxylate (25.2)

To a solution of the 25.1 (60 g, 119.0 mmol) in 1-4 dioxane (600 mL), were added bis(pinacolato)diboron (60.50 g, 239.0 mmol, 2.0 eq) and potassium acetate (35.01 g, 357.0 mmol, 3.0 eq). After degassing with nitrogen for 20 min, XPhos Pd G2 (9.36 g, 11.9 mmol, 0.1 eq) was added. After stirring at 90° C. for 2 h, the reaction was cool to RT, filtered through celite and the celite bed was washed with ethyl acetate (1.5 L). The combined organic layer was washed with water (1 L), dried over Na$_2$SO$_4$, and concentrated under reduced pressure. The residue was purified by silica gel chromatography to afford 25.2. (43 g, 60%) as brown solid. MS (ES): m/z 593.54 [M+1]$^+$.

Step-3 Synthesis of Tert-Butyl 7-((6-((dimethylamino)methyl)-5-(tetrahydro-2H-pyran-4-yl)pyridin-2-yl)amino)-4-(7-fluoroimidazo[1,2-a]pyridin-3-yl)-1-oxoisoindoline-2-carboxylate (25.3)

To a solution of the 25.2 (45 g, 76.01 mmol) in 1-4 dioxane (360 mL) and water (90 mL) were added 7-fluoro- 3-iodoimidazo[1,2-a]pyridine (Intermediate BB63) (24.47 g, 91.21 mmol, 1.2 eq) and potassium phosphate tribasic (48.33 g, 2.0 mmol, 3.0 eq). After degassing with nitrogen for 20 min, XPhos pdG2 (5.97 g, 7.6 mmol, 0.1 eq) and 2-dicyclohexylphosphino-2',4',6'-triisopropylbiphenyl (1.85 g, 3.8 mmol, 0.05 eq) were added. After stirring at 100° C. for 3 h, the reaction was cooled to RT, filtered through celite bed and the celite bed washed with ethyl acetate (1 L). The combined organic layer washed with water (1.5 L) and concentrated under reduced pressure. The residue was purified by silica gel chromatography eluting with 2-5% methanol in DCM to afford 25.3. (21 g, 48.17%). MS (ES): m/z 601.29 [M+1]$^+$.

Step-4 Synthesis of 7-((6-((dimethylamino)methyl)-5-(tetrahydro-2H-pyran-4-yl)pyridin-2-yl)amino)-4-(7-fluoroimidazo[1,2-a]pyridin-3-yl)isoindolin-1-one (I-792)

To a solution of 25.3 (21 g, 34.92 mmol) in DCM (210 mL) was added 4M hydrochloric acid in 1,4 dioxane (84 mL) at RT. After stirring at 50° C. for 2 h, the reaction mixture was evaporated in vacuum and pH adjusted to neutral using NaHCO$_3$ solution. The aqueous layer was extracted by 15% MeOH/DCM. The organic solution was evaporated under reduced pressure and the residue triturated with diethyl ether to afford I-792. (10 g, 57.14%). MS (ES): m/z 501.55. [M+1]$^+$. $^1$H NMR (400 MHz, DMSO): δ 10.03 (s, 1H), 8.83 (s, 1H), 8.78-8.76 (d, J=8 Hz, 1H), 7.47-7.44 (t, J=6.4 Hz, 1H), 7.83 (s, 1H), 7.74-7.72 (d, J=8.4 Hz, 1H), 7.68-7.66 (d, J=8 Hz, 1H), 7.55-7.52 (dd, J=2.4 Hz, 1H), 6.96-6.94 (t, J=2 Hz, 1H), 6.92 (s, 1H), 4.39 (s, 2H), 3.99-3.96 (dq, 2H), 3.59 (s, 2H), 3.47-3.42 (t, J=10.4 Hz, 2H), 3.28 (s, 1H), 3.20 (bs, 1H), 2.24 (s, 6H), 1.70-1.65 (m, 3H).

Example 26. Method Yp

Synthesis of (R)-4-(7-fluoroimidazo[1,2-a]pyridin-3-yl)-7-((5-(1-morpholinoethyl)pyridin-2-yl)amino)isoindolin-1-one (I-639) and (S)-4-(7-fluoroimidazo[1,2-a]pyridin-3-yl)-7-((5-(1-morpholinoethyl)pyridin-2-yl)amino)isoindolin-1-one (I-640)

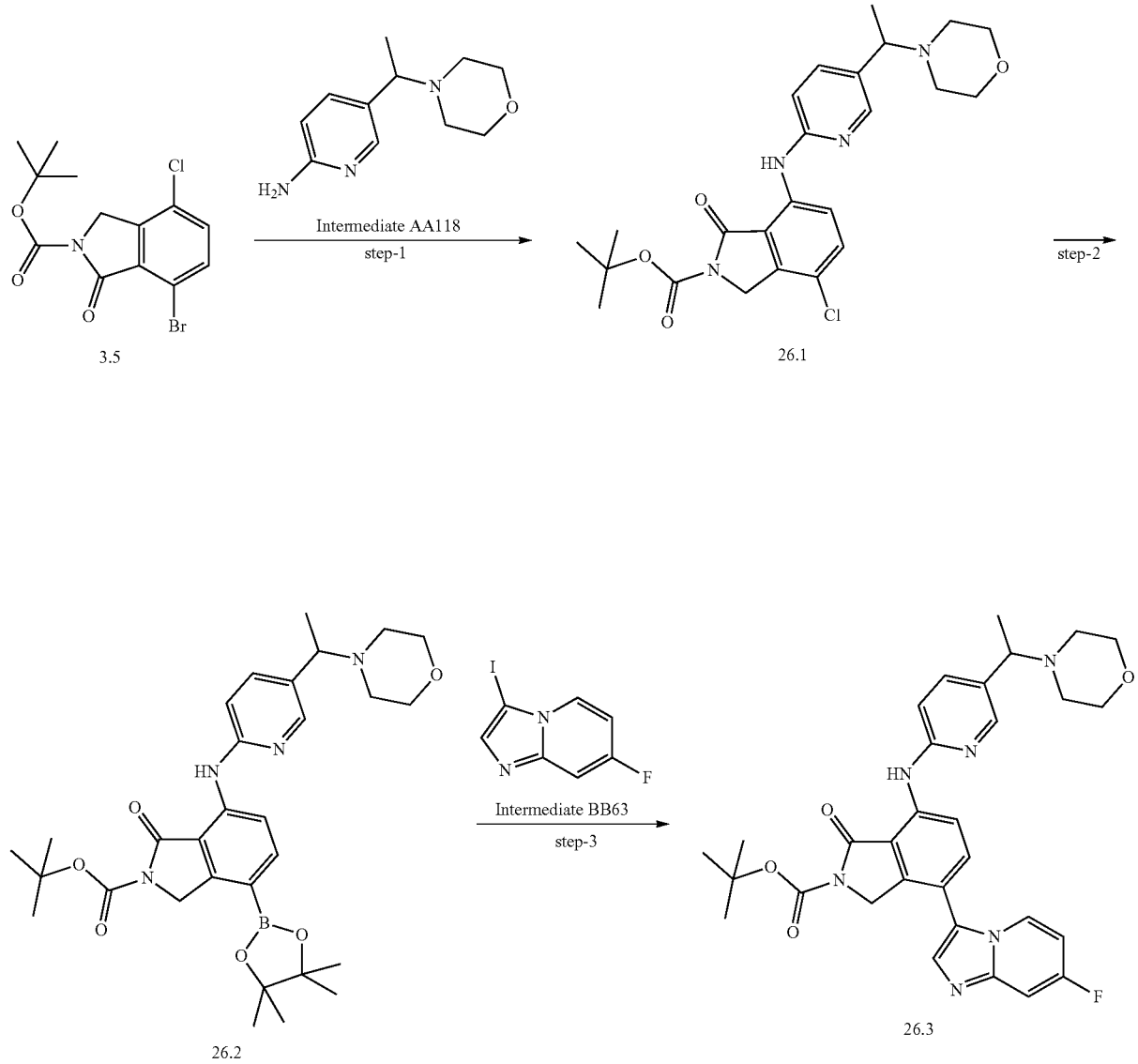

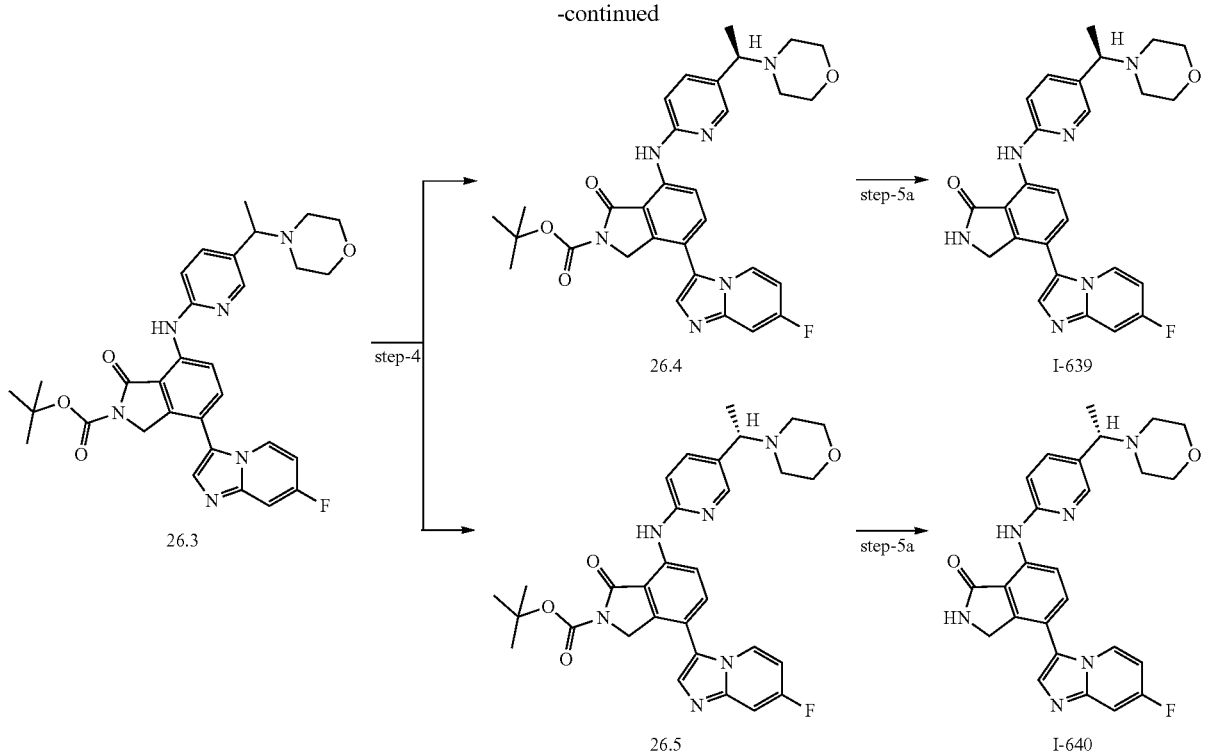

Step-1 Synthesis of Tert-Butyl 4-chloro-7-((5-(1-morpholinoethyl)pyridin-2-yl)amino)-1-oxoisoindoline-2-carboxylate (26.1)

To a solution of 3.5 (0.350 g, 1.01 mmol) and Intermediate AA118 (0.252 g, 1.21 mmol, 1.2 eq) in 1, 4-dioxane (8 mL) were added potassium carbonate (0.278 g, 2.02 mmol, 2.0 eq) and Xantphos (0.058 g, 0.10 mmol, 0.1 eq). After degassing under $N_2$ stream for 15 min, $Pd_2(dba)_3$ (0.046 g, 0.05 mmol, 0.05 eq) was added. After stirring at 100° C. and for 1 h, the reaction mixture was cooled to RT, diluted with water (50 mL) and extracted with ethyl acetate (3×30 mL). The combined organic extracts were washed with brine (30 mL), dried over $Na_2SO_4$, filtered, and concentrated under reduced pressure. The residue was purified by column chromatography 2% methanol gradient in DCM to afford 26.1 (0.250 g, 52.34%) as a brown solid. MS (ES): m/z=474.18 $[M+2]^+$

Step-2 Synthesis of Tert-Butyl 7-((5-(1-morpholinoethyl)pyridin-2-yl)amino)-1-oxo-4-(4,4,5,5-tetramethyl-1,3,2-dioxaborolan-2-yl)isoindoline-2-carboxylate (26.2)

To a solution of 26.1 (0.250 g, 0.52 mmol) in dioxane (6 mL). were added bis(pinacolato)diboron (0.336 g, 1.32 mmol, 2.5 eq) and potassium acetate (0.155 g, 1.58 mmol, 3.0 eq). After degassing with $N_2$ for 15 min, X-Phos Pd G3 (0.021 g, 0.026 mmol, 0.05 eq) was added. After stirring at 100° C. for 1 h, the reaction mixture was cooled to RT, diluted with water (40 mL) and extracted with ethyl acetate (3×20 mL). The combined organic extracts were washed with brine (40 mL), dried over $Na_2SO_4$, filtered, and concentrated under reduced pressure to afford 26.2 (0.3 g) which was used in the next step without further purification. MS (ES): m/z 565.32 $[M+H]^+$.

Step-3 Synthesis of Tert-Butyl 4-(7-fluoroimidazo[1,2-a]pyridin-3-yl)-7-((5-(1-morpholinoethyl)pyridin-2-yl)amino)-1-oxoisoindoline-2-carboxylate (26.3)

To a solution of 26.2 (0.3 g, 0.53 mmol)) in dioxane (3 mL) and water (1 mL) were added Intermediate BB63 (0.13 g, 0.63 mmol, 1.2 eq) and potassium phosphate tribasic (0.337 g, 1.59 mmol, 3.0 eq). After degassing with $N_2$ for 15 min, X-Phos Pd G2 (0.041 g, 0.053 mmol, 0.1 eq) was added. After stirring at 110° C. for 20 min in microwave, the reaction mixture was cooled to RT, diluted with water (40 mL) and extracted with ethyl acetate (3×20 mL). The combined organic extracts were washed with brine (40 mL), dried over $Na_2SO_4$, filtered, and concentrated under reduced pressure. The residue was purified by column chromatography eluting with 3.0% methanol gradient in DCM to afford 26.3 (0.2 g, 78%), MS (ES): m/z 573.26 $[M+H]^+$.

Step-4 Synthesis of Tert-Butyl (R)-4-(7-fluoroimidazo[1,2-a]pyridin-3-yl)-7-((5-(1-morpholinoethyl)pyridin-2-yl)amino)-1-oxoisoindoline-2-carboxylate (25.4) and Tert-Butyl (S)-4-(7-fluoroimidazo[1,2-a]pyridin-3-yl)-7-((5-(1-morpholinoethyl)pyridin-2-yl)amino)-1-oxoisoindoline-2-carboxylate (25.5)

26.3 (110 mg) was separated on Shimadzu LC-20AP and UV detector using CHIRALPAK (250*21.0) mm, 5 micron at 20.0 mL/min with mobile phase (A) 0.1% DEA IN n-Hexane and (B)0.1% DEA in propanol:methanol (50:50) to afford 26.4 (45 mg) and 26.5 (44 mg). Stereochemistry was arbitrary assigned.

Step-5a Synthesis of R)-4-(7-fluoroimidazo[1,2-a]pyridin-3-yl)-7-((5-(1-morpholinoethyl)pyridin-2-yl)amino)isoindolin-1-one (I-639)

To a solution of tert-butyl (R)-4-(7-fluoroimidazo[1,2-a]pyridin-3-yl)-7-((5-(1-morpholinoethyl)pyridin-2-yl)amino)-1-oxoisoindoline-2-carboxylate (26.4) (0.045 g, 0.07 mmol) in DCM (1 mL) at 0° C. was added 4M HCl in dioxane (0.4 mL). After stirring at RT for 1 h, the reaction mixture was neutralized using saturated sodium bicarbonate solution and extracted with 10% methanol in DCM (3×10 mL). The combine organic layer was concentrated under reduced pressure. The residue was purified by column chromatography to afford the title compound I-639 (0.030 g, 80.79%) as white solid. MS (ES): m/z 473.23 (M+H). $^1$H NMR (400 MHz, DMSO-d6) δ 10.10 (s, 1H), 8.87 (s, 1H), 8.74-8.72 (d, J=8.6 Hz, 1H), 8.47-8.43 (m, 1H), 8.22-8.21 (d, J=2.3 Hz, 1H), 7.84 (s, 1H), 7.76-7.74 (d, J=8.6 Hz, 1H), 7.67-7.65 (dd, J=8.4, 2.4 Hz, 1H), 7.56-7.53 (dd, J=10.1, 2.7 Hz, 1H), 7.05-6.99 (m, 2H), 4.41 (s, 2H), 3.58-3.56 (t, J=4.6 Hz, 3H), 3.45-3.40 (m, 2H), 2.40 (bs, 1H), 2.34-2.30 (m, 3H), 1.34-1.32 (dd, J=6.8 Hz, 3H).

Step-5b Synthesis of S)-4-(7-fluoroimidazo[1,2-a]pyridin-3-yl)-7-((5-(1-morpholinoethyl)pyridin-2-yl)amino)isoindolin-1-one (I-640)

To a solution of tert-butyl (S)-4-(7-fluoroimidazo[1,2-a]pyridin-3-yl)-7-((5-(1-morpholinoethyl)pyridin-2-yl)amino)-1-oxoisoindoline-2-carboxylate (26.5) (0.045 g, 0.07 mmol) in DCM (1 mL) at 0° C. was added 4M HCl in dioxane (0.4 mL). After stirring at RT for 1 h, the reaction mixture was neutralized using saturated sodium bicarbonate solution and extracted with 10% methanol in DCM (3×10 mL). The combine organic layer was concentrated under reduced pressure. The residue was purified by column chromatography to afford the title compound I-640 (0.025 g, 67.33%) as White solid. MS (ES): m/z 473.21 (M+H). 1H NMR (400 MHz, DMSO-d6) δ 10.10 (s, 1H), 8.87 (s, 1H), 8.74-8.72 (d, J=8.6 Hz, 1H), 8.47-8.43 (m, 1H), 8.22-8.21 (d, J=2.3 Hz, 1H), 7.84 (s, 1H), 7.76-7.74 (d, J=8.6 Hz, 1H), 7.67-7.65 (dd, J=8.4, 2.4 Hz, 1H), 7.56-7.53 (dd, J=10.1, 2.7 Hz, 1H), 7.05-6.99 (m, 2H), 4.41 (s, 2H), 3.58-3.56 (t, J=4.6 Hz, 3H), 3.45-3.40 (m, 2H), 2.40 (bs, 1H), 2.34-2.30 (m, 3H), 1.34-1.32 (dd, J=6.8 Hz, 3H).

Example 27. Method Zp

Synthesis of 7-((6-((3aS,6aS)-hexahydropyrrolo[3,4-b]pyrrol-1(2H)-yl)pyrazin-2-yl)amino)-4-(1-methyl-1H-pyrrolo[2,3-b]pyridin-4-yl)-2,3-dihydro-1H-pyrrolo[3,4-c]pyridin-1-one (I-660) and 7-((6-((3aR,6aR)-hexahydropyrrolo[3,4-b]pyrrol-1(2H)-yl)pyrazin-2-yl)amino)-4-(1-methyl-1H-pyrrolo[2,3-b]pyridin-4-yl)-2,3-dihydro-1H-pyrrolo[3,4-c]pyridin-1-one (I-661)

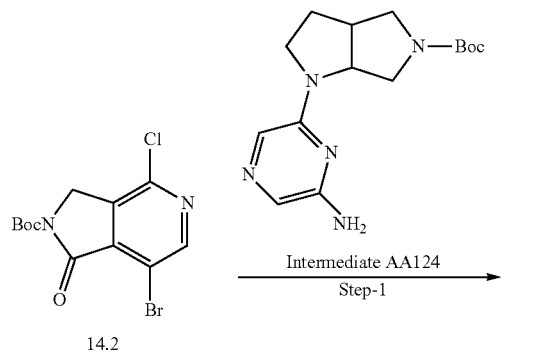

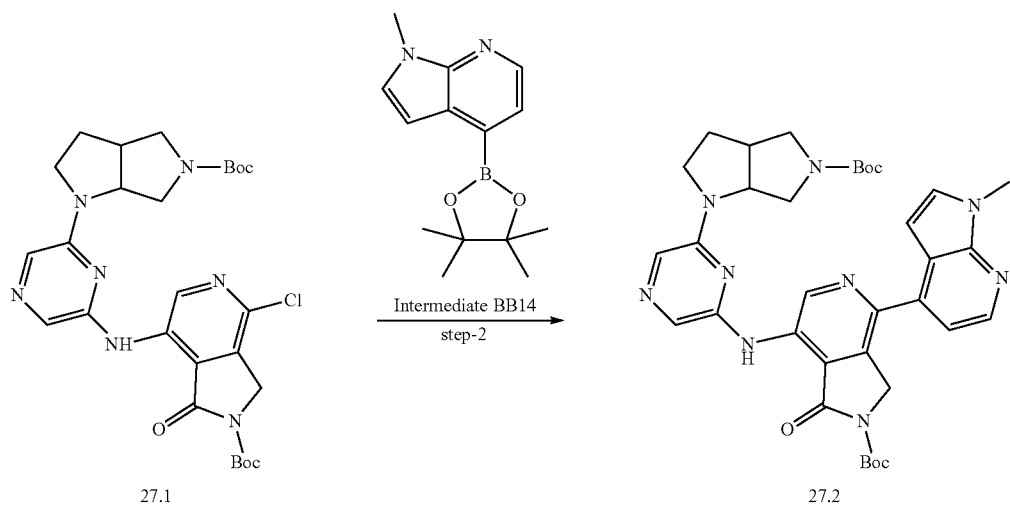

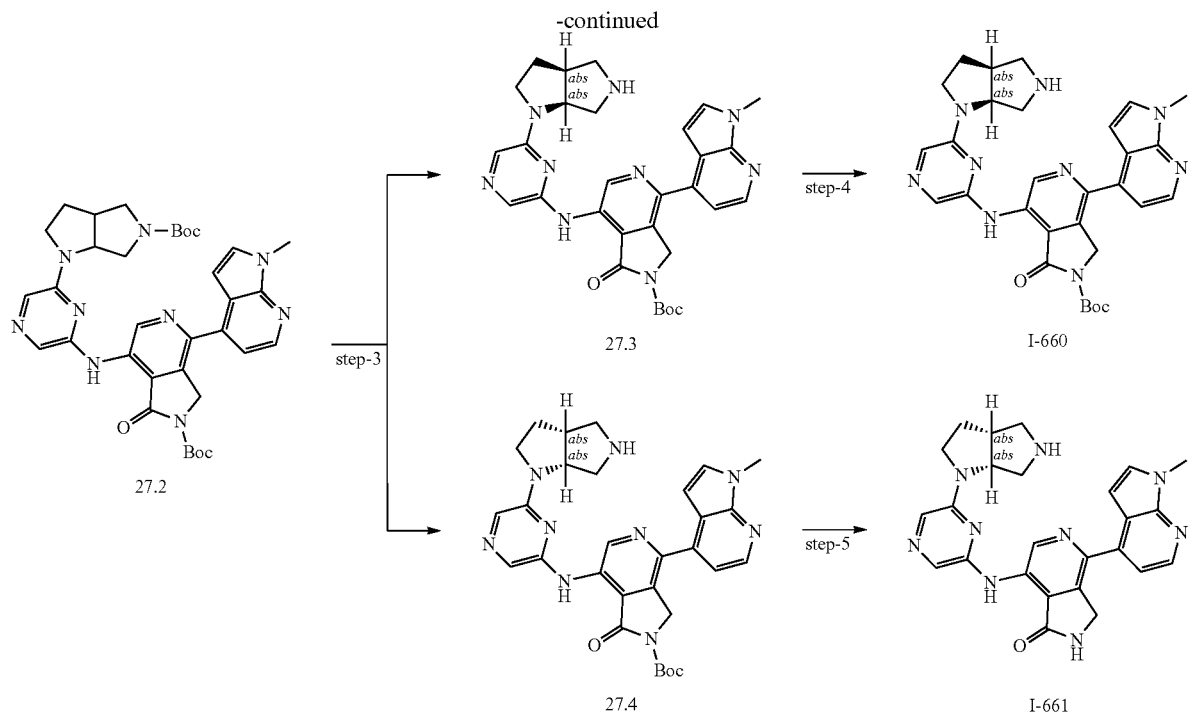

Step-1 Synthesis of Tert-Butyl 7-((6-(5-(tert-butoxycarbonyl)hexahydropyrrolo[3,4-b]pyrrol-1(2H)-yl)pyrazin-2-yl)amino)-4-chloro-1-oxo-1,3-dihydro-2H-pyrrolo[3,4-c]pyridine-2-carboxylate (27.1)

A solution of Intermediate AA124 (0.6 g, 1.72 mmol) and 14.2 (0.527 g, 1.72 mmol) in 1,4-dioxane (8 mL) was added $K_2CO_3$ (0.71 g, 5.16 mmol, 3.0 eq). After degassing under $N_2$ stream for 15 min, Xantphos (0.2 g, 0.34 mmol, 0.2 eq) and $Pd_2(dba)_3$ (0.157 g, 0.17 mmol, 0.1 eq) were added. After stirring at 110° C. for 5 h, the reaction mixture was cooled to RT, diluted water (50 mL) and extracted with ethyl acetate (3×20 mL). The combined organic extracts were washed with brine (50 mL), dried over $Na_2SO_4$, filtered, and concentrated under reduced pressure. The residue was purified by column chromatography eluting with 50% ethyl acetate gradient in hexane to afford 27.1 (0.5 g, 50.63%) as a brown solid. MS (ES): m/z=573.2 [M+H]$^+$.

Step-2 Synthesis of Tert-Butyl 7-((6-(5-(tert-butoxycarbonyl)hexahydropyrrolo[3,4-b]pyrrol-1(2H)-yl)pyrazin-2-yl)amino)-4-(1-methyl-1H-pyrrolo[2,3-b]pyridin-4-yl)-1-oxo-1,3-dihydro-2H-pyrrolo[3,4-c]pyridine-2-carboxylate (27.2)

To a solution of 27.1 (0.490 g, 0.85 mmol) and Intermediate BB14 (0.442 g, 1.71 mmol, 2.0 eq) in 1,4-dioxane:water (5 mL:1 mL) was added potassium phosphate tribasic (0.540 g, 2.55 mmol, 3.0 eq). After degassing with $N_2$ for 15 min, X-Phos Pd G2 (0.066 g, 0.085 mmol, 0.1 eq) was added. After stirring at 110° C. for 20 min in microwave, the reaction mixture was cooled to RT, diluted water (60 mL) and extracted with ethyl acetate (3×30 mL). The combined organic extracts were washed with brine (70 mL), dried over $Na_2SO_4$, filtered, and concentrated under reduced pressure. The residue was purified by column chromatography eluting with 2% methanol gradient in DCM to afford 27.2 (0.360 g, 62.94%), MS (ES): m/z 668.3 [M+H]$^+$

Step-3 Separation of Tert-Butyl 7-((6-((3aS,6aS)-hexahydropyrrolo[3,4-b]pyrrol-1(2H)-yl)pyrazin-2-yl)amino)-4-(1-methyl-1H-pyrrolo[2,3-b]pyridin-4-yl)-1-oxo-1,3-dihydro-2H-pyrrolo[3,4-c]pyridine-2-carboxylate (27.3) and Tert-Butyl 7-((6-((3aR,6aR)-hexahydropyrrolo[3,4-b]pyrrol-1(2H)-yl)pyrazin-2-yl)amino)-4-(1-methyl-1H-pyrrolo[2,3-b]pyridin-4-yl)-1-oxo-1,3-dihydro-2H-pyrrolo[3,4-c]pyridine-2-carboxylate (27.4)

27.2 (360 mg) was separated by Chiral SFC in Shimadzu LC-20AP and UV detector using CHIRALPAK IH (250*4.6 mm) 5 u 5 micron at 20 mL/min with mobile phase (A) 0.1% DEA IN n-Hexane and (B) 0.1% DEA in propanol:acetonitrile (70:30) to afford 27.3 (140 mg) and 27.4 (130 mg). Stereochemistry was arbitrary assigned.

Step-4 Synthesis of 7-((6-((3aS,6aS)-hexahydropyrrolo[3,4-b]pyrrol-1(2H)-yl)pyrazin-2-yl)amino)-4-(1-methyl-1H-pyrrolo[2,3-b]pyridin-4-yl)-2,3-dihydro-1H-pyrrolo[3,4-c]pyridin-1-one (I-660)

To solution of tert-butyl 7-((6-((3aS,6aS)-hexahydropyrrolo[3,4-b]pyrrol-1(2H)-yl)pyrazin-2-yl)amino)-4-(1-methyl-1H-pyrrolo[2,3-b]pyridin-4-yl)-1-oxo-1,3-dihydro-2H-pyrrolo[3,4-c]pyridine-2-carboxylate (27.3) (0.140 g, 0.246 mmol, 1.0 eq) into DCM (2 mL) at 0° C. was added dropwise TFA (0.5 mL). After stirring at RT for 30 min, the reaction mixture was neutralized using saturated sodium bicarbonate solution and extracted with 10% methanol in DCM (3×20 mL). The combine organic layer was concentrated under reduced pressure. The residue was purified by preparative HPLC to afford the title compound (I-660) (0.030 g, 26.02%) as off white solid. MS (ES): m/z 468.2

[M+H]+. 1H NMR (400 MHz, DMSO-d6) δ 9.95 (s, 1H), 9.74 (s, 1H), 9.29 (s, 1H), 8.37 (d, J=5.0 Hz, 1H), 8.28 (s, 1H), 7.67 (s, 1H), 7.62-7.50 (m, 2H), 7.41 (d, J=5.0 Hz, 1H), 6.88 (d, J=3.3 Hz, 1H), 4.72 (s, 2H), 4.48 (bs, 1H), 3.88 (s, 3H), 3.69 (d, J=3.5 Hz, 1H), 3.21 (s, 1H), 3.19 (d, J=6.0 Hz, 2H), 3.16-3.05 (m, 2H), 2.88 (dd, J=10.7, 3.1 Hz, 1H), 2.18-2.13 (dq, J=14.6, 7.4 Hz, 1H), 1.94-1.90 (dt, J=11.6, 6.2 Hz, 1H).

Step-5 Synthesis of 7-((6-((3aR,6aR)-hexahydropyrrolo[3,4-b]pyrrol-1(2H)-yl)pyrazin-2-yl)amino)-4-(1-methyl-1H-pyrrolo[2,3-b]pyridin-4-yl)-2,3-dihydro-1H-pyrrolo[3,4-c]pyridin-1-one (I-661)

To solution of tert-butyl 7-((6-((3aR,6aR)-hexahydropyrrolo[3,4-b]pyrrol-1(2H)-yl)pyrazin-2-yl)amino)-4-(1-methyl-1H-pyrrolo[2,3-b]pyridin-4-yl)-1-oxo-1,3-dihydro-2H-pyrrolo[3,4-c]pyridine-2-carboxylate (27.4) (0.130 g, 0.19 mmol, 1.0 eq) into DCM (2 mL) at 0° C. was added dropwise TFA (0.5 mL). After stirring at RT for 30 min, the reaction mixture was neutralized using saturated sodium bicarbonate solution and extracted with 10% methanol in DCM (3×20 mL). The combine organic layer was concentrated under reduced pressure. The residue was purified by preparative HPLC to afford the title compound (I-661) (0.025 g, 23.25%) as off white solid. MS (ES): m/z 468.2 [M+H]+. 1H NMR (400 MHz, DMSO-d6) δ 9.96 (s, 1H), 9.74 (s, 1H), 9.29 (s, 1H), 8.37 (d, J=4.9 Hz, 1H), 8.28 (s, 1H), 7.67 (s, 1H), 7.60 (d, J=3.5 Hz, 1H), 7.55 (s, 1H), 7.41 (d, J=4.9 Hz, 1H), 6.88 (d, J=3.4 Hz, 1H), 4.73 (s, 2H), 4.47 (s, 1H), 3.89 (s, 3H), 3.69-3.66 (m, 1H), 3.58 (d, J=8.6 Hz, 1H), 3.18 (s, 1H), 3.09 (d, J=12.0 Hz, 2H), 3.02 (d, J=11.5 Hz, 2H), 2.86 (d, J=9.6 Hz, 1H), 2.16 (dd, J=12.9, 6.9 Hz, 1H).

Example 28. Method AAp

Synthesis of 7-((6-((dimethylamino)methyl)-5-(3-(methoxymethyl)THF-3-yl)pyridin-2-yl)amino)-4-(7-fluoroimidazo[1,2-a]pyridin-3-yl)isoindolin-1-one (I-837)

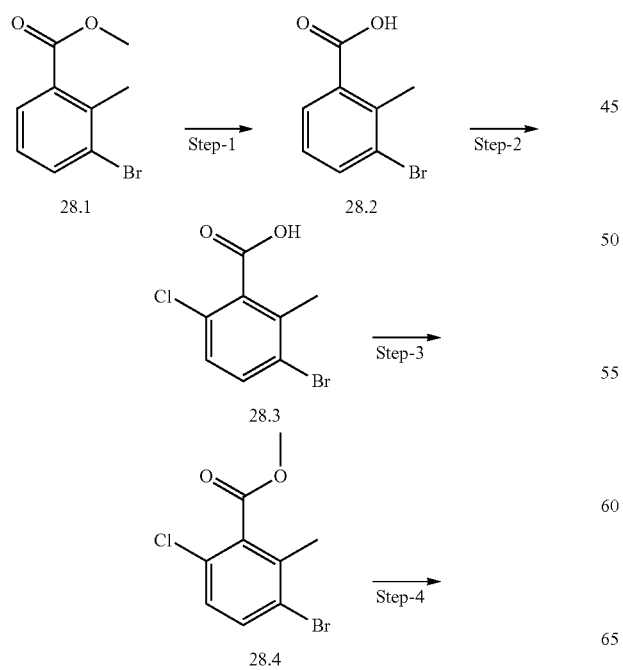

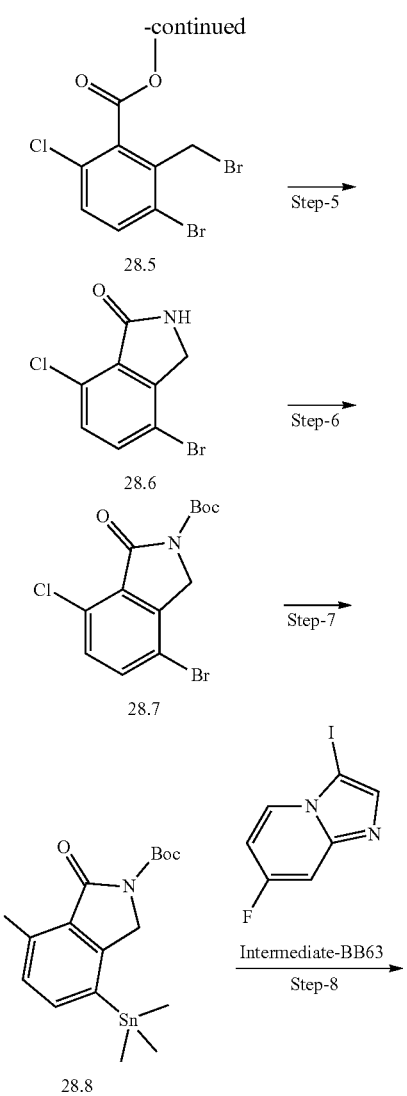

Step-1 Synthesis of 3-bromo-2-methylbenzoic acid (28.2)

To a solution of 28.1 (1 g, 4.3 mmol) in methanol (10 mL) was added NaOH (873 mg, 21.82 mmol, 5 eq). After stirring at 60° C. for 1 h, the reaction mixture was quenched with dilute HCl (100 mL) and extracted with ethyl acetate (100 mL×3). The combined organic layer was dried over sodium sulfate and concentrated under reduced pressure. The residue was purified by column chromatography using neutral alumina eluting with 5-10% methanol in DCM to afford 28.2 (730 mg, 77%). MS (ES): m/z 216.05 [M+2]⁺.

Step-2 Synthesis of 3-bromo-6-chloro-2-methylbenzoic Acid (28.3)

To a solution of 27.2 (9.3 g, 43.2 mmol) in DMF (90 mL) were added NCS (6.93 g, 51.9 mmol, 1.2 eq) and Pd(OAc)$_2$ (4.85 g, 224.5 mmol, 0.5 eq). After stirring at 110° C. for 16 h., the reaction was diluted with water (1.5 L) and extracted by ethyl acetate (2×2 L). The combined organic layer dried over sodium sulfate, filtered, and concentrated under vacuum. The residue was purified by column chromatography to afford 28.3 (9 g, 83.41%). MS (ES): m/z 247.92 [M+2]⁺.

Step-3 Synthesis of Methyl 3-bromo-6-chloro-2-methylbenzoate (28.4)

To a solution of 28.3 (9 g, 36.07 mmol) in DMF (90 mL) was added K$_2$CO$_3$ (12.4 g, 90.18 mmol, 2.5 eq). After stirring at RT for 30 min, methyl iodide (5.6 g, 39.68 mmol, 1.1 eq) was added. After stirring for 16 hr at RT, the reaction was diluted with dilute HCl (300 mL) and extracted by ethyl acetate (3×500 mL). The combined organic layer dried over sodium sulfate and dried under vacuum. The residue was purified by column chromatography to afford 28.4 (8 g, 84.16%). MS (ES): m/z 264.52 [M+2]⁺.

Step-4 Synthesis of Methyl 3-bromo-2-(bromomethyl)-6-chlorobenzoate (28.5)

To a solution of 28.4 (8 g, 30.36 mmol) in CCl$_4$ (80 mL) were added NBS (5.9 g, 33.39 mmol, 1.1 eq) and DBPO (14.7 mg, 0.06 mmol, 0.002 eq). After stirring at 110° C. for 16 h, the reaction was diluted with water (300 mL) and extracted by ethyl acetate (3×500 mL). The combined organic layer dried over sodium sulfate, filtered, and concentrated under vacuum to afford crude which was purified by Colum chromatography to afford 28.5 (8 g, 76.96%). MS (ES): m/z 342.41 [M+2]⁺.

Step-5 Synthesis of 4-bromo-7-chloroisoindolin-1-one (Intermediate 28.6)

To a solution of 28.5 (9.5 g, 27.7 mmol) in methanol (95 mL), ammonia gas was purged for 16 hr at RT. After completion of reaction, the reaction was diluted with water (300 mL) and extracted by ethyl acetate (3×500 mL). The combined organic layer dried over sodium sulfate and dried under vacuum. The residue was purified by trituration with diethyl ether to afford 28.6 (4 g, 61.74%). MS (ES): m/z 247.69 [M+2]⁺.

Step-6 Tert-Butyl 4-bromo-7-chloro-1-oxoisoindoline-2-carboxylate (28.7)

To a solution of 28.6 (3.8 g, 15.41 mmol) in THF (45 mL) were added (BOC)$_2$O (5.04 g, 23.12 mmol, 1.5 eq) and DMAP (2.3 g, 18.49 mmol, 1.2 eq). After stirring at RT for 4 h, the reaction was diluted with water (150 mL) and extracted by ethyl acetate (3×100 mL). The combined organic layer dried over sodium sulfate and concentrated under vacuum. The reside was purified by column chromatography to afford 28.7 (3.8 g, 80.51%). MS (ES): m/z 345.61 [M+2]⁺.

Step-7 Synthesis of Tert-Butyl 7-chloro-1-oxo-4-(trimethylstannyl)isoindoline-2-carboxylate (Intermediate 28.8)

To a solution of 28.7 (900 mg, 2.6 mmol) in toluene (9 mL) was added hexamethyldistin (1.2 g, 3.9 mmol, 1.5 eq). After degassing with flow of nitrogen for 20 min, bis(triphenylphosphine)palladium(II) dichloride (182 mg, 0.026 mmol, 0.1 eq) was added. After stirring at 110° C. for 2 h, the reaction was cool to RT, diluted with water (150 mL) and extracted with EtOAc (3×60 mL). The combined organic extract was dried over Na$_2$SO$_4$ and concentrated under reduced pressure. The residue was purified by silica gel chromatography to afford 28.8 (480 mg, 55.71%). MS (ES): m/z 401.09 [M+1]⁺

Step-8 Synthesis of Tert-Butyl 7-chloro-4-(7-fluoroimidazo[1,2-a]pyridin-3-yl)-1-oxoisoindoline-2-carboxylate (28.9)

To a solution of 28.8 (900 mg, 76.01 mmol) in 1-4 dioxane (9 mL) was added 3-bromo-7-fluoroimidazo[1,2-a]pyridine (658 mg, 2.5 mmol, 1.2 eq). After degassing with flow of nitrogen for 20 min, CuI (39 mg, 0.2 mmol, 0.1 eq) and tetrakis(triphenylphosphine)-palladium(O) (237 mg, 0.20 mmol, 0.1 eq) were added. After stirring at 100° C. for 1 h, the reaction was cool to RT, diluted with water (150 mL) and extracted with EtOAc (3×60 mL). The combined organic extract was dried over Na$_2$SO$_4$ and concentrated under reduced pressure. The residue was purified by silica gel chromatography to afford 28.9 (480 mg, 23%). MS (ES): m/z 401.09 [M+1]⁺

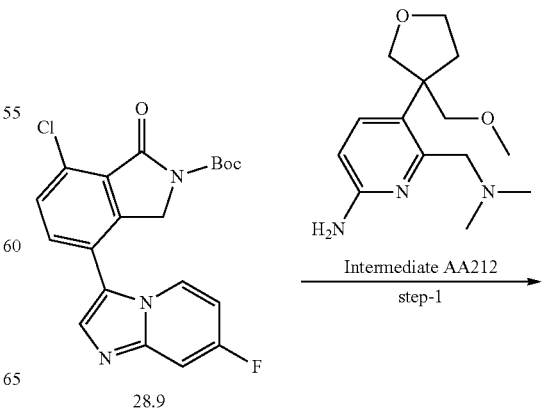

-continued

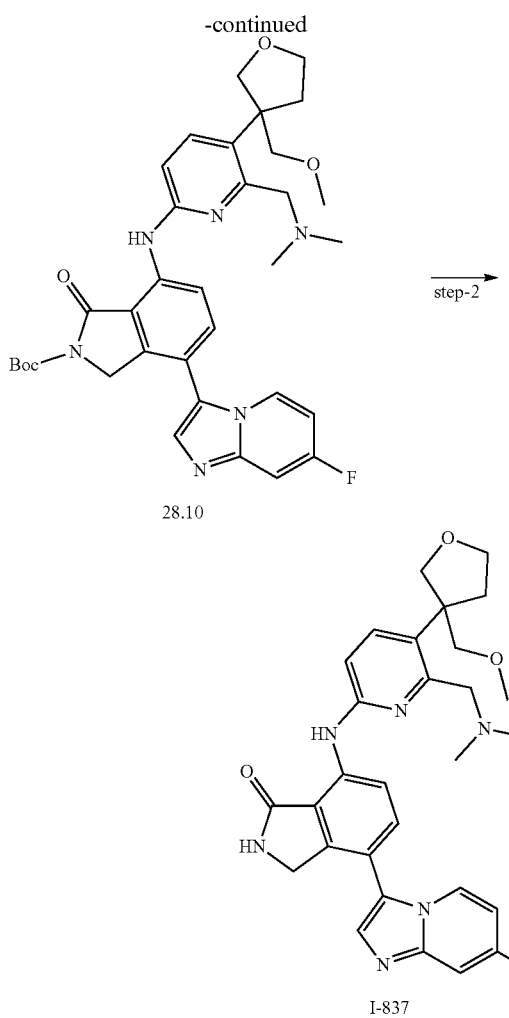

28.10

I-837

Step-1 Synthesis of Tert-Butyl 7-((6-((dimethyl-amino)methyl)-5-(3-(methoxymethyl)tetrahydro-furan-3-yl)pyridin-2-yl)amino)-4-(7-fluoroimidazo[1,2-a]pyridin-3-yl)-1-oxoisoindoline-2-carboxylate (28.10)

To a solution of 28.9 (290 mg, 0.7 mmol, 1.2 eq) in 1-4 dioxane (750 mL) were added Intermediate AA212 (160 mg, 0.6 mmol) and cesium carbonate (590 mg, 1.8 mmol, 3.0 eq) at RT. After degassing with flow of nitrogen for 20 min, 4,5-bis(diphenylphosphino)-9,9-dimethylxanthene (70 mg, 0.12 mmol, 0.2 eq) and tris(dibenzylideneacetone)dipalladium(O) (55 g, 0.06 mmol, 0.1 eq) were added. After stirring at 90° C. for 2 h, the reaction was cool to RT, diluted with water (20 mL) and extracted with EtOAc (3×20 mL). The combined organic layer was dried over Na$_2$SO$_4$ and concentrated under reduced pressure. The residue was purified by silica gel chromatography to afford 27.10 (170 mg, 67%). MS (ES): m/z 631.2 [M+1]$^+$ Step-2 Synthesis of 7-((6-((dimethylamino)methyl)-5-(3-(methoxymethyl) tetrahydrofuran-3-yl)pyridin-2-yl)amino)-4-(7-fluoroimidazo[1,2-a]pyridin-3-yl)isoindolin-1-one (I-837)

To a solution of 28.10 (120 mg, 0.2 mmol) in DCM (5 mL) was added 4M hydrochloric acid in 1-4 dioxane (2 mL)

at RT. After stirring at RT for 2 h, the reaction mixture was evaporated in vacuum, the pH was neutralized using NaHCO$_3$ solution and extracted by 15% MeOH/DCM. The organic extract was evaporated under reduced pressure and triturated by diethyl ether to afford I-837 (30 mg, 30%). MS (ES): m/z 531.34 [M+1]$^+$. $^1$H NMR (400 MHz, DMSO): δ 10.05 (s, 1H), 8.85 (bs, 2H), 8.46-8.42 (d, J=6 Hz, 1H), 7.95 (s, 1H), 7.74-7.72 (d, J=8.8 Hz, 1H), 7.55-7.54 (d, J=2.4 Hz, 1H), 7.45-7.43 (d, J=8.4 Hz, 1H), 6.99-6.97 (t, J=2.4 Hz 1H), 6.81 (s, 1H), 4.39 (s, 2H), 4.26-4.23 (d, J=8.4 Hz, 1H), 3.94-3.88 (m, 2H), 3.53-3.47 (m, 3H), 3.14 (s, 3H), 2.37 (s, 3H), 2.27 (s, 6H), 1.23 (s, 1H).

Example 29. Method ABp

Synthesis of (R)-7-((6-(((dimethylamino)methyl)-5-(6-hydroxy-1,4-oxazepan-4-yl)pyridin-2-yl)amino)-4-(7-fluoroimidazo[1,2-a]pyridin-3-yl)isoindolin-1-one (I-819) and (S)-7-((6-(((dimethylamino)methyl)-5-(6-hydroxy-1,4-oxazepan-4-yl)pyridin-2-yl)amino)-4-(7-fluoroimidazo[1,2-a]pyridin-3-yl)isoindolin-1-one (I-820)

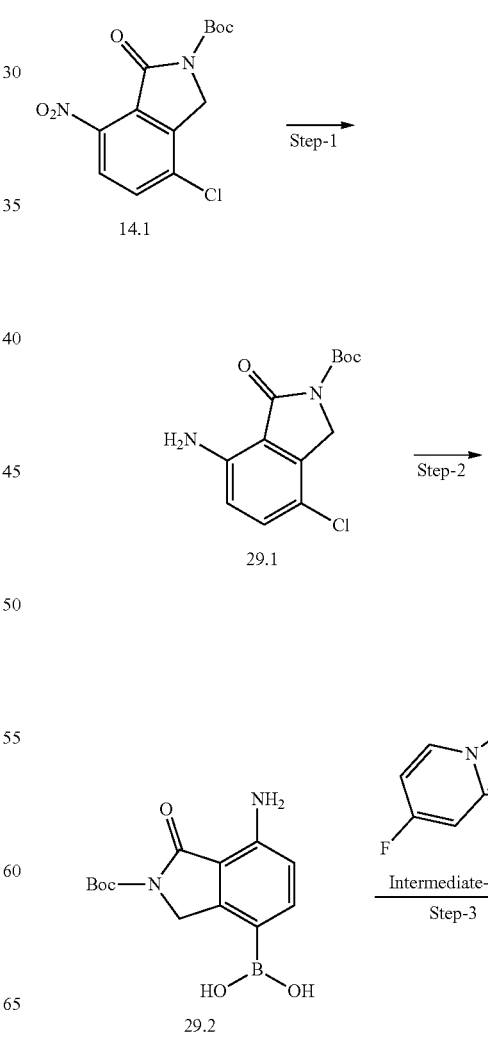

-continued

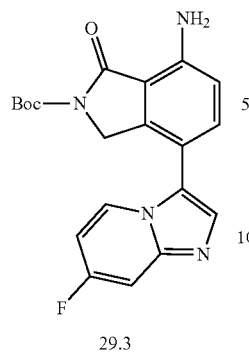

29.3

Step-1 Synthesis of Tert-Butyl 7-amino-4-chloro-1-oxoisoindoline-2-carboxylate (29.1)

To a solution of tert-butyl 4-chloro-7-nitro-1-oxoisoindoline-2-carboxylate (14.1) (170 g, 0.801 mol) in ethyl acetate (1360 mL) at 0° C. were added acetic acid (340 mL) dropwise and zinc (367 g, 5.61 mol) portion wise. After stirring overnight, the reaction mixture was cooled, neutralized with sodium bicarbonate solution, filtered through celite bed, and extracted with ethyl acetate (3×1 L). The combined organic extracts were washed with brine (1.2 L), dried over $Na_2SO_4$, filtered, and concentrated under reduced pressure to afford 29.1 (135 g, 88.13%), MS (ES): m/z=282.6 $[M+H]^+$.

Step-2 Synthesis of 7-amino-2-(tert-butoxycarbonyl)-1-oxoisoindolin-4-yl)boronic Acid (29.2)

To a solution of 29.1 (7 g, 24.8 mmol) in ethanol (10 mL) were added tetrahydroxy diborane (8.83 g, 99.0 mmol, 4 eq), ethylene glycol (4.46 g, 72.2 mmol, 3 eq) and potassium acetate (7.05 g, 72.1 mmol, 3 eq). After degassing with argon for 10 min, X-Phos Pd G2 (943 mg, 1.2 mmol, 0.05 eq) and X-Phos (571 mg, 1.2 mmol, 0.05 eq) were added. After stirring at 80° C. for 1 h, the reaction mixture was poured into water and extracted with EtOAc (30 mL×3). The combined organic layer was washed with brine solution, dried over sodium sulfate, and concentrated under reduced pressure. The residue was purified by trituration with Ether:pentane (1:1) to afford 29.2 (5.4 g, 77.5%). MS (ES): m/z 293.1 $(M+H)^+$.

Step-3 Synthesis of Tert-Butyl 7-amino-4-(7-fluoro-imidazo[1,2-a]pyridin-3-yl)-1-oxoisoindoline-2-carboxylate (29.3)

To a solution of 29.2 (5.4 g, 18.4 mmol) in dioxane:$H_2O$ (50:10 mL) were added 7-fluoro-3-iodoimidazo[1,2-a]pyridine (5.81 g, 22.0 mmol) and potassium phosphate tribasic (11.7 g, 55.2 mmol, 3.0 eq). After degassing using $N_2$ for 15 min, X-Phos Pd G2 (1.44 g, 1.84 mmol, 0.1 eq) was added. After stirring at 100° C. for 1 h, the reaction mixture was poured into water and extracted with EtOAc (50 mL×3). The combined organic layer was washed with brine solution, dried over sodium sulfate, and concentrated under reduced pressure. The residue was purified by column chromatography eluting with 0-100% gradient elution EtOAc in hexane to afford 29.3. (4.5 g, 63.3%). MS (ES): m/z 383.3 $(M+H)^+$.

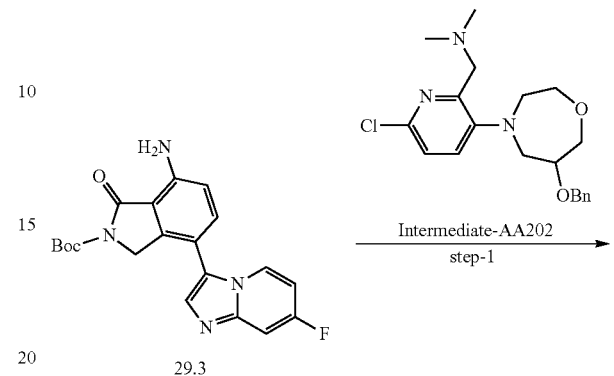

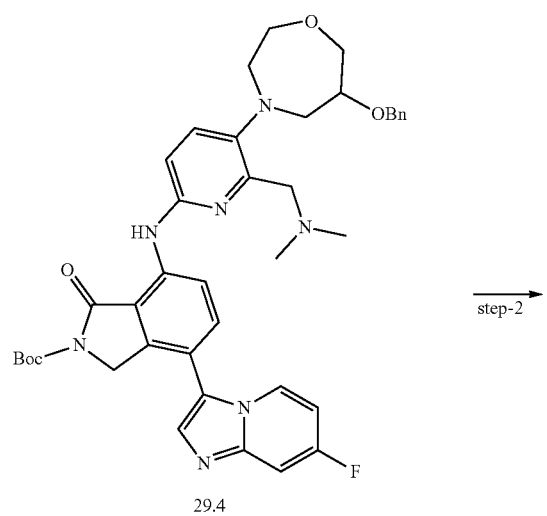

29.4

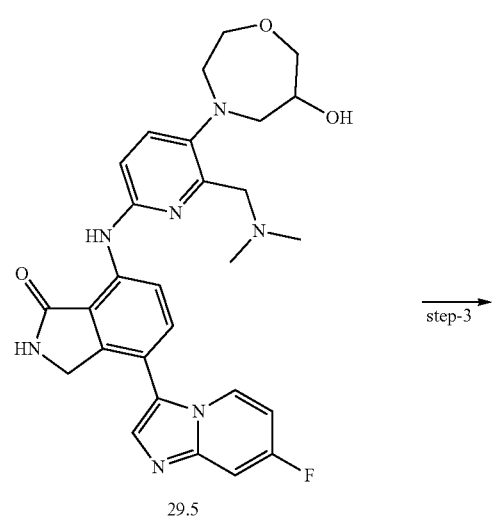

29.5

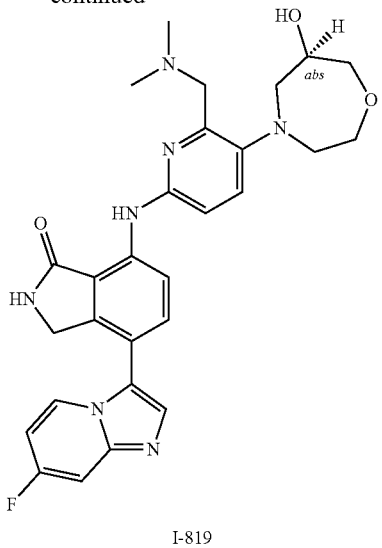

I-819

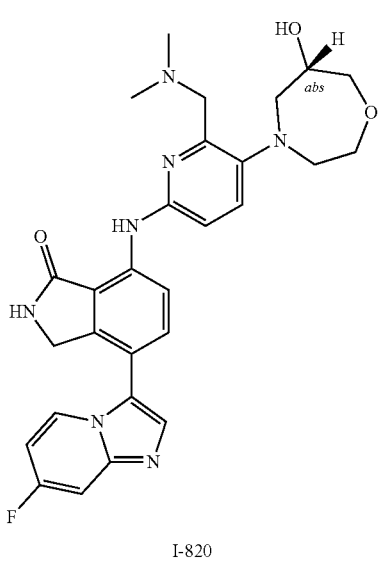

I-820

Step-1 Synthesis of Tert-Butyl 7-((5-(6-(benzy-loxy)-1,4-oxazepan-4-yl)-6-((dimethylamino) methyl)pyridin-2-yl)amino)-4-(7-fluoroimidazo[1,2-a]pyridin-3-yl)-1-oxoisoindoline-2-carboxylate (29.4)

To a solution of tert-butyl 7-amino-4-(7-fluoroimidazo[1,2-a]pyridine-3-yl)-1-oxoisoindoline-2-carboxylate (29.3) (0.300 g, 0.799 mmol) in 1,4-dioxane (5 mL) were added 1-(3-(6-(benzyloxy)-1,4-oxazepan-4-yl)-6-chloropyridine-2-yl)-N,N-dimethylmethanamine (Intermediate-AA202) (0.225 g, 0.588 mmol, 0.75 eq) and potassium carbonate (0.275 g, 1.99 mmol). After stirring at RT for 5 min under argon, 4,5-bis(diphenylphosphino)-9,9-dimethylxanthene (0.2 eq) and tris(dibenzylideneacetone)dipalladium (0.1 eq) were added. After stirring at 110° C. temperature for 1.5 h, the reaction mixture was cooled at RT, diluted with water (200 mL), and extracted with ethyl acetate (3×200 mL). The combined organic extracts were washed with brine (100 mL), dried over $Na_2SO_4$, filtered, and concentrated under reduced pressure. The residue was purified by column chromatography (3% methanol gradient in DCM) to afford 29.4 (0.330 g, 58.30%), MS (ES): m/z=721.2 $[M+H]^+$.

Step-2 Synthesis of 7-((6-((dimethylamino)methyl)-5-(6-hydroxy-1,4-oxazepan-4-yl)pyridin-2-yl) amino)-4-(7-fluoroimidazo[1,2-a]pyridin-3-yl)isoin-dolin-1-one (29.5)

To a solution of 29.4 (300 mg, 0.416 mmol) in DCM (10 mL) at 0° C. was added triflic acid (1 mL). After stirring for 10 min, the reaction mixture was neutralized with 1N sodium hydroxide solution and extracted with DCM. The combined organic layer was dried over sodium sulfate and concentrated under reduced pressure. The residue was purified by trituration with diethyl ether to afford 29.5 as racemic mixture (123 mg, Yield: 75.34%).

Step-3 Chiral Separation: (R)-7-((6-((dimethyl-amino)methyl)-5-(6-hydroxy-1,4-oxazepan-4-yl) pyridin-2-yl)amino)-4-(7-fluoroimidazo[1,2-a]pyri-din-3-yl)isoindolin-1-one (I-819) and (S)-7-((6-((dimethylamino)methyl)-5-(6-hydroxy-1,4-oxazepan-4-yl)pyridin-2-yl)amino)-4-(7-fluoroimidazo[1,2-a]pyridin-3-yl)isoindolin-1-one (I-820)

29.5 (123 mg) was separated by Chiral compound using Shimadzu LC-20AP and UV detector with CHIRALPAK IC (250*21.0) mm, 5 micron, at 18.0 mL/min with mobile phase (A) 0.1% DEA IN n-Hexane and (B) 0.1% DEA in propane-2-ol:acetonitrile (70:30) to afford compounds I-819 (17.5 mg) and I-820 (12 mg). Stereochemistry was arbitrary assigned.

I-819: MS (ES): m/z=532.2 [M+H]+, 1H NMR (400 MHz, DMSO-d6) Isomer-1-(I-522): δ 10.04 (s, 1H), 8.84 (s, 1H), 8.77-8.75 (d, J=8.4 Hz, 1H), 8.46-8.43 (t, J=6.4 Hz, 1H), 8.16 (s, 1H), 7.82 (s, 1H), 7.73-7.66 (dd, J=8.4 Hz, 2H), 7.54-7.52 (d, J=8 Hz 1H), 6.99-6.97 (t, J=8.4 Hz, 1H), 4.39 (s, 2H), 3.96-3.92 (m, 3H), 3.74-3.73 (d, J=4.8 Hz, 2H), 3.65-3.61 (m, 3H), 3.08 (bs, 2H), 3.03-2.98 (m, 2H), 2.34 (s, 6H).

I-820: MS (ES): m/z=532.2 [M+H]+1H NMR (400 MHz, DMSO-d6) Isomer-2 (1-523): δ 10.05 (s, 1H), 8.84 (s, 1H), 8.74-8.72 (d, J=8.4 Hz, 1H), 8.45-8.42 (t, J=6.4 Hz, 1H), 8.16 (s, 1H), 7.82 (s, 1H), 7.73-7.66 (dd, J=8.4 Hz, 2H), 7.54-7.52 (d, J=8 Hz 1H), 6.99-6.97 (t, J=8.4 Hz, 1H), 4.39 (s, 2H), 3.96-3.92 (m, 3H), 3.74-3.73 (d, J=4.8 Hz, 2H), 3.65-3.61 (m, 3H), 3.08 (bs, 2H), 3.03-2.98 (m, 2H), 2.34 (s, 6H).

Example 30. Method ACp
Synthesis of (R)-4-(7-fluoroimidazo[1,2-a]pyridin-3-yl)-7-((5-(3-hydroxy tetrahydrofuran-3-yl)pyridin-2-yl)amino)isoindolin-1-one (I-573) and (S)-4-(7-fluoroimidazo[1,2-a]pyridin-3-yl)-7-((5-(3-hydroxy tetrahydrofuran-3-yl)pyridin-2-yl)amino)isoindolin-1-one (I-574)
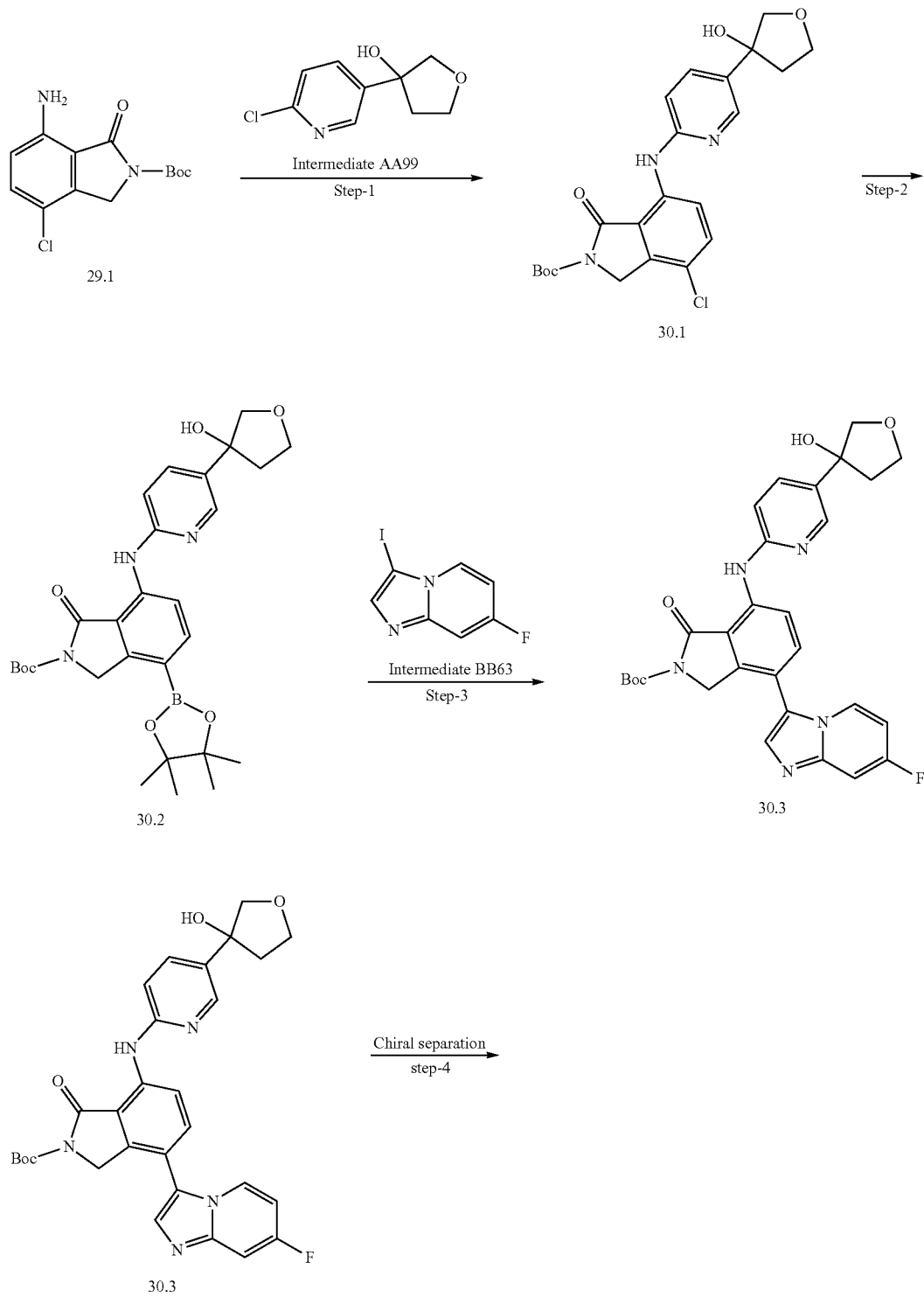

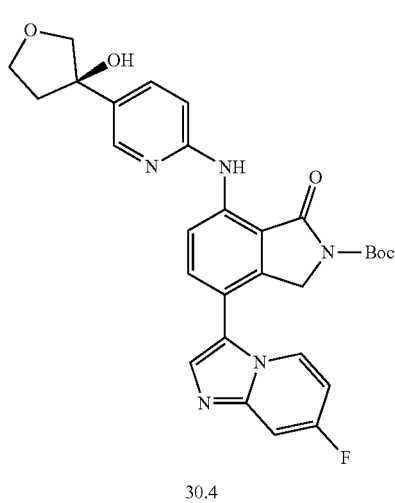

30.4

-continued

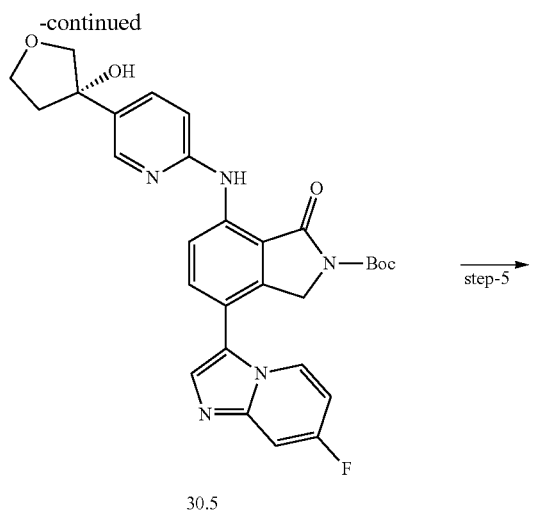

30.5 →step-5

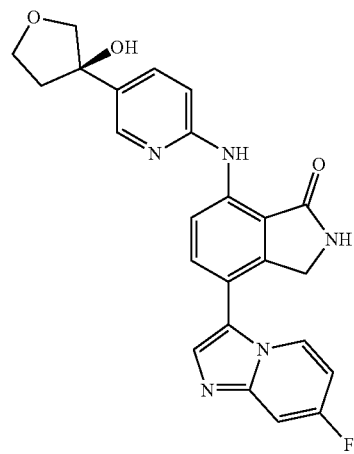

I-573

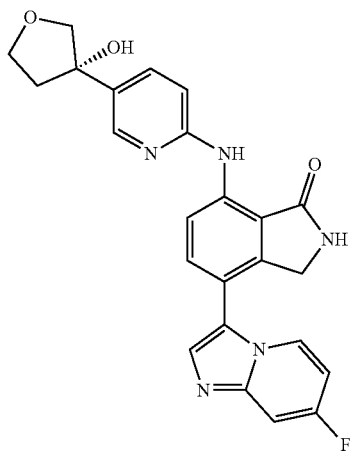

I-574

Step-1 Synthesis of Tert-Butyl 4-chloro-7-((5-(3-hydroxy tetrahydrofuran-3-yl)pyridin-2-yl)amino)-1-oxoisoindoline-2-carboxylate (30.1)

To a solution of 29.1 (700 mg, 4.1 mmol) in 1-4 dioxane (20 mL) were added Intermediate-AA99 (400 mg, 4.1 mmol) and potassium carbonate (1.6 g, 12 mmol, 3.0 eq) at RT. After degassing with nitrogen for 20 min, 4,5-bis(diphenylphosphino)-9,9-dimethylxanthene (120 mg, 0.41 mmol, 0.1 eq) and tris(dibenzylideneacetone)dipalladium (O) (187 mg, 0.41 mmol, 0.1 eq) were added. After stirring at 90° C. for 2 h, the reaction was cool to RT; filtered through celite bed and the celite bed washed with ethyl acetate (60 mL). The combined organic layers were washed with water (50 mL), dried over Na$_2$SO$_4$, and concentrated under reduced pressure. The residue was purified by silica gel chromatography to afford 30.1. (590 mg, 53%) as orange solid. MS (ES): m/z 446.3 [M+1]$^+$ Step 2, 3 4 and 5 were carried out following representative procedures described in Example 27 to afford I-573 and I-574.

I-573: (28 mg), MS (ES) m/z 446.8, $^1$H NMR (400 MHz, DMSO-d6) δ 10.13 (s, 1H), 8.86 (s, 1H), 8.74-8.72 (d, J=8.5 Hz, 1H), 8.51-8.40 (m, 2H), 7.89-7.72 (m, 3H), 7.55 (dd, J=10.0, 2.6 Hz, 1H), 7.10-6.93 (m, 2H), 5.49 (s, 1H), 4.42 (s, 2H), 4.08-3.96 (m, 2H), 3.85 (d, J=8.8 Hz, 1H), 3.77 (d, J=8.9 Hz, 1H), 3.19 (d, J=5.2 Hz, 1H), 2.30 (dt, J=12.7, 9.1 Hz, 1H).

I-574: (28 mg), MS (ES) m/z 446.8, 1H NMR (400 MHz, DMSO-d6) δ 10.12 (s, 1H), 8.87 (s, 1H), 8.73 (d, J=8.6 Hz, 1H), 8.51-8.38 (m, 2H), 7.89-7.69 (m, 3H), 7.55 (dd, J=10.0, 2.6 Hz, 1H), 7.11-6.94 (m, 2H), 5.49 (s, 1H), 4.42 (s, 2H), 4.07-3.96 (m, 2H), 3.85 (d, J=8.8 Hz, 1H), 3.77 (d, J=8.8 Hz, 1H), 3.19 (d, J=5.2 Hz, 1H), 2.31 (dd, J=12.6, 9.1 Hz, 1H).

Example 31. Method ADp

Synthesis of (R)-7-((6-(((2,2-difluoroethyl)amino) methyl)-5-(tetrahydrofuran-3-yl)pyridin-2-yl) amino)-4-(7-fluoroimidazo[1,2-a]pyridin-3-yl)isoindolin-1-one (I-739), (S)-7-((6-(((2,2-difluoroethyl) amino)methyl)-5-(tetrahydrofuran-3-yl)pyridin-2-yl) amino)-4-(7-fluoroimidazo[1,2-a]pyridin-3-yl) isoindolin-1-one (I-740), (R)-7-((6-(((2,2-difluoroethyl)(methyl)amino)methyl)-5-(tetrahydrofuran-3-yl)pyridin-2-yl)amino)-4-(7-fluoroimidazo[1,2-a]pyridin-3-yl)isoindolin-1-one (I-748), (S)-7-((6-(((2,2-difluoroethyl)(methyl) amino)methyl)-5-(tetrahydrofuran-3-yl)pyridin-2-yl) amino)-4-(7-fluoroimidazo[1,2-a]pyridin-3-yl)isoindolin-1-one (I-749)

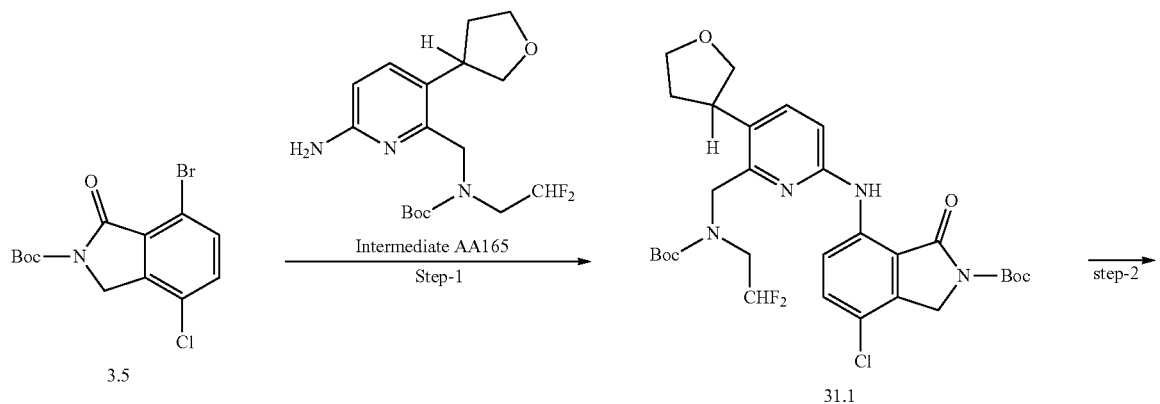

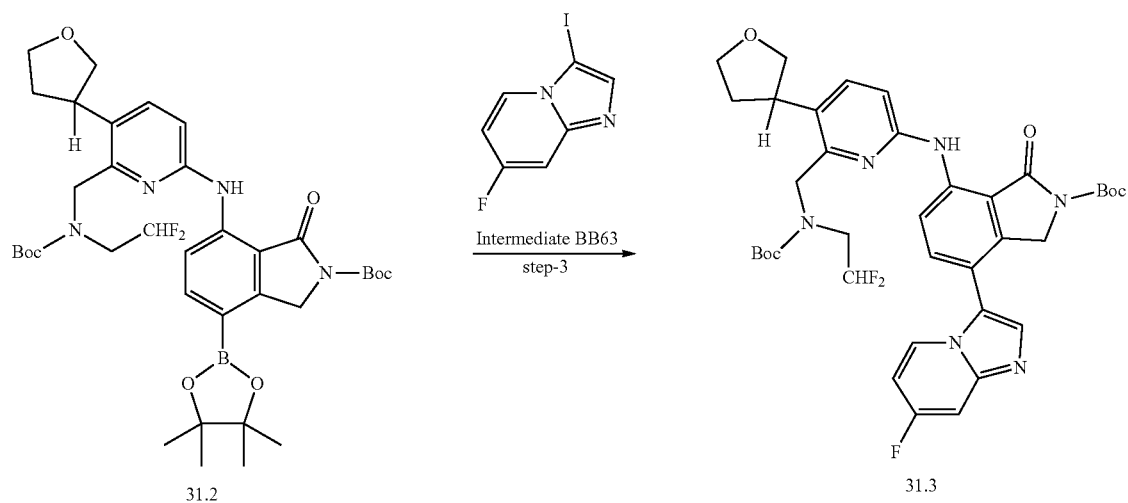

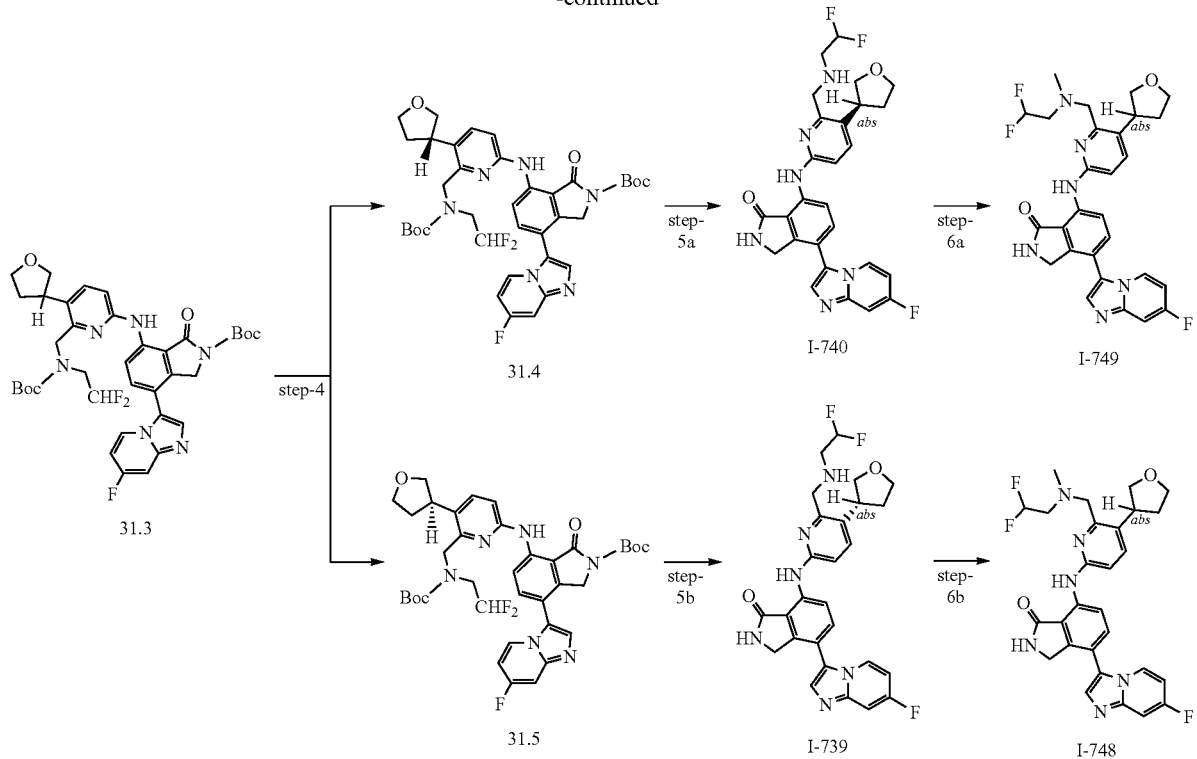

Step-1 Synthesis of Tert-Butyl 7-((6-(((tert-butoxy-carbonyl)(2,2-difluoroethyl)amino)methyl)-5-(tetra-hydrofuran-3-yl)pyridin-2-yl)amino)-4-chloro-1-oxoisoindoline-2-carboxylate (31.1)

To a solution of 3.5 (1.2 g, 3.46 mmol) and Intermediate AA165 (1.2 g, 3.46 mmol) in 1,4-dioxane (15 mL) were added Cs$_2$CO$_3$ (3.3 g, 10.38 mmol, 3.0 eq) and Xantphos (0.4 g, 0.69 mmol, 0.2 eq). After degassing under N$_2$ for 15 min, Pd$_2$(dba)$_3$ (0.316 g, 0.34 mmol, 0.1 eq) was added. After stirring at 110° C. for 1.5 h, the reaction mixture was cooled to RT, diluted water (30 mL) and extracted with ethyl acetate (30 mL). The organic layer was collected, and the aqueous phase was extracted with ethyl acetate (2×40 mL). The combined organic extracts were washed with brine (20 mL), dried over Na$_2$SO$_4$, filtered, and concentrated under reduced pressure. The residue was purified by column chromatography (2-8% methanol gradient in DCM). The residue was then triturated with diethyl ether and the resulting solid was collected by filtration to afford the title compound 31.1 (1.6 g, 76.48%) as a brown solid. MS (ES): m/z=623.5 [M+2]$^+$ Step-2 Synthesis of Tert-Butyl 7-((6-(((tert-butoxy-carbonyl)(2,2-difluoroethyl)amino)methyl)-5-(tetra-hydrofuran-3-yl)pyridin-2-yl)amino)-1-oxo-4-(4,4,5,5-tetramethyl-1,3,2-dioxaborolan-2-yl)isoindoline-2-carboxylate (31.2)

To a solution of 39.1 (0.970 g, 2.57 mmol) in dioxane (20 mL) were added bis(pinacolato)diboron (1.9 g, 7.71 mmol, 3.0 eq) and potassium acetate (0.755 g, 7.71 mmol, 3.0 eq). After degassing with N$_2$ for 15 min, X-Phos pd G2 (0.202 g, 0.25 mmol, 0.1 eq) was added. After stirring at 100° C. for 1 h, the reaction mixture was cooled to RT and diluted ethyl acetate (50 mL) and water (30 mL). The organic layer was collected, and the aqueous phase was extracted with ethyl acetate (2×20 mL). The combined organic extracts were washed with brine (10 mL), dried over Na$_2$SO$_4$, filtered, and concentrated under reduced pressure to afford 31.2 (1.2 g), which was used in the next step without further purification. MS (ES): m/z 715.36 [M+H]$^+$.

Step-3 Synthesis of Tert-Butyl 7-((6-(((tert-butoxy-carbonyl)(2,2-difluoroethyl)amino)methyl)-5-(tetra-hydrofuran-3-yl)pyridin-2-yl)amino)-4-(7-fluoroimi-dazo[1,2-a]pyridin-3-yl)-1-oxoisoindoline-2-carboxylate (31.3)

To a solution of 31.2 (1.2 g, 1.67 mmol) in dioxane (12 mL) and water (2 mL) were added Intermediate BB63 (0.87 g, 3.35 mmol, 2.0 eq) and potassium phosphate tribasic (1.0 g, 5.01 mmol, 3.0 eq). After degassing with N$_2$ for 15 min, X-Phos Pd G2 (0.125 g, 0.16 mmol, 0.1 eq) was added. After stirring at 110° C. for 2 h, the reaction mixture was cooled to RT and then diluted ethyl acetate (20 mL) and water (20 mL). The organic layer was collected, and the aqueous phase was extracted with ethyl acetate (2×20 mL). The combined organic extracts were washed with brine (20 mL), dried over Na$_2$SO$_4$, filtered, and concentrated under reduced pressure. The residue was purified by column chromatography eluting with 3.8% methanol gradient in DCM to afford 31.3 (0.6 g, 49.44%), MS (ES): m/z 723.5 [M+H]$^+$ Step-4 Synthesis of Tert-Butyl (S)-7-((6-(((tert-butoxycarbonyl)(2,2-difluoroethyl)amino)methyl)-5-(tetrahydrofuran-3-yl)pyridin-2-yl)amino)-4-(7-fluoroimidazo[1,2-a]pyridin-3-yl)-1-oxoisoindoline-2-carboxylate (31.4) and Tert-Butyl (R)-7-((6-(((tert-butoxycarbonyl)(2,2-difluoroethyl)amino)methyl)-5-(tetrahydrofuran-3-yl)pyridin-2-yl)amino)-4-(7-fluoroimidazo[1,2-a]pyridin-3-yl)-1-oxoisoindoline-2-carboxylate (31.5)

31.3 (600 mg) was separated on Waters SFC 200 and UV detector. using CHIRALPAK IC (250*21.0) mm, 5 micron, at 80.0 mL/min at 100 bar ABPR using mobile (A) Liquid Carbon dioxide (Liq. CO2) and (B) 0.1% DEA in propanol: acetonitrile (50:50) to afford compounds 31.4 (200 mg) and 31.5 (250 mg). Stereochemistry was arbitrary assigned.

Step-5b Synthesis of R)-7-((6-(((2,2-difluoroethyl) amino)methyl)-5-(tetrahydrofuran-3-yl)pyridin-2-yl) amino)-4-(7-fluoroimidazo[1,2-a]pyridin-3-yl)isoindolin-1-one (I-739)

To solution of 31.5 (0.250 g, 0.34 mmol, 1.0 eq) in DCM (3 mL) was added dropwise TFA (1.5 mL) at 0° C. After stirring at RT for 30 min, the reaction mixture was neutralized using saturated sodium bicarbonate solution and extracted with 10% methanol in DCM (3×30 mL). The combine organic layer was concentrated under reduced pressure and purified by triturating with n-pentane to afford the title compound I-739 (0.110 g, 60.86%) as white solid. MS (ES): m/z 523.20 [M+H]$^+$. $^1$H NMR (400 MHz, DMSO): δ 10.05 (s, 1H), 8.87 (s, 1H), 8.71-8.69 (d, J=8.8 Hz, 1H), 8.44-8.42 (t, J=2.6 Hz, 1H), 7.84 (s, 1H), 7.72-7.70 (d, J=8.8 Hz 1H), 7.67-7.65 (d, J=8.4 Hz, 1H), 7.57-7.53 (m, 1H), 7.02-7.01 (d, J=2.8 Hz, 1H), 6.94 (s, 1H), 4.40 (s, 2H), 3.99-3.93 (m, 4H), 3.84-3.79 (m, 1H), 3.65-3.61 (m, 3H), 3.58-3.54 (m, 1H), 2.99-2.98 (d, J=3.6 Hz, 2H), 1.94-1.85 (m, 1H), 1.26 (bs, 1H).

Step-6b Synthesis of R)-7-((6-(((2,2-difluoroethyl) (methyl)amino)methyl)-5-(tetrahydrofuran-3-yl) pyridin-2-yl)amino)-4-(7-fluoroimidazo[1,2-a]pyridin-3-yl) isoindolin-1-one (I-748)

To a solution 1-739 (0.090 g, 0.172 mmol, 1.0 eq) in dichloroethane (3 mL) at 0° C. were added formaldehyde (0.020 g, 0.688 mmol, 4.0 eq) and acetic acid (0.1 mL). After 20 min, sodium triacetoxyborohydride (0.182 g, 0.86 mmol, 5.0 eq) was added portion wise. After stirring at RT for 1 h, the reaction mixture was diluted with water (20 mL) and extracted with ethyl acetate (3×20 mL). The combined organic layer was washed with brine solution, dried over sodium sulfate, and concentrated under reduced pressure. The residue was purified by reverse phase column chromatography eluting with 1.8% methanol in DCM to afford the title compound I-748 (0.035 g, 37.87%) as White solid. MS (ES): m/z 537.28 [M+H]$^+$ $^1$H NMR (400 MHz, DMSO): δ 10.06 (s, 1H), 8.86 (s, 1H), 8.77-8.75 (d, J=8.4 Hz, 1H), 8.46-8.43 (t, J=6.4 Hz, 1H), 7.83 (s, 1H), 7.74-7.71 (d, J=8.4 Hz, 1H), 7.69-7.67 (d, J=8.4 Hz, 1H), 7.55-7.52 (d, J=10 Hz, 1H), 6.99-6.95 (t, J=7.2 Hz, 2H), 4.39 (s, 2H), 4.01-3.97 (m, 2H), 3.83-3.75 (m, 4H), 3.54-3.50 (t, J=7.2 Hz, 3H), 2.87-2.86 (t, J=3.6 Hz, 2H), 1.92-1.83 (m, 2H), 1.23 (bs, 2H).

Step-5a Synthesis of S)-7-((6-(((2,2-difluoroethyl) amino)methyl)-5-(tetrahydrofuran-3-yl)pyridin-2-yl) amino)-4-(7-fluoroimidazo[1,2-a]pyridin-3-yl)isoindolin-1-one (I-740)

To a solution of 31.5 (0.2 g, 0.27 mmol) in DCM (3 mL) at 0° C. was added dropwise TFA (1.4 mL). After stirring at RT for 30 min, the reaction mixture was neutralized using saturated sodium bicarbonate solution and extracted with 10% methanol in DCM (3×20 mL). The combine organic layer was concentrated under reduced pressure and purified by trituration with n-pentane to afford the title compound I-740 (0.1 g, 69.16%) as white solid. MS (ES): m/z 523.20 [M+H]$^+$ $^1$H NMR (400 MHz, DMSO): δ 10.06 (s, 1H), 8.87 (s, 1H), 8.70-8.69 (d, J=8.8 Hz, 1H), 8.44-8.42 (t, J=2.6 Hz, 1H), 7.84 (s, 1H), 7.72-7.70 (d, J=8.8 Hz 1H), 7.67-7.65 (d, J=8.4 Hz, 1H), 7.57-7.53 (m, 1H), 7.02-7.01 (d, J=2.8 Hz, 1H), 6.94 (s, 1H), 4.40 (s, 2H), 3.99-3.93 (m, 4H), 3.84-3.79 (m, 1H), 3.65-3.61 (m, 3H), 3.58-3.54 (m, 1H), 2.99-2.98 (d, J=3.6 Hz, 2H), 1.94-1.85 (m, 1H), 1.23 (bs, 1H).

Step-6a Synthesis of S)-7-((6-(((2,2-difluoroethyl) (methyl)amino)methyl)-5-(tetrahydrofuran-3-yl) pyridin-2-yl)amino)-4-(7-fluoroimidazo[1,2-a]pyridin-3-yl)isoindolin-1-one (I-749)

To a solution of I-740 (0.080 g, 0.153 mmol, 1.0 eq) in dichloroethane (3 mL) at 0° C. were added formaldehyde (0.018 g, 0.612 mmol, 4.0 eq) and acetic acid (0.5 mL). After 20 min, sodium triacetoxyborohydride (0.162 g, 0.765 mmol, 5.0 eq) was added portion wise. After stirring at RT for 1 h, the reaction mixture was diluted with water (20 mL) and extracted with ethyl acetate (3×20 mL). The combined organic layer was washed with brine solution, dried over sodium sulfate, and concentrated under reduced pressure. The residue was purified by reverse phase column chromatography eluting with 2% methanol in DCM to afford the title compound I-749 (0.025 g, 30.43%) as white solid. MS (ES): m/z 537.56 [M+H]$^+$. $^1$H NMR (400 MHz, DMSO): δ 10.06 (s, 1H), 8.86 (s, 1H), 8.77-8.75 (d, J=8.4 Hz, 1H), 8.46-8.43 (t, J=6.4 Hz, 1H), 7.83 (s, 1H), 7.74-7.71 (d, J=8.4 Hz, 1H), 7.69-7.67 (d, J=8.4 Hz, 1H), 7.55-7.52 (d, J=10 Hz, 1H), 6.99-6.95 (t, J=7.2 Hz, 2H), 4.39 (s, 2H), 4.01-3.97 (m, 2H), 3.83-3.75 (m, 4H), 3.54-3.50 (t, J=7.2 Hz, 3H), 2.87-2.86 (t, J=3.6 Hz, 2H), 1.92-1.83 (m, 2H), 1.23 (bs, 2H).

Example 32. Method AEp

Synthesis of 4-(7-fluoroimidazo[1,2-a]pyridin-3-yl)-7-((5-((R)-2-((R)-1-hydroxyethyl)morpholino)pyridin-2-yl)amino)isoindolin-1-one (I-619), 4-(7-fluoroimidazo[1,2-a]pyridin-3-yl)-7-((5-((S)-2-((S)-1-hydroxyethyl)morpholino)pyridin-2-yl)amino) isoindolin-1-one (I-620), 4-(7-fluoroimidazo[1,2-a] pyridin-3-yl)-7-((5-((R)-2-((S)-1-hydroxyethyl) morpholino)pyridin-2-yl)amino)isoindolin-1-one (I-634), and 4-(7-fluoroimidazo[1,2-a]pyridin-3-yl)-7-((5-((S)-2-((R)-1-hydroxyethyl)morpholino)pyridin-2-yl)amino)isoindolin-1-one (I-635)

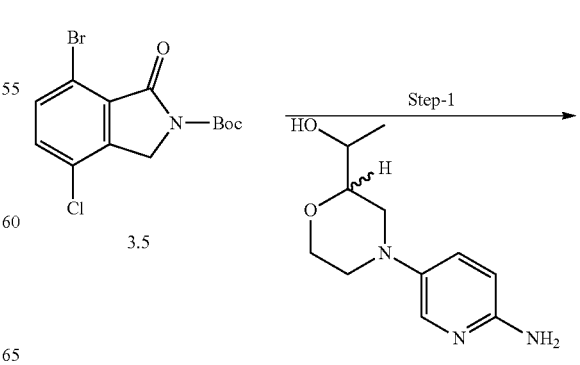

Intermediate AA111

-continued

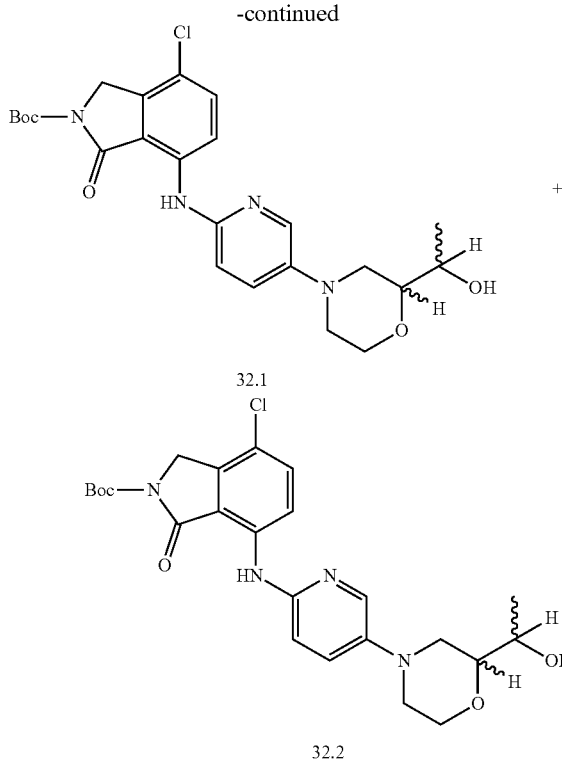

Step-1 Synthesis of Tert-Butyl 4-chloro-7-((5-(2-(1-hydroxyethyl)morpholino)pyridin-2-yl)amino)-1-oxoisoindoline-2-carboxylate (32.1) and Tert-Butyl 4-chloro-7-((5-(2-(1-hydroxyethyl)morpholino)pyridin-2-yl)amino)-1-oxoisoindoline-2-carboxylate (32.2)

To a solution of 3.5 (2.25 g, 6.4 mmol) and Intermediate AA111 (1.7 mg, 7.7 mmol, 1.2 eq) in 1, 4-dioxane (30 mL) was added $K_2CO_3$ (2.7 g, 19.4 mmol, 3 eq). After degassing with $N_2$ for 15 min, $Pd_2(dba)_3$ (0.594 g, 0.64 mmol, 0.05 eq) and Xantphos (0.748 g, 1.2 mmol, 0.2 eq) were added. After stirring at 110° C. for 1.5 h, the reaction mixture was cooled at RT and diluted with water (50 mL) and ethyl acetate (300 mL). The organic layer was collected, and the aqueous phase was extract with ethyl acetate (30 mL). The combined organic extracts were washed with brine (20 mL), dried over $Na_2SO_4$, filtered, and concentrated under reduced pressure. The residue was purified by column chromatography (1%-2.5% gradient elution MeOH in DCM) to afford diastereomer-1 as 32.1 and diastereomer-2 as 32.2.

32.1 was further triturated with diethyl ether to afford 32.1 (2.2 g, 45.6%). MS (ES): m/z=489.9 [M+1]+

32.2 was further triturated with diethyl ether to afford 32.2 (1.8 g, 66.5%). MS (ES): m/z=489.8 [M+1]+

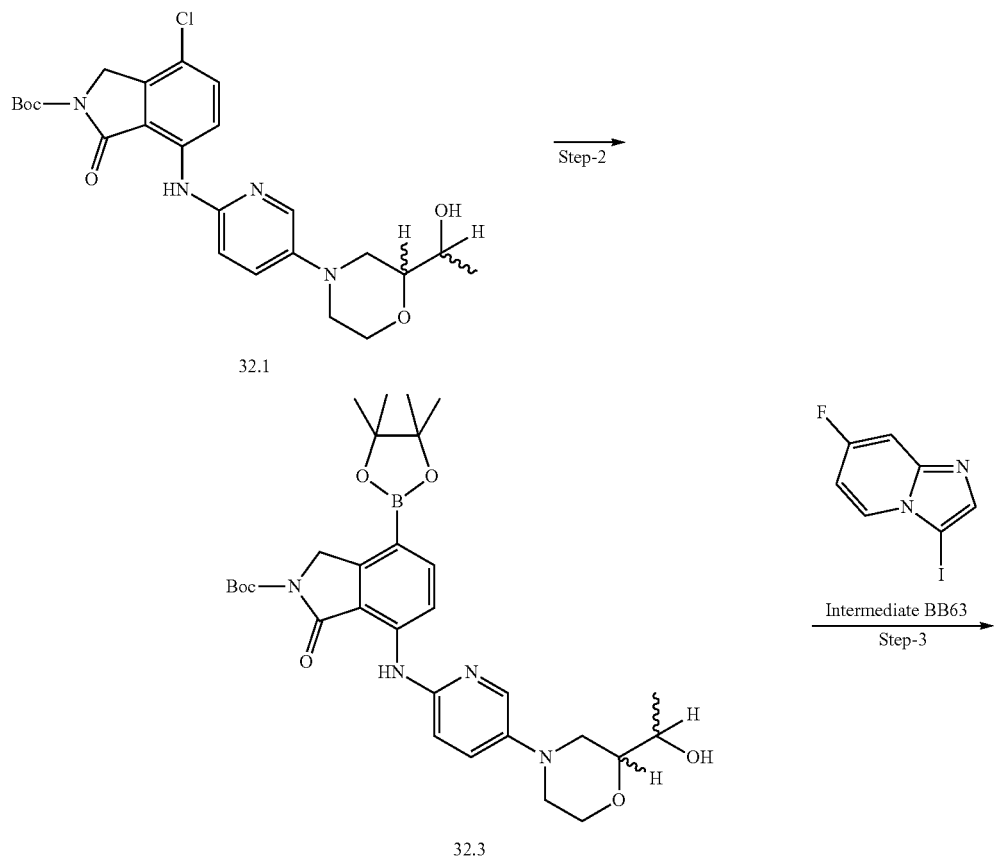

-continued
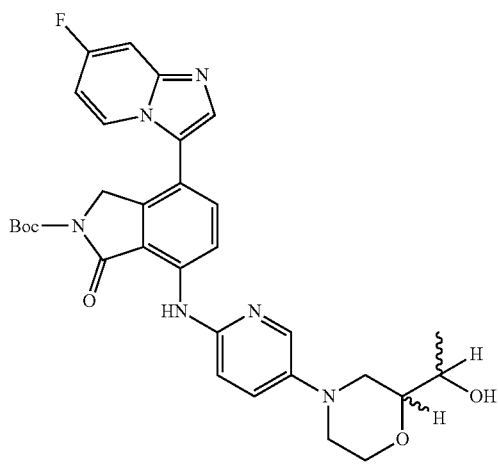
32.4
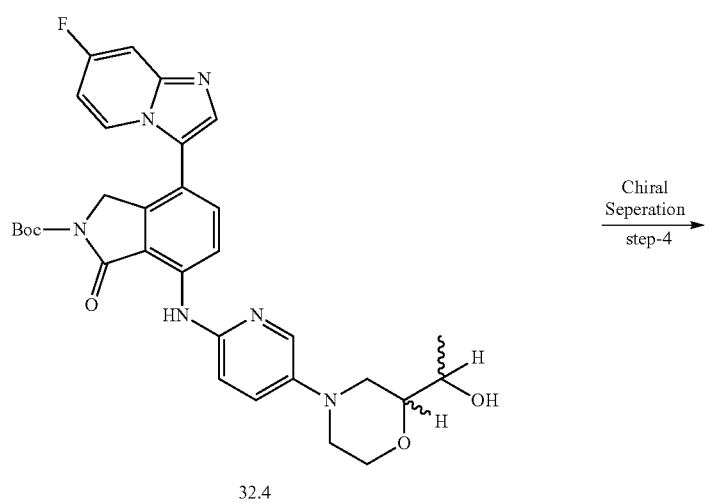
32.4
Chiral
Seperation
step-4
→
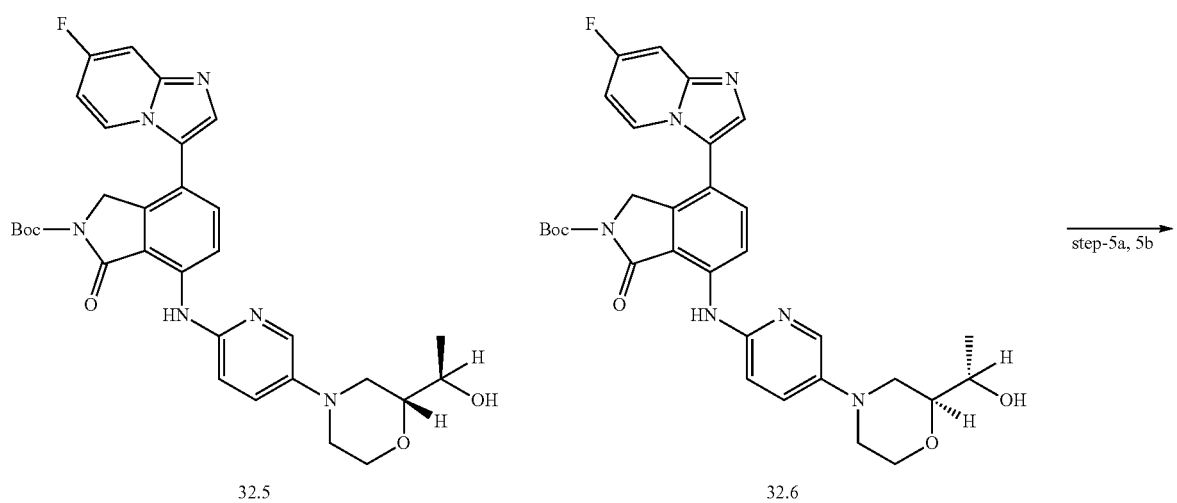
32.5
32.6
step-5a, 5b →

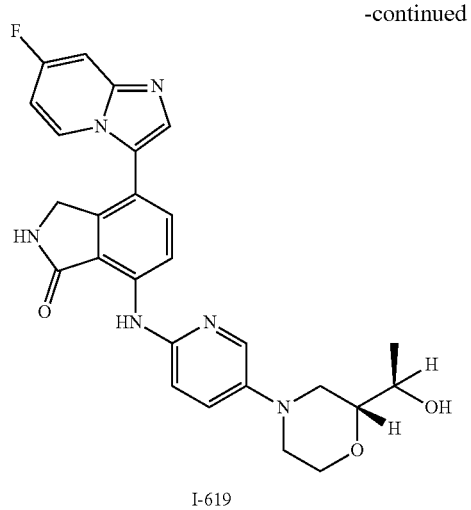

I-619

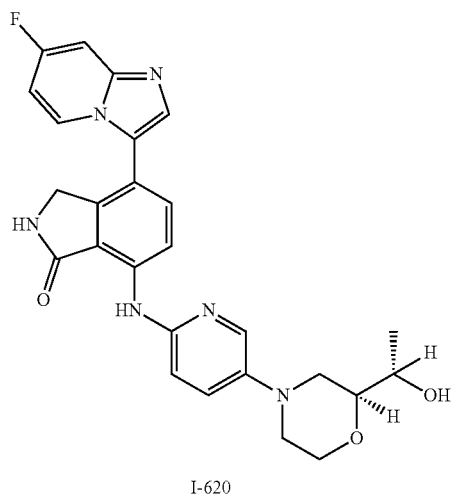

I-620

Step-2 Synthesis of Racemic Mixture Tert-Butyl 7-((5-(2-(1-hydroxyethyl)morpholino)pyridin-2-yl)amino)-1-oxo-4-(4,4,5,5-tetramethyl-1,3,2-dioxaborolan-2-yl)isoindoline-2-carboxylate (32.2)

To a solution of 32.1 (0.97 g, 1.9 mmol) in dioxane (5 mL) were added bis(pinacolato)diboron (2 g, 7.9 mmol, 4 eq) and potassium acetate (0.586 g, 5.9 mmol, 3.0 eq). After degassing with $N_2$ for 15 min, X-Phos Pd G2 (0.072 g, 0.078 mmol, 0.05 eq) was added. After stirring at 110° C. for 2 h, the reaction mixture was cooled at RT and diluted with ethyl acetate (20 mL) and water (15 mL). The organic layer was collected, and the aqueous phase was extracted with ethyl acetate (2×30 mL). The combined organic extracts were washed with brine (10 mL), dried over $Na_2SO_4$, filtered, and concentrated under reduced pressure. The residue was purified by column chromatography (0-1% gradient elution MeOH in DCM) to afford 32.3 (0.900 g), MS (ES): m/z=580.4 [M+H]$^+$.

Step-3 Synthesis of Racemic Mixture Tert-Butyl 4-(7-fluoroimidazo[1,2-a]pyridin-3-yl)-7-((5-(2-(1-hydroxyethyl)morpholino)pyridin-2-yl)amino)-1-oxoisoindoline-2-carboxylate (32.4)

To a solution of 32.3 (0.9 g, 1.5 mmol) in dioxane (8 mL) and water (2 mL). were added Intermediate BB63 (0.48 g, 1.8 mmol, 1.2 eq) and potassium phosphate tribasic (0.98 g, 4.6 mmol, 3.0 eq). After degassing with $N_2$ for 15 min, X-Phos Pd G2 (0.061 g, 0.07 mmol, 0.05 eq) was added. After stirring at 100° C. for 2 h, the reaction mixture was cooled at RT and diluted with ethyl acetate (20 mL) and water (20 mL). The organic layer was collected, and the aqueous phase was extracted with ethyl acetate (2×30 mL). The combined organic extracts were washed with brine (20 mL), dried over $Na_2SO_4$, filtered, and concentrated under reduced pressure. The residue was purified by column chromatography eluting with 1.8% methanol gradient in DCM to afford 32.4 (0.420 g, 46%), MS (ES): m/z=588.6 [M+H]+

Step-4 Synthesis of Tert-Butyl 4-(7-fluoroimidazo[1,2-a]pyridin-3-yl)-7-((5-((R)-2-((R)-1-hydroxyethyl)morpholino)pyridin-2-yl)amino)-1-oxoisoindoline-2-carboxylate (32.5) and Tert-Butyl 4-(7-fluoroimidazo[1,2-a]pyridin-3-yl)-7-((5-((S)-2-((S)-1-hydroxyethyl)morpholino)pyridin-2-yl)amino)-1-oxoisoindoline-2-carboxylate (32.6)

32.4 (420 mg) was separated on Shimadzu LC-20AP and UV detector using CHIRALPAK IC (250*21.0) mm column, 5 micron, at 18.0 mL/min using mobile phase (A) 0.1% DEA IN n-Hexane and (B)0.1% DEA in propanol:acetonitrile (70:30) to afford 32.5 (200 mg) and 32.6 (190 mg). The stereochemistry was arbitrarily assigned.

Step-5a Synthesis of 4-(7-fluoroimidazo[1,2-a]pyridin-3-yl)-7-((5-((R)-2-((R)-1-hydroxyethyl)morpholino)pyridin-2-yl)amino)isoindolin-1-one (I-619)

To a solution of 32.5 (0.200 g, 0.3 mmol) into DCM (5 mL) at 0° C. was added TFA (5 mL). After stirring at RT for 30 min, the reaction mixture was neutralized using saturated sodium bicarbonate solution and extracted with 10% methanol in DCM (3×20 mL). The combine organic layer was concentrated under reduced pressure. The residue was purified by column chromatography to afford the title compound I-619 (0.12 g, 72%) as an off white solid. MS (ES): m/z 488.5 (M+H). 1H NMR (400 MHz, DMSO-d6) δ 9.89 (s, 1H), 8.80 (s, 1H), 8.58 (d, J=8.5 Hz, 1H), 8.44 (t, J=6.6 Hz, 1H), 8.01 (d, J=2.9 Hz, 1H), 7.83 (s, 1H), 7.70 (d, J=8.6 Hz, 1H), 7.50 (ddd, J=31.9, 9.5, 2.8 Hz, 2H), 7.04-6.94 (m, 2H), 4.81 (d, J=5.4 Hz, 1H), 4.39 (s, 2H), 4.02-3.93 (m, 1H), 3.71-3.51 (m, 2H), 3.42 (dd, J=23.8, 9.3 Hz, 1H), 3.30 (ddd, J=9.9, 7.1, 2.4 Hz, 2H), 2.69 (td, J=11.7, 3.4 Hz, 1H), 2.46 (t, J=10.9 Hz, 1H), 1.19-1.06 (m, 3H).

Step-5b Synthesis of 4-(7-fluoroimidazo[1,2-a]pyridin-3-yl)-7-((5-((S)-2-((S)-1-hydroxyethyl)morpholino)pyridin-2-yl)amino)isoindolin-1-one (I-620)

To a solution of 32.6 (0.200 g, 0.3 mmol) in DCM (5 mL) at 0° C. was added TFA (5 mL). After stirring at RT for 30 min, the reaction mixture was neutralized using saturated sodium bicarbonate solution and extracted with 10% metha nol in DCM (3×20 mL). The combine organic layer was concentrated under reduced pressure. The residue was purified by column chromatography to afford the title compound I-620 (0.115 g, 72%) as an off white solid. MS (ES): m/z 488.5 (M+H). 1H NMR (400 MHz, DMSO-d6) δ 9.89 (s, 1H), 8.80 (s, 1H), 8.58 (d, J=8.5 Hz, 1H), 8.44 (t, J=6.7 Hz, 1H), 8.04-7.93 (m, 1H), 7.83 (s, 1H), 7.70 (d, J=8.5 Hz, 1H), 7.50 (ddd, J=32.0, 9.5, 2.8 Hz, 2H), 7.04-6.94 (m, 2H), 4.81 (d, J=5.3 Hz, 1H), 4.39 (s, 1H), 4.01-3.93 (m, 1H), 3.69-3.53 (m, 1H), 3.44 (t, J=13.2 Hz, 1H), 3.35 (s, 3H), 3.30 (ddd, J=9.8, 6.9, 2.3 Hz, 1H), 2.69 (td, J=11.7, 3.4 Hz, 1H), 2.46 (t, J=10.9 Hz, 1H), 1.16 (d, J=6.2 Hz, 3H).
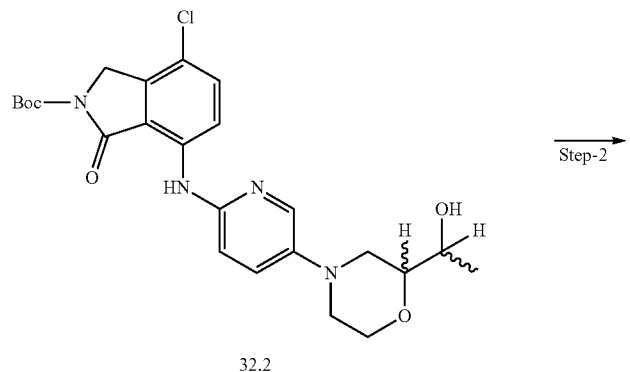
32.2
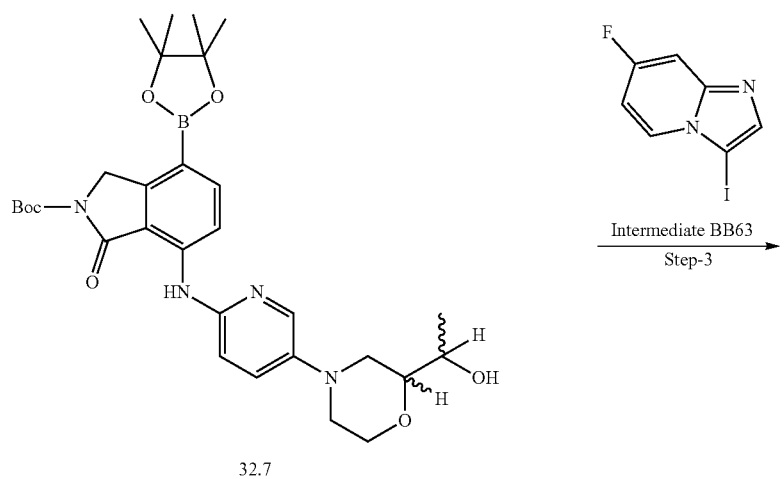
32.7
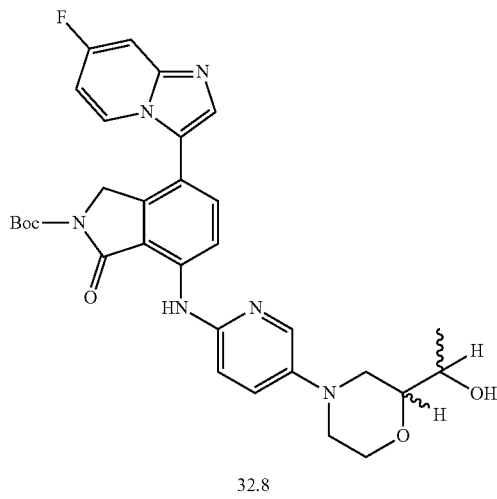
32.8

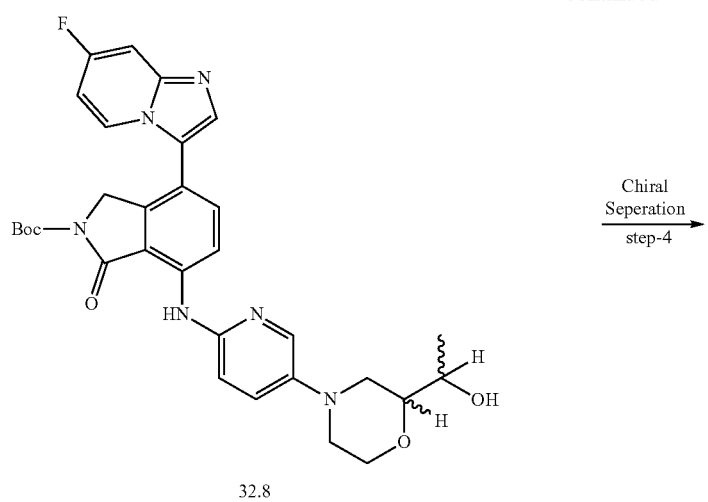
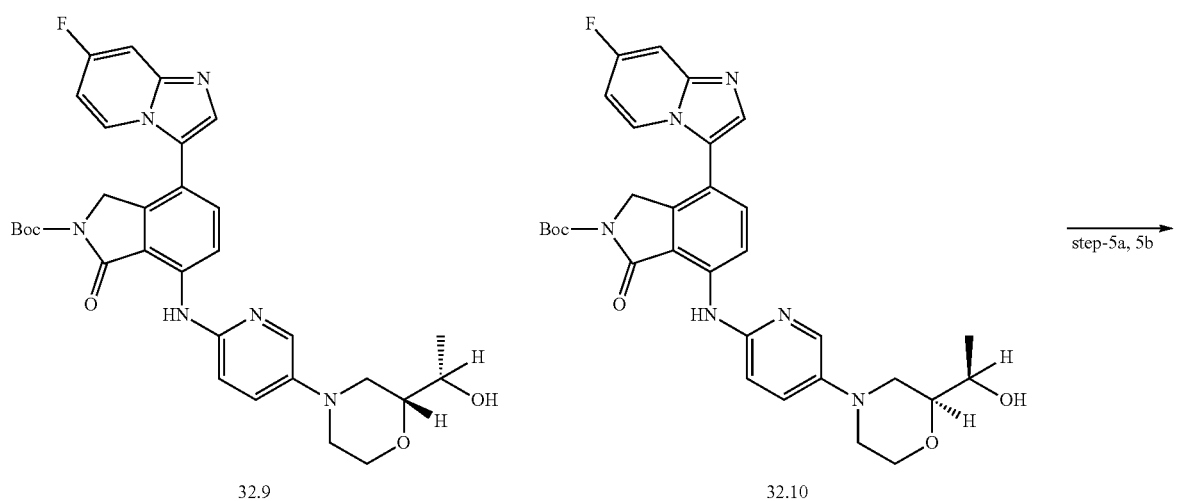
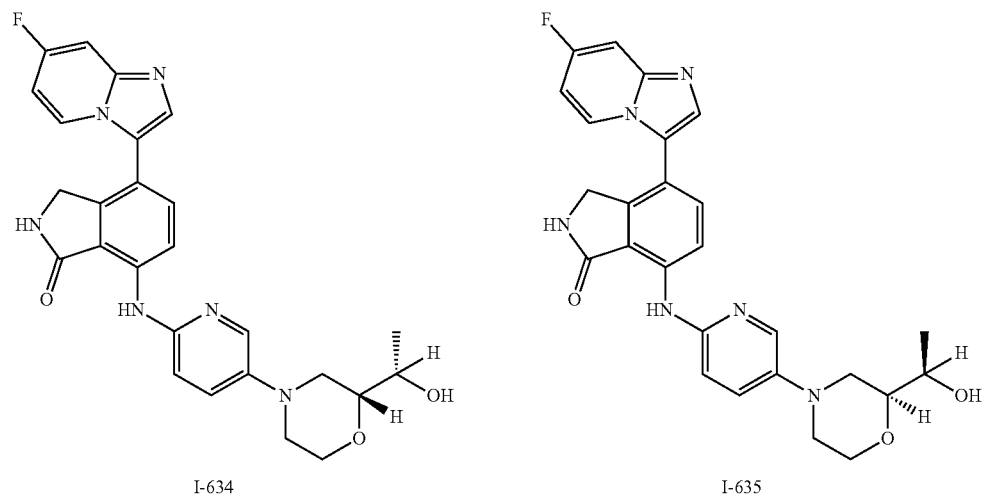

1211

Synthesis of 4-(7-fluoroimidazo[1,2-a]pyridin-3-yl)-7-((4-((R)-2-((S)-1-hydroxyethyl)morpholino)pyridin-2-yl)amino)isoindolin-1-one (I-634) and 4-(7-fluoroimidazo[1,2-a]pyridin-3-yl)-7-((5-((S)-2-((R)-1-hydroxyethyl) morpholino) pyridin-2-yl) Amino) isoindolin-1-one (I-635)

I-634 and I-635 were prepared from 32.2 followings step 2, step-3, step-4 and step-5a, step-5b as described above for other diastereomer 32.1.

I-634: (106 mg), MS (ES) m/z 489.2, 1H NMR (400 MHz, DMSO-d6) δ 9.87 (s, 1H), 8.79 (s, 1H), 8.58-8.56 (d, J=8.6 Hz, 1H), 8.44-8.40 (t, J=6.8 Hz, 1H), 8.02-8.01 (d, J=3.0 Hz, 1H), 7.81 (s, 1H), 7.70-7.68 (d, J=8.6 Hz, 1H), 7.54-7.48 (ddd, J=24.0, 9.5, 2.8 Hz, 2H), 6.99-6.96 (t, J=8.8 Hz, 2H), 4.67-4.65 (d, J=5.1 Hz, 1H), 4.38 (s, 2H), 3.99-3.97 (d, J=10.3 Hz, 1H), 3.67-3.62 (m, 2H), 3.50-3.42 (m, 3H), 2.69-2.60 (m, 2H), 1.12-1.10 (d, J=6.4 Hz, 3H).

I-635: (117 mg), MS (ES) m/z 489.2, 1H NMR (400 MHz, DMSO-d6) δ 9.87 (s, 1H), 8.79 (s, 1H), 8.58-8.56 (d, J=8.6 Hz, 1H), 8.44-8.40 (t, J=6.8 Hz, 1H), 8.02-8.01 (d, J=3.0 Hz, 1H), 7.81 (s, 1H), 7.70-7.68 (d, J=8.6 Hz, 1H), 7.54-7.48 (ddd, J=24.0, 9.5, 2.8 Hz, 2H), 6.99-6.96 (t, J=8.8 Hz, 2H), 4.67-4.65 (d, J=5.1 Hz, 1H), 4.38 (s, 2H), 3.99-3.97 (d, J=10.3 Hz, 1H), 3.67-3.62 (m, 2H), 3.50-3.42 (m, 3H), 2.69-2.60 (m, 2H), 1.12-1.10 (d, J=6.4 Hz, 3H).

Example 34. Method AHp

Synthesis of 7-((6-((dimethylamino)methyl)-5-(1-methoxycyclopropyl)pyridin-2-yl)amino)-4-(7-fluoroimidazo[1,2-a]pyridin-3-yl)isoindolin-1-one (I-823)

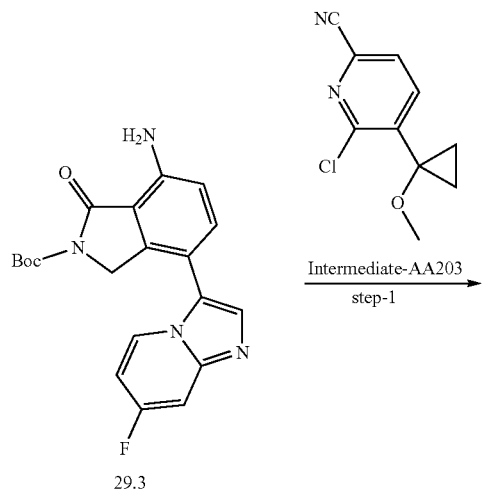

29.3

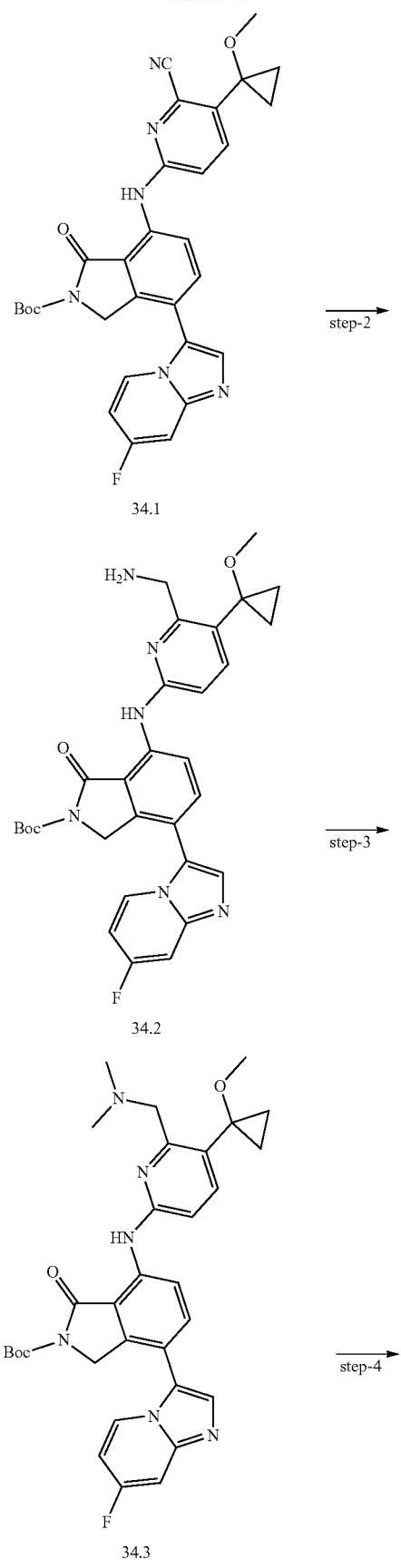

-continued

-continued

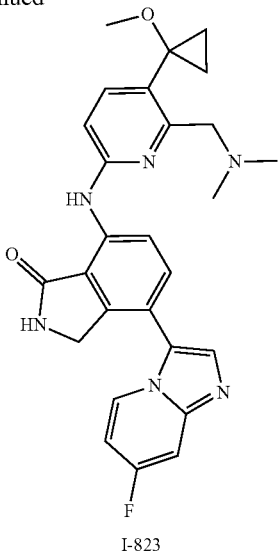

I-823

Step-1 Tert-Butyl 7-((6-cyano-5-(1-methoxycyclopropyl)pyridin-2-yl)amino)-4-(7-fluoroimidazo[1,2-a]pyridin-3-yl)-1-oxoisoindoline-2-carboxylate (34.1)

tert-butyl 7-((6-cyano-5-(1-methoxycyclopropyl)pyridin-2-yl)amino)-4-(7-fluoroimidazo[1,2-a]pyridin-3-yl)-1-oxoisoindoline-2-carboxylate 34.1 was prepared from tert-butyl 7-amino-4-(7-fluoroimidazo[1,2-a]pyridin-3-yl)-1-oxoisoindoline-2-carboxylate (29.3) and 6-chloro-5-(1-methoxycyclopropyl)picolinonitrile (Intermediate AA203) in a similar fashion to that described in step-1 tert-butyl 7-((5-(6-(benzyloxy)-1,4-oxazepan-4-yl)-6-((dimethylamino)methyl)pyridin-2-yl)amino)-4-(7-fluoroimidazo[1,2-a]pyridin-3-yl)-1-oxoisoindoline-2-carboxylate (29.4) (800 mg, 50%). m/z 559.61 [M+H]+.

Step-2 Tert-Butyl 7-((6-(aminomethyl)-5-(1-methoxycyclopropyl)pyridin-2-yl)amino)-4-(7-fluoroimidazo[1,2-a]pyridin-3-yl)-1-oxoisoindoline-2-carboxylate (34.2)

To a suspension of Raney nickel (400 mg) in methanol was added 34.1 (800 mg, 1.4 mmol, 1 eq). After stirring at 60° C. and at 20 psi for 12 h in autoclave with hydrogen gas, the reaction mixture was filter through Celite and washed with methanol (200 mL). The filtrate concentrated under vacuum to afford 34.2 (100 mg, 24.82%). MS (ES): m/z 183.5 [M+1]+

Step-3 Tert-Butyl 7-((6-((dimethylamino)methyl)-5-(1-methoxycyclopropyl)pyridin-2-yl)amino)-4-(7-fluoroimidazo[1,2-a]pyridin-3-yl)-1-oxoisoindoline-2-carboxylate (34.3)

To a solution of Intermediate 34.2 (90 mg, 185.1 mmol) in methanol (1 mL) at 0° C. were added paraformaldehyde (450 mg, 2 eq) and acetic acid (cat). After stirring for 30 min. NaCN(BH)3 (35 mg, 555 mmol, 3 eq) was added. After stirring at RT for 4 h, the reaction was washed with aqueous sodium bicarbonate solution (20 mL) and extracted with DCM (2×20 mL). The residue was concentrated and purified by silica gel chromatography to afford 34.3. (78 mg, 82%) as orange solid. MS (ES): m/z 587.67 [M+1]+

Step-4 7-((6-(((dimethylamino)methyl)-5-(1-methoxycyclopropyl)pyridin-2-yl)amino)-4-(7-fluoroimidazo[1,2-a]pyridin-3-yl)isoindolin-1-one (I-823)

To a solution of 34.3 (78 mg, 190.08 mmol) in DCM (1 mL) was added TFA (0.3 mL). After stirring at RT for 2 h, the reaction mixture was evaporated in vacuum and pH adjusted to neutral using NaHCO3 solution. The aqueous layer extracted by 15% MeOH/DCM. Solvent was evaporated under reduced pressure and the residue purified by trituration with diethyl ether to afford I-823 (27 mg, 41.74%). MS (ES): m/z 487.55. [M+1]+. 1H NMR (400 MHz, DMSO): δ 8.88 (s, 1H), 8.86 (s, 1H), 8.47-8.43 (t, J=6 Hz, 1H), 8.19 (s, 1H), 7.84 (s, 1H), 7.75-7.72 (d, J=8.4 Hz, 1H), 7.65-7.63 (d, J=8.4 Hz, 1H), 7.53 (bs, 1H), 7.00-6.98 (t, J=5.2 Hz, 1H), 6.89 (s, 1H), 4.41 (s, 2H), 3.81 (s, 2H), 3.02 (s, 3H), 1.24 (s, 2H), 1.07 (s, 6H), 0.95-0.92 (m, 2H).

Example 35. Method AIp

Synthesis of 7-((5-(4-hydroxypiperidin-1-yl)pyridin-2-yl)amino)-4-(imidazo[1,2-b]pyridazin-8-yl)-2,3-dihydro-1H-pyrrolo[3,4-c]pyridin-1-one (I-565)

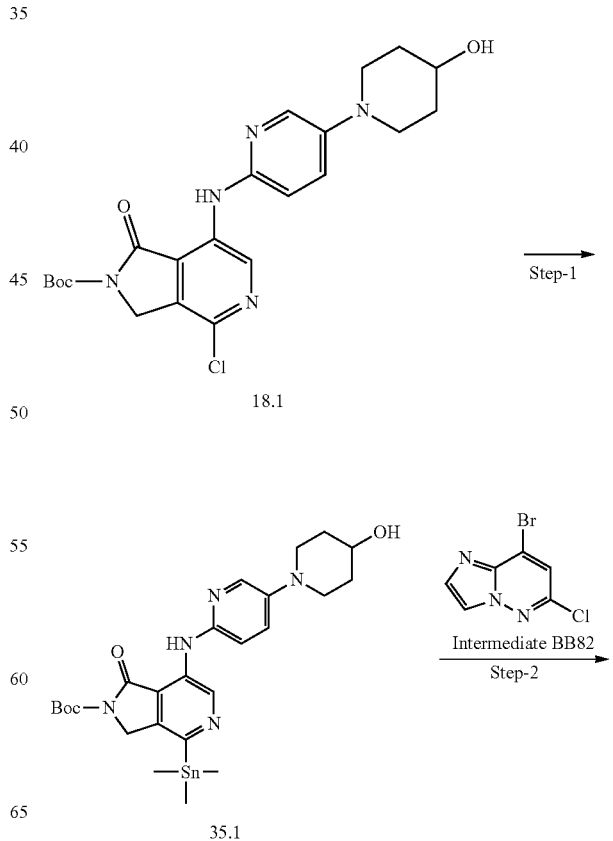

-continued

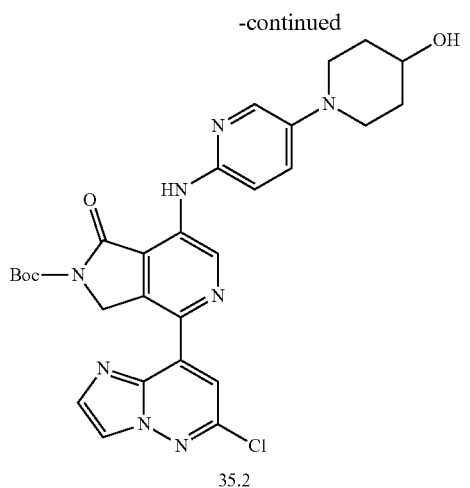

35.2

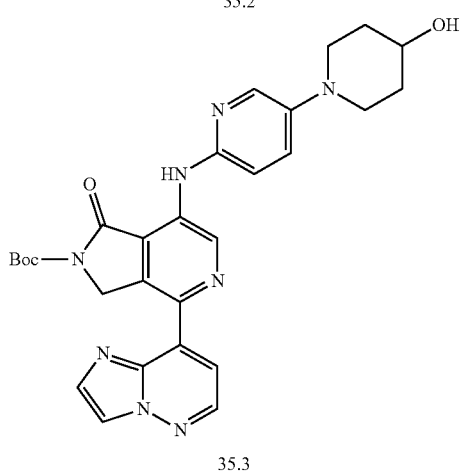

35.3

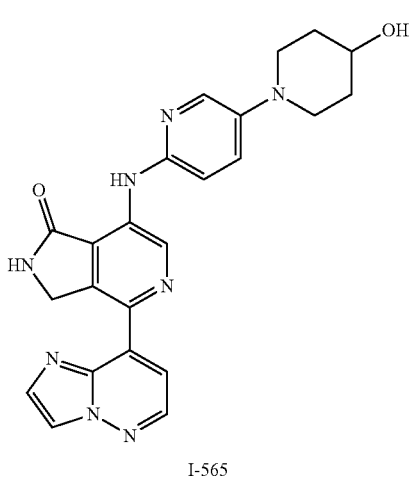 [SMILES: O=C1NCc2c(-c3ccnn4ccnc34)ncc(Nc3ccc(N4CCC(O)CC4)cn3)c21]

I-565

Step-1 Synthesis of Tert-Butyl 7-((5-(4-hydroxypiperidin-1-yl)pyridin-2-yl)amino)-1-oxo-4-(trimethylstannyl)-1,3-dihydro-2H-pyrrolo[3,4-c]pyridine-2-carboxylate (35.1)

To a solution of 18.1 (0.500 g, 1.08 mmol, 1.0 eq.) in toluene (8 mL) was added hexamethylditin (0.534 g, 1.6 mmol, 1.5 eq.) at RT. After degassing with Argon for 20 min, bis(triphenylphosphine)palladium(II) dichloride (0.076 g, 0.1 mmol, 0.1 eq.) was added. After stirring at 110° C. for 8 h, the reaction mixture was poured into water (50 mL) and extracted using ethyl acetate (50 mL×3). The combined organic layer was washed with brine (50 mL) and concentrated under reduced pressure. The residue was purified by column chromatography using basic alumina oxide as a stationary phase eluting with 0.5% methanol in DCM to afford 35.1 (450 mg, LCMS: 85%, MS (ES): m/z 588.5 (M+H)+

Step-2 Synthesis of Tert-Butyl 4-(6-chloroimidazo[1,2-b]pyridazin-8-yl)-7-((5-(4-hydroxypiperidin-1-yl)pyridin-2-yl)amino)-1-oxo-1,3-dihydro-2H-pyrrolo[3,4-c]pyridine-2-carboxylate (35.2)

To a solution of 35.1 (0.450 g, 0.76 mmol) in DMF (8 mL) were added Intermediate BB82 (0.212 g, 0.91 mmol, 1.2 eq.), tri-o-tolyl phosphine (0.046 g, 0.15 mmol, 0.2 eq.) and trimethylamine (0.32 mLg, 2.2 mmol, 3 eq) at RT. After degassing with argon for 20 min, $Pd_2(dba)_3$ (0.070 g, 0.076 mmol, 0.1 eq.) was added. After stirring at 110° C. for 3 h, the reaction mixture was poured into water and extracted using ethyl acetate. The organic layer was washed with brine (50 mL×3) solution, dried over sodium sulfate and concentrated under reduced pressure. The residue was purified by silica gel chromatography eluting 2.5% MeOH in DCM to afford 35.2 (0.140 g, 27.81%). MS (ES): m/z 578.6 (M+H)+.

Step-3 Synthesis of Tert-Butyl 7-((5-(4-hydroxypiperidin-1-yl)pyridin-2-yl)amino)-4-(imidazo[1,2-b]pyridazin-8-yl)-1-oxo-1,3-dihydro-2H-pyrrolo[3,4-c]pyridine-2-carboxylate (35.3)

To a solution of 35.2 (0.140 g, 0.243 mmol) in methanol was added 10% Pd/C in autoclave. After heating at 60° C. with 20 psi Hydrogen pressure for 16 h, the reaction mixture was filter through celite and the celite bed washed with MeOH. The filtrate was concentrated under reduced pressure. The residue was purified by column chromatography eluting with 3% methanol in DCM to afford 35.3 (0.070 g). MS (ES): m/z 543.5 (M+H)+.

Step-4 Synthesis of 7-((5-(4-hydroxypiperidin-1-yl)pyridin-2-yl)amino)-4-(imidazo[1,2-b]pyridazin-8-yl)-2,3-dihydro-1H-pyrrolo[3,4-c]pyridin-1-one (I-565)

To a solution of 35.3 (0.07 g, 0.129 mmol) in DCM (3 mL) was added 4 M HCl in dioxane (1 mL). After stirring at RT for 2 h, the reaction mixture was neutralized using saturated sodium bicarbonate solution whereby a solid precipitated from solution. The solid was collected by filtration and dried under high vacuum to afford I-565 (0.030 g, 46.08%) as a white solid. MS (ES): m/z 443.18 [M+H] +1H NMR (400 MHz, DMSO-d6) δ 9.90 (s, 1H), 9.57 (s, 1H), 9.09 (s, 1H), 8.66-8.65 (d, J=4.8 Hz, 1H), 8.43 (s, 1H), 8.07 (d, J=3.1 Hz, 1H), 7.88 (s, 1H), 7.55-7.53 (d, J=4.8 Hz, 1H), 7.48-7.47 (dd, J=9.1, 3.0 Hz, 1H), 7.08-7.07 (d, J=8.9 Hz, 1H), 4.82 (s, 2H), 4.72-4.71 (d, J=4.2 Hz, 1H), 3.65-3.64 (dq, J=9.1, 4.6 Hz, 1H), 3.55-3.47 (m, 3H), 2.88-2.83 (t, J=12.6 Hz, 2H), 1.86 (dd, J=12.8, 4.6 Hz, 2H), 1.25 (s, 1H).

Example 36. Method AJp

Synthesis of 7-((5-(4-hydroxypiperidin-1-yl)pyridin-2-yl)amino)-4-(pyrrolo[1,2-b]pyridazin-4-yl)-2,3-dihydro-1H-pyrrolo[3,4-c]pyridin-1-one (I-588)

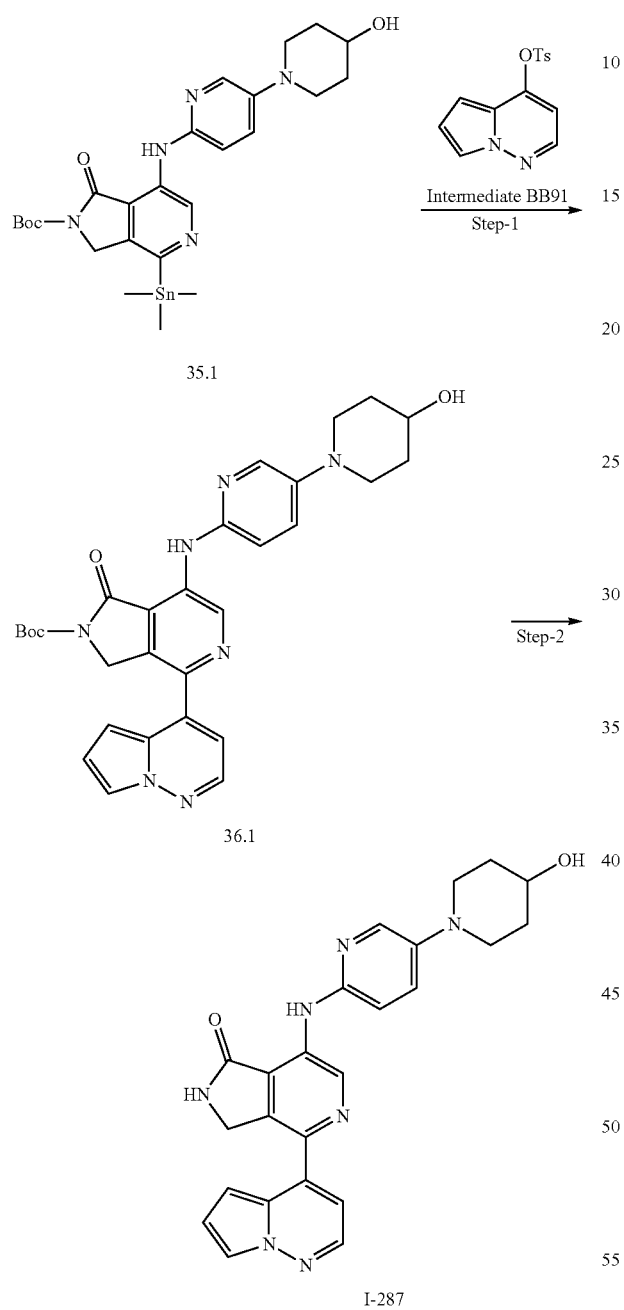

Step-1 Synthesis of Tert-Butyl 7-((5-(4-hydroxypiperidin-1-yl)pyridin-2-yl)amino)-1-oxo-4-(pyrrolo[1,2-b]pyridazin-4-yl)-1,3-dihydro-2H-pyrrolo[3,4-c]pyridine-2-carboxylate (36.1)

To a stirred solution of 35.1 (0.4 g, 01.38 mmol, 1.0 eq.) and Intermediate BB91 (0.98 g, 1.66 mmol, 1.2 eq.) in t-butanol (5 mL) was added cesium fluoride (0.464 g, 3.05 mmol, 2.2 eq.) at RT. After degassing with argon for 20 min, Pd(OAc)$_2$ (0.062 g, 0.27 mmol, 0.2 eq.) and 2-Dicyclohexylphosphino-2',4',6'-triisopropylbiphenyl (Xphose) (0.284 g, 0.55 mmole, 0.4 eq) was added. After stirring at 110° C. for 16 h, the reaction mixture was poured into water (80 mL) and extracted using ethyl acetate (100 mL×3). The combined organic layer was washed with brine (50 mL), dried over sodium sulfate, and concentrated under reduced pressure. The residue was purified by combi flash chromatography eluting 1.5% MeOH in DCM to afford 36.1 (0.220 g, 59.6%). MS (ES): m/z 562.7 (M+H)$^+$.

Step-2 7-((5-(4-hydroxypiperidin-1-yl)pyridin-2-yl)amino)-4-(pyrrolo[1,2-b]pyridazin-4-yl)-2,3-dihydro-1H-pyrrolo[3,4-c]pyridin-1-one (I-588)

I-588 was prepared from 36.1 in a similar fashion to that synthesis described in step-4 of Example 35 (0.025 g, 21%) as a white solid. MS (ES): m/z 442.2 [M+H] +1H NMR (400 MHz, DMSO-d6) δ 9.92 (s, 1H), 9.56 (s, 1H), 9.19 (s, 1H), 8.26-8.25 (d, J=4.7 Hz, 1H), 8.08-8.07 (d, J=3.0 Hz, 1H), 7.92 (t, J=2.1 Hz, 1H), 7.49-7.46 (dd, J=9.0, 3.1 Hz, 1H), 7.12-7.00 (m, 2H), 7.00-6.93 (m, 2H), 4.78-4.64 (m, 3H), 3.65 (dt, J=8.9, 4.4 Hz, 1H), 3.50 (d, J=11.9 Hz, 2H), 2.92-2.79 (m, 2H), 1.86 (d, J=10.5 Hz, 2H), 1.54 (s, 2H).

Example 37. Method Hc

Synthesis of (R)-4-(7-fluoroimidazo[1,2-a]pyridin-3-yl)-7-((5-(3-(2-hydroxypropan-2-yl)piperidin-1-yl)pyridin-2-yl)amino)-2,3-dihydro-1H-pyrrolo[3,4-c]pyridin-1-one (I-226)

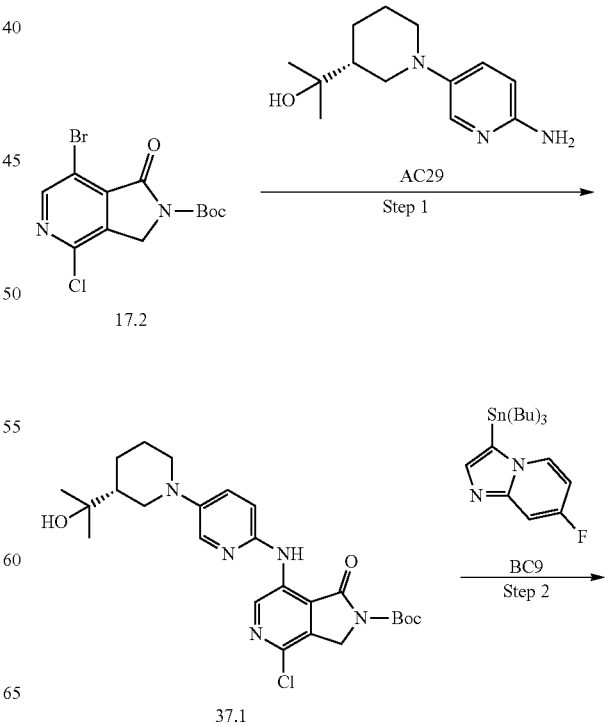

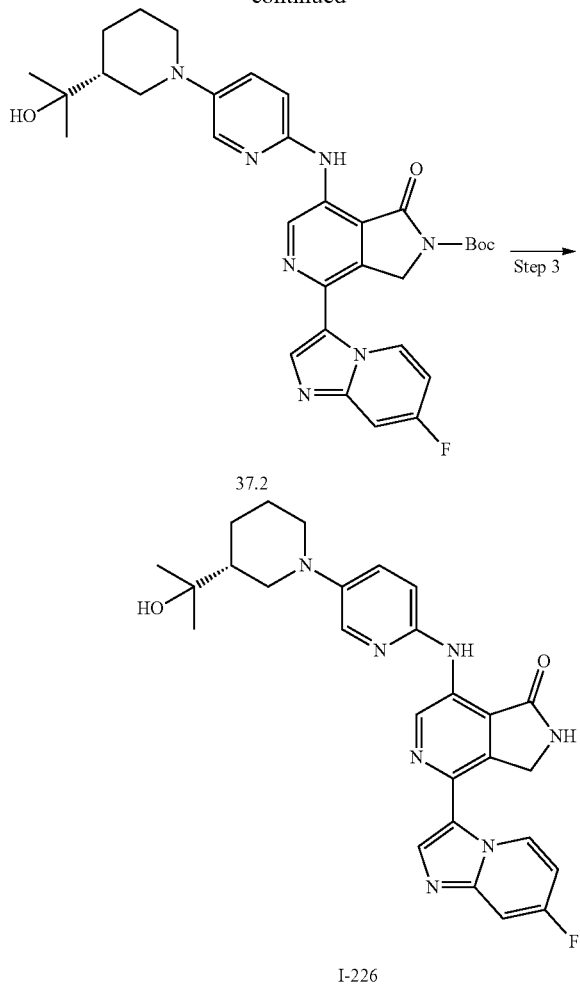

Step-1 Synthesis of Tert-Butyl (R)-4-chloro-7-((5-(3-(2-hydroxypropan-2-yl)piperidin-1-yl)pyridin-2-yl)amino)-1-oxo-1,3-dihydro-2H-pyrrolo[3,4-c]pyridine-2-carboxylate (37.1)

A mixture of tert-butyl 7-bromo-4-chloro-1-oxo-1,3-dihydro-2H-pyrrolo[3,4-c]pyridine-2-carboxylate (17.2) (430 mg, 1.23 mmol, 1 eq), (R)-2-(1-(6-aminopyridin-3-yl)piperidin-3-yl)propan-2-ol (AC29) (320 mg, 1.36 mmol, 1.1 eq), Cs$_2$CO$_3$ (805 mg, 12.47 mmol, 2 eq) and 4,5-Bis(diphenylphosphino)-9,9-dimethylxanthene (Xantphos) (71 mg, 0.12 mmol, 0.1 eq) was stirred in dry 1,4-dioxane (10 mL) and degassed under N$_2$ stream. After 15 mins Tris(dibenzylideneacetone)dipalladium(O)—Pd$_2$(dba)$_3$ (113 mg, 0.12 mmol, 0.1 eq) was added and the reaction was heated at 110° C. and stirred for 1.5 h. The reaction mixture was cooled to RT and then diluted with ethyl acetate (50 mL) and water (100 mL). The organic layer was collected and the aqueous phase was extracted with ethyl acetate (2×50 mL), and the combined organic extracts were washed with brine (50 mL), then dried over Na$_2$SO$_4$, filtered, and concentrated under reduced pressure. The crude residue was purified by column chromatography (0-4% gradient elution MeOH in DCM). The residue obtained was then triturated with diethyl ether and the resulting solid was collected by filtration to afford the title compound 37.1 (150 mg, 26%) as a beige solid. m/z=502.2 [M+H]$^+$ Step 2: Tert-Butyl (R)-4-(7-fluoroimidazo[1,2-a]pyridin-3-yl)-7-((5-(3-(2-hydroxypropan-2-yl)piperidin-1-yl)pyridin-2-yl)amino)-1-oxo-1,3-dihydro-2H-pyrrolo[3,4-c]pyridine-2-carboxylate (37.2)

A mixture of tert-butyl (R)-4-chloro-7-((5-(3-(2-hydroxypropan-2-yl)piperidin-1-yl)pyridin-2-yl)amino)-1-oxo-1,3-dihydro-2H-pyrrolo[3,4-c]pyridine-2-carboxylate (37.1) (200 mg, 0.398 mmol), 7-fluoro-3-(tributylstannyl)imidazo[1,2-a]pyridine (Intermediate BC9) (254 mg, 0.598 mmol) and Pd(PPh$_3$)$_4$ (46 mg, 0.04 mmol) in 1,4-dioxane (4 mL) was degassed, purged with nitrogen and heated at 150° C. for 20 minutes using microwave irradiation (Biotage Initiator®). The reaction mixture was filtered through Celite concentrated in vacuo and purified by silica gel chromatography (gradient: 0-20% methanol in DCM) to afford the title compound (37.2) (182 mg, 76%) as a pale red solid. This was taken directly into the next step.

Step 3: (R)-4-(7-fluoroimidazo[1,2-a]pyridin-3-yl)-7-((5-(3-(2-hydroxypropan-2-yl)piperidin-1-yl)pyridin-2-yl)amino)-2,3-dihydro-1H-pyrrolo[3,4-c]pyridin-1-one (I-226)

A solution of tert-butyl (R)-4-(7-fluoroimidazo[1,2-a]pyridin-3-yl)-7-((5-(3-(2-hydroxypropan-2-yl)piperidin-1-yl)pyridin-2-yl)amino)-1-oxo-1,3-dihydro-2H-pyrrolo[3,4-c]pyridine-2-carboxylate (37.2) (238 mg, 0.395 mmol) in methanol (6 mL) was treated with a hydrogen chloride solution (4N in 1,4-dioxane, 5.5 mL, 21.82) and stirred at ambient temperature for 1.5 hours. The mixture was concentrated in vacuo and dissolved in EtOAc (20 mL). The precipitate that formed was collected by filtration and purified by preparative HPLC to obtain the title compound (I-226) (18 mg, 9%) as a pale yellow solid. m/z=502 [M+H]$^+$, $^1$H NMR (400 MHz, DMSO): δ 9.94 (t, J=6.9 Hz, 1H), 9.89 (s, 1H), 9.38 (s, 1H), 9.27 (s, 1H), 8.05 (s, 1H), 8.02 (d, J=3.3 Hz, 1H), 7.59 (dd, J=2.7, 10.0 Hz, 1H), 7.43 (dd, J=3.2, 9.2 Hz, 1H), 7.14 (ddd, J=7.4, 7.4, 2.5 Hz, 1H), 7.01 (d, J=9.2 Hz, 1H), 4.74 (s, 2H), 4.29 (s, 1H), 3.76 (d, J=12.0 Hz, 1H), 3.65 (d, J=12.9 Hz, 1H), 2.57 (ddd, J=12.6, 12.6, 2.3 Hz, 1H), 2.45 (t, J=11.5 Hz, 1H), 1.86 (d, J=11.4 Hz, 1H), 1.77 (d, J=12.6 Hz, 1H), 1.62-1.54 (m, 2H), 1.21-1.16 (m, 1H), 1.14 (s, 3H), 1.12 (s, 3H).

Example 38. Additional Compounds of the Invention

The following compounds were made according to any of the Experimental methods A to U as described above in Examples 1-20.

TABLE 8

Characterization Data (LCMS and ¹H NMR).

| # | STRUCTURE | NAME | LCMS | ¹H NMR | Method Reagent AA BB |
|---|---|---|---|---|---|
| I-1 | 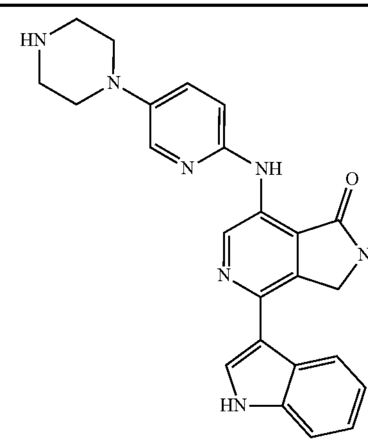 | 4-(1H-indol-3-yl)-7-[5-piperazin-1-yl-2-pyridyl]amino]-2,3-dihydropyrrolo[3,4-c]pyridin-1-one | Method 10 cm_Formic_AQ, m/z = 426 [M + H]+, Ret. time = 2.31 min. | ¹H NMR (400 MHz, DMSO): δ 11.97-11.95 (m, 1 H), 9.79 (s, 1 H), 9.67 (s, 1 H), 9.53-9.49 (m, 1 H), 9.15 (s, 2 H), 8.37-8.35 (m, 1 H), 8.03 (s, 1 H), 7.68-7.64 (m, 1 H), 7.57 (d, J = 8.3 Hz, 1 H), 7.30 (dd, J = 7.5, 7.5 Hz, 1 H), 7.26-7.19 (m, 2 H), 4.81 (s, 2 H), 3.45-3.39 (m, 4 H), 3.31 (d, J = 1.0 Hz, 4 H). | A AC8 BC10 |
| I-2 | 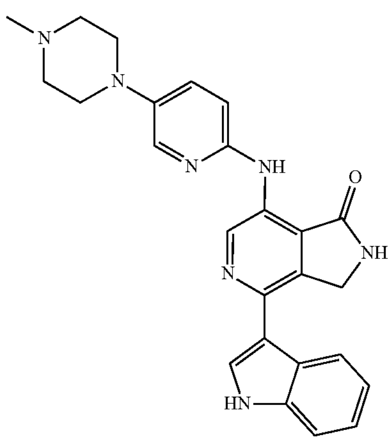 [SMILES: CN1CCN(c2ccc(Nc3cnc(-c4c[nH]c5ccccc45)c4c3C(=O)NC4)nc2)CC1] | 4-(1H-indol-3-yl)-7-[5-(4-methylpiperazin-1-yl)-2-pyridyl]amino]-2,3-dihydropyrrolo[3,4-c]pyridin-1-one | Method 10 cm_Formic_AQ, m/z = 440 [M + H]+, Ret. time = 2.3 min. | ¹H NMR (400 MHz, DMSO): δ 9.80 (s, 1 H), 9.22-9.22 (m, 1 H), 8.58 (d, J = 8.0 Hz, 1 H), 8.02 (d, J = 2.9 Hz, 1 H), 7.73 (s, 1 H), 7.48-7.43 (m, 2 H), 7.21-7.17 (m, 1 H), 7.12 (dd, J = 7.2, 7.2 Hz, 1 H), 6.99 (d, J = 9.0 Hz, 1 H), 4.68 (s, 2H), 3.55 (m, 6 H), 3.11 (dd, J = 4.7, 4.7 Hz, 4 H), 2.24 (s, 3 H). | A AC9 BC10 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-3 | 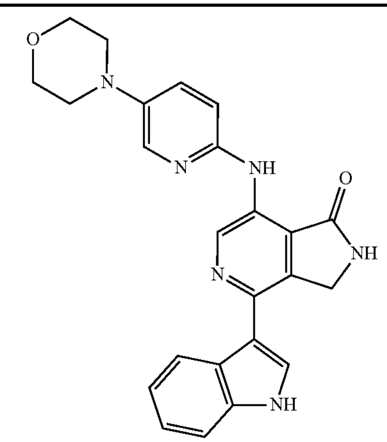 | 4-(1H-indol-3-yl)-7-[(5-morpholino-2-pyridyl)amino]-2,3-dihydropyrrolo[3,4-c]pyridin-1-one | Method AcHSS C18, m/z = 427 [M + H]+, Ret. time = 3.14 min. | ¹H NMR (400 MHz, DMSO): δ 11.51-11.49 (m, 1 H), 9.83 (s, 1 H), 9.29 (s, 1 H), 9.15 (s, 1 H), 8.61 (d, J = 7.9 Hz, 1 H), 8.04 (d, J = 2.9 Hz, 1 H), 7.76 (d, J = 2.6 Hz, 1 H), 7.46 (d, J = 6.5 Hz, 2 H), 7.21-7.16 (m, 1 H), 7.12 (dd, J = 7.1, 7.1 Hz, 1H), 7.02 (d, J = 8.9 Hz, 1 H), 4.70 (s, 2 H), 3.80-3.76 (m, 4H), 3.11 (dd, J = 4.8, 4.8 Hz, 4 H). | C AC10 BC10 |
| I-4 | 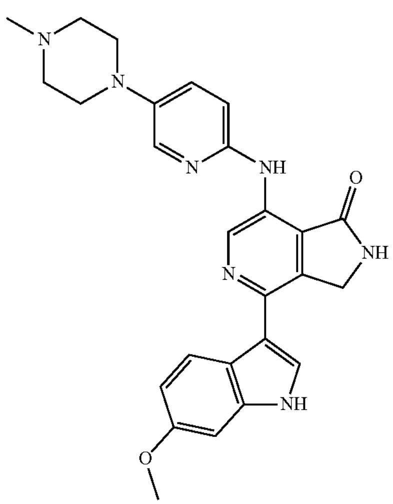 [SMILES: COc1ccc2c(-c3ncc(Nc4ccc(N5CCN(C)CC5)cn4)c4c3CNC4=O)c[nH]c2c1] | 4-(6-methoxy-1H-indol-3-yl)-7-[[5-(4-methylpiperazin-1-yl)-2-pyridyl]amino]-2,3-dihydropyrrolo[3,4-c]pyridin-1-one | Method AcHSS C18, m/z = 470 [M + H]+, Ret. time = 2.3 min. | ¹H NMR (400 MHz, DMSO): δ 11.29 (s, 1 H), 9.79 (s, 1 H), 9.26 (s, 1 H), 9.14 (s, 1 H), 8.48 (d, J = 8.8 Hz, 1 H), 8.03 (d, J = 2.9 Hz, 1 H), 7.60 (d, J = 2.4 Hz, 1 H), 7.44 (dd, J = 3.0, 9.0 Hz, 1 H), 6.99 (d, J = 8.9 Hz, 1 H), 6.94 (d, J = 2.3 Hz, 1 H), 6.78 (dd, J = 2.3, 8.8 Hz, 1 H), 4.67 (s, 2 H), 3.81 (s, 3 H), 3.12 (dd, J = 4.9, 4.9 Hz, 4 H), 2.48 (dd, J = 4.9, 4.9 Hz, 4 H), 2.25 (s, 3 H). | C AC9 BC11 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-5 | 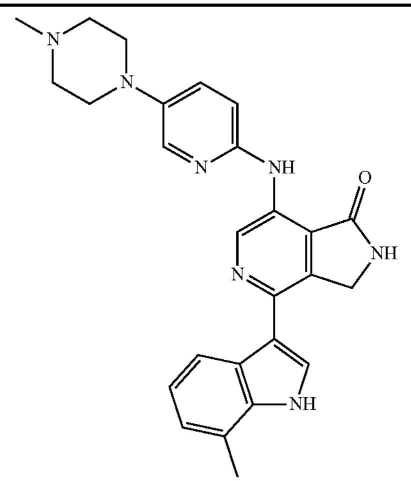 | 4-(7-methyl-1H-indol-3-yl)-7-[[5-(4-methylpiperazin-1-yl)-2-pyridyl]amino]-2,3-dihydropyrrolo[3,4-c]pyridin-1-one | Method AcHSS C18, m/z = 454 [M + H]+, Ret. time = 2.46 min. | ¹H NMR (400 MHz, DMSO): δ 11.44 (d, J = 1.9 Hz, 1 H), 9.81 (s, 1 H), 9.27 (s, 1 H), 9.14 (s, 1 H), 8.42 (d, J = 7.8 Hz, 1 H), 8.03 (d, J = 3.0 Hz, 1 H), 7.72 (d, J = 2.9 Hz, 1 H), 7.45 (dd, J = 3.0, 9.0 Hz, 1 H), 7.05-6.96 (m, 3 H), 4.72 (s, 2 H), 3.13 (dd, J = 4.9, 4.9 Hz, 4 H), 2.55-2.52 (m, 3 H), 2.50-2.46 (m, 4 H), 2.25 (s, 3 H). | C AC9 BC12 |
| I-6 | 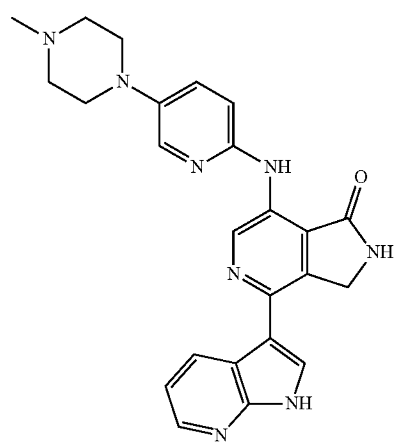 [SMILES: CN1CCN(c2ccc(Nc3cnc(-c4c[nH]c5ncccc45)c4c3C(=O)NC4)nc2)CC1] | 7-[[5-(4-methylpiperazin-1-yl)-2-pyridyl]amino]-4-(1H-pyrrolo[2,3-b]pyridin-3-yl)-2,3-dihydropyrrolo[3,4-c]pyridin-1-one | Method AcHSS C18, m/z = 441 [M + H]+, Ret. time = 2.06 min. | ¹H NMR (400 MHz, DMSO): δ 12.11-12.06 (m, 1 H), 9.87 (s, 1 H), 9.34 (s, 1 H), 9.21 (s, 1 H), 8.94 (d, J = 7.1 Hz, 1 H), 8.35 (d, J = 3.0 Hz, 1 H), 8.08 (d, J = 2.8 Hz, 1 H), 7.89 (d, J = 2.3 Hz, 1 H), 7.50 (dd, J = 2.8, 8.8 Hz, 1 H), 7.23 (dd, J = 4.5, 7.8 Hz, 1 H), 7.05 (d, J = 8.8 Hz, 1 H), 4.78 (s, 2 H), 3.21 (dd, J = 6.4, 6.4 Hz, 4 H), 2.70-2.63 (m, 4H), 2.38 (s, 3 H). | A AC9 BC13 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-7 | 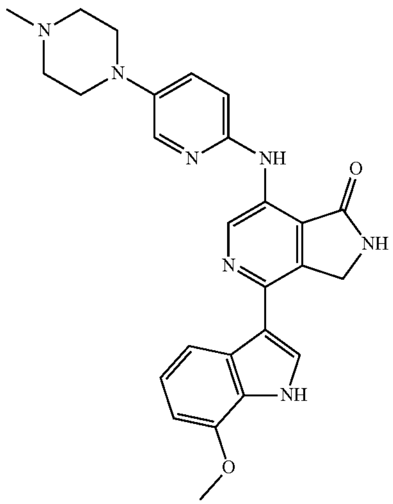 [SMILES: COc1cccc2c(-c3ncc(Nc4ccc(N5CCN(C)CC5)cn4)c4c3CNC4=O)c[nH]c12] | 4-(7-methoxy-1H-indol-3-yl)-7-[[5-(4-methylpiperazin-1-yl)-2-pyridyl]amino]-2,3-dihydropyrrolo[3,4-c]pyridin-1-one | Method AcHSS C18, m/z = 470 [M + H]+, Ret. time = 2.36 min. | ¹H NMR (400 MHz, DMSO): δ 11.62 (d, J = 1.8 Hz, 1 H), 9.80 (s, 1 H), 9.27 (s, 1 H), 9.12 (s, 1 H), 8.17 (d, J = 8.0 Hz, 1 H), 8.03 (d, J = 2.9 Hz, 1 H), 7.62 (d, J = 2.8 Hz, 1 H), 7.45 (dd, J = 3.1, 9.0 Hz, 1 H), 7.07-6.98 (m, 2 H), 6.76 (d, J = 7.4 Hz, 1 H), 4.70 (s, 2H), 3.96 (s, 3 H), 3.12 (dd, J = 4.8, 4.8 Hz, 4 H), 2.49 (dd, J = 4.8, 4.8 Hz, 4 H), 2.25 (s, 3 H). | C AC9 BC14 |
| I-8 | 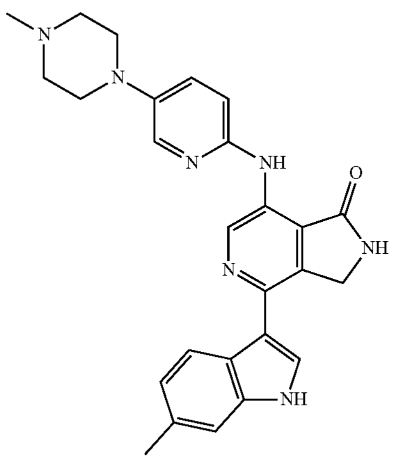 [SMILES: Cc1ccc2c(-c3ncc(Nc4ccc(N5CCN(C)CC5)cn4)c4c3CNC4=O)c[nH]c2c1] | 4-(6-methyl-1H-indol-3-yl)-7-[[5-(4-methylpiperazin-1-yl)-2-pyridyl]amino]-2,3-dihydropyrrolo[3,4-c]pyridin-1-one | Method AcHSS C18, m/z = 454 [M + H]+, Ret. time = 2.46 min. | ¹H NMR (400 MHz, DMSO): δ 11.38 (s, 1 H), 9.84 (s, 1 H), 9.30 (s, 1 H), 9.17 (s, 1 H), 8.52 (d, J = 8.1 Hz, 1 H), 8.07 (d, J = 2.8 Hz, 1 H), 7.69 (s, 1 H), 7.48 (dd, J = 2.9, 9.0 Hz, 1H), 7.28 (s, 1 H), 7.01 (dd, J = 8.6, 13.4 Hz, 2 H), 4.72 (s, 2 H), 3.16 (dd, J = 4.4, 4.4 Hz, 4 H), 2.54 (dd, J = 4.4, 4.4 Hz, 4 H), 2.49 (s, 3 H), 2.29 (s, 3 H). | C AC9 BC15 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-9 | 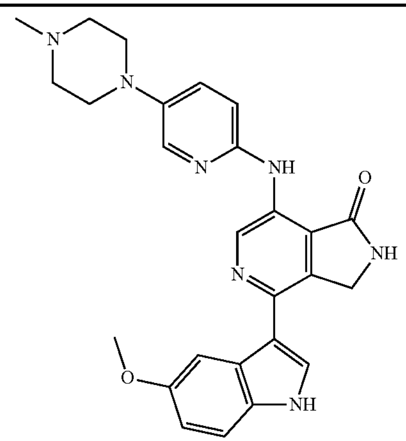 | 4-(5-methoxy-1H-indol-3-yl)-7-[[5-(4-methylpiperazin-1-yl)-2-pyridyl]amino]-2,3-dihydropyrrolo[3,4-c]pyridin-1-one | Method AcHSS C18, m/z = 470 [M + H]+, Ret. time = 2.27 min. | ¹H NMR (400 MHz, DMSO): δ 11.38 (d, J = 2.3 Hz, 1 H), 9.82 (s, 1 H), 9.28 (s, 1 H), 9.15 (s, 1H), 8.16 (d, J = 2.5 Hz, 1 H), 8.04 (d, J = 3.0 Hz, 1 H), 7.71 (d, J = 2.8 Hz, 1 H), 7.45 (dd, J = 3.0, 9.0 Hz, 1 H), 7.35 (d, J = 8.8 Hz, 1 H), 6.99 (d, J = 8.9 Hz, 1 H), 6.84 (dd, J = 2.6, 8.8 Hz, 1 H), 4.69 (s, 2 H), 3.83 (s, 3 H), 3.12 (dd, J = 4.9, 4.9 Hz, 4 H), 2.49 (dd, J = 4.9, 4.9 Hz, 4 H), 2.25 (s, 3 H). | C AC9 BC16 |
| I-10 | 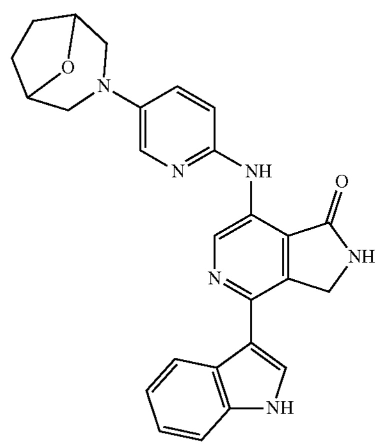 [SMILES: O=C1NCc2c(-c3c[nH]c4ccccc34)ncc(Nc3ccc(N4CC5CCC(C4)O5)cn3)c21] | 4-(1H-indol-3-yl)-7-[[5-(8-oxa-3-azabicyclo[3.2.1]octan-3-yl)-2-pyridyl]amino]-2,3-dihydropyrrolo[3,4-c]pyridin-1-one | Method AcHSS C18, m/z = 453 [M + H]+, Ret. time = 3.45 min. | ¹H NMR (400 MHz, DMSO): δ 11.41 (d, J = 1.6 Hz, 1 H), 9.71 (s, 1 H), 9.15 (s, 1 H), 9.06 (s, 1 H), 8.52 (d, J = 7.9 Hz, 1 H), 7.86 (d, J = 3.0 Hz, 1 H), 7.67 (d, J = 2.8 Hz, 1 H), 7.37 (d, J = 8.0 Hz, 1 H), 7.29 (dd, J = 3.1, 9.0 Hz, 1 H), 7.12-7.08 (m, 1 H), 7.04 (dd, J = 7.2, 7.2 Hz, 1 H), 6.92 (d, J = 8.9 Hz, 1 H), 4.61 (s, 2 H), 4.37 (s, 2 H), 3.30 (d, J = 10.4 Hz, 3 H), 3.10 (s, 2 H), 2.75 (dd, J = 2.2, 11.2 Hz, 2 H), 1.83-1.79 (m, 1 H). | C AC11 BC10 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-11 | 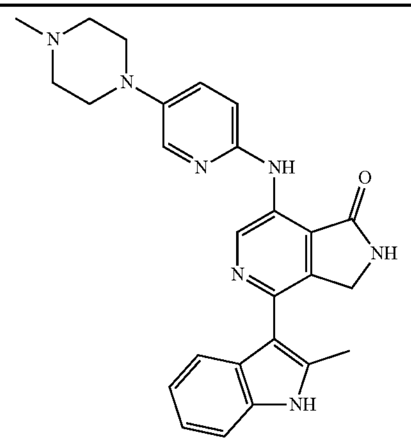 | 4-(2-methyl-1H-indol-3-yl)-7-[[5-(4-methylpiperazin-1-yl)-2-pyridyl]amino]-2,3-dihydropyrrolo[3,4-c]pyridin-1-one | Method BicarbB EHC18, m/z = 454 [M + H]+, Ret. time = 3.51 min. | ¹H NMR (400 MHz, DMSO): δ 11.27 (s, 1 H), 9.80 (s, 1 H), 9.26 (s, 1 H), 8.95 (s, 1 H), 8.03 (d, J = 3.0 Hz, 1 H), 7.46 (dd, J = 3.0, 9.0 Hz, 1 H), 7.36 (dd, J = 3.3, 8.0 Hz, 2 H), 7.09-6.96 (m, 3 H), 4.26 (s, 2 H), 3.13 (dd, J = 4.9, 4.9 Hz, 4 H), 2.49 (dd, J = 4.9, 4.9 Hz, 4 H), 2.40 (s, 3 H), 2.25 (s, 3 H). | A AC9 BC17 |
| I-12 | 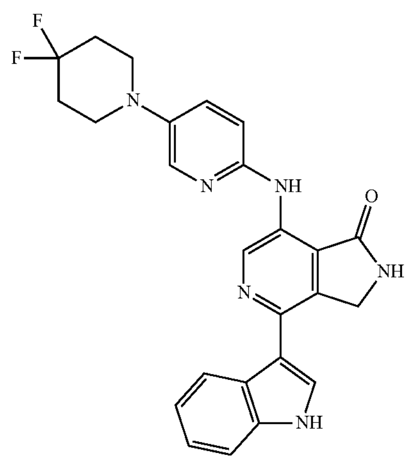 [SMILES: O=C1NCc2c(-c3c[nH]c4ccccc34)ncc(Nc3ccc(N4CCC(F)(F)CC4)cn3)c21] | 7-[[5-(4,4-difluoro-1-piperidyl)-2-pyridyl]amino]-4-(1H-indol-3-yl)-2,3-dihydropyrrolo[3,4-c]pyridin-1-one | Method AcHSS C18, m/z = 461 [M + H]+, Ret. time = 3.95 min. | ¹H NMR (400 MHz, DMSO): δ 11.54 (s, 1 H), 9.87 (s, 1 H), 9.35 (s, 1 H), 9.19 (s, 1 H), 8.65 (d, J = 7.8 Hz, 1 H), 8.14 (d, J = 2.5 Hz, 1 H), 7.80 (d, J = 2.3 Hz, 1 H), 7.56 (dd, J = 2.9, 9.0 Hz, 1 H), 7.50 (d, J = 8.1 Hz, 1 H), 7.23 (dd, J = 7.1, 7.1 Hz, 1 H), 7.16 (dd, J = 7.3, 7.3 Hz, 1 H), 7.06 (d, J = 9.1 Hz, 1 H), 4.74 (s, 2 H), 3.33 (dd, J = 5.4, 5.4 Hz, 4 H), 2.21-2.11 (m, 4H). | C AC5 BC10 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-13 | 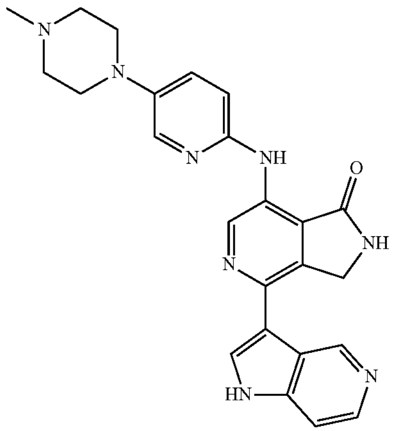 [SMILES: CN1CCN(c2ccc(Nc3cnc(-c4c[nH]c5ccncc45)c4c3C(=O)NC4)nc2)CC1] | 7-[[5-(4-methylpiperazin-1-yl)-2-pyridyl]amino]-4-(1H-pyrrolo[3,2-c]pyridin-3-yl)-2,3-dihydropyrrolo[3,4-c]pyridin-1-one | Method AcHSS C18, m/z = 441 [M + H]+, Ret. time = 1.85 min. | 1H NMR (400 MHz, Methanol-d4) δ 10.06 (s, 1H), 9.96 (s, 1H), 8.46 (d, J = 6.6 Hz, 1H), 8.19 (s, 1H), 8.12 (d, J = 2.9 Hz, 1H), 8.05 (d, J = 6.7 Hz, 1H), 7.60 (dd, J = 9.1, 3.0 Hz, 1H), 7.07 (d, J = 9.0 Hz, 1H), 4.82 (s, 2H), 3.83 (d, J = 13.2 Hz, 2H), 3.67 (s, 2H), 3.13 (s, 2H), 3.03 (s, 3H). | A, AC9 BB9 |
| I-14 | 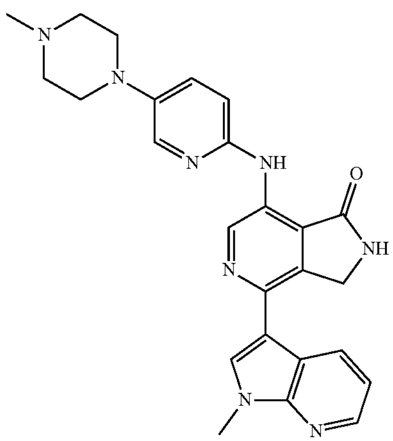 [SMILES: CN1CCN(c2ccc(Nc3cnc(-c4cn(C)c5ncccc45)c4c3C(=O)NC4)nc2)CC1] | 7-[[5-(4-methylpiperazin-1-yl)-2-pyridyl]amino]-4-(1-methylpyrrolo[2,3-b]pyridin-3-yl)-2,3-dihydropyrrolo[3,4-c]pyridin-1-one | Method AcHSS C18, m/z = 455 [M + H]+, Ret. time = 2.42 min. | 1H NMR (400 MHz, Methanol-d4) δ 9.93 (s, 1H), 8.66 (d, J = 8.1 Hz, 1H), 8.46 (d, J = 4.9 Hz, 1H), 8.10 (d, J = 3.0 Hz, 1H), 8.03 (s, 1H), 7.63 (dd, J = 9.1, 3.0 Hz, 1H), 7.37 (dd, J = 8.1, 4.7 Hz, 1H), 7.10 (d, J = 8.9 Hz, 1H), 4.78 (s, 2H), 4.03 (s, 3H), 3.82 (s, 2H), 3.67 (s, 2H), 3.14 (s, 3H), 3.03 (s, 3H). | A, AC9 BB10 |

| # | STRUCTURE | NAME | LCMS | ¹H NMR | Method Reagent AA BB |
|---|---|---|---|---|---|
| I-15 | 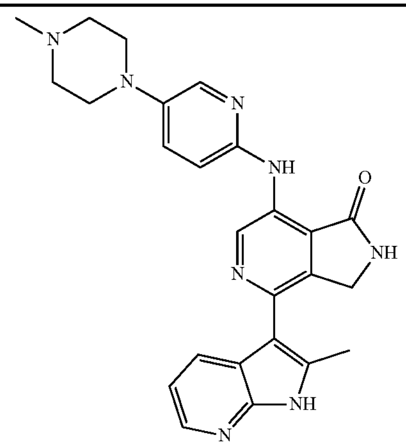 | 7-[[5-(4-methylpiperazin-1-yl)-2-pyridyl]amino]-4-(2-methyl-1H-pyrrolo[2,3-b]pyridin-3-yl)-2,3-dihydropyrrolo[3,4-c]pyridin-1-one | Method BicarbB EHC18, m/z = 455 [M + H]+, Ret. time = 2.99 min. | 1H NMR (400 MHz, DMSO-d6) δ 11.80 (s, 1H), 9.81 (s, 1H), 9.28 (s, 1H), 8.99 (s, 1H), 8.17 (dd, J = 4.7, 1.6 Hz, 1H), 8.02 (d, J = 3.0 Hz, 1H), 7.80 (dd, J = 7.8, 1.6 Hz, 1H), 7.45 (dd, J = 9.0, 3.0 Hz, 1H), 7.10-6.94 (m, 2H), 4.27 (s, 2H), 3.17 (s, 1H), 3.12 (t, J = 4.9 Hz, 4H), 2.42 (s, 3H), 2.24 (s, 3H). | A AC9 BB11 |
| I-16 | 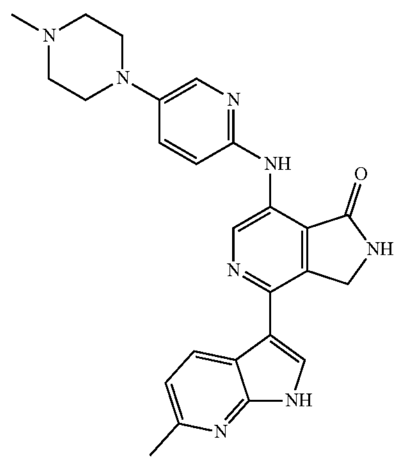 [SMILES: Cc1ccc2c(-c3ncc(Nc4ccc(N5CCN(C)CC5)cn4)c4c3CNC4=O)c[nH]c2n1] | 7-[[5-(4-methylpiperazin-1-yl)-2-pyridyl]amino]-4-(6-methyl-1H-pyrrolo[2,3-b]pyridin-3-yl)-2,3-dihydropyrrolo[3,4-c]pyridin-1-one | Method AcHSS C18, m/z = 455 [M + H]+, Ret. time = 2.11 min. | ¹H NMR (400 MHz, DMSO): δ 11.88 (s, 1 H), 9.85 (s, 1 H), 9.32 (s, 1H), 9.19 (s, 1 H), 8.82 (d, J = 8.1 Hz, 1 H), 8.07 (d, J = 2.5 Hz, 1 H), 7.77 (d, J = 2.8 Hz, 1 H), 7.49 (dd, J = 2.5, 8.8 Hz, 1H), 7.11 (d, J = 8.1 Hz, 1H), 7.04 (d, J = 8.8 Hz, 1H), 4.76 (s, 2H), 3.18-3.17 (m, 8 H), 2.61 (s, 3 H), 2.32 (s, 3 H). | A AC9 BB12 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-17 | 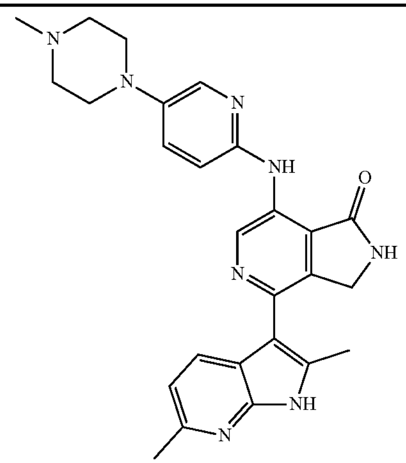 | 4-(2,6-dimethyl-1H-pyrrolo[2,3-b]pyridin-3-yl)-7-[[5-(4-methylpiperazin-1-yl)-2-pyridyl]amino]-2,3-dihydropyrrolo[3,4-c]pyridin-1-one | Method AcHSS C18, m/z = 469 [M + H]+, Ret. time = 1.88 min. | ¹H NMR (400 MHz, DMSO): δ 11.52 (s, 1 H), 9.73 (s, 1 H), 9.21 (s, 1 H), 8.91 (s, 1 H), 7.96 (d, J = 2.5 Hz, 1 H), 7.62 (d, J = 7.8 Hz, 1 H), 7.39 (dd, J = 2.9, 9.0 Hz, 1H), 6.96 (d, J = 8.8 Hz, 1H), 6.85 (d, J = 8.1 Hz, 1H), 4.21 (s, 2H), 3.05 (dd, J = 4.7, 4.7 Hz, 4 H), 2.47-2.38 (m, 4 H), 2.34 (m, 6H), 2.18 (s, 3 H). | A AC9 BB13 |
| I-18 | 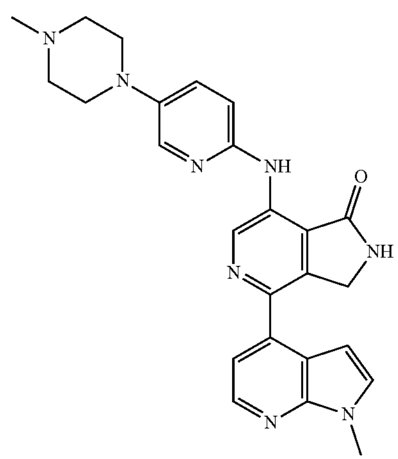 [SMILES: CN1CCN(c2ccc(Nc3cnc(-c4ccnc5c4ccn5C)c4c3C(=O)NC4)nc2)CC1] | 7-[[5-(4-methylpiperazin-1-yl)-2-pyridyl]amino]-4-(1-methylpyrrolo[2,3-b]pyridin-4-yl)-2,3-dihydropyrrolo[3,4-c]pyridin-1-one | Method AcHSS C18, m/z = 455 [M + H]+, Ret. time = 2.29 min. | 1H NMR (400 MHz, DMSO-d6) δ 9.93 (s, 1H), 9.52 (s, 1H), 9.18 (s, 1H), 8.36 (d, J = 5.0 Hz, 1H), 8.07 (d, J = 3.0 Hz, 1H), 7.58 (d, J = 3.4 Hz, 1H), 7.48 (dd, J = 9.5, 2.8 Hz, 1H), 7.39 (d, J = 5.1 Hz, 1H), 7.07 (d, J = 8.9 Hz, 1H), 6.92 (d, J = 3.4 Hz, 1H), 4.73 (s, 2H), 3.88 (s, 3H), 3.15 (t, J = 4.8 Hz, 4H), 2.26 (s, 3H). | A AC9 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-19 | 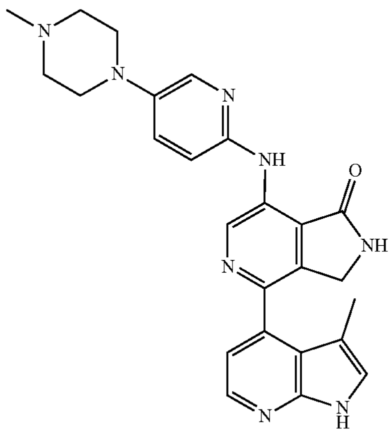 [SMILES: Cc1c[nH]c2nccc(-c3ncc(Nc4ccc(N5CCN(C)CC5)cn4)c4c3CNC4=O)c12] | 7-[[5-(4-methylpiperazin-1-yl)-2-pyridyl]amino]-4-(3-methyl-1H-pyrrolo[2,3-b]pyridin-4-yl)-2,3-dihydropyrrolo[3,4-c]pyridin-1-one | Method AcHSS C18, m/z = 455 [M + H]+, Ret. time = 1.98 min. | ¹H NMR (400 MHz, DMSO): δ 11.48 (s, 1 H), 9.89 (s, 1 H), 9.39 (s, 1 H), 9.08 (s, 1 H), 8.28 (d, J = 4.8 Hz, 1 H), 8.10 (d, J = 2.8 Hz, 1 H), 7.52 (dd, J = 2.8, 8.8 Hz, 1 H), 7.30 (s, 1 H), 7.22-7.18 (m, 1H), 7.09 (d, J = 8.8 Hz, 1 H), 4.45 (s, 2 H), 2.32 (s, 3 H), 2.09-2.02 (m, 4H), 1.88 (s, 3 H). | A AC9 BB15 |
| I-20 | 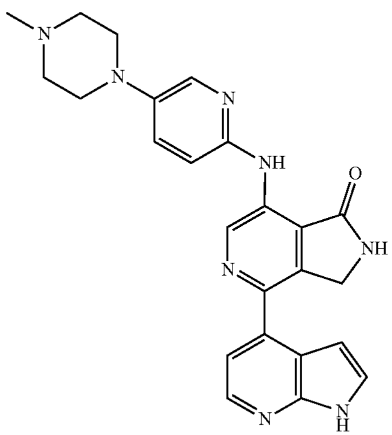 [SMILES: CN1CCN(c2ccc(Nc3cnc(-c4ccnc5[nH]ccc45)c4c3C(=O)NC4)nc2)CC1] | 7-[[5-(4-methylpiperazin-1-yl)-2-pyridyl]amino]-4-(1H-pyrrolo[2,3-b]pyridin-4-yl)-2,3-dihydropyrrolo[3,4-c]pyridin-1-one | Method AcHSS C18, m/z = 441 [M + H]+, Ret. time = 1.97 min. | 1H NMR (400 MHz, DMSO-d6) δ 11.74 (s, 1H), 9.94 (s, 1H), 9.52 (s, 1H), 9.18 (s, 1H), 8.31 (d, J = 5.2 Hz, 1H), 8.07 (s, 1H), 7.58-7.44 (m, 2H), 7.36 (d, J = 4.8 Hz, 1H), 7.07 (d, J = 9.1 Hz, 1H), 6.91 (s, 1H), 4.73 (s, 2H), 3.15 (s, 3H), 2.25 (s, 3H). | A AC9 BB16 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-21 | 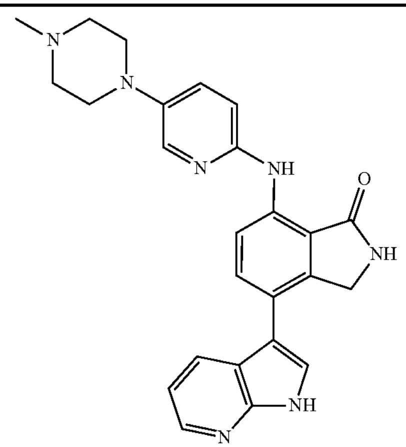 | 7-[[5-(4-methylpiperazin-1-yl)-2-pyridyl]amino]-4-(1H-pyrrolo[2,3-b]pyridin-3-yl)isoindolin-1-one | Method AcHSS C18, m/z = 440 [M + H]+, Ret. time = 2.17 min. | ¹H NMR (400 MHz, DMSO): δ 11.92-11.90 (m, 1 H), 9.79 (s, 1 H), 8.75 (s, 1 H), 8.50 (d, J = 8.5 Hz, 1H), 8.30 (dd, J = 1.5, 4.6 Hz, 1 H), 8.19-8.16 (m, 1H), 7.99 (d, J = 2.9 Hz, 1 H), 7.79-7.74 (m, 2H), 7.43 (dd, J = 3.0, 9.0 Hz, 1 H), 7.15 (dd, J = 4.6, 7.9 Hz, 1 H), 6.93 (d, J = 8.9 Hz, 1 H), 4.54 (s, 2 H), 3.11 (dd, J = 4.9, 4.9 Hz, 4 H), 2.49 (dd, J = 4.9, 4.9 Hz, 4 H), 2.24 (s, 3 H). | E AC9 BC13 |
| I-22 | 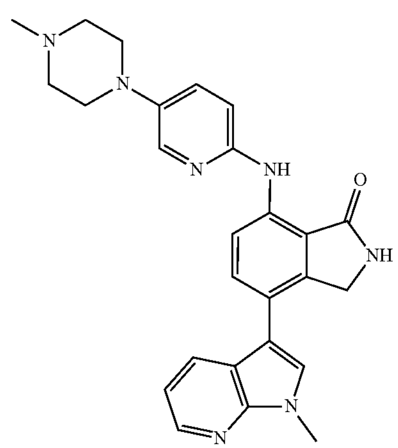 [SMILES: CN1CCN(c2ccc(Nc3ccc(-c4cn(C)c5ncccc45)c4c3C(=O)NC4)nc2)CC1] | 7-[[5-(4-methylpiperazin-1-yl)-2-pyridyl]amino]-4-(1-methylpyrrolo[2,3-b]pyridin-3-yl)isoindolin-1-one | Method AcHSS C18, m/z = 454 [M + H]+, Ret. time = 2.5 min. | ¹H NMR (400 MHz, DMSO): δ 9.83 (s, 1 H), 8.83 (s, 1 H), 8.54 (d, J = 8.6 Hz, 1 H), 8.39 (d, J = 3.5 Hz, 1 H), 8.25 (d, J = 7.8 Hz, 1 H), 8.03 (d, J = 2.5 Hz, 1 H), 7.90 (s, 1H), 7.81 (d, J = 8.6 Hz, 1 H), 7.47 (dd, J = 2.9, 9.0 Hz, 1 H), 7.23 (dd, J = 4.8, 7.8 Hz, 1 H), 6.97 (d, J = 8.8 Hz, 1 H), 4.57 (s, 2 H), 3.94 (s, 3 H), 3.15 (dd, J = 5.1, 5.1 Hz, 4 H), 2.52 (dd, J = 5.1, 5.1 Hz, 4 H), 2.28 (s, 3 H). | E AC9 BC18 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-23 | 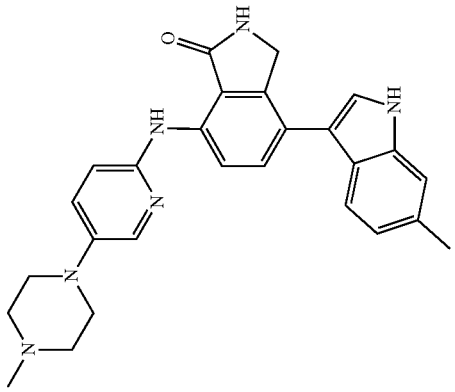 | 4-(6-methyl-1H-indol-3-yl)-7-[[5-(4-methylpiperazin-1-yl)-2-pyridyl]amino]isoindolin-1-one | Method AcHSS C18, m/z = 453 [M + H]+, Ret. time = 3.05 min. | ¹H NMR (400 MHz, DMSO) δ 11.21 (d, J = 2.1 Hz, 1 H), 9.76 (s, 1 H), 8.72-8.70 (m, 1 H), 8.49-8.45 (m, 1 H), 7.99 (d, J = 2.9 Hz, 1 H), 7.75-7.72 (m, 1 H), 7.64-7.55 (m, 2 H), 7.45-7.41 (m, 1 H), 7.24 (s, 1 H), 6.95-6.90 (m, 2 H), 4.49 (s, 2 H), 3.13-3.08 (m, 4 H), 2.53-2.50 (m, 4 H), 2.41 (s, 3 H), 2.25 (s, 3 H). | E AC9 BC15 |
| I-24 | 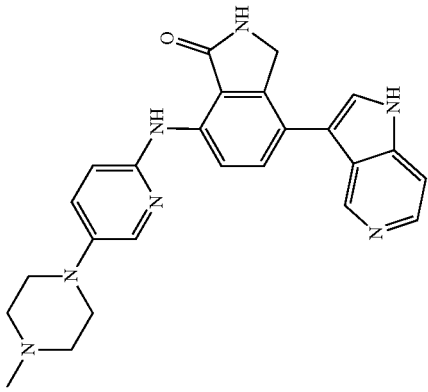 | 7-[[5-(4-methylpiperazin-1-yl)-2-pyridyl]amino]-4-(1H-pyrrolo[3,2-c]pyridin-3-yl)isoindolin-1-one | Method AcHSS C18, m/z = 440 [M + H]+, Ret. time = 1.74 min. | ¹H NMR (400 MHz, DMSO): δ 12.16-12.08 (m, 1 H), 9.86 (s, 1 H), 8.80 (s, 1 H), 8.57-8.54 (m, 1H), 8.31 (d, J = 6.0 Hz, 1 H), 8.15 (s, 1 H), 8.05 (d, J = 2.9 Hz, 1 H), 7.89-7.82 (m, 2H), 7.61 (d, J = 5.9 Hz, 1 H), 7.49 (dd, J = 3.0, 9.0 Hz, 1 H), 7.00-6.97 (m, 1 H), 4.56-4.54 (m, 2 H), 3.20-3.14 (m, 4 H), 2.71-2.68 (m, 4 H), 2.62 (s, 3 H). | E AC9 BC20 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-25 | 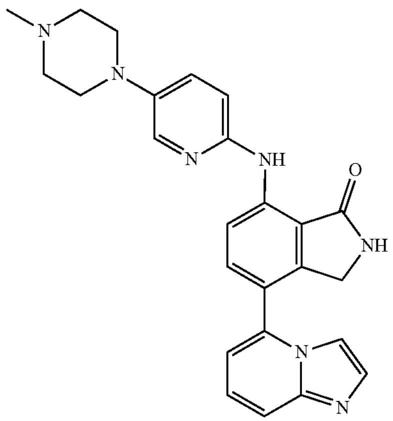 [SMILES: CN1CCN(c2ccc(Nc3ccc(-c4cccc5nccn45)c4c3C(=O)NC4)nc2)CC1] | 4-imidazo[1,2-a]pyridin-5-yl-7-[[5-(4-methyl)piperazin-1-yl)-2-pyridyl]amino]isoindolin-1-one | Method BicarbB EHC18, m/z = 440 [M + H]+, Ret. time = 3.33 min. | ¹H NMR (400 MHz, DMSO): δ 9.94-9.92 (m, 1 H), 8.75 (s, 1 H), 8.58-8.55 (m, 1 H), 8.02 (d, J = 3.0 Hz, 1 H), 7.76-7.73 (m, 1 H), 7.67-7.59 (m, 3 H), 7.46 (dd, J = 3.1, 9.0 Hz, 1 H), 7.34 (dd, J = 7.0, 9.1 Hz, 1 H), 7.04-6.98 (m, 2 H), 4.63 (s, 2H), 3.20-3.14 (m, 4 H), 2.71-2.68 (m, 4 H), 2.24 (s, 3 H). | E AC9 BC21 |
| I-26 | 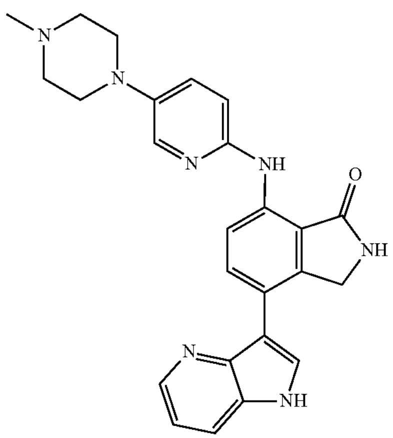 [SMILES: CN1CCN(c2ccc(Nc3ccc(-c4c[nH]c5cccnc45)c4c3C(=O)NC4)nc2)CC1] | 7-[[5-(4-methylpiperazin-1-yl)-2-pyridyl]amino]-4-(1H-pyrrolo[3,2-b]pyridin-3-yl)isoindolin-1-one | Method AcHSS C18, m/z = 440 [M + H]+, Ret. time = 1.76 min. | ¹H NMR (400 MHz, DMSO): δ 11.60 (d, J = 2.5 Hz, 1 H), 9.81 (s, 1 H), 8.75 (s, 1 H), 8.49-8.41 (m, 3 H), 8.01 (d, J = 2.9 Hz, 1 H), 7.91-7.84 (m, 2 H), 7.45 (dd, J = 3.0, 8.9 Hz, 1 H), 7.20 (dd, J = 4.5, 8.2 Hz, 1 H), 6.98-6.94 (m, 1 H), 4.63 (s, 2 H), 3.20-3.14 (m, 4 H), 2.71-2.68 (m, 4 H), 2.40 (s, 3 H). | D AC9 BC2 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-27 | 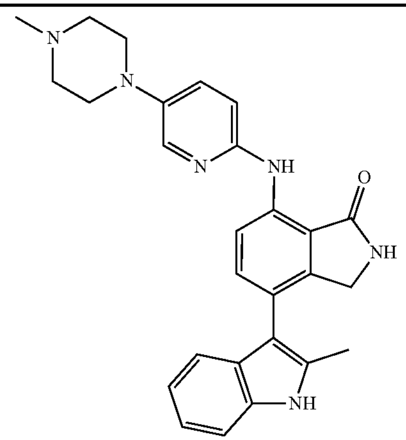 | 7-[[5-(4-methylpiperazin-1-yl)-2-pyridyl]amino]-4-(2-methyl-1H-pyrrolo[2,3-b]pyridin-3-yl)isoindolin-1-one | Method BicarbB EHC18, m/z = 454 [M + H]+, Ret. time = 3.54 min. | ¹H NMR (400 MHz, DMSO): δ 11.70 (s, 1 H), 9.76 (s, 1 H), 8.62 (s, 1 H), 8.46 (d, J = 8.5 Hz, 1 H), 8.16 (dd, J = 1.5, 4.6 Hz, 1 H), 7.99 (d, J = 3.0 Hz, 1 H), 7.64 (d, J = 6.7 Hz, 1 H), 7.46-7.41 (m, 2 H), 7.02 (dd, J = 4.7, 7.8 Hz, 1 H), 6.95 (d, J = 8.9 Hz, 1 H), 4.13 (s, 2 H), 3.11 (dd, J = 4.9, 4.9 Hz, 4 H), 2.48 (dd, J = 4.9, 4.9 Hz, 4 H), 2.35 (s, 3 H), 2.24 (s, 3 H). | D AC9 BC22 |
| I-28 | 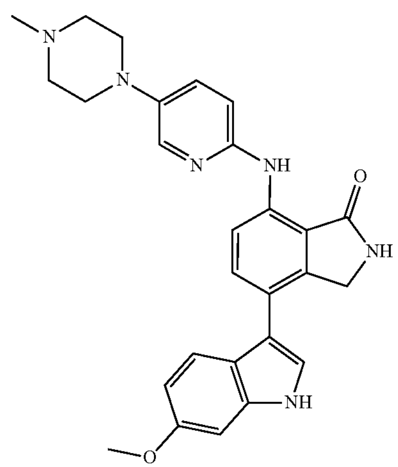 [SMILES: COc1ccc2c(-c3ccc(Nc4ccc(N5CCN(C)CC5)cn4)c4c3CNC4=O)c[nH]c2c1] | 4-(6-methoxy-1H-indol-3-yl)-7-[[5-(4-methylpiperazin-1-yl)-2-pyridyl]amino]isoindolin-1-one | Method AcHSS C18, m/z = 469 [M + H]+, Ret. time = 2.79 min. | ¹H NMR (400 MHz, DMSO): δ 11.15 (d, J = 1.6 Hz, 1 H), 9.76 (s, 1 H), 8.71 (s, 1 H), 8.47 (d, J = 8.5 Hz, 1 H), 7.99 (d, J = 3.0 Hz, 1 H), 7.73 (d, J = 8.5 Hz, 1 H), 7.61 (d, J = 8.8 Hz, 1 H), 7.50 (d, J = 2.5 Hz, 1 H), 7.43 (dd, J = 3.1, 9.0 Hz, 1 H), 6.96-6.91 (m, 2 H), 6.74 (dd, J = 2.3, 8.7 Hz, 1 H), 4.49 (s, 2 H), 3.81 (s, 3 H), 3.11 (dd, J = 4.9, 4.9 Hz, 4 H), 2.49 (dd, J = 4.9, 4.9 Hz, 4 H), 2.24 (s, 3 H). | E AC9 BC11 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-29 | 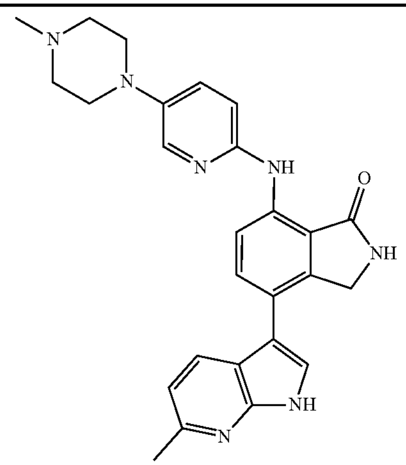 | 7-[[5-(4-methyl-piperazin-1-yl)-2-pyridyl]amino]-4-(6-methyl-1H-pyrrolo[2,3-b]pyridin-3-yl)isoindolin-1-one | Method AcHSS C18, m/z = 454 [M + H]+, Ret. time = 2.15 min. | ¹H NMR (400 MHz, DMSO): δ 11.71 (d, J = 1.6 Hz, 1 H), 9.78 (s, 1 H), 8.75 (s, 1 H), 8.49 (d, J = 8.7 Hz, 1 H), 8.06 (d, J = 8.2 Hz, 1 H), 7.99 (d, J = 2.9 Hz, 1 H), 7.74 (d, J = 8.5 Hz, 1 H), 7.66 (d, J = 2.5 Hz, 1 H), 7.43 (dd, J = 3.1, 9.0 Hz, 1 H), 7.03 (d, J = 8.2 Hz, 1H), 6.93 (d, J = 9.0 Hz, 1H), 4.53 (s, 2 H), 3.11 (dd, J = 4.9, 4.9 Hz, 4 H), 2.56 (s, 3 H), 2.48 (dd, J = 4.9, 4.9 Hz, 4 H), 2.25 (s, 3 H). | D AC9 BC19 |
| I-30 | 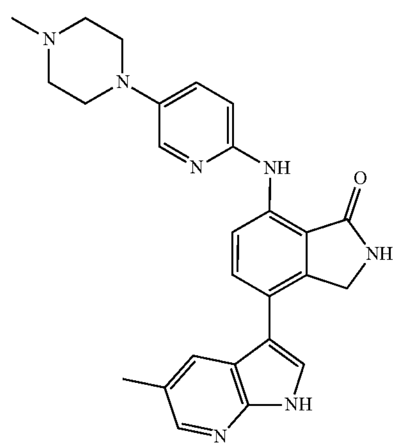 [SMILES: Cc1cnc2[nH]cc(-c3ccc(Nc4ccc(N5CCN(C)CC5)cn4)c4c3CNC4=O)c2c1] | 7-[[5-(4-methylpiperazin-1-yl)-2-pyridyl]amino]-4-(5-methyl-1H-pyrrolo[2,3-b]pyridin-3-yl)isoindolin-1-one | Method AcHSS C18, m/z = 454 [M + H]+, Ret. time = 2.28 min. | ¹H NMR (400 MHz, DMSO): δ 11.80 (s, 1 H), 9.82 (s, 1 H), 8.78 (s, 1 H), 8.54 (d, J = 8.6 Hz, 1 H), 8.18 (s, 1 H), 8.01 (s, 2 H), 7.80 (d, J = 8.6 Hz, 1 H), 7.76 (s, 1 H), 7.47 (dd, J = 2.8, 9.1 Hz, 1 H), 6.97 (d, J = 9.1 Hz, 1 H), 4.56 (s, 2 H), 3.15 (dd, J = 4.9, 4.9 Hz, 4 H), 2.53 (dd, J = 4.9, 4.9 Hz, 4 H), 2.46 (s, 3 H), 2.29 (s, 3 H). | D AC9 BC23 |

TABLE 8-continued

Characterization Data (LCMS and ¹H NMR).

| # | STRUCTURE | NAME | LCMS | ¹H NMR | Method AA Reagent BB |
|---|---|---|---|---|---|
| I-31 | 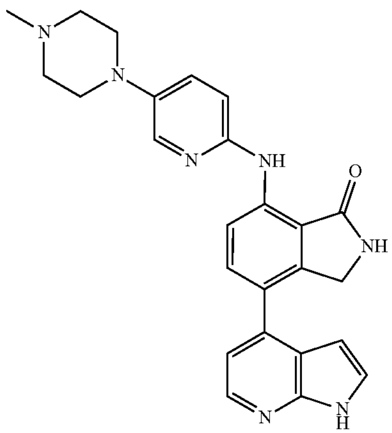 [SMILES: CN1CCN(c2ccc(Nc3ccc(-c4ccnc5[nH]ccc45)c4c3C(=O)NC4)nc2)CC1] | 7-[[5-(4-methylpiperazin-1-yl)-2-pyridyl]amino]-4-(1H-pyrrolo[2,3-b]pyridin-4-yl)isoindolin-1-one | Method BicarbB EHC18, m/z = 440 [M + H]+, Ret. time = 3.45 min. | ¹H NMR (400 MHz, DMSO): δ 11.78 (s, 1 H), 9.92 (s, 1 H), 8.75 (s, 1 H), 8.54 (d, J = 8.5 Hz, 1 H), 8.26 (d, J = 4.9 Hz, 1 H), 8.01 (d, J = 3.0 Hz, 1 H), 7.74 (d, J = 8.5 Hz, 1 H), 7.52 (dd, J = 3.0, 3.0 Hz, 1 H), 7.45 (dd, J = 3.0, 8.9 Hz, 1 H), 7.22 (d, J = 5.0 Hz, 1H), 6.97 (d, J = 8.9 Hz, 1 H), 6.46 (dd, J = 1.9, 3.5 Hz, 1 H), 4.47 (s, 2 H), 3.13 (dd, J = 4.9, 4.9 Hz, 4 H), 2.49 (dd, J = 4.9, 4.9 Hz, 4 H), 2.24 (s, 3 H). | E AC9 BC25 |
| I-32 | 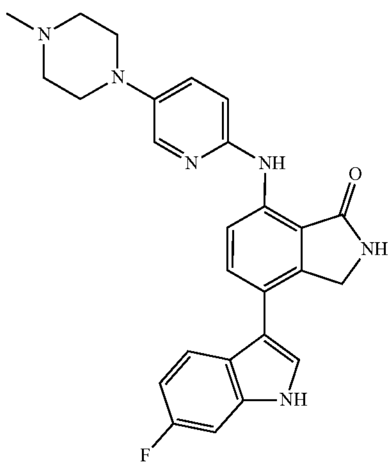 [SMILES: CN1CCN(c2ccc(Nc3ccc(-c4c[nH]c5cc(F)ccc45)c4c3C(=O)NC4)nc2)CC1] | 4-(6-fluoro-1H-indol-3-yl)-7-[[5-(4-methylpiperazin-1-yl)-2-pyridyl]amino]isoindolin-1-one | Method AcHSS C18, m/z = 457 [M + H]+, Ret. time = 2.94 min. | ¹H NMR (400 MHz, DMSO): δ 11.43 (s, 1 H), 9.77 (s, 1 H), 8.73 (s, 1 H), 8.49 (d, J = 8.5 Hz, 1 H), 7.99 (d, J = 3.0 Hz, 1 H), 7.74-7.69 (m, 2 H), 7.66 (d, J = 2.5 Hz, 1 H), 7.43 (dd, J = 3.0, 8.9 Hz, 1H), 7.23 (dd, J = 2.4, 9.9 Hz, 1 H), 6.97-6.92 (m, 2H), 4.49 (s, 2 H), 3.11 (dd, J = 4.9, 4.9 Hz, 4 H), 2.49 (dd, J = 4.9, 4.9 Hz, 4 H), 2.26 (s, 3 H). | F AC9 BC24 |

| # | STRUCTURE | NAME | LCMS | ¹H NMR | Method Reagent AA BB |
|---|---|---|---|---|---|
| I-33 | 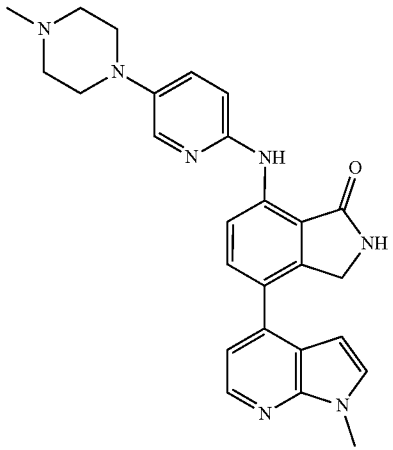 [SMILES: CN1CCN(c2ccc(Nc3ccc(-c4ccnc5c4ccn5C)c4c3C(=O)NC4)nc2)CC1] | 7-[[5-(4-methylpiperazin-1-yl)-2-pyridyl]amino]-4-(1-methylpyrrolo[2,3-b]pyridin-4-yl)isoindolin-1-one | Method BicarbB EHC18, m/z = 454 [M + H]+, Ret. time = 3.82 min. | ¹H NMR (400 MHz, DMSO): δ 9.92 (s, 1 H), 8.75 (s, 1 H), 8.54 (d, J = 8.5 Hz, 1 H), 8.31 (d, J = 4.9 Hz, 1 H), 8.01(d, J = 2.9 Hz, 1 H), 7.72 (d, J = 8.5 Hz, 1 H), 7.58 (d, J = 3.5 Hz, 1 H), 7.45 (dd, J = 3.0, 9.0 Hz, 1 H), 7.26 (d, J = 4.9 Hz, 1 H), 6.97 (d, J = 8.9 Hz, 1 H), 6.47 (d, J = 3.5 Hz, 1 H), 4.46 (s, 2H), 3.88 (s, 3 H), 3.12 (dd, J = 4.9, 4.9 Hz, 4 H), 2.49 (dd, J = 4.9, 4.9 Hz, 4 H), 2.24 (s, 3 H). | E AC9 BC26 |
| I-34 | 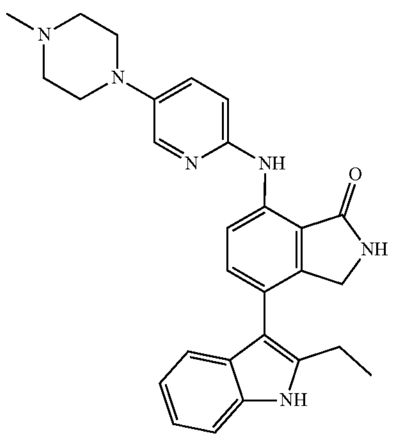 [SMILES: CCc1[nH]c2ccccc2c1-c1ccc(Nc2ccc(N3CCN(C)CC3)cn2)c2c1CNC2=O] | 4-(2-ethyl-1H-indol-3-yl)-7-[[5-(4-methylpiperazin-1-yl)-2-pyridyl]amino]iso-indolin-1-one | Method AcHSS C18, m/z = 467.2 [M + H]+, Ret. time = 3.11 min. | ¹H NMR (400 MHz, DMSO): δ 11.20 (s, 1 H), 9.77 (s, 1 H), 8.61 (s, 1 H), 8.48 (d, J = 8.6 Hz, 1 H), 8.02 (d, J = 2.8 Hz, 1 H), 7.48 (dd, J = 3.0, 8.8 Hz, 1 H), 7.41 (dd, J = 5.6, 8.1 Hz, 2 H), 7.21 (d, J = 7.8 Hz, 1 H), 7.10 (dd, J = 7.1, 7.1 Hz, 1 H), 7.03-6.96 (m, 2 H), 4.24-4.19 (m, 1 H), 4.06-4.00 (m, 1 H), 3.15 (dd, J = 4.4, 4.4 Hz, 4 H), 2.76-2.69 (m, 2 H), 2.53-2.48 (m, 4 H), 2.28 (s, 3 H), 1.27 (dd, J = 7.6, 7.6 Hz, 3 H). | F AC9 BC1 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-35 | 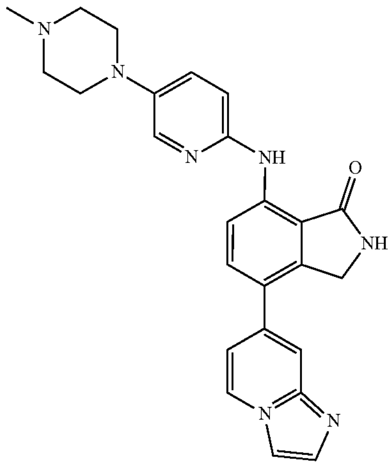 | 4-imidazo[1,2-a]pyridin-7-yl-7-[[5-(4-methylpiperazin-1-yl)-2-pyridyl]amino]isoindolin-1-one | Method AcHSS C18, m/z = 440 [M + H]+, Ret. time = 1.81 min. | ¹H NMR (400 MHz, DMSO): δ 9.93 (s, 1 H), 8.81 (s, 1 H), 8.61 (d, J = 7.4 Hz, 1 H), 8.52 (d, J = 8.7 Hz, 1 H), 8.01 (d, J = 2.9 Hz, 1 H), 7.98 (s, 1H), 7.72 (d, J = 8.7 Hz, 2 H), 7.63 (s, 1 H), 7.44 (dd, J = 3.0, 9.0 Hz, 1 H), 7.18 (dd, J = 1.8, 7.1 Hz, 1 H), 6.95 (d, J = 8.9 Hz, 1 H), 4.65 (s, 2 H), 3.12 (dd, J = 4.9, 4.9 Hz, 4 H), 2.48 (dd, J = 4.9, 4.9, 4 H), 2.24 (s, 3 H). | E AC9 BC27 |
| I-36 | 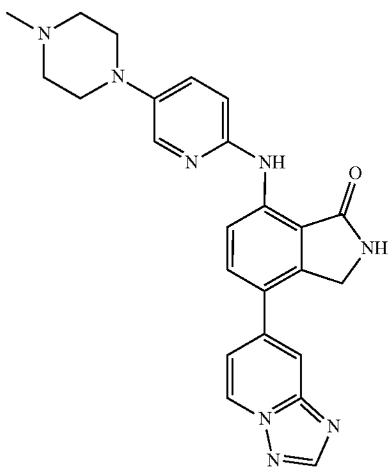 | 7-[[5-(4-methylpiperazin-1-yl)-2-pyridyl]amino]-4-([1,2,4]triazolo[1,5-a]pyridin-7-yl)isoindolin-1-one | Method AcHSS C18, m/z = 441 [M + H]+, Ret. time = 2.24 min. | ¹H NMR (400 MHz, DMSO): δ 10.00 (s, 1 H), 9.02 (d, J = 6.8 Hz, 1 H), 8.86 (s, 1 H), 8.57-8.54 (m, 2 H), 8.05-8.02 (m, 2H), 7.79 (d, J = 8.8 Hz, 1 H), 7.49-7.45 (m, 2 H), 6.98 (d, J = 9.0 Hz, 1H), 4.69 (s, 2 H), 3.24-3.19 (m, 4 H), 2.78-2.68 (m, 4 H), 2.42 (s, 3 H). | E AC9 BC28 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-37 | 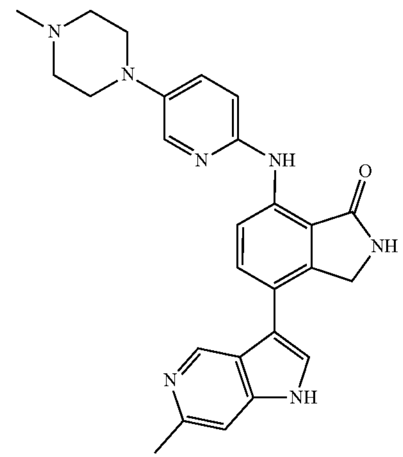 [SMILES: Cc1cc2[nH]cc(-c3ccc(Nc4ccc(N5CCN(C)CC5)cn4)c4c3CNC4=O)c2cn1] | 7-[[5-(4-methylpiperazin-1-yl)-2-pyridyl]amino]-4-(6-methyl-1H-pyrrolo[3,2-c]pyridin-3-yl)isoindolin-1-one | Method AcHSS C18, m/z = 454 [M + H]+, Ret. time = 1.87 min. | ¹H NMR (400 MHz, DMSO): δ 12.15-12.15 (m, 1 H), 9.86 (s, 1 H), 9.05 (s, 1 H), 8.81 (s, 1 H), 8.56 (d, J = 8.7 Hz, 1 H), 8.03 (d, J = 2.9 Hz, 1 H), 7.87-7.81 (m, 2 H), 7.52-7.46 (m, 2 H), 6.97 (d, J = 9.0 Hz, 1 H), 4.54 (s, 2 H), 3.25-3.21 (m, 3 H), 2.59-2.54 (m, 4 H), 2.96-2.88 (m, 4 H), 2.64 (s, 3 H). | F AC9 BC29 |
| I-38 | 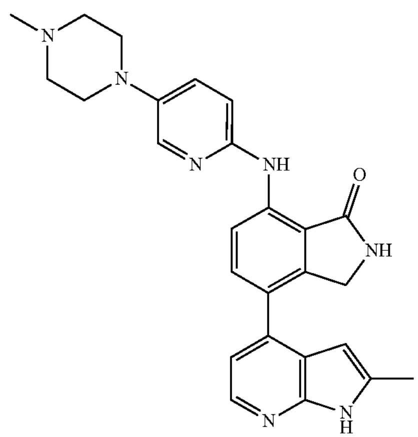 | 7-[[5-(4-methylpiperazin-1-yl)-2-pyridyl]amino]-4-(2-methyl-1H-pyrrolo[2,3-b]pyridin-4-yl)isoindolin-1-one | Method AcHSS C18, m/z = 454 [M + H]+, Ret. time = 2.22 min. | ¹H NMR (400 MHz, DMSO): δ 11.59 (s, 1 H), 9.90 (s, 1 H), 8.73 (s, 1 H), 8.52 (d, J = 8.7 Hz, 1 H), 8.17-8.13 (m, 1 H), 8.01 (d, J = 2.9 Hz, 1 H), 7.70 (d, J = 8.7 Hz, 1 H), 7.45 (dd, J = 3.1, 9.0 Hz, 1 H), 7.14 (d, J = 5.0 Hz, 1 H), 6.97 (d, J = 9.0 Hz, 1 H), 6.16 (s, 1 H), 4.44 (s, 2 H), 3.14 (dd, J = 4.9, 4.9 Hz, 4 H), 2.54 (dd, J = 4.9, 4.9 Hz, 4 H), 2.41 (s, 3 H), 2.28 (s, 3 H). | F AC9 BC30 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-39 | 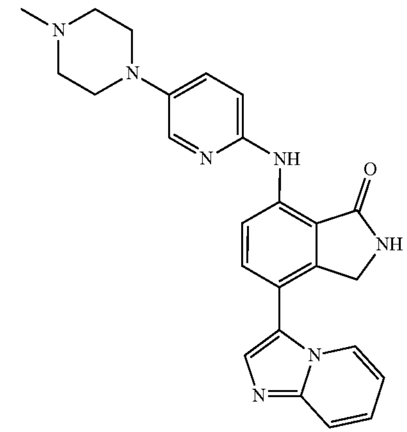 | 4-imidazo[1,2-a]pyridin-3-yl-7-[[5-(4-methylpiperazin-1-yl)-2-pyridyl]amino]isoindolin-1-one | Method AcHSS C18, m/z = 440 [M + H]+, Ret. time = 1.73 min. | ¹H NMR (400 MHz, DMSO): δ 9.86 (s, 1 H), 8.77 (s, 1 H), 8.57 (d, J = 8.5 Hz, 1 H), 8.39 (d, J = 6.9 Hz, 1 H), 8.01 (d, J = 3.0 Hz, 1 H), 7.84 (s, 1 H), 7.69 (dd, J = 8.8, 15.1 Hz, 2 H), 7.45 (dd, J = 3.1, 9.0 Hz, 1 H), 7.33-7.29 (m, 1 H), 6.99-6.92 (m, 2 H), 4.39 (s, 2 H), 3.12 (dd, J = 4.9, 4.9 Hz, 4 H), 2.48 (dd, J = 4.9, 4.9 Hz, 4 H), 2.24 (s, 3 H). | F AC9 BC31 |
| I-40 | 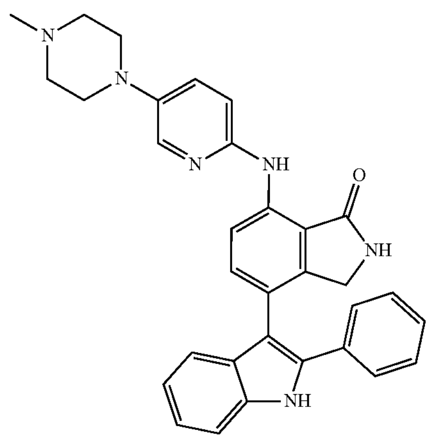 [SMILES: CN1CCN(c2ccc(Nc3ccc(-c4c(-c5ccccc5)[nH]c5ccccc45)c4c3C(=O)NC4)nc2)CC1] | 7-[[5-(4-methylpiperazin-1-yl)-2-pyridyl]amino]-4-(2-phenyl-1H-indol-3-yl)isoindolin-1-one | Method BicarbB EHC18, m/z = 515 [M + H]+, Ret. time = 5 min. | ¹H NMR (400 MHz, DMSO): δ 11.67 (s, 1 H), 9.77 (s, 1 H), 8.51 (d, J = 8.3 Hz, 1 H), 8.46 (s, 1 H), 8.04 (d, J = 2.5 Hz, 1 H), 7.56-7.46 (m, 6 H), 7.45-7.31 (m, 4 H), 7.22 (dd, J = 7.5, 7.5 Hz, 1 H), 7.08 (dd, J = 7.5, 7.5 Hz, 1 H), 7.00 (d, J = 9.1 Hz, 1 H), 3.94-3.92 (m, 1 H), 3.16 (dd, J = 4.8, 4.8 Hz, 4 H), 3.61-2.57 (m, 4 H), 2.31 (s, 3H). | F AC9 BC125 |

TABLE 8-continued

Characterization Data (LCMS and ¹H NMR).

| # | STRUCTURE | NAME | LCMS | ¹H NMR | Method AA Reagent BB |
|---|---|---|---|---|---|
| I-41 | 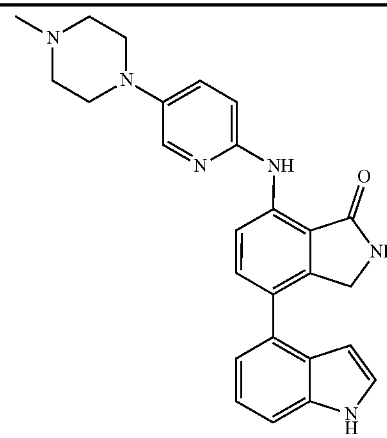 | 4-(1H-indol-4-yl)-7-[[5-(4-methylpiperazin-1-yl)-2-pyridyl]amino]isoindolin-1-one | Method AcHSS C18, m/z = 439 [M + H]+, Ret. time = 2.73 min. | ¹H NMR (400 MHz, DMSO): δ 11.25 (s, 1 H), 9.83 (s, 1 H), 8.49 (d, J = 8.4 Hz, 1 H), 8.00 (d, J = 2.9 Hz, 1 H), 7.62 (d, J = 8.5 Hz, 1 H), 7.46-7.38 (m, 3 H), 7.17 (dd, J = 7.6, 7.6 Hz, 1 H), 7.11 (d, J = 6.8 Hz, 1 H), 6.95 (d, J = 8.9 Hz, 1 H), 6.34 (dd, J = 2.6, 2.6 Hz, 1 H), 4.35 (s, 2 H), 3.11 (dd, J = 4.9, 4.9 Hz, 4 H), 2.48 (dd, J = 4.9, 4.9 Hz, 4 H), 2.24 (s, 3 H). | E AC9 BC32 |
| I-42 | 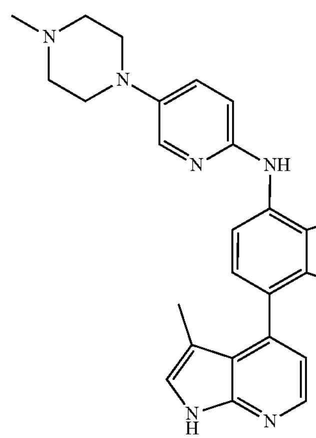 | 7-[[5-(4-methylpiperazin-1-yl)-2-pyridyl]amino]-4-(3-methyl-1H-pyrrolo[2,3-b]pyridin-4-yl)isoindolin-1-one | Method AcHSS C18, m/z = 454 [M + H]+, Ret. time = 2.12 min. | ¹H NMR (400 MHz, DMSO): δ 11.46 (d, J = 1.9 Hz, 1 H), 9.79 (s, 1 H), 8.66 (s, 1 H), 8.50 (d, J = 8.4 Hz, 1 H), 8.20 (d, J = 4.8 Hz, 1 H), 8.01 (d, J = 2.9 Hz, 1 H), 7.47-7.42 (m, 2 H), 7.25-7.25 (m, 1 H), 7.02 (d, J = 4.8 Hz, 1 H), 6.96 (d, J = 9.0 Hz, 1 H), 4.19 (s, 2 H), 3.11 (dd, J = 4.9, 4.9 Hz, 4 H), 2.49 (dd, J = 4.9, 4.9 Hz, 4 H), 2.24 (s, 3 H), 1.80 (s, 3 H). | F AC9 BC33 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-43 | 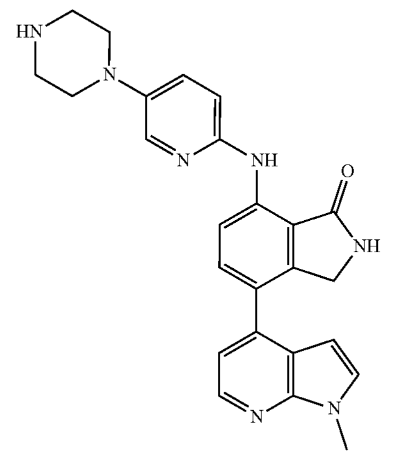 | 4-(1-methylpyrrolo[2,3-b]pyridin-4-yl)-7-[(5-piperazin-1-yl-2-pyridyl)amino]isoindolin-1-one | Method AcHSS C18, m/z = 440 [M + H]+, Ret. time = 2.44 min. | ¹H NMR (400 MHz, DMSO): δ 9.85 (s, 1 H), 8.68 (s, 1 H), 8.48 (d, J = 8.6 Hz, 1 H), 8.26 (d, J = 4.8 Hz, 1 H), 7.93 (d, J = 2.8 Hz, 1 H), 7.66 (d, J = 8.6 Hz, 1 H), 7.52 (d, J = 3.5 Hz, 1 H), 7.37 (dd, J = 2.9, 8.7 Hz, 1 H), 7.20 (d, J = 4.8 Hz, 1H), 6.91 (d, J = 8.8 Hz, 1 H), 6.41 (d, J = 3.5 Hz, 1H), 4.40 (s, 2H), 3.81 (s, 2 H), 2.96 (dd, J = 4.7, 4.7 Hz, 4 H), 2.80 (dd, J = 4.7, 4.7 Hz, 4 H), 2.03 (s, 2H). | E AC8 BC26 |
| I-44 | 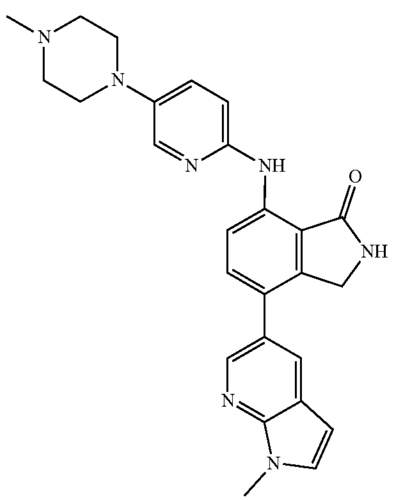 [SMILES: CN1CCN(c2ccc(Nc3ccc(-c4cnc5c(ccn5C)c4)c4c3C(=O)NC4)nc2)CC1] | 7-[[5-(4-methylpiperazin-1-yl)-2-pyridyl]amino]-4-(1-methylpyrrolo[2,3-b]pyridin-5-yl)isoindolin-1-one | Method AcHSS C18, m/z = 454 [M + H]+, Ret. time = 2.65 min. | ¹H NMR (400 MHz, DMSO): δ 9.88 (s, 1 H), 8.78 (s, 1 H), 8.54 (d, J = 8.3 Hz, 1 H), 8.50 (d, J = 2.0 Hz, 1 H), 8.18 (d, J = 2.0 Hz, 1 H), 8.04 (d, J = 2.8 Hz, 1 H), 7.66-7.61 (m, 2H), 7.48 (dd, J = 3.2, 9.0 Hz, 1 H), 6.98 (d, J = 8.8 Hz, 1 H), 6.56 (d, J = 3.5 Hz, 1 H), 4.58 (s, 2 H), 3.91 (s, 3 H), 3.36-3.30 (m, 4 H), 3.19-3.12 (m, 4 H), 2.30 (s, 3 H). | E AC9 BC34 |

TABLE 8-continued

Characterization Data (LCMS and $^1$H NMR).

| # | STRUCTURE | NAME | LCMS | $^1$H NMR | Method Reagent AA BB |
|---|---|---|---|---|---|
| I-45 | 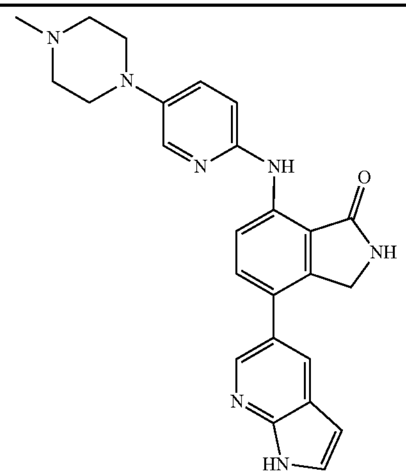 | 7-[[5-(4-methylpiperazin-1-yl)-2-pyridyl]amino]-4-(1H-pyrrolo[2,3-b]pyridin-5-yl)isoindolin-1-one | Method AcHSS C18, m/z = 440 [M + H]+, Ret. time = 2.34 min. | $^1$H NMR (400 MHz, DMSO): δ 11.76 (s, 1 H), 9.88 (s, 1 H), 8.77 (s, 1 H), 8.54 (d, J = 8.3 Hz, 1H), 8.45 (d, J = 1.8 Hz, 1 H), 8.17 (d, J = 1.8 Hz, 1 H), 8.04 (d, J = 2.8 Hz, 1 H), 7.64 (d, J = 8.3 Hz, 1 H), 7.57 (s, 1 H), 7.48 (dd, J = 2.8, 8.8 Hz, 1 H), 6.98 (d, J = 9.1 Hz, 1 H), 6.54 (d, J = 2.3 Hz, 1H), 4.59 (s, 2H), 3.15 (dd, J = 4.5, 4.5 Hz, 4 H), 2.53-2.50 (m, 4 H), 2.28 (s, 3 H). | E AC9 BC36 |
| I-46 | 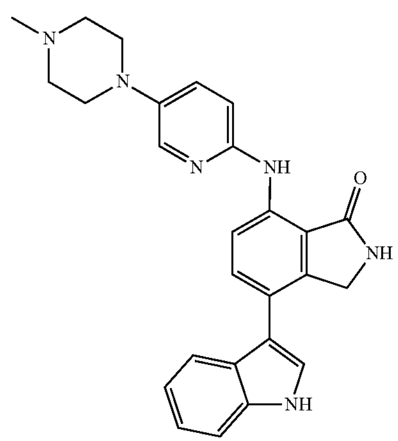 [SMILES: CN1CCN(c2ccc(Nc3ccc(-c4c[nH]c5ccccc45)c4c3C(=O)NC4)nc2)CC1] | 4-(1H-indol-3-yl)-7-[[5-(4-methylpiperazin-1-yl)-2-pyridyl]amino]isoindolin-1-one | Method AcHSS C18, m/z = 439 [M + H]+, Ret. time = 2.82 min. | $^1$H NMR (400 MHz, DMSO): δ 11.42-11.38 (m, 1 H), 9.82 (s, 1 H), 8.75 (s, 1 H), 8.52 (d, J = 8.3 Hz, 1 H), 8.04 (d, J = 2.8 Hz, 1 H), 7.81-7.74 (m, 2 H), 7.69 (d, J = 2.3 Hz, 1 H), 7.53-7.46 (m, 2H), 7.21 (dd, J = 7.3, 7.3 Hz, 1 H), 7.13 (dd, J = 7.2, 7.2 Hz, 1 H), 6.98 (d, J = 9.1 Hz, 1 H), 4.54 (s, 2H), 3.19 (dd, J = 5.3, 5.3 Hz, 4 H), 2.66 (dd, J = 5.3, 5.3 Hz, 4 H), 2.38 (s, 3 H). | E AC9 BC10 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-47 | (structure) | 4-[1-(2-methoxyethyl)pyrrolo[2,3-b]pyridin-4-yl]-7-[[5-(4-methylpiperazin-1-yl)-2-pyridyl]amino]isoindolin-1-one | Method AcHSS C18, m/z = 498 [M + H]+, Ret. time = 2.62 min. | ¹H NMR (400 MHz, DMSO): δ 9.96 (s, 1 H), 8.79 (s, 1 H), 8.58 (d, J = 8.6 Hz, 1 H), 8.34 (d, J = 4.8 Hz, 1 H), 8.05 (d, J = 2.3 Hz, 1 H), 7.77 (d, J = 8.6 Hz, 1 H), 7.64 (d, J = 3.3 Hz, 1 H), 7.49 (dd, J = 2.9, 9.0 Hz, 1 H), 7.31 (d, J = 4.8 Hz, 1 H), 7.01 (d, J = 8.8 Hz, 1 H), 6.52 (d, J = 3.5 Hz, 1 H), 4.52 (dd, J = 5.4, 5.4 Hz, 4 H), 3.79 (dd, J = 5.4, 5.4 Hz, 2 H), 3.32 (s, 3 H), 3.16 (dd, J = 4.7, 4.7 Hz, 4 H), 2.34 (dd, J = 4.7, 4.7 Hz, 4 H), 2.28 (s, 3 H). | D AC9 BC3 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-48 | 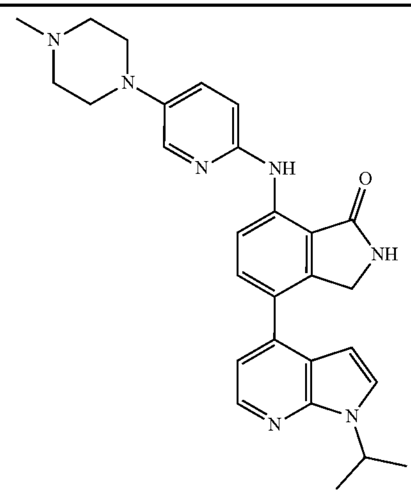 | 4-(1-isopropylpyrrolo[2,3-b]pyridin-4-yl)-7-[[5-(4-methylpiperazin-1-yl)-2-pyridyl]amino]isoindolin-1-one | Method AcHSS C18, m/z = 482 [M + H]+, Ret. time = 2.93 min. | ¹H NMR (400 MHz, DMSO): δ 9.96 (s, 1 H), 8.78 (s, 1 H), 8.58 (d, J = 8.3 Hz, 1 H), 8.34 (d, J = 4.8 Hz, 1 H), 8.05 (d, J = 2.8 Hz, 1 H), 7.78 (d, J = 8.3 Hz, 2 H), 7.49 (dd, J = 3.0, 8.8 Hz, 1 H), 7.30 (d, J = 4.8 Hz, 1 H), 7.01 (d, J = 9.1 Hz, 1 H), 6.54 (d, J = 3.5 Hz, 1 H), 5.24-5.15 (m, 1 H), 4.52 (s, 2 H), 3.16 (dd, J = 4.7, 4.7 Hz, 4 H), 2.48 (dd, J = 4.7, 4.7 Hz, 4 H), 2.28 (s, 3 H), 1.55 (d, J = 6.8 Hz, 6 H). | D AC9 BC37 |
| I-49 | 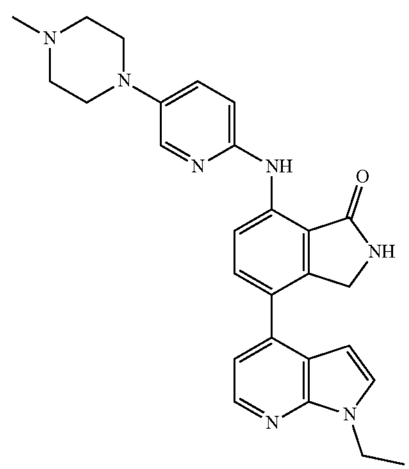 [SMILES: CCn1ccc2c(-c3ccc(Nc4ccc(N5CCN(C)CC5)cn4)c4c3CNC4=O)ccnc21] | 4-(1-ethylpyrrolo[2,3-b]pyridin-4-yl)-7-[[5-(4-methylpiperazin-1-yl)-2-pyridyl]amino]isoindolin-1-one | Method AcHSS C18, m/z = 468 [M + H]+, Ret. time = 2.71 min. | ¹H NMR (400 MHz, DMSO): δ 9.96 (s, 1 H), 8.78 (s, 1 H), 8.58 (d, J = 8.6 Hz, 1 H), 8.34 (d, J = 5.1 Hz, 1 H), 8.05 (d, J = 2.8 Hz, 1 H), 7.77 (d, J = 8.6 Hz, 1 H), 7.69 (d, J = 3.5 Hz, 1 H), 7.49 (dd, J = 2.8, 8.8 Hz, 1 H), 7.30 (d, J = 5.1 Hz, 1 H), 7.01 (d, J = 9.1 Hz, 1 H), 6.52 (d, J = 3.5 Hz, 1 H), 4.51 (s, 2H), 4.39 (q, J = 7.1 Hz, 2H), 3.16 (dd, J = 4.8, 4.8 Hz, 4 H), 2.53-2.52 (m, 4 H), 2.29 (s, 3H), 1.47 (dd, J = 7.1, 7.1 Hz, 3 H). | D AC9 BC38 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-50 | 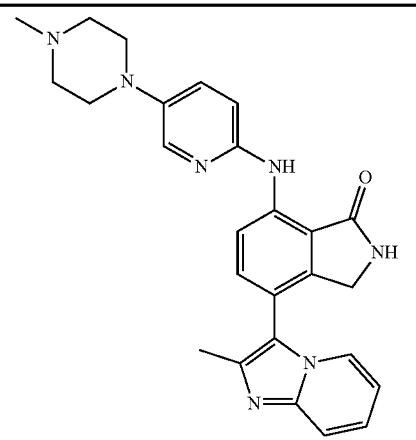 | 4-(2-methylimidazo[1,2-a]pyridin-3-yl)-7-[[5-(4-methylpiperazin-1-yl)-2-pyridyl]amino]isoindolin-1-one | Method BicarbB EHC18, m/z = 454 [M + H]+, Ret. time = 3.48 min. | ¹H NMR (400 MHz, DMSO): δ 9.77 (s, 1 H), 8.63 (s, 1 H), 8.46 (d, J = 8.5 Hz, 1 H), 7.93 (d, J = 3.0 Hz, 1H), 7.89 (d, J = 6.9 Hz, 1 H), 7.45 (dd, J = 3.6, 8.8 Hz, 2 H), 7.37 (dd, J = 3.0, 9.0 Hz, 1 H), 7.19-7.14 (m, 1 H), 6.90 (d, J = 8.9 Hz, 1 H), 6.775 (dd, J = 5.8, 6.7 Hz, 1 H), 3.98 (d, J = 8.2 Hz, 2 H), 3.03 (dd, J = 5.0, 5.0 Hz, 4 H), 2.46 (dd, J = 5.0, 5.0 Hz, 4 H), 2.18 (d, J = 17.6 Hz, 6 H). | F AC9 BC39 |
| I-51 | 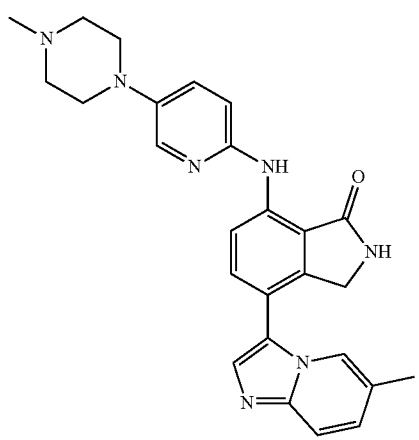 | 4-(6-methylimidazo[1,2-a]pyridin-3-yl)-7-[[5-(4-methylpiperazin-1-yl)-2-pyridyl]amino]isoindolin-1-one | Method AcHSS C18, m/z = 454 [M + H]+, Ret. time = 1.87 min. | ¹H NMR (400 MHz, DMSO): δ 9.77 (s, 1 H), 8.68 (s, 1 H), 8.49 (d, J = 8.5 Hz, 1 H), 8.08 (s, 1H), 7.92 (d, J = 3.0 Hz, 1 H), 7.68 (s, 1 H), 7.61 (d, J = 8.5 Hz, 1 H), 7.49 (d, J = 9.4 Hz, 1 H), 7.37 (dd, J = 3.1, 9.0 Hz, 1 H), 7.08 (dd, J = 1.5, 9.2 Hz, 1 H), 6.89 (d, J = 8.9 Hz, 1 H), 4.28 (s, 2 H), 3.04 (dd, J = 4.9, 4.9 Hz, 4 H), 2.44-2.42 (m, 4 H), 2.22 (s, 3 H), 2.16 (s, 3 H). | F AC9 BC40 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-52 | 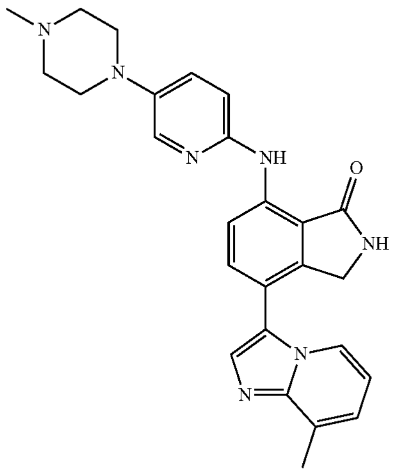 [SMILES: Cc1cccn2c(-c3ccc(Nc4ccc(N5CCN(C)CC5)cn4)c4c3CNC4=O)cnc12] | 4-(8-methylimidazo[1,2-a]pyridin-3-yl)-7-[[5-(4-methylpiperazin-1-yl)-2-pyridyl]amino]isoindolin-1-one | Method AcHSS C18, m/z = 454 [M + H]+, Ret. time = 1.85 min. | ¹H NMR (400 MHz, DMSO): δ 9.76 (s, 1 H), 8.68 (s, 1 H), 8.47 (d, J = 8.5 Hz, 1 H), 8.14 (d, J = 6.9 Hz, 1 H), 7.92 (d, J = 2.9 Hz, 1 H), 7.71 (s, 1 H), 7.59 (d, J = 8.5 Hz, 1 H), 7.37 (dd, J = 3.1, 9.0 Hz, 1 H), 7.04 (d, J = 6.8 Hz, 1 H), 6.89 (d, J = 8.9 Hz, 1 H), 6.77 (dd, J = 6.8, 6.8 Hz, 1 H), 4.30 (s, 2 H), 3.03 (dd, J = 4.9, 4.9 Hz, 4 H), 2.47 (m, 3 H), 2.40 (dd, J = 4.9, 4.9 Hz, 4 H), 2.16 (s, 3 H). | F AC9 BC41 |
| I-53 | 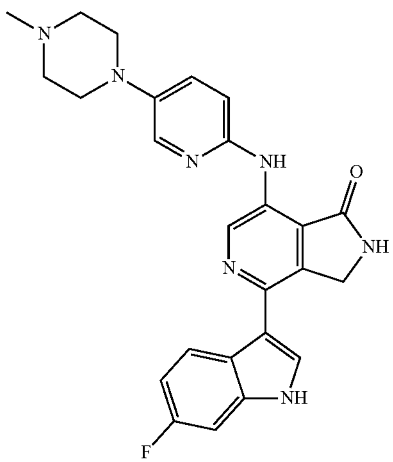 [SMILES: CN1CCN(c2ccc(Nc3cnc(-c4c[nH]c5cc(F)ccc45)c4c3C(=O)NC4)nc2)CC1] | 4-(6-fluoro-1H-indol-3-yl)-7-[[5-(4-methylpiperazin-1-yl)-2-pyridyl]amino]-2,3-dihydropyrrolo[3,4-c]pyridin-1-one | Method AcHSS C18, m/z = 458 [M + H]+, Ret. time = 2.5 min. | 1H NMR (400 MHz, DMSO-d6) δ 11.59 (s, 1H), 9.83 (d, J = 2.4 Hz, 1H), 9.30 (d, J = 2.5 Hz, 1H), 9.19 (s, 1H), 8.62 (s, 1H), 8.05 (s, 1H), 7.76 (d, J = 2.8 Hz, 1H), 7.47 (d, J = 9.0 Hz, 1H), 7.23 (d, J = 9.9 Hz, 1H), 7.06-6.88 (m, 2H), 4.70 (s, 2H), 3.18 (s, 4H). | A AC9 BB20 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-54 | 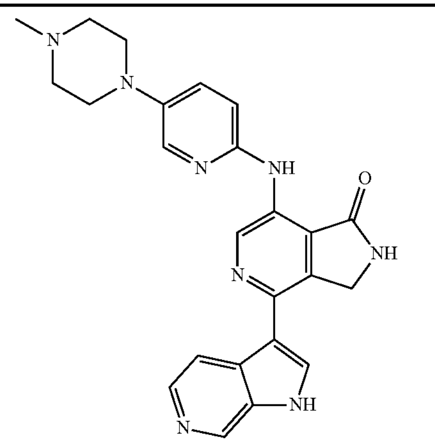 | 7-[[5-(4-methylpiperazin-1-yl)-2-pyridyl]amino]-4-(1H-pyrrolo[2,3-c]pyridin-3-yl)-2,3-dihydropyrrolo[3,4-c]pyridin-1-one | Method AcHSS C18, m/z = 441 [M + H]+, Ret. time = 1.76 min. | ¹H NMR (400 MHz, DMSO): δ 12.03-12.00 (m, 1 H), 9.88 (s, 1 H), 9.33 (s, 1 H), 9.22 (s, 1 H), 8.86 (s, 1 H), 8.50 (d, J = 5.3 Hz, 1 H), 8.26 (d, J = 5.3 Hz, 1 H), 8.08 (d, J = 2.5 Hz, 1 H), 8.01 (d, J = 2.3 Hz, 1 H), 7.50 (dd, J = 2.5, 8.8 Hz, 1 H), 7.05 (d, J = 9.1 Hz, 1 H), 4.77 (s, 2 H), 3.18 (dd, J = 4.2, 4.2 Hz, 4 H), 2.48 (dd, J = 4.2, 4.2 Hz, 4 H), 2.29 (s, 3 H). | A AC9 BB38 |
| I-55 | 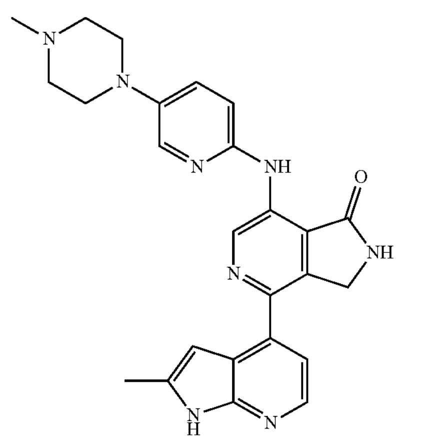 [SMILES: Cc1cc2c(-c3ncc(Nc4ccc(N5CCN(C)CC5)cn4)c4c3CNC4=O)ccnc2[nH]1] | 7-[[5-(4-methylpiperazin-1-yl)-2-pyridyl]amino]-4-(2-methyl-1H-pyrrolo[2,3-b]pyridin-4-yl)-2,3-dihydropyrrolo[3,4-c]pyridin-1-one | Method AcHSS C18, m/z = 455 [M + H]+, Ret. time = 2.03 min. | ¹H NMR (400 MHz, DMSO): δ 11.55-11.54 (m, 1 H), 9.91 (s, 1 H), 9.50 (s, 1 H), 9.14 (s, 1 H), 8.18 (s, 1 H), 8.06 (s, 1 H), 7.48 (d, J = 8.8 Hz, 1 H), 7.28 (s, 1 H), 7.05 (d, J = 8.8 Hz, 1 H), 6.61 (s, 1 H), 4.70 (s, 2 H), 3.15 (s, 6 H), 2.43 (s, 4 H), 2.25 (s, 4 H). | A AC9 BB25 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-56 | 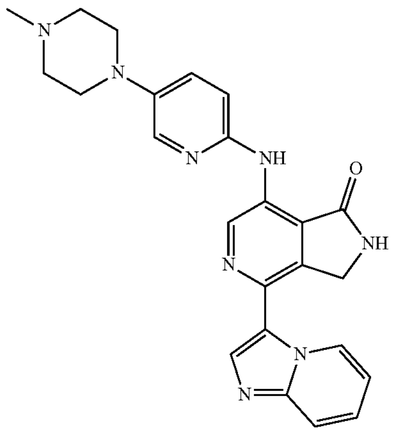 [SMILES: CN1CCN(c2ccc(Nc3cnc(-c4cnc5ccccn45)c4c3C(=O)NC4)nc2)CC1] | 4-imidazo[1,2-a]pyridin-3-yl-7-[[5-(4-methylpiperazin-1-yl)-2-pyridyl]amino]-2,3-dihydropyrrolo[3,4-c]pyridin-1-one | Method AcHSS C18, m/z = 441 [M + H]+, Ret. time = 1.84 min. | ¹H NMR (400 MHz, DMSO): δ 9.82-9.78 (m, 2 H), 9.33 (s, 1 H), 9.18 (s, 1 H), 8.00 (s, 1 H), 7.95 (d, J = 3.0 Hz, 1 H), 7.65 (d, J = 9.0 Hz, 1 H), 7.40-7.31 (m, 2 H), 7.03-6.99 (m, 1 H), 6.95 (d, J = 8.9 Hz, 1 H), 4.68 (s, 2 H), 3.05 (dd, J = 4.8, 4.8 Hz, 4 H), 2.42-2.38 (m, 4 H), 2.17 (s, 3 H). | C AC9 BC42 |
| I-57 | 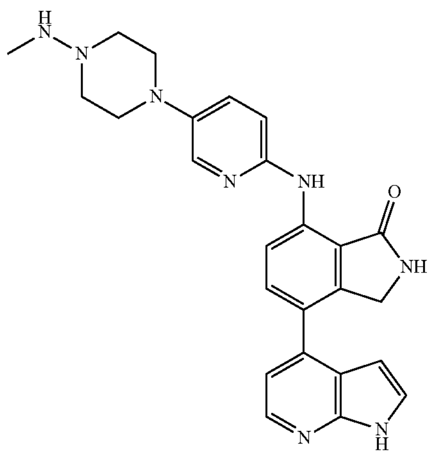 [SMILES: CNN1CCN(c2ccc(Nc3ccc(-c4ccnc5[nH]ccc45)c4c3C(=O)NC4)nc2)CC1] | 7-[[5-[4-(methylamino)-1-piperidyl]-2-pyridyl]amino]-4-(1H-pyrrolo[2,3-b]pyridin-4-yl)isoindolin-1-one | Method AcHSS C18, m/z = 454 [M + H]+, Ret. time = 2.13 min. | ¹H NMR (400 MHz, DMSO): δ 11.78 (s, 1 H), 9.90 (s, 1 H), 8.74 (s, 1 H), 8.54 (d, J = 8.5 Hz, 1 H), 8.26 (d, J = 4.9 Hz, 1 H), 8.02 (d, J = 2.9 Hz, 1 H), 7.73 (d, J = 8.5 Hz, 1 H), 7.52 (dd, J = 2.9, 2.9 Hz, 1 H), 7.45 (dd, J = 3.0, 8.9 Hz, 1 H), 7.22 (d, J = 5.0 Hz, 1 H), 6.96 (dd, J = 8.9 Hz, 1 H), 6.46 (dd, J = 1.8, 3.4 Hz, 1 H), 4.47 (s, 2 H), 3.58-3.54 (m, 2 H), 2.77-2.68 (m, 3 H), 2.47-2.41 (m, 1 H), 2.32 (s, 3H), 1.93-1.90 (m, 2 H), 1.43-1.33 (m, 2H). | E AC13 BC25 |

TABLE 8-continued

Characterization Data (LCMS and ¹H NMR).

| # | STRUCTURE | NAME | LCMS | ¹H NMR | Method AA Reagent BB |
|---|---|---|---|---|---|
| I-58 | (structure) | 4-imidazo[1,2-a]pyridin-3-yl-7-[[5-[4-(methylamino)-1-piperidyl]-2-pyridyl]amino]isoindolin-1-one | Method AcHSS C18, m/z = 454 [M + H]+, Ret. time = 1.77 min. | ¹H NMR (400 MHz, DMSO): δ 9.76 (s, 1 H), 8.68 (s, 1 H), 8.47 (d, J = 8.5 Hz, 1 H), 8.30 (d, J = 6.9 Hz, 1 H), 7.93 (d, J = 2.9 Hz, 1 H), 7.76 (s, 1 H), 7.60 (dd, J = 8.8, 13.8 Hz, 2 H), 7.36 (dd, J = 3.0, 9.0 Hz, 1 H), 7.24-7.20 (m, 1 H), 6.89-6.85 (m, 2 H), 4.31 (s, 2 H), 3.34-3.25 (m, 3 H), 2.69-2.60 (m, 2 H), 2.39-2.32 (m, 1 H), 2.23 (s, 3 H), 1.87-1.81 (m, 2 H), 1.35-1.23 (m, 2 H). | E AC13 BC42 |
| I-59 | (structure) | 4-imidazo[1,2-b]pyridazin-3-yl-7-[[5-(4-methylpiperazin-1-yl)-2-pyridyl]amino]isoindolin-1-one | Method AcHSS C18, m/z = 441 [M + H]+, Ret. time = 2.01 min. | ¹H NMR (400 MHz, DMSO): δ 9.90 (s, 1 H), 8.82 (s, 1 H), 8.62 (dd, J = 1.6, 4.4 Hz, 1 H), 8.51 (d, J = 8.7 Hz, 1 H), 8.23 (dd, J = 1.6, 9.3 Hz, 1 H), 8.14-8.10 (m, 2 H), 8.01 (d, J = 2.9 Hz, 1 H), 7.45 (dd, J = 3.1, 9.0 Hz, 1 H), 7.30 (dd, J = 4.4, 9.3 Hz, 1 H), 6.98 (d, J = 8.9 Hz, 1 H), 4.54 (s, 2 H), 3.12 (dd, J = 4.9, 4.9 Hz, 4 H), 2.49 (dd, J = 4.9, 4.9 Hz, 4 H), 2.24 (s, 3 H). | F AC9 BC43 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-60 | 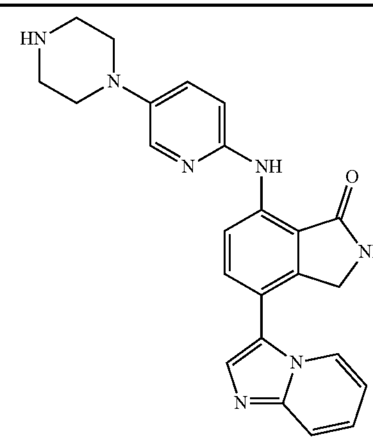 | 4-imidazo[1,2-a]pyridin-3-yl-7-[[5-piperazin-1-yl-2-pyridyl]amino]isoindolin-1-one | Method AcHSS C18, m/z = 426 [M + H]+, Ret. time = 1.7 min. | ¹H NMR (400 MHz, DMSO): δ 9.90 (s, 1 H), 8.79 (s, 1 H), 8.59 (d, J = 8.7 Hz, 1 H), 8.39 (d, J = 6.9 Hz, 1 H), 8.04 (d, J = 3.0 Hz, 1 H), 7.85 (s, 1 H), 7.70 (dd, J = 8.8, 17.8 Hz, 2 H), 7.48 (dd, J = 3.0, 9.0 Hz, 1 H), 7.33-7.29 (m, 1 H), 7.01 (dd, J = 8.9 Hz, 1 H), 6.95 (dd, J = 6.5, 6.5 Hz, 1 H), 4.40 (s, 2 H), 3.24-3.09 (m, 9 H). | E AC8 BC42 |
| I-61 | 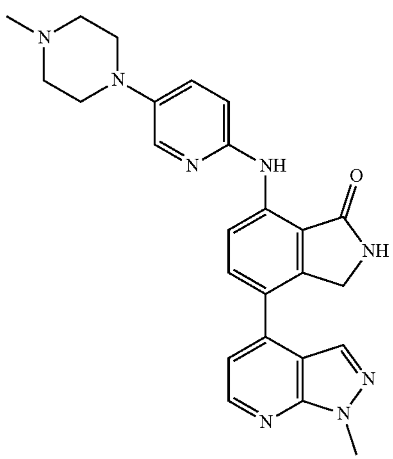 | 7-[[5-(4-methylpiperazin-1-yl)-2-pyridyl]amino]-4-(1-methylpyrazolo[3,4-b]pyridin-4-yl)isoindolin-1-one | Method AcHSS C18, m/z = 455 [M + H]+, Ret. time = 2.49 min. | ¹H NMR (400 MHz, DMSO): δ 10.00 (s, 1 H), 8.84 (s, 1 H), 8.62-8.58 (m, 2 H), 8.23 (s, 1 H), 8.03 (d, J = 3.0 Hz, 1 H), 7.86 (d, J = 8.6 Hz, 1 H), 7.46 (dd, J = 3.0, 9.0 Hz, 1 H), 7.42 (d, J = 4.8 Hz, 1 H), 6.99 (d, J = 9.4 Hz, 1 H), 4.57 (s, 2 H), 4.12 (s, 3 H), 3.13 (t, J = 4.9 Hz, 4 H), 2.49 (t, J = 4.3 Hz, 4 H), 2.25 (s, 3 H). | D AC9 BC44 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-62 | 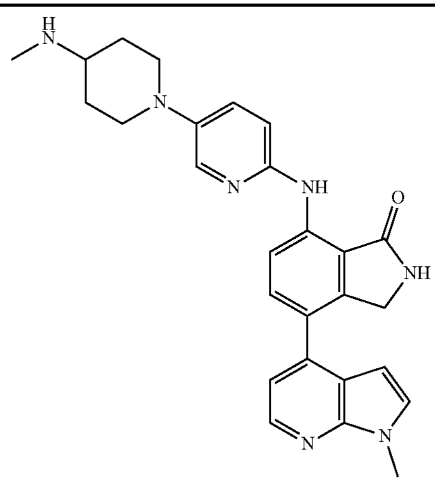 | 7-[[5-[4-(methylamino)-1-piperidyl]-2-pyridyl]amino]-4-(1-methylpyrrolo[2,3-b]pyridin-4-yl)isoindolin-1-one | Method AcHSS C18, m/z = 468 [M + H]+, Ret. time = 2.49 min. | ¹H NMR (400 MHz, DMSO): δ 9.89 (s, 1 H), 8.72 (s, 1 H), 8.52 (d, J = 8.6 Hz, 1 H), 8.30 (d, J = 4.8 Hz, 1 H), 8.01 (d, J = 3.0 Hz, 1 H), 7.70 (d, J = 8.6 Hz, 1 H), 7.56 (d, J = 3.5 Hz, 1 H), 7.44 (dd, J = 3.2, 9.0 Hz, 1 H), 7.24 (d, J = 5.1 Hz, 1 H), 6.95 (d, J = 9.1 Hz, 1 H), 6.45 (d, J = 3.5 Hz, 1 H), 4.44 (s, 2 H), 3.86 (s, 3 H), 3.60-3.55 (m, 2 H), 3.17 (d, J = 4.8 Hz, 1 H), 2.76-2.68 (m, 2 H), 2.56-2.54 (m, 1 H), 2.35 (s, 3 H), 1.94-1.90 (m, 2 H), 1.45-1.35 (m, 2 H). | E AC13 BC26 |
| I-63 | 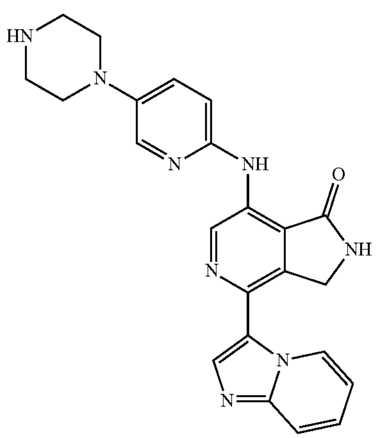 [SMILES: O=C1NCc2c(-c3cnc4ccccn34)ncc(Nc3ccc(N4CCNCC4)cn3)c21] | 4-imidazo[1,2-a]pyridin-3-yl-7-[[5-piperazin-1-yl-2-pyridyl]amino]-2,3-dihydropyrrolo[3,4-c]pyridin-1-one | Method AcHSS C18, m/z = 427 [M + H]+, Ret. time = 1.82 min. | ¹H NMR (400 MHz, DMSO): δ 9.90 (s, 1 H), 9.88 (td, J = 1.4, 7.0 Hz, 1 H), 9.40 (s, 1 H), 9.26 (s, 1 H), 8.08 (s, 1 H), 8.02 (d, J = 3.2 Hz, 1 H), 7.73 (td, J = 1.1, 9.0 Hz, 1 H), 7.46-7.39 (m, 2 H), 7.10 (ddd, J = 7.0, 7.0, 1.5 Hz, 1 H), 7.02 (d, J = 9.1 Hz, 1 H), 4.76 (s, 2H), 3.04 (t, J = 5.1 Hz, 4 H), 2.87 (t, J = 4.8 Hz, 4 H). | C AC8 BC42 |

| # | STRUCTURE | NAME | LCMS | ¹H NMR | Method Reagent AA BB |
|---|---|---|---|---|---|
| I-64 | 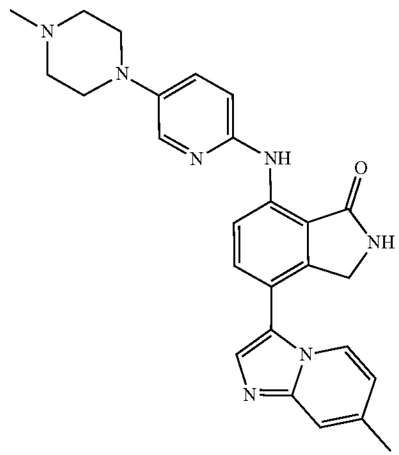 | 4-(7-methyl-imidazo[1,2-a]pyridin-3-yl)-7-[[5-(4-methylpiperazin-1-yl)-2-pyridyl]amino]isoindolin-1-one | Method AcHSS C18, m/z = 454 [M + H]+, Ret. time = 1.87 min. | ¹H NMR (400 MHz, DMSO): δ 9.85 (s, 1 H), 8.77 (s, 1 H), 8.56 (d, J = 8.5 Hz, 1 H), 8.28 (d, J = 6.9 Hz, 1 H), 8.00 (d, J = 2.7 Hz, 1 H), 7.74 (s, 1 H), 7.68 (d, J = 8.5 Hz, 1 H), 7.46 (dd, J = 2.5, 8.3 Hz, 1 H), 7.44 (s, 1 H), 6.97 (d, J = 9.2 Hz, 1 H), 6.79 (dd, J = 1.6, 7.1 Hz, 1 H), 4.38 (s, 2 H), 3.13 (t, J = 4.7 Hz, 4 H), 2.48 (t, J = 4.9 Hz, 4 H), 2.40 (s, 3 H), 2.24 (s, 3 H). | F AC9 BC45 |
| I-65 | 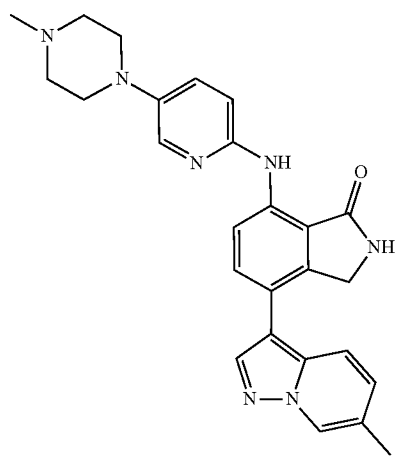 | 7-[[5-(4-methylpiperazin-1-yl)-2-pyridyl]amino]-4-(6-methylpyrazolo[1,5-a]pyridin-3-yl)isoindolin-1-one | Method AcHSS C18, m/z = 454 [M + H]+, Ret. time = 2.75 min. | ¹H NMR (400 MHz, DMSO) δ 9.80 (s, 1 H), 8.76 (s, 1 H), 8.60-8.58 (m, 1 H), 8.52-8.49 (m, 1 H), 8.25 (s, 1 H), 8.00 (d, J = 2.9 Hz, 1 H), 7.78-7.74 (m, 1 H), 7.68-7.65 (m, 1 H), 7.45 (dd, J = 3.0, 8.9 Hz, 1 H), 7.18 (dd, J = 1.3, 9.2 Hz, 1 H), 6.96-6.92 (m, 1 H), 4.52-4.49 (m, 2 H), 3.13 (s, 4 H), 2.61 (s, 4 H), 2.34 (d, J = 0.7 Hz, 3 H), 2.31 (s, 3 H). | F AC9 BC46 |

| # | STRUCTURE | NAME | LCMS | ¹H NMR | Method Reagent AA BB |
|---|---|---|---|---|---|
| I-66 | 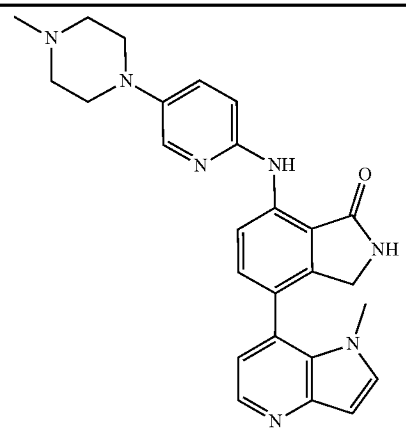 | 7-[[5-(4-methylpiperazin-1-yl)-2-pyridyl]amino]-4-(1-methylpyrrolo[3,2-b]pyridin-7-yl)isoindolin-1-one | Method AcHSS C18, m/z = 454 [M + H]+, Ret. time = 1.76 min. | ¹H NMR (400 MHz, DMSO): δ 9.80 (s, 1 H), 8.70 (s, 1 H), 8.53-8.50 (m, 1 H), 8.36-8.34 (m, 1H), 8.01 (d, J = 3.0 Hz, 1 H), 7.61-7.59 (1H, m), 7.51-7.43 (m, 2 H), 7.07 (d, J = 4.6 Hz, 1 H), 6.98-6.95 (m, 1 H), 6.64 (d, J = 3.3 Hz, 1 H), 4.32 (d, J = 17.7 Hz, 1 H), 4.05 (d, J = 17.9 Hz, 1 H), 3.35 (s, 3H), 3.12 (t, J = 4.9 Hz, 4H), 2.48 (d, J = 5.1 Hz, 4H), 2.25 (s, 3H). | F AC9 BC47 |
| I-67 | 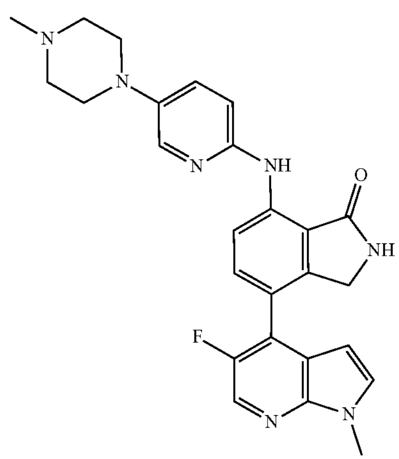 [SMILES: CN1CCN(c2ccc(Nc3ccc(-c4c(F)cnc5c4ccn5C)c4c3C(=O)NC4)nc2)CC1] | 4-(5-fluoro-1-methyl-pyrrolo[2,3-b]pyridin-4-yl)-7-[[5-(4-methylpiperazin-1-yl)-2-pyridyl]amino]isoindolin-1-one | Method AcHSS C18, m/z = 472 [M + H]+, Ret. time = 2.87 min. | ¹H NMR (400 MHz, DMSO): δ 9.95 (s, 1 H), 8.75 (s, 1 H), 8.58 (d, J = 8.8 Hz, 1 H), 8.41 (d, J = 3.3 Hz, 1 H), 8.20 (s, 1 H), 8.06 (d, J = 2.6 Hz, 1 H), 7.70 (d, J = 3.3 Hz, 1 H), 7.67 (d, J = 8.2 Hz, 1 H), 7.50 (dd, J = 3.0, 9.1 Hz, 1 H), 7.03 (d, J = 9.0 Hz, 1 H), 6.38 (d, J = 3.6 Hz, 1H), 4.27 (s, 2 H), 3.91 (s, 3 H), 3.17 (t, J = 5.1 Hz, 4 H), 2.63 (s, 4 H), 2.31 (s, 3 H). | D AC9 BC48 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-68 | 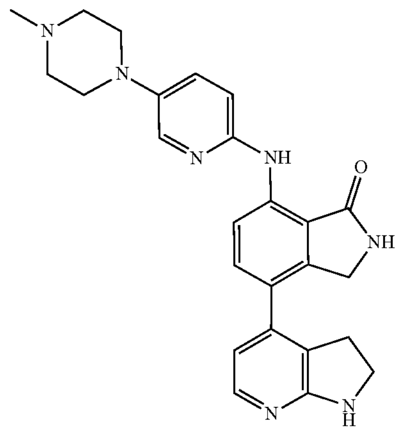 [SMILES: CN1CCN(c2ccc(Nc3ccc(-c4ccnc5c4CCN5)c4c3C(=O)NC4)nc2)CC1] | 4-(2,3-dihydro-1H-pyrrolo[2,3-b]pyridin-4-yl)-7-[[5-(4-methylpiperazin-1-yl)-2-pyridyl]amino]isoindolin-1-one | Method AcHSS C18, m/z = 442 [M + H]+, Ret. time = 1.82 min. | ¹H NMR (400 MHz, DMSO) δ 9.88-9.87 (m, 1 H), 8.73 (s, 1 H), 8.48-8.45 (m, 1 H), 8.15 (s, 0.4 H), 8.02-8.00 (m, 1 H), 7.74 (d, J = 5.5 Hz, 1 H), 7.53-7.44 (m, 2 H), 6.97-6.94 (m, 1 H), 6.60-6.58 (m, 1 H), 6.44 (s, 1 H), 4.41-4.39 (m, 2 H), 3.49-3.42 (m, 2 H), 3.18-3.14 (m, 4 H), 3.03-2.96 (m, 2 H), 2.73 (s, 4 H), 2.42 (s, 3 H). | F AC9 BC49 |
| I-69 | 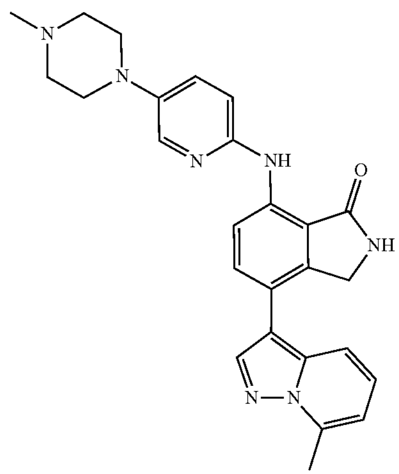 [SMILES: Cc1cccc2c(-c3ccc(Nc4ccc(N5CCN(C)CC5)cn4)c4c3CNC4=O)cnn12] | 7-[[5-(4-methylpiperazin-1-yl)-2-pyridyl]amino]-4-(7-methylpyrazolo[1,5-a]pyridin-3-yl)isoindolin-1-one | Method AcHSS C18, m/z = 454 [M + H]+, Ret. time = 2.79 min. | ¹H NMR (400 MHz, DMSO) δ 9.79 (s, 1 H), 8.77-8.75 (m, 1 H), 8.52-8.49 (m, 1 H), 8.38-8.37 (m, 1 H), 7.99 (d, J = 3.0 Hz, 1 H), 7.76-7.65 (m, 2 H), 7.44 (dd, J = 3.0, 8.9 Hz, 1 H), 7.27 (dd, J = 6.8, 8.9 Hz, 1 H), 6.96-6.90 (m, 2 H), 4.52-4.50 (m, 2 H), 3.12 (t, J = 4.7 Hz, 4 H), 2.73 (s, 3 H), 2.54-2.50 (m, 4 H), 2.27 (s, 3 H). | F AC9 BC50 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-70 | 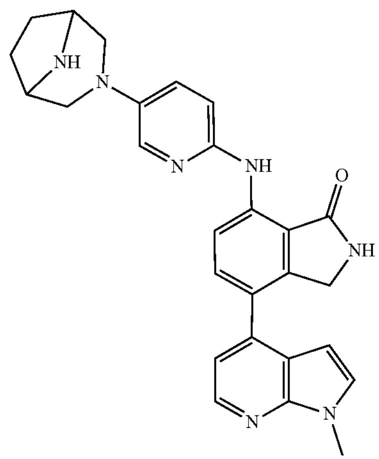 [SMILES: Cn1ccc2c(-c3ccc(Nc4ccc(N5CC6CCC(C5)N6)cn4)c4c3CNC4=O)ccnc21] | 7-[[5-(3,8-diaza-bicyclo[3.2.1]octan-3-yl)-2-pyridyl]amino]-4-(1-methylpyrrolo[2,3-b]pyridin-4-yl)isoindolin-1-one | Method AcHSS C18, m/z = 466 [M + H]+, Ret. time = 2.61 min. | ¹H NMR (400 MHz, DMSO): δ 9.89 (s, 1 H), 8.77 (s, 1 H), 8.53 (d, J = 9.5 Hz, 1 H), 8.36 (d, J = 5.2 Hz, 1 H), 7.93 (d, J = 3.9 Hz, 1 H), 7.75 (d, J = 9.2 Hz, 1 H), 7.62 (d, J = 3.6 Hz, 1 H), 7.37 (dd, J = 3.1, 9.0 Hz, 1 H), 7.29 (d, J = 5.6 Hz, 1 H), 6.99 (d, J = 9.2 Hz, 1 H), 6.51 (d, J = 3.8 Hz, 1 H), 4.49 (s, 2 H), 3.92 (s, 3 H), 3.59 (s, 2 H), 3.43 (d, J = 12.9 Hz, 2 H), 2.82 (d, J = 10.3 Hz, 2 H), 1.83-1.74 (m, 4 H). | E AC14 BC26 |
| I-71 | 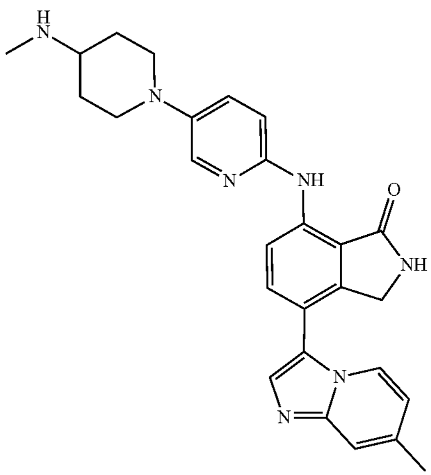 | 7-[[5-[4-(methylamino)-1-piperidyl]-2-pyridyl]amino]-4-(7-methylimidazo[1,2-a]pyridin-3-yl)isoindolin-1-one | Method AcHSS C18, m/z = 468 [M + H]+, Ret. time = 1.89 min. | ¹H NMR (400 MHz, DMSO): δ 9.83 (s, 1 H), 8.77 (s, 1 H), 8.55 (d, J = 8.6 Hz, 1 H), 8.28 (d, J = 7.1 Hz, 1 H), 8.00 (d, J = 3.2 Hz, 1 H), 7.74 (s, 1 H), 7.67 (d, J = 8.5 Hz, 1 H), 7.46-7.42 (m, 2 H), 6.95 (d, J = 9.4 Hz, 1 H), 6.79 (dd, J = 1.8, 7.2 Hz, 1 H), 4.39 (s, 2 H), 3.55 (ddd, J = 3.8, 3.8, 12.8 Hz, 2 H), 2.73 (ddd, J = 11.7, 11.7, 2.3 Hz, 2 H), 2.44-2.41 (m, 1 H), 2.40 (s, 3 H), 1.91 (dd, J = 3.4, 12.4 Hz, 2 H), 1.43-1.32 (m, 2 H). | F AC13 BC4 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-72 | 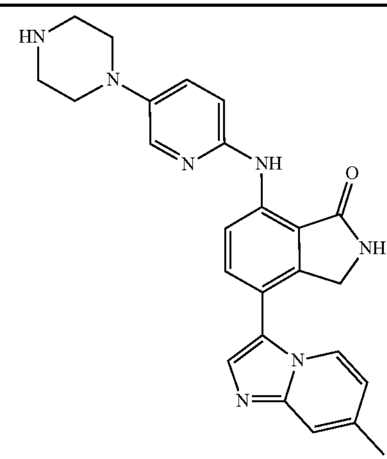 | 4-(7-methylimidazo[1,2-a]pyridin-3-yl)-7-[(5-piperazin-1-yl-2-pyridyl)amino]isoindolin-1-one | Method AcHSS C18, m/z = 440 [M + H]+, Ret. time = 1.83 min. | ¹H NMR (400 MHz, DMSO): δ 9.84 (s, 1 H), 8.77 (s, 1 H), 8.56 (d, J = 8.6 Hz, 1 H), 8.28 (d, J = 6.7 Hz, 1 H), 7.99 (d, J = 3.2 Hz, 1 H), 7.74 (s, 1 H), 7.68 (d, J = 9.1 Hz, 1 H), 7.45-7.41 (m, 2 H), 6.96 (d, J = 8.9 Hz, 1 H), 6.79 (dd, J = 1.9, 7.1 Hz, 1 H), 4.39 (s, 2 H), 3.03 (t, J = 5.1 Hz, 4 H), 2.86 (t, J = 5.0 Hz, 4 H), 2.40 (s, 3 H). | F AC8 BC4 |
| I-73 | 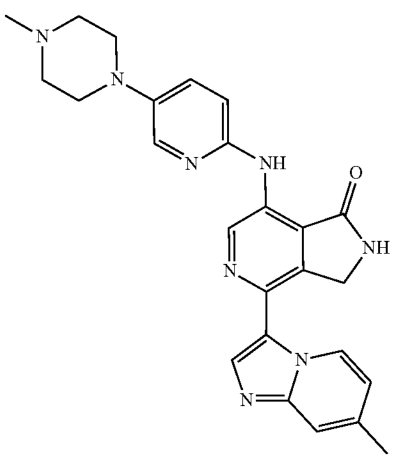 | 4-(7-methylimidazo[1,2-a]pyridin-3-yl)-7-[[5-(4-methylpiperazin-1-yl)-2-pyridyl]amino]-2,3-dihydropyrrolo[3,4-c]pyridin-1-one | Method AcHSS C18, m/z = 455 [M + H]+, Ret. time = 1.95 min. | ¹H NMR (400 MHz, DMSO) 9.90 (1H, s), 9.78 (1H, d, J = 7.1 Hz), 9.45 (1H, s), 9.28 (1H, s), 8.15 (1H, s), 8.09 (1H, d, J = 3.0 Hz), 8.01 (1H, s), 7.55-7.51 (2H, m), 7.09 (1H, d, J = 8.9 Hz), 6.96 (1H, dd, J = 1.9, 7.4 Hz), 4.74 (2H, s), 3.40 (4H, s), 3.28 (4H, s), 2.81 (3H, s), 2.43 (3H, s). | F AC9 BC4 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-74 | 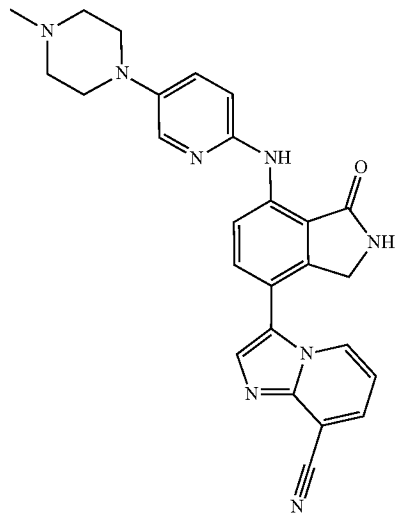 [SMILES: CN1CCN(c2ccc(Nc3ccc(-c4cnc5c(C#N)cccn45)c4c3C(=O)NC4)nc2)CC1] | 3-[7-[[5-(4-methylpiperazin-1-yl)-2-pyridyl]amino]-1-oxo-isoindolin-4-yl]imidazo[1,2-a]pyridine-8-carbonitrile | Method AcHSS C18, m/z = 465 [M + H]+, Ret. time = 2.34 min. | ¹H NMR (400 MHz, DMSO): δ 9.93 (s, 1 H), 8.83 (s, 1 H), 8.72 (dd, J = 1.0, 7.1 Hz, 1 H), 8.62 (d, J = 8.6 Hz, 1 H), 8.09-8.05 (m, 2 H), 8.05 (s, 1 H), 7.76 (d, J = 8.6 Hz, 1 H), 7.51 (dd, J = 3.2, 9.1 Hz, 1 H), 7.13 (t, J = 6.5 Hz, 1 H), 7.04 (d, J = 10.5 Hz, 1 H), 4.44 (s, 2 H), 3.24 (s, 4 H), 2.70 (s, 4 H), 2.42 (s, 3 H). | F AC9 BC51 |

| # | STRUCTURE | NAME | LCMS | ¹H NMR | Method Reagent AA BB |
|---|---|---|---|---|---|
| I-75 | 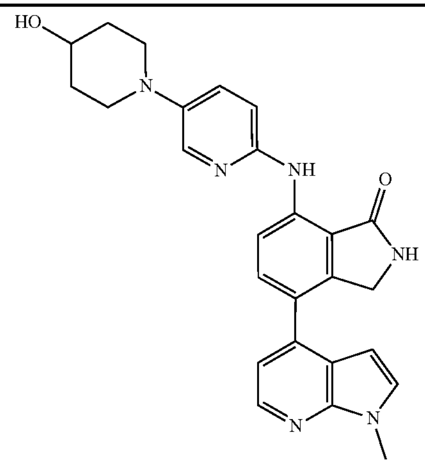 | 7-[[5-(4-hydroxy-1-piperidyl)-2-pyridyl]amino]-4-(1-methylpyrrolo[2,3-b]pyridin-4-yl)isoindolin-1-one | Method AcHSS C18, m/z = 455 [M + H]+, Ret. time = 2.79 min. | ¹H NMR (400 MHz, DMSO): δ 9.95 (s, 1 H), 8.79 (s, 1 H), 8.58 (d, J = 6.8 Hz, 1 H), 8.35 (d, J = 5.4 Hz, 1 H), 8.06 (d, J = 2.3 Hz, 1 H), 7.76 (d, J = 9.5 Hz, 1 H), 7.62 (d, J = 3.6 Hz, 1 H), 7.49 (dd, J = 2.9, 9.1 Hz, 1 H), 7.30 (d, J = 4.6 Hz, 1 H), 7.00 (d, J = 9.2 Hz, 1 H), 6.51 (d, J = 3.6 Hz, 1 H), 4.73 (d, J = 4.2 Hz, 1 H), 4.50 (s, 2 H), 3.92 (s, 3 H), 3.70-3.64 (m, 1 H), 3.54-3.47 (m, 2 H), 2.87 (ddd, J = 2.5, 10.3, 12.3 Hz, 2 H), 1.89 (dd, J = 3.9, 12.8 Hz, 2 H), 1.62-1.52 (m, 2 H). | E AC15 BC26 |
| I-76 | 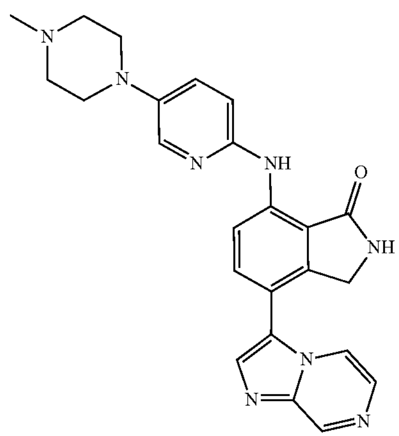 | 4-imidazo[1,2-a]pyrazin-3-yl-7-[[5-(4-methylpiperazin-1-yl)-2-pyridyl]amino]isoindolin-1-one | Method AcHSS C18, m/z = 441 [M + H]+, Ret. time = 2.04 min. | ¹H NMR (400 MHz, DMSO): δ 9.88 (s, 1 H), 9.15 (d, J = 1.5 Hz, 1 H), 8.81 (s, 1 H), 8.59 (d, J = 8.6 Hz, 1 H), 8.47 (dd, J = 1.6, 4.8 Hz, 1 H), 8.12 (s, 1 H), 8.02 (d, J = 3.4 Hz, 1 H), 7.92 (d, J = 5.0 Hz, 1 H), 7.77 (d, J = 8.4 Hz, 1 H), 7.46 (dd, J = 3.2, 9.0 Hz, 1 H), 6.98 (d, J = 9.0 Hz, 1 H), 4.45 (s, 2H), 3.14 (t, J = 5.0 Hz, 5 H), 2.49 (t, J = 4.6 Hz, 4 H), 2.25 (s, 3 H). | F AC9 BC52 |

TABLE 8-continued

Characterization Data (LCMS and ¹H NMR).

| # | STRUCTURE | NAME | LCMS | ¹H NMR | Method AA Reagent BB |
|---|---|---|---|---|---|
| I-77 | (structure) | 7-[[5-(4-methylpiperazin-1-yl)-2-pyridyl]amino]-4-(6-methyl-1H-pyrrolo[2,3-b]pyridin-4-yl)isoindolin-1-one | Method AcHSS C18, m/z = 454 [M + H]+, Ret. time = 2.04 min. | ¹H NMR (400 MHz, DMSO) 11.56 (1H, s), 9.94 (1H, s), 8.76 (1H, s), 8.54 (1H, d, J = 8.9 Hz), 8.04 (1H, d, J = 2.9 Hz), 7.71 (1H, d, J = 8.6 Hz), 7.47 (1H, dd, J = 3.1, 8.9 Hz), 7.41 (1H, dd, J = 2.5, 3.4 Hz), 7.10 (1H, s), 6.99 (1H, d, J = 8.9 Hz), 6.37 (1H, ddd, J = 1.8, 1.8, 1.8 Hz), 4.46 (2H, s), 3.20 (4H, s), 2.78 (4H, s), 2.57 (3H, s), 2.47 (3H, s) | F AC9 BC53 |
| I-78 | (structure) | 7-[[5-(4-methylpiperazin-1-yl)-2-pyridyl]amino]-4-(5-methyl-1H-pyrrolo[2,3-b]pyridin-4-yl)isoindolin-1-one | Method AcHSS C18, m/z = 454 [M + H]+, Ret. time = 2.12 min. | ¹H NMR (400 MHz, DMSO): δ 11.62 (s, 1 H), 9.81 (s, 1 H), 8.62 (s, 1 H), 8.51 (d, J = 8.7 Hz, 1 H), 8.19 (s, 1 H), 8.02 (d, J = 2.9 Hz, 1 H), 7.47 (dd, J = 3.2, 8.9 Hz, 1 H), 7.43–7.40 (m, 2 H), 6.99 (d, J = 9.3 Hz, 1 H), 5.99 (dd, J = 1.9, 3.5 Hz, 1 H), 4.06 (d, J = 18.1 Hz, 1 H), 3.96 (d, J = 18.2 Hz, 1 H), 3.22 (s, 4 H), 2.75 (s, 4 H), 2.45 (s, 3 H), 2.19 (s, 3 H). | F AC9 BC54 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-79 | 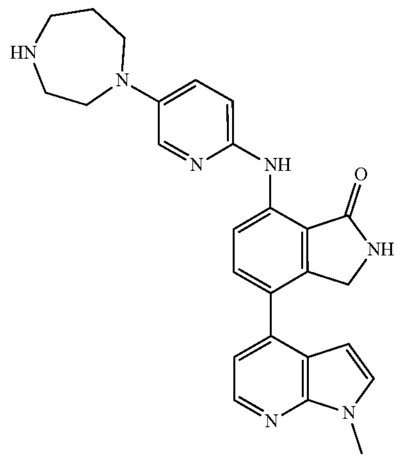 [SMILES: Cn1ccc2c(-c3ccc(Nc4ccc(N5CCCNCC5)cn4)c4c3CNC4=O)ccnc21] | 7-[[5-(1,4-diazepan-1-yl)-2-pyridyl]amino]-4-(1-methylpyrrolo[2,3-b]pyridin-4-yl)isoindolin-1-one | Method AcHSS C18, m/z = 454 [M + H]+, Ret. time = 2.46 min. | ¹H NMR (400 MHz, DMSO) 9.78 (1H, s), 8.72 (1H, s), 8.47 (1H, d, J = 7.2 Hz), 8.35 (1H, d, J = 5.1 Hz), 7.90 (1H, s), 7.74 (1H, d, J = 9.1 Hz), 7.62 (1H, d, J = 3.9 Hz), 7.30 (1H, d, J = 5.1 Hz), 7.25 (1H, dd, J = 3.0, 9.4 Hz), 6.98 (1H, d, J = 8.2 Hz), 6.51 (1H, d, J = 3.9 Hz), 4.50 (2H, s), 3.91 (3H, s), 3.60 (2H, t, J = 5.6 Hz), 3.52 (2H, t, J = 5.3 Hz), 2.92 (2H, t, J = 5.4 Hz), 2.71 (2H, t, J = 5.7 Hz), 1.85 (2H, tt, J = 5.8, 6.0 Hz) | E AC16 BC26 |
| I-80 | 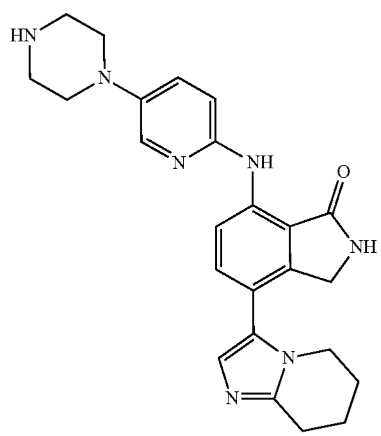 [SMILES: O=C1NCc2c(-c3cnc4n3CCCC4)ccc(Nc3ccc(N4CCNCC4)cn3)c21] | 7-[(5-piperazin-1-yl-2-pyridyl)amino]-4-(5,6,7,8-tetrahydroimidazo[1,2-a]pyridin-3-yl)isoindolin-1-one | Method AcHSS C18, m/z = 430 [M + H]+, Ret. time = 1.74 min. | ¹H NMR (400 MHz, DMSO): δ 9.76 (s, 1 H), 8.72 (s, 1 H), 8.46 (d, J = 8.8 Hz, 1 H), 7.96 (d, J = 2.9 Hz, 1 H), 7.49 (d, J = 8.6 Hz, 1 H), 7.41 (dd, J = 3.2, 8.6 Hz, 1 H), 7.04 (s, 1 H), 6.93 (d, J = 8.9 Hz, 1 H), 4.38 (s, 2 H), 3.88 (s, 2 H), 3.01 (t, J = 5.0 Hz, 4 H), 2.85 (t, J = 4.9 Hz, 4 H), 2.81 (s, 2 H), 1.88 (s, 4 H). | D AC9 BC55 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-81 | 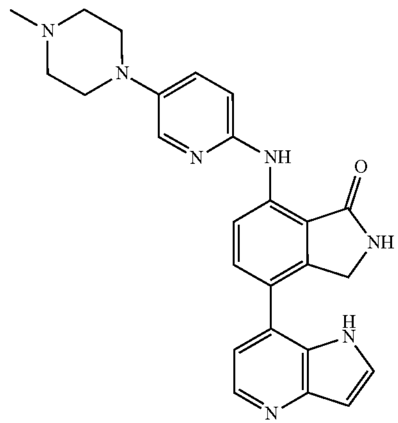 [SMILES: CN1CCN(c2ccc(Nc3ccc(-c4ccnc5cc[nH]c45)c4c3C(=O)NC4)nc2)CC1] | 7-[[5-(4-methylpiperazin-1-yl)-2-pyridyl]amino]-4-(1H-pyrrolo[3,2-b]pyridin-7-yl)isoindolin-1-one | Method AcHSS C18, m/z = 440 [M + H]+, Ret. time = 1.79 min. | ¹H NMR (400 MHz, DMSO) δ 11.28-11.25 (m, 1 H), 9.93-9.91 (m, 1 H), 8.75-8.73 (m, 1 H), 8.60-8.57 (m, 1 H), 8.38-8.37 (m, 1 H), 8.03-8.01 (m, 1 H), 7.67 (d, J = 8.5 Hz, 1 H), 7.61 (t, J = 3.0 Hz, 1 H), 7.48-7.44 (m, 1 H), 7.19 (d, J = 4.8 Hz, 1 H), 6.99-6.96 (m, 1 H), 6.65 (dd, J = 1.8, 3.1 Hz, 1 H), 4.36-4.34 (m, 2 H), 3.16-3.10 (m, 4 H), 2.54-2.50 (m, 4 H), 2.27 (s, 3 H). | F AC9 BC56 |
| I-82 | 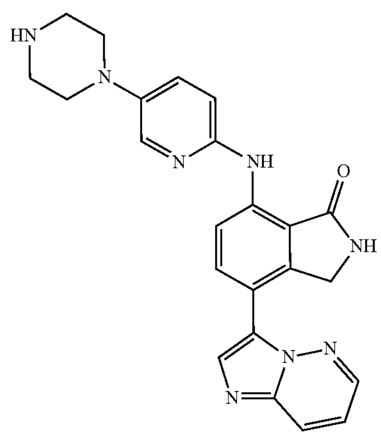 | 4-imidazo[1,2-b]pyridazin-3-yl-7-[(5-piperazin-1-yl-2-pyridyl)amino]isoindolin-1-one | Method AcHSS C18, m/z = 427 [M + H]+, Ret. time = 1.99 min. | ¹H NMR (400 MHz, DMSO): δ 9.90 (s, 1 H), 8.81 (s, 1 H), 8.62 (dd, J = 1.8, 4.4 Hz, 1 H), 8.51 (d, J = 9.0 Hz, 1 H), 8.23 (dd, J = 1.4, 9.1 Hz, 1H), 8.12 (d, J = 8.6 Hz, 1H), 8.10 (s, 1 H), 8.00 (d, J = 3.2 Hz, 1 H), 7.43 (dd, J = 2.9, 8.9 Hz, 1 H), 7.30 (dd, J = 4.3, 9.1 Hz, 1 H), 6.97 (d, J = 9.2 Hz, 1H), 4.54 (s, 2 H), 3.03 (t, J = 4.9 Hz, 4 H), 2.87 (t, J = 4.7 Hz, 4 H). | F AC9 BC57 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-83 | 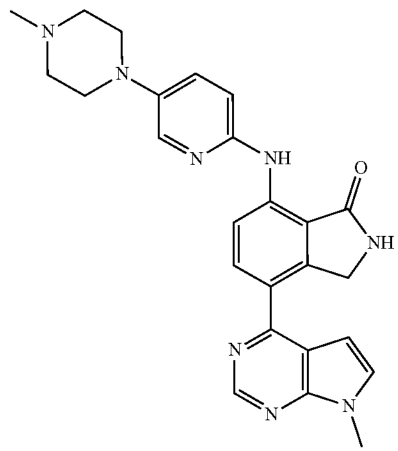 [SMILES: CN1CCN(c2ccc(Nc3ccc(-c4ncnc5c4ccn5C)c4c3C(=O)NC4)nc2)CC1] | 7-[[5-(4-methylpiperazin-1-yl)-2-pyridyl]amino]-4-(7-methylpyrrolo[2,3-d]pyrimidin-4-yl)isoindolin-1-one | Method AcHSS C18, m/z = 455 [M + H]+, Ret. time = 2.46 min. | ¹H NMR (400 MHz, DMSO) δ 10.13 (s, 1 H), 8.85-8.82 (m, 2 H), 8.59 (d, J = 8.8 Hz, 1 H), 8.32-8.27 (m, 1 H), 8.03 (d, J = 2.9 Hz, 1 H), 7.69 (d, J = 3.6 Hz, 1H), 7.47 (dd, J = 3.1, 9.0 Hz, 1 H), 7.01-6.98 (m, 2 H), 4.83 (s, 2 H), 3.88 (s, 3H), 3.14 (dd, J = 4.9, 4.9 Hz, 4 H), 2.53-2.46 (m, 4 H), 2.25 (s, 3 H). | F AC9 BC57 |
| I-84 | 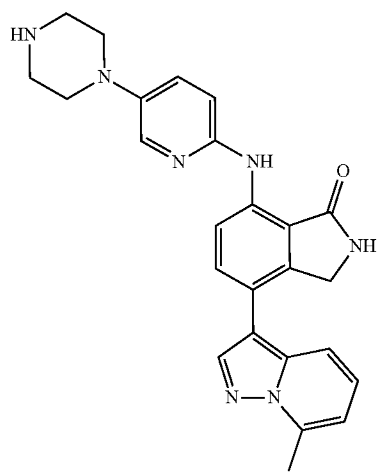 [SMILES: Cc1cccc2c(-c3ccc(Nc4ccc(N5CCNCC5)cn4)c4c3CNC4=O)cnn12] | 4-(7-methylpyrazolo[1,5-a]pyridin-3-yl)-7-[(5-piperazin-1-yl-2-pyridyl)amino]isoindolin-1-one | Method AcHSS C18, m/z = 440 [M + H]+, Ret. time = 2.73 min. | ¹H NMR (400 MHz, DMSO): δ 9.78 (s, 1 H), 8.76 (s, 1H), 8.51 (d, J = 8.5 Hz, 1 H), 8.37 (s, 1 H), 7.98 (d, J = 2.8 Hz, 1 H), 7.74 (d, J = 9.1 Hz, 1 H), 7.66 (d, J = 8.8 Hz, 1 H), 7.42 (dd, J = 2.8, 9.1 Hz, 1 H), 7.27 (dd, J = 6.8, 9.1 Hz, 1 H), 6.95-6.90 (m, 2 H), 4.51 (s, 2 H), 3.02 (t, J = 5.2 Hz, 4H), 2.88 (t, J = 5.0 Hz, 4 H), 2.73 (s, 3 H). | F AC8 BC50 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-85 | 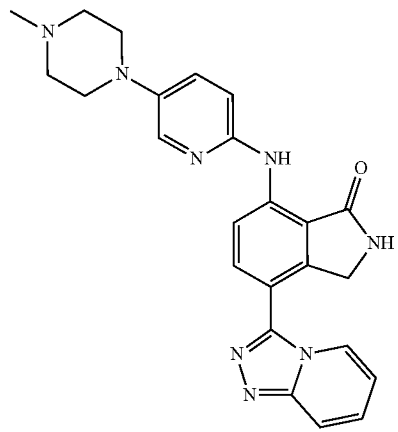 [SMILES: CN1CCN(c2ccc(Nc3ccc(-c4nnc5ccccn45)c4c3C(=O)NC4)nc2)CC1] | 7-[[5-(4-methylpiperazin-1-yl)-2-pyridyl]amino]-4-([1,2,4]triazolo[4,3-a]pyridin-3-yl)isoindolin-1-one | Method AcHSS C18, m/z = 441 [M + H]+, Ret. time = 2.09 min. | ¹H NMR (400 MHz, DMSO): δ 9.95 (s, 1 H), 8.82 (s, 1 H), 8.63-8.59 (m, 2 H), 8.03 (d, J = 3.3 Hz, 1 H), 7.98 (d, J = 8.5 Hz, 1 H), 7.87 (dd, J = 1.1, 9.2 Hz, 1 H), 7.48-7.42 (m, 2 H), 7.04 (ddd, J = 6.8, 6.8, 1.1 Hz, 1 H), 7.00 (d, J = 8.9 Hz, 1 H), 4.57 (s, 2 H), 3.13 (t, J = 5.2 Hz, 4 H), 2.49 (t, J = 5.6 Hz, 4 H), 2.25 (s, 3 H). | F AC9 BC58 |
| I-86 | 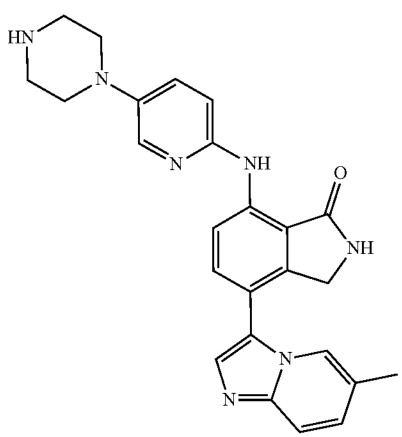 [SMILES: Cc1ccc2ncc(-c3ccc(Nc4ccc(N5CCNCC5)cn4)c4c3CNC4=O)n2c1] | 4-(6-methylimidazo[1,2-a]pyridin-3-yl)-7-[(5-piperazin-1-yl-2-pyridyl)amino]isoindolin-1-one | Method AcHSS C18, m/z = 440 [M + H]+, Ret. time = 1.83 min. | ¹H NMR (400 MHz, DMSO): δ 9.85 (s, 1 H), 8.75 (s, 1 H), 8.58 (d, J = 8.5 Hz, 1 H), 8.17 (s, 1 H), 7.99 (d, J = 3.7 Hz, 1 H), 7.76 (s, 1 H), 7.69 (d, J = 9.1 Hz, 1 H), 7.57 (d, J = 10.1 Hz, 1 H), 7.43 (dd, J = 3.0, 8.9 Hz, 1 H), 7.17 (dd, J = 1.5, 9.2 Hz, 1 H), 6.97 (d, J = 9.1 Hz, 1 H), 4.37 (s, 2 H), 3.19 (d, J = 4.5 Hz, 1 H), 3.03 (t, J = 4.8 Hz, 4 H), 2.87 (t, J = 4.9 Hz, 4 H), 2.30 (s, 3 H). | F AC8 BC40 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-87 | 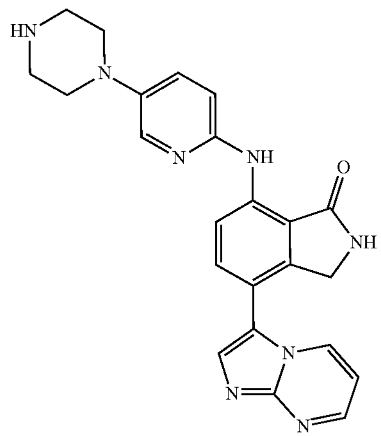 [SMILES: O=C1NCc2c(-c3cnc4ncccn34)ccc(Nc3ccc(N4CCNCC4)cn3)c21] | 4-imidazo[1,2-a]pyrimidin-3-yl-7-[(5-piperazin-1-yl-2-pyridyl)amino]isoindolin-1-one | Method AcHSS C18, m/z = 427 [M + H]+, Ret. time = 1.69 min. | ¹H NMR (400 MHz, DMSO): δ 9.90 (s, 1 H), 8.89 (dd, J = 1.9, 7.0 Hz, 1 H), 8.82 (s, 1 H), 8.64 (dd, J = 2.2, 4.2 Hz, 1 H), 8.61 (d, J = 8.6 Hz, 1 H), 8.05 (s, 1 H), 8.04 (d, J = 2.8 Hz, 1 H), 7.77 (d, J = 8.8 Hz, 1 H), 7.48 (dd, J = 3.0, 9.1 Hz, 1 H), 7.13 (dd, J = 3.9, 6.6 Hz, 1 H), 7.01 (d, J = 9.1 Hz, 1 H), 4.46 (s, 2 H), 3.08 (t, J = 5.0 Hz, 4 H), 2.93 (t, J = 4.7 Hz, 4 H). | F AC8 BB59 |
| I-88 | 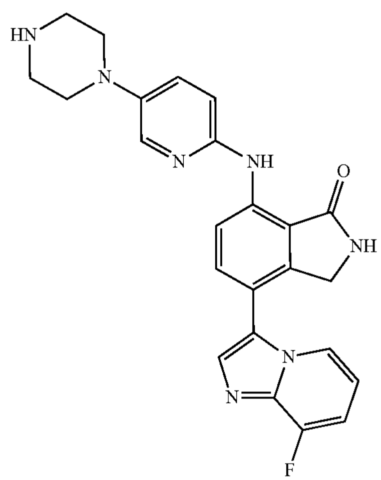 [SMILES: O=C1NCc2c(-c3cnc4c(F)cccn34)ccc(Nc3ccc(N4CCNCC4)cn3)c21] | 4-(8-fluoroimidazo[1,2-a]pyridin-3-yl)-7-[(5-piperazin-1-yl-2-pyridyl)amino]isoindolin-1-one | Method AcHSS C18, m/z = 444 [M + H]+, Ret. time = 2 min. | ¹H NMR (400 MHz, DMSO): δ 9.78 (s, 1 H), 8.69 (s, 1 H), 8.49 (d, J = 8.6 Hz, 1 H), 8.15 (d, J = 6.6 Hz, 1 H), 7.91 (d, J = 3.3 Hz, 1 H), 7.81 (s, 1H), 7.62 (d, J = 8.9 Hz, 1 H), 7.35 (dd, J = 2.4, 8.7 Hz, 1 H), 7.13 (dd, J = 7.5, 11.2 Hz, 1 H), 6.89 (d, J = 9.1 Hz, 1 H), 6.84 (ddd, J = 7.0, 7.0, 4.8 Hz, 1 H), 4.31 (s, 2 H), 2.95 (t, J = 4.8 Hz, 4 H), 2.79 (t, J = 5.1 Hz, 4 H). | F AC1 BC60 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-89 | 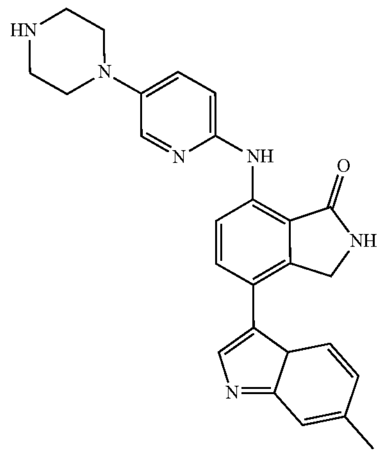 [SMILES: CC1=CC2=NC=C(c3ccc(Nc4ccc(N5CCNCC5)cn4)c4c3CNC4=O)C2C=C1] | 4-(6-methylpyrazolo[1,5-a]pyridin-3-yl)-7-[[5-(piperazin-1-yl)-2-pyridyl]amino]isoindolin-1-one | Method AcHSS C18, m/z = 440 [M + H]+, Ret. time = 2.69 min. | ¹H NMR (400 MHz, DMSO): δ 9.77 (s, 1 H), 8.76 (s, 1 H), 8.59 (s, 1 H), 8.50 (d, J = 8.7 Hz, 1 H), 8.25 (s, 1 H), 7.97 (d, J = 3.4 Hz, 1 H), 7.76 (d, J = 9.6 Hz, 1 H), 7.66 (d, J = 9.0 Hz, 1 H), 7.41 (dd, J = 3.0, 9.1 Hz, 1 H), 7.18 (dd, J = 1.2, 9.4 Hz, 1 H), 6.93 (d, J = 9.0 Hz, 1 H), 4.50 (s, 2H), 3.19 (d, J = 3.2 Hz, 1 H), 3.02 (t, J = 4.7 Hz, 4 H), 2.87 (t, J = 5.0 Hz, 4 H). | F AC8 BC46 |
| I-90 | 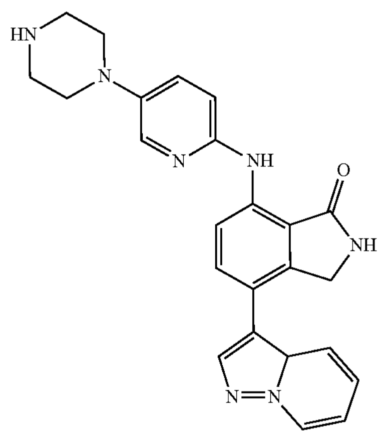 | 7-[[5-piperazin-1-yl-2-pyridyl]amino]-4-pyrazolo[1,5-a]pyridin-3-yl-isoindolin-1-one | Method AcHSS C18, m/z = 426 [M + H]+, Ret. time = 2.47 min. | ¹H NMR (400 MHz, DMSO): δ 9.79 (s, 1 H), 8.76-8.74 (m, 2 H), 8.51 (d, J = 8.6 Hz, 1 H), 8.34 (s, 1 H), 7.97 (d, J = 2.7 Hz, 1 H), 7.83 (td, J = 1.1, 9.1 Hz, 1 H), 7.67 (d, J = 8.5 Hz, 1 H), 7.42 (dd, J = 3.2, 8.9 Hz, 1 H), 7.31 (ddd, J = 1.2, 6.8, 9.1 Hz, 1 H), 6.97 (ddd, J = 6.9, 6.9, 1.2 Hz, 1 H), 6.93 (d, J = 8.9 Hz, 1 H), 4.51 (s, 2 H), 3.03 (t, J = 4.9 Hz, 4 H), 2.88 (t, J = 4.8 Hz, 4 H). | F AC8 BC61 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-91 | 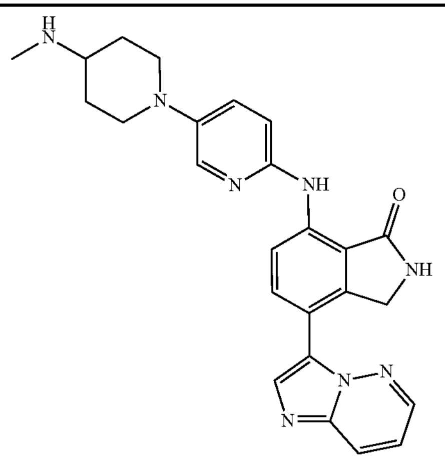 | 4-imidazo[1,2-b]pyridazin-3-yl-7-[[5-[4-(methylamino)-1-piperidyl]-2-pyridyl]amino]isoindolin-1-one | Method AcHSS C18, m/z = 455 [M + H]+, Ret. time = 2.06 min. | ¹H NMR (400 MHz, DMSO): δ 9.93 (s, 1 H), 8.85 (s, 1 H), 8.66 (dd, J = 1.7, 4.3 Hz, 1 H), 8.54 (d, J = 9.0 Hz, 1 H), 8.27 (dd, J = 1.7, 9.3 Hz, 1 H), 8.16 (d, J = 9.4 Hz, 1 H), 8.14 (s, 1 H), 8.05 (d, J = 3.1 Hz, 1 H), 7.48 (dd, J = 3.3, 9.3 Hz, 1 H), 7.34 (dd, J = 4.2, 9.3 Hz, 1 H), 7.00 (d, J = 9.3 Hz, 1 H), 4.58 (s, 2 H), 3.60 (ddd, J = 3.8, 3.8, 12.5 Hz, 2 H), 2.77 (ddd, J = 11.8, 11.8, 2.0 Hz, 2 H), 2.49 (ddd, J = 3.8, 10.5, 14.4 Hz, 1 H), 2.37 (s, 3 H), 1.95 (dd, J = 2.9, 13.3 Hz, 2 H), 1.48-1.38 (m, 2 H). | F AC13 BC43 |
| I-92 | 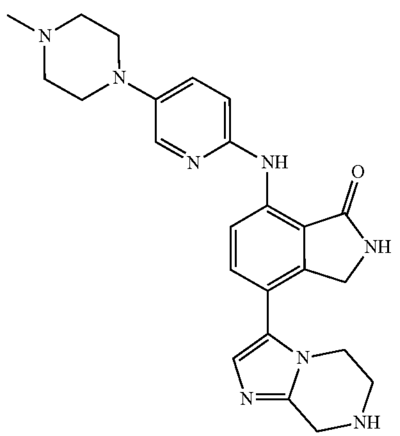 [SMILES: CN1CCN(c2ccc(Nc3ccc(-c4cnc5n4CCNC5)c4c3C(=O)NC4)nc2)CC1] | 7-[[5-(4-methylpiperazin-1-yl)-2-pyridyl]amino]-4-(5,6,7,8-tetrahydroimidazo[1,2-a]pyrazin-3-yl)isoindolin-1-one | Method AcHSS C18, m/z = 445 [M + H]+, Ret. time = 1.48 min. | ¹H NMR (400 MHz, DMSO): δ 9.78 (s, 1 H), 8.73 (s, 1 H), 8.47 (d, J = 8.6 Hz, 1 H), 7.98 (d, J = 3.4 Hz, 1 H), 7.50 (d, J = 8.8 Hz, 1 H), 7.43 (dd, J = 3.0, 8.9 Hz, 1 H), 7.07 (s, 1 H), 6.93 (d, J = 8.8 Hz, 1 H), 4.39 (s, 2 H), 3.93 (s, 2 H), 3.84 (t, J = 5.4 Hz, 2 H), 3.11 (t, J = 4.8 Hz, 4 H), 3.03 (t, J = 5.8 Hz, 2 H), 2.76 (s, 1 H), 2.48 (t, J = 4.7 Hz, 4 H), 2.24 (s, 3 H). | F AC8 BC62 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-93 | 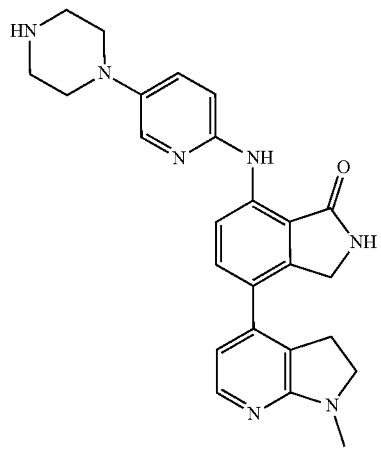 [SMILES: CN1CCc2c(-c3ccc(Nc4ccc(N5CCNCC5)cn4)c4c3CNC4=O)ccnc21] | 4-(1-methyl-2,3-dihydropyrrolo[2,3-b]pyridin-4-yl)-7-[[5-piperazin-1-yl-2-pyridyl]amino]isoindolin-1-one | Method AcHSS C18, m/z = 442 [M + H]+, Ret. time = 1.8 min. | ¹H NMR (400 MHz, DMSO) δ 9.85 (s, 1 H), 8.73 (s, 1 H), 8.46 (d, J = 8.7 Hz, 1 H), 7.97 (d, J = 3.0 Hz, 1 H), 7.83 (d, J = 5.4 Hz, 1 H), 7.50 (d, J = 8.7 Hz, 1 H), 7.41 (dd, J = 3.1, 9.0 Hz, 1 H), 6.93 (d, J = 8.9 Hz, 1 H), 6.63 (d, J = 5.5 Hz, 1 H), 4.39 (s, 2 H), 3.40 (t, J = 8.2 Hz, 2 H), 3.03-2.99 (m, 4 H), 2.94 (t, J = 8.2 Hz, 2 H), 2.87-2.83 (m, 7 H), 2.24 (s, 1 H). | H AC8 BC63 |
| I-94 | 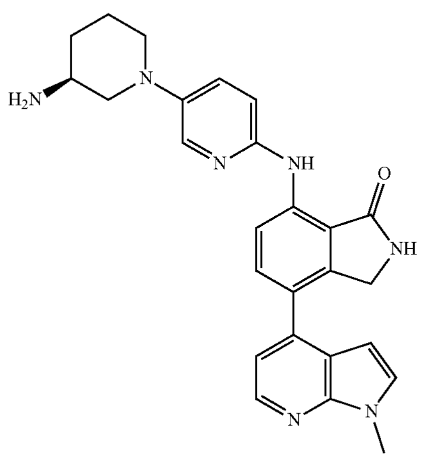 [SMILES: Cn1ccc2c(-c3ccc(Nc4ccc(N5CCC[C@H](N)C5)cn4)c4c3CNC4=O)ccnc21] | 7-[[5-[(3S)-3-amino-1-piperidyl]-2-pyridyl]amino]-4-(1-methylpyrrolo[2,3-b]pyridin-4-yl)isoindolin-1-one | Method AcHSS C18, m/z = 454 [M + H]+, Ret. time = 2.61 min. | ¹H NMR (400 MHz, DMSO) δ 9.91 (s, 1 H), 8.75 (s, 1 H), 8.53 (d, J = 8.5 Hz, 1 H), 8.31 (d, J = 4.9 Hz, 1 H), 7.99 (d, J = 2.9 Hz, 1 H), 7.72 (d, J = 8.5 Hz, 1 H), 7.58 (d, J = 3.4 Hz, 1 H), 7.42 (dd, J = 3.1, 9.0 Hz, 1 H), 7.26 (d, J = 4.9 Hz, 1 H), 6.47 (d, J = 8.8 Hz, 1 H), 4.46 (s, 2H), 3.88 (s, 3 H), 3.55-3.41 (m, 2H), 2.83-2.75 (m, 1 H), 2.67-2.58 (m, 1 H), 2.37 (dd, J = 9.4, 11.4 Hz, 1 H), 1.88-1.72 (m, 2H), 1.67-1.53 (m, 3 H), 1.18-1.07 (m, 1 H). | F AC17 BC26 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-95 | 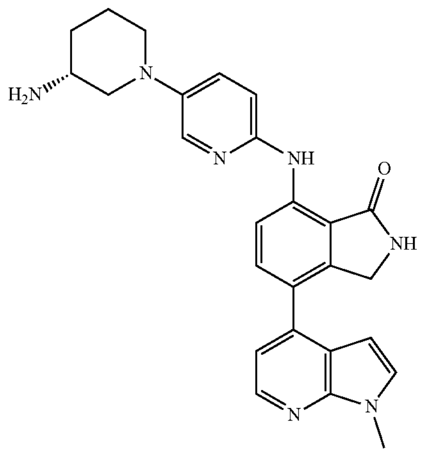 [SMILES: Cn1ccc2c(-c3ccc(Nc4ccc(N5CCC[C@@H](N)C5)cn4)c4c3CNC4=O)ccnc21] | 7-[[5-[(3R)-3-aminopiperidyl]-2-pyridyl]amino]-4-(1-methylpyrrolo[2,3-b]pyridin-4-yl)isoindolin-1-one | Method AcHSS C18, m/z = 454 [M + H]+, Ret. time = 2.61 min. | ¹H NMR (400 MHz, DMSO) δ 9.91 (s, 1 H), 8.75 (s, 1 H), 8.53 (d, J = 8.5 Hz, 1 H), 8.31 (d, J = 4.9 Hz, 1 H), 7.99 (d, J = 2.9 Hz, 1 H), 7.72 (d, J = 8.5 Hz, 1 H), 7.58 (d, J = 3.5 Hz, 1 H), 7.42 (dd, J = 3.0, 9.0 Hz, 1 H), 7.26 (d, J = 4.9 Hz, 1 H), 6.96 (d, J = 8.9 Hz, 1 H), 6.47 (d, J = 3.5 Hz, 1 H), 4.46 (s, 2H), 3.88 (s, 3 H), 3.55-3.42 (m, 2 H), 2.83-2.75 (m, 1 H), 2.66-2.58 (m, 1 H), 2.37 (dd, J = 9.4, 11.5 Hz, 1 H), 1.88-1.72 (m, 2 H), 1.64-1.53 (m, 3 H), 1.18-1.07 (m, 1 H). | E AC18 BC26 |
| I-96 | 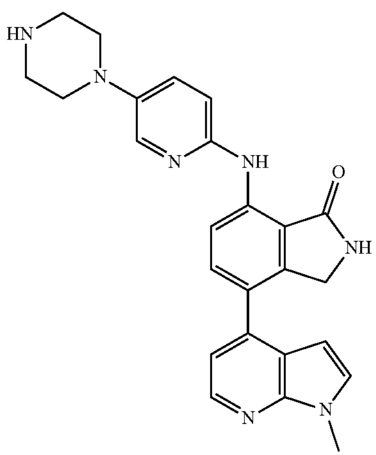 [SMILES: Cn1ccc2c(-c3ccc(Nc4ccc(N5CCNCC5)cn4)c4c3CNC4=O)ccnc21] | 4-(1-methylpyrrolo[2,3-b]pyridin-4-yl)-7-[[5-(4-piperidyl)-2-pyridyl]amino]isoindolin-1-one | Method AcHSS C18, m/z = 439.252 [M + H]+, Ret. time = 2.55 min. | ¹H NMR (400 MHz, DMSO): δ 10.15 (s, 1 H), 8.84 (s, 1 H), 8.71 (d, J = 8.7 Hz, 1 H), 8.36 (d, J = 5.8 Hz, 1 H), 8.24 (d, J = 2.9 Hz, 1 H), 7.78 (d, J = 8.7 Hz, 1 H), 7.64 (dd, J = 1.7, 8.7 Hz, 1 H), 7.62 (d, J = 3.3 Hz, 1 H), 7.30 (d, J = 5.0 Hz, 1 H), 7.02 (d, J = 8.7 Hz, 1H), 6.51 (d, J = 4.1 Hz, 1 H), 4.50 (s, 2 H), 3.91 (s, 3 H), 3.22 (d, J = 11.2 Hz, 2 H), 2.79 (t, J = 11.8 Hz, 2 H), 2.72 (s, 1 H), 1.83 (d, J = 12.4 Hz, 2 H), 1.70 (ddd, J = 12.6, 12.6, 4.1 Hz, 2 H). | E AC19 BC26 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-97 | 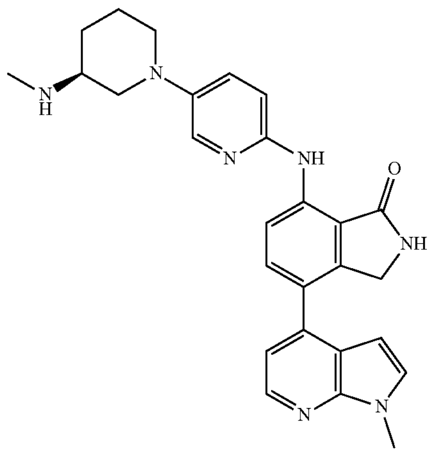 [SMILES: CN[C@H]1CCCN(c2ccc(Nc3ccc(-c4ccnc5c4ccn5C)c4c3C(=O)NC4)nc2)C1] | 7-[[5-[(3S)-3-(methylamino)-1-piperidyl]-2-pyridyl]amino]-4-(1-methylpyrrolo[2,3-b]pyridin-4-yl)isoindolin-1-one | Method AcHSS C18, m/z = 468 [M + H]+, Ret. time = 2.69 min. | ¹H NMR (400 MHz, DMSO) δ 9.91 (s, 1H), 8.76-8.74 (m, 1 H), 8.56-8.53 (m, 1 H), 8.31 (d, J = 4.9 Hz, 1 H), 8.01 (d, J = 3.0 Hz, 1 H), 7.74-7.71 (m, 1 H), 7.58 (d, J = 3.5 Hz, 1H), 7.44 (dd, J = 3.0, 9.0 Hz, 1 H), 7.26 (d, J = 4.9 Hz, 1 H), 6.98-6.94 (m, 1 H), 6.47 (d, J = 3.5 Hz, 1 H), 4.47-4.45 (m, 2 H), 3.88-3.87 (m, 3 H), 3.60 (dd, J = 3.1, 11.2 Hz, 1 H), 3.48-3.40 (m, 1 H), 2.73-2.64 (m, 1 H), 2.60-2.54 (m, 1 H), 2.48-2.42 (m, 1 H), 2.36 (s, 3 H), 1.96-1.88 (m, 1 H), 1.80-1.73 (m, 1 H), 1.65-1.53 (m, 1 H), 1.23-1.11 (m, 1 H). | E AC20 BC26 |
| I-98 | 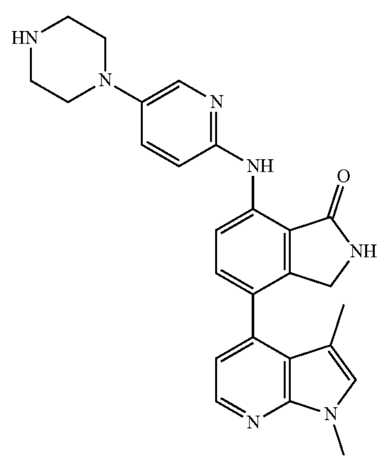 [SMILES: Cc1cn(C)c2nccc(-c3ccc(Nc4ccc(N5CCNCC5)cn4)c4c3CNC4=O)c12] | 4-(1,3-dimethylpyrrolo[2,3-b]pyridin-4-yl)-7-[[5-piperazin-1-yl-2-pyridyl]amino]isoindolin-1-one | Method AcHSS C18, m/z = 454 [M + H]+, Ret. time = 2.54 min. | ¹H NMR (400 MHz, DMSO): δ 9.83 (s, 1 H), 8.72 (s, 1 H), 8.54 (d, J = 7.8 Hz, 1 H), 8.29 (d, J = 4.8 Hz, 1 H), 8.02 (s, 1 H), 7.48 (s, 1 H), 7.45 (s, 1 H), 7.34 (s, 1 H), 7.09 (d, J = 4.5 Hz, 1 H), 6.99 (d, J = 8.7 Hz, 1 H), 4.20 (s, 2H), 3.84 (s, 3 H), 3.05 (s, 4 H), 2.92 (s, 4 H), 1.84 (s, 3 H) | F AC8 BC64 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-99 | 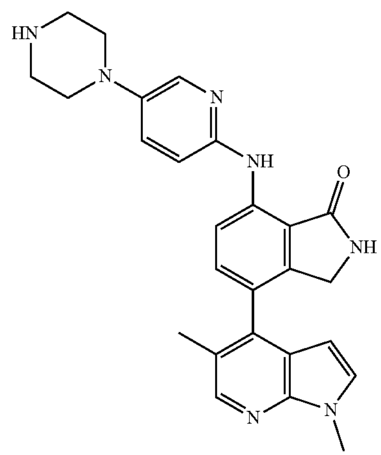 [SMILES: Cc1cnc2c(ccn2C)c1-c1ccc(Nc2ccc(N3CCNCC3)cn2)c2c1CNC2=O] | 4-(1,5-dimethylpyrrolo[2,3-b]pyridin-4-yl)-7-[(5-piperazin-1-yl-2-pyridyl)amino]isoindolin-1-one | Method AcHSS C18, m/z = 454 [M + H]+, Ret. time = 2.52 min. | ¹H NMR (400 MHz, DMSO): δ 9.83 (s, 1 H), 8.67 (s, 1 H), 8.53 (d, J = 9.0 Hz, 1 H), 8.28 (s, 1 H), 8.02 (d, J = 2.9 Hz, 1 H), 7.49 (d, J = 3.3 Hz, 1 H), 7.46 (dd, J = 2.6, 8.7 Hz, 1 H), 7.43 (d, J = 8.6 Hz, 1 H), 7.00 (d, J = 9.8 Hz, 1 H), 6.05 (d, J = 3.6 Hz, 1 H), 4.11 (d, J = 17.4 Hz, 1 H), 3.99 (d, J = 18.6 Hz, 1 H), 3.88 (s, 3 H), 3.06 (s, 4 H), 2.91 (s, 4 H), 2.25 (s, 3 H). | F AC8 BC65 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-100 | 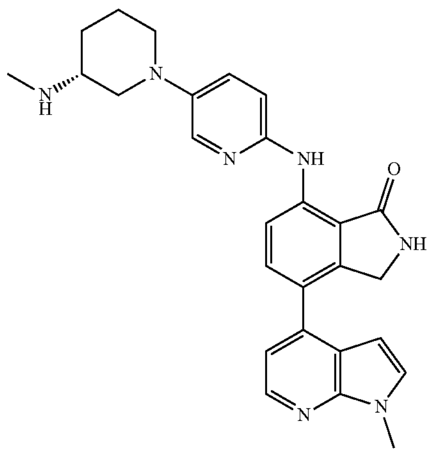 [SMILES: CN[C@@H]1CCCN(c2ccc(Nc3ccc(-c4ccnc5c4ccn5C)c4c3C(=O)NC4)nc2)C1] | 7-[5-[(3R)-3-(methylamino)-1-piperidyl]-2-pyridyl]amino]-4-(1-methylpyrrolo[2,3-b]pyridin-4-yl)isoindolin-1-one | Method AcHSS C18, m/z = 468 [M + H]+, Ret. time = 2.67 min. | ¹H NMR (400 MHz, DMSO) δ 9.91 (s, 1 H), 8.76-8.74 (m, 1 H), 8.56-8.53 (m, 1 H), 8.31 (d, J = 4.9 Hz, 1 H), 8.01 (d, J = 3.0 Hz, 1 H), 7.74-7.71 (m, 1 H), 7.58 (d, J = 3.5 Hz, 1 H), 7.44 (dd, J = 3.0, 9.0 Hz, 1 H), 7.26 (d, J = 4.9 Hz, 1 H), 6.98-6.94 (m, 1 H), 6.47 (d, J = 3.5 Hz, 1 H), 4.47-4.45 (m, 2 H), 3.88-3.87 (m, 3 H), 3.60 (dd, J = 3.1, 11.2 Hz, 1 H), 3.48-3.40 (m, 1 H), 2.73-2.64 (m, 1 H), 2.60-2.54 (m, 1 H), 2.48-2.42 (m, 1 H), 2.36 (s, 3 H), 1.96-1.88 (m, 1 H), 1.80-1.73 (m, 1 H), 1.65-1.53 (m, 1 H), 1.23-1.11 (m, 1 H). | E AC1 BC26 |
| I-101 | 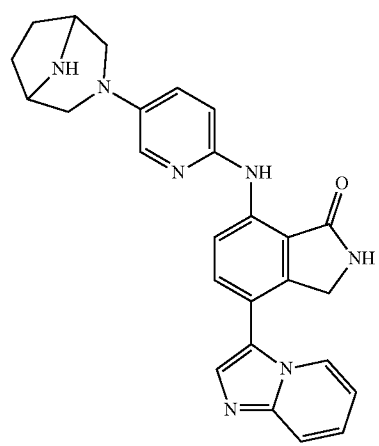 [SMILES: O=C1NCc2c(-c3cnc4ccccn34)ccc(Nc3ccc(N4CC5CCC(C4)N5)cn3)c21] | 7-[5-(3, 8-diazabicyclo[3.2.1]octan-3-yl)-2-pyridyl]amino]-4-imidazo[1,2-a]pyridin-3-yl-isoindolin-1-one | Method AcHSS C18, m/z = 452 [M + H]+, Ret. time = 1.88 min. | ¹H NMR (400 MHz, DMSO): δ 9.76 (s, 1 H), 8.73 (s, 1 H), 8.50 (d, J = 8.7 Hz, 1 H), 8.36 (d, J = 6.9 Hz, 1 H), 7.86 (d, J = 2.9 Hz, 1 H), 7.82 (s, 1 H), 7.66 (dd, J = 9.0, 9.0 Hz, 2 H), 7.33-7.27 (m, 2 H), 6.95-6.91 (m, 2 H), 4.37 (s, 2 H), 3.51-3.47 (m, 2 H), 3.38-3.34 (m, 2 H), 2.73 (dd, J = 1.8, 10.4 Hz, 2 H), 1.75-1.66 (m, 4 H), 1.23 (s, 1 H). | D AC14 BC42 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-102 | 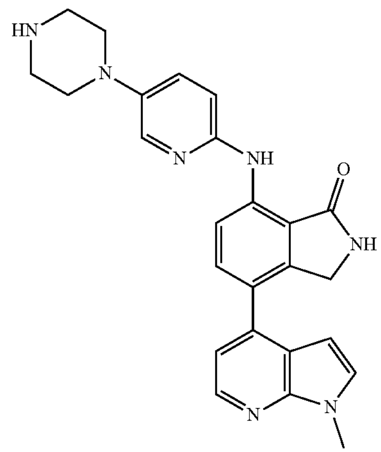 [SMILES: Cn1ccc2c(-c3ccc(Nc4ccc(N5CCNCC5)cn4)c4c3CNC4=O)ccnc21] | 4-(1-methylindol-4-yl)-7-[[5-piperazin-1-yl-2-pyridyl)amino]isoindolin-1-one | Method AcHSS C18, m/z = 439 [M + H]+, Ret. time = 3.1 min. | ¹H NMR (400 MHz, DMSO) δ 9.84 (s, 1 H), 8.66 (s, 1 H), 8.52-8.48 (m, 1 H), 8.01-7.99 (m, 1 H), 7.62-7.59 (m, 1 H), 7.47-7.37 (m, 3 H), 7.26-7.21 (m, 1 H), 7.15 (d, J = 6.5 Hz, 1 H), 6.98-6.94 (m, 1 H), 6.33 (d, J = 2.5 Hz, 1 H), 4.35-4.33 (m, 2 H), 3.85-3.84 (m, 3 H), 3.13-3.07 (m, 4 H), 3.00-2.94 (m, 4 H). | F AC8 BC66 |
| I-103 | 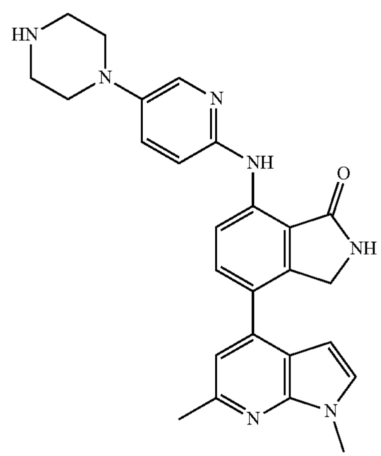 [SMILES: Cc1cc(-c2ccc(Nc3ccc(N4CCNCC4)cn3)c3c2CNC3=O)c2ccn(C)c2n1] | 4-(1,6-dimethylpyrrolo[2,3-b]pyridin-4-yl)-7-[[5-piperazin-1-yl-2-pyridyl)amino]isoindolin-1-one | Method AcHSS C18, m/z = 454 [M + H]+, Ret. time = 2.42 min. | ¹H NMR (400 MHz, DMSO): δ 9.94 (s, 1 H), 8.78 (s, 1 H), 8.56 (d, J = 8.8 Hz, 1 H), 8.03 (d, J = 3.1 Hz, 1 H), 7.73 (d, J = 8.6 Hz, 1 H), 7.49 (d, J = 3.8 Hz, 1 H), 7.47 (dd, J = 3.6, 9.1 Hz, 1 H), 7.17 (s, 1 H), 7.00 (d, J = 8.5 Hz, 1 H), 6.43 (d, J = 3.2 Hz, 1 H), 4.49 (s, 2 H), 3.88 (s, 3 H), 3.06 (t, J = 4.9 Hz, 4 H), 2.90 (t, J = 5.0 Hz, 4 H), 2.65 (s, 3 H). | F AC8 BC67 |

| # | STRUCTURE | NAME | LCMS | ¹H NMR | Method Reagent AA BB |
|---|---|---|---|---|---|
| I-104 | 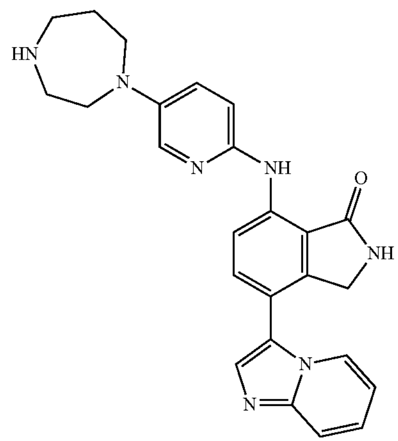 [SMILES: O=C1NCc2c(-c3cnc4ccccn34)ccc(Nc3ccc(N4CCCNCC4)cn3)c21] | 7-[[5-(1,4-diazepan-1-yl)-2-pyridyl]amino]-4-imidazo[1,2-a]pyridin-3-yl-isoindolin-1-one | Method AcHSS C18, m/z = 440 [M + H]+, Ret. time = 1.79 min. | ¹H NMR (400 MHz, DMSO): δ 9.72 (s, 1 H), 8.75 (s, 1 H), 8.49 (d, J = 8.1 Hz, 1 H), 8.41 (d, J = 5.8 Hz, 1 H), 7.88 (d, J = 3.1 Hz, 1 H), 7.86 (s, 1 H), 7.71 (d, J = 8.6 Hz, 2 H), 7.34 (ddd, J = 1.2, 6.7, 9.1 Hz, 1 H), 7.25 (dd, J = 3.3, 8.9 Hz, 1 H), 7.01-6.96 (m, 2 H), 4.42 (s, 2 H), 3.60 (t, J = 5.9 Hz, 2 H), 3.51 (t, J = 5.4 Hz, 2 H), 2.91 (t, J = 5.1 Hz, 2 H), 2.69 (t, J = 6.2 Hz, 2 H), 1.88-1.81 (m, 2 H). | D AC16 BC42 |
| I-105 | 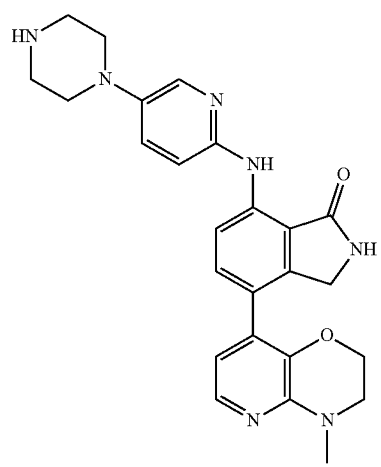 [SMILES: CN1CCOc2c(-c3ccc(Nc4ccc(N5CCNCC5)cn4)c4c3CNC4=O)ccnc21] | 4-(4-methyl-2,3-dihydropyrido[3,2-b][1,4]oxazin-8-yl)-7-[[5-piperazin-1-yl-2-pyridyl]amino]isoindolin-1-one | Method AcHSS C18, m/z = 458 [M + H]+, Ret. time = 1.8 min. | ¹H NMR (400 MHz, DMSO): δ 9.85 (s, 1 H), 8.71 (s, 1 H), 8.45 (d, J = 8.8 Hz, 1 H), 8.01 (d, J = 3.1 Hz, 1 H), 7.74 (d, J = 4.9 Hz, 1 H), 7.48-7.44 (m, 2 H), 6.97 (d, J = 9.6 Hz, 1 H), 6.59 (d, J = 5.3 Hz, 1 H), 4.32 (s, 2 H), 4.26 (t, J = 4.0 Hz, 2 H), 3.52 (t, J = 4.3 Hz, 2 H), 3.12 (s, 3 H), 3.06 (t, J = 4.8 Hz, 4 H), 2.91 (t, J = 4.8 Hz, 4 H). | F AC8 BC68 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-106 | 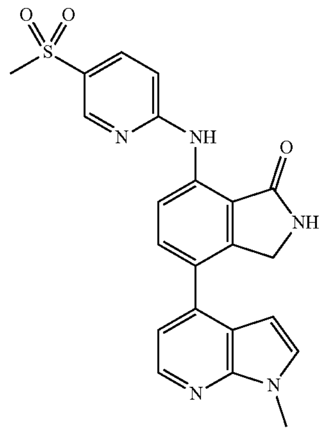 [SMILES: Cn1ccc2c(-c3ccc(Nc4ccc(S(C)(=O)=O)cn4)c4c3CNC4=O)ccnc21] | 4-(1-methylpyrrolo[2,3-b]pyridin-4-yl)-7-[(5-methylsulfonyl-2-pyridyl)amino]isoindolin-1-one | Method AcHSS C18, m/z = 434 [M + H]+, Ret. time = 3.67 min. | ¹H NMR (400 MHz, DMSO): δ 10.66 (s, 1 H), 8.95 (s, 1 H), 8.75 (s, 1 H), 8.75 (d, J = 10.9 Hz, 1 H), 8.33 (d, J = 4.8 Hz, 1 H), 8.10 (dd, J = 2.5, 8.8 Hz, 1 H), 7.82 (d, J = 8.6 Hz, 1H), 7.59 (d, J = 3.5 Hz, 1 H), 7.29 (d, J = 4.8 Hz, 1 H), 7.20 (d, J = 8.6 Hz, 1 H), 6.48 (d, J = 3.5 Hz, 1 H), 4.49 (s, 2 H), 3.87 (s, 3 H), 3.27 (s, 3 H). | E AC21 BC26 |
| I-107 | 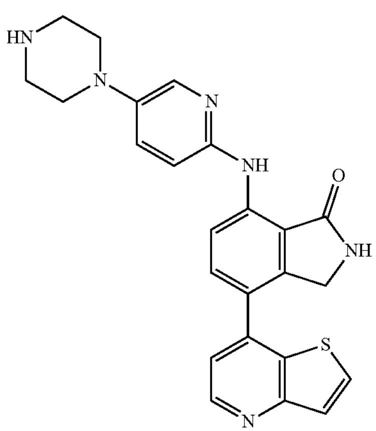 [SMILES: O=C1NCc2c(-c3ccnc4ccsc34)ccc(Nc3ccc(N4CCNCC4)cn3)c21] | 7-[(5-piperazin-1-yl-2-pyridyl)amino]-4-thieno[3,2-b]pyridin-7-yl-isoindolin-1-one | Method AcHSS C18, m/z = 443 [M + H]+, Ret. time = 2.27 min. | ¹H NMR (400 MHz, DMSO): δ 10.00 (s, 1 H), 8.86 (s, 1 H), 8.77 (d, J = 4.9 Hz, 1 H), 8.62 (d, J = 8.7 Hz, 1 H), 8.24 (d, J = 5.6 Hz, 1 H), 8.07 (d, J = 2.5 Hz, 1 H), 7.89 (d, J = 8.7 Hz, 1 H), 7.71 (d, J = 5.6 Hz, 1 H), 7.61 (d, J = 5.3 Hz, 1 H), 7.50 (dd, J = 3.1, 8.9 Hz, 1 H), 7.04 (d, J = 9.0 Hz, 1 H), 4.54 (s, 2 H), 3.14 (t, J = 5.1 Hz, 4 H), 3.00 (t, J = 5.3 Hz, 4 H). | F AC8 BC69 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-108 | 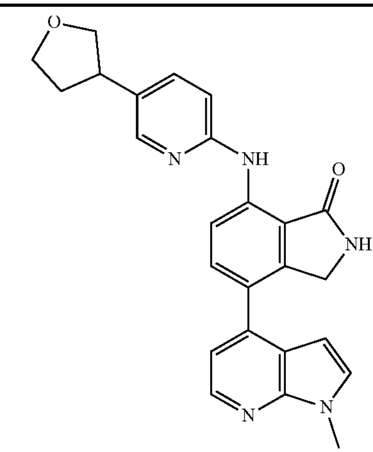 | 4-(1-methylpyrrolo[2,3-b]pyridin-4-yl)-7-[[5-THF-3-yl-2-pyridyl)amino]isoindolin-1-one | Method BicarbB EHC18, m/z = 426 [M + H]+, Ret. time = 4.23 min. | ¹H NMR (400 MHz, DMSO): δ 10.18 (s, 1 H), 8.86 (s, 1 H), 8.73 (d, J = 8.4 Hz, 1 H), 8.36 (d, J = 4.9 Hz, 1 H), 8.29 (d, J = 1.4 Hz, 1 H), 7.80 (d, J = 8.1 Hz, 1 H), 7.70 (dd, J = 2.3, 8.7 Hz, 1 H), 7.63 (d, J = 4.9 Hz, 1 H), 7.31 (d, J = 5.2 Hz, 1 H), 7.05 (d, J = 8.1 Hz, 1 H), 6.52 (d, J = 3.5 Hz, 1 H), 4.51 (s, 2 H), 4.08 (t, J = 7.7 Hz, 1 H), 4.02 (ddd, J = 4.0, 4.0, 12.1 Hz, 1 H), 3.87 (dd, J = 7.8, 15.4 Hz, 1 H), 3.60 (t, J = 8.0 Hz, 1 H), 3.47-3.39 (m, 1 H), 2.42-2.36 (m, 1 H), 2.03-1.96 (m, 1 H). | E AC22 BC26 |
| I-109 | 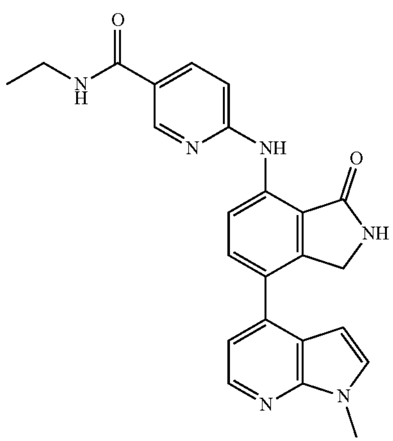 [SMILES: CCNC(=O)c1ccc(Nc2ccc(-c3ccnc4c3ccn4C)c3c2C(=O)NC3)nc1] | N-ethyl-6-[[7-(1-methylpyrrolo[2,3-b]pyridin-4-yl)-3-oxo-isoindolin-4-yl]amino]pyridine-3-carboxamide | Method AcHSS C18, m/z = 427 [M + H]+, Ret. time = 3.52 min. | ¹H NMR (400 MHz, DMSO): δ 10.43 (s, 1 H), 8.89 (s, 1 H), 8.78 (d, J = 2.3 Hz, 1 H), 8.74 (d, J = 8.6 Hz, 1 H), 8.44 (dd, J = 5.4, 5.4 Hz, 1 H), 8.33 (d, J = 5.1 Hz, 1 H), 8.11 (dd, J = 2.3, 8.6 Hz, 1 H), 7.80 (d, J = 8.6 Hz, 1H), 7.59 (d, J = 3.5 Hz, 1 H), 7.29 (d, J = 4.8 Hz, 1 H), 7.07 (d, J = 8.6 Hz, 1 H), 6.49 (d, J = 3.3 Hz, 1 H), 4.48 (s, 2 H), 3.87 (s, 3 H), 3.34-3.27 (m, 2 H), 1.14 (dd, J = 7.2, 7.2 Hz, 3 H). | E AC23 BC26 |

| # | STRUCTURE | NAME | LCMS | ¹H NMR | Method AA Reagent BB |
|---|---|---|---|---|---|
| I-110 | 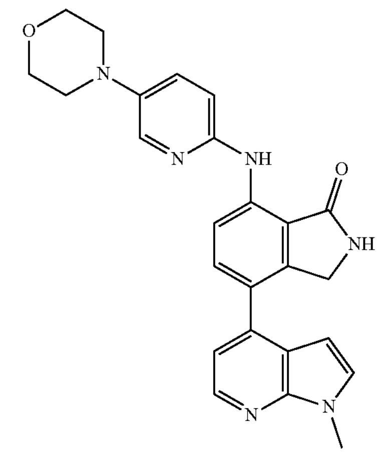 [SMILES: Cn1ccc2c(-c3ccc(Nc4ccc(N5CCOCC5)cn4)c4c3CNC4=O)ccnc21] | 4-(1-methylpyrrolo[2,3-b]pyridin-4-yl)-7-[(5-morpholino-2-pyridyl)amino]isoindolin-1-one | Method BicarbB EHC18, m/z = 441 [M + H]+, Ret. time = 4.04 min. | ¹H NMR (400 MHz, DMSO): δ 9.92 (s, 1 H), 8.73 (s, 1 H), 8.54 (d, J = 8.6 Hz, 1 H), 8.30 (d, J = 4.8 Hz, 1 H), 8.01 (d, J = 2.8 Hz, 1H), 7.71 (d, J = 8.6 Hz, 1 H), 7.56 (d, J = 3.5 Hz, 1 H), 7.45 (dd, J = 3.0, 9.1 Hz, 1 H), 7.24 (d, J = 4.8 Hz, 1 H), 6.98 (d, J = 8.8 Hz, 1 H), 6.46 (d, J = 3.5 Hz, 1 H), 4.44 (s, 2 H), 3.86 (s, 3 H), 3.78-3.74 (m, 4 H), 3.09 (dd, J = 4.7, 4.7 Hz, 4 H). | E AC10 BC26 |
| I-111 | 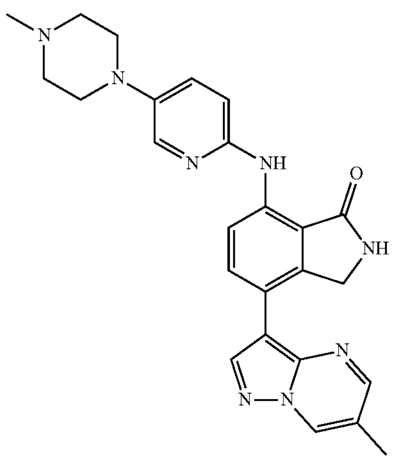 | 7-[[5-(4-methylpiperazin-1-yl)-2-pyridyl]amino]-4-(6-methylpyrazolo[1,5-a]pyrimidin-3-yl)isoindolin-1-one | Method BicarbB EHC18, m/z = 455 [M + H]+, Ret. time = 3.68 min. | ¹H NMR (400 MHz, DMSO): δ 9.82 (s, 1 H), 9.04 (dd, J = 1.2, 2.1 Hz, 1 H), 8.79 (s, 1 H), 8.57 (d, J = 2.2 Hz, 1 H), 8.45 (d, J = 8.6 Hz, 1 H), 8.44 (s, 1 H), 8.17 (d, J = 8.3 Hz, 1 H), 7.99 (d, J = 3.2 Hz, 1 H), 7.43 (dd, J = 3.1, 8.9 Hz, 1 H), 6.95 (d, J = 8.6 Hz, 1 H), 4.63 (s, 2 H), 3.11 (t, J = 4.4 Hz, 4 H), 2.49 (s, 4 H), 2.38 (s, 3 H), 2.24 (s, 3 H). | F AC9 BC70 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-112 | 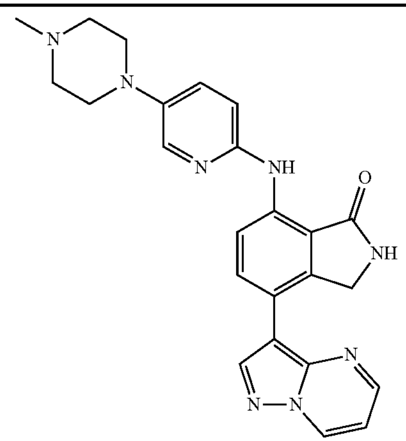 | 7-[[5-(4-methylpiperazin-1-yl)-2-pyridyl]amino]-4-pyrazolo[1,5-a]pyrimidin-3-yl-isoindolin-1-one | Method AcHSS C18, m/z = 441 [M + H]+, Ret. time = 2.25 min. | ¹H NMR (400 MHz, DMSO): δ 9.90 (s, 1 H), 9.20 (dd, J = 2.3, 7.3 Hz, 1 H), 8.81 (s, 1 H), 8.67 (dd, J = 1.6, 4.1 Hz, 1 H), 8.56 (s, 1 H), 8.49 (d, J = 9.1 Hz, 1 H), 8.18 (d, J = 8.7 Hz, 1 H), 8.05 (d, J = 3.1 Hz, 1 H), 7.49 (dd, J = 3.7, 8.0 Hz, 1 H), 7.15 (dd, J = 3.8, 6.8 Hz, 1 H), 6.99 (d, J = 9.2 Hz, 1 H), 4.65 (s, 2 H), 3.36 (s, 4 H), 3.17 (s, 4 H), 2.72 (s, 3 H). | F AC9 BC71 |
| I-113 | 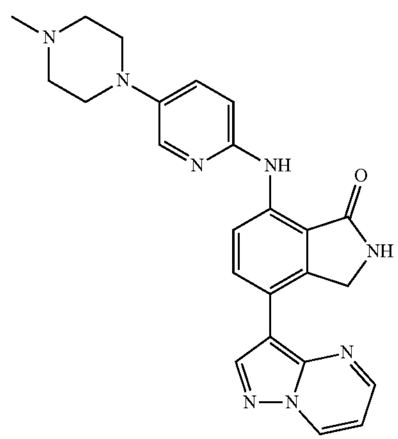 [SMILES: CN1CCN(c2ccc(Nc3ccc(-c4cnn5cccnc45)c4c3C(=O)NC4)nc2)CC1] | 7-[[5-(4-methylpiperazin-1-yl)-2-pyridyl]amino]-4-pyrazolo[1,5-a]pyrazin-3-yl-isoindolin-1-one | Method AcHSS C18, m/z = 441 [M + H]+, Ret. time = 2.25 min. | ¹H NMR (400 MHz, DMSO): δ 9.89 (s, 1 H), 9.33 (d, J = 1.4 Hz, 1 H), 8.85 (dd, J = 1.8, 4.8 Hz, 1 H), 8.83 (s, 1 H), 8.56 (d, J = 8.6 Hz, 1 H), 8.51 (s, 1 H), 8.05 (d, J = 3.2 Hz, 1 H), 7.98 (d, J = 4.9 Hz, 1 H), 7.83 (d, J = 8.1 Hz, 1 H), 7.49 (dd, J = 2.8, 8.9 Hz, 1 H), 6.98 (d, J = 7.7 Hz, 1 H), 4.58 (s, 2 H), 3.28 (s, 4 H), 2.99 (s, 4 H), 2.61 (s, 3 H). | F AC9 BC72 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-114 | 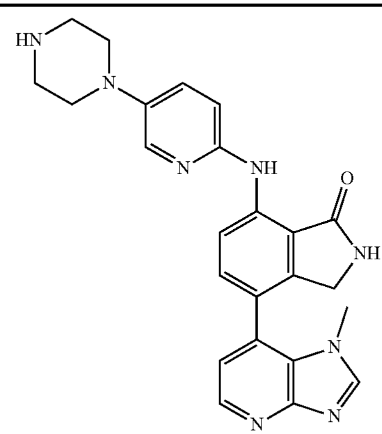 | 4-(1-methylimidazo[4,5-b]pyridin-7-yl)-7-[(5-piperazin-1-yl-2-pyridyl)amino]isoindolin-1-one | Method AcHSS C18, m/z = 441 [M + H]+, Ret. time = 2.11 min. | ¹H NMR (400 MHz, DMSO): δ 10.06 (s, 1 H), 8.81 (s, 1 H), 8.49 (d, J = 8.8 Hz, 1 H), 8.39 (s, 1 H), 8.11 (s, 2 H), 8.02 (s, 1 H), 7.83 (d, J = 8.7 Hz, 1 H), 7.44 (d, J = 13.3 Hz, 1 H), 6.92 (d, J = 9.3 Hz, 1 H), 4.88 (s, 2H), 3.88 (s, 3 H), 3.23 (s, 4 H), 3.13 (s, 4 H). | D AC8 BC73 |
| I-115 | 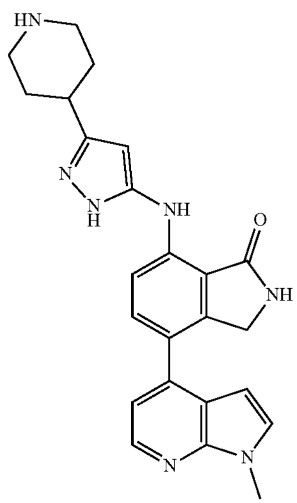 [SMILES: Cn1ccc2c(-c3ccc(Nc4cc(C5CCNCC5)n[nH]4)c4c3CNC4=O)ccnc21] | 4-(1-methylpyrrolo[2,3-b]pyridin-4-yl)-7-[[3-(4-piperidyl)-1H-pyrazol-5-yl]amino]isoindolin-1-one | Method AcHSS C18, m/z = 428 [M + H]+, Ret. time = 2.34 min. | ¹H NMR (400 MHz, DMSO): δ 12.18 (s, 1 H), 9.44 (s, 1 H), 8.70 (s, 1 H), 8.34 (d, J = 4.4 Hz, 1 H), 7.99 (s, 1 H), 7.73 (d, J = 9.8 Hz, 1 H), 7.61 (d, J = 3.6 Hz, 1 H), 7.28 (d, J = 4.6 Hz, 1 H), 6.50 (d, J = 3.6 Hz, 1 H), 5.98 (s, 1 H), 4.49 (s, 2 H), 3.91 (s, 3 H), 3.29-3.27 (m, 2 H), 2.96-2.90 (m, 3 H), 2.11-2.07 (m, 2 H), 1.79-1.73 (m, 2 H). | E AC24 BC26 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-116 | [structure] | 7-[[5-[(3S)-3-hydroxy-1-piperidyl]-2-pyridyl]amino]-4-(1-methylpyrrolo[2,3-b]pyridin-4-yl)isoindolin-1-one | Method BicarbB EHC18, m/z = 455 [M + H]+, Ret. time = 3.78 min. | ¹H NMR (400 MHz, DMSO): δ 9.95 (s, 1 H), 8.79 (s, 1 H), 8.57 (d, J = 8.5 Hz, 1 H), 8.36 (d, J = 5.1 Hz, 1 H), 8.03 (d, J = 2.8 Hz, 1 H), 7.77 (d, J = 8.5 Hz, 1 H), 7.62 (d, J = 3.2 Hz, 1 H), 7.46 (dd, J = 3.2, 9.2 Hz, 1 H), 7.30 (d, J = 5.0 Hz, 1 H), 7.01 (d, J = 9.6 Hz, 1 H), 6.51 (d, J = 3.5 Hz, 1 H), 4.87 (d, J = 7.4 Hz, 1 H), 4.51 (s, 2 H), 3.92 (s, 3 H), 3.73-3.65 (m, 1 H), 3.55 (dd, J = 3.7, 11.7 Hz, 1 H), 3.44 (d, J = 12.9 Hz, 1 H), 2.70 (ddd, J = 10.2, 10.2, 3.4 Hz, 1 H), 1.94 (dd, J = 4.9, 12.3 Hz, 1 H), 1.84 (ddd, J = 8.6, 8.6, 5.2 Hz, 1 H), 1.67-1.58 (m, 1 H), 1.37-1.27 (m, 2 H). | E AC25 BC26 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-117 | 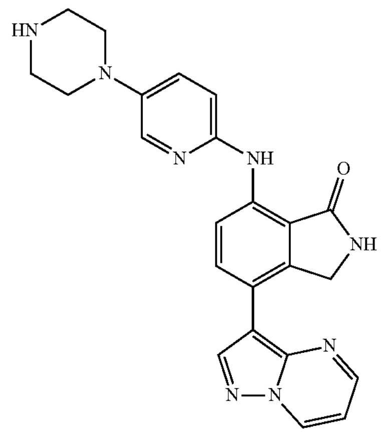 [SMILES: O=C1NCc2c(-c3cnn4cccnc34)ccc(Nc3ccc(N4CCNCC4)cn3)c21] | 7-[(5-piperazin-1-yl-2-pyridyl)amino]-4-pyrazolo[1,5-a]pyrimidin-3-yl-isoindolin-1-one | Method AcHSS C18, m/z = 427 [M + H]+, Ret. time = 2.19 min. | ¹H NMR (400 MHz, DMSO): δ 9.82 (s, 1 H), 9.20 (dd, J = 1.8, 7.1 Hz, 1 H), 8.79 (s, 1 H), 8.66 (dd, J = 1.8, 3.9 Hz, 1 H), 8.55 (s, 1 H), 8.46 (d, J = 8.8 Hz, 1 H), 8.16 (d, J = 8.2 Hz, 1 H), 7.98 (d, J = 3.5 Hz, 1 H), 7.42 (dd, J = 3.2, 8.5 Hz, 1 H), 7.14 (dd, J = 3.9, 7.4 Hz, 1 H), 6.95 (d, J = 8.8 Hz, 1 H), 4.65 (s, 2 H), 3.02 (t, J = 5.0 Hz, 4 H), 2.87 (t, J = 5.0 Hz, 4 H). | F AC8 BC71 |
| I-118 | 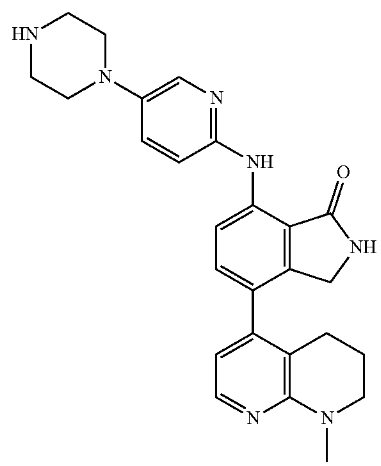 [SMILES: CN1CCCc2c(-c3ccc(Nc4ccc(N5CCNCC5)cn4)c4c3CNC4=O)ccnc21] | 4-(8-methyl-6,7-dihydro-5H-1,8-naphthyridin-4-yl)-7-[(5-piperazin-1-yl-2-pyridyl)amino]isoindolin-1-one | Method AcHSS C18, m/z = 456 [M + H]+, Ret. time = 1.84 min. | ¹H NMR (400 MHz, DMSO): δ 9.77 (s, 1 H), 8.69 (s, 1 H), 8.45 (d, J = 8.1 Hz, 1 H), 8.00 (d, J = 2.7 Hz, 1 H), 7.93 (d, J = 5.3 Hz, 1 H), 7.45 (dd, J = 3.1, 9.0 Hz, 1 H), 7.34 (d, J = 8.5 Hz, 1 H), 6.97 (d, J = 8.9 Hz, 1 H), 6.49 (d, J = 4.8 Hz, 1 H), 4.20 (s, 2 H), 3.42 (t, J = 6.1 Hz, 2 H), 3.12 (s, 3 H), 3.06 (t, J = 4.9 Hz, 4 H), 2.90 (t, J = 4.9 Hz, 4 H), 2.50 (s, 2 H), 1.83 (t, J = 5.1 Hz, 2 H). | F AC8 BC74 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-119 | 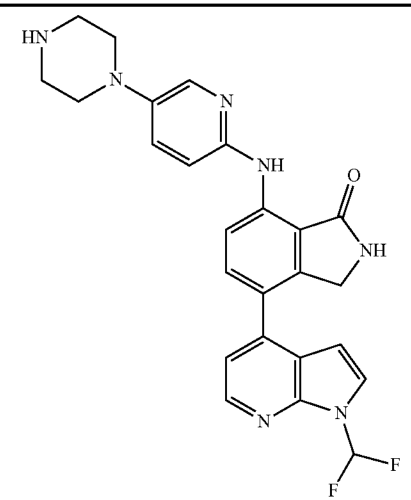 | 4-[1-(difluoromethyl)pyrrolo[2,3-b]pyridin-4-yl]-7-[(5-piperazin-1-yl-2-pyridyl)amino]isoindolin-1-one | Method AcHSS C18, m/z = 476 [M + H]+, Ret. time = 2.98 min. | ¹H NMR (400 MHz, DMSO): δ 9.98 (s, 1 H), 8.82 (s, 1 H), 8.61 (d, J = 9.7 Hz, 1 H), 8.45 (d, J = 5.9 Hz, 1 H), 8.25 (t, J = 59.3 Hz, 1 H), 8.04 (d, J = 2.5 Hz, 1 H), 7.94 (d, J = 3.4 Hz, 1H), 7.77 (d, J = 8.0 Hz, 1 H), 7.53 (d, J = 5.9 Hz, 1 H), 7.48 (dd, J = 3.4, 9.3 Hz, 1 H), 7.02 (d, J = 8.4 Hz, 1 H), 6.83 (d, J = 3.8 Hz, 1 H), 4.53 (s, 2 H), 3.07 (t, J = 5.1 Hz, 4 H), 2.92 (t, J = 4.9 Hz, 4 H). | F AC8 BC74 |
| I-120 | 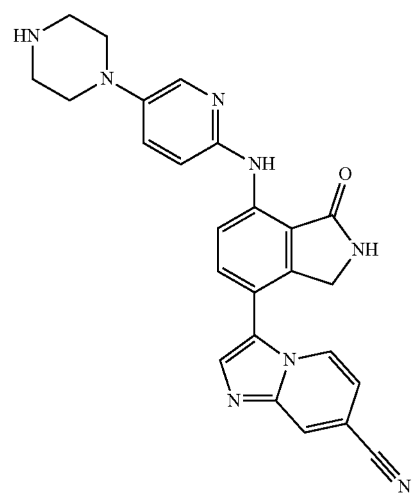 [SMILES: N#Cc1ccn2c(-c3ccc(Nc4ccc(N5CCNCC5)cn4)c4c3CNC4=O)cnc2c1] | 3-[1-oxo-7-[(5-piperazin-1-yl-2-pyridyl)amino]isoindolin-4-yl]imidazo[1,2-a]pyridine-7-carbonitrile | Method AcHSS C18, m/z = 451 [M + H]+, Ret. time = 2.21 min. | ¹H NMR (400 MHz, DMSO): δ 9.92 (s, 1 H), 8.83 (s, 1 H), 8.62 (d, J = 8.5 Hz, 1 H), 8.58 (dd, J = 0.9, 7.3 Hz, 1 H), 8.49 (dd, J = 0.9, 1.6 Hz, 1 H), 8.19 (s, 1 H), 8.04 (d, J = 2.9 Hz, 1 H), 7.78 (d, J = 8.5 Hz, 1 H), 7.48 (dd, J = 3.1, 9.2 Hz, 1 H), 7.26 (dd, J = 1.7, 7.2 Hz, 1 H), 7.02 (d, J = 9.3 Hz, 1 H), 4.45 (s, 2 H), 3.08 (t, J = 4.9 Hz, 4 H), 2.91 (t, J = 4.9 Hz, 4 H). | F AC8 BC76 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-121 | (structure) | 7-[[5-(3R)-3-hydroxy-1-piperidyl]-2-pyridyl]amino]-4-(1-methylpyrrolo[2,3-b]pyridin-4-yl)isoindolin-1-one | Method AcHSS C18, m/z = 455 [M + H]+, Ret. time = 3.02 min. | ¹H NMR (400 MHz, DMSO): δ 9.95 (s, 1 H), 8.79 (s, 1 H), 8.57 (d, J = 8.5 Hz, 1 H), 8.36 (d, J = 5.1 Hz, 1 H), 8.03 (d, J = 2.8 Hz, 1 H), 7.77 (d, J = 8.5 Hz, 1 H), 7.62 (d, J = 3.2 Hz, 1 H), 7.46 (dd, J = 3.2, 9.2 Hz, 1 H), 7.30 (d, J = 5.0 Hz, 1 H), 7.01 (d, J = 9.6 Hz, 1H), 6.51 (d, J = 3.5 Hz, 1 H), 4.87 (d, J = 7.4 Hz, 1 H), 4.51 (s, 2 H), 3.92 (s, 3 H), 3.73-3.65 (m, 1 H), 3.55 (dd, J = 3.7, 11.7 Hz, 1 H), 3.44 (d, J = 12.9 Hz, 1 H), 2.70 (ddd, J = 10.2, 10.2, 3.4 Hz, 1 H), 1.94 (dd, J = 4.9, 12.3 Hz, 1 H), 1.84 (ddd, J = 8.6, 8.6, 5.2 Hz, 1 H), 1.67-1.58 (m, 1 H), 1.37-1.27 (m, 2 H). | E AC26 BC26 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-122 | 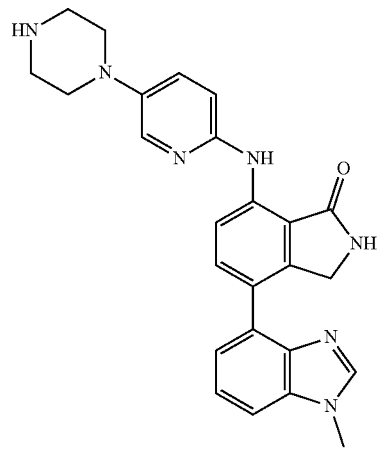 [SMILES: Cn1cnc2c(-c3ccc(Nc4ccc(N5CCNCC5)cn4)c4c3CNC4=O)cccc21] | 4-(1-methylbenzimidazol-4-yl)-7-[(5-piperazin-1-yl-2-pyridyl)amino]isoindolin-1-one | Method AcHSS C18, m/z = 440 [M + H]+, Ret. time = 2.12 min. | ¹H NMR (400 MHz, DMSO): δ 9.93 (s, 1 H), 8.68 (s, 1 H), 8.52 (d, J = 7.4 Hz, 1 H), 8.29 (s, 1 H), 8.05 (d, J = 3.2 Hz, 1 H), 7.78 (d, J = 8.3 Hz, 1 H), 7.64 (dd, J = 1.1, 7.9 Hz, 1 H), 7.49 (dd, J = 3.2, 8.8 Hz, 1 H), 7.42 (t, J = 7.8 Hz, 1 H), 7.36 (d, J = 7.5 Hz, 1 H), 7.01 (d, J = 8.8 Hz, 1 H), 4.53 (s, 2 H), 3.94 (s, 3 H), 3.15 (t, J = 5.5 Hz, 4H), 3.02 (t, J = 4.4 Hz, 4 H). | D AC8 BC77 |
| I-123 | 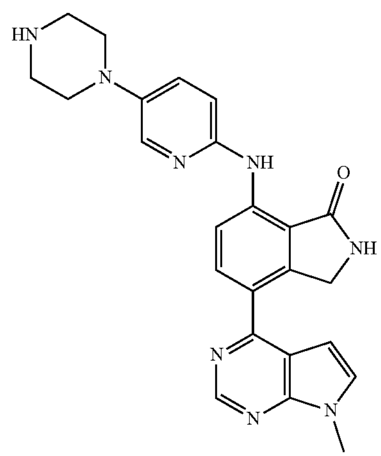 [SMILES: Cn1ccc2c(-c3ccc(Nc4ccc(N5CCNCC5)cn4)c4c3CNC4=O)ncnc21] | 4-(7-methylpyrrolo[2,3-d]pyrimidin-4-yl)-7-[(5-piperazin-1-yl-2-pyridyl)amino]isoindolin-1-one | Method AcHSS C18, m/z = 441 [M + H]+, Ret. time = 2.39 min. | ¹H NMR (400 MHz, DMSO) δ 10.12 (s, 1 H), 8.83 (d, J = 9.5 Hz, 2H), 8.61-8.57 (m, 1 H), 8.30-8.27 (m, 1 H), 8.02 (d, J = 2.9 Hz, 1 H), 7.69 (d, J = 3.6 Hz, 1 H), 7.46 (dd, J = 3.0, 8.9 Hz, 1 H), 7.01-6.98 (m, 2 H), 4.84-4.81 (m, 2 H), 3.88-3.87 (m, 3 H), 3.11-3.05 (m, 4 H), 2.91 (t, J = 4.6 Hz, 4 H). | F AC8 BC57 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-124 | 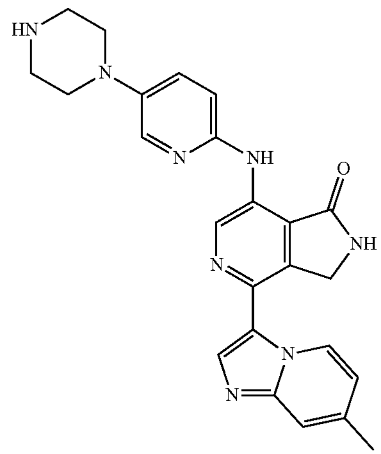 [SMILES: Cc1ccn2c(-c3ncc(Nc4ccc(N5CCNCC5)cn4)c4c3CNC4=O)cnc2c1] | 4-(7-methylimidazo[1,2-a]pyridin-3-yl)-7-[(5-piperazin-1-yl-2-pyridyl)amino]-2,3-dihydropyrrolo[3,4-c]pyridin-1-one | Method AcHSS C18, m/z = 441 [M + H]+, Ret. time = 1.97 min. | ¹H NMR (400 MHz, DMSO): δ 10.04 (s, 1 H), 9.93 (d, J = 7.5 Hz, 1 H), 9.55 (s, 1 H), 9.39 (s, 1 H), 8.20 (d, J = 2.8 Hz, 1 H), 8.13 (s, 1 H), 7.66-7.62 (m, 2 H), 7.20 (d, J = 9.1 Hz, 1 H), 7.09 (d, J = 7.3 Hz, 1 H), 4.89 (s, 2 H), 3.32 (s, 4 H), 3.22 (s, 4 H), 2.58 (s, 3 H). | A AC8 BC4 |
| I-125 | 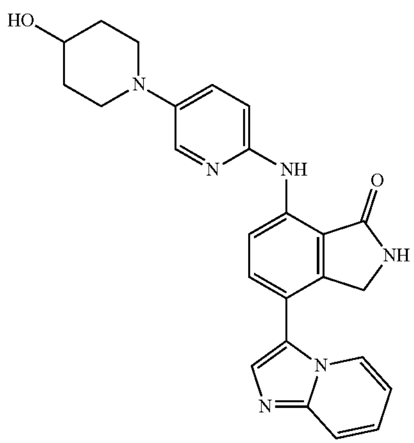 [SMILES: O=C1NCc2c(-c3cnc4ccccn34)ccc(Nc3ccc(N4CCC(O)CC4)cn3)c21] | 7-[[5-(4-hydroxy-1-piperidyl)-2-pyridyl]amino]-4-imidazo[1,2-a]pyridin-3-yl-isoindolin-1-one | Method AcHSS C18, m/z = 441 [M + H]+, Ret. time = 2.01 min. | ¹H NMR (400 MHz, DMSO) δ 9.85 (s, 1 H), 8.77 (s, 1 H), 8.56 (d, J = 9.2 Hz, 1 H), 8.39 (td, J = 1.0, 7.1 Hz, 1 H), 8.02 (d, J = 2.8 Hz, 1 H), 7.84 (s, 1 H), 7.70 (d, J = 8.6 Hz, 1 H), 7.67 (td, J = 1.0, 9.1 Hz, 1 H), 7.45 (dd, J = 3.0, 9.2 Hz, 1 H), 7.31 (ddd, J = 1.3, 6.8, 9.0 Hz, 1 H), 6.97-6.92 (m, 2 H), 4.72 (s, 1 H), 4.39 (s, 2 H), 3.68-3.61 (m, 1 H), 3.47 (td, J = 4.7, 12.5 Hz, 2 H), 2.88-2.79 (m, 2 H), 1.90-1.81 (m, 2 H), 1.58-1.48 (m, 2 H). | D AC15 BC42 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-126 | 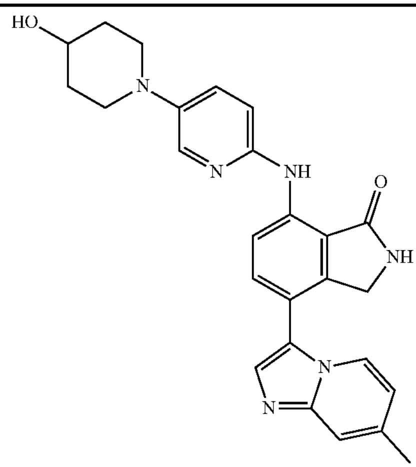 | 7-[[5-(4-hydroxy-1-piperidyl)-2-pyridyl]amino]-4-(7-methylimidazo[1,2-a]pyridin-3-yl)isoindolin-1-one | Method AcHSS C18, m/z = 455 [M + H]+, Ret. time = 2.13 min. | ¹H NMR (400 MHz, DMSO): δ 9.87 (s, 1 H), 8.80 (s, 1 H), 8.59 (d, J = 8.7 Hz, 1 H), 8.32 (d, J = 7.1 Hz, 1 H), 8.05 (d, J = 3.6 Hz, 1 H), 7.77 (s, 1 H), 7.71 (d, J = 8.7 Hz, 1 H), 7.51-7.48 (m, 2 H), 6.99 (d, J = 9.7 Hz, 1 H), 6.83 (dd, J = 1.6, 7.1 Hz, 1 H), 4.74 (d, J = 4.6 Hz, 1 H), 4.43 (s, 2H), 3.71-3.65 (m, 1 H), 3.54-3.46 (m, 2 H), 2.87 (ddd, J = 2.7, 9.9, 12.5 Hz, 2 H), 2.43 (s, 3H), 1.93-1.86 (m, 2 H), 1.62-1.53 (m, 2 H). | D AC15 BC4 |
| I-127 | 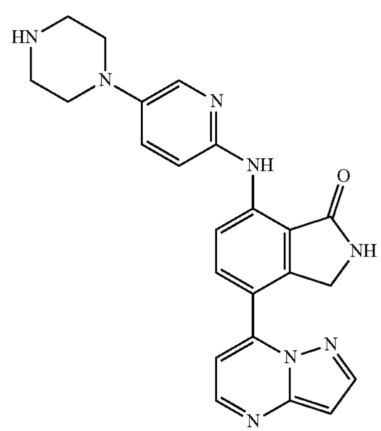 [SMILES: O=C1NCc2c(-c3ccnc4ccnn34)ccc(Nc3ccc(N4CCNCC4)cn3)c21] | 7-[(5-piperazin-1-yl-2-pyridyl)amino]-4-pyrazolo[1,5-a]pyrimidin-7-yl-isoindolin-1-one | Method AcHSS C18, m/z = 427 [M + H]+, Ret. time = 2.32 min. | ¹H NMR (400 MHz, DMSO): δ 10.09 (s, 1 H), 8.83 (s, 1 H), 8.64 (d, J = 4.2 Hz, 1 H), 8.57 (d, J = 8.9 Hz, 1 H), 8.31 (d, J = 2.4 Hz, 1 H), 8.06 (d, J = 2.8 Hz, 1 H), 8.04 (d, J = 8.9 Hz, 1 H), 7.49 (dd, J = 3.1, 9.0 Hz, 1 H), 7.27 (d, J = 4.6 Hz, 1 H), 7.05 (d, J = 8.7 Hz, 1 H), 6.88 (d, J = 2.4 Hz, 1 H), 4.52 (s, 2 H), 3.10 (t, J = 4.6 Hz, 4 H), 2.91 (t, J = 5.1 Hz, 4 H). | F AC8 BC78 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-128 | 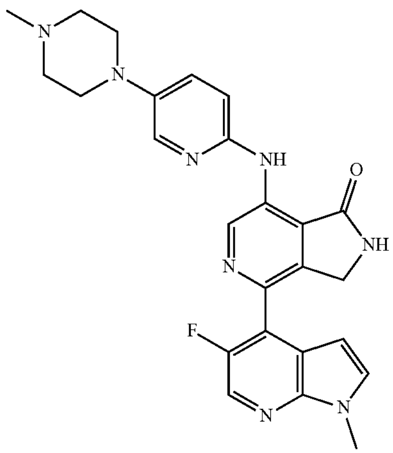 [SMILES: CN1CCN(c2ccc(Nc3cnc(-c4c(F)cnc5c4ccn5C)c4c3C(=O)NC4)nc2)CC1] | 4-(5-fluoro-1-methyl-pyrrolo[2,3-b]pyridin-4-yl)-7-[[5-(4-methylpiperazin-1-yl)-2-pyridyl]amino]-2,3-dihydropyrrolo[3,4-c]pyridin-1-one | Method AcHSS C18, m/z = 473 [M + H]+, Ret. time = 2.57 min. | ¹H NMR (400 MHz, DMSO) δ 9.91 (s, 1 H), 9.48 (s, 1 H), 9.06 (s, 1 H), 8.39 (d, J = 2.9 Hz, 1 H), 8.09 (d, J = 2.6 Hz, 1 H), 7.65 (d, J = 3.5 Hz, 1 H), 7.52 (dd, J = 2.7, 9.0 Hz, 1 H), 7.10 (d, J = 9.0 Hz, 1 H), 6.46 (d, J = 3.4 Hz, 1 H), 4.36 (s, 2 H), 3.87 (s, 3 H), 3.34 (s, 4 H), 2.95 (s, 4 H), 2.59 (s, 3 H). | A AC9 BC48 |
| I-129 | 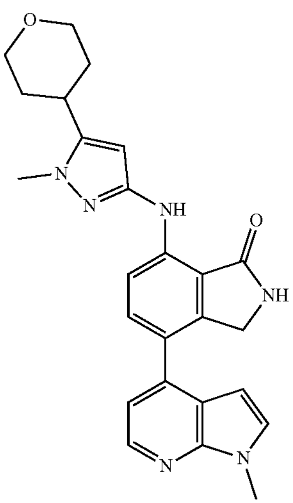 [SMILES: Cn1nc(Nc2ccc(-c3ccnc4c3ccn4C)c3c2C(=O)NC3)cc1C1CCOCC1] | 4-(1-methyl-pyrrolo[2,3-b]pyridin-4-yl)-7-[(1-methyl-5-tetrahydro-pyran-4-yl-pyrazol-3-yl)amino]iso-indolin-1-one | Method AcHSS C18, m/z = 443 [M + H]+, Ret. time = 3.73 min. | ¹H NMR (400 MHz, DMSO): δ 9.40 (s, 1 H), 8.65 (s, 1 H), 8.29 (d, J = 4.4 Hz, 1 H), 7.96 (d, J = 9.5 Hz, 1 H), 7.69 (d, J = 7.6 Hz, 1H), 7.56 (d, J = 3.2 Hz, 1 H), 7.23 (d, J = 5.7 Hz, 1 H), 6.45 (d, J = 3.5 Hz, 1 H), 5.94 (s, 1 H), 4.44 (s, 2 H), 3.96-3.90 (m, 2 H), 3.86 (s, 3 H), 3.74 (s, 3 H), 3.51-3.43 (m, 2 H), 3.01-2.91 (m, 1 H), 1.83-1.76 (m, 2 H), 1.68-1.56 (m, 2 H). | E AC27 BC26 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-130 | 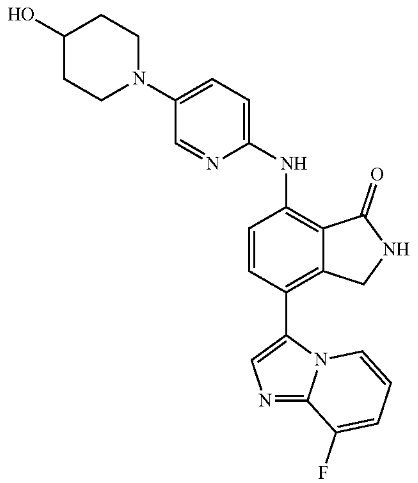 [SMILES: O=C1NCc2c(-c3cnc4c(F)cccn34)ccc(Nc3ccc(N4CCC(O)CC4)cn3)c21] | 4-(8-fluoro-imidazo[1,2-a]pyridin-3-yl)-7-[[5-(4-hydroxy-1-piperidyl)-2-pyridyl]amino]iso-indolin-1-one | Method BicarbB EHC18, m/z = 459 [M + H]+, Ret. time = 3.54 min. | ¹H NMR (400 MHz, DMSO) δ 9.86 (s, 1 H), 8.79 (s, 1 H), 8.56 (d, J = 8.8 Hz, 1 H), 8.24 (dd, J = 1.2, 7.0 Hz, 1 H), 8.01 (d, J = 3.5 Hz, 1 H), 7.89 (s, 1 H), 7.70 (d, J = 8.8 Hz, 1 H), 7.45 (dd, J = 3.1, 9.2 Hz, 1 H), 7.22 (ddd, J = 0.6, 7.6, 11.3 Hz, 1 H), 6.96 (d, J = 8.9 Hz, 1 H), 6.92 (dt, J = 4.7, 7.3 Hz, 1 H), 4.73 (s, 1 H), 4.40 (s, 2 H), 3.68-3.59 (m, 1 H), 3.51-3.43 (m, 2 H), 2.87-2.80 (m, 2 H), 1.89-1.81 (m, 2 H), 1.58-1.48 (m, 2 H). | F AC15 BC60 |
| I-131 | 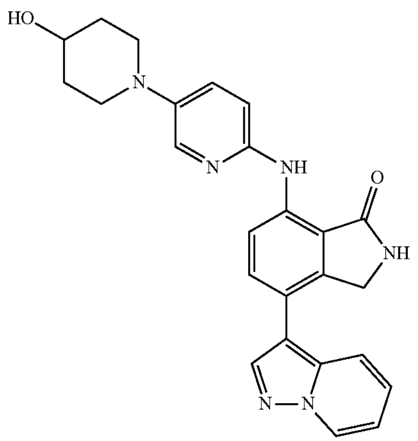 | 7-[[5-(4-hydroxy-1-piperidyl)-2-pyridyl]amino]-4-pyrazolo[1,5-a]pyridin-3-yl-isoindolin-1-one | Method AcHSS C18, m/z = 441 [M + H]+, Ret. time = 2.79 min. | ¹H NMR (400 MHz, DMSO) δ 9.69 (s, 1 H), 8.69-8.66 (m, 2 H), 8.42 (d, J = 8.0 Hz, 1 H), 8.26 (s, 1 H), 7.91 (d, J = 3.1 Hz, 1 H), 7.75 (td, J = 1.2, 9.1 Hz, 1 H), 7.59 (d, J = 8.6 Hz, 1 H), 7.35 (dd, J = 3.1, 8.6 Hz, 1 H), 7.22 (ddd, J = 1.5, 6.6, 8.9 Hz, 1 H), 6.89 (dt, J = 1.3, 6.9 Hz, 1 H), 6.84 (d, J = 8.6 Hz, 1 H), 4.62 (d, J = 4.3 Hz, 1 H), 4.42 (s, 2 H), 3.59-3.51 (m, 1 H), 3.41-3.33 (m, 2 H), 2.78-2.69 (m, 2 H), 1.82-1.73 (m, 2 H), 1.50-1.40 (m, 2 H). | F AC15 BC61 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-132 | 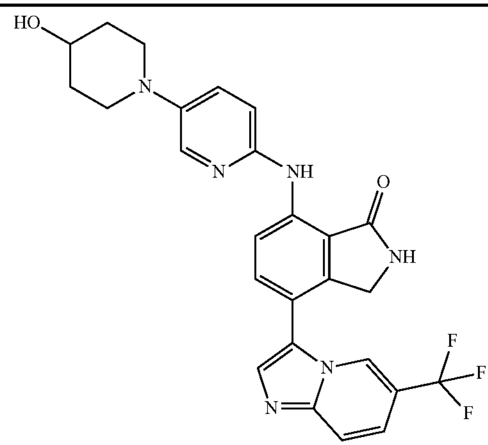 | 7-[[5-(4-hydroxy-1-piperidyl)-2-pyridyl]amino]-4-[6-(trifluoromethyl)imidazo[1,2-a]pyridin-3-yl]isoindolin-1-one | Method AcHSS C18, m/z = 509 [M + H]+, Ret. time = 2.78 min. | ¹H NMR (400 MHz, DMSO) δ 9.85 (s, 1 H), 8.76 (s, 1 H), 8.68 (s, 1 H), 8.57 (d, J = 8.5 Hz, 1H), 8.02 (s, 2 H), 7.89 (d, J = 9.5 Hz, 1 H), 7.79 (d, J = 8.7 Hz, 1 H), 7.54 (dd, J = 1.8, 9.5 Hz, 1 H), 7.45 (dd, J = 3.1, 9.0 Hz, 1 H), 6.97 (d, J = 9.0 Hz, 1 H), 4.71 (d, J = 3.9 Hz, 1 H), 4.40 (s, 2 H), 3.66-3.61 (m, 1 H), 3.49-3.44 (m, 2 H), 2.87-2.79 (m, 2 H), 1.85 (dd, J = 3.9, 12.8 Hz, 2 H), 1.58-1.48 (m, 2H). | F AC15 BC79 |
| I-133 | 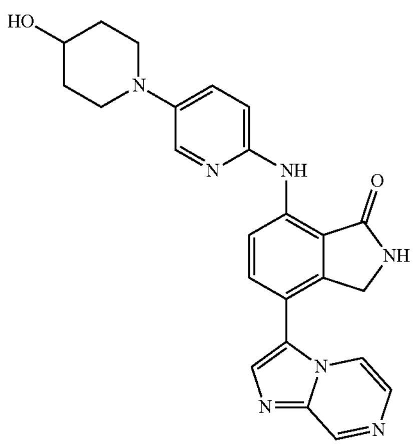 | 7-[[5-(4-hydroxy-1-piperidyl)-2-pyridyl]amino]-4-imidazo[1,2-a]pyrazin-3-yl-isoindolin-1-one | Method AcHSS C18, m/z = 442 [M + H]+, Ret. time = 2.23 min. | ¹H NMR (400 MHz, DMSO) δ 9.79 (s, 1 H), 9.07 (d, J = 1.4 Hz, 1 H), 8.72 (s, 1 H), 8.50 (d, J = 8.6 Hz, 1 H), 8.39 (dd, J = 1.5, 4.9 Hz, 1 H), 8.04 (s, 1 H), 7.94 (d, J = 2.0 Hz, 1 H), 7.68 (d, J = 8.1 Hz, 1 H), 7.37 (dd, J = 3.7, 9.1 Hz, 1 H), 6.88 (d, J = 8.7 Hz, 1 H), 4.62 (d, J = 4.9 Hz, 1 H), 4.37 (s, 2 H), 3.60-3.51 (m, 1 H), 3.43-3.35 (m, 2 H), 2.79-2.71 (m, 2 H), 1.81-1.73 (m, 2 H), 1.50-1.39 (m, 2 H). | F AC15 BC52 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-134 | 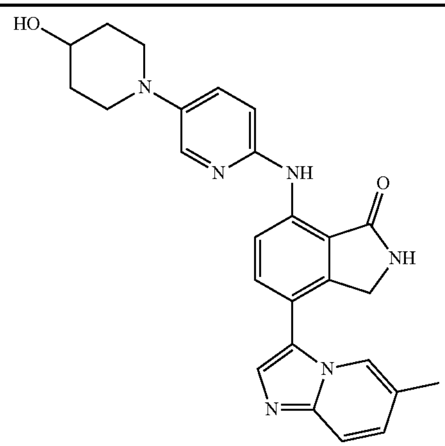 | 7-[[5-(4-hydroxy-1-piperidyl)-2-pyridyl]amino]-4-(6-methylimidazo[1,2-a]pyridin-3-yl)isoindolin-1-one | Method AcHSS C18, m/z = 455 [M + H]+, Ret. time = 2.13 min. | ¹H NMR (400 MHz, DMSO) δ 9.84 (s, 1 H), 8.75 (s, 1 H), 8.57 (d, J = 8.0 Hz, 1 H), 8.17 (s, 1 H), 8.01 (d, J = 3.2 Hz, 1 H), 7.76 (d, J = 9.5 Hz, 1 H), 7.69 (d, J = 9.5 Hz, 1 H), 7.58 (d, J = 9.5 Hz, 1 H), 7.45 (dd, J = 3.2, 9.1 Hz, 1 H), 7.17(dd, J = 2.0, 9.1 Hz, 1 H), 6.96 (d, J = 8.7 Hz, 1 H), 4.73 (s, 1 H), 4.37 (s, 2 H), 3.68-3.60 (m, 1H), 3.51-3.42 (m, 2 H), 2.87-2.80 (m, 2 H), 2.30 (s, 3 H), 1.87-1.82 (m, 2H), 1.56-1.49 (m, 2 H). | F AC15 BC40 |
| I-135 | 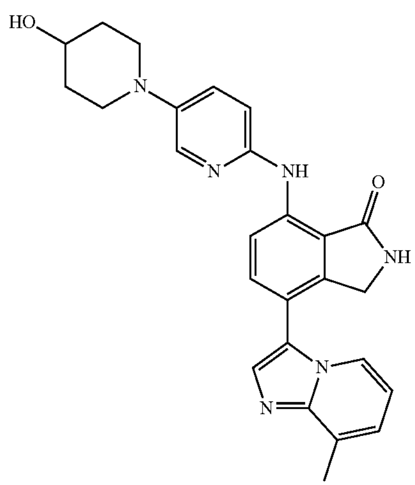 | 7-[[5-(4-hydroxy-1-piperidyl)-2-pyridyl]amino]-4-(8-methylimidazo[1,2-a]pyridin-3-yl)isoindolin-1-one | Method AcHSS C18, m/z = 455 [M + H]+, Ret. time = 2.11 min. | ¹H NMR (400 MHz, DMSO) δ 9.84 (s, 1 H), 8.77 (s, 1 H), 8.55 (d, J = 8.4 Hz, 1 H), 8.22 (d, J = 7.8 Hz, 1 H), 8.01 (d, J = 3.1 Hz, 1 H), 7.80 (s, 1 H), 7.68 (d, J = 8.4 Hz, 1 H), 7.45 (dd, J = 3.9, 9.1 Hz, 1 H), 7.12 (td, J = 1.1, 6.8 Hz, 1 H), 6.95 (d, J = 9.4 Hz, 1 H), 6.86 (t, J = 6.5 Hz, 1 H), 4.38 (s, 2 H), 3.67-3.59 (m, 1 H), 3.46 (td, J = 5.3, 11.5 Hz, 2 H), 2.87-2.79 (m, 2 H), 2.55 (s, 3 H), 1.89-1.82 (m, 2 H), 1.58-1.47 (m, 2 H). | F AC15 BC41 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-136 | 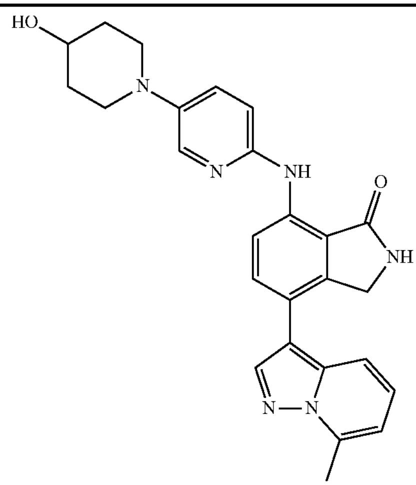 | 7-[[5-(4-hydroxy-1-piperidyl)-2-pyridyl]amino]-4-(7-methylpyrazolo[1,5-a]pyridin-3-yl)isoindolin-1-one | Method AcHSS C18, m/z = 455 [M + H]+, Ret. time = 3.08 min. | ¹H NMR (400 MHz, DMSO) δ 9.78 (s, 1 H), 8.76 (s, 1 H), 8.50 (d, J = 7.8 Hz, 1 H), 8.37 (s, 1 H), 7.99 (d, J = 3.4 Hz, 1 H), 7.74 (d, J = 9.3 Hz, 1 H), 7.66 (d, J = 8.3 Hz, 1 H), 7.43 (dd, J = 3.2, 8.6 Hz, 1 H), 7.27 (dd, J = 6.9, 9.3 Hz, 1 H), 6.93-6.89 (m, 2 H), 4.69 (d, J = 4.2 Hz, 1 H), 4.50 (s, 2 H), 3.68-3.58 (m, 1 H), 3.49-3.41 (m, 2 H), 2.85-2.77 (m, 2 H), 2.74 (s, 2 H), 1.89-1.82 (m, 2 H), 1.58-1.48 (m, 2 H). | F AC15 BC50 |
| I-137 | 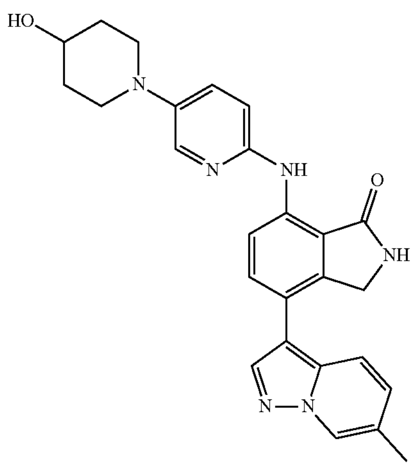 [SMILES: Cc1ccc2c(-c3ccc(Nc4ccc(N5CCC(O)CC5)cn4)c4c3CNC4=O)cnn2c1] | 7-[[5-(4-hydroxy-1-piperidyl)-2-pyridyl]amino]-4-(6-methylpyrazolo[1,5-a]pyridin-3-yl)isoindolin-1-one | Method AcHSS C18, m/z = 455 [M + H]+, Ret. time = 3.13 min. | ¹H NMR (400 MHz, DMSO) δ 9.77 (s, 1 H), 8.75 (s, 1 H), 8.60-8.58 (m, 1 H), 8.49 (d, J = 9.0 Hz, 1 H), 8.25 (s, 1 H), 7.99 (d, J = 3.4 Hz, 1 H), 7.76 (d, J = 9.8 Hz, 1 H), 7.66 (d, J = 9.0 Hz, 1 H), 7.43 (dd, J = 3.2, 8.8 Hz, 1 H), 7.18 (dd, J = 1.7, 9.0 Hz, 1 H), 6.92 (d, J = 8.8 Hz, 1 H), 4.70 (d, J = 3.0 Hz, 1 H), 4.50 (s, 2 H), 3.67-3.59 (m, 1 H), 3.49-3.42 (m, 2 H), 2.86-2.78 (m, 2 H), 2.33 (s, 3 H), 1.87-1.81 (m, 2 H), 1.59-1.47 (m, 2 H). | F AC15 BC46 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-138 | 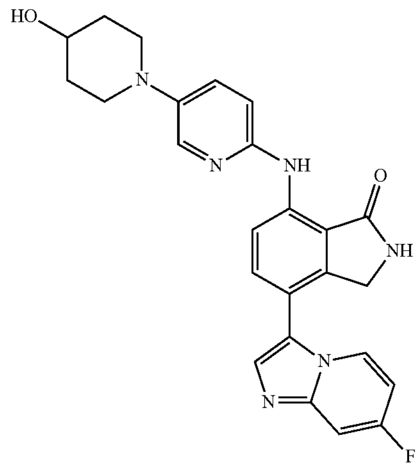 [SMILES: O=C1NCc2c(-c3cnc4cc(F)ccn34)ccc(Nc3ccc(N4CCC(O)CC4)cn3)c21] | 4-(7-fluoro-imidazo[1,2-a]pyridin-3-yl)-7-[[5-(4-hydroxy-1-piperidyl)-2-pyridyl]amino]isoindolin-1-one | Method AcHSS C18, m/z = 459 [M + H]+, Ret. time = 2.09 min. | ¹H NMR (400 MHz, DMSO) d 9.87 (s, 1H), 8.79 (s, 1H), 8.57 (d, J = 7.9 Hz, 1H), 8.52 (dd, J = 5.4, 7.9 Hz, 1H), 8.02 (d, J = 3.0 Hz, 1H), 7.98 (s, 1H), 7.71 (d, J = 9.4 Hz, 1H), 7.67 (dd, J = 2.7, 9.7 Hz, 1H), 7.47 (dd, J = 3.0, 8.9 Hz, 1H), 7.14 (dt, J = 2.5, 7.4 Hz, 1H), 6.97 (d, J = 8.9 Hz, 1H), 4.72 (s, 1H), 4.38 (s, 2H), 3.69-3.61 (m, 1H), 3.52-3.45 (m, 2H), 2.89-2.81 (m, 2H), 1.90-1.82 (m, 2H), 1.59-1.48 (m, 2H). | F AC15 BC80 |
| I-139 | 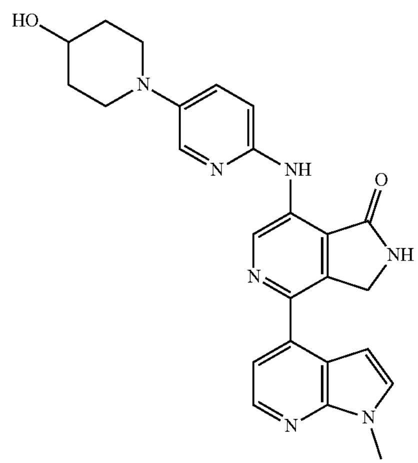 [SMILES: Cn1ccc2c(-c3ncc(Nc4ccc(N5CCC(O)CC5)cn4)c4c3CNC4=O)ccnc21] | 7-[[5-(4-hydroxy-1-piperidyl)-2-pyridyl]amino]-4-(1-methylpyrrolo[2,3-b]pyridin-4-yl)-2,3-dihydropyrrolo[3,4-c]pyridin-1-one | Method AcHSS C18, m/z = 456 [M + H]+, Ret. time = 2.57 min. | ¹H NMR (400 MHz, DMSO) d 9.91 (s, 1H), 9.49 (s, 1H), 9.14 (s, 1H), 8.34 (d, J = 5.4 Hz, 1H), 8.05 (d, J = 2.7 Hz, 1H), 7.56 (d, J = 3.1 Hz, 1H), 7.46 (dd, J = 2.7, 8.9 Hz, 1H), 7.37 (d, J = 5.4 Hz, 1H), 7.03 (d, J = 9.4 Hz, 1H), 6.90 (d, J = 3.6 Hz, 1H), 4.72-4.68 (m, 3H), 3.87 (s, 3H), 3.67-3.60 (m, 1H), 3.51-3.46 (m, 2H), 2.84 (ddd, J = 3.5, 9.5, 12.5 Hz, 2H), 1.87-1.83 (m, 2H), 1.56-1.46 (m, 2H). | A AC15 BC26 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-140 | 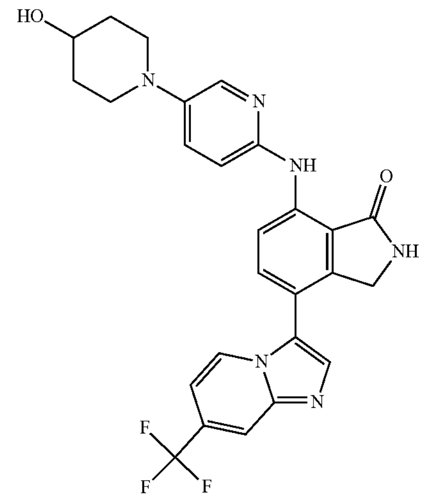 [SMILES: O=C1NCc2c(-c3cnc4cc(C(F)(F)F)ccn34)ccc(Nc3ccc(N4CCC(O)CC4)cn3)c21] | 7-[[5-(4-hydroxy-1-piperidyl)-2-pyridyl]amino]-4-[7-(trifluoromethyl)imidazo[1,2-a]pyridin-3-yl]isoindolin-1-one | Method BicarbB EHC18, m/z = 509 [M + H]+, Ret. time = 3.84 min. | ¹H NMR (400 MHz, DMSO) δ 9.86 (s, 1 H), 8.79 (s, 1 H), 8.58 (d, J = 8.5 Hz, 2H), 8.18 (s, 1 H), 8.09 (s, 1 H), 8.02 (d, J = 2.9 Hz, 1 H), 7.75 (d, J = 8.5 Hz, 1 H), 7.45 (dd, J = 3.1, 9.0 Hz, 1 H), 7.17 (dd, J = 1.9, 7.4 Hz, 1 H), 6.97 (d, J = 8.9 Hz, 1 H), 4.70 (d, J = 4.3 Hz, 1 H), 4.41 (s, 2 H), 3.68-3.59 (m, 1 H), 3.51-3.43 (m, 2 H), 2.88-2.79 (m, 2 H), 1.89-1.81 (m, 2 H), 1.58-1.47 (m, 2 H). | F AC15 BC81 |
| I-141 | 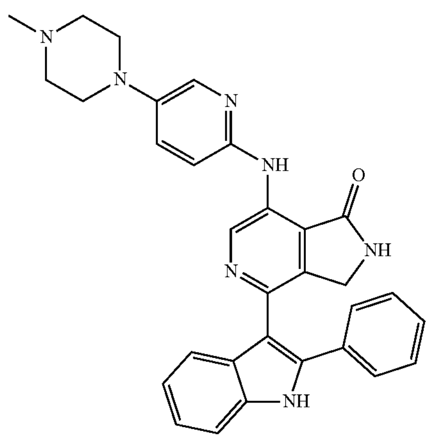 [SMILES: CN1CCN(c2ccc(Nc3cnc(-c4c(-c5ccccc5)[nH]c5ccccc45)c4c3C(=O)NC4)nc2)CC1] | 7-[[5-(4-methylpiperazin-1-yl)-2-pyridyl]amino]-4-(2-phenyl-1H-indol-3-yl)-2,3-dihydropyrrolo[3,4-c]pyridin-1-one | Method AcHSS C18, m/z = 516 [M + H]+, Ret. time = 2.61 min. | ¹H NMR (400 MHz, DMSO) δ 11.75 (s, 1 H), 9.92 (s, 1 H), 9.32 (s, 1 H), 8.78 (s, 1 H), 8.12 (d, J = 2.8 Hz, 1 H), 7.60-7.44 (m, 7 H), 7.42-7.38 (m, 1 H), 7.28-7.22 (m, 1 H), 7.13-7.09 (m, 2 H), 3.73 (s, 2 H), 3.28-3.25 (m, 4 H), 2.83 (s, 4 H), 2.51 (s, 3 H). | G AC15 BC82 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-142 | 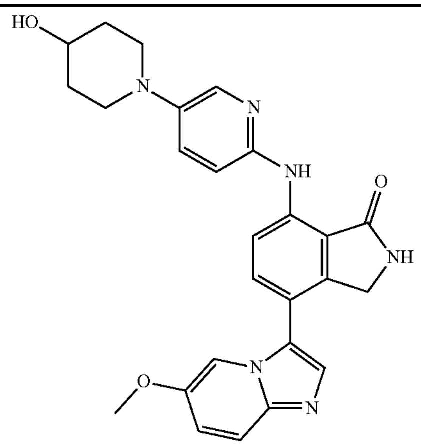 | 7-[[5-(4-hydroxy-1-piperidyl)-2-pyridyl]amino]-4-(6-methoxyimidazo[1,2-a]pyridin-3-yl)isoindolin-1-one | Method AcHSS C18, m/z = 471 [M + H]+, Ret. time = 2.19 min. | ¹H NMR (400 MHz, DMSO) δ 9.85 (s, 1 H), 8.76 (s, 1 H), 8.59 (d, J = 8.5 Hz, 1 H), 8.02 (d, J = 3.0 Hz, 1 H), 7.82 (d, J = 1.9 Hz, 1 H), 7.78 (t, J = 4.3 Hz, 2 H), 7.60 (d, J = 9.7 Hz, 1 H), 7.45 (dd, J = 3.1, 9.0 Hz, 1 H), 7.10 (dd, J = 2.3, 9.7 Hz, 1 H), 6.95 (d, J = 8.9 Hz, 1 H), 4.70 (s, 1 H), 4.41 (s, 2 H), 3.78 (s, 3 H), 3.66-3.63 (m, 1 H), 3.50-3.43 (m, 2 H), 2.87-2.79 (m, 2 H), 1.88-1.81 (m, 2 H), 1.58-1.47 (m, 2 H). | F AC15 BC82 |
| I-143 | 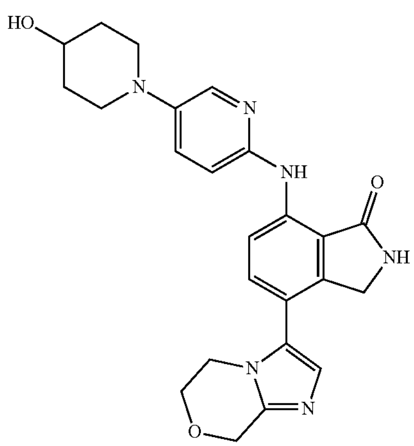 [SMILES: O=C1NCc2c(-c3cnc4n3CCOC4)ccc(Nc3ccc(N4CCC(O)CC4)cn3)c21] | 4-(6,8-dihydro-5H-imidazo[2,1-c][1,4]oxazin-3-yl)-7-[[5-(4-hydroxy-1-piperidyl)-2-pyridyl]amino]isoindolin-1-one | Method AcHSS C18, m/z = 447 [M + H]+, Ret. time = 1.87 min. | ¹H NMR (400 MHz, DMSO) δ 9.78 (s, 1 H), 8.75 (s, 1 H), 8.48 (d, J = 8.7 Hz, 1 H), 7.99 (d, J = 3.0 Hz, 1 H), 7.56 (d, J = 8.7 Hz, 1 H), 7.43 (dd, J = 3.1, 9.0 Hz, 1 H), 7.19 (s, 1 H), 6.92 (d, J = 8.9 Hz, 1 H), 4.83 (s, 2 H), 4.70 (d, J = 3.8 Hz, 1 H), 4.42 (s, 2 H), 4.00 (s, 4 H), 3.66-3.59 (m, 1 H), 3.49-3.41 (m, 2 H), 2.86-2.78 (m, 2 H), 1.89-1.81 (m, 2 H), 1.58-1.47 (m, 2 H). | F AC15 BC57 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-144 | 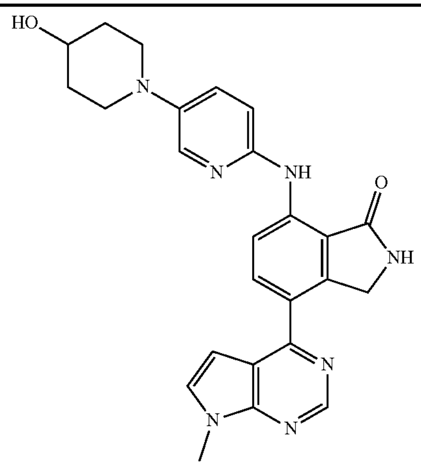 | 7-[[5-(4-hydroxy-1-piperidyl)-2-pyridyl]amino]-4-(7-methylpyrrolo[2,3-d]pyrimidin-4-yl)isoindolin-1-one | Method AcHSS C18, m/z = 456 [M + H]+, Ret. time = 2.79 min. | ¹H NMR (400 MHz, DMSO) δ 10.11 (s, 1 H), 8.85 (s, 1 H), 8.82 (s, 1 H), 8.58 (d, J = 8.8 Hz, 1 H), 8.28 (d, J = 8.8 Hz, 1 H), 8.03 (d, J = 3.0 Hz, 1 H), 7.69 (d, J = 3.5 Hz, 1 H), 7.46 (dd, J = 3.0, 9.0 Hz, 1 H), 6.99-6.96 (m, 2 H), 4.82 (s, 2 H), 3.87 (s, 3 H), 3.64 (s, 1 H), 3.53-3.45 (m, 2 H), 2.89-2.81 (m, 2 H), 1.90-1.82 (m, 2 H), 1.59-1.48 (m, 2 H). | F AC15 BC57 |
| I-145 | 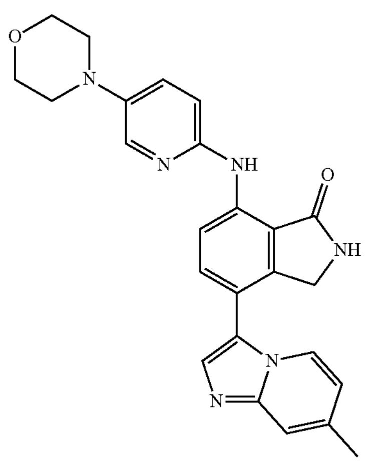 [SMILES: Cc1ccn2c(-c3ccc(Nc4ccc(N5CCOCC5)cn4)c4c3CNC4=O)cnc2c1] | 4-(7-methyl-imidazo[1,2-a]pyridin-3-yl)-7-[(5-morpholino-2-pyridyl)amino]iso-indolin-1-one | Method AcHSS C18, m/z = 441 [M + H]+, Ret. time = 2.66 min. | ¹H NMR (400 MHz, DMSO) δ 9.91 (s, 1 H), 8.81 (s, 1 H), 8.61 (d, J = 8.6 Hz, 1 H), 8.35 (d, J = 8.6 Hz, 1 H), 8.06 (d, J = 2.6 Hz, 1 H), 7.83 (s, 1 H), 7.73 (d, J = 9.1 Hz, 1 H), 7.52-7.48 (m, 2 H), 7.03 (d, J = 9.1 Hz, 1 H), 6.89 (dd, J = 1.6, 6.4 Hz, 1 H), 4.42 (s, 2 H), 3.82 (t, J = 4.6 Hz, 4 H), 3.15 (t, J = 4.9 Hz, 4 H), 2.44 (s, 3 H). | F AC4 BC26 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-146 | 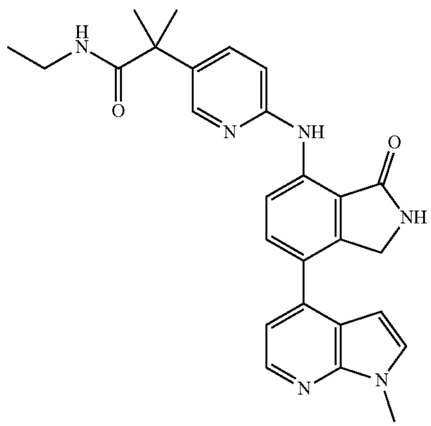 [SMILES: CCNC(=O)C(C)(C)c1ccc(Nc2ccc(-c3ccnc4c3ccn4C)c3c2C(=O)NC3)nc1] | N-ethyl-2-methyl-2-[6-[[7-(1-methylpyrrolo[2,3-b]pyridin-4-yl)-3-oxo-isoindolin-4-yl]amino]-3-pyridyl]propan amide | Method AcHSS C18, m/z = 469 [M + H]+, Ret. time = 3.61 min. | ¹H NMR (400 MHz, DMSO) δ 10.20 (s, 1 H), 8.87 (s, 1 H), 8.75 (d, J = 9.2 Hz, 1 H), 8.37 (d, J = 3.6 Hz, 1 H), 8.31 (d, J = 2.4 Hz, 1 H), 7.81 (d, J = 8.5 Hz, 1 H), 7.66 (dd, J = 2.6, 8.6 Hz, 1 H), 7.63 (d, J = 3.5 Hz, 1 H), 7.50 (t, J = 5.7 Hz, 1 H), 7.31 (d, J = 5.0 Hz, 1 H), 7.04 (d, J = 7.8 Hz, 1 H), 6.52 (d, J = 3.6 Hz, 1 H), 4.51 (s, 2 H), 3.92 (s, 3H), 3.12 (dq, J = 5.7, 7.1 Hz, 2 H), 1.53 (s, 6 H), 1.03 (t, J = 7.1 Hz, 3 H). | F AC4 BC26 |
| I-147 | 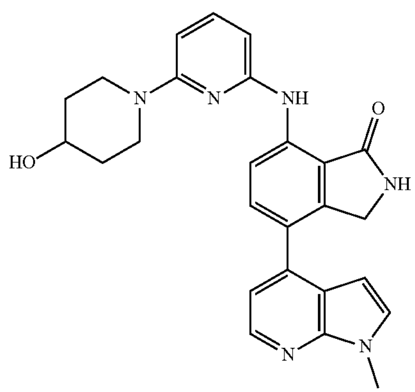 [SMILES: Cn1ccc2c(-c3ccc(Nc4cccc(N5CCC(O)CC5)n4)c4c3CNC4=O)ccnc21] | 7-[[6-(4-hydroxy-1-piperidyl)-2-pyridyl]amino]-4-(1-methylpyrrolo[2,3-b]pyridin-4-yl)isoindolin-1-one | Method BicarbB EHC18, m/z = 455 [M + H]+, Ret. time = 3.97 min. | ¹H NMR (400 MHz, DMSO) δ 10.00 (s, 1 H), 8.83 (s, 1 H), 8.54 (d, J = 9.0 Hz, 1 H), 8.37 (d, J = 5.2 Hz, 1 H), 7.78 (d, J = 7.9 Hz, 1 H), 7.63 (d, J = 3.2 Hz, 1 H), 7.50 (t, J = 7.9 Hz, 1 H), 7.31 (d, J = 5.3 Hz, 1 H), 6.52 (d, J = 3.7 Hz, 1 H), 6.42 (d, J = 7.9 Hz, 1 H), 6.26 (d, J = 7.4 Hz, 1 H), 4.74 (d, J = 3.1 Hz, 1 H), 4.50 (s, 2 H), 4.08 (dt, J = 4.8, 8.9 Hz, 2 H), 3.92 (s, 3 H), 3.81-3.74 (m, 1 H), 3.24-3.14 (m, 2 H), 1.92-1.84 (m, 2 H), 1.52-1.42 (m, 2 H). | F AC28 BC26 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-148 | 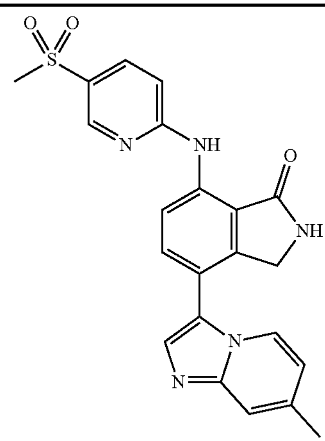 | 4-(7-methylimidazo[1,2-a]pyridin-3-yl)-7-[(5-methylsulfonyl-2-pyridyl)amino]isoindolin-1-one | Method AcHSS C18, m/z = 434 [M + H]+, Ret. time = 2.58 min. | ¹H NMR (400 MHz, DMSO) δ 10.65 (s, 1 H), 9.03 (s, 1 H), 8.82 (d, J = 5.0 Hz, 1 H), 8.81 (s, 1 H), 8.44 (d, J = 6.8 Hz, 1 H), 8.16 (dd, J = 2.6, 8.4 Hz, 1 H), 7.97 (s, 1 H), 7.89 (d, J = 8.7 Hz, 1 H), 7.58 (s, 1 H), 7.27 (d, J = 8.1 Hz, 1 H), 6.96 (d, J = 7.0 Hz, 1 H), 4.51 (s, 2 H), 3.33 (s, 3 H), 2.48 (s, 3 H). | F AC21 BC45 |
| I-149 | 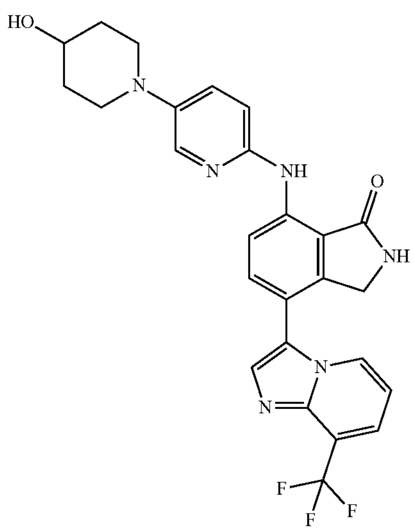 [SMILES: O=C1NCc2c(-c3cnc4c(C(F)(F)F)cccn34)ccc(Nc3ccc(N4CCC(O)CC4)cn3)c21] | 7-[[5-(4-hydroxy-1-piperidyl)-2-pyridyl]amino]-4-[8-(trifluoromethyl)imidazo[1,2-a]pyridin-3-yl]isoindolin-1-one | Method AcHSS C18, m/z = 509 [M + H]+, Ret. time = 2.95 min. | ¹H NMR (400 MHz, DMSO) δ 9.91 (s, 1 H), 8.81 (s, 1 H), 8.67 (d, J = 7.5 Hz, 1 H), 8.61 (d, J = 8.4 Hz, 1 H), 8.06 (s, 1 H), 8.01 (s, 1 H), 7.83 (d, J = 7.5 Hz, 1 H), 7.76 (d, J = 10.3 Hz, 1 H), 7.52 (dd, J = 2.5, 9.0 Hz, 1 H), 7.12 (t, J = 7.2 Hz, 1 H), 7.02 (d, J = 8.5 Hz, 1 H), 4.44 (s, 2 H), 3.72-3.64 (m, 1 H), 3.55-3.49 (m, 2 H), 2.93-2.87 (m, 2 H), 1.93-1.88 (m, 2 H), 1.62-1.52 (m, 2 H). | F AC15 BB85 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-150 | 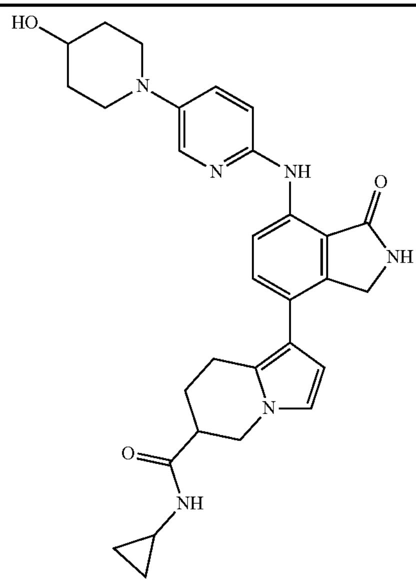 | N-cyclopropyl-3-[7-[[5-(4-hydroxy-1-piperidyl)-2-pyridyl]amino]-1-oxo-isoindolin-4-yl]-4,5,6,7-tetrahydropyrazolo[1,5-a]pyridine-6-carboxamide | Method AcHSS C18, m/z = 528 [M + H]+, Ret. time = 2.43 min. | ¹H NMR (400 MHz, DMSO) δ 9.73 (s, 1 H), 8.71 (s, 1 H), 8.41 (d, J = 9.3 Hz, 1 H), 8.18 (d, J = 4.4 Hz, 1 H), 7.97 (d, J = 3.4 Hz, 1 H), 7.72 (s, 1 H), 7.42 (td, J = 1.4, 9.1 Hz, 2 H), 6.89 (d, J = 9.7 Hz, 1 H), 4.69 (d, J = 4.0 Hz, 1 H), 4.55 (d, J = 18.3 Hz, 1 H), 4.34 (d, J = 17.4 Hz, 1 H), 4.28 (dd, J = 5.8, 12.5 Hz, 1 H), 4.09 (dd, J = 10.1, 12.7 Hz, 1 H), 3.66-3.59 (m, 1H), 3.46-3.40 (m, 2 H), 2.12-2.06 (m, 1 H), 1.87-1.78 (m, 3 H), 1.57-1.49 (m, 2 H), 0.68-0.63 (m, 2 H), 0.48-0.42 (m, 2 H). | F AC15 BC6 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-151 | 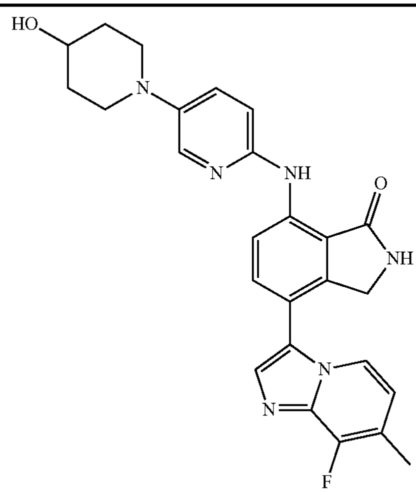 | 4-(8-fluoro-7-methyl-imidazo[1,2-a]pyridin-3-yl)-7-[[5-(4-hydroxy-1-piperidyl)-2-pyridyl]amino]isoindolin-1-one | Method AcHSS C18, m/z = 473 [M + H]+, Ret. time = 2.29 min. | ¹H NMR (400 MHz, DMSO) δ 9.84 (s, 1 H), 8.77 (s, 1 H), 8.56 (d, J = 8.4 Hz, 1 H), 8.15 (d, J = 7.8 Hz, 1 H), 8.01 (d, J = 3.6 Hz, 1 H), 7.80 (s, 1 H), 7.68 (d, J = 9.0 Hz, 1 H), 7.45 (dd, J = 2.9, 8.9 Hz, 1 H), 6.96 (d, J = 8.7 Hz, 1 H), 6.84 (t, J = 6.9 Hz, 1 H), 4.71 (d, J = 3.7 Hz, 1 H), 4.39 (s, 2 H), 3.68-3.60 (m, 1 H), 3.46 (dt, J = 4.1, 8.2 Hz, 2 H), 2.83 (ddd, J = 11.2, 11.2, 2.2 Hz, 2 H), 2.34 (d, J = 3.9 Hz, 3H), 1.90-1.81 (m, 2 H), 1.58-1.47 (m, 2 H). | F AC15 BC86 |
| I-152 | 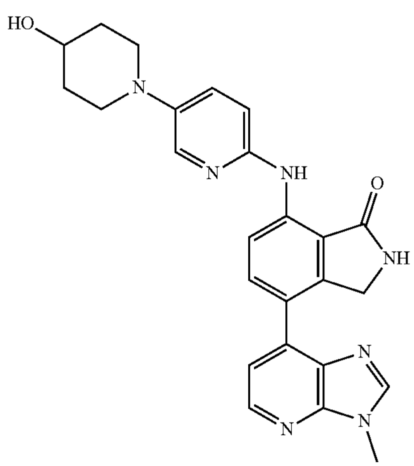 [SMILES: Cn1cnc2c(-c3ccc(Nc4ccc(N5CCC(O)CC5)cn4)c4c3CNC4=O)ccnc21] | 7-[[5-(4-hydroxy-1-piperidyl)-2-pyridyl]amino]-4-(3-methylimidazo[4,5-b]pyridin-7-yl)isoindolin-1-one | Method BicarbB EHC18, m/z = 456 [M + H]+, Ret. time = 3.04 min. | ¹H NMR (400 MHz, DMSO) δ 10.00 (s, 1 H), 8.79 (s, 1 H), 8.55 (d, J = 8.3 Hz, 1 H), 8.52 (s, 1 H), 8.47 (d, J = 5.1 Hz, 1 H), 8.06 (d, J = 3.0 Hz, 1 H), 8.02 (d, J = 8.6 Hz, 1 H), 7.49 (dd, J = 3.2, 9.1 Hz, 1 H), 7.46 (d, J = 5.3 Hz, 1 H), 7.00 (d, J = 9.1 Hz, 1 H), 4.73 (d, J = 3.8 Hz, 1 H), 4.66 (s, 2 H), 3.94 (s, 3 H), 3.71-3.64 (m, 1 H), 3.55-3.47 (m, 2 H), 2.92-2.83 (m, 2 H), 1.93-1.86 (m, 2 H), 1.62-1.52 (m, 2 H). | F AC15 BC86 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-153 | 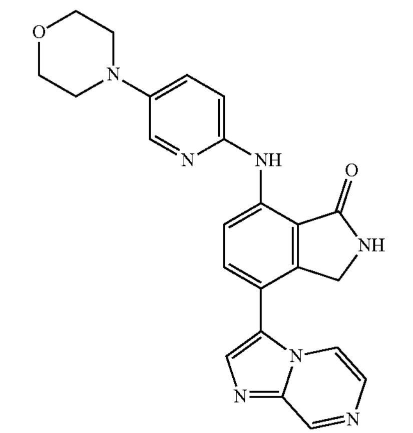 [SMILES: O=C1NCc2c(-c3cnc4cnccn34)ccc(Nc3ccc(N4CCOCC4)cn3)c21] | 4-imidazo[1,2-a]pyrazin-3-yl-7-[(5-morpholino-2-pyridyl)amino]isoindolin-1-one | Method AcHSS C18, m/z = 428 [M + H]+, Ret. time = 2.8 min. | ¹H NMR (400 MHz, DMSO) δ 9.95 (s, 1 H), 9.20 (d, J = 1.4 Hz, 1 H), 8.85 (s, 1 H), 8.64 (d, J = 8.5 Hz, 1 H), 8.51 (dd, J = 1.3, 4.8 Hz, 1 H), 8.17 (s, 1 H), 8.07 (d, J = 3.3 Hz, 1 H), 7.97 (d, J = 5.3 Hz, 1 H), 7.81 (d, J = 8.6 Hz, 1 H), 7.52 (dd, J = 3.3, 9.3 Hz, 1 H), 7.05 (d, J = 9.3 Hz, 1 H), 4.49 (s, 2 H), 3.82 (t, J = 4.4 Hz, 4 H), 3.15 (t, J = 4.4 Hz, 4 H). | F AC10 BC52 |
| I-154 | 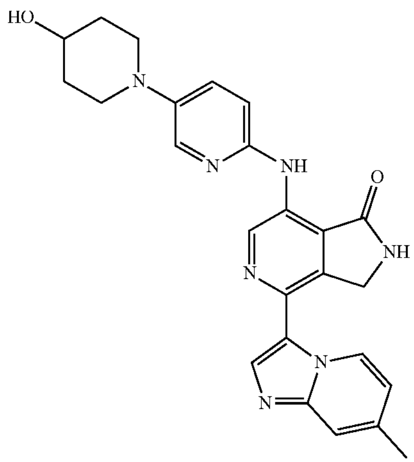 [SMILES: Cc1ccn2c(-c3ncc(Nc4ccc(N5CCC(O)CC5)cn4)c4c3CNC4=O)cnc2c1] | 7-[[5-(4-hydroxy-1-piperidyl)-2-pyridyl]amino]-4-(7-methylimidazo[1,2-a]pyridin-3-yl)-2,3-dihydropyrrolo[3,4-c]pyridin-1-one | Method AcHSS C18, m/z = 456 [M + H]+, Ret. time = 2.31 min. | ¹H NMR (400 MHz, DMSO) δ 9.88 (s, 1 H), 9.78 (d, J = 8.1 Hz, 1 H), 9.36 (s, 1 H), 9.26 (s, 1 H), 8.04 (d, J = 2.9 Hz, 1 H), 7.98 (s, 1 H), 7.51-7.49 (m, 1 H), 7.45 (dd, J = 2.9, 8.9 Hz, 1 H), 7.00 (d, J = 8.8 Hz, 1 H), 6.94 (dd, J = 1.8, 7.2 Hz, 1 H), 4.73 (s, 3 H), 3.68-3.60 (m, 1 H), 3.47 (td, J = 4.6, 12.3 Hz, 2 H), 2.87-2.80 (m, 2 H), 2.43 (s, 3 H), 1.90-1.82 (m, 2 H), 1.59-1.48 (m, 2 H). | A AC15 BC4 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-155 | 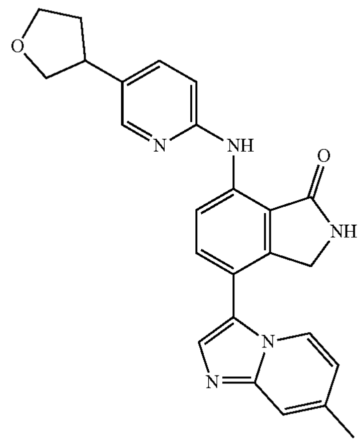 [SMILES: Cc1ccn2c(-c3ccc(Nc4ccc(C5CCOC5)cn4)c4c3CNC4=O)cnc2c1] | 4-(7-methyl-imidazo[1,2-a]pyridin-3-yl)-7-[(5-THF-3-yl-2-pyridyl)amino]iso-indolin-1-one | Method AcHSS C18, m/z = 426 [M + H]+, Ret. time = 2.82 min. | ¹H NMR (400 MHz, DMSO) δ 10.11 (s, 1 H), 8.88 (s, 1 H), 8.74 (d, J = 8.2 Hz, 1 H), 8.34 (d, J = 6.4 Hz, 1 H), 8.28 (d, J = 2.3 Hz, 1 H), 7.81 (s, 1 H), 7.77 (d, J = 9.4 Hz, 1 H), 7.70 (dd, J = 2.9, 8.2 Hz, 1 H), 7.49 (s, 1 H), 7.05 (d, J = 8.8 Hz, 1 H), 6.85 (dd, J = 1.5, 7.1 Hz, 1 H), 4.44 (s, 2 H), 4.08 (t, J = 8.1 Hz, 1 H), 4.02 (dt, J = 4.7, 8.2 Hz, 1 H), 3.87 (q, J = 7.7 Hz, 1 H), 3.60 (t, J = 7.9 Hz, 1 H), 3.47-3.39 (m, 1 H), 2.44 (s, 3 H), 2.41-2.32 (m, 1 H), 1.98 (dq, J = 12.2, 8.0 Hz, 1 H). | F AC22 BC45 |
| I-156 | 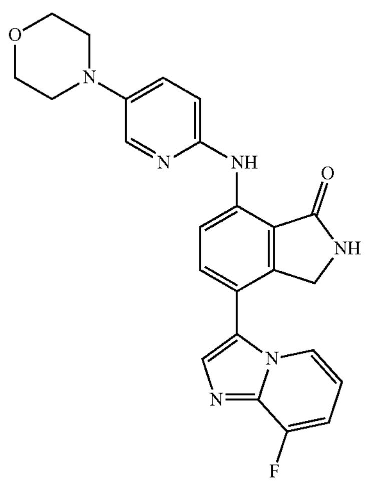 [SMILES: O=C1NCc2c(-c3cnc4c(F)cccn34)ccc(Nc3ccc(N4CCOCC4)cn3)c21] | 4-(8-fluoroimidazo[1,2-a]pyridin-3-yl)-7-[(5-morpholino-2-pyridyl)amino]iso-indolin-1-one | Method AcHSS C18, m/z = 445 [M + H]+, Ret. time = 2.9 min. | ¹H NMR (400 MHz, DMSO) δ 9.93 (s, 1 H), 8.82 (s, 1 H), 8.63 (d, J = 9.0 Hz, 1 H), 8.28 (d, J = 6.9 Hz, 1 H), 8.07 (d, J = 2.1 Hz, 1 H), 7.94 (s, 1 H), 7.76 (d, J = 9.0 Hz, 1H), 7.51 (dd, J = 3.7, 9.0 Hz, 1 H), 7.26 (dd, J = 7.9, 11.6 Hz, 1 H), 7.05 (d, J = 9.5 Hz, 1 H), 6.99-6.93 (m, 1 H), 4.44 (s, 2 H), 3.82 (t, J = 5.1 Hz, 4 H), 3.15 (t, J = 5.1 Hz, 4 H). | F AC10 BC60 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-157 | 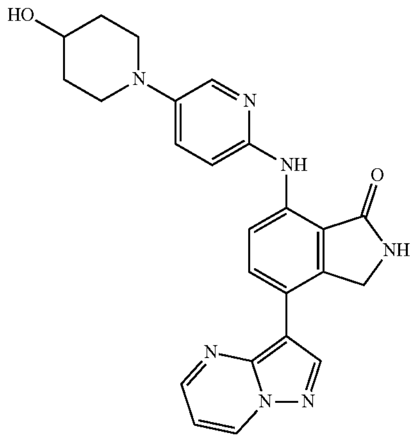 [SMILES: O=C1NCc2c(-c3cnn4cccnc34)ccc(Nc3ccc(N4CCC(O)CC4)cn3)c21] | 7-[[5-(4-hydroxy-1-piperidyl)-2-pyridyl]amino]-4-pyrazolo[1,5-a]pyrimidin-3-yl-isoindolin-1-one | Method AcHSS C18, m/z = 442 [M + H]+, Ret. time = 2.52 min. | ¹H NMR (400 MHz, DMSO) δ 9.81 (s, 1 H), 9.20 (dd, J = 1.6, 7.0 Hz, 1 H), 8.80 (s, 1 H), 8.67 (dd, J = 1.8, 4.0 Hz, 1 H), 8.55 (s, 1 H), 8.46 (d, J = 8.7 Hz, 1 H), 8.16 (d, J = 8.7 Hz, 1 H), 8.00 (d, J = 2.9 Hz, 1 H), 7.43 (dd, J = 3.1, 9.0 Hz, 1 H), 7.14 (dd, J = 4.0, 7.0 Hz, 1 H), 6.93 (d, J = 8.9 Hz, 1 H), 4.72-4.71 (m, 1 H), 4.64 (s, 2 H), 3.66-3.60 (m, 1 H), 3.49-3.41 (m, 2 H), 2.86-2.77 (m, 2 H), 1.89-1.81 (m, 2 H), 1.58-1.47 (m, 2 H). | F AC15 BC71 |
| I-158 | 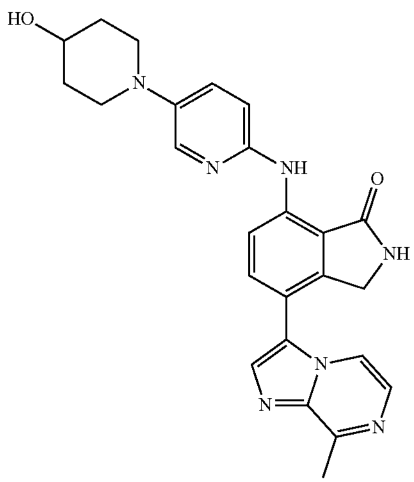 | 7-[[5-(4-hydroxy-1-piperidyl)-2-pyridyl]amino]-4-(8-methylimidazo[1,2-a]pyrazin-3-yl)isoindolin-1-one | Method AcHSS C18, m/z = 456 [M + H]+, Ret. time = 2.27 min. | ¹H NMR (400 MHz, DMSO) δ 9.87 (s, 1 H), 8.83 (s, 1 H), 8.58 (d, J = 8.3 Hz, 1 H), 8.31 (d, J = 4.7 Hz, 1 H), 8.03 (s, 1 H), 8.02 (d, J = 3.1 Hz, 1 H), 7.77 (d, J = 4.2 Hz, 1 H), 7.73 (d, J = 8.9 Hz, 1 H), 7.45 (dd, J = 3.4, 9.1 Hz, 1 H), 6.96 (d, J = 9.9 Hz, 1 H), 4.72 (s, 1 H), 4.42 (s, 2 H), 3.68-3.59 (m, 1 H), 3.47 (dt, J = 3.7, 9.0 Hz, 2 H), 2.87-2.79 (m, 5 H), 1.87-1.81 (m, 2 H), 1.57-1.47 (m, 2 H). | F AC15 BC87 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-159 | 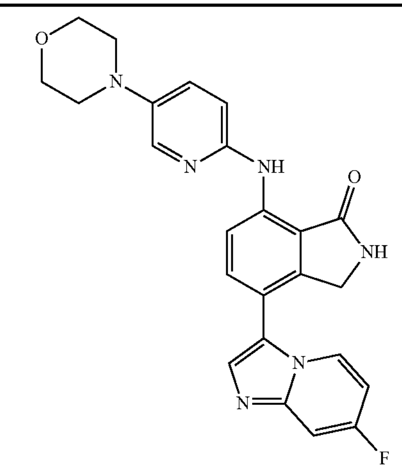 | 4-(7-fluoroimidazo[1,2-a]pyridin-3-yl)-7-[(5-morpholino-2-pyridyl)amino]isoindolin-1-one | Method AcHSS C18, m/z = 445 [M + H]+, Ret. time = 2.53 min. | ¹H NMR (400 MHz, DMSO) δ 9.90 (s, 1 H), 8.82 (s, 1 H), 8.60 (d, J = 8.5 Hz, 1 H), 8.51 (dd, J = 5.8, 7.8 Hz, 1 H), 8.02 (d, J = 4.0 Hz, 1 H), 7.97 (s, 1 H), 7.72 (d, J = 8.5 Hz, 1 H), 7.66 (dd, J = 2.5, 10.0 Hz, 1 H), 7.47 (dd, J = 2.5, 9.0 Hz, 1 H), 7.12 (dt, J = 2.7, 7.7 Hz, 1 H), 7.01 (d, J = 9.0 Hz, 1 H), 4.39 (s, 2 H), 3.78 (t, J = 4.8 Hz, 4 H), 3.10 (t, J = 4.5 Hz, 4 H). | F AC10 BC80 |
| I-160 | 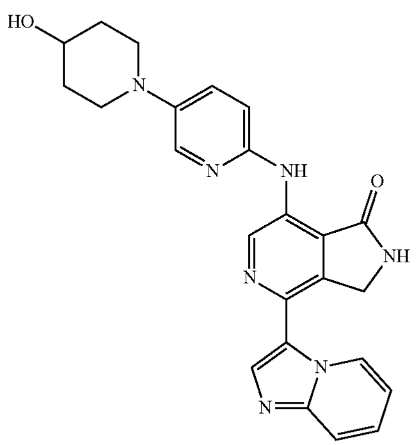 [SMILES: O=C1NCc2c(-c3cnc4ccccn34)ncc(Nc3ccc(N4CCC(O)CC4)cn3)c21] | 7-[[5-(4-hydroxy-1-piperidyl)-2-pyridyl]amino]-4-imidazo[1,2-a]pyridin-3-yl-2,3-dihydropyrrolo[3,4-c]pyridin-1-one | Method AcHSS C18, m/z = 442 [M + H]+, Ret. time = 2.11 min. | ¹H NMR (400 MHz, DMSO) δ 9.90 (s, 1 H), 9.88 (td, J = 1.1, 7.0 Hz, 1 H), 9.40 (s, 1 H), 9.27 (s, 1 H), 8.09 (s, 1 H), 8.04 (d, J = 3.2 Hz, 1 H), 7.74 (td, J = 1.1, 9.1 Hz, 1 H), 7.46 (dd, J = 3.2, 9.0 Hz, 1 H), 7.42 (ddd, J = 1.3, 6.7, 9.0 Hz, 1 H), 7.10 (dt, J = 1.3, 6.9 Hz, 1 H), 7.02 (d, J = 7.2 Hz, 1 H), 4.77 (s, 2 H), 4.73 (d, J = 4.3 Hz, 1 H), 3.69-3.61 (m, 1 H), 3.49 (td, J = 4.6, 12.5 Hz, 2 H), 2.88-2.81 (m, 2 H), 1.90-1.84 (m, 2 H), 1.58-1.48 (m, 2 H). | A AC15 BC42 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-161 | 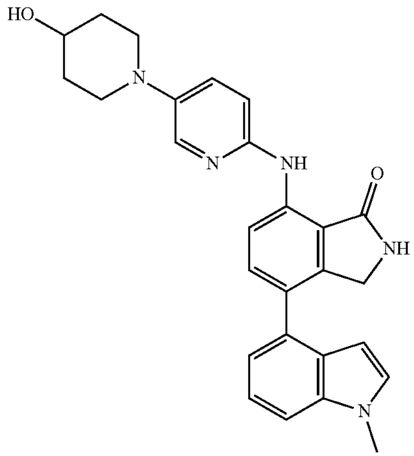 | 7-[[5-(4-hydroxy-1-piperidyl)-2-pyridyl]amino]-4-(1-methylindol-4-yl)isoindolin-1-one | Method AcHSS C18, m/z = 454 [M + H]+, Ret. time = 3.45 min. | ¹H NMR (400 MHz, DMSO) δ 9.83 (s, 1 H), 9.71 (s, 1 H), 9.34 (s, 1 H), 9.19 (s, 1 H), 7.97 (d, J = 2.7 Hz, 1 H), 7.93 (s, 1 H), 7.45 (s, 1 H), 7.40 (dd, J = 3.2, 8.6 Hz, 1 H), 6.98 (d, J = 9.0 Hz, 1 H), 6.90 (d, J = 8.1 Hz, 1 H), 4.66 (s, 2 H), 3.71 (t, J = 4.6 Hz, 4 H), 3.04 (t, J = 4.3 Hz, 4 H), 2.36 (s, 3 H). | F AC15 BC66 |
| I-162 | 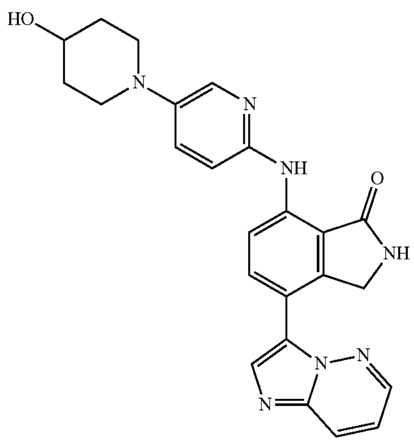 [SMILES: O=C1NCc2c(-c3cnc4cccnn34)ccc(Nc3ccc(N4CCC(O)CC4)cn3)c21] | 7-[[5-(4-hydroxy-1-piperidyl)-2-pyridyl]amino]-4-imidazo[1,2-b]pyridazin-3-yl-isoindolin-1-one | Method AcHSS C18, m/z = 442 [M + H]+, Ret. time = 2.29 min. | ¹H NMR (400 MHz, DMSO) δ 9.83 (s, 1 H), 9.71 (s, 1 H), 9.34 (s, 1 H), 9.19 (s, 1 H), 7.97 (d, J = 2.7 Hz, 1 H), 7.93 (s, 1 H), 7.45 (s, 1 H), 7.40 (dd, J = 3.2, 8.6 Hz, 1 H), 6.98 (d, J = 9.0 Hz, 1 H), 6.90 (d, J = 8.1 Hz, 1 H), 4.66 (s, 2 H), 3.71 (t, J = 4.6 Hz, 4 H), 3.04 (t, J = 4.3 Hz, 4 H), 2.36 (s, 3 H). | F AC15 BC43 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-163 | 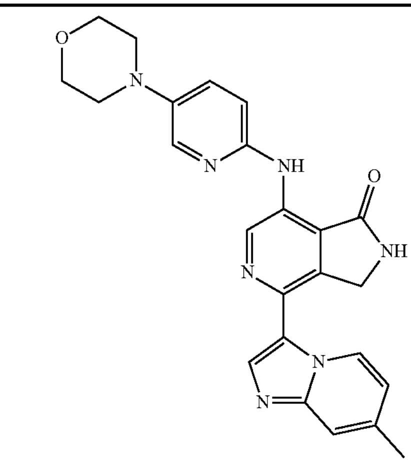 | 4-(7-methylimidazo[1,2-a]pyridin-3-yl)-7-[(5-morpholino-2-pyridyl)amino]-2,3-dihydropyrrolo[3,4-c]pyridin-1-one | Method AcHSS C18, m/z = 442 [M + H]+, Ret. time = 2.82 min. | ¹H NMR (400 MHz, DMSO) δ 9.83 (s, 1 H), 9.71 (s, 1 H), 9.34 (s, 1 H), 9.19 (s, 1 H), 7.97 (d, J = 2.7 Hz, 1 H), 7.93 (s, 1 H), 7.45 (s, 1 H), 7.40 (dd, J = 3.2, 8.6 Hz, 1 H), 6.98 (d, J = 9.0 Hz, 1 H), 6.90 (d, J = 8.1 Hz, 1 H), 4.66 (s, 2 H), 3.71 (t, J = 4.6 Hz, 4 H), 3.04 (t, J = 4.3 Hz, 4 H), 2.36 (s, 3 H). | C AC10 BC4 |
| I-164 | 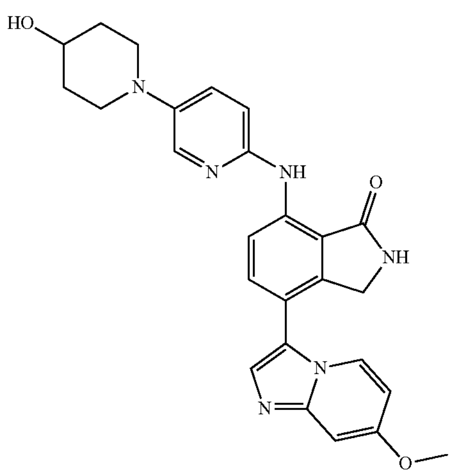 [SMILES: COc1ccn2c(-c3ccc(Nc4ccc(N5CCC(O)CC5)cn4)c4c3CNC4=O)cnc2c1] | 7-[[5-(4-hydroxy-1-piperidyl)-2-pyridyl]amino]-4-(7-methoxyimidazo[1,2-a]pyridin-3-yl)isoindolin-1-one | Method AcHSS C18, m/z = 471 [M + H]+, Ret. time = 2.19 min. | ¹H NMR (400 MHz, DMSO) δ 9.82 (s, 1 H), 8.76 (s, 1 H), 8.54 (d, J = 8.7 Hz, 1 H), 8.23 (d, J = 7.7 Hz, 1 H), 8.00 (d, J = 3.0 Hz, 1 H), 7.66 (d, J = 9.2 Hz, 2 H), 7.44 (dd, J = 3.0, 9.0 Hz, 1 H), 7.04 (d, J = 2.5 Hz, 1 H), 6.94 (d, J = 8.9 Hz, 1 H), 6.65 (dd, J = 2.5, 7.5 Hz, 1 H), 4.70 (d, J = 4.1 Hz, 1 H), 4.38 (s, 2 H), 3.88 (s, 3 H), 3.67-3.60 (m, 1 H), 3.50-3.42 (m, 2 H), 2.87-2.78 (m, 2 H), 1.89-1.81 (m, 2 H), 1.58-1.47 (m, 2 H). | F AC15 BC88 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-165 | 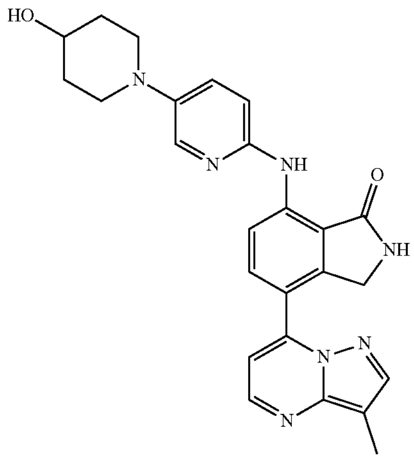 [SMILES: Cc1cnn2c(-c3ccc(Nc4ccc(N5CCC(O)CC5)cn4)c4c3CNC4=O)ccnc12] | 7-[[5-(4-hydroxy-1-piperidyl)-2-pyridyl]amino]-4-(3-methyl-pyrazolo[1,5-a]pyrimidin-7-yl)isoindolin-1-one | Method AcHSS C18, m/z = 456 [M + H]+, Ret. time = 2.87 min. | ¹H NMR (400 MHz, DMSO) δ 10.03 (s, 1 H), 8.79 (s, 1 H), 8.54-8.50 (m, 2 H), 8.13 (s, 1 H), 8.04 (d, J = 3.0 Hz, 1 H), 7.98 (d, J = 8.7 Hz, 1 H), 7.46 (dd, J = 3.0, 9.0 Hz, 1 H), 7.16 (d, J = 4.3 Hz, 1 H), 7.00 (d, J = 8.9 Hz, 1 H), 4.71 (d, J = 4.0 Hz, 1 H), 4.46 (s, 2 H), 3.67-3.61 (m, 1 H), 3.52-3.46 (m, 2 H), 2.89-2.80 (m, 2 H), 2.36 (s, 3 H), 1.89-1.81 (m, 2 H), 1.58-1.47 (m, 2 H). | F AC15 BC89 |
| I-166 | 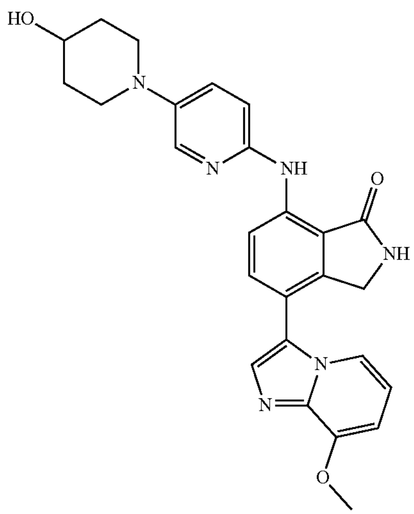 [SMILES: COc1cccn2c(-c3ccc(Nc4ccc(N5CCC(O)CC5)cn4)c4c3CNC4=O)cnc12] | 7-[[5-(4-hydroxy-1-piperidyl)-2-pyridyl]amino]-4-(8-methoxy-imidazo[1,2-a]pyridin-3-yl)isoindolin-1-one | Method AcHSS C18, m/z = 471 [M + H]+, Ret. time = 2.1 min. | ¹H NMR (400 MHz, DMSO) δ 9.83 (s, 1 H), 8.76 (s, 1 H), 8.55 (d, J = 8.5 Hz, 1 H), 8.01 (d, J = 3.0 Hz, 1 H), 7.95 (d, J = 6.5 Hz, 1 H), 7.74 (s, 1 H), 7.66 (d, J = 8.5 Hz, 1 H), 7.45 (dd, J = 3.0, 9.0 Hz, 1 H), 6.95 (d, J = 8.9 Hz, 1 H), 6.85 (dd, J = 7.2, 7.2 Hz, 1 H), 6.73 (d, J = 7.3 Hz, 1 H), 4.73-4.70 (m, 1 H), 4.37 (s, 2 H), 3.98 (s, 3 H), 3.67-3.61 (m, 1 H), 3.50-3.43 (m, 2 H), 2.87-2.79 (m, 2 H), 1.89-1.81 (m, 2 H), 1.58-1.48 (m, 2 H). | F AC15 BC90 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-167 | 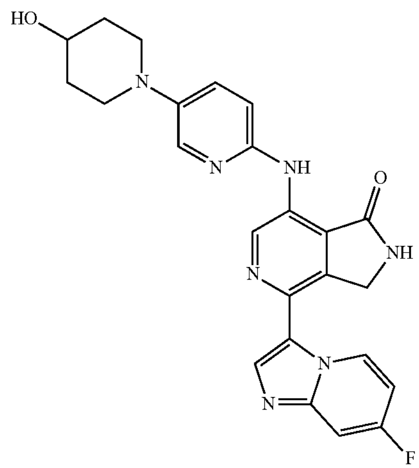 [SMILES: O=C1NCc2c(-c3cnc4cc(F)ccn34)ncc(Nc3ccc(N4CCC(O)CC4)cn3)c21] | 4-(7-fluoroimidazo[1,2-a]pyridin-3-yl)-7-[[5-(4-hydroxy-1-piperidyl)-2-pyridyl]amino]-2,3-dihydropyrrolo[3,4-c]pyridin-1-one | Method AcHSS C18, m/z = 460 [M + H]+, Ret. time = 2.28 min. | ¹H NMR (400 MHz, DMSO) δ 9.93 (dd, J = 6.5, 7.4 Hz, 1 H), 9.85 (s, 1 H), 9.36 (s, 1 H), 9.24 (s, 1 H), 8.03 (s, 1 H), 8.01 (d, J = 3.2 Hz, 1 H), 7.57 (dd, J = 2.7, 10.3 Hz, 1 H), 7.43 (dd, J = 3.0, 9.1 Hz, 1 H), 7.13 (td, J = 3.9, 10.3 Hz, 1 H), 6.97 (d, J = 9.1 Hz, 1 H), 4.73-4.68 (m, 3 H), 3.62 (dq, J = 4.4, 8.6 Hz, 1 H), 3.50-3.41 (m, 2 H), 2.82 (ddd, J = 3.2, 9.7, 12.4 Hz, 2 H), 1.88-1.80 (m, 2 H), 1.57-1.46 (m, 2 H). | A AC15 BC91 |
| I-168 | 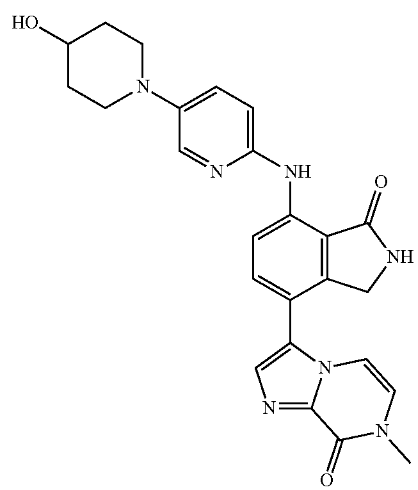 [SMILES: Cn1ccn2c(-c3ccc(Nc4ccc(N5CCC(O)CC5)cn4)c4c3CNC4=O)cnc2c1=O] | 3-[7-[[5-(4-hydroxy-1-piperidyl)-2-pyridyl]amino]-1-oxo-isoindolin-4-yl]-7-methyl-imidazo[1,2-a]pyrazin-8-one | Method AcHSS C18, m/z = 472 [M + H]+, Ret. time = 2.24 min. | ¹H NMR (400 MHz, DMSO) δ 9.93 (dd, J = 6.5, 7.4 Hz, 1 H), 9.85 (s, 1 H), 9.36 (s, 1 H), 9.24 (s, 1 H), 8.03 (s, 1 H), 8.01 (d, J = 3.2 Hz, 1 H), 7.57 (dd, J = 2.7, 10.3 Hz, 1 H), 7.43 (dd, J = 3.0, 9.1 Hz, 1 H), 7.13 (td, J = 3.9, 10.3 Hz, 1 H), 6.97 (d, J = 9.1 Hz, 1 H), 4.73-4.68 (m, 3 H), 3.62 (dq, J = 4.4, 8.6 Hz, 1 H), 3.50-3.41 (m, 2 H), 2.82 (ddd, J = 3.2, 9.7, 12.4 Hz, 2H), 1.88-1.80 (m, 2H), 1.57-1.46 (m, 2 H). | F AC15 BC92 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-169 | 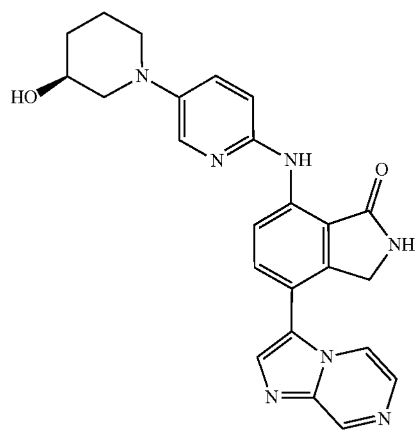 [SMILES: O=C1NCc2c(-c3cnc4cnccn34)ccc(Nc3ccc(N4CCC[C@H](O)C4)cn3)c21] | 7-[[5-(3S)-3-hydroxy-1-piperidyl]-2-pyridyl]amino]-4-imidazo[1,2-a]pyrazin-3-yl-isoindolin-1-one | Method BicarbB EHC18, m/z = 442 [M + H]+, Ret. time = 3.03 min. | ¹H NMR (400 MHz, DMSO) δ 9.87 (s, 1 H), 9.14 (d, J = 1.3 Hz, 1 H), 8.80 (s, 1 H), 8.56 (d, J = 8.6 Hz, 1 H), 8.45 (dd, J = 1.5, 4.6 Hz, 1 H), 8.11 (s, 1 H), 7.98 (d, J = 2.9 Hz, 1 H), 7.91 (d, J = 4.6 Hz, 1 H), 7.75 (d, J = 8.7 Hz, 1 H), 7.41 (dd, J = 3.0, 9.0 Hz, 1 H), 6.96 (d, J = 8.9 Hz, 1 H), 4.85-4.83 (m, 1 H), 4.43 (s, 2 H), 3.65-3.60 (m, 1 H), 3.50 (dd, J = 3.9, 11.4 Hz, 1 H), 3.41-3.37 (m, 1 H), 2.69-2.61 (m, 1 H), 2.55-2.47 (m, 1 H), 2.50 (t, J = 1.8 Hz, 1 H), 1.91-1.86 (m, 1 H), 1.80-1.74 (m, 1 H), 1.62-1.50 (m, 1 H), 1.32-1.21 (m, 1 H). | F AC25 BC52 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-170 | 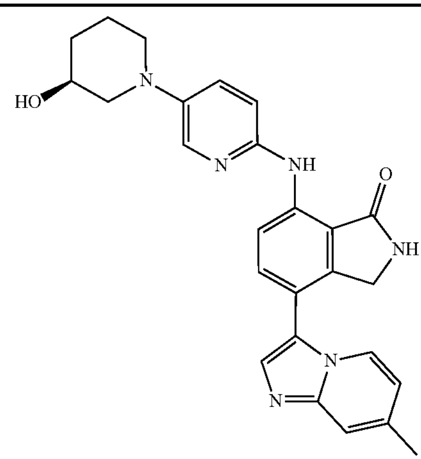 | 7-[[5-[(3S)-3-hydroxy-1-piperidyl]-2-pyridyl]amino]-4-(7-methylimidazo[1,2-a]pyridin-3-yl)isoindolin-1-one | Method AcHSS C18, m/z = 455 [M + H]+, Ret. time = 2.36 min. | ¹H NMR (400 MHz, DMSO): δ 9.83 (s, 1 H), 8.76 (s, 1 H), 8.54 (d, J = 8.7 Hz, 1 H), 8.34 (d, J = 7.0 Hz, 1 H), 7.97 (d, J = 2.9 Hz, 1 H), 7.87 (s, 1 H), 7.68 (d, J = 8.6 Hz, 1 H), 7.51 (s, 1 H), 7.41 (dd, J = 3.0, 9.0 Hz, 1 H), 6.95 (d, J = 9.0 Hz, 1 H), 6.91 (dd, J = 1.6, 7.1 Hz, 1 H), 4.83-4.83 (m, 1 H), 4.37 (s, 2 H), 3.63 (s, 1 H), 3.49 (dd, J = 3.9, 11.5 Hz, 1 H), 2.68-2.60 (m, 1 H), 2.42 (s, 3 H), 1.91-1.86 (m, 1 H), 1.81-1.74 (m, 1 H), 1.62-1.50 (m, 1 H), 1.32-1.21 (m, 1 H). | F AC25 BC45 |
| I-171 | 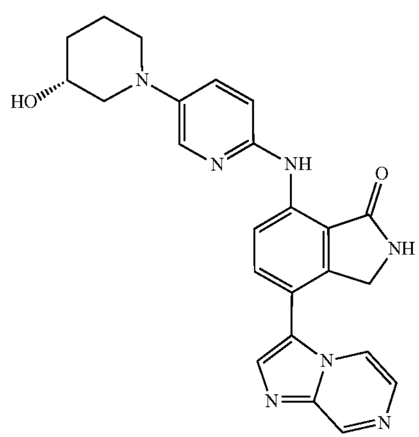 [SMILES: O=C1NCc2c(-c3cnc4cnccn34)ccc(Nc3ccc(N4CCC[C@@H](O)C4)cn3)c21] | 7-[[5-[(3R)-3-hydroxy-1-piperidyl]-2-pyridyl]amino]-4-imidazo[1,2-a]pyrazin-3-yl-isoindolin-1-one | Method AcHSS C18, m/z = 442 [M + H]+, Ret. time = 2.47 min. | ¹H NMR (400 MHz, DMSO) d 9.87 (s, 1H), 9.14 (d, J = 1.3 Hz, 1H), 8.80 (s, 1H), 8.56 (d, J = 8.6 Hz, 1H), 8.45 (dd, J = 1.5, 4.6 Hz, 1H), 8.11 (s, 1H), 7.98 (d, J = 2.9 Hz, 1H), 7.91 (d, J = 4.6 Hz, 1H), 7.75 (d, J = 8.7 Hz, 1H), 7.42 (dd, J = 3.1, 9.0 Hz, 1H), 6.96 (d, J = 9.0 Hz, 1H), 4.83 (s, 1H), 4.43 (s, 2H), 3.66-3.59 (m, 1H), 3.50 (dd, J = 4.0, 11.4 Hz, 1H), 3.42-3.37 (m, 1H), 2.69-2.61 (m, 1H), 1.92-1.86 (m, 1H), 1.81-1.74 (m, 1H), 1.61-1.50 (m, 1H), 1.32-1.21 (m, 1H). | F AC26 BC52 |

TABLE 8-continued

Characterization Data (LCMS and $^1$H NMR).

| # | STRUCTURE | NAME | LCMS | $^1$H NMR | Method AA Reagent BB |
|---|---|---|---|---|---|
| I-172 | (structure) | 7-[[5-[(3R)-3-hydroxy-1-piperidyl]-2-pyridyl]amino]-4-(7-methylimidazo[1,2-a]pyridin-3-yl)isoindolin-1-one | Method AcHSS C18, m/z = 455 [M + H]+, Ret. time = 2.35 min. | $^1$H NMR (400 MHz, DMSO): δ 9.83 (s, 1 H), 8.76 (s, 1 H), 8.54 (d, J = 8.7 Hz, 1 H), 8.31 (d, J = 7.1 Hz, 1 H), 7.97 (d, J = 2.9 Hz, 1 H), 7.81 (s, 1 H), 7.67 (d, J = 8.6 Hz, 1 H), 7.48 (s, 1 H), 7.41 (dd, J = 3.0, 9.0 Hz, 1 H), 6.94 (d, J = 8.9 Hz, 1 H), 6.86 (dd, J = 1.5, 7.1 Hz, 1 H), 4.83 (d, J = 3.1 Hz, 1 H), 4.37 (s, 2 H), 3.63 (s, 1 H), 3.49 (dd, J = 4.0, 11.3 Hz, 1 H), 3.40-3.34 (m, 1 H), 3.17 (s, 1 H), 2.68-2.60 (m, 1 H), 2.40 (s, 3 H), 1.92-1.86 (m, 1 H), 1.81-1.74 (m, 1 H), 1.61-1.50 (m, 1 H), 1.32-1.21 (m, 1 H). | F AC26 BC45 |
| I-173 | (structure) | 7-[[5-(4-hydroxy-1-piperidyl]-2-pyridyl]amino]-4-(1-methylbenzimidazol-4-yl)isoindolin-1-one | Method BicarbB EHC18, m/z = 455 [M + H]+, Ret. time = 3.5 min. | $^1$H NMR (400 MHz, DMSO) δ 9.85 (s, 1 H), 8.64 (s, 1 H), 8.46 (d, J = 8.5 Hz, 1 H), 8.25 (s, 1 H), 8.01 (d, J = 2.9 Hz, 1 H), 7.73 (d, J = 8.5 Hz, 1 H), 7.59 (d, J = 7.2 Hz, 1 H), 7.44 (dd, J = 3.0, 8.9 Hz, 1 H), 7.38 (dd, J = 7.7, 7.7 Hz, 1 H), 7.32 (d, J = 6.5 Hz, 1 H), 6.94 (d, J = 8.9 Hz, 1 H), 4.70 (d, J = 4.1 Hz, 1 H), 4.49 (s, 2 H), 3.90 (s, 3 H), 3.67-3.60 (m, 1 H), 3.50-3.42 (m, 2 H), 2.86-2.78 (m, 2 H), 1.89-1.82 (m, 2 H), 1.58-1.48 (m, 2 H). | F AC15 BC93 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-174 | 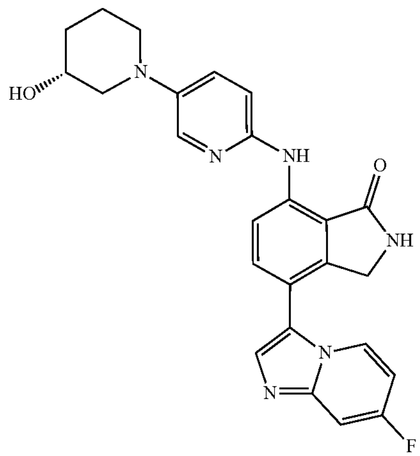 [SMILES: O=C1NCc2c(-c3cnc4cc(F)ccn34)ccc(Nc3ccc(N4CCC[C@@H](O)C4)cn3)c21] | 4-(7-fluoroimidazo[1,2-a]pyridin-3-yl)-7-[[5-[(3R)-3-hydroxy-1-piperidyl]-2-pyridyl]amino]isoindolin-1-one | Method AcHSS C18, m/z = 459 [M + H]+, Ret. time = 2.28 min. | ¹H NMR (400 MHz, DMSO): δ 9.86 (s, 1 H), 8.78 (s, 1 H), 8.56 (d, J = 8.0 Hz, 1 H), 8.45 (dd, J = 5.7, 7.6 Hz, 1 H), 7.99 (d, J = 3.1 Hz, 1H), 7.86 (s, 1 H), 7.70 (d, J = 8.4 Hz, 1 H), 7.56 (dd, J = 2.5, 9.6 Hz, 1 H), 7.43 (dd, J = 3.4, 8.7 Hz, 1 H), 7.02 (ddd, J = 7.3, 7.3, 2.3 Hz, 1 H), 6.96 (d, J = 9.0 Hz, 1 H), 4.85 (s, 1 H), 4.38 (s, 2 H), 3.69-3.61 (m, 1 H), 3.51 (dd, J = 3.7, 11.8 Hz, 1 H), 3.43-3.40 (m, 1 H), 3.40-3.37 (m, 1 H), 2.67 (ddd, J = 11.4, 11.4, 2.5 Hz, 1 H), 1.91 (dd, J = 4.5, 12.2 Hz, 1 H), 1.79 (dt, J = 3.6, 8.5 Hz, 1 H), 1.62-1.54 (m, 1 H), 1.34-1.23 (m, 1 H). | F AC26 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-175 | [structure] | 4-(7-fluoroimidazo[1,2-a]pyridin-3-yl)-7-[[5-[(3S)-3-hydroxy-1-piperidyl]-2-pyridyl]amino]isoindolin-1-one | Method BicarbB EHC18, m/z = 459 [M + H]+, Ret. time = 3.53 min. | ¹H NMR (400 MHz, DMSO): δ 9.86 (s, 1 H), 8.78 (s, 1 H), 8.56 (d, J = 8.0 Hz, 1 H), 8.45 (dd, J = 5.7, 7.6 Hz, 1 H), 7.99 (d, J = 3.1 Hz, 1 H), 7.86 (s, 1 H), 7.70 (d, J = 8.4 Hz, 1 H), 7.56 (dd, J = 2.5, 9.6 Hz, 1 H), 7.43 (dd, J = 3.4, 8.7 Hz, 1 H), 7.02 (ddd, J = 7.3, 7.3, 2.3 Hz, 1 H), 6.96 (d, J = 9.0 Hz, 1 H), 4.85 (s, 1 H), 4.38 (s, 2 H), 3.69-3.61 (m, 1 H), 3.51 (dd, J = 3.7, 11.8 Hz, 1 H), 3.43-3.40 (m, 1 H), 3.40-3.37 (m, 1 H), 2.67 (ddd, J = 11.4, 11.4, 2.5 Hz, 1 H), 1.91 (dd, J = 4.5, 12.2 Hz, 1 H), 1.79 (dt, J = 3.6, 8.5 Hz, 1 H), 1.62-1.54 (m, 1 H), 1.34-1.23 (m, 1 H). | F AC25 BC80 |

TABLE 8-continued

Characterization Data (LCMS and $^1$H NMR).

| # | STRUCTURE | NAME | LCMS | $^1$H NMR | Method Reagent AA BB |
|---|---|---|---|---|---|
| I-176 | 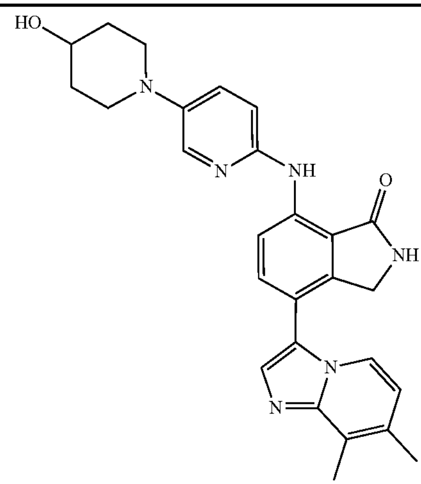 | 4-(7,8-dimethylimidazo[1,2-a]pyridin-3-yl)-7-[[5-(4-hydroxy-1-piperidyl)-2-pyridyl]amino]isoindolin-1-one | Method BicarbB EHC18, m/z = 469 [M + H]+, Ret. time = 3.62 min. | $^1$H NMR (400 MHz, DMSO): δ 9.86 (s, 1 H), 8.78 (s, 1 H), 8.58 (d, J = 8.2 Hz, 1 H), 8.24 (s, 1 H), 8.17 (d, J = 6.8 Hz, 1 H), 8.05 (d, J = 2.6 Hz, 1 H), 7.75 (s, 1 H), 7.69 (d, J = 9.7 Hz, 1 H), 7.48 (dd, J = 3.2, 9.1 Hz, 1 H), 6.99 (d, J = 9.1 Hz, 1 H), 6.82 (d, J = 6.5 Hz, 1 H), 4.41 (s, 2 H), 3.71-3.64 (m, 1 H), 3.54-3.46 (m, 2 H), 2.87 (ddd, J = 2.6, 10.0, 12.4 Hz, 2 H), 2.54 (s, 3 H), 2.38 (s, 3 H), 1.88 (d, J = 14.9 Hz, 2 H), 1.57 (ddt, J = 3.2, 10.5, 11.0 Hz, 2 H). | F AC15 BC5 |
| I-177 | 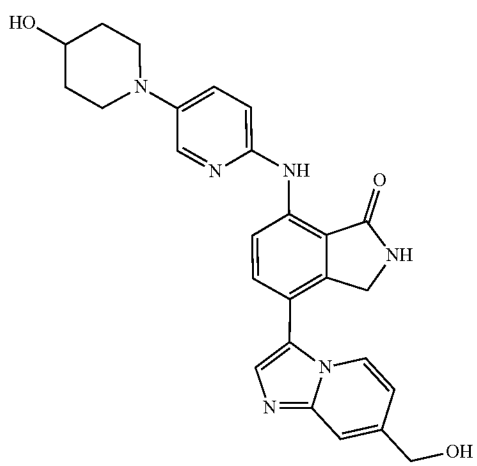 [SMILES: O=C1NCc2c(-c3cnc4cc(CO)ccn34)ccc(Nc3ccc(N4CCC(O)CC4)cn3)c21] | 4-[7-(hydroxymethyl)imidazo[1,2-a]pyridin-3-yl]-7-[[5-(4-hydroxy-1-piperidyl)-2-pyridyl]amino]isoindolin-1-one | Method BicarbB EHC18, m/z = 471 [M + H]+, Ret. time = 2.77 min. | $^1$H NMR (400 MHz, DMSO): δ 9.81 (s, 1 H), 8.74 (s, 1 H), 8.54 (d, J = 8.8 Hz, 1 H), 8.31 (d, J = 6.9 Hz, 1 H), 7.99 (d, J = 3.0 Hz, 1 H), 7.76 (s, 1 H), 7.67 (d, J = 8.5 Hz, 1 H), 7.51 (s, 1 H), 7.43 (dd, J = 3.0, 9.2 Hz, 1 H), 6.93 (d, J = 9.0 Hz, 1 H), 6.87 (dd, J = 1.5, 7.2 Hz, 1 H), 5.41 (t, J = 5.8 Hz, 1 H), 4.68 (d, J = 4.2 Hz, 1 H), 4.56 (d, J = 6.2 Hz, 2 H), 4.37(s, 2 H), 3.66-3.58 (m, 1 H), 3.49-3.41 (m, 2 H), 2.81 (ddd, J = 2.8, 9.7, 12.4 Hz, 2 H), 1.84 (dd, J = 4.4, 13.4 Hz, 2 H), 1.57-1.46 (m, 2 H). | F AC15 BC94 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-178 | 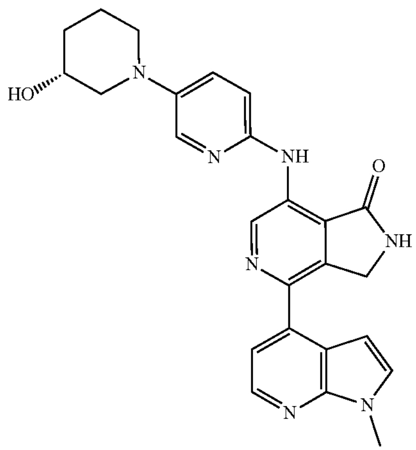 [SMILES: Cn1ccc2c(-c3ncc(Nc4ccc(N5CCC[C@@H](O)C5)cn4)c4c3CNC4=O)ccnc21] | 7-[[5-[(3R)-3-hydroxy-1-piperidyl]-2-pyridyl]amino]-4-(1-methylpyrrolo[2,3-b]pyridin-4-yl)-2,3-dihydropyrrolo[3,4-c]pyridin-1-one | Method AcHSS C18, m/z = 456 [M + H]+, Ret. time = 2.78 min. | ¹H NMR (400 MHz, DMSO) δ 9.93-9.92 (m, 1 H), 9.51 (s, 1 H), 9.17-9.15 (m, 1 H), 8.37-8.35 (m, 1 H), 8.05 (d, J = 3.0 Hz, 1 H), 7.58 (d, J = 3.5 Hz, 1 H), 7.45 (dd, J = 3.1, 9.0 Hz, 1 H), 7.39 (d, J = 4.9 Hz, 1 H), 7.07-7.04 (m, 1 H), 6.92 (d, J = 3.5 Hz, 1 H), 4.87-4.84 (m, 1 H), 4.73 (s, 2 H), 3.88 (s, 3 H), 3.71-3.62 (m, 1 H), 3.54 (dd, J = 4.0, 11.4 Hz, 1 H), 3.45-3.39 (m, 1 H), 2.73-2.64 (m, 1 H), 2.58-2.54 (m, 1 H), 1.94-1.88 (m, 1 H), 1.83-1.77 (m, 1 H), 1.64-1.53 (m, 1 H), 1.35-1.24 (m, 1 H). | C AC26 BC26 |

TABLE 8-continued

Characterization Data (LCMS and $^1$H NMR).

| # | STRUCTURE | NAME | LCMS | $^1$H NMR | Method Reagent AA BB |
|---|---|---|---|---|---|
| I-179 | 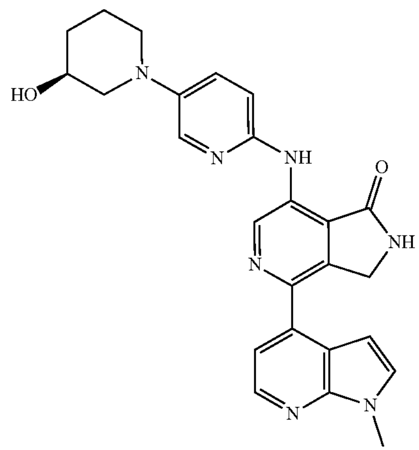 [SMILES: Cn1ccc2c(-c3ncc(Nc4ccc(N5CCC[C@H](O)C5)cn4)c4c3CNC4=O)ccnc21] | 7-[[5-[(3S)-3-hydroxy-1-piperidyl]-2-pyridyl]amino]-4-(1-methylpyrrolo[2,3-b]pyridin-4-yl)-2,3-dihydropyrrolo[3,4-c]pyridin-1-one | Method AcHSS C18, m/z = 456 [M + H]+, Ret. time = 2.77 min. | $^1$H NMR (400 MHz, DMSO) δ 9.93-9.92 (m, 1 H), 9.51 (s, 1 H), 9.18-9.16 (m, 1 H), 8.37-8.35 (m, 1 H), 8.06-8.04 (m, 1 H), 7.58-7.57 (m, 1 H), 7.45 (dd, J = 3.0, 9.0 Hz, 1 H), 7.39 (d, J = 5.1 Hz, 1 H), 7.07-7.04 (m, 1 H), 6.92 (d, J = 3.4 Hz, 1 H), 4.86 (d, J = 4.1 Hz, 1 H), 4.72 (s, 2 H), 3.88 (s, 3 H), 3.71-3.62 (m, 1 H), 3.54 (dd, J = 4.0, 11.4 Hz, 1 H), 3.46-3.41 (m, 1 H), 2.72-2.64 (m, 1 H), 2.57-2.53 (m, 1 H), 1.94-1.87 (m, 1 H), 1.83-1.76 (m, 1 H), 1.65-1.52 (m, 1 H), 1.35-1.24 (m, 1 H). | H AC25 BC26 |
| I-180 | 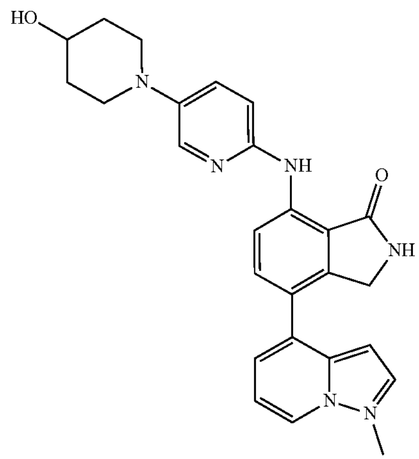 | 7-[[5-(4-hydroxy-1-piperidyl)-2-pyridyl]amino]-4-(3-methylimidazo[1,5-a]pyridin-8-yl)isoindolin-1-one | Method AcHSS C18, m/z = 455 [M + H]+, Ret. time = 2.1 min. | $^1$H NMR (400 MHz, DMSO): δ 9.91 (s, 1 H), 8.76 (s, 1 H), 8.53 (d, J = 8.9 Hz, 1 H), 8.12 (d, J = 7.4 Hz, 1 H), 8.05 (d, J = 3.1 Hz, 1 H), 7.76 (d, J = 8.2 Hz, 1 H), 7.48 (dd, J = 2.9, 8.7 Hz, 1 H), 7.22 (s, 1 H), 6.99 (d, J = 9.3 Hz, 1 H), 6.91 (d, J = 6.8 Hz, 1 H), 6.79 (t, J = 7.1 Hz, 1 H), 4.74 (d, J = 4.3 Hz, 1 H), 4.45 (s, 2 H), 3.71-3.64 (m, 1 H), 3.53-3.48 (m, 2 H), 2.87 (ddd, J = 2.6, 10.1, 12.3 Hz, 2 H), 2.67 (s, 3 H), 1.90 (dd, J = 3.9, 12.8 Hz, 2 H), 1.62-1.52 (m, 2 H). | F AC15 BC95 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-181 | 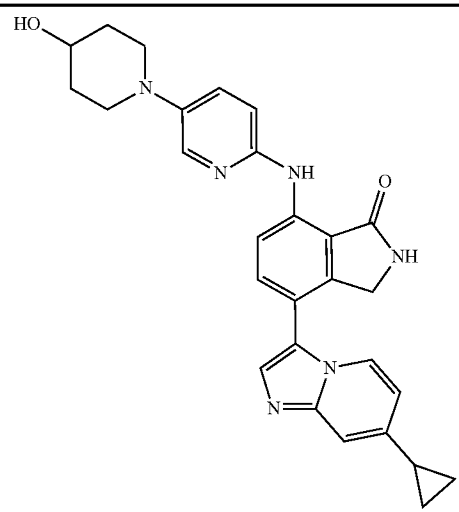 | 4-(7-cyclopropyl-imidazo[1,2-a]pyridin-3-yl)-7-[[5-(4-hydroxy-1-piperidyl)-2-pyridyl]amino]iso-indolin-1-one | Method AcHSS C18, m/z = 481 [M + H]+, Ret. time = 2.36 min. | ¹H NMR (400 MHz, DMSO): δ 9.87 (s, 1 H), 8.79 (s, 1 H), 8.58 (d, J = 8.3 Hz, 1 H), 8.28 (d, J = 6.8 Hz, 1 H), 8.05 (d, J = 3.1 Hz, 1 H), 7.77 (s, 1 H), 7.71 (d, J = 8.7 Hz, 1 H), 7.48 (dd, J = 3.4, 8.7 Hz, 1 H), 7.41 (s, 1 H), 6.99 (d, J = 9.0 Hz, 1 H), 6.70 (dd, J = 1.8, 7.3 Hz, 1 H), 4.74 (d, J = 4.2 Hz, 1 H), 4.42 (s, 2 H), 3.71-3.64 (m, 1 H), 3.54-3.46 (m, 2 H), 2.87 (ddd, J = 2.8, 9.4, 12.5 Hz, 2 H), 2.09 (ddd, J = 5.2, 8.2, 13.5 Hz, 1 H), 1.89 (dd, J = 4.1, 12.7 Hz, 2 H), 1.62-1.51 (m, 2 H), 1.07 (ddd, J = 4.3, 6.5, 8.1 Hz, 2 H), 0.85 (ddd, J = 4.7, 4.7, 6.8 Hz, 2 H). | F AC15 BC96 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-182 | 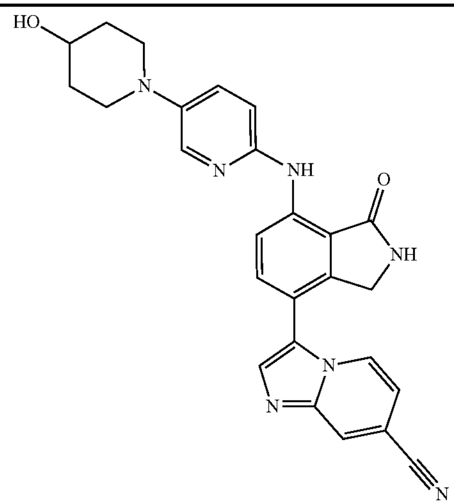 | 3-[7-[[5-(4-hydroxy-1-piperidyl)-2-pyridyl]amino]-1-oxo-isoindolin-4-yl]imidazo[1,2-a]pyridine-7-carbonitrile | Method AcHSS C18, m/z = 466 [M + H]+, Ret. time = 2.53 min. | ¹H NMR (400 MHz, DMSO): δ 9.86 (s, 1 H), 8.78 (s, 1 H), 8.57-8.51 (m, 2 H), 8.43 (s, 1 H), 8.14 (s, 1 H), 8.00 (d, J = 2.9 Hz, 1 H), 7.74-7.71 (m, 1 H), 7.44 (dd, J = 3.0, 9.0 Hz, 1 H), 7.20 (dd, J = 1.7, 7.2 Hz, 1 H), 6.97-6.93 (m, 1 H), 4.69 (s, 1 H), 4.39 (s, 2 H), 3.64-3.60 (m, 1 H), 3.49-3.43 (m, 2 H), 2.86-2.78 (m, 2 H), 1.86-1.81 (m, 2 H), 1.56-1.47 (m, 2 H). | F AC15 BC76 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-183 | 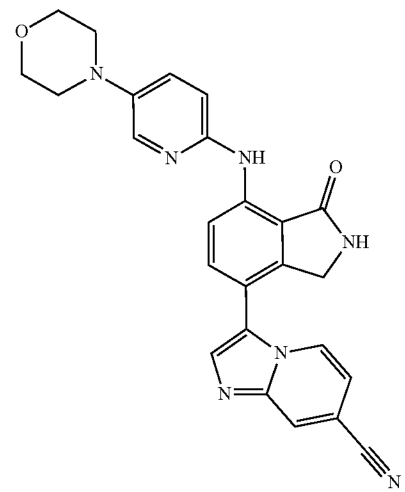 [SMILES: N#Cc1ccn2c(-c3ccc(Nc4ccc(N5CCOCC5)cn4)c4c3CNC4=O)cnc2c1] | 3-[7-[(5-morpholino-2-pyridyl)amino]-1-oxo-isoindolin-4-yl]imidazo[1,2-a]pyridine-7-carbonitrile | Method AcHSS C18, m/z = 452 [M + H]+, Ret. time = 3.23 min. | ¹H NMR (400 MHz, DMSO): δ 9.91 (s, 1 H), 8.81 (s, 1 H), 8.60 (d, J = 8.7 Hz, 1 H), 8.54 (dd, J = 0.9, 7.2 Hz, 1 H), 8.46 (dd, J = 1.0, 1.7 Hz, 1 H), 8.15 (s, 1 H), 8.03 (d, J = 2.9 Hz, 1 H), 7.75 (d, J = 9.0 Hz, 1 H), 7.47 (dd, J = 3.1, 9.0 Hz, 1 H), 7.22 (dd, J = 1.7, 7.2 Hz, 1 H), 7.01 (d, J = 9.0 Hz, 1 H), 4.42 (s, 2 H), 3.78 (t, J = 5.1 Hz, 4 H), 3.11 (t, J = 4.5 Hz, 4 H). | F AC10 BC76 |
| I-184 | 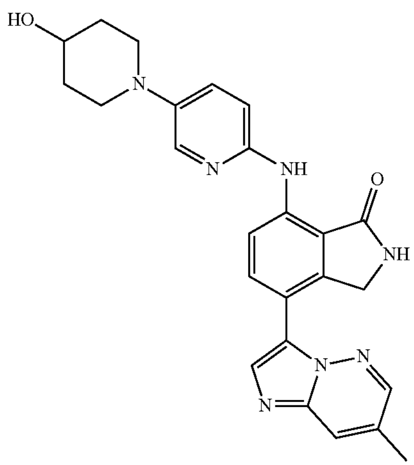 [SMILES: Cc1cnn2c(-c3ccc(Nc4ccc(N5CCC(O)CC5)cn4)c4c3CNC4=O)cnc2c1] | 7-[[5-(4-hydroxy-1-piperidyl)-2-pyridyl]amino]-4-(7-methylimidazo[1,2-b]pyridazin-3-yl)isoindolin-1-one | Method AcHSS C18, m/z = 456 [M + H]+, Ret. time = 2.3 min. | ¹H NMR (400 MHz, DMSO): δ 9.87 (s, 1 H), 8.79 (s, 1 H), 8.52 (d, J = 2.0 Hz, 1 H), 8.47 (d, J = 8.6 Hz, 1 H), 8.09 (d, J = 8.8 Hz, 1 H), 8.02-7.99 (m, 3 H), 7.44 (dd, J = 2.9, 9.0 Hz, 1 H), 6.95 (d, J = 8.8 Hz, 1 H), 4.51 (s, 2 H), 3.67-3.59 (m, 1 H), 3.48-3.42 (m, 2 H), 2.88-2.79 (m, 2 H), 2.43 (s, 3 H), 1.88-1.80 (m, 2 H), 1.57-1.47 (m, 2 H). | F AC15 BC97 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-185 | (structure shown) | 8-ethoxy-3-[7-[[5-(4-hydroxy-1-piperidyl)-2-pyridyl]amino]-1-oxo-isoindolin-4-yl]imidazo[1,2-a]pyridine-7-carbonitrile | Method BicarbB EHC18, m/z = 510 [M + H]+, Ret. time = 4.16 min. | ¹H NMR (400 MHz, DMSO): δ 9.85 (s, 1 H), 8.77 (s, 1 H), 8.54 (d, J = 8.6 Hz, 1 H), 8.10 (d, J = 7.1 Hz, 1 H), 8.04 (s, 1 H), 8.00 (d, J = 2.8 Hz, 1 H), 7.68 (d, J = 8.6 Hz, 1 H), 7.44 (dd, J = 3.0, 9.1 Hz, 1 H), 7.04 (d, J = 7.1 Hz, 1 H), 6.95 (d, J = 9.1 Hz, 1 H), 5.07 (q, J = 7.1 Hz, 2 H), 4.68 (d, J = 4.0 Hz, 1 H), 4.38 (s, 2 H), 3.66-3.59 (m, 1 H), 3.49-3.41 (m, 2 H), 2.86-2.78 (m, 2 H), 1.87-1.80 (m, 2 H), 1.56-1.46 (m, 2 H), 1.42 (dd, J = 6.9, 6.9 Hz, 3 H). | F AC15 BC98 By-product from synthesis of I-188 (SnAr of 8-F with ethanol) |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-186 | 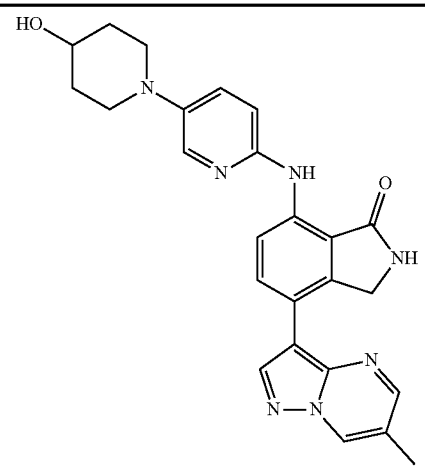 | 7-[[5-(4-hydroxy-1-piperidyl)-2-pyridyl]amino]-4-(6-methylpyrazolo[1,5-a]pyrimidin-3-yl)isoindolin-1-one | Method AcHSS C18, m/z = 456 [M + H]+, Ret. time = 2.84 min. | ¹H NMR (400 MHz, DMSO) δ 9.80 (s, 1 H), 9.04 (dd, J = 1.2, 2.1 Hz, 1 H), 8.78 (s, 1 H), 8.58 (d, J = 2.1 Hz, 1 H), 8.44 (t, J = 4.3 Hz, 2 H), 8.18-8.15 (m, 1 H), 7.99 (d, J = 3.0 Hz, 1 H), 7.43 (dd, J = 3.0, 9.0 Hz, 1 H), 6.95-6.91 (m, 1 H), 4.70 (d, J = 4.1 Hz, 1 H), 4.64-4.62 (m, 2 H), 3.66-3.60 (m, 1 H), 3.53-3.42 (m, 2 H), 2.86-2.78 (m, 2 H), 2.39-2.38 (m, 3 H), 1.88-1.82 (m, 2 H), 1.58-1.48 (m, 2 H). | F AC15 BC70 |
| I-187 | 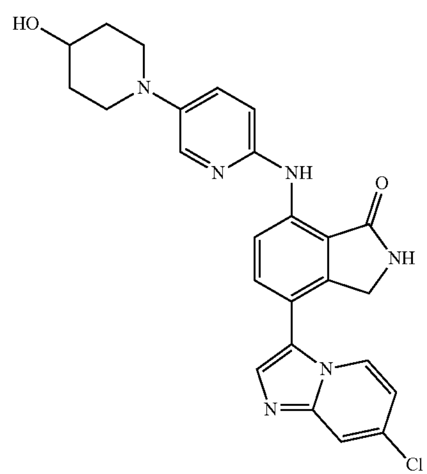 [SMILES: O=C1NCc2c(-c3cnc4cc(Cl)ccn34)ccc(Nc3ccc(N4CCC(O)CC4)cn3)c21] | 4-(7-chloroimidazo[1,2-a]pyridin-3-yl)-7-[[5-(4-hydroxy-1-piperidyl)-2-pyridyl]amino]iso-indolin-1-one | Method AcHSS C18, m/z = 475 [M + H]+, Ret. time = 2.34 min. | ¹H NMR (400 MHz, DMSO): δ 9.95 (s, 1 H), 8.87 (s, 1 H), 8.66 (d, J = 8.5 Hz, 1 H), 8.51 (d, J = 7.4 Hz, 1 H), 8.12 (d, J = 3.0 Hz, 1 H), 7.98 (s, 1 H), 7.95 (dd, J = 1.0, 2.1 Hz, 1 H), 7.81 (d, J = 8.7 Hz, 1 H), 7.55 (dd, J = 3.2, 8.9 Hz, 1 H), 7.09 (dd, J = 2.1, 7.0 Hz, 1 H), 7.06 (d, J = 8.9 Hz, 1 H), 4.80 (d, J = 4.3 Hz, 1 H), 4.50 (s, 2 H), 3.78-3.70 (m, 1 H), 3.61-3.53 (m, 2 H), 2.94 (ddd, J = 2.9, 9.9, 12.6 Hz, 2 H), 1.99-1.93 (m, 2 H), 1.68-1.58 (m, 2 H). | F AC15 BC99 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-188 | (structure) | 8-fluoro-3-[7-[[5-(4-hydroxy-1-piperidyl)-2-pyridyl]amino]-1-oxo-isoindolin-4-yl]imidazo[1,2-a]pyridine-7-carbonitrile | Method AcHSS C18, m/z = 484 [M + H]+, Ret. time = 2.94 min. | ¹H NMR (400 MHz, DMSO): δ 9.87 (s, 1 H), 8.79 (s, 1 H), 8.56 (d, J = 8.6 Hz, 1 H), 8.37 (d, J = 7.3 Hz, 1 H), 8.16 (s, 1 H), 8.00 (d, J = 3.0 Hz, 1 H), 7.71 (d, J = 8.6 Hz, 1 H), 7.44 (dd, J = 3.0, 9.1 Hz, 1 H), 7.22 (dd, J = 5.8, 7.1 Hz, 1 H), 6.95 (d, J = 9.1 Hz, 1 H), 4.69 (d, J = 4.0 Hz, 1 H), 4.39 (s, 2 H), 3.65-3.58 (m, 1 H), 3.49-3.42 (m, 2 H), 2.86-2.78 (m, 2 H), 1.87-1.81 (m, 2 H), 1.56-1.46 (m, 2 H). | F AC15 BC98 |

TABLE 8-continued
Characterization Data (LCMS and ¹H NMR).
| # | STRUCTURE | NAME | LCMS | ¹H NMR | Method Reagent AA BB |
|---|---|---|---|---|---|
| I-189 | 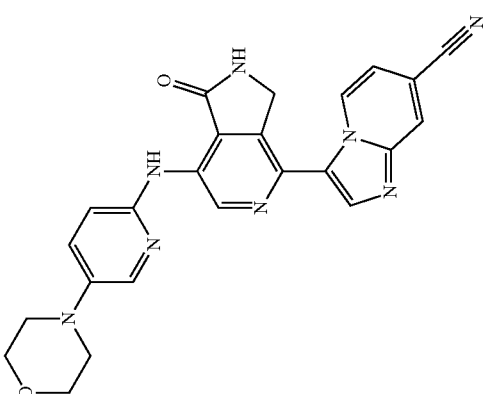 | 3-[7-[(5-morpholino-2-pyridyl)amino]-1-oxo-2,3-dihydropyrrolo[3,4-c]pyridin-4-yl]imidazo[1,2-a]pyridine-7-carbonitrile | Method BicarbB EHC18, m/z = 453 [M + H]+, Ret. time = 3.85 min. | ¹H NMR (400 MHz, DMSO): δ 9.98 (dd, J = 0.9, 7.4 Hz, 1 H), 9.96 (s, 1 H), 9.50 (s, 1 H), 9.31 (s, 1 H), 8.51 (dd, J = 1.0, 1.8 Hz, 1 H), 8.36 (s, 1 H), 8.06 (d, J = 2.9 Hz, 1 H), 7.49 (dd, J = 3.0, 8.9 Hz, 1 H), 7.39 (dd, J = 1.8, 7.4 Hz, 1 H), 7.09 (d, J = 8.9 Hz, 1 H), 4.81 (s, 2 H), 3.79 (t, J = 4.8 Hz, 4 H), 3.13 (t, J = 4.8 Hz, 4 H). | A, AC10 BC10 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-190 | (structure) | 5-chloro-7-[[5-(4-hydroxy-1-piperidyl)-2-pyridyl]amino]-4-(1-methylpyrrolo[2,3-b]pyridin-4-yl)isoindolin-1-one | Method BicarbB EHC18, m/z = 489 [M + H]+, Ret. time = 3.84 min. | ¹H NMR (400 MHz, DMSO): δ 9.79 (s, 1 H), 8.73 (s, 2 H), 8.36 (d, J = 4.6 Hz, 1 H), 8.06 (d, J = 2.7 Hz, 1 H), 7.57 (d, J = 3.0 Hz, 1 H), 7.46 (dd, J = 3.0, 9.5 Hz, 1 H), 7.14 (d, J = 4.5 Hz, 1 H), 6.96 (d, J = 8.5 Hz, 1 H), 6.21 (d, J = 3.4 Hz, 1 H), 4.71 (d, J = 2.8 Hz, 1 H), 4.19 (d, J = 18.0 Hz, 1 H), 3.95 (d, J = 17.6 Hz, 1 H), 3.89 (s, 3 H), 3.67-3.60 (m, 1 H), 3.50 (td, J = 4.5, 11.8 Hz, 2 H), 2.85 (ddd, J = 2.9, 9.7, 12.1 Hz, 2 H), 1.84 (dd, J = 3.8, 13.0 Hz, 2 H), 1.52 (tdd, J = 4.7, 12.1, 12.1 Hz, 2 H). | H AC15 BC26 |

| # | STRUCTURE | NAME | LCMS | 1H NMR | Method Reagent AA BB |
|---|---|---|---|---|---|
| I-191 | Isomer 1 - made from single ent AC22 | (R)-4-(7-methylimidazo[1,2-a]pyridin-3-yl)-7-((5-(tetrahydrofuran-3-yl)pyridin-2-yl)amino)isoindolin-1-one | Method AcHSS C18, m/z = 426 [M + H]+, Ret. time = 2.83 min. | 1H NMR (400 MHz, DMSO): δ 10.13 (s, 1 H), 8.88 (s, 1 H), 8.76 (d, J = 10.3 Hz, 1 H), 8.39 (d, J = 7.2 Hz, 1 H), 8.28 (d, J = 2.5 Hz, 1 H), 7.90 (s, 1 H), 7.78 (d, J = 8.9 Hz, 1 H), 7.70 (dd, J = 2.4, 8.0 Hz, 1 H), 7.55 (s, 1 H), 7.05 (d, J = 8.1 Hz, 1 H), 6.93 (dd, J = 1.6, 7.2 Hz, 1 H), 4.46 (s, 2 H), 4.09 (t, J = 7.6 Hz, 1 H), 4.02 (ddd, J = 8.2, 8.2, 4.5 Hz, 1 H), 3.87 (ddd, J = 7.7, 7.7, 7.7 Hz, 1 H), 3.60 (t, J = 8.1 Hz, 1 H), 3.49-3.45 (m, 1 H), 2.47 (s, 3 H), 2.42-2.31 (m, 1 H), 2.03-1.94 (m, 1 H). | F AC22 BC45 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-192 | Isomer 2 - made from single ent AC22 | (S)-4-(7-methylimidazo[1,2-a]pyridin-3-yl)-7-((5-(tetrahydrofuran-3-yl)pyridin-2-yl)amino)isoindolin-1-one | Method AcHSS C18, m/z = 426 [M + H]+, Ret. time = 2.82 min. | ¹H NMR (400 MHz, DMSO): δ 10.13 (s, 1 H), 8.88 (s, 1 H), 8.76 (d, J = 10.3 Hz, 1 H), 8.39 (d, J = 7.2 Hz, 1H), 8.28 (d, J = 2.5 Hz, 1 H), 7.90 (s, 1 H), 7.78 (d, J = 8.9 Hz, 1 H), 7.70 (dd, J = 2.4, 8.0 Hz, 1 H), 7.55 (s, 1 H), 7.05 (d, J = 8.1 Hz, 1 H), 6.93 (dd, J = 1.6, 7.2 Hz, 1 H), 4.46 (s, 2 H), 4.09 (t, J = 7.6 Hz, 1 H), 4.02 (ddd, J = 8.2, 8.2, 4.5 Hz, 1 H), 3.87 (ddd, J = 7.7, 7.7, 7.7 Hz, 1 H), 3.60 (t, J = 8.1 Hz, 1 H), 3.49-3.45 (m, 1 H), 2.47 (s, 3 H), 2.42-2.31 (m, 1 H), 2.03-1.94 (m, 1 H). | F AC22 BC45 |
| I-193 | 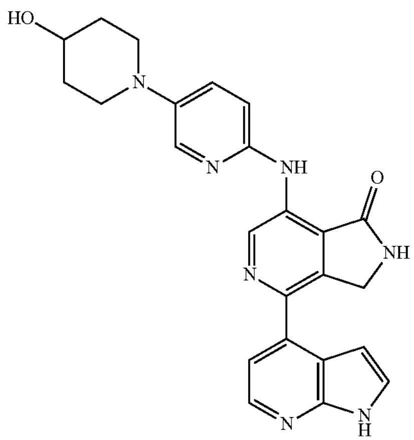 [SMILES: O=C1NCc2c(-c3ccnc4[nH]ccc34)ncc(Nc3ccc(N4CCC(O)CC4)cn3)c21] | 7-[[5-(4-hydroxy-1-piperidyl)-2-pyridyl]amino]-4-(1H-pyrrolo[2,3-b]pyridin-4-yl)-2,3-dihydropyrrolo[3,4-c]pyridin-1-one | Method AcHSS C18, m/z = 442 [M + H]+, Ret. time = 2.16 min. | ¹H NMR (400 MHz, DMSO) δ 11.74-11.70 (m, 1 H), 9.92 (s, 1 H), 9.50-9.49 (m, 1 H), 9.15 (s, 1 H), 8.31 (d, J = 5.0 Hz, 1 H), 8.07 (d, J = 3.0 Hz, 1 H), 7.53-7.45 (m, 2 H), 7.35 (d, J = 5.0 Hz, 1 H), 7.06-7.02 (m, 1 H), 6.91 (dd, J = 1.9, 3.4 Hz, 1 H), 4.73-4.71 (m, 3 H), 3.67-3.61 (m, 1 H), 3.53-3.47 (m, 2 H), 2.89-2.81 (m, 2 H), 1.89-1.82 (m, 2 H), 1.58-1.48 (m, 2 H). | A SC15 BC25 |

TABLE 8-continued

Characterization Data (LCMS and $^1$H NMR).

| # | STRUCTURE | NAME | LCMS | $^1$H NMR | Method Reagent AA BB |
|---|---|---|---|---|---|
| I-194 | 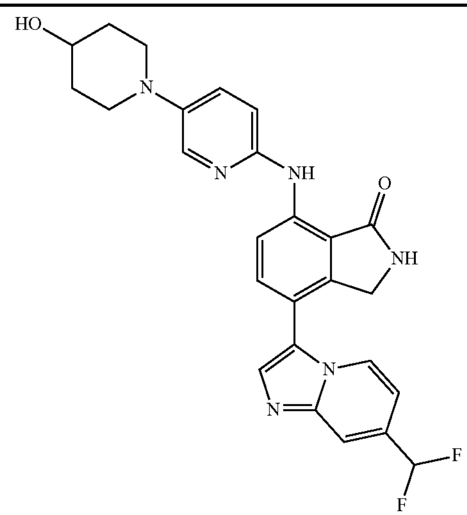 | 4-[7-(difluoromethyl)imidazo[1,2-a]pyridin-3-yl]-7-[[5-(4-hydroxy-1-piperidyl)-2-pyridyl]amino]isoindolin-1-one | Method AcHSS C18, m/z = 491 [M + H]+, Ret. time = 2.32 min. | $^1$H NMR (400 MHz, DMSO): δ 9.98 (s, 1 H), 8.85 (s, 1 H), 8.69 (d, J = 7.1 Hz, 1 H), 8.59 (d, J = 8.1 Hz, 1 H), 8.33 (s, 1 H), 8.17 (s, 1 H), 8.11 (d, J = 2.9 Hz, 1 H), 7.79 (d, J = 10.1 Hz, 1 H), 7.58 (dd, J = 2.6, 8.9 Hz, 1 H), 7.39 (dd, J = 1.8, 7.6 Hz, 1 H), 7.28 (t, J = 55.3 Hz, 1 H), 7.06 (d, J = 8.4 Hz, 1 H), 4.43 (s, 2 H), 4.37 (s, 1 H), 3.72-3.65 (m, 1 H), 3.55-3.48 (m, 2 H), 2.99-2.94 (m, 2 H), 1.92-1.87 (m, 2 H), 1.63-1.53 (m, 2 H). | F AC15 BC101 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-195 | (structure) | N-ethyl-3-[7-[[5-(4-hydroxy-1-piperidyl)-2-pyridyl]amino]-1-oxo-isoindolin-4-yl]imidazo[1,2-a]pyridine-7-carboxamide | Method BicarbB EHC18, m/z = 512 [M + H]+, Ret. time = 2.99 min. | ¹H NMR (400 MHz, DMSO): δ 9.84 (s, 1 H), 8.76 (s, 1 H), 8.69 (t, J = 5.6 Hz, 1 H), 8.56 (d, J = 8.6 Hz, 1 H), 8.44 (d, J = 6.6 Hz, 1 H), 8.20 (s, 1 H), 8.00 (d, J = 3.0 Hz, 1 H), 7.97 (s, 1 H), 7.71 (d, J = 8.6 Hz, 1 H), 7.43 (dd, J = 3.0, 9.1 Hz, 1 H), 7.36 (dd, J = 1.8, 7.3 Hz, 1 H), 6.94 (d, J = 8.8 Hz, 1 H), 4.68 (d, J = 4.3 Hz, 1 H), 4.39 (s, 2 H), 3.65-3.59 (m, 1 H), 3.49-3.41 (m, 2 H), 3.37-3.28 (m, 2 H), 2.86-2.78 (m, 2 H), 1.87-1.80 (m, 2 H), 1.56-1.46 (m, 2 H), 1.16 (dd, J = 7.2, 7.2 Hz, 3 H). | F SV15 BC7 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-196 | 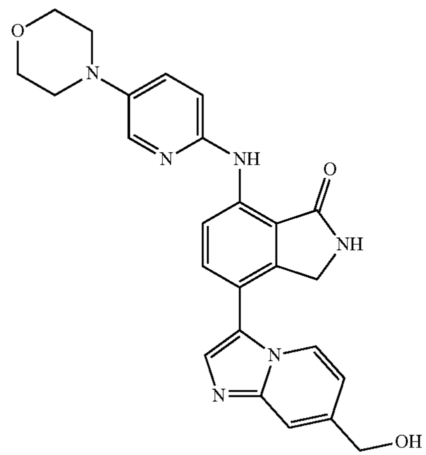 [SMILES: O=C1NCc2c(-c3cnc4cc(CO)ccn34)ccc(Nc3ccc(N4CCOCC4)cn3)c21] | 4-[7-(hydroxymethyl)imidazo[1,2-a]pyridin-3-yl]-7-[(5-morpholino-2-pyridyl)amino]isoindolin-1-one | Method AcHSS C18, m/z = 457 [M + H]+, Ret. time = 2.38 min. | ¹H NMR (400 MHz, DMSO): δ 9.87 (s, 1 H), 8.78 (s, 1 H), 8.58 (d, J = 8.0 Hz, 1 H), 8.35 (d, J = 7.9 Hz, 1 H), 8.01 (d, J = 3.0 Hz, 1 H), 7.82 (s, 1 H), 7.70 (d, J = 8.4 Hz, 1 H), 7.55 (s, 1 H), 7.46 (dd, J = 3.2, 8.8 Hz, 1 H), 6.99 (d, J = 8.8 Hz, 1 H), 6.87 (dd, J = 1.6, 7.2 Hz, 1 H), 5.46 (t, J = 5.4 Hz, 1 H), 4.59 (d, J = 5.2 Hz, 2 H), 4.39 (s, 2 H), 3.77 (t, J = 4.4 Hz, 4 H), 3.1 ((t, J = 4.6 Hz, 4 H) | F AC10 BC94 |
| I-197 | 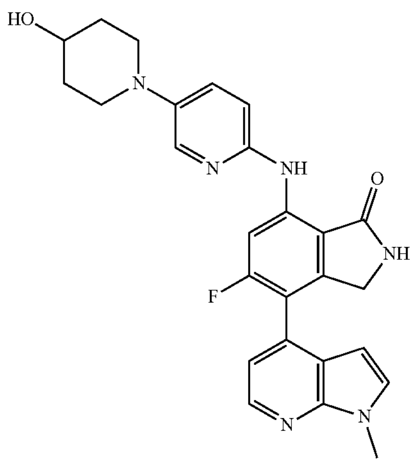 [SMILES: Cn1ccc2c(-c3c(F)cc(Nc4ccc(N5CCC(O)CC5)cn4)c4c3CNC4=O)ccnc21] | 5-fluoro-7-[[5-(4-hydroxy-1-piperidyl)-2-pyridyl]amino]-4-(1-methylpyrrolo[2,3-b]pyridin-4-yl)isoindolin-1-one | Method BicarbB EHC18, m/z = 473 [M + H]+, Ret. time = 4.07 min. | ¹H NMR (400 MHz, DMSO): δ 9.92 (s, 1 H), 8.73 (s, 1 H), 8.46 (d, J = 14.1 Hz, 1H), 8.34 (d, J = 5.1 Hz, 1 H), 8.06 (d, J = 2.6 Hz, 1H), 7.57 (d, J = 2.8 Hz, 1 H), 7.46 (dd, J = 2.9, 8.9 Hz, 1 H), 7.24 (d, J = 4.6 Hz, 1 H), 6.97 (d, J = 8.9 Hz, 1 H), 6.29 (dd, J = 2.5, 3.6 Hz, 1 H), 4.71 (d, J = 4.3 Hz, 1 H), 4.31 (s, 2 H), 3.88 (s, 3 H), 3.68-3.59 (m, 1 H), 3.52-3.44 (m, 2 H), 2.84 (ddd, J = 2.7, 10.1, 12.6 Hz, 2 H), 1.85 (dd, J = 4.0, 13.3 Hz, 2 H), 1.52 (ddt, J = 3.7, 10.6, 11.0 Hz, 2 H), | I AC15 BC26 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-198 | 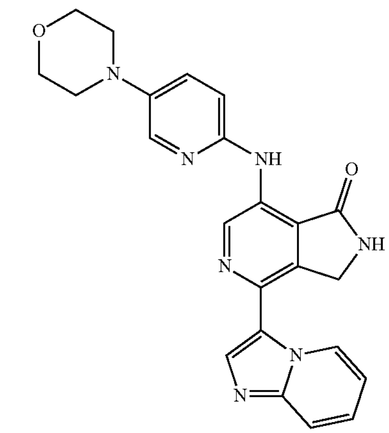 [SMILES: O=C1NCc2c(-c3cnc4ccccn34)ncc(Nc3ccc(N4CCOCC4)cn3)c21] | 4-imidazo[1,2-a]pyridin-3-yl-7-[[5-morpholino-2-pyridyl]amino]-2,3-dihydropyrrolo[3,4-c]pyridin-1-one | Method AcHSS C18, m/z = 428 [M + H]+, Ret. time = 2.68 min. | ¹H NMR (400 MHz, DMSO): δ 10.00 (d, J = 7.3 Hz, 1 H), 9.83 (s, 1 H), 9.68 (s, 1 H), 9.35 (s, 1 H), 8.66 (s, 1 H), 8.14-8.05 (m, 3 H), 7.66-7.62 (m, 2 H), 7.20 (d, J = 8.6 Hz, 1 H), 4.78 (s, 2 H), 3.81 (t, J = 4.6 Hz, 4 H), 3.19 (t, J = 4.4 Hz, 4 H). | Hc AC10 BC11 |
| I-199 | 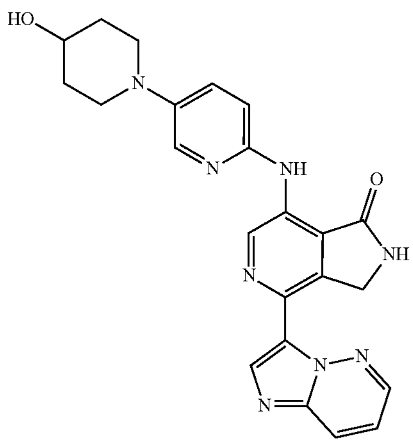 | 7-[[5-(4-hydroxy-1-piperidyl)-2-pyridyl]amino]-4-imidazo[1,2-b]pyridazin-3-yl-2,3-dihydropyrrolo[3,4-c]pyridin-1-one | Method AcHSS C18, m/z = 443 [M + H]+, Ret. time = 2.14 min. | ¹H NMR (400 MHz, DMSO): δ 9.84 (s, 1 H), 9.42 (s, 1 H), 9.10 (s, 1 H), 8.63 (dd, J = 1.6, 4.4 Hz, 1 H), 8.26 (dd, J = 1.9, 9.6 Hz, 1 H), 8.17 (s, 1 H), 8.06 (d, J = 2.9 Hz, 1 H), 7.48 (dd, J = 3.0, 8.9 Hz, 1 H), 7.34 (dd, J = 4.3, 9.5 Hz, 1 H), 7.05 (d, J = 9.2 Hz, 1 H), 4.72 (s, 1 H), 4.61 (s, 2 H), 3.68-3.60 (m, 1 H), 3.49 (td, J = 4.3, 12.4 Hz, 2 H), 2.85 (ddd, J = 3.1, 9.9, 12.9 Hz, 2 H), 1.86 (dd, J = 3.8, 13.3 Hz, 2 H), 1.53 (ddt, J = 3.7, 10.6, 11.1 Hz, 2 H). | Hc AC15 BC102 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-200 | 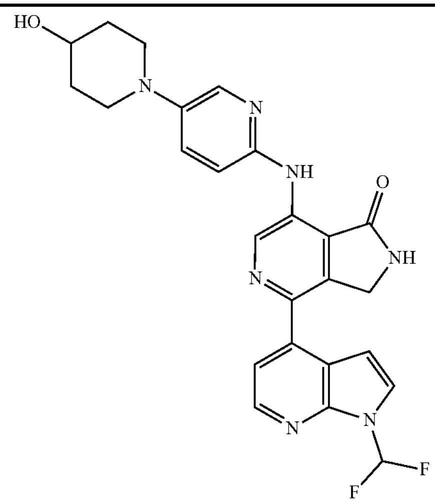 | 4-[1-(difluoromethyl)pyrrolo[2,3-b]pyridin-4-yl]-7-[[5-(4-hydroxy-1-piperidyl)-2-pyridyl]amino]-2,3-dihydropyrrolo[3,4-c]pyridin-1-one | Method BicarbB EHC18, m/z = 492 [M + H]+, Ret. time = 3.7 min. | ¹H NMR (400 MHz, DMSO): δ 9.99 (s, 1 H), 9.60 (s, 1 H), 9.24 (s, 1 H), 8.50 (d, J = 5.9 Hz, 1 H), 8.25 (t, J = 60.3 Hz, 1 H), 8.12 (d, J = 3.0 Hz, 1 H), 7.92 (d, J = 4.8 Hz, 1 H), 7.64 (d, J = 5.0 Hz, 1 H), 7.52 (dd, J = 3.0, 9.1 Hz, 1 H), 7.30 (d, J = 4.0 Hz, 1 H), 7.10 (d, J = 9.1 Hz, 1 H), 4.82 (s, 2 H), 4.75 (d, J = 4.1 Hz, 1 H), 3.73-3.65 (m, 1 H), 3.58-3.50 (m, 2 H), 2.90 (ddd, J = 2.7, 10.0, 12.6 Hz, 2 H), 1.90 (dd, J = 3.3, 13.2 Hz, 2 H), 1.62-1.52 (m, 2H). | A AC15 BC103 |
| I-201 | 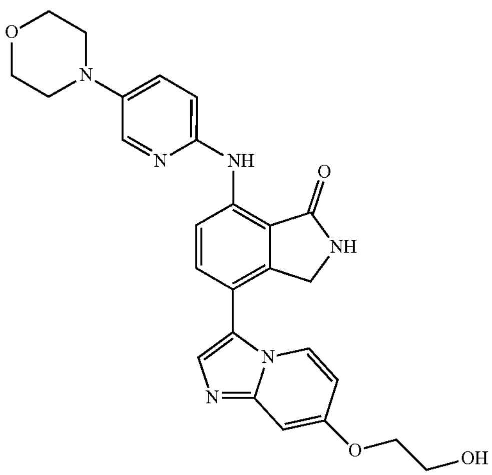 [SMILES: O=C1NCc2c(-c3cnc4cc(OCCO)ccn34)ccc(Nc3ccc(N4CCOCC4)cn3)c21] | 4-[7-(2-hydroxyethoxy)imidazo[1,2-a]pyridin-3-yl]-7-[(5-morpholino-2-pyridyl)amino]isoindolin-1-one | Method AcHSS C18, m/z = 487 [M + H]+, Ret. time = 2.43 min. | ¹H NMR (400 MHz, DMSO): δ 9.90 (s, 1 H), 8.81 (s, 1 H), 8.60 (d, J = 8.6 Hz, 1 H), 8.29 (d, J = 8.1 Hz, 1 H), 8.05 (d, J = 3.0 Hz, 1 H), 7.73 (s, 1 H), 7.71 (d, J = 8.4 Hz, 1 H), 7.50 (dd, J = 2.9, 9.2 Hz, 1 H), 7.09 (d, J = 2.5 Hz, 1 H), 7.03 (d, J = 2.8, 7.6 Hz, 1 H), 6.71 (dd, J = 5.6 Hz, 1 H), 4.99 (t, J = 5.6 Hz, 1 H), 4.43 (s, 2 H), 4.16 (t, J = 4.9 Hz, 2 H), 3.85-3.80 (m, 6 H), 3.14 (t, J = 4.9 Hz, 4 H). | F AC10 BC106 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-202 | 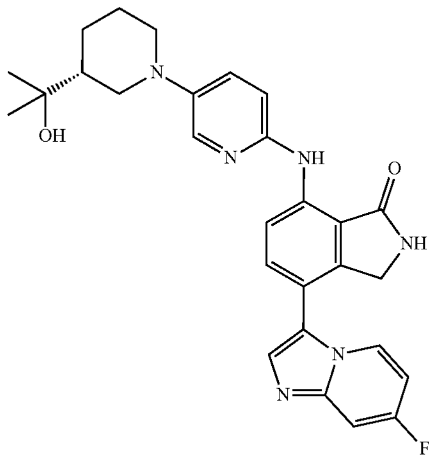 [SMILES: CC(C)(O)[C@@H]1CCCN(c2ccc(Nc3ccc(-c4cnc5cc(F)ccn45)c4c3C(=O)NC4)nc2)C1] | 4-(7-fluoroimidazo[1,2-a]pyridin-3-yl)-7-[[5-[(3R)-3-(1-hydroxy-1-methyl-ethyl)-1-piperidyl]-2-pyridyl]amino]isoindolin-1-one | Method AcHSS C18, m/z = 501 [M + H]+, Ret. time = 2.48 min. | ¹H NMR (400 MHz, DMSO): δ 9.87 (s, 1 H), 8.80 (s, 1 H), 8.59 (d, J = 8.4 Hz, 1 H), 8.46 (dd, J = 5.7, 7.5 Hz, 1 H), 8.04 (d, J = 2.7 Hz, 1 H), 7.86 (s, 1 H), 7.73 (d, J = 8.6 Hz, 1 H), 7.57 (dd, J = 2.9, 9.9 Hz, 1 H), 7.46 (dd, J = 3.0, 9.0 Hz, 1 H), 7.05-7.00 (m, 2 H), 4.43 (s, 2 H), 4.33 (s, 1 H), 3.79 (d, J = 12.5 Hz, 1 H), 3.66 (d, J = 12.5 Hz, 1 H), 2.63-2.59 (m, 1 H), 2.48 (t, J = 11.6 Hz, 1 H), 1.89 (d, J = 13.1 Hz, 1 H), 1.81 (d, J = 13.1 Hz, 1 H), 1.67-1.58 (m, 2 H), 1.24-1.19 (m, 1 H), 1.17 (s, 3 H), 1.14 (s, 3 H). | F AC29 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-203 | (structure) | 1-[6-[[7-(7-fluoroimidazo[1,2-a]pyridin-3-yl)-3-oxo-isoindolin-4-yl]amino]-3-pyridyl]piperidine-4-carboxylic acid | Method BicarbB EHC18, m/z = 487 [M + H]+, Ret. time = 2.57 min. | ¹H NMR (400 MHz, DMSO): δ 9.84 (s, 1 H), 8.77 (s, 1 H), 8.56 (d, J = 9.3 Hz, 1 H), 8.43 (dd, J = 5.4, 7.4 Hz, 1 H), 8.01 (d, J = 2.8 Hz, 1 H), 7.82 (s, 1 H), 7.69 (d, J = 8.4 Hz, 1 H), 7.53 (dd, J = 2.7, 10.0 Hz, 1 H), 7.46 (dd, J = 3.0, 9.0 Hz, 1 H), 7.01-6.95 (m, 2 H), 4.38 (s, 2 H), 3.56 (d, J = 3.7, 12.2 Hz, 2 H), 2.75 (ddd, J = 11.7, 11.7, 2.5 Hz, 2 H), 2.40-2.35 (m, 1 H), 1.93 (dd, J = 3.7, 13.9 Hz, 2 H), 1.74-1.69 (m, 2 H). | F AC31 BC80 |
| I-204 | (structure) | 4-(7-fluoroimidazo[1,2-a]pyridin-3-yl)-7-[[5-[4-(hydroxymethyl)-1-piperidyl]-2-pyridyl]amino]isoindolin-1-one | Method BicarbB EHC18, m/z = 473 [M + H]+, Ret. time = 3.48 min. | ¹H NMR (400 MHz, DMSO): δ 9.86 (s, 1 H), 8.79 (s, 1 H), 8.56 (d, J = 8.8 Hz, 1 H), 8.49 (dd, J = 5.7, 7.8 Hz, 1 H), 8.02 (d, J = 3.0 Hz, 1 H), 7.93 (s, 1 H), 7.70 (d, J = 8.8 Hz, 1 H), 7.63 (dd, J = 3.1, 9.9 Hz, 1 H), 7.46 (dd, J = 3.1, 9.0 Hz, 1 H), 7.09 (ddd, J = 7.5, 7.5, 2.7 Hz, 1 H), 6.97 (d, J = 9.2 Hz, 1 H), 4.52 (s, 1 H), 4.39 (s, 2 H), 3.64 (d, J = 11.8 Hz, 2 H), 2.65 (ddd, J = 12.1, 12.1, 2.3 Hz, 2 H), 1.79 (d, J = 11.5 Hz, 2 H), 1.56-1.49 (m, 1 H), 1.32 (dd, J = 3.7, 12.5 Hz, 1 H), 1.26 (dd, J = 4.1, 12.1 Hz, 1 H). | F AC32 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-205 | 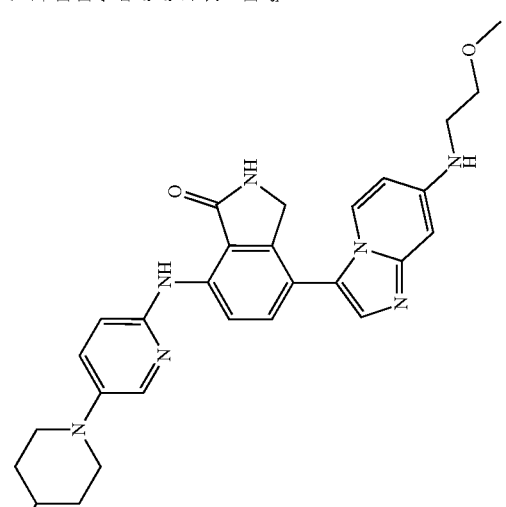 | 7-[[5-(4-hydroxy-1-piperidyl)-2-pyridyl]amino]-4-[7-(2-methoxyethylamino)imidazo[1,2-a]pyridin-3-yl]isoindolin-1-one Formic acid salt | Method AcHSS C18, m/z = 514 [M + H]+, Ret. time = 2.25 min. | ¹H NMR (400 MHz, DMSO) 9.83 (1H, s), 8.77 (1H, s), 8.55 (1H, d, J = 8.8 Hz), 8.38 (1H, s), 8.08 (1H, d, J = 8.2 Hz), 8.04 (1H, d, J = 2.3 Hz), 7.64 (1H, d, J = 7.9 Hz), 7.50-7.46 (2H, m), 6.97 (1H, d, J = 9.0 Hz), 6.57 (1H, dd, J = 2.8, 7.6 Hz), 6.39 (1H, d, J = 2.5 Hz), 6.34 (1H, t, J = 4.5 Hz), 4.58 (1H, s), 3.71-3.64 (1H, m), 3.60 (2H, t, J = 5.4 Hz), 3.53-3.47 (2H, m), 3.36 (3H, s), 3.31 (2H, q, J = 5.9 Hz), 2.86 (2H, ddd, J = 2.8, 10.0, 12.5 Hz), 1.89 (2H, dd, J = 3.7, 13.0 Hz), 1.62-1.52 (2H, m) | F AC15 BC8 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-206 | 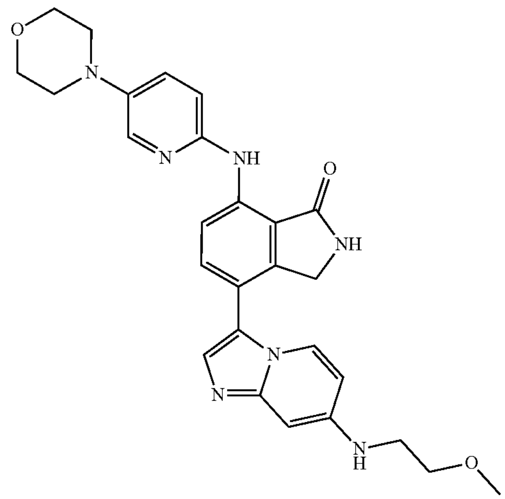 [SMILES: COCCNc1ccn2c(-c3ccc(Nc4ccc(N5CCOCC5)cn4)c4c3CNC4=O)cnc2c1] | 4-[7-(2-methoxyethyl-amino)imidazo[1,2-a]pyridin-3-yl]-7-[(5-morpholino-2-pyridyl)amino]iso-indolin-1-one | Method AcHSS C18, m/z = 500 [M + H]+, Ret. time = 2.7 min. | ¹H NMR (400 MHz, DMSO): δ 9.84 (s, 1 H), 8.76 (s, 1 H), 8.54 (d, J = 7.7 Hz, 1 H), 8.05 (d, J = 7.2 Hz, 1 H), 8.01 (d, J = 3.4 Hz, 1 H), 7.61 (d, J = 8.2 Hz, 1 H), 7.45 (s, 1 H), 6.97 (d, J = 8.9 Hz, 1 H), 6.54 (dd, J = 2.5, 7.5 Hz, 1 H), 6.36-6.33 (m, 2 H), 4.39 (s, 2 H), 3.78 (t, J = 4.6 Hz, 4 H), 3.56 (t, J = 5.8 Hz, 2 H), 3.32 (s, 3 H), 3.27 (q, J = 6.3 Hz, 2 H), 3.09 (t, J = 5.5 Hz, 4 H), 2.56 (s, 1 H). | F AC10 BC8 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-207 | 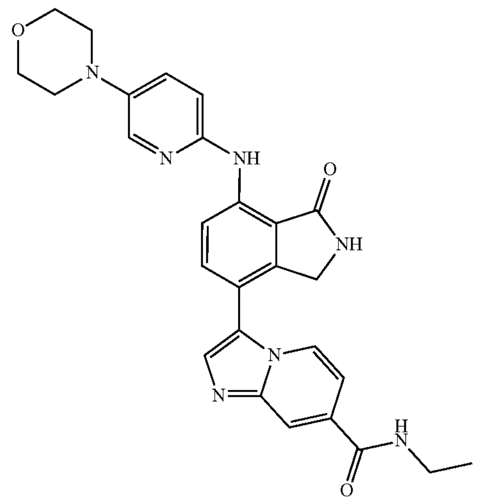 [SMILES: CCNC(=O)c1ccn2c(-c3ccc(Nc4ccc(N5CCOCC5)cn4)c4c3CNC4=O)cnc2c1] | N-ethyl-3-[7-[[5-morpholino-2-pyridyl]amino]-1-oxo-isoindolin-4-yl]imidazo[1,2-a]pyridine-7-carboxamide | Method BicarbB EHC18, m/z = 498 [M + H]+, Ret. time = 3.68 min. | ¹H NMR (400 MHz, DMSO): δ 9.94 (s, 1 H), 8.84 (s, 1 H), 8.75 (t, J = 5.7 Hz, 1 H), 8.64 (d, J = 8.4 Hz, 1 H), 8.49 (d, J = 8.1 Hz, 1 H), 8.26 (s, 1 H), 8.07 (d, J = 3.7 Hz, 1 H), 8.03 (s, 1 H), 7.78 (d, J = 8.4 Hz, 1 H), 7.51 (dd, J = 3.3, 9.1 Hz, 1 H), 7.42 (dd, J = 1.7, 7.1 Hz, 1 H), 7.04 (d, J = 9.1 Hz, 1 H), 4.46 (s, 2H), 3.82 (t, J = 4.8 Hz, 4 H), 3.41-3.37 (m, 2 H), 3.15 (t, J = 4.8 Hz, 4 H), 1.21 (t, J = 7.4 Hz, 3 H). | F AC10 BC7 |
| I-208 | 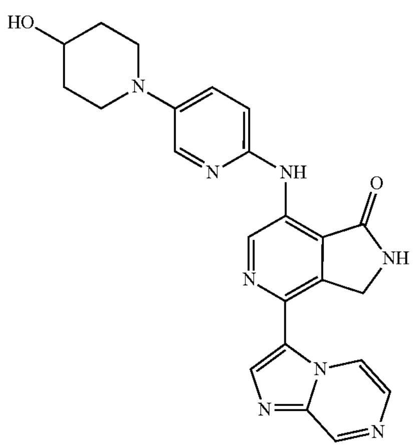 [SMILES: O=C1NCc2c(-c3cnc4cnccn34)ncc(Nc3ccc(N4CCC(O)CC4)cn3)c21] | 7-[[5-(4-hydroxy-1-piperidyl)-2-pyridyl]amino]-4-imidazo[1,2-a]pyrazin-3-yl-2,3-dihydropyrrolo[3,4-c]pyridin-1-one | Method AcHSS C18, m/z = 443 [M + H]+, Ret. time = 2.43 min. | ¹H NMR (400 MHz, DMSO): δ 9.93 (s, 1 H), 9.76 (dd, J = 1.4, 5.1 Hz, 1 H), 9.43 (s, 1 H), 9.30 (s, 1 H), 9.21 (d, J = 1.7 Hz, 1 H), 8.29 (s, 1 H), 8.07 (d, J = 4.6 Hz, 1 H), 8.04 (d, J = 3.4 Hz, 1 H), 7.46 (dd, J = 2.8, 9.1 Hz, 1 H), 7.02 (d, J = 9.5 Hz, 1 H), 4.80 (s, 2 H), 4.71 (s, 1 H), 3.69-3.60 (m, 1 H), 3.53-3.44 (m, 2 H), 2.85 (ddd, J = 2.8, 9.9, 12.4 Hz, 2 H), 1.86 (dd, J = 4.7, 12.6 Hz, 2 H), 1.59-1.48 (m, 2H). | Hc AC15 BC104 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-209 | 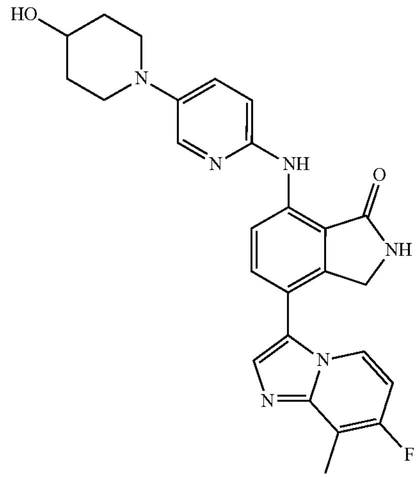 [SMILES: Cc1c(F)ccn2c(-c3ccc(Nc4ccc(N5CCC(O)CC5)cn4)c4c3CNC4=O)cnc12] | 4-(7-fluoro-8-methyl-imidazo[1,2-a]pyridin-3-yl)-7-[[5-(4-hydroxy-1-piperidyl)-2-pyridyl]amino]iso-indolin-1-one | Method AcHSS C18, m/z = 473 [M + H]+, Ret. time = 2.18 min. | ¹H NMR (400 MHz, DMSO): δ 9.88 (s, 1 H), 8.79 (s, 1 H), 8.58 (d, J = 8.7 Hz, 1 H), 8.31 (t, J = 6.2 Hz, 1 H), 8.05 (d, J = 3.4 Hz, 1 H), 7.82 (s, 1 H), 7.71 (d, J = 8.7 Hz, 1 H), 7.48 (dd, J = 3.0, 9.0 Hz, 1 H), 7.01-6.96 (m, 2 H), 4.74 (d, J = 4.3 Hz, 1 H), 4.42 (s, 2 H), 3.72-3.63 (m, 1 H), 3.53-3.46 (m, 2 H), 2.87 (ddd, J = 3.1, 9.9, 12.8 Hz, 2 H), 2.49 (d, J = 1.7 Hz, 3 H), 1.89 (dd, J = 4.2, 12.8 Hz, 2 H), 1.62-1.52 (m, 2 H). | F AC15 BC105 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-210 | (structure) | 7-[[5-[(3S)-3-(1-hydroxy-1-methyl-ethyl)-1-piperidyl]-2-pyridyl]amino]-4-imidazo[1,2-a]pyridin-3-yl-2,3-dihydropyrrolo[3,4-c]pyridin-1-one | Method AcHSS C18, m/z = 484 [M + H]+, Ret. time = 2.54 min. | ¹H NMR (400 MHz, DMSO): δ 9.86 (s, 1 H), 9.83 (d, J = 7.2 Hz, 1 H), 9.35 (s, 1 H), 9.21 (s, 1 H), 8.05 (s, 1 H), 7.99 (d, J = 3.3 Hz, 1 H), 7.69 (d, J = 8.9 Hz, 1 H), 7.42-7.35 (m, 2 H), 7.05 (ddd, J = 7.0, 7.0, 1.2 Hz, 1 H), 6.99 (d, J = 8.7 Hz, 1 H), 4.73 (s, 2 H), 4.23 (s, 1 H), 3.72 (d, J = 12.9 Hz, 1 H), 3.60 (d, J = 12.7 Hz, 1 H), 2.54 (ddd, J = 12.3, 12.3, 2.7 Hz, 1 H), 2.41 (t, J = 11.8 Hz, 1 H), 1.81 (d, J = 11.3 Hz, 1 H), 1.73 (d, J = 12.6 Hz, 1 H), 1.59-1.50 (m, 2 H), 1.17-1.12 (m, 1 H), 1.09 (s, 3 H), 1.07 (s, 3 H). | R AC30 BC42 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-211 | 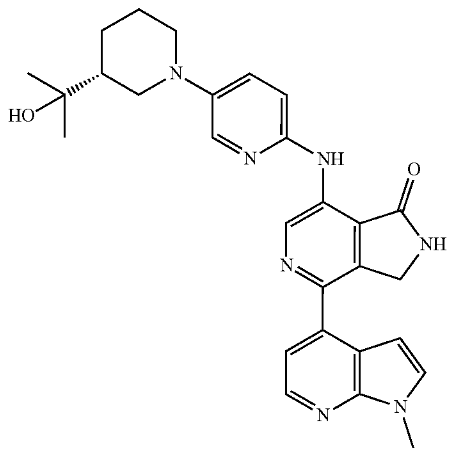 [SMILES: Cn1ccc2c(-c3ncc(Nc4ccc(N5CCC[C@@H](C(C)(C)O)C5)cn4)c4c3CNC4=O)ccnc21] | 7-[[5-[(3S)-3-(1-hydroxy-1-methyl-ethyl)-1-piperidyl]-2-pyridyl]amino]-4-(1-methylpyrrolo[2,3-b]pyridin-4-yl)-2,3-dihydropyrrolo[3,4-c]pyridin-1-one | Method BicarbB EHC18, m/z = 498 [M + H]+, Ret. time = 4.27 min. | ¹H NMR (400 MHz, DMSO) d 9.94 (s, 1H), 9.50 (s, 1H), 9.17 (s, 1H), 8.35 (d, J = 5.0 Hz, 1H), 8.05 (d, J = 3.1 Hz, 1H), 7.57 (d, J = 3.6 Hz, 1H), 7.44 (dd, J = 2.9, 9.2 Hz, 1H), 7.38 (d, J = 4.6 Hz, 1H), 7.06 (d, J = 8.9 Hz, 1H), 6.92 (d, J = 3.4 Hz, 1H), 4.73 (s, 2H), 4.29 (s, 1H), 3.88 (s, 3H), 3.78 (d, J = 10.4 Hz, 1H), 3.65 (d, J = 12.5 Hz, 1H), 2.58 (ddd, J = 12.2, 12.2, 2.7 Hz, 1H), 2.46 (t, J = 11.9 Hz, 1H), 1.86 (d, J = 12.5 Hz, 1H), 1.77 (d, J = 13.0 Hz, 1H), 1.64-1.55 (m, 2H), 1.21-1.16 (m, 1H), 1.14 (s, 3H), 1.11 (s, 3H). | R AC30 BC26 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-212 | (structure) | 7-[[5-[(3R)-3-(1-hydroxy-1-methyl-ethyl)-1-piperidyl]-2-pyridyl]amino]-4-(1-methylpyrrolo[2,3-b]pyridin-4-yl)-2,3-dihydropyrrolo[3,4-c]pyridin-1-one | Method AcHSS C18, m/z = 498 [M + H]+, Ret. time = 2.96 min. | ¹H NMR (400 MHz, DMSO): δ 9.93 (s, 1 H), 9.50 (s, 1 H), 9.16 (s, 1 H), 8.36 (d, J = 5.0 Hz, 1 H), 8.06 (d, J = 2.6 Hz, 1 H), 7.57 (d, J = 3.4 Hz, 1 H), 7.45 (dd, J = 2.8, 9.0 Hz, 1 H), 7.38 (d, J = 5.0 Hz, 1 H), 7.06 (d, J = 8.9 Hz, 1 H), 6.92 (d, J = 3.4 Hz, 1 H), 4.72 (s, 2 H), 4.31-4.29 (m, 1 H), 3.88 (s, 3 H), 3.78 (d, J = 11.5 Hz, 1 H), 3.65 (d, J = 11.8 Hz, 1 H), 2.63-2.55 (m, 1 H), 2.45 (dd, J = 11.7, 11.7 Hz, 1 H), 1.82 (dd, J = 12.7, 34.6 Hz, 2 H), 1.63-1.55 (m, 2 H), 1.22-1.17 (m, 1 H), 1.13 (d, J = 10.2 Hz, 6 H). | R AC29 BC26 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-213 | 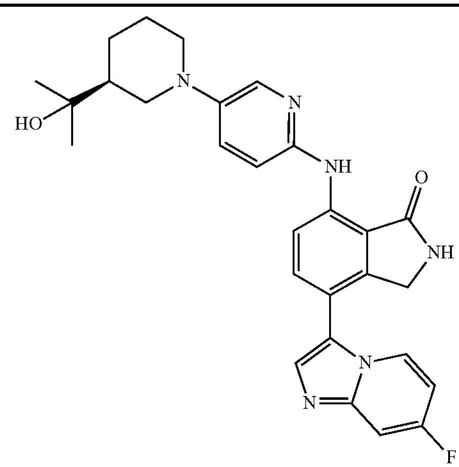 | 4-(7-fluoroimidazo[1,2-a]pyridin-3-yl)-7-[[5-[(3S)-3-(1-hydroxy-1-methyl-ethyl)-1-piperidyl]-2-pyridyl]amino]isoindolin-1-one | Method AcHSS C18, m/z = 501 [M + H]+, Ret. time = 2.51 min. | ¹H NMR (400 MHz, DMSO): δ 9.84 (s, 1 H), 8.78 (s, 1 H), 8.56 (d, J = 8.5 Hz, 1 H), 8.43 (dd, J = 6.0, 7.4 Hz, 1 H), 8.00 (d, J = 3.0 Hz, 1 H), 7.83 (s, 1 H), 7.69 (d, J = 8.5 Hz, 1 H), 7.54 (dd, J = 2.3, 10.1 Hz, 1 H), 7.42 (dd, J = 3.0, 9.0 Hz, 1 H), 6.99 (ddd, J = 7.5, 7.5, 2.6 Hz, 1 H), 6.97 (d, J = 9.0 Hz, 1 H), 4.38 (s, 2 H), 4.28 (s, 1 H), 3.75 (d, J = 11.7 Hz, 1 H), 3.64-3.59 (m, 1 H), 2.60-2.57 (m, 1 H), 2.44 (t, J = 11.9 Hz, 1 H), 1.87 (d, J = 11.6 Hz, 1 H), 1.77 (d, J = 13.5 Hz, 1 H), 1.63-1.51 (m, 2 H), 1.20-1.15 (m, 1 H), 1.13 (s, 3 H), 1.10 (s, 3 H). | F AC25 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-214 | 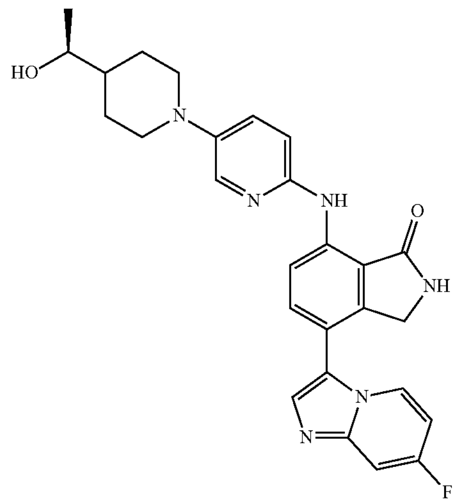 [SMILES: C[C@H](O)C1CCN(c2ccc(Nc3ccc(-c4cnc5cc(F)ccn45)c4c3C(=O)NC4)nc2)CC1] | 4-(7-fluoroimidazo[1,2-a]pyridin-3-yl)-7-[[5-[4-[(1S)-1-hydroxyethyl]-1-piperidyl]-2-pyridyl]amino]isoindolin-1-one | Method AcHSS C18, m/z = 487 [M + H]+, Ret. time = 2.19 min. | ¹H NMR (400 MHz, DMSO): δ 9.84 (s, 1 H), 8.77 (s, 1 H), 8.55 (d, J = 8.6 Hz, 1 H), 8.42 (dd, J = 5.9, 7.6 Hz, 1 H), 8.00 (d, J = 3.1 Hz, 1 H), 7.82 (s, 1 H), 7.69 (d, J = 8.6 Hz, 1 H), 7.53 (dd, J = 2.8, 10.1 Hz, 1 H), 7.44 (dd, J = 3.0, 9.0 Hz, 1 H), 6.98 (ddd, J = 7.4, 7.4, 2.9 Hz, 1 H), 6.95 (d, J = 9.0 Hz, 1 H), 4.43 (d, J = 5.1 Hz, 1 H), 4.38 (s, 2 H), 3.65 (d, J = 11.2 Hz, 2 H), 3.43 (q, J = 5.5 Hz, 1 H), 2.63-2.57 (m, 2 H), 1.88 (d, J = 10.6 Hz, 1 H), 1.66 (d, J = 12.2 Hz, 1 H), 1.40-1.32 (m, 3 H), 1.08 (d, J = 6.1 Hz, 3 H). | F AC3 BC80 |
| I-215 | 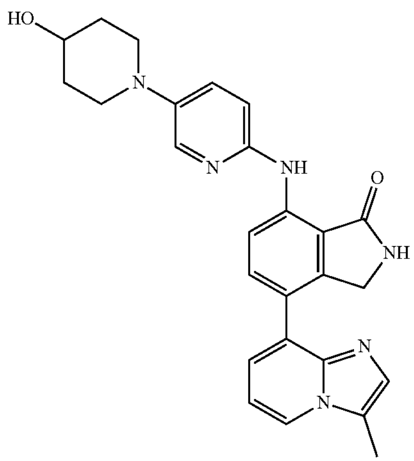 [SMILES: Cc1cnc2c(-c3ccc(Nc4ccc(N5CCC(O)CC5)cn4)c4c3CNC4=O)cccn12] | 7-[[5-(4-hydroxy-1-piperidyl)-2-pyridyl]amino]-4-(3-methylimidazo[1,2-a]pyridin-8-yl)isoindolin-1-one | Method AcHSS C18, m/z = 455 [M + H]+, Ret. time = 2.1 min. | ¹H NMR (400 MHz, DMSO): δ 9.88 (s, 1 H), 8.66 (s, 1 H), 8.46 (d, J = 8.4 Hz, 1 H), 8.30 (dd, J = 0.7, 6.9 Hz, 1 H), 8.01 (d, J = 2.9 Hz, 1 H), 7.79 (d, J = 8.8 Hz, 1 H), 7.44 (dd, J = 3.0, 8.9 Hz, 1 H), 7.42 (d, J = 1.0 Hz, 1 H), 7.33 (dd, J = 1.1, 7.1 Hz, 1 H), 7.05 (t, J = 6.9 Hz, 1 H), 6.95 (d, J = 9.9 Hz, 1 H), 4.70 (s, 1 H), 4.49 (s, 2 H), 3.67-3.60 (m, 1 H), 3.46 (d, J = 13.4 Hz, 2 H), 2.86-2.78 (m, 2 H), 2.09 (s, 3 H), 1.85 (dd, J = 3.9, 12.2 Hz, 2 H), 1.53 (ddt, J = 3.0, 10.4, 10.9 Hz, 2 H). | D AC8 BC107 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-216 | 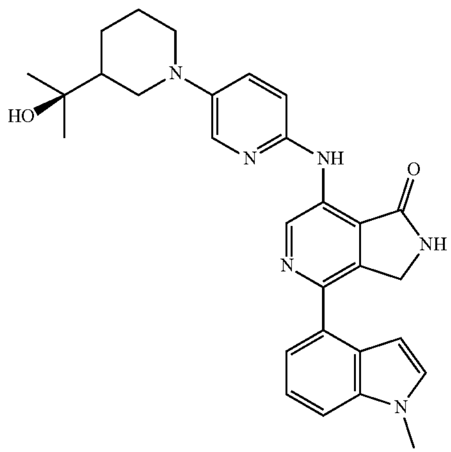 | 7-[[5-[(3S)-3-(1-hydroxy-1-methyl-ethyl)-1-piperidyl]-2-pyridyl]amino]-4-(1-methylindol-4-yl)-2,3-dihydropyrrolo[3,4-c]pyridin-1-one | Method AcHSS C18, m/z = 497 [M + H]+, Ret. time = 3.19 min. | ¹H NMR (400 MHz, DMSO) δ 9.86 (s, 1 H), 9.38 (s, 1 H), 9.06 (s, 1 H), 8.05-8.03 (m, 1 H), 7.51 (d, J = 8.4 Hz, 1 H), 7.44 (dd, J = 2.8, 8.8 Hz, 1 H), 7.38 (d, J = 3.2 Hz, 1 H), 7.36-7.32 (m, 1 H), 7.28-7.24 (m, 1 H), 7.05-7.02 (m, 1 H), 6.74 (d, J = 2.3 Hz, 1 H), 4.58 (s, 2 H), 4.28-4.28 (m, 1 H), 3.85 (s, 3 H), 3.78-3.75 (m, 1 H), 3.67-3.61 (m, 1 H), 2.61-2.41 (m, 2 H), 1.88-1.75 (m, 2 H), 1.64-1.52 (m, 2 H), 1.21-1.09 (m, 7 H). | R AC30 BC108 |
| I-217 | 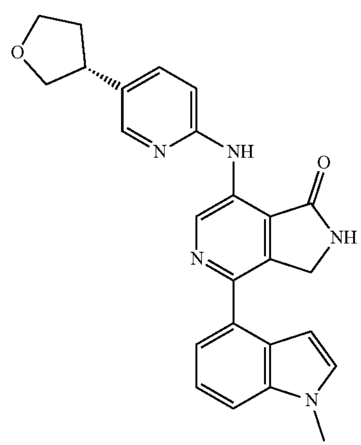 [SMILES: Cn1ccc2c(-c3ncc(Nc4ccc([C@H]5CCOC5)cn4)c4c3CNC4=O)cccc21] | (R)-4-(1-methyl-1H-pyrrolo[2,3-b]pyridin-4-yl)-7-((5-(tetrahydrofuran-3-yl)pyridin-2-yl)amino)-2,3-dihydro-1H-pyrrolo[3,4-c]pyridin-1-one | Method AcHSS C18, m/z = 427 [M + H]+, Ret. time = 3.57 min. | ¹H NMR (400 MHz, DMSO) δ 10.02 (s, 1H), 9.71 (s, 1H), 9.21 (s, 1H), 8.35 (d, J = 5.0 Hz, 1H), 8.29 (d, J = 2.4 Hz, 1H), 7.67 (dd, J = 2.4, 8.5 Hz, 1H), 7.57 (d, J = 3.4 Hz, 1H), 7.38 (d, J = 5.0 Hz, 1H), 7.09 (d, J = 8.5 Hz, 1H), 6.90 (d, J = 3.4 Hz, 1H), 4.72 (s, 2H), 4.04 (t, J = 7.8 Hz, 1H), 4.00-3.94 (m, 1H), 3.87 (s, 3H), 3.85-3.78 (m, 1H), 3.56 (dd, J = 7.9, 7.9 Hz, 1H), 3.44-3.35 (m, 1H), 2.37-2.28 (m, 1H), 1.99-1.89 (m, 1H). | R AC22 BC26 |

| # | STRUCTURE | NAME | LCMS | ¹H NMR | Method AA Reagent BB |
|---|---|---|---|---|---|
| I-218 | 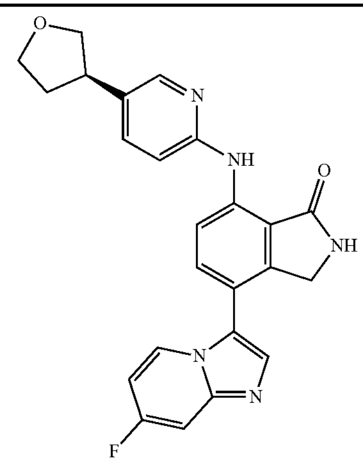 | (R)-4-(7-fluoroimidazo[1,2-a]pyridin-3-yl)-7-((5-(tetrahydrofuran-3-yl)pyridin-2-yl)amino)isoindolin-1-one | Method AcHSS C18, m/z = 430 [M + H]+, Ret. time = 2.65 min. | ¹H NMR (400 MHz, DMSO): δ 10.07 (s, 1 H), 8.85 (s, 1 H), 8.71 (d, J = 8.4 Hz, 1 H), 8.45 (dd, J = 6.2, 7.3 Hz, 1 H), 8.24 (d, J = 2.5 Hz, 1 H), 7.84 (s, 1 H), 7.74 (d, J = 8.4 Hz, 1 H), 7.66 (dd, J = 2.4, 8.6 Hz, 1 H), 7.54 (dd, J = 2.7, 10.0 Hz, 1 H), 7.01 (d, J = 8.2 Hz, 1 H), 6.99 (ddd, J = 7.5, 7.5, 2.5 Hz, 1 H), 4.41 (s, 2 H), 4.04 (t, J = 7.8 Hz, 1 H), 3.98 (ddd, J = 8.3, 8.3, 4.7 Hz, 1 H), 3.83 (q, J = 7.8 Hz, 1 H), 3.56 (t, J = 7.9 Hz, 1 H), 3.43-3.39 (m, 1 H), 2.37-2.28 (m, 1 H), 1.99-1.89 (m, 1 H). | F AC22 BC80 |
| I-219 | 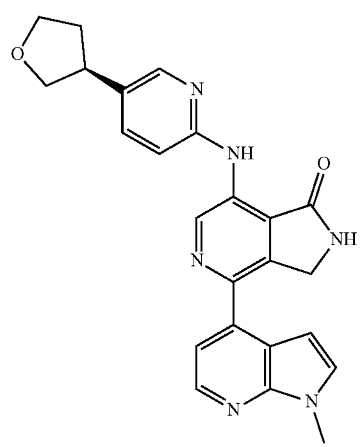 | (S)-4-(1-methyl-1H-pyrrolo[2,3-b]pyridin-4-yl)-7-((5-(tetrahydrofuran-3-yl)pyridin-2-yl)amino)-2,3-dihydro-1H-pyrrolo[3,4-c]pyridin-1-one | Method AcHSS C18, m/z = 427 [M + H]+, Ret. time = 3.43 min. | ¹H NMR (400 MHz, DMSO): δ 10.04 (s, 1 H), 9.72 (s, 1 H), 9.23 (s, 1 H), 8.37 (d, J = 5.0 Hz, 1 H), 8.30 (d, J = 2.4 Hz, 1 H), 7.69 (dd, J = 2.4, 8.6 Hz, 1 H), 7.59 (d, J = 3.7 Hz, 1 H), 7.40 (d, J = 5.0 Hz, 1 H), 7.11 (d, J = 8.2 Hz, 1 H), 6.92 (d, J = 3.5 Hz, 1 H), 4.73 (s, 2 H), 4.05 (t, J = 7.8 Hz, 1 H), 3.99 (ddd, J = 8.5, 8.5, 4.7 Hz, 1 H), 3.89 (s, 3 H), 3.83 (dd, J = 8.1, 15.7 Hz, 1 H), 3.57 (t, J = 8.2 Hz, 1 H), 3.46-3.38 (m, 1 H), 2.39-2.30 (m, 1 H), 2.01-1.91 (m, 1 H). | R AC22 BC26 |

TABLE 8-continued

Characterization Data (LCMS and ¹H NMR).

| # | STRUCTURE | NAME | LCMS | ¹H NMR | Method AA Reagent BB |
|---|---|---|---|---|---|
| I-220 | 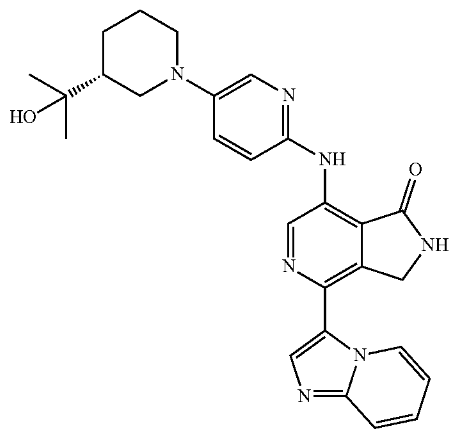 [SMILES: CC(C)(O)[C@@H]1CCCN(c2ccc(Nc3cnc(-c4cnc5ccccn45)c4c3C(=O)NC4)nc2)C1] | 7-[[5-[(3R)-3-(1-hydroxy-1-methyl-ethyl)-1-piperidyl]-2-pyridyl]amino]-4-imidazo[1,2-a]pyridin-3-yl-2,3-dihydropyrrolo[3,4-c]pyridin-1-one | Method AcHSS C18, m/z = 484 [M + H]+, Ret. time = 2.58 min. | ¹H NMR (400 MHz, DMSO): δ 9.86 (s, 1 H), 9.83 (d, J = 7.2 Hz, 1 H), 9.35 (s, 1 H), 9.21 (s, 1 H), 8.05 (s, 1 H), 7.99 (d, J = 3.3 Hz, 1 H), 7.69 (d, J = 8.9 Hz, 1 H), 7.42-7.35 (m, 2 H), 7.05 (ddd, J = 7.0, 7.0, 1.2 Hz, 1 H), 6.99 (d, J = 8.7 Hz, 1 H), 4.73 (s, 2 H), 4.23 (s, 1 H), 3.72 (d, J = 12.9 Hz, 1 H), 3.60 (d, J = 12.7 Hz, 1 H), 2.54 (ddd, J = 12.3, 12.3, 2.7 Hz, 1 H), 2.41 (t, J = 11.8 Hz, 1 H), 1.81 (d, J = 11.3 Hz, 1 H), 1.73 (d, J = 12.6 Hz, 1 H), 1.59-1.50 (m, 2 H), 1.17-1.12 (m, 1 H), 1.09 (s, 3 H), 1.07 (s, 3 H). | R AC29 BC42 |
| I-221 | 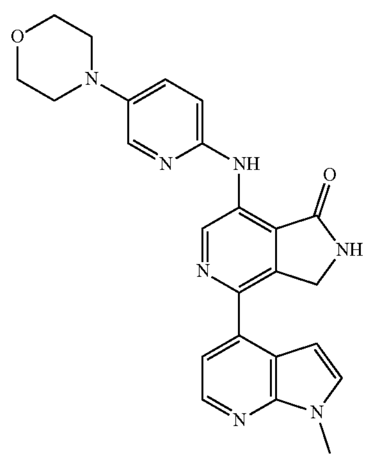 [SMILES: Cn1ccc2c(-c3ncc(Nc4ccc(N5CCOCC5)cn4)c4c3CNC4=O)ccnc21] | 4-(1-methylindol-4-yl)-7-[[5-morpholino-2-pyridyl]amino]-2,3-dihydropyrrolo[3,4-c]pyridin-1-one | Method AcHSS C18, m/z = 441 [M + H]+, Ret. time = 3.3 min. | ¹H NMR (400 MHz, DMSO) δ 9.88-9.87 (m, 1 H), 9.42 (s, 1 H), 9.07 (s, 1 H), 8.52 (s, 0.25 H), 8.06 (d, J = 2.9 Hz, 1 H), 7.53-7.46 (m, 2 H), 7.39-7.24 (m, 3 H), 7.08-7.05 (m, 1 H), 6.75-6.74 (m, 1 H), 4.58 (s, 2 H), 3.86-3.85 (m, 3 H), 3.80-3.76 (m, 4 H), 3.14-3.09 (m, 4 H). | A AC10 BC108 |

TABLE 8-continued

Characterization Data (LCMS and ¹H NMR).

| # | STRUCTURE | NAME | LCMS | ¹H NMR | Method AA Reagent BB |
|---|---|---|---|---|---|
| I-222 | 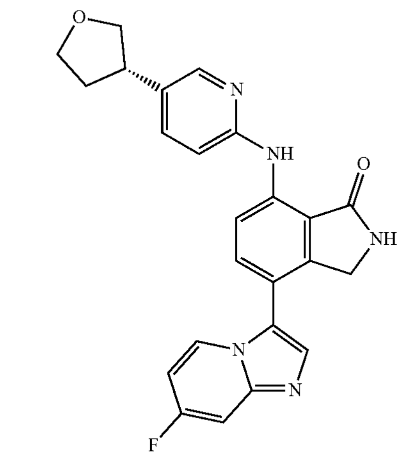 [SMILES: O=C1NCc2c(-c3cnc4cc(F)ccn34)ccc(Nc3ccc([C@@H]4CCOC4)cn3)c21] | (S)-4-(7-fluoroimidazo[1,2-a]pyridin-3-yl)-7-((5-(tetrahydrofuran-3-yl)pyridin-2-yl)amino)isoindolin-1-one | Method BicarbB EHC18, m/z = 430 [M + H]+, Ret. time = 4.19 min. | ¹H NMR (400 MHz, DMSO): δ 10.07 (s, 1 H), 8.85 (s, 1 H), 8.71 (d, J = 8.4 Hz, 1 H), 8.45 (dd, J = 6.2, 7.3 Hz, 1 H), 8.24 (d, J = 2.5 Hz, 1 H), 7.84 (s, 1 H), 7.74 (d, J = 8.4 Hz, 1 H), 7.66 (dd, J = 2.4, 8.6 Hz, 1 H), 7.54 (dd, J = 2.7, 10.0 Hz, 1 H), 7.01 (d, J = 8.2 Hz, 1 H), 6.99 (ddd, J = 7.5, 7.5, 2.5 Hz, 1 H), 4.41 (s, 2 H), 4.04 (t, J = 7.8 Hz, 1 H), 3.98 (ddd, J = 8.3, 8.3, 4.7 Hz, 1 H), 3.83 (q, J = 7.8 Hz, 1 H), 3.56 (t, J = 7.9 Hz, 1 H), 3.43-3.39 (m, 1 H), 2.37-2.28 (m, 1 H), 1.99-1.89 (m, 1 H). | F AC22 BC80 |
| I-223 | 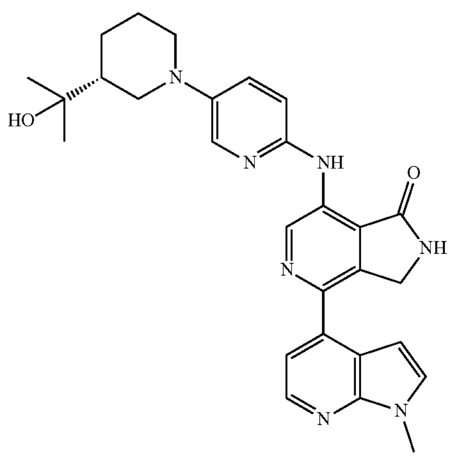 [SMILES: Cn1ccc2c(-c3ncc(Nc4ccc(N5CCC[C@@H](C(C)(C)O)C5)cn4)c4c3CNC4=O)ccnc21] | 7-[[5-[(3R)-3-(1-hydroxy-1-methyl-ethyl)-1-piperidyl]-2-pyridyl]amino]-4-(1-methylindol-4-yl)-2,3-dihydropyrrolo[3,4-c]pyridin-1-one | Method AcHSS C18, m/z = 497 [M + H]+, Ret. time = 3.2 min. | ¹H NMR (400 MHz, DMSO): δ 9.86 (s, 1 H), 9.39 (s, 1 H), 9.06 (s, 1 H), 8.04 (d, J = 3.0 Hz, 1H), 7.51 (d, J = 7.1 Hz, 1 H), 7.44 (dd, J = 2.9, 9.0 Hz, 1 H), 7.38 (d, J = 3.2 Hz, 1 H), 7.36-7.32 (m, 1 H), 7.29-7.24 (m, 1 H), 7.05-7.01 (m, 1 H), 6.75 (d, J = 2.6 Hz, 1 H), 4.58 (d, J = 2 H), 4.29 (s, 1 H), 3.86-3.84 (m, 3 H), 3.76 (d, J = 11.7 Hz, 1 H), 3.64 (d, J = 11.5 Hz, 1 H), 2.62-2.41 (m, 2 H), 1.88-1.73 (m, 2 H), 1.64-1.54 (m, 2 H), 1.15-1.10 (m, 7 H). | R AC29 BC108 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-224 | (structure) | 4-(7-fluoroimidazo[1,2-a]pyridin-3-yl)-7-[[5-[4-(1-hydroxy-1-methyl-ethyl)-1-piperidyl]-2-pyridyl]amino]isoindolin-1-one | Method AcHSS C18, m/z = 501 [M + H]+, Ret. time = 2.35 min. | ¹H NMR (400 MHz, DMSO): δ 9.82 (s, 1 H), 8.74 (s, 1 H), 8.54 (d, J = 8.6 Hz, 1 H), 8.41 (dd, J = 6.2, 7.5 Hz, 1 H), 7.99 (d, J = 3.0 Hz, 1 H), 7.80 (s, 1 H), 7.67 (d, J = 8.6 Hz, 1 H), 7.51 (dd, J = 2.3, 10.1 Hz, 1 H), 7.43 (dd, J = 3.0, 9.1 Hz, 1 H), 6.99-6.92 (m, 2 H), 4.36 (s, 2 H), 4.13 (s, 1 H), 3.67 (d, J = 11.9 Hz, 2 H), 2.59-2.53 (m, 2H), 1.79 (d, J = 11.4 Hz, 2 H), 1.42-1.28 (m, 3H), 1.07 (s, 6 H). | F AC33 BC80 |
| I-225 | (structure) | 7-[[5-(3S)-3-(1-hydroxy-1-methyl-ethyl)-1-piperidyl]-2-pyridyl]amino]-4-(7-methylimidazo[1,2-a]pyrimidin-3-yl)isoindolin-1-one | Method AcHSS C18, m/z = 498 [M + H]+, Ret. time = 2.42 min. | ¹H NMR (400 MHz, DMSO): δ 9.83 (s, 1 H), 8.78 (s, 1 H), 8.71 (d, J = 7.0 Hz, 1 H), 8.56 (d, J = 8.0 Hz, 1 H), 8.00 (d, J = 3.0 Hz, 1 H), 7.88 (s, 1 H), 7.68 (d, J = 8.5 Hz, 1 H), 7.42 (dd, J = 3.0, 9.0 Hz, 1 H), 6.99 (d, J = 7.2 Hz, 1 H), 6.96 (d, J = 9.1 Hz, 1 H), 4.41 (s, 2 H), 4.29 (s, 1 H), 3.74 (d, J = 11.5 Hz, 1 H), 3.61 (d, J = 11.7 Hz, 1 H), 2.58 (m, 4 H), 2.44 (t, J = 11.8 Hz, 1 H), 1.84 (d, J = 14.2 Hz, 1 H), 1.76 (d, J = 14.2 Hz, 1 H), 1.63-1.53 (m, 2 H), 1.20-1.16 (m, 1 H), 1.13 (s, 3 H), 1.11 (s, 3 H). | F AC30 BC109 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-226 | 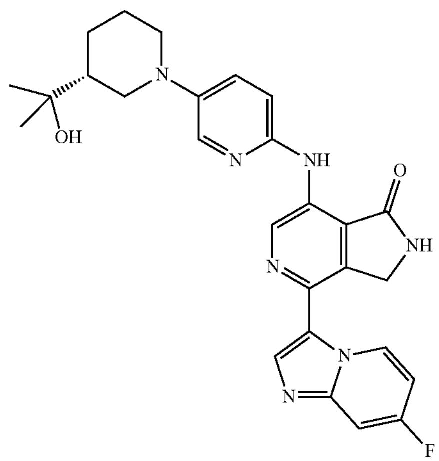 [SMILES: CC(C)(O)[C@@H]1CCCN(c2ccc(Nc3cnc(-c4cnc5cc(F)ccn45)c4c3C(=O)NC4)nc2)C1] | 4-(7-fluoroimidazo[1,2-a]pyridin-3-yl)-7-[[5-[(3R)-3-(1-hydroxy-1-methyl-ethyl)-1-piperidyl]-2-pyridyl]amino]-2,3-dihydropyrrolo[3,4-c]pyridin-1-one | Method AcHSS C18, m/z = 502 [M + H]+, Ret. time = 2.72 min. | ¹H NMR (400 MHz, DMSO): δ 9.94 (t, J = 6.9 Hz, 1 H), 9.89 (s, 1 H), 9.38 (s, 1 H), 9.27 (s, 1 H), 8.05 (s, 1 H), 8.02 (d, J = 3.3 Hz, 1 H), 7.59 (dd, J = 2.7, 10.0 Hz, 1 H), 7.43 (dd, J = 3.2, 9.2 Hz, 1 H), 7.14 (ddd, J = 7.4, 7.4, 2.5 Hz, 1 H), 7.01 (d, J = 9.2 Hz, 1 H), 4.74 (s, 2 H), 4.29 (s, 1 H), 3.76 (d, J = 12.0 Hz, 1 H), 3.65 (d, J = 12.9 Hz, 1 H), 2.57 (ddd, J = 12.6, 12.6, 2.3 Hz, 1 H), 2.45 (t, J = 11.5 Hz, 1 H), 1.86 (d, J = 11.4 Hz, 1 H), 1.77 (d, J = 12.6 Hz, 1 H), 1.62-1.54 (m, 2 H), 1.21-1.16 (m, 1 H), 1.14 (s, 3 H), 1.12 (s, 3 H). | Hc AC29 BC9 |
| I-227 | 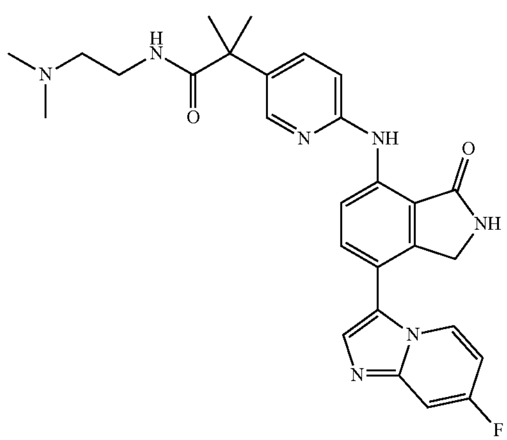 [SMILES: CN(C)CCNC(=O)C(C)(C)c1ccc(Nc2ccc(-c3cnc4cc(F)ccn34)c3c2C(=O)NC3)nc1] | N-[2-(dimethylamino)ethyl]-2-[6-[[7-(7-fluoroimidazo[1,2-a]pyridin-3-yl)-3-oxo-isoindolin-4-yl]amino]-3-pyridyl]-2-methyl-propanamide | Method AcHSS C18, m/z = 516 [M + H]+, Ret. time = 2.12 min. | ¹H NMR (400 MHz, DMSO): δ 10.10 (s, 1 H), 8.85 (s, 1 H), 8.73 (d, J = 9.1 Hz, 1 H), 8.44 (dd, J = 5.5, 7.3 Hz, 1 H), 8.28 (d, J = 1.8 Hz, 1 H), 8.21 (s, 1 H), 7.84 (s, 1 H), 7.75 (d, J = 8.7 Hz, 1 H), 7.64 (dd, J = 2.7, 8.7 Hz, 1 H), 7.54 (dd, J = 2.5, 10.2 Hz, 1 H), 7.37 (t, J = 5.7 Hz, 1 H), 7.01-6.98 (m, 2 H), 4.40 (s, 2 H), 3.15 (dd, J = 6.5, 13.2 Hz, 2 H), 2.29 (t, J = 7.3 Hz, 2 H), 2.16 (s, 6 H), 1.48 (s, 6 H). | F AC34 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-228 | 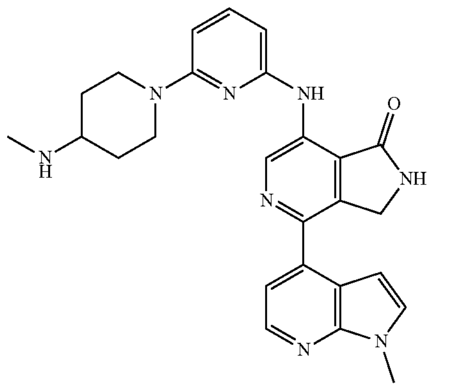 [SMILES: CNC1CCN(c2cccc(Nc3cnc(-c4ccnc5c4ccn5C)c4c3C(=O)NC4)n2)CC1] | 7-[[6-[4-(methylamino)-1-piperidyl]-2-pyridyl]amino]-4-(1-methylpyrrolo[2,3-b]pyridin-4-yl)-2,3-dihydropyrrolo[3,4-c]pyridin-1-one | Method AcHSS C18, m/z = 469 [M + H]+, Ret. time = 2.67 min. | ¹H NMR (400 MHz, DMSO): δ 9.84 (s, 1 H), 9.56 (s, 1 H), 9.20 (s, 1 H), 8.37 (d, J = 3.8 Hz, 2 H), 7.59 (d, J = 3.1 Hz, 1 H), 7.52 (t, J = 7.7 Hz, 1 H), 7.39 (d, J = 5.2 Hz, 1 H), 6.87 (d, J = 4.5 Hz, 1 H), 6.46 (d, J = 8.6 Hz, 1 H), 6.32 (d, J = 7.9 Hz, 1 H), 4.71 (s, 2 H), 4.29 (d, J = 13.8 Hz, 2 H), 3.88 (s, 3 H), 3.02 (t, J = 10.6 Hz, 2 H), 2.93-2.91 (m, 1 H), 2.45 (s, 3 H), 2.03 (d, J = 15.6 Hz, 2 H), 1.48-1.39 (m, 2 H). | R AC5 BC26 |
| I-229 | 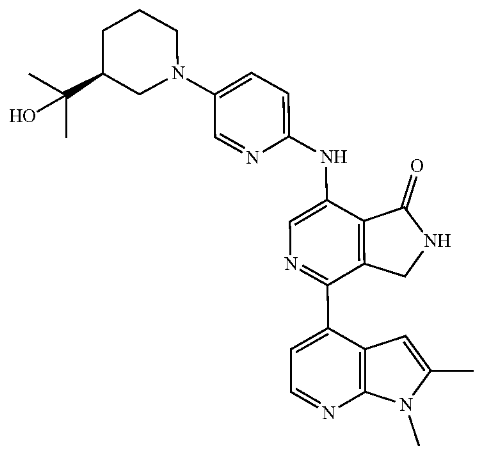 [SMILES: Cc1cc2c(-c3ncc(Nc4ccc(N5CCC[C@H](C(C)(C)O)C5)cn4)c4c3CNC4=O)ccnc2n1C] | 4-(1,2-dimethylpyrrolo[2,3-b]pyridin-4-yl)-7-[[5-[(3S)-3-(1-hydroxy-1-methyl-ethyl)-1-piperidyl]-2-pyridyl]amino]-2,3-dihydropyrrolo[3,4-c]pyridin-1-one | Method AcHSS C18, m/z = 512 [M + H]+, Ret. time = 3.08 min. | ¹H NMR (400 MHz, DMSO): δ 9.91 (s, 1 H), 9.47 (s, 1 H), 9.13 (s, 1 H), 8.23 (d, J = 5.0 Hz, 1 H), 8.05 (s, 1 H), 7.43 (d, J = 6.9 Hz, 1 H), 7.30 (d, J = 5.0 Hz, 1 H), 7.04 (d, J = 8.8 Hz, 1 H), 6.71 (s, 1 H), 4.69 (s, 2 H), 4.27-4.27 (m, 1 H), 3.79-3.74 (m, 4 H), 3.63 (d, J = 11.0 Hz, 1 H), 2.58 (d, J = 11.9 Hz, 1 H), 2.47 (s, 4H), 1.86-1.74 (m, 2 H), 1.61-1.55 (m, 2 H), 1.20-1.16 (m, 1 H), 1.11 (d, J = 10.2 Hz, 6 H). | R AC30 BC110 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-230 | 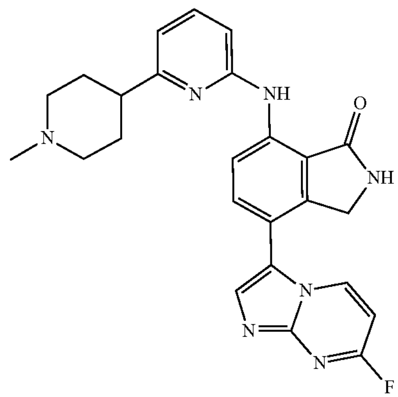 [SMILES: CN1CCC(c2cccc(Nc3ccc(-c4cnc5nc(F)ccn45)c4c3C(=O)NC4)n2)CC1] | 4-(7-fluoroimidazo[1,2-a]pyridin-3-yl)-7-[[6-(4-methylpiperazin-1-yl)-2-pyridyl]amino]isoindolin-1-one | Method AcHSS C18, m/z = 458 [M + H]+, Ret. time = 1.99 min. | ¹H NMR (400 MHz, DMSO): δ 9.94 (s, 1 H), 8.82 (s, 1 H), 8.52 (d, J = 8.1 Hz, 1 H), 8.45 (dd, J = 6.3, 7.8 Hz, 1 H), 7.83 (s, 1 H), 7.73 (d, J = 8.1 Hz, 1 H), 7.53 (dd, J = 2.8, 10.1 Hz, 1 H), 7.49 (t, J = 8.2 Hz, 1 H), 6.99 (ddd, J = 7.5, 7.5, 2.6 Hz, 1 H), 6.37 (d, J = 8.4 Hz, 1 H), 6.27 (d, J = 7.7 Hz, 1 H), 4.39 (s, 2 H), 3.53 (t, J = 4.9 Hz, 4 H), 2.45 (t, J = 5.7 Hz, 4 H), 2.24 (s, 3 H). | F AC35 BC80 |
| I-231 | 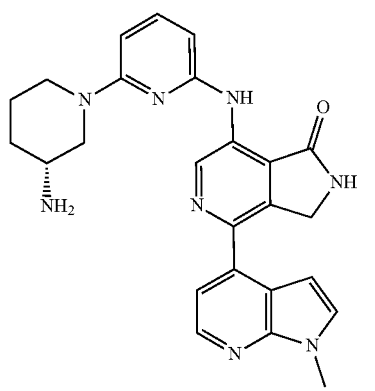 [SMILES: Cn1ccc2c(-c3ncc(Nc4cccc(N5CCC[C@@H](N)C5)n4)c4c3CNC4=O)ccnc21] | 7-[[6-[(3R)-3-amino-1-piperidyl]-2-pyridyl]amino]-4-(1-methylpyrrolo[2,3-b]pyridin-4-yl)-2,3-dihydropyrrolo[3,4-c]pyridin-1-one | Method AcHSS C18, m/z = 455 [M + H]+, Ret. time = 2.73 min. | ¹H NMR (400 MHz, DMSO): δ 9.83 (s, 1 H), 9.53 (s, 1 H), 9.18 (s, 1 H), 8.35 (d, J = 5.0 Hz, 1 H), 7.57 (d, J = 3.4 Hz, 1 H), 7.49 (t, J = 8.0 Hz, 1 H), 7.37 (d, J = 5.0 Hz, 1 H), 6.83 (d, J = 3.5 Hz, 1 H), 6.38 (d, J = 8.3 Hz, 1 H), 6.30 (d, J = 7.7 Hz, 1 H), 4.67 (s, 2 H), 3.87 (s, 3 H), 3.45 (dd, J = 5.0, 5.0 Hz, 4 H), 3.38 (d, J = 8.8 Hz, 1 H), 2.83 (dd, J = 4.9, 4.9 Hz, 4 H). | R AC36 BC26 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-232 | 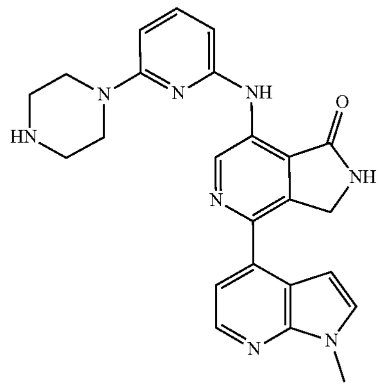 [SMILES: Cn1ccc2c(-c3ncc(Nc4cccc(N5CCNCC5)n4)c4c3CNC4=O)ccnc21] | 4-(1-methylpyrrolo[2,3-b]pyridin-4-yl)-7-[(6-piperazin-1-yl-2-pyridyl)amino]-2,3-dihydropyrrolo[3,4-c]pyridin-1-one | Method AcHSS C18, m/z = 441 [M + H]+, Ret. time = 2.48 min. | ¹H NMR (400 MHz, DMSO): δ 9.83 (s, 1 H), 9.53 (s, 1 H), 9.18 (s, 1 H), 8.35 (d, J = 5.0 Hz, 1 H), 7.57 (d, J = 3.4 Hz, 1 H), 7.49 (t, J = 8.0 Hz, 1 H), 7.37 (d, J = 5.0 Hz, 1 H), 6.83 (d, J = 3.5 Hz, 1 H), 6.38 (d, J = 8.3 Hz, 1 H), 6.30 (d, J = 7.7 Hz, 1 H), 4.67 (s, 2 H), 3.87 (s, 3 H), 3.45 (dd, J = 5.0, 5.0 Hz, 4 H), 3.38 (d, J = 8.8 Hz, 1 H), 2.83 (dd, J = 4.9, 4.9 Hz, 4 H) | R AC37 BC26 |
| I-233 | 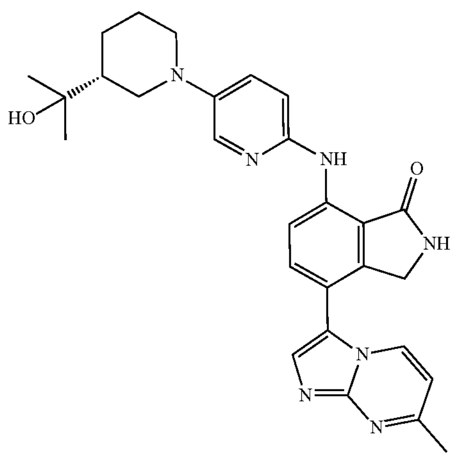 [SMILES: Cc1ccn2c(-c3ccc(Nc4ccc(N5CCC[C@@H](C(C)(C)O)C5)cn4)c4c3CNC4=O)cnc2n1] | 7-[[5-[(3R)-3-(1-hydroxy-1-methyl-ethyl)-1-piperidyl]-2-pyridyl]amino]-4-(7-methylimidazo[1,2-a]pyrimidin-3-yl)isoindolin-1-one | Method AcHSS C18, m/z = 498 [M + H]+, Ret. time = 2.42 min. | ¹H NMR (400 MHz, DMSO): δ 9.83 (s, 1 H), 8.78 (s, 1 H), 8.71 (d, J = 7.0 Hz, 1 H), 8.56 (d, J = 9.4 Hz, 1 H), 8.00 (d, J = 3.0 Hz, 1 H), 7.88 (s, 1 H), 7.69 (d, J = 8.6 Hz, 1 H), 7.42 (dd, J = 3.0, 9.0 Hz, 1 H), 6.99 (d, J = 7.2 Hz, 1 H), 6.96 (d, J = 9.6 Hz, 1 H), 4.42 (s, 2 H), 4.28 (s, 1 H), 3.74 (d, J = 12.1 Hz, 1 H), 3.62 (d, J = 12.0 Hz, 1 H), 2.58 (m, 4 H), 2.44 (t, J = 11.7 Hz, 1 H), 1.85 (d, J = 11.4 Hz, 1 H), 1.78-1.73 (m, 1 H), 1.63-1.51 (m, 2 H), 1.20-1.16 (m, 1 H), 1.13 (s, 3 H), 1.11 (s, 3 H). | F AC29 BC109 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-234 | 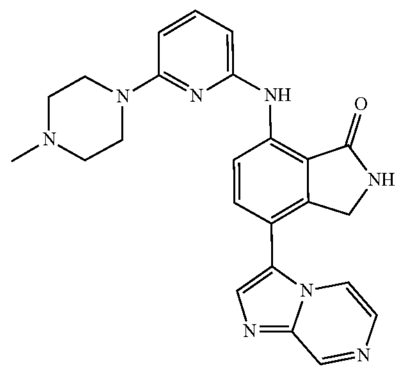 [SMILES: CN1CCN(c2cccc(Nc3ccc(-c4cnc5cnccn45)c4c3C(=O)NC4)n2)CC1] | 4-imidazo[1,2-a]pyrazin-3-yl-7-[[6-(4-methylpiperazin-1-yl)-2-pyridyl]amino]isoindolin-1-one | Method AcHSS C18, m/z = 441 [M + H]+, Ret. time = 2.33 min. | ¹H NMR (400 MHz, DMSO): δ 9.97 (s, 1 H), 9.16 (d, J = 1.4 Hz, 1 H), 8.86 (s, 1 H), 8.55 (d, J = 8.5 Hz, 1 H), 8.50 (dd, J = 1.6, 4.8 Hz, 1 H), 8.13 (s, 1 H), 7.93 (d, J = 4.7 Hz, 1 H), 7.81 (d, J = 7.6 Hz, 1 H), 7.49 (t, J = 9.2 Hz, 1 H), 6.39 (d, J = 9.5 Hz, 1 H), 6.28 (d, J = 7.8 Hz, 1 H), 4.44 (s, 2 H), 3.54 (t, J = 5.1 Hz, 4 H), 2.48 (t, J = 4.7 Hz, 4 H), 2.27 (s, 3 H). | F AC35 BC52 |
| I-235 | 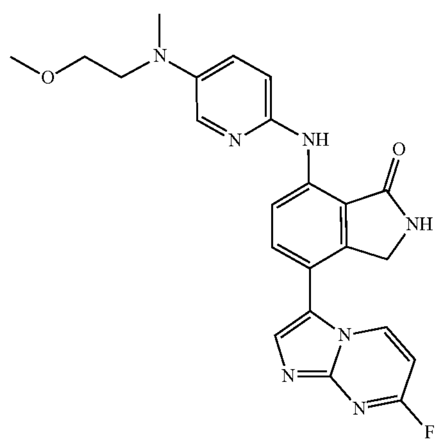 [SMILES: COCCN(C)c1ccc(Nc2ccc(-c3cnc4nc(F)ccn34)c3c2C(=O)NC3)nc1] | 4-(7-fluoroimidazo[1,2-a]pyridin-3-yl)-7-[[5-[2-methoxyethyl(methyl)amino]-2-pyridyl]amino]isoindolin-1-one | Method BicarbB EHC18, m/z = 447 [M + H]+, Ret. time = 4.06 min. | ¹H NMR (400 MHz, DMSO): δ 9.75 (s, 1 H), 8.77 (s, 1 H), 8.54 (dd, J = 6.4, 7.7 Hz, 1 H), 8.49 (d, J = 9.2 Hz, 1 H), 8.03 (s, 1 H), 7.85 (d, J = 2.6 Hz, 1 H), 7.72 (dd, J = 3.1, 9.4 Hz, 1 H), 7.69 (d, J = 9.2 Hz, 1 H), 7.28 (dd, J = 3.3, 8.6 Hz, 1 H), 7.19 (dd, J = 2.6, 7.3 Hz, 1 H), 6.97 (d, J = 9.2 Hz, 1 H), 4.37 (s, 2 H), 3.52-3.48 (m, 4 H), 3.28 (s, 3 H), 2.94 (s, 3 H). | F AC39 BC80 |

| # | STRUCTURE | NAME | LCMS | ¹H NMR | Method Reagent AA BB |
|---|---|---|---|---|---|
| I-236 | 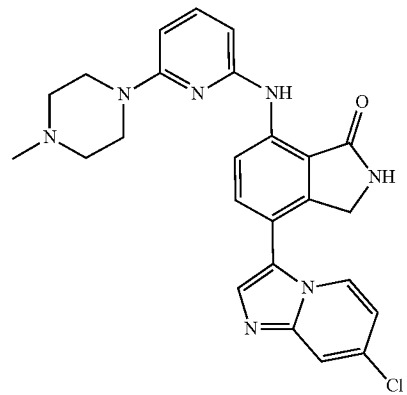 [SMILES: CN1CCN(c2cccc(Nc3ccc(-c4cnc5cc(Cl)ccn45)c4c3C(=O)NC4)n2)CC1] | 4-(7-chloroimidazo[1,2-a]pyridin-3-yl)-7-[[6-(4-methylpiperazin-1-yl)-2-pyridyl]amino]isoindolin-1-one | Method AcHSS C18, m/z = 474 [M + H]+, Ret. time = 2.22 min. | ¹H NMR (400 MHz, DMSO): δ 9.94 (s, 1 H), 8.83 (s, 1 H), 8.52 (d, J = 8.5 Hz, 1 H), 8.42 (d, J = 7.0 Hz, 1 H), 7.89 (s, 1 H), 7.85 (d, J = 2.1 Hz, 1 H), 7.74 (d, J = 8.5 Hz, 1 H), 7.49 (dd, J = 8.0, 8.0 Hz, 1 H), 7.00 (dd, J = 2.2, 7.3 Hz, 1 H), 6.38 (d, J = 8.3 Hz, 1 H), 6.28 (d, J = 7.8 Hz, 1 H), 4.40 (s, 2 H), 4.11 (q, J = 5.2 Hz, 1 H), 3.53-3.53 (m, 4 H), 3.31 (s, 1 H), 3.18 (d, J = 5.3 Hz, 1 H), 2.56 (s, 1 H), 2.26 (s, 3 H). | F AC35 BC99 |
| I-237 | 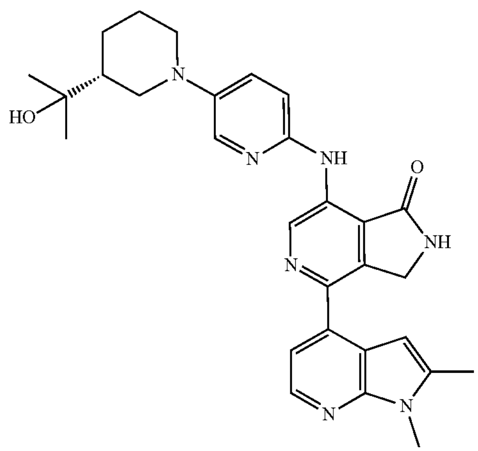 [SMILES: Cc1cc2c(-c3ncc(Nc4ccc(N5CCC[C@@H](C(C)(C)O)C5)cn4)c4c3CNC4=O)ccnc2n1C] | 4-(1,2-dimethylpyrrolo[2,3-b]pyridin-4-yl)-7-[[5-[(3R)-3-(1-hydroxy-1-methyl-ethyl)-1-piperidyl]-2-pyridyl]amino]-2,3-dihydropyrrolo[3,4-c]pyridin-1-one | Method BicarbB EHC18, m/z = 512 [M + H]+, Ret. time = 4.17 min. | ¹H NMR (400 MHz, DMSO): δ 9.93 (s, 1 H), 9.49 (s, 1 H), 9.15 (s, 1 H), 8.24 (d, J = 5.0 Hz, 1 H), 8.05 (d, J = 3.0 Hz, 1 H), 7.44 (dd, J = 2.9, 9.2 Hz, 1 H), 7.32 (d, J = 5.0 Hz, 1 H), 7.05 (d, J = 9.2 Hz, 1 H), 6.73 (d, J = 0.8 Hz, 1 H), 4.71 (s, 2 H), 4.29 (s, 1 H), 3.78 (s, 3 H), 3.77 (s, 1 H), 3.66 (d, J = 13.3 Hz, 1 H), 2.58 (ddd, J = 12.3, 12.3, 2.4 Hz, 1 H), 2.45 (d, J = 12.3 Hz, 1 H), 1.86 (d, J = 11.7 Hz, 1 H), 1.77 (d, J = 13.3 Hz, 1 H), 1.64-1.56 (m, 2 H), 1.18 (ddd, J = 5.4, 5.4, 15.9 Hz, 1 H), 1.14 (s, 3 H), 1.11 (s, 3 H). | R AC29 BC110 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-238 | 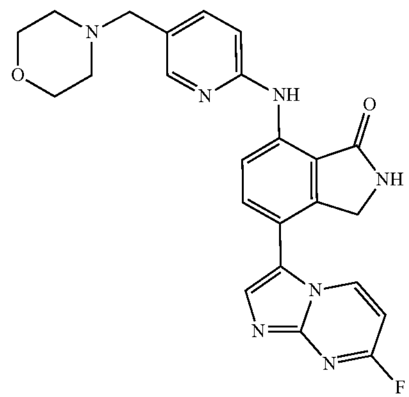 [SMILES: O=C1NCc2c(-c3cnc4nc(F)ccn34)ccc(Nc3ccc(CN4CCOCC4)cn3)c21] | 4-(7-fluoroimidazo[1,2-a]pyridin-3-yl)-7-[[5-(morpholinomethyl)-2-pyridyl]amino]isoindolin-1-one | Method AcHSS C18, m/z = 459 [M + H]+, Ret. time = 1.78 min. | ¹H NMR (400 MHz, DMSO): δ 10.16 (s, 1 H), 8.89 (s, 1 H), 8.76 (d, J = 8.6 Hz, 1 H), 8.49 (dd, J = 5.9, 7.6 Hz, 1 H), 8.26 (s, 1 H), 7.88 (s, 1 H), 7.79 (d, J = 8.5 Hz, 1 H), 7.70 (dd, J = 2.0, 8.3 Hz, 1 H), 7.58 (dd, J = 2.5, 10.3 Hz, 1 H), 7.07-7.02 (m, 2 H), 4.47 (s, 2 H), 3.65 (s, 4 H), 3.49 (s, 2 H), 2.44 (s, 4 H). | F AC38 BC80 |
| I-239 | 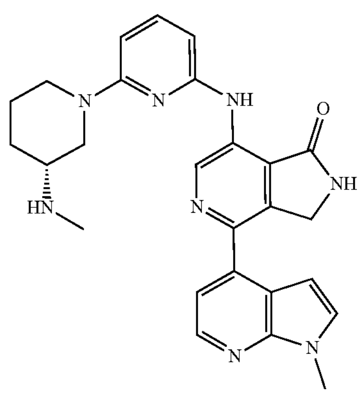 [SMILES: CN[C@@H]1CCCN(c2cccc(Nc3cnc(-c4ccnc5c4ccn5C)c4c3C(=O)NC4)n2)C1] | 7-[[6-((3R)-3-(methylamino)-1-piperidyl]-2-pyridyl]amino]-4-(1-methylpyrrolo[2,3-b]pyridin-4-yl)-2,3-dihydropyrrolo[3,4-c]pyridin-1-one | Method AcHSS C18, m/z = 469 [M + H]+, Ret. time = 2.8 min. | ¹H NMR (400 MHz, DMSO) δ 9.95 (s, 1 H), 9.56 (s, 1 H), 9.20 (s, 1 H), 8.36 (d, J = 5.0 Hz, 1 H), 7.58 (d, J = 3.4 Hz, 1 H), 7.49 (t, J = 8.0 Hz, 1 H), 7.39 (d, J = 5.0 Hz, 1 H), 6.90 (d, J = 3.4 Hz, 1 H), 6.43-6.39 (m, 1 H), 6.26 (d, J = 7.7 Hz, 1 H), 4.75-4.71 (m, 2 H), 4.49 (d, J = 11.2 Hz, 1 H), 4.08-4.02 (m, 1 H), 3.88 (s, 3 H), 3.34 (s, 1 H), 3.03-2.95 (m, 1 H), 2.76-2.68 (m, 2 H), 2.46 (s, 3 H), 1.99-1.92 (m, 1 H), 1.79-1.75 (m, 1 H), 1.58-1.48 (m, 1 H), 1.37-1.25 (m, 1 H). | R AC40 BC26 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-240 | 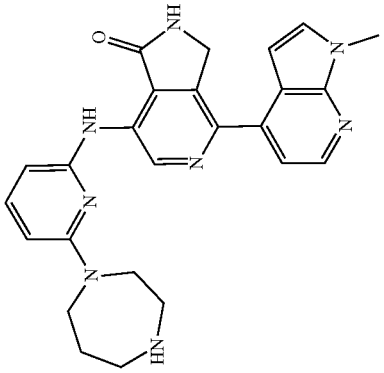 | 7-[[6-(1,4-diazepan-1-yl)-2-pyridyl]amino]-4-(1-methylpyrrolo[2,3-b]pyridin-4-yl)-2,3-dihydropyrrolo[3,4-c]pyridin-1-one | Method AcHSS C18, m/z = 455 [M + H]+, Ret. time = 2.65 min. | ¹H NMR (400 MHz, DMSO): δ 9.98 (s, 1 H), 9.57 (s, 1 H), 9.22 (s, 1 H), 8.40 (d, J = 4.9 Hz, 1 H), 7.62 (d, J = 3.4 Hz, 1 H), 7.49 (t, J = 7.9 Hz, 1 H), 7.42 (d, J = 5.1 Hz, 1 H), 6.91 (d, J = 3.5 Hz, 1 H), 6.26 (d, J = 8.3 Hz, 1 H), 6.22 (d, J = 7.5 Hz, 1 H), 4.75 (s, 2 H), 3.92 (s, 3 H), 3.79 (t, J = 6.0 Hz, 2 H), 3.73 (t, J = 5.3 Hz, 2 H), 2.98 (t, J = 5.1 Hz, 2 H), 2.75 (t, J = 5.8 Hz, 2 H), 1.94-1.85 (m, 2 H). | R AC41 BC26 |
| I-241 | 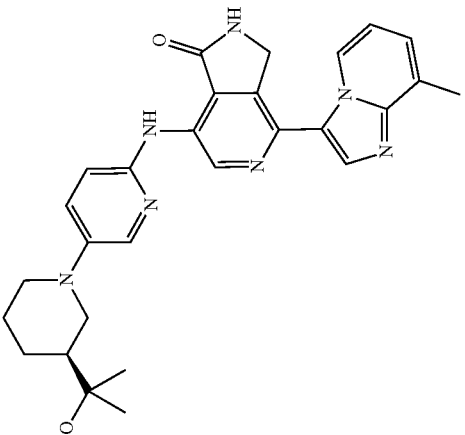 | 7-[[5-[(3S)-3-(1-hydroxy-1-methyl-ethyl)-1-piperidyl]-2-pyridyl]amino]-4-(8-methylimidazo[1,2-a]pyridin-3-yl)-2,3-dihydropyrrolo[3,4-c]pyridin-1-one | Method AcHSS C18, m/z = 498 [M + H]+, Ret. time = 2.71 min. | ¹H NMR (400 MHz, DMSO): δ 9.89 (s, 1 H), 9.72 (d, J = 7.1 Hz, 1 H), 9.38 (s, 1 H), 9.25 (s, 1 H), 8.04 (s, 1 H), 8.02 (d, J = 3.2 Hz, 1 H), 7.43 (dd, J = 3.0, 8.3 Hz, 1 H), 7.24 (d, J = 7.1 Hz, 1 H), 7.04-6.98 (m, 2 H), 4.75 (s, 2 H), 4.29 (s, 1 H), 3.76 (d, J = 14.8 Hz, 1 H), 3.63 (d, J = 11.3 Hz, 1 H), 2.62-2.60 (m, 1 H), 2.59 (s, 3 H), 2.45 (t, J = 11.6 Hz, 1 H), 1.86 (d, J = 13.5 Hz, 1 H), 1.77 (d, J = 14.2 Hz, 1 H), 1.63-1.56 (m, 2 H), 1.22-1.15 (m, 1 H), 1.14 (s, 3 H), 1.12 (s, 3 H). | Hc AC30 BC113 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-242 | 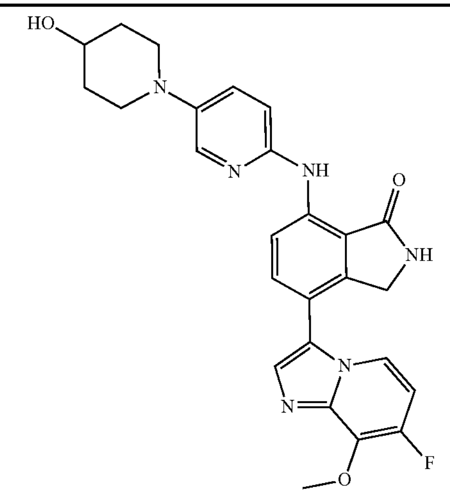 | 4-(7-fluoro-8-methoxy-imidazo[1,2-a]pyridin-3-yl)-7-[[5-(4-hydroxy-1-piperidyl)-2-pyridyl]amino]isoindolin-1-one | Method AcHSS C18, m/z = 489 [M + H]+, Ret. time = 2.19 min. | ¹H NMR (400 MHz, DMSO): δ 9.84 (s, 1 H), 8.78 (s, 1 H), 8.55 (d, J = 9.2 Hz, 1 H), 8.11 (dd, J = 4.8, 7.7 Hz, 1 H), 8.01 (d, J = 3.5 Hz, 1 H), 7.80 (s, 1 H), 7.67 (d, J = 8.8 Hz, 1 H), 7.44 (dd, J = 2.8, 9.0 Hz, 1 H), 7.01 (dd, J = 7.6, 9.7 Hz, 1 H), 6.95 (d, J = 9.0 Hz, 1 H), 4.70 (d, J = 4.2 Hz, 1 H), 4.38 (s, 2 H), 4.25 (s, 3 H), 3.68-3.59 (m, 1 H), 3.50-3.44 (m, 2 H), 2.83 (ddd, J = 2.9, 10.1, 12.7 Hz, 2 H), 1.85 (dd, J = 4.1, 13.0 Hz, 2 H), 1.57-1.47 (m, 2 H). | F AC15 BC116 |
| I-243 | 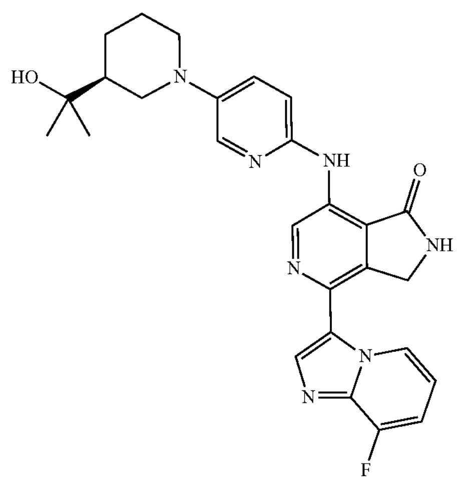 [SMILES: CC(C)(O)[C@H]1CCCN(c2ccc(Nc3cnc(-c4cnc5c(F)cccn45)c4c3C(=O)NC4)nc2)C1] | 4-(8-fluoroimidazo[1,2-a]pyridin-3-yl)-7-[[5-[(3S)-3-(1-hydroxy-1-methyl-ethyl)-1-piperidyl]-2-pyridyl]amino]-2,3-dihydropyrrolo[3,4-c]pyridin-1-one | Method BicarbB EHC18, m/z = 502 [M + H]+, Ret. time = 4.24 min. | ¹H NMR (400 MHz, DMSO): δ 9.91 (s, 1 H), 9.69 (d, J = 7.4 Hz, 1 H), 9.41 (s, 1 H), 9.28 (s, 1 H), 8.11 (s, 1 H), 8.03 (d, J = 2.5 Hz, 1 H), 7.43 (dd, J = 3.0, 9.0 Hz, 1 H), 7.32 (dd, J = 7.9, 11.1 Hz, 1 H), 7.10-7.04 (m, 1 H), 7.03 (d, J = 9.5 Hz, 1 H), 4.76 (s, 2 H), 4.29 (s, 1 H), 3.75 (d, J = 11.2 Hz, 1 H), 3.65 (d, J = 12.4 Hz, 1 H), 2.58 (ddd, J = 12.5, 12.5, 3.0 Hz, 1 H), 2.45 (t, J = 11.6 Hz, 1 H), 1.86 (d, J = 10.7 Hz, 1 H), 1.77 (d, J = 12.4 Hz, 1 H), 1.61-1.54 (m, 2 H), 1.22-1.16 (m, 1 H), 1.13 (s, 3 H), 1.11 (s, 3 H). | Hc AC30 BC114 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-244 | 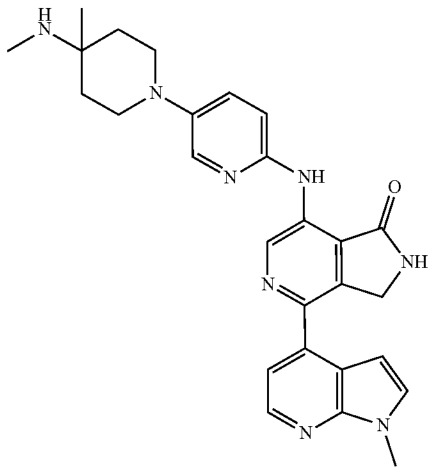 [SMILES: CNC1(C)CCN(c2ccc(Nc3cnc(-c4ccnc5c4ccn5C)c4c3C(=O)NC4)nc2)CC1] | 7-[[5-[4-methyl-4-(methylamino)-1-piperidyl]-2-pyridyl]amino]-4-(1-methylpyrrolo[2,3-b]pyridin-4-yl)-2,3-dihydropyrrolo[3,4-c]pyridin-1-one | Method AcHSS C18, m/z = 483 [M + H]+, Ret. time = 2.39 min. | ¹H NMR (400 MHz, DMSO): δ 9.95 (s, 1 H), 9.53 (s, 1 H), 9.17 (s, 1 H), 8.71 (s, 1 H), 8.36 (d, J = 4.9 Hz, 1 H), 8.11 (d, J = 3.0 Hz, 1 H), 7.58 (d, J = 3.4 Hz, 1 H), 7.53 (dd, J = 3.4, 8.4 Hz, 1 H), 7.39 (d, J = 5.2 Hz, 1 H), 7.10 (d, J = 9.0 Hz, 1 H), 6.91 (d, J = 3.5 Hz, 1 H), 4.74 (s, 2H), 3.90 (s, 3 H), 3.61 (d, J = 12.5 Hz, 2 H), 2.96 (t, J = 10.9 Hz, 2 H), 2.54 (s, 3 H), 1.95-1.81 (m, 4 H), 1.37 (s, 3 H). | R AC2 BC26 |
| I-245 | 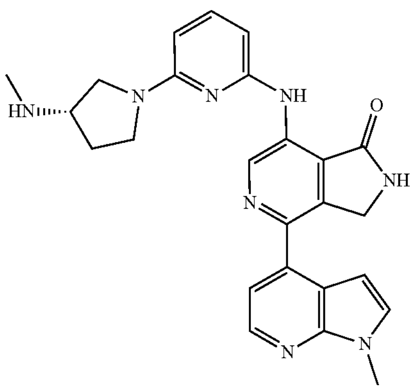 [SMILES: CN[C@H]1CCN(c2cccc(Nc3cnc(-c4ccnc5c4ccn5C)c4c3C(=O)NC4)n2)C1] | 7-[[6-[(3S)-3-(methylamino)pyrrolidin-1-yl]-2-pyridyl]amino]-4-(1-methylpyrrolo[2,3-b]pyridin-4-yl)-2,3-dihydropyrrolo[3,4-c]pyridin-1-one | Method AcHSS C18, m/z = 455 [M + H]+, Ret. time = 2.58 min. | ¹H NMR (400 MHz, DMSO): δ 10.11 (s, 1 H), 9.60 (s, 1 H), 9.20 (s, 1 H), 8.36 (d, J = 4.2 Hz, 1 H), 8.28 (s, 1 H), 7.59 (t, J = 2.9 Hz, 1 H), 7.46 (t, J = 8.0 Hz, 1 H), 7.38 (d, J = 5.2 Hz, 1 H), 6.88 (d, J = 3.7 Hz, 1 H), 6.20 (d, J = 8.1 Hz, 1 H), 6.04 (d, J = 8.4 Hz, 1 H), 4.71 (s, 2 H), 3.75-3.67 (m, 1 H), 3.65-3.60 (m, 1 H), 3.51-3.47 (m, 1 H), 3.39 (dd, J = 4.4, 10.3 Hz, 2 H), 2.43 (s, 3 H), 2.26-2.16 (m, 1 H), 2.02-1.94 (m, 1 H). | R AC6 BC26 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-246 | 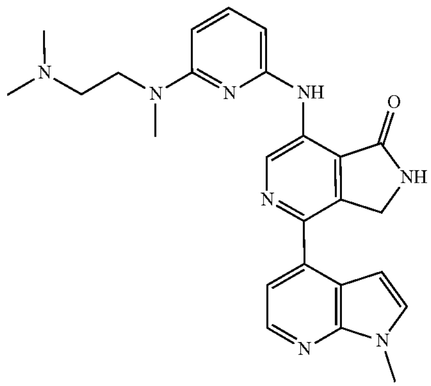 [SMILES: CN(C)CCN(C)c1cccc(Nc2cnc(-c3ccnc4c3ccn4C)c3c2C(=O)NC3)n1] | 7-[[6-[2-(dimethyl-amino)ethyl-methyl-amino]-2-pyridyl]amino]-4-(1-methyl-pyrrolo[2,3-b]pyridin-4-yl)-2,3-dihydropyrrolo[3,4-c]pyridin-1-one | Method AcHSS C18, m/z = 457 [M + H]+, Ret. time = 2.77 min. | ¹H NMR (400 MHz, DMSO): δ 10.06 (s, 1 H), 9.63 (s, 1 H), 9.24 (s, 1 H), 8.40 (d, J = 6.1 Hz, 1 H), 7.62 (d, J = 3.9 Hz, 1 H), 7.51 (dd, J = 8.2, 8.2 Hz, 1 H), 7.43 (d, J = 4.8 Hz, 1 H), 6.97 (d, J = 3.3 Hz, 1 H), 6.27-6.20 (m, 2 H), 4.77 (s, 2 H), 3.92 (s, 3 H), 3.76 (t, J = 7.2 Hz, 2 H), 3.12 (s, 3 H), 2.62-2.59 (m, 2 H), 2.31 (s, 6 H). | R AC35 BC26 |
| I-247 | 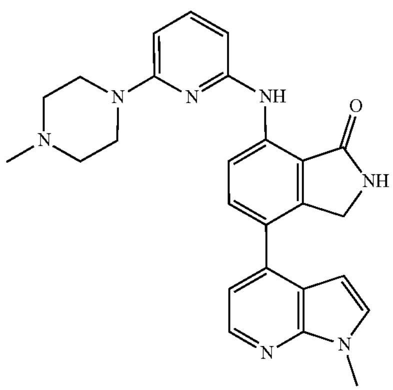 [SMILES: CN1CCN(c2cccc(Nc3ccc(-c4ccnc5c4ccn5C)c4c3C(=O)NC4)n2)CC1] | 7-[[6-(4-methylpiperazin-1-yl)-2-pyridyl]amino]-4-(1-methylpyrrolo[2,3-b]pyridin-4-yl)isoindolin-1-one | Method AcHSS C18, m/z = 454 [M + H]+, Ret. time = 2.71 min. | ¹H NMR (400 MHz, DMSO): δ 9.98 (s, 1 H), 8.80 (s, 1 H), 8.49 (d, J = 7.6 Hz, 1 H), 8.32 (d, J = 4.8 Hz, 1 H), 7.75 (d, J = 8.1 Hz, 1 H), 7.59 (d, J = 3.1 Hz, 1 H), 7.49 (t, J = 7.9 Hz, 1 H), 7.27 (d, J = 4.8 Hz, 1 H), 6.49 (d, J = 2.6 Hz, 1 H), 6.37 (d, J = 9.0 Hz, 1 H), 6.27 (d, J = 8.4 Hz, 1 H), 4.46 (s, 2 H), 3.88 (s, 3 H), 3.53 (t, J = 5.2 Hz, 4 H), 2.45 (t, J = 3.9 Hz, 4 H), 2.24 (s, 3 H). | E AC35 BC26 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-248 | 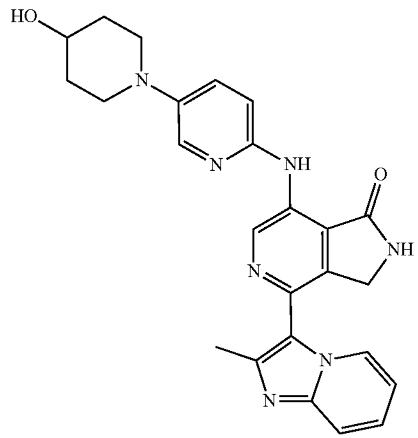 [SMILES: Cc1nc2ccccn2c1-c1ncc(Nc2ccc(N3CCC(O)CC3)cn2)c2c1CNC2=O] | 7-[[5-(4-hydroxy-1-piperidyl)-2-pyridyl]amino]-4-(2-methylimidazo[1,2-a]pyridin-3-yl)-2,3-dihydropyrrolo[3,4-c]pyridin-1-one | Method AcHSS C18, m/z = 456 [M + H]+, Ret. time = 1.91 min. | ¹H NMR (400 MHz, DMSO): δ 9.94 (s, 1 H), 9.44 (s, 1 H), 9.11 (s, 1 H), 8.35 (d, J = 6.8 Hz, 1 H), 8.09 (d, J = 3.0 Hz, 1 H), 7.59 (d, J = 9.4 Hz, 1 H), 7.51 (dd, J = 3.6, 8.5 Hz, 1 H), 7.33 (ddd, J = 1.5, 6.5, 9.0 Hz, 1 H), 7.10 (d, J = 9.0 Hz, 1 H), 6.91 (dt, J = 1.3, 6.8 Hz, 1 H), 4.75 (s, 1 H), 4.36 (s, 2 H), 3.70-3.50 (m, 2 H), 3.57-3.50 (ddd, J = 2.7, 10.2, 12.5 Hz, 2 H), 2.89 (ddd, J = 2.7, 10.2, 12.5 Hz, 2 H), 2.40 (s, 3 H), 1.90 (dd, J = 4.3, 14.0 Hz, 2 H), 1.54 (ddd, J = 4.9, 4.9, 4.9 Hz, 2 H). | Hc AC15 BC112 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-249 | 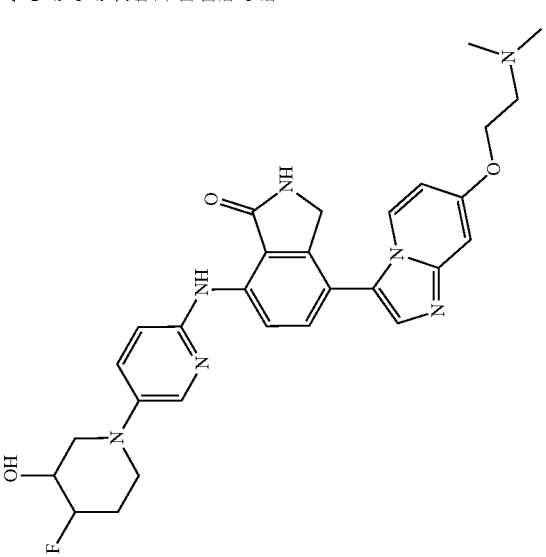<br>Unknown trans isomer | 4-[7-[2-(dimethyl-amino)ethoxy]imi-dazo[1,2-a]pyridin-3-yl]-7-[[5-(4-fluoro-3-hydroxy-1-piperidyl)-2-pyridyl]amino]iso-indolin-1-one, trans isomer | Method AcHSS C18, m/z = 546 [M + H]+, Ret. time = 1.97 min. | ¹H NMR (400 MHz, DMSO): δ 9.85 (s, 1 H), 8.78 (s, 1 H), 8.55 (d, J = 8.7 Hz, 1 H), 8.24 (d, J = 8.3 Hz, 1 H), 8.02 (d, J = 2.8 Hz, 1 H), 7.66 (t, J = 4.2 Hz, 2 H), 7.47 (dd, J = 3.3, 8.9 Hz, 1 H), 7.08 (d, J = 2.8 Hz, 1 H), 6.97 (d, J = 9.0 Hz, 1 H), 6.64 (dd, J = 2.6, 7.6 Hz, 1 H), 5.43 (d, J = 5.3 Hz, 1 H), 4.53-4.40 (m, 1 H), 4.39 (s, 2 H), 4.20 (t, J = 5.6 Hz, 2 H), 3.74-3.63 (m, 1 H), 3.59-3.51 (m, 2 H), 2.85-2.76 (m, 3 H), 2.65 (dd, J = 9.0, 12.1 Hz, 1 H), 2.34 (s, 6 H), 2.16-2.09 (m, 1H), 1.81-1.69 (m, 1 H). | F<br>AC42<br>BC115 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-250 | 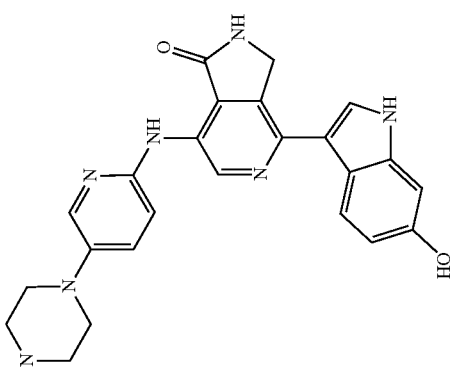 | 4-(6-hydroxy-1H-indol-3-yl)-7-((5-(4-methylpiperazin-1-yl)pyridin-2-yl)amino)-2,3-dihydro-1H-pyrrolo[3,4-c]pyridin-1-one | LCMS Method C m/z = 456.52 [M + H]+, Ret. time = 1.27 min. | 1H NMR (400 MHz, DMSO-d6) δ 11.15 (s, 1H), 9.80 (s, 1H), 9.31 (s, 1H), 9.17 (s, 1H), 9.07 (s, 1H), 8.08 (s, 1H), 7.61-7.39 (m, 2H), 7.04 (d, J = 9.0 Hz, 1H), 6.80 (s, 1H), 6.64 (d, J = 8.8 Hz, 1H), 4.66 (s, 2H), 3.24 (s, 5H), 2.76 (s, 3H), 1.21 (dt, J = 22.9, 7.5 Hz, 4H). | A AA2 BB50 |
| I-251 | 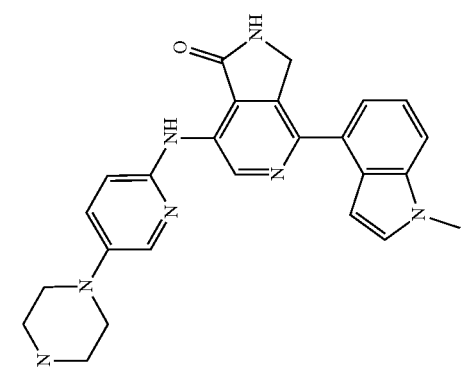 | 4-(1-methyl-1H-indol-4-yl)-7-((5-(4-methylpiperazin-1-yl)pyridin-2-yl)amino)-2,3-dihydro-1H-pyrrolo[3,4-c]pyridin-1-one | LCMS Method C m/z = 454.6 [M + H]+, Ret. time = 1.30 min. | 1H NMR (400 MHz, DMSO-d6) δ 9.86 (s, 1H), 9.39 (s, 1H), 9.07 (s, 1H), 8.03 (d, J = 3.1 Hz, 1H), 7.54-7.41 (m, 2H), 7.41-7.29 (m, 2H), 7.24 (t, J = 7.7 Hz, 1H), 7.02 (d, J = 9.0 Hz, 1H), 6.73 (d, J = 3.1 Hz, 1H), 4.57 (s, 2H), 3.84 (s, 3H), 3.12 (t, J = 4.9 Hz, 4H), 2.48-2.44 (m, 4H), 2.23 (s, 3H). | A AA2 BB41 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-252 | 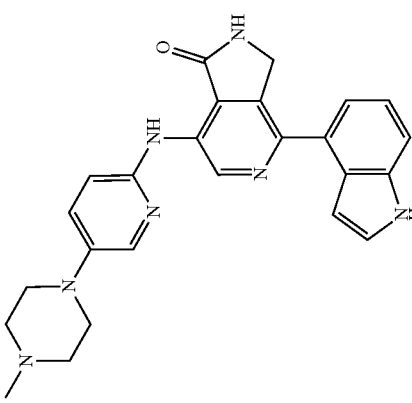 | 4-(1H-indol-4-yl)-7-(5-(4-methylpiperazin-1-yl)pyridin-2-ylamino)-2,3-dihydro-1H-pyrrolo[3,4-c]pyridin-1-one | Method C m/z = 440.5 [M + H]+, Ret. time = 1.26 min. | 1H NMR (400 MHz, DMSO-d6) δ 11.22 (s, 1H), 9.88 (s, 1H), 9.46 (s, 1H), 9.08 (s, 1H), 8.10 (s, 1H), 7.52 (d, J = 9.7 Hz, 1H), 7.45 (d, J = 8.0 Hz, 1H), 7.38 (s, 1H), 7.29 (d, J = 7.3 Hz, 1H), 7.17 (t, J = 7.8 Hz, 1H), 7.09 (d, J = 8.9 Hz, 1H), 6.73 (s, 1H), 4.58 (s, 2H), 2.82 (s, 3H). | A AA2 BB42 |
| I-253 | 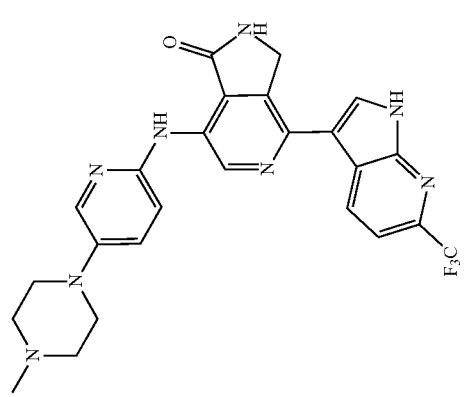 | 7-((5-(4-methylpiperazin-1-yl)pyridin-2-yl)amino)-4-(6-(trifluoromethyl)-1H-pyrrolo[2,3-b]pyridin-3-yl)-2,3-dihydro-1H-pyrrolo[3,4-c]pyridin-1-one | LCMS Method C m/z = 509.6 [M + H]+, Ret. time = 1.38 min. | 1H NMR (400 MHz, DMSO-d6) δ 12.60 (s, 1H), 9.87 (s, 1H), 9.39-9.02 (m, 2H), 8.08 (d, J = 37.9 Hz, 2H), 7.67 (s, 1H), 7.45 (s, 1H), 7.01 (s, 1H), 4.76 (s, 1H), 3.12 (s, 3H), 2.24 (s, 4H). | A AA2 BB4 |

| # | STRUCTURE | NAME | LCMS | ¹H NMR | Method Reagent AA BB |
|---|---|---|---|---|---|
| I-254 | 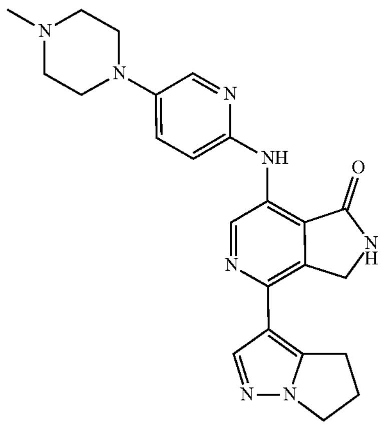 | 4-(5,6-dihydro-4H-pyrrolo[1,2-b]pyrazol-3-yl)-7-((5-(4-methylpiperazin-1-yl)pyridin-2-yl)amino)-2,3-dihydro-1H-pyrrolo[3,4-c]pyridin-1-one | LCMS Method C m/z = 431.5 [M + H]+, Ret. time = 1.23 min. | 1H NMR (400 MHz, DMSO-d6) δ 9.71 (s, 1H), 9.21 (s, 1H), 9.13 (s, 1 H), 8.00 (s, 1H), 7.81 (s, 1H), 7.44 (d, J = 7.9 Hz, 1H), 6.98 (d, J = 8.9 Hz, 1H), 4.63 (s, 2H), 4.13 (t, J = 7.2 Hz, 2H), 3.11 (s, 6H), 2.62 (s, 2H), 2.24 (s, 3H). | A AA2 BB45 |
| I-255 | 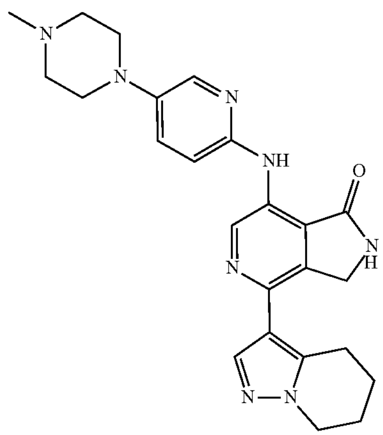 | 7-((5-(4-methylpiperazin-1-yl)pyridin-2-yl)amino)-4-(4,5,6,7-tetrahydropyrazolo[1,5-a]pyridin-3-yl)-2,3-dihydro-1H-pyrrolo[3,4-c]pyridin-1-one | LCMS Method C m/z = 445.6 [M + H]+, Ret. time = 1.25 min | 1H NMR (400 MHz, DMSO-d6) δ 9.71 (s, 1H), 9.22 (s, 1H), 9.11 (s, 1H), 7.98 (d, J = 3.0 Hz, 1H), 7.77 (s, 1H), 7.42 (dd, J = 9.1, 3.1 Hz, 1H), 6.96 (d, J = 8.9 Hz, 1H), 4.61 (s, 2H), 4.12 (t, J = 6.0 Hz, 2H), 3.09 (s, 6H), 2.22 (s, 3H), 1.99 (d, J = 6.9 Hz, 2H), 1.83 (d, J = 7.5 Hz, 2H). | A AA2 BB46 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-256 | 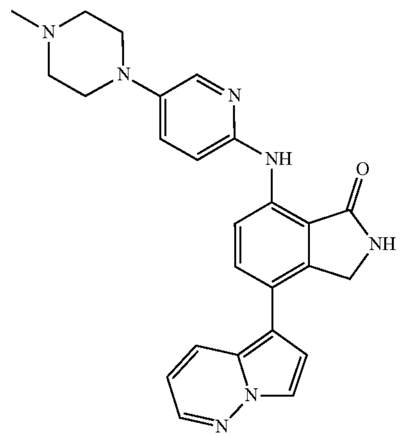 [SMILES: CN1CCN(c2ccc(Nc3ccc(-c4ccn5ncccc45)c4c3C(=O)NC4)nc2)CC1] | 7-((5-(4-methylpiperazin-1-yl)pyridin-2-yl)amino)-4-(pyrrolo[1,2-b]pyridazin-5-yl)isoindolin-1-one | LCMS Method C m/z = 440.57 [M + H]+, Ret. time = 1.37 min | 1H NMR (400 MHz, DMSO-d6) δ 9.78 (d, J = 4.6 Hz, 1H), 8.75 (d, J = 4.5 Hz, 1H), 8.48 (dd, J = 8.5, 4.5 Hz, 1H), 8.19 (s, 1H), 8.05 (dd, J = 9.4, 4.4 Hz, 1H), 7.97 (q, J = 3.4, 3.0 Hz, 2H), 7.59 (dd, J = 8.6, 4.7 Hz, 1H), 7.42 (dt, J = 8.7, 3.9 Hz, 1H), 7.18 (t, J = 3.8 Hz, 1H), 6.91 (dd, J = 9.0, 4.6 Hz, 1H), 6.70 (dt, J = 9.1, 4.6 Hz, 1H), 4.47 (d, J = 4.6 Hz, 2H), 3.09 (q, J = 4.9 Hz, 4H), 2.23 (d, J = 4.7 Hz, 3H). | F AA2 BB47 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-257 | 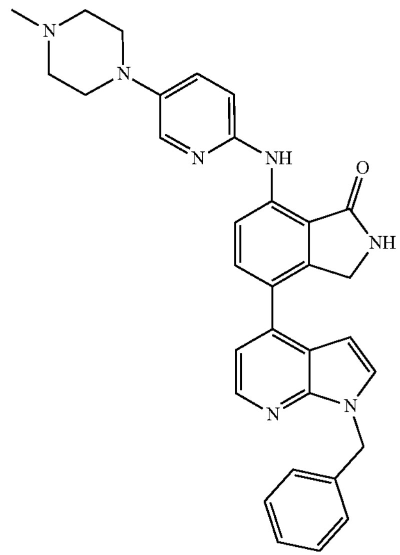 [SMILES: CN1CCN(c2ccc(Nc3ccc(-c4ccnc5c4ccn5Cc4ccccc4)c4c3C(=O)NC4)nc2)CC1] | 4-(1-benzyl-1H-pyrrolo[2,3-b]pyridin-4-yl)-7-((5-(4-methylpiperazin-1-yl)pyridin-2-yl)amino)isoindolin-1-one | LCMS Method C m/z = 530.44 [M + H]+, Ret. time = 1.45 min | 1H NMR (400 MHz, DMSO-d6) δ 9.94 (s, 1H), 8.78 (s, 1H), 8.55 (d, J = 8.6 Hz, 1H), 8.32 (d, J = 5.0 Hz, 1H), 8.01 (d, J = 3.0 Hz, 1H), 7.73 (dd, J = 15.9, 6.1 Hz 2H), 7.45 (dd, J = 8.9, 3.1 Hz, 1H), 7.31 (h, J = 7.3, 6.8 Hz, 6H), 6.97 (d, J = 8.9 Hz, 1H), 6.54 (d, J = 3.6 Hz, 1H), 5.54 (s, 2H), 4.49 (s, 2H), 3.12 (t, J = 4.8 Hz, 4H), 2.48 (s, 5H), 2.24 (s, 3H). | A AA2 BB48 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-258 | 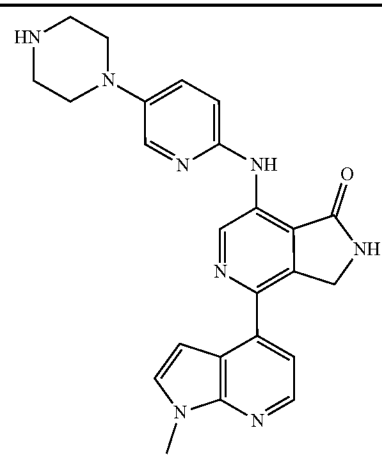 | 4-(1-methyl-1H-pyrrolo[2,3-b]pyridin-4-yl)-7-((5-(piperazin-1-yl)pyridin-2-yl)amino)-2,3-dihydro-1H-pyrrolo[3,4-c]pyridin-1-one | LCMS Method J m/z = 441.2 [M + H]+, Ret. time = 2.91 min | 1H NMR (400 MHz, DMSO-d6) δ 9.92 (s, 1H), 9.52 (s, 1H), 9.18 (s, 1H), 8.41-8.24 (m, 2H), 8.05 (d, J = 3.0 Hz, 1H), 7.56 (d, J = 3.5 Hz, 1H), 7.47 (dd, J = 9.0, 3.0 Hz, 1H), 7.37 (d, J = 5.0 Hz, 1H), 7.06 (d, J = 8.9 Hz, 1H), 6.90 (d, J = 3.4 Hz, 1H), 4.71 (s, 2H), 3.86 (s, 3H), 3.16-3.09 (m, 4H), 2.98 (t, J = 4.9 Hz, 4H). | A AA1 BB14 |
| I-259 | 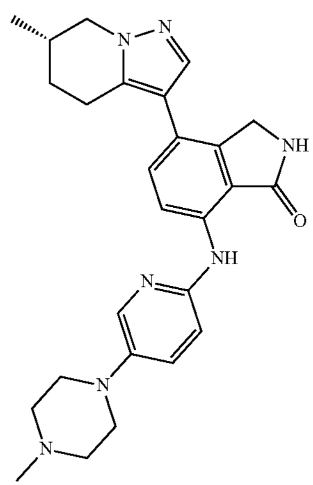 [SMILES: C[C@H]1CCc2c(-c3ccc(Nc4ccc(N5CCN(C)CC5)cn4)c4c3CNC4=O)cnn2C1] | (R)-4-(6-methyl-6,7-dihydro-5H-pyrazolo[5,1-b][1,3]oxazin-3-yl)-7-((5-(4-methylpiperazin-1-yl)pyridin-2-yl)amino)isoindolin-1-one | LCMS Method C m/z = 460.36 [M + H]+, Ret. time = 1.26 min Chiral HPLC Method X1 = Ret. time = 15.33 | 1H NMR (400 MHz, DMSO-d6) δ 9.71 (s, 1H), 8.74 (s, 1H), 8.34 (d, J = 8.6 Hz, 1H), 7.94 (d, J = 3.0 Hz, 1H), 7.58 (d, J = 10.3 Hz, 2H), 7.40 (dd, J = 9.0, 3.1 Hz, 1H), 6.89 (d, J = 9.0 Hz, 1H), 4.41 (dd, J = 12.1, 4.5 Hz, 3H), 4.22 (dd, J = 12.0, 5.3 Hz, 1H), 4.02 (t, J = 10.0 Hz, 1H), 3.75 (dd, J = 12.0, 8.8 Hz, 1H), 3.07 (s, 4H), 2.45 (s, 4H), 2.22 (s, 3H), 1.05 (d, J = 6.8 Hz, 3H). | F AA2 BB50 |

| # | STRUCTURE | NAME | LCMS | 1H NMR | Method Reagent AA BB |
|---|---|---|---|---|---|
| I-260 | 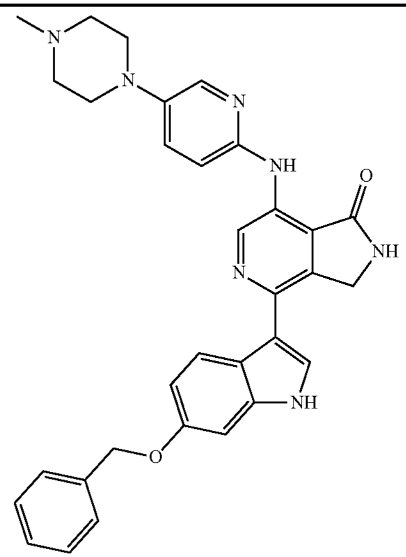 | 4-(6-(benzyloxy)-1H-indol-3-yl)-7-((5-(4-methylpiperazin-1-yl)pyridin-2-yl)amino)-2,3-dihydro-1H-pyrrolo[3,4-c]pyridin-1-one | LCMS Method C m/z = 546.46 [M + H]+, Ret. time = 1.37 min | 1H NMR (400 MHz, DMSO-d6) δ 11.32 (s, 1H), 9.79 (s, 1H), 9.24 (s, 1H), 9.15 (s, 1H), 8.48 (d, J = 8.8 Hz, 1H), 8.01 (d, J = 3.0 Hz, 1H), 7.59 (s, 1H), 7.49 (d, J = 7.5 Hz, 2H), 7.42 (q, J = 8.5, 7.5 Hz, 3H), 7.33 (t, J = 7.3 Hz, 1H), 6.98 (d, J = 10.0 Hz, 2H), 6.85 (d, J = 8.6 Hz, 1H), 5.15 (s, 2H), 4.65 (s, 2H), 3.10 (t, J = 4.9 Hz, 4H), 2.23 (s, 3H). | A AA2 BB50 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-261 | 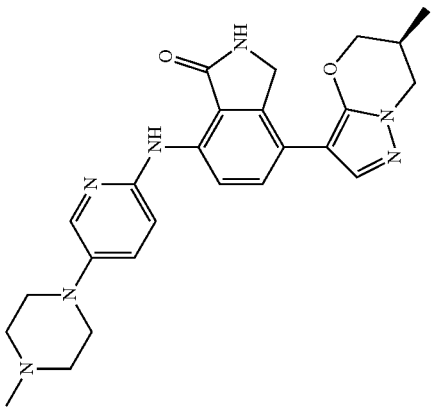 | (S)-4-(6-methyl-6,7-dihydro-5H-pyrazolo[5,1-b][1,3]oxazin-3-yl)-7-(5-(4-methylpiperazin-1-yl)pyridin-2-yl)amino)isoindolin-1-one | LCMS Method C m/z = 460.53 [M + H]+, Ret. time = 1.30 min Chiral HPLC method X2: Ret. time = 8.09 | 1H NMR (400 MHz, DMSO-d6) δ 9.73 (s, 1H), 8.75 (s, 1H), 8.35 (d, J = 8.6 Hz, 1H), 7.96 (d, J = 2.9 Hz, 1H), 7.59 (d, J = 10.5 Hz, 2H), 7.41 (dd, J = 8.9, 3.0 Hz, 1H), 6.90 (d, J = 8.9 Hz, 1H), 4.43 (dd, J = 11.6, 4.3 Hz, 3H), 4.24 (dd, J = 11.7, 5.4 Hz, 1H), 4.04 (t, J = 10.0 Hz, 1H), 3.80-3.71 (m, 1H), 3.09 (t, J = 4.9 Hz, 4H), 2.48 (s, 4H), 2.24 (s, 3H), 1.07 (d, J = 6.8 Hz, 3H). | F AA2 BB51 |
| I-262 | 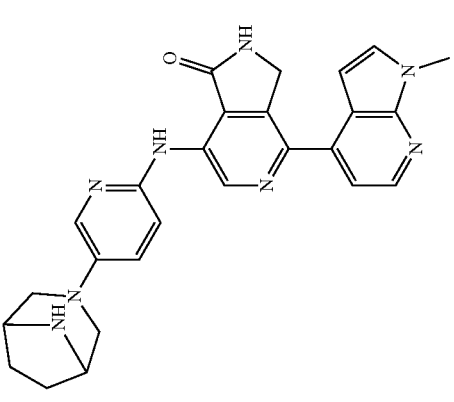 | 7-((5-(3,8-diazabicyclo[3.2.1]octan-3-yl)pyridin-2-yl)amino)-4-(1-methyl-1H-pyrrolo[2,3-b]pyridin-4-yl)-2,3-dihydro-1H-pyrrolo[3,4-c]pyridin-1-Fone | LCMS Method J m/z = 467.2 [M + H]+, Ret. time = 3.01 min | 1H NMR (400 MHz, DMSO-d6) δ 9.90 (s, 1H), 9.47 (s, 1H), 9.16 (s, 1H), 8.36 (d, J = 5.0 Hz, 1H), 8.28 (s, 1H), 7.96 (d, J = 3.0 Hz, 1H), 7.58 (d, J = 3.5 Hz, 1H), 7.37 (dd, J = 8.6, 3.8 Hz, 2H), 7.06 (d, J = 9.1 Hz, 1H), 6.92 (d, J = 3.5 Hz, 1H), 4.73 (s, 2H), 3.88 (s, 3H), 3.64 (s, 2H), 2.83 (d, J = 10.2 Hz, 2H), 1.79 (t, J = 9.6 Hz, 4H). | A AA6 BB14 |

| # | STRUCTURE | NAME | LCMS | ¹H NMR | Method Reagent AA BB |
|---|---|---|---|---|---|
| I-263 | 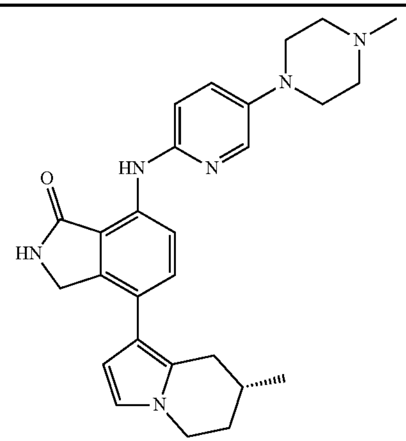 | (FR)-4-(5-mFethyl-4,5,A,6,7-tetrahydropyrazolo[1,5-a]pyridin-3-yl)-7-((5-(4-methylpiperazin-1-yl)pyridin-2-yl)amino)isoindolin-1-one | LCMS Method H m/z = 446.1 [M + H]+, Ret. time = 3.20 min Chiral HPLC method X1: Ret. time = 11.97 | 1H NMR (400 MHz, DMSO-d6) δ 9.74 (s, 1H), 8.73 (s, 1H), 8.42 (d, J = 8.5 Hz, 1H), 7.96 (d, J = 3.0 Hz, 1H), 7.70 (s, 1H), 7.50-7.31 (m, 2H), 6.91 (d, J = 8.9 Hz, 1H), 4.58 (d, J = 18.1 Hz, 1H), 4.36-4.15 (m, 2H), 4.05 (td, J = 12.4, 11.9, 4.9 Hz, 1H), 3.09 (d, J = 5.3 Hz, 4H), 2.89 (dd, J = 16.2, 4.8 Hz, 1H), 2.25 (s, 3H), 2.04 (d, J = 13.0 Hz, 1H), 1.94 (s, 1H), 1.76 (s, 1H), 1.10 (d, J = 6.4 Hz, 4H). | F AA2 BB52 |
| I-264 | 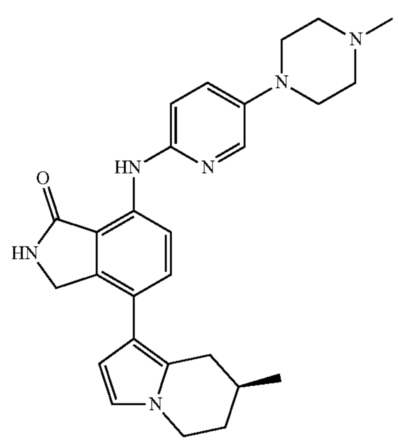 [SMILES: C[C@H]1CCn2ccc(-c3ccc(Nc4ccc(N5CCN(C)CC5)cn4)c4c3CNC4=O)c2C1] | (S)-4-(5-methyl-4,5,6,7-tetrahydropyrazolo[1,5-a]pyridin-3-yl)-7-((5-(4-methylpiperazin-1-yl)pyridin-2-yl)amino)isoindolin-1-one | LCMS Method C m/z = 458.4 [M + H]+, Ret. time = 1.30 min Chiral HPLC method X1: Ret. time = 14.44 | 1H NMR (400 MHz, DMSO-d6) δ 9.74 (s, 1H), 8.73 (s, 1H), 8.42 (d, J = 8.5 Hz, 1H), 7.96 (d, J = 3.0 Hz, 1H), 7.70 (s, 1H), 7.50-7.31 (m, 2H), 6.91 (d, J = 8.9 Hz, 1H), 4.58 (d, J = 18.1 Hz, 1H), 4.36-4.15 (m, 2H), 4.05 (td, J = 12.4, 11.9, 4.9 Hz, 1H), 3.09 (d, J = 5.3 Hz, 4H), 2.89 (dd, J = 16.2, 4.8 Hz, 1H), 2.25 (s, 3H), 2.04 (d, J = 13.0 Hz, 1H), 1.94 (s, 1H), 1.76 (s, 1H), 1.10 (d, J = 6.4 Hz, 4H). | F AA2 BB52 |

TABLE 8-continued

Characterization Data (LCMS and ¹H NMR).

| # | STRUCTURE | NAME | LCMS | ¹H NMR | Method AA Reagent BB |
|---|---|---|---|---|---|
| I-265 | 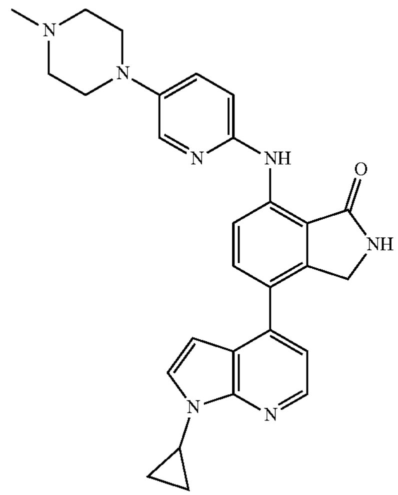 [SMILES: CN1CCN(c2ccc(Nc3ccc(-c4ccnc5c4ccn5C4CC4)c4c3C(=O)NC4)nc2)CC1] | 4-(1-cyclopropyl-1H-pyrrolo[2,3-b]pyridin-4-yl)-7-((5-(4-methylpiperazin-1-yl)pyridin-2-yl)amino)isoindolin-1-one | LCMS Method C m/z = 480.6 [M + H]+, Ret. time = 1.34 min | 1H NMR (400 MHz, DMSO-d6) δ 9.93 (s, 1H), 8.78 (s, 1H), 8.55 (d, J = 8.6 Hz, 1H), 8.33 (d, J = 4.9 Hz, 1H), 8.01 (d, J = 3.0 Hz, 1H), 7.71 (d, J = 8.6 Hz, 1H), 7.54 (d, J = 3.6 Hz, 1H), 7.46 (dd, J = 9.0, 3.1 Hz, 1H), 7.29 (d, J = 5.0 Hz, 1H), 6.97 (d, J = 9.0 Hz, 1H), 6.44 (d, J = 3.6 Hz, 1H), 4.47 (s, 2H), 3.65 (dq, J = 7.1, 4.1, 3.5 Hz, 1H), 3.12 (t, J = 5.0 Hz, 4H), 2.49 (d, J = 5.1 Hz, 4H), 2.24 (s, 3H), 1.08 (ddd, J = 11.1, 5.6, 2.8 Hz, 4H). | F AA2 BB53 |
| I-266 | 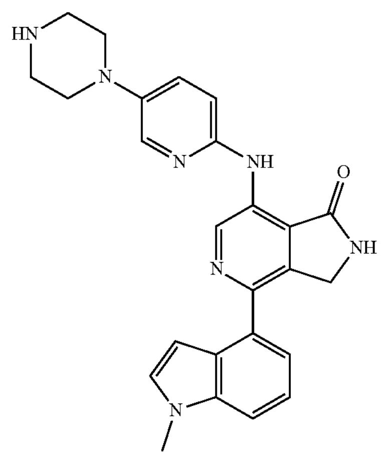 [SMILES: Cn1ccc2c(-c3ncc(Nc4ccc(N5CCNCC5)cn4)c4c3CNC4=O)cccc21] | 4-(1-methyl-1H-indol-4-yl)-7-((5-(piperazin-1-yl)pyridin-2-yl)amino)-2,3-dihydro-1H-pyrrolo[3,4-c]pyridin-1-one | LCMS Method J m/z = 440.2 [M + H]+, Ret. time = 3.14 min | 1H NMR (400 MHz, DMSO-d6) δ 9.86 (s, 1H), 9.41 (s, 1H), 9.07 (s, 1H), 8.04 (d, J = 3.0 Hz, 1H), 7.48 (dd, J = 14.9, 9.2 Hz, 3H), 7.39-7.30 (m, 2H), 7.24 (t, J = 7.7 Hz, 1H), 7.04 (d, J = 8.9 Hz, 1H), 6.72 (d, J = 3.1 Hz, 1H), 4.57 (s, 2H), 3.83 (s, 3H), 3.10 (d, J = 5.1 Hz, 4H), 2.97 (s, 4H). | A AA1 BB41 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-267 | 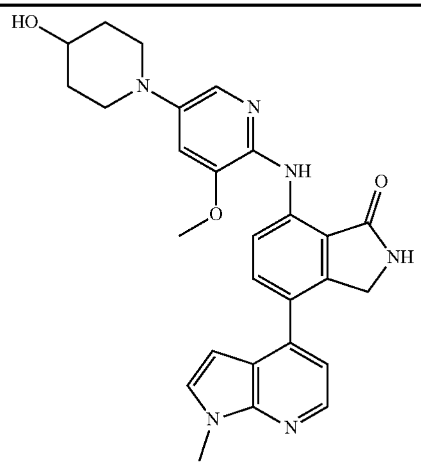 | 7-((5-(4-hydroxypiperidin-1-yl)-3-methoxypyridin-2-yl)amino)-4-(1-methyl-1H-pyrrolo[2,3-b]pyridin-4-yl)isoindolin-1-one | LCMS Method C m/z = 485.4 [M + H]+, Ret. time = 1.36 min | 1H NMR (400 MHz, DMSO-d6) δ 10.30 (s, 1H), 8.87 (d, J = 8.6 Hz, 1H), 8.67 (s, 1H), 8.31 (d, J = 4.9 Hz, 1H), 7.73 (d, J = 8.6 Hz, 1H), 7.56 (dd, J = 18.3, 3.0 Hz, 2H), 7.27 (d, J = 5.0 Hz, 1H), 7.11 (d, J = 2.5 Hz, 1H), 6.48 (d, J = 3.5 Hz, 1H), 4.73 (d, J = 4.1 Hz, 1H), 4.46 (s, 2H), 3.94 (s, 3H), 3.88 (s, 3H), 3.64 (td, J = 9.1, 4.6 Hz, 1H), 3.50 (dt, J = 11.3, 4.3 Hz, 2H), 2.89-2.78 (m, 2H), 1.91-1.82 (m, 2H), 1.58-1.48 (m, 2H). | D AA7 BB14 |
| I-268 | 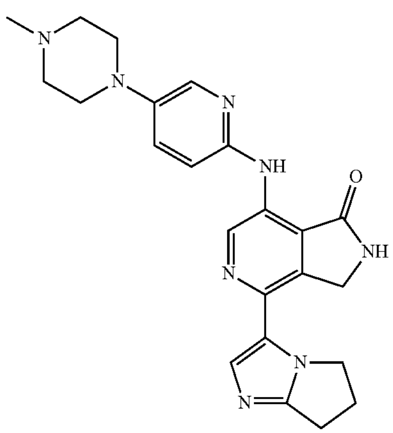 [SMILES: CN1CCN(c2ccc(Nc3cnc(-c4cnc5n4CCC5)c4c3C(=O)NC4)nc2)CC1] | 4-(6,7-dihydro-5H-pyrrolo[1,2-a]imidazol-3-yl)-7-((5-(4-methylpiperazin-1-yl)pyridin-2-yl)amino)-2,3-dihydro-1H-pyrrolo[3,4-c]pyridin-1-one | LCMS Method C m/z = 431.4 [M + H]+, Ret. time = 1.20 min | 1H NMR (400 MHz, DMSO-d6) δ 9.76 (s, 1H), 9.28 (s, 1H), 9.19 (s, 1H), 8.02 (d, J = 3.0 Hz, 1H), 7.45 (dd, J = 9.0, 3.1 Hz, 1H), 7.27 (s, 1H), 7.00 (d, J = 9.0 Hz, 1H), 4.57 (s, 2H), 4.36 (t, J = 7.1 Hz, 2H), 3.12 (t, J = 4.8 Hz, 4H), 2.81 (t, J = 7.5 Hz, 1H), 2.59 (dd, J = 14.5, 6.6 Hz, 4H), 2.26 (s, 4H), 1.24 (s, 2H). | A AA2 BB54 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-269 | 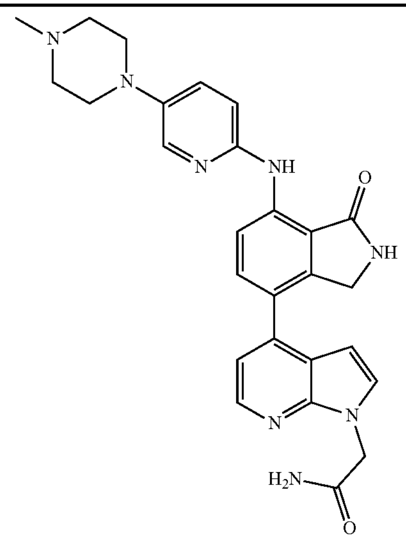 | 2-(4-(7-((5-(4-methylpiperazin-1-yl)pyridin-2-yl)amino)-1-oxoisoindolin-4-yl)-1H-pyrrolo[2,3-b]pyridin-1-yl)acetamide | LCMS Method C m/z = 497.4 [M + H]+, Ret. time = 1.25 min | 1H NMR (400 MHz, DMSO-d6) δ 9.94 (s, 1H), 8.79 (s, 1H), 8.57 (d, J = 8.6 Hz, 1H), 8.27 (d, J = 4.9 Hz, 1H), 8.02 (d, J = 3.1 Hz, 1H), 7.75 (d, J = 8.6 Hz, 1H), 7.66 (s, 1H), 7.57 (d, J = 3.6 Hz, 1H), 7.46 (dd, J = 9.0, 3.2 Hz, 1H), 7.35-7.18 (m, 2H), 6.98 (d, J = 9.0 Hz, 1H), 6.49 (d, J = 3.6 Hz, 1H), 4.95 (s, 2H), 4.50 (s, 2H), 3.12 (t, J = 4.9 Hz, 4H), 2.53 (s 4H), 2.25 (s, 3H). | F AA2 BB55 |
| I-270 | 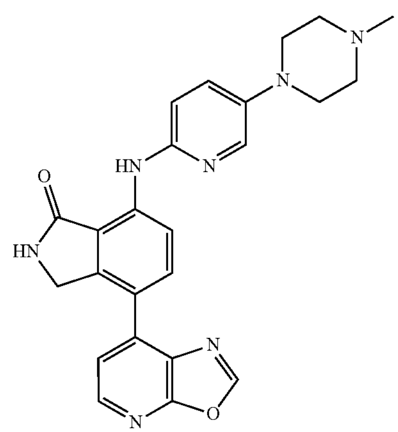 [SMILES: CN1CCN(c2ccc(Nc3ccc(-c4ccnc5ocnc45)c4c3C(=O)NC4)nc2)CC1] | 7-((5-(4-methylpiperazin-1-yl)pyridin-2-yl)amino)-4-(oxazolo[5,4-b]pyridin-7-yl)isoindolin-1-one | LCMS Method C m/z = 442.6 [M + H]+, Ret. time = 1.32 min | 1H NMR (400 MHz, DMSO-d6) δ 10.12 (s, 1H), 9.00 (s, 1H), 8.95 (d, J = 8.9 Hz, 1H), 8.85 (s, 1H), 8.65 (d, J = 5.5 Hz, 1H), 8.52 (d, J = 8.8 Hz, 1H), 8.02 (d, J = 3.0 Hz, 1H), 7.79 (d, J = 5.5 Hz, 1H), 7.45 (dd, J = 9.0, 3.1 Hz, 1H), 6.99 (d, J = 9.0 Hz, 1H), 4.83 (s, 2H), 3.12 (t, J = 4.8 Hz, 4H), 2.47 (s, 4H), 2.23 (s, 3H). | F AA2 BB56 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-271 | 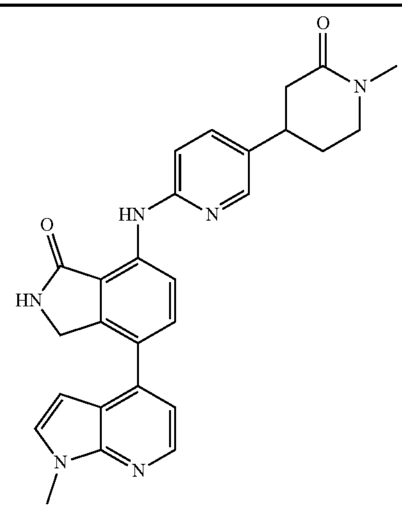 | 4-(1-methyl-1H-pyrrolo[2,3-b]pyridin-4-yl)-7-((5-(1-methyl-2-oxopiperidin-4-yl)pyridin-2-yl)amino)isoindolin-1-one | LCMS Method C m/z = 467.6 [M + H]+, Ret. time = 1.42 min | 1H NMR (400 MHz, DMSO-d6) δ 10.15 (s, 1H), 8.84 (s, 1H), 8.71 (d, J = 8.5 Hz, 1H), 8.33 (d, J = 4.9 Hz, 1H), 8.24 (d, J = 2.4 Hz, 1H), 7.77 (d, J = 8.5 Hz, 1H), 7.67 (dd, J = 8.5, 2.5 Hz, 1H), 7.60 (d, J = 3.5 Hz, 1H), 7.28 (d, J = 4.9 Hz, 1H), 7.01 (d, J = 8.5 Hz, 1H), 6.49 (d, J = 3.5 Hz, 1H), 4.48 (s, 2H), 3.88 (s, 3H), 3.44 (dd, J = 18.7, 6.8 Hz, 1H), 2.88 (s, 3H), 2.50-2.38 (m, 5H), 2.01 (s, 2H). | E AA8 BB14 |
| I-272 | 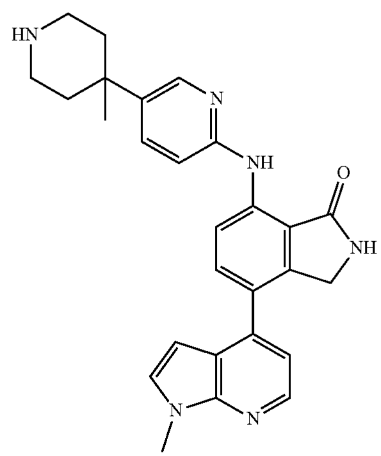 [SMILES: Cn1ccc2c(-c3ccc(Nc4ccc(C5(C)CCNCC5)cn4)c4c3CNC4=O)ccnc21] | 4-(1-methyl-1H-pyrrolo[2,3-b]pyridin-4-yl)-7-((5-(4-methylpiperidin-4-yl)pyridin-2-yl)amino)isoindolin-1-one | LCMS Method C m/z = 453.4 [M + H]+, Ret. time = 1.31 min | 1H NMR (400 MHz, Chloroform-d) δ 8.75 (d, J = 8.5 Hz, 1H), 8.50 (s, 1H), 8.35 (d, J = 5.0 Hz, 1H), 8.30 (d, J = 2.6 Hz, 1H), 7.73 (d, J = 8.6 Hz, 1H), 7.63-7.54 (m, 1H), 7.25 (d, J = 3.5 Hz, 1H), 7.08 (d, J = 5.0 Hz, 1H), 6.94 (d, J = 8.6 Hz, 1H), 6.41 (d, J = 3.5 Hz, 1H), 4.44 (s, 2H), 3.94 (s, 3H), 3.39 (s, 3H), 3.30-3.14 (m, 2H), 3.01 (s, 2H), 2.39-2.24 (m, 2H), 1.97 (s, 3H). | E AA9 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-273 | 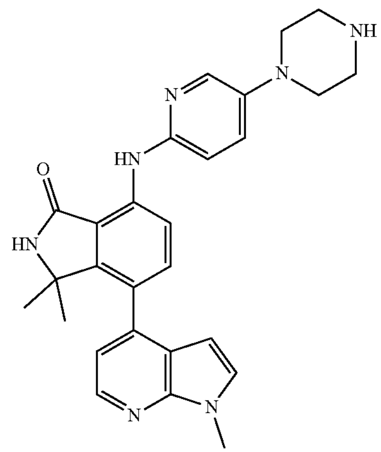 [SMILES: Cn1ccc2c(-c3ccc(Nc4ccc(N5CCNCC5)cn4)c4c3C(C)(C)NC4=O)ccnc21] | 3,3-dimethyl-4-(1-methyl-1H-pyrrolo[2,3-b]pyridin-4-yl)-7-((5-(piperazin-1-yl)pyridin-2-yl)amino)isoindolin-1-one | LCMS Method J m/z = 468.2 [M + H]+, Ret. time = 3.59 min | ¹H NMR (400 MHz, DMSO): δ 9.98 (s, 1 H), 8.77 (s, 1 H), 8.44-8.42 (d, J = 8 Hz, 1 H), 8.31-8.27 (m, 2 H), 7.98-7.97 (s, 1 H), 7.51-7.50 (m, 1 H), 7.44-7.42 (d, J = 8 Hz, 1 H), 7.22-7.20 (d, J = 8 Hz, 1 H), 7.01-7.00 (d, J = 4 Hz, 1 H), 6.95-6.93 (d, J = 8 Hz, 1 H), 6.05-6.04 (m, 1 H), 3.86 (s, 1 H), 3.098 (s, 1 H), 2.97 (s, 1 H), 1.14 (s, 6 H) | K AA1 BB14 |
| I-274 | 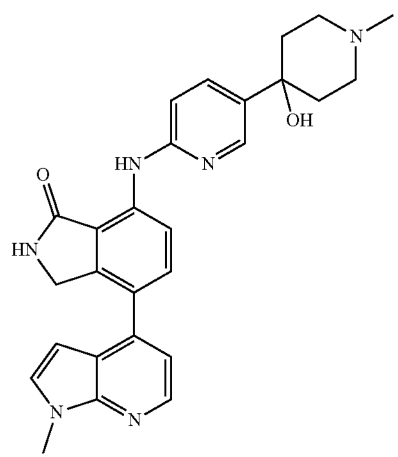 [SMILES: CN1CCC(O)(c2ccc(Nc3ccc(-c4ccnc5c4ccn5C)c4c3C(=O)NC4)nc2)CC1] | 7-((5-(4-hydroxy-1-methylpiperidin-4-yl)pyridin-2-yl)amino)-4-(1-methyl-1H-pyrrolo[2,3-b]pyridin-4-yl)isoindolin-1-one | LCMS Method J m/z = 469.2 [M + H]+, Ret. time = 3.36 min | 1H NMR (400 MHz, DMSO-d6) δ 10.13 (s, 1H), 8.81 (s, 1H), 8.69 (d, J = 8.6 Hz, 1H), 8.40 (d, J = 2.5 Hz, 1H), 8.31 (d, J = 4.9 Hz, 1H), 7.82-7.71 (m, 2H), 7.58 (d, J = 3.5 Hz, 1H), 7.26 (d, J = 4.9 Hz, 1H), 6.97 (d, J = 8.6 Hz, 1H), 6.47 (d, J = 3.5 Hz, 1H), 4.89 (s, 1H), 4.46 (s, 2H), 3.86 (s, 3H), 3.42 (d, J = 5.4 Hz, 1H), 2.56 (m, 1H), 2.21 (s, 3H), 1.95 (t, J = 12.3 Hz, 2H), 1.64 (d, J = 12.7 Hz, 2H). | E AA82 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-275 | 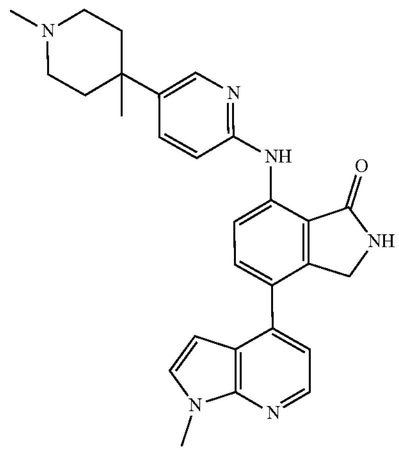 [SMILES: CN1CCC(C)(c2ccc(Nc3ccc(-c4ccnc5c4ccn5C)c4c3C(=O)NC4)nc2)CC1] | 7-((5-(1,4-dimethylpiperidin-4-yl)pyridin-2-yl)amino)-4-(1-methyl-1H-pyrrolo[2,3-b]pyridin-4-yl)isoindolin-1-one | LCMS Method C m/z = 467.8 [M + H]+, Ret. time = 1.40 min | 1H NMR (400 MHz, Methanol-d4) δ 8.72 (d, J = 8.5 Hz, 1H), 8.56 (s, 1H), 8.36 (dd, J = 15.0, 3.8 Hz, 2H), 7.83-7.71 (m, 2H), 7.46 (d, J = 3.5 Hz, 1H), 7.24 (d, J = 5.0 Hz, 1H), 7.06 (d, J = 8.7 Hz, 1H), 6.49 (d, J = 3.5 Hz, 1H), 4.49 (s, 2H), 3.95 (s, 3H), 3.21 (s, 2H), 3.00 (s, 2H), 2.74 (s, 3H), 2.41 (s, 2H), 2.03 (s, 2H), 1.39 (s, 3H). | E AA10 BB14 |
| I-276 | 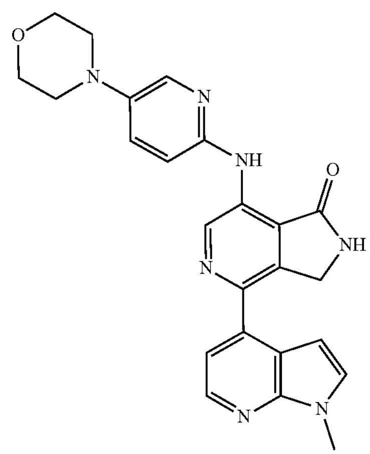 | 4-(1-methyl-1H-pyrrolo[2,3-b]pyridin-4-yl)-7-((5-morpholino-pyridin-2-yl)amino)-2,3-dihydro-1H-pyrrolo[3,4-c]pyridin-1-one | LCMS Method J m/z = 280 [M + H]+, Ret. time = 2.57 min | ¹H NMR (400 MHz, DMSO): δ 8.54 (s, 1 H), 8.350-8.297 (m, 2 H), 7.59-7.58 (m, 1 H), 7.22-7.21 (d, J = 4.8 Hz, 1H), 6.88 (s, 2 H), 6.49-6.48 (m, 1 H), 4.45 (s, 2 H), 3.87 (s, 3 H) | E AA10 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-278 | 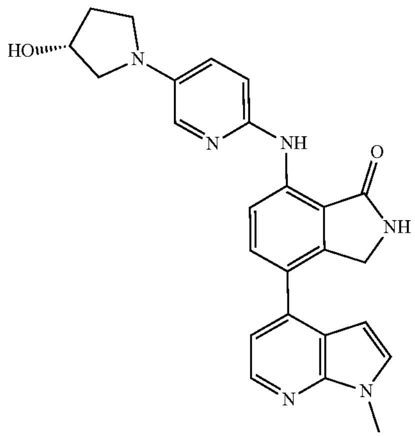 [SMILES: Cn1ccc2c(-c3ccc(Nc4ccc(N5CC[C@@H](O)C5)cn4)c4c3CNC4=O)ccnc21] | (R)-7-((5-(3-hydroxy-pyrrolidin-1-yl)pyridin-2-yl)amino)-4-(1-methyl-1H-pyrrolo[2,3-b]pyridin-4-yl)isoindolin-1-one | LCMS Method C m/z = 441.6 [M + H]+, Ret. time = 1.36 min | 1H NMR (400 MHz, DMSO-d6) δ 9.75 (s, 1H), 8.73 (s, 1H), 8.43 (d, J = 8.6 Hz, 1H), 8.31 (d, J = 5.0 Hz, 1H), 7.74-7.65 (m, 2H), 7.58 (d, J = 3.5 Hz, 1H), 7.26 (d, J = 5.0 Hz, 1H), 7.05 (dd, J = 8.9, 3.0 Hz, 1H), 6.96 (d, J = 8.8 Hz, 1H), 6.48 (d, J = 3.5 Hz, 1H), 5.01 (s, 1H), 4.44 (d, J = 11.8 Hz, 3H), 3.87 (s, 3H), 3.45 (dd, J = 10.0, 5.0 Hz, 1H), 3.28 (dd, J = 8.6, 3.8 Hz, 2H), 3.09 (d, J = 9.7 Hz, 1H), 2.06 (dt, J = 17.2, 6.7 Hz, 1H), 1.95-1.87 (m, 1H). | E AA11 BB14 |
| I-279 | 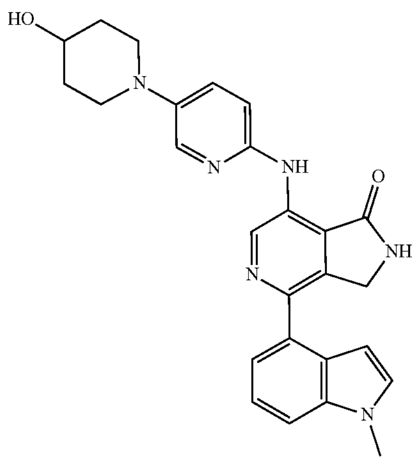 [SMILES: Cn1ccc2c(-c3ncc(Nc4ccc(N5CCC(O)CC5)cn4)c4c3CNC4=O)cccc21] | 7-((5-(4-hydroxypiperidin-1-yl)pyridin-2-yl)amino)-4-(1-methyl-1H-indol-4-yl)-2,3-dihydro-1H-pyrrolo[3,4-c]pyridin-1-one | LCMS Method C m/z = 455.6 [M + H]+, Ret. time = 1.38 min | 1H NMR (400 MHz, DMSO-d6) δ 9.84 (s, 1H), 9.53 (s, 1H), 9.19 (s, 1H), 8.10 (s, 1H), 7.56 (d, J = 8.2 Hz, 2H), 7.43-7.34 (m, 2H), 7.28 (t, J = 7.7 Hz, 1H), 7.10 (d, J = 8.9 Hz, 1H), 6.72 (d, J = 3.1 Hz, 1H), 4.59 (s, 2H), 3.86 (s, 3H), 3.67 (s, 2H), 2.92 (s, 2H), 1.87 (s, 2H), 1.56 (d, J = 11.5 Hz, 2H). | Q AA12 BB41 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-280 | 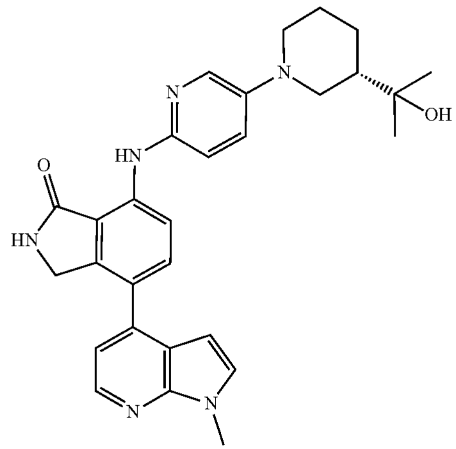 [SMILES: Cn1ccc2c(-c3ccc(Nc4ccc(N5CCC[C@H](C(C)(C)O)C5)cn4)c4c3CNC4=O)ccnc21] | rel-(R)-7-((5-(3-(2-hydroxypropan-2-yl)piperidin-1-yl)pyridin-2-yl)amino)-4-(1-methyl-1H-pyrrolo[2,3-b]pyridin-4-yl)isoindolin-1-one | LCMS Method J m/z = 497.2 [M + H]+, Ret. time = 3.69 min Chiral HPLC method X2: Ret. time = 25.31 | 1H NMR (400 MHz, DMSO-d6) δ 9.91 (s, 1H), 8.55 (d, J = 8.6 Hz, 1H), 8.31 (d, J = 5.0 Hz, 1H), 8.00 (d, J = 3.0 Hz, 1H), 7.72 (d, J = 8.6 Hz, 1H), 7.59 (d, J = 3.6 Hz, 1H), 7.42 (dd, J = 9.0, 3.0 Hz, 1H), 7.27 (d, J = 4.9 Hz, 1H), 6.97 (d, J = 8.9 Hz, 1H), 6.48 (d, J = 3.5 Hz, 1H), 4.46 (s, 2H), 4.30 (s, 1H), 3.88 (s, 3H), 3.75 (d, J = 11.9 Hz, 1H), 3.62 (d, J = 11.9 Hz, 1H), 2.43 (t, J = 11.5 Hz, 2H), 1.81 (dd, J = 35.4, 12.7 Hz, 2H), 1.58 (s, 2H), 1.12 (d, J = 10.1 Hz, 6H). | E AA13 BB14 |
| I-281 | 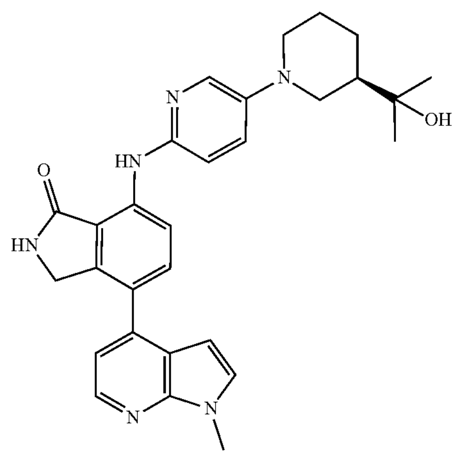 [SMILES: Cn1ccc2c(-c3ccc(Nc4ccc(N5CCC[C@@H](C(C)(C)O)C5)cn4)c4c3CNC4=O)ccnc21] | rel-(R)-7-((5-(3-(2-hydroxypropan-2-yl)piperidin-1-yl)pyridin-2-yl)amino)-4-(1-methyl-1H-pyrrolo[2,3-b]pyridin-4-yl)isoindolin-1-one | LCMS Method J m/z = 497.4 [M + H]+, Ret. time = 3.31 min Chiral HPLC method X2: Ret. time = 33.37 | 1H NMR (400 MHz, DMSO-d6) δ 9.91 (s, 1H), 8.78 (s, 1H), 8.55 (d, J = 8.5 Hz, 1H), 8.31 (d, J = 4.9 Hz, 1H), 8.00 (d, J = 3.1 Hz, 1H), 7.72 (d, J = 8.6 Hz, 1H), 7.59 (d, J = 3.6 Hz, 1H), 7.42 (dd, J = 8.9, 3.0 Hz, 1H), 7.27 (d, J = 4.9 Hz, 1H), 6.97 (d, J = 8.9 Hz, 1H), 6.48 (d, J = 3.5 Hz, 1H), 4.47 (s, 2H), 4.30 (s, 1H), 3.88 (s, 3H), 3.75 (d, J = 11.7 Hz, 1H), 3.63 (d, J = 11.9 Hz, 1H), 2.43 (t, J = 11.5 Hz, 2H), 1.81 (dd, J = 35.2, 12.7 Hz, 2H), 1.58 (t, J = 12.1 Hz, 2H), 1.12 (d, J = 10.1 Hz, 6H). | E AA13 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-282 | 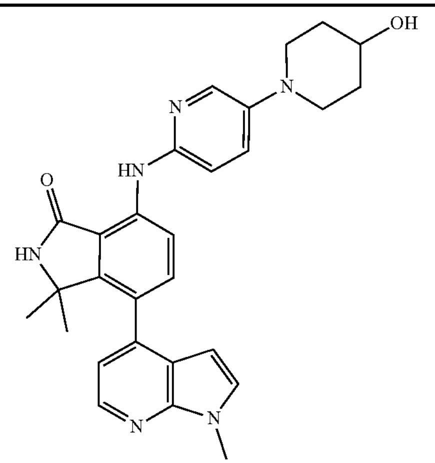 | 7-(5-(4-hydroxypiperidin-1-yl)pyridin-2-yl)amino)-3,3-dimethyl-4-(1-methyl-1H-pyrrolo[2,3-b]pyridin-4-yl)isoindolin-1-one | LCMS Method J m/z = 483.3 [M + H]+, Ret. time = 3.63 min | 1H NMR (400 MHz, DMSO-d6) δ 9.96 (s, 1H), 8.77 (s, 1H), 8.42 (d, J = 8.5 Hz, 1H), 8.32 (d, J = 4.7 Hz, 1H), 7.99 (d, J = 3.0 Hz, 1H), 7.52 (d, J = 3.5 Hz, 1H), 7.44 (dd, J = 9.1, 2.9 Hz, 1H), 7.22 (d, J = 8.5 Hz, 1H), 7.02 (d, J = 4.8 Hz, 1H), 6.93 (d, J = 8.9 Hz, 1H), 6.07 (d, J = 3.5 Hz, 1H), 4.72 (s, 1H), 3.88 (s, 3H), 3.62 (s, 1H), 3.45 (d, J = 11.2 Hz, 2H), 2.81 (t, J = 10.7 Hz, 2H), 1.85 (d, J = 11.3 Hz, 2H), 1.52 (d, J = 10.6 Hz, 2H), 1.16 (s, 6H). | K AA12 BB14 |
| I-283 | 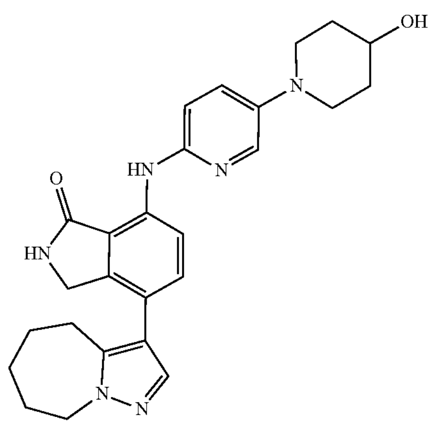 [SMILES: O=C1NCc2c(-c3cnn4c3CCCCC4)ccc(Nc3ccc(N4CCC(O)CC4)cn3)c21] | 7-(5-(4-hydroxypiperidin-1-yl)pyridin-2-yl)amino)-4-(5,6,7,8-tetrahydro-4H-pyrazolo[1,5-a]azepin-3-yl)isoindolin-1-one | LCMS Method C m/z = 459.4 [M + H]+, Ret. time = 1.34 min | 1H NMR (400 MHz, Methanol-d4) δ 8.24 (d, J = 8.5 Hz, 1H), 8.00 (d, J = 2.9 Hz, 1H), 7.77 (s, 1H), 7.58 (s, 1H), 7.46-7.36 (m, 2H), 6.97 (d, J = 8.9 Hz, 1H), 4.43 (s, 2H), 4.20 (t, J = 6.2 Hz, 2H), 3.78 (dq, J = 8.8, 4.5 Hz, 1H), 3.48 (dd, J = 11.7, 5.4 Hz, 2H), 2.97-2.83 (m, 4H), 2.18-2.09 (m, 2H), 2.06-1.99 (m, 2H), 1.93 (q, J = 6.0 Hz, 2H), 1.73 (ddt, J = 13.2, 9.3, 4.7 Hz, 2H). | F AA12 BB57 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-284 | (structure) | 7-((5-(4-hydroxypiperidin-1-yl)pyridin-2-yl)amino)-4-(4,5,6,7-tetrahydropyrazolo[1,5-a]pyridin-3-yl)isoindolin-1-one | LCMS Method C m/z = 445.6 [M + H]+, Ret. time = 1.33 min | 1H NMR (400 MHz, DMSO-d6) δ 9.75 (s, 1H), 8.72 (s, 1H), 8.43 (d, J = 8.6 Hz, 1H), 8.31 (d, J = 4.9 Hz, 1H), 7.70 (d, J = 8.6 Hz, 2H), 7.58 (d, J = 3.5 Hz, 1H), 7.26 (d, J = 4.9 Hz, 1H), 7.05 (dd, J = 8.8, 3.0 Hz, 1H), 6.97 (d, J = 8.7 Hz, 1H), 6.48 (d, J = 3.5 Hz, 1H), 5.00 (d, J = 3.8 Hz, 1H), 4.44 (d, J = 10.4 Hz, 3H), 3.87 (s, 3H), 3.45 (dd, J = 10.0, 5.0 Hz, 1H), 3.28 (dd, J = 8.4, 3.8 Hz, 1H), 3.10 (d, J = 9.7 Hz, 1H), 2.57 (s, 3H), 2.11-2.02 (m, 1H), 1.92 (t, J = 8.6 Hz, 1H). | F 12 BB46 |
| I-285 | (structure) | (S)-7-((5-(3-hydroxypyrrolidin-1-yl)pyridin-2-yl)amino)-4-(1-methyl-1H-pyrrolo[2,3-b]pyridin-4-yl)isoindolin-1-one | LCMS Method J m/z = 441.6 [M + H]+, Ret. time = 2.90 min | ¹H NMR (400 MHz, DMSO): δ 9.905 (s, 1 H), 8.809 (s, 1 H), 8.51-8.49 (d, J = 8 Hz, 1 H), 8.32-8.30 (m, 1 H), 8.00 (s, 1 H), 7.60-7.57 (m, 2 H), 7.45-7.43 (m, 1 H), 7.25-7.24 (m, 1 H), 6.95-6.93 (d, J = 8, 1H), 6.42-6.41 (m, 1 H), 5.05-5.04 (m, 1 H), 4.724 (s, 1 H), 3.882 (s, 3H), 3.628 (s, 1H), 3.47-3.44 (m, 3H), 2.84-2.79 (t, J = 20, 2 H), 1.86-1.83 (m, 2 H), 1.55-1.51 (m, 2 H), 0.80-0.78 (m, 3 H) | E AA11BB 14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-286 | (structure with 4-hydroxypiperidine, pyridine, isoindolinone, methyl-pyrrolopyridine) | rel-(R)-7-((5-(4-hydroxypiperidin-1-yl)pyridin-2-yl)amino)-3-methyl-4-(1-methyl-1H-pyrrolo[2,3-b]pyridin-4-yl)isoindolin-1-one | LCMS Method J m/z = 469.7 [M + H]+, Ret. Time = 2.95 min Chiral HPLC method X3: Ret. time = 5.7 | ¹H NMR (400 MHz, DMSO): δ 9.905 (s, 1 H), 8.809 (s, 1 H), 8.51-8.49 (d, J = 8 Hz, 1 H), 8.32-8.30 (m, 1 H), 8.00 (s, 1 H), 7.60-7.57 (m, 2 H), 7.45-7.43 (m, 1 H), 7.25-7.24 (m, 1 H), 6.95-6.93 (d, J = 8, 1H), 6.42-6.41 (m, 1 H), 5.05-5.04 (m, 1 H), 4.724 (s, 1 H), 3.882 (s, 3H), 3.628 (s, 1H), 3.47-3.44 (m, 3H), 2.84-2.79 (t, J = 20, 2 H), 1.86-1.83 (m, 2 H), 1.55-1.51 (m, 2 H), 0.80-0.78 (m, 3 H) | L AA12 BB14 |
| I-287 | (structure with 4-hydroxypiperidine, pyridine, isoindolinone, methyl-pyrrolopyridine) | rel-(R)-7-((5-(4-hydroxypiperidin-1-yl)pyridin-2-yl)amino)-3-methyl-4-(1-methyl-1H-pyrrolo[2,3-b]pyridin-4-yl)isoindolin-1-one | LCMS Method J m/z = 469.7 [M + H]+, Ret. time = 2.94 min Chiral HPLC method X3: Ret. time = 6.04 | ¹H NMR (400 MHz, DMSO): δ 9.90 (s, 1 H), 8.80 (s, 1 H), 8.51-8.49 (d, J = 8 Hz, 1 H), 8.32-8.31 (m, 1 H), 8.01 (s, 1 H), 7.60-7.57 (m, 2 H), 7.45-7.43 (m, 1 H), 7.25-7.24 (m, 1 H), 6.95-6.93 (d, J = 8, 1H), 6.42-6.41 (m, 1 H), 5.05-5.04 (m, 1 H), 4.72 (s, 1 H), 3.88 (s, 3H), 3.63 (s, 1H), 3.47-3.44 (m, 3H), 2.84-2.79 (t, J = 20, 2 H), 1.86-1.84 (m, 2 H), 1.53-1.51 (m, 2 H), 0.80-0.79 (m, 3 H) | L AA12 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-288 | 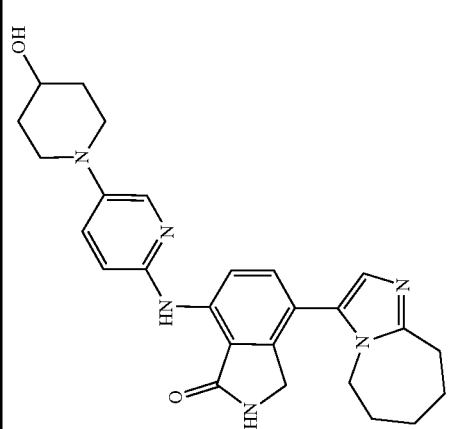 | 7-(5-(4-hydroxypiperidin-1-yl)pyridin-2-ylamino)-4-(6,7,8,9-tetrahydro-5H-imidazo[1,2-a]azepin-3-yl)isoindolin-1-one | LCMS Method J m/z = 459.3 [M + H]+, Ret. time = 2.88 min | 1H NMR (400 MHz, DMSO-d6) δ 9.75 (s, 1H), 8.73 (s, 1H), 8.47 (d, J = 8.5 Hz, 1H), 7.99 (d, J = 3.0 Hz, 1H), 7.43 (dd, J = 9.0, 3.1 Hz, 1H), 7.27 (d, J = 8.5 Hz, 1H), 6.92 (d, J = 8.9 Hz, 1H), 6.86 (s, 1H), 4.72 (d, J = 3.9 Hz, 1H), 4.32 (s, 2H), 3.83 (d, J = 7.0 Hz, 2H), 3.63 (s, 1H), 3.45 (d, J = 12.8 Hz, 2H), 2.88 (s, 2H), 2.86-2.79 (m, 2H), 1.83 (s, 4H), 1.66 (d, J = 23.9 Hz, 4H), 1.53 (dd, J = 11.7, 7.9 Hz, 2H). | F AA12 BB58 |
| I-289 | 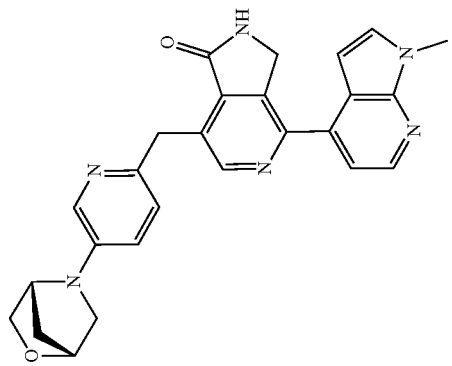 | 7-(5-((1R,4R)-2-oxa-5-azabicyclo[2.2.1]heptan-5-yl)pyridin-2-ylamino)-4-(1-methyl-1H-pyrrolo[2,3-b]pyridin-4-yl)-2,3-dihydro-1H-pyrrolo[3,4-c]pyridin-1-one | LCMS Method C m/z = 454.4 [M + H]+, Ret. time = 1.37 min | ¹H NMR (400 MHz, DMSO): δ 9.86 (s, 1 H), 9.42 (s, 1 H), 9.14 (s, 1 H), 8.36-8.34 (m, 1 H), 7.84 (s, 1 H), 7.57-7.56 (m, 1 H), 7.38-7.37 (m, 1 H), 7.20-7.17 (m, 1 H), 7.07-7.05 (d, J = 8 Hz, 1 H), 6.92-6.92 (m, 1 H), 4.72 (s, 2 H), 4.64-4.61 (d, J = 12 Hz, 2 H), 3.88 (s, 3 H), 3.77-3.70 (dd, J = 22.5 Hz, 22.5 Hz, 2 H), 3.57-3.55 (d, J = 8 Hz, 1 H), 3.00-2.98 (d, J = 8 Hz, 1 H), 1.97-1.94 (d, J = 12 Hz, 1 H), 1.88-1.86 (d, J = 8 Hz, 1 H). | Q AA14 BB14 |

| # | STRUCTURE | NAME | LCMS | ¹H NMR | Method Reagent AA BB |
|---|---|---|---|---|---|
| I-290 | 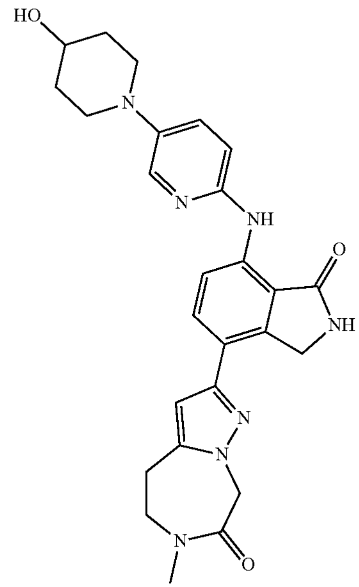 [SMILES: CN1CCc2cc(-c3ccc(Nc4ccc(N5CCC(O)CC5)cn4)c4c3CNC4=O)nn2CC1=O] | 2-(7-((5-(4-hydroxypiperidin-1-yl)pyridin-2-yl)amino)-1-oxoisoindolin-4-yl)-6-methyl-5,6-dihydro-4H-pyrazolo[1,5-d][1,4]diazepin-7(8H)-one | LCMS Method J m/z = 488.2 [M + H]+, time = 3.13 min | 1H NMR (400 MHz, DMSO-d6) δ 9.82 (s, 1H), 8.76 (s, 1H), 8.40 (d, J = 8.7 Hz, 1H), 7.99 (d, J = 3.0 Hz, 1H), 7.82 (d, J = 8.6 Hz, 1H), 7.42 (dd, J = 9.0, 3.1 Hz, 1H), 6.90 (d, J = 8.9 Hz, 1H), 6.59 (s, 1H), 5.13 (s, 2H), 4.70 (d, J = 4.2 Hz, 1H), 4.56 (s, 2H), 3.89 (t, J = 5.8 Hz, 3H), 3.45 (d, J = 11.9 Hz, 3H), 3.14 (t, J = 5.5 Hz, 3H), 2.98 (s, 3H), 2.81 (t, J = 10.6 Hz, 2H), 1.83 (d, J = 10.3 Hz, 4H), 1.52 (d, J = 10.3 Hz, 4H). | F AA12 BB59 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-291 | 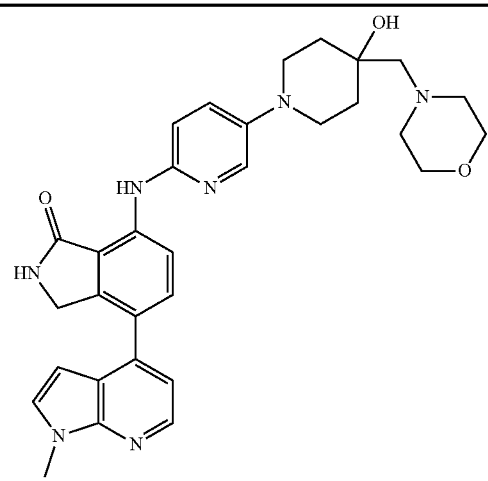 | 7-((5-(4-hydroxy-4-(morpholinomethyl)piperidin-1-yl)pyridin-2-yl)amino)-4-(1-methyl-1H-pyrrolo[2,3-b]pyridin-4-yl)isoindolin-1-one | LCMS Method C m/z = 554.6, [M + H]+, Ret. time = 1.32 min | 1H NMR (400 MHz, DMSO-d6) δ 9.90 (s, 1H), 8.76 (s, 1H), 8.54 (d, J = 8.5 Hz, 1H), 8.31 (d, J = 4.9 Hz, 1H), 8.02 (d, J = 2.9 Hz, 1H), 7.72 (d, J = 8.5 Hz, 1H), 7.58 (d, J = 3.5 Hz, 1H), 7.44 (dd, J = 8.9, 3.0 Hz, 1H), 7.26 (d, J = 4.9 Hz, 1H), 6.95 (d, J = 8.9 Hz, 1H), 6.48 (d, J = 3.5 Hz, 1H), 4.46 (s, 2H), 4.19 (s, 1H), 3.88 (s, 3H), 3.58 (t, J = 4.5 Hz, 4H), 3.29 (d, J = 11.3 Hz, 2H), 3.12-3.00 (m, 2H), 2.30 (s, 2H), 1.76-1.65 (m, 2H), 1.60 (d, J = 13.2 Hz, 2H). | E AA15 BB14 |
| I-292 | 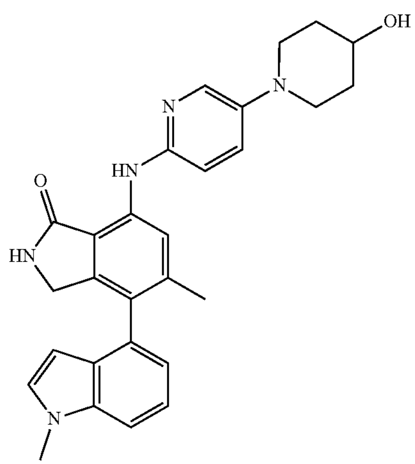 [SMILES: Cc1cc(Nc2ccc(N3CCC(O)CC3)cn2)c2c(c1-c1cccc3c1ccn3C)CNC2=O] | 7-((5-(4-hydroxypiperidin-1-yl)pyridin-2-yl)amino)-5-methyl-4-(1-methyl-1H-indol-4-yl)isoindolin-1-one | LCMS Method C m/z = 469.3 [M + H]+, Ret. time = 1.33 min | ¹H NMR (400 MHz, DMSO): δ 9.55 (s, 1 H), 8.35-8.34 (d, J = 4.8 Hz, 1 H), 8.26 (s, 1 H), 8.19 (s, 1 H), 8.03-8.03 (s, 1 H), 7.49-7.49 (d, J = 3.2 Hz, 1 H), 7.43-7.40 (m, 1H), 7.04-7.03 (m, 1 H), 6.96-6.94 (m, 1H), 6.12-6.11 (m, 1 H), 4.44 (s, 1 H), 4.10-4.06 (d, J = 18 Hz, 1 H), 3.89 (s, 3H), 3.63 (s, 1H), 3.84 (s, 1H), 3.67 (s, 1 H), 3.48-3.45 (m, 2 H), 2.90-2.86 (t, J = 19.2, 2 H), 2.15 (s, 3 H), 1.87 (s, 2H), 1.57-1.55 (m, 2H) | M AA12 BB41 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-293 | 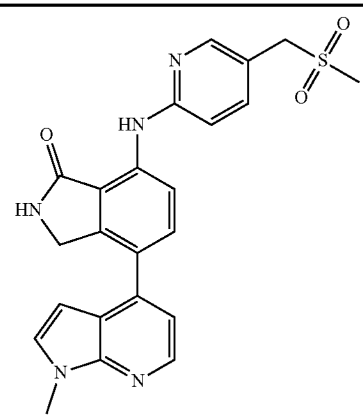 | 4-(1-methyl-1H-pyrrolo[2,3-b]pyridin-4-yl)-7-((5-((methyl-sulfonyl)meth-yl)pyridin-2-yl)amino)iso-indolin-1-one | LCMS Method C m/z = 448.3 [M + H]+, Ret. time = 1.41 min | ¹H NMR (400 MHz, DMSO): δ 10.298 (s, 1 H), 8.872 (s, 1 H), 8.74-8.72 (d, J = 8.6 Hz, 1 H), 8.33 (s, 2 H), 7.80-7.73 (m, 2 H), 7.60 (s, 1 H), 7.29-7.28 (m, 1 H), 7.10-7.07 (d, J = 8.6 Hz, 1 H), 6.49 (s, 1 H), 4.49 (s, 1H), 3.88 (s, 1 H), 2.96 (S, 3 H) | O AA16 BB14 |
| I-294 | 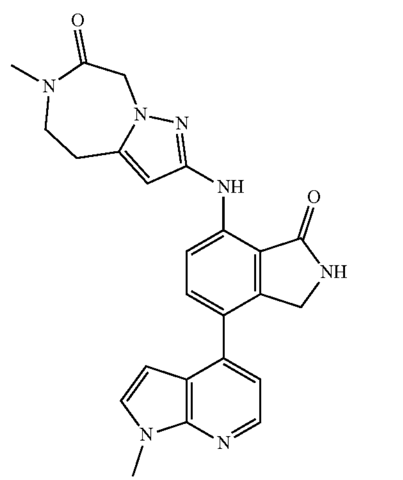 [SMILES: CN1CCc2cc(Nc3ccc(-c4ccnc5c4ccn5C)c4c3C(=O)NC4)nn2CC1=O] | 6-methyl-2-((7-(1-methyl-1H-pyrrolo[2,3-b]pyridin-4-yl)-3-oxoisoindolin-4-yl)amino)-5,6-dihydro-4H-pyrazolo[1,5-d][1,4]diazepin-7(8H)-one | LCMS Method J m/z = 442.0 [M + H]+, Ret. time = 3.59 min | 1H NMR (400 MHz, DMSO-d6) δ 9.42 (s, 1H), 8.71 (s, 1H), 8.31 (d, J = 4.9 Hz, 1H), 7.97 (d, J = 8.5 Hz, 1H), 7.72 (d, J = 8.5 Hz, 1H), 7.58 (d, J = 3.5 Hz, 1H), 7.25 (d, J = 5.0 Hz, 1H), 6.47 (d, J = 3.5 Hz, 1H), 6.03 (s, 1H), 5.02 (s, 2H), 4.45 (s, 2H), 3.86(d, J = 9.3 Hz, 5H), 3.08 (t, J = 5.6 Hz, 2H), 2.98 (s, 3H). | O AA17 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-295 | 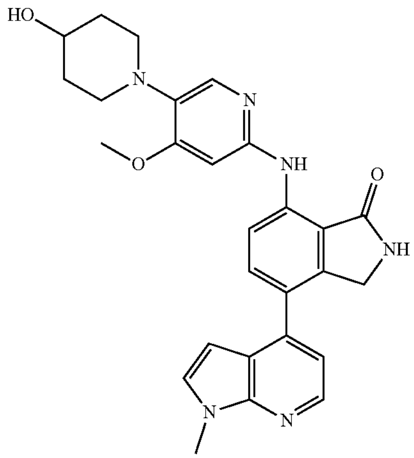 [SMILES: COc1cc(Nc2ccc(-c3ccnc4c3ccn4C)c3c2C(=O)NC3)ncc1N1CCC(O)CC1] | 7-((5-(4-hydroxypiperidin-1-yl)-4-methoxypyridin-2-yl)amino)-4-(1-methyl-1H-pyrrolo[2,3-b]pyridin-4-yl)isoindolin-1-one | LCMS Method C m/z = 486.7 [M + H]+, Ret. time = 1.33 min | 1H NMR (400 MHz, DMSO-d6) δ 9.96 (s, 1H), 8.80 (s, 1H), 8.73 (d, J = 8.6 Hz, 1H), 8.32 (d, J = 4.9 Hz, 1H), 7.78 (s, 1H), 7.73 (d, J = 8.6 Hz, 1H), 7.59 (d, J = 3.5 Hz, 1H), 7.27 (d, J = 4.9 Hz, 1H), 6.56 (s, 1H), 6.48 (d, J = 3.6 Hz, 1H), 4.68 (d, J = 4.2 Hz, 1H), 4.47 (s, 2H), 3.89 (d, J = 13.7 Hz, 6H), 3.60 (dd, J = 9.0, 4.7 Hz, 1H), 3.20 (dd, J = 11.1, 5.8 Hz, 3H), 2.70 (t, J = 10.5 Hz, 2H), 1.84 (d, J = 10.0 Hz, 2H), 1.54 (d, J = 10.5 Hz, 2H). | E AA18 BB14 |
| I-296 | 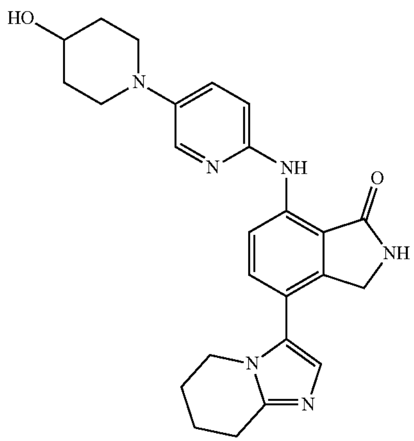 [SMILES: O=C1NCc2c(-c3cnc4n3CCCC4)ccc(Nc3ccc(N4CCC(O)CC4)cn3)c21] | 7-((5-(4-hydroxy-piperidin-1-yl)pyridin-2-yl)amino)-4-(5,6,7,8-tetrahydroimidazo[1,2-a]pyridin-3-yl)isoindolin-1-one | LCMS Method J m/z = 445.2 [M + H]+, Ret. time = 2.74 min | 1H NMR (400 MHz, DMSO-d6) δ 9.76 (s, 1H), 8.72 (s, 1H), 8.45 (d, J = 8.6 Hz, 1H), 7.99 (d, J = 3.1 Hz, 1H), 7.54-7.34 (m, 2H), 7.05 (s, 1H), 6.91 (d, J = 8.9 Hz, 1H), 4.71 (d, J = 4.2 Hz, 1H), 4.38 (s, 2H), 3.87 (s, 2H), 3.62 (s, 1H), 3.45 (d, J = 12.2 Hz, 2H), 2.81 (s, 4H), 1.86 (d, J = 16.7 Hz, 6H), 1.61-1.44 (m, 2H), 1.25 (s, 1H). | F AA12 BB60 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-297 | (structure) | 7-((5-(6-hydroxy-2-azaspiro[3.3]heptan-2-yl)pyridin-2-yl)amino)-4-(1-methyl-1H-pyrrolo[2,3-b]pyridin-4-yl)isoindolin-1-one | LCMS Method J m/z = 467.2 [M + H]+, Ret. time = 3.51 min | 1H NMR (400 MHz, DMSO-d6) δ 9.83 (s, 1H), 8.75 (s, 1H), 8.47 (d, J = 8.6 Hz, 1H), 8.31 (d, J = 4.9 Hz, 1H), 7.71 (d, J = 8.6 Hz, 1H), 7.65-7.50 (m, 2H), 7.26 (d, J = 4.9 Hz, 1H), 6.94 (s, 2H), 6.47 (d, J = 3.5 Hz, 1H), 5.08 (d, J = 5.3 Hz, 1H), 4.46 (s, 2H), 4.03 (s, 1H), 3.88 (s, 3H), 3.78 (d, J = 17.2 Hz, 3H), 2.46 (s, 5H), 2.04 (d, J = 10.0 Hz, 2H). | E AA19 BB14 |
| I-298 | (structure) | 7-((5-(4-hydroxy-4-(methoxymethyl)piperidin-1-yl)pyridin-2-yl)amino)-4-(1-methyl-1H-pyrrolo[2,3-b]pyridin-4-yl)isoindolin-1-one | LCMS Method J m/z = 499.2 [M + H]+, Ret. time = 3.42 min | 1H NMR (400 MHz, DMSO-d6) δ 9.90 (s, 1H), 8.77 (s, 1H), 8.54 (d, J = 8.6 Hz, 1H), 8.31 (d, J = 5.0 Hz, 1H), 8.02 (d, J = 3.0 Hz, 1H), 7.72 (d, J = 8.6 Hz, 1H), 7.58 (d, J = 3.6 Hz, 1H), 7.45 (dd, J = 9.1, 3.0 Hz, 1H), 7.26 (d, J = 4.9 Hz, 1H), 6.95 (d, J = 8.9 Hz, 1H), 6.48 (d, J = 3.5 Hz, 1H), 4.45 (d, J = 9.0 Hz, 3H), 3.87 (s, 3H), 3.30 (s, 3H), 3.20 (s, 2H), 3.08-2.97 (m, 2H), 1.72 (td, J = 12.8, 4.5 Hz, 3H), 1.51 (d, J = 13.0 Hz, 2H). | E AA20 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-299 | 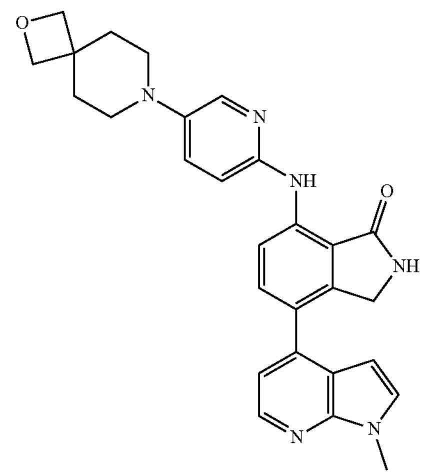 [SMILES: Cn1ccc2c(-c3ccc(Nc4ccc(N5CCC6(CC5)COC6)cn4)c4c3CNC4=O)ccnc21] | 7-((5-(2-oxa-7-aza-spiro[3.5]nonan-7-yl)pyridin-2-yl)amino)-4-(1-methyl-1H-pyrrolo[2,3-b]pyridin-4-yl)isoindolin-1-one | LCMS Method H m/z = 481.2 [M + H]+, Ret. time = 2.72 min | 1H NMR (400 MHz, DMSO-d6) δ 10.51 (s, 1H), 8.96 (s, 1H), 8.84-8.63 (m, 2H), 8.34 (d, J = 4.9 Hz, 1H), 8.18 (dd, J = 9.1, 3.1 Hz, 1H), 7.82 (d, J = 8.5 Hz, 1H), 7.61 (d, J = 3.5 Hz, 1H), 7.30 (dd, J = 6.9, 4.3 Hz, 2H), 6.48 (d, J = 3.5 Hz, 1H), 5.32 (s, 1H), 4.50 (s, 2H), 4.40 (s, 2H), 4.13 (s, 1H), 3.98 (s, 2H), 3.89 (s, 5H), 3.73 (s, 2H), 3.18 (s, 3H), 2.24 (s, 2H), 1.90 (s, 2H). | E AA21 BB14 |
| I-300 | 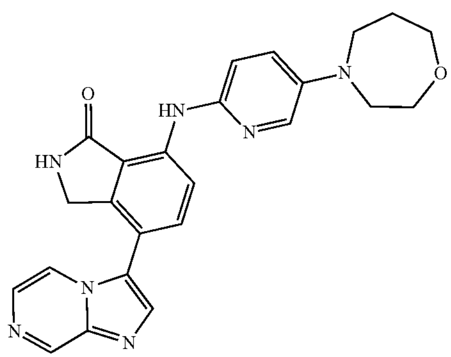 [SMILES: O=C1NCc2c(-c3cnc4cnccn34)ccc(Nc3ccc(N4CCCOCC4)cn3)c21] | 7-((5-(1,4-oxazepan-4-yl)pyridin-2-yl)amino)-4-(imidazo[1,2-a]pyrazin-3-yl)isoindolin-1-one | LCMS Method C m/z = 442.3 [M + H]+, Ret. time = 1.28 min | 1H NMR (400 MHz, DMSO-d6) δ 9.74 (s, 1H), 9.14 (s, 1H), 8.78 (s, 1H), 8.55-8.39 (m, 2H), 8.10 (s, 1H), 7.89 (dd, J = 7.3, 4.0 Hz, 2H), 7.73 (d, J = 8.6 Hz, 1H), 7.32-7.24 (m, 1H), 6.94 (d, J = 9.0 Hz, 1H), 4.42 (s, 2H), 3.73 (s, 2H), 3.58 (d, J = 7.2 Hz, 6H), 1.91 (d, J = 7.7 Hz, 2H). | F AA22 BB61 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-301 | 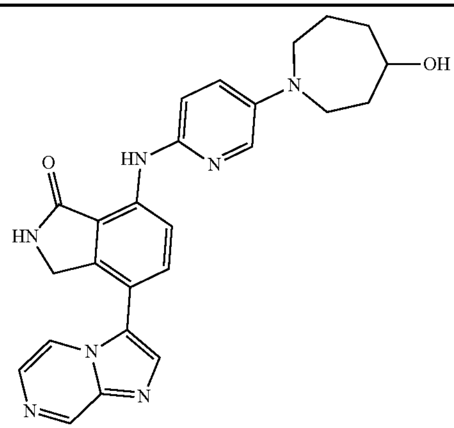 | 7-(5-(4-hydroxyazepan-1-yl)pyridin-2-yl)amino)-4-(imidazo[1,2-a]pyrazin-3-yl)isoindolin-1-one | LCMS Method J m/z = 456.3 [M + H]+, Ret. time = 3.07 min | 1H NMR (400 MHz, DMSO-d6) δ 9.70 (s, 1H), 9.14 (s, 1H), 8.77 (s, 1H), 8.46 (t, J = 7.1 Hz, 2H), 8.10 (s, 1H), 7.90 (d, J = 4.7 Hz, 1H), 7.81 (d, J = 3.3 Hz, 1H), 7.72 (d, J = 8.6 Hz, 1H), 6.94 (d, J = 8.9 Hz, 1H), 4.53 (d, J = 4.0 Hz, 1H), 4.42 (s, 2H), 3.68 (s, 1H), 3.52-3.40 (m, 2H), 1.91 (s, 2H), 1.65 (s, 3H), 1.53 (s, 2H). | F AA37 BB61 |
| I-302 | 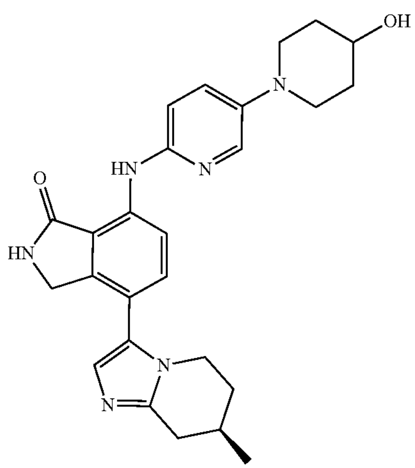 [SMILES: C[C@@H]1CCn2c(-c3ccc(Nc4ccc(N5CCC(O)CC5)cn4)c4c3CNC4=O)cnc2C1] | rel-(R)-7-(5-(4-hydroxypiperidin-1-yl)pyridin-2-yl)amino)-4-(7-methyl-5,6,7,8-tetrahydroimidazo[1,2-a]pyridin-3-yl)isoindolin-1-one | LCMS Method C m/z = 459.2 [M + H]+, Ret. time = 1.31 min Chiral HPLC method X4: Ret. time = 12.55 | 1H NMR (400 MHz, DMSO-d6) δ 9.74 (s, 1H), 8.72 (s, 1H), 8.44 (d, J = 8.6 Hz, 1H), 7.97 (d, J = 3.0 Hz, 1H), 7.49 (d, J = 8.7 Hz, 1H), 7.41 (dd, J = 9.0, 3.0 Hz, 1H), 7.03 (s, 1H), 6.90 (d, J = 9.0 Hz, 1H), 4.71 (d, J = 4.2 Hz, 1H), 4.47 (d, J = 18.2 Hz, 1H), 4.25 (d, J = 18.3 Hz, 1H), 3.88 (d, J = 14.8 Hz, 2H), 3.43 (d, J = 11.1 Hz, 2H), 2.92 (d, J = 18.5 Hz, 1H), 2.84-2.74 (m, 2H), 2.35 (d, J = 5.8 Hz, 1H), 2.09-1.91 (m, 2H), 1.83 (d, J = 12.1 Hz, 2H), 1.59-1.45 (m, 3H), 1.08 (d, J = 6.4 Hz, 3H), 1.03 (d, J = 6.1 Hz, 1H). | J AA12 BB62 |

TABLE 8-continued

Characterization Data (LCMS and ¹H NMR).

| # | STRUCTURE | NAME | LCMS | ¹H NMR | Method AA Reagent BB |
|---|---|---|---|---|---|
| I-303 | (structure) | (S)-7-((5-(4-hydroxy-piperidin-1-yl)pyridin-2-yl)amino)-4-(7-methyl-5,6,7,8-tetrahydroimidazo[1,2-a]pyridin-3-yl)isoindolin-1-one | LCMS Method C m/z = 459.7 [M + H]+, Ret. time = 1.26 min Chiral HPLC method X4: Ret. time = 13.67 | 1H NMR (400 MHz, DMSO-d6) δ 9.75 (s, 1H), 8.73 (s, 1H), 8.45 (d, J = 8.6 Hz, 1H), 7.97 (d, J = 3.1 Hz, 1H), 7.50 (d, J = 8.6 Hz, 1H), 7.41 (dd, J = 9.0, 3.0 Hz, 1H), 7.07 (s, 1H), 6.90 (d, J = 8.9 Hz, 1H), 4.71 (d, J = 4.1 Hz, 1H), 4.47 (d, J = 18.3 Hz, 1H), 4.25 (d, J = 18.4 Hz, 1H), 3.89 (d, J = 14.6 Hz, 2H), 3.61 (s, 1H), 3.45 (s, 1H), 2.94 (d, J = 16.9 Hz, 1H), 2.79 (t, J = 10.8 Hz, 2H), 2.39 (d, J = 11.1 Hz, 1H), 2.07-1.92 (m, 2H), 1.81 (s, 2H), 1.59-1.41 (m, 3H), 1.23 (s, 1H), 1.09 (d, J = 6.4 Hz, 3H). | J AA12 BB62 |
| I-304 | (structure) | 7-(5-((1R,3r,5S)-3-hydroxy-8-azabicyclo[3.2.1]octan-8-yl)pyridin-2-yl)amino)-4-(imidazo[1,2-a]pyrazin-3-yl)isoindolin-1-one | LCMS Method J m/z = 468.2 [M + H]+, Ret. time = 3.16 min Chiral HPLC method X2: Ret. time = 12.73 | 1H NMR (400 MHz, DMSO-d6) δ 9.76 (s, 1H), 9.14 (s, 1H), 8.78 (s, 1H), 8.51 (d, J = 8.6 Hz, 1H), 8.45 (d, J = 4.7 Hz, 1H), 8.11 (s, 1H), 7.90 (dd, J = 8.0, 3.8 Hz, 2H), 7.73 (d, J = 8.6 Hz, 1H), 7.26 (dd, J = 9.0, 3.0 Hz, 1H), 6.94 (d, J = 8.8 Hz, 1H), 4.58 (d, J = 2.4 Hz, 1H), 4.42 (s, 2H), 4.16 (s, 2H), 2.28 (d, J = 6.9 Hz, 2H), 1.99 (d, J = 14.5 Hz, 2H), 1.90 (s, 2H), 1.51 (d, J = 14.4 Hz, 3H). | F AA23 BB61 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-305 | 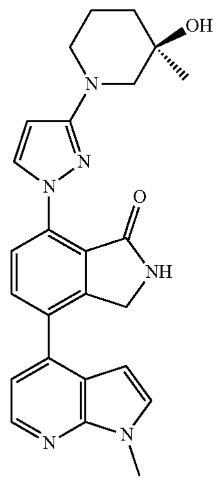 [SMILES: Cn1ccc2c(-c3ccc(-n4ccc(N5CCC[C@@](C)(O)C5)n4)c4c3CNC4=O)ccnc21] | rel-(R)-7-(3-(3-hydroxy-3-methylpiperidin-1-yl)-1H-pyrazol-1-yl)-4-(1-methyl-1H-pyrrolo[2,3-b]pyridin-4-yl)isoindolin-1-one | LCMS Method J m/z = 443.0 [M + H]+, Ret. time = 4.02 min Chiral HPLC method X1: Ret. time = 11.07 | 1H NMR (400 MHz, DMSO-d6) δ 8.80 (s, 2H), 8.35 (d, J = 4.9 Hz, 1H), 8.00 (d, J = 8.4 Hz, 1H), 7.81 (d, J = 8.4 Hz, 1H), 7.61 (d, J = 3.5 Hz, 1H), 7.29 (d, J = 4.9 Hz, 1H), 6.42 (d, J = 3.5 Hz, 1H), 6.10 (d, J = 2.8 Hz, 1H), 4.44 (d, J = 33.0 Hz, 3H), 3.87 (s, 3H), 3.19 (d, J = 6.2 Hz, 2H), 3.13-3.03 (m, 2H), 1.80 (d, J = 7.3 Hz, 1H), 1.53 (s, 3H), 1.18 (s, 3H), 1.08-0.97 (m, 1H). | J AA24 BB14 |
| I-306 | 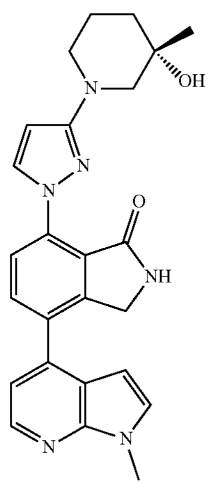 [SMILES: Cn1ccc2c(-c3ccc(-n4ccc(N5CCC[C@](C)(O)C5)n4)c4c3CNC4=O)ccnc21] | rel-(R)-7-(3-(3-hydroxy-3-methylpiperidin-1-yl)-1H-pyrazol-1-yl)-4-(1-methyl-1H-pyrrolo[2,3-b]pyridin-4-yl)isoindolin-1-one | LCMS Method J m/z = 443.2 [M + H]+, Ret. time = 4.02 min Chiral HPLC method X1: Ret. time = 11.15 | 1H NMR (400 MHz, DMSO-d6) δ 8.80 (s, 2H), 8.34 (d, J = 4.8 Hz, 1H), 8.00 (d, J = 8.2 Hz, 1H), 7.81 (d, J = 8.4 Hz, 1H), 7.60 (d, J = 3.5 Hz, 1H), 7.29 (d, J = 4.8 Hz, 1H), 6.42 (d, J = 3.6 Hz, 1H), 6.10 (d, J = 2.9 Hz, 1H), 4.48 (s, 1H), 4.39 (s, 2H), 3.87 (s, 3H), 3.19 (d, J = 6.2 Hz, 2H), 3.15-3.04 (m, 2H), 1.81 (s, 1H), 1.53 (s, 3H), 1.18 (s, 4H), 1.03 (d, J = 6.0 Hz, 1H). | J AA24 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-307 | 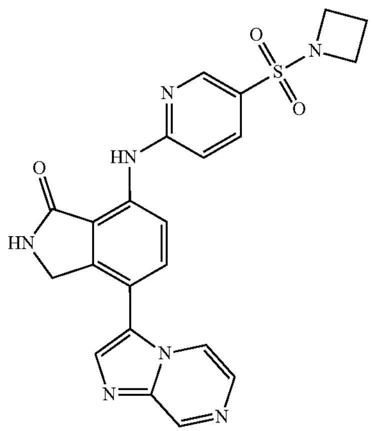 [SMILES: O=C1NCc2c(-c3cnc4cnccn34)ccc(Nc3ccc(S(=O)(=O)N4CCC4)cn3)c21] | 7-((5-(azetidin-1-ylsulfonyl)pyridin-2-yl)amino)-4-(imidazo[1,2-a]pyrazin-3-yl)isoindolin-1-one | LCMS Method J m/z = 462.0 [M + H]+, Ret. time = 3.67 min | 1H NMR (400 MHz, DMSO-d6) δ 10.64 (s, 1H), 9.17 (s, 1H), 9.05 (s, 1H), 8.81 (d, J = 8.5 Hz, 1H), 8.68 (s, 1H), 8.52 (d, J = 4.7 Hz, 1H), 8.18 (s, 1H), 8.02 (d, J = 8.9 Hz, 1H), 7.93 (t, J = 7.4 Hz, 2H), 7.26 (d, J = 8.9 Hz, 1H), 4.52 (s, 2H), 3.71 (t, J = 7.6 Hz, 4H), 2.05 (d, J = 7.0 Hz, 2H). | F AA25 BB61 |
| I-308 | 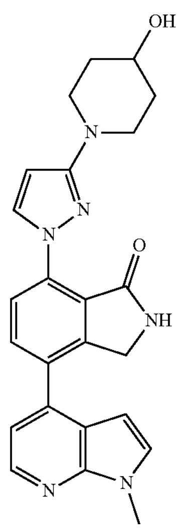 [SMILES: Cn1ccc2c(-c3ccc(-n4ccc(N5CCC(O)CC5)n4)c4c3CNC4=O)ccnc21] | 7-(3-(4-hydroxypiperidin-1-yl)-1H-pyrazol-1-yl)-4-(1-methyl-1H-pyrrolo[2,3-b]pyridin-4-yl)isoindolin-1-one | LCMS Method J m/z = 429.4 [M + H]+, Ret. time = 3.52 min | 1H NMR (400 MHz, DMSO-d6) δ 8.85-8.73 (m, 2H), 8.35 (d, J = 4.9 Hz, 1H), 7.99 (d, J = 8.4 Hz, 1H), 7.80 (d, J = 8.4 Hz, 1H), 7.60 (d, J = 3.5 Hz, 1H), 7.29 (d, J = 4.9 Hz, 1H), 6.42 (d, J = 3.5 Hz, 1H), 6.12 (d, J = 2.8 Hz, 1H), 4.71 (d, J = 4.2 Hz, 1H), 4.39 (s, 2H), 3.88 (s, 3H), 3.66 (d, J = 13.0 Hz, 3H), 2.92 (t, J = 11.2 Hz, 2H), 2.41 (s, 2H), 1.82 (d, J = 11.8 Hz, 2H), 1.55-1.41 (m, 2H). | E AA26 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-309 | 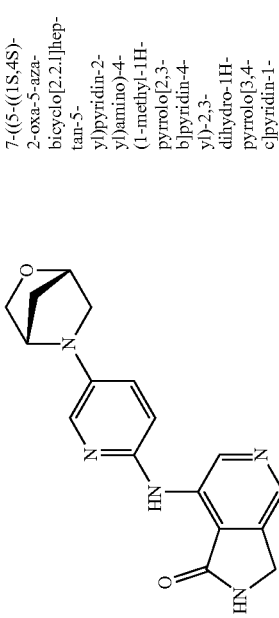 | 7-(5-((1S,4S)-2-oxa-5-azabicyclo[2.2.1]heptan-5-yl)pyridin-2-ylamino)-4-(1-methyl-1H-pyrrolo[2,3-b]pyridin-4-yl)-2,3-dihydro-1H-pyrrolo[3,4-c]pyridin-1-one | LCMS Method C m/z = 454.3 [M + H]+, Ret. time = 1.39 min | ¹H NMR (400 MHz, DMSO): δ 9.85(s, 1 H), 9.41 (s, 1 H), 9.13 (s, 1 H), 8.34-8.33 (m, 1 H), 7.83-7.82 (m, 1 H), 7.56-7.55 (m, 1 H), 7.37-7.35 (m, 1 H), 7.19-7.16 (m, 1 H), 7.05-7.03 (d, J = 8 Hz, 1 H), 6.91-6.90 (m, 1 H), 4.70 (s, 2 H), 4.62-4.59 (d, J = 12 Hz, 2 H), 3.86 (s, 3 H), 3.76-3.74 (d, J = 8 Hz, 1 H), 3.70-3.68 (d, J = 8 Hz, 1 H), 3.55-3.53 (d, J = 8 Hz, 1 H), 2.98-2.96 (d, J = 8 Hz, 1 H), 1.95-1.93 (d, J = 8 Hz, 1 H) 1.87-1.84 (d, J = 12 Hz, 1H) | R AA14 BB14 |
| I-310 | 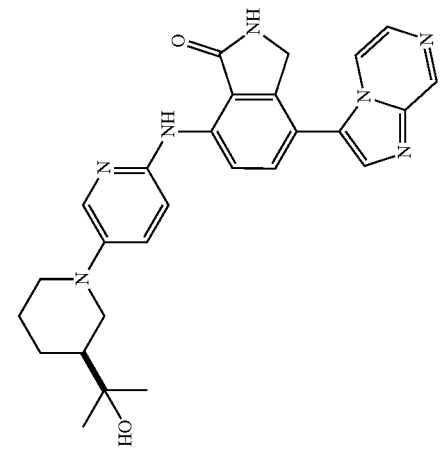 | (S)-7-(5-(3-(2-hydroxypropan-2-yl)piperidin-1-yl)pyridin-2-ylamino)-4-(imidazo[1,2-a]pyrazin-3-yl)isoindolin-1-one | LCMS Method J m/z = 484.2 [M + H]+, Ret. time = 3.25 min Chiral HPLC method X2: Ret. time = 26.20 | 1H NMR (400 MHz, DMSO-d6) δ 9.86 (s, 1H), 9.14 (s, 1H), 8.80 (s, 1H), 8.57 (d, J = 8.7 Hz, 1H), 8.45 (d, J = 4.7 Hz, 1H), 8.04-7.87 (m, 2H), 7.75 (d, J = 8.8 Hz, 1H), 7.42 (d, J = 8.9 Hz, 1H), 6.96 (d, J = 9.0 Hz, 1H), 4.43 (s, 2H), 4.27 (s, 1H), 3.74 (d, J = 12.0 Hz, 1H), 3.62 (d, J = 13.1 Hz, 1H), 1.80 (dd, J = 35.7, 12.8 Hz, 2H), 1.56 (s, 2H), 1.37-0.99 (m, 6H). | J AA13 BB61 |

TABLE 8-continued

Characterization Data (LCMS and ¹H NMR).

| # | STRUCTURE | NAME | LCMS | ¹H NMR | Method AA Reagent BB |
|---|---|---|---|---|---|
| I-311 | 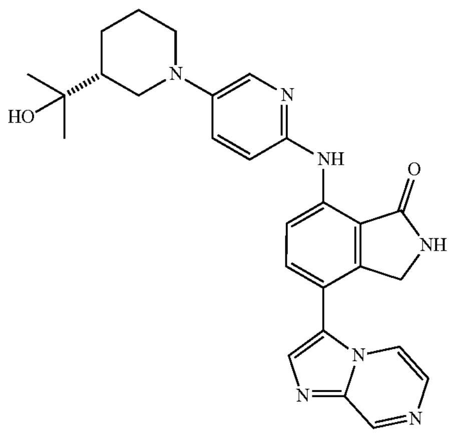 [SMILES: CC(C)(O)[C@@H]1CCCN(c2ccc(Nc3ccc(-c4cnc5cnccn45)c4c3C(=O)NC4)nc2)C1] | (R)-7-((5-(3-(2-hydroxypropan-2-yl)piperidin-1-yl)pyridin-2-yl)amino)-4-(imidazo[1,2-a]pyrazin-3-yl)isoindolin-1-one | LCMS Method J m/z = 484.2 [M + H]+, Ret. time = 3.28 min Chiral HPLC method X2: Ret. time = 20.95 | 1H NMR (400 MHz, DMSO-d6) δ 9.86 (s, 1H), 9.14 (s, 1H), 8.80 (s, 1H), 8.57 (d, J = 8.7 Hz, 1H), 8.45 (d, J = 4.7 Hz, 1H), 8.04-7.87 (m, 2H), 7.75 (d, J = 8.8 Hz, 1H), 7.42 (d, J = 8.9 Hz, 1H), 6.96 (d, J = 9.0 Hz, 1H), 4.43 (s, 2H), 4.27 (s, 1H), 3.74 (d, J = 12.0 Hz, 1H), 3.62 (d, J = 13.1 Hz, 1H), 1.80 (dd, J = 35.7, 12.8 Hz, 2H), 1.56 (s, 2H), 1.37-0.99 (m, 6H). | J AA13 BB61 |
| I-312 | 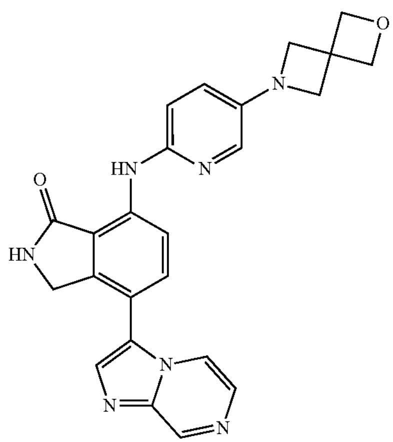 [SMILES: O=C1NCc2c(-c3cnc4cnccn34)ccc(Nc3ccc(N4CC5(COC5)C4)cn3)c21] | 7-((5-(2-oxa-6-aza-spiro[3.3]heptan-6-yl)pyridin-2-yl)amino)-4-(imidazo[1,2-a]pyrazin-3-yl)isoindolin-1-one | LCMS Method J m/z = 440.2 [M + H]+, Ret. time = 3.26 min | 1H NMR (400 MHz, DMSO-d6) δ 9.81 (s, 1H), 9.14 (s, 1H), 8.80 (s, 1H), 8.48 (dd, J = 22.6, 6.4 Hz, 2H), 8.10 (s, 1H), 7.90 (d, J = 4.7 Hz, 1H), 7.74 (d, J = 8.6 Hz, 1H), 7.60 (d, J = 2.7 Hz, 1H), 6.96 (d, J = 4.0 Hz, 2H), 4.72 (s, 4H), 4.42 (s, 2H), 3.99 (s, 4H). | F AA47 BB61 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-313 | 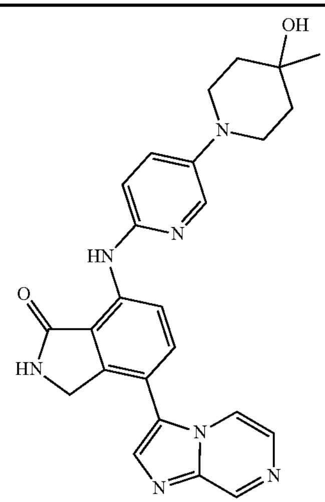 | 7-((5-(4-hydroxy-4-methylpiperidin-1-yl)pyridin-2-yl)amino)-4-(imidazo[1,2-a]pyrazin-3-yl)isoindolin-1-one | LCMS Method J m/z = 456.2 [M + H]+, Ret. time = 2.99 min | 1H NMR (400 MHz, DMSO-d6) δ 9.85 (s, 1H), 9.14 (s, 1H), 8.80 (s, 1H), 8.57 (d, J = 8.7 Hz, 1H), 8.46 (d, J = 4.7 Hz, 1H), 8.11 (s, 1H), 8.01 (d, J = 3.0 Hz, 1H), 7.91 (d, J = 4.7 Hz, 1H), 7.75 (d, J = 8.6 Hz, 1H), 7.44 (dd, J = 8.7, 3.0 Hz, 1H), 6.95 (d, J = 8.9 Hz, 1H), 4.43 (s, 2H), 4.31 (s, 1H), 3.23 (d, J = 11.8 Hz, 2H), 3.09 (d, J = 8.3 Hz, 2H), 1.58 (d, J = 5.5 Hz, 4H), 1.16 (s, 3H). | F AA27 BB61 |
| I-314 | 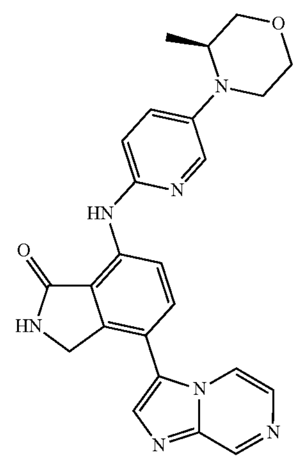 [SMILES: C[C@H]1COCCN1c1ccc(Nc2ccc(-c3cnc4cnccn34)c3c2C(=O)NC3)nc1] | (S)-4-(imidazo[1,2-a]pyrazin-3-yl)-7-((5-(3-methylmorpholino)pyridin-2-yl)amino)isoindolin-1-one | LCMS Method J m/z = 442.0 [M + H]+, Ret. time = 3.43 min | 1H NMR (400 MHz, DMSO-d6) δ 9.91 (s, 1H), 9.14 (s, 1H), 8.82 (s, 1H), 8.60 (d, J = 8.6 Hz, 1H), 8.46 (d, J = 4.8 Hz, 1H), 8.12 (s, 1H), 8.04-7.85 (m, 2H), 7.76 (d, J = 8.7 Hz, 1H), 7.44 (d, J = 9.1 Hz, 1H), 6.99 (d, J = 9.1 Hz, 1H), 4.44 (s, 2H), 3.85 (s, 1H), 3.76 (d, J = 10.9 Hz, 1H), 3.62 (dd, J = 27.5, 16.1 Hz, 4H), 3.08 (s, 1H), 3.01 (s, 1H), 0.95 (d, J = 6.5 Hz, 3H). | F AA28 BB61 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-315 | 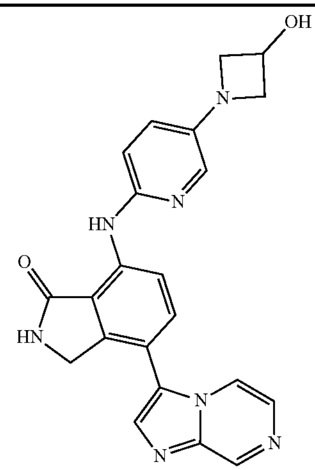 | 7-((5-(3-hydroxyazetidin-1-yl)pyridin-2-yl)amino)-4-(imidazo[1,2-a]pyrazin-3-yl)isoindolin-1-one | LCMS Method C m/z = 414.6 [M + H]+, Ret. time = 1.28 min | 1H NMR (400 MHz, DMSO-d6) δ 9.80 (s, 1H), 9.14 (s, 1H), 8.79 (s, 1H), 8.50 (d, J = 8.5 Hz, 1H), 8.45 (d, J = 4.9 Hz, 1H), 8.11 (s, 1H), 7.91 (d, J = 4.8 Hz, 1H), 7.74 (d, J = 8.5 Hz, 1H), 7.59 (s, 1H), 6.96 (d, J = 4.4 Hz, 2H), 5.63 (d, J = 6.6 Hz, 1H), 4.58 (d, J = 6.3 Hz, 1H), 4.58 (d, J = 6.3 Hz, 1H), 4.43 (s, 2H), 4.10 (t, J = 7.0 Hz, 2H), 3.55-3.49 (m, 2H). | F AA29 BB61 |
| I-316 | 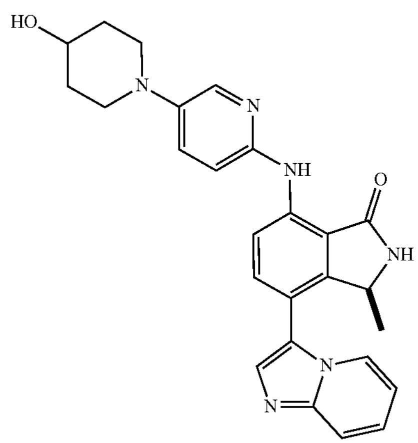 [SMILES: C[C@@H]1NC(=O)c2c(Nc3ccc(N4CCC(O)CC4)cn3)ccc(-c3cnc4ccccn34)c21] | (S)-7-((5-(4-hydroxypiperidin-1-yl)pyridin-2-yl)amino)-4-(imidazo[1,2-a]pyridin-3-yl)-3-methylisoindolin-1-one | LCMS Method J m/z = 455.2 [M + H]+, Ret. time = 2.79 min | 1H NMR (400 MHz, DMSO-d6) δ 9.85 (s, 1H), 8.80 (s, 1H), 8.51 (d, J = 8.6 Hz, 1H), 8.20 (d, J = 6.9 Hz, 1H), 8.00 (d, J = 3.1 Hz, 1H), 7.75 (s, 1H), 7.62 (dd, J = 3.16, 8.8 Hz, 2H), 7.43 (dd, J = 8.9, 3.2 Hz, 1H), 7.30 (t, J = 7.8 Hz, 1H), 6.93 (dd, J = 11.5, 6.0 Hz, 2H), 4.77 (d, J = 6.9 Hz, 1H), 3.61 (s, 1H), 2.88-2.72 (m, 3H), 1.83 (s, 3H), 1.51 (d, J = 10.3 Hz, 3H), 0.76 (d, J = 6.7 Hz, 3H). | L AA12 BB26 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-317 | (structure) | (R)-7-((5-(4-hyperoxypiperidin-1-yl)pyridin-2-yl)amino)-4-(imidazo[1,2-a]pyridin-3-yl)-3-methylisoindolin-1-one | LCMS Method J m/z = 455.2 [M + H]+, Ret. time = 2.79 min | 1H NMR (400 MHz, DMSO-d6) δ 9.85 (s, 1H), 8.80 (s, 1H), 8.51 (d, J = 8.5 Hz, 1H), 8.20 (d, J = 6.9 Hz, 1H), 8.00 (d, J = 3.1 Hz, 1H), 7.75 (s, 1H), 7.66 (d, J = 9.1 Hz, 1H), 7.58 (d, J = 8.6 Hz, 1H), 7.43 (dd, J = 8.9, 3.1 Hz, 1H), 7.35-7.23 (m, 1H), 6.93 (dd, J = 11.6, 6.0 Hz, 2H), 4.77 (d, J = 6.8 Hz, 1H), 3.66-3.57 (m, 1H), 3.45 (d, J = 11.2 Hz, 3H), 2.88-2.76 (m, 2H), 1.58-1.44 (m, 3H), 0.76 (d, J = 6.6 Hz, 3H). | L AA12 BB26 |
| I-318 | (structure) | 4-(imidazo[1,2-a]pyrazin-3-yl)-7-((5-((3aR,6aS)-tetrahydro-1H-furo[3,4-c]pyrrol-5(3H)-yl)pyridin-2-yl)amino)isoindolin-1-one | LCMS Method J m/z = 454.2 [M + H]+, Ret. time = 3.39 min Chiral HPLC method X5: Ret. time = 5.11 | 1H NMR (400 MHz, DMSO-d6) δ 9.79 (s, 1H), 9.14 (s, 1H), 8.79 (s, 1H), 8.52 (d, J = 8.6 Hz, 1H), 8.46 (d, J = 4.7 Hz, 1H), 8.11 (s, 1H), 7.91 (d, J = 4.7 Hz, 1H), 7.76 (dd, J = 16.1, 5.8 Hz, 2H), 7.18 (dd, J = 8.9, 3.1 Hz, 1H), 6.97 (d, J = 8.8 Hz, 1H), 4.43 (s, 2H), 3.86 (t, J = 7.4 Hz, 2H), 3.54 (dd, J = 8.7, 3.4 Hz, 2H), 3.30 (s 2H), 3.23-3.15 (m, 2H), 2.99 (s, 2H). | F AA30 BB61 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-319 | 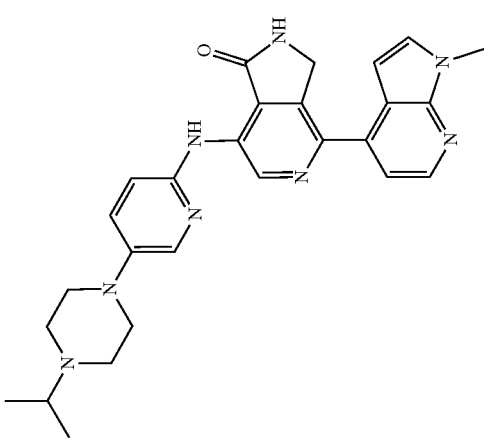 | 7-(5-(4-isopropylpiperazin-1-yl)pyridin-2-ylamino)-4-(1-methyl-1H-pyrrolo[2,3-b]pyridin-4-yl)-2,3-dihydro-1H-pyrrolo[3,4-c]pyridin-1-one | LCMS Method J m/z = 483.2 [M + H]+, Ret. time = 3.14 min | 1H NMR (400 MHz, DMSO-d6) δ 9.93 (s, 1H), 9.52 (s, 1H), 9.18 (s, 1H), 8.34 (d, J = 4.9 Hz, 1H), 8.06 (s, 1H), 7.56 (d, J = 3.7 Hz, 1H), 7.47 (d, J = 8.1 Hz, 1H), 7.38 (s, 1H), 7.07 (d, J = 8.7 Hz, 1H), 6.90 (d, J = 3.7 Hz, 1H), 4.72 (s, 2H), 3.86 (s, 3H), 3.14 (s, 3H), 1.06 (s, 6H). | E AA31 BB14 |
| I-320 | 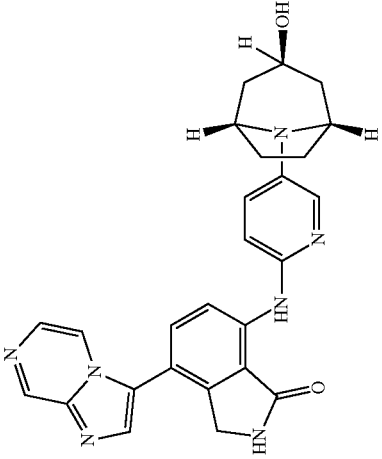 | 7-((5-((1R,3s,5S)-3-hydroxy-8-azabicyclo[3.2.1]octan-8-yl)pyridin-2-yl)amino)-4-(imidazo[1,2-a]pyrazin-3-yl)isoindolin-1-one | LCMS Method J m/z = 468.3 [M + H]+, Ret. time = 3.22 min | 1H NMR (400 MHz, DMSO-d6) δ 9.78 (s, 1H), 9.14 (s, 1H), 8.80 (s, 1H), 8.53 (d, J = 8.6 Hz, 1H), 8.46 (d, J = 4.8 Hz, 1H), 8.11 (s, 1H), 7.91 (t, J = 4.5 Hz, 2H), 7.74 (d, J = 8.6 Hz, 1H), 7.30 (dd, J = 8.9, 3.0 Hz, 1H), 6.97 (d, J = 8.8 Hz, 1H), 4.44 (d, J = 5.1 Hz, 3H), 4.25 (d, J = 4.7 Hz, 2H), 4.01-3.88 (m, 1H), 1.93 (d, J = 6.8 Hz, 2H), 1.73 (d, J = 7.3 Hz, 2H), 1.66 (d, J = 13.4 Hz, 2H), 1.50 (t, J = 11.9 Hz, 3H). | F AA23 BB61 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-321 | 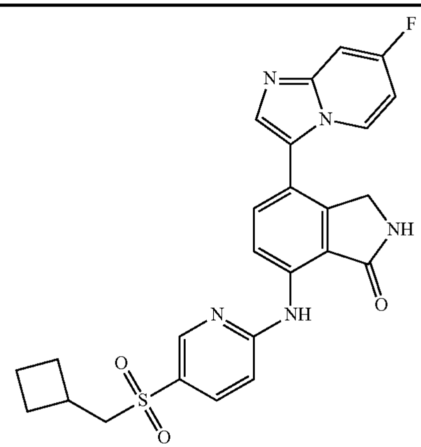 | 7-(5-((cyclobutylmethyl)sulfonyl)pyridin-2-yl)amino)-4-(7-fluoroimidazo[1,2-a]pyridin-3-yl)isoindolin-1-one | LCMS Method C m/z = 492.0 [M + H]+, Ret. time = 1.72 min | 1H NMR (400 MHz, DMSO-d6) δ 10.59 (s, 1H), 9.00 (s, 1H), 8.75 (d, 1H), 8.67 (s, 1H), 8.48 (t, J = 6.8 Hz 1H), 8.02 (dd, J = 7 Hz, 1H), 7.85 (m, 1H), 7.55 (d, J = 10 Hz 1H), 7.20 (d, J = 8.8 Hz, 1H), 6.99 (m 1H), 4.45 (s, 1H), 3.47 (d, J = 9.2 Hz, 2H), 2.40 (s, 2H), 1.93 (s, 1H), 1.80 (m, 1H), 1.73 (s, 2H). | F AA32 BB63 |
| I-322 | 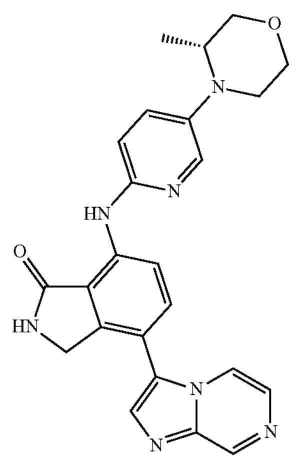 [SMILES: C[C@@H]1COCCN1c1ccc(Nc2ccc(-c3cnc4cnccn34)c3c2C(=O)NC3)nc1] | (R)-4-(imidazo[1,2-a]pyrazin-3-yl)-7-((5-(3-methylmorpholino)pyridin-2-yl)amino)isoindolin-1-one | LCMS Method J m/z = 442.2 [M + H]+, Ret. time = 3.42 min | 1H NMR (400 MHz, DMSO-d6) δ 9.91 (s, 1H), 9.15 (s, 1H), 8.83 (s, 1H), 8.60 (d, J = 8.6 Hz, 1H), 8.47 (d, J = 4.7 Hz, 1H), 8.12 (s, 1H), 7.99 (d, J = 3.0 Hz, 1H), 7.91 (d, J = 4.7 Hz, 1H), 7.77 (d, J = 8.6 Hz, 1H), 7.45 (dd, J = 9.3, 3.0 Hz, 1H), 7.00 (d, J = 9.0 Hz, 1H), 4.44 (s, 2H), 3.86 (d, J = 11.4 Hz, 1H), 3.76 (d, J = 10.8 Hz, 1H), 3.73-3.54 (m, 3H), 3.06 (dd, J = 32.1, 10.8 Hz, 2H), 0.95 (d, J = 6.4 Hz, 3H). | F AA28 BB61 |

TABLE 8-continued
Characterization Data (LCMS and $^1$H NMR).
| # | STRUCTURE | NAME | LCMS | $^1$H NMR | Method Reagent AA BB |
|---|---|---|---|---|---|
| I-323 | 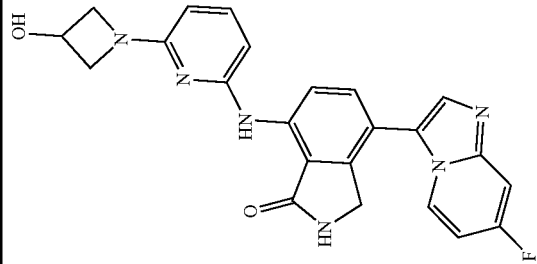 | 4-(7-fluoroimidazo[1,2-a]pyridin-3-yl)-7-((6-(3-hydroxyazetidin-1-yl)pyridin-2-yl)amino)isoindolin-1-one | LCMS Method C m/z = 431.4 [M + H]+, Ret. time = 1.29 min | 1H NMR (400 MHz, DMSO-d6) δ 9.97 (s, 1H), 8.83 (s, 1H), 8.75 (d, J = 8.6 Hz, 1H), 8.45 (t, J = 6.6 Hz, 1H), 7.83 (s, 1H), 7.71 (d, J = 8.6 Hz, 1H), 7.53 (dd, J = 10.0, 2.7 Hz, 1H), 7.43 (t, J = 7.9 Hz, 1H), 6.98 (td, J = 7.5, 2.7 Hz, 1H), 6.19 (d, J = 7.8 Hz, 1H), 5.91 (d, J = 8.0 Hz, 1H), 5.67 (d, J = 6.7 Hz, 1H), 4.61 (q, J = 5.9 Hz, 1H), 4.38 (s, 2H), 4.21 (t, J = 7.4 Hz, 2H), 3.73 (dd, J = 8.6, 4.7 Hz, 2H), 2.0 (s, 1H). | F AA33 BB63 |

TABLE 8-continued
Characterization Data (LCMS and ¹H NMR).
| # | STRUCTURE | NAME | LCMS | ¹H NMR | Method Reagent AA BB |
|---|---|---|---|---|---|
| I-324 | 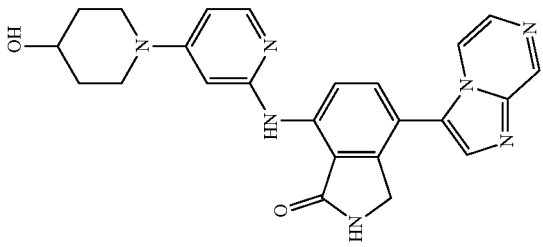 | 7-((4-(4-hydroxy-piperidin-1-yl)pyridin-2-yl)amino)-4-(imidazo[1,2-a]pyrazin-3-yl)isoindolin-1-one | LCMS Method G m/z = 442.2 [M + H]+, Ret. time = 7.96 min | 1H NMR (400 MHz, DMSO-d6) δ 9.85 (s, 1H), 9.14 (s, 1H), 8.84 (s, 1H), 8.77 (d, J = 8.6 Hz, 1H), 8.47 (d, J = 4.7 Hz, 1H), 8.12 (s, 1H), 7.92 (dd, J = 11.6, 5.4 Hz, 2H), 7.76 (d, J = 8.7 Hz, 1H), 6.54 (dd, J = 6.2, 2.2 Hz, 1H), 6.30 (d, J = 2.2 Hz, 1H), 4.81-4.68 (m, 1H), 4.44 (s, 2H), 3.73 (dt, J = 13.8, 4.6 Hz, 3H), 3.05 (ddd, J = 13.2, 9.9, 3.1 Hz, 2H), 1.85-1.74 (m, 2H), 1.39 (dtd, J = 12.9, 9.4, 3.7 Hz, 2H). | F AA34 BB61 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-325 | (structure) | (R)-4-(imidazo[1,2-a]pyrazin-3-yl)-7-((5-(1-methyl-6-oxopiperidin-3-yl)pyridin-2-yl)amino)isoindolin-1-one | LCMS Method J m/z = 445.2 [M + H]+, Ret. time = 3.21 min Chiral HPLC method X5: Ret. time = 5.56 | 1H NMR (400 MHz, DMSO-d6) δ 10.10 (s, 1H), 9.15 (s, 1H), 8.88 (s, 1H), 8.74 (d, J = 8.7 Hz, 1H), 8.47 (d, J = 4.7 Hz, 1H), 8.23 (s, 1H), 8.13 (s, 1H), 7.91 (d, J = 5.0 Hz, 1H), 7.80 (d, J = 8.5 Hz, 1H), 7.01 (d, J = 8.5 Hz, 1H), 7.70-7.63 (m, 1H), 7.01 (d, J = 8.5 Hz, 1H), 4.45 (s, 2H), 3.09 (s, 2H), 2.86 (s, 2H), 1.99 (s, 3H), 1.24 (d, J = 9.6 Hz, 2H). | J AA35 BB61 |
| I-325 | (structure) | (S)-4-(imidazo[1,2-a]pyrazin-3-yl)-7-((5-(1-methyl-6-oxopiperidin-3-yl)pyridin-2-yl)amino)isoindolin-1-one | LCMS Method J m/z = 454.4 [M + H]+, Ret. time = 2.80 min Chiral HPLC method X5: Ret. time = 6.37 | 1H NMR (400 MHz, DMSO-d6) δ 10.10 (s, 1H), 9.15 (s, 1H), 8.89 (s, 1H), 8.74 (d, J = 8.5 Hz, 1H), 8.48 (d, J = 4.8 Hz, 1H), 8.23 (s, 1H), 8.13 (s, 1H), 7.92 (d, J = 4.7 Hz, 1H), 7.81 (d, J = 8.6 Hz, 1H), 7.67 (d, J = 8.6 Hz, 1H), 7.01 (d, J = 8.5 Hz, 1H), 4.46 (s, 2H), 3.44 (m, 1H), 3.08 (d, J = 10.0 Hz, 1H), 2.86 (s, 3H), 1.99 (d, J = 5.7 Hz, 2H). | J AA35 BB61 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-327 | 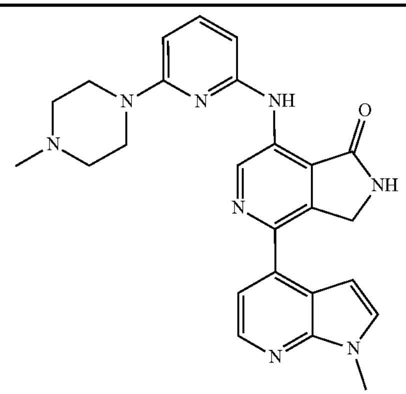 | 4-(1-methyl-1H-pyrrolo[2,3-b]pyridin-4-yl)-7-((6-(4-methylpiperazin-1-yl)pyridin-2-yl)amino)-2,3-dihydro-1H-pyrrolo[3,4-c]pyridin-1-one | LCMS Method C m/z = 455.4 [M + H]+, Ret. time = 1.32 min | 1H NMR (400 MHz, DMSO-d6) δ 9.81 (s, 1H), 9.54 (s, 1H), 9.20 (s, 1H), 8.34 (d, J = 5.0 Hz, 1H), 7.57 (d, J = 3.5 Hz, 1H), 7.49 (q, J = 7.1, 6.2 Hz, 1H), 7.37 (d, J = 5.0 Hz, 1H), 6.85 (d, J = 3.4 Hz, 1H), 6.36 (dd, J = 32.6, 8.0 Hz, 2H), 4.68 (s, 2H), 3.87 (s, 3H), 3.53 (t, J = 5.0 Hz, 4H), 2.48-2.44 (m, 4H), 2.24 (s, 3H). | R AA36 BB14 |
| I-328 | 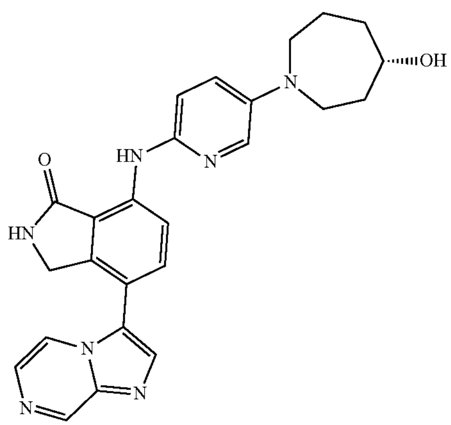 [SMILES: O=C1NCc2c(-c3cnc4cnccn34)ccc(Nc3ccc(N4CCC[C@H](O)CC4)cn3)c21] | (S)-7-((5-(4-hydroxyazepan-1-yl)pyridin-2-yl)amino)-4-(imidazo[1,2-a]pyrazin-3-yl)isoindolin-1-one | LCMS Method C m/z = 456.3 [M + H]+, Ret. time = 1.26 min Chiral HPLC method X5: Ret. time = 6.85 | 1H NMR (400 MHz, DMSO-d6) δ 9.70 (s, 1H), 9.13 (s, 1H), 8.76 (s, 1H), 8.45 (t, J = 6.6 Hz, 2H), 8.10 (s, 1H), 7.90 (d, J = 4.8 Hz, 1H), 7.81 (d, J = 3.1 Hz, 1H), 7.72 (d, J = 8.6 Hz, 1H), 7.22-7.12 (m, 1H), 6.94 (d, J = 8.9 Hz, 1H), 4.42 (s, 2H), 3.68 (s, 1H), 1.90 (s, 3H), 1.64 (d, J = 8.0 Hz, 4H), 1.53 (s, 2H). | T AA37 BB61 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-329 | 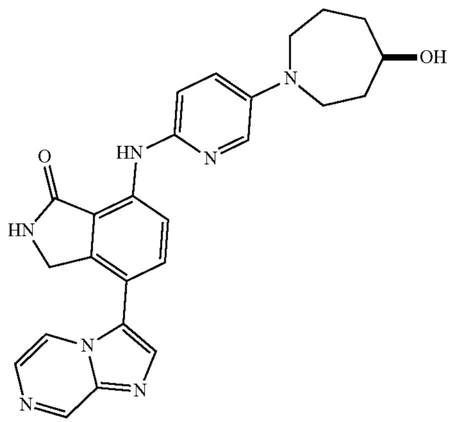 [SMILES: O=C1NCc2c(-c3cnc4cnccn34)ccc(Nc3ccc(N4CCC[C@@H](O)CC4)cn3)c21] | (R)-7-((5-(4-hydroxyazepan-1-yl)pyridin-2-yl)amino)-4-(imidazo[1,2-a]pyrazin-3-yl)isoindolin-1-one | LCMS Method C m/z = 456.4 [M + H]+, Ret. time = 1.25 min Chiral HPLC method X5: Ret. time = 4.67 | 1H NMR (400 MHz, DMSO-d6) δ 9.72 (s, 1H), 9.15 (s, 1H), 8.78 (s, 1H), 8.47 (t, J = 6.9 Hz, 2H), 8.12 (s, 1H), 7.92 (d, J = 4.7 Hz, 1H), 7.83 (d, J = 3.2 Hz, 1H), 7.74 (d, J = 8.6 Hz, 1H), 7.24-7.12 (m, 1H), 6.96 (d, J = 9.0 Hz, 1H), 4.54 (s, 1H), 4.44 (s, 2H), 3.71 (s, 1H), 1.92 (s, 2H), 1.54 (d, J = 10.4 Hz, 1H), 1.25 (m, 1H). | T AA37 BB61 |
| I-330 | 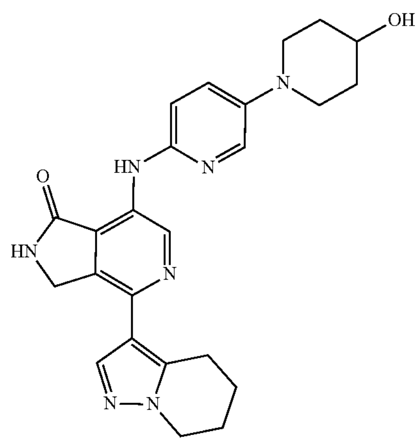 [SMILES: O=C1NCc2c(-c3cnn4c3CCCC4)ncc(Nc3ccc(N4CCC(O)CC4)cn3)c21] | 7-((5-(4-hydroxypiperidin-1-yl)pyridin-2-yl)amino)-4-(4,5,6,7-tetrahydropyrazolo[1,5-a]pyridin-3-yl)-2,3-dihydro-1H-pyrrolo[3,4-c]pyridin-1-one | LCMS Method J m/z = 446.7 [M + H]+, Ret. time = 2.70 min | 1H NMR (400 MHz, DMSO-d6) δ 9.71 (d, J = 4.6 Hz, 1H), 9.20 (d, J = 5.0 Hz, 1H), 9.11 (s, 1H), 7.99 (s, 1H), 7.42 (s, 1H), 6.95 (s, 1H), 4.72 (s, 1H), 4.61 (s, 2H), 4.12 (d, J = 5.9 Hz, 2H), 3.6 (m, 1H), 3.43 (s, 2H), 3.11 (s, 2H), 2.80 (s, 2H), 1.99 (s, 2H), 1.83 (s, 3H), 1.52 (s, 2H), 1.22 (s, 1H). | R AA12 BB46 |

| # | STRUCTURE | NAME | LCMS | 1H NMR | Method Reagent AA BB |
|---|---|---|---|---|---|
| I-331 | 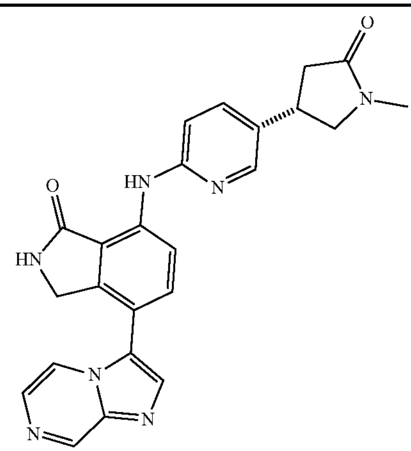 | (S)-4-(imidazo[1,2-a]pyrazin-3-yl)-7-((5-(1-methyl-5-oxopyrrolidin-3-yl)pyridin-2-yl)amino)isoindolin-1-one | LCMS Method C m/z = 440.6 [M + H]+, Ret. time = 1.32 min Chiral HPLC method X5: Ret. time = 14.60 | 1H NMR (400 MHz, DMSO-d6) δ 10.12 (s, 1H), 9.15 (s, 1H), 8.90 (s, 1H), 8.73 (d, J = 8.6 Hz, 1H), 8.48 (d, J = 4.7 Hz, 1H), 8.25 (d, J = 2.5 Hz, 1H), 8.13 (s, 1H), 7.92 (d, J = 4.7 Hz, 1H), 7.81 (d, J = 8.5 Hz, 1H), 7.70 (dd, J = 8.6, 2.5 Hz, 1H), 7.03 (d, J = 8.5 Hz, 1H), 4.46, (s, 2H), 3.70 (t, J = 8.8 Hz, 1H), 3.58 (q, J = 8.4 Hz, 1H), 3.42 (d, J = 5.2 Hz, 1H), 2.78 (s, 3H), 2.64 (d, J = 7.7 Hz, 1H), 2.42-2.34 (m, 2H), 1.23 (s, 5H), 0.85 (s, 2H). | J AA38 BB61 |
| I-332 | 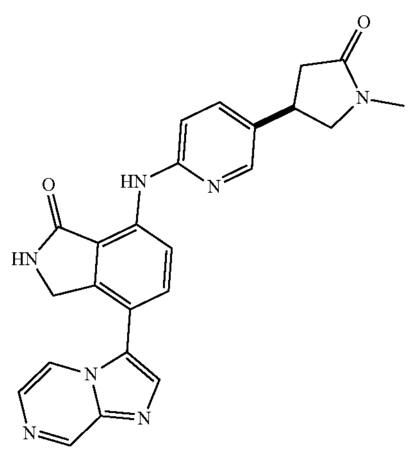 | (R)-4-(imidazo[1,2-a]pyrazin-3-yl)-7-((5-(1-methyl-5-oxopyrrolidin-3-yl)pyridin-2-yl)amino)isoindolin-1-one | LCMS Method C m/z = 440.6 [M + H]+, Ret. time = 1.32 min Chiral HPLC method X5: Ret. time = 13.17 | 1H NMR (400 MHz, DMSO-d6) δ 10.12 (s, 1H), 9.15 (s, 1H), 8.89 (s, 1H), 8.73 (d, J = 8.6 Hz, 1H), 8.48 (d, J = 4.7 Hz, 1H), 8.25 (s, 1H), 8.13 (s, 1H), 7.92 (d, J = 4.8 Hz, 1H), 7.81 (d, J = 8.6 Hz, 1H), 7.70 (d, J = 8.7 Hz, 1H), 7.03 (d, J = 8.5 Hz, 1H), 4.46 (s, 2H), 3.70 (t, J = 8.8 Hz, 1H), 3.57 (t, J = 8.3 Hz, 1H), 3.51-3.46 (m, 1H), 3.41 (t, J = 5.2 Hz, 1H), 2.78 (s, 3H), 2.65 (s, 1H), 2.41-2.36 (m, 1H), 1.98 (s, 1H). | J AA38 BB61 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-333 | 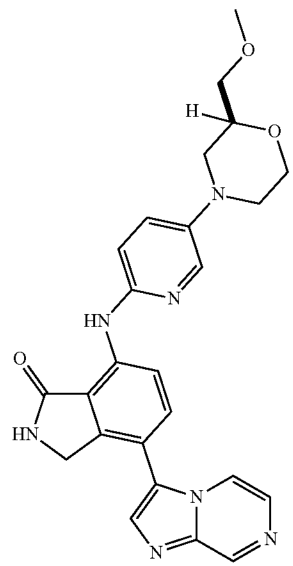 [SMILES: COC[C@@H]1CN(c2ccc(Nc3ccc(-c4cnc5cnccn45)c4c3C(=O)NC4)nc2)CCO1] | (S)-4-(imidazo[1,2-a]pyrazin-3-yl)-7-((5-(2-(methoxymethyl)morpholino)pyridin-2-yl)amino)isoindolin-1-one | LCMS Method J m/z = 472.2 [M + H]+, Ret. time = 3.29 min Chiral HPLC method X1: Ret. time = 24.11 | 1H NMR (400 MHz, DMSO-d6) δ 9.91 (s, 1H), 9.14 (s, 1H), 8.84 (s, 1H), 8.60 (d, J = 8.5 Hz, 1H), 8.47 (d, J = 4.7 Hz, 1H), 8.12 (s, 1H), 8.01 (d, J = 3.0 Hz, 1H), 7.91 (d, J = 4.7 Hz, 1H), 7.77 (d, J = 8.7 Hz, 1H), 7.46 (d, J = 6.9 Hz, 1H), 6.99 (d, J = 9.0 Hz, 1H), 4.44 (s, 2H), 3.95 (d, J = 11.4 Hz, 1H), 3.77-3.63 (m, 2H), 3.55-3.39 (m, 5H), 3.29 (s, 4H). | F AA39 BB61 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-334 | 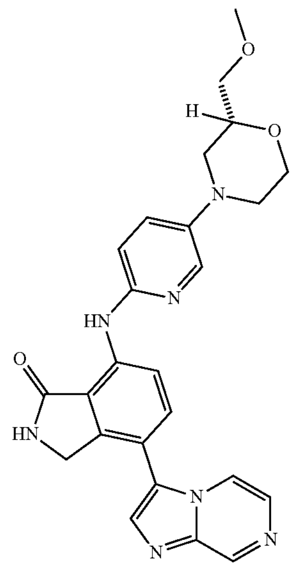 [SMILES: COC[C@H]1CN(c2ccc(Nc3ccc(-c4cnc5cnccn45)c4c3C(=O)NC4)nc2)CCO1] | (R)-4-(imidazo[1,2-a]pyrazin-3-yl)-7-((5-(2-(methoxymethyl)morpholino)pyridin-2-yl)amino)isoindolin-1-one | LCMS Method J m/z = 472.2 [M + H]+, Ret. time = 3.32 min Chiral HPLC method X1: Ret. time = 26.69 | 1H NMR (400 MHz, DMSO-d6) δ 9.91 (s, 1H), 9.14 (s, 1H), 8.84 (s, 1H), 8.60 (d, J = 8.6 Hz, 1H), 8.47 (d, J = 4.2 Hz, 1H), 8.12 (s, 1H), 8.01 (d, J = 3.1 Hz, 1H), 7.91 (d, J = 4.7 Hz, 1H), 7.77 (d, J = 8.6 Hz, 1H), 7.46 (dd, J = 9.0, 3.1 Hz, 1H), 6.99 (d, J = 8.8 Hz, 1H), 4.44 (s, 2H), 3.95 (d, J = 12.7 Hz, 1H), 3.74 (s, 1H), 3.66 (t, J = 10.7 Hz, 1H), 3.47 (dd, J = 32.3, 8.2 Hz, 5H), 3.29 (s, 5H), 1.23 (s, 10H) 0.86 (d, J = 8.1 Hz, 4H) | F AA39 BB61 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-335 | 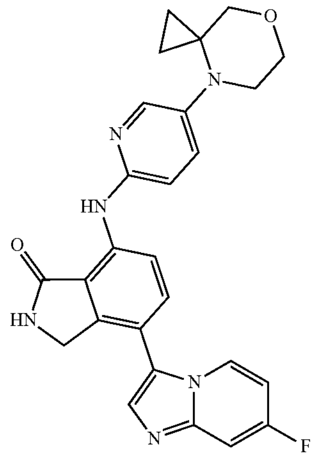 [SMILES: O=C1NCc2c(-c3cnc4cc(F)ccn34)ccc(Nc3ccc(N4CCOCC45CC5)cn3)c21] | 7-((5-(7-oxa-4-aza-spiro[2.5]octan-4-yl)pyridin-2-yl)amino)-4-(7-fluoro-imidazo[1,2-a]pyridin-3-yl)isoindolin-1-one | LCMS Method C m/z = 471.5 [M + H]+, Ret. time = 1.33 min | 1H NMR (400 MHz, DMSO-d6) δ 9.83 (s, 1H), 8.78 (s, 1H), 8.57 (d, J = 8.5 Hz, 1H), 8.41 (s, 1H), 8.10 (s, 1H), 7.81 (d, J = 3.1 Hz, 1H), 7.68 (d, J = 8.8 Hz, 1H), 7.53 (d, J = 10.5 Hz, 1H) 7.45 (d, J = 8.8 Hz, 1H), 6.96 (s, 2H), 4.37 (s, 2H), 3.59 (d, J = 17.7 Hz, 2H), 1.23 (s, 3H), 0.90 (s, 2H), 0.72 (s, 2H). | F AA40 BB63 |
| I-336 | 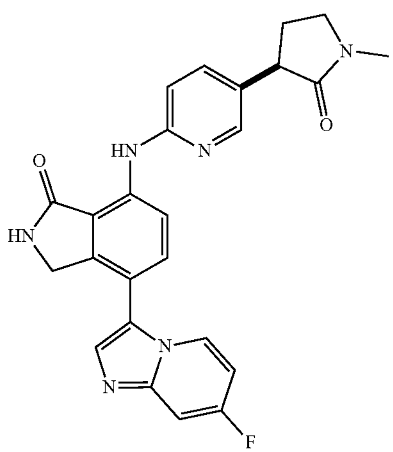 | (R)-4-(7-fluoroimidazo[1,2-a]pyridin-3-yl)-7-((5-(1-methyl-2-oxopyrrolidin-3-yl)pyridin-2-yl)amino)isoindolin-1-one | LCMS Method J m/z = 457.2 [M + H]+, Ret. time = 2.95 min Chiral HPLC method X3: Ret. time = 4.05 | 1H NMR (400 MHz, DMSO-d6) δ 10.09 (s, 1H), 8.71 (d, J = 8.6 Hz, 1H), 8.44 (t, J = 6.8 Hz, 1H), 8.18 (s, 1H), 7.83 (s, 1H), 7.74 (d, J = 8.6 Hz, 1H), 7.55 (t, J = 11.7 Hz, 2H), 7.12-6.87 (m, 2H), 4.40 (s, 2H), 3.63 (t, J = 9.2 Hz, 1H), 3.43 (dt, J = 16.1, 9.1 Hz, 3H), 2.81 (s, 2H), 2.03 (s, 1H), 1.91 (s, 1H). | F AA41 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-338 | 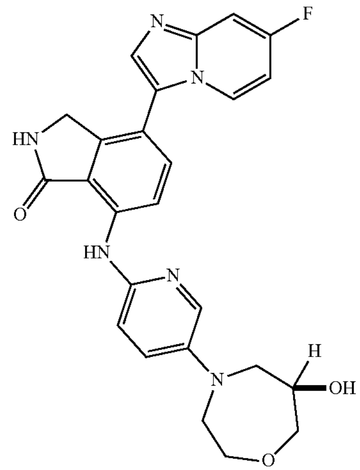 [SMILES: O=C1NCc2c(-c3cnc4cc(F)ccn34)ccc(Nc3ccc(N4CCOC[C@H](O)C4)cn3)c21] | (R)-4-(7-fluoroimidazo[1,2-a]pyridin-3-yl)-7-((5-(6-hydroxy-1,4-oxazepan-4-yl)pyridin-2-yl)amino)isoindolin-1-one | LCMS Method J m/z = 475.2 [M + H]+, Ret. time = 2.88 min Chiral HPLC method X5: Ret. time = 16.94 | ¹H NMR (400 MHz, DMSO): δ 8.94 (s, 1 H), 8.85 (s, 1 H), 8.45-8.43 (m, 2 H), 8.32-8.30 (m, 1 H), 7.98-7.96 (m, 1 H), 7.59-7.58 (d, J = 4 Hz, 1 H), 7.25-7.24 (m, 1 H), 6.88-6.86 (d, J = 8.6 Hz, 1 H), 6.52-6.51 (d, J = 4 Hz, 1 H), 4.69 (s, 1 H), 4.52 (s, 2 H), 3.98-3.97 (m, 2 H), 3.95-3.81 (m, 3 H), 3.67-3.65 (d, J = 8 Hz, 1H), 3.06-2.99 (m, 2 H), 1.79-1.77 (m, 2 H), 1.41-1.33 (m, 2 H). | J AA43 BB63 |
| I-339 | 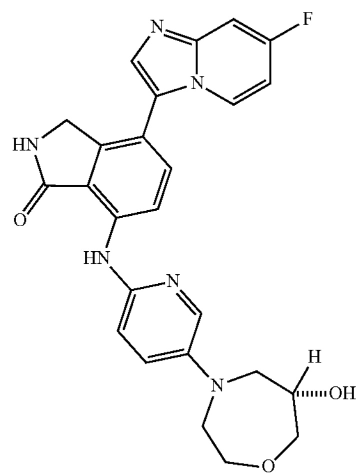 [SMILES: O=C1NCc2c(-c3cnc4cc(F)ccn34)ccc(Nc3ccc(N4CCOC[C@@H](O)C4)cn3)c21] | (S)-4-(7-fluoroimidazo[1,2-a]pyridin-3-yl)-7-((5-(6-hydroxy-1,4-oxazepan-4-yl)pyridin-2-yl)amino)isoindolin-1-one | LCMS Method J m/z = 475.2 [M + H]+, Ret. time = 2.88 min Chiral HPLC method X5: Ret. time = 18.82 | 1H NMR (400 MHz, DMSO-d6) δ 9.70 (s, 1H), 8.74 (s, 1H), 8.47 (d, J = 8.7 Hz, 1H), 8.41 (t, J = 6.7 Hz, 1H), 7.93 (d, J = 3.1 Hz, 1H), 7.80 (s, 1H), 7.65 (d, J = 8.5 Hz, 1H), 7.52 (d, J = 9.9 Hz, 1H), 7.31 (d, J = 8.9 Hz, 1H), 6.96 (q, J = 9.0, 8.6 Hz, 2H), 5.03 (d, J = 4.8 Hz, 1H), 4.36 (s, 2H), 3.97 (s, 1H), 3.82 (d, J = 15.3 Hz, 1H), 3.73 (d, J = 5.0 Hz, 2H), 3.66 (d, J = 15.0 Hz, 1H), 3.58 (d, J = 14.2 Hz, 1H), 3.47 (dd, J = 12.9, 6.1 Hz, 2H), 3.27 (dd, J = 14.8, 7.7 Hz, 1H). | J AA43 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-340 | 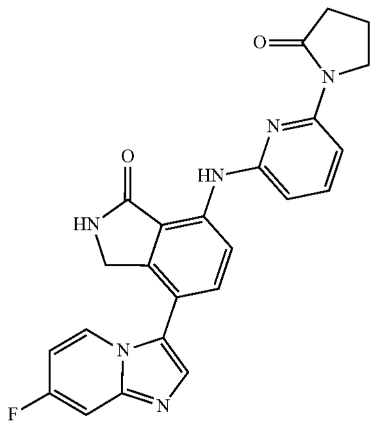 [SMILES: O=C1NCc2c(-c3cnc4cc(F)ccn34)ccc(Nc3cccc(N4CCCC4=O)n3)c21] | 4-(7-fluoroimidazo[1,2-a]pyridin-3-yl)-7-((6-(2-oxopyrrolidin-1-yl)pyridin-2-yl)amino)isoindolin-1-one | LCMS Method J m/z = 443.0 [M + H]+, Ret. time = 3.41 min | 1H NMR (400 MHz, DMSO-d6) δ 10.17 (s, 1H), 8.90 (s, 1H), 8.63 (d, J = 8.5 Hz, 1H), 8.46 (t, J = 6.7 Hz, 1H), 7.84 (t, J = 4.1 Hz, 2H), 7.81-7.65 (m, 2H), 7.54 (dd, J = 10.1, 2.6 Hz, 1H), 7.00 (dt, J = 8.3, 4.2 Hz, 1H), 6.71 (d, J = 7.9 Hz, 1H), 4.41 (s, 2H), 4.13 (t, J = 7.1 Hz, 2H), 2.60 (t, J = 8.0 Hz, 2H), 2.10 (p, J = 7.6 Hz, 2H). | F AA44 BB63 |
| I-341 | 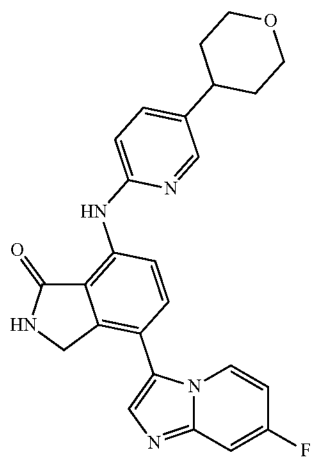 [SMILES: O=C1NCc2c(-c3cnc4cc(F)ccn34)ccc(Nc3ccc(C4CCOCC4)cn3)c21] | 4-(7-fluoroimidazo[1,2-a]pyridin-3-yl)-7-((5-(tetrahydro-2H-pyran-4-yl)pyridin-2-yl)amino)isoindolin-1-one | LCMS Method C m/z = 444.3 [M + H]+, Ret. time = 1.33 min | 1H NMR (400 MHz, DMSO-d6) δ 10.04 (s, 1H), 8.84 (s, 1H), 8.70 (d, J = 8.7 Hz, 1H), 8.43 (t, J = 6.8 Hz, 1H), 8.21 (s, 1H), 7.83 (s, 1H), 7.73 (d, J = 8.6 Hz, 1H), 7.63 (d, J = 9.0 Hz, 1H), 7.53 (d, J = 10.1 Hz, 1H), 7.01-6.89 (m, 2H), 6.13 (s, 2H), 4.39 (s, 2H), 3.96 (d, J = 11.1 Hz, 2H), 3.43 (s, 2H), 2.77 (s, 2H), 1.69 (s, 5H). | F AA45 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-342 | 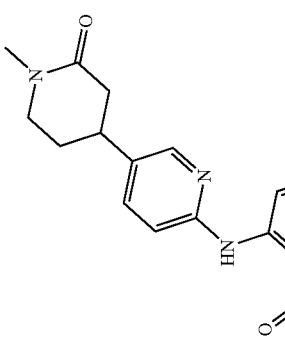 | 4-(imidazo[1,2-a]pyrazin-3-yl)-7-((5-(4-methyl-3-oxopiperazin-1-yl)pyridin-2-yl)amino)isoindolin-1-one | LCMS Method C m/z = 455.6 [M + H]+, Ret. time = 1.29 min | 1H NMR (400 MHz, DMSO-d6) δ 9.92 (d, J = 4.0 Hz, 1H), 9.15 (d, J = 4.2 Hz, 1H), 8.84 (d, J = 3.8 Hz, 1H), 8.60 (dd, J = 8.7, 4.0 Hz, 1H), 8.47 (d, J = 4.7 Hz, 1H), 8.12 (d, J = 4.1 Hz, 1H), 8.03 (t, J = 3.8 Hz, 1H), 7.91 (t, J = 4.5 Hz, 1H), 7.77 (dd, J = 8.7, 3.9 Hz, 1H), 7.49 (dd, J = 8.6, 3.4 Hz, 1H), 7.01 (dd, J = 9.1, 4.1 Hz, 1H), 4.58 (t, J = 5.2 Hz, 1H), 4.44 (d, J = 4.1 Hz, 2H), 3.76 (d, J = 4.2 Hz, 2H), 3.45 (ddt, J = 14.0, 9.4, 5.1 Hz, 7H), 2.91 (d, J = 4.1 Hz, 3H). | F AA46 BB61 |
| I-343 | 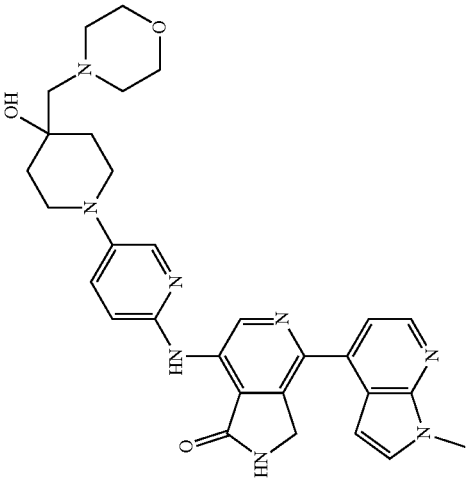 | 7-((5-(4-hydroxy-4-(morpholinomethyl)piperidin-1-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 555.3 [M + H]+, Ret. time = 2.93 min | 1H NMR (400 MHz, DMSO-d6) δ 9.92 (s, 1H), 9.49 (s, 1H), 9.17 (s, 1H), 8.34 (d, J = 5.0 Hz, 1H), 8.06 (d, J = 3.0 Hz, 1H), 7.56 (d, J = 3.5 Hz, 1H), 7.46 (dd, J = 9.1, 2.9 Hz, 1H), 7.37 (d, J = 5.0 Hz, 1H), 7.03 (d, J = 8.9 Hz, 1H), 6.91 (d, J = 3.5 Hz, 1H), 4.71 (s, 2H), 4.21 (s, 1H), 3.86 (s, 3H), 3.56 (t, J = 4.6 Hz, 4H), 3.30 (d, J = 11.4 Hz, 2H), 3.05 (t, J = 10.6 Hz, 2H), 2.28 (s, 2H), 1.68 (t, J = 10.8 Hz, 2H), 1.59 (d, J = 13.1 Hz, 2H). | R AA15 BB14 |

| # | STRUCTURE | NAME | LCMS | $^1$H NMR | Method Reagent AA BB |
|---|---|---|---|---|---|
| I-344 | 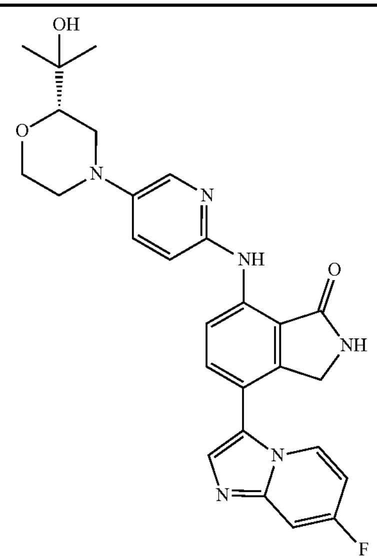 | (R)-4-(7-fluoroimidazo[1,2-a]pyridin-3-yl)-7-((5-(2-(2-hydroxypropan-2-yl)morpholino)pyridin-2-yl)amino)isoindolin-1-one | LCMS Method J m/z = 503.4 [M + H]+, Ret. time = 2.88 min Chiral HPLC method X5: Ret. time = 13.59 | $^1$H NMR (400 MHz, DMSO): δ 9.87 (s, 1 H), 8.80 (s, 1 H), 8.58-8.55 (m, 1 H), 8.42 (s, 1 H), 8.00 (s, 1H), 7.81-7.86 (m, 1 H), 7.70-7.67 (m, 1 H), 7.53-7.43 (m, 2 H), 6.99-6.96 (m, 2 H), 4.50 (s, 1 H), 4.37 (s, 2 H), 4.00-3.98 (d, J = 10.8 Hz, 1 H), 3.67-3.57 (m, 2 H), 3.46 (m, 2 H), 3.39-3.33 (m, 3 H), 1.21-1.09 (m, 6 H) | J AA48 BB63 |

TABLE 8-continued
Characterization Data (LCMS and ¹H NMR).
| # | STRUCTURE | NAME | LCMS | ¹H NMR | Method Reagent AA BB |
|---|---|---|---|---|---|
| I-345 | 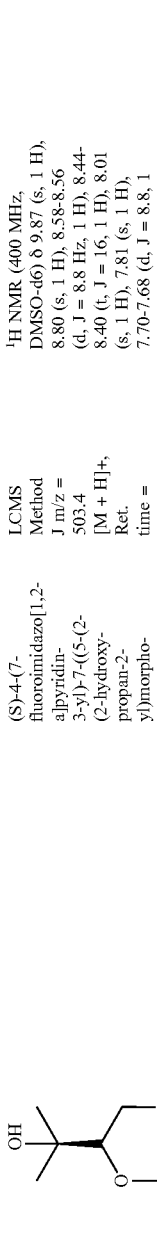 | (S)-4-(7-fluoroimidazo[1,2-a]pyridin-3-yl)-7-((5-(2-hydroxy-2-ylmorpholino)propan-2-ylmorpho-linopyridin-2-yl)amino)iso-indolin-1-one | LCMS Method J m/z = 503.4 [M + H]+, Ret. time = 2.89 min Chiral HPLC method X5: Ret. time = 16.64 | ¹H NMR (400 MHz, DMSO-d6) δ 9.87 (s, 1 H), 8.80 (s, 1 H), 8.58-8.56 (d, J = 8.8 Hz, 1 H), 8.44-8.40 (t, J = 16, 1 H), 8.01 (s, 1 H), 7.81 (s, 1 H), 7.70-7.68 (d, J = 8.8, 1 H), 7.54-7.51 (d, J = 9.6 Hz, 1 H), 7.46-7.44 (m, 1 H), 6.99-6.95 (m, 2 H), 4.51 (s, 1 H), 4.37 (s, 2 H), 4.00-3.98 (d, J = 10.8 Hz, 1 H), 3.67-3.57 (m, 2 H), 3.46-3.44 (m, 2 H), 3.34-3.19 (m, 3 H), 1.23-1.06 (m, 6 H) | J AA48 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-346 | 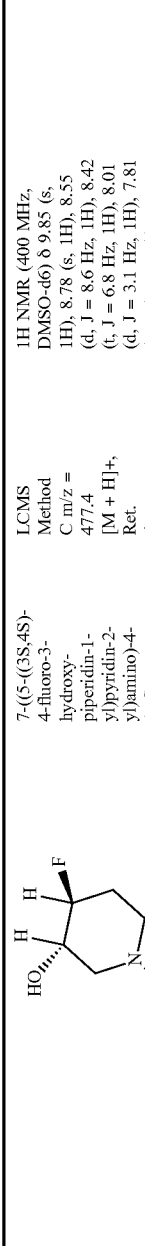 | 7-((5-((3S,4S)-4-fluoro-3-hydroxy-piperidin-1-yl)pyridin-2-yl)amino)-4-(7-fluoro-imidazo[1,2-a]pyridin-3-yl)isoindolin-1-one | LCMS Method C m/z = 477.4 [M + H]+, Ret. time = 1.31 min Chiral HPLC method X3: Ret. time = 8.6 | 1H NMR (400 MHz, DMSO-d6) δ 9.85 (s, 1H), 8.78 (s, 1H), 8.55 (d, J = 8.6 Hz, 1H), 8.42 (t, J = 6.8 Hz, 1H), 8.01 (d, J = 3.1 Hz, 1H), 7.81 (s, 1H), 7.69 (d, J = 8.6 Hz, 1H), 7.57-7.36 (m, 2H), 6.96 (d, J = 8.8 Hz, 2H), 5.43 (s, 1H), 4.37 (s, 2H), 3.67 (s, 1H), 3.54 (t, J = 14.3 Hz, 2H), 2.81 (t, J = 11.7 Hz, 1H), 2.62 (d, J = 10.6 Hz, 1H), 2.11 (s, 1H), 1.73 (s, 1H). | F AA49 BB63 |

| # | STRUCTURE | NAME | LCMS | ¹H NMR | Method Reagent AA BB |
|---|---|---|---|---|---|
| I-347 | 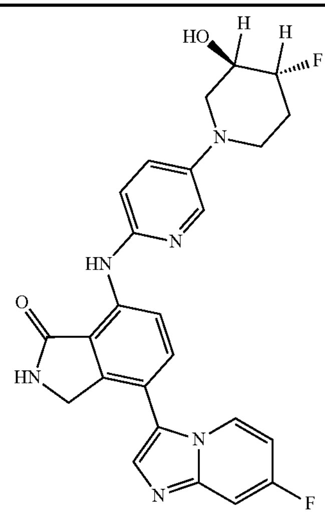 | 7-((5-((3R,4R)-4-fluoro-3-hydroxy-piperidin-1-yl)pyridin-2-yl)amino)-4-(7-fluoro-imidazo[1,2-a]pyridin-3-yl)isoindolin-1-one | LCMS Method J m/z = 477.2 [M + H]+, Ret. time = 3.02 min Chiral HPLC method X3: Ret. time = 8.28 | 1H NMR (400 MHz, DMSO-d6) δ 9.85 (s, 1H), 8.78 (s, 1H), 8.55 (d, J = 8.5 Hz, 1H), 8.42 (t, J = 6.7 Hz, 1H), 8.01 (d, J = 3.0 Hz, 1H), 7.81 (s, 1H), 7.69 (d, J = 8.5 Hz, 1H), 7.49 (ddd, J = 27.0, 9.5, 2.9 Hz, 2H), 6.96 (d, J = 8.6 Hz, 2H), 5.43 (d, J = 4.9 Hz, 1H), 4.48 (s, 1H), 3.66 (s, 1H), 3.54 (t, J = 14.3 Hz, 2H), 2.81 (t, J = 11.5 Hz, 1H), 2.62 (d, J = 10.5 Hz, 2H), 2.11 (s, 1H), 1.73 (s, 1H). | F AA49 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-348 | 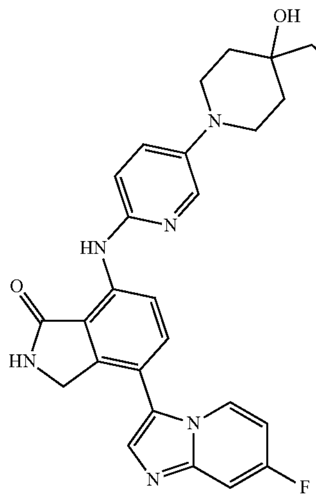 | 4-(7-fluoro-imidazo[1,2-a]pyridin-3-yl)-7-(5-(4-hydroxy-4-(morpholino-methyl)piperidin-1-yl)pyridin-2-yl)amino)isoindolin-1-one | LCMS Method C m/z = 558.2 [M + H]+, Ret. time = 1.52 min | 1H NMR (400 MHz, DMSO-d6) δ 9.82 (s, 1H), 8.78 (s, 1H), 8.55 (d, J = 8.5 Hz, 1H), 8.42 (t, J = 6.7 Hz, 1H), 8.00 (d, J = 3.0 Hz, 1H), 7.81 (s, 1H), 7.68 (d, J = 8.6 Hz, 1H), 7.48 (ddd, J = 36.9, 9.6, 2.9 Hz, 2H), 7.03-6.87 (m, 2H), 4.37 (s, 2H), 4.21 (s, 1H), 3.57 (t, J = 4.6 Hz, 4H), 3.27 (d, J = 11.8 Hz, 3H), 3.03 (t, J = 10.1 Hz, 2H), 2.29 (s, 3H), 1.75-1.64 (m, 2H), 1.58 (d, J = 13.0 Hz, 2H). | F AA15 BB63 |
| I-349 | 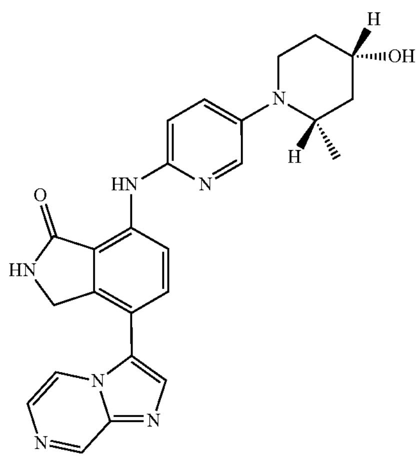 [SMILES: C[C@H]1C[C@@H](O)CCN1c1ccc(Nc2ccc(-c3cnc4cnccn34)c3c2C(=O)NC3)nc1] | 7-((5-((2S, 4S)-4-hydroxy-2-methylpiperidin-1-yl)pyridin-2-yl)amino)-4-(imidazo[1,2-a]pyrazin-3-yl)isoindolin-1-one | LCMS Method J m/z = 456.2 [M + H]+, Ret. time = 2.85 min Chiral HPLC method X6: Ret. time = 20.19 | 1H NMR (400 MHz, DMSO-d6) δ 10.02 (s, 1H), 9.14 (s, 1H), 8.85 (s, 1H), 8.66 (d, J = 8.6 Hz, 1H), 8.47 (d, J = 4.7 Hz, 1H), 8.09 (d, J = 27.0 Hz, 2H), 7.91 (d, J = 4.7 Hz, 1H), 7.79 (d, J = 8.5 Hz, 1H), 7.54 (d, J = 8.7 Hz, 1H), 6.98 (d, J = 8.8 Hz, 1H), 4.71 (d, J = 4.1 Hz, 1H), 4.45 (s, 2H), 3.11-2.96 (m, 2H), 2.82 (d, J = 12.1 Hz, 1H), 1.91 (d, J = 12.5 Hz, 1H), 1.81 (s, 1H), 1.54 (s, 1H), 1.36-1.19 (m, 2H), 0.88 (d, J = 6.1 Hz, 3H). | F AA50 BB61 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-350 | (structure) | 7-(5-((2R,4R)-4-hydroxy-2-methylpiperidin-1-yl)pyridin-2-yl)amino)-4-(imidazo[1,2-a]pyrazin-3-yl)isoindolin-1-one | LCMS Method J m/z = 456.2 [M + H]+, Ret. time = 2.85 min | 1H NMR (400 MHz, DMSO-d6) δ 10.02 (s, 1H), 9.14 (s, 1H), 8.85 (s, 1H), 8.66 (d, J = 8.7 Hz, 1H), 8.47 (d, J = 4.7 Hz, 1H), 8.09 (d, J = 27.1 Hz, 2H), 7.91 (d, J = 4.7 Hz, 1H), 7.79 (d, J = 8.5 Hz, 1H), 7.54 (d, J = 9.0 Hz, 1H), 6.98 (d, J = 8.7 Hz, 1H), 4.71 (d, J = 4.3 Hz, 2H), 4.45 (s, 2H), 3.60 (s, 2H), 3.10-2.98 (m, 2H), 2.82 (d, J = 11.3 Hz, 2H), 1.95-1.80 (m, 2H), 1.52 (d, J = 10.7 Hz, 2H), 1.29 (d, J = 11.2 Hz, 2H), 0.88 (d, J = 6.1 Hz, 3H). | F AA50 BB61 |
| I-351 | (structure) | 7-(5-((2R,4S)-4-hydroxy-2-methylpiperidin-1-yl)pyridin-2-yl)amino)-4-(imidazo[1,2-a]pyrazin-3-yl)isoindolin-1-one | LCMS Method J m/z = 456.2 [M + H]+, Ret. time = 2.92 min Chiral HPLC method X5: Ret. time = 10.60 | 1H NMR (400 MHz, DMSO-d6) δ 9.86 (s, 1H), 9.14 (s, 1H), 8.80 (s, 1H), 8.57 (d, J = 8.5 Hz, 1H), 8.46 (d, J = 4.7 Hz, 1H), 8.11 (s, 1H), 7.93 (dd, J = 21.2, 3.9 Hz, 2H), 7.75 (d, J = 8.6 Hz, 1H), 7.48-7.33 (m, 1H), 6.95 (d, J = 8.8 Hz, 1H), 4.64 (d, J = 4.4 Hz, 1H), 4.43 (s, 2H), 4.04 (s, 1H), 3.82 (s, 1H), 2.90 (t, J = 11.1 Hz, 1H), 1.88 (s, 1H), 1.76 (d, J = 12.6 Hz, 1H), 1.64 (d, J = 13.4 Hz, 1H), 1.43 (d, J = 12.0 Hz, 1H), 0.94 (d, J = 6.6 Hz, 3H). | F AA50 BB61 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-352 | 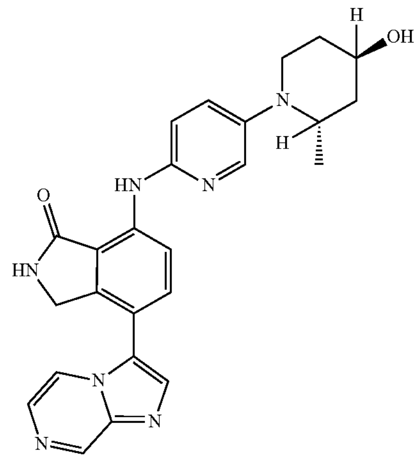 [SMILES: C[C@H]1C[C@H](O)CCN1c1ccc(Nc2ccc(-c3cnc4cnccn34)c3c2C(=O)NC3)nc1] | 7-((5-((2S,4R)-4-hydroxy-2-methylpiperidin-1-yl)pyridin-2-yl)amino)-4-(imidazo[1,2-a]pyrazin-3-yl)isoindolin-1-one | LCMS Method J m/z = 456.2 [M + H]+, Ret. time = 2.90 min Chiral HPLC method X5: Ret. time = 11.48 | 1H NMR (400 MHz, DMSO-d6) δ 9.86 (s, 1H), 9.14 (s, 1H), 8.81 (s, 1H), 8.57 (d, J = 8.6 Hz, 1H), 8.46 (d, J = 4.7 Hz, 1H), 8.11 (s, 1H), 7.96 (d, J = 3.0 Hz, 1H), 7.91 (d, J = 4.8 Hz, 1H), 7.75 (d, J = 8.6 Hz, 1H), 7.42 (dd, J = 9.1, 3.0 Hz, 1H), 6.95 (d, J = 8.9 Hz, 1H), 4.64 (d, J = 4.5 Hz, 1H), 4.43 (s, 2H), 4.04 (s, 1H), 3.29 (d, J = 4.5 Hz, 1H), 2.90 (t, J = 11.1 Hz, 1H), 1.89 (d, J = 12.2 Hz, 1H), 1.76 (d, J = 12.6 Hz, 1H), 1.62 (s, 1H), 1.43 (s, 1H), 0.94 (d, J = 6.6 Hz, 3H). | F AA50 BB61 |
| I-353 | 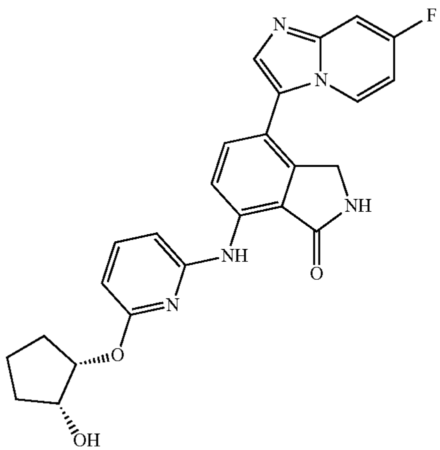 [SMILES: O=C1NCc2c(-c3cnc4cc(F)ccn34)ccc(Nc3cccc(O[C@H]4CCC[C@H]4O)n3)c21] | 4-(7-fluoroimidazo[1,2-a]pyridin-3-yl)-7-(((1S,2R)-2-hydroxycyclopentyl)oxy)pyridin-2-yl)amino)isoindolin-1-one | LCMS Method C m/z = 460.7 [M + H]+, Ret. time = 1.40 min Chiral HPLC method X3: Ret. time = 5.57 | 1H NMR (400 MHz, DMSO-d6) δ 9.99 (s, 1H), 8.55 (d, J = 8.5 Hz, 1H), 8.39 (s, 1H), 7.80 (s, 1H), 7.73 (d, J = 8.4 Hz, 1H), 7.59 (t, J = 7.6 Hz, 1H), 7.49 (d, J = 9.8 Hz, 1H), 6.99 (s, 1H), 6.52 (d, J = 7.9 Hz, 1H), 6.34 (d, J = 8.2 Hz, 1H), 5.06 (s, 1H), 4.36 (s, 2H), 4.19 (s, 1H), 2.03 (s, 1H), 1.77 (s, 3H), 1.64 (s, 1H), 1.54 (s, 1H). | F AA51 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-354 | 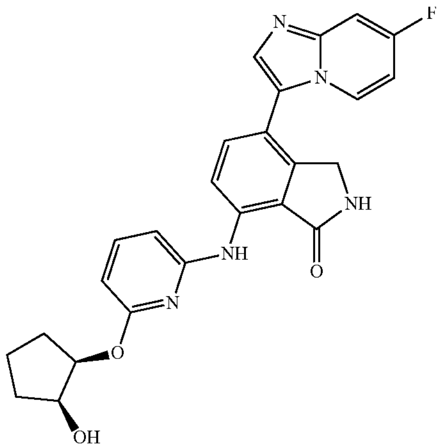 [SMILES: O=C1NCc2c(-c3cnc4cc(F)ccn34)ccc(Nc3cccc(O[C@@H]4CCC[C@@H]4O)n3)c21] | 4-(7-fluoroimidazo[1,2-a]pyridin-3-yl)-7-(((1R,2S)-2-hydroxycyclopentyl)oxy)pyridin-2-yl)amino)isoindolin-1-one | LCMS Method C m/z = 460.4 [M + H]+, Ret. time = 1.35 min Chiral HPLC method X3: Ret. time = 5.35 | 1H NMR (400 MHz, DMSO-d6) δ 10.07 (s, 1H), 8.88 (s, 1H), 8.56 (d, J = 8.5 Hz, 1H), 8.47-8.36 (m, 1H), 7.83 (s, 1H), 7.74 (d, J = 8.6 Hz, 1H), 7.65-7.48 (m, 2H), 6.99 (s, 1H), 6.52 (d, J = 7.9 Hz, 1H), 6.34 (d, J = 8.0 Hz, 1H), 5.08 (s, 1H), 4.63 (d, J = 4.9 Hz, 1H), 4.39 (s, 2H), 4.21 (s, 1H), 2.03 (s, 1H), 1.80 (d, J = 15.3 Hz, 3H), 1.65 (s, 1H), 1.55 (s, 1H). | F AA51 BB63 |
| I-355 | 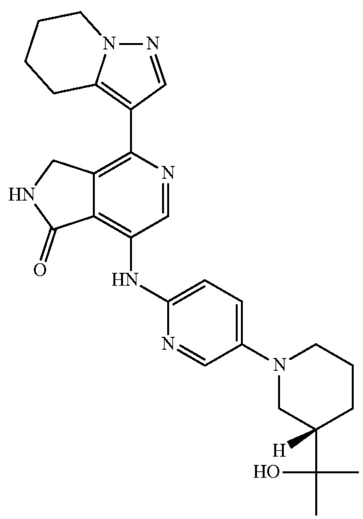 [SMILES: CC(C)(O)[C@H]1CCCN(c2ccc(Nc3cnc(-c4cnn5c4CCCC5)c4c3C(=O)NC4)nc2)C1] | (S)-7-((5-(3-(2-hydroxypropan-2-yl)piperidin-1-yl)pyridin-2-yl)amino)-4-(4,5,6,7-tetrahydropyrazolo[1,5-a]pyridin-3-yl)-2,3-dihydro-1H-pyrrolo[3,4-c]pyridin-1-one | LCMS Method C m/z = 488.8 [M + H]+, Ret. time = 1.38 min Chiral HPLC method X3: Ret. time = 5.89 | 1H NMR (400 MHz, DMSO-d6) δ 9.71 (s, 1H), 9.20 (s, 1H), 9.12 (s, 1H), 7.98 (d, J = 3.0 Hz, 1H), 7.78 (s, 1H), 7.39 (dd, J = 9.0, 3.0 Hz, 1H), 6.95 (d, J = 9.0 Hz, 1H), 4.61 (s, 2H), 4.28 (s, 1H), 4.12 (t, J = 6.0 Hz, 2H), 3.71 (d, J = 12.1 Hz, 1H), 3.59 (d, J = 11.9 Hz, 1H), 3.11 (t, J = 6.4 Hz, 2H), 2.39 (d, J = 11.7 Hz, 2H), 1.77 (d, J = 35.8 Hz, 4H), 1.55 (s, 3H), 1.10 (d, J = 10.5 Hz, 6H). | R AA13 BB46 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-356 | 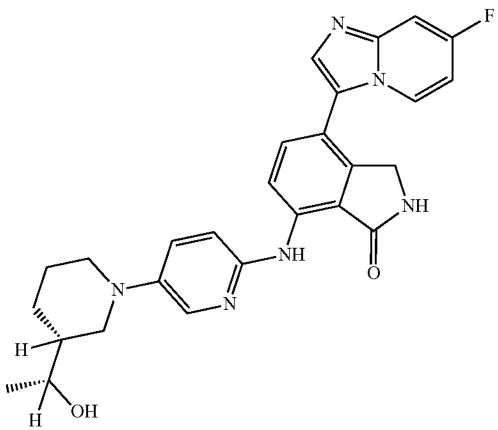 [SMILES: C[C@@H](O)[C@@H]1CCCN(c2ccc(Nc3ccc(-c4cnc5cc(F)ccn45)c4c3C(=O)NC4)nc2)C1] | 4-(7-fluoroimidazo[1,2-a]pyridin-3-yl)-7-((5-((R)-3-((R)-1-(hydroxy-ethyl)piperidin-1-yl)pyridin-2-yl)amino)iso-indolin-1-one | LCMS Method J m/z = 487.2 [M + H]+, Ret. time = 2.95 min Chiral HPLC method X1: Ret. time = 16.66 | 1H NMR (400 MHz, DMSO-d6) δ 9.83 (s, 1H), 8.79 (s, 1H), 8.56 (d, J = 8.5 Hz, 1H), 8.42 (t, J = 6.6 Hz, 1H), 7.98 (d, J = 3.0 Hz, 1H), 7.81 (s, 1H), 7.68 (d, J = 8.4 Hz, 1H), 7.59-7.35 (m, 2H), 7.04-6.86 (m, 2H), 4.48 (d, J = 4.9 Hz, 1H), 4.38 (s, 2H), 3.58-3.48 (m, 2H), 2.24 (s, 1H), 1.85 (d, J = 12.7 Hz, 1H), 1.75 (d, J = 13.0 Hz, 1H), 1.54 (s, 2H), 1.19 (d, J = 31.0 Hz, 3H), 1.09 (d, J = 6.2 Hz, 3H). | F AA52 BB63 |
| I-357 | 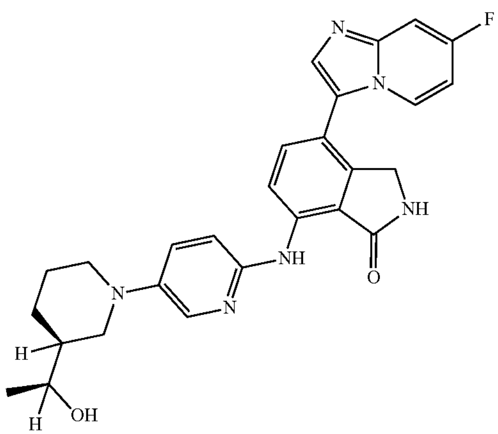 [SMILES: C[C@H](O)[C@H]1CCCN(c2ccc(Nc3ccc(-c4cnc5cc(F)ccn45)c4c3C(=O)NC4)nc2)C1] | 4-(7-fluoroimidazo[1,2-a]pyridin-3-yl)-7-((5-((S)-3-((S)-1-hydroxy-ethyl)piperidin-1-yl)pyridin-2-yl)amino)iso-indolin-1-one | LCMS Method J m/z = [M + H]+, Ret. time = 2.96 min Chiral HPLC method X1: Ret. time = 18.39 | 1H NMR (400 MHz, DMSO-d6) δ 9.83 (s, 1H), 8.79 (s, 1H), 8.56 (d, J = 8.6 Hz, 1H), 8.43 (t, J = 6.6 Hz, 1H), 7.98 (d, J = 3.0 Hz, 1H), 7.83 (s, 1H), 7.68 (d, J = 8.6 Hz, 1H), 7.60-7.48 (m, 1H), 7.42 (dd, J = 8.9, 3.1 Hz, 1H), 7.03-6.87 (m, 2H), 4.48 (s, 1H), 4.43 (d, J = 43.4 Hz, 3H), 3.62-3.43 (m, 3H), 1.80 (dd, J = 38.6, 13.0 Hz, 3H), 1.54 (s, 2H), 1.30-0.96 (m, 6H), | F AA52 BB63 |

TABLE 8-continued
Characterization Data (LCMS and ¹H NMR).
| # | STRUCTURE | NAME | LCMS | ¹H NMR | Method Reagent AA BB |
|---|---|---|---|---|---|
| I-358 | 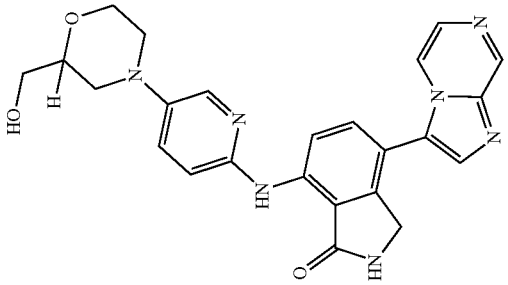 | 7-((5-(2-(hydroxymethyl)morpholino)pyridin-2-yl)amino)-4-(imidazo[1,2-a]pyrazin-3-yl)isoindolin-1-one | LCMS Method J m/z = 458.2 [M + H]+, Ret. time = 3.11 min | 1H NMR (400 MHz, DMSO-d6) δ 9.90 (s, 1H), 9.14 (s, 1H), 8.82 (s, 1H), 8.59 (d, J = 8.6 Hz, 1H), 8.46 (d, J = 4.5 Hz, 1H), 8.11 (s, 1H), 8.00 (s, 1H), 7.91 (d, J = 4.7 Hz, 1H), 7.76 (d, J = 8.7 Hz, 1H), 7.46 (t, J = 5.5 Hz, 1H), 6.99 (d, J = 9.0 Hz, 1H), 4.79 (s, 1H), 4.43 (s, 2H), 3.95 (d, J = 11.3 Hz, 1H), 3.72-3.40 (m, 1H), 3.72-3.40 (m, 7H), 2.72-2.65 (m, 1H), 1.23 (s, 2H). | F AA53 BB61 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-359 | 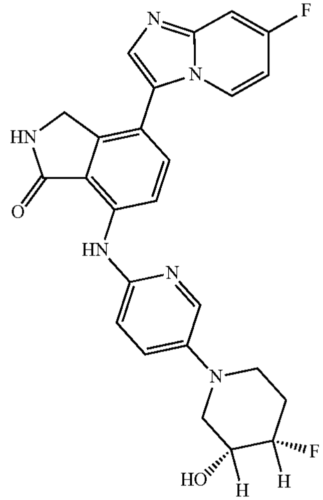 [SMILES: O=C1NCc2c(-c3cnc4cc(F)ccn34)ccc(Nc3ccc(N4CC[C@H](F)[C@H](O)C4)cn3)c21] | 7-((5-((3R,4S)-4-fluoro-3-hydroxypiperidin-1-yl)pyridin-2-yl)amino)-4-(7-fluoro-imidazo[1,2-a]pyridin-3-yl)isoindolin-1-one | LCMS Method J m/z = 477.4 [M + H]+, Ret. time = 2.56 min Chiral HPLC method X3: Ret. time = 6.35 | 1H NMR (400 MHz, DMSO-d6) δ 9.85 (s, 1H), 8.77 (s, 1H), 8.64-8.27 (m, 2H), 8.01 (s, 1H), 7.88-7.59 (m, 2H), 7.48 (dd, J = 25.7, 9.4 Hz, 2H), 6.96 (t, J = 8.0 Hz, 2H), 5.19 (d, J = 5.7 Hz, 1H), 4.79 (d, J = 50.8 Hz, 1H), 4.37 (s, 2H), 4.16-4.00 (m, 1H), 3.76 (d, J = 27.2 Hz, 2H), 3.28-3.06 (m, 3H), 2.94 (d, J = 12.9 Hz, 2H), 2.13-1.75 (m, 3H). | T AA54 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-360 | 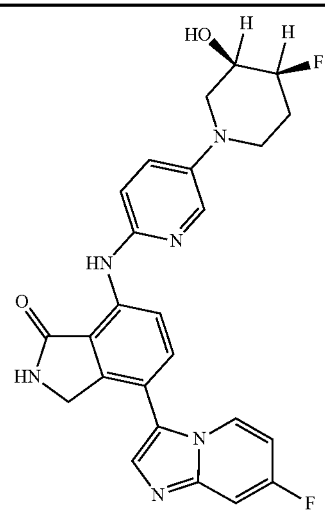 | 7-((5-((3R,4S)-4-fluoro-3-hydroxypiperidin-1-yl)pyridin-2-yl)amino)-4-(7-fluoroimidazo[1,2-a]pyridin-3-yl)isoindolin-1-one | LCMS Method J m/z = 477.4 [M + H]+, Ret. time = 2.51 min Chiral HPLC method X3: Ret. time = 6.29 | 1H NMR (400 MHz, DMSO-d6) δ 9.85 (s, 1H), 8.78 (s, 1H), 8.55 (d, J = 8.6 Hz, 1H), 8.42 (dd, J = 7.6, 5.7 Hz, 1H), 8.01 (d, J = 3.0 Hz, 1H), 7.81 (s, 1H), 7.69 (d, J = 8.6 Hz, 1H), 7.49 (ddd, J = 27.0, 9.6, 2.9 Hz, 2H), 6.97 (td, J = 8.6, 8.0, 3.1 Hz, 1H), 5.20 (d, J = 5.5 Hz, 1H), 4.93-4.82 (m, 1H), 4.73 (t, J = 3.5 Hz, 1H), 4.38 (s, 2H), 3.73 (t, J = 27.3 Hz, 1H), 3.31-3.19 (m, 2H), 2.95 (q, J = 9.6, 9.1 Hz, 2H), 2.12-1.98 (m, 1H), 1.88 (dd, J = 35.7, 11.9 Hz, 1H). | T AA54 BB63 |
| I-361 | 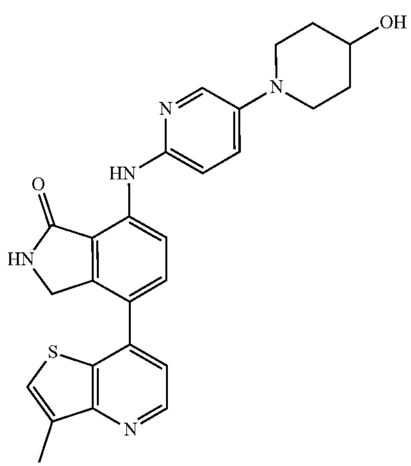 [SMILES: Cc1csc2c(-c3ccc(Nc4ccc(N5CCC(O)CC5)cn4)c4c3CNC4=O)ccnc12] | 7-((5-(4-hydroxypiperidin-1-yl)pyridin-2-yl)amino)-4-(3-methylthieno[3,2-b]pyridin-7-yl)isoindolin-1-one | LCMS Method J m/z = 472.4 [M + H]+, Ret. time = 2.98 min | 1H NMR (400 MHz, DMSO-d6) δ 9.91 (s, 1H), 8.82 (s, 1H), 8.73 (d, J = 4.8 Hz, 1H), 8.55 (d, J = 8.5 Hz, 1H), 8.01 (d, J = 3.0 Hz, 1H), 7.82 (d, J = 9.4 Hz, 2H), 7.58 (d, J = 4.8 Hz, 1H), 7.44 (dd, J = 9.0, 3.1 Hz, 1H), 6.95 (d, J = 9.0 Hz, 1H), 4.72 (d, J = 4.1 Hz, 1H), 4.47 (s, 2H), 3.46 (d, J = 11.2 Hz, 2H), 2.83 (d, J = 12.7 Hz, 2H), 2.47 (s, 6H), 1.82 (m, 2H), 1.57-1.45 (m, 2H). | E AA12 BB64 |

TABLE 8-continued
Characterization Data (LCMS and $^1$H NMR).
| # | STRUCTURE | NAME | LCMS | $^1$H NMR | Method Reagent AA BB |
|---|---|---|---|---|---|
| I-362 | 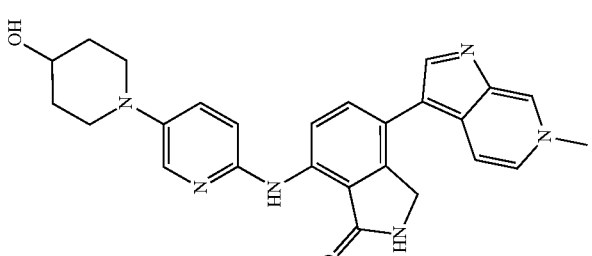 | 7-((5-(4-hydroxypiperidin-1-yl)pyridin-2-yl)amino)-4-(6-methyl-6H-pyrrolo[2,3-c]pyridin-3-yl)isoindolin-1-one | LCMS Method C m/z = 455.7 [M + H]+, Ret. time = 1.24 min | 1H NMR (400 MHz, DMSO-d6) δ 9.76 (s, 1H), 8.92 (s, 1H), 8.75 (s, 1H), 8.56-8.30 (m, 2H), 7.95 (d, J = 15.9 Hz, 3H), 7.71 (d, J = 8.5 Hz, 1H), 7.41 (dd, J = 8.9, 3.1 Hz, 1H), 6.89 (d, J = 8.9 Hz, 1H), 4.71 (s, 1H), 4.50 (s, 2H), 4.23 (s, 2H), 3.66-3.56 (m, 1H), 2.79 (t, J = 10.4 Hz, 2H), 2.45 (s, 4H), 1.84 (d, J = 10.4 Hz, 2H), 1.60-1.44 (m, 2H). | F AA12 BB65 |

| # | STRUCTURE | NAME | LCMS | ¹H NMR | Method Reagent AA BB |
|---|---|---|---|---|---|
| I-363 | 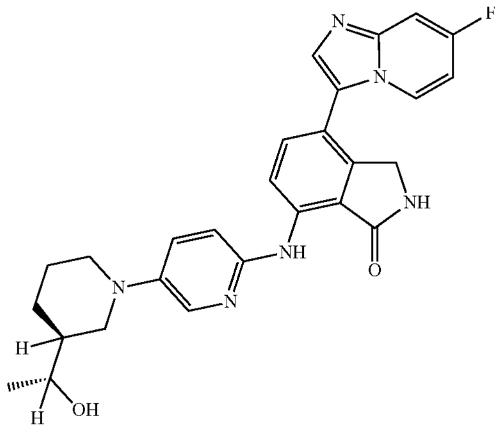 [SMILES: C[C@@H](O)[C@H]1CCCN(c2ccc(Nc3ccc(-c4cnc5cc(F)ccn45)c4c3C(=O)NC4)nc2)C1] | 4-(7-fluoro-imidazo[1,2-a]pyridin-3-yl)-7-((5-((S)-3-((R)-1-hydroxy-ethyl)piperidin-1-yl)pyridin-2-yl)amino)isoindolin-1-one | LCMS Method J m/z = 487.4 [M + H]+, Ret. time = 3.05 min Chiral HPLC method X4: Ret. time = 8.5 | 1H NMR (400 MHz, DMSO-d6) δ 9.83 (s, 1H), 8.79 (s, 1H), 8.55 (d, J = 8.5 Hz, 1H), 8.42 (t, J = 6.7 Hz, 1H), 7.98 (d, J = 2.9 Hz, 1H), 7.81 (s, 1H), 7.68 (d, J = 8.6 Hz, 1H), 7.53 (dd, J = 10.1, 2.6 Hz, 1H), 7.41 (dd, J = 9.1, 3.0 Hz, 1H), 6.97 (td, J = 9.0, 8.2, 3.5 Hz, 2H), 4.54 (s, 1H), 4.37 (s, 2H), 3.74 (d, J = 11.1 Hz, 1H), 3.54 (d, J = 11.9 Hz, 1H), 2.61-2.54 (m, 2H), 2.40 (t, J = 11.2 Hz, 2H), 1.72 (s, 2H), 1.65-1.46 (m, 2H), 1.10 (d, J = 6.1 Hz, 4H). | T AA52 BB63 |
| I-364 | 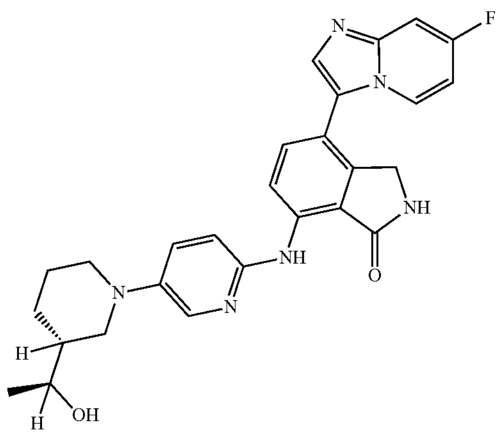 [SMILES: C[C@H](O)[C@@H]1CCCN(c2ccc(Nc3ccc(-c4cnc5cc(F)ccn45)c4c3C(=O)NC4)nc2)C1] | 4-(7-fluoro-imidazo[1,2-a]pyridin-3-yl)-7-((5-((R)-3-((S)-1-hydroxy-ethyl)piperidin-1-yl)pyridin-2-yl)amino)isoindolin-1-one | LCMS Method J m/z = 487.5 [M + H]+, Ret. time = 2.60 min Chiral HPLC method X4: Ret. time = 9.52 | 1H NMR (400 MHz, DMSO-d6) δ 9.83 (s, 1H), 8.79 (s, 1H), 8.55 (d, J = 8.5 Hz, 1H), 8.47-8.34 (m, 1H), 7.98 (d, J = 3.0 Hz, 1H), 7.81 (s, 1H), 7.68 (d, J = 8.6 Hz, 1H), 7.53 (dd, J = 10.0, 2.6 Hz, 1H), 7.41 (dd, J = 9.0, 3.0 Hz, 1H), 6.97 (td, J = 8.9, 8.1, 3.3 Hz, 2H), 4.54 (s, 1H), 4.37 (s, 2H), 3.74 (d, J = 11.7 Hz, 1H), 3.54 (d, J = 11.9 Hz, 2H), 2.38 (d, J = 11.2 Hz, 2H), 1.72 (s, 2H), 1.52 (d, J = 13.7 Hz, 3H), 1.10 (d, J = 6.1 Hz, 4H). | T AA52 BB63 |

TABLE 8-continued
Characterization Data (LCMS and ¹H NMR).
| # | STRUCTURE | NAME | LCMS | ¹H NMR | Method Reagent AA BB |
|---|---|---|---|---|---|
| I-365 | 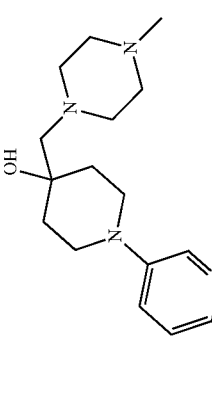 | 4-(7-fluoro-imidazo[1,2-a]pyridin-3-yl)-7-((5-(4-hydroxy-4-((4-methylpiperazin-1-yl)methyl)piperidin-1-yl)pyridin-2-yl)amino)isoindolin-1-one | LCMS Method J m/z = 571.3 [M + H]+, Ret. time = 2.70 min | 1H NMR (400 MHz, DMSO-d6) δ 9.81 (s, 1H), 8.77 (s, 1H), 8.54 (d, J = 8.5 Hz, 1H), 8.41 (t, J = 6.7 Hz, 1H), 8.00 (d, J = 2.9 Hz, 1H), 7.81 (s, 1H), 7.68 (d, J = 8.5 Hz, 1H), 7.43 (dd, J = 9.0, 3.1 Hz, 1H), 7.00-6.90 (m, 2H), 4.37 (s, 3H), 4.12 (s, 2H), 3.27 (d, J = 12.6 Hz, 6H), 3.02 (t, J = 11.0 Hz, 3H), 2.27 (s, 10H), 2.13 (s, 4H), 1.67 (t, J = 11.0 Hz, 3H), 1.55 (d, J = 13.0 Hz, 3H). | F AA55 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-366 | 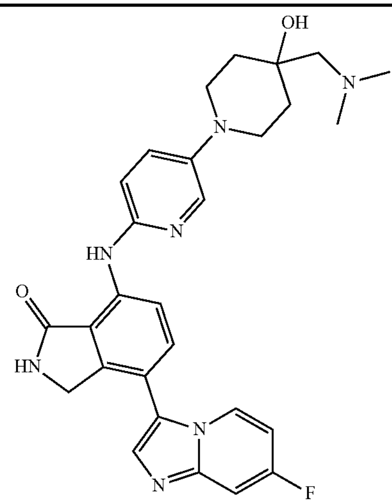 | 7-((5-(4-((dimethylamino)methyl)-4-hydroxypiperidin-1-yl)pyridin-2-yl)amino)-4-(7-fluoroimidazo[1,2-a]pyridin-3-yl)isoindolin-1-one | LCMS Method J m/z = 516.2 [M + H]+, Ret. time = 2.55 min | 1H NMR (400 MHz, DMSO-d6) δ 9.82 (s, 1H), 8.77 (s, 1H), 8.54 (d, J = 8.6 Hz, 1H), 8.42 (t, J = 6.7 Hz, 1H), 8.00 (d, J = 3.0 Hz, 1H), 7.81 (s, 1H), 7.68 (d, J = 8.6 Hz, 1H), 7.48 (ddd, J = 36.7, 9.5, 2.8 Hz, 2H), 7.05-6.84 (m, 2H), 4.37 (s, 2H), 3.27 (d, J = 12.0 Hz, 4H), 3.10-2.98 (m, 2H), 2.27 (s, 6H), 1.76-1.47 (m, 4H). | F AA56 BB63 |
| I-367 | 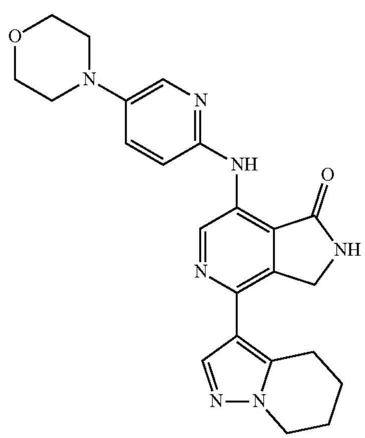 [SMILES: O=C1NCc2c(-c3cnn4c3CCCC4)ncc(Nc3ccc(N4CCOCC4)cn3)c21] | 7-((5-morpholinopyridin-2-yl)amino)-2-(4,5,6,7-tetrahydropyrazolo[1,5-a]pyridin-3-yl)-2,3-dihydro-1H-pyrrolo[3,4-c]pyridin-1-one | LCMS Method C m/z = 432.4 [M + H]+, Ret. time = 1.41 min | 1H NMR (400 MHz, DMSO-d6) δ 9.72 (s, 1H), 9.24 (s, 1H), 9.12 (s, 1H), 8.00 (d, J = 3.1 Hz, 1H), 7.78 (s, 1H), 7.44 (dd, J = 9.0, 3.0 Hz, 1H), 7.06 (s, 1H), 6.99 (d, J = 9.0 Hz, 1H), 4.61 (s, 2H), 4.12 (t, J = 6.1 Hz, 2H), 3.75 (t, J = 4.7 Hz, 4H), 3.18-3.00 (m, 6H), 1.99 (s, 2H), 1.83 (d, J = 6.3 Hz, 2H), 1.55 (s, 1H), 1.23 (s, 3H), 0.85 (s, 1H). | R AA3 BB46 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-368 | (structure) | 7-((5-(4-hydroxypiperidin-1-yl)pyridin-2-yl)amino)-4-(pyrazolo[1,5-a]pyridin-7-yl)-2,3-dihydro-1H-pyrrolo[3,4-c]pyridin-1-one | LCMS Method J m/z = 442.3 [M + H]+, Ret. time = 2.79 min | 1H NMR (400 MHz, DMSO-d6) δ 9.83 (s, 1H), 9.45 (s, 1H), 9.02 (s, 1H), 8.04 (s, 2H), 7.82 (d, J = 8.8 Hz, 1H), 7.50-7.42 (m, 1H), 7.39-7.31 (m, 1H), 7.08 (dd, J = 27.2, 7.9 Hz, 2H), 6.77 (d, J = 2.4 Hz, 1H), 4.71 (d, J = 4.1 Hz, 1H), 4.39 (s, 2H), 3.48 (d, J = 12.1 Hz, 2H), 2.83 (t, J = 10.4 Hz, 2H), 1.83 (s, 2H), 1.51 (d, J = 10.8 Hz, 2H). | R AA12 BB66 |
| I-369 | (structure) | 7-((5-(4-hydroxypiperidin-1-yl)pyridin-2-yl)amino)-4-(pyrrolo[1,2-a]pyrazin-6-yl)isoindolin-1-one | LCMS Method C m/z = 441.4 [M + H]+, Ret. time = 1.23 min | 1H NMR (400 MHz, DMSO-d6) δ 9.84 (s, 1H), 8.88 (s, 1H), 8.76 (s, 1H), 8.54 (d, J = 8.6 Hz, 1H), 8.10 (d, J = 5.0 Hz, 1H), 7.99 (d, J = 3.0 Hz, 1H), 7.69 (d, J = 8.6 Hz, 1H), 7.53-7.38 (m, 2H), 7.17 (d, J = 4.2 Hz, 1H), 6.96 (dd, J = 20.9, 6.6 Hz, 2H), 4.70 (d, J = 4.1 Hz, 1H), 4.36 (s, 2H), 3.45 (d, J = 12.3 Hz, 2H), 2.81 (t, J = 11.2 Hz, 2H), 1.84 (d, J = 12.3 Hz, 2H), 1.55-1.43 (m, 2H). | F AA12 BB67 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-370 | (structure) | 7-((5-(4-hydroxypiperidin-1-yl)pyridin-2-yl)amino)-4-(pyrazolo[1,5-a]pyridin-4-yl)-2,3-dihydro-1H-pyrrolo[3,4-c]pyridin-1-one | LCMS Method J m/z = 442.2 [M + H]+, Ret. time = 3.08 min | 1H NMR (400 MHz, DMSO-d6) δ 9.88 (s, 1H), 9.47 (s, 1H), 9.15 (s, 1H), 8.72 (d, J = 6.9 Hz, 1H), 8.04 (t, J = 3.3 Hz, 2H), 7.55-7.39 (m, 2H), 7.08-6.89 (m, 3H), 4.76-4.55 (m, 3H), 3.62 (dt, J = 9.0, 4.5 Hz, 1H), 3.47 (d, J = 11.6 Hz, 2H), 2.90-2.76 (m, 2H), 2.45 (s, 2H), 1.84 (d, J = 12.3 Hz, 2H), 1.51 (td, J = 9.6, 5.9 Hz, 2H). | R AA12 BB68 |
| I-371 | (structure) | 4-(7-fluoroimidazo[1,2-a]pyridin-3-yl)-7-((5-(4-hydroxytetrahydro-2H-pyran-4-yl)pyridin-2-yl)amino)isoindolin-1-one | LCMS Method C m/z = 460.3 [M + H]+, Ret. time = 1.26 min | 1H NMR (400 MHz, DMSO-d6) δ 10.08 (s, 1H), 8.93-8.57 (m, 2H), 8.43 (d, J = 14.6 Hz, 2H), 7.98-7.65 (m, 3H), 7.55 (d, J = 9.7 Hz, 1H), 6.99 (d, J = 8.3 Hz, 2H), 5.14 (s, 1H), 4.40 (s, 2H), 3.78 (dd, J = 25.6, 14.5 Hz, 4H), 2.00 (d, J = 16.0 Hz, 2H), 1.60 (d, J = 13.5 Hz, 2H). | F AA57 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-372 | 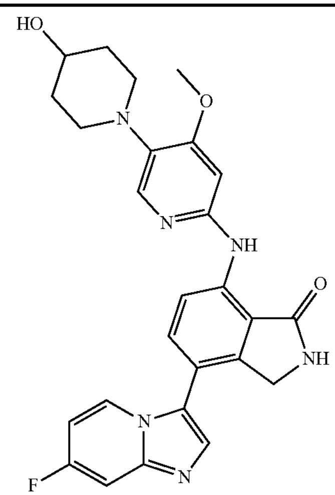 | 4-(7-fluoroimidazo[1,2-a]pyridin-3-yl)-7-((5-(4-hydroxypiperidin-1-yl)-4-methoxypyridin-2-yl)amino)isoindolin-1-one | LCMS Method C m/z = 489.5 [M + H]+, Ret. time = 1.20 min | 1H NMR (400 MHz, DMSO-d6) δ 9.87 (s, 1H), 8.83-8.65 (m, 2H), 8.42 (t, J = 6.6 Hz, 1H), 7.85-7.61 (m, 3H), 7.52 (dd, J = 10.0, 2.7 Hz, 1H), 6.97 (dt, J = 8.5, 4.2 Hz, 1H), 6.55 (s, 1H), 4.66 (s, 1H), 4.38 (s, 2H), 3.89 (s, 3H), 3.58 (s, 2H), 3.18 (d, J = 11.6 Hz, 3H), 2.69 (d, J = 10.7 Hz, 7H), 1.81 (s, 2H), 1.52 (d, J = 10.5 Hz, 2H). | F AA58 BB63 |
| I-373 | 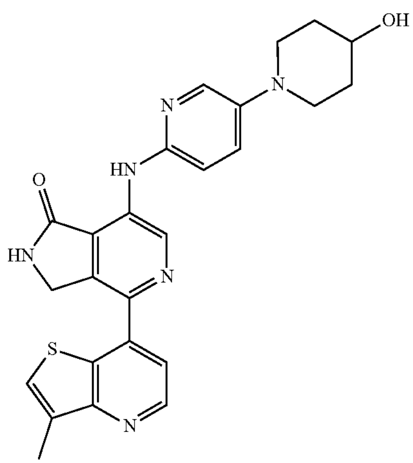 [SMILES: Cc1csc2c(-c3ncc(Nc4ccc(N5CCC(O)CC5)cn4)c4c3CNC4=O)ccnc12] | 7-((5-(4-hydroxypiperidin-1-yl)pyridin-2-yl)amino)-4-(3-methylthieno[3,2-b]pyridin-7-yl)-2,3-dihydro-1H-pyrrolo[3,4-c]pyridin-1-one | LCMS Method C m/z = 473.4 [M + H]+, Ret. time = 1.35 min | 1H NMR (400 MHz, DMSO-d6) δ 10.00 (s, 1H), 9.67 (s, 1H), 9.33 (s, 1H), 8.77 (s, 1H), 8.46 (s, 1H), 8.10 (s, 1H), 7.80 (s, 1H), 7.66-7.48 (d, J = 8.9 Hz, 2H), 7.05 (s, 1H), 3.64 (s, 1H), 3.50 (m, 2H), 2.84 (t, J = 10.2 Hz, 2H), 2.44 (s, 3H), 1.83 (m, 2H), 1.52 (m, 2H). | R AA12 BB64 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-374 | 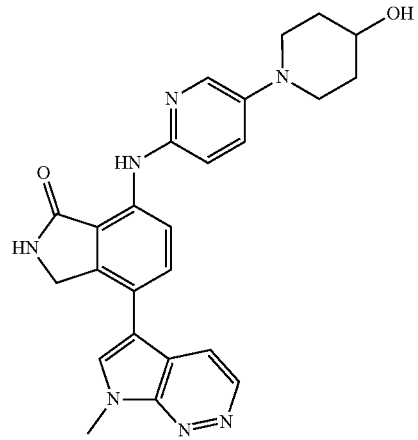 [SMILES: Cn1cc(-c2ccc(Nc3ccc(N4CCC(O)CC4)cn3)c3c2CNC3=O)c2ccnnc21] | 7-((5-(4-hydroxypiperidin-1-yl)pyridin-2-yl)amino)-4-(7-methyl-7H-pyrrolo[2,3-c]pyridazin-5-yl)isoindolin-1-one | LCMS Method C m/z = 456.5 [M + H]+, Ret. time = 1.20 min | 1H NMR (400 MHz, DMSO-d6) δ 9.76 (s, 1H), 8.77 (s, 1H), 8.50 (d, J = 6.0 Hz, 2H), 8.37 (d, J = 8.0 Hz, 2H), 7.97 (s, 1H), 7.75 (d, J = 8.4 Hz, 1H), 7.41 (d, J = 8.7 Hz, 1H), 6.89 (d, J = 9.3 Hz, 1H), 4.70 (s, 1H), 4.55 (s, 4H), 3.61 (s, 1H), 3.42 (s, 4H), 2.79 (t, J = 11.3 Hz, 3H), 2.46 (s, 4H), 1.84 (d, J = 12.9 Hz, 2H), 1.51 (d, J = 11.6 Hz, 2H). | F AA12 BB69 |
| I-375 | 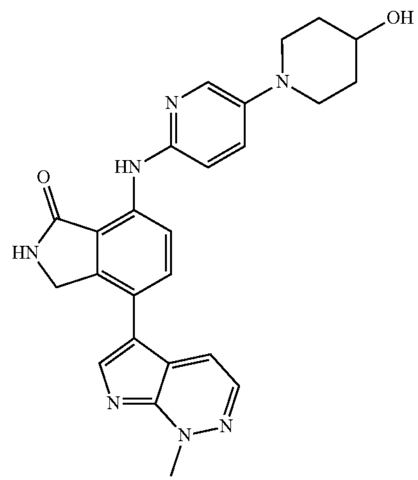 [SMILES: Cn1nccc2c(-c3ccc(Nc4ccc(N5CCC(O)CC5)cn4)c4c3CNC4=O)cnc1-2] | 7-((5-(4-hydroxypiperidin-1-yl)pyridin-2-yl)amino)-4-(1-methyl-1H-pyrrolo[2,3-c]pyridazin-5-yl)isoindolin-1-one | LCMS Method C m/z = 456.4 [M + H]+, Ret. time = 1.23 min | 1H NMR (400 MHz, DMSO-d6) δ 9.78 (d, J = 7.6 Hz, 1H), 8.96 (s, 1H), 8.51 (s, 1H), 8.29-8.02 (m, 1H), 8.02-7.61 (m, 1H), 7.42 (s, 1H), 6.91 (d, J = 9.1 Hz, 1H), 4.70 (s, 1H), 4.60-4.45 (m, 2H), 4.05 (d, J = 7.8 Hz, 3H), 3.61 (s, 4H), 1.83 (s, 2H), 1.51 (s, 2H). | F AA12 BB70 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-376 | (structure) | 7-((5-(4-hydroxypiperidin-1-yl)pyridin-2-yl)amino)-4-(imidazo[1,2-a]pyrazin-5-yl)-2,3-dihydro-1H-pyrrolo[3,4-c]pyridin-1-one | LCMS Method C m/z = 443.2 [M + H]+, Ret. time = 1.24 min | ¹H NMR (400 MHz, DMSO): δ 9.94 (s, 1 H), 9.76-9.75 (m, 1 H), 9.44 (s, 1 H), 9.30 (s, 1 H), 9.21 (s, 1 H), 8.29 (s, 1 H), 8.07-8.05 (m, 2 H), 7.48-7.45 (m, 1 H), 7.04-7.02 (d, J = 8 Hz, 1 H), 4.80 (s, 2 H), 4.72-4.70 (m, 1 H), 3.63 (s, 1 H), 3.46-3.38 (m, 2 H), 2.86-2.81 (t, J = 8 Hz, 2 H), 1.84 (s, 2 H), 1.53-1.51 (m, 2 H) | S AA12 BB40 |
| I-377 | (structure) | 4-(7-fluoroimidazo[1,2-a]pyridin-3-yl)-7-((5-((oxetan-3-ylmethyl)sulfonyl)pyridin-2-yl)amino)isoindolin-1-one | LCMS Method C m/z = 494.4 [M + H]+, Ret. time = 1.28 min | 1H NMR (400 MHz, DMSO-d6) δ 10.62 (s, 1H), 9.01 (s, 1H), 8.75 (d, J = 8.5 Hz, 1H), 8.68 (d, J = 2.5 Hz, 1H), 8.53-8.45 (m, 1H), 8.04 (dd, J = 8.9, 2.5 Hz, 1H), 7.91-7.81 (m, 2H), 7.56 (dd, J = 9.9, 2.8 Hz, 1H), 7.22 (d, J = 8.9 Hz, 1H), 7.05-6.96 (m, 1H), 4.58 (dd, J = 8.1, 6.0 Hz, 2H), 4.36 (t, J = 6.4 Hz, 2H), 3.80 (d, J = 7.3 Hz, 2H), 2.61 (s, 1H). | F AA59 BB63 |

TABLE 8-continued

Characterization Data (LCMS and ¹H NMR).

| # | STRUCTURE | NAME | LCMS | ¹H NMR | Method AA Reagent BB |
|---|---|---|---|---|---|
| I-378 | 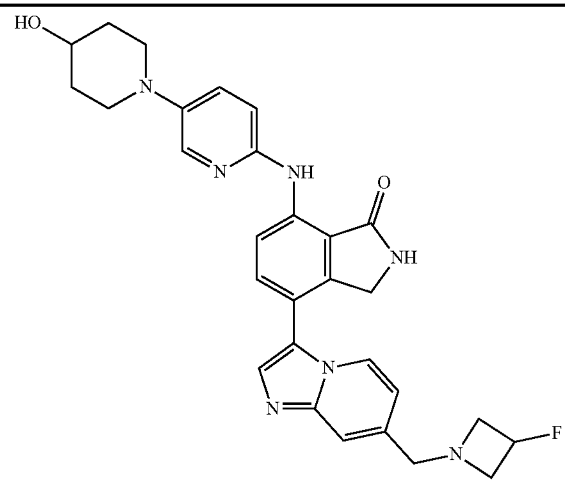 | 4-(7-fluoroazetidin-1-yl)methyl)imidazo[1,2-a]pyridin-3-yl)-7-((5-(4-hydroxypiperidin-1-yl)pyridin-2-yl)amino)isoindolin-1-one | LCMS Method C m/z = 528.6 [M + H]+, Ret. time = 1.18 min | 1H NMR (400 MHz, DMSO-d6) δ 9.82 (s, 1H), 8.75 (s, 1H), 8.54 (d, J = 8.6 Hz, 1H), 8.31 (d, J = 8.0 Hz, 1H), 8.00 (s, 1H), 7.78 (s, 1H), 7.67 (d, J = 8.7 Hz, 1H), 7.50 (s, 1H), 7.43 (d, J = 8.9 Hz, 1H), 6.94 (d, J = 9.0 Hz, 1H), 6.85 (d, J = 7.2 Hz, 1H), 4.70 (s, 1H), 4.38 (s, 2H), 3.69 (s, 2H), 3.60 (dt, J = 14.6, 7.2 Hz, 3H), 3.44 (d, J = 10.7 Hz, 3H), 3.26-3.15 (m, 2H), 2.83 (d, J = 11.3 Hz, 2H), 1.84 (s, 2H), 1.52 (s, 2H). | F AA12 BB71 |
| I-379 | 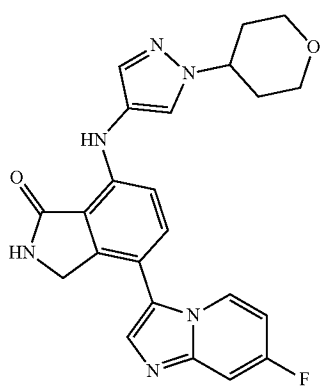 [SMILES: O=C1NCc2c(-c3cnc4cc(F)ccn34)ccc(Nc3cnn(C4CCOCC4)c3)c21] | 4-(7-fluoroimidazo[1,2-a]pyridin-3-yl)-7-((1-(tetrahydro-2H-pyran-4-yl)-1H-pyrazol-4-yl)amino)isoindolin-1-one | LCMS Method J m/z = 453.7 [M + H]+, Ret. time = 2.651 min | 1H NMR (400 MHz, DMSO-d6) δ 8.60 (s, 1H), 8.50 (s, 1H), 8.33 (t, J = 6.7 Hz, 1H), 8.00 (s, 1H), 7.76 (s, 1H), 7.59-7.47 (m, 3H), 6.96 (d, J = 8.2 Hz, 2H), 4.39 (s, 2H), 4.33 (s, 2H), 3.98 (d, J = 11.5 Hz, 2H), 3.48 (s, 2H), 2.04-1.93 (m, 4H). | F AA60 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-380 | 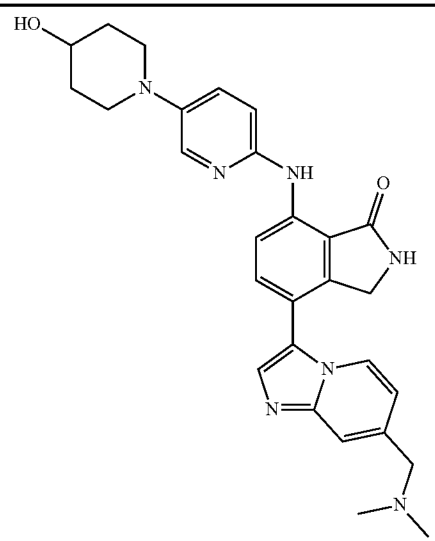 | 4-(7-((dimethyl-amino)methyl)imi-dazo[1,2-a]pyridin-3-yl)-7-((5-(4-hydroxy-piperidin-1-yl)pyridin-2-yl)amino)isoindolin-1-one | LCMS Method J m/z = 498.2 [M + H]+, Ret. time = 2.521 min | 1H NMR (400 MHz, DMSO-d6) δ 9.83 (s, 1H), 8.77 (s, 1H), 8.55 (d, J = 8.6 Hz, 1H), 8.34 (d, J = 7.1 Hz, 1H), 8.00 (d, J = 3.0 Hz, 1H), 7.79 (s, 1H), 7.69 (d, J = 8.6 Hz, 1H), 7.51 (s, 1H), 7.44 (dd, J = 9.0, 3.0 Hz, 1H), 6.98-6.88 (m, 2H), 4.70 (d, J = 4.2 Hz, 1H), 4.39 (s, 2H), 3.66-3.59 (m, 1H), 3.52-3.41 (m, 5H), 2.82 (s, 1H), 2.82 (dd, J = 22.5, 2.9 Hz, 1H), 2.56 (s, 1H), 2.23 (s, 6H), 1.89-1.80 (m, 2H), 1.53 (dd, J = 13.3, 9.4 Hz, 2H). | F AA12 BB72 |
| I-381 | 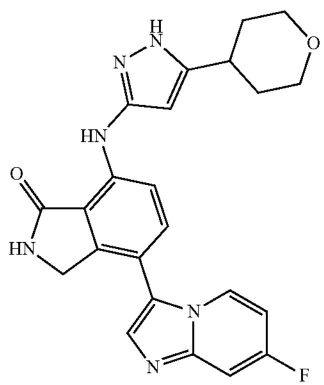 [SMILES: O=C1NCc2c(-c3cnc4cc(F)ccn34)ccc(Nc3cc(C4CCOCC4)[nH]n3)c21] | 4-(7-fluoroimidazo[1,2-a]pyridin-3-yl)-7-((5-(tetrahydro-2H-pyran-4-yl)-1H-pyrazol-3-yl)amino)isoindolin-1-one | LCMS Method J m/z = 433.2 [M + H]+, Ret. time = 3.043 min | 1H NMR (400 MHz, DMSO-d6) δ 12.09 (s, 1H), 9.33 (s, 1H), 8.68 (s, 1H), 8.39 (t, J = 6.7 Hz, 1H), 7.96 (d, J = 8.4 Hz, 1H), 7.78 (s, 1H), 7.64 (d, J = 8.5 Hz, 1H), 7.51 (dd, J = 10.1, 2.6 Hz, 1H), 6.96 (td, J = 7.5, 2.7 Hz, 1H), 5.93 (s, 1H), 4.35 (s, 2H), 3.92 (dd, J = 11.6, 3.6 Hz, 2H), 3.49-3.38 (m, 2H), 2.89 (tt, J = 11.7, 4.0 Hz, 1H), 2.46 (s, 1H), 1.85 (dd, J = 14.1, 3.7 Hz, 2H), 1.67 (qd, J = 12.2, 4.4 Hz, 2H). | F AA61 BB63 |

TABLE 8-continued
Characterization Data (LCMS and ¹H NMR).
| # | STRUCTURE | NAME | LCMS | ¹H NMR | Method Reagent AA BB |
|---|---|---|---|---|---|
| I-382 | 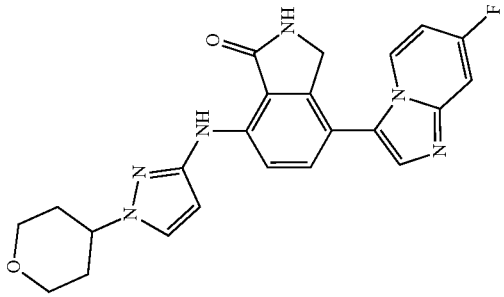 | 4-(7-fluoroimidazo[1,2-a]pyridin-3-yl)-7-((1-(tetrahydro-2H-pyran-4-yl)-1H-pyrazol-3-yl)amino)isoindolin-1-one | LCMS Method J m/z = 433.6 [M + H]+, Ret. time = 2.673 min | 1H NMR (400 MHz, DMSO-d6) δ 8.90 (s, 1H), 8.76 (s, 1H), 8.36 (t, J = 6.7 Hz, 1H), 7.80 (s, 1H), 7.60 (d, J = 8.4 Hz, 1H), 7.53 (d, J = 12.4 Hz, 2H), 6.97 (dd, J = 8.8, 6.1 Hz, 1H), 6.80 (d, J = 8.4 Hz, 1H), 6.26 (s, 1H), 4.39 (s, 3H), 4.02-3.93 (m, 2H), 3.44 (t, J = 11.9 Hz, 3H), 2.05 (s, 2H), 1.88-1.79 (m, 2H). | F AA62 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-383 | 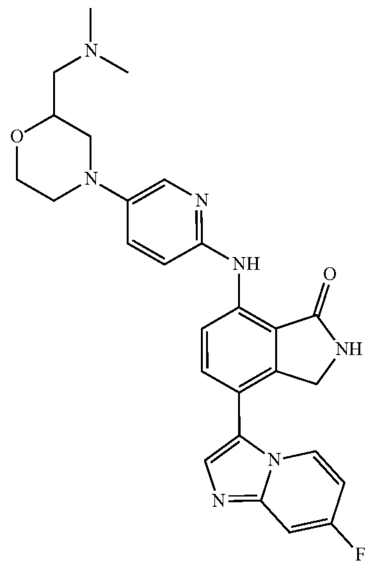 [SMILES: CN(C)CC1CN(c2ccc(Nc3ccc(-c4cnc5cc(F)ccn45)c4c3C(=O)NC4)nc2)CCO1] | 7-((5-(2-((dimethylamino)methyl)morpholino)pyridin-2-yl)amino)-4-(7-fluoroimidazo[1,2-a]pyridin-3-yl)isoindolin-1-one | LCMS Method J m/z = 502.7 [M + H]+, Ret. time = 2.39 min | 1H NMR (400 MHz, DMSO-d6) δ 9.87 (s, 1H), 8.78 (s, 1H), 8.56 (d, J = 8.5 Hz, 1H), 8.42 (t, J = 6.7 Hz, 1H), 7.99 (d, J = 3.0 Hz, 1H), 7.81 (s, 1H), 7.69 (d, J = 8.6 Hz, 1H), 7.48 (ddd, J = 30.1, 9.6, 2.9 Hz, 2H), 6.97 (dd, J = 9.6, 7.1 Hz, 2H), 4.38 (s, 2H), 3.93 (d, J = 11.4 Hz, 1H), 3.74-3.61 (m, 2H), 3.46 (dt, J = 28.5, 14.3 Hz, 2H), 2.74-2.62 (m, 1H), 2.41 (dd, J = 23.8, 13.1 Hz, 2H), 2.37 (s, 2H), 2.20 (s, 6H), 1.23 (s, 1H). | F AA63 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-384 | (structure shown) | 7-((5-(4-hydroxypiperidin-1-yl)pyridin-2-yl)amino)-4-(imidazo[1,2-a]pyridin-8-yl)-2,3-dihydro-1H-pyrrolo[3,4-c]pyridin-1-one | LCMS Method C m/z = 442.4 [M + H]+, Ret. time = 1.256 min | 1H NMR (400 MHz, DMSO-d6) δ 9.82 (s, 1H), 9.42 (s, 1H), 9.00 (s, 1H), 8.68 (d, J = 6.7 Hz, 1H), 8.09 (s, 1H), 8.04 (s, 1H), 7.65 (s, 1H), 7.53 (d, J = 7.0 Hz, 1H), 7.45 (d, J = 9.0 Hz, 1H), 7.10-6.99 (m, 2H), 4.65 (s, 2H), 3.62 (s, 1H), 3.47 (d, J = 12.0 Hz, 2H), 2.83 (s, 1H), 1.84 (t, J = 8.2 Hz, 2H), 1.51 (d, J = 11.0 Hz, 2H). | S AA12 BB72 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-385 | 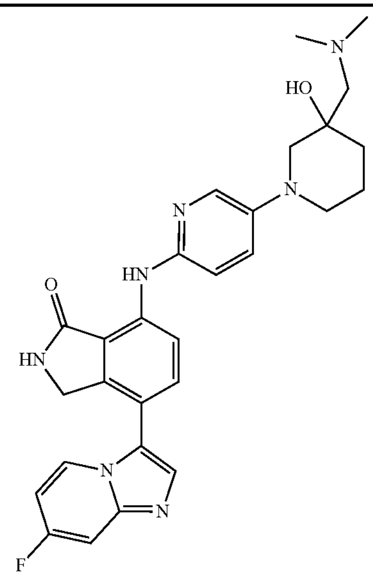 | 7-((5-(3-((dimethyl-amino)methyl)-3-hydroxypiperidin-1-yl)pyridin-2-yl)amino)-4-(7-fluoro-imidazo[1,2-a]pyridin-3-yl)isoindolin-1-one | LCMS Method J m/z = 516.2 [M + H]+, Ret. time = 2.72 min | 1H NMR (400 MHz, DMSO-d6) δ 9.84 (s, 1H), 8.79 (s, 1H), 8.55 (d, J = 8.5 Hz, 1H), 8.45 (s, 1H), 7.97 (d, J = 2.9 Hz, 1H), 7.68 (d, J = 8.6 Hz, 1H), 7.53 (s, 1H), 7.40 (dd, J = 8.9, 2.9 Hz, 1H), 7.02-6.92 (m, 2H), 3.08 (d, J = 10.8 Hz, 2H), 2.93 (t, J = 9.2 Hz, 1H), 2.79 (d, J = 11.5 Hz, 1H), 2.55 (d, J = 4.8 Hz, 1H), 2.44 (d, J = 13.6 Hz, 1H), 2.33 (s, 6H), 1.75 (dd, J = 28.2, 11.4 Hz, 2H), 1.56 (s, 1H), 1.42 (t, J = 9.9 Hz, 1H). | F AA64 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-386 | 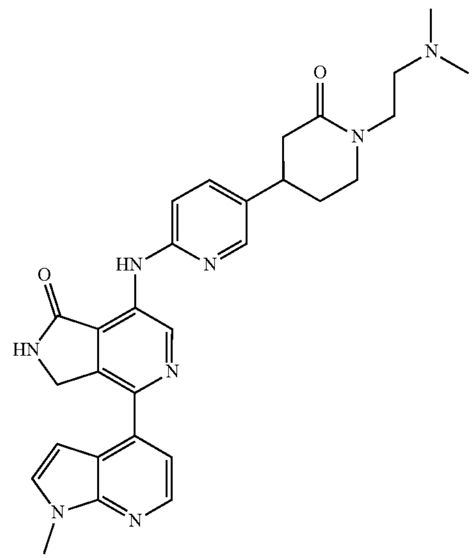 [SMILES: CN(C)CCN1CCC(c2ccc(Nc3cnc(-c4ccnc5c4ccn5C)c4c3C(=O)NC4)nc2)CC1=O] | 7-((5-(1-(2-(dimethylamino)ethyl)-2-oxopiperidin-4-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method C m/z = 525.9 [M + H]+, Ret. time = 1.301 min | 1H NMR (400 MHz, DMSO-d6) δ 10.03 (d, J = 6.3 Hz, 1H), 9.71 (d, J = 6.0 Hz, 1H), 9.22 (s, 1H), 8.32 (dd, J = 24.4, 3.7 Hz, 2H), 7.70 (dd, J = 8.5, 2.5 Hz, 1H), 7.57 (d, J = 3.5 Hz, 1H), 7.38 (t, J = 5.5 Hz, 1H), 7.09 (d, J = 8.5 Hz, 1H), 6.91 (d, J = 3.5 Hz, 1H), 4.73 (s, 2H), 3.87 (s, 3H), 3.41 (dq, J = 19.5, 7.1 Hz, 8H), 3.13-3.03 (m, 1H), 2.42 (q, J = 8.6, 6.7 Hz, 4H), 2.20 (s, 6H), 2.00 (s, 2H). | R AA65 BB14 |

TABLE 8-continued
Characterization Data (LCMS and ¹H NMR).
| # | STRUCTURE | NAME | LCMS | ¹H NMR | Method Reagent AA BB |
|---|---|---|---|---|---|
| I-387 | 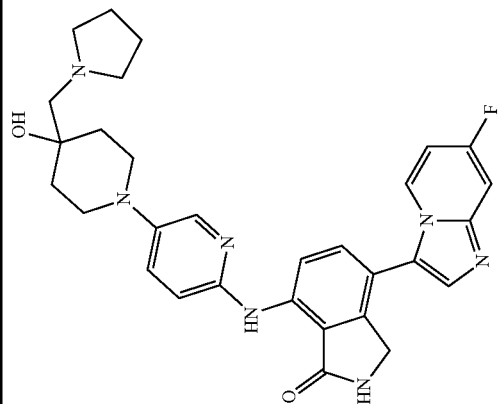 | 4-(7-fluoro imidazo[1,2-a]pyridin-3-yl)-7-((5-(4-hydroxy-4-(pyrrolidin-1-ylmethyl)piperidin-1-yl)pyridin-2-yl)amino)isoindolin-1-one | LCMS Method J m/z = 542.2 [M + H]+, Ret. time = 2.635 min | 1H NMR (400 MHz, DMSO-d6) δ 9.81 (s, 1H), 8.76 (s, 1H), 8.54 (d, J = 8.5 Hz, 1H), 8.41 (t, J = 6.7 Hz, 1H), 8.22 (s, 1H), 8.01 (d, J = 2.9 Hz, 1H), 7.80 (s, 1H), 7.68 (d, J = 8.5 Hz, 1H), 7.48 (ddd, J = 28.9, 9.5, 2.8 Hz, 2H), 6.97 (dt, J = 13.5, 5.7 Hz, 2H), 4.37 (s, 2H), 3.53 (s, 3H), 3.48 (s, 6H), 3.35-3.25 (m, 2H), 3.10-2.98 (m, 2H), 2.70 (s, 3H), 2.70 (d, J = 12.0 Hz, 1H), 2.57 (s, 2H), 1.74-1.62 (m, 6H), 1.60 (d, J = 13.0 Hz, 2H). | F AA66 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-388 | 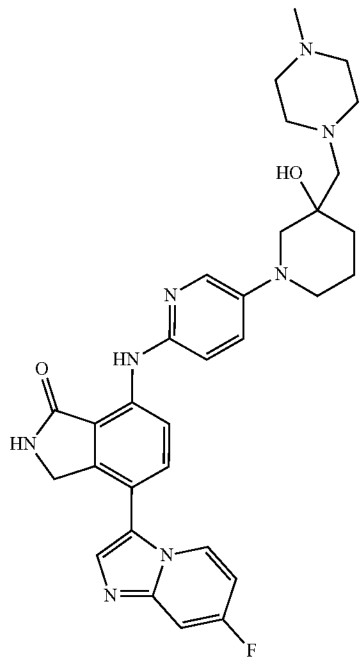 [SMILES: CN1CCN(CC2(O)CCCN(c3ccc(Nc4ccc(-c5cnc6cc(F)ccn56)c5c4C(=O)NC5)nc3)C2)CC1] | 4-(7-fluoro-imidazo[1,2-a]pyridin-3-yl)-7-((5-(3-hydroxy-3-((4-methylpiperazin-1-yl)methyl)piperidin-1-yl)pyridin-2-yl)amino)iso-indolin-1-one | LCMS Method J m/z = 571.5 [M + H]+, Ret. time = 2.772 min | 1H NMR (400 MHz, DMSO-d6) δ 9.83 (s, 1H), 8.77 (s, 1H), 8.53 (d, J = 8.6 Hz, 1H), 8.48-8.34 (m, 1H), 7.95 (d, J = 3.0 Hz, 1H), 7.80 (s, 1H), 7.68 (d, J = 8.6 Hz, 1H), 7.52 (dd, J = 10.1, 2.7 Hz, 1H), 7.41 (dd, J = 9.0, 3.1 Hz, 1H), 6.96 (td, J = 8.9, 8.2, 3.4 Hz, 2H), 4.36 (d, J = 10.2 Hz, 3H), 3.11 (dd, J = 18.2, 9.0 Hz, 2H), 3.01-2.83 (m, 1H), 2.74 (d, J = 11.5 Hz, 1H), 2.35 (d, J = 34.8 Hz, 6H), 2.14 (s, 4H), 1.72 (d, J = 28.7 Hz, 2H), 1.52 (s, 1H), 1.39 (s, 1H). | F AA67 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-389 | 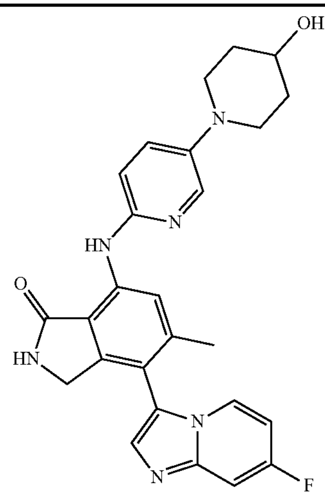 | 4-(7-fluoro-imidazo[1,2-a]pyridin-3-yl)-7-((5-(4-hydroxypiperidin-1-yl)pyridin-2-yl)amino)-5-methylisoindolin-1-one | LCMS Method J m/z = 473.2 [M + H]+, Ret. time = 2.81 min | 1H NMR (400 MHz, DMSO-d6) δ 9.66 (s, 1H), 8.56 (s, 1H), 8.39 (s, 1H), 8.08-7.86 (m, 2H), 7.70 (s, 1H), 7.48 (ddd, J = 38.1, 9.5, 2.9 Hz, 2H), 7.06-6.85 (m, 2H), 4.70 (d, J = 4.2 Hz, 1H), 4.26 (d, J = 18.1 Hz, 1H), 3.89 (d, J = 18.1 Hz, 1H), 3.63 (dt, J = 10.3, 5.2 Hz, 1H), 3.46 (d, J = 8.7 Hz, 2H), 2.89-2.71 (m, 2H), 2.07 (s, 3H), 1.96-1.74 (m, 2H), 1.63-1.43 (m, 2H). | M AA12 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-390 | 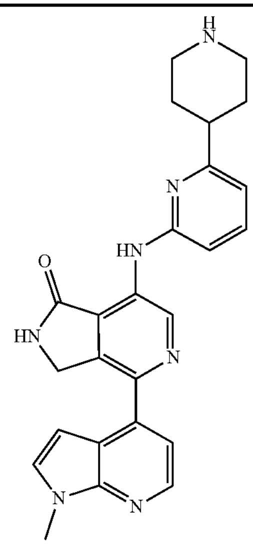 | 4-(1-methyl-1H-pyrrolo[2,3-b]pyridin-4-yl)-7-((6-(piperidin-4-yl)pyridin-2-yl)amino)-2,3-dihydro-1H-pyrrolo[3,4-c]pyridin-1-one | LCMS Method J m/z = 440.2 [M + H]+, Ret. time = 4.735 min | 1H NMR (400 MHz, DMSO-d6) δ 10.07 (s, 1H), 9.77 (s, 1H), 9.23 (s, 1H), 8.43-8.34 (m, 2H), 7.69 (t, J = 7.8 Hz, 1H), 7.59 (d, J = 3.4 Hz, 1H), 7.39 (d, J = 5.0 Hz, 1H), 6.97-6.85 (m, 3H), 4.70 (s, 2H), 3.88 (s, 3H), 3.27 (d, J = 12.2 Hz, 2H), 2.90 (dt, J = 23.3, 12.6 Hz, 3H), 2.02-1.84 (m, 4H). | R AA68 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-391 | (structure) | 7-((5-(4-hydroxy-4-methylpiperidin-1-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 440.2 [M + H]+, Ret. time = 3.194 min | 1H NMR (400 MHz, DMSO-d6) δ 9.47 (s, 1H), 9.14 (s, 1H), 8.33 (d, J = 5.0 Hz, 1H), 8.05 (d, J = 3.0 Hz, 1H), 7.55 (d, J = 3.4 Hz, 1H), 7.45 (dd, J = 9.0, 3.0 Hz, 1H), 7.36 (d, J = 5.0 Hz, 1H), 7.02 (d, J = 9.0 Hz, 1H), 4.70 (s, 2H), 4.35 (s, 1H), 3.86 (s, 4H), 3.29-3.20 (m, 4H), 3.16-3.04 (m, 3H), 1.60 (d, J = 6.3 Hz, 5H), 1.16 (s, 5H). | R AA27 BB14 |
| I-392 | (structure) | 4-(1-methyl-1H-pyrrolo[2,3-b]pyridin-4-yl)-7-((5-(1-methyl-2-oxopiperidin-4-yl)pyridin-2-yl)amino)-2,3-dihydro-1H-pyrrolo[3,4-c]pyridin-1-one | LCMS Method C m/z = 446.3 [M + H]+, Ret. time = 1.398 min | 1H NMR (400 MHz, DMSO-d6) δ 10.04 (s, 1H), 9.72 (s, 1H), 9.22 (s, 1H), 8.32 (d, J = 28.0 Hz, 2H), 7.74-7.52 (m, 2H), 7.39 (d, J = 5.3 Hz, 1H), 7.10 (d, J = 8.7 Hz, 1H), 6.91 (s, 1H), 4.73 (s, 2H), 3.88 (d, J = 5.6 Hz, 3H), 3.11 (s, 1H), 2.87 (d, J = 5.2 Hz, 3H), 2.01 (s, 3H). | R AA8 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-393 | 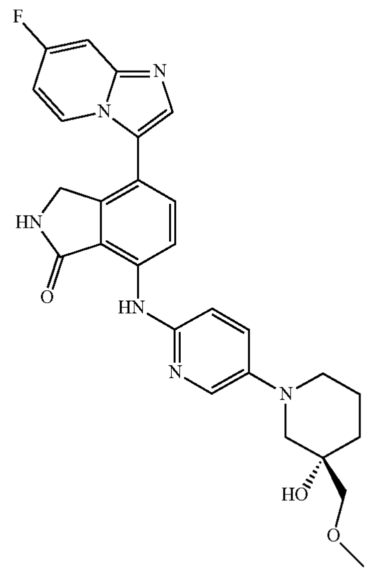 [SMILES: COC[C@]1(O)CCCN(c2ccc(Nc3ccc(-c4cnc5cc(F)ccn45)c4c3C(=O)NC4)nc2)C1] | (S)-4-(7-fluoroimidazo[1,2-a]pyridin-3-yl)-7-((5-(3-hydroxy-3-(methoxymethyl)piperidin-1-yl)pyridin-2-yl)amino)isoindolin-1-one | LCMS Method J m/z = 503.8 [M + H]+, Ret. time = 2.305 min Chiral HPLC method X5: Ret. time = 8.19 | 1H NMR (400 MHz, DMSO-d6) δ 9.84 (s, 1H), 8.79 (s, 1H), 8.55 (d, J = 8.6 Hz, 1H), 8.44 (dd, J = 7.6, 5.8 Hz, 1H), 7.96 (d, J = 2.9 Hz, 1H), 7.83 (s, 1H), 7.70 (d, J = 8.6 Hz, 1H), 7.54 (dd, J = 10.1, 2.7 Hz, 1H), 7.40 (dd, J = 9.0, 3.0 Hz, 1H), 7.03-6.93 (m, 1H), 4.59 (s, 1H), 4.39 (s, 1H), 3.36-3.28 (m, 1H), 3.31 (s, 2H), 3.16-2.89 (m, 3H), 1.89-1.79 (m, 1H), 1.66 (ddd, J = 12.0, 8.2, 4.1 Hz, 1H), 1.59 (s, 1H), 1.43 (dt, J = 10.7, 5.1 Hz, 1H). | J AA69 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-394 | 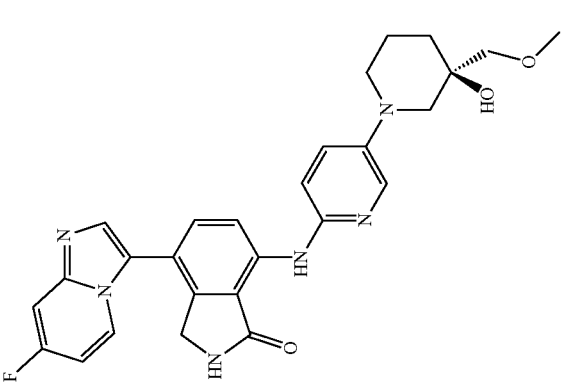 | (R)-4-(7-fluoroimidazo[1,2-a]pyridin-3-yl)-7-(5-(3-hydroxy-3-(methoxymethyl)piperidin-1-yl)pyridin-2-yl)amino)isoindolin-1-one | LCMS Method J m/z = 503.8 [M + H]+, Ret. time = 2.805 min Chiral HPLC method X5: Ret. time = 11.02 | 1H NMR (400 MHz, DMSO-d6) δ 9.83 (s, 1H), 8.77 (s, 1H), 8.54 (d, J = 8.6 Hz, 1H), 8.42 (t, J = 6.7 Hz, 1H), 7.95 (d, J = 3.0 Hz, 1H), 7.81 (s, 1H), 7.68 (d, J = 8.6 Hz, 1H), 7.53 (dd, J = 10.0, 2.7 Hz, 1H), 7.39 (dd, J = 8.9, 3.0 Hz, 1H), 6.97 (td, J = 9.5, 8.8, 6.5 Hz, 2H), 4.58 (s, 1H), 4.38 (s, 2H), 3.01 (ddd, J = 39.0, 24.1, 9.4 Hz, 5H), 2.46 (s, 2H), 1.88-1.80 (m, 1H), 1.71-1.60 (m, 2H), 1.57 (s, 1H), 1.47-1.36 (m, 1H). | J AA69 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-395 | 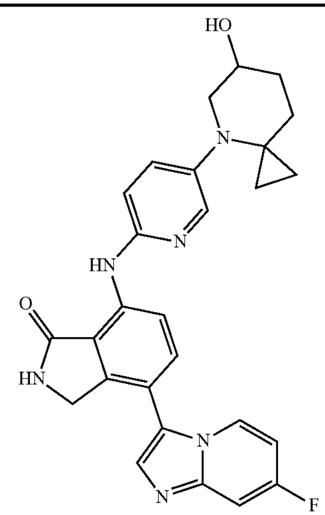 | 4-(7-(fluoroimidazo[1,2-a]pyridin-3-yl)-7-((5-(6-hydroxy-4-azaspiro[2.5]octan-4-yl)pyridin-2-yl)amino)isoindolin-1-one | LCMS Method C m/z = 485.8 [M + H]+, Ret. time = 1.385 min | 1H NMR (400 MHz, DMSO-d6) δ 9.69 (s, 1H), 8.73 (s, 1H), 8.50-8.36 (m, 2H), 7.88-7.77 (m, 2H), 7.65 (d, J = 8.5 Hz, 1H), 7.52 (dd, J = 10.1, 2.6 Hz, 1H), 7.24 (dd, J = 9.0, 3.1 Hz, 1H), 7.02-6.90 (m, 2H), 4.99 (d, J = 16.0 Hz, 2H), 4.88 (s, 1H), 4.36 (s, 2H), 4.17 (d, J = 15.8 Hz, 1H), 3.94 (d, J = 15.8 Hz, 1H), 3.72 (d, J = 15.1 Hz, 2H), 3.08 (dd, J = 14.8, 9.3 Hz, 1H), 2.58 (d, J = 19.8 Hz, 2H), 2.44 (d, J = 16.0 Hz, 8H), 1.87 (d, J = 13.5 Hz, 2H), 1.48 (q, J = 11.2 Hz, 1H). | F AA70 BB63 |
| I-396 | 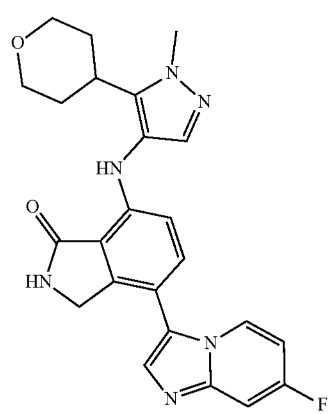 [SMILES: Cn1ncc(Nc2ccc(-c3cnc4cc(F)ccn34)c3c2C(=O)NC3)c1C1CCOCC1] | 4-(7-fluoroimidazo[1,2-a]pyridin-3-yl)-7-((1-methyl-5-(tetrahydro-2H-pyran-4-yl)-1H-pyrazol-4-yl)amino)isoindolin-1-one | LCMS Method J m/z = 447.2 [M + H]+, Ret. time = 2.982 min | 1H NMR (400 MHz, DMSO-d6) δ 8.57 (s, 1H), 8.33 (dd, J = 7.6, 5.7 Hz, 1H), 8.06 (s, 1H), 7.75 (s, 0H), 7.50 (td, J = 7.6, 6.9, 3.4 Hz, 1H), 7.41 (s, 0H), 6.95 (td, J = 7.5, 2.5 Hz, 1H), 6.53 (d, J = 8.4 Hz, 1H), 4.34 (s, 2H), 3.93-3.86 (m, 1H), 3.87 (s, 3H), 3.41 (t, J = 11.6 Hz, 2H), 3.17-3.06 (m, 1H), 1.91 (qd, J = 12.5, 4.2 Hz, 2H), 1.69 (d, J = 12.9 Hz, 2H). | F AA71 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-397 | 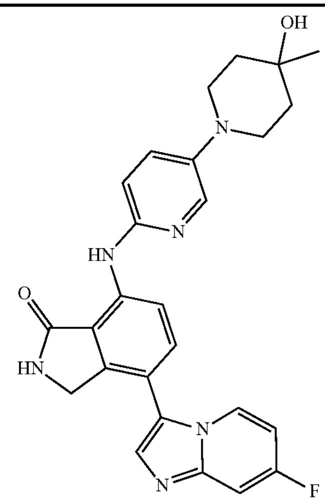 | 4-(7-fluoroimidazo[1,2-a]pyridin-3-yl)-7-((5-(4-hydroxy-4-methylpiperidin-1-yl)pyridin-2-yl)amino)isoindolin-1-one | LCMS Method J m/z = 473.2 [M + H]+, Ret. time = 2.842 min | 1H NMR (400 MHz, DMSO-d6) δ 9.83 (s, 0H), 8.77 (s, 0H), 8.55 (d, J = 8.6 Hz, 0H), 8.43 (dd, J = 7.6, 5.7 Hz, 0H), 8.02 (d, J = 2.9 Hz, 0H), 7.82 (d, J = 1.6 Hz, 0H), 7.69 (d, J = 8.6 Hz, 0H), 7.53 (dd, J = 10.1, 2.6 Hz, 0H), 7.45 (dd, J = 9.0, 3.0 Hz, 1H), 6.97 (td, J = 9.2, 8.3, 6.0 Hz, 1H), 4.38 (s, 1H), 3.33-3.16 (m, 2H), 3.10 (dt, J = 12.5, 6.5 Hz, 1H), 1.61 (d, J = 11.5 Hz, 1H), 1.61 (s, 4H), 1.25 (s, 1H), 1.18 (s, 3H). | F AA27 BB63 |
| I-398 | 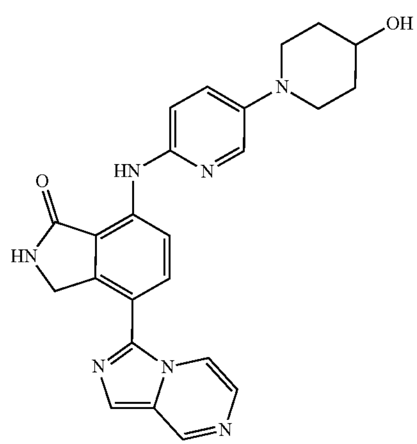 [SMILES: O=C1NCc2c(-c3ncc4cnccn34)ccc(Nc3ccc(N4CCC(O)CC4)cn3)c21] | 7-((5-(4-hydroxypiperidin-1-yl)pyridin-2-yl)amino)-4-(imidazo[1,5-a]pyrazin-3-yl)isoindolin-1-one | LCMS Method C m/z = 442.3 [M + H]+, Ret. time = 1.259 min | 1H NMR (400 MHz, DMSO-d6) δ 9.93 (s, 1H), 9.14 (d, J = 1.5 Hz, 1H), 8.79 (s, 1H), 8.58 (d, J = 8.7 Hz, 1H), 8.41 (d, J = 5.2 Hz, 1H), 8.05-7.94 (m, 3H), 7.58 (d, J = 5.2 Hz, 1H), 7.46 (dd, J = 9.0, 3.0 Hz, 1H), 6.97 (d, J = 9.0 Hz, 1H), 4.71 (d, J = 4.2 Hz, 1H), 4.57 (s, 2H), 3.48 (d, J = 12.0 Hz, 3H), 3.39 (s, 4H), 2.84 (t, J = 10.3 Hz, 3H), 1.91-1.82 (m, 2H), 1.53 (d, J = 9.9 Hz, 2H). | F AA12 BB73 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-399 | 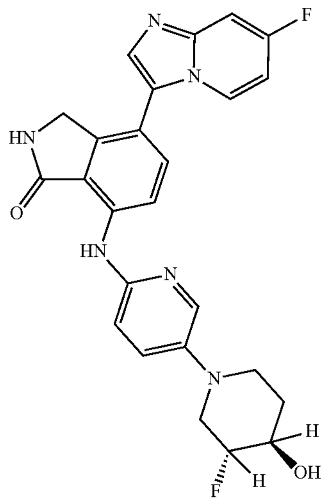 [SMILES: O=C1NCc2c(-c3cnc4cc(F)ccn34)ccc(Nc3ccc(N4CC[C@@H](O)[C@H](F)C4)cn3)c21] | 7-((5-((3R,4R)-3-fluoro-4-hydroxypiperidin-1-yl)pyridin-2-yl)amino)-4-(7-fluoroimidazo[1,2-a]pyridin-3-yl)isoindolin-1-one | LCMS Method C m/z = 477.4 [M + H]+, Ret. time = 1.371 min Chiral HPLC method X1: Ret. time = 19.03 | 1H NMR (400 MHz, DMSO-d6) δ 9.86 (s, 1H), 8.77 (s, 1H), 8.56 (d, J = 8.5 Hz, 1H), 8.42 (s, 1H), 8.03 (s, 1H), 7.81 (s, 1H), 7.69 (d, J = 8.7 Hz, 1H), 7.50 (t, J = 12.5 Hz, 2H), 6.96 (d, J = 8.8 Hz, 2H), 5.30 (d, J = 4.7 Hz, 1H), 4.38 (s, 2H), 3.69 (d, J = 13.9 Hz, 2H), 3.33 (s, 5H), 2.87 (d, J = 17.0 Hz, 2H), 1.96 (s, 1H), 1.58 (d, J = 10.7 Hz, 1H), 1.24 (s, 2H). | T AA72 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-400 | 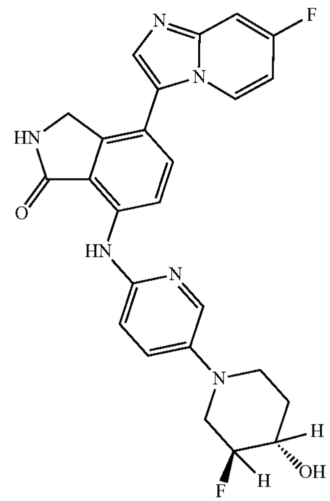 [SMILES: O=C1NCc2c(-c3cnc4cc(F)ccn34)ccc(Nc3ccc(N4CC[C@H](O)[C@@H](F)C4)cn3)c21] | 7-(5-((3S,4S)-3-fluoro-4-hydroxypiperidin-1-yl)pyridin-2-yl)amino)-4-(7-fluoroimidazo[1,2-a]pyridin-3-yl)isoindolin-1-one | LCMS Method C m/z = 477.4 [M + H]+, Ret. time = 1.368 min Chiral HPLC method X1: Ret. time = 22.79 | 1H NMR (400 MHz, DMSO-d6) δ 9.88 (s, 1H), 8.80 (s, 1H), 8.58 (d, J = 8.6 Hz, 1H), 8.44 (t, J = 6.7 Hz, 1H), 8.04 (d, J = 3.0 Hz, 1H), 7.83 (s, 1H), 7.70 (d, J = 8.6 Hz, 1H), 7.52 (ddd, J = 16.0, 9.5, 2.8 Hz, 2H), 6.97 (t, J = 5.6 Hz, 2H), 5.33 (s, 1H), 4.55-4.42 (m, 1H), 4.39 (s, 2H), 3.77-3.61 (m, 3H), 2.89 (ddd, J = 24.4, 15.4, 8.7 Hz, 3H), 2.57 (s, 2H), 2.39 (d, J = 15.0 Hz, 1H), 1.59 (d, J = 10.1 Hz, 1H). | T AA72 BB63 |
| I-401 | 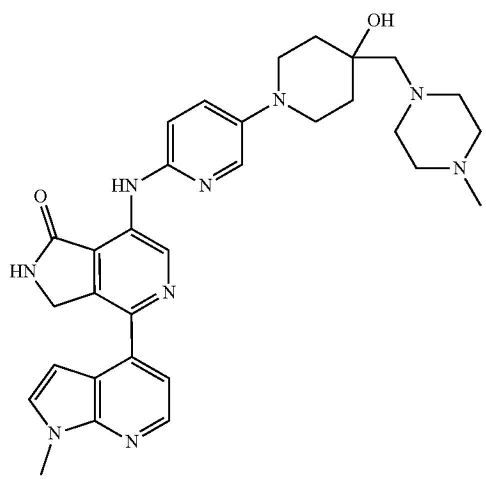 [SMILES: CN1CCN(CC2(O)CCN(c3ccc(Nc4cnc(-c5ccnc6c5ccn6C)c5c4C(=O)NC5)nc3)CC2)CC1] | 7-(5-(4-hydroxy-4-((4-methylpiperazin-1-yl)methyl)piperidin-1-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 568.4 [M + H]+, Ret. time = 2.879 min | 1H NMR (400 MHz, DMSO-d6) δ 9.93 (s, 1H), 9.50 (s, 1H), 9.16 (s, 1H), 8.36 (d, J = 5.0 Hz, 1H), 8.08 (d, J = 3.0 Hz, 1H), 7.58 (d, J = 3.4 Hz, 1H), 7.47 (dd, J = 9.1, 3.0 Hz, 1H), 7.38 (d, J = 5.0 Hz, 1H), 7.05 (d, J = 8.9 Hz, 1H), 6.92 (d, J = 3.4 Hz, 1H), 4.73 (s, 2H), 4.19 (s, 1H), 3.88 (s, 3H), 3.25 (s, 1H), 3.07 (t, J = 11.6 Hz, 3H), 2.61 (s, 2H), 2.32 (d, J = 10.6 Hz, 4H), 1.70 (t, J = 10.1 Hz, 2H), 1.59 (d, J = 13.0 Hz, 2H). | R AA55 BB14 |

| # | STRUCTURE | NAME | LCMS | 1H NMR | Method Reagent AA BB |
|---|---|---|---|---|---|
| I-402 | 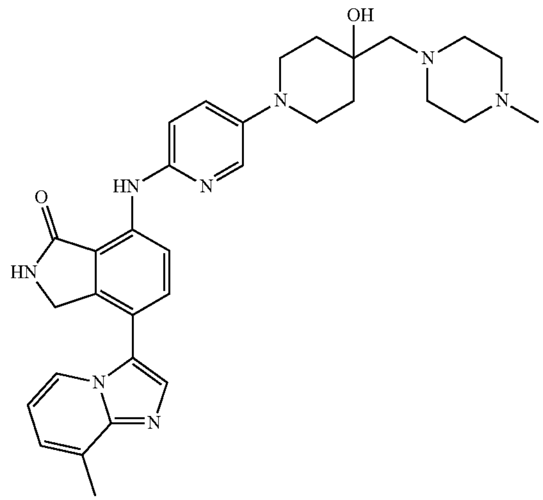 [SMILES: Cc1cccn2c(-c3ccc(Nc4ccc(N5CCC(O)(CN6CCN(C)CC6)CC5)cn4)c4c3CNC4=O)cnc12] | 7-((5-(4-hydroxy-4-((4-methylpiperazin-1-yl)methyl)piperidin-1-yl)pyridin-2-yl)amino)-4-(8-methyl-imidazo[1,2-a]pyridin-3-yl)isoindolin-1-one | LCMS Method J m/z = 567.3 [M + H]+, Ret. time = 2.620 min | 1H NMR (400 MHz, DMSO-d6) δ 9.82 (s, 1H), 8.76 (s, 1H), 8.55 (d, J = 8.6 Hz, 1H), 8.22 (d, J = 6.9 Hz, 1H), 8.01 (d, J = 2.9 Hz, 1H), 7.80 (d, J = 1.7 Hz, 1H), 7.67 (d, J = 8.6 Hz, 1H), 7.44 (dd, J = 9.1, 3.1 Hz, 1H), 7.12 (d, J = 6.8 Hz, 1H), 6.95 (d, J = 9.0 Hz, 1H), 6.86 (t, J = 6.9 Hz, 1H), 4.38 (s, 2H), 4.13 (s, 1H), 3.37 (s, 3H), 3.33-3.24 (m, 3H), 3.04 (t, J = 11.0 Hz, 3H), 2.55 (s, 6H), 2.30 (d, J = 9.9 Hz, 5H), 2.14 (s, 3H), 1.76-1.64 (m, 3H), 1.57 (d, J = 13.1 Hz, 2H), 1.25 (s, 1H). | F AA55 BB37 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-403 | (structure) | 7-((5-(4-hydroxy-4-((4-methylpiperazin-1-yl)methyl)piperidin-1-yl)pyridin-2-yl)amino)-4-(imidazo[1,2-a]pyridin-3-yl)isoindolin-1-one | LCMS Method J m/z = 553.4 [M + H]+, Ret. time = 2.522 min | 1H NMR (400 MHz, DMSO-d6) δ 9.83 (s, 1H), 8.77 (s, 1H), 8.56 (d, J = 8.5 Hz, 1H), 8.39 (d, J = 6.9 Hz, 1H), 8.02 (d, J = 2.9 Hz, 1H), 7.84 (s, 1H), 7.69 (dd, J = 13.8, 8.8 Hz, 2H), 7.45 (dd, J = 9.0, 2.9 Hz, 1H), 7.36-7.27 (m, 1H), 6.95 (dd, J = 7.9, 5.8 Hz, 2H), 4.39 (s, 2H), 4.13 (s, 1H), 3.53-3.37 (m, 5H), 3.29 (d, J = 10.3 Hz, 3H), 3.10-2.95 (m, 3H), 2.38 (s, 1H), 2.29 (s, 3H), 2.14 (s, 3H), 1.76-1.64 (m, 2H), 1.57 (d, J = 12.7 Hz, 2H), 1.25 (s, 1H). | F AA55 BB74 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-404 | (structure) | 4-(7-fluoroimidazo[1,2-a]pyridin-3-yl)-7-((5-((1R,5S)-8-hydroxy-3-azabicyclo[3.2.1]octan-3-yl)pyridin-2-yl)amino)isoindolin-1-one | LCMS Method J m/z = 485.2 [M + H]+, Ret. time = 3.183 min Chiral HPLC method X3: Ret. time = 7.37 | 1H NMR (400 MHz, DMSO-d6) δ 9.76 (s, 1H), 8.75 (s, 1H), 8.51 (d, J = 8.7 Hz, 1H), 8.43 (t, J = 6.7 Hz, 1H), 7.94 (d, J = 3.0 Hz, 1H), 7.82 (s, 1H), 7.68 (d, J = 8.6 Hz, 1H), 7.53 (d, J = 9.9 Hz, 1H), 131 (dd, J = 9.1, 3.1 Hz, 1H), 7.02-6.92 (m, 2H), 5.02 (d, J = 3.1 Hz, 1H), 4.38 (s, 2H), 3.90 (q, J = 4.5 Hz, 1H), 3.31-3.12 (m, 5H), 2.57 (s, 1H), 2.08 (s, 2H), 1.76-1.65 (m, 3H), 1.62 (t, J = 6.1 Hz, 2H), 1.25 (s, 2H), 1.19 (s, 1H), 0.86 (d, J = 8.3 Hz, 1H). | F AA73 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-405 | 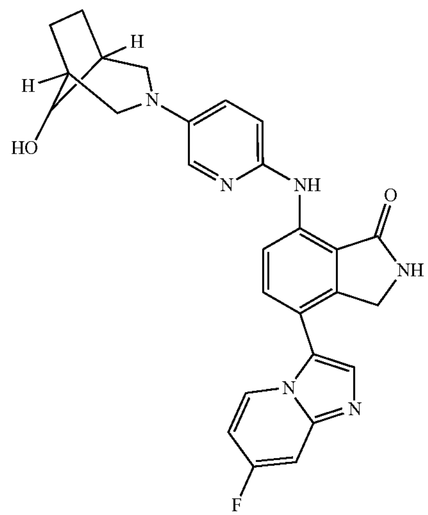 [SMILES: O=C1NCc2c(-c3cnc4cc(F)ccn34)ccc(Nc3ccc(N4CC5CCC(C4)C5O)cn3)c21] | 4-(7-fluoroimidazo[1,2-a]pyridin-3-yl)-7-((5-(8-hydroxy-3-azabicyclo[3.2.1]octan-3-yl)pyridin-2-yl)amino)isoindolin-1-one | LCMS Method C m/z = 485.5 [M + H]+, Ret. time = 1.263 min | 1H NMR (400 MHz, DMSO-d6) δ 9.77 (s, 1H), 8.76 (s, 1H), 8.51 (d, J = 8.6 Hz, 1H), 8.42 (t, J = 6.8 Hz, 1H), 7.94-7.88 (m, 1H), 7.81 (s, 1H), 7.68 (d, J = 8.6 Hz, 1H), 7.53 (d, J = 9.5 Hz, 1H), 7.40-7.32 (m, 1H), 7.02-6.90 (m, 2H), 4.74 (s, 1H), 4.38 (s, 2H), 3.78 (s, 1H), 3.47 (d, J = 11.8 Hz, 4H), 2.77 (d, J = 10.7 Hz, 2H), 2.17 (s, 2H), 1.87 (s, 2H), 1.58-1.50 (m, 2H). | F AA73 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-406 | 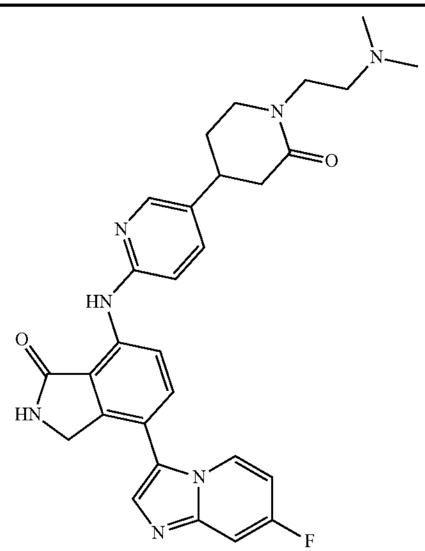 | 7-((5-(1-(2-(dimethylamino)ethyl)-2-oxopiperidin-4-yl)pyridin-2-yl)amino)-4-(7-fluoroimidazo[1,2-a]pyridin-3-yl)isoindolin-1-one | LCMS Method J m/z 528.2 = [M + H]+, Ret. time = 2.687 min | 1H NMR (400 MHz, DMSO-d6) δ 10.08 (s, 1H), 8.86 (s, 1H), 8.72 (d, J = 8.5 Hz, 1H), 8.49-8.41 (m, 1H), 8.24 (d, J = 2.6 Hz, 1H), 7.85 (d, J = 2.7 Hz, 1H), 7.78-7.64 (m, 2H), 7.59-7.50 (m, 1H), 7.00 (dd, J = 8.2, 3.5 Hz, 2H), 4.41 (s, 2H), 3.51-3.37 (m, 5H), 3.08 (s, 1H), 2.47-2.34 (m, 4H), 2.19 (d, J = 2.5 Hz, 6H), 2.00 (s, 1H), 1.25 (s, 1H). | AA65 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-407 | 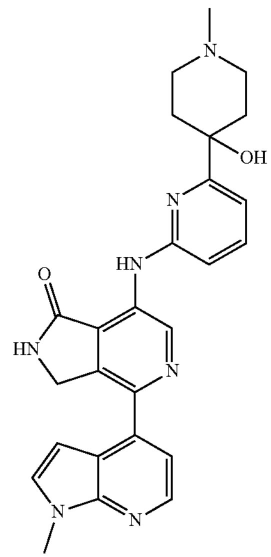 [SMILES: CN1CCC(O)(c2cccc(Nc3cnc(-c4ccnc5c4ccn5C)c4c3C(=O)NC4)n2)CC1] | 7-((6-(4-hydroxy-1-methylpiperidin-4-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method C m/z = 470.8 [M + H]+, Ret. time = 1.303 min | 1H NMR (400 MHz, DMSO-d6) δ 10.05 (s, 1H), 9.76 (s, 1H), 9.23 (s, 1H), 8.37 (d, J = 4.9 Hz, 1H), 7.74 (t, J = 7.9 Hz, 1H), 7.60 (d, J = 3.4 Hz, 1H), 7.40 (d, J = 5.0 Hz, 1H), 7.29 (d, J = 7.6 Hz, 1H), 6.94 (d, J = 8.1 Hz, 1H), 6.82 (d, J = 3.4 Hz, 1H), 5.04 (s, 1H), 4.69 (s, 2H), 3.89 (s, 3H), 3.30 (s, 1H), 2.65 (d, J = 10.3 Hz, 2H), 2.49-2.34 (m, 3H), 2.34-2.26 (m, 2H), 2.24 (s, 3H), 1.61 (d, J = 12.5 Hz, 2H). | R AA74 BB14 |
| I-408 | 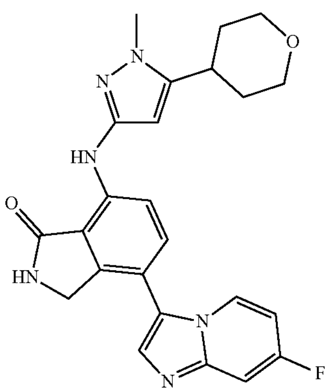 [SMILES: Cn1nc(Nc2ccc(-c3cnc4cc(F)ccn34)c3c2C(=O)NC3)cc1C1CCOCC1] | 4-(7-fluoroimidazo[1,2-a]pyridin-3-yl)-7-((1-methyl-5-(tetrahydro-2H-pyran-4-yl)-1H-pyrazol-3-yl)amino)isoindolin-1-one | LCMS Method J m/z = 447.2 [M + H]+, Ret. time = 3.238 min | 1H NMR (400 MHz, DMSO-d6) δ 9.35 (s, 1H), 8.70 (s, 1H), 8.41 (t, J = 6.5 Hz, 1H), 8.00 (d, J = 8.4 Hz, 1H), 7.79 (d, J = 3.9 Hz, 1H), 7.67 (d, J = 8.4 Hz, 1H), 7.57-7.49 (m, 1H), 6.97 (td, J = 7.5, 3.0 Hz, 1H), 5.95 (s, 1H), 4.37 (s, 2H), 3.95 (dd, J = 11.2, 4.2 Hz, 2H), 3.75 (s, 3H), 3.54-3.38 (m, 4H), 3.19 (d, J = 5.1 Hz, 1H), 3.03-2.92 (m, 1H), 1.81 (d, J = 12.9 Hz, 2H), 1.71-1.59 (m, 2H). | F AA75 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-411 | (structure) | 7-((5-(4-hydroxypiperidin-1-yl)pyridin-2-yl)amino)-4-(7-(1-methylazetidin-3-yl)imidazo[1,2-a]pyridin-3-yl)isoindolin-1-one | LCMS Method C m/z = 510.4 [M + H]+, Ret. time = 1.197 min | 1H NMR (400 MHz, DMSO-d6) δ 9.84 (s, 2H), 8.77 (s, 2H), 8.56 (d, J = 8.5 Hz, 2H), 8.34 (d, J = 7.1 Hz, 2H), 8.02 (d, J = 3.0 Hz, 2H), 7.78 (s, 2H), 7.69 (d, J = 8.5 Hz, 2H), 7.53 (s, 2H), 7.45 (dd, J = 9.0, 3.0 Hz, 2H), 7.03 (dd, J = 7.2, 1.8 Hz, 2H), 6.95 (d, J = 9.0 Hz, 2H), 4.71 (d, J = 4.2 Hz, 2H), 4.39 (s, 3H), 3.63 (p, J = 7.0 Hz, 8H), 3.51-3.42 (m, 5H), 3.16 (t, J = 5.6 Hz, 4H), 2.83 (t, J = 9.9 Hz, 4H), 2.29 (s, 5H), 1.86 (d, J = 11.8 Hz, 4H), 1.59-1.52 (m, 3H). | F AA12 BB75 |

TABLE 8-continued

Characterization Data (LCMS and ¹H NMR).

| # | STRUCTURE | NAME | LCMS | ¹H NMR | Method AA Reagent BB |
|---|---|---|---|---|---|
| I-412 | 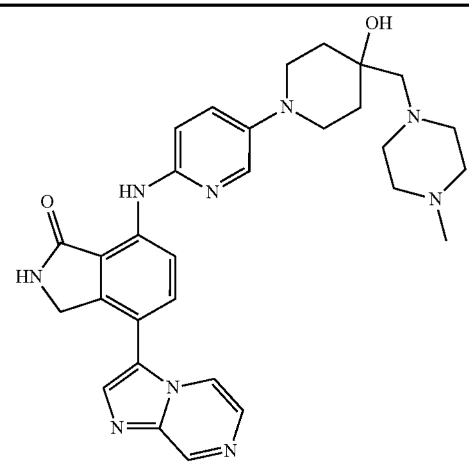 | 7-((5-(4-hydroxy-4-((4-methylpiperazin-1-yl)methyl)piperidin-1-yl)pyridin-2-yl)amino)-4-(imidazo[1,2-a]pyrazin-3-yl)isoindolin-1-one | LCMS Method J m/z = 554.2 [M + H]+, Ret. time = 2.658 min | 1H NMR (400 MHz, DMSO-d6) δ 9.86 (s, 1H), 9.15 (s, 1H), 8.82 (s, 1H), 8.58 (d, J = 8.6 Hz, 1H), 8.46 (d, J = 4.6 Hz, 1H), 8.12 (s, 1H), 8.01 (d, J = 2.9 Hz, 1H), 7.91 (d, J = 4.7 Hz, 1H), 7.76 (d, J = 8.5 Hz, 1H), 7.44 (dd, J = 9.0, 2.9 Hz, 1H), 6.95 (d, J = 8.9 Hz, 1H), 4.44 (s, 2H), 4.14 (s, 1H), 3.28 (d, J = 12.1 Hz, 3H), 3.03 (t, J = 11.0 Hz, 2H), 2.59 (d, J = 15.6 Hz, 3H), 2.43 (s, 2H), 2.29 (d, J = 11.0 Hz, 5H), 2.14 (s, 3H), 1.74-1.62 (m, 2H), 1.56 (d, J = 12.7 Hz, 2H). | F AA55 BB61 |
| I-413 | 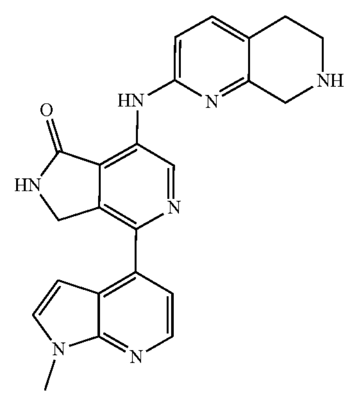 [SMILES: Cn1ccc2c(-c3ncc(Nc4ccc5c(n4)CNCC5)c4c3CNC4=O)ccnc21] | 4-(1-methyl-1H-pyrrolo[2,3-b]pyridin-4-yl)-7-((7-methyl-5,6,7,8-tetrahydro-1,7-naphthyridin-2-yl)amino)-2,3-dihydro-1H-pyrrolo[3,4-c]pyridin-1-one | LCMS Method J m/z = 412.2 [M + H]+, Ret. time = 3.023 min | 1H NMR (400 MHz, DMSO-d6) δ 8.44-8.19 (m, 3H), 7.56 (dd, J = 14.5, 6.0 Hz, 2H), 7.33 (d, J = 5.0 Hz, 1H), 6.79 (d, J = 3.3 Hz, 1H), 6.67 (s, 2H), 5.17 (s, 2H), 3.85 (d, J = 23.4 Hz, 4H), 2.96 (t, J = 5.8 Hz, 2H), 2.70 (s, 2H). | U AA76 BB14 |

TABLE 8-continued

Characterization Data (LCMS and $^1$H NMR).

| # | STRUCTURE | NAME | LCMS | $^1$H NMR | Method Reagent AA BB |
|---|---|---|---|---|---|
| I-414 | 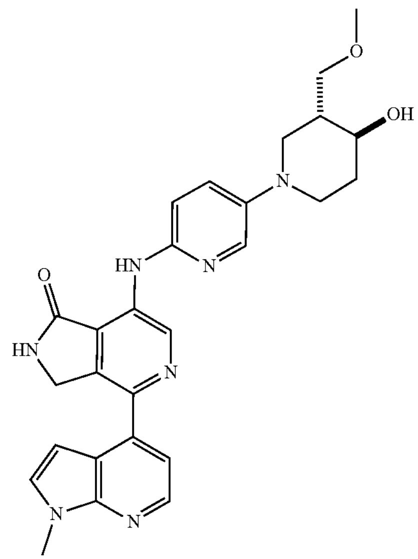 [SMILES: COC[C@H]1CN(c2ccc(Nc3cnc(-c4ccnc5c4ccn5C)c4c3C(=O)NC4)nc2)CC[C@@H]1O] | 7-((5-((3R,4S)-4-hydroxy-3-(methoxymethyl)piperidin-1-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 500.2 [M + H]+, Ret. time = 3.397 min | 1H NMR (400 MHz, DMSO-d6) δ 9.93 (s, 1H), 9.51 (s, 1H), 9.17 (s, 1H), 8.36 (d, J = 5.0 Hz, 1H), 8.07 (d, J = 3.0 Hz, 1H), 7.58 (d, J = 3.4 Hz, 1H), 7.52-7.36 (m, 2H), 7.06 (d, J = 8.9 Hz, 1H), 6.92 (d, J = 3.4 Hz, 1H), 4.73 (s, 2H), 4.52 (t, J = 5.3 Hz, 1H), 3.88 (s, 3H), 3.57-3.43 (m, 3H), 3.30 (s, 2H), 3.25 (dd, J = 12.0, 3.7 Hz, 2H), 3.05 (t, J = 10.3 Hz, 1H), 2.98-2.89 (m, 1H), 1.97 (s, 2H), 1.67 (s, 1H). | R AA77 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-415 | 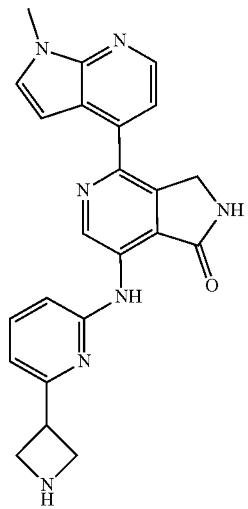 [SMILES: Cn1ccc2c(-c3ncc(Nc4cccc(C5CNC5)n4)c4c3CNC4=O)ccnc21] | 7-((6-(azetidin-3-yl)pyridin-2-yl)amino)-4-(1-methyl-1H-pyrrolo[2,3-b]pyridin-4-yl)2,3-dihydro-1H-pyrrolo[3,4-c]pyridin-1-one | LCMS Method C m/z = 412.5 [M + H]+, Ret. time = 1.374 min | 1H NMR (400 MHz, DMSO-d6) δ 10.31 (s, 1H), 8.57 (s, 1H), 8.42 (t, J = 5.2 Hz, 1H), 7.74 (dd, J = 8.3, 7.3 Hz, 1H), 7.52 (d, J = 3.5 Hz, 1H), 7.41 (d, J = 5.1 Hz, 1H), 7.03 (d, J = 8.3 Hz, 1H), 6.94 (d, J = 7.3 Hz, 1H), 6.77 (d, J = 3.5 Hz, 1H), 4.70 (s, 2H), 4.46-4.53 (m, 2H), 4.64-4.37 (m, 3H), 3.97 (s, 3H), 3.71-3.65 (m, 1H), 3.21 (s, 1H), 1.32 (s, 1H). | R AA78 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-416 | (structure) | 7-(5-((3R,4R)-4-fluoro-3-hydroxypiperidin-1-yl)pyridin-2-ylamino)-4-(1-methyl-1H-pyrrolo[2,3-b]pyridin-4-yl)-2,3-dihydro-1H-pyrrolo[3,4-c]pyridin-1-one | LCMS Method C m/z = 474.4 [M + H]+, Ret. time = 1.509 min | 1H NMR (400 MHz, DMSO-d6) δ 9.93 (s, 1H), 9.53 (s, 1H), 9.18 (s, 1H), 8.36 (d, J = 4.9 Hz, 1H), 8.09 (d, J = 3.0 Hz, 1H), 7.58 (d, J = 3.4 Hz, 1H), 7.50 (dd, J = 9.0, 3.0 Hz, 1H), 7.39 (d, J = 5.0 Hz, 1H), 7.07 (d, J = 8.9 Hz, 1H), 6.92 (d, J = 3.4 Hz, 1H), 5.45 (d, J = 5.0 Hz, 1H), 4.73 (s, 2H), 4.51 (td, J = 8.6, 7.5, 5.0 Hz, 1H), 3.88 (s, 3H), 3.75-3.56 (m, 3H), 2.86 (t, J = 12.0 Hz, 1H), 2.68 (dd, J = 12.1, 9.3 Hz, 1H), 2.14 (s, 1H), 1.83-1.73 (m, 1H). | R AA49 BB14 |
| I-417 | (structure) | 7-((5-((3S,4S)-4-fluoro-3-hydroxypiperidin-1-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 489.2 [M + H]+, Ret. time = 3.263 min Chiral HPLC method X4: Ret. time = 13.11 | 1H NMR (400 MHz, DMSO-d6) δ 9.93 (s, 1H), 9.53 (s, 1H), 9.18 (s, 1H), 8.36 (d, J = 5.0 Hz, 1H), 8.09 (d, J = 3.0 Hz, 1H), 7.61-7.34 (m, 3H), 7.07 (d, J = 8.9 Hz, 1H), 6.92 (d, J = 3.5 Hz, 1H), 5.45 (d, J = 4.9 Hz, 1H), 4.73 (s, 2H), 4.45 (d, J = 49.8 Hz, 1H), 3.88 (s, 3H), 2.85 (t, J = 11.9 Hz, 1H), 2.68 (dd, J = 12.0, 9.2 Hz, 1H), 2.13 (s, 1H), 1.75 (s, 1H). | R AA49 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-418 | 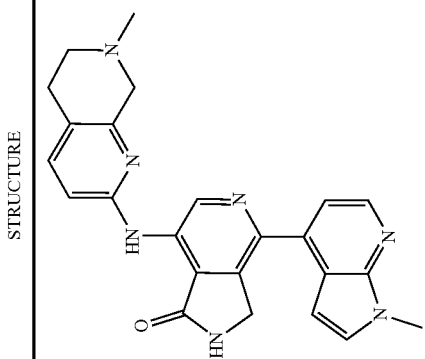 | 4-(1-methyl-1H-pyrrolo[2,3-b]pyridin-4-yl)-7-((7-methyl-5,6,7,8-tetrahydro-1,7-naphthyridin-2-yl)amino)-2,3-dihydro-1H-pyrrolo[3,4-c]pyridin-1-one | LCMS Method J m/z = 426.2 [M + H]+, Ret. time = 3.046 min | ¹H NMR (400 MHz, DMSO: δ 8.39-8.38 (d, J = 4 Hz, 1 H), 8.32-8.30 (m, 2 H), 7.67-7.65 (d, J = 8 Hz, 1 H), 7.56-7.55 (d, J = 4 Hz, 1 H), 7.33-7.32 (d, J = 4 Hz, 1 H), 6.81-6.80 (d, J = 4 Hz, 1 H), 6.69 (s, 2 H), 5.17 (s, 2 H), 3.88 (s, 3 H), 3.64 (s, 2 H), 2.85-2.84 (m, 2 H), 2.77 (s, 2 H), 2.47 (s, 3 H) | U AA79 BB14 |
| I-419 | 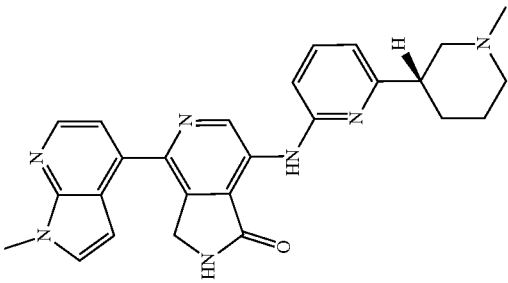 | (S)-4-(1-methyl-1H-pyrrolo[2,3-b]pyridin-4-yl)-7-((6-(1-methylpiperidin-3-yl)pyridin-2-yl)amino)-2,3-dihydro-1H-pyrrolo[3,4-c]pyridin-1-one | LCMS Method J m/z = 454.8 [M + H]+, Ret. time = 2.913 min Chiral HPLC method X3: Ret. time = 5.22 | 1H NMR (400 MHz, DMSO-d6) δ 10.08 (s, 1H), 9.72 (s, 1H), 9.22 (s, 1H), 8.37 (d, J = 4.9 Hz, 1H), 7.78-7.52 (m, 2H), 7.40 (d, J = 5.0 Hz, 1H), 7.07-6.77 (m, 3H), 4.71 (s, 2H), 3.88 (s, 2H), 2.96 (ddd, J = 44.0, 33.0, 10.8 Hz, 3H), 2.27 (s, 3H), 1.99 (s, 1H), 1.76 (s, 1H), 1.63 (s, 2H). | R AA80 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-420 | 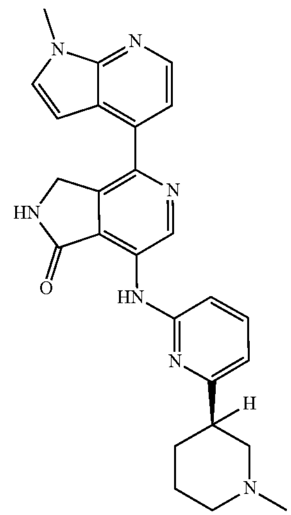 [SMILES: CN1CCC[C@@H](c2cccc(Nc3cnc(-c4ccnc5c4ccn5C)c4c3C(=O)NC4)n2)C1] | (R)-4-(1-methyl-1H-pyrrolo[2,3-b]pyridin-4-yl)-7-((6-(1-methylpiperidin-3-yl)pyridin-2-yl)amino)-2,3-dihydro-1H-pyrrolo[3,4-c]pyridin-1-one | LCMS Method J m/z = 454.8 [M + H]+, Ret. time = 2.913 min Chiral HPLC method X3: Ret. time = 6.22 | 1H NMR (400 MHz, DMSO-d6) δ 10.07 (s, 1H), 9.74 (s, 1H), 9.24 (s, 1H), 8.38 (d, J = 5.0 Hz, 1H), 7.79-7.56 (m, 2H), 7.41 (d, J = 5.0 Hz, 1H), 7.03-6.84 (m, 3H), 4.72 (s, 2H), 3.89 (s, 3H), 3.22-2.93 (m, 3H), 2.36 (s, 2H), 2.24-1.98 (m, 2H), 1.67 (s, 3H), 1.25 (s, 1H). | R AA80 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-421 | 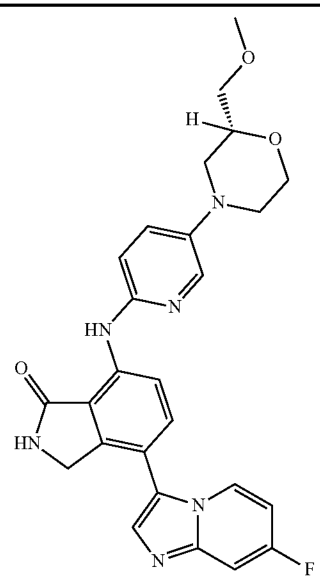 | (R)-4-(7-fluoroimidazo[1,2-a]pyridin-3-yl)-7-((5-(2-(methoxymethyl)morpholino)pyridin-2-yl)amino)isoindolin-1-one | LCMS Method J m/z = 489.2 [M + H]+, Ret. time = 3.263 min Chiral HPLC method X6: Ret. time = 14.20 | 1H NMR (400 MHz, DMSO-d6) δ 9.89 (s, 1H), 8.80 (s, 1H), 8.58 (d, J = 8.6 Hz, 1H), 8.44 (dd, J = 7.6, 5.7 Hz, 1H), 8.02 (d, J = 2.9 Hz, 1H), 7.83 (s, 1H), 7.71 (d, J = 8.6 Hz, 1H), 7.51 (ddd, J = 28.0, 9.6, 2.8 Hz, 2H), 7.05-6.95 (m, 2H), 4.39 (s, 2H), 3.99-3.93 (m, 1H), 3.76 (d, J = 9.3 Hz, 1H), 3.72-3.64 (m, 1H), 3.52 (d, J = 11.3 Hz, 1H), 3.48-3.42 (m, 3H), 3.31 (d, J = 1.3 Hz, 3H), 2.74-2.66 (m, 1H), 2.46 (d, J = 10.7 Hz, 1H). | J AA39 BB63 |

TABLE 8-continued
Characterization Data (LCMS and ¹H NMR).
| # | STRUCTURE | NAME | LCMS | ¹H NMR | Method Reagent AA BB |
|---|---|---|---|---|---|
| I-422 | 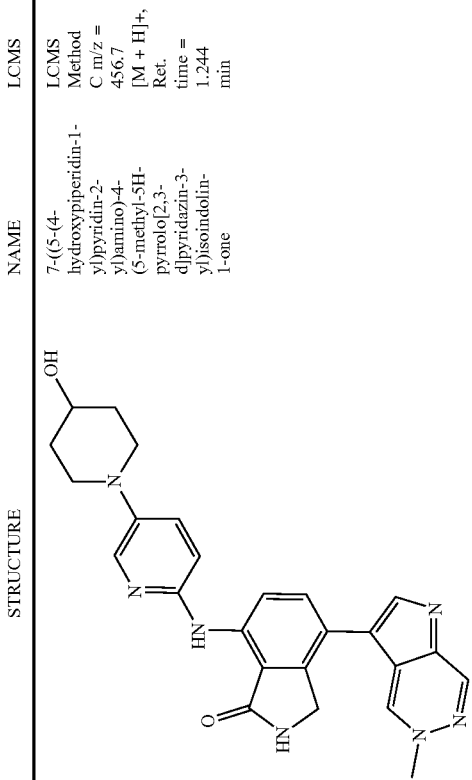 | 7-((5-(4-hydroxypiperidin-1-yl)pyridin-2-yl)amino)-4-(5-methyl-5H-pyrrolo[2,3-d]pyridazin-3-yl)isoindolin-1-one | LCMS Method C m/z = 456.7 [M + H]+, Ret. time = 1.244 min | 1H NMR (400 MHz, DMSO-d6) δ 14.23-14.05 (m, 1H), 10.30 (s, 1H), 9.87 (s, 1H), 9.63 (s, 1H), 8.92 (s, 1H), 8.70-8.49 (m, 2H), 8.06-7.82 (m, 2H), 7.56-7.41 (m, 1H), 6.95 (d, J = 8.8 Hz, 2H), 4.74 (s, 1H), 4.57 (d, J = 18.9 Hz, 4H), 3.64 (s, 1H), 3.50-3.43 (m, 2H), 2.83 (s, 2H), 1.87 (d, J = 12.5 Hz, 2H), 1.53 (d, J = 11.5 Hz, 2H), 1.25 (s, 1H). | F AA12 BB76 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-423 | 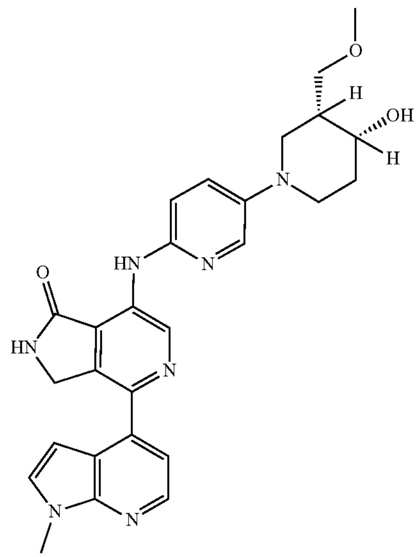 [SMILES: COC[C@H]1CN(c2ccc(Nc3cnc(-c4ccnc5c4ccn5C)c4c3C(=O)NC4)nc2)CC[C@H]1O] | 7-((5-((3R,4R)-4-hydroxy-3-(methoxymethyl)piperidin-1-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 500.2 [M + H]+, Ret. time = 3.351 min | 1H NMR (400 MHz, DMSO-d6) δ 9.93 (s, 1H), 9.51 (s, 1H), 9.18 (s, 1H), 8.36 (d, J = 5.0 Hz, 1H), 8.06 (d, J = 3.0 Hz, 1H), 7.58 (d, J = 3.5 Hz, 1H), 7.48-7.36 (m, 2H), 7.05 (d, J = 9.0 Hz, 1H), 6.93 (d, J = 3.4 Hz, 1H), 4.78-4.64 (m, 3H), 3.88 (s, 4H), 3.48-3.44 (m, 1H), 3.29 (s, 3H), 3.23 (d, J = 3.9 Hz, 1H), 3.13 (t, J = 10.3 Hz, 1H), 2.93 (t, J = 10.9 Hz, 1H), 2.06-1.99 (m, 1H), 1.79-1.69 (m, 2H), 1.25 (s, 3H). | R AA77 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-424 | 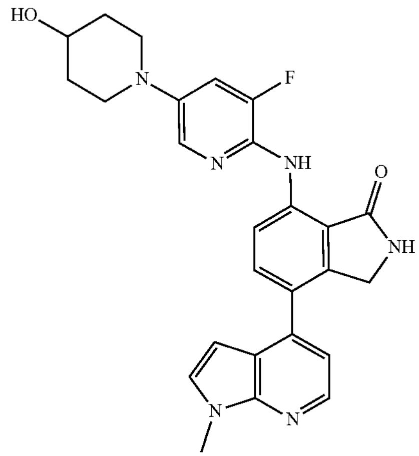 [SMILES: Cn1ccc2c(-c3ccc(Nc4ncc(N5CCC(O)CC5)cc4F)c4c3CNC4=O)ccnc21] | 7-((3-fluoro-5-(4-hydroxy-piperidin-1-yl)pyridin-2-yl)amino)-4-(1-methyl-1H-pyrrolo[2,3-b]pyridin-4-yl)isoindolin-1-one | LCMS Method J m/z = 473.8 [M + H]+, Ret. time = 3.479 min | 1H NMR (400 MHz, DMSO-d6) δ 10.21 (d, J = 2.6 Hz, 1H), 8.82 (s, 1H), 8.70 (d, J = 8.5 Hz, 1H), 8.32 (d, J = 4.9 Hz, 1H), 7.86 (d, J = 2.5 Hz, 1H), 7.76 (d, J = 8.6 Hz, 1H), 7.64-7.50 (m, 2H), 7.28 (d, J = 4.9 Hz, 1H), 6.48 (d, J = 3.5 Hz, 1H), 4.73 (d, J = 4.1 Hz, 1H), 4.48 (s, 2H), 3.88 (s, 3H), 3.65 (tt, J = 8.4, 4.4 Hz, 1H), 3.51 (dd, J = 11.3, 5.8 Hz, 2H), 2.88 (ddd, J = 12.7, 9.9, 3.1 Hz, 2H), 1.89-1.80 (m, 2H), 1.60-1.46 (m, 2H). | O AA88 BB14 |
| I-425 | 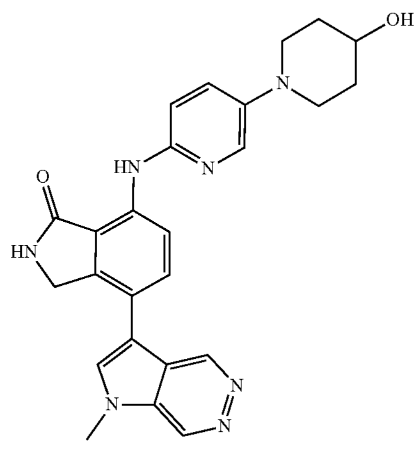 [SMILES: Cn1cc(-c2ccc(Nc3ccc(N4CCC(O)CC4)cn3)c3c2CNC3=O)c2cnncc21] | 7-(5-(4-hydroxypiperidin-1-yl)pyridin-2-yl)amino)-4-(1-methyl-1H-pyrrolo[2,3-d]pyridazin-3-yl)isoindolin-1-one | LCMS Method C m/z = 456.5 [M + H]+, Ret. time = 1.202 min | 1H NMR (400 MHz, DMSO-d6) δ 9.81 (s, 1H), 9.47 (s, 1H), 9.30 (s, 1H), 8.78 (s, 1H), 8.59-8.45 (m, 2H), 7.99 (d, J = 3.0 Hz, 1H), 7.82 (d, J = 8.5 Hz, 1H), 7.43 (dd, J = 9.0, 3.1 Hz, 1H), 6.91 (d, J = 8.9 Hz, 1H), 4.72 (s, 1H), 4.57 (s, 2H), 4.34 (s, 3H), 3.63 (tt, J = 8.6, 4.1 Hz, 1H), 3.46 (ddd, J = 15.5, 7.7, 4.0 Hz, 2H), 2.87-2.76 (m, 2H), 1.90-1.82 (m, 2H), 1.60-1.49 (m, 2H). | F AA12 BB77 |

TABLE 8-continued

Characterization Data (LCMS and ¹H NMR).

| # | STRUCTURE | NAME | LCMS | ¹H NMR | Method AA Reagent BB |
|---|---|---|---|---|---|
| I-426 | (structure) | 7-((5-(4-hydroxypiperidin-1-yl)pyridin-2-yl)amino)-4-(2-methyl-2H-pyrrolo[2,3-c]pyridazin-5-yl)isoindolin-1-one | LCMS Method C m/z = 456.4 [M + H]+, Ret. time = 1.307 min | 1H NMR (400 MHz, DMSO-d6) δ 9.79 (s, 1H), 8.80 (d, J = 27.5 Hz, 2H), 8.61 (d, J = 6.6 Hz, 1H), 8.51 (d, J = 8.6 Hz, 1H), 8.29-8.13 (m, 2H), 7.99 (d, J = 3.0 Hz, 1H), 7.78 (d, J = 8.5 Hz, 1H), 7.43 (dd, J = 9.0, 3.1 Hz, 1H), 6.91 (d, J = 9.0 Hz, 1H), 4.56 (s, 2H), 4.43 (s, 3H), 3.64 (dq, J = 9.0, 4.3 Hz, 1H), 3.45 (d, J = 12.5 Hz, 2H), 2.82 (ddd, J = 12.6, 10.0, 3.0 Hz, 2H), 2.05-1.95 (m, 1H), 1.85 (dt, J = 12.7, 4.0 Hz, 2H), 1.61-1.45 (m, 2H). | F AA12 BB78 |
| I-427 | (structure) | 7-((5-(4-hydroxytetrahydro-2H-pyran-4-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 457.4 [M + H]+, Ret. time = 2.798 min | 1H NMR (400 MHz, DMSO-d6) δ 10.07 (s, 1H), 9.74 (s, 1H), 9.23 (s, 1H), 8.48 (d, J = 2.2 Hz, 1H), 8.36 (d, J = 5.0 Hz, 1H), 7.84 (d, J = 8.7 Hz, 1H), 7.58 (d, J = 3.4 Hz, 1H), 7.40 (d, J = 5.1 Hz, 1H), 7.10 (d, J = 8.7 Hz, 1H), 6.92 (d, J = 3.4 Hz, 1H), 5.18 (s, 1H), 4.73 (s, 2H), 3.88 (s, 3H), 3.84-3.70 (m, 4H), 3.52-3.42 (m, 2H), 2.00 (d, J = 10.3 Hz, 2H), 1.61 (d, J = 13.1 Hz, 2H). | R AA57 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-428 | 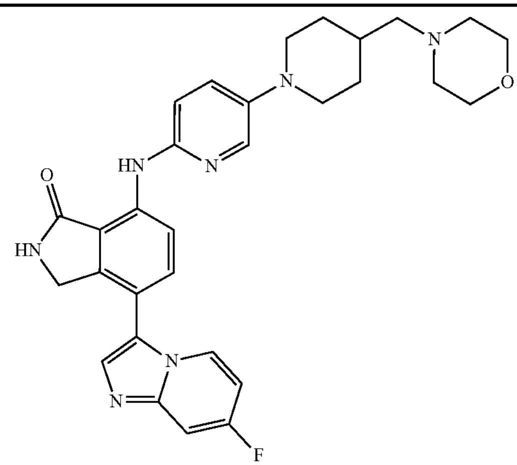 | 4-(7-fluoroimidazo[1,2-a]pyridin-3-yl)-7-((5-(4-(morpholinomethyl)piperidin-1-yl)pyridin-2-yl)amino)isoindolin-1-one | LCMS Method J m/z = 542.2 [M + H]+, Ret. time = 2.682 min | 1H NMR (400 MHz, DMSO-d6) δ 9.84 (s, 1H), 8.78 (s, 1H), 8.56 (d, J = 8.6 Hz, 1H), 8.43 (t, J = 6.8 Hz, 1H), 8.00 (d, J = 3.0 Hz, 1H), 7.82 (d, J = 3.7 Hz, 1H), 7.69 (d, J = 8.6 Hz, 1H), 7.53 (dd, J = 10.0, 2.7 Hz, 1H), 7.44 (dd, J = 9.0, 3.1 Hz, 1H), 7.02-6.93 (m, 2H), 4.38 (s, 2H), 3.59 (t, J = 4.8 Hz, 6H), 2.66 (d, J = 12.3 Hz, 3H), 2.35 (s, 5H), 2.18 (d, J = 7.3 Hz, 2H), 1.82 (d, J = 12.9 Hz, 3H), 1.67 (s, 2H), 1.25 (s, 5H). | F AA89 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-429 | 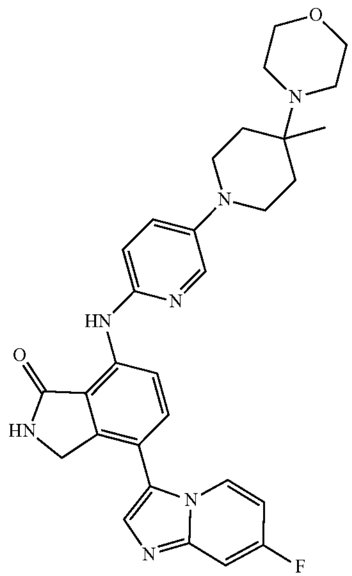 [SMILES: CC1(N2CCOCC2)CCN(c2ccc(Nc3ccc(-c4cnc5cc(F)ccn45)c4c3C(=O)NC4)nc2)CC1] | 4-(7-fluoroimidazo[1,2-a]pyridin-3-yl)-7-((5-(4-methyl-4-morpholino-piperidin-1-yl)pyridin-2-yl)amino)iso-indolin-1-one | LCMS Method J m/z = 542.2 [M + H]+, Ret. time = 2.736 min | 1H NMR (400 MHz, DMSO-d6) δ 9.82 (d, J = 3.0 Hz, 1H), 8.59-8.40 (m, 2H), 8.01 (d, J = 2.9 Hz, 1H), 7.81 (d, J = 6.4 Hz, 1H), 7.68 (dd, J = 8.6, 3.1 Hz, 1H), 7.54-7.38 (m, 2H), 7.04-6.92 (m, 2H), 4.38 (d, J = 3.9 Hz, 2H), 3.59 (t, J = 4.3 Hz, 4H), 3.16 (dt, J = 19.7, 5.5 Hz, 4H), 2.48 (d, J = 4.2 Hz, 3H), 1.87 (dd, J = 13.4, 5.0 Hz, 2H), 1.56 (ddd, J = 13.4, 9.0, 4.1 Hz, 2H), 0.94 (s, 3H). | F AA84 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-430 | 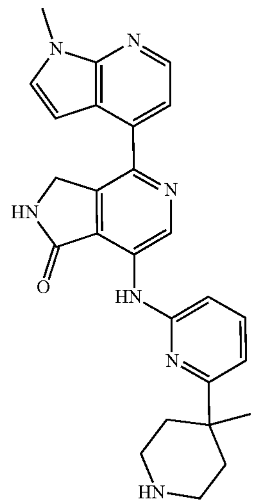 [SMILES: Cn1ccc2c(-c3ncc(Nc4cccc(C5(C)CCNCC5)n4)c4c3CNC4=O)ccnc21] | 4-(1-methyl-1H-pyrrolo[2,3-b]pyridin-4-yl)-7-((6-(4-methylpiperidin-4-yl)pyridin-2-yl)amino)-2,3-dihydro-1H-pyrrolo[3,4-c]pyridin-1-one | LCMS Method J m/z = 454.2 [M + H]+, Ret. time = 3.493 min | 1H NMR (400 MHz, DMSO-d6) δ 8.38 (d, J = 4.9 Hz, 1H), 8.36-8.29 (m, 2H), 7.90 (t, J = 8.0 Hz, 1H), 7.57 (d, J = 3.5 Hz, 1H), 7.37 (d, J = 4.9 Hz, 1H), 7.29 (d, J = 7.7 Hz, 1H), 6.85 (d, J = 3.4 Hz, 1H), 6.72 (s, 2H), 5.30 (s, 2H), 3.88 (s, 3H), 3.03 (d, J = 12.7 Hz, 2H), 2.78 (t, J = 10.9 Hz, 2H), 2.30 (s, 2H), 1.74 (t, J = 11.2 Hz, 2H), 1.24 (s, 3H). | U AA90 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-431 | 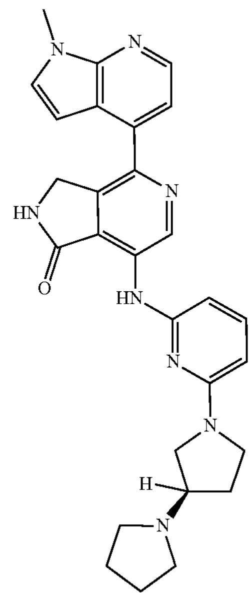 [SMILES: Cn1ccc2c(-c3ncc(Nc4cccc(N5CC[C@@H](N6CCCC6)C5)n4)c4c3CNC4=O)ccnc21] | (R)-7-((6-([1,3'-bipyrrolidin]-1'-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 495.8 [M + H]+, Ret. time = 3.015 min | 1H NMR (400 MHz, DMSO-d6) δ 10.12 (s, 1H), 9.57 (s, 1H), 8.36 (d, J = 4.9 Hz, 1H), 7.57 (d, J = 3.3 Hz, 1H), 7.49-7.35 (m, 2H), 6.89 (d, J = 3.5 Hz, 1H), 6.19 (d, J = 7.7 Hz, 1H), 6.04 (d, J = 8.1 Hz, 1H), 4.71 (s, 2H), 3.89 (s, 3H), 3.69 (dt, J = 28.2, 8.3 Hz, 2H), 3.48 (q, J = 8.9 Hz, 1H), 2.96-2.84 (m, 1H), 2.59 (d, J = 8.6 Hz, 3H), 2.25-2.17 (m, 1H), 2.03-1.89 (m, 1H), 1.79-1.68 (m, 4H), 1.25 (s, 1H). | T AA83 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-432 | 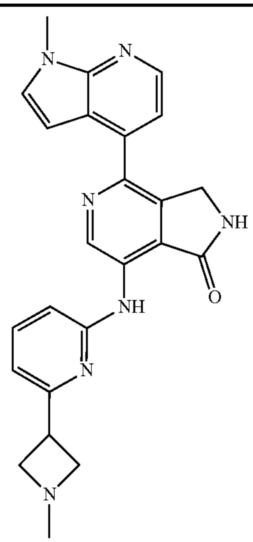 | 4-(1-methyl-1H-pyrrolo[2,3-b]pyridin-4-yl)-7-((6-(1-methylazetidin-3-yl)pyridin-2-yl)amino)-2,3-dihydro-1H-pyrrolo[3,4-c]pyridin-1-one | LCMS Method C m/z = 426.6 [M + H]+, Ret. time = 1.350 min | 1H NMR (400 MHz, DMSO-d6) δ 8.38-8.31 (m, 2H), 8.24 (s, 1H), 7.87-7.79 (m, 1H), 7.57 (d, J = 3.4 Hz, 1H), 7.42 (d, J = 4.9 Hz, 1H), 7.16 (d, J = 7.4 Hz, 1H), 6.87 (d, J = 3.4 Hz, 1H), 6.72 (s, 2H), 5.38 (s, 2H), 3.88 (s, 3H), 3.79-3.69 (m, 3H), 2.35 (s, 3H). | R AA92 BB14 |

TABLE 8-continued
Characterization Data (LCMS and $^1$H NMR).
| # | STRUCTURE | NAME | LCMS | $^1$H NMR | Method Reagent AA BB |
|---|---|---|---|---|---|
| I-433 | 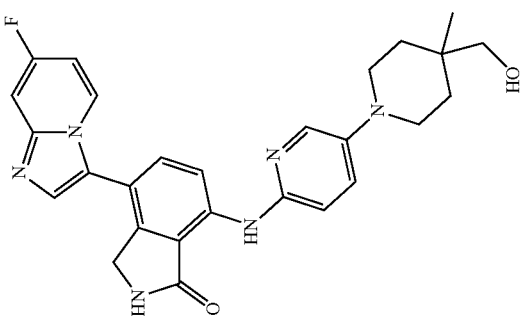 | 4-(7-fluoroimidazo[1,2-a]pyridin-3-yl)-7-((5-(4-(hydroxymethyl)-4-methylpiperidin-1-yl)pyridin-2-yl)amino)isoindolin-1-one | LCMS Method J m/z = 487.8 [M + H]+, Ret. time = 2.611 min | 1H NMR (400 MHz, DMSO-d6) δ 9.71 (s, 1H), 8.53-8.32 (m, 2H), 7.98 (d, J = 3.0 Hz, 1H), 7.77 (s, 1H), 7.67 (d, J = 8.6 Hz, 1H), 7.46 (t, J = 9.9 Hz, 2H), 6.99 (dt, J = 14.6, 5.6 Hz, 2H), 4.35 (s, 2H), 3.30-3.14 (m, 4H), 2.94 (t, J = 10.6 Hz, 2H), 1.63-1.52 (m, 2H), 1.34 (d, J = 12.8 Hz, 2H), 0.91 (s, 3H). | F AA85 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-434 | 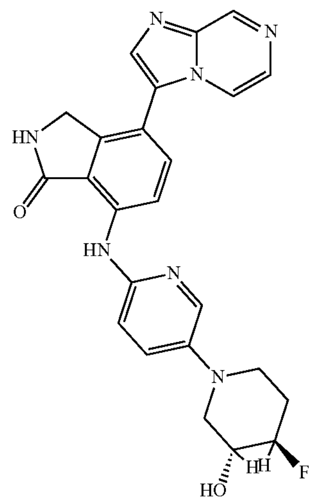 [SMILES: O=C1NCc2c(-c3cnc4cnccn34)ccc(Nc3ccc(N4CC[C@@H](F)[C@H](O)C4)cn3)c21] | 7-(5-((3R,4R)-4-fluoro-3-hydroxypiperidin-1-yl)pyridin-2-ylamino)-4-(imidazo[1,2-a]pyrazin-3-yl)isoindolin-1-one | LCMS Method J m/z = 460.7 [M + H]+, Ret. time = 2.906 min Chiral HPLC method X4: Ret. time = 16.74 | ¹H NMR (400 MHz, DMSO): δ 9.90 (s, 1 H), 9.15-9.15 (m, 1 H), 8.82 (s, 1 H), 8.60-8.58 (d, J = 9 Hz, 1 H), 8.48-8.46 (m, 1 H), 8.48-8.46 (m, 1 H), 8.12 (s, 1 H), 8.04-8.03 (d, J = 4 Hz, 1 H), 7.93-7.91 (d, J = 8 Hz, 1 H), 7.78-7.76 (d, J = 8 Hz, 1 H), 7.49-7.46 (dd, J = 8.8 Hz, 12 Hz, 1 H), 6.99-6.97 (d, J = 8 Hz 1 H), 5.43 (s, 1 H), 4.53-4.34 (m, 3 H), 3.71-3.64 (m, 1 H), 3.61-3.52 (m, 2H), 2.86-2.81 (m, 1 H), 2.69-2.63 (m, 1 H), 2.16-2.10 (m, 1 H) 1.78-1.74 (m, 1H) | T AA49 BB61 |
| I-435 | 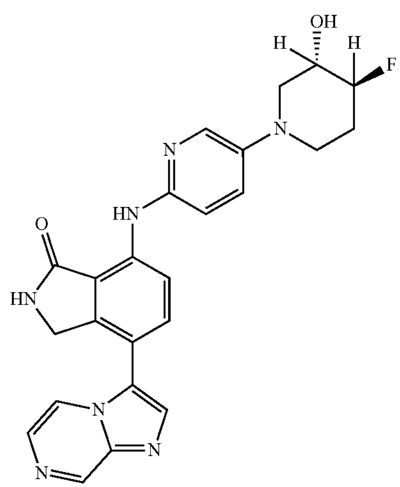 [SMILES: O=C1NCc2c(-c3cnc4cnccn34)ccc(Nc3ccc(N4CC[C@H](F)[C@@H](O)C4)cn3)c21] | 7-(5-((3S,4S)-4-fluoro-3-hydroxypiperidin-1-yl)pyridin-2-ylamino)-4-(imidazo[1,2-a]pyrazin-3-yl)isoindolin-1-one | LCMS Method J m/z = 460.7 [M + H]+, Ret. time = 2.906 min Chiral HPLC method X4: Ret. time = 17.28 | ¹H NMR (400 MHz, DMSO): δ 9.91 (s, 1 H), 9.15 (s, 1 H), 8.83 (s, 1 H), 8.60-8.58 (d, J = 8 Hz, 1 H), 8.48-8.46 (m, 1 H), 8.16 (s, 1 H), 8.12-8.10 (d, J = 8 Hz, 1 H), 8.04-8.03 (d, J = 4 Hz, 1 H), 7.93-7.91 (d, J = 8 Hz, 1 H), 7.78-7.76 (d, J = 8 Hz, 1 H), 7.49-7.46 (dd, J = 8 Hz, 8 Hz, 1H) 4.51 (s, 1 H), 4.510-4.35 (m, 3 H), 3.71-3.64 (m, 1 H), 3.60-3.53 (m, 2 H), 2.86-2.81 (m, 1 H), 2.68-2.63 (m, 1 H), 2.15-2.09 (m, 1 H) 1.78-1.74 (m, 1H) | T AA49 BB61 |

| # | STRUCTURE | NAME | LCMS | 1H NMR | Method Reagent AA BB |
|---|---|---|---|---|---|
| I-436 | 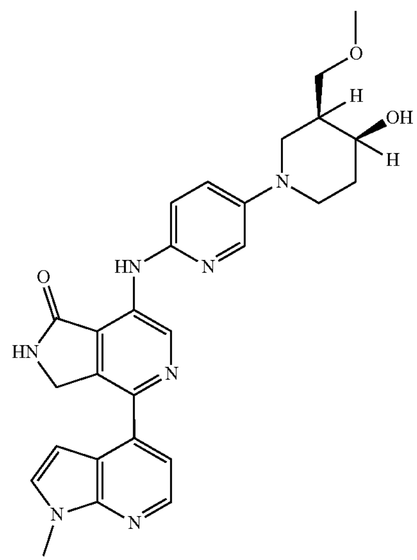 [SMILES: COC[C@@H]1CN(c2ccc(Nc3cnc(-c4ccnc5c4ccn5C)c4c3C(=O)NC4)nc2)CC[C@@H]1O] | 7-((5-((3S,4S)-4-hydroxy-3-(methoxymethyl)piperidin-1-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 500.2 [M + H]+, Ret. time = 3.345 min Chiral HPLC method X4: Ret. time = 8.03 | 1H NMR (400 MHz, DMSO-d6) δ 9.93 (s, 1H), 9.51 (s, 1H), 9.17 (s, 1H), 8.36 (d, J = 5.0 Hz, 1H), 8.06 (d, J = 3.0 Hz, 1H), 7.58 (d, J = 3.4 Hz, 1H), 7.58 (d, J = 3.4 Hz, 1H), 7.47-7.37 (m, 2H), 7.05 (d, J = 8.9 Hz, 1H), 6.93 (d, J = 3.5 Hz, 1H), 4.70 (d, J = 25.4 Hz, 3H), 3.88 (s, 4H), 3.45 (dd, J = 9.3 5.8 Hz, 1H), 3.29 (s, 5H), 3.14 (td, J = 10.4, 2.9 Hz, 1H), 2.94 (dd, J = 11.8, 10.0 Hz, 1H), 2.10-1.96 (m, 1H), 1.79-1.68 (m, 2H). | R AA77 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-437 | (structure) | 4-(7-chloro-imidazo[1,2-a]pyridin-3-yl)-7-((5-(4-hydroxy-4-((4-methylpiperazin-1-yl)methyl)piperidin-1-yl)pyridin-2-yl)amino)isoindolin-1-one | LCMS Method J m/z = 587.3 [M + H]+, Ret. time = 2.738 min | 1H NMR (400 MHz, DMSO-d6) δ 9.84 (s, 1H), 8.79 (s, 1H), 8.56 (d, J = 8.6 Hz, 1H), 8.41 (d, J = 7.4 Hz, 1H), 8.02 (d, J = 3.0 Hz, 1H), 7.94-7.83 (m, 2H), 7.70 (d, J = 8.6 Hz, 1H), 7.45 (dd, J = 9.0, 3.0 Hz, 1H), 7.11-6.91 (m, 2H), 4.40 (s, 2H), 4.15 (s, 1H), 3.04 (t, J = 10.6 Hz, 2H), 2.30 (s, 6H), 2.18 (s, 3H), 1.73-1.65 (m, 2H), 1.57 (d, J = 13.0 Hz, 2H), 1.25 (s, 1H). | F AA55 BB79 |

TABLE 8-continued
Characterization Data (LCMS and ¹H NMR).
| # | STRUCTURE | NAME | LCMS | ¹H NMR | Method Reagent AA BB |
|---|---|---|---|---|---|
| I-438 | 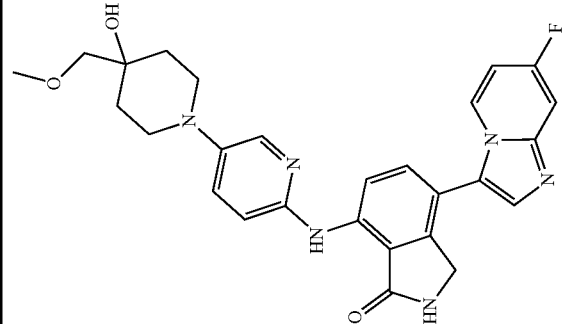 | 4-(7-fluoro-imidazo[1,2-a]pyridin-3-yl)-7-((5-(4-hydroxy-4-(methoxymethyl)piperidin-1-yl)pyridin-2-yl)amino)isoindolin-1-one | LCMS Method J m/z = 502.2 [M + H]+, Ret. time = 2.931 min | 1H NMR (400 MHz, DMSO-d6) δ 9.83 (s, 1H), 8.77 (s, 1H), 8.56 (d, J = 8.6 Hz, 1H), 8.43 (dd, J = 7.6, 5.7 Hz, 1H), 8.02 (d, J = 3.0 Hz, 1H), 7.82 (s, 1H), 7.69 (d, J = 8.6 Hz, 1H), 7.49 (ddd, J = 33.7, 9.5, 2.8 Hz, 2H), 7.04-6.91 (m, 2H), 4.41 (d, J = 17.1 Hz, 3H), 3.37 (d, J = 3.7 Hz, 5H), 3.20 (s, 2H), 3.03 (td, J = 12.0, 2.8 Hz, 2H), 1.73 (td, J = 12.7, 4.4 Hz, 2H), 1.52 (d, J = 12.8 Hz, 2H). | F AA20 BB63 |

TABLE 8-continued
Characterization Data (LCMS and ¹H NMR).
| # | STRUCTURE | NAME | LCMS | ¹H NMR | Method Reagent AA BB |
|---|---|---|---|---|---|
| I-439 | 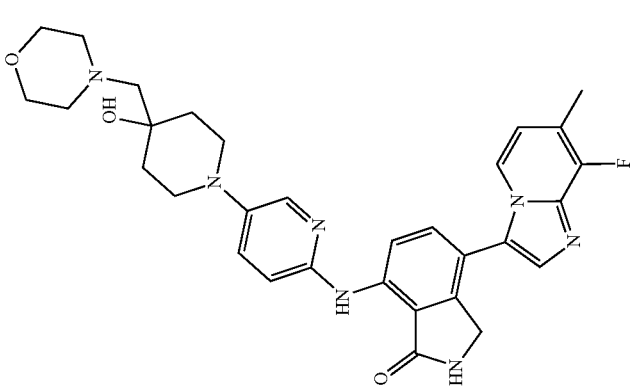 | 4-(8-fluoro-7-methylimidazo[1,2-a]pyridin-3-yl)-7-((5-(4-hydroxy-4-(morpholinomethyl)piperidin-1-yl)pyridin-2-yl)amino)isoindolin-1-one | LCMS Method J m/z = 572.3 [M + H]+, Ret. time = 2.836 min | 1H NMR (400 MHz, DMSO-d6) δ 9.82 (s, 1H), 8.73 (s, 1H), 8.54 (d, J = 8.7 Hz, 1H), 8.14 (d, J = 8 Hz, 1H), 8.01 (d, J = 2.9 Hz, 1H), 7.78 (s, 1H), 7.67 (s, 1H), 7.44 (d, J = 8 Hz, 1H), 6.93 (d, 1H), 6.82 (m, 1H), 4.37 (s, 2H), 4.15 (s, 1H), 3.57 (t, J = 4.5 Hz, 4H), 3.13-2.98 (m, 4H), 2.35-2.27 (m, 5H), 1.78-1.50 (m, 4H). | F AA15 BB80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-440 | 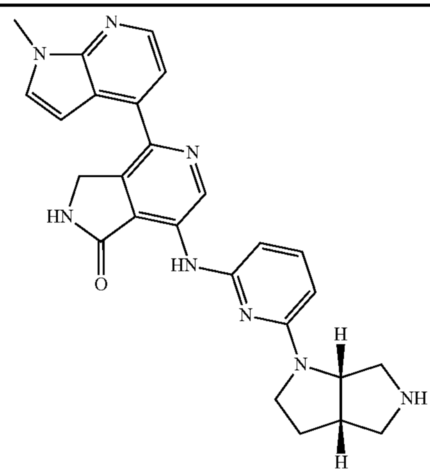 | 7-((6-((3aS,6aS)-hexahydro-pyrrolo[3,4-b]pyrrol-1(2H)-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 467.2 [M + H]+, Ret. time = 2.964 min Chiral HPLC method X6: Ret. time = 13.85 | 1H NMR (400 MHz, DMSO-d6) δ 10.09 (s, 1H), 9.58 (s, 1H), 9.20 (s, 1H), 8.36 (d, J = 5.0 Hz, 1H), 7.59 (d, J = 11.0 Hz, 2H), 7.44 (d, J = 8.5 Hz, 1H), 7.38 (d, J = 3.4 Hz, 1H), 6.87 (d, J = 5.0 Hz, 1H), 6.21 (d, J = 3.4 Hz, 1H), 6.0 (s, 1H), 4.70 (s, 2H), 4.32 (s, 1H), 3.88 (s, 3H), 3.64-3.44 (m, 4H), 2.99-2.66 (m, 4H), 1.99 (m 1H), 1.83 (m, 1H). | R AA86 BB14 |
| I-441 | 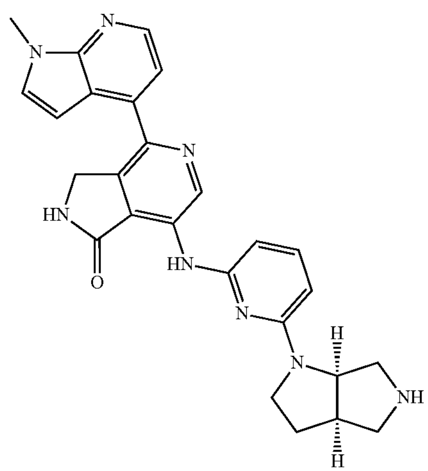 [SMILES: Cn1ccc2c(-c3ncc(Nc4cccc(N5CC[C@@H]6CNC[C@@H]65)n4)c4c3CNC4=O)ccnc21] | 7-((6-((3aR,6aR)-hexahydro-pyrrolo[3,4-b]pyrrol-1(2H)-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 467.2 [M + H]+, Ret. time = 2.967 min Chiral HPLC method X6, Ret. Time: 15.77 | 1H NMR (400 MHz, DMSO-d6) δ 10.04 (s, 1H), 9.59 (s, 1H), 9.22 (s, 1H), 8.41-8.30 (m, 2H), 7.59 (d, J = 3.5 Hz, 1H), 7.49 (t, J = 7.9 Hz, 1H), 7.39 (d, J = 5.0 Hz, 1H), 6.88 (d, J = 3.4 Hz, 1H), 6.25 (d, J = 7.7 Hz, 1H), 6.09 (d, J = 8.2 Hz, 1H), 4.71 (s, 2H), 4.43 (d, J = 7.0 Hz, 1H), 3.93 (s, 3H), 3.64 (dt, J = 9.9, 6.9 Hz, 4H), 3.21-3.14 (m, 1H), 3.05 (ddd, J = 20.2, 15.8, 9.7 Hz, 3H), 2.89 (dd, J = 10.5, 3.0 Hz, 1H), 2.15 (dt, J = 13.1, 6.9 Hz, 1H), 2.05-1.86 (m, 2H). | R AA86 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-442 | 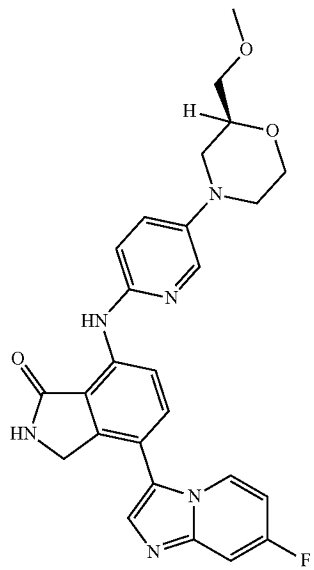 | (S)-4-(7-fluoroimidazo[1,2-a]pyridin-3-yl)-7-((5-(2-(methoxymethyl)morpholino)pyridin-2-yl)amino)isoindolin-1-one | LCMS Method J m/z = 489.2 [M + H]+, Ret. time = 3.262 min Chiral HPLC method x6: Ret. time = 15.77 | 1H NMR (400 MHz, DMSO-d6) δ 9.89 (s, 1H), 8.80 (s, 1H), 8.58 (d, J = 8.6 Hz, 1H), 8.44 (dd, J = 7.7, 5.7 Hz, 1H), 8.02 (d, J = 3.0 Hz, 1H), 7.83 (s, 1H), 7.71 (d, J = 8.6 Hz, 1H), 7.50 (ddd, J = 27.5, 9.5, 2.8 Hz, 2H), 7.04-6.94 (m, 2H), 4.39 (s, 2H), 4.03-3.91 (m, 1H), 3.76 (dtd, J = 10.4, 5.0, 2.4 Hz, 1H), 3.72-3.65 (m, 1H), 3.58-3.50 (m, 2H), 3.48-3.40 (m, 3H), 3.31 (s, 3H), 2.72-2.67 (m, 1H), 1.25 (s, 2H). | J AA39 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-443 | 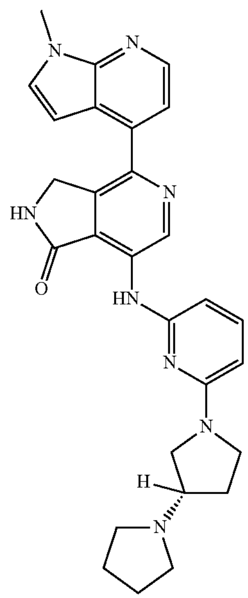 [SMILES: Cn1ccc2c(-c3ncc(Nc4cccc(N5CC[C@H](N6CCCC6)C5)n4)c4c3CNC4=O)ccnc21] | (S)-7-((6-([1,3'-bipyrrolidin]-1'-yl)pyridin-2-yl)amino)-4-(1-methyl-1H-pyrrolo[2,3-b]pyridin-4-yl)-2,3-dihydro-1H-pyrrolo[3,4-c]pyridin-1-one | Method J m/z = 495.8 [M + H]+, Ret. time = 3.02 min | 1H NMR (400 MHz, DMSO-d6) δ 10.12 (s, 1H), 9.57 (s, 1H), 9.20 (s, 1H), 8.36 (d, J = 5.0 Hz, 1H), 7.58 (d, J = 3.5 Hz, 1H), 7.51-7.35 (m, 2H), 6.89 (d, J = 3.5 Hz, 1H), 6.19 (d, J = 7.7 Hz, 1H), 6.04 (d, J = 8.1 Hz, 1H), 4.71 (s, 2H), 3.88 (s, 3H), 3.69 (d, J = 27.4 Hz, 2H), 3.48 (q, J = 8.8 Hz, 1H), 3.32 (s, 1H), 2.90 (t, J = 7.5 Hz, 3H), 2.60-2.56 (m, 3H), 2.20 (s, 1H), 1.96 (dq, J = 11.8, 8.7 Hz, 1H), 1.74 (p, J = 3.2 Hz, 4H). | T AA83 BB14 |

| # | STRUCTURE | NAME | LCMS | 1H NMR | Method Reagent AA BB |
|---|---|---|---|---|---|
| I-444 | 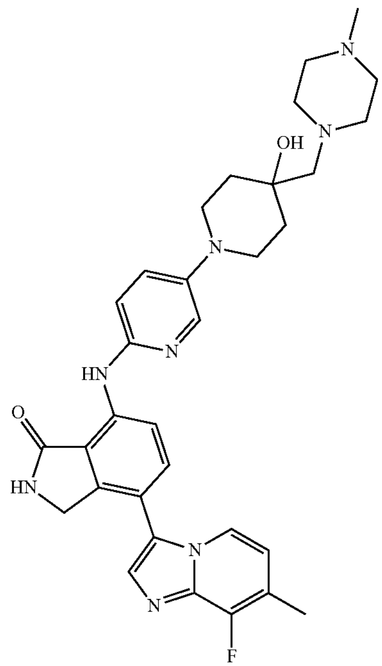 [SMILES: Cc1ccn2c(-c3ccc(Nc4ccc(N5CCC(O)(CN6CCN(C)CC6)CC5)cn4)c4c3CNC4=O)cnc2c1F] | 4-(8-fluoro-7-methylimidazo[1,2-a]pyridin-3-yl)-7-((5-(4-hydroxy-4-((4-methylpiperazin-1-yl)methyl)piperidin-1-yl)pyridin-2-yl)amino)isoindolin-1-one | LCMS Method J m/z = 585.4 [M + H]+, Ret. time = 2.761 min | 1H NMR (400 MHz, DMSO-d6) δ 9.83 (s, 1H), 8.78 (s, 1H), 8.56 (d, J = 8.6 Hz, 1H), 8.25-8.12 (m, 1H), 8.02 (d, J = 3.0 Hz, 1H), 7.81 (s, 1H), 7.68 (d, J = 8.6 Hz, 1H), 7.45 (dd, J = 9.0, 3.0 Hz, 1H), 6.95 (d, J = 8.9 Hz, 1H), 6.84 (t, J = 6.8 Hz, 1H), 4.39 (s, 2H), 3.29 (dt, J = 11.9, 4.2 Hz, 2H), 3.07-2.99 (m, 2H), 2.39-2.28 (m, 8H), 2.17 (s, 3H), 1.69 (ddd, J = 13.0, 11.0, 4.3 Hz, 2H), 1.57 (d, J = 13.2 Hz, 2H). | F AA55 BB80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-445 | 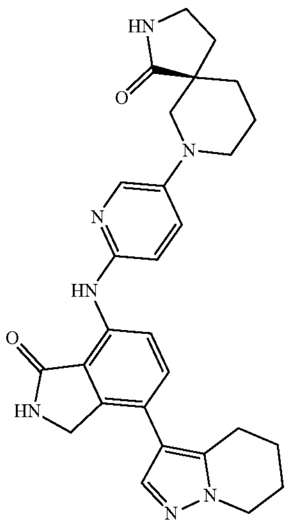 [SMILES: O=C1NCc2c(-c3cnn4c3CCCC4)ccc(Nc3ccc(N4CCC[C@]5(CCNC5=O)C4)cn3)c21] | (R)-7-(6-((3-oxo-7-(4,5,6,7-tetrahydro-pyrazolo[1,5-a]pyridin-3-yl)isoindolin-4-yl)amino)pyridin-3-yl)-2,7-diaza-spiro[4.5]decan-1-one | LCMS Method J m/z = 498.2 [M + H]+, Ret. time = 3.60 min Chiral HPLC method X3: Ret. time = 7.22 | 1H NMR (400 MHz, DMSO-d6) δ 9.75 (s, 1H), 8.73 (s, 1H), 8.42 (d, J = 8.5 Hz, 1H), 7.97 (d, J = 3.0 Hz, 1H), 7.69 (d, J = 9.7 Hz, 2H), 7.48-7.36 (m, 2H), 6.89 (d, J = 8.9 Hz, 1H), 4.44 (s, 2H), 4.12 (t, J = 6.1 Hz, 2H), 3.51 (d, J = 11.4 Hz, 1H), 3.33-3.25 (m, 2H), 3.22-3.17 (m, 1H), 2.85 (t, J = 6.3 Hz, 2H), 2.62 (d, J = 11.6 Hz, 2H), 2.22 (ddd, J = 12.8, 8.1, 4.8 Hz, 1H), 2.06-1.91 (m, 3H), 1.83 (d, J = 6.3 Hz, 2H), 1.70 (d, J = 26.7 Hz, 2H), 1.66-1.48 (m, 3H). | J AA87 BB46 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-446 | 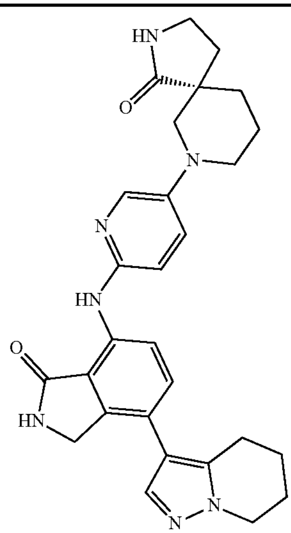 | (S)-7-(6-((3-oxo-7-(4,5,6,7-tetrahydro-pyrazolo[1,5-a]pyridin-3-yl)isoindolin-4-yl)amino)pyridin-3-yl)-2,7-diaza-spiro[4.5]decan-1-one | LCMS Method J m/z = 498.2 [M + H]+, Ret. time = 3.60 min Chiral HPLC method X3: Ret. time = 8.36 | 1H NMR (400 MHz, DMSO-d6) δ 9.76 (s, 1H), 8.73 (s, 1H), 8.42 (d, J = 8.5 Hz, 1H), 7.97 (d, J = 3.0 Hz, 1H), 7.69 (d, J = 9.0 Hz, 2H), 7.47-7.37 (m, 2H), 6.89 (d, J = 9.0 Hz, 1H), 4.44 (s, 2H), 4.12 (t, J = 6.1 Hz, 2H), 3.51 (d, J = 11.3 Hz, 1H), 3.23 (dtd, J = 33.3, 9.2, 8.8, 5.5 Hz, 3H), 2.85 (t, J = 6.3 Hz, 2H), 2.64-2.56 (m, 3H), 2.22 (ddd, J = 12.8, 8.1, 4.8 Hz, 1H), 2.05-1.91 (m, 3H), 1.86-1.78 (m, 2H), 1.77-1.66 (m, 2H), 1.64-1.56 (m, 1H), 1.51 (d, J = 12.1 Hz, 1H). | J AA87 BB46 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-447 | 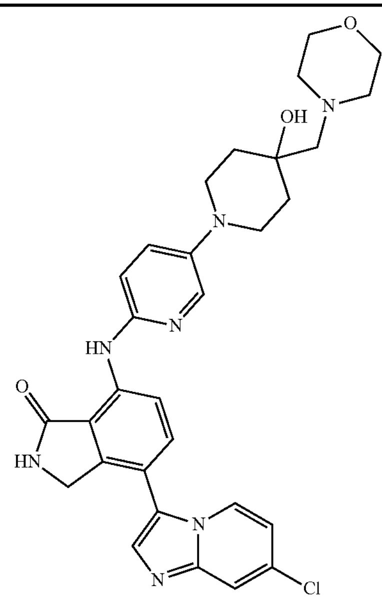 | 4-(7-chloro-imidazo[1,2-a]pyridin-3-yl)-7-((5-(4-hydroxy-4-(morpholino-methyl)piperidin-1-yl)pyridin-2-yl)amino)iso-indolin-1-one | LCMS Method J m/z = 574.53 [M + H]+, Ret. time = 2.365 min | 1H NMR (400 MHz, DMSO-d6) δ 9.84 (s, 1H), 8.79 (s, 1H), 8.57 (d, J = 8.6 Hz, 1H), 8.41 (d, J = 7.4 Hz, 1H), 8.02 (d, J = 3.0 Hz, 1H), 7.95-7.82 (m, 2H), 7.70 (d, J = 8.6 Hz, 1), 7.45 (dd, J = 9.0, 3.1 Hz, 1H), 7.04-6.90 (m, 2H), 4.40 (s, 2H), 4.20 (s, 1H), 3.58 (t, J = 4.6 Hz, 3H), 3.29 (dt, J = 13.0, 4.1 Hz, 2H), 3.05 (td, J = 11.5, 3.1 Hz, 2H), 2.30 (s, 2H), 1.76-1.57 (m, 4H). | F AA15 BB79 |

| # | STRUCTURE | NAME | LCMS | 1H NMR | Method Reagent AA BB |
|---|---|---|---|---|---|
| I-448 | 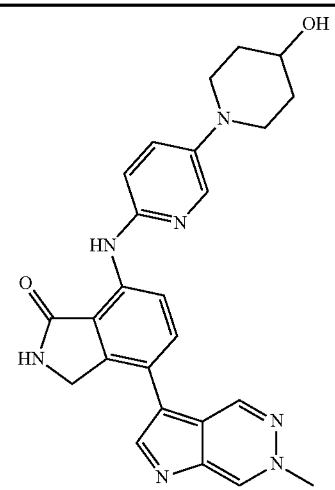 | 7-(5-(4-hydroxypiperidin-1-yl)pyridin-2-yl)amino)-4-(6-methyl-6H-pyrrolo[2,3-d]pyridazin-3-yl)isoindolin-1-one | LCMS Method J m/z = 456.7 [M + H]+, Ret. time = 2.39 min | 1H NMR (400 MHz, DMSO-d6) δ 14.21 (s, 1H), 10.07 (s, 1H), 9.87 (d, J = 34.9 Hz, 2H), 8.90 (s, 1H), 8.75 (s, 1H), 8.61 (d, J = 8.6 Hz, 1H), 8.05 (s, 1H), 7.89 (d, J = 8.5 Hz, 1H), 7.51 (d, J = 8.9 Hz, 1H), 6.98 (d, J = 9.0 Hz, 1H), 4.58 (d, J = 6.6 Hz, 5H), 3.67 (s, 3H), 3.49 (d, J = 12.1 Hz, 3H), 2.89 (s, 2H), 1.88 (d, J = 12.1 Hz, 2H), 1.56 (d, J = 9.9 Hz, 2H). | F AA12 BB43 |
| I-449 | 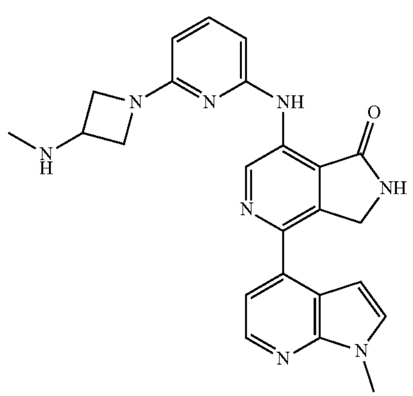 [SMILES: CNC1CN(c2cccc(Nc3cnc(-c4ccnc5c4ccn5C)c4c3C(=O)NC4)n2)C1] | 7-[[6-[3-(methyl-amino)azetidin-1-yl]-2-pyridyl]amino]-4-(1-methyl-pyrrolo[2,3-b]pyridin-4-yl)-2,3-dihydro-pyrrolo[3,4-c]pyridin-1-one Formic acid salt | Method AcHSS C18, m/z = 441 [M + H]+, Ret. time = 2.45 min. | 1H NMR (400 MHz, DMSO): δ 10.08 (s, 1 H), 9.63 (s, 1 H), 9.20 (s, 1 H), 8.37 (d, J = 5.0 Hz, 1 H), 8.18 (s, 1 H), 7.59 (d, J = 3.4 Hz, 1 H), 7.48 (t, J = 7.9 Hz, 1 H), 7.39 (d, J = 5.0 Hz, 1 H), 6.89 (d, J = 3.4 Hz, 1 H), 6.29-6.26 (m, 1 H), 5.99-5.96 (m, 1 H), 4.71 (s, 2 H), 4.22-4.17 (m, 2 H), 3.88 (s, 3 H), 3.80-3.67 (m, 3 H), 2.33 (s, 3 H). | O AC43 BC26 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-450 | 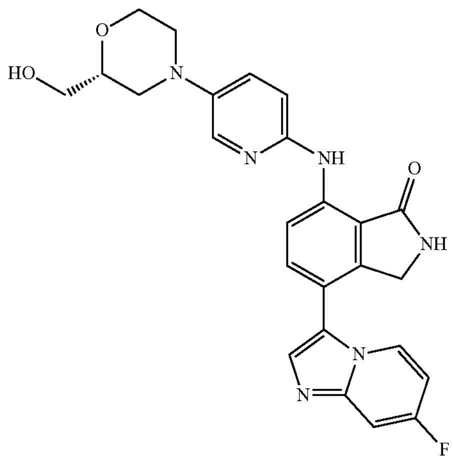 [SMILES: O=C1NCc2c(-c3cnc4cc(F)ccn34)ccc(Nc3ccc(N4CCO[C@@H](CO)C4)cn3)c21] | 4-(7-fluoro-imidazo[1,2-a]pyridin-3-yl)-7-[[5-[(2R)-2-(hydroxymethyl)morpholin-4-yl]-2-pyridyl]amino]isoindolin-1-one | Method AcHSS C18, m/z = 475 [M + H]+, Ret. time = 2.21 min. | ¹H NMR (400 MHz, DMSO): δ 9.93 (s, 1 H), 8.83 (s, 1 H), 8.62 (d, J = 8.5 Hz, 1 H), 8.49 (dd, J = 6.2, 7.2 Hz, 1 H), 8.06 (d, J = 3.0 Hz, 1 H), 7.89 (s, 1 H), 7.75 (d, J = 8.4 Hz, 1 H), 7.60 (dd, J = 2.4, 10.2 Hz, 1 H), 7.51 (dd, J = 3.0, 8.8 Hz, 1 H), 7.08-7.02 (m, 2 H), 4.83-4.81 (m, 1 H), 4.45-4.42 (m, 2 H), 4.04-3.99 (m, 1 H), 3.77-3.48 (m, 6 H), 2.80-2.72 (m, 1 H), 1.31-1.29 (m, 1 H). | H AC44 BC80 |
| I-451 | 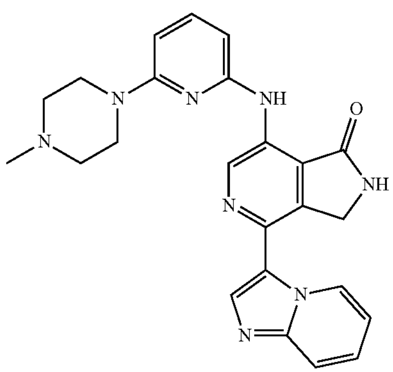 [SMILES: CN1CCN(c2cccc(Nc3cnc(-c4cnc5ccccn45)c4c3C(=O)NC4)n2)CC1] | 4-imidazo[1,2-a]pyridin-3-yl-7-[[6-(4-methylpiperazin-1-yl)-2-pyridyl]amino]-2,3-dihydropyrrolo[3,4-c]pyridin-1-one Bis formate | Method AcHSS C18, m/z = 441 [M + H]+, Ret. time = 1.96 min. | ¹H NMR (400 MHz, DMSO): δ 9.82 (d, J = 7.7 Hz, 1 H), 9.75 (s, 1 H), 9.49 (s, 1 H), 9.32 (s, 1 H), 8.15 (s, 2 H), 8.11 (s, 1 H), 7.75 (d, J = 8.8 Hz, 1 H), 7.53 (t, J = 7.9 Hz, 1 H), 7.44 (t, J = 7.4 Hz, 1 H), 7.12 (t, J = 6.3 Hz, 1 H), 6.44 (d, J = 8.1 Hz, 1 H), 6.36 (d, J = 8.4 Hz, 1 H), 4.78 (s, 2 H), 3.64 (s, 4 H), 2.74 (s, 4 H), 2.42 (s, 3 H). | O AC35 BC42 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-452 | 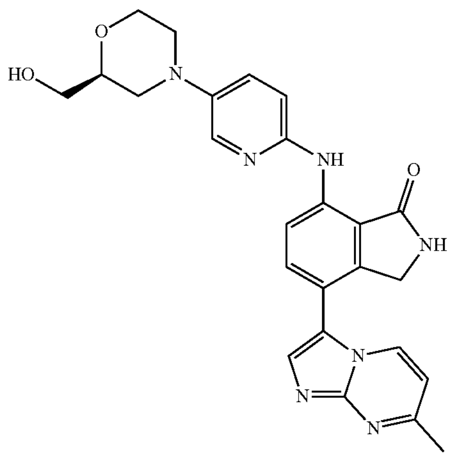 [SMILES: Cc1ccn2c(-c3ccc(Nc4ccc(N5CCO[C@H](CO)C5)cn4)c4c3CNC4=O)cnc2n1] | 7-[[5-[(2S)-2-(hydroxymethyl)morpholin-4-yl]-2-pyridyl]amino]-4-(7-methylimidazo[1,2-a]pyrimidin-3-yl)isoindolin-1-one | Method AcHSS C18, m/z = 472 [M + H]+, Ret. time = 2.16 min. | ¹H NMR (400 MHz, DMSO): δ 9.92 (s, 1 H), 8.83 (s, 1 H), 8.76 (d, J = 7.1 Hz, 1 H), 8.61 (d, J = 8.6 Hz, 1 H), 8.05 (d, J = 3.0 Hz, 1 H), 7.92 (s, 1 H), 7.74 (d, J = 8.8 Hz, 1 H), 7.50 (dd, J = 3.0, 9.1 Hz, 1 H), 7.05-7.01 (m, 2 H), 4.82 (t, J = 5.7 Hz, 1 H), 4.46 (s, 2 H), 4.01 (dd, J = 1.9, 11.2 Hz, 1 H), 3.76-3.45 (m, 6H), 2.78-2.71 (m, 1 H), 2.62 (s, 1 H). | C AC45 BC109 |
| I-453 | 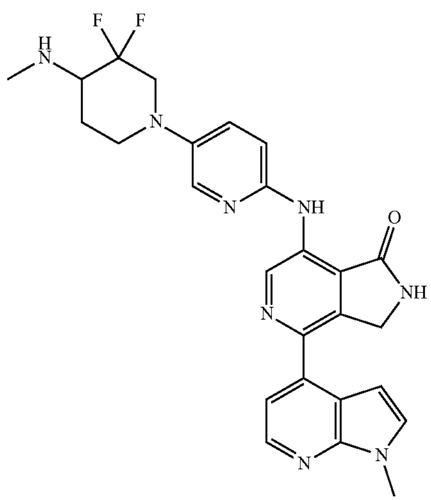 [SMILES: CNC1CCN(c2ccc(Nc3cnc(-c4ccnc5c4ccn5C)c4c3C(=O)NC4)nc2)CC1(F)F] | 7-[[5-[3,3-difluoro-4-(methylamino)-1-piperidyl]-2-pyridyl]amino]-4-(1-methylpyrrolo[2,3-b]pyridin-4-yl)-2,3-dihydropyrrolo[3,4-c]pyridin-1-one | Method BicarbB EHC18, m/z = 505.2 [M + H]+, Ret. time = 3.98 min. | ¹H NMR (400 MHz, DMSO): δ 9.94 (s, 1 H), 9.54 (s, 1 H), 9.17 (s, 1 H), 8.36 (d, J = 4.9 Hz, 1 H), 8.11 (d, J = 2.5 Hz, 1 H), 7.59-7.51 (m, 2 H), 7.39 (d, J = 5.0 Hz, 1 H), 7.09-7.05 (m, 1 H), 6.92 (d, J = 3.4 Hz, 1 H), 4.73 (s, 2 H), 3.88 (s, 3 H), 3.77-3.68 (m, 1 H), 3.50-3.46 (m, 1 H), 3.25-3.19 (m, 1 H), 3.03 (t, J = 9.9 Hz, 1 H), 2.92-2.83 (m, 1 H), 2.42 (s, 3 H), 2.02-1.99 (m, 1 H), 1.78-1.64 (m, 1 H). | O AC48 BC26 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-454 | 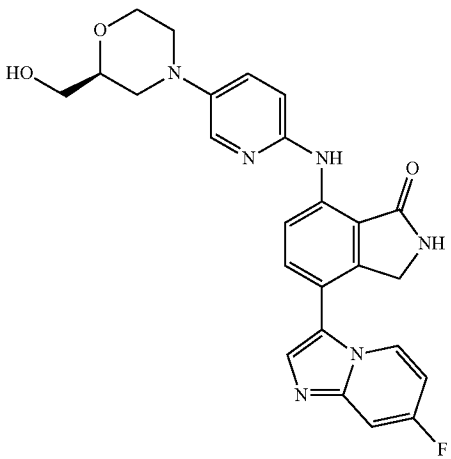 [SMILES: O=C1NCc2c(-c3cnc4cc(F)ccn34)ccc(Nc3ccc(N4CCO[C@H](CO)C4)cn3)c21] | 4-(7-fluoro-imidazo[1,2-a]pyridin-3-yl)-7-[[5-[(2S)-2-(hydroxymethyl)morpholin-4-yl]-2-pyridyl]amino]isoindolin-1-one | Method AcHSS C18, m/z = 475.2 [M + H]+, Ret. time = 2.22 min. | ¹H NMR (400 MHz, DMSO): δ 9.92 (s, 1 H), 8.82 (s, 1 H), 8.61 (d, J = 8.5 Hz, 1 H), 8.47 (dd, J = 6.1, 7.6 Hz, 1 H), 8.05 (d, J = 3.0 Hz, 1 H), 7.86 (s, 1 H), 7.74 (d, J = 8.6 Hz, 1 H), 7.59-7.48 (m, 2 H), 7.06-6.99 (m, 2 H), 4.82 (t, J = 5.7 Hz, 1H), 4.43 (s, 2H), 4.03-3.98 (m, 1 H), 3.76-3.46 (m, 6 H), 2.79-2.70 (m, 1 H), 2.53-2.46 (m, 1 H). | C AC45 BC80 |
| I-455 | 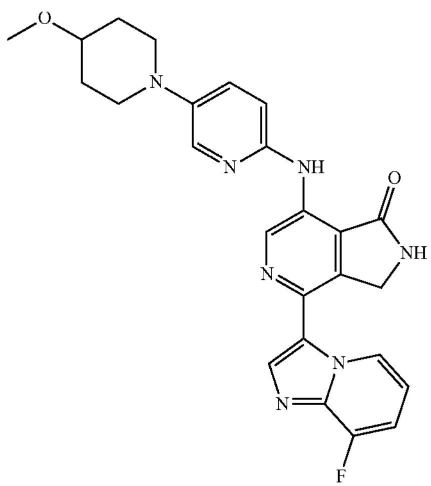 [SMILES: COC1CCN(c2ccc(Nc3cnc(-c4cnc5c(F)cccn45)c4c3C(=O)NC4)nc2)CC1] | 4-(8-fluoro-imidazo[1,2-a]pyridin-3-yl)-7-[[5-(4-methoxy-1-piperidyl)-2-pyridyl]amino]-2,3-dihydropyrrolo[3,4-c]pyridin-1-one | Method AcHSS C18, m/z = 474.2 [M + H]+, Ret. time = 3.40 min. | ¹H NMR (400 MHz, DMSO): δ 9.96 (s, 1 H), 9.75-9.73 (m, 1 H), 9.48 (s, 1 H), 9.31 (s, 1 H), 8.17 (s, 1 H), 8.10 (d, J = 3.0 Hz, 1 H), 7.52 (dd, J = 3.0, 8.8 Hz, 1 H), 7.37 (dd, J = 7.2, 11.5 Hz, 1 H), 7.14-7.06 (m, 2 H), 4.82 (s, 2 H), 3.53-3.45 (m, 2 H), 3.44-3.39 (m, 1H), 2.98-2.90 (m, 2 H), 2.06-1.96 (m, 2 H), 1.67-1.58 (m, 2 H). | Hc AC49 BC114 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-456 | 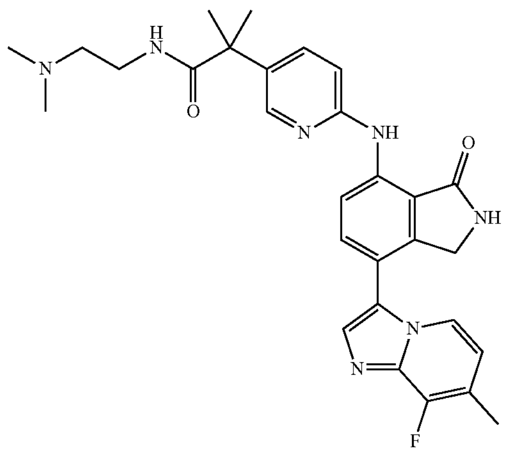 | N-[2-(dimethylamino)ethyl]-2-[6-[[7-(8-fluoro-7-methylimidazo[1,2-a]pyridin-3-yl)-3-oxoisoindolin-4-yl]amino]-3-pyridyl]-2-methylpropanamide | Method AcHSS C18, m/z = 530 [M + H]+, Ret. time = 2.40 min. | ¹H NMR (400 MHz, DMSO): δ 10.10 (s, 1 H), 8.86 (s, 1 H), 8.73 (d, J = 8.3 Hz, 1 H), 8.27 (d, J = 3.1 Hz, 1 H), 8.17 (d, J = 7.3 Hz, 1 H), 7.82 (s, 1 H), 7.73 (d, J = 8.7 Hz, 1 H), 7.64 (dd, J = 2.8, 8.7 Hz, 1 H), 7.37 (t, J = 6.4 Hz, 1 H), 7.00 (d, J = 8.7 Hz, 1 H), 6.85 (t, J = 6.6 Hz, 1 H), 4.41 (s, 2 H), 3.19-3.13 (m, 2 H), 2.35 (d, J = 2.4 Hz, 3 H), 2.29 (t, J = 6.8 Hz, 2 H), 2.15 (s, 6 H), 1.49 (s, 6 H). | C AC34 BC117 |
| I-457 | 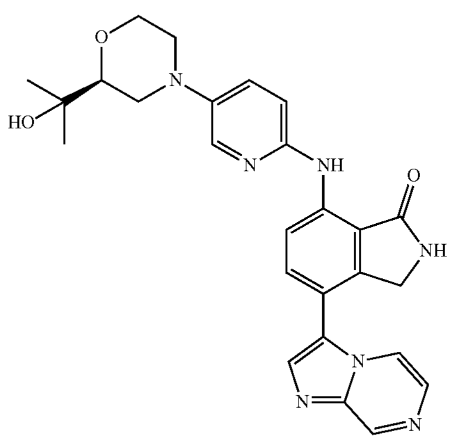 [SMILES: CC(C)(O)[C@@H]1CN(c2ccc(Nc3ccc(-c4cnc5cnccn45)c4c3C(=O)NC4)nc2)CCO1] | 7-[[5-[(2S)-2-(1-hydroxy-1-methylethyl)morpholin-4-yl]-2-pyridyl]amino]-4-imidazo[1,2-a]pyrazin-3-yl-isoindolin-1-one | Method AcHSS C18, m/z = 486 [M + H]+, Ret. time = 2.87 min. | ¹H NMR (400 MHz, DMSO): δ 9.92 (s, 1 H), 9.15 (d, J = 1.7 Hz, 1 H), 8.83 (s, 1 H), 8.61 (d, J = 8.6 Hz, 1 H), 8.47 (dd, J = 1.6, 4.7 Hz, 1 H), 8.12 (s, 1 H), 8.04 (d, J = 2.9 Hz, 1 H), 7.93 (d, J = 4.8 Hz, 1 H), 7.77 (d, J = 8.7 Hz, 1 H), 7.47 (dd, J = 3.0, 9.0 Hz, 1 H), 7.01 (d, J = 7.2 Hz, 1 H), 4.51 (s, 1 H), 4.45 (s, 2 H), 4.01 (dd, J = 2.7, 11.4 Hz, 1 H), 3.67 (dt, J = 2.7, 11.4 Hz, 1 H), 3.62 (d, J = 11.4 Hz, 1 H), 3.48 (d, J = 12.0 Hz, 1 H), 3.34-3.30 (m, 1 H), 2.67 (dt, J = 4.2, 12.0 Hz, 1 H), 2.58-2.54 (m, 1 H), 1.18 (s, 3 H), 1.13 (s, 3 H). | F AC47 BC52 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-458 | 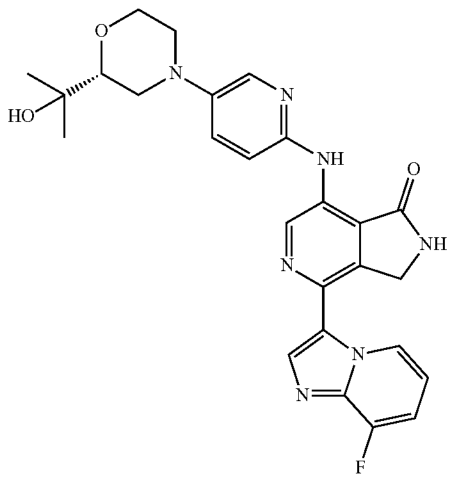 [SMILES: CC(C)(O)[C@H]1CN(c2ccc(Nc3cnc(-c4cnc5c(F)cccn45)c4c3C(=O)NC4)nc2)CCO1] | 4-(8-fluoro-imidazo[1,2-a]pyridin-3-yl)-7-[[5-[(2R)-2-(1-hydroxy-1-methyl-ethyl)morpholin-4-yl]-2-pyridyl]amino]-2,3-dihydropyrrolo[3,4-c]pyridin-1-one | Method AcHSS C18, m/z = 504 [M + H]+, Ret. time = 3.40 min. | ¹H NMR (400 MHz, DMSO): δ 9.93 (s, 1 H), 9.69 (dd, J = 0.9, 7.2 Hz, 1 H), 9.47 (s, 1 H), 9.30 (s, 1 H), 8.13 (s, 1 H), 8.06 (d, J = 2.9 Hz, 1 H), 7.48 (dd, J = 3.0, 9.0 Hz, 1 H), 7.33 (dd, J = 6.8, 11.1 Hz, 1 H), 7.11-7.05 (m, 2 H), 4.78 (s, 2 H), 4.50 (s, 1 H), 4.02 (dd, J = 2.6, 11.0 Hz, 1 H), 3.72-3.60 (m, 2 H), 3.50 (d, J = 11.4 Hz, 1 H), 2.72-2.65 (m, 1 H), 2.72-2.65 (m, 1 H), 2.58-2.54 (m, 1 H), 1.19 (s, 3 H), 1.14-1.13 (m, 3 H). | Hc AC46 BC114 |
| I-459 | 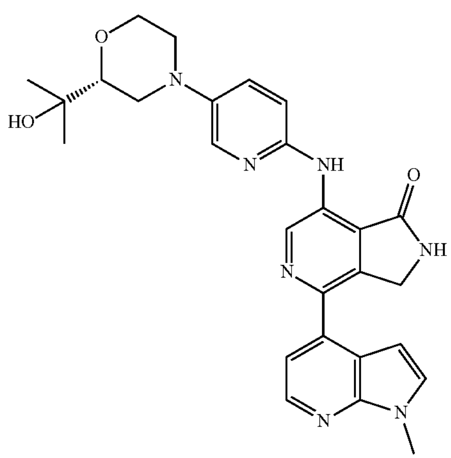 | 7-[[5-[(2R)-2-(1-hydroxy-1-methyl-ethyl)morpholin-4-yl]-2-pyridyl]amino]-4-(1-methyl-pyrrolo[2,3-b]pyridin-4-yl)-2,3-dihydropyrrolo[3,4-c]pyridin-1-one | Method AcHSS C18, m/z = 500 [M + H]+, Ret. time = 3.20 min. | ¹H NMR (400 MHz, DMSO): δ 9.94 (s, 1 H), 9.95 (s, 1 H), 9.17 (s, 1 H), 8.36 (d, J = 5.0 Hz, 1 H), 8.08 (d, J = 3.0 Hz, 1 H), 7.58 (d, J = 3.4 Hz, 1 H), 7.49 (dd, J = 3.0, 9.0 Hz, 1 H), 7.39 (d, J = 5.0 Hz, 1 H), 7.09 (d, J = 9.2 Hz, 1H), 6.92 (d, J = 3.4 Hz, 1 H), 4.73 (s, 2 H), 4.50 (s, 1 H), 4.02 (dd, J = 2.4, 11.2 Hz, 1 H), 3.88 (s, 3 H), 3.72-3.60 (m, 2 H), 3.53-3.46 (m, 1 H), 2.73-2.64 (m, 1 H), 2.58-2.53 (m, 1 H), 1.19 (s, 3 H), 1.13 (s, 3 H). | O AC46 BC26 |

TABLE 8-continued

Characterization Data (LCMS and ¹H NMR).

| # | STRUCTURE | NAME | LCMS | ¹H NMR | Method AA Reagent BB |
|---|---|---|---|---|---|
| I-460 | 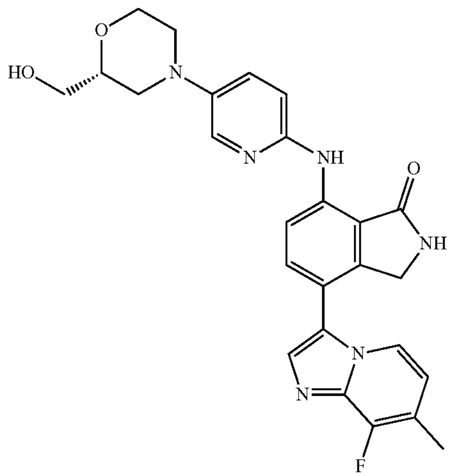 [SMILES: Cc1ccn2c(-c3ccc(Nc4ccc(N5CCO[C@@H](CO)C5)cn4)c4c3CNC4=O)cnc2c1F] | 4-(8-fluoro-7-methyl-imidazo[1,2-a]pyridin-3-yl)-7-[[5-[(2R)-2-(hydroxymethyl)morpholin-4-yl]-2-pyridyl]amino]isoindolin-1-one | Method AcHSS C18, m/z = 489 [M + H]+, Ret. time = 2.40 min. | ¹H NMR (400 MHz, DMSO): δ 9.89 (s, 1 H), 8.78 (s, 1 H), 8.58 (d, J = 8.1 Hz, 1 H), 8.16 (d, J = 7.3 Hz, 1 H), 8.01 (d, J = 3.0 Hz, 1 H), 7.81 (s, 1 H), 7.69 (d, J = 8.6 Hz, 1 H), 7.46 (dd, J = 2.9, 9.1 Hz, 1 H), 7.00 (d, J = 9.1 Hz, 1 H), 6.84 (t, J = 6.8 Hz, 1 H), 4.79 (t, J = 5.7 Hz, 1 H), 4.39 (s, 2 H), 3.96 (dd, J = 1.9, 11.5 Hz, 1 H), 3.68 (ddd, J = 11.3, 11.3, 2.7 Hz, 1 H), 3.63-3.59 (m, 1 H), 3.58-3.53 (m, 2 H), 3.50-3.43 (m, 2 H), 2.74-2.69 (m, 1 H), 2.45 (dd, J = 10.5, 11.6 Hz, 1 H), 2.35 (d, J = 2.1 Hz, 3 H). | F AC44 BC117 |
| I-461 | 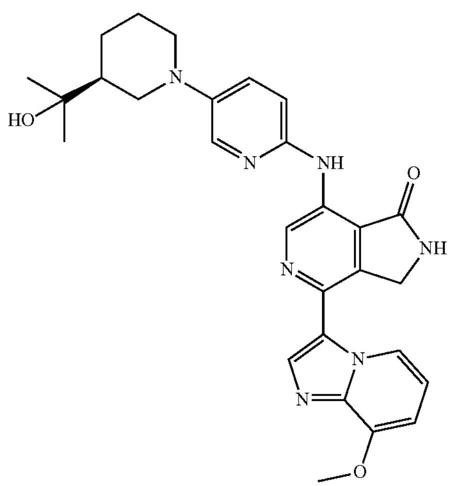 [SMILES: COc1cccn2c(-c3ncc(Nc4ccc(N5CCC[C@H](C(C)(C)O)C5)cn4)c4c3CNC4=O)cnc12] | 7-[[5-[(3S)-3-(1-hydroxy-1-methyl-ethyl)-1-piperidyl]-2-pyridyl]amino]-4-(8-methoxy-imidazo[1,2-a]pyridin-3-yl)-2,3-dihydro-pyrrolo[3,4-c]pyridin-1-one | Method AcHSS C18, m/z = 514 [M + H]+, Ret. time = 2.66 min. | ¹H NMR (400 MHz, DMSO): δ 9.93 (s, 1 H), 9.49 (d, J = 7.0 Hz, 1 H), 9.43 (s, 1 H), 9.28 (s, 1 H), 8.07 (d, J = 2.7 Hz, 1 H), 8.02 (s, 1 H), 7.47 (dd, J = 2.9, 9.2 Hz, 1 H), 7.07 (d, J = 9.0 Hz, 1 H), 7.03 (t, J = 7.4 Hz, 1 H), 6.88 (d, J = 7.9 Hz, 1 H), 4.79 (s, 2 H), 4.33 (s, 1 H), 4.03 (s, 3 H), 3.80 (d, J = 11.2 Hz, 1 H), 3.68 (d, J = 12.5 Hz, 1 H), 2.61 (ddd, J = 12.4, 12.4, 2.3 Hz, 1 H), 2.50 (t, J = 11.6 Hz, 1 H), 1.91 (d, J = 14.2 Hz, 1 H), 1.81 (d, J = 12.5 Hz, 1 H), 1.63 (ddd, J = 4.1, 10.4, 15.9 Hz, 2 H), 1.25-1.20 (m, 1 H), 1.16 (d, J = 10.4 Hz, 6 H). | O AC30 BC124 |

| # | STRUCTURE | NAME | LCMS | ¹H NMR | Method Reagent AA BB |
|---|---|---|---|---|---|
| I-462 | 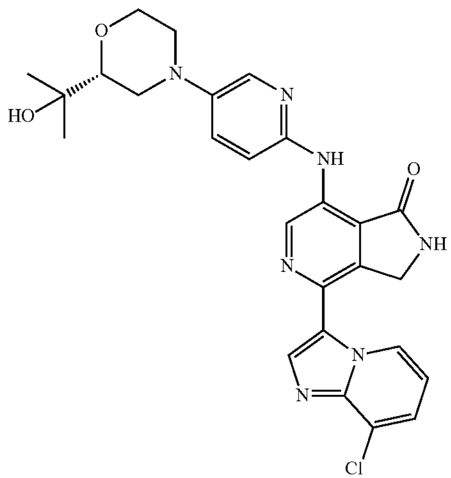 [SMILES: CC(C)(O)[C@H]1CN(c2ccc(Nc3cnc(-c4cnc5c(Cl)cccn45)c4c3C(=O)NC4)nc2)CCO1] | 4-(8-chloro-imidazo[1,2-a]pyridin-3-yl)-7-[[5-[(2R)-2-(1-hydroxy-1-methyl-ethyl)morpholin-4-yl]-2-pyridyl]amino]-2,3-dihydro-pyrrolo[3,4-c]pyridin-1-one | Method AcHSS C18, m/z = 520 [M + H]+, Ret. time = 3.50 min. | ¹H NMR (400 MHz, DMSO): δ 9.84 (s, 1 H), 9.74 (dd, J = 0.9, 7.2 Hz, 1 H), 9.38 (s, 1 H), 9.20 (s, 1 H), 8.06 (s, 1 H), 7.98 (d, J = 3.4 Hz, 1 H), 7.54 (dd, J = 1.1, 7.4 Hz, 1 H), 7.40 (dd, J = 3.1, 9.1 Hz, 1 H), 7.01 (t, J = 7.2 Hz, 1 H), 6.99 (d, J = 8.9 Hz, 1 H), 4.70 (s, 2 H), 4.41 (s, 1 H), 3.94 (dd, J = 2.5, 11.4 Hz, 1 H), 3.59 (ddd, J = 11.5, 11.5, 2.6 Hz, 1 H), 3.53 (d, J = 12.5 Hz, 1 H), 3.40 (d, J = 11.7 Hz, 1 H), 3.27-3.25 (m, 1 H), 2.60 (ddd, J = 6.9, 6.9, 17.2 Hz, 1 H), 2.49-2.45 (m, 1 H), 1.11 (s, 3 H), 1.05 (s, 3 H). | O AC46 BC127 |

| # | STRUCTURE | NAME | LCMS | 1H NMR | Method Reagent AA BB |
|---|---|---|---|---|---|
| I-463 | 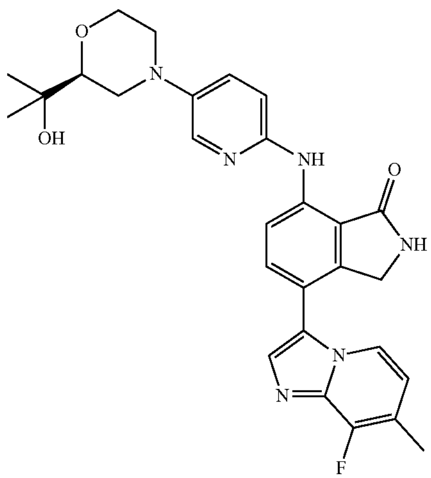 [SMILES: Cc1ccn2c(-c3ccc(Nc4ccc(N5CCO[C@H](C(C)(C)O)C5)cn4)c4c3CNC4=O)cnc2c1F] | 4-(8-fluoro-7-methyl-imidazo[1,2-a]pyridin-3-yl)-7-[[5-[(2S)-2-(1-hydroxy-1-methyl-ethyl)morpholin-4-yl]-2-pyridyl]amino]iso-indolin-1-one | Method BicarbB EHC18, m/z = 517.2 [M + H]+, Ret. time = 3.89 min. | 1H NMR (400 MHz, DMSO): δ 9.92 (s, 1 H), 8.82 (s, 1 H), 8.62 (d, J = 8.8 Hz, 1 H), 8.19 (d, J = 7.1 Hz, 1 H), 8.07 (d, J = 3.0 Hz, 1 H), 7.84 (s, 1 H), 7.72 (d, J = 8.6 Hz, 1 H), 7.50 (dd, J = 3.0, 9.1 Hz, 1 H), 7.04 (d, J = 9.1 Hz, 1 H), 6.88 (t, J = 6.9 Hz, 1 H), 4.53 (s, 1 H), 4.43 (s, 2 H), 4.05 (dd, J = 2.7, 11.3 Hz, 1 H), 3.71 (ddd, J = 11.7, 11.7, 3.1 Hz, 1 H), 3.64 (d, J = 11.7 Hz, 1 H), 3.50 (d, J = 11.5 Hz, 1 H), 3.37-3.33 (m, 1 H), 2.71 (ddd, J = 11.9, 11.9, 3.6 Hz, 1 H), 2.55-2.54 (m, 1 H), 2.39 (d, J = 2.1 Hz, 3 H), 1.23 (s, 3H), 1.17 (s, 3 H). | F AC47 BC117 |
| I-464 | 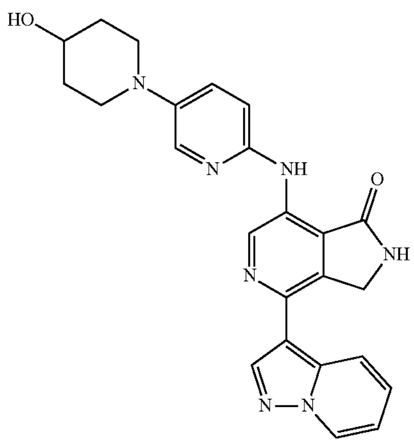 [SMILES: O=C1NCc2c(-c3cnn4ccccc34)ncc(Nc3ccc(N4CCC(O)CC4)cn3)c21] | 7-[[5-(4-hydroxy-1-piperidyl)-2-pyridyl]amino]-4-pyrazolo[1,5-a]pyridin-3-yl-2,3-dihydro-pyrrolo[3,4-c]pyridin-1-one | Method AcHSS C18, m/z = 442 [M + H]+, Ret. time = 2.60 min. | 1H NMR (400 MHz, DMSO): δ 9.83 (s, 1 H), 9.29 (s, 1 H), 9.20 (s, 1 H), 8.79 (d, J = 6.9 Hz, 1 H), 8.63 (d, J = 9.1 Hz, 1 H), 8.41 (s, 1 H), 8.03 (s, 1 H), 7.45-7.39 (m, 2 H), 7.05 (t, J = 6.5 Hz, 1 H), 6.99 (d, J = 8.3 Hz, 1 H), 4.77 (s, 2 H), 4.71 (dd, J = 1.4, 4.4 Hz, 1 H), 3.68-3.59 (m, 1 H), 3.47 (ddd, J = 4.4, 4.4, 11.7 Hz, 2 H), 2.84 (t, J = 9.8 Hz, 2 H), 1.86 (t, J = 6.2 Hz, 2 H), 1.60-1.51 (m, 2 H). | O AC15 BC121 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-465 | 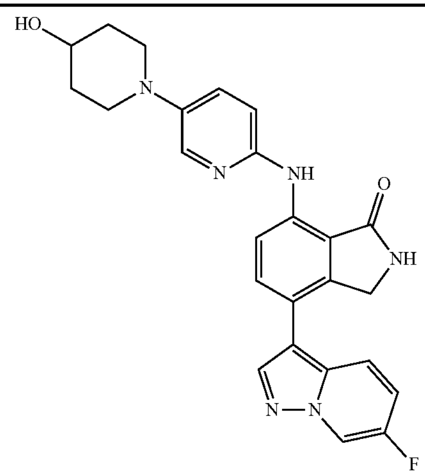 | 4-(6-fluoro-pyrazolo[1,5-a]pyridin-3-yl)-7-[[5-(4-hydroxy-1-piperidyl)-2-pyridyl]amino]isoindolin-1-one | Method AcHSS C18, m/z = 459.1 [M + H]+, Ret. time = 2.96 min. | ¹H NMR (400 MHz, DMSO): δ 9.70 (s, 1 H), 8.98 (dd, J = 2.0, 4.8 Hz, 1 H), 8.67 (s, 1 H), 8.42 (d, J = 8.6 Hz, 1 H), 8.28 (s, 1 H), 7.91 (d, J = 3.1 Hz, 1 H), 7.80 (dd, J = 5.7, 9.7 Hz, 1 H), 7.58 (d, J = 8.4 Hz, 1 H), 7.37-7.29 (m, 2 H), 6.83 (d, J = 9.0 Hz, 1 H), 4.61 (d, J = 4.3 Hz, 1 H), 4.42 (s, 2 H), 3.59-3.50 (m, 1 H), 3.41-3.33 (m, 2 H), 2.73 (ddd, J = 2.6, 9.9, 12.4 Hz, 2 H), 1.77 (dd, J = 4.5, 12.5 Hz, 2 H), 1.44 (ddt, J = 3.2, 10.6, 11.3 Hz, 2 H). | F AC15 BC122 |
| I-467 | 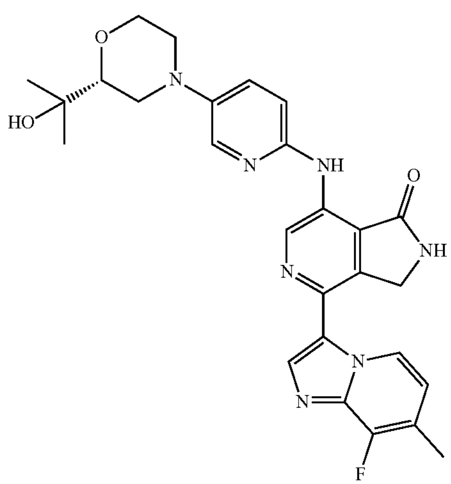 [SMILES: Cc1ccn2c(-c3ncc(Nc4ccc(N5CCO[C@@H](C(C)(C)O)C5)cn4)c4c3CNC4=O)cnc2c1F] | 4-(8-fluoro-7-methyl-imidazo[1,2-a]pyridin-3-yl)-7-[[5-[(2R)-2-(1-hydroxy-1-methyl-ethyl)morpholin-4-yl]-2-pyridyl]amino]-2,3-dihydropyrrolo[3,4-c]pyridin-1-one | Method AcHSS C18, m/z = 518 [M + H]+, Ret. time = 3.37 min. | ¹H NMR (400 MHz, DMSO): δ 9.91 (s, 1 H), 9.62 (d, J = 7.1 Hz, 1 H), 9.45 (s, 1 H), 9.29 (s, 1 H), 8.06 (s, 2 H), 7.48 (dd, J = 3.1, 9.1 Hz, 1 H), 7.08 (d, J = 8.9 Hz, 1 H), 7.01 (t, J = 7.1 Hz, 1 H), 4.76 (s, 2 H), 4.47 (s, 1 H), 4.02 (dd, J = 3.2, 11.6 Hz, 1 H), 3.68 (ddd, J = 11.9, 11.9, 3.1 Hz, 1 H), 3.62 (d, J = 12.8 Hz, 1 H), 3.49 (d, J = 12.6 Hz, 1 H), 3.34 (dd, J = 2.2, 10.6 Hz, 1 H), 2.68 (ddd, J = 12.2, 12.2, 3.5 Hz, 1 H), 2.57-2.53 (m, 1 H), 2.38 (d, J = 2.3 Hz, 3 H), 1.19 (s, 3 H), 1.13 (s, 3 H). | Hc AC46 BC123 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-468 | 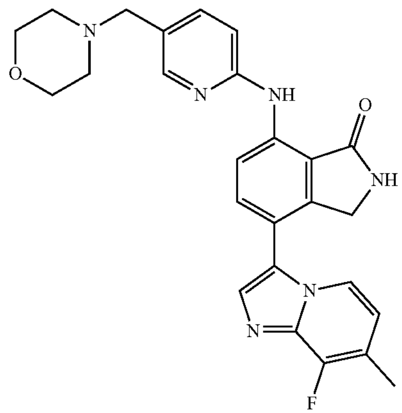 [SMILES: Cc1ccn2c(-c3ccc(Nc4ccc(CN5CCOCC5)cn4)c4c3CNC4=O)cnc2c1F] | 4-(8-fluoro-7-methyl-imidazo[1,2-a]pyridin-3-yl)-7-[[5-(morpholino-methyl)-2-pyridyl]amino]isoindolin-1-one | Method BicarbB EHC18, m/z = 473 [M + H]+, Ret. time = 3.82 min. | ¹H NMR (400 MHz, DMSO): δ 10.16 (s, 1 H), 8.89 (s, 1 H), 8.76 (d, J = 8.7 Hz, 1 H), 8.26 (d, J = 1.8 Hz, 1 H), 8.21 (d, J = 7.2 Hz, 1 H), 7.86 (s, 1 H), 7.78 (d, J = 8.6 Hz, 1 H), 7.70 (dd, J = 2.2, 8.4 Hz, 1 H), 7.05 (d, J = 8.4 Hz, 1 H), 6.89 (t, J = 6.8 Hz, 1 H), 4.45 (s, 2 H), 3.64 (t, J = 4.1 Hz, 4 H), 3.49 (s, 2 H), 2.43 (t, J = 3.7 Hz, 4 H), 2.39 (d, J = 2.1 Hz, 3 H). | F AC38 BC117 |
| I-469 | 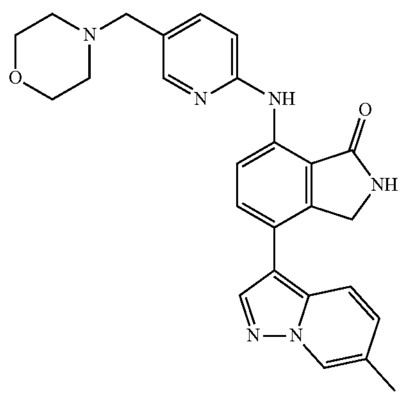 [SMILES: Cc1ccc2c(-c3ccc(Nc4ccc(CN5CCOCC5)cn4)c4c3CNC4=O)cnn2c1] | 4-(6-methyl-pyrazolo[1,5-a]pyridin-3-yl)-7-[[5-(morpholino-methyl)-2-pyridyl]amino]isoindolin-1-one | Method AcHSS C18, m/z = 455 [M + H]+, Ret. time = 2.92 min. | ¹H NMR (400 MHz, DMSO): δ 10.09 (s, 1 H), 8.88 (s, 1 H), 8.69 (d, J = 8.4 Hz, 1 H), 8.63 (d, J = 1.6 Hz, 1 H), 8.30 (s, 1 H), 8.23 (d, J = 2.2 Hz, 1 H), 7.82 (d, J = 9.3 Hz, 1 H), 7.75 (d, J = 8.8 Hz, 1 H), 7.67 (dd, J = 2.3, 8.5 Hz, 1 H), 7.23 (dd, J = 1.4, 9.3 Hz, 1 H), 7.01 (d, J = 8.6 Hz, 1 H), 4.57 (s, 2 H), 3.63 (t, J = 4.6 Hz, 4 H), 3.48 (s, 2 H), 2.42 (t, J = 4.7 Hz, 4 H), 2.38 (s, 3 H). | F AC38 BC46 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-470 | 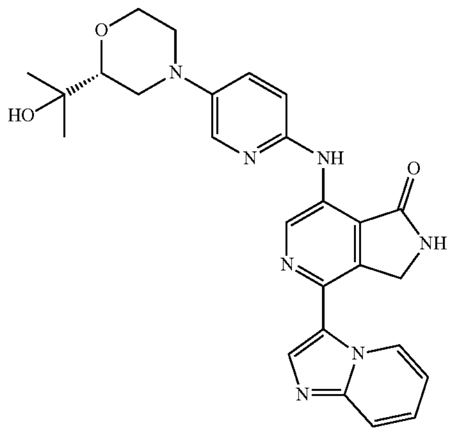 [SMILES: CC(C)(O)[C@H]1CN(c2ccc(Nc3cnc(-c4cnc5ccccn45)c4c3C(=O)NC4)nc2)CCO1] | 7-[[5-[(2R)-2-(1-hydroxy-1-methylethyl)morpholin-4-yl]-2-pyridyl]amino]-4-imidazo[1,2-a]pyridin-3-yl-2,3-dihydropyrrolo[3,4-c]pyridin-1-one | Method AcHSS C18, m/z = 486 [M + H]+, Ret. time = 2.70 min. | ¹H NMR (400 MHz, DMSO): δ 10.09 (s, 1 H), 8.88 (s, 1 H), 8.69 (d, J = 8.4 Hz, 1 H), 8.63 (d, J = 1.6 Hz, 1 H), 8.30 (s, 1 H), 8.23 (d, J = 2.2 Hz, 1 H), 7.82 (d, J = 9.3 Hz, 1 H), 7.75 (d, J = 8.8 Hz, 1 H), 7.67 (dd, J = 2.3, 8.5 Hz, 1 H), 7.23 (dd, J = 1.4, 9.3 Hz, 1 H), 7.01 (d, J = 8.6 Hz, 1 H), 4.57 (s, 2 H), 3.63 (t, J = 4.6 Hz, 4 H), 3.48 (s, 2 H), 2.42 (t, J = 4.7 Hz, 4 H), 2.38 (s, 3 H). | O AC46 BC42 |
| I-471 | 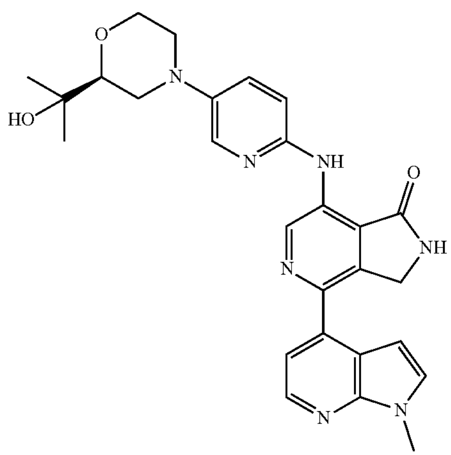 [SMILES: Cn1ccc2c(-c3ncc(Nc4ccc(N5CCO[C@H](C(C)(C)O)C5)cn4)c4c3CNC4=O)ccnc21] | 7-[[5-[(2S)-2-(1-hydroxy-1-methylethyl)morpholin-4-yl]-2-pyridyl]amino]-4-(1-methylpyrrolo[2,3-b]pyridin-4-yl)-2,3-dihydropyrrolo[3,4-c]pyridin-1-one | Method AcHSS C18, m/z = 500.6 [M + H]+, Ret. time = 3.20 min. | ¹H NMR (400 MHz, DMSO): δ 9.94 (s, 1 H), 9.54 (s, 1 H), 9.17 (s, 1 H), 8.36 (d, J = 4.9 Hz, 1 H), 8.08 (d, J = 3.0 Hz, 1 H), 7.58 (d, J = 3.5 Hz, 1 H), 7.49 (dd, J = 3.0, 9.0 Hz, 1 H), 7.38 (d, J = 5.0 Hz, 1 H), 7.11-7.08 (m, 1 H), 6.92 (d, J = 3.4 Hz, 1 H), 4.72 (s, 2 H), 4.52-4.49 (m, 1 H), 4.02 (dd, J = 2.4, 11.3 Hz, 1 H), 3.88 (s, 3 H), 3.71-3.60 (m, 2 H), 3.50 (d, J = 11.2 Hz, 1 H), 3.35 (s, 1 H), 2.73-2.64 (m, 1 H), 2.58-2.54 (m, 1 H), 1.19 (s, 3 H), 1.13 (s, 3 H). | O AC47 BC26 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-472 | 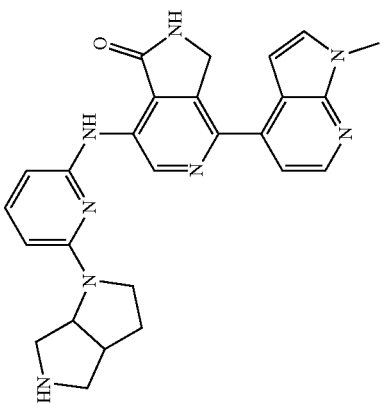 | 7-[[6-(3,3a,4,5,6,6a-hexahydro-2H-pyrrolo[2,3-c]pyrrol-1-yl)-2-pyridyl]amino]-4-(1-methyl-pyrrolo[2,3-b]pyridin-4-yl)-2,3-di-hydropyrrolo[3,4-c]pyridin-1-one | Method AcHSS C18, m/z = 467 [M + H]+, Ret. time = 2.83 min. | ¹H NMR (400 MHz, DMSO): δ 10.00 (s, 1 H), 8.41 (s, 1 H), 8.39 (d, J = 5.0 Hz, 1 H), 7.59 (d, J = 3.6 Hz, 1 H), 7.54 (t, J = 7.9 Hz, 1 H), 7.40 (d, J = 5.5 Hz, 1 H), 6.86 (d, J = 3.4 Hz, 1 H), 6.32 (d, J = 7.7 Hz, 1 H), 6.16 (d, J = 8.3 Hz, 1 H), 4.69 (s, 2 H), 4.60 (s, 1 H), 3.90 (s, 3 H), 3.81-3.77 (m, 1 H), 3.57-3.52 (m, 1 H), 3.45-3.41 (m, 1 H), 3.35-3.27 (m, 2 H), 3.20-3.15 (m, 1 H), 3.11-3.07 (m, 1 H), 2.26-2.16 (m, 1 H), 2.02-1.93 (m, 1 H). | O AC51 BC26 |
| I-473 | 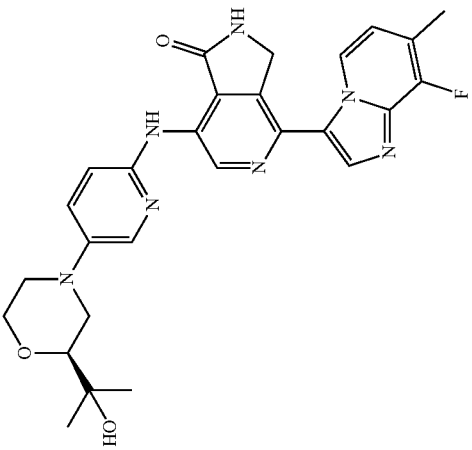 | 4-(8-fluoro-7-methyl-imidazo[1,2-a]pyridin-3-yl)-7-[[5-[(2S)-2-(1-hydroxy-1-methyl-ethyl)morpholin-4-yl]-2-pyridyl]amino]-2,3-dihydro-pyrrolo[3,4-c]pyridin-1-one | Method AcHSS C18, m/z = 518 [M + H]+, Ret. time = 3.37 min. | ¹H NMR (400 MHz, DMSO): δ 9.91 (s, 1 H), 9.61 (d, J = 7.0 Hz, 1 H), 9.44 (s, 1 H), 9.28 (s, 1 H), 8.05 (d, J = 3.0 Hz, 1 H), 8.03 (s, 1 H), 7.48 (dd, J = 3.0, 9.1 Hz, 1 H), 7.06 (d, J = 9.5 Hz, 1 H), 6.99 (t, J = 6.9 Hz, 1 H), 4.76 (s, 2 H), 4.50 (s, 1 H), 4.02 (dd, J = 2.6, 11.7 Hz, 1 H), 3.68 (ddd, J = 11.6, 11.6, 3.1 Hz, 1 H), 3.63 (d, J = 10.9 Hz, 1 H), 3.48 (d, J = 9.8 Hz, 1 H), 3.33-3.32 (m, 1 H), 2.68 (ddd, J = 11.8, 11.8, 3.5 Hz, 1 H), 2.58-2.54 (m, 1 H), 2.37 (d, J = 2.3 Hz, 3 H), 1.19 (s, 3 H), 1.14 (s, 3 H). | Hc AC47 BC123 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-474 | 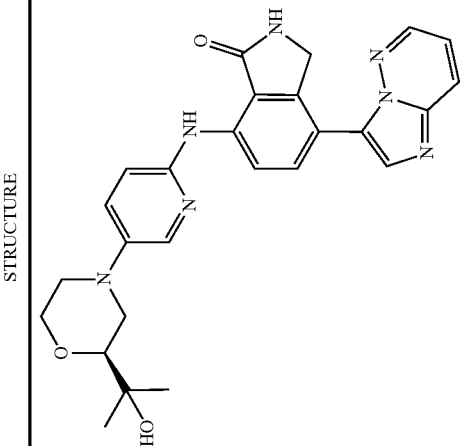 | 7-[[5-[(2S)-2-(1-hydroxy-1-methylethyl)morpholin-4-yl]-2-pyridyl]amino]-4-imidazo[1,2-b]pyridazin-3-yl-isoindolin-1-one | Method AcHSS C18, m/z = 486 [M + H]+, Ret. time = 2.92 min. | ¹H NMR (400 MHz, DMSO): δ 9.95 (s, 1 H), 8.85 (s, 1 H), 8.65 (dd, J = 1.6, 4.7 Hz, 1 H), 8.55 (d, J = 8.9 Hz, 1 H), 8.25 (dd, J = 1.5, 9.1 Hz, 1 H), 8.15 (d, J = 8.2 Hz, 1 H), 8.13 (s, 1 H), 8.05 (d, J = 3.1 Hz, 1 H), 7.49 (dd, J = 2.9, 9.2 Hz, 1 H), 7.33 (dd, J = 4.4, 9.1 Hz, 1 H), 7.03 (d, J = 8.9 Hz, 1 H), 4.57 (s, 2 H), 4.53 (s, 1 H), 4.03 (dd, J = 3.2, 11.1 Hz, 1 H), 3.69 (ddd, J = 11.5, 11.5, 2.7 Hz, 1 H), 3.63 (d, J = 11.8 Hz, 1 H), 3.49 (d, J = 11.3 Hz, 1 H), 3.35-3.34 (m, 1 H), 2.69 (dt, J = 3.9, 11.8 Hz, 1 H), 2.53-2.51 (m, 1 H), 1.21 (s, 3 H), 1.15 (s, 3 H). | F AC47 BC43 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-475 | 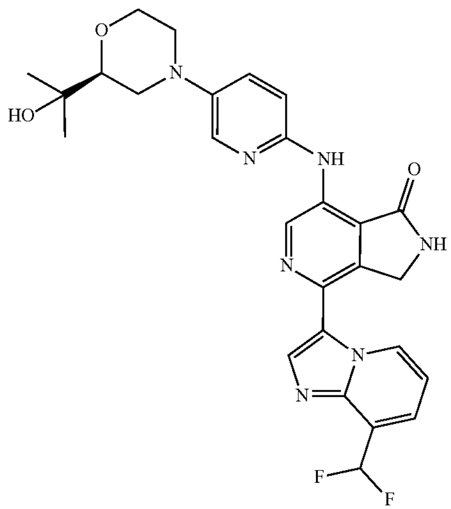 [SMILES: CC(C)(O)[C@@H]1CN(c2ccc(Nc3cnc(-c4cnc5c(C(F)F)cccn45)c4c3C(=O)NC4)nc2)CCO1] | 4-[8-(difluoromethyl)imidazo[1,2-a]pyridin-3-yl]-7-[[5-[(2S)-2-(1-hydroxy-1-methylethyl)morpholin-4-yl]-2-pyridyl]amino]-2,3-dihydropyrrolo[3,4-c]pyridin-1-one Formic acid salt | Method AcHSS C18, m/z = 536.5 [M + H]+, Ret. time = 3.62 min. | ¹H NMR (400 MHz, DMSO): δ 9.96 (dd, J = 1.0, 7.2 Hz, 1 H), 9.93 (s, 1 H), 9.45 (s, 1 H), 9.29 (s, 1 H), 8.15 (s, 1 H), 8.06 (d, J = 2.9 Hz, 1 H), 7.70 (dd, J = 1.0, 7.1 Hz, 1 H), 7.50 (s, 1 H), 7.50 (d, J = 108.7 Hz, 1 H), 7.48 (dd, J = 3.0, 9.0 Hz, 1 H), 7.22 (t, J = 7.1 Hz, 1 H), 7.07 (d, J = 9.0 Hz, 1 H), 4.78 (s, 2 H), 4.50 (s, 1 H), 4.02 (dd, J = 2.4, 11.4 Hz, 1 H), 3.67 (ddd, J = 11.6, 11.6, 2.7 Hz, 1 H), 3.62 (d, J = 11.9 Hz 1 H), 3.50 (d, J = 10.7 Hz, 1 H), 3.33-3.30 (m, 1 H), 2.69 (dt, J = 3.1, 11.7 Hz, 1 H), 2.56 (d, J = 11.1 Hz, 1 H). | Hc AC47 BC120 |
| I-476 | 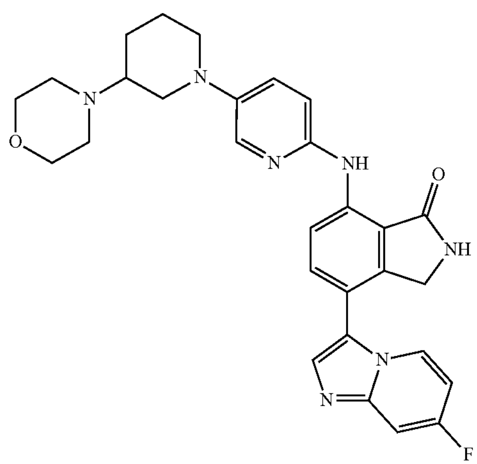 [SMILES: O=C1NCc2c(-c3cnc4cc(F)ccn34)ccc(Nc3ccc(N4CCCC(N5CCOCC5)C4)cn3)c21] | 4-(7-fluoroimidazo[1,2-a]pyridin-3-yl)-7-[[5-(3-morpholino-1-piperidyl)-2-pyridyl]amino]isoindolin-1-one | Method AcHSS C18, m/z = 528 [M + H]+, Ret. time = 2.04 min. | ¹H NMR (400 MHz, DMSO): δ 9.78 (s, 1 H), 8.70 (s, 1 H), 8.49 (d, J = 8.6 Hz, 1 H), 8.34 (dd, J = 5.8, 7.6 Hz, 1 H), 7.96 (d, J = 3.3 Hz, 1 H), 7.74 (s, 1 H), 7.61 (d, J = 8.6 Hz, 1 H), 7.45 (dd, J = 2.8, 10.1 Hz, 1 H), 7.39 (dd, J = 2.9, 9.0 Hz, 1 H), 6.90 (ddd, J = 6.7, 6.7, 2.0 Hz, 1 H), 6.89 (d, J = 9.3 Hz, 1 H), 4.30 (s, 2 H), 3.66-3.58 (m, 5 H), 3.44 (d, J = 13.5 Hz, 2 H), 2.67-2.54 (m, 6 H), 1.91 (d, J = 10.1 Hz, 1 H), 1.75 (d, J = 15.5 Hz, 1 H), 1.67-1.47 (m, 1 H), 1.32-1.29 (m, 1 H). | F AC52 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-477 | 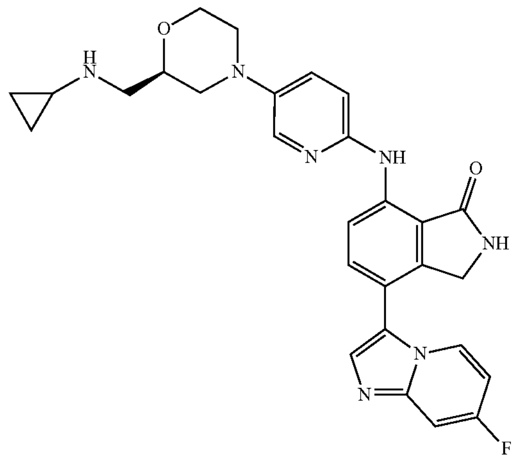 [SMILES: O=C1NCc2c(-c3cnc4cc(F)ccn34)ccc(Nc3ccc(N4CCO[C@H](CNC5CC5)C4)cn3)c21] | 7-[[5-[(2R)-2-[(cyclopropyl-amino)meth-yl]morpholin-4-yl]-2-pyridyl]amino]-4-(7-fluoro-imidazo[1,2-a]pyridin-3-yl)isoindolin-1-one | Method AcHSS C18, m/z = 514 [M + H]+, Ret. time = 1.96 min. | ¹H NMR (400 MHz, DMSO): δ 9.78 (s, 1 H), 8.70 (s, 1 H), 8.49 (d, J = 8.6 Hz, 1 H), 8.34 (dd, J = 5.8, 7.6 Hz, 1 H), 7.96 (d, J = 3.3 Hz, 1 H), 7.74 (s, 1 H), 7.61 (d, J = 8.6 Hz, 1 H), 7.45 (dd, J = 2.8, 10.1 Hz, 1 H), 7.39 (dd, J = 2.9, 9.0 Hz, 1 H), 6.90 (ddd, J = 6.7, 6.7, 2.0 Hz, 1 H), 6.89 (d, J = 9.3 Hz, 1 H), 4.30 (s, 2H), 3.66-3.58 (m, 5 H), 3.44 (d, J = 13.5 Hz, 2 H), 2.67-2.54 (m, 6 H), 1.91 (d, J = 10.1 Hz, 1 H), 1.75 (d, J = 15.5 Hz, 1 H), 1.67-1.47 (m, 1 H), 1.32-1.29 (m, 1 H). | F AC53 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-478 | Isomer 1 Separated by Chiral SFC | (R)-7-((6-((dimethylamino)methyl)-5-(tetrahydrofuran-3-yl)pyridin-2-yl)amino)-4-(7-fluoroimidazo[1,2-a]pyridin-3-yl)isoindolin-1-one | Method AcHSS C18, m/z = 487.2 [M + H]+, Ret. time = 1.98 min. | ¹H NMR (400 MHz, DMSO): δ 10.09 (s, 1 H), 8.88 (s, 1 H), 8.81 (d, J = 8.5 Hz, 1 H), 8.50 (dd, J = 5.7, 7.7 Hz, 1 H), 7.87 (s, 1 H), 7.77 (d, J = 8.7 Hz, 1 H), 7.71 (d, J = 8.5 Hz, 1 H), 7.57 (dd, J = 2.7, 10.3 Hz, 1 H), 7.02 (ddd, J = 4.3, 4.3, 10.5 Hz, 1 H), 6.99 (d, J = 8.5 Hz, 1 H), 4.44 (s, 2 H), 4.07-3.99 (m, 2 H), 3.92-3.82 (m, 2 H), 3.70 (d, J = 13.3 Hz, 1 H), 3.63-3.54 (m, 2 H), 2.39-2.31 (m, 1 H), 2.27 (s, 6 H), 1.98-1.90 (m, 1 H). | Sp AC50 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-479 | Isomer 2 Separated by Chiral SFC | (S)-7-((6-((dimethylamino)methyl)-5-(tetrahydrofuran-3-yl)pyridin-2-yl)amino)-4-(7-fluoroimidazo[1,2-a]pyridin-3-yl)isoindolin-1-one | Method AcHSS C18, m/z = 487.2 [M + H]+, Ret. time = 1.99 min. | ¹H NMR (400 MHz, DMSO): δ 10.09 (s, 1 H), 8.88 (s, 1 H), 8.81 (d, J = 8.5 Hz, 1 H), 8.50 (dd, J = 5.7, 7.7 Hz, 1 H), 7.87 (s, 1 H), 7.77 (d, J = 8.7 Hz, 1 H), 7.71 (d, J = 8.5 Hz, 1 H), 7.57 (dd, J = 2.7, 10.3 Hz, 1 H), 7.02 (ddd, J = 4.3, 4.3, 10.5 Hz, 1 H), 6.99 (d, J = 8.5 Hz, 1 H), 4.44 (s, 2 H), 4.07-3.99 (m, 2 H), 3.92-3.82 (m, 2 H), 3.70 (d, J = 13.3 Hz, 1 H), 3.63-3.54 (m, 2 H), 2.39-2.31 (m, 1 H), 2.27 (s, 6H ), 1.98-1.90 (m, 1 H). | Sp AC50 BC80 |
| I-480 | 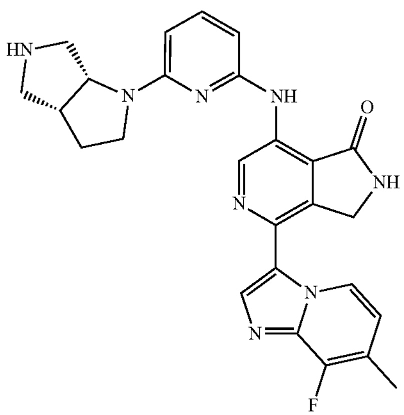 [SMILES: Cc1ccn2c(-c3ncc(Nc4cccc(N5CC[C@@H]6CNC[C@@H]65)n4)c4c3CNC4=O)cnc2c1F] | 7-[[6-[(3aR,6aR)-3,3a,4,5,6,6a-hexahydro-2H-pyrrolo[2,3-c]pyrrol-1-yl]-2-pyridyl]amino]-4-(8-fluoro-7-methylimidazo[1,2-a]pyridin-3-yl)-2,3-dihydropyrrolo[3,4-c]pyridin-1-one Formic acid salt | Method AcHSS C18, m/z = 485 [M + H]+, Ret. time = 2.79 min. | ¹H NMR (400 MHz, DMSO): δ 9.92 (s, 1 H), 9.53 (d, J = 7.4 Hz, 1 H), 9.46 (s, 1 H), 9.32 (s, 1 H), 8.36 (s, 1 H), 8.01 (s, 1 H), 7.46 (t, J = 7.9 Hz, 1 H), 6.99 (t, J = 7.0 Hz, 1 H), 6.21 (d, J = 7.6 Hz, 1 H), 6.06 (d, J = 8.1 Hz, 1 H), 4.72 (s, 2 H), 4.43 (s, 1 H), 3.25-3.20 (m, 2 H), 3.08 (t, J = 11.4 Hz, 2 H), 3.03-2.98 (m, 2 H), 2.90 (dd, J = 2.3, 10.6 Hz, 2 H), 2.35 (s, 3 H), 2.19-2.11 (m, 1 H), 1.95-1.87 (m, 1 H). | Hc AC54 BC123 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-481 | 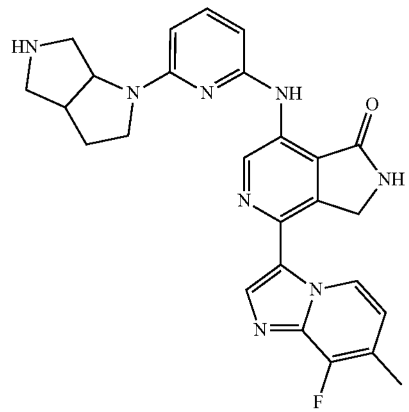 [SMILES: Cc1ccn2c(-c3ncc(Nc4cccc(N5CCC6CNCC65)n4)c4c3CNC4=O)cnc2c1F] | 7-[[6-(3,3a,4,5,6,6a-hexahydro-2H-pyrrolo[2,3-c]pyrrol-1-yl)-2-pyridyl]amino]-4-(8-fluoro-7-methyl-imidazo[1,2-a]pyridin-3-yl)-2,3-dihydro-pyrrolo[3,4-c]pyridin-1-one Formic acid salt | Method AcHSS C18, m/z = 485 [M + H]+, Ret. time = 2.82 min. | ¹H NMR (400 MHz, DMSO): δ 9.92 (s, 1 H), 9.53 (d, J = 7.4 Hz, 1 H), 9.46 (s, 1 H), 9.32 (s, 1 H), 8.36 (s, 1 H), 8.01 (s, 1 H), 7.46 (t, J = 7.9 Hz, 1 H), 6.99 (t, J = 7.0 Hz, 1 H), 6.21 (d, J = 7.6 Hz, 1 H), 6.06 (d, J = 8.1 Hz, 1 H), 4.72 (s, 2 H), 4.43 (s, 1 H), 3.25-3.20 (m, 2 H), 3.08 (t, J = 11.4 Hz, 2 H), 3.03-2.98 (m, 2 H), 2.90 (dd, J = 2.3, 10.6 Hz, 2 H), 2.35 (s, 3H), 2.19-2.11 (m, 1 H), 1.95-1.87 (m, 1 H). | Hc AC51 BC123 |
| I-482 | racemic | 7-[[5-[(2R)-2-[(3-fluoroazetidin-1-yl)methyl]morpholin-4-yl]-2-pyridyl]amino]-4-(7-fluoro-imidazo[1,2-a]pyridin-3-yl)isoindolin-1-one | Method AcHSS C18, m/z = 532 [M + H]+, Ret. time = 2.03 min. | ¹H NMR (400 MHz, DMSO): δ 9.79 (s, 1 H), 8.69 (s, 1 H), 8.48 (d, J = 8.7 Hz, 1 H), 8.34 (dd, J = 5.8, 7.5 Hz, 1 H), 7.92 (d, J = 2.8 Hz, 1 H), 7.73 (d, J = 2.8 Hz, 1 H), 7.61 (d, J = 8.8 Hz, 1 H), 7.44 (dd, J = 2.7, 10.1 Hz, 1 H), 7.37 (dd, J = 2.9, 9.1 Hz, 1 H), 6.92-6.87 (m, 2 H), 5.17-4.96 (m, 1 H), 4.30 (s, 2 H), 3.85 (td, J = 1.5, 10.3 Hz, 1 H), 3.60-3.47 (m, 4 H), 3.43-3.33 (m, 2 H), 3.15-3.03 (m, 2 H), 2.60 (dt, J = 3.9, 11.9 Hz, 1 H), 2.52 (t, J = 5.6 Hz, 2 H), 2.36 (t, J = 11.0 Hz, 1 H). | F AC55 BC80 |

| # | STRUCTURE | NAME | LCMS | ¹H NMR | Method Reagent AA BB |
|---|---|---|---|---|---|
| I-483 | 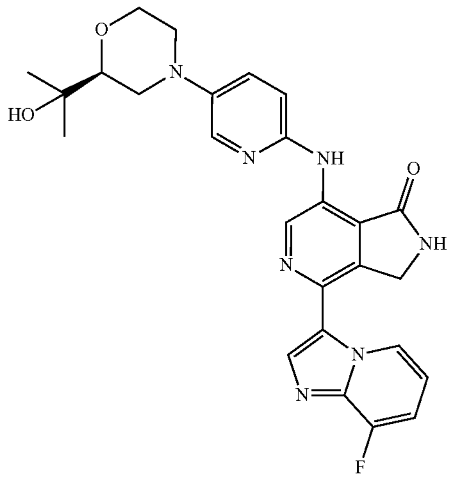 [SMILES: CC(C)(O)[C@@H]1CN(c2ccc(Nc3cnc(-c4cnc5c(F)cccn45)c4c3C(=O)NC4)nc2)CCO1] | 4-(8-fluoro-imidazo[1,2-a]pyridin-3-yl)-7-[[5-[(2S)-2-(1-hydroxy-1-methyl-ethyl)morpholin-4-yl]-2-pyridyl]amino]-2,3-dihydropyrrolo[3,4-c]pyridin-1-one | Method AcHSS C18, m/z = 504 [M + H]+, Ret. time = 3.38 min. | ¹H NMR (400 MHz, DMSO): δ 9.97 (s, 1 H), 9.73 (d, J = 7.3 Hz, 1 H), 9.51 (s, 1 H), 9.32 (s, 1 H), 8.18 (s, 1 H), 8.11 (s, 1 H), 7.52 (d, J = 8.0 Hz, 1 H), 7.37 (t, J = 10.0 Hz, 1 H), 7.12 (d, J = 9.8 Hz, 2 H), 4.83 (s, 2 H), 4.53 (s, 1 H), 4.06 (d, J = 10.6 Hz, 1 H), 3.75-3.65 (m, 2 H), 3.53 (d, J = 11.3 Hz, 2 H), 2.76-2.70 (m, 1 H), 2.64 (d, J = 19.4 Hz, 1 H), 1.24 (s, 3 H), 1.16 (s, 3 H). | Hc AC47 BC118 |
| I-484 | 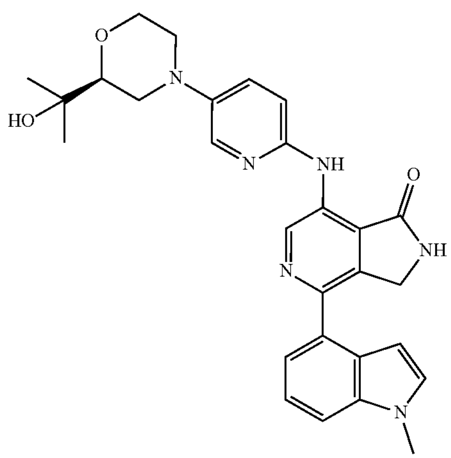 [SMILES: Cn1ccc2c(-c3ncc(Nc4ccc(N5CCO[C@H](C(C)(C)O)C5)cn4)c4c3CNC4=O)cccc21] | 7-[[5-[(2S)-2-(1-hydroxy-1-methyl-ethyl)morpholin-4-yl]-2-pyridyl]amino]-4-(1-methylindol-4-yl)-2,3-dihydropyrrolo[3,4-c]pyridin-1-one | Method AcHSS C18, m/z = 499 [M + H]+, Ret. time = 3.32 min. | ¹H NMR (400 MHz, DMSO): δ 9.80 (s, 1 H), 9.36 (s, 1 H), 8.98 (s, 1 H), 8.00 (d, J = 2.4 Hz, 1 H), 7.44 (d, J = 8.4 Hz, 1 H), 7.40 (dd, J = 3.9, 9.4 Hz, 1 H), 7.31 (d, J = 3.0 Hz, 1 H), 7.27 (d, J = 7.2 Hz, 1 H), 7.19 (t, J = 8.0 Hz, 1 H), 6.99 (d, J = 8.7 Hz, 1 H), 6.66 (d, J = 3.6 Hz, 1 H), 4.51 (s, 2 H), 4.41 (s, 1 H), 3.94 (dd, J = 3.6, 11.8 Hz, 1 H), 3.78 (s, 3 H), 3.60 (dt, J = 2.6, 11.5 Hz 1 H), 3.54 (d, J = 12.4 Hz, 1 H), 3.40 (d, J = 11.5 Hz, 1 H), 2.61 (dt, J = 3.1, 11.8 Hz, 1 H), 2.48 (t, J = 5.7 Hz, 1 H), 1.12 (s, 3 H), 1.06 (s, 3 H). | O AC47 BC108 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-485 | 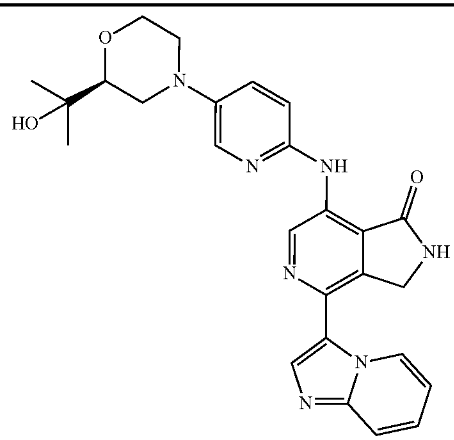 | 7-[[5-[(2S)-2-(1-hydroxy-1-methylethyl)morpholin-4-yl]-2-pyridyl]amino]-4-imidazo[1,2-a]pyridin-3-yl-2,3-dihydropyrrolo[3,4-c]pyridin-1-one | Method AcHSS C18, m/z = 486 [M + H]+, Ret. time = 2.80 min. | ¹H NMR (400 MHz, DMSO): δ 9.90 (s, 1 H), 9.86 (td, J = 1.3, 7.1 Hz, 1 H), 9.43 (s, 1 H), 9.25 (s, 1 H), 8.08 (s, 1 H), 8.05 (d, J = 2.7 Hz, 1 H), 7.72 (td, J = 1.1, 9.1 Hz, 1 H), 7.47 (dd, J = 3.2, 9.2 Hz, 1 H), 7.41 (ddt, J = 1.4, 5.2, 4.5 Hz, 1 H), 7.09 (dd, J = 2.1, 7.7 Hz, 1 H), 7.06 (d, J = 8.4 Hz, 1 H), 4.76 (s, 2 H), 4.47 (s, 1 H), 4.03 (M, 1 H), 3.99 (dd, J = 2.1, 3.8 Hz, 1 H), 3.66 (ddd, J = 11.7, 11.7, 2.5 Hz, 1 H), 3.60 (d, J = 12.0 Hz, 1 H), 3.46 (d, J = 11.8 Hz, 1 H), 2.68 (ddd, J = 11.8, 11.8, 2.9 Hz, 1 H), 2.56-2.52 (m, 1 H), 1.17 (s, 3 H), 1.12 (s, 3 H). | O AC47 BC42 |

| # | STRUCTURE | NAME | LCMS | ¹H NMR | Method Reagent AA BB |
|---|---|---|---|---|---|
| I-486 | 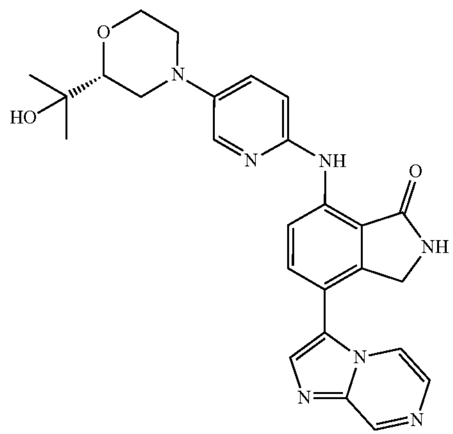 [SMILES: CC(C)(O)[C@H]1CN(c2ccc(Nc3ccc(-c4cnc5cnccn45)c4c3C(=O)NC4)nc2)CCO1] | 7-[[5-[(2R)-2-(1-hydroxy-1-methylethyl)morpholin-4-yl]-2-pyridyl]amino]-4-imidazo[1,2-a]pyrazin-3-yl-isoindolin-1-one | Method AcHSS C18, m/z = 486 [M + H]+, Ret. time = 2.85 min. | ¹H NMR (400 MHz, DMSO): δ 9.96 (s, 1 H), 9.19 (d, J = 1.9 Hz, 1 H), 8.85 (s, 1 H), 8.65 (d, J = 9.0 Hz, 1 H), 8.51 (dd, J = 1.3, 4.8 Hz, 1 H), 8.16 (s, 1 H), 8.08 (d, J = 3.3 Hz, 1 H), 7.96 (d, J = 4.7 Hz, 1 H), 7.81 (d, J = 9.1 Hz, 1 H), 7.51 (dd, J = 2.7, 8.9 Hz, 1 H), 7.05 (d, J = 8.9 Hz, 1 H), 4.52 (s, 1 H), 4.49 (s, 2 H), 4.05 (dd, J = 2.8, 11.1 Hz, 1 H), 3.71 (dt, J = 2.3, 11.6 Hz, 1 H), 3.65 (d, J = 11.1 Hz, 1 H), 3.52 (d, J = 11.4 Hz, 1 H), 3.40-3.38 (m, 1 H), 2.72 (ddd, J = 12.2, 12.2, 3.6 Hz, 1 H), 2.61-2.59 (m, 1 H), 1.23 (s, 3 H), 1.17 (s, 3 H). | F AC46 BC52 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-487 | 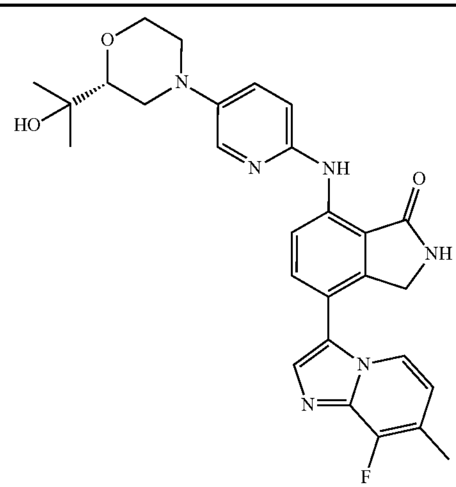 | 4-(8-fluoro-7-methyl-imidazo[1,2-a]pyridin-3-yl)-7-[[5-[(2R)-2-(1-hydroxy-1-methyl-ethyl)morpholin-4-yl]-2-pyridyl]amino]iso-indolin-1-one | Method AcHSS C18, m/z = 517 [M + H]+, Ret. time = 2.91 min. | ¹H NMR (400 MHz, DMSO): δ 9.92 (s, 1 H), 8.82 (s, 1 H), 8.62 (d, J = 8.8 Hz, 1 H), 8.19 (d, J = 7.1 Hz, 1 H), 8.07 (d, J = 3.0 Hz, 1 H), 7.84 (s, 1 H), 7.72 (d, J = 8.6 Hz, 1 H), 7.50 (dd, J = 3.0, 9.1 Hz, 1 H), 7.04 (d, J = 9.1 Hz, 1 H), 6.88 (t, J = 6.9 Hz, 1 H), 4.53 (s, 1 H), 4.43 (s, 2 H), 4.05 (dd, J = 2.7, 11.3 Hz, 1 H), 3.71 (ddd, J = 11.7, 11.7, 3.1 Hz, 1 H), 3.64 (d, J = 11.7 Hz, 1 H), 3.50 (d, J = 11.5 Hz, 1 H), 3.37-3.33 (m, 1 H), 2.71 (ddd, J = 11.9, 11.9, 3.6 Hz, 1 H), 2.55-2.54 (m, 1 H), 2.39 (d, J = 2.1 Hz, 3 H), 1.23 (s, 3 H), 1.17 (s, 3 H). | F AC46 BC117 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-488 | 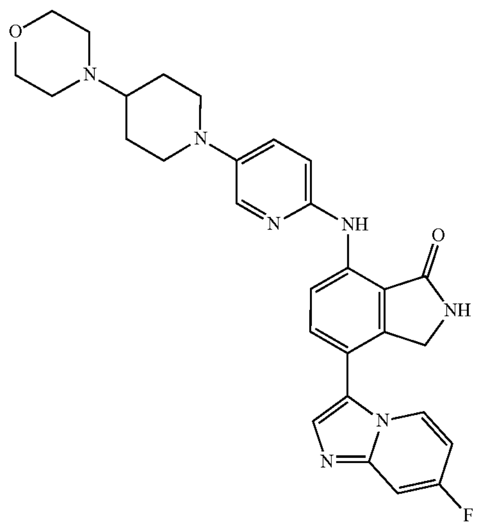 [SMILES: O=C1NCc2c(-c3cnc4cc(F)ccn34)ccc(Nc3ccc(N4CCC(N5CCOCC5)CC4)cn3)c21] | 4-(7-fluoro-imidazo[1,2-a]pyridin-3-yl)-7-[[5-(4-morpholino-1-piperidyl)-2-pyridyl]amino]isoindolin-1-one | Method BicarbB EHC18, m/z = 528 [M + H]+, Ret. time = 4.08 min. | ¹H NMR (400 MHz, DMSO): δ 9.89 (s, 1 H), 8.80 (s, 1 H), 8.60 (d, J = 8.9 Hz, 1 H), 8.46 (dd, J = 5.9, 7.4 Hz, 1 H), 8.06 (d, J = 3.1 Hz, 1 H), 7.86 (s, 1 H), 7.73 (d, J = 8.4 Hz, 1 H), 7.57 (dd, J = 3.2, 10.5 Hz, 1 H), 7.50 (dd, J = 3.3, 9.4 Hz, 1 H), 7.05-6.98 (m, 2 H), 4.42 (s, 2 H), 4.09 (d, J = 12 Hz, 2 H), 3.86 (d, J = 12 Hz, 2 H), 3.75 (t, J = 12 Hz, 2H), 3.55 (d, J = 12 Hz, 2 H), 3.39 (m, 1 H), 3.19 (m, 2 H), 2.76 (t, J = 12 Hz, 2 H), 2.38 (m, 2 H), 1.80 (m, 2 H) | F AC56 BC80 |

| # | STRUCTURE | NAME | LCMS | ¹H NMR | Method Reagent AA BB |
|---|---|---|---|---|---|
| I-489 | 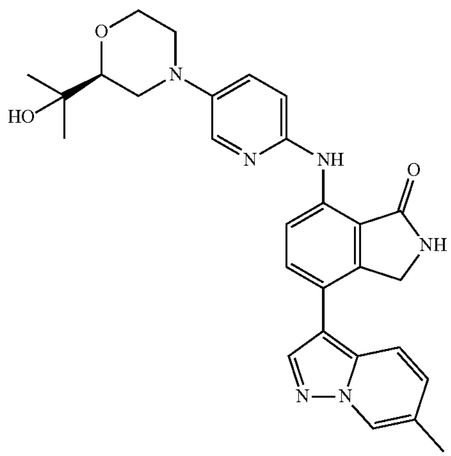 [SMILES: Cc1ccc2c(-c3ccc(Nc4ccc(N5CCO[C@H](C(C)(C)O)C5)cn4)c4c3CNC4=O)cnn2c1] | 7-[[5-[(2S)-2-(1-hydroxy-1-methylethyl)morpholin-4-yl]-2-pyridyl]amino]-4-(6-methyl-pyrazolo[1,5-a]pyridin-3-yl)isoindolin-1-one | Method AcHSS C18, m/z = 499.7 [M + H]+, Ret. time = 3.76 min. | ¹H NMR (400 MHz, DMSO): δ 9.74 (s, 1 H), 8.67 (s, 1 H), 8.51 (s, 1 H), 8.43 (d, J = 9.4 Hz, 1 H), 8.16 (s, 1 H), 7.92 (d, J = 2.8 Hz, 1 H), 7.67 (d, J = 9.2 Hz, 1 H), 7.58 (d, J = 8.6 Hz, 1 H), 7.36 (dd, J = 2.9, 9.0 Hz, 1 H), 7.10 (dd, J = 1.6, 9.3 Hz, 1 H), 6.88 (d, J = 9.1 Hz, 1 H), 4.42 (s, 2 H), 4.39 (s, 1 H), 3.93 (dd, J = 2.5, 11.1 Hz, 1 H), 3.59 (ddd, J = 11.6, 11.6, 2.5 Hz, 1 H), 3.50 (d, J = 11.0 Hz, 1 H), 3.36 (d, J = 12.1 Hz, 1 H), 2.58 (dd, J = 11.8, 15.1 Hz, 1 H), 2.47-2.45 (m, 1 H), 2.26 (s, 3 H), 1.10 (s, 3 H), 1.04 (s, 3 H). | F AC47 BC46 |
| I-490 | 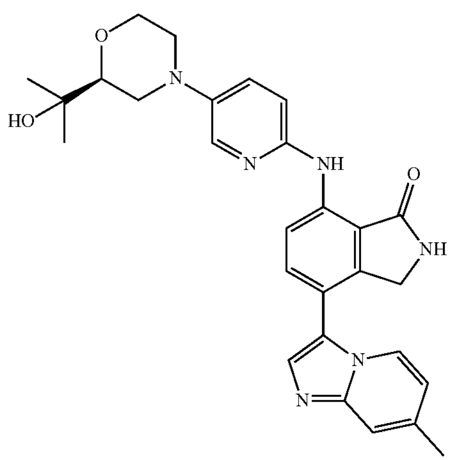 [SMILES: Cc1ccn2c(-c3ccc(Nc4ccc(N5CCO[C@H](C(C)(C)O)C5)cn4)c4c3CNC4=O)cnc2c1] | 7-[[5-[(2S)-2-(1-hydroxy-1-methylethyl)morpholin-4-yl]-2-pyridyl]amino]-4-(7-methyl-imidazo[1,2-a]pyridin-3-yl)isoindolin-1-one | Method AcHSS C18, m/z = 499 [M + H]+, Ret. time = 2.69 min. | ¹H NMR (400 MHz, DMSO): δ 9.88 (s, 1 H), 8.79 (s, 1 H), 8.58 (d, J = 9.0 Hz, 1 H), 8.31 (d, J = 7.1 Hz, 1 H), 8.02 (d, J = 3.2 Hz, 1 H), 7.80 (s, 1H), 7.69 (d, J = 8.6 Hz, 1 H), 7.48-7.44 (m, 2 H), 7.00 (d, J = 8.9 Hz, 1 H), 6.85 (dd, J = 1.5, 7.0 Hz, 1 H), 4.51 (s, 1 H), 4.39 (s, 2 H), 4.01 (dd, J = 3.4, 11.0 Hz, 1 H), 3.67 (ddd, J = 11.4, 11.4, 2.5 Hz, 1 H), 3.61 (d, J = 10.8 Hz, 1 H), 3.48 (d, J = 12.2 Hz, 1 H), 3.33-3.31 (m, 1 H), 2.67 (dt, J = 3.5, 12.0 Hz, 1 H), 2.51-2.50 (m, 1 H), 2.40 (s, 3 H), 1.19 (s, 3 H), 1.13 (s, 3 H). | F AC47 BC45 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-491 | 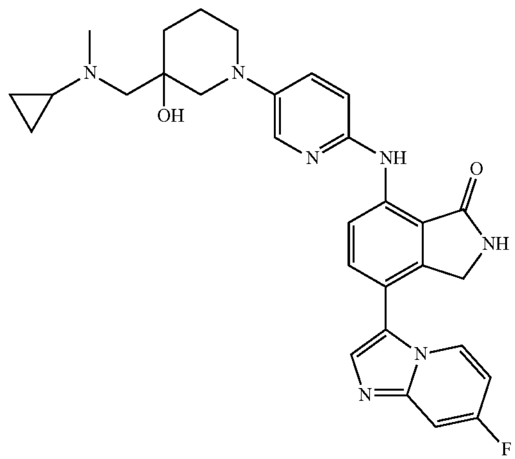 [SMILES: CN(CC1(O)CCCN(c2ccc(Nc3ccc(-c4cnc5cc(F)ccn45)c4c3C(=O)NC4)nc2)C1)C1CC1] | 7-[[5-[3-[[cyclopropyl(methyl)amino]methyl]-3-hydroxy-1-piperidyl]-2-pyridyl]amino]-4-(7-fluoroimidazo[1,2-a]pyridin-3-yl)isoindolin-1-one | Method AcHSS C18, m/z = 542 [M + H]+, Ret. time = 2.02 min. | ¹H NMR (400 MHz, DMSO): δ 9.85 (s, 1 H), 8.78 (s, 1 H), 8.56 (d, J = 9.1 Hz, 1 H), 8.43 (dd, J = 6.3, 7.4 Hz, 1 H), 7.97 (s, 1 H), 7.83 (s, 1 H), 7.70 (d, J = 9.0 Hz, 1 H), 7.54 (dd, J = 2.8, 10.4 Hz, 1 H), 7.41 (d, J = 9.7 Hz, 1 H), 7.02-6.95 (m, 2 H), 4.39 (s, 2 H), 4.29 (s, 1 H), 3.11 (q, J = 8.4 Hz, 2 H), 2.92 (s, 2 H), 2.72 (s, 2 H), 1.81 (s, 2 H), 1.66 (s, 1 H), 1.58 (s, 1 H), 1.42 (s, 1 H), 0.41 (s, 4 H). | F AC58 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-492 | 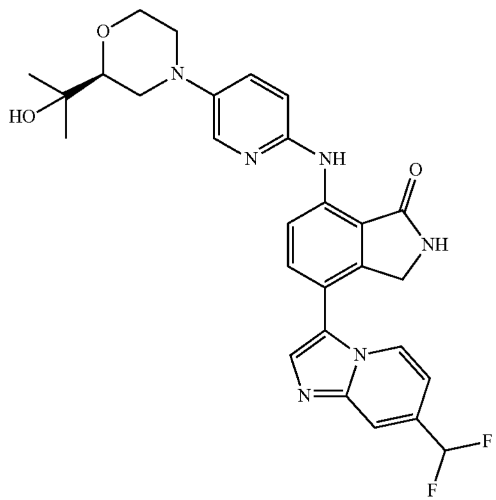 [SMILES: CC(C)(O)[C@@H]1CN(c2ccc(Nc3ccc(-c4cnc5cc(C(F)F)ccn45)c4c3C(=O)NC4)nc2)CCO1] | 4-[7-(difluoromethyl)imidazo[1,2-a]pyridin-3-yl]-7-[[5-[(2S)-2-(1-hydroxy-1-methylethyl)morpholin-4-yl]-2-pyridyl]amino]isoindolin-1-one | Method AcHSS C18, m/z = 535 [M + H]+, Ret. time = 3.07 min. | ¹H NMR (400 MHz, DMSO): δ 9.94 (s, 1 H), 8.84 (s, 1 H), 8.64 (d, J = 8.4 Hz, 1 H), 8.55 (d, J = 7.4 Hz, 1 H), 8.07 (d, J = 3.5 Hz, 1 H), 8.02 (s, 1 H), 7.99 (s, 1 H), 7.78 (d, J = 8.4 Hz, 1 H), 7.51 (dd, J = 3.4, 9.2 Hz, 1 H), 7.12 (dd, J = 1.6, 7.4 Hz, 1 H), 7.05 (d, J = 55.6 Hz, 1 H), 4.52 (s, 10.0 Hz, 1 H), 4.45 (s, 2 H), 4.05 (dd, J = 2.9, 10.6 Hz, 1 H), 3.71 (ddd, J = 6.4, 6.4, 11.8 Hz, 1 H), 3.65 (d, J = 11.9 Hz, 1 H), 3.52 (d, J = 12.2 Hz, 1 H), 3.40-3.38 (m, 1 H), 2.72 (ddd, J = 11.7, 11.7, 4.0 Hz, 1 H), 2.59 (d, J = 8.4 Hz, 1 H), 1.22 (s, 3 H), 1.17 (s, 3 H). | F AC47 BC101 |
| I-493 | 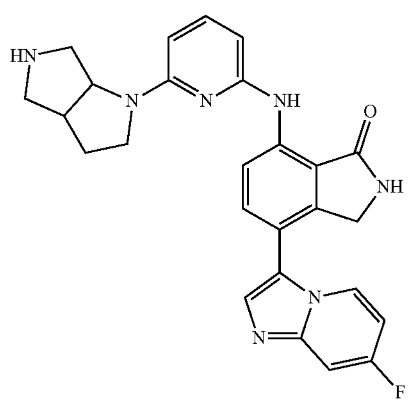 [SMILES: O=C1NCc2c(-c3cnc4cc(F)ccn34)ccc(Nc3cccc(N4CCC5CNCC54)n3)c21] | 7-[[6-(3,3a,4,5,6,6a-hexahydro-2H-pyrrolo[2,3-c]pyrrol-1-yl)-2-pyridyl]amino]-4-(7-fluoroimidazo[1,2-a]pyridin-3-yl)isoindolin-1-one | Method AcHSS C18, m/z = 470 [M + H]+, Ret. time = 2.32 min. | ¹H NMR (400 MHz, MeOD) δ 8.73-8.70 (m, 1 H), 8.56 (s, 1 H), 8.33 (dd, J = 5.6, 7.6 Hz, 1 H), 7.72-7.69 (m, 2 H), 7.53 (t, J = 8.0 Hz, 1 H), 7.36 (dd, J = 2.1, 9.3 Hz, 1 H), 6.99-6.94 (m, 1 H), 6.34-6.32 (m, 1 H), 6.18-6.15 (m, 1 H), 4.41-4.38 (m, 2 H), 3.80-3.73 (m, 1 H), 3.64-3.46 (m, 6 H), 3.32-3.26 (m, 2 H), 2.42-2.32 (m, 1 H), 2.09-1.96 (m, 1 H). | F AC51 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-494 | 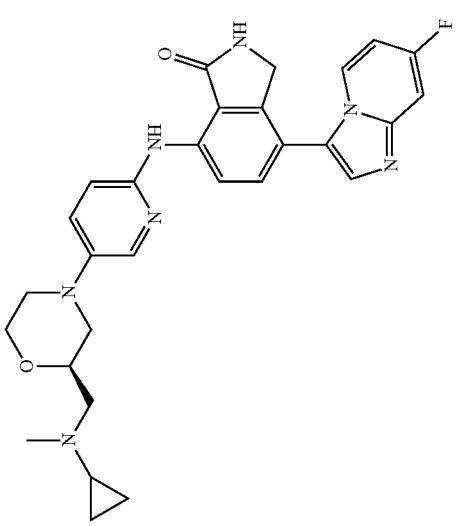 | 7-[[5-[(2R)-2-[[cyclopropyl(meth-yl)amino]meth-yl]morpholin-4-yl]-2-pyridyl]amino]-4-(7-fluoro-imidazo[1,2-a]pyridin-3-yl)isoindolin-1-one | Method AcHSS C18, m/z = 528 [M + H]+, Ret. time = 2.09 min. | ¹H NMR (400 MHz, DMSO): δ 9.88 (s, 1 H), 8.79 (s, 1 H), 8.58 (d, J = 8.5 Hz, 1 H), 8.43 (dd, J = 6.5, 8.1 Hz, 1 H), 8.00 (d, J = 2.7 Hz, 1 H), 7.82 (s, 1 H), 7.70 (d, J = 8.3 Hz, 1 H), 7.53 (dd, J = 2.6, 10.0 Hz, 1 H), 7.45 (dd, J = 3.1, 9.0 Hz, 1 H), 7.01-6.96 (m, 2 H), 4.39 (s, 2 H), 3.95 (d, J = 10.1 Hz, 1 H), 3.79-3.73 (m, 1 H), 3.66 (ddd, J = 11.6, 11.6, 2.4 Hz, 1 H), 3.47 (d, J = 11.3 Hz, 2 H), 2.70 (ddd, J = 11.8, 11.8, 3.3 Hz, 1 H), 2.62 (dd, J = 4.3, 5.3 Hz, 2 H), 2.39 (t, J = 10.0 Hz, 1 H), 2.34 (s, 3 H), 1.78-1.71 (m, 1 H), 0.48-0.43 (m, 2 H), 0.36-0.32 (m, 2 H). | F AC60 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-495 | 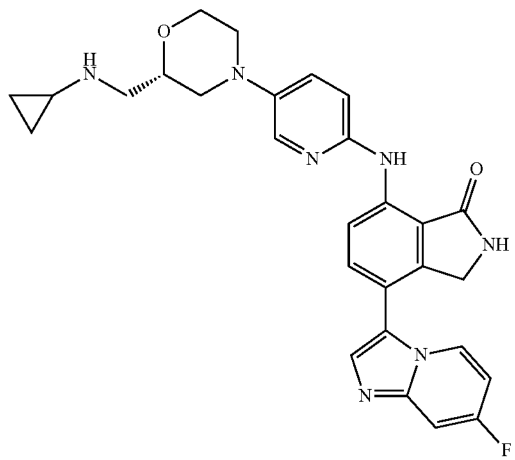 [SMILES: O=C1NCc2c(-c3cnc4cc(F)ccn34)ccc(Nc3ccc(N4CCO[C@@H](CNC5CC5)C4)cn3)c21] | 7-[[5-[(2S)-2-[(cyclopropyl-amino)meth-yl]morpholin-4-yl]-2-pyridyl]amino]-4-(7-fluoro-imidazo[1,2-a]pyridin-3-yl)isoindolin-1-one | Method AcHSS C18, m/z = 514 [M + H]+, Ret. time = 2.01 min. | ¹H NMR (400 MHz, DMSO): δ 9.62 (s, 1 H), 8.54 (s, 1 H), 8.33 (d, J = 8.7 Hz, 1 H), 8.18 (dd, J = 5.9, 7.5 Hz, 1 H), 7.77 (d, J = 3.0 Hz, 1 H), 7.57 (s, 1 H), 7.45 (d, J = 8.7 Hz, 1 H), 7.29 (d, J = 2.2 Hz, 1 H), 7.27 (d, J = 2.4 Hz, 1 H), 7.21 (dd, J = 3.1, 9.2 Hz, 1 H), 6.76-6.71 (m, 2 H), 4.14 (s, 2 H), 3.71 (dd, J = 1.8, 11.5 Hz, 1 H), 3.46-3.38 (m, 2 H), 3.34 (d, J = 11.9 Hz, 1 H), 3.21 (d, J = 12.0 Hz, 1 H), 2.52-2.42 (m, 3 H), 2.16 (dd, J = 10.6, 11.3 Hz, 1 H), 1.91-1.85 (m, 1 H), 0.16-0.13 (m, 2 H), 0.02-0.02 (m, 2 H). | F AC61 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-496 | 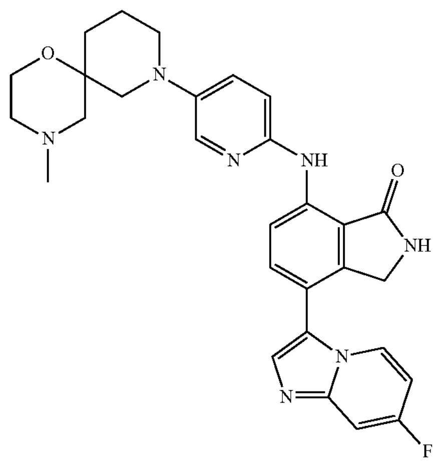 [SMILES: CN1CCOC2(CCCN(c3ccc(Nc4ccc(-c5cnc6cc(F)ccn56)c5c4C(=O)NC5)nc3)C2)C1] | 4-(7-fluoro-imidazo[1,2-a]pyridin-3-yl)-7-[[5-(4-methyl-1-oxa-4,8-diazaspiro[5.5]jun-decan-8-yl)-2-pyridyl]amino]iso-indolin-1-one | Method AcHSS C18, m/z = 528 [M + H]+, Ret. time = 2.09 min. | ¹H NMR (400 MHz, DMSO): δ 9.89 (s, 1 H), 8.81 (s, 1 H), 8.59 (d, J = 8.7 Hz, 1 H), 8.46 (dd, J = 5.9, 7.5 Hz, 1 H), 8.03 (d, J = 2.8 Hz, 1 H), 7.86 (s, 1 H), 7.73 (d, J = 8.2 Hz, 1 H), 7.57 (dd, J = 2.7, 10.2 Hz, 1 H), 7.45 (dd, J = 2.8, 8.8 Hz, 1 H), 7.05-6.98 (m, 2 H), 4.42 (s, 2 H), 3.76 (ddd, J = 3.3, 8.5, 11.8 Hz, 1 H), 3.67 (td, J = 4.4, 12.0 Hz, 1 H), 3.32 (d, J = 12.0 Hz, 2 H), 3.19 (d, J = 11.3 Hz, 2 H), 3.12-3.08 (m, 1 H), 2.48 (d, J = 10.4 Hz, 1 H), 2.22 (s, 4 H), 2.12 (d, J = 14.4 Hz, 1 H), 1.88-1.79 (m, 1 H), 1.77-1.70 (m, 1 H), 1.63 (d, J = 12.8 Hz, 2 H). | F AC63 BC80 |
| I-497 | Isomer 1 Separated by Chiral SFC | 4-(7-fluoro-imidazo[1,2-a]pyridin-3-yl)-7-((6-((3aS,6aS)-hexahydro-pyrrolo[3,4-b]pyrrol-1(2H)-yl)pyridin-2-yl)amino)iso-indolin-1-one | Method AcHSS C18, m/z = 470 [M + H]+, Ret. time = 2.25 min. | ¹H NMR (400 MHz, DMSO): δ 9.95 (s, 1 H), 8.82 (s, 1 H), 8.76 (d, J = 9.0 Hz, 1 H), 8.44 (dd, J = 6.1, 7.5 Hz, 1 H), 8.33 (s, 1 H), 7.83 (s, 1 H), 7.73 (d, J = 8.8 Hz, 1 H), 7.54 (dd, J = 3.1, 10.4 Hz, 1 H), 7.44 (t, J = 7.8 Hz, 1 H), 7.00 (ddd, J = 7.6, 7.6, 2.5 Hz, 1 H), 6.15 (d, J = 7.6 Hz, 1 H), 4.40 (s, 2 H), 4.37 (s, 1 H), 3.64-3.57 (m, 2 H), 3.52-3.47 (m, 1 H), 3.15-3.10 (m, 1 H), 2.99-2.90 (m, 3 H), 2.80 (d, J = 7.8 Hz, 1 H), 2.17-2.08 (m, 1 H), 1.90-1.81 (m, 1 H). | F AC51 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-498 | Isomer 2 Separated by Chiral SFC | 4-(7-fluoro-imidazo[1,2-a]pyridin-3-yl)-7-(((3aR,6aR)-hexahydro-pyrrolo[3,4-b]pyrrol-1(2H)-yl)pyridin-2-yl)amino)isoindolin-1-one | Method AcHSS C18, m/z = 470 [M + H]+, Ret. time = 2.25 min. | ¹H NMR (400 MHz, DMSO): δ 9.95 (s, 1 H), 8.82 (s, 1 H), 8.76 (d, J = 9.0 Hz, 1 H), 8.44 (dd, J = 6.1, 7.5 Hz, 1 H), 8.33 (s, 1 H), 7.83 (s, 1 H), 7.73 (d, J = 8.8 Hz, 1 H), 7.54 (dd, J = 3.1, 10.4 Hz, 1 H), 7.44 (t, J = 7.8 Hz, 1 H), 7.00 (ddd, J = 7.6, 7.6, 2.5 Hz, 1 H), 6.15 (d, J = 7.6 Hz, 1 H), 4.40 (s, 2 H), 4.37 (s, 1 H), 3.64-3.57 (m, 2 H), 3.52-3.47 (m, 1 H), 3.15-3.10 (m, 1 H), 2.99-2.90 (m, 3 H), 2.80 (d, J = 7.8 Hz, 1 H), 2.17-2.08 (m, 1 H), 1.90-1.81 (m, 1 H). | F AC51 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-499 | 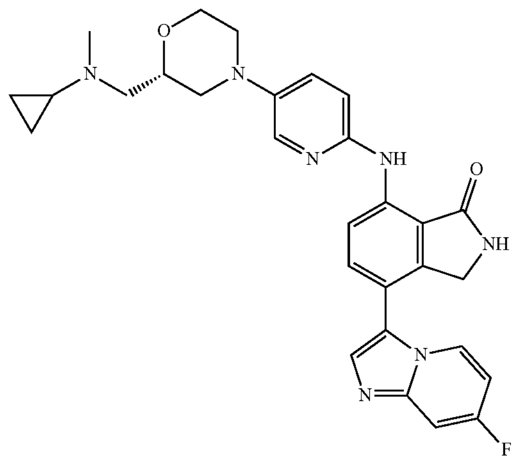 [SMILES: CN(C[C@H]1CN(c2ccc(Nc3ccc(-c4cnc5cc(F)ccn45)c4c3C(=O)NC4)nc2)CCO1)C1CC1] | 7-[[5-[(2S)-2-[[cyclo-propyl(meth-yl)amino]meth-yl]morpho-lin-4-yl]-2-pyridyl]amino]-4-(7-fluoro-imidazo[1,2-a]pyridin-3-yl)isoindolin-1-one | Method AcHSS C18, m/z = 528 [M + H]+, Ret. time = 2.05 min. | ¹H NMR (400 MHz, DMSO): δ 9.88 (s, 1 H), 8.79 (s, 1 H), 8.58 (d, J = 8.5 Hz, 1 H), 8.43 (dd, J = 6.5, 8.1 Hz, 1 H), 8.00 (d, J = 2.7 Hz, 1 H), 7.82 (s, 1 H), 7.70 (d, J = 8.3 Hz, 1 H), 7.53 (dd, J = 2.6, 10.0 Hz, 1 H), 7.45 (dd, J = 3.1, 9.0 Hz, 1 H), 7.01-6.96 (m, 2 H), 4.39 (s, 2 H), 3.95 (d, J = 10.1 Hz, 1 H), 3.79-3.73 (m, 1 H), 3.66 (ddd, J = 11.6, 11.6, 2.4 Hz, 1 H), 3.47 (d, J = 11.3 Hz, 2 H), 2.70 (ddd, J = 11.8, 11.8, 3.3 Hz, 1 H), 2.62 (dd, J = 4.3, 5.3 Hz, 2 H), 2.39 (t, J = 10.0 Hz, 1 H), 2.34 (s, 3 H), 1.78-1.71 (m, 1 H), 0.48-0.43 (m, 2 H), 0.36-0.32 (m, 2 H). | F AC64 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-500 | (structure) | 4-(7-fluoro-imidazo[1,2-a]pyridin-3-yl)-7-[[5-(1-oxa-4,8-diazaspiro[5.5]undecan-8-yl]-2-pyridyl]amino]isoindolin-1-one | Method AcHSS C18, m/z = 514 [M + H]+, Ret. time = 2.09 min. | ¹H NMR (400 MHz, DMSO): δ 9.84 (s, 1 H), 8.79 (s, 1 H), 8.57 (d, J = 8.6 Hz, 1 H), 8.43 (dd, J = 5.5, 7.7 Hz, 1 H), 8.02 (d, J = 3.1 Hz, 1 H), 7.82 (s, 1 H), 7.69 (d, J = 8.7 Hz, 1 H), 7.53 (dd, J = 2.6, 9.9 Hz, 1 H), 7.45 (dd, J = 3.0, 9.0 Hz, 1 H), 6.99 (ddd, J = 7.2, 7.2, 2.5 Hz, 1 H), 6.96 (d, J = 9.4 Hz, 1 H), 4.38 (s, 3 H), 3.63 (ddd, J = 4.9, 4.9, 14.5 Hz, 1 H), 3.52 (ddd, J = 4.0, 4.0, 11.8 Hz, 1 H), 3.24 (d, J = 11.8 Hz, 1 H), 3.20 (d, J = 12.0 Hz, 1 H), 3.11-3.06 (m, 2 H), 2.81 (d, J = 12.5 Hz, 1 H), 2.74-2.65 (m, 2 H), 2.57 (d, J = 12.7 Hz, 1 H), 1.81-1.76 (m, 1 H), 1.66 (t, J = 7.2 Hz, 1 H), 1.55 (d, J = 12.3 Hz, 2 H). | F AC65 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-501 | Isomer 1 Separated by Chiral SFC | (S)-4-(7-fluoro-imidazo[1,2-a]pyridin-3-yl)-7-(5-(3-morpholino-piperidin-1-yl)pyridin-2-yl)amino)isoindolin-1-one | Method AcHSS C18, m/z = 528 [M + H]+, Ret. time = 1.98 min. | ¹H NMR (400 MHz, DMSO): δ 9.88 (s, 1 H), 8.81 (s, 1 H), 8.60 (d, J = 9.5 Hz, 1 H), 8.46 (dd, J = 6.3, 7.6 Hz, 1 H), 8.06 (d, J = 2.9 Hz, 1 H), 7.86 (s, 1 H), 7.73 (d, J = 8.5 Hz, 1 H), 7.57 (dd, J = 2.5, 10.3 Hz, 1 H), 7.50 (dd, J = 3.2, 9.0 Hz, 1 H), 7.05-6.97 (m, 2 H), 4.42 (s, 2 H), 3.73 (d, J = 14.6 Hz, 1 H), 3.63 (t, J = 4.6 Hz, 4 H), 3.58 (d, J = 13.7 Hz, 1 H), 2.67-2.59 (m, 6 H), 2.53-2.45 (m, 1 H), 1.99-1.96 (m, 1 H), 1.86 (td, J = 3.2, 13.5 Hz, 1 H), 1.69-1.56 (m, 1 H), 1.39 (dd, J = 3.6, 11.5 Hz, 1 H), 1.33 (dd, J = 4.1, 12.7 Hz, 1 H). | F AC52 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-502 | Isomer 2 Separated by Chiral SFC | (R)-4-(7-fluoro-imidazo[1,2-a]pyridin-3-yl)-7-(5-(3-morpholino-piperidin-1-yl)pyridin-2-yl)amino)isoindolin-1-one | Method AcHSS C18, m/z = 528 [M + H]+, Ret. time = 1.99 min. | ¹H NMR (400 MHz, DMSO): δ 9.88 (s, 1 H), 8.81 (s, 1 H), 8.60 (d, J = 9.5 Hz, 1 H), 8.46 (dd, J = 6.3, 7.6 Hz, 1 H), 8.06 (d, J = 2.9 Hz, 1 H), 7.86 (s, 1 H), 7.73 (d, J = 8.5 Hz, 1 H), 7.57 (dd, J = 2.5, 10.3 Hz, 1 H), 7.50 (dd, J = 3.2, 9.0 Hz, 1 H), 7.05-6.97 (m, 2 H), 4.42 (s, 2 H), 3.73 (d, J = 14.6 Hz, 1 H), 3.63 (t, J = 4.6 Hz, 4 H), 3.58 (d, J = 13.7 Hz, 1 H), 2.67-2.59 (m, 6 H), 2.53-2.45 (m, 1 H), 1.99-1.96 (m, 1 H), 1.86 (td, J = 3.2, 13.5 Hz, 1 H), 1.69-1.56 (m, 1 H), 1.39 (dd, J = 3.6, 11.5 Hz, 1 H), 1.33 (dd, J = 4.1, 12.7 Hz, 1 H). | F AC52 BC80 |
| I-503 | 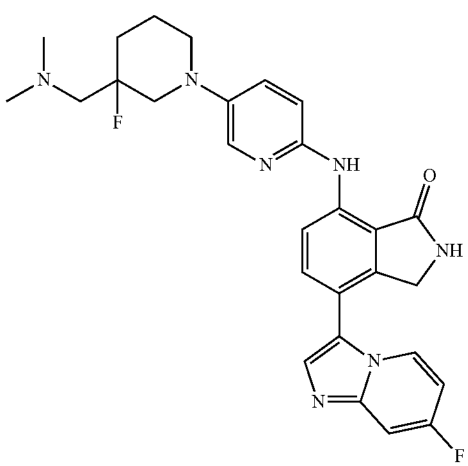 [SMILES: CN(C)CC1(F)CCCN(c2ccc(Nc3ccc(-c4cnc5cc(F)ccn45)c4c3C(=O)NC4)nc2)C1] | 7-[[5-[3-[(dimethyl-amino)methyl]-3-fluoro-1-piperidyl]-2-pyridyl]amino]-4-(7-fluoro-imidazo[1,2-a]pyridin-3-yl)isoindolin-1-one | Method AcHSS C18, m/z = 518 [M + H]+, Ret. time = 2.03 min. | ¹H NMR (400 MHz, DMSO): δ 9.86 (s, 1 H), 8.78 (s, 1 H), 8.57 (d, J = 8.5 Hz, 1 H), 8.43 (dd, J = 6.0, 7.4 Hz, 1 H), 8.01 (d, J = 2.9 Hz, 1 H), 7.82 (s, 1 H), 7.70 (d, J = 8.5 Hz, 1 H), 7.53 (dd, J = 2.4, 10.0 Hz, 1 H), 7.44 (dd, J = 2.9, 9.0 Hz, 1 H), 7.01-6.95 (m, 2 H), 4.39 (s, 2 H), 3.32-3.09 (m, 3 H), 3.05-2.96 (m, 1 H), 2.60 (s, 1 H), 2.55 (s, 1 H), 2.26 (s, 6 H), 1.86-1.73 (m, 3 H), 1.64-1.59 (m, 1 H). | F AC72 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-504 | 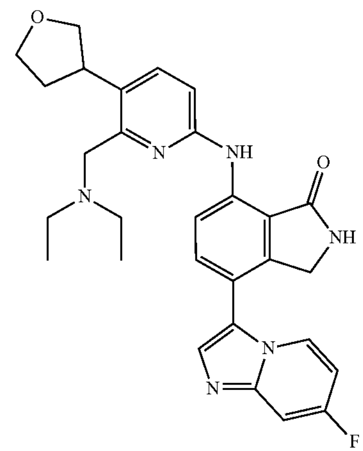 [SMILES: CCN(CC)Cc1nc(Nc2ccc(-c3cnc4cc(F)ccn34)c3c2C(=O)NC3)ccc1C1CCOC1] | 7-[[6-(diethylaminomethyl)-5-tetrahydrofuran-3-yl-2-pyridyl]amino]-4-(7-fluoroimidazo[1,2-a]pyridin-3-yl)isoindolin-1-one | Method AcHSS C18, m/z = 515 [M + H]+, Ret. time = 2.15 min. | ¹H NMR (400 MHz, DMSO): δ 10.03 (s, 1 H), 8.82 (s, 1 H), 8.78 (d, J = 8.5 Hz, 1 H), 8.46-8.41 (m, 1 H), 7.81 (s, 1 H), 7.71 (d, J = 8.5 Hz, 1 H), 7.65 (d, J = 8.5 Hz, 1 H), 7.52 (dd, J = 2.4, 10.0 Hz, 1 H), 6.99-6.91 (m, 2 H), 4.38 (s, 2 H), 4.02-3.66 (m, 7 H), 3.55-3.49 (m, 1 H), 2.56-2.52 (m, 2 H), 2.33-2.24 (m, 1 H), 1.93-1.83 (m, 1 H), 1.23 (s, 1 H), 0.99 (t, J = 7.1, 7.1 Hz, 6 H). | F AC66 BC80 |
| I-505 | 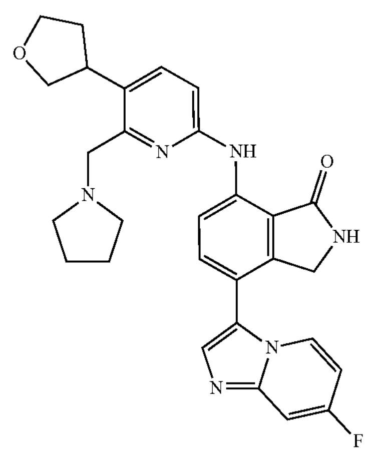 [SMILES: O=C1NCc2c(-c3cnc4cc(F)ccn34)ccc(Nc3ccc(C4CCOC4)c(CN4CCCC4)n3)c21] | 4-(7-fluoroimidazo[1,2-a]pyridin-3-yl)-7-[[6-(pyrrolidin-1-ylmethyl)-5-tetrahydrofuran-3-yl-2-pyridyl]amino]isoindolin-1-one | Method AcHSS C18, m/z = 513 [M + H]+, Ret. time = 2.17 min. | ¹H NMR (400 MHz, DMSO): δ 10.09 (s, 1 H), 8.91 (s, 1 H), 8.53-8.39 (m, 2 H), 7.89 (s, 1 H), 7.78 (d, J = 8.4 Hz, 2 H), 7.59 (dd, J = 2.6, 10.6 Hz, 1 H), 7.13-7.03 (m, 2 H), 4.45 (s, 2 H), 4.08-4.00 (m, 2 H), 3.87-3.77 (m, 3 H), 3.61 (t, J = 7.6 Hz, 2 H), 3.34-3.25 (m, 2 H), 2.98 (t, J = 4.4 Hz, 1 H), 2.38-2.35 (m, 2 H), 1.97-1.88 (m, 8 H). | F AC67 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-506a | Isomer 1 Separated by Chiral SFC | (R)-4-(7-fluoro-imidazo[1,2-a]pyridin-3-yl)-7-((5-(4-methyl-1-oxa-4,8-diaza-spiro[5.5]un-decan-8-yl)pyridin-2-yl)amino)iso-indolin-1-one | Method AcHSS C18, m/z = 528 [M + H]+, Ret. time = 2.02 min. | ¹H NMR (400 MHz, DMSO): δ 9.89 (s, 1 H), 8.81 (s, 1 H), 8.59 (d, J = 8.7 Hz, 1 H), 8.46 (dd, J = 5.9, 7.5 Hz, 1 H), 8.03 (d, J = 2.8 Hz, 1 H), 7.86 (s, 1 H), 7.73 (d, J = 8.2 Hz, 1 H), 7.57 (dd, J = 2.7, 10.2 Hz, 1 H), 7.45 (dd, J = 2.8, 8.8 Hz, 1 H), 7.05-6.98 (m, 2 H), 4.42 (s, 2 H), 3.76 (ddd, J = 3.3, 8.5, 11.8 Hz, 1 H), 3.67 (td, J = 4.4, 12.0 Hz, 1 H), 3.32 (d, J = 12.0 Hz, 2 H), 3.19 (d, J = 11.3 Hz, 2 H), 3.12-3.08 (m, 1 H), 2.48 (d, J = 10.4 Hz, 1 H), 2.22 (s, 4 H), 2.12 (d, J = 14.4 Hz, 1 H), 1.88-1.79 (m, 1 H), 1.77-1.70 (m, 1 H), 1.63 (d, J = 12.8 Hz, 2 H). | F AC63 BC80 |

TABLE 8-continued

Characterization Data (LCMS and $^1$H NMR).

| # | STRUCTURE | NAME | LCMS | $^1$H NMR | Method Reagent AA BB |
|---|---|---|---|---|---|
| I-506 | Isomer 2 Separated by Chiral SFC | (S)-4-(7-fluoro-imidazo[1,2-a]pyridin-3-yl)-7-((5-(4-methyl-1-oxa-4,8-diaza-spiro[5.5]un-decan-8-yl)pyridin-2-yl)amino)iso-indolin-1-one | Method AcHSS C18, m/z = 528 [M + H]+, Ret. time = 2.01 min. | $^1$H NMR (400 MHz, DMSO): δ 9.89 (s, 1 H), 8.81 (s, 1 H), 8.59 (d, J = 8.7 Hz, 1 H), 8.46 (dd, J = 5.9, 7.5 Hz, 1 H), 8.03 (d, J = 2.8 Hz, 1 H), 7.86 (s, 1 H), 7.73 (d, J = 8.2 Hz, 1 H), 7.57 (dd, J = 2.7, 10.2 Hz, 1 H), 7.45 (dd, J = 2.8, 8.8 Hz, 1 H), 7.05-6.98 (m, 2 H), 4.42 (s, 2 H), 3.76 (ddd, J = 3.3, 8.5, 11.8 Hz, 1 H), 3.67 (td, J = 4.4, 12.0 Hz, 1 H), 3.32 (d, J = 12.0 Hz, 2 H), 3.19 (d, J = 11.3 Hz, 2 H), 3.12-3.08 (m, 1 H), 2.48 (d, J = 10.4 Hz, 1 H), 2.22 (s, 4 H), 2.12 (d, J = 14.4 Hz, 1 H), 1.88-1.79 (m, 1 H), 1.77-1.70 (m, 1 H), 1.63 (d, J = 12.8 Hz, 2 H). | F AC63 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-507 | Isomer 1 Separated by Chiral SFC | (R)-7-((5-(1-oxa-4,8-diazaspiro[5.5]undecan-8-yl)pyridin-2-yl)amino)-4-(7-fluoroimidazo[1,2-a]pyridin-3-yl)isoindolin-1-one | Method AcHSS C18, m/z = 514.2 [M + H]+, Ret. time = 2.07 min. | ¹H NMR (400 MHz, DMSO): δ 9.84 (s, 1 H), 8.79 (s, 1 H), 8.57 (d, J = 8.6 Hz, 1 H), 8.43 (dd, J = 5.5, 7.7 Hz, 1 H), 8.02 (d, J = 3.1 Hz, 1 H), 7.82 (s, 1 H), 7.69 (d, J = 8.7 Hz, 1 H), 7.53 (dd, J = 2.6, 9.9 Hz, 1 H), 7.45 (dd, J = 3.0, 9.0 Hz, 1 H), 6.99 (ddd, J = 7.2, 7.2, 2.5 Hz, 1 H), 6.96 (d, J = 9.4 Hz, 1 H), 4.38 (s, 3 H), 3.63 (ddd, J = 4.9, 4.9, 14.5 Hz, 1 H), 3.52 (ddd, J = 4.0, 4.0, 11.8 Hz, 1 H), 3.24 (d, J = 11.8 Hz, 1 H), 3.20 (d, J = 12.0 Hz, 1 H), 3.11-3.06 (m, 2 H), 2.81 (d, J = 12.5 Hz, 1 H), 2.74-2.65 (m, 2 H), 2.57 (d, J = 12.7 Hz, 1 H), 1.81-1.76 (m, 1 H), 1.66 (t, J = 7.2 Hz, 1 H), 1.55 (d, J = 12.3 Hz, 2 H). | F AC65 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-508 | Isomer 2 Separated by Chiral SFC | (S)-7-((5-(1-oxa-4,8-diaza-spiro[5.5]un-decan-8-yl)pyridin-2-yl)amino)-4-(7-fluoroimidazo[1,2-a]pyridin-3-yl)isoindolin-1-one | Method AcHSS C18, m/z = 514 [M + H]+, Ret. time = 2.02 min. | ¹H NMR (400 MHz, DMSO): δ 9.84 (s, 1 H), 8.79 (s, 1 H), 8.57 (d, J = 8.6 Hz, 1 H), 8.43 (dd, J = 5.5, 7.7 Hz, 1 H), 8.02 (d, J = 3.1 Hz, 1 H), 7.82 (s, 1 H), 7.69 (d, J = 8.7 Hz, 1 H), 7.53 (dd, J = 2.6, 9.9 Hz, 1 H), 7.45 (dd, J = 3.0, 9.0 Hz, 1 H), 6.99 (ddd, J = 7.2, 7.2, 2.5 Hz, 1 H), 6.96 (d, J = 9.4 Hz, 1 H), 4.38 (s, 3 H), 3.63 (ddd, J = 4.9, 4.9, 14.5 Hz, 1 H), 3.52 (ddd, J = 4.0, 4.0, 11.8 Hz, 1 H), 3.24 (d, J = 11.8 Hz, 1 H), 3.20 (d, J = 12.0 Hz, 1 H), 3.11-3.06 (m, 2 H), 2.81 (d, J = 12.5 Hz, 1 H), 2.74-2.65 (m, 2 H), 2.57 (d, J = 12.7 Hz, 1 H), 1.81-1.76 (m, 1 H), 1.66 (t, J = 7.2 Hz, 1 H), 1.55 (d, J = 12.3 Hz, 2 H). | F AC65 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-509 | 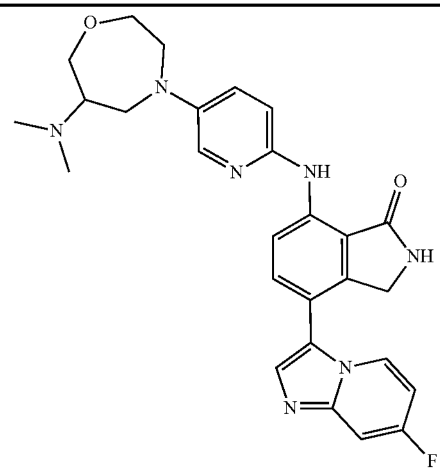 | 7-[[5-[6-(dimethylamino)-1,4-oxazepan-4-yl]-2-pyridyl]amino]-4-(7-fluoro-imidazo[1,2-a]pyridin-3-yl)isoindolin-1-one Formic acid salt | Method AcHSS C18, m/z = 502 [M + H]+, Ret. time = 1.94 min. | ¹H NMR (400 MHz, DMSO) δ 9.74 (s, 1 H), 8.74 (s, 1 H), 8.51-8.48 (m, 1 H), 8.40 (dd, J = 5.7, 7.3 Hz, 1 H), 7.95 (d, J = 3.0 Hz, 1 H), 7.81 (s, 1 H), 7.68-7.65 (m, 1 H), 7.53 (dd, J = 2.3, 10.1 Hz, 1 H), 7.33 (dd, J = 3.2, 9.1 Hz, 1 H), 7.01-6.95 (m, 2 H), 6.54 (s, 1 H), 4.38-4.36 (m, 2 H), 4.03-3.82 (m, 4 H), 3.67-3.60 (m, 1 H), 3.34 (s, 4 H), 2.43 (s, 6 H). | F AC68 BC80 |
| I-510 | Isomer 1 Separated by Chiral SFC | (R)-7-((6-((diethyl-amino)methyl)-5-(tetrahydrofuran-3-yl)pyridin-2-yl)amino)-4-(7-fluoro-imidazo[1,2-a]pyridin-3-yl)isoindolin-1-one | Method AcHSS C18, m/z = 515 [M + H]+, Ret. time = 2.22 min. | ¹H NMR (400 MHz, DMSO): δ 10.03 (s, 1 H), 8.82 (s, 1 H), 8.78 (d, J = 8.5 Hz, 1 H), 8.46-8.41 (m, 1 H), 7.81 (s, 1 H), 7.71 (d, J = 8.5 Hz, 1 H), 7.65 (d, J = 8.5 Hz, 1 H), 7.52 (dd, J = 2.4, 10.0 Hz, 1 H), 6.99-6.91 (m, 2 H), 4.38 (s, 2 H), 4.02-3.66 (m, 7 H), 3.55-3.49 (m, 1 H), 2.56-2.52 (m, 2 H), 2.33-2.24 (m, 1 H), 1.93-1.83 (m, 1 H), 1.23 (s, 1 H), 0.99 (t, J = 7.1, 7.1 Hz, 6 H). | F AC66 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-511 | Isomer 2 Separated by Chiral SFC | (S)-7-((6-((diethyl-amino)methyl)-5-(tetrahydrofuran-3-yl)pyridin-2-yl)amino)-4-(7-fluoro-imidazo[1,2-a]pyridin-3-yl)isoindolin-1-one | Method AcHSS C18, m/z = 515 [M + H]+, Ret. time = 2.23 min. | ¹H NMR (400 MHz, DMSO): δ 10.03 (s, 1 H), 8.82 (s, 1 H), 8.78 (d, J = 8.5 Hz, 1 H), 8.46-8.41 (m, 1 H), 7.81 (s, 1 H), 7.71 (d, J = 8.5 Hz, 1 H), 7.65 (d, J = 8.5 Hz, 1 H), 7.52 (dd, J = 2.4, 10.0 Hz, 1 H), 6.99-6.91 (m, 2 H), 4.38 (s, 2 H), 4.02-3.66 (m, 7 H), 3.55-3.49 (m, 1 H), 2.56-2.52 (m, 2 H), 2.33-2.24 (m, 1 H), 1.93-1.83 (m, 1 H), 1.23 (s, 1 H), 0.99 (t, J = 7.1, 7.1 Hz, 6 H). | F AC66 BC80 |

TABLE 8-continued

Characterization Data (LCMS and $^1$H NMR).

| # | STRUCTURE | NAME | LCMS | $^1$H NMR | Method Reagent AA BB |
|---|---|---|---|---|---|
| I-512 | 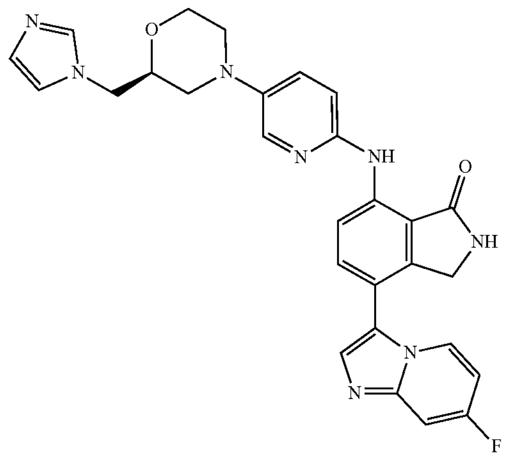 [SMILES: O=C1NCc2c(-c3cnc4cc(F)ccn34)ccc(Nc3ccc(N4CCO[C@H](Cn5ccnc5)C4)cn3)c21] | 4-(7-fluoro-imidazo[1,2-a]pyridin-3-yl)-7-[[5-[(2S)-2-(imidazol-1-ylmethyl)morpholin-4-yl]-2-pyridyl]amino]isoindolin-1-one | Method AcHSS C18, m/z = 525 [M + H]+, Ret. time = 2.01 min. | $^1$H NMR (400 MHz, DMSO): δ 9.89 (s, 1 H), 8.79 (s, 1 H), 8.59 (d, J = 8.3 Hz, 1 H), 8.43 (dd, J = 6.4, 6.4 Hz, 1 H), 8.02 (d, J = 3.4 Hz, 1 H), 7.82 (s, 1 H), 7.70 (d, J = 8.7 Hz, 1 H), 7.65 (s, 1 H), 7.54 (dd, J = 2.9, 10.2 Hz, 1 H), 7.45 (dd, J = 3.1, 9.1 Hz, 1 H), 7.22 (s, 1 H), 7.02-6.96 (m, 2 H), 6.92 (s, 1 H), 4.39 (s, 2 H), 4.20 (dd, J = 4.0, 13.7 Hz, 1 H), 4.12 (dd, J = 7.4, 13.9 Hz, 1 H), 3.99 (d, J = 10.5 Hz, 1 H), 3.90 (ddd, J = 5.8, 5.8, 10.8 Hz, 1 H), 3.54 (d, J = 10.8 Hz, 1 H), 3.46 (d, J = 10.8 Hz, 1 H), 3.15 (t, J = 13.5 Hz, 1 H), 2.93 (ddd, J = 12.3, 12.3, 3.9 Hz, 1 H), 2.42 (t, J = 11.5 Hz, 1 H). | F AC70 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-513 | Isomer 1 Separated by Chiral SFC | 4-(7-fluoro-imidazo[1,2-a]pyridin-3-yl)-7-((S)-1-((S)-3-hydroxy-piperidin-1-yl)ethyl)pyridin-2-yl)amino)isoindolin-1-one | Method AcHSS C18, m/z = 487 [M + H]+, Ret. time = 1.93 min. | ¹H NMR (400 MHz, DMSO): δ 10.14 (s, 1 H), 8.90 (s, 1 H), 8.78 (d, J = 8.7 Hz, 1 H), 8.49 (dd, J = 6.1, 7.6 Hz, 1 H), 8.26 (d, J = 2.8 Hz, 1 H), 7.89 (s, 1 H), 7.80 (d, J = 8.4 Hz, 1 H), 7.70 (dd, J = 2.4, 8.6 Hz, 1 H), 7.59 (dd, J = 2.5, 10.2 Hz, 1 H), 7.06 (d, J = 8.0 Hz, 1 H), 7.04 (ddd, J = 7.4, 7.4, 3.0 Hz, 1 H), 4.59 (d, J = 5.2 Hz, 1 H), 4.46 (s, 2 H), 3.60 (q, J = 7.4 Hz, 1 H), 3.50-3.48 (m, 1 H), 2.87 (d, J = 9.3 Hz, 1 H), 2.80 (d, J = 11.6 Hz, 1 H), 1.92-1.83 (m, 3 H), 1.67 (t, J = 10.3 Hz, 2 H), 1.51-1.45 (m, 1 H), 1.38 (d, J = 7.0 Hz, 3 H), 1.08 (dd, J = 4.1, 12.2 Hz, 1 H), 1.02 (dd, J = 5.8, 13.7 Hz, 1 H). | F AC71 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-514 | Isomer 2 Separated by Chiral SFC | 4-(7-fluoro-imidazo[1,2-a]pyridin-3-yl)-7-((5-((R)-1-((S)-3-hydroxy-piperidin-1-yl)ethyl)pyridin-2-yl)amino)iso-indolin-1-one | Method AcHSS C18, m/z = 487 [M + H]+, Ret. time = 1.93 min. | ¹H NMR (400 MHz, DMSO): δ 10.14 (s, 1 H), 8.90 (s, 1 H), 8.78 (d, J = 8.7 Hz, 1 H), 8.49 (dd, J = 6.1, 7.6 Hz, 1 H), 8.26 (d, J = 2.8 Hz, 1 H), 7.89 (s, 1 H), 7.80 (d, J = 8.4 Hz, 1 H), 7.70 (dd, J = 2.4, 8.6 Hz, 1 H), 7.59 (dd, J = 2.5, 10.2 Hz, 1 H), 7.06 (d, J = 8.0 Hz, 1 H), 7.04 (ddd, J = 7.4, 7.4, 3.0 Hz, 1 H), 4.59 (d, J = 5.2 Hz, 1 H), 4.46 (s, 2 H), 3.60 (q, J = 7.4 Hz, 1 H), 3.50-3.48 (m, 1 H), 2.87 (d, J = 9.3 Hz, 1 H), 2.80 (d, J = 11.6 Hz, 1 H), 1.92-1.83 (m, 3 H), 1.67 (t, J = 10.3 Hz, 2 H), 1.51-1.45 (m, 1 H), 1.38 (d, J = 7.0 Hz, 3 H), 1.08 (dd, J = 4.1, 12.2 Hz, 1 H), 1.02 (dd, J = 5.8, 13.7 Hz, 1 H). | F AC70 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-515 | Isomer 1 Separated by Chiral SFC | (R)-4-(7-fluoro-imidazo[1,2-a]pyridin-3-yl)-7-((6-(pyrrolidin-1-ylmethyl)-5-(tetrahydrofuran-3-yl)pyridin-2-yl)amino)isoindolin-1-one | Method AcHSS C18, m/z = 513 [M + H]+, Ret. time = 2.10 min. | ¹H NMR (400 MHz, DMSO): δ 10.09 (s, 1 H), 8.91 (s, 1 H), 8.53-8.39 (m, 2 H), 7.89 (s, 1 H), 7.78 (d, J = 8.4 Hz, 2 H), 7.59 (dd, J = 2.6, 10.6 Hz, 1 H), 7.13-7.03 (m, 2 H), 4.45 (s, 2 H), 4.08-4.00 (m, 2 H), 3.87-3.77 (m, 3 H), 3.61 (t, J = 7.6 Hz, 2 H), 3.34-3.25 (m, 2 H), 2.98 (t, J = 4.4 Hz, 1 H), 2.38-2.35 (m, 2 H), 1.97-1.88 (m, 8 H). | F AC67 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-516 | Isomer 2 Separated by Chiral SFC | (S)-4-(7-fluoro-imidazo[1,2-a]pyridin-3-yl)-7-((6-(pyrrolidin-1-ylmethyl)-5-(tetrahydrofuran-3-yl)pyridin-2-yl)amino)iso-indolin-1-one Formic acid salt | Method AcHSS C18, m/z = 513 [M + H]+, Ret. time = 2.17 min. | ¹H NMR (400 MHz, DMSO): δ 10.09 (s, 1 H), 8.91 (s, 1 H), 8.53-8.39 (m, 2 H), 7.89 (s, 1 H), 7.78 (d, J = 8.4 Hz, 2 H), 7.59 (dd, J = 2.6, 10.6 Hz, 1 H), 7.13-7.03 (m, 2 H), 4.45 (s, 2 H), 4.08-4.00 (m, 2 H), 3.87-3.77 (m, 3 H), 3.61 (t, J = 7.6 Hz, 2 H), 3.34-3.25 (m, 2 H), 2.98 (t, J = 4.4 Hz, 1 H), 2.38-2.35 (m, 2 H), 1.97-1.88 (m, 8 H). | F AC67 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-517 | (structure) | 7-[[5-[3-[(dimethylamino)methyl]morpholin-4-yl]-2-pyridyl]amino]-4-(7-fluoroimidazo[1,2-a]pyridin-3-yl)isoindolin-1-one | Method AcHSS C18, m/z = 502 [M + H]+, Ret. time = 2.01 min. | ¹H NMR (400 MHz, DMSO): δ 9.85 (s, 1 H), 8.78 (s, 1 H), 8.55 (d, J = 9.4 Hz, 1 H), 8.43 (dd, J = 6.2, 7.5 Hz, 1 H), 7.98 (d, J = 2.3 Hz, 1 H), 7.83 (s, 1 H), 7.70 (d, J = 8.4 Hz, 1 H), 7.53 (dd, J = 2.7, 9.8 Hz, 1 H), 7.45 (dd, J = 3.1, 9.0 Hz, 1 H), 7.01-6.95 (m, 2 H), 4.39 (s, 2 H), 3.96 (d, J = 10.8 Hz, 1 H), 3.91 (d, J = 10.5 Hz, 1 H), 3.73 (d, J = 11.0 Hz, 1 H), 3.67 (dd, J = 1.8, 10.8 Hz, 1 H), 3.60 (ddd, J = 10.9, 10.9, 3.0 Hz, 1 H), 3.14 (td, J = 2.4, 12.6 Hz, 1 H), 3.04 (ddd, J = 11.4, 11.4, 3.5 Hz, 1 H), 2.75 (t, J = 11.6 Hz, 1 H), 2.13 (s, 6 H), 1.85 (d, J = 13.3 Hz, 2 H). | F AC69 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-518 | Isomer 1 Separated by Chiral SFC | (S)-7-((5-(6-(dimethyl-amino)-1,4-oxazepan-4-yl)pyridin-2-yl)amino)-4-(7-fluoro-imidazo[1,2-a]pyridin-3-yl)isoindolin-1-one | Method AcHSS C18, m/z = 502 [M + H]+, Ret. time = 1.88 min. | ¹H NMR (400 MHz, DMSO): δ 9.73 (s, 1 H), 8.74 (s, 1 H), 8.48 (d, J = 8.6 Hz, 1 H), 8.41 (dd, J = 6.0, 7.8 Hz, 1 H), 7.92 (d, J = 3.1 Hz, 1 H), 7.81 (s, 1 H), 7.67 (d, J = 9.0 Hz, 1 H), 7.53 (dd, J = 2.3, 10.0 Hz, 1 H), 7.31 (dd, J = 3.1, 9.0 Hz, 1 H), 7.01-6.94 (m, 2H), 4.37 (s, 2 H), 3.97-3.80 (m, 4 H), 3.67-3.59 (m, 1 H), 3.38-3.27 (m, 3 H), 3.12-3.08 (m, 1 H), 2.30-2.28 (m, 6 H). | F AC68 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-519 | Isomer 2 Separated by Chiral SFC | (R)-7-(5-(6-(dimethyl-amino)-1,4-oxazepan-4-yl)pyridin-2-yl)amino)-4-(7-fluoro-imidazo[1,2-a]pyridin-3-yl)isoindolin-1-one | Method AcHSS C18, m/z = 502 [M + H]+, Ret. time = 1.88 min. | ¹H NMR (400 MHz, DMSO): δ 9.72 (s, 1 H), 8.74 (s, 1 H), 8.48 (d, J = 8.4 Hz, 1 H), 8.41 (dd, J = 5.9, 7.4 Hz, 1 H), 7.92 (d, J = 3.0 Hz, 1 H), 7.81 (s, 1 H), 7.67 (d, J = 8.6 Hz, 1 H), 7.53 (dd, J = 2.3, 10.1 Hz, 1 H), 7.31 (dd, J = 3.1, 9.0 Hz, 1H), 7.01-6.94 (m, 2 H), 4.37 (s, 2 H), 3.97-3.75 (m, 4 H), 3.67-3.59 (m, 1 H), 3.38-3.25 (m, 3 H), 3.12-3.05 (m, 1 H), 2.30-2.28 (m, 6 H). | F AC68 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-520 | Isomer 1 Separated by Chiral SFC | (S)-7-((5-(1-(dimethylamino)ethyl)pyridin-2-yl)amino)-4-(7-fluoroimidazo[1,2-a]pyridin-3-yl)isoindolin-1-one | Method AcHSS C18, m/z = 431 [M + H]+, Ret. time = 1.83 min. | ¹H NMR (400 MHz, DMSO): δ 10.13 (s, 1 H), 8.78-8.76 (m, 1 H), 8.48 (dd, J = 5.8, 7.6 Hz, 1 H), 8.25 (d, J = 2.3 Hz, 1 H), 7.88 (s, 1 H), 7.79 (d, J = 8.5 Hz, 1 H), 7.70 (dd, J = 2.3, 8.5 Hz, 1 H), 7.56 (dd, J = 2.3, 10.0 Hz, 1 H), 7.05-7.00 (m, 2 H), 4.45 (s, 2 H), 3.19-3.16 (m, 1 H), 2.17 (s, 6 H), 1.36 (d, J = 7.2 Hz, 3 H). | F AC73 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-521 | Isomer 2 Separated by Chiral SFC | (R)-7-((5-(1-(dimethyl-amino)ethyl)pyridin-2-yl)amino)-4-(7-fluoro-imidazo[1,2-a]pyridin-3-yl)isoindolin-1-one | Method AcHSS C18, m/z = 431 [M + H]+, Ret. time = 1.83 min. | ¹H NMR (400 MHz, DMSO): δ 10.13 (s, 1 H), 8.77 (d, J = 8.7 Hz, 1 H), 8.48 (dd, J = 5.7, 7.6 Hz, 1 H), 8.25 (d, J = 2.3 Hz, 1 H), 7.87 (s, 1 H), 7.78 (d, J = 8.4 Hz, 1 H), 7.69 (dd, J = 2.4, 8.5 Hz, 1 H), 7.55 (dd, J = 2.3, 10.0 Hz, 1 H), 7.05-6.99 (m, 2 H), 4.44 (s, 2 H), 3.19-3.16 (m, 1 H), 2.17 (s, 6H), 1.36 (d, J = 6.5 Hz, 3 H). | F AC73 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-522 | Isomer 1 Separated by Chiral SFC | 4-(7-fluoro-imidazo[1,2-a]pyridin-3-yl)-7-((5-((S)-1-((S)-2-methylmorpho-lino)ethyl)pyridin-2-yl)amino)iso-indolin-1-one | Method AcHSS C18, m/z = 487 [M + H]+, Ret. time = 2.02 min. | ¹H NMR (400 MHz, DMSO): δ 10.11 (s, 1 H), 8.86 (s, 1 H), 8.73 (d, J = 8.6 Hz, 1 H), 8.45 (dd, J = 5.9, 7.5 Hz, 1 H), 8.22 (s, 1 H), 7.85 (s, 1 H), 7.75 (d, J = 8.4 Hz, 1 H), 7.67 (d, J = 8.6 Hz, 1 H), 7.54 (dd, J = 2.3, 10.0 Hz, 1 H), 7.04-6.97 (m, 2 H), 4.42 (s, 2 H), 3.80-3.77 (m, 1 H), 3.57-3.39 (m, 3 H), 2.84-2.78 (m, 1 H), 2.62-2.56 (m, 1 H), 2.09-2.00 (m, 1 H), 1.66-1.61 (m, 1 H), 1.33 (d, J = 6.5 Hz, 3 H), 0.99 (d, J = 6.3 Hz, 3 H). | F AC74 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-523 | Isomer 2 Separated by Chiral SFC | 4-(7-fluoro imidazo[1,2-a]pyridin-3-yl)-7-((5-((R)-1-((S)-2-methylmorpholino)ethyl)pyridin-2-yl)amino)isoindolin-1-one | Method AcHSS C18, m/z = 487 [M + H]+, Ret. time = 1.95 min. | ¹H NMR (400 MHz, DMSO): δ 10.09 (s, 1 H), 8.74 (d, J = 8.6 Hz, 1 H), 8.43 (dd, J = 6.0, 7.3 Hz, 1 H), 8.21 (d, J = 2.1 Hz, 1 H), 7.82 (s, 1 H), 7.73 (d, J = 8.8 Hz, 1 H), 7.65 (dd, J = 2.3, 8.5 Hz, 1 H), 7.49 (dd, J = 2.4, 10.0 Hz, 1 H), 7.01-6.95 (m, 2 H), 4.40 (s, 2 H), 3.71-3.67 (m, 1 H), 3.57-3.50 (m, 1 H), 3.49-3.40 (m, 1 H), 3.15-3.13 (m, 2 H), 2.89-2.84 (m, 1 H), 1.98-1.91 (m, 1 H), 1.77-1.70 (m, 1 H), 1.33 (d, J = 6.8 Hz, 3 H), 1.06 (d, J = 6.4 Hz, 3 H) | F AC74 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-524 | 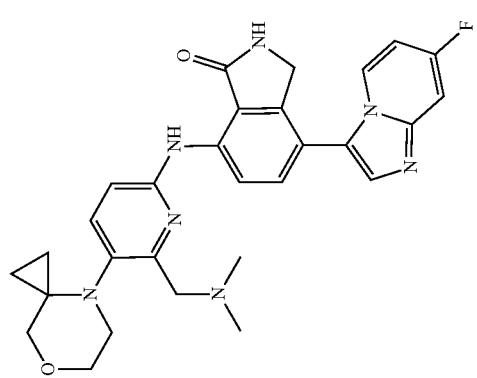 | 7-[[6-[(dimethyl-amino)methyl]-5-[(3R)-3-hydroxy-1-piperidyl]-2-pyridyl]amino]-4-(7-fluoro-imidazo[1,2-a]pyridin-3-yl)isoindolin-1-one Formic acid salt | Method AcHSS C18, m/z = 516.2 [M + H]+, Ret. time = 2.18 min. | ¹H NMR (400 MHz, DMSO): δ 10.04 (s, 1 H), 8.84 (s, 1 H), 8.67 (d, J = 8.7 Hz, 1 H), 8.43 (dd, J = 5.9, 7.5 Hz, 1 H), 8.16 (s, 1 H), 7.83 (s, 1 H), 7.71 (d, J = 8.5 Hz, 1 H), 7.60 (d, J = 9.1 Hz, 1 H), 7.54 (dd, J = 2.7, 10.1 Hz, 1 H), 7.03-6.97 (m, 2 H), 6.55 (s, 1 H), 4.40 (s, 2 H), 3.91-3.83 (m, 2 H), 3.75-3.70 (m, 1 H), 3.12-3.08 (m, 1 H), 3.02-2.99 (m, 1 H), 2.70-2.67 (m, 2 H), 2.54 (s, 6 H), 1.87-1.80 (m, 2 H), 1.66-1.59 (m, 1 H), 1.37-1.30 (m, 1 H). | ACp AC75 BC80 |
| I-525 | Separated by Chiral SFC | 7-[[6-[(dimethyl-amino)methyl]-5-(7-oxa-4-azaspiro[2.5]octan-4-yl)-2-pyridyl]amino]-4-(7-fluoro-imidazo[1,2-a]pyridin-3-yl)isoindolin-1-one | Method AcHSS C18, m/z = 528 [M + H]+, Ret. time = 2.24 min. | ¹H NMR (400 MHz, DMSO): δ 9.92 (s, 1 H), 8.74 (s, 1 H), 8.64 (d, J = 8.4 Hz, 1 H), 8.35 (dd, J = 5.9, 7.5 Hz, 1 H), 7.74 (s, 1 H), 7.62 (d, J = 8.7 Hz, 1 H), 7.46-7.43 (m, 2 H), 6.93-6.87 (m, 1 H), 6.83 (d, J = 8.6 Hz, 1 H), 4.31 (s, 2H), 3.66-3.60 (m, 2 H), 3.57-3.45 (m, 4 H), 3.23-3.15 (m, 2 H), 2.27 (s, 6H), 0.53-0.47 (m, 2 H), 0.27-0.21 (m, 2 H). | ACp AC76 BC80 |

| # | STRUCTURE | NAME | LCMS | ¹H NMR | Method Reagent AA BB |
|---|---|---|---|---|---|
| I-526 | Isomer 1 Separated by Chiral SFC | (S)-4-(7-fluoro-imidazo[1,2-a]pyridin-3-yl)-7-((5-(1-(4-hydroxy-piperidin-1-yl)ethyl)pyridin-2-yl)amino)iso-indolin-1-one | Method AcHSS C18, m/z = 487 [M + H]+, Ret. time = 1.91 min. | ¹H NMR (400 MHz, DMSO): δ 10.13 (s, 1 H), 8.89 (s, 1 H), 8.77 (d, J = 7.9 Hz, 1 H), 8.49 (dd, J = 5.8, 7.6 Hz, 1 H), 8.25 (d, J = 2.1 Hz, 1 H), 7.89 (s, 1 H), 7.79 (d, J = 8.5 Hz, 1 H), 7.69 (dd, J = 2.4, 8.5 Hz, 1 H), 7.59 (dd, J = 2.3, 10.1 Hz, 1 H), 7.06-7.01 (m, 2 H), 4.55 (d, J = 4.0 Hz, 1 H), 4.46 (s, 2 H), 3.58 (q, J = 6.7 Hz, 1 H), 2.80-2.70 (m, 3 H), 2.15-2.01 (m, 2 H), 1.75-1.72 (m, 2 H), 1.48-1.33 (m, 5 H). | F AC77 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-527 | (Isomer 2, Separated by Chiral SFC) | (R)-4-(7-fluoro-imidazo[1,2-a]pyridin-3-yl)-7-((5-(1-(4-hydroxy-piperidin-1-yl)ethyl)pyridin-2-yl)amino)iso-indolin-1-one | Method AcHSS C18, m/z = 487 [M + H]+, Ret. time = 1.91 min. | ¹H NMR (400 MHz, DMSO): δ 10.13 (s, 1 H), 8.89 (s, 1 H), 8.77 (d, J = 7.9 Hz, 1 H), 8.49 (dd, J = 5.8, 7.6 Hz, 1 H), 8.25 (d, J = 2.1 Hz, 1 H), 7.89 (s, 1 H), 7.79 (d, J = 8.5 Hz, 1 H), 7.69 (dd, J = 2.4, 8.5 Hz, 1 H), 7.59 (dd, J = 2.3, 10.1 Hz, 1 H), 7.06-7.01 (m, 2 H), 4.55 (d, J = 4.0 Hz, 1 H), 4.46 (s, 2 H), 3.58 (q, J = 6.7 Hz, 1 H), 2.80-2.70 (m, 3 H), 2.15-2.01 (m, 2 H), 1.75-1.72 (m, 2 H), 1.48-1.33 (m, 5 H). | F AC77 BC80 |
| I-528 | 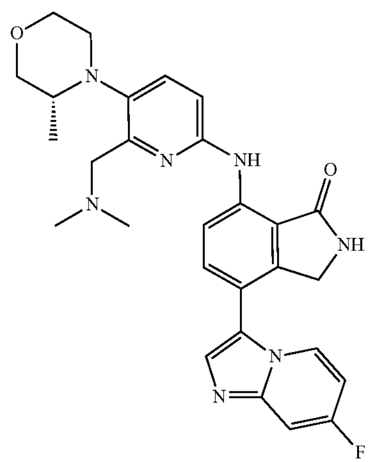 [SMILES: C[C@@H]1COCCN1c1ccc(Nc2ccc(-c3cnc4cc(F)ccn34)c3c2C(=O)NC3)nc1CN(C)C] | 7-[[6-[(dimethyl-amino)methyl]-5-[(3R)-3-methylmorpho-lin-4-yl]-2-pyridyl]amino]-4-(7-fluoro-imidazo[1,2-a]pyridin-3-yl)isoindolin-1-one Formic acid salt | Method AcHSS C18, m/z = 516 [M + H]+, Ret. time = 2.24 min. | ¹H NMR (400 MHz, DMSO): δ 10.08 (s, 1 H), 8.84 (s, 1 H), 8.79 (d, J = 8.6 Hz, 1 H), 8.44 (dd, J = 5.8, 7.6 Hz, 1 H), 8.20 (s, 1 H), 7.83 (s, 1 H), 7.70 (dd, J = 8.7, 17.7 Hz, 2 H), 7.54 (dd, J = 2.3, 10.0 Hz, 1 H), 7.01-6.96 (m, 2 H), 6.59 (br s, 1 H), 4.40 (s, 2 H), 3.98 (d, J = 11.7 Hz, 1 H), 3.86-3.78 (m, 2 H), 3.70-3.63 (m, 1 H), 3.30-3.17 (m, 1 H), 3.09-3.05 (m, 2 H), 2.74-2.61 (m, 1 H), 2.32 (s, 6 H), 0.71 (d, J = 5.7 Hz, 3 H). | ACp AC78 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-529 | 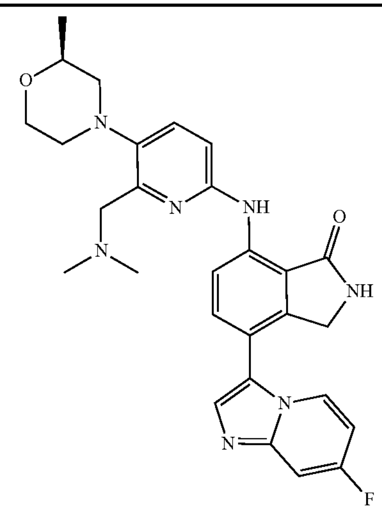 | 7-[[6-[(dimethylamino)methyl]-5-[(2S)-2-methylmorpholin-4-yl]-2-pyridyl]amino]-4-(7-fluoroimidazo[1,2-a]pyridin-3-yl)isoindolin-1-one Bis formic acid salt | Method AcHSS C18, m/z = 516 [M + H]+, Ret. time = 2.27 min. | ¹H NMR (400 MHz, DMSO): δ 10.00 (s, 1 H), 8.81 (s, 1 H), 8.63-8.58 (m, 1 H), 8.41 (dd, J = 5.8, 7.5 Hz, 1H), 8.18 (s, 2 H), 7.82 (s, 1 H), 7.71 (d, J = 9.2 Hz, 1 H), 7.66 (d, J = 8.2 Hz, 1 H), 7.52 (dd, J = 2.6, 10.0 Hz, 1 H), 7.07-6.98 (m, 2 H), 5.74 (s, 1 H), 4.38 (s, 2 H), 3.96 (m, 2 H), 3.91-3.84 (m, 1 H), 3.79-3.68 (m, 2 H), 3.06-2.92 (m, 2 H), 2.83-2.74 (m, 1 H), 2.58 (s, 6 H), 1.12 (d, J = 6.9 Hz, 3 H). | ACp AC79 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-530 | 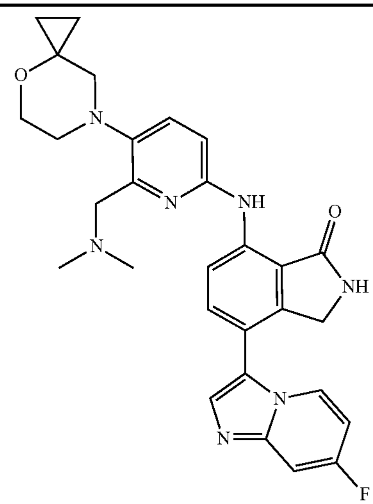 | 7-[[6-[(dimethyl-amino)methyl]-5-(4-oxa-7-azaspiro[2.5]octan-7-yl)-2-pyridyl]amino]-4-(7-fluoro-imidazo[1,2-a]pyridin-3-yl)isoindolin-1-one Formic acid salt | Method AcHSS C18, m/z = 528 [M + H]+, Ret. time = 2.34 min. | ¹H NMR (400 MHz, DMSO): δ 10.04 (s, 1 H), 8.83 (s, 1 H), 8.76 (d, J = 8.0 Hz, 1 H), 8.44 (dd, J = 5.9, 7.5 Hz, 1 H), 8.26 (s, 1 H), 7.83 (s, 1 H), 7.71 (d, J = 8.6 Hz, 1 H), 7.61 (d, J = 8.6 Hz, 1 H), 7.53 (dd, J = 2.8, 10.6 Hz, 1 H), 7.01-6.94 (m, 2 H), 6.68 (br s, 1 H), 4.40-4.38 (m, 2 H), 3.83-3.79 (m, 2 H), 3.62-3.58 (m, 2 H), 3.06-3.02 (m, 2 H), 2.95 (m, 2 H), 2.30 (s, 6 H), 0.77-0.74 (m, 2 H), 0.62-0.58 (m, 2 ` 1H). | Acp AC80 BC80 |
| I-531 | 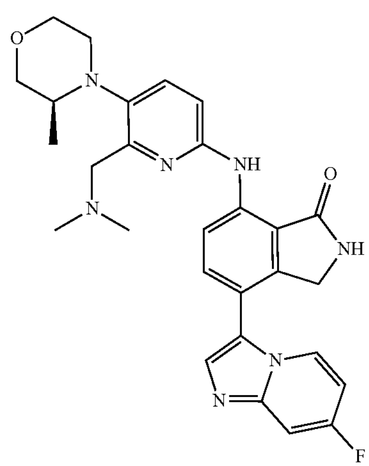 [SMILES: C[C@H]1COCCN1c1ccc(Nc2ccc(-c3cnc4cc(F)ccn34)c3c2C(=O)NC3)nc1CN(C)C] | 7-[[6-[(dimethyl-amino)methyl]-5-[(3S)-3-methylmorpho-lin-4-yl]-2-pyridyl]amino]-4-(7-fluoro-imidazo[1,2-a]pyridin-3-yl)isoindolin-1-one | Method AcHSS C18, m/z = 516 [M + H]+, Ret. time = 2.23 min. | ¹H NMR (400 MHz, DMSO): δ 10.08 (s, 1 H), 8.84 (s, 1 H), 8.78-8.76 (m, 1 H), 8.44 (dd, J = 5.9, 7.4 Hz, 1 H), 7.84 (s, 1 H), 7.71 (t, J = 8.8 Hz, 2 H), 7.54 (dd, J = 2.4, 10.2 Hz, 1 H), 7.02-6.97 (m, 2 H), 4.40 (s, 2 H), 4.12-3.96 (m, 1 H), 3.86-3.79 (m, 2 H), 3.70-3.64 (m, 1 H), 3.30-3.15 (m, 3 H), 3.06-3.00 (m, 1 H), 2.74-2.67 (m, 1 H), 2.38-2.33 (m, 6 H), 0.70 (d, J = 5.9 Hz, 3 H). | ACp AC81 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-532 | 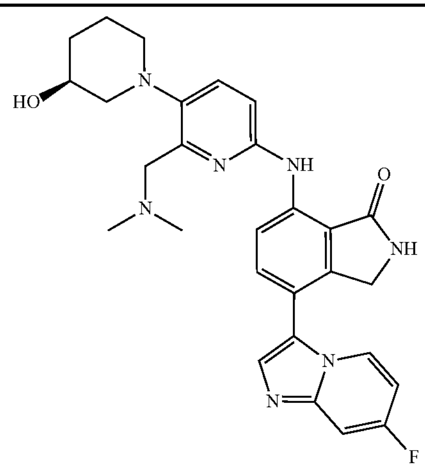 | 7-[[6-[(dimethyl-amino)methyl]-5-[(3S)-3-hydroxy-1-piperidyl]-2-pyridyl]amino]-4-(7-fluoro-imidazo[1,2-a]pyridin-3-yl)isoindolin-1-one | Method AcHSS C18, m/z = 516 [M + H]+, Ret. time = 2.18 min. | ¹H NMR (400 MHz, DMSO): δ 10.02 (s, 1 H), 8.82 (s, 1H), 8.72 (d, J = 9.2 Hz, 1 H), 8.44 (dd, J = 5.9, 7.5 Hz, 1 H), 7.83 (s, 1 H), 7.71 (d, J = 8.7 Hz, 1 H), 7.55-7.51 (m, 2 H), 7.01-6.93 (m, 2 H), 4.87-4.78 (m, 1H), 4.39 (s, 2 H), 3.73-3.63 (m, 3 H), 3.18-3.10 (m, 1 H), 3.09-3.01 (m, 1 H), 2.64-2.55 (m, 1 H), 2.43-2.29 (m, 6 H), 1.94-1.85 (m, 1 H), 1.83-1.73 (m, H), 1.66-1.57 (m, 1 H), 1.34-1.21 (m, 1 H). | ACp AC82 BC80 |
| I-533 | 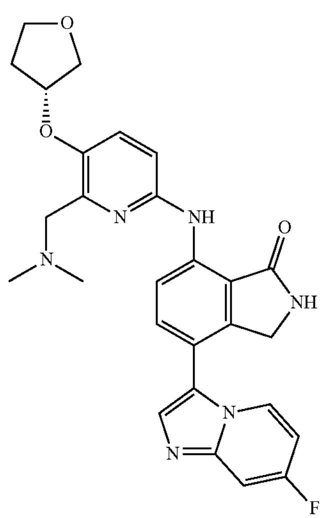 [SMILES: CN(C)Cc1nc(Nc2ccc(-c3cnc4cc(F)ccn34)c3c2C(=O)NC3)ccc1O[C@@H]1CCOC1] | 7-[[6-[(dimethyl-amino)methyl]-5-[(3R)-tetrahydrofuran-3-yl]oxy-2-pyridyl]amino]-4-(7-fluoro-imidazo[1,2-a]pyridin-3-yl)isoindolin-1-one | Method AcHSS C18, m/z = 503 [M + H]+, Ret. time = 2.05 min. | ¹H NMR (400 MHz, DMSO): δ 9.95 (s, 1 H), 8.80 (s, 1 H), 8.66 (d, J = 8.9 Hz, 1 H), 8.44 (dd, J = 6.0, 7.4 Hz, 1 H), 7.82 (s, 1 H), 7.70 (d, J = 8.9 Hz, 1 H), 7.53 (dd, J = 2.9, 10.3 Hz, 1 H), 7.49 (d, J = 8.9 Hz, 1 H), 7.01-6.95 (m, 2 H), 5.06-5.02 (m, 1 H), 4.39 (s, 2 H), 3.92-3.77 (m, 4 H), 3.55-3.52 (m, 2 H), 2.27 (s, 6 H), 2.23-2.12 (m, 1 H), 2.07-1.99 (m, 1 H). | ACp AC84 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-534 | 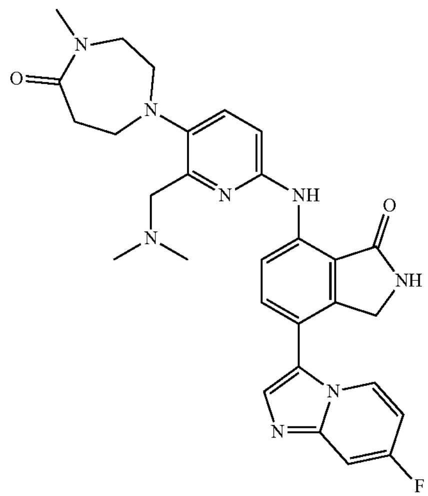 [SMILES: CN(C)Cc1nc(Nc2ccc(-c3cnc4cc(F)ccn34)c3c2C(=O)NC3)ccc1N1CCC(=O)N(C)CC1] | 7-[[6-[(dimethylamino)methyl]-5-(4-methyl-5-oxo-1,4-diazepan-1-yl)-2-pyridyl]amino]-4-(7-fluoroimidazo[1,2-a]pyridin-3-yl)isoindolin-1-one Formic acid salt | Method AcHSS C18, m/z = 543 [M + H]+, Ret. time = 2.00 min. | ¹H NMR (400 MHz, DMSO): δ 10.04 (s, 1 H), 8.83 (s, 1 H), 8.75 (d, J = 8.9 Hz, 1 H), 8.44 (dd, J = 5.8, 7.5 Hz, 1 H), 8.18 (s, 1 H), 7.83 (s, 1 H), 7.72 (d, J = 7.7 Hz, 1 H), 7.59 (d, J = 9.5 Hz, 1 H), 7.54 (dd, J = 2.6, 10.0 Hz, 1 H), 7.01-6.96 (m, 1 H), 6.94 (d, J = 8.9 Hz, 1 H), 4.39 (s, 2 H), 3.64-3.58 (m, 4 H), 3.11-3.02 (m, 4 H), 2.93-2.92 (m, 3 H), 2.74-2.67 (m, 2 H), 2.35 (s, 6H). | Acp AC83 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-535 | 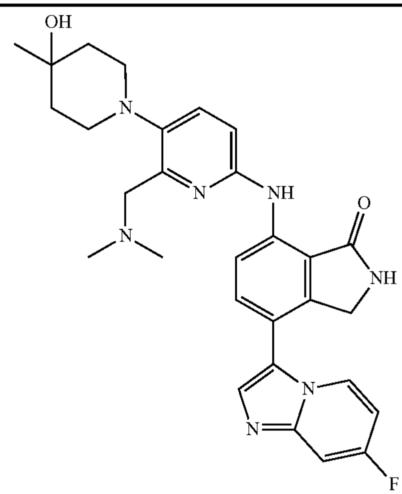 | 7-[[6-[(dimethyl-amino)methyl]-5-(4-hydroxy-4-methyl-1-piperidyl)-2-pyridyl]amino]-4-(7-fluoro-imidazo[1,2-a]pyridin-3-yl)isoindolin-1-one Formic acid salt | Method AcHSS C18, m/z = 530 [M + H]+, Ret. time = 2.13 min. | ¹H NMR (400 MHz, DMSO): δ 10.01 (s, 1 H), 8.81 (s, 1 H), 8.73 (d, J = 8.9 Hz, 1 H), 8.44 (dd, J = 6.6, 6.6 Hz, 1 H), 8.21 (s, 1 H), 7.82 (s, 1 H), 7.70 (d, J = 8.6 Hz, 1 H), 7.57 (d, J = 8.8 Hz, 1 H), 7.53 (dd, J = 3.0, 10.5 Hz, 1 H), 6.98 (ddd, J = 7.5, 7.5, 2.7 Hz, 1 H), 6.93 (d, J = 8.8 Hz, 1 H), 4.39 (s, 2 H), 3.04-2.95 (m, 2 H), 2.92-2.85 (m, 2 H), 2.35 (s, 6 H), 1.68-1.61 (m, 4 H), 1.21 (s, 3 H). | ACp AC85 BC80 |
| I-536 | 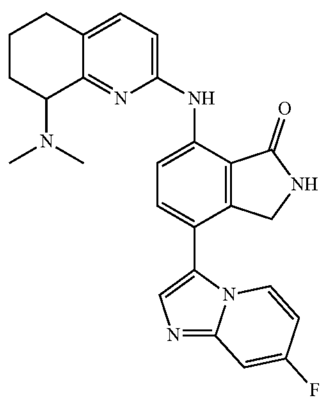 [SMILES: CN(C)C1CCCc2ccc(Nc3ccc(-c4cnc5cc(F)ccn45)c4c3C(=O)NC4)nc21] | 7-[[8-(dimethylamino)-5,6,7,8-tetrahydro-quinolin-2-yl]amino]-4-(7-fluoro-imidazo[1,2-a]pyridin-3-yl)isoindolin-1-one Formic acid salt | Method AcHSS C18, m/z = 457 [M + H]+, Ret. time = 2.21 min. | ¹H NMR (400 MHz, DMSO): δ 10.00 (s, 1 H), 8.83 (s, 1 H), 8.81 (d, J = 4.7 Hz, 1 H), 8.43 (dd, J = 6.0, 8.0 Hz, 1 H), 8.25 (s, 1 H), 7.83 (s, 1 H), 7.70 (d, J = 8.2 Hz, 1 H), 7.53 (dd, J = 2.4, 9.9 Hz, 1 H), 7.44 (dt, J = 9.3 Hz, 1 H), 6.99 (dt, J = 3.0, 7.7 Hz, 1 H), 6.85 (d, J = 8.2 Hz, 1 H), 4.39 (s, 2 H), 3.56 (t, J = 5.8 Hz, 1 H), 2.74-2.65 (m, 2 H), 2.33 (s, 6 H), 1.86-1.76 (m, 2 H), 1.69-1.61 (m, 2 H). | ACp AC86 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-537 | Isomer 1 Separated by Chiral SFC | (R)-7-((6-((dimethylamino)methyl)-5-(tetrahydrofuran-3-yl)pyridin-2-yl)amino)-4-(7-methylimidazo[1,2-b]pyridazin-3-yl)isoindolin-1-one | Method AcHSS C18, m/z = 484 [M + H]+, Ret. time = 2.36 min. | ¹H NMR (400 MHz, DMSO): δ 10.09 (s, 1 H), 8.90 (s, 1 H), 8.74 (d, J = 8.9 Hz, 1 H), 8.53 (d, J = 2.7 Hz, 1 H), 8.18 (d, J = 8.0 Hz, 1 H), 8.02 (s, 2 H), 7.67 (d, J = 8.4 Hz, 1 H), 6.95 (d, J = 8.2 Hz, 1 H), 4.56 (s, 2 H), 4.01-3.94 (m, 2 H), 3.87-3.78 (m, 2 H), 3.66 (d, J = 12.2 Hz, 1 H), 3.56-3.51 (m, 2 H), 2.44 (d, J = 1.0 Hz, 3 H), 2.31-2.27 (m, 1 H), 2.23 (s, 6 H), 1.95-1.85 (m, 1 H). | F AC50 BC97 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-538 | Isomer 2 Separated by Chiral SFC | (S)-7-((6-(dimethylamino)methyl)-5-(tetrahydrofuran-3-yl)pyridin-2-yl)amino)-4-(7-methyl-imidazo[1,2-b]pyridazin-3-yl)isoindolin-1-one | Method AcHSS C18, m/z = 484 [M + H]+, Ret. time = 2.36 min | ¹H NMR (400 MHz, DMSO): δ 10.09 (s, 1 H), 8.90 (s, 1 H), 8.74 (d, J = 8.9 Hz, 1 H), 8.53 (d, J = 2.7 Hz, 1 H), 8.18 (d, J = 8.0 Hz, 1 H), 8.02 (s, 2 H), 7.67 (d, J = 8.4 Hz, 1 H), 6.95 (d, J = 8.2 Hz, 1 H), 4.56 (s, 2 H), 4.01-3.94 (m, 2 H), 3.87-3.78 (m, 2 H), 3.66 (d, J = 12.2 Hz, 1 H), 3.56-3.51 (m, 2 H), 2.44 (d, J = 1.0 Hz, 3 H), 2.31-2.27 (m, 1 H), 2.23 (s, 6 H), 1.95-1.85 (m, 1 H). | F AC50 BC97 |
| I-539 | 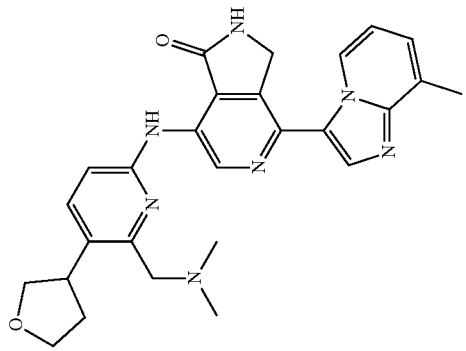 | 7-[[6-[(dimethylamino)methyl]-5-tetrahydrofuran-3-yl-2-pyridyl]amino]-4-(8-methyl-imidazo[1,2-a]pyridin-3-yl)-2,3-dihydropyrrolo[3,4-c]pyridin-1-one | Method AcHSS C18, m/z = 484 [M + H]+, Ret. time = 2.16 min. | ¹H NMR (400 MHz, DMSO): δ 9.98 (s, 1 H), 9.69 (s, 1 H), 9.64 (s, 1 H), 9.33 (s, 1 H), 8.08 (s, 1 H), 7.73 (d, J = 8.7 Hz, 1 H), 7.26 (d, J = 5.6 Hz, 1 H), 7.08 (d, J = 7.7 Hz, 1 H), 7.04 (t, J = 7.1 Hz, 1 H), 4.78 (s, 2 H), 4.04-3.98 (m, 2 H), 3.87-3.82 (m, 2 H), 3.79 (s, 2 H), 3.58-3.53 (m, 1 H), 2.59 (s, 3 H), 2.42 (s, 6 H), 2.35-2.28 (m, 1 H), 1.96-1.86 (m, 1 H). | Hc AC50 BC113 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-540 | Isomer 1 Separated by Chiral SFC | (S)-7-((6-(((dimethylamino)methyl)-5-(tetrahydrofuran-3-yl)pyridin-2-yl)amino)-4-(1-methyl-1H-indol-4-yl)-2,3-dihydro-1H-pyrrolo[3,4-c]pyridin-1-one | Method AcHSS C18, m/z = 483 [M + H]+, Ret. time = 2.89 min. | ¹H NMR (400 MHz, DMSO): δ 10.06 (s, 1 H), 9.60 (s, 1 H), 9.11 (s, 1 H), 7.69 (d, J = 8.5 Hz, 1 H), 7.52 (d, J = 9.1 Hz, 1 H), 7.39 (d, J = 2.7 Hz, 1 H), 7.35 (d, J = 8.5 Hz, 1 H), 7.26 (t, J = 7.4 Hz, 1 H), 7.02 (d, J = 8.5 Hz, 1 H), 6.71 (dd, J = 0.8, 3.1 Hz, 1 H), 4.57 (s, 2 H), 4.03-3.95 (m, 2 H), 3.86 (s, 3 H), 3.85-3.80 (m, 2 H), 3.67 (d, J = 13.1 Hz, 1 H), 3.59-3.53 (m, 2 H), 2.34-2.26 (m, 1 H), 2.24 (s, 6 H), 1.96-1.87 (m, 1 H). | O AC50 BC108 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-541 | 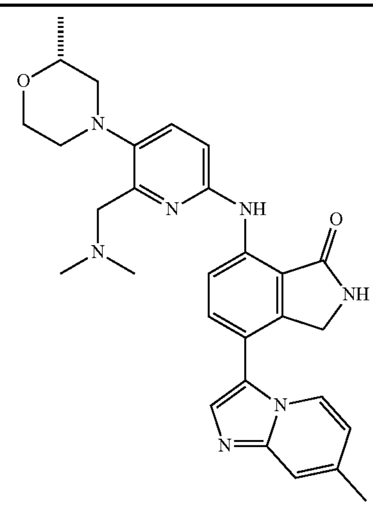 | 7-[[6-[(dimethylamino)methyl]-5-[(2R)-2-methylmorpholin-4-yl]-2-pyridyl]amino]-4-(7-fluoroimidazo[1,2-a]pyridin-3-1-one | Method AcHSS C18, m/z = 516 [M + H]+, Ret. time = 2.19 min. | ¹H NMR (400 MHz, DMSO): δ 10.03 (s, 1 H), 8.82 (s, 1 H), 8.72 (d, J = 11.5 Hz, 1 H), 8.43 (dd, J = 5.9, 7.4 Hz, 1 H), 7.83 (s, 1 H), 7.72 (d, J = 9.5 Hz, 1 H), 7.59 (d, J = 8.3 Hz, 1 H), 7.53 (dd, J = 2.5, 9.9 Hz, 1 H), 7.02-6.95 (m, 2 H), 4.39 (s, 2 H), 3.88 (d, J = 14.0 Hz, 1 H), 3.78-3.69 (m, 2 H), 3.43 (s, 2 H), 3.17-3.12 (m, 1 H), 3.08-3.04 (m, 1 H), 2.77 (ddd, J = 11.5, 11.5, 4.1 Hz, 2 H), 2.37 (s, 6 H), 1.13 (d, J = 6.0 Hz, 3 H). | ACp AC87 BC80 |
| I-542 | Isomer 1 Separated by Chiral SFC | (R)-7-((6-((dimethylamino)methyl)-5-(tetrahydrofuran-3-yl)pyridin-2-yl)amino)-4-(6-fluoropyrazolo[1,5-a]pyridin-3-yl)isoindolin-1-one | Method AcHSS C18, m/z = 487 [M + H]+, Ret. time = 3.14 min. | ¹H NMR (400 MHz, DMSO): δ 10.00 (s, 1 H), 9.09-9.06 (m, 1 H), 8.83 (s, 1 H), 8.72 (d, J = 8.3 Hz, 1 H), 8.38 (s, 1 H), 7.93 (dd, J = 5.5, 9.9 Hz, 1 H), 7.71 (d, J = 8.8 Hz, 1 H), 7.65 (d, J = 8.7 Hz, 1 H), 7.42 (ddd, J = 2.2, 8.0, 10.0 Hz, 1 H), 6.92 (d, J = 8.8 Hz, 1 H), 4.51 (s, 2 H), 4.02-3.94 (m, 2 H), 3.85-3.78 (m, 2 H), 3.65 (d, J = 12.6 Hz, 1 H), 3.55-3.50 (m, 2 H), 2.32-2.26 (m, 1 H), 2.23 (s, 6 H), 1.95-1.85 (m, 1 H). | F AC50 BC122 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-543 | Isomer 2 Separated by Chiral SFC | (S)-7-((6-((dimethyl-amino)methyl)-5-(tetrahydrofuran-3-yl)pyridin-2-yl)amino)-4-(6-fluoro-pyrazolo[1,5-a]pyridin-3-yl)isoindolin-1-one | Method AcHSS C18, m/z = 487 [M + H]+, Ret. time = 3.14 min. | ¹H NMR (400 MHz, DMSO): δ 10.00 (s, 1 H), 9.09-9.06 (m, 1 H), 8.83 (s, 1 H), 8.72 (d, J = 8.3 Hz, 1 H), 8.38 (s, 1 H), 7.93 (dd, J = 5.5, 9.9 Hz, 1 H), 7.71 (d, J = 8.8 Hz, 1 H), 7.65 (d, J = 8.7 Hz, 1 H), 7.42 (ddd, J = 2.2, 8.0, 10.0 Hz, 1 H), 6.92 (d, J = 8.8 Hz, 1 H), 4.51 (s, 2 H), 4.02-3.94 (m, 2 H), 3.85-3.78 (m, 2 H), 3.65 (d, J = 12.6 Hz, 1 H), 3.55-3.50 (m, 2 H), 2.32-2.26 (m, 1 H), 2.23 (s, 6 H), 1.95-1.85 (m, 1 H). | F AC50 BC122 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-544 | 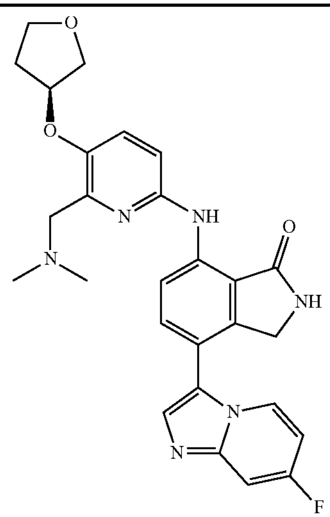 | 7-[[6-[(dimethyl-amino)methyl]-5-[(3S)-tetrahydrofuran-3-yl]oxy-2-pyridyl]amino]-4-(7-fluoro-imidazo[1,2-a]pyridin-3-yl)isoindolin-1-one | Method AcHSS C18, m/z = 503 [M + H]+, Ret. time = 2.06 min. | ¹H NMR (400 MHz, DMSO): δ 9.95 (s, 1 H), 8.81 (s, 1 H), 8.66 (d, J = 8.3 Hz, 1 H), 8.44 (dd, J = 6.2, 7.7 Hz, 1 H), 7.83 (s, 1 H), 7.70 (d, J = 8.5 Hz, 1 H), 7.53 (dd, J = 2.6, 10.2 Hz, 1 H), 7.49 (d, J = 9.0 Hz, 1 H), 7.00-6.95 (m, 2 H), 5.07-5.02 (m, 1 H) 4.39 (s, 2 H), 3.92-3.86 (m, 2 H), 3.85-3.79 (m, 2 H), 3.59-3.50 (m, 2 H), 2.27 (s, 6 H), 2.22-2.13 (m, 1 H), 2.05-1.98 (m, 1 H). | ACp AC88 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-545 | Isomer 1 Separated by Chiral SFC | (S)-7-((6-((dimethylamino)methyl)-5-(tetrahydrofuran-3-yl)pyridin-2-yl)amino)-4-(1-methyl-1H-pyrrolo[2,3-b]pyridin-4-yl)isoindolin-1-one | Method AcHSS C18, m/z = 483 [M + H]+, Ret. time = 2.85 min. | ¹H NMR (400 MHz, DMSO): δ 10.11 (s, 1 H), 8.81 (s, 1 H), 8.73 (d), J = 8.8 Hz, 1 H), 8.33 (d, J = 4.5 Hz, 1 H), 7.75 (d, J = 8.6 Hz, 1 H), 7.68 (d, J = 8.2 Hz, 1 H), 7.59 (d, J = 3.7 Hz, 1 H), 7.27 (d, J = 5.2 Hz, 1 H), 6.97 (d, J = 8.6 Hz, 1 H), 6.48 (d, J = 3.3 Hz, 1 H), 4.47 (s, 2 H), 4.03-3.95 (m, 2 H), 3.88 (s, 3 H), 3.86-3.78 (m, 2 H), 3.65 (d, J = 39.8 Hz, 1 H), 3.54 (t, J = 8.3 Hz, 1 H), 3.43 (d, J = 22.1 Hz, 1 H), 2.35-2.30 (m, 1 H), 2.23 (s, 6 H), 1.96-1.85 (m, 1 H). | D AC50 BC26 |
| I-546 | Isomer 2 Separated by Chiral SFC | (R)-7-((6-((dimethylamino)methyl)-5-(tetrahydrofuran-3-yl)pyridin-2-yl)amino)-4-(1-methyl-1H-pyrrolo[2,3-b]pyridin-4-yl)isoindolin-1-one | Method AcHSS C18, m/z = 483 [M + H]+, Ret. time = 2.89 min. | ¹H NMR (400 MHz, DMSO): δ 10.11 (s, 1 H), 8.81 (s, 1 H), 8.73 (d), J = 8.8 Hz, 1 H), 8.33 (d, J = 4.5 Hz, 1 H), 7.75 (d, J = 8.6 Hz, 1 H), 7.68 (d, J = 8.2 Hz, 1 H), 7.59 (d, J = 3.7 Hz, 1 H), 7.27 (d, J = 5.2 Hz, 1 H), 6.97 (d, J = 8.6 Hz, 1 H), 6.48 (d, J = 3.3 Hz, 1 H), 4.47 (s, 2 H), 4.03-3.95 (m, 2 H), 3.88 (s, 3 H), 3.86-3.78 (m, 2 H), 3.65 (d, J = 39.8 Hz, 1 H), 3.54 (t, J = 8.3 Hz, 1 H), 3.43 (d, J = 22.1 Hz, 1 H), 2.35-2.30 (m, 1 H), 2.23 (s, 6 H), 1.96-1.85 (m, 1 H). | D AC50 BC26 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-547 | 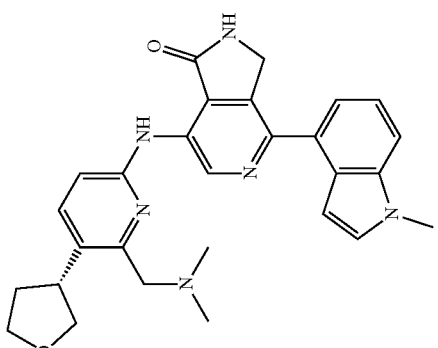 Isomer 2 Separated by Chiral SFC | (R)-7-((6-((dimethylamino)methyl)-5-(tetrahydrofuran-3-yl)pyridin-2-yl)amino)-4-(1-methyl-1H-indol-4-yl)-2,3-dihydro-1H-pyrrolo[3,4-c]pyridin-1-one | Method AcHSS C18, m/z = 483 [M + H]+, Ret. time = 2.88 min. | ¹H NMR (400 MHz, DMSO): δ 10.06 (s, 1 H), 9.60 (s, 1 H), 9.11 (s, 1 H), 7.69 (d, J = 8.5 Hz, 1 H), 8.33 (d, J = 9.1 Hz, 1 H), 7.39 (d, J = 2.7 Hz, 1 H), 7.35 (d, J = 8.5 Hz, 1 H), 7.26 (d, J = 7.4 Hz, 1 H), 7.02 (d, J = 8.5 Hz, 1 H), 6.71 (dd, J = 0.8, 3.1 Hz, 1 H), 4.57 (s, 2 H), 4.03-3.95 (m, 2 H), 3.86 (s, 3 H), 3.85-3.80 (m, 2 H), 3.67 (d, J = 13.1 Hz, 1 H), 3.59-3.53 (m, 2 H), 2.34-2.26 (m, 1 H), 2.24 (s, 6 H), 1.96-1.87 (m, 1 H). | O AC50 BC108 |
| I-548 | 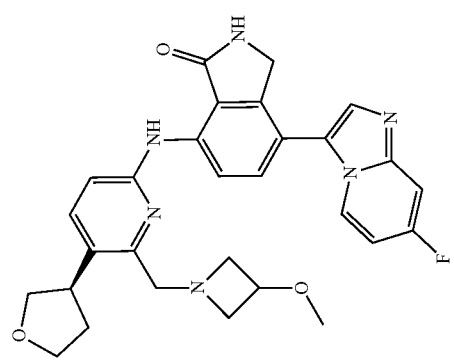 Isomer 1 Separated by Chiral SFC | (R)-4-(7-fluoroimidazo[1,2-a]pyridin-3-yl)-7-((6-((3-methoxyazetidin-1-yl)methyl)-5-(tetrahydrofuran-3-yl)pyridin-2-yl)amino)isoindolin-1-one | Method AcHSS C18, m/z = 529 [M + H]+, Ret. time = 2.15 min. | ¹H NMR (400 MHz, DMSO): δ 10.11 (s, 1 H), 8.90 (s, 1 H), 8.87 (s, 1 H), 8.51 (t, J = 6.7 Hz, 1 H), 7.88 (s, 1 H), 7.82 (d, J = 8.0 Hz, 1 H), 7.69 (d, J = 8.9 Hz, 1 H), 7.59 (dd, J = 2.4, 10.1 Hz, 1 H), 7.03 (dt, J = 2.8, 7.6 Hz, 1 H), 6.97 (d, J = 8.5 Hz, 1 H), 4.45 (s, 2 H), 4.07-3.99 (m, 2 H), 3.90-3.83 (m, 2 H), 3.81-3.72 (m, 2 H), 3.62-3.53 (m, 2 H), 3.35 (s, 2 H), 3.20 (s, 3 H), 3.04 (t, J = 6.6 Hz, 2 H), 2.38-2.32 (m, 1 H), 2.00-1.91 (m, 1 H). | F AC89 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-549 | Isomer 2 Separated by Chiral SFC | (S)-4-(7-fluoroimidazo[1,2-a]pyridin-3-yl)-7-((6-((3-methoxyazetidin-1-yl)methyl)-5-(tetrahydrofuran-3-yl)pyridin-2-yl)amino)isoindolin-1-one | Method AcHSS C18, m/z = 529 [M + H]+, Ret. time = 2.17 min. | ¹H NMR (400 MHz, DMSO): δ 10.11 (s, 1 H), 8.90 (s, 1 H), 8.87 (s, 1 H), 8.51 (t, J = 6.7 Hz, 1 H), 7.88 (s, 1 H), 7.82 (d, J = 8.0 Hz, 1 H), 7.69 (d, J = 8.9 Hz, 1 H), 7.59 (dd, J = 2.4, 10.1 Hz, 1 H), 7.03 (dt, J = 2.8, 7.6 Hz, 1 H), 6.97 (d, J = 8.5 Hz, 1 H), 4.45 (s, 2 H), 4.07-3.99 (m, 2 H), 3.90-3.83 (m, 2 H), 3.81-3.72 (m, 2 H), 3.62-3.53 (m, 2 H), 3.35 (s, 2 H), 3.20 (s, 3 H), 3.04 (t, J = 6.6 Hz, 2 H), 2.38-2.32 (m, 1 H), 2.00-1.91 (m, 1 H). | F AC89 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-550 | Isomer 1 Separated by Chiral SFC | (R)-7-((6-((dimethylamino)methyl)-5-(tetrahydro-2H-pyran-3-yl)pyridin-2-yl)amino)-4-(7-fluoroimidazo[1,2-a]pyridin-3-yl)isoindolin-1-one | Method AcHSS C18, m/z = 501 [M + H]+, Ret. time = 2.26 min. | ¹H NMR (400 MHz, DMSO): δ 10.05 (s, 1 H), 8.84 (s, 1 H), 8.78 (d, J = 8.8 Hz, 1 H), 8.46 (t, J = 6.4 Hz, 1 H), 7.83 (s, 1 H), 7.74 (d, J = 10.4 Hz, 1 H), 7.68 (d, J = 8.6 Hz, 1 H), 7.53 (dd, J = 2.4, 10.3 Hz, 1 H), 6.98 (ddd, J = 7.5, 7.5, 2.8 Hz, 1 H), 6.93 (d, J = 8.3 Hz, 1 H), 4.40 (s, 2 H), 3.90 (d, J = 11.7 Hz, 1 H), 3.82 (d, J = 10.8 Hz, 1 H), 3.62 (d, J = 12.2 Hz, 1 H), 3.53 (d, J = 12.0 Hz, 1 H), 3.26-3.19 (m, 2 H), 2.23 (s, 6 H), 1.77-1.66 (m, 4 H). | D AC90 BC91 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-551 | Isomer 2 Separated by Chiral SFC | (S)-7-((6-((dimethylamino)methyl)-5-(tetrahydro-2H-pyran-3-yl)pyridin-2-yl)amino)-4-(7-fluoroimidazo[1,2-a]pyridin-3-yl)isoindolin-1-one | Method AcHSS C18, m/z = 501 [M + H]+, Ret. time = 2.26 min. | ¹H NMR (400 MHz, DMSO): δ 10.05 (s, 1 H), 8.84 (s, 1 H), 8.78 (d, J = 8.8 Hz, 1 H), 8.46 (t, J = 6.4 Hz, 1 H), 7.83 (s, 1 H), 7.74 (d, J = 10.4 Hz, 1 H), 7.68 (d, J = 8.6 Hz, 1 H), 7.53 (dd, J = 2.4, 10.3 Hz, 1 H), 6.98 (ddd, J = 7.5, 7.5, 2.8 Hz, 1 H), 6.93 (d, J = 8.3 Hz, 1 H), 4.40 (s, 2 H), 3.90 (d, J = 11.7 Hz, 1 H), 3.82 (d, J = 10.8 Hz, 1 H), 3.62 (d, J = 12.2 Hz, 1 H), 3.53 (d, J = 12.0 Hz, 1 H), 3.45-3.39 (m, 1 H), 3.26-3.19 (m, 2 H), 2.23 (s, 6 H), 1.77-1.66 (m, 4 H). | D AC90 BC91 |

| # | STRUCTURE | NAME | LCMS | $^1$H NMR | Method Reagent AA BB |
|---|---|---|---|---|---|
| I-552 | Isomer 1 Separated by Chiral SFC | 4-(1-methyl-pyrrolo[2,3-b]pyridin-4-yl)-7-[[6-(pyrrolidin-1-ylmethyl)-5-tetrahydrofuran-3-yl-2-pyridyl]amino]-2,3-dihydro-pyrrolo[3,4-c]pyridin-1-one | Method AcHSS C18, m/z = 510 [M + H]+, Ret. time = 2.7 min. | $^1$H NMR (400 MHz, DMSO): δ 10.17 (s, 1 H), 9.71 (s, 1 H), 9.22 (s, 1 H), 8.37 (d, J = 4.9 Hz, 1 H), 7.69 (d, J = 7.7 Hz, 1 H), 7.59 (d, J = 3.7 Hz, 1 H), 7.40 (d, J = 4.9 Hz, 1 H), 7.03 (d, J = 8.5 Hz, 1 H), 6.90 (d, J = 3.6 Hz, 1 H), 4.73 (s, 2 H), 4.03-3.95 (m, 2 H), 3.90 (d, J = 2.4 Hz, 1 H), 3.89 (s, 3 H), 3.85-3.75 (m, 3 H), 3.56 (dd, J = 6.8, 8.0 Hz, 1 H), 2.57-2.54 (m, 4 H), 2.32-2.27 (m, 1 H), 1.95-1.88 (m, 1 H), 1.74 (s, 4 H). | O AC67 BC26 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-553 | 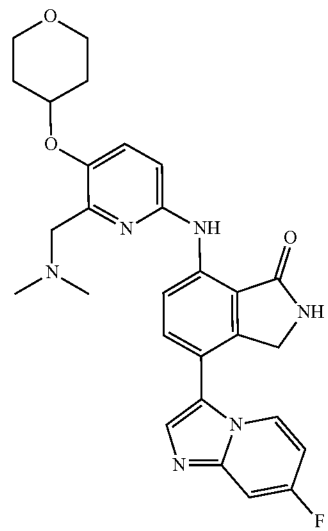 [SMILES: CN(C)Cc1nc(Nc2ccc(-c3cnc4cc(F)ccn34)c3c2C(=O)NC3)ccc1OC1CCOCC1] | 7-[[6-[(dimethyl-amino)methyl]-5-tetrahydropyran-4-yloxy-2-pyridyl]amino]-4-(7-fluoro-imidazo[1,2-a]pyridin-3-yl)isoindolin-1-one | Method AcHSS C18, m/z = 517 [M + H]+, Ret. time = 2.13 min. | ¹H NMR (400 MHz, DMSO): δ 9.95 (s, 1 H), 8.80 (s, 1 H), 8.67 (d, J = 8.7 Hz, 1 H), 8.44 (dd, J = 6.2, 7.7 Hz, 1 H), 7.82 (s, 1 H), 7.70 (d, J = 8.5 Hz, 1 H), 7.55-7.52 (m, 2 H), 6.98 (ddd, J = 7.5, 7.5, 3.0 Hz, 1 H), 6.95 (d, J = 9.0 Hz, 1 H), 4.58-4.51 (m, 1 H), 4.39 (s, 2 H), 3.91-3.84 (m, 2 H), 3.57 (s, 2 H), 3.50 (ddd, J = 3.1, 8.6, 11.5 Hz, 2 H), 2.29 (s, 6 H), 1.98-1.93 (m, 2 H), 1.69-1.59 (m, 2 H). | ACp AC91 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-554 | Isomer 2 Seperated by Chiral SFC | (R)-7-((6-((dimethylamino)methyl)-5-(tetrahydrofuran-2-yl)pyridin-2-yl)amino)-4-(7-fluoroimidazo[1,2-a]pyridin-3-yl)isoindolin-1-one | Method AcHSS C18, m/z = 487 [M + H]+, Ret. time = 2.22 min. | ¹H NMR (400 MHz, DMSO): δ 10.10 (s, 1 H), 8.85 (s, 1 H), 8.80 (d, J = 8.3 Hz, 1 H), 7.84 (s, 1 H), 7.74 (dd, J = 7.2, 8.6 Hz, 2 H), 7.54 (dd, J = 2.7, 10.0 Hz, 1 H), 6.98 (ddd, J = 7.4, 7.4, 2.7 Hz, 1 H), 6.95 (d, J = 8.6 Hz, 1 H), 5.19 (t, J = 7.4 Hz, 1 H), 4.05 (dd, J = 7.4, 14.5 Hz, 1 H), 3.81 (dd, J = 6.9, 14.3 Hz, 1 H), 3.64 (d, J = 12.9 Hz, 1 H), 3.47 (d, J = 12.2 Hz, 1 H), 2.21 (s, 6 H), 2.02-1.92 (m, 2 H), 1.63 (m, J = 4.1, 4.7, 4.4 Hz, 2 H). | C AC92 BC91 |
| I-555 | 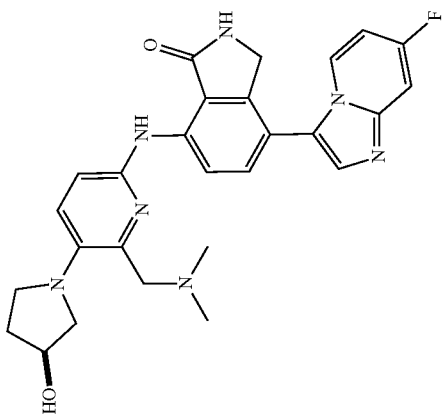 | 7-[[6-[(dimethylamino)methyl]-5-[(3S)-3-hydroxypyrrolidin-1-yl]-2-pyridyl]amino]-4-(7-fluoroimidazo[1,2-a]pyridin-3-yl)isoindolin-1-one | Method AcHSS C18, m/z = 502 [M + H]+, Ret. time = 2.01 min. | ¹H NMR (400 MHz, DMSO): δ 10.02 (s, 1 H), 8.93 (s, 1 H), 8.59 (d, J = 7.3 Hz, 1 H), 7.98 (t, J = 6.8 Hz, 1 H), 7.84 (d, J = 7.3 Hz, 1 H), 7.69 (dd, J = 2.6, 10.2 Hz, 1 H), 7.51 (d, J = 8.3 Hz, 1 H), 7.14 (ddd, J = 7.6, 7.6, 2.8 Hz, 1 H), 7.06 (d, J = 8.4 Hz, 1 H), 5.07 (s, 1 H), 4.54 (s, 3 H), 3.75 (s, 2 H), 3.63 (dd, J = 4.9, 9.7 Hz, 1 H), 3.55-3.52 (m, 1 H), 3.39-3.33 (m, 1 H), 3.28 (dd, J = 3.2, 9.6 Hz, 1 H), 2.46 (s, 6 H), 2.23 (dt, J = 7.3, 13.3 Hz, 1 H), 2.00-1.94 (m, 1 H). | ACp AC93 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-556 | Isomer 1 Separated by Chiral SFC | (S)-7-((6-((dimethyl-amino)methyl)-5-(1-methyl-2-oxopiperidin-4-yl)pyridin-2-yl)amino)-4-(7-fluoro-imidazo[1,2-a]pyridin-3-yl)isoindolin-1-one | Method AcHSS C18, m/z = 528 [M + H]+, Ret. time = 2.0 min. | ¹H NMR (400 MHz, DMSO): δ 10.06 (s, 1 H), 8.84 (s, 1 H), 8.78 (d, J = 9.1 Hz, 1 H), 8.46 (dd, J = 5.8, 7.7 Hz, 1 H), 7.84 (s, 1 H), 7.74 (d, J = 8.5 Hz, 1 H), 7.71 (d, J = 8.2 Hz, 1 H), 7.54 (dd, J = 2.5, 9.9 Hz, 1 H), 6.99 (ddd, J = 7.4, 7.4, 2.4 Hz, 1 H), 6.96 (d, J = 8.4 Hz, 1 H), 4.40 (s, 2 H), 3.60 (dd, J = 12.9, 20.5 Hz, 1 H), 3.51-3.42 (m, 1 H), 3.32 (s, 2 H), 2.89 (s, 3 H), 2.45-2.34 (m, 3 H), 2.23 (s, 6 H), 2.02-1.92 (m, 2 H). | D AC94 BC91 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-557 | Isomer 2 Separated by Chiral SFC | (R)-7-((6-((dimethylamino)methyl)-5-(1-methyl-2-oxopiperidin-4-yl)pyridin-2-yl)amino)-4-(7-fluoroimidazo[1,2-a]pyridin-3-yl)isoindolin-1-one | Method AcHSS C18, m/z = 528 [M + H]+, Ret. time = 1.99 min. | ¹H NMR (400 MHz, DMSO): δ 10.06 (s, 1 H), 8.84 (s, 1 H), 8.78 (d, J = 9.1 Hz, 1 H), 8.46 (dd, J = 5.8, 7.7 Hz, 1 H), 7.84 (s, 1 H), 7.74 (d, J = 8.5 Hz, 1 H), 7.71 (d, J = 8.2 Hz, 1 H), 7.54 (dd, J = 2.5, 9.9 Hz, 1 H), 6.99 (ddd, J = 7.4, 7.4, 2.4 Hz, 1 H), 6.96 (d, J = 8.4 Hz, 1 H), 4.40 (s, 2 H), 3.60 (dd, J = 12.9, 20.5 Hz, 1 H), 3.51-3.42 (m, 1 H), 3.32 (s, 2 H), 2.89 (s, 3 H), 2.45-2.34 (m, 3 H), 2.23 (s, 6 H), 2.02-1.92 (m, 2 H). | D AC94 BC91 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-558 | Isomer 1 Separated by Chiral SFC | (S)-4-(7-fluoro-imidazo[1,2-a]pyridin-3-yl)-7-((6-((isopropyl-amino)methyl)-5-(tetrahydrofuran-3-yl)pyridin-2-yl)amino)iso-indolin-1-one | Method AcHSS C18, m/z = 501 [M + H]+, Ret. time = 2.16 min. | ¹H NMR (400 MHz, DMSO): δ 10.04 (s, 1 H), 8.86 (s, 1 H), 8.64 (d, J = 8.8 Hz, 1 H), 8.42 (dd, J = 6.4, 7.6 Hz, 1 H), 7.84 (s, 1 H), 7.72 (d, J = 9.1 Hz, 1 H), 7.66 (d, J = 8.1 Hz, 1 H), 7.54 (dd, J = 2.3, 10.1 Hz, 1 H), 7.00 (ddd, J = 7.5, 7.5, 2.6 Hz, 1 H), 6.97 (d, J = 8.8 Hz, 1 H), 4.41 (s, 2 H), 4.04-3.94 (m, 4 H), 3.83 (q, J = 7.6 Hz, 1 H), 3.71-3.62 (m, 1 H), 3.60-3.56 (m, 1 H), 2.94 (t, J = 7.5 Hz, 1 H), 2.37-2.28 (m, 1 H), 1.95-1.87 (m, 1 H), 1.13 (d, J = 5.7 Hz, 6 H). | F AC95 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-559 | 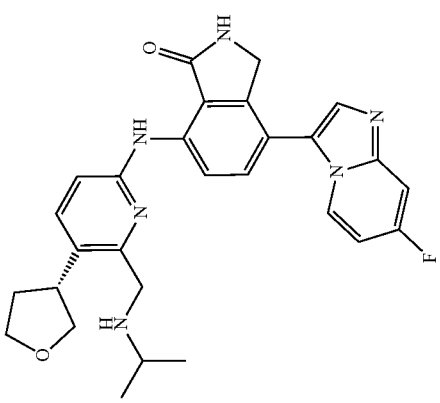<br>Isomer 2<br>Seperated by Chiral SFC | (R)-4-(7-fluoro-imidazo[1,2-a]pyridin-3-yl)-7-((6-((isopropyl-amino)methyl)-5-(tetrahydrofuran-3-yl)pyridin-2-yl)amino)iso-indolin-1-one | Method AcHSS C18, m/z = 501 [M + H]+, Ret. time = 2.16 min. | ¹H NMR (400 MHz, DMSO): δ 10.04 (s, 1 H), 8.86 (s, 1 H), 8.64 (d, J = 8.8 Hz, 1 H), 8.42 (dd, J = 6.4, 7.6 Hz, 1 H), 7.84 (s, 1 H), 7.72 (d, J = 9.1 Hz, 1 H), 7.66 (d, J = 8.1 Hz, 1 H), 7.54 (dd, J = 2.3, 10.1 Hz, 1 H), 7.00 (ddd, J = 7.5, 7.5, 2.6 Hz, 1 H), 6.97 (d, J = 8.8 Hz, 1 H), 4.41 (s, 2 H), 4.04-3.94 (m, 4 H), 3.83 (q, J = 7.6 Hz, 1 H), 3.71-3.62 (m, 1 H), 3.60-3.56 (m, 1 H), 2.94 (t, J = 7.5 Hz, 1 H), 2.37-2.28 (m, 1 H), 1.95-1.87 (m, 1 H), 1.13 (d, J = 5.7 Hz, 6 H). | F AC95 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-560 | Isomer 1 Separated by Chiral | (S)-7-((6-(dimethyl-amino)methyl)-5-(tetrahydrofuran-2-yl)pyridin-2-yl)amino)-4-(7-fluoro-imidazo[1,2-a]pyridin-3-yl)isoindolin-1-one | Method BicarbB EHC18, m/z = 487 [M + H]+, Ret. time = 3.78 min. | ¹H NMR (400 MHz, DMSO): δ 10.10 (s, 1 H), 8.85 (s, 1 H), 8.80 (d, J = 8.3 Hz, 1 H), 7.84 (s, 1 H), 7.74 (dd, J = 7.2, 8.6 Hz, 2 H), 7.54 (dd, J = 2.7, 10.0 Hz, 1 H), 6.98 (ddd, J = 7.4, 7.4, 2.7 Hz, 1 H), 6.95 (d, J = 8.6 Hz, 1 H), 5.19 (t, J = 7.4 Hz, 1 H), 4.05 (dd, J = 7.4, 14.5 Hz, 1 H), 3.81 (dd, J = 6.9, 14.3 Hz, 1 H), 3.64 (d, J = 12.9 Hz, 1 H), 3.47 (d, J = 12.2 Hz, 1 H), 2.21 (s, 6 H), 2.02-1.92 (m, 2 H), 1.63 (m, J = 4.1, 4.7 4.4 Hz, 2 H). | D AC90 BC91 |
| I-561 | 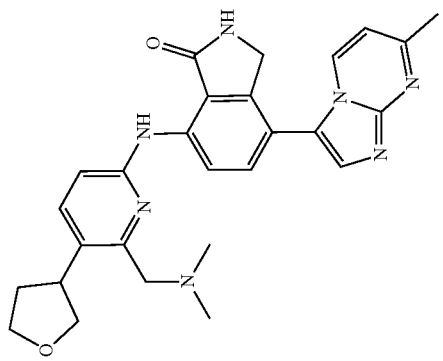 | 7-[[6-[(dimethyl-amino)methyl]-5-tetrahydrofuran-3-yl-2-pyridyl]amino]-4-(7-methyl-imidazo[1,2-a]pyrimidin-3-yl)isoindolin-1-one | Method AcHSS C18, m/z = 484 [M + H]+, Ret. time = 2.04 min. | ¹H NMR (400 MHz, DMSO): δ 10.06 (s, 1 H), 8.86 (s, 1 H), 8.75 (d, J = 7.2 Hz, 2 H), 7.90 (s, 1 H), 7.74 (d, J = 8.8 Hz, 1 H), 7.69 (d, J = 8.8 Hz, 1 H), 7.01-6.96 (m, 2 H), 4.43 (s, 2 H), 4.03-3.95 (m, 2 H), 3.82 (q, J = 8.6 Hz, 2 H), 3.54 (t, J = 7.8 Hz, 1 H), 3.31 (s, 2 H), 2.58 (s, 3 H), 2.33-2.28 (m, 1 H), 2.23 (s, 6 H), 1.96-1.86 (m, 1 H). | D AC50 BC109 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-562 | 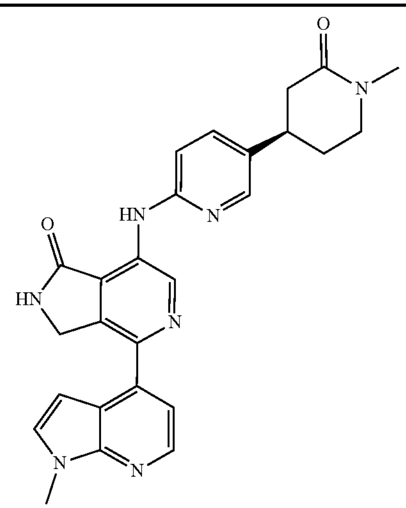 | (R)-4-(1-methyl-1H-pyrrolo[2,3-b]pyridin-4-yl)-7-((5-((1-methyl-2-oxopiperidin-4-yl(pyridin-2-yl)amino)-2,3-dihydro-1H-pyrrolo[3,4-c]pyridin-1-one | LCMS Method J m/z = 469.2 [M + H]+, Ret. time = 3.46 min Chiral HPLC method X7: Ret. time = 6.7 | 1H NMR (400 MHz, DMSO-d6) δ 10.06 (s, 1H), 9.73 (s, 1H), 9.24 (s, 1H), 8.37-8.36 (d, J = 5.0 Hz, 1H), 8.30 (d, J = 2.5 Hz, 1H), 7.71 (dd, J = 8.5, 2.6 Hz, 1H), 7.59 (d, J = 3.5 Hz, 1H), 7.41 (d, J = 5.1 Hz, 1H), 7.12 (d, J = 8.5 Hz, 1H), 6.92 (d, J = 3.4 Hz, 1H), 4.74 (s, 2H), 3.88 (s, 3H), 3.19-3.07 (m, 2H), 2.88 (s, 3H), 2.45 (dd, J = 15.4, 4.4 Hz, 3H), 2.10-1.95 (m, 2H). | Zp AA8 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-563 | 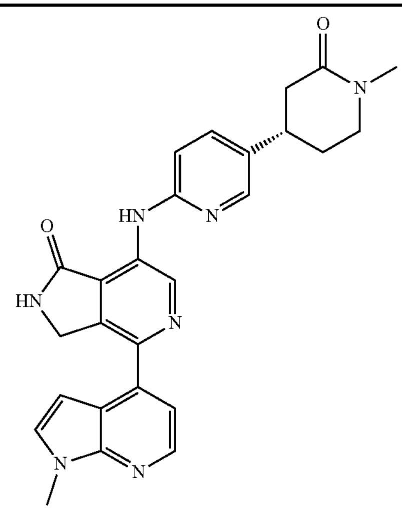 | (S)-4-(1-methyl-1H-pyrrolo[2,3-b]pyridin-4-yl)-7-((5-(1-methyl-2-oxopiperidin-4-yl)pyridin-2-yl)amino)-2,3-dihydro-1H-pyrrolo[3,4-c]pyridin-1-one | LCMS Method J m/z = 469.3 [M + H]+, Ret. time = 3.46 min Chiral HPLC method X7: Ret. time = 7.05 | 1H NMR (400 MHz, DMSO-d6) δ 10.06 (s, 1H), 9.73 (s, 1H), 9.24 (s, 1H), 8.37 (d, J = 5.0 Hz, 1H), 8.30 (d, J = 2.5 Hz, 1H), 7.71 (dd, J = 8.5, 2.5 Hz, 1H), 7.59 (d, J = 3.5 Hz, 1H), 7.41 (d, J = 5.0 Hz, 1H), 7.11 (d, J = 8.5 Hz, 1H), 6.92 (d, J = 3.4 Hz, 1H), 4.74 (s, 2H), 3.88 (s, 3H), 3.49-3.39 (m, 2H), 3.12 (tt, J = 10.5, 5.6 Hz, 1H), 2.88 (s, 3H), 2.49-2.39 (m, 3H), 2.02-1.98 (dd, J = 8.7, 4.6 Hz, 1H). | Zp AA8 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-564 | 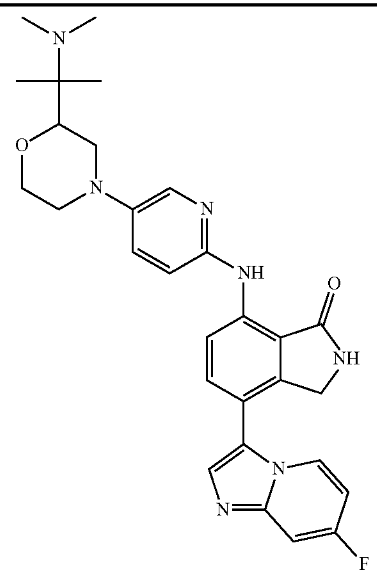 | 7-((5-(2-(dimethyl-amino)propan-2-yl)morpho-lino)pyridin-2-yl)amino)-4-(7-fluoro-imidazo[1,2-a]pyridin-3-yl)isoindolin-1-one | LCMS Method J m/z = 530.9 [M + H]+, Ret. time = 2.46 min | 1H NMR (400 MHz, DMSO-d6) δ 9.91 (s, 1H), 8.83 (s, 1H), 8.62 (d, J = 8.5 Hz, 1H), 8.46 (t, J = 6.7 Hz, 1H), 8.05 (d, J = 3.1 Hz, 1H), 7.86 (s, 1H), 7.73 (d, J = 8.6 Hz, 1H), 7.57 (d, J = 10.1 Hz, 1H), 7.48 (dd, J = 8.8, 3.0 Hz, 1H), 7.03 (d, J = 8.5 Hz, 2H), 4.42 (s, 2H), 4.06 (d, J = 11.5 Hz, 1H), 3.61 (dd, J = 17.5, 11.5 Hz, 3H), 2.24 (s, 6H), 1.28 (s, 3H), 1.05 (d, J = 18.2 Hz, 6H). | Xp AA93 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-565 | 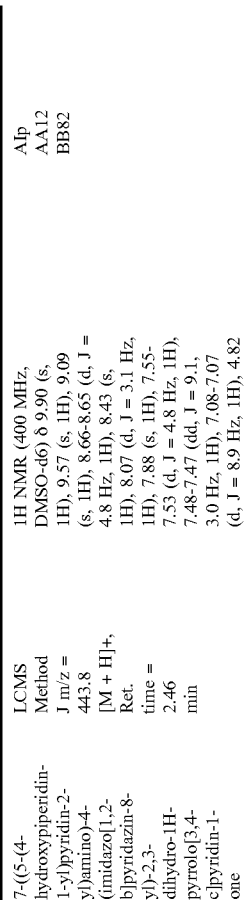 | 7-(5-(4-hydroxypiperidin-1-yl)pyridin-2-ylamino)-4-(imidazo[1,2-b]pyridazin-8-yl)-2,3-dihydro-1H-pyrrolo[3,4-c]pyridin-1-one | LCMS Method J m/z = 443.8 [M + H]+, Ret. time = 2.46 min | 1H NMR (400 MHz, DMSO-d6) δ 9.90 (s, 1H), 9.57 (s, 1H), 9.09 (s, 1H), 8.66-8.65 (d, J = 4.8 Hz, 1H), 8.43 (s, 1H), 8.07 (d, J = 3.1 Hz, 1H), 7.88 (s, 1H), 7.55-7.53 (d, J = 4.8 Hz, 1H), 7.48-7.47 (dd, J = 9.1, 3.0 Hz, 1H), 7.08-7.07 (d, J = 8.9 Hz, 1H), 4.82 (s, 2H), 4.72-4.71 (d, J = 4.2 Hz, 1H), 3.65-3.64 (dq, J = 9.1, 4.6 Hz, 1H), 3.55-3.47 (m, 3H), 2.88-2.83 (t, J = 12.6 Hz, 2H), 1.86 (dd, J = 12.8, 4.6 Hz, 2H), 1.25 (s, 1H). | Alp AA12 BB82 |
| I-566 | 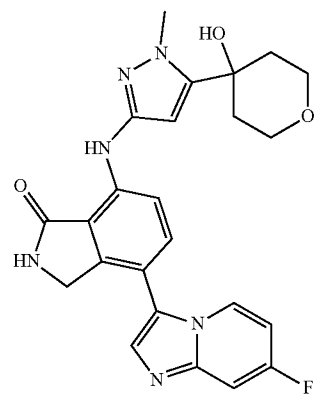 [SMILES: Cn1nc(Nc2ccc(-c3cnc4cc(F)ccn34)c3c2C(=O)NC3)cc1C1(O)CCOCC1] | 4-(7-fluoroimidazo[1,2-a]pyridin-3-yl)-7-((5-(4-hydroxytetrahydro-2H-pyran-4-yl)-1-methyl-1H-pyrazol-3-yl)amino)isoindolin-1-one | LCMS Method J m/z = 463.2 [M + H]+, Ret. time = 2.98 min | 1H NMR (400 MHz, DMSO-d6) δ 9.35 (s, 1H), 8.70 (s, 1H), 8.43-8.39 (t, J = 7.6, 1H), 8.02-8.00 (d, J = 8.5 Hz, 1H), 7.80 (s, 1H), 7.68-7.66 (d, J = 8.5 Hz, 1H), 7.53-7.51 (dd, J = 10.0, 2.6 Hz, 1H), 6.97-6.95 (td, J = 7.6, 2.7 Hz, 1H), 6.02 (s, 1H), 5.45 (s, 1H), 4.37 (s, 2H), 3.94 (s, 3H), 3.84-3.74 (m, 2H), 3.70 (dt, J = 11.2, 3.4 Hz, 2H), 1.98 (dd, J = 14.4, 10.1 Hz, 2H), 1.86 (d, J = 13.1 Hz, 2H). | Xp AA94 BB63 |

| # | STRUCTURE | NAME | LCMS | ¹H NMR | Method Reagent AA BB |
|---|---|---|---|---|---|
| I-567 | 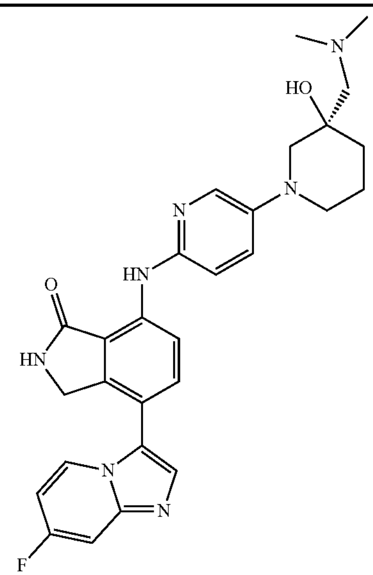 | (R)-7-(5-((3-(dimethylamino)methyl)-3-hydroxypiperidin-1-yl)pyridin-2-yl)amino)-4-(7-fluoroimidazo[1,2-a]pyridin-3-yl)isoindolin-1-one | LCMS Method J m/z = 516.2 [M + H]+, Ret. time = 2.75 min Chiral HPLC method X9: Ret. time = 7.51 | 1H NMR (400 MHz, DMSO-d6) δ 9.85 (s, 1H), 8.78 (s, 1H), 8.57-8.55 (d, J = 8.6 Hz, 1H), 8.44-8.42 (dd, J = 7.6, 5.7 Hz, 1H), 7.98 (d, J = 3.0 Hz, 1H), 7.82 (s, 1H), 7.70-7.68 (d, J = 8.6 Hz, 1H), 7.54 (dd, J = 10.1, 2.6 Hz, 1H), 7.42 (dd, J = 9.0, 3.0 Hz, 1H), 6.98 (td, J = 8.9, 8.2, 3.4 Hz, 2H), 4.39 (s, 3H), 3.10 (d, J = 11.3 Hz, 2H), 2.95 (ddd, J = 11.9, 8.2, 3.5 Hz, 1H), 2.81 (d, J = 11.6 Hz, 1H), 2.33 (s, 6H), 1.84-1.71 (m, 2H), 1.49-1.38 (m, 1H), 1.25 (m, 2H). | Yp AA95 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-568 | 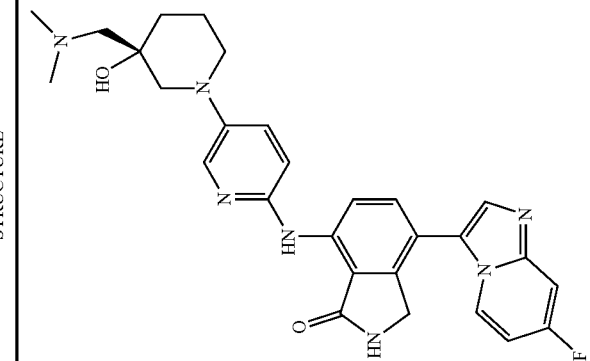 | (S)-7-((5-(3-((dimethylamino)methyl)-3-hydroxypiperidin-1-yl)pyridin-2-yl)amino)-4-(7-fluoroimidazo[1,2-a]pyridin-3-yl)isoindolin-1-one | LCMS Method J m/z = 516.2 [M + H]+, Ret. time = 2.76 min Chiral HPLC method X9: Ret. time = 9.01 | 1H NMR (400 MHz, DMSO-d6) δ 9.84 (s, 1H), 8.78 (s, 1H), 8.56 (d, J = 8.5 Hz, 1H), 8.43 (dd, J = 7.6, 5.7 Hz, 1H), 7.98 (d, J = 3.0 Hz, 1H), 7.82 (s, 1H), 7.70 (d, J = 8.6 Hz, 1H), 7.53 (dd, J = 10.1, 2.7 Hz, 1H), 7.42 (dd, J = 9.0, 3.0 Hz, 1H), 6.98 (td, J = 9.0, 8.2, 2.2 Hz, 2H), 4.39 (s, 3H), 3.15-3.05 (m, 2H), 2.95 (ddd, J = 11.7, 8.2, 3.4 Hz, 1H), 2.80 (d, J = 11.6 Hz, 1H), 2.29 (s, 6H), 1.85-1.69 (m, 2H), 1.43 (td, J = 8.8, 4.8 Hz, 2H), 1.25 (m, 2H). | Yp AA95 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-569 | 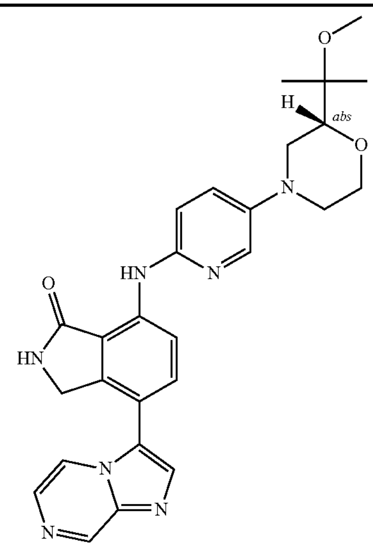 | (R)-4-(imidazo[1,2-a]pyrazin-3-yl)-7-((5-(2-(2-methoxy-propan-2-yl)morpho-linopyridin-2-yl)amino)iso-indolin-1-one | LCMS Method J m/z = 500.9 [M + H]+, Ret. time = 3.46 min Chiral HPLC method X4: Ret. time = 14.02 | 1H NMR (400 MHz, DMSO-d6) δ 9.93 (s, 1H), 9.16 (d, J = 1.4 Hz, 1H), 8.84 (s, 1H), 8.62 (d, J = 8.6 Hz, 1H), 8.47 (dd, J = 4.7, 1.5 Hz, 1H), 8.13 (s, 1H), 8.04 (d, J = 3.0 Hz, 1H), 7.93 (d, J = 4.7 Hz, 1H), 7.78 d, J = 8.6 Hz, 1H), 7.48 (dd, J = 9.0, 3.0 Hz, 1H), 7.00 (d, J = 9.0 Hz, 1H), 4.45 (s, 2H), 4.08-3.96 (m, 1H), 3.67 (td, J = 11.5, 2.6 Hz, 1H), 3.56-3.43 (m, 3H), 3.19 (s, 3H), 2.69 (td, J = 11.8, 3.4 Hz, 2H), 1.18 (d, J = 18.9 Hz, 6H). | G AA97 BB61 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-570 | 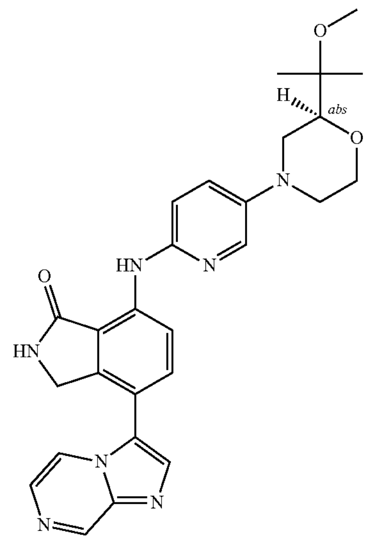 [SMILES: COC(C)(C)[C@@H]1CN(c2ccc(Nc3ccc(-c4cnc5cnccn45)c4c3C(=O)NC4)nc2)CCO1] | (S)-4-(imidazo[1,2-a]pyrazin-3-yl)-7-((5-(2-(2-methoxy-propan-2-yl)morpho-lino)pyridin-2-yl)amino)iso-dinolin-1-one | LCMS Method J m/z = 500.9 [M + H]+, Ret. time = 3.45 min Chiral HPLC method X4: Ret. time = 16.95 | 1H NMR (400 MHz, DMSO-d6) δ 9.93 (s, 1H), 9.16 (d, J = 1.4 Hz, 1H), 8.84 (s, 1H), 8.62 (d, J = 8.6 Hz, 1H), 8.47 (dd, J = 4.7, 1.5 Hz, 1H), 8.13 (s, 1H), 8.05 (d, J = 3.0 Hz, 1H), 7.93 (d, J = 4.7 Hz, 1H), 7.78 (d, J = 8.6 Hz, 1H), 7.49 (dd, J = 9.0, 3.1 Hz, 1H), 7.01 (d, J = 8.9 Hz, 1H), 4.45 (s, 2H), 4.07-3.98 (m, 1H), 3.67 (td, J = 11.4, 2.6 Hz, 1H), 3.55-3.42 (m, 3H), 3.19 (s, 3H), 2.69 (td, J = 11.7, 3.4 Hz, 1H), 2.57 (dd, J = 11.6, 1.9 Hz, 1H), 1.18 (d, J = 18.9 Hz, 6H). | G AA97 BB61 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-571 | 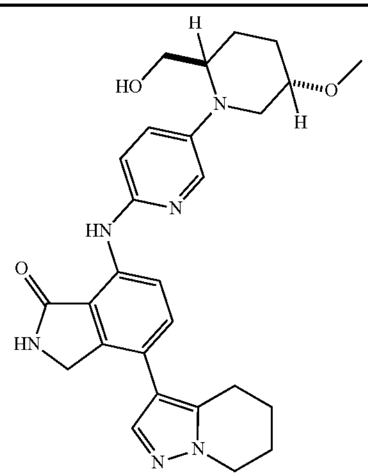 | 7-((5-((2R,5S)-2-(hydroxymethyl)-5-methoxypiperidin-1-yl)pyridin-2-yl)amino)-4-(4,5,6,7-tetrahydropyrazolo[1,5-a]pyridin-3-yl)isoindolin-1-one | LCMS Method J m/z = 489.2 [M + H]+, Ret. time = 3.44 min Chiral HPLC method X7: Ret. time = 6.37 | 1H NMR (400 MHz, DMSO-d6) δ 9.73 (s, 1H), 8.75 (s, 1H), 8.43 (d, J = 8.6 Hz, 1H), 7.99 (d, J = 3.1 Hz, 1H), 7.73 (s, 1H), 7.43 (d, J = 8.6 Hz, 2H), 6.92 (d, J = 9.0 Hz, 1H), 4.64 (t, J = 5.4 Hz, 1H), 4.47 (s, 2H), 4.15 (t, J = 5.9 Hz, 2H), 3.70 (s, 1H), 3.58 (s, 2H), 2.87 (d, J = 6.8 Hz, 2H), 2.71 (t, J = 10.7 Hz, 1H), 2.01 (d, J = 26.0 Hz, 4H), 1.85 (s, 2H), 1.69 (s, 1H), 1.47 (d, J = 12.2 Hz, 1H). | G AA98 BB46 |
| I-572 | 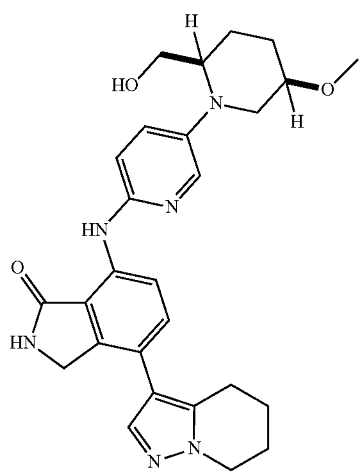 [SMILES: CO[C@@H]1CC[C@H](CO)N(c2ccc(Nc3ccc(-c4cnn5c4CCCC5)c4c3C(=O)NC4)nc2)C1] | 7-((5-((2R,5R)-2-(hydroxymethyl)-5-methoxypiperidin-1-yl)pyridin-2-yl)amino)-4-(4,5,6,7-tetrahydropyrazolo[1,5-a]pyridin-3-yl)isoindolin-1-one | LCMS Method J m/z = 489.3 [M + H]+, Ret. time = 3.51 min Chiral HPLC method X7: Ret. time = 6.78 | 1H NMR (400 MHz, DMSO-d6) δ 9.70 (s, 1H), 8.71 (s, 1H), 8.40 (d, J = 8.5 Hz, 1H), 7.96 (d, J = 3.0 Hz, 1H), 7.70 (s, 1H), 7.40 (dt, J = 9.1, 1.8 Hz, 2H), 6.89 (d, J = 9.0 Hz, 1H), 4.60 (t, J = 5.5 Hz, 1H), 4.44 (s, 2H), 4.12 (t, J = 6.1 Hz, 2H), 3.67 (s, 1H), 3.55 (ddd, J = 13.9, 10.3, 3.7 Hz, 2H), 3.38 (dd, J = 10.2, 4.9 Hz, 3H), 2.85 (t, J = 6.3 Hz, 2H), 2.68 (dd, J = 11.8, 9.9 Hz, 2H), 2.08-1.96 (m, 3H), 1.96-1.87 (m, 2H), 1.82 (ddd, J = 11.4, 8.0, 5.4 Hz, 2H), 1.66 (ddd, J = 14.3, 9.1, 4.6 Hz, 1H), 1.44 (dt, J = 12.9, 9.6 Hz, 1H). | G AA98 BB46 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-573 | 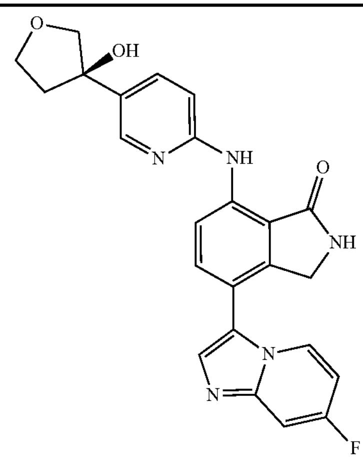 | (R)-4-(7-fluoro-imidazo[1,2-a]pyridin-3-yl)-7-(5-(3-hydroxytetra-hydrofuran-3-yl)pyridin-2-yl)amino)isoindolin-1-one | LCMS Method J m/z = 446.8 [M + H]+, Ret. time = 2.53 min Chiral HPLC method X11: Ret. time = 18.66 | 1H NMR (400 MHz, DMSO-d6) δ 10.13 (s, 1H), 8.86 (s, 1H), 8.74-8.72 (d, J = 8.5 Hz, 1H), 8.51-8.40 (m, 2H), 7.89-7.72 (m, 3H), 7.55 (dd, J = 10.0, 2.6 Hz, 1H), 7.10-6.93 (m, 2H), 5.49 (s, 1H), 4.42 (s, 2H), 3.85 (d, J = 8.8 Hz, 1H), 3.77 (d, J = 8.9 Hz, 1H), 3.19 (d, J = 5.2 Hz, 1H), 2.30 (dt, J = 12.7, 9.1 Hz, 1H). | ACp AA99 BB63 |
| I-574 | 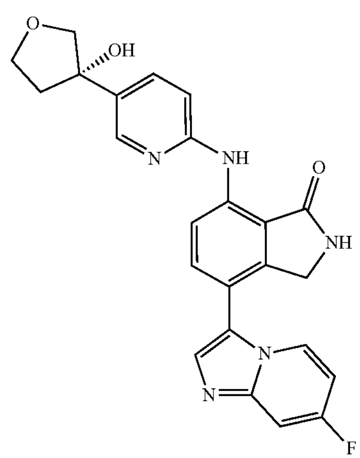 [SMILES: O=C1NCc2c(-c3cnc4cc(F)ccn34)ccc(Nc3ccc([C@@]4(O)CCOC4)cn3)c21] | (S)-4-(7-fluoroimidazo[1,2-a]pyridin-3-yl)-7-(5-(3-hydroxytetra-hydrofuran-3-yl)pyridin-2-yl)amino)isoindolin-1-one | LCMS Method J m/z = 446.8 [M + H]+, Ret. time = 2.53 min Chiral HPLC method X11: Ret. time = 16.71 | 1H NMR (400 MHz, DMSO-d6) δ 10.12 (s, 1H), 8.87 (s, 1H), 8.73 (d, J = 8.6 Hz, 1H), 8.51-8.38 (m, 2H), 7.89-7.69 (m, 3H), 7.55 (dd, J = 10.0, 2.6 Hz, 1H), 7.11-6.94 (m, 2H), 5.49 (s, 1H), 4.42 (s, 2H), 4.07-3.96 (m, 2H), 3.85 (d, J = 8.8 Hz, 1H), 3.77 (d, J = 8.8 Hz, 1H), 3.19 (d, J = 5.2 Hz, 1H), 2.31 (dd, J = 12.6, 9.1 Hz, 1H). | ACp AA99 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-575 | 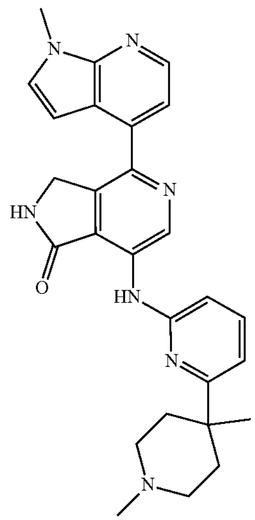 [SMILES: CN1CCC(C)(c2cccc(Nc3cnc(-c4ccnc5c4ccn5C)c4c3C(=O)NC4)n2)CC1] | 7-((6-(1,4-dimethylpiperidin-4-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 468.8 [M + H]+, Ret. time = 3.13 min | 1H NMR (400 MHz, DMSO-d6) δ 8.41-8.33 (m, 1H), 8.30 (s, 1H), 7.82 (s, 3H), 7.57 (d, J = 3.5 Hz, 1H), 7.37 (d, J = 5.3 Hz, 1H), 7.29 (s, 1H), 6.85 (s, 1H), 6.71 (s, 1H), 5.30 (s, 3H), 3.88 (s, 3H), 2.52-2.51 (m, 3H), 2.37 (s, 3H), 1.80 (s, 3H), 1.24 (d, J = 7.8 Hz, 4H). | O AA100 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-576 | 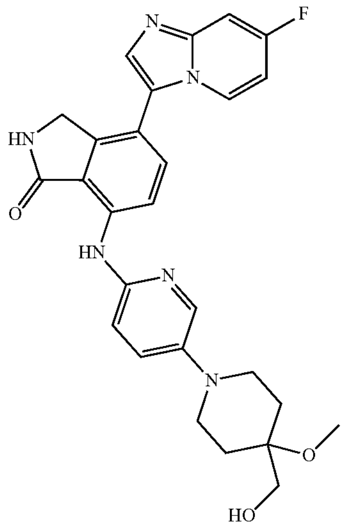 [SMILES: COC1(CO)CCN(c2ccc(Nc3ccc(-c4cnc5cc(F)ccn45)c4c3C(=O)NC4)nc2)CC1] | 4-(7-fluoro-imidazo[1,2-a]pyridin-3-yl)-7-((5-(4-(hydroxymethyl)-4-methoxypiperidin-1-yl)pyridin-2-yl)amino)isoindolin-1-one | LCMS Method J m/z = 503.9 [M + H]+, Ret. time = 2.49 min | 1H NMR (400 MHz, DMSO-d6) δ 9.84 (s, 1H), 8.78 (s, 1H), 8.56 (d, J = 8.6 Hz, 1H), 8.44 (dd, J = 7.6, 5.7 Hz, 1H), 8.02 (d, J = 3.0 Hz, 1H), 7.83 (s, 1H), 7.70 (d, J = 8.6 Hz, 1H), 7.54 (dd, J = 10.1, 2.7 Hz, 1H), 7.46 (dd, J = 8.9, 3.0 Hz, 1H), 7.02-6.91 (m, 2H), 4.59 (t, J = 5.6 Hz, 1H), 4.39 (s, 2H), 3.41 (d, J = 5.7 Hz, 2H), 3.32 (s, 2H), 3.19 (s, 3H), 2.93 (td, J = 11.7, 2.8 Hz, 2H), 1.77 (d, J = 13.4 Hz, 2H), 1.63 (td, J = 13.6, 12.7, 4.3 Hz, 2H). | Xp AA101 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-577 | 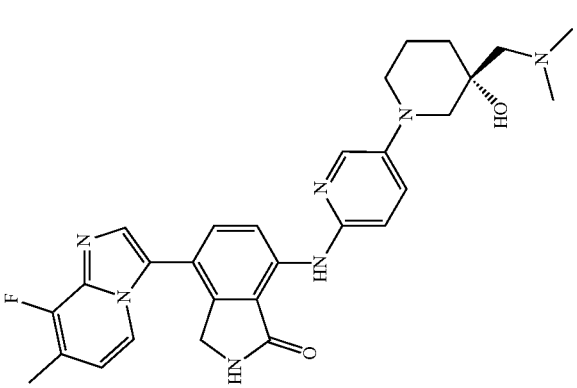 | (R)-7-((5-(3-((dimethyl-amino)methyl)-3-hydroxypiperidin-1-yl)pyridin-2-yl)amino)-4-(8-fluoro-7-methyl-imidazo[1,2-a]pyridin-3-yl)isoindolin-1-one | LCMS Method J m/z = 531.0 [M + 1]+, Ret. time = 2.62 min Chiral HPLC method X9: Ret. time = 7.58 | 1H NMR (400 MHz, DMSO-d6) δ 9.85 (s, 1H), 8.78 (s, 1H), 8.56 (d, J = 8.6 Hz, 1H), 8.16 (d, J = 7.0 Hz, 1H), 7.98 (d, J = 3.0 Hz, 1H), 7.68 (d, J = 8.6 Hz, 1H), 7.42 (dd, J = 9.0, 3.1 Hz, 1H), 6.97 (d, J = 8.9 Hz, 1H), 6.84 (t, J = 6.7 Hz, 1H), 4.39 (s, 3H), 3.11 (dd, J = 12.2, 5.4 Hz, 2H), 2.96 (s, 1H), 2.80 (d, J = 11.6 Hz, 2H), 2.62 (s, 2H), 2.43-2.18 (m, 9H), 1.80 (s, 2H), 1.44 (d, J = 9.3 Hz, 2H). | Yp AA95 BB80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-578 | 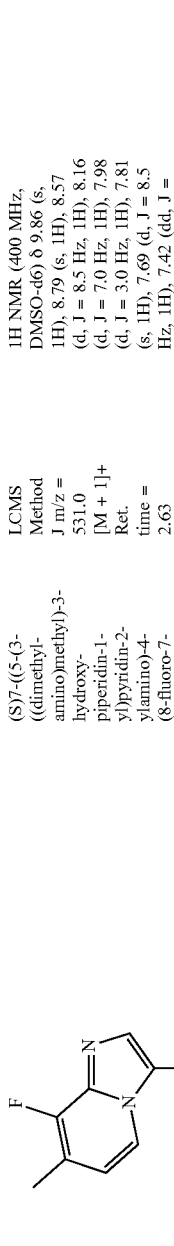 | (S)7-((5-(3-((dimethylamino)methyl)-3-hydroxy-piperidin-1-yl)pyridin-2-yl)amino)-4-(8-fluoro-7-methyl-imidazo[1,2-a]pyridin-3-yl)isoindolin-1-one | LCMS Method J m/z = 531.0 [M + 1]+ Ret. time = 2.63 min Chiral HPLC method X9: Ret. time = 20.19 | 1H NMR (400 MHz, DMSO-d6) δ 9.86 (s, 1H), 8.79 (s, 1H), 8.57 (d, J = 8.5 Hz, 1H), 8.16 (d, J = 7.0 Hz, 1H), 7.98 (d, J = 3.0 Hz, 1H), 7.81 (s, 1H), 7.69 (d, J = 8.5 Hz, 1H), 7.42 (dd, J = 9.0, 3.0 Hz, 1H), 6.97 (d, J = 8.9 Hz, 1H), 6.85 (t, J = 6.7 Hz, 1H), 4.39 (s, 3H), 3.10 (d, J = 11.1 Hz, 2H), 2.95 (dd, J = 10.8, 7.0 Hz, 1H), 2.80 (d, J = 11.5 Hz, 1H), 2.42-2.23 (m, 9H), 1.86-1.69 (m, 2H), 1.57 (s, 2H), 1.44 (d, J = 10.8 Hz, 2H). | Yp AA95 BB80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-579 | 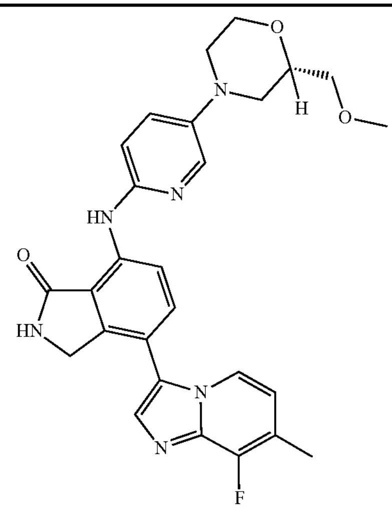 | (S)-4-(8-fluoro-7-methyl-imidazo[1,2-a]pyridin-3-yl)-7-((5-(2-(methoxymethyl)morpho-lino)pyridin-2-yl)amino)iso-indolin-1-one | LCMS Method J m/z = 503.2 [M + H]+, Ret. time = 3.52 min Chiral HPLC method X10: Ret. time = 7.14 | 1H NMR (400 MHz, DMSO-d6) δ 9.89 (s, 1H), 8.79 (s, 1H), 8.58 (d, J = 8.6 Hz, 1H), 8.16 (d, J = 7.0 Hz, 1H), 8.02 (d, J = 3.0 Hz, 1H), 7.81 (s, 1H), 7.69 (d, J = 8.6 Hz, 1H), 7.47 (dd, J = 9.0, 3.0 Hz, 1H), 7.00 (d, J = 9.0 Hz, 1H), 6.84 (t, J = 6.7 Hz, 1H), 4.39 (s, 2H), 4.01-3.93 (m, 1H), 3.76 (dtd, J = 10.4, 5.0, 2.3 Hz, 1H), 3.68 (td, J = 11.4, 2.6 Hz, 1H), 3.52 (d, J = 11.6 Hz, 1H), 3.45 (h, J = 5.4 Hz, 3H), 3.31 (s, 3H), 2.71 (td, J = 11.7, 3.4 Hz, 1H), 2.50-2.43 (m, 1H), 2.34 (d, J = 2.3 Hz, 3H). | G AA39 BB80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-580 | 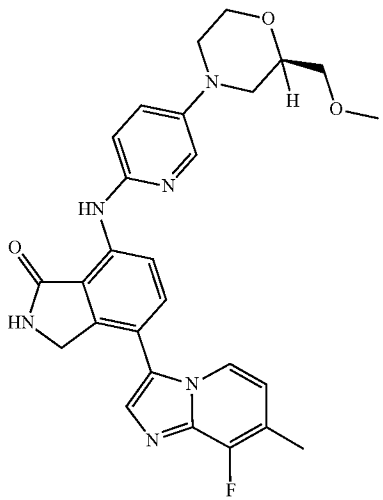 [SMILES: COC[C@H]1CN(c2ccc(Nc3ccc(-c4cnc5c(F)c(C)ccn45)c4c3C(=O)NC4)nc2)CCO1] | (R)-4-(8-fluoro-7-methylimidazo[1,2-a]pyridin-3-yl)-7-((5-(-2-(methoxymethyl)morpholino)pyridin-2-yl)amino)isoindolin-1-one | LCMS Method J m/z = 503.2 [M + H]+, Ret. time = 2.53 min Chiral HPLC method X10: Ret. time = 7.08 | 1H NMR (400 MHz, DMSO-d6) δ 9.89 (s, 1H), 8.79 (s, 1H), 8.58 (d, J = 8.5 Hz, 1H), 8.16 (d, J = 7.0 Hz, 1H), 8.02 (d, J = 3.0 Hz, 1H), 7.81 (s, 1H), 7.69 (d, J = 8.6 Hz, 1H), 7.47 (dd, J = 9.0, 3.0 Hz, 1H), 7.00 (d, J = 9.0 Hz, 1H), 6.84 (t, J = 6.8 Hz, 1H), 4.39 (s, 2H), 4.01-3.93 (m, 1H), 3.81-3.72 (m, 1H), 3.68 (td, J = 11.4, 2.6 Hz, 1H), 3.52 (d, J = 11.7 Hz, 1H), 3.45 (td, J = 10.5, 5.0 Hz, 3H), 3.31 (s, 3H), 2.71 (td, J = 11.6, 3.4 Hz, 1H), 2.50-2.43 (m, 1H), 2.34 (d, J = 2.4 Hz, 3H). | G AA39 BB80 |
| I-581 | 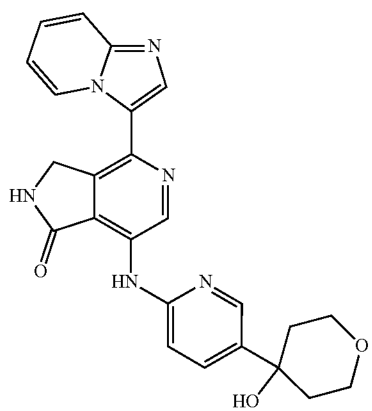 [SMILES: O=C1NCc2c(-c3cnc4ccccn34)ncc(Nc3ccc(C4(O)CCOCC4)cn3)c21] | 7-((5-(4-hydroxytetrahydro-2H-pyran-4-yl)pyridin-2-yl)amino)-4-(imidazo[1,2-a]pyridin-3-yl)-2,3-dihydro-1H-pyrrolo[3,4-c]pyridin-1-one | LCMS Method J m/z = 443.8 [M + H]+, Ret. time = 2.63 min | 1H NMR (400 MHz, DMSO-d6) δ 10.04 (s, 1H), 9.92-9.90 (d, J = 7.0 Hz, 1H), 9.64 (s, 1H), 9.33 (s, 1H), 8.47-8.46 (d, J = 2.0 Hz, 1H), 8.12 (s, 1H), 7.85-7.82 (d, J = 9.0 Hz, 1H), 7.76-7.73 (t, J = 9.2 Hz, 1H), 7.45-7.41 (t, J = 7.2 Hz, 1H), 7.13-7.07 (m, 2H), 5.25 (s, 1H), 4.36 (s, 2H), 3.84-3.75 (m, 4H), 2.05-2.01 (m, 2H), 1.24 (s, 2H). | O AA57 BB26 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-582 | 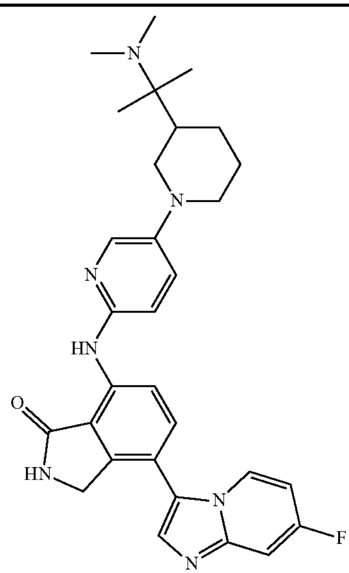 | 7-((5-(3-(2-(dimethyl-amino)propan-2-yl)piperidin-1-yl)pyridin-2-yl)amino)-4-(7-fluoro-imidazo[1,2-a]pyridin-3-yl)isoindolin-1-one | LCMS Method J m/z = 528.4 [M + H]+, Ret. time = 2.94 min | 1H NMR (400 MHz, DMSO-d6) δ 9.84 (s, 1H), 8.78 (s, 1H), 8.57-8.55 (d, J = 8.6 Hz, 1H), 8.44-8.41 (dd, J = 7.6, 5.7 Hz, 1H), 8.32 (s, 1H), 7.99-7.98 (d, J = 3.0 Hz, 1H), 7.82 (s, 1H), 7.70-7.68 (d, J = 8.6 Hz, 1H), 7.55-7.52 (dd, J = 10.0, 2.7 Hz, 1H), 7.39 (dd, J = 9.0, 3.0 Hz, 1H), 6.98 (td, J = 8.9, 8.2, 3.3 Hz, 1H), 4.38 (s, 2H), 3.75-3.70 (m, 2H), 2.39-2.33 (m, 1H), 2.16 (s, 6H), 1.86-1.77 (m, 3H), 1.62-1.59 (m, 1H), 1.18-1.10 (m, 2H), 1.25 (s, 1H), 0.95 (s, 3H), 0.87 (s, 3H). | G AA103 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-583 | 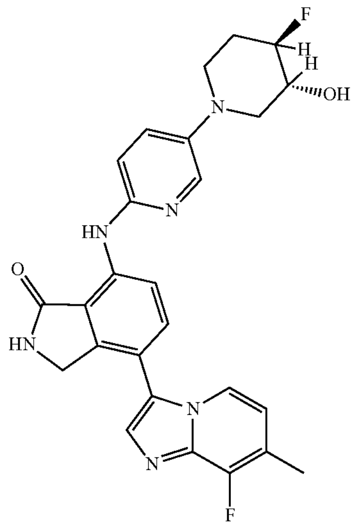 [SMILES: Cc1ccn2c(-c3ccc(Nc4ccc(N5CC[C@@H](F)[C@H](O)C5)cn4)c4c3CNC4=O)cnc2c1F] | 7-((5-((3R,4R)-4-fluoro-3-hydroxypiperidin-1-yl)pyridin-2-yl)amino)-4-(8-fluoro-7-methylimidazo[1,2-a]pyridin-3-yl)isoindolin-1-one | LCMS Method J m/z = 491.8 [M + H]+, Ret. time = 3.00 min Chiral HPLC method X8: Ret. time = 21.07 | 1H NMR (400 MHz, DMSO-d6) δ 9.87 (s, 1H), 8.80 (s, 1H), 8.58-8.56 (d, J = 8.6 Hz, 1H), 8.17-8.15 (d, J = 6.9 Hz, 1H), 8.02 (d, J = 3.0 Hz, 1H), 7.81 (s, 1H), 7.70-7.67 (d, J = 8.6 Hz, 1H), 7.48-7.45 (dd, J = 9.1, 3.0 Hz, 1H), 6.96 (d, J = 9.0 Hz, 1H), 6.85-6.82 (t, J = 6.7 Hz, 1H), 5.45-5.44 (d, J = 5.0 Hz, 1H), 4.39 (s, 3H), 3.62 (d, J = 48.9 Hz, 3H), 2.83 (t, J = 11.7 Hz, 1H), 2.65 (dd, J = 12.1, 9.4 Hz, 1H), 2.34 (d, J = 2.3 Hz, 3H), 2.12 (s, 1H), 1.82-1.69 (m, 1H). | Q AA49 BB80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-584 | 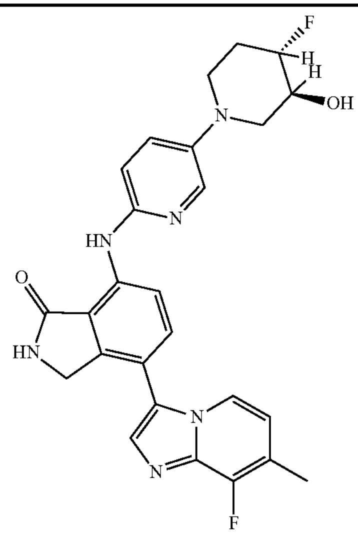 | 7-(5-((3S,4S)-4-fluoro-3-hydroxy-piperidin-1-yl)pyridin-2-ylamino)-4-(8-fluoro-7-methylimidazo[1,2-a]pyridin-3-yl)isoindolin-1-one | LCMS Method J m/z = 491.8 [M + H]+, Ret. time = 3.00 min Chiral HPLC method X8: Ret. time = 22.47 | 1H NMR (400 MHz, DMSO-d6) δ 9.87 (s, 1H), 8.79 (s, 1H), 8.58-8.55 (d, J = 8.6 Hz, 1H), 8.16-8.14 (d, J = 7.0 Hz, 1H), 8.02 (d, J = 3.1 Hz, 1H), 7.82 (s, 1H), 7.69-7.67 (d, J = 8.6 Hz, 1H), 7.48-7.45 (m, 1H), 6.97 (d, J = 8.9 Hz, 1H), 6.85-6.82 (d, J = 6.8 Hz, 1H), 5.44-5.43 (d, J = 5.0 Hz, 1H), 4.39 (s, 3H), 3.69 (s, 1H), 3.56-3.52 (m, 2H), 2.85-2.80 (t, J = 11.3 Hz, 1H), 2.68-2.62 (m, 1H), 2.34-2.33 (d, J = 2.4 Hz, 3H), 2.15-2.10 (s, 1H), 1.56 (s, 1H). | Q AA49 BB80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-585 | 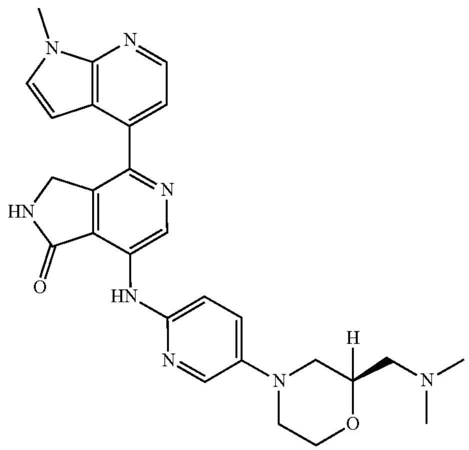 [SMILES: CN(C)C[C@@H]1CN(c2ccc(Nc3cnc(-c4ccnc5c4ccn5C)c4c3C(=O)NC4)nc2)CCO1] | (R)-7-((5-(2-((dimethyl-amino)methyl)mor-pholino)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 499.9 [M + H]+, Ret. time = 2.75 min Chiral HPLC method X3: Ret. time = 6.86 | 1H NMR (400 MHz, DMSO-d6) δ 9.93 (s, 1H), 9.54 (s, 1H), 9.17 (s, 1H), 8.36-8.35 (d, J = 5.0 Hz, 1H), 8.07-8.06 (d, J = 3.0 Hz, 1H), 7.58-7.57 (d, J = 3.4 Hz, 1H), 7.50-7.47 (dd, J = 9.0, 3.0 Hz, 1H), 7.39-7.38 (d, J = 5.0 Hz, 1H), 7.10-7.08 (d, J = 9.0 Hz, 1H), 6.92-6.91 (d, J = 3.5 Hz, 1H), 4.00-3.92 (m, 2H), 3.78-3.65 (m, 1H), 3.56 (d, J = 11.5 Hz, 1H), 3.49 (d, J = 11.9 Hz, 1H), 2.74 (dd, J = 11.6, 3.4 Hz, 2H), 2.46-2.37 (m, 3H), 2.34 (s, 2H), 2.24 (s, 6H). | Zp AA63 BB14 |
| I-586 | 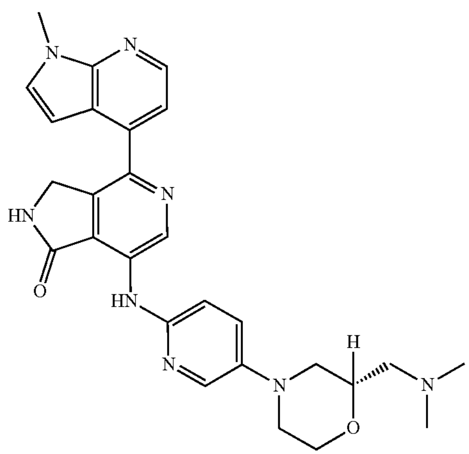 [SMILES: CN(C)C[C@H]1CN(c2ccc(Nc3cnc(-c4ccnc5c4ccn5C)c4c3C(=O)NC4)nc2)CCO1] | (S)-7-((5-(2-((dimethyl-amino)methyl)mor-pholino)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 499.9 [M + H]+, Ret. time = 2.76 min Chiral HPLC method X3: Ret. time = 6.83 | 1H NMR (400 MHz, DMSO-d6) δ 9.97 (s, 1H), 9.57 (s, 1H), 9.20 (s, 1H), 8.39 (d, J = 5.0 Hz, 1H), 8.10-8.09 (d, J = 3.0 Hz, 1H), 7.61-7.60 (d, J = 3.5 Hz, 1H), 7.53-7.50 (dd, J = 9.0, 3.1 Hz, 1H), 7.42-7.41 (d, J = 5.1 Hz, 1H), 7.13-7.10 (d, J = 8.9 Hz, 1H), 6.95-6.94 (d, J = 3.5 Hz, 1H), 4.72 (s, 2H), 4.00-3.92 (m, 1H), 3.78-3.65 (m, 2H), 3.56 (d, J = 11.5 Hz, 1H), 3.49 (d, J = 11.9 Hz, 1H), 2.74 (dd, J = 11.6, 3.4 Hz, 2H), 2.46-2.37 (m, 3H), 2.34 (s, 2H), 2.24 (s, 6H). | Zp AA63 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-587 | 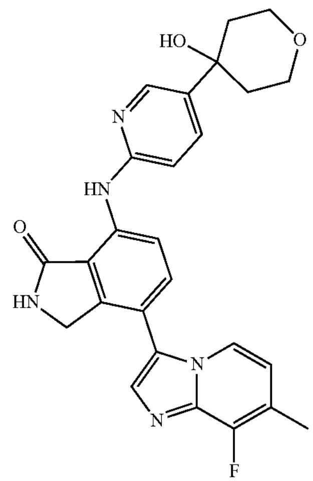 [SMILES: Cc1ccn2c(-c3ccc(Nc4ccc(C5(O)CCOCC5)cn4)c4c3CNC4=O)cnc2c1F] | 4-(8-fluoro-7-methylimidazo[1,2-a]pyridin-3-yl)-7-(5-(4-hydroxytetrahydro-2H-pyran-4-yl)pyridin-2-ylamino)isoindolin-1-one | LCMS Method J m/z = 474.2 [M + H]+, Ret. time = 3.15 min | 1H NMR (400 MHz, DMSO-d6) δ 10.10 (s, 1H), 8.86 (s, 1H), 8.75-8.73 (d, J = 8.6 Hz, 1H), 8.43-8.42 (d, J = 2.5 Hz, 1H), 8.18-8.17 (d, J = 7.0 Hz, 1H), 7.87-7.76 (m, 2H), 7.75-7.73 (d, J = 8.5 Hz, 1H), 7.02-7.00 (d, J = 8.6 Hz, 1H), 6.86-6.83 (t, J = 6.8 Hz, 1H), 5.15 (s, 1H), 4.41 (s, 2H), 3.87-3.70 (m, 4H), 2.35 (d, J = 2.4 Hz, 3H), 2.00 (dd, J = 12.8, 5.0 Hz, 2H), 1.62 (d, J = 13.0 Hz, 2H). | ACp AA57 BB80 |
| I-588 | 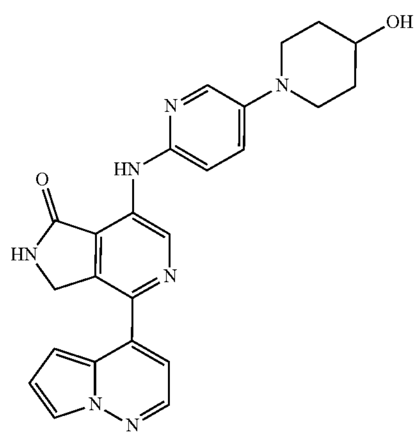 [SMILES: O=C1NCc2c(-c3ccnn4cccc34)ncc(Nc3ccc(N4CCC(O)CC4)cn3)c21] | 7-((5-(4-hydroxypiperidin-1-yl)pyridin-2-yl)amino)-4-(pyrrolo[1,2-b]pyridazin-4-yl)-2,3-dihydro-1H-pyrrolo[3,4-c]pyridin-1-one | LCMS Method J m/z = 442.2 [M + H]+, Ret. time = 3.48 min | 1H NMR (400 MHz, DMSO-d6) δ 9.92 (s, 1H), 9.56 (s, 1H), 9.19 (s, 1H), 8.26-8.25 (d, J = 4.7 Hz, 1H), 8.08-8.07 (d, J = 3.0 Hz, 1H), 7.92 (t, J = 2.1 Hz, 1H), 7.49-7.46 (dd, J = 9.0, 3.1 Hz, 1H), 7.12-7.00 (m, 2H), 7.00-6.93 (m, 2H), 4.78-4.64 (m, 3H), 3.65 (dt, J = 8.9, 4.4 Hz, 1H), 3.50 (d, J = 11.9 Hz, 2H), 2.92-2.79 (m, 2H), 1.86 (d, J = 10.5 Hz, 2H), 1.54 (s, 2H). | AJp AA12 BB92 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-589 | 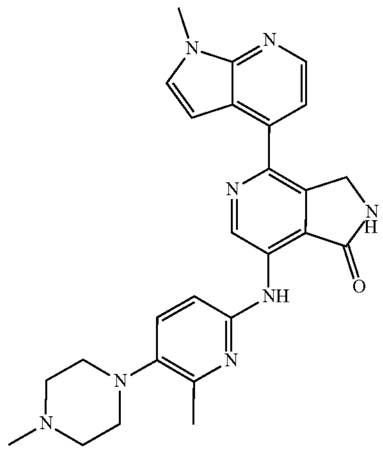 | 4-(1-methyl-1H-pyrrolo[2,3-b]pyridin-4-yl)-7-((6-methyl-5-(4-methylpiperazin-1-yl)pyridin-2-yl)amino)-2,3-dihydro-1H-pyrrolo[3,4-c]pyridin-1-one | LCMS Method J m/z = 469.5 [M + H]+, Ret. time = 2.75 min | 1H NMR (400 MHz, Methanol-d4) δ 10.12 (s, 1H), 8.37 (d, J = 5.0 Hz, 1H), 7.69 (s, 1H), 7.48 (d, J = 8.6 Hz, 1H), 7.40 (d, J = 3.5 Hz, 1H), 7.29 (d, J = 5.0 Hz, 1H), 6.85 (d, J = 8.5 Hz, 1H), 6.71 (d, J = 3.4 Hz, 1H), 4.60 (s, 2H), 3.95 (s, 4H), 2.96 (t, J = 4.7 Hz, 4H), 2.68 (s, 3H), 2.56 (s, 3H), 2.41 (s, 3H). | O AA105 BB14 |

TABLE 8-continued

Characterization Data (LCMS and $^1$H NMR).

| # | STRUCTURE | NAME | LCMS | $^1$H NMR | Method Reagent AA BB |
|---|---|---|---|---|---|
| I-590 | 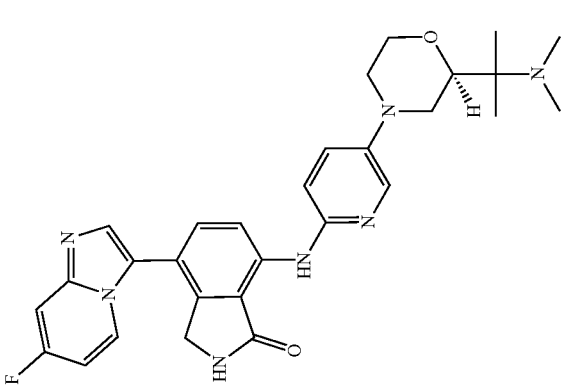 | (R)-7-((5-(2-(2-(dimethyl-amino)propan-2-yl)morpho-lino)pyridin-2-yl)amino)-4-(7-fluoro-imidazo[1,2-a]pyridin-3-yl)isoindolin-1-one | LCMS Method J m/z = 530.5 [M + H]+, Ret. time = 2.48 min Chiral HPLC method X8: Ret. time = 16.89 | 1H NMR (400 MHz, DMSO-d6) δ 9.89 (s, 1H), 8.80 (s, 1H), 8.60-8.58 (d, J = 8.6 Hz, 1H), 8.44-8.41 (dd, J = 7.7, 5.8 Hz, 1H), 8.05 (s, 1H), 7.83 (s, 1H), 7.70 (d, J = 8.6 Hz, 1H), 7.57-7.42 (m, 2H), 7.04-6.92 (m, 2H), 4.39 (s, 2H), 4.04 (d, J = 10.1 Hz, 2H), 3.72 (s, 2H), 3.56 (d, J = 11.8 Hz, 1H), 3.48 (d, J = 11.8 Hz, 1H), 2.72 (d, J = 12.5 Hz, 1H), 2.26 (s, 6H), 1.09 (s, 6H). | G AA93 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-591 | 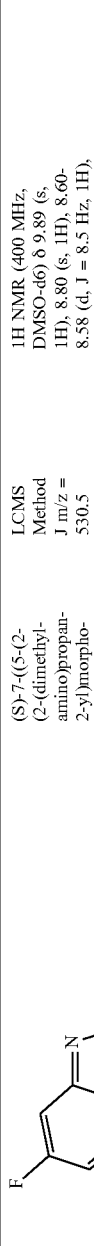 | (S)-7-((5-(2-(2-(dimethyl-amino)propan-2-yl)morpho-lino)pyridin-2-yl)amino)-4-(7-fluoro-imidazo[1,2-a]pyridin-3-yl)isoindolin-1-one | LCMS Method J m/z = 530.5 [M + H]+, Ret. time = 1.38 min Chiral HPLC method X8: Ret. time = 21.10 | 1H NMR (400 MHz, DMSO-d6) δ 9.89 (s, 1H), 8.80 (s, 1H), 8.60-8.58 (d, J = 8.5 Hz, 1H), 8.44-8.40 (dd, J = 7.7, 5.7 Hz, 1H), 8.05 (s, 1H), 7.82 (s, 1H), 7.71-7.69 (d, J = 8.6 Hz, 1H), 7.54-7.48 (m, 2H), 7.01-6.94 (m, 2H), 4.39 (s, 2H), 4.05 (dd, J = 10.9, 3.2 Hz, 1H), 3.74 (s, 2H), 3.53 (dd, J = 25.2, 11.8 Hz, 2H), 2.71 (t, J = 11.7 Hz, 1H), 2.41 (s, 6H), 1.74-1.68 (m, 1H), 1.15 (s, 6H). | G AA93 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-592 | ![structure] | 7-((5-(4-hydroxy-piperidin-1-yl)pyridin-2-yl)amino)-4-(1,7-naphthyridin-4-yl)-2,3-dihydro-1H-pyrrolo[3,4-c]pyridin-1-one | LCMS Method J m/z = 454.2 [M + H]+, Ret. time = 8.16 min | 1H NMR (400 MHz, DMSO-d6) δ 9.48 (s, 2H), 9.15 (t, J = 3.6 Hz, 2H), 8.62 (d, J = 5.9 Hz, 1H), 8.48 (s, 1H), 8.15-7.98 (m, 3H), 7.49 (dd, J = 9.1, 3.0 Hz, 1H), 7.08 (d, J = 8.9 Hz, 1H), 4.73 (s, 1H), 4.59 (s, 2H), 2.86 (s, 3H), 1.91-1.79 (m, 2H), 1.61-1.43 (m, 2H), 1.24 (s, 2H). | Alp AA12 BB83 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-593 | 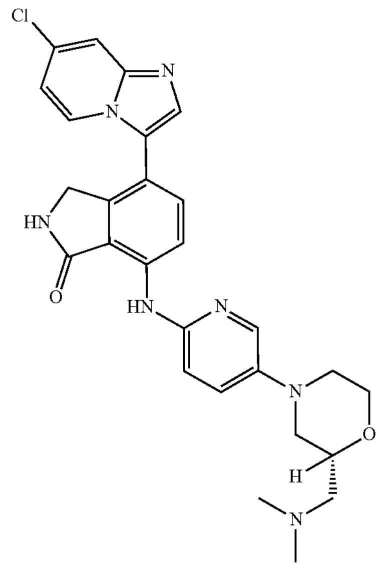 [SMILES: CN(C)C[C@@H]1CN(c2ccc(Nc3ccc(-c4cnc5cc(Cl)ccn45)c4c3C(=O)NC4)nc2)CCO1] | (R)-4-(7-chloroimidazo[1,2-a]pyridin-3-yl)-7-((5-(2-((dimethylamino)methyl)morpholino)pyridin-2-yl)amino)isoindolin-1-one | LCMS Method J m/z = 518.1 [M + H]+, Ret. time = 2.56 min Chiral HPLC method X9: Ret. time = 8.91 | 1H NMR (400 MHz, DMSO-d6) δ 9.89 (s, 1H), 8.80 (s, 1H), 8.59-8.57 (d, J = 8.6 Hz, 1H), 8.41-8.39 (d, J = 7.5 Hz, 1H), 8.01-8.00 (d, J = 3.0 Hz, 1H), 7.94-7.81 (m, 2H), 7.72-7.70 (d, J = 8.4 Hz, 1H), 7.47-7.44 (d, J = 8.5 Hz, 1H), 7.00-6.98 (dd, J = 9.0, 3.0 Hz, 2H), 4.40 (s, 2H), 4.01-3.90 (m, 1H), 3.74-3.63 (m, 2H), 3.53 (d, J = 11.7 Hz, 1H), 3.46 (d, J = 12.0 Hz, 1H), 2.74-2.67 (m, 1H), 2.74-2.67 (m, 1H), 2.37 (dd, J = 5.9, 2.8 Hz, 3H), 2.21 (s, 6H). | G AA63 BB79 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-594 | 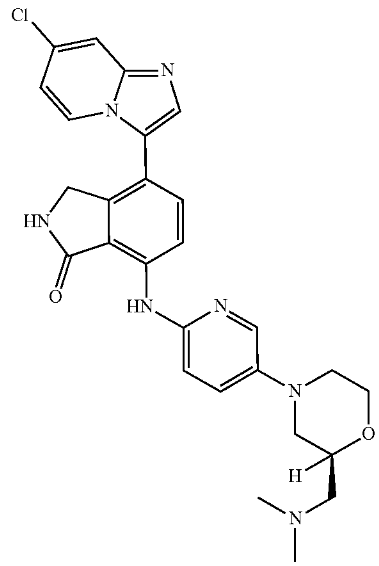 [SMILES: CN(C)C[C@H]1CN(c2ccc(Nc3ccc(-c4cnc5cc(Cl)ccn45)c4c3C(=O)NC4)nc2)CCO1] | (S)-4-(7-chloroimidazo[1,2-a]pyridin-3-yl)-7-((5-(2-((dimethyl-amino)methyl)mor-pholino)pyridin-2-yl)amino)iso-indolin-1-one | LCMS Method J m/z = 518.9 [M + H]+, Ret. time = 2.56 min Chiral HPLC method X9: Ret. time = 9.07 | 1H NMR (400 MHz, DMSO-d6) δ 9.89 (s, 1H), 8.80 (s, 1H), 8.59-8.57 (d, J = 8.6 Hz, 1H), 8.41-8.39 (d, J = 7.4 Hz, 1H), 8.01-8.00 (d, J = 3.1 Hz, 1H), 7.91-7.79 (m, 2H), 7.72-7.70 (d, J = 8.6 Hz, 1H), 7.47-7.44 (dd, J = 9.0, 3.1 Hz, 1H), 7.00-6.98 (m, 2H), 4.40 (s, 2H), 4.00-3.88 (m, 1H), 3.75-3.63 (m, 2H), 3.50 (dd, J = 28.9, 11.6 Hz, 2H), 2.70 (td, J = 2.37 (dd, J = 5.9, 2.8 Hz, 3H), 2.21 (s, 6H). | G AA63 BB79 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-595 | 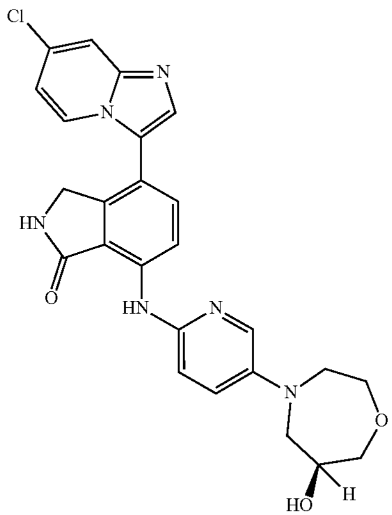 [SMILES: O=C1NCc2c(-c3cnc4cc(Cl)ccn34)ccc(Nc3ccc(N4CCOC[C@@H](O)C4)cn3)c21] | (S)-4-(7-chloro-imidazo[1,2-a]pyridin-3-yl)-7-((5-(6-hydroxy-1,4-oxazepan-4-yl)pyridin-2-yl)amino)iso-indolin-1-one | LCMS Method J m/z = 491.2 [M + H]+, Ret. time = 3.04 min Chiral HPLC method X9: Ret. time = 11.31 | 1H NMR (400 MHz, DMSO-d6) δ 9.72 (s, 1H), 8.74 (s, 1H), 8.48-8.46 (d, J = 8.6 Hz, 1H), 8.39-8.38 (d, J = 7.4 Hz, 1H), 7.94 (d, J = 3.1 Hz, 1H), 7.92-7.81 (m, 2H), 7.68-7.66 (d, J = 8.6 Hz, 1H), 7.32 (dd, J = 9.0, 3.1 Hz, 1H), 7.02-6.88 (m, 2H), 4.38 (s, 2H), 3.99 (s, 1H), 3.83 (dd, J = 14.9, 5.0 Hz, 2H), 3.75 (d, J = 4.8 Hz, 1H), 3.71-3.62 (m, 1H), 3.62-3.55 (m, 1H), 3.49 (dd, J = 12.7, 6.0 Hz, 3H), 3.26 (s, 1H). | G AA43 BB79 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-596 | 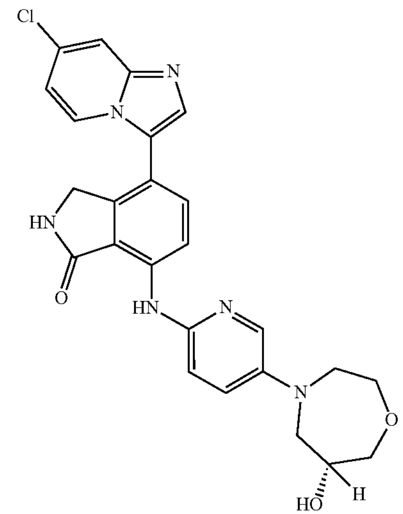 [SMILES: O=C1NCc2c(-c3cnc4cc(Cl)ccn34)ccc(Nc3ccc(N4CCOC[C@H](O)C4)cn3)c21] | (R)-4-(7-chloroimidazo[1,2-a]pyridin-3-yl)-7-((5-(6-hydroxy-1,4-oxazepan-4-yl)pyridin-2-yl)amino)isoindolin-1-one | LCMS Method J m/z = 491.2 [M + H]+, Ret. time = 3.05 min Chiral HPLC method X9: Ret. time = 11.87 | 1H NMR (400 MHz, DMSO-d6) δ 9.72 (d, J = 2.1 Hz, 1H), 8.74 (s, 1H), 8.49-8.46 (dd, J = 8.6, 2.1 Hz, 1H), 8.40-8.38 (dd, J = 7.4, 2.1 Hz, 1H), 7.95-7.94 (d, J = 2.9 Hz, 1H), 7.89-7.75 (m, 2H), 7.68-7.66 (dd, J = 8.5, 1.9 Hz, 1H), 7.33-7.30 (dd, J = 9.0, 3.2 Hz, 1H), 7.00-6.94 (m, 2H), 4.38 (s, 2H), 3.99 (s, 1H), 3.83 (dd, J = 15.0, 5.1 Hz, 1H), 3.78-3.71 (m, 2H), 3.71-3.55 (m, 3H), 3.54-3.42 (m, 2H), 3.30-3.25 (m, 1H). | G AA43 BB79 |

TABLE 8-continued

Characterization Data (LCMS and ¹H NMR).

| # | STRUCTURE | NAME | LCMS | ¹H NMR | Method AA Reagent BB |
|---|---|---|---|---|---|
| I-597 | 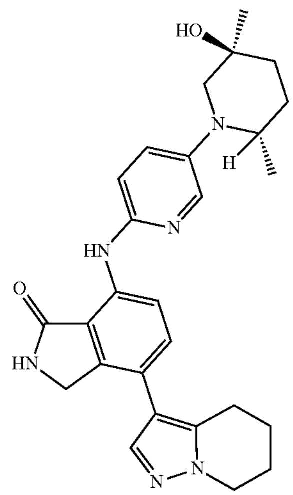 [SMILES: C[C@H]1CC[C@](C)(O)CN1c1ccc(Nc2ccc(-c3cnn4c3CCCC4)c3c2C(=O)NC3)nc1] | 7-((5-((2S,5S)-5-hydroxy-2,5-dimethyl-piperidin-1-yl)pyridin-2-yl)amino)-4-(4,5,6,7-tetrahydro-pyrazolo[1,5-a]pyridin-3-yl)isoindolin-1-one | LCMS Method J m/z = 473.8 [M + H]+, Ret. time = 3.04 min Chiral HPLC method X10: Ret. time = 5.4 | 1H NMR (400 MHz, DMSO-d6) δ 9.76 (s, 1H), 8.73 (s, 1H), 8.42 (d, J = 8.5 Hz, 1H), 7.94 (d, J = 2.9 Hz, 1H), 7.70 (s, 1H), 7.47-7.32 (m, 2H), 6.90 (d, J = 8.9 Hz, 1H), 4.52 (s, 1H), 4.44 (s, 2H), 4.12 (t, J = 6.1 Hz, 2H), 3.62 (q, J = 5.4 Hz, 1H), 2.94-2.80 (m, 3H), 2.76 (d, J = 11.5 Hz, 1H), 2.02 (td, J = 8.0, 7.0, 4.3 Hz, 2H), 1.79 (ddt, J = 16.8, 9.2, 3.9 Hz, 3H), 1.73-1.53 (m, 2H), 1.48 (dd, J = 12.3, 5.8 Hz, 1H), 1.17 (s, 3H), 0.92 (d, J = 6.4 Hz, 3H). | G AA106 BB46 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-598 | 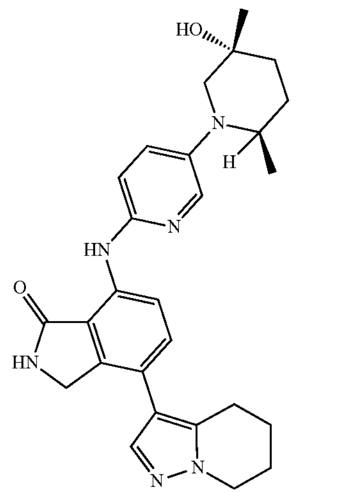 [SMILES: C[C@@H]1CC[C@@](C)(O)CN1c1ccc(Nc2ccc(-c3cnn4c3CCCC4)c3c2C(=O)NC3)nc1] | 7-(5-((2R,5R)-5-hydroxy-2,5-dimethyl-piperidin-1-yl)pyridin-2-yl)amino)-4-(4,5,6,7-tetrahydro-pyrazolo[1,5-a]pyridin-3-yl)isoindolin-1-one | LCMS Method J m/z = 473.9 [M + H]+, Ret. time = 3.04 min Chiral HPLC method X10: Ret. time = 5.74 | 1H NMR (400 MHz, DMSO-d6) δ 9.76 (s, 1H), 8.73 (s, 1H), 8.42 (d, J = 8.6 Hz, 1H), 7.94 (d, J = 2.9 Hz, 1H), 7.70 (s, 1H), 7.49-7.35 (m, 2H), 6.90 (d, J = 8.9 Hz, 1H), 4.52 (s, 1H), 4.44 (s, 2H), 4.12 (t, J = 6.1 Hz, 2H), 3.62 (q, J = 5.3 Hz, 1H), 2.92-2.80 (m, 3H), 2.76 (d, J = 11.4 Hz, 1H), 2.08-1.95 (m, 1H), 1.88-1.73 (m, 3H), 1.62 (d, J = 34.6 Hz, 3H), 1.48 (dd, J = 12.1, 5.9 Hz, 1H), 1.17 (s, 3H), 0.92 (d, J = 6.4 Hz, 3H). | G AA106 BB46 |
| I-599 | 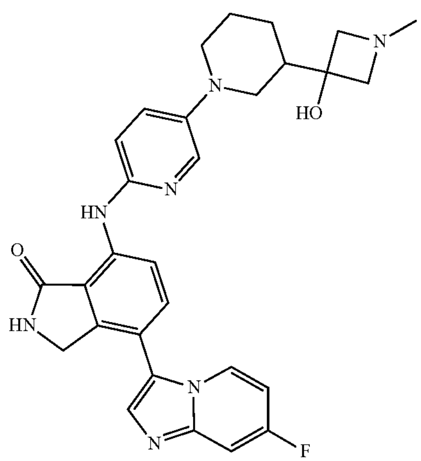 [SMILES: CN1CC(O)(C2CCCN(c3ccc(Nc4ccc(-c5cnc6cc(F)ccn56)c5c4C(=O)NC5)nc3)C2)C1] | 4-(7-fluoro-imidazo[1,2-a]pyridin-3-yl)-7-((5-(3-(3-hydroxy-1-methylazetidin-3-yl)piperidin-1-yl)pyridin-2-yl)amino)iso-indolin-1-one | LCMS Method J m/z = 528.2 [M + H]+, Ret. time = 2.78 min | 1H NMR (400 MHz, DMSO-d6) δ 9.84 (s, 1H), 8.79 (s, 1H), 8.57-8.55 (d, J = 8.5 Hz, 1H), 8.50-8.39 (m, 1H), 8.00 (d, J = 3.0 Hz, 1H), 7.83 (s, 1H), 7.70-7.68 (d, J = 8.6 Hz, 1H), 7.54 (d, J = 10.0 Hz, 1H), 7.45 (dd, J = 9.0, 3.1 Hz, 1H), 7.02-6.90 (m, 2H), 4.39 (s, 2H), 3.62 (d, J = 12.0 Hz, 4H), 3.53-3.50 (m, 1H), 3.44 (d, J = 5.1 Hz, 1H), 2.91 (s, 2H), 2.29 (s, 2H), 1.82 (dt, J = 20.7, 10.9 Hz, 3H), 1.59 (d, J = 13.5 Hz, 2H), 1.39-1.06 (m, 2H). | Xp AA136 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-600 | 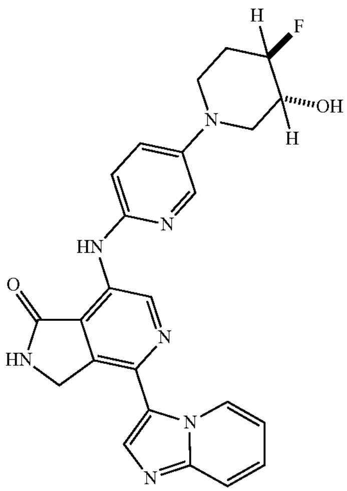 [SMILES: O=C1NCc2c(-c3cnc4ccccn34)ncc(Nc3ccc(N4CC[C@@H](F)[C@H](O)C4)cn3)c21] | 7-((5-((3R,4R)-4-fluoro-3-hydroxy-piperidin-1-yl)pyridin-2-yl)amino)-4-(imidazo[1,2-a]pyridin-3-yl)-2,3-dihydro-1H-pyrrolo[3,4-c]pyridin-1-one | LCMS Method J m/z = 460.8 [M + H]+, Ret. time = 2.79 min Chiral HPLC method X2: Ret. time = 10.96 + 15.96 | 1H NMR (400 MHz, DMSO-d6) δ 9.97-9.79 (m, 2H), 9.42 (s, 1H), 9.27 (s, 1H), 8.08-8.05 (d, J = 13.9 Hz, 2H), 7.74-7.72 (d, J = 9.1 Hz, 1H), 7.51-7.33 (m, 2H), 5.45 (d, J = 5.0 Hz, 2H), 4.76 (s, 2H), 4.44 (d, J = 51.0 Hz, 1H), 3.63 (d, J = 46.9 Hz, 3H), 2.86-2.81 (t, J = 11.8 Hz, 1H), 2.74-2.60 (m, 1H), 2.13 (s, 1H), 1.75 (t, J = 10.9 Hz, 1H). | Alp & Q AA49 BB26 |
| I-601 | 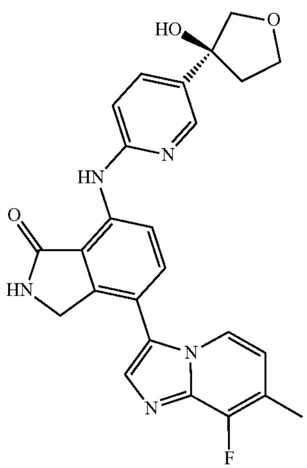 [SMILES: Cc1ccn2c(-c3ccc(Nc4ccc([C@@]5(O)CCOC5)cn4)c4c3CNC4=O)cnc2c1F] | (S)-4-(8-fluoro-7-methyl-imidazo[1,2-a]pyridin-3-yl)-7-((5-(3-hydroxytetra-hydrofuran-3-yl)pyridin-2-yl)amino)iso-indolin-1-one | LCMS Method J m/z = 460.8 [M + H]+, Ret. time = 2.74 min Chiral HPLC method X10: Ret. time = 10.05 | 1H NMR (400 MHz, DMSO-d6) δ 10.12 (s, 1H), 8.86 (s, 1H), 8.74-8.72 (d, J = 8.4 Hz, 1H), 8.43-8.42 (d, J = 2.4 Hz, 1H), 8.18-8.17 (d, J = 7.2 Hz, 1H), 7.82-7.81 (m, 2H), 7.75-7.73 (d, J = 8.4 Hz, 1H), 7.03-7.01 (d, J = 8.4 Hz, 1H), 6.86-6.83 (t, J = 6.4 Hz, 1H), 5.49 (s, 1H), 4.41 (s, 2H), 4.07-3.99 (m, 2H), 3.85-3.83 (d, J = 9.2 Hz, 1H), 3.77-3.75 (d, J = 8.8 Hz, 1H), 2.34 (s, 3H), 2.19-2.17 (m, 1H), 2.16-2.13 (m, 1H). | ACp AA99 BB80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-602 | 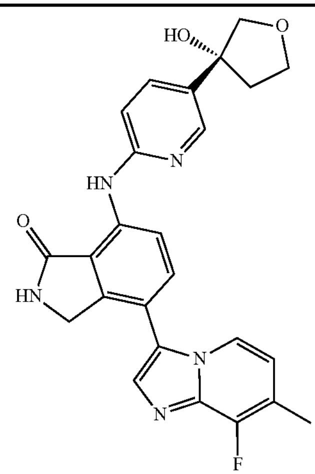 | (R)-4-(8-fluoro-7-methyl-imidazo[1,2-a]pyridin-3-yl)-7-((5-(3-hydroxytetra-hydrofuran-3-yl)pyridin-2-yl)amino)iso-indolin-1-one | LCMS Method J m/z = 460.9 [M + H]+, Ret. time = 2.74 min Chiral HPLC method X10: Ret. time = 7.52 | 1H NMR (400 MHz, DMSO-d6) δ 10.12 (s, 1H), 8.86 (s, 1H), 8.74-8.72 (d, J = 8.6 Hz, 1H), 8.43-8.42 (d, J = 2.4 Hz, 1H), 8.18-8.17 (d, J = 6.9 Hz, 1H), 7.82-7.78 (m, 2H), 7.75-7.73 (d, J = 8.6 Hz, 1H), 7.03-7.01 (d, J = 8.4 Hz, 1H) 6.86-6.83 (t, J = 6.4 Hz, 1H), 5.49 (s, 1H), 4.41 (s, 2H), 4.07-3.99 (m, 2H), 3.85-3.83 (d, J = 9.2 Hz, 1H), 3.77-3.75 (d, J = 8.8 Hz, 1H), 2.34 (s, 3H), 2.19-2.17 (m, 1H), 2.16-2.13 (m, 1H). | ACp AA99 BB80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-603 | 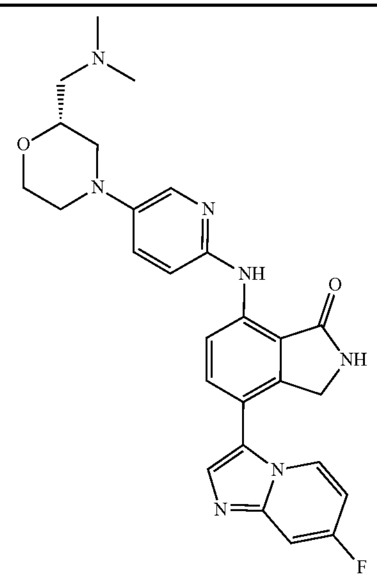 | (R)-7-((5-(2-((dimethyl-amino)methyl)mor-pholino)pyridin-2-yl)amino)-4-(7-fluoro imidazo[1,2-a]pyridin-3-yl)isoindolin-1-one | LCMS Method J m/z = 502.8 [M + H]+, Ret. time = 2.43 min Chiral HPLC method X3: Ret. time = 6.74 | 1H NMR (400 MHz, DMSO-d6) δ 9.88 (s, 1H), 8.79 (s, 1H), 8.58-8.56 (d, J = 8.6 Hz, 1H), 8.43-8.41 (t, J = 5.7 Hz, 1H), 8.01-8.00 (d, J = 3.0 Hz, 1H), 7.82 (s, 1H), 7.71-7.69 (d, J = 8.6 Hz, 1H), 7.55-7.52 (ddd, J = 29.7, 9.5, 2.9 Hz, 2H), 7.00-6.98 (m, 2H), 4.39 (s, 2H), 4.01-3.89 (m, 1H), 3.70 (dddd, J = 19.4, 14.1 9.9, 4.2 Hz, 2H), 3.53 (d, J = 11.5 Hz, 1H), 3.46 (d, J = 11.5 Hz, 2H), 2.38 (td, J = 6.5, 6.0, 3.8 Hz, 2H), 2.21 (s, 6H), 1.25 (s, 1H). | G AA63 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-604 | 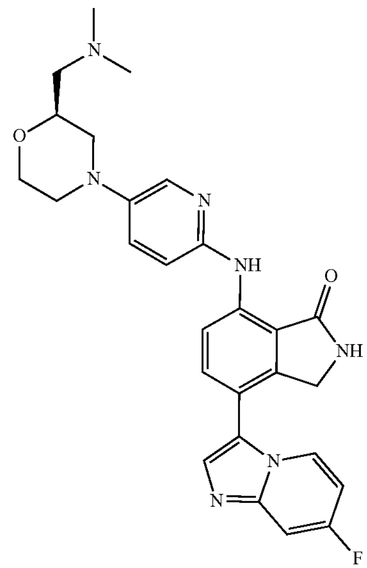 [SMILES: CN(C)C[C@H]1CN(c2ccc(Nc3ccc(-c4cnc5cc(F)ccn45)c4c3C(=O)NC4)nc2)CCO1] | (S)-7-((5-(2-((dimethylamino)methyl)morpholino)pyridin-2-yl)amino)-4-(7-fluoroimidazo[1,2-a]pyridin-3-yl)isoindolin-1-one | LCMS Method J m/z = 502.8 [M + H]+, Ret. time = 2.43 min Chiral HPLC method X3: Ret. time = 6.7 | 1H NMR (400 MHz, DMSO-d6) δ 9.88 (s, 1H), 8.79 (s, 1H), 8.58-8.56 (d, J = 8.6 Hz, 1H), 8.45-8.41 (t, J = 6.6 Hz, 1H), 8.01-8.00 (d, J = 3.0 Hz, 1H), 7.82 (s, 1H), 7.71-7.69 (d, J = 8.6 Hz, 1H), 7.55-7.52 (ddd, J = 29.7, 9.5, 2.9 Hz, 2H), 7.00-6.98 (m, 2H), 4.39 (s, 2H), 4.01-3.89 (m, 1H), 3.70 (dddd, J = 19.4, 14.1, 9.9, 4.2 Hz, 2H), 3.53 (d, J = 11.5 Hz, 1H), 3.46 (d, J = 11.5 Hz, 2H), 2.38 (td, J = 6.5, 6.0, 3.8 Hz, 2H), 2.21 (s, 6H), 1.25 (s, 1H). | G AA63 BB63 |
| I-605 | 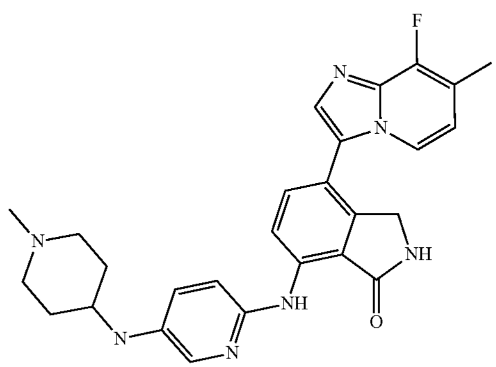 | 4-(8-fluoro-7-methylimidazo[1,2-a]pyridin-3-yl)-7-((4-methylpiperazin-1-yl)methyl)pyridin-2-yl)amino)isoindolin-1-one | LCMS Method J m/z = 486.2 [M + H]+, Ret. time = 2.49 min | 1H NMR (400 MHz, DMSO-d6) δ 10.11 (s, 1H), 8.86 (s, 1H), 8.73-8.71 (d, J = 8.6 Hz, 1H), 8.27-8.12 (m, 2H), 7.83 (s, 1H), 7.75-7.72 (d, J = 8.5 Hz, 1H), 7.64-7.63 (dd, J = 8.4, 2.4 Hz, 1H), 7.01 (d, J = 8.4 Hz, 1H), 6.86-6.83 (t, J = 6.7 Hz, 1H), 4.41 (s, 2H), 3.37 (bs, 4H), 2.42 (bs, 4H), 2.34 (s, 4H), 2.22 (s, 3H), 1.24 (bs, 1H). | ACp AA108 BB80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-606 | 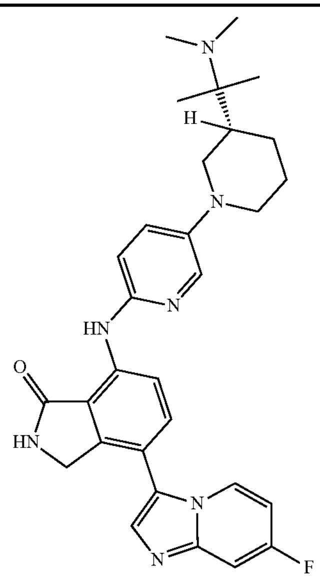 | (R)-7-((5-(3-(dimethylamino)propan-1-yl)piperidin-1-yl)pyridin-2-yl)amino)-4-(7-fluoroimidazo[1,2-a]pyridin-3-yl)isoindolin-1-one | LCMS Method J m/z = 528.5 [M + H]+, Ret. time = 2.96 min Chiral HPLC method X1: Ret. time = 18.93 | 1H NMR (400 MHz, DMSO-d6) δ 9.83 (s, 1H), 8.78 (s, 1H), 8.57-8.55 (d, J = 8.5 Hz, 1H), 8.44-8.40 (dd, J = 7.7, 5.7 Hz, 1H), 7.99-7.98 (d, J = 3.0 Hz, 1H), 7.82 (s, 1H), 7.70-7.67 (d, J = 8.6 Hz, 1H), 7.54-7.51 (dd, J = 10.1, 2.7 Hz, 1H), 7.40-7.37 (dd, J = 8.9, 3.0 Hz, 1H), 6.95 (td, J = 8.8, 8.1, 3.3 Hz, 2H), 4.38 (s, 2H), 3.75-3.72 (d, J = 11.7 Hz, 1H), 3.62-3.59 (m, 1H), 2.38-2.33 (m, 2H), 2.16 (s, 1H), 1.83-1.77 (dt, J = 17.2, 12.1 Hz, 3H), 1.62 (bs, 2H), 1.24 (s, 3H), 1.14-1.12 (d, J = 13.1, 6.7 Hz, 2H), 0.94 (s, 3H), 0.87 (s, 3H). | G AA103 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-607 | 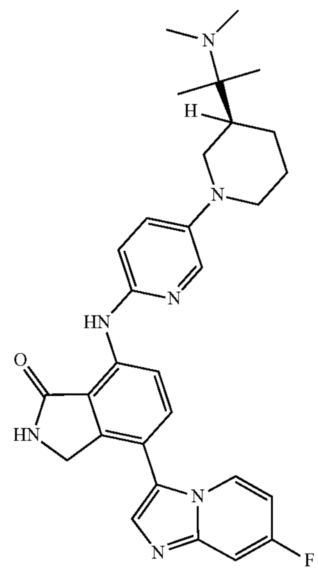 [SMILES: CN(C)C(C)(C)[C@H]1CCCN(c2ccc(Nc3ccc(-c4cnc5cc(F)ccn45)c4c3C(=O)NC4)nc2)C1] | (S)-7-((5-(3-(2-(dimethyl-amino)propan-2-yl)piperidin-1-yl)pyridin-2-yl)amino)-4-(7-fluoro-imidazo[1,2-a]pyridin-3-yl)isoindolin-1-one | LCMS Method J m/z = 528.5 [M + H]+, Ret. time = 2.55 min Chiral HPLC method X1: Ret. time = 20.97 | 1H NMR (400 MHz, DMSO-d6) δ 9.83 (s, 1H), 8.78 (s, 1H), 8.57-8.55 (d, J = 8.5 Hz, 1H), 8.44-8.40 (dd, J = 7.7, 5.7 Hz, 1H), 7.99-7.98 (d, J = 3.0 Hz, 1H), 7.82 (s, 1H), 7.70-7.67 (d, J = 8.6 Hz, 1H), 7.54-7.51 (dd, J = 10.1, 2.7 Hz, 1H), 7.40-7.37 (dd, J = 8.9, 3.0 Hz, 1H), 6.95 (td, J = 8.8, 8.1, 3.3 Hz, 2H), 4.38 (s, 2H), 3.75-3.72 (d, J = 11.7 Hz, 1H), 3.62-3.59 (m, 1H), 2.38-2.33 (m, 2H), 2.16 (s, 1H), 1.83-1.77 (dt, J = 17.2, 12.1 Hz, 3H), 1.62 (bs, 2H), 1.24 (s, 3H), 1.14-1.12 (d, J = 13.1, 6.7 Hz, 2H), 0.94 (s, 3H), 0.87 (s, 3H). | G AA103 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-608 | 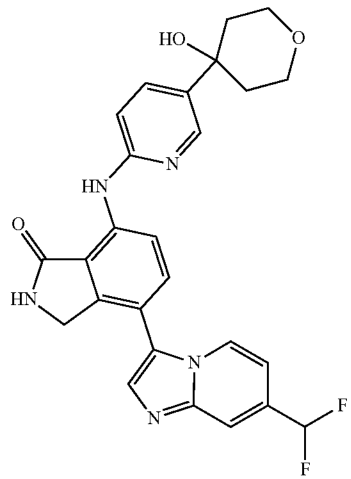 [SMILES: O=C1NCc2c(-c3cnc4cc(C(F)F)ccn34)ccc(Nc3ccc(C4(O)CCOCC4)cn3)c21] | 4-(7-(difluoro-methyl)imidazo[1,2-a]pyridin-3-yl)-7-((5-(4-hydroxytetrahydro-2H-pyran-4-yl)pyridin-2-yl)amino)isoindolin-1-one | LCMS Method J m/z = 492.8 [M + H]+, Ret. time = 2.85 min | 1H NMR (400 MHz, DMSO-d6) δ 10.11 (s, 1H), 8.87 (s, 1H), 8.76-8.74 (d, J = 8.6 Hz, 1H), 8.54-8.52 (d, J = 7.2 Hz, 1H), 8.43 (d, J = 2.4 Hz, 1H), 8.01 (s, 1H), 7.95 (q, J = 1.5 Hz, 1H), 7.86-7.73 (m, 2H), 7.09 (dd, J = 7.3, 1.8 Hz, 1H), 7.05-6.97 (m, 1H), 5.15 (s, 1H), 4.43 (s, 2H), 3.81 (td, J = 11.4, 2.0 Hz, 2H), 3.77-3.65 (m, 3H), 2.00 (td, J = 12.8, 5.1 Hz, 2H), 1.67-1.55 (m, 2H). | ACp AA57 BB84 |
| I-609 | 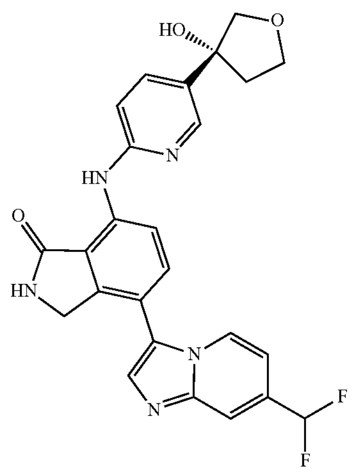 [SMILES: O=C1NCc2c(-c3cnc4cc(C(F)F)ccn34)ccc(Nc3ccc([C@]4(O)CCOC4)cn3)c21] | (R)-4-(7-(difluoro-methyl)imidazo[1,2-a]pyridin-3-yl)-7-((5-(3-hydroxytetrahydrofuran-3-yl)pyridin-2-yl)amino)isoindolin-1-one | LCMS Method J m/z = 478.8 [M + H]+, Ret. time = 2.81 min Chiral HPLC method X6: Ret. time = 11.12 | 1H NMR (400 MHz, DMSO-d6) δ 10.13 (s, 1H), 8.74 (d, J = 8.5 Hz, 1H), 8.53 (d, J = 7.2 Hz, 1H), 8.43 (s, 1H), 7.97 (d, J = 23.3 Hz, 2H), 7.80 (dd, J = 8.4, 3.9 Hz, 2H), 7.19-6.96 (m, 3H), 5.49 (s, 1H), 4.42 (s, 2H), 4.00-4.04 (dq, J = 9.6, 5.7, 3.6 Hz, 2H), 3.89-3.70 (m, 2H), 2.27 (s, 2H), 2.17 (s, 1H). | ACp AA99 BB84 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-610 | 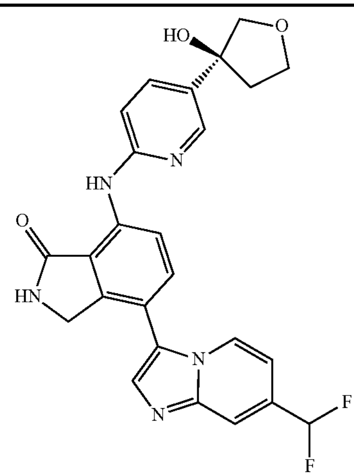 | (S)-4-(7-(difluoromethyl)imidazo[1,2-a]pyridin-3-yl)-7-((5-(3-hydroxytetrahydrofuran-3-yl)pyridin-2-yl)amino)isoindolin-1-one | LCMS Method J m/z = 478.2 [M + H]+, Ret. time = 3.21 min Chiral HPLC method X6: Ret. time = 11.71 | 1H NMR (400 MHz, DMSO-d6) δ 10.13 (s, 1H), 8.88 (s, 1H), 8.76-8.73 (d, J = 8.6 Hz, 1H), 8.54-8.52 (d, J = 7.1 Hz, 1H), 8.44-8.43 (d, J = 2.5 Hz, 1H), 8.01 (s, 1H), 7.95 (s, 1H), 7.86-7.73 (m, 2H), 7.14-7.08 (s, 1H), 7.03-7.01 (s, 1H), 5.49 (s, 1H), 4.42 (s, 2H), 4.00-4.04 (dq, J = 9.6, 5.7, 3.6 Hz, 2H), 3.89-3.70 (m, 2H), 2.27 (s, 2H), 2.17 (s, 1H). | ACp AA99 BB84 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-611 | 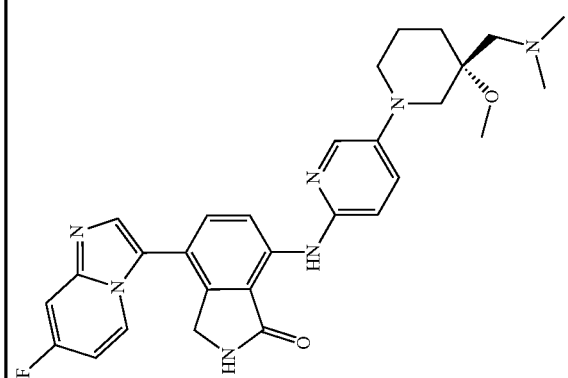 | (R)-7-((5-(3-((dimethylamino)methyl)-3-methoxypiperidin-1-yl)pyridin-2-yl)amino)-4-(7-fluoroimidazo[1,2-a]pyridin-3-yl)isoindolin-1-one | LCMS Method J m/z = 530.8 [M + H]+, Ret. time = 2.57 min Chiral HPLC method XL Ret. time = 17.47 | 1H NMR (400 MHz, DMSO-d6) δ 9.84 (s, 1H), 8.78 (s, 1H), 8.57-8.55 (d, J = 8.4 Hz, 1H), 8.44-8.41 (d, J = 6.4 Hz, 1H), 8.00 (bs, 1H), 7.81 (bs, 1H), 7.70-7.68 (d, J = 8.4 Hz, 1H), 7.54-7.52 (d, J = 9.6 Hz, 1H), 7.44-7.42 (d, J = 8 Hz, 1H), 6.97-6.95 (t, J = 9.2 Hz, 2H), 4.38 (bs, 2H), 3.23 (bs, 3H), 3.04 (bs, 3H), 2.85-2.82 (m, 4H), 1.78 (bs, 3H), 1.57 (bs, 4H), 1.24 (bs, 2H). | G AA109 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-612 | 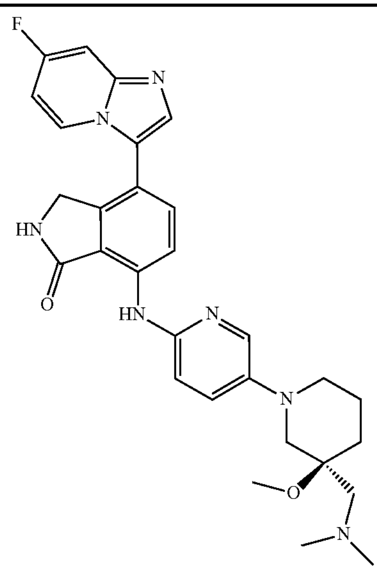 | (S)-7-(5-((3-(dimethylamino)methyl)-3-methoxy-piperidin-1-yl)pyridin-2-yl)amino)-4-(7-fluoro-imidazo[1,2-a]pyridin-3-yl)isoindolin-1-one | LCMS Method J m/z = 530.9 [M + H]+, Ret. time = 2.57 min Chiral HPLC method X1: Ret. time = 20.29 | 1H NMR (400 MHz, DMSO-d6) δ 9.84 (s, 1H), 8.78 (s, 1H), 8.57-8.55 (d, J = 8.4 Hz, 1H), 8.44-8.41 (d, J = 6.4 Hz, 1H), 8.00 (bs, 1H), 7.81 (bs, 1H), 7.70-7.68 (d, J = 8.4 Hz, 1H), 7.54-7.52 (d, J = 9.6 Hz, 1H), 7.44-7.42 (d, J = 8 Hz, 1H), 6.97-6.95 (t, J = 9.2 Hz, 2H), 4.38 (bs, 2H), 3.23 (bs, 3H), 3.04 (bs, 3H), 2.85-2.82 (m, 4H), 1.78 (bs, 3H), 1.57 (bs, 4H), 1.24 (bs, 2H). | G AA109 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-613 | (structure) | (S)-7-((5-((2-(dimethylamino)methyl)morpholino)pyridin-2-yl)amino)-4-(8-fluoro-7-methylimidazo[1,2-a]pyridin-3-yl)isoindolin-1-one | LCMS Method J m/z = 516.3 [M + H]+, Ret. time = 2.94 min Chiral HPLC method X4: Ret. time = 8.25 | 1H NMR (400 MHz, DMSO-d6) δ 9.89 (s, 1H), 8.81 (s, 1H), 8.58 (d, J = 8.5 Hz, 1H), 8.16 (d, J = 7.0 Hz, 1H), 8.01 (d, J = 3.0 Hz, 1H), 7.81 (s, 1H), 7.69 (d, J = 8.6 Hz, 1H), 7.46 (dd, J = 9.0, 3.0 Hz, 1H), 7.00 (d, J = 9.0 Hz, 1H), 6.84 (t, J = 6.7 Hz, 1H), 4.39 (s, 2H), 3.96-3.93 (m, 1H), 3.71-3.65 (m, 2H), 3.54-3.44 (m, 2H), 2.72-2.68 (m, 2H), 2.41 (s, 2H), 2.34 (bs, 3H), 2.23 (s, 6H). | G AA63 BB80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-614 | 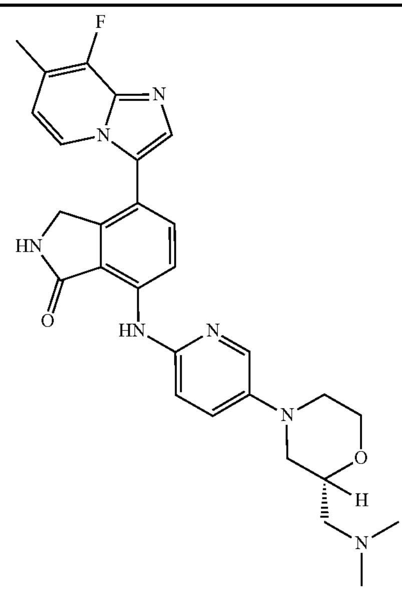 | (R)-7-((5-(2-((dimethylamino)methyl)morpholino)pyridin-2-yl)amino)-4-(8-fluoro-7-methylimidazo[1,2-a]pyridin-3-yl)isoindolin-1-one | LCMS Method J m/z = 516.2 [M + H]+, Ret. time = 2.93 min Chiral HPLC method X4: Ret. time = 11.07 | 1H NMR (400 MHz, DMSO-d6) δ 9.88 (s, 1H), 8.80 (s, 1H), 8.58-8.56 (d, J = 8.5 Hz, 1H), 8.16-8.14 (d, J = 7.0 Hz, 1H), 8.01-8.00 (d, J = 3.0 Hz, 1H), 7.80 (s, 1H), 7.69-7.67 (d, J = 8.6 Hz, 1H), 7.47-7.44 (dd, J = 9.0, 3.0 Hz, 1H), 7.00 (d, J = 9.0 Hz, 1H), 6.84 (t, J = 6.7 Hz, 1H), 4.39 (s, 2H), 3.96-3.93 (m, 1H), 3.71-3.65 (m, 2H), 3.54-3.44 (m, 2H) 2.72-2.68 (m, 2H), 2.41 (s, 2H), 2.34 (bs, 3H), 2.23 (s, 6H). | G AA63 BB80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-615 | 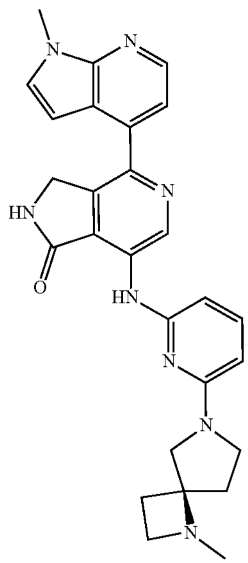 [SMILES: CN1CC[C@]12CCN(c1cccc(Nc3cnc(-c4ccnc5c4ccn5C)c4c3C(=O)NC4)n1)C2] | (R)-7-((6-(1-methyl-1,6-diazaspiro[3.4]octan-6-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 481.2 [M + H]+, Ret. time = 3.35 min Chiral HPLC method X9: Ret. time = 11.33 | 1H NMR (400 MHz, DMSO-d6) δ 10.09 (s, 1H), 9.59 (s, 1H), 9.20 (s, 1H), 8.36-8.34 (d, J = 5.0 Hz, 1H), 7.59-7.58 (d, J = 3.5 Hz, 1H), 7.47-7.43 (t, J = 8 Hz, 1H), 7.38-7.37 (d, J = 4.8 Hz, 1H), 6.85-6.84 (d, J = 2.8 Hz 1H), 6.19-6.17 (d, J = 7.6 Hz, 1H), 6.03-6.01 (d, J = 8.4 Hz, 1H), 4.68 (s, 2H), 3.87 (s, 3H), 3.63-3.60 (d, J = 25.0 Hz, 2H), 3.47-3.44 (d, J = 9.5 Hz, 2H), 3.24 (s, 1H), 3.10 (s, 1H), 2.22 (s, 4H), 2.09 (s, 3H). | Zp AA110 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-616 | 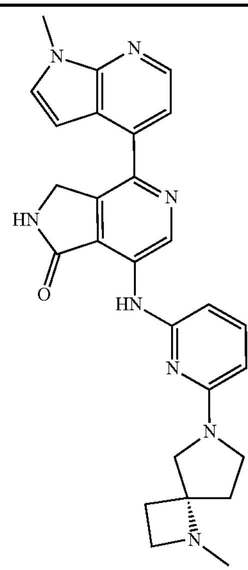 | (S)-7-((6-(1-methyl-1,6-diazaspiro[3.4]octan-6-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 481.2 [M + H]+, Ret. time = 3.35 min Chiral HPLC method X9: Ret. time = 13.73 | 1H NMR (400 MHz, DMSO-d6) δ 10.09 (s, 1H), 9.59 (s, 1H), 9.20 (s, 1H), 8.36-8.34 (d, J = 5.0 Hz, 1H), 7.59-7.58 (d, J = 3.4 Hz, 1H), 7.47-7.43 (t, J = 8 Hz, 1H), 7.38-7.37 (d, J = 4.8 Hz, 1H), 6.85-6.84 (d, J = 2.8 Hz 1H), 6.19-6.17 (d, J = 7.6 Hz, 1H), 6.03-6.01 (d, J = 8.4 Hz, 1H), 4.68 (s, 2H), 3.87 (s, 3H), 3.63-3.60 (d, J = 25.0 Hz, 2H), 3.47-3.44 (d, J = 9.5 Hz, 2H), 3.24 (s, 1H), 3.10 (s, 1H), 2.22 (s, 4H), 2.09 (s, 3H). | Zp AA110 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-617 | 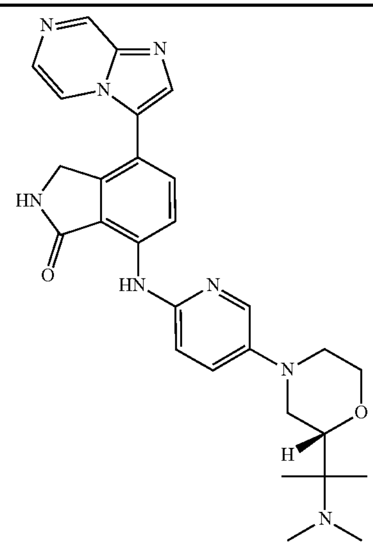 | (S)-7-((5-(2-(2-(dimethylamino)propan-2-yl)morpholino)pyridin-2-yl)amino)-4-(imidazo[1,2-a]pyrazin-3-yl)isoindolin-1-one | LCMS Method J m/z = 513.5 [M + H]+, Ret. time = 2.58 min Chiral HPLC method X6: Ret. time = 15.73 | 1H NMR (400 MHz, DMSO-d6) δ 9.92 (s, 1H), 9.15 (s, 1H), 8.84 (s, 1H), 8.62-8.60 (d, J = 8.6 Hz, 1H), 8.47-8.46 (dd, J = 4.7, 1.5 Hz, 1H), 8.12 (s, 1H), 8.02-8.01 (d, J = 3.0 Hz, 1H), 7.93-7.91 (d, J = 4.7 Hz, 1H), 7.78-7.76 (d, J = 8.6 Hz, 1H), 7.46-7.43 (dd, J = 8.9, 3.1 Hz, 1H), 7.01-6.99 (m, 1H), 4.44 (s, 2H), 4.03-4.01 (dd, J = 11.0, 3.2 Hz, 1H), 3.74-3.63 (m, 1H), 3.58 (t, J = 13.1 Hz, 2H), 3.46 (d, J = 11.6 Hz, 1H), 2.70-2.67 (t, J = 11.7, 3.4 Hz, 1H), 2.51 (s, 1H), 2.20 (s, 6H), 1.01 (d, J = 18.6 Hz, 6H). | G AA93 BB61 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-618 | 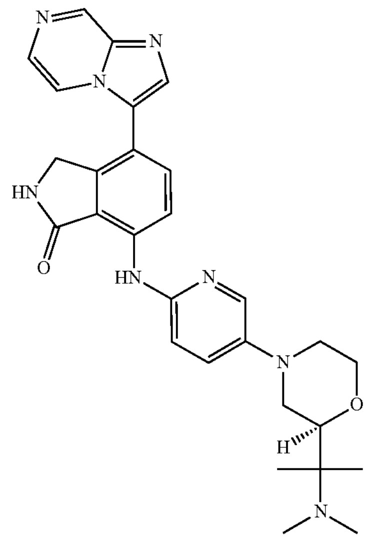 [SMILES: CN(C)C(C)(C)[C@H]1CN(c2ccc(Nc3ccc(-c4cnc5cnccn45)c4c3C(=O)NC4)nc2)CCO1] | (R)-7-((5-(2-(2-(dimethyl-amino)propan-2-yl)morpho-lino)pyridin-2-yl)amino)-4-(imidazo[1,2-a]pyrazin-3-yl)isoindolin-1-one | LCMS Method J m/z = 513.5 [M + H]+, Ret. time = 2.57 min Chiral HPLC method X6: Ret. time = 16.06 | 1H NMR (400 MHz, DMSO-d6) δ 9.92 (s, 1H), 9.15 (s, 1H), 8.84 (s, 1H), 8.62-8.60 (d, J = 8.6 Hz, 1H), 8.47-8.46 (dd, J = 4.7, 1.5 Hz, 1H), 8.12 (s, 1H), 8.02-8.01 (d, J = 3.0 Hz, 1H), 7.93-7.91 (d, J = 4.7 Hz, 1H), 7.78-7.76 (d, J = 8.6 Hz, 1H), 7.46-7.43 (dd, J = 8.9, 3.1 Hz, 1H), 7.01-6.99 (m, 1H), 4.44 (s, 2H), 4.03-4.01 (dd, J = 11.0, 3.2 Hz, 1H), 3.74-3.63 (m, 1H), 3.58 (t, J = 13.1 Hz, 2H), 3.46 (d, J = 11.6 Hz, 1H), 2.70-2.67 (t, J = 11.7, 3.4 Hz, 1H), 2.51 (s, 1H), 2.19 (s, 6H), 1.03-0.98 (d, J = 18.6 Hz, 6H). | G AA93 BB61 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-619 | 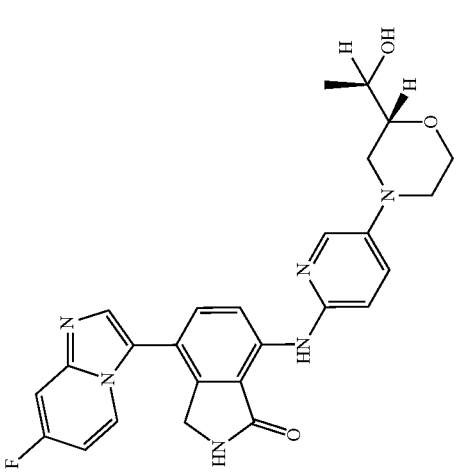 | 4-(7-fluoro-imidazo[1,2-a]pyridin-3-yl)-7-((5-((R)-2-((R)-1-hydroxy-ethyl)morpho-lino)pyridin-2-yl)amino)iso-indolin-1-one | LCMS Method J m/z = 489.9 [M + H]+, Ret. time = 2.65 min Chiral HPLC method X6: Ret. time = 13.35 | 1H NMR (400 MHz, DMSO-d6) δ 9.88 (s, 1H), 8.79 (s, 1H), 8.58-8.56 (d, J = 8.5 Hz, 1H), 8.45-8.41 (t, J = 6.6 Hz, 1H), 8.01-8.00 (d, J = 3.0 Hz, 1H), 7.82 (s, 1H), 7.71-7.69 (d, J = 8.5 Hz, 1H), 7.55-7.54 (dd, J = 31.9, 9.5, 2.9 Hz, 2H), 7.01-6.96 (t, J = 6.7 Hz, 2H), 4.81 (d, J = 5.4 Hz, 1H), 4.39 (s, 2H), 4.03-3.92 (m, 1H), 3.66 (td, J = 11.2, 2.4 Hz, 2H), 3.57 (p, J = 6.2 Hz, 2H), 3.46 (d, J = 11.8 Hz, 1H), 3.30 (ddd, J = 9.8, 6.7, 2.3 Hz, 1H), 2.69 (td, J = 11.7, 3.4 Hz, 1H), 2.45 (d, J = 10.9 Hz, 1H), 1.16 (d, J = 6.2 Hz, 3H). | AEp AA111 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-620 | 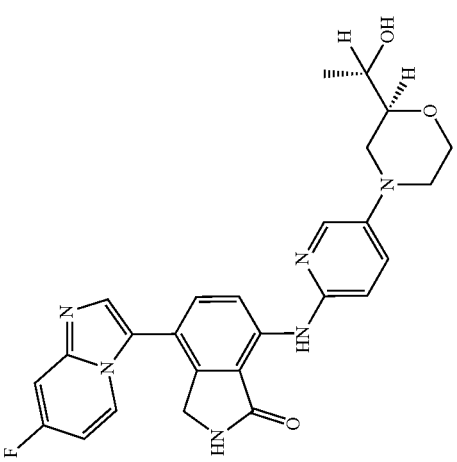 | 4-(7-fluoro-imidazo[1,2-a]pyridin-3-yl)-7-((5-((S)-2-((S)-1-hydroxyethyl)morpholino)pyridin-2-yl)amino)isoindolin-1-one | LCMS Method J m/z = 489.1 [M + H]+, Ret. time = 2.65 min Chiral HPLC method X6: Ret. time = 13.11 | 1H NMR (400 MHz, DMSO-d6) δ 9.88 (s, 1H), 8.79 (s, 1H), 8.58-8.56 (d, J = 8.5 Hz, 1H), 8.45-8.41 (t, J = 6.7 Hz, 1H), 8.01-8.00 (d, J = 3.0 Hz, 1H), 7.82 (s, 1H), 7.71-7.69 (d, J = 8.5 Hz, 1H), 7.55-7.44 (ddd, J = 31.9, 9.5, 2.8 Hz, 2H), 7.01-6.96 (t, J = 6.7 Hz, 2H), 4.81 (d, J = 5.4 Hz, 1H), 4.39 (s, 2H), 4.03-3.92 (m, 1H), 3.66 (td, J = 11.2, 2.4 Hz, 2H), 3.57 (p, J = 6.2 Hz, 1H), 3.46 (d, J = 11.8 Hz, 1H), 3.30 (ddd, J = 9.8, 6.7, 2.3 Hz, 1H), 2.69 (td, J = 11.7, 3.4 Hz, 1H), 2.45 (d, J = 10.9 Hz, 1H), 1.16 (d, J = 6.2 Hz, 3H). | AEp AA111 BB63 |
| I-621 | 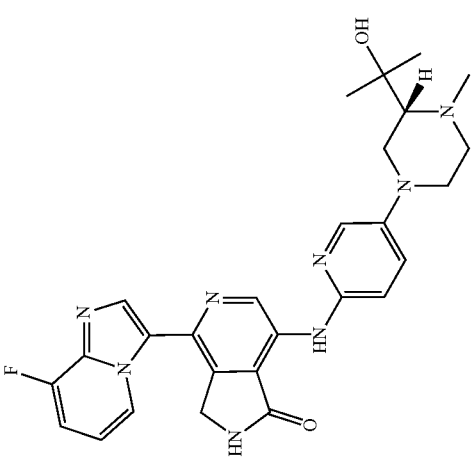 | (R)-4-(8-fluoro-imidazo[1,2-a]pyridin-3-yl)-7-((5-(3-(2-hydroxypropan-2-yl)-4-methylpiperazin-1-yl)pyridin-2-yl)amino)-2,3-dihydro-1H-pyrrolo[3,4-c]pyridin-1-one | LCMS Method C m/z = 517.5 [M + H]+, Ret. time = 1.31 min Chiral HPLC method X10: Ret. time = 7.44 | 1H NMR (400 MHz, DMSO-d6) δ 9.83 (s, 1H), 9.67-9.65 (d, J = 7.0 Hz, 1H), 9.36 (s, 1H), 8.99 (s, 1H), 8.14-7.97 (m, 2H), 7.41-7.39 (t, J = 2.8 Hz, 1H), 7.28-7.23 (t, J = 8 Hz, 1H), 7.04-7.02 (d, J = 8.4 Hz, 2H), 4.74 (s, 2H), 4.09 (s, 1H), 3.42 2.98 (d, J = 12.4 Hz, 3H), 2.82-2.77 (t, J = 10.8 Hz, 1H), 2.65-2.63 (d, J = 8.6 Hz, 1H), 2.49 (s, 3H), 2.41-2.32 (m, 2H), 1.19 (s, 6H). | Zp AA112 BB87 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-622 | 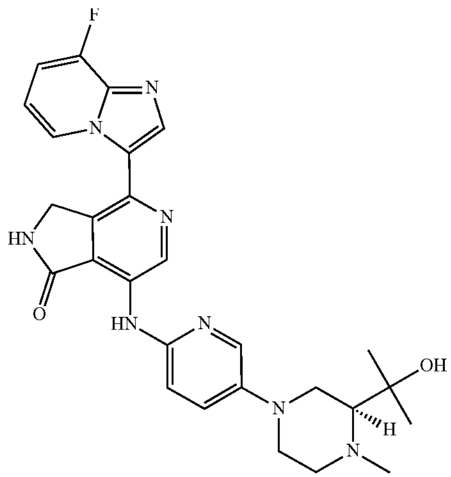 [SMILES: CN1CCN(c2ccc(Nc3cnc(-c4cnc5c(F)cccn45)c4c3C(=O)NC4)nc2)C[C@H]1C(C)(C)O] | (S)-4-(8-fluoro-imidazo[1,2-a]pyridin-3-yl)-7-((5-(3-(2-hydroxypropan-2-yl)-4-methylpiperazin-1-yl)pyridin-2-yl)amino)-2,3-dihydro-1H-pyrrolo[3,4-c]pyridin-1-one | LCMS Method C m/z = 517.02 [M + H]+, Ret. time = 1.29 min Chiral HPLC method X10: Ret. time = 12.14 | 1H NMR (400 MHz, DMSO-d6) δ 9.92 (s, 1H), 9.70-9.68 (d, J = 7.0 Hz, 1H), 9.42 (s, 1H), 8.29 (s, 1H), 8.12-8.02 (m, 2H), 7.45-7.42 (t, J = 2.8 Hz, 1H), 7.35-7.31 (t, J = 8 Hz, 1H), 7.04-7.06-7.04 (d, J = 8.4 Hz, 2H), 4.74 (s, 2H), 4.09 (s, 1H), , 3.42 2.98 (d, J = 12.4 Hz, 3H), 2.82-2.77 (t, J = 10.8 Hz, 1H), 2.65-2.63 (d, J = 8.6 Hz, 1H), 2.49 (s, 3H), 2.41-2.32 (m, 2H), 1.19 (s, 6H). | Zp AA112 BB87 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-623 | 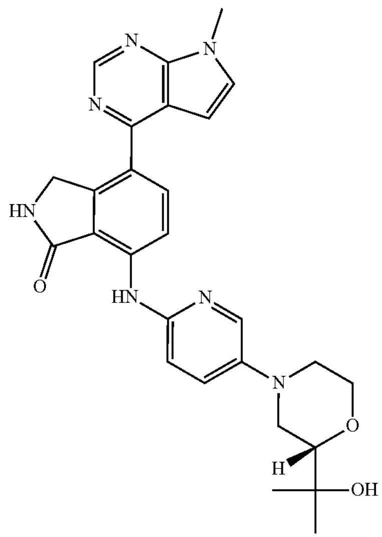 [SMILES: Cn1ccc2c(-c3ccc(Nc4ccc(N5CCO[C@H](C(C)(C)O)C5)cn4)c4c3CNC4=O)ncnc21] | (S)-7-((5-(2-(2-hydroxy-propan-2-yl)morpho-lino)pyridin-2-yl)amino)-4-(7-methyl-7H-pyrrolo[2,3-d]pyrimidin-4-yl)isoindolin-1-one | LCMS Method J m/z = 501.2 [M + 1]+, Ret. time = 3.36 min Chiral HPLC method X10: Ret. time = 7.32 | 1H NMR (400 MHz, DMSO-d6) δ 10.15 (s, 1H), 8.85 (s, 2H), 8.62-8.59 (d, J = 8.8 Hz, 1H), 8.29-8.27 (d, J = 8.7 Hz, 1H), 8.05-8.04 (d, J = 3.0 Hz, 1H), 7.70-7.69 (d, J = 3.6 Hz, 1H), 7.49-7.46 (dd, J = 9.0, 3.0 Hz, 1H), 7.03-6.98 (m, 2H), 4.83 (s, 2H), 4.51 (s, 1H), 4.02 (dd, J = 11.5, 2.9 Hz, 1H), 3.88 (s, 3H), 3.67-3.61 (dt, J = 14.8, 10.4 Hz, 2H), 3.50-3.47 (d, J = 12.0 Hz, 1H), 2.68-2.65 (td, J = 11.8, 3.3 Hz, 1H), 2.51 (s, 1H), 1.25 (s, 1H), 1.19 (s, 3H), 1.13 (s, 3H). | G AA48 BB86 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-624 | 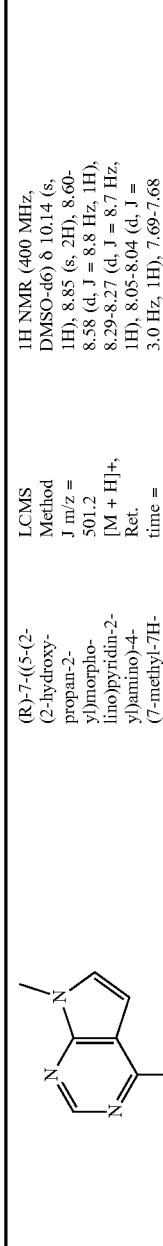 | (R)-7-((5-(2-(2-hydroxypropan-2-yl)morpholino)pyridin-2-yl)amino)-4-(7-methyl-7H-pyrrolo[2,3-d]pyrimidin-4-yl)isoindolin-1-one | LCMS Method J m/z = 501.2 [M + H]+, Ret. time = 3.99 min Chiral HPLC method X10: Ret. time = 99.23 | 1H NMR (400 MHz, DMSO-d6) δ 10.14 (s, 1H), 8.85 (s, 2H), 8.60-8.58 (d, J = 8.8 Hz, 1H), 8.29-8.27 (d, J = 8.7 Hz, 1H), 8.05-8.04 (d, J = 3.0 Hz, 1H), 7.69-7.68 (d, J = 3.6 Hz, 1H), 7.49-7.46 (dd, J = 9.0, 3.0 Hz, 1H), 7.03-6.97 (m, 2H), 4.83 (s, 2H), 4.51 (s, 1H), 4.02 (dd, J = 11.5, 2.9 Hz, 1H), 3.88 (s, 3H), 3.67-3.61 (dt, J = 14.8, 10.4 Hz, 2H), 3.50-3.47 (d, J = 12.0 Hz, 1H), 2.68-2.65 (td, J = 11.8, 3.3 Hz, 1H), 2.51 (s, 1H), 1.25 (s, 1H), 1.19 (s, 3H), 1.13 (s, 3H). | G AA48 BB86 |

TABLE 8-continued
Characterization Data (LCMS and ¹H NMR).
| # | STRUCTURE | NAME | LCMS | ¹H NMR | Method Reagent AA BB |
|---|---|---|---|---|---|
| I-626 | 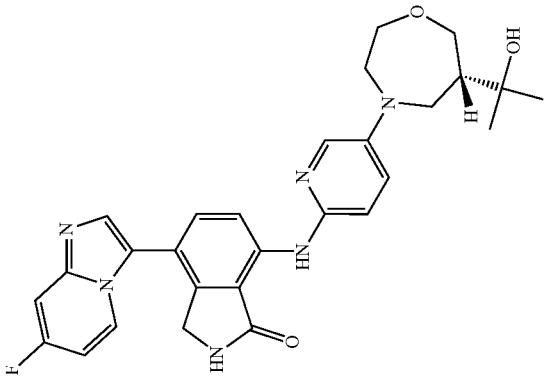 | (R)-4-(7-fluoro-imidazo[1,2-a]pyridin-3-yl)-7-((5-(6-(2-hydroxypropan-2-yl)-1,4-oxazepan-4-yl)pyridin-2-yl)amino)isoindolin-1-one | LCMS Method J m/z = 517.4 [M + H]+, Ret. time = 2.83 min Chiral HPLC method X10: Ret. time = 8.49 | 1H NMR (400 MHz, DMSO-d6) δ 9.70 (s, 1H), 8.72 (s, 1H), 8.54-8.37 (m, 2H), 7.93 (d, J = 3.1 Hz, 1H), 7.80 (s, 1H), 7.66 (d, J = 8.6 Hz, 1H), 7.52 (dd, J = 10.1, 2.7 Hz, 1H), 7.28 (dd, J = 9.1, 3.1 Hz, 1H), 7.04-6.88 (m, 2H), 4.44 (s, 1H), 4.37 (s, 2H), 3.94 (dd, J = 14.8, 5.0 Hz, 1H), 3.81-3.68 (m, 3H), 3.55-3.47 (m, 2H), 3.23-3.14 (m, 1H), 2.14 (dd, J = 11.4, 5.9 Hz, 1H), 1.25 (s, 1H), 1.14 (s, 6H). | G AA113 BB63 |

TABLE 8-continued
Characterization Data (LCMS and ¹H NMR).
| # | STRUCTURE | NAME | LCMS | ¹H NMR | Method Reagent AA BB |
|---|---|---|---|---|---|
| I-627 | 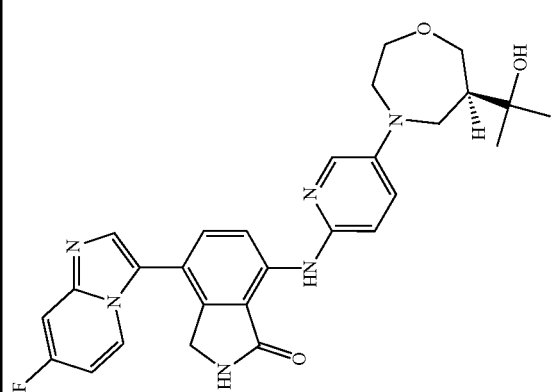 | (S)-4-(7-fluoro-imidazo[1,2-a]pyridin-3-yl)-7-((5-(6-(2-hydroxypropan-2-yl)-1,4-oxazepan-4-yl)pyridin-2-yl)amino)iso-indolin-1-one | LCMS Method J m/z = 517.4 [M + H]+, Ret. time = 2.83 min Chiral HPLC method X10: Ret. time = 11.02 | 1H NMR (400 MHz, DMSO-d6) δ 9.71 (s, 1H), 8.73 (s, 1H), 8.57-8.28 (m, 2H), 7.93 (d, J = 3.1 Hz, 1H), 7.81 (s, 1H), 7.66 (d, J = 8.6 Hz, 1H), 7.53 (dd, J = 10.1, 2.7 Hz, 1H), 7.29 (dd, J = 9.0, 3.2 Hz, 1H), 7.07-6.88 (m, 2H), 4.44 (s, 1H), 4.37 (s, 2H), 3.94 (dd, J = 14.8, 5.0 Hz, 1H), 3.81-3.68 (m, 3H), 3.55-3.47 (m, 2H), 3.23-3.14 (m, 1H), 2.14 (dd, J = 11.4, 5.9 Hz, 1H), 1.25 (s, 1H), 1.14 (s, 6H). | G AA113 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-628 | 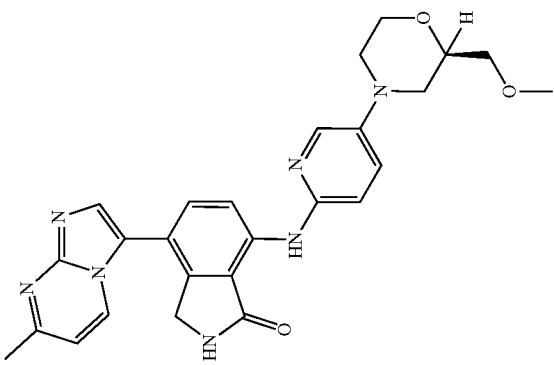 | (R)-7-(5-(2-(methoxymethyl)morpholino)pyridin-2-yl)amino)-4-(7-methylimidazo[1,2-a]pyrimidin-3-yl)isoindolin-1-one | LCMS Method J m/z = 486.2 [M + H]+, Ret. time = 3.19 min Chiral HPLC method X7: Ret. time = 4.45 | 1H NMR (400 MHz, DMSO-d6) δ 9.89 (s, 1H), 8.82 (s, 1H), 8.73 (d, J = 7.2 Hz, 1H), 8.58 (d, J = 8.6 Hz, 1H), 8.01 (d, J = 2.9 Hz, 1H), 7.89 (s, 1H), 7.70 (d, J = 8.6 Hz, 1H), 7.47 (dd, J = 9.0, 3.0 Hz, 1H), 7.06-6.87 (m, 2H), 4.42 (s, 2H), 4.04-3.91 (m, 1H), 3.76 (s, 1H), 3.68 (td, J = 11.4, 2.6 Hz, 1H), 3.52 (d, J = 11.3 Hz, 1H), 3.49-3.39 (m, 3H), 3.31 (d, J = 1.0 Hz, 3H), 2.70 (td, J = 11.6, 3.3 Hz, 1H), 2.58 (s, 3H), 2.47 (d, J = 10.9 Hz, 1H). | G AA39 BB85 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-629 | 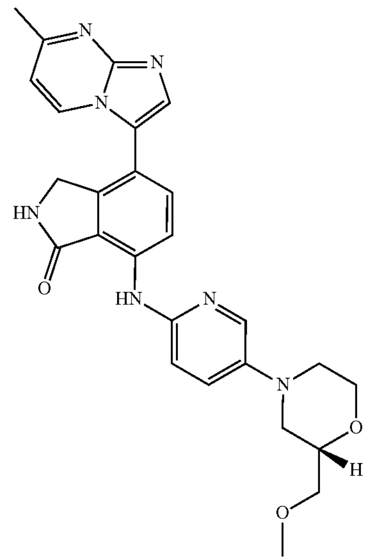 [SMILES: COC[C@@H]1CN(c2ccc(Nc3ccc(-c4cnc5nc(C)ccn45)c4c3C(=O)NC4)nc2)CCO1] | (S)-7-(5-((2-(methoxymethyl)morpholino)pyridin-2-yl)amino)-4-(7-methylimidazo[1,2-a]pyrimidin-3-yl)isoindolin-1-one | LCMS Method J m/z = 486.2 [M + H]+, Ret. time = 3.19 min Chiral HPLC method X7: Ret. time = 4.25 | 1H NMR (400 MHz, DMSO-d6) δ 9.89 (s, 1H), 8.82 (s, 1H), 8.73 (d, J = 7.0 Hz, 1H), 8.58 (d, J = 8.5 Hz, 1H), 8.01 (d, J = 3.0 Hz, 1H), 7.89 (s, 1H), 7.71 (d, J = 8.7 Hz, 1H), 7.47 (dd, J = 9.0, 3.0 Hz, 1H), 7.08-6.94 (m, 2H), 4.42 (s, 2H), 4.02-3.92 (m, 1H), 3.76 (d, J = 9.8 Hz, 1H), 3.68 (td, J = 11.2, 2.5 Hz, 1H), 3.52 (d, J = 11.4 Hz, 1H), 3.45 (dt, J = 10.4, 4.7 Hz, 3H), 3.31 (s, 3H), 2.76-2.67 (m, 1H), 2.58 (s, 3H), 2.47 (d, J = 10.9 Hz, 1H). | G AA39 BB85 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-630 | 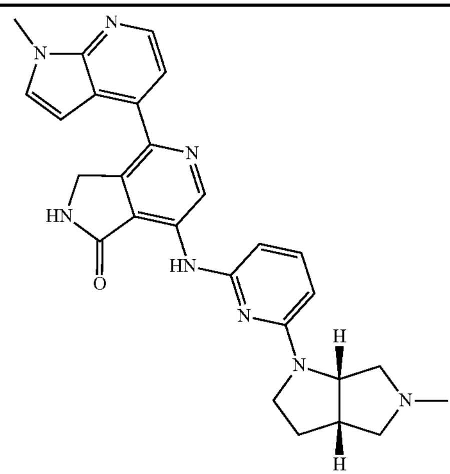 | 4-(1-methyl-1H-pyrrolo[2,3-b]pyridin-4-yl)-7-((6-((3aS,6aS)-5-methylhexahydropyrrolo[3,4-b]pyrrol-1(2H)-yl)pyridin-2-yl)amino)-2,3-dihydro-1H-pyrrolo[3,4-c]pyridin-1-one | LCMS Method J m/z = 481.2 [M + H]+, Ret. time = 3.41 min Chiral HPLC method X10: Ret. time = 5.89 | 1H NMR (400 MHz, DMSO-d6) δ 10.08 (s, 1H), 9.57 (s, 1H), 9.20 (s, 1H), 8.37-8.36 (d, J = 5.0 Hz, 1H), 7.59-7.58 (d, J = 3.5 Hz, 1H), 7.48-7.44 (t, J = 7.9 Hz, 1H), 7.40-7.39 (d, J = 5.0 Hz, 1H), 6.91-6.90 (d, J = 3.4 Hz, 1H), 6.22-6.20 (d, J = 7.7 Hz, 1H), 6.08-6.06 (d, J = 8.2 Hz, 1H), 4.45 (s, 1H), 3.88 (s, 3H), 3.54 (s, 2H), 2.96 (s, 1H), 2.78 (d, J = 9.8 Hz, 1H), 2.58 (dd, J = 9.8, 6.4 Hz, 2H), 2.41 (t, J = 8.0 Hz, 1H), 2.22 (s, 2H), 2.16 (s, 2H), 1.25 (s, 1H). | ADp AA114 BB14 |
| I-631 | 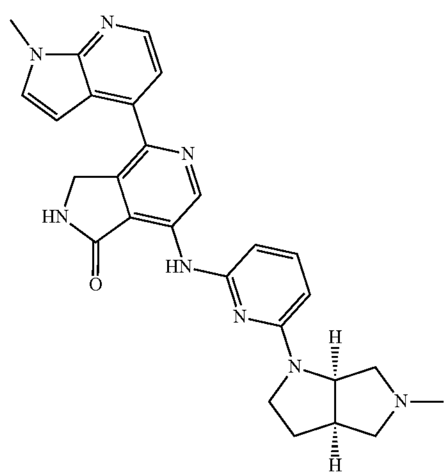 | 4-(1-methyl-1H-pyrrolo[2,3-b]pyridin-4-yl)-7-((6-((3aR,6aR)-5-methylhexahydropyrrolo[3,4-b]pyrrol-1(2H)-yl)pyridin-2-yl)amino)-2,3-dihydro-1H-pyrrolo[3,4-c]pyridin-1-one | LCMS Method J m/z = 481.2 [M + H]+, Ret. time = 3.42 min Chiral HPLC method X10: Ret. time = 6.97 | 1H NMR (400 MHz, DMSO-d6) δ 10.09 (s, 1H), 9.57 (s, 1H), 9.21 (s, 1H), 8.37-8.36 (d, J = 5.0 Hz, 1H), 7.59-7.58 (d, J = 3.5 Hz, 1H), 7.48-7.44 (t, J = 7.9 Hz, 1H), 7.40-7.39 (d, J = 5.0 Hz, 1H), 6.91-6.90 (d, J = 3.4 Hz, 1H), 6.22-6.20 (d, J = 7.7 Hz, 1H), 6.08-6.06 (d, J = 8.2 Hz, 1H), 4.71 (s, 2H), 4.45 (s, 1H), 3.88 (s, 3H), 3.54 (s, 2H), 2.96 (s, 1H), 2.78 (d, J = 9.8 Hz, 1H), 2.58 (dd, J = 9.8, 6.4 Hz, 2H), 2.41 (t, J = 8.0 Hz, 1H), 2.22 (s, 2H), 2.16 (s, 2H), 1.25 (s, 1H). | ADp AA114 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-632 | 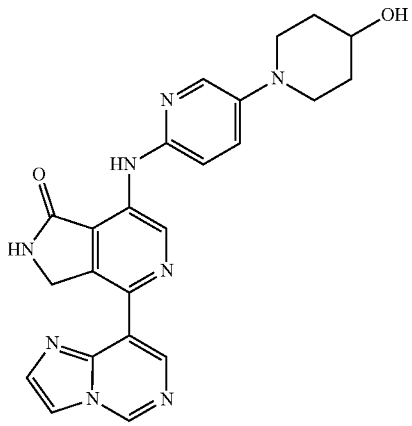 [SMILES: O=C1NCc2c(-c3cncn4ccnc34)ncc(Nc3ccc(N4CCC(O)CC4)cn3)c21] | 7-(5-(4-hydroxy-piperidin-1-yl)pyridin-2-ylamino)-4-(imidazo[1,2-c]pyrimidin-8-yl)-2,3-dihydro-1H-pyrrolo[3,4-c]pyridin-1-one | LCMS Method J m/z = 443.7 [M + H]+, Ret. time = 2.33 min | 1H NMR (400 MHz, DMSO-d6) δ 9.86 (s, 1H), 9.54 (s, 1H), 9.45 (s, 1H), 9.04 (s, 1H), 8.21-8.19 (d, J = 8.2 Hz, 2H), 8.06-8.05 (d, J = 3.0 Hz, 1H), 7.76 (s, 1H), 7.48-7.46 (dd, J = 9.1, 3.1 Hz, 1H), 7.06-7.03 (d, J = 9.0 Hz, 1H), 4.71 (d, J = 4.7 Hz, 3H), 3.66-3.57 (m, 1H), 3.51 (t, J = 5.1 Hz, 2H), 2.95-2.80 (m, 2H), 1.92-1.81 (m, 2H), 1.25 (d, J = 3.6 Hz, 2H). | Alp AA12 BB88 |
| I-633 | 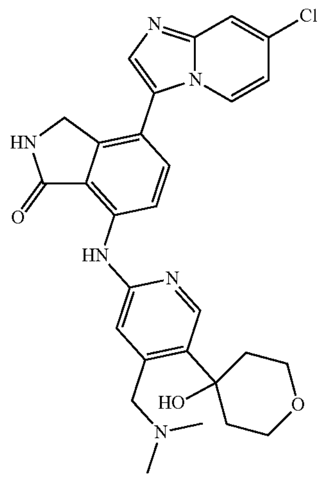 [SMILES: CN(C)Cc1cc(Nc2ccc(-c3cnc4cc(Cl)ccn34)c3c2C(=O)NC3)ncc1C1(O)CCOCC1] | 4-(7-chloro-imidazo[1,2-a]pyridin-3-yl)-7-((4-((dimethyl-amino)methyl)-5-(4-hydroxytetra-hydro-2H-pyran-4-yl)pyridin-2-yl)amino)iso-indolin-1-one | LCMS Method J m/z = 533.2 [M + H]+, Ret. time = 2.99 min | 1H NMR (400 MHz, DMSO-d6) δ 10.13 (s, 1H), 8.91 (s, 1H), 8.80-8.78 (d, J = 8.5 Hz, 1H), 8.43-8.41 (d, J = 7.3 Hz, 1H), 8.30 (s, 1H), 7.90 (s, 1H), 7.86-7.85 (d, J = 2 Hz, 1H), 7.78-7.76 (d, J = 8.4 Hz, 1H), 7.18 (s, 1H), 7.12-6.94 (m, 1H), 4.42 (s, 2H), 3.89-3.84 (t, J = 11.2 Hz, 2H), 3.73 (s, 4H), 2.24 (s, 6H), 2.07-2.00 (m, 2H), 1.82-1.80 (d, J = 12.7 Hz, 2H), 1.12-1.08 (t, J = 6.8 Hz, 1H). | Xp AA115 BB79 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-634 | 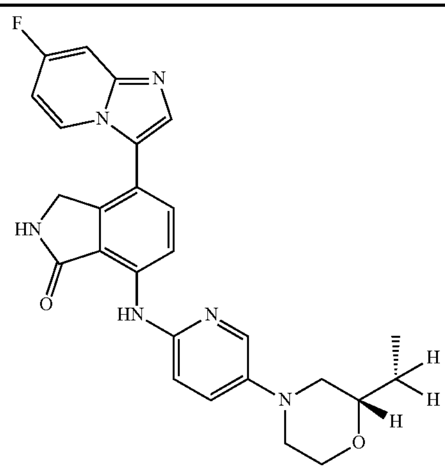 | 4-(7-fluoro-imidazo[1,2-a]pyridin-3-yl)-7-((5-((R)-2-((S)-1-hydroxyethyl)mor-pholino)pyridin-2-yl)amino)iso-indolin-1-one | LCMS Method J m/z = 489.2 [M + H]+, Ret. time = 3.06 min Chiral HPLC method X6: Ret. time = 14.37 | 1H NMR (400 MHz, DMSO-d6) δ 9.87 (s, 1H), 8.79 (s, 1H), 8.58-8.56 (d, J = 8.6 Hz, 1H), 8.44-8.40 (t, J = 6.8 Hz, 1H), 8.02-8.01 (d, J = 3.0 Hz, 1H), 7.81 (s, 1H), 7.70-7.68 (d, J = 8.6 Hz, 1H), 7.54-7.48 (ddd, J = 24.0, 9.5, 2.8 Hz, 2H), 6.99-6.96 (t, J = 8.8 Hz, 2H), 4.67-4.65 (d, J = 5.1 Hz, 1H), 4.38 (s, 2H), 3.99-3.97 (d, J = 10.3 Hz, 1H), 3.67-3.62 (m, 2H), 3.50-3.42 (m, 3H), 2.69-2.60 (m, 2H), 1.12-1.10 (d, J = 6.4 Hz, 3H). | AEp AA111 BB63 |
| I-635 | 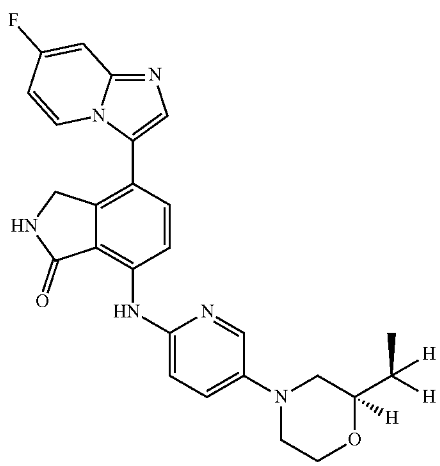 | 4-(7-fluoro-imidazo[1,2-a]pyridin-3-yl)-7-((5-((S)-2-((R)-1-hydroxy-ethyl)morpho-linopyridin-2-yl)amino)iso-indolin-1-one | LCMS Method J m/z = 489.2 [M + H]+, Ret. time = 3.01 min Chiral HPLC method X6: Ret. time = 16.47 | 1H NMR (400 MHz, DMSO-d6) δ 9.87 (s, 1H), 8.79 (s, 1H), 8.58-8.56 (d, J = 8.6 Hz, 1H), 8.44-8.40 (t, J = 6.8 Hz, 1H), 8.02-8.01 (d, J = 3.0 Hz, 1H), 7.81 (s, 1H), 7.70-7.68 (d, J = 8.6 Hz, 1H), 7.54-7.48 (ddd, J = 24.0, 9.5, 2.8 Hz, 2H), 6.99-6.96 (t, J = 8.8 Hz, 2H), 4.67-4.65 (d, J = 5.1 Hz, 1H), 4.38 (s, 2H), 3.99-3.97 (d, J = 10.3 Hz, 1H), 3.67-3.62 (m, 2H), 3.50-3.42 (m, 3H), 2.69-2.60 (m, 2H), 1.12-1.10 (d, J = 6.4 Hz, 3H). | AEp AA111 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-639 | 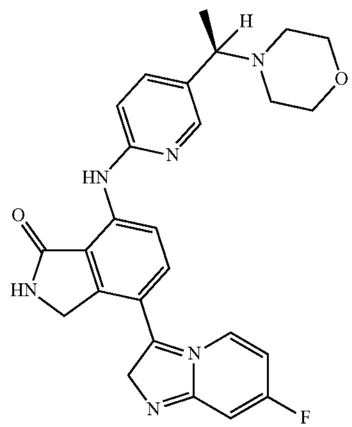 | (R)-4-(7-fluoro-imidazo[1,2-a]pyridin-3-yl)-7-((5-(1-morpholino-ethyl)pyridin-2-yl)amino)isoindolin-1-one | LCMS Method J m/z = 473.2 [M + H]+, Ret. time = 2.71 min Chiral HPLC method X10: Ret. time = 6.82 | 1H NMR (400 MHz, DMSO-d6) δ 10.10 (s, 1H), 8.87 (s, 1H), 8.74-8.72 (d, J = 8.6 Hz, 1H), 8.47-8.43 (m, 1H), 8.22-8.21 (d, J = 2.3 Hz, 1H), 7.84 (s, 1H), 7.76-7.74 (d, J = 8.6 Hz, 1H), 7.67-7.65 (dd, J = 8.4, 2.4 Hz, 1H), 7.56-7.53 (dd, J = 10.1, 2.7 Hz, 1H), 7.05-6.99 (m, 2H), 4.41 (s, 2H), 3.58-3.56 (t, J = 4.6 Hz, 3H), 3.45-3.40 (m, 2H), 2.40 (bs, 1H), 2.34-2.30 (m, 3H), 1.34-1.32 (dd, J = 6.8 Hz, 3H). | Yp AA118 BB63 |
| I-640 | 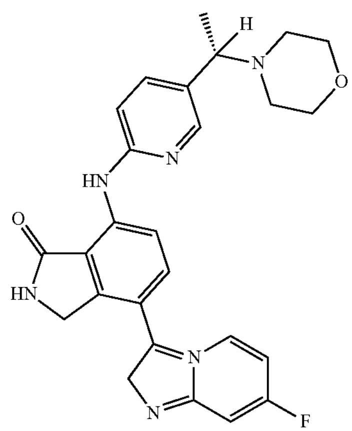 | (S)-4-(7-fluoro-imidazo[1,2-a]pyridin-3-yl)-7-((5-(1-morpholino-ethyl)pyridin-2-yl)amino)isoindolin-1-one | LCMS Method J m/z = 473.2 [M + H]+, Ret. time = 2.69 min Chiral HPLC method X10: Ret. time = 6.65 | 1H NMR (400 MHz, DMSO-d6) δ 10.10 (s, 1H), 8.87 (s, 1H), 8.74-8.72 (d, J = 8.6 Hz, 1H), 8.47-8.43 (m, 1H), 8.22-8.21 (d, J = 2.3 Hz, 1H), 7.84 (s, 1H), 7.76-7.74 (d, J = 8.6 Hz, 1H), 7.67-7.65 (dd, J = 8.4, 2.4 Hz, 1H), 7.56-7.53 (dd, J = 10.1, 2.7 Hz, 1H), 7.05-6.99 (m, 2H), 4.41 (s, 2H), 3.58-3.56 (t, J = 4.6 Hz, 3H), 3.45-3.40 (m, 2H), 2.40 (bs, 1H), 2.34-2.30 (m, 3H), 1.34-1.32 (dd, J = 6.8 Hz, 3H). | Yp AA118 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-641 | 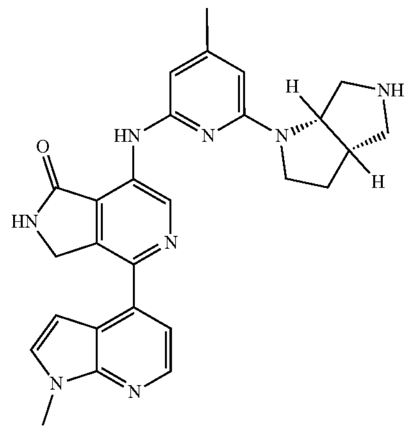 [SMILES: Cc1cc(Nc2cnc(-c3ccnc4c3ccn4C)c3c2C(=O)NC3)nc(N2CC[C@H]3CNC[C@H]32)c1] | 7-((6-((3aS,6aS)-hexahydropyrrolo[3,4-b]pyrrol-1(2H)-yl)-4-methylpyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 481.8 [M + H]+, Ret. time = 3.25 min Chiral HPLC method X13: Ret. time = 7.59 | 1H NMR (400 MHz, DMSO-d6) δ 10.08 (s, 1H), 9.53 (s, 1H), 9.19 (s, 1H), 8.36-8.35 (d, J = 5.0 Hz, 1H), 7.59-7.58 (d, J = 3.5 Hz, 1H), 7.38-7.37 (d, J = 5.0 Hz, 1H), 6.87-6.86 (d, J = 3.4 Hz, 1H), 6.06 (s, 1H), 5.90 (s, 1H), 4.69 (s, 2H), 4.32 (s, 1H), 3.88 (s, 3H), 3.66-3.56 (m, 1H), 3.49 (t, J = 8.2 Hz, 1H), 3.00 (dd, J = 11.8, 5.7 Hz, 1H), 2.95-2.77 (m, 3H), 2.70 (d, J = 9.1 Hz, 1H), 2.22 (s, 3H), 2.11 (dq, J = 14.1, 7.3 Hz, 1H), 1.83 (dq, J = 12.8, 6.6 Hz, 1H), 1.24 (bs, 1H). | Zp AA119 BB14 |
| I-642 | 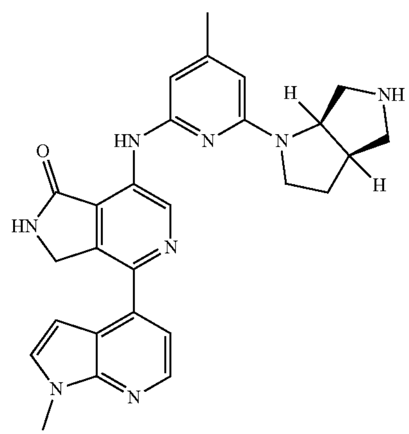 [SMILES: Cc1cc(Nc2cnc(-c3ccnc4c3ccn4C)c3c2C(=O)NC3)nc(N2CC[C@@H]3CNC[C@@H]32)c1] | 7-((6-((3aR,6aR)-hexahydropyrrolo[3,4-b]pyrrol-1(2H)-yl)-4-methylpyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 481.2 [M + H]+, Ret. time = 3.57 min Chiral HPLC method X13: Ret. time = 9.73 | 1H NMR (400 MHz, DMSO-d6) δ 10.08 (s, 1H), 9.53 (s, 1H), 9.19 (s, 1H), 8.36-8.35 (d, J = 5.0 Hz, 1H), 7.59-7.58 (d, J = 3.5 Hz, 1H), 7.38-7.37 (d, J = 5.0 Hz, 1H), 6.87-6.86 (d, J = 3.4 Hz, 1H), 6.06 (s, 1H), 5.90 (s, 1H), 4.69 (s, 2H), 4.32 (s, 1H), 3.88 (s, 3H), 3.66-3.56 (m, 1H), 3.49 (t, J = 8.2 Hz, 1H), 3.00 (dd, J = 11.8, 5.7 Hz, 1H), 2.95-2.77 (m, 3H), 2.70 (d, J = 9.1 Hz, 1H), 2.22 (s, 3H), 2.11 (dq, J = 14.1, 7.3 Hz, 1H), 1.83 (dq, J = 12.8, 6.6 Hz, 1H), 1.24 (bs, 1H). | Zp AA119 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-643 | 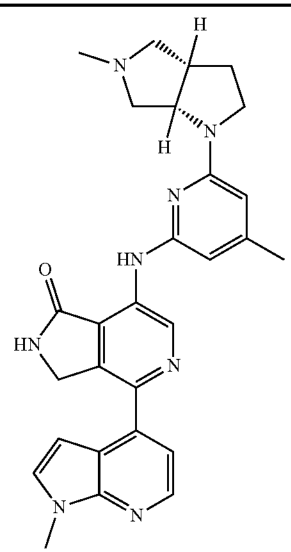 | 4-(1-methyl-1H-pyrrolo[2,3-b]pyridin-4-yl)-7-((4-methyl-6-((3aS,6aS)-5-methylhexahydropyrrolo[3,4-b]pyrrol-1(2H)-yl)pyridin-2-yl)amino)-2,3-dihydro-1H-pyrrolo[3,4-c]pyridin-1-one | LCMS Method J m/z = 495.2 [M + H]+, Ret. time = 3.60 min Chiral HPLC method X13: Ret. time = 5.42 | 1H NMR (400 MHz, DMSO-d6) δ 10.07 (s, 1H), 9.53 (s, 1H), 9.19 (s, 1H), 8.36-8.35 (d, J = 4.9 Hz, 1H), 7.59-7.58 (d, J = 3.4 Hz, 1H), 7.39-7.38 (d, J = 5.0 Hz, 1H), 6.90-6.89 (d, J = 3.4 Hz, 1H), 6.07 (s, 1H), 5.92 (s, 1H), 4.70 (s, 2H), 4.44 (bs, 1H), 3.88 (s, 3H), 3.52 (bs, 2H), 2.94 (bs, 1H), 2.74 (s, 1H), 2.58 (dd, J = 9.3, 5.8 Hz, 2H), 2.40 (dd, J = 9.1, 6.9 Hz, 1H), 2.21 (d, J = 3.7 Hz, 6H), 2.17-2.07 (m, 1H), 1.92-1.88 (dq, J = 12.1, 6.1 Hz, 1H). | Zp & ADp AA119 BB14 |

| # | STRUCTURE | NAME | LCMS | ¹H NMR | Method Reagent AA BB |
|---|---|---|---|---|---|
| I-644 | 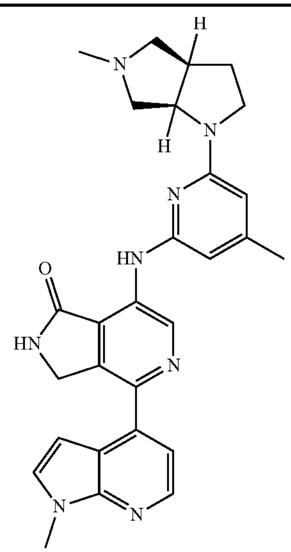 | 4-(1-methyl-1H-pyrrolo[2,3-b]pyridin-4-yl)-7-(((3aR,6aR)-5-methylhexahydro-pyrrolo[3,4-b]pyrrol-1(2H)-yl)pyridin-2-yl)amino)-2,3-dihydro-1H-pyrrolo[3,4-c]pyridin-1-one | LCMS Method J m/z = 495.2 [M + H]+, Ret. time = 3.60 min Chiral HPLC method X13: Ret. time = 5.47 | 1H NMR (400 MHz, DMSO-d6) δ 10.07 (s, 1H), 9.52 (s, 1H), 9.20 (s, 1H), 8.36-8.35 (d, J = 4.9 Hz, 1H), 7.59-7.58 (d, J = 3.4 Hz, 1H), 7.39-7.38 (d, J = 5.0 Hz, 1H), 6.90-6.89 (d, J = 3.4 Hz, 1H), 6.09 (s, 1H), 5.91 (s, 1H), 4.70 (s, 2H), 4.43 (bs, 1H), 3.88 (s, 3H), 3.52 (bs, 2H), 2.94 (bs, 1H), 2.74 (s, 1H), 2.58 (dd, J = 9.3, 5.8 Hz, 2H), 2.40 (dd, J = 9.1, 6.9 Hz, 1H), 2.21 (d, J = 3.7 Hz, 6H), 2.17-2.07 (m, 1H), 1.92-1.88 (dq, J = 12.1, 6.1 Hz, 1H). | Zp & ADp AA119 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-645 | 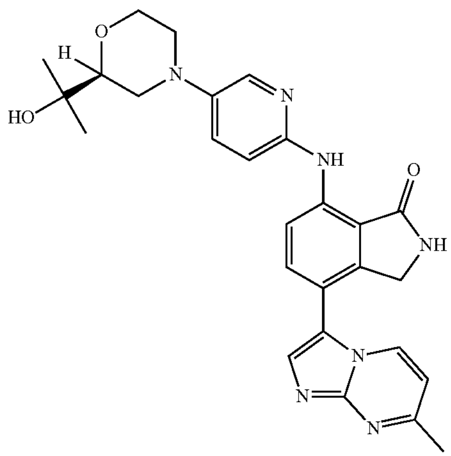 [SMILES: Cc1ccn2c(-c3ccc(Nc4ccc(N5CCO[C@H](C(C)(C)O)C5)cn4)c4c3CNC4=O)cnc2n1] | (S)-7-((5-(2-(2-hydroxypropan-2-yl)morpholino)pyridin-2-yl)amino)-4-(7-methylimidazo[1,2-a]pyrimidin-3-yl)isoindolin-1-one | LCMS Method J m/z = 500.2 [M + H]+, Ret. time = 3.21 min Chiral HPLC method X8: Ret. time = 31.93 | 1H NMR (400 MHz, DMSO-d6) δ 9.89 (s, 1H), 8.82 (s, 1H), 8.72 (d, J = 7.0 Hz, 1H), 8.59 (d, J = 8.6 Hz, 1H), 8.02 (d, J = 3.0 Hz, 1H), 7.89 (s, 1H), 7.70 (d, J = 8.6 Hz, 1H), 7.47 (dd, J = 9.0, 3.0 Hz, 1H), 6.99 (dd, J = 8.1, 3.2 Hz, 2H), 4.51 (s, 1H), 4.42 (s, 2H), 4.01 (dd, J = 10.6, 3.4 Hz, 1H), 3.74-3.56 (m, 2H), 3.47 (d, J = 11.8 Hz, 1H), 3.33 (dd, J = 10.5, 2.3 Hz, 2H), 2.66 (td, J = 11.8, 3.5 Hz, 1H), 2.58 (s, 3H), 1.18 (s, 3H), 1.12 (s, 3H). | G AA48 BB85 |
| I-646 | 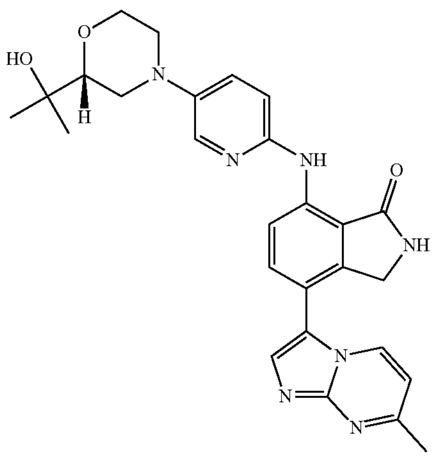 [SMILES: Cc1ccn2c(-c3ccc(Nc4ccc(N5CCO[C@@H](C(C)(C)O)C5)cn4)c4c3CNC4=O)cnc2n1] | (R)-7-((5-(2-(2-hydroxypropan-2-yl)morpholino)pyridin-2-yl)amino)-4-(7-methylimidazo[1,2-a]pyrimidin-3-yl)isoindolin-1-one | LCMS Method J m/z = 500.2 [M + H]+, Ret. time = 3.22 min Chiral HPLC method X8: Ret. time = 37.50 | 1H NMR (400 MHz, DMSO-d6) δ 9.89 (s, 1H), 8.82 (s, 1H), 8.72 (d, J = 7.0 Hz, 1H), 8.59 (d, J = 8.6 Hz, 1H), 8.02 (d, J = 3.0 Hz, 1H), 7.89 (s, 1H), 7.70 (d, J = 8.6 Hz, 1H), 7.47 (dd, J = 9.0, 3.1 Hz, 1H), 6.99 (dd, J = 8.1, 3.2 Hz, 2H), 4.51 (s, 1H), 4.42 (s, 2H), 4.01 (dd, J = 10.6, 3.4 Hz, 1H), 3.74-3.56 (m, 2H), 3.47 (d, J = 11.8 Hz, 1H), 3.33 (dd, J = 10.5, 2.3 Hz, 2H), 2.66 (td, J = 11.8, 3.5 Hz, 1H), 2.58 (s, 3H), 1.18 (s, 3H), 1.12 (s, 3H). | G AA48 BB85 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-648 | 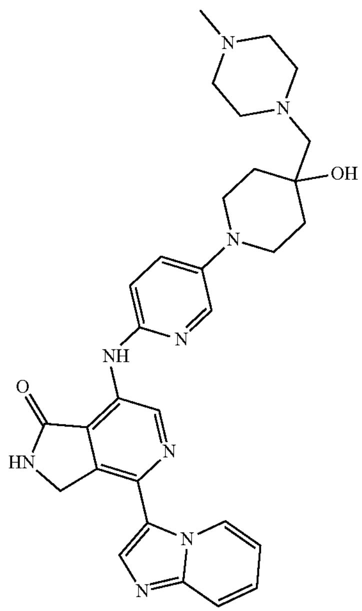 [SMILES: CN1CCN(CC2(O)CCN(c3ccc(Nc4cnc(-c5cnc6ccccn56)c5c4C(=O)NC5)nc3)CC2)CC1] | 7-((5-(4-hydroxy-4-((4-methylpiperazin-1-yl)methyl)piperidin-1-yl)pyridin-2-yl)amino)-4-(imidazo[1,2-a]pyridin-3-yl)-2,3-dihydro-1H-pyrrolo[3,4-c]pyridin-1-one | LCMS Method J m/z = 554.2 [M + H]+, Ret. time = 2.66 min | 1H NMR (400 MHz, DMSO-d6) δ 9.95 (d, J = 6.8 Hz, 2H), 9.50 (s, 1H), 9.34 (s, 1H), 8.47 (s, 1H), 8.09 (d, J = 2.9 Hz, 1H), 8.00 (d, J = 9.0 Hz, 1H), 7.87 (t, J = 8.0 Hz, 1H), 7.59-7.39 (m, 2H), 7.09 (d, J = 8.9 Hz, 1H), 4.78 (s, 2H), 4.05-4.03 (d, J = 6.8 Hz, 2H), 3.35 (d, J = 11.2 Hz, 6H), 3.12 (d, J = 10.0 Hz, 4H), 2.80 (s, 4H), 2.68-2.58 (m, 2H), 1.70-1.69 (d, J = 9.8 Hz, 4H). | O AA55 BB26 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-649 | 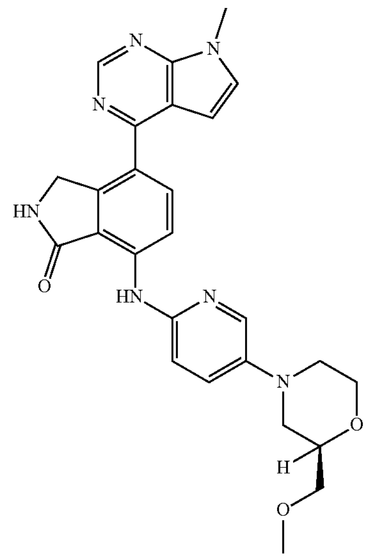 [SMILES: COC[C@H]1CN(c2ccc(Nc3ccc(-c4ncnc5c4ccn5C)c4c3C(=O)NC4)nc2)CCO1] | (R)-7-(5-(2-(methoxymethyl)morpholino)pyridin-2-ylamino)-4-(7-methyl-7H-pyrrolo[2,3-d]pyrimidin-4-yl)isoindolin-1-one | LCMS Method J m/z = 486.2 [M + H]+, Ret. time = 3.91 min Chiral HPLC method X7: Ret. time = 7.57 | 1H NMR (400 MHz, DMSO-d6) δ 10.16 (s, 1H), 8.85 (s, 2H), 8.60 (d, J = 8.7 Hz, 1H), 8.29 (d, J = 8.7 Hz, 1H), 8.04 (d, J = 3.0 Hz, 1H), 7.70 (d, J = 3.6 Hz, 1H), 7.48 (dd, J = 9.0, 3.0 Hz, 1H), 7.08-6.94 (m, 2H), 4.82 (s, 2H), 4.00-3.94 (m, 1H), 3.87 (s, 3H), 3.68 (td, J = 11.4, 2.5 Hz, 1H), 3.54 (d, J = 11.8 Hz, 1H), 3.52 (bs, 3H), 3.48-3.42 (m, 2H), 3.31 (s, 3H), 2.72 (td, J = 11.6, 3.3 Hz, 1H). | G AA39 BB86 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-650 | 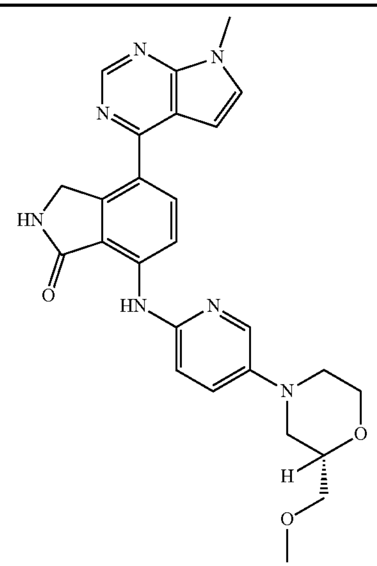 | (S)-7-((5-(2-(methoxymethyl)morpholino)pyridin-2-yl)amino)-4-(7-methyl-7H-pyrrolo[2,3-d]pyrimidin-4-yl)isoindolin-1-one | LCMS Method J m/z = 486.2 [M + H]+, Ret. time = 3.91 min Chiral HPLC method X7: Ret. time = 7.51 | 1H NMR (400 MHz, DMSO-d6) δ 10.16 (s, 1H), 8.85 (s, 2H), 8.60 (d, J = 8.7 Hz, 1H), 8.29 (d, J = 8.7 Hz, 1H), 8.04 (d, J = 3.0 Hz, 1H), 7.70 (d, J = 3.5 Hz, 1H), 7.48 (dd, J = 9.0, 3.1 Hz, 1H), 7.09-6.93 (m, 2H), 4.83 (s, 2H), 3.97 (d, J = 11.3 Hz, 1H), 3.88 (s, 3H), 3.82-3.73 (m, 1H), 3.73-3.63 (m, 1H), 3.57-3.40 (m, 4H), 3.31 (s, 3H), 2.71 (td, J = 11.7, 3.3 Hz, 1H), 2.47 (d, J = 11.0 Hz, 1H). | G AA39 BB86 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-651 | 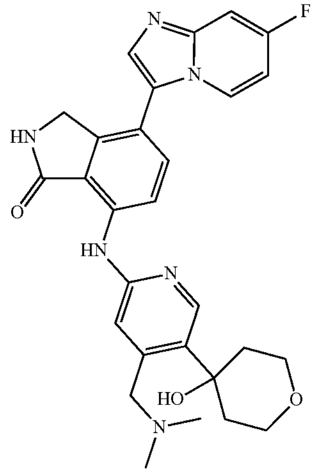 [SMILES: CN(C)Cc1cc(Nc2ccc(-c3cnc4cc(F)ccn34)c3c2C(=O)NC3)ncc1C1(O)CCOCC1] | 7-((4-((dimethylamino)methyl)-5-(4-hydroxytetrahydro-2H-pyran-4-yl)pyridin-2-yl)amino)-4-(7-fluoroimidazo[1,2-a]pyridin-3-yl)isoindolin-1-one | LCMS Method J m/z = 517.9 [M + H]+, Ret. time = 2.50 min | 1H NMR (400 MHz, DMSO-d6) δ 10.12 (s, 1H), 8.90 (s, 1H), 8.79 (d, J = 8.6 Hz, 1H), 8.46 (dd, J = 7.6, 5.7 Hz, 1H), 8.30 (s, 1H), 7.85 (s, 1H), 7.76 (d, J = 8.6 Hz, 1H), 7.55 (dd, J = 10.2, 2.6 Hz, 1H), 7.18 (s, 1H), 7.06 (s, 1H), 7.00 (td, J = 7.5, 2.6 Hz, 1H), 4.42 (s, 2H), 3.87 (t, J = 11.3 Hz, 2H), 3.73 (d, J = 7.3 Hz, 4H), 2.24 (s, 6H), 2.04 (td, J = 12.2, 11.7, 4.6 Hz, 2H), 1.82 (d, J = 12.6 Hz, 2H). | Xp AA122 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-652 | 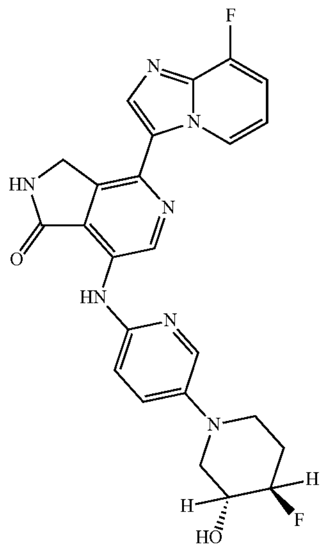 [SMILES: O=C1NCc2c(-c3cnc4c(F)cccn34)ncc(Nc3ccc(N4CC[C@@H](F)[C@H](O)C4)cn3)c21] | 7-((5-((3R,4R)-4-fluoro-3-hydroxy-piperidin-1-yl)pyridin-2-yl)amino)-4-(8-fluoro-imidazo[1,2-a]pyridin-3-yl)-2,3-dihydro-1H-pyrrolo[3,4-c]pyridin-1-one | LCMS Method J m/z = 478.2 [M + H]+, Ret. time = 3.69 min Chiral HPLC method X12: Ret. time = 16.21 | 1H NMR (400 MHz, DMSO-d6) δ 9.92 (s, 1H), 9.70 (d, J = 7.1 Hz, 1H), 9.45 (s, 1H), 9.30 (s, 1H), 8.13 (s, 1H), 8.06 (d, J = 3.0 Hz, 1H), 7.49 (dd, J = 9.0, 3.0 Hz, 1H), 7.34 (dd, J = 11.1, 7.6 Hz, 1H), 7.13-7.01 (m, 2H), 5.46 (d, J = 5.0 Hz, 1H), 4.78 (s, 2H), 3.69 (s, 1H), 3.58 (t, J = 14.4 Hz, 1H), 2.85 (t, J = 11.6 Hz, 1H), 2.75 (d, J = 15.3 Hz, 1H), 2.67 (dd, J = 12.0, 9.2 Hz, 2H), 2.13 (s, 1H), 1.80-1.70 (m, 1H). | Zp AA49 BB87 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-653 | 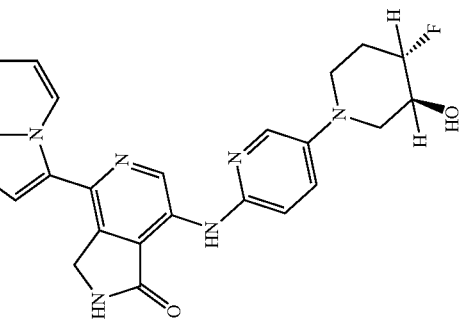 | 7-((5-((3S,4S)-4-fluoro-3-hydroxy-piperidin-1-yl)pyridin-2-yl)amino)-4-(8-fluoro-imidazo[1,2-a]pyridin-3-yl)-2,3-dihydro-1H-pyrrolo[3,4-c]pyridin-1-one | LCMS Method J m/z = 478.2 [M + H]+, Ret. time = 3.68 min Chiral HPLC method X12: Ret. time = 14.71 | 1H NMR (400 MHz, DMSO-d6) δ 9.92 (s, 1H), 9.70 (d, J = 7.0 Hz, 1H), 9.45 (s, 1H), 9.31 (s, 1H), 8.13 (s, 1H), 8.06 (d, J = 3.0 Hz, 1H), 7.49 (dd, J = 8.8, 3.0 Hz, 1H), 7.34 (dd, J = 11.1, 7.6 Hz, 1H), 7.16-6.99 (m, 2H), 5.47 (s, 1H), 4.78 (s, 2H), 4.44 (d, J = 52.8 Hz, 1H), 3.69 (s, 1H), 3.56 (d, J = 14.9 Hz, 2H), 2.84 (t, J = 11.8 Hz, 1H), 2.67 (dd, J = 11.9, 9.2 Hz, 1H), 2.13 (s, 1H), 1.76 (t, J = 11.3 Hz, 1H). | Zp AA49 BB87 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-654 | 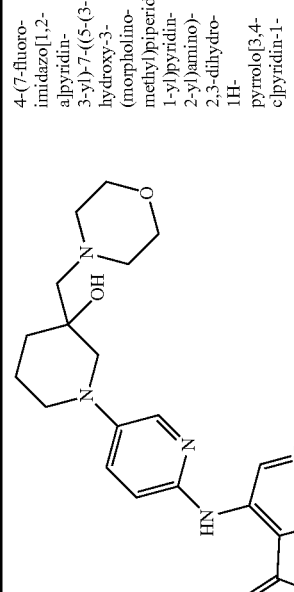 | 4-(7-fluoro-imidazo[1,2-a]pyridin-3-yl)-7-((5-(3-hydroxy-3-(morpholino-methyl)piperidin-1-yl)pyridin-2-yl)amino)-2,3-dihydro-1H-pyrrolo[3,4-c]pyridin-1-one | LCMS Method J m/z = 559.2 [M + H]+, Ret. time = 2.99 min | 1H NMR (400 MHz, DMSO-d6) δ 9.95 (dd, J = 7.8, 6.1 Hz, 1H), 9.89 (s, 1H), 9.40 (s, 1H), 9.28 (s, 1H), 8.07 (s, 1H), 8.01 (d, J = 3.0 Hz, 1H), 7.61 (dd, J = 9.9, 2.8 Hz, 1H), 7.44 (dd, J = 9.0, 3.0 Hz, 1H), 7.16 (td, J = 7.6, 2.8 Hz, 1H), 7.03 (d, J = 8.9 Hz, 1H), 4.75 (s, 2H), 4.42 (s, 1H), 3.60 (t, J = 4.6 Hz, 4H), 3.21-3.13 (m, 3H), 2.96-2.92 (ddd, J = 11.8, 8.6, 3.3 Hz, 2H), 2.79 (d, J = 11.5 Hz, 2H), 2.42 (s, 2H), 1.77 (td, J = 15.5, 14.8, 7.5 Hz, 2H), 1.65-1.54 (m, 2H), 1.48-1.40 (m, 1H). | O AA15 BB63 |
| I-655 | 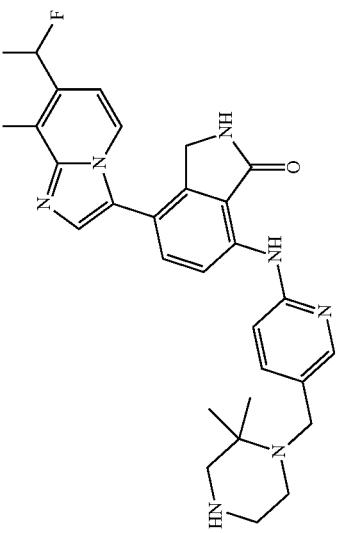 | 4-(7-(difluoro-methyl)-8-fluoro-imidazo[1,2-a]pyridin-3-yl)-7-((5-((2,2-dimethyl-piperazin-1-yl)methyl)pyridin-2-yl)amino)isoindolin-1-one | LCMS Method J m/z = 536.2 [M + H]+, Ret. time = 3.52 min | 1H NMR (400 MHz, DMSO-d6) δ 10.11 (s, 1H), 8.89 (s, 1H), 8.76 (d, J = 8.6 Hz, 1H), 8.37 (d, J = 7.2 Hz, 1H), 8.21 (d, J = 2.4 Hz, 1H), 8.06 (s, 1H), 7.78 (d, J = 8.6 Hz, 1H), 7.66 (dd, J = 8.5, 2.4 Hz, 1H), 7.45 (s, 1H), 7.12-6.92 (m, 2H), 4.43 (s, 2H), 3.54-3.40 (m, 2H), 2.69 (s, 2H), 2.59 (s, 2H), 2.30 (s, 2H), 1.56 (s, 1H), 1.12 (s, 6H). | ACp AA104 BB89 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-656 | 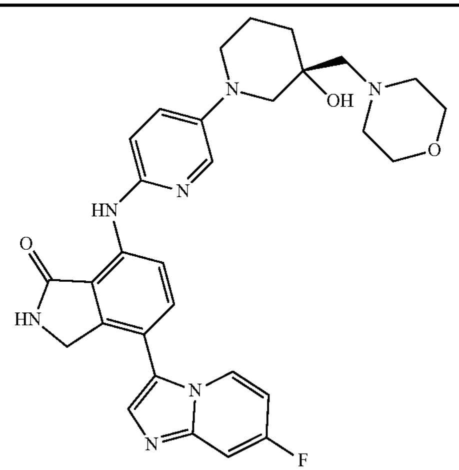 | (R)-4-(7-fluoro-imidazo[1,2-a]pyridin-3-yl)-7-((5-(3-hydroxy-3-(morpholino-methyl)piperidin-1-yl)pyridin-2-yl)amino)iso-indolin-1-one | LCMS Method J m/z = 558.3 [M + H]+, Ret. time = 2.83 min Chiral HPLC method X9: Ret. time = 8.56 | 1H NMR (400 MHz, DMSO-d6) δ 9.85 (s, 1H), 8.79 (s, 1H), 8.56 (d, J = 8.5 Hz, 1H), 8.44 (t, J = 6.6 Hz, 1H), 7.98 (d, J = 3.0 Hz, 1H), 7.83 (s, 1H), 7.70 (d, J = 8.6 Hz, 1H), 7.54 (dd, J = 10.0, 2.6 Hz, 1H), 7.44 (dd, J = 8.9, 2.9 Hz, 1H), 6.98 (t, J = 7.7 Hz, 2H), 4.41 (d, J = 14.4 Hz, 3H), 3.60 (s, 4H), 3.16 (dd, J = 19.9, 12.1 Hz, 2H), 2.93 (t, J = 9.4 Hz, 1H), 2.77 (d, J = 11.5 Hz, 1H), 2.42 (s, 2H), 2.34 (s, 2H), 1.75 (d, J = 12.6 Hz, 2H), 1.58 (s, 1H), 1.43 (s, 1H), 1.24 (s, 2H). | Yp AA123 BB63 |
| I-657 | 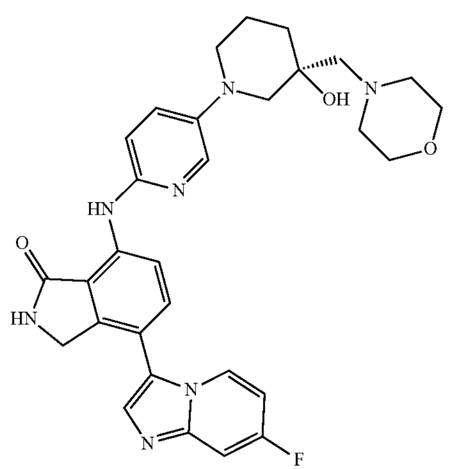 [SMILES: O=C1NCc2c(-c3cnc4cc(F)ccn34)ccc(Nc3ccc(N4CCC[C@](O)(CN5CCOCC5)C4)cn3)c21] | (S)-4-(7-fluoro-imidazo[1,2-a]pyridin-3-yl)-7-((5-(3-hydroxy-3-(morpholino-methyl)piperidin-1-yl)pyridin-2-yl)amino)iso-indolin-1-one | LCMS Method J m/z = 558.2 [M + H]+, Ret. time = 2.82 min Chiral HPLC method X9: Ret. time = 9.95 | 1H NMR (400 MHz, DMSO-d6) δ 9.85 (s, 1H), 8.79 (s, 1H), 8.56 (d, J = 8.5 Hz, 1H), 8.44 (dd, J = 7.6, 5.7 Hz, 1H), 7.98 (d, J = 2.9 Hz, 1H), 7.83 (s, 1H), 7.70 (d, J = 8.5 Hz, 1H), 7.54 (dd, J = 10.1, 2.7 Hz, 1H), 7.43 (dd, J = 9.0, 3.0 Hz, 1H), 6.99 (td, J = 8.7, 8.1, 3.1 Hz, 2H), 4.41 (d, J = 13.9 Hz, 3H), 3.60 (t, J = 4.5 Hz, 3H), 3.33 (s, 2H), 3.16 (dd, J = 20.1, 12.1 Hz, 2H), 2.93 (t, J = 9.2 Hz, 1H), 2.77 (d, J = 11.5 Hz, 1H), 2.42 (s, 2H), 2.34 (s, 1H), 1.75 (d, J = 12.6 Hz, 2H), 1.57 (s, 1H), 1.44 (d, J = 9.8 Hz, 1H), 1.24 (s, 2H). | Yp AA123 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-658 | 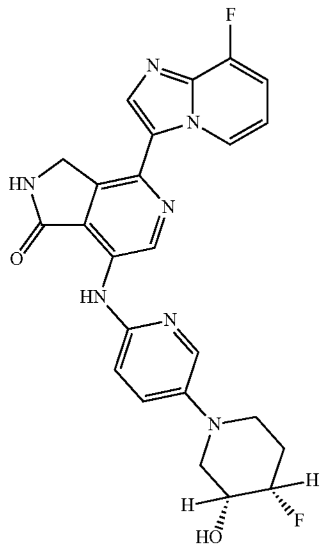 [SMILES: O=C1NCc2c(-c3cnc4c(F)cccn34)ncc(Nc3ccc(N4CC[C@H](F)[C@H](O)C4)cn3)c21] | 7-((5-((3R,4S)-4-fluoro-3-hydroxy-piperidin-1-yl)pyridin-2-yl)amino)-4-(8-fluoro-imidazo[1,2-a]pyridin-3-yl)-2,3-dihydro-1H-pyrrolo[3,4-c]pyridin-1-one | LCMS Method J m/z = 478.7 [M + H]+, Ret. time = 3.18 min | 1H NMR (400 MHz, DMSO-d6) δ 9.92 (s, 1H), 9.70 (d, J = 7.0 Hz, 1H), 9.44 (s, 1H), 9.30 (s, 1H), 8.43 (s, 1H), 8.12 (s, 1H), 8.06 (d, J = 3.0 Hz, 1H), 7.50-7.47 (dd, J = 8.9, 3.0 Hz, 1H), 7.36-7.31 (dd, J = 11.1, 7.6 Hz, 1H), 7.10-7.03 (td, J = 10.7, 9.1, 6.3 Hz, 2H), 4.78 (s, 2H), 3.82-3.81 (d, J = 3.6 Hz, 1H), 2.75 (bs, 1H), 1.24 (bs, 3H), 1.10 (s, 2H), 0.86 (s, 1H). | Zp AA54 BB87 |

| # | STRUCTURE | NAME | LCMS | 1H NMR | Method Reagent AA BB |
|---|---|---|---|---|---|
| I-659 | 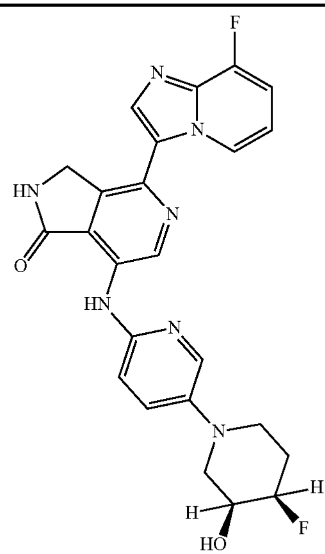 | 7-((5-((3S,4R)-4-fluoro-3-hydroxy-piperidin-1-yl)pyridin-2-yl)amino)-4-(8-fluoro-imidazo[1,2-a]pyridin-3-yl)-2,3-dihydro-1H-pyrrolo[3,4-c]pyridin-1-one | LCMS Method J m/z = 478.2 [M + H]+, Ret. time = 3.62 min | 1H NMR (400 MHz, DMSO-d6) δ 9.93 (s, 1H), 9.70 (d, J = 7.0 Hz, 1H), 9.45 (s, 1H), 9.31 (s, 1H), 8.13 (s, 1H), 8.07 (d, J = 3.0 Hz, 1H), 7.49 (dd, J = 9.0, 3.1 Hz, 1H), 7.34 (dd, J = 11.1, 7.6 Hz, 1H), 7.16-6.98 (m, 2H), 5.23 (d, J = 5.6 Hz, 1H), 4.77 (d, J = 14.2 Hz, 2H), 3.79 (d, J = 26.1 Hz, 1H), 3.29 (s, 1H), 2.06 (d, J = 11.4 Hz, 2H), 1.24 (s, 1H), 1.10 (s, 2H), 0.86 (s, 1H). | Zp AA54 BB87 |
| I-660 | 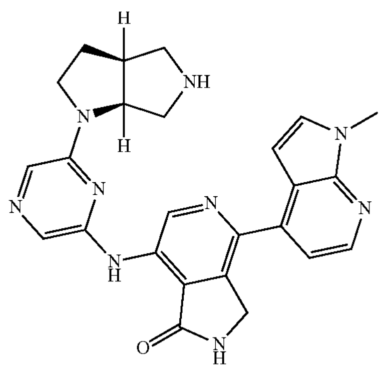 [SMILES: Cn1ccc2c(-c3ncc(Nc4cncc(N5CC[C@H]6CNC[C@H]65)n4)c4c3CNC4=O)ccnc21] | 7-((6-((3aS,6aS)-hexahydro-pyrrolo[3,4-b]pyrrol-1(2H)-yl)pyrazin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 468.2 [M + H]+, Ret. time = 3.19 min Chiral HPLC method X9: Ret. time = 8.55 | 1H NMR (400 MHz, DMSO-d6) δ 9.95 (s, 1H), 9.74 (s, 1H), 9.29 (s, 1H), 8.37 (d, J = 5.0 Hz, 1H), 8.28 (s, 1H), 7.67 (s, 1H), 7.62-7.50 (m, 2H), 7.41 (d, J = 5.0 Hz, 1H), 6.88 (d, J = 3.3 Hz, 1H), 4.72 (s, 2H), 4.48 (bs, 1H), 3.88 (s, 3H), 3.69 (d, J = 3.5 Hz, 1H), 3.21 (s, 1H), 3.19 (d, J = 6.0 Hz, 2H), 3.16-3.05 (m, 2H), 2.88 (dd, J = 10.7, 3.1 Hz, 1H), 2.18-2.13 (dq, J = 14.6, 7.4 Hz, 1H), 1.94-1.90 (dt, J = 11.6, 6.2 Hz, 1H). | Zp AA124 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-661 | 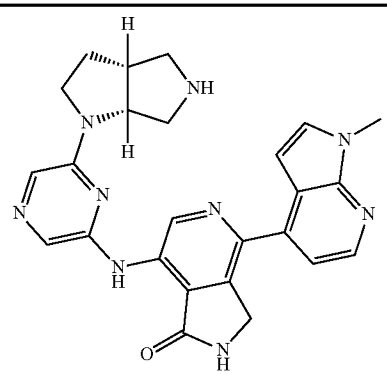 | 7-((6-((3aR,6aR)-hexahydro-pyrrolo[3,4-b]pyrrol-1(2H)-yl)pyrazin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 468.2 [M + H]+, Ret. time = 3.20 min Chiral HPLC method X9: Ret. time = 9.04 | 1H NMR (400 MHz, DMSO-d6) δ 9.96 (s, 1H), 9.74 (s, 1H), 9.29 (s, 1H), 8.37 (d, J = 4.9 Hz, 1H), 8.28 (s, 1H), 7.67 (s, 1H), 7.60 (d, J = 3.5 Hz, 1H), 7.55 (s, 1H), 7.41 (d, J = 4.9 Hz, 1H), 6.88 (d, J = 3.4 Hz, 1H), 4.73 (s, 2H), 4.47 (s, 1H), 3.89 (s, 3H), 3.69-3.66 (m, 1H), 3.58 (d, J = 8.6 Hz, 1H), 3.18 (s, 1H), 3.09 (d, J = 12.0 Hz, 2H), 3.02 (d, J = 11.5 Hz, 2H), 2.86 (d, J = 9.6 Hz, 1H), 2.16 (dd, J = 12.9, 6.9 Hz, 1H). | Zp AA124 BB14 |
| I-662 | 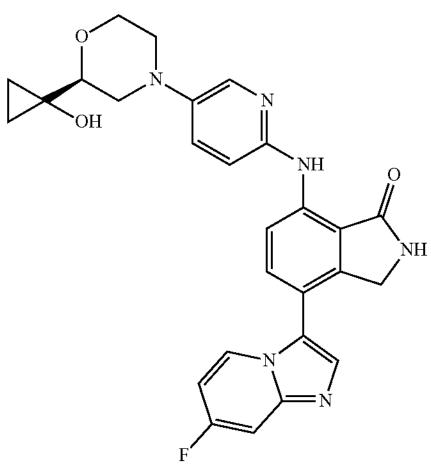 [SMILES: O=C1NCc2c(-c3cnc4cc(F)ccn34)ccc(Nc3ccc(N4CCO[C@H](C5(O)CC5)C4)cn3)c21] | rel-(R)-4-(7-fluoro-imidazo[1,2-a]pyridin-3-yl)-7-((5-(2-(1-hydroxycyclo-propyl)morpho-lino)pyridin-2-yl)amino)iso-indolin-1-one | LCMS Method J m/z = 501.2 [M + H]+, Ret. time = 3.23 min Chiral HPLC method X7: Ret. time = 6.77 | 1H NMR (400 MHz, DMSO-d6) δ 9.88 (d, J = 4.1 Hz, 1H), 8.80 (d, J = 4.1 Hz, 1H), 8.57 (dd, J = 8.6, 4.1 Hz, 1H), 8.44 (q, J = 6.1, 5.4 Hz, 1H), 8.02 (t, J = 3.5 Hz, 1H), 7.83 (d, J = 4.1 Hz, 1H), 7.70 (dd, J = 8.6, 4.1 Hz, 1H), 7.61-7.39 (m, 2H), 6.99 (dt, J = 7.4, 3.7 Hz, 2H), 5.45 (d, J = 4.1 Hz, 1H), 4.39 (d, J = 4.2 Hz, 2H), 3.96 (d, J = 11.1 Hz, 1H), 3.64 (d, J = 12.3 Hz, 2H), 3.46 (d, J = 12.2 Hz, 1H), 3.17 (d, J = 4.9 Hz, 1H), 2.72-2.62 (m, 2H), 0.73-0.46 (m, 4H). | Yp AA125 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-663 | 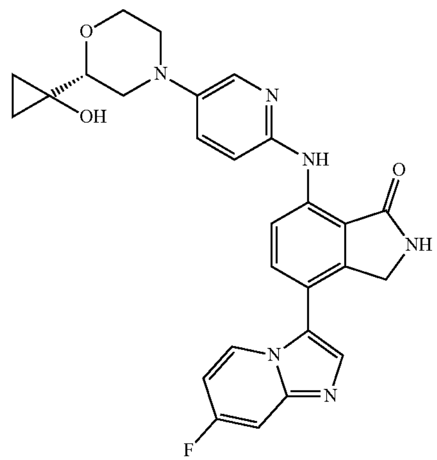 [SMILES: O=C1NCc2c(-c3cnc4cc(F)ccn34)ccc(Nc3ccc(N4CCO[C@@H](C5(O)CC5)C4)cn3)c21] | rel-(R)-4-(7-fluoro-imidazo[1,2-a]pyridin-3-yl)-7-((5-(2-(1-hydroxycyclopropyl)morpholino)pyridin-2-yl)amino)isoindolin-1-one | LCMS Method J m/z = 501.2 [M + H]+, Ret. time = 3.23 min Chiral HPLC method X7: Ret. time = 6.4 | 1H NMR (400 MHz, DMSO-d6) δ 9.80 (s, 1H), 8.81 (s, 1H), 8.58 (d, J = 8.6 Hz, 1H), 8.03 (d, J = 3.0 Hz, 1H), 7.83 (s, 1H), 7.71 (d, J = 8.6 Hz, 1H), 7.51 (ddd, J = 22.9, 9.5, 2.9 Hz, 2H), 7.08-6.89 (m, 2H), 5.46 (s, 1H), 4.39 (d, J = 4.2 Hz, 2H), 3.96 (d, J = 11.1 Hz, 1H), 3.64 (d, J = 12.3 Hz, 2H), 3.46 (d, J = 12.2 Hz, 1H), 3.17 (d, J = 4.9 Hz, 2H), 2.72-2.62 (m, 2H), 0.73-0.46 (m, 4H). | Yp AA125 BB63 |
| I-667 | 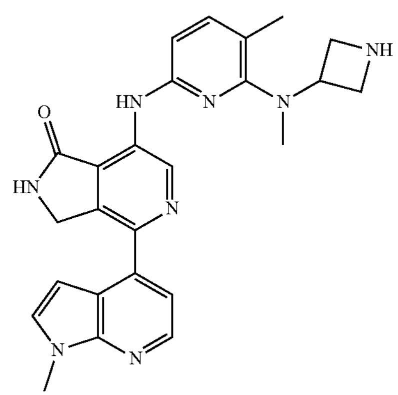 [SMILES: Cc1ccc(Nc2cnc(-c3ccnc4c3ccn4C)c3c2C(=O)NC3)nc1N(C)C1CNC1] | 7-((6-(azetidin-3-yl(methyl)amino)-5-methylpyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 455.2 [M + H]+, Ret. time = 2.82 min | 1H NMR (400 MHz, DMSO-d6) δ 8.55 (s, 1H), 8.38-8.30 (m, 2H), 8.25 (s, 1H), 7.55 (d, J = 3.5 Hz, 1H), 7.36 (d, J = 5.0 Hz, 1H), 6.92 (d, J = 3.5 Hz, 1H), 6.82 (d, J = 8.9 Hz, 1H), 5.72 (d, J = 3.5 Hz, 1H), 4.54 (d, J = 8.8 Hz, 1H), 4.30 (d, J = 12.5, 9.8 Hz, 1H), 3.95 (dd, J = 12.5, 7.9 Hz, 2H), 3.87 (s, 4H), 3.13 (s, 3H), 2.98 (t, J = 4.5 Hz, 2H), 2.15 (s, 3H). | O AA128 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-668 | 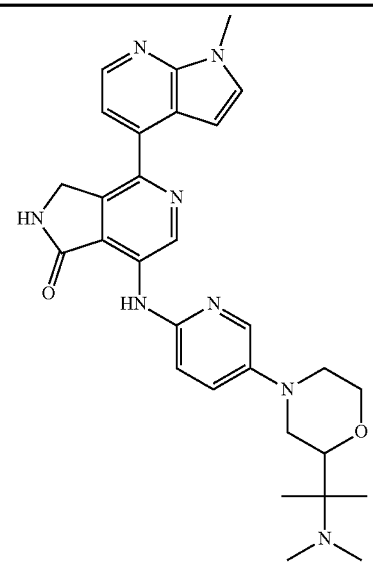 | 7-((5-(2-(dimethylamino)propan-2-yl)morpholino)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 527.2 [M + H]+, Ret. time = 3.28 min | 1H NMR (400 MHz, DMSO-d6) δ 9.95 (s, 1H), 9.55 (s, 1H), 9.19 (s, 1H), 8.36 (d, J = 5.0 Hz, 1H), 8.07 (d, J = 3.0 Hz, 1H), 7.58 (d, J = 3.5 Hz, 1H), 7.47 (dd, J = 9.0, 3.0 Hz, 1H), 7.39 (d, J = 5.0 Hz, 1H), 7.09 (d, J = 8.8 Hz, 1H), 6.92 (d, J = 3.5 Hz, 1H), 4.72 (s, 2H), 4.03 (dd, J = 11.1, 3.2 Hz, 1H), 3.88 (s, 3H), 3.74-3.65 (m, 1H), 3.59 (t, J = 9.7 Hz, 2H), 3.49 (d, J = 11.3 Hz, 1H), 2.69 (td, J = 11.8, 3.5 Hz, 1H), 2.20 (s, 6H), 1.24 (s, 1H), 1.02 (d, J = 19.3 Hz, 6H). | O AA93 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-669 | 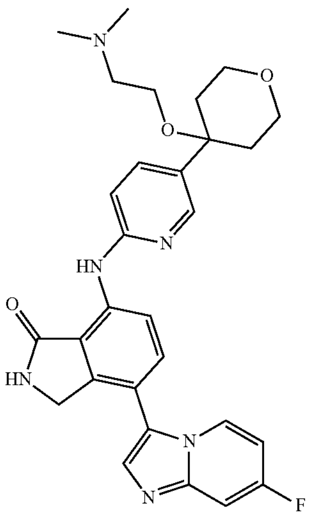 [SMILES: CN(C)CCOC1(c2ccc(Nc3ccc(-c4cnc5cc(F)ccn45)c4c3C(=O)NC4)nc2)CCOCC1] | 7-((5-(4-(2-(dimethyl-amino)eth-oxy)tetra-hydro-2H-pyran-4-yl)pyridin-2-yl)amino)-4-(7-fluoro-imidazo[1,2-a]pyridin-3-yl)isoindolin-1-one | LCMS Method C m/z = 531.5 [M + H]+, Ret. time = 2.47 min | 1H NMR (400 MHz, DMSO-d6) δ 10.16 (s, 1H), 8.88 (s, 1H), 8.76 (d, J = 8.5 Hz, 1H), 8.46 (dd, J = 7.6, 5.7 Hz, 1H), 8.35 (d, J = 2.5 Hz, 1H), 7.85 (s, 1H), 7.76 (dd, J = 8.7, 2.5 Hz, 2H), 7.55 (dd, J = 10.1, 2.7 Hz, 1H), 7.14-6.90 (m, 2H), 4.42 (s, 2H), 3.83-3.65 (m, 4H), 3.12 (t, J = 6.0 Hz, 2H), 2.41 (t, J = 5.9 Hz, 2H), 2.15 (s, 6H), 1.98 (dt, J = 8.9, 4.1 Hz, 4H). | Xp AA129 BB63 |
| I-670 | 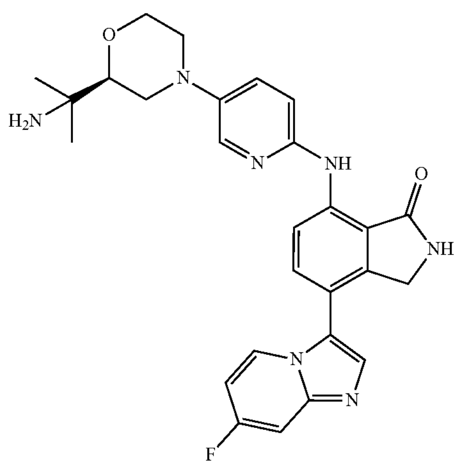 [SMILES: CC(C)(N)[C@@H]1CN(c2ccc(Nc3ccc(-c4cnc5cc(F)ccn45)c4c3C(=O)NC4)nc2)CCO1] | rel-(R)-7-((5-(2-(2-aminopropan-2-yl)morpho-lino)pyridin-2-yl)amino)-4-(7-fluoro-imidazo[1,2-a]pyridin-3-yl)isoindolin-1-one | LCMS Method J m/z = 502.2 [M + H]+, Ret. time = 2.86 min Chiral HPLC method X9: Ret. time = 8.18 | 1H NMR (400 MHz, DMSO-d6) δ 9.88 (s, 1H), 8.80 (s, 1H), 8.59 (d, J = 8.5 Hz, 1H), 8.43 (dd, J = 7.6, 5.7 Hz, 1H), 8.06 (d, J = 3.0 Hz, 1H), 7.83 (s, 1H), 7.70 (d, J = 8.6 Hz, 1H), 7.52 (ddd, J = 15.4, 9.5, 2.9 Hz, 2H), 7.04-6.87 (m, 2H), 4.39 (s, 2H), 4.02 (dd, J = 11.1, 2.9 Hz, 1H), 3.72-3.57 (m, 2H), 3.47 (d, J = 11.7 Hz, 1H), 3.25 (dd, J = 10.5, 2.3 Hz, 2H), 2.65 (td, J = 11.7, 3.4 Hz, 1H), 1.56 (s, 2H), 1.06 (d, J = 6.5 Hz, 6H). | Yp AA130 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-671 | 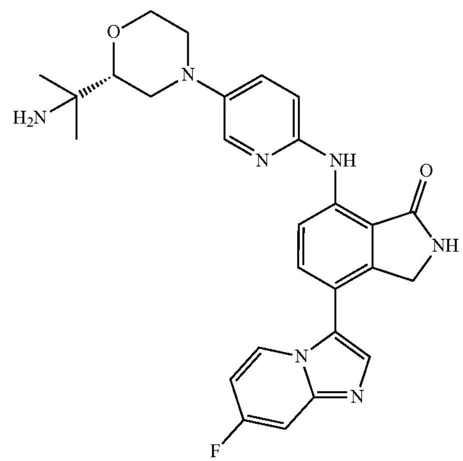 | rel-(R)-7-(5-(2-(2-aminopropan-2-yl)morpholino)pyridin-2-yl)amino)-4-(7-fluoroimidazo[1,2-a]pyridin-3-yl)isoindolin-1-one | LCMS Method J m/z = 498.2 [M + H]+, Ret. time = 2.87 min Chiral HPLC method X9: Ret. time = 8.13 | 1H NMR (400 MHz, DMSO-d6) δ 9.88 (s, 1H), 8.80 (s, 1H), 8.59 (d, J = 8.5 Hz, 1H), 8.43 (dd, J = 7.6, 5.7 Hz, 1H), 8.06 (d, J = 3.0 Hz, 1H), 7.83 (s, 1H), 7.70 (d, J = 8.6 Hz, 1H), 7.52 (ddd, J = 15.3, 9.5, 2.9 Hz, 2H), 7.06-6.90 (m, 2H), 4.39 (s, 2H), 4.02 (dd, J = 10.9, 3.2 Hz, 1H), 3.65 (dt, J = 13.7, 10.1 Hz, 2H), 3.47 (d, J = 11.7 Hz, 1H), 3.25 (dd, J = 10.6, 2.3 Hz, 2H), 2.65 (td, J = 11.9, 3.6 Hz, 1H), 1.62 (s, 2H), 1.06 (d, J = 6.4 Hz, 6H). | Yp AA130 BB63 |
| I-672 | 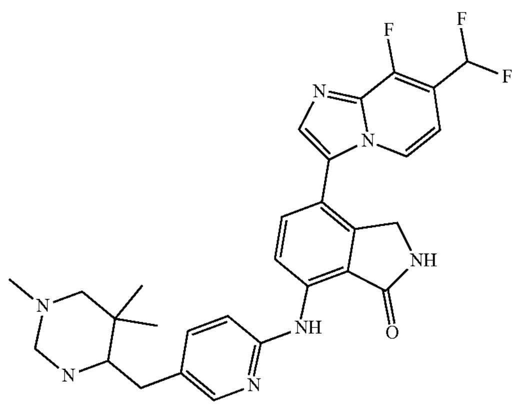 [SMILES: CN1CNC(Cc2ccc(Nc3ccc(-c4cnc5c(F)c(C(F)F)ccn45)c4c3C(=O)NC4)nc2)C(C)(C)C1] | 4-(7-(difluoromethyl)-8-fluoroimidazo[1,2-a]pyridin-3-yl)-7-((5-((2,2,4-trimethylpiperazin-1-yl)methyl)pyridin-2-yl)amino)isoindolin-1-one | LCMS Method J m/z = 550.2 [M + H]+, Ret. time = 3.72 min | 1H NMR (400 MHz, DMSO-d6) δ 10.10 (s, 1H), 8.88 (s, 1H), 8.76-8.74 (d, J = 8.6 Hz, 1H), 8.37-8.36 (d, J = 7.2 Hz, 1H), 8.20 (d, J = 2.3 Hz, 1H), 8.05 (s, 1H), 7.79-7.77 (d, J = 8.6 Hz, 1H), 7.66-7.63 (dd, J = 8.4, 2.3 Hz, 1H), 7.44 (s, 1H), 7.09-7.06 (t, J = 6.4 Hz, 1H), 7.09-6.99 (m, 1H), 4.43 (s, 2H), 2.36 (d, J = 5.3 Hz, 3H), 2.13 (s, 3H), 1.39 (s, 2H), 1.24 (d, J = 10.7 Hz, 3H), 1.13 (s, 6H). | ACp & ADp AA104 BB89 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-673 | 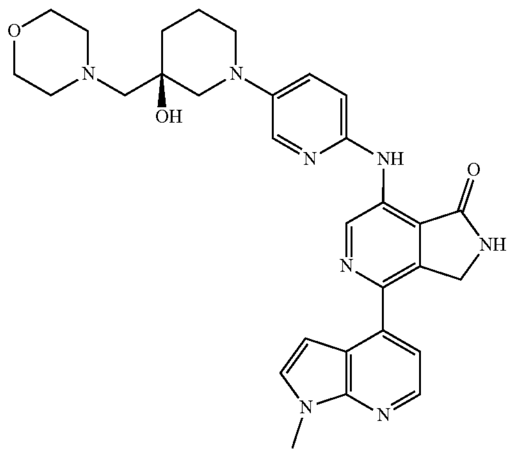 [SMILES: Cn1ccc2c(-c3ncc(Nc4ccc(N5CCC[C@@](O)(CN6CCOCC6)C5)cn4)c4c3CNC4=O)ccnc21] | rel-(R)-7-((5-(3-hydroxy-3-(morpholino-methyl)piperidin-1-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 555.3 [M + H]+, Ret. time = 3.21 min Chiral HPLC method X9: Ret. time = 14.37 | 1H NMR (400 MHz, DMSO-d6) δ 9.92 (s, 1H), 9.51 (s, 1H), 9.18 (s, 1H), 8.36 (d, J = 5.0 Hz, 1H), 8.04 (d, J = 3.0 Hz, 1H), 7.58 (d, J = 3.5 Hz, 1H), 7.45 (dd, J = 8.9, 3.0 Hz, 1H), 7.39 (d, J = 5.1 Hz, 1H), 7.06 (d, J = 9.0 Hz, 1H), 6.92 (d, J = 3.5 Hz, 1H), 4.73 (s, 2H), 4.44 (s, 1H), 3.88 (s, 3H), 3.60 (t, J = 4.6 Hz, 4H), 3.18 (dd, J = 24.2, 9.0 Hz, 3H), 3.01-2.92 (m, 1H), 2.80 (d, J = 11.6 Hz, 1H), 2.42 (d, J = 2.4 Hz, 3H), 1.76 (d, J = 11.2 Hz, 2H), 1.57 (d, J = 9.2 Hz, 1H), 1.44 (t, J = 9.3 Hz, 1H), 1.24 (s, 3H). | Zp AA132 BB14 |
| I-674 | 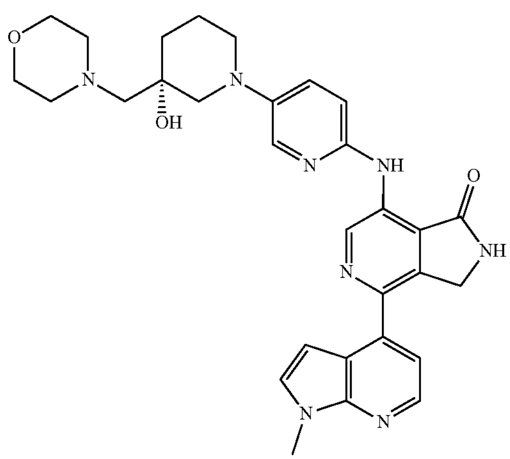 [SMILES: Cn1ccc2c(-c3ncc(Nc4ccc(N5CCC[C@](O)(CN6CCOCC6)C5)cn4)c4c3CNC4=O)ccnc21] | rel-(R)-7-((5-(3-hydroxy-3-(morpholino-methyl)piperidin-1-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 555.3 [M + H]+, Ret. time = 3.21 min Chiral HPLC method X9: Ret. time = 17.55 | 1H NMR (400 MHz, DMSO-d6) δ 9.92 (s, 1H), 9.51 (s, 1H), 9.18 (s, 1H), 8.36 (d, J = 5.0 Hz, 1H), 8.04 (d, J = 3.0 Hz, 1H), 7.58 (d, J = 3.5 Hz, 1H), 7.46 (dd, J = 8.9, 3.0 Hz, 1H), 7.39 (d, J = 5.0 Hz, 1H), 7.06 (d, J = 8.9 Hz, 1H), 6.92 (d, J = 3.5 Hz, 1H), 4.72 (s, 2H), 4.43 (s, 1H), 3.88 (s, 3H), 3.60 (t, J = 4.6 Hz, 4H), 3.19 (dd, J = 20.4, 11.8 Hz, 2H), 3.02-2.92 (m, 1H), 2.80 (d, J = 11.6 Hz, 1H), 2.42 (s, 3H), 1.77 (s, 2H), 1.57 (s, 1H), 1.45 (d, J = 9.6 Hz, 1H), 1.25 (s, 3H). | Zp AA132 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-675 | 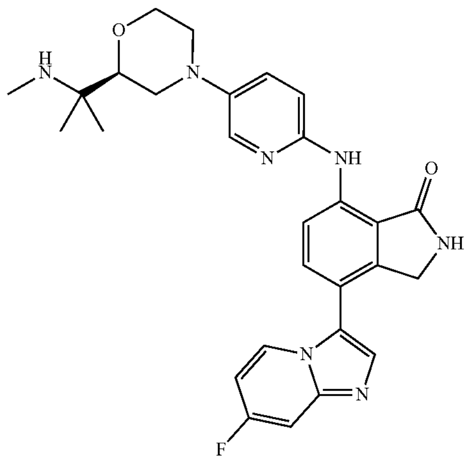 [SMILES: CNC(C)(C)[C@@H]1CN(c2ccc(Nc3ccc(-c4cnc5cc(F)ccn45)c4c3C(=O)NC4)nc2)CCO1] | rel-(R)-4-(7-fluoro-imidazo[1,2-a]pyridin-(3-yl)-7-((5-(2-2-(methylamino)propan-2-yl)morpho-lino)pyridin-2-yl)amino)iso-indolin-1-one | LCMS Method J m/z = 516.9 [M + H]+, Ret. time = 2.46 min Chiral HPLC method X4: Ret. time = 12.13 | 1H NMR (400 MHz, DMSO-d6) δ 10.01 (s, 1H), 9.88 (s, 1H), 8.80 (s, 1H), 8.59 (d, J = 8.5 Hz, 1H), 8.43 (t, J = 6.6 Hz, 1H), 8.05 (d, J = 3.0 Hz, 1H), 7.83 (s, 1H), 7.70 (d, J = 8.6 Hz, 1H), 7.52 (ddd, J = 20.0, 9.5, 2.9 Hz, 2H), 6.99 (dd, J = 8.2, 5.0 Hz, 2H), 4.39 (s, 2H), 4.02 (dd, J = 11.0, 3.2 Hz, 1H), 3.66 (td, J = 11.5, 2.7 Hz, 2H), 3.56 (d, J = 11.7 Hz, 1H), 3.50-3.41 (m, 2H), 2.66 (td, J = 11.6, 3.4 Hz, 1H), 2.23 (s, 3H), 1.04 (d, J = 11.3 Hz, 6H). | Yp AA133 BB63 |
| I-676 | 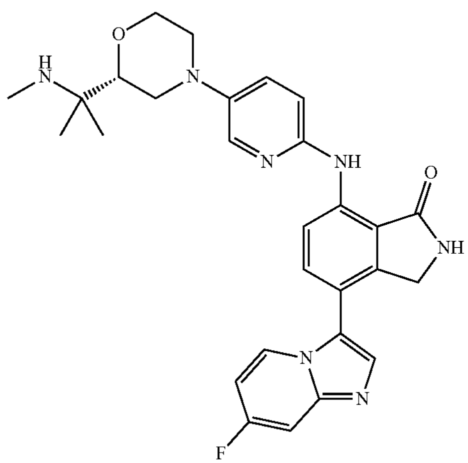 [SMILES: CNC(C)(C)[C@H]1CN(c2ccc(Nc3ccc(-c4cnc5cc(F)ccn45)c4c3C(=O)NC4)nc2)CCO1] | rel-(R)-4-(7-fluoro-imidazo[1,2-a]pyridin-3-yl)-7-((5-(2-(2-(methylamino)propan-2-yl)morpho-lino)pyridin-2-yl)amino)iso-indolin-1-one | LCMS Method J m/z = 516.9 [M + H]+, Ret. time = 2.46 min Chiral HPLC method X4: Ret. time = 11.71 | 1H NMR (400 MHz, DMSO-d6) δ 10.02 (s, 1H), 9.88 (s, 1H), 8.81 (s, 1H), 8.59 (d, J = 8.6 Hz, 1H), 8.43 (dd, J = 7.6, 5.7 Hz, 1H), 8.06 (d, J = 3.0 Hz, 1H), 7.83 (s, 1H), 7.70 (d, J = 8.6 Hz, 1H), 7.52 (ddd, J = 16.7, 9.5, 2.9 Hz, 2H), 6.99 (dd, J = 8.2, 5.2 Hz, 2H), 4.39 (s, 2H), 4.03 (dd, J = 11.3, 3.1 Hz, 1H), 3.68 (td, J = 11.6, 2.7 Hz, 1H), 3.56 (d, J = 11.7 Hz, 1H), 3.47 (dd, J = 11.1, 5.3 Hz, 2H), 2.67 (td, J = 11.8, 3.6 Hz, 2H), 2.26 (s, 3H), 1.07 (d, J = 8.0 Hz, 6H). | Yp AA133 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-677 | 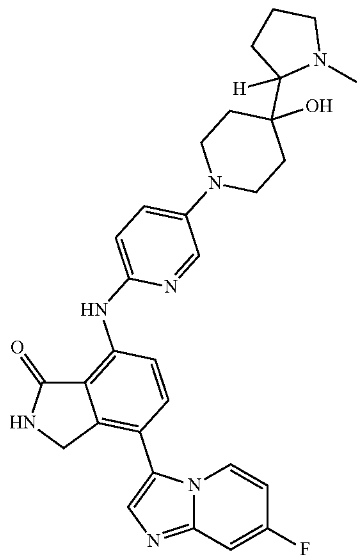 [SMILES: CN1CCCC1C1(O)CCN(c2ccc(Nc3ccc(-c4cnc5cc(F)ccn45)c4c3C(=O)NC4)nc2)CC1] | 4-(7-fluoro-imidazo[1,2-a]pyridin-3-yl)-7-((5-(4-hydroxy-4-(1-methylpyrrolidin-2-yl)piperidin-1-yl)pyridin-2-yl)amino)iso-indolin-1-one | LCMS Method C m/z = 542.9 [M + H]+, Ret. time = 1.25 min | 1H NMR (400 MHz, DMSO-d6) δ 9.83 (s, 1H), 8.79 (s, 1H), 8.56 (d, J = 8.6 Hz, 1H), 8.43 (dd, J = 7.6, 5.7 Hz, 1H), 8.33 (s, 1H), 8.02 (d, J = 3.0 Hz, 1H), 7.82 (s, 1H), 7.70 (d, J = 8.6 Hz, 1H), 7.54 (dd, J = 10.1, 2.7 Hz, 1H), 7.45 (dd, J = 9.0, 3.1 Hz, 1H), 7.04-6.90 (m, 2H), 4.38 (s, 2H), 2.96 (dtt, J = 12.2, 6.6, 3.0 Hz, 3H), 2.43 (s, 3H), 2.33-2.28 (m, 3H), 1.75 (td, J = 8.7, 4.4 Hz, 3H), 1.70-1.60 (m, 3H), 1.59-1.48 (m, 3H). | Xp AA134 BB63 |

| # | STRUCTURE | NAME | LCMS | ¹H NMR | Method Reagent AA BB |
|---|---|---|---|---|---|
| I-678 | (structure) | (R)-4-(7-fluoro-imidazo[1,2-a]pyridin-3-yl)-7-((5-(3-(3-hydroxy-1-methylazetidin-3-yl)piperidin-1-yl)pyridin-2-yl)amino)iso-indolin-1-one | LCMS Method C m/z = 528.2 [M + H]+, Ret. time = 1.24 min Chiral HPLC method X4: Ret. time = 11.31 | 1H NMR (400 MHz, DMSO-d6) δ 9.84 (s, 1H), 8.79 (s, 1H), 8.57 (d, J = 8.5 Hz, 1H), 8.43 (dd, J = 7.6, 5.7 Hz, 1H), 8.00 (d, J = 3.1 Hz, 1H), 7.82 (s, 1H), 7.70 (d, J = 8.6 Hz, 1H), 7.54 (dd, J = 10.1, 2.7 Hz, 1H), 7.45 (dd, J = 9.0, 3.0 Hz, 1H), 7.04-6.90 (m, 2H), 5.22 (s, 1H), 4.39 (s, 2H), 3.62 (d, J = 12.0 Hz, 2H), 3.47 (dd, J = 27.8, 7.3 Hz, 4H), 2.88 (dd, J = 15.8, 7.4 Hz, 2H), 2.59 (d, J = 11.2 Hz, 1H), 2.28 (s, 1H), 1.81 (td, J = 16.2, 12.0, 7.0 Hz, 3H), 1.58 (d, J = 13.0 Hz, 1H), 1.37-1.23 (m, 2H). | Yp AA135 BB63 |
| I-679 | (structure) | (S)-4-(7-fluoro-imidazo[1,2-a]pyridin-3-yl)-7-((5-(3-(3-hydroxy-1-methylazetidin-3-yl)piperidin-1-yl)pyridin-2-yl)amino)iso-indolin-1-one | LCMS Method C m/z = 528.6 [M + H]+, Ret. time = 1.22 min Chiral HPLC method X4: Ret. time = 12.86 | 1H NMR (400 MHz, DMSO-d6) δ 9.84 (s, 1H), 8.79 (s, 1H), 8.57 (d, J = 8.5 Hz, 1H), 8.43 (dd, J = 7.6, 5.7 Hz, 1H), 8.01 (d, J = 3.0 Hz, 1H), 7.82 (s, 1H), 7.70 (d, J = 8.6 Hz, 1H), 7.54 (dd, J = 10.1, 2.7 Hz, 1H), 7.45 (dd, J = 9.0, 3.0 Hz, 1H), 6.98 (ddd, J = 10.8, 6.7, 3.0 Hz, 2H), 5.26 (s, 1H), 4.39 (s, 2H), 4.12 (s, 1H), 3.62 (d, J = 11.7 Hz, 2H), 3.54 (d, J = 7.6 Hz, 2H), 3.47 (s, 1H), 3.18 (s, 2H), 2.92 (dd, J = 16.0, 7.5 Hz, 2H), 2.30 (s, 3H), 1.82 (dt, J = 21.0, 10.5 Hz, 3H), 1.25 (s, 1H), | Yp AA136 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-680 | 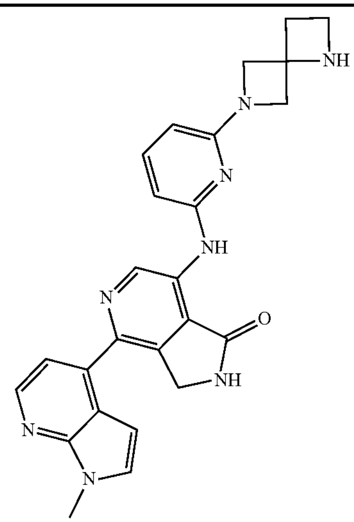 | 7-((6-(1,6-diazaspiro[3.3]heptan-6-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 453.2 [M + H]+, Ret. time = 3.54 min | 1H NMR (400 MHz, DMSO-d6) δ 9.96 (s, 1H), 9.56 (s, 1H), 9.22 (s, 1H), 8.38-8.24 (m, 2H), 7.63-7.47 (m, 2H), 7.38 (d, J = 5.0 Hz, 1H), 6.87 (d, J = 3.5 Hz, 1H), 6.37 (d, J = 7.8 Hz, 2H), 4.71 (s, 2H), 4.48 (d, J = 10.0 Hz, 2H), 3.91 (t, J = 7.0 Hz, 2H), 3.87 (s, 3H), 3.83 (d, J = 10.3 Hz, 2H), 2.59 (t, J = 7.0 Hz, 2H). | O AA137 BB14 |
| I-681 | 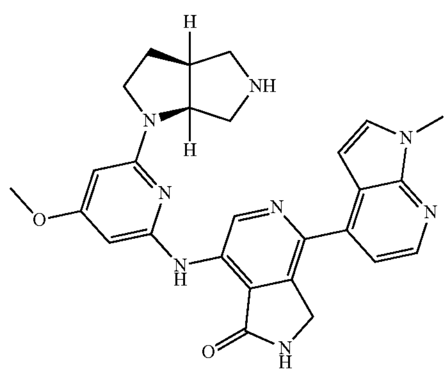 | 7-((6-((3aS,6aS)-hexahydro-pyrrolo[3,4-b]pyrrol-1(2H)-yl)-4-methoxypyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 497.2 [M + H]+, Ret. time = 3.57 min Chiral HPLC method X3: Ret. time = 6.05 | 1H NMR (400 MHz, DMSO-d6) δ 10.02 (s, 1H), 9.52 (s, 1H), 9.22 (s, 1H), 8.42-8.24 (m, 2H), 7.58 (d, J = 3.5 Hz, 1H), 7.39 (d, J = 5.0 Hz, 1H), 6.88 (d, J = 3.5 Hz, 1H), 5.92 (d, J = 1.7 Hz, 1H), 5.62 (d, J = 1.7 Hz, 1H), 4.70 (s, 2H), 4.45 (s, 1H), 3.88 (s, 3H), 3.62 (dd, J = 10.2, 6.6 Hz, 2H), 3.49 (s, 1H), 3.21 (dd, J = 12.1, 5.9 Hz, 1H), 3.16-3.05 (m, 2H), 3.01 (s, 2H), 2.89 (dd, J = 11.0, 3.6 Hz, 2H), 2.13 (dq, J = 14.2, 7.4 Hz, 1H), 1.89 (dq, J = 12.6, 6.5 Hz, 1H). | Zp AA138 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-682 | 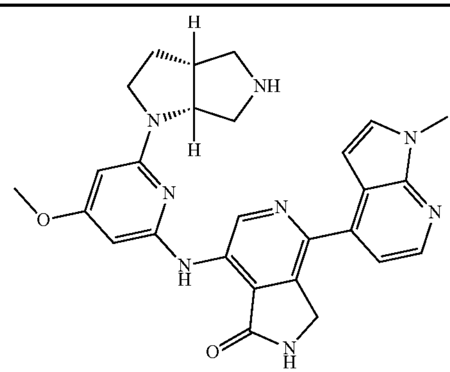 | 7-(((3aR,6aR)-hexahydro-pyrrolo[3,4-b]pyrrol-1(2H)-yl)-4-methoxypyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 497.2 [M + H]+, Ret. time = 3.56 min Chiral HPLC method X3: Ret. time = 5.99 | 1H NMR (400 MHz, DMSO-d6) δ 10.02 (d, J = 2.9 Hz, 1H), 9.53 (d, J = 3.0 Hz, 1H), 9.22 (s, 1H), 8.44-8.21 (m, 2H), 7.58 (d, J = 3.4 Hz, 1H), 7.38 (dd, J = 5.2, 2.9 Hz, 1H), 6.88 (d, J = 3.4 Hz, 1H), 5.92 (d, J = 1.7 Hz, 1H), 5.62 (d, J = 1.7 Hz, 1H), 4.70 (s, 2H), 4.45 (s, 1H), 3.88 (s, 3H), 3.62 (dd, J = 10.2, 6.6 Hz, 2H), 3.49 (s, 1H), 3.21 (dd, J = 12.1, 5.9 Hz, 1H), 3.16-3.05 (m, 2H), 3.01 (s, 2H), 2.89 (dd, J = 11.0, 3.6 Hz, 2H), 2.13 (dq, J = 14.2, 7.4 Hz, 1H), 1.89 (dq, J = 12.6, 6.5 Hz, 1H). | Zp AA138 BB14 |
| I-683 | 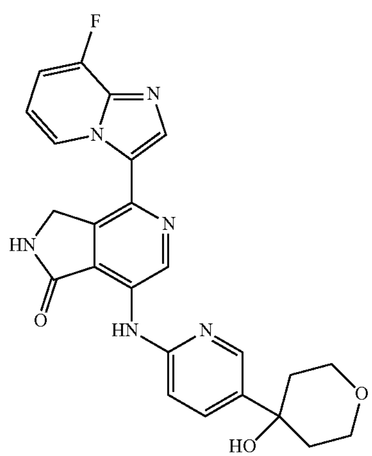 [SMILES: O=C1NCc2c(-c3cnc4c(F)cccn34)ncc(Nc3ccc(C4(O)CCOCC4)cn3)c21] | 4-(8-fluoro-imidazo[1,2-a]pyridin-3-yl)-7-(5-(4-hydroxytetra-hydro-2H-pyran-4-yl)pyridin-2-yl)amino)-2,3-dihydro-1H-pyrrolo[3,4-c]pyridin-1-one | LCMS Method J m/z = 461.2 [M + H]+, Ret. time = 3.55 min | 1H NMR (400 MHz, DMSO-d6) δ 10.05 (s, 1H), 9.66 (s, 2H), 9.36 (s, 1H), 8.54-8.39 (m, 1H), 8.15 (s, 1H), 7.91-7.73 (m, 1H), 7.35 (dd, J = 11.1, 7.6 Hz, 1H), 7.09 (t, J = 8.4 Hz, 2H), 5.20 (s, 1H), 4.79 (s, 2H), 3.98-3.69 (m, 6H), 1.62 (d, J = 13.1 Hz, 1H), 1.23 (s, 1H). | O AA57 BB87 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-684 | 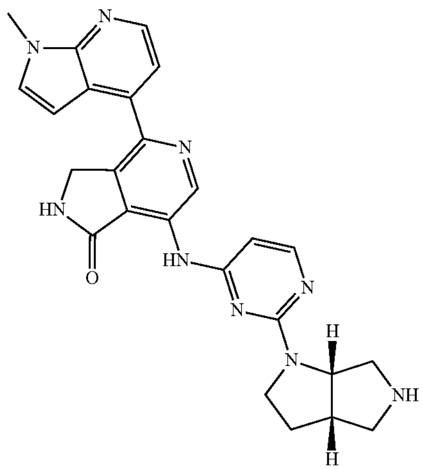 [SMILES: Cn1ccc2c(-c3ncc(Nc4ccnc(N5CC[C@H]6CNC[C@H]65)n4)c4c3CNC4=O)ccnc21] | 7-((3aS,6aS)-hexahydro-pyrrolo[3,4-b]pyrrol-1(2H)-yl)pyrimidin-4-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 468.2 [M + H]+, Ret. time = 2.84 min Chiral HPLC method X9: Ret. time = 13.77 | 1H NMR (400 MHz, DMSO-d6) δ 10.03 (s, 1H), 9.79 (s, 1H), 9.33 (s, 1H), 8.43-8.22 (m, 2H), 8.12 (d, J = 5.6 Hz, 1H), 7.60 (d, J = 3.4 Hz, 1H), 7.41 (d, J = 4.9 Hz, 1H), 6.87 (d, J = 3.4 Hz, 1H), 6.32 (d, J = 5.5 Hz, 1H), 4.71 (s, 2H), 4.49 (s, 2H), 3.88 (s, 3H), 3.20 (s, 2H), 3.11-3.08 (m, 1H), 3.00 (dq, J = 8.1, 4.7, 4.2 Hz, 1H), 2.91 (s, 2H), 2.10 (s, 1H), 1.89 (s, 1H). | Zp AA139 BB14 |
| I-685 | 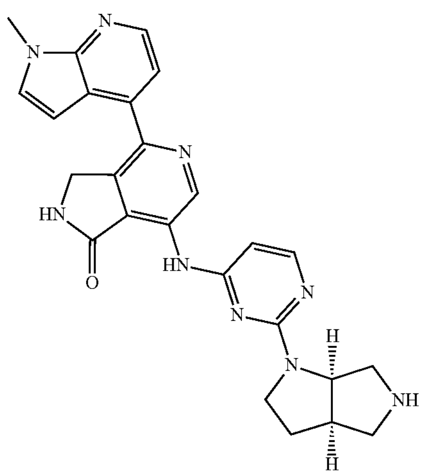 [SMILES: Cn1ccc2c(-c3ncc(Nc4ccnc(N5CC[C@@H]6CNC[C@@H]65)n4)c4c3CNC4=O)ccnc21] | 7-((3aR,6aR)-hexahydro-pyrrolo[3,4-b]pyrrol-1(2H)-yl)pyrimidin-4-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 468.2 [M + H]+, Ret. time = 2.84 min Chiral HPLC method X9: Ret. time = 8.89 | 1H NMR (400 MHz, DMSO-d6) δ 10.03 (s, 1H), 9.79 (s, 1H), 9.33 (s, 1H), 8.37 (d, J = 5.0 Hz, 1H), 8.30 (s, 1H), 8.12 (d, J = 5.6 Hz, 1H), 7.60 (d, J = 3.5 Hz, 1H), 7.41 (d, J = 5.0 Hz, 1H), 6.86 (d, J = 3.4 Hz, 1H), 6.33 (d, J = 5.6 Hz, 1H), 4.72 (s, 2H), 4.52 (s, 1H), 3.22 (d, J = 13.9 Hz, 2H), 3.16 (d, J = 19.5 Hz, 3H), 2.97 (d, J = 32.7 Hz, 3H), 2.00 (d, J = 85.8 Hz, 2H), 2.10 (s, 1H), 1.89 (s, 1H). | Zp AA139 BB14 |

| # | STRUCTURE | NAME | LCMS | 1H NMR | Method Reagent AA BB |
|---|---|---|---|---|---|
| I-686 | 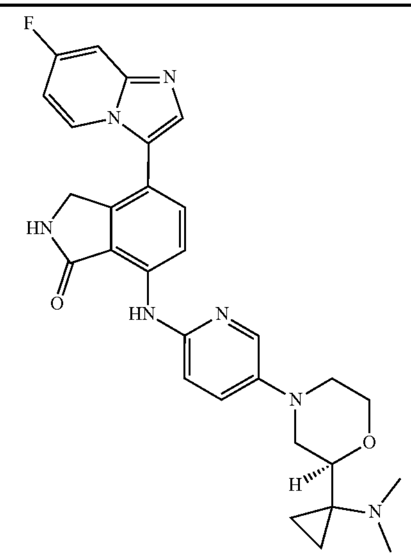 | (R)-7-((5-(2-(1-(dimethyl-amino)cyclo-propyl)mor-pholino)pyridin-2-yl)amino)-4-(7-fluoro-imidazo[1,2-a]pyridin-3-yl)isoindolin-1-one | LCMS Method J m/z = 528.2 [M + H]+, Ret. time = 2.99 min Chiral HPLC method X9: Ret. time = 7.30 | 1H NMR (400 MHz, DMSO-d6) δ 9.88 (s, 1H), 8.81 (s, 1H), 8.59 (d, J = 8.5 Hz, 1H), 8.50-8.36 (m, 1H), 8.03 (d, J = 3.0 Hz, 1H), 7.83 (s, 1H), 7.70 (d, J = 8.5 Hz, 1H), 7.51 (ddd, J = 21.0, 9.5, 2.9 Hz, 2H), 6.99 (dd, J = 9.4, 5.5 Hz, 2H), 4.39 (s, 2H), 3.94 (dd, J = 11.1, 3.2 Hz, 1H), 3.79 (d, J = 10.5 Hz, 1H), 3.73-3.60 (m, 1H), 3.49-3.37 (m, 2H), 2.62 (td, J = 11.6, 3.4 Hz, 2H), 2.33 (s, 6H), 0.71 (d, J = 6.9 Hz, 2H), 0.53 (s, 2H). | Yp AA140 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-687 | 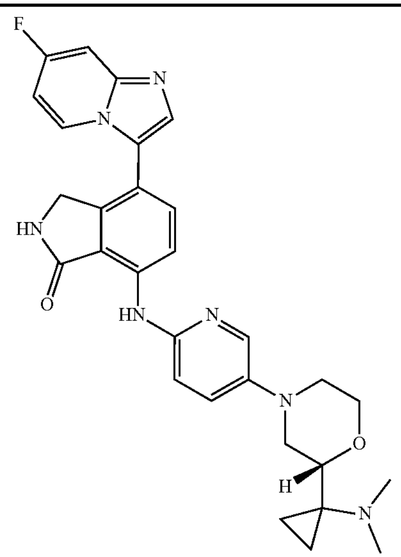 | (S)-7-(5-((2-(1-(dimethyl-amino)cyclopropyl)morpholino)pyridin-2-yl)amino)-4-(7-fluoro-imidazo[1,2-a]pyridin-3-yl)isoindolin-1-one | LCMS Method J m/z = 528.2 [M + H]+, Ret. time = 2.98 min Chiral HPLC method X9: Ret. time = 7.45 | 1H NMR (400 MHz, DMSO-d6) δ 9.88 (s, 1H), 8.81 (s, 1H), 8.59 (d, J = 8.6 Hz, 1H), 8.43 (dd, J = 7.6, 5.7 Hz, 1H), 8.03 (d, J = 3.0 Hz, 1H), 7.83 (s, 1H), 7.70 (d, J = 8.6 Hz, 1H), 7.51 (ddd, J = 20.8, 9.5, 2.8 Hz, 2H), 7.05-6.91 (m, 2H), 4.39 (s, 2H), 3.94 (dd, J = 11.1, 3.1 Hz, 1H), 3.79 (dd, J = 10.5, 2.4 Hz, 1H), 3.73-3.63 (m, 2H), 3.49-3.37 (m, 2H), 2.62 (td, J = 11.7, 3.3 Hz, 1H), 2.33 (s, 6H), 0.80-0.66 (m, 2H), 0.53 (d, J = 3.0 Hz, 2H). | Yp AA140 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-688 | 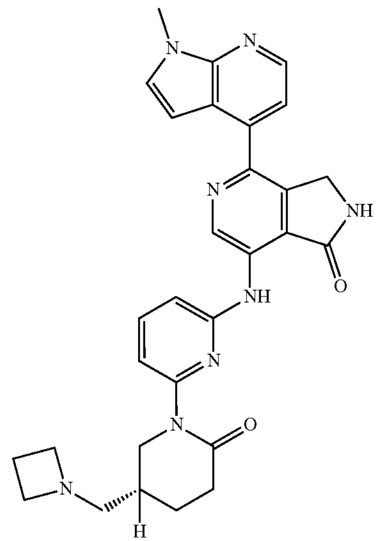 [SMILES: Cn1ccc2c(-c3ncc(Nc4cccc(N5C[C@@H](CN6CCC6)CCC5=O)n4)c4c3CNC4=O)ccnc21] | (R)-7-((6-(5-(azetidin-1-ylmethyl)-2-oxopiperidin-1-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 523.2 [M + H]+, Ret. time = 3.13 min Chiral HPLC method X9: Ret. time = 8.90 | 1H NMR (400 MHz, DMSO-d6) δ 9.91 (s, 1H), 9.81 (s, 1H), 9.27 (s, 1H), 8.37 (d, J = 5.0 Hz, 1H), 7.74 (t, J = 8.0 Hz, 1H), 7.59 (d, J = 3.5 Hz, 1H), 7.42 (d, J = 5.0 Hz, 1H), 7.33 (d, J = 7.9 Hz, 1H), 7.02-6.85 (m, 2H), 4.75 (s, 2H), 4.12 (dd, J = 12.5, 4.6 Hz, 1H), 3.88 (s, 3H), 3.63 (dd, J = 12.4, 9.7 Hz, 1H), 3.19 (s, 4H), 2.51 (s, 2H), 2.00 (s, 1H), 1.92 (dp, J = 17.6, 5.8, 5.0 Hz, 3H), 1.65-1.49 (m, 2H), 1.24 (s, 1H). | Zp AA141 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-689 | 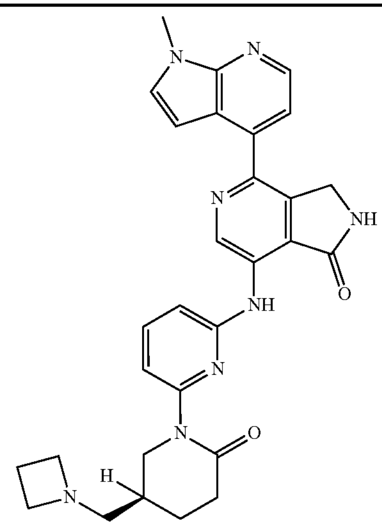 | (S)-7-((6-(5-(azetidin-1-ylmethyl)-2-oxopiperidin-1-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 523.2 [M + H]+, Ret. time = 3.13 min Chiral HPLC method X9: Ret. time = 8.63 | 1H NMR (400 MHz, DMSO-d6) δ 9.91 (s, 1H), 9.81 (s, 1H), 9.28 (s, 1H), 8.37 (d, J = 5.0 Hz, 1H), 7.74 (t, J = 8.0 Hz, 1H), 7.59 (d, J = 3.5 Hz, 1H), 7.42 (d, J = 5.0 Hz, 1H), 7.33 (d, J = 7.9 Hz, 1H), 7.02-6.85 (m, 2H), 4.75 (s, 2H), 4.12 (dd, J = 12.5, 4.6 Hz, 1H), 3.88 (s, 3H), 3.63 (dd, J = 12.4, 9.7 Hz, 1H), 3.19 (s, 4H), 2.51 (s, 2H), 2.00 (s, 1H), 1.92 (dp, J = 17.6, 5.8, 5.0 Hz, 3H), 1.65-1.49 (m, 2H), 1.24 (s, 1H). | Zp AA141 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-690 | 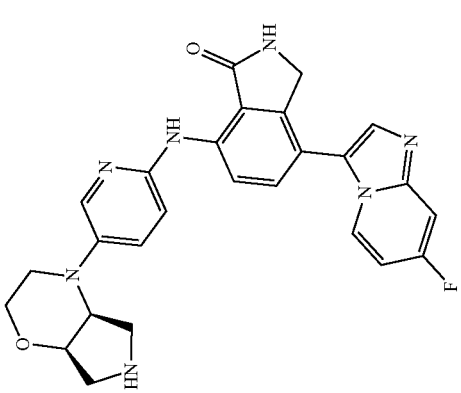 | 4-(7-fluoro-imidazo[1,2-a]pyridin-3-yl)-7-((5-((4aS,7aR)-hexahydro-pyrrolo[3,4-b][1,4]oxazin-4(4aH)-yl)pyridin-2-yl)amino)iso-indolin-1-one | LCMS Method J m/z = 486.2 [M + H]+, Ret. time = 2.87 min Chiral HPLC method X3: Ret. time = 8.87 | 1H NMR (400 MHz, DMSO-d6) δ 9.81 (s, 1H), 8.79 (s, 1H), 8.54 (d, J = 8.4 Hz, 1H), 8.43 (t, J = 6.7 Hz, 1H), 7.99 (d, J = 3.0 Hz, 1H), 7.82 (s, 1H), 7.69 (d, J = 8.6 Hz, 1H), 7.54 (dd, J = 10.0, 2.6 Hz, 1H), 7.44 (dd, J = 9.1, 3.0 Hz, 1H), 6.98 (dd, J = 8.3, 5.8 Hz, 2H), 4.39 (s, 2H), 3.99 (dt, J = 16.1, 10.0 Hz, 3H), 3.68-3.58 (m, 1H), 3.28 (d, J = 11.9 Hz, 1H), 3.14 (dd, J = 12.3, 4.3 Hz, 1H), 3.03-2.92 (m, 1H), 2.84 (dd, J = 10.3, 6.9 Hz, 1H), 2.76 (d, J = 12.3 Hz, 1H), 2.61 (t, J = 9.9 Hz, 1H), 1.24 (s, 1H). | Yp AA142 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-691 | 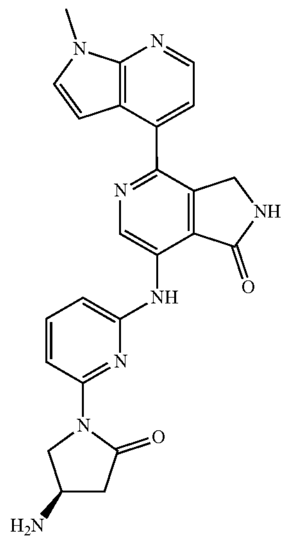 [SMILES: Cn1ccc2c(-c3ncc(Nc4cccc(N5C[C@H](N)CC5=O)n4)c4c3CNC4=O)ccnc21] | (R)-7-((6-(4-amino-2-oxopyrrolidin-1-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 455.2 [M + H]+, Ret. time = 3.23 min Chiral HPLC method X10: Ret. time = 10.17 | 1H NMR (400 MHz, DMSO-d6) δ 9.92 (s, 1H), 9.79 (s, 1H), 9.27 (s, 1H), 8.37 (d, J = 4.9 Hz, 1H), 7.91 (d, J = 8.1 Hz, 1H), 7.74 (t, J = 8.0 Hz, 1H), 7.60 (d, J = 3.5 Hz, 1H), 7.40 (d, J = 5.0 Hz, 1H), 6.88 (d, J = 3.5 Hz, 1H), 6.82 (d, J = 7.9 Hz, 1H), 4.70 (d, J = 3.9 Hz, 2H), 4.24 (dd, J = 10.7, 6.1 Hz, 1H), 3.88 (s, 3H), 3.73 (tt, J = 6.5, 3.3 Hz, 1H), 2.86 (dd, J = 16.8, 6.9 Hz, 1H), 2.31 (dd, J = 16.8, 3.6 Hz, 1H), 1.24 (s, 3H). | Zp AA143 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-692 | 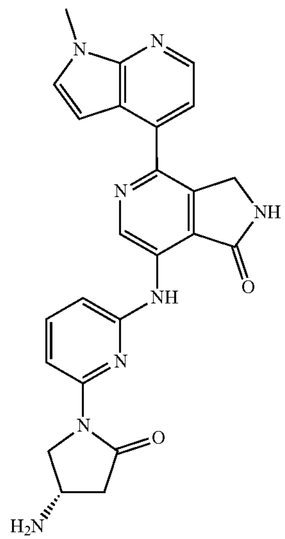 [SMILES: Cn1ccc2c(-c3ncc(Nc4cccc(N5C[C@@H](N)CC5=O)n4)c4c3CNC4=O)ccnc21] | (S)-7-((6-(4-amino-2-oxopyrrolidin-1-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 455.2 [M + H]+, Ret. time = 3.23 min Chiral HPLC method X10: Ret. time = 10.06 | 1H NMR (400 MHz, DMSO-d6) δ 9.93 (s, 1H), 9.79 (s, 1H), 9.26 (s, 1H), 8.37 (d, J = 5.0 Hz, 1H), 7.90 (d, J = 8.1 Hz, 1H), 7.74 (t, J = 8.0 Hz, 1H), 7.60 (d, J = 3.5 Hz, 1H), 7.40 (d, J = 5.0 Hz, 1H), 6.88 (d, J = 3.5 Hz, 1H), 6.81 (d, J = 7.9 Hz, 1H), 4.70 (dd, J = 3.6 Hz, 2H), 4.22 (dd, J = 10.7, 6.0 Hz, 1H), 3.94-3.81 (m, 3H), 3.70 (dt, J = 8.9, 4.2 Hz, 1H), 2.89-2.80 (m, 1H), 2.29 (dd, J = 16.6, 3.9 Hz, 1H), 1.24 (s, 3H). | Zp AA143 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-693 | 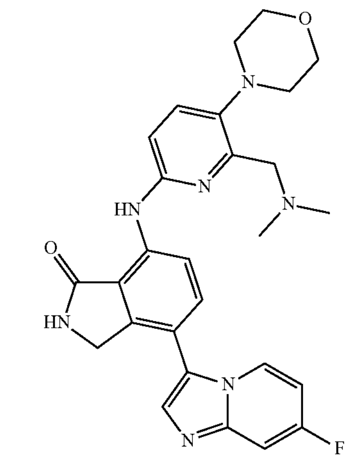 [SMILES: CN(C)Cc1nc(Nc2ccc(-c3cnc4cc(F)ccn34)c3c2C(=O)NC3)ccc1N1CCOCC1] | 7-((6-((dimethyl-amino)methyl)-5-morpholino-pyridin-2-yl)amino)-4-(7-fluoro-imidazo[1,2-a]pyridin-3-yl)isoindolin-1-one | LCMS Method J m/z = 502.2 [M + H]+, Ret. time = 2.84 min | 1H NMR (400 MHz, DMSO-d6) δ 10.04 (s, 1H), 8.84 (s, 1H), 8.76 (d, J = 8.6 Hz, 1H), 8.45 (t, J = 6.7 Hz, 1H), 7.83 (s, 1H), 7.71 (d, J = 8.6 Hz, 1H), 7.63-7.44 (m, 2H), 6.98 (dt, J = 13.9, 5.6 Hz, 2H), 4.39 (s, 2H), 3.76 (t, J = 4.4 Hz, 4H), 3.57 (s, 2H), 2.98 (t, J = 4.2 Hz, 3H), 2.32 (s, 6H), 1.24 (s, 1H). | Xp AA144 BB63 |
| I-694 | 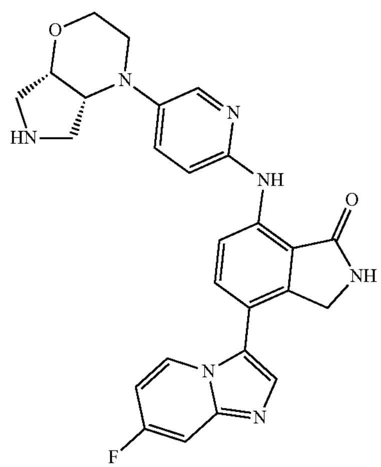 [SMILES: O=C1NCc2c(-c3cnc4cc(F)ccn34)ccc(Nc3ccc(N4CCO[C@H]5CNC[C@H]54)cn3)c21] | 4-(7-fluoro-imidazo[1,2-a]pyridin-3-yl)-7-((5-((4aR,7aS)-hexahydro-pyrrolo[3,4-b][1,4]oxazin-4(4aH)-yl)pyridin-2-yl)amino)iso-indolin-1-one | LCMS Method J m/z = 486.7 [M + H]+, Ret. time = 2.40 min Chiral HPLC method X3: Ret. time = 10.32 | 1H NMR (400 MHz, DMSO-d6) δ 9.84 (d, J = 4.8 Hz, 1H), 8.79 (s, 1H), 8.55 (d, J = 8.4 Hz, 1H), 8.43 (s, 1H), 8.29 (s, 1H), 8.02 (d, J = 10.0 Hz, 1H), 7.82 (s, 1H), 7.70 (d, J = 8.6 Hz, 1H), 7.62-7.37 (m, 2H), 7.00 (q, J = 8.1, 7.4 Hz, 2H), 4.39 (s, 2H), 4.24 (s, 1H), 4.12 (d, J = 19.3 Hz, 1H), 3.99 (d, J = 11.4 Hz, 1H), 3.00 (q, J = 13.6, 12.4 Hz, 4H), 2.80 (t, J = 9.8 Hz, 1H), 1.25 (s, 2H). | Yp AA142 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-695 | 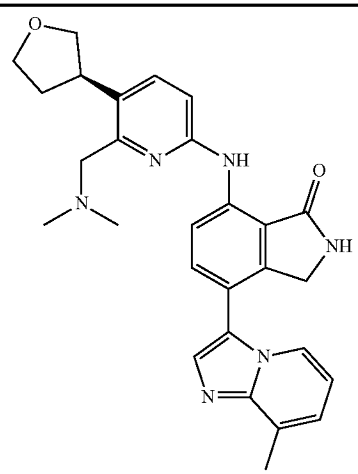 | (S)-7-((6-((dimethyl-amino)methyl)-5-(tetrahydrofuran-3-yl)pyridin-2-yl)amino)-4-(8-methyl-imidazo[1,2-a]pyridin-3-yl)isoindolin-1-one | LCMS Method J m/z = 483.2 [M + H]+, Ret. time = 2.96 min Chiral HPLC method X10: Ret. time = 6.83 | 1H NMR (400 MHz, DMSO-d6) δ 10.05 (s, 1H), 8.84 (s, 1H), 8.78 (d, J = 8.5 Hz, 1H), 8.26 (d, J = 6.9 Hz, 1H), 7.81 (s, 1H), 7.70 (dd, J = 19.8, 8.5 Hz, 2H), 7.13 (d, J = 6.8 Hz, 1H), 6.95 (d, J = 8.4 Hz, 1H), 6.86 (t, J = 6.8 Hz, 1H), 4.40 (s, 2H), 3.98 (dt, J = 13.1, 7.8 Hz, 2H), 3.82 (q, J = 7.8 Hz, 2H), 3.65 (d, J = 12.0 Hz, 1H), 3.61-3.49 (m, 3H), 2.55 (s, 3H), 2.22 (s, 6H), 1.91 (dd, J = 12.0, 7.6 Hz, 1H). | Sp AA145 BB37 |
| I-696 | 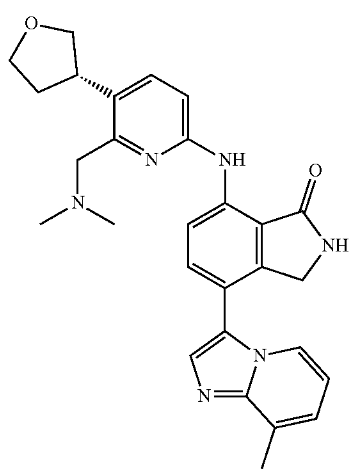 [SMILES: Cc1cccn2c(-c3ccc(Nc4ccc([C@@H]5CCOC5)c(CN(C)C)n4)c4c3CNC4=O)cnc12] | (R)-7-((6-((dimethyl-amino)methyl)-5-(tetrahydrofuran-3-yl)pyridin-2-yl)amino)-4-(8-methyl-imidazo[1,2-a]pyridin-3-yl)isoindolin-1-one | LCMS Method J m/z = 483.2 [M + H]+, Ret. time = 2.97 min Chiral HPLC method X10: Ret. time = 6.56 | 1H NMR (400 MHz, DMSO-d6) δ 10.04 (d, J = 3.6 Hz, 1H), 8.94-8.71 (m, 2H), 8.25 (d, J = 6.8 Hz, 1H), 7.91-7.78 (m, 1H), 7.70 (ddd, J = 19.6, 9.5, 4.1 Hz, 2H), 7.13 (d, J = 6.6 Hz, 1H), 7.01-6.74 (m, 2H), 4.40 (d, J = 3.6 Hz, 2H), 3.98 (ddt, J = 13.1, 8.3, 4.8 Hz, 2H), 3.82 (t, J = 7.7 Hz, 2H), 3.60-3.43 (m, 3H), 2.55 (d, J = 3.8 Hz, 3H), 2.31-2.17 (m, 6H), 1.90 (dd, J = 13.5, 7.7 Hz, 1H), 1.24 (s, 1H). | Sp AA145 BB37 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-697 | 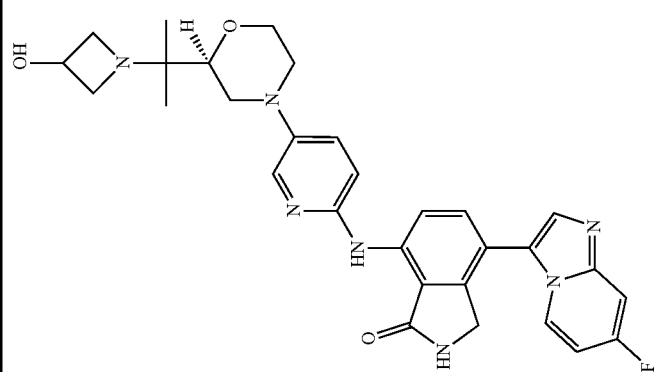 | (S)-4-(7-fluoroimidazo[1,2-a]pyridin-3-yl)-7-((5-(2-(2-(3-hydroxyazetidin-1-yl)propan-2-yl)morpholino)pyridin-2-yl)amino)isoindolin-1-one | LCMS Method J m/z = 558.2 [M + H]+, Ret. time = 2.93 min Chiral HPLC method X4: Ret. time = 10.45 | 1H NMR (400 MHz, DMSO-d6) δ 9.89 (s, 1H), 8.81 (s, 1H), 8.60 (d, J = 8.6 Hz, 1H), 8.43 (dd, J = 7.6, 5.7 Hz, 1H), 8.03 (s, 1H), 7.83 (s, 1H), 7.70 (d, J = 8.6 Hz, 1H), 7.59-7.37 (m, 2H), 6.99 (dd, J = 8.0, 5.1 Hz, 2H), 5.21 (s, 1H), 4.39 (s, 2H), 4.17 (s, 1H), 4.00 (d, J = 11.3 Hz, 2H), 3.63 (s, 1H), 3.57-3.40 (m, 3H), 2.98 (s, 2H), 2.66 (s, 1H), 1.52 (s, 1H), 1.25 (s, 1H), 0.95 (d, J = 33.4 Hz, 6H). | Yp AA146 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-698 | 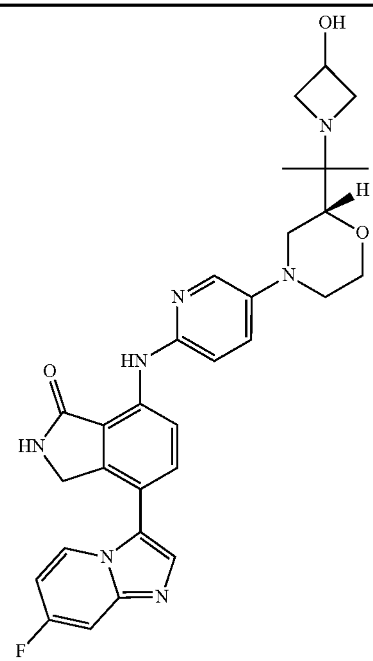 | (R)-4-(7-fluoro-imidazo[1,2-a]pyridin-3-yl)-7-((5-(2-(2-(3-hydroxyazetidin-1-yl)propan-2-yl)morpholino)pyridin-2-yl)amino)isoindolin-1-one | LCMS Method J m/z = 558.2 [M + H]+, Ret. time = 2.94 min Chiral HPLC method X4: Ret. time = 11.32 | 1H NMR (400 MHz, DMSO-d6) δ 10.69 (s, 1H), 9.62 (s, 1H), 9.40 (d, J = 8.5 Hz, 1H), 9.24 (dd, J = 7.6, 5.7 Hz, 1H), 8.83 (d, J = 3.0 Hz, 1H), 8.64 (s, 1H), 8.51 (d, J = 8.6 Hz, 1H), 8.35 (dd, J = 10.1, 2.7 Hz, 1H), 8.27 (dd, J = 9.0, 3.0 Hz, 1H), 7.80 (dq, J = 7.5, 3.0 Hz, 2H), 6.02 (s, 1H), 5.20 (s, 2H), 4.95 (dq, J = 10.4, 5.8, 5.2 Hz, 2H), 4.80 (d, J = 10.7 Hz, 1H), 4.43 (dd, J = 12.4, 9.8 Hz, 1H), 4.34 (d, J = 11.6 Hz, 1H), 4.25 (d, J = 11.8 Hz, 1H), 3.99 (d, J = 5.3 Hz, 2H), 3.80 (s, 2H), 2.06 (s, 1H), 1.25 (s, 1H), 1.76 (d, J = 28.7 Hz, 6H). | Yp AA146 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-699 | 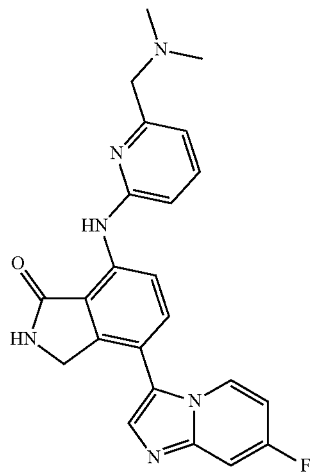 [SMILES: CN(C)Cc1cccc(Nc2ccc(-c3cnc4cc(F)ccn34)c3c2C(=O)NC3)n1] | 7-((6-((dimethyl-amino)meth-yl)pyridin-2-yl)amino)-4-(7-fluoro-imidazo[1,2-a]pyridin-3-yl)isoindolin-1-one | LCMS Method J m/z = 417.0 [M + H]+, Ret. time = 2.57 min | 1H NMR (400 MHz, DMSO-d6) δ 10.13 (s, 1H), 8.88 (s, 1H), 8.80-8.78 (d, J = 8.4 Hz, 1H), 8.49-8.46 (t, J = 6 Hz, 1H), 7.85 (s, 1H), 7.76-7.67 (dd, J = 8.4 Hz, 2H), 8.56-7.53 (m, 1H), 7.00-6.96 (dd, J = 10.1, 2.7 Hz, 2H), 6.89-6.87 (d, J = 8.4 Hz, 1H), 4.42 (s, 2H), 3.55 (s, 2H), 2.27 (s, 6H). | ACp AA147 BB63 |
| I-700 | 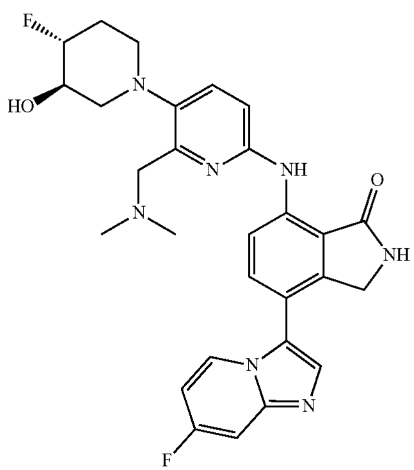 [SMILES: CN(C)Cc1nc(Nc2ccc(-c3cnc4cc(F)ccn34)c3c2C(=O)NC3)ccc1N1CC[C@@H](F)[C@H](O)C1] | 7-((6-(((dimethyl-amino)methyl)-5-((3R,4R)-4-fluoro-3-hydroxy-piperidin-1-yl)pyridin-2-yl)amino)-4-(7-fluoro-imidazo[1,2-a]pyridin-3-yl)isoindolin-1-one | LCMS Method J m/z = 534.2 [M + H]+, Ret. time = 2.84 min Chiral HPLC method X6: Ret. time = 11.31 | 1H NMR (400 MHz, DMSO-d6) δ 10.03 (s, 1H), 8.84 (s, 1H), 8.76-8.74 (d, J = 8.8 Hz, 1H), 8.46-8.43 (t, J = 6.4 Hz, 1H), 7.83 (s, 1H), 7.72-7.70 (d, J = 8.8 Hz, 1H), 8.55-7.53 (d, J = 8.8 Hz, 2H), 6.98-6.92 (m, 2H), 5.43 (bs, 1H), 4.39 (s, 3H), 3.59 (bs, 2H), 3.56-3.51 (m, 2H), 3.26 (bs, 2H), 2.32 (s, 6H), 2.13 (s, 1H), 1.81 (s, 1H), 1.24 (s, 1H), | Sp AA148 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-701 | 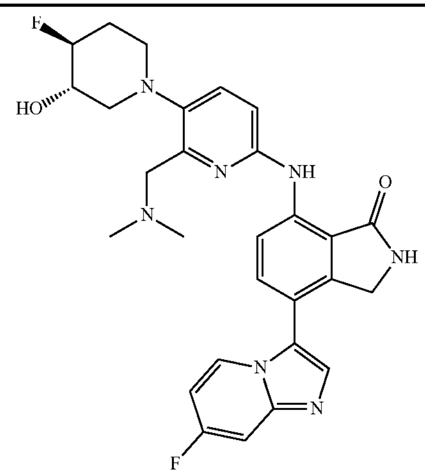 | 7-((6-((dimethyl-amino)methyl)-5-((3S,4S)-4-fluoro-3-hydroxy-piperidin-1-yl)pyridin-2-yl)amino)-4-(7-fluoro-imidazo[1,2-a]pyridin-3-yl)isoindolin-1-one | LCMS Method J m/z = 534.3 [M + H]+, Ret. time = 2.83 min Chiral HPLC method X6: Ret. time = 11.31 | 1H NMR (400 MHz, DMSO-d6) δ 10.03 (s, 1H), 8.84 (s, 1H), 8.74-8.72 (d, J = 8.8 Hz, 1H), 8.46-8.43 (t, J = 6.4 Hz, 1H), 7.83 (s, 1H), 7.72-7.70 (d, J = 8.8 Hz, 1H), 8.55-7.53 (d, J = 8.8 Hz, 2H), 6.94-6.94 (m, 2H), 5.43 (bs, 1H), 4.39 (s, 3H), 3.59 (bs, 2H), 3.56-3.51 (m, 2H), 3.26 (bs, 2H), 2.32 (s, 6H), 2.13 (s, 1H), 1.81 (s, 1H), 1.24 (s, 1H), | Sp AA148 BB63 |
| I-702 | 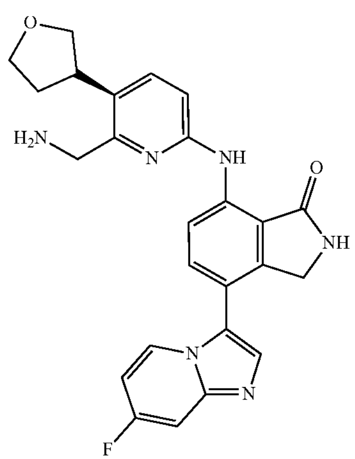 | (S)-7-((6-(aminomethyl)-5-(tetrahydrofuran-3-yl)pyridin-2-yl)amino)-4-(7-fluoro-imidazo[1,2-a]pyridin-3-yl)isoindolin-1-one | LCMS Method J m/z = 459.2 [M + H]+, Ret. time = 2.65 min Chiral HPLC method X9: Ret. time = 8.64 | 1H NMR (400 MHz, DMSO-d6) δ 10.05 (s, 1H), 8.87 (s, 1H), 8.61-8.59 (d, J = 8.4 Hz, 2H), 8.42-8.39 (t, J = 6.4 Hz, 1H), 8.28 (s, 1H), 7.84 (s, 1H), 7.73-7.67 (dd, J = 8.4 Hz, 2H), 7.56-7.53 (d, J = 9.6 Hz, 1H), 7.01-6.99 (m, 2H), 4.40 (s, 2H), 4.12 (s, 2H), 4.01-3.95 (m, 2H), 3.81 (bs, 1H), 3.57 (s, 2H), 1.89 (bs, 2H). | Sp AA149 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-703 | 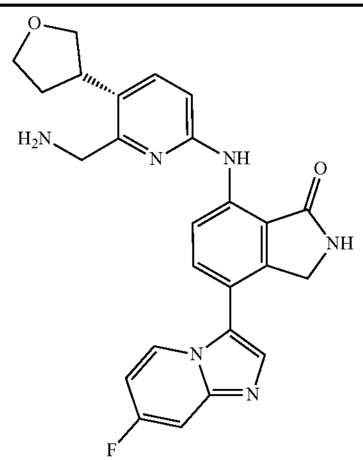 | (R)-7-((6-(aminomethyl)-5-(tetrahydrofuran-3-yl)pyridin-2-yl)amino)-4-(7-fluoro-imidazo[1,2-a]pyridin-3-yl)isoindolin-1-one | LCMS Method J m/z = 459.2 [M + H]+, Ret. time = 2.64 min Chiral HPLC method X9: Ret. time = 8.62 | 1H NMR (400 MHz, DMSO-d6) δ 10.06 (s, 1H), 8.89 (s, 1H), 8.62-8.60 (d, J = 8.4 Hz, 2H), 8.44-8.40 (t, J = 6.4 Hz, 1H), 8.28 (s, 1H), 7.85 (s, 1H), 7.74-7.68 (dd, J = 8.4 Hz, 2H), 7.57-7.54 (d, J = 9.6 Hz, 1H), 7.04-7.00 (m, 2H), 4.41 (s, 2H), 4.14 (s, 2H), 4.01-3.95 (m, 2H), 3.81 (bs, 1H), 3.57 (s, 2H), 1.89 (bs, 2H). | Sp AAA149 BB63 |
| I-704 | 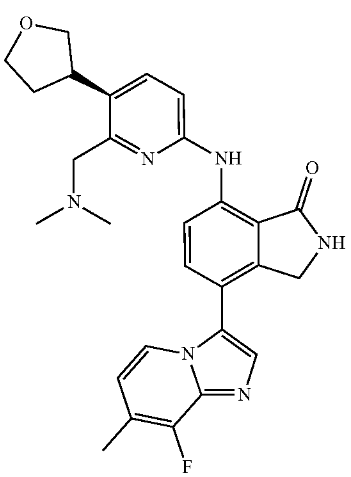 | (S)-7-((dimethyl-amino)methyl)-5-(tetrahydrofuran-3-yl)pyridin-2-yl)amino)-4-(8-fluoro-7-methyl-imidazo[1,2-a]pyridin-3-yl)isoindolin-1-one | LCMS Method J m/z = 501.2 [M + H]+, Ret. time = 3.15 min Chiral HPLC method X6: Ret. time = 14.65 | 1H NMR (400 MHz, DMSO-d6) δ 10.05 (s, 1H), 8.85 (d, J = 8.4 Hz, 1H), 8.77-8.75 (d, J = 8.4 Hz, 1H), 8.18-8.16 (d, J = 6.8 Hz, 1H), 7.81 (s, 1H), 7.72-7.68 (dd, J = 8.4 Hz, 2H), 6.96-6.94 (d, J = 8.4 Hz, 1H), 6.85-6.81 (t, J = 6.8 Hz, 1H), 4.40 (s, 2H), 4.00-3.98 (m, 1H), 3.82-3.81 (d, J = 7.6 Hz, 2H), 3.64 (bs, 1H), 3.55-3.53 (t, J = 7.2 Hz, 3H), 2.34 (s, 3H), 2.22 (s, 6H), 1.90 (bs, 1H), 1.24 (s, 1H). | Sp AA145 BB80 |

| # | STRUCTURE | NAME | LCMS | 1H NMR | Method Reagent AA BB |
|---|---|---|---|---|---|
| I-705 | 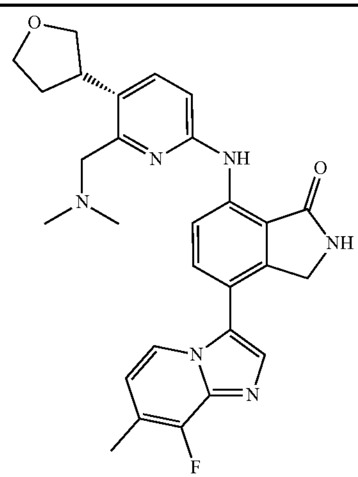 | (R)-7-((6-((dimethyl-amino)methyl)-5-(tetrahydrofuran-3-yl)pyridin-2-yl)amino)-4-(8-fluoro-7-methylimidazo[1,2-a]pyridin-3-yl)isoindolin-1-one | LCMS Method J m/z = 501.2 [M + H]+, Ret. time = 2.99 min Chiral HPLC method X6: Ret. time = 13.43 | 1H NMR (400 MHz, DMSO-d6) δ 10.06 (s, 1H), 8.86 (s, 1H), 8.79-8.77 (d, J = 8.4 Hz, 1H), 8.19-8.18 (d, J = 6.8 Hz, 1H), 7.82 (s, 1H), 7.72-7.68 (dd, J = 8.4 Hz, 2H), 6.96-6.94 (d, J = 8.4 Hz, 1H), 6.85-6.84 (t, J = 6.8 Hz, 1H), 4.40 (s, 2H), 4.00-3.98 (m, 1H), 3.82-3.81 (d, J = 7.6 Hz, 2H), 3.64 (bs, 1H), 3.55-3.53 (t, J = 7.2 Hz, 3H), 2.34 (s, 3H), 2.22 (s, 6H), 1.90 (bs, 1H), 1.24 (s, 1H). | Sp AA145 BB80 |
| I-706 | 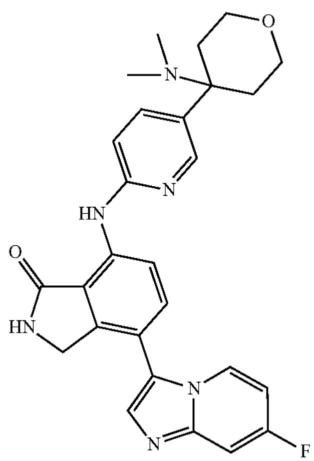 [SMILES: CN(C)C1(c2ccc(Nc3ccc(-c4cnc5cc(F)ccn45)c4c3C(=O)NC4)nc2)CCOCC1] | 7-((5-(4-(dimethyl-amino)tetrahydro-2H-pyran-4-yl)pyridin-2-yl)amino)-4-(7-fluoro-imidazo[1,2-a]pyridin-3-yl)isoindolin-1-one | LCMS Method J m/z = 488.2 [M + H]+, Ret. time = 2.58 min | 1H NMR (400 MHz, DMSO-d6) δ 10.11 (s, 1H), 8.87 (d, J = 8.4 Hz, 1H), 8.78-8.75 (d, J = 8.4 Hz, 1H), 8.46-8.42 (t, J = 6.8 Hz, 1H), 8.29 (s, 1H), 7.84 (s, 1H), 7.76-7.74 (d, J = 8.8 Hz, 1H), 7.68-7.66 (d, J = 7.2 Hz, 1H), 7.55-7.53 (d, J = 10 Hz, 1H), 7.05-7.03 (d, J = 8.8 Hz, 1H), 7.00-6.97 (t, J = 7.2 Hz, 1H), 4.41 (s, 2H), 3.79 (bs, 2H), 2.19 (bs, 2H), 2.06 (bs, 2H), 1.98 (s, 6H), 1.24 (s, 2H). | Xp AA150 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-707 | 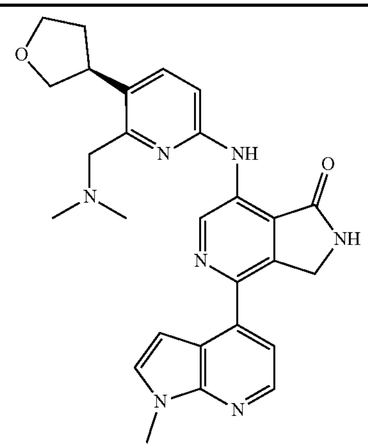 | (S)-7-((6-((dimethylamino)methyl)-5-(tetrahydrofuran-3-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 484.2 [M + H]+, Ret. time = 3.09 min Chiral HPLC method X14: Ret. time = 10.12 | 1H NMR (400 MHz, DMSO-d6) δ 10.11 (s, 1H), 9.69 (s, 1H), 9.22 (s, 1H), 8.36-8.35 (d, J = 4.8 Hz, 1H), 7.70-7.68 (d, J = 8.4 Hz, 1H), 7.59-7.58 (d, J = 3.2 Hz, 1H), 7.39-7.38 (d, J = 4.8 Hz, 1H), 7.05-7.03 (d, J = 8.4 Hz, 1H), 6.88-6.87 (d, J = 3.2 Hz, 1H), 4.70 (s, 2H), 4.02-3.94 (m, 2H), 3.87 (s, 3H), 3.84-3.80 (m, 2H), 3.66 (s, 1H), 3.55-3.51 (t, J = 7.2 Hz, 2H), 2.23 (s, 6H), 1.94-1.86 (m, 1H), 1.24 (s, 1H). | Up AA145 BB14 |
| I-708 | 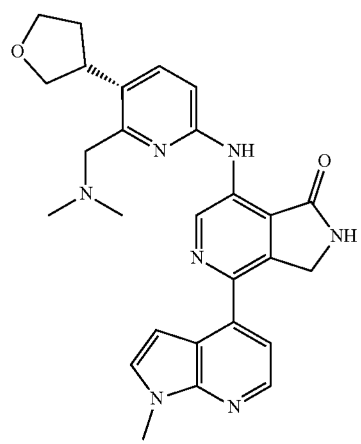 | (R)-7-((6-((dimethylamino)methyl)-5-(tetrahydrofuran-3-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 484.2 [M + H]+, Ret. time = 3.09 min Chiral HPLC method X14: Ret. time = 10.02 | 1H NMR (400 MHz, DMSO-d6) δ 10.11 (s, 1H), 9.69 (s, 1H), 9.22 (s, 1H), 8.36-8.35 (d, J = 4.8 Hz, 1H), 7.70-7.68 (d, J = 8.4 Hz, 1H), 7.59-7.58 (d, J = 3.2 Hz, 1H), 7.39-7.38 (d, J = 4.8 Hz, 1H), 7.05-7.03 (d, J = 8.4 Hz, 1H), 6.88-6.87 (d, J = 3.2 Hz, 1H), 4.70 (s, 2H), 4.02-3.94 (m, 2H), 3.87 (s, 3H), 3.84-3.80 (m, 2H), 3.66 (s, 1H), 3.55-3.51 (t, J = 7.2 Hz, 2H), 2.23 (s, 6H), 1.94-1.86 (m, 1H), 1.23 (s, 1H). | Up AA145 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-709 | 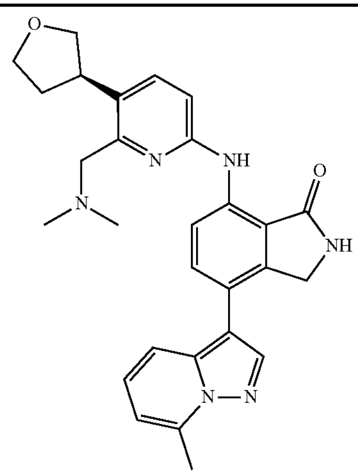 | (S)-7-((6-((dimethylamino)methyl)-5-(tetrahydrofuran-3-yl)pyridin-2-yl)amino)-4-(7-methylpyrazolo[1,5-a]pyridin-3-yl)isoindolin-1-one | LCMS Method J m/z = 483.2 [M + H]+, Ret. time = 3.66 min Chiral HPLC method X4: Ret. time = 9.05 | 1H NMR (400 MHz, DMSO-d6) δ 9.98 (s, 1H), 8.83 (s, 1H), 8.71-8.69 (d, J = 6.8 Hz, 1H), 8.38 (s, 1H), 7.77-7.75 (d, J = 8.8 Hz, 1H), 7.70-7.66 (dd, J = 8.4 Hz, 2H), 7.29-7.25 (d, J = 7.2 Hz, 1H), 6.92-6.91 (d, J = 6.4 Hz, 2H), 4.51 (s, 2H), 4.01-3.93 (m, 2H), .83-3.78 (m, 2H), 3.63 (s, 1H), 3.53-3.50 (t, J = 7.6 Hz, 2H), 2.72 (s, 3H), 2.22 (s, 6H), 1.93-1.85 (m, 1H), 1.23 (s, 1H). | Sp AA145 BB90 |
| I-710 | 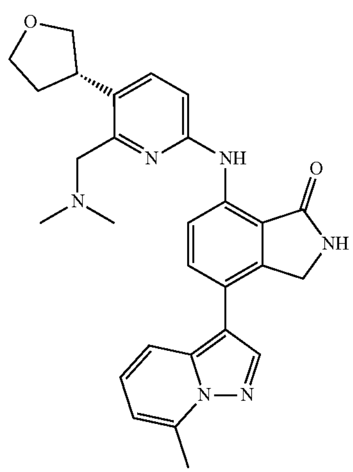 [SMILES: Cc1cccc2c(-c3ccc(Nc4ccc([C@@H]5CCOC5)c(CN(C)C)n4)c4c3CNC4=O)cnn12] | (R)-7-((6-((dimethylamino)methyl)-5-(tetrahydrofuran-3-yl)pyridin-2-yl)amino)-4-(7-methylpyrazolo[1,5-a]pyridin-3-yl)isoindolin-1-one | LCMS Method J m/z = 483.2 [M + H]+, Ret. time = 3.65 min Chiral HPLC method X4: Ret. time = 9.03 | 1H NMR (400 MHz, DMSO-d6) δ 9.98 (s, 1H), 8.84 (s, 1H), 8.71-8.69 (d, J = 6.8 Hz, 1H), 8.38 (s, 1H), 7.77-7.75 (d, J = 8.8 Hz, 1H), 7.70-7.66 (dd, J = 8.4 Hz, 2H), 7.29-7.25 (d, J = 7.2 Hz, 1H), 6.92-6.91 (d, J = 6.4 Hz, 2H), 4.51 (s, 2H), 4.01-3.93 (m, 2H), .83-3.78 (m, 2H), 3.63 (s, 1H), 3.53-3.50 (t, J = 7.6 Hz, 2H), 2.72 (s, 3H), 2.22 (s, 6H), 1.93-1.85 (m, 1H), 1.23 (s, 1H). | Sp AA145 BB90 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-711 | 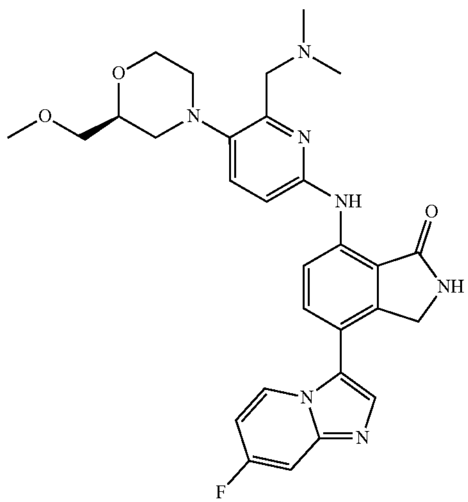 [SMILES: COC[C@@H]1CN(c2ccc(Nc3ccc(-c4cnc5cc(F)ccn45)c4c3C(=O)NC4)nc2CN(C)C)CCO1] | (R)-7-((6-((dimethyl-amino)methyl)-5-(2-(methoxymeth-yl)morpho-linopyridin-2-yl)amino)-4-(7-fluoro-imidazo[1,2-a]pyridin-3-yl)isoindolin-1-one | LCMS Method J m/z = 546.2 [M + H]+, Ret. time = 2.84 min Chiral HPLC method X4: Ret. time = 9.19 | 1H NMR (400 MHz, DMSO-d6) δ 10.03 (s, 1H), 8.85 (s, 1H), 8.72-8.71 (d, J = 6.8 Hz, 1H), 8.45-8.44 (d, J = 5.6 Hz, 1H), 7.83 (s, 1H), 7.72-7.70 (d, J = 8.0 Hz, 2H), 7.58-7.52 (t, J = 11.6 Hz, 1H), 6.98 (bs, 2H), 4.39 (s, 2H), 3.89 (s, 1H), 3.77 (s, 1H), 3.72-3.67 (t, J = 9.2 Hz, 2H), 3.64 (s, 1H), 3.40 (s, 1H), 3.27 (s, 3H), 3.17-3.15 (d, J = 7.6 Hz, 1H), 3.09-3.06 (d, J = 11.2 Hz, 1H), 2.80-2.78 (t, J = 10 Hz, 1H), 2.67 (bs, 2H), 2.37 (s, 6H). | Sp AA151 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-712 | 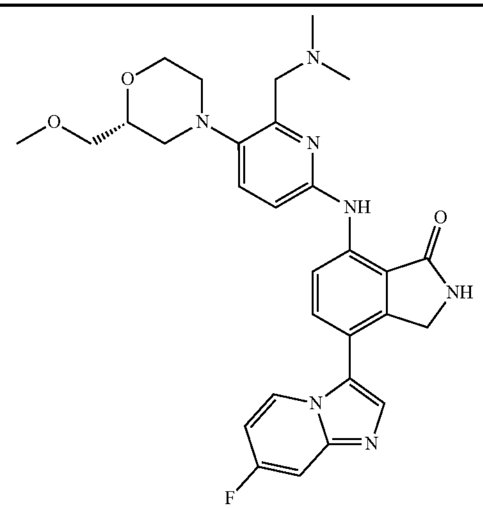 | (S)-7-((6-((dimethyl-amino)methyl)-5-(2-(methoxymeth-yl)morpho-linopyridin-2-yl)amino)-4-(7-fluoro-imidazo[1,2-a]pyridin-3-yl)isoindolin-1-one | LCMS Method J m/z = 546.2 [M + H]+, Ret. time = 2.83 min Chiral HPLC method X4: Ret. time = 9.31 | 1H NMR (400 MHz, DMSO-d6) δ 10.03 (s, 1H), 8.85 (s, 1H), 8.72-8.71 (d, J = 6.8 Hz, 1H), 8.45-8.42 (d, J = 5.6 Hz, 1H), 7.83 (s, 1H), 7.72-7.70 (d, J = 8.0 Hz, 2H), 7.55-7.52 (t, J = 11.6 Hz, 1H), 6.98 (bs, 2H), 4.39 (s, 2H), 3.89 (s, 1H), 3.77 (s, 1H), 3.72-3.67 (t, J = 9.2 Hz, 2H), 3.64 (s, 1H), 3.40 (s, 1H), 3.27 (s, 3H), 3.17-3.15 (d, J = 7.6 Hz, 1H), 3.09-3.06 (d, J = 11.2 Hz, 1H), 2.80-2.78 (t, J = 10 Hz, 1H), 2.67 (bs, 2H), 2.35 (s, 6H). | Sp AA151 BB63 |
| I-713 | 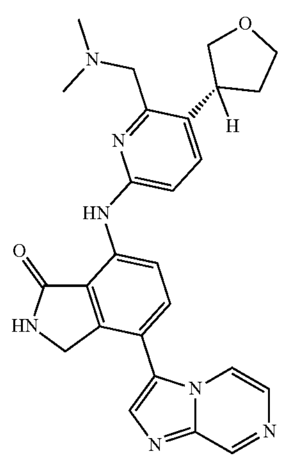 [SMILES: CN(C)Cc1nc(Nc2ccc(-c3cnc4cnccn34)c3c2C(=O)NC3)ccc1[C@H]1CCOC1] | (R)-7-((6-((dimethyl-amino)methyl)-5-(tetrahydrofuran-3-yl)pyridin-2-yl)amino)-4-(imidazo[1,2-a]pyrazin-3-yl)isoindolin-1-one | LCMS Method J m/z = 470.2 [M + H]+, Ret. time = 2.94 min Chiral HPLC method X6: Ret. time = 17.33 | 1H NMR (400 MHz, DMSO-d6) δ 10.08 (s, 1H), 9.15 (s, 1H), 8.89 (s, 1H), 8.82-8.79 (d, J = 8.4 Hz, 1H), 7.50-7.49 (dd, J = 1.6 Hz, 1H), 8.13 (s, 1H), 8.92-8.91 (d, J = 4.4 Hz, 1H), 7.82-7.80 (d, J = 8.8 Hz, 1H), 7.68-7.66 (d, J = 8.4 Hz, 1H), 6.96-6.94 (d, J = 8.4 Hz, 1H), 4.45 (s, 2H), 4.01-3.94 (m, 2H), 3.86-3.78 (m, 2H), 3.63 (bs, 1H), 3.54-3.50 (t, J = 8 Hz, 3H), 2.21 (s, 6H), 1.92-1.85 (m, 1H). | Sp AA145 BB61 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-714 | 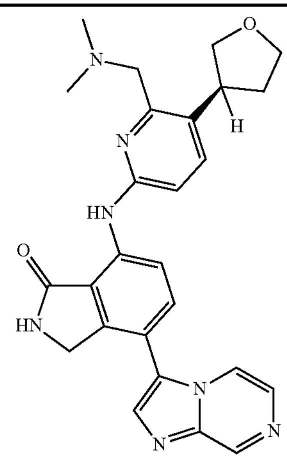 | (S)-7-((6-((dimethylamino)methyl)-5-(tetrahydrofuran-3-yl)pyridin-2-yl)amino)-4-(imidazo[1,2-a]pyrazin-3-yl)isoindolin-1-one | LCMS Method J m/z = 470.2 [M + H]+, Ret. time = 2.94 min Chiral HPLC method X6: Ret. time = 15.28 | 1H NMR (400 MHz, DMSO-d6) δ 10.08 (s, 1H), 9.15 (s, 1H), 8.89 (s, 1H), 8.82-8.79 (d, J = 8.4 Hz, 1H), 7.50-7.49 (dd, J = 1.6 Hz, 1H), 8.13 (s, 1H), 8.92-8.91 (d, J = 4.4 Hz, 1H), 7.82-7.80 (d, J = 8.8 Hz, 1H), 7.68-7.66 (d, J = 8.4 Hz, 1H), 6.96-6.94 (d, J = 8.4 Hz, 1H), 4.45 (s, 2H), 4.01-3.94 (m, 2H), 3.86-3.78 (m, 2H), 3.63 (bs, 1H), 3.54-3.50 (t, J = 8 Hz, 3H), 2.21 (s, 6H), 1.93-1.85 (m, 1H). | Sp AA145 BB61 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-715 | 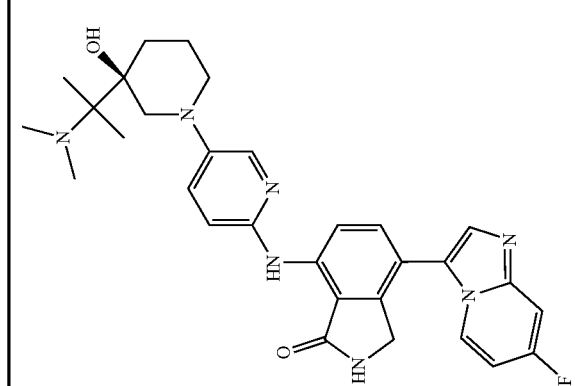 | (S)-7-((5-(3-(2-(dimethylamino)propan-2-yl)-3-hydroxypiperidin-1-yl)pyridin-2-yl)amino)-4-(7-fluoroimidazo[1,2-a]pyridin-3-yl)isoindolin-1-one | LCMS Method J m/z = 544.3 [M + H]+, Ret. time = 2.83 min Chiral HPLC method X15: Ret. time = 10.85 | 1H NMR (400 MHz, DMSO-d6) δ 9.85 (s, 1H), 8.78 (s, 1H), 8.58-8.55 (d, J = 8.8 Hz, 1H), 8.43-8.40 (t, J = 6 Hz, 1H), 8.01 (s, 1H), 7.81 (s, 1H), 7.69-7.67 (d, J = 8.8 Hz, 1H), 7.54-7.52 (dd, J = 2.4 Hz, 1H), 7.44-7.42 (d, J = 8 Hz, 1H), 7.00-6.98 (t, J = 5.2 Hz, 1H), 6.95 (s, 1H), 4.37 (s, 2H), 4.00 (bs, 1H), 3.49-3.42 (m, 2H), 2.73-2.67 (m, 2H), 2.33 (s, 6H), 1.96-1.91 (m, 1H), 1.69 (bs, 1H), 1.56 (bs, 1H), 1.52-1.46 (m, 1H), 1.05 (s, 6H). | Yp AA152 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-716 | [structure] | (R)-7-(5-(3-(2-(dimethylamino)propan-2-yl)-3-hydroxy-piperidin-1-yl)pyridin-2-yl)amino)-4-(7-fluoro-imidazo[1,2-a]pyridin-3-yl)isoindolin-1-one | LCMS Method J m/z = 544.3 [M + H]+, Ret. time = 2.81 min Chiral HPLC method X15: Ret. time = 11.41 | 1H NMR (400 MHz, DMSO-d6) δ 9.85 (s, 1H), 8.77 (s, 1H), 8.58-8.56 (d, J = 8.8 Hz, 1H), 8.43-8.40 (t, J = 6 Hz, 1H), 8.01 (s, 1H), 7.81 (s, 1H), 7.69-7.67 (d, J = 8.8 Hz, 1H), 7.54-7.52 (dd, J = 2.4 Hz, 1H), 7.44-7.42 (d, J = 8 Hz, 1H), 7.00-6.98 (t, J = 5.2 Hz, 1H), 6.95 (s, 1H), 4.37 (s, 2H), 4.00 (bs, 1H), 3.49-3.42 (m, 2H), 2.73-2.67 (m, 2H), 2.33 (s, 6H), 1.96-1.91 (m, 1H), 1.69 (bs, 1H), 1.56 (bs, 1H), 1.52-1.46 (m, 1H), 1.05 (s, 6H). | Yp AA152 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-717 | 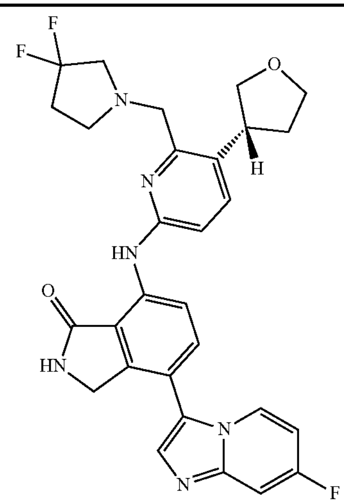 | (R)-7-((6-((3,3-difluoropyrrolidin-1-yl)methyl)-5-(tetrahydrofuran-3-yl)pyridin-2-yl)amino)-4-(7-fluoroimidazo[1,2-a]pyridin-3-yl)isoindolin-1-one | LCMS Method J m/z = 549.2 [M + H]+, Ret. time = 3.03 min Chiral HPLC method X10: Ret. time = 6.32 | 1H NMR (400 MHz, DMSO-d6) δ 10.07 (s, 1H), 8.86 (s, 1H), 8.82-8.79 (d, J = 8.4 Hz, 1H), 8.46-8.44 (t, J = 5.6 Hz, 1H), 7.83 (s, 1H), 7.73-7.68 (dd, J = 8.4 Hz, 2H), 7.55-7.52 (d, J = 10 Hz, 1H), 6.98-6.94 (t, J = 7.6 Hz, 2H), 4.39 (s, 2H), 3.98-3.89 (m, 3H), 3.77-3.71 (m, 3H), 3.57-3.53 (t, J = 7.6 Hz, 1H), 2.96-2.94 (d, J = 8.4 Hz, 2H), 2.78-2.77 (d, J = 5.6 Hz, 2H), 2.28-2.25 (m, 3H), 1.91-1.87 (m, 1H). | Sp AA153 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-718 | 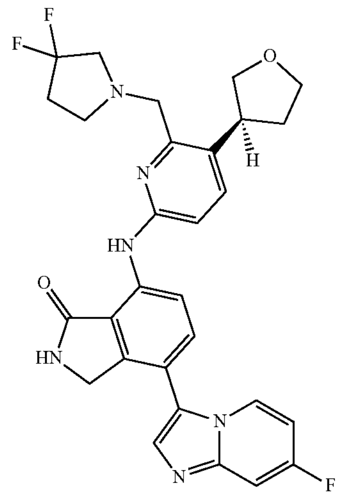 [SMILES: O=C1NCc2c(-c3cnc4cc(F)ccn34)ccc(Nc3ccc([C@@H]4CCOC4)c(CN4CCC(F)(F)C4)n3)c21] | (S)-7-((6-((3,3-difluoropyrrolidin-1-yl)methyl)-5-(tetrahydrofuran-3-yl)pyridin-2-yl)amino)-4-(7-fluoroimidazo[1,2-a]pyridin-3-yl)isoindolin-1-one | LCMS Method J m/z = 549.2 [M + H]+, Ret. time = 3.00 min Chiral HPLC method X10: Ret. time = 5.73 | 1H NMR (400 MHz, DMSO-d6) δ 10.07 (s, 1H), 8.86 (s, 1H), 8.82-8.79 (d, J = 8.4 Hz, 1H), 8.46-8.44 (t, J = 5.6 Hz, 1H), 7.83 (s, 1H), 7.73-7.68 (dd, J = 8.4 Hz, 2H), 7.55-7.52 (d, J = 10 Hz, 1H), 6.98-6.94 (t, J = 7.6 Hz, 2H), 4.39 (s, 2H), 3.98-3.89 (m, 3H), 3.77-3.71 (m, 3H), 3.57-3.53 (t, J = 7.6 Hz, 1H), 2.96-2.94 (d, J = 8.4 Hz, 2H), 2.78-2.77 (d, J = 5.6 Hz, 2H), 2.28-2.25 (m, 3H), 1.91-1.87 (m, 1H). | Sp AA153 BB63 |
| I-719 | 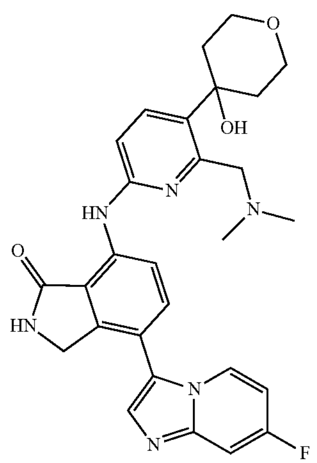 [SMILES: CN(C)Cc1nc(Nc2ccc(-c3cnc4cc(F)ccn34)c3c2C(=O)NC3)ccc1C1(O)CCOCC1] | 7-((6-((dimethylamino)methyl)-5-(4-hydroxytetrahydro-2H-pyran-4-yl)pyridin-2-yl)amino)-4-(7-fluoroimidazo[1,2-a]pyridin-3-yl)isoindolin-1-one | LCMS Method J m/z = 517.2 [M + H]+, Ret. time = 2.65 min | 1H NMR (400 MHz, DMSO-d6) δ 10.10 (s, 1H), 8.87 (s, 1H), 8.76-8.74 (d, J = 8.4 Hz, 1H), 8.49-8.45 (t, J = 6.8 Hz, 1H), 8.04 (s, 1H), 7.85 (s, 1H), 7.77-7.73 (t, J = 8 Hz, 2H), 7.55-7.53 (d, J = 10 Hz, 1H), 6.99-6.97 (t, J = 8.4 Hz, 2H), 4.41 (s, 2H), 3.83 (s, 4H), 3.72 (s, 2H), 2.25 (s, 6H), 1.98-1.95 (m, 2H), 1.74-1.71 (m, 2H). | Xp AA154 BB63 |

| # | STRUCTURE | NAME | LCMS | 1H NMR | Method Reagent AA BB |
|---|---|---|---|---|---|
| I-720 | 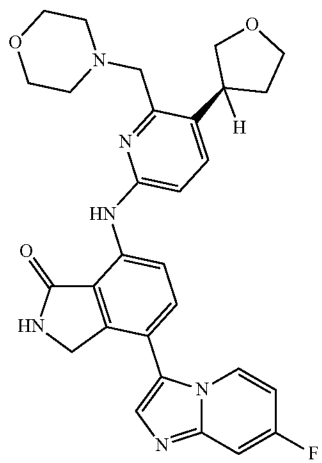 [SMILES: O=C1NCc2c(-c3cnc4cc(F)ccn34)ccc(Nc3ccc([C@@H]4CCOC4)c(CN4CCOCC4)n3)c21] | (S)-4-(7-fluoro-imidazo[1,2-a]pyridin-3-yl)-7-((6-(morpholino-methyl)-5-(tetrahydrofuran-3-yl)pyridin-2-yl)amino)iso-indolin-1-one | LCMS Method J m/z = 529.2 [M + H]+, Ret. time = 2.71 min Chiral HPLC method X16: Ret. time = 8.42 | 1H NMR (400 MHz, DMSO-d6) δ 10.06 (s, 1H), 8.86 (s, 1H), 8.80-8.78 (d, J = 8 Hz, 1H), 8.46 (s, 1H), 7.84 (s, 1H), 7.77-7.75 (d, J = 8.4 Hz, 1H), 7.69-7.67 (d, J = 8 Hz, 1H), 7.55-7.53 (d, J = 8.8 Hz, 1H), 6.99-6.94 (t, J = 8.4 Hz, 2H), 4.40 (s, 2H), 4.06-4.02 (m, 1H), 3.98 (bs, 1H), 3.83-3.77 (m, 3H), 3.65 (s, 1H), 3.58 (s, 6H), 2.44 (bs, 3H), 2.34 (s, 1H), 1.93 (bs, 1H). | Sp AA155 BB63 |
| I-721 | 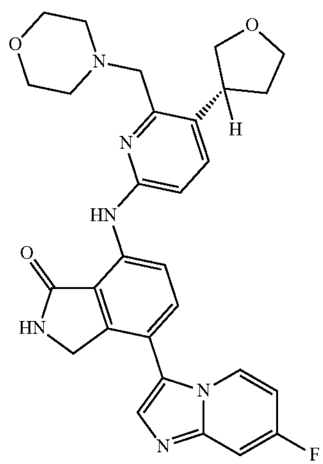 [SMILES: O=C1NCc2c(-c3cnc4cc(F)ccn34)ccc(Nc3ccc([C@H]4CCOC4)c(CN4CCOCC4)n3)c21] | (R)-4-(7-fluoro-imidazo[1,2-a]pyridin-3-yl)-7-((6-(morpholino-methyl)-5-(tetrahydrofuran-3-yl)pyridin-2-yl)amino)iso-indolin-1-one | LCMS Method J m/z = 529.2 [M + H]+, Ret. time = 2.70 min Chiral HPLC method X16: Ret. time = 8.57 | 1H NMR (400 MHz, DMSO-d6) δ 10.06 (s, 1H), 8.85 (s, 1H), 8.80-8.78 (d, J = 8 Hz, 1H), 8.46 (s, 1H), 7.84 (s, 1H), 7.77-7.75 (d, J = 8.4 Hz, 1H), 7.69-7.67 (d, J = 8 Hz, 1H), 7.55-7.53 (d, J = 8.8 Hz, 1H), 6.99-6.94 (t, J = 8.4 Hz, 2H), 4.40 (s, 2H), 4.04-4.02 (m, 1H), 3.98 (bs, 1H), 3.83-3.80 (m, 3H), 3.65 (s, 1H), 3.58 (s, 6H), 2.44 (bs, 3H), 2.34 (s, 1H), 1.91 (bs, 1H). | Sp AA155 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-722 | 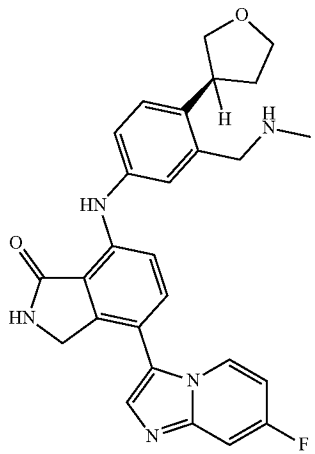 [SMILES: CNCc1cc(Nc2ccc(-c3cnc4cc(F)ccn34)c3c2C(=O)NC3)ccc1[C@@H]1CCOC1] | (S)-4-(7-fluoroimidazo[1,2-a]pyridin-3-yl)-7-((6-((methylamino)methyl)-5-(tetrahydrofuran-3-yl)pyridin-2-yl)amino)isoindolin-1-one | LCMS Method J m/z = 473.2 [M + H]+, Ret. time = 2.65 min Chiral HPLC method X16: Ret. time = 6.36 | 1H NMR (400 MHz, DMSO-d6) δ 10.04 (s, 1H), 8.86 (s, 1H), 8.72-8.70 (d, J = 8 Hz, 1H), 8.46 (s, 1H), 7.84 (s, 1H), 7.76-7.74 (d, J = 8.4 Hz, 1H), 7.66-7.64 (d, J = 8 Hz, 1H), 7.55-7.53 (d, J = 8.8 Hz, 1H), 6.99 (s, 1H), 6.94-6.92 (d, J = 8.4 Hz, 1H), 4.00-3.96 (m, 2H), 3.83 (s, 3H), 3.71-3.67 (d, J = 6.8 Hz, 2H), 3.56 (bs, 1H), 3.35 (s, 1H), 2.40 (s, 3H), 2.30 (bs, 1H), 1.90 (s, 1H). | Sp AA157 BB63 |
| I-723 | 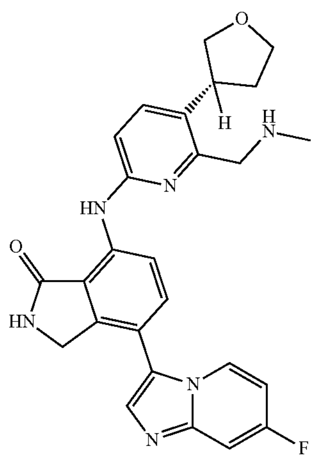 [SMILES: CNCc1nc(Nc2ccc(-c3cnc4cc(F)ccn34)c3c2C(=O)NC3)ccc1[C@H]1CCOC1] | (R)-4-(7-fluoroimidazo[1,2-a]pyridin-3-yl)-7-((6-((methylamino)methyl)-5-(tetrahydrofuran-3-yl)pyridin-2-yl)amino)isoindolin-1-one | LCMS Method J m/z = 473.2 [M + H]+, Ret. time = 2.67 min Chiral HPLC method X16: Ret. time = 6.34 | 1H NMR (400 MHz, DMSO-d6) δ 10.04 (s, 1H), 8.85 (s, 1H), 8.70-8.68 (d, J = 8.4 Hz, 1H), 8.46 (s, 1H), 7.84 (s, 1H), 7.75-7.73 (d, J = 8.4 Hz, 1H), 7.66-7.64 (d, J = 8 Hz, 1H), 7.56-7.53 (d, J = 8.8 Hz, 1H), 6.99 (s, 1H), 6.95-6.93 (d, J = 8.4 Hz, 1H), 4.40 (s, 2H), 3.83 (s, 3H), 3.71-3.67 (d, J = 6.8 Hz, 1H), 3.56 (bs, 1H), 3.35 (s, 1H), 2.40 (s, 3H), 2.30 (bs, 1H), 1.90 (s, 1H). | Sp AA157 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-724 | 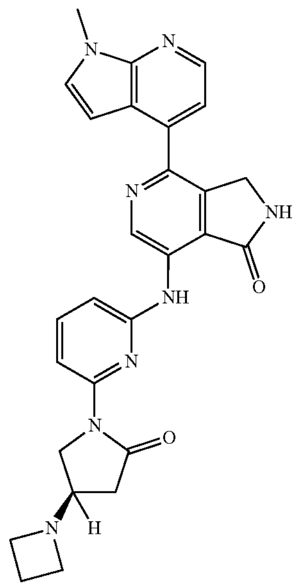 [SMILES: Cn1ccc2c(-c3ncc(Nc4cccc(N5C[C@H](N6CCC6)CC5=O)n4)c4c3CNC4=O)ccnc21] | (R)-7-((6-(4-(azetidin-1-yl)-2-oxopyrrolidin-1-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 495.2 [M + H]+, Ret. time = 3.03 min Chiral HPLC method X16: Ret. time = 6.77 | 1H NMR (400 MHz, DMSO-d6) δ 9.87 (s, 1H), 9.74 (s, 1H), 9.25 (s, 1H), 8.37-8.35 (d, J = 4.4 Hz, 1H), 7.82-7.80 (d, J = 7.6 Hz, 1H), 7.76-7.72 (t, J = 8 Hz, 1H), 7.59-7.58 (d, J = 2.4 Hz, 1H), 7.40-7.39 (d, J = 4.4 Hz, 1H), 6.87 (s, 1H), 6.84-6.82 (d, J = 7.6 Hz, 1H), 4.72-4.70 (d, J = 7.6 Hz, 2H), 4.06-4.02 (m, 1H), 3.87 (s, 4H), 3.17-3.16 (d, J = 5.2 Hz, 4H), 3.08 (s, 1H), 2.78-2.72 (m, 1H), 2.23 (s, 1H), 1.96-1.92 (t, J = 6.4 Hz, 2H). | Zp AA158 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-725 | 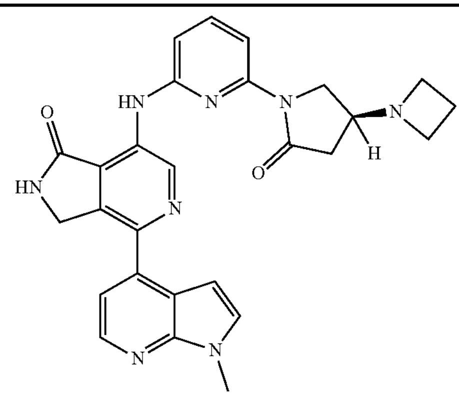 | (S)-7-((6-(4-(azetidin-1-yl)-2-oxopyrrolidin-1-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 495.2 [M + H]+, Ret. time = 3.03 min Chiral HPLC method X16: Ret. time = 6.77 | 1H NMR (400 MHz, DMSO-d6) δ 9.87 (s, 1H), 9.73 (s, 1H), 9.25 (s, 1H), 8.37-8.35 (d, J = 4.4 Hz, 1H), 7.82-7.80 (d, J = 7.6 Hz, 1H), 7.76-7.72 (t, J = 8 Hz, 1H), 7.59-7.58 (d, J = 2.4 Hz, 1H), 7.40-7.39 (d, J = 4.4 Hz, 1H), 6.88 (s, 1H), 6.84-6.82 (d, J = 7.6 Hz, 1H), 4.72-4.70 (d, J = 7.6 Hz, 2H), 4.05-4.01 (m, 1H), 3.87 (s, 4H), 3.17-3.16 (d, J = 5.2 Hz, 4H), 3.08 (s, 1H), 2.78-2.72 (m, 1H), 2.19 (s, 1H), 1.96-1.92 (t, J = 6.4 Hz, 2H). | Zp AA158 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-726 | 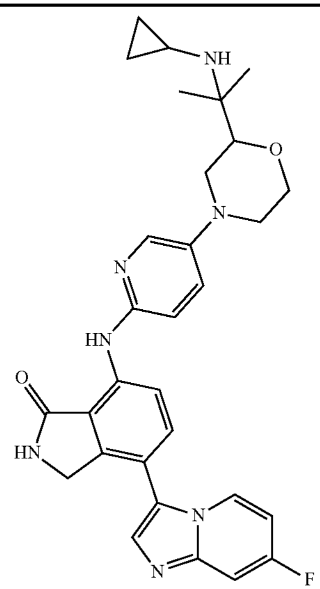 | 7-((5-(2-(2-(cyclopropyl-amino)propan-2-yl)morpho-lino)pyridin-2-yl)amino)-4-(7-fluoro-imidazo[1,2-a]pyridin-3-yl)isoindolin-1-one | LCMS Method J m/z = 543.2 [M + H]+, Ret. time = 2.83 min | 1H NMR (400 MHz, DMSO-d6) δ 9.87 (s, 1H), 9.80 (s, 1H), 8.60-8.58 (d, J = 8.4 Hz, 1H), 8.44-8.41 (t, J = 6.8 Hz, 1H), 8.05 (s, 1H), 7.82 (s, 1H), 7.70-7.68 (d, J = 8.8 Hz, 1H), 7.55-7.48 (dd, J = 10 Hz, 2H), 7.00-6.98 (d, J = 6.8 Hz, 2H), 4.35 (s, 2H), 4.04-4.01 (d, J = 10.4 Hz, 1H), 3.69-3.64 (t, J = 11.2 Hz, 1H), 3.57-3.51 (m, 1H), 3.38 (s, 4H), 2.12 (bs, 1H), 1.24 (s, 1H), 1.12-1.11 (d, J = 4.4 Hz, 6H), 0.42-0.41 (d, J = 4.8 Hz, 2H), 0.23 (s, 2H). | Xp AA159 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-727 | 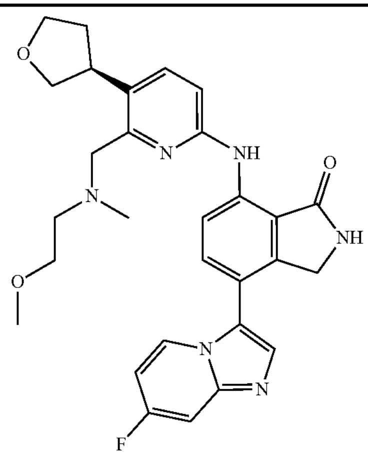 | (R)-4-(7-fluoro-imidazo[1,2-a]pyridin-3-yl)-7-(((2-methoxy-ethyl)(meth-yl)amino)methyl)-5-((4-(tetrahydrofuran-3-yl)pyridin-2-yl)amino)iso-indolin-1-one | LCMS Method J m/z = 531.2 [M + H]+, Ret. time = 2.81 min Chiral HPLC method X6: Ret. time = 12.24 | 1H NMR (400 MHz, DMSO-d6) δ 10.05 (s, 1H), 8.85 (s, 1H), 8.78-8.76 (d, J = 6.4 Hz, 1H), 8.45 (s, 1H), 7.83 (s, 1H), 7.74-7.72 (d, J = 8 Hz, 1H), 7.67-7.65 (d, J = 8 Hz, 1H), 7.55-7.53 (d, J = 9.2 Hz, 1H), 6.98-6.93 (m, 2H), 4.39 (s, 2H), 4.00-3.98 (m, 2H), 3.85-3.77 (m, 2H), 3.66 (s, 1H), 3.45 (s, 3H), 3.21 (s, 3H), 2.58 (bs, 2H), 2.28 (bs, 1H), 2.21 (s, 2H), 1.90-1.88 (m, 1H), 1.23 (s, 2H). | Sp AA160 BB63 |
| I-728 | 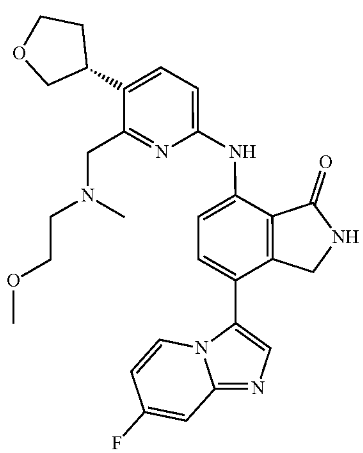 [SMILES: COCCN(C)Cc1nc(Nc2ccc(-c3cnc4cc(F)ccn34)c3c2C(=O)NC3)ccc1[C@H]1CCOC1] | (S)-4-(7-fluoro-imidazo[1,2-a]pyridin-3-yl)-7-(((2-methoxy-ethyl)(meth-yl)amino)methyl)-5-((4-(tetrahydrofuran-3-yl)pyridin-2-yl)amino)iso-indolin-1-one | LCMS Method J m/z = 531.2 [M + H]+, Ret. time = 2.81 min Chiral HPLC method X6: Ret. time = 11.71 | 1H NMR (400 MHz, DMSO-d6) δ 10.05 (s, 1H), 8.85 (s, 1H), 8.78-8.76 (d, J = 6.4 Hz, 1H), 8.45 (s, 1H), 7.83 (s, 1H), 7.74-7.72 (d, J = 8 Hz, 1H), 7.67-7.66 (d, J = 8 Hz, 1H), 7.55-7.52 (d, J = 9.2 Hz, 1H), 6.97-6.95 (m, 2H), 4.39 (s, 2H), 4.00-3.98 (m, 2H), 3.85-3.77 (m, 2H), 3.66 (s, 1H), 3.45 (s, 3H), 3.21 (s, 3H), 2.58 (bs, 2H), 2.28 (bs, 1H), 2.21 (s, 2H), 1.90-1.88 (m, 1H), 1.23 (s, 2H). | Sp AA160 BB63 |

| # | STRUCTURE | NAME | LCMS | 1H NMR | Method Reagent AA BB |
|---|---|---|---|---|---|
| I-729 | 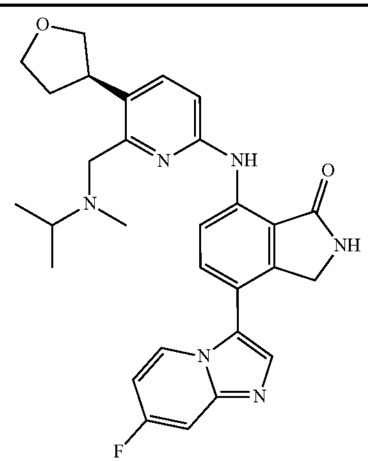 | (S)-4-(7-fluoro-imidazo[1,2-a]pyridin-3-yl)-7-((6-((isopropyl(methyl)amino)methyl)-5-(tetrahydrofuran-3-yl)pyridin-2-yl)amino)isoindolin-1-one | LCMS Method J m/z = 515.2 [M + H]+, Ret. time = 2.86 min Chiral HPLC method X15: Ret. time = 7.65 | 1H NMR (400 MHz, DMSO-d6) δ 10.04 (s, 1H), 8.85 (s, 1H), 8.80-8.78 (d, J = 8.4 Hz, 1H), 8.47-8.43 (t, J = 6.4 Hz, 1H), 7.83 (s, 1H), 7.73-7.71 (d, J = 8 Hz, 1H), 7.66-7.64 (d, J = 8 Hz, 1H), 7.55-7.52 (d, J = 9.2 Hz, 1H), 6.99-6.96 (t, J = 5.6 Hz, 1H), 6.91 (s, 1H), 4.39 (s, 2H), 4.01-3.94 (m, 2H), 3.85-3.77 (m, 2H), 3.76-3.67 (m, 1H), 3.64 (s, 1H), 3.54-3.50 (t, J = 7.2 Hz, 1H), 2.89-2.85 (t, J = 6.4 Hz, 1H), 2.29-2.26 (m, 1H), 2.09 (s, 3H), 1.91-1.86 (dq, 1H), 1.04-1.02 (d, J = 6.4 Hz, 6H). | Sp AA161 BB63 |
| I-730 | 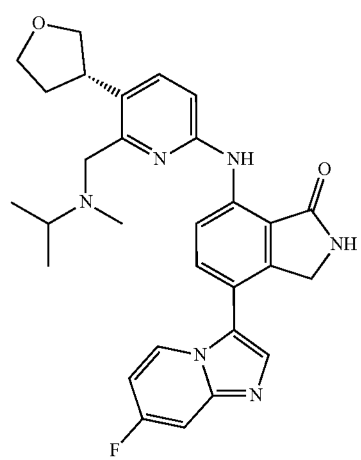 [SMILES: CC(C)N(C)Cc1nc(Nc2ccc(-c3cnc4cc(F)ccn34)c3c2C(=O)NC3)ccc1[C@@H]1CCOC1] | (R)-4-(7-fluoro-imidazo[1,2-a]pyridin-3-yl)-7-((6-((isopropyl(methyl)amino)methyl)-5-(tetrahydrofuran-3-yl)pyridin-2-yl)amino)isoindolin-1-one | LCMS Method J m/z = 515.2 [M + H]+, Ret. time = 2.86 min Chiral HPLC method X15: Ret. time = 7.74 | 1H NMR (400 MHz, DMSO-d6) δ 10.03 (s, 1H), 8.85 (s, 1H), 8.80-8.78 (d, J = 8.4 Hz, 1H), 8.47-8.43 (t, J = 6.4 Hz, 1H), 7.83 (s, 1H), 7.73-7.71 (d, J = 8 Hz, 1H), 7.66-7.64 (d, J = 8 Hz, 1H), 7.55-7.52 (d, J = 9.2 Hz, 1H), 6.99-6.96 (t, J = 5.6 Hz, 1H), 6.91 (s, 1H), 4.39 (s, 2H), 4.01-3.94 (m, 2H), 3.85-3.77 (m, 2H), 3.76-3.67 (m, 1H), 3.64 (s, 1H), 3.54-3.50 (t, J = 7.2 Hz, 1H), 2.89-2.86 (t, J = 6.4 Hz, 1H), 2.28-2.26 (m, 1H), 2.09 (s, 3H), 1.93-1.86 (dq, 1H), 1.04-1.03 (d, J = 6.4 Hz, 6H). | Sp AA161 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-731 | 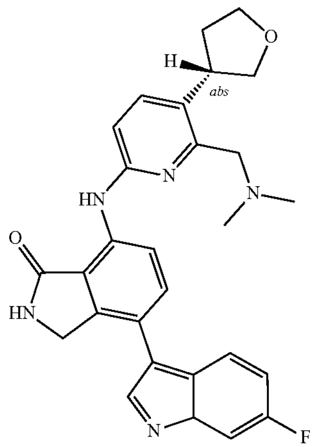 | (S)-7-((6-((dimethyl-amino)methyl)-5-(tetrahydrofuran-3-yl)pyridin-2-yl)amino)-4-(6-methyl-pyrazolo[1,5-a]pyridin-3-yl)isoindolin-1-one | LCMS Method J m/z = 483.2 [M + H]+, Ret. time = 3.63 min Chiral HPLC method X13: Ret. time = 10.32 | 1H NMR (400 MHz, DMSO-d6) δ 9.98 (s, 1H), 8.84 (s, 1H), 8.71-8.69 (d, J = 8.8 Hz, 1H), 8.59 (s, 1H), 8.26 (s, 1H), 7.80-7.77 (d, J = 9.2 Hz, 1H), 7.70-7.63 (dd, J = 8.4 Hz, 2H), 7.19-7.17 (d, J = 9.2 Hz, 1H), 6.91-6.89 (t, J = 8.4 Hz, 1H), 4.51 (s, 2H), 4.00-3.95 (dq, 2H), 3.83-3.78 (m, 2H), 3.62 (bs, 1H), 3.53-3.51 (t, J = 8.8 Hz, 2H), 2.33 (s, 3H), 2.21 (s, 6H), 1.91-.86 (m, 1H), 1.23 (s, 1H). | Sp AA145 BB91 |
| I-732 | 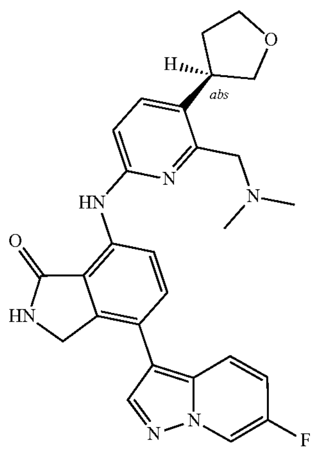 | (R)-7-((6-((dimethyl-amino)methyl)-5-(tetrahydrofuran-3-yl)pyridin-2-yl)amino)-4-(6-methyl-pyrazolo[1,5-a]pyridin-3-yl)isoindolin-1-one | LCMS Method J m/z = 483.2 [M + H]+, Ret. time = 3.63 min Chiral HPLC method X13: Ret. time = 12.43 | 1H NMR (400 MHz, DMSO-d6) δ 9.98 (s, 1H), 8.84 (s, 1H), 8.71-8.69 (d, J = 8.8 Hz, 1H), 8.59 (s, 1H), 8.26 (s, 1H), 7.80-7.77 (d, J = 9.2 Hz, 1H), 7.70-7.63 (dd, J = 8.4 Hz, 2H), 7.19-7.17 (d, J = 9.2 Hz, 1H), 6.91-6.89 (t, J = 8.4 Hz, 1H), 4.51 (s, 2H), 4.00-3.95 (dq, 2H), 3.83-3.78 (m, 2H), 3.62 (bs, 1H), 3.53-3.51 (t, J = 8.8 Hz, 2H), 2.33 (s, 3H), 2.21 (s, 6H), 1.91-.86 (m, 1H), 1.23 (s, 1H). | Sp AA145 BB91 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-733 | 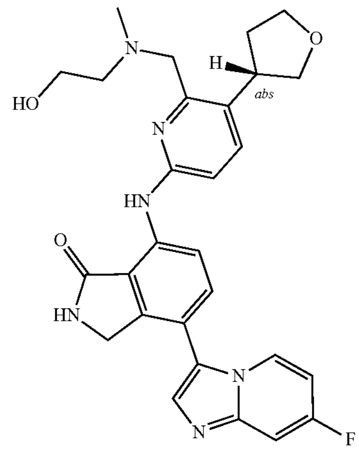 [SMILES: CN(CCO)Cc1nc(Nc2ccc(-c3cnc4cc(F)ccn34)c3c2C(=O)NC3)ccc1[C@@H]1CCOC1] | (S)-4-(7-fluoroimidazo[1,2-a]pyridin-3-yl)-7-(((6-(((2-hydroxyethyl)(methyl)amino)methyl)-5-(tetrahydrofuran-3-yl)pyridin-2-yl)amino)isoindolin-1-one | LCMS Method J m/z = 517.2 [M + H]+, Ret. time = 3.68 min Chiral HPLC method X4: Ret. time = 9.86 | 1H NMR (400 MHz, DMSO-d6) δ 10.04 (s, 1H), 8.86 (s, 1H), 8.79-8.77 (d, J = 8.4 Hz, 1H), 8.47-8.44 (t, J = 6.4 Hz, 1H), 7.83 (s, 1H), 7.74-7.72 (d, J = 8.4 Hz, 1H), 7.65-7.63 (d, J = 7.6 Hz, 1H), 7.55-7.52 (dd, J = 2.4 Hz, 4.4 Hz, 1H), 6.99-6.97 (d, J = 4.4 Hz, 1H), 6.96 (s, 1H), 4.35 (s, 3H), 4.02-3.93 (m, 2H), 3.87-3.79 (m, 2H), 3.69 (s, 1H), 3.62 (s, 1H), 3.51 (bs, 4H), 2.33-2.25 (m, 1H), 2.20 (s, 3H), 1.90-1.83 (m, 1H), 1.23 (s, 1H). | Sp AA162 BB63 |
| I-734 | 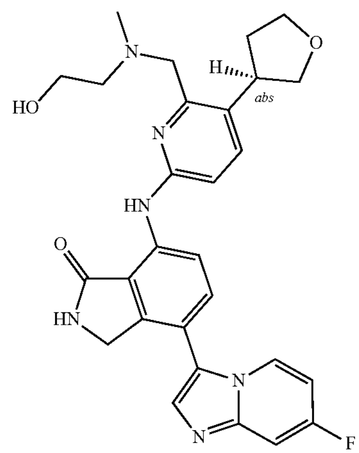 [SMILES: CN(CCO)Cc1nc(Nc2ccc(-c3cnc4cc(F)ccn34)c3c2C(=O)NC3)ccc1[C@H]1CCOC1] | (R)-4-(7-fluoroimidazo[1,2-a]pyridin-3-yl)-7-(((6-(((2-hydroxyethyl)(methyl)amino)methyl)-5-(tetrahydrofuran-3-yl)pyridin-2-yl)amino)isoindolin-1-one | LCMS Method J m/z = 517.2 [M + H]+, Ret. time = 2.67 min Chiral HPLC method X4: Ret. time = 9.99 | 1H NMR (400 MHz, DMSO-d6) δ 10.04 (s, 1H), 8.83 (s, 1H), 8.78-8.76 (d, J = 8.4 Hz, 1H), 8.47-8.43 (t, J = 6.4 Hz, 1H), 7.83 (s, 1H), 7.74-7.72 (d, J = 8.4 Hz, 1H), 7.67-7.65 (d, J = 7.6 Hz, 1H), 7.54-7.51 (dd, J = 2.4 Hz, 4.4 Hz, 1H), 6.99-6.97 (d, J = 4.4 Hz, 1H), 6.93 (s, 1H), 4.39 (s, 3H), 4.02-3.93 (m, 2H), 3.87-3.79 (m, 2H), 3.69 (s, 1H), 3.62 (s, 1H), 3.51 (bs, 4H), 2.33-2.25 (m, 1H), 2.21 (s, 3H), 1.90-1.85 (m, 1H), 1.24 (s, 1H). | Sp AA162 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-735 | 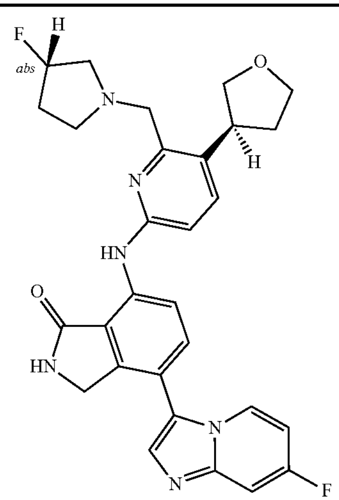 | 4-(7-fluoro-imidazo[1,2-a]pyridin-3-yl)-7-((6-(((S)-3-fluoropyrrolidin-1-yl)methyl)-5-((S)-tetrahydrofuran-3-yl)pyridin-2-yl)amino)isoindolin-1-one | LCMS Method J m/z = 531.2 [M + H]+, Ret. time = 2.77 min Chiral HPLC method X12: Ret. time = 16.45 | 1H NMR (400 MHz, DMSO-d6) δ 10.06 (s, 1H), 8.86 (s, 1H), 8.82-8.80 (d, J = 8.4 Hz, 1H), 8.47-8.43 (t, J = 6 Hz, 1H), 7.83 (s, 1H), 7.73-7.65 (dd, J = 8.4 Hz, 2H), 7.55-7.52 (d, J = 10 Hz, 1H), 6.99-6.95 (t, J = 5.2 Hz, 1H), 6.93 (s, 1H), 5.27 (s, 1H), 4.39 (s, 2H), 4.01-3.90 (m, 3H), 3.79-3.71 (s, 3H), 3.53-3.50 (t, J = 7.2 Hz, 1H), 2.86-2.80 (m, 2H), 2.38-2.30 (m, 2H), 1.92-1.89 (dq, 1H), 1.87-1.81 (m, 2H), 1.23 (s, 1H). | Sp AA163 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-736 | 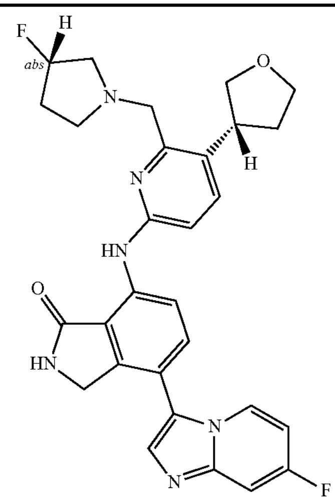 | 4-(7-fluoro-imidazo[1,2-a]pyridin-3-yl)-7-(((S)-3-fluoro-pyrrolidin-1-yl)methyl)-5-((R)-tetrahydrofuran-3-yl)pyridin-2-yl)amino)isoindolin-1-one | LCMS Method J m/z = 531.2 [M + H]+, Ret. time = 2.77 min Chiral HPLC method X12: Ret. time = 17.48 | 1H NMR (400 MHz, DMSO-d6) δ 10.06 (s, 1H), 8.86 (s, 1H), 8.82-8.80 (d, J = 8.4 Hz, 1H), 8.47-8.43 (t, J = 6 Hz, 1H), 7.83 (s, 1H), 7.73-7.65 (dd, J = 8.4 Hz, 2H), 7.55-7.52 (d, J = 10 Hz, 1H), 6.99-6.93 (t, J = 5.2 Hz, 1H), 6.93 (s, 1H), 5.27 (s, 1H), 4.39 (s, 2H), 4.01-3.90 (m, 3H), 3.79-3.71 (s, 3H), 3.53-3.50 (t, J = 7.2 Hz, 1H), 2.86-2.80 (m, 2H), 2.38-2.30 (m, 2H), 1.92-1.89 (dq, 1H), 1.87-1.81 (m, 2H), 1.23 (s, 1H). | Sp AA163 BB63 |
| I-737 | 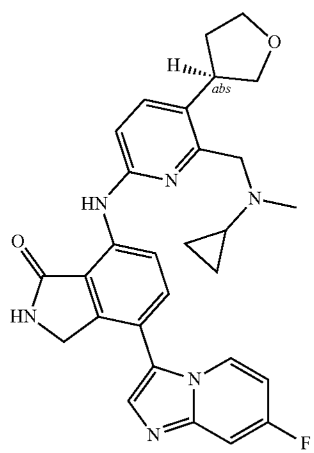 [SMILES: CN(Cc1nc(Nc2ccc(-c3cnc4cc(F)ccn34)c3c2C(=O)NC3)ccc1[C@H]1CCOC1)C1CC1] | (R)-7-((6-((cyclopropyl(methyl)amino)methyl)-5-(tetrahydrofuran-3-yl)pyridin-2-yl)amino)-4-(7-fluoro-imidazo[1,2-a]pyridin-3-yl)isoindolin-1-one | LCMS Method J m/z = 513.2 [M + H]+, Ret. time = 2.84 min Chiral HPLC method X15: Ret. time = 7.87 | 1H NMR (400 MHz, DMSO-d6) δ 10.04 (s, 1H), 8.86 (s, 1H), 8.82-8.80 (d, J = 8.4 Hz, 1H), 8.47-8.44 (t, J = 6 Hz, 1H), 7.83 (s, 1H), 7.74-7.72 (d, J = 8.8 Hz, 1H), 7.64-7.62 (d, J = 8.4 Hz, 1H), 7.55-7.53 (d, J = 7.6 Hz, 1H), 7.00-6.98 (t, J = 5.2 Hz, 1H), 6.92 (s, 1H), 4.39 (s, 2H), 3.97-3.90 (m, 4H), 3.86-3.75 (m, 2H), 3.71-3.67 (t, J = 7.6 Hz, 1H), 4.51-4.42 (dq, 1H), 2.22 (s, 3H), 1.90-1.83 (m, 2H), 0.44-0.42 (d, J = 6.4 Hz, 2H), 0.32-0.30 (m, 2H). | Sp AA164 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-738 | 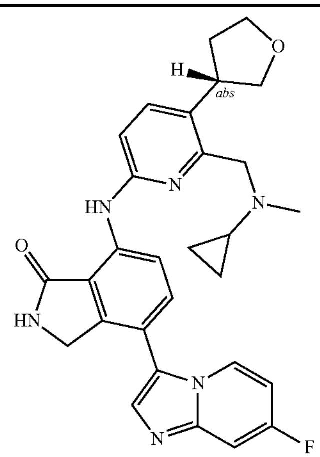 | (S)-7-((6-((cyclopropyl(methyl)amino)methyl)-5-(tetrahydrofuran-3-yl)pyridin-2-yl)amino)-4-(7-fluoroimidazo[1,2-a]pyridin-3-yl)isoindolin-1-one | LCMS Method J m/z = 513.2 [M + H]+, Ret. time = 2.83 min Chiral HPLC method X15: Ret. time = 8.04 | 1H NMR (400 MHz, DMSO-d6) δ 10.04 (s, 1H), 8.86 (s, 1H), 8.82-8.80 (d, J = 8.4 Hz, 1H), 8.47-8.44 (t, J = 6 Hz, 1H), 7.83 (s, 1H), 7.74-7.72 (d, J = 8.8 Hz, 1H), 7.64-7.62 (d, J = 8.4 Hz, 1H), 7.55-7.53 (d, J = 7.6 Hz, 1H), 7.00-6.98 (t, J = 5.2 Hz, 1H), 6.92 (s, 1H), 4.39 (s, 2H), 3.97-3.90 (m, 4H), 3.86-3.75 (m, 2H), 3.71-3.67 (t, J = 7.6 Hz, 1H), 4.51-4.42 (dq, 1H), 2.22 (s, 3H), 1.90-1.83 (m, 2H), 0.44-0.42 (d, J = 6.4 Hz, 2H), 0.32-0.30 (m, 2H). | Sp AA164 BB63 |

TABLE 8-continued

Characterization Data (LCMS and $^1$H NMR).

| # | STRUCTURE | NAME | LCMS | $^1$H NMR | Method Reagent AA BB |
|---|---|---|---|---|---|
| I-739 | 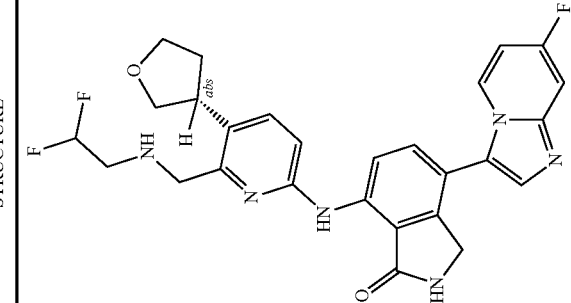 | (R)-7-(((6-fluoro-(((2,2-difluoro-ethyl)amino)methyl)-5-(tetrahydro-furan-3-yl)pyridin-2-yl)amino)-4-(7-fluoro-imidazo[1,2-a]pyridin-3-yl)isoindolin-1-one | LCMS Method J m/z = 523.2 [M + H]+, Ret. time = 2.73 min Chiral HPLC method X6: Ret. time = 12.59 | 1H NMR (400 MHz, DMSO-d6) δ 10.05 (s, 1H), 8.87 (s, 1H), 8.71-8.69 (d, J = 8.8 Hz, 1H), 8.44-8.42 (t, J = 6 Hz, 1H), 7.84 (s, 1H), 7.72-7.65 (dd, J = 8.8 Hz, 2H), 7.57-7.56 (d, J = 2.4 Hz, 1H), 7.02-7.00 (t, J = 2.4 Hz, 1H), 6.93 (s, 1H), 4.40 (s, 2H), 4.02-3.93 (m, 4H), 3.84-3.79 (dq, 1H), 3.67-3.63 (m, 1H), 3.58-3.54 (t, J = 8 Hz, 1H), 2.99-2.98 (d, J = 3.6 Hz, 2H), 2.35-2.26 (m, 1H), 1.94-1.85 (t, J = 6 Hz, 1H), 1.24 (s, 2H). | ADp AA165 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-740 | 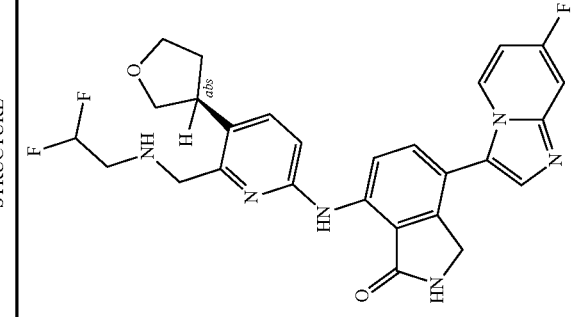 | (S)-7-(((6-(((2,2-difluoroethyl)amino)methyl)-5-(tetrahydrofuran-3-yl)pyridin-2-yl)amino)-4-(7-fluoro imidazo[1,2-a]pyridin-3-yl)isoindolin-1-one | LCMS Method J m/z = 523.2 [M + H]+, Ret. time = 2.73 min Chiral HPLC method X6: Ret. time = 12.63 | 1H NMR (400 MHz, DMSO-d6) δ 10.05 (s, 1H), 8.88 (s, 1H), 8.64-8.62 (d, J = 8 Hz, 1H), 8.44-8.40 (t, J = 6 Hz, 1H), 7.85 (s, 1H), 7.71-7.67 (dd, J = 8.8 Hz, 2H), 7.57-7.56 (d, J = 2.4 Hz, 1H), 7.03-7.00 (t, J = 2.4 Hz, 1H), 6.99 (s, 1H), 4.41 (s, 2H), 4.11 (s, 2H), 4.02-3.93 (m, 2H), 3.84-3.79 (dq, 1H), 3.67-3.63 (m, 1H), 3.58-3.54 (t, J = 8 Hz, 1H), 2.99-2.98 (d, J = 3.6 Hz, 2H), 2.35-2.26 (m, 1H), 1.94-1.85 (t, J = 6 Hz, 1H), 1.24 (s, 2H). | ADp AA165 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-741 | 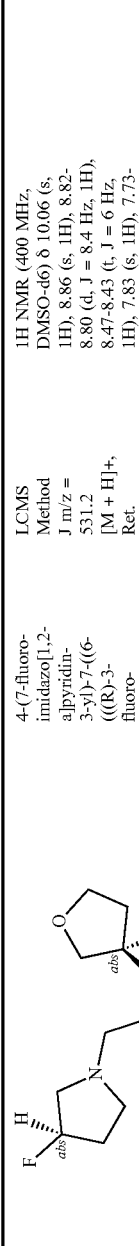 | 4-(7-fluoro-imidazo[1,2-a]pyridin-3-yl)-7-((6-(((R)-3-fluoropyrrolidin-1-yl)methyl)-5-((S)-tetrahydrofuran-3-yl)pyridin-2-yl)amino)isoindolin-1-one | LCMS Method J m/z = 531.2 [M + H]+, Ret. time = 2.80 min Chiral HPLC method X15: Ret. time = 7.84 | 1H NMR (400 MHz, DMSO-d6) δ 10.06 (s, 1H), 8.86 (s, 1H), 8.82-8.80 (d, J = 8.4 Hz, 1H), 8.47-8.43 (t, J = 6 Hz, 1H), 7.83 (s, 1H), 7.73-7.65 (dd, J = 8.4 Hz, 2H), 7.55-7.53 (dd, J = 2.4 Hz, 1H), 7.00-6.98 (t, J = 5.2 Hz, 1H), 6.93 (s, 1H), 5.28 (bs, 1H), 4.39 (s, 2H), 4.02-3.94 (m, 3H), 3.78-3.72 (m, 3H), 3.55-3.51 (t, J = 8 Hz, 1H), 2.88-2.81 (dq, 2H), 2.66-2.62 (m, 1H), 2.42-2.34 (m, 2H), 1.93-1.90 (m, 2H), 1.24 (s, 1H). | Sp AA166 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-742 | 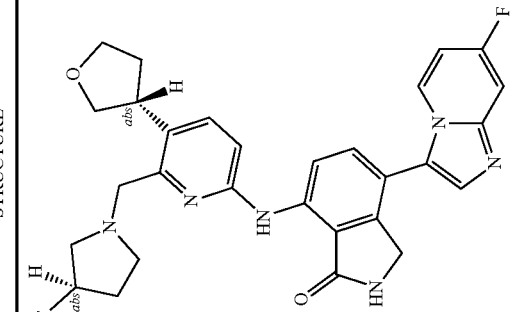 | 4-(7-fluoro-imidazo[1,2-a]pyridin-3-yl)-7-((6-(((R)-3-fluoro-pyrrolidin-1-yl)methyl)-5-((R)-tetra-hydrofuran-3-yl)pyridin-2-yl)amino)iso-indolin-1-one | LCMS Method J m/z = 531.2 [M + H]+, Ret. time = 2.79 min Chiral HPLC method X15: Ret. time = 7.96 | 1H NMR (400 MHz, DMSO-d6) δ 10.07 (s, 1H), 8.86 (s, 1H), 8.83-8.81 (d, J = 8.4 Hz, 1H), 8.47-8.44 (t, J = 6 Hz, 1H), 7.84 (s, 1H), 7.74-7.66 (dd, J = 8.4 Hz, 2H), 7.56-7.53 (dd, J = 2.4 Hz, 1H), 7.00-6.98 (t, J = 5.2 Hz, 1H), 6.93 (s, 1H), 5.28 (bs, 1H), 4.39 (s, 2H), 4.02-3.94 (m, 3H), 3.78-3.72 (m, 3H), 3.55-3.51 (t, J = 8 Hz, 1H), 2.88-2.81 (dq, 2H), 2.66-2.62 (m, 1H), 2.42-2.34 (m, 2H), 1.93-1.90 (m, 2H), 1.24 (s, 1H). | Sp AA166 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-743 | 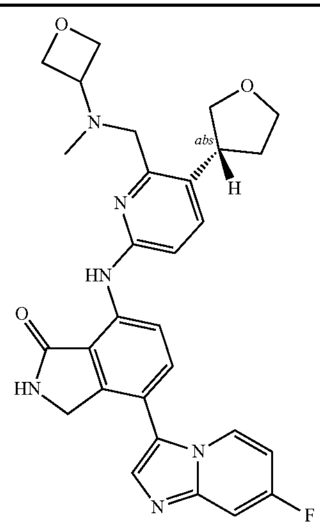 | (R)-4-(7-fluoro-imidazo[1,2-a]pyridin-3-yl)-7-((6-((methyl(oxetan-3-yl)amino)methyl)-5-(tetrahydrofuran-3-yl)pyridin-3-yl)amino)iso-indolin-1-one | LCMS Method J m/z = 529.2 [M + H]+, Ret. time = 2.72 min Chiral HPLC method X11: Ret. time = 18.81 | 1H NMR (400 MHz, DMSO-d6) δ 10.06 (s, 1H), 8.86 (s, 1H), 8.77-8.76 (d, J = 3.6 Hz, 1H), 8.47-8.44 (t, J = 6.8 Hz, 1H), 7.84 (s, 1H), 7.76-7.73 (dd, J = 3.6 Hz, 1H), 7.69-7.66 (dd, J = 3.6 Hz, 1H), 7.55-7.52 (d, J = 9.6 Hz, 1H), 6.97-6.95 (t, J = 3.2 Hz, 1H), 6.94 (s, 1H), 4.47 (bs, 2H), 4.39 (s, 2H), 4.35-4.34 (d, J = 3.2 Hz, 2H), 4.05-4.03 (t, J = 4 Hz, 1H), 3.99-3.97 (t, J = 4 Hz, 1H), 3.64 (s, 1H), 3.58-3.52 (t, J = 6.8 Hz, 3H), 3.35-3.34 (d, J = 3.6 Hz, 1H), 2.35-2.33 (s, 1H), 2.05 (s, 3H), 1.93-1.91 (m, 2H). | Sp AA167 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-744 | 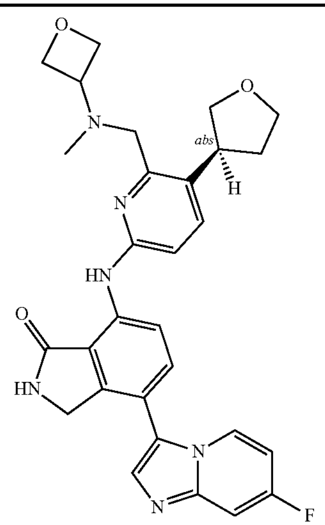 | (S)-4-(7-fluoroimidazo[1,2-a]pyridin-3-yl)-7-((6-((methyl(oxetan-3-yl)amino)methyl)-5-(tetrahydrofuran-3-yl)pyridin-2-yl)amino)isoindolin-1-one | LCMS Method J m/z = 529.2 [M + H]+, Ret. time = 2.73 min Chiral HPLC method X11: Ret. time = 13.49 | 1H NMR (400 MHz, DMSO-d6) δ 10.06 (s, 1H), 8.86 (s, 1H), 8.79-8.77 (d, J = 3.6 Hz, 1H), 8.47-8.44 (t, J = 6.8 Hz, 1H), 7.83 (s, 1H), 7.75-7.73 (dd, J = 3.6 Hz, 1H), 7.68-7.66 (dd, J = 3.6 Hz, 1H), 7.55-7.52 (d, J = 9.6 Hz, 1H), 6.97-6.95 (t, J = 3.2 Hz, 1H), 6.94 (s, 1H), 4.47 (bs, 2H), 4.39 (s, 2H), 4.35-4.34 (d, J = 3.2 Hz, 2H), 4.05-4.03 (t, J = 4 Hz, 1H), 3.99-3.97 (t, J = 4 Hz, 1H), 3.64 (s, 1H), 3.58-3.52 (t, J = 6.8 Hz, 3H), 3.35-3.34 (d, J = 3.6 Hz, 1H), 2.35-2.33 (s, 1H), 2.05 (s, 3H), 1.93-1.91 (m, 2H). | Sp AA167 BB63 |
| I-745 | 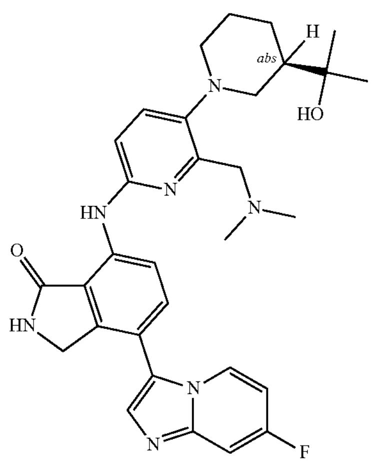 [SMILES: CN(C)Cc1nc(Nc2ccc(-c3cnc4cc(F)ccn34)c3c2C(=O)NC3)ccc1N1CCC[C@@H](C(C)(C)O)C1] | (R)-7-(6-((dimethylamino)methyl)-5-(3-(2-hydroxypropan-2-yl)piperidin-1-yl)pyridin-2-yl)amino)-4-(7-fluoroimidazo[1,2-a]pyridin-3-yl)isoindolin-1-one | LCMS Method J m/z = 558.3 [M + H]+, Ret. time = 3.16 min Chiral HPLC method X12: Ret. time = 11.05 | 1H NMR (400 MHz, DMSO-d6) δ 10.01 (s, 1H), 8.85 (s, 1H), 8.79-8.77 (d, J = 3.6 Hz, 1H), 8.45-8.42 (t, J = 6.8 Hz, 1H), 7.83 (s, 1H), 7.72-7.70 (dd, J = 8 Hz, 1H), 7.59-7.54 (dd, J = 6.8 Hz, 2H), 7.01-6.98 (t, J = 6.4 Hz, 2H), 4.39 (s, 2H), 4.19 (s, 2H), 3.30 (s, 3H), 2.39 (bs, 6H), 1.88-1.86 (d, J = 10.4 Hz, 1H), 1.80 (s, 1H), 1.62 (bs, 2H), 1.10-1.08 (d, J = 7.2 Hz 6H), 0.07-0.06 (d, J = 3.6 Hz, 3H). | Sp AA168 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-746 | 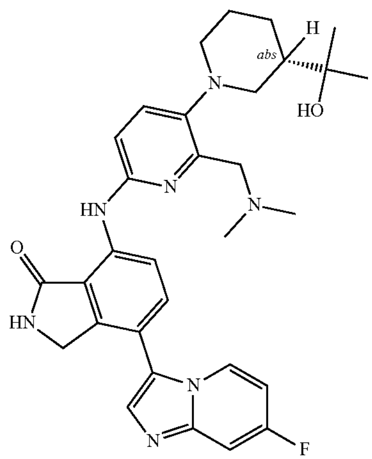 [SMILES: CN(C)Cc1nc(Nc2ccc(-c3cnc4cc(F)ccn34)c3c2C(=O)NC3)ccc1N1CCC[C@H](C(C)(C)O)C1] | (S)-7-((6-((dimethylamino)methyl)-5-(3-(2-hydroxypropan-2-yl)piperidin-1-yl)pyridin-2-yl)amino)-4-(7-fluoroimidazo[1,2-a]pyridin-3-yl)isoindolin-1-one | LCMS Method J m/z = 558.3 [M + H]+, Ret. time = 3.15 min Chiral HPLC method X12: Ret. time = 11.29 | 1H NMR (400 MHz, DMSO-d6) δ 10.02 (s, 1H), 8.87 (s, 1H), 8.79-8.77 (d, J = 3.6 Hz, 1H), 8.44-8.40 (t, J = 6.8 Hz, 1H), 7.84 (s, 1H), 7.72-7.65 (dd, J = 8 Hz, 1H), 7.57-7.54 (dd, J = 6.8 Hz, 2H), 7.02-6.99 (t, J = 6.4 Hz, 2H), 4.40 (s, 2H), 4.22 (s, 2H), 3.30 (s, 3H), 2.39 (bs, 6H), 1.88-1.86 (d, J = 10.4 Hz, 1H), 1.80 (s, 1H), 1.62 (bs, 2H), 1.10-1.08 (d, J = 7.2 Hz 6H), 0.07-0.06 (d, J = 3.6 Hz, 3H). | Sp AA168 BB63 |
| I-747 | 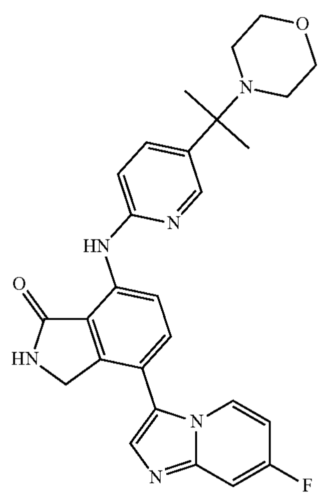 [SMILES: CC(C)(c1ccc(Nc2ccc(-c3cnc4cc(F)ccn34)c3c2C(=O)NC3)nc1)N1CCOCC1] | 4-(7-fluoroimidazo[1,2-a]pyridin-3-yl)-7-((5-(2-morpholinopropan-2-yl)pyridin-2-yl)amino)isoindolin-1-one | LCMS Method J m/z = 487.2 [M + H]+, Ret. time = 2.93 min | 1H NMR (400 MHz, DMSO-d6) δ 10.08 (s, 1H), 8.86 (s, 1H), 8.75-8.73 (d, J = 8 Hz, 1H), 8.37 (s, 1H), 8.25-8.23 (d, J = 6.4 Hz, 1H), 7.90 (s, 1H), 7.83-7.73 (dd, J = 8 Hz, 2H), 7.24-7.19 (t, J = 8 Hz, 1H), 6.99-6.97 (d, J = 8 Hz, 1H), 6.91 (bs, 1H), 4.41 (s, 2H), 3.56 (bs, 4H), 2.39 (bs, 4H), 1.33 (s, 6H). | ACp AA169 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-748 | 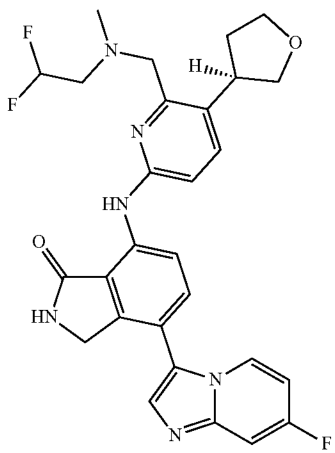 [SMILES: CN(Cc1nc(Nc2ccc(-c3cnc4cc(F)ccn34)c3c2C(=O)NC3)ccc1[C@H]1CCOC1)CC(F)F] | (R)-7-((6-((((2,2-difluoroethyl)(methyl)amino)methyl)-5-(tetrahydrofuran-3-yl)pyridin-2-yl)amino)-4-(7-fluoroimidazo[1,2-a]pyridin-3-yl)isoindolin-1-one | LCMS Method J m/z = 537.2 [M + H]+, Ret. time = 2.96 min Chiral HPLC method X6: Ret. time = 11.37 | 1H NMR (400 MHz, DMSO-d6) δ 10.06 (s, 1H), 8.86 (s, 1H), 8.77-8.75 (d, J = 8.4 Hz, 1H), 8.46-8.43 (t, J = 6.4 Hz, 1H), 7.83 (s, 1H), 7.74-7.67 (dd, J = 8.4 Hz, 2H), 7.55-7.52 (d, J = 10 Hz, 1H), 6.99-6.95 (t, J = 7.2 Hz, 2H), 6.12 (bs, 1H), 4.39 (s, 2H), 4.01-3.97 (dq, 2H), 3.83-3.75 (m, 4H), 3.54-3.50 (t, J = 7.2 Hz, 1H), 2.87-2.86 (td, J = 3.6 Hz, 2H), 2.30 (s, 3H), 1.92-1.83 (m, 1H), 1.23 (s, 1H). | ADp AA170 BB63 |
| I-749 | 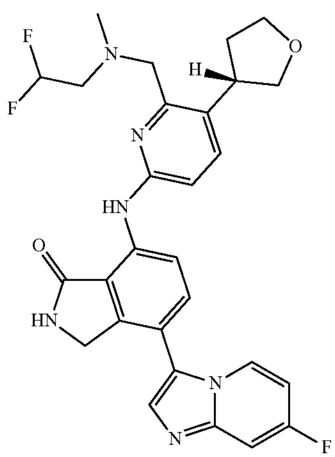 [SMILES: CN(Cc1nc(Nc2ccc(-c3cnc4cc(F)ccn34)c3c2C(=O)NC3)ccc1[C@@H]1CCOC1)CC(F)F] | (S)-7-((6-((((2,2-difluoroethyl)(methyl)amino)methyl)-5-(tetrahydrofuran-3-yl)pyridin-2-yl)amino)-4-(7-fluoroimidazo[1,2-a]pyridin-3-yl)isoindolin-1-one | LCMS Method J m/z = 537.2 [M + H]+, Ret. time = 2.96 min Chiral HPLC method X6: Ret. time = 10.85 | 1H NMR (400 MHz, DMSO-d6) δ 10.06 (s, 1H), 8.86 (s, 1H), 8.77-8.75 (d, J = 8.4 Hz, 1H), 8.46-8.43 (t, J = 6.4 Hz, 1H), 7.83 (s, 1H), 7.74-7.67 (dd, J = 8.4 Hz, 2H), 7.55-7.52 (d, J = 10 Hz, 1H), 6.99-6.95 (t, J = 7.2 Hz, 2H), 6.12 (bs, 1H), 4.39 (s, 2H), 4.01-3.97 (dq, 2H), 3.83-3.75 (m, 4H), 3.54-3.50 (t, J = 7.2 Hz, 1H), 2.87-2.86 (td, J = 3.6 Hz, 2H), 2.27 (s, 3H), 1.92-1.83 (m, 1H), 1.23 (s, 1H). | ADp AA170 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-750 | 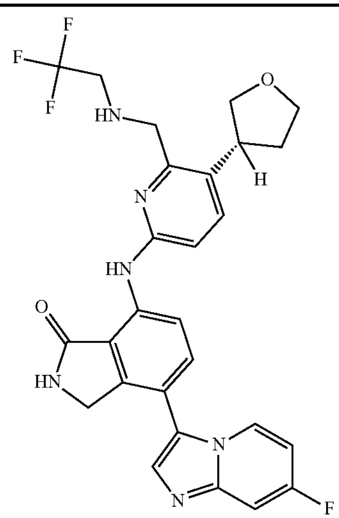 | (R)-4-(7-fluoro-imidazo[1,2-a]pyridin-3-yl)-7-(5-(tetrahydrofuran-3-yl)-6-(((2,2,2-trifluoroeth-yl)amino)meth-yl)pyridin-2-yl)amino)iso-indolin-1-one | LCMS Method J m/z = 541.2 [M + H]+, Ret. time = 3.29 min Chiral HPLC method X6: Ret. time = 10.97 | 1H NMR (400 MHz, DMSO-d6) δ 10.05 (s, 1H), 8.87 (s, 1H), 8.70-8.68 (d, J = 8.4 Hz, 1H), 8.43-8.42 (d, J = 1.6 Hz 1H), 7.84 (s, 1H), 7.71-7.65 (dd, J = 8.4 Hz, 2H), 7.56-7.53 (dd, J = 2.4 Hz, 1H), 7.02-6.98 (dt, J = 2.8 Hz, 1H), 6.94 (bs, 1H), 4.38 (s, 2H), 4.02-3.97 (m, 3H), 3.84-3.78 (dq, 1H), 3.68-3.64 (t, J = 7.2 Hz, 1H), 3.58-3.55 (t, J = 7.6 Hz, 1H), 3.44-3.39 (m, 2H), 2.93-2.90 (t, J = 6.4 Hz, 1H), 2.34-2.26 (m, 1H), 1.94-1.85 (m, 1H), 1.24 (s, 1H). | ADp AA171 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-751 | 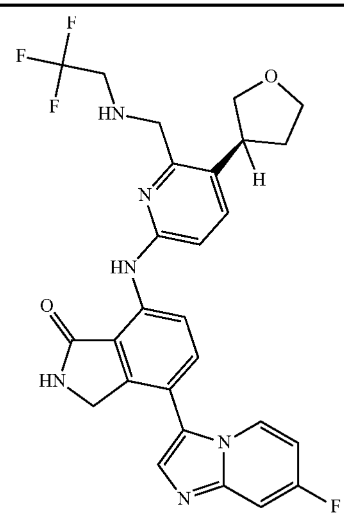 | (S)-4-(7-fluoro-imidazo[1,2-a]pyridin-3-yl)-7-(5-(tetrahydrofuran-3-yl)-6-(((2,2,2-trifluoroethyl)amino)methyl)pyridin-2-yl)amino)iso-indolin-1-one | LCMS Method J m/z = 541.2 [M + H]+, Ret. time = 3.30 min Chiral HPLC method X6: Ret. time = 10.89 | 1H NMR (400 MHz, DMSO-d6) δ 10.05 (s, 1H), 8.86 (s, 1H), 8.70-8.68 (d, J = 8.4 Hz, 1H), 8.44-8.41 (d, J = 1.6 Hz, 1H), 7.84 (s, 1H), 7.71-7.65 (dd, J = 8.4 Hz, 2H), 7.56-7.54 (dd, J = 2.4 Hz, 1H), 7.02-6.98 (dt, J = 2.8 Hz, 1H), 6.94 (bs, 1H), 4.40 (s, 2H), 4.02-3.97 (m, 3H), 3.84-3.78 (dq, 1H), 3.68-3.64 (t, J = 7.2 Hz, 1H), 3.58-3.55 (t, J = 7.6 Hz, 1H), 3.44-3.39 (m, 2H), 2.93-2.90 (t, J = 6.4 Hz, 1H), 2.34-2.26 (m, 1H), 1.92-1.87 (m, 1H), 1.24 (s, 1H). | ADp AA171 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-752 | 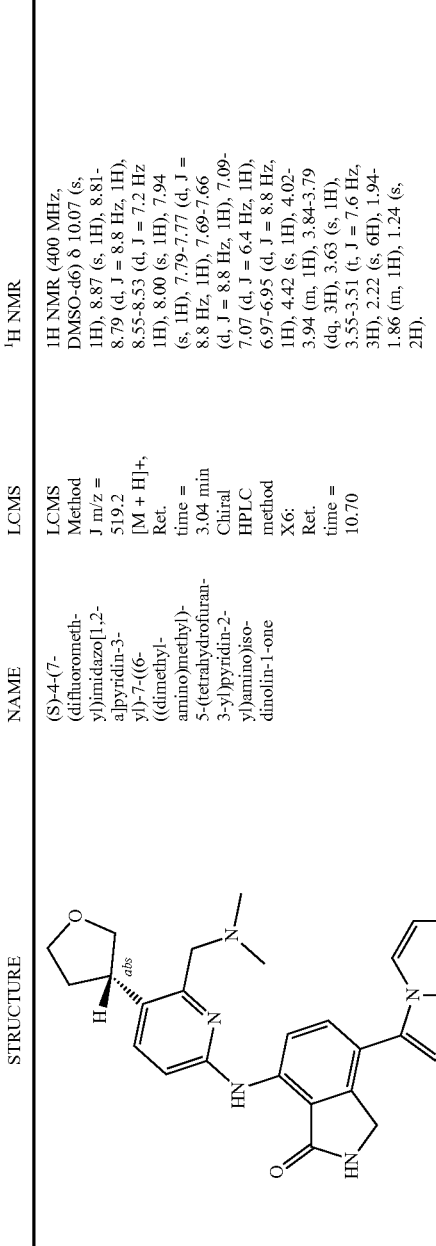 | (S)-4-(7-(difluoromethyl)imidazo[1,2-a]pyridin-3-yl)-7-((6-((dimethylamino)methyl)-5-(tetrahydrofuran-3-yl)pyridin-2-yl)amino)isoindolin-1-one | LCMS Method J m/z = 519.2 [M + H]+, Ret. time = 3.04 min Chiral HPLC method X6: Ret. time = 10.70 | 1H NMR (400 MHz, DMSO-d6) δ 10.07 (s, 1H), 8.87 (s, 1H), 8.81-8.79 (d, J = 8.8 Hz, 1H), 8.55-8.53 (d, J = 7.2 Hz 1H), 8.00 (s, 1H), 7.94 (s, 1H), 7.79-7.77 (d, J = 8.8 Hz, 1H), 7.69-7.66 (d, J = 8.8 Hz, 1H), 7.09-7.07 (d, J = 6.4 Hz, 1H), 6.97-6.95 (d, J = 8.8 Hz, 1H), 4.42 (s, 1H), 4.02-3.94 (m, 1H), 3.84-3.79 (dq, 3H), 3.63 (s, 1H), 3.55-3.51 (t, J = 7.6 Hz, 3H), 2.22 (s, 6H), 1.94-1.86 (m, 1H), 1.24 (s, 2H). | Sp AA145 BB84 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-753 | 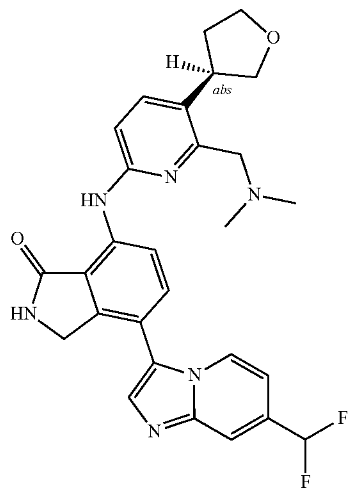 [SMILES: CN(C)Cc1nc(Nc2ccc(-c3cnc4cc(C(F)F)ccn34)c3c2C(=O)NC3)ccc1[C@H]1CCOC1] | (R)-4-(7-(difluoromethyl)imidazo[1,2-a]pyridin-3-yl)-7-((6-((dimethylamino)methyl)-(5-tetrahydrofuran-3-yl)pyridin-2-yl)amino)isoindolin-1-one | LCMS Method J m/z = 519.2 [M + H]+, Ret. time = 3.06 min Chiral HPLC method X6: Ret. time = 10.27 | 1H NMR (400 MHz, DMSO-d6) δ 10.05 (s, 1H), 8.86 (s, 1H), 8.77-8.75 (d, J = 7.6 Hz, 1H), 8.54-8.52 (d, J = 7.2 Hz 1H), 8.00 (s, 1H), 7.94 (s, 1H), 7.79-7.77 (d, J = 8.8 Hz, 1H), 7.69-7.66 (d, J = 8.8 Hz, 1H), 7.09-7.07 (d, J = 6.4 Hz, 1H), 6.97-6.95 (d, J = 8.8 Hz, 1H), 4.42 (s, 1H), 4.02-3.94 (m, 1H), 3.84-3.79 (dq, 3H), 3.63 (s, 1H), 3.55-3.51 (t, J = 7.6 Hz, 3H), 2.22 (s, 6H), 1.94-1.86 (m, 1H), 1.24 (s, 2H). | Sp AA145 BB84 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-754 | 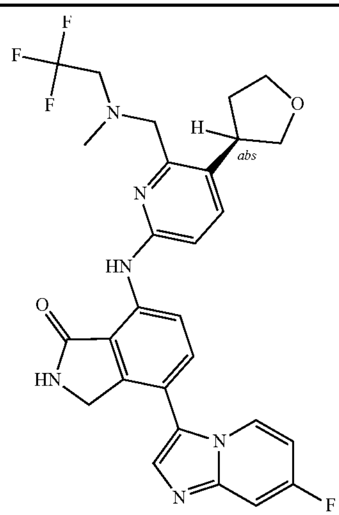 | (S)-4-(7-fluoro-imidazo[1,2-a]pyridin-3-yl)-7-((6-((methyl(2,2,2-trifluoroethyl)amino)methyl)-5-(tetrahydrofuran-3-yl)pyridin-2-yl)amino)iso-indolin-1-one | LCMS Method J m/z = 555.2 [M + H]+, Ret. time = 4.03 min | 1H NMR (400 MHz, DMSO-d6) δ 10.07 (s, 1H), 8.87 (s, 1H), 8.77-8.75 (d, J = 8.4 Hz, 1H), 8.45-8.43 (t, J = 5.6 Hz 1H), 7.84 (s, 1H), 7.74-7.68 (dd, J = 8.8 Hz, 2H), 7.56-7.55 (d, J = 2 Hz, 1H), 6.99-6.97 (t, J = 2.4 Hz, 1H), 6.90 (s, 1H), 4.45 (s, 2H), 4.00-3.90 (m, 2H), 3.87-3.81 (dq, 2H), 3.78-3.72 (s, 2H), 3.55-3.52 (t, J = 8 Hz, 1H), 2.37 (s, 3H), 2.31-2.27 (m, 2H), 1.93-1.89 (m, 1H). | ADp AA171 BB63 |
| I-755 | 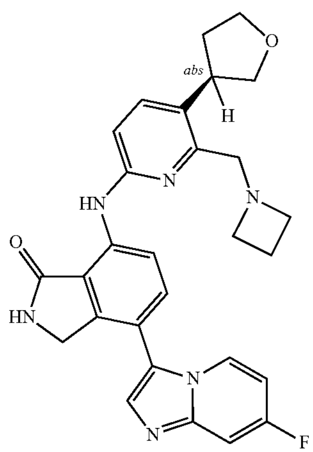 [SMILES: O=C1NCc2c(-c3cnc4cc(F)ccn34)ccc(Nc3ccc([C@H]4CCOC4)c(CN4CCC4)n3)c21] | (R)-7-((6-(azetidin-1-ylmethyl)-5-(tetrahydrofuran-3-yl)pyridin-2-yl)amino)-4-(7-fluoro-imidazo[1,2-a]pyridin-3-yl)isoindolin-1-one | LCMS Method C m/z = 499.7 [M + H]+, Ret. time = 1.23 min Chiral HPLC method X5: Ret. time = 11.52 | 1H NMR (400 MHz, DMSO-d6) δ 10.05 (s, 1H), 8.85-8.83 (m, 2H), 8.48-8.44 (t, J = 6 Hz, 1H), 7.83 (s, 1H), 7.77-7.75 (d, J = 8.4 Hz, 1H), 7.64-7.62 (d, J = 8.8 Hz, 1H), 7.55-7.52 (dd, J = 2.4 Hz, 1H), 6.99-6.98 (td, J = 2.8 Hz, 1H), 6.90 (s, 1H), 4.39 (s, 2H), 3.96-3.93 (dq, 2H), 3.77-3.72 (m, 3H), 3.55-3.52 (t, J = 8 Hz 2H), 3.24-3.18 (m, 3H), 2.32-2.28 (m, 1H), 2.03-2.00 (t, J = 6.4 Hz, 3H), 1.24 (s, 1H). | Sp AA173 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-756 | 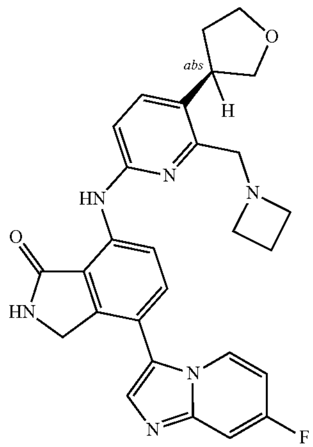 [SMILES: O=C1NCc2c(-c3cnc4cc(F)ccn34)ccc(Nc3ccc([C@H]4CCOC4)c(CN4CCC4)n3)c21] | (R)-7-((6-(azetidin-1-ylmethyl)-5-(tetrahydrofuran-3-yl)pyridin-2-yl)amino)-4-(7-fluoro-imidazo[1,2-a]pyridin-3-yl)isoindolin-1-one | LCMS Method J m/z = 499.2 [M + H]+, Ret. time = 2.78 min Chiral HPLC method X5: Ret. time = 13.55 | 1H NMR (400 MHz, DMSO-d6) δ 10.04 (s, 1H), 8.85-8.83 (m, 2H), 8.48-8.44 (t, J = 6 Hz, 1H), 7.83 (s, 1H), 7.77-7.75 (d, J = 8.4 Hz, 1H), 7.64-7.62 (d, J = 8.8 Hz, 1H), 7.55-7.52 (dd, J = 2.4 Hz, 1H), 6.99-6.98 (td, J = 2.8 Hz, 1H), 6.90 (s, 1H), 4.39 (s, 2H), 3.96-3.93 (dq, 2H), 3.77-3.72 (m, 3H), 3.55-3.52 (t, J = 8 Hz, 2H), 3.24-3.18 (m, 1H), 2.32-2.28 (m, 1H), 2.03-2.00 (t, J = 6.4 Hz, 3H), 1.24 (s, 1H). | Sp AA173 BB63 |
| I-757 | 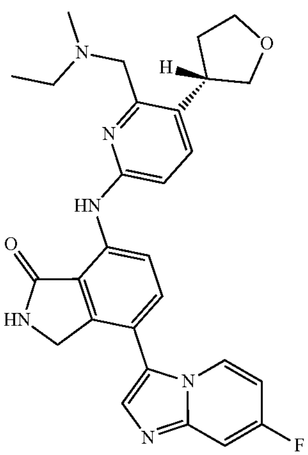 [SMILES: CCN(C)Cc1nc(Nc2ccc(-c3cnc4cc(F)ccn34)c3c2C(=O)NC3)ccc1[C@@H]1CCOC1] | (S)-7-((6-((ethyl(methyl)amino)methyl)-5-(tetrahydrofuran-3-yl)pyridin-2-yl)amino)-4-(7-fluoro-imidazo[1,2-a]pyridin-3-yl)isoindolin-1-one | LCMS Method J m/z = 500.6 [M + H]+, Ret. time = 2.86 min Chiral HPLC method X15: Ret. time = 7.97 | 1H NMR (400 MHz, DMSO-d6) δ 10.04 (s, 1H), 8.84 (s, 1H), 8.78-8.76 (d, J = 6 Hz, 1H), 8.46-8.43 (t, J = 6.8 Hz, 1H), 7.82 (s, 1H), 7.73-7.71 (d, J = 8.4 Hz, 1H), 7.67-7.65 (d, J = 8.8 Hz, 1H), 7.54-7.51 (dd, J = 2.4 Hz, 1H), 6.99-6.97 (t, J = 2.4 Hz, 1H), 6.93 (s, 1H), 4.39 (s, 2H), 4.01-3.94 (m, 2H), 3.85-3.77 (dq, 3H), 3.60 (s, 1H), 3.57 (s, 1H), 3.54-3.50 (t, J = 7.6 Hz, 2H), 2.33-2.30 (s, 2H), 1.91-1.86 (dq, 2H), 1.23 (s, 1H), 1.05-1.02 (t, J = 6.4 Hz, 3H). | Sp AA174 BB63 |

| # | STRUCTURE | NAME | LCMS | 1H NMR | Method Reagent AA BB |
|---|---|---|---|---|---|
| I-758 | 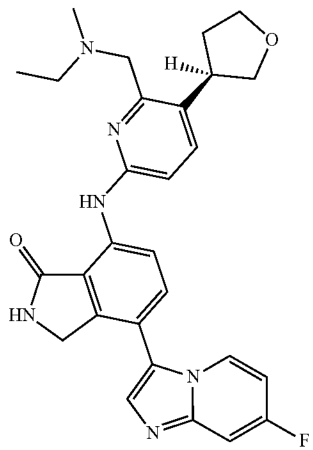 [SMILES: CCN(C)Cc1nc(Nc2ccc(-c3cnc4cc(F)ccn34)c3c2C(=O)NC3)ccc1[C@H]1CCOC1] | (R)-7-((6-((ethyl(methyl)amino)methyl)-5-(tetrahydrofuran-3-yl)pyridin-2-yl)amino)-4-(7-fluoroimidazo[1,2-a]pyridin-3-yl)isoindolin-1-one | LCMS Method J m/z = 500.6 [M + H]+, Ret. time = 2.86 min Chiral HPLC method X15: Ret. time = 8.18 | 1H NMR (400 MHz, DMSO-d6) δ 10.04 (s, 1H), 8.84 (s, 1H), 8.78-8.76 (d, J = 6 Hz, 1H), 8.46-8.43 (t, J = 6.8 Hz, 1H), 7.82 (s, 1H), 7.73-7.71 (d, J = 8.4 Hz, 1H), 7.67-7.65 (d, J = 8.8 Hz, 1H), 7.54-7.51 (dd, J = 2.4 Hz, 1H), 6.99-6.97 (t, J = 2.4 Hz, 1H), 6.93 (s, 1H), 4.39 (s, 2H), 4.01-3.94 (m, 2H), 3.85-3.77 (dq, 3H), 3.60 (s, 1H), 3.57 (s, 1H), 3.54-3.50 (t, J = 7.6 Hz, 2H), 2.33-2.30 (s, 2H), 1.91-1.86 (dq, 2H), 1.23 (s, 1H), 1.05-1.02 (t, J = 6.4 Hz, 3H). | Sp AA174 BB63 |
| I-759 | 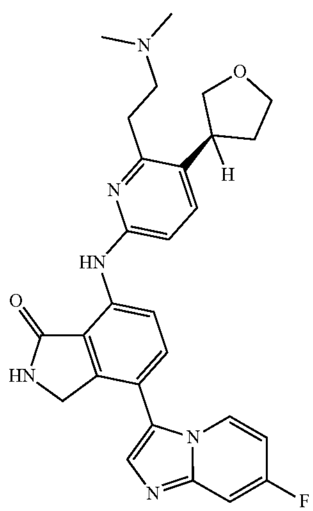 [SMILES: CN(C)CCc1nc(Nc2ccc(-c3cnc4cc(F)ccn34)c3c2C(=O)NC3)ccc1[C@@H]1CCOC1] | (S)-7-((6-(2-(dimethylamino)ethyl)-5-(tetrahydrofuran-3-yl)pyridin-2-yl)amino)-4-(7-fluoroimidazo[1,2-a]pyridin-3-yl)isoindolin-1-one | LCMS Method J m/z = 500.6 [M + H]+, Ret. time = 2.87 min Chiral HPLC method X4: Ret. time = 9.20 | 1H NMR (400 MHz, DMSO-d6) δ 10.01 (s, 1H), 8.83 (s, 1H), 8.73 (d, J = 8.6 Hz, 1H), 8.44 (t, J = 7.6, 5.7 Hz, 1H), 7.83 (s, 1H), 7.73 (d, J = 8.6 Hz, 1H), 7.64-7.49 (m, 1H), 7.0-6.9 (m, J = 7.6, 1H), 6.86-6.84 (d, J = 8.5 Hz, 2H), 4.39 (s, 2H), 4.02-3.93 (m, 2H), 3.85-379 (q, J = 7.7 Hz, 1H), 3.57-3.56 (d, J = 6.3 Hz, 2H), 2.97 (t, J = 7.7 Hz, 2H), 2.68-2.64 (t, J = 7.7 Hz, 2H), 2.24 (s, 6H), 1.90-1.83 (m, 1H). | Sp AA175 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-760 | 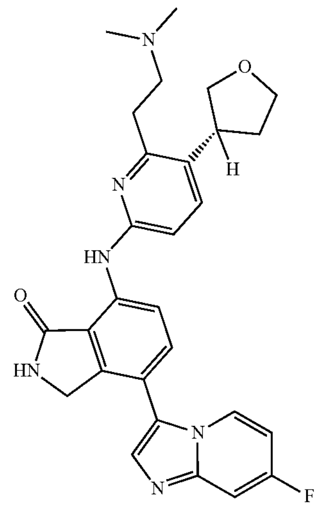 [SMILES: CN(C)CCc1nc(Nc2ccc(-c3cnc4cc(F)ccn34)c3c2C(=O)NC3)ccc1[C@H]1CCOC1] | (R)-7-(6-(2-(dimethylamino)ethyl)-5-(tetrahydrofuran-3-yl)pyridin-2-yl)amino)-4-(7-fluoroimidazo[1,2-a]pyridin-3-yl)isoindolin-1-one | LCMS Method J m/z = 500.6 [M + H]+, Ret. time = 2.88 min Chiral HPLC method X4: Ret. time = 9.33 | 1H NMR (400 MHz, DMSO-d6) δ 10.01 (s, 1H), 8.83 (s, 1H), 8.74-8.72 (d, J = 8.6 Hz, 1H), 8.45-8.42 (d, J = 7.7, Hz, 1H), 7.82 (s, 1H), 7.74-7.71 (d, J = 8.6 Hz, 1H), 7.61-7.58 (d, 2H), 7.54-7.51 (d, J = 7.5, Hz, 1H), 7.0-6.95 (m, 1H), 6.86-6.84 (d, J = 8 Hz, 1H) 4.39 (s, 2H), 4.03-3.91 (m, 2H), 3.85-3.79 (m, 1H), 3.61-3.50 (m, 2H), 2.98-2.94 (dd, J = 9.1, 6.3 Hz, 2H), 2.68-2.64 (t, J = 8.7, 6.7 Hz, 1H), 2.35 (d, J = 4.6 Hz, 2H), 2.24 (s, 6H), 1.92-1.85 (m, J = 14.7, 1H). | Sp AA175 BB63 |
| I-761 | 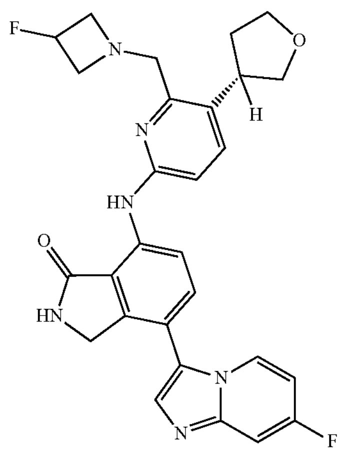 [SMILES: O=C1NCc2c(-c3cnc4cc(F)ccn34)ccc(Nc3ccc([C@@H]4CCOC4)c(CN4CC(F)C4)n3)c21] | (S)-7-(6-((3-fluoroazetidin-1-yl)methyl)-5-(tetrahydrofuran-3-yl)pyridin-2-yl)amino)-4-(7-fluoroimidazo[1,2-a]pyridin-3-yl)isoindolin-1-one | LCMS Method J m/z = 516.6 [M + H]+, Ret. time = 2.81 min Chiral HPLC method X15: Ret. time = 7.72 | 1H NMR (400 MHz, DMSO-d6) δ 10.06 (s, 1H), 8.84-8.81 (t, J = 12 Hz, 2H), 8.47-8.44 (t, J = 12 Hz, 1H), 7.84 (s, 1H), 7.77-7.75 (d, J = 8.5 Hz, 1H), 7.55-7.56 (d, J = 4 Hz, 1H), 7.53-7.52 (d, J = 4 Hz, 1H), 7.01-6.92 (m, 3H), 5.28-5.27 (d, 1H), 5.14-5.13 (d, J = 4 Hz, 1H) 4.40 (s, 1H), 4.00 (t, J = 7.7 Hz, 2H), 4.02-3.87 (m, 2H), 3.85 (d, J = 16.0 Hz, 1H), 3.84-3.61 (m, 3H), 3.57 (dt, J = 21.0, 7.5 Hz, 1H), 3.31 (s, 6H), 3.24 (s, 1H), 2.29 (s, 1H), 1.92-1.88 (m, 1H) 1.24 (S, 1H). | Sp AA176 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-762 | 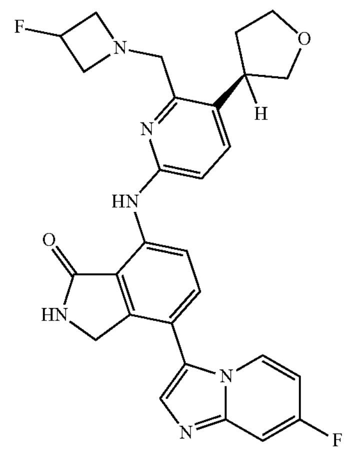 [SMILES: O=C1NCc2c(-c3cnc4cc(F)ccn34)ccc(Nc3ccc([C@H]4CCOC4)c(CN4CC(F)C4)n3)c21] | (R)-7-((6-((3-fluoroazetidin-1-yl)methyl)-5-(tetrahydrofuran-3-yl)pyridin-2-yl)amino)-4-(7-fluoroimidazo[1,2-a]pyridin-3-yl)isoindolin-1-one | LCMS Method J m/z = 516.7 [M + H]+, Ret. time = 2.84 min Chiral HPLC method X15: Ret. time = 7.62 | 1H NMR (400 MHz, DMSO-d6) δ 10.05 (s, 1H), 8.84-8.80 (t, J = 16 Hz, 2H), 8.47-8.43 (t, J = 6.6 Hz, 1H), 7.83 (s, 1H), 7.77-7.75 (d, J = 8.5 Hz, 1H), 7.65-7.63 (d, J = 8.4 Hz, 1H), 7.55-7.54 (d, J = 4 Hz 1H), 7.52-7.51 (d, J = 4 Hz 1H), 6.98-6.97 (d, J = 4 Hz, 2H), 5.27-5.25 (t, J = 8 Hz, 2H), 4.39 (s, 2H), 4.04-3.75 (m, 4H), 3.74-3.65 (m, 1H), 3.63 (s, 1H), 3.58-3.49 (m, 1H), 3.30 (d, J = 10.0 Hz, 1H), 3.23 (s, 1H), 1.96-1.85 (m, 1H), 1.54 (s, 1H), 1.36 (d, J = 13.6 Hz, 1H), 1.24 (d, J = 4.0 Hz, 1H). | Sp AA176 BB63 |
| I-763 | 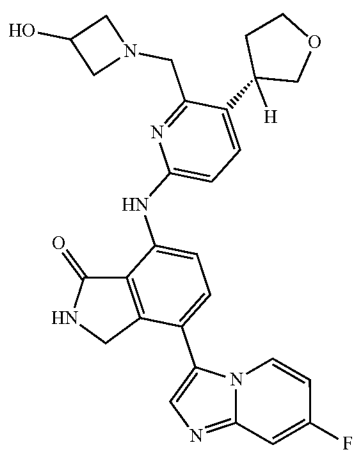 [SMILES: O=C1NCc2c(-c3cnc4cc(F)ccn34)ccc(Nc3ccc([C@@H]4CCOC4)c(CN4CC(O)C4)n3)c21] | (S)-4-(7-fluoroimidazo[1,2-a]pyridin-3-yl)-7-((6-((3-hydroxyazetidin-1-yl)methyl)-5-(tetrahydrofuran-3-yl)pyridin-2-yl)amino)isoindolin-1-one | LCMS Method J m/z = 514.5 [M + H]+, Ret. time = 2.79 min Chiral HPLC method X6: Ret. time = 13.55 | 1H NMR (400 MHz, DMSO-d6) δ 10.05 (s, 1H), 8.84-8.81 (t, J = 12 Hz, 2H), 8.47-8.44 (t, J = 12 Hz, 1H), 7.83 (s, 1H), 7.75-7.73 (d, J = 8.5 Hz, 1H), 7.64-7.61 (d, J = 8.5 Hz, 1H), 7.55-7.52 (d, J = 12 Hz, 2H), 7.03-6.88 (s, 1H), 5.30 (s, 1H), 4.40 (s, 1H), 4.19 (s, 1H), 4.03-3.90 (m, 2H), 3.86-3.76 (m, 2H), 3.71 (q, J = 6.6, 5.5 Hz, 2H), 3.51 (m, 7.1 Hz, 2H), 3.31 (s, 1H), 2.93-2.90 (t, J = 6.6 Hz, 2H), 2.29-2.25 (t, J = 16 Hz, 2H) 1.93-1.86 (m, 2H), 1.24 (s, 1H), 0.85 (s, 1H) | Sp AA177 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-764 | 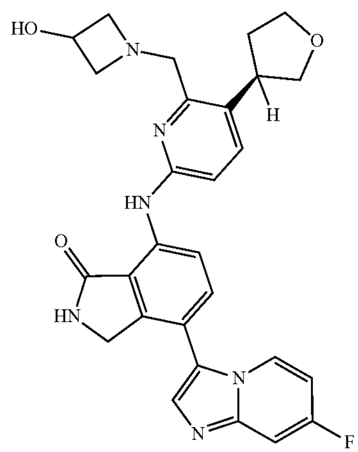 [SMILES: O=C1NCc2c(-c3cnc4cc(F)ccn34)ccc(Nc3ccc([C@H]4CCOC4)c(CN4CC(O)C4)n3)c21] | (R)-4-(7-fluoro-imidazo[1,2-a]pyridin-3-yl)-7-((6-((3-hydroxy-azetidin-1-yl)methyl)-5-(tetrahydrofuran-3-yl)pyridin-2-yl)amino)isoindolin-1-one | LCMS Method J m/z = 514.6 [M + H]+, Ret. time = 2.80 min Chiral HPLC method X6: Ret. time = 13.12 | 1H NMR (400 MHz, DMSO-d6) δ 10.05 (s, 1H), 8.84-8.82 (d, J = 8 Hz, 2H), 8.47-8.44 (t, J = 8 Hz 2H), 7.84 (s, 1H), 7.75-7.73 (d, J = 8.5 Hz, 1H), 7.64-7.61 (d, J = 8.5 Hz, 1H), 7.55-7.52 (dd, J = 10.1, 2.7 Hz, 2H), 6.99-6.96 (Q, J = 16 Hz 1H), 6.92-6.90 (d, J = 8 Hz, 1H) 5.30 (s, 1H), 4.40 (s, 1H), 4.19 (s, 1H), 4.03-3.90 (m, 2H), 3.86-3.76 (m, 2H), 3.71 (q, J = 6.5, 5.3 Hz, 2H), 3.51 (dt, J = 18.2, 6.8 Hz, 2H), 2.93-2.90 (t, J = 6.6 Hz, 1H), 2.30-2.29 (dt, J = 8.0 Hz, 1H), 1.91-1.86 (m, 1H), 1.24 (s, 4H), 0.89-085 (dq, J = 16 Hz, 2H) | Sp AA177 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-765 | 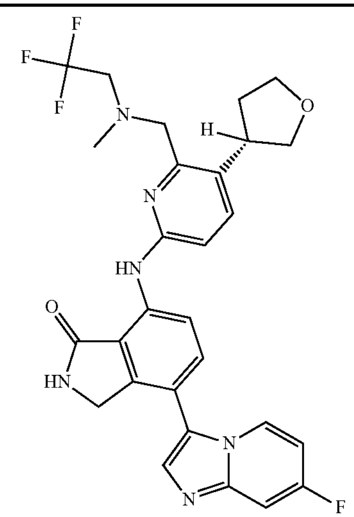 | (R)-4-(7-fluoroimidazo[1,2-a]pyridin-3-yl)-7-((6-(((methyl(2,2,2-trifluoroethyl)amino)methyl)-5-(tetrahydrofuran-3-yl)pyridin-2-yl)amino)isoindolin-1-one | LCMS Method J m/z = 555.2 [M + H]+, Ret. time = 4.03 min Chiral HPLC method X4: Ret. time = 9.81 | 1H NMR (400 MHz, DMSO): δ 10.08 (s, 1H), 8.87 (s, 1 H), 8.77-8.75 (d , J = 8.4 Hz, 1H), 8.47-8.43 (t, J = 6.4 Hz, 1H), 7.84 (s, 1H), 7.71-7.70 (d, J = 2.8 Hz, 2H), 7.56-7.53 (m, 1H), 6.99-6.97 (m, 2H), 4.50 (s, 2H), 3.98-3.92 (m, 4H), 3.81-3.69 (m, 2H), 3.35 (s, 3H), 2.37 (s, 3H), 1.91 (m, 1H), 1.86-1.80 (m, 1H) 1.24 (bs, 1H). | ADp AA171 BB63 |
| I-766 | 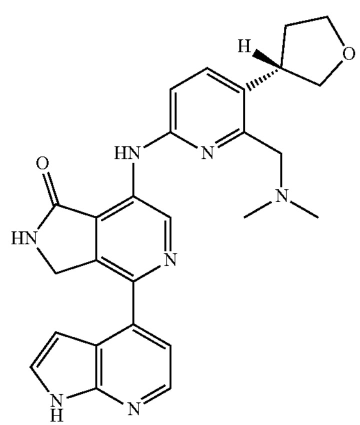 [SMILES: CN(C)Cc1nc(Nc2cnc(-c3ccnc4[nH]ccc34)c3c2C(=O)NC3)ccc1[C@@H]1CCOC1] | (S)-7-((6-(((dimethylamino)methyl)-5-(tetrahydrofuran-3-yl)pyridin-2-yl)amino)-4-(1H-pyrrolo[2,3-b]pyridin-4-yl)-2,3-dihydro-1H-pyrrolo[3,4-c]pyridin-1-one | LCMS Method J m/z = 470.0 [M + H]+, Ret. time = 2.88 min Chiral HPLC method X6: Ret. time = 11.10 | 1H NMR (400 MHz, DMSO-d6) 10.12 (s, 1H), 9.69 (s, 2H), 9.222 (S, 1H), 8.31-8.30 (d, J = 5.0 Hz, 1H), 7.71-7.69 (d , J = 8.4 Hz, 1H), 7.53 (S, 1H), 7.36-7.35 (d, J = 5.0 Hz, 1H), 7.05-7.03 (d, J = 8.3 Hz, 1H), 6.87 (d, J = 3.4 Hz, 1H), 4.71 (s, 2H), 3.99 (q, J = 9.2, 8.6 Hz, 2H), 3.82 (q, J = 8.0 Hz, 2H), 3.67 (d, J = 12.3 Hz, 1H), 3.58 (s, 1H), 3.54 (s, 2H), 2.23 (s, 6H), 1.91 (s, 1H). | Up AA145 BB16 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-767 | 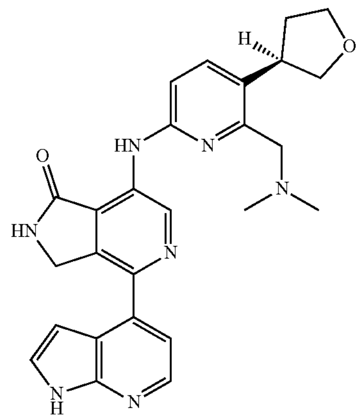 [SMILES: CN(C)Cc1nc(Nc2cnc(-c3ccnc4[nH]ccc34)c3c2C(=O)NC3)ccc1[C@H]1CCOC1] | (R)-7-((dimethylamino)methyl)-5-(tetrahydrofuran-3-yl)pyridin-2-yl)amino)-4-(1H-pyrrolo[2,3-b]pyridin-4-yl)-2,3-dihydro-1H-pyrrolo[3,4-c]pyridin-1-one | LCMS Method J m/z = 470.0 [M + H]+, Ret. time = 2.90 min Chiral HPLC method X6: Ret. time = 11.24 | 1H NMR (400 MHz, DMSO-d6) δ 11.75 (s, 1H), 10.12 (s, 1H), 9.70 (s, 1H), 9.22 (s, 1H), 8.32-8.30 (d, J = 4.9 Hz, 1H), 7.71-7.69 (d, J = 8.5 Hz, 1H), 7.54-7.52 (t, J = 3.0 Hz, 1H), 7.36-7.35 (d, J = 5.0 Hz, 1H), 7.06-7.04 (d, J = 8.5 Hz, 1H), 6.87-6.86 (dd, J = 3.4, 1.9 Hz, 1H), 4.72 (s, 2H), 4.05-3.93 (m, 2H), 3.83 (q, J = 7.7 Hz, 1H), 3.68 (s, 1H), 3.60-3.50 (m, 1H), 3.31 (d, J = 10.3 Hz, 1H), 2.46 (s, 1H), 2.38-2.26 (m, 1H), 2.25 (s, 6H), 1.91 (dd, J = 12.4, 7.6 Hz, 1H). | Up AA145 BB16 |
| I-768 | 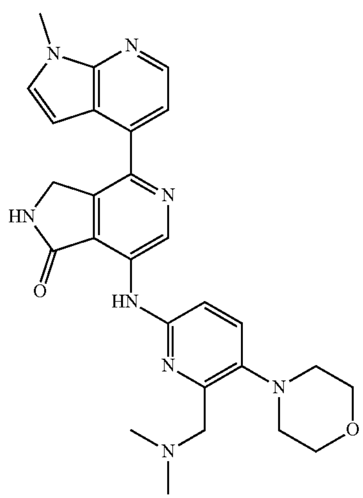 [SMILES: CN(C)Cc1nc(Nc2cnc(-c3ccnc4c3ccn4C)c3c2C(=O)NC3)ccc1N1CCOCC1] | 7-((6-((dimethylamino)methyl)-5-morpholinopyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 499.2 [M + H]+, Ret. time = 3.14 min | 1H NMR (400 MHz, DMSO-d6) δ 10.07 (S, 1H), 9.68 (S, 1H), 9.21 (S, 1H), 8.36-8.35 (d, J = 4 Hz, 1H), 7.63-7.51 (m, 2H), 7.39-7.38 (d, J = 4 Hz, 1H), 7.08-7.06 (d, J = 8 Hz, 1H), 6.88-6.87 (d, J = 4 Hz, 1h), 4.71 (S, 1H), 3.82 (S, 3H), 3.77 (S, 6H), 2.96 (S, 5H), 2.41 (S, 6H) | Up AA144 BB14 |

| # | STRUCTURE | NAME | LCMS | 1H NMR | Method Reagent AA BB |
|---|---|---|---|---|---|
| I-769 | 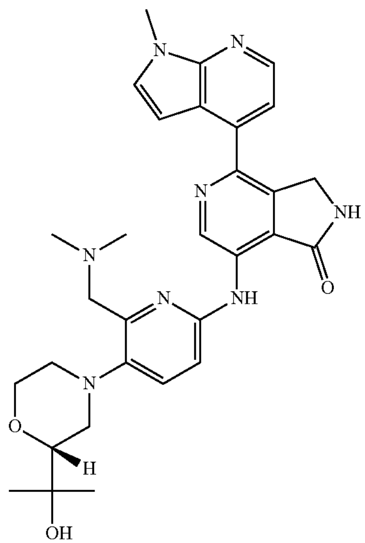 [SMILES: CN(C)Cc1nc(Nc2cnc(-c3ccnc4c3ccn4C)c3c2C(=O)NC3)ccc1N1CCO[C@@H](C(C)(C)O)C1] | (R)-7-((6-((dimethyl-amino)methyl)-5-(2-(2-hydroxypropan-2-yl)morpho-lino)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 557.2 [M + H]+, Ret. time = 3.21 min Chiral HPLC method X17: Ret. time = 6.42 | 1H NMR (400 MHz, DMSO-d6) δ 10.08 (S, 1H), 9.68 (S, 1H), 9.21 (S, 1H), 8.36-8.35 (d, J = 8 Hz, 1H), 7.64-7.58 (m, 2h), 7.39-7.38 (d, J = 4 Hz, 1H), 7.08-7.06 (d, J = 8 Hz, 1H), 4.71 (S, 1H), 4.39 (S, 1H), 3.98-3.95 (d, J = 12 Hz, 2H), 3.88 (s, 3H), 3.74-3.69 (t, J = 15 Hz, 2H), 3.41-3.38 (m, 2H), 3.29-3.24 (m, 2H), 3.11-3.08 (d, J = 12 Hz, 2H), 2.77-2.72 (t, J = 15 Hz, 1H), 2.65-2.59 (t, J = 18 Hz, 1H), 2.39 (S, 6H), 1.18-1.08 (m, 8H), 0.86 (S, 2H) | Up AA178 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-770 | 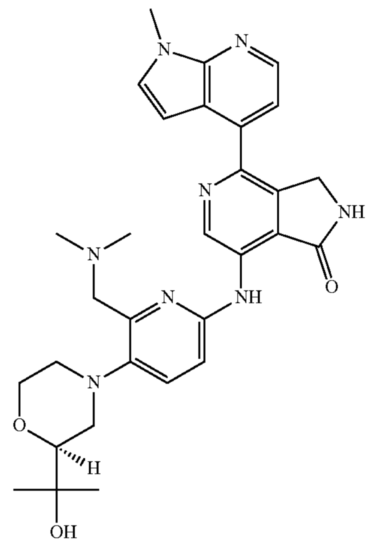 [SMILES: CN(C)Cc1nc(Nc2cnc(-c3ccnc4c3ccn4C)c3c2C(=O)NC3)ccc1N1CCO[C@H](C(C)(C)O)C1] | (S)-7-((6-((dimethylamino)methyl)-5-(2-(2-hydroxy-propan-2-yl)morpholino)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 557.2 [M + H]+, Ret. time = 3.22 min Chiral HPLC method X17: Ret. time = 6.48 | 1H NMR (400 MHz, DMSO-d6) δ 10.06 (S, 1H), 9.69 (S, 1H), 9.22 (S, 1H), 8.37-8.35 (d, J = 8 Hz 1H), 7.66-7.58 (m, 2h), 7.39-7.38 (d, J = 4 Hz, 1H), 7.10-7.08 (d, J = 8 Hz, 1H), 6.88-6.87 (d, J = 8 Hz, 1H), 4.71 (S, 1H), 4.40 (S, 1H), 3.98-3.95 (d, J = 12 Hz, 2H), 3.88 (s, 3H), 3.74-3.69 (t, J = 15 Hz, 2H), 3.41-3.38 (m, 2H), 3.29-3.24 (m, 2H), 3.11-3.08 (d, J = 12 Hz, 2h), 2.77-2.72 (t, J = 15 Hz, 1H), 2.65-2.59 (t, J = 18 Hz, 1H), 2.34 (S, 6H), 1.15-1.08 (m, 8H). | Up AA178 BB14 |

| # | STRUCTURE | NAME | LCMS | 1H NMR | Method Reagent AA BB |
|---|---|---|---|---|---|
| I-771 | 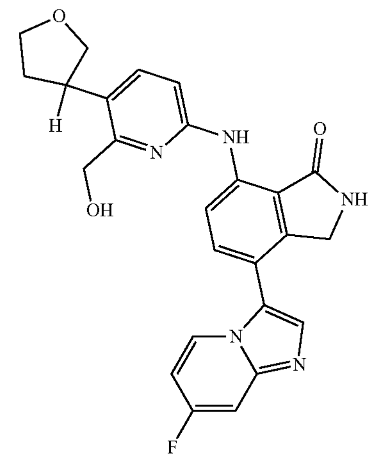 [SMILES: O=C1NCc2c(-c3cnc4cc(F)ccn34)ccc(Nc3ccc(C4CCOC4)c(CO)n3)c21] | 4-(7-fluoro-imidazo[1,2-a]pyridin-3-yl)-7-((6-(hydroxy-methyl)-5-(tetrahydrofuran-3-yl)pyridin-2-yl)amino)iso-indolin-1-one | LCMS Method J m/z = 460.0 [M + H]+, Ret. time = 3.00 min | 1H NMR (400 MHz, DMSO-d6) δ 10.07 (s, 1H), 8.86 (s, 1H), 8.79-8.77 (d, J = 8.5 Hz, 1H), 8.48-8.44 (t, J = 7.7, 5.6 Hz, 1H), 7.96 (s, 1H), 7.75-7.73 (dd, J = 24.7, 8.5 Hz, 2H), 7.56-7.52 (dd, J = 10.0, 2.8 Hz, 1H), 6.99 (td, J = 8.7, 8.1, 3.8 hz, 2H), 5.23 (S, 1H), 4.70-4.63 (m, 2H), 4.41 (s, 2H), 4.05-3.93 (m, 2H), 3.77 (dq, J = 38.3, 7.5 Hz, 1H), 3.61-3.51 (m, 2H), 2.31 (ddq, J = 12.5, 8.0, 4.7 Hz, 1H), 1.92 (dq, J = 12.4, 7.7 Hz, 1H). | V AA180 BB63 |
| I-772 | | (S)-4-(7-fluoro-imidazo[1,2-a]pyridin-3-yl)-7-((6-(piperazin-1-yl)-5-(tetrahydrofuran-3-yl)pyridin-2-yl)amino)iso-indolin-1-one | LCMS Method J m/z = 514.1 [M + H]+, Ret. time = 2.86 min Chiral HPLC method X8: Ret. time = 14.94 | 1H NMR (400 MHz, DMSO-d6) δ 10.05 (S, 1H), 8.86 (S, 1H), 8.70-8.63 (dd, 1H), 8.45 (S, 1H), 7.84 (S, 1H), 7.74-7.72 (d, J = 8 Hz, 1H), 7.62-7.60 (d, J = 8 Hz, 1H), 7.55-7.53 (d, J = 8 Hz, 1H), 6.99 (S, 1H), 6.69-6.67 (d, J = 8.3 Hz, 2H), 4.40 (s, 2H), 4.06-4.02 (t, J = 12.3 Hz, 2H), 3.82-3.80 (d, J = 8.5 Hz, 2H), 3.62-3.60 (d, |J = 7.8 HZp, 2H), 3.51-3.49 (d, J = 12.3 Hz, 2H), 3.10 (s, 3H), 2.99 (S, 3H), 2.36-2.34 (d, J = 8.6 Hz, 1H), 1.87-1.86 (d, J = 4.3 Hz, 1H) | Sp AA181 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-773 | | (R)-4-(7-fluoro-imidazo[1,2-a]pyridin-3-yl)-7-((6-(piperazin-1-yl)-5-(tetrahydrofuran-3-yl)pyridin-2-yl)amino)isoindolin-1-one | LCMS Method J m/z = 514.2 [M + H]+, Ret. time = 2.90 min Chiral HPLC method X8: Ret. time = 14.65 | 1H NMR (400 MHz, DMSO-d6) δ 10.05 (S, 1H), 8.86 (S, 1H), 8.69-8.67 (dd, 1H), 8.45 (S, 1H), 7.83 (S, 1H), 7.74-7.72 (d, J = 8 Hz, 1H), 7.62-7.60 (d, J = 8 Hz, 1H), 7.55-7.53 (d, J = 8 Hz, 1H), 6.99 (S, 1H), 6.69-6.67 (d, J = 8.3 Hz, 2H), 4.39 (s, 2H), 4.06-4.02 (t, J = 12.3 Hz, 2H), 3.82-3.80 (d, J = 8.5 Hz, 2H), 3.62-3.60 (d, J = 7.8 HZp, 2H), 3.51-3.49 (d, J = 12.3 Hz, 2H), 3.10 (s, 3H), 2.99 (S, 3H), 2.36-2.34 (d, J = 8.6 Hz, 1H), 1.87-1.85 (d, J = 8.1 Hz, 1H) | Sp AA181 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-774 | 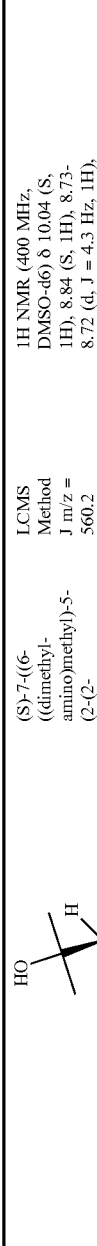 | (S)-7-((6-((dimethyl-amino)methyl)-5-(2-(2-hydroxy-propan-2-yl)morpho-linopyridin-2-yl)amino)-4-(7-fluoro-imidazo[1,2-a]pyridin-3-yl)isoindolin-1-one | LCMS Method J m/z = 560.2 [M + H]+, Ret. time = 2.93 min Chiral HPLC method X10: Ret. time = 6.29 | 1H NMR (400 MHz, DMSO-d6) δ 10.04 (S, 1H), 8.84 (S, 1H), 8.73-8.72 (d, J = 4.3 Hz, 1H), 8.46-8.42 (t, J = 16 Hz, 1H), 7.83 (S, 1H), 7.72-7.70 (d, J = 8.2 Hz, 1H), 7.62-7.59 (d, J = 12 Hz, 1H), 7.53-7.52 (d, J = 4.3 Hz, 2H), 6.99-6.97 (t, J = 8.3 Hz, 2H), 4.39 (S, 3H), 3.98-3.95 (d, J = 12.5 Hz, 2H), 3.73-3.68 (m, 2H), 3.25 (s, 1H), 2.77-2.72 (m, 1H), 2.61-2.59 (d, J = 12 Hz, 1H), 2.38 (S, 6H), 1.24 (S, 2H), 1.14-1.03 (dd, 6H), | , Sp AA178 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-775 | 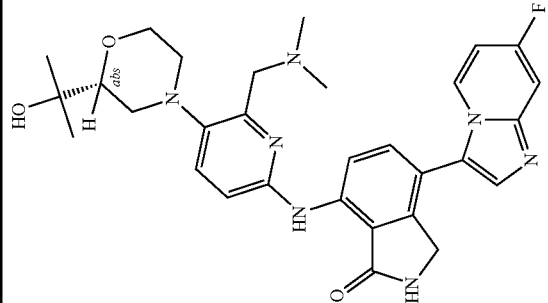 | (R)-7-((6-((dimethyl-amino)methyl)-5-(2-(2-hydroxy-propan-2-yl)morpho-linopyridin-2-yl)amino)-4-(7-fluoro-imidazo[1,2-a]pyridin-3-yl)isoindolin-1-one | LCMS Method J m/z = 560.2 [M + H]+, Ret. time = 2.96 min Chiral HPLC method X10: Ret. time = 6.27 | 1H NMR (400 MHz, DMSO-d6) δ 10.04 (S, 1H), 8.84 (S, 1H), 8.75-8.73 (d, J = 4.3 Hz, 1H), 8.46-8.43 (t, J = 12.3 Hz, 1H), 7.83 (S, 1H), 7.72-7.70 (d, J = 8.2 Hz, 1H), 7.62-7.59 (d, J = 12 Hz, 1H), 7.53-7.52 (d, J = 4.3 Hz, 2H), 6.98-6.96 (t, J = 8.3 Hz, 2H), 4.39 (S, 3H), 3.98-3.95 (d, J = 12.5 Hz, 2H), 3.73-3.68 (m, 2H), 3.25 (s, 1H), 2.77-2.72 (m, 1H), 2.61-2.59 (d, J = 12 Hz, 1H), 2.38 (S, 6H), 1.24 (S, 2H), 1.14-1.03 (d, 6H) | Sp AA178 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-776 | 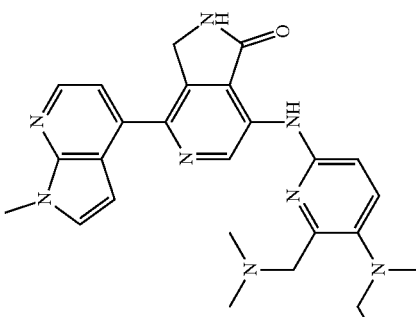 | 7-((6-((dimethylamino)methyl)-5-(4-hydroxypiperidin-1-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 512.8 [M + H]+, Ret. time = 3.17 min | 1H NMR (400 MHz, DMSO-d6) δ 10.10 (s, 1H), 9.65 (S, 1H), 8.36-8.33 (d, J = 12, 1H), 7.59-7.58 (d, J = 4.6 Hz, 1H), 7.39-7.38 (d, J = 4.2 Hz, 1H), 7.02-6.99 (d, J = 12.8 Hz, 1H), 6.88-6.87 (d, J = 4.6 Hz, 1H), 4.71 (S, 3H), 4.13-4.12 (d, J = 4.6 Hz, 1H), 3.88 (S, 3H), 3.59 (s, 3H), 3.18 (s, 6H), 2.76-2.71 (t, J = 18.3 Hz, 2H), 2.34 (s, 6H), 1.89-1.86 (d, J = 12 Hz, 2H), 1.60-1.58 (d, J = 8 Hz, 2H) | Sp AA182 BB14 |
| I-777 | 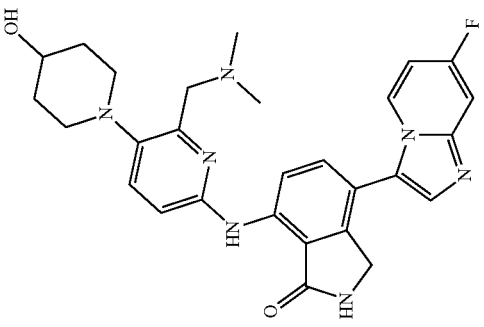 | 7-((6-((dimethylamino)methyl)-5-(4-hydroxypiperidin-1-yl)pyridin-2-yl)amino)-4-(7-fluoroimidazo[1,2-a]pyridin-3-yl)isoindolin-1-one | LCMS Method J m/z = 516.2 [M + H]+, Ret. time = 2.71 min | ¹H NMR (400 MHz, DMSO): δ 9.99 (s, 1H), 8.82 (s, 1H), 8.74-8.72 (d, J = 8 Hz, 1H), 8.45-8.42 (t, J = 6 Hz, 1H), 8.18 (s, 1H), 7.82 (s, 1H), 7.70-7.68 (d, J = 8.8 Hz, 1H), 7.54-7.51 (d, J = 8.4 Hz, 2H), 6.99-6.97 (t, J = 5.2 Hz, 1H), 4.38 (s, 2H), 3.56 (bs, 3H), 2.68-2.67 (m, 3H), 2.33 (s, 6H), 1.85 (s, 2H), 1.58-1.56 (m, 3H), 1.24 (s, 1H) | Xp AA182 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-778 | 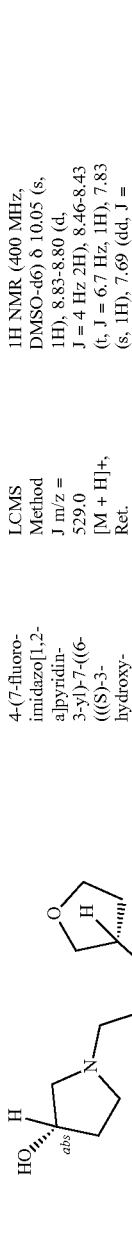 | 4-(7-fluoro-imidazo[1,2-a]pyridin-3-yl)-7-(((S)-3-hydroxy-pyrrolidin-1-yl)methyl)-5-((R)-tetrahydrofuran-3-yl)pyridin-2-yl)amino)isoindolin-1-one | LCMS Method J m/z = 529.0 [M + H]+, Ret. time = 2.91 min Chiral HPLC method X6: Ret. time = 14.76 | 1H NMR (400 MHz, DMSO-d6) δ 10.05 (s, 1H), 8.83-8.80 (d, J = 4 Hz 2H), 8.46-8.43 (t, J = 6.7 Hz, 1H), 7.83 (s, 1H), 7.69 (dd, J = 33.0, 8.5 Hz, 1H), 7.54-7.51 (dd, J = 10.1, 2.6 Hz, 2H), 7.02-6.89 (m, 2H), 4.65 (d, J = 4.2 Hz, 1H), 4.39 (s, 1H), 4.19 (t, J = 7.7, 3.8 Hz, 2H), 4.05-3.87 (m, 1H), 3.89-3.71 (m, 2H), 3.67 (d, J = 12.1 Hz, 1H), 3.60-3.48 (m, 2H), 3.31 (s, 1H), 2.76 (dd, J = 9.7, 6.3 Hz, 2H), 2.65 (t, J = 7.9 Hz, 1H), 2.50-2.42 (m, 2H), 2.40-2.22 (m, 1H), 2.05-1.82 (m, 1H), 1.54 (s, 1H). | Vp AA185 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-779 | 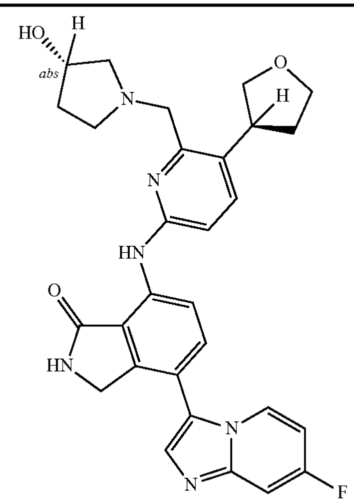 | 4-(7-fluoro-imidazo[1,2-a]pyridin-3-yl)-7-((6-(((S)-3-hydroxy-pyrrolidin-1-yl)methyl)-5-((S)-tetrahydrofuran-3-yl)pyridin-2-yl)amino)isoindolin-1-one | LCMS Method J m/z = 529.1 [M + H]+, Ret. time = 2.75 min Chiral HPLC method X6: Ret. time = 13.56 | 1H NMR (400 MHz, DMSO-d6) δ 10.05 (s, 1H), 8.83-8.80 (d, J = 12 Hz, 2H), 8.47-8.43 (t, J = 12 Hz, 1H), 7.83 (s, 1H), 7.74-7.71 (d, J = 12 Hz, 1H), 7.65-7.63 (d, J = 8.5 Hz, 1H), 7.53 (dd, J = 10.0, 2.7 Hz, 1H), 7.02-6.89 (m, 2H), 4.67 (d, J = 4.2 Hz, 1H), 4.39 (s, 1H), 4.19 (s, 1H), 4.04-3.90 (m, 2H), 3.83-3.68 (m, 2H), 3.60-3.48 (m, 2H), 3.34 (s, 2H), 2.73 (dd, J = 9.6, 6.2 Hz, 1H), 2.62 (q, J = 7.7 Hz, 1H), 2.48 (s, 1H), 2.39 (dd, J = 9.6, 3.8 Hz, 1H), 2.28 (dd, J = 12.6, 8.4, 4.9 Hz, 2H), 2.05-1.83 (m, 1H), 1.56-1.44 (m, 1H) | Vp AA183 BB63 |
| I-780 | 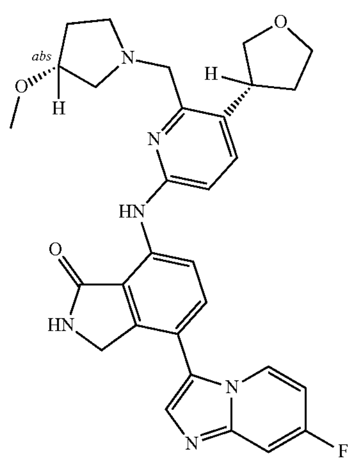 [SMILES: CO[C@@H]1CCN(Cc2nc(Nc3ccc(-c4cnc5cc(F)ccn45)c4c3C(=O)NC4)ccc2[C@H]2CCOC2)C1] | 4-(7-fluoro-imidazo[1,2-a]pyridin-3-yl)-7-((6-(((R)-3-methoxy-pyrrolidin-1-yl)methyl)-5-((R)-tetrahydrofuran-3-yl)pyridin-2-yl)amino)isoindolin-1-one | LCMS Method J m/z = 543.1 [M + H]+, Ret. time = 3.01 min Chiral HPLC method X10: Ret. time = 6.81 | 1H NMR (400 MHz, DMSO-d6) δ 10.06 (s, 1H), 8.83 (S, 2H), 8.47-8.43 (t, J = 16 Hz, 1H), 7.74-7.65 (dd, 3H), 7.55-7.52 (d, 2H), 6.99-6.92 (m, 2H), 4.40 (s, 2H), 4.12-3.62 (m, 8H), 3.55-3.51 (t, J = 12.6 Hz, 1H), 3.19-3.17 (d, J = 8 Hz, 3H), 2.77-2.73 (q, 1H), 2.34-2.27 (m, 1H), 2.01-1.87 (m, 2H), 1.65 (S, 1H) | Sp AA184 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-781 | 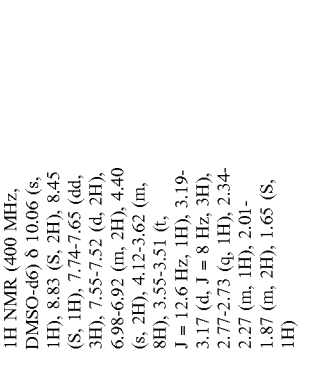 | 4-(7-fluoro-imidazo[1,2-a]pyridin-3-yl)-7-((6-(((R)-3-methoxy-pyrrolidin-1-yl)methyl)-5-((S)-tetrahydrofuran-3-yl)pyridin-2-yl)amino)iso-indolin-1-one | LCMS Method J m/z = 543.0 [M + H]+, Ret. time = 3.00 min Chiral HPLC method X10: Ret. time = 12.43 | 1H NMR (400 MHz, DMSO-d6) δ 10.06 (s, 1H), 8.83 (s, 2H), 8.45 (s, 1H), 7.74-7.65 (dd, 3H), 7.55-7.52 (d, 2H), 6.98-6.92 (m, 2H), 4.40 (s, 2H), 4.12-3.62 (m, 8H), 3.55-3.51 (t, J = 12.6 Hz, 1H), 3.19-3.17 (d, J = 8 Hz, 3H), 2.77-2.73 (q, 1H), 2.34-2.27 (m, 1H), 2.01-1.87 (m, 2H), 1.65 (S, 1H) | Sp AA184 BB63 |
| I-782 | 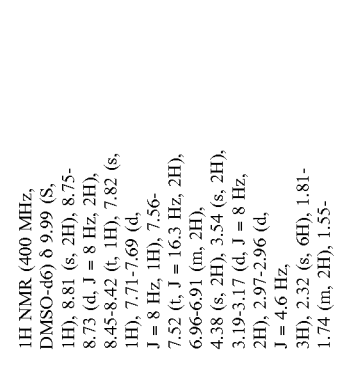 | 7-((6-(((dimethyl-amino)methyl)-5-(4-hydroxy-4-(methoxymeth-yl)piperidin-1-yl)pyridin-2-yl)amino)-4-(7-fluoro imidazo[1,2-a]pyridin-3-yl)isoindolin-1-one | LCMS Method J m/z = 560.2 [M + H]+, Ret. time = 2.83 min | 1H NMR (400 MHz, DMSO-d6) δ 9.99 (s, 1H), 8.81 (s, 2H), 8.75-8.73 (d, J = 8 Hz, 2H), 8.45-8.42 (t, 1H), 7.82 (s, 1H), 7.71-7.69 (d, J = 8 Hz, 1H), 7.56-7.52 (t, J = 16.3 Hz, 2H), 6.96-6.91 (m, 2H), 4.38 (s, 2H), 3.54 (s, 2H), 3.19-3.17 (d, J = 8 Hz, 2H), 2.97-2.96 (d, J = 4.6 Hz, 3H), 2.32 (s, 6H), 1.81-1.74 (m, 2H), 1.55-1.52 (d, J = 12.3 Hz, 2H) | Sp AA185 BB63 |

TABLE 8-continued

Characterization Data (LCMS and $^1$H NMR).

| # | STRUCTURE | NAME | LCMS | $^1$H NMR | Method Reagent AA BB |
|---|---|---|---|---|---|
| I-783 | 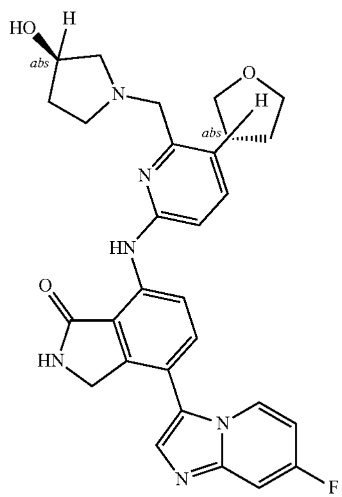 | 4-(7-fluoro-imidazo[1,2-a]pyridin-3-yl)-7-((6-(((R)-3-hydroxy-pyrrolidin-1-yl)methyl)-5-((R)-tetrahydrofuran-3-yl)pyridin-2-yl)amino)iso-indolin-1-one | LCMS Method J m/z = 529.1 [M + H]+, Ret. time = 2.91 min Chiral HPLC method X6: Ret. time = 14.64 | 1H NMR (400 MHz, DMSO-d6) δ 10.05 (s, 1H), 8.83-8.81 (d, J = 8.9 Hz, 2H), 8.46-8.43 (t, J = 7.6, 5.8 Hz, 1H), 7.82 (s, 1H), 7.74-7.63 (dd, J = 8.5 Hz, 1H), 7.54-7.51 (dd, J = 4 Hz, 1H), 6.99-6.91 (m, 2H), 4.66 (d, J = 4.2 Hz, 2H), 4.39 (s, 1H), 4.20 (s, 1H), 4.05-3.91 (m, 2H), 3.87-3.68 (m, 4H), 3.53 (t, J = 7.4 Hz, 1H), 3.31 (s, 1H), 2.74 (s, 1H), 2.63 (d, J = 7.8 Hz, 1H), 2.39 (d, J = 7.7 Hz, 1H), 2.34-2.25 (m, 1H), 2.04-1.83 (m, 1H), 1.54 (s, 1H), 1.24 (s, 1H) | Sp AA199 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-784 | 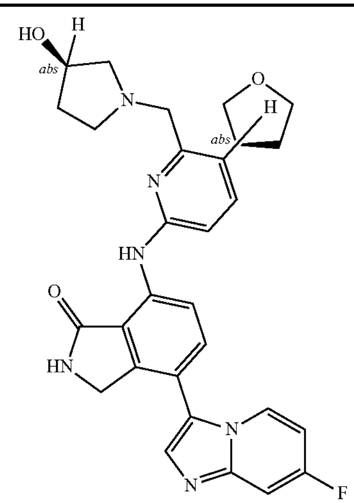 | 4-(7-fluoro-imidazo[1,2-a]pyridin-3-yl)-7-(6-(((R)-3-hydroxy-pyrrolidin-1-yl)methyl)-5-((S)-tetrahydrofuran-3-yl)pyridin-2-yl)amino)iso-indolin-1-one | LCMS Method J m/z = 529.2 [M + H]+, Ret. time = 2.44 min Chiral HPLC method X6: Ret. time = 14.89 | 1H NMR (400 MHz, DMSO-d6) δ 10.06 (s, 1H), 8.84 (d, J = 4.9 Hz, 1H), 8.47-8.44 (t, J = 6.8 Hz, 1H), 7.83 (s, 1H), 7.75-7.65 (dd, J = 8.5 Hz, 2H), 7.55-7.52 (d, J = 12 Hz, 1H), 6.98-6.92 (m, 1H), 4.67 (s, 1H), 4.40 (s, 3H), 4.22 (s, 1H), 4.1-3.6 (m, 8H), 3.91-3.52 (m, 1H), 2.9-2.6 (s, 3H), 2.42 (s, 2H), 2.00 (s, 3H), 1.56 (s, 2H), 1.25 (s, 1H), 0.87 (s, 1H). | Sp AA199 BB63 |
| I-785 | 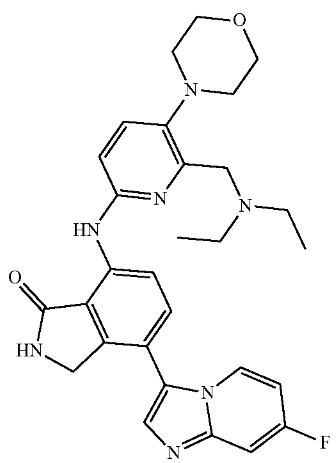 [SMILES: CCN(CC)Cc1nc(Nc2ccc(-c3cnc4cc(F)ccn34)c3c2C(=O)NC3)ccc1N1CCOCC1] | 7-((6-((diethyl-amino)meth-yl)-5-morpholino-pyridin-2-yl)amino)-4-(7-fluoro imidazo[1,2-a]pyridin-3-yl)isoindolin-1-one | LCMS Method J m/z = 530.2 [M + H]+, Ret. time = 3.19 min | ¹H NMR (400 MHz, DMSO): δ 10.12 (s, 1H), 9.12 (s, 1H), 8.92 (s, 1H), 8.68-8.65 (q, J = 12 Hz, 1H), 8.42-8.40 (d, J = 8.3 Jz, 2H), 8.09-8.07 (t, J = 8.2 Hz, 1H), 7.84-7.76 (dd, 2H), 7.58-7.54 (q, J = 12 Hz, 1H), 7.29-7.27 (d, J = 8 Hz, 1H), 4.51-4.50 (d, J = 4 Hz, 2H), 4.40 (s, 2H), 3.78 (s, 4H), 3.33-3.30 (t, J = 12.6 Hz, 4H), 1.34-1.30 (t, J = 16.3 Hz, 6H) | Sp AA186 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-786 | 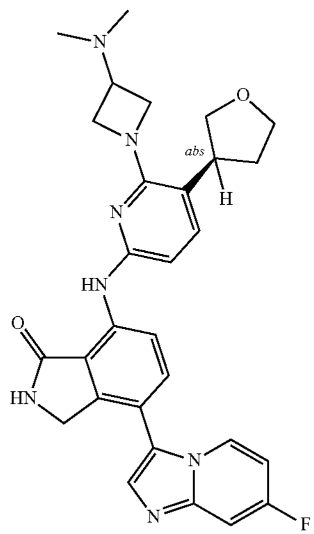 [SMILES: CN(C)C1CN(c2nc(Nc3ccc(-c4cnc5cc(F)ccn45)c4c3C(=O)NC4)ccc2[C@@H]2CCOC2)C1] | (S)-7-((6-(3-(dimethylamino)azetidin-1-yl)-5-(tetrahydrofuran-3-yl)pyridin-2-yl)amino)-4-(7-fluoroimidazo[1,2-a]pyridin-3-yl)isoindolin-1-one | LCMS Method C m/z = 528.2 [M + H]+, Ret. time = 1.27 min Chiral HPLC method X6: Ret. time = 13.61 | ¹H NMR (400 MHz, DMSO): δ 9.92 (s, 1H), 8.80 (s, 1H), 8.69-8.67 (d, J = 8.4 Hz, 1H), 8.44-8.41 (t, J = 6.8 Hz, 1H), 7.81 (s, 1H), 7.73-7.71 (d, J = 8.4 Hz 1H), 7.55-7.50 (m, 1H), 7.43-7.41 (d, J = 8.4 Hz, 1H), 6.99-6.95 (m, 1H), 6.36-6.34 (d, J = 8 Hz, 1H), 4.42 (s, 2H), 4.19-4.16 (m, 2H), 3.97-3.92 (m, 4H), 3.82-3.77 (m, 2H), 3.57-3.53 (t, J = 6.8 Hz, 2H), 2.16 (s, 6H), 1.90-1.83 (s, 1H) | Sp AA187 BB63 |

| # | STRUCTURE | NAME | LCMS | 1H NMR | Method Reagent AA BB |
|---|---|---|---|---|---|
| I-787 | 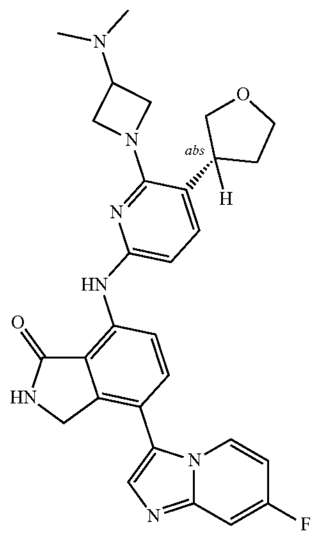 [SMILES: CN(C)C1CN(c2nc(Nc3ccc(-c4cnc5cc(F)ccn45)c4c3C(=O)NC4)ccc2[C@H]2CCOC2)C1] | (R)-7-(6-(3-(dimethylamino)azetidin-1-yl)-5-(tetrahydrofuran-3-yl)pyridin-2-yl)amino)-4-(7-fluoroimidazo[1,2-a]pyridin-3-yl)isoindolin-1-one | LCMS Method C m/z = 528.2 [M + H]+, Ret. time = 1.28 min Chiral HPLC method X6: Ret. time = 13.20 | 1H NMR (400 MHz, DMSO): δ 9.92 (s, 1H), 8.80 (s, 1H), 8.69-8.67 (d, J = 8.4 Hz, 1H), 8.44-8.41 (t, J = 6.8 Hz, 1H), 7.81 (s, 1H), 7.73-7.71 (d, J = 8.4 Hz 1H), 7.55-7.50 (m, 1H), 7.43-7.41 (d, J = 8.4 Hz, 1H), 6.99-6.95 (m, 1H), 6.36-6.34 (d, J = 8 Hz, 1H), 4.42 (s, 2H), 4.19-4.16 (m, 2H), 3.97-3.92 (m, 4H), 3.82-3.77 (m, 2H), 3.57-3.53 (t, J = 6.8 Hz, 2H), 2.16 (s, 6H), 1.90-1.83 (s, 1H) | Sp AA187 BB63 |
| I-788 | 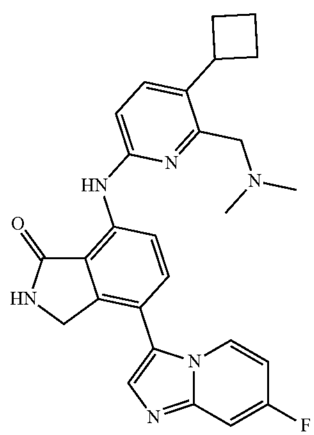 [SMILES: CN(C)Cc1nc(Nc2ccc(-c3cnc4cc(F)ccn34)c3c2C(=O)NC3)ccc1C1CCC1] | 7-(5-cyclobutyl-6-((dimethylamino)methyl)pyridin-2-yl)amino)-4-(7-fluoroimidazo[1,2-a]pyridin-3-yl)isoindolin-1-one | LCMS Method J m/z = 471.0 [M + H]+, Ret. time = 3.15 min | 1H NMR (400 MHz, DMSO-d6) δ 10.07 (s, 1H), 9.54 (s, 1H), 8.92 (s, 1H), 8.54-8.51 (t, J = 12 Hz 2H), 8.39-8.37 (d, J = 8.5 Hz, 1H), 8.12 (s, 1H), 7.86-7.74 (m, 2H), 7.33-7.13 (m, 1H), 4.45-4.41 (m, 4H), 2.95-2.94 (d, J = 4.1 Hz, 6H), 2.47 (s, 3H), 2.40-2.28 (m, 2H), 2.18-1.96 (m, 2H), 1.86 (q, J = 10.3, 9.5 Hz, 1H) | Xp AA188 BB63 |

| # | STRUCTURE | NAME | LCMS | $^1$H NMR | Method Reagent AA BB |
|---|---|---|---|---|---|
| I-789 | 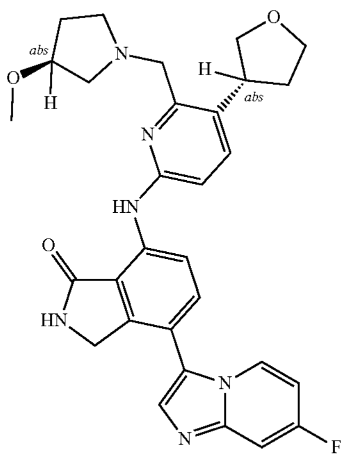 [SMILES: CO[C@H]1CCN(Cc2nc(Nc3ccc(-c4cnc5cc(F)ccn45)c4c3C(=O)NC4)ccc2[C@H]2CCOC2)C1] | 4-(7-fluoro-imidazo[1,2-a]pyridin-3-yl)-7-((6-(((S)-3-methoxy-pyrrolidin-1-yl)methyl)-5-(((R)-tetrahydrofuran-3-yl)pyridin-2-yl)amino)iso-indolin-1-one | LCMS Method J m/z = 543.2 [M + H]+, Ret. time = 2.84 min Chiral HPLC method X12: Ret. time = 9.97 | 1H NMR (400 MHz, DMSO-d6) δ 10.07 (s, 1H), 8.85-8.81 (m, 2H), 8.47-8.44 (q, J = 12 Hz, 1H), 7.84 (s, 1H), 7.74-7.65 (dd, J = 8.5 Hz 1H), 7.55-7.52 (dd, J = 10.0, 2.6 Hz, 1H), 7.00-6.92 (m, 2H), 4.40 (s, 2H), 4.04-3.91 (m, 2H), 3.93-3.69 (m, 3H), 3.58-3.46 (m, 2H), 3.15 (s, 1H), 2.75 (dd, J = 10.1, 6.3 Hz, 2H), 2.66-2.52 (m, 2H), 2.48 (d, J = 8.9 Hz, 1H), 2.06-1.83 (m, 3H), 1.71-1.61 (m, 1H) | Sp AA189 BB63 |
| I-790 | 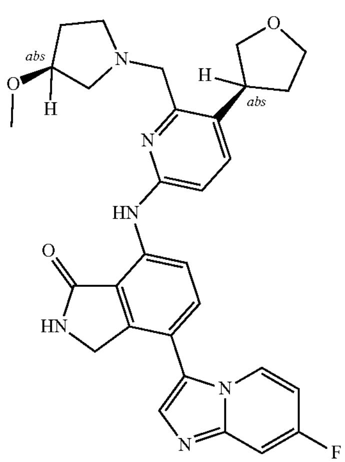 [SMILES: CO[C@H]1CCN(Cc2nc(Nc3ccc(-c4cnc5cc(F)ccn45)c4c3C(=O)NC4)ccc2[C@@H]2CCOC2)C1] | 4-(7-fluoro-imidazo[1,2-a]pyridin-3-yl)-7-((6-(((S)-3-methoxy-pyrrolidin-1-yl)methyl)-5-((S)-tetrahydrofuran-3-yl)pyridin-2-yl)amino)iso-indolin-1-one | LCMS Method J m/z = 544.2 [M + H]+, Ret. time = 2.87 min Chiral HPLC method X12: Ret. time = 10.81 | 1H NMR (400 MHz, DMSO-d6) δ 10.06 (s, 1H), 8.85-8.81 (t, J = 12 Hz, 2H), 8.47-8.44 (t, J = 12 Hz, 1H), 7.74-7.65 (dd, J = 8.5 Hz, 1H), 7.55-7.52 (dd, J = 10.0, 2.6 Hz, 1H), 7.00-6.92 (m, 2H), 4.40 (s, 2H), 4.05-3.92 (m, 2H), 3.90 (d, J = 6.5 Hz, 2H), 3.90-3.65 (m, 2H), 3.53 (dd, J = 8.2, 6.8 Hz, 1H), 3.15 (s, 3H), 2.77 (dd, J = 10.1, 6.2 Hz, 2H), 2.70-2.54 (m, 1H), 2.48 (dd, J = 11.5, 5.2 Hz, 1H), 2.04-1.84 (m, 2H), 1.25 (s, 1H) | Sp AA189 BB63 |

| # | STRUCTURE | NAME | LCMS | ¹H NMR | Method Reagent AA BB |
|---|---|---|---|---|---|
| I-791 | 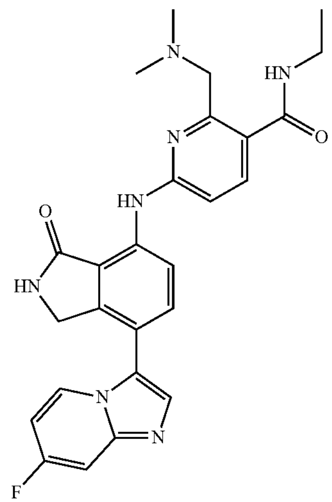 [SMILES: CCNC(=O)c1ccc(Nc2ccc(-c3cnc4cc(F)ccn34)c3c2C(=O)NC3)nc1CN(C)C] | 2-(((dimethyl-amino)methyl)-N-ethyl-6-((7-(7-fluoroimidazo[1,2-a]pyridin-3-yl)-3-oxoisoindolin-4-yl)amino)nicotinamide | LCMS Method J m/z = 488.2 [M + H]+, Ret. time = 2.40 min | 1H NMR (400 MHz, DMSO-d6) δ 10.34 (s, 1H), 9.94 (s, 1H), 8.93 (s, 1H), 8.84-8.82 (d, J = 8 Hz, 2H), 8.50-8.47 (q, J = 12.9 Hz, 1H), 8.00-7.97 (d, J = 12 Hz, 1H), 7.86 (s, 1H), 7.81-7.79 (d, 1H), 7.56-7.53 (dd, 1H), 7.04-6.97 (m, 2H), 4.43, (s, 1H), 3.68 (s, 1H), 3.43-3.36 (m, 3H), 2.3 (s, 6H), 1.20-1.17 (t, J = 12 Hz, 4H) | Xp AA190 BB63 |
| I-792 | 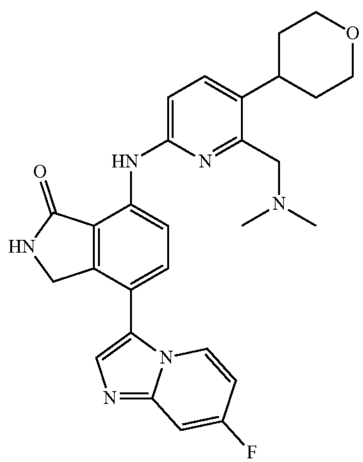 [SMILES: CN(C)Cc1nc(Nc2ccc(-c3cnc4cc(F)ccn34)c3c2C(=O)NC3)ccc1C1CCOCC1] | 7-((6-(((dimethyl-amino)methyl)-5-(tetrahydro-2H-pyran-4-yl)pyridin-2-yl)amino)-4-(7-fluoro-imidazo[1,2-a]pyridin-3-yl)isoindolin-1-one | LCMS Method J m/z = 500.6 [M + H]+, Ret. time = 2.84 min | ¹H NMR (400 MHz, DMSO): δ 10.03 (s, 1H), 8.83 (s, 1H), 8.78-8.76 (d, J = 8 Hz, 1H), 7.47-7.44 (t, J = 6.4 Hz, 1H), 7.83 (s, 1H), 7.74-7.72 (d, J = 8.4 Hz, 1H), 7.68-7.66 (d, J = 8 Hz, 1H), 7.55-7.52 (dd, J = 2.4 Hz, 1H), 6.96-6.94 (t, J = 2 Hz, 1H), 6.92 (s, 1H), 4.39 (s, 2H), 3.99-3.96 (dq, 2H), 3.59 (s, 2H), 3.47-3.42 (t, J = 10.4 Hz, 2H), 3.28 (s, 1H), 3.20 (bs, 1H), 2.24 (s, 6H), 1.70-1.65 (m, 3H). | Xp AA191 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-793 | 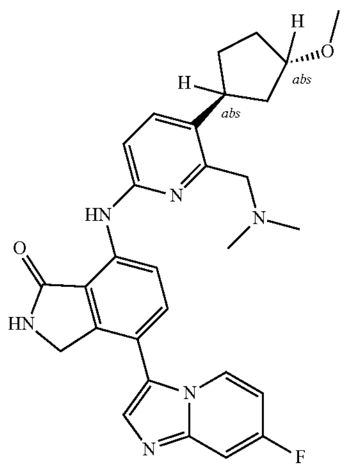 [SMILES: CO[C@H]1CC[C@H](c2ccc(Nc3ccc(-c4cnc5cc(F)ccn45)c4c3C(=O)NC4)nc2CN(C)C)C1] | 7-((6-((dimethyl-amino)methyl)-5-((1S,3S)-3-methoxycyclo-pentyl)pyridin-2-yl)amino)-4-(7-fluoro-imidazo[1,2-a]pyridin-3-yl)isoindolin-1-one | LCMS Method J m/z = 515.2 [M + H]+, Ret. time = 2.76 min Chiral HPLC method X4: Ret. time = 7.75 | ¹H NMR (400 MHz, DMSO): δ 10.02 (s, 1H), 8.83 (s, 1H), 8.73-8.71 (d, J = 7.2 Hz, 1H), 7.45-7.42 (t, J = 6.4 Hz, 1H), 7.82 (s, 1H), 7.73-7.69 (t, J = 8.4 Hz, 2H), 7.54-7.52 (dd, J = 2.4 Hz, 1H), 6.98-6.96 (t, J = 8 Hz, 2H), 4.39 (s, 2H), 3.89 (bs, 1H), 3.66 (bs, 2H), 3.44-3.42 (d, J = 8.8 Hz, 1H), 3.24 (s, 3H), 2.30 (s, 6H), 1.96-1.91 (dq, 1H), 1.83 (bs, 1H), 1.70 (bs, 1H), 1.63 (bs, 1H), 1.49-1.46 (dq, 1H), 1.23 (s, 1H). | Yp AA192 BB63 |
| I-794 | 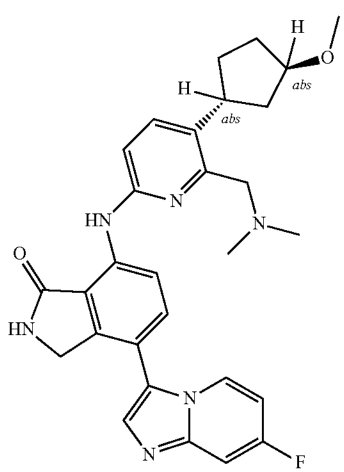 [SMILES: CO[C@@H]1CC[C@@H](c2ccc(Nc3ccc(-c4cnc5cc(F)ccn45)c4c3C(=O)NC4)nc2CN(C)C)C1] | 7-((6-((dimethyl-amino)methyl)-5-((1R,3R)-3-methoxycyclo-pentyl)pyridin-2-yl)amino)-4-(7-fluoro-imidazo[1,2-a]pyridin-3-yl)isoindolin-1-one | LCMS Method J m/z = 515.2 [M + H]+, Ret. time = 2.73 min Chiral HPLC method X4: Ret. time = 7.85 | ¹H NMR (400 MHz, DMSO): δ 10.03 (s, 1H), 8.83 (s, 1H), 8.73-8.71 (d, J = 7.2 Hz, 1H), 7.46-7.42 (t, J = 6.4 Hz, 1H), 7.88 (s, 1H), 7.73-7.69 (t, J = 8.4 Hz, 2H), 7.54-7.52 (dd, J = 2.4 Hz, 1H), 6.99-6.97 (t, J = 8 Hz, 2H), 4.40 (s, 2H), 3.89 (bs, 1H), 3.66 (bs, 2H), 3.44-3.42 (d, J = 8.8 Hz, 1H), 3.24 (s, 3H), 2.30 (s, 6H), 1.96-1.91 (dq, 1H), 1.83 (bs, 1H), 1.70 (bs, 1H), 1.63 (bs, 1H), 1.49-1.46 (dq, 1H), 1.24 (s, 1H). | Yp AA192 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-795 | 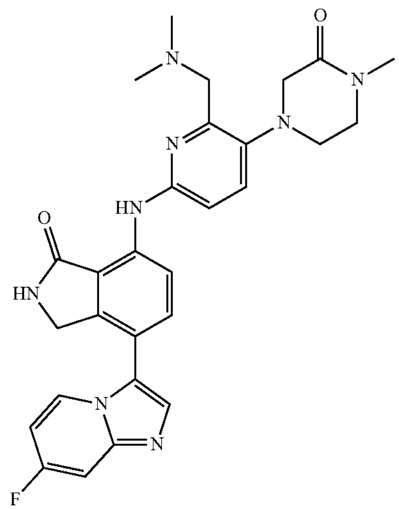 [SMILES: CN(C)Cc1nc(Nc2ccc(-c3cnc4cc(F)ccn34)c3c2C(=O)NC3)ccc1N1CCN(C)C(=O)C1] | 7-((6-((dimethyl-amino)methyl)-5-(4-methyl-3-oxopiperazin-1-yl)pyridin-2-yl)amino)-4-(7-fluoro-imidazo[1,2-a]pyridin-3-yl)isoindolin-1-one | LCMS Method J m/z = 529.0 [M + H]+, Ret. time = 2.63 min | ¹H NMR (400 MHz, DMSO): δ 10.05 (s, 1H), 8.83 (s, 1H), 8.77-8.75 (d, J = 8.4 Hz, 1H), 8.45-8.42 (t, J = 5.6 Hz, 1H), 7.82 (s, 1H), 7.72-7.70 (d, J = 8.4 Hz, 1H), 7.59-7.51 (dd, J = 8.4 Hz, 2H), 6.98-6.96 (t, J = 8 Hz, 2H), 4.38 (s, 2H), 3.60 (bs, 2H), 3.54 (bs, 2H), 3.41 (bs, 2H), 2.91 (s, 3H), 2.30 (s, 6H), 1.23 (s, 2H), | Xp AA193 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-796 | 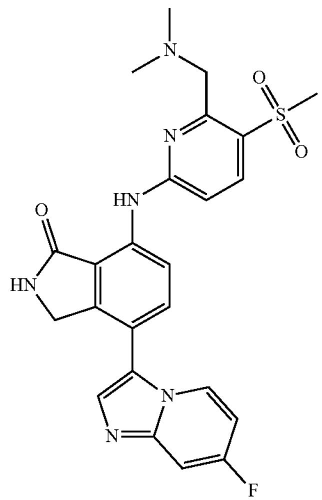 [SMILES: CN(C)Cc1nc(Nc2ccc(-c3cnc4cc(F)ccn34)c3c2C(=O)NC3)ccc1S(C)(=O)=O] | 7-((6-((dimethylamino)methyl)-5-(methylsulfonyl)pyridin-2-yl)amino)-4-(7-fluoroimidazo[1,2-a]pyridin-3-yl)isoindolin-1-one | LCMS Method H m/z = 495.0 [M + H]+, Ret. time = 2.81 min | ¹H NMR (400 MHz, DMSO): δ 9.01 (s, 1H), 8.84-8.82 (d, J = 8 Hz, 1H), 8.51-8.48 (t, J = 6 Hz, 1H), 8.18 (s, 1H), 8.12-8.10 (d, J = 8.8 Hz, 1H), 7.88 (s, 1H), 7.85-7.83 (d, J = 8.4 Hz, 1H), 7.57-7.53 (dd, J = 2.4 Hz, 1H), 7.15-7.13 (d, J = 8.8 Hz 1H), 7.02-6.99 (t, J = 7.6 Hz, 1H), 4.45 (s, 2H), 3.89 (s, 2H), 3.43 (s, 3H), 2.27 (s, 6H). | Xp AA194 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-797 | 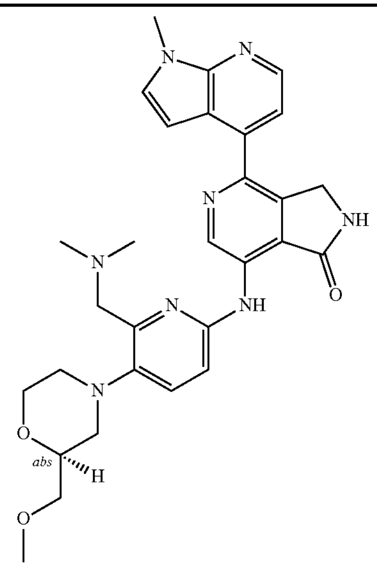 | (S)-7-((6-((dimethylamino)methyl)-5-(2-(methoxymethyl)morpholino)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 543.2 [M + H]+, Ret. time = 3.22 min Chiral HPLC method X9: Ret. time = 6.70 | ¹H NMR (400 MHz, DMSO): δ 10.09 (s, 1H), 9.67 (s, 1H), 9.20 (s, 1H), 8.36-8.34 (d, J = 5.2 Hz, 1H), 7.60 (s, 1H), 7.59-7.58 (d, J = 3.6 Hz, 1H), 7.38-7.37 (d, J = 4.8 Hz, 1H), 7.04-7.02 (d, J = 8.8 Hz, 1H), 6.87-6.86 (d, J = 3.2 Hz 1H), 4.70 (s, 2H), 3.92-3.80 (dq, 3H), 3.79 (s, 1H), 3.73-3.71 (t, J = 3.2 Hz, 1H), 3.60 (s, 2H), 3.44-3.39 (m, 1H), 3.27 (s, 3H), 3.23-3.21 (d, J = 8 Hz, 1H), 3.12-3.09 (d, J = 11.6 Hz, 1H), 2.79-2.76 (t, J = 1.6 Hz, 1H), 2.60-2.55 (m, 1H), 2.34 (s, 6H), 1.23 (s, 1H), 1.11-1.07 (t, J = 7.2 Hz, 1H). | Sp AA151 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-798 | 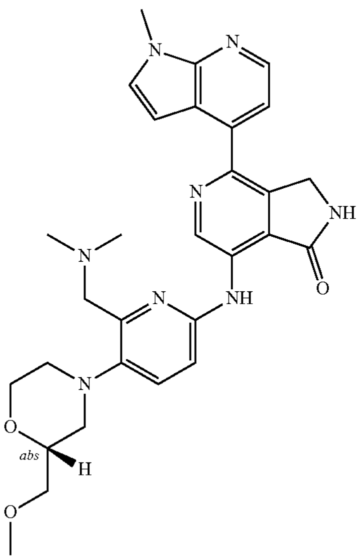 [SMILES: COC[C@H]1CN(c2ccc(Nc3cnc(-c4ccnc5c4ccn5C)c4c3C(=O)NC4)nc2CN(C)C)CCO1] | (R)-7-((6-((dimethylamino)methyl)-5-(2-(methoxymethyl)morpholino)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 543.2 [M + H]+, Ret. time = 3.22 min Chiral HPLC method X9: Ret. time = 6.99 | ¹H NMR (400 MHz, DMSO): δ 10.03 (s, 1H), 9.69 (s, 1H), 9.22 (s, 1H), 8.36-8.35 (d, J = 5.2 Hz, 1H), 7.60 (s, 1H), 7.59-7.58 (d, J = 3.6 Hz, 1H), 7.39-7.38 (d, J = 4.8 Hz, 1H), 7.04-7.02 (d, J = 8.8 Hz, 1H), 6.87-6.86 (d, J = 3.2 Hz 1H), 4.71 (s, 2H), 3.92-3.80 (dq, 3H), 3.79 (s, 1H), 3.73-3.71 (t, J = 3.2 Hz, 1H), 3.60 (s, 2H), 3.44-3.39 (m, 1H), 3.27 (s, 3H), 3.23-3.21 (d, J = 8 Hz, 1H), 3.12-3.09 (d, J = 11.6 Hz, 1H), 2.79-2.76 (t, J = 1.6 Hz, 1H), 2.60-2.55 (m, 1H), 2.34 (s, 6H), 1.23 (s, 1H), 1.11-1.07 (t, J = 7.2 Hz, 1H). | Sp AA151 BB14 |

| # | STRUCTURE | NAME | LCMS | ¹H NMR | Method Reagent AA BB |
|---|---|---|---|---|---|
| I-799 | 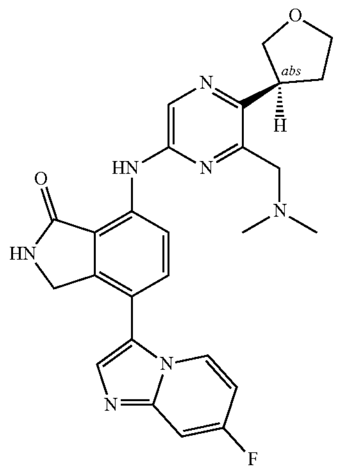 [SMILES: CN(C)Cc1nc(Nc2ccc(-c3cnc4cc(F)ccn34)c3c2C(=O)NC3)cnc1[C@@H]1CCOC1] | (S)-7-((6-((dimethyl-amino)methyl)-5-(tetrahydro-furan-3-yl)pyrazin-2-yl)amino)-4-(7-fluoro-imidazo[1,2-a]pyridin-3-yl)isoindolin-1-one | LCMS Method J m/z = 488.0 [M + H]+, Ret. time = 2.59 min Chiral HPLC method X4: Ret. time = 8.58 | ¹H NMR (400 MHz, DMSO): δ 10.25 (s, 1H), 8.93 (s, 1H), 8.72-8.70 (d, J = 8.4 Hz, 1H), 8.49-8.46 (t, J = 6.4 Hz, 1H), 8.36 (s, 1H), 7.85 (s, 1H), 7.79-7.77 (d, J = 8.4 Hz, 1H), 7.55-7.53 (d, J = 10 Hz 1H), 6.99-6.96 (t, J = 4.8 Hz, 1H), 4.42 (s, 2H), 4.09-4.05 (t, J = 8 Hz, 1H), 3.96-36.87 (m, 2H), 3.85-3.82 (t, J = 7.2 Hz, 1H), 3.67-3.62 (dq, 2H), 3.60 (s, 1H), 2.22 (s, 6H), 1.23 (s, 1H), 1.11-1.07 (t, J = 6.8 Hz 1H). | Sp AA195 BB63 |
| I-800 | 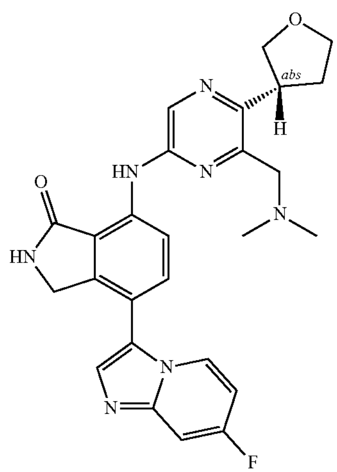 [SMILES: CN(C)Cc1nc(Nc2ccc(-c3cnc4cc(F)ccn34)c3c2C(=O)NC3)cnc1[C@H]1CCOC1] | (R)-7-((6-((dimethyl-amino)methyl)-5-(tetrahydrofuran-3-yl)pyrazin-2-yl)amino)-4-(7-fluoro-imidazo[1,2-a]pyridin-3-yl)isoindolin-1-one | LCMS Method J m/z = 488.0 [M + H]+, Ret. time = 2.58 min Chiral HPLC method X4: Ret. time = 8.52 | ¹H NMR (400 MHz, DMSO): δ 10.25 (s, 1H), 8.93 (s, 1H), 8.72-8.69 (d, J = 8.4 Hz, 1H), 8.49-8.46 (t, J = 6.4 Hz, 1H), 8.37 (s, 1H), 7.85 (s, 1H), 7.79-7.77 (d, J = 8.4 Hz, 1H), 7.55-7.53 (d, J = 10 Hz 1H), 6.99-6.96 (t, J = 4.8 Hz, 1H), 4.42 (s, 2H), 4.12-4.07 (t, J = 8 Hz, 1H), 3.96-36.87 (m, 2H), 3.85-3.82 (t, J = 7.2 Hz, 1H), 3.67-3.62 (dq, 2H), 3.60 (s, 1H), 2.22 (s, 6H), 1.23 (s, 1H), 1.11-1.07 (t, J = 6.8 Hz 1H). | Sp AA195 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-801 | 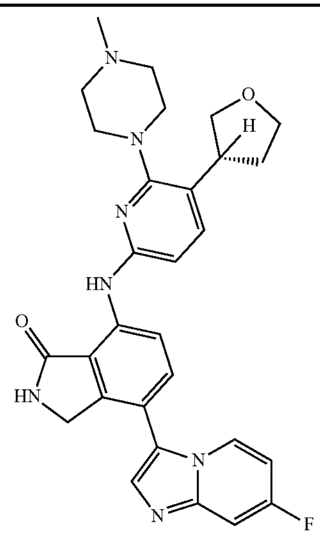 | (R)-4-(7-fluoro-imidazo[1,2-a]pyridin-3-yl)-7-((6-(4-methylpiperazin-1-yl)-5-(tetrahydrofuran-3-yl)pyridin-2-yl)amino)iso-indolin-1-one | LCMS Method J m/z = 528.1 [M + H]+, Ret. time = 2.88 min Chiral HPLC method X6: Ret. time = 11.83 | ¹H NMR (400 MHz, DMSO): δ 10.04 (s, 1H), 8.84 (s, 1H), 8.72-8.70 (d, J = 8.8 Hz, 1H), 8.47-8.44 (t, J = 8.8 Hz, 1H), 7.83 (s, 1H), 7.76-7.74 (d, J = 8.4 Hz, 1H), 7.61-7.59 (d, J = 8.4 Hz, 1H), 7.54-7.51 (d, J = 2.0 Hz 1H), 6.97-6.95 (t, J = 4.8 Hz 1H), 6.67-6.65 (d, J = 8.4 Hz, 1H), 4.39 (s, 2H), 4.05-3.97 (m, 2H), 3.83-3.77 (dq, 1H), 3.63-3.56 (m, 1H), 3.52-3.48 (t, J = 7.6 Hz, 1H), 3.39 (s, 1H), 3.12-3.05 (m, 4H), 2.36-2.30 (m, 1H), 2.26 (s, 3H), 1.89-1.80 (m, 1H), 1.23 (s, 2H), 1.11-1.07 (t, J = 7.2 Hz, 1H). | Sp AA196 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-802 | 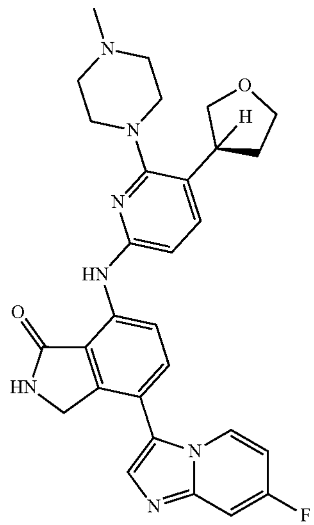 | (S)-4-(7-fluoroimidazo[1,2-a]pyridin-3-yl)-7-((6-(4-methylpiperazin-1-yl)-5-(tetrahydrofuran-3-yl)pyridin-2-yl)amino)isoindolin-1-one | LCMS Method J m/z = 528.2 [M + H]+, Ret. time = 2.87 min Chiral HPLC method X6: Ret. time = 6.02 | ¹H NMR (400 MHz, DMSO): δ 10.04 (s, 1H), 8.84 (s, 1H), 8.71-8.69 (d, J = 8.8 Hz, 1H), 8.47-8.44 (t, J = 8.8 Hz, 1H), 7.83 (s, 1H), 7.76-7.74 (d, J = 8.4 Hz, 1H), 7.61-7.59 (d, J = 8.4 Hz, 1H), 7.55-7.52 (d, J = 2.0 Hz 1H), 6.99-6.96 (t, J = 4.8 Hz, 1H), 6.68-6.66 (d, J = 8.4 Hz, 1H), 4.39 (s, 2H), 4.05-3.97 (m, 2H), 3.83-3.77 (dq, 1H), 3.63-3.56 (m, 1H), 3.52-3.48 (t, J = 7.6 Hz, 1H), 3.39 (s, 1H), 3.12-3.05 (m, 4H), 2.36-2.30 (m, 1H), 2.26 (s, 3H), 1.89-1.80 (m, 1H), 1.23 (s, 2H), 1.11-1.07 (t, J = 7.2 Hz, 1H). | Sp AA196 BB63 |
| I-803 | 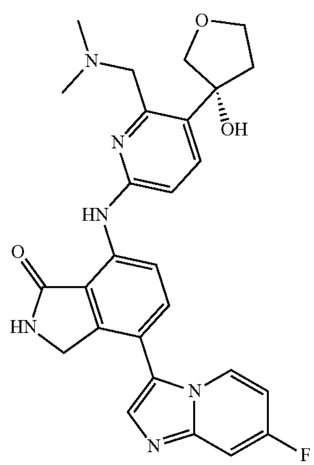 [SMILES: CN(C)Cc1nc(Nc2ccc(-c3cnc4cc(F)ccn34)c3c2C(=O)NC3)ccc1[C@]1(O)CCOC1] | (R)-7-((6-((dimethylamino)methyl)-5-(3-hydroxytetrahydrofuran-3-yl)pyridin-2-yl)amino)-4-(7-fluoroimidazo[1,2-a]pyridin-3-yl)isoindolin-1-one | LCMS Method J m/z = 503.0 [M + H]+, Ret. time = 2.59 min Chiral HPLC method X12: Ret. time = 11.01 | ¹H NMR (400 MHz, DMSO): δ 10.145 (s, 1H), 8.898 (s, 1H), 8.760 (d, J = 8.4 Hz, 1H), 8.475 (t, J = 6 Hz, 1H), 7.850 (s, 1H), 7.754 (dd, J = 8.8 Hz, 3H), 7.558 (dd, J = 2.8 Hz, 1H), 7.013-6.946 (m, 2H), 4.417 (s, 2H), 4.086 (d, J = 8.8 Hz, 1H), 3.978-3.845 (m, 4H), 3.694 (d, J = 12.4 Hz, 1H), 2.337-2.292 (m, 1H), 2.251 (s, 6H). | Sp AA197 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-804 | 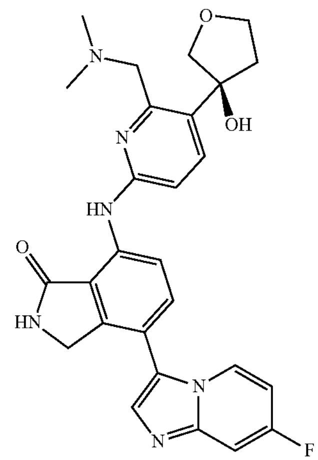 [SMILES: CN(C)Cc1nc(Nc2ccc(-c3cnc4cc(F)ccn34)c3c2C(=O)NC3)ccc1[C@@]1(O)CCOC1] | (S)-7-(((dimethyl-amino)methyl)-5-(3-hydroxy-tetrahydro-furan-3-yl)pyridin-2-yl)amino)-4-(7-fluoro-imidazo[1,2-a]pyridin-3-yl)isoindolin-1-one | LCMS Method J m/z = 503.0 [M + H]+, Ret. time = 2.60 min Chiral HPLC method X12: Ret. time = 17.22 | ¹H NMR (400 MHz, DMSO): δ 10.145 (s, 1H), 8.89 (s, 1H), 8.760 (d, J = 8.8 Hz, 1H), 8.475 (t, J = 6 Hz, 1H), 7.851 (s, 1H), 7.719 (dd, J = 8.8 Hz, 2H), 7.697 (d, J = 2.4 Hz, 1H), 7.558 (dd, J = 2.4 Hz, 1H), 7.013-6.946 (m, 2H), 4.417 (s, 1H), 4.086 (d, J = 8.8 Hz, 1H), 3.978-3.876 (m, 4H), 3.694 (d, J = 12.4 Hz, 1H), 2.337-2.314 (m, 1H), 2.250 (s, 6H). | Sp AA197 BB63 |
| I-805 | 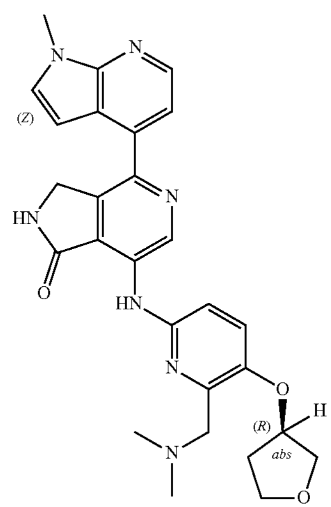 | (R)-7-(((dimethyl-amino)methyl)-5-((tetrahydrofuran-3-yl)oxy)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 500.1 [M + H]+, Ret. time = 2.83 min Chiral HPLC method X15: Ret. time = 9.27 | ¹H NMR (400 MHz, DMSO): δ 10.030 (s, 1H), 9.605 (s, 1H), 9.185 (s, 1H), 8.363 (d, J = 4.4 Hz, 1H), 7.590 (d, J = 2.8 Hz, 1H), 7.520 (d, J = 8.8 Hz, 1H), 7.388 (d, J = 4.4 Hz, 1H), 7.060 (d, J = 8.8 Hz, 1H), 6.880 (d, J = 2.8 Hz, 1H), 5.065 (s, 1H), 4.713 (s, 2H), 3.846-3.821 (m, 6H), 3.573 (s, 2H), 2.288 (s, 6H), | Up AA198 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-806 | 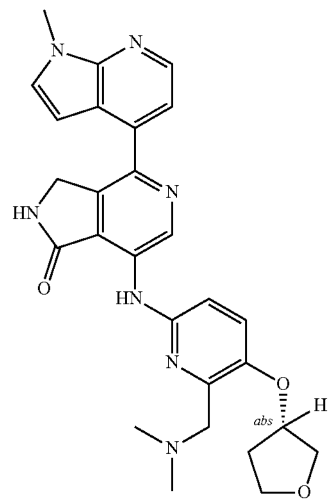 [SMILES: CN(C)Cc1nc(Nc2cnc(-c3ccnc4c3ccn4C)c3c2C(=O)NC3)ccc1O[C@H]1CCOC1] | (S)-7-((6-((dimethylamino)methyl)-5-((tetrahydrofuran-3-yl)oxy)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 500.2 [M + H]+, Ret. time = 3.15 min Chiral HPLC method X15: Ret. time = 9.18 | ¹H NMR (400 MHz, DMSO): δ 10.030 (s, 1H), 9.605 (s, 1H), 9.185 (s, 1H), 8.363 (d, J = 4.4 Hz, 1H), 7.590 (d, J = 2.8 Hz, 1H), 7.520 (d, J = 8.8 Hz, 1H), 7.388 (d, J = 4.4 Hz, 1H), 7.060 (d, J = 8.8 Hz, 1H), 6.880 (d, J = 2.8 Hz, 1H), 5.065 (s, 1H), 4.713 (s, 2H), 3.846-3.821 (m, 6H), 3.573-3.565 (s, 2H), 2.288 (s, 6H). | Up AA198 BB14 |
| I-807 | 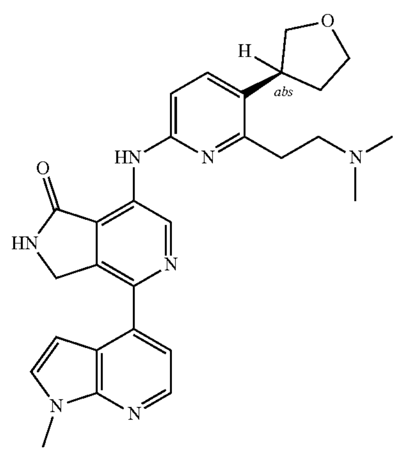 [SMILES: CN(C)CCc1nc(Nc2cnc(-c3ccnc4c3ccn4C)c3c2C(=O)NC3)ccc1[C@@H]1CCOC1] | (R)-7-((6-(2-(dimethylamino)ethyl)-5-(tetrahydrofuran-3-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 498.2 [M + H]+, Ret. time = 3.24 min Chiral HPLC method X14: Ret. time = 11.85 | ¹H NMR (400 MHz, DMSO): δ 10.078 (s, 1H), 9.647 (s, 1H), 9.215 (s, 1H), 8.360 (d, J = 5.8 Hz, 1H), 7.618 (dd, J = 8.8 Hz 2H), 7.390 (d, J = 5.2 Hz, 1H), 6.898, (dd, J = 3.2 Hz, 2H), 4.716 (s, 2H), 3.972-3.965 (m, 2H), 3.820-3.812, (m, 3H), 3.575-3.564 (m, 2H), 3.010 (t, J = 7.2 Hz, 2 H), 2.719 (t, 7.6 Hz, 2H), 2.335 (m, 6H), 1.895 (m, 1H). | Up AA175 BB14 |

| # | STRUCTURE | NAME | LCMS | ¹H NMR | Method Reagent AA BB |
|---|---|---|---|---|---|
| I-808 | 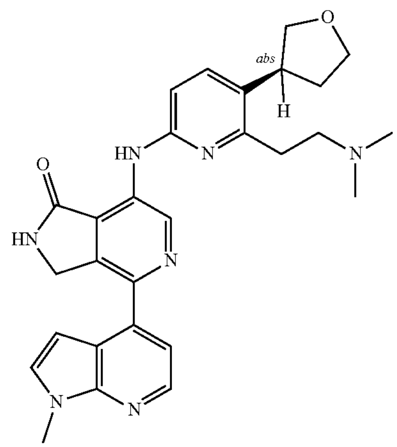 [SMILES: CN(C)CCc1nc(Nc2cnc(-c3ccnc4c3ccn4C)c3c2C(=O)NC3)ccc1[C@@H]1CCOC1] | (S)-7-((6-(2-(dimethylamino)ethyl)-5-(tetrahydrofuran-3-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 498.2 [M + H]+, Ret. time = 3.24 min Chiral HPLC method X14: Ret. time = 14.48 | ¹H NMR (400 MHz, DMSO): δ 10.078 (s, 1H), 9.647 (s, 1H), 9.215 (s, 1H), 8.360 (d, J = 5.8 Hz, 1H), 7.618 (dd, J = 8.8 Hz 2H), 7.390 (d, J = 5.2 Hz, 1H), 6.898, (dd, J = 3.2 Hz, 2H), 4.716 (s, 2H), 3.972-3.963 (m, 2H), 3.820-3.812, (m, 4H), 3.575-3.561 (m, 2H), 3.010 (t, J = 7.2 Hz, 2 H), 2.719 (t, 7.6 Hz, 2H), 2.335-2.329 (m, 7H), 1.895-1.883 (m, 1H). | Up AA175 BB14 |
| I-809 | 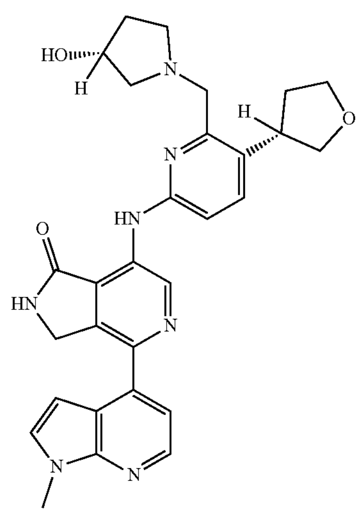 [SMILES: Cn1ccc2c(-c3ncc(Nc4ccc([C@@H]5CCOC5)c(CN5CC[C@@H](O)C5)n4)c4c3CNC4=O)ccnc21] | 7-((6-(((R)-3-hydroxypyrrolidin-1-yl)methyl)-5-((S)-THF-3-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 526.2 [M + H]+, Ret. time = 3.18 min Chiral HPLC method X12: Ret. time = 10.24 | ¹H NMR (400 MHz, DMSO): δ 10.163 (s, 1H), 9.710 (s, 1H), 9.232 (s, 1H), 8.370 (d, J = 4.8 Hz, 1H), 7.693 (d, J = 4.8 Hz, 1H), 7.596 (d, J = 3.2 Hz, 1H), 7.402 (d, J = 4.8 Hz, 1H), 7.030 (d, J = 8.4 Hz 1H), 6.900 (d, J = 3.6 Hz 1H), 4.682 (s, 3H), ), 4.225 (s, 1 H), 3.991-3.985 (m, 2H), 3.857 (s 2H), 3.819-3.811 (m, 7H), 3.549 (q J = 7.2 Hz, 1H), 2.788-2.881 (m 1H), 2.559-2.551 (m, 1H), 2.537-2.527 (m, 1H), 2.394 (q, J = 4.1 Hz 1H), 2.329-2.325 (m, 1H), 2.004-1.995 (m, 1H). | Up AA183 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-810 | 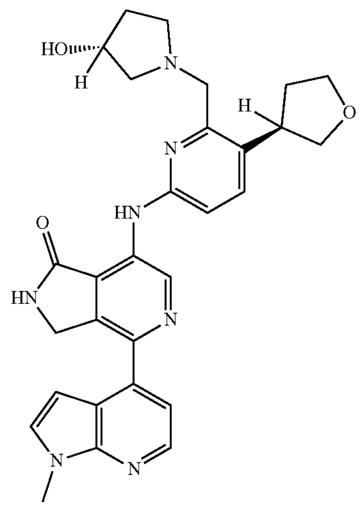 [SMILES: Cn1ccc2c(-c3ncc(Nc4ccc([C@H]5CCOC5)c(CN5CC[C@@H](O)C5)n4)c4c3CNC4=O)ccnc21] | 7-((6-(((R)-3-hydroxypyrrolidin-1-yl)methyl)-5-((R)-THF-3-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 526.2 [M + H]+, Ret. time = 3.19 min Chiral HPLC method X12: Ret. time = 10.43 | ¹H NMR (400 MHz, DMSO): δ 10.163 (s, 1H), 9.710 (s, 1H), 9.232 (s, 1H), 8.370 (d, J = 4.8 Hz, 1H), 7.693 (d, J = 4.8 Hz, 1H), 7.596 (d, J = 3.2 Hz, 1H), 7.402 (d, J = 4.8 Hz, 1H), 7.030 (d, J = 8.4 Hz 1H), 6.900 (d, J = 3.6 Hz 1H), 5.779 (s, 1H), 4.721 (s, 3H), 4.225 (s, 1 H), 3.991-3.989 (m, 2H), 3.857 (s 4H), 3.819-3.825 (m, 2H), 3.549-3.535 (m, 2H), 2.81 (d, J = 7.6 Hz, 1H), 2.689 (t, J = 1.6 Hz, 1H), 2.337-2.325 (m, 2H), 1.986-1.975 (m, 2H). | Up AA183 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-811 | 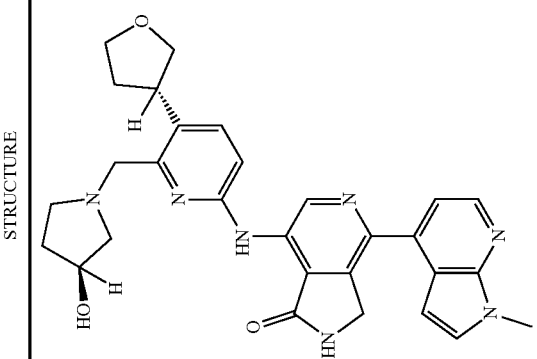 | 7-((6-(((S)-3-hydroxy-pyrrolidin-1-yl)methyl)-5-((S)-THF-3-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 526.2 [M + H]+, Ret. time = 3.14 min Chiral HPLC method X10: Ret. time = 6.57 | ¹H NMR (400 MHz, DMSO): δ 10.15 (s, 1H), 9.70 (s, 1H), 9.22 (s, 1H), 9.36-9.35 (d, J = 4.8 Hz, 1H), 7.69-7.66 (d, J = 8.4 Hz, 1H), 7.60-7.58 (d, J = 3.6 Hz, 1H), 7.39-7.38 (d, J = 4.8 Hz, 1H), 7.02-7.00 (d, J = 8.4 Hz, 1H), 6.89-6.88 (d, J = 2.8 Hz, 1H), 4.70 (s, 3H), 4.20 (bs, 1H), 3.99-3.93 (m, 3H), 3.79-3.69 (m, 2H), 3.55-3.51 (t, J = 7.6 Hz, 1H), 2.82-2.78 (t, J = 9.2 Hz 1H), 2.69-2.64 (m, 1H), 2.36-2.28 (m, 2H), 1.99-1.93 (m, 2H), 1.54 (bs, 1H), 1.23 (m, 3H), 1.19-1.16 (m, 2H). | Wp AA199 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-812 | 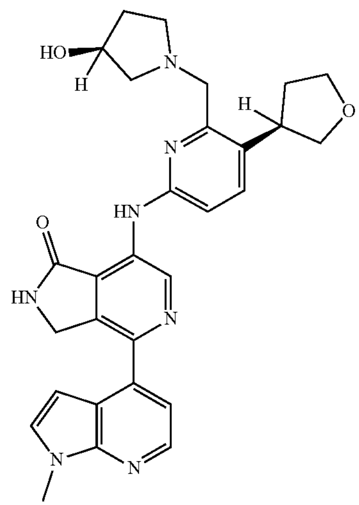 [SMILES: Cn1ccc2c(-c3ncc(Nc4ccc([C@H]5CCOC5)c(CN5CC[C@H](O)C5)n4)c4c3CNC4=O)ccnc21] | 7-((6-(((S)-3-hydroxy-pyrrolidin-1-yl)methyl)-5-((R)-THF-3-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 526.2 [M + H]+, Ret. time = 3.13 min Chiral HPLC method X10: Ret. time = 6.62 | ¹H NMR (400 MHz, DMSO): δ 10.15 (s, 1H), 9.69 (s, 1H), 9.22 (s, 1H), 9.36-9.35 (d, J = 4.8 Hz, 1H), 7.69-7.66 (d, J = 8.4 Hz, 1H), 7.60-7.58 (d, J = 3.6 Hz, 1H), 7.39-7.38 (d, J = 4.8 Hz, 1H), 7.02-7.00 (d, J = 8.4 Hz, 1H), 6.89-6.88 (d, J = 2.8 Hz, 1H), 4.70 (s, 3H), 4.20 (bs, 1H), 3.99-3.93 (m, 3H), 3.79-3.69 (m, 2H), 3.55-3.51 (t, J = 7.6 Hz, 1H), 2.82-2.78 (t, J = 9.2 Hz 1H), 2.69-2.64 (m, 1H), 2.36-2.28 (m, 2H), 1.99-1.93 (m, 2H), 1.54 (bs, 1H), 1.23 (m, 3H), 1.19-1.16 (m, 2H). | Wp AA199 BB14 |
| I-813 | 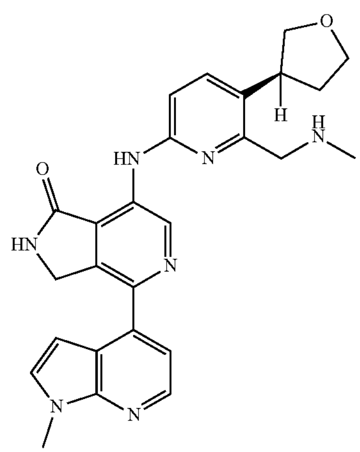 [SMILES: CNCc1nc(Nc2cnc(-c3ccnc4c3ccn4C)c3c2C(=O)NC3)ccc1[C@@H]1CCOC1] | rel-(R)-4-(1-methyl-1H-pyrrolo[2,3-b]pyridin-4-yl)-7-((6-((methyl-amino)methyl)-5-(THF-3-yl)pyridin-2-yl)amino)-2,3-dihydro-1H-pyrrolo[3,4-c]pyridin-1-one | LCMS Method J m/z = 470.0 [M + H]+, Ret. time = 3.13 min Chiral HPLC method X10: Ret. time = 6.46 | ¹H NMR (400 MHz, DMSO): δ 10.05 (s, 1H), 9.68 (s, 1H), 9.22 (s, 1H), 9.36-9.35 (d, J = 4.8 Hz, 1H), 7.68-7.66 (d, J = 8.4 Hz, 1H), 7.60-7.59 (d, J = 3.6 Hz, 1H), 7.41-7.39 (d, J = 4.8 Hz, 1H), 7.03-7.01 (d, J = 8.4 Hz, 1H), 6.91-6.90 (d, J = 3.6 Hz, 1H), 4.71 (s, 2H), 3.86 (s, 4H), 3.74-3.70 (m, 1H), 3.72-3.69 (m, 2H), 4.02-3.99 (m, 1H), 2.41 (s, 3H), 2.30-2.28 (m, 1H), 1.94-1.87 (m, 1H), 1.24 (s, 2H). | Wp AA157 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-814 | 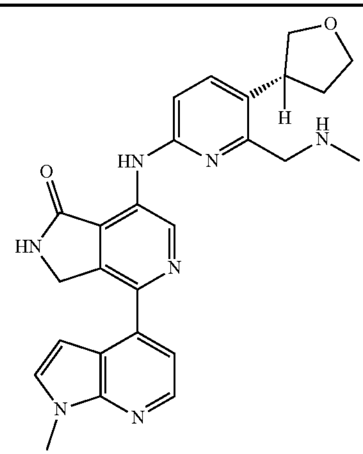 | rel-(R)-4-(1-methyl-1H-pyrrolo[2,3-b]pyridin-4-yl)-7-((6-((methylamino)methyl)-5-(THF-3-yl)pyridin-2-yl)amino)-2,3-dihydro-1H-pyrrolo[3,4-c]pyridin-1-one | LCMS Method J m/z = 470.0 [M + H]+, Ret. time = 3.13 min Chiral HPLC method X10: Ret. time = 9.99 | ¹H NMR (400 MHz, DMSO): δ 10.06 (s, 1H), 9.69 (s, 1H), 9.23 (s, 1H), 9.37-9.36 (d, J = 4.8 Hz, 1H), 7.69-7.67 (d, J = 8.4 Hz, 1H), 7.60-7.59 (d, J = 3.6 Hz, 1H), 7.41-7.39 (d, J = 4.8 Hz, 1H), 7.04-7.02 (d, J = 8.4 Hz, 1H), 6.91-6.90 (d, J = 3.6 Hz, 1H), 4.72 (s, 2H), 4.02-3.99 (m, 2H), 3.86 (s, 4H), 3.74-3.70 (m, 1H), 3.72-3.69 (t, J = 7.2 Hz, 1H), 3.56 (s, 1H), 2.41 (s, 3H), 2.30-2.28 (m, 1H), 1.94-1.87 (m, 1H), 1.24 (s, 2H). | Wp AA157 BB14 |
| I-815 | 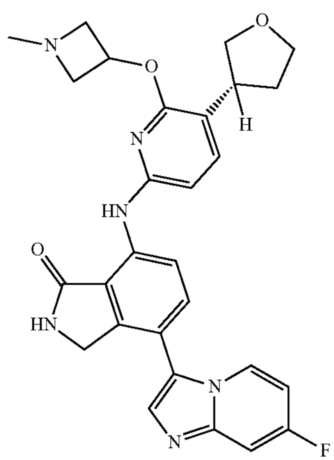 [SMILES: CN1CC(Oc2nc(Nc3ccc(-c4cnc5cc(F)ccn45)c4c3C(=O)NC4)ccc2[C@H]2CCOC2)C1] | (R)-4-(7-fluoroimidazo[1,2-a]pyridin-3-yl)-7-((6-((1-methylazetidin-3-yl)oxy)-5-(THF-3-yl)pyridin-2-yl)amino)isoindolin-1-one | LCMS Method J m/z = 515.0 [M + H]+, Ret. time = 3.00 min Chiral HPLC method X12: Ret. time = 7.45 | ¹H NMR (400 MHz, DMSO): δ 10.02 (s, 1H), 8.86 (s, 1H), 8.46-8.42 (d, J = 5.6 Hz, 2H), 7.83 (s, 1H), 7.79-7.77 (d, J = 8.8 Hz, 1H), 7.58-7.53 (m, 2H), 7.00-6.98 (t, J = 5.2 Hz, 1H), 6.59-6.57 (d, J = 8 Hz, 1H), 5.27-5.24 (t, J = 5.6 Hz, 1H), 4.39 (s, 2H), 4.04-4.00 (t, J = 7.6 Hz, 1H), 3.93-3.89 (m, 1H), 3.84-3.79 (m, 3H), 3.55-3.49 (m, 2H), 3.13 (bs, 2H), 2.33 (s, 3H), 2.25-2.19 (m, 1H), 2.00-1.95 (m, 1H). | Sp AA200 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-816 | 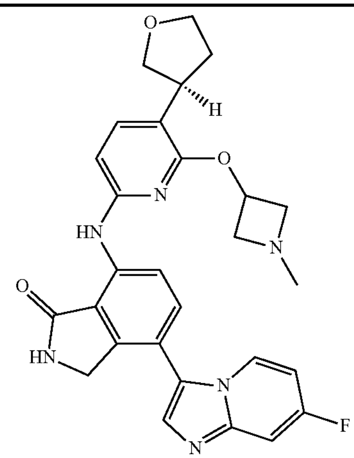 | (S)-4-(7-fluoro-imidazo[1,2-a]pyridin-3-yl)-7-((6-((1-methylazetidin-3-yl)oxy)-5-((THF-3-yl)pyridin-2-yl)amino)isoindolin-1-one | LCMS Method J m/z = 515.0 [M + H]+, Ret. time = 2.99 min Chiral HPLC method X12: Ret. time = 7.71 | ¹H NMR (400 MHz, DMSO): δ 10.02 (s, 1H), 8.86 (s, 1H), 8.46-8.42 (d, J = 5.6 Hz, 2H), 7.83 (s, 1H), 7.79-7.77 (d, J = 8.8 Hz, 1H), 7.58-7.52 (m, 2H), 7.00-6.98 (t, J = 5.2 Hz, 1H), 6.59-6.57 (d, J = 8 Hz, 1H), 5.27-5.24 (t, J = 5.6 Hz, 1H), 4.39 (s, 2H), 4.04-4.00 (t, J = 7.6 Hz, 1H), 3.93-3.89 (m, 1H), 3.84-3.79 (m, 2H), 3.55-3.49 (m, 2H), 3.13 (bs, 2H), 2.33 (s, 3H), 2.25-2.19 (m, 1H), 2.00-1.95 (m, 1H). | Sp AA200 BB63 |
| I-817 | 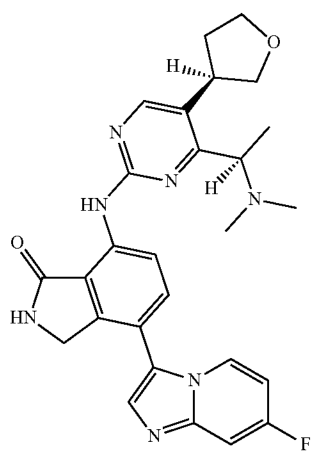 [SMILES: C[C@H](c1nc(Nc2ccc(-c3cnc4cc(F)ccn34)c3c2C(=O)NC3)ncc1[C@H]1CCOC1)N(C)C] | 7-((6-((R)-1-(dimethyl-amino)ethyl)-5-((R)-THF-3-yl)pyridin-2-yl)amino)-4-(7-fluoro-imidazo[1,2-a]pyridin-3-yl)isoindolin-1-one | LCMS Method C m/z = 501.1 [M + H]+, Ret. time = 2.63 min Chiral HPLC method X6: Ret. time = 10.78 | ¹H NMR (400 MHz, DMSO): δ 10.05 (s, 1H), 8.83 (s, 1H), 8.78-8.76 (d, J = 8.4 Hz, 1H), 8.46-8.43 (t, J = 6.4 Hz, 1H), 7.82 (s, 1H), 7.75-7.72 (dd, J = 8.4 Hz, 2H), 7.54-7.52 (d, J = 8 Hz 1H), 6.90-6.88 (t, J = 8.4 Hz, 2H), 4.39 (s, 2H), 3.97-3.95 (m, 2H), 3.84-3.78 (m, 2H), 3.58-3.50 (m, 1H), 2.25 (bs, 6H), 1.86-1.81 (m, 1H), 1.40-1.38 (d, J = 6.4 Hz, 3H), 1.23 (s, 2H). | AEp AA201 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-818 | 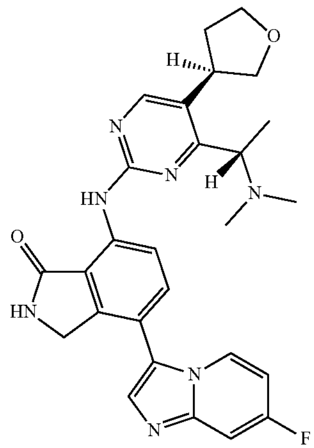 [SMILES: C[C@@H](c1nc(Nc2ccc(-c3cnc4cc(F)ccn34)c3c2C(=O)NC3)ncc1[C@H]1CCOC1)N(C)C] | 7-((6-((S)-1-(dimethyl-amino)ethyl)-5-((R)-THF-3-yl)pyridin-2-yl)amino)-4-(7-fluoro-imidazo[1,2-a]pyridin-3-yl)isoindolin-1-one | LCMS Method J m/z = 501.1 [M + H]+, Ret. time = 2.62 min Chiral HPLC method X6: Ret. time = 12.63 | ¹H NMR (400 MHz, DMSO): δ 10.05 (s, 1H), 8.85 (s, 1H), 8.74-8.73 (d, J = 8.4 Hz, 1H), 8.46-8.43 (t, J = 6.4 Hz, 1H), 7.83 (s, 1H), 7.75-7.72 (dd, J = 8.4 Hz, 2H), 7.54-7.52 (d, J = 8 Hz 1H), 6.99-6.97 (t, J = 8.4 Hz, 2H), 4.39 (s, 2H), 3.97-3.95 (m, 2H), 3.84-3.78 (m, 2H), 3.58-3.50 (m, 1H), 1.86-1.81 (m, 6H), 1.40-1.38 (d, J = 6.4 Hz, 3H), 1.23 (s, 2H). | AEp AA201 BB63 |
| I-819 | 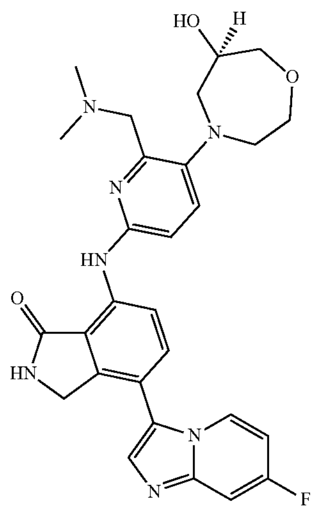 [SMILES: CN(C)Cc1nc(Nc2ccc(-c3cnc4cc(F)ccn34)c3c2C(=O)NC3)ccc1N1CCOC[C@H](O)C1] | (R)-7-((6-(((dimethyl-amino)methyl)-5-(6-hydroxy-1,4-oxazepan-4-yl)pyridin-2-yl)amino)-4-(7-fluoro-imidazo[1,2-a]pyridin-3-yl)isoindolin-1-one | LCMS Method J m/z = 532.2 [M + H]+, Ret. time = 2.76 min Chiral HPLC method X6: Ret. time = 13.97 | ¹H NMR (400 MHz, DMSO): δ 10.04 (s, 1H), 8.84 (s, 1H), 8.77-8.75 (d, J = 8.4 Hz, 1H), 8.46-8.43 (t, J = 6.4 Hz, 1H), 8.16 (s, 1H), 7.82 (s, 1H), 7.73-7.66 (dd, J = 8.4 Hz, 2H), 7.54-7.52 (d, J = 8 Hz 1H), 6.99-6.97 (t, J = 8.4 Hz, 1H), 4.39 (s, 2H), 3.96-3.92 (m, 3H), 3.74-3.73 (d, J = 4.8 Hz, 2H), 3.65-3.61 (m, 3H), 3.08 (bs, 2H), 3.03-2.98 (m, 2H), 2.34 (s, 6H). | ABp AA202 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-820 | 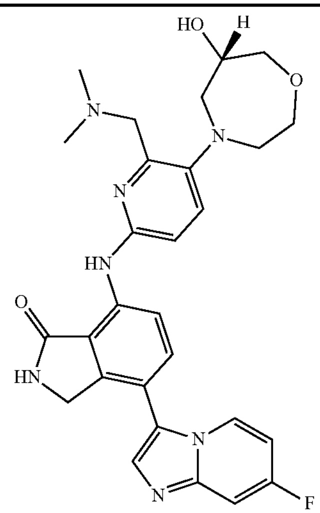 | (S)-7-((6-((dimethyl-amino)methyl)-5-(6-hydroxy-1,4-oxazepan-4-yl)pyridin-2-yl)amino)-4-(7-fluoro-imidazo[1,2-a]pyridin-3-yl)isoindolin-1-one | LCMS Method J m/z = 532.2 [M + H]+, Ret. time = 2.77 min Chiral HPLC method X6: Ret. time = 17.83 | ¹H NMR (400 MHz, DMSO): δ 10.05 (s, 1H), 8.84 (s, 1H), 8.74-8.72 (d, J = 8.4 Hz, 1H), 8.45-8.42 (t, J = 6.4 Hz, 1H), 8.16 (s, 1H), 7.82 (s, 1H), 7.73-7.66 (dd, J = 8.4 Hz, 2H), 7.54-7.52 (d, J = 8 Hz 1H), 6.99-6.97 (t, J = 8.4 Hz, 1H), 4.39 (s, 2H), 3.96-3.92 (m, 3H), 3.74-3.73 (d, J = 4.8 Hz, 2H), 3.65-3.61 (m, 3H), 3.08 (bs, 2H), 3.03-2.98 (m, 2H), 2.34 (s, 6H). | ABp AA202 BB63 |
| I-821 | 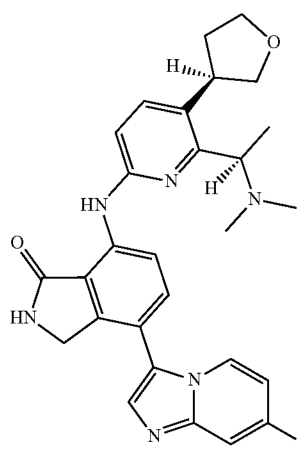 | 7-((6-((R)-1-(dimethyl-amino)ethyl)-5-((R)-THF-3-yl)pyridin-2-yl)amino)-4-(7-fluoro-imidazo[1,2-a]pyridin-3-yl)isoindolin-1-one | LCMS Method J m/z = 501.2 [M + H]+, Ret. time = 2.86 min Chiral HPLC method X18: Ret. time = 10.87 | 1H NMR (400 MHz, DMSO): δ 10.07 (s, 1H), 8.86 (s, 1H), 8.80-8.78 (d, J = 8.4 Hz, 1H), 8.46-8.43 (t, J = 6.8 Hz, 1H), 7.84 (s, 1H), 7.76-7.73 (d, J = 8.8 Hz, 1H), 7.68-7.66 (d, J = 8.4 Hz, 1H), 7.55-7.52 (m, 1H), 6.99-6.97 (t, J = 2 Hz, 1H), 6.89 (s, 1H), 4.40 (s, 2H), 3.99-3.93 (m, 4H), 3.84-3.78 (m, 1H), 3.52-3.49 (m, 1H), 2.20 (s, 6H), 1.39-1.36 (d, J = 11.2 Hz, 3H), 1.24 (s, 2H). | AEp AA201 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-822 | 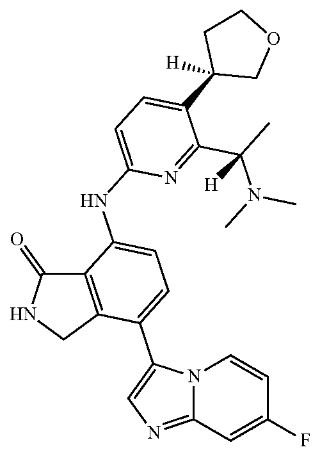 [SMILES: C[C@@H](c1nc(Nc2ccc(-c3cnc4cc(F)ccn34)c3c2C(=O)NC3)ccc1[C@H]1CCOC1)N(C)C] | 7-((6-((S)-1-(dimethyl-amino)ethyl)-5-((R)-THF-3-yl)pyridin-2-yl)amino)-4-(7-fluoro-imidazo[1,2-a]pyridin-3-yl)isoindolin-1-one | LCMS Method J m/z = 501.0 [M + H]+, Ret. time = 2.86 min Chiral HPLC method X18: Ret. time = 12.29 | ¹H NMR (400 MHz, DMSO): δ 10.06 (s, 1H), 8.86 (s, 1H), 8.80-8.78 (d, J = 8.4 Hz, 1H), 8.47-8.44 (t, J = 6.8 Hz, 1H), 7.84 (s, 1H), 7.76-7.73 (d, J = 8.8 Hz, 1H), 7.68-7.66 (d, J = 8.4 Hz, 1H), 7.55-7.52 (m, 1H), 6.99-6.97 (t, J = 2 Hz, 1H), 6.89 (s, 1H), 4.40 (s, 2H), 3.99-3.93 (m, 4H), 3.84-3.78 (m, 1H), 3.52-3.49 (m, 1H), 2.20 (s, 6H), 1.39-1.36 (d, J = 11.2 Hz, 3H), 1.24 (s, 2H). | AEp AA201 BB63 |
| I-823 | 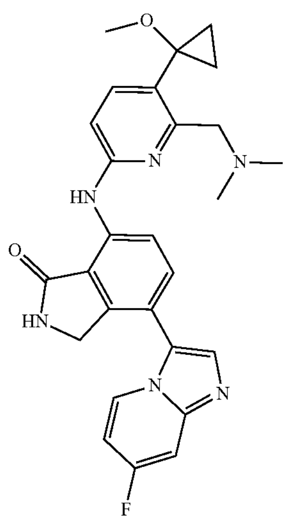 [SMILES: COC1(c2ccc(Nc3ccc(-c4cnc5cc(F)ccn45)c4c3C(=O)NC4)nc2CN(C)C)CC1] | 7-((6-(((dimethyl-amino)methyl)-5-(1-methoxycyclo-propyl)pyridin-2-yl)amino)-4-(7-fluoro-imidazo[1,2-a]pyridin-3-yl)isoindolin-1-one | LCMS Method J m/z = 487.0 [M + H]+, Ret. time = 2.95 min | ¹H NMR (400 MHz, DMSO): δ 8.88 (s, 1H), 8.86 (s, 1H), 8.47-8.43 (t, J = 6 Hz, 1H), 8.19 (s, 1H), 7.84 (s, 1H), 7.75-7.72 (d, J = 8.4 Hz, 1H), 7.65-7.63 (d, J = 8.4 Hz, 1H), 7.53 (bs, 1H), 7.00-6.98 (t, J = 5.2 Hz, 1H), 6.89 (s, 1H), 4.41 (s, 2H), 3.81 (s, 2H), 3.02 (s, 3H), 1.24 (s, 2H), 1.07 (s, 6H), 0.95-0.92 (m, 2H). | AHp AA203 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-824 | 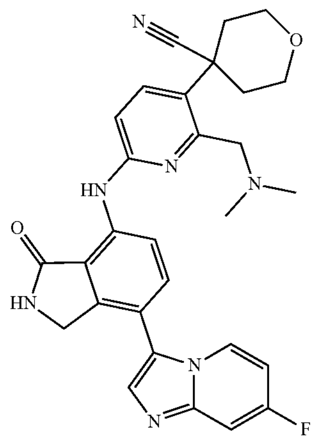 [SMILES: CN(C)Cc1nc(Nc2ccc(-c3cnc4cc(F)ccn34)c3c2C(=O)NC3)ccc1C1(C#N)CCOCC1] | 4-(2-((dimethylamino)methyl)-6-((7-(7-fluoroimidazo[1,2-a]pyridin-3-yl)-3-oxoisoindolin-4-yl)amino)pyridin-3-yl)tetrahydro-2H-pyran-4-carbonitrile | LCMS Method J m/z = 526.0 [M + H]+, Ret. time = 2.85 min | ¹H NMR (400 MHz, DMSO): δ 8.90 (s, 1H), 8.82-8.80 (d, J = 8.4 Hz, 1H), 8.49-8.45 (t, J = 6 Hz, 1H), 8.15 (s, 1H), 7.84 (s, 2H), 7.79-7.76 (d, J = 8.4 Hz, 1H), 7.56-7.53 (dd, J = 2.4 Hz, 1H), 7.04-7.01 (m, 1H), 6.99-6.97 (t, J = 4.8 Hz, 1H), 4.42 (s, 2H), 4.03 (bs, 2H), 3.92 (bs, 2H), 3.78-3.72 (t, J = 11.6 Hz, 3H), 2.41 (s, 2H), 2.37 (s, 1H), 2.29 (s, 6H). | ACp AA204 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-825 | 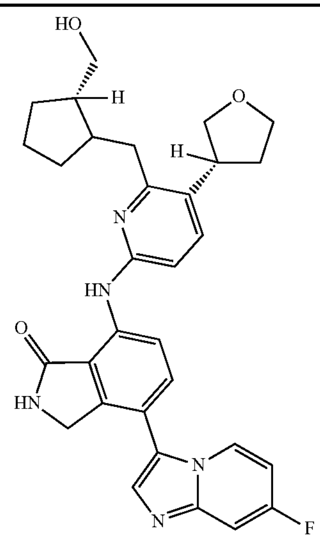 | 4-(7-fluoro-imidazo[1,2-a]pyridin-3-yl)-7-((6-(((R)-2-(hydroxymethyl)pyrrolidin-1-yl)methyl)-5-((R)-THF-3-yl)pyridin-2-yl)amino)iso-indolin-1-one | LCMS Method J m/z = 543.2 [M + H]+, Ret. time = 2.78 min Chiral HPLC method X4: Ret. time = 10.33 | ¹H NMR (400 MHz, DMSO): δ 10.06 (s, 1H), 8.86 (s, 1H), 8.46-8.43 (t, J = 7.2 Hz, 1H), 8.15 (s, 1H), 7.84 (s, 1H), 7.75-7.72 (d, J = 8.8 Hz, 2H), 7.56-7.53 (m, 1H), 7.00-6.98 (t, J = 4.8 Hz, 2H), 4.40 (s, 2H), 3.99-3.95 (m, 2H), 3.84-3.79 (m, 2H), 3.53 (bs, 3H), 2.68 (bs, 1H), 2.34 (bs, 3H), 1.93-1.87 (m, 3H), 1.62 (bs, 3H), 1.24 (s, 2H). | Sp AA205 BB63 |

TABLE 8-continued

Characterization Data (LCMS and $^1$H NMR).

| # | STRUCTURE | NAME | LCMS | $^1$H NMR | Method Reagent AA BB |
|---|---|---|---|---|---|
| I-826 | 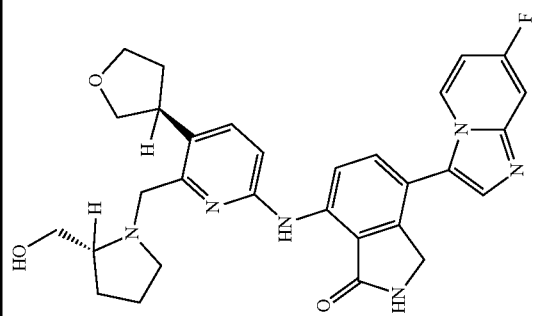 | 4-(7-fluoro-imidazo[1,2-a]pyridin-3-yl)-7-((6-(((R)-2-(hydroxymethyl)pyrrolidin-1-yl)methyl)-5-((S)-THF-3-yl)pyridin-2-yl)amino)iso-indolin-1-one | LCMS Method J m/z = 543.2 [M + H]+, Ret. time = 2.80 min Chiral HPLC method X4: Ret. time = 10.43 | $^1$H NMR (400 MHz, DMSO): δ 10.06 (s, 1H), 8.86 (s, 1H), 8.46-8.43 (t, J = 7.2 Hz, 1H), 8.15 (s, 1H), 7.84 (s, 1H), 7.75-7.72 (d, J = 8.8 Hz, 2H), 7.56-7.53 (m, 1H), 7.00-6.98 (t, J = 4.8 Hz, 2H), 4.40 (s, 2H), 3.99-3.95 (m, 2H), 3.84-3.79 (m, 2H), 3.53 (bs, 3H), 2.68 (bs, 1H), 2.34 (bs, 3H), 1.93-1.87 (m, 3H), 1.62 (bs, 3H), 1.24 (s, 2H). | Sp AA205 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-827 | 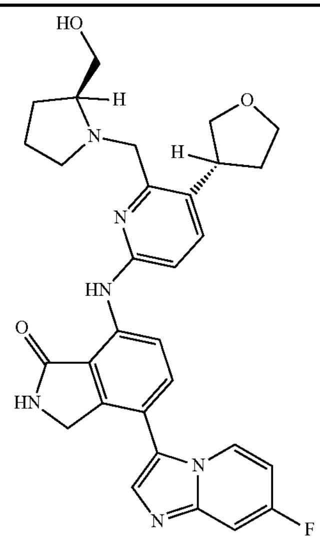 | 4-(7-fluoro-imidazo[1,2-a]pyridin-3-yl)-7-((6-(((S)-2-(hydroxymethyl)pyrrolidin-1-yl)methyl)-5-((R)-THF-3-yl)pyridin-2-yl)amino)iso-indolin-1-one | LCMS Method J m/z = 543.2 [M + H]+, Ret. time = 2.51 min Chiral HPLC method X4: Ret. time = 9.59 | ¹H NMR (400 MHz, DMSO): δ 10.05 (s, 1H), 8.81 (s, 2H), 8.47-8.44 (t, J = 6.4 Hz, 1H), 7.84 (s, 1H), 7.74-7.72 (d, J = 8.8 Hz, 1H), 7.66-7.64 (d, J = 8 Hz, 1H), 7.55-7.53 (d, J = 8.4 Hz, 1H), 6.99-6.94 (d, J = 7.6 Hz, 2H), 4.49 (bs, 1H), 4.40 (s, 2H), 4.02-3.97 (m, 2H), 3.89 (bs, 1H), 3.83-3.77 (m, 1H), 3.57-3.51 (m, 2H), 3.40 (bs, 1H), 3.26 (bs, 1H), 2.77 (bs, 1H), 2.68 (s, 2H), 2.30 (s, 3H), 1.88 (bs, 2H), 1.58 (s, 2H). | SP AA206 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-828 | 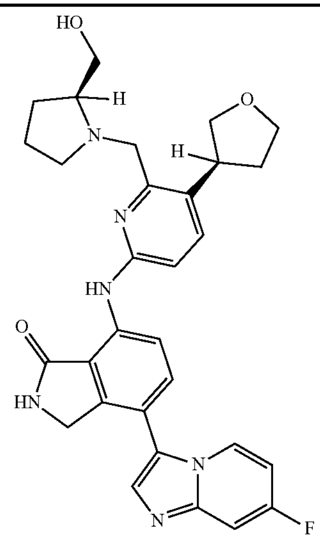 | 4-(7-fluoro-imidazo[1,2-a]pyridin-3-yl)-7-(6-(((S)-2-(hydroxymethyl)pyrrolidin-1-yl)methyl)-5-((S)-THF-3-yl)pyridin-2-yl)amino)isoindolin-1-one | LCMS Method J m/z = 543.0 [M + H]+, Ret. time = 2.51 min Chiral HPLC method X4: Ret. time = 9.59 | ¹H NMR (400 MHz, DMSO): δ 10.04 (s, 1H), 8.81 (s, 2H), 8.47-8.44 (t, J = 6.4 Hz, 1H), 7.84 (s, 1H), 7.74-7.72 (d, J = 8.8 Hz, 1H), 7.66-7.64 (d, J = 8 Hz, 1H), 7.55-7.53 (d, J = 8.4 Hz, 1H), 6.99-6.94 (d, J = 7.6 Hz, 2H), 4.49 (bs, 1H), 4.40 (s, 2H), 4.02-3.97 (m, 2H), 3.89 (bs, 1H), 3.83-3.77 (m, 1H), 3.57-3.51 (m, 2H), 3.40 (bs, 1H), 3.26 (bs, 1H), 2.77 (bs, 1H), 2.68 (s, 2H), 2.30 (s, 3H), 1.88 (bs, 2H), 1.58 (s, 2H). | Sp AA206 BB63 |
| I-829 | 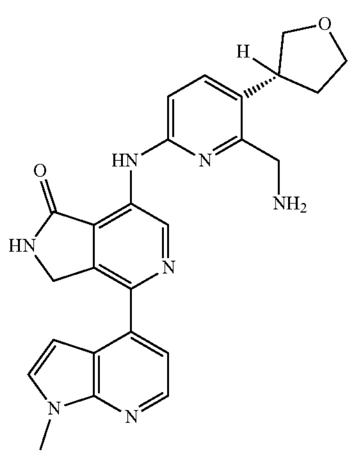 [SMILES: Cn1ccc2c(-c3ncc(Nc4ccc([C@H]5CCOC5)c(CN)n4)c4c3CNC4=O)ccnc21] | (R)-7-((6-(aminomethyl)-5-(THF-3-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 456.0 [M + H]+, Ret. time = 3.02 min Chiral HPLC method X9: Ret. time = 9.21 | ¹H NMR (400 MHz, DMSO): δ 9.92 (s, 1H), 9.77 (s, 1H), 9.30 (s, 1H), 8.46 (bs, 3H), 8.40-8.39 (d, J = 4.8 Hz, 1H), 7.77-7.75 (d, J = 8.4 Hz, 1H), 7.44-7.43 (d, J = 4.8 Hz, 1H), 7.18-7.16 (d, J = 8.8 Hz, 1H), 6.97-6.96 (d, J = 3.6 Hz, 1H), 4.75 (bs, 2H), 4.36-4.35 (d, J = 5.2 Hz, 2H), 3.99-3.95 (m, 3H), 3.86 (s, 4H), 3.44-3.40 (m, 2H), 2.37-2.34 (m, 1H). | Wp AA149 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-830 | 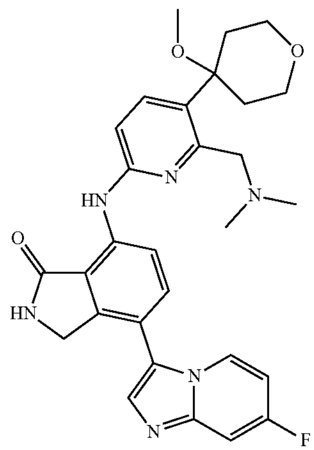 [SMILES: COC1(c2ccc(Nc3ccc(-c4cnc5cc(F)ccn45)c4c3C(=O)NC4)nc2CN(C)C)CCOCC1] | 7-((6-((dimethylamino)methyl)-5-(4-methoxytetrahydro-2H-pyran-4-yl)pyridin-2-yl)amino)-4-(7-fluoroimidazo[1,2-a]pyridin-3-yl)isoindolin-1-one | LCMS Method J m/z = 531.2 [M + H]+, Ret. time = 2.84 min | ¹H NMR (400 MHz, DMSO): δ 10.14 (s, 1H), 8.93-8.91 (d, J = 8.8 Hz, 1H), 8.87 (s, 1H), 8.46-8.43 (t, J = 7.2 Hz, 1H), 7.84 (s, 1H), 7.75-7.73 (d, J = 8.4 Hz, 1H), 7.68-7.66 (d, J = 8.8 Hz, 1H), 7.56-7.53 (m, 1H), 6.99-6.97 (t, J = 5.2 Hz, 1H), 6.94-6.92 (d, J = 8.8 Hz, 1H), 4.41 (s, 2H), 3.79 (s, 5H), 2.87 (s, 3H), 2.30 (s, 6H), 2.01-1.96 (m, 3H), 1.25 (s, 2H). | Xp AA207 BB63 |
| I-831 | 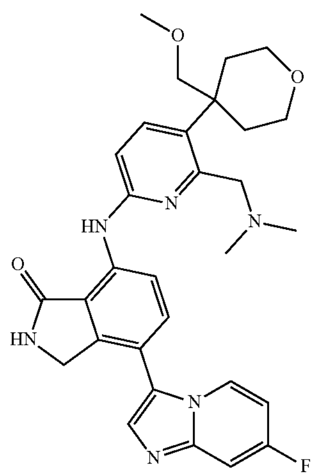 [SMILES: COCC1(c2ccc(Nc3ccc(-c4cnc5cc(F)ccn45)c4c3C(=O)NC4)nc2CN(C)C)CCOCC1] | 7-((6-((dimethylamino)methyl)-5-(4-(methoxymethyl)tetrahydro-2H-pyran-4-yl)pyridin-2-yl)amino)-4-(7-fluoroimidazo[1,2-a]pyridin-3-yl)isoindolin-1-one | LCMS Method J m/z = 545.2 [M + H]+, Ret. time = 2.92 min | ¹H NMR (400 MHz, DMSO): δ 10.04 (s, 1H), 8.85 (s, 1H), 8.82-8.80 (d, J = 8.8 Hz, 1H), 8.46-8.43 (t, J = 6.8 Hz, 1H), 8.17 (s, 1H), 7.83 (s, 1H), 7.73-7.69 (dd, J = 8.4 Hz, 2H), 7.55-7.52 (m, 1H), 6.99-6.97 (t, J = 2.4 Hz, 1H), 4.40 (s, 2H), 3.71 (bs, 2H), 3.57 (s, 3H), 3.45-3.40 (d, J = 9.6 Hz, 3H), 3.15 (s, 3H), 2.20 (s, 2H), 2.23 (s, 6H), 1.93-1.88 (t, J = 9.6 Hz, 2H). | Xp AA208 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-832 | 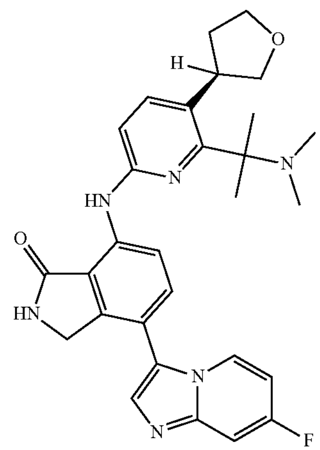 [SMILES: CN(C)C(C)(C)c1nc(Nc2ccc(-c3cnc4cc(F)ccn34)c3c2C(=O)NC3)ccc1[C@H]1CCOC1] | (R)-7-((6-(2-(dimethyl-amino)propan-2-yl)-5-(THF-3-yl)pyridin-2-yl)amino)-4-(7-fluoro-imidazo[1,2-a]pyridin-3-yl)isoindolin-1-one | LCMS Method J m/z = 515.0 [M + H]+, Ret. time = 2.88 min Chiral HPLC method X12: Ret. time = 8.07 | ¹H NMR (400 MHz, DMSO): δ 10.01 (s, 1H), 8.83 (s, 1H), 8.69-8.67 (d, J = 8.8 Hz, 1H), 8.46-8.42 (t, J = 7.2 Hz, 1H), 7.82 (s, 1H), 7.72-7.68 (d, J = 8.8 Hz, 2H), 7.54-7.51 (m, 1H), 6.98-6.96 (t, J = 2.4 Hz 1H), 6.90-6.87 (d, J = 8.4 Hz 1H), 4.93-4.89 (m, 1H), 4.39 (s, 2H), 4.04-3.99 (m, 2H), 3.82-3.76 (m, 2H), 3.49-3.45 (m, 1H), 2.16 (s, 3H), 1.82-1.77 (m, 1H), 1.46-1.44 (d, J = 7.6 Hz, 6H), 1.04-1.03 (d, J = 6 Hz, 3H). | Sp AA209 BB63 |
| I-833 | 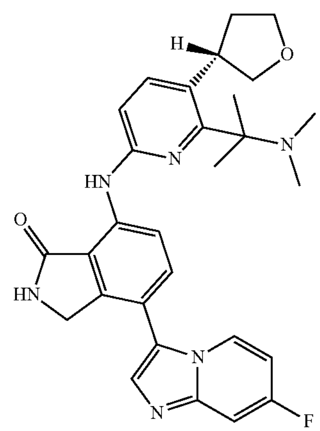 [SMILES: CN(C)C(C)(C)c1nc(Nc2ccc(-c3cnc4cc(F)ccn34)c3c2C(=O)NC3)ccc1[C@@H]1CCOC1] | (S)-7-((6-(2-(dimethyl-amino)propan-2-yl)-5-(THF-3-yl)pyridin-2-yl)amino)-4-(7-fluoro-imidazo[1,2-a]pyridin-3-yl)isoindolin-1-one | LCMS Method J m/z = 515.2 [M + H]+, Ret. time = 2.89 min Chiral HPLC method X12: Ret. time = 9.43 | ¹H NMR (400 MHz, DMSO): δ 10.01 (s, 1H), 8.83 (s, 1H), 8.69-8.67 (d, J = 8.8 Hz, 1H), 8.46-8.42 (t, J = 7.2 Hz, 1H), 7.82 (s, 1H), 7.72-7.68 (d, J = 8.8 Hz, 2H), 7.54-7.51 (m, 1H), 6.98-6.96 (t, J = 2.4 Hz 1H), 6.90-6.87 (d, J = 8.4 Hz 1H), 4.93-4.89 (m, 1H), 4.39 (s, 2H), 4.04-3.99 (m, 2H), 3.82-3.76 (m, 2H), 3.49-3.45 (m, 1H), 2.16 (s, 3H), 1.82-1.77 (m, 1H), 1.46-1.44 (d, J = 7.6 Hz, 6H), 1.04-1.03 (d, J = 6 Hz, 3H). | Sp AA209 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-834 | 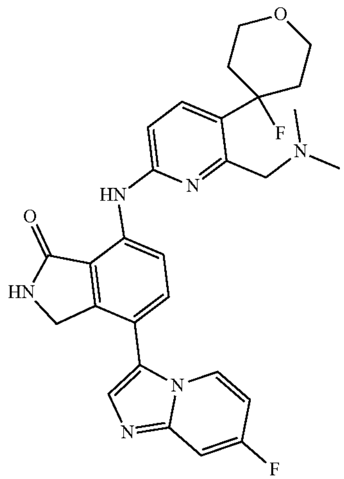 [SMILES: CN(C)Cc1nc(Nc2ccc(-c3cnc4cc(F)ccn34)c3c2C(=O)NC3)ccc1C1(F)CCOCC1] | 7-((6-((dimethylamino)methyl)-5-(4-fluorotetrahydro-2H-pyran-4-yl)pyridin-2-yl)amino)-4-(7-fluoroimidazo[1,2-a]pyridin-3-yl)isoindolin-1-one | LCMS Method J m/z = 519.0 [M + H]+, Ret. time = 2.84 min | ¹H NMR (400 MHz, DMSO): δ 10.17 (s, 1H), 8.88 (s, 1H), 8.84-8.82 (d, J = 8.4 Hz, 1H), 8.47-8.44 (t, J = 6.4 Hz, 1H), 7.84 (s, 1H), 7.75-7.74 (d, J = 4.8 Hz, 2H), 7.55-7.53 (d, J = 8 Hz, 1H), 7.02-6.97 (m, 2H), 4.41 (s, 2H), 3.89-3.85 (m, 2H), 3.77-3.72 (m, 4H), 2.32 (s, 6H), 2.25-2.16 (m, 2H), 1.25 (s, 2H). | Xp AA210 BB63 |
| I-835 | 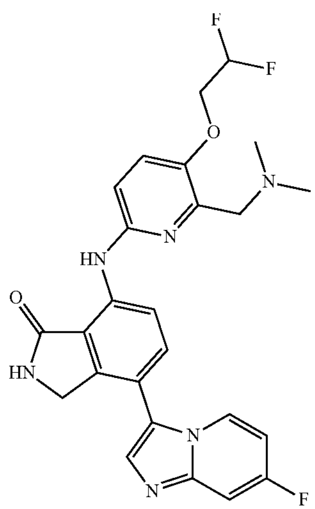 [SMILES: CN(C)Cc1nc(Nc2ccc(-c3cnc4cc(F)ccn34)c3c2C(=O)NC3)ccc1OCC(F)F] | 7-((5-(2,2-difluoroethoxy)-6-((dimethylamino)methyl)pyridin-2-yl)amino)-4-(7-fluoroimidazo[1,2-a]pyridin-3-yl)isoindolin-1-one | LCMS Method J m/z = 495.6 [M − H]+, Ret. time = 2.51 min | ¹H NMR (400 MHz, DMSO): δ 9.99 (s, 1H), 8.83 (s, 1H), 8.69-8.67 (d, J = 8.4 Hz, 1H), 8.42 (d, J = 6.8 Hz, 1H), 7.66-7.82 (s, 1H), 7.71-7.69 (d, J = 8.8 Hz, 1H), 7.57-7.51 (m, 2H), 6.99-6.95 (m, 2H), 6.41-6.39 (t, J = 3.6 Hz, 1H), 4.39 (s, 2H), 4.34-4.29 (m, 2H), 3.55 (s, 2H), 2.27 (s, 6H). | Xp AA211 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-836 | 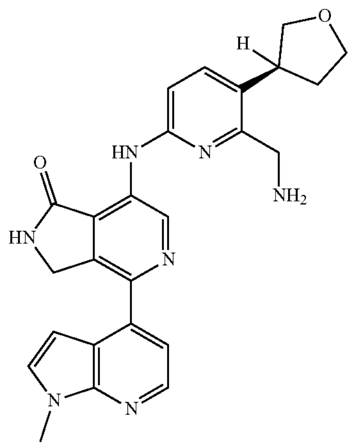 [SMILES: Cn1ccc2c(-c3ncc(Nc4ccc([C@@H]5CCOC5)c(CN)n4)c4c3CNC4=O)ccnc21] | (S)-7-((6-(aminomethyl)-5-(THF-3-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method C m/z = 456.2 [M + H]+, Ret. time = 1.35 min Chiral HPLC method X9: Ret. time = 9.09 | ¹H NMR (400 MHz, DMSO): δ 10.09 (bs, 1H), 9.67 (bs, 2H), 9.23 (bs, 1H), 8.36-8.35 (d, J = 5.2 Hz, 1H), 7.66-7.56 (m, 2H), 7.40-7.37 (t, J = 5.2 Hz, 1H), 6.99 (s, 1H), 6.91-6.90 (d, J = 2.8 Hz, 2H), 4.72 (bs, 2H), 4.34 (bs, 1H), 3.95-3.87 (m, 3H), 3.82 (s, 4H), 3.64-3.57 (m, 2H), 2.33-2.29 (m, 1H), 1.87 (bs, 1H). | Wp AA149 BB14 |
| I-837 | 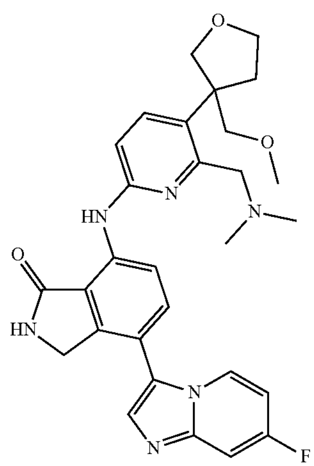 [SMILES: COCC1(c2ccc(Nc3ccc(-c4cnc5cc(F)ccn45)c4c3C(=O)NC4)nc2CN(C)C)CCOC1] | 7-((6-((dimethylamino)methyl)-5-(3-(methoxymethyl)THF-3-yl)pyridin-2-yl)amino)-4-(7-fluoroimidazo[1,2-a]pyridin-3-yl)isoindolin-1-one | LCMS Method J m/z = 530.8 [M − H]+, Ret. time = 2.71 min Ret. time = 6.32, 6.82 | ¹H NMR (400 MHz, DMSO): δ 10.05 (s, 1H), 8.85 (bs, 2H), 8.46-8.42 (d, J = 6 Hz, 1H), 7.95 (s, 1 H), 7.74-7.72 (d, J = 8.8 Hz, 1H), 7.55-7.54 (d, J = 2.4 Hz, 1H), 7.45-7.43 (d, J = 8.4 Hz, 1H), 6.99-6.97 (t, J = 2.4 Hz 1H), 6.81 (s, 1H), 4.39 (s, 2H), 4.26-4.23 (d, J = 8.4 Hz, 1H), 3.94-3.88 (m, 2H), 3.53-3.47 (m, 3H), 3.14 (s, 3H), 2.37 (s, 3H), 2.27 (s, 6H), 1.23 (s, 1H). | AAp AA212 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-838 | 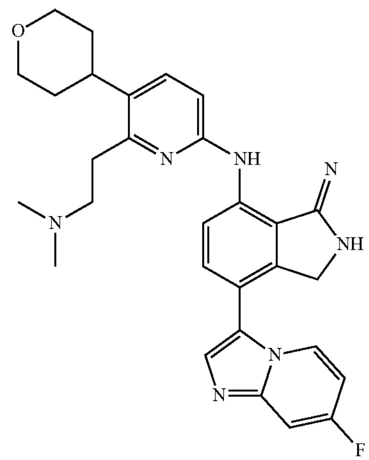 [SMILES: CN(C)CCc1nc(Nc2ccc(-c3cnc4cc(F)ccn34)c3c2C(=N)NC3)ccc1C1CCOCC1] | 7-((6-(2-(dimethylamino)ethyl)-5-(tetrahydro-2H-pyran-4-yl)pyridin-2-yl)amino)-4-(7-fluoroimidazo[1,2-a]pyridin-3-yl)isoindolin-1-one | LCMS Method J m/z = 515.2 [M − H]+, Ret. time = 2.43 min | ¹H NMR (400 MHz, DMSO): δ 10.00 (s, 1H), 8.83 (s, 1H), 8.74-8.72 (d, J = 8.4 Hz, 1H), 8.46-8.43 (t, J = 6.8 Hz, 1H), 7.83 (s, 1H), 7.74-7.72 (d, J = 8.8 Hz, 1H), 7.61-7.59 (d, J = 8.4 Hz, 1H), 7.55-7.52 (d, J = 10.4 Hz, 1H), 7.00-6.97 (t, J = 5.2 Hz, 1H), 6.86-6.84 (d, J = 8.8 Hz, 1H), 4.39 (s, 2H), 3.99-3.97 (m, 2H), 3.52-3.47 (t, J = 11.6 Hz, 3H), 2.99-2.95 (t, J = 6.8 Hz, 3H), 2.70-2.67 (t, J = 7.2 Hz, 3H), 2.26 (s, 6H), 1.60 (bs, 2H). | Xp AA102 BB63 |
| I-839 | 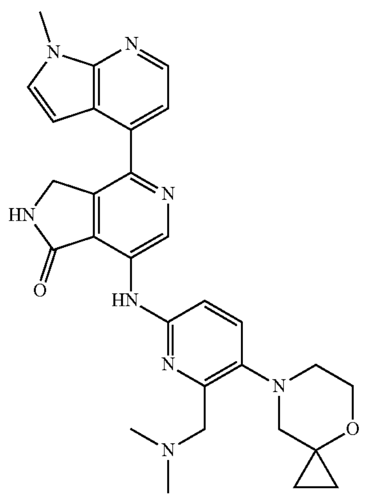 [SMILES: CN(C)Cc1nc(Nc2cnc(-c3ccnc4c3ccn4C)c3c2C(=O)NC3)ccc1N1CCOC2(CC2)C1] | 7-((6-(((dimethylamino)methyl)-5-(4-oxa-7-azaspiro[2.5]octan-7-yl)pyridin-2-yl)amino)-4-(1-methyl-1H-pyrrolo[2,3-b]pyridin-4-yl)-2,3-dihydro-1H-pyrrolo[3,4-c]pyridin-1-one | LCMS Method J m/z = 525.2 [M − H]+, Ret. time = 2.38 min | ¹H NMR (400 MHz, DMSO): δ 10.11 (s, 1H), 9.67 (s, 1H), 9.19 (s, 1H), 8.36-8.34 (d, J = 5.2 Hz, 1H), 7.65-7.63 (d, J = 8.8 Hz, 1H), 7.58-7.57 (d, J = 3.6 Hz, 1H), 7.38-7.37 (d, J = 5.2 Hz, 1H), 7.05-7.02 (t, J = 7.6 Hz, 1H), 6.87-6.86 (d, J = 3.2 Hz, 1H), 4.96 (s, 1H), 4.70 (s, 2H), 4.35 (s, 1H), 3.87 (s, 3H), 3.81 (s, 1H), 3.75 (s, 1H), 3.60 (bs, 1H), 3.18-3.16 (d, J = 5.2 Hz, 1H), 3.04 (bs, 1H), 2.94 (bs, 1H), 2.33 (s, 6H), 1.23 (bs, 2H), 0.75 (bs, 1H), 0.60 (bs, 1H). | Op AA135 BB14 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-840 | 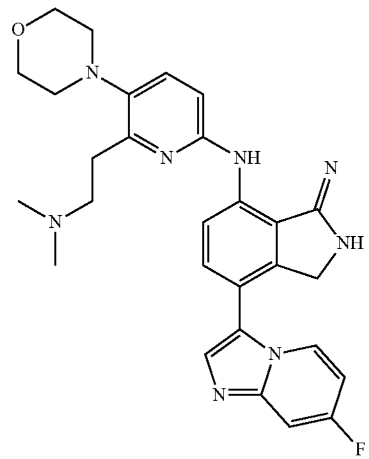 [SMILES: CN(C)CCc1nc(Nc2ccc(-c3cnc4cc(F)ccn34)c3c2C(=N)NC3)ccc1N1CCOCC1] | 7-((6-(2-(dimethyl-amino)ethyl)-5-morpholino-pyridin-2-yl)amino)-4-(7-fluoro-imidazo[1,2-a]pyridin-3-yl)isoindolin-1-one | LCMS Method J m/z = 516.2 [M − H]+, Ret. time = 2.86 min | ¹H NMR (400 MHz, DMSO): δ 9.99 (s, 1H), 8.82 (s, 1H), 8.70-8.68 (d, J = 8.8 Hz, 1H), 8.46-8.43 (t, J = 6 Hz, 1H), 7.83 (s, 1H), 7.74-7.72 (d, J = 8.8 Hz, 1H), 7.58-7.52 (m, 2H), 6.98-6.96 (t, J = 4.8 Hz, 1H), 6.88-6.85 (d, J = 8.8 Hz, 1H), 4.39 (s, 2H), 3.77-3.75 (d, J = 4 Hz, 4H), 3.00-2.97 (m, 2H), 2.83-2.81 (d, J = 4 Hz, 4H), 2.75-2.71 (m, 2H), 2.23 (s, 6H). | Xp AA156 BB63 |
| I-841 | 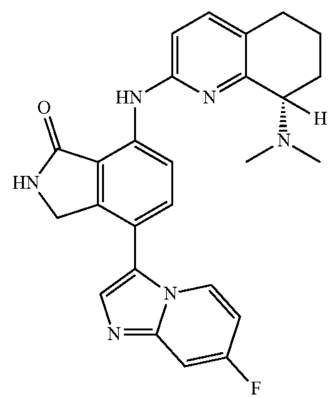 | (S)-7-((8-(dimethylamino)-5,6,7,8-tetrahydroquinolin-2-yl)amino)-4-(7-fluoro-imidazo[1,2-a]pyridin-3-yl)isoindolin-1-one | LCMS Method J m/z = 457.0 [M + H]+, Ret. time = 2.92 min Chiral HPLC method X14: Ret. time = 17.92 | ¹H NMR (400 MHz, DMSO): δ 10.00 (s, 1H), 8.84-8.82 (d, J = 8 Hz, 2H), 8.45-8.42 (t, J = 6.4 Hz, 1H), 7.83 (s, 1 H), 7.71-7.69 (d, J = 8.4 Hz, 1H), 7.55-7.52 (d, J = 9.6 Hz, 1H), 7.45-7.43 (d, J = 8.4 Hz, 1H), 7.00-6.97 (t, J = 7.2 Hz, 1H), 6.85-6.83 (d, J = 8.4 Hz, 1H), 4.39 (s, 2H), 3.54 (bs, 1 H), 2.75-2.69 (bs, 1 H), 2.32 (s, 6 H), 1.97 (bs, 2 H), 1.81 (bs, 1H), 1.65 (bs, 1H), 1.25 (s, 1 H). | ABp AA179 BB63 |

TABLE 8-continued

Characterization Data (LCMS and ¹H NMR).

| # | STRUCTURE | NAME | LCMS | ¹H NMR | Method AA Reagent BB |
|---|---|---|---|---|---|
| I-842 | 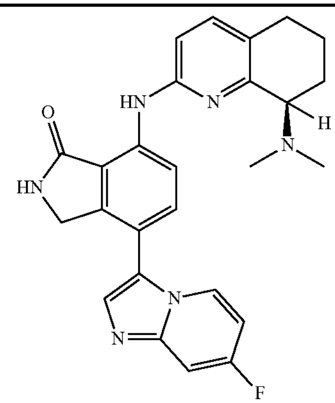 | (R)-7-((8-(dimethylamino)-5,6,7,8-tetrahydroquinolin-2-yl)amino)-4-(7-fluoroimidazo[1,2-a]pyridin-3-yl)isoindolin-1-one | LCMS Method J m/z = 457.0 [M + H]+, Ret. time = 2.91 min Chiral HPLC method X14: Ret. time = 12.33 | ¹H NMR (400 MHz, DMSO): δ 10.00 (s, 1H), 8.84-8.82 (s, 1H), 8.45-8.42 (t, J = 8 Hz, 2H), 8.45-8.42 (t, J = 6.4 Hz, 1H), 7.83 (s, 1 H), 7.71-7.69 (d, J = 8.4 Hz, 1H), 7.55-7.52 (d, J = 9.6 Hz, 1H), 7.45-7.43 (d, J = 8.4 Hz, 1H), 7.00-6.97 (t, J = 7.2 Hz, 1H), 6.85-6.83 (d, J = 8.4 Hz, 1H), 4.39 (s, 2H), 3.54 (bs, 1 H), 2.75-2.69 (bs, 1 H), 2.32 (s, 6H), 1.97 (bs, 2 H), 1.81 (bs, 1H), 1.65 (bs, 1H), 1.25 (s, 1 H). | ABp AA179 BB63 |
| I-843 | 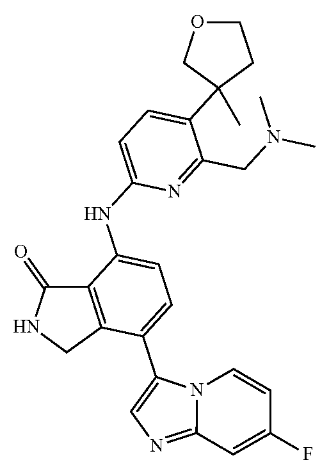 | 7-((6-(((dimethylamino)methyl)-5-(3-methylTHF-3-yl)pyridin-2-yl)amino)-4-(7-fluoroimidazo[1,2-a]pyridin-3-yl)isoindolin-1-one | LCMS Method J m/z = 501.0 [M + H]+, Ret. time = 2.85 min Chiral HPLC method X10: Ret. time = 6.28, 6.89 | ¹H NMR (400 MHz, DMSO): δ 9.98 (s, 1 H), 8.87 (bs, 1H), 8.58-8.42 (bs, 1H), 7.84 (s, 1 H), 7.55-7.52 (d, J = 8.4 Hz, 1H), 7.60 (bs, 1H), 7.56-7.53 (d, J = 9.2 Hz, 1H), 7.00 (bs, 2H), 4.40 (m, 2H), 4.12-4.09 (m, 2H), 3.94-3.87 (m, 2H), 3.74 (bs, 1H), 3.17-3.16 (d, J = 5.2 Hz, 3H), 2.30 (bs, 1H), 2.18 (s, 1 H), 1.35 (s, 3H), 1.23 (s, 3H), 0.85 (bs, 2 H). | AAp AA213 BB63 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-844 | 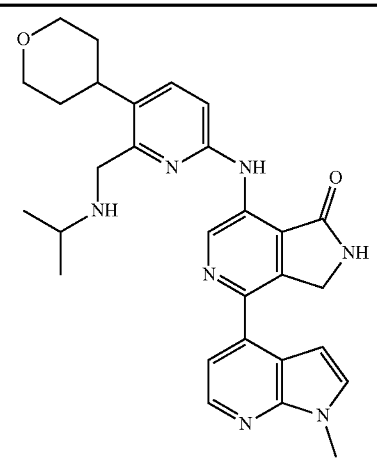 | 7-[[6-[(isopropyl-amino)methyl]-5-tetrahydro-pyran-4-yl-2-pyridyl]amino]-4-(1-methyl-pyrrolo[2,3-b]pyridin-4-yl)-2,3-dihydro-pyrrolo[3,4-c]pyridin-1-one Formic acid salt | Method AcHSS C18, m/z = 512 [M + H]+, Ret. time = 2.75 min. | ¹H NMR (400 MHz, DMSO): δ 10.01 (s, 1 H), 9.68 (s, 1 H), 9.23 (s, 1 H), 8.38 (d, J = 4.7 Hz, 1H), 8.25 (s, 1 H), 7.71 (d, J = 8.8 Hz, 1 H), 7.59 (d, J = 3.5 Hz, 1 H), 7.41 (d, J = 4.9 Hz, 1 H), 7.05 (d, J = 8.7 Hz, 1 H), 6.93 (d, J = 3.3 Hz, 1 H), 4.75 (s, 2 H), 4.08 (s, 2 H), 3.98 (dd, J = 3.1, 10.3 Hz, 2 H), 3.88 (s, 3 H), 3.52-3.48 (m, 2 H), 3.12-3.01 (m, 2 H), 1.78-1.65 (m, 4 H), 1.19 (d, J = 6.4 Hz, 6 H). | O AC96 BC26 |
| I-845 | 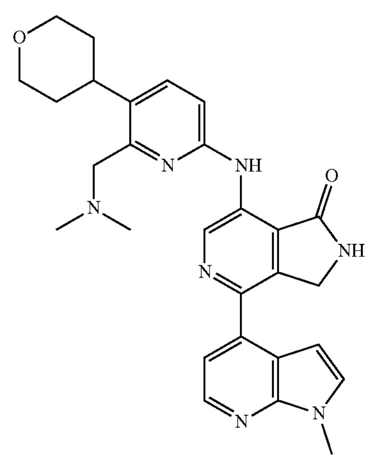 | 7-[[6-[(dimethyl-amino)methyl]-5-tetrahydropyran-4-yl-2-pyridyl]amino]-4-(1-methyl-pyrrolo[2,3-b]pyridin-4-yl)-2,3-dihydro-pyrrolo[3,4-c]pyridin-1-one Formic acid salt | Method BicarbB EHC18, m/z = 498 [M + H]+, Ret. time = 3.49 min. | ¹H NMR (400 MHz, DMSO): δ 10.14 (s, 1 H), 9.69 (s, 1 H), 9.21 (s, 1 H), 8.37 (d, J = 5.1 Hz, 1 H), 8.25 (s, 1 H), 7.71 (d, J = 8.6 Hz, 1H), 7.59 (d, J = 3.4 Hz, 1H), 7.40 (d, J = 4.9 Hz, 1H), 7.03 (d, J = 8.4 Hz, 1H), 6.89 (d, J = 3.5 Hz, 1H), 4.72 (s, 2H), 3.98 (dd, J = 3.5, 11.0 Hz, 2 H), 3.89 (s, 3 H), 3.63 (s, 2 H), 3.46 (ddd, J = 11.4, 11.4, 2.9 Hz, 2 H), 3.24-3.21 (m, 1 H), 2.26 (s, 6 H), 1.76-1.63 (m, 4 H). | O AC97 BC26 |

TABLE 8-continued

Characterization Data (LCMS and 1H NMR).

| # | STRUCTURE | NAME | LCMS | 1H NMR | Method Reagent AA BB |
|---|---|---|---|---|---|
| I-846 | 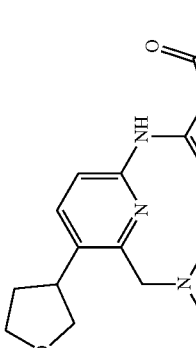 | 7-[[6-[(dimethylamino)methyl]-5-tetrahydrofuran-3-yl)pyridyl]amino]-4-(7-methylimidazo[1,2-a]pyrimidin-3-yl)isoindolin-1-one | Method AcHSS C18, m/z = 484 [M + H]+, Ret. time = 2.04 min. | 1H NMR (400 MHz, DMSO): δ 10.06 (s, 1 H), 8.86 (s, 1 H), 8.75 (d, J = 7.2 Hz, 2 H), 7.90 (s, 1 H), 7.74 (d, J = 8.8 Hz, 1 H), 7.69 (d, J = 8.8 Hz, 1 H), 7.01-6.96 (m, 2 H), 4.43 (s, 2 H), 4.03-3.95 (m, 2 H), 3.82 (q, J = 8.6 Hz, 2 H), 3.54 (t, J = 7.8 Hz, 1 H), 3.31 (s, 2 H), 2.58 (s, 3 H), 2.33-2.28 (m, 1 H), 2.23 (s, 6 H), 1.96-1.86 (m, 1 H). | F AC50 BC109 |
| I-847 | 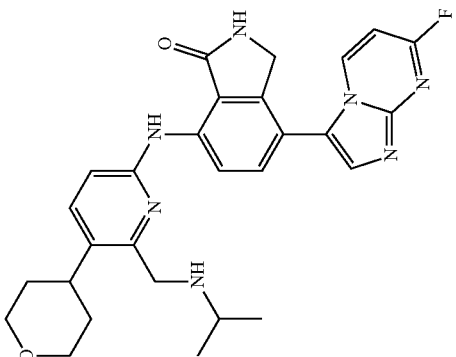 | 4-(7-fluoroimidazo[1,2-a]pyridin-3-yl)-7-[[6-[(isopropylamino)methyl]-5-tetrahydropyran-4-yl-2-pyridyl]amino]isoindolin-1-one Formic acid salt | Method BicarbB EHC18, m/z = 515 [M + H]+, Ret. time = 3.54 min. | 1H NMR (400 MHz, DMSO): δ 10.01 (s, 1 H), 8.84 (s, 1 H), 8.66 (d, J = 8.8 Hz, 1 H), 8.43 (dd, J = 5.5, 7.3 Hz, 1 H), 8.32 (s, 1 H), 7.83 (s, 1 H), 7.71 (d, J = 8.4 Hz, 1 H), 7.65 (d, J = 9.0 Hz, 1 H), 7.54 (dd, J = 2.7, 10.2 Hz, 1 H), 6.99 (ddd, J = 7.5, 7.5, 2.7 Hz, 1 H), 6.93 (d, J = 9.1 Hz, 1 H), 4.40 (s, 2 H), 3.98 (dd, J = 2.9, 10.7 Hz, 2 H), 3.95 (s, 2 H), 3.49 (ddd, J = 11.1, 11.1, 2.7 Hz, 2 H), 3.09 (ddd, J = 11.1, 11.1, 3.8 Hz, 1 H), 2.94-2.85 (m, 1 H), 1.76-1.63 (m, 4 H), 1.10 (d, J = 6.4 Hz, 6 H). | F AC96 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-848 | 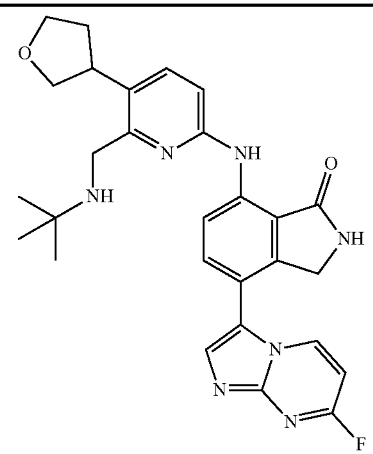 | 7-[[6-[(tert-butylamino)methyl]-5-tetrahydrofuran-3-yl-2-pyridyl]amino]-4-(7-fluoroimidazo[1,2-a]pyridin-3-yl)isoindolin-1-one | Method BicarbB EHC18, m/z = 515 [M + H]+, Ret. time = 3.71 min. | ¹H NMR (400 MHz, DMSO): δ 10.04 (s, 1 H), 8.89 (s, 1 H), 8.85 (s, 1 H), 8.43 (d, J = 8.9 Hz, 1 H), 8.34 (dd, J = 6.0, 7.1 Hz, 1 H), 7.85 (s, 1 H), 7.79 (d, J = 9.2 Hz, 1 H), 7.69 (d, J = 8.5 Hz, 1 H), 7.57 (dd, J = 2.9, 10.5 Hz, 1 H), 7.19 (ddd, J = 7.6, 7.6, 2.6 Hz, 1 H), 7.04 (d, J = 8.5 Hz, 1 H), 4.77 (s, 1 H), 4.42 (s, 2 H), 4.37 (s, 2 H), 4.06 (t, J = 7.9 Hz, 1 H), 4.01 (ddd, J = 8.5, 8.5, 5.1 Hz, 1 H), 3.85 (dd, J = 7.5, 15.4 Hz, 1 H), 3.69-3.62 (m, 1 H), 3.61 (ddd, J = 8.1, 8.1, 8.1 Hz, 1 H), 2.41-2.35 (m, 1 H), 1.95-1.85 (m, 1 H), 1.46 (s, 9 H). | F AC98 BC80 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-849 | 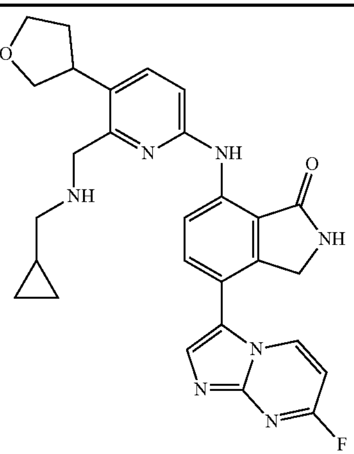 | 7-[[6-[(cyclo-propylmethyl-amino)methyl]-5-tetrahydrofuran-3-yl-2-pyridyl]amino]-4-(7-fluoro-imidazo[1,2-a]pyridin-3-yl)isoindolin-1-one Formic acid salt | Method BicarbB EHC18, m/z = 513 [M + H]+, Ret. time = 3.62 min | ¹H NMR (400 MHz, DMSO): δ 9.85 (s, 1 H), 8.66 (s, 1 H), 8.43 (d, J = 8.8 Hz, 1 H), 8.21 (dd, J = 6.0, 7.8 Hz, 1 H), 8.00 (s, 1 H), 7.64 (s, 1 H), 7.52 (d, J = 8.6 Hz, 1 H), 7.47 (d, J = 8.6 Hz, 1 H), 7.34 (dd, J = 2.8, 10.4 Hz, 1 H), 6.83-6.77 (m, 2 H), 4.21 (s, 2 H), 3.86 (s, 2 H), 3.81 (dd, J = 7.0, 7.9 Hz, 1 H), 3.78-3.73 (m, 1 H), 3.62 (dd, J = 7.6, 15.8 Hz, 1 H), 3.48-3.40 (m, 1 H), 3.38 (dd, J = 5.9, 13.4 Hz, 1 H), 2.43 (d, J = 6.9 Hz, 2 H), 2.13-2.07 (m, 1 H), 1.75-1.65 (m, 1 H), 0.87-0.81 (m, 1 H), 0.30-0.25 (m, 2 H), 0.01 (ddd, J = 5.4, 5.4, 3.8 Hz, 2 H). | F AC99 BC80 |
| I-850 | 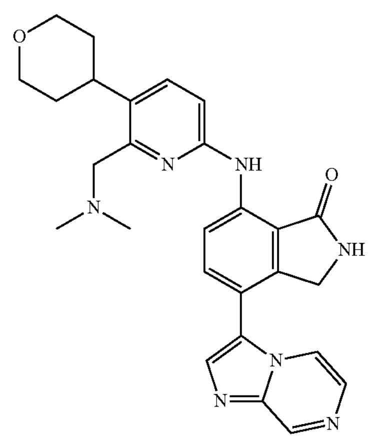 | 7-[6-[(dimethyl-amino)methyl]-5-tetrahydropyran-4-yl-2-pyridyl]amino]-4-imidazo[1,2-a]pyrazin-3-yl-isoindolin-1-one | Method AcHSS C18, m/z = 484 [M + H]+, Ret. time = 2.48 min. | ¹H NMR (400 MHz, DMSO): δ 10.12 (s, 1 H), 9.21 (s, 1 H), 8.90 (s, 1 H), 8.85 (d, J = 8.8 Hz, 1 H), 8.54 (d, J = 5.0 Hz, 1 H), 8.18 (s, 1 H), 7.97 (d, J = 4.3 Hz, 1 H), 7.85 (d, J = 8.5 Hz, 1 H), 7.72 (d, J = 8.4 Hz, 1 H), 6.98 (d, J = 8.4 Hz, 1 H), 4.49 (s, 2 H), 4.02 (dd, J = 2.8, 11.2 Hz, 2 H), 3.63 (s, 2 H), 3.49 (ddd, J = 11.5, 11.5, 2.6 Hz, 2 H), 3.25 (dt, J = 4.1, 11.4 Hz, 1 H), 2.28 (s, 6 H), 1.77-1.66 (m, 4 H). | F AC97 BC80 |

| # | STRUCTURE | NAME | LCMS | ¹H NMR | Method Reagent AA BB |
|---|---|---|---|---|---|
| I-851 | 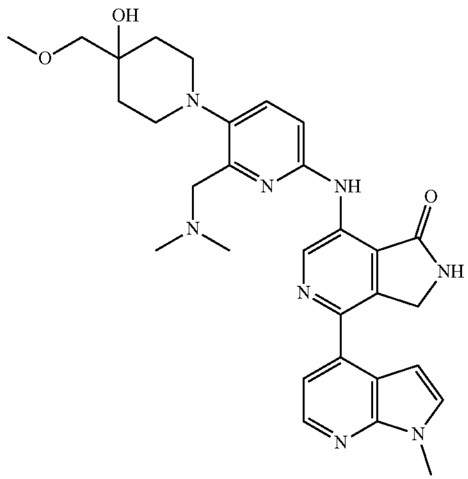 | 7-[[6-[(dimethyl-amino)methyl]-5-[4-hydroxy-4-(methoxymeth-yl)-1-piperidyl]-2-pyridyl]amino]-4-(1-methyl-pyrrolo[2,3-b]pyridin-4-yl)-2,3-dihydro-pyrrolo[3,4-c]pyridin-1-one Formate salt | Method AcHSS C18, m/z = 557 [M + H]+, Ret. time = 2.62 min. | ¹H NMR (400 MHz, DMSO): δ 10.10 (s, 1 H), 9.65 (s, 1 H), 9.19 (s, 1 H), 8.37 (d, J = 5.4 Hz, 1H), 8.24 (s, 1 H), 7.59 (s, 1 H), 7.58 (d, J = 6.1 Hz, 1 H), 7.39 (d, J = 4.9 Hz, 1 H), 7.01 (d, J = 8.9 Hz, 1 H), 6.88 (d, J = 3.4 Hz, 1 H), 4.72 (s, 2H), 4.37 (s, 1 H), 3.89 (s, 3 H), 3.59 (s, 2 H), 3.24 (s, 3 H), 3.01-2.95 (m, 4 H), 2.35 (s, 6 H), 1.82-1.74 (m, 2 H), 1.55 (d, J = 13.7 Hz, 2 H). | O AC100 BC26 |
| I-852 | 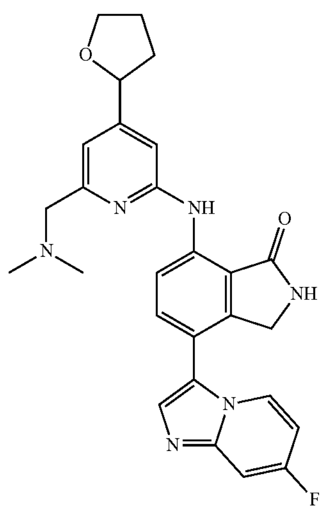 | 7-((6-((dimethyl-amino)methyl)-4-(tetrahydrofuran-2-yl)pyridin-2-yl)amino)-4-(7-fluoro-imidazo[1,2-a]pyridin-3-yl)isoindolin-1-one Formate salt | Method AcHSS C18, m/z = 487.0 [M + H]+, Ret. time = 2.09 min. | ¹H NMR (400 MHz, DMSO): δ 10.17 (s, 1 H), 8.92 (s, 1 H), 8.86 (d, J = 8.2 Hz, 1 H), 8.52 (t, J = 6.8 Hz, 1 H), 8.21 (s, 1 H), 7.89 (s, 1 H), 7.79 (d, J = 8.6 Hz, 1 H), 7.58 (d, J = 9.1 Hz, 1 H), 7.02 (t, J = 7.2 Hz, 1 H), 6.97 (s, 1 H), 6.81 (s, 1 H), 4.46 (s, 2 H), 4.08 (dt, J = 8.0, 4.9, 8.0 Hz, 1 H), 3.85 (q, J = 7.7 Hz, 1 H), 3.69 (t, J = 7.8 Hz, 1 H), 3.59 (s, 2 H), 3.50-3.45 (m, 1 H), 2.43-2.37 (m, 1 H), 2.32 (s, 6 H), 2.04-2.00 (m, 1 H). | A AB85 BC91 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-853 | 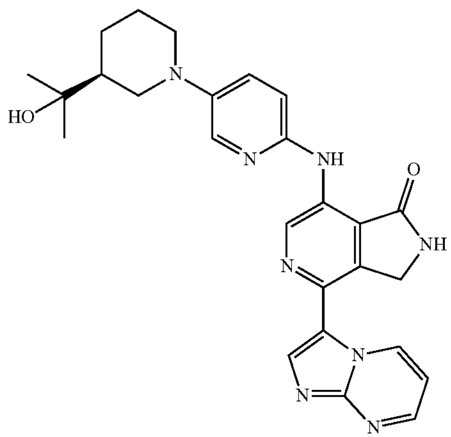 | 7-[[5-((3S)-3-(1-hydroxy-1-methyl-ethyl)-1-piperidyl]-2-pyridyl]amino]-4-imidazo[1,2-a]pyrimidin-3-yl-2,3-dihydropyrrolo[3,4-c]pyridin-1-one | Method AcHSS C18, m/z = 485 [M + H]+, Ret. time = 2.67 min. | ¹H NMR (400 MHz, DMSO): δ 10.21 (dd, J = 2.1, 7.0 Hz, 1 H), 9.90 (s, 1 H), 9.39 (s, 1 H), 9.29 (s, 1 H), 8.67 (dd, J = 2.0, 4.0 Hz, 1 H), 8.22 (s, 1 H), 8.02 (d, J = 3.0 Hz, 1 H), 7.43 (dd, J = 3.0, 9.0 Hz, 1 H), 7.24 (dd, J = 4.1, 7.0 Hz, 1 H), 7.02 (d, J = 8.7 Hz, 1 H), 4.78 (s, 2 H), 4.32-4.24 (m, 1 H), 3.76 (d, J = 11.8 Hz, 1 H), 3.64 (d, J = 11.5 Hz, 1 H), 1.87-1.74 (m, 2 H), 1.62-1.51 (m, 2 H), 1.12 (d, J = 10.3 Hz, 6H). | Hc AC30 BC126 |

TABLE 8-continued

Characterization Data (LCMS and $^1$H NMR).

| # | STRUCTURE | NAME | LCMS | $^1$H NMR | Method Reagent AA BB |
|---|---|---|---|---|---|
| I-854 | 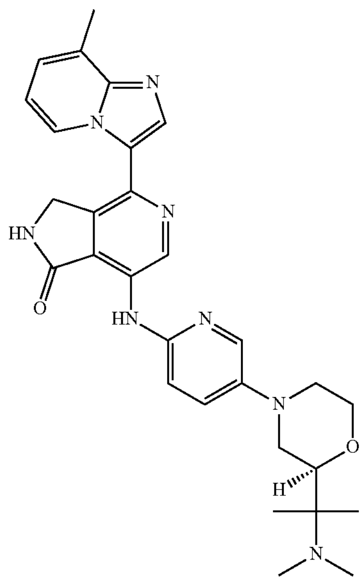 | rel-(R)-7-((5-(2-(2-(dimethylamino)propan-2-yl)morpholino)pyridin-2-yl)amino)-4-(8-methylimidazo[1,2-a]pyridin-3-yl)-2,3-dihydro-1H-pyrrolo[3,4-c]pyridin-1-one | LCMS Method J m/z = 527.6 [M + H]+, Ret. time = 2.64 min Chiral HPLC method X7: Ret. time = 5.81 | 1H NMR (400 MHz, DMSO-d6) δ 9.92 (s, 1H), 9.71 (d, J = 7.1 Hz, 1H), 9.43 (s, 1H), 9.29 (s, 1H), 8.05 (s, 2H), 7.46 (d, J = 8.5 Hz, 1H), 7.24 (d, J = 6.8 Hz, 1H), 7.07 (d, J = 9.0 Hz, 1H), 7.01 (t, J = 6.9 Hz, 1H), 4.76 (s, 2H), 4.03 (d, J = 11.2 Hz, 1H), 3.57 (d, J = 13.3 Hz, 2H), 3.48 (d, J = 11.7 Hz, 2H), 2.58 (d, J = 5.8 Hz, 6H), 2.21 (s, 3H), 1.25 (s, 2H), 1.02 (d, J = 19.0 Hz, 6H). | Zp AA93 BB37 |

TABLE 8-continued

Characterization Data (LCMS and ¹H NMR).

| # | STRUCTURE | NAME | LCMS | ¹H NMR | Method Reagent AA BB |
|---|---|---|---|---|---|
| I-855 | 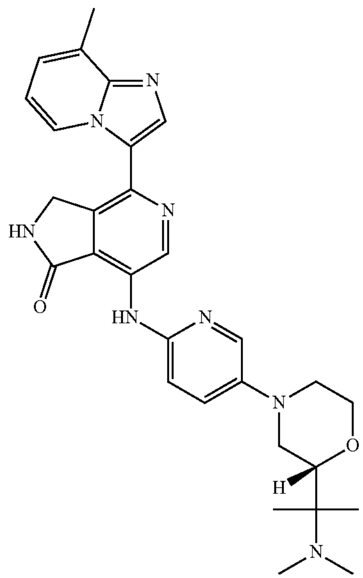 | rel-(R)-7-((5-(2-(2-(dimethylamino)propan-2-yl)morpholino)pyridin-2-yl)amino)-4-(8-methylimidazo[1,2-a]pyridin-3-yl)-2,3-dihydro-1H-pyrrolo[3,4-c]pyridin-1-one | LCMS Method J m/z = 527.2 [M + H]+, Ret. time = 3.04 min Chiral HPLC method X7: Ret. time = 7.92 | 1H NMR (400 MHz, DMSO-d6) δ 9.92 (s, 1H), 9.71 (d, J = 7.1 Hz, 1H), 9.43 (s, 1H), 9.29 (s, 1H), 8.05 (d, J = 4.5 Hz, 2H), 7.46 (dd, J = 9.0, 3.0 Hz, 1H), 7.24 (d, J = 6.8 Hz, 1H), 7.13-6.94 (m, 2H), 4.76 (s, 2H), 4.03 (d, J = 10.4 Hz, 1H), 3.69 (t, J = 11.3 Hz, 2H), 3.59 (t, J = 12.0 Hz, 1H), 3.47 (d, J = 11.6 Hz, 1H), 2.58 (s, 3H), 2.20 (s, 6H), 1.25 (s, 2H), 1.02 (d, J = 19.2 Hz, 6H). | Zp AA93 BB37 |

TABLE 9

LC MS analytical methods Protocols

| Method | Instrument | Column | Flow Rate | Mobile Phase A | Mobile Phase B | Gradient |
|---|---|---|---|---|---|---|
| AcHSSC18 | UPLC + Waters DAD + Waters SQD2, single quadrapole UPLC-MS | Acquity UPLC HSS C18 1.8 um 100 × 2.1 mm. (Plus guard cartridge) | 0.4 mL/min | Water (High purity via PureLab Option unit) with 0.1% formic acid | Acetonitrile (Far UV grade) with 0.1% (V/V) formic acid | 95% A to 5% A over 6 min |
| Bicarb BEHC18 | UPLC + Waters DAD + Waters SQD2, single quadrapole UPLC-MS | Acquity UPLC BEH Shield RP18 1.7 um 100 × 2.1 mm. | 0.4 mL/min | UPLC + Waters DAD + Waters SQD2, single quadrapole UPLC-MS | Acetonitrile | 95% A to 5% A over 6 min |
| CHIRAL HPLC Analytical Method X1 | Agilent 1260 Series HPLC and PDA detector | Chiralpak IB-N (250*4.6) mm, 5 micron or Chiralcel OX-H (250*4.6 mm), 5 micron | 1.0 ml/min | 0.1% DEA in n-Hexane | 0.1% DEA in Propane 2-ol:Methanol | Isocratic at 10% A for 30 min. |
| CHIRAL HPLC Analytical Method X2 | Agilent 1260 Series HPLC and PDA detector | Chiralpak AD-H (250*4.6 mm), 5 micron | 1.0 ml/min | Methanol | Acetonitrile | Isocratic at 50% A for 50 min |
| CHIRAL SFC Analytical Method X3 | Waters SFC Investigator and PDA detector | Chiralcel OJ-H (250*4.6 mm), 5 micron | 4.0 ml/min ABPR at 100 bar | Liq. $CO_2$ | 0.1% DEA in Methanol | Isocratic at 50% A for 50 min |
| CHIRAL HPLC Analytical Method X4 | Agilent 1260 Series HPLC and PDA detector | Chiralpak IB-N (250*4.6 mm), 5 micron | 1.0 ml/min | 0.1% DEA in n-Hexane | 0.1% DEA in Proapne 2-ol:Acetonitrile (70:30). | 80% A to 45% A over 5 min, then to 30% A over 5 min and isocratic at 30% A for 10 min |
| CHIRAL HPLC Analytical Method X5 | Agilent 1260 Series HPLC and PDA detector | Chiralpak IC (250*4.6 mm), 5 micron | 1.0 ml/min | 0.1% DEA in n-Hexane | 0.1% DEA in Propan-2-ol: Acetonitrile (70:30) | Isocratic at 65% A for 20 min |
| CHIRAL HPLC Analytical Method X6 | Agilent 1260 Series HPLC and PDA detector | Chiralpak IC (250*4.6 mm), 5 micron | 1.0 ml/min | 0.1% DEA in n-Hexane | 0.1% DEA in Propan-2-ol: Acetonitrile (70:30) | 80% A to 45% A over 5 min, then to 30% A over 5 min and isocratic at 30% A for 10 min |
| CHIRAL HPLC Analytical Method X7 | Waters SFC Investigator and PDA detector | Chiralcel OJ-H (250*4.6) mm, 5 micron, column flow | 4.0 ml/min ABPR at 100 bar | Liq. $CO_2$ | 0.1% Diethylamine in Propan-2-ol: Acetonitrile (50:50) or 0.1% DEA in IPA:ACN (30:70) | Isocratic at 50% A for 50 min |
| CHIRAL HPLC Analytical Method X8 | Agilent 1260 Series HPLC and PDA detector | Chiralpak IB-N (250*4.6) mm, 5 micron | 1.0 ml/min | 0.1% Diethylamine in Propan-2-ol | 0.1% Diethylamine in Methanol or IPA-ACN (70-30) | Isocratic at 30% A for 40 min |
| CHIRAL HPLC Analytical Method X9 | Agilent 1260 Series HPLC and PDA detector | Chiralpak IH (250*4.6 mm), 5 micron | 1.0 ml/min | 0.1% DEA in n-Hexane | 0.1% DEA in Propan-2-ol: Acetonitrile (70:30) | Eluting with 80% A to 45% A over 5 min, then to 30% A over 5 min and isocratic at 30% A for 10 min |
| CHIRAL HPLC Analytical Method X10 | Waters SFC Investigator and PDA detector | CHIRALPAK IH (250*4.6 mm) 5 micron | 4.0 ml/min at ABPR was 100 bar | Liq. $CO_2$ | 0.1% Diethylamine in MeOH. or (B) 0.1% DEA in IPA:ACN (50:50) | Isocratic at 50% A for 50 min |
| CHIRAL HPLC Analytical Method X11 | Agilent 1260 Series HPLC and PDA detector | Chiralpak IC (250*4.6 mm), 5 micron | 1.0 ml/min | 0.1% Diethylamine in n-Hexane | 0.1% Diethylamine in Propan-2-ol | Isocratic at 30% A for 40 min |
| CHIRAL HPLC Analytical Method X12 | Agilent 1260 Series HPLC and PDA detector | Chiralpak IB-N (250*4.6 mm), 5 micron | 1.0 ml/min | 0.1% Diethylamine in n-Hexane | 0.1% DEA in Proapne 2-ol: MeOH (50:50) | 80% A to 45% A over 5 minutes, then to 30% A over 5 minutes and isocratic at 30% A for 10 minutes |
| CHIRAL HPLC | Agilent 1260 Series HPLC | Chiralpak IC (250*4.6 mm, | 1.0 ml/min | 0.1% Diethylamine | 0.1% DEA in Propan-2-ol: | Isocratic at 65% A |

TABLE 9-continued

LC MS analytical methods Protocols

| Method | Instrument | Column | Flow Rate | Mobile Phase A | Mobile Phase B | Gradient |
|---|---|---|---|---|---|---|
| Analytical Method X13 | and PDA detector | 5 micron | | in n-Hexane | Acetonitrile (70:30) | |
| CHIRAL HPLC Analytical Method X14 | Agilent 1260 Series HPLC and PDA detector | Chiralcel OX-H (250*4.6) mm, 5 micron | 1.0 ml/min | 0.1% Diethylamine in n-Hexane | 0.1% DEA in Propan-2-ol: Acetonitrile (70:30) | 80% A to 45% A over 5 minutes, then to 30% A over 5 minutes and isocratic at 30% A for 10 minutes |
| CHIRAL HPLC Analytical Method X15 | Waters SFC Investigator and PDA detector | CHIRALPAK IB-N (250*4.6 mm) 5 micron | 4.0 ml/min at ABPR was 100 bar | Liq. $CO_2$ | 0.1% DEA in IPA:ACN (50:50) | Isocratic at 50% A for 50 min |
| CHIRAL HPLC Analytical Method X16 | Waters SFC Investigator and PDA detector | CHIRALPAK IH (250*4.6 mm) 5 micron | 4.0 ml/min at ABPR was 100 bar | Liq. $CO_2$ | 0.1% DEA in MeOH:ACN (50:50) | Isocratic at 50% A for 50 min |
| CHIRAL HPLC Analytical | Agilent 1260 Series HPLC and PDA detector | Chiralpak OX-H (250*4.6) mm, 5 micron | 1.0 ml/min | 0.1% DEA in n-Hexane | 0.1% DEA in Propan-2-ol: Acetonitrile (70:30). | Isocratic at 65% A for 25 min |
| CHIRAL HPLC Analytical Method X18 | Agilent 1260 Series HPLC and PDA detector | Chiralpak IH (250*4.6 mm), 5 micron | 1.0 ml/min | 0.1% DEA in n-Hexane | 0.1% DEA in Propan-2-ol: MeOH (50:50). | Isocratic at 75% A for 20 min |
| CHIRAL HPLC Analytical Method-X19 | Agilent 1260 Series HPLC and PDA detector | Chiralpak IB-N (250*4.6) mm, 5 micron | 1.0 ml/min | 0.1% DEA in n-Hexane | 0.1% DEA in Propan-2-ol: Acetonitrile (70:30). | Isocratic at 50% A for 30 min |

Example 39. Chiral Supercritical Fluid Chromatography (SFC) Separation Protocol

The diastereomeric/enantiomeric separation of compounds was achieved by Supercritical Fluid Chromatography (SFC) using a Waters Thar Prep100 preparative SFC system (P200 CO2 pump, 2545 modifier pump, 2998 UV/VIS detector, 2767 liquid handler with Stacked Injection Module). Appropriate columns were selected from LUX Cellulose-4 21.2×250 mm, 5 um; YMC Amylose-C 4.6×250 mm, 5 um; YMC Cellulose-C 4.6×250 mm, 5 um; or YMC Cellulose-SC 4.6×250 mm, 5 um. Appropriate isocratic methods were selected based on methanol, ethanol, or isopropanol solvent systems under un-modified or basic conditions. The standard SFC method used was modifier, $CO_2$, 100 mL/min, 120 Bar backpressure, 40° C. column temperature. The modifier used under basic conditions was diethylamine (0.1% V/V). The modifier used under acidic conditions was either formic acid (0.1% V/V) or trifluoroacetic acid (0.1% V/V). The SFC purification was controlled by Waters Fractionlynx software through monitoring at 210-400 nm and triggered at a threshold collection value, typically 260 nm. Collected fractions were analyzed by SFC (Waters/Thar SFC systems with Waters SQD). The fractions that contained the desired product were concentrated by vacuum centrifugation.

Example 40. HPK1 Biochemical Enzyme Assay

HPK1 biochemical enzyme assay: HPK1 enzyme inhibition was measured using a microfluidic mobility shift assay. Reactions were performed in a 384-well plate, containing 1.5 nM HPK1 (Invitrogen), in assay buffer (Carna Biosciences; pH 7.4). Test compounds were titrated in ten point curves (top final assay concentration 3 µM), and preincubated with enzyme/substrate mix for 30 min prior to initiation of the reaction by addition of ATP (1 mM final concentration) and substrate (1 µM final concentration; Carna Biosciences) diluted in assay buffer supplemented by $MgCl_2$ (final assay concentration of 5 mM). Following 60 min incubation at RT, the reaction was terminated by addition of 60 µl/well termination buffer (Carna Biosciences) and signal determination using a Caliper EZ Reader (Perkin Elmer, UK).

Table 10 shows the activity of selected compounds of this invention in the HPK1 biochemical enzyme assay. The compound numbers correspond to the compound numbers in Table 1. Compounds having an activity designated as "A" provided an $IC_{50} \leq 100$ nM; compounds having an activity designated as "B" provided an $IC_{50} > 100$ nM and $\leq 1,000$ nM; compounds having an activity designated as "C" provided an $IC_{50} > 1,000$ nM.

TABLE 10

HPK1 Assay results.

| Compound | HPK1 1000UMATP caliper IC50 (nM) |
|---|---|
| I-1 | B |
| I-2 | B |
| I-3 | B |
| I-4 | B |
| I-5 | B |

TABLE 10-continued

HPK1 Assay results.

| Compound | HPK1 1000UMATP caliper IC50 (nM) |
|---|---|
| I-6 | A |
| I-7 | B |
| I-8 | B |
| I-9 | B |
| I-10 | C |
| I-11 | B |
| I-12 | C |
| I-13 | B |
| I-14 | C |
| I-15 | B |
| I-17 | C |
| I-18 | A |
| I-19 | A |
| I-20 | A |
| I-21 | A |
| I-22 | B |
| I-23 | B |
| I-24 | A |
| I-25 | B |
| I-26 | B |
| I-27 | B |
| I-28 | A |
| I-29 | A |
| I-30 | B |
| I-31 | A |
| I-32 | A |
| I-33 | A |
| I-34 | A |
| I-35 | B |
| I-36 | B |
| I-37 | A |
| I-38 | A |
| I-39 | A |
| I-40 | A |
| I-41 | A |
| I-42 | A |
| I-43 | A |
| I-44 | B |
| I-45 | A |
| I-46 | A |
| I-47 | A |
| I-48 | B |
| I-49 | A |
| I-50 | B |
| I-51 | A |
| I-52 | A |
| I-53 | B |
| I-55 | A |
| I-56 | A |
| I-57 | A |
| I-58 | A |
| I-59 | A |
| I-60 | A |
| I-61 | B |
| I-62 | A |
| I-63 | A |
| I-64 | A |
| I-65 | A |
| I-66 | B |
| I-67 | A |
| I-68 | A |
| I-69 | A |
| I-70 | A |
| I-71 | A |
| I-72 | A |
| I-73 | A |
| I-74 | A |
| I-75 | A |
| I-76 | A |
| I-77 | B |
| I-78 | B |
| I-79 | A |
| I-80 | A |
| I-81 | A |
| I-82 | A |
| I-83 | A |
| I-84 | A |
| I-85 | A |
| I-86 | A |
| I-87 | A |
| I-88 | A |
| I-89 | A |
| I-90 | A |
| I-91 | A |
| I-92 | A |
| I-93 | A |
| I-94 | A |
| I-95 | A |
| I-96 | A |
| I-97 | A |
| I-98 | A |
| I-99 | B |
| I-100 | A |
| I-101 | A |
| I-102 | A |
| I-103 | B |
| I-104 | A |
| I-105 | A |
| I-106 | A |
| I-107 | A |
| I-108 | A |
| I-109 | A |
| I-110 | A |
| I-111 | A |
| I-112 | A |
| I-113 | A |
| I-114 | C |
| I-115 | A |
| I-116 | A |
| I-117 | A |
| I-118 | B |
| I-119 | A |
| I-120 | A |
| I-121 | A |
| I-122 | A |
| I-123 | A |
| I-124 | A |
| I-125 | A |
| I-126 | A |
| I-127 | C |
| I-128 | A |
| I-129 | A |
| I-130 | A |
| I-131 | A |
| I-132 | C |
| I-133 | A |
| I-134 | A |
| I-135 | A |
| I-136 | A |
| I-137 | A |
| I-138 | A |
| I-139 | A |
| I-140 | A |
| I-141 | A |
| I-142 | A |
| I-143 | A |
| I-144 | A |
| I-145 | A |
| I-146 | A |
| I-147 | B |
| I-148 | A |
| I-149 | A |
| I-150 | B |
| I-151 | A |
| I-152 | A |
| I-153 | A |
| I-154 | A |
| I-155 | A |
| I-156 | A |
| I-157 | A |

TABLE 10-continued

HPK1 Assay results.

| Compound | HPK1 1000UMATP caliper IC50 (nM) |
|---|---|
| I-158 | A |
| I-159 | A |
| I-160 | A |
| I-161 | A |
| I-162 | A |
| I-163 | B |
| I-164 | A |
| I-165 | C |
| I-166 | A |
| I-167 | A |
| I-168 | A |
| I-169 | A |
| I-170 | A |
| I-171 | A |
| I-172 | A |
| I-173 | A |
| I-174 | A |
| I-175 | A |
| I-176 | A |
| I-177 | A |
| I-178 | A |
| I-179 | A |
| I-180 | B |
| I-181 | A |
| I-182 | A |
| I-183 | A |
| I-184 | A |
| I-185 | B |
| I-186 | A |
| I-187 | A |
| I-188 | A |
| I-189 | B |
| I-190 | A |
| I-191 | A |
| I-192 | A |
| I-193 | A |
| I-194 | A |
| I-195 | B |
| I-196 | A |
| I-197 | A |
| I-198 | B |
| I-199 | B |
| I-200 | A |
| I-201 | A |
| I-202 | A |
| I-203 | A |
| I-204 | A |
| I-205 | B |
| I-206 | B |
| I-207 | B |
| I-208 | B |
| I-209 | A |
| I-210 | A |
| I-211 | A |
| I-212 | A |
| I-213 | A |
| I-214 | A |
| I-215 | B |
| I-216 | A |
| I-217 | A |
| I-218 | A |
| I-219 | A |
| I-220 | A |
| I-221 | A |
| I-222 | A |
| I-223 | A |
| I-224 | A |
| I-225 | A |
| I-226 | B |
| I-227 | A |
| I-228 | B |
| I-229 | A |
| I-230 | A |
| I-231 | A |
| I-232 | A |
| I-233 | A |
| I-234 | B |
| I-235 | A |
| I-236 | A |
| I-237 | B |
| I-238 | A |
| I-239 | B |
| I-240 | B |
| I-241 | A |
| I-242 | A |
| I-243 | A |
| I-244 | A |
| I-245 | A |
| I-246 | A |
| I-247 | A |
| I-248 | C |
| I-249 | B |
| I-250 | B |
| I-251 | A |
| I-252 | B |
| I-253 | C |
| I-254 | B |
| I-255 | A |
| I-256 | A |
| I-257 | B |
| I-258 | A |
| I-259 | B |
| I-260 | C |
| I-261 | A |
| I-262 | A |
| I-263 | A |
| I-264 | A |
| I-265 | A |
| I-266 | A |
| I-267 | C |
| I-268 | B |
| I-269 | A |
| I-270 | B |
| I-271 | A |
| I-272 | A |
| I-273 | C |
| I-274 | A |
| I-275 | A |
| I-276 | A |
| I-278 | A |
| I-279 | A |
| I-280 | A |
| I-281 | A |
| I-282 | C |
| I-283 | B |
| I-284 | A |
| I-285 | A |
| I-286 | C |
| I-287 | A |
| I-288 | B |
| I-289 | A |
| I-290 | C |
| I-291 | A |
| I-292 | A |
| I-293 | A |
| I-294 | A |
| I-295 | A |
| I-296 | B |
| I-297 | A |
| I-298 | A |
| I-299 | A |
| I-300 | A |
| I-301 | A |
| I-302 | B |
| I-303 | A |
| I-304 | A |
| I-305 | C |
| I-306 | C |
| I-307 | B |
| I-308 | C |

TABLE 10-continued

HPK1 Assay results.

| Compound | HPK1 1000UMATP caliper IC50 (nM) |
|---|---|
| I-309 | A |
| I-310 | A |
| I-311 | A |
| I-312 | A |
| I-313 | A |
| I-314 | A |
| I-315 | A |
| I-316 | C |
| I-317 | A |
| I-318 | A |
| I-319 | A |
| I-320 | A |
| I-321 | A |
| I-322 | A |
| I-323 | C |
| I-324 | C |
| I-325 | A |
| I-326 | A |
| I-327 | A |
| I-328 | A |
| I-329 | A |
| I-330 | B |
| I-331 | A |
| I-332 | A |
| I-333 | A |
| I-334 | A |
| I-335 | A |
| I-336 | A |
| I-338 | A |
| I-339 | A |
| I-340 | C |
| I-341 | A |
| I-343 | A |
| I-344 | A |
| I-345 | A |
| I-346 | A |
| I-347 | A |
| I-348 | A |
| I-349 | A |
| I-350 | A |
| I-351 | A |
| I-352 | A |
| I-353 | B |
| I-354 | C |
| I-355 | A |
| I-356 | A |
| I-357 | A |
| I-358 | A |
| I-359 | A |
| I-360 | A |
| I-361 | A |
| I-362 | A |
| I-363 | A |
| I-364 | A |
| I-365 | A |
| I-366 | A |
| I-367 | A |
| I-368 | C |
| I-369 | A |
| I-370 | B |
| I-371 | A |
| I-372 | A |
| I-373 | A |
| I-374 | A |
| I-375 | C |
| I-376 | B |
| I-377 | B |
| I-378 | B |
| I-379 | B |
| I-380 | B |
| I-381 | A |
| I-382 | C |
| I-383 | A |
| I-384 | C |
| I-385 | A |
| I-386 | A |
| I-387 | A |
| I-388 | A |
| I-389 | A |
| I-390 | B |
| I-391 | A |
| I-392 | A |
| I-393 | A |
| I-394 | A |
| I-395 | A |
| I-396 | C |
| I-397 | A |
| I-398 | B |
| I-399 | A |
| I-400 | A |
| I-401 | A |
| I-402 | A |
| I-403 | A |
| I-404 | A |
| I-405 | A |
| I-406 | A |
| I-407 | A |
| I-408 | A |
| I-411 | A |
| I-412 | A |
| I-413 | C |
| I-414 | A |
| I-415 | A |
| I-416 | A |
| I-417 | A |
| I-418 | C |
| I-419 | C |
| I-420 | A |
| I-421 | A |
| I-422 | B |
| I-423 | A |
| I-424 | A |
| I-425 | A |
| I-426 | A |
| I-427 | A |
| I-428 | A |
| I-429 | A |
| I-430 | C |
| I-431 | A |
| I-432 | C |
| I-433 | A |
| I-434 | A |
| I-435 | A |
| I-436 | A |
| I-437 | A |
| I-438 | A |
| I-439 | A |
| I-440 | A |
| I-441 | B |
| I-442 | A |
| I-443 | A |
| I-444 | A |
| I-445 | B |
| I-446 | A |
| I-447 | A |
| I-448 | B |
| I-449 | A |
| I-450 | A |
| I-451 | A |
| I-452 | A |
| I-453 | A |
| I-454 | A |
| I-455 | B |
| I-456 | A |
| I-457 | A |
| I-458 | A |
| I-459 | A |
| I-460 | A |
| I-461 | A |
| I-462 | A |

TABLE 10-continued

HPK1 Assay results.

| Compound | HPK1 1000UMATP caliper IC50 (nM) |
|---|---|
| I-463 | A |
| I-464 | A |
| I-465 | A |
| I-467 | A |
| I-468 | A |
| I-469 | A |
| I-470 | C |
| I-471 | A |
| I-472 | A |
| I-473 | A |
| I-474 | A |
| I-475 | A |
| I-476 | A |
| I-477 | A |
| I-478 | A |
| I-479 | A |
| I-480 | B |
| I-481 | A |
| I-482 | A |
| I-483 | A |
| I-484 | A |
| I-485 | A |
| I-486 | A |
| I-487 | A |
| I-488 | A |
| I-489 | A |
| I-490 | A |
| I-491 | A |
| I-492 | A |
| I-493 | A |
| I-494 | A |
| I-495 | A |
| I-496 | A |
| I-497 | A |
| I-498 | A |
| I-499 | A |
| I-500 | A |
| I-501 | A |
| I-502 | A |
| I-503 | A |
| I-504 | A |
| I-505 | A |
| I-506a | A |
| I-506 | A |
| I-507 | A |
| I-508 | A |
| I-509 | A |
| I-510 | A |
| I-511 | A |
| I-512 | A |
| I-513 | A |
| I-514 | A |
| I-515 | A |
| I-516 | A |
| I-517 | A |
| I-518 | A |
| I-519 | A |
| I-520 | A |
| I-521 | A |
| I-522 | A |
| I-523 | A |
| I-524 | A |
| I-525 | A |
| I-526 | A |
| I-527 | A |
| I-528 | A |
| I-529 | A |
| I-530 | A |
| I-531 | A |
| I-532 | A |
| I-533 | A |
| I-534 | A |
| I-535 | A |
| I-536 | A |
| I-537 | A |
| I-538 | A |
| I-539 | A |
| I-540 | A |
| I-541 | A |
| I-542 | A |
| I-543 | A |
| I-544 | A |
| I-545 | A |
| I-546 | A |
| I-547 | A |
| I-548 | A |
| I-549 | A |
| I-550 | A |
| I-551 | A |
| I-552 | A |
| I-553 | A |
| I-554 | A |
| I-555 | A |
| I-556 | A |
| I-557 | A |
| I-558 | A |
| I-559 | A |
| I-560 | A |
| I-561 | A |
| I-562 | A |
| I-563 | A |
| I-564 | A |
| I-565 | C |
| I-566 | A |
| I-567 | A |
| I-568 | A |
| I-569 | A |
| I-570 | A |
| I-571 | A |
| I-572 | A |
| I-573 | A |
| I-574 | A |
| I-575 | B |
| I-576 | A |
| I-577 | A |
| I-578 | A |
| I-579 | A |
| I-580 | A |
| I-581 | A |
| I-582 | A |
| I-583 | A |
| I-584 | A |
| I-585 | A |
| I-586 | A |
| I-587 | A |
| I-588 | C |
| I-589 | A |
| I-590 | A |
| I-591 | A |
| I-592 | C |
| I-593 | A |
| I-594 | A |
| I-595 | A |
| I-596 | A |
| I-597 | A |
| I-598 | A |
| I-599 | A |
| I-600 | A |
| I-601 | A |
| I-602 | A |
| I-603 | A |
| I-604 | A |
| I-605 | A |
| I-606 | A |
| I-607 | A |
| I-608 | A |
| I-609 | A |
| I-610 | A |
| I-611 | A |
| I-612 | A |

TABLE 10-continued

HPK1 Assay results.

| Compound | HPK1 1000UMATP caliper IC50 (nM) |
|---|---|
| I-613 | A |
| I-614 | A |
| I-615 | B |
| I-616 | A |
| I-617 | A |
| I-618 | A |
| I-619 | A |
| I-620 | A |
| I-621 | A |
| I-622 | A |
| I-623 | A |
| I-624 | A |
| I-626 | A |
| I-627 | A |
| I-628 | A |
| I-629 | A |
| I-630 | A |
| I-631 | C |
| I-632 | C |
| I-633 | A |
| I-634 | A |
| I-635 | A |
| I-639 | A |
| I-640 | A |
| I-641 | A |
| I-642 | B |
| I-643 | A |
| I-644 | B |
| I-645 | A |
| I-646 | A |
| I-648 | A |
| I-649 | A |
| I-650 | A |
| I-651 | B |
| I-652 | A |
| I-653 | A |
| I-654 | A |
| I-655 | A |
| I-656 | A |
| I-657 | A |
| I-658 | A |
| I-659 | A |
| I-660 | A |
| I-661 | B |
| I-662 | A |
| I-663 | A |
| I-667 | C |
| I-668 | A |
| I-669 | A |
| I-670 | A |
| I-671 | A |
| I-672 | A |
| I-673 | A |
| I-674 | A |
| I-675 | A |
| I-676 | A |
| I-677 | A |
| I-678 | A |
| I-679 | A |
| I-680 | B |
| I-681 | A |
| I-682 | B |
| I-683 | A |
| I-684 | A |
| I-685 | B |
| I-686 | A |
| I-687 | A |
| I-688 | C |
| I-689 | B |
| I-690 | A |
| I-691 | A |
| I-692 | A |
| I-693 | A |
| I-694 | A |
| I-695 | A |
| I-696 | A |
| I-697 | A |
| I-698 | A |
| I-699 | A |
| I-700 | A |
| I-701 | A |
| I-702 | A |
| I-703 | A |
| I-704 | A |
| I-705 | A |
| I-706 | A |
| I-707 | A |
| I-708 | A |
| I-709 | A |
| I-710 | A |
| I-711 | A |
| I-712 | A |
| I-713 | A |
| I-714 | A |
| I-715 | A |
| I-716 | A |
| I-717 | A |
| I-718 | A |
| I-719 | A |
| I-720 | A |
| I-721 | A |
| I-722 | A |
| I-723 | A |
| I-724 | B |
| I-725 | A |
| I-726 | A |
| I-727 | A |
| I-728 | A |
| I-729 | A |
| I-730 | A |
| I-731 | A |
| I-732 | A |
| I-733 | A |
| I-734 | A |
| I-735 | A |
| I-736 | A |
| I-737 | A |
| I-738 | A |
| I-739 | A |
| I-740 | A |
| I-741 | A |
| I-742 | A |
| I-743 | A |
| I-744 | A |
| I-745 | A |
| I-746 | A |
| I-747 | A |
| I-748 | A |
| I-749 | A |
| I-750 | A |
| I-751 | A |
| I-752 | A |
| I-753 | A |
| I-754 | A |
| I-755 | A |
| I-756 | A |
| I-757 | A |
| I-758 | A |
| I-759 | A |
| I-760 | A |
| I-761 | A |
| I-762 | A |
| I-763 | A |
| I-764 | A |
| I-765 | A |
| I-766 | A |
| I-767 | A |
| I-768 | A |
| I-769 | A |
| I-770 | A |

TABLE 10-continued

HPK1 Assay results.

| Compound | HPK1 1000UMATP caliper IC50 (nM) |
|---|---|
| I-771 | A |
| I-772 | A |
| I-773 | B |
| I-774 | A |
| I-775 | A |
| I-776 | A |
| I-777 | A |
| I-778 | A |
| I-779 | A |
| I-780 | A |
| I-781 | A |
| I-782 | A |
| I-783 | A |
| I-784 | A |
| I-785 | A |
| I-786 | A |
| I-787 | A |
| I-788 | A |
| I-789 | A |
| I-790 | A |
| I-791 | A |
| I-792 | A |
| I-793 | A |
| I-794 | A |
| I-795 | A |
| I-796 | A |
| I-797 | A |
| I-798 | A |
| I-799 | A |
| I-800 | A |
| I-801 | A |
| I-802 | A |
| I-803 | A |
| I-804 | A |
| I-805 | A |
| I-806 | A |
| I-807 | A |
| I-808 | A |
| I-809 | A |
| I-810 | A |
| I-811 | A |
| I-812 | A |
| I-813 | A |
| I-814 | A |
| I-815 | A |
| I-816 | A |
| I-817 | A |
| I-818 | B |
| I-819 | A |
| I-820 | A |
| I-821 | A |
| I-822 | A |
| I-823 | A |
| I-824 | A |
| I-825 | A |
| I-826 | A |
| I-827 | A |
| I-828 | A |
| I-829 | A |
| I-830 | A |
| I-831 | A |
| I-832 | B |
| I-833 | B |
| I-834 | A |
| I-835 | A |
| I-836 | A |
| I-837 | A |
| I-838 | A |
| I-839 | A |
| I-840 | A |
| I-841 | B |
| I-842 | A |
| I-843 | A |
| I-844 | A |
| I-845 | A |
| I-846 | A |
| I-847 | A |
| I-848 | A |
| I-849 | A |
| I-850 | A |
| I-851 | A |
| I-852 | A |

While we have described a number of embodiments of this invention, it is apparent that our examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A compound of formula I:

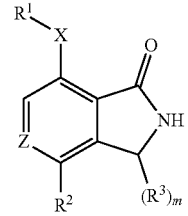

or a pharmaceutically acceptable salt thereof, wherein:
Z is CR or N;
X is a covalent bond or —NR—;
$R^1$ is selected from the group consistig of $C_{1-6}$ aliphatic; phenyl; a 3-7 membered saturated or partially unsaturated monocyclic carbocyclic ring; a 5-6 membered monocyclic heteroaryl ring having 1-4 heteroatoms independently selected from the group consisting of nitrogen, oxygen, and sulfur; a 3-7 membered saturated or partially unsaturated monocyclic heterocyclic ring having 1-2 heteroatoms independently selected from the group consisting of nitrogen, oxygen, and sulfur; and an 8-10 membered saturated or partially unsaturated bicyclic heterocyclic ring having 1-4 heteroatoms independently selected from the group consisting of nitrogen, oxygen, and sulfur; each of which is substituted with q instances of $R^C$;
$R^2$ is selected from the group consisting of 6-11 membered saturated, partially unsaturated, or unsaturated fused bicyclic ring having 0-3 heteroatoms independently selected from the group consisting of nitrogen, oxygen, and sulfur; each of which is substituted with q instances of $R^C$;
each instance of $R^3$ is independently hydrogen or an optionally substituted $C_{1-6}$ aliphatic group;
each instance of $R^C$ is independently oxo, halogen, —CN, —$NO_2$, —OR, —SR, —$NR_2$, —$S(O)_2R$, —$S(O)_2NR_2$, —S(O)R, —$S(O)NR_2$, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)C(NR)$NR_2$, —N(R)$NR_2$, —N(R)S(O)$_2NR_2$, —N(R)S(O)$_2R$, —N=S(O)$R_2$, —S(NR)(O)R, —N(R)

S(O)R, —N(R)CN, —P(O)(R)NR$_2$, —P(O)(R)OR or —P(O)R$_2$; or each instance of R$^C$ is independently an optionally substituted group selected from C$_{1-6}$ aliphatic; phenyl; naphthyl; a 3-7 membered saturated or partially unsaturated monocyclic carbocyclic ring; a 3-7 membered saturated or partially unsaturated monocyclic heterocyclic ring having 1-2 heteroatoms independently selected from the group consisting of nitrogen, oxygen, phosphorous, silicon and sulfur; a 5-6 membered monocyclic heteroaryl ring having 1-4 heteroatoms independently selected from the group consisting of nitrogen, oxygen, and sulfur; an 8-10 membered bicyclic heteroaryl ring having 1-5 heteroatoms independently selected from the group consisting of nitrogen, oxygen, and sulfur; a 5-8 membered saturated or partially unsaturated bridged bicyclic ring having 0-3 heteroatoms independently selected from the group consisting of nitrogen, oxygen, and sulfur; a 6-11 membered saturated or partially unsaturated spirocyclic ring having 0-3 heteroatoms independently selected from the group consisting of nitrogen, oxygen, and sulfur; and a 6-11 membered saturated or partially unsaturated bicyclic heterocyclic ring having 1-3 heteroatoms independently selected from nitrogen, oxygen, and sulfur; each of which is substituted with r instances of R and s instances of R$^D$;

each instance of R$^D$ is independently oxo, halogen, —CN, —NO$_2$, —OR, —SR, —NR$_2$, —S(O)$_2$R, —S(O)$_2$NR$_2$, —S(O)R, —S(O)NR$_2$, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)C(NR)NR$_2$, —N(R)NR$_2$, —N(R)S(O)$_2$NR$_2$, —N(R)S(O)$_2$R, —N=S(O)R$_2$, —S(NR)(O)R, —N(R)S(O)R, —N(R)CN, —P(O)(R)NR$_2$, —P(O)(R)OR or —P(O)R$_2$;

each R is independently hydrogen, —CN, halogen, or an optionally substituted group selected from C$_{1-6}$ aliphatic; phenyl; naphthyl; a 3-7 membered saturated or partially unsaturated monocyclic carbocyclic ring; a 3-7 membered saturated or partially unsaturated monocyclic heterocyclic ring having 1-2 heteroatoms independently selected from the group consisting of nitrogen, oxygen, and sulfur; a 5-6 membered monocyclic heteroaryl ring having 1-4 heteroatoms independently selected from the group consisting of nitrogen, oxygen, and sulfur; an 8-10 membered bicyclic heteroaryl ring having 1-4 heteroatoms independently selected from the group consisting of nitrogen, oxygen, and sulfur; a 7-12 membered saturated or partially unsaturated bicyclic heterocyclic ring having 1-4 heteroatoms independently selected from the group consisting of nitrogen, oxygen, and sulfur; a 5-8 membered saturated or partially unsaturated bridged bicyclic ring having 0-3 heteroatoms independently selected from the group consisting of nitrogen, oxygen, and sulfur; a 6-10 membered saturated or partially unsaturated spirocyclic ring having 0-3 heteroatoms independently selected from the group consisting of nitrogen, oxygen, and sulfur; and a 6-11 membered saturated or partially unsaturated bicyclic carbocyclic ring having 1-2 heteroatoms independently selected from the group consisting of nitrogen, oxygen, and sulfur; or:

two R groups on the same nitrogen are taken together with the nitrogen to form an optionally substituted 4-7 membered monocyclic saturated, partially unsaturated, or heteroaryl ring having, in addition to the nitrogen, 0-3 heteroatoms independently selected from the group consisting of nitrogen, oxygen, and sulfur; an 8-10 membered bicyclic heteroaryl ring having 1-4 heteroatoms independently selected from the group consisting of nitrogen, oxygen, and sulfur; or a 7-12 membered saturated or partially unsaturated bicyclic heterocyclic ring having 1-4 heteroatoms independently selected from the group consisting of nitrogen, oxygen, and sulfur;

m is 0, 1, or 2;

each q is independently 0, 1, 2, 3, or 4;

each r is independently 0, 1, 2, 3, or 4; and each s is independently 0, 1, 2, 3, or 4.

2. The compound of claim 1, wherein the compound is any one of formulae II, IV, V, or VII:

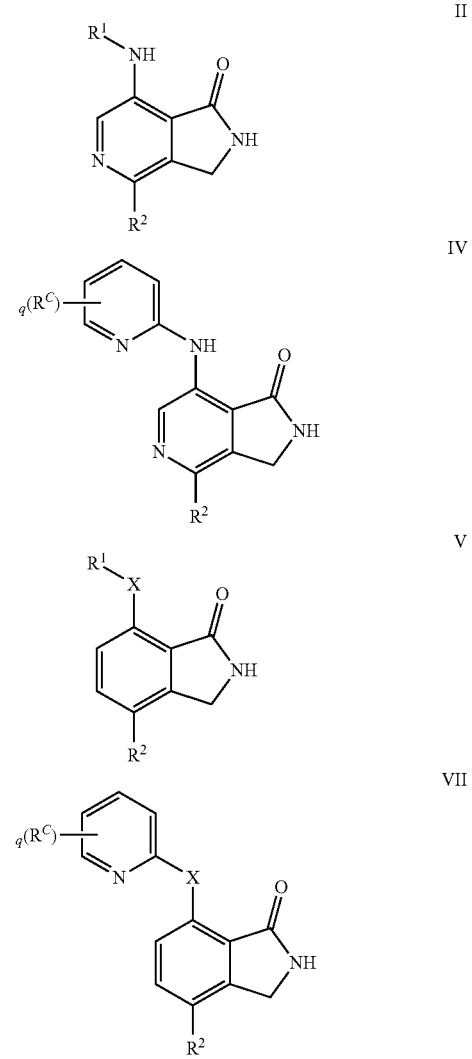

or a pharmaceutically acceptable salt thereof, wherein X, R$^1$, R$^2$, R$^C$, and q are as defined in claim 1.

3. The compound of claim 1, wherein the compound is any one of formulae XI-a, XI-b, XIV-a, XIV-b, XVII-a, XVII-b, XX-a, or XX-b:

XI-a
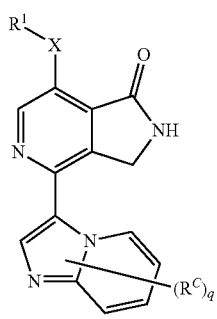
XI-b
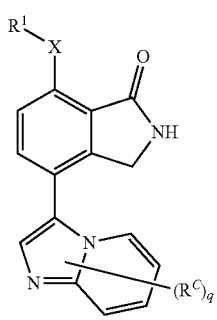
XIV-a
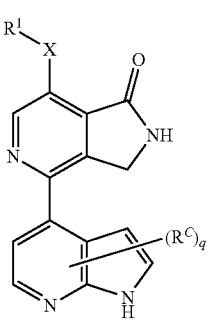
XIV-b
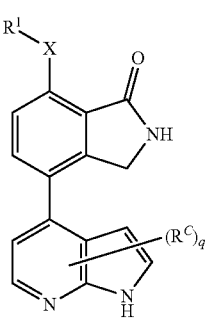
XVII-a
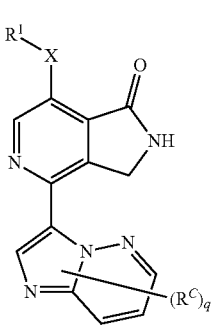
XVII-b
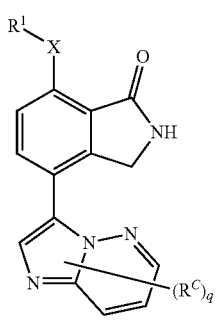
XX-a
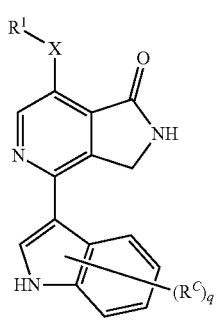
XX-b
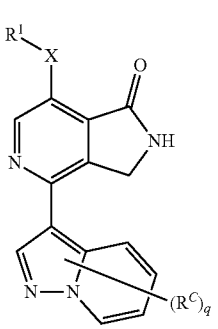
or a pharmaceutically acceptable salt thereof, wherein X, $R^1$, $R^C$, and q are as defined in claim 1.
4. The compound of claim 1, wherein the compound is any one of formulae XXIII-a, XXIII-b, XXVI-a, XXVI-b, XXIX-a, or XXIX-b:
XXIII-a -continued XXIII-b
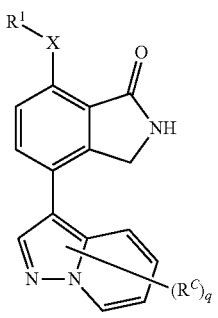

XXVI-a
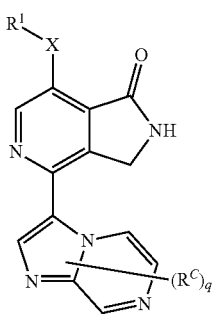

XXVI-b
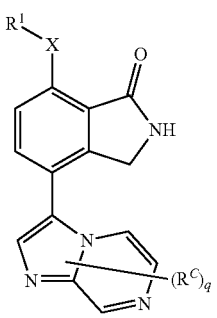

XXIX-a
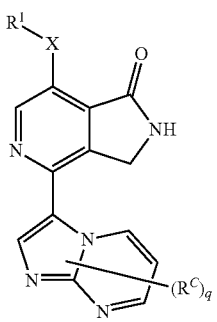

XXIX-b
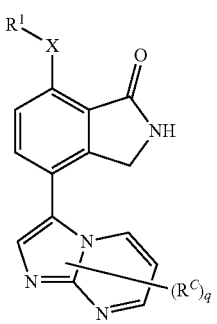

or a pharmaceutically acceptable salt thereof, wherein X, $R^1$, $R^C$, and q are as defined in claim 1.

5. The compound of claim 1, wherein X is —NR—.

6. The compound of claim 1, wherein $R^1$ is $C_{1-6}$ aliphatic which is substituted with q instances of $R^C$; phenyl which is substituted with q instances of $R^C$; a 3-7 membered saturated or partially unsaturated monocyclic carbocyclic ring, which is substituted with q instances of $R^C$; a 5-6 membered monocyclic heteroaryl ring having 1-4 heteroatoms independently selected from the group consisting of nitrogen, oxygen, and sulfur, which is substituted with q instances of $R^C$; or a 3-7 membered saturated or partially unsaturated monocyclic heterocyclic ring having 1-2 heteroatoms independently selected from the group consisting of nitrogen, oxygen, and sulfur, which is substituted with q instances of $R^C$.

7. The compound of claim 6, wherein $R^1$ is phenyl or a 5-6 membered monocyclic heteroaryl ring having 1-4 heteroatoms independently selected from the group consisting of nitrogen, oxygen, and sulfur, each of which is substituted with q instances of $R^C$.

8. The compound of claim 1, wherein $R^1$ is phenyl, furanyl, furazanyl, imidazolidinyl, imidazolinyl, imidazolyl, isothiazolyl, isoxazolyl, morpholinyl, oxadiazolyl, 1,2,3-oxadiazolyl, 1,2,4-oxadiazolyl, 1,2,5oxadiazolyl, 1,3,4-oxadiazolyl, oxazolidinyl, oxazolyl, oxazolidinyl, oxetanyl, pyrimidinyl, piperazinyl, piperidinyl, pyranyl, pyrazinyl, pyrazolidinyl, pyrazolinyl, pyrazolyl, pyridazinyl, pyridinyl, pyridyl, pyrimidinyl, pyrrolidinyl, pyrrolinyl, 2H-pyrrolyl, pyrrolyl, tetrahydrofuranyl, tetrahydropyranyl, thiazolyl, thienyl, triazinyl, 1,2,3-triazolyl, 1,2,4-triazolyl, 1,2,5-triazolyl, 1,3,4-triazolyl, oxetanyl, azetidinyl, or xanthenyl; each of which is substituted by q instances of $R^C$.

9. The compound of claim 8, wherein $R^1$ is phenyl, pyrazolyl, pyridinyl, pyrazinyl, or pyrimidinyl; each of which is substituted by q instances of $R^C$.

10. The compound of claim 1, wherein $R^1$ is

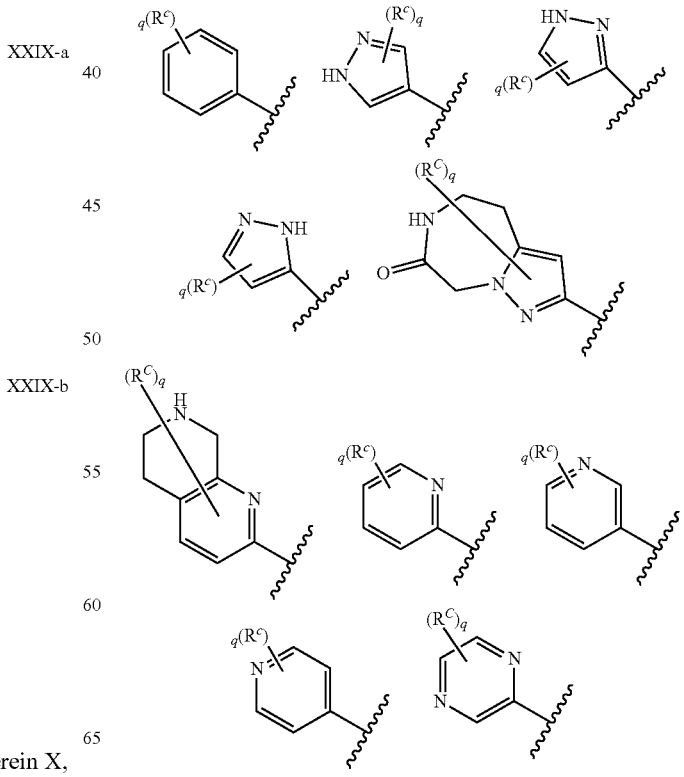

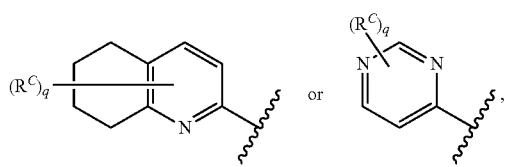
wherein R^C and q are as defined in claim 1.
11. The compound of claim 1, wherein R^1 is
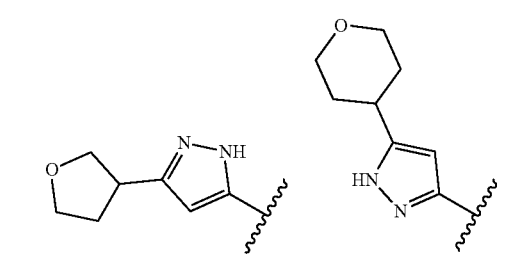
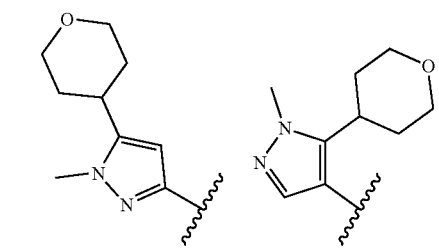
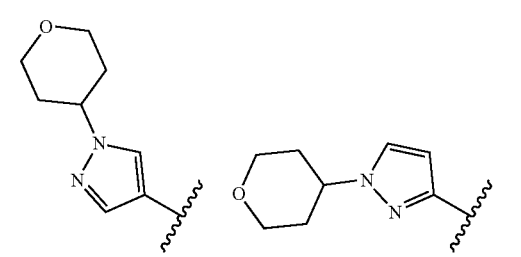
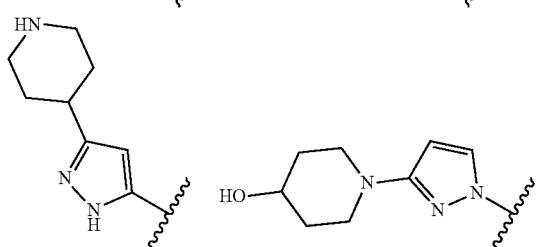
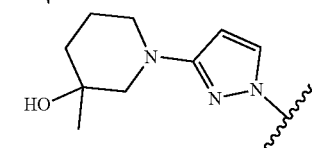
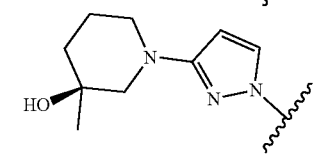
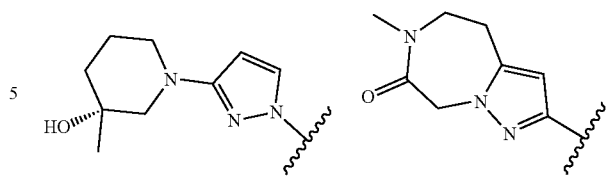
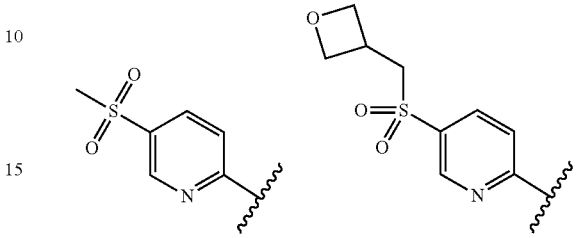
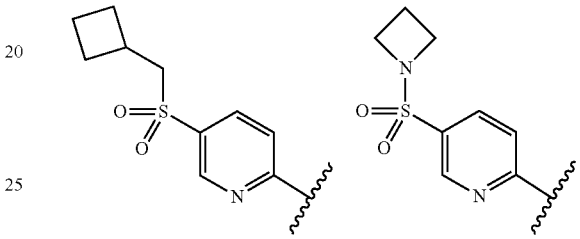
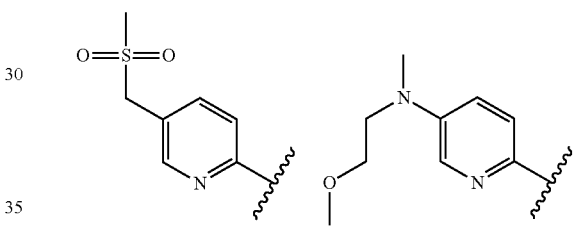
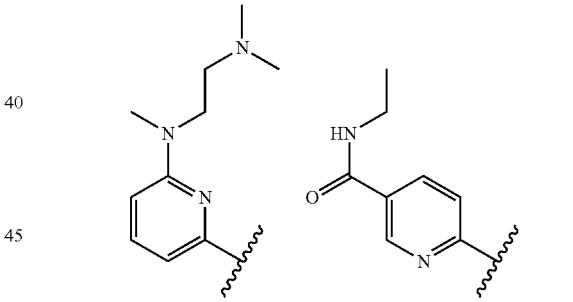
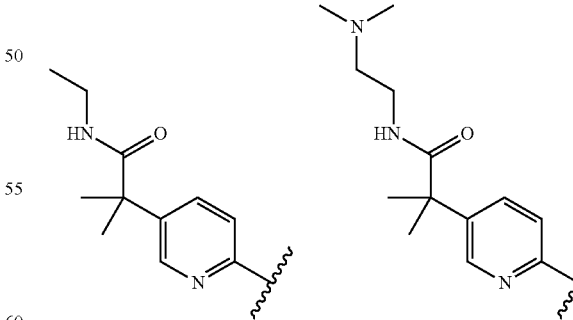
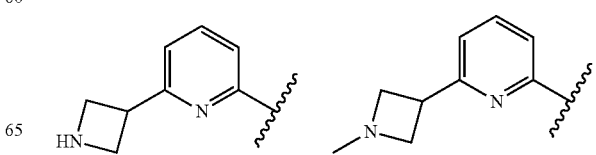

2329 | 2330
-continued | -continued
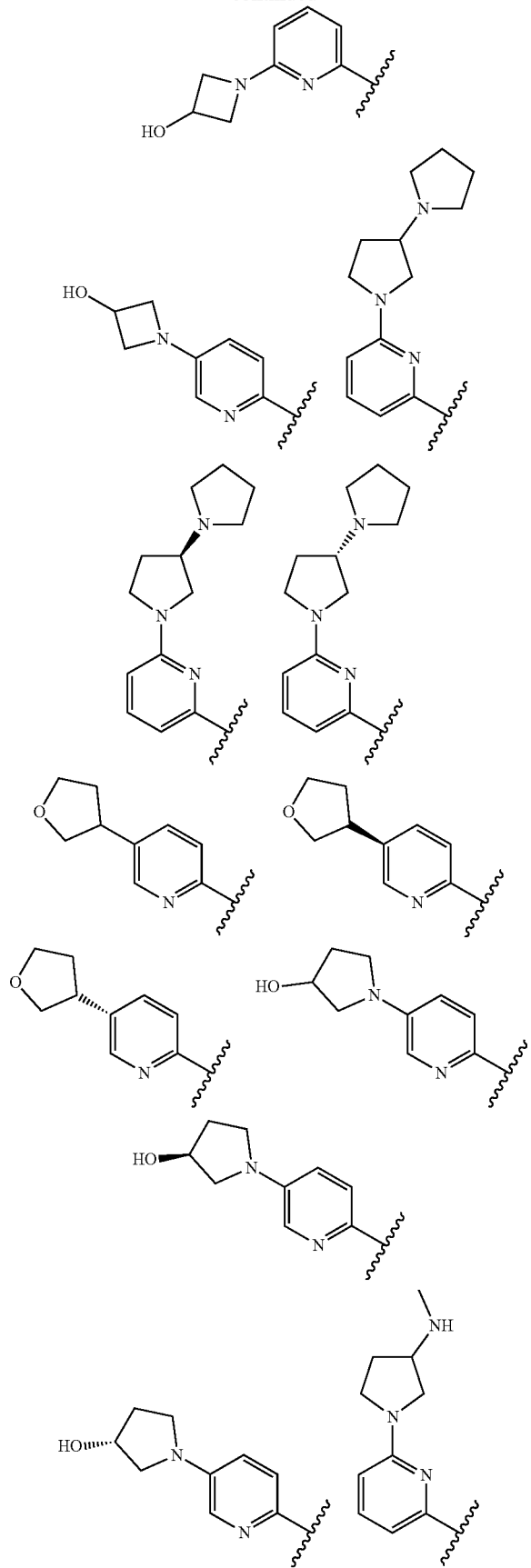
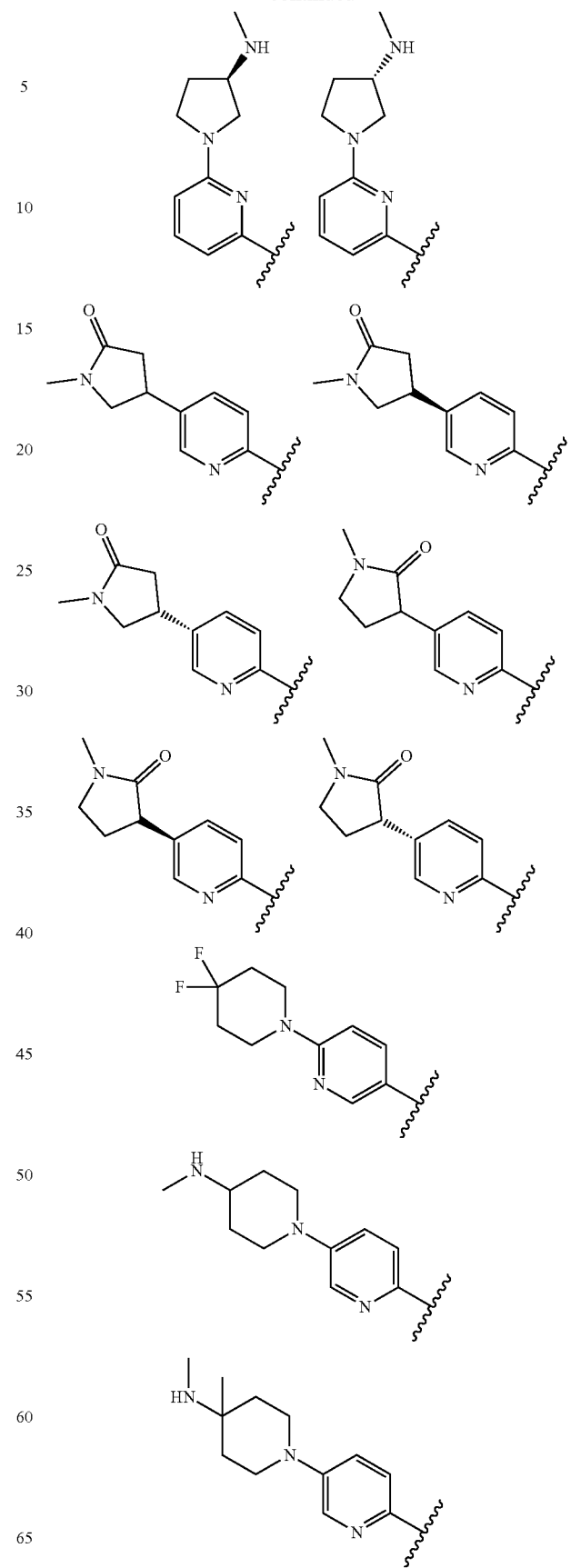

2331
-continued
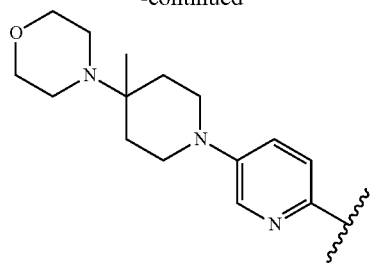
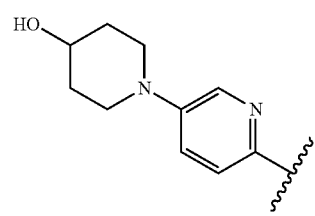
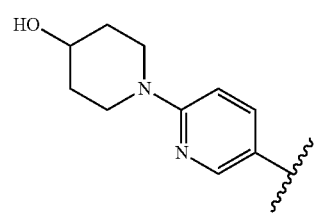
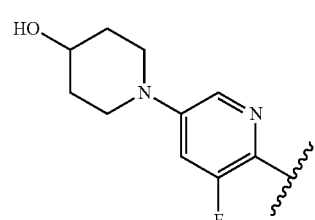
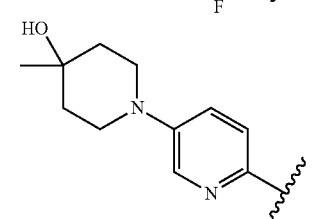
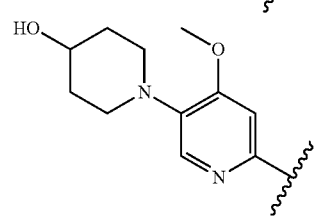
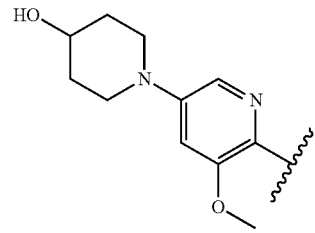
2332
-continued
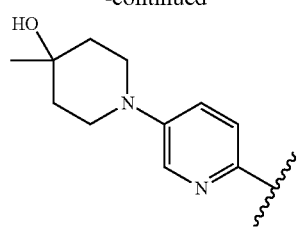
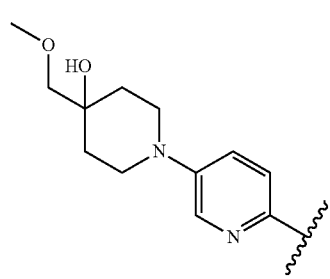
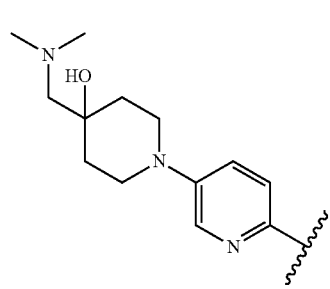
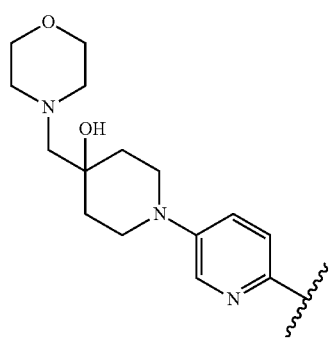
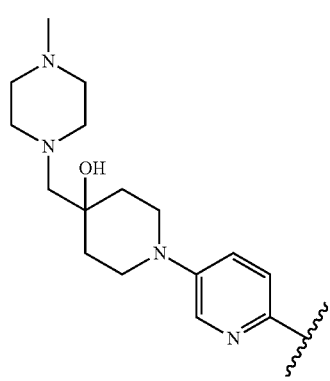

2333
-continued
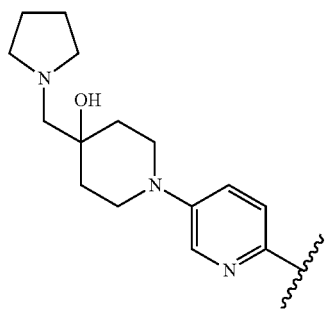
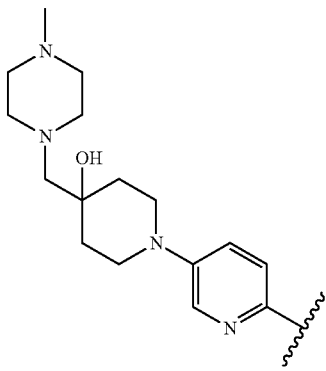
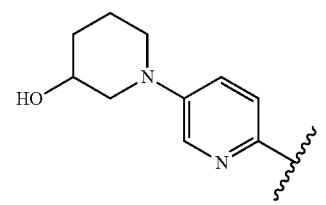
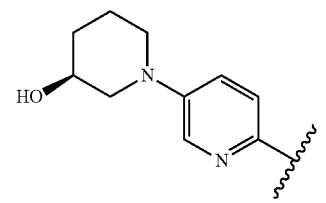
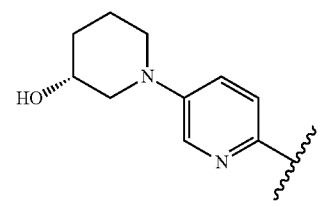
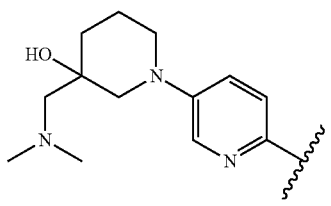
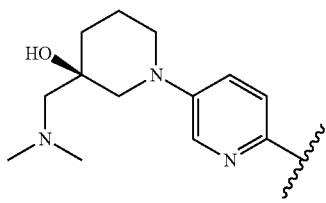
2334
-continued
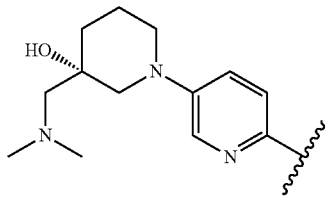
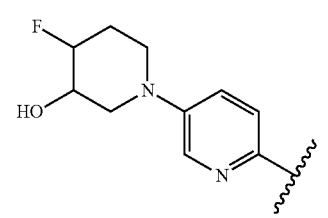
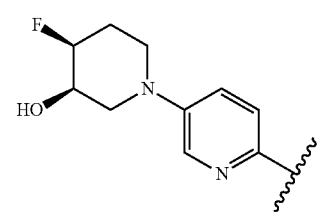
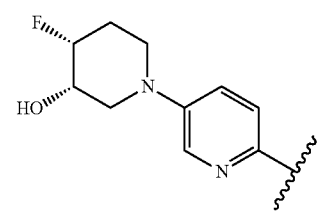
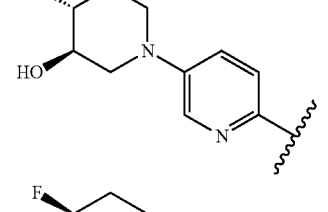
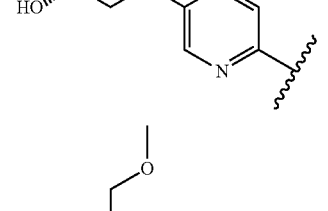
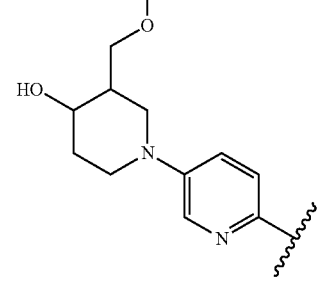

2335
-continued
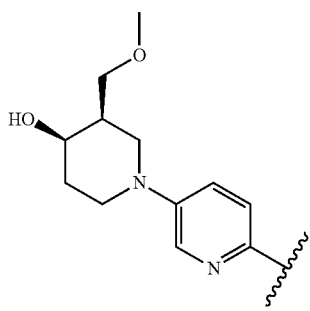
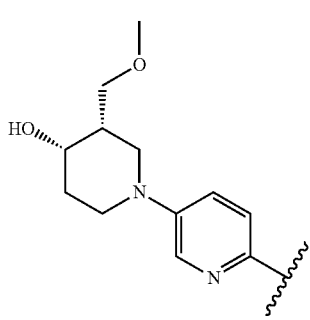
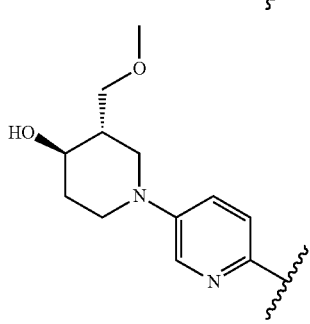
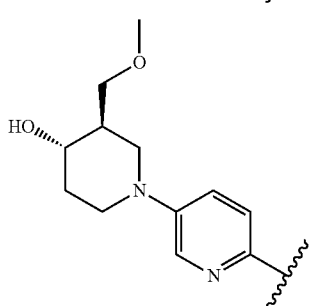
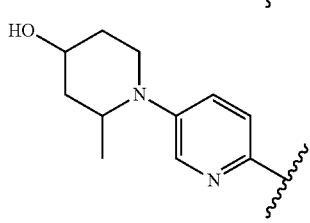
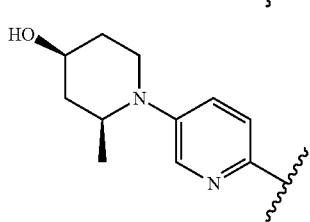
2336
-continued
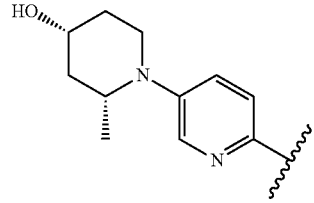
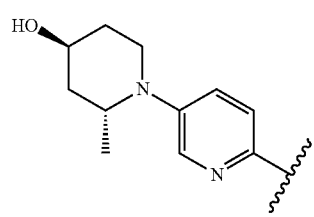
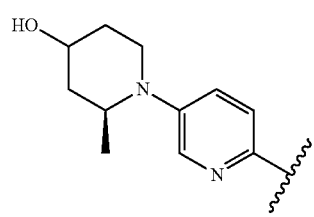
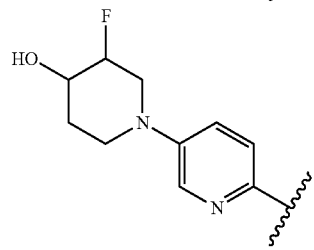
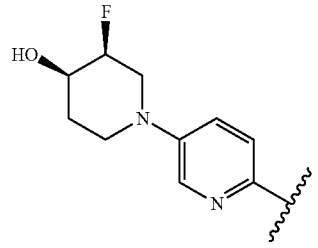
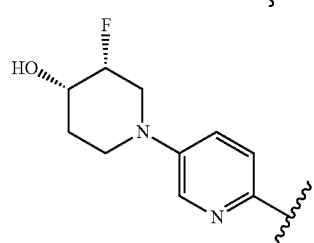
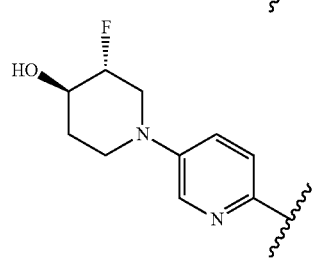

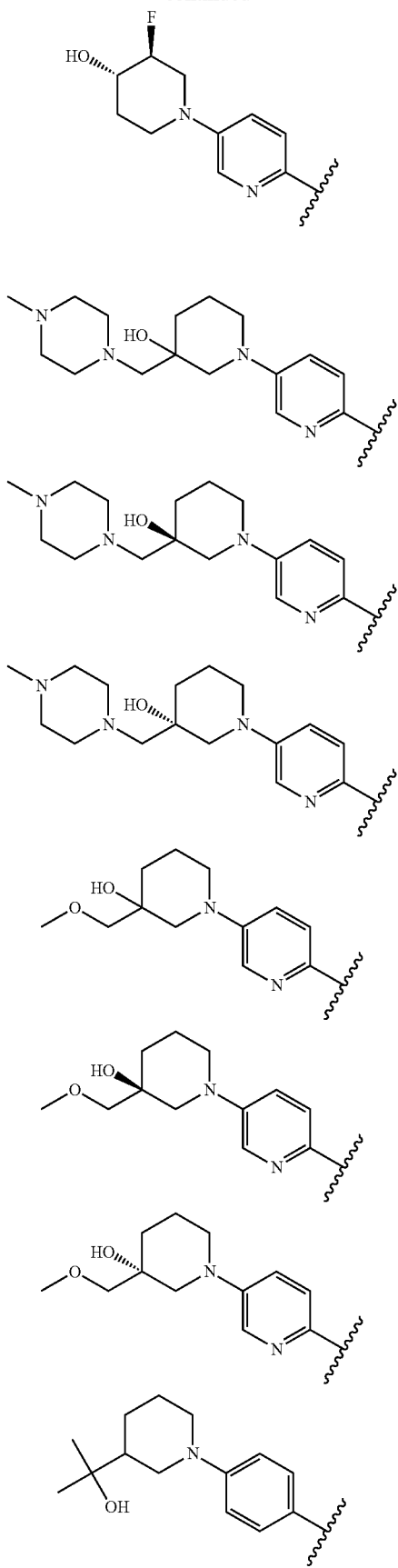
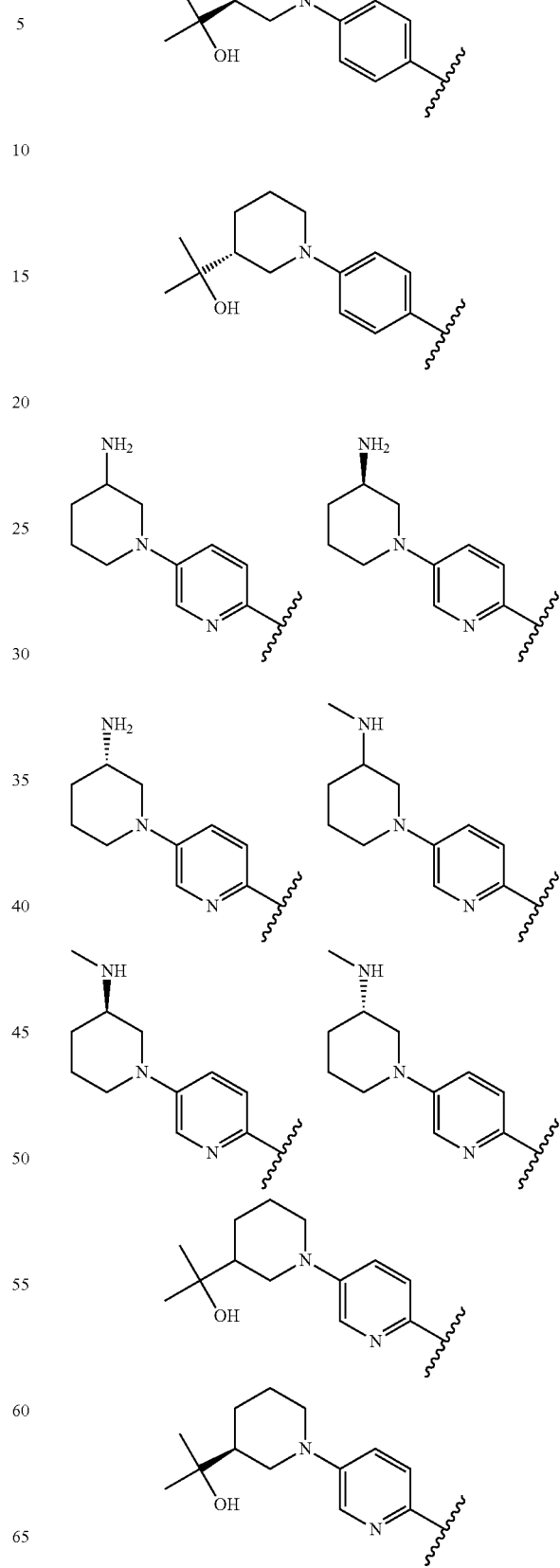

2339
-continued
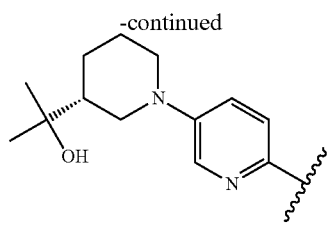
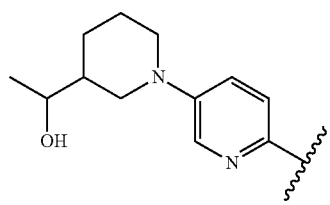
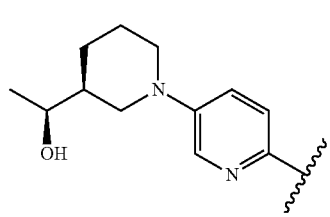
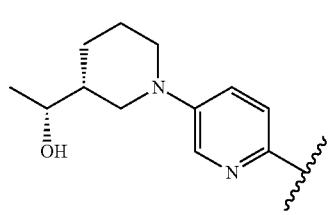
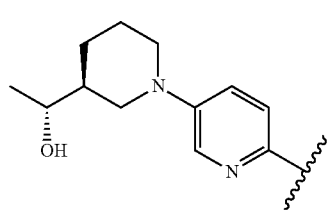
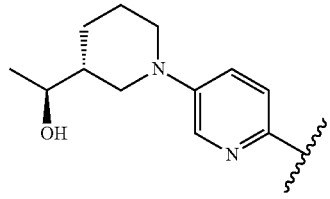
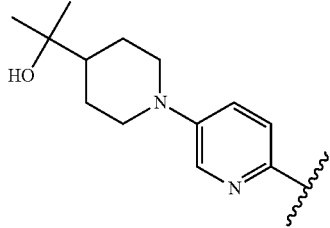
2340
-continued
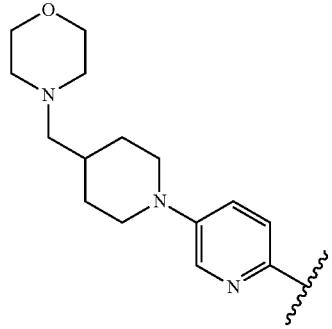
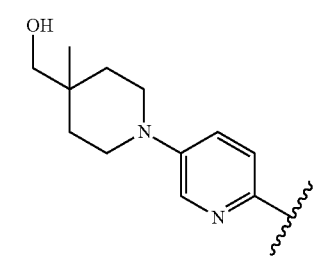
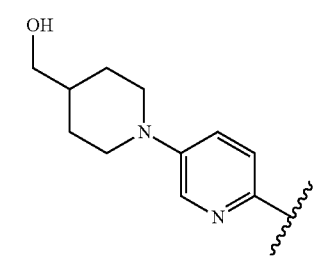
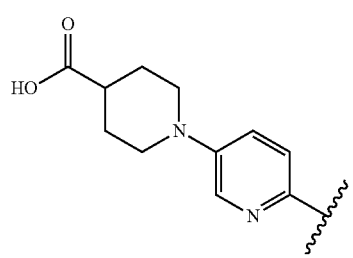
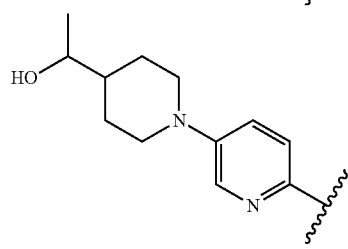
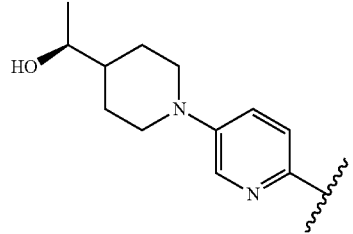

2341
-continued
2342
-continued
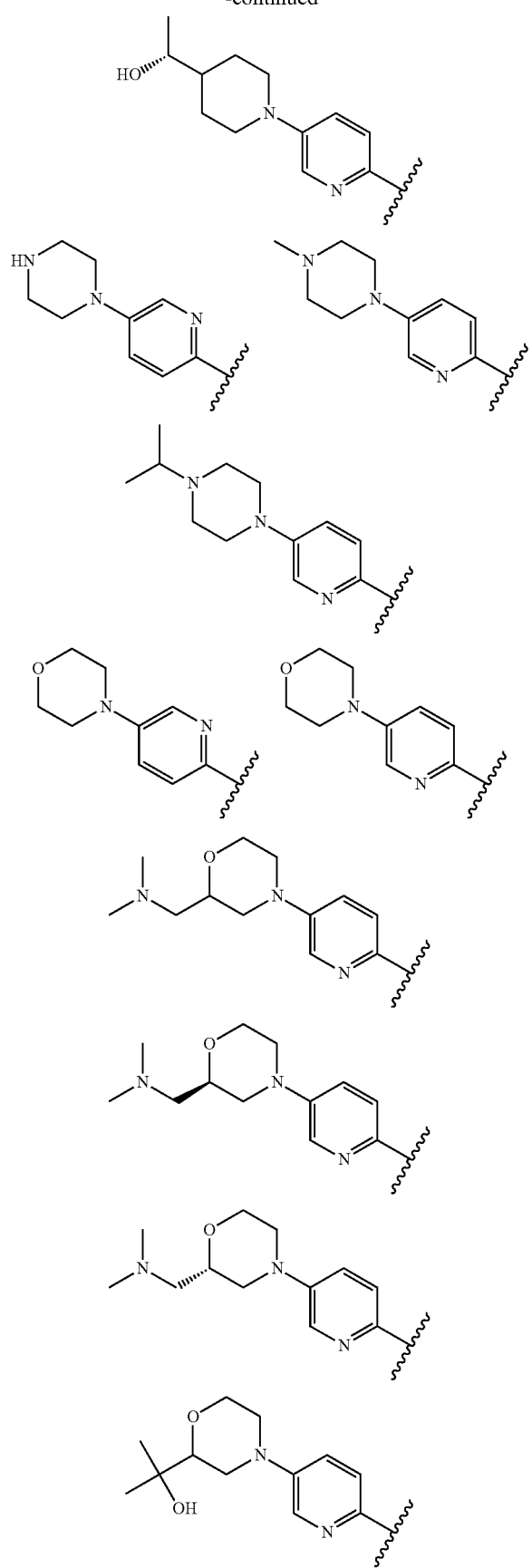
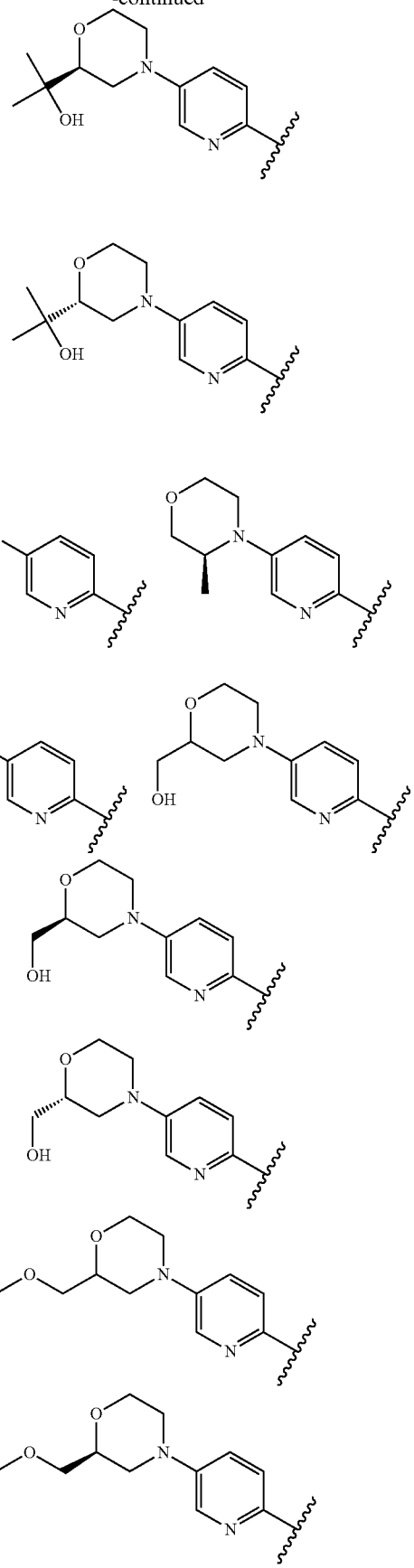

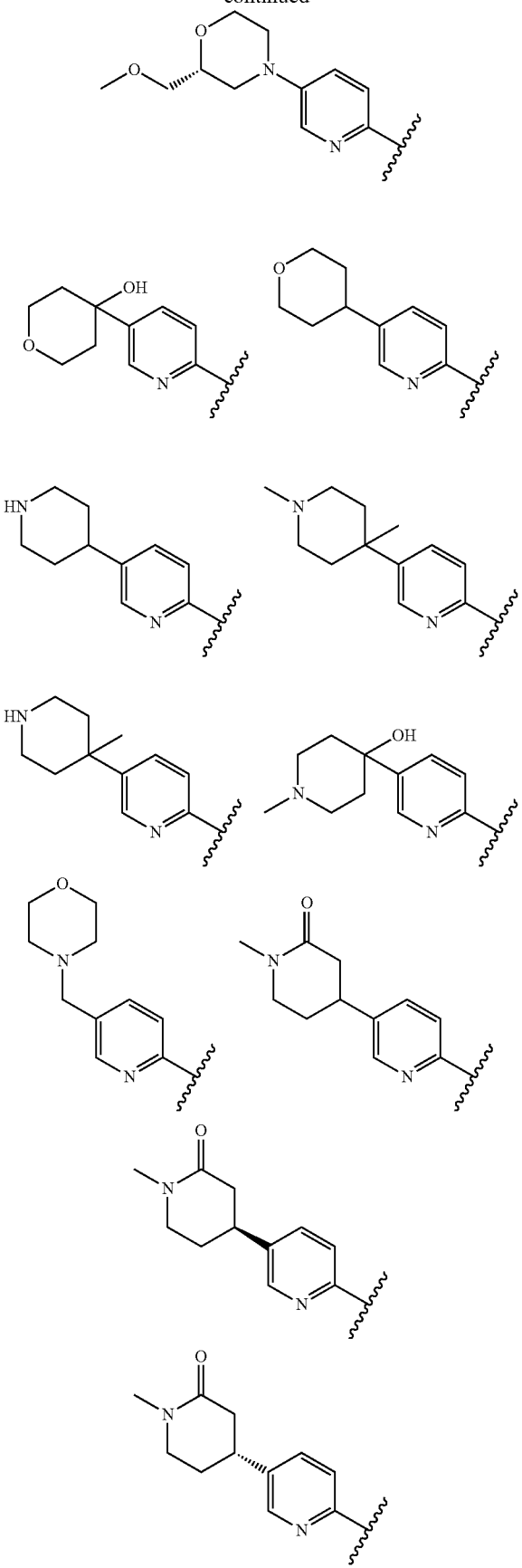
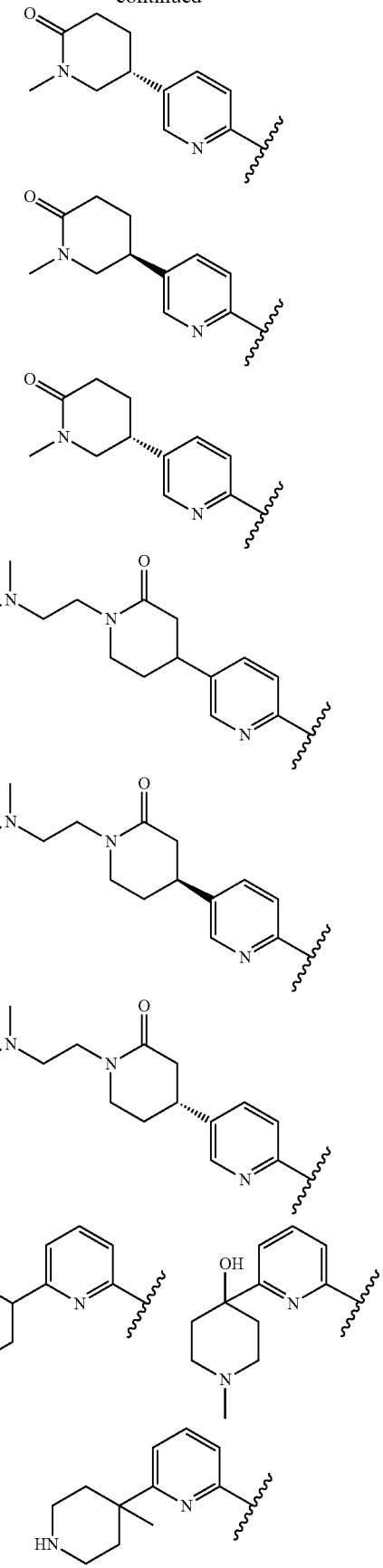

2345
-continued
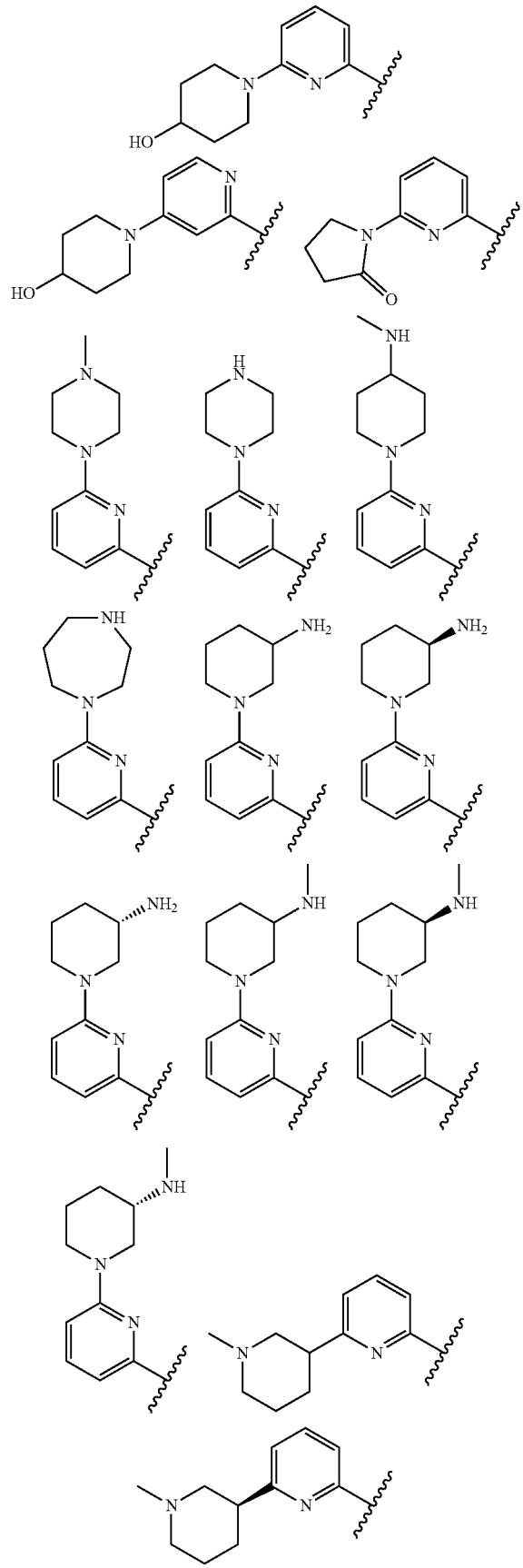
2346
-continued
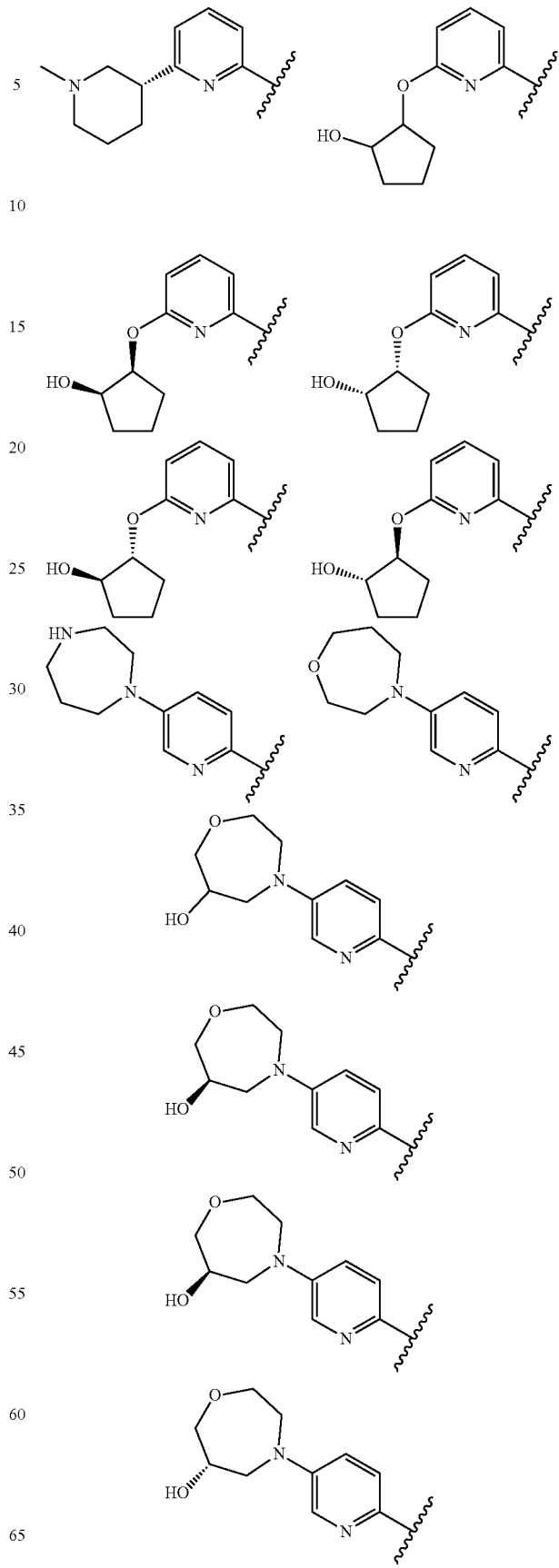

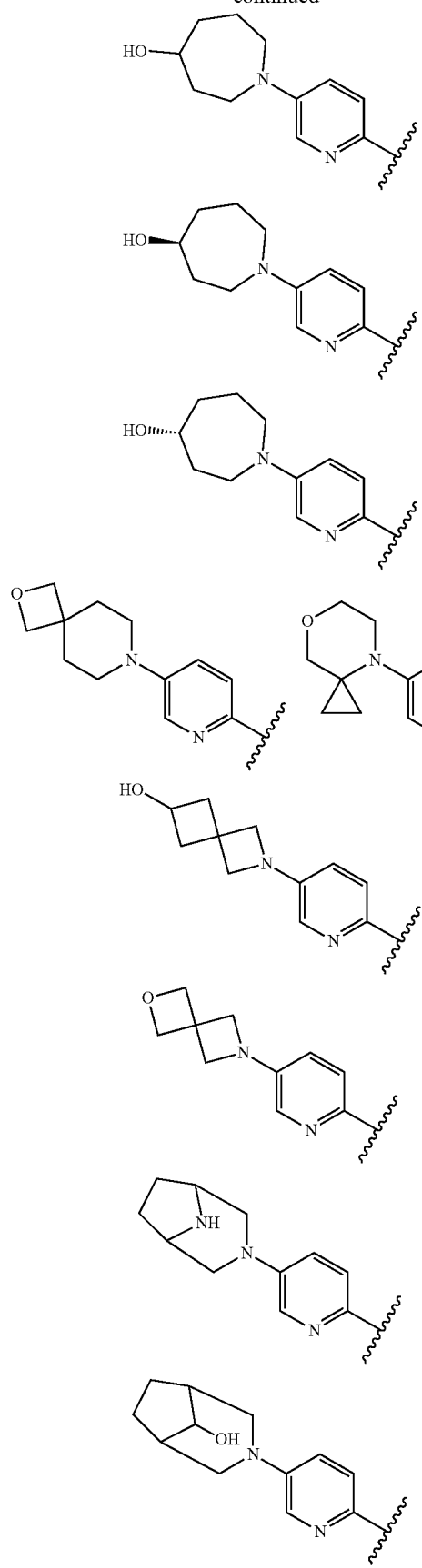
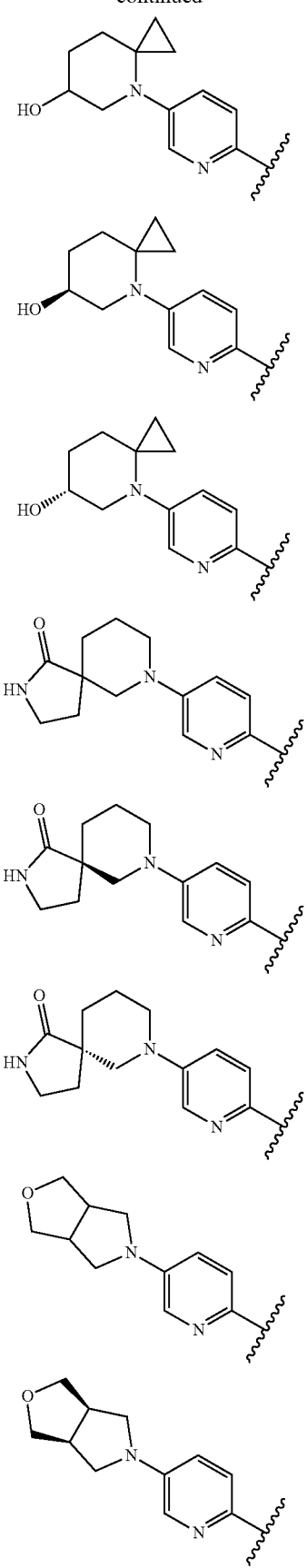

2349
-continued
2350
-continued
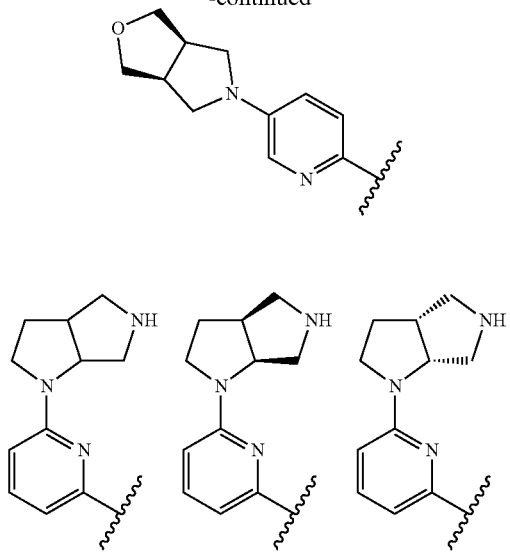
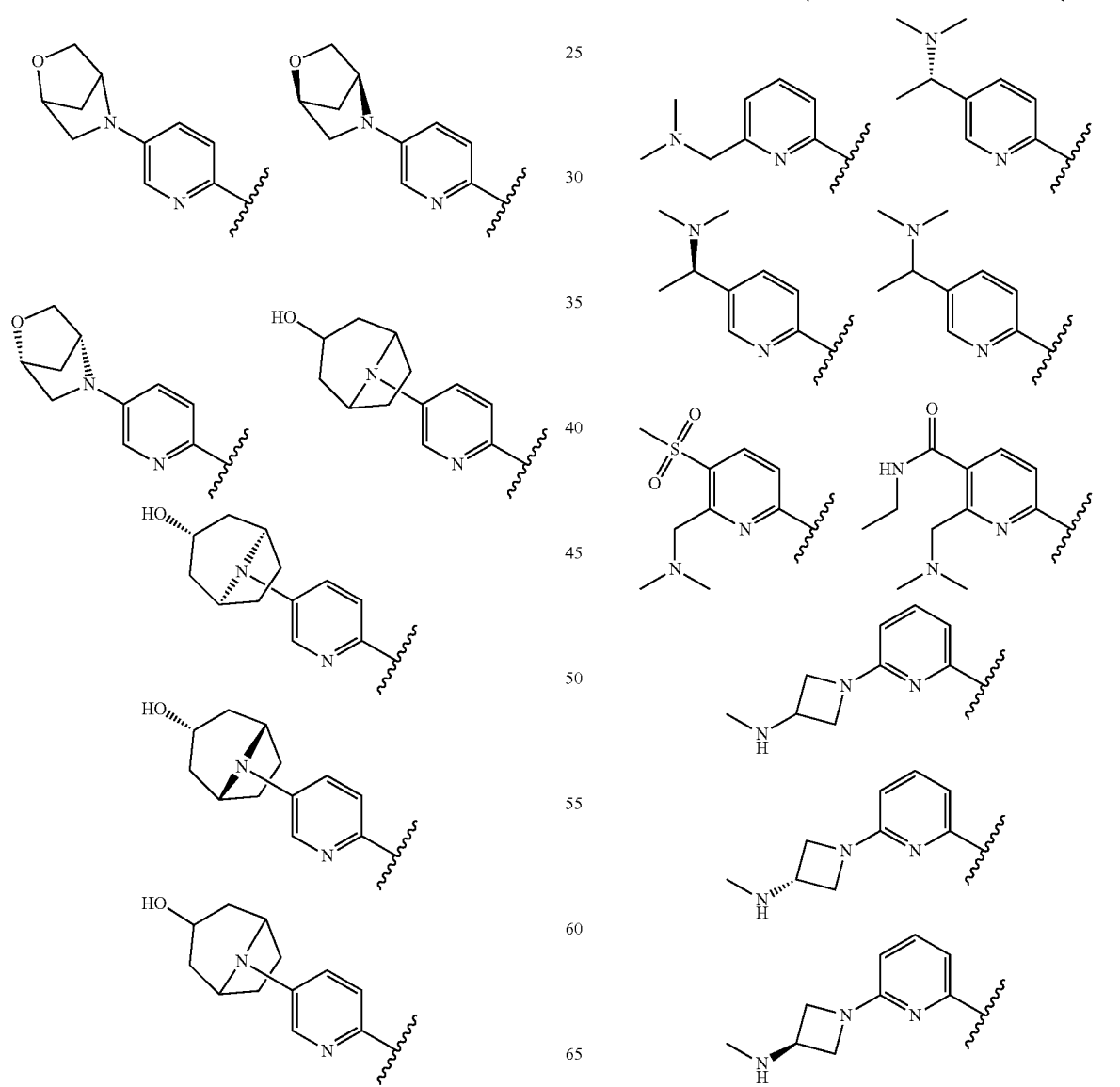

2351
-continued
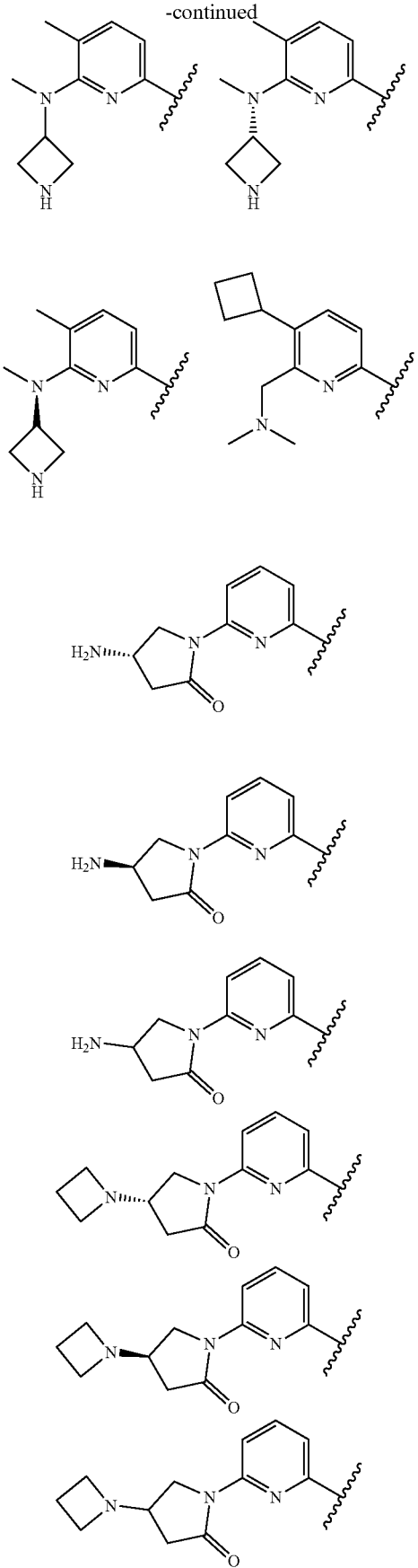
2352
-continued
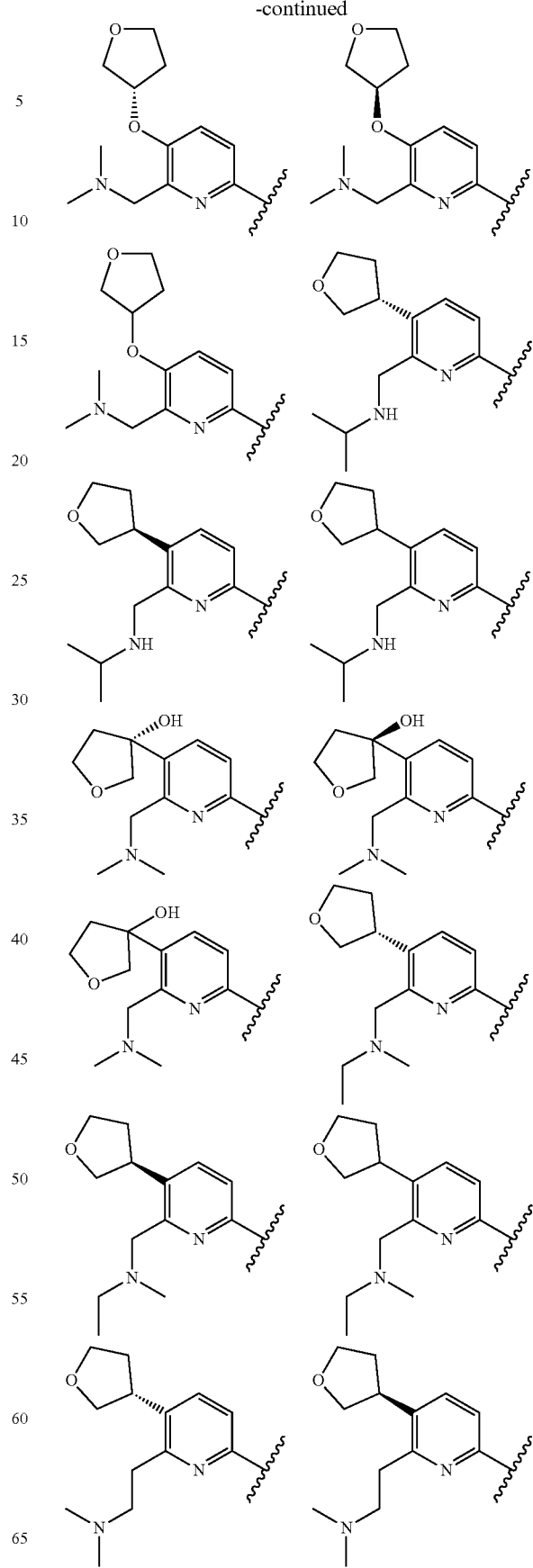

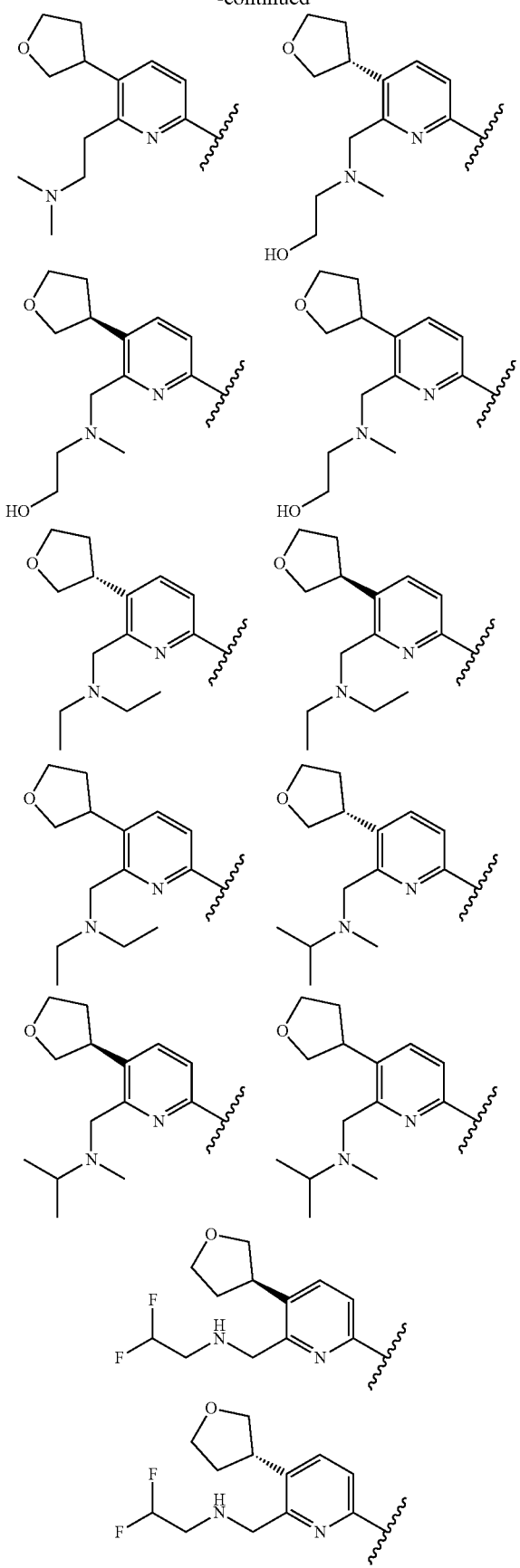
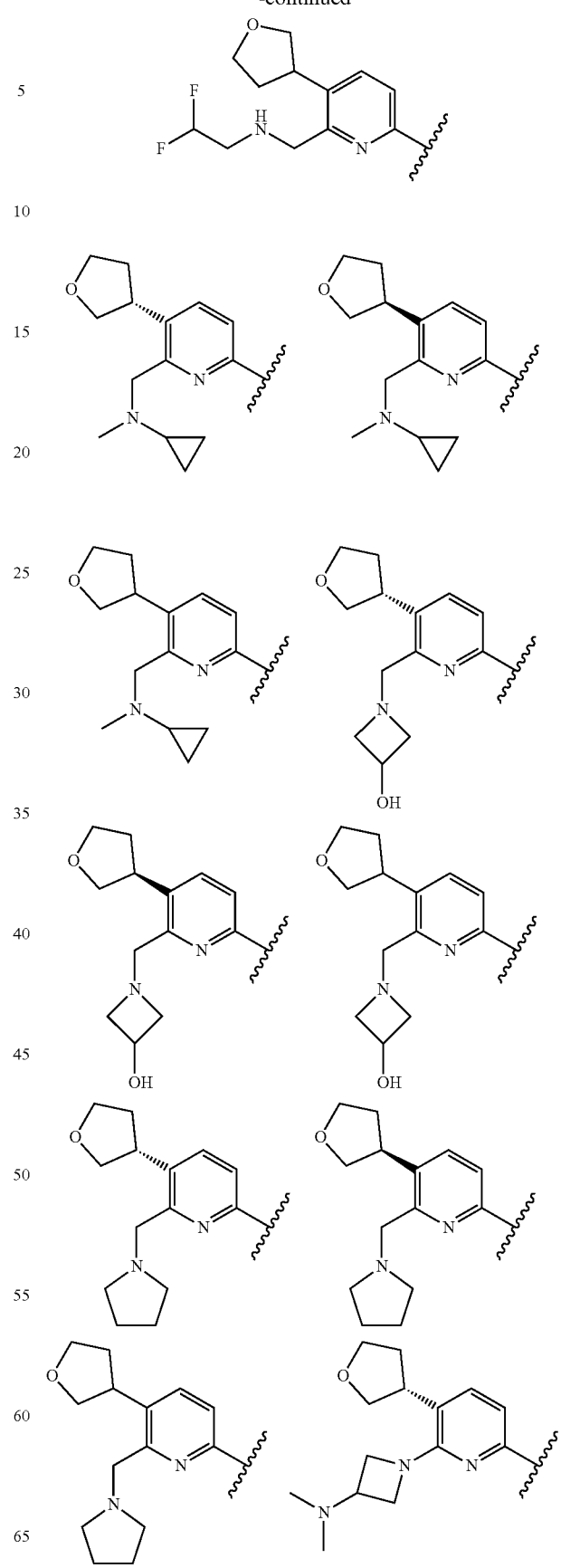

2355
-continued
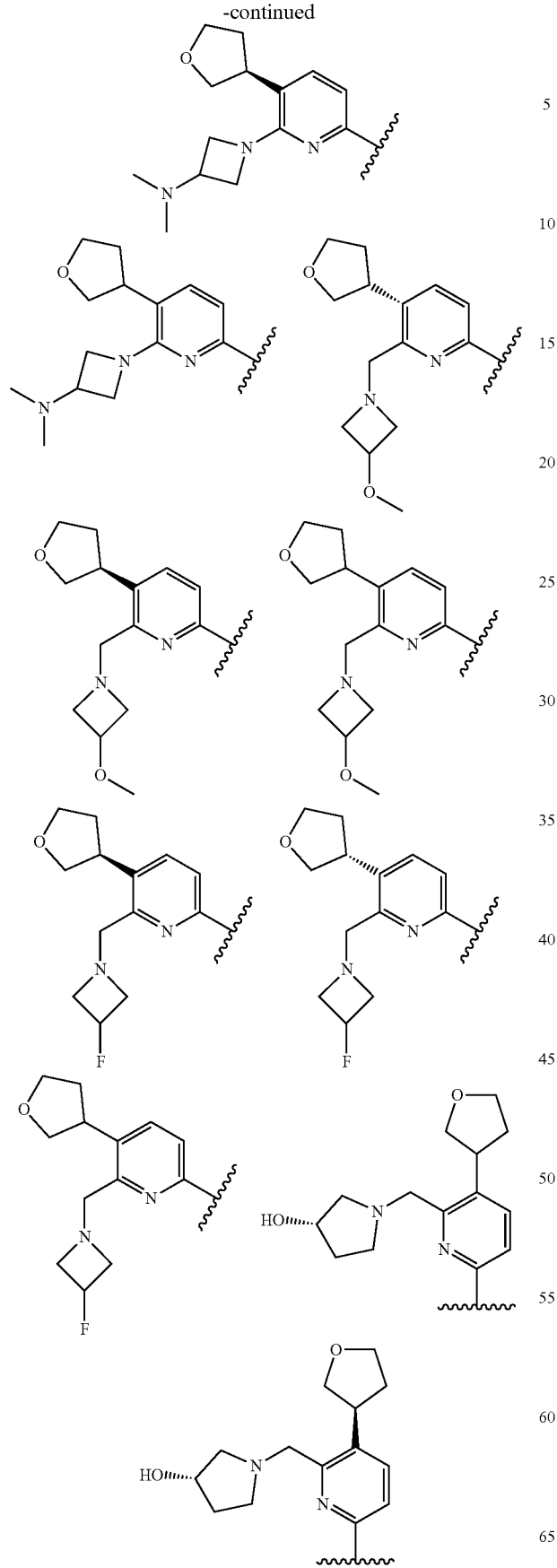
2356
-continued
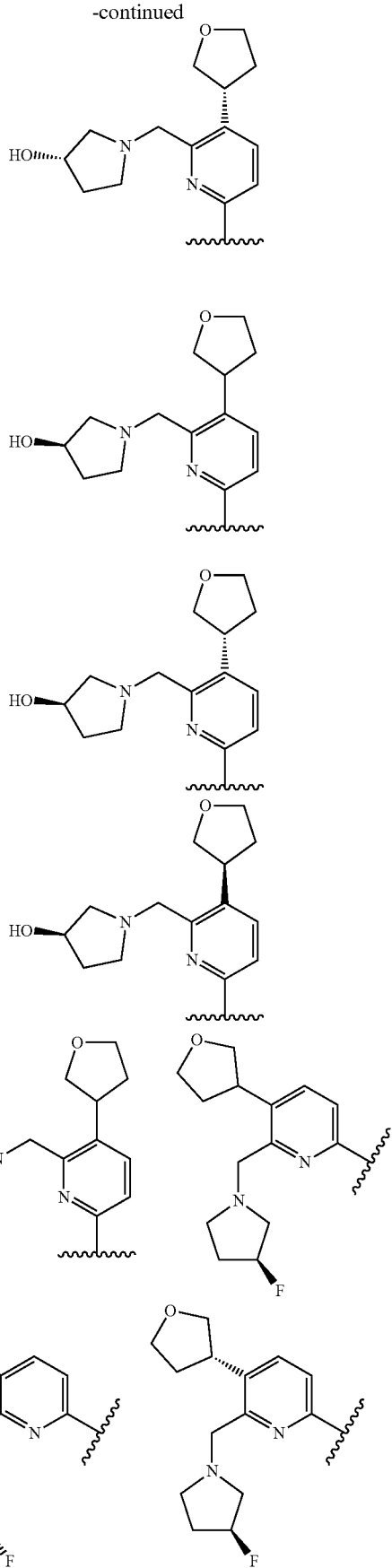

2357
-continued
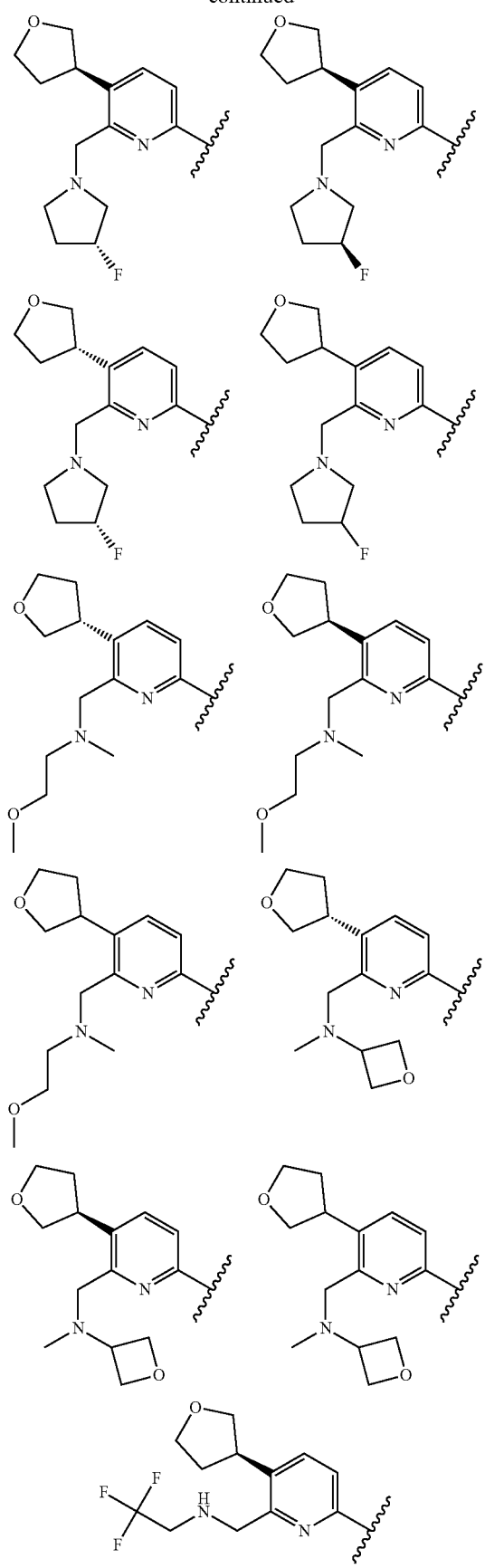
2358
-continued
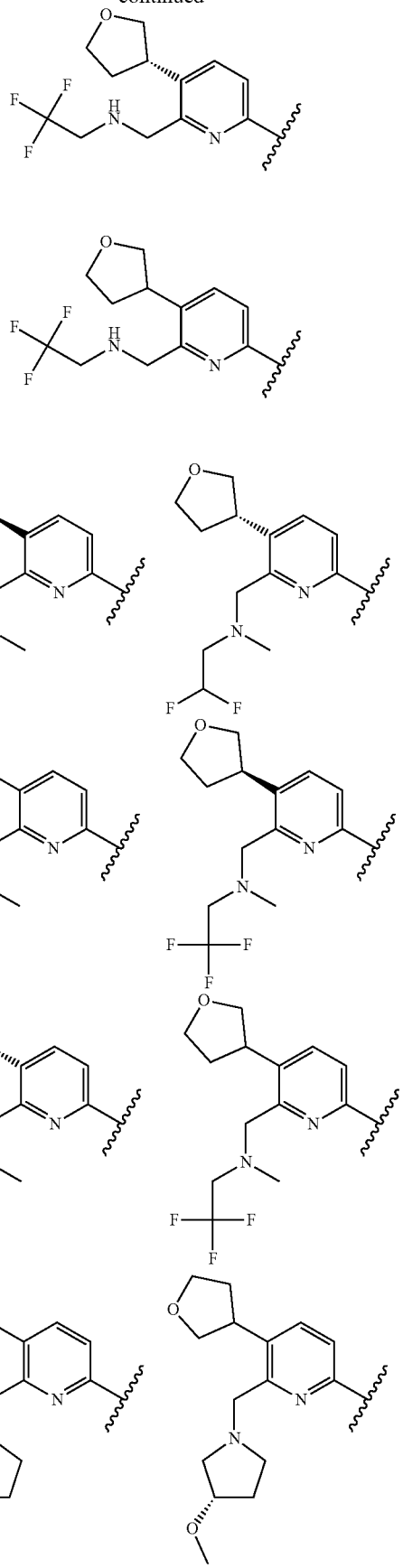

2359
-continued
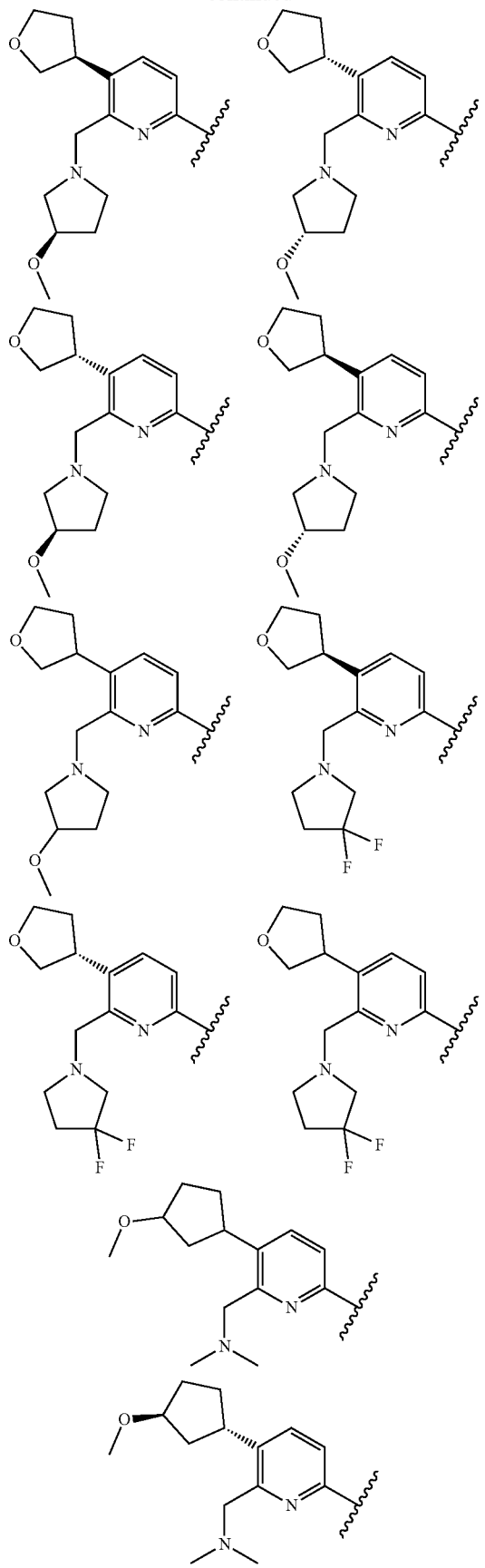
2360
-continued
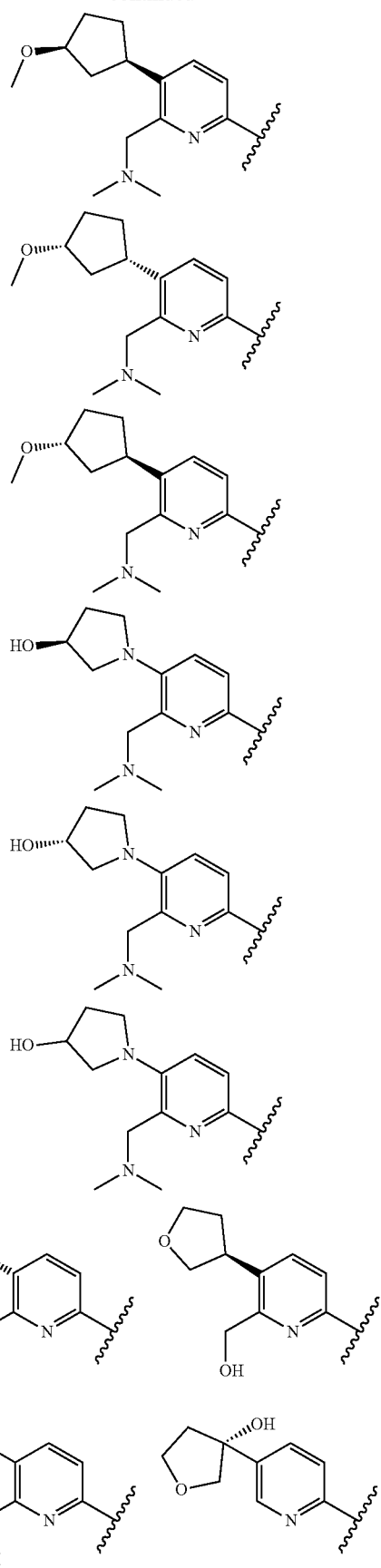

2361
-continued
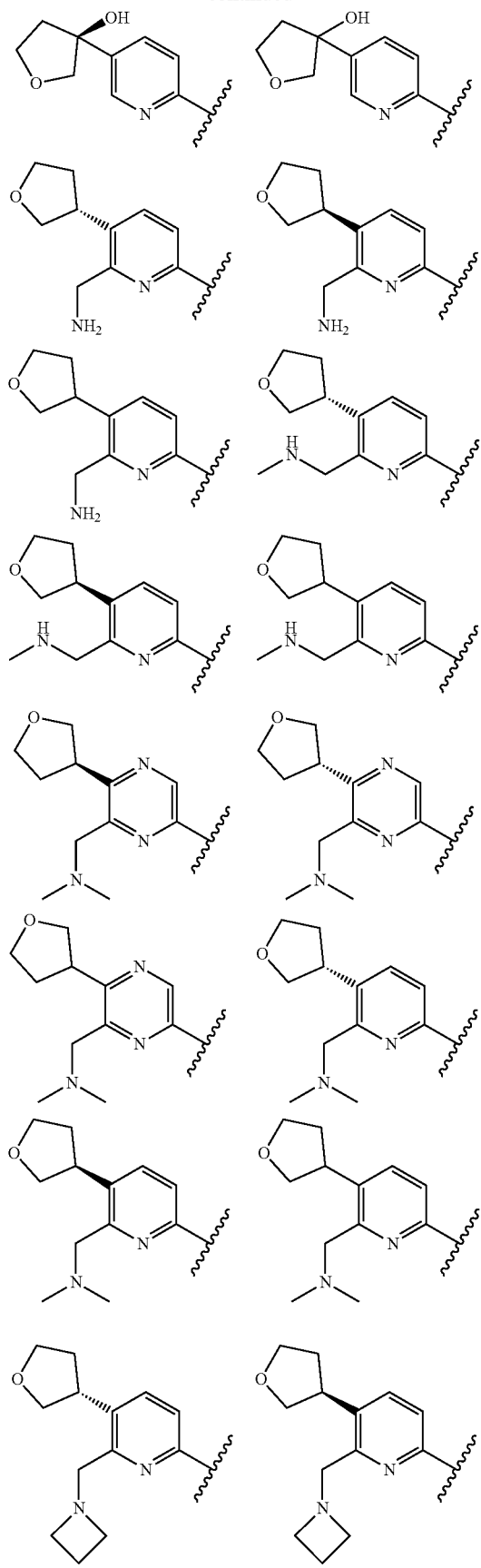
2362
-continued
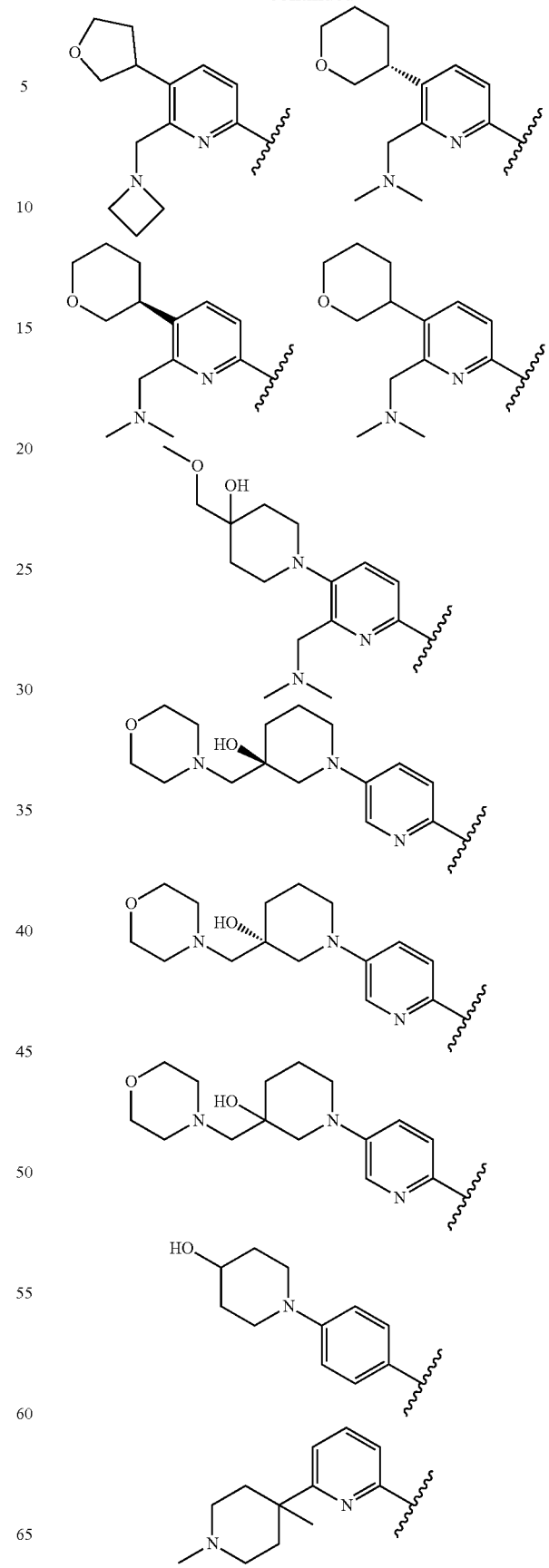

2363
-continued
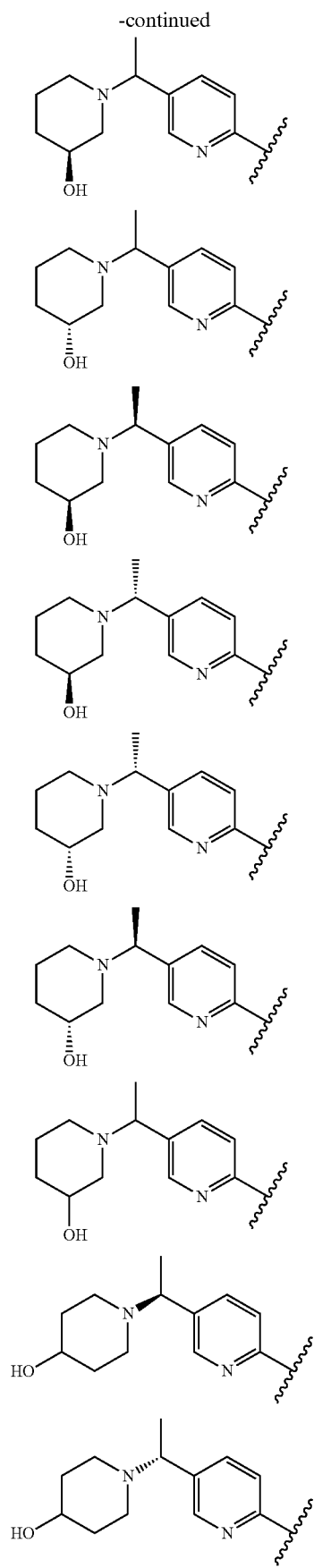
2364
-continued
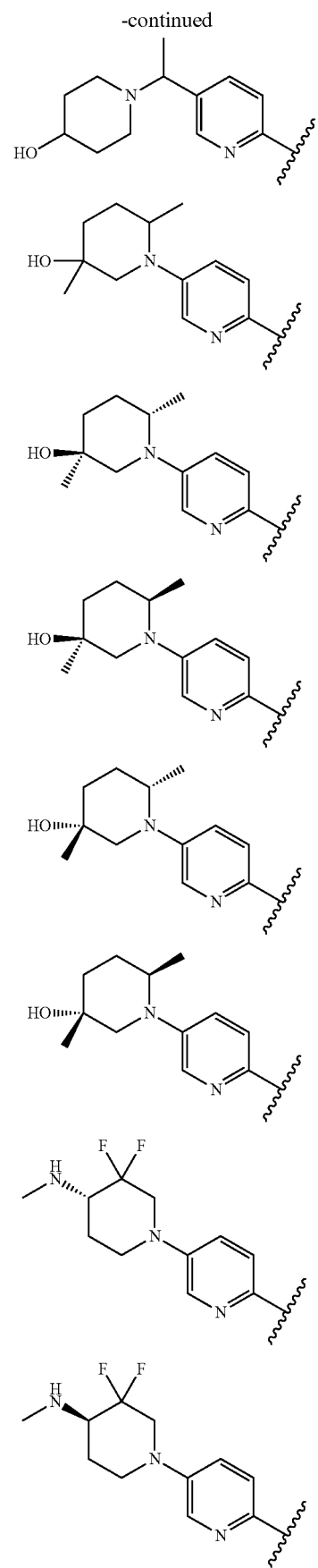

2365
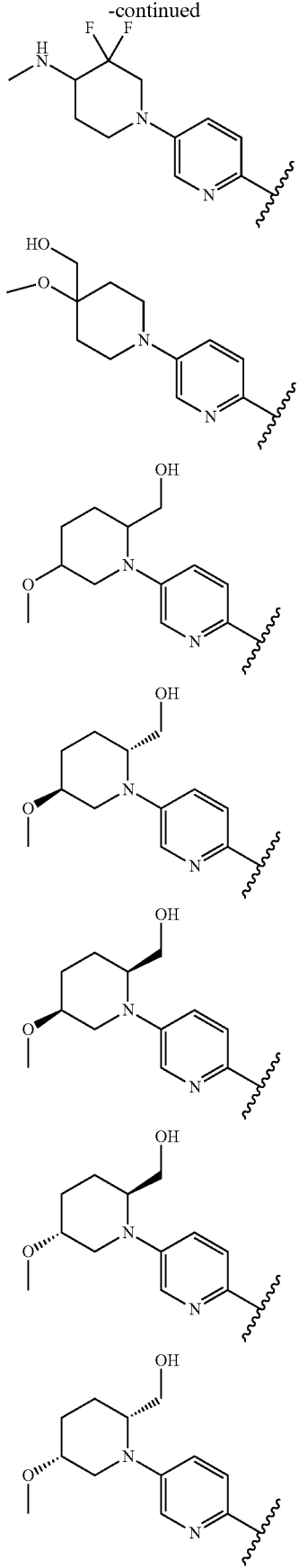
2366
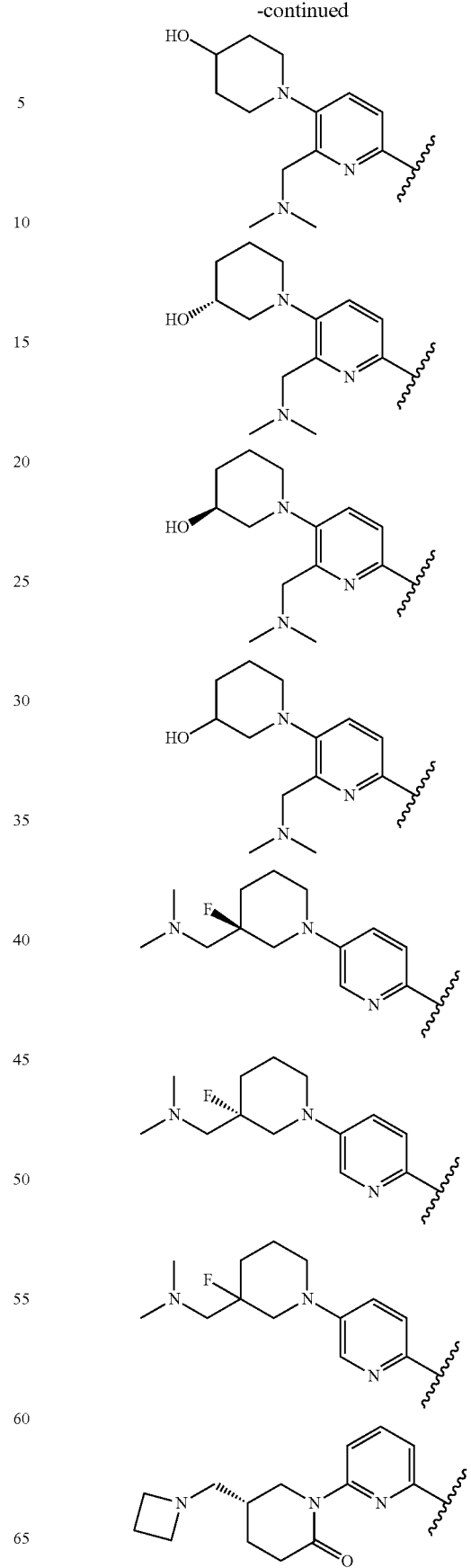

-continued

2369
-continued
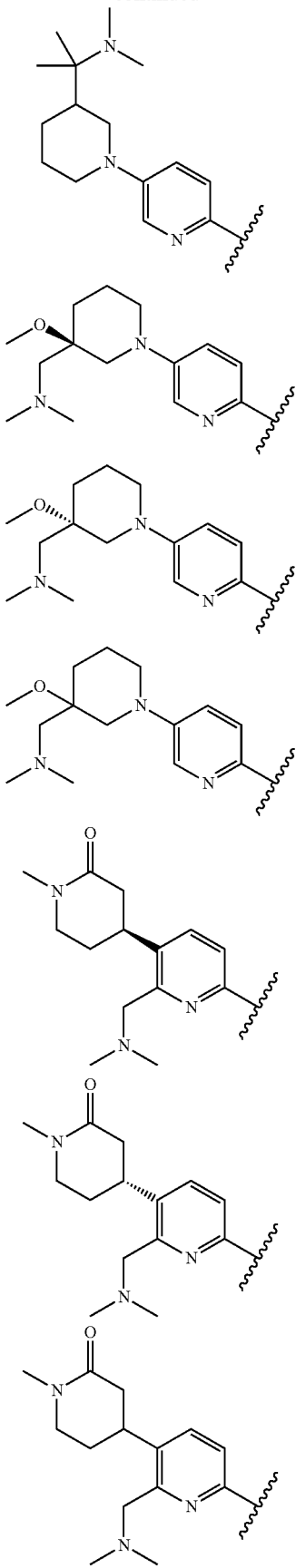
2370
-continued
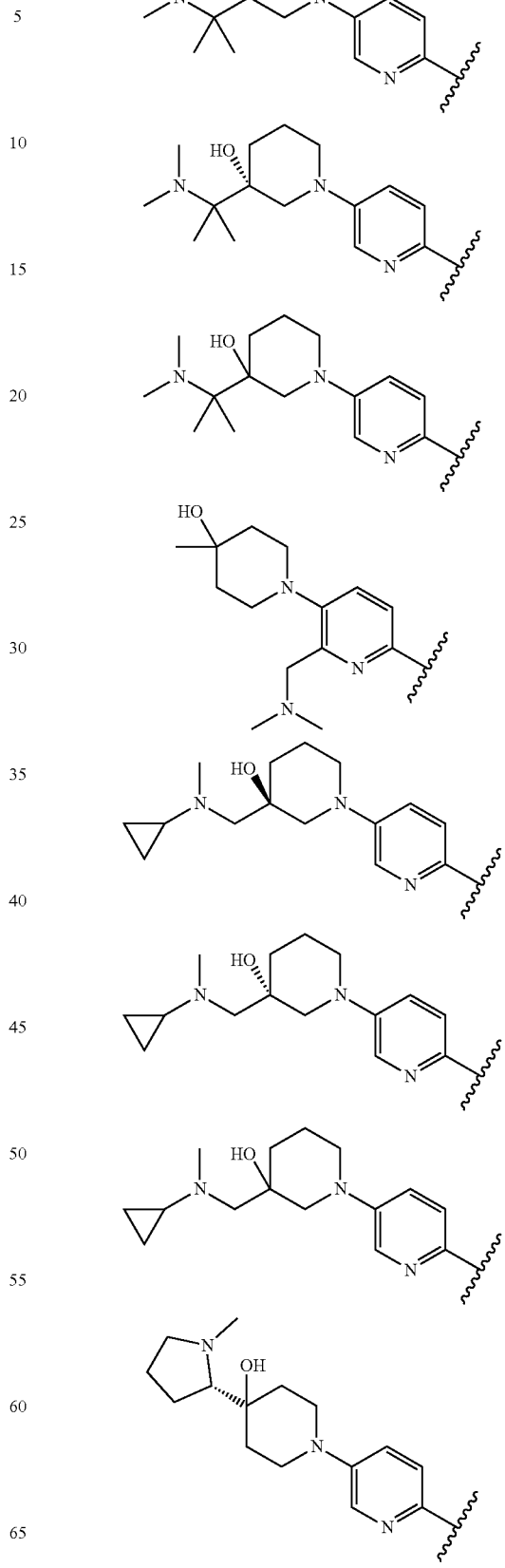

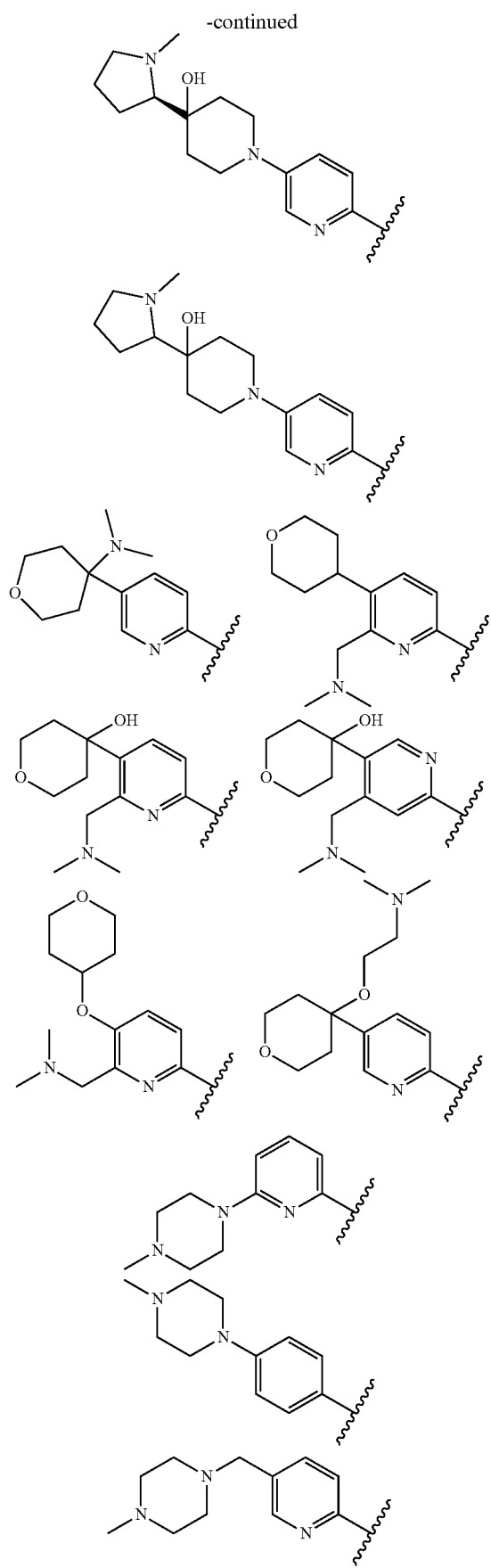
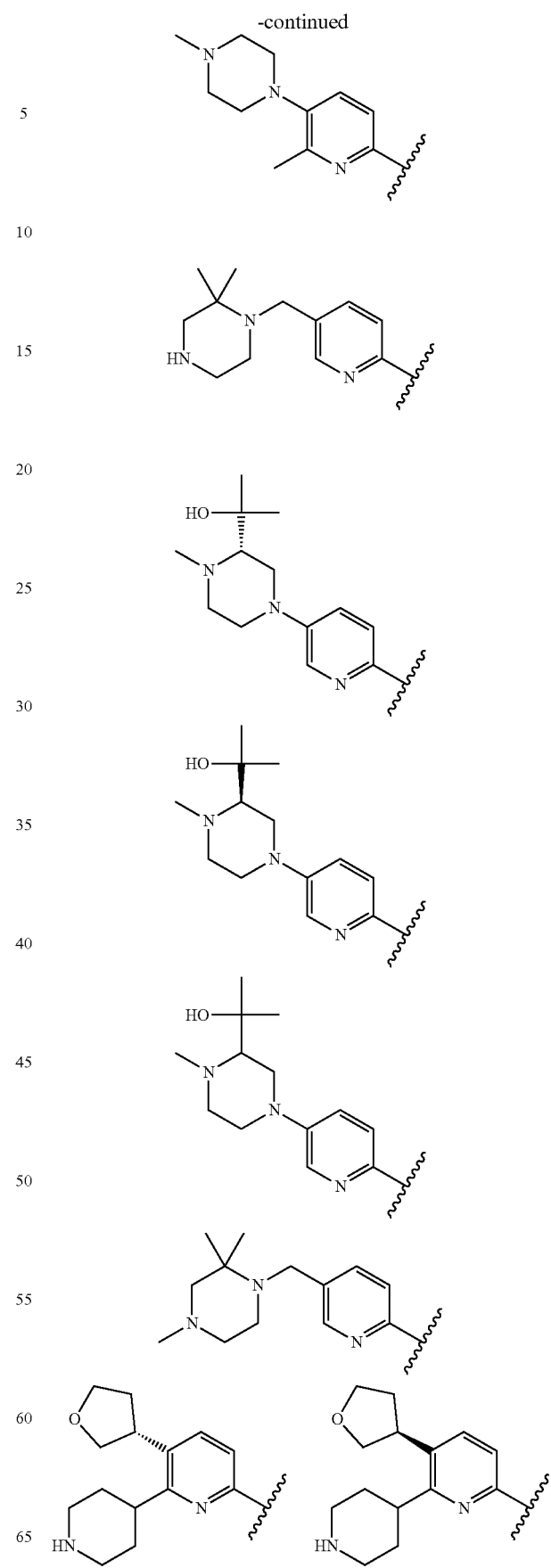

2373
-continued
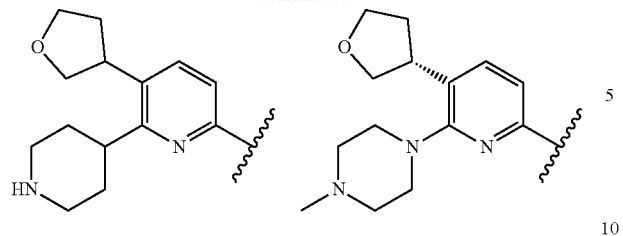
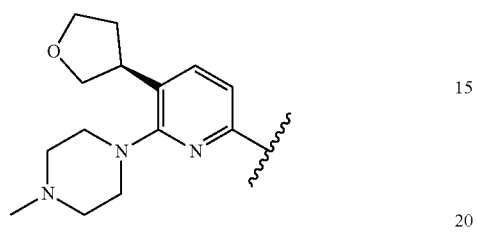
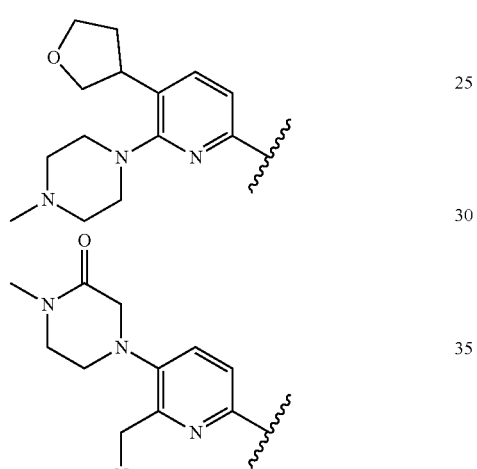
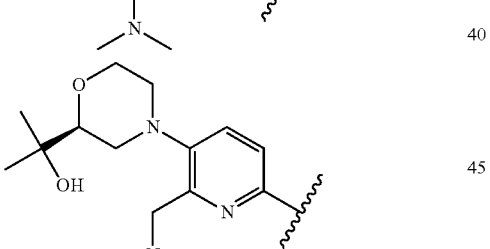
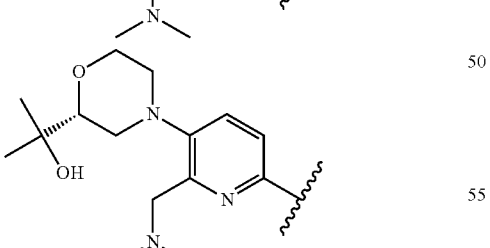
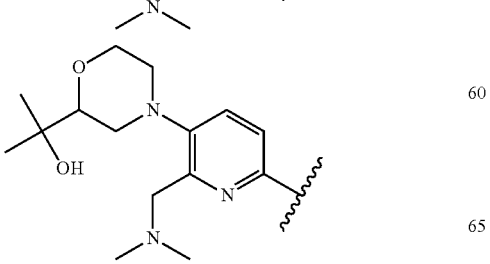
2374
-continued
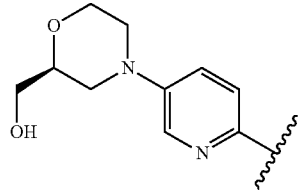
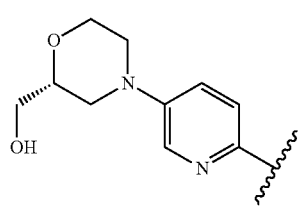
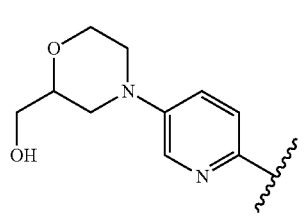
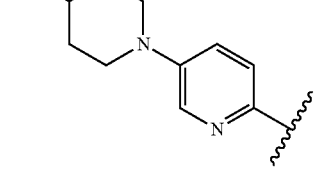
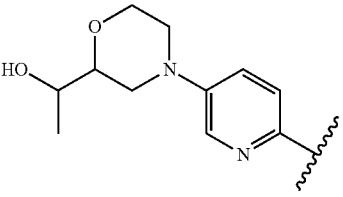
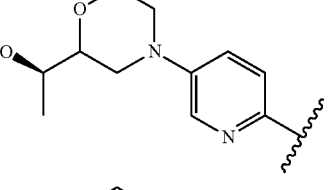
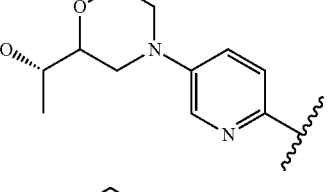
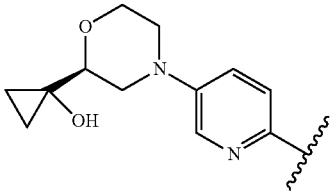

2375
-continued
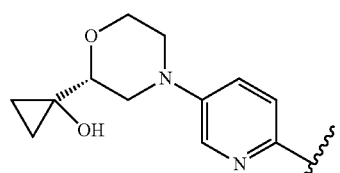
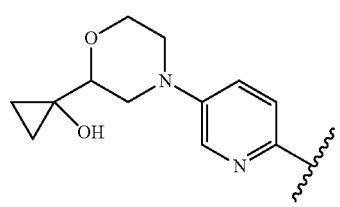
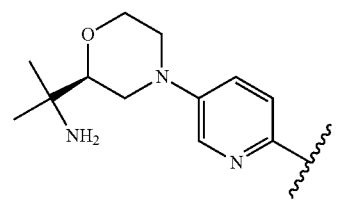
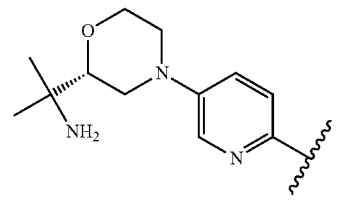
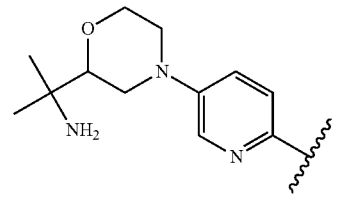
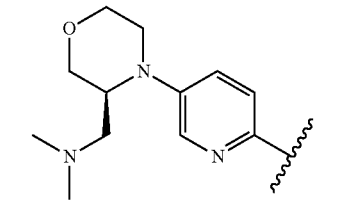
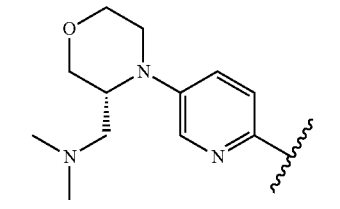
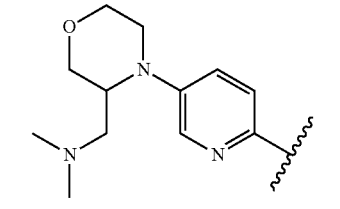
2376
-continued
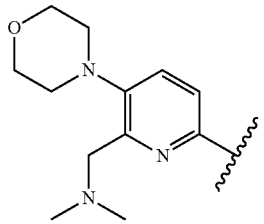
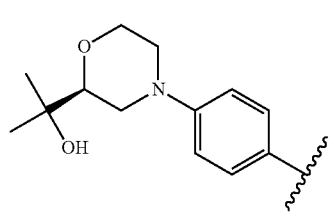
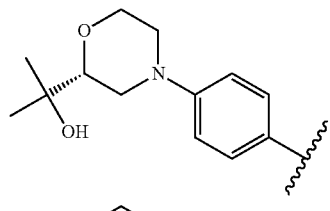
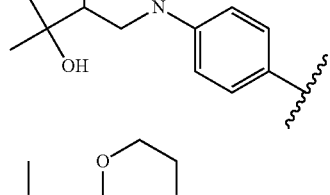
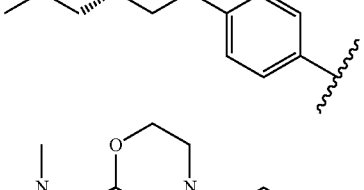
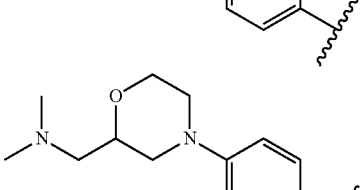
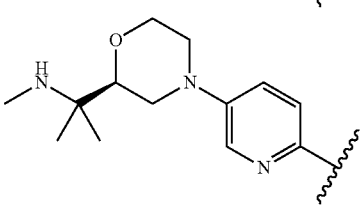

2377 2378
-continued -continued
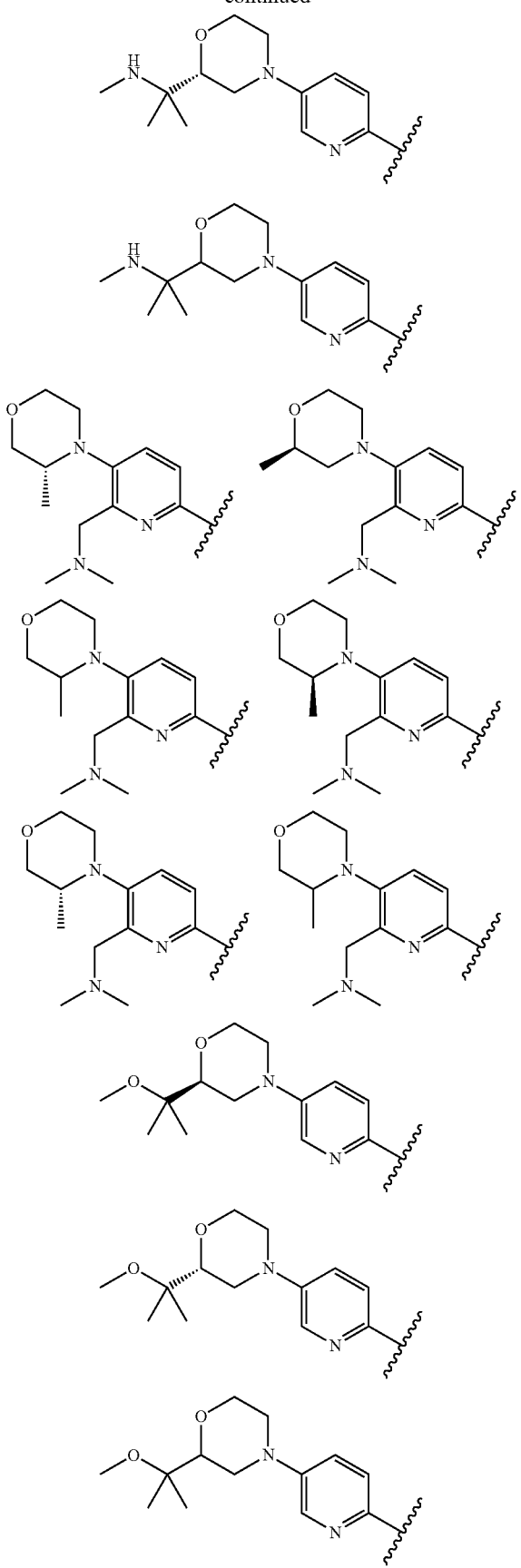
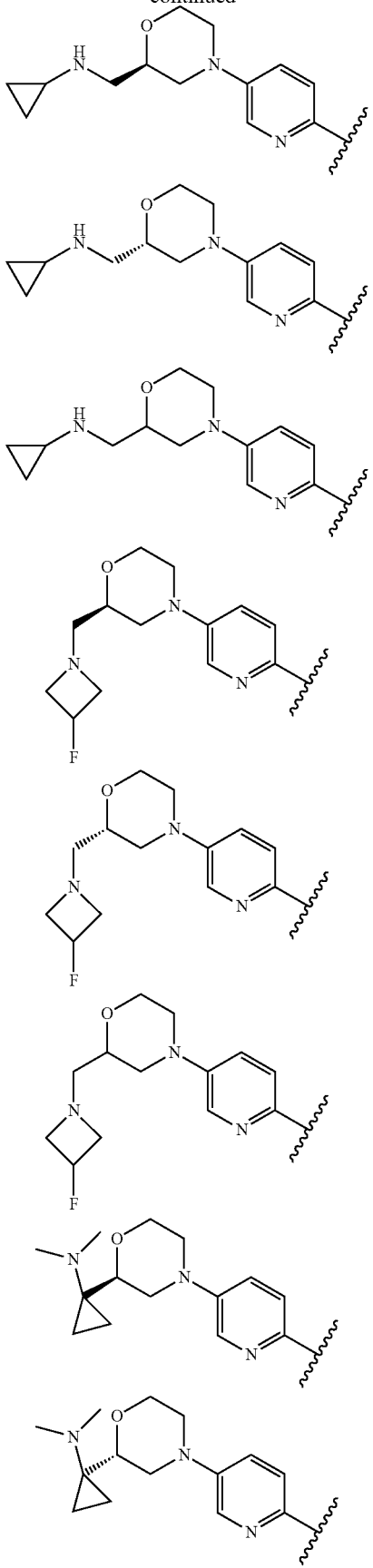

2379
-continued
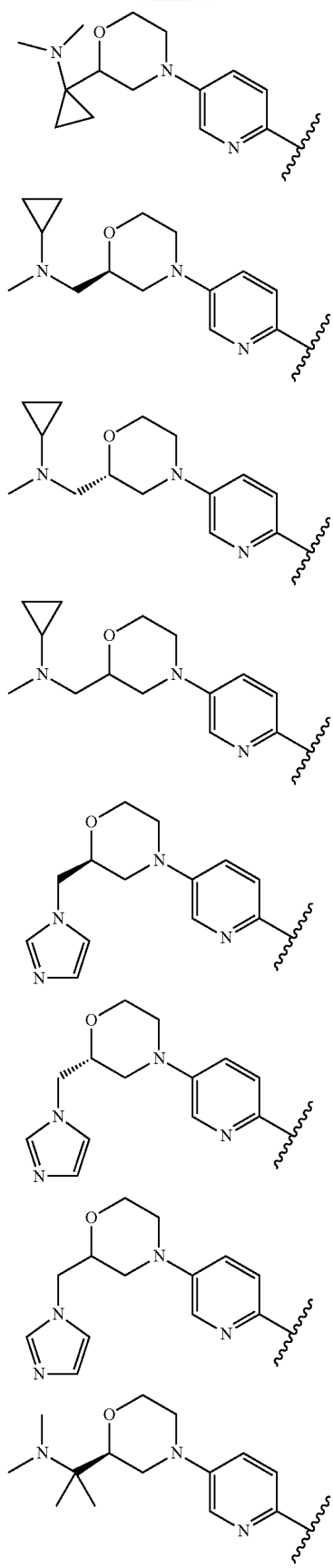
2380
-continued
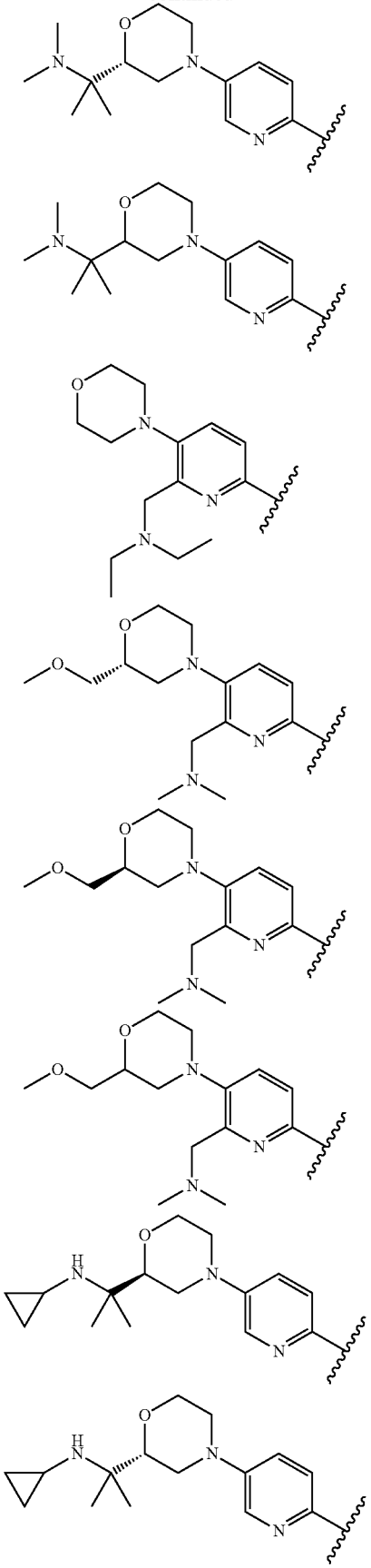

2381
-continued
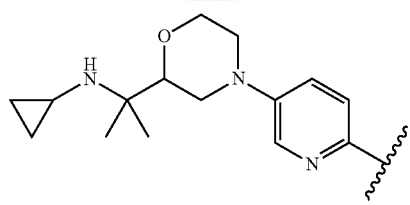
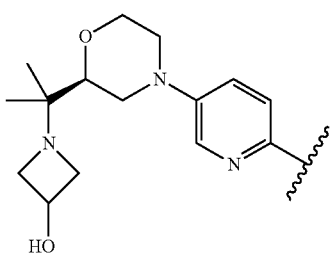
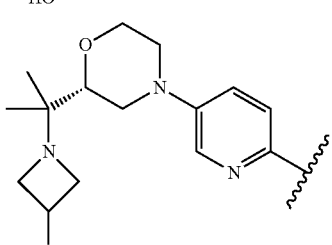
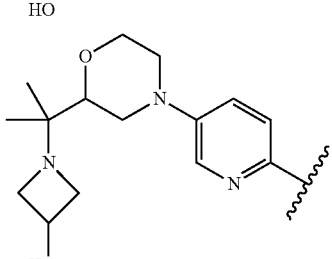
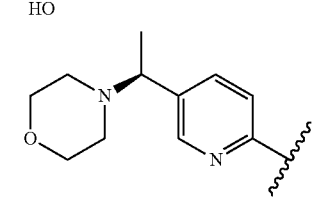
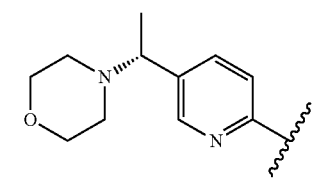
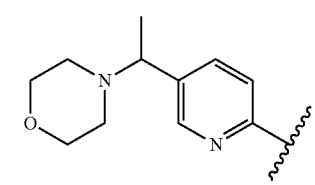
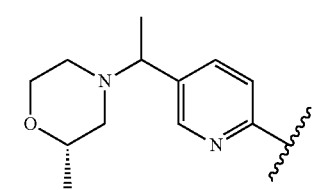
2382
-continued
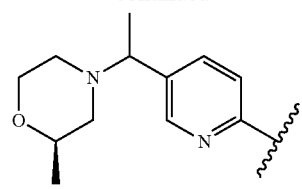
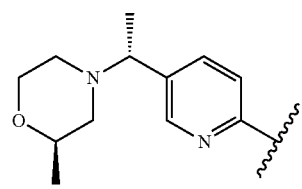
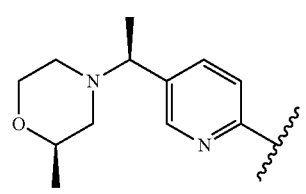
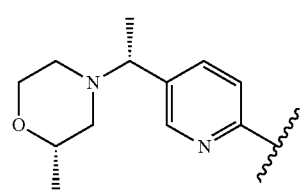
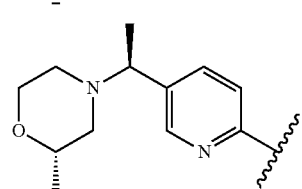
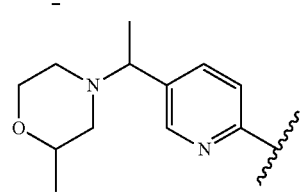
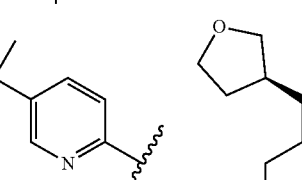
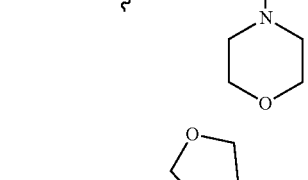
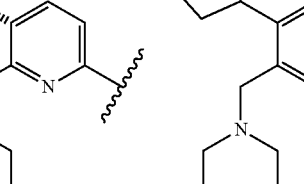

2383
-continued
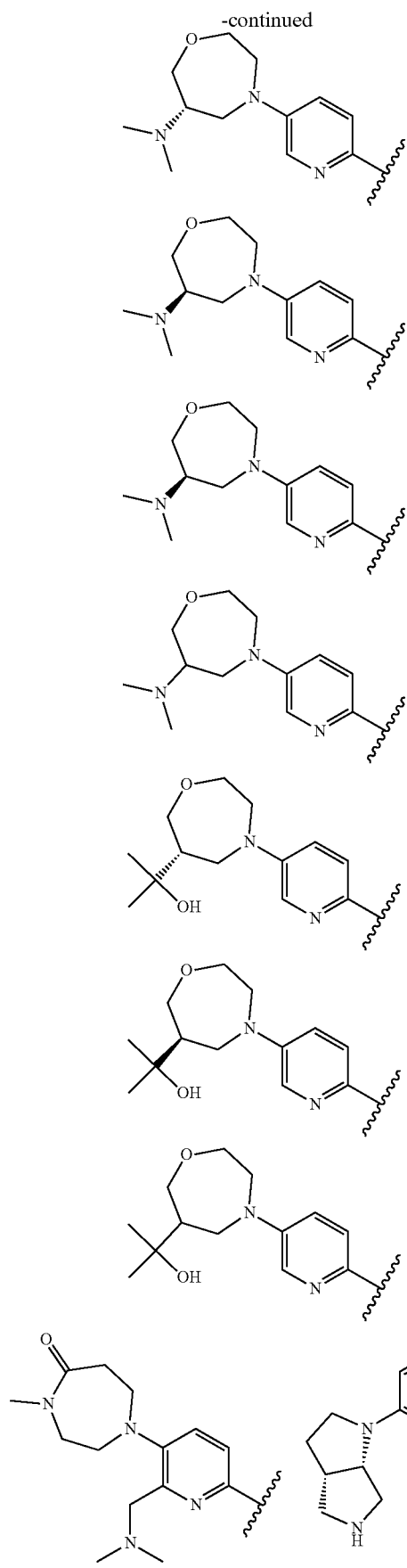
2384
-continued
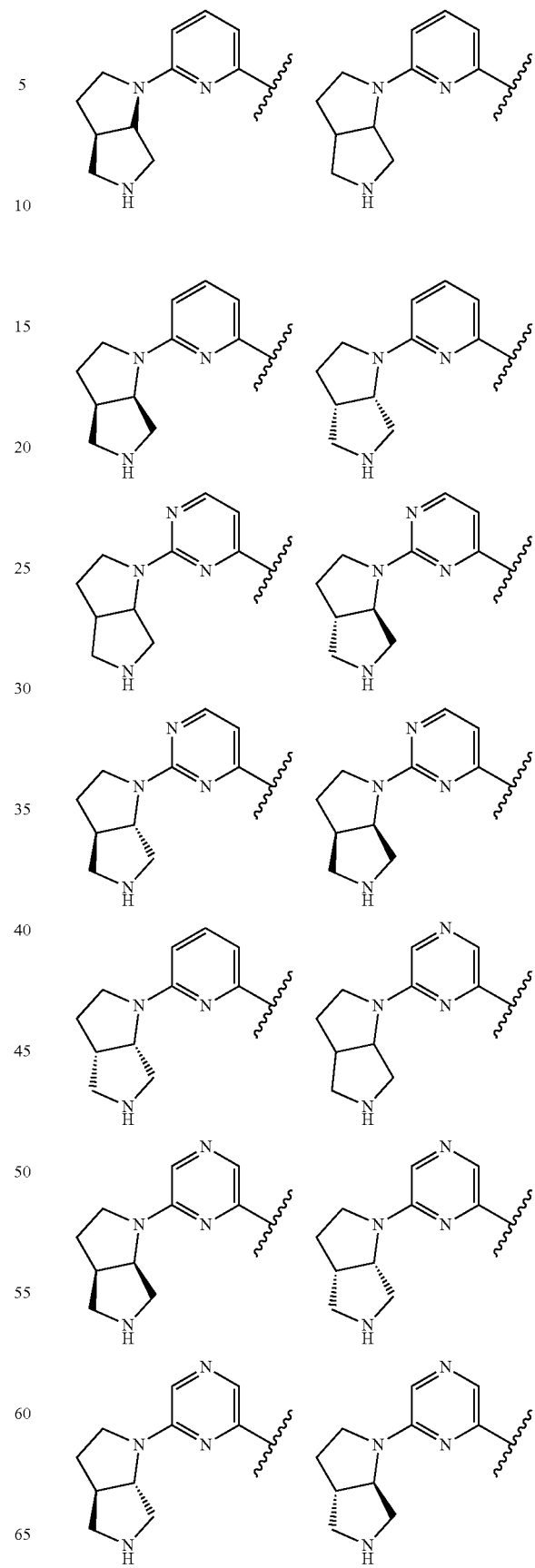

-continued

2387
-continued
2388
-continued
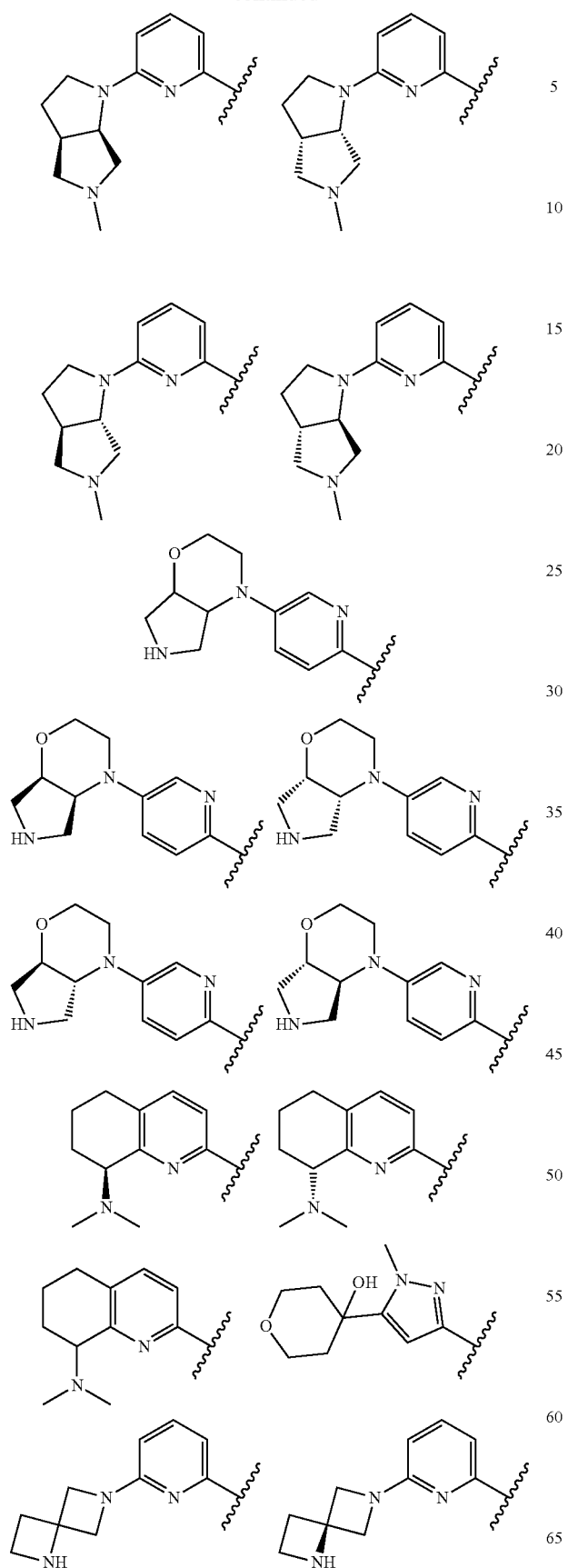
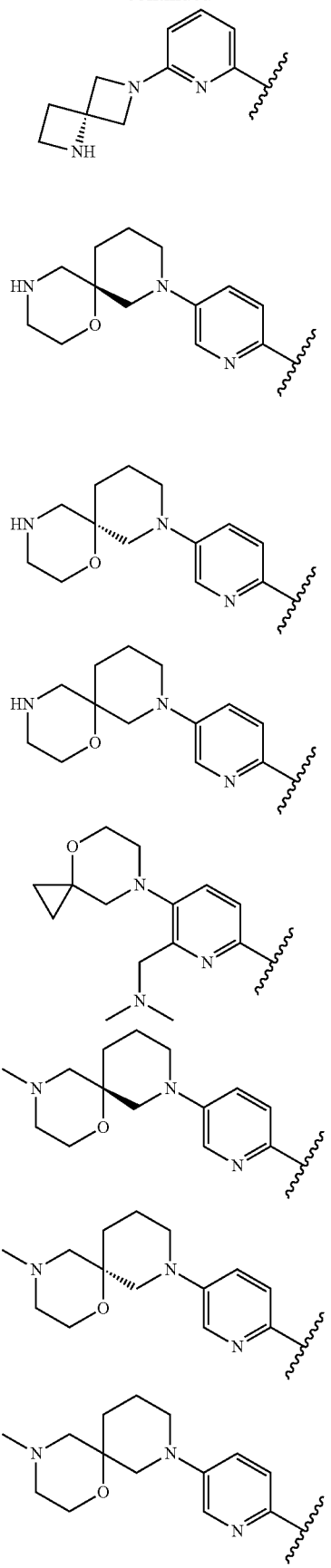

2389
-continued
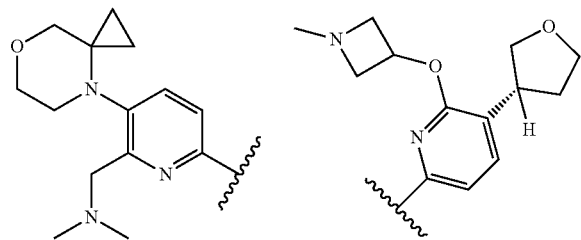
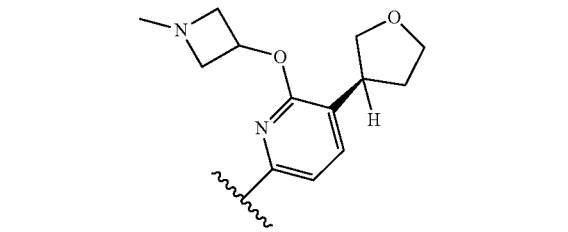
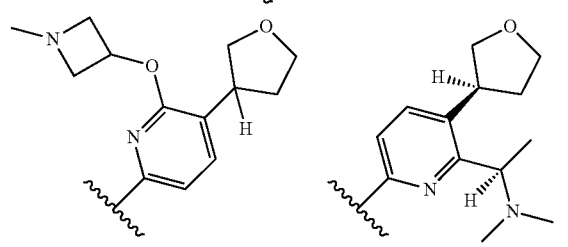

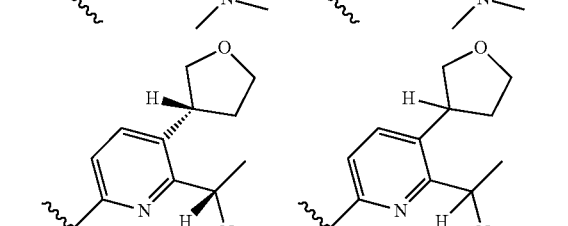
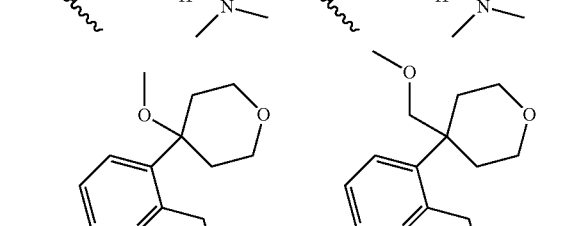
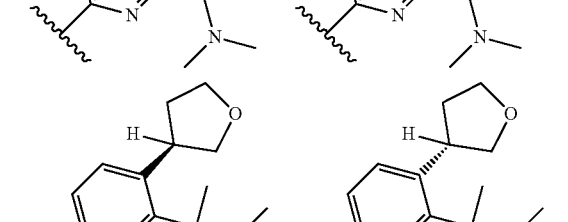
2390
-continued
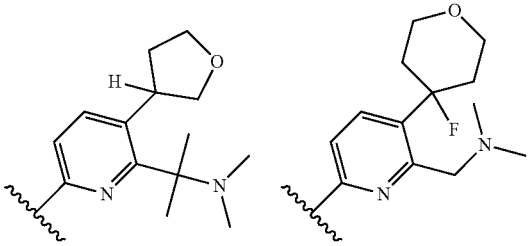
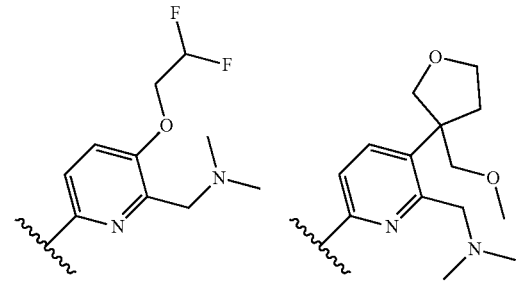
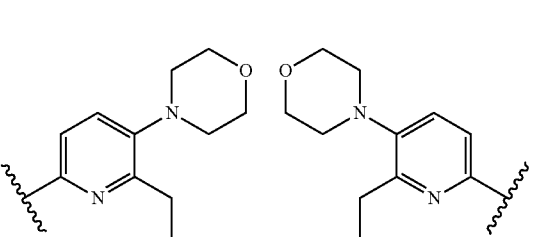
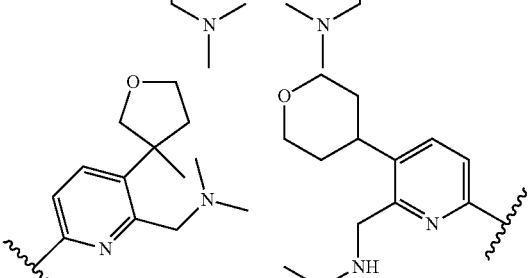
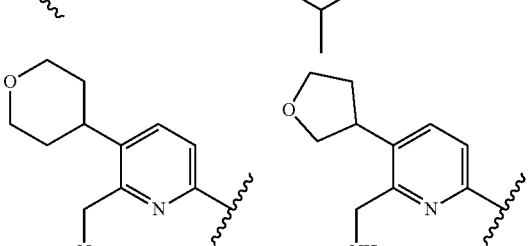
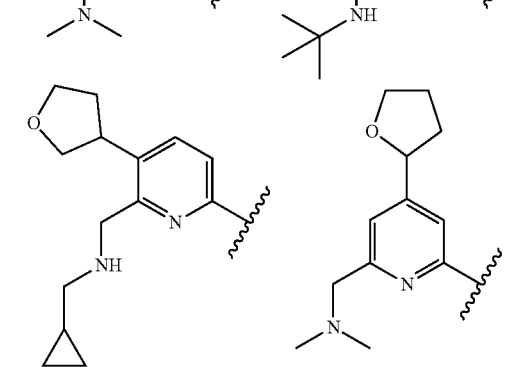

2391
-continued

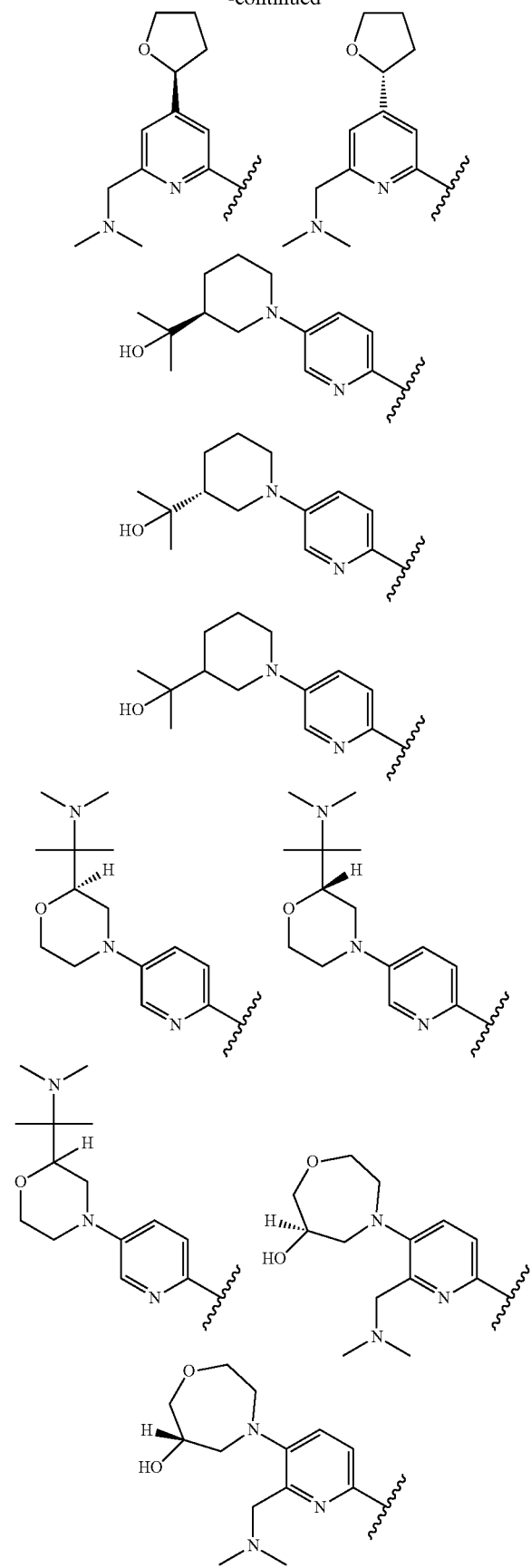

2392
-continued

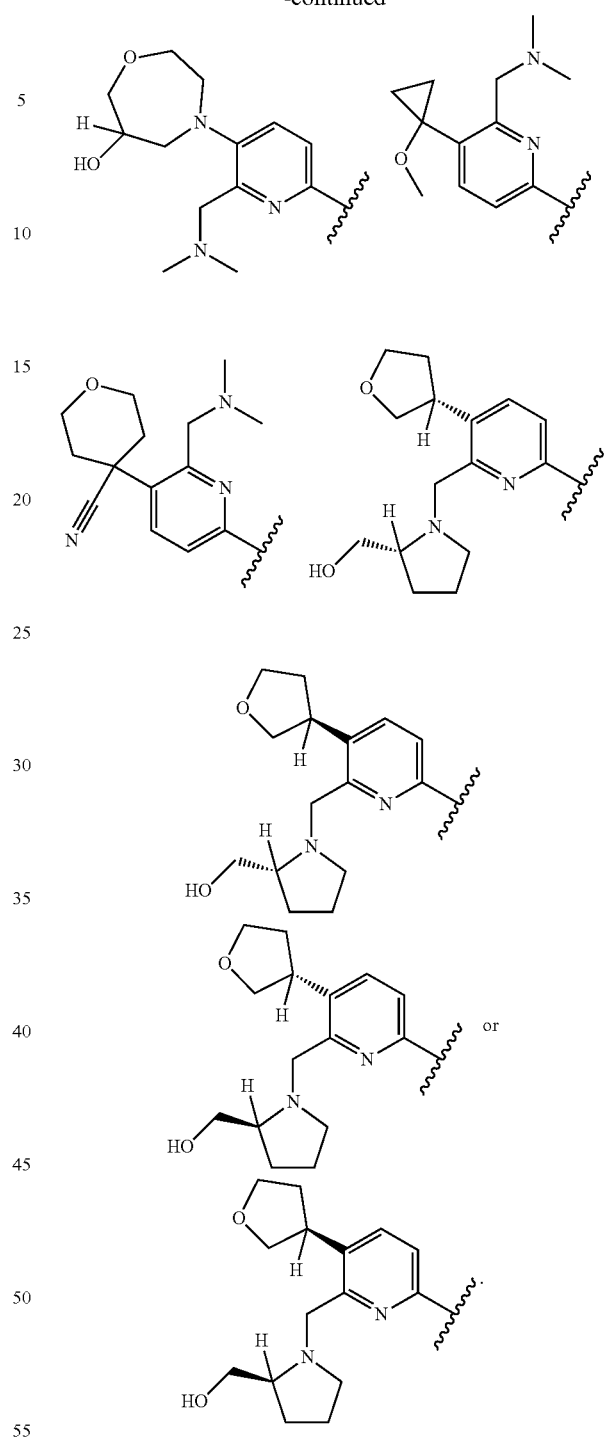

12. The compound of claim 1, wherein $R^2$ is a 6-11 membered saturated, partially unsaturated, or unsaturated fused bicyclic ring having 1-3 heteroatoms independently selected from the group consisting of nitrogen, oxygen, and sulfur; each of which is substituted with q instances of $R^C$; wherein each instance of $R^C$ is independently optionally substituted by r instances of R and s instances of $R^D$.

13. The compound of claim 12, wherein $R^2$ is a 7-10-membered fused bicyclic ring having 1-3 nitrogen atoms; each of which is substituted by q instances of $R^C$.

14. The compound of claim 12, wherein $R^2$ is
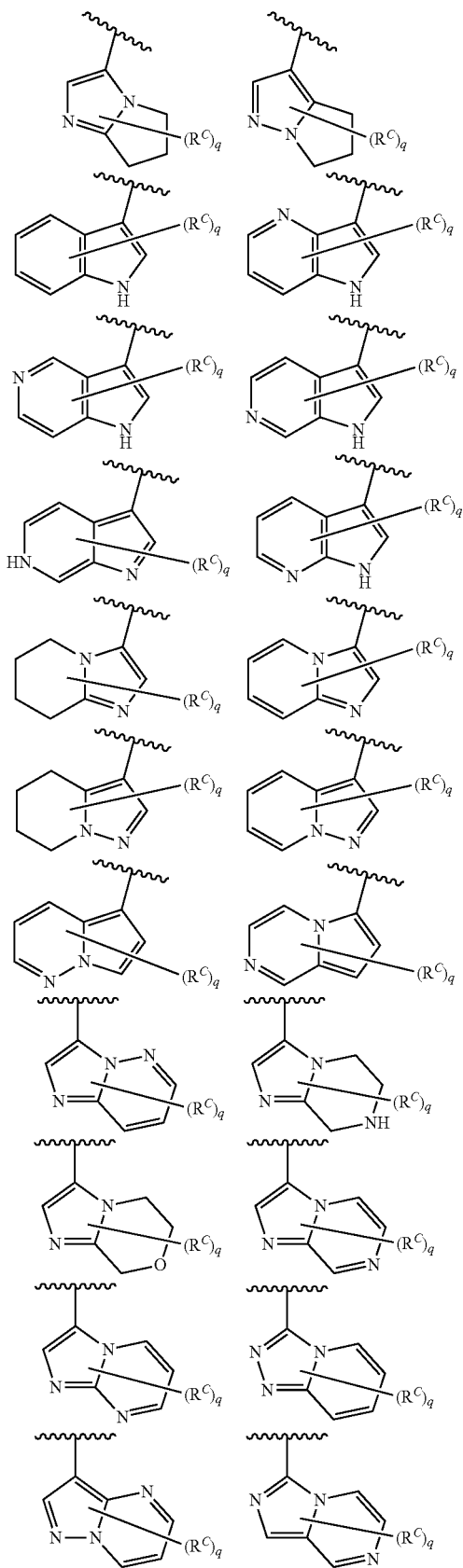
-continued
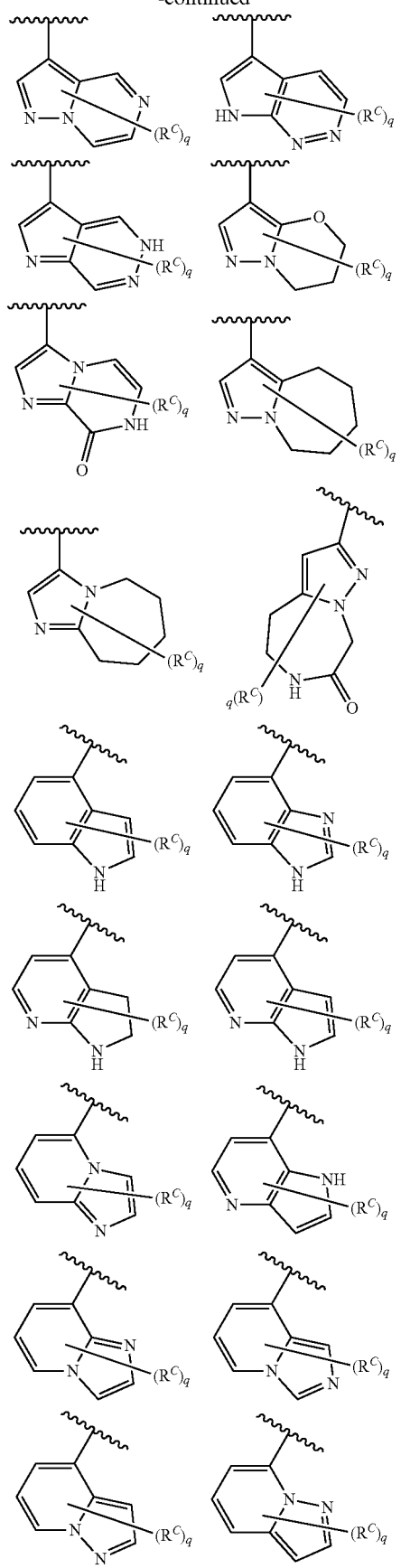

-continued
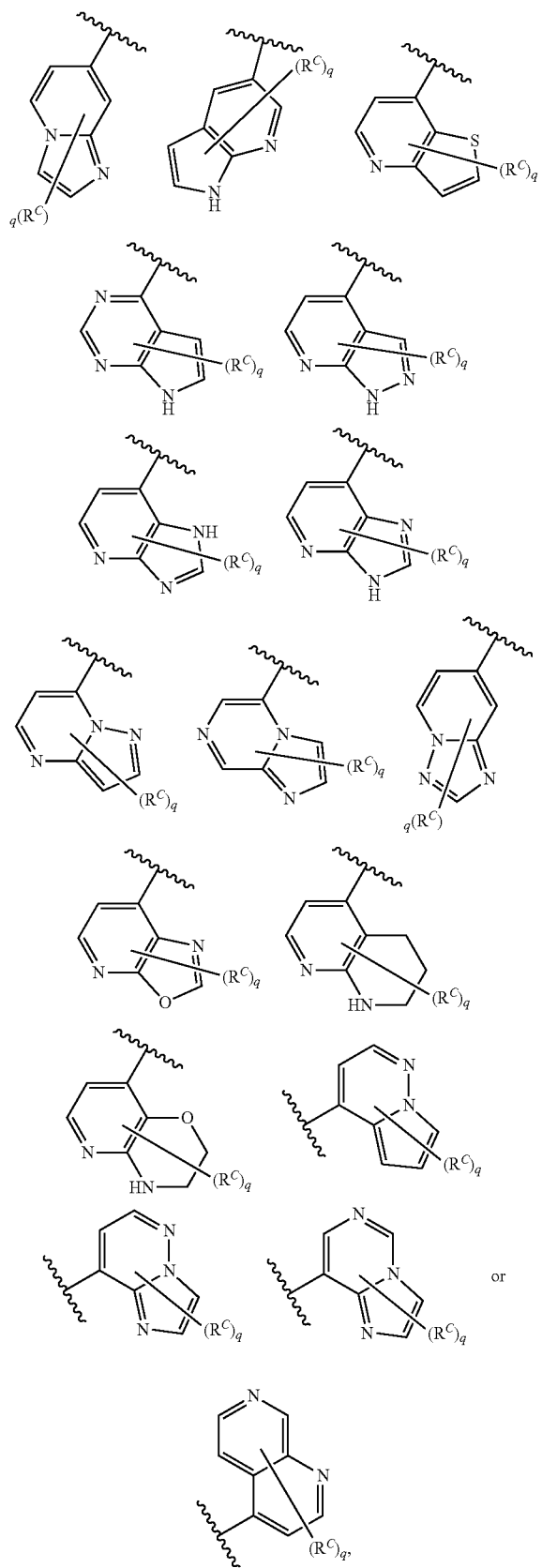
wherein $R^C$ and q are as defined in claim 1.
15. The compound of claim 1, wherein $R^2$ is
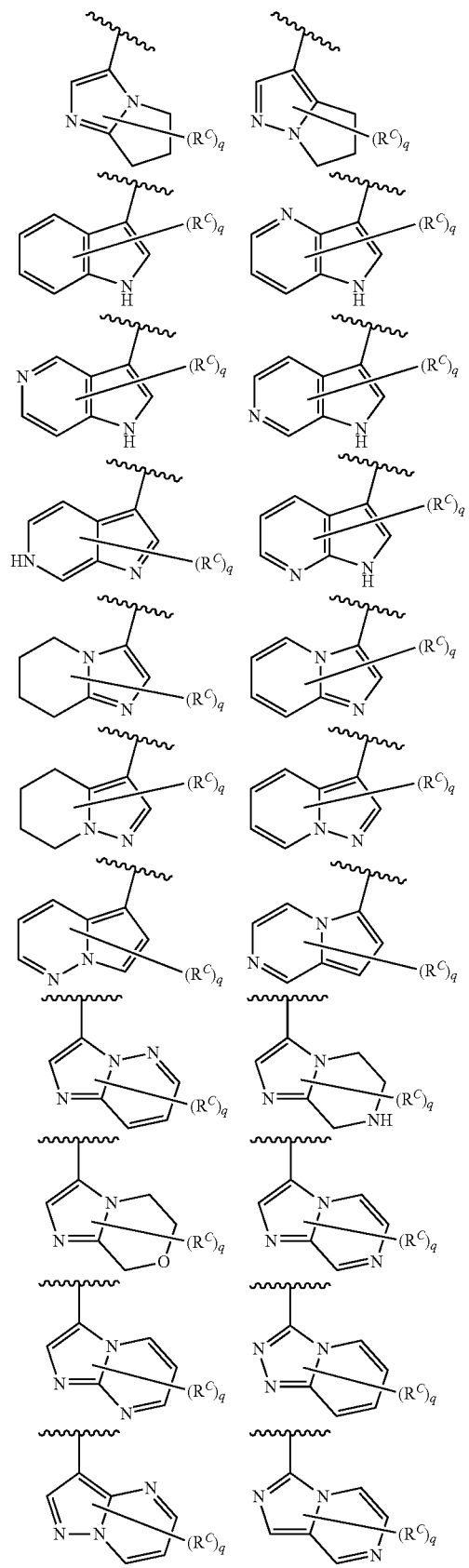
or

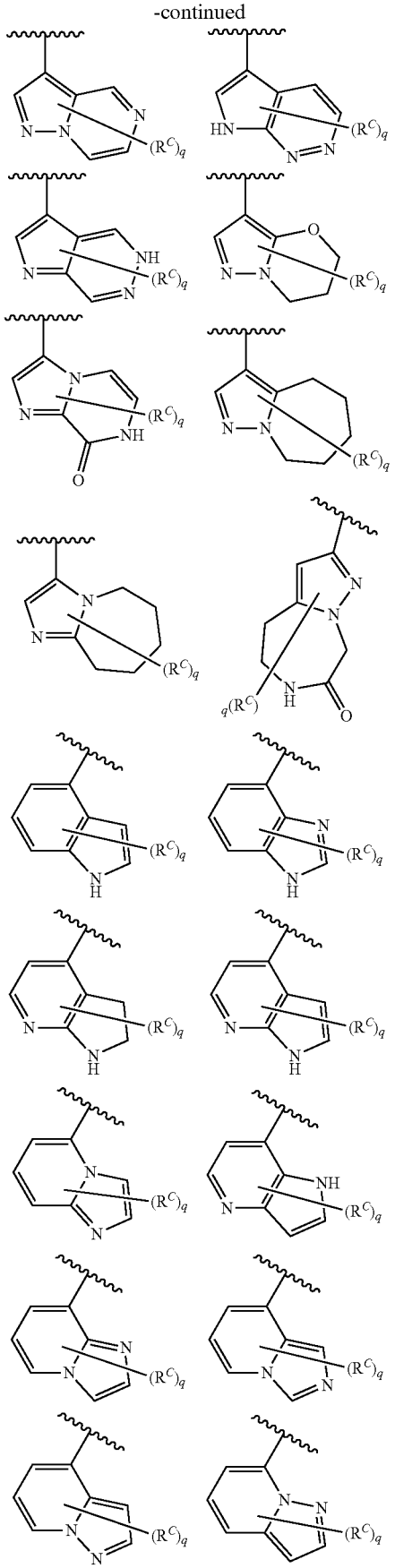
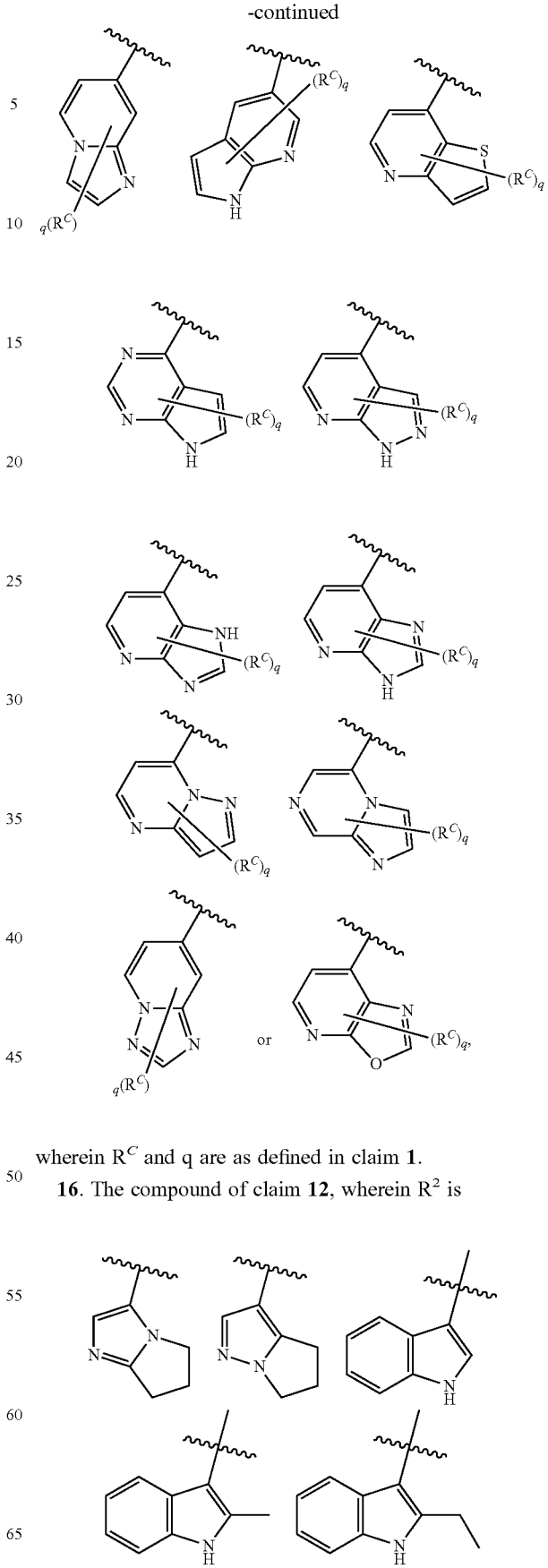
wherein $R^C$ and q are as defined in claim 1.
16. The compound of claim 12, wherein $R^2$ is 2399
-continued
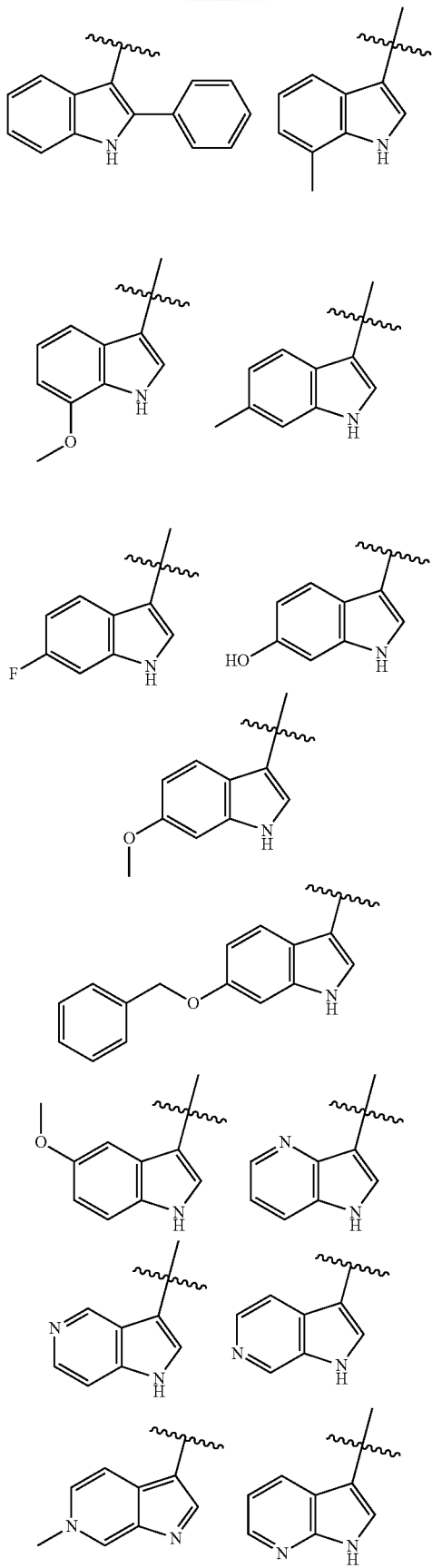
2400
-continued
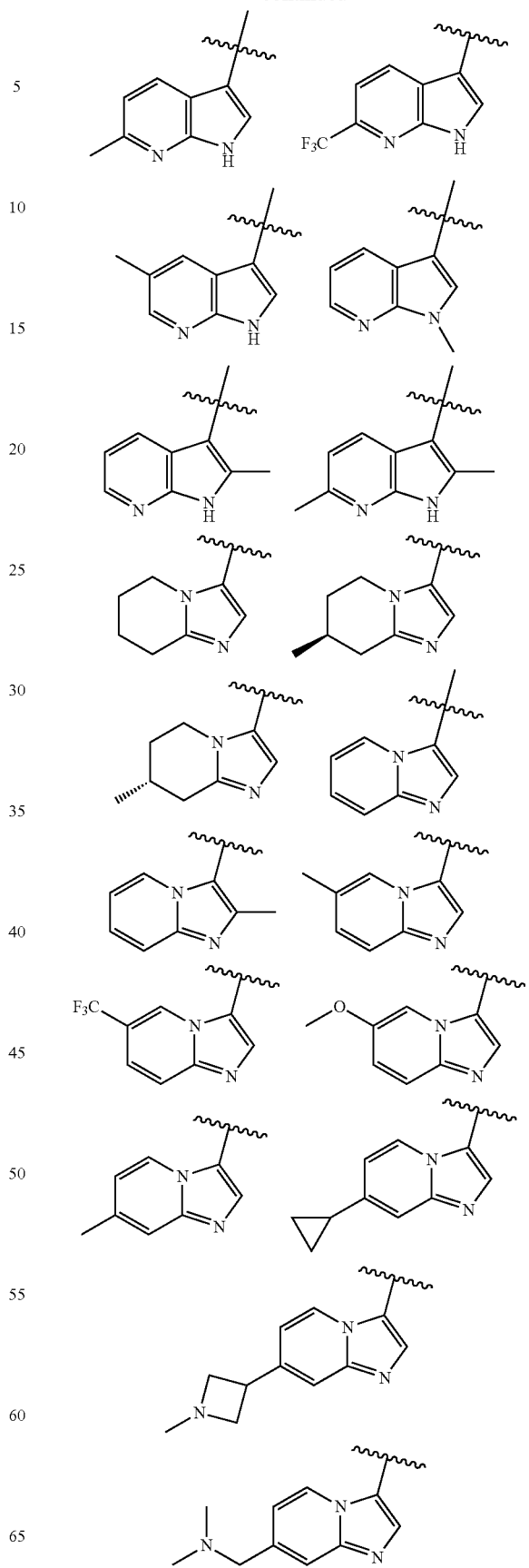

2401
-continued
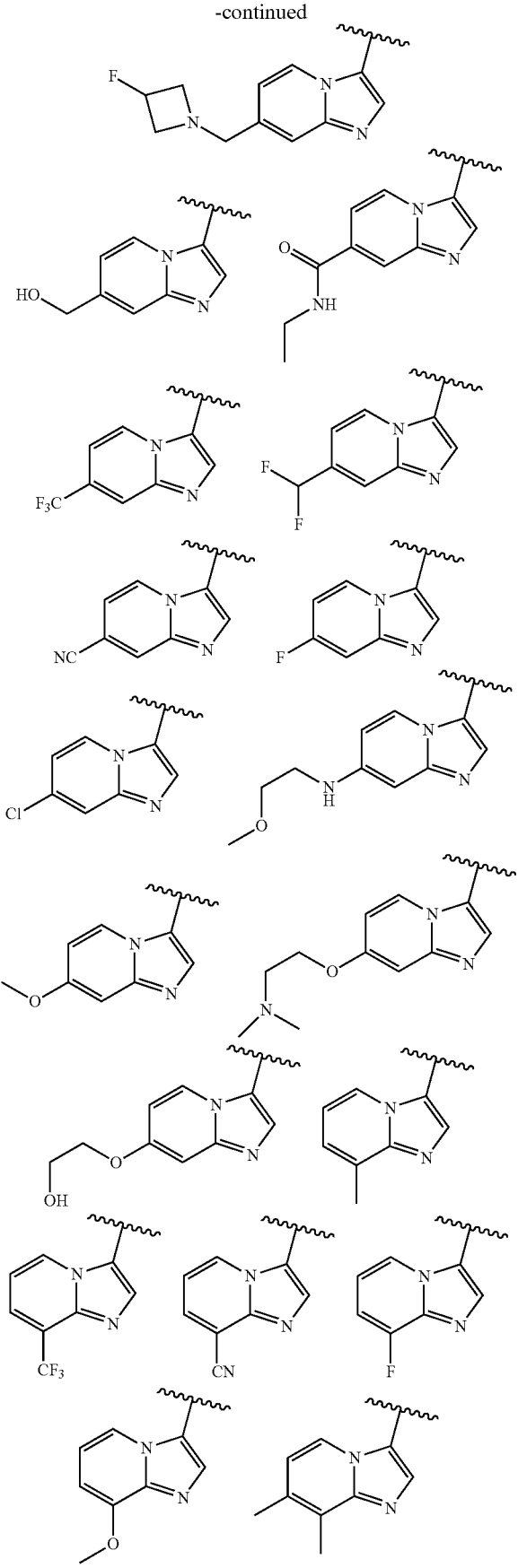
2402
-continued
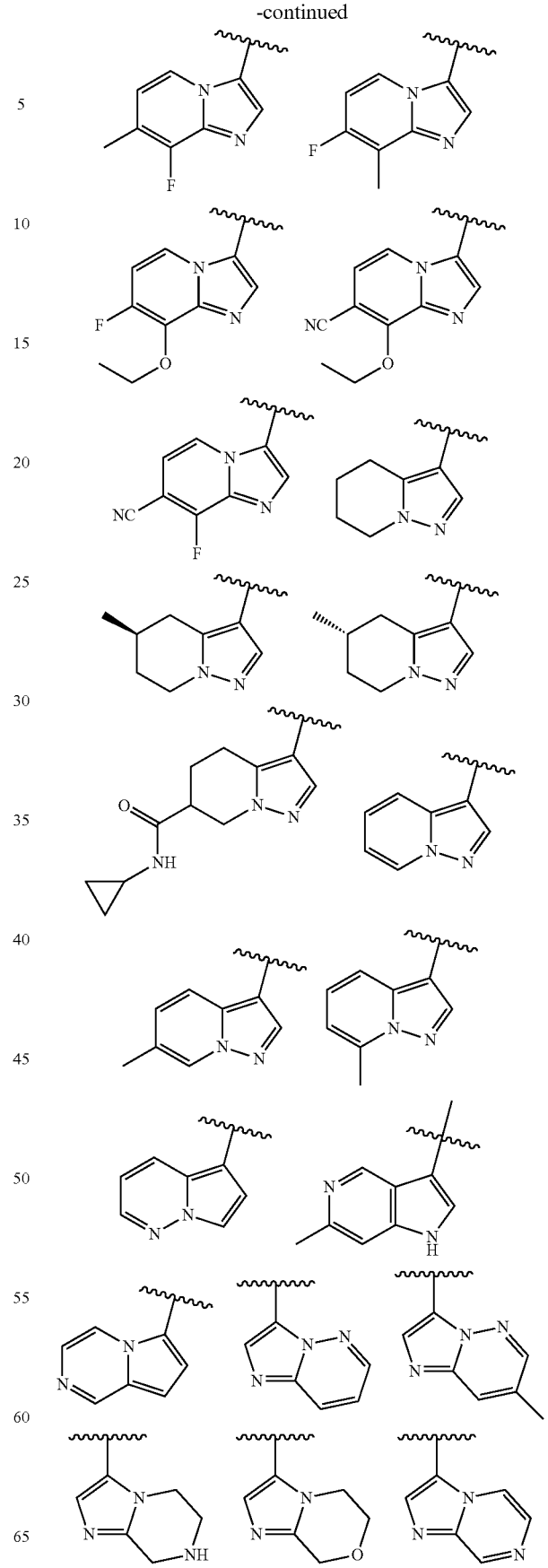

2403
-continued
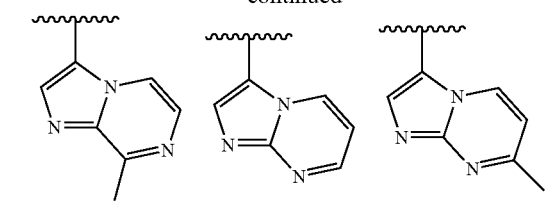
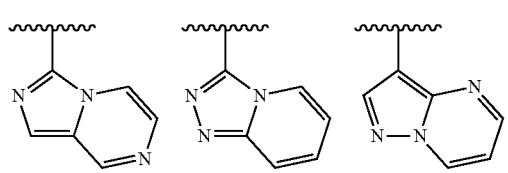
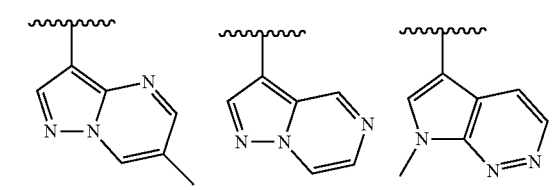
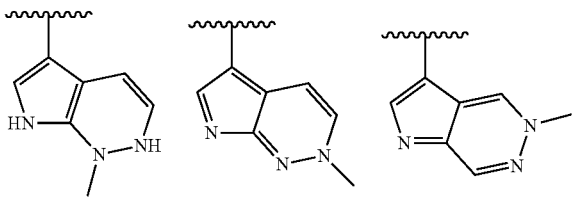
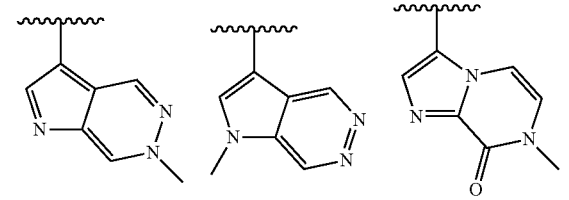
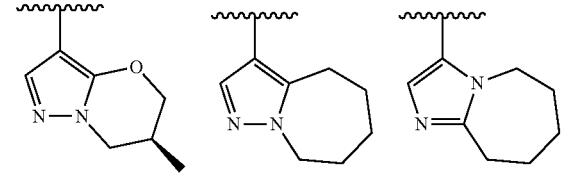
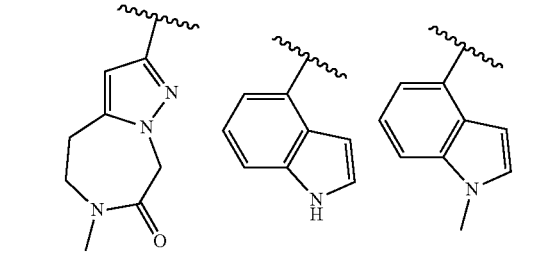
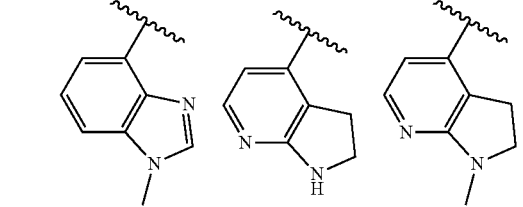
2404
-continued
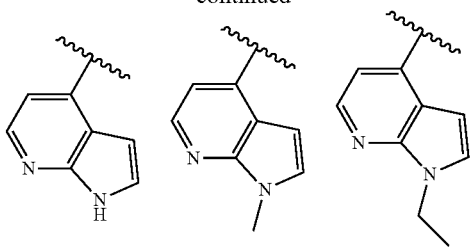
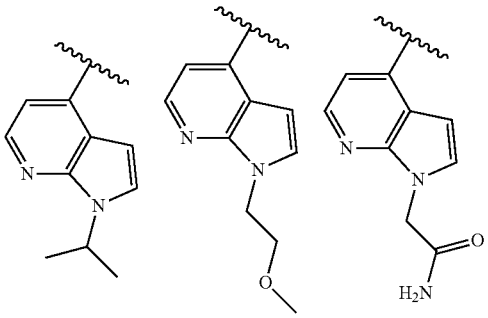
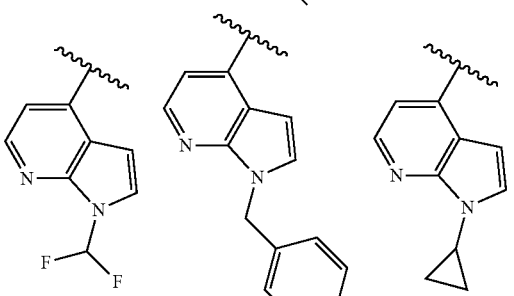
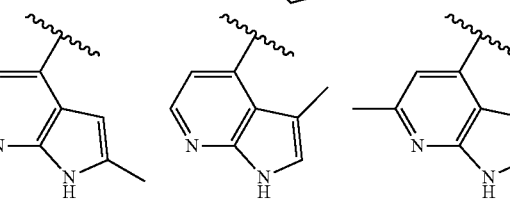
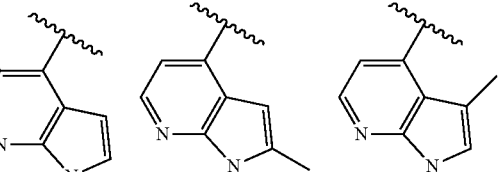
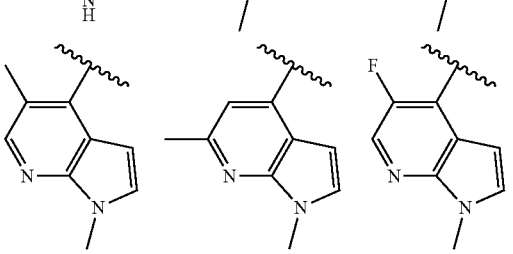
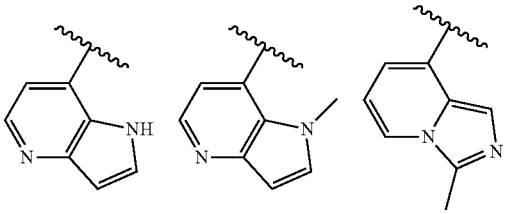

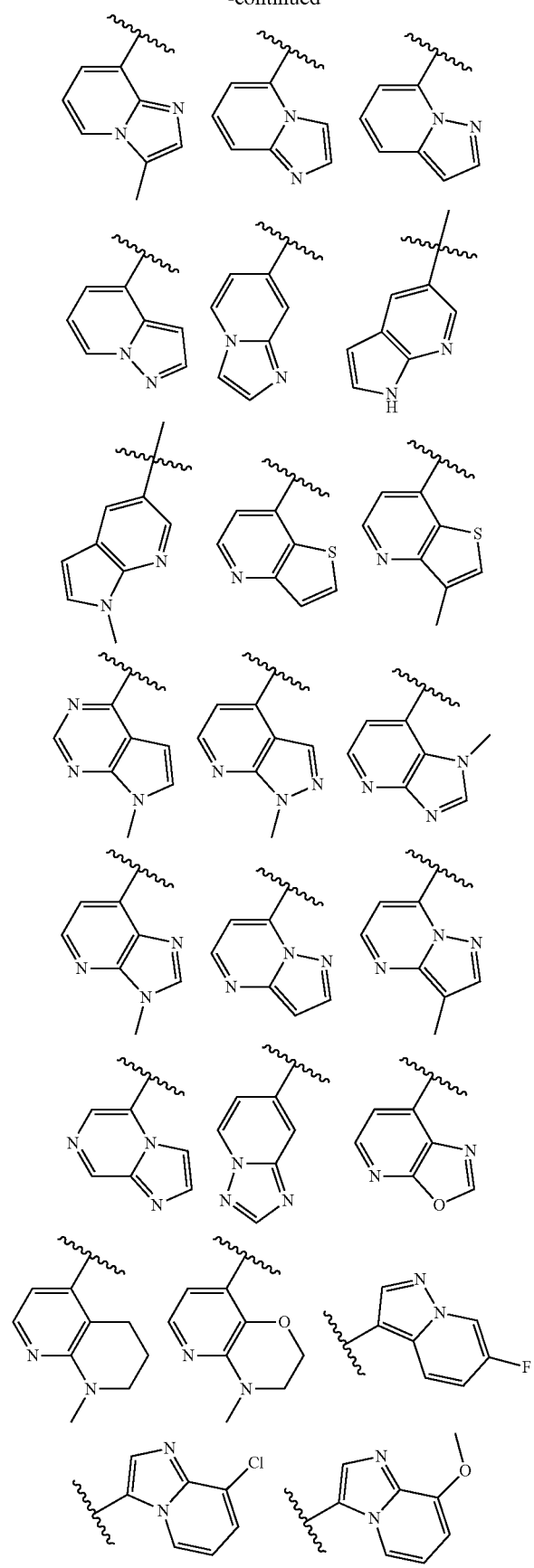
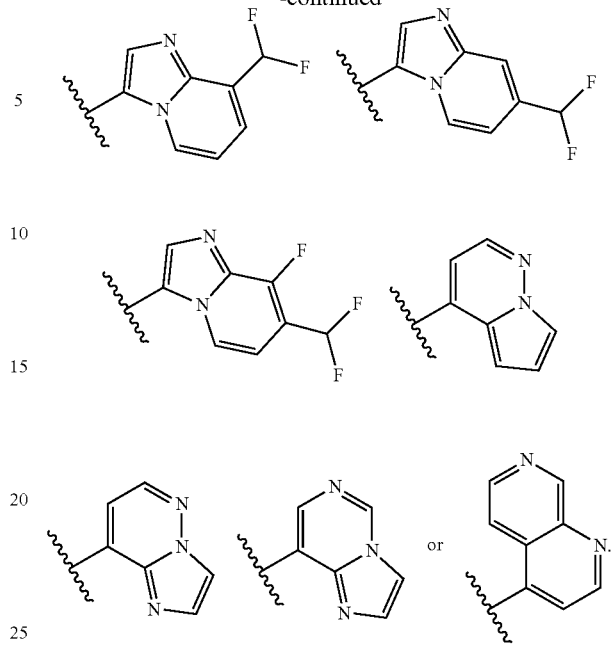
17. The compound of claim 1, wherein the compound is selected from the group consisting of:
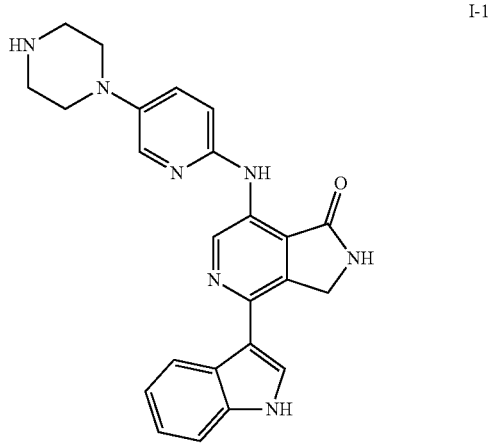
I-1
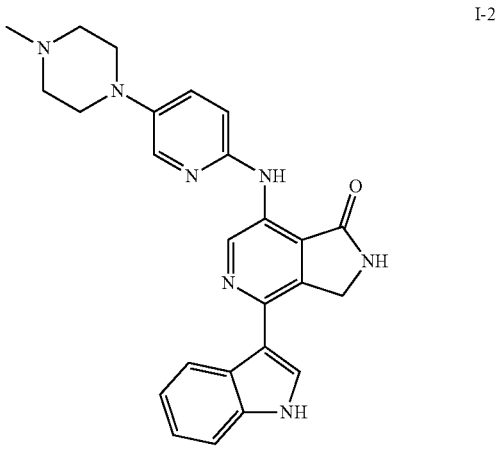
I-2

-continued
I-3
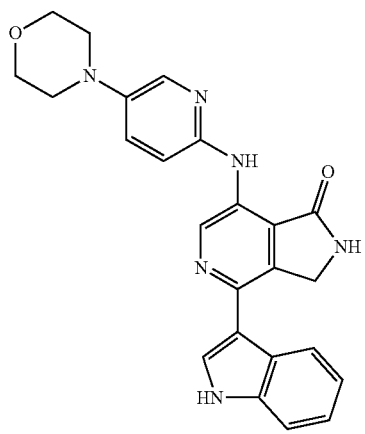
I-4
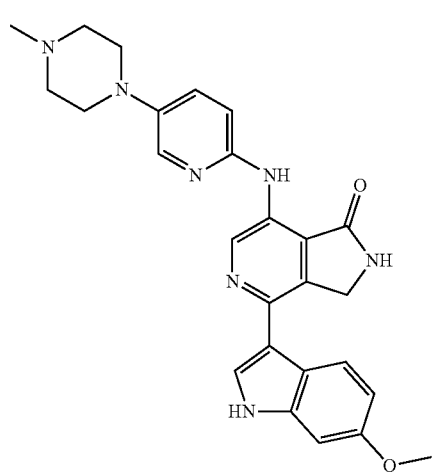
I-5
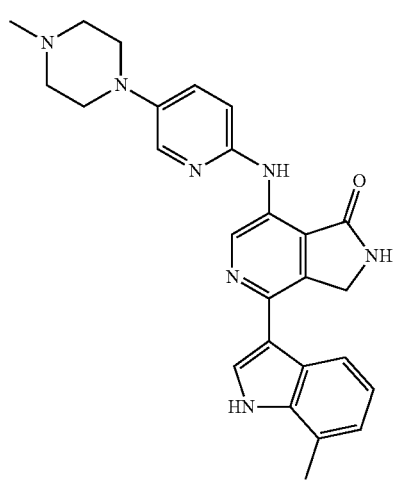
-continued
I-6
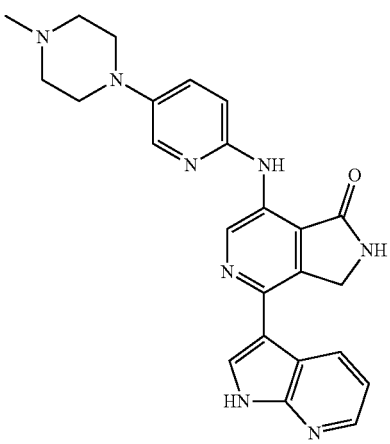
I-7
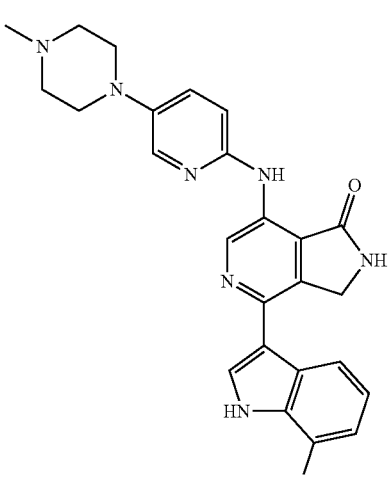
I-8
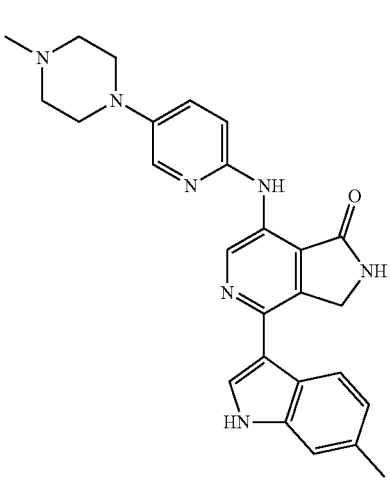

2409
-continued
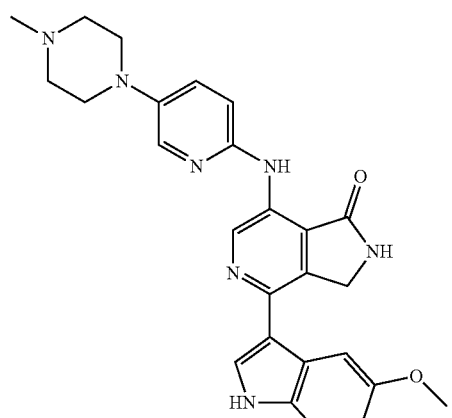
I-9
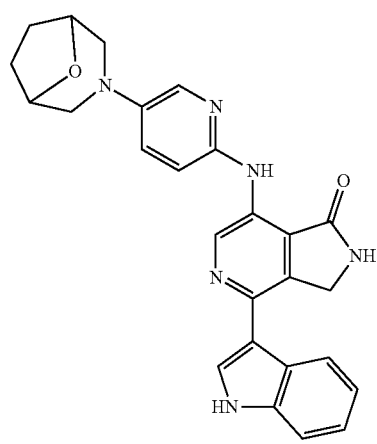
I-10
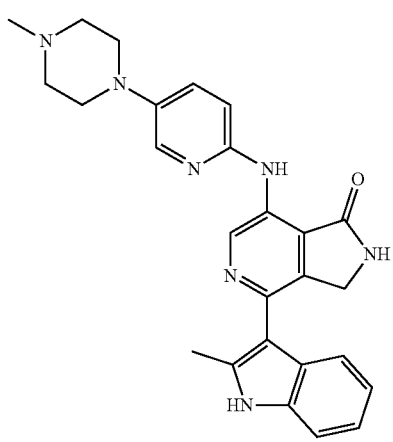
I-11
2410
-continued
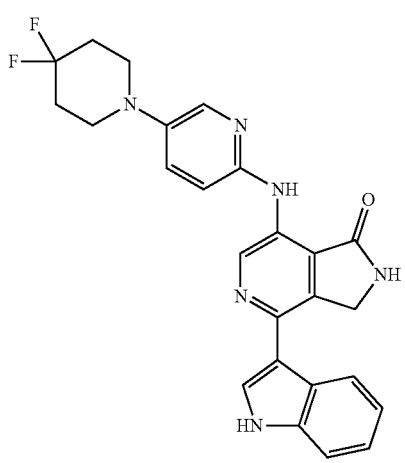
I-12
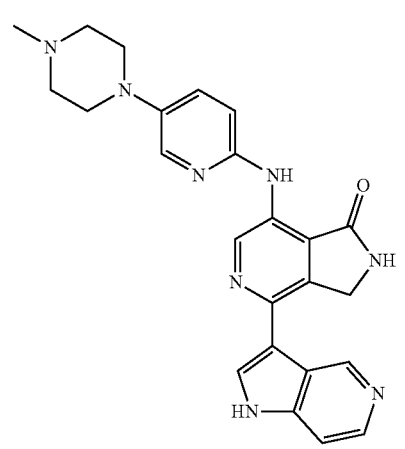
I-13
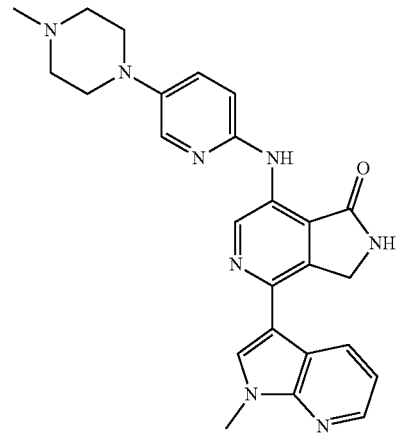
I-14

I-15
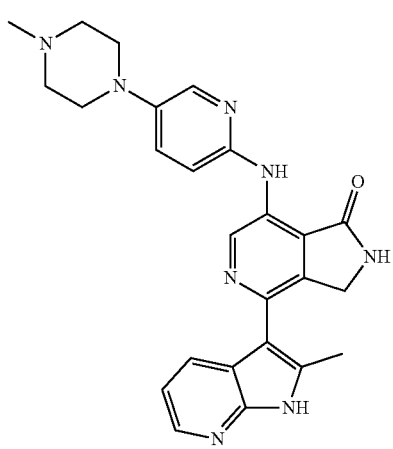
I-16
I-17
I-18
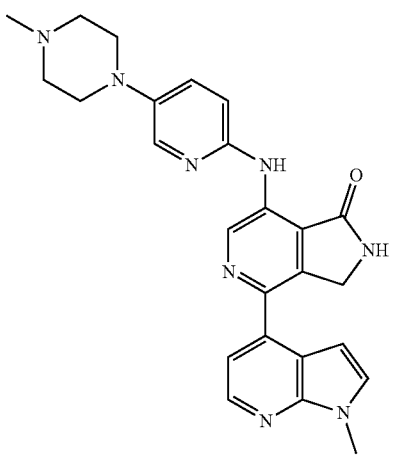
I-19
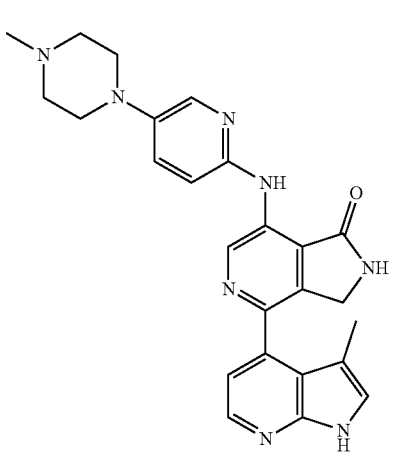
I-20
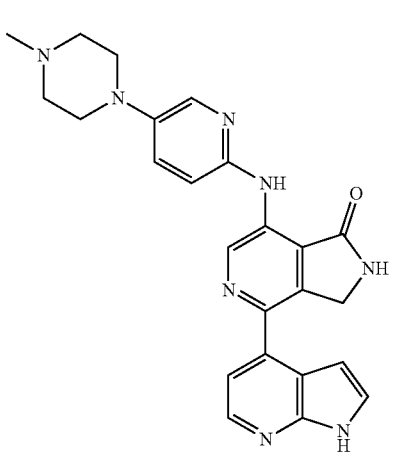

I-21
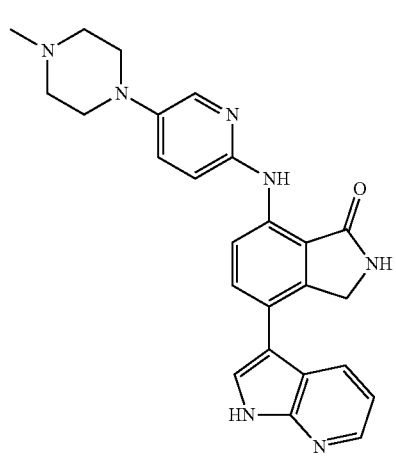
I-22
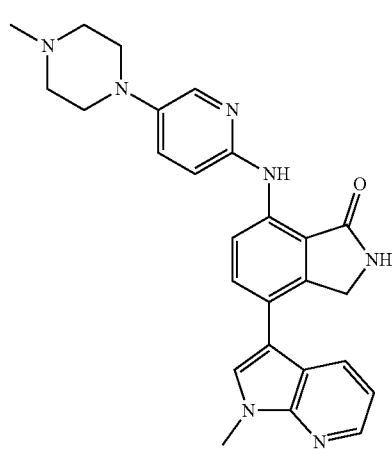
I-23
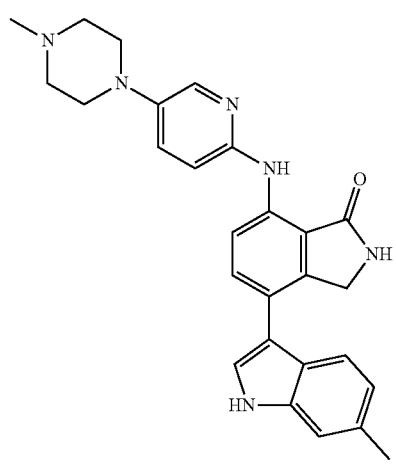
I-24
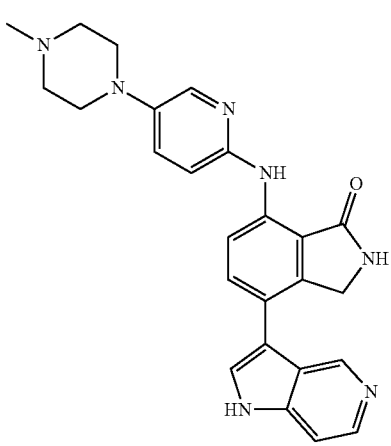
I-25
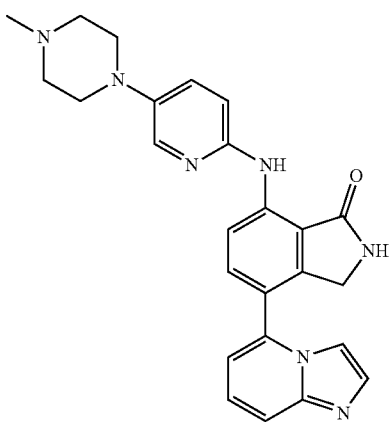
I-26
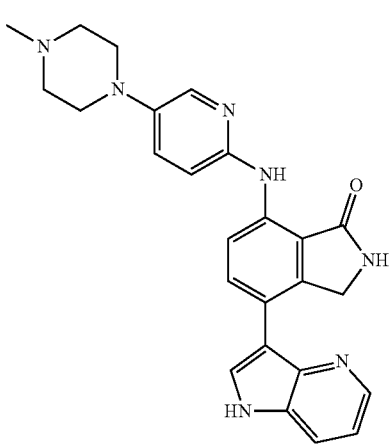

I-27
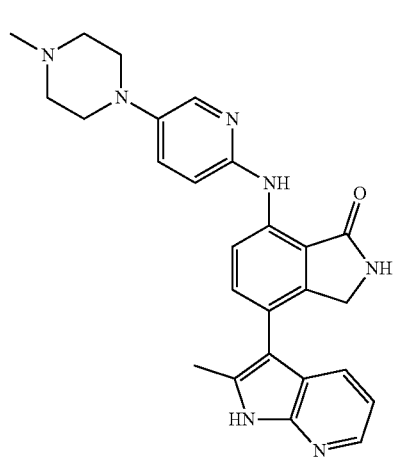
I-28
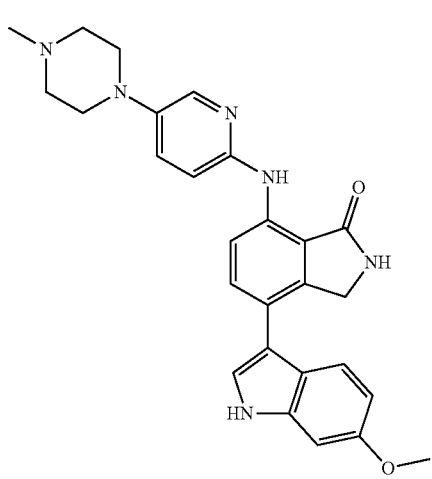
I-29
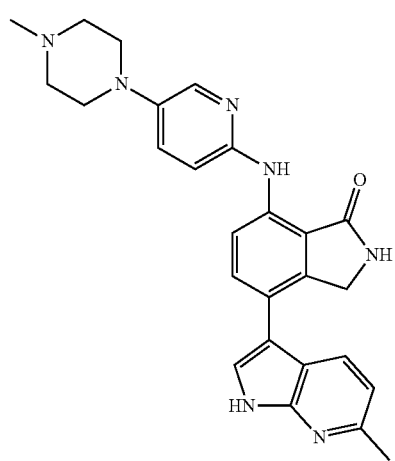
I-30
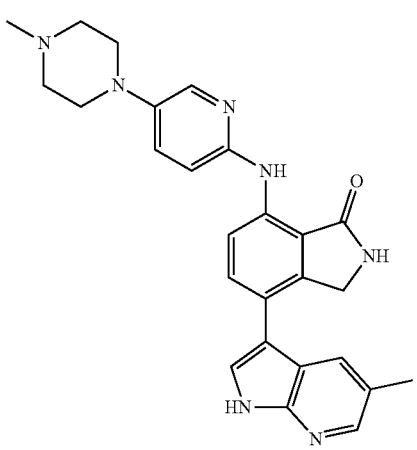
I-31
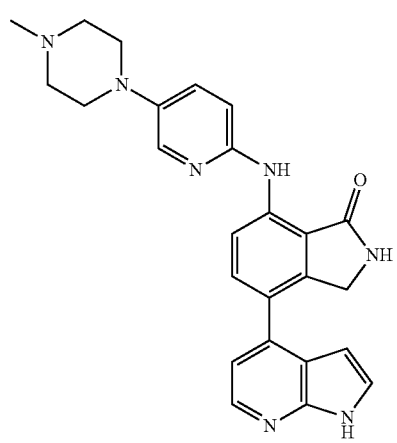
I-32
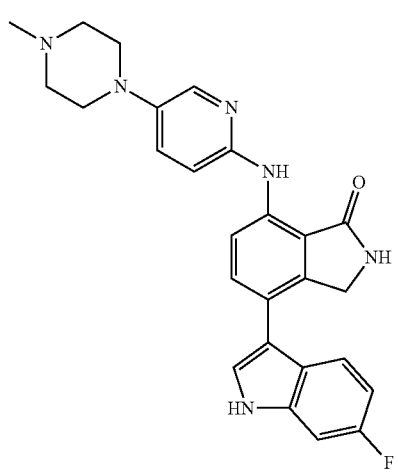

I-33
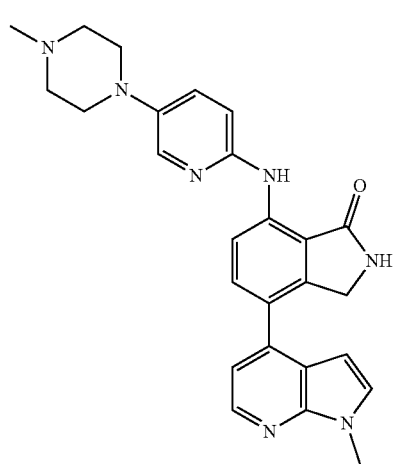
I-34
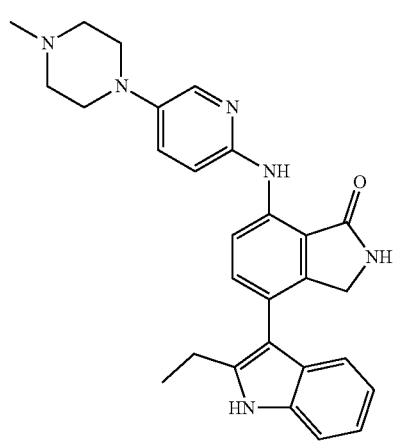
I-35
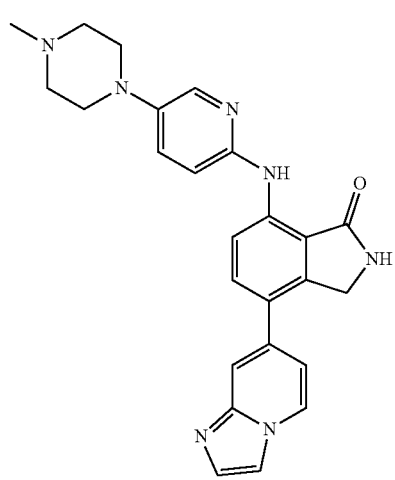
I-36
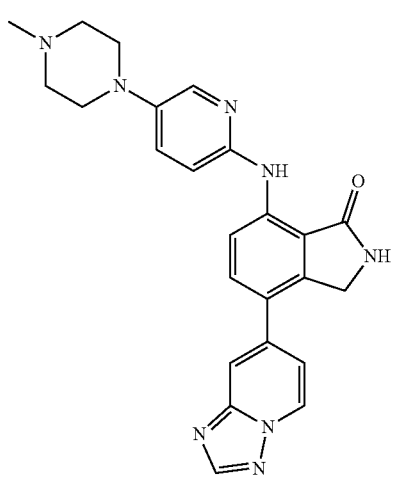
I-37
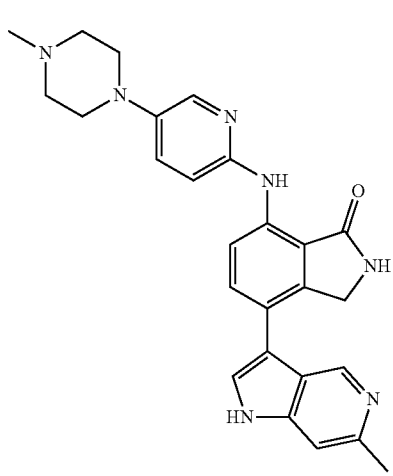
I-38
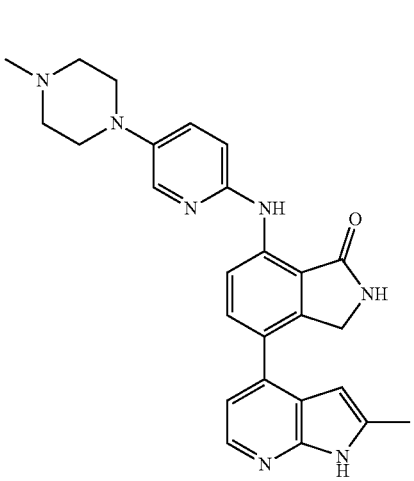

I-39
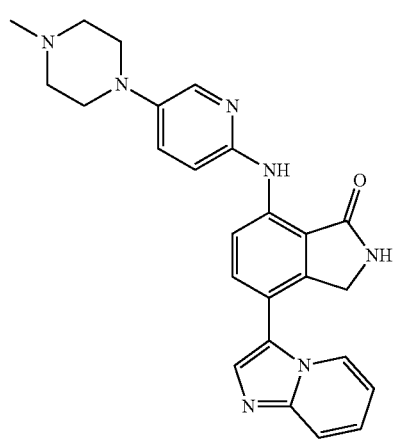
I-42
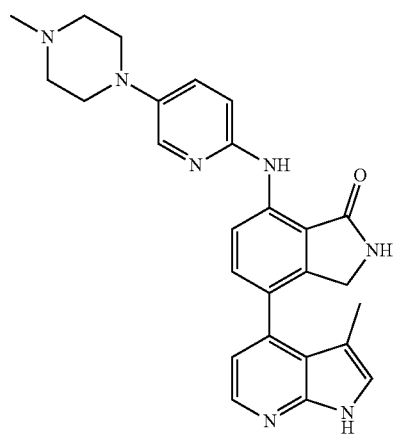
I-40
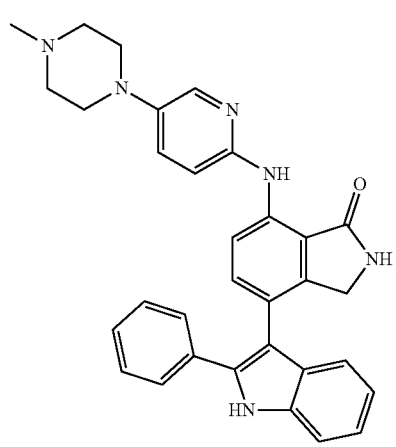
I-43
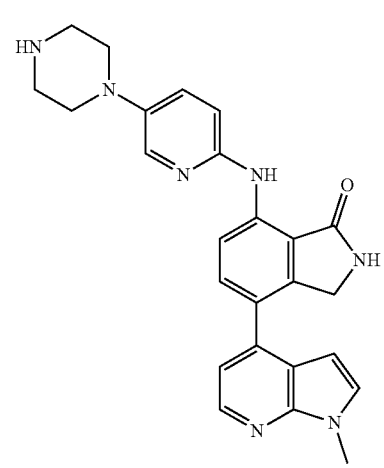
I-41
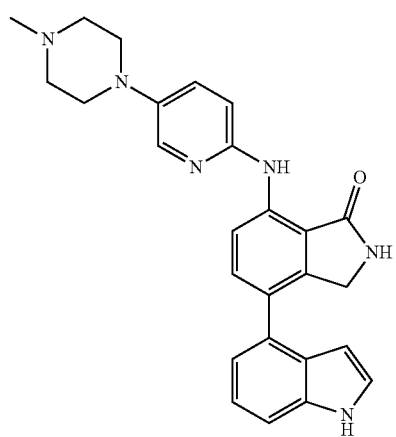
I-44
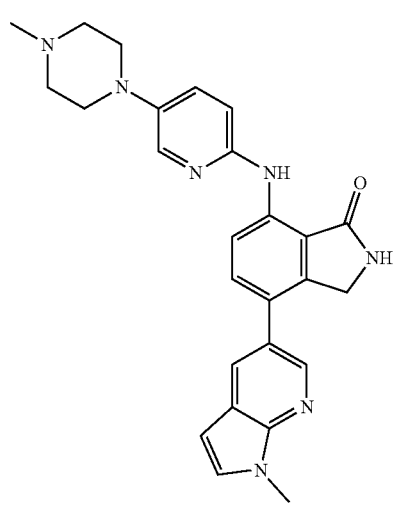

-continued
I-45
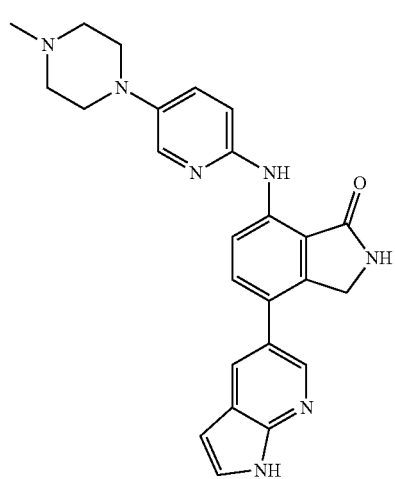
I-48
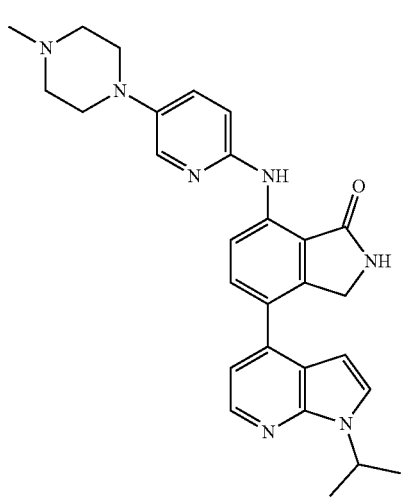
I-46
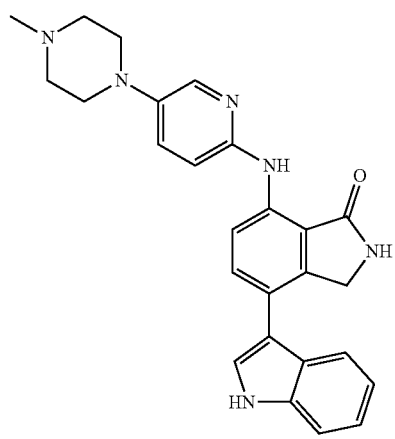
I-49
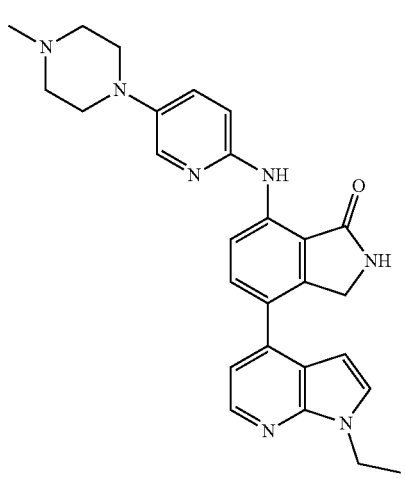
I-47
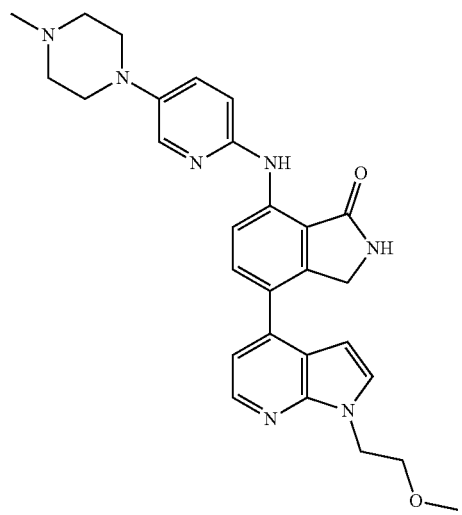
I-50
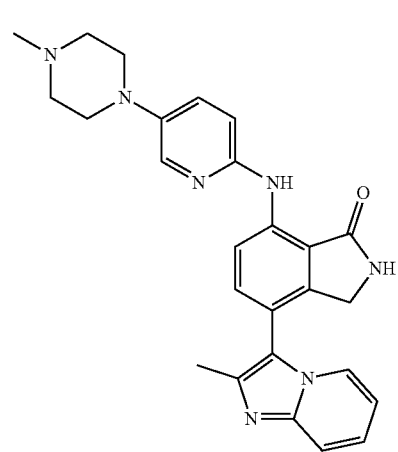

I-51
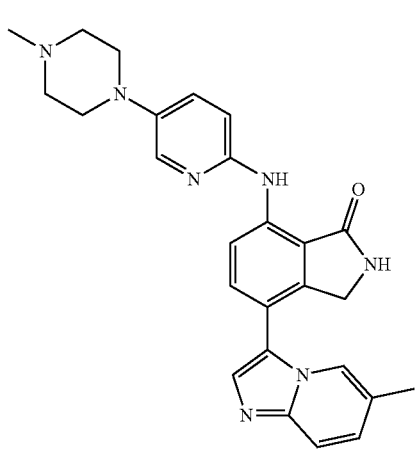
I-54
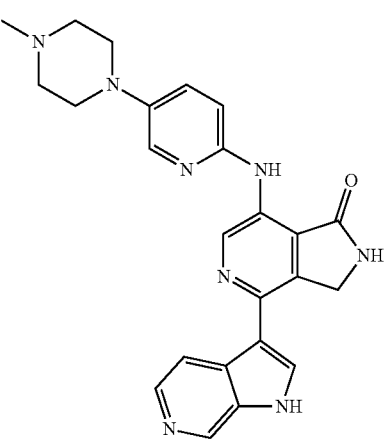
I-52
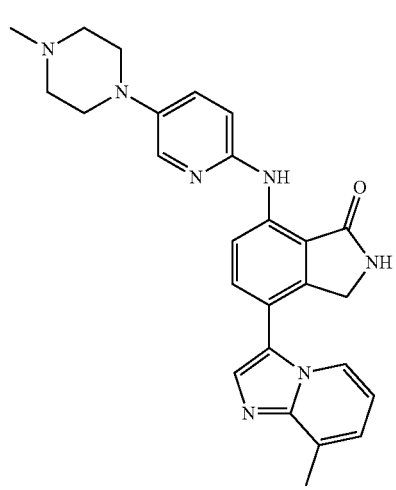
I-55
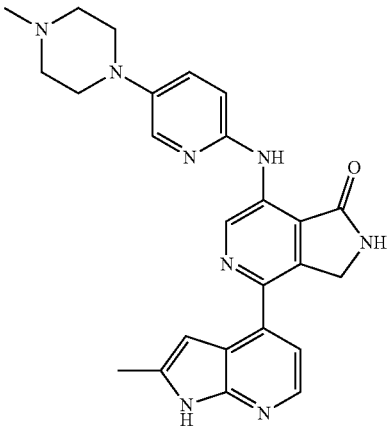
I-53
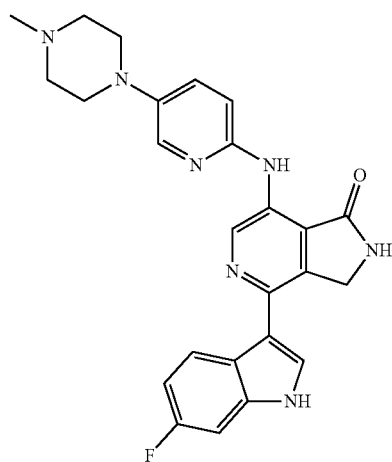
I-56
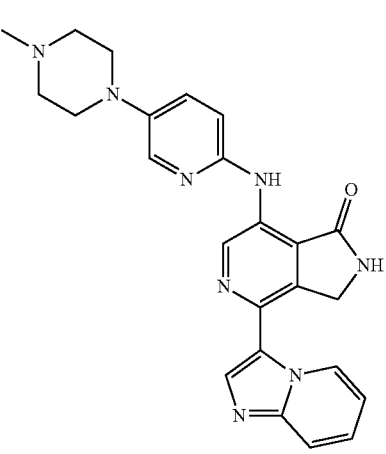

2425
-continued
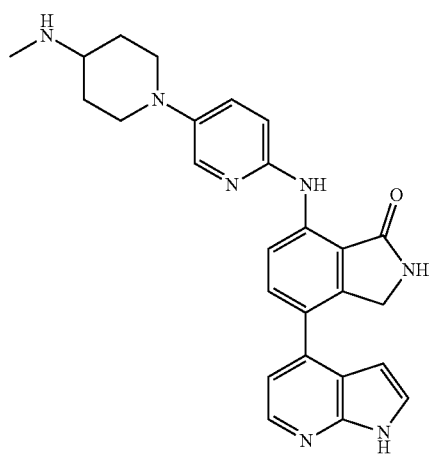
I-57
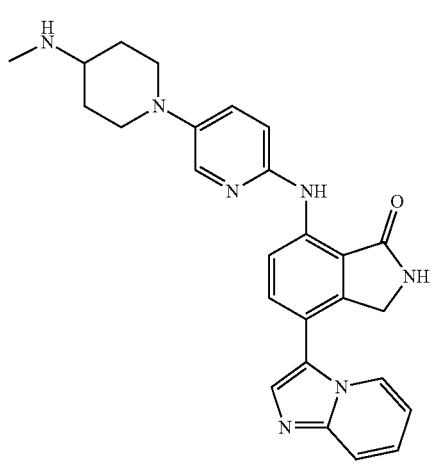
I-58
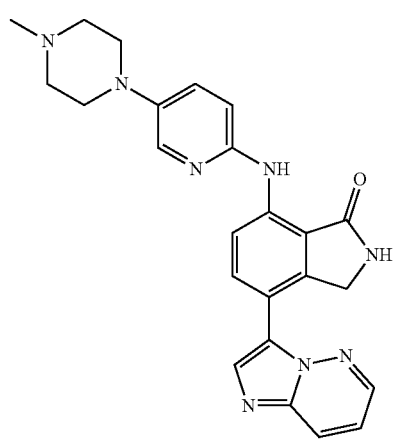
I-59
2426
-continued
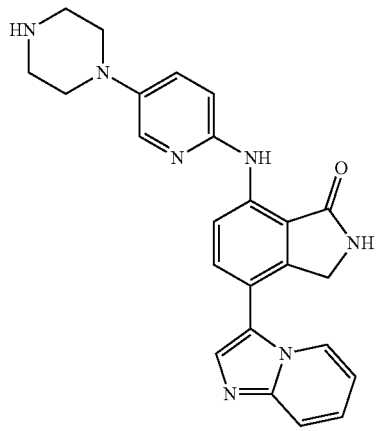
I-60
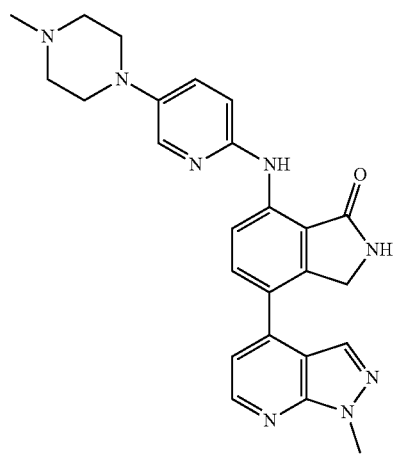
I-61
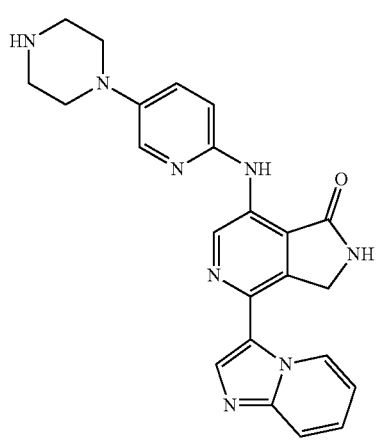
I-63

I-64
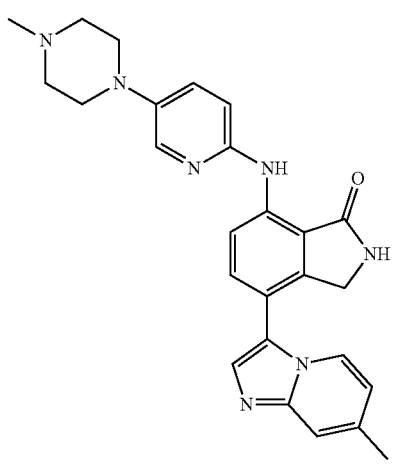
I-68
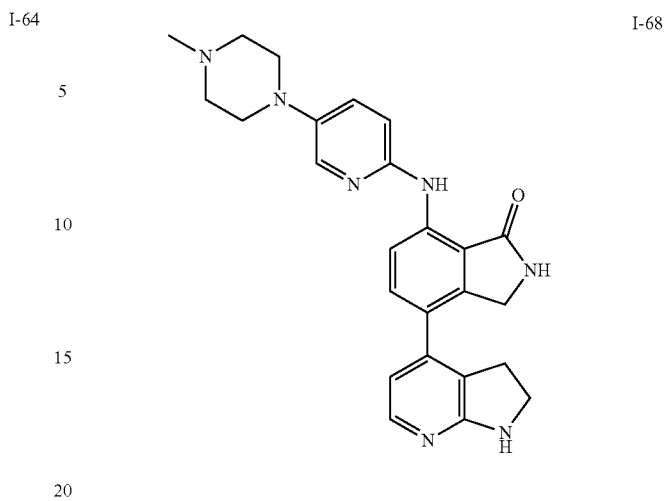
I-66
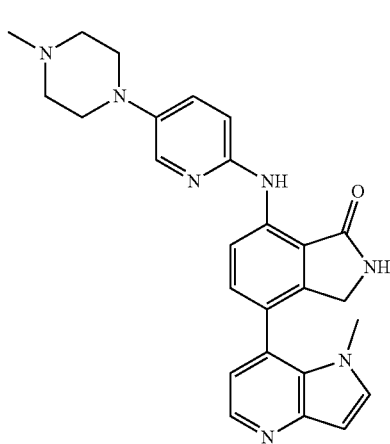
I-69
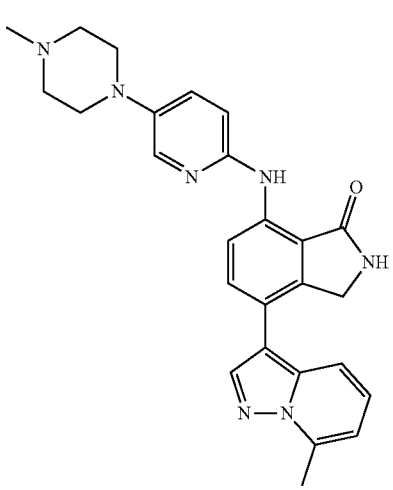
I-67
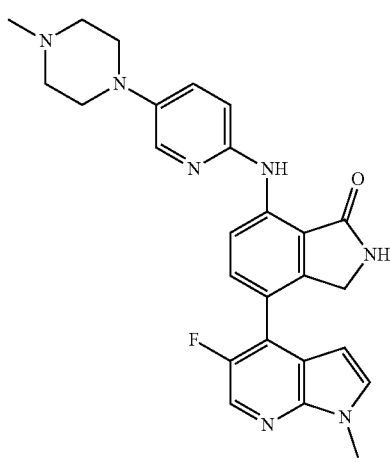
I-70
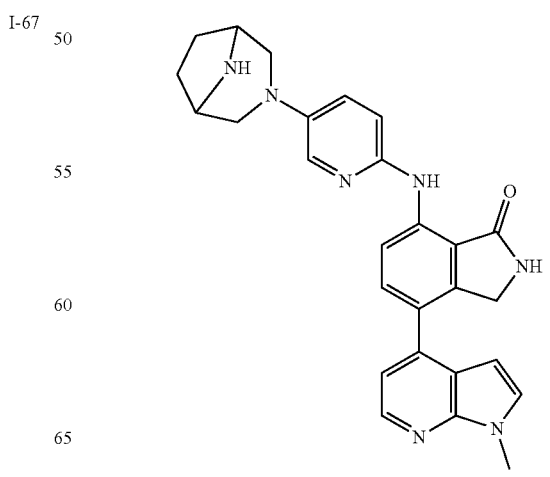

I-71
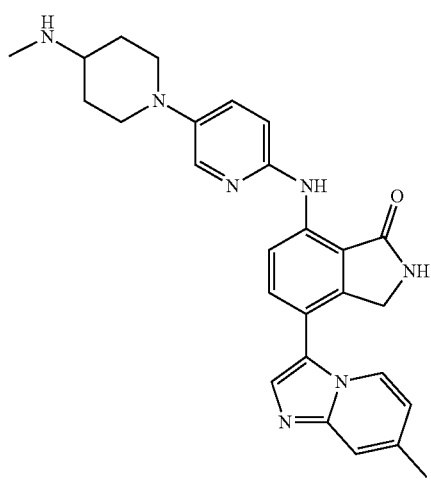
I-72
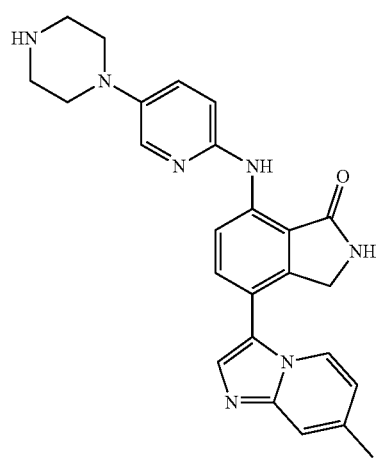
I-74
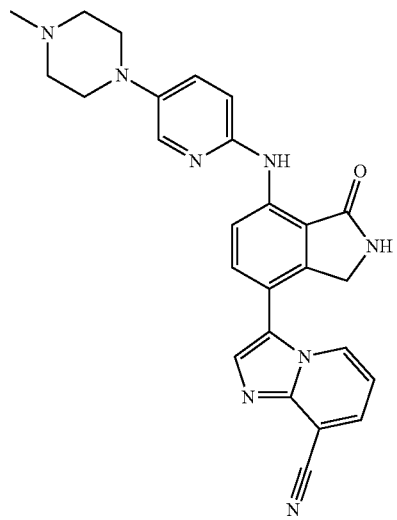
I-75
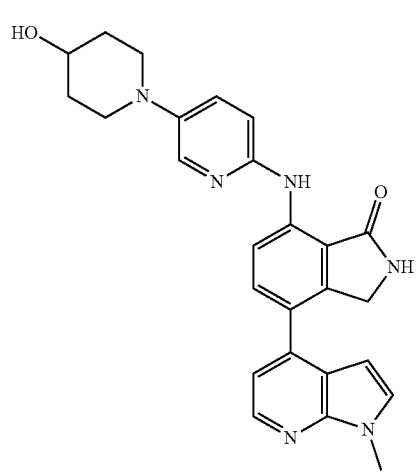
I-73
I-76
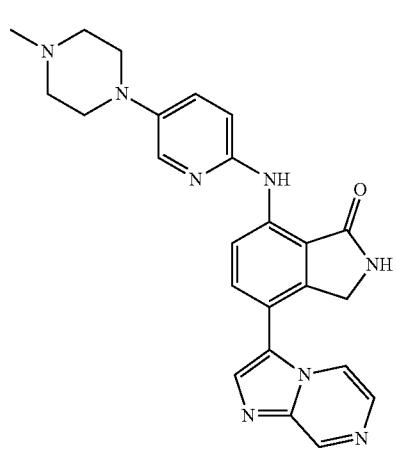

2431
-continued
I-77
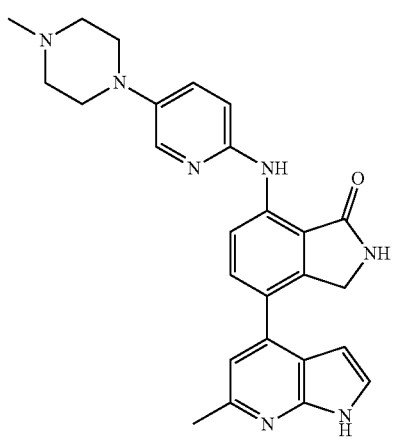
I-78
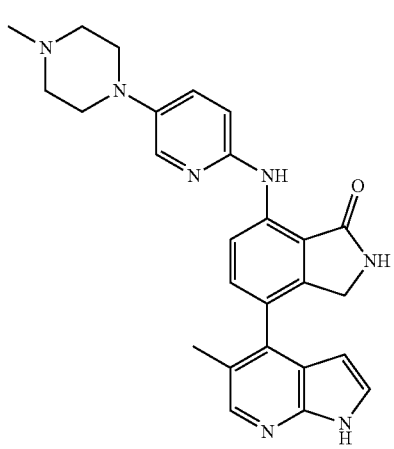
I-79
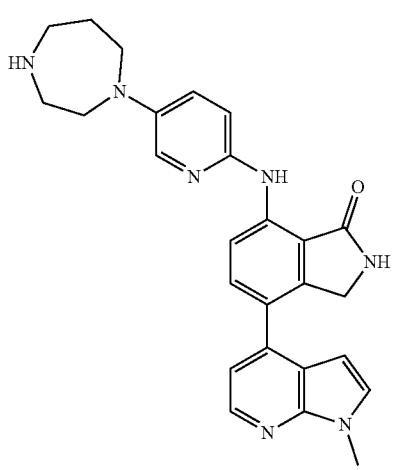
2432
-continued
I-80
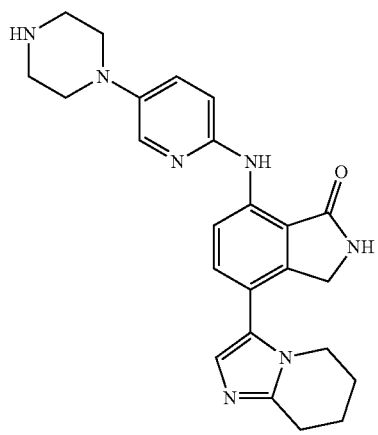
I-81
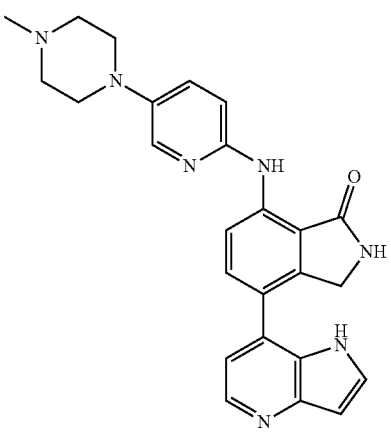
I-82
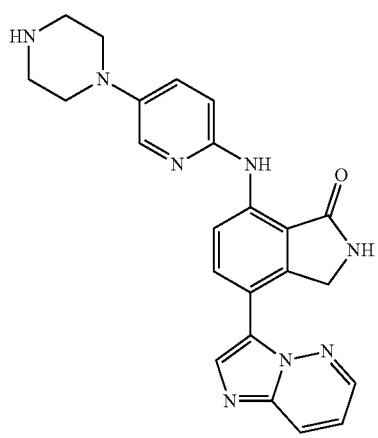

I-83
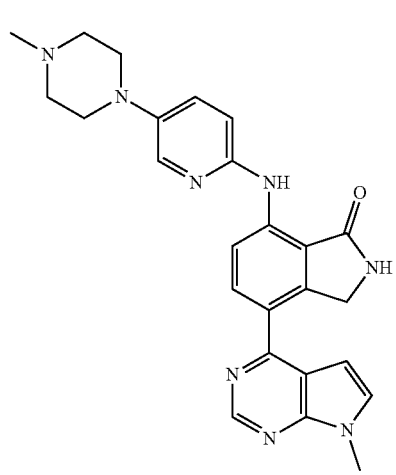
I-84
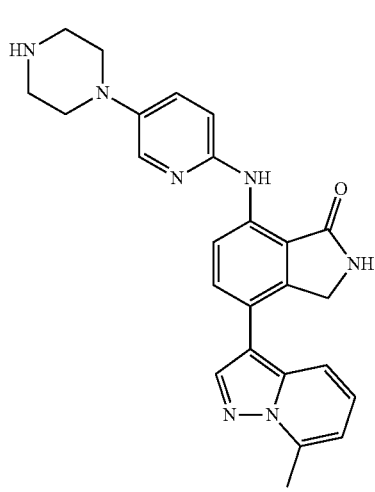
I-85
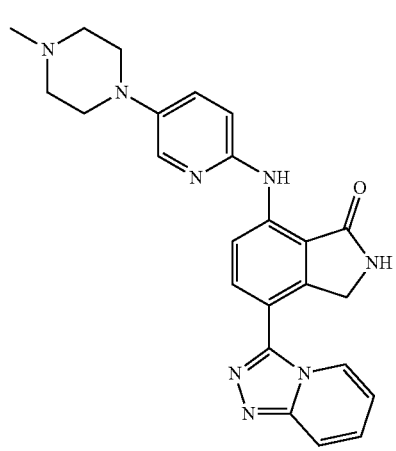
I-86
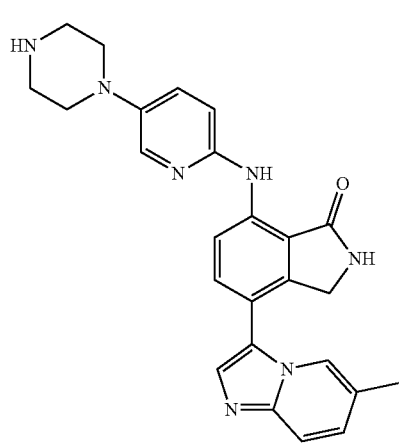
I-87
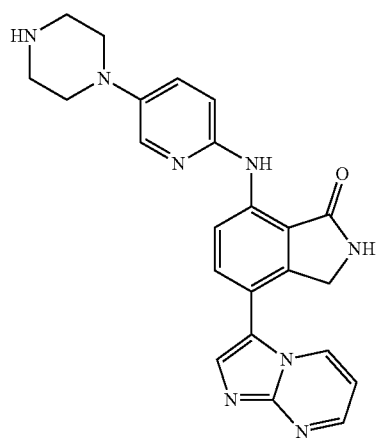
I-88
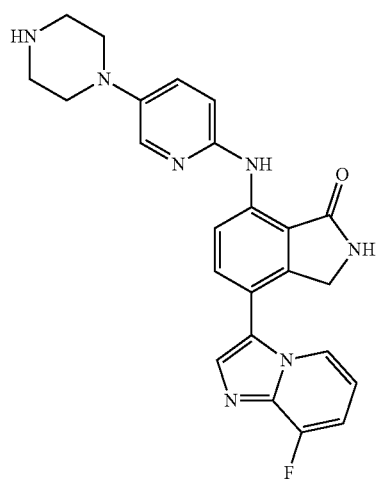

I-90
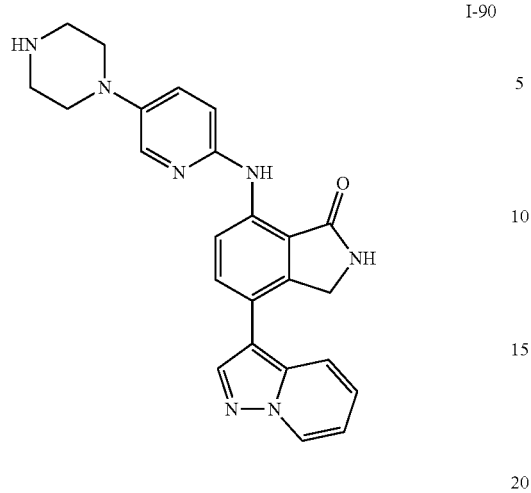
I-93
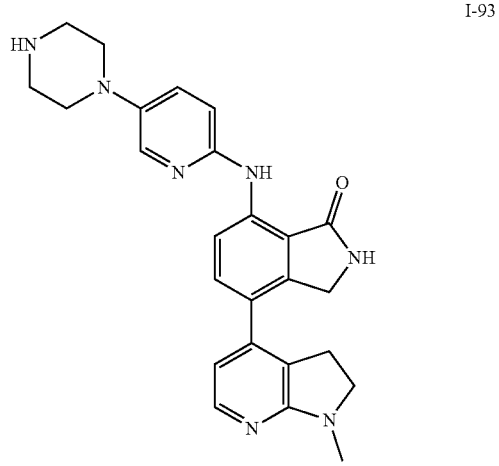
I-91
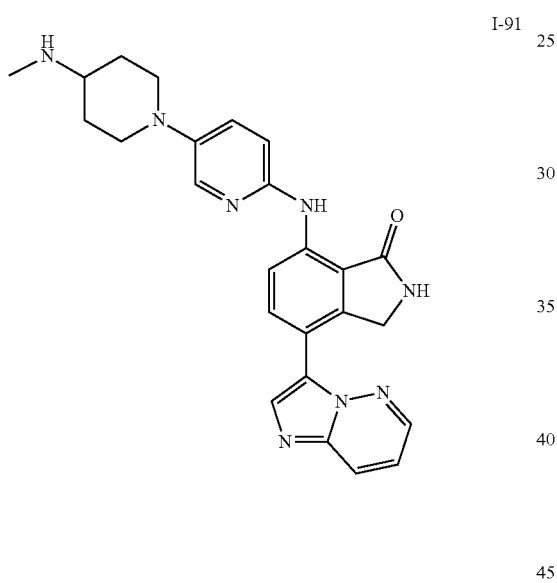
I-94
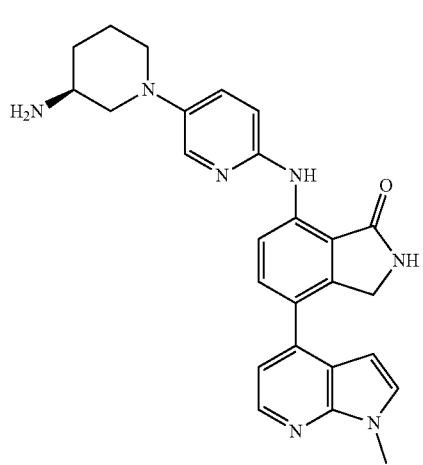
I-92
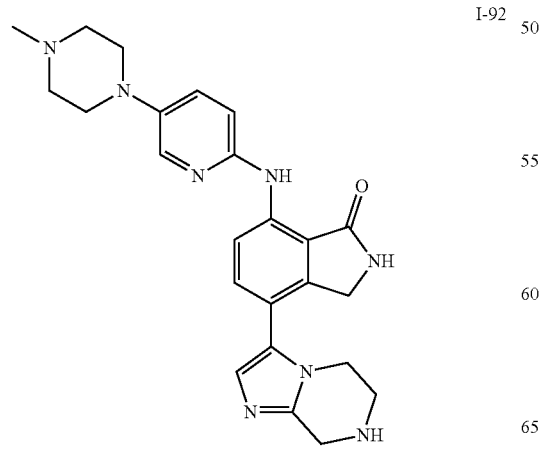
I-95
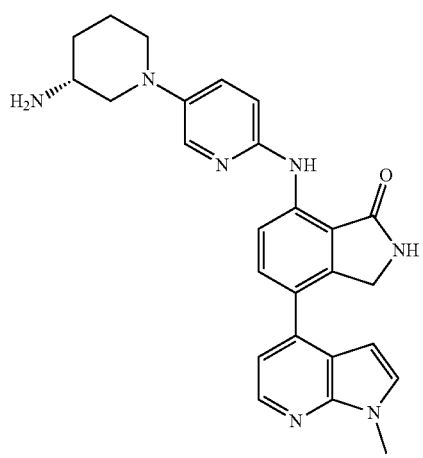

2437
-continued
I-96
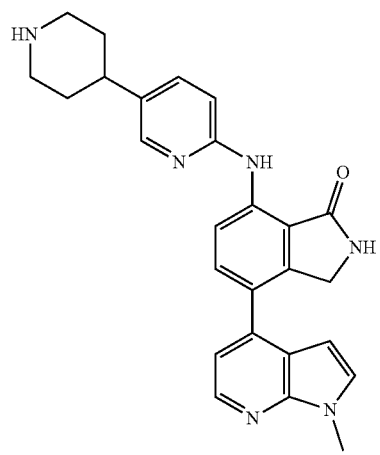
I-97
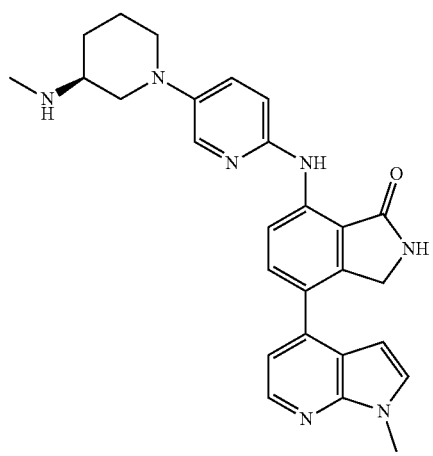
I-98
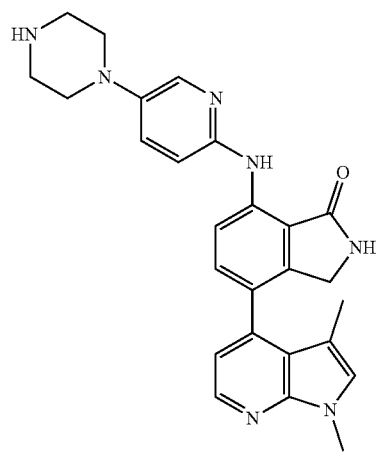
2438
-continued
I-99
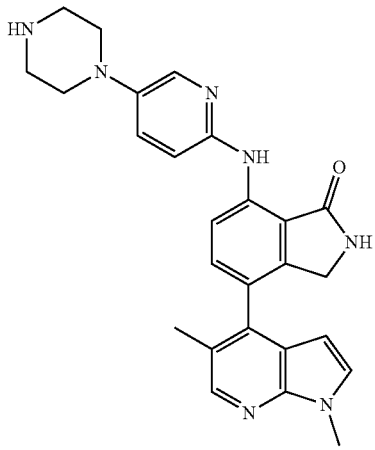
I-100
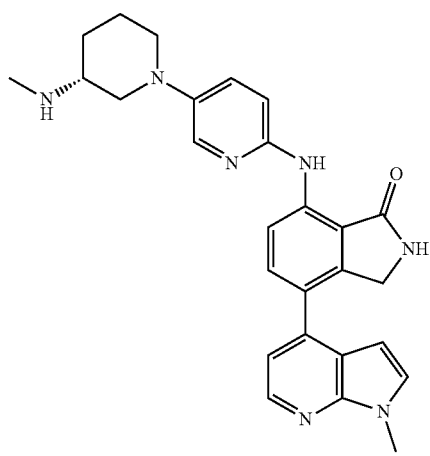
I-101
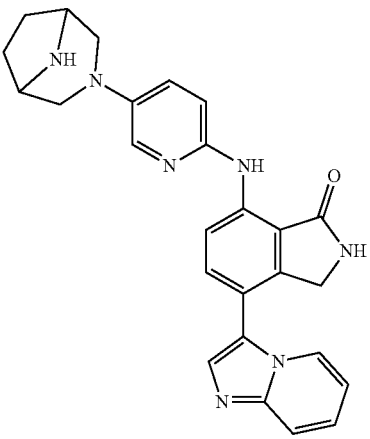

I-102
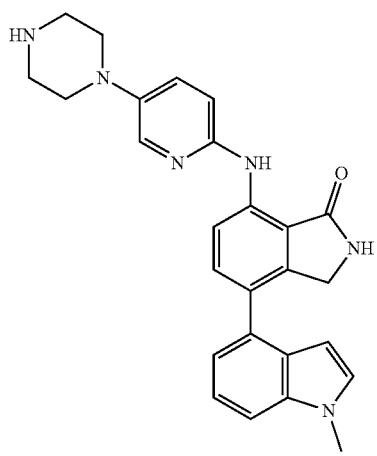
I-103
I-104
I-105
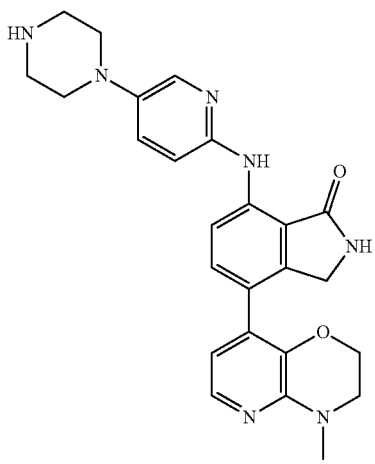
I-106
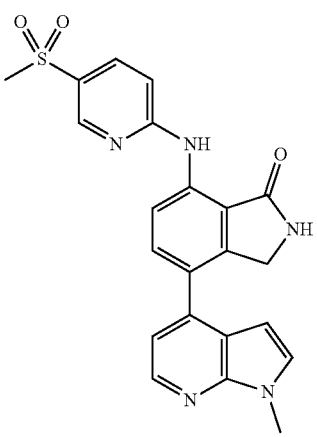
I-107
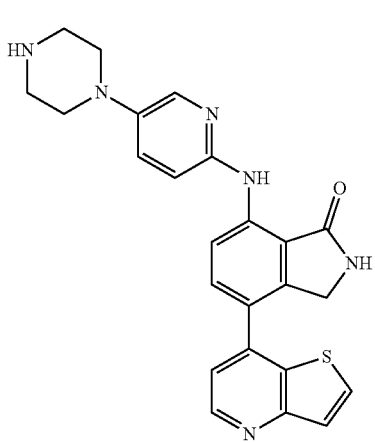

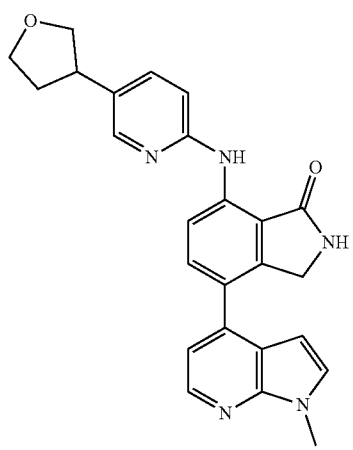
I-108
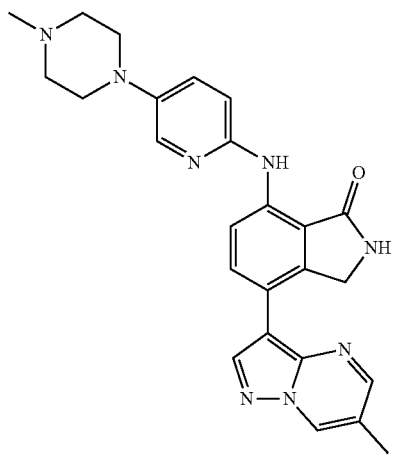
I-111
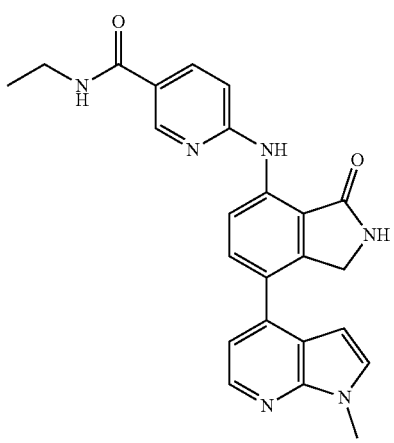
I-109
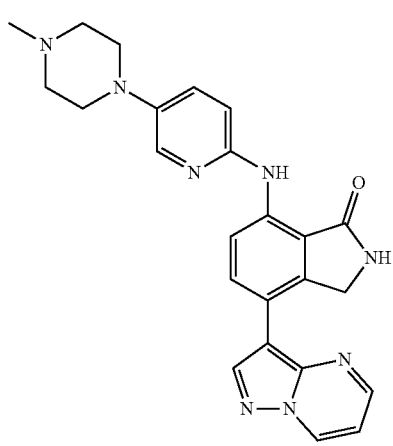
I-112
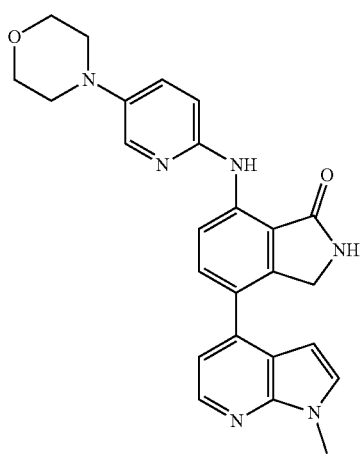
I-110
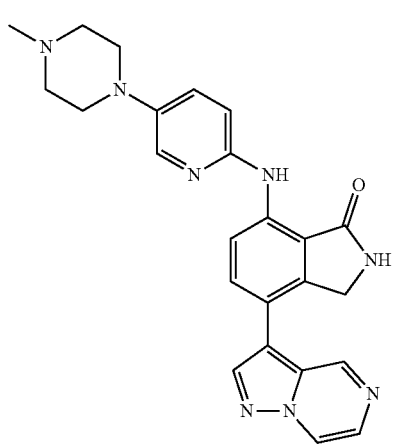
I-113

-continued
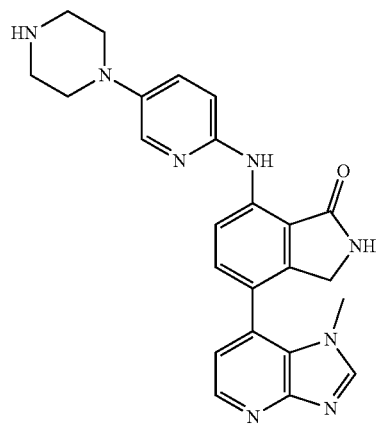
I-114
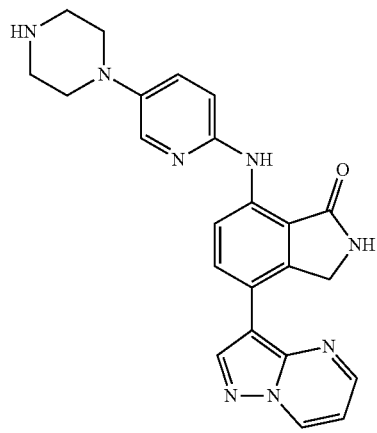
I-117
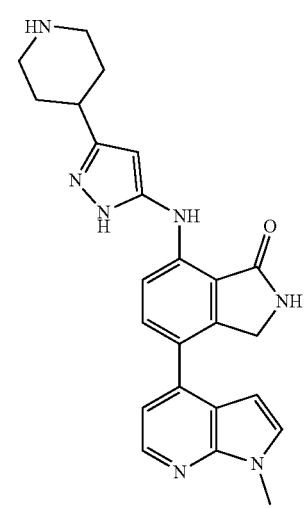
I-115
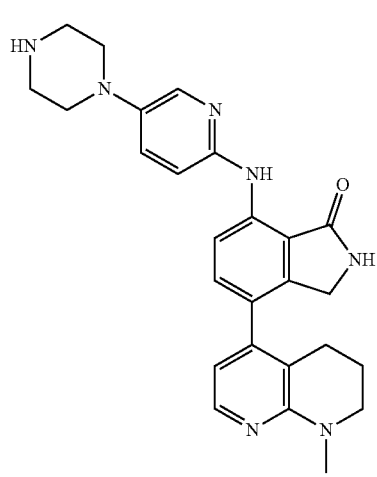
I-118
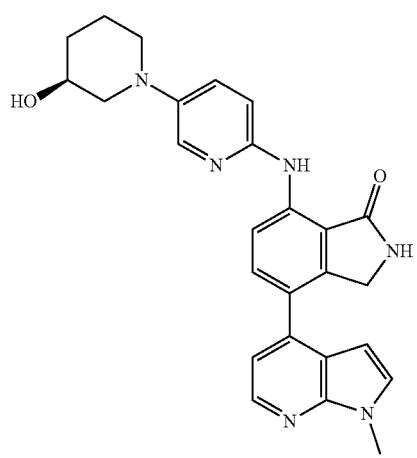
I-116
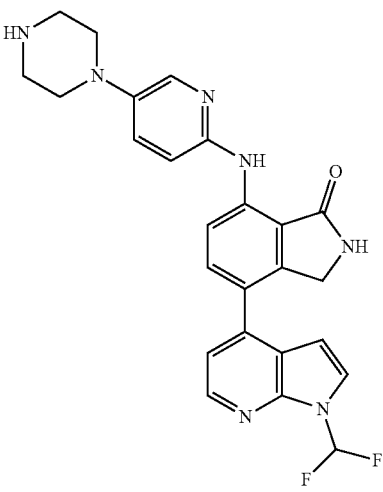
I-119

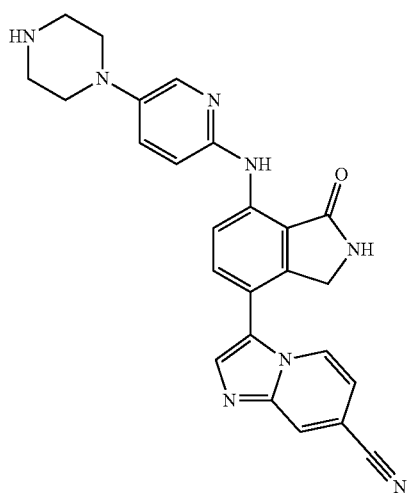
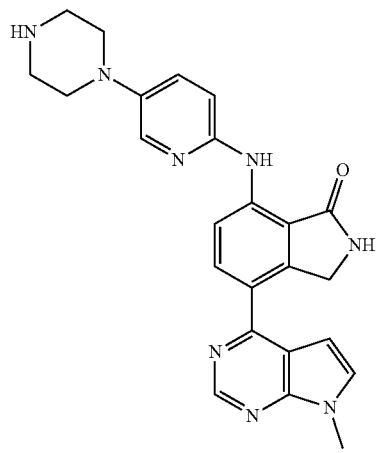
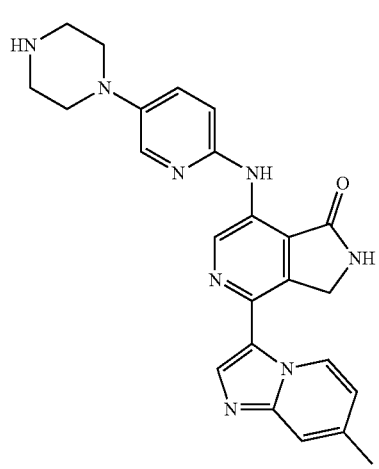

I-126
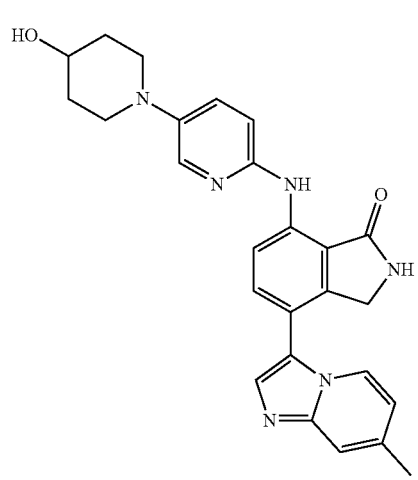
I-127
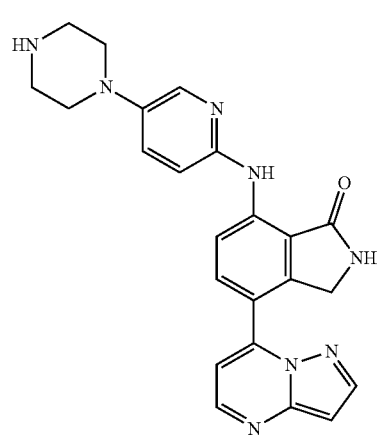
I-128
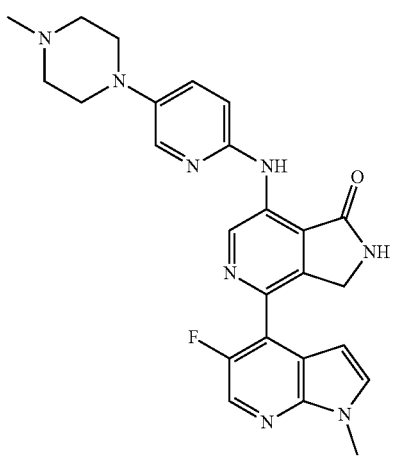
I-129
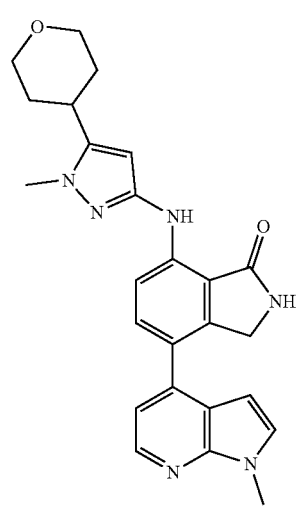
I-130
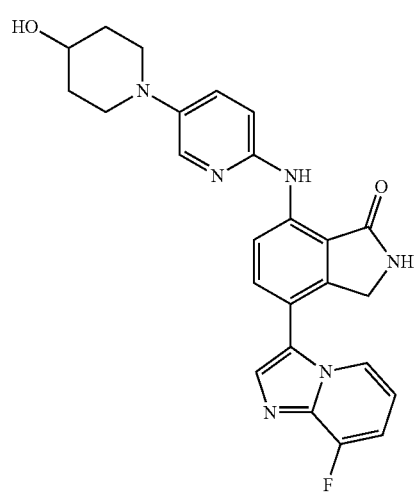
I-131
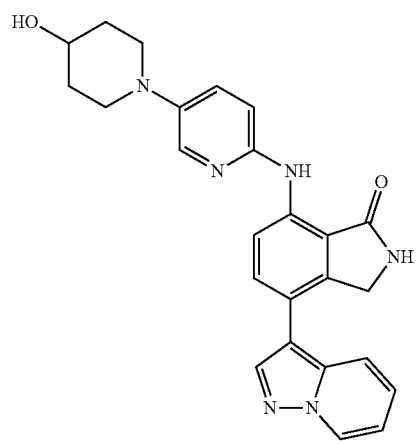

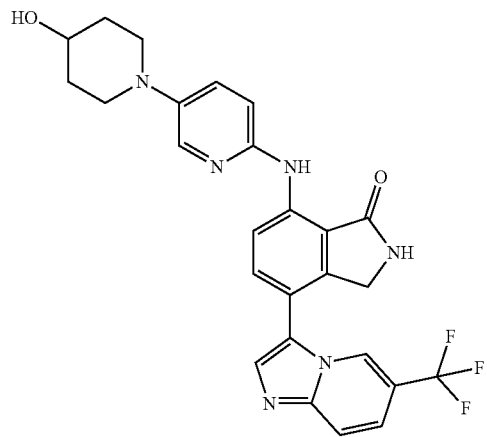
I-132
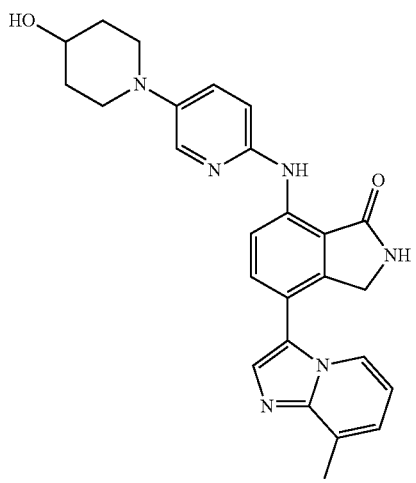
I-135
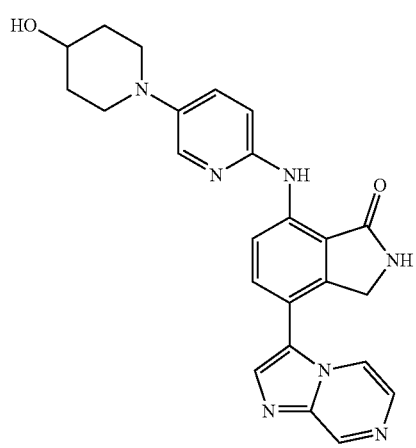
I-133
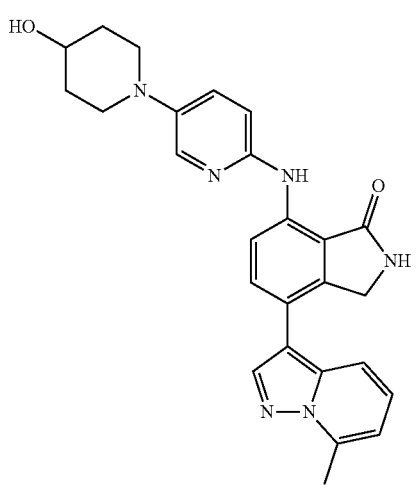
I-136
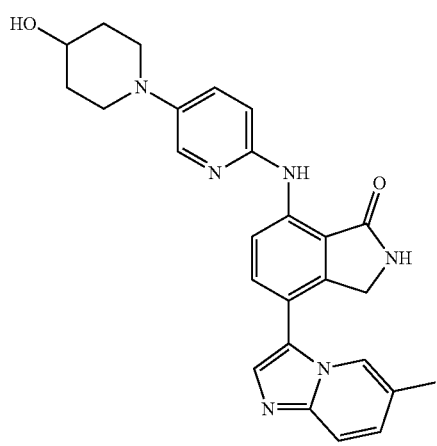
I-134
I-137

I-138
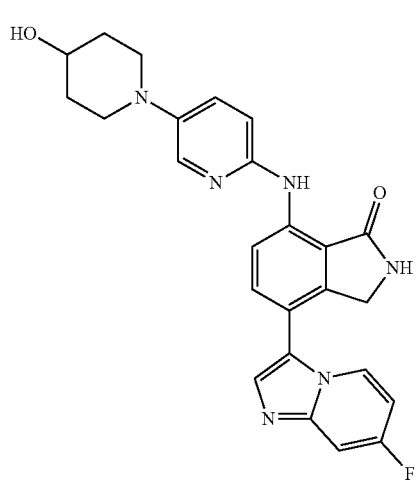
I-141
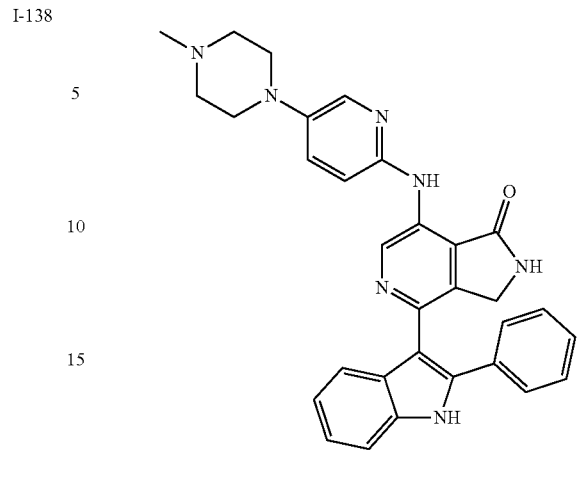
I-139
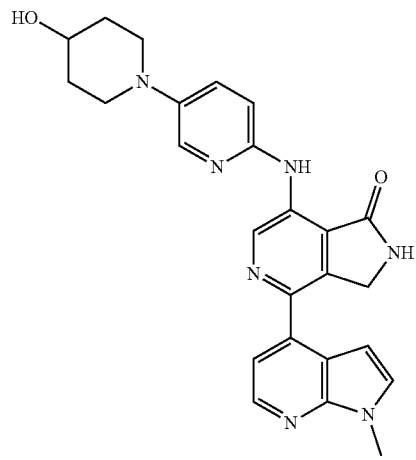
I-142
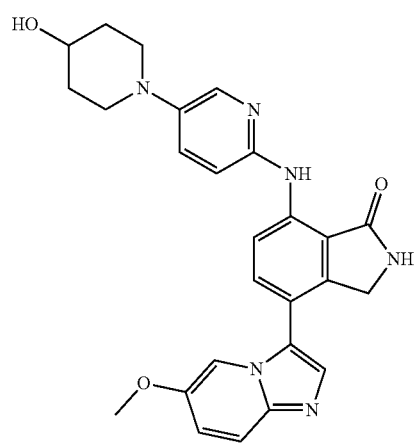
I-140
I-143
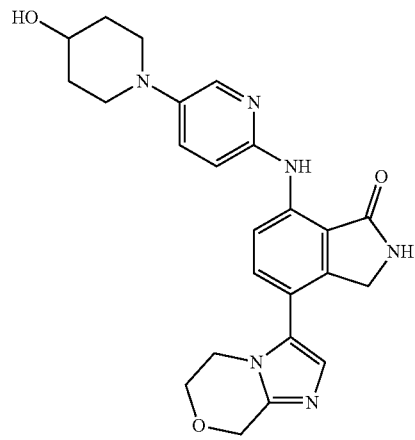

2453
-continued
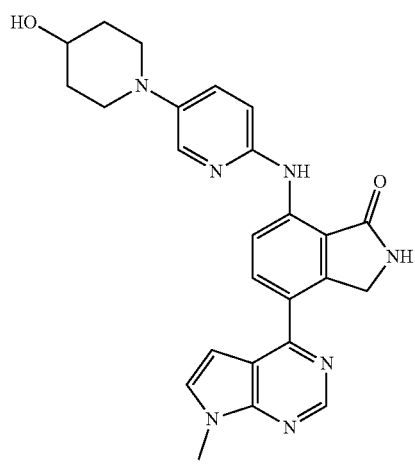
I-144
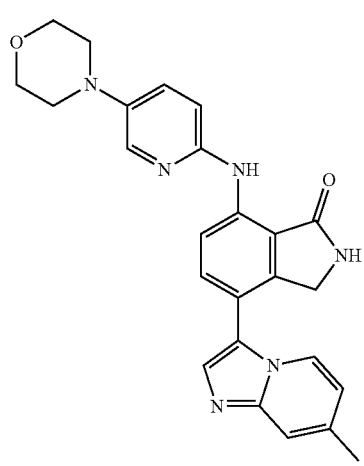
I-145
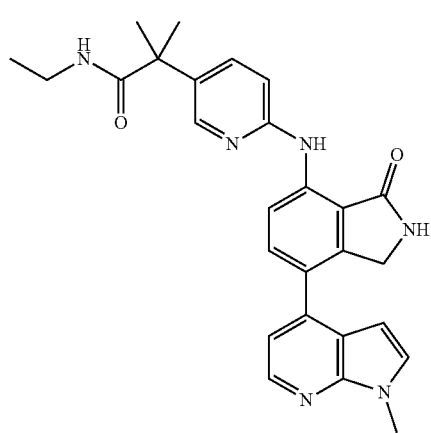
I-146
2454
-continued
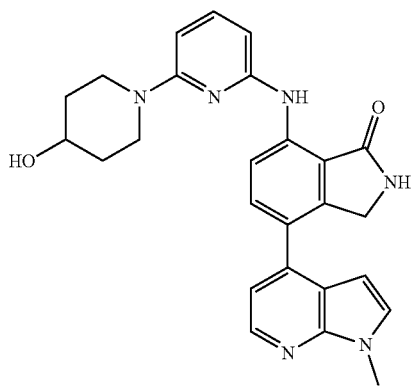
I-147
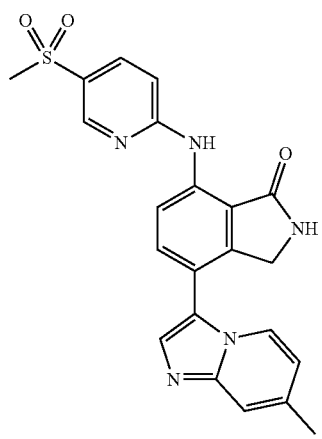
I-148
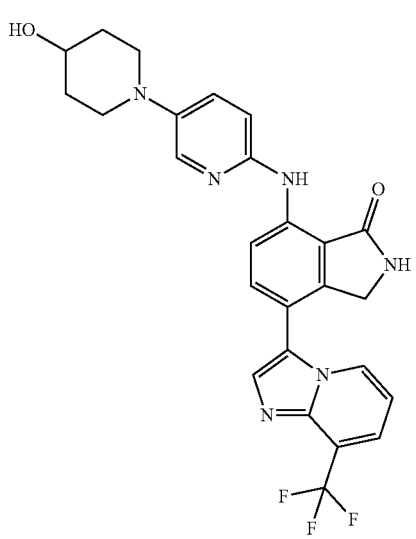
I-149

2455
-continued
I-150
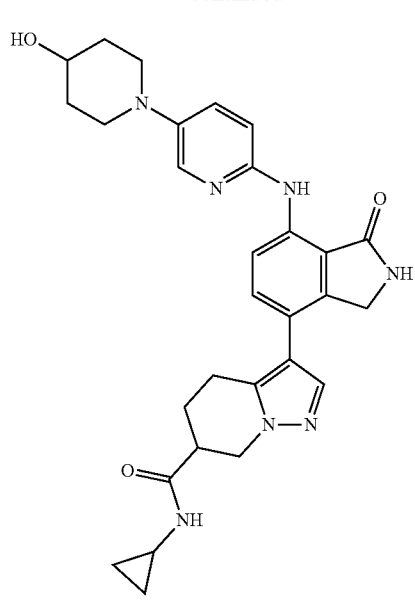
I-152
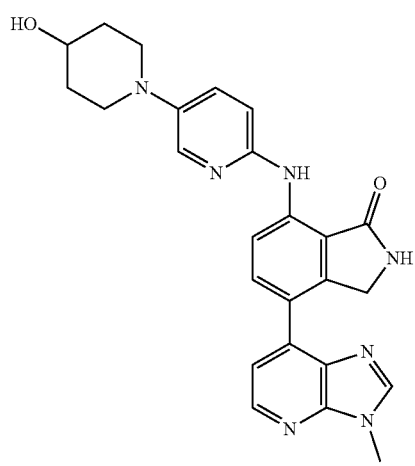
I-153
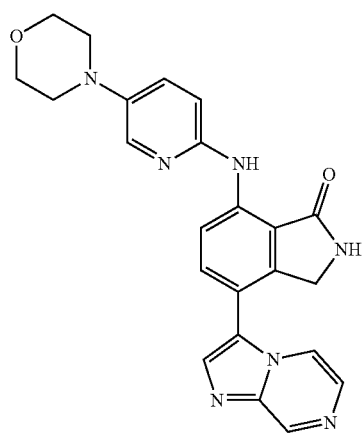
2456
-continued
I-154
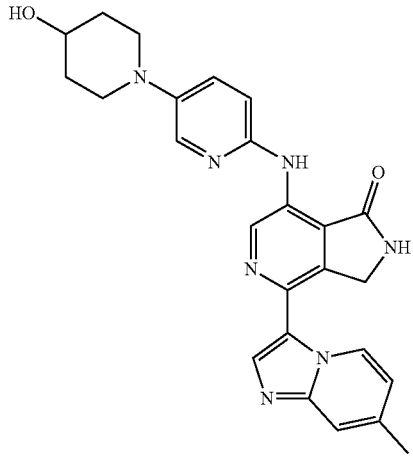
I-155
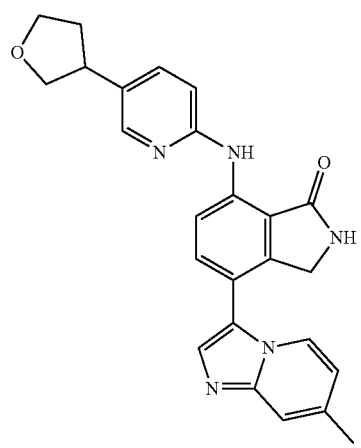
I-156
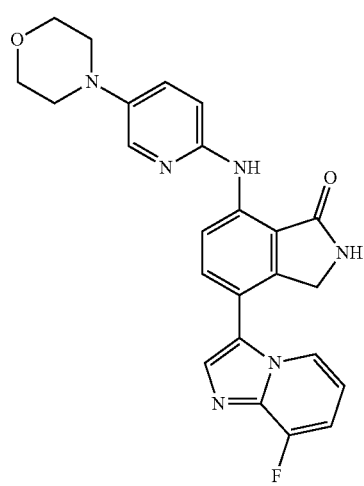

I-157
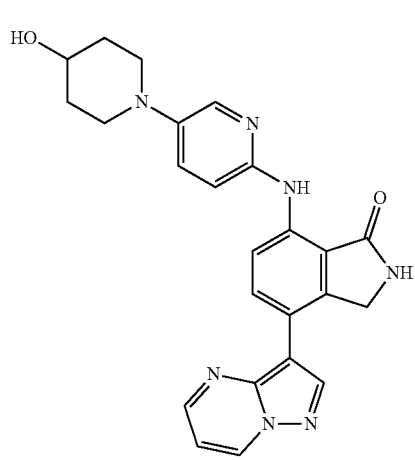
I-160
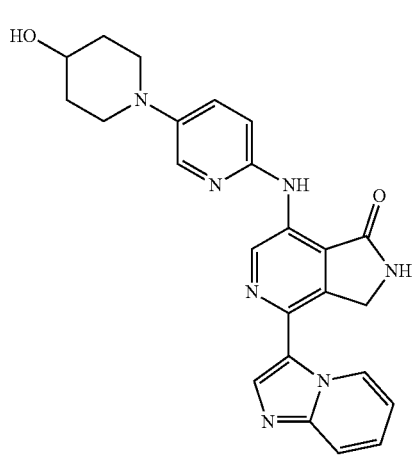
I-158
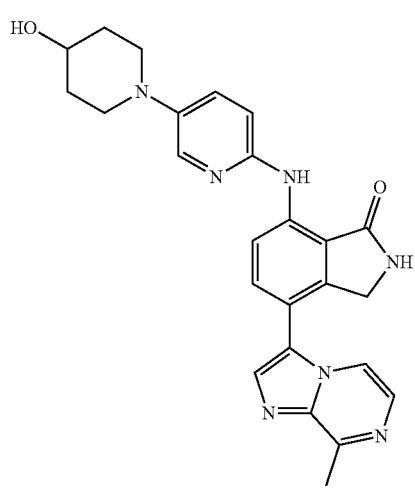
I-161
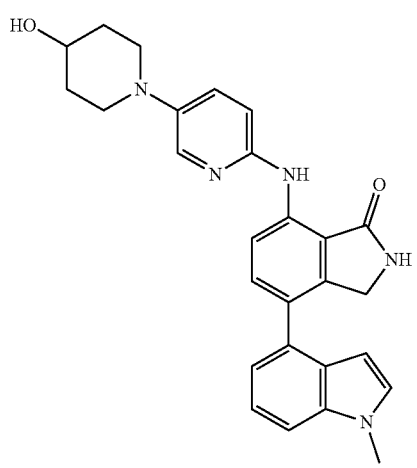
I-159
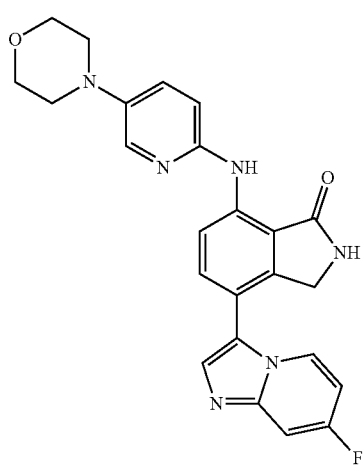
I-162
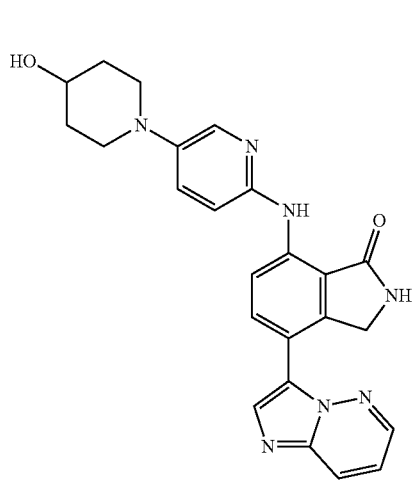

I-163
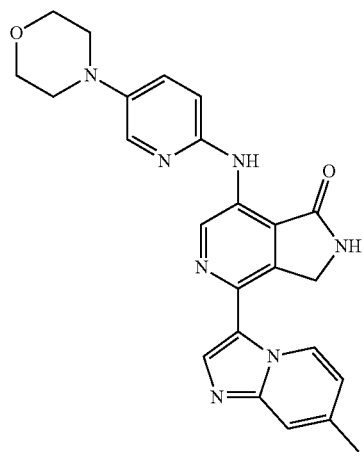
I-164
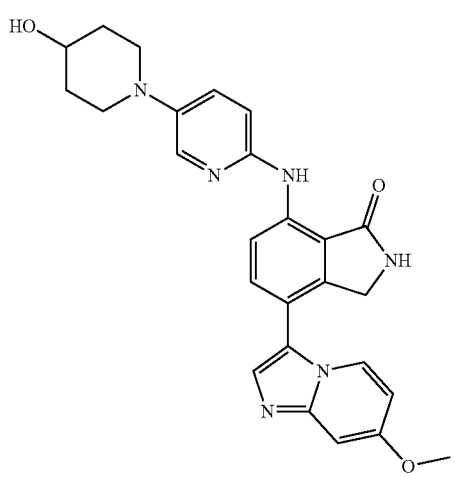
I-165
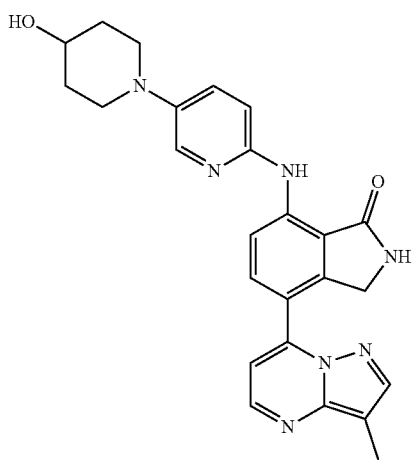
I-166
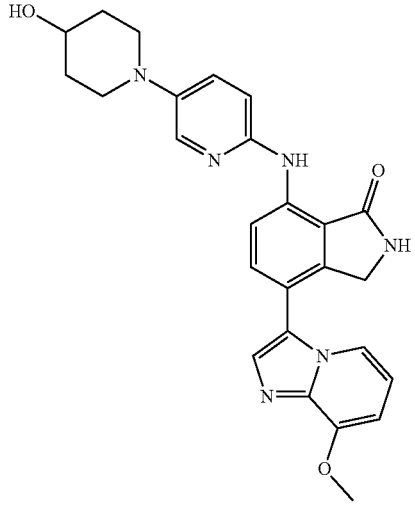
I-167
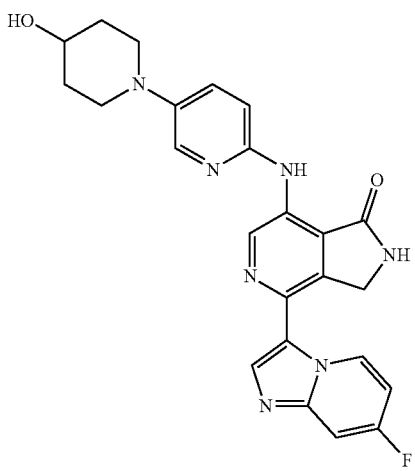
I-168
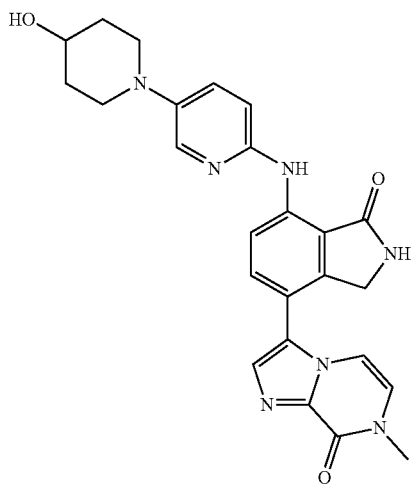

I-169
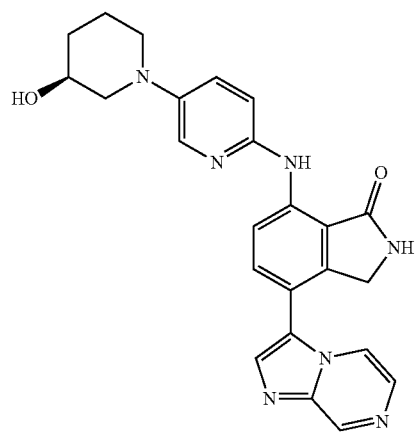
I-172
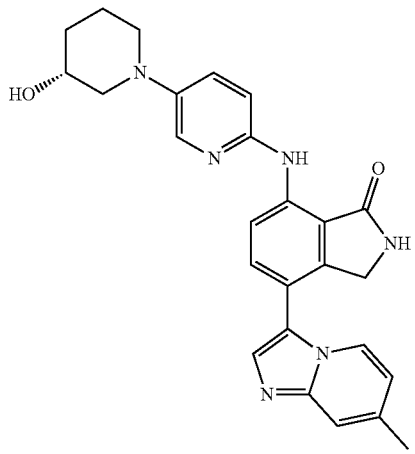
I-170
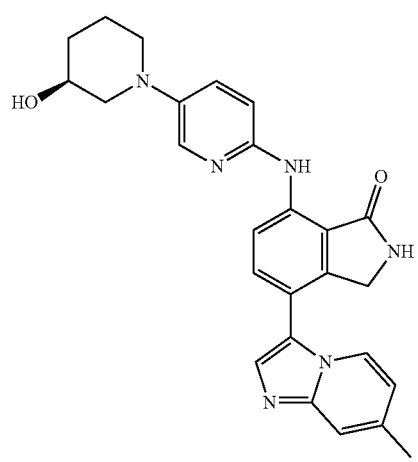
I-173
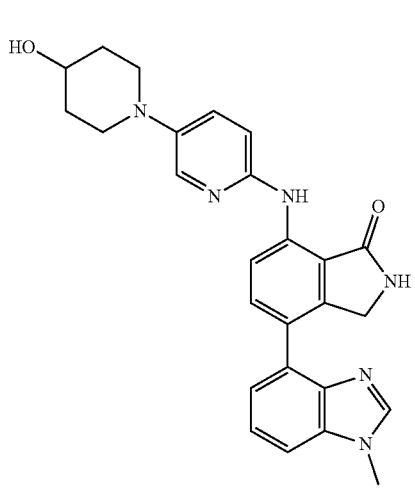
I-171
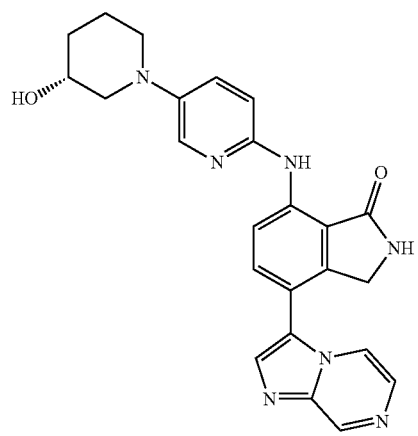
I-174
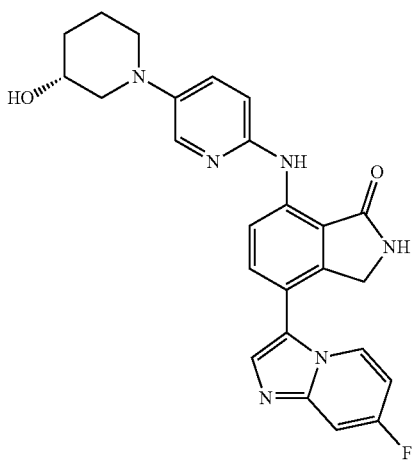

I-175
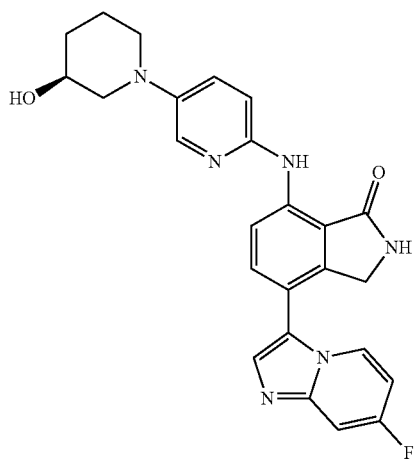
I-178
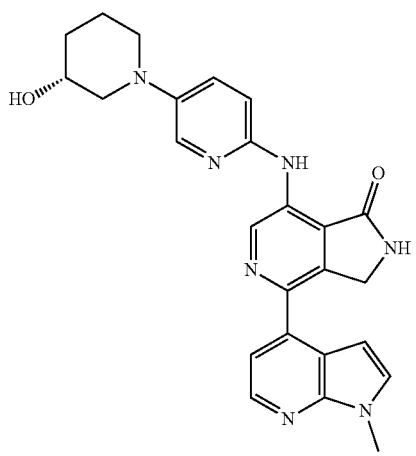
I-176
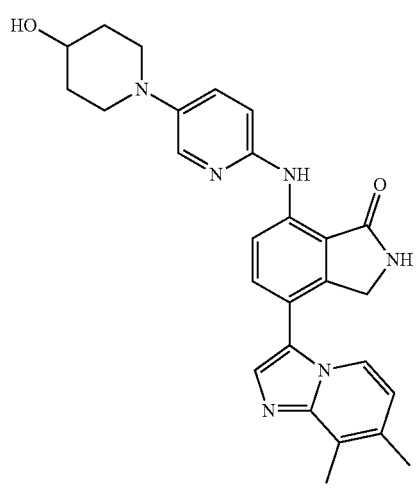
I-179
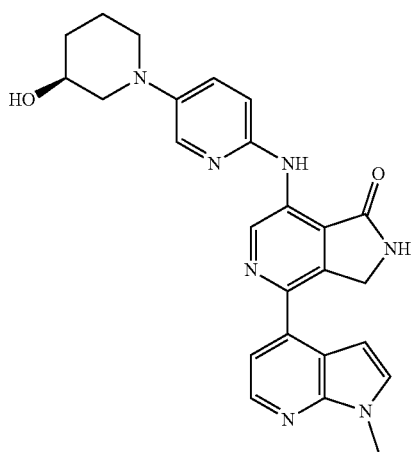
I-177
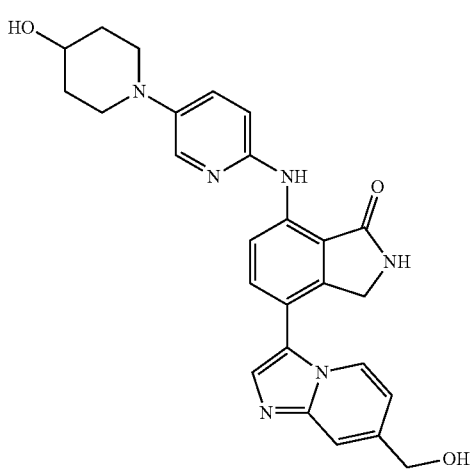
I-180
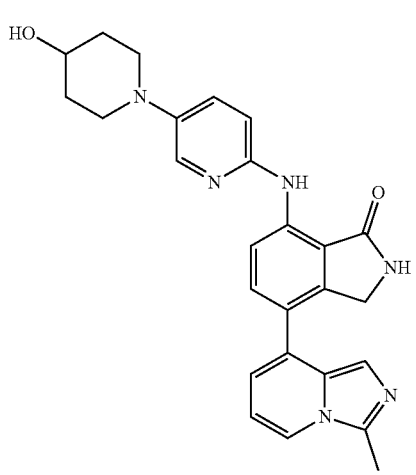

I-181
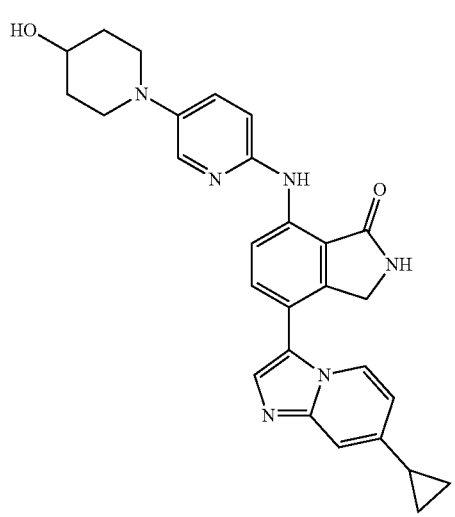
I-182
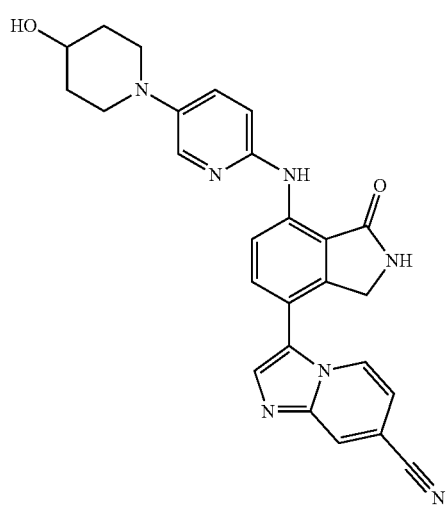
I-183
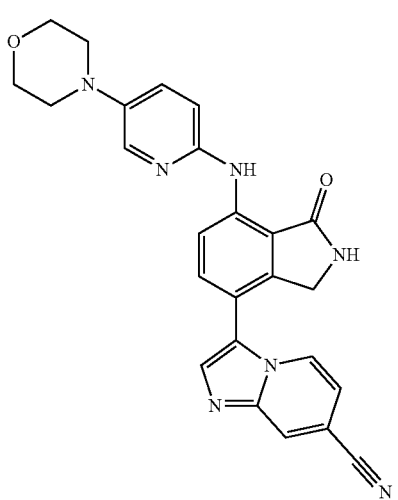
I-184
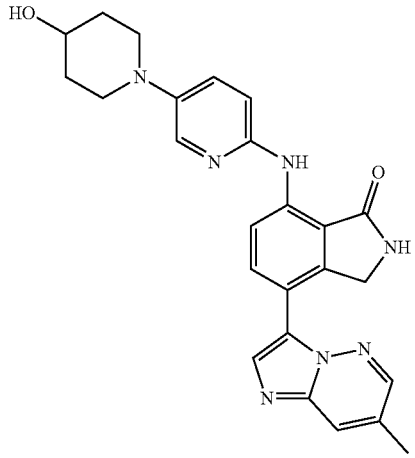
I-185
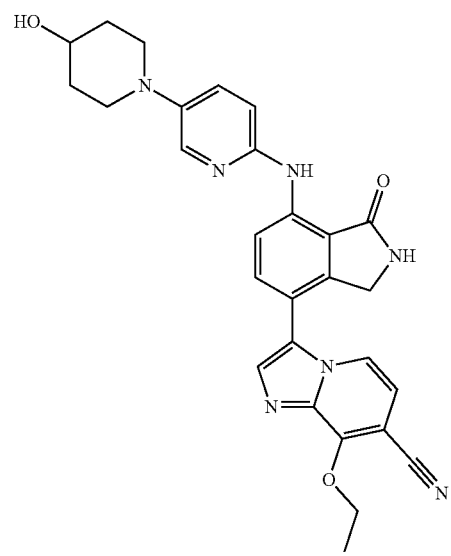
I-186
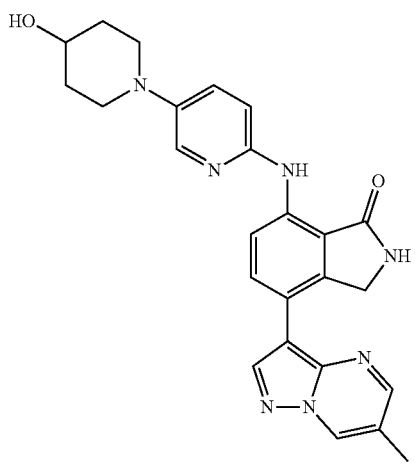

2467
-continued
I-187
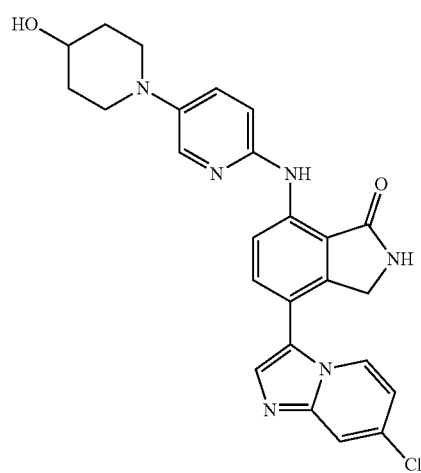
I-188
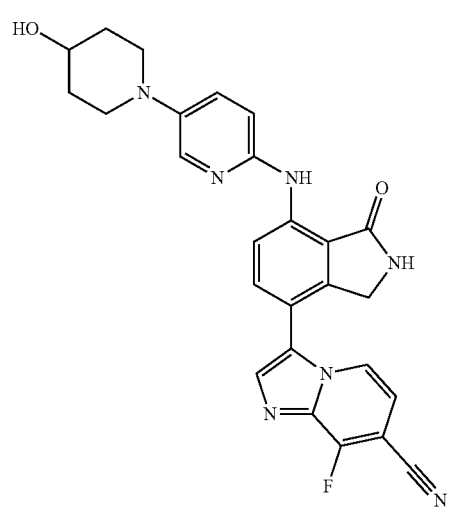
I-189
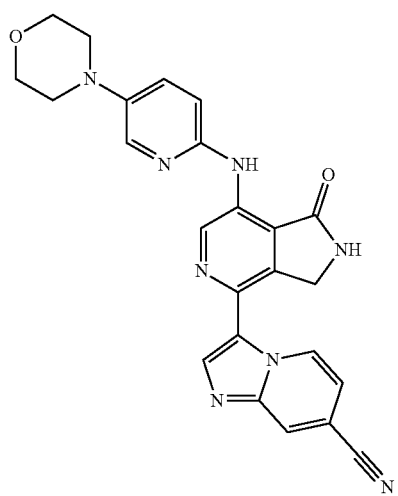
2468
-continued
I-190
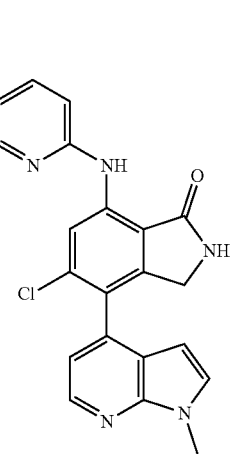
I-191
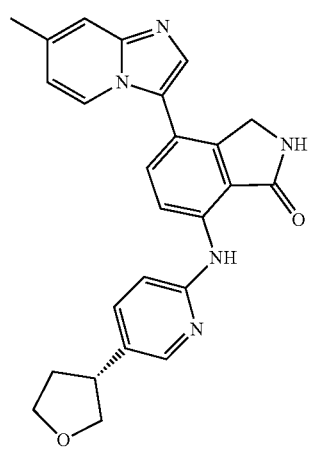
I-192

I-193
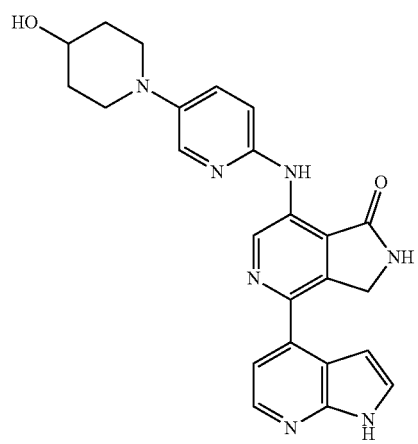
I-194
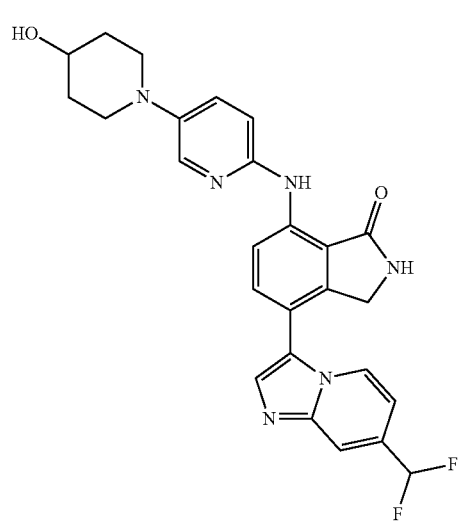
I-195
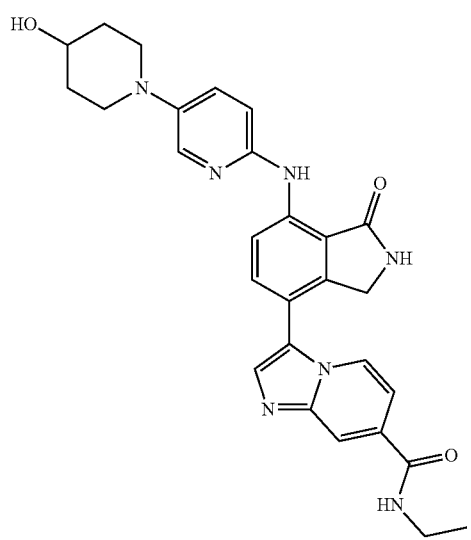
I-196
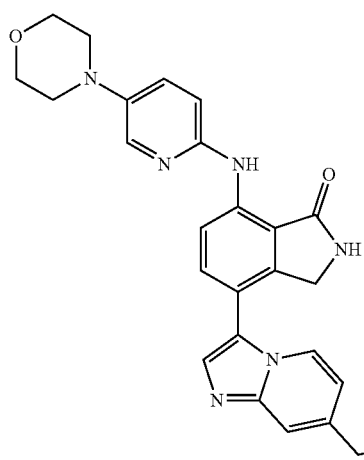
I-197
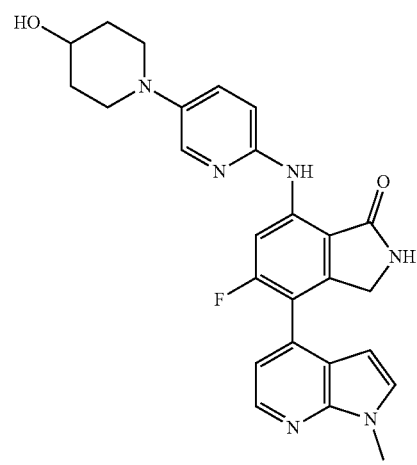
I-198
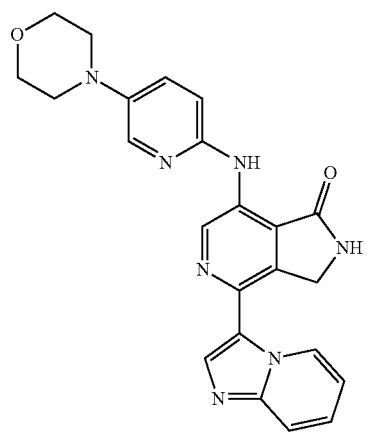

I-199
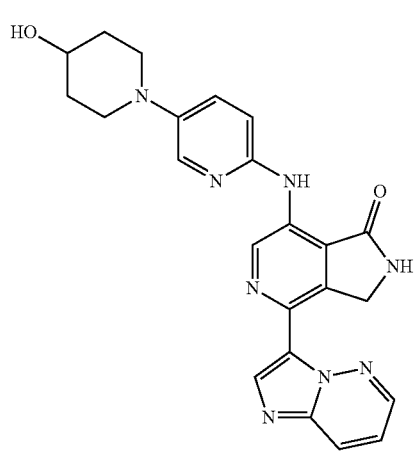
I-202
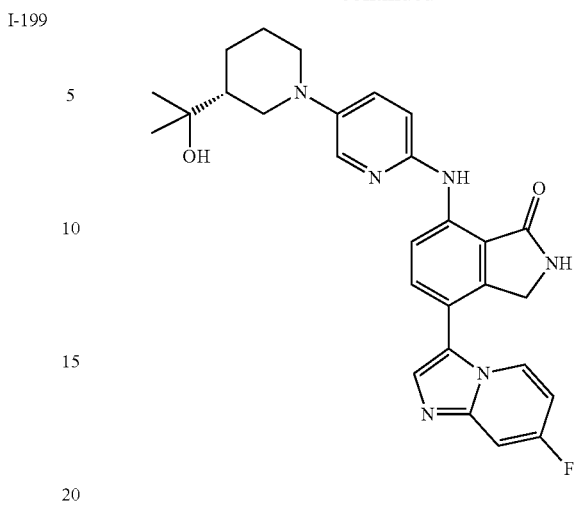
I-200
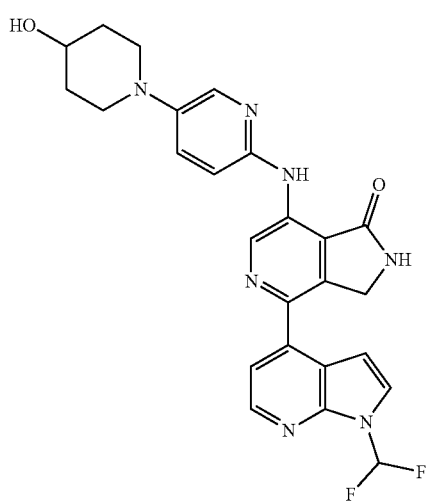
I-203
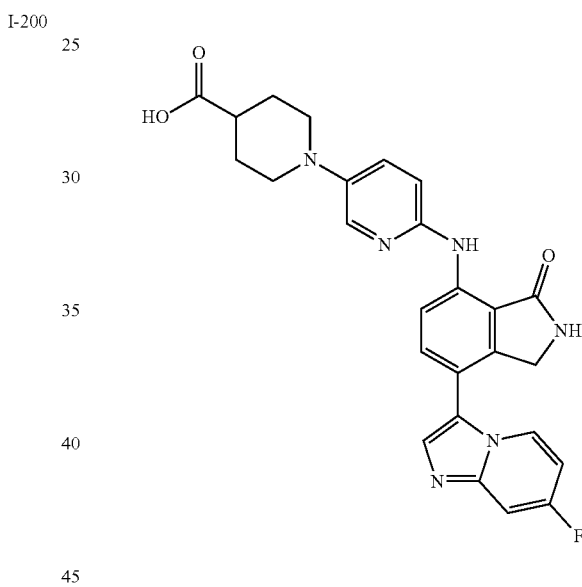
I-201
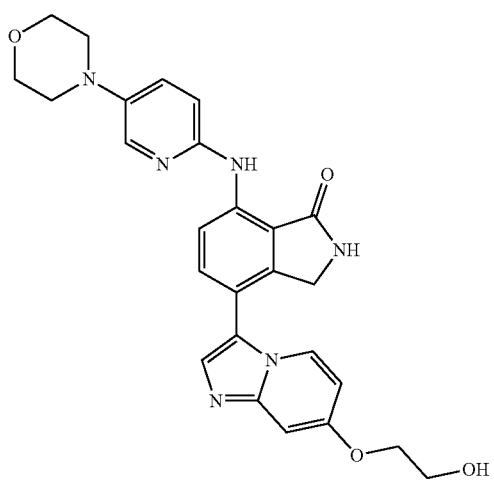
I-204
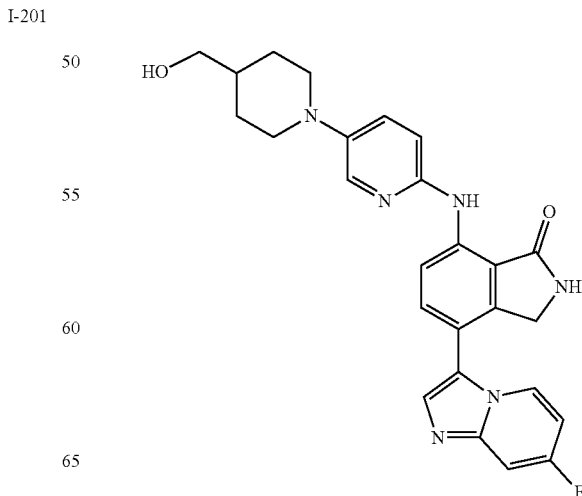

2473
-continued
I-205
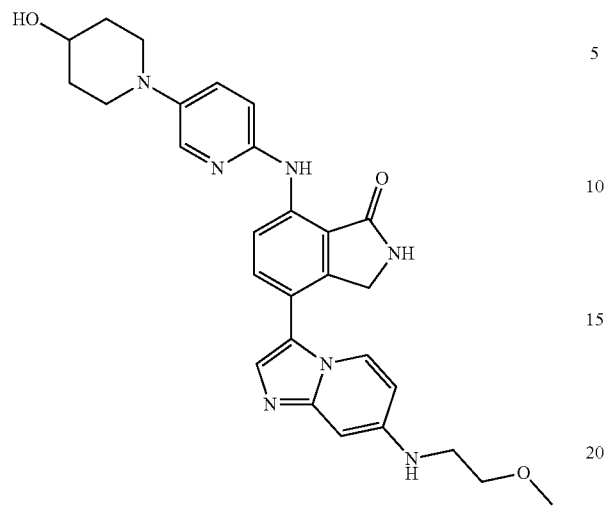
I-206
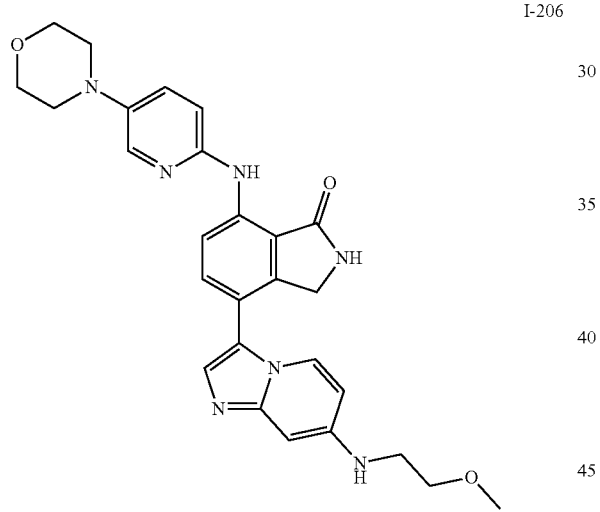
I-207
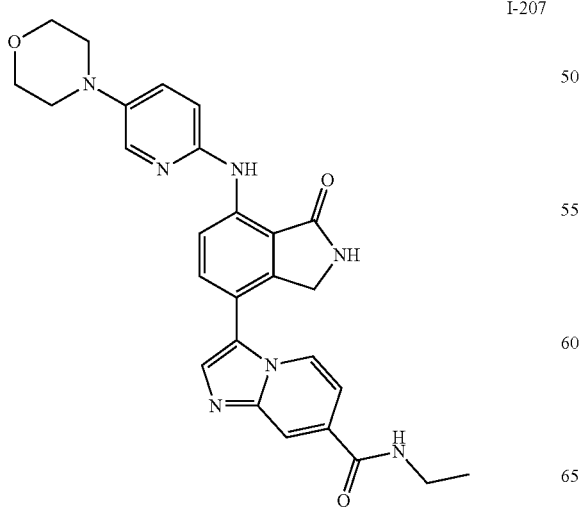
2474
-continued
I-208
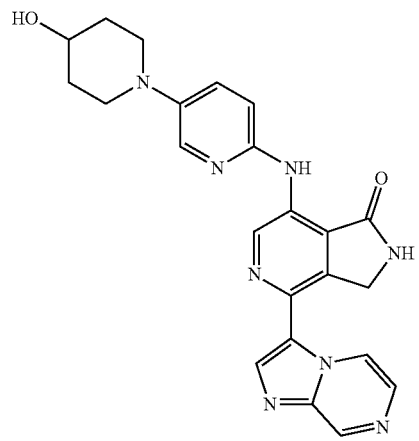
I-209
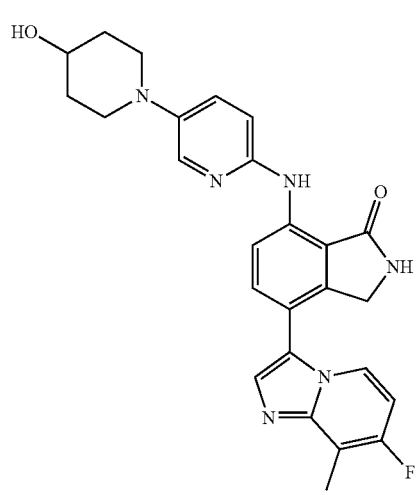
I-210
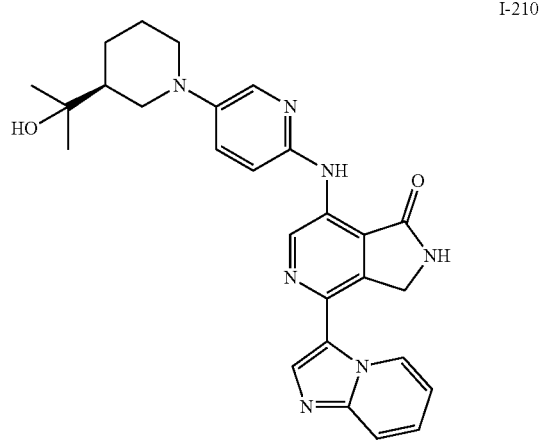

2475 I-211
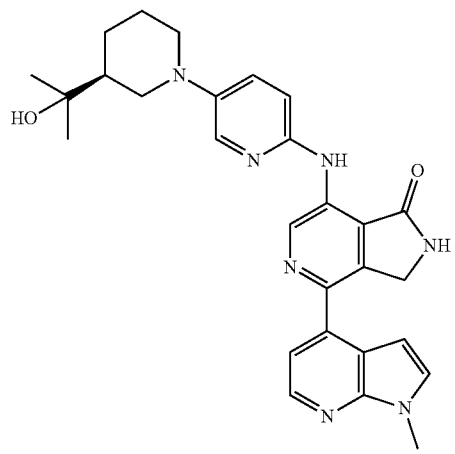
I-212
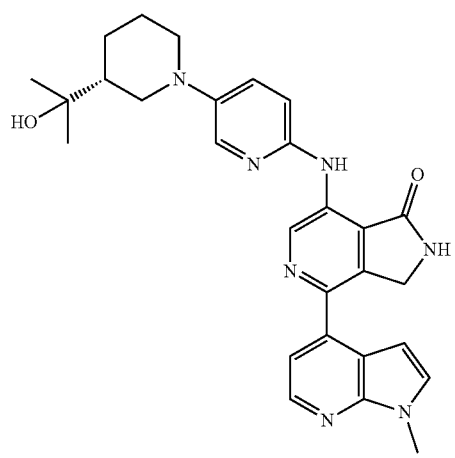
I-213
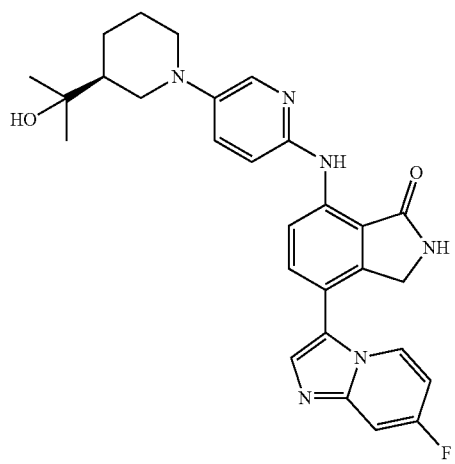
2476 I-214
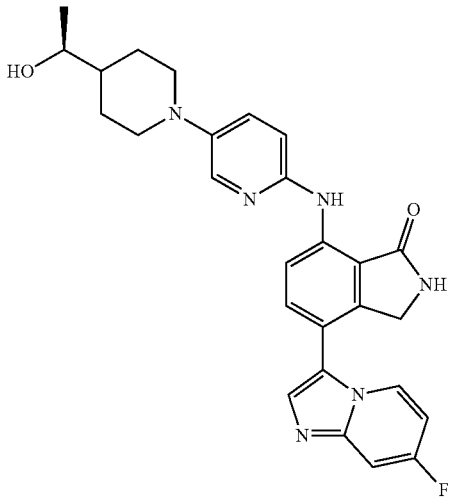
I-215
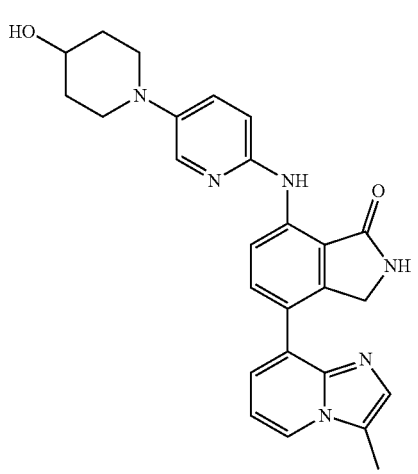
I-216
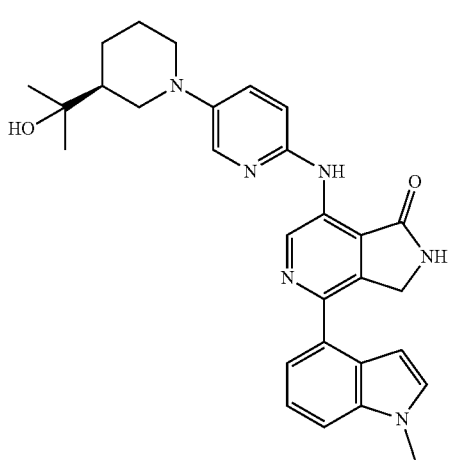

I-217
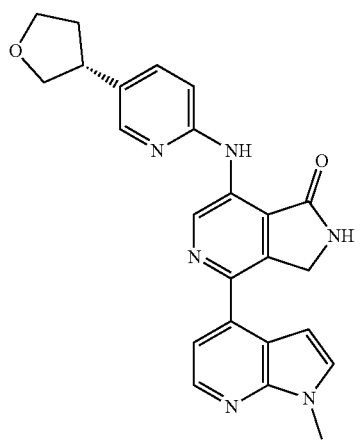
I-218
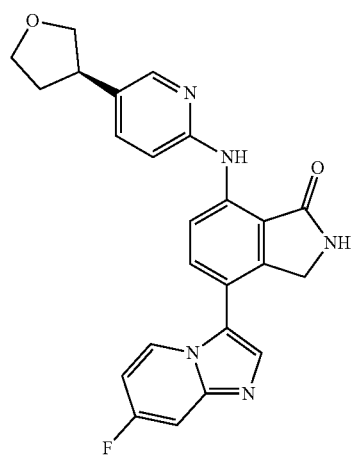
I-219
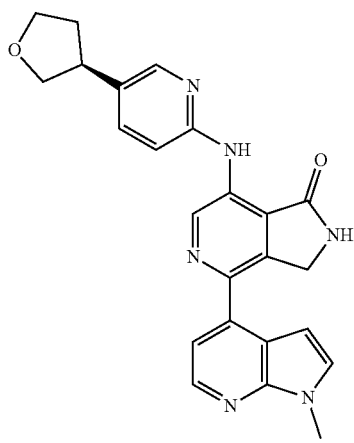
I-220
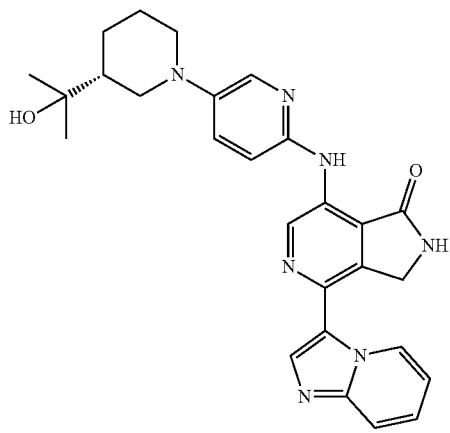
I-221
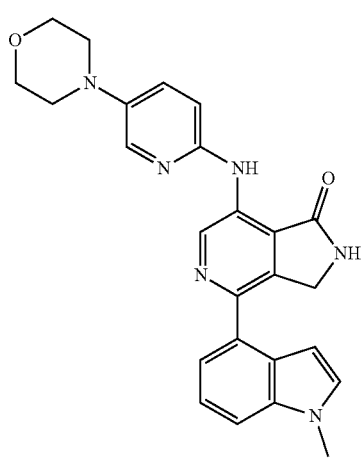
I-222
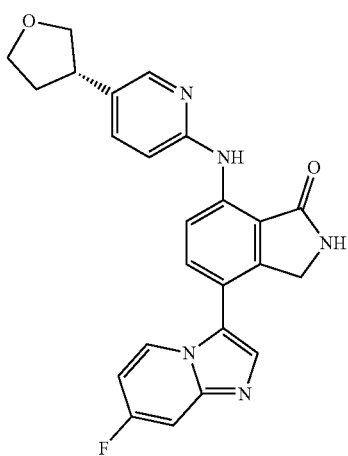

I-223
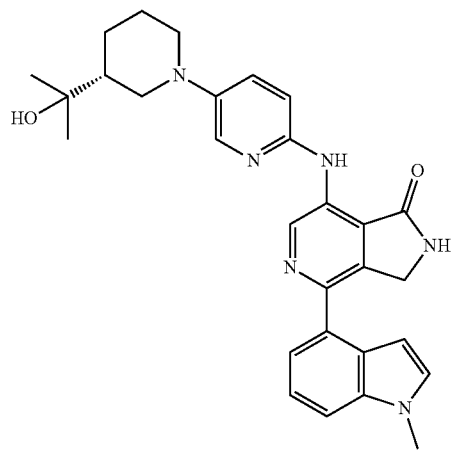
I-227
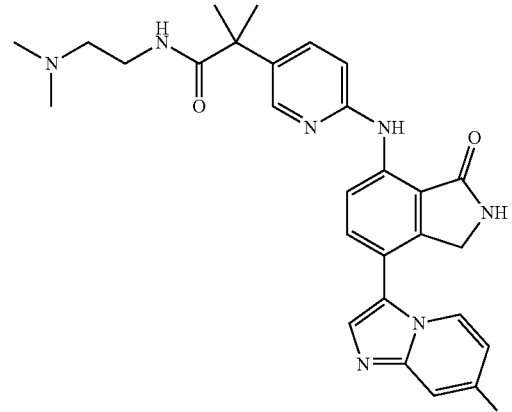
I-224
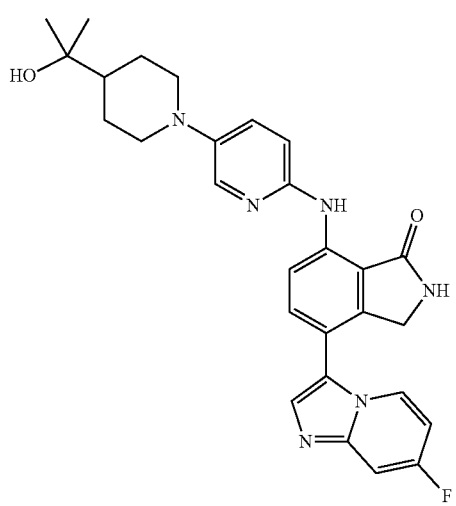
I-228
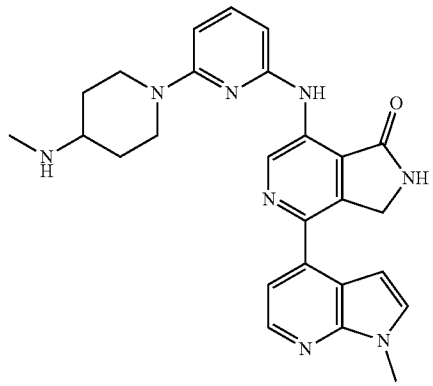
I-225
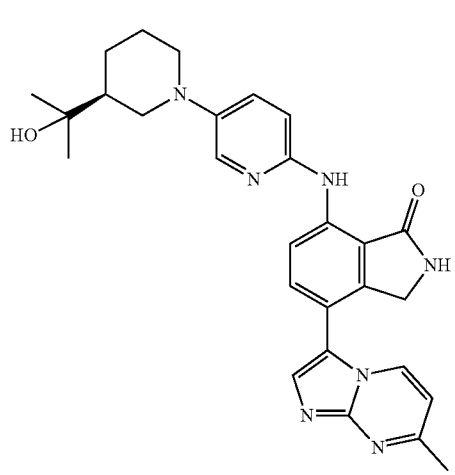
I-229
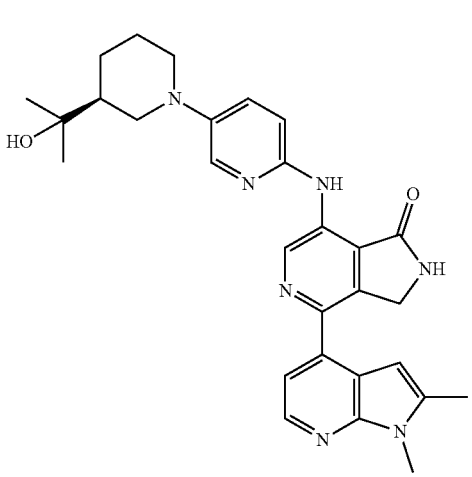

I-230

I-231

I-232

I-233

I-234

I-235

I-236

I-237

I-238
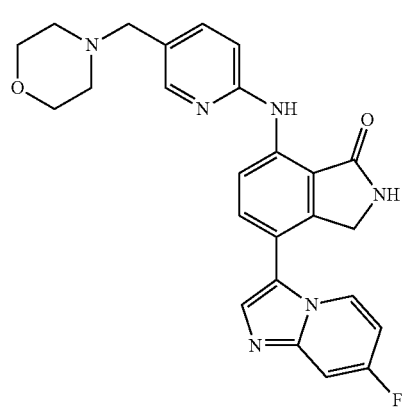
I-239
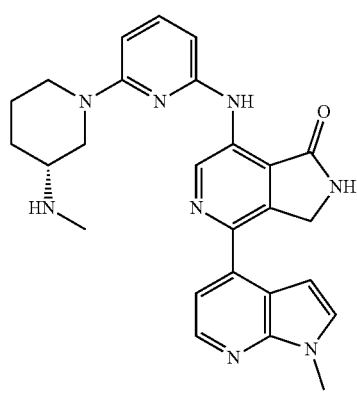
I-240
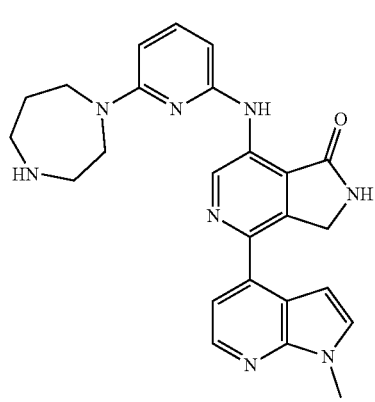
I-241
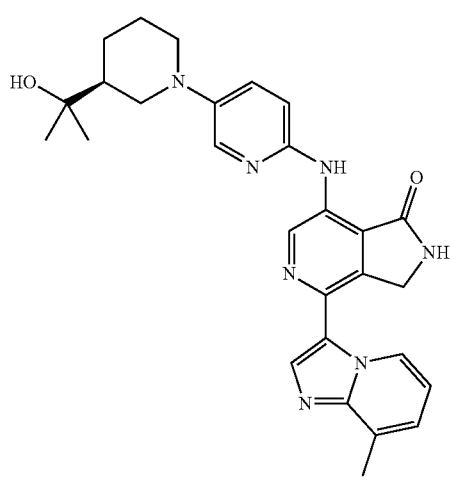
I-242
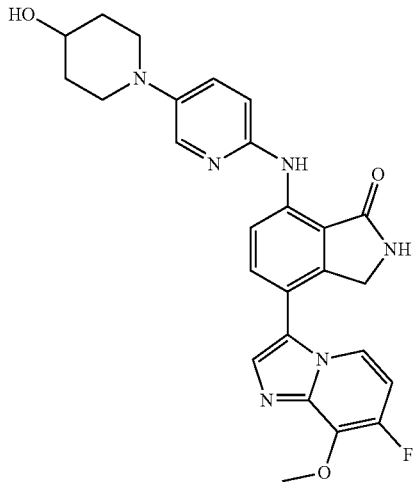
I-244
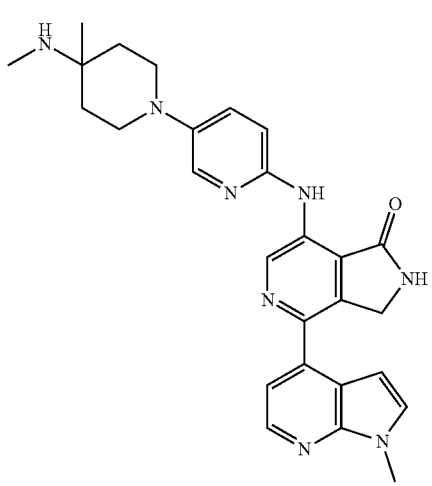
I-245
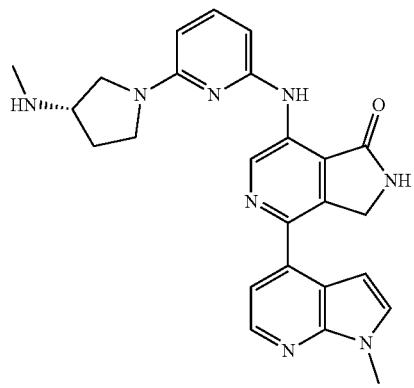

I-246
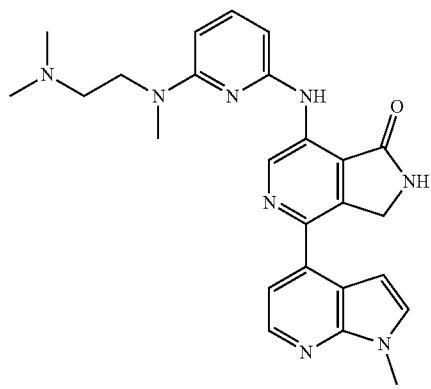
I-249
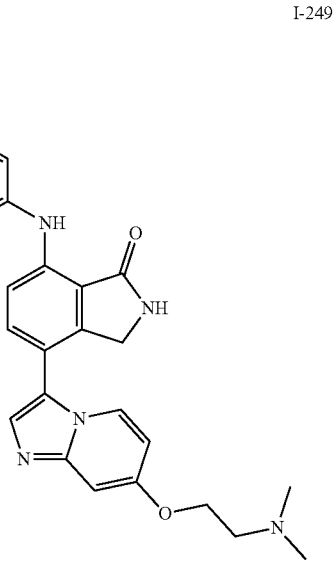
I-247
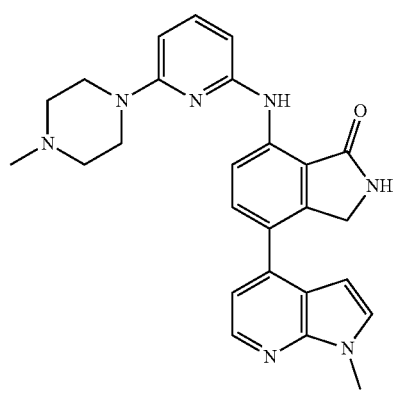
I-250
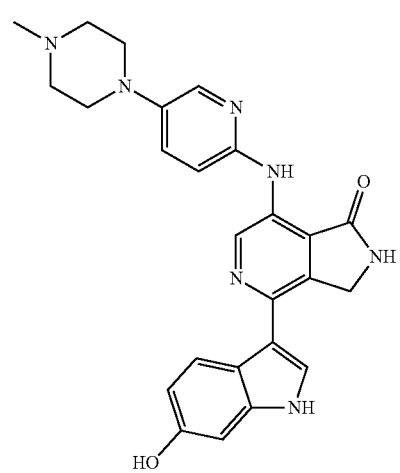
I-248
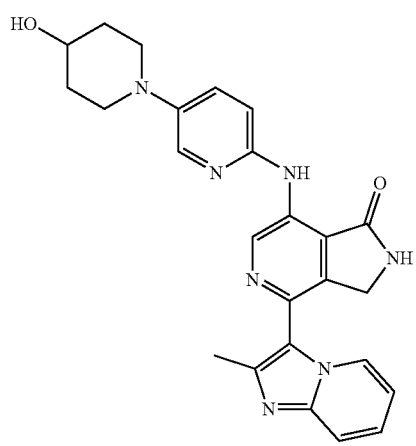
I-251
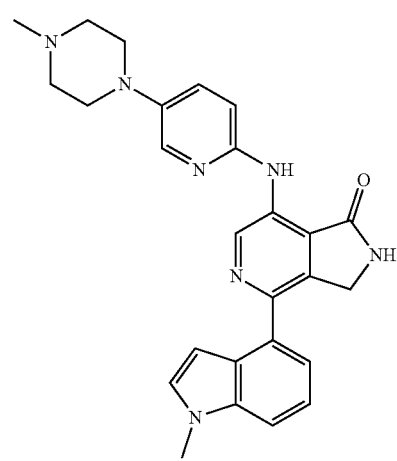

I-252
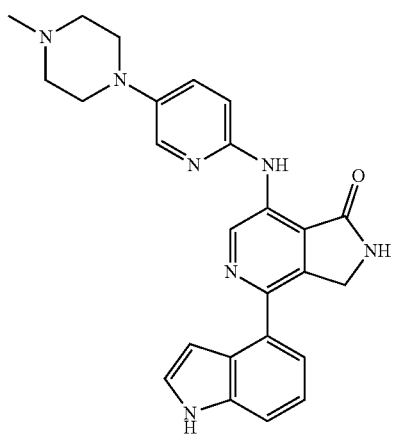
I-255
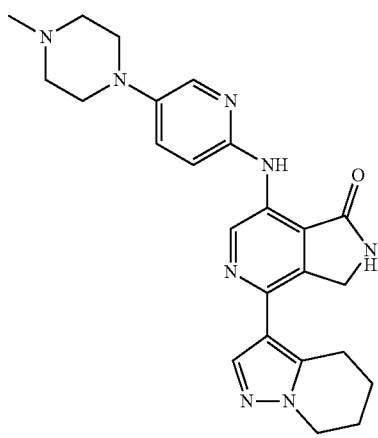
I-253
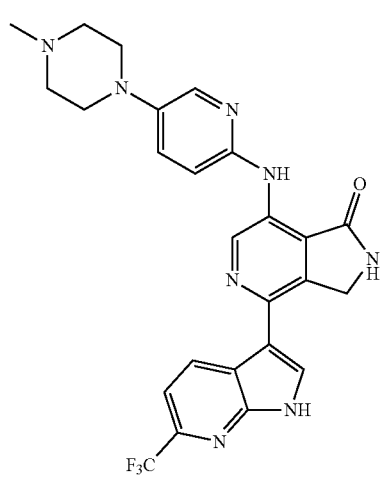
I-256
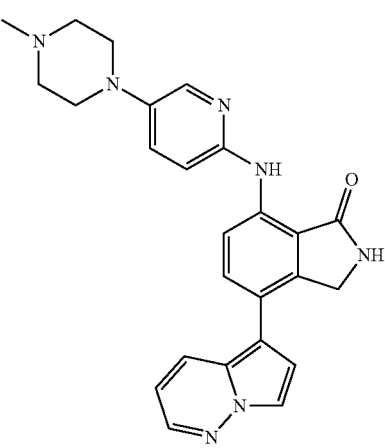
I-254
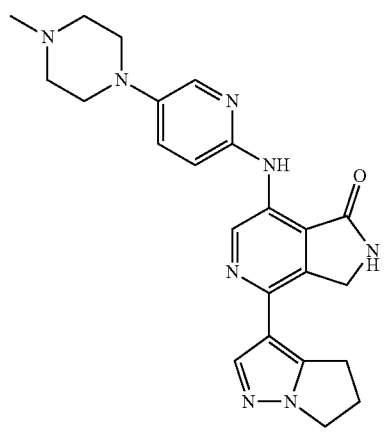
I-257
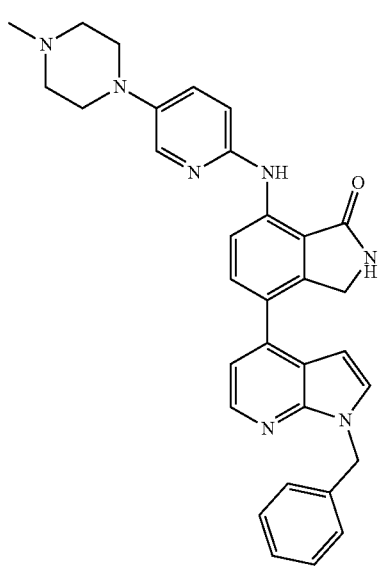

| 2489 -continued | 2490 -continued |
|---|---|
| 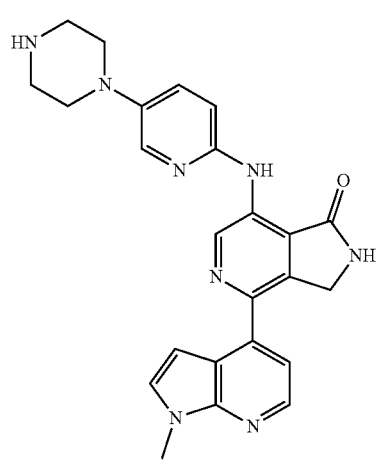 I-258 | 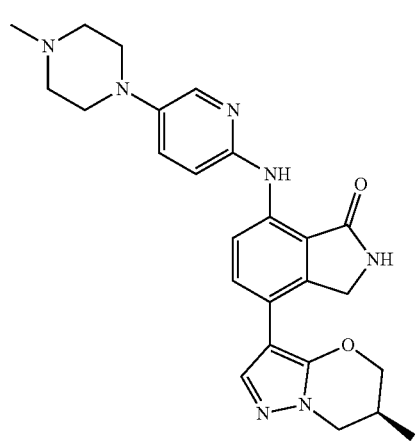 I-261 |
| 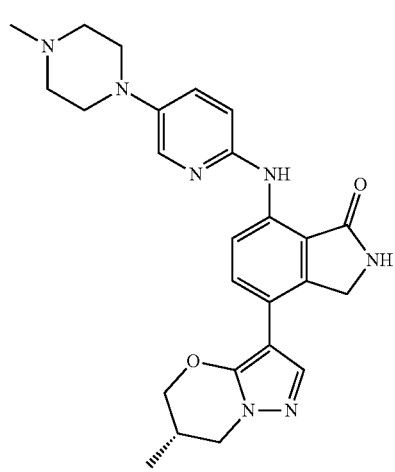 I-259 | 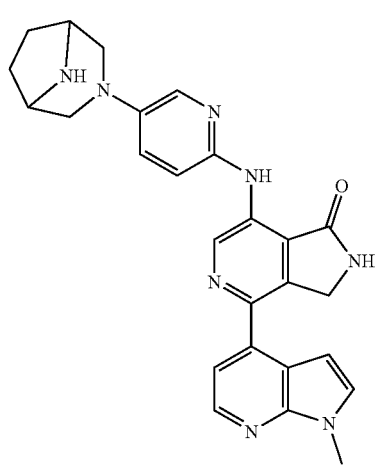 I-262 |
| 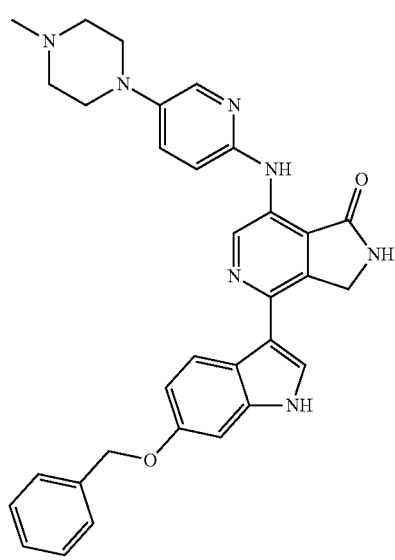 I-260 | 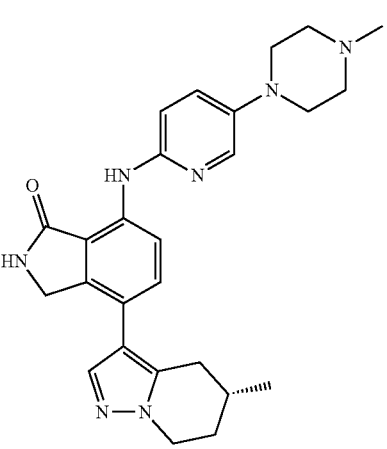 I-263 |

-continued
I-264
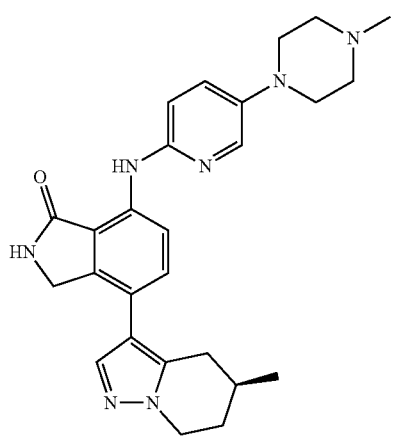
I-267
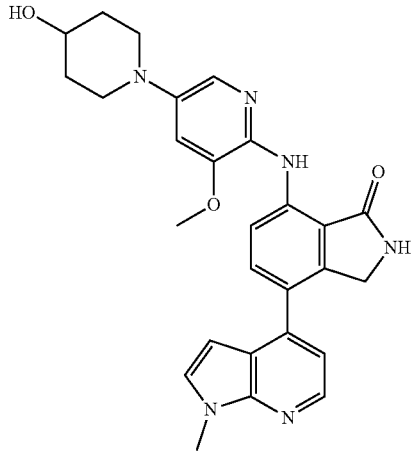
I-265
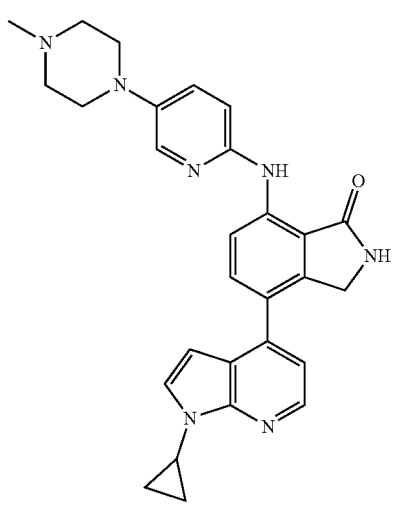
I-268
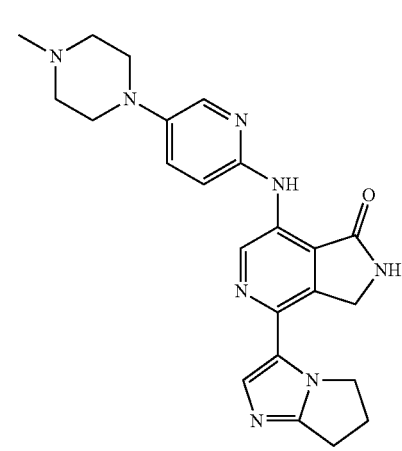
I-266
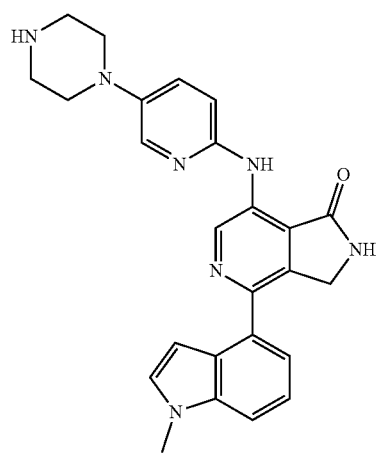
I-269
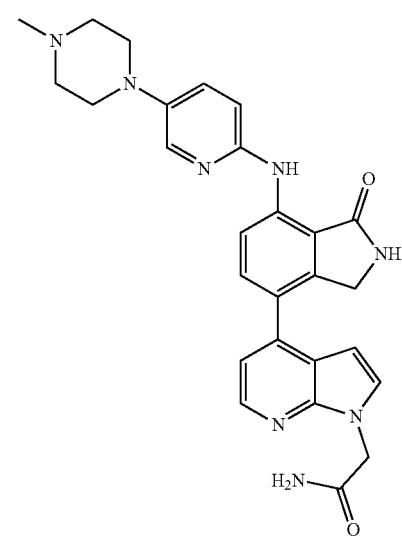

2493 -continued
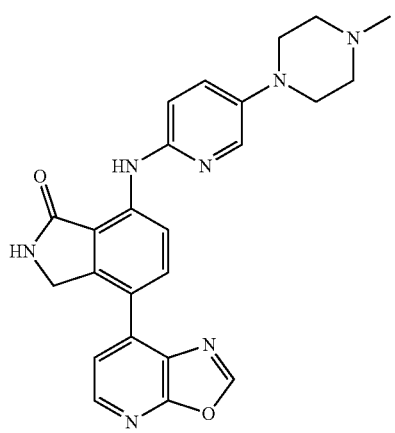
I-270
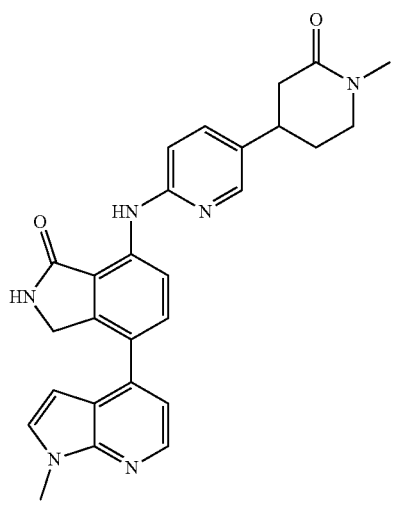
I-271
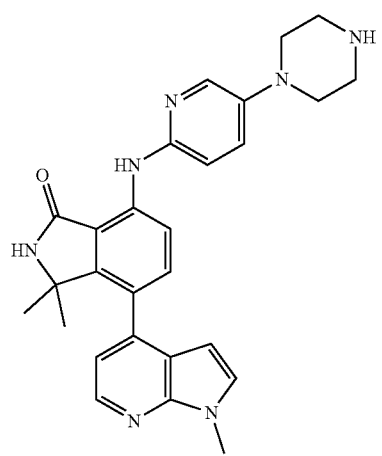
I-273
2494 -continued
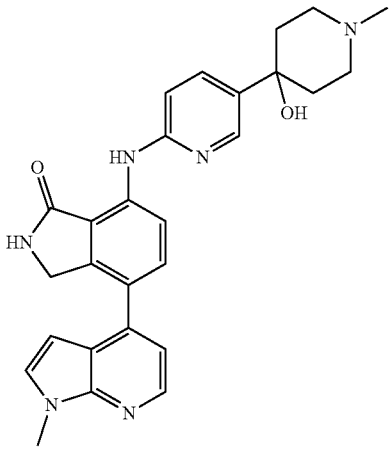
I-274
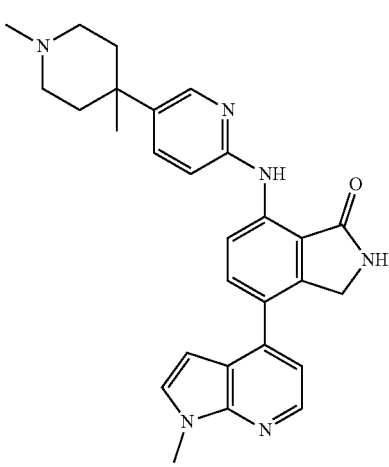
I-275
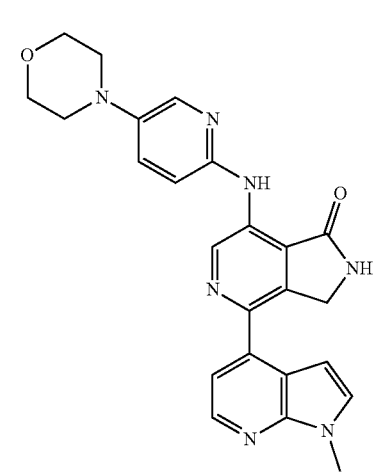
I-276

I-278
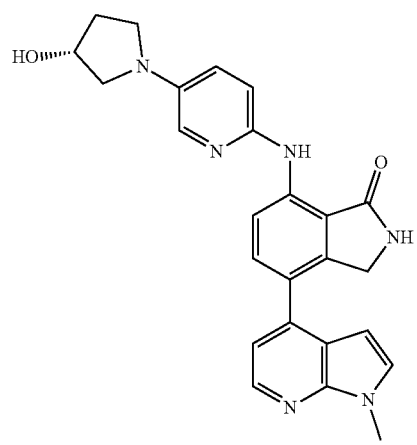
I-279
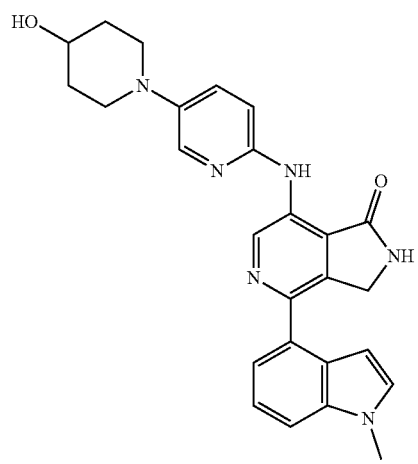
I-282
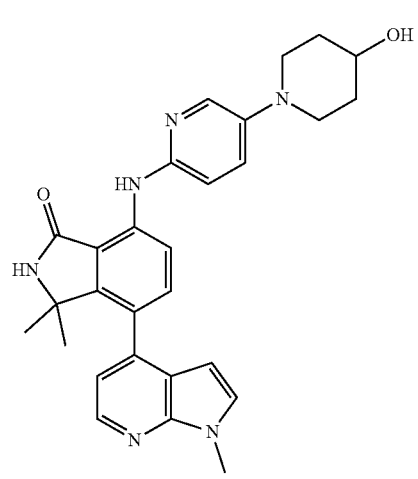
I-283
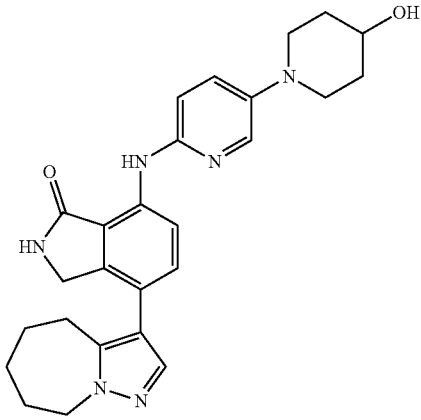
I-284
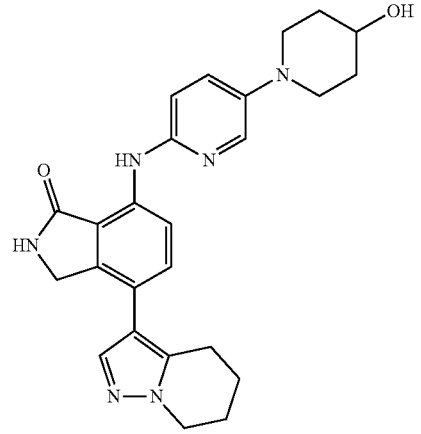
I-285
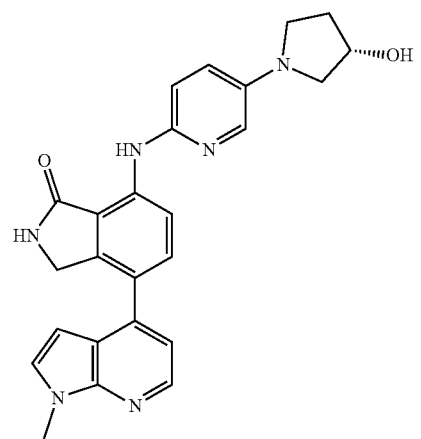

I-286
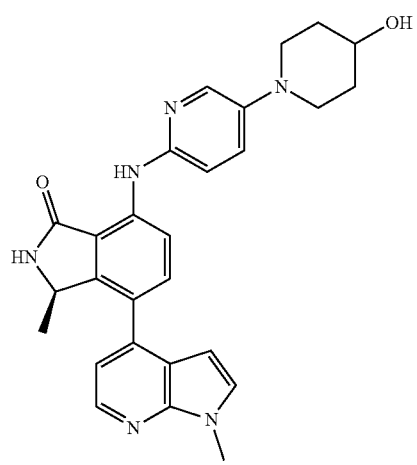
I-289
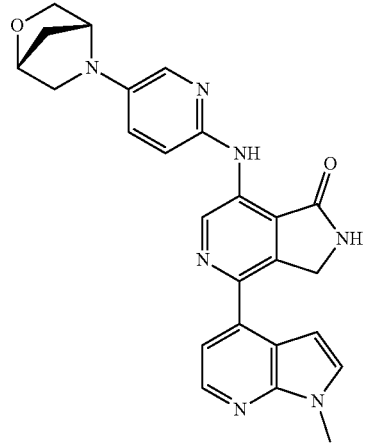
I-287
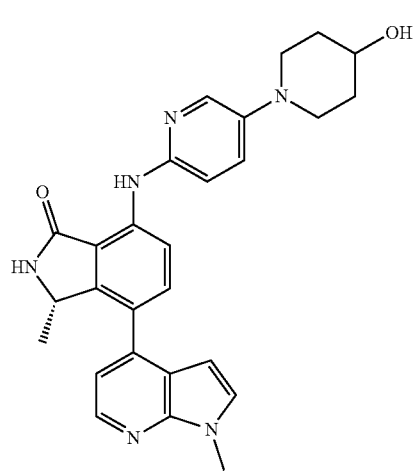
I-290
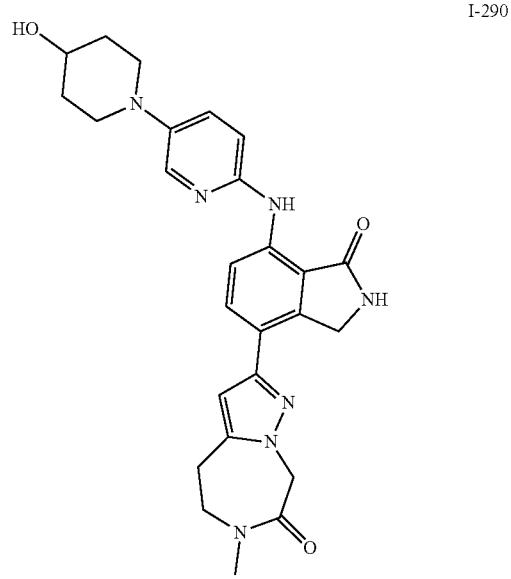
I-288
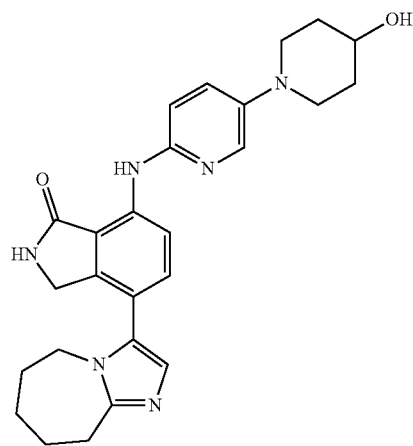
I-291
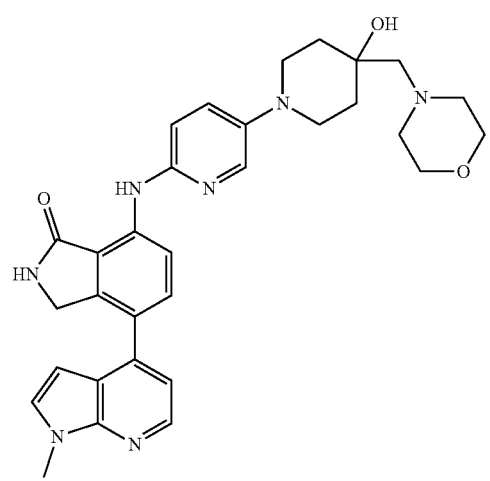

I-292
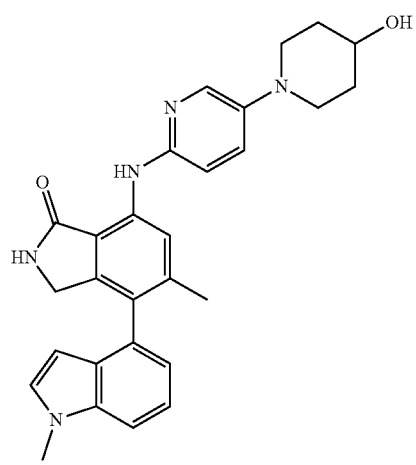
I-293
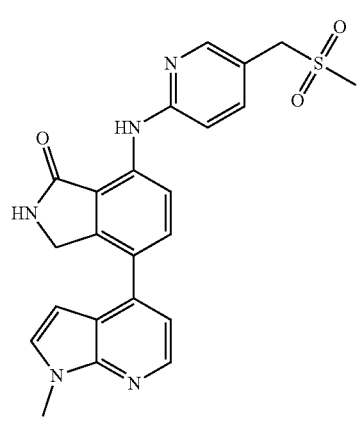
I-294
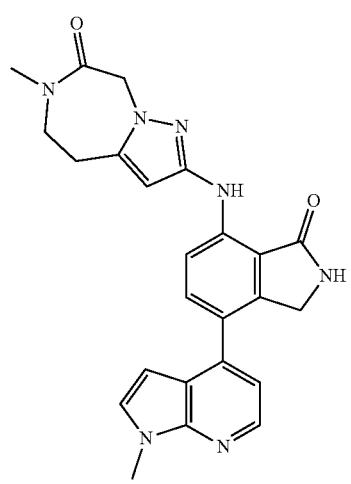
I-295
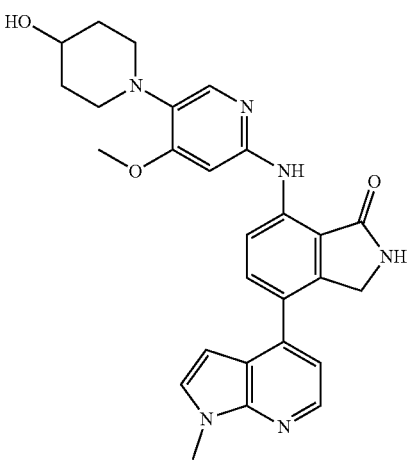
I-296
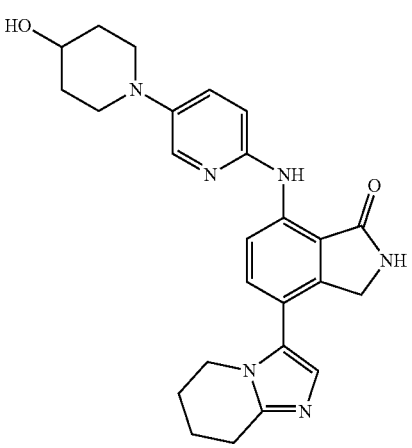
I-297
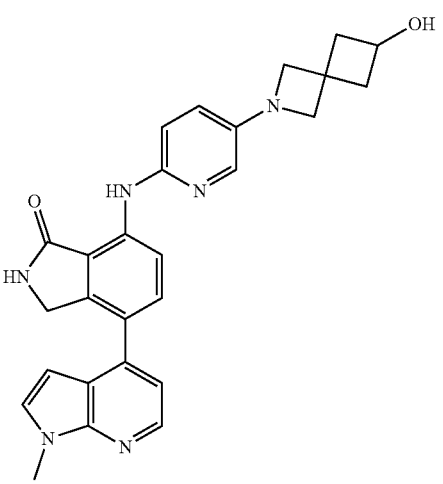

-continued
I-298
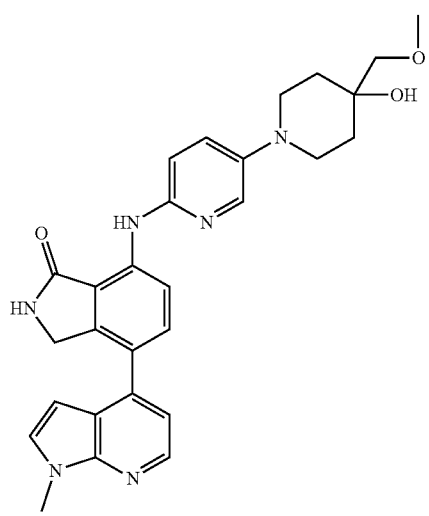
I-299
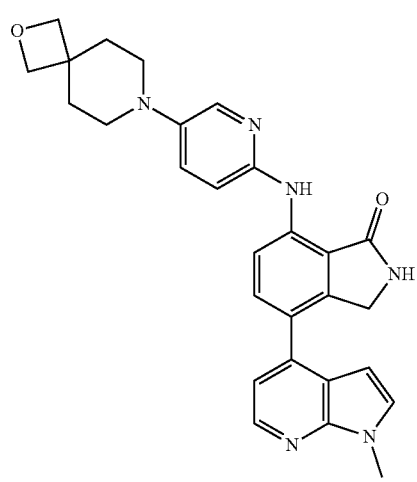
I-300
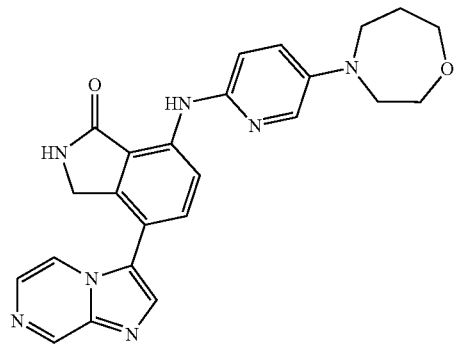
-continued
I-301
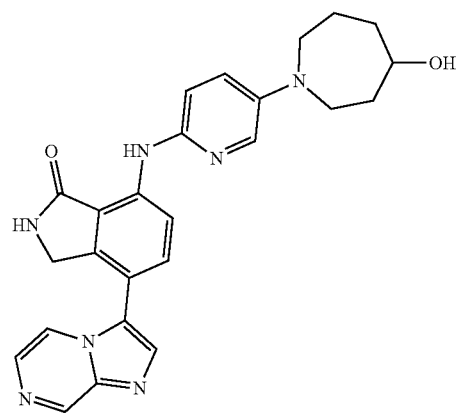
I-302
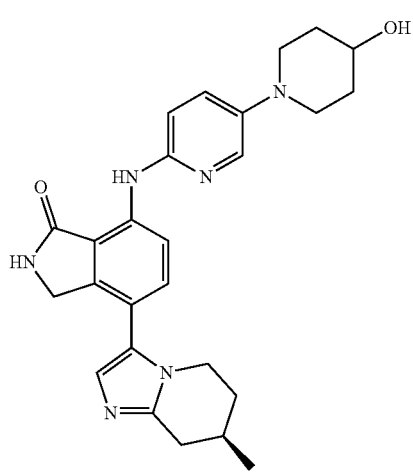
I-303
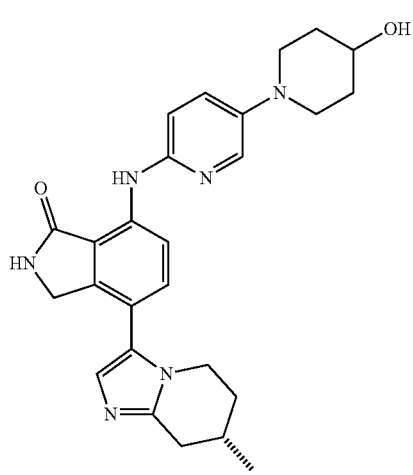

I-304
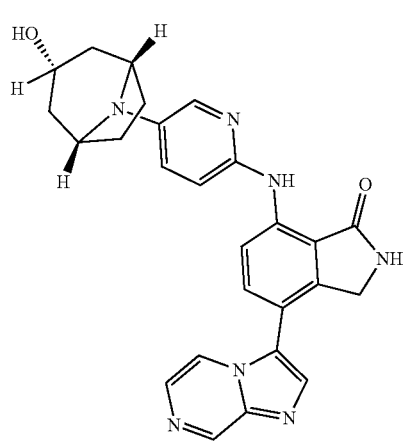
I-307
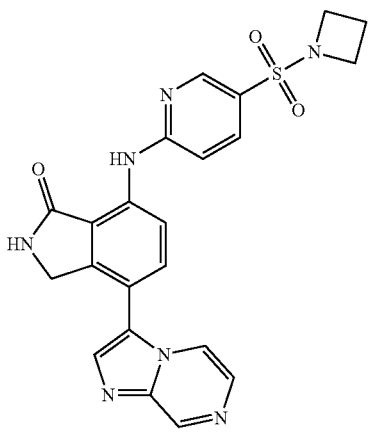
I-305
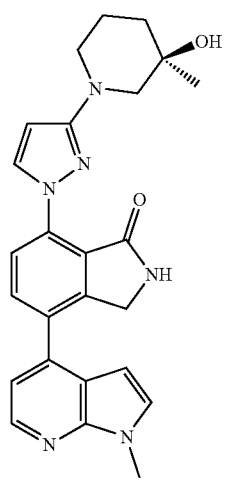
I-308
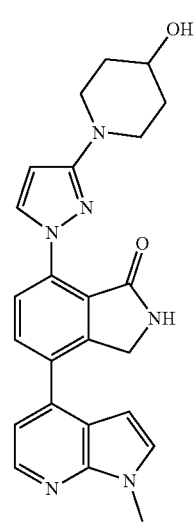
I-306
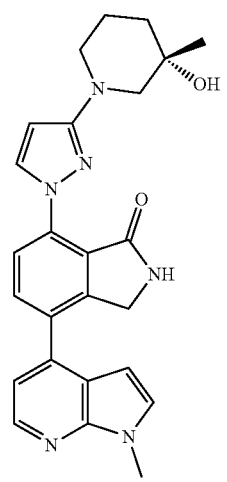
I-309
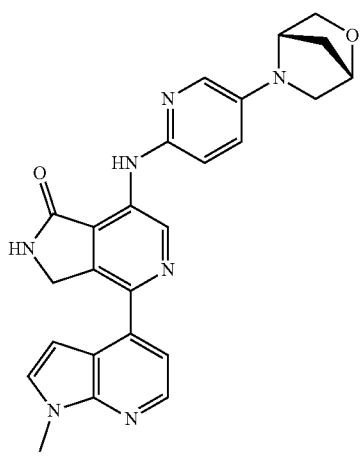

I-310
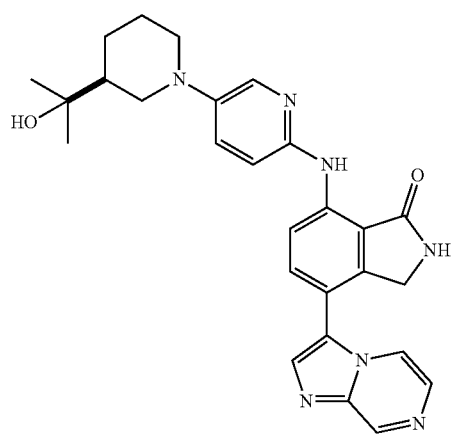
I-313
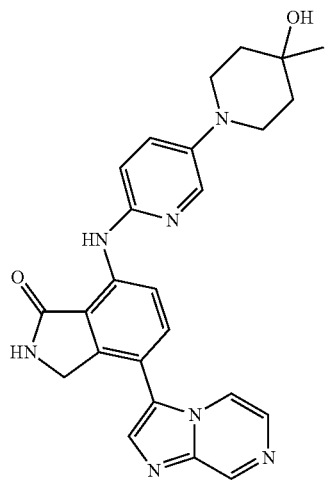
I-311
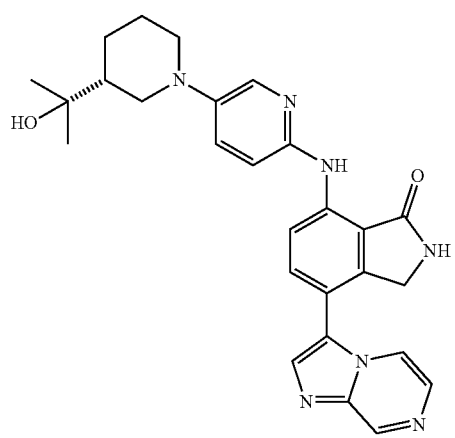
I-314
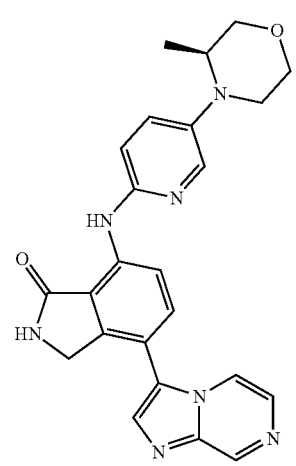
I-312
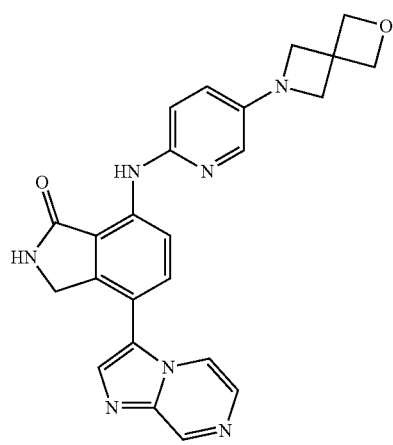
I-315
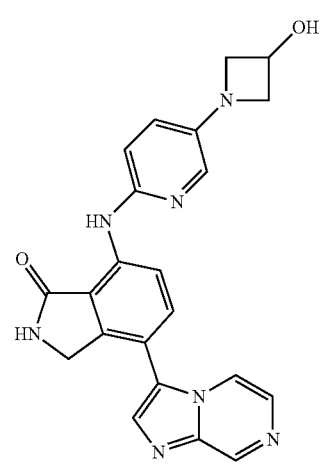

-continued
I-316
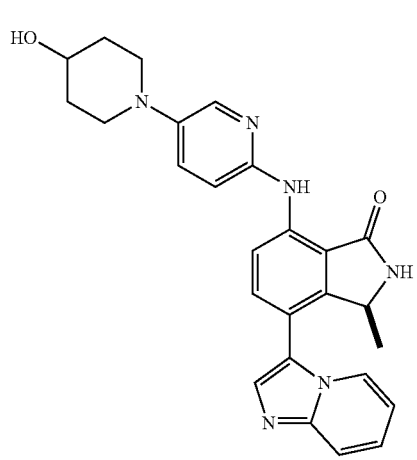
I-317
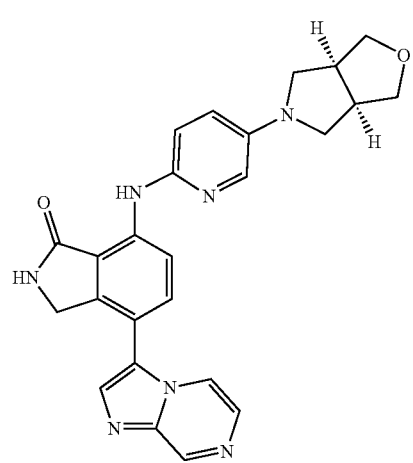
I-318
-continued
I-319
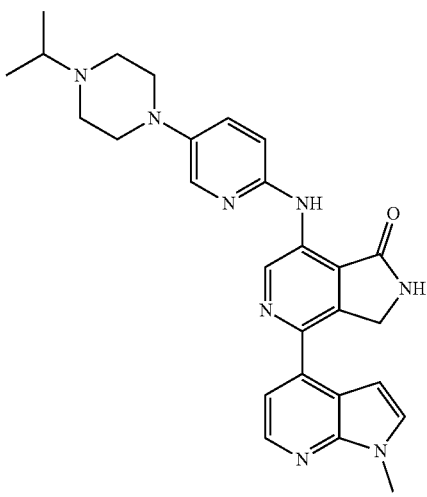
I-320
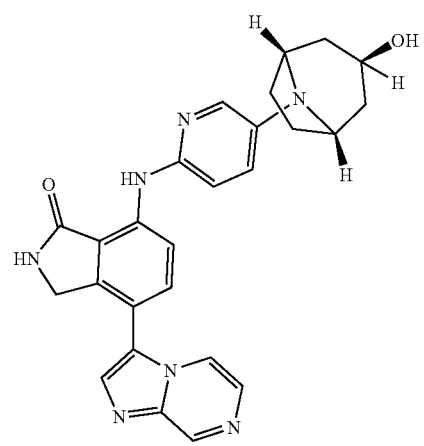
I-321
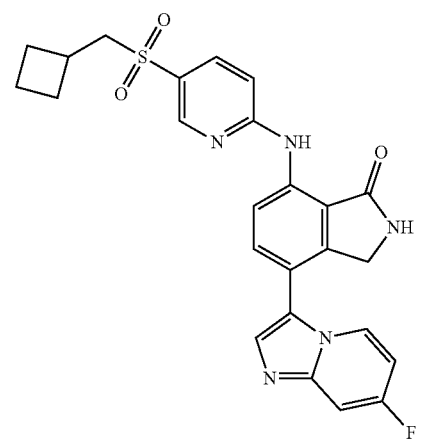

I-322
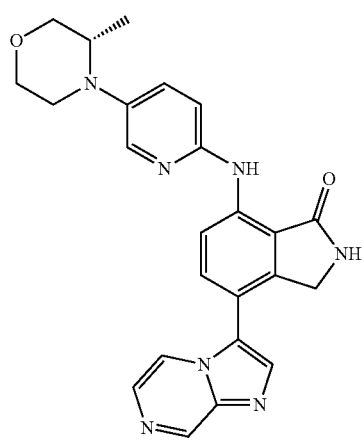
I-323
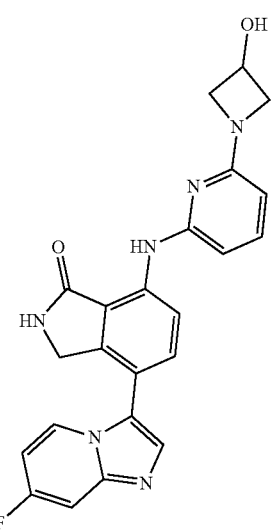
I-324
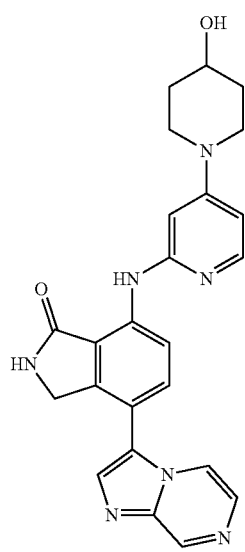
I-325
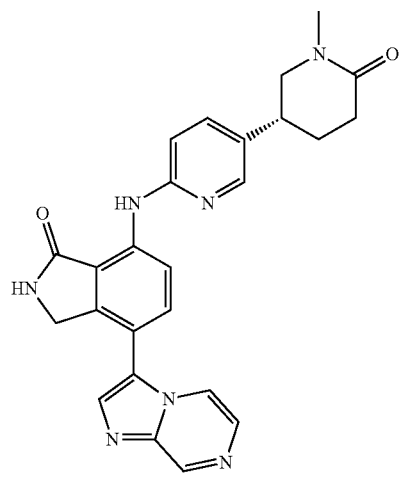
I-326
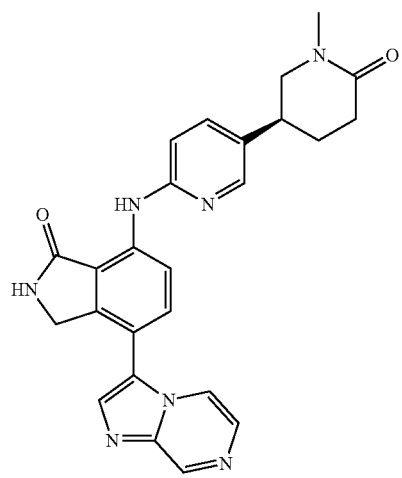
I-327
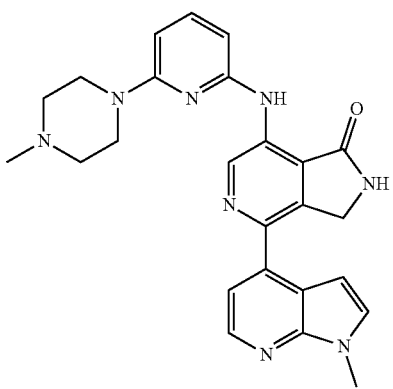

I-328
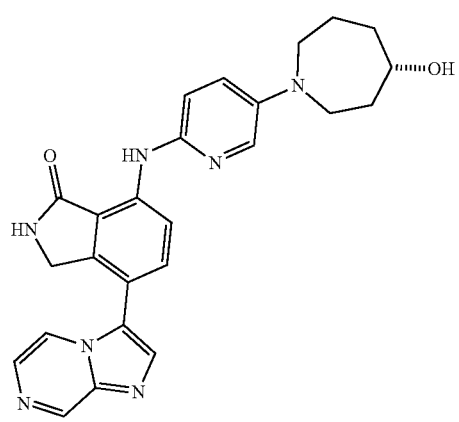
I-331
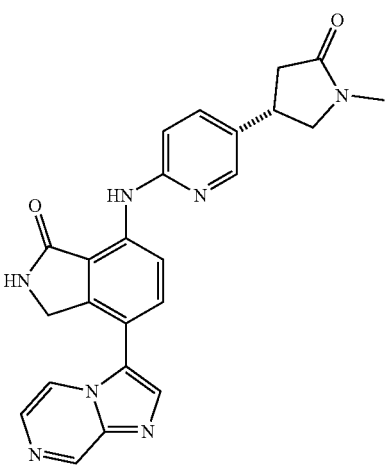
I-329
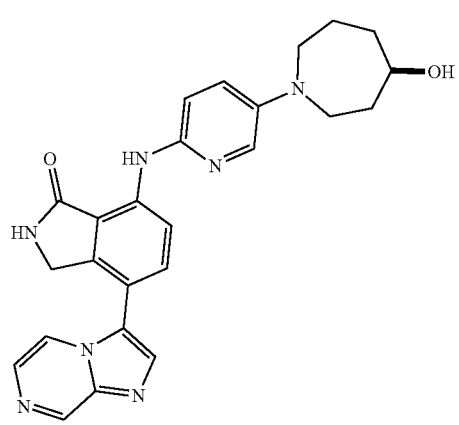
I-332
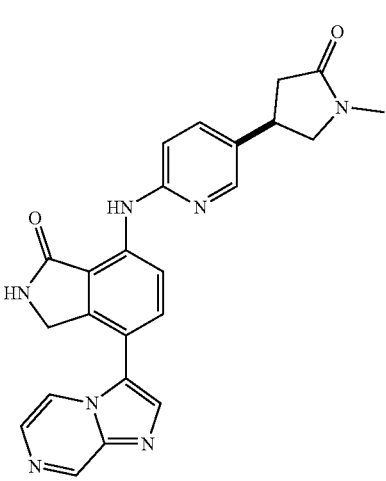
I-330
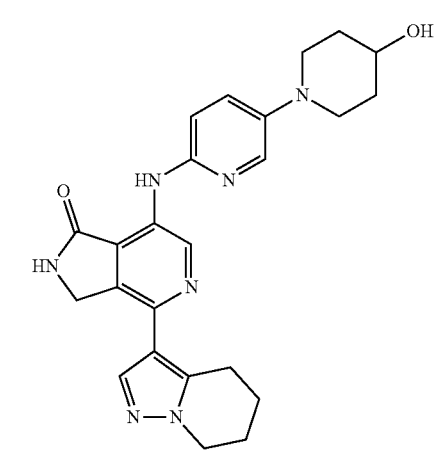
I-333
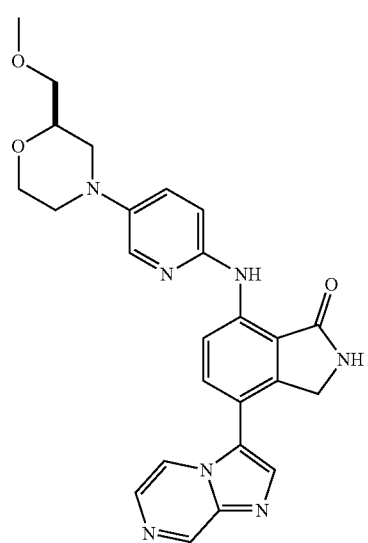

I-334
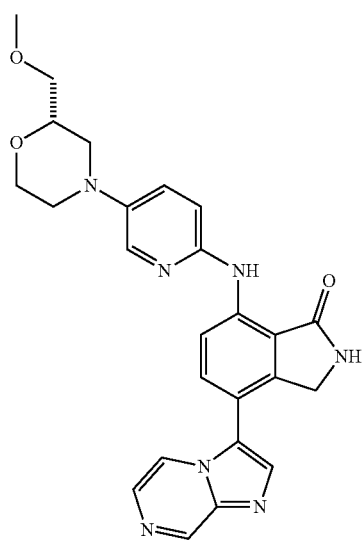
I-338
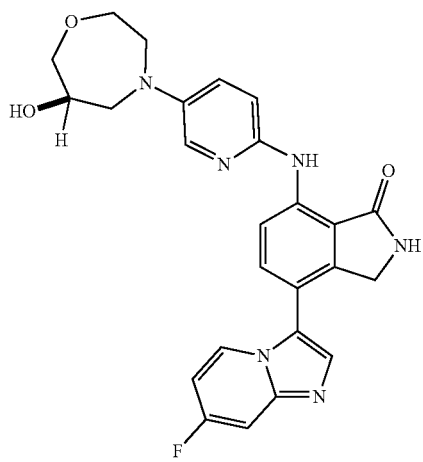
I-335
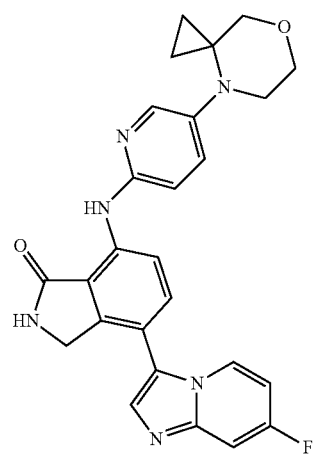
I-339
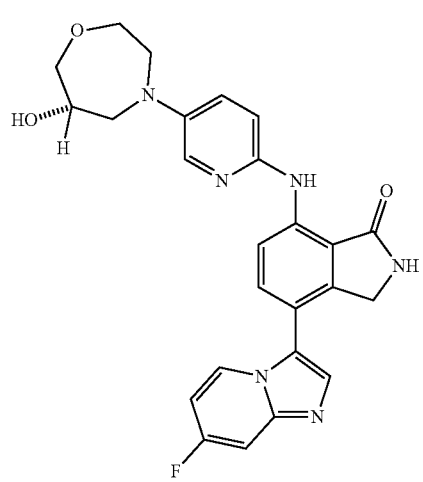
I-336
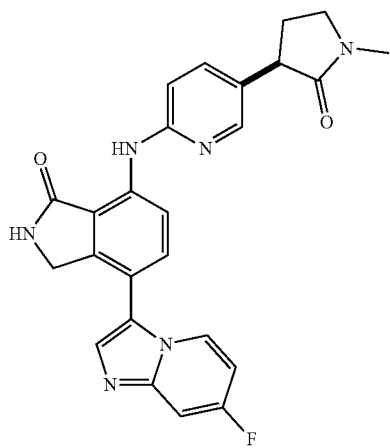
I-340
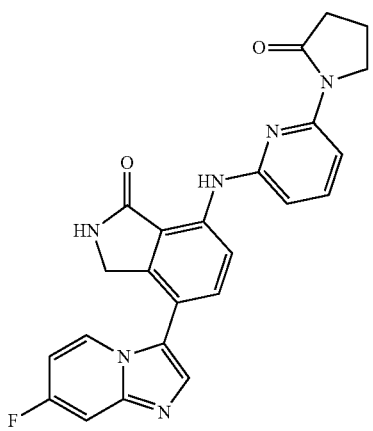

I-341 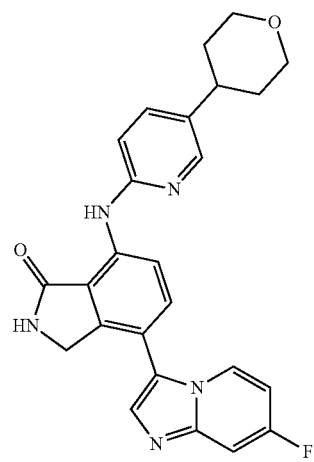
I-346 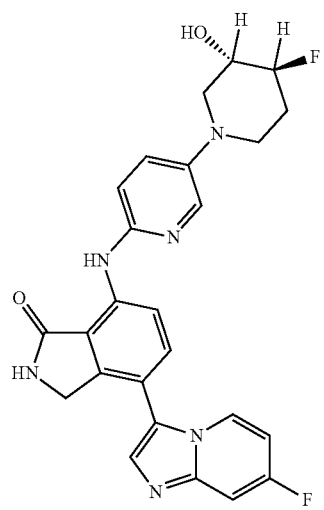
I-342 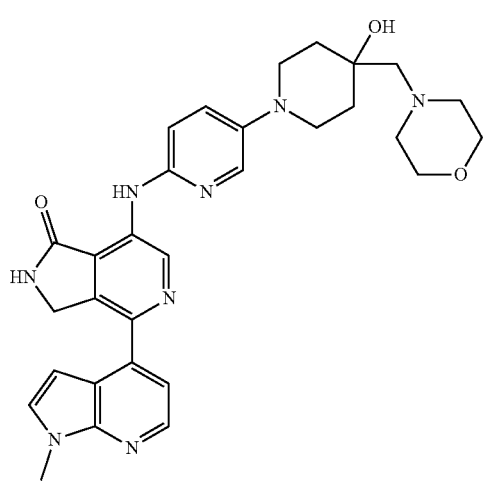
I-347 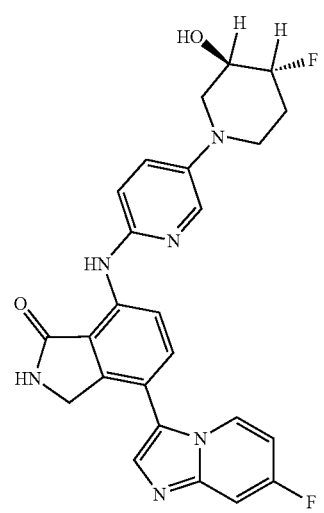
I-343 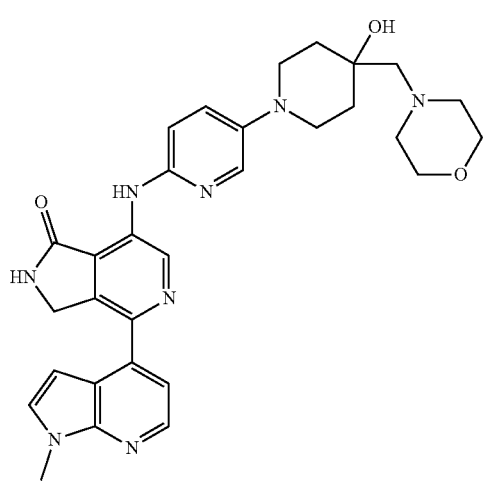
I-349 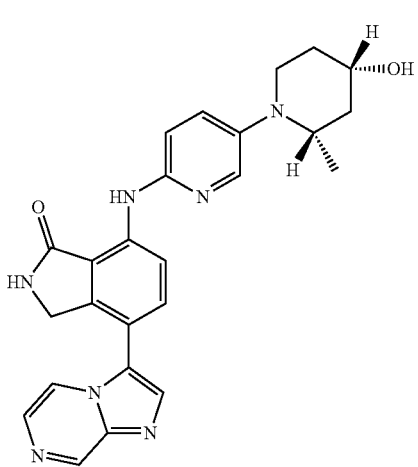

I-350
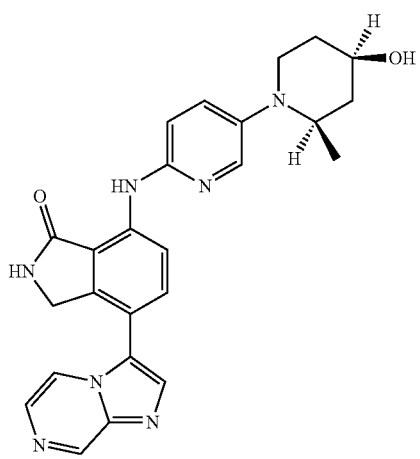
I-353
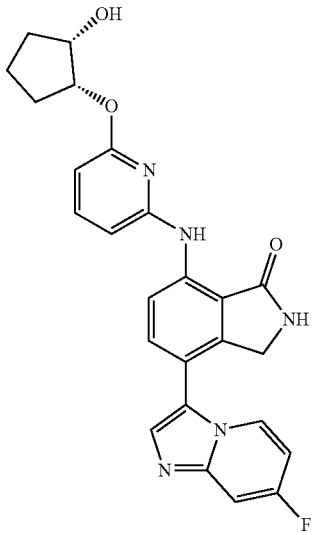
I-351
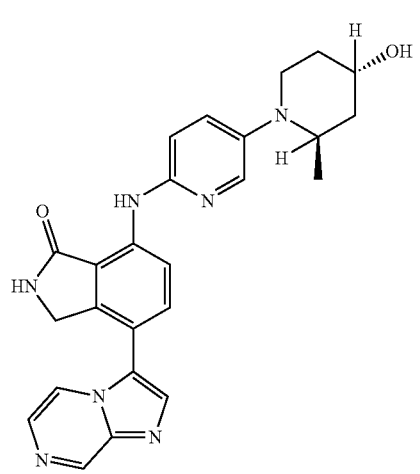
I-354
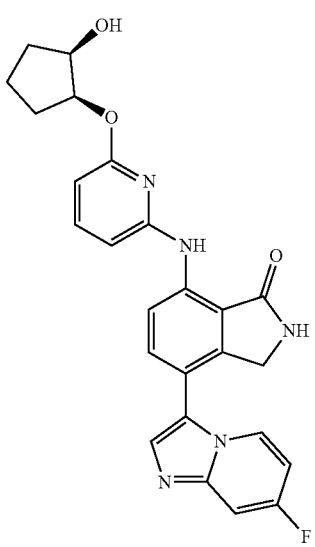
I-352
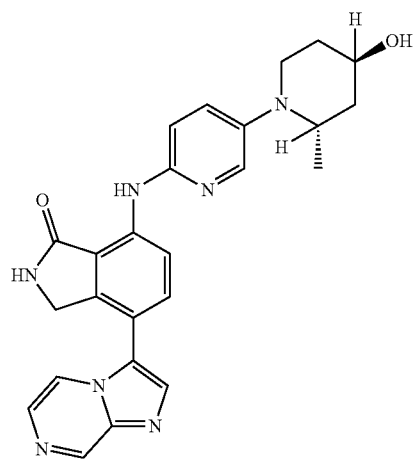
I-355
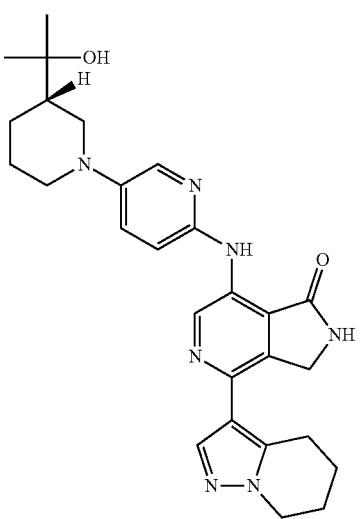

2519
-continued
I-356
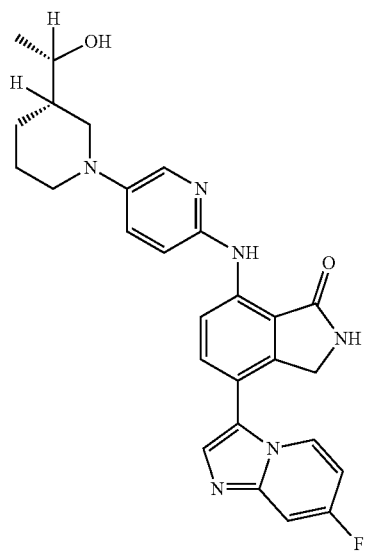
I-357
I-358
2520
-continued
I-359
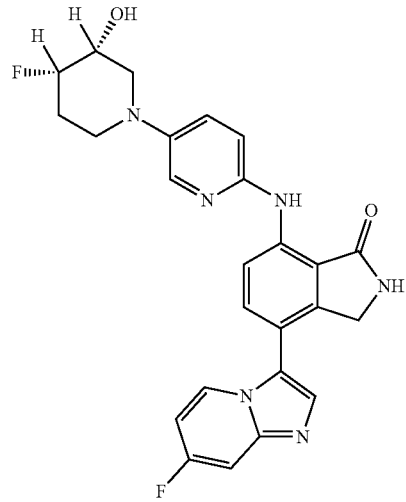
I-360
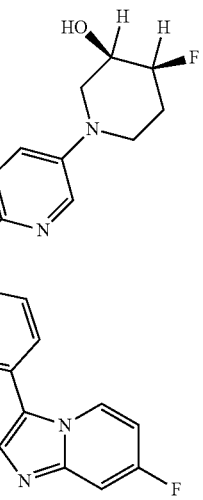
I-361
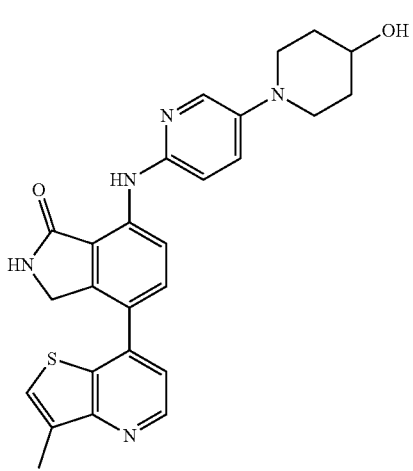

-continued
I-362
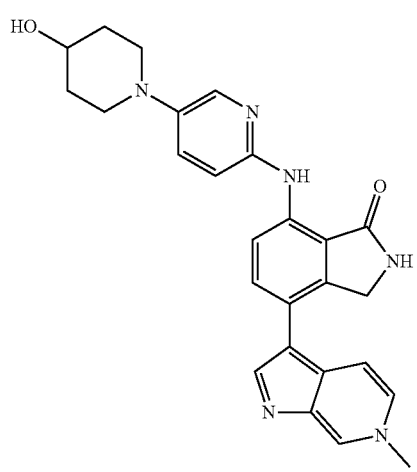
I-363
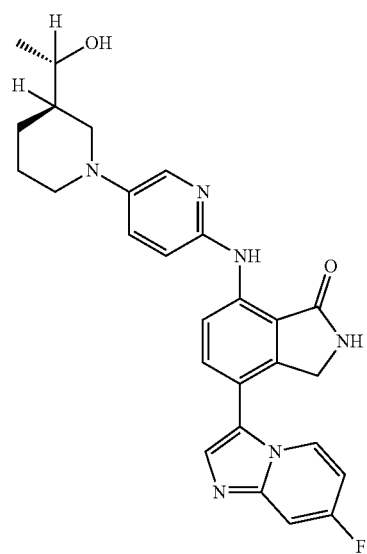
I-364
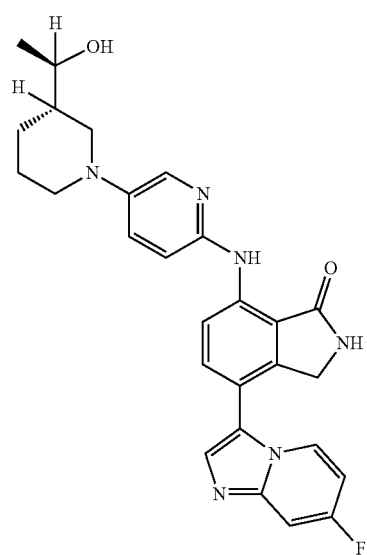
-continued
I-365
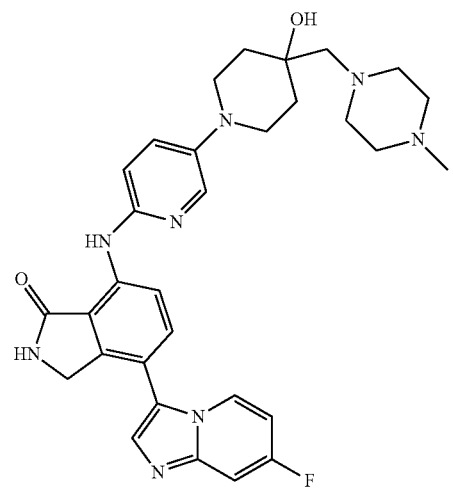
I-366
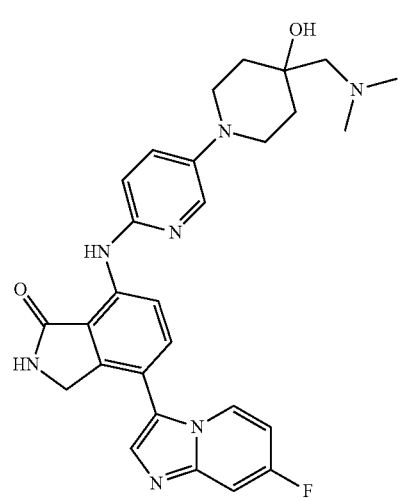
I-367
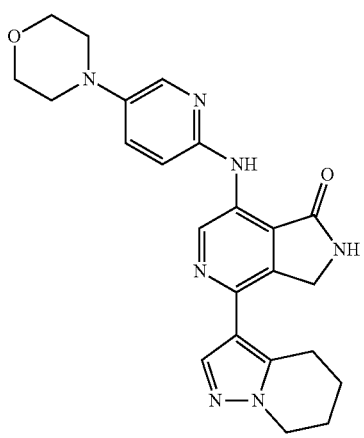

I-368
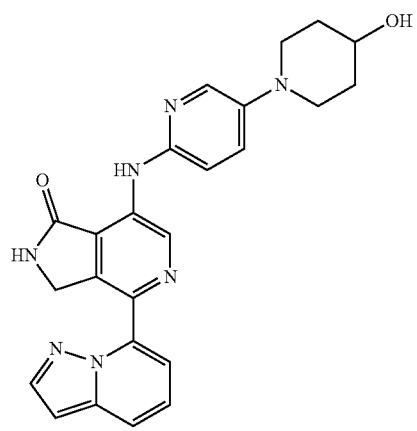
I-371
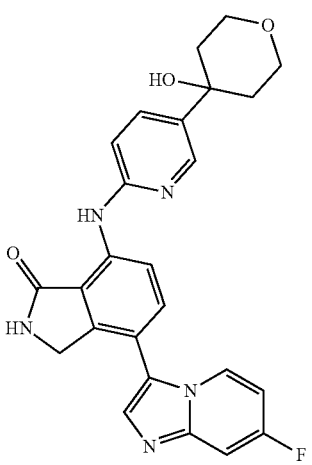
I-369
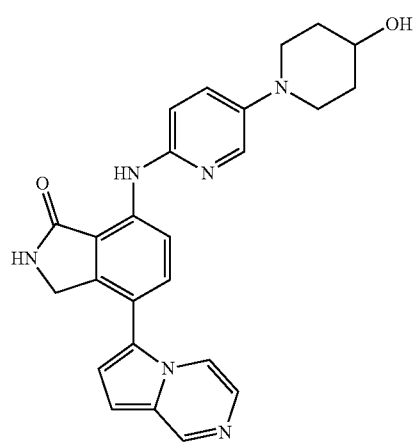
I-372
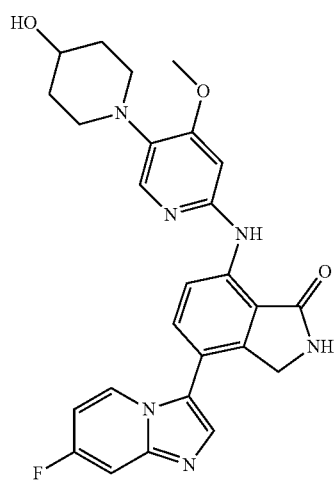
I-370
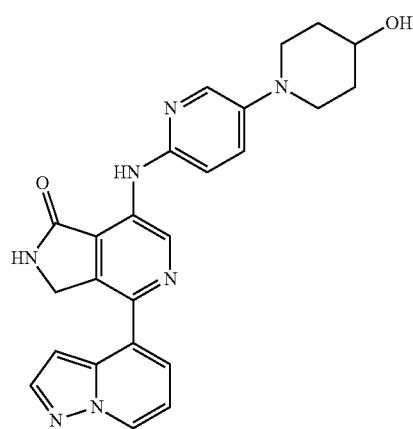
I-373
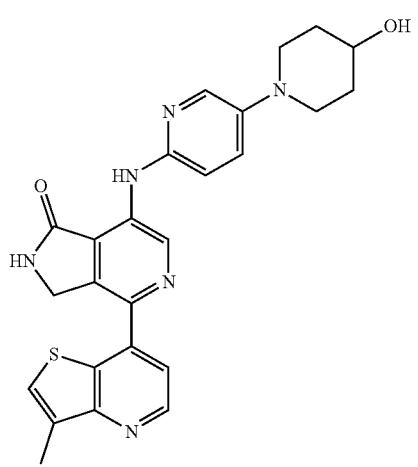

-continued
I-374
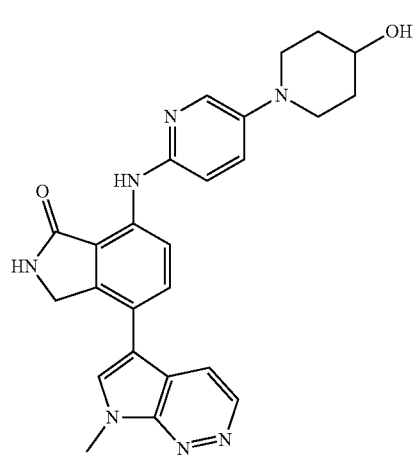
I-375
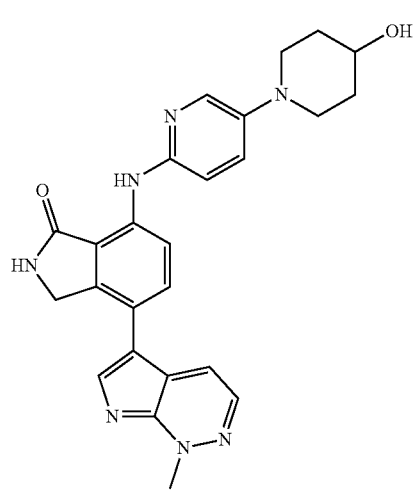
I-376
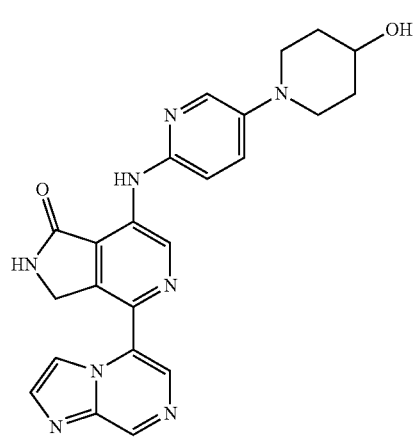
-continued
I-377
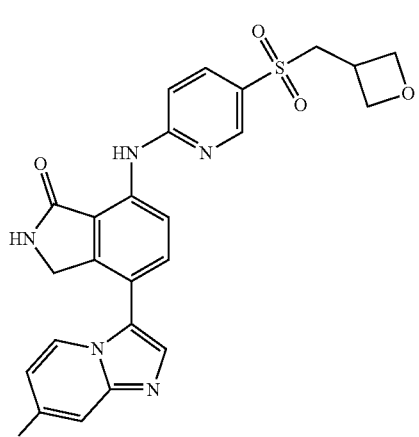
I-378
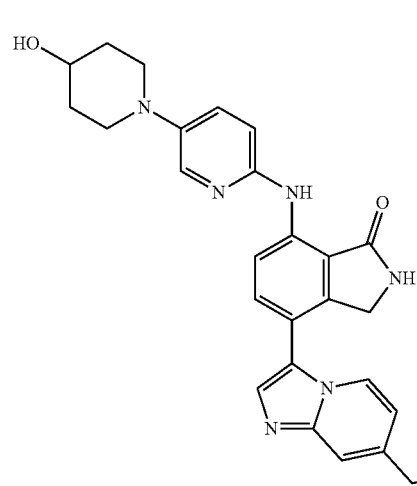
I-379
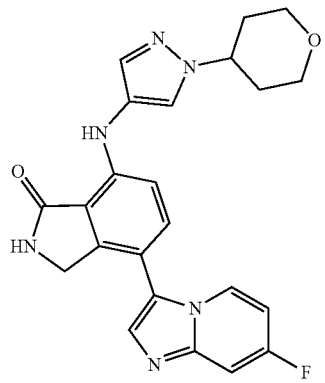

-continued
I-380
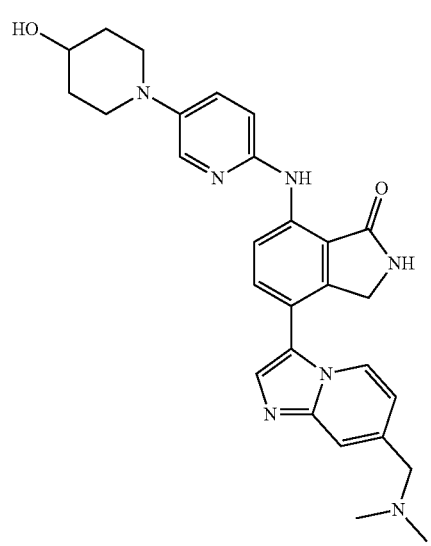
I-381
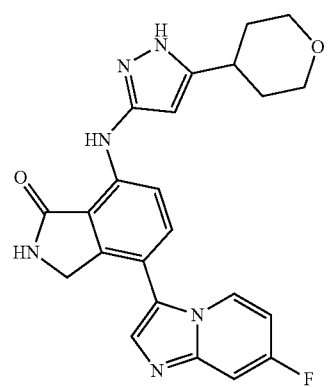
I-382
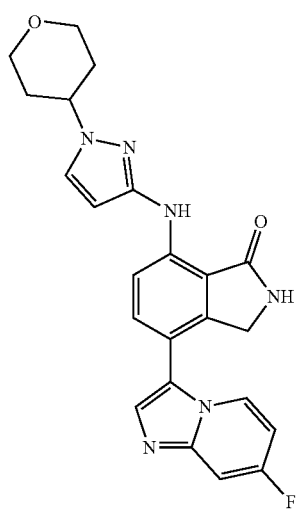
-continued
I-383
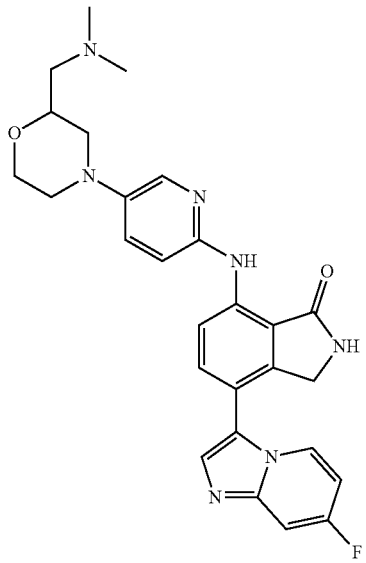
I-384
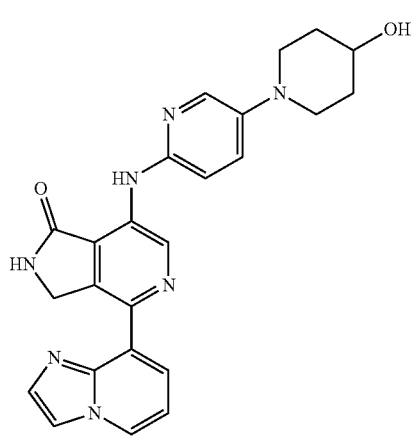
I-385
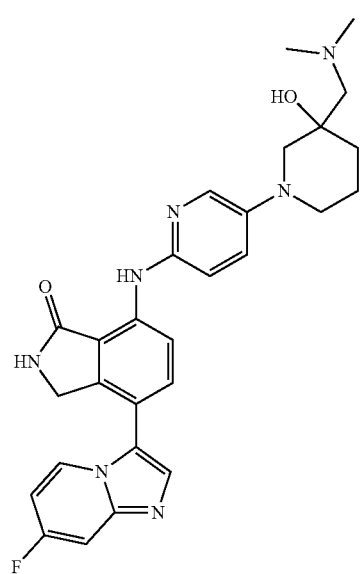

I-386
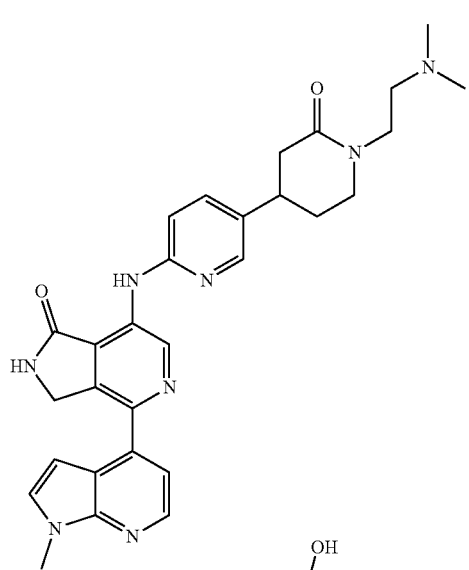
I-387
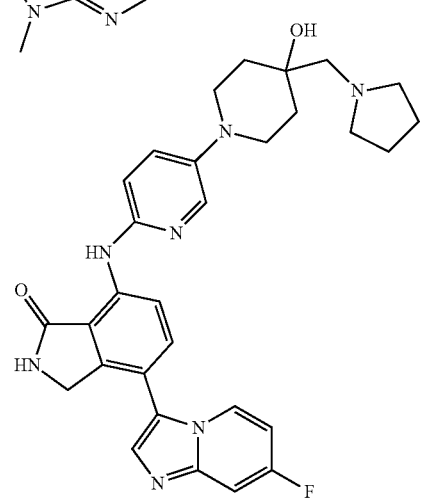
I-388
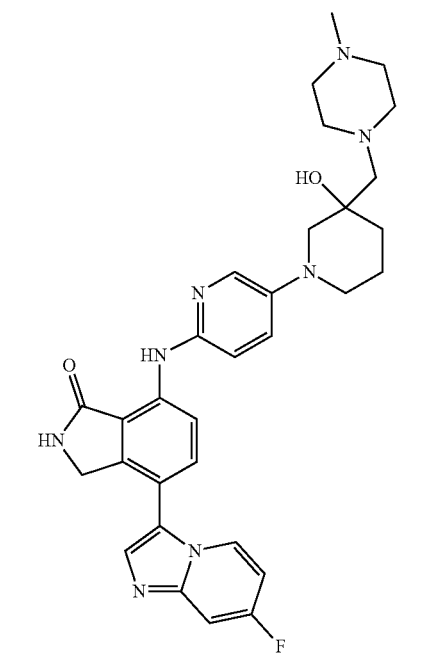
I-389
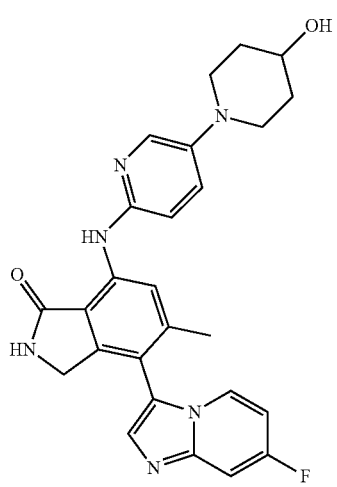
I-390
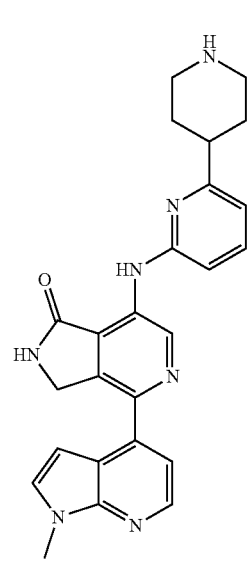
I-391
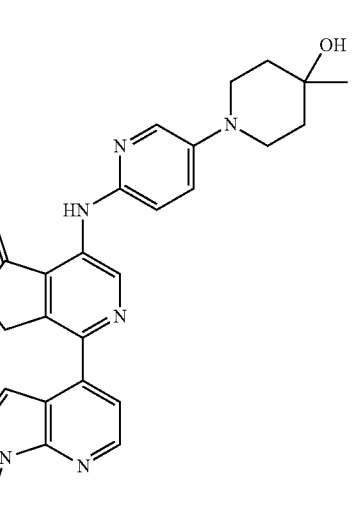

I-392
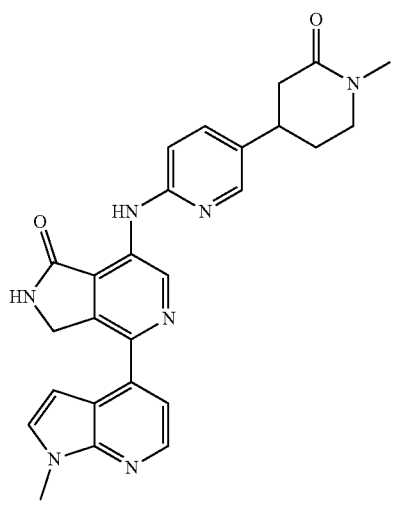
I-393
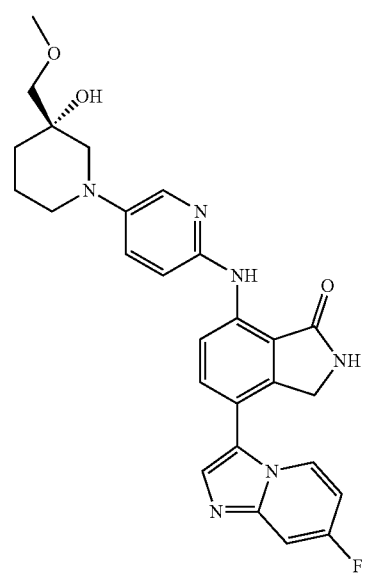
I-394
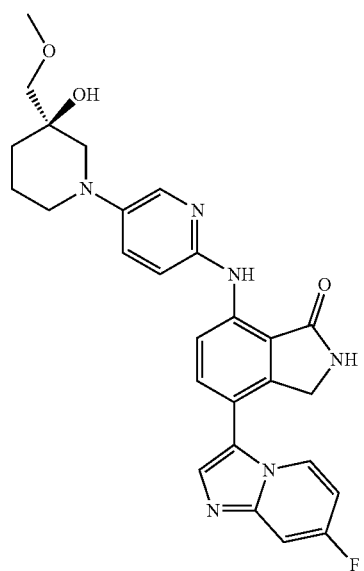
I-395
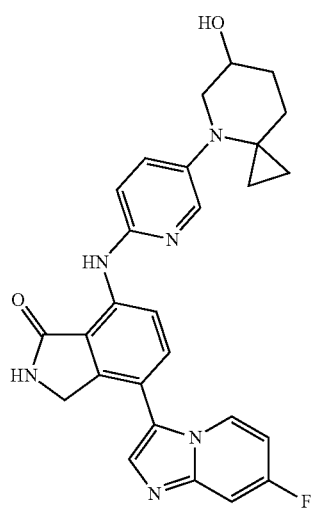
I-396
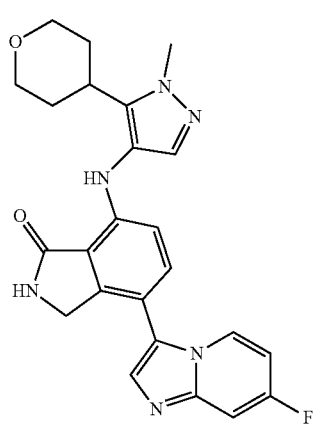
I-397
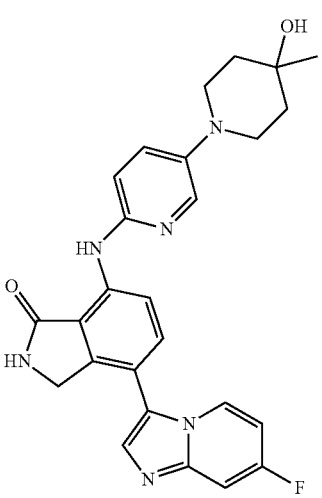

I-398 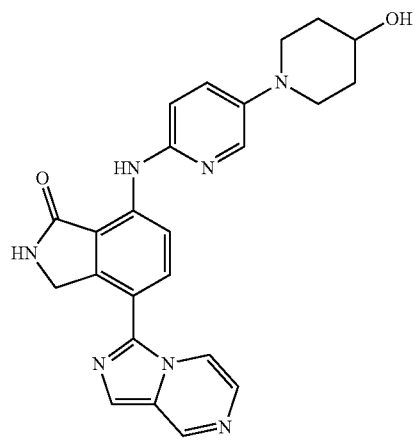
I-401 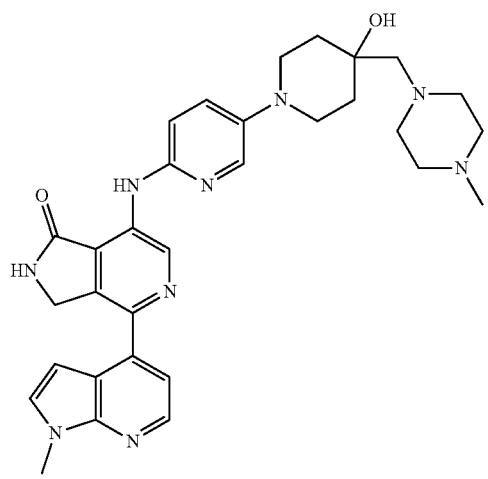
I-399 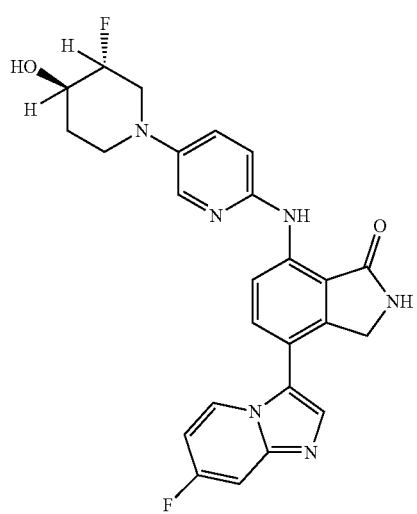
I-402 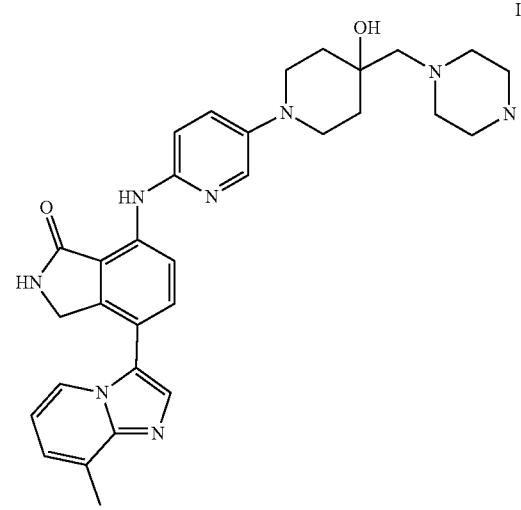
I-400 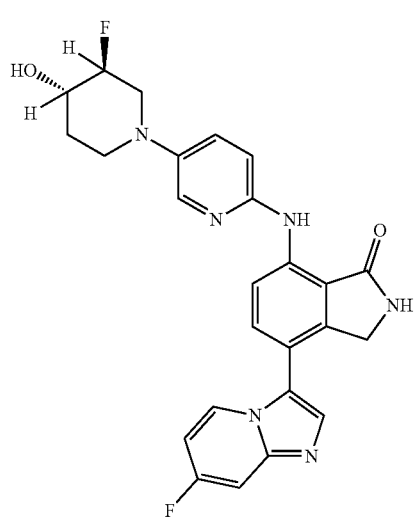
I-403 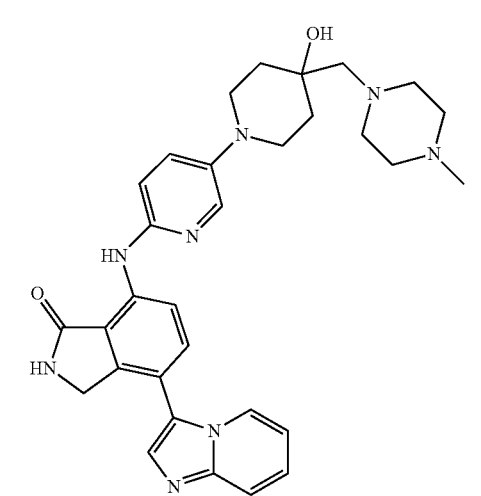

2535
-continued
I-404
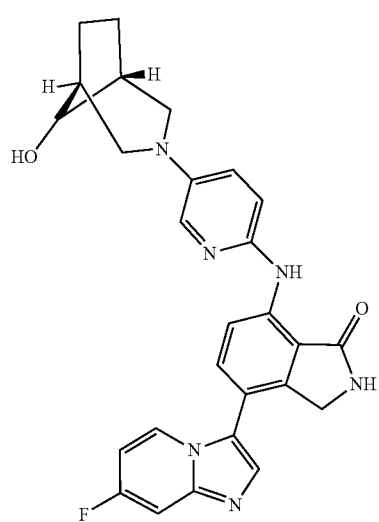
I-405
I-406
2536
-continued
I-407
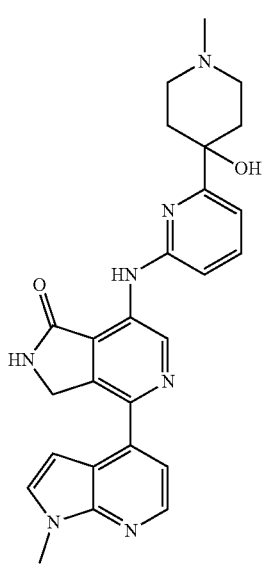
I-408
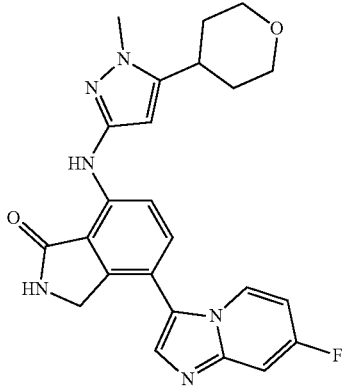
I-411
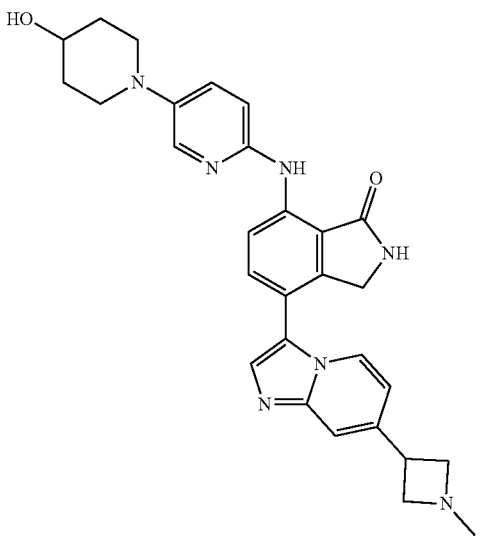

I-412
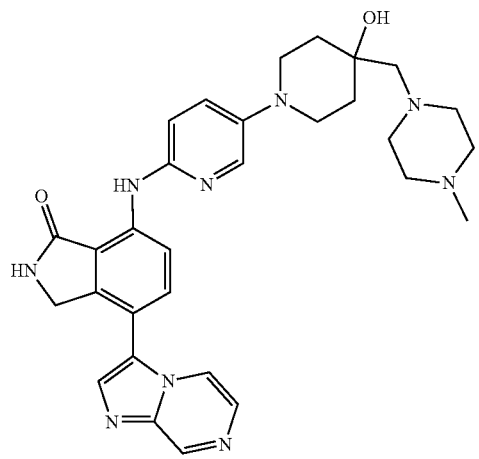
I-415
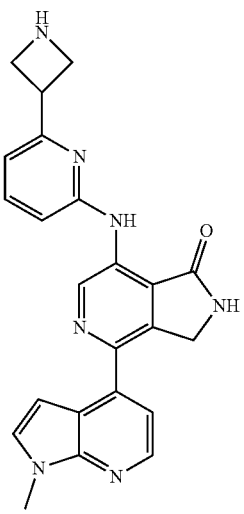
I-413
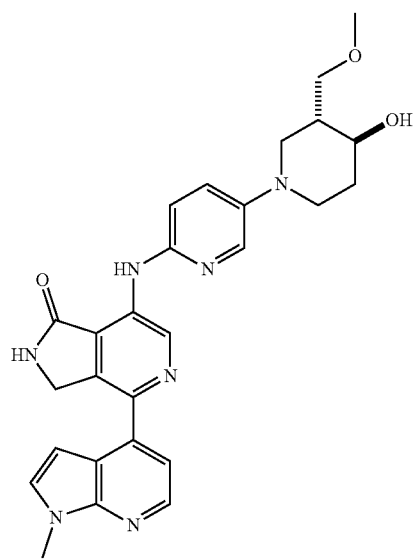
I-416
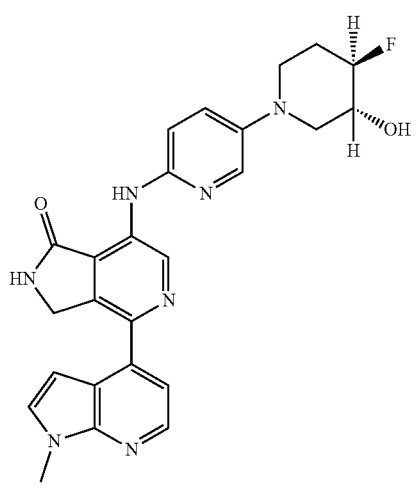
I-414
I-417
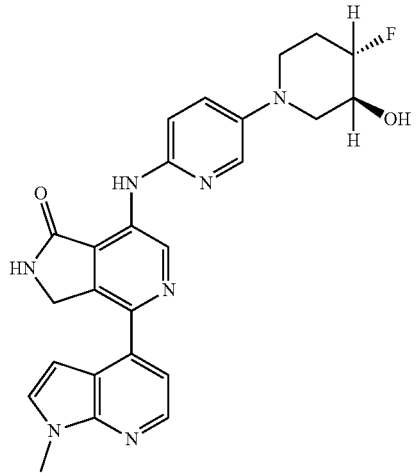

I-418
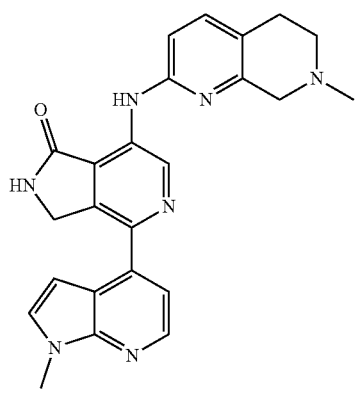
I-421
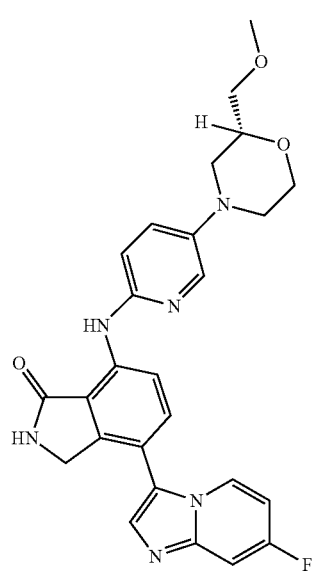
I-419
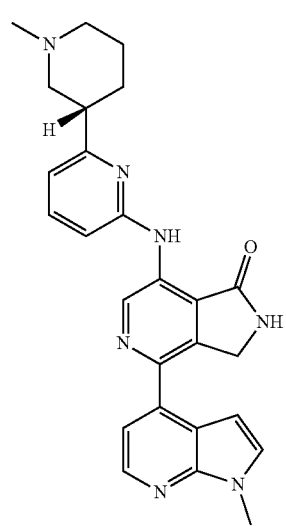
I-422
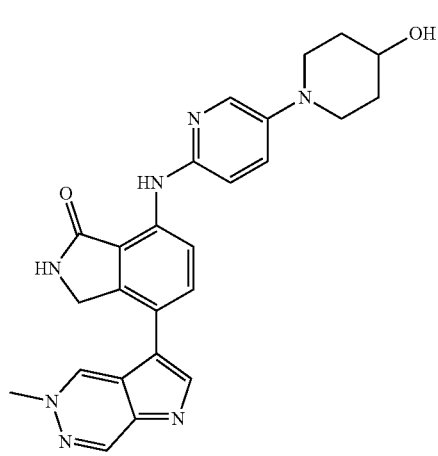
I-420
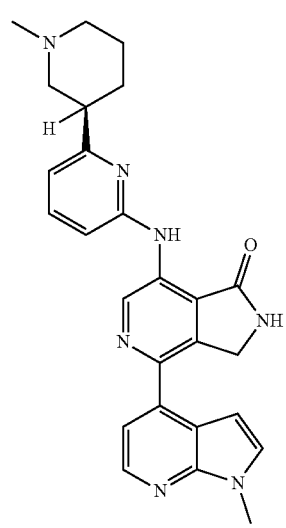
I-423
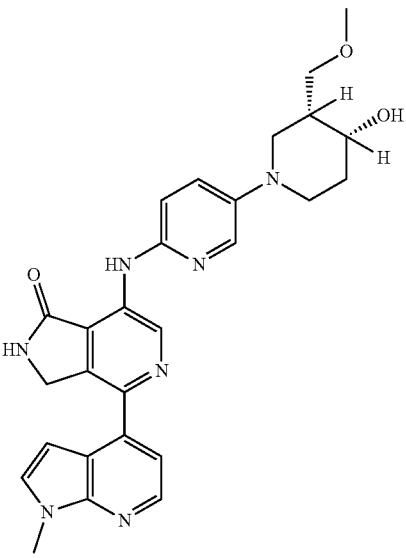

| 2541 -continued | 2542 -continued |
|---|---|
| I-424 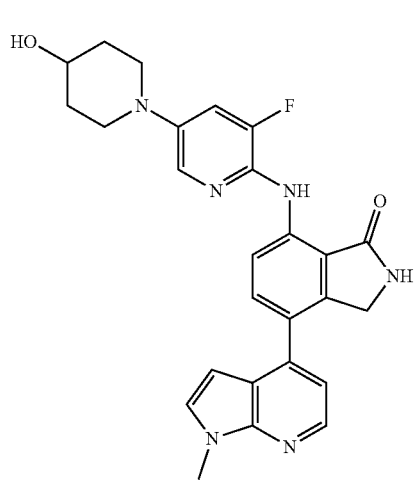 | I-427 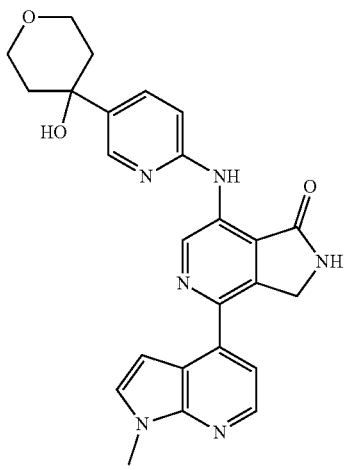 |
| I-425 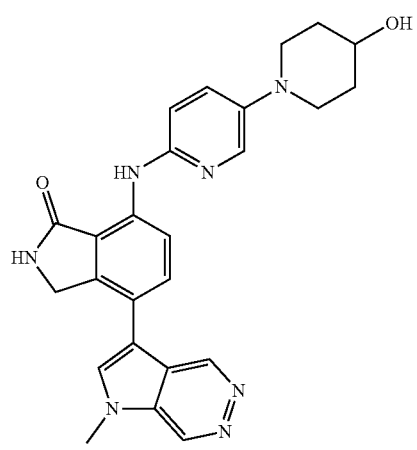 | I-428 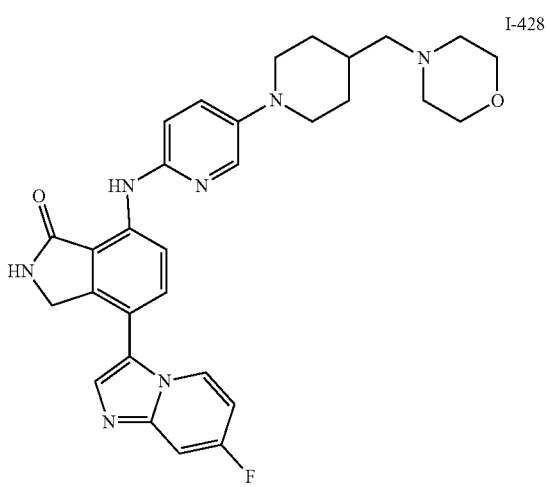 |
| I-426 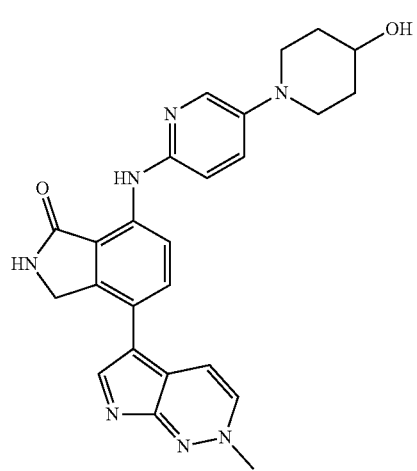 | I-429 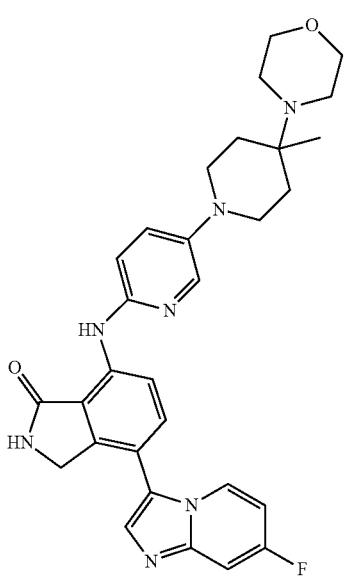 |

I-430
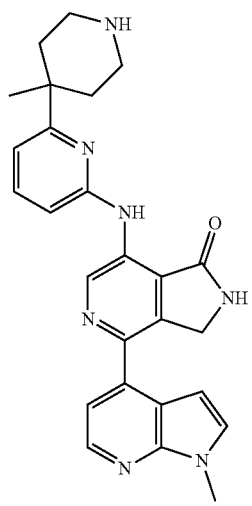
I-431
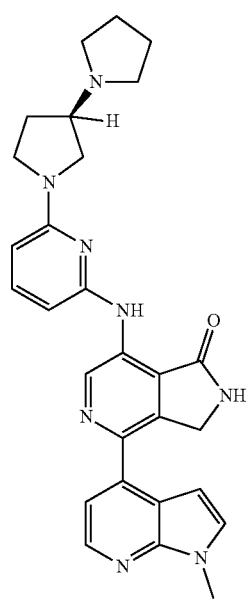
I-432
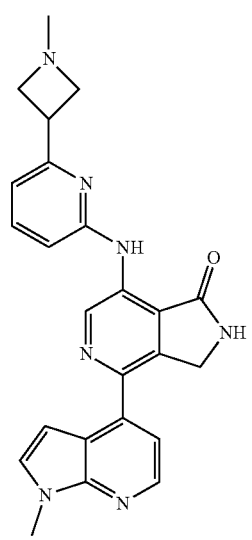
I-433
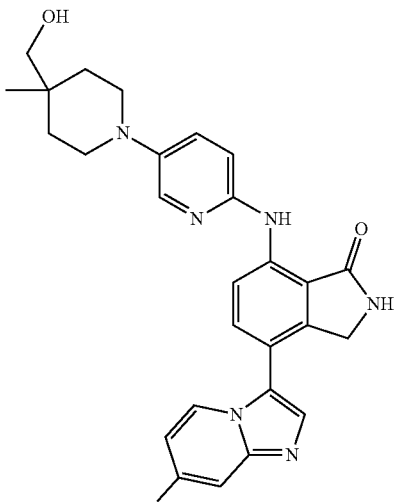
I-434
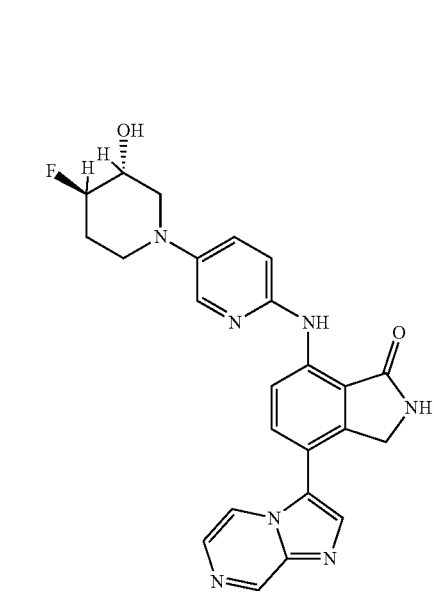
I-435
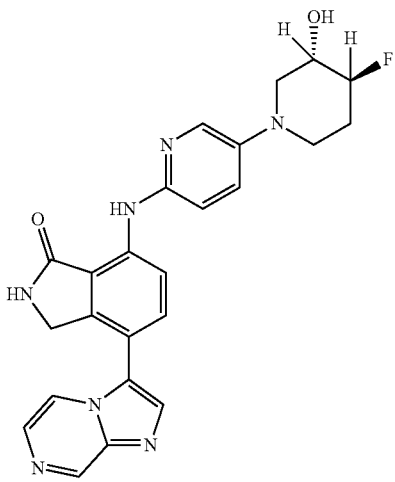

I-436
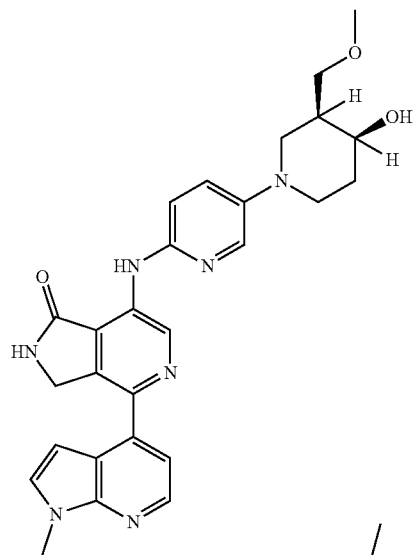
I-437
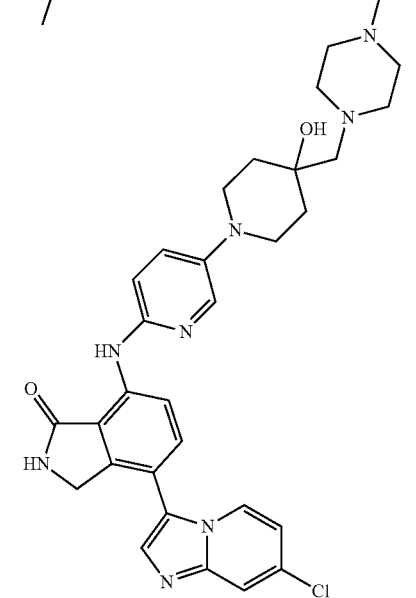
I-438
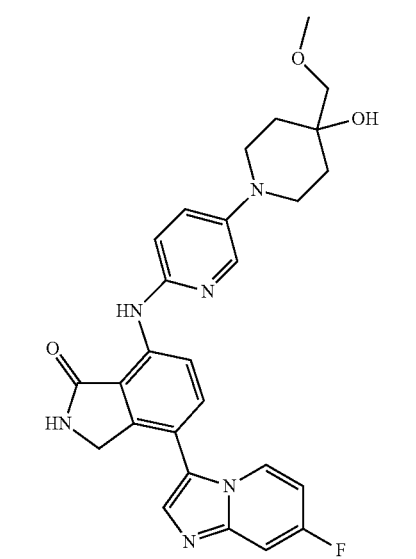
I-439
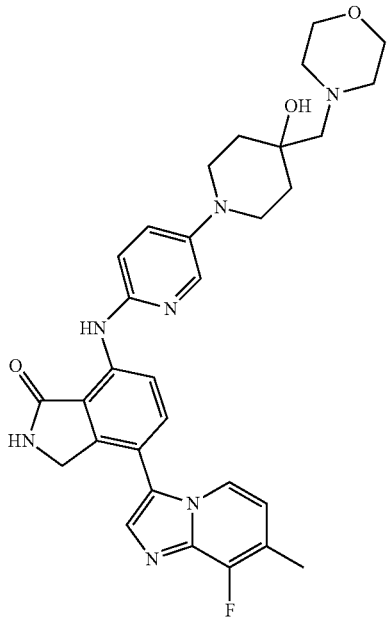
I-442
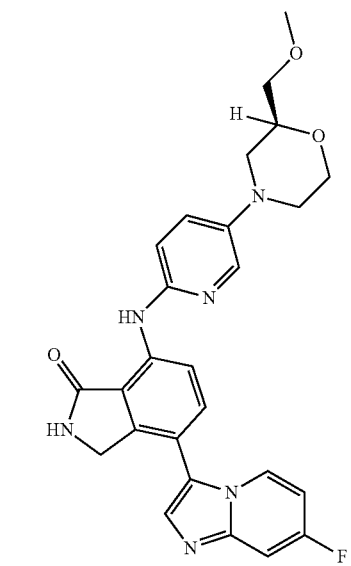

2547
-continued
I-443
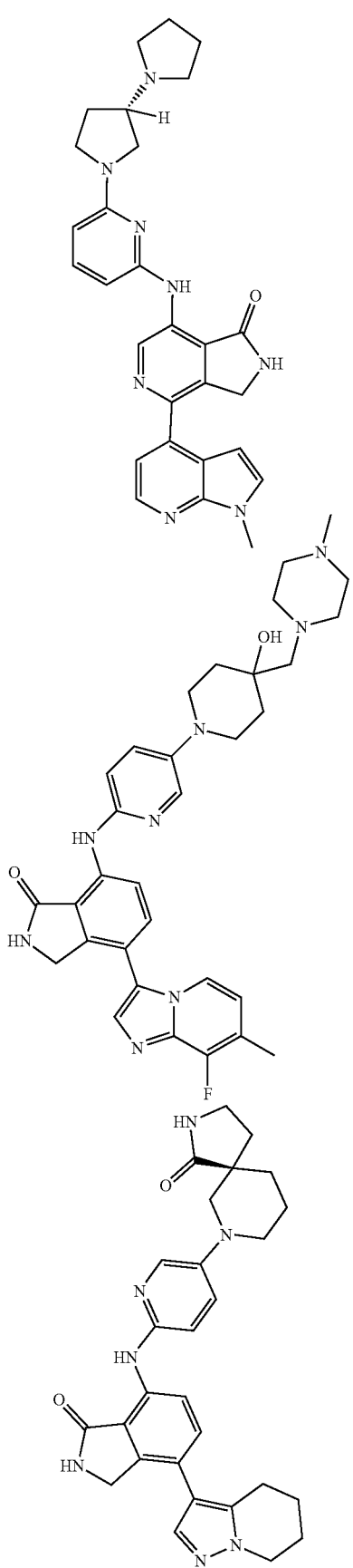
I-444
I-445
2548
-continued
I-446
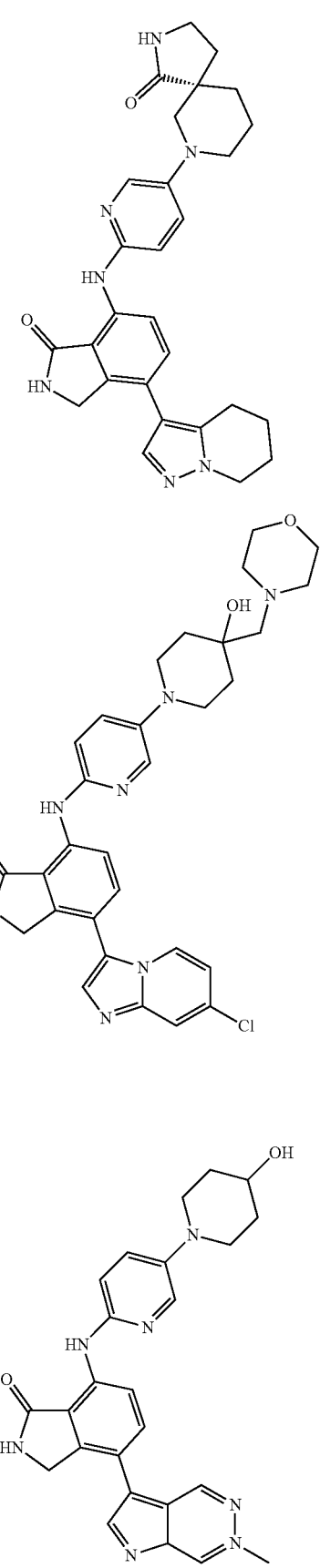
I-447
I-448

I-449
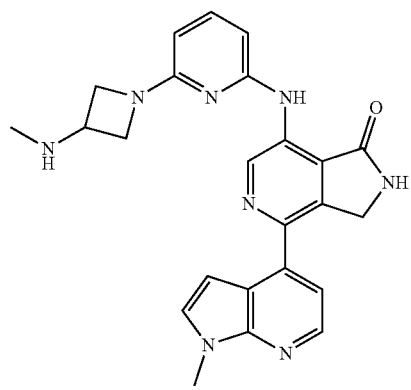
I-450
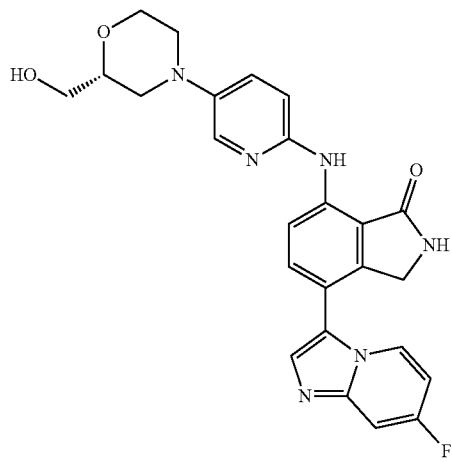
I-451
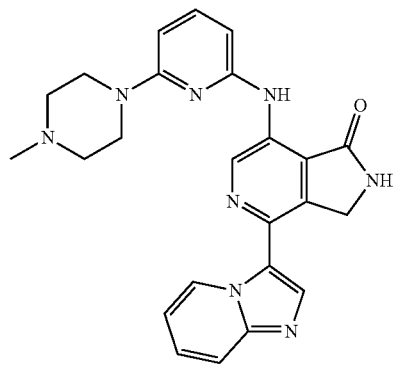
I-452
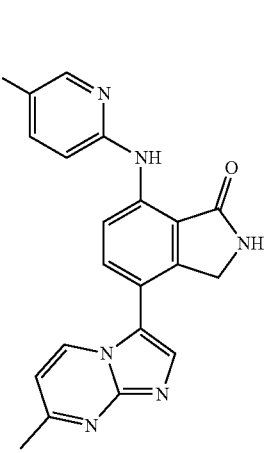
I-453
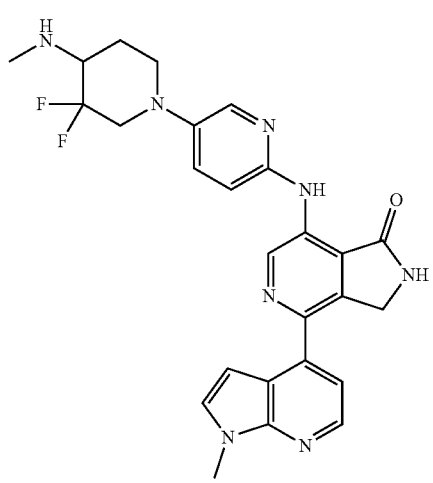
I-454
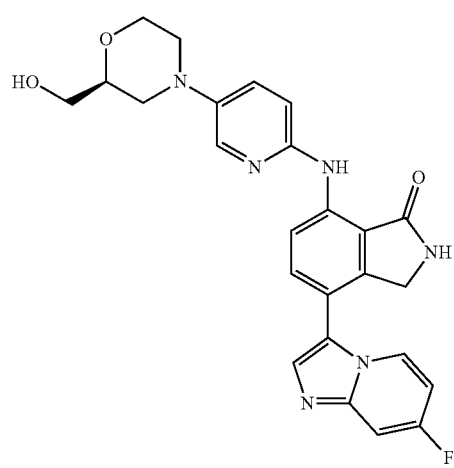

I-455
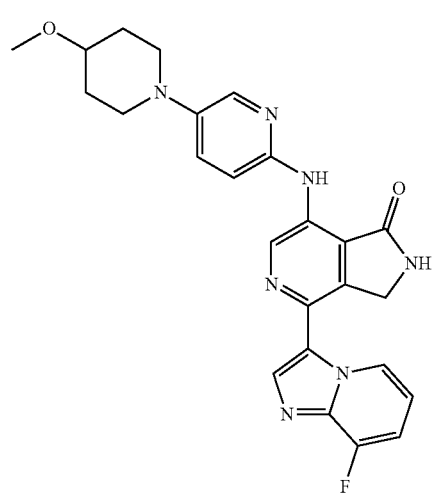
I-458
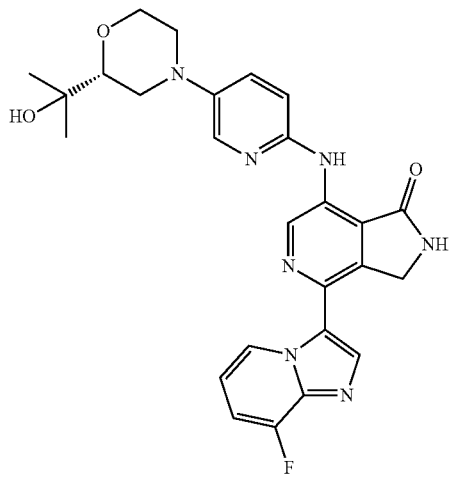
I-456
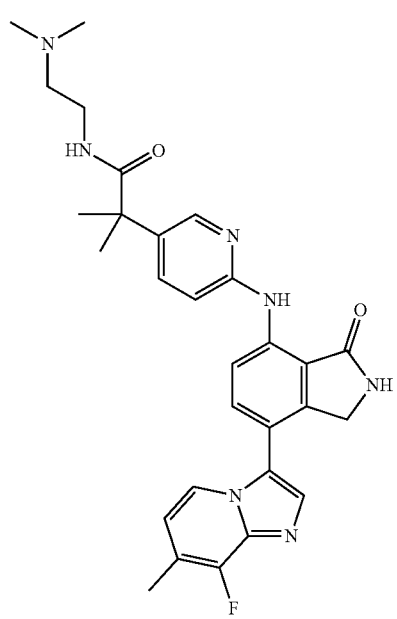
I-459
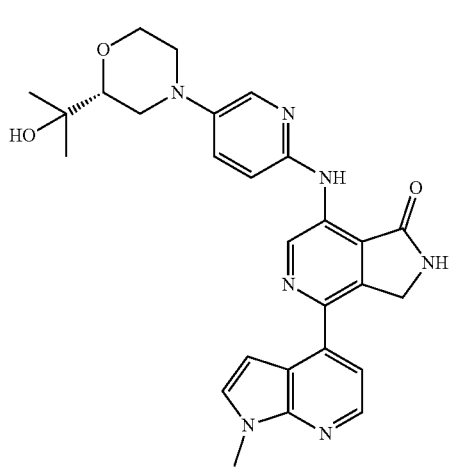
I-457
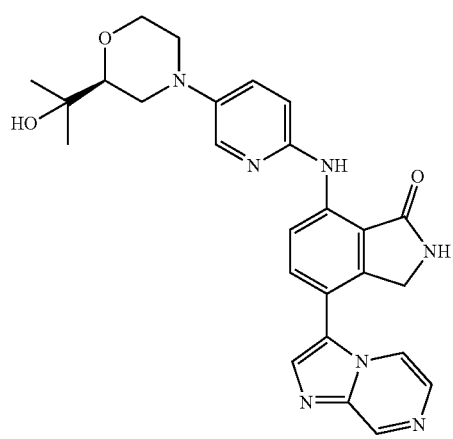
I-460
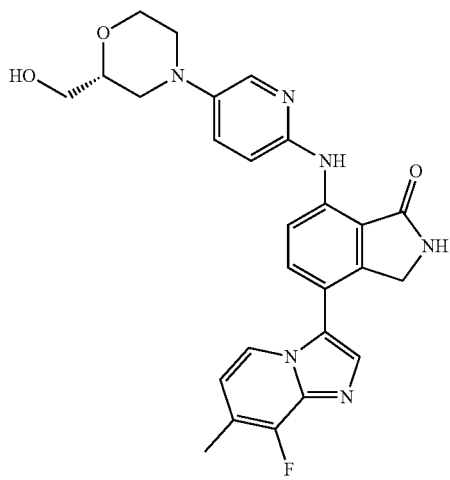

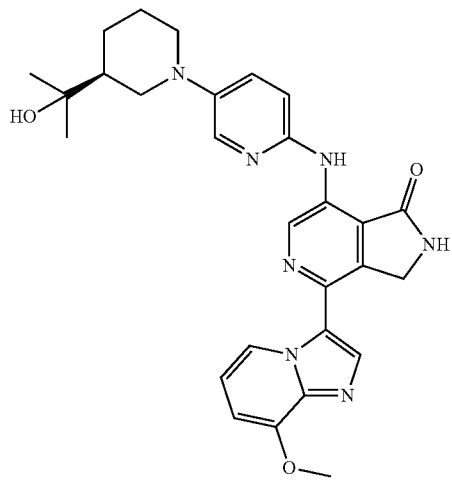
I-461
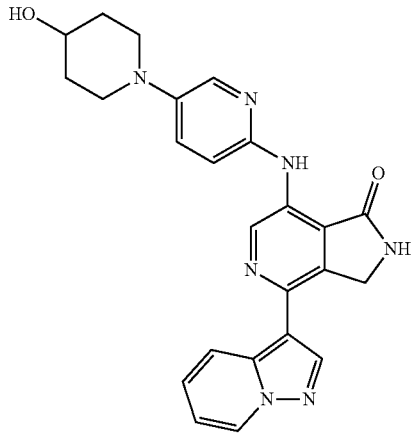
I-464
I-462
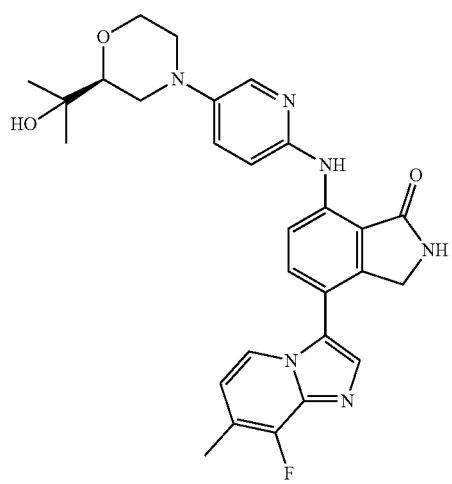
I-465
I-463
I-467

I-468
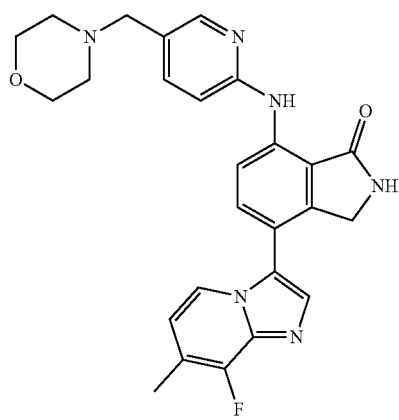
I-469
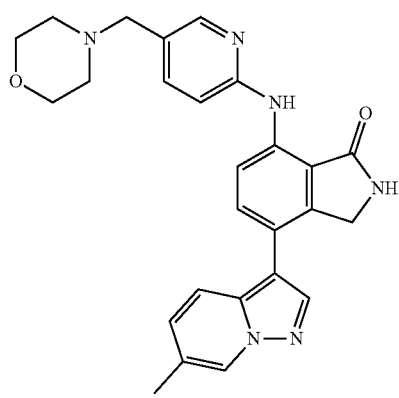
I-470
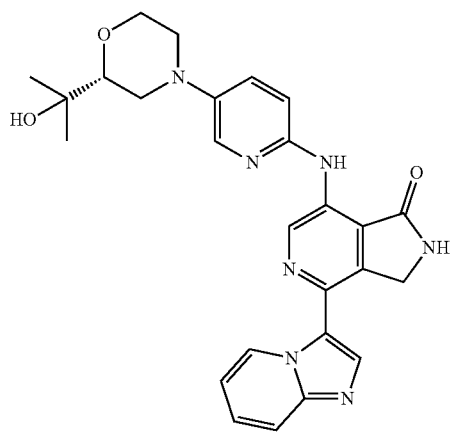
I-471
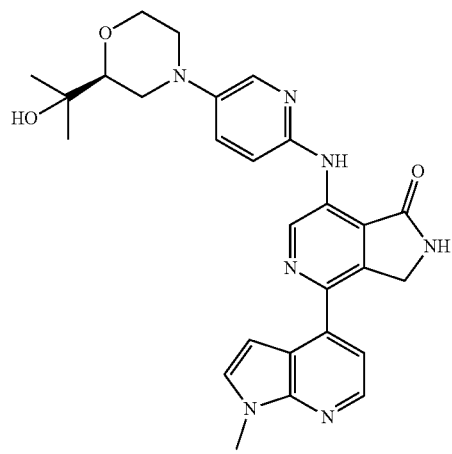
I-472
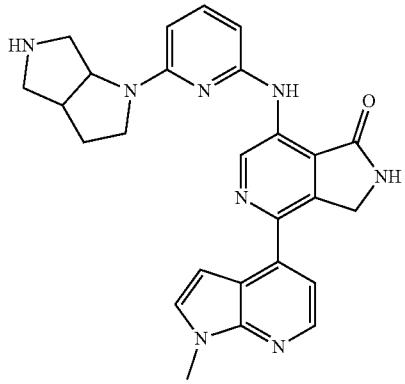
I-473
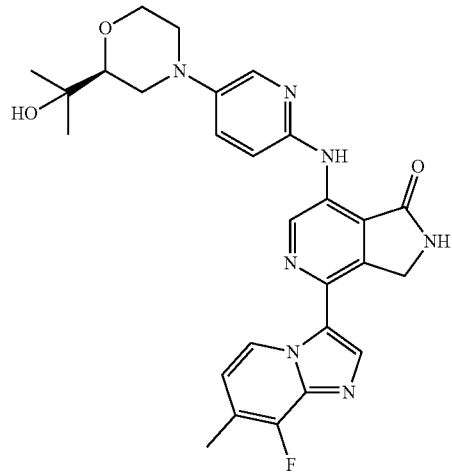

I-474
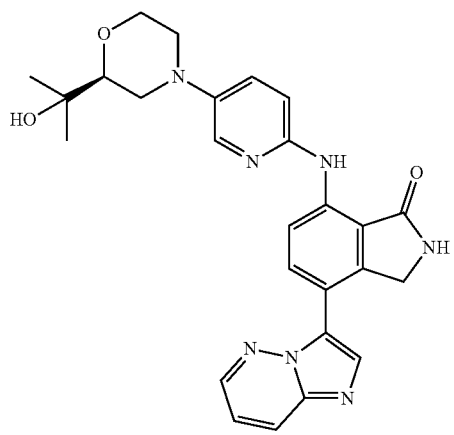
I-477
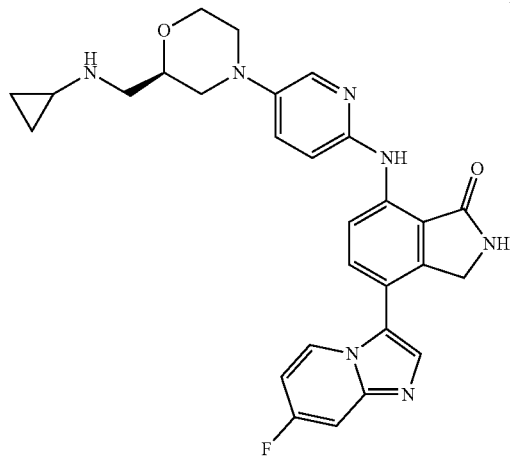
I-475
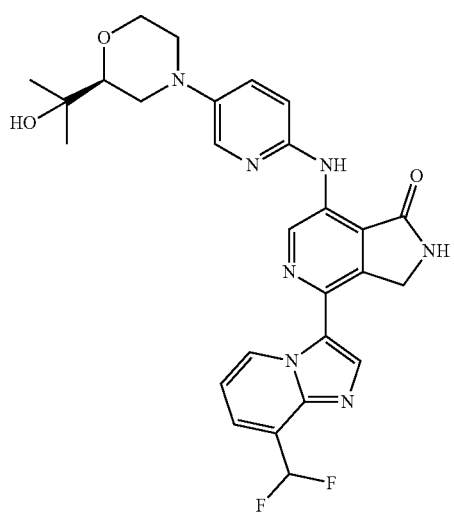
I-480
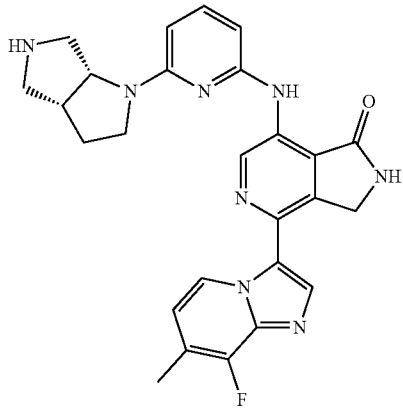
I-476
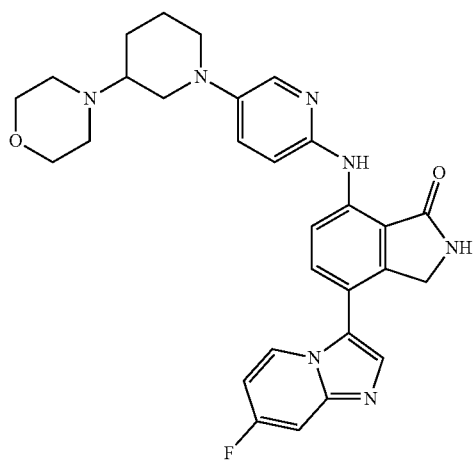
I-481

2559
-continued
I-482
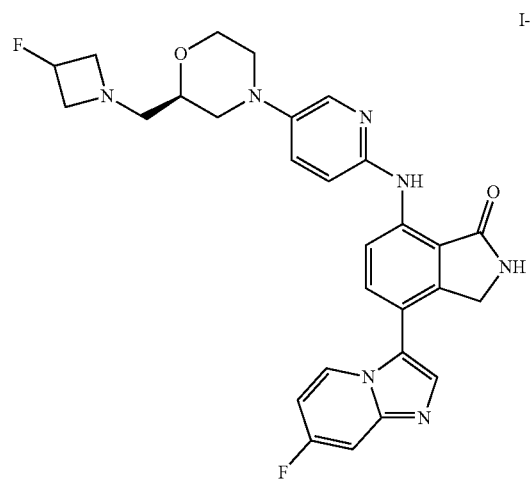
I-483
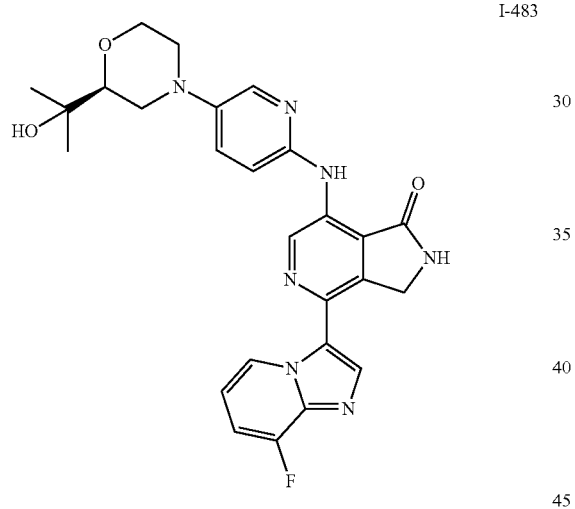
I-484
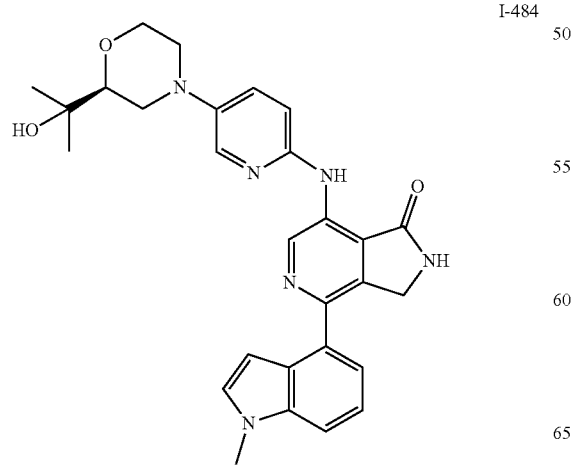
2560
-continued
I-485
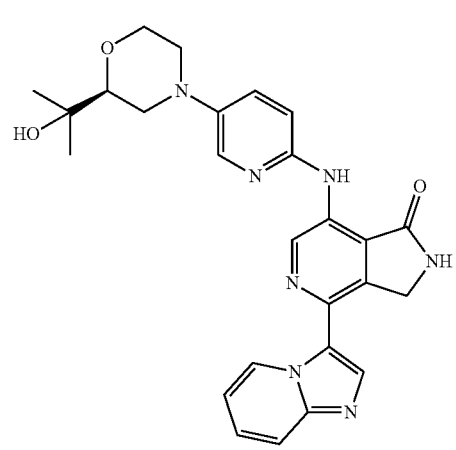
I-486
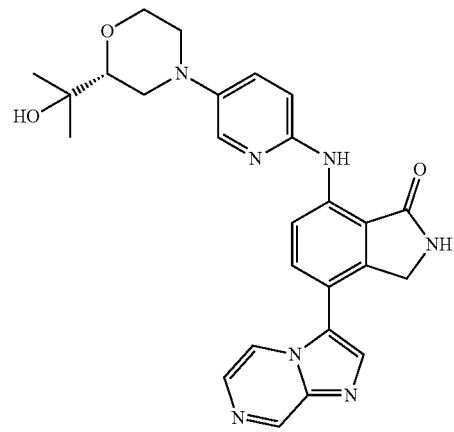
I-487
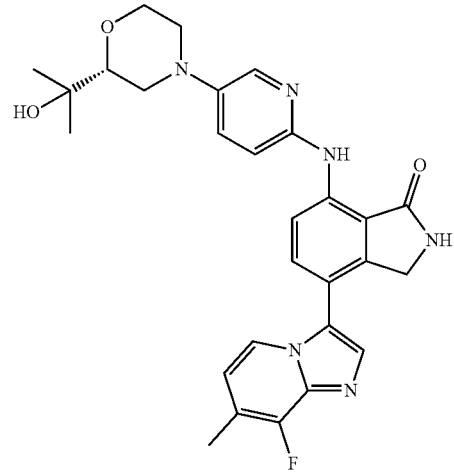

2561
-continued
I-488
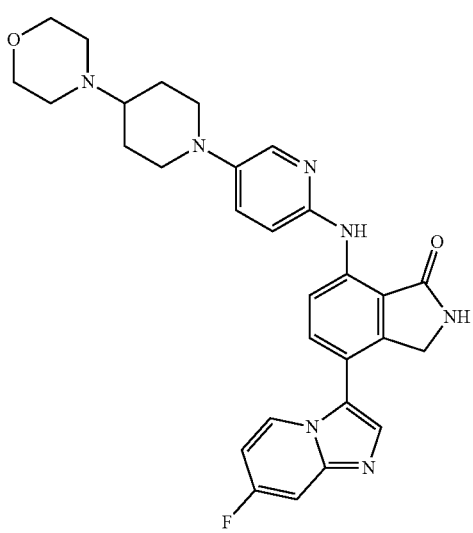
I-491
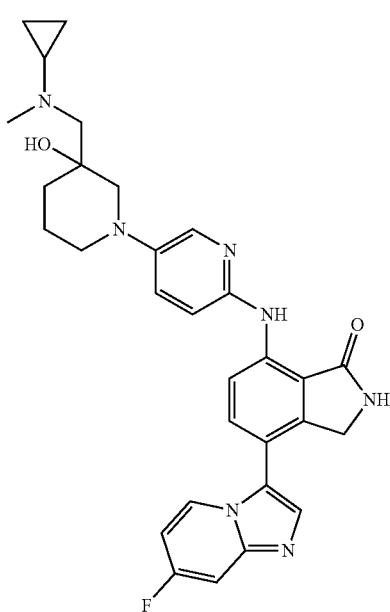
I-493
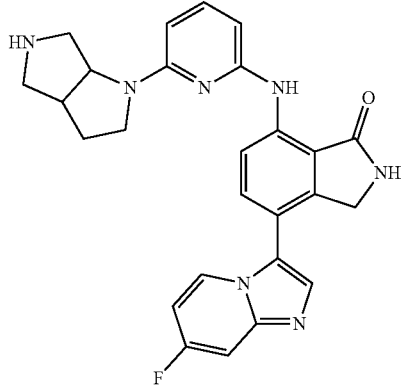
2562
-continued
I-494
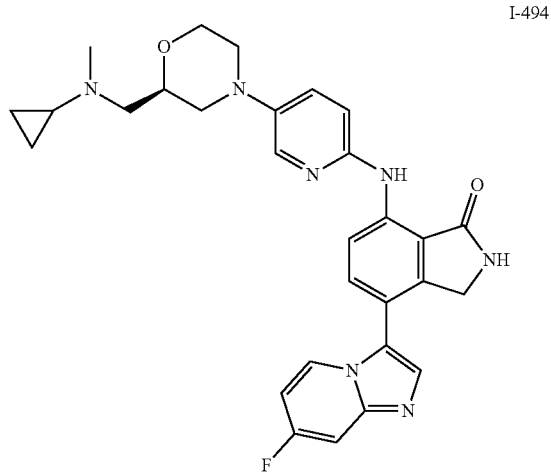
I-495
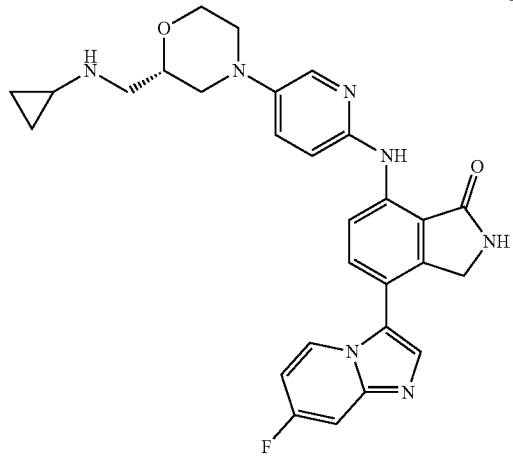
I-496
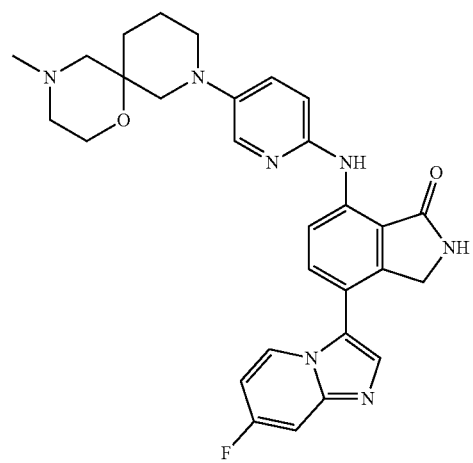

2563
-continued
I-497
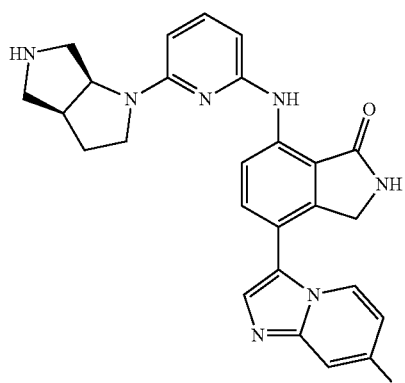
I-498
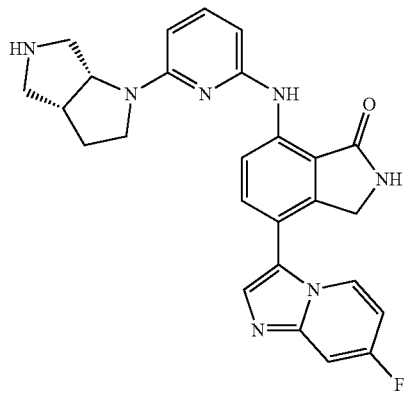
I-499
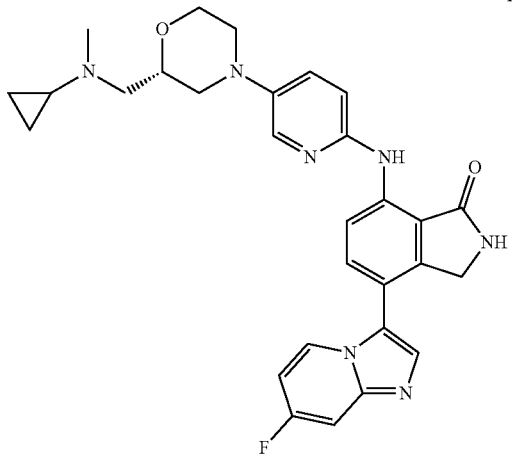
2564
-continued
I-500
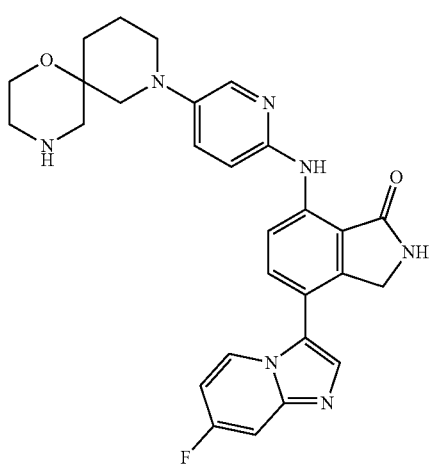
I-501
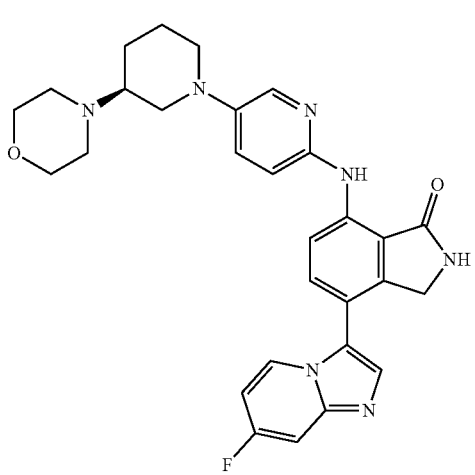
I-502
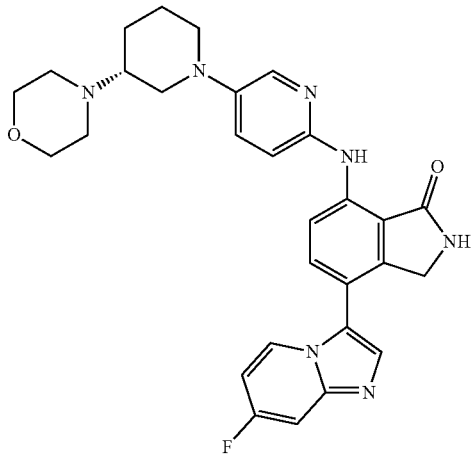

I-503 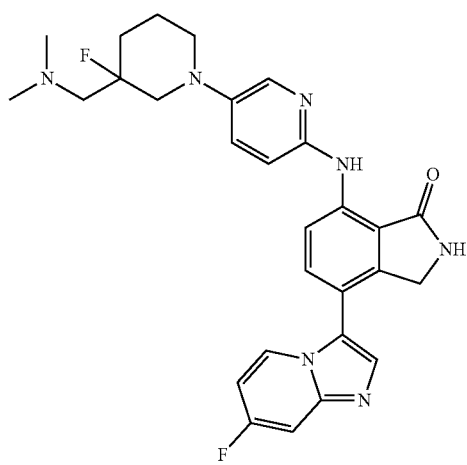
I-504 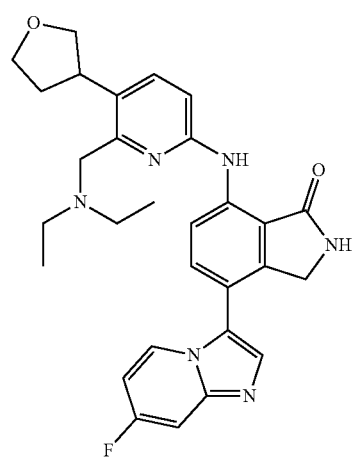
I-505 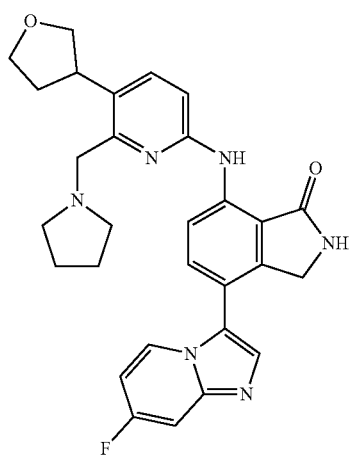
I-506a 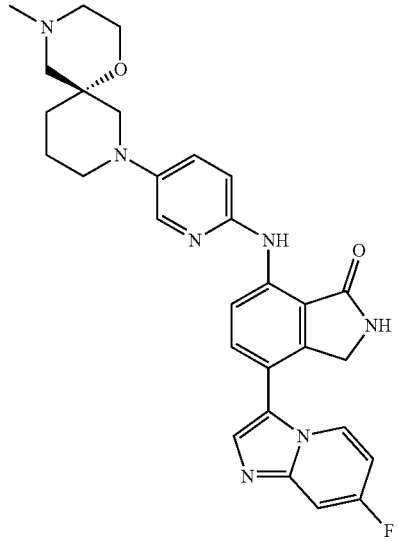
I-506 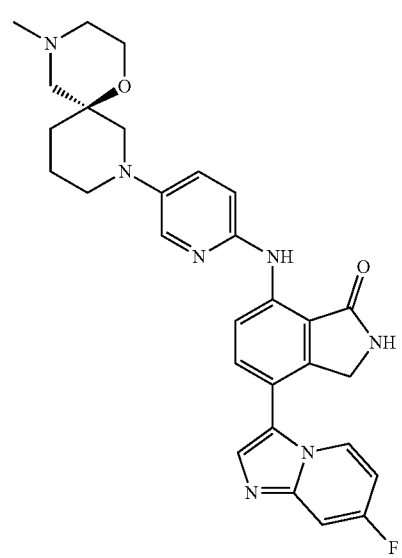
I-507 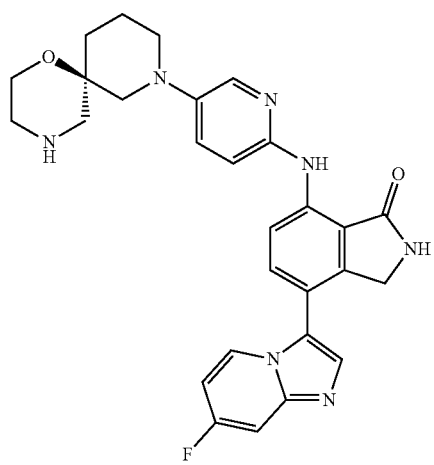

I-508
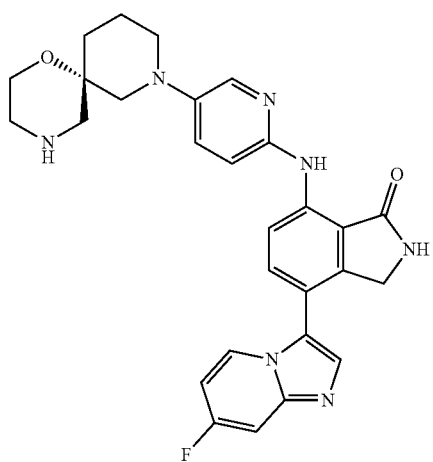
I-511
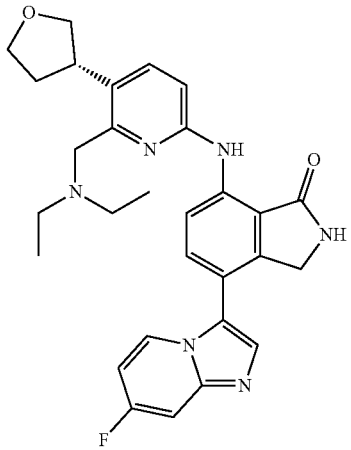
I-509
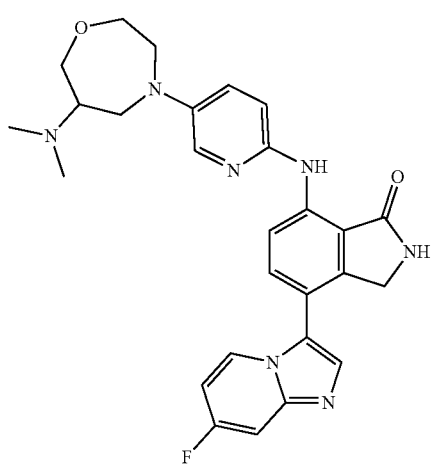
I-512
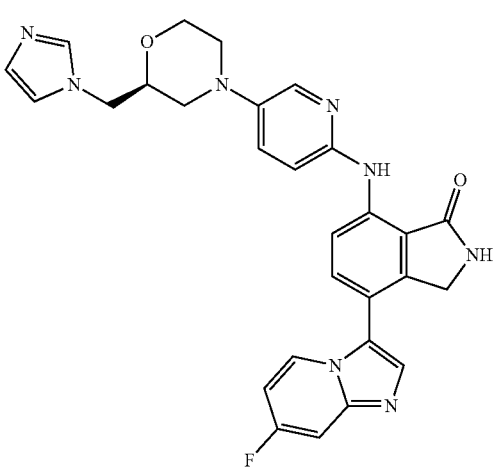
I-510
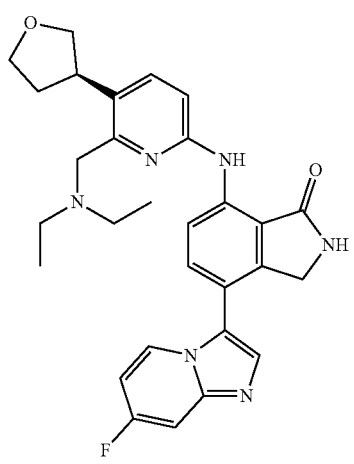
I-513
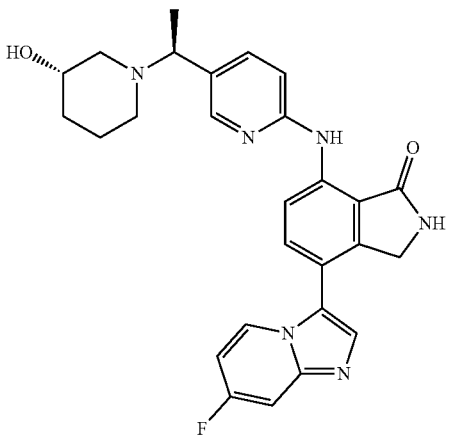

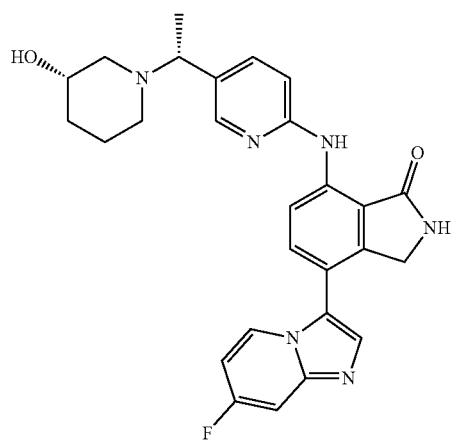
I-514
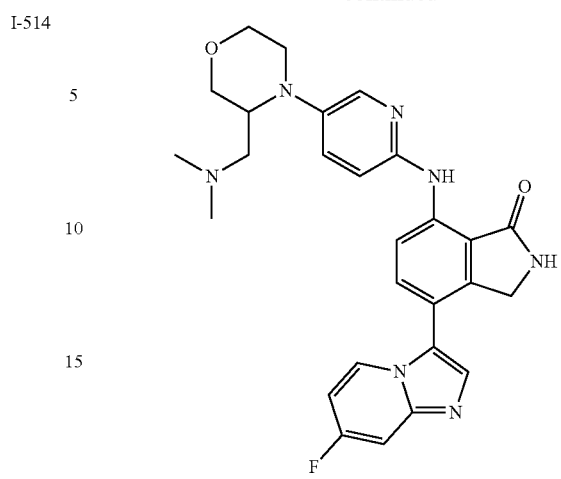
I-517
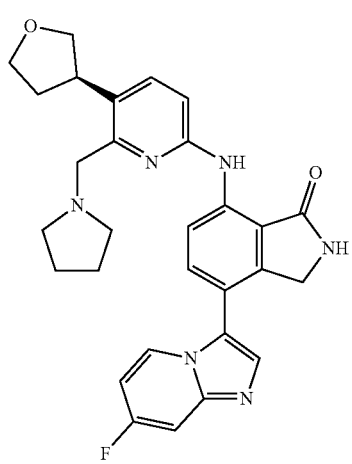
I-515
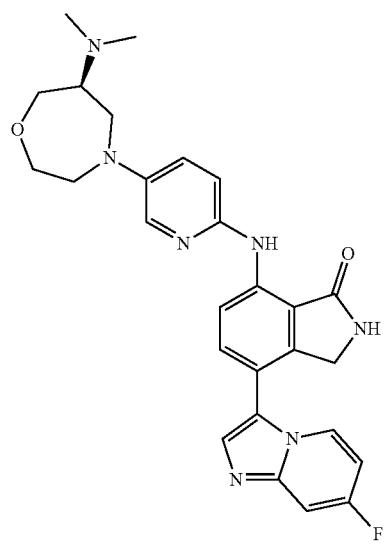
I-518
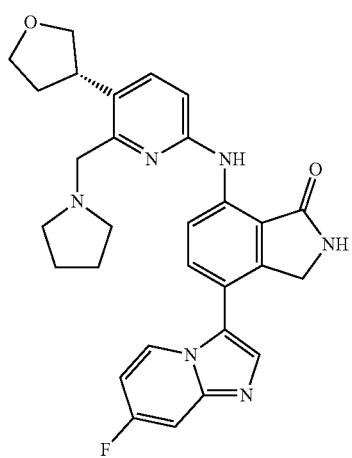
I-516
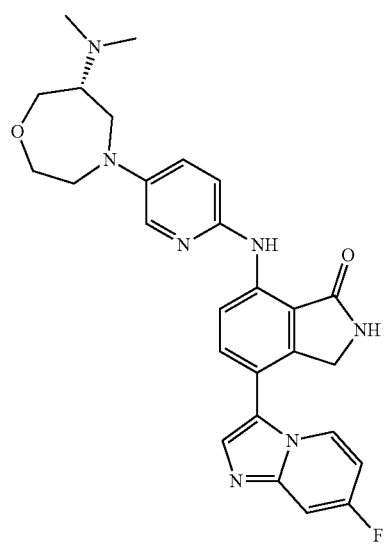
I-519

| 2571 -continued | 2572 -continued |
|---|---|
| I-520 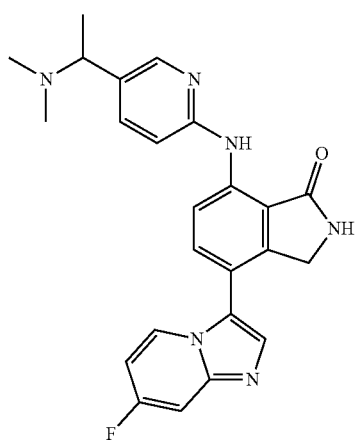 | I-526 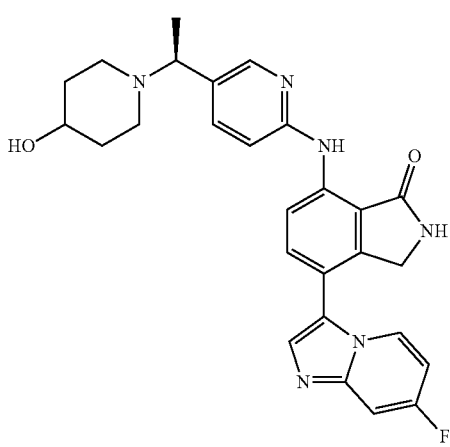 |
| I-521 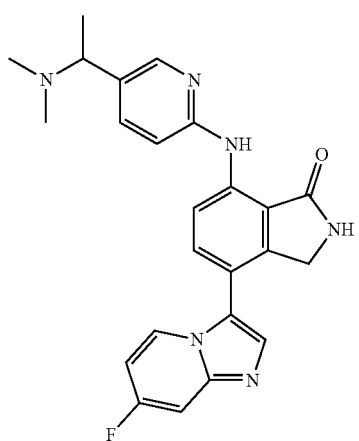 | I-527 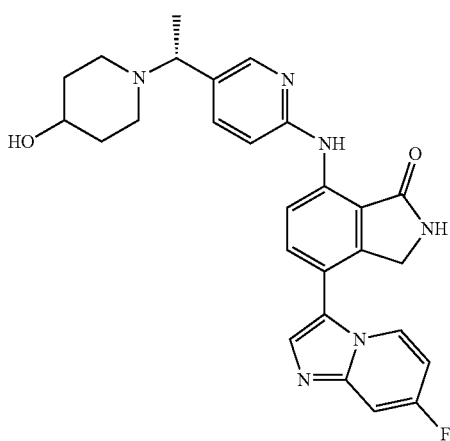 |
| I-525 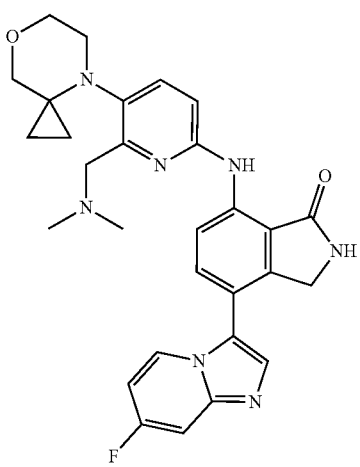 | I-528 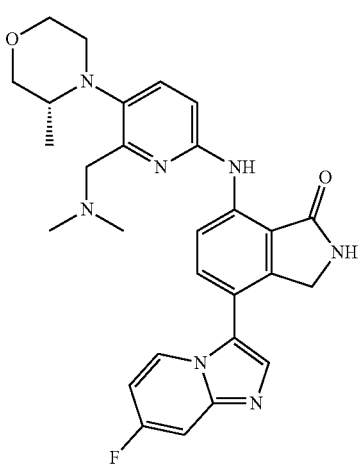 |

I-529
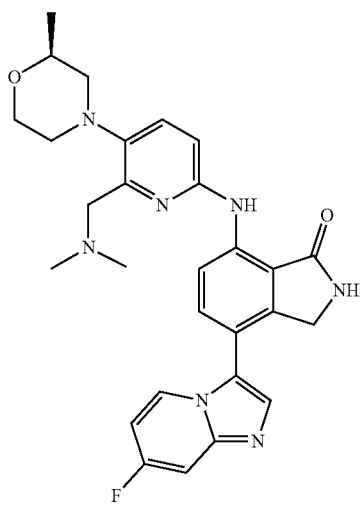
I-530
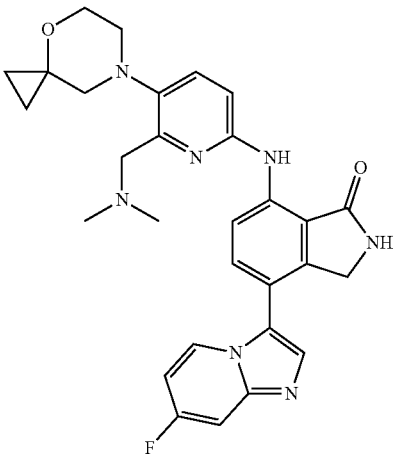
I-531
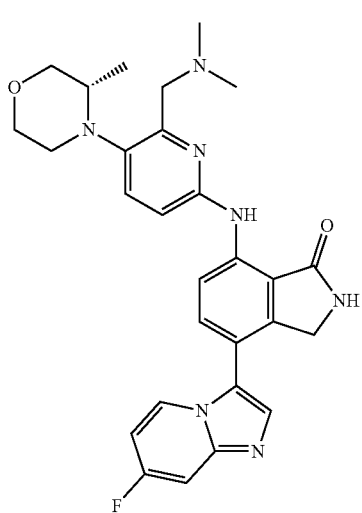
I-535
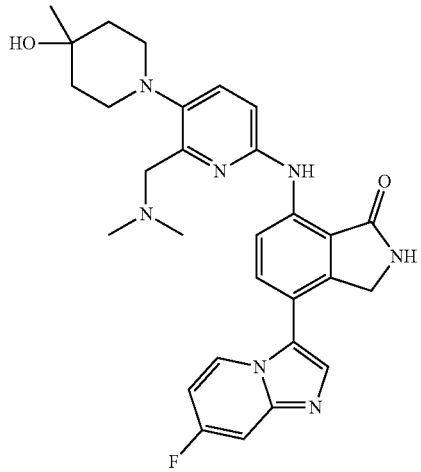
I-536
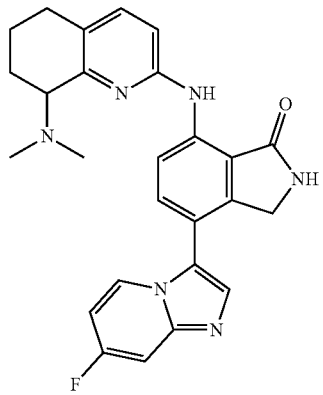
I-537
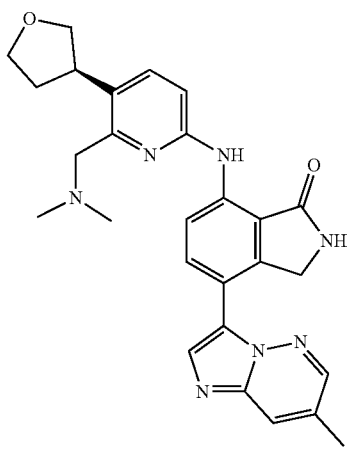

2575
-continued
I-538
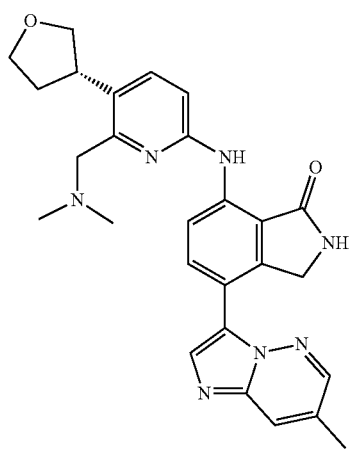
I-539
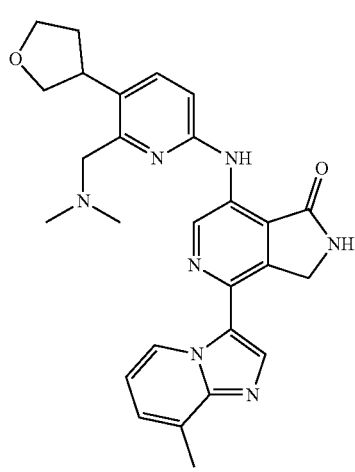
I-540
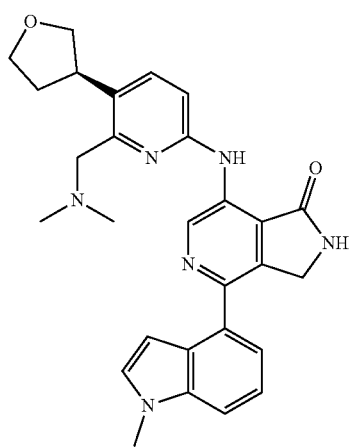
2576
-continued
I-541
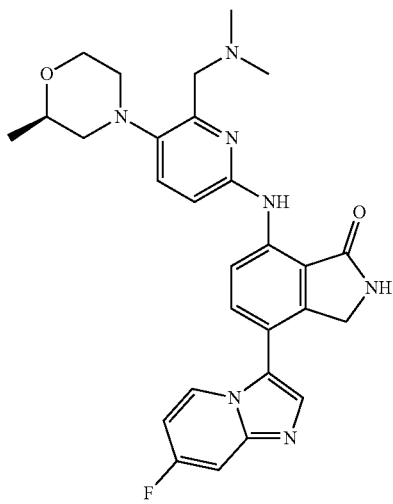
I-542
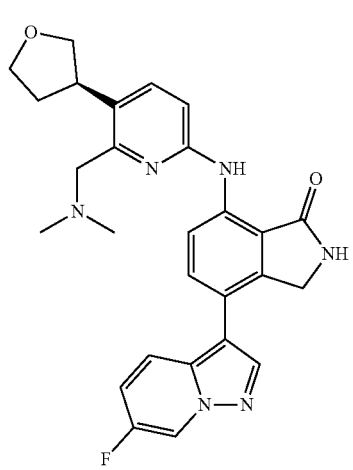
I-543
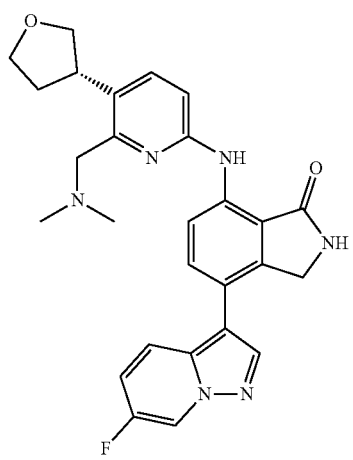

2577
-continued
I-545
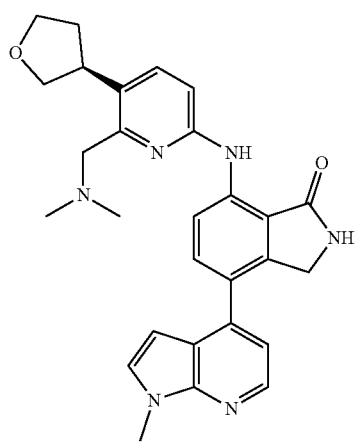
I-546
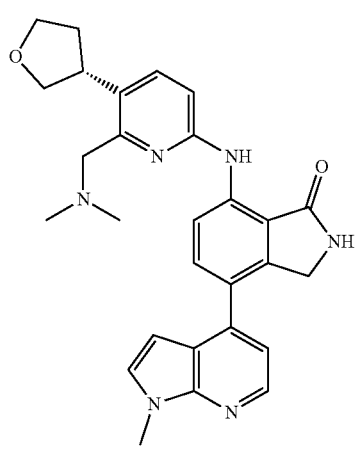
I-547
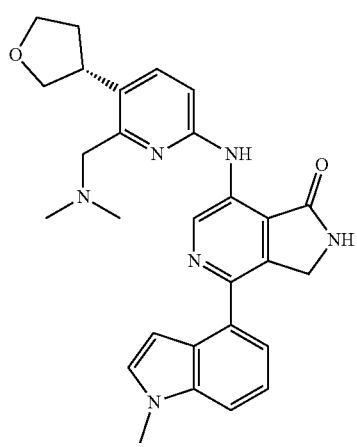
2578
-continued
I-548
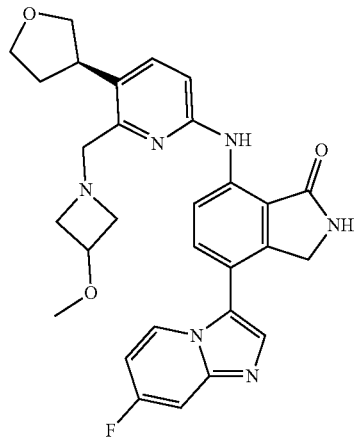
I-549
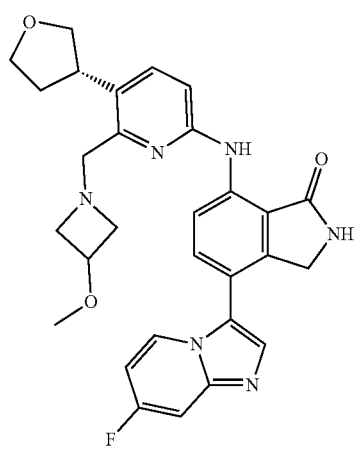
I-552
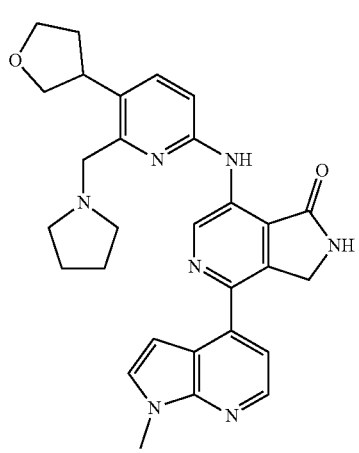

-continued
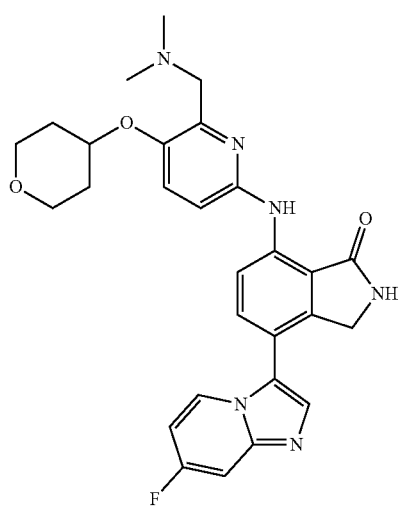
I-553
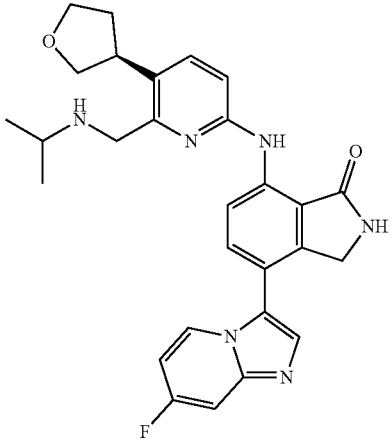
I-558
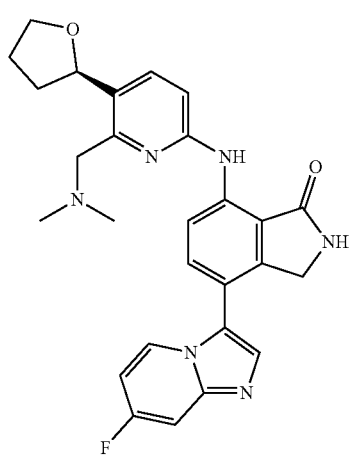
I-554
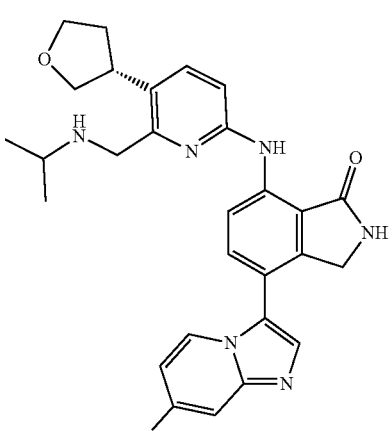
I-559
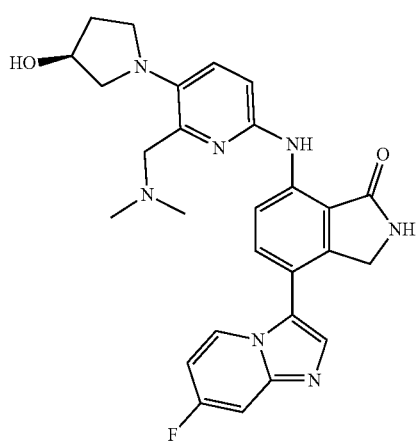
I-555
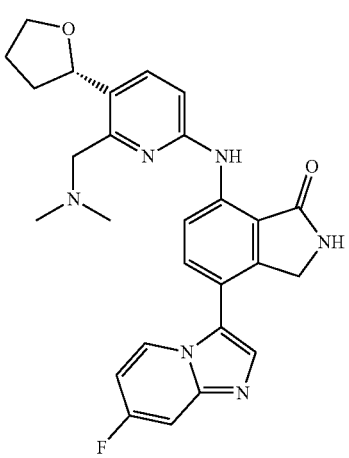
I-560

2581
-continued
I-561
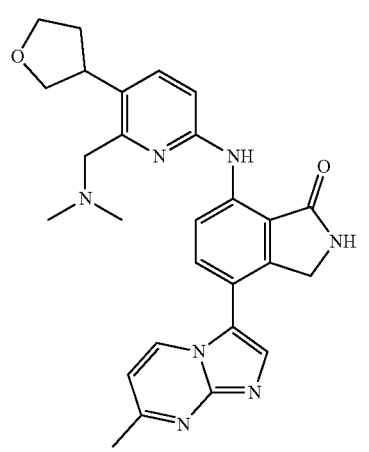
I-562
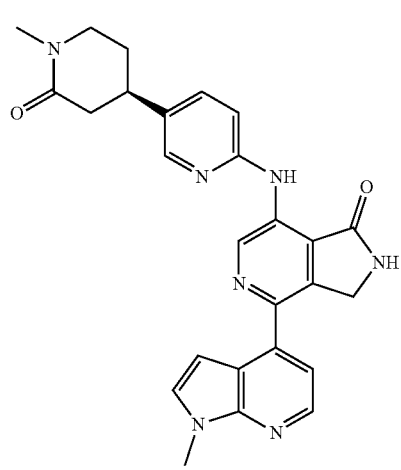
I-563
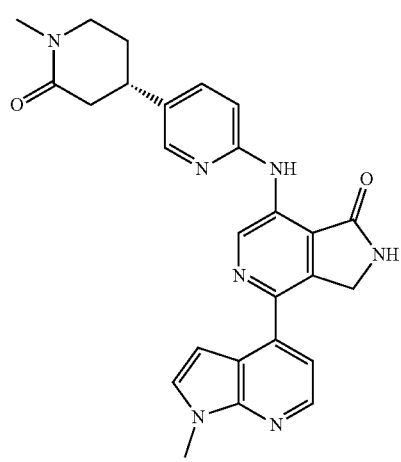
2582
-continued
I-564
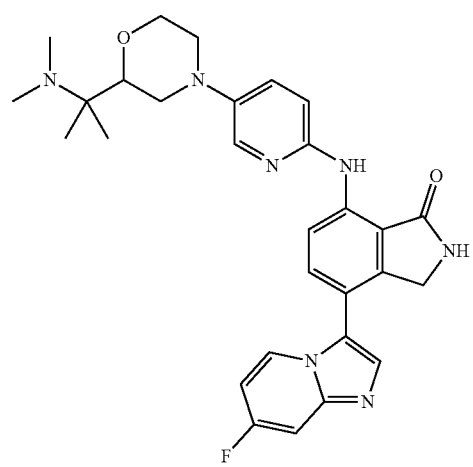
I-565
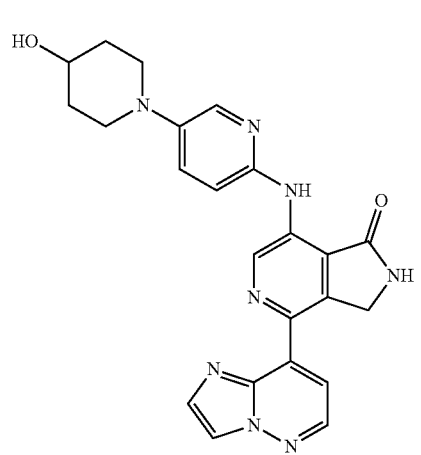
I-566
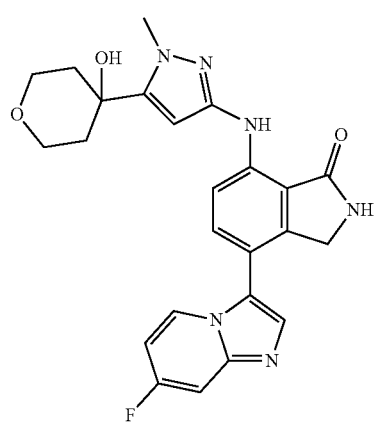

I-567
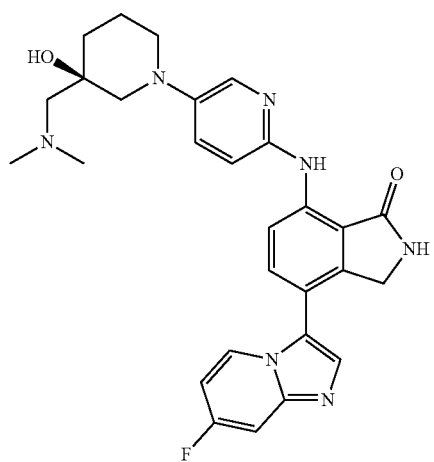
I-568
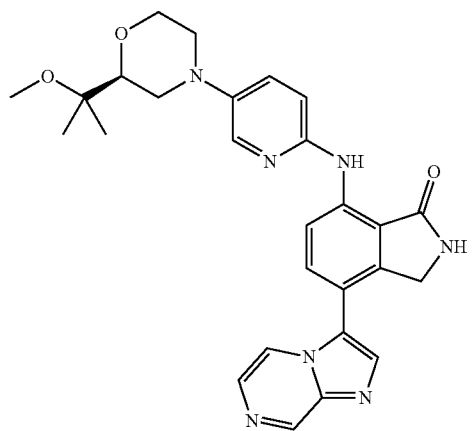
I-569
I-570
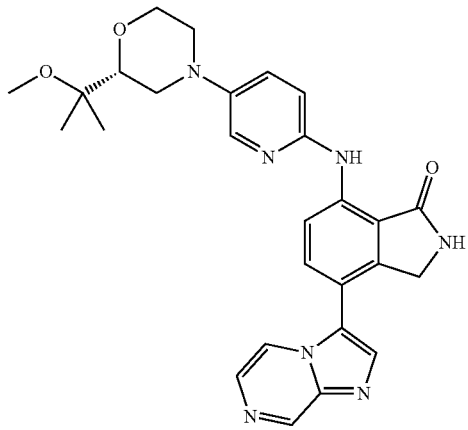
I-571
I-572
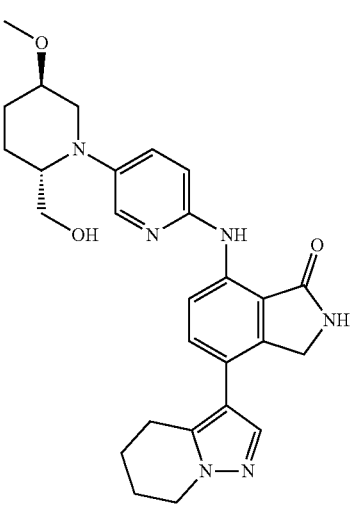

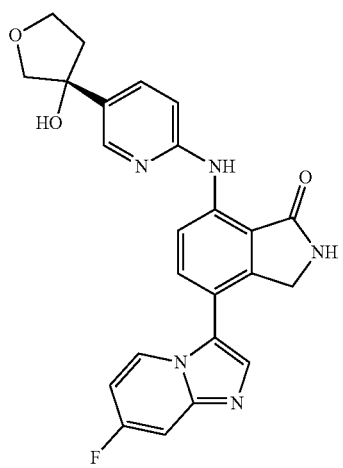
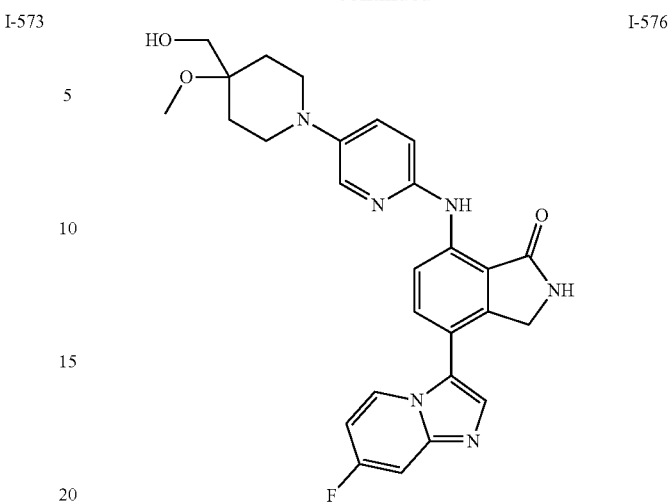

2587 -continued
I-579
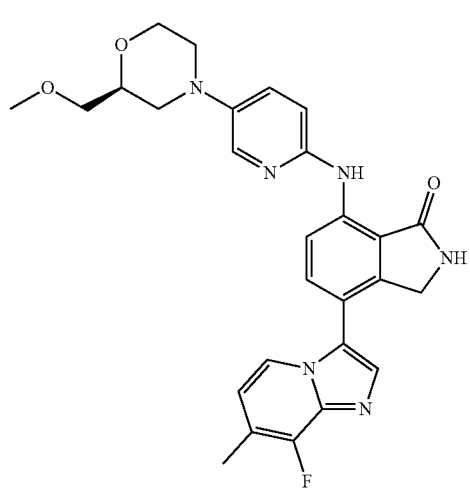
I-580
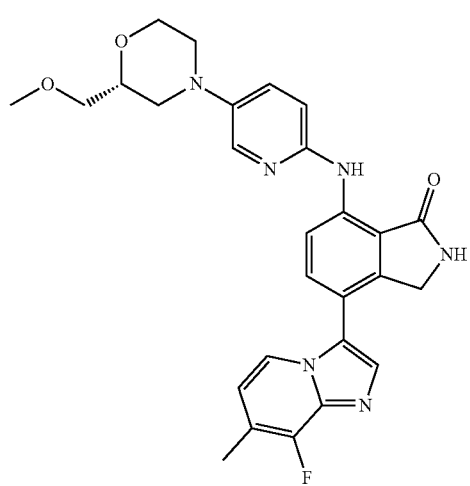
I-581
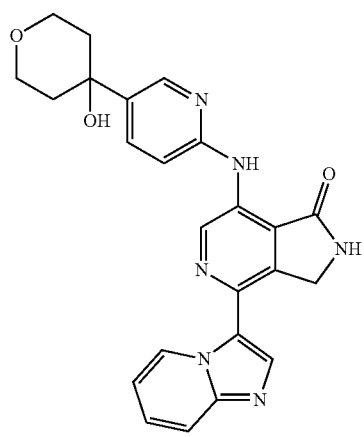
2588 -continued
I-582
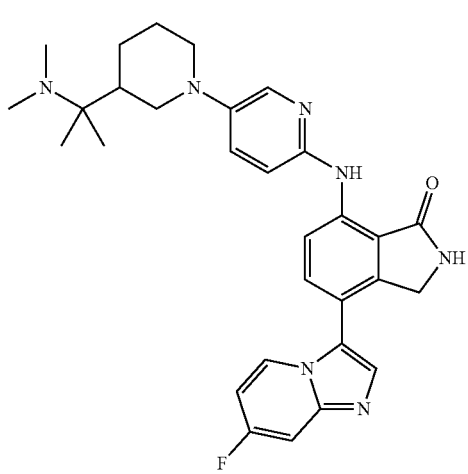
I-583
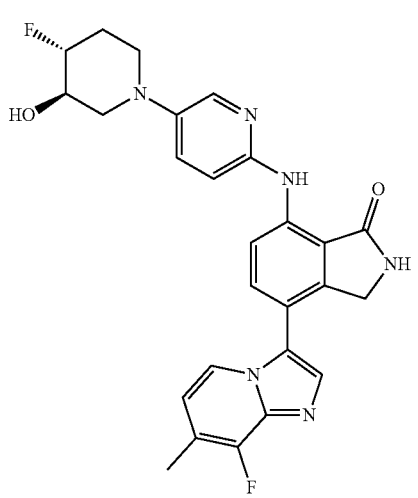
I-584
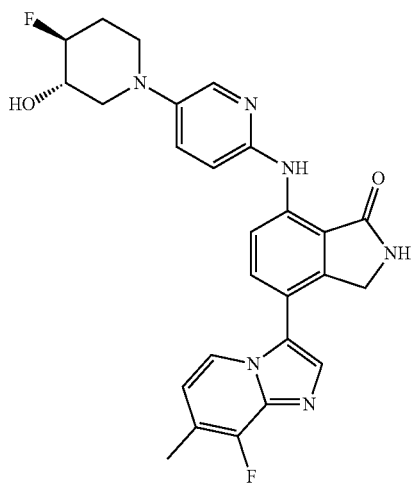

2589
-continued
I-585
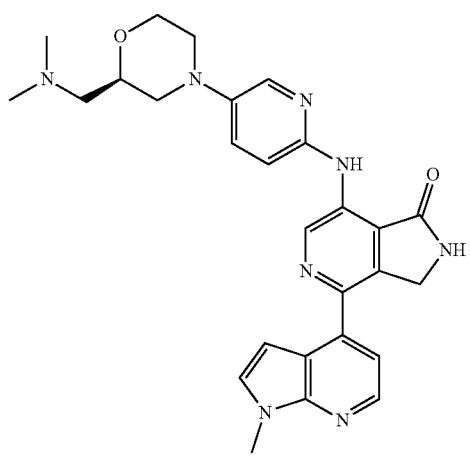
I-586
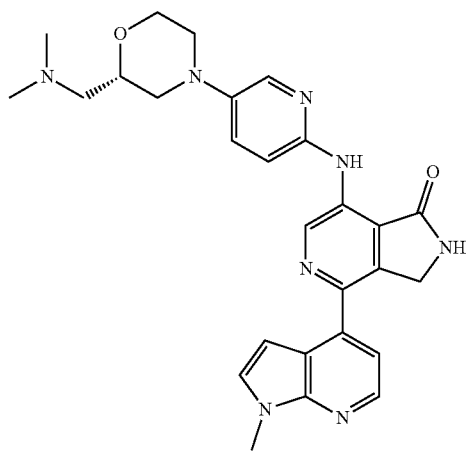
I-587
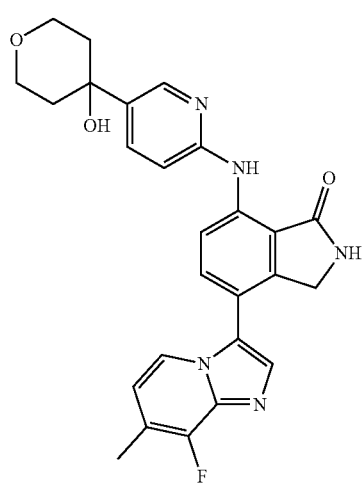
2590
-continued
I-588
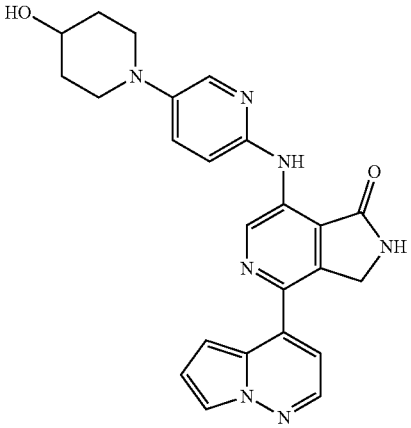
I-589
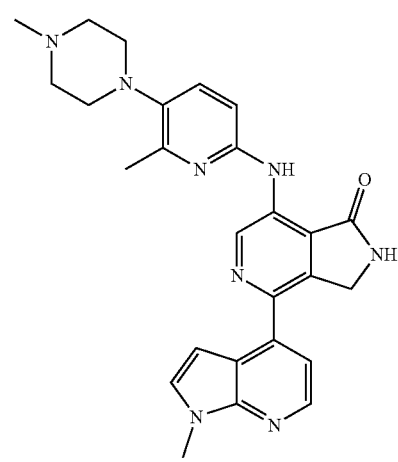
I-590
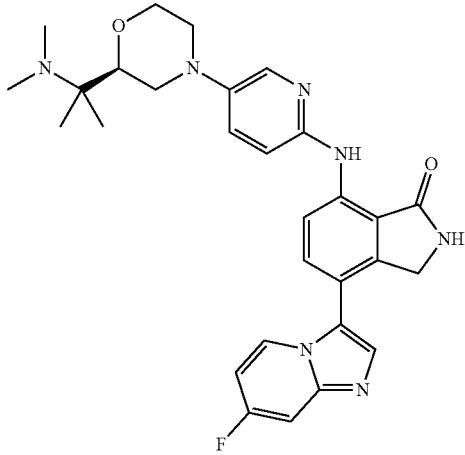

I-591
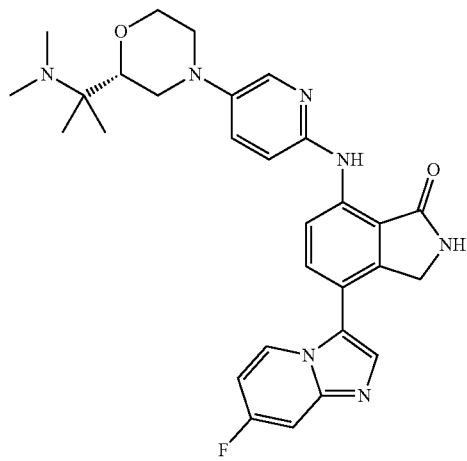
I-594
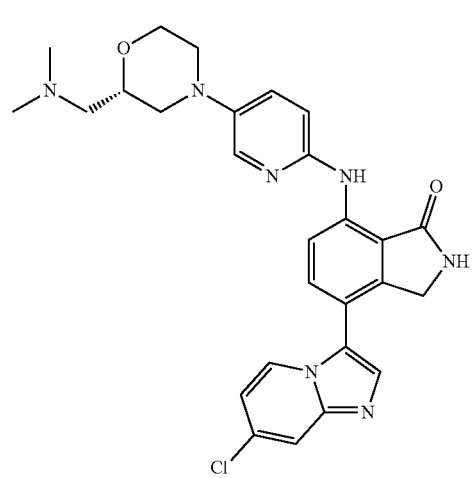
I-592
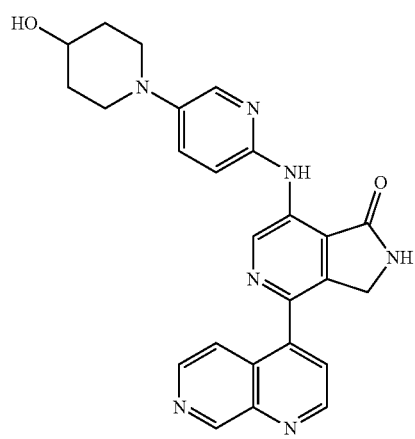
I-595
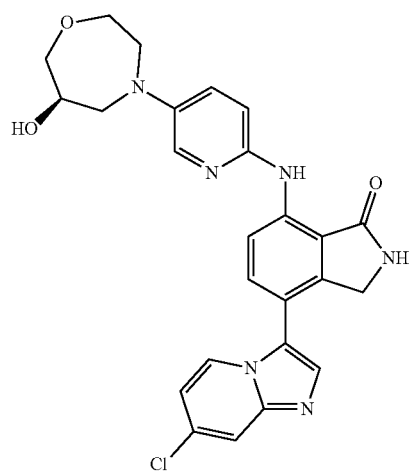
I-593
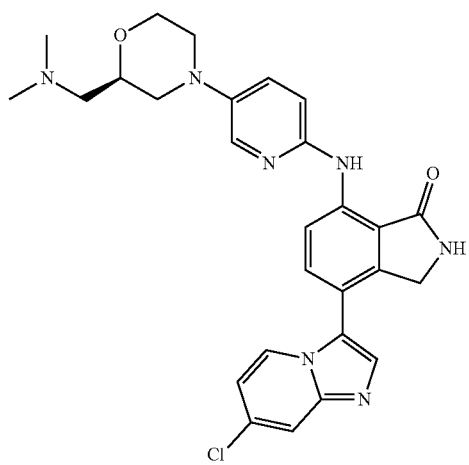
I-596
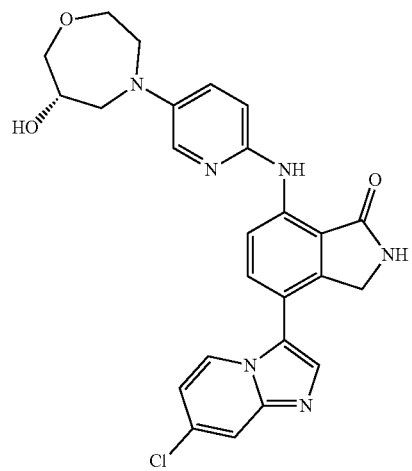

2593
-continued
I-597
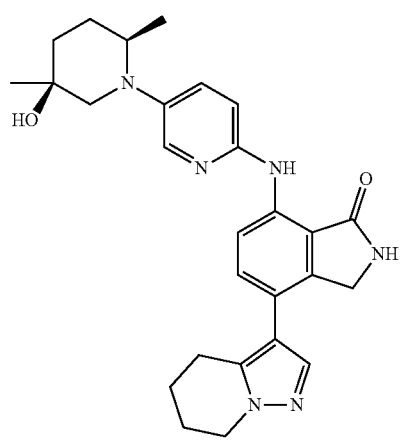
I-598
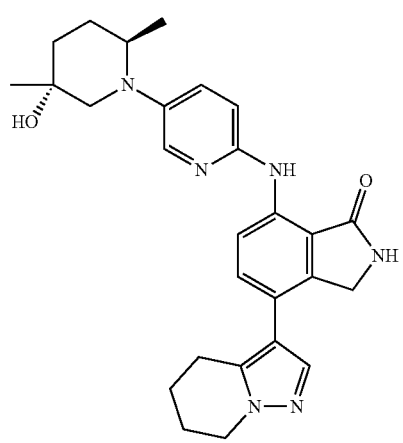
I-599
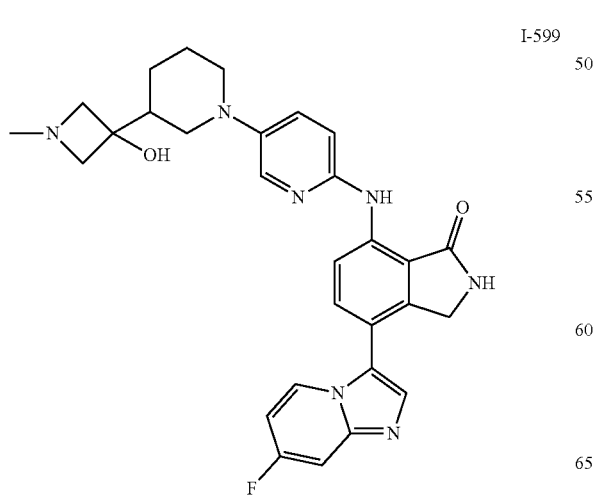
2594
-continued
I-600
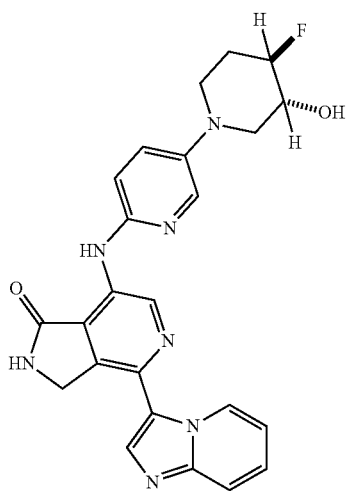
I-601
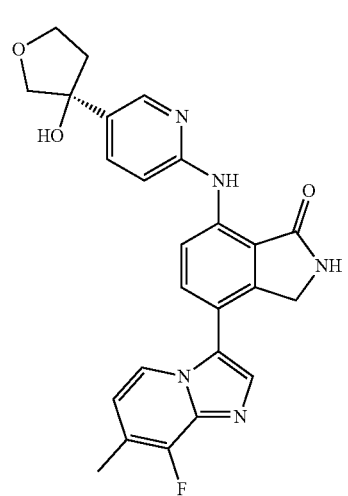
I-602

I-603
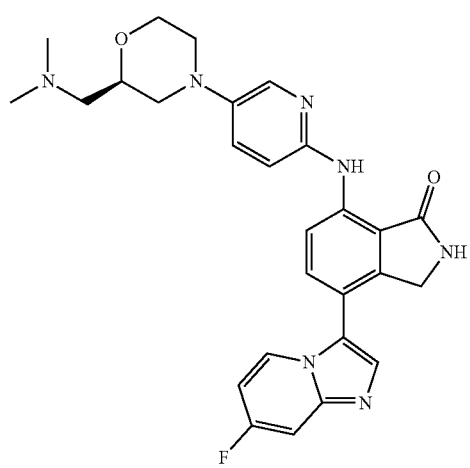
I-604
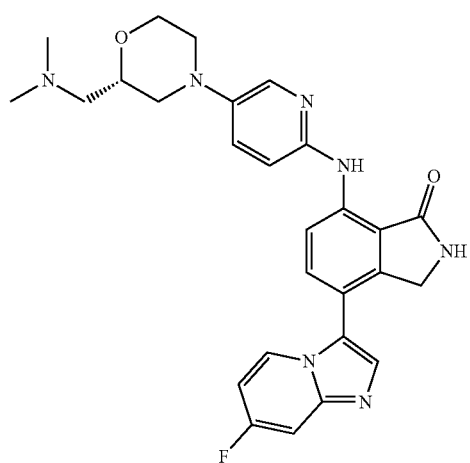
I-605
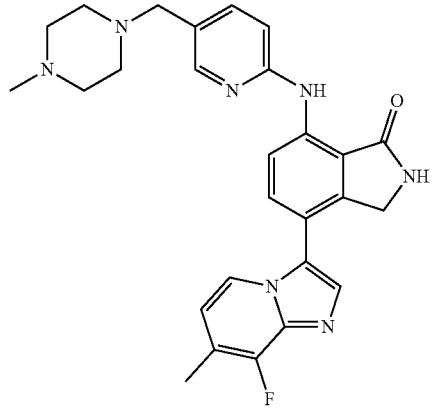
I-606
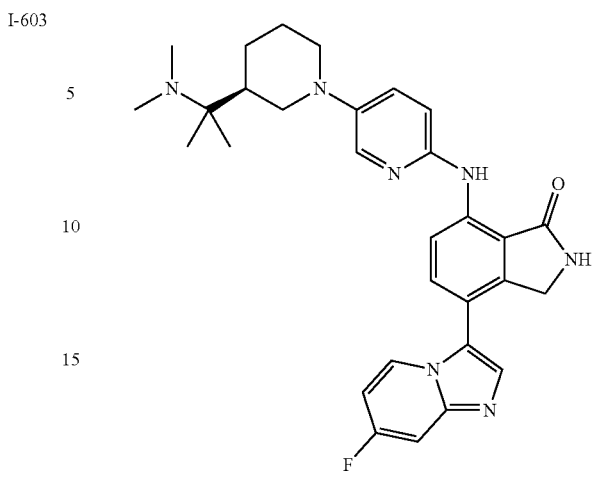
I-607
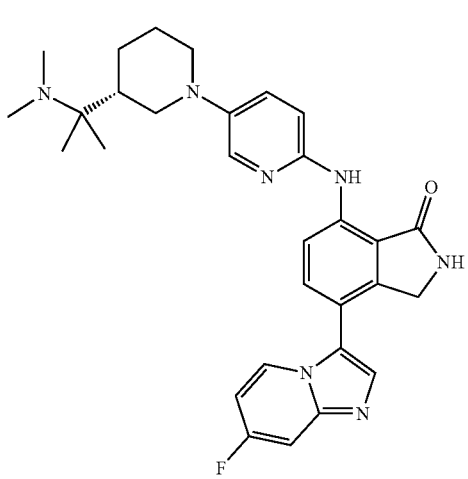
I-608
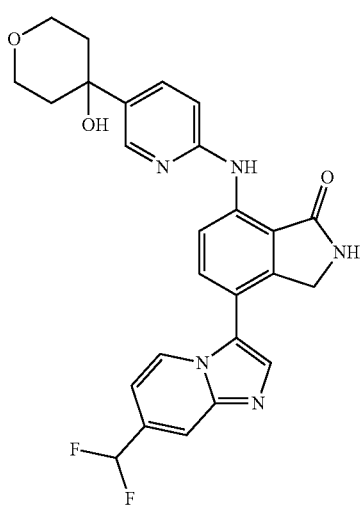

I-609
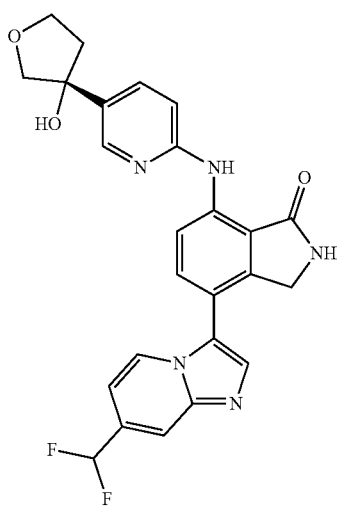
I-610
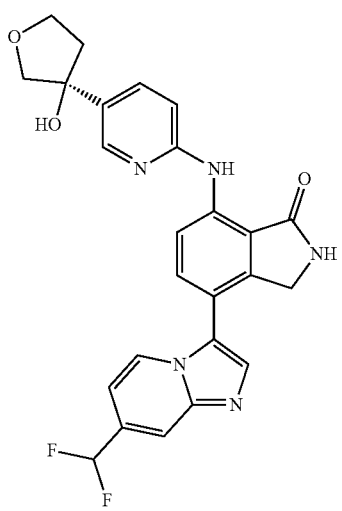
I-611
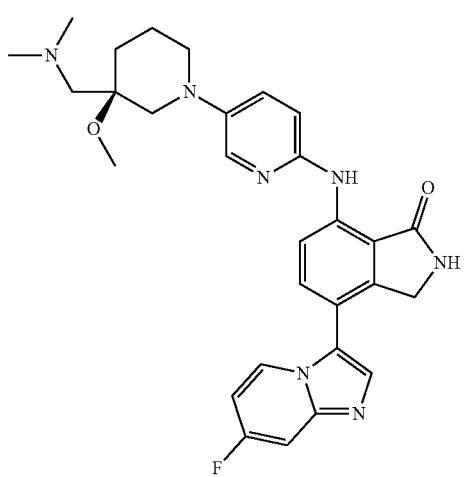
I-612
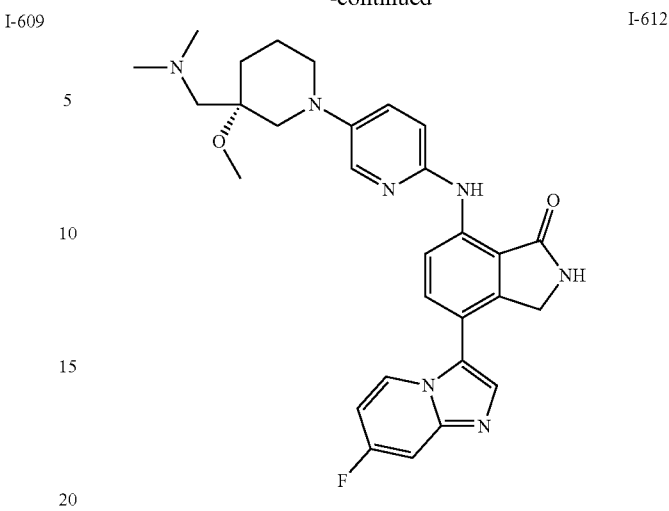
I-613
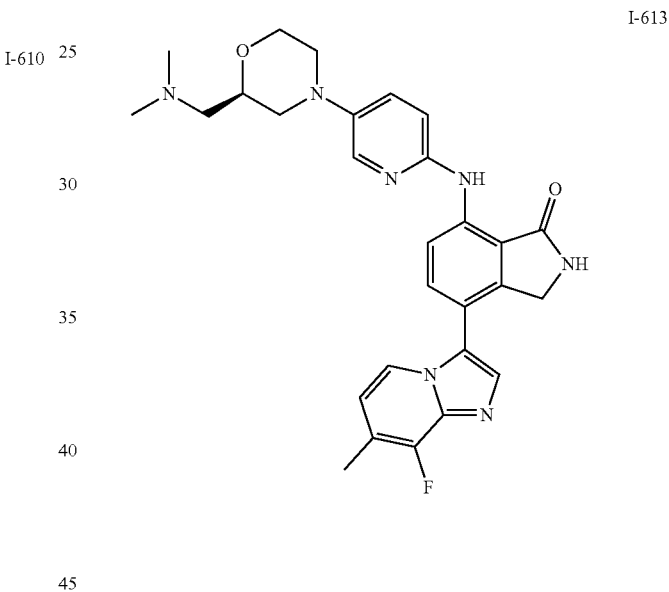
I-614
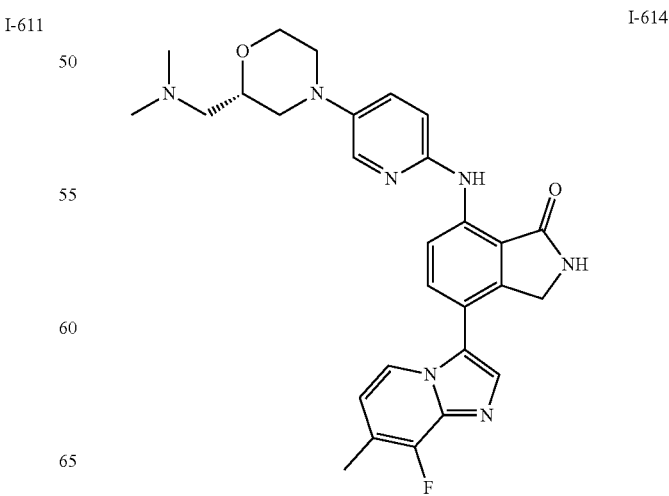

I-615
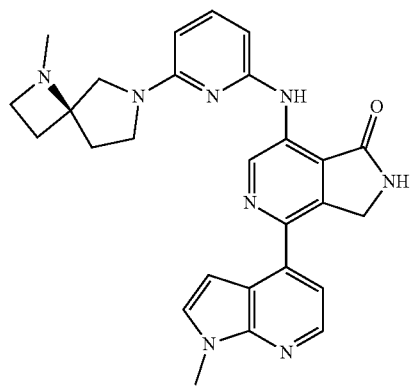
I-616
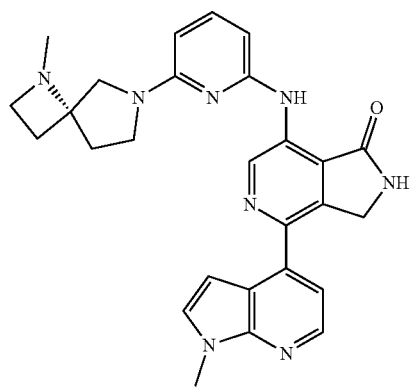
I-617
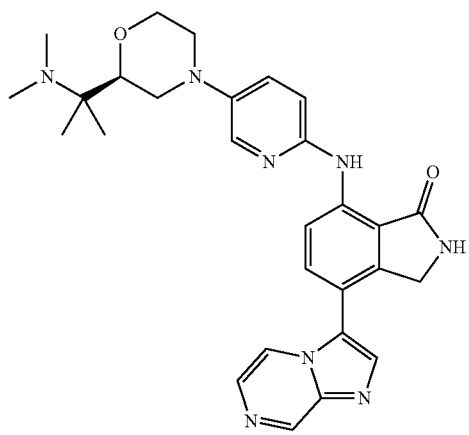
I-618
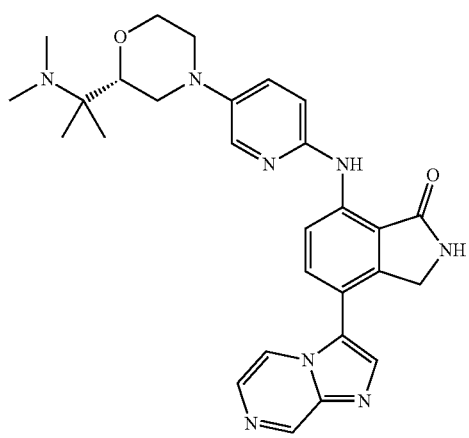
I-621
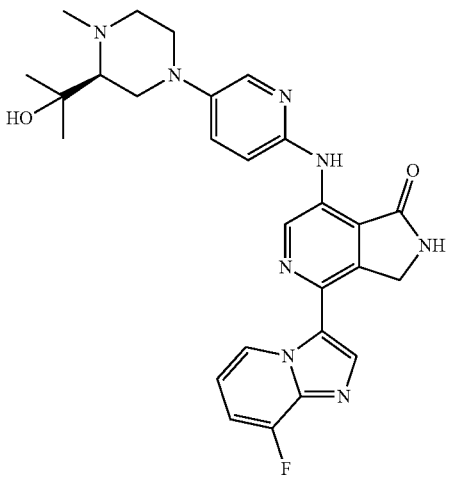
I-622
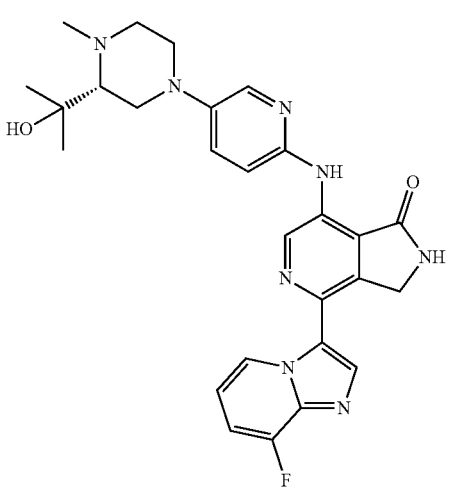
I-623
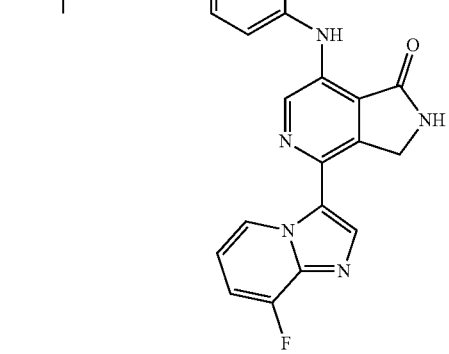

I-624
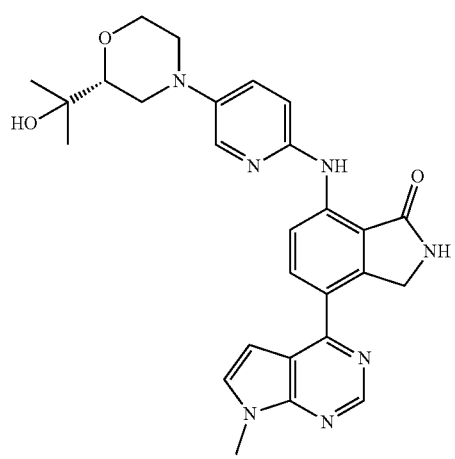
I-628
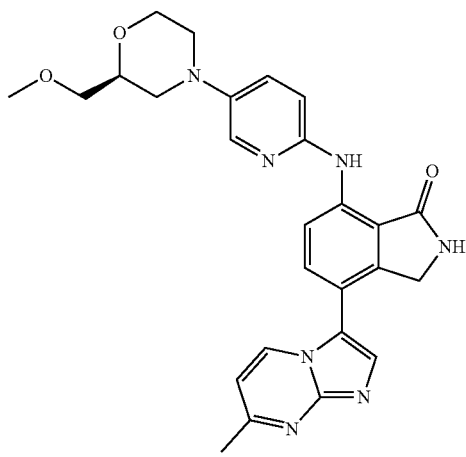
I-626
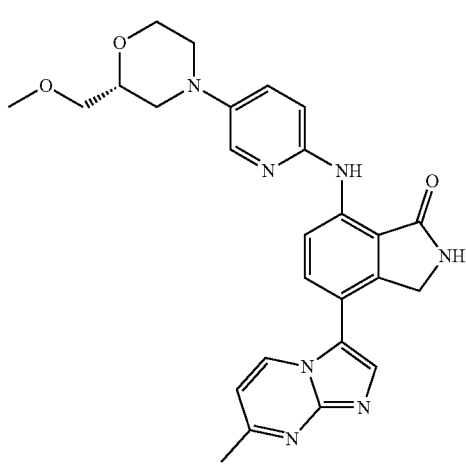
I-629
I-627
I-630
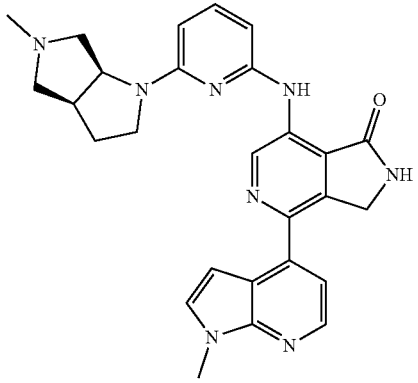

I-631
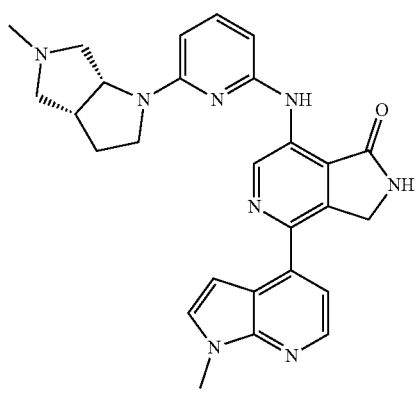
I-632
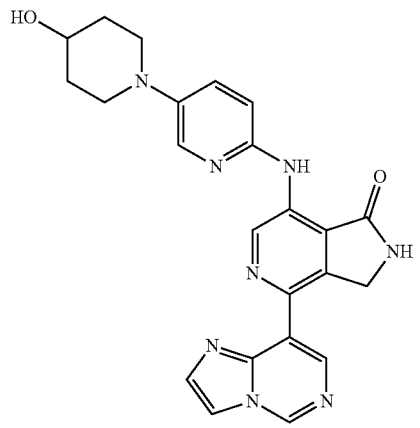
I-633
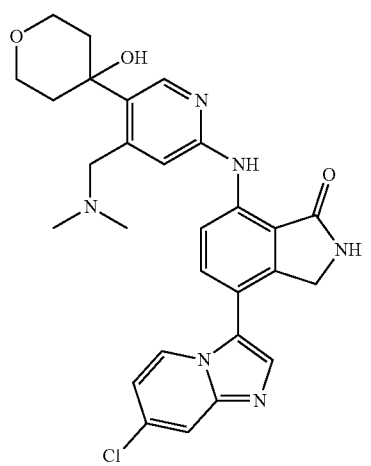
I-634
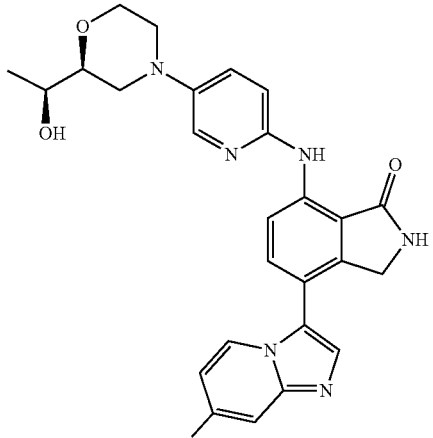
I-635
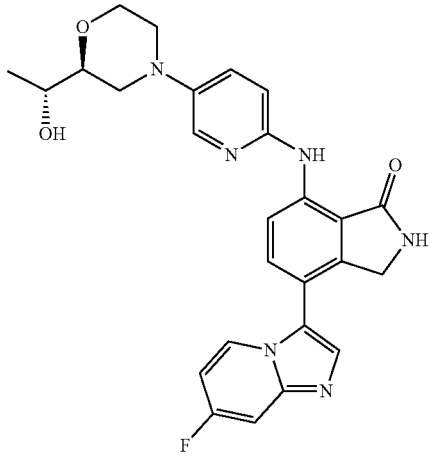
I-639
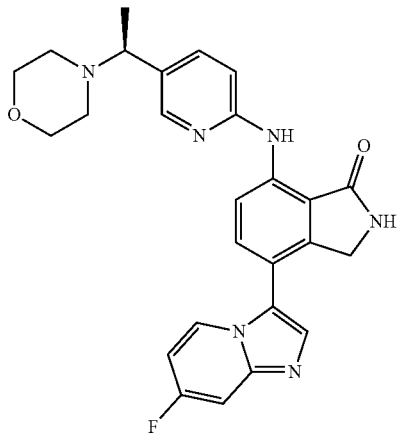

I-640
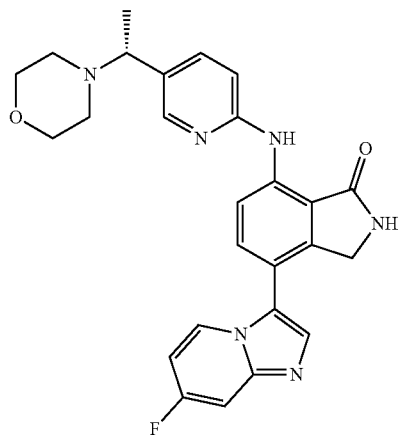
I-645
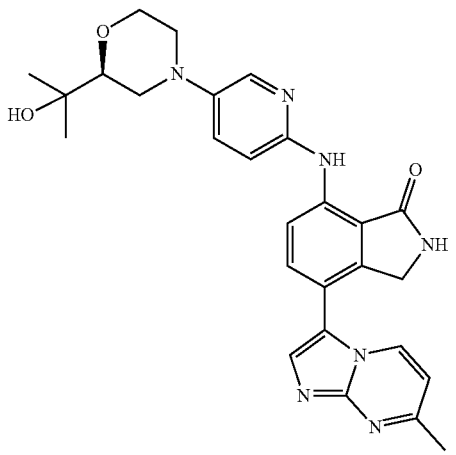
I-643
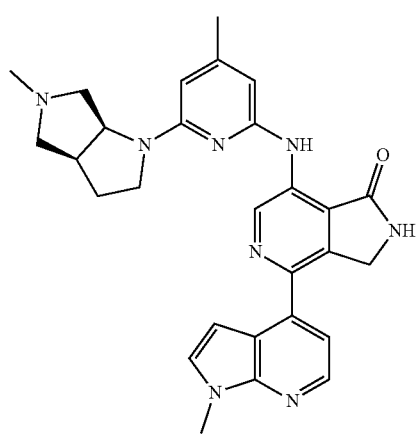
I-646
I-644
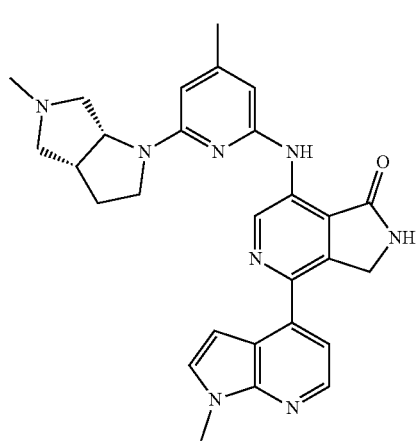
I-648
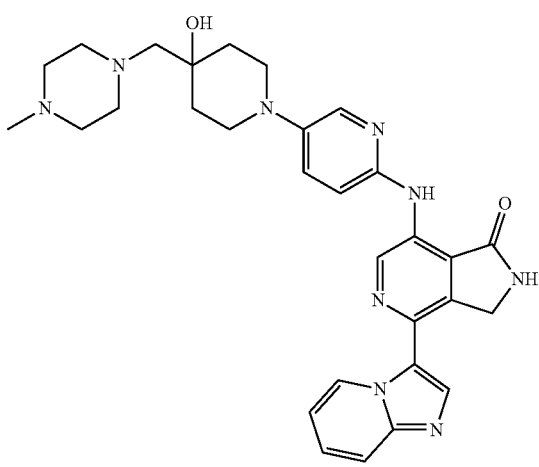

I-649
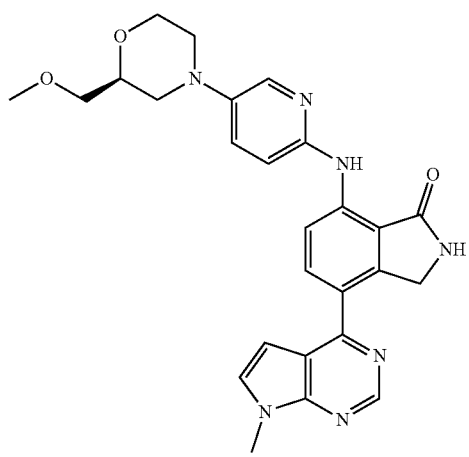
I-650
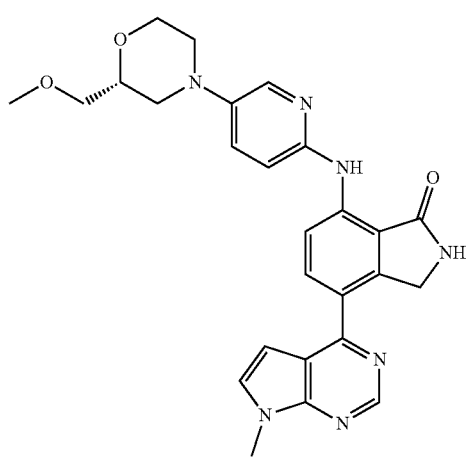
I-651
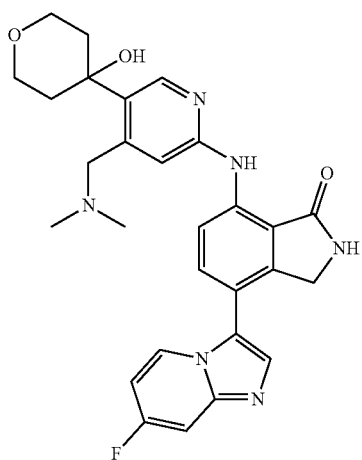
I-652
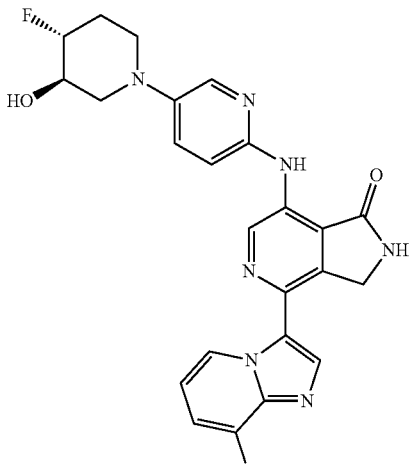
I-653
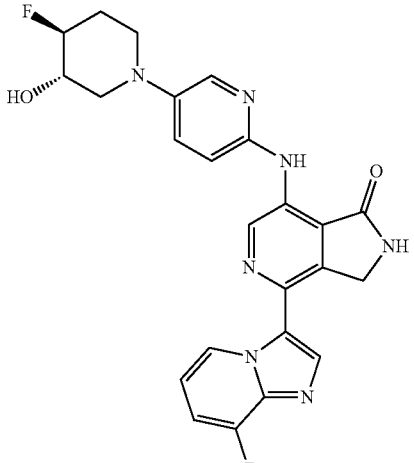
I-654
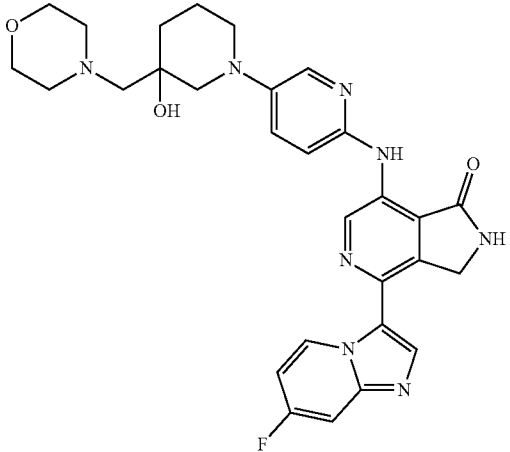

I-655
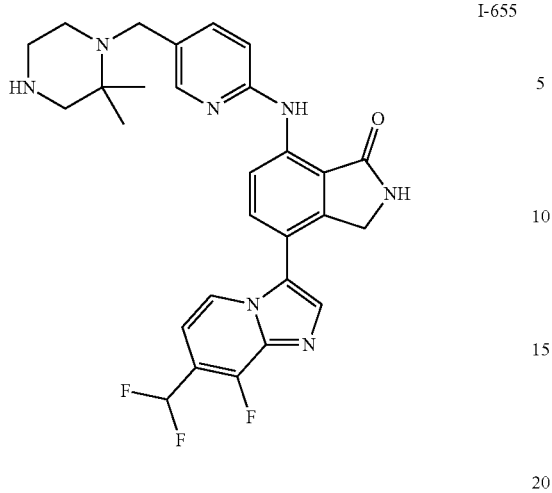
I-658
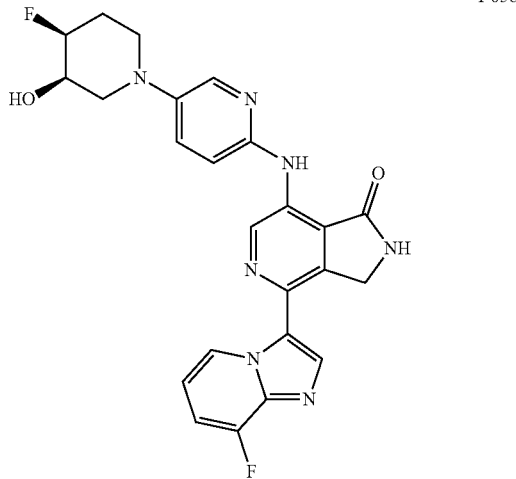
I-656
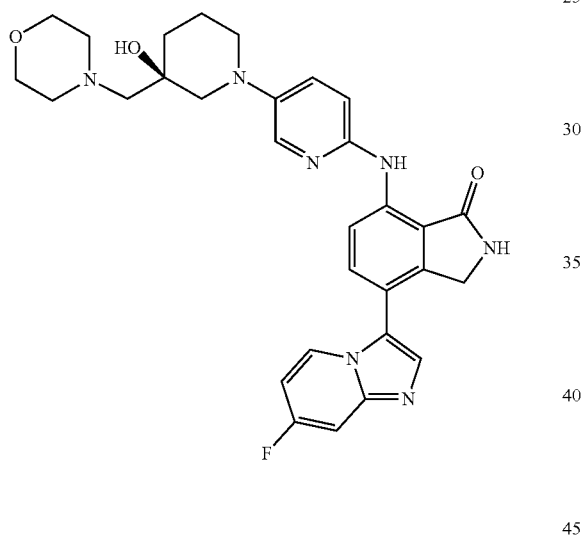
I-659
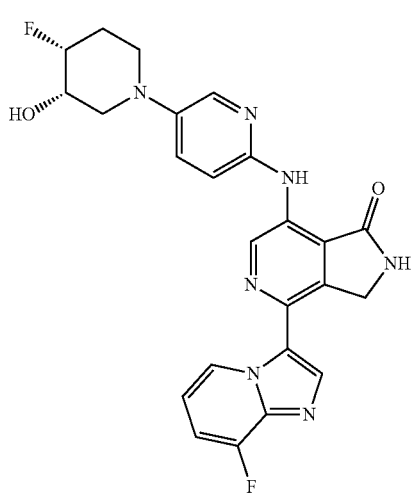
I-657
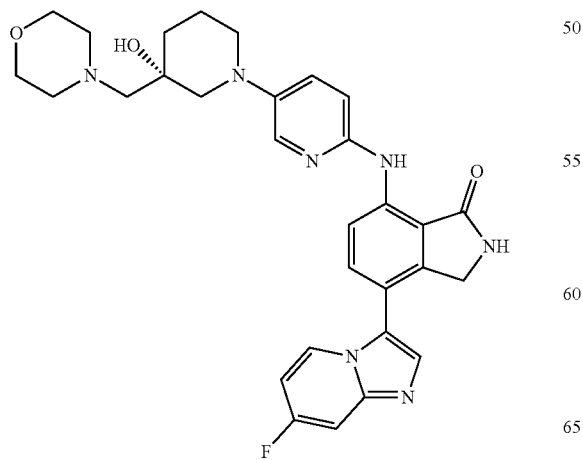
I-660
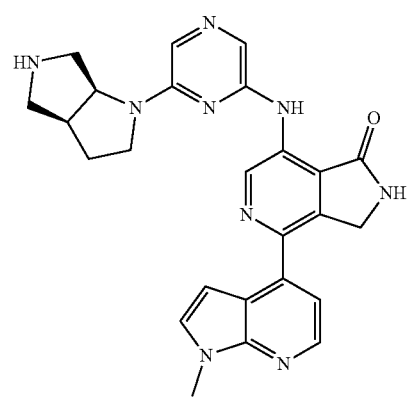

2611
-continued
I-661
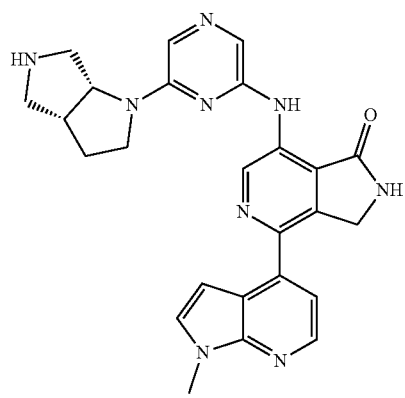
I-667
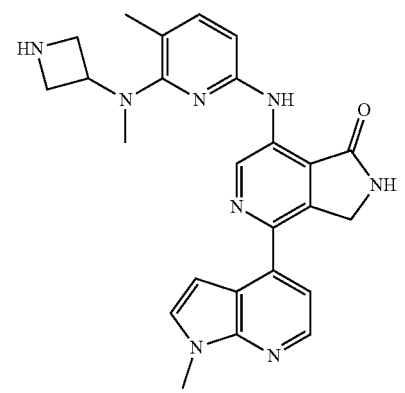
I-668
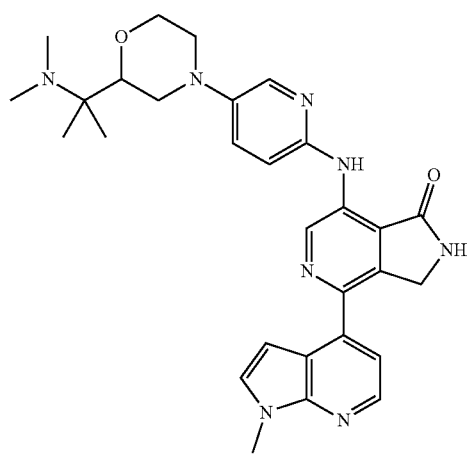
2612
-continued
I-669
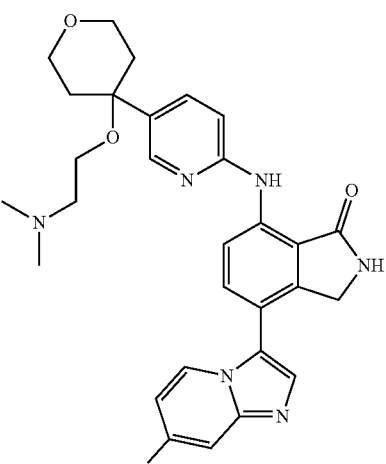
I-672
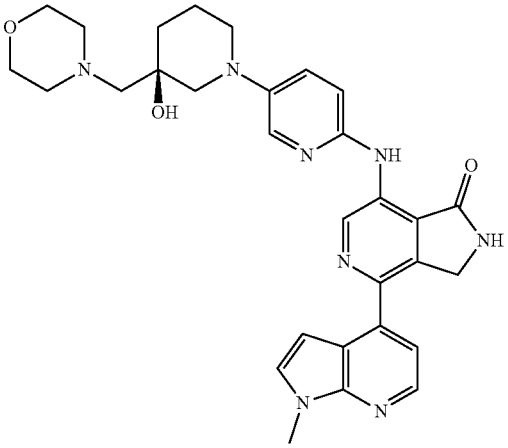
I-673

2613
-continued
I-674
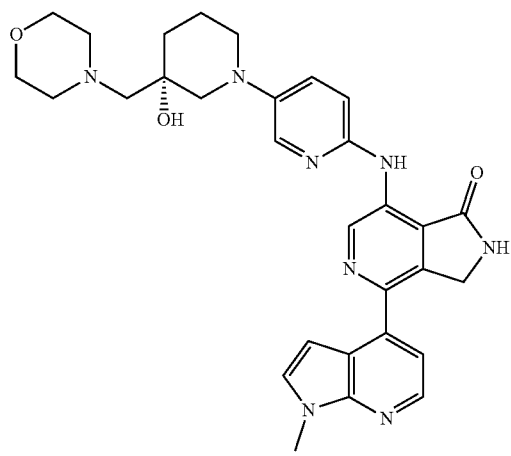
I-677
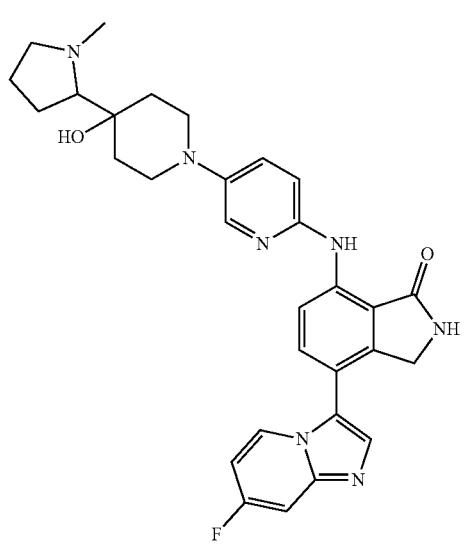
I-678
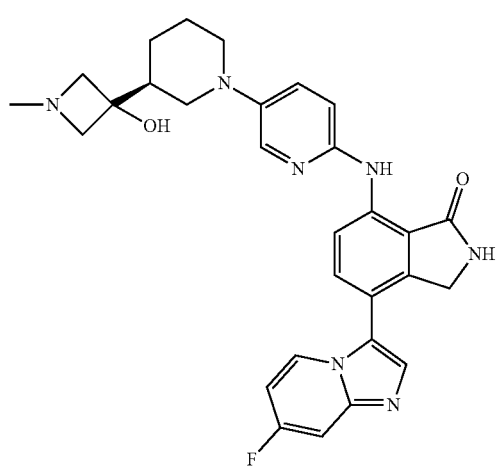
2614
-continued
I-679
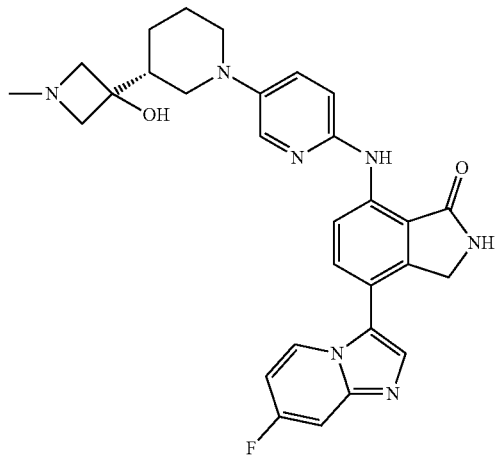
I-680
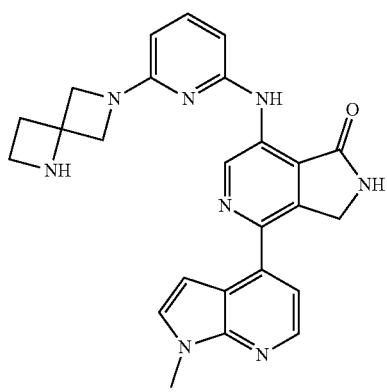
I-681
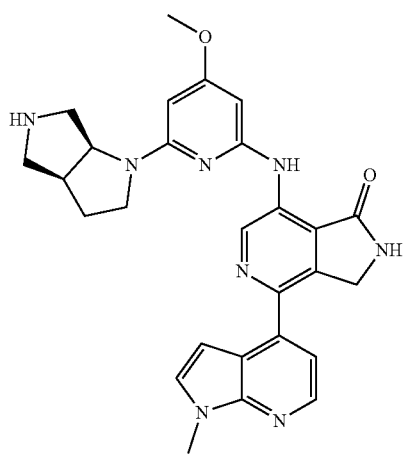

2615
-continued
I-682
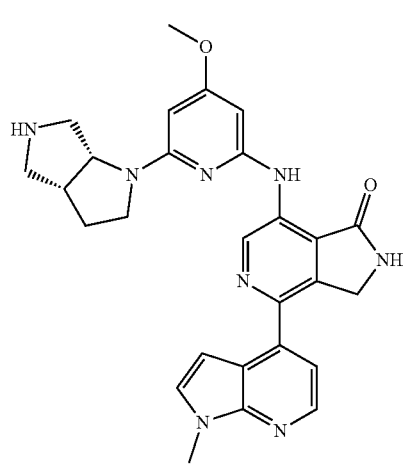
I-683
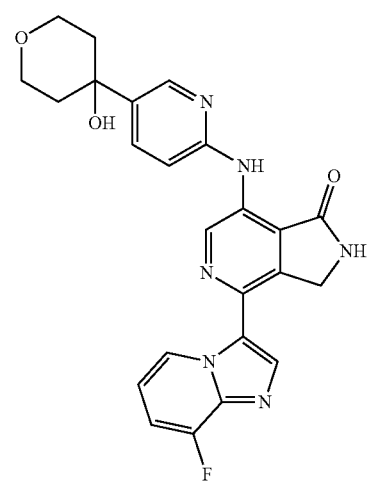
I-684
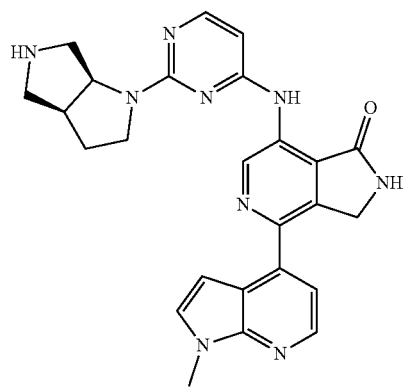
2616
-continued
I-685
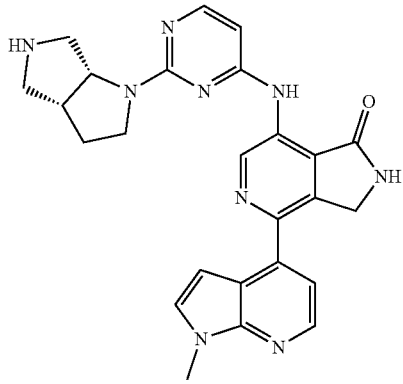
I-686
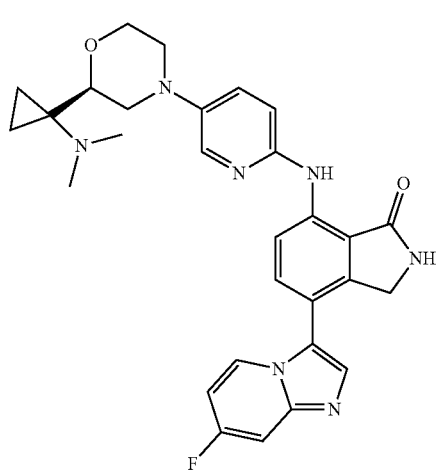
I-687
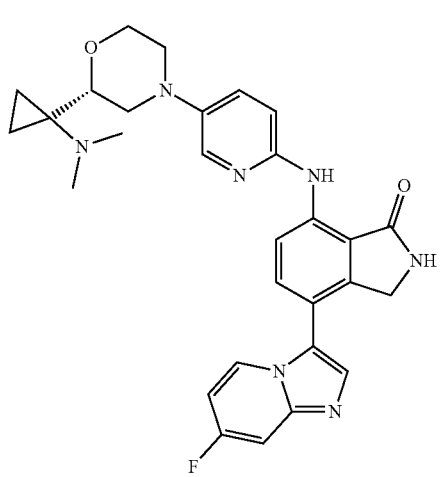

2617
-continued
I-688
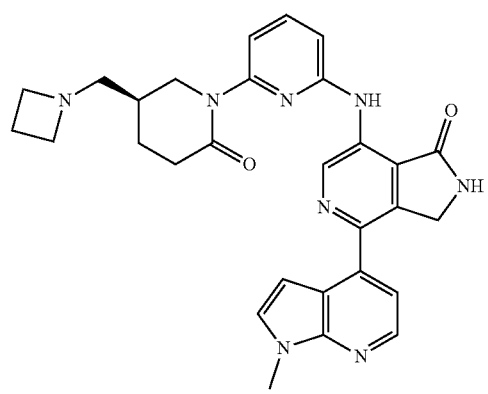
I-689
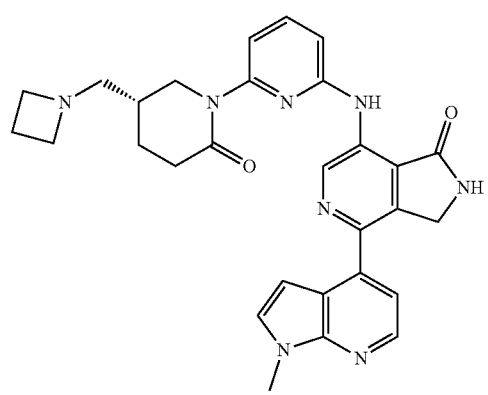
I-690
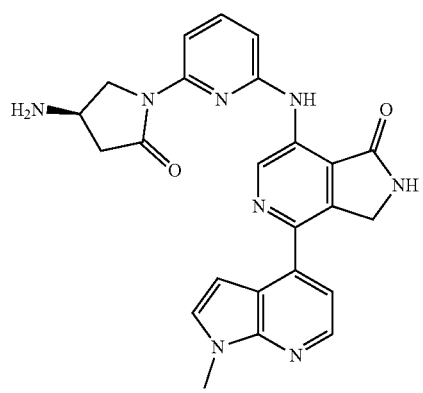
I-691
2618
-continued
I-692
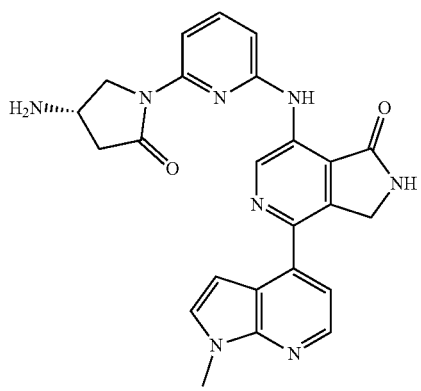
I-693
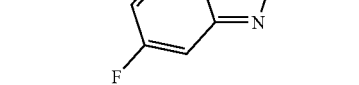
I-694

I-695
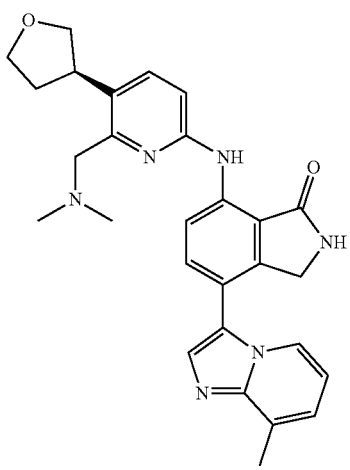
I-696
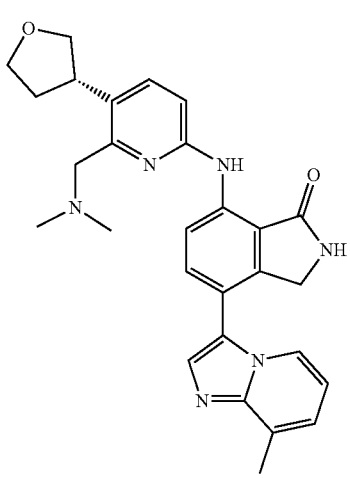
I-699
I-702
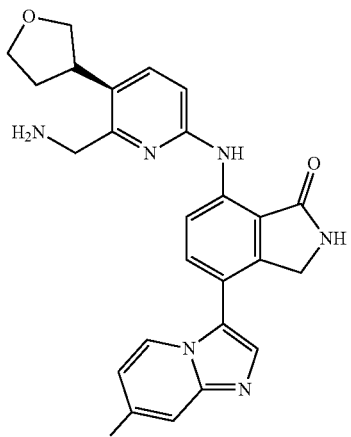
I-703
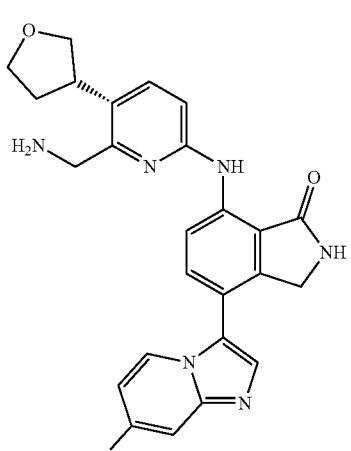
I-704
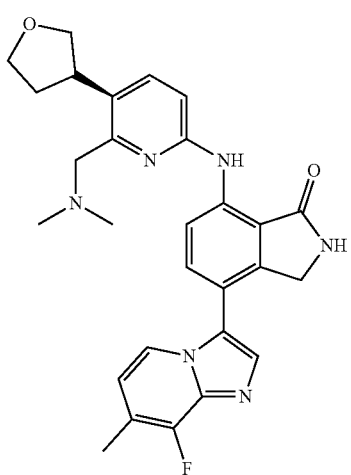

I-705
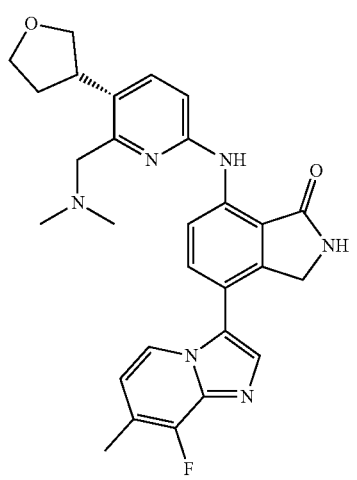
I-710
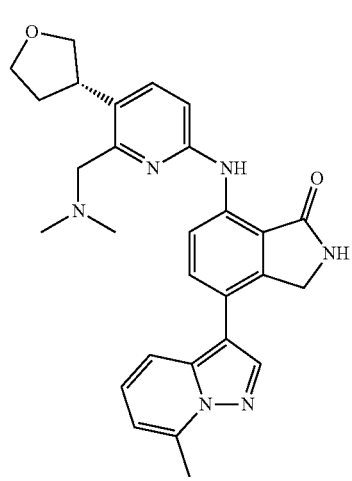
I-706
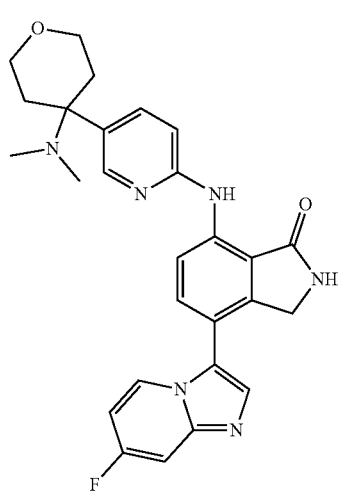
I-713
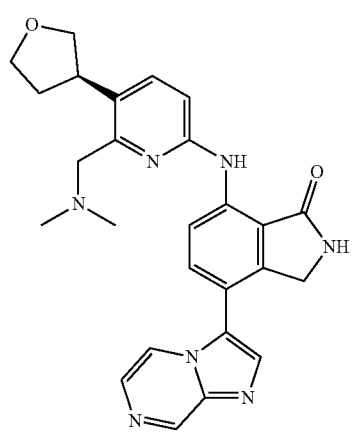
I-709
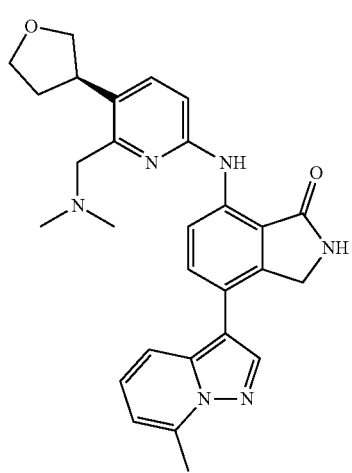
I-714
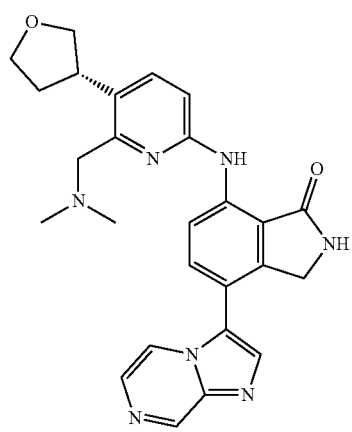

I-715
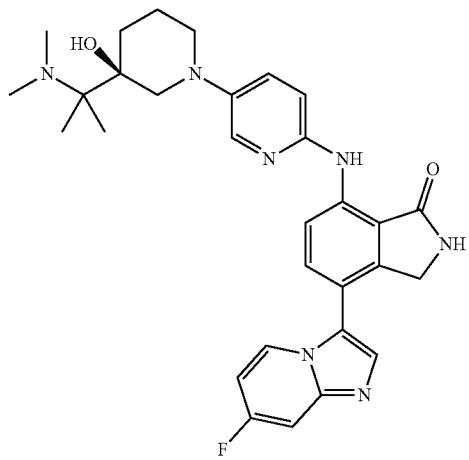
I-718
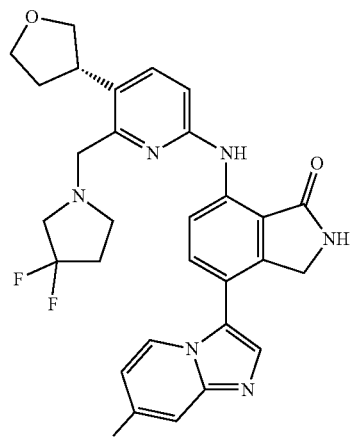
I-716
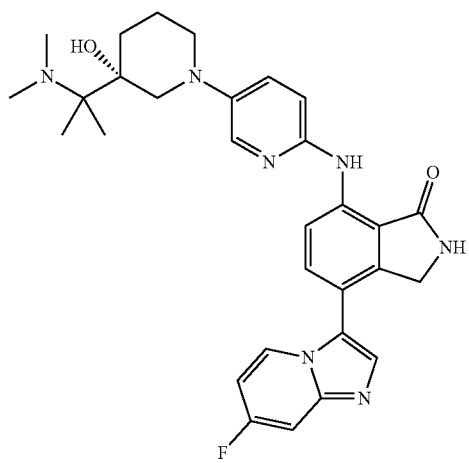
I-720
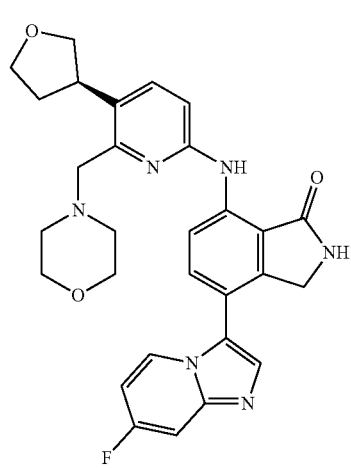
I-717
I-721
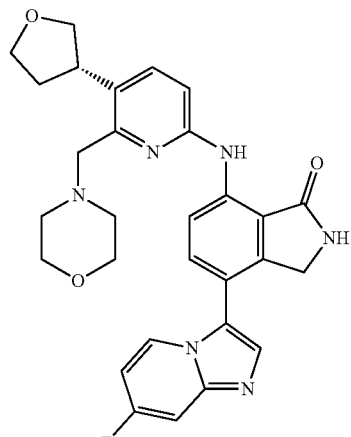

2625
-continued
I-722
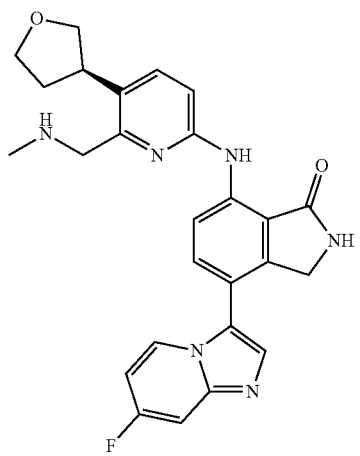
I-723
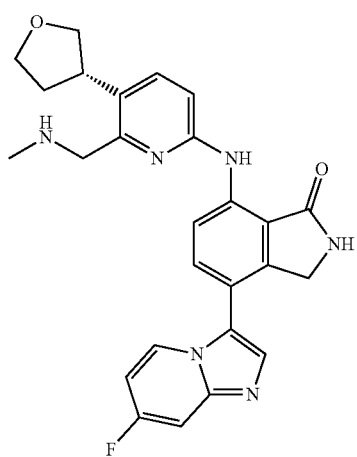
I-724
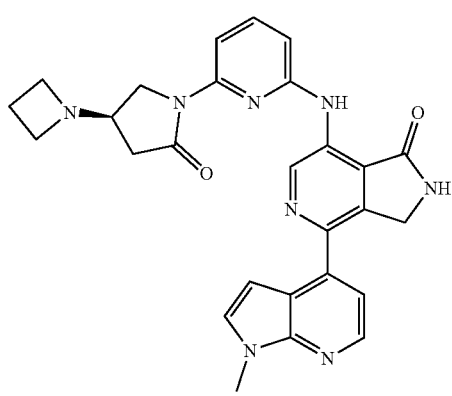
2626
-continued
I-725
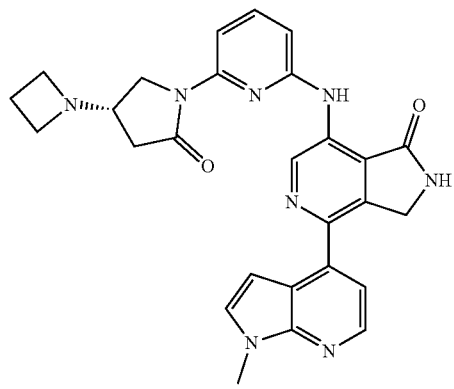
I-726
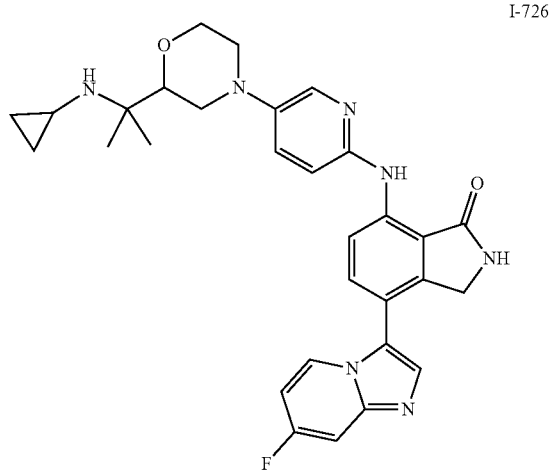
I-727
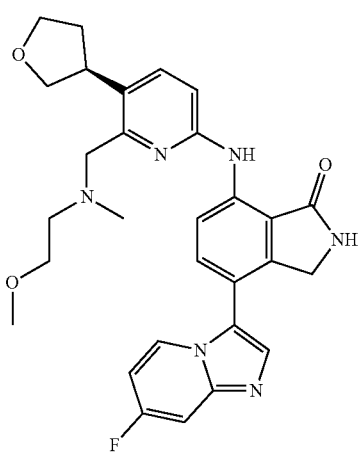

2627
-continued
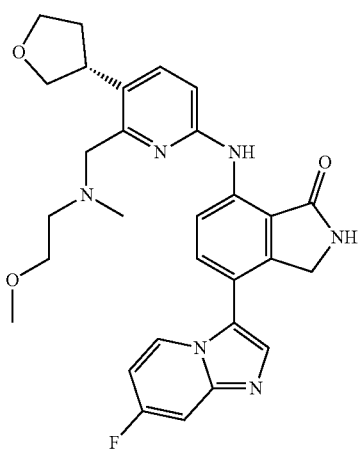
I-728
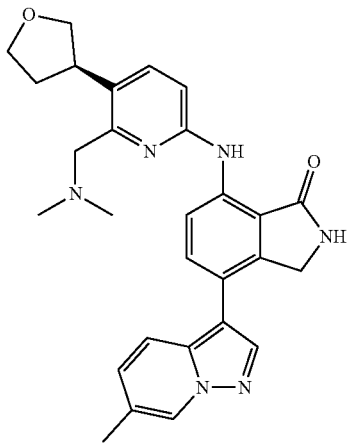
I-731
2628
-continued
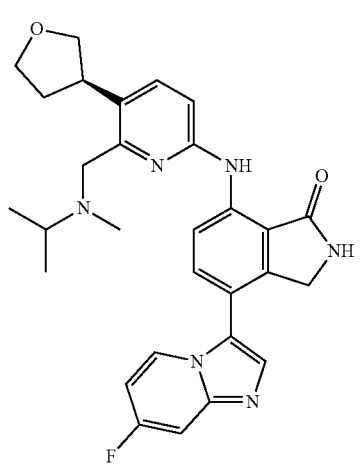
I-729
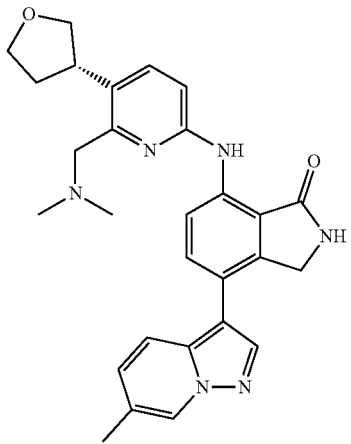
I-732
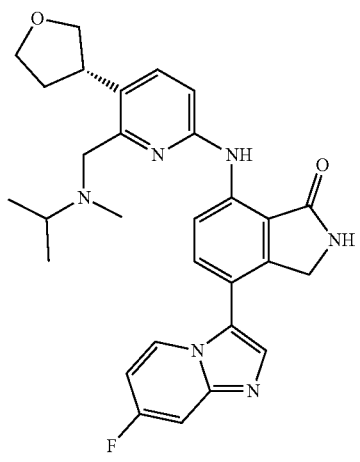
I-730
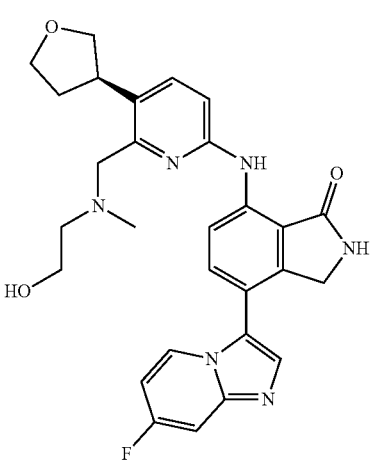
I-733

| 2629 -continued | 2630 -continued |
|---|---|
| 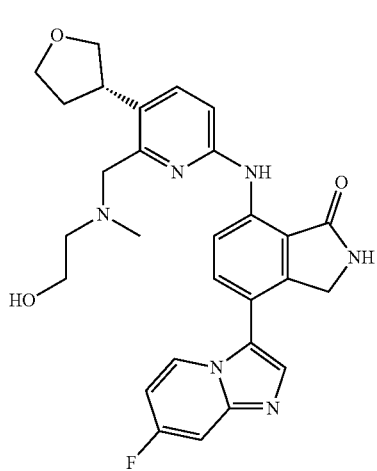 I-734 | 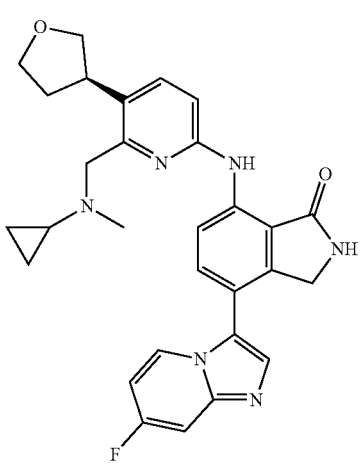 I-737 |
| 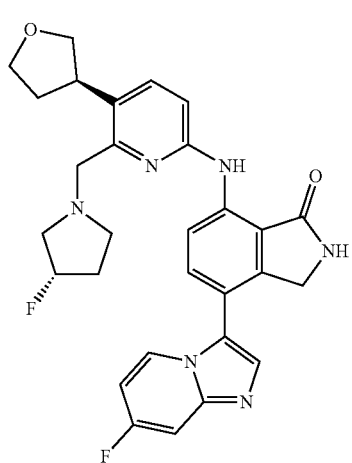 I-735 | 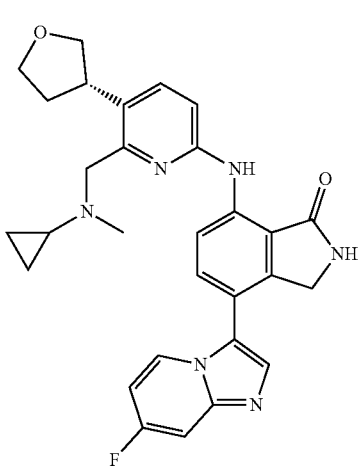 I-738 |
| 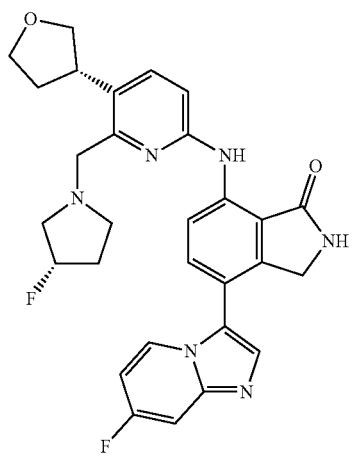 I-736 | 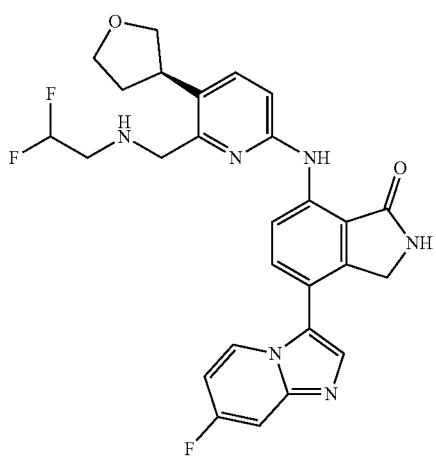 I-739 |

I-740
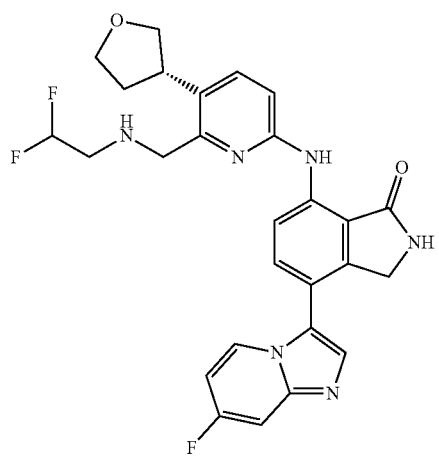
I-743
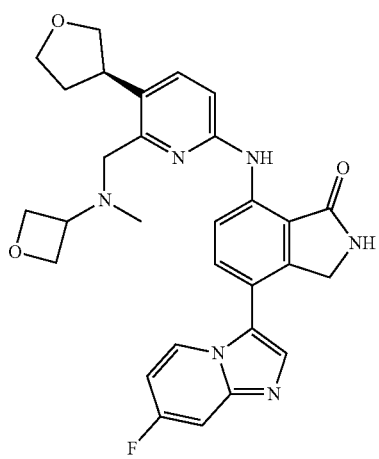
I-741
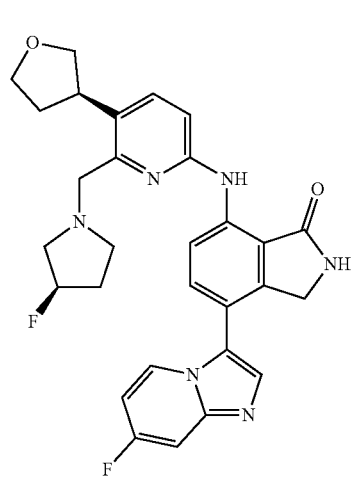
I-744
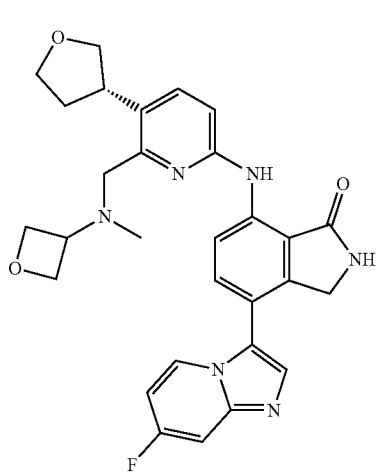
I-742
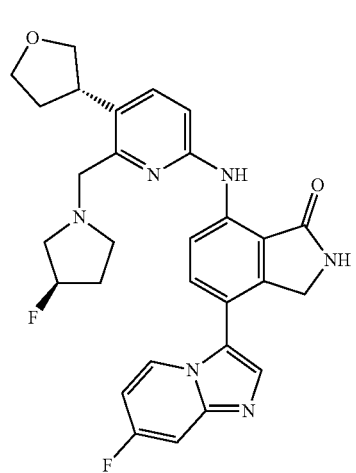
I-745
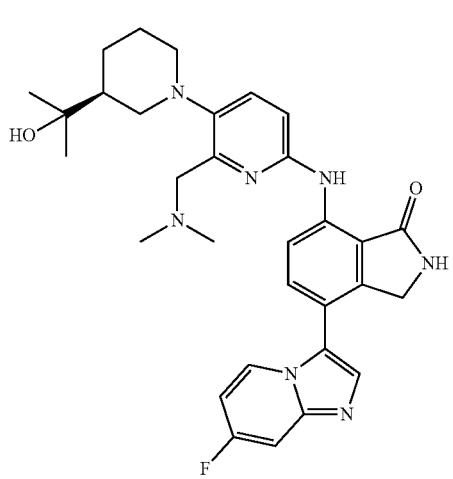

| 2633 -continued | 2634 -continued |
|---|---|
| I-746 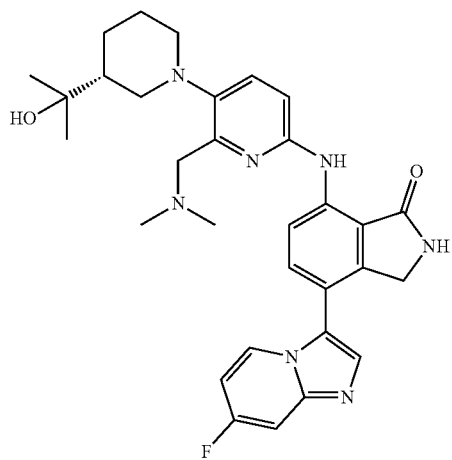 | I-749 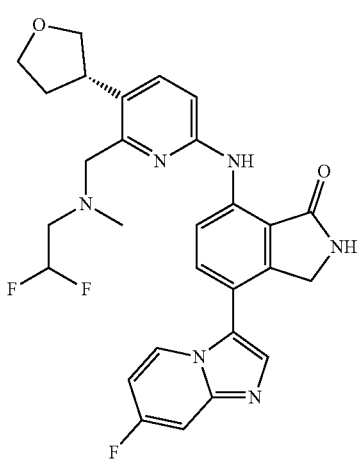 |
| I-747 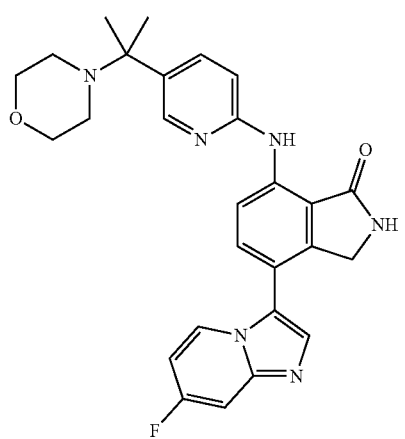 | I-750 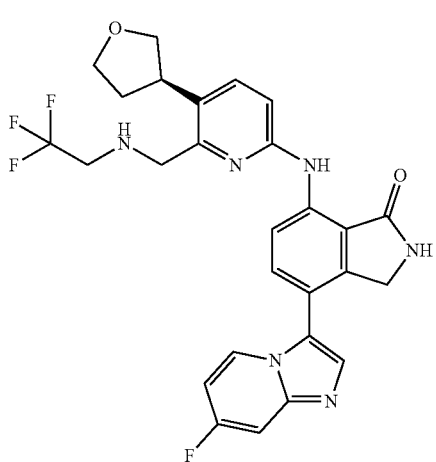 |
| I-748 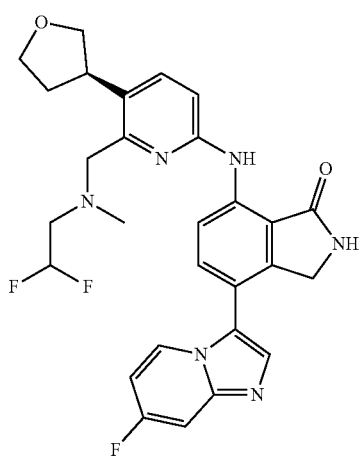 | I-751 |

I-752
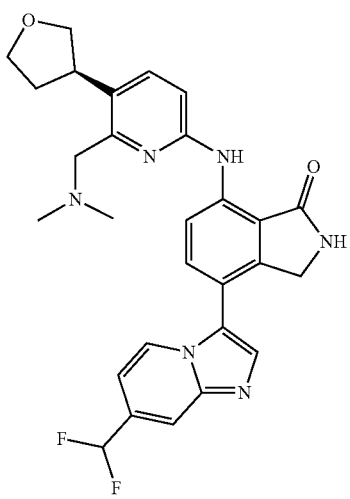
I-753
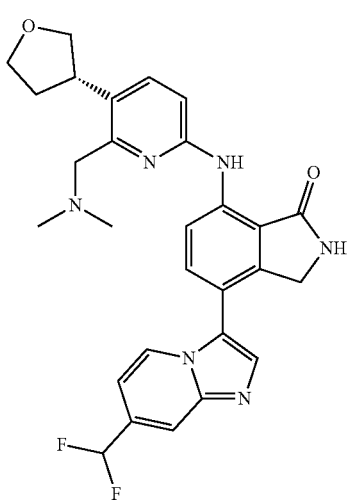
I-754
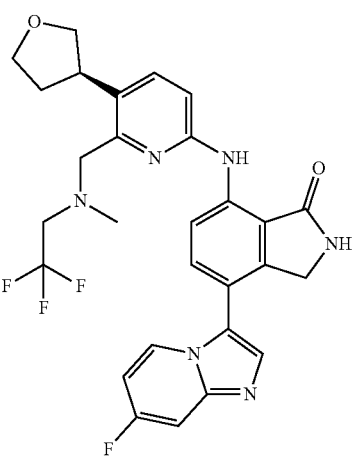
I-755
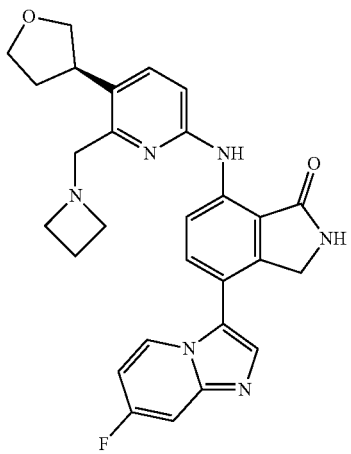
I-756
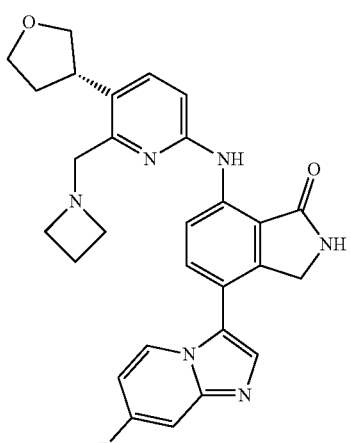
I-757
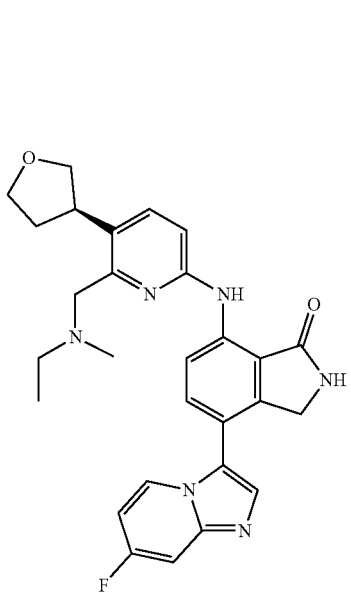

2637
-continued
I-758
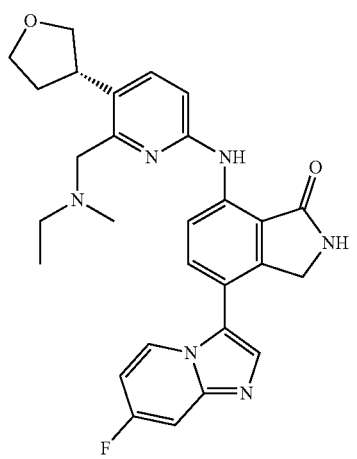
I-759
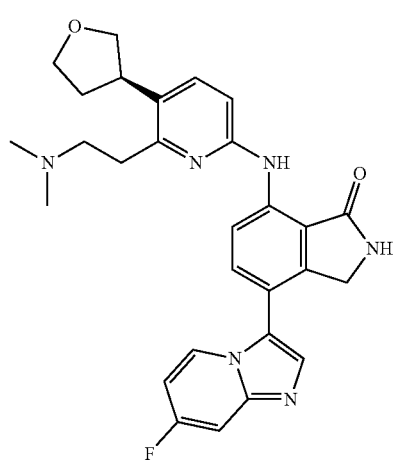
I-760
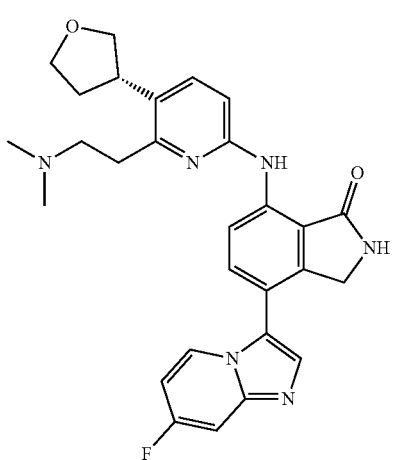
2638
-continued
I-761
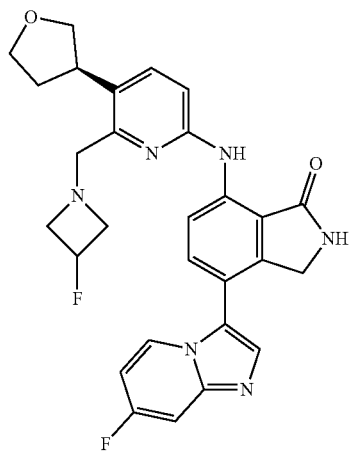
I-762
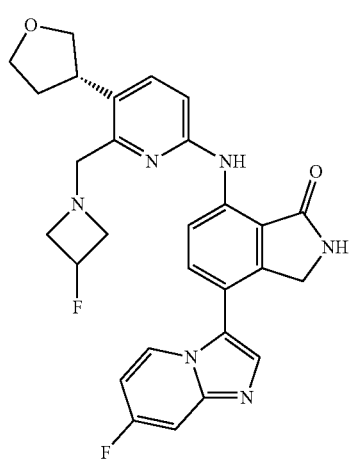
I-763
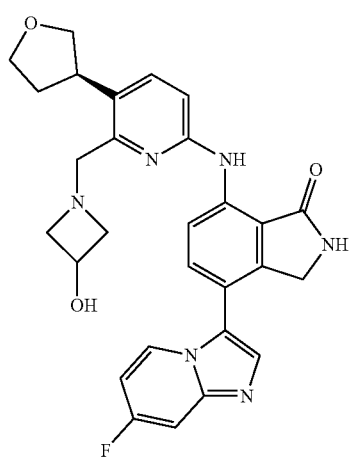

I-764
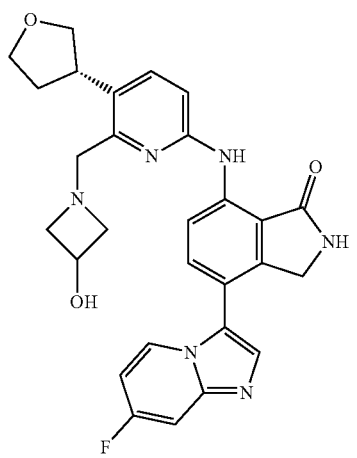
I-765
I-766
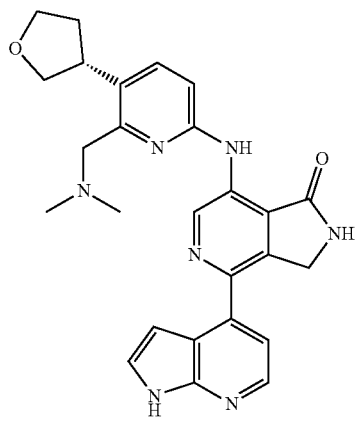
I-767
I-771
I-772
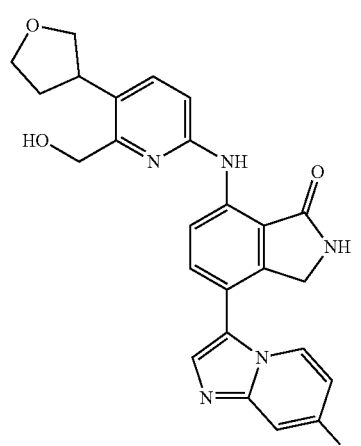
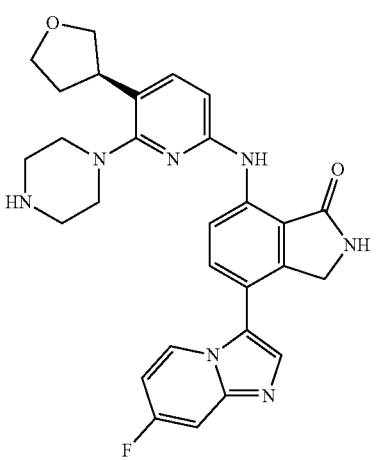

I-773
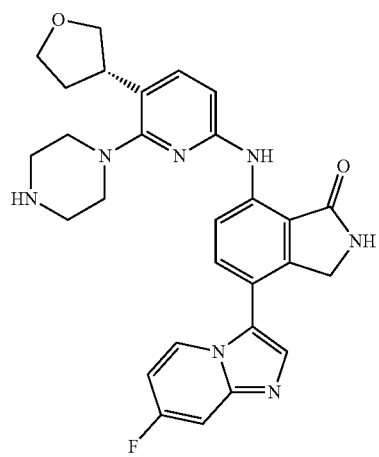
I-777
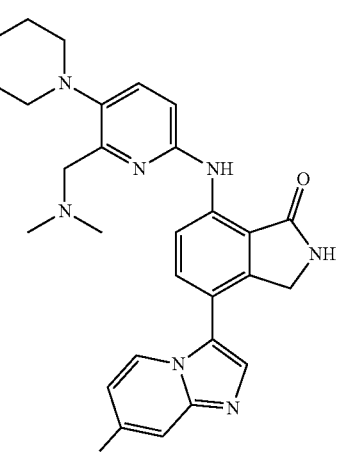
I-774
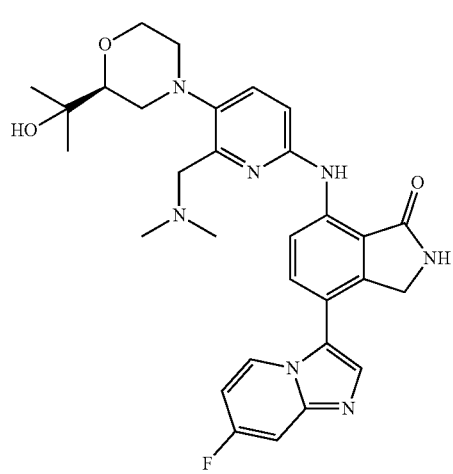
I-778
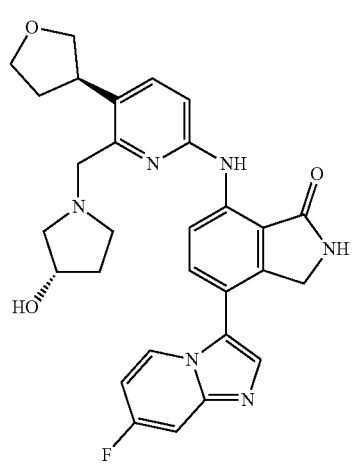
I-775
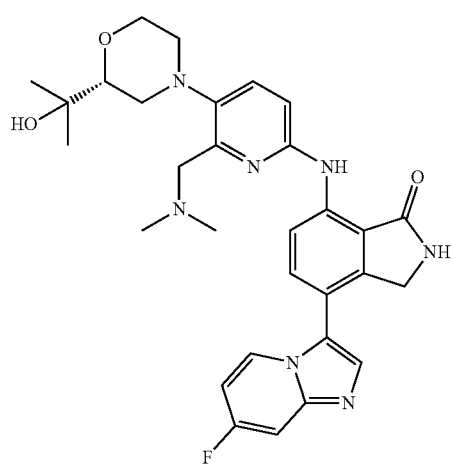
I-779
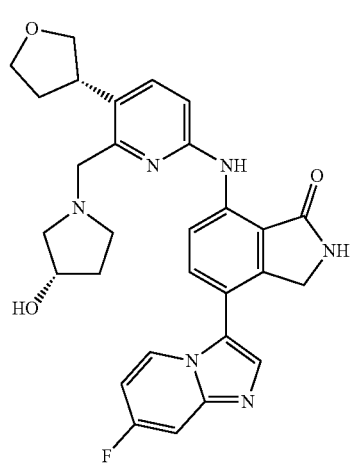

2643
-continued
I-780
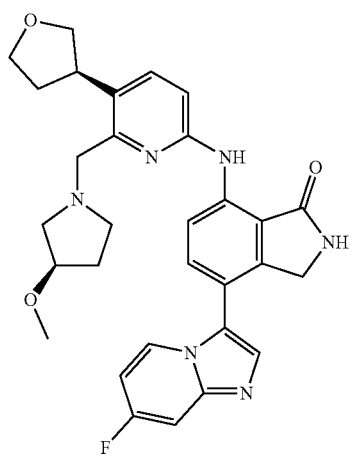
I-781
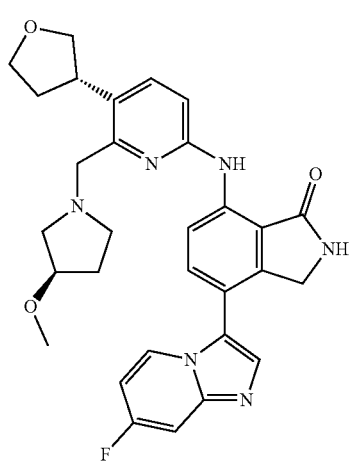
I-783
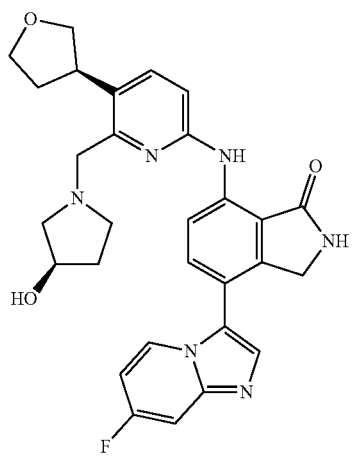
2644
-continued
I-784
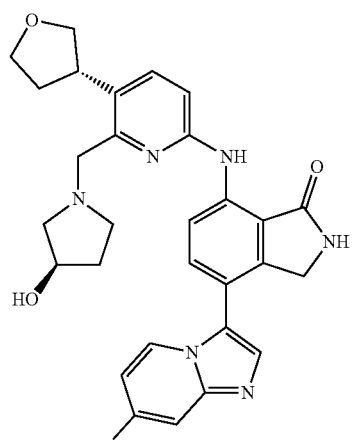
I-785
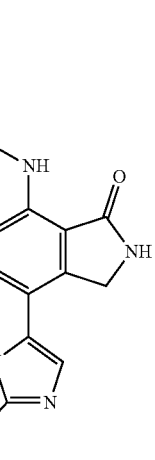
I-786
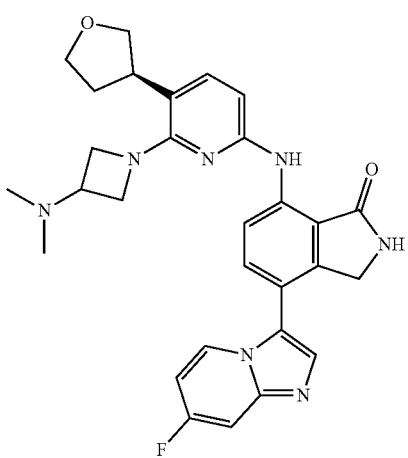

I-787
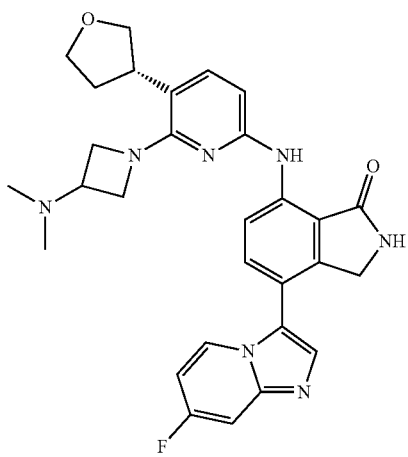
I-788
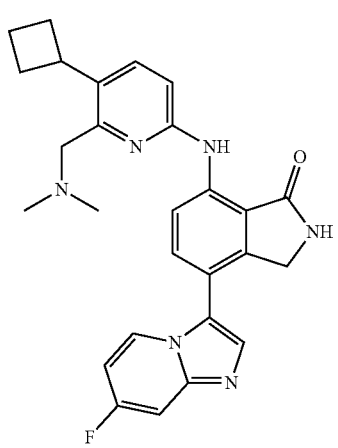
I-789
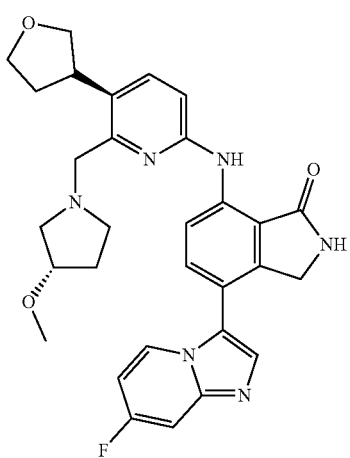
I-790
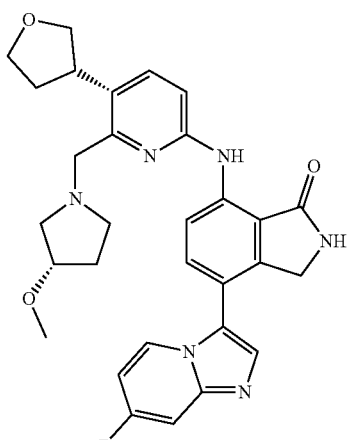
I-791
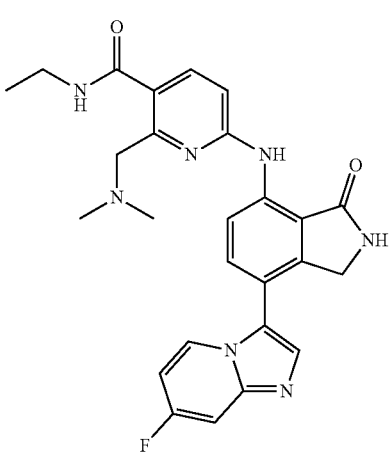
I-793
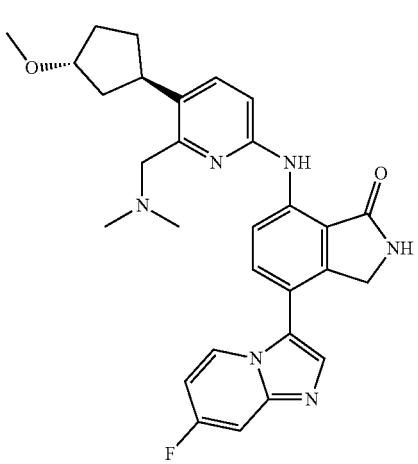

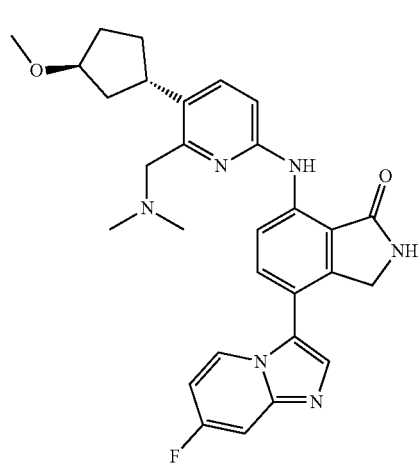
I-794
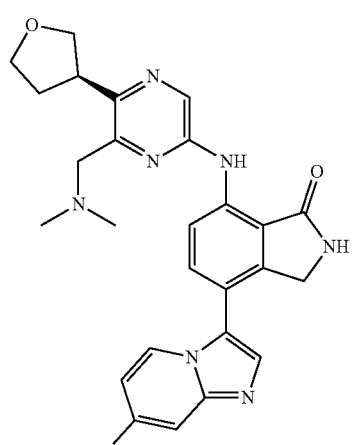
I-799
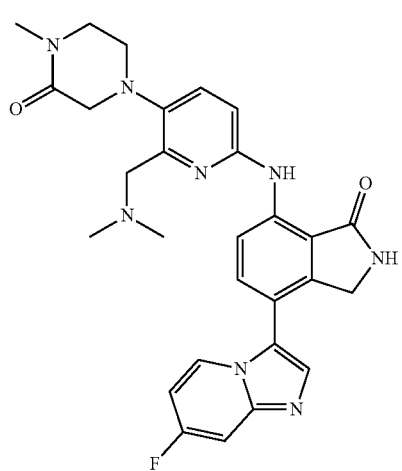
I-795
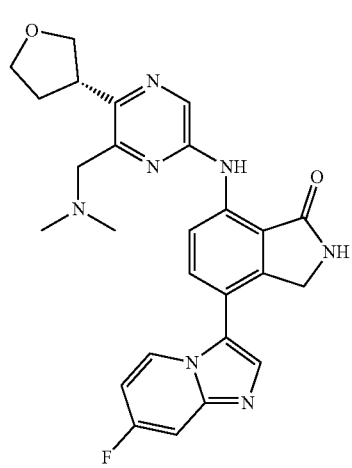
I-800
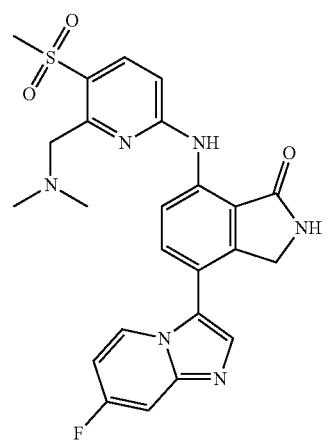
I-796
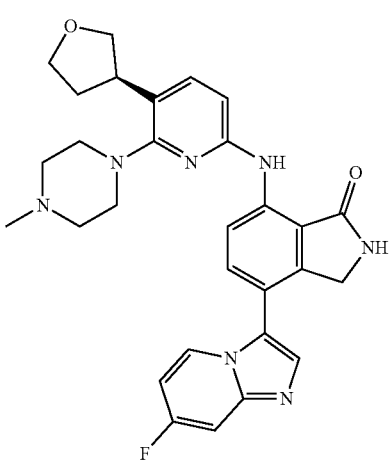
I-801

I-802
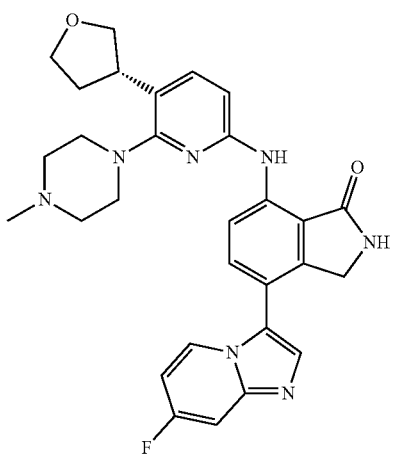
I-803
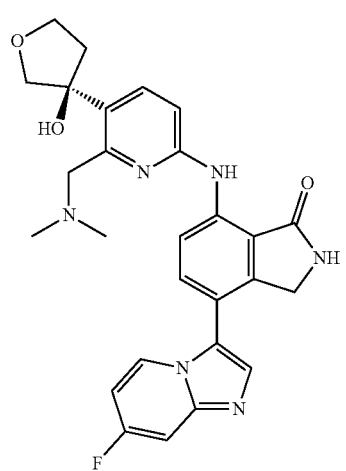
I-804
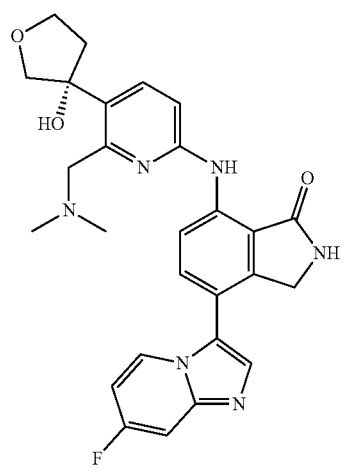
I-807
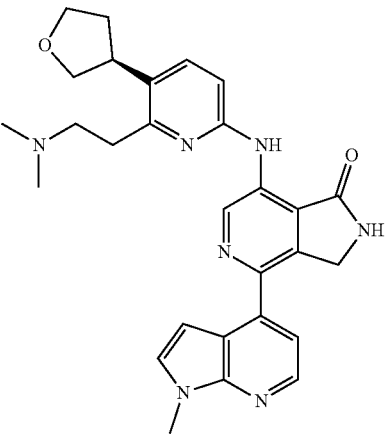
I-808
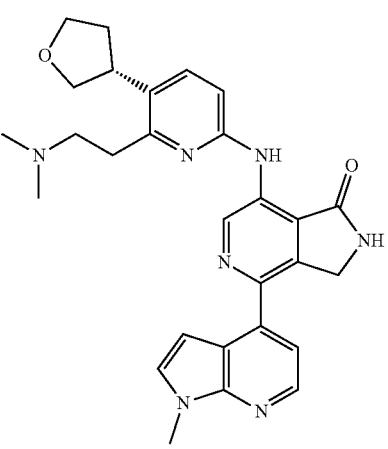
I-809
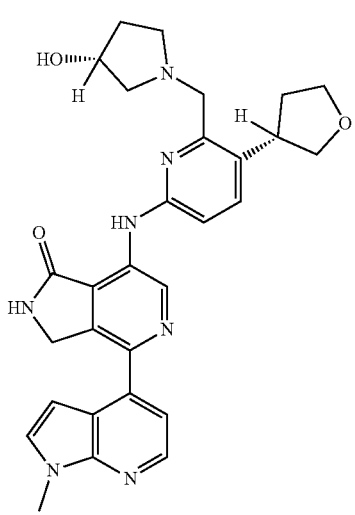

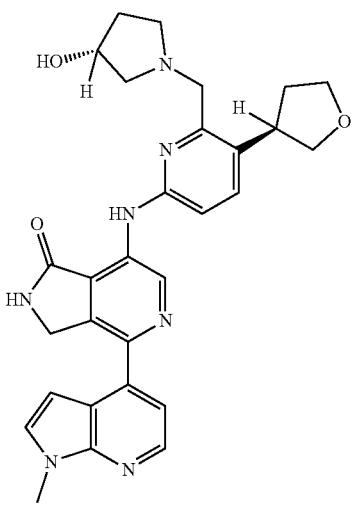
I-810
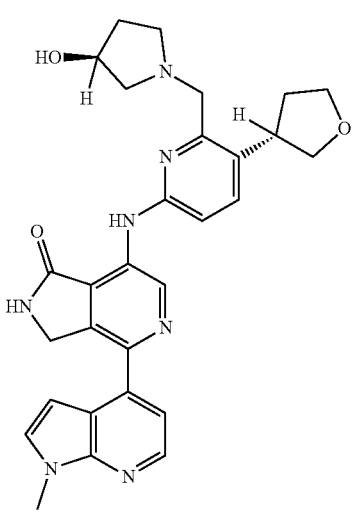
I-811
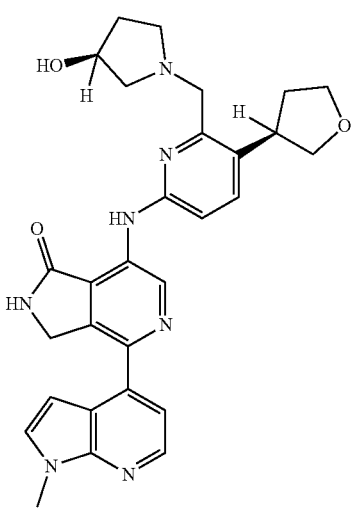
I-812
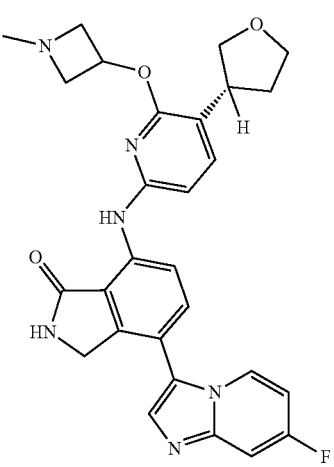
I-815
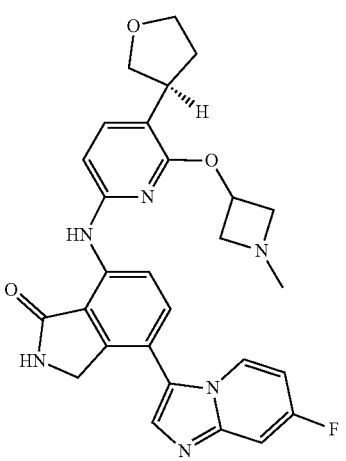
I-816
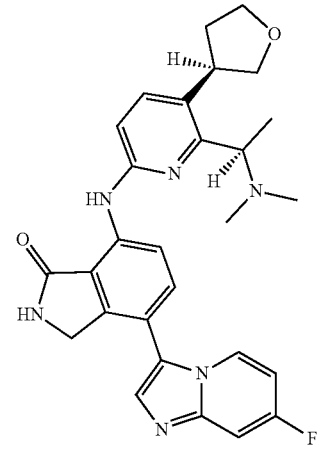
I-817

2653
-continued
I-818
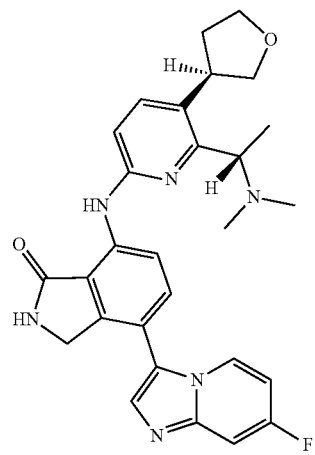
I-821
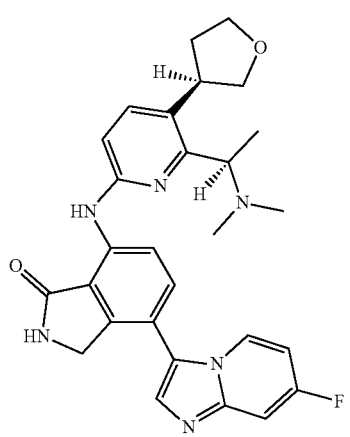
I-822
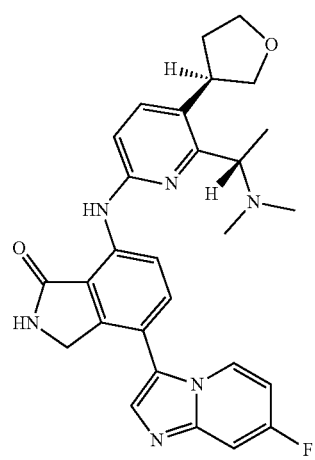
2654
-continued
I-823
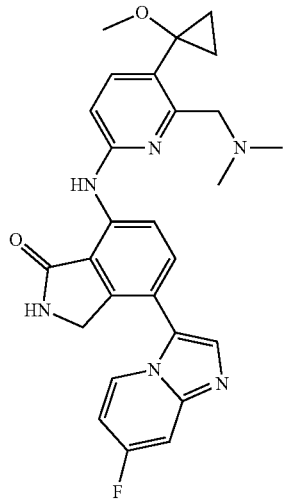
I-824
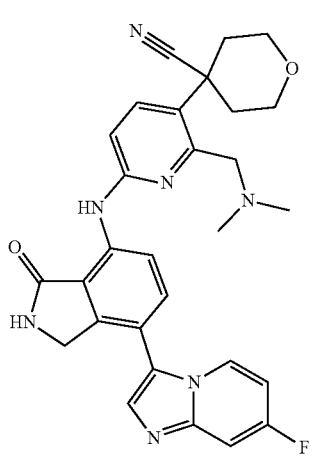
I-825
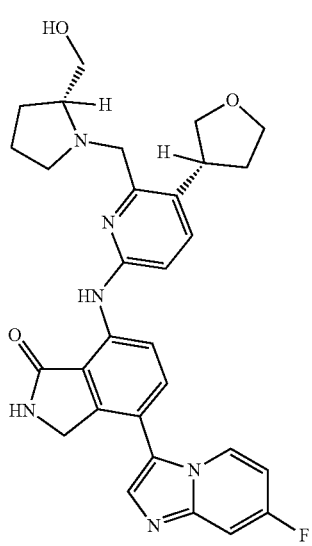

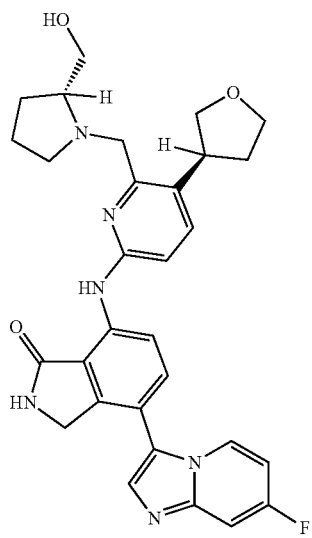
I-826
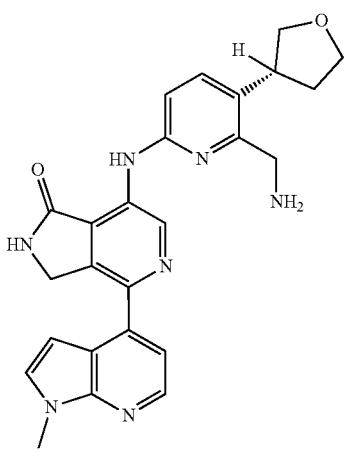
I-829
I-827
I-830
I-828
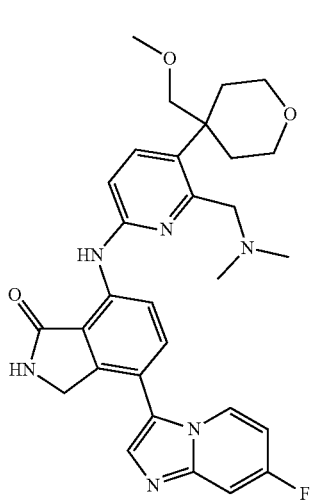
I-831

I-832 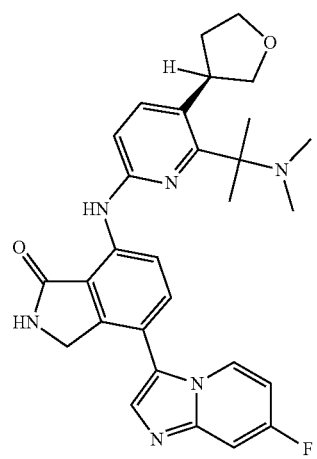
I-833 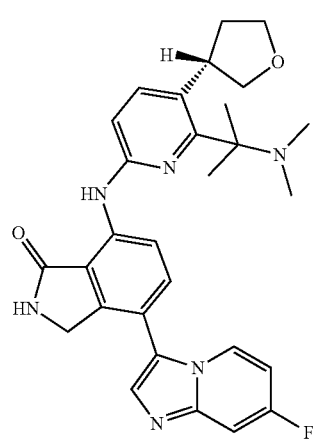
I-834 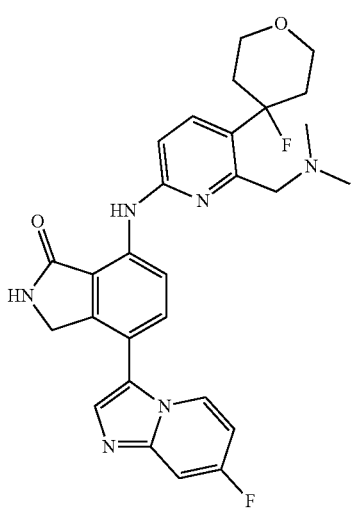
I-835 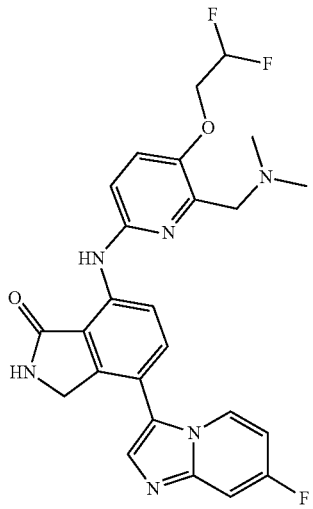
I-836 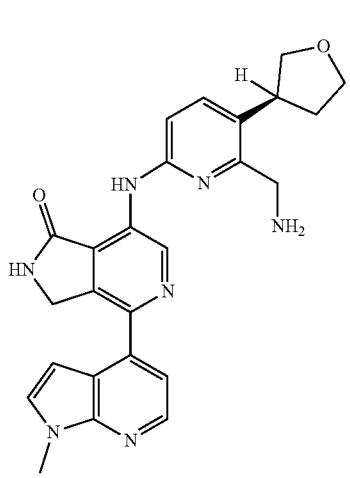
I-837 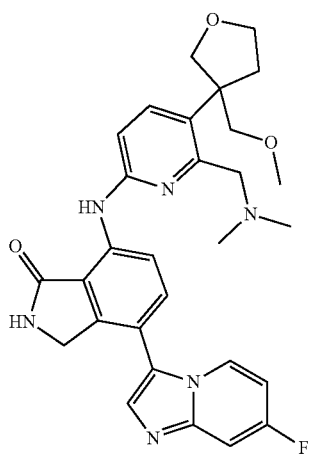

I-838
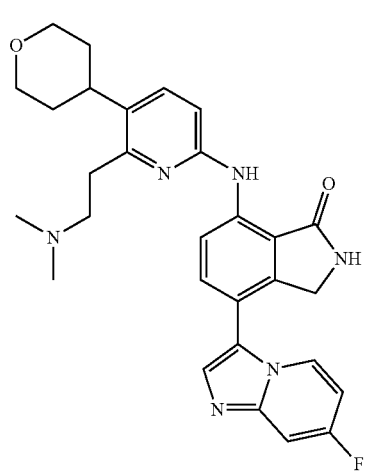
I-841
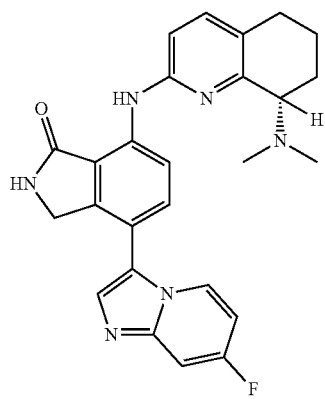 [SMILES: CN(C)[C@H]1CCCc2ccc(Nc3ccc(-c4cnc5cc(F)ccn45)c4c3C(=O)NC4)nc21]
I-839
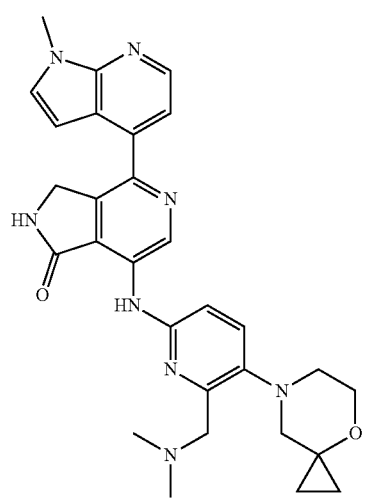
I-842
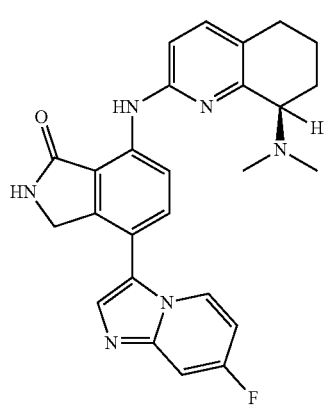 [SMILES: CN(C)[C@@H]1CCCc2ccc(Nc3ccc(-c4cnc5cc(F)ccn45)c4c3C(=O)NC4)nc21]
I-840
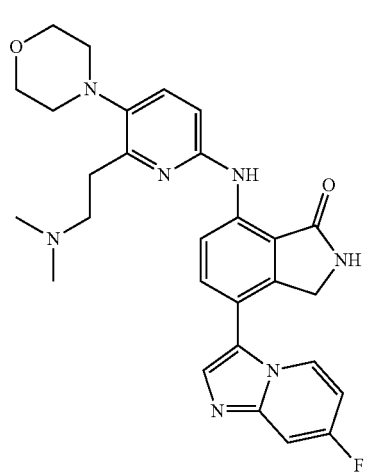
I-843
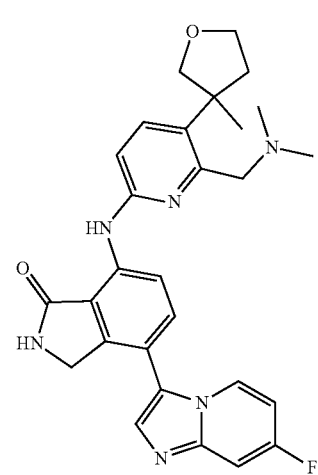

2661
-continued
I-844
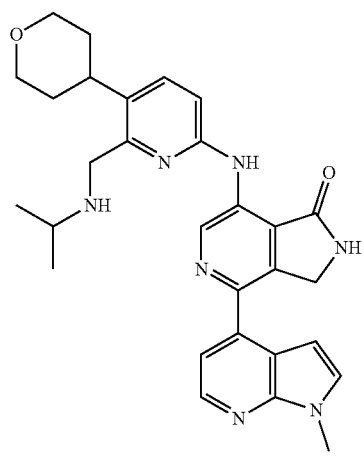 [SMILES: CC(C)NCc1nc(Nc2cnc(-c3ccnc4c3ccn4C)c3c2C(=O)NC3)ccc1C1CCOCC1]
I-845
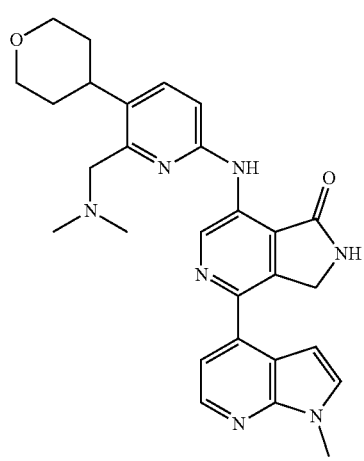 [SMILES: CN(C)Cc1nc(Nc2cnc(-c3ccnc4c3ccn4C)c3c2C(=O)NC3)ccc1C1CCOCC1]
I-846
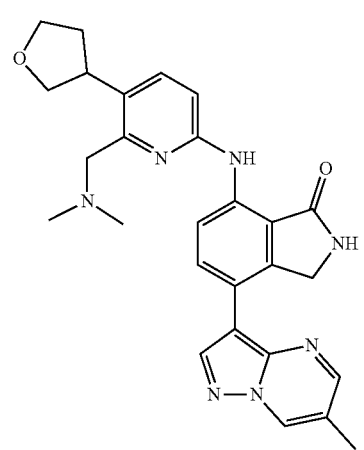 [SMILES: Cc1ccn2c(-c3ccc(Nc4ccc(C5CCOC5)c(CN(C)C)n4)c4c3CNC4=O)cnc2n1]
2662
-continued
I-847
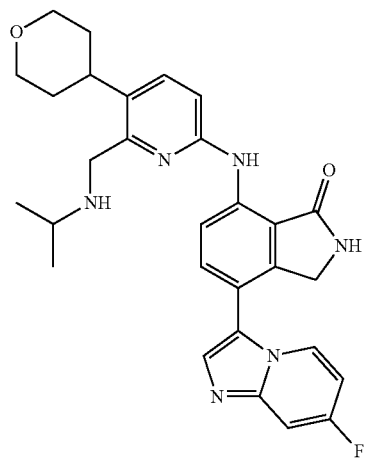 [SMILES: CC(C)NCc1nc(Nc2ccc(-c3cnc4nc(F)ccn34)c3c2C(=O)NC3)ccc1C1CCOCC1]
I-848
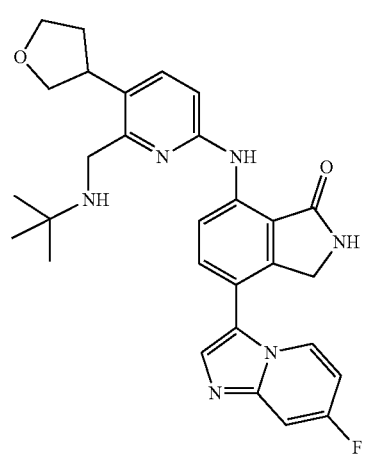 [SMILES: CC(C)(C)NCc1nc(Nc2ccc(-c3cnc4nc(F)ccn34)c3c2C(=O)NC3)ccc1C1CCOC1]
I-849
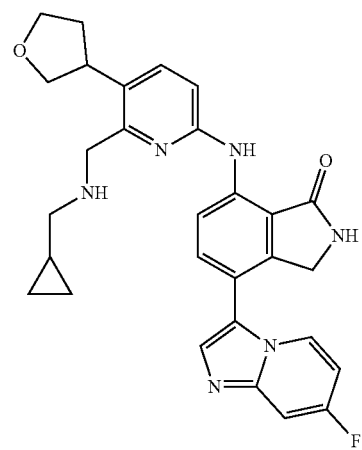 [SMILES: O=C1NCc2c(-c3cnc4nc(F)ccn34)ccc(Nc3ccc(C4CCOC4)c(CNCC4CC4)n3)c21]

I-851
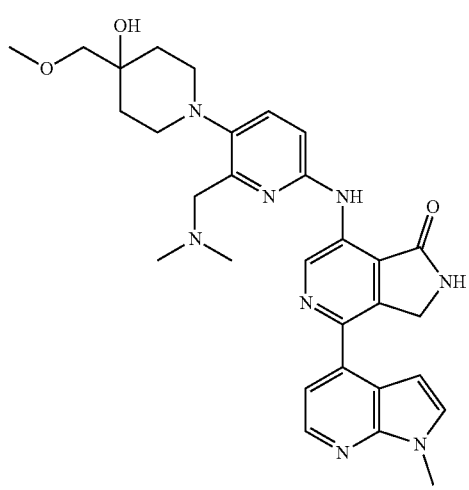 [SMILES: COCC1(O)CCN(c2ccc(Nc3cnc(-c4ccnc5c4ccn5C)c4c3C(=O)NC4)nc2CN(C)C)CC1]
I-852
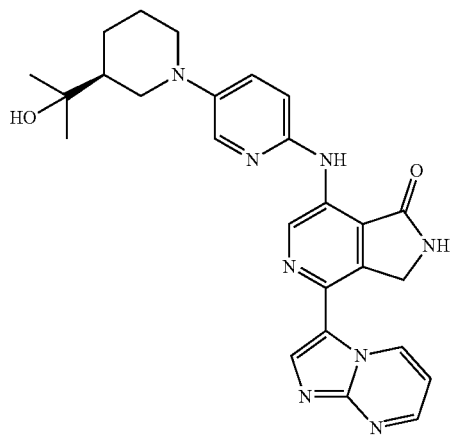 [SMILES: CC(C)(O)[C@H]1CCCN(c2ccc(Nc3cnc(-c4cnc5ncccn45)c4c3C(=O)NC4)nc2)C1]
I-853
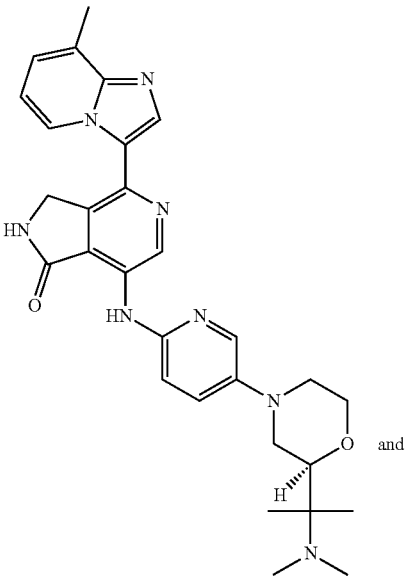
I-854
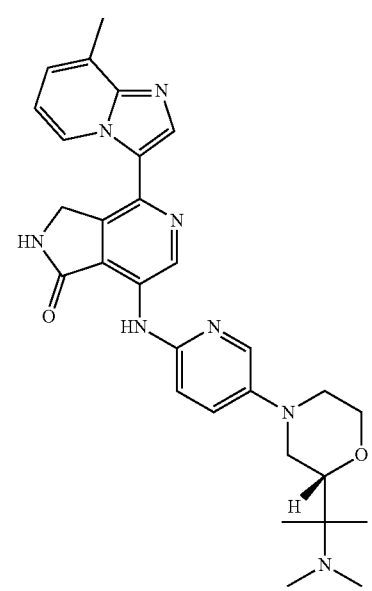
and
I-855
or a pharmaceutically acceptable salt thereof.
18. A pharmaceutical composition comprising a compound according to claim 1, or a pharmaceutically acceptable salt thereof, and a pharmaceutically acceptable carrier, adjuvant, or vehicle.
* * * * *